(12) United States Patent
Clemens et al.

(10) Patent No.: US 12,324,802 B2
(45) Date of Patent: Jun. 10, 2025

(54) MODULATORS OF CYSTIC FIBROSIS TRANSMEMBRANE CONDUCTANCE REGULATOR

(71) Applicant: Vertex Pharmaceuticals Incorporated, Boston, MA (US)

(72) Inventors: Jeremy J. Clemens, San Diego, CA (US); William Schulz Bechara, Laval (CA); Brett C. Bookser, San Diego, CA (US); Thomas Cleveland, San Marcos, CA (US); Timothy R. Coon, Carlsbad, CA (US); Michel Gallant, Pierrefonds (CA); Peter Grootenhuis, Del Mar, CA (US); Sara Sabina Hadida Ruah, La Jolla, CA (US); Julie Laterreur, San Diego, CA (US); Mark Thomas Miller, Rancho Santa Fe, CA (US); Prasuna Paraselli, San Diego, CA (US); Yeeman K. Ramtohul, Pierrefonds (CA); Thumkunta Jagadeeswar Reddy, Pierrefonds (CA); Claudio Sturino, Ile Bizard (CA); Lino Valdez, San Diego, CA (US); Jinglan Zhou, San Diego, CA (US); Minson Baek, San Diego, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 601 days.

(21) Appl. No.: 17/528,729

(22) Filed: Nov. 17, 2021

(65) Prior Publication Data

US 2023/0099745 A1    Mar. 30, 2023

Related U.S. Application Data

(60) Provisional application No. 63/115,552, filed on Nov. 18, 2020.

(51) Int. Cl.

| | | |
|---|---|---|
| *A61K 31/436* | (2006.01) | |
| *A61K 31/404* | (2006.01) | |
| *A61K 31/439* | (2006.01) | |
| *A61K 31/443* | (2006.01) | |
| *A61K 31/4439* | (2006.01) | |
| *A61K 31/4995* | (2006.01) | |
| *A61K 31/529* | (2006.01) | |
| *A61P 3/00* | (2006.01) | |
| *A61P 43/00* | (2006.01) | |
| *C07D 498/18* | (2006.01) | |
| *C07D 498/22* | (2006.01) | |
| *C07D 515/04* | (2006.01) | |

(52) U.S. Cl.
CPC .......... *A61K 31/439* (2013.01); *A61K 31/404* (2013.01); *A61K 31/443* (2013.01); *A61K 31/4439* (2013.01); *A61K 31/4995* (2013.01); *A61K 31/529* (2013.01); *C07D 498/18* (2013.01); *C07D 498/22* (2013.01)

(58) Field of Classification Search
CPC .......... A61P 3/00; A61P 43/00; C07D 515/04; A61K 31/436
See application file for complete search history.

(56) References Cited

U.S. PATENT DOCUMENTS

| | | |
|---|---|---|
| 7,407,976 B2 | 8/2008 | Miller et al. |
| 7,495,103 B2 | 2/2009 | Hadida-Ruah et al. |
| 7,553,855 B2 | 6/2009 | Young et al. |
| 7,598,412 B2 | 10/2009 | Hadida Ruah et al. |
| 7,645,789 B2 | 1/2010 | Hadida Ruah et al. |
| 7,659,268 B2 | 2/2010 | Hadida-Ruah et al. |
| 7,671,221 B2 | 3/2010 | Hadida Ruah et al. |
| 7,691,902 B2 | 4/2010 | Hadida Ruah et al. |
| 7,741,321 B2 | 6/2010 | Hadida Ruah et al. |
| 7,754,739 B2 | 7/2010 | Hadida Ruah et al. |
| 7,776,905 B2 | 8/2010 | Hadida Ruah et al. |
| 7,846,951 B2 | 12/2010 | Miller et al. |
| 7,956,052 B2 | 6/2011 | Hadida Ruah et al. |
| 7,973,038 B2 | 7/2011 | Hadida Ruah et al. |
| 7,973,169 B2 | 7/2011 | Hadida Ruah et al. |
| 7,977,322 B2 | 7/2011 | Ruah et al. |
| 7,999,113 B2 | 8/2011 | Hadida-Ruah et al. |
| 8,012,999 B2 | 9/2011 | Hadida Ruah et al. |
| 8,039,491 B2 | 10/2011 | Hadida Ruah et al. |
| 8,076,357 B2 | 12/2011 | Young et al. |
| 8,101,767 B2 | 1/2012 | Ruah et al. |

(Continued)

FOREIGN PATENT DOCUMENTS

| | | |
|---|---|---|
| WO | WO 2004/058717 A1 | 7/2004 |
| WO | WO 2004/080972 A1 | 9/2004 |

(Continued)

OTHER PUBLICATIONS

Bastin, Richard J., et al., "Salt selection and optimization procedures for pharmaceutical new chemical entities," *Org. Pro. Res. Dev.* 2000, 4(5), 427-435.

(Continued)

*Primary Examiner* — Amanda L. Aguirre
*Assistant Examiner* — Chris E Simmons
(74) *Attorney, Agent, or Firm* — Finnegan, Henderson, Farabow, Garrett & Dunner, LLP

(57) ABSTRACT

This disclosure provides modulators of Cystic Fibrosis Transmembrane Conductance Regulator (CFTR), pharmaceutical compositions containing at least one such modulator, methods of treatment of cystic fibrosis using such modulators and pharmaceutical compositions, and processes for making such modulators.

53 Claims, 20 Drawing Sheets

(56) References Cited

U.S. PATENT DOCUMENTS

| | | |
|---|---|---|
| 8,124,781 B2 | 2/2012 | Siesel |
| 8,163,772 B2 | 4/2012 | DeMattei et al. |
| 8,188,283 B2 | 5/2012 | Binch et al. |
| 8,227,615 B2 | 7/2012 | Hadida-Ruah et al. |
| 8,232,302 B2 | 7/2012 | Miller et al. |
| 8,242,149 B2 | 8/2012 | Ruah et al. |
| 8,299,099 B2 | 10/2012 | Ruah et al. |
| 8,314,239 B2 | 11/2012 | Binch et al. |
| 8,314,256 B2 | 11/2012 | Ruah et al. |
| 8,318,733 B2 | 11/2012 | Hadida-Ruah et al. |
| 8,324,207 B2 | 12/2012 | Hadida Ruah et al. |
| 8,324,242 B2 | 12/2012 | Ruah et al. |
| 8,344,147 B2 | 1/2013 | Ambhaikar et al. |
| 8,354,427 B2 | 1/2013 | Van Goor |
| 8,362,253 B2 | 1/2013 | DeMattei et al. |
| 8,367,660 B2 | 2/2013 | Binch et al. |
| 8,389,727 B2 | 3/2013 | Zhang et al. |
| 8,399,479 B2 | 3/2013 | Binch et al. |
| 8,404,849 B2 | 3/2013 | Sun et al. |
| 8,404,865 B2 | 3/2013 | Ambhaikar et al. |
| 8,410,132 B2 | 4/2013 | Binch et al. |
| 8,410,274 B2 | 4/2013 | Hurter et al. |
| 8,415,387 B2 | 4/2013 | Ruah et al. |
| 8,431,605 B2 | 4/2013 | Hadida Ruah et al. |
| 8,436,014 B2 | 5/2013 | Zhang et al. |
| 8,461,156 B2 | 6/2013 | Hadida Ruah et al. |
| 8,461,342 B2 | 6/2013 | Siesel |
| 8,461,352 B2 | 6/2013 | Ambhaikar et al. |
| 8,471,029 B2 | 6/2013 | Arekar et al. |
| 8,476,442 B2 | 7/2013 | DeMattei et al. |
| 8,507,524 B2 | 8/2013 | Ruah et al. |
| 8,507,534 B2 | 8/2013 | Keshavarz-Shokri et al. |
| 8,507,687 B2 | 8/2013 | Keshavarz-Shokri et al. |
| 8,513,282 B2 | 8/2013 | Binch et al. |
| 8,524,767 B2 | 9/2013 | Miller et al. |
| 8,524,910 B2 | 9/2013 | Hadida Ruah et al. |
| 8,541,453 B2 | 9/2013 | Hadida-Ruah et al. |
| 8,552,006 B2 | 10/2013 | Binch et al. |
| 8,552,034 B2 | 10/2013 | Verwijs et al. |
| 8,563,573 B2 | 10/2013 | Ruah et al. |
| 8,563,593 B2 | 10/2013 | Alargova et al. |
| 8,575,209 B2 | 11/2013 | Ruah et al. |
| 8,586,615 B2 | 11/2013 | Hadida-Ruah et al. |
| 8,592,602 B2 | 11/2013 | Siesel |
| 8,598,181 B2 | 12/2013 | Hadida Ruah et al. |
| 8,598,205 B2 | 12/2013 | Binch et al. |
| 8,604,203 B2 | 12/2013 | Binch et al. |
| 8,609,703 B2 | 12/2013 | Ruah et al. |
| 8,614,325 B2 | 12/2013 | Yang et al. |
| 8,614,327 B2 | 12/2013 | Sheth et al. |
| 8,623,894 B2 | 1/2014 | DeMattei et al. |
| 8,623,905 B2 | 1/2014 | Ruah et al. |
| 8,629,162 B2 | 1/2014 | Hadida-Ruah et al. |
| 8,633,189 B2 | 1/2014 | Binch et al. |
| 8,642,609 B2 | 2/2014 | Makings et al. |
| 8,653,103 B2 | 2/2014 | Keshavarz-Shokri et al. |
| 8,674,108 B2 | 3/2014 | Luisi et al. |
| 8,710,075 B2 | 4/2014 | Binch et al. |
| 8,716,338 B2 | 5/2014 | Young |
| 8,722,704 B2 | 5/2014 | Hadida Ruah et al. |
| 8,741,922 B2 | 6/2014 | Zhang et al. |
| 8,741,925 B2 | 6/2014 | Hadida-Ruah et al. |
| 8,741,933 B2 | 6/2014 | Hadida Ruah et al. |
| 8,741,939 B2 | 6/2014 | Hadida Ruah et al. |
| 8,742,122 B2 | 6/2014 | Keshavarz-Shokri et al. |
| 8,748,612 B2 | 6/2014 | Binch et al. |
| 8,754,222 B2 | 6/2014 | Ambhaikar et al. |
| 8,754,224 B2 | 6/2014 | Hurter et al. |
| 8,759,335 B2 | 6/2014 | Hadida Ruah et al. |
| 8,765,957 B2 | 7/2014 | DeMattei et al. |
| 8,785,476 B2 | 7/2014 | Arekar et al. |
| 8,785,640 B2 | 7/2014 | Binch et al. |
| 8,796,308 B2 | 8/2014 | Yang et al. |
| 8,796,312 B2 | 8/2014 | Hadida Ruah et al. |
| 8,802,700 B2 | 8/2014 | Sheth et al. |
| 8,802,844 B2 | 8/2014 | Gallardo-Godoy |
| 8,802,868 B2 | 8/2014 | Keshavarz-Shokri et al. |
| 8,816,093 B2 | 8/2014 | Siesel |
| 8,822,451 B2 | 9/2014 | Ruah et al. |
| 8,829,204 B2 | 9/2014 | Hadida-Ruah et al. |
| 8,835,639 B2 | 9/2014 | DeMattei et al. |
| 8,846,718 B2 | 9/2014 | Keshavarz-Shokri et al. |
| 8,846,753 B2 | 9/2014 | Hadida Ruah et al. |
| 8,853,254 B2 | 10/2014 | Hadida Ruah et al. |
| 8,853,415 B2 | 10/2014 | Hadida Ruah et al. |
| 8,865,902 B2 | 10/2014 | Morgan |
| 8,883,206 B2 | 11/2014 | Doukou et al. |
| 8,884,018 B2 | 11/2014 | Ambhaikar et al. |
| 8,889,875 B2 | 11/2014 | Ruah et al. |
| 8,912,199 B2 | 12/2014 | Hadida Ruah et al. |
| 8,952,049 B2 | 2/2015 | Ruah et al. |
| 8,952,050 B2 | 2/2015 | Ruah et al. |
| 8,962,856 B2 | 2/2015 | Hadida-Ruah et al. |
| 8,969,382 B2 | 3/2015 | Binch et al. |
| 8,969,386 B2 | 3/2015 | Hadida-Ruah et al. |
| 8,969,574 B2 | 3/2015 | Keshavarz-Shokri et al. |
| 8,993,600 B2 | 3/2015 | Hadida Ruah et al. |
| 8,999,976 B2 | 4/2015 | Binch et al. |
| 9,012,473 B2 | 4/2015 | Hadida Ruah et al. |
| 9,012,496 B2 | 4/2015 | Alargova et al. |
| 9,012,652 B2 | 4/2015 | Siesel |
| 9,035,072 B2 | 5/2015 | Belmont et al. |
| 9,045,425 B2 | 6/2015 | Luisi et al. |
| 9,051,303 B2 | 6/2015 | Keshavarz-Shokri et al. |
| 9,051,324 B2 | 6/2015 | Binch et al. |
| 9,079,916 B2 | 7/2015 | Hadida Ruah et al. |
| 9,090,619 B2 | 7/2015 | Hadida-Ruah et al. |
| 9,102,672 B2 | 8/2015 | Hadida-Ruah et al. |
| 9,139,530 B2 | 9/2015 | Hurter et al. |
| 9,150,552 B2 | 10/2015 | Keshavarz-Shokri et al. |
| 9,181,192 B2 | 11/2015 | Morgan |
| 9,192,606 B2 | 11/2015 | Young |
| 9,216,969 B2 | 12/2015 | Ruah et al. |
| 9,241,934 B2 | 1/2016 | Verwijs et al. |
| 9,249,131 B2 | 2/2016 | Hadida Ruah et al. |
| 9,254,291 B2 | 2/2016 | Looker et al. |
| 9,314,455 B2 | 4/2016 | Keshavarz-Shokri et al. |
| 9,321,725 B2 | 4/2016 | Miller et al. |
| 9,351,962 B2 | 5/2016 | Ruah et al. |
| 9,371,287 B2 | 6/2016 | DeMattei et al. |
| 9,399,648 B2 | 7/2016 | Gallardo-Godoy |
| 9,434,717 B2 | 9/2016 | Keshavarz-Shokri et al. |
| 9,504,683 B2 | 11/2016 | Hadida Ruah et al. |
| 9,512,079 B2 | 12/2016 | Morgan |
| 9,522,145 B2 | 12/2016 | Hadida Ruah et al. |
| 9,550,761 B2 | 1/2017 | Hadida-Ruah et al. |
| 9,670,163 B2 | 6/2017 | Hurter et al. |
| 9,701,639 B2 | 7/2017 | Strohmeier et al. |
| 9,725,440 B2 | 8/2017 | Hadida-Ruah et al. |
| 9,732,080 B2 | 8/2017 | Hadida-Ruah et al. |
| 9,751,839 B2 | 9/2017 | DeMattei et al. |
| 9,751,890 B2 | 9/2017 | Hadida Ruah et al. |
| 9,758,510 B2 | 9/2017 | Hadida Ruah et al. |
| 9,776,968 B2 | 10/2017 | Siesel |
| 9,782,408 B2 | 10/2017 | Miller et al. |
| 9,840,499 B2 | 12/2017 | Keshavarz-Shokri et al. |
| 9,931,334 B2 | 4/2018 | Hurter et al. |
| 9,974,781 B2 | 5/2018 | Hadida Ruah et al. |
| 10,022,352 B2 | 7/2018 | Hadida Ruah et al. |
| 10,047,053 B2 | 8/2018 | Morgan |
| 10,058,546 B2 | 8/2018 | Alargova et al. |
| 10,071,979 B2 | 9/2018 | Tanoury et al. |
| 10,076,513 B2 | 9/2018 | Verwijs et al. |
| 10,081,621 B2 | 9/2018 | Keshavarz-Shokri et al. |
| 10,206,877 B2 | 2/2019 | Phenix et al. |
| 10,231,932 B2 | 3/2019 | Swinney et al. |
| 10,239,867 B2 | 3/2019 | Hadida Ruah et al. |
| 10,258,624 B2 | 4/2019 | Miller et al. |
| 10,272,046 B2 | 4/2019 | Dokou et al. |
| 10,302,602 B2 | 5/2019 | Borsje et al. |
| 10,479,766 B2 | 11/2019 | Morgan et al. |
| 10,537,565 B2 | 1/2020 | Hurter et al. |
| 10,570,115 B2 | 2/2020 | Alcacio et al. |
| 10,597,384 B2 | 3/2020 | Keshavarz-Shokri et al. |

(56) References Cited

U.S. PATENT DOCUMENTS

| | | |
|---|---|---|
| 10,626,111 B2 | 4/2020 | Hadida Ruah et al. |
| 10,646,481 B2 | 5/2020 | William et al. |
| 10,654,829 B2 | 5/2020 | Dhamankar et al. |
| 10,662,192 B2 | 5/2020 | Hadida-Ruah et al. |
| 10,758,534 B2 | 9/2020 | Miller et al. |
| 10,759,721 B2 | 9/2020 | Morgan et al. |
| 10,793,547 B2 | 10/2020 | Abela et al. |
| 10,894,773 B2 | 1/2021 | Morgan et al. |
| 10,906,891 B2 | 2/2021 | Keshavarz-Shokri et al. |
| 10,975,061 B2 | 4/2021 | Hadida Ruah et al. |
| 10,980,746 B2 | 4/2021 | Phenix et al. |
| 10,987,348 B2 | 4/2021 | Hadida Ruah et al. |
| 11,052,075 B2 | 7/2021 | Verwijs et al. |
| 11,084,804 B2 | 8/2021 | Hadida Ruah et al. |
| 11,155,533 B2 | 10/2021 | Dhamankar et al. |
| 11,179,367 B2 | 11/2021 | Chu et al. |
| 11,186,566 B2 | 11/2021 | Alcacio et al. |
| 11,253,509 B2 | 2/2022 | Chen et al. |
| 11,291,662 B2 | 4/2022 | Hurter et al. |
| 11,414,439 B2 | 8/2022 | Abela et al. |
| 11,426,407 B2 | 8/2022 | Miller et al. |
| 11,434,201 B2 | 9/2022 | Angell et al. |
| 11,453,655 B2 | 9/2022 | Abela et al. |
| 11,465,985 B2 | 10/2022 | Angell et al. |
| 11,517,564 B2 | 12/2022 | Chen et al. |
| 11,564,916 B2 | 1/2023 | Rowe et al. |
| 11,578,062 B2 | 2/2023 | Keshavarz-Shokri et al. |
| 11,584,761 B2 | 2/2023 | Angell et al. |
| 11,639,347 B2 | 5/2023 | Hadida Ruah et al. |
| 11,708,331 B2 | 7/2023 | Lewandowski et al. |
| 2005/0113423 A1 | 5/2005 | Van Goor et al. |
| 2007/0105833 A1 | 5/2007 | Ruah et al. |
| 2007/0218138 A1 | 9/2007 | Bittorf et al. |
| 2009/0105272 A1 | 4/2009 | Grootenhuis et al. |
| 2009/0176839 A1 | 7/2009 | Keshavarz-Shokri et al. |
| 2009/0246820 A1 | 10/2009 | Singh et al. |
| 2010/0036130 A1 | 2/2010 | Siesel |
| 2010/0074949 A1 | 3/2010 | Rowe et al. |
| 2010/0125090 A1 | 5/2010 | Hadida Ruah et al. |
| 2010/0144798 A1 | 6/2010 | Van Goor et al. |
| 2010/0227888 A1 | 9/2010 | Hadida Ruah et al. |
| 2010/0256184 A1 | 10/2010 | Rowe et al. |
| 2011/0064811 A1 | 3/2011 | Hurter et al. |
| 2011/0098311 A1 | 4/2011 | Van Goor et al. |
| 2011/0177999 A1 | 7/2011 | Singh et al. |
| 2011/0251253 A1 | 10/2011 | Keshavarz-Shokri et al. |
| 2011/0257223 A1 | 10/2011 | Van Goor et al. |
| 2011/0288122 A1 | 11/2011 | Van Goor et al. |
| 2012/0035179 A1 | 2/2012 | Hadida-Ruah et al. |
| 2012/0046330 A1 | 2/2012 | Alargova et al. |
| 2012/0064157 A1 | 3/2012 | Dokou et al. |
| 2012/0122921 A1 | 5/2012 | DeMattei et al. |
| 2012/0122922 A1 | 5/2012 | Young et al. |
| 2012/0184583 A1 | 7/2012 | Van Goor et al. |
| 2012/0220625 A1 | 8/2012 | Rowe et al. |
| 2012/0232059 A1 | 9/2012 | Hadida-Ruah et al. |
| 2012/0258983 A1 | 10/2012 | Rowe et al. |
| 2013/0012536 A1 | 1/2013 | Hadida Ruah et al. |
| 2013/0018071 A1 | 1/2013 | Arekar et al. |
| 2013/0085158 A1 | 4/2013 | Keshavarz-Shokri et al. |
| 2013/0090354 A1 | 4/2013 | Van Goor et al. |
| 2013/0095181 A1 | 4/2013 | Verwijs et al. |
| 2013/0131107 A1 | 5/2013 | Van Goor et al. |
| 2013/0143919 A1 | 6/2013 | Van Goor et al. |
| 2013/0158071 A1 | 6/2013 | Van Goor et al. |
| 2013/0186801 A1 | 7/2013 | Verwijs et al. |
| 2013/0224293 A1 | 8/2013 | Dokou et al. |
| 2013/0231368 A1 | 9/2013 | Zhang et al. |
| 2013/0245010 A1 | 9/2013 | Hadida Ruah et al. |
| 2013/0245011 A1 | 9/2013 | Hadida Ruah et al. |
| 2013/0303484 A1 | 11/2013 | Grootenhuis et al. |
| 2013/0331567 A1 | 12/2013 | Hadida-Ruah et al. |
| 2014/0023706 A1 | 1/2014 | Verwijs et al. |
| 2014/0094499 A1 | 4/2014 | Alargova et al. |
| 2014/0112988 A1 | 4/2014 | Rowe et al. |
| 2014/0142138 A1 | 5/2014 | Van Goor et al. |
| 2014/0155431 A1 | 6/2014 | Hadida-Ruah et al. |
| 2014/0155626 A1 | 6/2014 | Hadida-Ruah et al. |
| 2014/0163011 A1 | 6/2014 | Hadida-Ruah et al. |
| 2014/0163068 A1 | 6/2014 | Verwijs et al. |
| 2014/0221424 A1 | 8/2014 | Zha |
| 2014/0235668 A1 | 8/2014 | Binch et al. |
| 2014/0243289 A1 | 8/2014 | Grootenhuis et al. |
| 2014/0303204 A1 | 10/2014 | Binch et al. |
| 2014/0303205 A1 | 10/2014 | Yang et al. |
| 2014/0315948 A1 | 10/2014 | Rowe et al. |
| 2014/0323521 A1 | 10/2014 | Van Goor et al. |
| 2014/0329855 A1 | 11/2014 | Arekar et al. |
| 2014/0336393 A1 | 11/2014 | Ambhaikar et al. |
| 2014/0343098 A1 | 11/2014 | Sheth et al. |
| 2014/0350281 A1 | 11/2014 | DeMattei et al. |
| 2015/0010628 A1 | 1/2015 | Dokou et al. |
| 2015/0024047 A1 | 1/2015 | Dokou et al. |
| 2015/0031722 A1 | 1/2015 | Hadida-Ruah et al. |
| 2015/0065487 A1 | 3/2015 | Hadida-Ruah et al. |
| 2015/0065497 A1 | 3/2015 | Hadida-Ruah et al. |
| 2015/0065500 A1 | 3/2015 | Hadida-Ruah et al. |
| 2015/0080431 A1 | 3/2015 | Van Goor et al. |
| 2015/0094304 A1 | 4/2015 | Ruah et al. |
| 2015/0119441 A1 | 4/2015 | Hadida Ruah et al. |
| 2015/0150879 A2 | 6/2015 | Van Goor et al. |
| 2015/0174098 A1 | 6/2015 | Ruah et al. |
| 2015/0182517 A1 | 7/2015 | Alargova et al. |
| 2015/0231142 A1 | 8/2015 | Van Goor et al. |
| 2015/0246031 A1 | 9/2015 | Dokou et al. |
| 2015/0293078 A1 | 10/2015 | Singh et al. |
| 2015/0315186 A2 | 11/2015 | Hadida-Ruah et al. |
| 2015/0336898 A1 | 11/2015 | Grootenhuis et al. |
| 2016/0022664 A2 | 1/2016 | Van Goor et al. |
| 2016/0022665 A2 | 1/2016 | Van Goor et al. |
| 2016/0039800 A1 | 2/2016 | Young |
| 2016/0067239 A9 | 3/2016 | Van Goor et al. |
| 2016/0120841 A1 | 5/2016 | Kym et al. |
| 2016/0143898 A1 | 5/2016 | Hadida Ruah et al. |
| 2016/0166540 A1 | 6/2016 | Looker et al. |
| 2016/0221952 A1 | 8/2016 | Yang et al. |
| 2016/0228414 A1 | 8/2016 | Hadida Ruah et al. |
| 2016/0318931 A1 | 11/2016 | Hadida Ruah et al. |
| 2016/0324788 A1 | 11/2016 | Verwijs |
| 2016/0324846 A1 | 11/2016 | Verwijs et al. |
| 2016/0354316 A1 | 12/2016 | Swinney et al. |
| 2017/0100340 A1 | 4/2017 | Dokou et al. |
| 2017/0101405 A1 | 4/2017 | Akkari et al. |
| 2017/0107205 A1 | 4/2017 | Hadida Ruah et al. |
| 2017/0107206 A1 | 4/2017 | Hadida Ruah et al. |
| 2017/0137383 A1 | 5/2017 | Morgan |
| 2018/0008546 A1 | 1/2018 | Verwijs et al. |
| 2018/0125838 A1 | 5/2018 | Uttamsingh |
| 2018/0127398 A1 | 5/2018 | Keshavarz-Shokri et al. |
| 2018/0153874 A1 | 6/2018 | Van Goor et al. |
| 2018/0280349 A1 | 10/2018 | Van Goor et al. |
| 2018/0353500 A1 | 12/2018 | Braman |
| 2019/0038615 A1 | 2/2019 | Van Goor et al. |
| 2019/0055220 A1 | 2/2019 | Bear et al. |
| 2019/0070155 A1 | 3/2019 | Verwijs et al. |
| 2019/0076419 A1 | 3/2019 | Hadida Ruah et al. |
| 2019/0210991 A1 | 7/2019 | Tanoury et al. |
| 2019/0274959 A1 | 9/2019 | Dokou et al. |
| 2020/0031776 A1 | 1/2020 | Morgan et al. |
| 2020/0085750 A1 | 3/2020 | Verwijs |
| 2020/0115366 A1 | 4/2020 | Hadida Ruah et al. |
| 2020/0171015 A1 | 6/2020 | Haseltine et al. |
| 2020/0338063 A1 | 10/2020 | Verwijs et al. |
| 2020/0352930 A1 | 11/2020 | Hurter et al. |
| 2020/0377484 A1 | 12/2020 | Keshavarz-Shokri et al. |
| 2021/0023070 A1 | 1/2021 | Rowe et al. |
| 2021/0024505 A1 | 1/2021 | Hadida Ruah et al. |
| 2021/0052570 A1 | 2/2021 | Uttamsingh |
| 2021/0069174 A1 | 3/2021 | Chu et al. |
| 2021/0139514 A1 | 5/2021 | Abela et al. |
| 2021/0228489 A1 | 7/2021 | Dokou et al. |
| 2021/0238158 A1 | 8/2021 | Tanoury et al. |
| 2021/0308053 A1 | 10/2021 | Phenix et al. |
| 2021/0340128 A1 | 11/2021 | Keshavarz-Shokri et al. |

(56) References Cited

U.S. PATENT DOCUMENTS

| | | |
|---|---|---|
| 2022/0031679 A1 | 2/2022 | Verwijs et al. |
| 2022/0041621 A1 | 2/2022 | Clemens et al. |
| 2022/0153729 A1 | 5/2022 | Hadida Ruah et al. |
| 2022/0257564 A1 | 8/2022 | Chu et al. |
| 2022/0306606 A1 | 9/2022 | Alcacio et al. |
| 2022/0354797 A1 | 11/2022 | Verwijs et al. |
| 2023/0127655 A1 | 4/2023 | Hadida Ruah et al. |
| 2023/0233560 A1 | 7/2023 | Miller et al. |
| 2023/0241045 A1 | 8/2023 | Chen et al. |
| 2023/0357191 A1 | 11/2023 | Abela et al. |
| 2024/0025877 A1 | 1/2024 | Angell et al. |

FOREIGN PATENT DOCUMENTS

| | | |
|---|---|---|
| WO | WO 2004/111014 A1 | 12/2004 |
| WO | WO 2005/026137 A2 | 3/2005 |
| WO | WO 2005/049018 A1 | 6/2005 |
| WO | WO 2005/075435 A1 | 8/2005 |
| WO | WO 2006/002421 A2 | 1/2006 |
| WO | WO 2006/099256 A2 | 9/2006 |
| WO | WO 2006/127588 A2 | 11/2006 |
| WO | WO 2007/021982 A2 | 2/2007 |
| WO | WO 2007/044560 A2 | 4/2007 |
| WO | WO 2007/056341 A1 | 5/2007 |
| WO | WO 2007/075901 A2 | 7/2007 |
| WO | WO 2007/075946 A1 | 7/2007 |
| WO | WO 2007/079139 A2 | 7/2007 |
| WO | WO 2007/087066 A2 | 8/2007 |
| WO | WO 2007/109605 A2 | 9/2007 |
| WO | WO 2007/117715 A2 | 10/2007 |
| WO | WO 2007/134279 A2 | 11/2007 |
| WO | WO 2008/092231 A1 | 8/2008 |
| WO | WO 2008/127399 A2 | 10/2008 |
| WO | WO 2008/147952 A1 | 12/2008 |
| WO | WO 2009/006315 A1 | 1/2009 |
| WO | WO 2009/023509 A2 | 2/2009 |
| WO | WO 2009/036412 A1 | 3/2009 |
| WO | WO 2009/038683 A2 | 3/2009 |
| WO | WO 2009/038913 A2 | 3/2009 |
| WO | WO 2009/073757 A1 | 6/2009 |
| WO | WO 2009/076141 A2 | 6/2009 |
| WO | WO 2009/076142 A2 | 6/2009 |
| WO | WO 2009/076593 A1 | 6/2009 |
| WO | WO 2009/108657 A2 | 9/2009 |
| WO | WO 2010/019239 A2 | 2/2010 |
| WO | WO 2010/037066 A2 | 4/2010 |
| WO | WO 2010/048526 A2 | 4/2010 |
| WO | WO 2010/053471 A1 | 5/2010 |
| WO | WO 2010/054138 A2 | 5/2010 |
| WO | WO 2010/078103 A1 | 7/2010 |
| WO | WO 2010/108155 A1 | 9/2010 |
| WO | WO 2010/108162 A1 | 9/2010 |
| WO | WO 2011/019413 A1 | 2/2011 |
| WO | WO 2011/050325 A1 | 4/2011 |
| WO | WO 2011/072241 A1 | 6/2011 |
| WO | WO 2011/116397 A1 | 9/2011 |
| WO | WO 2011/119984 A1 | 9/2011 |
| WO | WO 2011/127241 A2 | 10/2011 |
| WO | WO 2011/127290 A2 | 10/2011 |
| WO | WO 2011/133751 A2 | 10/2011 |
| WO | WO 2011/133951 A1 | 10/2011 |
| WO | WO 2011/133953 A1 | 10/2011 |
| WO | WO 2012/027247 A2 | 3/2012 |
| WO | WO 2012/027731 A2 | 3/2012 |
| WO | WO 2012/158885 A1 | 11/2012 |
| WO | WO 2012/170061 A1 | 12/2012 |
| WO | WO 2013/038386 A1 | 3/2013 |
| WO | WO 2013/070961 A1 | 5/2013 |
| WO | WO 2013/112804 A1 | 8/2013 |
| WO | WO 2013/130669 A1 | 9/2013 |
| WO | WO 2013/158121 A1 | 10/2013 |
| WO | WO 2013/185112 A1 | 12/2013 |
| WO | WO 2014/014841 A1 | 1/2014 |
| WO | WO 2014/071122 A1 | 5/2014 |
| WO | WO 2014/078842 A1 | 5/2014 |
| WO | WO 2015/048301 A1 | 4/2015 |
| WO | WO 2015/073231 A1 | 7/2015 |
| WO | WO 2015/160787 A1 | 10/2015 |
| WO | WO 2016/057572 A1 | 4/2016 |
| WO | WO 2016/057730 A1 | 4/2016 |
| WO | WO 2016/081556 A1 | 5/2016 |
| WO | WO 2016/105485 A2 | 6/2016 |
| WO | WO 2016/160945 A1 | 10/2016 |
| WO | WO 2017/009804 A1 | 1/2017 |
| WO | WO 2017/053455 A1 | 3/2017 |
| WO | WO 2017/053711 A2 | 3/2017 |
| WO | WO 2017/062581 A1 | 4/2017 |
| WO | WO 2017/173274 A1 | 10/2017 |
| WO | WO 2018/064632 A1 | 4/2018 |
| WO | WO 2018/065921 A1 | 4/2018 |
| WO | WO 2018/080591 A1 | 5/2018 |
| WO | WO 2018/107100 A1 | 6/2018 |
| WO | WO 2018/183367 A1 | 10/2018 |
| WO | WO 2018/227049 A1 | 12/2018 |
| WO | WO 2019/010092 A1 | 1/2019 |
| WO | WO 2019/014352 A1 | 1/2019 |
| WO | WO 2019/018353 A1 | 1/2019 |
| WO | WO 2019/018395 A1 | 1/2019 |
| WO | WO 2019/028228 A1 | 2/2019 |
| WO | WO 2019/079760 A1 | 4/2019 |
| WO | WO 2019/109021 A1 | 6/2019 |
| WO | WO 2019/113089 A1 | 6/2019 |
| WO | WO 2019/113476 A1 | 6/2019 |
| WO | WO 2019/152940 A1 | 8/2019 |
| WO | WO 2019/161078 A1 | 8/2019 |
| WO | WO 2019/026075 A1 | 10/2019 |
| WO | WO 2019/191620 A1 | 10/2019 |
| WO | WO 2019/195739 A1 | 10/2019 |
| WO | WO 2019/200246 A1 | 10/2019 |
| WO | WO 2020/102346 A1 | 5/2020 |
| WO | WO 2020/206080 A1 | 10/2020 |
| WO | WO 2020/214921 A1 | 10/2020 |
| WO | WO 2020/242935 A1 | 12/2020 |
| WO | WO 2021/030552 A1 | 2/2021 |
| WO | WO 2021/030554 A1 | 2/2021 |
| WO | WO 2021/030555 A1 | 2/2021 |
| WO | WO 2021/030556 A1 | 2/2021 |
| WO | WO 2022/032068 A1 | 2/2022 |
| WO | WO 2022/036060 A1 | 2/2022 |
| WO | WO 2022/076618 A1 | 4/2022 |
| WO | WO 2022/076624 A1 | 4/2022 |
| WO | WO 2022/109573 A1 | 5/2022 |

OTHER PUBLICATIONS

Bose, S. et al., "Towards next generation therapies for cystic fibrosis: Folding, function and pharmacology of CFTR," *J. Cyst. Fibros.* 2020, 19 Suppl 1, S25-S32.

Brasell, E.J. et al., "The novel aminoglycoside, ELX-02, permits $CTNS^{W138X}$ translational read-through and restores lysosomal cystine efflux in cystinosis," *PLoS One* 2019, 14 (12), e0223954.

Caira, M.R. (1998) "Crystalline Polymorphism of Organic Compounds." In: Weber, E., et al., Design of Organic Solids. Topics in Current Chemistry, vol. 198. Springer, Berlin, Heidelberg.

Crawford, D.K. et al., "Open AccessELX-02 Generates Protein via Premature Stop Codon Read-Through without Inducing Native Stop Codon Read-Through Proteins," *J. Pharmacol. Exp. Ther.* 2020, 374 (2), 264-272.

Donaldson, Scott H. et al. "Tezacaftor/Ivacaftor in Subjects with Cystic Fibrosis and F508del/F508del-CFTR or F508del/G551D-CFTR", *Am. J. Respir. Crit. Care Med.* 2017, 197(2): 214-224.

International Patent Application No. PCT/US2021/072475: International Search Report and Written Opinion, mailed Feb. 25, 2022 (12 pages).

Kunzelmann, K. et al., "TMEM16A in Cystic Fibrosis: Activating or Inhibiting?" *Front. Pharmacol.* 2019, 10, 3. doi.org/10.3389/fphar.2019.00003.

Lopes-Pacheco, M., "CFTR Modulators: The Changing Face of Cystic Fibrosis in the Era of Precision Medicine," *Front. Pharmacol.* 2020, 10, 1662.

(56) References Cited

OTHER PUBLICATIONS

Pedemonte, N. et al., "Discovery of a picomolar potency pharmacological corrector of the mutant CFTR chloride channel," *Sci. Adv.* 2020, 6 (8), eaay9669.

Phuan, P.-W. et al., "Combination potentiator ('co-potentiator') therapy for CF caused by CFTR mutants, including N1303K, that are poorly responsive to single potentiators," *J. Cyst. Fibros.* 2018, 17(5), 595-606.

Phuan, P.-W. et al., "Nanomolar-potency 'co-potentiator' therapy for cystic fibrosis caused by a defined subset of minimal function CFTR mutants," *Sci. Rep.* 2019, 9 (1), 17640.

Sabnis, R. W., "Novel Macrocyclic 1,3,4-Oxadiazoles as CFTR Modulators for Treating Cystic Fibrosis," *ACS Med. Chem. Lett.* 2022, 13, 7, 1014-1015.

Smith, N. J., Solovay, C. F., "Epithelial Na+ channel inhibitors for the treatment of cystic fibrosis," *Pharm. Pat. Anal.* 2017, 6 (4), 179-188.

Son, J.-H. et al., "1-benzylspiro[piperidine-4,1'-pyrido[3,4-b]indole] 'co-potentiators' for minimal function CFTR mutants," *Eur. J. Med. Chem.* 2021, 209, 112888.

Notice of Allowance and Fee(s) Due for U.S. Appl. No. 17/395,838, mailed Sep. 10, 2024.

Temperature (°C)

MODULATORS OF CYSTIC FIBROSIS TRANSMEMBRANE CONDUCTANCE REGULATOR

This application claims the benefit of U.S. Provisional Application No. 63/115,552, filed on Nov. 18, 2020, the contents of which are incorporated by reference in its entirety.

The invention relates to modulators of Cystic Fibrosis Transmembrane Conductance Regulator (CFTR), pharmaceutical compositions containing the modulators, methods of treatment of cystic fibrosis and CFTR-mediated disorders using such modulators and pharmaceutical compositions, and processes for making such modulators.

Cystic fibrosis (CF) is a recessive genetic disease that affects approximately 83,000 children and adults worldwide. Despite progress in the treatment of CF, there is no cure.

In patients with CF, mutations in CFTR endogenously expressed in respiratory epithelia lead to reduced apical anion secretion causing an imbalance in ion and fluid transport. The resulting decrease in anion transport contributes to increased mucus accumulation in the lung and accompanying microbial infections that ultimately cause death in CF patients. In addition to respiratory disease, CF patients typically suffer from gastrointestinal problems and pancreatic insufficiency that, if left untreated, result in death. In addition, the majority of males with cystic fibrosis are infertile, and fertility is reduced among females with cystic fibrosis.

Sequence analysis of the CFTR gene has revealed a variety of disease-causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, greater than 2000 mutations in the CF gene have been identified; currently, the CFTR2 database contains information on only 322 of these identified mutations, with sufficient evidence to define 281 mutations as disease-causing. The most prevalent disease-causing mutation is a deletion of phenylalanine at position 508 of the CFTR amino acid sequence and is commonly referred to as the F508del mutation. This mutation occurs in many of the cases of cystic fibrosis and is associated with severe disease.

CFTR is a cAMP/ATP-mediated anion channel that is expressed in a variety of cell types, including absorptive and secretory epithelia cells, where it regulates anion flux across the membrane, as well as the activity of other ion channels and proteins. In epithelial cells, normal functioning of CFTR is critical for the maintenance of electrolyte transport throughout the body, including respiratory and digestive tissue. CFTR is composed of 1480 amino acids that encode a protein which is made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

Chloride transport takes place by the coordinated activity of ENaC (epithelial sodium channel) and CFTR present on the apical membrane and the $Na^+$—$K^+$-ATPase pump and $Cl^-$ channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride. Because water is probably never actively transported itself, its flow across epithelia depends on tiny transepithelial osmotic gradients generated by the bulk flow of sodium and chloride.

A number of CFTR modulators have recently been identified. These modulators can be characterized as, for example, potentiators, correctors, potentiator enhancers/co-potentiators, amplifiers, readthrough agents, and nucleic acid therapies. CFTR modulators that increase the channel gating activity of mutant and wild-type CFTR at the epithelial cell surface are known as potentiators. Correctors improve faulty protein processing and resulting trafficking to the epithelial surface. Ghelani and Schneider-Futschik (2020) ACS Pharmacol. Transl. Sci. 3:4-10. There are three CFTR correctors approved by the U.S. FDA for treatment of cystic fibrosis. However, monotherapy with some CFTR correctors has not been found to be effective enough and as a result combination therapy with a potentiator is needed to enhance CFTR activity. There is currently only one CFTR potentiator that is approved for the treatment of cystic fibrosis. Thus, although the treatment of cystic fibrosis has been transformed by these new small molecule CFTR modulators, new and better modulators are needed to prevent disease progression, reduce the severity of the cystic fibrosis and other CFTR-mediated diseases, and to treat the more severe forms of these diseases.

One aspect of the invention provides novel compounds, including compounds of Formulae I, I', I", Ia, Ia', IIa, IIa', IIb, IIb', IIc, IIc', IId, IId', IIe, IIe', IIf, IIf', IIg, IIg', IIh, and IIh', Compounds 1 to 213, Compounds 214 to 222, deuterated derivatives thereof and pharmaceutically acceptable salts of any of the foregoing.

For example, compounds of Formula I can be depicted as:

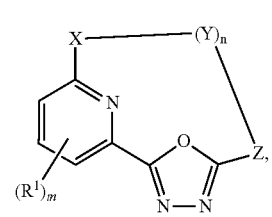

I and deuterated derivatives and pharmaceutically acceptable salts thereof, wherein:

X is selected from —N($R^{X1}$)— and

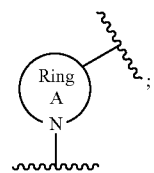

Ring A is a 4- to 6-membered heterocyclyl optionally substituted with 1-3 groups independently selected from $C_1$-$C_6$ alkyl and oxo;

$R^{X1}$ is selected from H, $C_1$-$C_6$ alkyl (optionally substituted with 1-3 groups independently selected from hydroxy, oxo, —$OR^{X2}$, and —N($R^{X2}$)$_2$), and $C_3$-$C_8$ cycloalkyl;

each $R^{X1}$ is independently selected from H and $C_1$-$C_6$ alkyl;

each Y is independently selected from —$C(R^Y)_2$—, —O—, —CO—, —$NR^{YN}$—, and

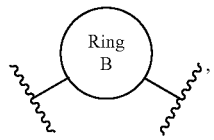

wherein each $R^{YN}$ is independently selected from H, $C_1$-$C_4$ alkyl, and $CO_2R^{YN1}$, wherein each $R^{YN1}$ is independently selected from $C_1$-$C_4$ alkyl and $C_3$-$C_6$ cycloalkyl;

each $R^Y$ is independently selected from hydrogen, hydroxy, halogen, $C_1$-$C_6$ alkyl (optionally substituted with 1-3 groups independently selected from hydroxy, $C_1$-$C_6$ alkoxy, and Q), $C_3$-$C_8$ cycloalkyl, $C_6$-$C_{10}$ aryl (optionally substituted with 1-3 groups independently selected from halogen), 5- to 10-membered heteroaryl, —$OR^{Y1}$, —$CO_2R^{Y1}$, —$COR^{Y1}$, —$CON(R^{Y1})_2$, and —$N(R^{Y1})_2$;

or two $R^Y$ on the same atom are taken together to form a ring selected from $C_3$-$C_8$ cycloalkyl and 3- to 7-membered heterocyclyl; or two $R^Y$, one of which is on one atom and the second of which is on an adjacent atom, are taken together to form a pi bond;

each $R^{Y1}$ is independently selected from hydrogen and $C_1$-$C_6$ alkyl, or two $R^{Y1}$ bonded to the same nitrogen taken together form a 3- to 6-membered heterocyclyl;

Ring B is selected from:
  $C_6$-$C_{10}$ aryl (optionally substituted with 1-3 groups independently selected from halogen, $C_1$-$C_6$ alkyl, and $C_1$-$C_6$ alkoxy),
  $C_3$-$C_8$ cycloalkyl,
  5- to 10-membered heteroaryl, and
  3- to 6-membered heterocyclyl (optionally substituted with 1-3 groups independently selected from $C_1$-$C_6$ alkyl);

each Q is independently selected from:
  $C_1$-$C_6$ alkyl optionally substituted with 1-3 groups independently selected from:
    halogen,
    oxo,
    $C_6$-$C_{10}$ aryl (optionally substituted with 1-3 groups independently selected from halogen and —$OCF_3$), and
    $C_3$-$C_8$ cycloalkyl,
  $C_3$-$C_8$ cycloalkyl optionally substituted with 1-3 groups independently selected from:
    halogen,
    CN,
    $C_1$-$C_6$ alkyl (optionally substituted with 1-3 groups independently selected from halogen, —$NH_2$, and —NHCOMe),
    $C_1$-$C_6$ alkoxy,
    $C_6$-$C_{10}$ aryl (optionally substituted with $C_1$-$C_6$ alkyl), and
    $C_3$-$C_8$ cycloalkyl,
  $C_6$-$C_{10}$ aryl optionally substituted with 1-3 groups independently selected from:
    halogen,
    CN,
    $C_1$-$C_6$ alkyl (optionally substituted with 1-3 groups independently selected from halogen and hydroxy),
    $C_1$-$C_6$ alkoxy optionally substituted with 1-4 groups independently selected from:
      halogen,
      $C_3$-$C_8$ cycloalkyl (optionally substituted with $CF_3$),
      $C_3$-$C_8$ cycloalkyl (optionally substituted with 1-3 groups independently selected from halogen, $CF_3$, $OCF_3$, and $C_1$-$C_6$ alkyl), and
      $C_6$-$C_{10}$ aryl,
  5- to 10-membered heteroaryl optionally substituted with 1-3 groups independently selected from:
    halogen,
    $C_1$-$C_6$ alkyl (optionally substituted with 1-3 groups independently selected from halogen),
    $C_3$-$C_8$ cycloalkyl (optionally substituted with 1-3 $CF_3$ groups), and
    3- to 10-membered heterocyclyl,
  3- to 10-membered heterocyclyl optionally substituted with 1-3 groups independently selected from:
    $C_1$-$C_6$ alkyl (optionally substituted with 1-3 groups independently selected from oxo and $C_3$-$C_8$ cycloalkyl), and
    oxo;

each $R^1$ is independently selected from halogen, $C_1$-$C_6$ fluoroalkyl, $C_1$-$C_6$ alkyl (optionally substituted with a group selected from hydroxy, $C_6$-$C_{10}$ aryl, and 5- to 6-membered heteroaryl), —$OR^2$, —$N(R^2)_2$, —$CO_2R^2$, —CO—$N(R^2)_2$, —CN, $C_3$-$C_8$ cycloalkyl, $C_6$-$C_{10}$ aryl, 5- to 6-membered heteroaryl (optionally substituted with 1-3 groups independently selected from $C_1$-$C_6$ alkyl), 3- to 6-membered heterocyclyl, —$B(OR^2)_2$, —$SO_2R^2$, —$SR^2$, —$SOR^2$, —$PO(OR^2)_2$, and —$PO(R^2)_2$;

each $R^2$ is independently selected from hydrogen, $C_1$-$C_6$ alkyl (optionally substituted with 1-6 groups independently selected from halogen), $C_1$-$C_6$ fluoroalkyl, and $C_6$-$C_{10}$ aryl (optionally substituted with 1-3 groups independently selected from $C_1$-$C_6$ fluoroalkyl and $C_1$-$C_6$ fluoroalkoxy);

Z is selected from

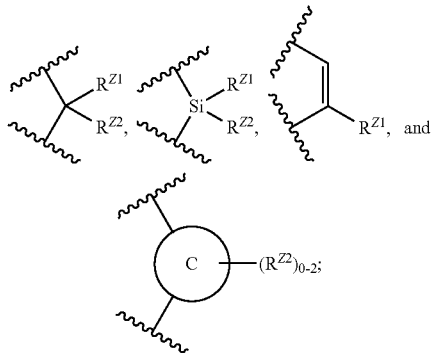

wherein Ring C is selected from $C_6$-$C_{10}$ aryl and 5- to 10-membered heteroaryl;

$R^{Z1}$ is selected from hydrogen, —CN, $C_1$-$C_6$ alkyl (optionally substituted with 1-3 hydroxy), $C_1$-$C_6$ fluoroalkyl, 3- to 6-membered heterocyclyl, $C_3$-$C_6$ cycloalkyl, $C_6$-$C_{10}$ aryl, and 5- to 6-membered heteroaryl;

$R^{Z2}$ is selected from hydrogen, halogen, hydroxy, $NH_2$, $NH(CO)(C_1-C_6$ alkyl), and $C_1-C_6$ alkoxy (optionally substituted with 1-3 groups independently selected from $C_3-C_{10}$ cycloalkyl), or $R^{Z1}$ and $R^{Z2}$ taken together form a group selected from oxo and =N—OH;

each $R^{Z3}$ is independently selected from hydroxy, $C_1-C_6$ alkoxy, $C_1-C_6$ alkyl, and $C_6-C_{10}$ aryl; or two $R^{Z3}$ are taken together to form a 3- to 6-membered heterocyclyl;

n is selected from 4, 5, 6, 7, and 8; and m is selected from 0, 1, 2, and 3.

In some embodiments of Formula I, X is —N($R^{X1}$)—.

In some embodiments of Formula I, X is

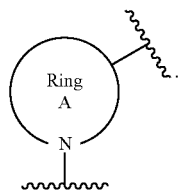

In some embodiments of Formula I, X is selected from:

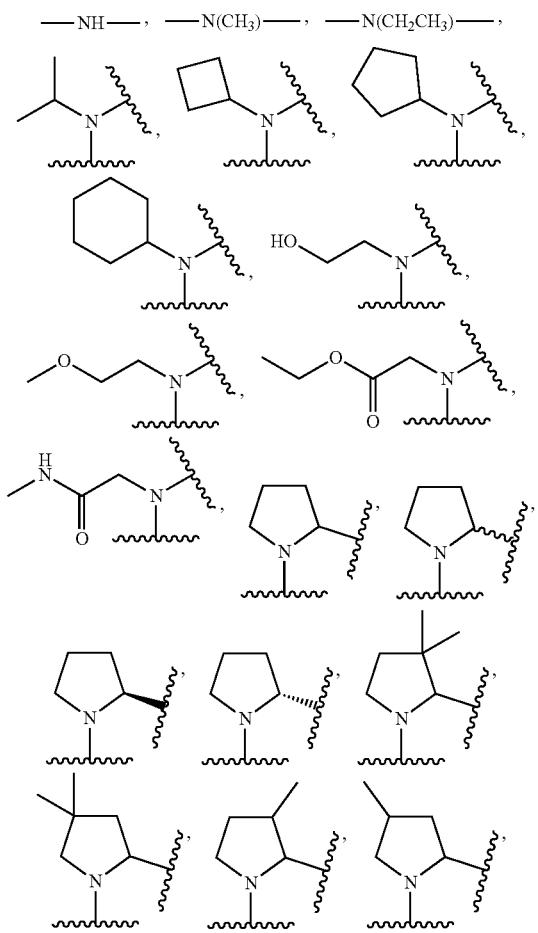

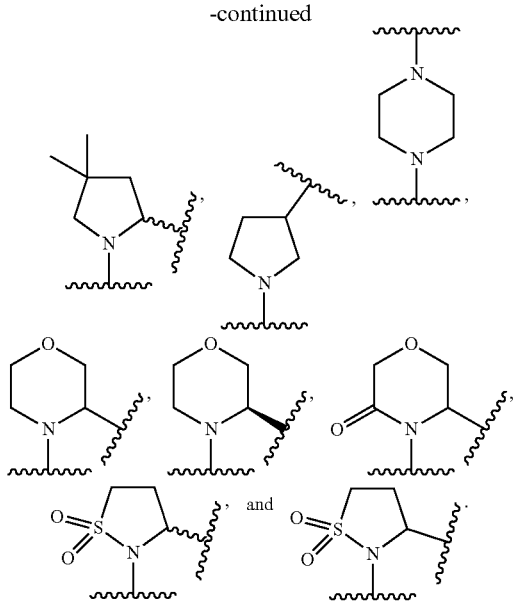

In some embodiments of Formula I, each $R^Y$ is independently selected from hydrogen, hydroxy, halogen, $C_1-C_6$ alkyl (optionally substituted with 1-3 groups independently selected from hydroxy, $C_1-C_6$ alkoxy, and Q), $C_3-C_8$ cycloalkyl, $C_6-C_{10}$ aryl (optionally substituted with 1-3 groups independently selected from halogen), 5- to 10-membered heteroaryl, —$CO_2R^{Y1}$, and —$CON(R^{Y1})_2$;

or two $R^Y$ on the same atom are taken together to form a ring selected from $C_3-C_8$ cycloalkyl and 3- to 7-membered heterocyclyl;

or two $R^Y$, one of which is on one atom and the second of which is on an adjacent atom, are taken together to form a pi bond.

In some embodiments of Formula I, each $R^{Y1}$ is independently selected from hydrogen and $C_1-C_6$ alkyl, or two $R^{Y1}$ bonded to the same nitrogen taken together form a 3- to 6-membered heterocyclyl.

In some embodiments of Formula I, each Q is independently selected from $C_6-C_{10}$ aryl.

In some embodiments of Formula I, each Q is phenyl.

In some embodiments of Formula I, each $R^Y$ is independently selected from:

hydrogen, hydroxy, —$CH_3$, —$CD_3$, —$CH_2CH_3$,

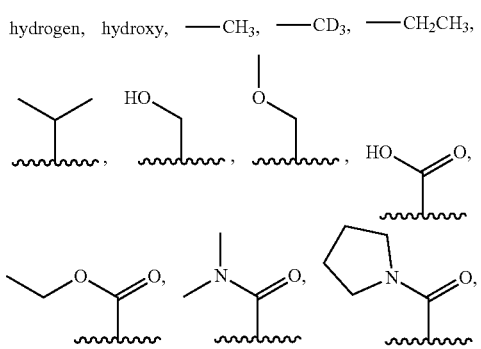

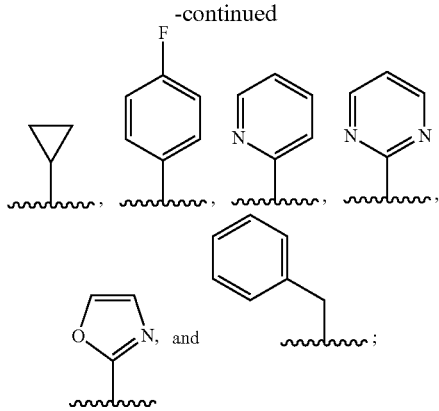

or two $R^Y$ on the same atom are taken together to form a ring selected from cyclobutyl, cyclopentyl, cyclohexyl, tetrahydropyryl, and tetrahydrofuryl;

or two $R^Y$, one of which is on one atom and the second of which is on an adjacent atom, are taken together to form a pi bond.

In some embodiments of Formula I, Ring B is selected from $C_6$-$C_{10}$ aryl (optionally substituted with 1-3 groups independently selected from halogen and $C_1$-$C_6$ alkoxy) and 5- to 10-membered heteroaryl.

In some embodiments of Formula I, Ring B is selected from phenyl(optionally substituted with 1-3 groups independently selected from halogen and $C_1$-$C_6$ alkoxy) and pyridyl.

In some embodiments of Formula I, Ring B is selected from:

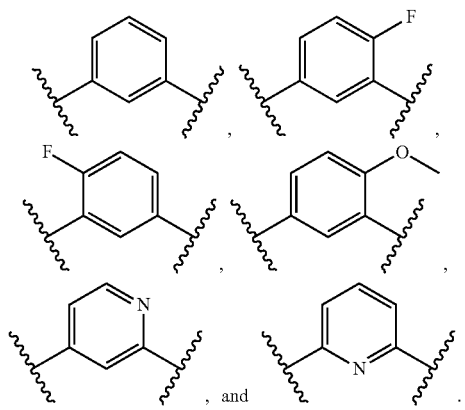

In some embodiments of Formula I, n is selected from 4, 5, 6, and 7.

In some embodiments of Formula I, —(Y)$_n$— is a group selected from:

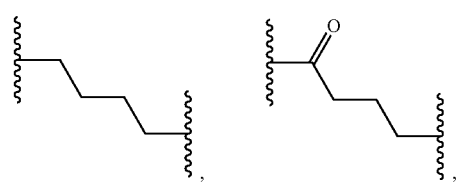

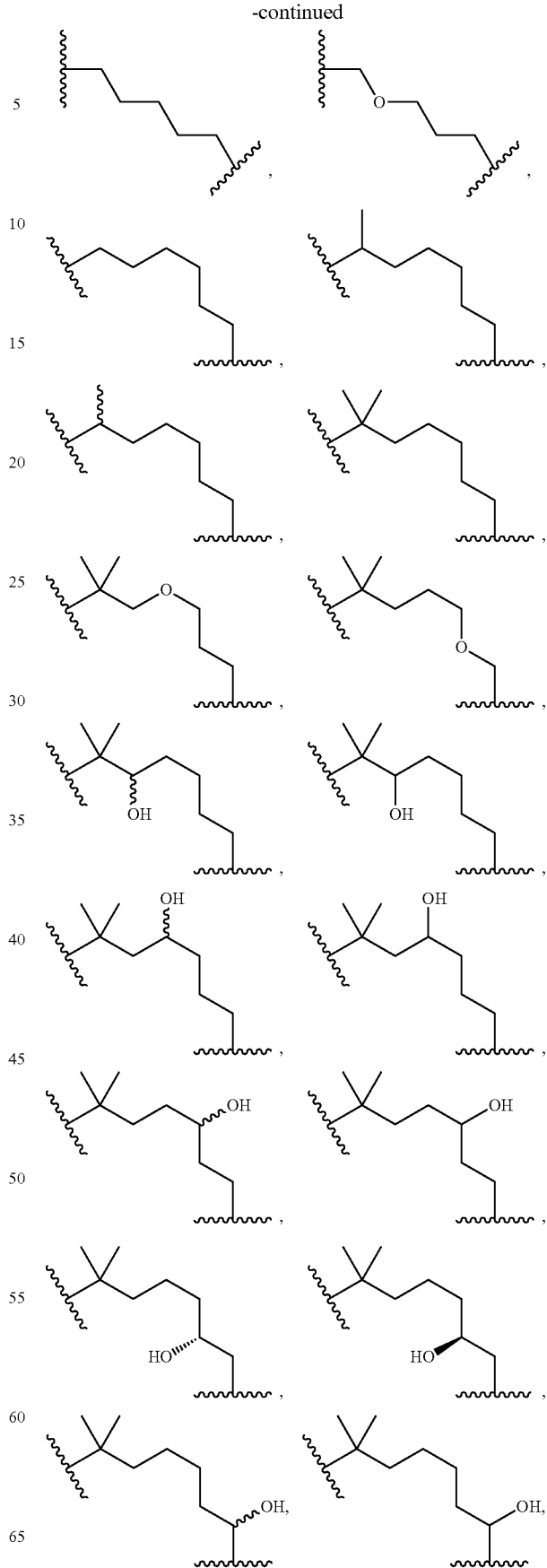

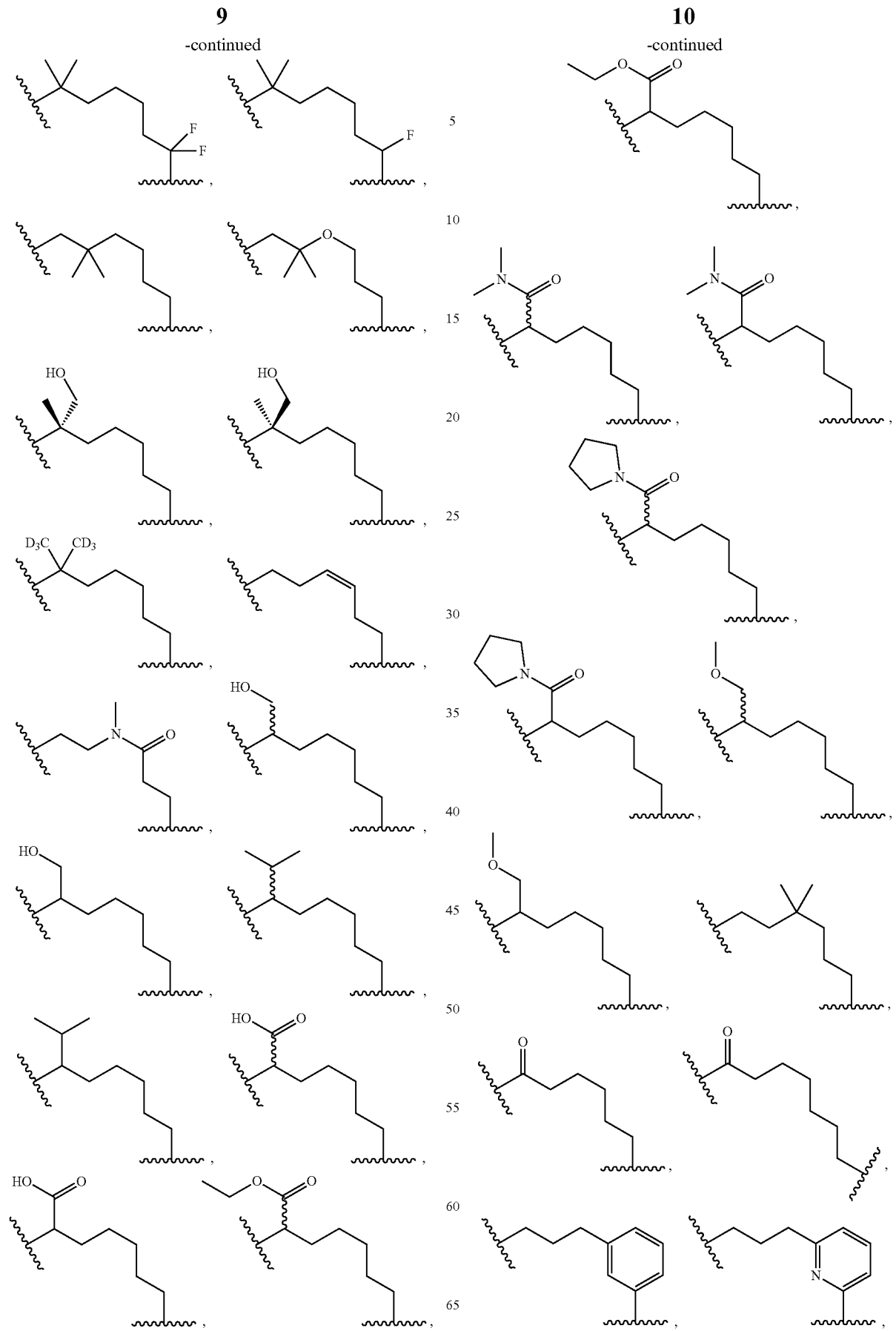

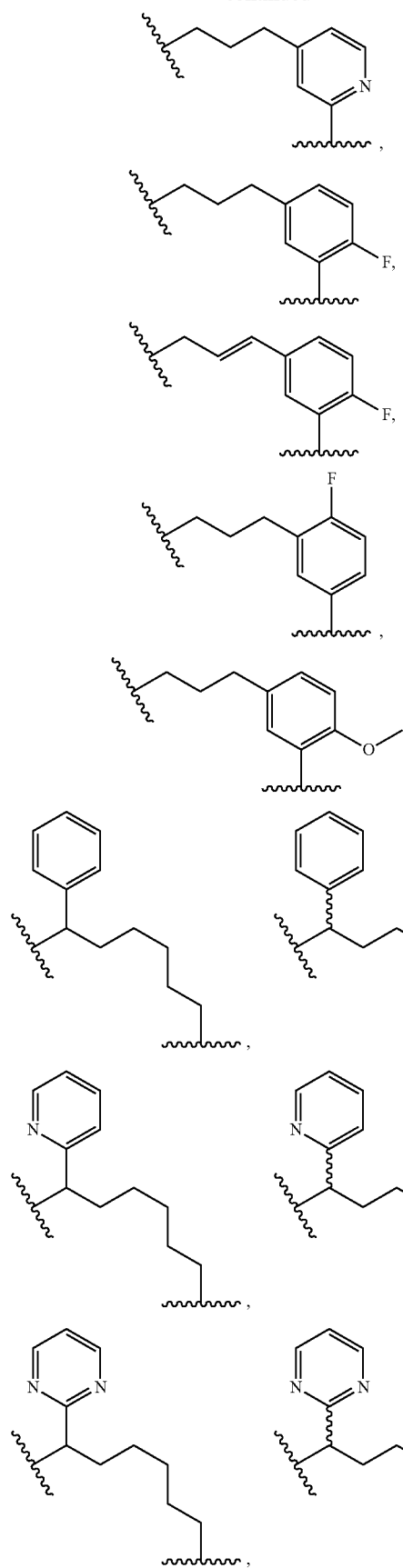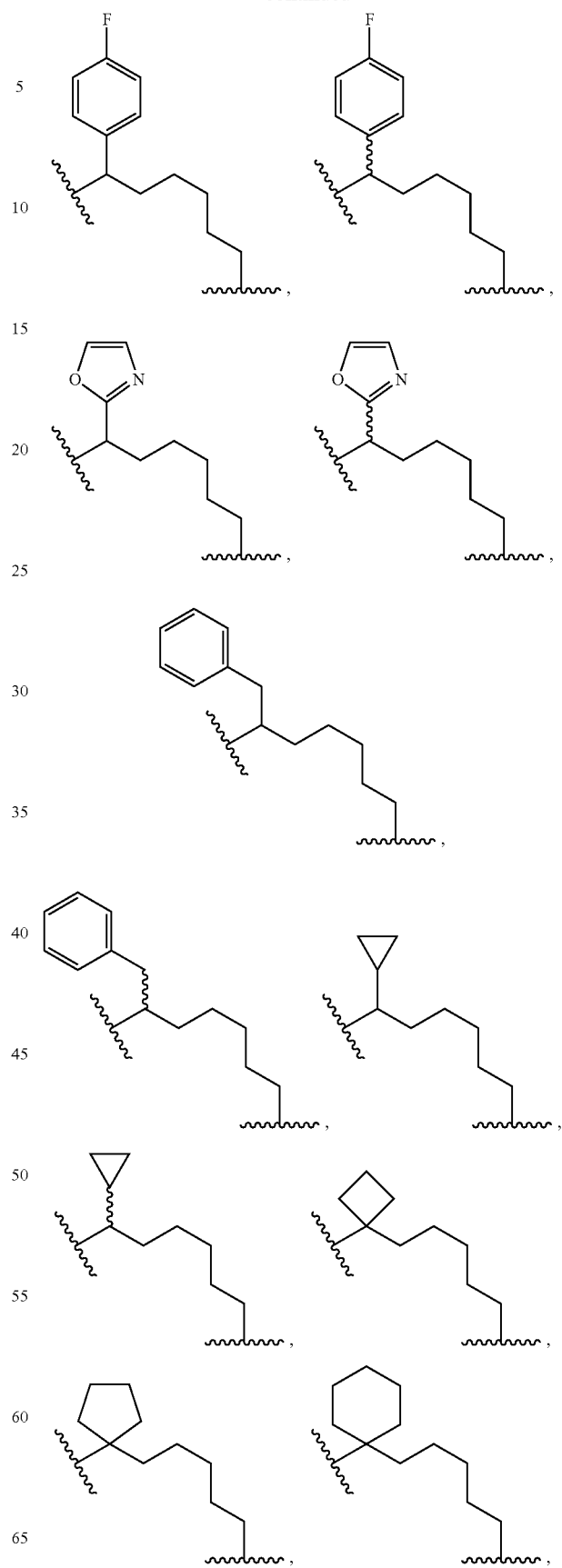

-continued

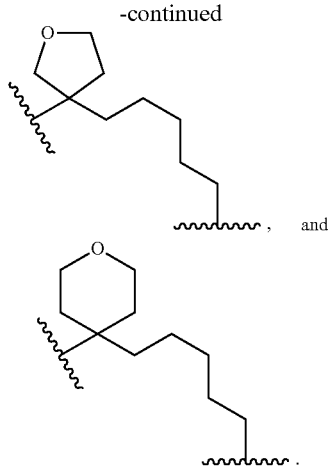
and

In some embodiments of Formula I, each R¹ is independently selected from halogen, $C_1$-$C_6$ fluoroalkyl, $C_1$-$C_6$ alkyl (optionally substituted with a group selected from $C_6$-$C_{10}$ aryl), —OR², —N(R²)₂, —CO₂R², —CO—N(R²)₂, —CN, $C_1$-$C_6$ alkoxy, $C_3$-$C_8$ cycloalkyl, $C_6$-$C_{10}$ aryl, 5- to 6-membered heteroaryl (optionally substituted with 1-3 groups independently selected from $C_1$-$C_6$ alkyl), 3- to 6-membered heterocyclyl, —B(OR²)₂, —SO₂R², —SR², —SOR², and —PO(R²)₂.

In some embodiments of Formula I, each R² is independently selected from $C_6$-$C_{10}$ aryl (optionally substituted with 1-3 groups independently selected from $C_1$-$C_6$ fluoroalkoxy).

In some embodiments of Formula I, each R¹ is independently selected from —Br, —CF₃, —NH₂, —CH₃, —CH(CH₃)₂, —CN, —OH, —OCH₃, —NH(CH₃), —NH(CH₂CH₃), —CONH₂, —CO₂CH₃, —SO₂CH₃, —SO₂Ph, PO(CH₃)₂, B(OH)₂, phenyl, pyridyl, tetrahydropyranyl, tetrahydrofuranyl, cyclopropyl, cyclohexyl, imidazolyl,

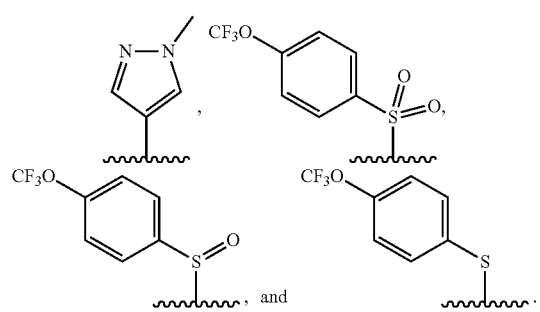
, and

In some embodiments of Formula I, Z is selected from

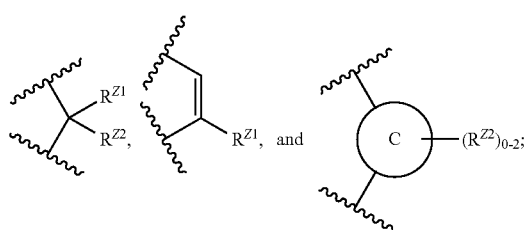

wherein Ring C is selected from $C_6$-$C_{10}$ aryl.

In some embodiments of Formula I, the group:

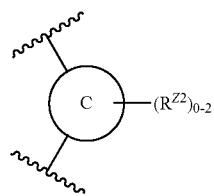

is selected from:

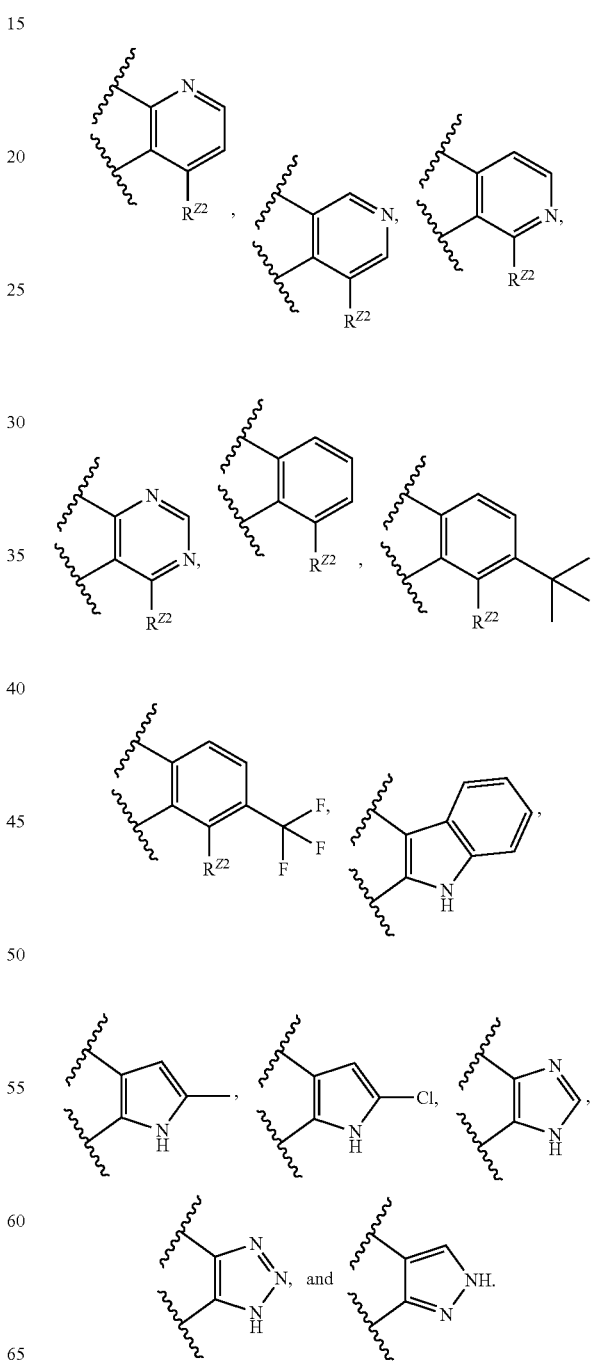

In some embodiments of Formula I, the group:

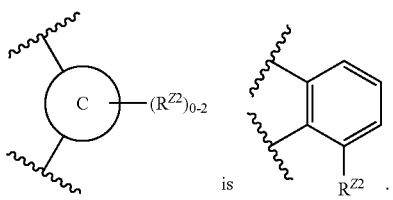

is

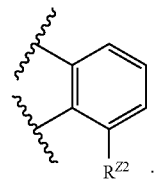

In some embodiments of Formula I, $R^{Z1}$ is selected from hydrogen, $C_1$-$C_6$ alkyl (optionally substituted with 1-3 hydroxy), $C_1$-$C_6$ fluoroalkyl, 3- to 6-membered heterocyclyl, $C_3$-$C_6$ cycloalkyl, $C_6$-$C_{10}$ aryl, and 5- to 6-membered heteroaryl.

In some embodiments of Formula I, $R^{Z2}$ is selected from hydrogen, halogen, hydroxy, and $C_1$-$C_6$ alkoxy (optionally substituted with 1-3 groups independently selected from $C_3$-$C_{10}$ cycloalkyl).

In some embodiments of Formula I,
  $R^{Z1}$ is selected from hydrogen, $C_1$-$C_6$ alkyl (optionally substituted with 1-3 hydroxy), $C_1$-$C_6$ fluoroalkyl, 3- to 6-membered heterocyclyl, $C_3$-$C_6$ cycloalkyl, and $C_6$-$C_{10}$ aryl; and
  $R^{Z2}$ is selected from hydrogen, halogen, and hydroxy;
  or $R^{Z1}$ and $R^{Z2}$ taken together form a group selected from oxo and =N—OH.

In some embodiments of Formula I,
  $R^{Z1}$ is selected from hydrogen, $CH_3$, $CF_3$, $CH_2OH$, phenyl, cyclopropyl, and tetrahydropyranyl; and
  $R^{Z2}$ is selected from hydrogen, halogen, and hydroxy;
  or $R^{Z1}$ and $R^{Z2}$ taken together form a group selected from oxo and =N—OH.

In some embodiments of Formula I, $R^{Z2}$ is hydroxy.

In some embodiments of Formula I, Z is selected from:

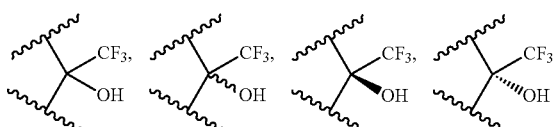

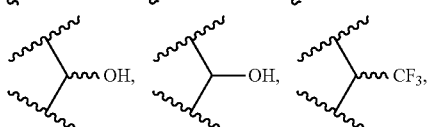

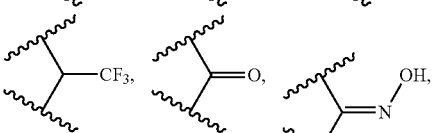

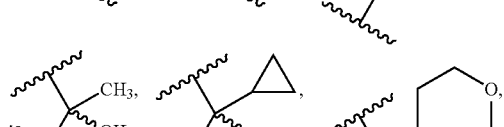

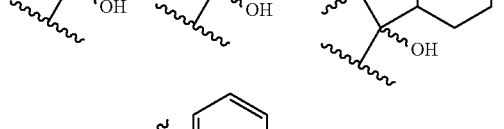

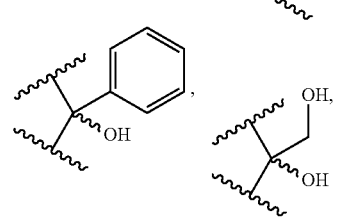

-continued

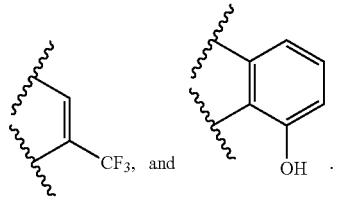

In some embodiments of Formula I, Z is

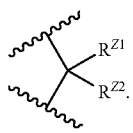

In some embodiments of Formula I, Z is

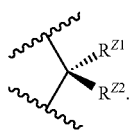

In some embodiments of Formula I, Z is

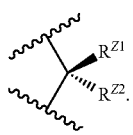

In some embodiments of Formula I, Z is

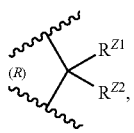

wherein (R) refers to the stereochemical designation of the central carbon atom under the Cahn-Ingold-Prelog convention. In some embodiments of Formula I, Z is

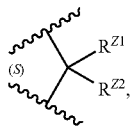

wherein (S) refers to the stereochemical designation of the central carbon atom under the Cahn-Ingold-Prelog convention.

In some embodiments of Formula I, m is selected from 1 and 2.

In some embodiments, compounds of the invention are encompassed by Formula I':

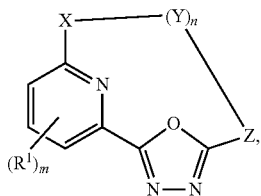

I' and includes deuterated derivatives thereof, and pharmaceutically acceptable salts of those compounds and deuterated derivatives, wherein:

X is selected from —N(R$^{X1}$)— and

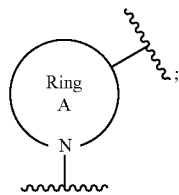

Ring A is a 4- to 6-membered heterocyclyl optionally substituted with 1-3 groups independently selected from C$_1$-C$_6$ alkyl and oxo;

R$^{X1}$ is selected from H, C$_1$-C$_6$ alkyl (optionally substituted with 1-3 groups independently selected from hydroxy, oxo, —OR$^{X2}$, and —N(R$^{X2}$)$_2$), and C$_3$-C$_8$ cycloalkyl;

each R$^{X1}$ is independently selected from H and C$_1$-C$_6$ alkyl;

each Y is independently selected from —C(R$^Y$)$_2$—, —O—, —CO—, —NR$^{YN}$—, and

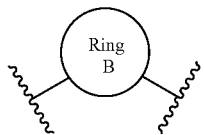

wherein each R$^{YN}$ is independently selected from H, C$_1$-C$_4$ alkyl, and CO$_2$Me;

each R$^Y$ is independently selected from hydrogen, hydroxy, halogen, C$_1$-C$_6$ alkyl (optionally substituted with 1-3 groups independently selected from hydroxy, C$_1$-C$_6$ alkoxy, and Q), C$_3$-C$_8$ cycloalkyl, C$_6$-C$_{10}$ aryl (optionally substituted with 1-3 groups independently selected from halogen), 5- to 10-membered heteroaryl, —OR$^{Y1}$, —CO$_2$R$^{Y1}$, —COR$^{Y1}$, —CON(R$^{Y1}$)$_2$, and —N(R$^{Y1}$)$_2$;

or two R$^Y$ on the same atom are taken together to form a ring selected from C$_3$-C$_8$ cycloalkyl and 3- to 7-membered heterocyclyl; or two R$^Y$, one of which is on one atom and the second of which is on an adjacent atom, are taken together to form a pi bond;

each R$^{Y1}$ is independently selected from hydrogen and C$_1$-C$_6$ alkyl, or two R$^{Y1}$ bonded to the same nitrogen taken together form a 3- to 6-membered heterocyclyl;

Ring B is selected from:
C$_6$-C$_{10}$ aryl (optionally substituted with 1-3 groups independently selected from halogen, C$_1$-C$_6$ alkyl, and C$_1$-C$_6$ alkoxy),
C$_3$-C$_8$ cycloalkyl,
5- to 10-membered heteroaryl, and
3- to 6-membered heterocyclyl (optionally substituted with 1-3 groups independently selected from C$_1$-C$_6$ alkyl);

each Q is independently selected from:
C$_1$-C$_6$ alkyl optionally substituted with 1-3 groups independently selected from:
halogen,
oxo,
C$_6$-C$_{10}$ aryl (optionally substituted with 1-3 groups independently selected from halogen and —OCF$_3$), and
C$_3$-C$_8$ cycloalkyl,
C$_3$-C$_8$ cycloalkyl optionally substituted with 1-3 groups independently selected from:
halogen,
CN,
C$_1$-C$_6$ alkyl (optionally substituted with 1-3 groups independently selected from halogen, —NH$_2$, and —NHCOMe),
C$_1$-C$_6$ alkoxy,
C$_6$-C$_{10}$ aryl (optionally substituted with 1-3 groups independently selected from C$_1$-C$_6$ alkyl), and
C$_3$-C$_8$ cycloalkyl,
C$_6$-C$_{10}$ aryl optionally substituted with 1-3 groups independently selected from:
halogen,
CN,
C$_1$-C$_6$ alkyl (optionally substituted with 1-3 groups independently selected from halogen and hydroxy),
C$_1$-C$_6$ alkoxy optionally substituted with 1-4 groups independently selected from:
halogen,
C$_3$-C$_8$ cycloalkyl (optionally substituted with CF$_3$),
C$_3$-C$_8$ cycloalkyl (optionally substituted with 1-3 groups independently selected from halogen, CF$_3$, OCF$_3$, and C$_1$-C$_6$ alkyl), and
C$_6$-C$_{10}$ aryl,
5- to 10-membered heteroaryl optionally substituted with 1-3 groups independently selected from:
halogen,
C$_1$-C$_6$ alkyl (optionally substituted with 1-3 groups independently selected from halogen),
C$_3$-C$_8$ cycloalkyl (optionally substituted with 1-3 CF$_3$ groups), and
3- to 10-membered heterocyclyl,
3- to 10-membered heterocyclyl optionally substituted with 1-3 groups independently selected from:
C$_1$-C$_6$ alkyl (optionally substituted with 1-3 groups independently selected from oxo and C$_3$-C$_8$ cycloalkyl), and
oxo;

each R$^1$ is independently selected from halogen, C$_1$-C$_6$ fluoroalkyl, C$_1$-C$_6$ alkyl (optionally substituted with a group selected from C$_6$-C$_{10}$ aryl and 5- to 6-membered heteroaryl), —OR$^2$, —N(R$^2$)$_2$, —CO$_2$R$^2$, —CO—N(R$^2$)$_2$, —CN, C$_1$-C$_6$ alkoxy, C$_3$-C$_8$ cycloalkyl, C$_6$-C$_{10}$ aryl, 5- to 6-membered heteroaryl (optionally substituted with 1-3 groups independently selected from C$_1$-C$_6$ alkyl), 3- to 6-membered heterocyclyl, —SO$_2$R$^2$, —SR$^2$, —SOR$^2$, —PO(OR$^2$)$_2$, and —PO(R$^2$)$_2$;

each R$^2$ is independently selected from hydrogen, C$_1$-C$_6$ alkyl (optionally substituted with 1-6 groups independently selected from halogen), $C_1$-$C_6$ fluoroalkyl, and $C_6$-$C_{10}$ aryl (optionally substituted with 1-3 groups independently selected from $C_1$-$C_6$ fluoroalkyl and $C_1$-$C_6$ fluoroalkoxy);

Z is selected from

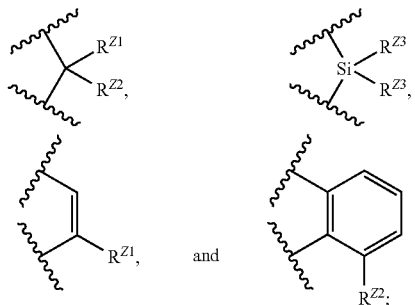

$R^{Z1}$ is selected from hydrogen, —CN, $C_1$-$C_6$ alkyl (optionally substituted with 1-3 hydroxy), $C_1$-$C_6$ fluoroalkyl, 3- to 6-membered heterocyclyl, $C_3$-$C_6$ cycloalkyl, $C_6$-$C_{10}$ aryl, and 5- to 6-membered heteroaryl;

$R^{Z2}$ is selected from hydrogen, halogen, hydroxy, and $C_1$-$C_6$ alkoxy (optionally substituted with 1-3 groups independently selected from $C_3$-$C_{10}$ cycloalkyl), or $R^{Z1}$ and $R^{Z2}$ taken together form a group selected from oxo and =N—OH;

each $R^{Z3}$ is independently selected from hydroxy, $C_1$-$C_6$ alkoxy, $C_1$-$C_6$ alkyl, and $C_6$-$C_{10}$ aryl; or two $R^{Z3}$ are taken together to form a 3- to 6-membered heterocyclyl;

n is selected from 4, 5, 6, and 7; and m is selected from 0, 1, 2, and 3.

In some embodiments, the compound of Formula I is selected from compounds of Formula I":

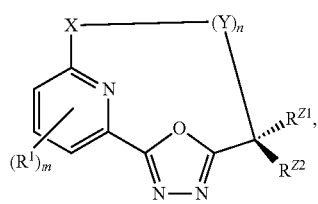

I"

and deuterated derivatives and pharmaceutically acceptable salts thereof, wherein all variables are as defined for Formula I.

In some embodiments of Formula I", the portion of the compound represented by:

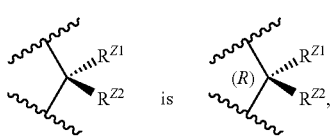

wherein (R) refers to the stereochemical designation of the central carbon atom under the Cahn-Ingold-Prelog convention. In some embodiments of Formula I", the portion of the compound represented by

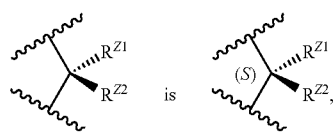

wherein (S) refers to the stereochemical designation of the central carbon atom under the Cahn-Ingold-Prelog convention.

The compounds of the invention also include compounds of Formulae Ia, IIa, IIb, IIc, IId, IIe, IIf, IIg, and IIh:

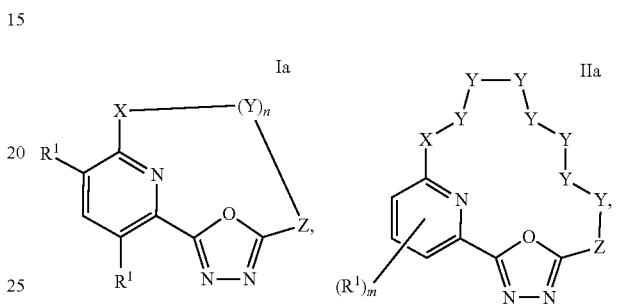

Ia

IIa

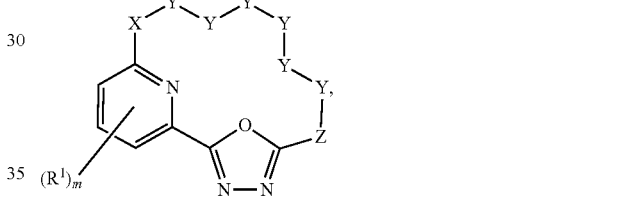

IIb

IIc

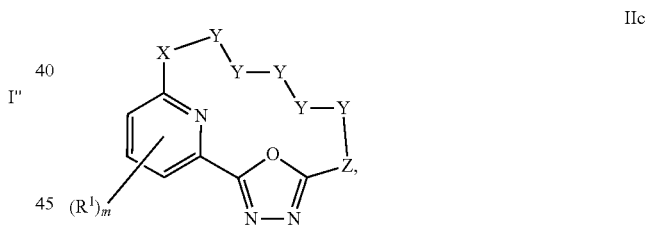

IId

IIe

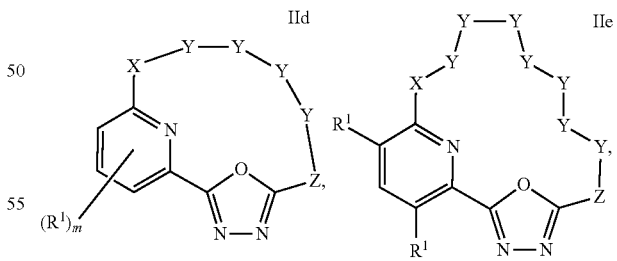

IIf

IIg

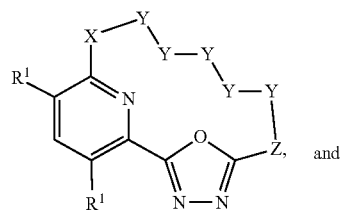

and

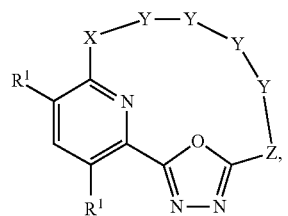

and deuterated derivatives and pharmaceutically acceptable salts thereof, wherein all variables are as defined for Formula I'.

The compounds of the invention also include compounds of Formulae Ia', IIa', IIb', IIc', IId', IIe', IIg', and IIh':

Ia'

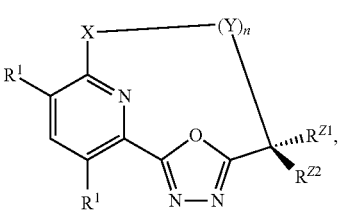

IIa'

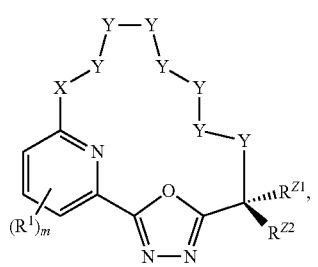

IIb'

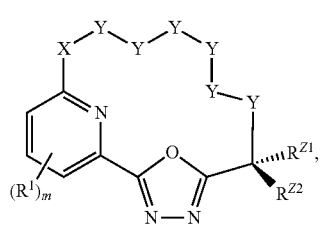

IIc'

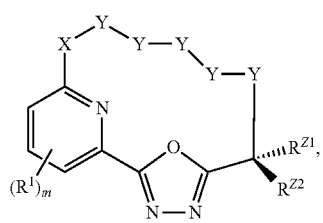

IId'

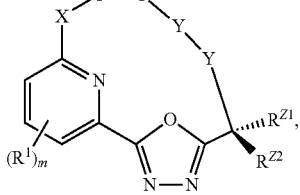

IIe'

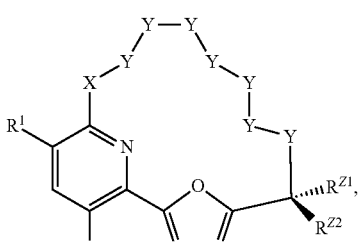

IIf'

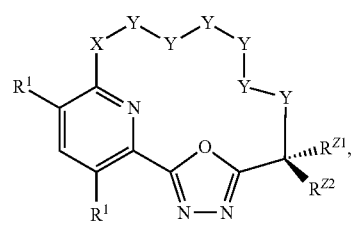

IIg'

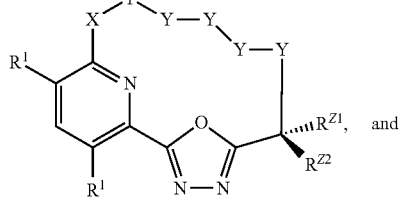

and

IIh'

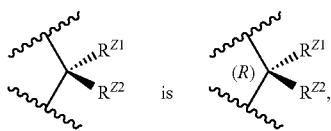

and deuterated derivatives and pharmaceutically acceptable salts thereof, wherein all variables are as defined for Formula I.

In some embodiments of Formulae Ia', IIa', IIc', IId', IIe', IIf', IIg', and IIh', the portion of the compound represented by:

is wherein (R) refers to the stereochemical designation of the central carbon atom under the Cahn-Ingold-Prelog convention. In some embodiments of Formula I'', the portion of the compound represented by

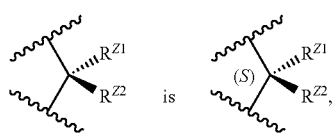

wherein (S) refers to the stereochemical designation of the central carbon atom under the Cahn-Ingold-Prelog convention.

Another aspect of the invention provides pharmaceutical compositions comprising at least one compound chosen from compounds of Formulae I, I', I", Ia, Ia', IIa, IIa', IIb, IIb', IIc, IIc', IId, IId', IIe, IIe', IIf, IIf', IIg, IIg', IIh, and IIh', Compounds 1 to 213, Compounds 214 to 222, deuterated derivatives thereof, and pharmaceutically acceptable salts of any of the foregoing, and at least one pharmaceutically acceptable carrier, which compositions may further include at least one additional active pharmaceutical ingredient. Thus, another aspect of the invention provides methods of treating the CFTR-mediated disease cystic fibrosis comprising administering at least one of compound chosen from compounds of Formulae I, I', I", Ia, Ia', IIa, IIa', IIb, IIb', IIc, IIc', IId, IId', IIe, IIe', IIf, IIf', IIg, IIg', IIh, and IIh', Compounds 1 to 213, Compounds 214 to 222, deuterated derivatives thereof, and pharmaceutically acceptable salts of any of the foregoing, and at least one pharmaceutically acceptable carrier, optionally as part of a pharmaceutical composition comprising at least one additional component, to a subject in need thereof.

In certain embodiments, the pharmaceutical compositions of the invention comprise at least one compound chosen from compounds of Formulae I, I', I", Ia, Ia', IIa, IIa', IIb, IIb', IIc, IIc', IId, IId', IIe, IIe', IIf, IIf', IIg, IIg', IIh, and IIh', Compounds 1 to 213, Compounds 214 to 222, deuterated derivatives thereof, and pharmaceutically acceptable salts of any of the foregoing. In some embodiments, compositions comprising at least one compound chosen from compounds of Formulae I, I', I", Ia, Ia', IIa, IIa', IIb, IIb', IIc, IIc', IId, IId', IIe, IIe', IIf, IIf', IIg, IIg', IIh, and IIh', Compounds 1 to 213, Compounds 214 to 222, deuterated derivatives thereof, and pharmaceutically acceptable salts of any of the foregoing may optionally further comprise at least one compound chosen from Compound II, Compound IV, Compound V, Compound VI, Compound VII, Compound VIII, Compound IX, Compound X, deuterated derivatives thereof, and pharmaceutically acceptable salts of any of the foregoing.

Another aspect of the invention provides methods of treating the CFTR-mediated disease cystic fibrosis comprising administering to a patient in need thereof at least one compound chosen from the novel compounds disclosed herein, pharmaceutically acceptable salts thereof, and deuterated derivatives of any of the foregoing, and optionally further administering one or more additional CFTR modulating agents selected from (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound II), N-[2,4-bis(1,1-dimethylethyl)-5-hydroxyphenyl]-1,4-dihydro-4-oxoquinoline-3-carboxamide (Compound III) or N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide (Compound III-d), 3464142,2-difluorobenzo[d][1,3]dioxol-5-yl)cyclopropane carboxamido)-3-methylpyridin-2-yl)benzoic acid (Compound IV), N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (Compound V), N-(benzenesulfonyl)-6-[3-[2-[1-(trifluoromethyl) cyclopropyl]ethoxy]pyrazol-1-yl]-2-[(4S)-2,2,4-trimethylpyrrolidin-1-yl]pyridine-3-carboxamide (Compound VI), (14S)-8-[3-(2-{dispiro[2.0.2.1]heptan-7-yl}ethoxy)-1H-pyrazol-1-yl]-12,12-dimethyl-2λ⁶-thia-3,9,11,18,23-pentaazatetracyclo[17.3.1.111,14.0⁵,¹⁰]tetracosa-1(22),5,7,9,19(23),20-hexaene-2,2,4-trione (Compound VII), (11R)-6-(2,6-dimethylphenyl)-11-(2-methylpropyl)-12-{spiro[2.3]hexan-5-yl}-9-oxa-2λ⁶-thia-3,5,12,19-tetraazatricyclo[12.3.1.14,8]nonadeca-1(17),4(19),5,7,14(18),15-hexaene-2,2,13-trione (Compound VIII); N-(benzenesulfonyl)-6-(3-fluoro-5-isobutoxy-phenyl)-2-[(4S)-2,2,4-trimethylpyrrolidin-1-yl]pyridine-3-carboxamide (Compound IX), and N-[(6-amino-2-pyridyl)sulfonyl]-6-(3-fluoro-5-isobutoxy-phenyl)-2-[(4S)-2,2,4-trimethylpyrrolidin-1-yl]pyridine-3-carboxamide (Compound X).

Another aspect of the invention provides methods of treating the CFTR-mediated disease cystic fibrosis comprising administering to a patient in need thereof at least one compound chosen from compounds of Formulae I, I', I", Ia, Ia', IIa, IIa', IIb, IIb', IIc, IIc', IId, IId', IIe, IIe', IIf, IIf', IIg, IIg', IIh, and IIh', Compounds 1 to 213, Compounds 214 to 222, deuterated derivatives thereof, and pharmaceutically acceptable salts of any of the foregoing, and optionally further administering one or more additional CFTR modulating agents selected from:

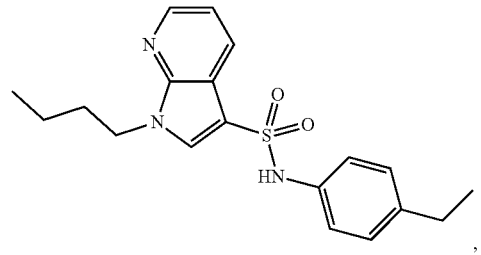

(ASP-11)

disclosed in *Journal of Cystic Fibrosis* (2018), 17(5), 595-606, and:

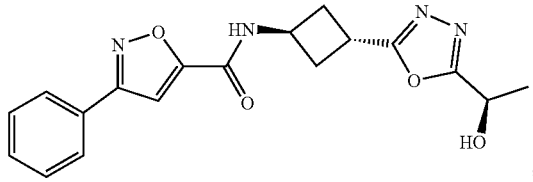

(nesolicaftor or PTI-428)

disclosed in WO 2016/105485. In one embodiment, the additional CFTR modulating agent is ASP-11. In one embodiment, the additional CFTR modulating agent comprises PTI-428.

Another aspect of the invention provides methods of treating the CFTR-mediated disease cystic fibrosis comprising administering to a patient in need thereof at least one compound chosen from compounds of Formulae I, I', I", Ia, Ia', IIa, IIa', IIb, IIb', IIc, IIc', IId, IId', IIe, IIe', IIf, IIf', IIg, IIg', IIh, and IIh', Compounds 1 to 213, Compounds 214 to 222, deuterated derivatives thereof, and pharmaceutically acceptable salts of any of the foregoing, and optionally further administering one or more additional CFTR modulating agents selected from:

(galicaftor or ABBV-2222)

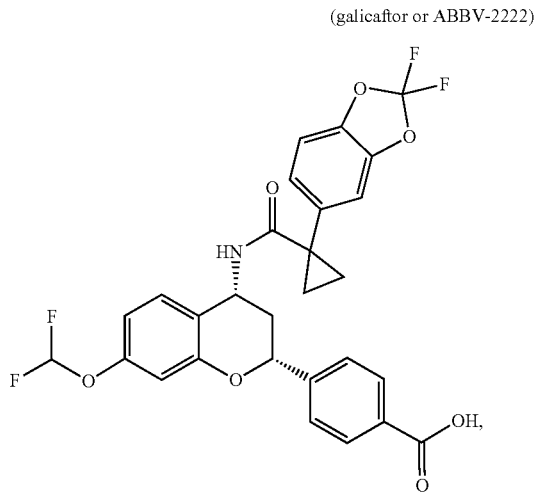 [SMILES: O=C(O)c1ccc([C@H]2C[C@@H](NC(=O)C3(c4ccc5c(c4)OC(F)(F)O5)CC3)c3ccc(OC(F)F)cc3O2)cc1]

disclosed in United States Patent Application Publication No. 2016-0120841;

(ABBV-3221)

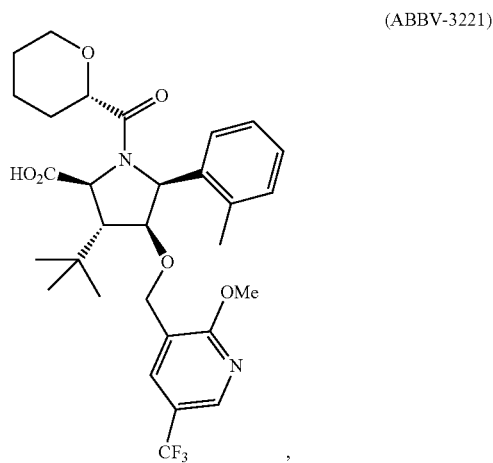 [SMILES: COc1ncc(C(F)(F)F)cc1CO[C@H]1[C@H](C(C)(C)C)[C@@H](C(=O)O)N(C(=O)[C@@H]2CCCCO2)[C@H]1c1ccccc1C]

disclosed in WO 2018/065921;

(posenacaftor or PTI-801)

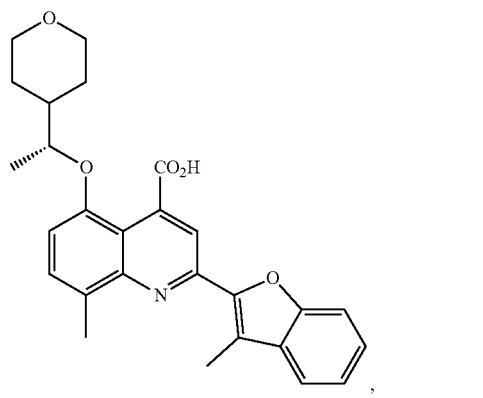

disclosed in WO 2017/062581; ABBV-2851, disclosed in WO 2017/009804; GLPG2737, disclosed in United States Patent Application Publication No. 2017-0101405; ABBV-3748; ABBV-3903; and ABBV-119.

DEFINITIONS

Figure 1:
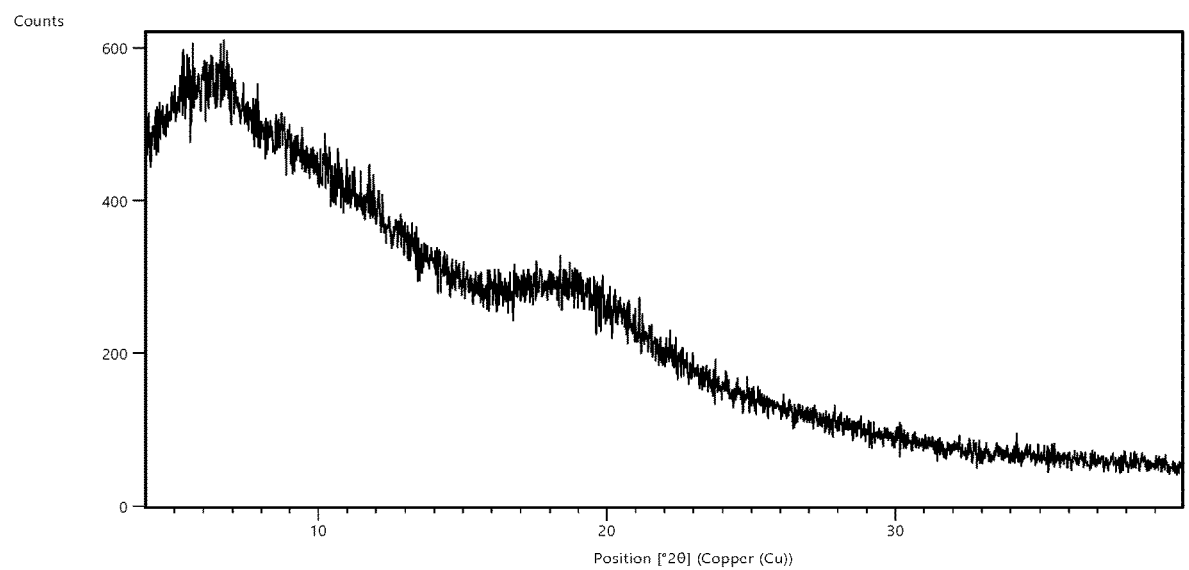
FIG. 1 provides an X-ray power diffraction (XRPD) pattern of amorphous Compound 4 (neat form).

"Compound II" as used herein, refers to (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, which can be depicted with the following structure:

Compound II

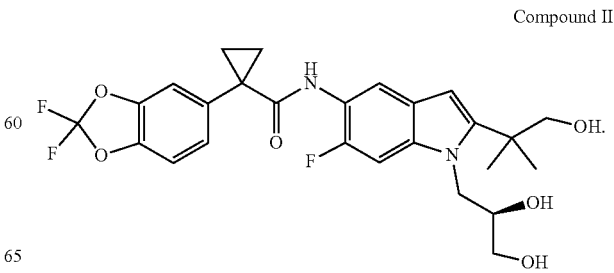

Compound II may be in the form of a pharmaceutically acceptable salt. Compound II and methods of making and using Compound II are disclosed in WO 2010/053471, WO 2011/119984, WO 2011/133751, WO 2011/133951, and WO 2015/160787, each incorporated herein by reference.

"Compound III" as used throughout this disclosure refers to N-(5-hydroxy-2,4-di-tert-butyl-phenyl)-4-oxo-1H-quinoline-3-carboxamide which is depicted by the structure:

Compound III

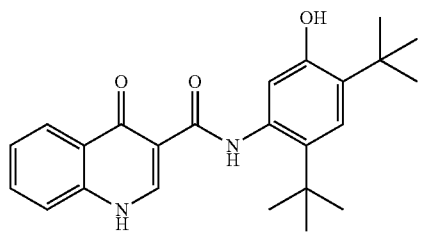

Compound III may also be in the form of a pharmaceutically acceptable salt. Compound III and methods of making and using Compound III are disclosed in WO 2006/002421, WO 2007/079139, WO 2010/108162, and WO 2010/019239, each incorporated herein by reference.

In some embodiments, a deuterated derivative of Compound III (Compound III-d) is employed in the compositions and methods disclosed herein. A chemical name for Compound III-d is N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide, as depicted by the structure:

Compound III-d

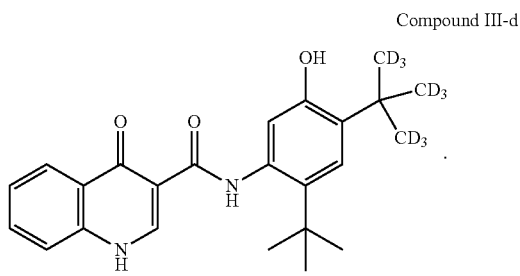 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

Compound III-d may be in the form of a pharmaceutically acceptable salt. Compound III-d and methods of making and using Compound III-d are disclosed in WO 2012/158885, WO 2014/078842, and U.S. Pat. No. 8,865,902, incorporated herein by reference.

"Compound IV" as used herein, refers to 3-(6-(1-(2,2-difluorobenzo[d][1,3]dioxol-5-yl)cyclopropanecarboxamido)-3-methylpyridin-2-yl)benzoic acid, which is depicted by the chemical structure:

Compound IV

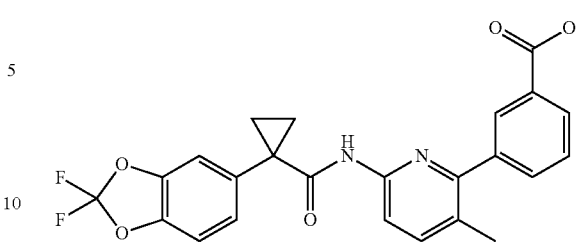

Compound IV may be in the form of a pharmaceutically acceptable salt. Compound IV and methods of making and using Compound IV are disclosed in WO 2007/056341, WO 2009/073757, and WO 2009/076142, incorporated herein by reference.

"Compound V" as used herein, refers to N-(1,3-dimethylpyrazol-4-yl)sulfonyl-6-[3-(3,3,3-trifluoro-2,2-dimethylpropoxy)pyrazol-1-yl]-2-[(4S)-2,2,4-trimethylpyrrolidin-1-yl]pyridine-3-carboxamide, which is depicted by the chemical structure:

Compound V

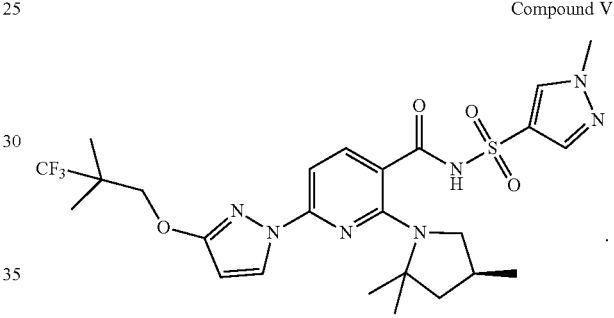

Compound V may be in the form of a pharmaceutically acceptable salt. Compound V and methods of making and using Compound V are disclosed in WO 2018/107100 and WO 2019/113476, incorporated herein by reference.

"Compound VI" as used herein, refers to N-(benzenesulfonyl)-6-[3-[2-[1-(trifluoromethyl) cyclopropyl]ethoxy]pyrazol-1-yl]-2-[(4S)-2,2,4-trimethylpyrrolidin-1-yl]pyridine-3-carboxamide, which is depicted by the chemical structure:

Compound VI

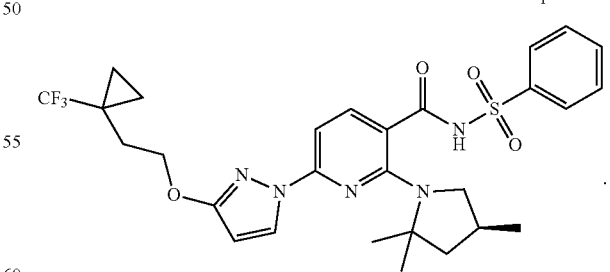

Compound VI may be in the form of a pharmaceutically acceptable salt. Compound VI and methods of making and using Compound VI are disclosed in WO 2018/064632, incorporated herein by reference.

"Compound VII" as used herein, refers to (14S)-8-[3-(2-{dispiro[2.0.2.1]heptan-7-yl}ethoxy)-1H-pyrazol-1-yl]-12, 12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione, which is depicted by the chemical structure:

Compound VII

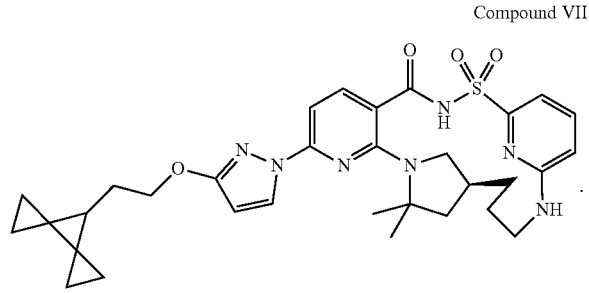 [SMILES: CC1(C)C[C@@H]2CCCNc3cccc(n3)S(=O)(=O)NC(=O)c3ccc(-n4ccc(OCCC5C6(CC6)C56CC6)n4)nc3N1C2]

Compound VII may be in the form of a pharmaceutically acceptable salt. Compound VII and methods of making and using Compound VII are disclosed in WO 2019/161078, WO 2020/102346, and PCT Application No. PCT/US2020/046116, incorporated herein by reference.

"Compound VIII" as used herein, refers to (11R)-6-(2,6-dimethylphenyl)-11-(2-methylpropyl)-12-{spiro[2.3]hexan-5-yl}-9-oxa-2λ⁶-thia-3,5,12,19-tetraazatricyclo[12.3.1.1⁴,⁸]nonadeca-1(17),4(19),5,7,14(18),15-hexaene-2,2,13-trione, which is depicted by the chemical structure:

Compound VIII

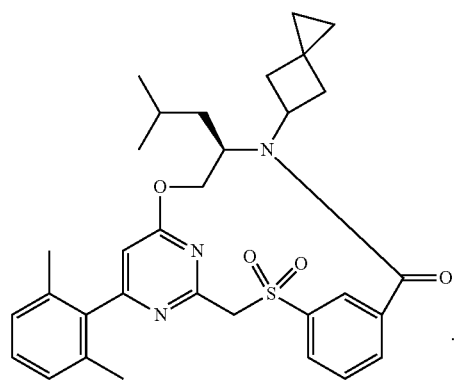

Compound VIII may be in the form of a pharmaceutically acceptable salt. Compound VIII and methods of making and using Compound VIII are disclosed in WO 2020/206080, incorporated herein by reference.

"Compound IX" as used herein, refers to N-(benzenesulfonyl)-6-(3-fluoro-5-isobutoxy-phenyl)-2-[(4S)-2,2,4-trimethylpyrrolidin-1-yl]pyridine-3-carboxamide, which is depicted by the chemical structure:

Coompound IX

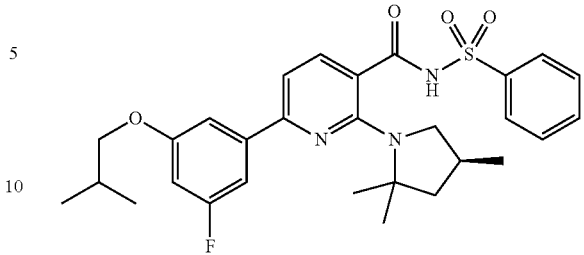

Compound IX may be in the form of a pharmaceutically acceptable salt. Compound IX and methods of making and using Compound IX are disclosed in WO 2016/057572, incorporated herein by reference.

"Compound X" as used herein, refers to N-[(6-amino-2-pyridyl)sulfonyl]-6-(3-fluoro-5-isobutoxy-phenyl)-2-[(4S)-2,2,4-trimethylpyrrolidin-1-yl]pyridine-3-carboxamide, which is depicted by the chemical structure:

Coompound X

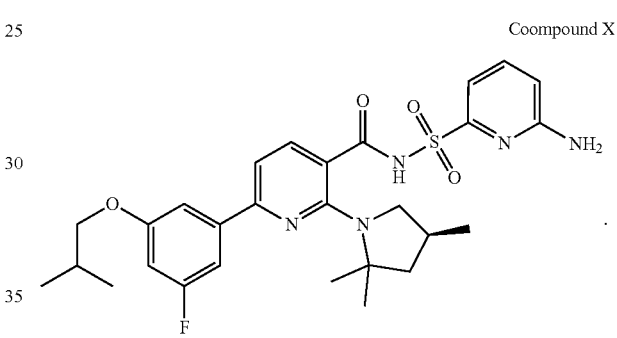

Compound X may be in the form of a pharmaceutically acceptable salt. Compound X and methods of making and using Compound X are disclosed in WO 2016/057572, incorporated herein by reference.

As used herein, the term "alkyl" refers to a saturated, branched or unbranched aliphatic hydrocarbon containing carbon atoms (such as, for example, 1, 2, 3, 4, 5, 6, 7, 8, 9, 10, 11, 12, 13, 14, 15, 16, 17, 18, 19, or 20 carbon atoms). Alkyl groups may be substituted or unsubstituted.

As used herein, the term "pi bond" refers to a covalent bond formed by the p orbitals of adjacent atoms. Pi bonds exist where there is a multiple bond, i.e., a double or triple bond, between two atoms. For example, a carbon-carbon double bond consists of one pi bond, and a carbon-carbon triple bond consists of two pi bonds.

As used herein, the term "haloalkyl group" refers to an alkyl group substituted with one or more halogen atoms.

As used herein, the term "fluoroalkyl" refers to an alkyl group substituted with one or more fluorine atoms. In some embodiments, a fluoroalkyl group is substituted by 1-6 fluorine atoms. In some embodiments, a fluoroalkyl group is perfluorinated.

The term "alkoxy" as used herein refers to an alkyl or cycloalkyl covalently bonded to an oxygen atom. Alkoxy groups may be substituted or unsubstituted.

As used herein, the term "haloalkoxyl group" refers to an alkoxy group substituted with one or more halogen atoms.

As used herein, the term "fluoroalkoxy" refers to an alkoxy group substituted with one or more fluorine atoms. In some embodiments, a fluoroalkoxy group is substituted by 1-6 fluorine atoms. In some embodiments, a fluoroalkoxy group is perfluorinated.

As used herein, "cycloalkyl" refers to a cyclic, bicyclic, tricyclic, or polycyclic non-aromatic hydrocarbon groups having 3 to 12 carbons (such as, for example 3-10 carbons). "Cycloalkyl" groups encompass monocyclic, bicyclic, tricyclic, bridged, fused, and spiro rings, including mono spiro and dispiro rings. Non-limiting examples of cycloalkyl groups are cyclopropyl, cyclobutyl, cyclopentyl, cyclohexyl, adamantyl, norbornyl, and dispiro[2.0.2.1]heptane. Cycloalkyl groups may be substituted or unsubstituted.

The term "heteroaryl ring" as used herein refers to an aromatic ring comprising at least one ring atom that is a heteroatom, such as O, N, or S.

As used herein, the terms "heterocyclyl ring" and "heterocyclyl" refer to a non-aromatic hydrocarbon containing 3 to 12 atoms in a ring (such as, for example 3-10 atoms) comprising at least one ring atom that is a heteroatom, such as O, N, S, or Si. "Heterocyclyl" rings encompass monocyclic, bicyclic, tricyclic, polycyclic, bridged, fused, and spiro rings, including mono spiro and dispiro rings.

"Substituted" indicates that at least one hydrogen of the "substituted" group is replaced by a substituent. Unless otherwise indicated, an "optionally substituted" group may have a suitable substituent at each substitutable position of the group, and when more than one position in any given structure may be substituted with more than one substituent chosen from a specified group, the substituent may be either the same or different at each position.

Examples of protecting groups for nitrogen include, for example, t-butyl carbamate (Boc), benzyl (Bn), para-methoxybenzyl (PMB), tetrahydropyranyl (THP), 9-fluorenylmethyl carbamate (Fmoc), benzyl carbamate (Cbz), methyl carbamate, ethyl carbamate, 2,2,2-trichloroethyl carbamate (Troc), 2-trimethylsilylethyl carbamate (Teoc), allyl carbamate (Aloc or Alloc), formamide, acetamide, benzamide, allylamine, trifluoroacetamide, triphenylmethylamine, benzylideneamine, and p-toluenesulfonamide. A comprehensive list of nitrogen protecting groups can be found in Wuts, P. G. M. "Greene's Protective Groups in Organic Synthesis: Fifth Edition," 2014, John Wiley and Sons.

As used herein, "deuterated derivative(s)" means the same chemical structure, with one or more hydrogen atoms replaced by a deuterium atom.

As used herein, "CFTR" means cystic fibrosis transmembrane conductance regulator.

As used herein, the term "CFTR modulator" refers to a compound that increases the activity of CFTR. The increase in activity resulting from a CFTR modulator includes but is not limited to compounds that correct, potentiate, stabilize and/or amplify CFTR.

As used herein, the term "CFTR corrector" refers to a compound that facilitates the processing and trafficking of CFTR to increase the amount of CFTR at the cell surface.

As used herein, the term "CFTR potentiator" refers to a compound that increases the channel activity of CFTR protein located at the cell surface, resulting in enhanced ion transport. The novel compounds disclosed herein are CFTR potentiators.

As used herein, the terms "CFTR potentiator enhancer", CFTR potentiation enhancer", and "CFTR co-potentiator" are used interchangeably and refer to a compound that enhances CFTR potentiation.

As used herein, the term "active pharmaceutical ingredient" ("API") or "therapeutic agent" refers to a biologically active compound.

The terms "patient" and "subject" are used interchangeably and refer to an animal including humans.

The terms "effective dose" and "effective amount" are used interchangeably herein and refer to that amount of a compound that produces the desired effect for which it is administered (e.g., improvement in CF or a symptom of CF, or lessening the severity of CF or a symptom of CF). The exact amount of an effective dose will depend on the purpose of the treatment and will be ascertainable by one skilled in the art using known techniques (see, e.g., Lloyd (1999) The Art, Science and Technology of Pharmaceutical Compounding).

As used herein, the terms "treatment," "treating," and the like generally mean the improvement in one or more symptoms of CF or lessening the severity of CF or one or more symptoms of CF in a subject. "Treatment," as used herein, includes, but is not limited to, the following: increased growth of the subject, increased weight gain, reduction of mucus in the lungs, improved pancreatic and/or liver function, reduction of chest infections, and/or reductions in coughing or shortness of breath. Improvements in or lessening the severity of any of these symptoms can be readily assessed according to standard methods and techniques known in the art.

As used herein, the term "in combination with," when referring to two or more compounds, agents, or additional active pharmaceutical ingredients, means the administration of two or more compounds, agents, or active pharmaceutical ingredients to the patient prior to, concurrent with, or subsequent to each other.

The terms "about" and "approximately", when used in connection with doses, amounts, or weight percent of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent. The terms "about" and "approximately" may refer to an acceptable error for a particular value as determined by one of skill in the art, which depends in part on how the values is measured or determined. In some embodiments, the terms "about" and "approximately" mean within 20%, 15%, 10%, 5%, 4%, 3%, 2%, 1%, or 0.5% of a given value or range. As used herein, the symbol "~" appearing immediately before a numerical value has the same meaning as the terms "about" and "approximately."

As used herein, the term "solvent" refers to any liquid in which the product is at least partially soluble (solubility of product>1 g/L).

As used herein, the term "room temperature" or "ambient temperature" means 15° C. to 30° C.

It will be appreciated that certain compounds of this invention may exist as separate stereoisomers or enantiomers and/or mixtures of those stereoisomers or enantiomers. As used in the chemical structures disclosed herein, a "wedge" (╱) or "hash" (╲) bond to a stereogenic atom indicates a chiral center of known absolute stereochemistry (i.e. one stereoisomer). As used in the chemical structures disclosed herein, a "wavy" bond (∼) to a stereogenic atom indicates a chiral center of unknown absolute stereochemistry (i.e. one stereoisomer). As used in the chemical structures disclosed herein, a "wavy" bond (∼) to a double-bonded carbon indicates a mixture of E/Z isomers. As used in the chemical structures disclosed herein, a ╱ ("straight") bond to a stereogenic atom indicates where there is a mixture (e.g., a racemate or enrichment). As used herein, two ╱ ("straight") bonds to a double-bonded carbon indicates that the double bond possesses the E/Z stereochemistry as drawn. As used in the chemical structures disclosed herein, a

(i.e., a "wavy" line perpendicular to a "straight" bond to group "A") indicates that group "A" is a substituent whose point of attachment is at the end of the bond that terminates at the "wavy" line.

Certain compounds disclosed herein may exist as tautomers and both tautomeric forms are intended, even though only a single tautomeric structure is depicted. For example, a description of Compound A is understood to include its tautomer Compound B and vice versa, as well as mixtures thereof:

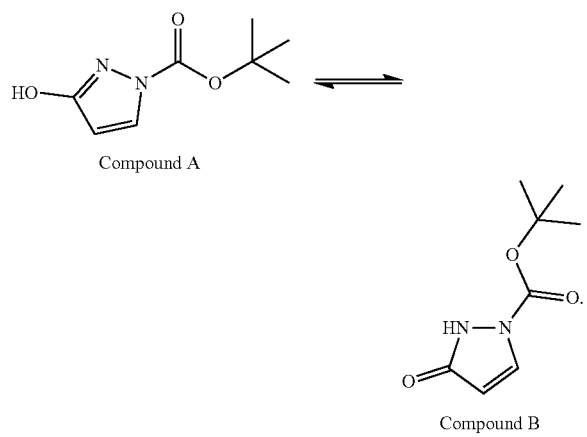

As used herein, "minimal function (MF) mutations" refer to CFTR gene mutations associated with minimal CFTR function (little-to-no functioning CFTR protein) and include, for example, mutations associated with severe defects in ability of the CFTR channel to open and close, known as defective channel gating or "gating mutations"; mutations associated with severe defects in the cellular processing of CFTR and its delivery to the cell surface; mutations associated with no (or minimal) CFTR synthesis; and mutations associated with severe defects in channel conductance.

As used herein, the term "pharmaceutically acceptable salt" refers to a salt form of a compound of this disclosure wherein the salt is nontoxic. Pharmaceutically acceptable salts of the compounds of this disclosure include those derived from suitable inorganic and organic acids and bases. A "free base" form of a compound, for example, does not contain an ionically bonded salt.

The phrase "and pharmaceutically acceptable salts and deuterated derivatives thereof" is used interchangeably with "and pharmaceutically acceptable salts thereof and deuterated derivatives of any of the forgoing" in reference to one or more compounds or formulae of the invention. These phrases are intended to encompass pharmaceutically acceptable salts of any one of the referenced compounds, deuterated derivatives of any one of the referenced compounds, and pharmaceutically acceptable salts of those deuterated derivatives.

One of ordinary skill in the art would recognize that, when an amount of "a compound or a pharmaceutically acceptable salt thereof" is disclosed, the amount of the pharmaceutically acceptable salt form of the compound is the amount equivalent to the concentration of the free base of the compound. It is noted that the disclosed amounts of the compounds or their pharmaceutically acceptable salts thereof herein are based upon their free base form.

Suitable pharmaceutically acceptable salts are, for example, those disclosed in S. M. Berge, et al. *J. Pharmaceutical Sciences*, 1977, 66, 1-19. For example, Table 1 of that article provides the following pharmaceutically acceptable salts:

TABLE 1

| | | |
|---|---|---|
| Acetate | Iodide | Benzathine |
| Benzenesulfonate | Isethionate | Chloroprocaine |
| Benzoate | Lactate | Choline |
| Bicarbonate | Lactobionate | Diethanolamine |
| Bitartrate | Malate | Ethylenediamine |
| Bromide | Maleate | Meglumine |
| Calcium edetate | Mandelate | Procaine |
| Camsylate | Mesylate | Aluminum |
| Carbonate | Methylbromide | Calcium |
| Chloride | Methylnitrate | Lithium |
| Citrate | Methylsulfate | Magnesium |
| Dihydrochloride | Mucate | Potassium |
| Edetate | Napsylate | Sodium |
| Edisylate | Nitrate | Zinc |
| Estolate | Pamoate (Embonate) | |
| Esylate | Pantothenate | |
| Fumarate | Phosphate/diphosphate | |
| Gluceptate | Polygalacturonate | |
| Gluconate | Salicylate | |
| Glutamate | Stearate | |
| Glycollylarsanilate | Subacetate | |
| Hexylresorcinate | Succinate | |
| Hydrabamine | Sulfate | |
| Hydrobromide | Tannate | |
| Hydrochloride | Tartrate | |
| Hydroxynaphthoate | Teociate | |
| | Triethiodide | |

Non-limiting examples of pharmaceutically acceptable acid addition salts include: salts formed with inorganic acids, such as hydrochloric acid, hydrobromic acid, phosphoric acid, sulfuric acid, or perchloric acid; salts formed with organic acids, such as acetic acid, oxalic acid, maleic acid, tartaric acid, citric acid, succinic acid or malonic acid; and salts formed by using other methods used in the art, such as ion exchange. Non-limiting examples of pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Pharmaceutically acceptable salts derived from appropriate bases include alkali metal, alkaline earth metal, ammonium, and $N^+(C_1\text{-}4alkyl)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other suitable, non-limiting examples of pharmaceutically acceptable salts include besylate and glucosamine salts.

As used herein, the term "amorphous" refers to a solid material having no long-range order in the position of its molecules. Amorphous solids are generally supercooled liquids in which the molecules are arranged in a random manner so that there is no well-defined arrangement, e.g., molecular packing, and no long-range order. Amorphous solids are generally isotropic, i.e., exhibit similar properties in all directions and do not have definite melting points. For example, an amorphous material is a solid material having no sharp characteristic crystalline peak(s) in its X-ray power diffraction (XRPD) pattern (i.e., is not crystalline as determined by XRPD). Instead, one or several broad peaks (e.g., halos) appear in its XRPD pattern. Broad peaks are characteristic of an amorphous solid. See, US 2004/0006237 for a comparison of XRPDs of an amorphous material and crystalline material. In some embodiments, a solid material may comprise an amorphous compound, and the material may, for example, be characterized by a lack of sharp characteristic crystalline peak(s) in its XRPD spectrum (i.e., the material is not crystalline, but is amorphous, as determined by XRPD). Instead, one or several broad peaks (e.g., halos) may appear in the XRPD pattern of the material. See US 2004/0006237 for a comparison of XRPDs of an amorphous material and crystalline material. A solid material, comprising an amorphous compound, may be characterized by, for example, a glass transition temperature which is lower than the melting point of a pure crystalline solid. Other techniques, such as, for example, solid state NMR may also be used to characterize crystalline or amorphous forms.

As used herein, the terms "crystal form," "crystalline form," and "Form" interchangeably refer to a crystal structure (or polymorph) having a particular molecular packing arrangement in the crystal lattice. Crystalline forms can be identified and distinguished from each other by one or more characterization techniques including, for example, X-ray powder diffraction (XRPD), single crystal X-ray diffraction, and $^{13}C$ solid state nuclear magnetic resonance ($^{13}C$ SSNMR). Accordingly, as used herein, the term "crystalline Form [X] of Compound (I)" refers to a unique crystalline form that can be identified and distinguished from other crystalline forms by one or more characterization techniques including, for example, XRFD, single crystal X-ray diffraction, and $^{13}C$ SSNMR. In some embodiments, the novel crystalline forms are characterized by an X-ray powder diffractogram having one or more signals at one or more specified two-theta values (° 2θ).

As used herein, the term "free form" refers to a non-ionized version of the compound in the solid state. Examples of free forms include free bases and free acids.

As used herein, the term "solvate" refers to a crystal form comprising one or more molecules of a compound of the present disclosure and, incorporated into the crystal lattice, one or more molecules of a solvent or solvents in stoichiometric or nonstoichiometric amounts. When the solvent is water, the solvate is referred to as a "hydrate."

In some embodiments, a solid material may comprise a mixture of crystalline solids and amorphous solids. A solid material comprising an amorphous compound may also, for example, contain up to 30% of a crystalline solid. In some embodiments, a solid material prepared to comprise an amorphous compound may also, for example, contain up to 25%, 20%, 15%, 10%, 5%, or 2% of a crystalline solid. In embodiments wherein the solid material contains a mixture of crystalline solids and amorphous solids, the characterizing data, such as XRFD, may contain indicators of both crystalline and amorphous solids. In some embodiments, a crystalline form of this disclosure may contain up to 30% amorphous compound. In some embodiments, a crystalline preparation of a compound of Formula I may contain up to 25%, 20%, 15%, 10%, 5%, or 2% of an amorphous solid.

As used herein, the term "substantially amorphous" refers to a solid material having little or no long-range order in the position of its molecules. For example, substantially amorphous materials have less than 15% crystallinity (e.g., less than 10% crystallinity, less than 5% crystallinity, or less than 2% crystallinity). It is also noted that the term "substantially amorphous" includes the descriptor, "amorphous," which refers to materials having no (0%) crystallinity.

As used herein, the term "substantially crystalline" refers to a solid material having little or no amorphous molecules. For example, substantially crystalline materials have less than 15% amorphous molecules (e.g., less than 10% amorphous molecules, less than 5% amorphous molecules, or less than 2% amorphous molecules). It is also noted that the term "substantially crystalline" includes the descriptor "crystalline," which refers to materials that are 100% crystalline form.

As used herein, a crystalline form is "substantially pure" when it accounts for an amount by weight equal to or greater than 90% of the sum of all solid form(s) in a sample as determined by a method in accordance with the art, such as quantitative XRPD. In some embodiments, the solid form is "substantially pure" when it accounts for an amount by weight equal to or greater than 95% of the sum of all solid form(s) in a sample. In some embodiments, the solid form is "substantially pure" when it accounts for an amount by weight equal to or greater than 99% of the sum of all solid form(s) in a sample. It is also noted that the term "substantially pure" includes the descriptor "pure."

As used herein, the term "XRPD" refers to the analytical characterization method of X-ray powder diffraction. XRPD patterns disclosed herein were recorded at ambient conditions in transmission or reflection geometry using a diffractometer.

As used herein, the term "ambient conditions" means room temperature, open air condition and uncontrolled humidity condition. The terms "room temperature" and "ambient temperature" mean 15° C. to 30° C.

As used herein, the terms "X-ray powder diffractogram," "X-ray powder diffraction pattern," "XRPD pattern," "XRPD spectrum" interchangeably refer to an experimentally obtained pattern plotting signal positions (on the abscissa) versus signal intensities (on the ordinate). For an amorphous material, an X-ray powder diffractogram may include one or more broad signals; and for a crystalline material, an X-ray powder diffractogram may include one or more signals, each identified by its angular value as measured in degrees 2θ (° 2θ), depicted on the abscissa of an X-ray powder diffractogram, which may be expressed as "a signal at . . . degrees two-theta," "a signal at [a] two-theta value(s) of . . . " and/or "a signal at at least . . . two-theta value(s) selected from . . . ."

A "signal" or "peak" as used herein refers to a point in the XRPD pattern where the intensity as measured in counts is at a local maximum. One of ordinary skill in the art would recognize that one or more signals (or peaks) in an XRPD pattern may overlap and may, for example, not be apparent to the naked eye. Indeed, one of ordinary skill in the art would recognize that some art-recognized methods are capable of and suitable for determining whether a signal exists in a pattern, such as Rietveld refinement.

As used herein, "a signal at . . . degrees two-theta" refer to X-ray reflection positions as measured and observed in X-ray powder diffraction experiments (° 2θ).

The repeatability of the measured angular values is in the range of ±0.2° 2θ, i.e., the angular value can be at the recited angular value+0.2 degrees two-theta, the angular value−0.2 degrees two-theta, or any value between those two end points (angular value+0.2 degrees two-theta and angular value−0.2 degrees two-theta).

The terms "signal intensities" and "peak intensities" interchangeably refer to relative signal intensities within a given X-ray powder diffractogram. Factors that can affect the relative signal or peak intensities include sample thickness and preferred orientation (e.g., the crystalline particles are not distributed randomly).

As used herein, an X-ray powder diffractogram is "substantially similar to that in [a particular] Figure" when at least 90%, such as at least 95%, at least 98%, or at least 99%, of the signals in the two diffractograms overlap. In determining "substantial similarity," one of ordinary skill in the art will understand that there may be variation in the intensities and/or signal positions in XRPD diffractograms even for the same crystalline form. Thus, those of ordinary skill in the art will understand that the signal maximum values in XRPD diffractograms (in degrees two-theta) generally mean that value is identified as ±0.2 degrees two-theta of the reported value, an art-recognized variance.

As used herein, a solid state nuclear magnetic resonance (SSNMR) spectrum is "substantially similar to that in [a particular] Figure" when at least 90%, such as at least 95%, at least 98%, or at least 99%, of the signals in the two spectra overlap. In determining "substantial similarity," one of ordinary skill in the art will understand that there may be variation in the intensities and/or signal positions in SSNMR spectra even for the same crystalline form. Thus, those of ordinary skill in the art will understand that the chemical shifts in SSNMR spectra (in parts per million (ppm) referred to herein) generally mean that value is identified as ±0.2 ppm of the reported value, an art-recognized variance.

The term "X-ray powder diffractogram having a signal at . . . two-theta values" as used herein refers to an XRPD pattern that contains X-ray reflection positions as measured and observed in X-ray powder diffraction experiments (° two-theta).

As used herein, the term "DSC" refers to the analytical method of Differential Scanning calorimetry.

As used herein, the term "onset of decomposition" refers to the intersection point of the baseline before transition and the interflection tangent.

As used herein, the term "glass transition temperature" or "Tg" refers to the temperature above which a hard and brittle "glassy" amorphous solid becomes viscous or rubbery.

As used herein, the term "melting temperature", "melting point", or "Tm" refers to the temperature at which a material transitions from a solid to a liquid phase.

As used herein, the term "TGA" refers to the analytical method of Thermo Gravimetric (or thermogravimetric) Analysis.

DETAILED DESCRIPTION OF EMBODIMENTS

In addition to compounds of Formula I, pharmaceutically acceptable salts thereof, and deuterated derivatives of those compounds and salts, the invention provides compounds of Formulae I', I", Ia, Ia', IIa, IIa', IIb, IIb', IIc, IIc', IId, IId', IIe, IIe', IIf, IIf', IIg, IIg', IIh, and IIh', Compounds 1 to 213, Compounds 214 to 222, deuterated derivatives thereof, and pharmaceutically acceptable salts of any of the foregoing.

For example, in some embodiments, the compound of Formula I is selected from compounds of any one of Formulae Ia, IIa, IIb, IIc, IId, IIe, IIf, IIg, and IIh:

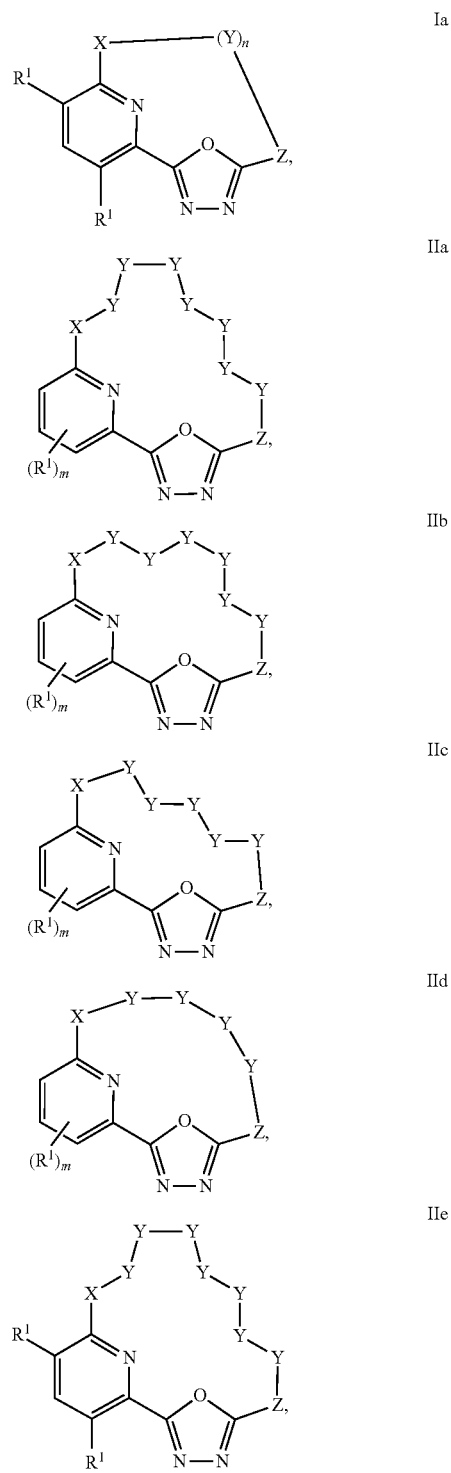

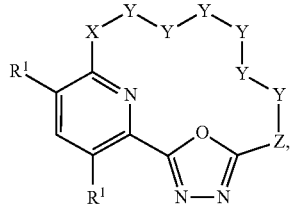
IIf

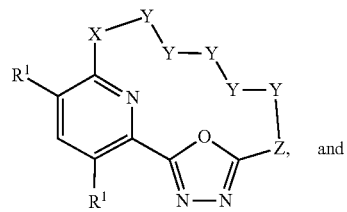
IIg

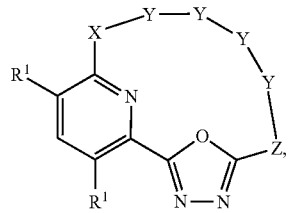
IIh and deuterated derivatives and pharmaceutically acceptable salts thereof, wherein all variables are as defined for Formula I'.

In some embodiments, the compound of Formula I is selected from compounds of Formula I":

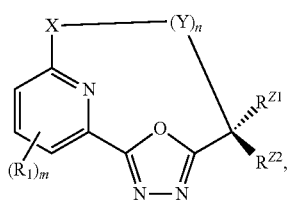
I"

and deuterated derivatives and pharmaceutically acceptable salts thereof, wherein all variables are as defined for Formula I.

In some embodiments, the compound of Formula I is selected from compounds of any one of Formulae Ia', IIa', IIb', IIc', IId', IIe', IIf', IIg', and IIh':

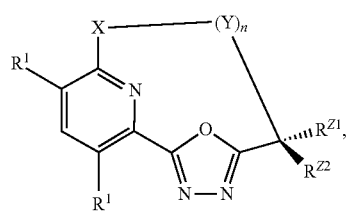
Ia'

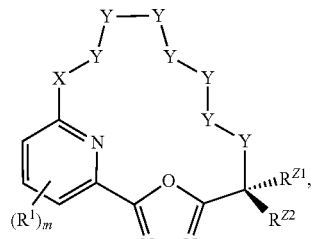
IIa'

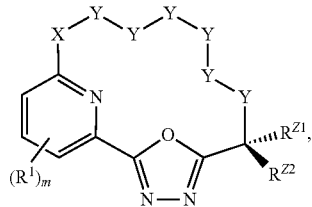
IIb'

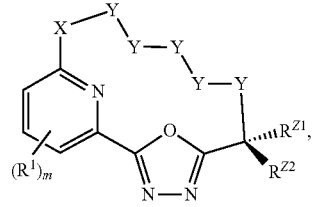
IIc'

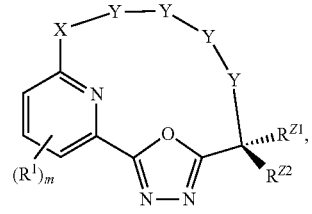
IId'

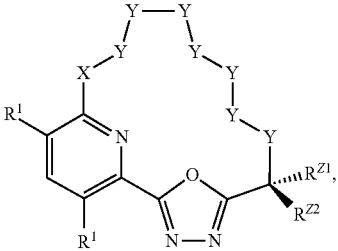
IIe'

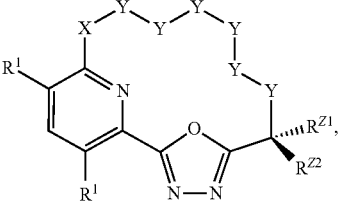
IIf'

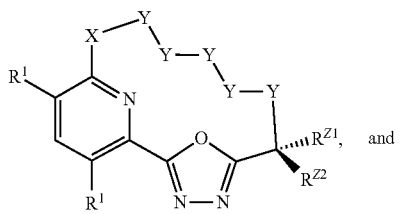
IIg' and

-continued

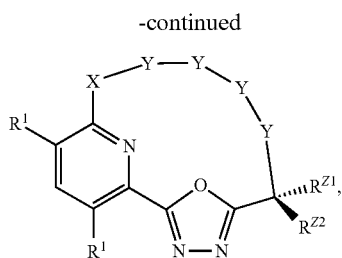

IIh' and deuterated derivatives and pharmaceutically acceptable salts thereof, wherein all variables are as defined for Formula I.

Also disclosed herein are compounds having a formula chosen from any one of the formulae depicted in Table 10, deuterated derivatives thereof, and pharmaceutically acceptable salts of any of those compounds and deuterated derivatives.

Solid Forms

Another aspect of the disclosure provides solid forms of the compounds of Formula I (e.g., compounds of Formulae I', I'', Ia, Ia', IIa, IIa', IIb, IIb', IIc, IIc', IId, IIc', IId, IId', IIe, IIe', IIf, IIf', IIg, IIg', IIh, and IIh', Compounds 1 to 213, Compounds 214 to 222, deuterated derivatives thereof, and pharmaceutically acceptable salts of any of the foregoing), which can be used in the methods of treatment and pharmaceutical compositions described herein.

Amorphous Compound 4 (Neat Form)

In some embodiments, the invention provides neat solid forms of Compound 4. In some embodiments, the invention provides a neat amorphous form of Compound 4. In some embodiments, the invention provides amorphous Compound 4 (neat form). FIG. 1 provides an X-ray powder diffractogram of amorphous Compound 4 (neat form) at room temperature.

In some embodiments, amorphous Compound 4 (neat form) is substantially pure. In some embodiments, amorphous Compound 4 (neat form) is substantially amorphous. In some embodiments, amorphous Compound 4 (neat form) is characterized by an X-ray powder diffractogram generated by an X-ray powder diffraction analysis with an incident beam of Cu Kα radiation.

In some embodiments, amorphous Compound 4 (neat form) is characterized by an X-ray powder diffractogram substantially similar to FIG. 1.

Crystalline Compound 5 Form A (Neat)

In some embodiments, the invention provides neat solid forms of Compound 5. In some embodiments, the invention provides neat crystalline forms of Compound 5. In some embodiments, the invention provides crystalline Compound 5 Form A (neat).

In some embodiments, crystalline Compound 5 Form A (neat) is substantially pure. In some embodiments, crystalline Compound 5 Form A (neat) is substantially crystalline.

In some embodiments, crystalline Compound 5 Form A (neat) is characterized by a tetragonal crystal system, an $I4_1$ space group, and the following unit cell dimensions measured at 100 K on a Bruker diffractometer utilizing Cu Kα radiation ($\lambda$=1.54178 Å):

| a | 18.1 ± .1 Å | α | 90° |
|---|---|---|---|
| b | 18.1 ± .1 Å | β | 90° |
| c | 13.1 ± .1 Å | γ | 90°. |

Amorphous Compound 19 (Neat Form)

Figure 4:
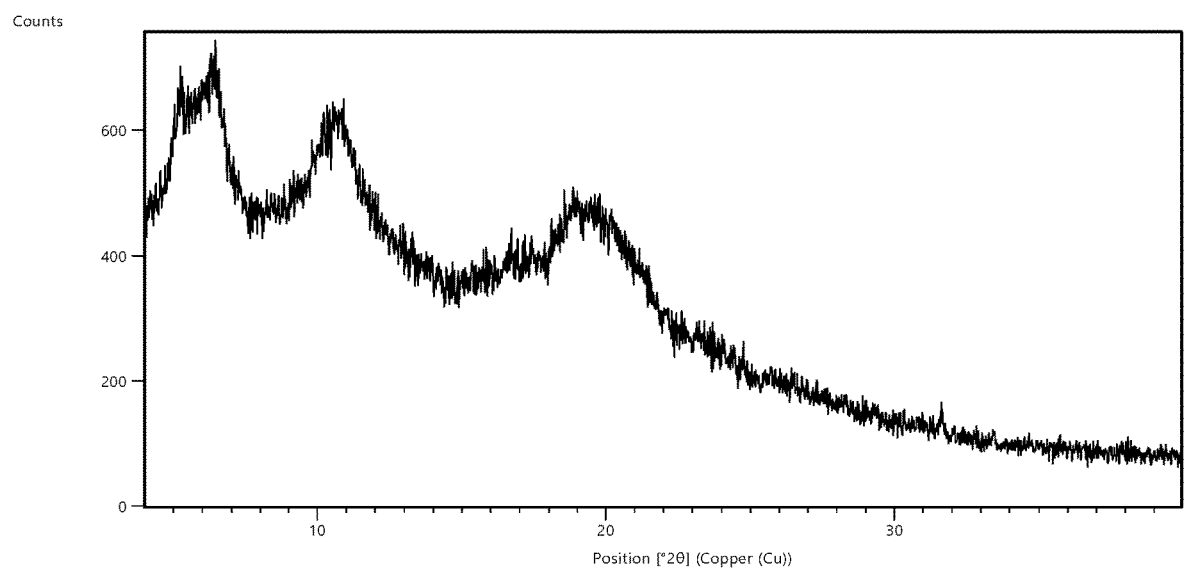
FIG. 4 provides an XRPD pattern of amorphous Compound 19 (neat form).

In some embodiments, the invention provides neat solid forms of Compound 19. In some embodiments, the invention provides a neat amorphous form of Compound 19. In some embodiments, the invention provides amorphous Compound 19 (neat form). FIG. 4 provides an X-ray powder diffractogram of amorphous Compound 19 (neat form) at room temperature.

In some embodiments, amorphous Compound 19 (neat form) is substantially pure. In some embodiments, amorphous Compound 19 (neat form) is substantially amorphous. In some embodiments, amorphous Compound 19 (neat form) is characterized by an X-ray powder diffractogram generated by an X-ray powder diffraction analysis with an incident beam of Cu Kα radiation.

In some embodiments, amorphous Compound 19 (neat form) is characterized by an X-ray powder diffractogram substantially similar to FIG. 4.

Crystalline Compound 41 Form A

Figure 7:
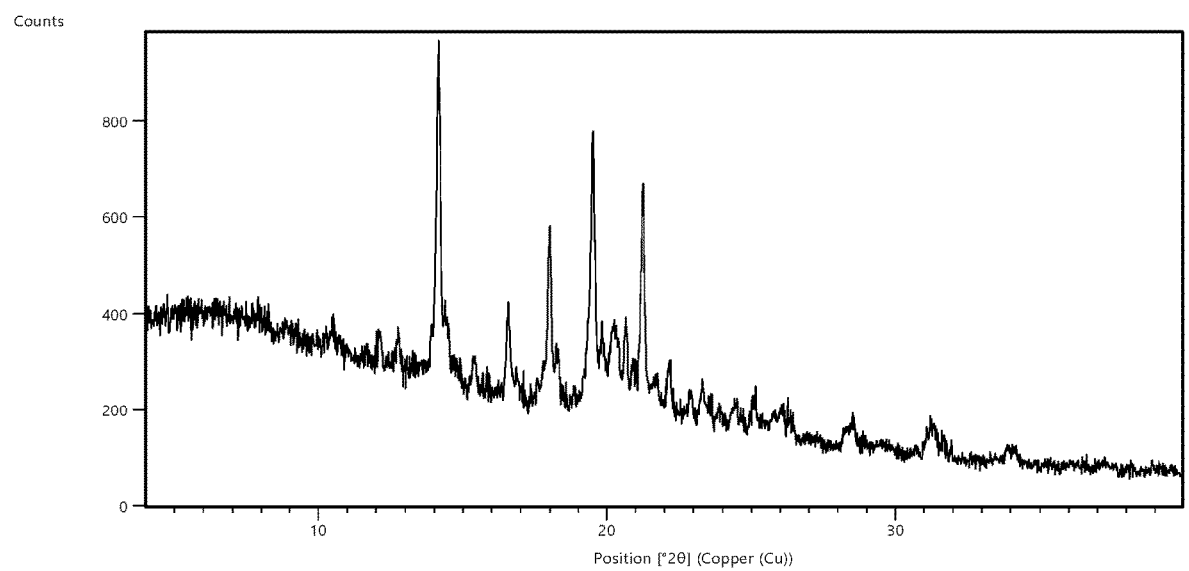
FIG. 7 provides an XRPD pattern of crystalline Compound 41 Form A.

In some embodiments, the invention provides solid forms of Compound 41. In some embodiments, the invention provides crystalline forms of Compound 41. In some embodiments, the invention provides crystalline Compound 41 Form A. FIG. 7 provides an X-ray powder diffractogram of crystalline Compound 41 Form A.

In some embodiments, crystalline Compound 41 Form A is substantially pure. In some embodiments, crystalline Compound 41 Form A is substantially crystalline. In some embodiments, crystalline Compound 41 Form A is characterized by an X-ray powder diffractogram generated by an X-ray powder diffraction analysis with an incident beam of Cu Kα radiation.

In some embodiments, crystalline Compound 41 Form A is characterized by an X-ray powder diffractogram having a signal at one or more of 14.2±0.2 degrees two-theta, 19.5±0.2 degrees two-theta, and 21.2±0.2 degrees two-theta. In some embodiments, crystalline Compound 41 Form A is characterized by an X-ray powder diffractogram having a signal at two or more of 14.2±0.2 degrees two-theta, 19.5±0.2 degrees two-theta, and 21.2±0.2 degrees two-theta. In some embodiments, crystalline Compound 41 Form A is characterized by an X-ray powder diffractogram having a signal at 14.2±0.2 degrees two-theta, 19.5±0.2 degrees two-theta, and 21.2±0.2 degrees two-theta.

In some embodiments, crystalline Compound 41 Form A is characterized by an X-ray powder diffractogram having a signal at three or more of 14.2±0.2 degrees two-theta, 19.5±0.2 degrees two-theta, 21.2±0.2 degrees two-theta, 18.0±0.2 degrees two-theta, 16.6±0.2 degrees two-theta, and 20.7±0.2 degrees two-theta. In some embodiments, crystalline Compound 41 Form A is characterized by an X-ray powder diffractogram having a signal at four or more of 14.2±0.2 degrees two-theta, 19.5±0.2 degrees two-theta, 21.2±0.2 degrees two-theta, 18.0±0.2 degrees two-theta, 16.6±0.2 degrees two-theta, and 20.7±0.2 degrees two-theta. In some embodiments, crystalline Compound 41 Form A is characterized by an X-ray powder diffractogram having a signal at five or more of 14.2±0.2 degrees two-theta, 19.5±0.2 degrees two-theta, 21.2±0.2 degrees two-theta, 18.0±0.2 degrees two-theta, 16.6±0.2 degrees two-theta, and 20.7±0.2 degrees two-theta. In some embodiments, crystalline Compound 41 Form A is characterized by an X-ray powder diffractogram having a signal at 14.2±0.2 degrees two-theta, 19.5±0.2 degrees two-theta, 21.2±0.2 degrees two-theta, 18.0±0.2 degrees two-theta, 16.6±0.2 degrees two-theta, and 20.7±0.2 degrees two-theta.

In some embodiments, crystalline Compound 41 Form A is characterized by an X-ray powder diffractogram having a signal at one, two, three, four, five, six, seven, eight, or more of 14.2±0.2 degrees two-theta, 16.6±0.2 degrees two-theta, 18.0±0.2 degrees two-theta, 19.5±0.2 degrees two-theta, 20.3±0.2 degrees two-theta, 20.7±0.2 degrees two-theta, 21.2±0.2 degrees two-theta, 22.2±0.2 degrees two-theta, and 25.1±0.2 degrees two-theta.

In some embodiments, crystalline Compound 41 Form A is characterized by an X-ray powder diffractogram substantially similar to FIG. 7.

Crystalline Compound 52 Form A (Neat)

Figure 9:
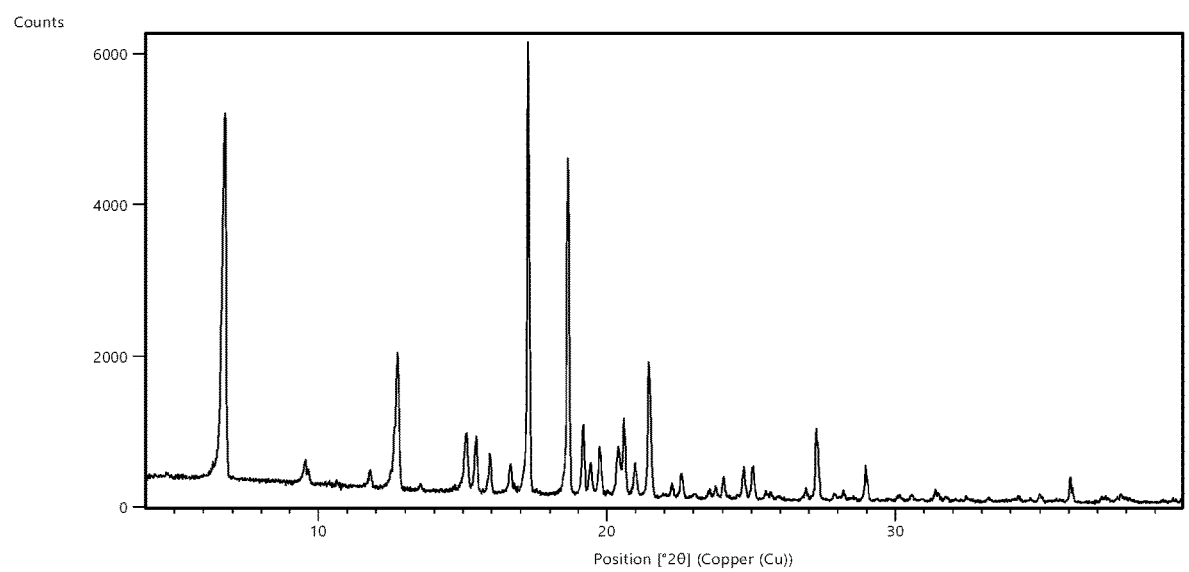
FIG. 9 provides an XRPD pattern of crystalline Compound 52 Form A (neat).

In some embodiments, the invention provides neat solid forms of Compound 52. In some embodiments, the invention provides neat crystalline forms of Compound 52. In some embodiments, the invention provides crystalline Compound 52 Form A (neat). FIG. 9 provides an X-ray powder diffractogram of crystalline Compound 52 Form A (neat).

In some embodiments, crystalline Compound 52 Form A (neat) is substantially pure. In some embodiments, crystalline Compound 52 Form A (neat) is substantially crystalline. In some embodiments, crystalline Compound 52 Form A (neat) is characterized by an X-ray powder diffractogram generated by an X-ray powder diffraction analysis with an incident beam of Cu Kα radiation.

In some embodiments, crystalline Compound 52 Form A (neat) is characterized by an X-ray powder diffractogram having a signal at one or more of 6.8±0.2 degrees two-theta, 17.3±0.2 degrees two-theta, and 18.6±0.2 degrees two-theta. In some embodiments, crystalline Compound 52 Form A (neat) is characterized by an X-ray powder diffractogram having a signal at two or more of 6.8±0.2 degrees two-theta, 17.3±0.2 degrees two-theta, and 18.6±0.2 degrees two-theta. In some embodiments, crystalline Compound 52 Form A (neat) is characterized by an X-ray powder diffractogram having a signal at 6.8±0.2 degrees two-theta, 17.3±0.2 degrees two-theta, and 18.6±0.2 degrees two-theta.

In some embodiments, crystalline Compound 52 Form A (neat) is characterized by an X-ray powder diffractogram having a signal at three or more of 6.8±0.2 degrees two-theta, 12.7±0.2 degrees two-theta, 17.3±0.2 degrees two-theta, 18.6±0.2 degrees two-theta, 20.6±0.2 degrees two-theta, and 21.4±0.2 degrees two-theta. In some embodiments, crystalline Compound 52 Form A (neat) is characterized by an X-ray powder diffractogram having a signal at four or more of 6.8±0.2 degrees two-theta, 12.7±0.2 degrees two-theta, 17.3±0.2 degrees two-theta, 18.6±0.2 degrees two-theta, 20.6±0.2 degrees two-theta, and 21.4±0.2 degrees two-theta. In some embodiments, crystalline Compound 52 Form A (neat) is characterized by an X-ray powder diffractogram having a signal at five or more of 6.8±0.2 degrees two-theta, 12.7±0.2 degrees two-theta, 17.3±0.2 degrees two-theta, 18.6±0.2 degrees two-theta, 20.6±0.2 degrees two-theta, and 21.4±0.2 degrees two-theta. In some embodiments, crystalline Compound 52 Form A (neat) is characterized by an X-ray powder diffractogram having a signal at 12.7±0.2 degrees two-theta, 17.3±0.2 degrees two-theta, 18.6±0.2 degrees two-theta, 20.6±0.2 degrees two-theta, and 21.4±0.2 degrees two-theta.

In some embodiments, crystalline Compound 52 Form A (neat) is characterized by an X-ray powder diffractogram having a signal at one, two, three, four, five, six, seven, eight, nine, ten, eleven, or more of 6.8±0.2 degrees two-theta, 12.7±0.2 degrees two-theta, 15.1±0.2 degrees two-theta, 15.5±0.2 degrees two-theta, 17.3±0.2 degrees two-theta, 18.6±0.2 degrees two-theta, 19.2±0.2 degrees two-theta, 19.7±0.2 degrees two-theta, 20.4±0.2 degrees two-theta, 20.6±0.2 degrees two-theta, 21.4±0.2 degrees two-theta, and 27.2±0.2 degrees two-theta.

In some embodiments, crystalline Compound 52 Form A (neat) is characterized by an X-ray powder diffractogram substantially similar to FIG. 9.

Amorphous Compound 60 (Neat Form)

Figure 12:
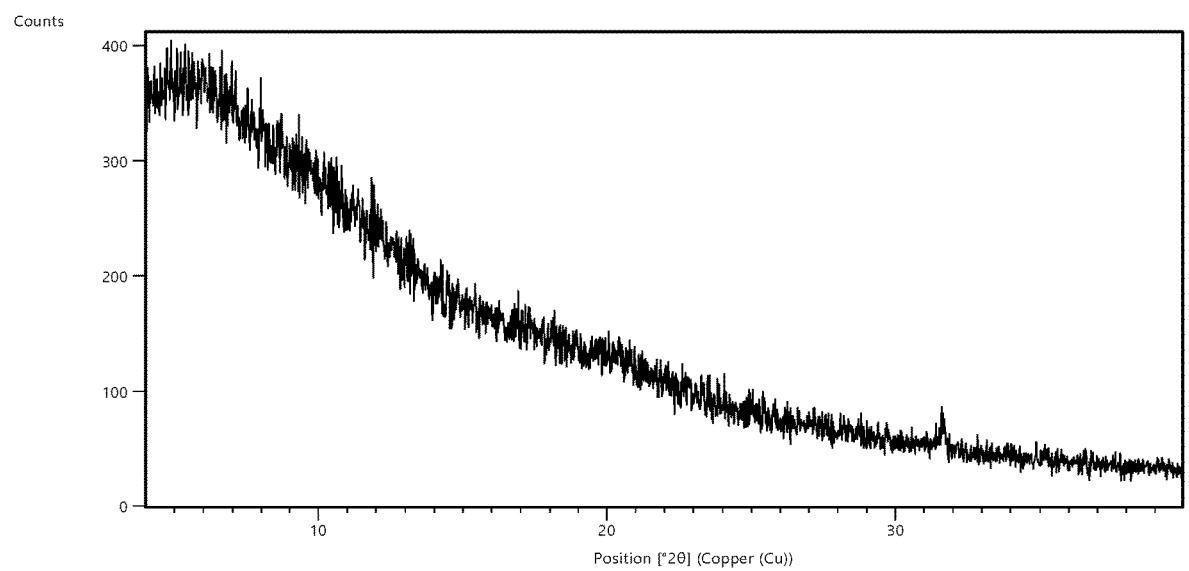
FIG. 12 provides an XRPD pattern of amorphous Compound 60 (neat form).

In some embodiments, the invention provides neat solid forms of Compound 60. In some embodiments, the invention provides a neat amorphous form of Compound 60. In some embodiments, the invention provides amorphous Compound 60 (neat form). FIG. 12 provides an X-ray powder diffractogram of amorphous Compound 60 (neat form) at room temperature.

In some embodiments, amorphous Compound 60 (neat form) is substantially pure. In some embodiments, amorphous Compound 60 (neat form) is substantially amorphous. In some embodiments, amorphous Compound 60 (neat form) is characterized by an X-ray powder diffractogram generated by an X-ray powder diffraction analysis with an incident beam of Cu Kα radiation.

In some embodiments, amorphous Compound 60 (neat form) is characterized by an X-ray powder diffractogram substantially similar to FIG. 12.

Amorphous Compound 70 (Neat Form)

Figure 15:
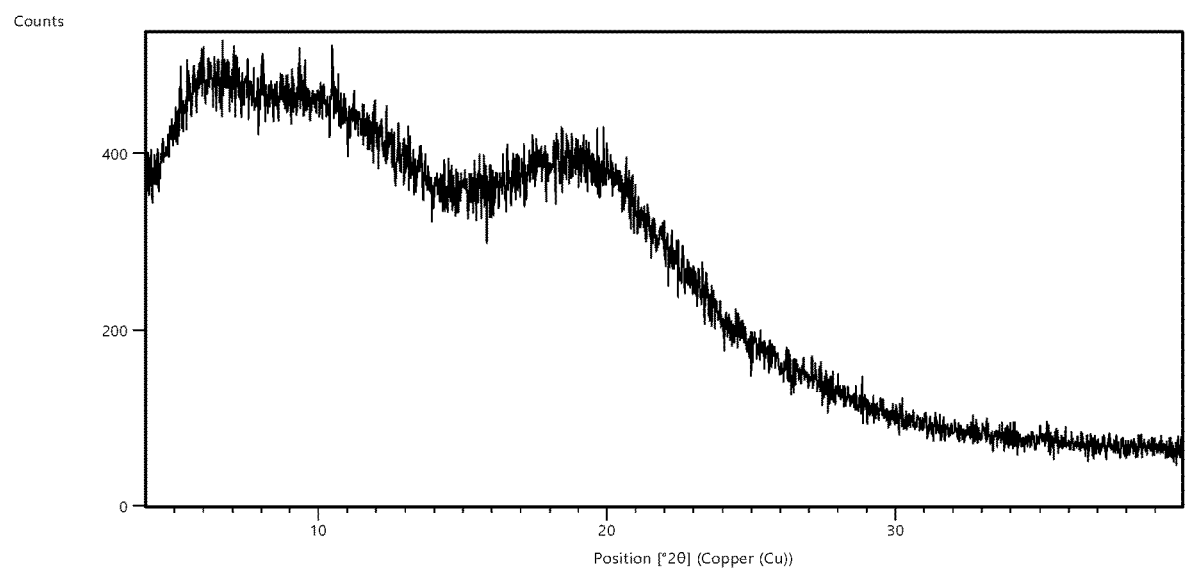
FIG. 15 provides an XRPD pattern of amorphous Compound 70 (neat form).

In some embodiments, the invention provides neat solid forms of Compound 70. In some embodiments, the invention provides a neat amorphous form of Compound 70. In some embodiments, the invention provides amorphous Compound 70 (neat form). FIG. 15 provides an X-ray powder diffractogram of amorphous Compound 70 (neat form) at room temperature.

In some embodiments, amorphous Compound 70 (neat form) is substantially pure. In some embodiments, amorphous Compound 70 (neat form) is substantially amorphous. In some embodiments, amorphous Compound 70 (neat form) is characterized by an X-ray powder diffractogram generated by an X-ray powder diffraction analysis with an incident beam of Cu Kα radiation.

In some embodiments, amorphous Compound 70 (neat form) is characterized by an X-ray powder diffractogram substantially similar to FIG. 15.

Crystalline Compound 163 Form A (Neat)

Figure 16:
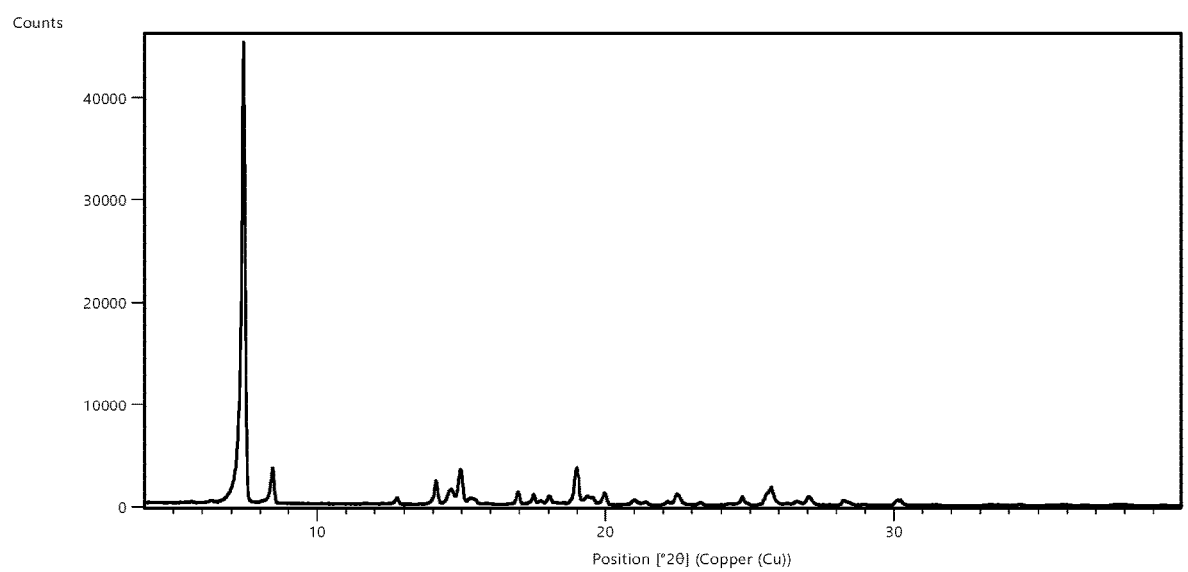
FIG. 16 provides an XRPD pattern of crystalline Compound 163 Form A (neat).

In some embodiments, the invention provides neat solid forms of Compound 163. In some embodiments, the invention provides neat crystalline forms of Compound 163. In some embodiments, the invention provides crystalline Compound 163 Form A (neat). FIG. 16 provides an X-ray powder diffractogram of crystalline Compound 163 Form A (neat).

In some embodiments, crystalline Compound 163 Form A (neat) is substantially pure. In some embodiments, crystalline Compound 163 Form A (neat) is substantially crystalline. In some embodiments, crystalline Compound 163 Form A (neat) is characterized by an X-ray powder diffractogram generated by an X-ray powder diffraction analysis with an incident beam of Cu Kα radiation.

In some embodiments, crystalline Compound 163 Form A (neat) is characterized by an X-ray powder diffractogram having a signal at 7.4±0.2 degrees two-theta.

In some embodiments, crystalline Compound 163 Form A (neat) is characterized by an X-ray powder diffractogram having a signal at one or more of 7.4±0.2 degrees two-theta, 8.4±0.2 degrees two-theta, and 15.0±0.2 degrees two-theta. In some embodiments, crystalline Compound 163 Form A (neat) is characterized by an X-ray powder diffractogram having a signal at two or more of 7.4±0.2 degrees two-theta, 8.4±0.2 degrees two-theta, and 15.0±0.2 degrees two-theta. In some embodiments, crystalline Compound 163 Form A (neat) is characterized by an X-ray powder diffractogram having a signal at 7.4±0.2 degrees two-theta, 8.4±0.2 degrees two-theta, and 15.0±0.2 degrees two-theta.

In some embodiments, crystalline Compound 163 Form A (neat) is characterized by an X-ray powder diffractogram having a signal at three or more of 7.4±0.2 degrees two-theta, 8.4±0.2 degrees two-theta, 14.1±0.2 degrees two-theta, 15.0±0.2 degrees two-theta, 19.1±0.2 degrees two-theta, and 25.8±0.2 degrees two-theta. In some embodiments, crystalline Compound 163 Form A (neat) is characterized by an X-ray powder diffractogram having a signal at four or more of 7.4±0.2 degrees two-theta, 8.4±0.2 degrees two-theta, 14.1±0.2 degrees two-theta, 15.0±0.2 degrees two-theta, 19.1±0.2 degrees two-theta, and 25.8±0.2 degrees two-theta. In some embodiments, crystalline Compound 163 Form A (neat) is characterized by an X-ray powder diffractogram having a signal at five or more of 7.4±0.2 degrees two-theta, 8.4±0.2 degrees two-theta, 14.1±0.2 degrees two-theta, 15.0±0.2 degrees two-theta, 19.1±0.2 degrees two-theta, and 25.8±0.2 degrees two-theta. In some embodiments, crystalline Compound 163 Form A (neat) is characterized by an X-ray powder diffractogram having a signal at 7.4±0.2 degrees two-theta, 8.4±0.2 degrees two-theta, 14.1±0.2 degrees two-theta, 15.0±0.2 degrees two-theta, 19.1±0.2 degrees two-theta, and 25.8±0.2 degrees two-theta.

In some embodiments, crystalline Compound 163 Form A (neat) is characterized by an X-ray powder diffractogram having a signal at one, two, three, four, five, six, seven, eight, nine, ten, or more of 7.4±0.2 degrees two-theta, 8.4±0.2 degrees two-theta, 14.1±0.2 degrees two-theta, 14.6±0.2 degrees two-theta, 15.0±0.2 degrees two-theta, 16.9±0.2 degrees two-theta, 19.1±0.2 degrees two-theta, 20.0±0.2 degrees two-theta, 22.5±0.2 degrees two-theta, 25.6±0.2 degrees two-theta, and 25.8±0.2 degrees two-theta.

In some embodiments, crystalline Compound 163 Form A (neat) is characterized by an X-ray powder diffractogram substantially similar to FIG. 16.

Amorphous Compound 173 (Neat Form) and Crystalline Compound 173 Form A (Neat)

Figure 18:
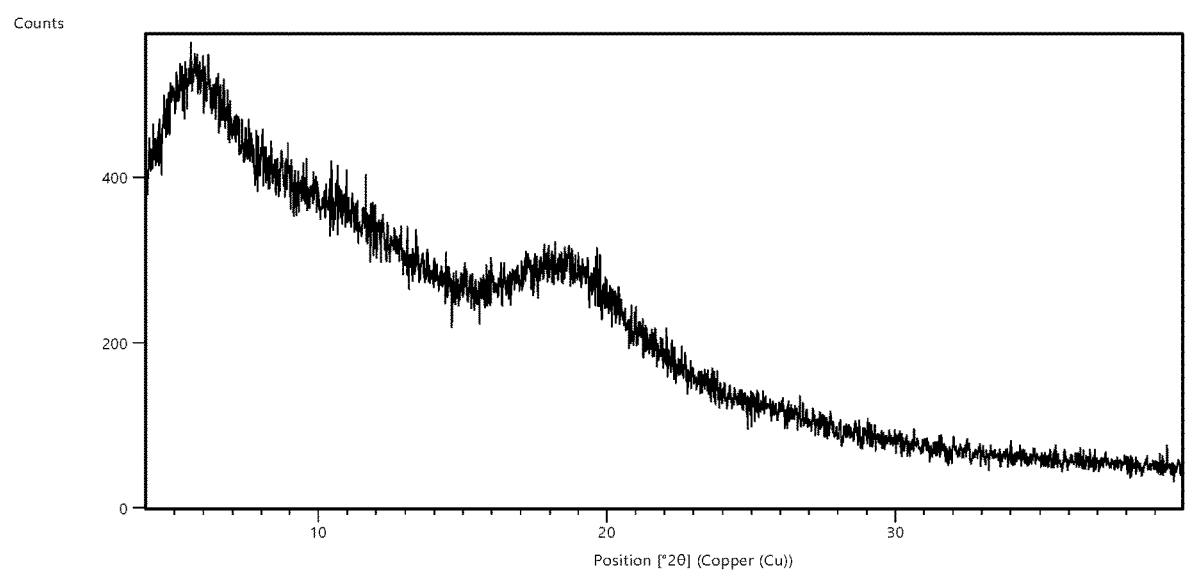
FIG. 18 provides an XRPD pattern of amorphous Compound 173 (neat form).

In some embodiments, the invention provides neat solid forms of Compound 173. In some embodiments, the invention provides a neat amorphous form of Compound 173. In some embodiments, the invention provides amorphous Compound 173 (neat form). FIG. 18 provides an X-ray powder diffractogram of amorphous Compound 173 (neat form) at room temperature.

In some embodiments, amorphous Compound 173 (neat form) is substantially pure. In some embodiments, amorphous Compound 173 (neat form) is substantially amorphous. In some embodiments, amorphous Compound 173 (neat form) is characterized by an X-ray powder diffractogram generated by an X-ray powder diffraction analysis with an incident beam of Cu Kα radiation.

In some embodiments, amorphous Compound 173 (neat form) is characterized by an X-ray powder diffractogram substantially similar to FIG. 18.

In some embodiments, the invention provides neat crystalline forms of Compound 173. In some embodiments, the invention provides crystalline Compound 173 Form A (neat).

In some embodiments, crystalline Compound 173 Form A (neat) is substantially pure. In some embodiments, crystalline Compound 173 Form A (neat) is substantially crystalline.

In some embodiments, crystalline Compound 173 Form A (neat) is characterized by a triclinic crystal system, a P1 space group, and the following unit cell dimensions measured at 150 K on a Bruker diffractometer utilizing Cu Kα radiation ($\lambda$=1.54178 Å):

| a | 6.7 ± .1 Å | α | 76.0 ± .1° |
|---|---|---|---|
| b | 11.9 ± .1 Å | β | 82.2 ± .1° |
| c | 13.1 ± .1 Å | γ | 85.4 ± .1°. |

Crystalline Compound 175 Form A (Neat)

In some embodiments, the invention provides neat solid forms of Compound 175. In some embodiments, the invention provides neat crystalline forms of Compound 175. In some embodiments, the invention provides crystalline Compound 175 Form A (neat).

In some embodiments, crystalline Compound 175 Form A (neat) is substantially pure. In some embodiments, crystalline Compound 175 Form A (neat) is substantially crystalline.

In some embodiments, crystalline Compound 175 Form A (neat) is characterized by an orthorhombic crystal system, a $P2_12_12_1$ space group, and the following unit cell dimensions measured at 100 K on a Bruker diffractometer utilizing Cu Kα radiation ($\lambda$=1.54178 Å):

| a | 9.8 ± .1 Å | α | 90° |
|---|---|---|---|
| b | 10.1 ± .1 Å | β | 90° |
| c | 20.5 ± .1 Å | γ | 90°. |

Crystalline Compound 188 Dichloromethane Solvate Form A

In some embodiments, the invention provides solvated crystalline forms of Compound 188. In some embodiments, the solvated crystalline form is a dichloromethane solvate. In some embodiments, the invention provides crystalline Compound 188 dichloromethane solvate Form A.

In some embodiments, crystalline Compound 188 dichloromethane solvate Form A is substantially pure. In some embodiments, crystalline Compound 188 dichloromethane solvate Form A is substantially crystalline.

In some embodiments, crystalline Compound 188 dichloromethane solvate Form A is characterized by a monoclinic crystal system, a $P2_1$ space group, and the following unit cell dimensions measured at 100 K on a Bruker diffractometer utilizing Cu Kα radiation ($\lambda$=1.54178 Å):

| a | 16.2 ± .1 Å | α | 90° |
|---|---|---|---|
| b | 13.3 ± .1 Å | β | 99.7 ± .1° |
| c | 23.2 ± .1 Å | γ | 90°. |

Methods of Treatment

Any of the novel compounds and solid forms disclosed herein, such as for example, compounds of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, deuterated derivatives thereof, and pharmaceutically acceptable salts of any of the foregoing can act as a CFTR modulator, i.e., it modulates CFTR activity in the body. Individuals suffering from a mutation in the gene encoding CFTR may benefit from receiving a CFTR modulator. A CFTR mutation may affect the CFTR quantity, i.e., the number of CFTR channels at the cell surface, or it may impact CFTR function, i.e., the functional ability of each channel to open and transport ions. Mutations affecting CFTR quantity include mutations that cause defective synthesis (Class I defect), mutations that cause defective processing and trafficking (Class II defect), mutations that cause reduced synthesis of CFTR (Class V defect), and mutations that reduce the surface stability of CFTR (Class VI defect). Mutations that affect CFTR function include mutations that cause defective gating (Class III defect) and mutations that cause defective conductance (Class IV defect). Some CFTR mutations exhibit characteristics of multiple classes. Certain mutations in the CFTR gene result in cystic fibrosis.

Thus, in some embodiments, the invention provides methods of treating, lessening the severity of, or symptomatically treating cystic fibrosis in a patient comprising administering to the patient an effective amount of any of the novel compounds and solid forms disclosed herein, such as for example, compounds of Formulae I, I', I'', Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, deuterated derivatives thereof, and pharmaceutically acceptable salts of any of the foregoing, alone or in combination with another active ingredient, such as another CFTR modulating agent. In some embodiments, the patient has an F508del/minimal function (MF) genotype, F508del/F508del genotype (homozygous for the F508del mutation), F508del/gating genotype, or F508del/residual function (RF) genotype. In some embodiments the patient is heterozygous and has one F508del mutation. In some embodiments the patient is homozygous for the N1303K mutation.

In some embodiments, 1 mg to 1000 mg of a compound disclosed herein, a deuterated derivative thereof or a pharmaceutically acceptable salt of the compound or deuterated derivative are administered daily.

In some embodiments, the patient is heterozygous and has an F508del mutation on one allele and a mutation on the other allele selected from Table 2:

TABLE 2

CFTR Mutations
Mutation

| | | | | |
|---|---|---|---|---|
| Q2X | L218X | Q525X | R792X | E1104X |
| S4X | Q220X | G542X | E822X | W1145X |
| W19X | Y275X | G550X | W882X | R1158X |
| G27X | C276X | Q552X | W846X | R1162X |
| Q39X | Q290X | R553X | Y849X | S1196X |
| W57X | G330X | E585X | R851X | W1204X |
| E60X | W401X | G673X | Q890X | L1254X |
| R75X | Q414X | Q685X | S912X | S1255X |
| L88X | S434X | R709X | Y913X | W1282X |
| E92X | S466X | K710X | Q1042X | Q1313X |
| Q98X | S489X | Q715X | W1089X | Q1330X |
| Y122X | Q493X | L732X | Y1092X | E1371X |
| E193X | W496X | R764X | W1098X | Q1382X |
| W216X | C524X | R785X | R1102X | Q1411X |
| 185 + 1G→T | 711 + 5G→A | 1717 − 8G→A | 2622 + 1G→A | 3121 − 1G→A |
| 296 + 1G→A | 712 − 1G→T | 1717 − 1G→A | 2790 − 1G→C | 3500 − 2A→G |
| 296 + 1G→T | 1248 + 1G→A | 1811 + 1G→C | 3040G→C | 3600 + 2insT |
| 405 + 1G→A | 1249 − 1G→A | 1811 + 1.6kbA→G | (G970R) | 3850 − 1G→A |
| 405 + 3A→C | 1341 + 1G→A | 1811 + 1643G→T | 3120G→A | 4005 + 1G→A |
| 406 − 1G→A | 1525 − 2A→G | 1812 − 1G→A | 3120 + 1G→A | 4374 + 1G→T |
| 621 + 1G→T | 1525 − 1G→A | 1898 + 1G→A | 3121 − 2A→G | |
| 711 + 1G→T | | 1898 + 1G→C | | |
| 182delT | 1078delT | 1677delTA | 2711delT | 3737delA |
| 306insA | 1119delA | 1782delA | 2732insA | 3791delC |
| 306delTAGA | 1138insG | 1824delA | 2869insG | 3821delT |
| 365-366insT | 1154insTC | 1833delT | 2896insAG | 3876delA |
| 394delTT | 1161delC | 2043delG | 2942insT | 3878delG |
| 442delA | 1213delT | 2143delT | 2957delT | 3905insT |
| 444delA | 1259insA | 2183AA→G | 3007delG | 4016insT |
| 457TAT→G | 1288insTA | 2184delA | 3028delA | 4021dupT |
| 541delC | 1343delG | 2184insA | 3171delC | 4022insT |
| 574delA | 1471delA | 2307insA | 3171insC | 4040delA |
| 663delT | 1497delGG | 2347delG | 3271delGG | 4279insA |
| 849delG | 1548delG | 2585delT | 3349insT | 4326delTC |
| 935delA | 1609del CA | 2594delGT | 3659delC | |
| CFTRdele1 | | CFTRdele16-17b | 1461ins4 | |
| CFTRdele2 | | CFTRdele17a, 17b | 1924del7 | |
| CFTRdele2, 3 | | CFTRdele17a-18 | 2055del9→A | |
| CFTRdele2-4 | | CFTRdele19 | 2105-2117del13insAGAAA | |
| CFTRdele3-10, 14b-16 | | CFTRdele19-21 | 2372del8 | |
| CFTRdele4-7 | | CFTRdele21 | 2721del11 | |
| CFTRdele4-11 | | CFTRdele22-24 | 2991del32 | |
| CFTR50kbdel | | CFTRdele22, 23 | 3667ins4 | |
| CFTRdup6b-10 | | 124del23bp | 4010del4 | |
| CFTRdele11 | | 602del14 | 4209TGTT→AA | |
| CFTRdele13, 14a | | 852del22 | | |
| CFTRdele14b-17b | | 991del5 | | |
| A46D | V520F | Y569D | N1303K | |
| G85E | A559T | L1065P | | |
| R347P | R560T | R1066C | | |
| L467P | R560S | L1077P | | |
| I507del | A561E | M1101K | | |

In some embodiments, the disclosure also is directed to methods of treatment using isotope-labelled compounds of the afore-mentioned compounds, or pharmaceutically acceptable salts thereof, wherein the formula and variables of such compounds and salts are each and independently as described above or any other embodiments described above, provided that one or more atoms therein have been replaced by an atom or atoms having an atomic mass or mass number which differs from the atomic mass or mass number of the atom which usually occurs naturally (isotope labelled). Examples of isotopes which are commercially available and suitable for the disclosure include isotopes of hydrogen, carbon, nitrogen, oxygen, phosphorus, fluorine and chlorine, for example $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively.

The isotope-labelled compounds and salts can be used in a number of beneficial ways. They can be suitable for medicaments and/or various types of assays, such as substrate tissue distribution assays. For example, tritium ($^{3}H$)— and/or carbon-14 ($^{14}C$)-labelled compounds are particularly useful for various types of assays, such as substrate tissue distribution assays, due to relatively simple preparation and excellent detectability. For example, deuterium ($^{2}H$)-labelled ones are therapeutically useful with potential therapeutic advantages over the non-$^{2}H$-labelled compounds. In general, deuterium ($^{2}H$)-labelled compounds and salts can have higher metabolic stability as compared to those that are not isotope-labelled owing to the kinetic isotope effect described below. Higher metabolic stability translates directly into an increased in vivo half-life or lower dosages, which could be desired. The isotope-labelled compounds and salts can usually be prepared by carrying out the procedures disclosed in the synthesis schemes and the related description, in the example part and in the preparation part in the present text, replacing a non-isotope-labelled reactant by a readily available isotope-labelled reactant.

In some embodiments, the isotope-labelled compounds and salts are deuterium ($^{2}H$)-labelled ones. In some specific embodiments, the isotope-labelled compounds and salts are deuterium ($^{2}H$)-labelled, wherein one or more hydrogen atoms therein have been replaced by deuterium. In chemical structures, deuterium is represented as "$^{2}H$" or "D."

When discovering and developing therapeutic agents, the person skilled in the art attempts to optimize pharmacokinetic parameters while retaining desirable in vitro properties. It may be reasonable to assume that many compounds with poor pharmacokinetic profiles are susceptible to oxidative metabolism.

The deuterium ($^{2}H$)-labelled compounds and salts can modulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. For a further discussion, see S. L. Harbeson and R. D. Tung, *Deuterium In Drug Discovery and Development*, Ann. Rep. Med. Chem. 2011, 46, 403-417, which is incorporated herein by reference.

The concentration of the isotope(s) (e.g., deuterium) incorporated into the isotope-labelled compounds and salt of the disclosure may be defined by the isotopic enrichment factor. The term "isotopic enrichment factor" as used herein means the ratio between the isotopic abundance and the natural abundance of a specified isotope. In some embodiments, if a substituent in a compound of the disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Combination Therapies

One aspect disclosed herein provides methods of treating cystic fibrosis and other CFTR-mediated diseases using any of the novel compounds and solid forms disclosed herein, such as for example, compounds of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, deuterated derivatives thereof, and pharmaceutically acceptable salts of any of the foregoing, in combination with at least one additional active pharmaceutical ingredient.

Thus, in some embodiments, the invention provides methods of treating, lessening the severity of, or symptomatically treating cystic fibrosis in a patient comprising administering to the patient an effective amount of any of the novel compounds and solid forms disclosed herein, such as for example, compounds of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, deuterated derivatives thereof, and pharmaceutically acceptable salts of any of those compounds and deuterated derivatives, alone or in combination with at least one additional active pharmaceutical ingredient, such as, e.g., a CFTR modulating agent.

In some embodiments, at least one additional active pharmaceutical ingredient is selected from mucolytic agents, bronchodilators, antibiotics, anti-infective agents, and anti-inflammatory agents.

In some embodiments, the additional therapeutic agent is an antibiotic. Exemplary antibiotics useful herein include tobramycin, including tobramycin inhaled powder (TIP), azithromycin, aztreonam, including the aerosolized form of aztreonam, amikacin, including liposomal formulations thereof, ciprofloxacin, including formulations thereof suitable for administration by inhalation, levoflaxacin, including aerosolized formulations thereof, and combinations of two antibiotics, e.g., fosfomycin and tobramycin.

In some embodiments, the additional agent is a mucolyte. Exemplary mucolytes useful herein includes Pulmozyme®.

In some embodiments, the additional agent is a bronchodilator. Exemplary bronchodilators include albuterol, metaprotenerol sulfate, pirbuterol acetate, salmeterol, or tetrabuline sulfate.

In some embodiments, the additional agent is an anti-inflammatory agent, i.e., an agent that can reduce the inflammation in the lungs. Exemplary such agents useful herein include ibuprofen, docosahexanoic acid (DHA), sildenafil, inhaled glutathione, pioglitazone, hydroxychloroquine, or simavastatin.

In some embodiments, the additional agent is a nutritional agent. Exemplary nutritional agents include pancrelipase (pancreating enzyme replacement), including Pancrease®, Pancreacarb®, Ultrase®, or Creon®, Liprotomase® (formerly Trizytek®), Aquadeks®, or glutathione inhalation. In one embodiment, the additional nutritional agent is pancrelipase.

In some embodiments, at least one additional active pharmaceutical ingredient is selected from CFTR modulating agents. In some embodiments, the CFTR modulating agent is a CFTR corrector. In some embodiments, the CFTR modulating agent is a CFTR potentiator enhancer/co-potentiator (for example, ASP-11). In some embodiments, the at least one additional active pharmaceutical ingredient is a CFTR amplifier. In some embodiments, the at least one additional active pharmaceutical ingredient is a CFTR read-through agent. In some embodiments, the at least one additional active pharmaceutical ingredient is a CFTR nucleic acid therapy.

In some embodiments, the at least one additional active pharmaceutical ingredient is a ENaC inhibitor. In some embodiments, the at least one additional active pharmaceutical ingredient is a TMEM16A modulator. In some embodiments, the at least one additional active pharmaceutical ingredient is a GPR39 agonist.

In some embodiments, the at least one additional active pharmaceutical ingredient is chosen from (a) Compound II and deuterated derivatives and pharmaceutically acceptable salts thereof; (b) Compound IV and deuterated derivatives and pharmaceutically acceptable salts thereof; (c) Compound V and deuterated derivatives and pharmaceutically acceptable salts thereof; (d) Compound VI and deuterated derivatives and pharmaceutically acceptable salts thereof; (e) Compound VII and deuterated derivatives and pharmaceutically acceptable salts thereof; and (f) Compound VIII and deuterated derivatives and pharmaceutically acceptable salts thereof. Thus, in some embodiments, the combination therapies provided herein comprise a compound selected from compounds and solid forms of Formulae I, I', I", Ia, Ia', IIa, IIa', IIb IIb', IIc, IIc', IId, IId', IIe, IIe', IIf, IIf', IIg, IIg', IIh, IIh', Compounds 1 to 213, Compounds 214 to 222, deuterated derivatives of those compounds, and pharmaceutically acceptable salts of any of the foregoing compounds and deuterated derivatives; and at least one compound chosen from Compound II, Compound IV, Compound V, Compound VI, Compound VII, Compound VIII, Compound IX, Compound X, and deuterated derivatives and pharmaceutically acceptable salts thereof. In some embodiments, the combination therapies provided herein comprise (a) at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, deuterated derivatives of those compounds, and pharmaceutically acceptable salts of any of the foregoing compounds and deuterated derivatives; (b) at least one compound chosen from Compound II, Compound IV, and pharmaceutically acceptable salts and deuterated derivatives thereof; and (c) at least one compound chosen from Compound V, Compound VI, Compound VII, Compound VIII, Compound IX, Compound X, and deuterated derivatives and pharmaceutically acceptable salts thereof. In some embodiments, the combination therapies provided herein comprise (a) at least one compound chosen from compounds and solid forms of Formulae I, I', I", Ia, Ia, IIa, IIa', IIb, IIb', IIc, IIc', IId, IId', IIe, IIe', IIg, IIg', IIh, IIh', Compounds 1 to 213, Compounds 214 to 222, deuterated derivatives of those compounds, and pharmaceutically acceptable salts of any of the foregoing compounds and deuterated derivatives; (b) at least one compound selected from Compound II and pharmaceutically acceptable salts and deuterated derivatives thereof; and (c) at least one compound chosen from Compound VII and deuterated derivatives and pharmaceutically acceptable salts thereof.

In some embodiments, the combination therapies provided herein comprise (a) a compound selected from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, deuterated derivatives of those compounds, and pharmaceutically acceptable salts of any of the foregoing compounds and deuterated derivatives; (b) at least one compound chosen from Compound II, Compound IV, Compound V, Compound VI, Compound VII, Compound VIII, Compound IX, Compound X, and deuterated derivatives and pharmaceutically acceptable salts thereof; and (c) at least one compound chosen from compounds disclosed in WO 2016/105485, United States Patent Application Publication No. 2016-0120841, United States Patent Application Publication No. 2017-0101405, WO 2017/009804, WO 2018/065921, WO 2017/062581; Phuan, P.-W. et al. *J. Cyst. Fibros.* 2018, 17 (5), 595-606; Pedemonte, N. et al. *Sci. Adv.* 2020, 6 (8), eaay9669; Phuan, P.-W. et al. *Sci. Rep.* 2019, 9 (1), 17640; Bose, S. et al. *J. Cyst. Fibros.* 2020, 19 Suppl 1, S25-S32; Crawford, D. K. *J. Pharmacol. Exp. Ther.* 2020, 374 (2), 264-272; Brasell, E. J. et al. *PLoS One* 2019, 14 (12), e0223954; Smith, N. J, Solovay, C. F., *Pharm. Pat. Anal.* 2017, 6 (4), 179-188; Kunzelmann, K. et al., *Front. Pharmacol.* 2019, 10, 3; or Son, J.-H. et al., *Eur. J. of Med. Chem.* 2020, 112888.

In some embodiments, the combination therapies provided herein comprise (a) a compound selected from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, deuterated derivatives of those compounds, and pharmaceutically acceptable salts of any of the foregoing compounds and deuterated derivatives; (b) at least one compound chosen from Compound II, Compound IV, Compound V, Compound VI, Compound VII, Compound VIII, Compound IX, Compound X, and deuterated derivatives and pharmaceutically acceptable salts thereof; and (c) at least one compound chosen from PTI-428, ASP-11, ABBV-2222, ABBV-2851, GLPG2737, ABBV-3221, ABBV-3748, ABBV-3903, ABBV-119, FDL-169, ARN5562, ARN21586, ARN22081, ARN22652, ARN23765, ARN23766, PTI-801, FDL-176, PTI-808, GLPG1837, GLPG2451/ABBV-2451 (Icenticaftor), GLPG3067/ABBV-3067 (Navocaftor), ABBV-191, ELX-02, MRT5005, Lunar-CF, RCT223, amiloride, ETD001, $CF_{552}$, GS-9411, GS-5737, P-1037 (VX-371), P-1055 (VX-551), AZD5634, SPX-101, Ionis-ENaC-2.5 Rx, BI 1265162, AZ5634, ARO-ENaC1001, ETD002, and DS-1039.

In some embodiments, the combination therapies provided herein comprise (a) a compound selected from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, deuterated derivatives of those compounds, and pharmaceutically acceptable salts of any of the foregoing compounds and deuterated derivatives; and (b) at least two compounds chosen from compounds disclosed in WO 2019/195739, WO 2019/200246, WO 2021/030555, WO 2021/030556, WO 2010/053471, WO 2011/119984, WO 2011/133751, WO 2011/133951, WO 2015/160787, WO 2007/056341, WO 2009/073757, WO 2009/076142, WO 2018/107100, WO 2019/113476, WO 2018/064632, WO 2019/152940, WO 2016/057572, WO 2021/030554, WO 2020/206080, WO 2016/105485, United States Patent Application Publication No. 2016-0120841, United States Patent Application Publication No. 2017-0101405, WO 2017/009804, WO 2018/065921, WO 2017/062581; Phuan, P.-W. et al. *J. Cyst. Fibros.* 2018, 17 (5), 595-606; Pedemonte, N. et al. *Sci. Adv.* 2020, 6 (8), eaay9669; Phuan, P.-W. et al. *Sci. Rep.* 2019, 9 (1), 17640; Bose, S. et al. *J. Cyst. Fibros.* 2020, 19 Suppl 1, S25-S32; Crawford, D. K. *J. Pharmacol. Exp. Ther.* 2020, 374 (2), 264-272; Brasell, E. J. et al. *PLoS One* 2019, 14 (12), e0223954; Smith, N. J, Solovay, C. F., *Pharm. Pat. Anal.* 2017, 6 (4), 179-188; Kunzelmann, K. et al., *Front. Pharmacol.* 2019, 10, 3; or Son, J.-H. et al., *Eur. J. of Med. Chem.* 2020, 112888.

In some embodiments, the combination therapies provided herein comprise (a) a compound selected from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, deuterated derivatives of those compounds, and pharmaceutically acceptable salts of any of the foregoing compounds and deuterated derivatives; and (b) at least two compounds chosen from Compound II, Compound IV, Compound V, Compound VI, Compound VII, Compound VIII, Compound IX, Compound X, PTI-428, ASP-11, ABBV-2222, ABBV-2851, GLPG2737, ABBV-3221, ABBV-3748, ABBV-3903, ABBV-119, FDL-169, ARN5562, ARN21586, ARN22081, ARN22652, ARN23765, ARN23766, PTI-801, FDL-176, PTI-808, GLPG1837, GLPG2451/ABBV-2451 (Icenticaftor), GLPG3067/ABBV-3067 (Navocaftor), ABBV-191, ELX-02, MRT5005, Lunar-CF, RCT223, amiloride, ETD001, CF552, GS-9411, GS-5737, P-1037 (VX-371), P-1055 (VX-551), AZD5634, SPX-101, Ionis-ENaC-2.5 Rx, BI 1265162, AZ5634, ARO-ENaC1001, ETD002, and DS-1039, and deuterated derivatives and pharmaceutically acceptable salts thereof.

In some embodiments, at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, deuterated derivatives of those compounds, and pharmaceutically acceptable salts of any of the foregoing compounds and deuterated derivatives, is administered in combination with at least one compound chosen from Compound II and deuterated derivatives and pharmaceutically acceptable salts thereof. In some embodiments, at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, deuterated derivatives of those compounds, and pharmaceutically acceptable salts of those compounds and deuterated derivatives, is administered in combination with at least one compound chosen from Compound IV and deuterated derivatives and pharmaceutically acceptable salts thereof. In some embodiments, at least one compound chosen from compounds and solid forms Formulae I, I', I", Ia, Ia', IIa, IIa', IIb, IIc, IIc', IId, IId', IIe, IIe', IIf, IIf', IIg, IIg', IIh, IIh', Compounds 1 to 213, Compounds 214 to 222, deuterated derivatives of those compounds, and pharmaceutically acceptable salts of those compounds and deuterated derivatives, is administered in combination with at least one compound chosen from Compound V and deuterated derivatives and pharmaceutically acceptable slats thereof. In some embodiments, at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, deuterated derivatives of those compounds, and pharmaceutically acceptable salts of any of those compounds and deuterated derivatives, is administered in combination with at least one compound chosen from Compound VI and deuterated derivatives and pharmaceutically acceptable salts thereof. In some embodiments, at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, deuterated derivatives of those compounds, and pharmaceutically acceptable salts of any of the foregoing compounds and deuterated derivatives, is administered in combination with at least one compound chosen from Compound VII and deuterated derivatives and pharmaceutically acceptable salts thereof. In some embodiments, at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, deuterated derivatives of those compounds, and pharmaceutically acceptable salts of any of the foregoing compounds and deuterated derivatives, is administered in combination with at least one compound chosen from Compound VIII and deuterated derivatives and pharmaceutically acceptable salts thereof.

Each of the compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, Compound II, Compound IV, Compound V, Compound VI, Compound VII, Compound VIII, Compound IX, Compound X, and their deuterated derivatives and pharmaceutically acceptable salts thereof, independently can be administered once daily, twice daily, or three times daily. In some embodiments, at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof is administered once daily. In some embodiments, at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof is administered twice daily. In some embodiments, at least one compound chosen from compounds and solid forms of Formulae I, I', I", Ia, Ia, IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof and at least one compound chosen from Compound II and pharmaceutically acceptable salts thereof are administered once daily. In some embodiments, at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof and at least one compound chosen from Compound II and pharmaceutically acceptable salts thereof are administered twice daily. In some embodiments, at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof and at least one compound chosen from Compound IV and pharmaceutically acceptable salts thereof are administered once daily. In some embodiments, at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof and at least one compound chosen from Compound IV and pharmaceutically acceptable salts thereof are administered twice daily. In some embodiments, at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof and at least one compound chosen from Compound V and pharmaceutically acceptable salts thereof are administered once daily. In some embodiments, at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof and at least one compound chosen from Compound V and pharmaceutically acceptable salts thereof are administered twice daily. In some embodiments, at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof and at least one compound chosen from Compound VI and pharmaceutically acceptable salts thereof are administered once daily. In some embodiments, at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof and at least one compound chosen from Compound VI and pharmaceutically acceptable salts thereof are administered twice daily. In some embodiments, at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof and at least one compound chosen from Compound VII and pharmaceutically acceptable salts thereof are administered once daily. In some embodiments, at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof and at least one compound chosen from Compound VII and pharmaceutically acceptable salts thereof are administered twice daily. In some embodiments, at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof and at least one compound chosen from Compound VIII and pharmaceutically acceptable salts thereof are administered once daily. In some embodiments, at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof and at least one compound chosen from Compound VIII and pharmaceutically acceptable salts thereof are administered twice daily.

In some embodiments, at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof; at least one compound chosen from Compound II, Compound IV, and pharmaceutically acceptable salts thereof; and at least one compound chosen from Compound V, Compound VI, Compound VII, Compound VIII, Compound IX, Compound X, and pharmaceutically acceptable salts thereof are administered once daily. In some embodiments, at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof; at least one compound chosen from Compound II, Compound IV, and pharmaceutically acceptable salts thereof; and at least one compound chosen from Compound V, Compound VI, Compound VII, Compound VIII, Compound IX, Compound X, and pharmaceutically acceptable salts thereof are administered twice daily. In some embodiments, at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof; at least one compound chosen from Compound II and pharmaceutically acceptable salts thereof; and at least one compound chosen from Compound VII and pharmaceutically acceptable salts thereof are administered once daily. In some embodiments, at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof; at least one compound chosen from Compound II and pharmaceutically acceptable salts thereof; and at least one compound chosen from Compound VII and pharmaceutically acceptable salts thereof are administered twice daily.

Compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, Compound II, Compound IV, Compound V, Compound VI, Compound VII, Compound VIII, Compound IX, Compound X, and their deuterated derivatives and pharmaceutically acceptable salts thereof can be administered in a single pharmaceutical composition or separate pharmaceutical compositions. Such pharmaceutical compositions can be administered once daily or multiple times daily, such as twice daily. As used herein, the phrase that a given amount of API (e.g., Compound II, Compound VII, or pharmaceutically acceptable salts thereof) is administered once or twice daily or per day means that said given amount is administered per dosing, which may occur once or twice daily.

In some embodiments, at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof is administered in a first pharmaceutical composition; and at least one compound chosen from Compound VII and pharmaceutically acceptable salts thereof is administered in a second pharmaceutical composition.

In some embodiments, at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof is administered in a first pharmaceutical composition; at least one compound chosen from Compound II and pharmaceutically acceptable salts thereof is administered in a second pharmaceutical composition; and at least one compound chosen from Compound VII and pharmaceutically acceptable salts thereof is administered in a third pharmaceutical composition.

Any suitable pharmaceutical compositions known in the art can be used for compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, Compound II, Compound IV, Compound V, Compound VI, Compound VII, Compound VIII, Compound IX, Compound X, and deuterated derivatives and pharmaceutically acceptable salts thereof. Some exemplary pharmaceutical compositions for Compound II and its pharmaceutically acceptable salts can be found in WO 2011/119984 and WO 2014/014841, incorporated herein by reference. Some exemplary pharmaceutical compositions for Compound III and its pharmaceutically acceptable salts can be found in WO 2007/134279, WO 2010/019239, WO 2011/019413, WO 2012/027731, and WO 2013/130669, and some exemplary pharmaceutical compositions for Compound III-d and its pharmaceutically acceptable salts can be found in U.S. Pat. Nos. 8,865,902, 9,181,192, 9,512,079, WO 2017/053455, and WO 2018/080591, all of which are incorporated herein by reference. Some exemplary pharmaceutical compositions for Compound IV and its pharmaceutically acceptable salts can be found in WO 2010/037066, WO 2011/127421, and WO 2014/071122, incorporated herein by reference. Some exemplary pharmaceutical compositions for Compound V and its pharmaceutically acceptable salts can be found in WO 2019/152940, incorporated herein by reference. Some exemplary pharmaceutical compositions for Compound VI and its pharmaceutically acceptable salts can be found in WO 2019/079760, incorporated herein by reference.

Pharmaceutical Compositions

Another aspect of the invention provides a pharmaceutical composition comprising at least one compound chosen from compounds and solid forms of Formulae I, I', I", Ia, Ia', IIa, IIa', IIb, IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof, and at least one pharmaceutically acceptable carrier.

In some embodiments, the invention provides pharmaceutical compositions comprising at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof in combination with at least one additional active pharmaceutical ingredient. In some embodiments, the at least one additional active pharmaceutical ingredient is a CFTR modulator. In some embodiments, the at least one additional active pharmaceutical ingredient is a CFTR corrector. In some embodiments, the at least one additional active pharmaceutical ingredient is a CFTR potentiator. In some embodiments, the at least one additional active pharmaceutical ingredient is a compound that enhances CFTR potentiation, i.e., a CFTR potentiator enhancer/co-potentiator. In some embodiments, the at least one additional active pharmaceutical ingredient is a CFTR amplifier. In some embodiments, the at least one additional active pharmaceutical ingredient is a CFTR readthrough agent. In some embodiments, the at least one additional active pharmaceutical ingredient is a CFTR nucleic acid therapy. In some embodiments, the at least one additional active pharmaceutical ingredient is a ENaC inhibitor. In some embodiments, the at least one additional active pharmaceutical ingredient is a TMEM16A modulator. In some embodiments, the at least one additional active pharmaceutical ingredient is a GPR39 agonist. In some embodiments, the pharmaceutical composition comprises at least one compound chosen from compounds and solid forms of Formulae I, I', I", Ia, Ia', IIa, IIa', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof and at least two additional active pharmaceutical ingredients, each of which is a CFTR corrector. In some embodiments, the pharmaceutical composition comprises at least one compound chosen from compounds and solid forms of Formulae I, I', I", Ia, Ia, IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof and at least two additional active pharmaceutical ingredients, one of which is a CFTR corrector and one of which is a CFTR potentiator enhancer.

In some embodiments, the invention provides a pharmaceutical composition comprising (a) at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof, (b) at least one compound chosen from Compound II, Compound IV, Compound V, Compound VI, Compound VII, Compound VIII, Compound IX, Compound X, and pharmaceutically acceptable salts thereof, and (c) at least one pharmaceutically acceptable carrier.

In some embodiments, the invention provides a pharmaceutical composition comprising (a) at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof, (b) at least one compound chosen from Compound II and pharmaceutically acceptable salts thereof, and (c) at least one pharmaceutically acceptable carrier.

In some embodiments, the invention provides a pharmaceutical composition comprising (a) at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof, (b) at least one compound chosen from Compound VII and pharmaceutically acceptable salts thereof, and (c) at least one pharmaceutically acceptable carrier.

In some embodiments, the disclosure provides a pharmaceutical composition comprising (a) at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof, (b) at least one compound chosen from Compound II, Compound IV, and pharmaceutically acceptable salts thereof, (c) at least one compound chosen from Compound V, Compound VI, Compound VII, Compound VIII, Compound IX, Compound X, and pharmaceutically acceptable salts thereof, and (d) at least one pharmaceutically acceptable carrier.

In some embodiments, the disclosure provides a pharmaceutical composition comprising (a) at least one compound chosen from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof, (b) at least one compound chosen from Compound II and pharmaceutically acceptable salts thereof, (c) at least one compound chosen from Compound VII and pharmaceutically acceptable salts thereof, and (d) at least one pharmaceutically acceptable carrier.

In some embodiments, the pharmaceutical compositions provided herein comprise (a) a compound selected from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof; (b) at least one compound chosen from Compound II, Compound IV, Compound V, Compound VI, Compound VII, Compound VIII, Compound IX, Compound X, and pharmaceutically acceptable salts and deuterated derivatives thereof; (c) at least one compound chosen from compounds disclosed in WO 2016/105485, United States Patent Application Publication No. 2016-0120841, United States Patent Application Publication No. 2017-0101405, WO 2017/009804, WO 2018/065921, WO 2017/062581; Phuan, P.-W. et al. *J. Cyst. Fibros.* 2018, 17 (5), 595-606; Pedemonte, N. et al. *Sci. Adv.* 2020, 6 (8), eaay9669; Phuan, P.-W. et al. *Sci. Rep.* 2019, 9 (1), 17640; Bose, S. et al. *J. Cyst. Fibros.* 2020, 19 Suppl 1, S25-S32; Crawford, D. K. *J. Pharmacol. Exp. Ther.* 2020, 374 (2), 264-272; Brasell, E. J. et al. *PLoS One* 2019, 14 (12), e0223954; Smith, N. J, Solovay, C. F., *Pharm. Pat. Anal.* 2017, 6 (4), 179-188; Kunzelmann, K. et al., *Front. Pharmacol.* 2019, 10, 3; or Son, J.-H. et al., *Eur. J. of Med. Chem.* 2020, 112888; and (d) at least one pharmaceutically acceptable carrier.

In some embodiments, the pharmaceutical compositions provided herein comprise (a) a compound selected from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof; (b) at least one compound chosen from Compound II, Compound IV, Compound V, Compound VI, Compound VII, Compound VIII, Compound IX, Compound X, and pharmaceutically acceptable salts and deuterated derivatives thereof; (c) at least one compound chosen from PTI-428, ASP-11, ABBV-2222, ABBV-2851, GLPG2737, ABBV-3221, ABBV-3748, ABBV-3903, ABBV-119, FDL-169, ARN5562, ARN21586, ARN22081, ARN22652, ARN23765, ARN23766, PTI-801, FDL-176, PTI-808, GLPG1837, GLPG2451/ABBV-2451 (Icenticaftor), GLPG3067/ABBV-3067 (Navocaftor), ABBV-191, ELX-02, MRT5005, Lunar-CF, RCT223, amiloride, ETD001, $CF_{552}$, GS-9411, GS-5737, P-1037 (VX-371), P-1055 (VX-551), AZD5634, SPX-101, Ionis-ENaC-2.5 Rx, BI 1265162, AZ5634, ARO-ENaC1001, ETD002, and DS-1039; and (d) at least one pharmaceutically acceptable carrier.

In some embodiments, the pharmaceutical compositions provided herein comprise (a) a compound selected from compounds and solid forms of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof; (b) at least two compounds chosen from compounds disclosed in WO 2019/195739, WO 2019/200246, WO 2021/030555, WO 2021/030556, WO 2010/053471, WO 2011/119984, WO 2011/133751, WO 2011/133951, WO 2015/160787, WO 2007/056341, WO 2009/073757, WO 2009/076142, WO 2018/107100, WO 2019/113476, WO 2018/064632, WO 2019/152940, WO 2016/057572, WO 2021/030554, WO 2020/206080, WO 2016/105485, United States Patent Application Publication No. 2016-0120841, United States Patent Application Publication No. 2017-0101405, WO 2017/009804, WO 2018/065921, WO 2017/062581; Phuan, P.-W. et al. *J. Cyst. Fibros.* 2018, 17 (5), 595-606; Pedemonte, N. et al. *Sci. Adv.* 2020, 6 (8), eaay9669; Phuan, P.-W. et al. *Sci. Rep.* 2019, 9 (1), 17640; Bose, S. et al. *J. Cyst. Fibros.* 2020, 19 Suppl 1, S25-S32; Crawford, D. K. *J. Pharmacol. Exp. Ther.* 2020, 374 (2), 264-272; Brasell, E. J. et al. *PLoS One* 2019, 14 (12), e0223954; Smith, N. J, Solovay, C. F., *Pharm. Pat. Anal.* 2017, 6 (4), 179-188; Kunzelmann, K. et al., *Front. Pharmacol.* 2019, 10, 3; or Son, J.-H. et al., *Eur. J. of Med. Chem.* 2020, 112888; and (c) at least one pharmaceutically acceptable carrier.

In some embodiments, the pharmaceutical compositions provided herein comprise (a) a compound selected from compounds and solid forms of Formulae I, I', I", Ia, Ia, IIa, IIa', IIb, IIb', IIc, IIc', IId, IId', IIe, IIe', IIf, IIf', IIg, IIg', IIh, IIh', Compounds 1 to 213, Compounds 214 to 222, and deuterated derivatives and pharmaceutically acceptable salts thereof; (b) at least two compounds chosen from Compound II, Compound IV, Compound V, Compound VI, Compound VII, Compound VIII, Compound IX, Compound X, PTI-428, ASP-11, ABBV-2222, ABBV-2851, GLPG2737, ABBV-3221, ABBV-3748, ABBV-3903, ABBV-119, FDL-169, ARN5562, ARN21586, ARN22081, ARN22652, ARN23765, ARN23766, PTI-801, FDL-176, PTI-808, GLPG1837, GLPG2451/ABBV-2451 (Icenticaftor), GLPG3067/ABBV-3067 (Navocaftor), ABBV-191, ELX-02, MRT5005, Lunar-CF, RCT223, amiloride, ETD001, CF552, GS-9411, GS-5737, P-1037 (VX-371), P-1055 (VX-551), AZD5634, SPX-101, Ionis-ENaC-2.5 Rx, BI 1265162, AZ5634, ARO-ENaC1001, ETD002, and DS-1039, and pharmaceutically acceptable salts and deuterated derivatives thereof; and (c) at least one pharmaceutically acceptable carrier.

Any pharmaceutical composition disclosed herein may comprise at least one pharmaceutically acceptable carrier. In some embodiments, the at least one pharmaceutically acceptable carrier is chosen from pharmaceutically acceptable vehicles and pharmaceutically acceptable adjuvants. In some embodiments, the at least one pharmaceutically acceptable is chosen from pharmaceutically acceptable fillers, disintegrants, surfactants, binders, lubricants.

The pharmaceutical compositions described herein are useful for treating cystic fibrosis and other CFTR-mediated diseases.

As described above, pharmaceutical compositions disclosed herein may optionally further comprise at least one pharmaceutically acceptable carrier. The at least one pharmaceutically acceptable carrier may be chosen from adjuvants and vehicles. The at least one pharmaceutically acceptable carrier, as used herein, includes any and all solvents, diluents, other liquid vehicles, dispersion aids, suspension aids, surface active agents, isotonic agents, thickening agents, emulsifying agents, preservatives, solid binders, and lubricants, as suited to the particular dosage form desired. Remington: *The Science and Practice of Pharmacy*, 21st edition, 2005, ed. D. B. Troy, Lippincott Williams &

Wilkins, Philadelphia, and *Encyclopedia of Pharmaceutical Technology*, eds. J. Swarbrick and J. C. Boylan, 1988-1999, Marcel Dekker, New York discloses various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include, but are not limited to, ion exchangers, alumina, aluminum stearate, lecithin, serum proteins (such as human serum albumin), buffer substances (such as phosphates, glycine, sorbic acid, and potassium sorbate), partial glyceride mixtures of saturated vegetable fatty acids, water, salts, and electrolytes (such as protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as lactose, glucose and sucrose), starches (such as corn starch and potato starch), cellulose and its derivatives (such as sodium carboxymethyl cellulose, ethyl cellulose and cellulose acetate), powdered tragacanth, malt, gelatin, talc, excipients (such as cocoa butter and suppository waxes), oils (such as peanut oil, cottonseed oil, safflower oil, sesame oil, olive oil, corn oil and soybean oil), glycols (such as propylene glycol and polyethylene glycol), esters (such as ethyl oleate and ethyl laurate), agar, buffering agents (such as magnesium hydroxide and aluminum hydroxide), alginic acid, pyrogen-free water, isotonic saline, Ringer's solution, ethyl alcohol, phosphate buffer solutions, non-toxic compatible lubricants (such as sodium lauryl sulfate and magnesium stearate), coloring agents, releasing agents, coating agents, sweetening agents, flavoring agents, perfuming agents, preservatives, and antioxidants.

Non-Limiting Exemplary Embodiments

1. A compound selected from compounds of Formula I:

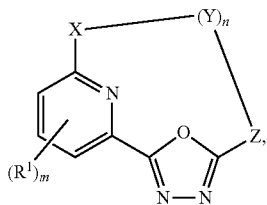

and deuterated derivatives and pharmaceutically acceptable salts thereof, wherein:

X is selected from —N($R^{X1}$)— and

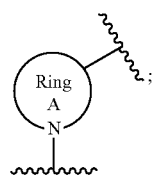

Ring A is a 4- to 6-membered heterocyclyl optionally substituted with 1-3 groups independently selected from $C_1$-$C_6$ alkyl and oxo;

$R^{X1}$ is selected from H, $C_1$-$C_6$ alkyl (optionally substituted with 1-3 groups independently selected from hydroxy, oxo, —$OR^{X2}$, and —N($R^{X2}$)$_2$), and $C_3$-$C_8$ cycloalkyl;

each $R^{X1}$ is independently selected from H and $C_1$-$C_6$ alkyl;

each Y is independently selected from —C($R^Y$)$_2$—, —O—, —CO—, —$NR^{YN}$—, and

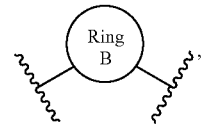

wherein each $R^{YN}$ is independently selected from H, $C_1$-$C_4$ alkyl, and $CO_2R^{YN1}$, wherein each $R^{YN1}$ is independently selected from $C_1$-$C_4$ alkyl and $C_3$-$C_6$ cycloalkyl;

each $R^Y$ is independently selected from hydrogen, hydroxy, halogen, $C_1$-$C_6$ alkyl (optionally substituted with 1-3 groups independently selected from hydroxy, $C_1$-$C_6$ alkoxy, and Q), $C_3$-$C_8$ cycloalkyl, $C_6$-$C_{10}$ aryl (optionally substituted with 1-3 groups independently selected from halogen), 5- to 10-membered heteroaryl, —$OR^{Y1}$, —$CO_2R^{Y1}$, —$COR^{Y1}$, —CON($R^{Y1}$)$_2$, and —N($R^{Y1}$)$_2$;

or two $R^Y$ on the same atom are taken together to form a ring selected from $C_3$-$C_8$ cycloalkyl and 3- to 7-membered heterocyclyl; or two $R^Y$, one of which is on one atom and the second of which is on an adjacent atom, are taken together to form a pi bond;

each $R^{Y1}$ is independently selected from hydrogen and $C_1$-$C_6$ alkyl, or two $R^{Y1}$ bonded to the same nitrogen taken together form a 3- to 6-membered heterocyclyl;

Ring B is selected from:
$C_6$-$C_{10}$ aryl (optionally substituted with 1-3 groups independently selected from halogen, $C_1$-$C_6$ alkyl, and $C_1$-$C_6$ alkoxy),
$C_3$-$C_8$ cycloalkyl,
5- to 10-membered heteroaryl, and
3- to 6-membered heterocyclyl (optionally substituted with 1-3 groups independently selected from $C_1$-$C_6$ alkyl);

each Q is independently selected from:
$C_1$-$C_6$ alkyl optionally substituted with 1-3 groups independently selected from:
halogen,
oxo,
$C_6$-$C_{10}$ aryl (optionally substituted with 1-3 groups independently selected from halogen and —$OCF_3$), and
$C_3$-$C_8$ cycloalkyl,
$C_3$-$C_8$ cycloalkyl optionally substituted with 1-3 groups independently selected from:
halogen,
CN,
$C_1$-$C_6$ alkyl (optionally substituted with 1-3 groups independently selected from halogen, —$NH_2$, and —NHCOMe),
$C_1$-$C_6$ alkoxy,
$C_6$-$C_{10}$ aryl (optionally substituted with 1-3 groups independently selected from $C_1$-$C_6$ alkyl), and
$C_3$-$C_8$ cycloalkyl, $C_6$-$C_{10}$ aryl optionally substituted with 1-3 groups independently selected from:
halogen,
CN,
$C_1$-$C_6$ alkyl (optionally substituted with 1-3 groups independently selected from halogen and hydroxy),
$C_1$-$C_6$ alkoxy optionally substituted with 1-4 groups independently selected from:
halogen,
$C_3$-$C_8$ cycloalkyl (optionally substituted with $CF_3$),
$C_3$-$C_8$ cycloalkyl (optionally substituted with 1-3 groups independently selected from halogen, $CF_3$, $OCF_3$, and $C_1$-$C_6$ alkyl), and
$C_6$-$C_{10}$ aryl,
5- to 10-membered heteroaryl optionally substituted with 1-3 groups independently selected from:
halogen,
$C_1$-$C_6$ alkyl (optionally substituted with 1-3 groups independently selected from halogen),
$C_3$-$C_8$ cycloalkyl (optionally substituted with 1-3 $CF_3$ groups), and
3- to 10-membered heterocyclyl,
3- to 10-membered heterocyclyl optionally substituted with 1-3 groups independently selected from:
$C_1$-$C_6$ alkyl (optionally substituted with 1-3 groups independently selected from oxo and $C_3$-$C_8$ cycloalkyl), and
oxo;
each $R^{X1}$ is independently selected from halogen, $C_1$-$C_6$ fluoroalkyl, $C_1$-$C_6$ alkyl (optionally substituted with a group selected from hydroxy, $C_6$-$C_{10}$ aryl, and 5- to 6-membered heteroaryl), $-OR^2$, $-N(R^2)_2$, $-CO_2R^2$, $-CO-N(R^2)_2$, $-CN$, $C_3$-$C_8$ cycloalkyl, $C_6$-$C_{10}$ aryl, 5- to 6-membered heteroaryl (optionally substituted with 1-3 groups independently selected from $C_1$-$C_6$ alkyl), 3- to 6-membered heterocyclyl, $-B(OR^2)_2$, $-SO_2R^2$, $-SR^2$, $-SOR^2$, $-PO(OR^2)_2$, and $-PO(R^2)_2$;
each $R^2$ is independently selected from hydrogen, $C_1$-$C_6$ alkyl (optionally substituted with 1-6 groups independently selected from halogen), $C_1$-$C_6$ fluoroalkyl, and $C_6$-$C_{10}$ aryl (optionally substituted with 1-3 groups independently selected from $C_1$-$C_6$ fluoroalkyl and $C_1$-$C_6$ fluoroalkoxy);
Z is selected from

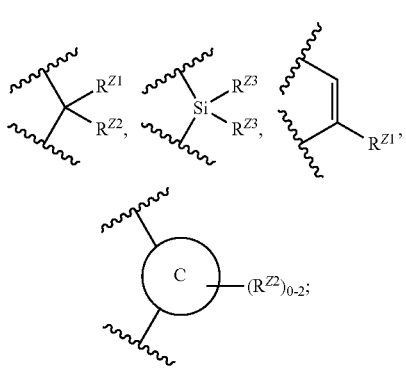

wherein Ring C is selected from $C_6$-$C_{10}$ aryl and 5- to 10-membered heteroaryl;

$R^{Z1}$ is selected from hydrogen, $-CN$, $C_1$-$C_6$ alkyl (optionally substituted with 1-3 hydroxy), $C_1$-$C_6$ fluoroalkyl, 3- to 6-membered heterocyclyl, $C_3$-$C_6$ cycloalkyl, $C_6$-$C_{10}$ aryl, and 5- to 6-membered heteroaryl;
$R^{Z2}$ is selected from hydrogen, halogen, hydroxy, $NH_2$, $NH(CO)(C_1$-$C_6$ alkyl), and $C_1$-$C_6$ alkoxy (optionally substituted with 1-3 groups independently selected from $C_3$-$C_{10}$ cycloalkyl),
or $R^{Z1}$ and $R^{Z2}$ taken together form a group selected from oxo and $=N-OH$;
each $R^{Z3}$ is independently selected from hydroxy, $C_1$-$C_6$ alkoxy, $C_1$-$C_6$ alkyl, and $C_6$-$C_{10}$ aryl; or two $R^{Z3}$ are taken together to form a 3- to 6-membered heterocyclyl;
n is selected from 4, 5, 6, 7, and 8; and
m is selected from 0, 1, 2, and 3.

2. The compound, deuterated derivative, or pharmaceutically acceptable salt according to Embodiment 1, wherein:
X is selected from $-N(R^{X1})-$ and

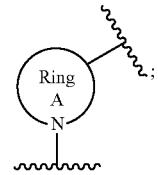

Ring A is a 4- to 6-membered heterocyclyl optionally substituted with 1-3 groups independently selected from $C_1$-$C_6$ alkyl and oxo;
$R^{X1}$ is selected from H, $C_1$-$C_6$ alkyl (optionally substituted with 1-3 groups independently selected from hydroxy, oxo, $-OR^{X2}$, and $-N(R^{X2})_2$), and $C_3$-$C_5$ cycloalkyl;
each $R^{X2}$ is independently selected from H and $C_1$-$C_6$ alkyl;
each Y is independently selected from $-C(R^Y)_2-$, $-O-$, $-CO-$, $-NR^{YN}-$, and

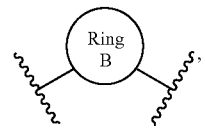

wherein each $R^{YN}$ is independently selected from H, $C_1$-$C_4$ alkyl, and $CO_2Me$;
each $R^Y$ is independently selected from hydrogen, hydroxy, halogen, $C_1$-$C_6$ alkyl (optionally substituted with 1-3 groups independently selected from hydroxy, $C_1$-$C_6$ alkoxy, and Q), $C_3$-$C_8$ cycloalkyl, $C_6$-$C_{10}$ aryl (optionally substituted with 1-3 groups independently selected from halogen), 5- to 10-membered heteroaryl, $-OR^{Y1}$, $-CO_2R^{Y1}$, $-COR^{Y1}$, $-CON(R^{Y1})_2$, and $-N(R^{Y1})_2$;
or two $R^Y$ on the same atom are taken together to form a ring selected from $C_3$-$C_8$ cycloalkyl and 3- to 7-membered heterocyclyl; or two $R^Y$, one of which is on one atom and the second of which is on an adjacent atom, are taken together to form a pi bond;
each $R^{Y1}$ is independently selected from hydrogen and $C_1$-$C_6$ alkyl, or two $R^{Y1}$ bonded to the same nitrogen taken together form a 3- to 6-membered heterocyclyl;

Ring B is selected from:
C$_6$-C$_{10}$ aryl (optionally substituted with 1-3 groups independently selected from halogen, C$_1$-C$_6$ alkyl, and C$_1$-C$_6$ alkoxy),
C$_3$-C$_8$ cycloalkyl,
5- to 10-membered heteroaryl, and
3- to 6-membered heterocyclyl (optionally substituted with 1-3 groups independently selected from C$_1$-C$_6$ alkyl);
each Q is independently selected from:
C$_1$-C$_6$ alkyl optionally substituted with 1-3 groups independently selected from:
halogen,
oxo,
C$_6$-C$_{10}$ aryl (optionally substituted with 1-3 groups independently selected from halogen and —OCF$_3$), and
C$_3$-C$_8$ cycloalkyl,
C$_3$-C$_8$ cycloalkyl optionally substituted with 1-3 groups independently selected from:
halogen,
CN,
C$_1$-C$_6$ alkyl (optionally substituted with 1-3 groups independently selected from halogen, —NH$_2$, and —NHCOMe),
C$_1$-C$_6$ alkoxy,
C$_6$-C$_{10}$ aryl (optionally substituted with 1-3 groups independently selected from C$_1$-C$_6$ alkyl), and
C$_3$-C$_8$ cycloalkyl,
C$_6$-C$_{10}$ aryl optionally substituted with 1-3 groups independently selected from:
halogen,
CN,
C$_1$-C$_6$ alkyl (optionally substituted with 1-3 groups independently selected from halogen and hydroxy),
C$_1$-C$_6$ alkoxy optionally substituted with 1-4 groups independently selected from:
halogen,
C$_3$-C$_8$ cycloalkyl (optionally substituted with CF$_3$),
C$_3$-C$_8$ cycloalkyl (optionally substituted with 1-3 groups independently selected from halogen, CF$_3$, OCF$_3$, and C$_1$-C$_6$ alkyl), and
C$_6$-C$_{10}$ aryl,
5- to 10-membered heteroaryl optionally substituted with 1-3 groups independently selected from:
halogen,
C$_1$-C$_6$ alkyl (optionally substituted with 1-3 groups independently selected from halogen),
C$_3$-C$_8$ cycloalkyl (optionally substituted with 1-3 CF$_3$ groups), and
3- to 10-membered heterocyclyl,
3- to 10-membered heterocyclyl optionally substituted with 1-3 groups independently selected from:
C$_1$-C$_6$ alkyl (optionally substituted with 1-3 groups independently selected from oxo and C$_3$-C$_8$ cycloalkyl), and
oxo;
each R$^1$ is independently selected from halogen, C$_1$-C$_6$ fluoroalkyl, C$_1$-C$_6$ alkyl (optionally substituted with a group selected from C$_6$-C$_{10}$ aryl and 5- to 6-membered heteroaryl), —OR$^2$, —N(R$^2$)$_2$, —CO$_2$R$^2$, —CO—N(R$^2$)$_2$, —CN, C$_1$-C$_6$ alkoxy, C$_3$-C$_8$ cycloalkyl, C$_6$-C$_{10}$ aryl, 5- to 6-membered heteroaryl (optionally substituted with 1-3 groups independently selected from C$_1$-C$_6$ alkyl), 3- to 6-membered heterocyclyl, —SO$_2$R$^2$, —SR$^2$, —SOR$^2$, —PO(OR$^2$)$_2$, and —PO(R$^2$)$_2$;

each R$^2$ is independently selected from hydrogen, C$_1$-C$_6$ alkyl (optionally substituted with 1-6 groups independently selected from halogen), C$_1$-C$_6$ fluoroalkyl, and C$_6$-C$_{10}$ aryl (optionally substituted with 1-3 groups independently selected from C$_1$-C$_6$ fluoroalkyl and C$_1$-C$_6$ fluoroalkoxy);

Z is selected from

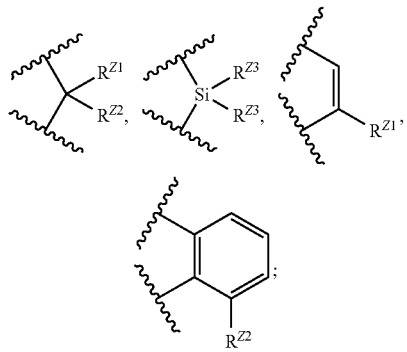

R$^{Z1}$ is selected from hydrogen, —CN, C$_1$-C$_6$ alkyl (optionally substituted with 1-3 hydroxy), C$_1$-C$_6$ fluoroalkyl, 3- to 6-membered heterocyclyl, C$_3$-C$_6$ cycloalkyl, C$_6$-C$_{10}$ aryl, and 5- to 6-membered heteroaryl;
R$^{Z2}$ is selected from hydrogen, halogen, hydroxy, and C$_1$-C$_6$ alkoxy (optionally substituted with 1-3 groups independently selected from C$_3$-C$_{10}$ cycloalkyl),
or R$^{Z1}$ and R$^{Z2}$ taken together form a group selected from oxo and =N—OH;
each R$^{Z3}$ is independently selected from hydroxy, C$_1$-C$_6$ alkoxy, C$_1$-C$_6$ alkyl, and C$_6$-C$_{10}$ aryl; or two R$^{Z3}$ are taken together to form a 3- to 6-membered heterocyclyl;
n is selected from 4, 5, 6, and 7; and
m is selected from 0, 1, 2, and 3.

3. The compound, deuterated derivative, or salt according to Embodiment 1 or 2, wherein X is —NR$^{X1}$.

4. The compound, deuterated derivative, or salt according to any one of Embodiments 1-3, wherein X is selected from:

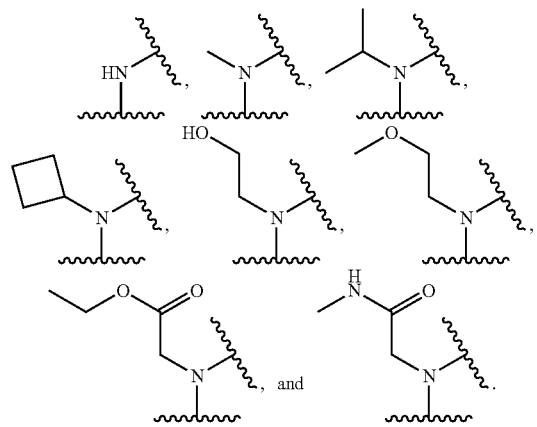

5. The compound, deuterated derivative, or salt according to Embodiment 1 or 2, wherein X is

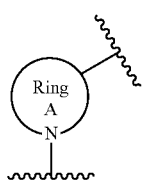

6. The compound, deuterated derivative, or salt according to Embodiment 1, 2, or 5, wherein Ring A is selected from pyrrolidine, piperazine, morpholine, and isothiazolidine.

7. The compound, deuterated derivative, or salt according to Embodiment 1, 2, 5, or 6, wherein X is selected from:

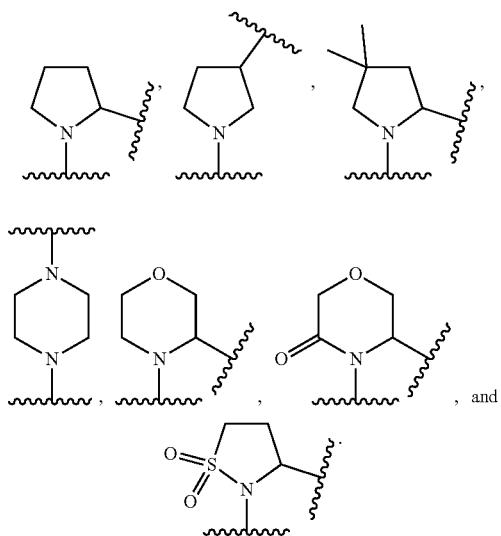

8. The compound, deuterated derivative, or salt according to any one of Embodiments 1-7, wherein each $R^Y$ is independently selected from: hydrogen, hydroxy, methyl,

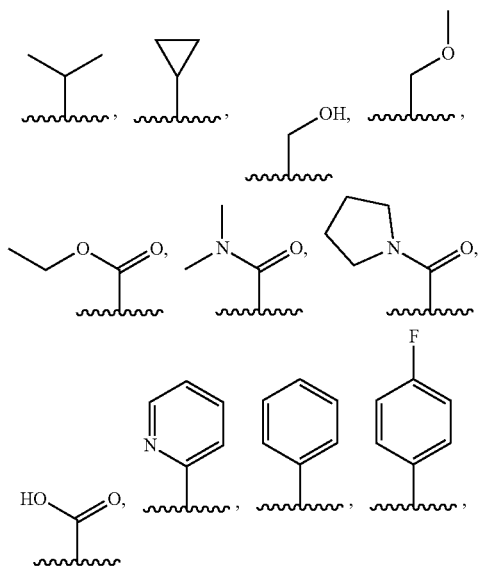

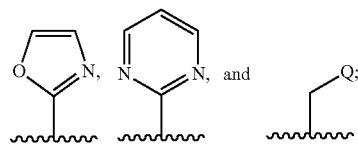

or wherein two $R^Y$ on the same atom are taken together to form a ring selected from cyclobutyl, cyclopentyl, cyclohexyl, tetrahydrofuranyl, and tetrahydropyranyl; or wherein two $R^Y$, one of which is on one atom and the second of which is on an adjacent atom, are taken together to form a pi bond.

9. The compound, deuterated derivative, or salt according to any one of Embodiments 1-8, wherein each Q is independently selected from $C_6$-$C_{10}$ aryl optionally substituted with 1-3 groups independently selected from halogen and $C_1$-$C_6$ alkyl.

10. The compound, deuterated derivative, or salt according to any one of Embodiments 1-9, wherein each Q is phenyl.

11. The compound, deuterated derivative, or salt according to any one of Embodiments 1-10, wherein each Ring B is independently selected from $C_6$-$C_{10}$ aryl (optionally substituted with 1-3 groups independently selected from halogen and $C_1$-$C_6$ alkoxy) and 5- to 10-membered heteroaryl.

12. The compound, deuterated derivative, or salt according to any one of Embodiments 1-11, wherein each Ring B is independently selected from:

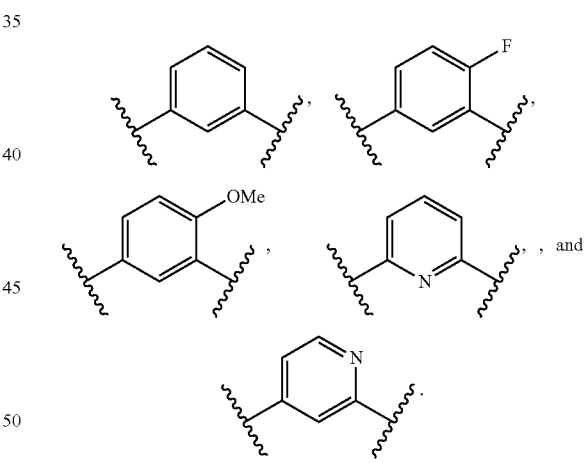

13. The compound, deuterated derivative, or salt according to any one of Embodiments 1-12, wherein —(Y)$_n$— is a group selected from:

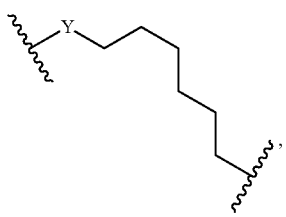

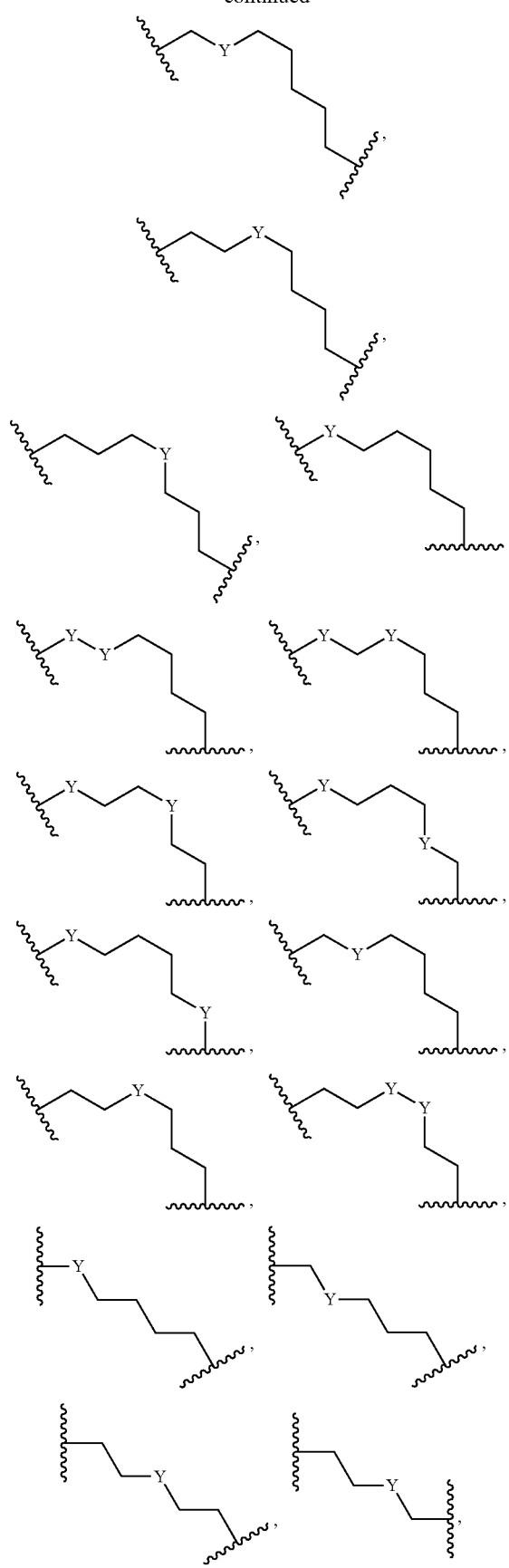
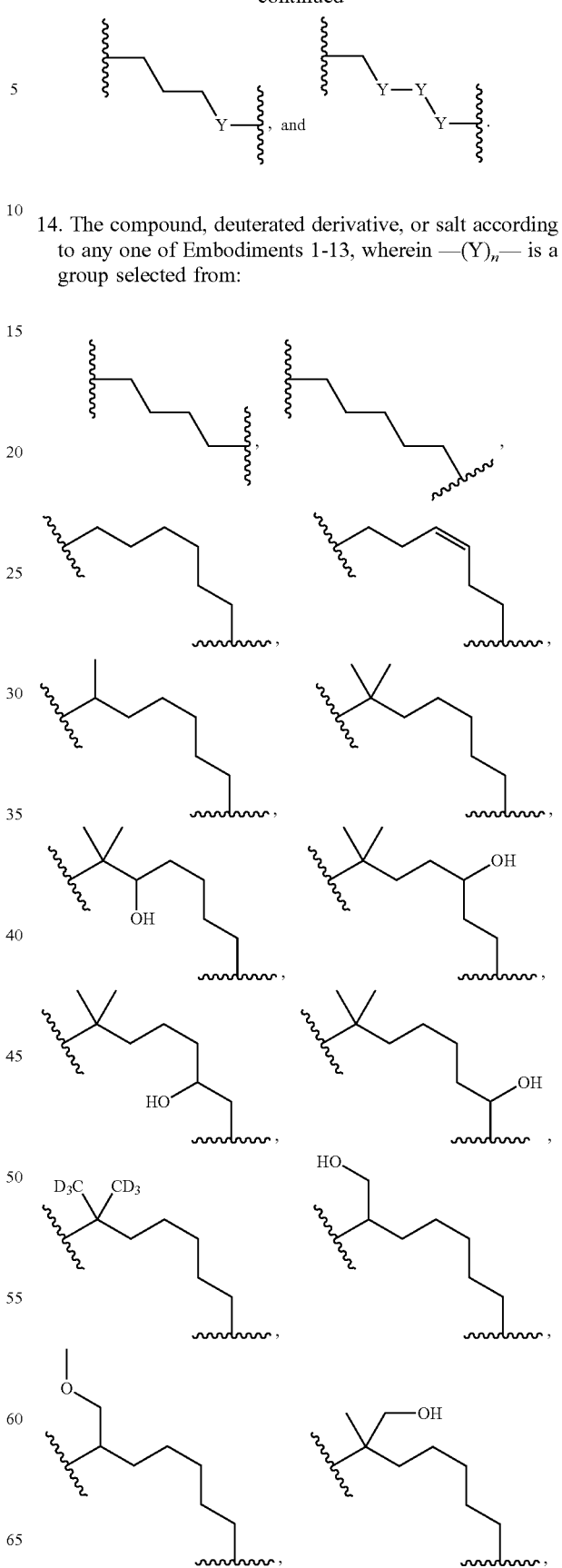
14. The compound, deuterated derivative, or salt according to any one of Embodiments 1-13, wherein —(Y)$_n$— is a group selected from:

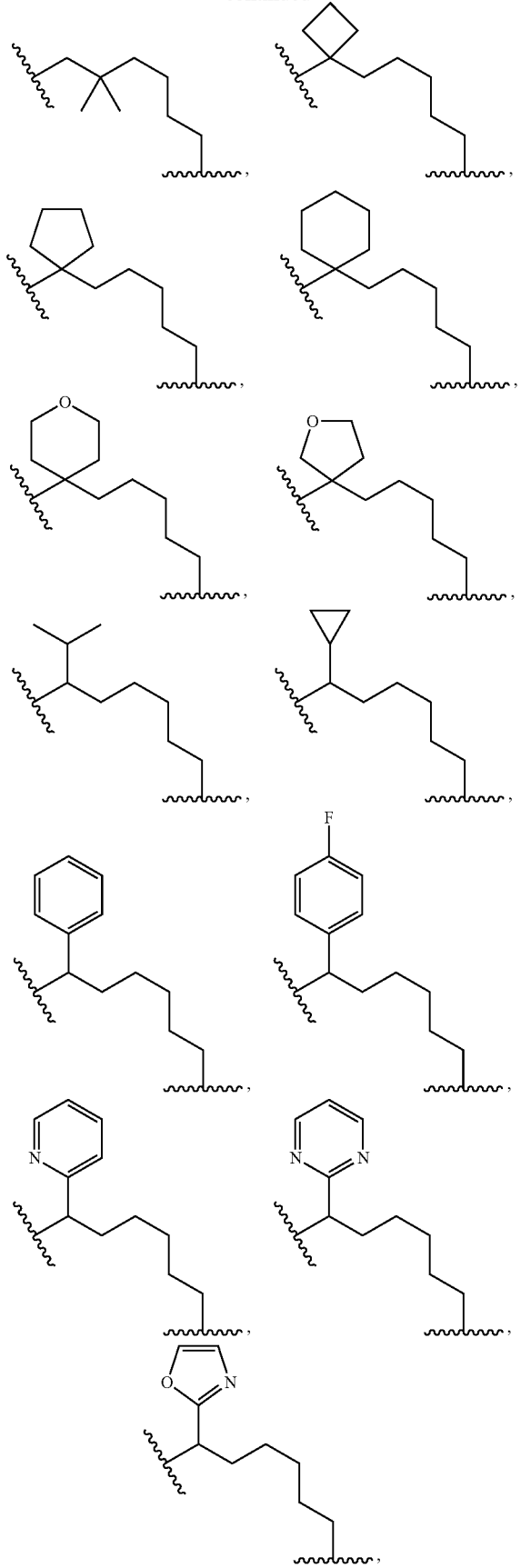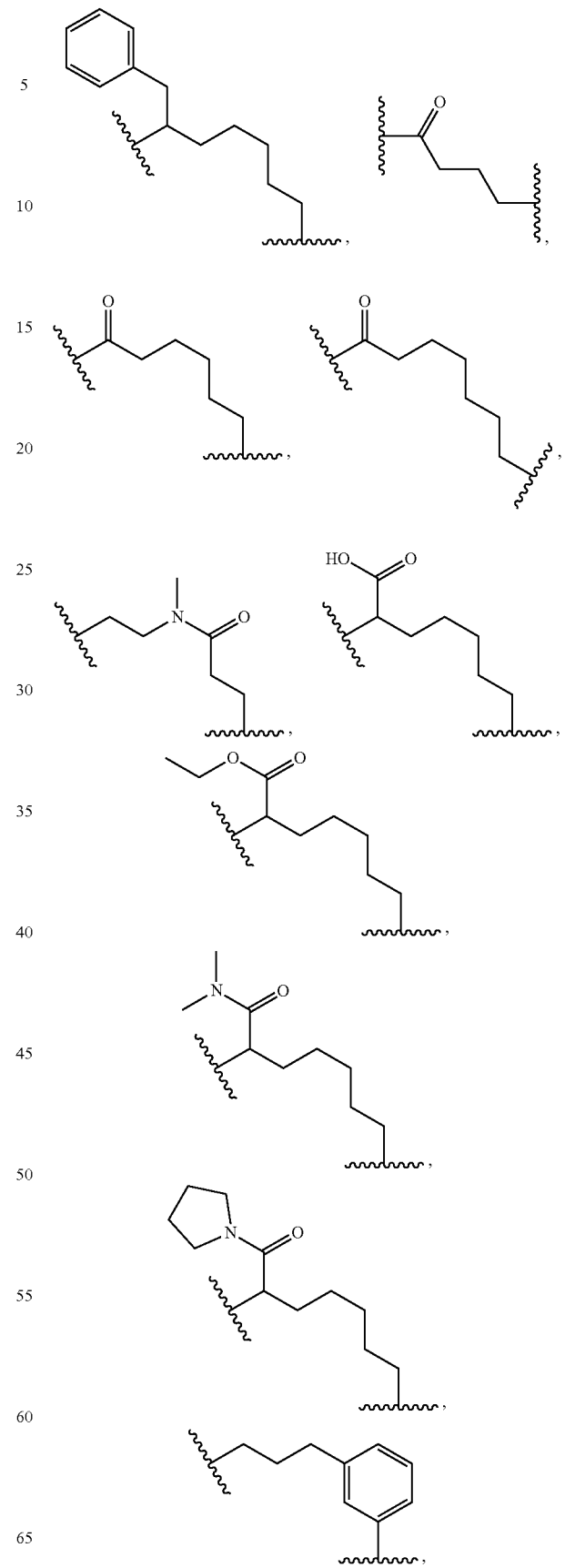

-continued

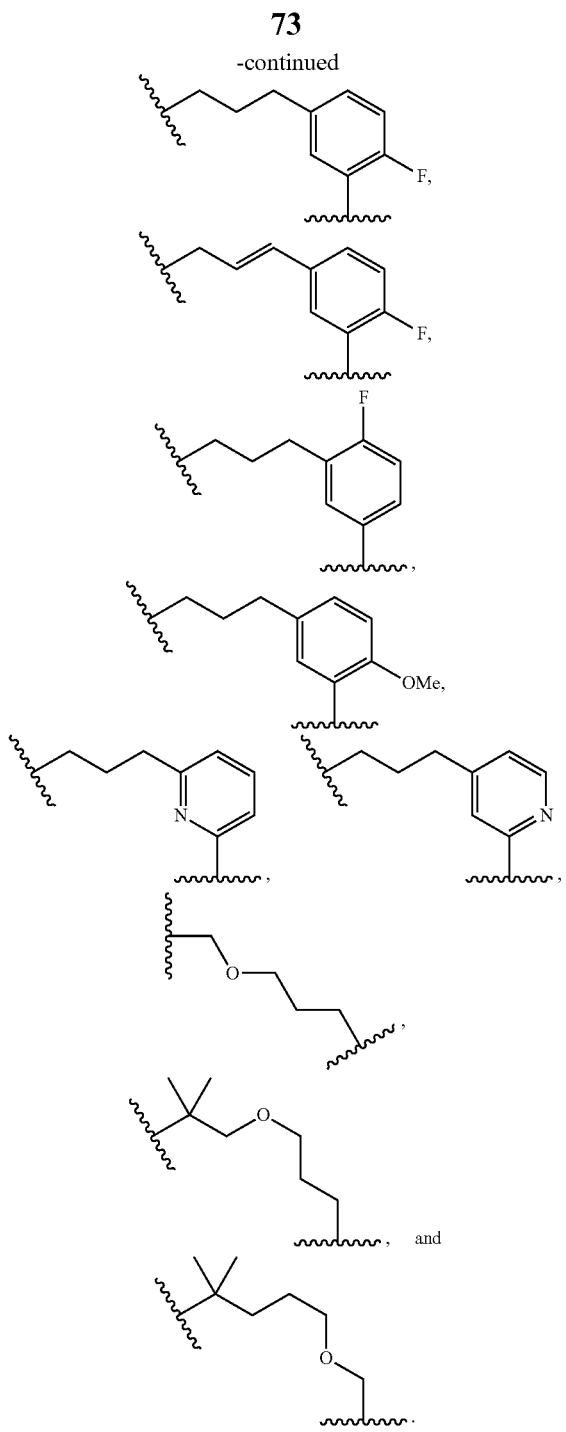

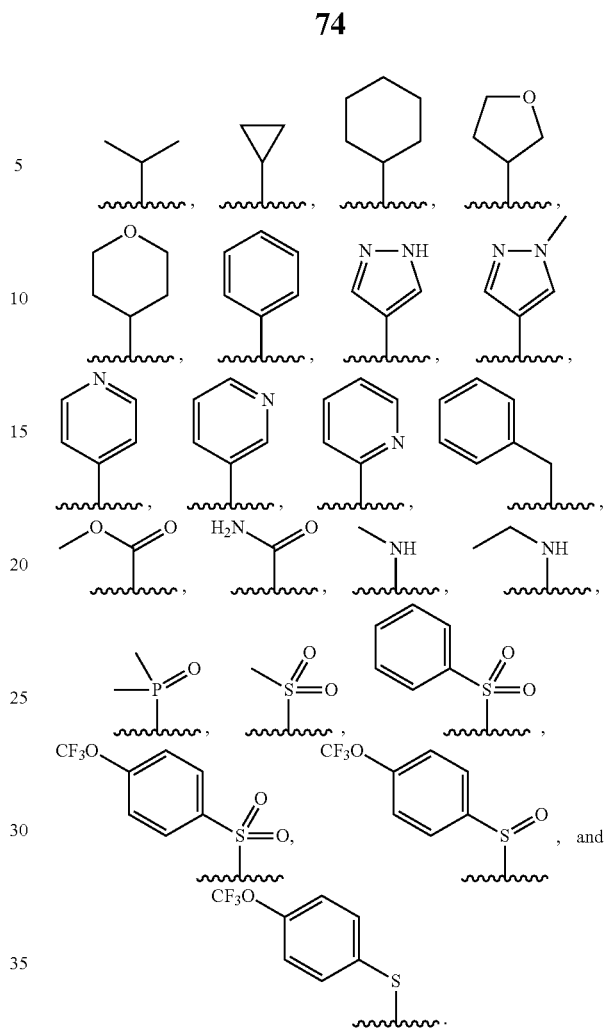

15. The compound, deuterated derivative, or salt according to any one of Embodiments 1-14, wherein each Y is —C(R$^Y$)$_2$—.

16. The compound, deuterated derivative, or salt according to Embodiment 15, wherein each Y is independently selected from —CH$_2$— and —C(Me)$_2$-.

17. The compound, deuterated derivative, or salt according to any one of Embodiments 1-16, wherein each R$^1$ is independently selected from C$_1$-C$_6$ fluoroalkyl and —N(R$^2$)$_2$.

18. The compound, deuterated derivative, or salt according to any one of Embodiments 1-16, wherein each R$^1$ is independently selected from Br, —CH$_3$, —CF$_3$, —CHF$_2$, —OH, —OCH$_3$, —CN, —NH$_2$, 19. The compound, deuterated derivative, or salt according to any one of Embodiments 1-18, wherein each R$^1$ is independently selected from —CF$_3$ and —NH$_2$.

20. The compound, deuterated derivative, or salt according to any one of Embodiments 1-19, wherein Z is selected from:

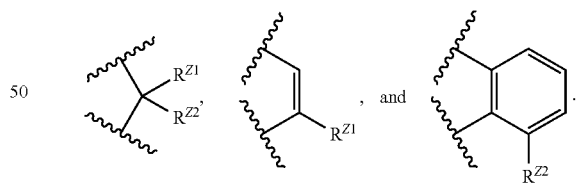

21. The compound, deuterated derivative, or salt according to any one of Embodiments 1-20, wherein:
R$^{Z1}$ is selected from hydrogen, C$_1$-C$_6$ alkyl (optionally substituted with 1-3 hydroxy), C$_1$-C$_6$ fluoroalkyl, 3- to 6-membered heterocyclyl, C$_3$-C$_6$ cycloalkyl, and C$_6$-C$_{10}$ aryl,
R$^{Z2}$ is selected from hydrogen, hydroxy, and C$_1$-C$_6$ alkoxy (optionally substituted with 1-3 groups independently selected from C$_3$-C$_{10}$ cycloalkyl),
or R$^{Z1}$ and R$^{Z2}$ taken together form a group selected from oxo and =N—OH;

22. The compound, deuterated derivative, or salt according to any one of Embodiments 1-21, wherein Z is

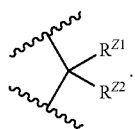

23. The compound, deuterated derivative, or salt according to any one of Embodiments 1-22, wherein

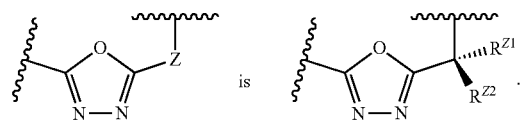

24. The compound, deuterated derivative, or salt according to any one of Embodiments 1-23, wherein $R^{Z1}$ is selected from $C_1$-$C_6$ fluoroalkyl.
25. The compound, deuterated derivative, or salt according to any one of Embodiments 1-24, wherein $R^{Z1}$ is —$CF_3$.
26. The compound, deuterated derivative, or salt according to any one of Embodiments 1-25, wherein $R^{Z2}$ is hydroxy.
27. The compound, deuterated derivative, or salt according to any one of Embodiments 1-21, wherein Z is selected from:

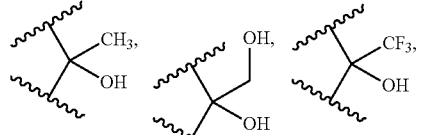

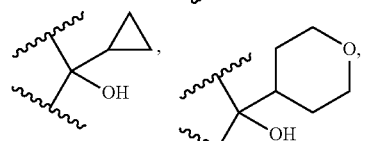

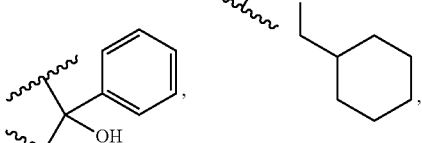

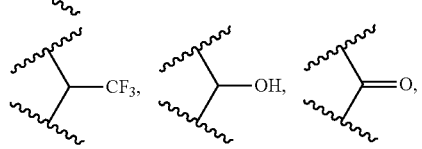

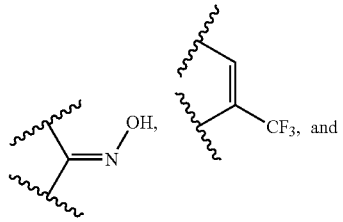

-continued

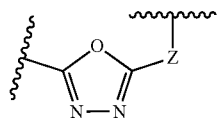

28. The compound, deuterated derivative, or salt according to any one of Embodiments 1-21, wherein

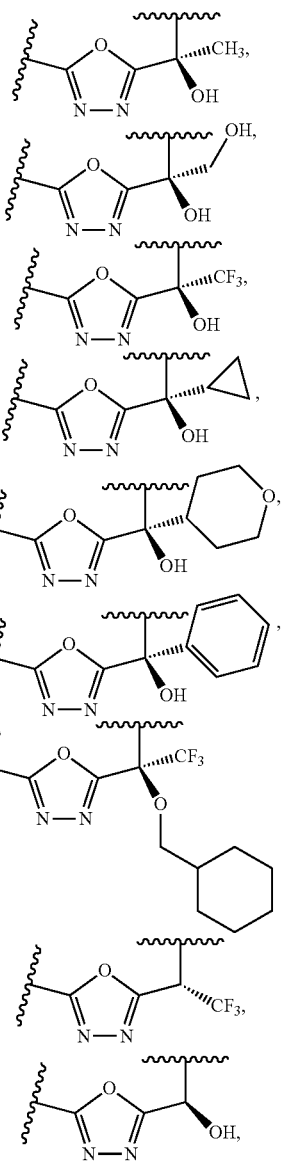

is selected from:

-continued

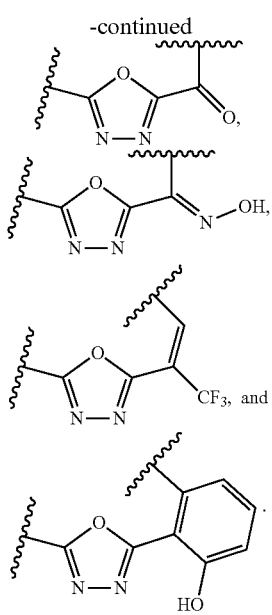

29. The compound, deuterated derivative, or salt according to any one of Embodiments 1-28, wherein n is selected from 4, 5, and 6.
30. The compound, deuterated derivative, or salt according to any one of Embodiments 1-29, wherein n is 5.
31. The compound, deuterated derivative, or salt according to any one of Embodiments 1-29, wherein n is 6.
32. The compound, deuterated derivative, or salt according to any one of Embodiments 1-31, wherein m is selected from 1 and 2.
33. The compound, deuterated derivative, or salt according to any one of Embodiments 1-32, wherein m is 2.
34. A compound selected from compounds of Formula Ia:

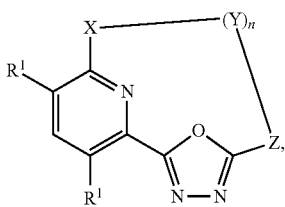

and deuterated derivatives and pharmaceutically acceptable salts thereof, wherein:

X is selected from $-NR^{X1}-$ and

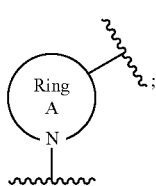

Ring A is a 4- to 6-membered heterocyclyl optionally substituted with 1-3 groups independently selected from $C_1$-$C_6$ alkyl and oxo;

$R^{X1}$ is selected from H, $C_1$-$C_6$ alkyl (optionally substituted with 1-3 groups independently selected from hydroxy, oxo, $-OR^{X2}$, and $-N(R^{X2})_2$), and $C_3$-$C_8$ cycloalkyl;

each $R^{X2}$ is independently selected from H and $C_1$-$C_6$ alkyl;

each Y is independently selected from $-C(R^Y)_2-$, $-O-$, $-CO-$, $-NR^{YN}-$, and

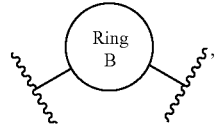

wherein each $R^{YN}$ is independently selected from H, $C_1$-$C_4$ alkyl, and $CO_2Me$;

each $R^Y$ is independently selected from hydrogen, hydroxy, halogen, $C_1$-$C_6$ alkyl (optionally substituted with 1-3 groups independently selected from hydroxy, $C_1$-$C_6$ alkoxy, and Q), $C_3$-$C_8$ cycloalkyl, $C_6$-$C_{10}$ aryl (optionally substituted with 1-3 groups independently selected from halogen), 5- to 10-membered heteroaryl, $-CO_2R^{Y1}$, $-COR^{Y1}$, $-CON(R^{Y1})_2$, and $-N(R^{Y1})_2-$;

or two $R^Y$ on the same atom are taken together to form a ring selected from $C_3$-$C_8$ cycloalkyl and 3- to 7-membered heterocyclyl; or two $R^Y$, one of which is on one atom and the second of which is on an adjacent atom, are taken together to form a pi bond;

each $R^{Y1}$ is independently selected from hydrogen and $C_1$-$C_6$ alkyl, or two $R^{Y1}$ bonded to the same nitrogen taken together form a 3- to 6-membered heterocyclyl;

Ring B is selected from:
  $C_6$-$C_{10}$ aryl (optionally substituted with 1-3 groups independently selected from halogen, $C_1$-$C_6$ alkyl, and $C_1$-$C_6$ alkoxy),
  $C_3$-$C_8$ cycloalkyl,
  5- to 10-membered heteroaryl, and
  3- to 6-membered heterocyclyl (optionally substituted with 1-3 groups independently selected from $C_1$-$C_6$ alkyl);

each Q is independently selected from:
  $C_1$-$C_6$ alkyl optionally substituted with 1-3 groups independently selected from:
    halogen,
    oxo,
    $C_6$-$C_{10}$ aryl (optionally substituted with 1-3 groups independently selected from halogen and $-OCF_3$), and
    $C_3$-$C_8$ cycloalkyl,
  $C_3$-$C_8$ cycloalkyl optionally substituted with 1-3 groups independently selected from:
    halogen,
    CN,
    $C_1$-$C_6$ alkyl (optionally substituted with 1-3 groups independently selected from halogen, $-NH_2$, and $-NHCOMe$),
    $C_1$-$C_6$ alkoxy,
    $C_6$-$C_{10}$ aryl (optionally substituted with 1-3 groups independently selected from $C_1$-$C_6$ alkyl), and
    $C_3$-$C_8$ cycloalkyl,
  $C_6$-$C_{10}$ aryl optionally substituted with 1-3 groups independently selected from:
    halogen,
    CN, C$_1$-C$_6$ alkyl (optionally substituted with 1-3 groups independently selected from halogen and hydroxy),
C$_1$-C$_6$ alkoxy optionally substituted with 1-4 groups independently selected from:
halogen,
C$_3$-C$_8$ cycloalkyl (optionally substituted with CF$_3$),
C$_3$-C$_8$ cycloalkyl (optionally substituted with 1-3 groups independently selected from halogen, CF$_3$, OCF$_3$, and C$_1$-C$_6$ alkyl), and
C$_6$-C$_{10}$ aryl,
5- to 10-membered heteroaryl optionally substituted with 1-3 groups independently selected from:
halogen,
C$_1$-C$_6$ alkyl (optionally substituted with 1-3 groups independently selected from halogen),
C$_3$-C$_8$ cycloalkyl (optionally substituted with 1-3 CF$_3$ groups), and
3- to 10-membered heterocyclyl,
3- to 10-membered heterocyclyl optionally substituted with 1-3 groups independently selected from:
C$_1$-C$_6$ alkyl (optionally substituted with 1-3 groups independently selected from oxo and C$_3$-C$_8$ cycloalkyl), and
oxo;
each R$^{X1}$ is independently selected from halogen, C$_1$-C$_6$ fluoroalkyl, C$_1$-C$_6$ alkyl (optionally substituted with a group selected from C$_6$-C$_{10}$ aryl and 5- to 6-membered heteroaryl), —OR$^2$, —N(R$^2$)$_2$, —CO$_2$R$^2$, —CO—N(R$^2$)$_2$, —CN, C$_1$-C$_6$ alkoxy, C$_3$-C$_8$ cycloalkyl, C$_6$-C$_{10}$ aryl, 5- to 6-membered heteroaryl (optionally substituted with 1-3 groups independently selected from C$_1$-C$_6$ alkyl), 3- to 6-membered heterocyclyl, —SO$_2$R$^2$, —SR$^2$, —SOR$^2$, —PO(OR$^2$)$_2$, and —PO(R$^2$)$_2$;
each R$^2$ is independently selected from hydrogen, C$_1$-C$_6$ alkyl (optionally substituted with 1-6 groups independently selected from halogen), C$_1$-C$_6$ fluoroalkyl, and C$_6$-C$_{10}$ aryl (optionally substituted with 1-3 groups independently selected from C$_1$-C$_6$ fluoroalkyl and C$_1$-C$_6$ fluoroalkoxy);
Z is selected from

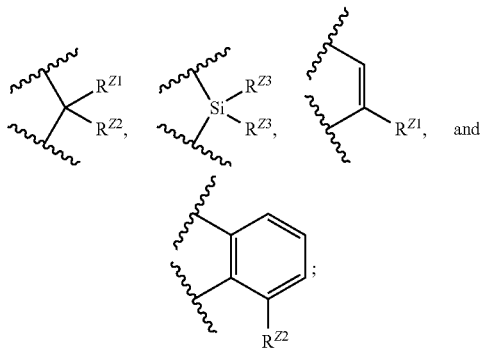

R$^{Z1}$ is selected from hydrogen, —CN, C$_1$-C$_6$ alkyl (optionally substituted with 1-3 hydroxy), C$_1$-C$_6$ fluoroalkyl, 3- to 6-membered heterocyclyl, C$_3$-C$_6$ cycloalkyl, C$_6$-C$_{10}$ aryl, and 5- to 6-membered heteroaryl;
R$^{Z2}$ is selected from hydrogen, halogen, hydroxy, and C$_1$-C$_6$ alkoxy (optionally substituted with 1-3 groups independently selected from C$_3$-C$_{10}$ cycloalkyl),
or R$^{Z1}$ and R$^{Z2}$ taken together form a group selected from oxo and =N—OH;
each R$^{Z3}$ is independently selected from hydroxy, C$_1$-C$_6$ alkoxy, C$_1$-C$_6$ alkyl, and C$_6$-C$_{10}$ aryl; or two R$^{Z3}$ are taken together to form a 3- to 6-membered heterocyclyl; and
n is selected from 4, 5, 6, and 7.

35. The compound, deuterated derivative, or salt according to Embodiment 34, wherein X is —NR$^{X1}$.

36. The compound, deuterated derivative, or salt according to Embodiment 34 or 35, wherein X is selected from:

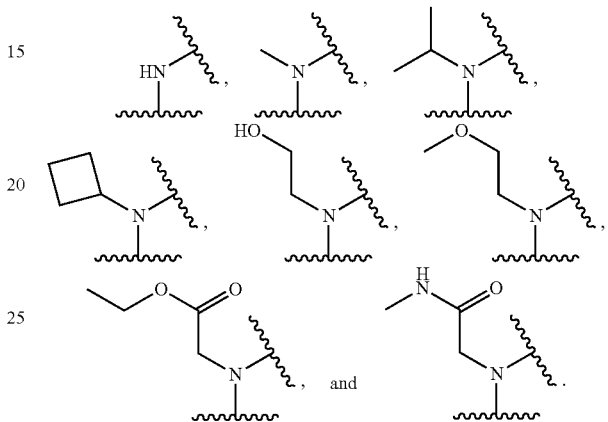

37. The compound, deuterated derivative, or salt according to Embodiment 34, wherein X is

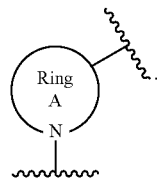

38. The compound, deuterated derivative, or salt according to Embodiment 34 or 37, wherein Ring A is selected from pyrrolidine, piperazine, morpholine, and isothiazolidine.

39. The compound, deuterated derivative, or salt according to Embodiment 34, 37, or 38, wherein X is selected from:

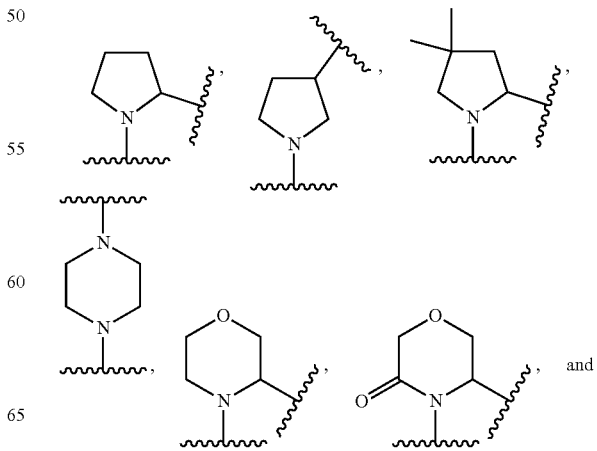

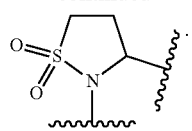

40. The compound, deuterated derivative, or salt according to any one of Embodiments 34-39, wherein each $R^Y$ is independently selected from: hydrogen, hydroxy, methyl,

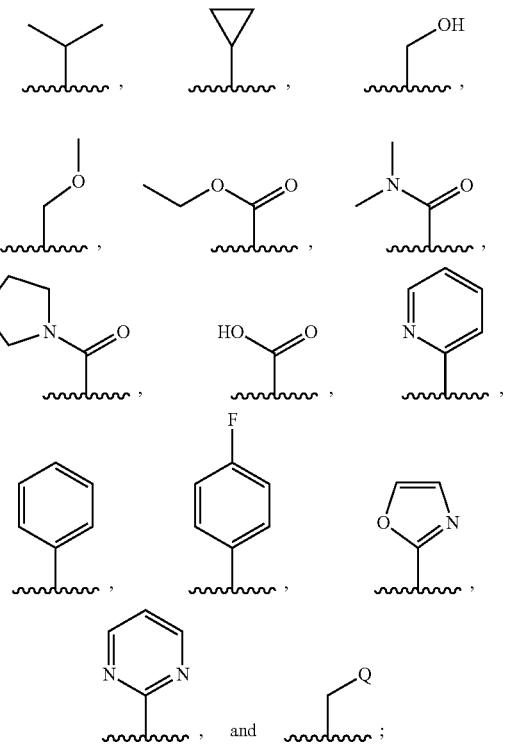

or wherein two $R^Y$ on the same atom are taken together to form a ring selected from cyclobutyl, cyclopentyl, cyclohexyl, tetrahydrofuranyl, and tetrahydropyranyl; or wherein two $R^Y$, one of which is on one atom and the second of which is on an adjacent atom, are taken together to form a pi bond.

41. The compound, deuterated derivative, or salt according to any one of Embodiments 34-40, wherein each Q is independently selected from $C_6$-$C_{10}$ aryl optionally substituted with 1-3 groups independently selected from halogen and $C_1$-$C_6$ alkyl.

42. The compound, deuterated derivative, or salt according to any one of Embodiments 34-41, wherein each Q is phenyl.

43. The compound, deuterated derivative, or salt according to any one of Embodiments 34-42, wherein each Ring B is independently selected from $C_6$-$C_{10}$ aryl (optionally substituted with 1-3 groups independently selected from halogen and $C_1$-$C_6$ alkoxy) and 5- to 10-membered heteroaryl.

44. The compound, deuterated derivative, or salt according to any one of Embodiments 34-43, wherein each Ring B is independently selected from:

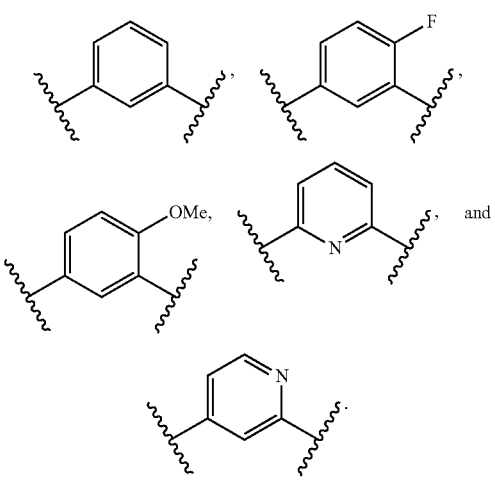

45. The compound, deuterated derivative, or salt according to any one of Embodiments 34-44, wherein —$(Y)_n$— is a group selected from:

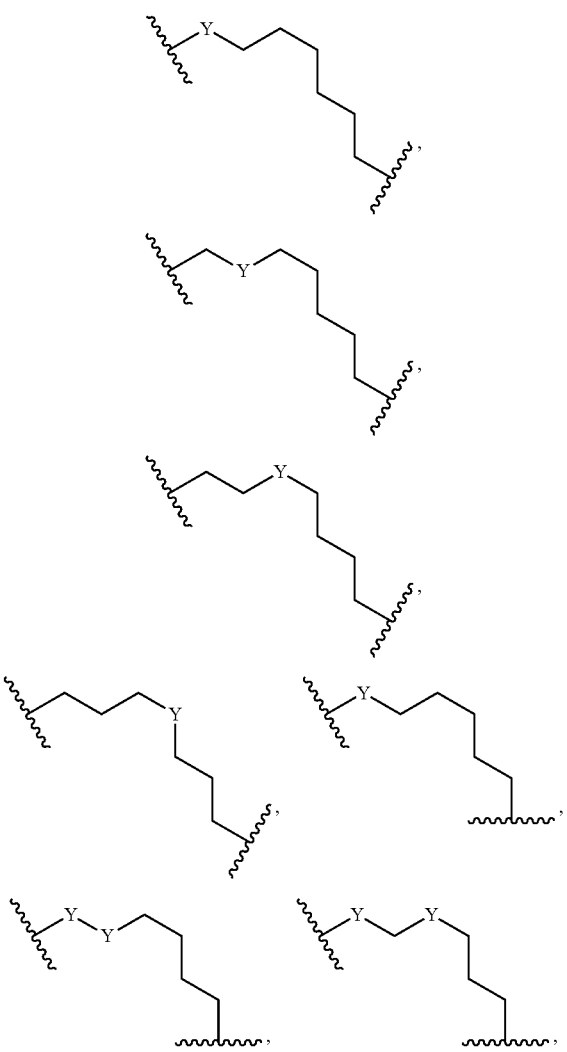

-continued
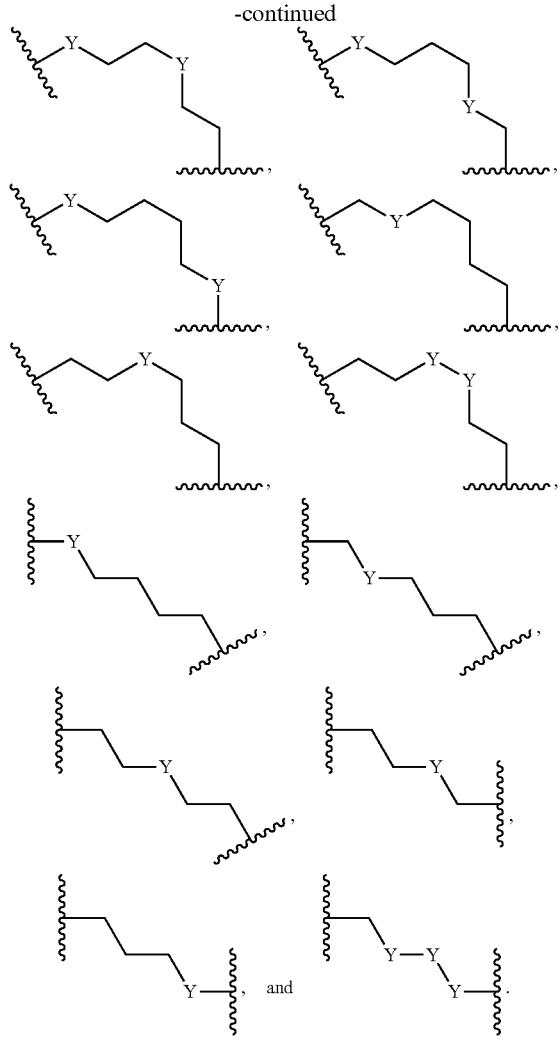
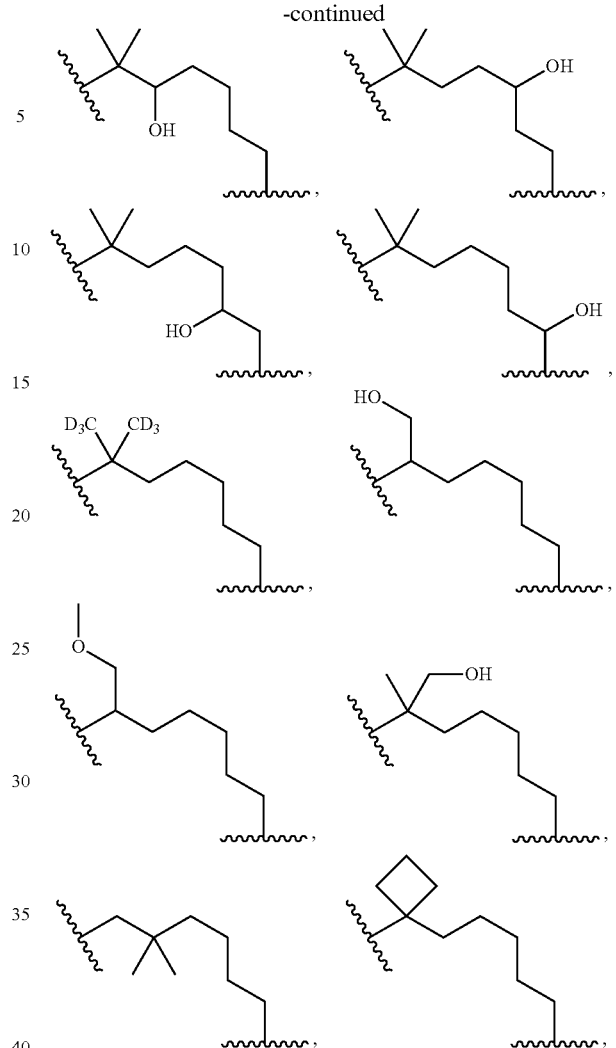
46. The compound, deuterated derivative, or salt according to any one of Embodiments 34-45, wherein —(Y)$_n$— is a group selected from:
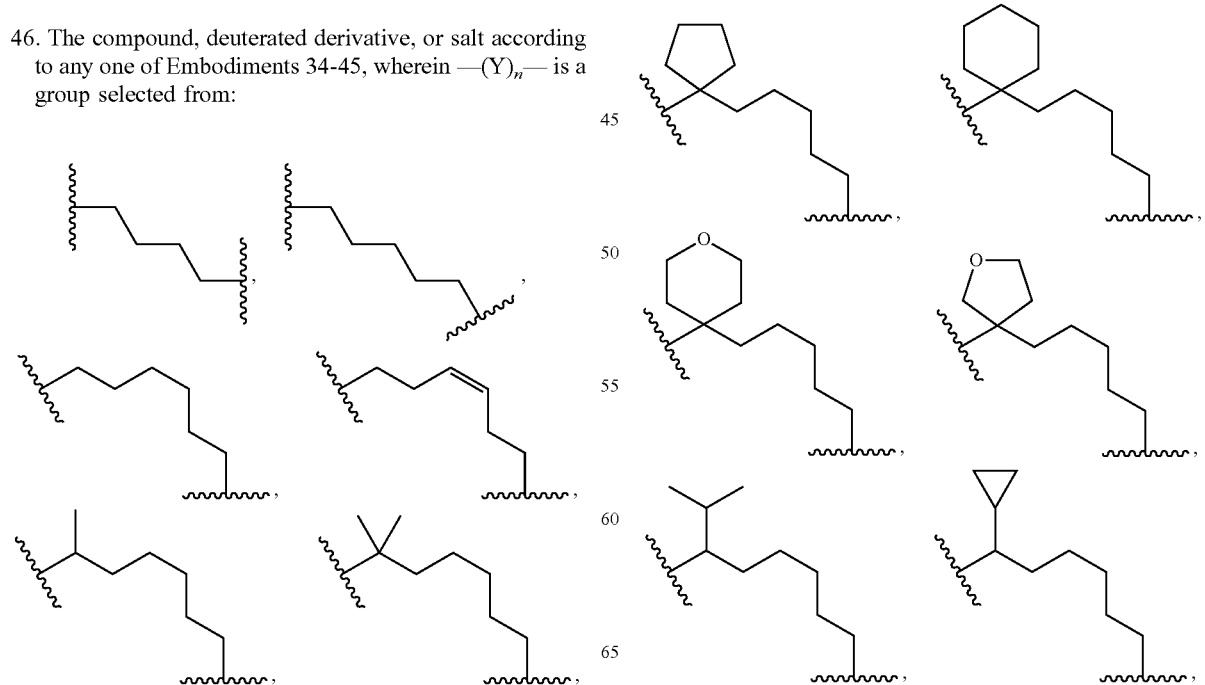

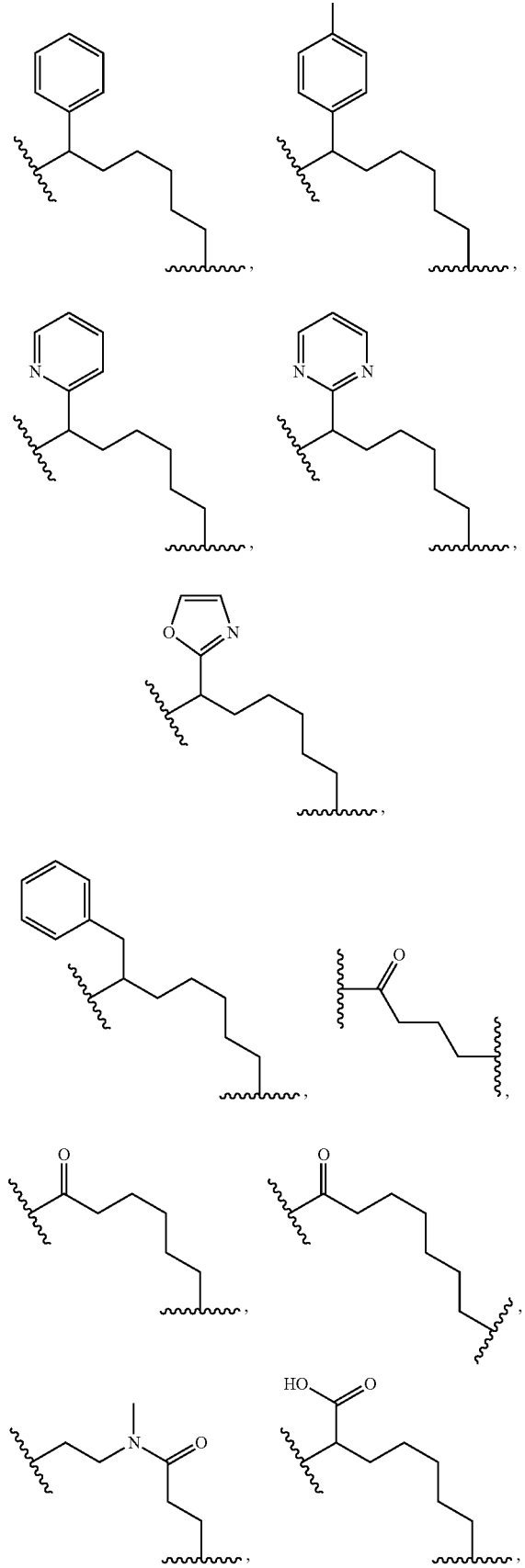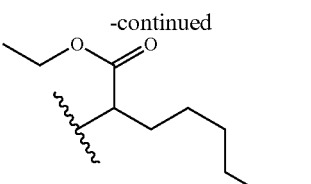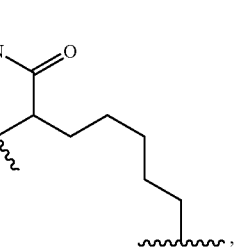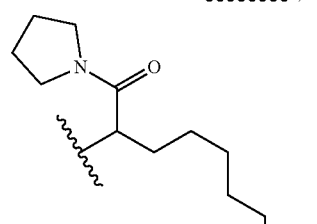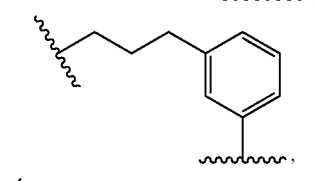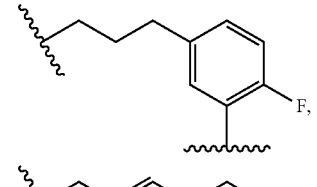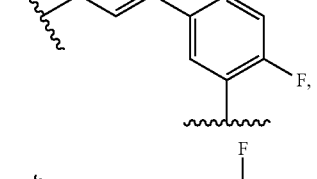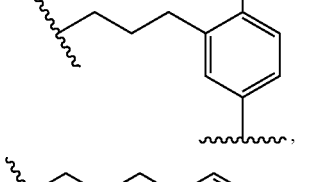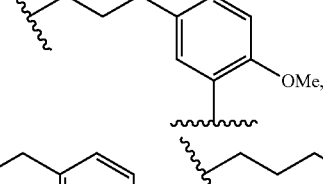

-continued

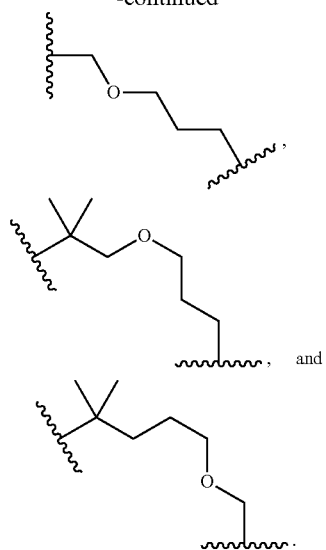

47. The compound, deuterated derivative, or salt according to any one of Embodiments 34-45, wherein each Y is —C(R$^Y$)$_2$—.

48. The compound, deuterated derivative, or salt according to Embodiment 47, wherein each Y is independently selected from —CH$_2$— and —C(Me)$_2$-.

49. The compound, deuterated derivative, or salt according to any one of Embodiments 34-48, wherein each R$^1$ is independently selected from C$_1$-C$_6$ fluoroalkyl and —N(R$^2$)$_2$.

50. The compound, deuterated derivative, or salt according to any one of Embodiments 34-48, wherein each R$^1$ is independently selected from Br, —CH$_3$, —CF$_3$, —CHF$_2$, —OH, —OCH$_3$, —CN, —NH$_2$,

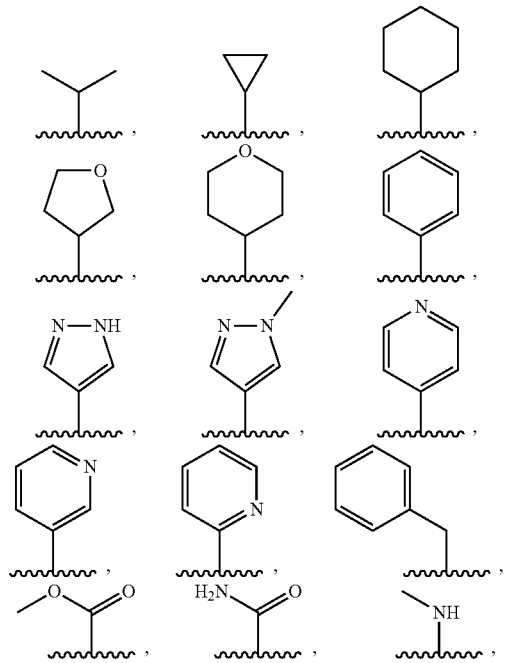

-continued

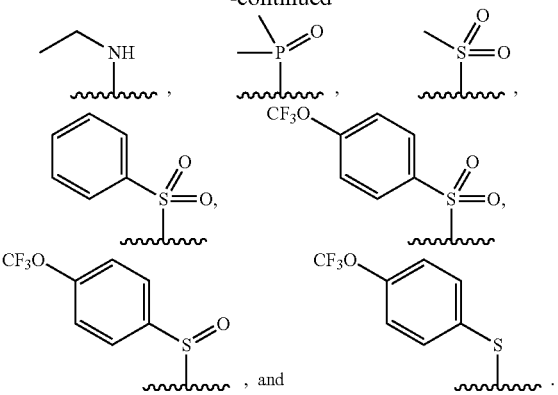

51. The compound, deuterated derivative, or salt according to any one of Embodiments 34-50, wherein each R$^1$ is independently selected from —CF$_3$ and —NH$_2$.

52. The compound, deuterated derivative, or salt according to any one of Embodiments 34-51 wherein Z is selected from:

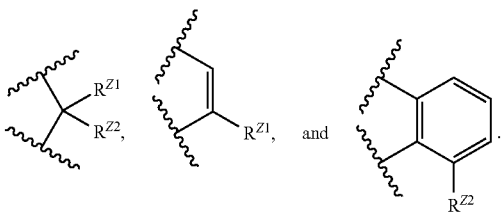

53. The compound, deuterated derivative, or salt according to any one of Embodiments 34-52, wherein:
R$^{Z1}$ is selected from hydrogen, C$_1$-C$_6$ alkyl (optionally substituted with 1-3 hydroxy), C$_1$-C$_6$ fluoroalkyl, 3- to 6-membered heterocyclyl, C$_3$-C$_6$ cycloalkyl, and C$_6$-C$_{10}$ aryl,
R$^{Z2}$ is selected from hydrogen, hydroxy, and C$_1$-C$_6$ alkoxy (optionally substituted with 1-3 groups independently selected from C$_3$-C$_{10}$ cycloalkyl),
or R$^{Z1}$ and R$^{Z2}$ taken together form a group selected from oxo and =N—OH;

54. The compound, deuterated derivative, or salt according to any one of Embodiments 34-53, wherein Z is

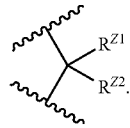

55. The compound, deuterated derivative, or salt according to any one of Embodiments 34-54, wherein

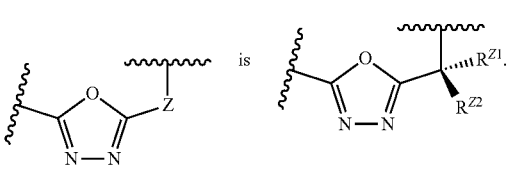

56. The compound, deuterated derivative, or salt according to any one of Embodiments 34-55, wherein $R^{Z1}$ is selected from $C_1$-$C_6$ fluoroalkyl.

57. The compound, deuterated derivative, or salt according to any one of Embodiments 34-56, wherein $R^{Z1}$ is —$CF_3$.

58. The compound, deuterated derivative, or salt according to any one of Embodiments 34-57, wherein $R^{Z2}$ is hydroxy.

59. The compound, deuterated derivative, or salt according to any one of Embodiments 34-53, wherein Z is selected from:

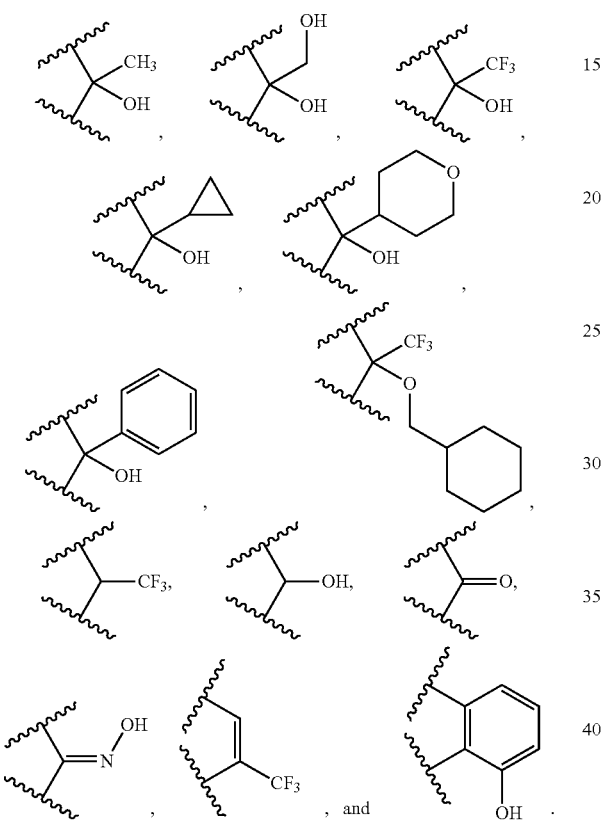

60. The compound, deuterated derivative, or salt according to any one of Embodiments 34-53, wherein

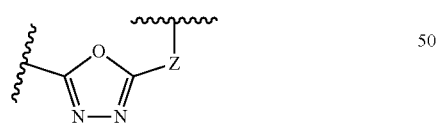

is selected from:

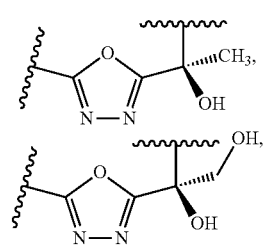

-continued

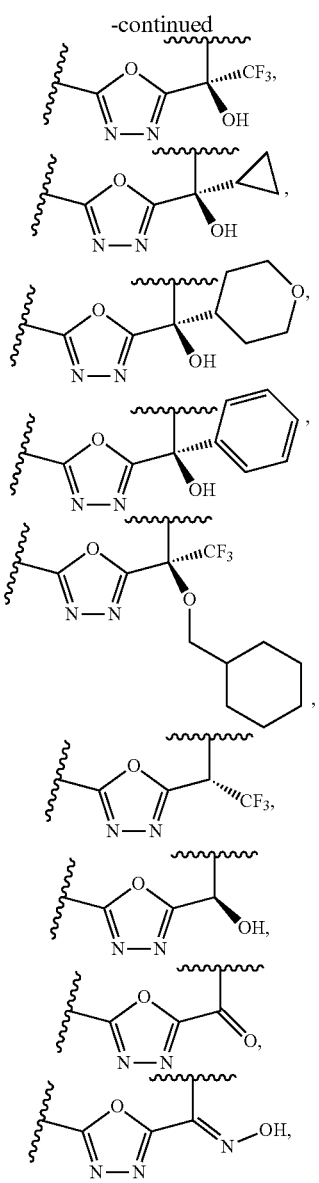

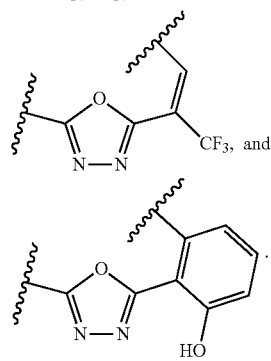

61. The compound, deuterated derivative, or salt according to any one of Embodiments 34-60, wherein n is selected from 4, 5, and 6.

62. The compound, deuterated derivative, or salt according to any one of Embodiments 34-61, wherein n is 5.

63. The compound, deuterated derivative, or salt according to any one of Embodiments 34-62, wherein n is 6.

64. A compound selected from compounds of Formulae IIa, IIb, IIc, and IId:

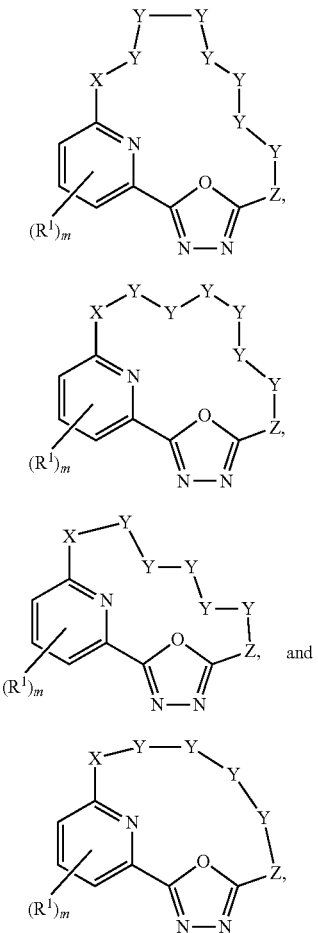

and deuterated derivatives and pharmaceutically acceptable salts thereof, wherein:

X is selected from —NR$^{X1}$— and

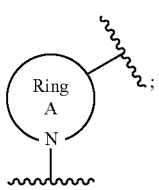

Ring A is a 4- to 6-membered heterocyclyl optionally substituted with 1-3 groups independently selected from $C_1$-$C_6$ alkyl and oxo;

R$^{X1}$ is selected from H, $C_1$-$C_6$ alkyl (optionally substituted with 1-3 groups independently selected from hydroxy, oxo, —OR$^{X2}$, and —N(R$^{X2}$)$_2$), and $C_3$-$C_8$ cycloalkyl;

each R$^{X2}$ is independently selected from H and $C_1$-$C_6$ alkyl;

each Y is independently selected from —C(R$^Y$)$_2$—, —O—, —CO—, —NR$^{YN}$—, and

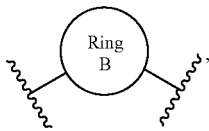

wherein each R$^{YN}$ is independently selected from H, $C_1$-$C_4$ alkyl, and CO$_2$Me;

each R$^Y$ is independently selected from hydrogen, hydroxy, halogen, $C_1$-$C_6$ alkyl (optionally substituted with 1-3 groups independently selected from hydroxy, $C_1$-$C_6$ alkoxy, and Q), $C_3$-$C_8$ cycloalkyl, $C_6$-$C_{10}$ aryl (optionally substituted with 1-3 groups independently selected from halogen), 5- to 10-membered heteroaryl, —OR$^{Y1}$, —CO$_2$R$^{Y1}$, —COR$^{Y1}$, —CON(R$^{Y1}$)$_2$, and —N(R$^{Y1}$)$_2$—;

or two R$^Y$ on the same atom are taken together to form a ring selected from $C_3$-$C_8$ cycloalkyl and 3- to 7-membered heterocyclyl; or two R$^Y$, one of which is on one atom and the second of which is on an adjacent atom, are taken together to form a pi bond;

each R$^{Y1}$ is independently selected from hydrogen and $C_1$-$C_6$ alkyl, or two R$^{Y1}$ bonded to the same nitrogen taken together form a 3- to 6-membered heterocyclyl;

Ring B is selected from:
  $C_6$-$C_{10}$ aryl (optionally substituted with 1-3 groups independently selected from halogen, $C_1$-$C_6$ alkyl, and $C_1$-$C_6$ alkoxy),
  $C_3$-$C_8$ cycloalkyl,
  5- to 10-membered heteroaryl, and
  3- to 6-membered heterocyclyl (optionally substituted with 1-3 groups independently selected from $C_1$-$C_6$ alkyl);

each Q is independently selected from:
  $C_1$-$C_6$ alkyl optionally substituted with 1-3 groups independently selected from:
    halogen,
    oxo,
    $C_6$-$C_{10}$ aryl (optionally substituted with 1-3 groups independently selected from halogen and —OCF$_3$), and
    $C_3$-$C_8$ cycloalkyl,
  $C_3$-$C_8$ cycloalkyl optionally substituted with 1-3 groups independently selected from:
    halogen,
    CN,
    $C_1$-$C_6$ alkyl (optionally substituted with 1-3 groups independently selected from halogen, —NH$_2$, and —NHCOMe),
    $C_1$-$C_6$ alkoxy,
    $C_6$-$C_{10}$ aryl (optionally substituted with 1-3 groups independently selected from $C_1$-$C_6$ alkyl), and
    $C_3$-$C_8$ cycloalkyl,
  $C_6$-$C_{10}$ aryl optionally substituted with 1-3 groups independently selected from:
    halogen,
    CN,
    $C_1$-$C_6$ alkyl (optionally substituted with 1-3 groups independently selected from halogen and hydroxy),
    $C_1$-$C_6$ alkoxy optionally substituted with 1-4 groups independently selected from:
      halogen,
      $C_3$-$C_8$ cycloalkyl (optionally substituted with CF$_3$), C₃-C₈ cycloalkyl (optionally substituted with 1-3 groups independently selected from halogen, CF₃, OCF₃, and C₁-C₆ alkyl), and
C₆-C₁₀ aryl,
5- to 10-membered heteroaryl optionally substituted with 1-3 groups independently selected from:
halogen,
C₁-C₆ alkyl (optionally substituted with 1-3 groups independently selected from halogen),
C₃-C₈ cycloalkyl (optionally substituted with 1-3 CF₃ groups), and
3- to 10-membered heterocyclyl,
3- to 10-membered heterocyclyl optionally substituted with 1-3 groups independently selected from:
C₁-C₆ alkyl (optionally substituted with 1-3 groups independently selected from oxo and C₃-C₈ cycloalkyl), and
oxo;
each R¹ is independently selected from halogen, C₁-C₆ fluoroalkyl, C₁-C₆ alkyl (optionally substituted with a group selected from C₆-C₁₀ aryl and 5- to 6-membered heteroaryl), —OR², —N(R²)₂, —CO₂R², —CO—N(R²)₂, —CN, C₁-C₆ alkoxy, C₃-C₈ cycloalkyl, C₆-C₁₀ aryl, 5- to 6-membered heteroaryl (optionally substituted with 1-3 groups independently selected from C₁-C₆ alkyl), 3- to 6-membered heterocyclyl, —SO₂R², —SR², —SOR², —PO(OR²)₂, and —PO(R²)₂;
each R² is independently selected from hydrogen, C₁-C₆ alkyl (optionally substituted with 1-6 groups independently selected from halogen), C₁-C₆ fluoroalkyl, and C₆-C₁₀ aryl (optionally substituted with 1-3 groups independently selected from C₁-C₆ fluoroalkyl and C₁-C₆ fluoroalkoxy);
Z is selected from

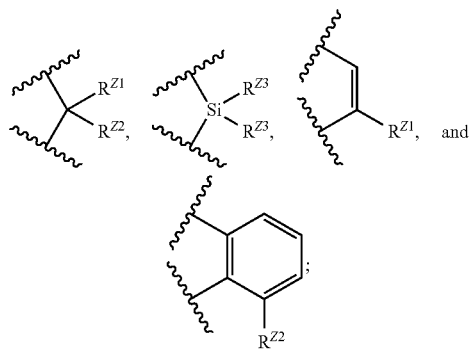

R^Z1 is selected from hydrogen, —CN, C₁-C₆ alkyl (optionally substituted with 1-3 hydroxy), C₁-C₆ fluoroalkyl, 3- to 6-membered heterocyclyl, C₃-C₆ cycloalkyl, C₆-C₁₀ aryl, and 5- to 6-membered heteroaryl;
R^Z2 is selected from hydrogen, halogen, hydroxy, and C₁-C₆ alkoxy (optionally substituted with 1-3 groups independently selected from C₃-C₁₀ cycloalkyl),
or R^Z1 and R^Z2 taken together form a group selected from oxo and =N—OH;
each R^Z3 is independently selected from hydroxy, C₁-C₆ alkoxy, C₁-C₆ alkyl, and C₆-C₁₀ aryl; or two R^Z3 are taken together to form a 3- to 6-membered heterocyclyl; and
m is selected from 0, 1, 2, and 3.

65. The compound according to Embodiment 64, wherein m is selected from 1 and 2.
66. The compound according to Embodiment 64 or 65, wherein m is 2.
67. A compound selected from compounds of Formulae IIe, IIf, IIg, and IIh:

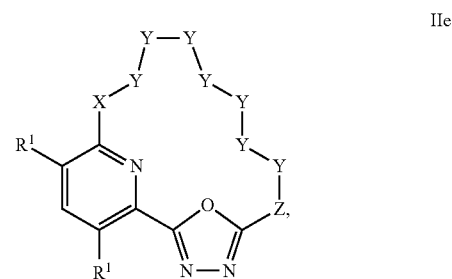

IIe

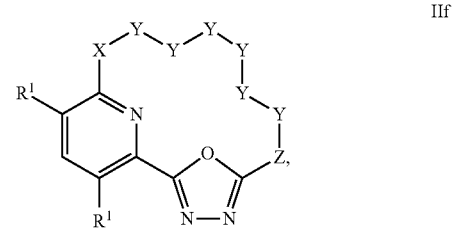

IIf

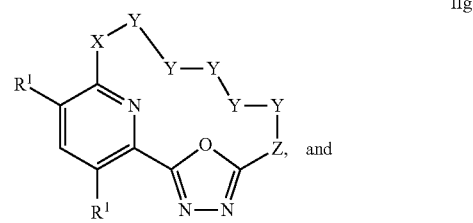

IIg, and

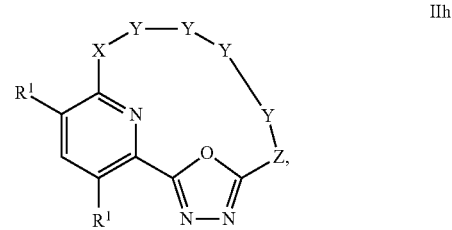

IIh and deuterated derivatives and pharmaceutically acceptable salts thereof, wherein:
X is selected from —NR^X1— and

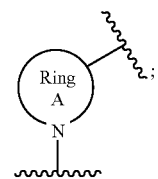

Ring A is a 4- to 6-membered heterocyclyl optionally substituted with 1-3 groups independently selected from C₁-C₆ alkyl and oxo;
R^X1 is selected from H, C₁-C₆ alkyl (optionally substituted with 1-3 groups independently selected from hydroxy, oxo, —OR^X2, and —N(R^X2)₂), and C₃-C₈ cycloalkyl;

each $R^{X1}$ is independently selected from H and $C_1$-$C_6$ alkyl;

each Y is independently selected from —C($R^Y$)$_2$—, —O—, —CO—, —N$R^{YN}$—, and

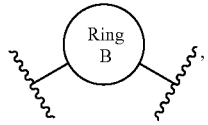

wherein each $R^{YN}$ is independently selected from H, $C_1$-$C_4$ alkyl, and CO$_2$Me;

each $R^Y$ is independently selected from hydrogen, hydroxy, halogen, $C_1$-$C_6$ alkyl (optionally substituted with 1-3 groups independently selected from hydroxy, $C_1$-$C_6$ alkoxy, and Q), $C_3$-$C_8$ cycloalkyl, $C_6$-$C_{10}$ aryl (optionally substituted with 1-3 groups independently selected from halogen), 5- to 10-membered heteroaryl, —O$R^{Y1}$, —CO$_2R^{Y1}$, —CON($R^{Y1}$)$_2$, and —N($R^{Y1}$)$_2$—;

or two $R^Y$ on the same atom are taken together to form a ring selected from $C_3$-$C_8$ cycloalkyl and 3- to 7-membered heterocyclyl; or two $R^Y$, one of which is on one atom and the second of which is on an adjacent atom, are taken together to form a pi bond;

each $R^{Y1}$ is independently selected from hydrogen and $C_1$-$C_6$ alkyl, or two $R^{Y1}$ bonded to the same nitrogen taken together form a 3- to 6-membered heterocyclyl;

Ring B is selected from:
  $C_6$-$C_{10}$ aryl (optionally substituted with 1-3 groups independently selected from halogen, $C_1$-$C_6$ alkyl, and $C_1$-$C_6$ alkoxy),
  $C_3$-$C_8$ cycloalkyl,
  5- to 10-membered heteroaryl, and
  3- to 6-membered heterocyclyl (optionally substituted with 1-3 groups independently selected from $C_1$-$C_6$ alkyl);

each Q is independently selected from:
  $C_1$-$C_6$ alkyl optionally substituted with 1-3 groups independently selected from:
    halogen,
    oxo,
    $C_6$-$C_{10}$ aryl (optionally substituted with 1-3 groups independently selected from halogen and —OCF$_3$), and
    $C_3$-$C_8$ cycloalkyl,
  $C_3$-$C_8$ cycloalkyl optionally substituted with 1-3 groups independently selected from:
    halogen,
    CN,
    $C_1$-$C_6$ alkyl (optionally substituted with 1-3 groups independently selected from halogen, —NH$_2$, and —NHCOMe),
    $C_1$-$C_6$ alkoxy,
    $C_6$-$C_{10}$ aryl (optionally substituted with 1-3 groups independently selected from $C_1$-$C_6$ alkyl), and
    $C_3$-$C_8$ cycloalkyl,
  $C_6$-$C_{10}$ aryl optionally substituted with 1-3 groups independently selected from:
    halogen,
    CN,
    $C_1$-$C_6$ alkyl (optionally substituted with 1-3 groups independently selected from halogen and hydroxy),
  $C_1$-$C_6$ alkoxy optionally substituted with 1-4 groups independently selected from:
    halogen,
    $C_3$-$C_8$ cycloalkyl (optionally substituted with CF$_3$),
    $C_3$-$C_8$ cycloalkyl (optionally substituted with 1-3 groups independently selected from halogen, CF$_3$, OCF$_3$, and $C_1$-$C_6$ alkyl), and
    $C_6$-$C_{10}$ aryl,
  5- to 10-membered heteroaryl optionally substituted with 1-3 groups independently selected from:
    halogen,
    $C_1$-$C_6$ alkyl (optionally substituted with 1-3 groups independently selected from halogen),
    $C_3$-$C_8$ cycloalkyl (optionally substituted with 1-3 CF$_3$ groups), and
    3- to 10-membered heterocyclyl,
  3- to 10-membered heterocyclyl optionally substituted with 1-3 groups independently selected from:
    $C_1$-$C_6$ alkyl (optionally substituted with 1-3 groups independently selected from oxo and $C_3$-$C_8$ cycloalkyl), and
    oxo;

each $R^1$ is independently selected from halogen, $C_1$-$C_6$ fluoroalkyl, $C_1$-$C_6$ alkyl (optionally substituted with a group selected from $C_6$-$C_{10}$ aryl and 5- to 6-membered heteroaryl), —O$R^2$, —N($R^2$)$_2$, —CO$_2R^2$, —CO—N($R^2$)$_2$, —CN, $C_1$-$C_6$ alkoxy, $C_3$-$C_8$ cycloalkyl, $C_6$-$C_{10}$ aryl, 5- to 6-membered heteroaryl (optionally substituted with 1-3 groups independently selected from $C_1$-$C_6$ alkyl), 3- to 6-membered heterocyclyl, —SO$_2R^2$, —S$R^2$, —SO$R^2$, —PO(O$R^2$)$_2$, and —PO($R^2$)$_2$;

each $R^2$ is independently selected from hydrogen, $C_1$-$C_6$ alkyl (optionally substituted with 1-6 groups independently selected from halogen), $C_1$-$C_6$ fluoroalkyl, and $C_6$-$C_{10}$ aryl (optionally substituted with 1-3 groups independently selected from $C_1$-$C_6$ fluoroalkyl and $C_1$-$C_6$ fluoroalkoxy);

Z is selected from

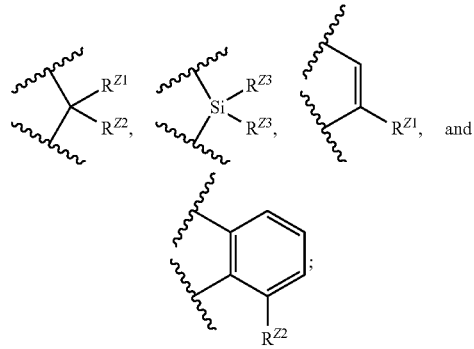

$R^{Z1}$ is selected from hydrogen, —CN, $C_1$-$C_6$ alkyl (optionally substituted with 1-3 hydroxy), $C_1$-$C_6$ fluoroalkyl, 3- to 6-membered heterocyclyl, $C_3$-$C_6$ cycloalkyl, $C_6$-$C_{10}$ aryl, and 5- to 6-membered heteroaryl;

$R^{Z2}$ is selected from hydrogen, halogen, hydroxy, and $C_1$-$C_6$ alkoxy (optionally substituted with 1-3 groups independently selected from $C_3$-$C_{10}$ cycloalkyl), or $R^{Z1}$ and $R^{Z2}$ taken together form a group selected from oxo and =N—OH; and each $R^{Z3}$ is independently selected from hydroxy, $C_1$-$C_6$ alkoxy, $C_1$-$C_6$ alkyl, and $C_6$-$C_{10}$ aryl; or two $R^{Z3}$ are taken together to form a 3- to 6-membered heterocyclyl.

68. The compound, deuterated derivative, or salt according to any one of Embodiments 64-67, wherein X is —$NR^{X1}$.

69. The compound, deuterated derivative, or salt according to any one of Embodiments 64-68, wherein X is selected from:

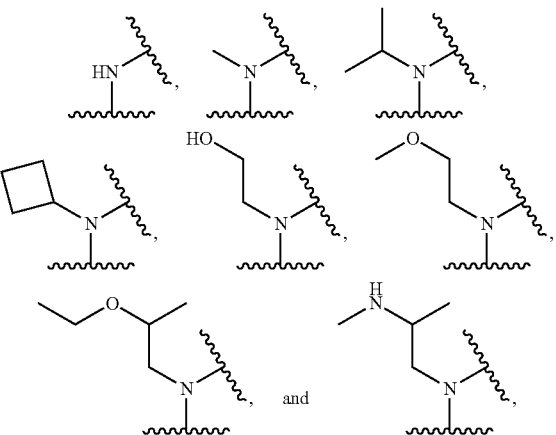

70. The compound, deuterated derivative, or salt according to any one of Embodiments 64-67, wherein X is

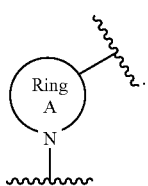

71. The compound, deuterated derivative, or salt according to any one of Embodiments 64-67 or 70, wherein Ring A is selected from pyrrolidine, piperazine, morpholine, and isothiazolidine.

72. The compound, deuterated derivative, or salt according to any one of Embodiments 64-67, 70, or 71, wherein X is selected from:

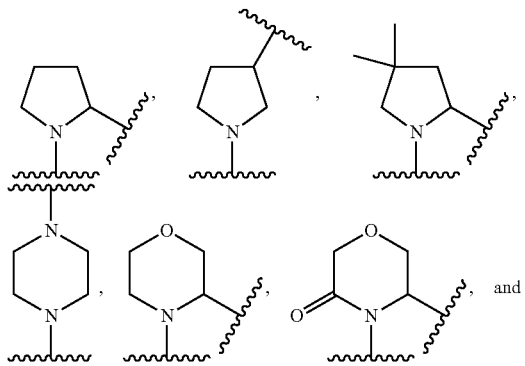

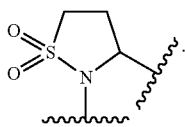

73. The compound, deuterated derivative, or salt according to any one of Embodiments 64-72, wherein each $R^Y$ is independently selected from: hydrogen, hydroxy, methyl,

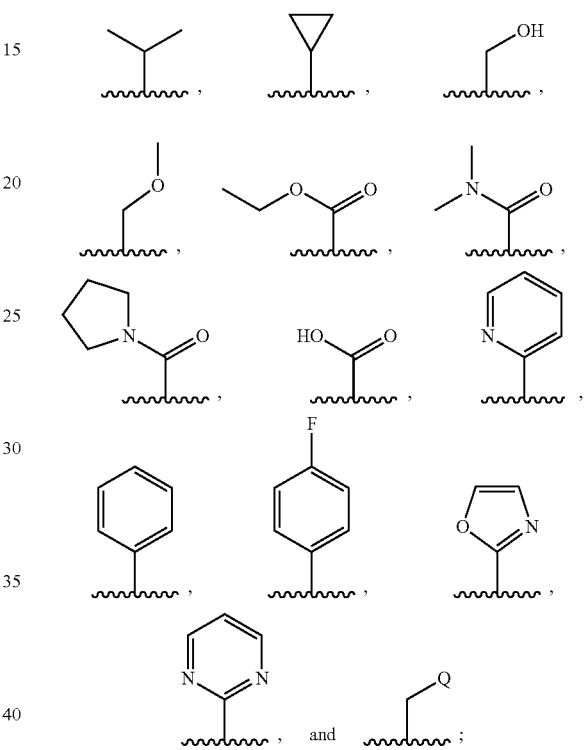

or wherein two $R^Y$ on the same atom are taken together to form a ring selected from cyclobutyl, cyclopentyl, cyclohexyl, tetrahydrofuranyl, and tetrahydropyranyl; or wherein two $R^Y$, one of which is on one atom and the second of which is on an adjacent atom, are taken together to form a pi bond.

74. The compound, deuterated derivative, or salt according to any one of Embodiments 64-73, wherein each Q is independently selected from $C_6$-$C_{10}$ aryl optionally substituted with 1-3 groups independently selected from halogen and $C_1$-$C_6$ alkyl.

75. The compound, deuterated derivative, or salt according to any one of Embodiments 64-74, wherein each Q is phenyl.

76. The compound, deuterated derivative, or salt according to any one of Embodiments 64-75, wherein each Ring B is independently selected from $C_6$-$C_{10}$ aryl (optionally substituted with 1-3 groups independently selected from halogen and $C_1$-$C_6$ alkoxy) and 5- to 10-membered heteroaryl.

77. The compound, deuterated derivative, or salt according to any one of Embodiments 64-76, wherein each Ring B is independently selected from:

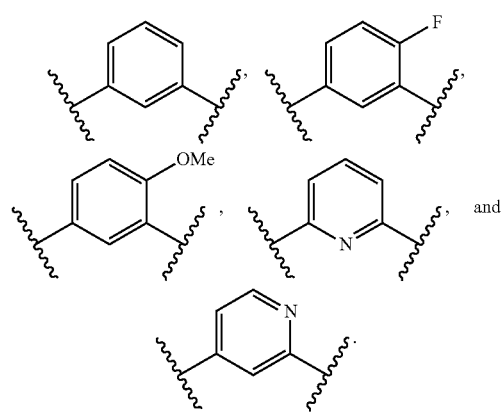

78. The compound, deuterated derivative, or salt according to any one of Embodiments 64-77, wherein (—Y—Y—Y—Y—Y—Y—Y—) is a group selected from:

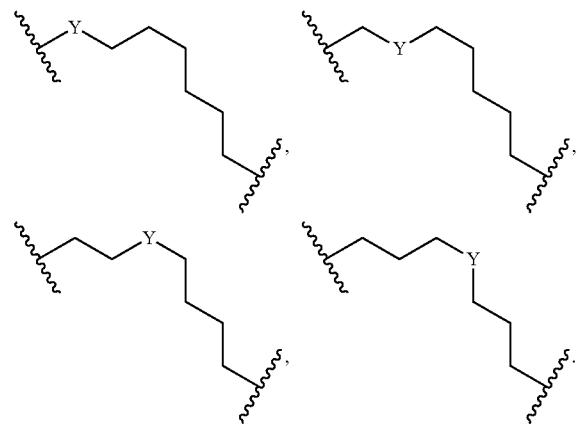

79. The compound, deuterated derivative, or salt according to Embodiment 78, wherein (—Y—Y—Y—Y—Y—Y—Y—) is

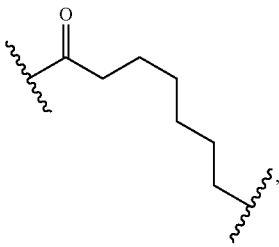 [SMILES: *CCCCCCC(*)=O]

80. The compound, deuterated derivative, or salt according to any one of Embodiments 64-77, wherein (—Y—Y—Y—Y—Y—Y—) is a group selected from:

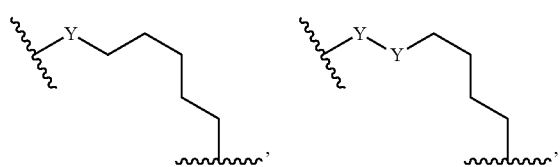

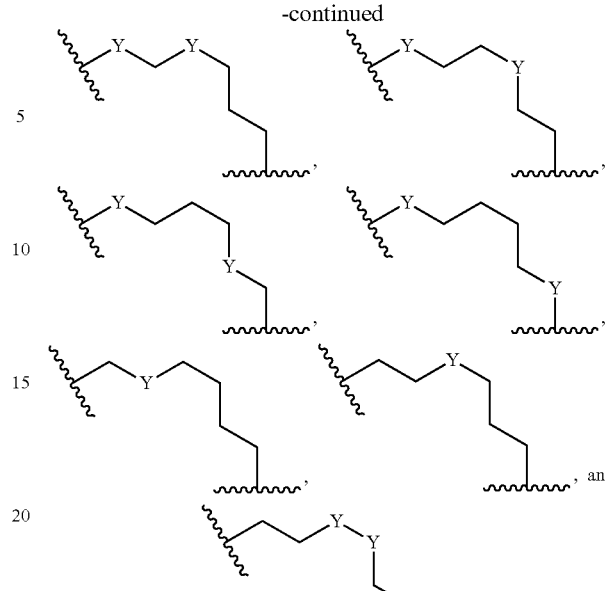

81. The compound, deuterated derivative, or salt according to Embodiment 80, wherein (—Y—Y—Y—Y—Y—Y—) is a group selected from:

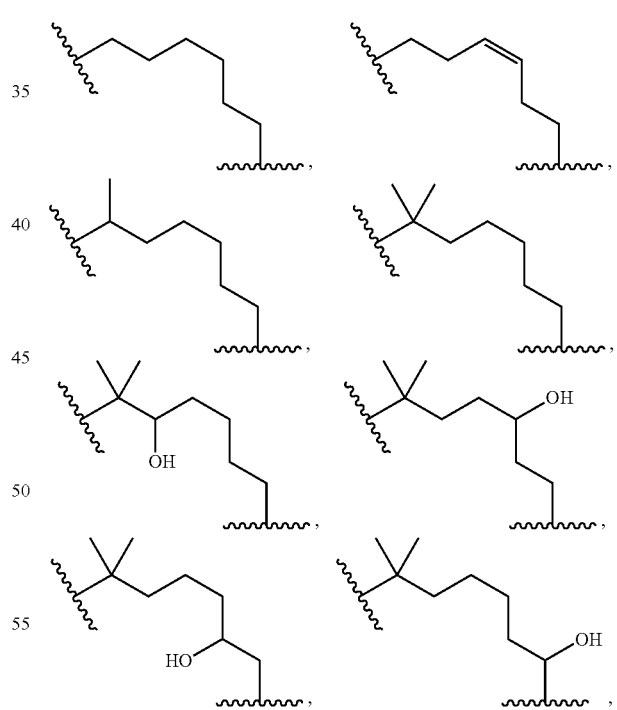

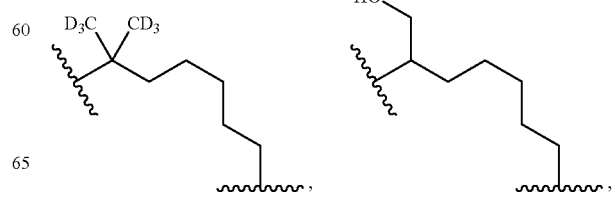

101
-continued
102
-continued
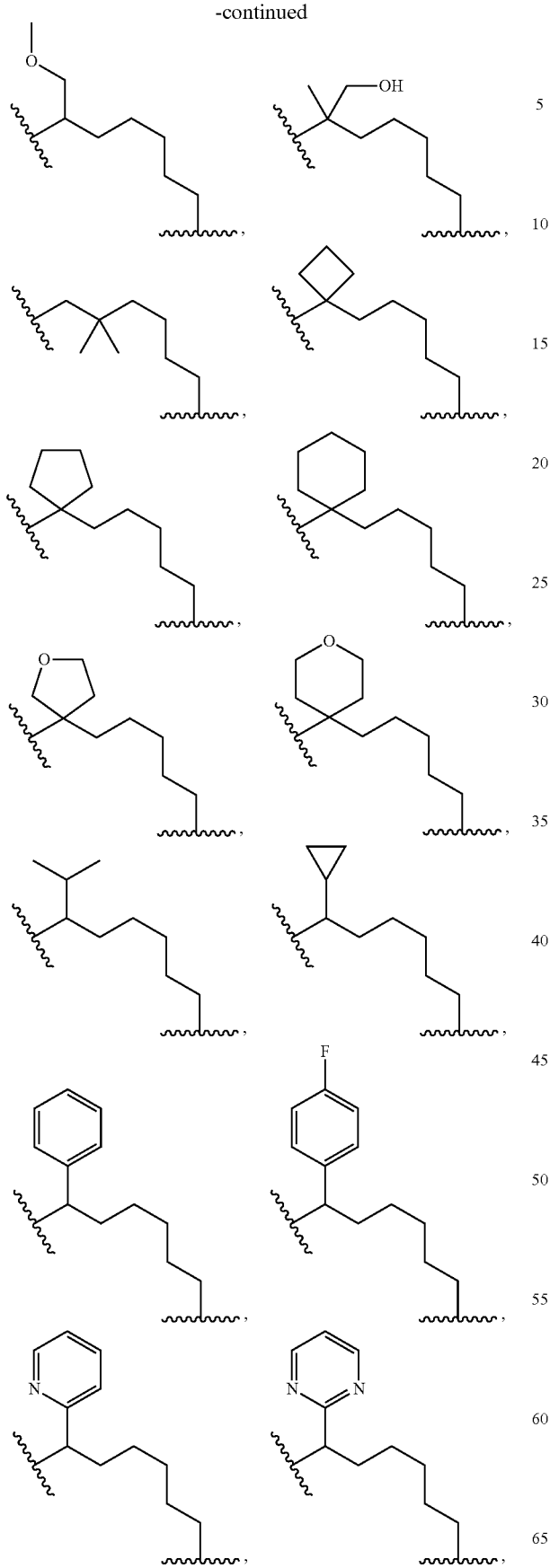
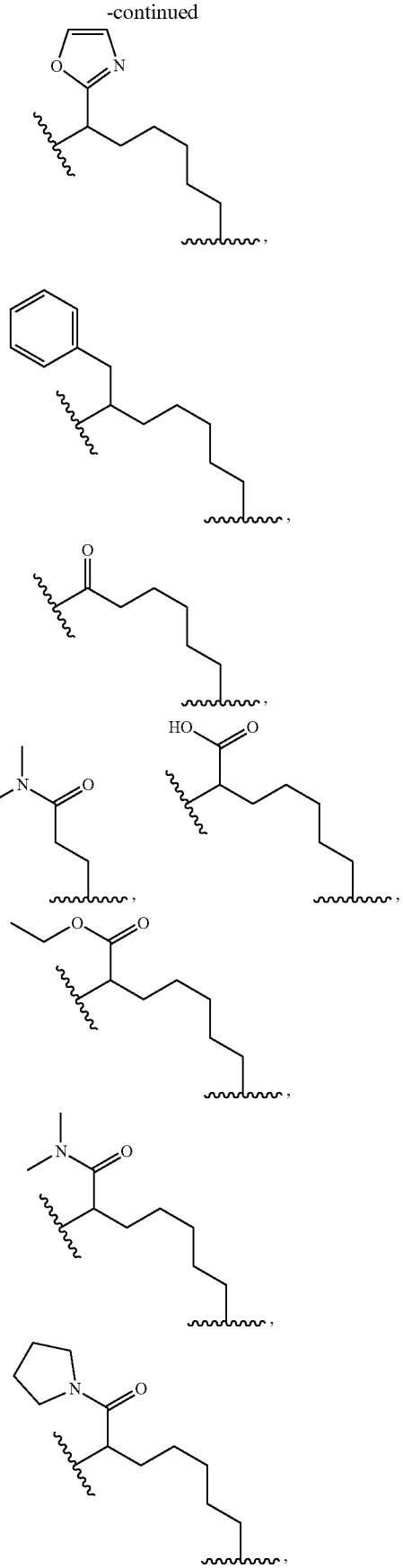

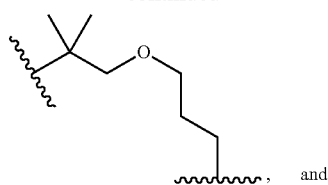, and

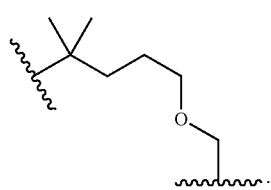.

82. The compound, deuterated derivative, or salt according to any one of Embodiments 64-77, wherein (—Y—Y—Y—Y—Y—) is a group selected from:

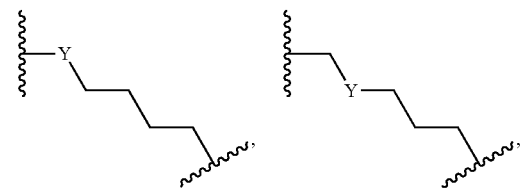

83. The compound, deuterated derivative, or salt according to any one of Embodiments 82, wherein (—Y—Y—Y—Y—Y—) is a group selected from:

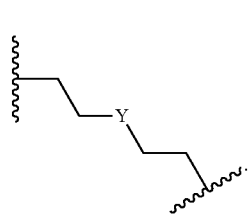

84. The compound, deuterated derivative, or salt according to Embodiments 64-77, wherein (—Y—Y—Y—Y—) is a group selected from:

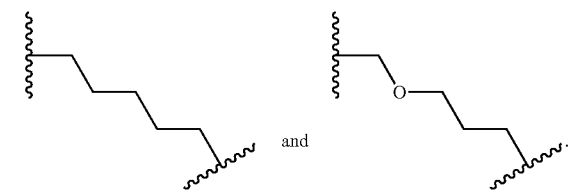 [SMILES: *CCCCC* ; *CCCOC*]

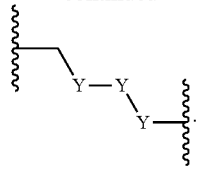

85. The compound, deuterated derivative, or salt according to Embodiment 84, wherein (—Y—Y—Y—Y—) is a group selected from:

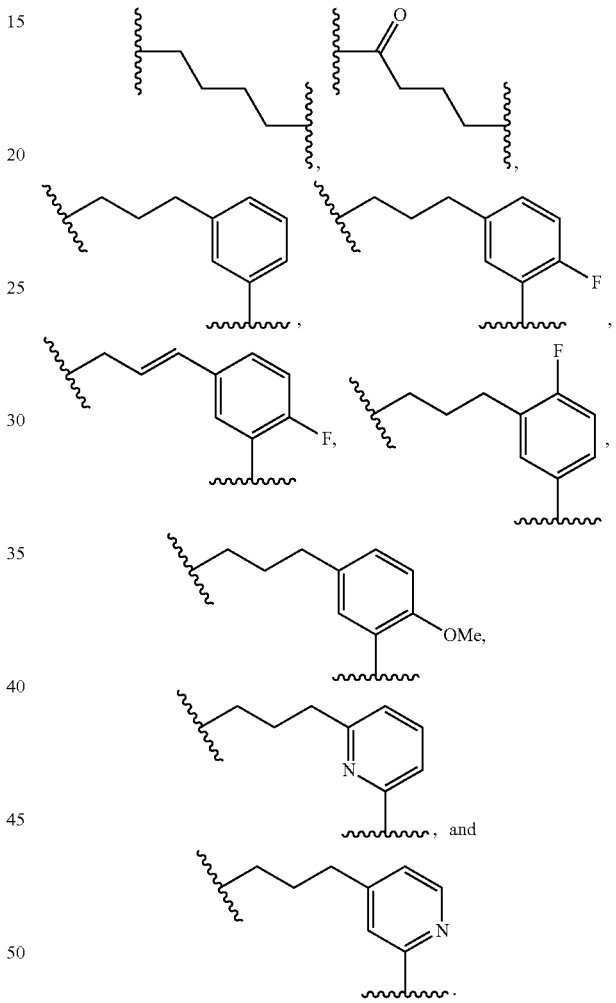

86. The compound, deuterated derivative, or salt according to any one of Embodiments 64-77, wherein each Y is —C(R$^Y$)$_2$—.
87. The compound, deuterated derivative, or salt according to Embodiment 86, wherein each Y is independently selected from —CH$_2$— and —C(Me)$_2$.
88. The compound, deuterated derivative, or salt according to any one of Embodiments 64-87, wherein each R$^1$ is independently selected from C$_1$-C$_6$ fluoroalkyl and —N(R$^2$)$_2$.
89. The compound, deuterated derivative, or salt according to any one of Embodiments 64-87, wherein each R$^1$ is independently selected from Br, —CH$_3$, —CF$_3$, —CHF$_2$, —OH, —OCH$_3$, —CN, —NH$_2$,

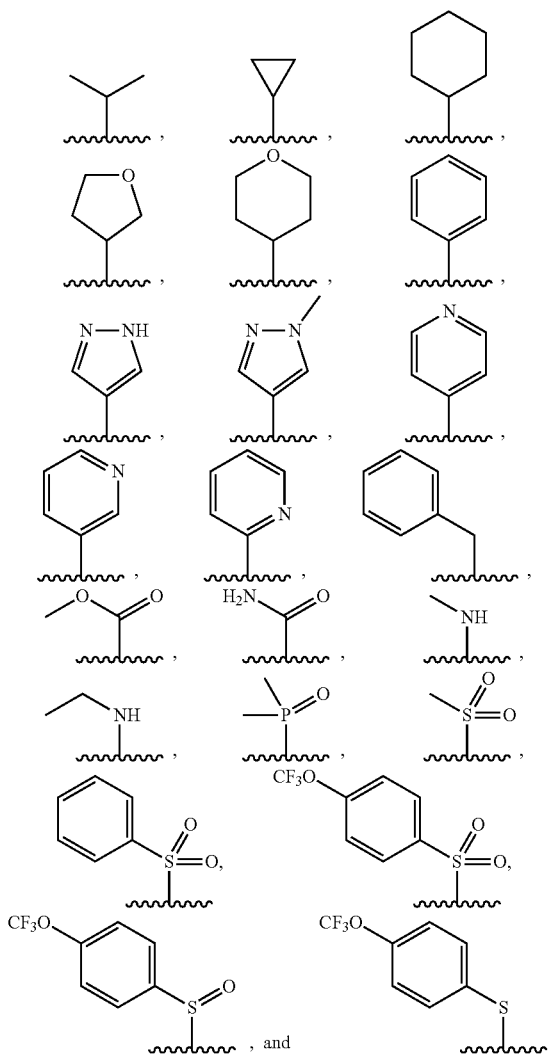

90. The compound, deuterated derivative, or salt according to any one of Embodiments 64-89, wherein each $R^1$ is independently selected from —$CF_3$ and —$NH_2$.
91. The compound, deuterated derivative, or salt according to any one of Embodiments 64-90, wherein Z is selected from:

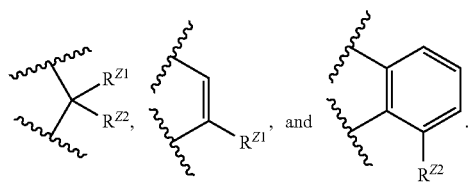

92. The compound, deuterated derivative, or salt according to any one of Embodiments 64-91, wherein:
   $R^{Z1}$ is selected from hydrogen, $C_1$-$C_6$ alkyl (optionally substituted with 1-3 hydroxy), $C_1$-$C_6$ fluoroalkyl, 3- to 6-membered heterocyclyl, $C_3$-$C_6$ cycloalkyl, and $C_6$-$C_{10}$ aryl,
   $R^{Z2}$ is selected from hydrogen, hydroxy, and $C_1$-$C_6$ alkoxy (optionally substituted with 1-3 groups independently selected from $C_3$-$C_{10}$ cycloalkyl), or $R^{Z1}$ and $R^{Z2}$ taken together form a group selected from oxo and =N—OH;
93. The compound, deuterated derivative, or salt according to any one of Embodiments 64-92, wherein Z is

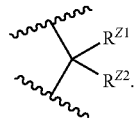

94. The compound, deuterated derivative, or salt according to any one of Embodiments 64-93, wherein

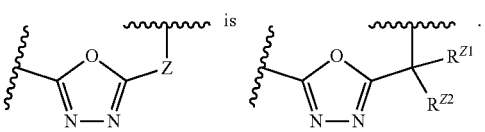

95. The compound, deuterated derivative, or salt according to any one of Embodiments 64-94, wherein $R^{Z1}$ is selected from $C_1$-$C_6$ fluoroalkyl.
96. The compound, deuterated derivative, or salt according to any one of Embodiments 64-95, wherein $R^{Z1}$ is —$CF_3$.
97. The compound, deuterated derivative, or salt according to any one of Embodiments 64-96, wherein $R^{Z2}$ is hydroxy.
98. The compound, deuterated derivative, or salt according to any one of Embodiments 64-92, wherein Z is selected from:

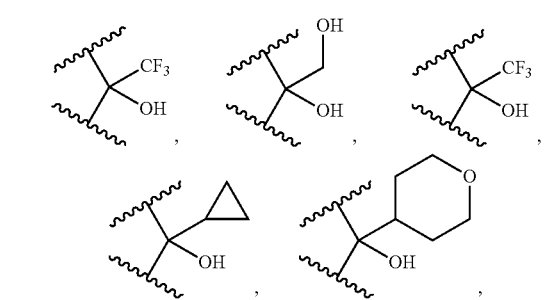

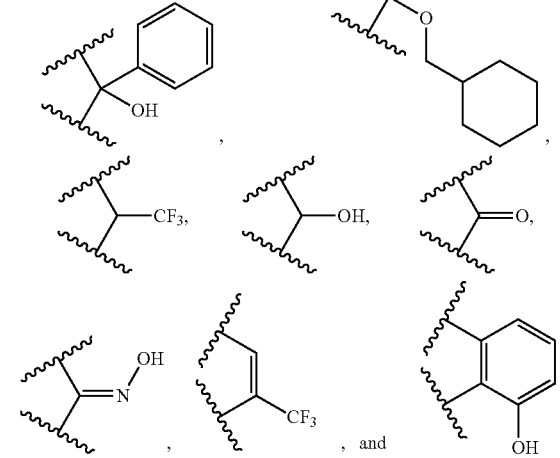

99. The compound, deuterated derivative, or salt according to any one of Embodiments 64-92, wherein

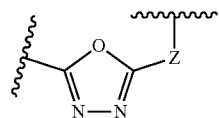

is selected from:

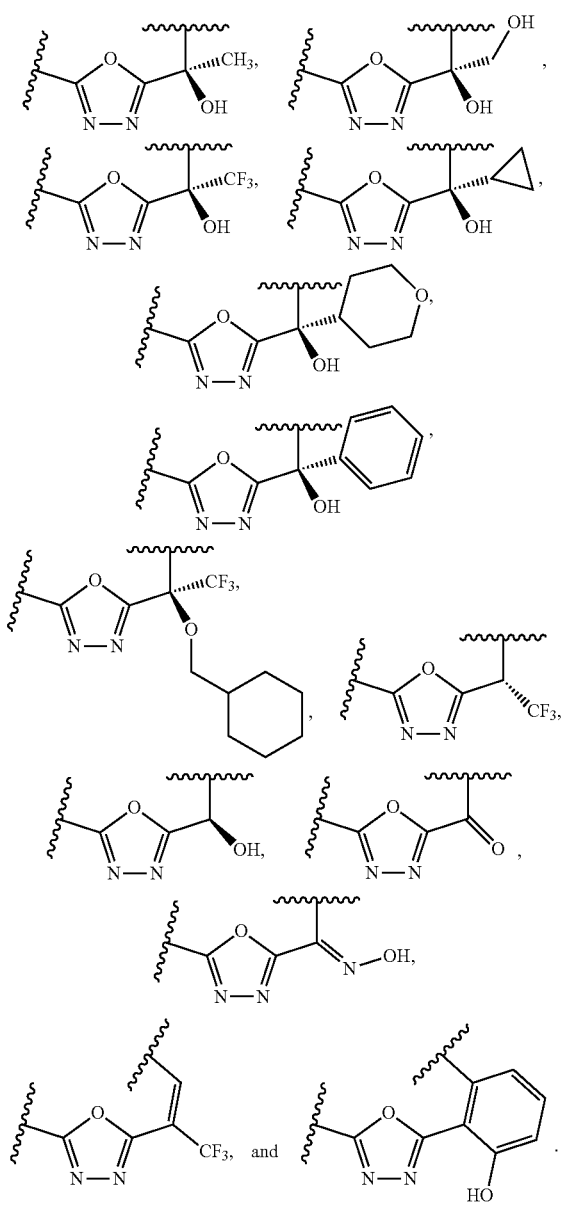

100. The compound, deuterated derivative, or pharmaceutically acceptable salt according to Embodiment 1, wherein X is —N(R$^{X1}$)—.

101. The compound, deuterated derivative, or pharmaceutically acceptable salt according to Embodiment 1, wherein X is

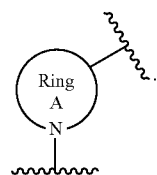

102. The compound, deuterated derivative, or pharmaceutically acceptable salt according to Embodiment 1, wherein X is selected from:

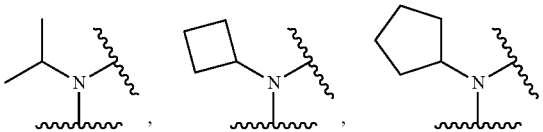
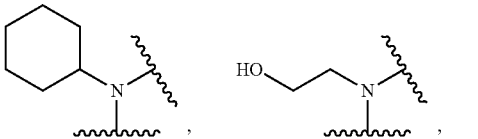
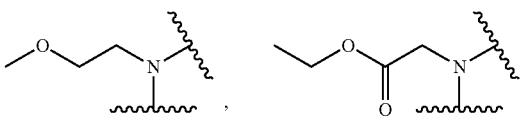
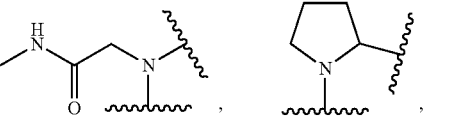
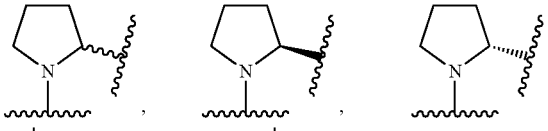

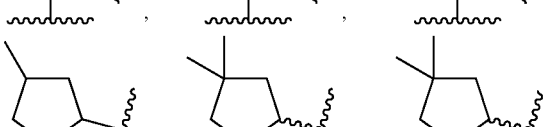
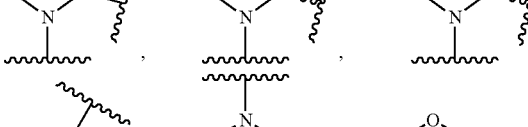
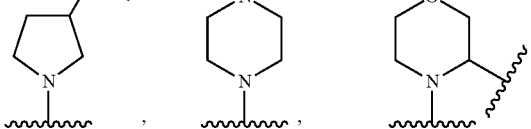
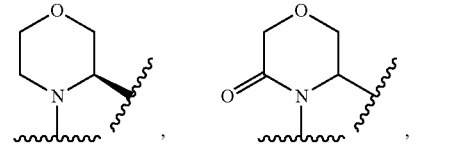

-continued

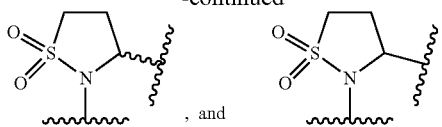

, and .

103. The compound, deuterated derivative, or pharmaceutically acceptable salt according to any one of Embodiments 1 and 100-102, wherein:
  each $R^Y$ is independently selected from hydrogen, hydroxy, halogen, $C_1$-$C_6$ alkyl (optionally substituted with 1-3 groups independently selected from hydroxy, $C_1$-$C_6$ alkoxy, and Q), $C_3$-$C_8$ cycloalkyl, $C_6$-$C_{10}$ aryl (optionally substituted with 1-3 groups independently selected from halogen), 5- to 10-membered heteroaryl, —$CO_2R^{Y1}$, and —$CON(R^{Y1})_2$;
  or two $R^Y$ on the same atom are taken together to form a ring selected from $C_3$-$C_8$ cycloalkyl and 3- to 7-membered heterocyclyl;
  or two $R^Y$, one of which is on one atom and the second of which is on an adjacent atom, are taken together to form a pi bond.
104. The compound, deuterated derivative, or pharmaceutically acceptable salt according to any one of Embodiments 1 and 100-103, wherein each $R^{Y1}$ is independently selected from hydrogen and $C_1$-$C_6$ alkyl, or two $R^{Y1}$ bonded to the same nitrogen taken together form a 3- to 6-membered heterocyclyl.
105. The compound, deuterated derivative, or pharmaceutically acceptable salt according to any one of Embodiments 1 and 100-104, wherein each Q is independently selected from $C_6$-$C_{10}$ aryl.
106. The compound, deuterated derivative, or pharmaceutically acceptable salt according to any one of Embodiments 1 and 100-105, wherein each Q is phenyl.
107. The compound, deuterated derivative, or pharmaceutically acceptable salt according to any one of Embodiments 1 and 100-106, wherein:
  each $R^Y$ is independently selected from:

hydrogen, hydroxy, —$CH_3$, —$CD_3$, —$CH_2CH_3$,

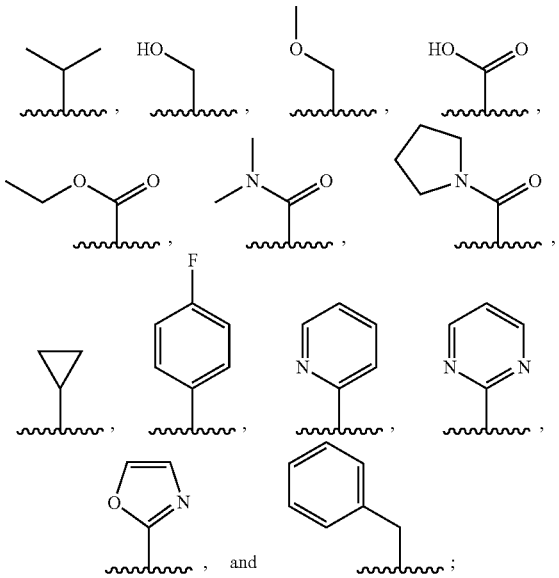

, and ;

or two $R^Y$ on the same atom are taken together to form a ring selected from cyclobutyl, cyclopentyl, cyclohexyl, tetrahydropyrrol, and tetrahydrofuryl;
or two $R^Y$, one of which is on one atom and the second of which is on an adjacent atom, are taken together to form a pi bond.

108. The compound, deuterated derivative, or pharmaceutically acceptable salt according to any one of Embodiments 1 and 100-107, wherein Ring B is selected from $C_6$-$C_{10}$ aryl (optionally substituted with 1-3 groups independently selected from halogen and $C_1$-$C_6$ alkoxy) and 5- to 10-membered heteroaryl.
109. The compound, deuterated derivative, or pharmaceutically acceptable salt according to any one of Embodiments 1 and 100-108, wherein Ring B is selected from phenyl (optionally substituted with 1-3 groups independently selected from halogen and $C_1$-$C_6$ alkoxy) and pyridyl.
110. The compound, deuterated derivative, or pharmaceutically acceptable salt according to any one of Embodiments 1 and 100-109, wherein Ring B is selected from:

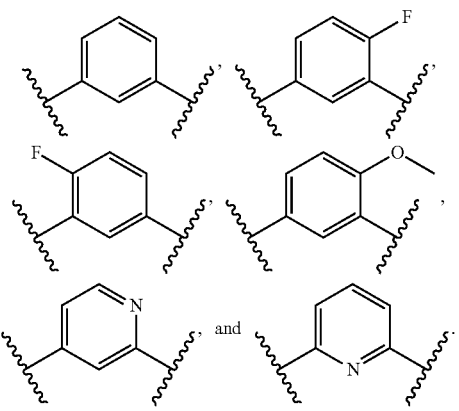

111. The compound, deuterated derivative, or pharmaceutically acceptable salt according to any one of Embodiments 1 and 100-110, wherein n is selected from 4, 5, 6, and 7.
112. The compound, deuterated derivative, or pharmaceutically acceptable salt according to any one of Embodiments 1 and 100-111, wherein —$(Y)_n$— is a group selected from:

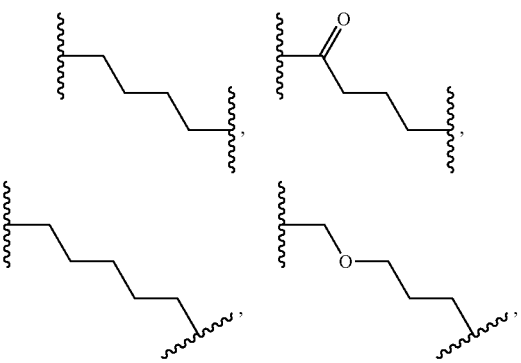

111
-continued
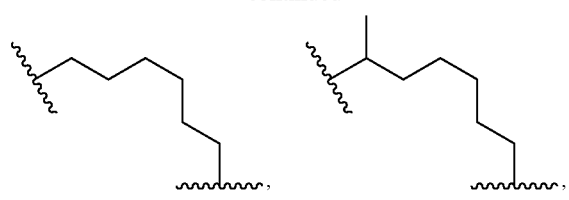
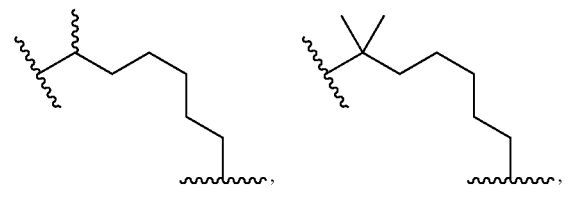
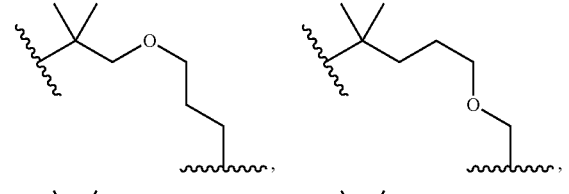
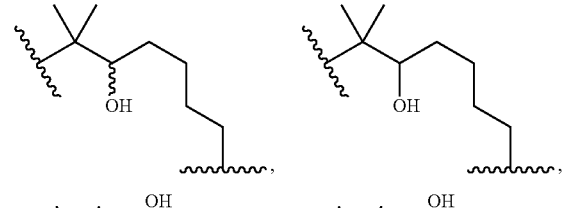
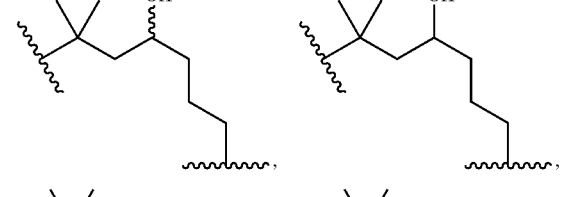
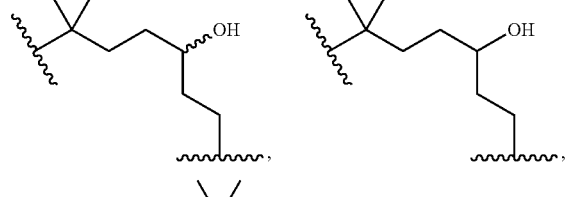
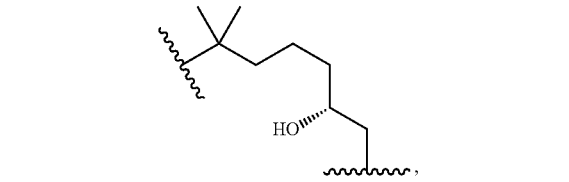
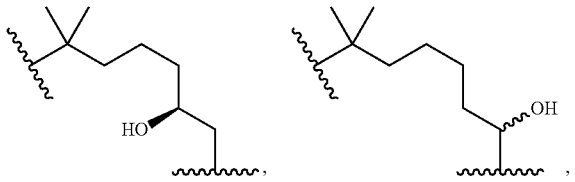 [SMILES: *C[C@@H](O)CCCC(*)(C)C ; *C(O)CCCCC(*)(C)C]
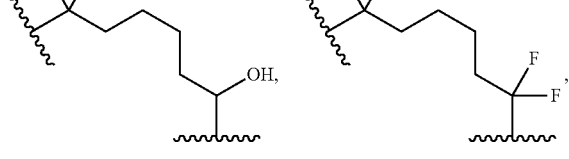
112
-continued
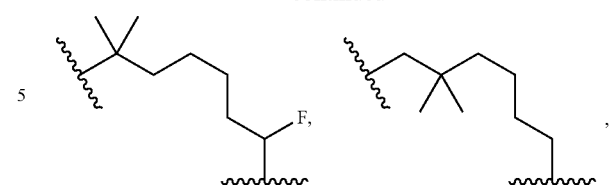
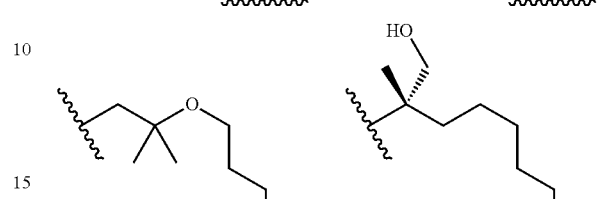
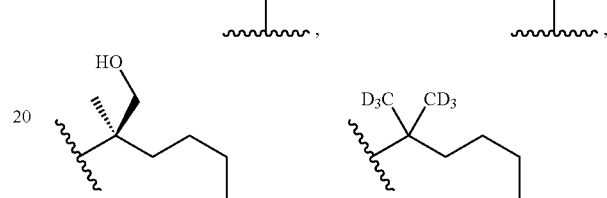
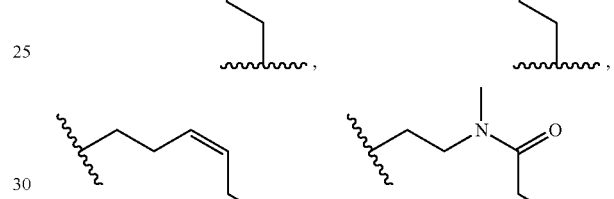
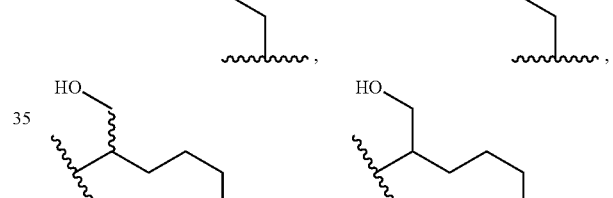
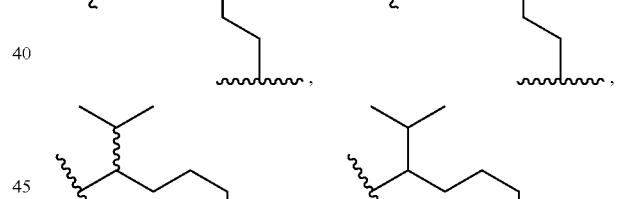
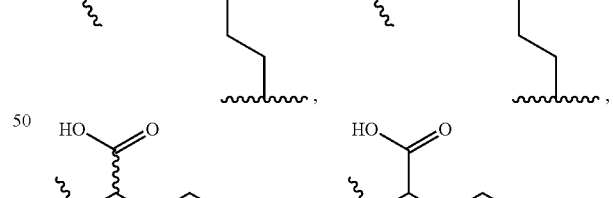
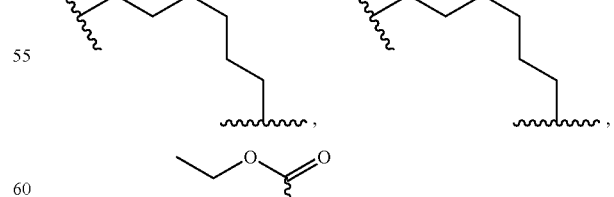
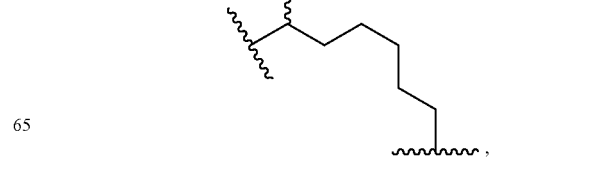

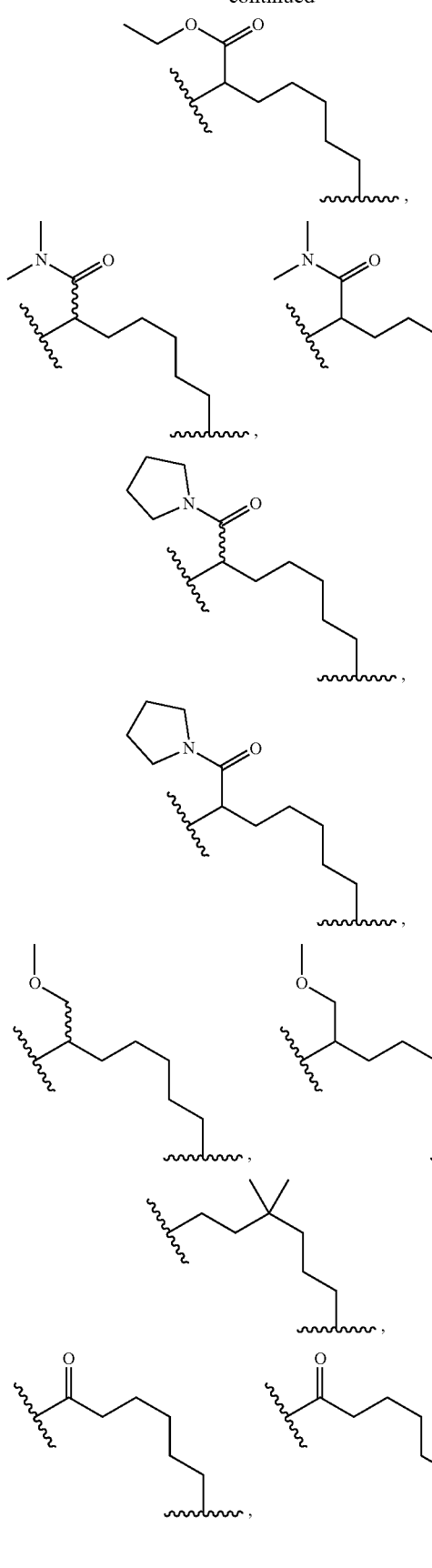
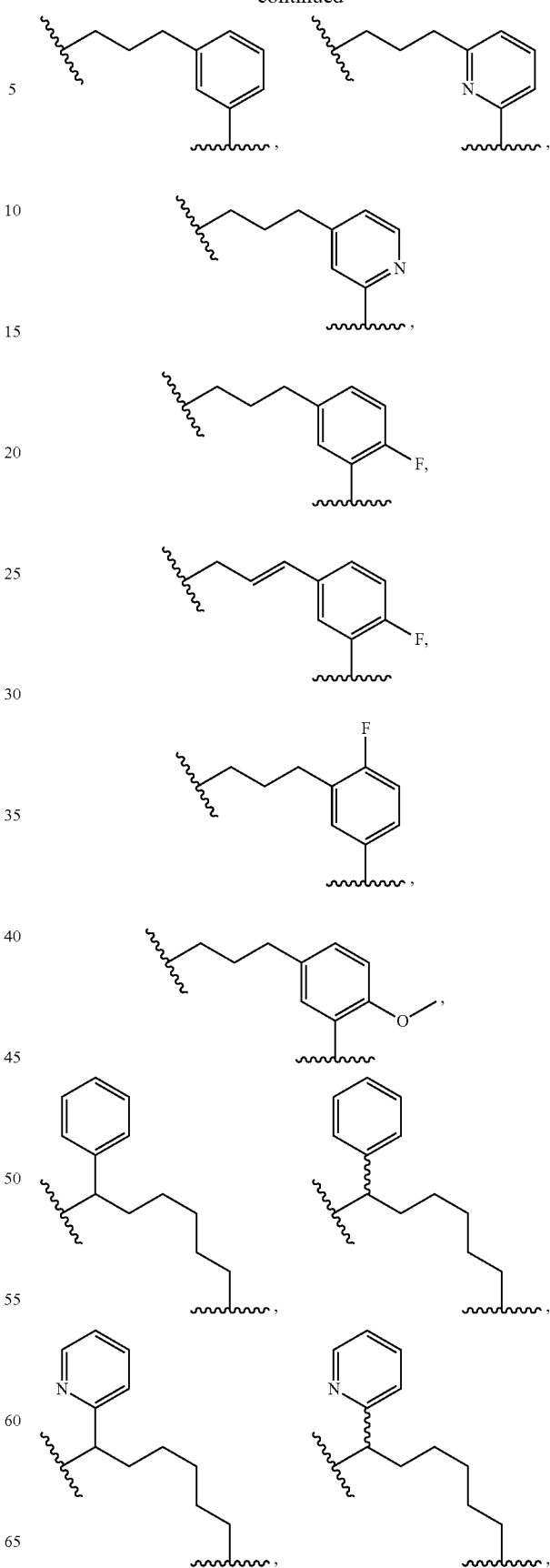

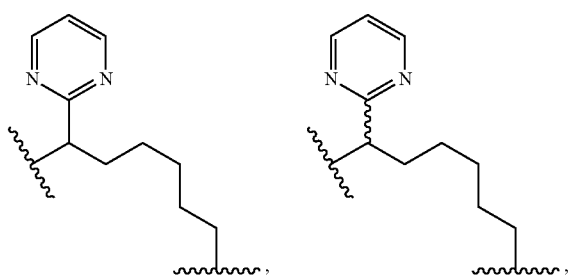

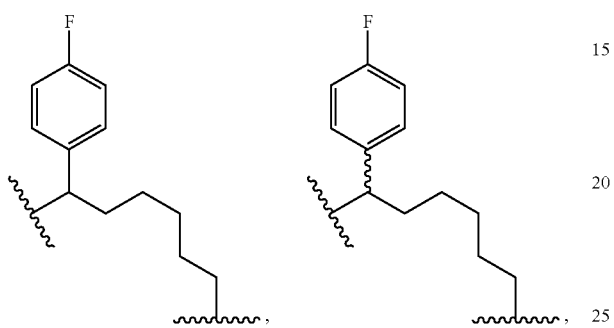

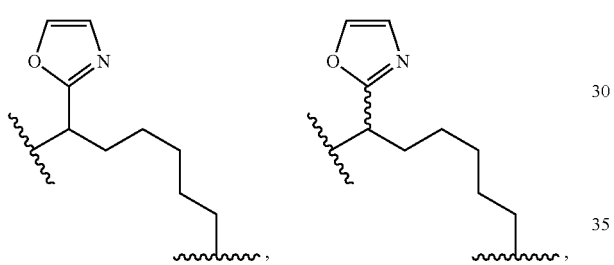

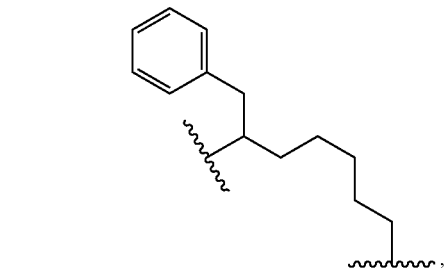

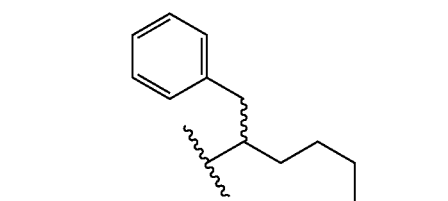

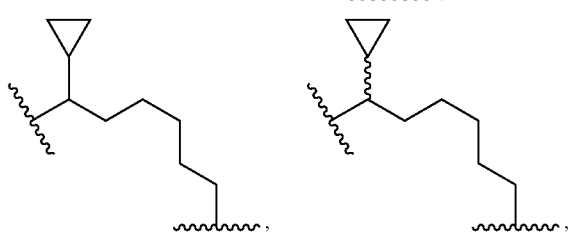

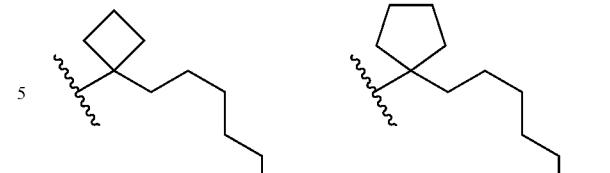

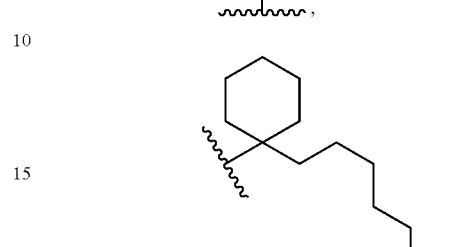

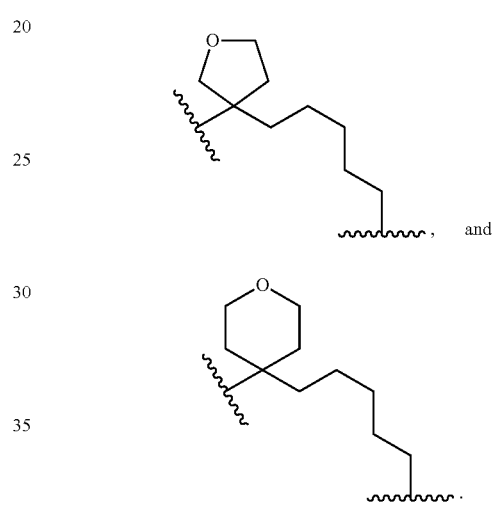

113. The compound, deuterated derivative, or pharmaceutically acceptable salt according to any one of Embodiments 1 and 100-112, wherein each $R^1$ is independently selected from halogen, $C_1$-$C_6$ fluoroalkyl, $C_1$-$C_6$ alkyl (optionally substituted with a group selected from $C_6$-$C_{10}$ aryl), —$OR^2$, —$N(R^2)_2$, —$CO_2R^2$, —CO—$N(R^2)_2$, —CN, $C_1$-$C_6$ alkoxy, $C_3$-$C_8$ cycloalkyl, $C_6$-$C_{10}$ aryl, 5- to 6-membered heteroaryl (optionally substituted with 1-3 groups independently selected from $C_1$-$C_6$ alkyl), 3- to 6-membered heterocyclyl, —$B(OR^2)_2$, —$SO_2R^2$, —$SR^2$, —$SOR^2$, and —$PO(R^2)_2$.

114. The compound, deuterated derivative, or pharmaceutically acceptable salt according to any one of Embodiments 1 and 100-113, wherein each $R^2$ is independently selected from $C_6$-$C_{10}$ aryl (optionally substituted with 1-3 groups independently selected from $C_1$-$C_6$ fluoroalkoxy).

115. The compound, deuterated derivative, or pharmaceutically acceptable salt according to any one of Embodiments 1 and 100-114, wherein each $R^{X1}$ is independently selected from —Br, —$CF_3$, —$NH_2$, —$CH_3$, —$CH(CH_3)_2$, —CN, —OH, —$OCH_3$, —$NH(CH_3)$, —$NH(CH_2CH_3)$, —$CONH_2$, —$CO_2CH_3$, —$SO_2CH_3$, —$SO_2Ph$, $PO(CH_3)_2$, $B(OH)_2$, phenyl, pyridyl, tetrahydropyranyl, tetrahydrofuranyl, cyclopropyl, cyclohexyl, imidazolyl,

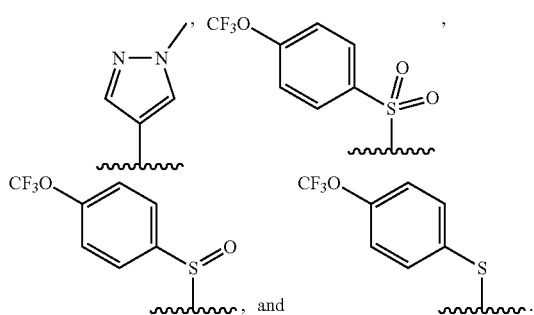

116. The compound, deuterated derivative, or pharmaceutically acceptable salt according to any one of Embodiments 1 and 100-115, wherein Z is selected from

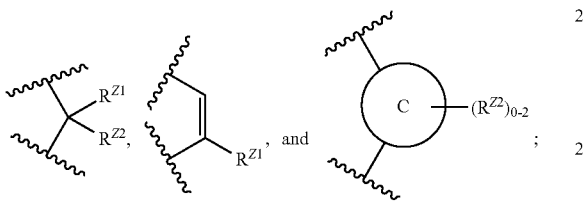

wherein Ring C is selected from $C_6$-$C_{10}$ aryl.

117. The compound, deuterated derivative, or pharmaceutically acceptable salt according to any one of Embodiments 1 and 100-116, wherein the group:

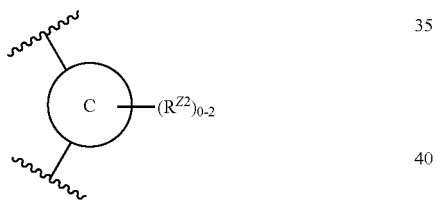

is selected from:

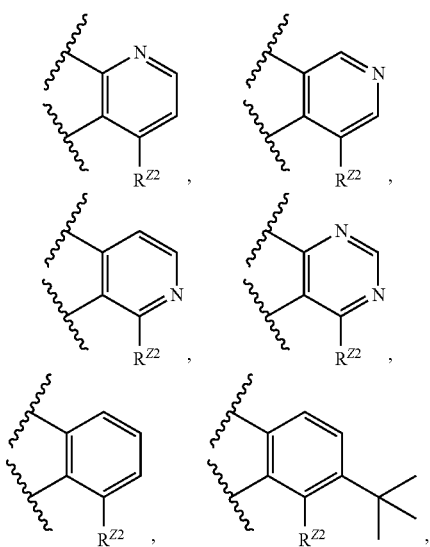

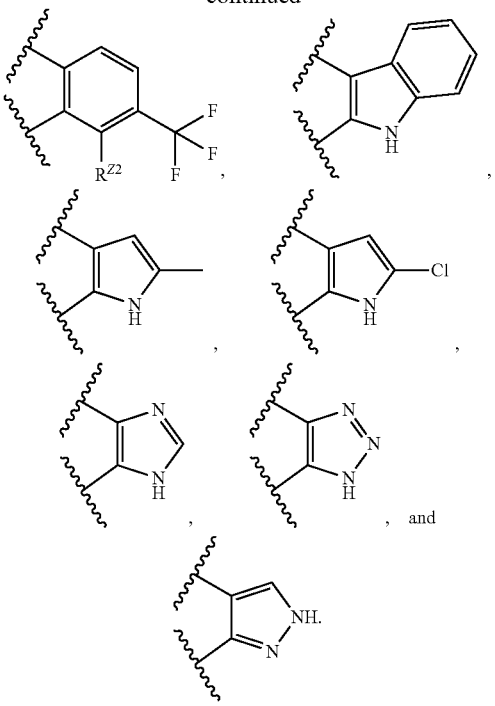

118. The compound, deuterated derivative, or pharmaceutically acceptable salt according to any one of Embodiments 1 and 100-117, wherein the group:

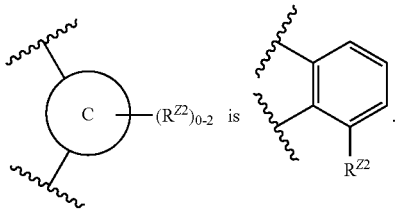

118A. The compound, deuterated derivative, or pharmaceutically acceptable salt according to any one of Embodiments 1 and 100-117, wherein $R^{Z1}$ is selected from hydrogen, $C_1$-$C_6$ alkyl (optionally substituted with 1-3 hydroxy), $C_1$-$C_6$ fluoroalkyl, 3- to 6-membered heterocyclyl, $C_3$-$C_6$ cycloalkyl, $C_6$-$C_{10}$ aryl, and 5- to 6-membered heteroaryl.

118B. The compound, deuterated derivative, or pharmaceutically acceptable salt according to any one of Embodiments 1 and 100-117, wherein $R^{Z2}$ is selected from hydrogen, halogen, hydroxy, and $C_1$-$C_6$ alkoxy (optionally substituted with 1-3 groups independently selected from $C_3$-$C_{10}$ cycloalkyl).

119. The compound, deuterated derivative, or pharmaceutically acceptable salt according to any one of Embodiments 1 and 100-118, wherein:
$R^{Z1}$ is selected from hydrogen, $C_1$-$C_6$ alkyl (optionally substituted with 1-3 hydroxy), $C_1$-$C_6$ fluoroalkyl, 3- to 6-membered heterocyclyl, $C_3$-$C_6$ cycloalkyl, and $C_6$-$C_{10}$ aryl; and
$R^{Z2}$ is selected from hydrogen, halogen, and hydroxy;
or $R^{Z1}$ and $R^{Z2}$ taken together form a group selected from oxo and =N—OH.

120. The compound, deuterated derivative, or pharmaceutically acceptable salt according to any one of Embodiments 1 and 100-119, wherein:
R$^{Z1}$ is selected from hydrogen, CH$_3$, CF$_3$, CH$_2$OH, phenyl, cyclopropyl, and tetrahydropyranyl; and
R$^{Z2}$ is selected from hydrogen, halogen, and hydroxy;
or R$^{Z1}$ and R$^{Z2}$ taken together form a group selected from oxo and =N—OH.

121. The compound, deuterated derivative, or pharmaceutically acceptable salt according to any one of Embodiments 1 and 100-120, wherein R$^{Z2}$ is hydroxy.

122. The compound, deuterated derivative, or pharmaceutically acceptable salt according to any one of Embodiments 1 and 100-121, wherein Z is selected from:

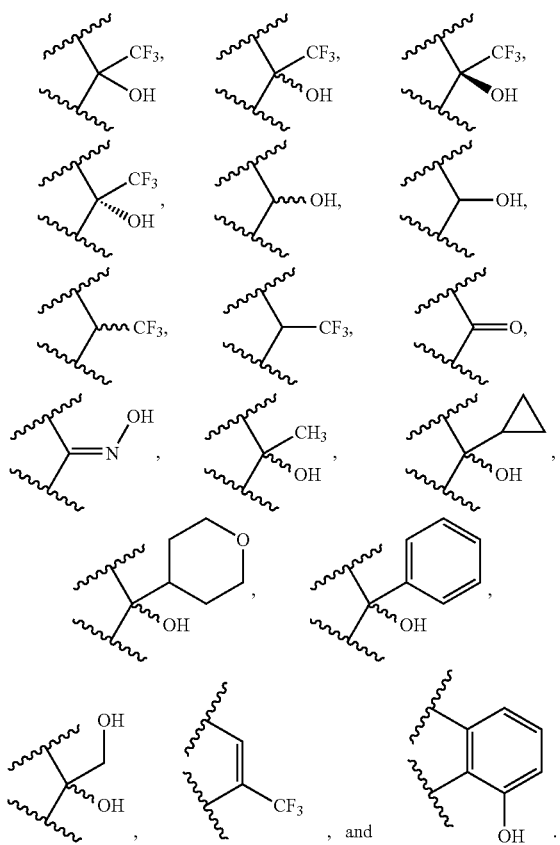

123. The compound, deuterated derivative, or pharmaceutically acceptable salt according to any one of Embodiments 1 and 100-122, wherein m is selected from 1 and 2.

124. The compound, deuterated derivative, or pharmaceutically acceptable salt according to any one of Embodiments 1 and 100-123, wherein:
X is selected from —N(R$^{X1}$)— and

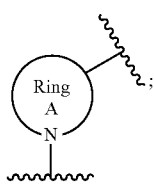

Ring A is a 4- to 6-membered heterocyclyl;
R$^{X1}$ is selected from H and C$_1$-C$_6$ alkyl;
each Y is independently selected from —C(R$^Y$)$_2$— and

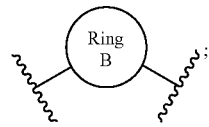

each R$^Y$ is independently selected from hydrogen, C$_1$-C$_6$ alkyl, and C$_3$-C$_8$ cycloalkyl, C$_6$-C$_{10}$ aryl (optionally substituted with 1-3 groups independently selected from halogen);
or two R$^Y$ on the same atom are taken together to form a ring selected from C$_3$-C$_8$ cycloalkyl and 3- to 7-membered heterocyclyl; or two R$^Y$, one of which is on one atom and the second of which is on an adjacent atom, are taken together to form a pi bond;
Ring B is C$_6$-C$_{10}$ aryl (optionally substituted with 1-3 groups independently selected from halogen),
each R$^1$ is independently selected from C$_1$-C$_6$ fluoroalkyl and —NH$_2$;
Z is

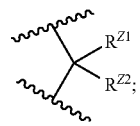

R$^{Z1}$ is C$_1$-C$_6$ fluoroalkyl;
R$^{Z2}$ is hydroxy,
n is selected from 4, 5, and 6; and
m is 2.

125. The compound, deuterated derivative, or pharmaceutically acceptable salt according to any one of Embodiments 1 and 100-124, wherein Ring A is pyrrolidine.

126. The compound, deuterated derivative, or pharmaceutically acceptable salt according to any one of Embodiments 1 and 100-125, wherein X is selected from: —NH—, —N(CH$_3$)—,

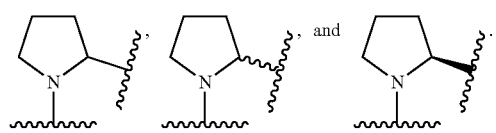

127. The compound, deuterated derivative, or pharmaceutically acceptable salt according to any one of Embodiments 1 and 100-126, wherein:
each R$^Y$ is independently selected from:
hydrogen, —CH$_3$, —CD$_3$,

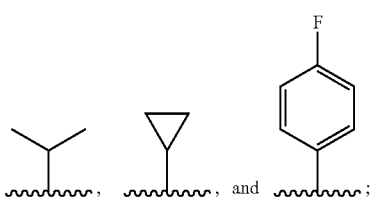

or two $R^Y$ on the same atom are taken together to form a ring selected from cyclobutyl, cyclopentyl, cyclohexyl, and tetrahydropyrrol;

or two $R^Y$, one of which is on one atom and the second of which is on an adjacent atom, are taken together to form a pi bond.

128. The compound, deuterated derivative, or pharmaceutically acceptable salt according to any one of Embodiments 1 and 100-127, wherein Ring B is phenyl(optionally substituted with 1-3 groups independently selected from halogen).

129. The compound, deuterated derivative, or pharmaceutically acceptable salt according to any one of Embodiments 1 and 100-128, wherein Ring B is

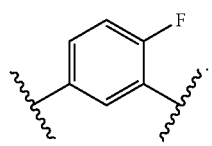 [SMILES: *c1ccc(F)c(*)c1]

130. The compound, deuterated derivative, or pharmaceutically acceptable salt according to any one of Embodiments 1 and 100-129, wherein —(Y)$_n$— is a group selected from:

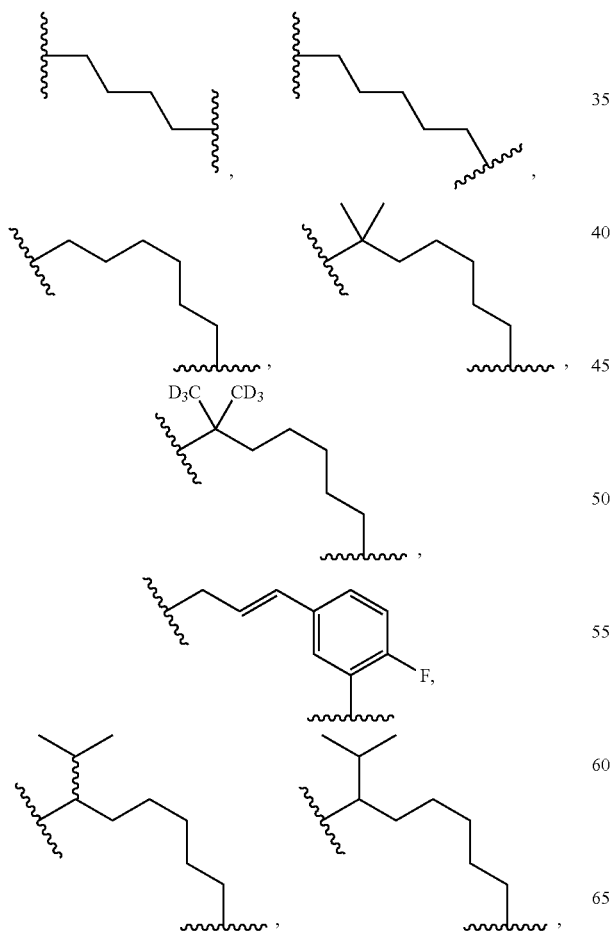

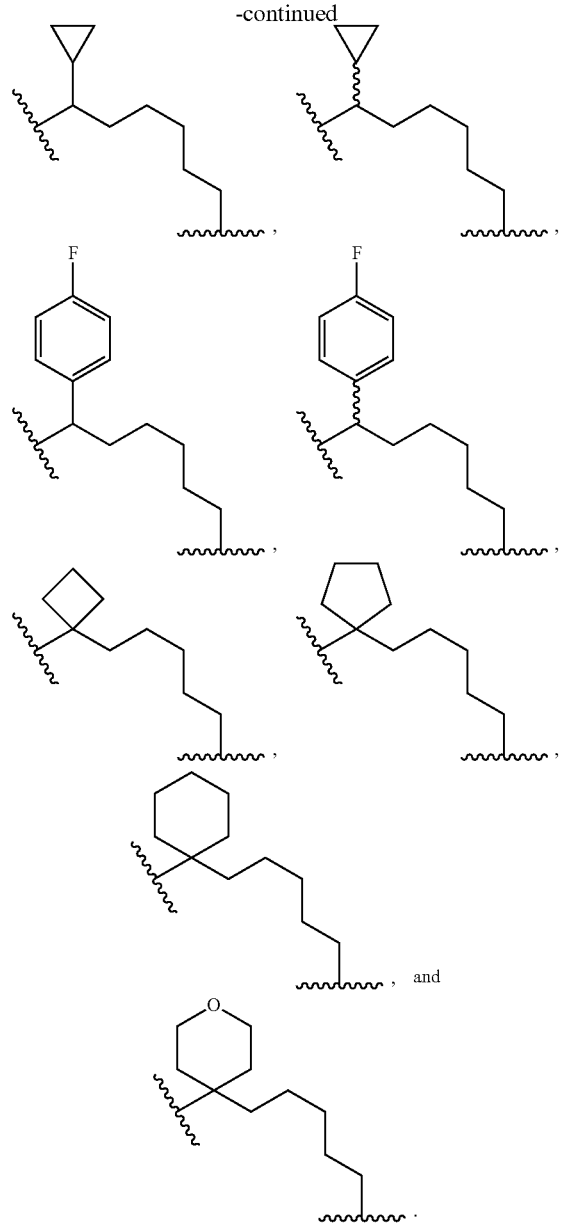

131. The compound, deuterated derivative, or pharmaceutically acceptable salt according to any one of Embodiments 1 and 100-130, wherein each $R^{X1}$ is independently selected from $CF_3$ and —$NH_2$.

132. The compound, deuterated derivative, or pharmaceutically acceptable salt according to any one of Embodiments 1 and 100-131, wherein $R^{Z1}$ is $CF_3$.

133. The compound, deuterated derivative, or pharmaceutically acceptable salt according to any one of Embodiments 1 and 100-132, wherein Z is selected from:

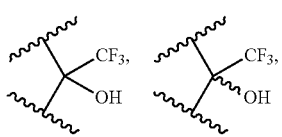

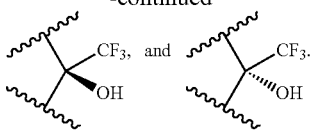
134. A compound selected from compounds of Table 10, pharmaceutically acceptable salts thereof, and deuterated derivatives of any of the foregoing.
135. A compound according to Embodiment 134, wherein the compound is selected from:
| Comp. No. | Structure |
|---|---|
| 4 | 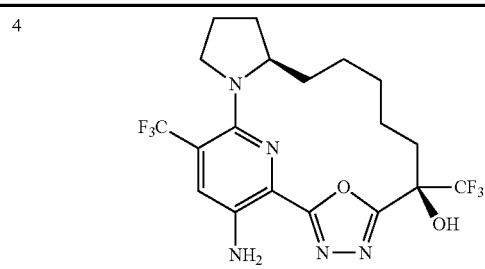 |
| 19 | 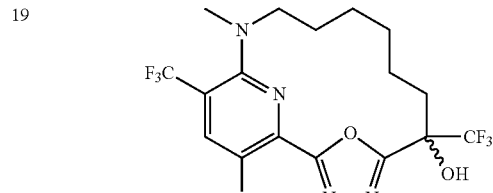 |
| 32 | 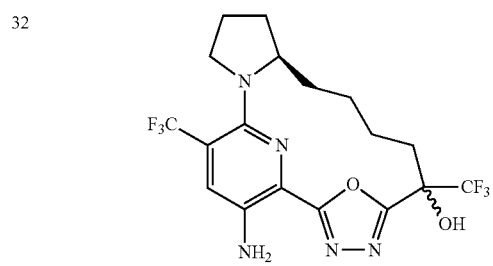 |
| 138 | 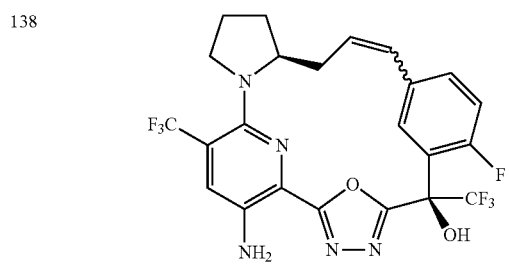 |
| 163 | 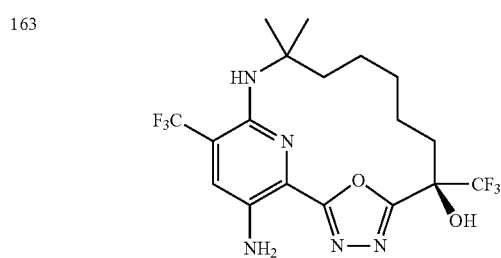 |
| Comp. No. | Structure |
|---|---|
| 173 | 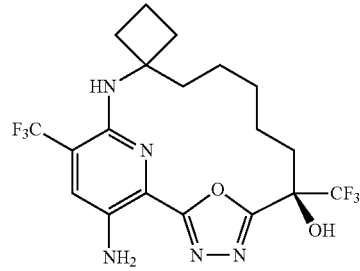 |
| 176 | 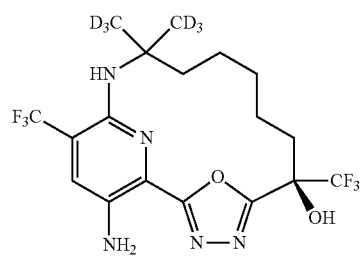 [SMILES: [2H]C([2H])([2H])C1(C([2H])([2H])[2H])CCCCC[C@](O)(C(F)(F)F)C2=NN=C(O2)c2nc(c(C(F)(F)F)cc2N)N1] |
| 177 | 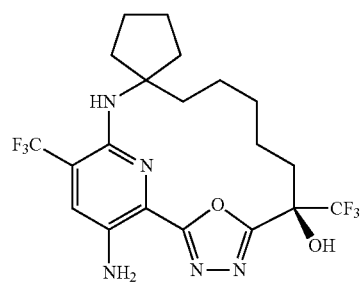 [SMILES: Nc1cc(C(F)(F)F)c2nc1C1=NN=C(O1)[C@@](O)(C(F)(F)F)CCCCCC1(CCCC1)N2] |
| 178 | 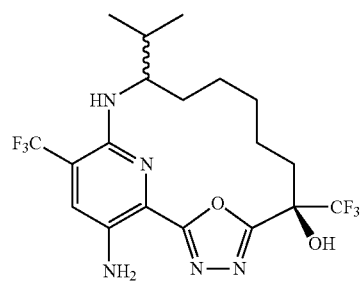 [SMILES: CC(C)C1CCCCC[C@](O)(C(F)(F)F)C2=NN=C(O2)c2nc(c(C(F)(F)F)cc2N)N1] |
| 182 | 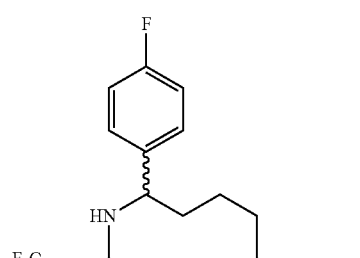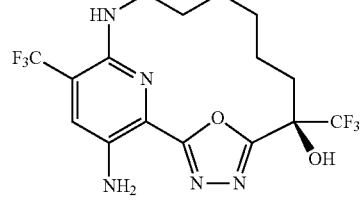 |

| Comp. No. | Structure |
|---|---|
| 192 | 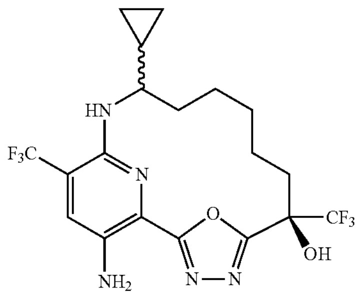 [SMILES: Nc1cc(C(F)(F)F)c2nc1C1=NN=C(O1)[C@@](O)(C(F)(F)F)CCCCCC(C1CC1)N2] |
| 193 | 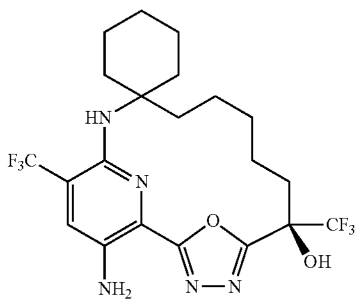 [SMILES: Nc1cc(C(F)(F)F)c2nc1C1=NN=C(O1)[C@@](O)(C(F)(F)F)CCCCCC1(CCCCC1)N2] |
| 205 | 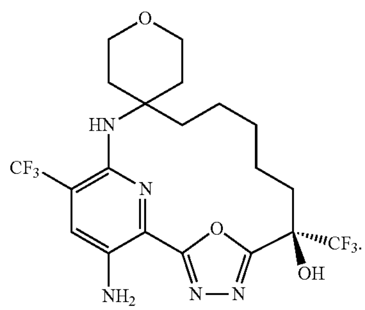 [SMILES: Nc1cc(C(F)(F)F)c2nc1C1=NN=C(O1)[C@@](O)(C(F)(F)F)CCCCCC1(CCOCC1)N2] |

136. A pharmaceutical composition comprising a compound, salt, or deuterated derivative of any one of Embodiments 1-135 and a pharmaceutically acceptable carrier.

137. The pharmaceutical composition according to Embodiment 136, further comprising one or more additional therapeutic agent(s).

138. The pharmaceutical composition according to Embodiment 137, wherein the one or more additional therapeutic agent(s) comprise(s) a compound with CFTR modulating activity or a salt or deuterated derivative thereof 139. The pharmaceutical composition according to Embodiment 137 or 138, wherein the one or more additional therapeutic agent(s) comprise(s) a CFTR corrector.

140. The pharmaceutical composition according to any one of Embodiments 137-139, wherein the one or more additional therapeutic agent(s) comprise(s) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound II):

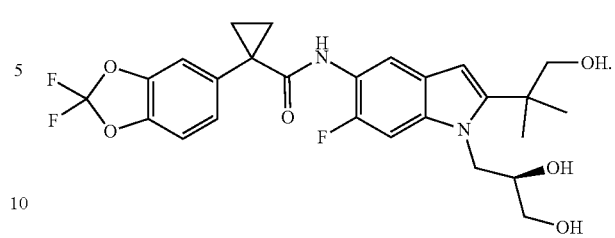

141. The pharmaceutical composition according to any one of Embodiments 137-140, wherein the one or more additional therapeutic agent(s) comprise(s) 3-(6-(1-(2,2-difluorobenzo[d][1,3]dioxol-5-yl)cyclopropanecarboxamido)-3-methylpyridin-2-yl)benzoic acid (Compound IV):

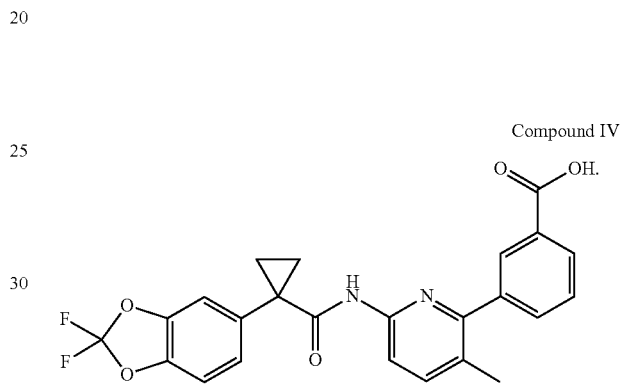

Compound IV

142. The pharmaceutical composition according to any one of Embodiments 137-141, wherein the one or more additional therapeutic agent(s) comprise(s) N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (Compound V):

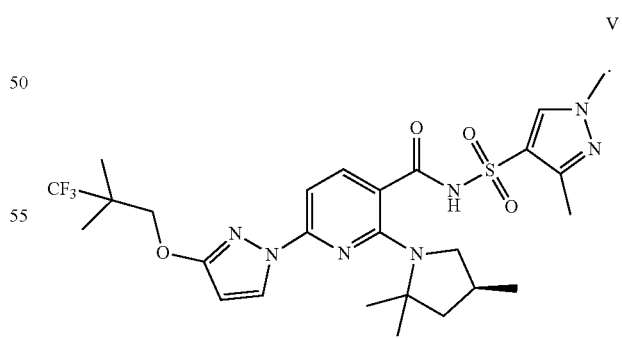

143. The pharmaceutical composition according to any one of Embodiments 137-142, wherein the one or more additional therapeutic agent(s) comprise(s) N-(benzenesulfonyl)-6-[3-[2-[1-(trifluoromethyl) cyclopropyl]ethoxy]pyrazol-1-yl]-2-[(4S)-2,2,4-trimethylpyrrolidin-1-yl]pyridine-3-carboxamide (Compound VI):

Compound VI

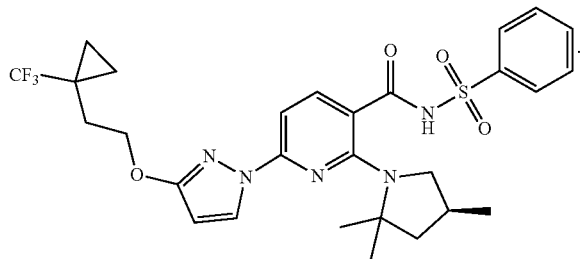

144. The pharmaceutical composition according to any one of Embodiments 137-143, wherein the one or more additional therapeutic agent(s) comprise(s) (14S)-8-[3-(2-{dispiro[2.0.2.1]heptan-7-yl}ethoxy)-1H-pyrazol-1-yl]-12,12-dimethyl-2$\lambda^6$-thia-3,9,11,18,23-pentaazatetracyclo[17.3.1.1^{11,14}.0^{5,10}]tetracosa-1(22),5,7,9,19(23),20-hexaene-2,2,4-trione (Compound VII):

Compound VII

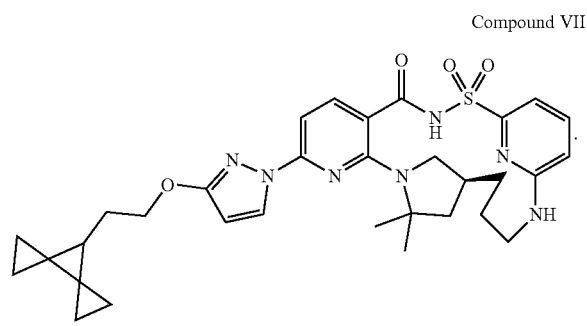 [SMILES: CC1(C)C[C@@H]2CCCNc3cccc(n3)S(=O)(=O)NC(=O)c3ccc(-n4ccc(OCCC5C6(CC6)C56CC6)n4)nc3N1C2]

145. The pharmaceutical composition according to any one of Embodiments 137-144, wherein the one or more additional therapeutic agent(s) comprise(s) (11R)-6-(2,6-dimethylphenyl)-11-(2-methylpropyl)-12-{spiro[2.3]hexan-5-yl}-9-oxa-2$\lambda^6$-thia-3,5,12,19-tetraazatricyclo[12.3.1.1^{4,8}]nonadeca-1(17),4(19),5,7,14(18),15-hexaene-2,2,13-trione (Compound VIII):

Compound VIII

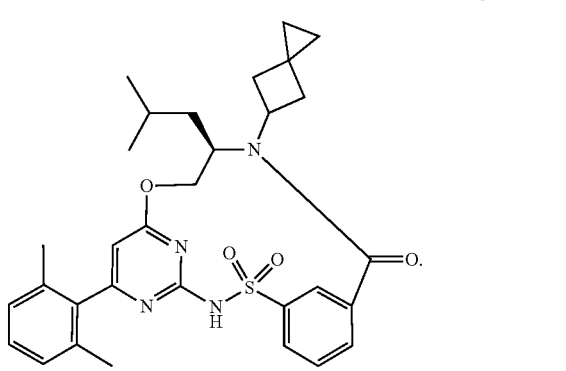

146. The pharmaceutical composition according to any one of Embodiments 137-145, wherein the one or more additional therapeutic agent(s) comprise(s) at least one compound selected from PTI-428, ABBV-2222, ABBV-2851, GLPG2737, ABBV-3221, ABBV-3748, ABBV-3903, ABBV-119, FDL-169, ARN5562, ARN21586, ARN22081, ARN22652, ARN23765, ARN23766, and PTI-801.

147. The pharmaceutical composition according to any one of Embodiments 137-146, wherein the one or more additional therapeutic agent(s) comprise(s) a CFTR potentiator enhancer.

148. The pharmaceutical composition according to any one of Embodiments 137-147, wherein the one or more additional therapeutic agent(s) comprise(s) ASP-11.

149. The pharmaceutical composition according to any one of Embodiments 137-148, wherein the one or more additional therapeutic agent(s) comprise(s) a CFTR potentiator.

150. The pharmaceutical composition according to any one of Embodiments 137-149, wherein the one or more additional therapeutic agent(s) comprise(s) a compound selected from N-(5-hydroxy-2,4-di-tert-butyl-phenyl)-4-oxo-1H-quinoline-3-carboxamide (Compound III):

Compound III

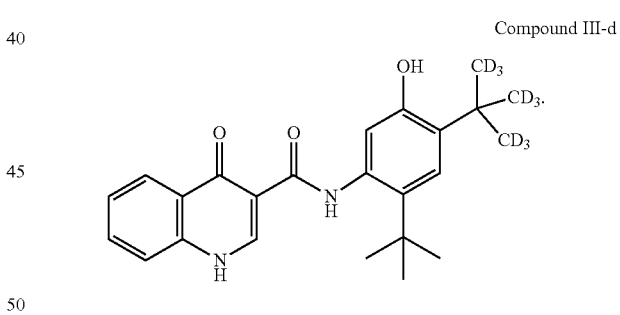

and N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide (Compound III-d):

Compound III-d

151. The pharmaceutical composition according to any one of Embodiments 137-150, wherein the one or more additional therapeutic agent(s) comprise(s) at least one compound selected from FDL-176, PTI-808, GLPG1837, GLPG2451/ABBV-2451 (Icenticaftor), GLPG3067/ABBV-3067 (Navocaftor), and ABBV-191.

152. The pharmaceutical composition according to any one of Embodiments 137-151, wherein the one or more additional therapeutic agent(s) comprise(s) a CFTR amplifier.

153. The pharmaceutical composition according to any one of Embodiments 137-152, wherein the one or more additional therapeutic agent(s) comprise(s) PTI-428.

154. The pharmaceutical composition according to any one of Embodiments 137-153, wherein the one or more additional therapeutic agent(s) comprise(s) a CFTR read-through agent.

155. The pharmaceutical composition according to any one of Embodiments 137-154, wherein the one or more additional therapeutic agent(s) comprise(s) ELX-02.
156. The pharmaceutical composition according to any one of Embodiments 137-155, wherein the one or more additional therapeutic agent(s) comprise(s) a nucleic acid therapy.
157. The pharmaceutical composition according to any one of Embodiments 137-156, wherein the one or more additional therapeutic agent(s) comprise(s) at least one agent selected from MRT5005, Lunar-CF, and RCT223.
158. The pharmaceutical composition according to any one of Embodiments 137-157, wherein the one or more additional therapeutic agent(s) comprise(s) an ENaC inhibitor.
159. The pharmaceutical composition according to any one of Embodiments 137-158, wherein the one or more additional therapeutic agent(s) comprise(s) amiloride, ETD001, CF552, GS-9411, GS-5737, P-1037 (VX-371), P-1055 (VX-551), AZD5634, SPX-101, Ionis-ENaC-2.5 Rx, BI 1265162, AZ5634, and ARO-ENaC1001.
160. The pharmaceutical composition according to any one of Embodiments 137-159, wherein the one or more additional therapeutic agent(s) comprise(s) a TMEM16A modulator.
161. The pharmaceutical composition according to any one of Embodiments 137-160, wherein the one or more additional therapeutic agent(s) comprise(s) ETD002.
162. The pharmaceutical composition according to any one of Embodiments 137-161, wherein the one or more additional therapeutic agent(s) comprise(s) a GPR39 Agonist.
163. The pharmaceutical composition according to any one of Embodiments 137-162, wherein the one or more additional therapeutic agent(s) comprise(s) DS-1039.
164. A method of treating cystic fibrosis, comprising administering an effective amount of the compound, salt, or deuterated derivative according to any one of Embodiments 1-135 or the pharmaceutical composition according to any one of Embodiments 136-163 to a patient in need thereof.
165. The method according to Embodiment 164, further comprising administering one or more additional therapeutic agent(s).
166. The method according to Embodiment 165, wherein the one or more additional therapeutic agent(s) comprise(s) a compound with CFTR modulating activity or a salt or deuterated derivative thereof.
167. The method according to Embodiment 165 or 166, wherein the one or more additional therapeutic agent(s) comprise(s) a CFTR corrector.
168. The method according to any one of Embodiments 165-167, wherein the one or more additional therapeutic agent(s) comprise(s) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound II):

Compound II

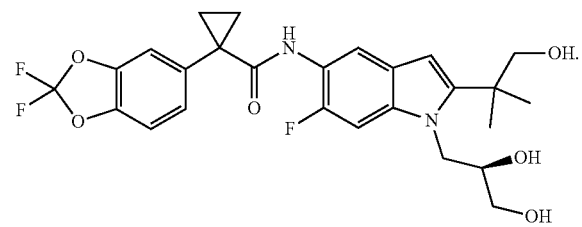

169. The method according to any one of Embodiments 165-168, wherein the one or more additional therapeutic agent(s) comprise(s) 3-(6-(1-(2,2-difluorobenzo[d][1,3]dioxol-5-yl)cyclopropanecarboxamido)-3-methylpyridin-2-yl)benzoic acid (Compound IV):

Compound IV

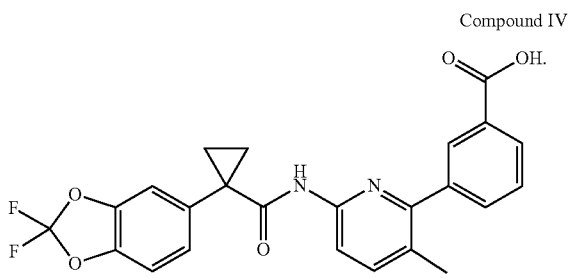 [SMILES: Cc1ccc(NC(=O)C2(c3ccc4c(c3)OC(F)(F)O4)CC2)nc1-c1cccc(C(=O)O)c1]

170. The method according to any one of Embodiments 165-169, wherein the one or more additional therapeutic agent(s) comprise(s) N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (Compound V):

Compound V

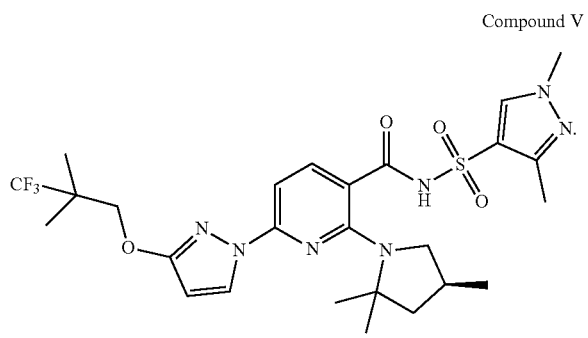 [SMILES: Cc1nn(C)cc1S(=O)(=O)NC(=O)c1ccc(-n2ccc(OCC(C)(C)C(F)(F)F)n2)nc1N1C[C@@H](C)CC1(C)C]

171. The method according to any one of Embodiments 165-170, wherein the one or more additional therapeutic agent(s) comprise(s) N-(benzenesulfonyl)-6-[3-[2-[1-(trifluoromethyl) cyclopropyl]ethoxy]pyrazol-1-yl]-2-[(4S)-2,2,4-trimethylpyrrolidin-1-yl]pyridine-3-carboxamide (Compound VI):

Compound VI

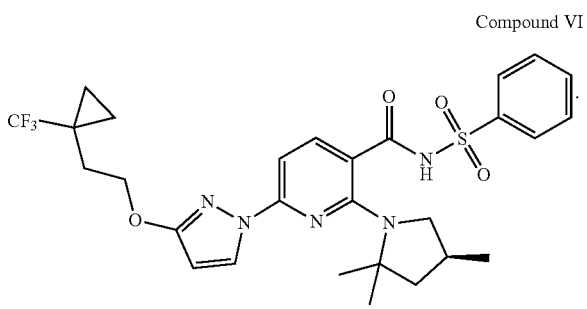 [SMILES: C[C@@H]1CN(c2nc(-n3ccc(OCCC4(C(F)(F)F)CC4)n3)ccc2C(=O)NS(=O)(=O)c2ccccc2)C(C)(C)C1]

172. The method according to any one of Embodiments 165-171, wherein the one or more additional therapeutic agent(s) comprise(s) (14S)-8-[3-(2-{dispiro[2.0.2.1]heptan-7-yl}ethoxy)-1H-pyrazol-1-yl]-12,12-dimethyl-2$\lambda^6$-thia-3,9,11,18,23-pentaazatetracyclo [17.3.1.111,14.05,10]tetracosa-1(22),5,7,9,19(23),20-hexaene-2,2,4-trione (Compound VII):

Compound VII

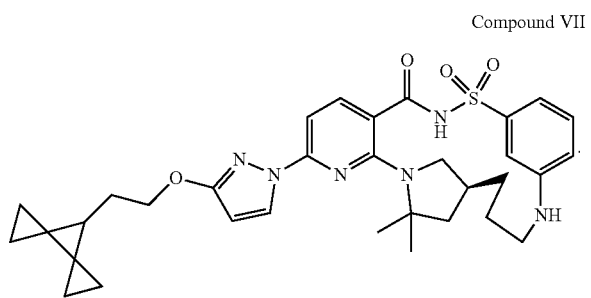 [SMILES: CC1(C)C[C@@H]2CCCNc3cccc(c3)S(=O)(=O)NC(=O)c3ccc(-n4ccc(OCCC5C6(CC6)C56CC6)n4)nc3N1C2]

173. The method according to any one of Embodiments 165-172, wherein the one or more additional therapeutic agent(s) comprise(s) (11R)-6-(2,6-dimethylphenyl)-11-(2-methylpropyl)-12-{spiro[2.3]hexan-5-yl}-9-oxa-2λ⁶-thia-3,5,12,19-tetraazatricyclo[12.3.1.14,8]nonadeca-1(17),4(19),5,7,14(18),15-hexaene-2,2,13-trione (Compound VIII):

Compound VIII

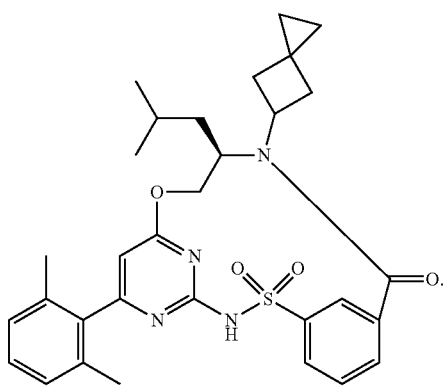

174. The method according to any one of Embodiments 165-173, wherein the one or more additional therapeutic agent(s) comprise(s) at least one compound selected from PTI-428, ABBV-2222, ABBV-2851, GLPG2737, ABBV-3221, ABBV-3748, ABBV-3903, ABBV-119, ABBV-2851, FDL-169, ARN5562, ARN21586, ARN22081, ARN22652, ARN23765, ARN23766, and PTI-801.

175. The method according to any one of Embodiments 165-174, wherein the one or more additional therapeutic agent(s) comprise(s) a CFTR potentiator enhancer.

176. The method according to any one of Embodiments 165-175, wherein the one or more additional therapeutic agent(s) comprise(s) ASP-11.

177. The method according to any one of Embodiments 165-176, wherein the one or more additional therapeutic agent(s) comprise(s) a CFTR potentiator.

178. The method according to any one of Embodiments 165-177, wherein the one or more additional therapeutic agent(s) comprise(s) a compound selected from N-(5-hydroxy-2,4-di-tert-butyl-phenyl)-4-oxo-1H-quinoline-3-carboxamide (Compound III):

Compound III

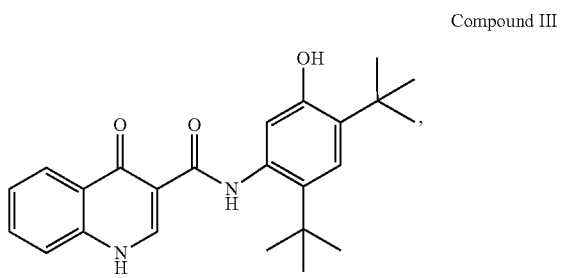 [SMILES: CC(C)(C)c1cc(C(C)(C)C)c(NC(=O)c2c[nH]c3ccccc3c2=O)cc1O]

and N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide (Compound III-d):

Compound III-d

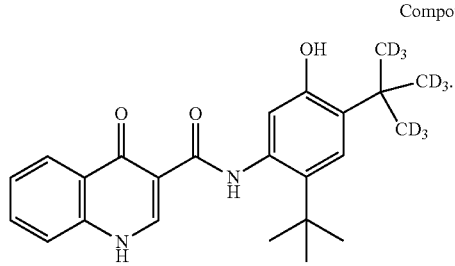

179. The method according to any one of Embodiments 165-178, wherein the one or more additional therapeutic agent(s) comprise(s) at least one compound selected from FDL-176, PTI-808, GLPG1837, GLPG2451/ABBV-2451 (Icenticaftor), GLPG3067/ABBV-3067 (Navocaftor), and ABBV-191.

180. The method according to any one of Embodiments 165-179, wherein the one or more additional therapeutic agent(s) comprise(s) a CFTR amplifier.

181. The method according to any one of Embodiments 165-180, wherein the one or more additional therapeutic agent(s) comprise(s) PTI-428.

182. The method according to any one of Embodiments 165-181, wherein the one or more additional therapeutic agent(s) comprise(s) a CFTR readthrough agent.

183. The method according to any one of Embodiments 165-182, wherein the one or more additional therapeutic agent(s) comprise(s) ELX-02.

184. The method according to any one of Embodiments 165-183, wherein the one or more additional therapeutic agent(s) comprise(s) a nucleic acid therapy.

185. The method according to any one of Embodiments 165-184, wherein the one or more additional therapeutic agent(s) comprise(s) at least one agent selected from MRT5005, Lunar-CF, and RCT223.

186. The method according to any one of Embodiments 165-185, wherein the one or more additional therapeutic agent(s) comprise(s) an ENaC inhibitor.

187. The method according to any one of Embodiments 165-186, wherein the one or more additional therapeutic agent(s) comprise(s) amiloride, ETD001, CF552, GS-9411, GS-5737, P-1037 (VX-371), P-1055 (VX-551), AZD5634, SPX-101, Ionis-ENaC-2.5 Rx, BI 1265162, AZ5634, and ARO-ENaC1001.

188. The method according to any one of Embodiments 165-187, wherein the one or more additional therapeutic agent(s) comprise(s) a TMEM16A modulator.

189. The method according to any one of Embodiments 165-188, wherein the one or more additional therapeutic agent(s) comprise(s) ETD002.
190. The method according to any one of Embodiments 165-180, wherein the one or more additional therapeutic agent(s) comprise(s) a GPR39 Agonist.
191. The method according to any one of Embodiments 165-190, wherein the one or more additional therapeutic agent(s) comprise(s) DS-1039.
192. The compound, salt, or deuterated derivative of any one of Embodiments 1-135 or the pharmaceutical composition according to any one of Embodiments 136-163 for use in the treatment of cystic fibrosis.
193. Use of the compound, salt, or deuterated derivative of any one of Embodiments 1-135 or the pharmaceutical composition according to any one of Embodiments 136-163 in the manufacture of a medicament for the treatment of cystic fibrosis.
194. Substantially amorphous Compound 4 (neat form) (i.e., wherein less than 15% of Compound 4 is in crystalline form, wherein less than 10% of Compound 4 is in crystalline form, wherein less than 5% of Compound 4 is in crystalline form).
195. The substantially amorphous Compound 4 (neat form) according to Embodiment 194, wherein Compound 4 is 100% amorphous.
196. The substantially amorphous Compound 4 (neat form) according to Embodiment 194 or 195, characterized by an X-ray powder diffractogram substantially similar to FIG. 1.
197. Substantially crystalline Compound 5 Form A (neat) (i.e., wherein less than 15% of Compound 5 is in amorphous form, wherein less than 10% of Compound 5 is in amorphous form, wherein less than 5% of Compound 5 is in amorphous form).
198. The substantially crystalline Compound 5 Form A (neat) according to Embodiment 197, wherein Compound 5 Form A (neat) is 100% crystalline.
199. The substantially crystalline Compound 5 Form A (neat) according to Embodiment 197 or 198, characterized by a tetragonal crystal system, an I41 space group, and unit cell dimensions measured at 100 K on a Bruker diffractometer utilizing Cu $K_\alpha$ radiation ($\lambda$=1.54178 Å) of:

| a | 18.1 ± .1 Å | α | 90° |
| b | 18.1 ± .1 Å | β | 90° |
| c | 13.1 ± .1 Å | γ | 90°. |

200. Substantially amorphous Compound 19 (neat form) (i.e., wherein less than 15% of Compound 19 is in crystalline form, wherein less than 10% of Compound 19 is in crystalline form, wherein less than 5% of Compound 19 is in crystalline form).
201. The substantially amorphous Compound 19 (neat form) according to Embodiment 200, wherein Compound 19 is 100% amorphous.
202. The substantially amorphous Compound 19 (neat form) according to Embodiment 200 or 201, characterized by an X-ray powder diffractogram substantially similar to FIG. 4.
203. Substantially crystalline Compound 41 Form A (i.e., wherein less than 15% of Compound 41 is in amorphous form, wherein less than 10% of Compound 41 is in amorphous form, wherein less than 5% of Compound 41 is in amorphous form).
204. The substantially crystalline Compound 41 Form A according to Embodiment 203, wherein Compound 41 Form A is 100% crystalline.
205. The substantially crystalline Compound 41 Form A according to Embodiment 203 or 204, characterized by an X-ray powder diffractogram having one, two, or three signals selected from 14.2±0.2 degrees two-theta, 19.5±0.2 degrees two-theta, and 21.2±0.2 degrees two-theta.
206. The substantially crystalline Compound 41 Form A according to any one of Embodiments 203-205, characterized by an X-ray powder diffractogram having one, two, three, four, five, or six signals selected from 14.2±0.2 degrees two-theta, 19.5±0.2 degrees two-theta, 21.2±0.2 degrees two-theta, 18.0±0.2 degrees two-theta, 16.6±0.2 degrees two-theta, and 20.7±0.2 degrees two-theta.
207. The substantially crystalline Compound 41 Form A according to any one of Embodiments 203-206, characterized by an X-ray powder diffractogram having one, two, three, four, five, six, seven, eight, or nine signals selected from 14.2±0.2 degrees two-theta, 16.6±0.2 degrees two-theta, 18.0±0.2 degrees two-theta, 19.5±0.2 degrees two-theta, 20.3±0.2 degrees two-theta, 20.7±0.2 degrees two-theta, 21.2±0.2 degrees two-theta, 22.2±0.2 degrees two-theta, and 25.1±0.2 degrees two-theta.
208. The substantially crystalline Compound 41 Form A according to any one of Embodiments 203-207, characterized by an X-ray powder diffractogram substantially similar to FIG. 7.
209. Substantially crystalline Compound 52 Form A (neat) (i.e., wherein less than 15% of Compound 52 is in amorphous form, wherein less than 10% of Compound 52 is in amorphous form, wherein less than 5% of Compound 52 is in amorphous form).
210. The substantially crystalline Compound 52 Form A (neat) according to Embodiment 209, wherein Compound 52 Form A (neat) is 100% crystalline.
211. The substantially crystalline Compound 52 Form A (neat) according to Embodiment 209 or 210, characterized by an X-ray powder diffractogram having one, two, or three signals selected from 6.8±0.2 degrees two-theta, 17.3±0.2 degrees two-theta, and 18.6±0.2 degrees two-theta.
212. The substantially crystalline Compound 52 Form A (neat) according to any one of Embodiments 209-211, characterized by an X-ray powder diffractogram having one, two, three, four, five, or six signals selected from 6.8±0.2 degrees two-theta, 12.7±0.2 degrees two-theta, 17.3±0.2 degrees two-theta, 18.6±0.2 degrees two-theta, 20.6±0.2 degrees two-theta, and 21.4±0.2 degrees two-theta.
213. The substantially crystalline Compound 52 Form A (neat) according to any one of Embodiments 209-212, characterized by an X-ray powder diffractogram having one, two, three, four, five, six, seven, eight, nine, ten, eleven, or twelve signals selected from 6.8±0.2 degrees two-theta, 12.7±0.2 degrees two-theta, 15.1±0.2 degrees two-theta, 15.5±0.2 degrees two-theta, 17.3±0.2 degrees two-theta, 18.6±0.2 degrees two-theta, 19.2±0.2 degrees two-theta, 19.7±0.2 degrees two-theta, 20.4±0.2 degrees two-theta, 20.6±0.2 degrees two-theta, 21.4±0.2 degrees two-theta, and 27.2±0.2 degrees two-theta.
214. The substantially crystalline Compound 52 Form A (neat) according to any one of Embodiments 209-213, characterized by an X-ray powder diffractogram substantially similar to FIG. 9.

215. Substantially amorphous Compound 60 (neat form) (i.e., wherein less than 15% of Compound 60 is in crystalline form, wherein less than 10% of Compound 60 is in crystalline form, wherein less than 5% of Compound 60 is in crystalline form).

216. The substantially amorphous Compound 60 (neat form) according to Embodiment 215, wherein Compound 60 is 100% amorphous.

217. The substantially amorphous Compound 60 (neat form) according to Embodiment 215 or 216, characterized by an X-ray powder diffractogram substantially similar to FIG. 12.

218. Substantially amorphous Compound 70 (neat form) (i.e., wherein less than 15% of Compound 70 is in crystalline form, wherein less than 10% of Compound 70 is in crystalline form, wherein less than 5% of Compound 70 is in crystalline form).

219. The substantially amorphous Compound 70 (neat form) according to Embodiment 218, wherein Compound 70 is 100% amorphous.

220. The substantially amorphous Compound 70 (neat form) according to Embodiment 218 or 219, characterized by an X-ray powder diffractogram substantially similar to FIG. 15.

221. Substantially crystalline Compound 163 Form A (neat) (i.e., wherein less than 15% of Compound 163 is in amorphous form, wherein less than 10% of Compound 163 is in amorphous form, wherein less than 5% of Compound 163 is in amorphous form).

222. The substantially crystalline Compound 163 Form A (neat) according to Embodiment 221, wherein Compound 163 Form A (neat) is 100% crystalline.

223. The substantially crystalline Compound 163 Form A (neat) according to Embodiment 221 or 222, characterized by an X-ray powder diffractogram having a signal at 7.4±0.2 degrees two-theta.

224. The substantially crystalline Compound 163 Form A (neat) according to any one of Embodiments 221-223, characterized by an X-ray powder diffractogram having one, two, or three signals selected from 7.4±0.2 degrees two-theta, 8.4±0.2 degrees two-theta, and 15.0±0.2 degrees two-theta.

225. The substantially crystalline Compound 163 Form A (neat) according to any one of Embodiments 221-224, characterized by an X-ray powder diffractogram having one, two, three, four, five, or six signals selected from 7.4±0.2 degrees two-theta, 8.4±0.2 degrees two-theta, 14.1±0.2 degrees two-theta, 15.0±0.2 degrees two-theta, 19.1±0.2 degrees two-theta, and 25.8±0.2 degrees two-theta.

226. The substantially crystalline Compound 163 Form A (neat) according to any one of Embodiments 221-225, characterized by an X-ray powder diffractogram having one, two, three, four, five, six, seven, eight, nine, ten, or eleven signals selected from 7.4±0.2 degrees two-theta, 8.4±0.2 degrees two-theta, 14.1±0.2 degrees two-theta, 14.6±0.2 degrees two-theta, 15.0±0.2 degrees two-theta, 16.9±0.2 degrees two-theta, 19.1±0.2 degrees two-theta, 20.0±0.2 degrees two-theta, 22.5±0.2 degrees two-theta, 25.6±0.2 degrees two-theta, and 25.8±0.2 degrees two-theta.

227. The substantially crystalline Compound 163 Form A (neat) according to any one of Embodiments 221-226, characterized by an X-ray powder diffractogram substantially similar to FIG. 16.

228. Substantially amorphous Compound 173 (neat form) (i.e., wherein less than 15% of Compound 173 is in crystalline form, wherein less than 10% of Compound 173 is in crystalline form, wherein less than 5% of Compound 173 is in crystalline form).

229. The substantially amorphous Compound 173 (neat form) according to Embodiment 228, wherein Compound 173 is 100% amorphous.

230. The substantially amorphous Compound 173 (neat form) according to Embodiment 228 or 229, characterized by an X-ray powder diffractogram substantially similar to FIG. 18.

231. Substantially crystalline Compound 173 (neat form) (i.e., wherein less than 15% of Compound 173 is in amorphous form, wherein less than 10% of Compound 173 is in amorphous form, wherein less than 5% of Compound 173 is in amorphous form).

232. The substantially crystalline Compound 173 Form A (neat) according to Embodiment 231, wherein Compound 173 Form A (neat) is 100% crystalline.

233. The substantially crystalline Compound 173 Form A (neat) according to Embodiment 231 or 232, characterized by a triclinic crystal system, a P1 space group, and unit cell dimensions measured at 150 K on a Bruker diffractometer utilizing Cu $K_\alpha$ radiation ($\kappa$=1.54178 Å) of:

| | | | |
|---|---|---|---|
| a | 6.7 ± .1 Å | α | 76.0 ± .1° |
| b | 11.9 ± .1 Å | β | 82.2 ± .1° |
| c | 13.1 ± .1 Å | γ | 85.4 ± .1°. |

234. Substantially crystalline Compound 175 Form A (neat) (i.e., wherein less than 15% of Compound 175 is in amorphous form, wherein less than 10% of Compound 175 is in amorphous form, wherein less than 5% of Compound 175 is in amorphous form).

235. The substantially crystalline Compound 175 Form A (neat) according to Embodiment 234, wherein Compound 175 Form A (neat) is 100% crystalline.

236. The substantially crystalline Compound 175 Form A (neat) according to Embodiment 234 or 235, characterized by an orthorhombic crystal system, a $P2_12_12_1$ space group, and unit cell dimensions measured at 100 K on a Bruker diffractometer utilizing Cu $K_\alpha$ radiation ($\lambda$=1.54178 Å) of:

| | | | |
|---|---|---|---|
| a | 9.8 ± .1 Å | α | 90° |
| b | 10.1 ± .1 Å | β | 90° |
| c | 20.5 ± .1 Å | γ | 90°. |

237. Substantially crystalline Compound 188 dichloromethane solvate Form A (i.e., wherein less than 15% of Compound 188 dichloromethane solvate is in amorphous form, wherein less than 10% of Compound 188 dichloromethane solvate is in amorphous form, wherein less than 5% of Compound 188 dichloromethane solvate is in amorphous form).

238. The substantially crystalline Compound 188 dichloromethane solvate Form A according to Embodiment 237, wherein Compound 188 dichloromethane solvate Form A is 100% crystalline.

239. The substantially crystalline Compound 188 dichloromethane solvate Form A according to Embodiment 237 or 238, characterized by a monoclinic crystal system, a $P2_1$ space group, and unit cell dimensions measured at 100 K on a Bruker diffractometer utilizing Cu $K_\alpha$ radiation ($\lambda$=1.54178 Å) of:

| a | 16.2 ± .1 Å | α | 90° |
| b | 13.3 ± .1 Å | β | 99.7 ± .1° |
| c | 23.2 ± .1 Å | γ | 90°. |

EXAMPLES

General Experimental Procedures
Abbreviations
  AcOH: Acetic acid
  Boc anhydride ($(Boc)_2O$): Di-tert-butyl dicarbonate
  Boc: Butoxy carbonyl
  BOP: Benzotriazol-1-yloxytris(dimethylamino)phosphonium hexafluorophosphate
  t-BuOH: tert-Butanol
  $CDCl_3$: Chloroform-d
  CDI: 1,1'-Carbonyldiimidazole
  $CD_3OD$: Methyl-d4 alcohol-d
  $CH_2Cl_2$: Dichloromethane
  $CH_3CN$: Acetonitrile
  $CO_2$: Carbon dioxide
  $Cs_2CO_3$: Cesium carbonate
  CuI Copper(I) iodide
  DCE: 1,2-Dichloroethane
  DCM: Dichloromethane
  DIEA: (DIPEA; N,N-Diisopropylethylamine)
  DMAP: 4-Dimethylaminopyridine
  DMF: N,N-Dimethylformamide
  DMP: Dess-Martin Periodinane
  DMSO: Dimethyl sulfoxide
  DMSO-d6: Dimethyl sulfoxide-d6
  EDCI: 1-Ethyl-3-(3-dimethylaminopropyl)carbodiimide
  ESI-MS: Electrospray ionization mass spectrometry
  $Et_2O$: Diethyl ether
  $Et_3N$ or TEA: Triethylamine
  EtOAc: Ethyl acetate
  EtOH: Ethanol
  $Et_2O$: Diethyl ether
  ESI-MS: Electrospray ionization mass spectrometry
  Grubbs catalyst 2nd Generation: [1,3-Bis(2,4,6-trimethylphenyl)imidazolidin-2-ylidene]-dichloro-[(2-isopropoxyphenyl)methylene]ruthenium
  $H_2$: Hydrogen
  HATU: N-[(Dimethylamino)-1H-1,2,3-triazolo-[4,5-b]pyridin-1-ylmethylene]-N-methylmethanaminium hexafluorophosphate N-oxide
  HCl: Hydrochloric acid
  HOBT: Hydroxybenzotriazole
  HPLC: High performance liquid chromatography
  $H_2$: Hydrogen
  $H_2O_2$: Hydrogen peroxide
  $KHSO_4$: Potassium bisulfate
  KOH: Potassium hydroxide
  $K_2CO_3$: Potassium carbonate
  $KMnO_4$: Potassium permanganate
  $KHCO_3$: Potassium bicarbonate
  LC: Liquid chromatography
  $LiAlH_4$: Lithium aluminum hydride
  LiOH: Lithium hydroxide
  MeMgCl: Methyl magnesium chloride
  MeTHF or 2-MeTHF or 2-Me-THF: 2-Methyltetrahydrofuran
  MeOH: Methanol
  MTBE: Methyl tert-butyl ether
  $MgSO_4$: Magnesium sulfate
  MS: Mass spectrometry
  n-$Bu_4NF·H_2O$: Tetra-n-butylammonium fluoride monohydrate
  Na: Sodium
  NaH: Sodium hydride
  $NaHCO_3$: Sodium bicarbonate
  NaOAc: Sodium acetate
  NaOH: Sodium hydroxide
  $Na_2SO_4$: Sodium sulfate
  NBS: N-bromosuccinimide
  $NH_3$: Ammonia
  $NH_4Cl$: Ammonium chloride
  $NH_4HCO_3$: Ammonium bicarbonate
  NMP: N-Methyl-2-pyrrolidone
  NMR: Nuclear magnetic resonance
  $N_2$: Nitrogen
  Pd/C: Palladium on carbon
  $Pd_2(dba)_3$: Tris(dibenzylideneacetone)dipalladium(0)
  $Pd(dppf)Cl_2$: 1,1'-Bis(diphenylphosphino)ferrocene palladium(II) chloride
  $Pd(OAc)_2$: Palladium(II) acetate
  $PhI(OAc)_2$: (Diacetoxyiodo)benzene
  $POCl_3$: Phosphoryl chloride
  $PtO_2$: Platinum oxide
  RT or rt: Room temperature
  SFC: Supercritical fluid chromatography
  Silica Cat Pd: Palladium on silica
  $SiO_2$: Silica gel
  TBAF: Tetra-n-butylammonium fluoride
  TBAI: Tetrabutylammonium iodide
  TBDPS-Cl or TBDPSCl: tert-Butyldiphenylchlorosilane
  TEA: Triethylamine
  TEMPO: 2,2,6,6-Tetramethylpiperidinyloxy
  TFA: Trifluoroacetic acid
  THF: Tetrahydrofuran
  $Ti(OEt)_4$: Titanium (IV)ethoxide
  TMEDA: Tetramethylethylenediamine
  $TMSCF_3$: Trifluoromethyltrimethylsilane
  p-TsCl or tosyl chloride: p-Toluenesulfonyl chloride or 4-Toluenesulfonyl chloride
  $T_3P$: 1-Propanephosphonic anhydride
  UPLC: Ultra Performance Liquid Chromatography
  Xantphos: 4,5-Bis(diphenylphosphino)-9,9-dimethylxanthene Zhan catalyst-1B: Dichloro[1,3-bis(2,4,6-trimethylphenyl)-2-imidazolidinylidene][[5-[(dimethylamino)sulfonyl]-2-(1-methylethoxy-0)phenyl]methylene-C]ruthenium(II)

General UPLC-MS/HPLC-MS/GC Analytical Methods:
LC Method A: Analytical reverse phase UPLC-MS using an Acquity UPLC-MS BEH $C_{18}$ column (50×2.1 mm, 1.7 μm particle size) made by Waters (pn: 186002350), and a dual gradient run from 1% to 99% mobile phase B over 3.0 minutes. Mobile phase A=water (+0.05% trifluoroacetic acid). Mobile phase B=acetonitrile (+0.035% trifluoroacetic acid). Flow rate=1.2 mL/min, injection volume=1.5 μL, and column temperature=60° C.

LC Method B: Analytical reverse phase HPLC-MS using a Kinetex $C_{18}$ column (4.6×50 mm, 2.6 μm particle size). Temp: 45° C.; Flow: 2.0 mL/min; Run Time: 3 min. Mobile phase: Initial 95% water (+0.1% formic acid) and 5% acetonitrile (+0.1% formic acid) linear gradient to 95% acetonitrile (+0.1% formic acid) for 2.0 min then hold at 95% acetonitrile (+0.1% formic acid) for 1.0 min.

LC Method C: Analytical reverse phase HPLC-MS using a Kinetex Polar Cis column (3.0×50 mm, 2.6 μm particle size), Temp: 45° C.; Flow: 1.2 mL/min; Run time: 6 min. Mobile phase: Initial 95% water (+0.1% formic acid) and 5% acetonitrile (+0.1% formic acid) linear gradient to 95% acetonitrile (+0.1% formic acid) for 4.0 min then hold at 95% acetonitrile (+0.1% formic acid) for 2.0 min.

LC Method D: Analytical reverse phase UPLC-MS using an Acquity UPLC-MS BEH $C_{18}$ column (50×2.1 mm, 1.7 µm particle size) made by Waters (pn: 186002350), and a dual gradient run from 1% to 99% mobile phase B over 5.0 minutes. Mobile phase A=water (+0.05% trifluoroacetic acid). Mobile phase B=acetonitrile (+0.035% trifluoroacetic acid). Flow rate=1.2 mL/min, injection volume=1.5 µL, and column temperature=60° C.

LC Method E: Analytical reverse phase HPLC-MS using a Kinetex Polar Cis column (3.0×50 mm, 2.6 µm particle size), Temp: 45° C.; Flow: 1.2 mL/min; Run time: 3 min. Mobile phase: Initial 95% water (+0.1% formic acid) and 5% acetonitrile (+0.1% formic acid) linear gradient to 95% acetonitrile (+0.1% formic acid) for 2.0 min then hold at 95% acetonitrile (+0.1% formic acid) for 1.0 min.

LC Method F: Analytical reverse phase HPLC-MS using a Kinetex $C_{18}$ column (4.6×50 mm, 2.6 µm particle size), Temp: 45° C.; Flow: 2.0 mL/min; Run Time: 6 min. Mobile phase: Initial 95% water (+0.1% formic acid) and 5% acetonitrile (+0.1% formic acid) linear gradient to 95% acetonitrile (+0.1% formic acid) for 4.0 min then hold at 95% acetonitrile (+0.1% formic acid) for 2.0 min.

LC Method G: Analytical reverse phase HPLC-MS using a Merckmillipore Chromolith SpeedROD $C_{18}$ column (50×4.6 mm) and a dual gradient run from 5% to 100% mobile phase B over 6 minutes. Mobile phase A=water (+0.1% trifluoroacetic acid). Mobile phase B=acetonitrile (+0.1% trifluoroacetic acid).

LC Method H: Analytical reverse phase HPLC-MS using a Waters Cortex $C_{18}$ column (3.0×50 mm, 2.7 µm particle size) made by Waters (pn: 186007370), Temp: 55° C.; Flow: 1.2 mL/min; Mobile phase A: Water (+0.1% trifluoroacetic acid). Mobile phase B: Acetonitrile (+0.1% trifluoroacetic acid). Gradient: 5% to 100% B over 4 min, with equilibration at 100% B for 0.5 min, equilibration to 5 B over 1.5 min.

LC Method I: Analytical reverse phase UPLC-MS using an Acquity UPLC-MS BEH $C_{18}$ column (30×2.1 mm, 1.7 µm particle size) made by Waters (pn: 186002349), and a dual gradient run from 1% to 99% mobile phase B over 1.2 minutes. Mobile phase A=water (+0.05% trifluoroacetic acid). Mobile phase B=acetonitrile (+0.035% trifluoroacetic acid). Flow rate=1.5 mL/min, injection volume=1.5 µL, and column temperature=60° C.

LC Method J: Analytical reverse phase UPLC-MS using an Acquity UPLC-MS BEH $C_{18}$ column (50×2.1 mm, 1.7 µm particle size) made by Waters (pn: 186002350), and a dual gradient run from 30% to 99% mobile phase B over 3.0 minutes. Mobile phase A=water (+0.05% trifluoroacetic acid). Mobile phase B=acetonitrile (+0.035% trifluoroacetic acid). Flow rate=1.2 mL/min, injection volume=1.5 µL, and column temperature=60° C.

LC Method K: Analytical reverse phase HPLC-MS using a Kinetex EVO $C_{18}$ column (4.6×50 mm, 2.6 µm particle size), Temp: 45° C.; Flow: 2.0 mL/min; Run time: 4 min. Mobile phase: Initial 95% water (+0.1% formic acid) and 5% acetonitrile (+0.1% formic acid) linear gradient to 95% acetonitrile (+0.1% formic acid) for 2.0 min then hold at 95% acetonitrile (+0.1% formic acid) for 2.0 min.

LCMS Method L: Analytical reverse phase HPLC-MS using an X-Terra MS $C_{18}$ column (4.6×150 mm, 5 µm particle size), Temperature: 40° C.; Flow: 1.5 mL/min; Run Time: 10 min. Mobile phase: Initial 95% water (+10 mM ammonium bicarbonate) and 5% acetonitrile linear gradient to 95% acetonitrile for 6.5 min then hold at 95% acetonitrile for 3.5 min.

LC Method M: Analytical reverse phase UPLC-MS using an Acquity UPLC-MS BEH $C_{18}$ column (50×2.1 mm, 1.7 µm particle size) made by Waters (pn: 186002350), and a dual gradient run from 50% to 99% mobile phase B over 3.0 minutes. Mobile phase A=water (+0.05% trifluoroacetic acid). Mobile phase B=acetonitrile (+0.035% trifluoroacetic acid). Flow rate=1.2 mL/min, injection volume=1.5 µL, and column temperature=60° C.

LC Method N: Analytical reverse phase UPLC-MS using an Acquity UPLC-MS BEH $C_{18}$ column (50×2.1 mm, 1.7 µm particle size) made by Waters (pn: 186002350), and a dual gradient run from 1% to 99% mobile phase B over 3.0 minutes. Mobile phase A=water (0.05% ammonium formate). Mobile phase B=acetonitrile. Flow rate=1.2 mL/min, injection volume=1.5 µL, and column temperature=60° C.

LC Method O: Analytical reverse phase HPLC-MS using a Kinetex Polar $C_{18}$ column (3.0×50 mm, 2.6 µm particle size), Temp: 45° C.; Flow: 1.2 mL/min; Run time: 4 min. Mobile phase: Initial 95% water (+0.1% formic acid) and 5% acetonitrile (+0.1% formic acid) linear gradient to 95% acetonitrile (+0.1% formic acid) for 3.0 min then hold at 95% acetonitrile (+0.1% formic acid) for 1.0 min.

LC Method P: Analytical reverse phase UPLC-MS using an Acquity UPLC-MS BEH $C_{18}$ column (100×2.1 mm, 1.7 µm particle size) made by Waters (pn: 186002352), and a dual gradient run from 1% to 99% mobile phase B over 13.5 minutes. Mobile phase A=water (+0.05% trifluoroacetic acid). Mobile phase B=acetonitrile (+0.035% trifluoroacetic acid). Flow rate=0.8 mL/min, injection volume=1.5 µL, and column temperature=60° C.

LC Method Q: Analytical reverse phase HPLC-MS using an Onyx Monolithic Cis column (50×4.6 mm) sold by Phenomenex (pn: CHO-7644), and a dual gradient run from 1% to 99% mobile phase B over 2.9 minutes. Mobile phase A=water (+0.05% trifluoroacetic acid). Mobile phase B=acetonitrile (+0.035% trifluoroacetic acid). Flow rate=12 mL/min, injection volume=50 µL, and column temperature=25° C.

LC Method R: Analytical reverse phase UPLC-MS using an Acquity UPLC-MS BEH $C_{18}$ column (30×2.1 mm, 1.7 µm particle size) made by Waters (pn: 186002349), and a dual gradient run from 30% to 99% mobile phase B over 1.0 minutes. Mobile phase A=water (+0.05% trifluoroacetic acid). Mobile phase B=acetonitrile (+0.035% trifluoroacetic acid). Flow rate=1.2 mL/min, injection volume=1.5 µL, and column temperature=60° C.

LC Method S: Analytical reverse phase UPLC-MS using an Acquity UPLC-MS BEH $C_{18}$ column (30×2.1 mm, 1.7 µm particle size) made by Waters (pn: 186002349), and a dual gradient run from 1% to 99% mobile phase B over 1.0 minutes. Mobile phase A=water (+0.05% trifluoroacetic acid). Mobile phase B=acetonitrile (+0.035% trifluoroacetic acid). Flow rate=1.5 mL/min, injection volume=1.5 µL, and column temperature=60° C.

LC Method T: Analytical reverse phase UPLC-MS using an Acquity UPLC-MS BEH $C_{18}$ column (30×2.1 mm, 1.7 µm particle size) made by Waters (pn: 186002349), and a dual gradient run from 50% to 99% mobile phase B over 1.0 minutes. Mobile phase A=water (+0.05% trifluoroacetic acid). Mobile phase B=acetonitrile (+0.035% trifluoroacetic acid). Flow rate=1.2 mL/min, injection volume=1.5 µL, and column temperature=60° C.

LC Method U: Analytical reverse phase UPLC-MS using an Acquity UPLC-MS BEH $C_{18}$ column (30×2.1 mm, 1.7 µm particle size) made by Waters (pn: 186002349), and a dual gradient run from 75% to 99% mobile phase B over 1.0 minutes. Mobile phase A=water (+0.05% trifluoroacetic acid). Mobile phase B=acetonitrile (+0.035% trifluoroacetic acid). Flow rate=1.2 mL/min, injection volume=1.5 μL, and column temperature=60° C.

LC Method V: Analytical reverse phase HPLC-MS using a Kinetex EVO $C_{18}$ column (2.1×50 mm 2.6 μm particle size), Temp: 45° C.; Flow: 1.0 mL/min; Run time: 1.5 min. Mobile phase: Initial 98% of mobile phase A (10 mM ammonium formate in water: acetonitrile, 95:5, pH 9) and 2% mobile phase B (acetonitrile) linear gradient to 98% acetonitrile for 1.15 min then hold at 98% acetonitrile for 0.2 min then return to 98% water and 10 mM ammonium formate for 0.05 min and hold for 0.1 min.

LC Method W: Analytical reverse phase HPLC-MS using a Kinetex Polar $C_{18}$ column (3.0×50 mm, 2.6 μm particle size), Temp: 45° C.; Flow: 1.2 mL/min; Run time: 4 min. Mobile phase: Initial 95% water (+0.1% formic acid) and 5% acetonitrile (+0.1% formic acid) linear gradient to 95% acetonitrile (+0.1% formic acid) for 3.0 min then hold at 95% acetonitrile (+0.1% formic acid) for 1.0 min.

LC Method X: Analytical reverse phase HPLC-MS using a Kinetex Polar $C_{18}$ column (3.0×50 mm, 2.6 μm particle size), Temp: 45° C.; Flow: 1.2 mL/min; Run time: 5 min. Mobile phase: Initial 95% water (+0.1% formic acid) and 5% acetonitrile (+0.1% formic acid) linear gradient to 95% acetonitrile (+0.1% formic acid) for 4.0 min then hold at 95% acetonitrile (+0.1% formic acid) for 1.0 min.

LC Method Y: Analytical reverse phase HPLC-MS using a Luna $C_{18}$ column (3.0×50 mm, 3 μm particle size), Temp: 45° C.; Flow: 1.5 mL/min; Run time: 3.5 min. Mobile phase: Initial 95% water (+0.1% formic acid) and 5% acetonitrile (+0.1% formic acid) linear gradient to 95% acetonitrile (+0.1% formic acid) for 1.3 min then hold at 95% acetonitrile (+0.1% formic acid) for 2.2 min.

LC Method Z: Analytical reverse phase HPLC-MS using a Luna $C_{18}$ column (3.0×50 mm, 3 μm particle size), Temp: 45° C.; Flow: 1.5 mL/min; Run time: 2.5 min. Mobile phase: Initial 95% water (+0.1% formic acid) and 5% acetonitrile (+0.1% formic acid) linear gradient to 95% acetonitrile (+0.1% formic acid) for 1.3 min then hold at 95% acetonitrile (+0.1% formic acid) for 1.2 min.

LC Method AA: Analytical reverse phase HPLC-MS using a SunFire $C_{18}$ column (4.6×75 mm, 3.5 μm particle size), Temp: 45° C.; Flow: 1.5 mL/min; Run time: 6 min. Mobile phase: Initial 95% water (+0.1% formic acid) and 5% acetonitrile (+0.1% formic acid) linear gradient to 95% acetonitrile (+0.1% formic acid) for 4.0 min then hold at 95% acetonitrile (+0.1% formic acid) for 2.0 min.

LC Method BB: Analytical reverse phase HPLC-MS using an)(Bridge Cis column (4.6×75 mm, 5 μm particle size); Flow: 1.5 mL/min; Run time: 6 min. Mobile phase: Initial 95% water (+10 mM ammonium bicarbonate) and 5% acetonitrile to 5% water (+10 mM ammonium bicarbonate) and 95% acetonitrile for 3 min then hold at 95% acetonitrile and 5% water (+10 mM ammonium bicarbonate) for 3 min.

LC Method CC: Analytical GC using a Phenomenex ZB-1MS column (0.25×30 mm, 0.25 μm particle size); start temp 50° C., ramp 20° C./min to 300° C. and hold for 5 min.

LC Method DD: Analytical reverse phase HPLC-MS using a Merckmillipore Chromolith SpeedROD $C_{18}$ column (50×4.6 mm) and a dual gradient run from 5% to 100% mobile phase B over 12 minutes. Mobile phase A=water (+0.1% trifluoroacetic acid). Mobile phase B=acetonitrile (+0.1% trifluoroacetic acid).

LC Method EE: Analytical reverse phase HPLC-MS using a Kinetex EVO Cis column (4.6×50 mm, 2.6 μm particle size), Temp: 45° C., Flow: 2.0 ml/min, Run Time: 3 minutes. Mobile Phase Conditions: Initial 95% water (+0.1% formic acid) and 5% acetonitrile (+0.1% formic acid) linear gradient to 95% acetonitrile (+0.1% formic acid) for 2.0 min then hold at 95% acetonitrile (+0.1% formic acid) for 1.0 min.

General X-Ray Powder Diffraction (XRPD) Method

The X-ray powder diffraction (XRPD) pattern was recorded at room temperature in continuous mode using a PANalytical Empyrean X-ray Diffract meter (Almelo, The Netherlands). The X-ray was generated using Cu tube operated at 45 kV and 40 mA. Pixel 1d detector was used with anti-scatter slit P8. The Divergence optics was Bragg Brentano High Definition (BBHD) with a 10 mm mask, ⅛ divergence slit, and ½ anti-scatter slit. The continuous scan mode utilized a 0.0131 degree step size and count time of 13.77 seconds per step, integrated over the range from 4 to 40 degrees two-theta. The powder sample was placed on an indented area within a zero background holder and flattened with a glass slide.

General Thermogravimetric Analysis (TGA) Method

TGA was used to investigate the presence of residual solvents in the lots characterized and identify the temperature at which decomposition of the sample occurs. Unless provided otherwise in the following Examples, TGA data were collected on a Mettler Toledo TGA/DSC 3+ STARe System. TGA data for Compound 4 were collected on a TA instrument Discovery series with TRIOS system.

General Differential Scanning Calorimetry (DSC) Method

Unless provided otherwise in the following Examples, the melting point or glass transition point of the material was measured using a Mettler Toledo TGA/DSC 3+ STARe System. DSC data for Compound 4 were collected on a TA instrument Discovery series with TRIOS system.

General Synthetic Schemes:

Another aspect of the disclosure provides methods for making compounds of Formulae I, I', I", Ia, Ia', IIa, IIa', IIb, IIb', IIc, IIc', IId, IId', IIe, IIe', IIf, IIf', IIg, IIg', IIh, IIh', Compounds 1 to 213, Compounds 214 to 222, deuterated derivatives thereof, and pharmaceutically acceptable salts of those compounds and deuterated derivatives, and intermediates for making any of the foregoing. In some embodiments of the following Schemes and Examples, each nitrogen and oxygen atom may optionally have, in addition to or in place of a specified variable substituent, one or more protecting groups selected from the range of protecting groups disclosed herein. In some embodiments of the following Schemes and Examples, each compound may be replaced with its deuterated derivative.

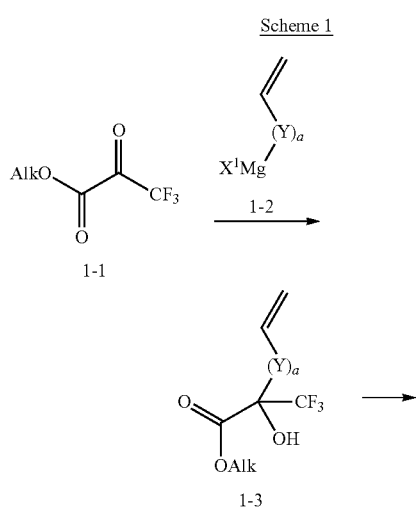

Scheme 1

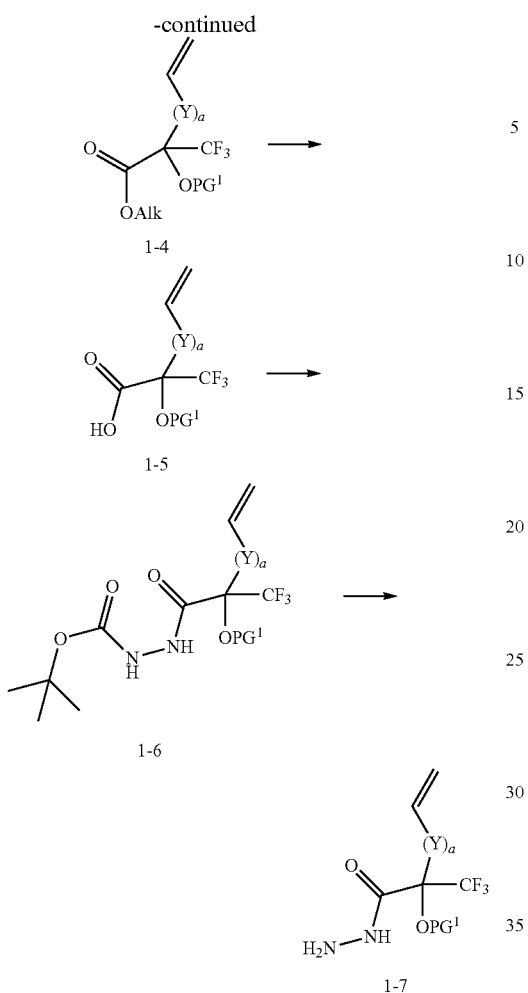

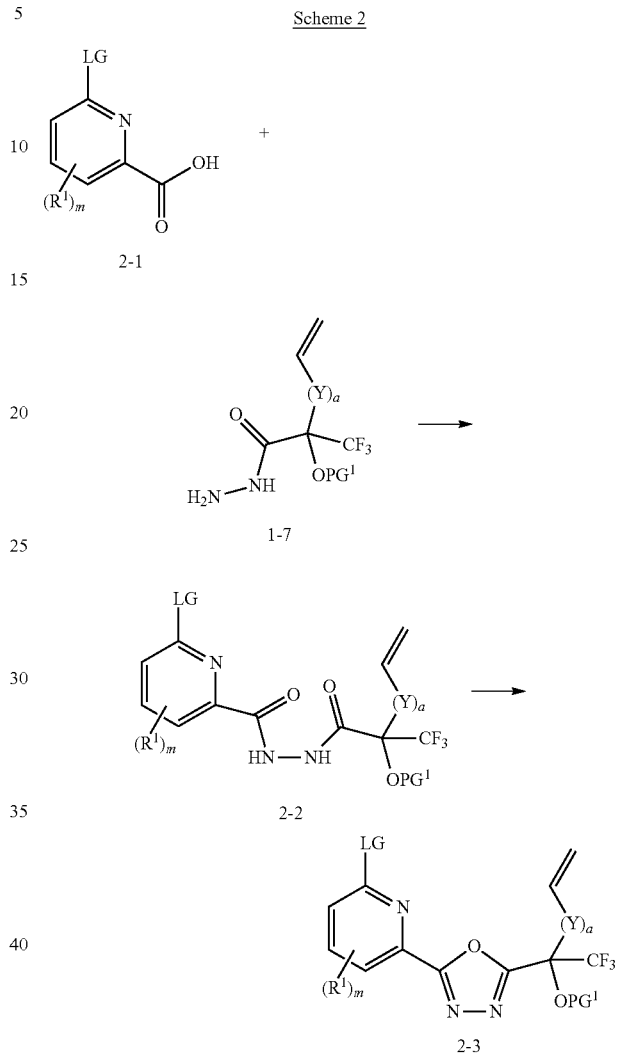

Scheme 1 refers to processes for preparing an intermediate compound of Formula 1-7 from a compound of Formula 1-1. Alk is selected from $C_1$-$C_6$ linear or branched alkyl groups. $X^1$ is selected from halogens, such as Cl, I, or Br. $PG^1$ is selected from suitable oxygen protecting groups, such as benzyl and silyl moieties (e.g., TBDPS, TBS, and TMS). a is an integer selected from 2, 3, 4, and 5. Y is as defined for Formula I above.

Any suitable conditions for a Grignard-type addition can be used to react a compound of Formula 1-1 with a compound of Formula 1-2 to form a compound of Formula 1-3. For example, the Grignard addition of a compound of Formula 1-1 with a compound of Formula 1-2 may be performed in $Et_2O$ at −78° C., followed by addition of 1 N aqueous HCl to yield a compound of Formula 1-3. Conversion of a compound of Formula 1-3 to a compound of Formula 1-4 may be accomplished by any suitable procedure to install an oxygen protecting group. Conversion of an ester of Formula 1-4 to a carboxylic acid of Formula 1-5 may be accomplished by any suitable hydrolysis conditions. For example, conversion of a carboxylic acid of Formula 1-5 to a compound of Formula 1-6 may be accomplished by reacting a compound of Formula 1-5 with HATU and $Et_3N$ in DMF, followed by addition of tert-butyl N-aminocarbamate. Any suitable hydrolysis conditions may be used to convert a carbamate of Formula 1-6 to a hydrazide of Formula 1-7. For example, a compound of Formula 1-7 may be obtained by reacting a compound of Formula 1-6 with HCl in $CH_2Cl_2$ at ambient temperature.

Scheme 2 refers to processes for preparing an intermediate compound of Formula 2-3 from a compound of Formula 2-1. LG is selected from halogen and oxygen-based leaving groups such as OTf and OTs. $PG^1$ is selected from suitable oxygen protecting groups, such as benzyl and silyl moieties (e.g., TBDPS, TBS, and TMS). a is an integer selected from 2, 3, 4, and 5. $R^1$, m, and Y are as defined for Formula I above.

Any suitable conditions to form an amide bond can be used to produce a compound of Formula 2-3 from a compound of Formula 2-1 and a compound of Formula 1-7. For example, a compound of Formula 2-1 can be reacted with CDI in acetonitrile and DMF, followed by addition of a compound of Formula 1-7, to yield a compound of Formula S2-2. A compound of Formula 2-2 can be converted to a compound of Formula 2-3 using any conditions suitable for oxadiazole formation. For example, a compound of Formula 2-2 can be reacted with DIPEA in acetonitrile, followed by addition of p-toluenesulfonyl chloride, to yield an oxadiazole of Formula 2-3.

Scheme 3

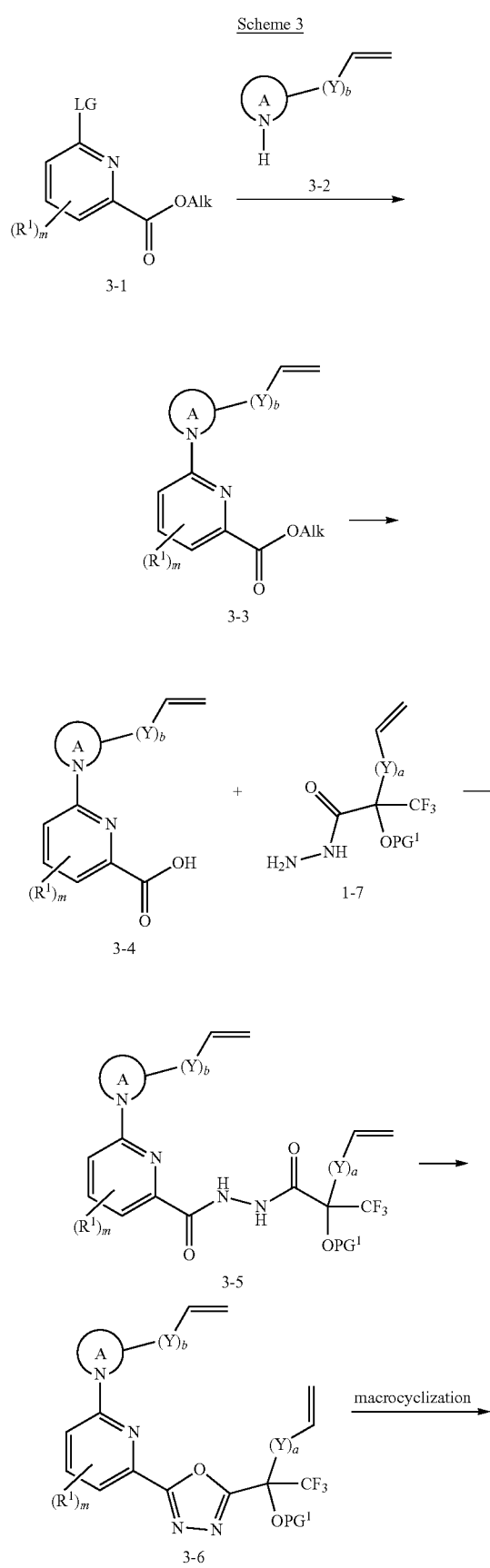

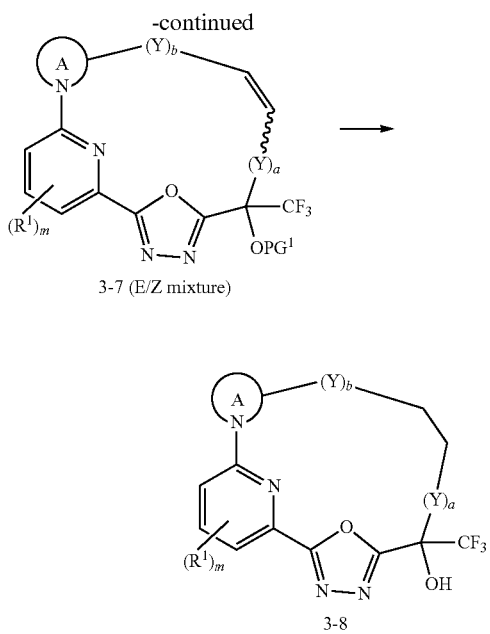

Scheme 3 refers to processes for preparing a compound of Formula 3-8 from a compound of Formula 3-1. Alk is selected from $C_1$-$C_6$ linear or branched alkyl groups. LG is selected from halogen and oxygen-based leaving groups such as OTf and OTs. $PG^1$ is selected from suitable oxygen protecting groups, such as benzyl and silyl moieties (e.g., TBDPS, TBS, and TMS). a is an integer selected from 1, 2, 3, and 4, and b is an integer selected from 0, 1, 2, 3, and 4 provided that a+b is not greater than 5. Ring A, $R^1$, m, and Y are as defined for Formula I above.

The reaction of a compound of Formula 3-1 with a compound of Formula 3-2 to yield a compound of Formula 3-3 may be accomplished by any suitable aromatic substitution conditions. Conversion of an ester of Formula 3-3 to a carboxylic acid of Formula 3-4 may be accomplished by any suitable hydrolysis conditions. A compound of Formula 3-5 may be prepared from a compound of Formula 3-4 and a compound of Formula 1-7 using any suitable amide bond formation conditions. A compound of Formula 3-5 can be converted to a compound of Formula 3-6 using any conditions suitable for oxadiazole formation. For example, a compound of Formula 3-5 can be reacted with DIPEA in acetonitrile, followed by addition of p-toluenesulfonyl chloride, to yield an oxadiazole of Formula 3-6. Macrocyclization of a compound of Formula 3-6 may be accomplished by any suitable ring-closing metathesis conditions. For example, a compound of Formula 3-6 may be reacted in the presence of Grubbs $2^{nd}$ generation catalyst in DCE to yield a macrocycle of Formula 3-7 as a mixture of E/Z isomers (as denoted by the ∼ bond). Conversion of an unsaturated compound of Formula 3-7 to a macrocycle of Formula 3-8 can be accomplished using any suitable procedure for olefin reduction and alcohol deprotection.

Scheme 4

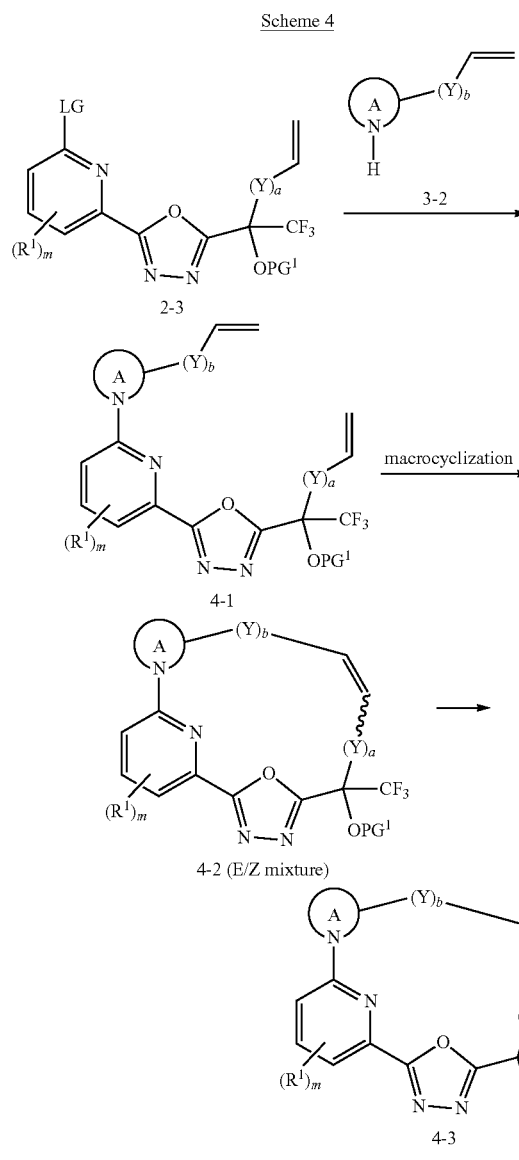

4-3

Scheme 5

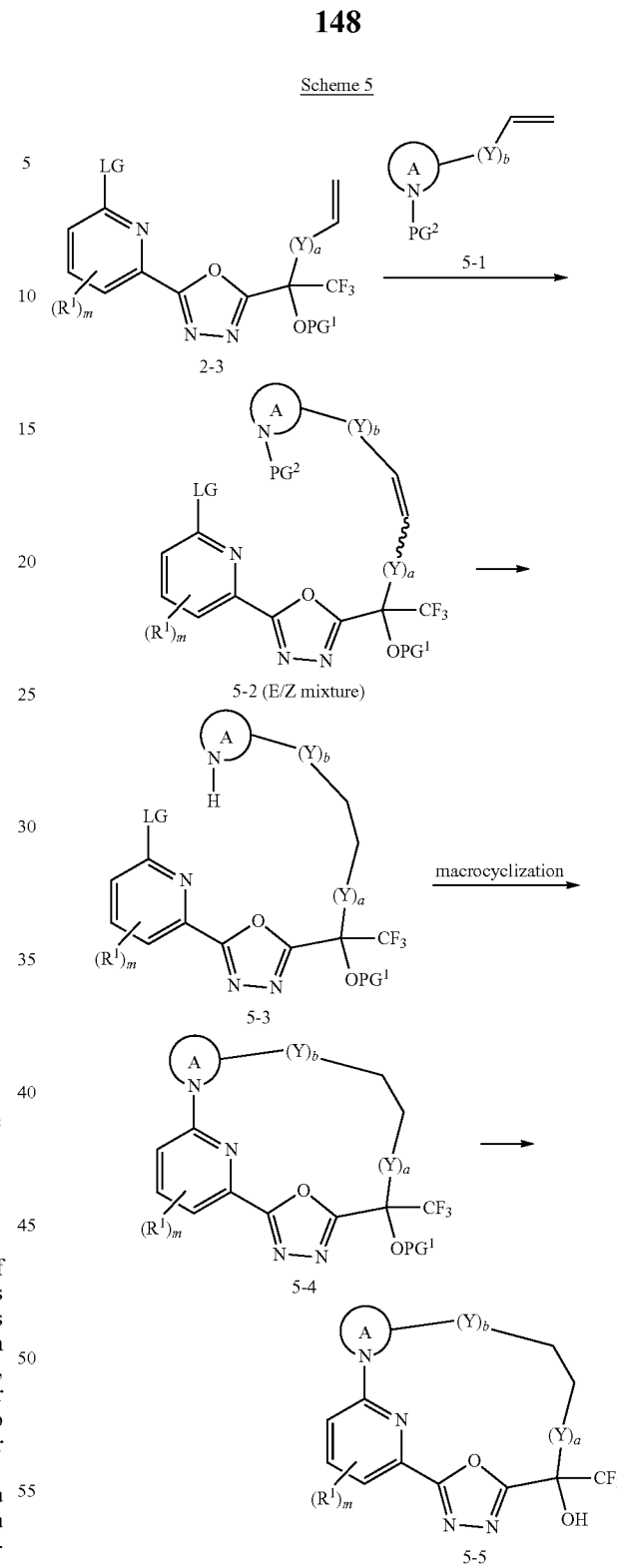

5-5

Scheme 4 refers to processes for preparing a compound of Formula 4-3 from a compound of Formula 2-3. LG is selected from halogen and oxygen-based leaving groups such as OTf and OTs. $PG^1$ is selected from suitable oxygen protecting groups, such as benzyl and silyl moieties (e.g., TBDPS, TBS, and TMS). Each of a and b is an integer independently selected from 1, 2, 3, and 4, provided that a+b is not greater than 5. Ring A, $R^1$, m, and Y are as defined for Formula I above.

The reaction of a compound of Formula 2-3 with a compound of Formula 3-2 to yield a compound of Formula 4-1 may be accomplished by any suitable aromatic substitution conditions. Macrocyclization of a compound of Formula 4-1 to produce a compound of Formula 4-2 may be accomplished by any suitable ring-closing metathesis conditions. For example, a compound of Formula 4-1 may be reacted in the presence of Zhan catalyst-1B in DCE to yield a macrocycle of Formula 4-2 as a mixture of E/Z isomers (as denoted by the ∼ bond). Conversion of an unsaturated compound of Formula 4-2 to a macrocycle of Formula 4-3 can be accomplished using any suitable procedure for olefin reduction and alcohol deprotection.

Scheme 5 refers to processes for preparing a compound of Formula 5-5 from a compound of Formula 2-3. LG is selected from halogen and oxygen-based leaving groups such as OTf and OTs. $PG^1$ is selected from suitable oxygen protecting groups, such as benzyl and silyl moieties (e.g., TBDPS, TBS, and TMS). $PG^2$ is selected from suitable nitrogen protecting groups, such as Boc and Fmoc. Each of a and b is an integer independently selected from 1, 2, 3, and 4, provided that a+b is not greater than 5. Ring A, $R^1$, m, and Y are as defined for Formula I above.

The reaction of a compound of Formula 2-3 with a compound of Formula 5-1 to yield a compound of Formula 5-2 may be accomplished by any cross-metathesis conditions. For example, a terminal olefin-containing compound of Formula 2-3 may be reacted a terminal olefin-containing compound of Formula 5-1 in the presence of Grubbs $2^{nd}$ generation catalyst in DCE to yield a cross-metatheis product of Formula 5-2. Conversion of an unsaturated compound of Formula 5-2 to a compound of Formula 5-3 can be accomplished using any suitable procedure for olefin reduction and amine deprotection. Macrocyclization of a compound of Formula 5-3 to produce a compound of Formula 5-4 may be accomplished by any suitable aromatic substitution conditions. Conversion of a compound of Formula 5-4 to an alcohol of Formula 5-5 can be accomplished using any suitable procedure for alcohol deprotection.

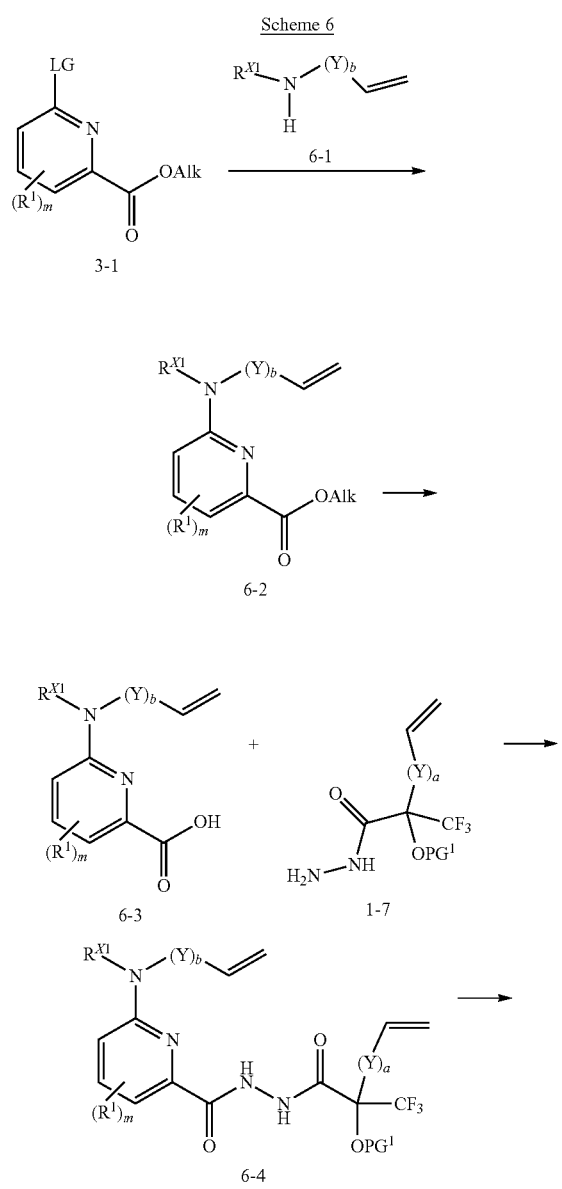

Scheme 6 refers to processes for preparing a compound of Formula 6-7 from a compound of Formula 3-1. Alk is selected from $C_1$-$C_6$ linear or branched alkyl groups. LG is selected from halogen and oxygen-based leaving groups such as OTf and OTs. $PG^1$ is selected from suitable oxygen protecting groups, such as benzyl and silyl moieties (e.g., TBDPS, TBS, and TMS). Each of a and b is an integer independently selected from 1, 2, 3, and 4, provided that a+b is not greater than 5. $R^1$, m, Y and $R^{X1}$ are as defined for Formula I above.

The reaction of a compound of Formula 3-1 with a compound of Formula 6-1 to yield a compound of Formula 6-2 may be accomplished by any suitable aromatic substitution conditions. Conversion of an ester of Formula 6-2 to a carboxylic acid of Formula 6-3 may be accomplished by any suitable hydrolysis conditions. A compound of Formula 6-4 may be prepared from a compound of Formula 6-3 and a compound of Formula 1-7 using any suitable amide bond formation conditions. A compound of Formula 6-4 can be converted to a compound of Formula 6-5 using any conditions suitable for oxadiazole formation. For example, a compound of Formula 6-4 can be reacted with DIEA in acetonitrile, followed by addition of p-toluenesulfonyl chloride, to yield an oxadiazole of Formula 6-5. Macrocyclization of a compound of Formula 6-5 to produce a compound of Formula 6-6 may be accomplished by any suitable ring-closing metathesis conditions. For example, a compound of Formula 6-5 may be reacted in the presence of Zhan catalyst-1B in DCE to yield a macrocycle of Formula 6-6 as a mixture of E/Z isomers (as denoted by the ⁓ bond). Conversion of an unsaturated compound of Formula 6-6 to a macrocycle of Formula 6-7 can be accomplished using any suitable procedure for olefin reduction and alcohol deprotection.

Scheme 7

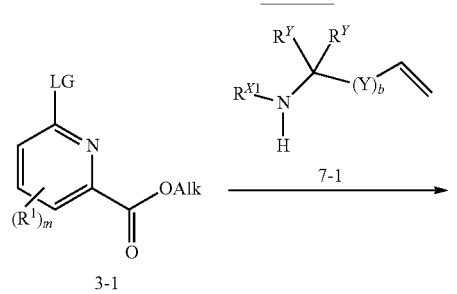

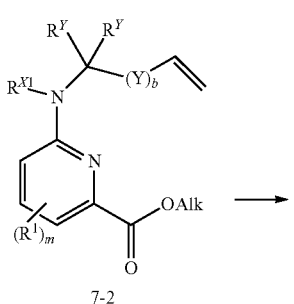

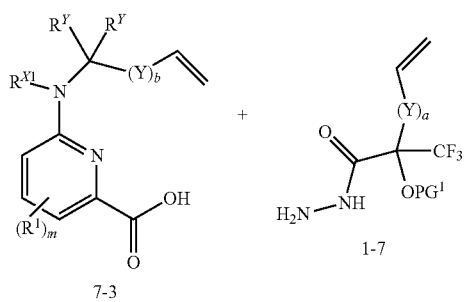

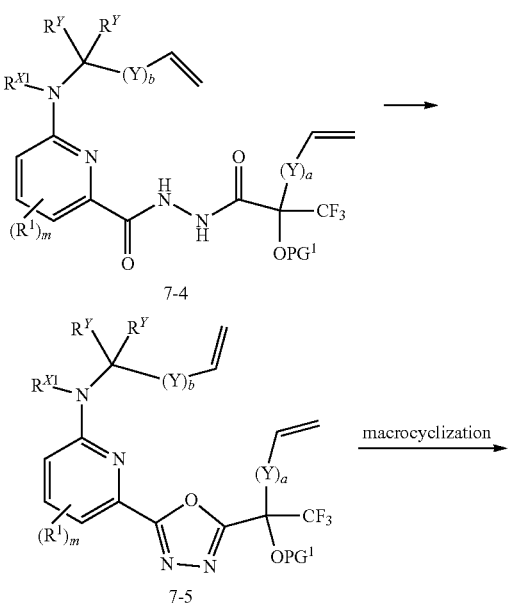

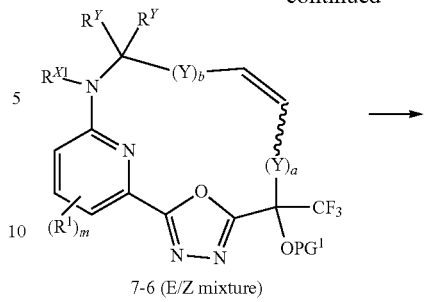

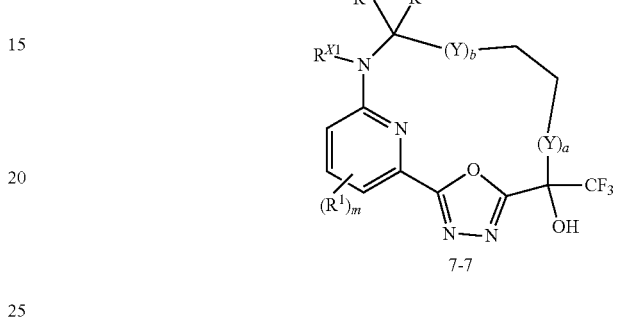

Scheme 7 refers to processes for preparing a compound of Formula 7-7 from a compound of Formula 3-1. Alk is selected from $C_1$-$C_6$ linear or branched alkyl groups. LG is selected from halogen and oxygen-based leaving groups such as OTf and OTs. PG is selected from suitable oxygen protecting groups, such as benzyl and silyl moieties (e.g., TBDPS, TBS, and TMS). Each of a and b is an integer independently selected from 0, 1, 2, and 3, provided that a+b is not greater than 4. $R^1$, m, Y, $R^{X1}$, and $R^Y$ are as defined for Formula I above.

The reaction of a compound of Formula 3-1 with a compound of Formula 7-1 to yield a compound of Formula 7-2 may be accomplished by any suitable aromatic substitution conditions. Conversion of an ester of Formula 7-2 to a carboxylic acid of Formula 7-3 may be accomplished by any suitable hydrolysis conditions. A compound of Formula 7-4 may be prepared from a compound of Formula 7-3 and a compound of Formula 1-7 using any suitable amide bond formation conditions. A compound of Formula 7-4 can be converted to a compound of Formula 7-5 using any conditions suitable for oxadiazole formation. For example, a compound of Formula 7-4 can be reacted with DIEA in acetonitrile, followed by addition of p-toluenesulfonyl chloride, to yield an oxadiazole of Formula 7-5. Macrocyclization of a compound of Formula 7-5 to produce a compound of Formula 7-6 may be accomplished by any suitable ring-closing metathesis conditions. For example, a compound of Formula 7-5 may be reacted in the presence of Zhan catalyst-1B in DCE to yield a macrocycle of Formula 7-6 as a mixture of E/Z isomers (as denoted by the ∿ bond). Conversion of an unsaturated compound of Formula 7-6 to a macrocycle of Formula 7-7 can be accomplished using any suitable procedure for olefin reduction and alcohol deprotection.

Scheme 8

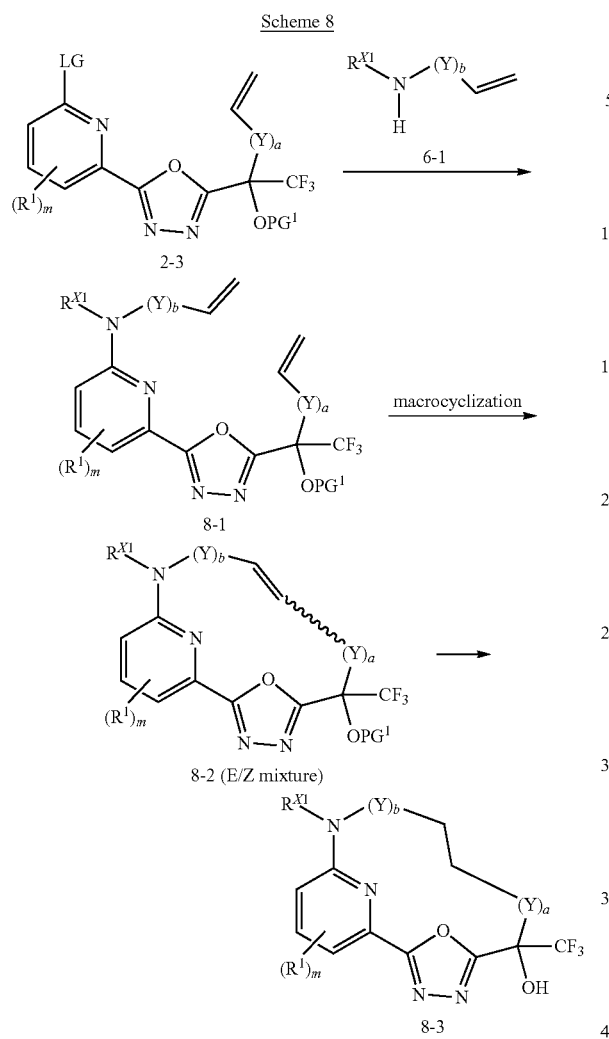

Scheme 8 refers to processes for preparing a compound of Formula 8-3 from a compound of Formula 2-3. LG is selected from halogen and oxygen-based leaving groups such as OTf and OTs. $PG^1$ is selected from suitable oxygen protecting groups, such as benzyl and silyl moieties (e.g., TBDPS, TBS, and TMS). Each of a and b is an integer independently selected from 1, 2, 3, and 4, provided that a+b is not greater than 5. $R^1$, m, Y, and $R^{X1}$ are as defined for Formula I above.

The reaction of a compound of Formula 2-3 with a compound of Formula 6-1 to yield a compound of Formula 8-1 may be accomplished by any suitable aromatic substitution conditions. For example, a compound of Formula 2-3 can be reacted with DIEA in acetonitrile and heated to yield a compound of Formula 8-1. Macrocyclization of a compound of Formula 8-1 to produce a compound of Formula 8-2 may be accomplished by any suitable ring-closing metathesis conditions. For example, a compound of Formula 8-1 may be reacted in the presence of Zhan catalyst-1B in DCE to yield a macrocycle of Formula 8-2 as a mixture of E/Z isomers (as denoted by the ⁓ bond). Conversion of an unsaturated compound of Formula 8-2 to a macrocycle of Formula 8-3 can be accomplished using any suitable procedure for olefin reduction and alcohol deprotection.

Scheme 9

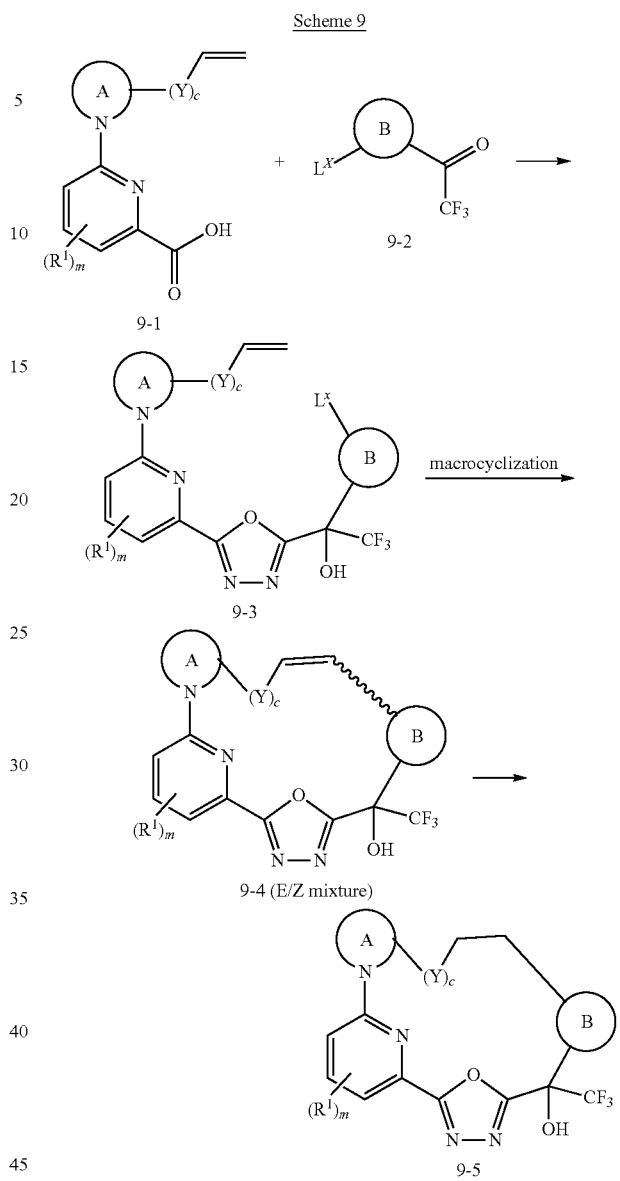

Scheme 9 refers to processes for preparing a compound of Formula 9-5 from a compound of Formula 9-1. $L^X$ is selected from halogens such as Cl, I, or Br. c is an integer independently selected from 1, 2, 3, and 4. Ring A, Ring B, m, and Y are as defined for Formula I above.

The reaction of a compound of Formula 9-1 with a compound of Formula 9-2 to yield a compound of Formula 9-3 may be accomplished by any suitable oxadiazole formation conditions. For example, a compound of Formula 9-2 may be reacted with (N-isocyanoimino)triphenylphosphorane in DCM, followed by dropwise addition of a compound of Formula 9-1, to yield a compound of Formula 9-3. Macrocyclization of a compound of Formula 9-3 to produce a compound of Formula 9-4 may be accomplished by any suitable palladium-catalyzed olefin coupling conditions. For example, a compound of Formula 9-3 in acetonitrile may be reacted with tris-o-tolylphosphane and $Pd(OAc)_2$, followed by addition of triethylamine, to yield a macrocycle of Formula 9-4 as a mixture of E/Z isomers (as denoted by the ⁓ bond). Conversion of an unsaturated compound of Formula 9-4 to a macrocycle of Formula 9-5 can be accomplished using any suitable procedure for olefin reduction.

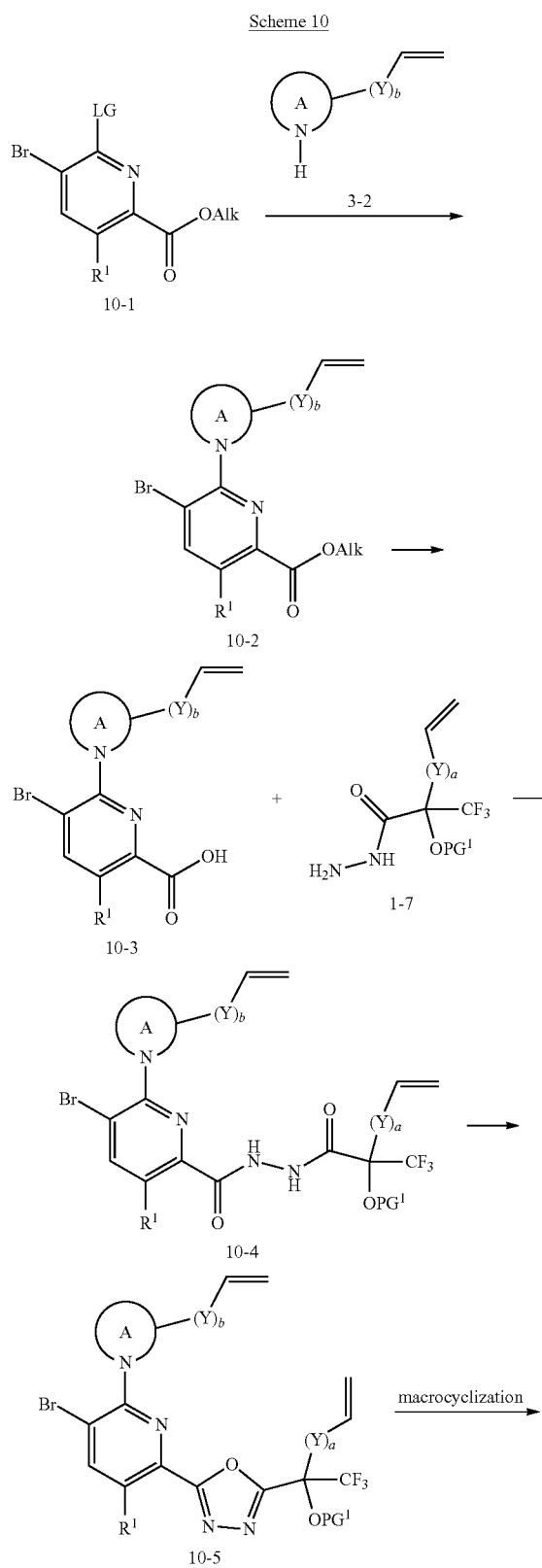

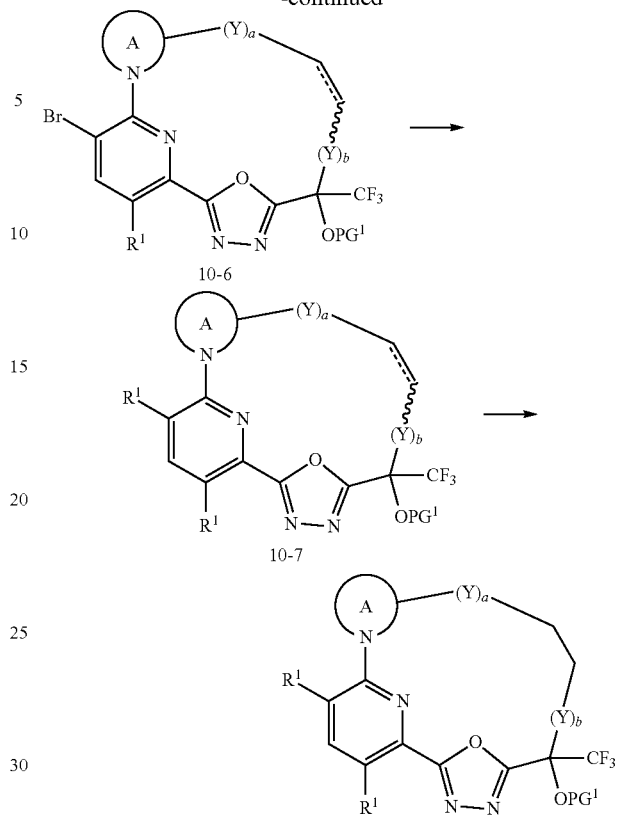

Scheme 10 refers to processes for preparing a compound of Formula 10-8 from a compound of Formula 10-1. Alk is selected from $C_1$-$C_6$ linear or branched alkyl groups. LG is selected from halogen and oxygen-based leaving groups such as OTf and OTs. Each of a and b is an integer independently selected from 1, 2, 3, and 4, provided that a+b is not greater than 5. Ring A, $R^1$, and Y are as defined for Formula I above.

The reaction of a compound of Formula 10-1 with a compound of Formula 3-2 to yield a compound of Formula 10-2 may be accomplished by any suitable aromatic substitution conditions. For example, a compound of Formula 10-1 may be reacted with a compound of Formula 3-2 and DIEA in acetonitrile to yield a compound of Formula 10-2. Conversion of an ester of Formula 10-2 to a carboxylic acid of Formula 10-3 may be accomplished by any suitable hydrolysis conditions. A compound of Formula 10-4 may be prepared from a compound of Formula 10-3 and a compound of Formula 1-7 using any suitable amide bond formation conditions. A compound of Formula 10-4 can be converted to a compound of Formula 10-5 using any conditions suitable for oxadiazole formation. For example, a compound of Formula 10-4 can be reacted with DIEA in acetonitrile, followed by addition of p-toluenesulfonyl chloride, to yield an oxadiazole of Formula 10-5. Macrocyclization of a compound of Formula 10-5 to produce a compound of Formula 10-6 may be accomplished by any suitable ring-closing metathesis conditions. For example, a compound of Formula 10-5 may be reacted in the presence of Zhan catalyst-1B in DCE to yield a macrocycle of Formula 10-6 as a mixture of E/Z isomers (as denoted by the ⁓ bond). The conversion of a compound of Formula 10-7 to a compound of Formula 10-8 may be accomplished by any suitable aromatic substitution conditions. Conversion of an unsaturated compound of Formula 10-7 to a macrocycle of Formula 10-8 may be accomplished using any suitable procedure for olefin reduction and alcohol deprotection.

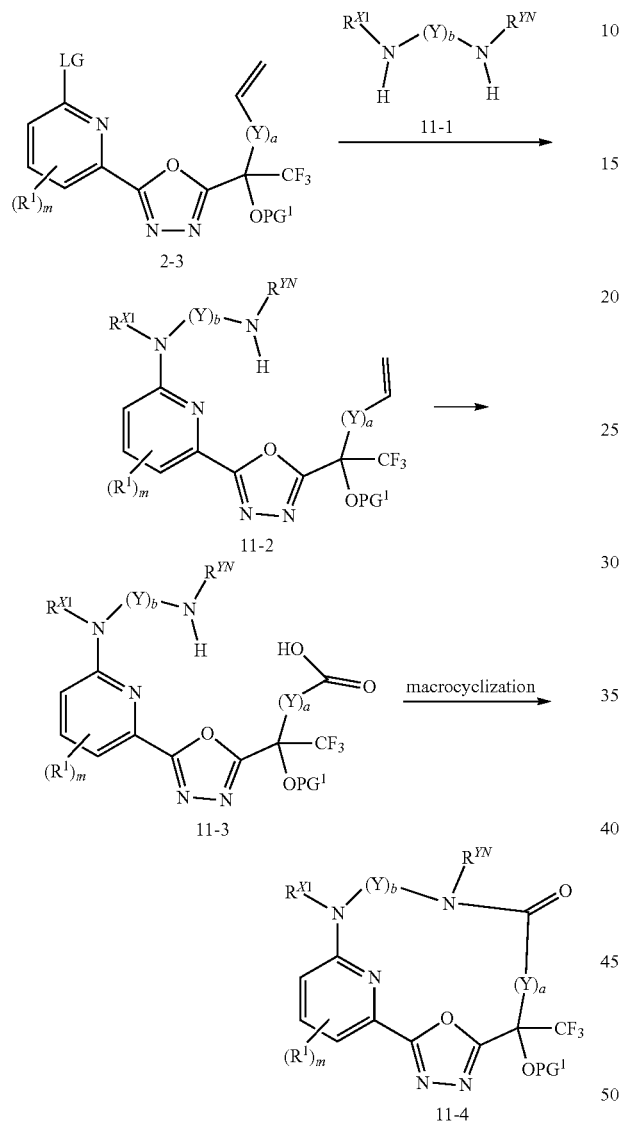

in the presence of heat to yield a compound of Formula 11-2. Conversion of a terminal olefin-containing compound of Formula 11-2 to a carboxylic acid of Formula 11-3 may be accomplished by any oxiditative cleavage conditions. For example, a compound of Formula 11-2 may be reacted in a mixture of dioxane and water in the presence of osmium tetroxide and sodium periodate to yield a compound of Formula 11-3. Macrocyclization of a compound of Formula 11-3 to produce a compound of Formula 11-4 may be accomplished by any suitable amide bond formation conditions. For example, a compound of Formula 11-3 may be reacted in DMF with IDEA, followed by addition of HATU, to yield a compound of Formula 11-4.

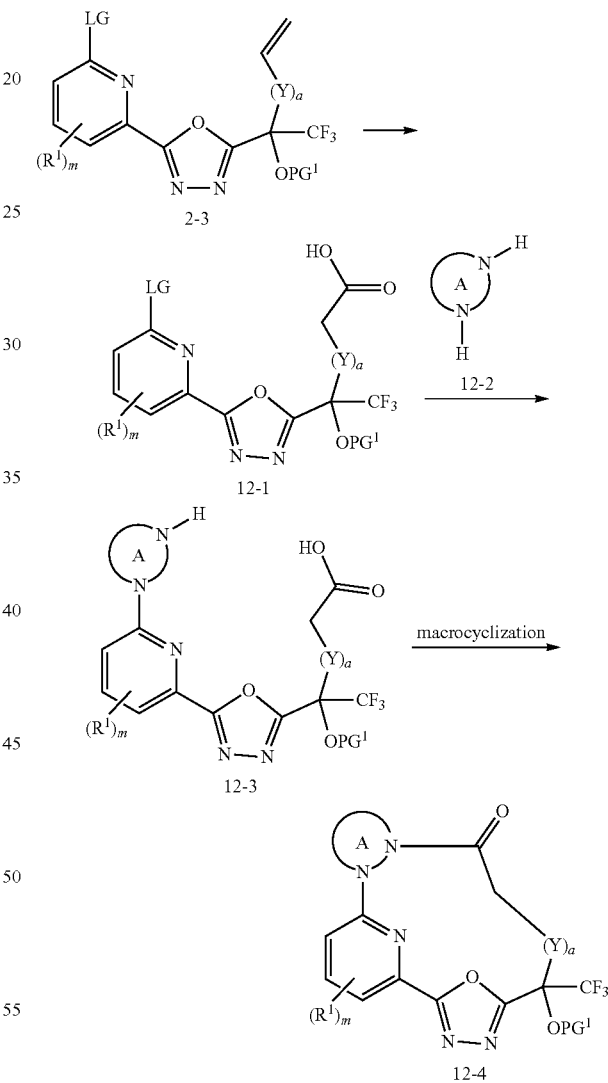

Scheme 11 refers to processes for preparing a compound of Formula 11-4 from a compound of Formula 2-3. LG is selected from halogen and oxygen-based leaving groups such as OTf and OTs. $PG^1$ is selected from suitable oxygen protecting groups, such as benzyl and silyl moieties (e.g., TBDPS, TBS, and TMS). Each of a and b is an integer independently selected from 1, 2, 3, and 4, provided that a+b is not greater than 5. $R^1$, m, Y, $R^{X1}$, and $R^{YN}$ are as defined for Formula I above.

The reaction of a compound of Formula 2-3 with a compound of Formula 11-1 to yield a compound of Formula 11-2 may be accomplished by any suitable aromatic substitution conditions. For example, a compound of Formula 2-3 and a compound of Formula 11-1 may be reacted in DMSO Scheme 12 refers to processes for preparing a compound of Formula 12-4 from a compound of Formula 2-3. LG is selected from halogen and oxygen-based leaving groups such as OTf and OTs. $PG^1$ is selected from suitable oxygen protecting groups, such as benzyl and silyl moieties (e.g., TBDPS, TBS, and TMS). a is an integer selected from 3, 4, 5, and 6. Ring A, $R^1$, m, and Y are as defined for Formula I above.

Conversion of a terminal olefin-containing compound of Formula 2-3 to a carboxylic acid of Formula 12-1 may be accomplished by any suitable oxidative conditions. For example, a compound of Formula 2-3 can be converted to an alcohol by hydroboration/oxidation, followed by oxidation of the alcohol to a carboxylic acid, to yield a compound of Formula 12-1. The reaction of a compound of Formula 12-1 with a compound of Formula 12-2 to yield a compound of Formula 12-3 may be accomplished by any suitable aromatic substitution conditions. For example, a compound of Formula 12-1 may be reacted with a compound of Formula 12-2 and diisopropylethylamine in a microwave to yield a compound of Formula 12-3. Macrocyclization of a compound of Formula 12-3 to produce a compound of Formula 12-4 may be accomplished by any suitable amide bond formation conditions. For example, a compound of Formula 12-3 may be reacted with DIEA in DMF, followed by addition of HATU, to produce a compound of Formula 12-4.

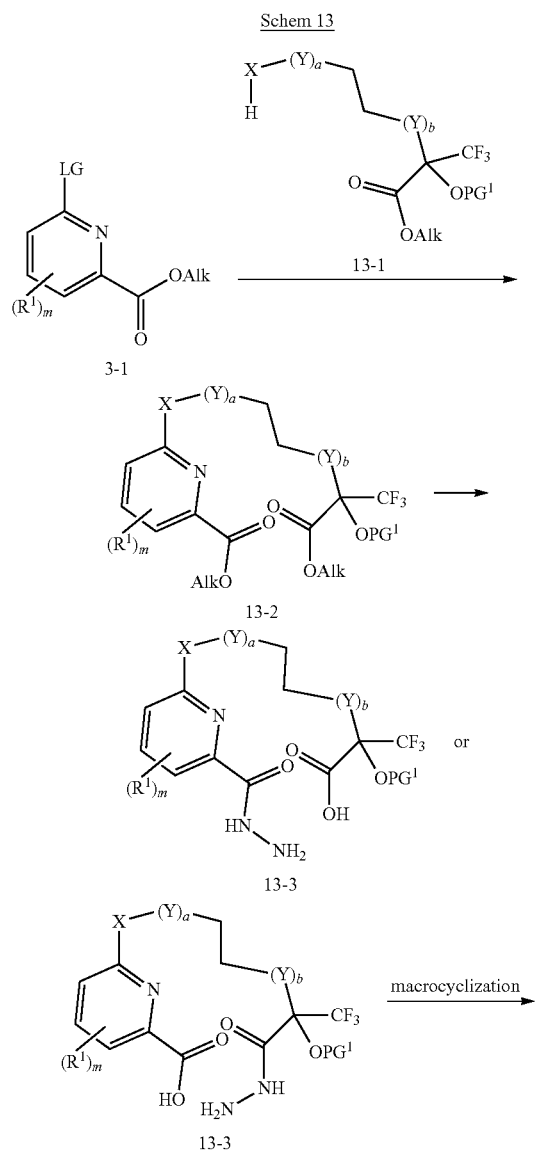

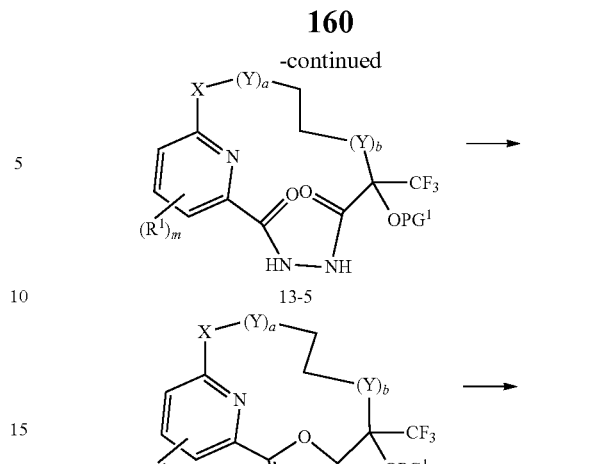

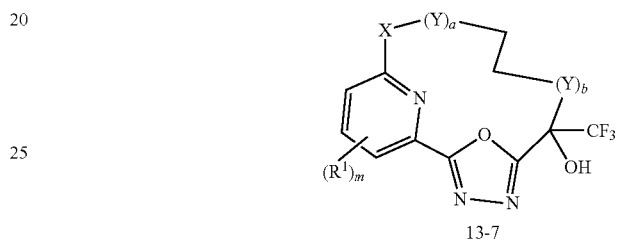

Scheme 13 refers to processes for preparing a compound of Formula 13-7 from a compound of Formula 3-1. Each Alk is independently selected from $C_1$-$C_6$ linear or branched alkyl groups. LG is selected from halogen and oxygen-based leaving groups such as OTf and OTs. PG is selected from suitable oxygen protecting groups, such as benzyl and silyl moieties (e.g., TBDPS, TBS, and TMS). Each of a and b is an integer independently selected from 1, 2, 3, and 4, provided that a+b is not greater than 5. $R^1$, m, X, Y, $R^{X1}$, and $R^Y$ are as defined for Formula I above.

The reaction of a compound of Formula 3-1 with a compound of Formula 13-1 to yield a compound of Formula 13-2 may be accomplished by any suitable aromatic substitution conditions. For example, a compound of Formula 3-1 and a compound of Formula 13-1 may be stirred in acetonitrile, followed by dropwise addition of diisopropylethylamine and heating to yield a compound of Formula 13-2. Conversion of a diester of Formula 13-2 to a carboxylic acid of Formula 13-3 or Formula 13-4 may be accomplished by any suitable hydrolysis conditions, followed by suitable amide bond formation conditions. For example, a compound of Formula 13-2 may be reacted with hydrazine monohydrate in methanol to yield a compound of Formula 13-3 or Formula 13-4. Conversion of a compound of Formula 13-3 or Formula 13-4 to a compound of Formula 13-5 may be accomplished by any suitable amide bond formation conditions. Conversion of a compound of Formula 13-5 to a compound of Formula 13-6 may be accomplished using any conditions suitable for oxadiazole formation. For example, a compound of Formula 13-5 may be reacted with N,N-diisopropylethylamine in acetonitrile, followed by addition of 4-methylbenzenesulfonyl chloride, to yield an oxadiazole of Formula 13-6. Conversion of a compound of Formula 13-6 to an alcohol of Formula 13-7 may be accomplished by any suitable alcohol deprotection procedure.

Scheme 14

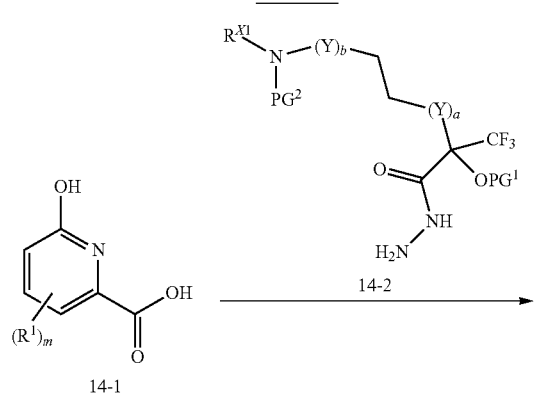

14-1

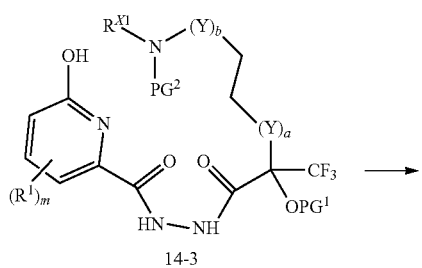

14-3

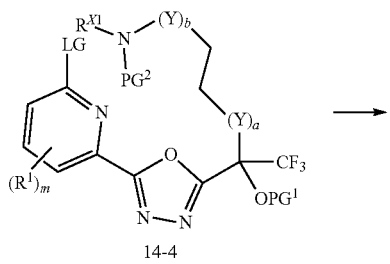

14-4

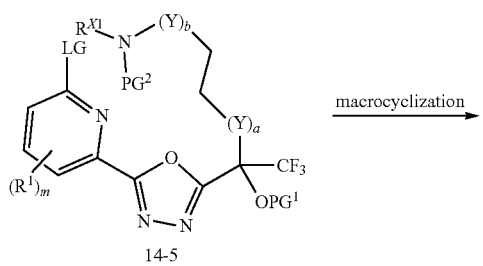

14-5

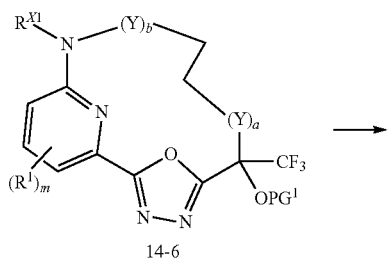

14-6

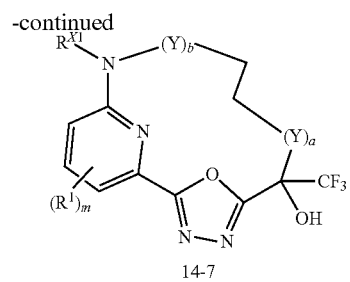

14-7

Scheme 14 refers to processes for preparing a compound of Formula 14-7 from a compound of Formula 14-1. LG is selected from halogen and oxygen-based leaving groups such as OTf and OTs. $PG^1$ is selected from suitable oxygen protecting groups, such as benzyl and silyl moieties (e.g., TBDPS, TBS, and TMS). $PG^2$ is selected from suitable nitrogen protecting groups, such as Boc and Fmoc. Each of a and b is an integer independently selected from 1, 2, 3, and 4, provided that a+b is not greater than 5. $R^1$, m, X, Y, and $R^{X1}$ are as defined for Formula I above.

The reaction of a compound of Formula 14-1 with a compound of Formula 14-2 to yield a compound of Formula 14-3 may be accomplished by any suitable amide bond formation conditions. Conversion of compound of Formula 14-3 to a compound of Formula 14-4 may be accomplished by any suitable procedure to convert an alcohol to a leaving group. For example, a compound of Formula 14-3 may be reacted with triphenylphosphine followed by 2,2,2-trichloroacetonitrile in anhydrous THF to yield a compound of Formula 14-4. Conversion of a compound of Formula 14-4 to a compound of Formula 14-5 may be accomplished by any suitable amine deprotection conditions. Macrocyclization of a compound of Formula 14-5 to produce a compound of Formula 14-6 may be accomplished by any suitable aromatic substitution conditions. For example, a compound of Formula 14-5 may be reacted with TFA in DCM to yield a compound of Formula 14-6. Conversion of a compound of Formula 14-6 to an alcohol of Formula 14-7 may be accomplished by any suitable alcohol deprotection procedure.

Scheme 15

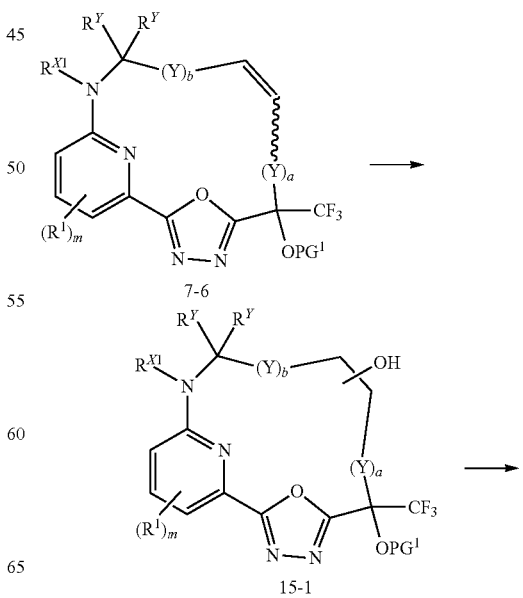

7-6

15-1

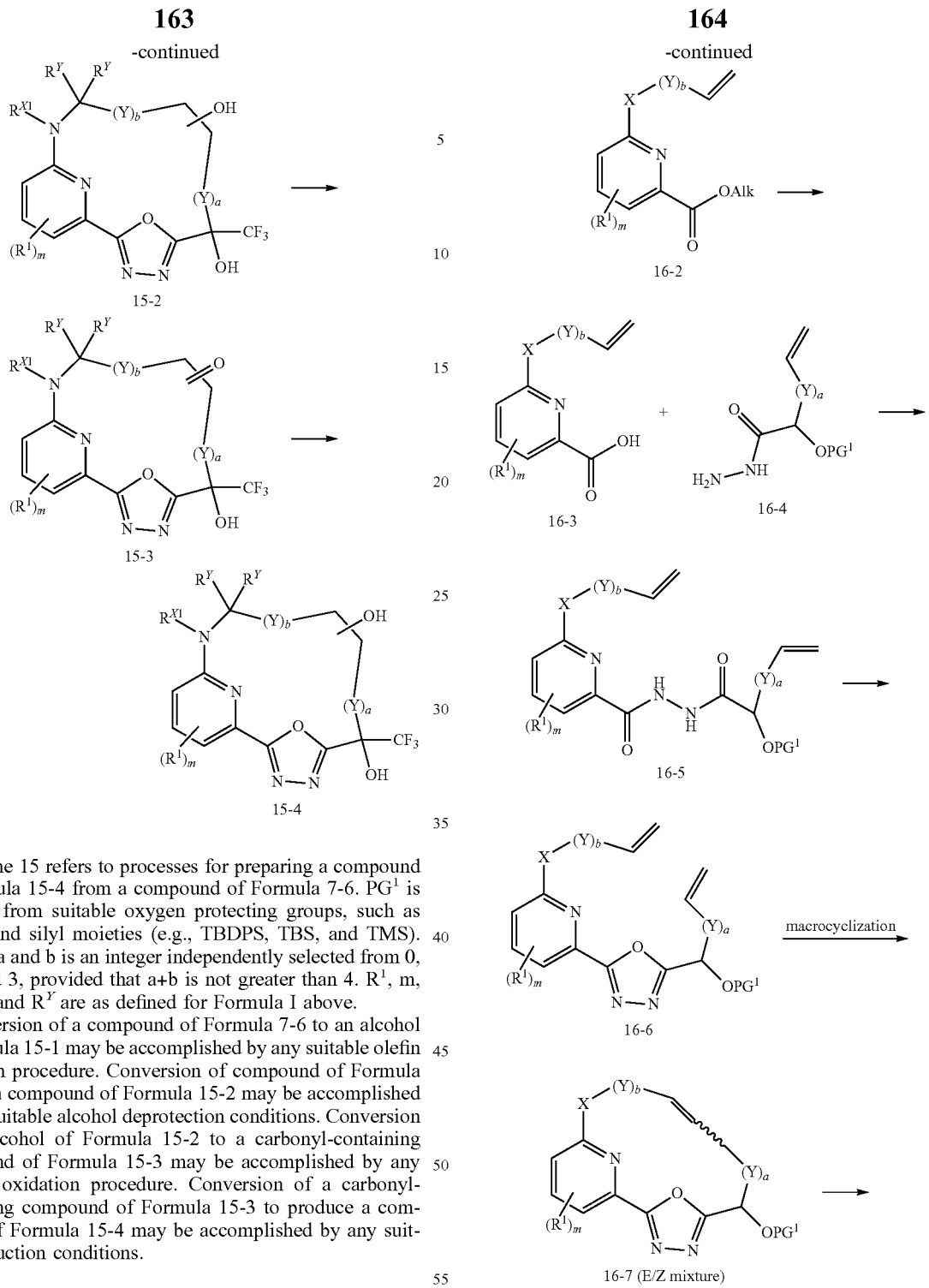

Scheme 15 refers to processes for preparing a compound of Formula 15-4 from a compound of Formula 7-6. $PG^1$ is selected from suitable oxygen protecting groups, such as benzyl and silyl moieties (e.g., TBDPS, TBS, and TMS). Each of a and b is an integer independently selected from 0, 1, 2, and 3, provided that a+b is not greater than 4. $R^1$, m, Y, $R^{X1}$, and $R^Y$ are as defined for Formula I above.

Conversion of a compound of Formula 7-6 to an alcohol of Formula 15-1 may be accomplished by any suitable olefin oxidation procedure. Conversion of compound of Formula 15-1 to a compound of Formula 15-2 may be accomplished by any suitable alcohol deprotection conditions. Conversion of an alcohol of Formula 15-2 to a carbonyl-containing compound of Formula 15-3 may be accomplished by any suitable oxidation procedure. Conversion of a carbonyl-containing compound of Formula 15-3 to produce a compound of Formula 15-4 may be accomplished by any suitable reduction conditions.

Scheme 16

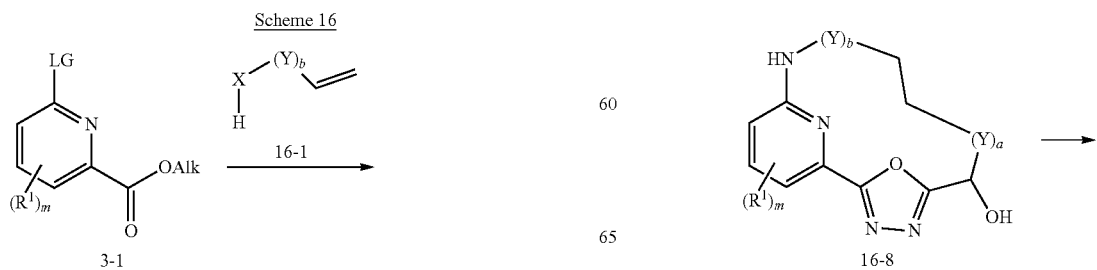

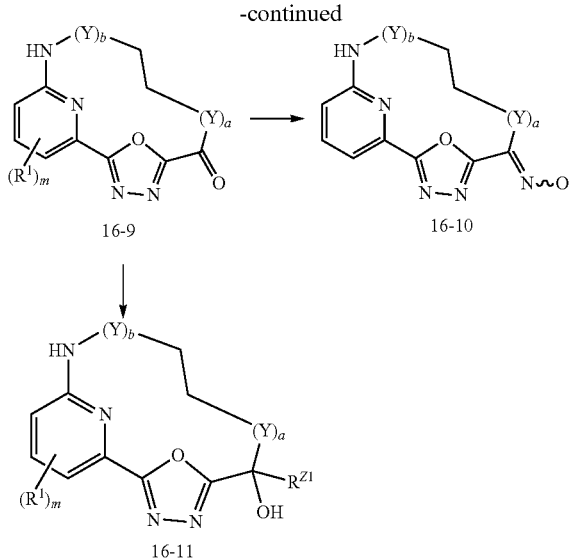

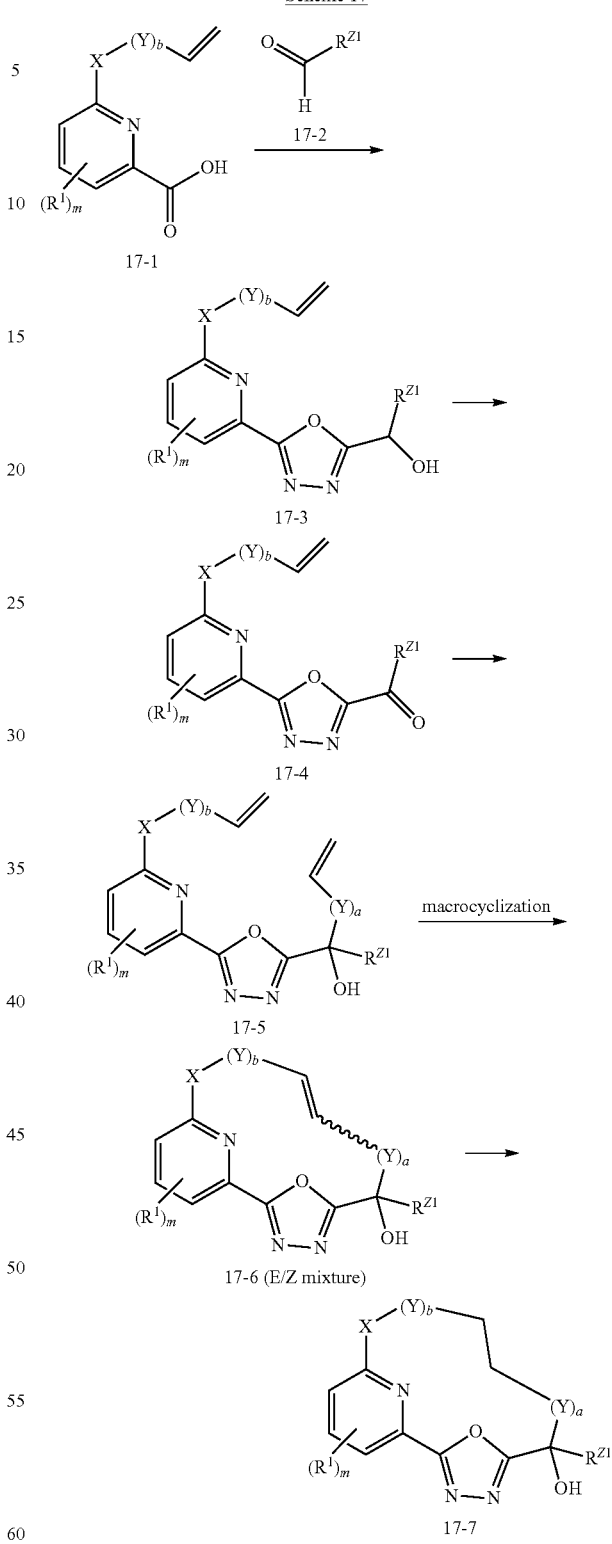

Scheme 16 refers to processes for preparing compounds of Formula 16-10 and Formula 16-11 from a compound of Formula 3-1. Alk is selected from $C_1$-$C_6$ linear or branched alkyl groups. LG is selected from halogen and oxygen-based leaving groups such as OTf and OTs. $PG^1$ is selected from suitable oxygen protecting groups, such as benzyl and silyl moieties (e.g., TBDPS, TBS, and TMS). Each of a and b is an integer independently selected from 1, 2, 3, and 4, provided that a+b is not greater than 5. $R^1$, m, X, Y, and $R^{Z1}$ are as defined for Formula I above.

The reaction of a compound of Formula 3-1 with a compound of Formula 16-1 to yield a compound of Formula 16-2 may be accomplished by any suitable aromatic substitution conditions. Conversion of an ester of Formula 16-2 to a carboxylic acid of Formula 16-3 may be accomplished by any suitable hydrolysis conditions. A compound of Formula 16-5 may be prepared from a compound of Formula 16-3 and a compound of Formula 16-4 using any suitable amide bond formation conditions. A compound of Formula 16-5 can be converted to a compound of Formula 16-6 using any conditions suitable for oxadiazole formation. For example, a compound of Formula 16-5 can be reacted with DIEA in acetonitrile, followed by addition of p-toluenesulfonyl chloride, to yield an oxadiazole of Formula 16-6. Macrocyclization of a compound of Formula 16-6 to produce a compound of Formula 16-7 may be accomplished by any suitable ring-closing metathesis conditions. For example, a compound of Formula 16-6 may be reacted in the presence of Zhan catalyst-1B in DCE to yield a macrocycle of Formula 16-7 as a mixture of E/Z isomers (as denoted by the ⌇ bond). The conversion of a compound of Formula 16-7 to a compound of Formula 16-8 may be accomplished using any suitable procedure for olefin reduction and alcohol deprotection. The conversion of a compound of Formula 16-8 to a carbonyl-containing compound of Formula 16-9 may be accomplished using any suitable oxidation conditions. Conversion of a carbonyl-containing compound of Formula 16-9 to an oxime of Formula 16-10 may be accomplished using any suitable oxime formation procedure. Conversion of a carbonyl-containing compound of Formula 16-9 to an alcohol of Formula 16-11 may be accomplished using any suitable procedure for nucleophilic addition to carbonyls.

Scheme 17 refers to processes for preparing a compound of Formula 17-7 from a compound of Formula 17-1. Each of a and b is an integer independently selected from 1, 2, 3, and 4, provided that a+b is not greater than 5. $R^1$, m, X, Y, and $R^{Z1}$ are as defined for Formula I above.

The reaction of a carboxylic acid of Formula 17-1 with an aldehyde of Formula 17-2 to yield a compound of Formula 17-3 may be accomplished using any conditions suitable for oxadiazole formation. For example, a compound of Formula 17-1 may be reacted with a compound of Formula 17-2 and N-isocyanoimino)triphenylphosphorane in DCM to yield a compound of Formula 17-3. Conversion of an alcohol of Formula 17-3 to a carbonyl-containing compound of Formula 17-4 may be accomplished by any suitable oxidation conditions. Conversion of a carbonyl-containing compound of Formula 17-4 to an alcohol of Formula 17-5 may be accomplished using any suitable procedure for nucleophilic addition to carbonyls. Macrocyclization of a compound of Formula 17-5 to produce a compound of Formula 17-6 may be accomplished by any suitable ring-closing metathesis conditions. For example, a compound of Formula 17-5 may be reacted in the presence of [1,3-bis(2,4,6-trimethylphenyl)imidazolidin-2-ylidene]-dichloro-[(2-isopropoxy-5-nitrophenyl)methylene]ruthenium in DCE to yield a macrocycle of Formula 17-6 as a mixture of E/Z isomers (as denoted by the ⌇ bond). The conversion of a compound of Formula 17-6 to a compound of Formula 17-7 may be accomplished using any suitable procedure for olefin reduction.

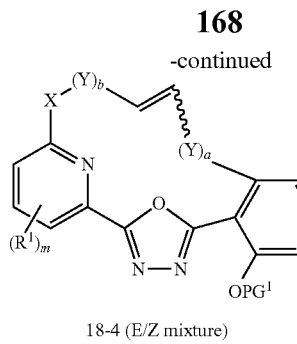

18-4 (E/Z mixture)

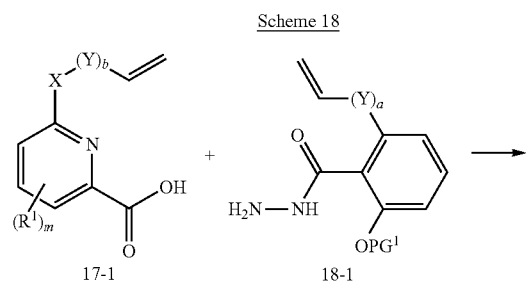

18-5

Scheme 18 refers to processes for preparing a compound of Formula 18-5 from a compound of Formula 17-1. PG$^1$ is selected from suitable oxygen protecting groups, such as benzyl and silyl moieties (e.g., TBDPS, TBS, and TMS). Each of a and b is an integer independently selected from 1, 2, 3, and 4, provided that a+b is not greater than 5. R$^1$, m, X, and Y are as defined for Formula I above.

The reaction of a compound of Formula 17-1 with a compound of Formula 18-1 to yield a compound of Formula 18-2 may be accomplished using any suitable amide bond formation conditions. A compound of Formula 18-2 can be converted to a compound of Formula 18-3 using any conditions suitable for oxadiazole formation. For example, a compound of Formula 18-2 can be reacted with diisopropylethylamine and p-toluenesulfonyl chloride to yield an oxadiazole of Formula 18-3. Macrocyclization of a compound of Formula 18-3 to produce a compound of Formula 18-4 may be accomplished by any suitable ring-closing metathesis conditions. For example, a compound of Formula 18-3 may be reacted in the presence of Zhan catalyst-1B in DCE to yield a macrocycle of Formula 18-4 as a mixture of E/Z isomers (as denoted by the ⌇ bond). The conversion of a compound of Formula 18-4 to a compound of Formula 18-5 may be accomplished using any suitable procedure for olefin reduction and alcohol deprotection.

Scheme 18

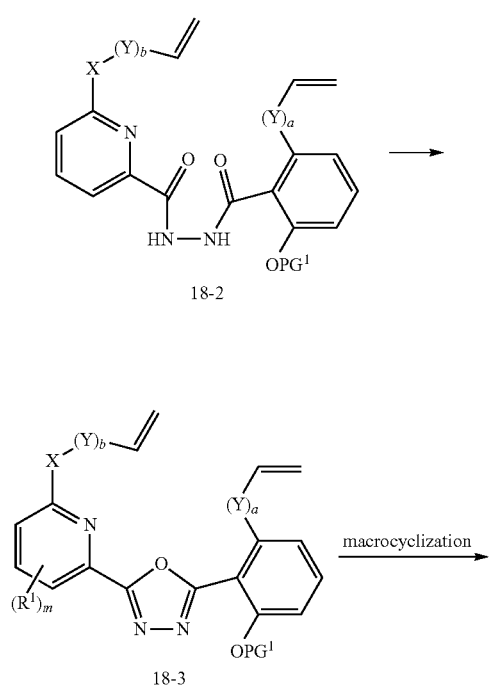

Scheme 19

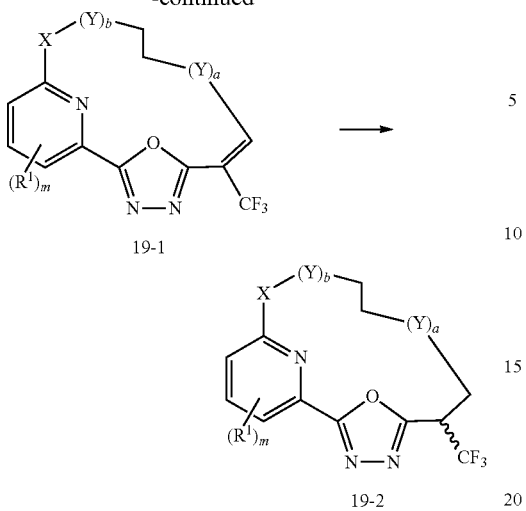

19-1

19-2

Scheme 19 refers to processes for preparing a compound of Formula 19-2 from a compound of Formula 13-7. Each of a and b is an integer independently selected from 1, 2, 3, and 4, provided that a+b is not greater than 5. $R^1$, m, X, and Y are as defined for Formula I above.

Conversion of an alcohol of Formula 13-7 to an olefin of Formula 19-1 may be accomplished using any suitable dehydration procedure. Conversion of a compound of Formula 19-1 to a compound of Formula 19-2 may be accomplished using any suitable olefin reduction conditions.

Scheme 20

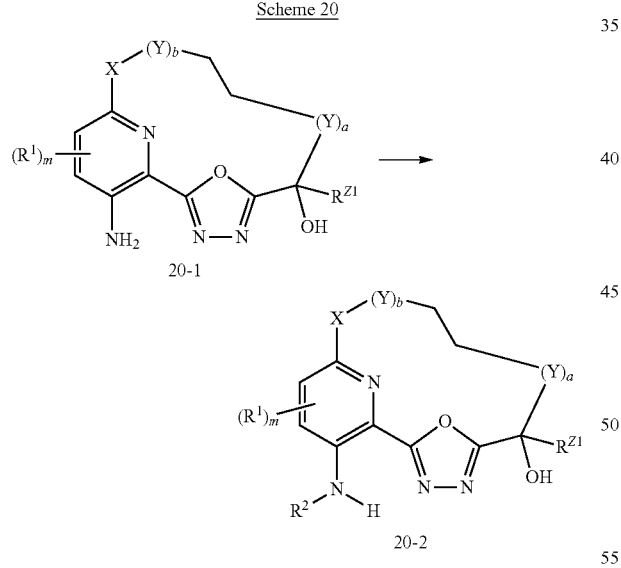

20-1

20-2

Scheme 20 refers to processes for preparing a compound of Formula 20-2 from a compound of Formula 20-1. Each of a and b is an integer independently selected from 1, 2, 3, and 4, provided that a+b is not greater than 5. $R^1$, m, X, Y, $R^{Z1}$, and $R^2$ are as defined for Formula I above.

Conversion of an amine of Formula 20-1 to an amine of Formula 20-2 may be accomplished using any suitable amination procedure. For example, an amine of Formula 20-1 may be reacted with an alkyl halide in the presence of bis(trimethylsilyl)amino]sodium to yield a compound of Formula 20-2.

Preparation of Intermediates

Intermediate 1: Preparation of methyl 3-[bis(tert-butoxycarbonyl)amino]-6-bromo-5-(trifluoromethyl)pyridine-2-carboxylate

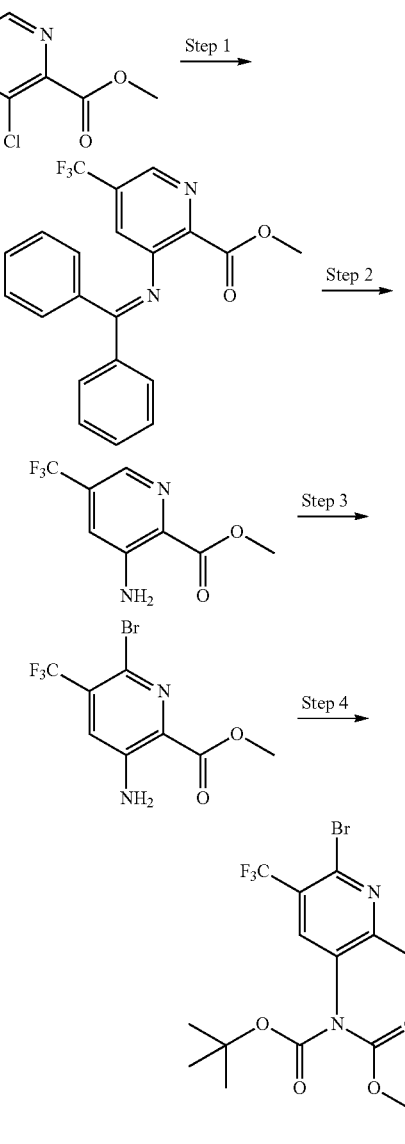

Step 1: Methyl 3-(benzhydrylideneamino)-5-(trifluoromethyl)pyridine-2-carboxylate

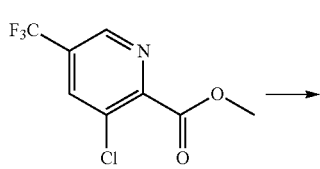

-continued

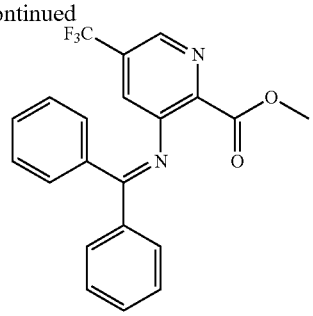

A mixture of methyl 3-chloro-5-(trifluoromethyl)pyridine-2-carboxylate (47.3 g, 197.43 mmol), diphenylmethanimine (47 g, 259.33 mmol), Xantphos (9.07 g, 15.675 mmol), and cesium carbonate (131 g, 402.06 mmol) in dioxane (800 mL) was degassed by bubbling nitrogen for 30 minutes. Pd(OAc)$_2$ (3.52 g, 15.679 mmol) was added and the system was purged with nitrogen three times. The reaction mixture was heated at 100° C. for 18 h. The reaction was cooled to room temperature and filtered on a pad of Celite. The cake was washed with EtOAc and solvents were evaporated under reduced pressure to give methyl 3-(benzhydrylideneamino)-5-(trifluoromethyl)pyridine-2-carboxylate (90 g, 84%) as yellow solid. ESI-MS m/z calc. 384.10855, found 385.1 (M+1)$^+$; Retention time: 2.24 minutes (LC Method B).

Step 2: Methyl 3-amino-5-(trifluoromethyl)pyridine-2-carboxylate

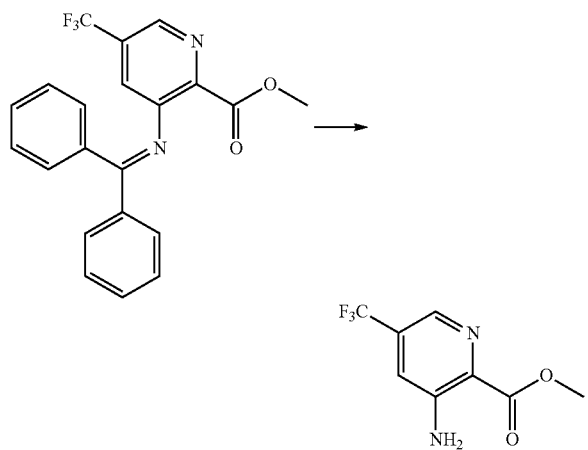

To a suspension of methyl 3-(benzhydrylideneamino)-5-(trifluoromethyl)pyridine-2-carboxylate (65 g, 124.30 mmol) in methanol (200 mL) was added HCl (3 M in methanol) (146 mL of 3 M, 438.00 mmol). The mixture was stirred at room temperature for 1.5 hour then the solvent was removed under reduced pressure. The residue was taken up in ethyl acetate (2 L) and dichloromethane (500 mL). The organic phase was washed with 5% aqueous sodium bicarbonate solution (3×500 mL) and brine (2×500 mL), dried over anhydrous sodium sulfate, filtered and the solvent was removed under reduced pressure. The residue was triturated with heptanes (2×50 mL) and the mother liquors were discarded. The solid obtained was triturated with a mixture of dichloromethane and heptanes (1:1, 40 mL) and filtered to afford methyl 3-amino-5-(trifluoromethyl)pyridine-2-carboxylate (25.25 g, 91%) as yellow solid. $^1$H NMR (300 MHz, CDCl$_3$) δ 8.24 (s, 1H), 7.28 (s, 1H), 5.98 (br. s, 2H), 4.00 (s, 3H) ppm. $^{19}$F NMR (282 MHz, CDCl$_3$) δ−63.23 (s, 3F) ppm. ESI-MS m/z calc. 220.046, found 221.1 (M+1)$^+$; Retention time: 1.62 minutes (LC Method E).

Step 3: Methyl 3-amino-6-bromo-5-(trifluoromethyl)pyridine-2-carboxylate

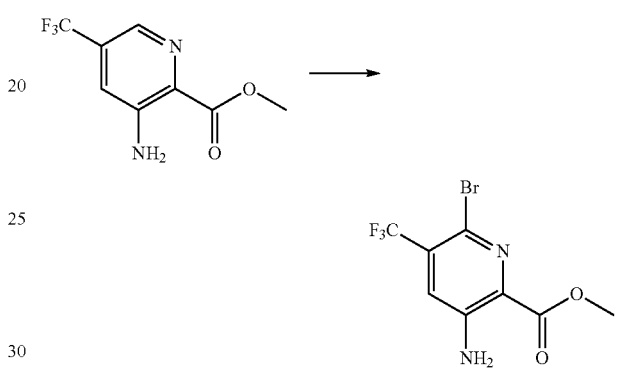

To a solution of methyl 3-amino-5-(trifluoromethyl)pyridine-2-carboxylate (18.75 g, 80.91 mmol) in acetonitrile (300 mL) at 0° C. was added portion wise N-bromosuccinimide (18.7 g, 105.3 mmol). The mixture was stirred overnight at 25° C. Ethyl acetate (1000 mL) was added. The organic layer was washed with 10% sodium thiosulfate solution (3×200 mL) which were back extracted with ethyl acetate (2×200 mL). The combined organic extracts were washed with saturated sodium bicarbonate solution (3×200 mL), brine (200 mL), dried over sodium sulfate and concentrated in vacuo to provide methyl 3-amino-6-bromo-5-(trifluoromethyl)pyridine-2-carboxylate (25.46 g, 98%). $^1$H NMR (300 MHz, CDCl$_3$) δ 3.93-4.03 (m, 3H), 6.01 (br. s., 2H), 7.37 (s, 1H) ppm. $^{19}$F NMR (282 MHz, CDCl$_3$) δ−64.2 (s, 3F) ppm. ESI-MS m/z calc. 297.9565, found 299.0 (M+1)$^+$; Retention time: 2.55 minutes (LC Method F).

Step 4: Methyl 3-[bis(tert-butoxycarbonyl)amino]-6-bromo-5-(trifluoromethyl)pyridine-2-carboxylate

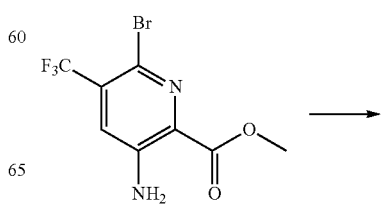

173

-continued

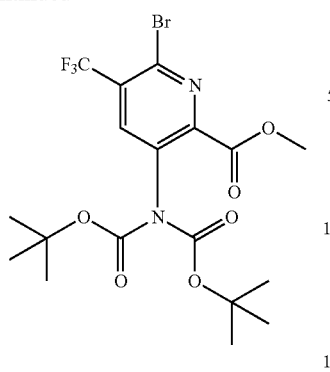

A mixture of methyl 3-amino-6-bromo-5-(trifluoromethyl)pyridine-2-carboxylate (5 g, 15.549 mmol), (Boc)$_2$O (11 g, 11.579 mL, 50.402 mmol), DMAP (310 mg, 2.5375 mmol) and CH$_2$Cl$_2$ (150 mL) was stirred at room temperature overnight. The reaction mixture was concentrated under reduced pressure and purification by silica gel chromatography (0% to 15% ethyl acetate in heptane) provided methyl 3-[bis(tert-butoxycarbonyl)amino]-6-bromo-5-(trifluoromethyl)pyridine-2-carboxylate (6.73 g, 87%) as light yellow solid. $^1$H NMR (300 MHz, CDCl$_3$) δ 1.42 (s, 18H), 3.96 (s, 3H), 7.85 (s, 1H) ppm. $^{19}$F NMR (282 MHz, CDCl$_3$) δ −63.9 (s, 3F) ppm. ESI-MS m/z calc. 498.06134, Retention time: 2.34 minutes (LC Method B).

Intermediate 2: Preparation of 6-(2-allylpyrrolidin-1-yl)-3-(tert-butoxycarbonylamino)-5-(trifluoromethyl)pyridine-2-carboxylic Acid

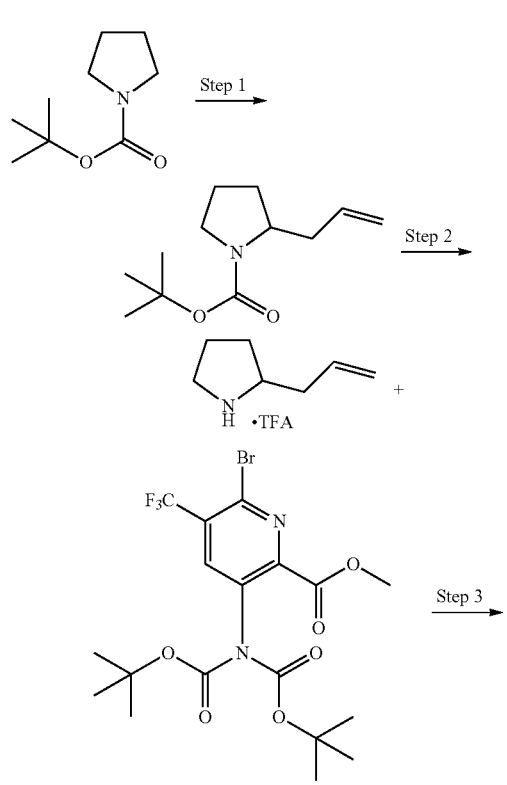

174

-continued

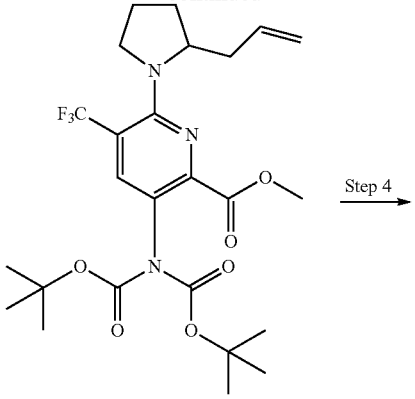

Step 4 →

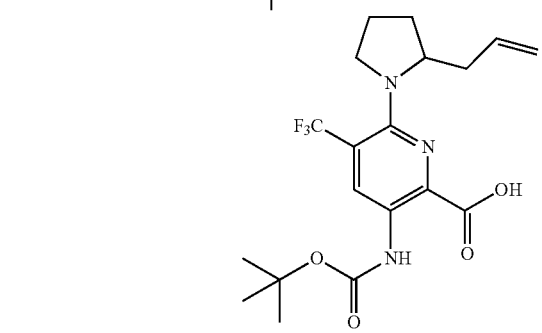

Step 1: tert-Butyl 2-allylpyrrolidine-1-carboxylate

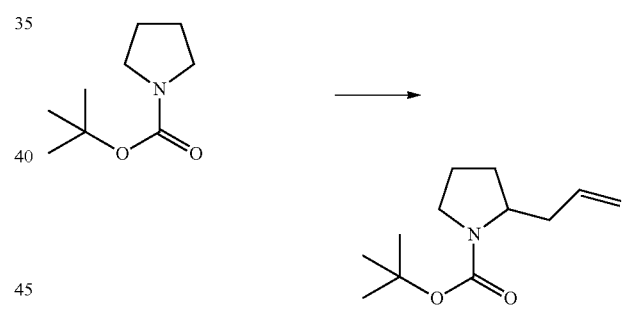

s-Butyllithium (20.4 mL of 1.4 M in cyclohexanes, 28.56 mmol) was added dropwise to a solution of tert-butyl pyrrolidine-1-carboxylate (3.5 g, 20.44 mmol) and tetramethylethylenediamine (2.8675 g, 3.7 mL, 24.676 mmol) in diethyl ether (80 mL) at −78° C. and the mixture was stirred for 2 h. Then zinc chloride (57 mL of 0.5 M in THF, 28.5 mmol) was added slowly at −78° C. and the mixture was stirred for 90 min. A solution of copper(I) cyanide (2.2 g, 24.564 mmol) in lithium chloride (82 mL of 0.5 M in THF, 41 mmol) was added slowly at −78° C. and the mixture was stirred for 90 min then 3-bromoprop-1-ene (7.4094 g, 5.3 mL, 61.247 mmol) was added slowly at −78° C. and the mixture was stirred at room temperature overnight. Aqueous ammonium hydroxide (60 mL) was added and the mixture was stirred at room temperature for 1 h. The phases were separated, and the aqueous phase was extracted with diethyl ether (2×60 mL). The organic phases were combined, washed with brine (60 mL), dried over anhydrous sodium sulfate, filtered and concentrated under reduced pressure. Purification by silica gel chromatography (gradient from 0% to 20% of ethyl acetate in heptanes) provided as a clear oil, tert-butyl 2-allylpyrrolidine-1-carboxylate (2.9 g, 67%). ¹H NMR (300 MHz, CDCl₃) δ 1.46 (s, 9H), 1.66-1.95 (m, 4H), 1.99-2.23 (m, 1H), 2.33-2.62 (m, 1H), 3.22-3.46 (m, 2H), 3.67-3.94 (m, 1H), 4.97-5.11 (m, 2H), 5.62-5.84 (m, 1H) ppm. ESI-MS m/z calc. 211.1572, found 234.2 (M+Na)⁺; Retention time: 2.17 minutes (LC Method B).

Step 2: 2-Allylpyrrolidine (trifluoroacetate Salt)

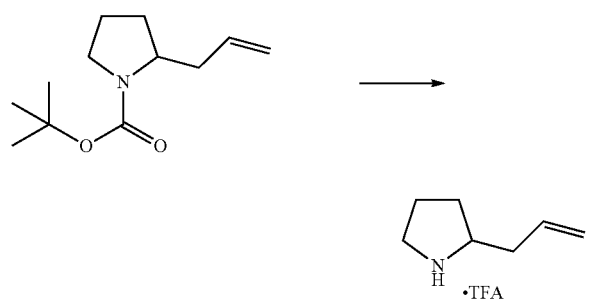

Trifluoroacetic acid (13.468 g, 9.1 mL, 118.12 mmol) was added slowly to tert-butyl 2-allylpyrrolidine-1-carboxylate (1.6 g, 7.5721 mmol) in dichloromethane (12 mL) at 0° C. The mixture was stirred for 3 h at room temperature then concentrated. Toluene (10 mL) was added and the mixture was concentrated (repeated 4 times) to afford as an amber oil, 2-allylpyrrolidine (trifluoroacetate salt) (1.9 g, 99%). ¹H NMR (300 MHz, CDCl₃) δ 1.57-1.85 (m, 1H), 1.89-2.31 (m, 3H), 2.35-2.71 (m, 2H), 3.32 (br. s., 2H), 3.61 (br. s., 1H), 4.95-5.35 (m, 2H), 5.51-5.91 (m, 1H), 8.27 (br. s., 1H), 9.31 (br. s., 1H) ppm. ¹⁹F NMR (282 MHz, CDCl₃) δ −75.9 (s, 3F) ppm. ESI-MS m/z calc. 111.1048, found 112.2 (M+1)⁺; Retention time: 0.36 minutes (LC Method B).

Step 3: Methyl 6-(2-allylpyrrolidin-1-yl)-3-[bis(tert-butoxycarbonyl)amino]-5-(trifluoromethyl)pyridine-2-carboxylate

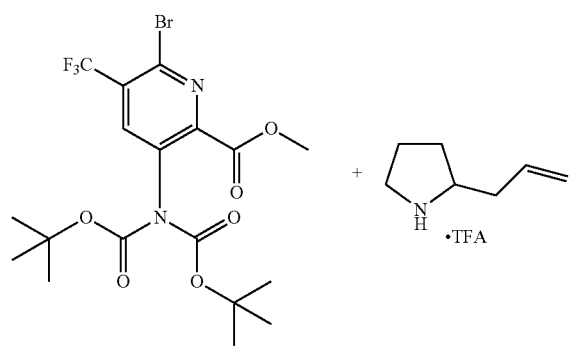

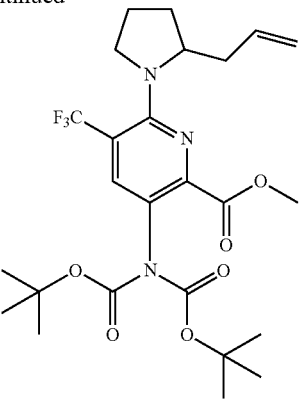

In a sealed tube, 2-allylpyrrolidine (trifluoroacetate salt) (338 mg, 1.5008 mmol) was added to methyl 3-[bis(tert-butoxycarbonyl)amino]-6-bromo-5-(trifluoromethyl)pyridine-2-carboxylate (500 mg, 1.0015 mmol) and DIPEA (964.60 mg, 1.3 mL, 7.4635 mmol) in acetonitrile (10 mL). The tube was sealed, and the mixture was heated at 80° C. overnight. Saturated sodium bicarbonate solution (25 mL) was added and extracted with ethyl acetate (3×25 mL). The organic phases were combined, washed with brine (25 mL), dried over anhydrous sodium sulfate, filtered and concentrated under reduced pressure. Purification by silica gel chromatography (gradient from 0% to 20% of ethyl acetate in heptanes) provided as a yellow oil, methyl 6-(2-allylpyrrolidin-1-yl)-3-[bis(tert-butoxycarbonyl)amino]-5-(trifluoromethyl)pyridine-2-carboxylate (480 mg, 91%). ¹H NMR (300 MHz, CDCl₃) δ 1.42 (s, 18H), 1.65-1.90 (m, 2H), 1.94-2.18 (m, 2H), 2.24-2.40 (m, 1H), 2.51-2.65 (m, 1H), 3.41-3.52 (m, 1H), 3.55-3.69 (m, 1H), 3.88 (s, 3H), 4.46-4.60 (m, 1H), 4.95-5.11 (m, 2H), 5.65-5.87 (m, 1H), 7.63 (s, 1H) ppm. ¹⁹F NMR (282 MHz, CDCl₃) δ −56.0 (s, 3F) ppm. ESI-MS m/z calc. 529.24, found 530.3 (M+1)⁺; Retention time: 2.63 minutes (LC Method E).

Step 4: 6-(2-Allylpyrrolidin-1-yl)-3-(tert-butoxycarbonylamino)-5-(trifluoromethyl)pyridine-2-carboxylic Acid

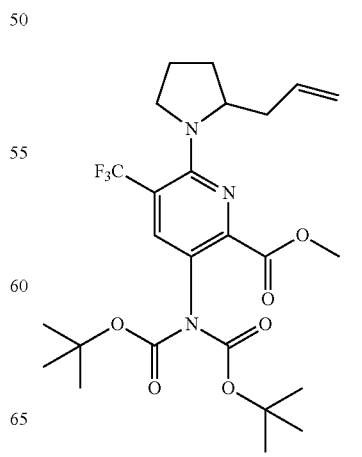

-continued

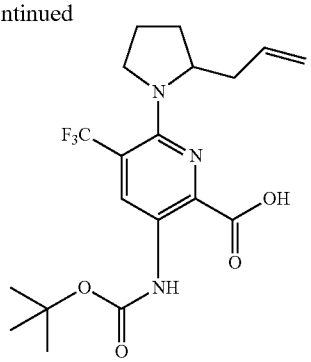

To a solution of methyl 6-(2-allylpyrrolidin-1-yl)-3-[bis(tert-butoxycarbonyl)amino]-5-(trifluoromethyl)pyridine-2-carboxylate (13.1 g, 24.74 mmol) in THF (156 mL) was added methanol (125 mL) and water (100 mL). Lithium hydroxide anhydrous (2.116 g, 86.6 mmol) was added to the mixture in three portions. The mixture was stirred at 60° C. for 3.5 h. THF and methanol were removed under reduced pressure and then 70 mL of 10% aqueous HCl was added and the resulting mixture was extracted with EtOAc (3×100 mL). The organic phases were combined, washed with brine (50 mL), dried over anhydrous sodium sulfate, filtered and concentrated under reduced pressure. Purification by silica gel chromatography (gradient from 0% to 50% EtOAc in hexanes) provided as a yellow solid, 6-(2-allylpyrrolidin-1-yl)-3-(tert-butoxycarbonylamino)-5-(trifluoromethyl)pyridine-2-carboxylic acid (7.85 g, 76%). $^1$H NMR (400 MHz, CDCl$_3$) δ 1.52 (s, 9H), 1.74-1.81 (m, 2H), 1.98-2.01 (m, 1H), 2.15-2.26 (m, 2H), 2.44-2.50 (m, 1H), 3.38-3.43 (m, 1H), 3.63-3.69 (m, 1H), 4.25-4.32 (m, 1H), 5.04-5.08 (m, 2H), 5.70-5.80 (m, 1H), 9.13 (s, 1H), 9.67 (s, 1H), 11.11 (br. s, 1H). ESI-MS m/z calc. 415.1719, found 416.3 (M+1)$^+$; Retention time: 2.01 minutes (LC Method A).

Intermediate 3: Preparation of (2S)-2-Allylpyrrolidine (trifluoroacetate Salt)

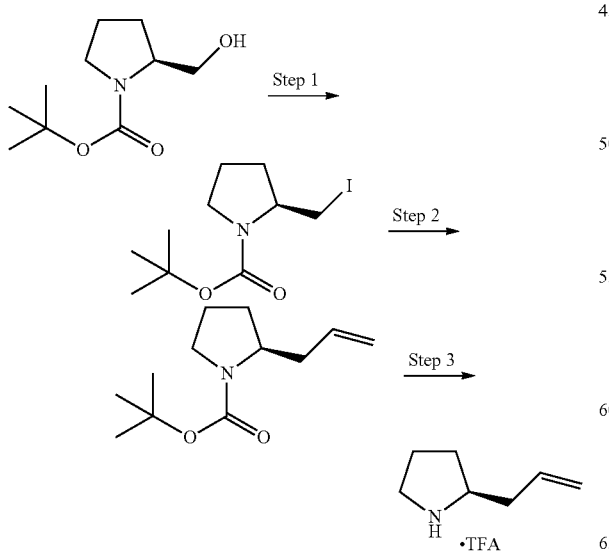

Step 1: tert-Butyl (2S)-2-(iodomethyl)pyrrolidine-1-carboxylate

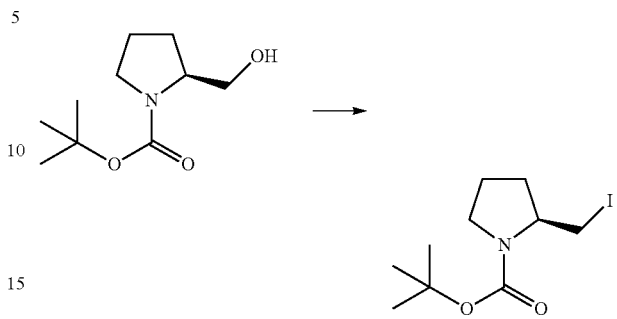

To a solution of imidazole (16.9 g, 248.2 mmol) and triphenylphosphane (35.8 g, 136.5 mmol) in 2-methyltetrahydrofuran (300 mL) at 0° C. was added iodine (34.8 g, 137.1 mmol) portion-wise over 30 min. The reaction temperature was kept at <6° C. and the mixture became a dark orange taffy which then became light yellow and granular on stirring. The mixture was allowed to warm to ambient temperature and a solution of tert-butyl (2S)-2-(hydroxymethyl)pyrrolidine-1-carboxylate (25 g, 124.2 mmol) in 2-methyltetrahydrofuran (150 mL) was added portion-wise. The mixture was stirred at ambient temperature for 16 h affording a light yellow slurry. The slurry was filtered over Celite to remove the salts and the filtrate was concentrated in vacuo. The residue was dissolved in 150 mL of EtOAc. To the mixture was added 150 mL of hexane which gave an oil. This oil would not dissolve on addition of EtOAc (~300 mL). The oil was removed by aspiration and was found by analysis to be triphenylphosphine oxide. The solvent phase left after removal of the oil was concentrated in vacuo. A precipitate formed upon standing and was stirred in 100 mL of MTBE. The precipitate was removed by filtration and washed with MTBE. The filtrate was concentrated in vacuo and purified by silica gel chromatography (0% to 40% EtOAc/hexanes) which provided as a light yellow oil, tert-butyl (2S)-2-(iodomethyl)pyrrolidine-1-carboxylate (36.5 g, 94%). $^1$H NMR (499 MHz, Chloroform-d) δ 3.89 (d, J=14.0 Hz, 1H), 3.42 (d, J=34.7 Hz, 4H), 2.06 (s, 1H), 2.00-1.86 (m, 2H), 1.82 (q, J=6.9 Hz, 1H), 1.47 (s, 9H) ppm. ESI-MS m/z calc. 311.0382, found 312.0 (M+1)$^+$; Retention time: 1.82 minutes (LC Method A).

Step 2: tert-Butyl (2S)-2-allylpyrrolidine-1-carboxylate

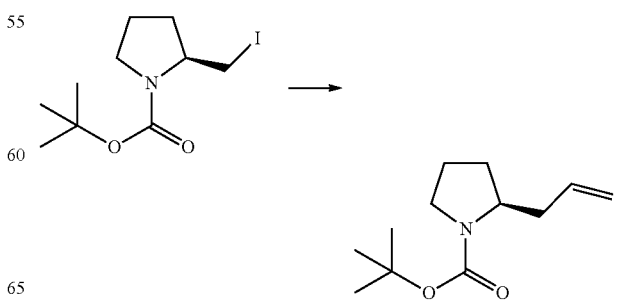

Iodocopper (103 g, 540.8 mmol) was suspended in THF (525 mL) under nitrogen and cooled to −40° C. under stirring. Bromo(vinyl)magnesium (1 L of 1 M, 1.000 mol) was slowly added via an addition funnel over 40 minutes keeping the internal temperature between −40° C. and −45° C. The thick suspension was stirred for 1 h allowing to warm to −10° C. The black suspension was cooled to −40° C. and a solution of tert-butyl (2S)-2-(iodomethyl)pyrrolidine-1-carboxylate (105 g, 337.4 mmol) in THF (260 mL) was added dropwise over 30 min keeping the internal temperature between −40° C. and −45° C. The thick suspension was stirred for additional 3 h with slow warming to 18° C. The black suspension was concentrated under reduced pressure and treated with saturated aqueous ammonium chloride solution (300 mL) and MTBE (300 mL). The solid was removed by filtration and the phases separated. The organic phase was washed twice more with saturated aqueous ammonium chloride solution (2×100 mL) and the aqueous phases were back-extracted once with MTBE (100 mL). The combined organic phases were dried, filtered and evaporated. Purification by silica gel chromatography (hexane to 5% acetone in hexane (product absorbs at 200-210 nm)) provided tert-butyl (2S)-2-allylpyrrolidine-1-carboxylate (32 g, 45%). $^1$H NMR (400 MHz, DMSO-d6) δ 5.74 (ddt, J=17.3, 10.3, 7.2 Hz, 1H), 5.13-4.97 (m, 2H), 3.70 (s, 1H), 3.23 (dq, J=19.2, 11.3, 9.4 Hz, 2H), 2.46-1.52 (m, 6H), 1.40 (s, 9H) ppm. ESI-MS m/z calc. 211.15723, found 212.0 (M+1)$^+$; Retention time: 1.82 minutes (LC Method A).

Step 3: (2S)-2-Allylpyrrolidine (trifluoroacetate Salt)

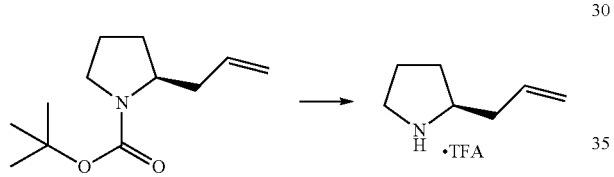

To a solution of tert-butyl (2S)-2-allylpyrrolidine-1-carboxylate (17 g, 80.45 mmol) in DCM (120 mL) was added TFA (30 mL, 389.4 mmol) dropwise. The mixture was stirred at ambient temperature for 24 h. The solvent was removed in vacuo and the product treated 3 times with a toluene (200 mL) azeotrope. The product was dried under vacuum for 16 h giving as a dark oil, (2S)-2-allylpyrrolidine (trifluoroacetate salt) (17 g, 94%). ESI-MS m/z calc. 111.1048, found 112.1 (M+1)$^+$; Retention time: 0.4 minutes (LC Method A).

Intermediate 4: Preparation of 6-[(2S)-2-allylpyrrolidin-1-yl]-3-(tert-butoxycarbonylamino)-5-(trifluoromethyl)pyridine-2-carboxylic Acid

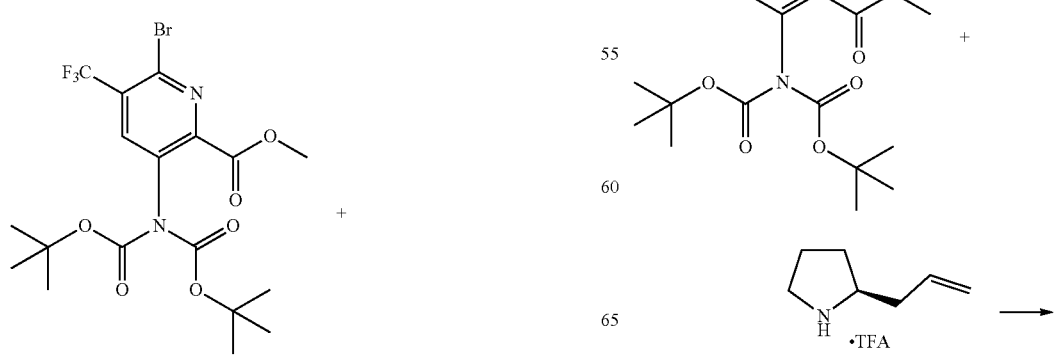

Step 1: Methyl 6-[(2S)-2-allylpyrrolidin-1-yl]-3-[bis(tert-butoxycarbonyl)amino]-5-(trifluoromethyl)pyridine-2-carboxylate

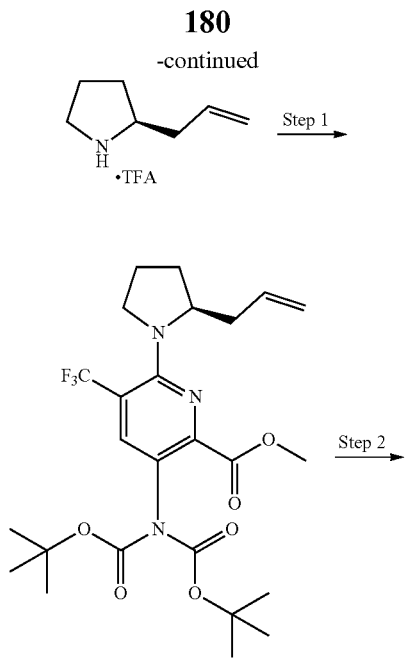

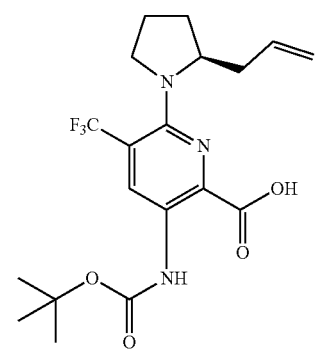

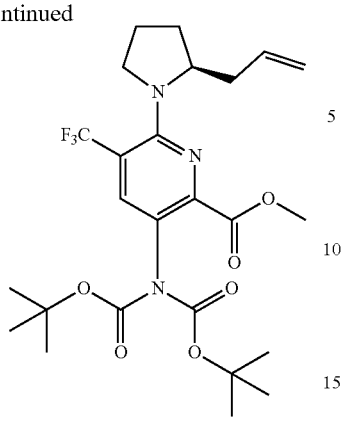

To a solution of methyl 3-[bis(tert-butoxycarbonyl)amino]-6-bromo-5-(trifluoromethyl)pyridine-2-carboxylate (31.6 g, 63.29 mmol) and (2S)-2-allylpyrrolidine (trifluoroacetate salt) (17 g, 75.49 mmol) in acetonitrile (400 mL) was added DIEA (45 mL, 258.4 mmol) and the mixture heated at 80° C. for 2 h. Added more DIEA (10 mL, 57.41 mmol) and stirred at 80° C. for 18 h. The reaction mixture was cooled to ambient temperature and the solvent was removed in vacuo. The residue was diluted with EtOAc (700 mL) and washed twice with 250 mL of brine, dried over MgSO$_4$, filtered and concentrated in vacuo. Purification by silica gel chromatography (gradient from 0% to 30% EtOAc in hexanes) provided methyl 6-[(2S)-2-allylpyrrolidin-1-yl]-3-[bis(tert-butoxycarbonyl)amino]-5-(trifluoromethyl)pyridine-2-carboxylate (15 g, 45%). $^1$H NMR (400 MHz, Chloroform-d) δ 7.63 (s, 1H), 5.78 (ddt, J=17.3, 10.2, 7.2 Hz, 1H), 5.15-4.91 (m, 2H), 4.54 (qd, J=7.5, 3.1 Hz, 1H), 3.88 (s, 3H), 3.61 (t, J=8.6 Hz, 1H), 3.48 (d, J=8.4 Hz, 1H), 2.69-2.53 (m, 1H), 2.32 (dt, J=13.7, 7.5 Hz, 1H), 2.07 (d, J=5.6 Hz, 1H), 2.02-1.94 (m, 1H), 1.86-1.69 (m, 2H), 1.43 (s, 18H) ppm. ESI-MS m/z calc. 529.24, found 530.3 (M+1)$^+$; Retention time: 2.06 minutes (LC Method A).

Step 2: 6-[(2S)-2-Allylpyrrolidin-1-yl]-3-(tert-butoxycarbonylamino)-5-(trifluoromethyl)pyridine-2-carboxylic Acid

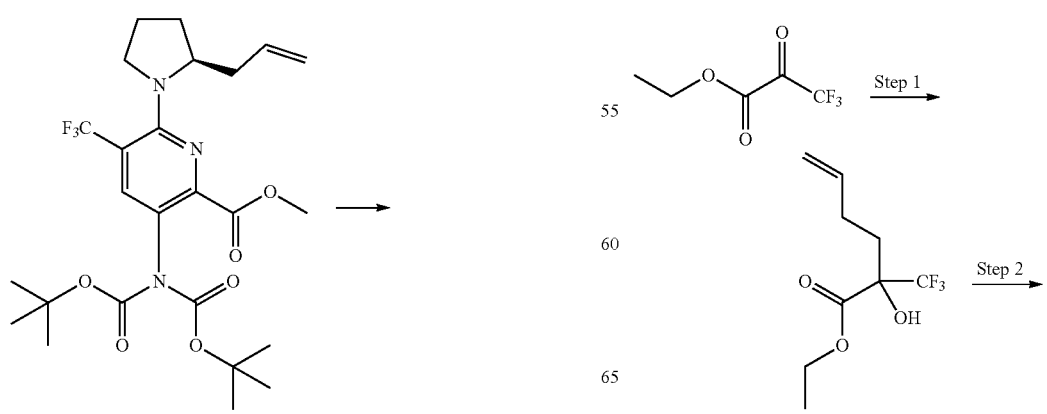

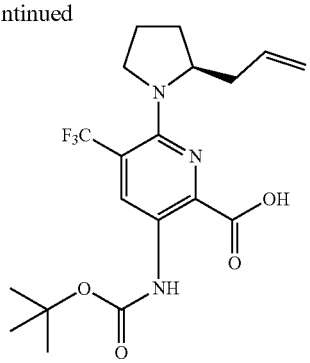

Methyl 6-[(2S)-2-allylpyrrolidin-1-yl]-3-[bis(tert-butoxycarbonyl)amino]-5-(trifluoromethyl)pyridine-2-carboxylate (20.5 g, 38.71 mmol) was dissolved in THF (150 mL) and MeOH (150 mL) (yellow solution) then treated with water (150 mL) (yellow emulsion) followed by LiOH (3.5 g, 146.1 mmol). The mixture was heated to 60° C. and stirred for 3.5 h. The yellow mixture was concentrated under reduced pressure to remove most of the THF and MeOH to give a yellow emulsion which was cooled in an ice bath to give a yellow sticky suspension (pH=14). The suspension was acidified by slow addition of HCl (160 mL of 1 M, 160 mmol), keeping the internal temperature around 10° C. (foaming) and then stirred in a cold-water bath for 1 h. The solid was collected by filtration and washed with cold water and dried overnight. The solid was purified by silica gel chromatography eluting with a linear gradient of 100% hexane to 50% ethyl acetate in hexane giving as a bright yellow solid, 6-[(2S)-2-allylpyrrolidin-1-yl]-3-(tert-butoxycarbonylamino)-5-(trifluoromethyl)pyridine-2-carboxylic acid (13.4 g, 83%) $^1$H NMR (400 MHz, Chloroform-d) δ 11.11 (s, 1H), 9.68 (s, 1H), 9.13 (s, 1H), 5.83-5.67 (m, 1H), 5.12-5.02 (m, 2H), 4.29 (qd, J=7.8, 3.1 Hz, 1H), 3.66 (q, J=9.0 Hz, 1H), 3.41 (t, J=8.5 Hz, 1H), 2.47 (ddd, J=13.8, 7.6, 3.2 Hz, 1H), 2.29-2.17 (m, 1H), 2.21-2.12 (m, 1H), 2.06-1.93 (m, 1H), 1.87-1.69 (m, 2H), 1.53 (s, 9H) ppm. ESI-MS m/z calc. 415.1719, found 416.0 (M+1)$^+$; Retention time: 1.38 minutes (LC Method M).

Intermediate 5: Preparation of 2-benzyloxy-2-(trifluoromethyl)hex-5-enehydrazide (hydrochloride Salt)

183
-continued

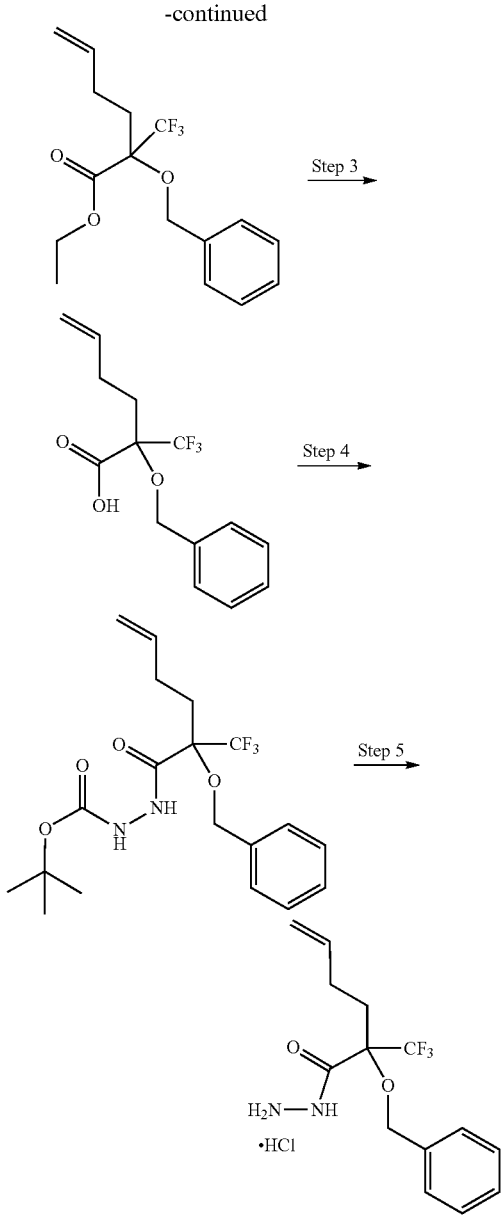

Step 1: Ethyl
2-hydroxy-2-(trifluoromethyl)hex-5-enoate

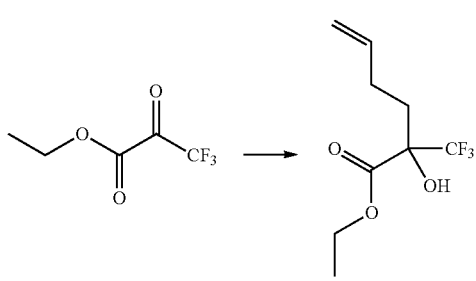

To a solution of ethyl 3,3,3-trifluoro-2-oxo-propanoate (25.15 g, 147.87 mmol) in Et$_2$O (270 mL) at −78° C. was added bromo(but-3-enyl)magnesium in THF (190 mL of 0.817 M, 155.23 mmol) dropwise over a period of 1.5 h (inner temperature −72° C. to −76° C.). The mixture was stirred at −78° C. for 20 min. The dry ice-acetone bath was removed. The mixture was slowly warm to 5° C. during 1 h, added to a mixture of 1 N aqueous HCl (170 mL) and crushed ice (150 g) (pH=4). The two layers were separated. The organic layer was concentrated, and the residue was combined with aqueous phase and extracted with EtOAc (2×150 mL). The combined organic phase was washed with 5% aqueous NaHCO$_3$ (50 mL) and brine (20 mL), dried with Na$_2$SO$_4$. The mixture was filtered and concentrated and co-evaporated with THF (2×40 mL) to give ethyl 2-hydroxy-2-(trifluoromethyl)hex-5-enoate (37.44 g, 96%) as colorless oil. $^1$H NMR (300 MHz, CDCl$_3$) δ 5.77 (ddt, J=17.0, 10.4, 6.4 Hz, 1H), 5.15-4.93 (m, 2H), 4.49-4.28 (m, 2H), 3.88 (s, 1H), 2.35-2.19 (m, 1H), 2.17-1.89 (m, 3H), 1.34 (t, J=7.0 Hz, 3H) ppm. $^{19}$F NMR (282 MHz, CDCl$_3$) δ −78.74 (s, 3F) ppm.

Step 2: Ethyl
2-benzyloxy-2-(trifluoromethyl)hex-5-enoate

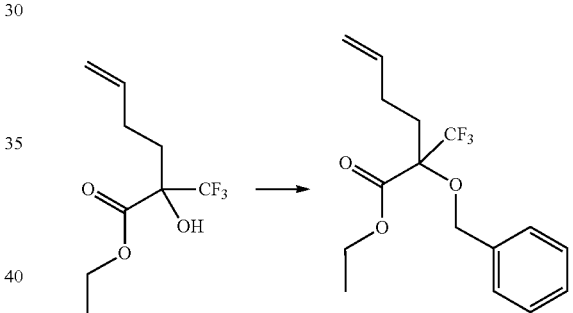

To a solution of ethyl 2-hydroxy-2-(trifluoromethyl)hex-5-enoate (24.29 g, 87.6% purity, 94.070 mmol) in DMF (120 mL) at 0° C. was added NaH (60% in mineral oil, 5.64 g, 141.01 mmol) portion-wise. The mixture was stirred at 0° C. for 10 min. Benzyl bromide (24.13 g, 141.08 mmol) and TBAI (8.68 g, 23.500 mmol) were added. The mixture was stirred at room temperature overnight. NH$_4$Cl (3 g, 0.6 eq) was added. The mixture was stirred for 10 min. 30 mL of EtOAc was added, then ice-water (400 g). The mixture was extracted with CH$_2$Cl$_2$ and the combined organic layer was concentrated. Purification by silica gel chromatography (0% to 20% CH$_2$Cl$_2$ in heptanes) provided as a pink oil, ethyl 2-benzyloxy-2-(trifluoromethyl)hex-5-enoate (26.05 g, 88%). $^1$H NMR (300 MHz, CDCl$_3$) δ 1.34 (t, J=7.2 Hz, 3H), 2.00-2.19 (m, 3H), 2.22-2.38 (m, 1H), 4.33 (q, J=7.2 Hz, 2H), 4.64 (d, J=10.6 Hz, 1H), 4.84 (d, J=10.9 Hz, 1H), 4.91-5.11 (m, 2H), 5.62-5.90 (m, 1H), 7.36 (s, 5H) ppm. $^{19}$F NMR (282 MHz, CDCl$_3$) δ −70.5 (s, 3F)$_{pp}$m. ESI-MS m/z calc. 316.12863, found 317.1 (M+1)$^+$; Retention time: 2.47 minutes (LC Method B).

Step 3: 2-Benzyloxy-2-(trifluoromethyl)hex-5-enoic Acid

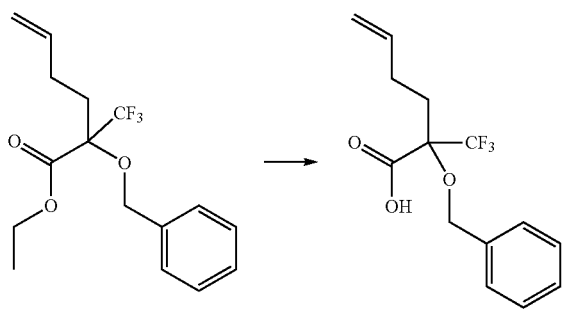 [SMILES: C=CCCC(OCc1ccccc1)(C(=O)OCC)C(F)(F)F ; C=CCCC(OCc1ccccc1)(C(=O)O)C(F)(F)F]

A solution of sodium hydroxide (7.86 g, 196.51 mmol) in water (60 mL) was added to a solution of ethyl 2-benzyloxy-2-(trifluoromethyl)hex-5-enoate (24.86 g, 78.593 mmol) in methanol (210 mL). The reaction was heated at 50° C. overnight. The reaction was concentrated to remove methanol, diluted with water (150 mL) and the carboxylate sodium salt was washed with heptane (1×100 mL). The aqueous solution was acidified to pH=2 with aqueous 3 N solution of HCl. The carboxylic acid was extracted with dichloromethane (3×100 mL) and dried over sodium sulfate. The solution was filtered and concentrated to give 2-benzyloxy-2-(trifluoromethyl)hex-5-enoic acid (22.57 g, 97%) as pale yellow oil. $^1$H NMR (300 MHz, DMSO-d6) δ 14.31 (br. s., 1H), 7.55-7.20 (m, 5H), 5.93-5.70 (m, 1H), 5.17-4.91 (m, 2H), 4.85-4.68 (m, 1H), 4.67-4.55 (m, 1H), 2.32-1.94 (m, 4H) ppm. $^{19}$F NMR (282 MHz, DMSO-d6) δ −70.29 (s, 3F) ppm. ESI-MS m/z calc. 288.09732, found 287.1 (M−1); Retention time: 3.1 minutes (LC Method C).

Step 4: tert-Butyl N-[[2-benzyloxy-2-(trifluoromethyl)hex-5-enoyl]amino]carbamate

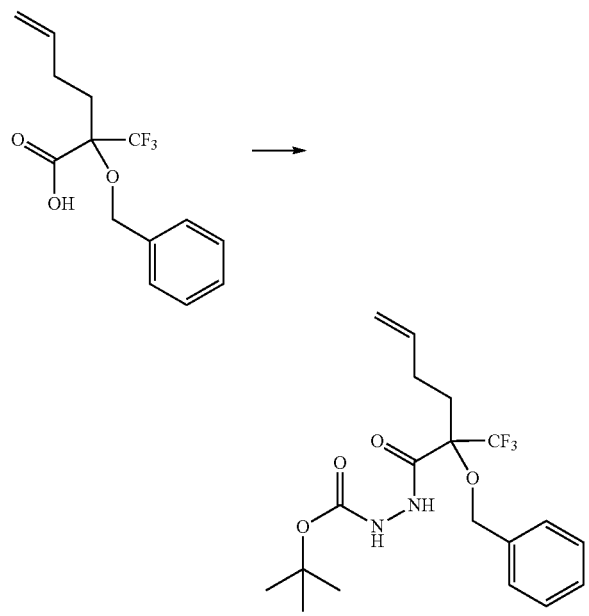

To a solution of 2-benzyloxy-2-(trifluoromethyl)hex-5-enoic acid (21.92 g, 92.4% purity, 70.263 mmol) in DMF (130 mL) was added HATU (37.2 g, 97.836 mmol) and Et$_3$N (15 g, 148.24 mmol). The mixture was stirred for 10 minutes then tert-butyl N-aminocarbamate (12.2 g, 92.312 mmol) was added. The mixture was stirred at 25° C. overnight and at 40° C. for 1 h. The mixture was diluted with ice-water (500 g) and extracted with CH$_2$Cl$_2$. The organic layer dried over anhydrous sodium sulfate and was concentrated. Purification by silica gel chromatography (0% to 30% EtOAc in heptanes) provided as a white solid, tert-butyl N-[[2-benzyloxy-2-(trifluoromethyl)hex-5-enoyl]amino]carbamate (26.08 g, 92%). $^1$H NMR (300 MHz, CDCl$_3$) δ 1.46 (s, 9H), 2.10-2.31 (m, 3H), 2.34-2.51 (m, 1H), 4.60-4.72 (m, 1H), 4.73-4.86 (m, 1H), 4.95-5.19 (m, 2H), 5.83 (ddt, J=16.7, 10.4, 6.1 Hz, 1H), 6.28 (br. s., 1H), 7.30-7.51 (m, 5H), 8.34 (d, J=2.6 Hz, 1H) ppm. $^{19}$F NMR (282 MHz, CDCl$_3$) δ−73.6 (s, 3F) ppm.

Step 5: 2-Benzyloxy-2-(trifluoromethyl)hex-5-enehydrazide (hydrochloride Salt)

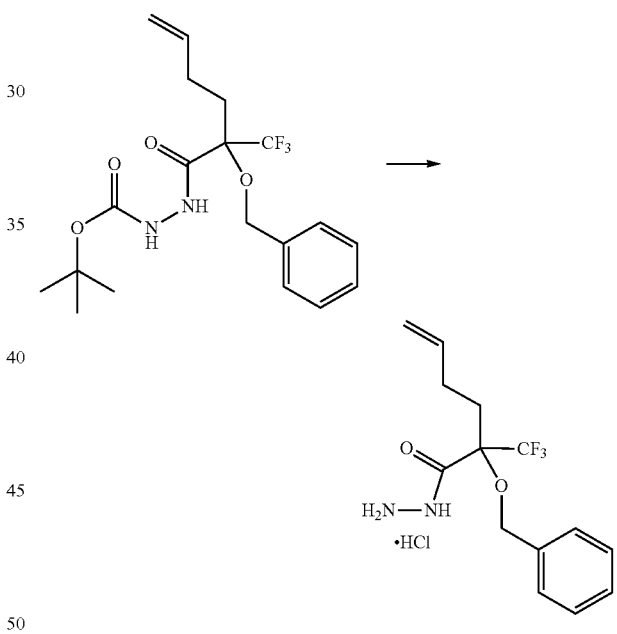

To a solution of tert-butyl N-[[2-benzyloxy-2-(trifluoromethyl)hex-5-enoyl]amino]carbamate (43.12 g, 107.2 mmol) in CH$_2$Cl$_2$ (200 mL) was added HCl (100 mL of 4 M, 400.0 mmol) and the mixture was stirred at ambient temperature for 7 h. The solvent was removed in vacuo, the residue stripped 2 times from heptane and the resultant solid was dried in vacuo using a high vac for 20 h giving 2-benzyloxy-2-(trifluoromethyl)hex-5-enehydrazide (hydrochloride salt) (35 g, 96%) $^1$H NMR (400 MHz, Chloroform-d) δ 9.92 (s, 2H), 7.41-7.31 (m, 2H), 7.30-7.24 (m, 2H), 7.24-7.16 (m, 1H), 5.72-5.57 (m, 1H), 5.02-4.87 (m, 2H), 4.71 (d, J=10.9 Hz, 1H), 4.62 (d, J=11.0 Hz, 1H), 3.70 (s, 2H), 2.34-1.85 (m, 4H). ESI-MS m/z calc. 302.1242, found 303.2 (M+1)$^+$; Retention time: 1.5 minutes (LC Method A).

Intermediate 6: Preparation of 2-benzyloxy-2-(trifluoromethyl)hex-5-enehydrazide

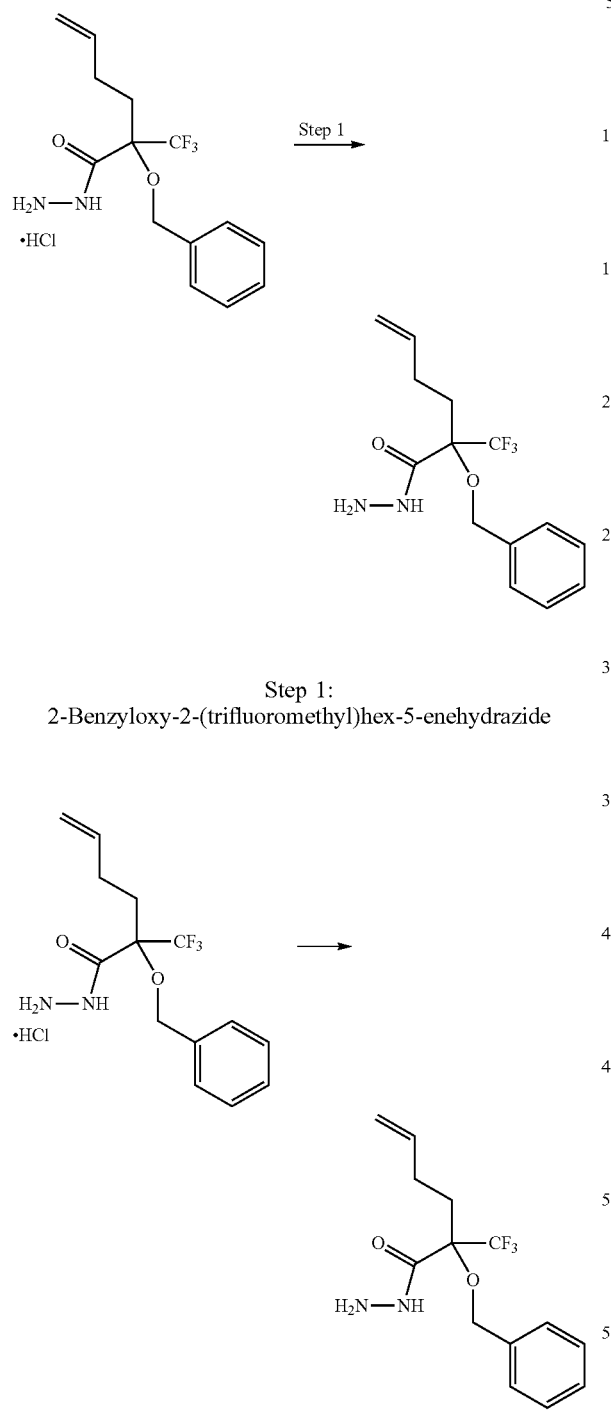

Step 1: 2-Benzyloxy-2-(trifluoromethyl)hex-5-enehydrazide

2-Benzyloxy-2-(trifluoromethyl)hex-5-enehydrazide (hydrochloride salt) was dissolved in ethyl acetate (500 mL) and carefully treated with saturated aqueous $NaHCO_3$ (500 mL) and stirred for 0.5 h. The phases were separated and the organic phase was washed once with 1:1 saturated aqueous $NaHCO_3$/water (500 mL), once with 1:4 saturated aqueous $NaHCO_3$/water (500 mL), once with water (500 mL) and once with brine (300 mL). The aqueous phases were back extracted once with ethyl acetate (200 mL) and the combined organic phases were dried, filtered, evaporated and then co-evaporated with toluene and further dried under vacuum to give as a yellow oil, 2-benzyloxy-2-(trifluoromethyl)hex-5-enehydrazide (50 g, 99%). $^1$H NMR (400 MHz, DMSO-d6) δ 9.33 (s, 1H), 7.53-7.27 (m, 5H), 5.81 (ddt, J=16.6, 10.2, 6.3 Hz, 1H), 5.10-4.93 (m, 2H), 4.71 (s, 2H), 4.57-4.28 (m, 2H), 2.27-1.84 (m, 4H) ppm. ESI-MS m/z calc. 302.1242, found 303.0 (M+1)$^+$; Retention time: 1.5 minutes (LC Method A).

Intermediate 7: Preparation of tert-butyl N-[2-[5-[1-benzyloxy-1-(trifluoromethyl)pent-4-enyl]-1,3,4-oxadiazol-2-yl]-6-bromo-5-(trifluoromethyl)-3-pyridyl]carbamate

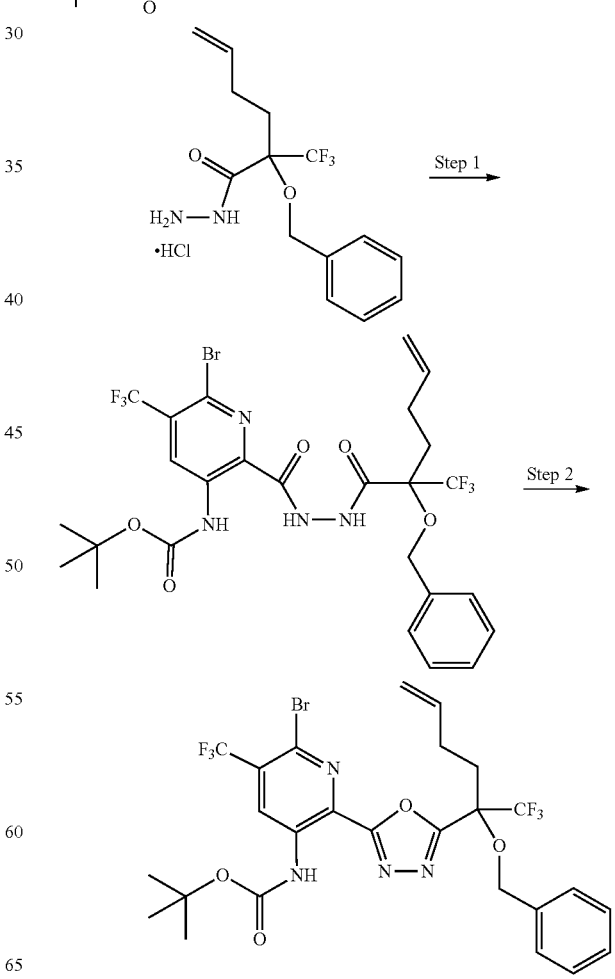

Step 1: tert-Butyl N-[2-[[[2-benzyloxy-2-(trifluoromethyl)hex-5-enoyl]amino]carbamoyl]-6-bromo-5-(trifluoromethyl)-3-pyridyl]carbamate

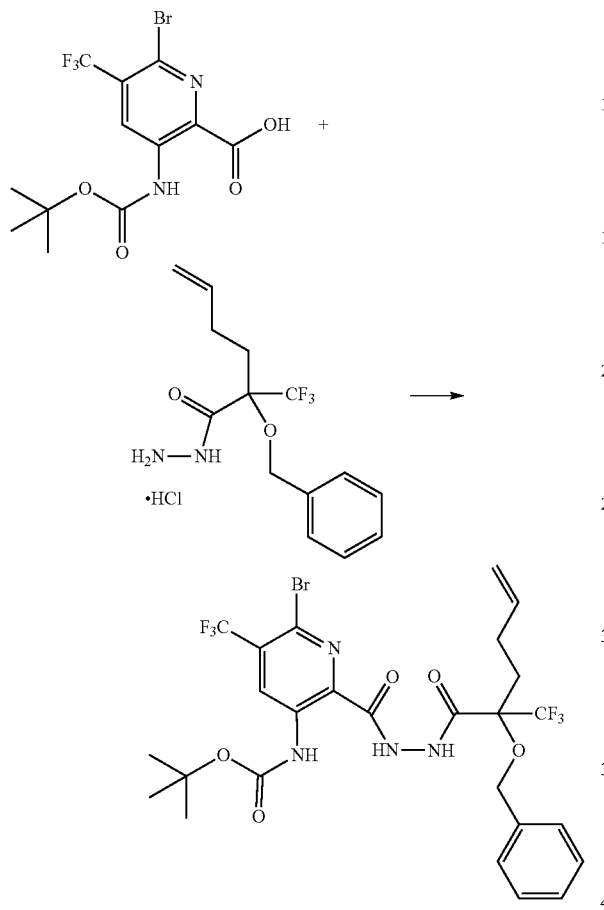

To a mixture of 6-bromo-3-(tert-butoxycarbonylamino)-5-(trifluoromethyl)pyridine-2-carboxylic acid (239.2 g, 621.1 mmol) and 2-benzyloxy-2-(trifluoromethyl)hex-5-enehydrazide (hydrochloride salt) (230.1 g, 761.2 mmol) in EtOAc (2.2 L) at ambient temperature was added pyridine (200 mL, 2.473 mol) which afforded a precipitate. To the mixture was added 1-propanephosphonic anhydride (500 g of 50% w/w, 785.7 mmol) and the reaction mixture was stirred at ambient temperature for 12 h. The reaction was quenched with the slow addition of NaOH (149 g of 50 w/w, 1.863 mol) in water (2 L) and the mixture was stirred for 15 min. The organic phase was separated, and the aqueous phase extracted with EtOAc (1 L). The combined organic phases washed with brine, dried over MgSO₄, filtered and concentrated in vacuo. After half of the solvent was removed, the organic phase was washed 2 times with aqueous HCl (1000 mL of 1 M, 1.000 mol). The organic phase was dried over MgSO₄, filtered and concentrated in vacuo. The crude product was slurried in warm heptane (2.5 L) and MTBE (0.25 L) and the mixture stirred at ambient temperature for 12 h affording a light yellow slurry. The slurry was filtered, and the resultant filter cake was washed 2 times with 1 L of 10% MTBE/heptane. The off-white solid was air dried for 2 h, then in vacuo at 40° C. for 20 h giving tert-butyl N-[2-[[[2-benzyloxy-2-(trifluoromethyl)hex-5-enoyl]amino]carbamoyl]-6-bromo-5-(trifluoromethyl)-3-pyridyl]carbamate (379.9 g, 91%) $^1$H NMR (400 MHz, DMSO-d6) δ 11.09 (s, 1H), 10.92 (s, 1H), 10.35 (s, 1H), 9.15 (s, 1H), 7.50 (d, J=7.4 Hz, 2H), 7.36 (dt, J=24.4, 7.2 Hz, 3H), 5.87 (ddt, J=16.0, 10.4, 5.2 Hz, 1H), 5.09 (d, J=16.9 Hz, 1H), 5.02 (d, J=10.1 Hz, 1H), 4.84 (q, J=11.4 Hz, 2H), 2.35-2.12 (m, 4H), 1.49 (s, 9H) ppm. ESI-MS m/z calc. 668.1069, found 670.9 (M+3, Br isotope)⁺; Retention time: 3.5 minutes (LC Method D).

Step 2: tert-Butyl N-[2-[5-[1-benzyloxy-1-(trifluoromethyl)pent-4-enyl]-1,3,4-oxadiazol-2-yl]-6-bromo-5-(trifluoromethyl)-3-pyridyl]carbamate

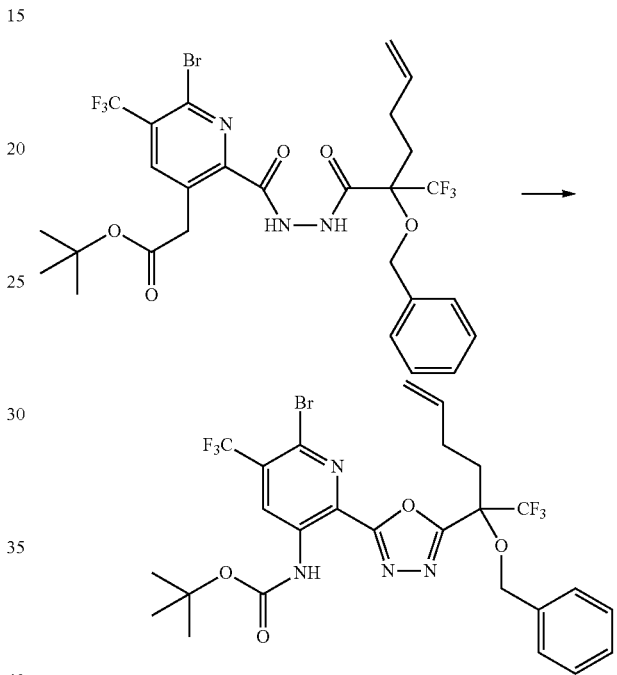

tert-Butyl N-[2-[[[2-benzyloxy-2-(trifluoromethyl)hex-5-enoyl]amino]carbamoyl]-6-bromo-5-(trifluoromethyl)-3-pyridyl]carbamate (102 g, 150.8 mmol) was dissolved in anhydrous acetonitrile (1000 mL) and DIPEA (92 mL, 528.2 mmol) was added. The resultant orange solution was heated to 70° C. (internal temp) making a clear yellow solution. Then p-toluenesulfonyl chloride (37.4 g, 196.2 mmol) was added in 3 equal portions of 12.47 g separated by 10 minutes and then the reaction was heated for another 30 min. The reaction was cooled to room temperature and the acetonitrile was concentrated under reduced pressure. To the mixture was added 1000 mL MTBE, then 800 mL water, and the mixture was stirred, and the layers were separated. The organic layer was washed with a solution of citric acid (36.3 g, 188.9 mmol) in 700 mL water, then 400 mL saturated NaHCO₃, then 300 mL brine. The organic layer was then dried over anhydrous MgSO₄ and concentrated under reduced pressure. The material was purified using silica gel chromatography with a gradient of 15% to 50% of an 8% solution of EtOAc in hexanes to pure hexanes to provide tert-butyl N-[2-[5-[1-benzyloxy-1-(trifluoromethyl)pent-4-enyl]-1,3,4-oxadiazol-2-yl]-6-bromo-5-(trifluoromethyl)-3-pyridyl]carbamate (91.7 g, 93%), $^1$H NMR (400 MHz, Chloroform-d) δ 10.18 (s, 1H), 9.35 (s, 1H), 7.55-7.47 (m, 2H), 7.45-7.37 (m, 2H), 7.36-7.28 (m, 1H), 5.83-5.68 (m, 1H), 5.10-4.93 (m, 2H), 4.82 (d, J=10.5 Hz, 1H), 4.69 (d, J=10.5 Hz, 1H), 2.59-2.13 (m, 4H), 1.56 (s, 9H) ppm. ESI-MS m/z calc. 650.0963, found 651.0 (M+1)⁺; Retention time: 3.81 minutes (LC Method D).

Intermediate 8: Preparation of tert-butyl N-[2-[5-[1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate

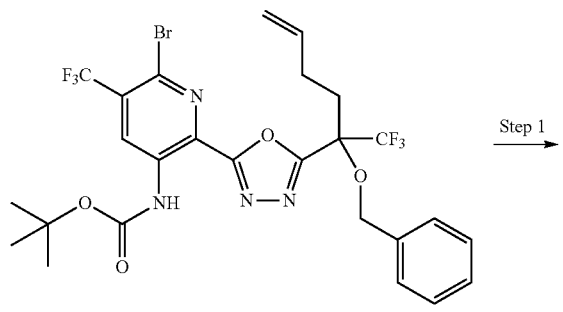

Step 1: tert-Butyl N-[2-[5-[1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate

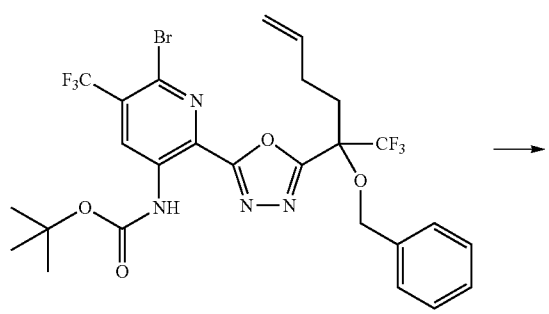

-continued

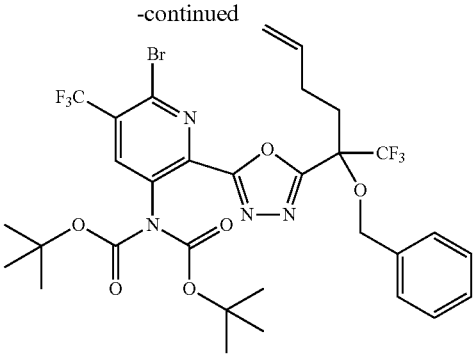

Into a solution of tert-butyl N-[2-[5-[1-benzyloxy-1-(trifluoromethyl)pent-4-enyl]-1,3,4-oxadiazol-2-yl]-6-bromo-5-(trifluoromethyl)-3-pyridyl]carbamate (30 g, 41.910 mmol) in MTBE (300 mL) was added DIEA (6.6780 g, 9 mL, 51.670 mmol), DMAP (0.28 g, 2.2919 mmol) and Boc anhydride (20.1 g, 21.158 mL, 92.097 mmol). The resulting yellow cloudy solution was stirred at 35° C. overnight. After cooling to room temperature, the solvent was evaporated. The yellow oily residue was then dissolved in 300 mL DCM and was washed with water (300 mL), followed by brine (300 mL). The organic layer was separated, dried over anhydrous sodium sulfate, filtered, and concentrated. Purification by silica gel chromatography (0% to 20% EtOAc in hexanes) provided tert-butyl N-[2-[5-[1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate (28.68 g, 87%) as white solid. ¹H NMR (500 MHz, DMSO-d6) δ 8.89 (s, 1H), 7.51 (d, J=7.4 Hz, 2H), 7.43 (t, J=7.5 Hz, 2H), 7.35 (t, J=7.3 Hz, 1H), 5.96-5.76 (m, 1H), 5.11 (d, J=17.2 Hz, 1H), 5.01 (d, J=10.1 Hz, 1H), 4.73 (d, J=10.7 Hz, 1H), 4.66 (d, J=10.6 Hz, 1H), 2.65-2.51 (m, 2H), 2.36-2.17 (m, 2H), 1.27 (d, J=23.5 Hz, 18H) ppm. ESI-MS m/z calc. 750.1488, found 751.6 (M+1)⁺; Retention time: 3.9 minutes (LC Method G).

Intermediate 9: Preparation of 2-benzyloxy-2-(trifluoromethyl)pent-4-enehydrazide (hydrochloride Salt)

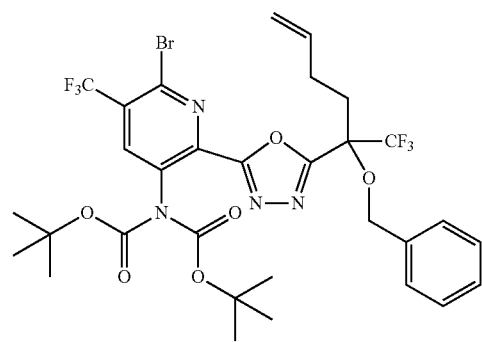

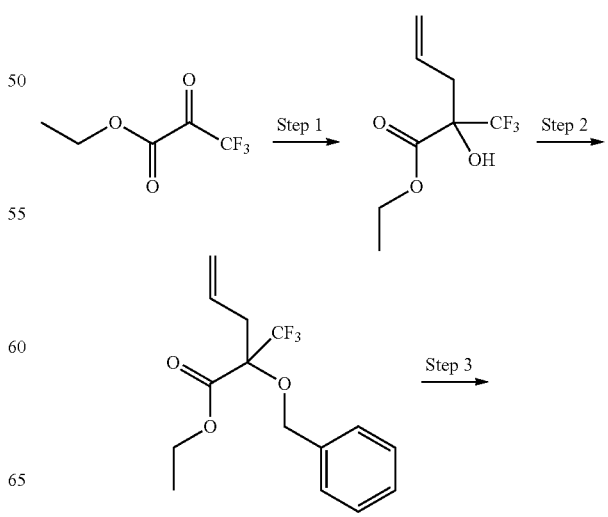

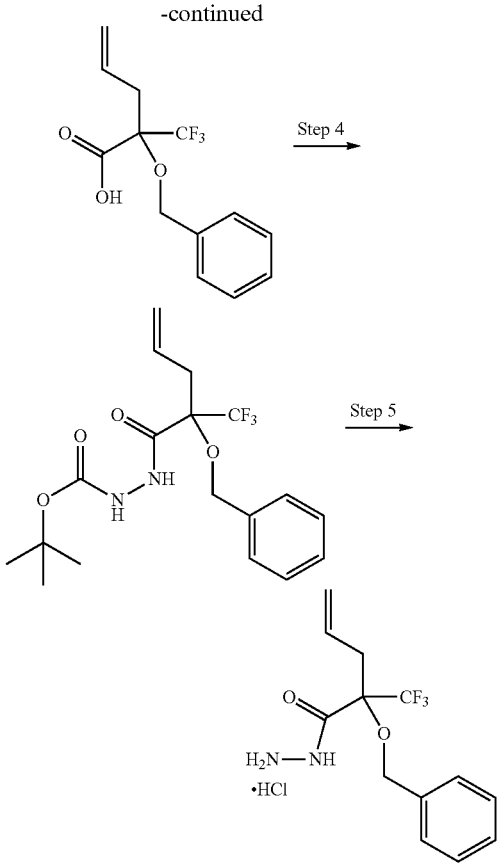

Step 1: Ethyl 2-hydroxy-2-(trifluoromethyl)pent-4-enoate

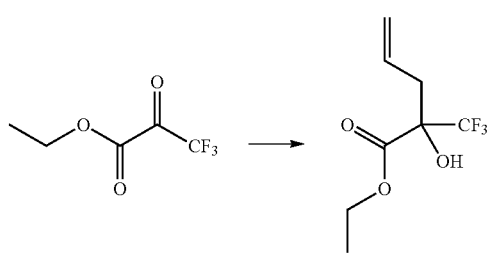

To a solution of ethyl 3,3,3-trifluoro-2-oxo-propanoate (30 g, 176.38 mmol) in diethyl ether (300 mL) at −78° C. was added allyl(bromo)magnesium (185 mL of 1 M, 185.00 mmol) dropwise over a period of 3 hours (internal temperature: −74° C.--76° C.). The mixture was stirred at −78° C. for 45 min. The dry ice-acetone bath was removed. The mixture was allowed to warm to about 10° C. over a period of 1 h and added to a mixture of 1N aqueous HCl (210 mL) and crushed ice (400 g) (pH 4). The mixture was extracted with EtOAc, washed with 5% aqueous NaHCO₃, brine and dried over anhydrous Na₂SO₄. The mixture was filtered, concentrated and co-evaporated with hexane to give as a light yellow oil, ethyl 2-hydroxy-2-(trifluoromethyl)pent-4-enoate (42.2 g, 90%). $^1$H NMR (300 MHz, CDCl₃) δ 1.33 (t, J=7.1 Hz, 3H), 2.60-2.79 (m, 2H), 3.84 (br. s., 1H), 4.24-4.48 (m, 2H), 5.09-5.33 (m, 2H), 5.59-5.82 (m, 1H) ppm. $^{19}$F NMR (282 MHz, CDCl₃) δ −78.5 (s, 3F) ppm.

Step 2: Ethyl 2-benzyloxy-2-(trifluoromethyl)pent-4-enoate

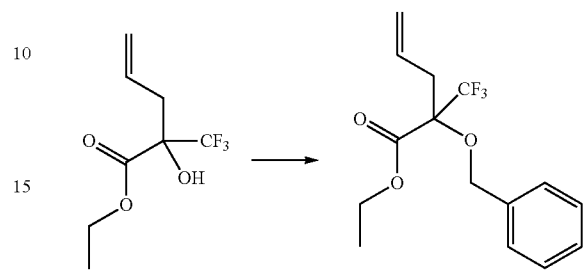

To a solution of ethyl 2-hydroxy-2-(trifluoromethyl)pent-4-enoate (18.56 g, 83.105 mmol) in DMF (100 mL) was added NaH (5.3 g, 60% w/w, 132.51 mmol) at 0° C. The reaction was stirred for 15 minutes and benzyl bromide (21.14 g, 15 mL, 121.12 mol) and tetrabutyl ammonium iodide (8.5 g, 23.012 mmol) were added. The mixture was stirred at room temperature overnight. The reaction was quenched with water (300 mL) and extracted with ethyl acetate (3×300 mL). The combined organic layers were washed with brine (500 mL) and dried over sodium sulfate. Purification by silica gel chromatography (20% to 60% DCM in hexanes) provided ethyl 2-benzyloxy-2-(trifluoromethyl)pent-4-enoate (22.01 g, 70%) as colorless oil. $^1$H NMR (250 MHz, CDCl₃) δ 7.55-7.25 (m, 5H), 6.00-5.80 (m, 1H), 5.30-5.10 (m, 2H), 4.86 (d, J=10.5 Hz, 1H), 4.68 (d, J=10.5 Hz, 1H), 4.33 (q, J=7.0 Hz, 2H), 2.81 (d, J=7.0 Hz, 2H), 1.34 (t, J=7.1 Hz, 3H) ppm. ESI-MS m/z calc. 302.113, found 303.5 (M+1)$^+$; Retention time: 4.14 minutes (LC Method G).

Step 3: 2-Benzyloxy-2-(trifluoromethyl)pent-4-enoic Acid

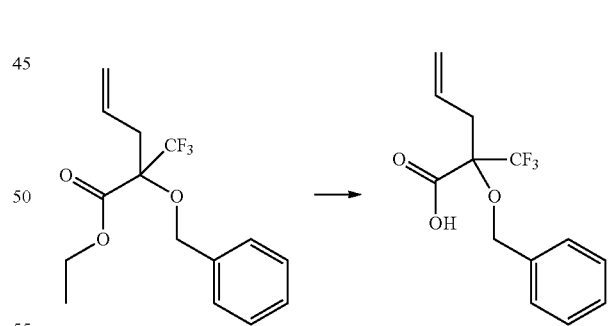

Into a solution of ethyl 2-benzyloxy-2-(trifluoromethyl)pent-4-enoate (28.99 g, 95.902 mmol) in methanol (150 mL) was added a solution of NaOH (7.6714 g, 191.80 mmol) in water (50 mL). The reaction mixture was stirred at 40° C. for 3 hours. The reaction mixture was concentrated under vacuum, the residue was diluted with water (200 mL) and washed with diethyl ether (200 mL). The aqueous layer was acidified with concentrated HCl to pH 1 and extracted with diethyl ether (3×200 mL). The combined organic layers were washed with brine, dried over anhydrous sodium sulfate, and concentrated under vacuum to furnish as a light yellow liquid, 2-benzyloxy-2-(trifluoromethyl)pent-4-enoic acid (28.04 g, 99%). $^1$H NMR (250 MHz, CDCl$_3$) δ 7.55-7.28 (m, 5H), 5.97-5.69 (m, 1H), 5.33-5.17 (m, 2H), 4.95-4.66 (m, 2H), 2.91 (d, J=7.1 Hz, 2H) ppm. One exchangeable proton not observed in NMR.

Step 4: tert-Butyl N-[[2-benzyloxy-2-(trifluoromethyl)pent-4-enoyl]amino]carbamate

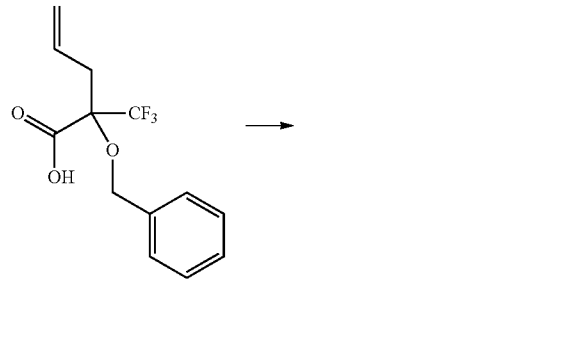

To a solution of 2-benzyloxy-2-(trifluoromethyl)pent-4-enoic acid (300 g, 1.094 mol) in DMF (2 L) was added HATU (530 g, 1.394 mol) and DIEA (400 mL, 2.296 mol) and the mixture was stirred at ambient temperature for 10 min. To the mixture was added tert-butyl N-aminocarbamate (152 g, 1.150 mol) and the mixture stirred at ambient temperature for 36 h. The reaction was quenched with cold water (4 L) and the mixture extracted with EtOAc (2×2 L). The organic phase was washed brine, dried over MgSO$_4$, filtered and concentrated in vacuo. Purification by silica gel chromatography (0% to 40% EtOAc/hexanes) provided tert-butyl N-[[2-benzyloxy-2-(trifluoromethyl)pent-4-enoyl]amino]carbamate (386.49 g, 91%) as an oil which slowly crystallized to an off-white solid. $^1$H NMR (400 MHz, DMSO) δ 10.00 (d, J=37.9 Hz, 1H), 8.93 (s, 1H), 7.46-7.39 (m, 2H), 7.38-7.29 (m, 3H), 6.01-5.64 (m, 1H), 5.32 (d, J=17.1 Hz, 1H), 5.17 (d, J=10.1 Hz, 1H), 4.77 (s, 2H), 2.96 (qd, J=15.4, 6.8 Hz, 2H), 1.39 (d, J=17.3 Hz, 9H) ppm. ESI-MS m/z calc. 388.16098, found 389.0 (M+1)$^+$; Retention time: 2.51 minutes (LC Method D).

Step 5: 2-Benzyloxy-2-(trifluoromethyl)pent-4-enehydrazide (hydrochloride salt)

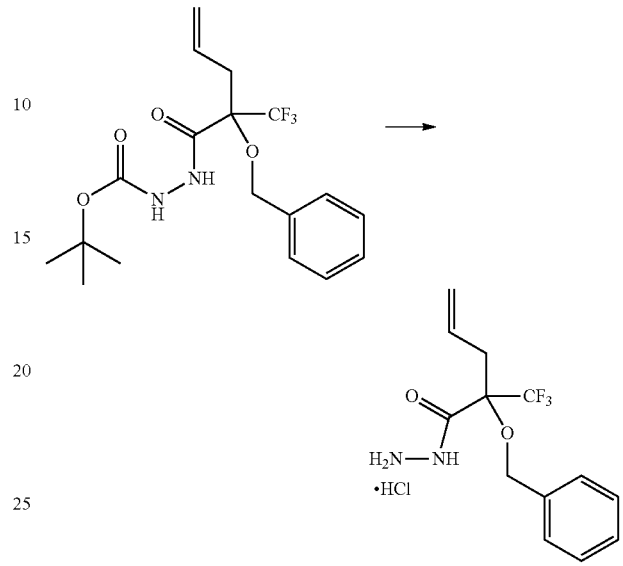

To a solution of tert-butyl N-[[2-benzyloxy-2-(trifluoromethyl)pent-4-enoyl]amino]carbamate (98.5 g, 240.94 mmol) in DCM (400 mL) was added HCl in dioxane (200 mL of 4 M, 800.00 mmol). The mixture was stirred at room temperature for 2 hours, concentrated and co-evaporated with DCM and hexanes to give 2-benzyloxy-2-(trifluoromethyl)pent-4-enehydrazide (hydrochloride salt) (81.15 g, 97%) as an off white solid. $^1$H NMR (500 MHz, DMSO-d6) δ 11.07 (s, 1H), 7.70-7.16 (m, 5H), 5.87-5.61 (m, 1H), 5.45-5.09 (m, 2H), 4.79 (s, 2H), 3.6-3.4 (m, 2H), 3.23-3.07 (m, 1H), 3.04-2.87 (m, 1H) ppm. ESI-MS m/z calc. 288.10855, found 289.2 (M+1)$^+$; Retention time: 2.0 minutes (LC Method H).

Intermediate 10: Preparation of methyl 3-[bis(tert-butoxycarbonyl)amino]-6-bromo-5-methylsulfonyl-pyridine-2-carboxylate

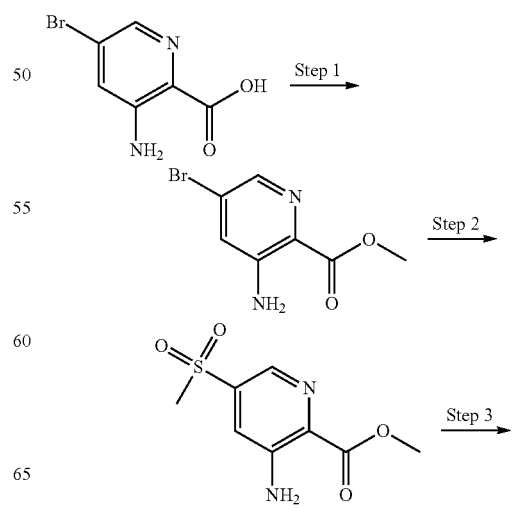

-continued

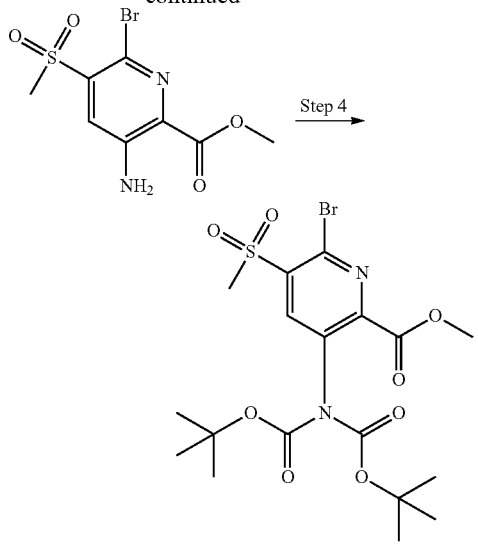

Step 1: Methyl 3-amino-5-bromo-pyridine-2-carboxylate

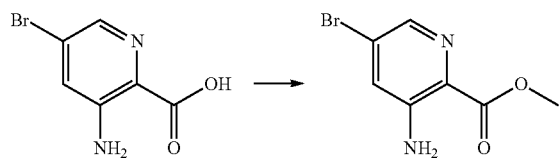

Sulfuric acid (10 mL, 187.6 mmol) was added to a solution of 3-amino-5-bromo-pyridine-2-carboxylic acid (10 g, 43.77 mmol) in methanol (250 mL). The reaction was heated at 75° C. for 3 days. The reaction mixture was cooled to room temperature and about ⅔ of the solvent was removed under reduced pressure. The resulting mixture was poured onto a mixture of brine (200 mL) and ice (200 mL). The aqueous layer was extracted with EtOAc (3×200 mL). The organic layers were combined and washed with water (70 mL), 5% NaHCO$_3$ (70 mL) and brine (70 mL), dried over sodium sulfate, filtered and evaporated to give as a yellow solid, methyl 3-amino-5-bromo-pyridine-2-carboxylate (4.56 g, 45%). $^1$H NMR (300 MHz, CDCl$_3$) δ 3.96 (s, 3H), 5.82 (br. s, 2H), 7.24 (d, J=1.8 Hz, 1H), 8.06 (d, J=1.8 Hz, 1H) ppm. ESI-MS m/z calc. 229.96909, found 231.1 (M+1)$^+$; Retention time: 1.51 minutes (LC Method EE).

Step 2: Methyl 3-amino-5-methylsulfonyl-pyridine-2-carboxylate

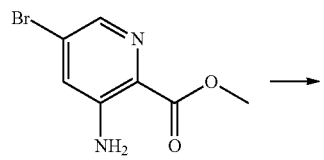

-continued

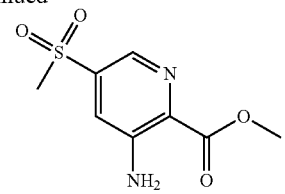

A mixture of methyl 3-amino-5-bromo-pyridine-2-carboxylate (9.79 g, 42.372 mmol), methylsulfinyloxysodium (8.8 g, 86.2 mmol), copper(I) iodide (8.8 g, 46.206 mmol), L-proline (34 mg, 0.2953 mmol) and DMF (195 mL) under nitrogen was heated at 130° C. for 3 h. The mixture was cooled to room temperature and added to EtOAc (1.2 L) with stirring. The mixture was filtered through diatomaceous earth and washed with EtOAc. The filtrate was washed with 28% aqueous NH$_3$ (1×100 mL then 1×50 mL) and brine (50 mL), dried with Na$_2$SO$_4$, filtered and concentrated to about 160 mL resulting in a precipitate. The precipitate was collected by filtration and dried to give as a yellow solid, methyl 3-amino-5-methylsulfonyl-pyridine-2-carboxylate (6.35 g, 65%). $^1$H NMR (300 MHz, DMSO-d6) δ 8.23 (d, J=2.1 Hz, 1H), 7.73 (d, J=2.1 Hz, 1H), 7.09 (s, 2H), 3.83 (s, 3H), 3.29 (s, 3H) ppm. ESI-MS m/z calc. 230.03613, found 231.1 (M+1)$^+$; Retention time: 1.22 minutes (LC Method E).

Step 3: Methyl 3-amino-6-bromo-5-methylsulfonyl-pyridine-2-carboxylate

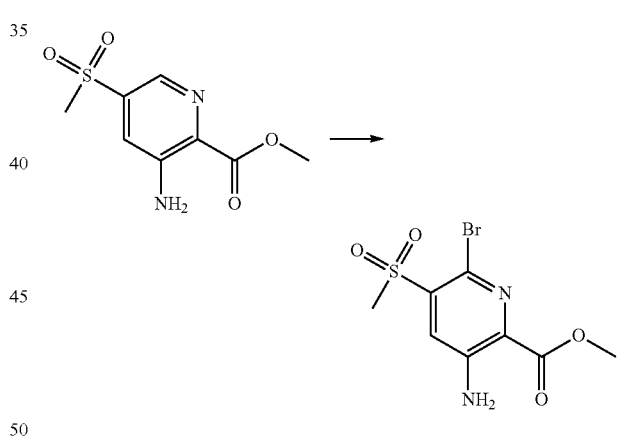

To a solution of methyl 3-amino-5-methylsulfonyl-pyridine-2-carboxylate (8 g, 34.746 mmol) in acetonitrile (515 mL) was added NBS (12.7 g, 71.355 mmol). The mixture was stirred at 35° C. for 64 h. The mixture was concentrated to remove most of acetonitrile. The residue was diluted with ethyl acetate (200 mL) and treated with a solution of 10% aqueous sodium thiosulfate solution (100 mL). After stirring for 10 min at room temperature, saturated aqueous sodium bicarbonate solution (100 mL) was added. After stirring for 5 min, the resulting precipitate was collected by filtration, washed with water and ethyl acetate then dried to afford as a yellow solid, methyl 3-amino-6-bromo-5-methylsulfonyl-pyridine-2-carboxylate (6.2 g, 55%). $^1$H NMR (300 MHz, DMSO-d6) δ 7.99 (s, 1H), 7.25 (br. s., 2H), 3.83 (s, 3H), 3.42 (s, 3H) ppm. ESI-MS m/z calc. 307.94666, found 308.8 (M+1)$^+$; Retention time: 1.57 minutes (LC Method E).

Step 4: Methyl 3-[bis(tert-butoxycarbonyl)amino]-6-bromo-5-methylsulfonyl-pyridine-2-carboxylate

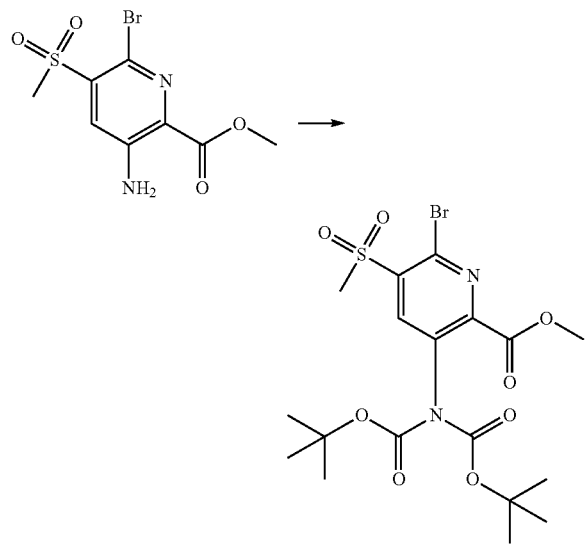

A mixture of methyl 3-amino-6-bromo-5-methylsulfonyl-pyridine-2-carboxylate (6.2 g, 19.153 mmol), tert-butoxycarbonyl tert-butyl carbonate (12.825 g, 13.5 mL, 58.764 mmol), DMAP (373 mg, 3.0532 mmol) and DCM (185 mL) was stirred at room temperature overnight. The reaction mixture was concentrated under reduced pressure. Purification by silica gel chromatography (gradient from 0% to 30% of ethyl acetate in heptanes) provided as a yellow solid, methyl 3-[bis(tert-butoxycarbonyl)amino]-6-bromo-5-methylsulfonyl-pyridine-2-carboxylate (8.72 g, 89%). $^1$H NMR (300 MHz, CDCl$_3$) δ 8.33 (s, 1H), 3.97 (s, 3H), 3.38 (s, 3H), 1.43 (s, 18H) ppm. ESI-MS m/z calc. 508.0515, found 352.8 (M-155)$^+$; Retention time: 2.08 minutes (LC Method E).

Intermediate 11: Preparation of methyl 6-chloro-3-nitro-5-(trifluoromethyl)pyridine-2-carboxylate

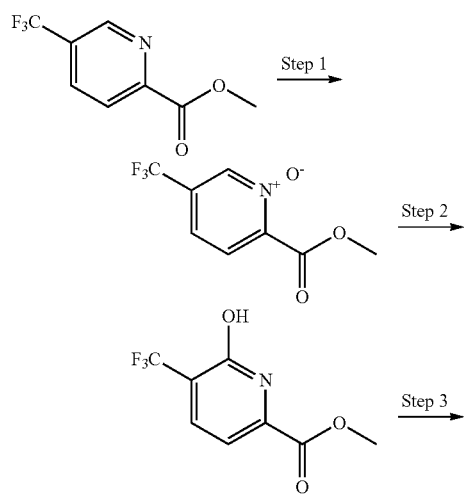

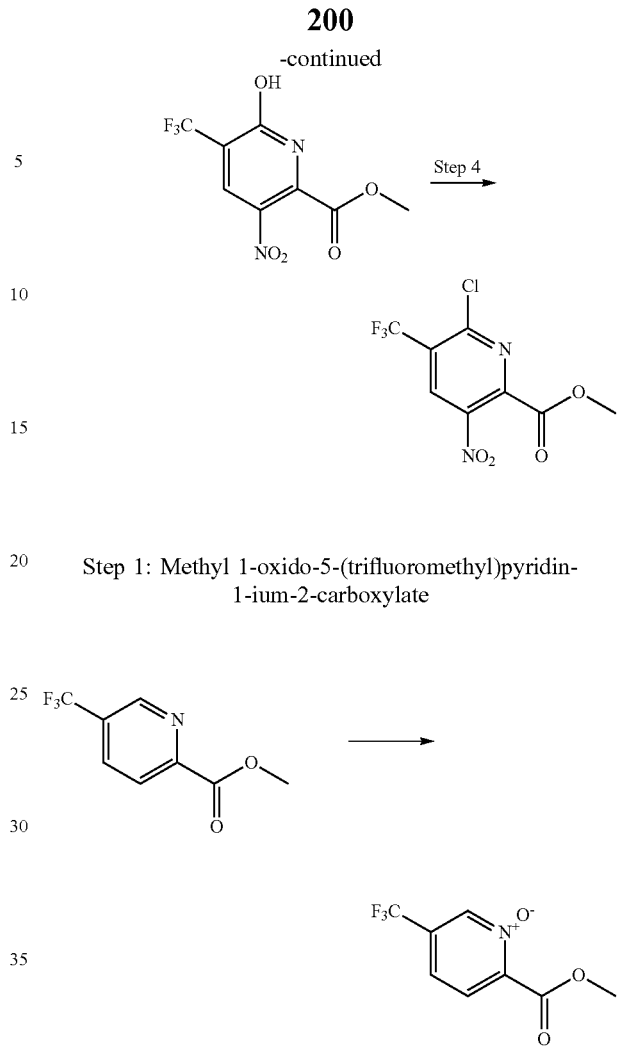

Step 1: Methyl 1-oxido-5-(trifluoromethyl)pyridin-1-ium-2-carboxylate

Urea hydrogen peroxide (62.7 g, 646.53 mmol) was added portion-wise to a stirred solution of methyl 5-(trifluoromethyl)pyridine-2-carboxylate (40 g, 191.09 mmol) in 1,2-dichloroethane (300 mL) at 0° C. Trifluoroacetic anhydride (107.70 g, 72 mL, 507.65 mmol) was then added over 30 minutes at a temperature of −10° C., with cooling bath (CO$_2$/acetone bath). The reaction mixture was then stirred for a further 30 minutes at a temperature of 0° C. and then for 1 hour at ambient temperature. The reaction mixture was then poured into cooled ice-water (600 mL). The mixture was diluted with dichloromethane (300 mL) and then layers were separated. The aqueous phase was extracted with dichloromethane (2×200 mL). The combined organic phase was washed with water (2×300 mL) and brine (1×200 mL), dried over anhydrous sodium sulfate, filtered and concentrated under reduced pressure to give as a light yellow solid, methyl 1-oxido-5-(trifluoromethyl)pyridin-1-ium-2-carboxylate (47.6 g, 90%). $^1$H NMR (300 MHz, DMSO-d6) δ 8.89 (s, 1H), 8.02-7.90 (m, 1H), 7.86-7.72 (m, 1H), 3.89 (s, 3H) ppm. $^{19}$F NMR (282 MHz, DMSO-d6) δ−62.00 (s, 3F) ppm. ESI-MS m/z calc. 221.02998, found 222.1 (M+1)$^+$; Retention time: 1.24 minutes (LC Method E).

Step 2: Methyl 6-hydroxy-5-(trifluoromethyl)pyridine-2-carboxylate

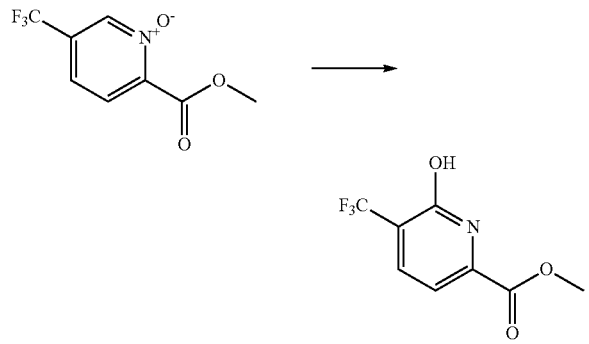

Trifluoroacetic anhydride (291.62 g, 193 mL, 1.3885 mol) was added drop-wise to a mixture of methyl 1-oxido-5-(trifluoromethyl)pyridin-1-ium-2-carboxylate (51.058 g, 230.66 mmol) in DMF (305 mL) at 0° C. The mixture was then stirred at room temperature overnight. The mixture was concentrated under reduced pressure to remove excess of trifluoroacetic acid. The residual DMF solution was poured dropwise to a 0° C. cooled and stirring water volume (1000 mL). The precipitated solid was collected by filtration and then washed with water (300 mL). The solid was dried under vacuum to afford methyl 6-hydroxy-5-(trifluoromethyl)pyridine-2-carboxylate (45.24 g, 86%) as a white solid. $^1$H NMR (300 MHz, CDCl$_3$) δ 7.90 (d, J=7.2 Hz, 1H), 7.03 (d, J=7.2 Hz, 1H), 4.02 (s, 3H) ppm. One exchangeable proton not observed in NMR. $^{19}$F NMR (282 MHz, CDCl$_3$) δ−66.39 (s, 3F) ppm. ESI-MS m/z calc. 221.03, found 222.1 (M+1)$^+$; Retention time: 1.43 minutes (LC Method E).

Step 3: Methyl 6-hydroxy-3-nitro-5-(trifluoromethyl)pyridine-2-carboxylate

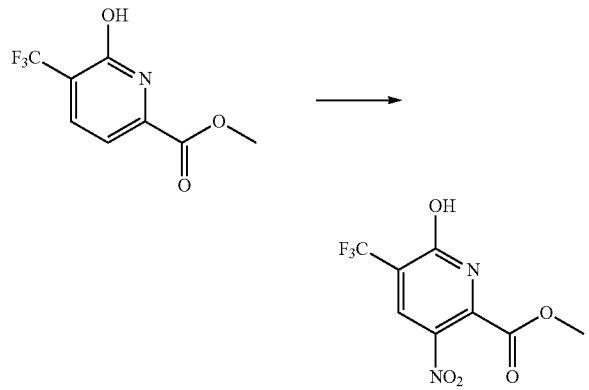

To an ice-cooled solution of methyl 6-hydroxy-5-(trifluoromethyl)pyridine-2-carboxylate (33.04 g, 149.41 mmol) in sulfuric acid (200 mL of 18.4 M, 3.6800 mol) was added nitric acid (13 mL of 15.8 M, 205.40 mmol) dropwise. After 5 min, the ice bath was removed, and the reaction mixture was stirred at 38° C. overnight. The reaction was not completed, nitric acid (3 mL of 15.8 M, 47.400 mmol) was added dropwise at room temperature and the reaction was heated at 38° C. for 4.5 hours. The reaction was poured slowly on ice-cold water (900 mL) and the mixture was cooled at 0° C. for 15 minutes. Then the resultant solid was isolated by filtration and washed with water (600 mL). The solid was dried overnight under vacuum to give as a white solid, methyl 6-hydroxy-3-nitro-5-(trifluoromethyl)pyridine-2-carboxylate (39.49 g, 99%). $^1$H NMR (300 MHz, DMSO-d6) δ 8.54 (s, 1H), 3.95 (s, 3H) ppm. One exchangeable proton not observed in NMR. $^{19}$F NMR (282 MHz, DMSO-d6) δ−64.56 (s, 3F) ppm. ESI-MS m/z calc. 266.0151, found 267.1 (M+1)$^+$; Retention time: 1.64 minutes (LC Method E).

Step 4: Methyl 6-chloro-3-nitro-5-(trifluoromethyl)pyridine-2-carboxylate

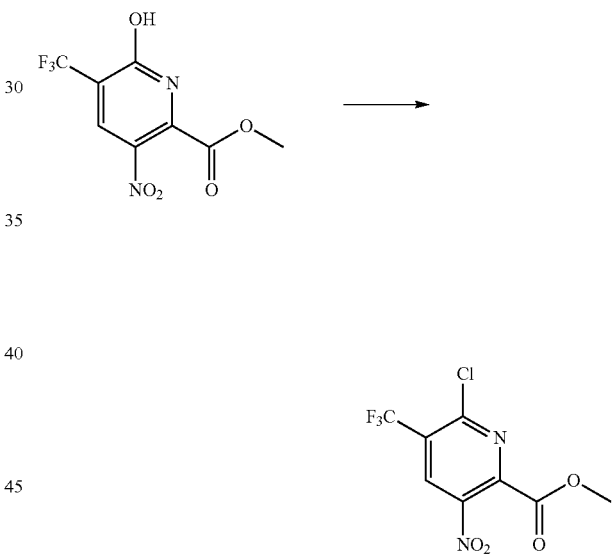

A mixture of methyl 6-hydroxy-3-nitro-5-(trifluoromethyl)pyridine-2-carboxylate (10 g, 37.575 mmol) and phenyl dichlorophosphate (48.008 g, 34 mL, 227.55 mmol) was heated at 170° C. for 90 minutes. After cooling to room temperature, the mixture was diluted with ethyl acetate (400 mL) and washed with brine (2×200 mL). The organic phase was dried on anhydrous sodium sulfate, filtered and concentrated under reduced pressure. Purification by silica gel chromatography (0% to 15% of ethyl acetate in heptanes) provided methyl 6-chloro-3-nitro-5-(trifluoromethyl)pyridine-2-carboxylate (5.45 g, 50%) as a yellow solid. $^1$H NMR (300 MHz, CDCl$_3$) δ 8.75 (s, 1H), 4.07 (s, 3H) ppm. $^{19}$F NMR (282 MHz, CDCl$_3$) δ−64.12 (s, 3F) ppm. ESI-MS m/z calc. 283.9812, found 285.0 (M+1)$^+$; Retention time: 1.95 minutes (LC Method E).

Intermediate 12: Preparation of 6-hydroxy-3-nitro-5-(trifluoromethyl)pyridine-2-carboxylic acid

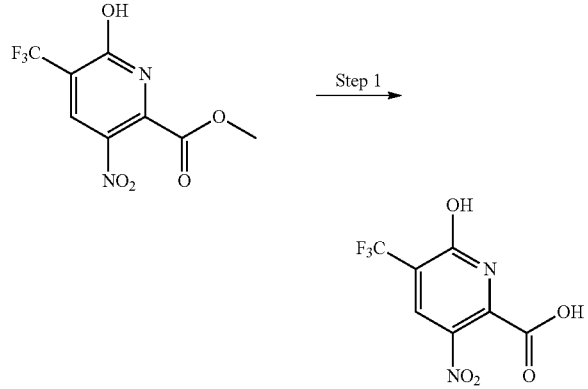

Step 1: 6-Hydroxy-3-nitro-5-(trifluoromethyl)pyridine-2-carboxylic acid

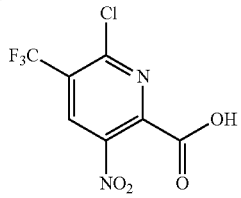

A mixture of methyl 6-hydroxy-3-nitro-5-(trifluoromethyl)pyridine-2-carboxylate (32 g, 120.24 mmol) in THF (180 mL) and water (180 mL) was treated with lithium hydroxide monohydrate (15.14 g, 360.79 mmol) and stirred at 27° C. overnight. The crude reaction mixture was cooled at room temperature and the pH adjusted to 2 with a 0.5 M aqueous solution of hydrochloric acid (380 mL), then transferred to a 1-L separatory funnel with 2-methyl THF and extracted. The layers were separated and the organic layer was then washed with water (150 mL), brine (150 mL), dried over sodium sulfate, filtered and concentrated under reduced pressure to afford as an off-white solid, 6-hydroxy-3-nitro-5-(trifluoromethyl)pyridine-2-carboxylic acid (29.61 g, 96%). $^1$H NMR (300 MHz, DMSO-d6) δ 8.45 (s, 1H) ppm. One exchangeable proton not observed in NMR. $^{19}$F NMR (282 MHz, DMSO-d6) δ −64.53 (s, 3F) ppm. ESI-MS m/z calc. 251.9994, found 253.0 (M+1)$^+$; Retention time: 0.79 minutes (LC Method E).

Intermediate 13: Preparation of [6-[5-[1-benzyloxy-1-(trifluoromethyl)pent-4-enyl]-1,3,4-oxadiazol-2-yl]-5-nitro-3-(trifluoromethyl)-2-pyridyl]trifluoromethanesulfonate

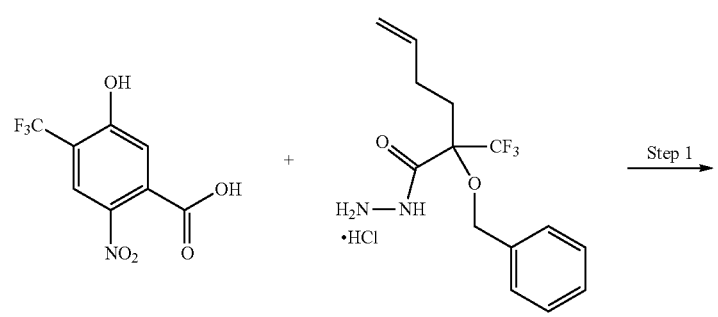

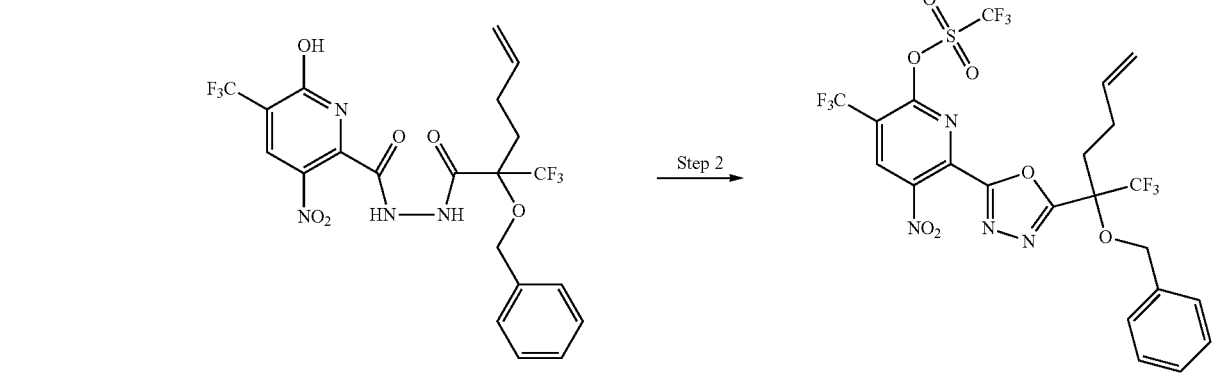

Step 1: N'-[2-Benzyloxy-2-(trifluoromethyl)hex-5-enoyl]-6-hydroxy-3-nitro-5-(trifluoromethyl)pyridine-2-carbohydrazide

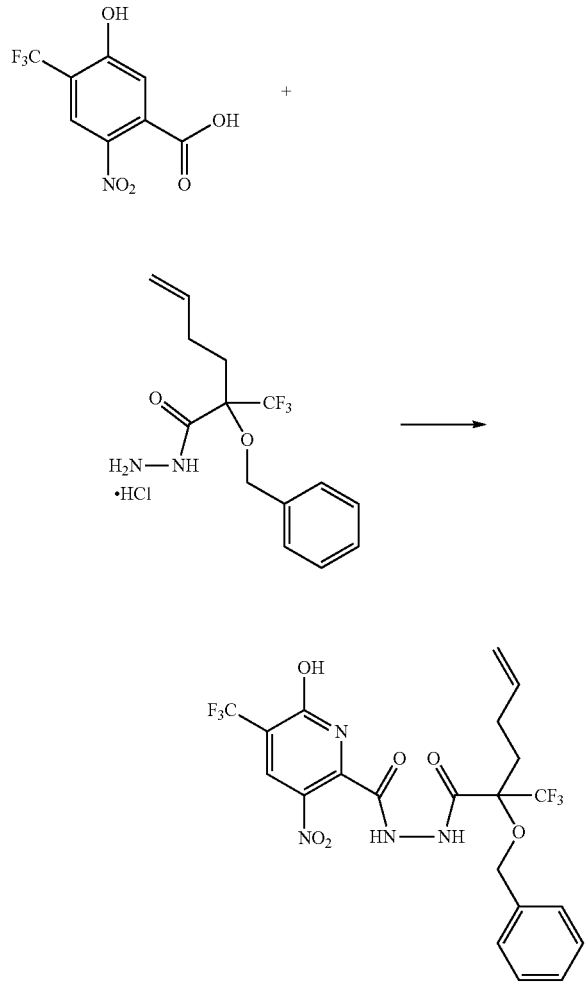

To a solution of 6-hydroxy-3-nitro-5-(trifluoromethyl) pyridine-2-carboxylic acid (29.92 g, 102.66 mmol) in acetonitrile (300 mL) and DMF (60 mL) was added CDI (17.48 g, 107.80 mmol). The mixture was stirred for 0.5 h at room temperature, then 2-benzyloxy-2-(trifluoromethyl) hex-5-enehydrazide (hydrochloride salt) (33.04 g, 97.534 mmol) was added in portions. The reaction mixture was stirred at 26° C. for 19 hours. The reaction mixture was transferred to an extraction funnel rinsing with water (300 mL) and 2-Me THF (400 mL). The mixture was extracted with 2-Me THF (3×400 mL). The combined organic layer was washed with 0.5 N aqueous solution of HCl (3×300 mL), brine (3×250 mL), dried over anhydrous $Na_2SO_4$, filtered and concentrated by evaporation under reduced pressure. It was then solubilized twice in dichloromethane (2×300 mL) and the volatiles were removed by evaporation under reduced pressure to provide as a brown foam residue, N'-[2-benzyloxy-2-(trifluoromethyl)hex-5-enoyl]-6-hydroxy-3-nitro-5-(trifluoromethyl)pyridine-2-carbohydrazide (58.5 g, 94%). ESI-MS m/z calc. 536.11304, found 537.2 $(M+1)^+$. Retention time: 2.03 minutes (LC Method E).

Step 2: [6-[5-[1-Benzyloxy-1-(trifluoromethyl)pent-4-enyl]-1,3,4-oxadiazol-2-yl]-5-nitro-3-(trifluoromethyl)-2-pyridyl]trifluoromethanesulfonate

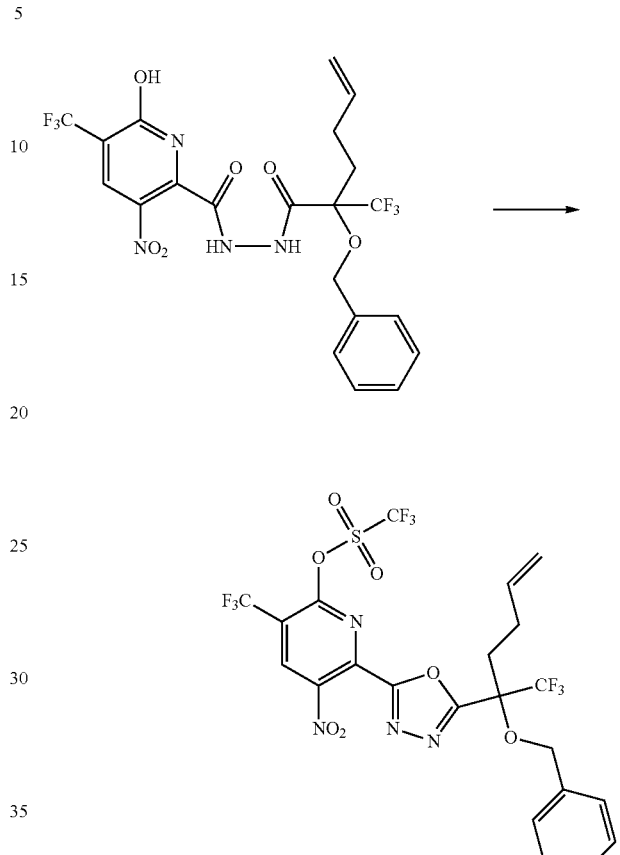

To a 0° C. solution of N'-[2-benzyloxy-2-(trifluoromethyl)hex-5-enoyl]-6-hydroxy-3-nitro-5-(trifluoromethyl) pyridine-2-carbohydrazide (9.76 g, 16.922 mmol) in dichloromethane (190 mL) was added DIPEA (8.0136 g, 10.8 mL, 62.004 mmol) followed by trifluoromethylsulfonyl trifluoromethanesulfonate (12.410 g, 7.4 mL, 43.985 mmol). The ice-cold bath was removed after 20 min and the reaction was stirred at room temperature for 2.5 hours. The mixture was transferred to a separatory funnel provided with ice-cold aqueous 1.0 N solution of HCl, and EtOAc (300 mL). The organic layer was separated, and the aqueous phase extracted with ethyl acetate (2×150 mL). The combined organic layer was washed again with ice-cold HCl 1.0 N aqueous solution (60 mL) and brine (3×40 mL), dried over anhydrous $Na_2SO_4$, filtered and concentrated under reduced pressure. Purification by silica gel chromatography (0% to 10% EtOAc in heptanes) provided as an orange oil, [6-[5-[1-benzyloxy-1-(trifluoromethyl)pent-4-enyl]-1,3,4-oxadiazol-2-yl]-5-nitro-3-(trifluoromethyl)-2-pyridyl] trifluoromethanesulfonate (5.334 g, 40%). $^1$H NMR (300 MHz, $CDCl_3$) δ 8.74 (s, 1H), 7.50-7.27 (m, 5H), 5.87-5.68 (m, 1H), 5.12-4.96 (m, 2H), 4.88 (d, J=10.6 Hz, 1H), 4.67 (d, J=10.9 Hz, 1H), 2.60-2.16 (m, 4H) ppm. $^{19}$F NMR (282 MHz, $CDCl_3$) δ −62.68 (s, 3F), −71.80 (s, 3F), −73.04 (s, 3F) ppm. ESI-MS m/z calc. 650.0518, found 651.1 $(M+1)^+$; Retention time: 3.94 minutes (LC Method C).

Intermediate 14: Preparation of 6-chloro-3-nitro-5-(trifluoromethyl)pyridine-2-carboxylic Acid

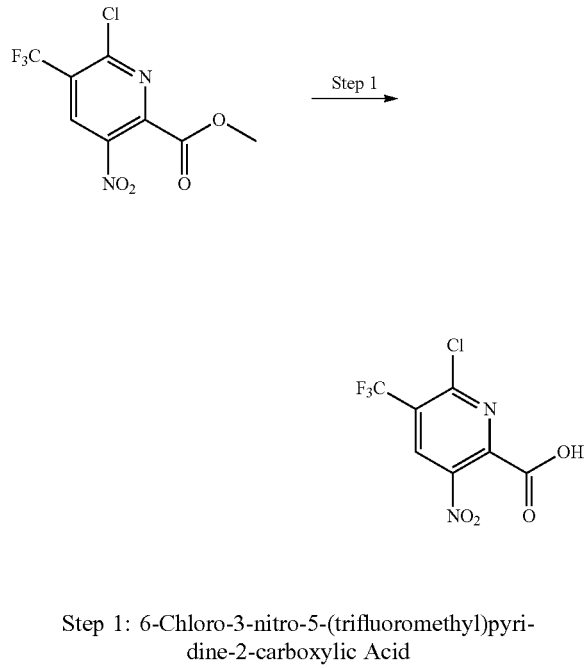

Step 1: 6-Chloro-3-nitro-5-(trifluoromethyl)pyridine-2-carboxylic Acid

To a solution of methyl 6-chloro-3-nitro-5-(trifluoromethyl)pyridine-2-carboxylate (1.14 g, 4.006 mmol) in THF (48.51 mL) and water (24.26 mL) at 0° C. was added lithium hydroxide monohydrate (201.7 mg, 4.807 mmol). The reaction was allowed to warm to room temperature then stirred for 2 hours. Acidified the solution to pH ~2-3 by the addition of 1N HCl then extracted with EtOAc. The organic phase was washed with water and brine, then dried over sodium sulfate, filtered and concentrated to give as a clear syrup, 6-chloro-3-nitro-5-(trifluoromethyl)pyridine-2-carboxylic acid (1.05 g, 97%). ESI-MS m/z calc. 269.9655, found 271.0 (M+1)+; Retention time: 0.37 minutes (LC Method S).

Intermediate 15: Preparation of tert-butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate

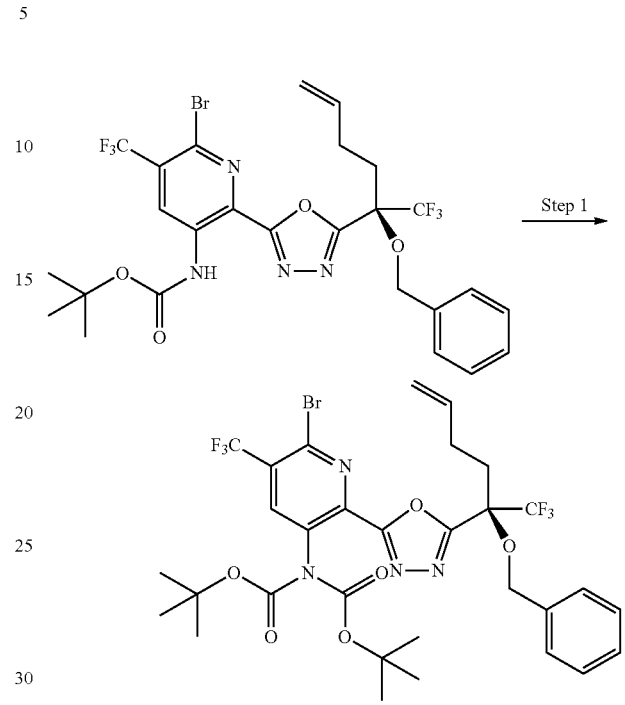

Step 1: tert-Butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate

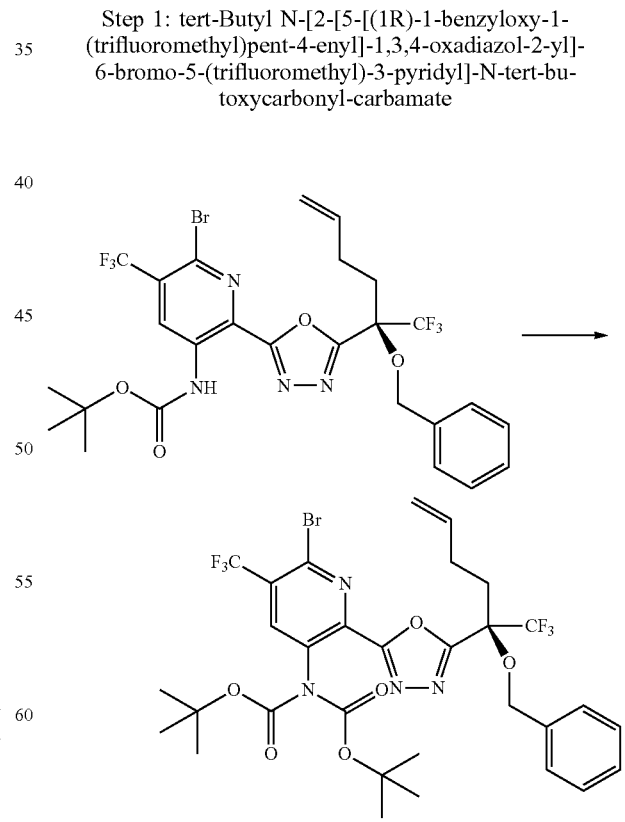

To a solution of tert-butyl N-[2-[5-[(1R)-1-benzyloxy-1-(trifluoromethyl)pent-4-enyl]-1,3,4-oxadiazol-2-yl]-6- bromo-5-(trifluoromethyl)-3-pyridyl]carbamate (222 g, 340.8 mmol) in MTBE (1.333 L) was added DIPEA (65.3 mL, 374.9 mmol) followed DMAP (2.09 g, 17.11 mmol). Added a solution of di-tert-butyl dicarbonate (111.6 g, 511.3 mmol) in MTBE (250 mL) over 8 minutes (no exotherm), and the reaction was stirred for additional 30 min. Added 1 L of water and separated the layers. The organic layer was washed with KHSO$_4$ (886 mL of 0.5 M, 443.0 mmol), 300 mL brine, dried with MgSO$_4$ and most (>95%) of the MTBE was evaporated by rotary evaporation at 45° C., leaving a thick oil. Added 1.125 L of heptane, spun in the 45° C. rotovap bath until dissolved, then evaporated out 325 mL of solvent by rotary evaporation. The rotovap bath temp was allowed to drop to room temperature and product started crystallizing out during the evaporation. Then put the flask in a −20° C. freezer overnight. The resultant solid was filtered and washed with cold heptane and dried at room temperature for 3 days to give tert-butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate (240.8 g, 94%). $^1$H NMR (400 MHz, Chloroform-d) δ 7.95 (s, 1H), 7.52-7.45 (m, 2H), 7.44-7.36 (m, 2H), 7.36-7.29 (m, 1H), 5.83-5.67 (m, 1H), 5.08-5.00 (m, 1H), 5.00-4.94 (m, 1H), 4.79 (d, J=10.4 Hz, 1H), 4.64 (d, J=10.4 Hz, 1H), 2.57-2.26 (m, 3H), 2.26-2.12 (m, 1H), 1.41 (s, 18H) ppm. ESI-MS m/z calc. 750.14874, found 751.1 (M+1)$^+$; Retention time: 3.76 minutes (LC Method D).

Intermediate 16: Preparation of (2R)-2-benzyloxy-2-(trifluoromethyl)pent-4-enehydrazide and (2S)-2-benzyloxy-2-(trifluoromethyl)pent-4-enehydrazide

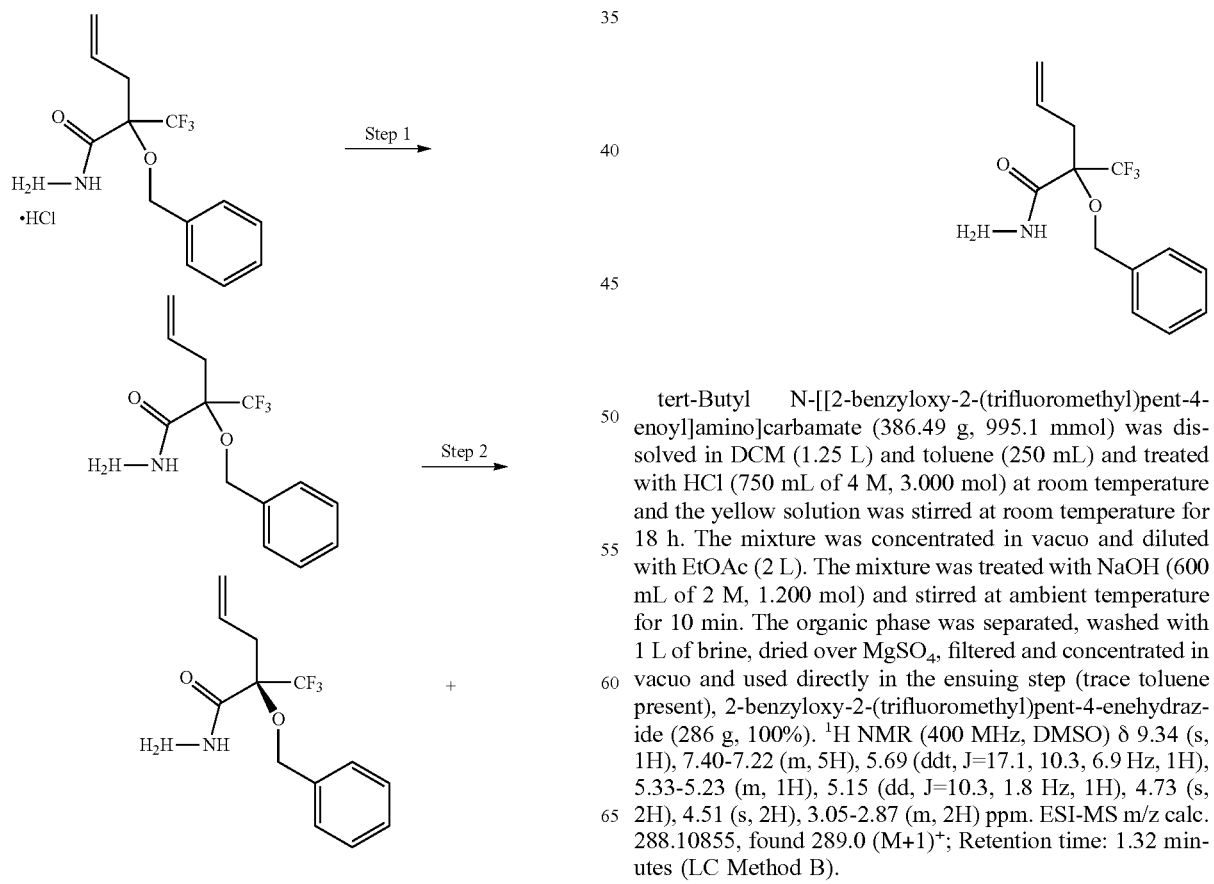

Step 1:
2-Benzyloxy-2-(trifluoromethyl)pent-4-enehydrazide

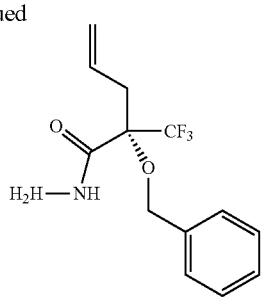

tert-Butyl N-[[2-benzyloxy-2-(trifluoromethyl)pent-4-enoyl]amino]carbamate (386.49 g, 995.1 mmol) was dissolved in DCM (1.25 L) and toluene (250 mL) and treated with HCl (750 mL of 4 M, 3.000 mol) at room temperature and the yellow solution was stirred at room temperature for 18 h. The mixture was concentrated in vacuo and diluted with EtOAc (2 L). The mixture was treated with NaOH (600 mL of 2 M, 1.200 mol) and stirred at ambient temperature for 10 min. The organic phase was separated, washed with 1 L of brine, dried over MgSO$_4$, filtered and concentrated in vacuo and used directly in the ensuing step (trace toluene present), 2-benzyloxy-2-(trifluoromethyl)pent-4-enehydrazide (286 g, 100%). $^1$H NMR (400 MHz, DMSO) δ 9.34 (s, 1H), 7.40-7.22 (m, 5H), 5.69 (ddt, J=17.1, 10.3, 6.9 Hz, 1H), 5.33-5.23 (m, 1H), 5.15 (dd, J=10.3, 1.8 Hz, 1H), 4.73 (s, 2H), 4.51 (s, 2H), 3.05-2.87 (m, 2H) ppm. ESI-MS m/z calc. 288.10855, found 289.0 (M+1)$^+$; Retention time: 1.32 minutes (LC Method B).

Step 2: (2R)-2-Benzyloxy-2-(trifluoromethyl)pent-4-enehydrazide and (2S)-2-benzyloxy-2-(trifluoromethyl)pent-4-enehydrazide

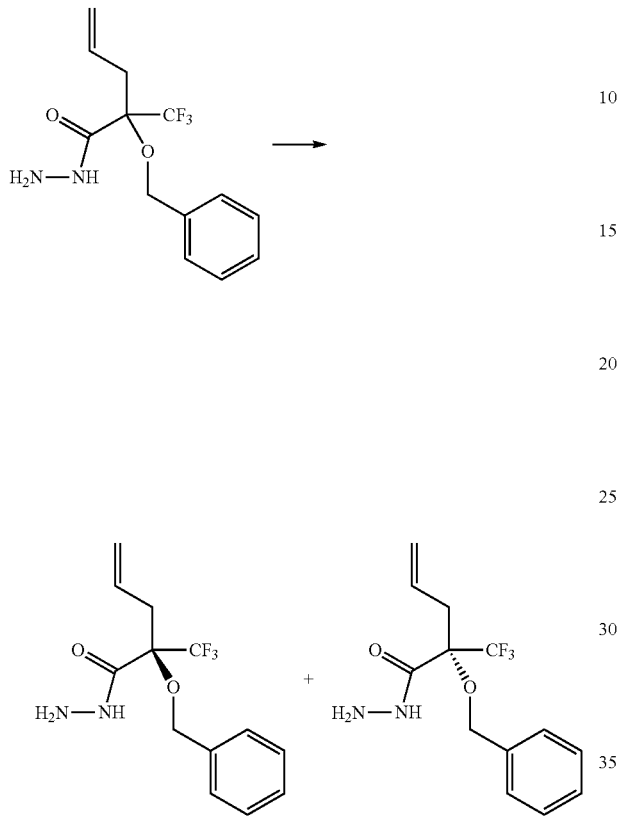

Racemic 2-benzyloxy-2-(trifluoromethyl)pent-4-enehydrazide (5.0 g, 17.35 mmol) was separated by chiral SFC using a ChiralPak IG column (250×21.2 mm; 5 μm) at 40° C. using a mobile phase of 7% MeOH (plus 20 mM NH$_3$)/93% CO$_2$ at a 70 mL/min flow and concentration of the sample was 111 mg/mL in methanol (no modifier), injection volume=160 μL with an outlet pressure of 136 bar, detection wavelength of 210 nm providing two single enantiomer products:

The first enantiomer to elute was isolated as (2S)-2-benzyloxy-2-(trifluoromethyl)pent-4-enehydrazide (1.79 g, 72%). $^1$H NMR (400 MHz, DMSO-d6) δ 9.31 (s, 1H), 7.45-7.39 (m, 2H), 7.38-7.26 (m, 3H), 5.77-5.62 (m, 1H), 5.28 (dq, J=17.1, 1.6 Hz, 1H), 5.15 (dq, J=10.2, 1.3 Hz, 1H), 4.72 (s, 2H), 4.44 (d, J=4.2 Hz, 2H), 2.99 (dd, J 7.4, 1.3 Hz, 1H), 2.91 (dd, J=15.4, 6.4 Hz, 1H) ppm. ESI-MS m/z calc. 288.10855, found 289.2 (M+1)$^+$; Retention time: 1.28 minutes (LC Method J).

The second enantiomer to elute was isolated as (2R)-2-benzyloxy-2-(trifluoromethyl)pent-4-enehydrazide (1.7 g, 68%) as a white solid. $^1$H NMR (400 MHz, DMSO-d6) δ 9.31 (s, 1H), 7.48-7.39 (m, 2H), 7.39-7.25 (m, 3H), 5.77-5.62 (m, 1H), 5.28 (dq, J 17.1, 1.6 Hz, 1H), 5.15 (dq, J 10.2, 1.5 Hz, 1H), 4.73 (s, 2H), 4.51 (s, 2H), 3.00 (dd, J=15.3, 7.5 Hz, 1H), 2.91 (dd, J=15.3, 6.4 Hz, 1H) ppm. ESI-MS m/z calc. 288.10855, found 289.2 (M+1)$^+$; Retention time: 1.28 minutes (LC Method J).

Intermediate 17: Preparation of [6-[5-[1-benzyloxy-1-(trifluoromethyl)but-3-enyl]-1,3,4-oxadiazol-2-yl]-5-nitro-3-(trifluoromethyl)-2-pyridyl]trifluoromethanesulfonate

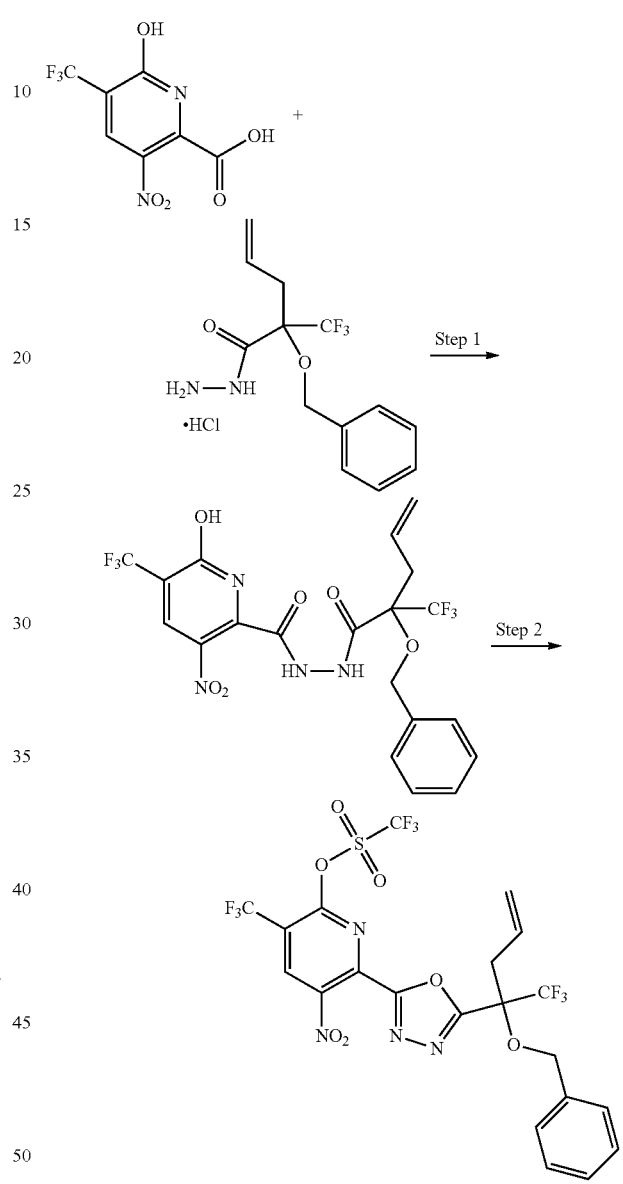

Step 1: N'-[2-Benzyloxy-2-(trifluoromethyl)pent-4-enoyl]-6-hydroxy-3-nitro-5-(trifluoromethyl)pyridine-2-carbohydrazide

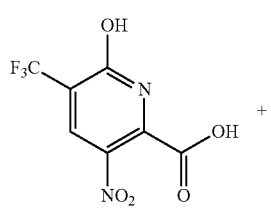

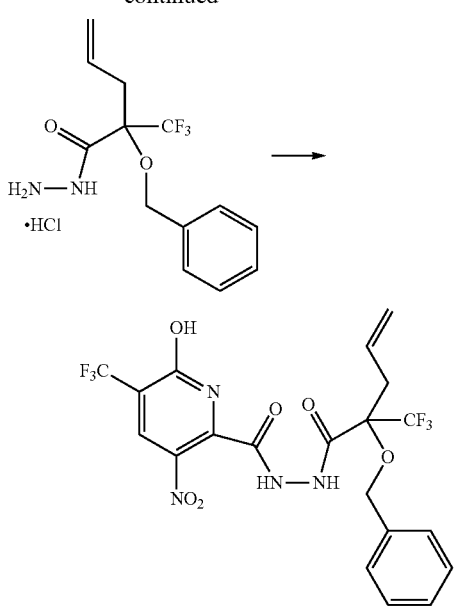

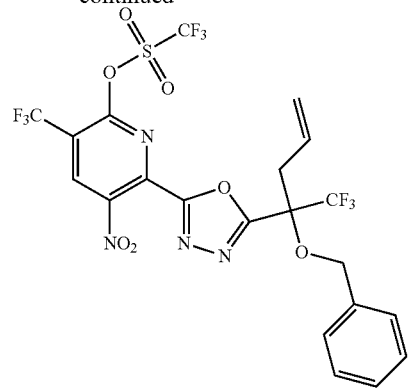

To a solution of 6-hydroxy-3-nitro-5-(trifluoromethyl)pyridine-2-carboxylic acid (8.5 g, 29.165 mmol) in acetonitrile (90 mL) and DMF (18 mL) was added CDI (5 g, 30.836 mmol). The mixture was stirred for 0.5 h at room temperature, then 2-benzyloxy-2-(trifluoromethyl)pent-4-enehydrazide (hydrochloride salt) (9 g, 27.716 mmol) was added. The reaction mixture was stirred at room temperature overnight. The reaction mixture was transferred to an extraction funnel rinsing with water (300 mL) and 2-Me THF (400 mL). The mixture was extracted with 2-methyl tetrahydrofuran (3×400 mL). The combined organic layer was washed with 0.5 N aqueous solution of HCl (3×300 mL), brine (3×250 mL), dried over anhydrous Na$_2$SO$_4$, filtered and concentrated under reduced pressure. It was then solubilized twice in dichloromethane (2×300 mL) and the volatiles were removed under reduced pressure giving N'-[2-benzyloxy-2-(trifluoromethyl)pent-4-enoyl]-6-hydroxy-3-nitro-5-(trifluoromethyl)pyridine-2-carbohydrazide (14.7 g, 75%) as yellow solid. ESI-MS m/z calc. 522.0974, found 523.1 (M+1)$^+$; Retention time: 2.08 minutes (LC Method E).

Step 2: [6-[5-[1-Benzyloxy-1-(trifluoromethyl)but-3-enyl]-1,3,4-oxadiazol-2-yl]-5-nitro-3-(trifluoromethyl)-2-pyridyl]trifluoromethanesulfonate Trifluoromethylsulfonyl trifluoromethanesulfonate (14.758 g, 8.8 mL, 52.308 mmol) was added to N'-[2-benzyloxy-2-(trifluoromethyl)pent-4-enoyl]-6-hydroxy-3-nitro-5-(trifluoromethyl)pyridine-2-carbohydrazide (14.7 g, 20.712 mmol) and DIPEA (9.79 g, 13.2 mL, 75.783 mmol) in dichloromethane (175 mL) at 0° C. The ice-cold bath was removed after 20 min and the reaction was stirred at room temperature for 2.5 h. The mixture was transferred to a separatory funnel with ice-cold aqueous 1.0 N solution of HCl (180 mL), and EtOAc (500 mL). The organic layer was separated, and the aqueous phase extracted with ethyl acetate (2×120 mL). The combined organic layer was washed again with ice-cold HCl 1.0 N aqueous solution (120 mL) and brine (3×120 mL), dried over anhydrous Na$_2$SO$_4$, filtered and concentrated by evaporation under reduced pressure. Purification by silica gel chromatography (0% to 20% of ethyl acetate in heptanes) provided [6-[5-[1-benzyloxy-1-(trifluoromethyl)but-3-enyl]-1,3,4-oxadiazol-2-yl]-5-nitro-3-(trifluoromethyl)-2-pyridyl]trifluoromethanesulfonate (5.425 g, 40%) as an orange viscous oil. $^1$H NMR (300 MHz, CDCl$_3$) δ 8.65 (s, 1H), 7.36-7.21 (m, 5H), 5.93-5.74 (m, 1H), 5.28-5.10 (m, 2H), 4.78 (d, J=10.9 Hz, 1H), 4.60 (d, J=10.6 Hz, 1H), 3.21-3.05 (m, 2H) ppm. $^{19}$F NMR (282 MHz, CDCl$_3$) δ −62.69 (s, 3F), −71.82 (s, 3F), −73.32 (s, 3F) ppm. ESI-MS m/z calc. 636.03613, found 637.1 (M+1)$^+$; Retention time: 4.0 minutes (LC Method C).

Intermediate 18: Preparation of (2R)-2-benzyloxy-2-(trifluoromethyl)hex-5-enehydrazide

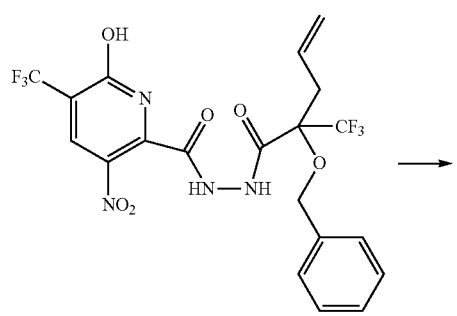

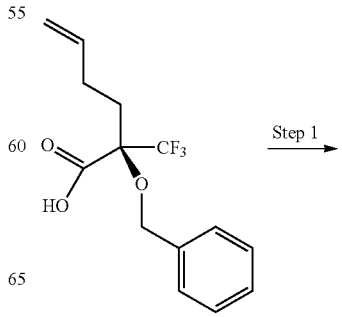

Step 1: tert-Butyl N-[[(2R)-2-benzyloxy-2-(trifluoromethyl)hex-5-enoyl]amino]carbamate

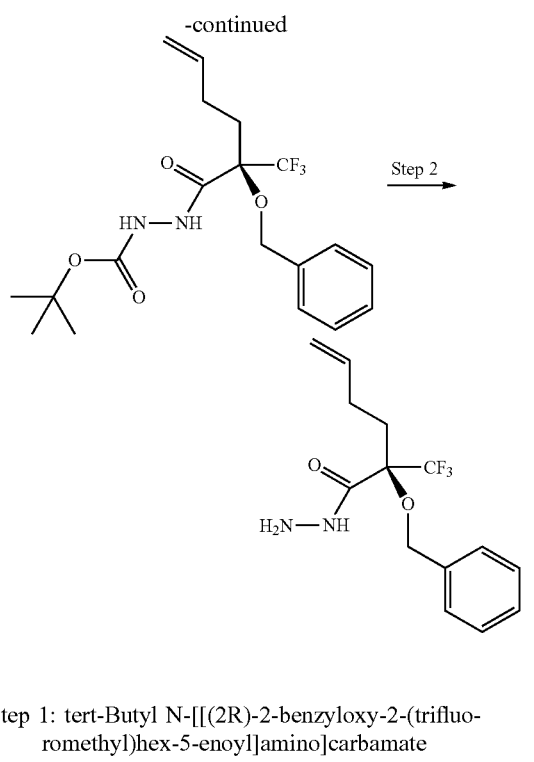

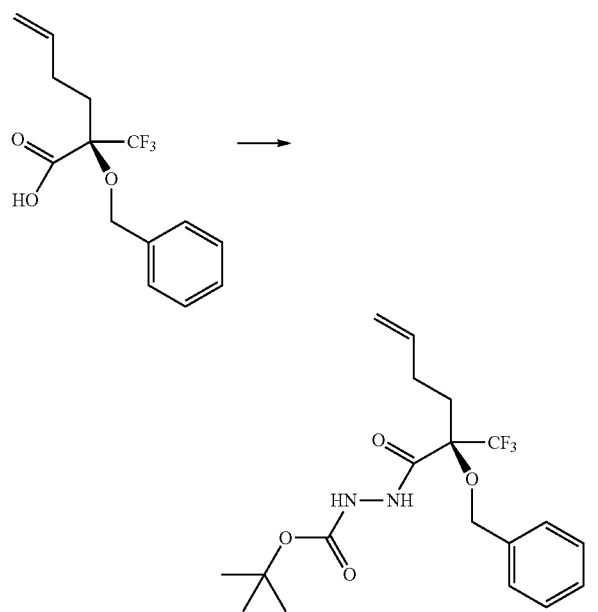

To a solution of (2R)-2-benzyloxy-2-(trifluoromethyl)hex-5-enoic acid (365 g, 1.266 mol) in DMF (2 L) was added HATU (612 g, 1.610 mol) and DIEA (450 mL, 2.584 mol) and the mixture was stirred at ambient temperature for 10 min. To the mixture was added tert-butyl N-aminocarbamate (200 g, 1.513 mol) (slight exotherm upon addition) and the mixture was stirred at ambient temperature for 16 h. The reaction was poured into ice water (5 L). The resultant precipitate was collected by filtration and washed with water. The solid was dissolved in EtOAc (2 L) and washed with brine. The organic phase was dried over MgSO$_4$, filtered and concentrated in vacuo. The oil was diluted with EtOAc (500 mL) followed by heptane (3 L) and stirred at ambient temperature for several hours affording a thick slurry. The slurry was diluted with additional heptane and filtered to collect fluffy white solid (343 g). The filtrate was concentrated and purification by silica gel chromatography (0-40% EtOAc/hexanes) provided tert-butyl N-[[(2R)-2-benzyloxy-2-(trifluoromethyl)hex-5-enoyl]amino]carbamate (464 g, 91%, combined with product from crystallization). ESI-MS m/z calc. 402.17664, found 303.0 (M+1-Boc)$^+$; Retention time: 2.68 minutes (LC Method D).

Step 2: (2R)-2-Benzyloxy-2-(trifluoromethyl)hex-5-enehydrazide

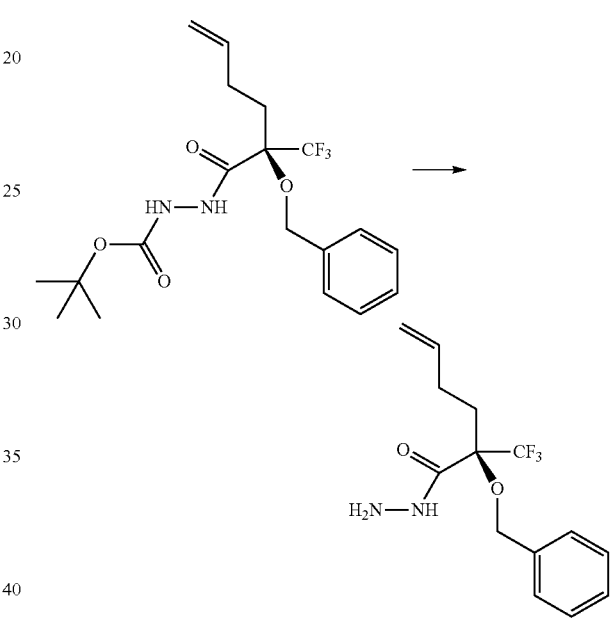

To a solution of tert-butyl N-[[(2R)-2-benzyloxy-2-(trifluoromethyl)hex-5-enoyl]amino]carbamate (464 g, 1.153 mol) in DCM (1.25 L) and was added HCl (925 mL of 4 M, 3.700 mol) and the mixture stirred at ambient temperature for 20 h. The mixture was concentrated in vacuo removing most of the DCM. The mixture was diluted with isopropyl acetate (1 L) and basified to pH=6 with NaOH (140 g of 50 w/w, 1.750 mol) in 1 L of ice water. The organic phase was separated and washed with 1 L of brine and the combined aqueous phases were extracted with isopropyl acetate (1 L). The combined organic phases were dried over MgSO$_4$, filtered and concentrated in vacuo affording a dark yellow oil. (2R)-2-benzyloxy-2-(trifluoromethyl)hex-5-enehydrazide (358 g, quant.) $^1$H NMR (400 MHz, CDCl$_3$) δ 8.02 (s, 1H), 7.44-7.29 (m, 5H), 5.81 (ddt, J=16.8, 10.1, 6.4 Hz, 1H), 5.13-4.93 (m, 2H), 4.75 (dd, J=10.5, 1.5 Hz, 1H), 4.61 (d, J=10.5 Hz, 1H), 3.78 (s, 2H), 2.43 (ddd, J=14.3, 11.0, 5.9 Hz, 1H), 2.26-1.95 (m, 3H) ppm. ESI-MS m/z calc. 302.1242, found 303.0 (M+1)$^+$; Retention time: 2.0 minutes (LC Method D).

Intermediate 19: Preparation of 2-[(1R)-1-benzyloxy-1-(trifluoromethyl)but-3-enyl]-5-[6-chloro-3-nitro-5-(trifluoromethyl)-2-pyridyl]-1,3,4-oxadiazole

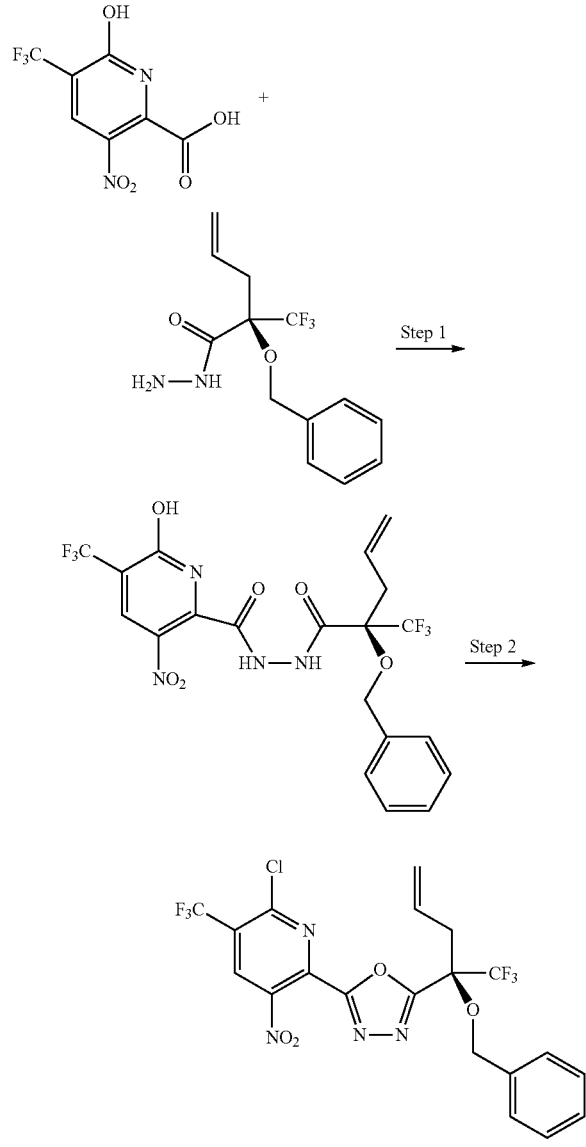

Step 1: N'-[(2R)-2-Benzyloxy-2-(trifluoromethyl)pent-4-enoyl]-6-hydroxy-3-nitro-5-(trifluoromethyl)pyridine-2-carbohydrazide

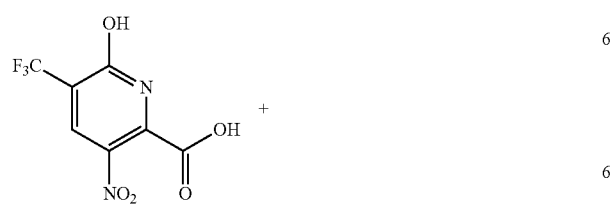

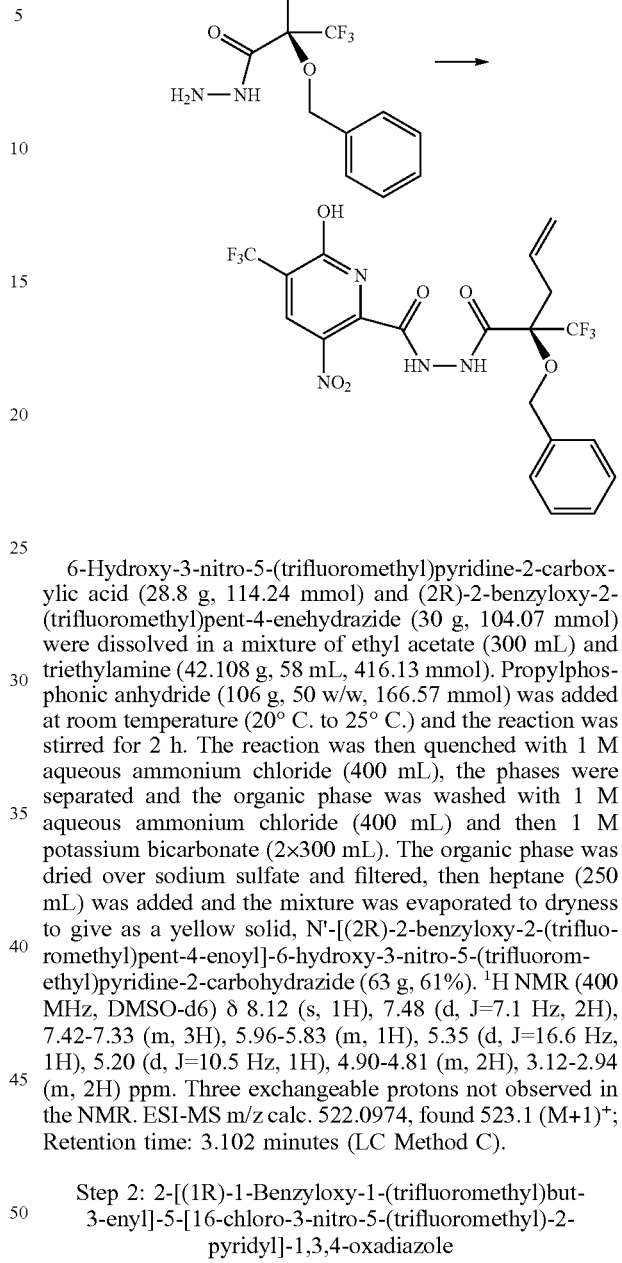

6-Hydroxy-3-nitro-5-(trifluoromethyl)pyridine-2-carboxylic acid (28.8 g, 114.24 mmol) and (2R)-2-benzyloxy-2-(trifluoromethyl)pent-4-enehydrazide (30 g, 104.07 mmol) were dissolved in a mixture of ethyl acetate (300 mL) and triethylamine (42.108 g, 58 mL, 416.13 mmol). Propylphosphonic anhydride (106 g, 50 w/w, 166.57 mmol) was added at room temperature (20° C. to 25° C.) and the reaction was stirred for 2 h. The reaction was then quenched with 1 M aqueous ammonium chloride (400 mL), the phases were separated and the organic phase was washed with 1 M aqueous ammonium chloride (400 mL) and then 1 M potassium bicarbonate (2×300 mL). The organic phase was dried over sodium sulfate and filtered, then heptane (250 mL) was added and the mixture was evaporated to dryness to give as a yellow solid, N'-[(2R)-2-benzyloxy-2-(trifluoromethyl)pent-4-enoyl]-6-hydroxy-3-nitro-5-(trifluoromethyl)pyridine-2-carbohydrazide (63 g, 61%). $^1$H NMR (400 MHz, DMSO-d6) δ 8.12 (s, 1H), 7.48 (d, J=7.1 Hz, 2H), 7.42-7.33 (m, 3H), 5.96-5.83 (m, 1H), 5.35 (d, J=16.6 Hz, 1H), 5.20 (d, J=10.5 Hz, 1H), 4.90-4.81 (m, 2H), 3.12-2.94 (m, 2H) ppm. Three exchangeable protons not observed in the NMR. ESI-MS m/z calc. 522.0974, found 523.1 (M+1)$^+$; Retention time: 3.102 minutes (LC Method C).

Step 2: 2-[(1R)-1-Benzyloxy-1-(trifluoromethyl)but-3-enyl]-5-[16-chloro-3-nitro-5-(trifluoromethyl)-2-pyridyl]-1,3,4-oxadiazole

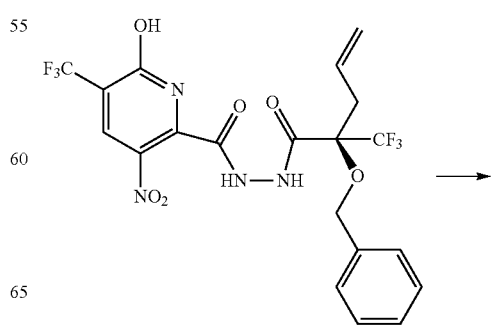

-continued

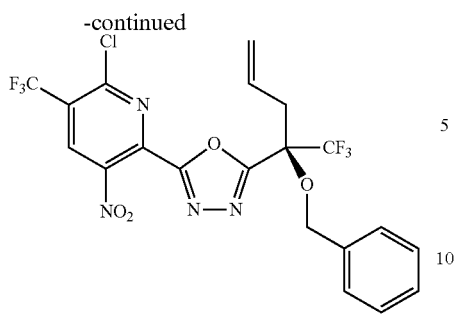

N'-[(2R)-2-Benzyloxy-2-(trifluoromethyl)pent-4-enoyl]-6-hydroxy-3-nitro-5-(trifluoromethyl)pyridine-2-carbohydrazide (45 g, 80.979 mmol) was dissolved in a mixture of phosphoryl trichloride (90 mL) and acetonitrile (90 mL) and dimethylformamide (45 mL) was added. The mixture was heated at 70° C. for 2 h. The reaction was then quenched with a 1 M aqueous potassium bicarbonate solution (1.3 L) while monitoring the pH and adjusting with 6 M sodium hydroxide (300 mL). The product was then extracted with ethyl acetate (3×500 mL). The organic phases were combined and dried over sodium sulfate (150 g), then filtered and concentrated. The product was then dry packed using 125 g of silica gel and purified on a 600 g silica pad, eluting with heptanes (2 L) and then 10% MTBE in heptanes (8 L) giving some pure product and some contaminated product. This contaminated product was dry packed using 50 g of silica and purified on a 400 g silica pad eluting with heptanes (1 L) and then 10% MTBE in heptanes (6 L) again giving pure product and some contaminated product. This contaminated product was further purified by reverse phase chromatography using a 100 g C$_{18}$ column and eluting with a gradient from 0.1% aqueous formic acid to methanol (product elutes at ~80% methanol). The fractions containing the product were combined, the methanol evaporated under vacuum and then the aqueous solution was extracted with ethyl acetate (2×50 mL). The organic phase was dried over sodium sulfate, filtered and then evaporated to dryness to give more desired pure product. All the lots of the desired product from each purification were combined to give as a light yellow oil, 2-[(1R)-1-benzyloxy-1-(trifluoromethyl)but-3-enyl]-5-[6-chloro-3-nitro-5-(trifluoromethyl)-2-pyridyl]-1,3,4-oxadiazole (13.5 g, 30%). $^1$H NMR (400 MHz, DMSO-d6) δ 9.26 (s, 1H), 7.46-7.31 (m, 5H), 5.92 (dd, J=16.9, 9.5 Hz, 1H), 5.39 (d, J=16.6 Hz, 1H), 5.26 (d, J=10.3 Hz, 1H), 4.79 (d, J=10.8 Hz, 1H), 4.63 (d, J=10.8 Hz, 1H), 3.31 (d, J=6.8 Hz, 2H) ppm. ESI-MS m/z calc. 522.053, found 523.0 (M+1)$^+$; Retention time: 3.784 minutes (LC Method C).

Intermediate 20: Preparation of methyl 6-chloro-5-(difluoromethyl)-3-nitro-pyridine-2-carboxylate

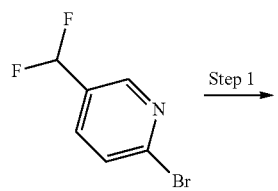

Step 1

-continued

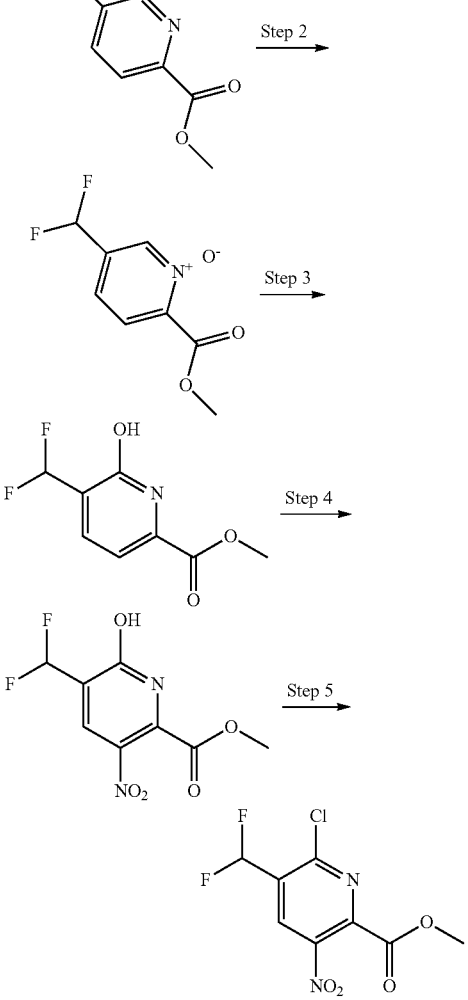

Step 1: Methyl 5-(difluoromethyl)pyridine-2-carboxylate

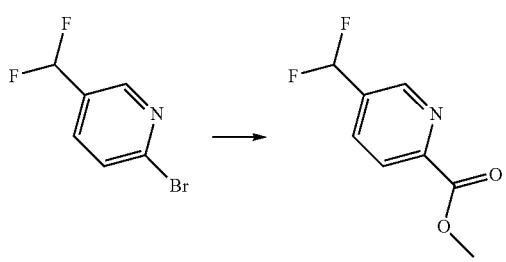

In an autoclave was added 2-bromo-5-(difluoromethyl)pyridine (25 g, 120.19 mmol), methanol (250 mL), triethylamine (29.04 g, 40 mL, 286.98 mmol) and [1,1'-bis(diphenylphosphino)ferrocene]dichloropalladium(II) (2.6 g, 3.5533 mmol). The autoclave was purged with nitrogen, then with carbon monoxide. The mixture was heated at 130° C. and the carbon monoxide pressure was adjusted to 120 psi. The mixture was stirred for 3 h at 130° C., then cooled to 25° C. The mixture was purged with nitrogen and concentrated under vacuum. The resulting solid was diluted with ethyl acetate (500 mL) then water (200 mL) and sodium carbonate (20 g) were added. The mixture was vigorously stirred for 10 minutes and the layers were separated. The organic layer was washed with water (200 mL) and brine (200 mL), dried over sodium sulfate, filtered and evaporated under reduced pressure. The residue was purified by silica gel chromatography using a gradient from 20% to 50% ethyl acetate in heptanes to afford as an off-white solid, methyl 5-(difluoromethyl)pyridine-2-carboxylate (11.41 g, 51%). ESI-MS m/z calc. 187.0445, found 188.2 (M+1)+; Retention time: 1.48 minutes (LC Method E).

Step 2: Methyl 5-(difluoromethyl)-1-oxido-pyridin-1-ium-2-carboxylate

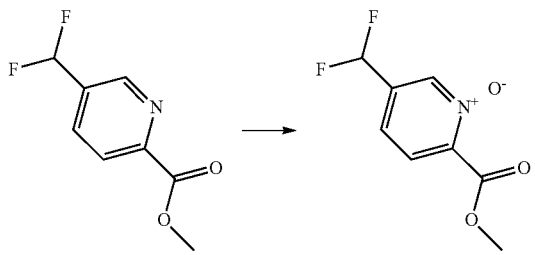

Urea hydrogen peroxide (13.7 g, 145.64 mmol) was added to a solution of methyl 5-(difluoromethyl)pyridine-2-carboxylate (8.1 g, 43.282 mmol) in DCE (70 mL). Trifluoroacetic anhydride (24.025 g, 15.9 mL, 114.39 mmol) was added over 20 minutes at a temperature of −10° C. in cooling bath (CO$_2$/acetone bath). The reaction mixture was stirred for a further 30 minutes at 0° C. and then for 1 hour at ambient temperature. The reaction mixture was poured into ice-water (150 mL) and adjusted to pH=2 to 3 with ~150 mL of 1 N aqueous sodium hydroxide solution. The mixture was diluted with dichloromethane (200 mL) and the layers were separated. The aqueous phase was extracted with dichloromethane (2×150 mL). The combined organic phases were washed with brine (150 mL), dried over anhydrous sodium sulfate, filtered and concentrated under reduced pressure to give as a yellow solid, methyl 5-(difluoromethyl)-1-oxido-pyridin-1-ium-2-carboxylate (8.39 g, 87%). $^1$H NMR (400 MHz, Chloroform-d) δ 8.41 (s, 1H), 7.72 (d, J=8.1 Hz, 1H), 7.43-7.36 (m, 1H), 6.84-6.47 (m, 1H), 4.03 (s, 3H) ppm. $^{19}$F NMR (377 MHz, Chloroform-d) δ−115.27 (d, J=55.9 Hz, 2F) ppm. ESI-MS m/z calc. 203.0394, found 204.1 (M+1)+; Retention time: 0.73 minutes (LC Method E).

Step 3: Methyl 5-(difluoromethyl)-6-hydroxy-pyridine-2-carboxylate

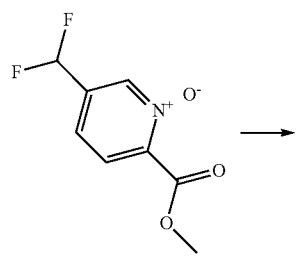

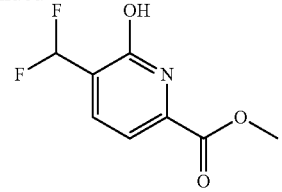

Trifluoroacetic anhydride (84.616 g, 56 mL, 402.87 mmol) was added dropwise to a mixture of methyl 5-(difluoromethyl)-1-oxido-pyridin-1-ium-2-carboxylate (11.63 g, 47.060 mmol) in DMF (130 mL) at 0° C. over 30 minutes. The mixture was stirred at 48° C. for 4 h, then the reaction was stirred at room temperature overnight. The reaction mixture was concentrated under reduced pressure to remove trifluoroacetic anhydride. The residual DMF solution was poured over 30 minutes into water (1 L) at 0° C. The precipitated solid was collected by filtration and washed with water (200 mL). The solid was dried under vacuum to give as an off-white solid, methyl 5-(difluoromethyl)-6-hydroxy-pyridine-2-carboxylate (5.74 g, 60%). $^1$H NMR (400 MHz, DMSO-d6) δ 12.29 (br. s., 1H), 7.88 (d, J=7.3 Hz, 1H), 7.13 (s, 1H), 7.07-6.76 (m, 1H), 3.87 (s, 3H) ppm. $^{19}$F NMR (377 MHz, DMSO-d6) δ−118.60 (br. s., 2F) ppm. ESI-MS m/z calc. 203.0394, found 204.1 (M+1)+; Retention time: 1.34 minutes (LC Method E).

Step 4: Methyl 5-(difluoromethyl)-6-hydroxy-3-nitro-pyridine-2-carboxylate

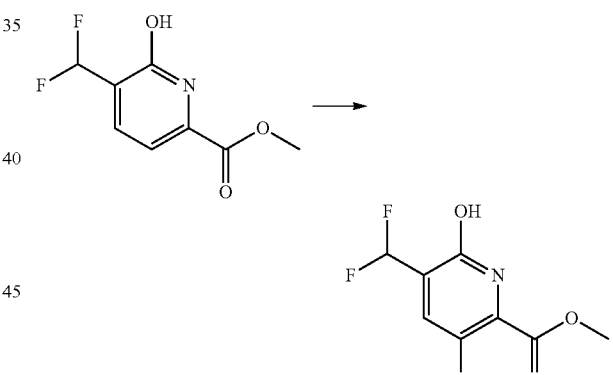

To an ice-cooled solution of methyl 5-(difluoromethyl)-6-hydroxy-pyridine-2-carboxylate (7.43 g, 36.575 mmol) in sulfuric acid (48 mL of 18.4 M, 883.2 mmol) was added nitric acid (2.5 mL of 15.8 M, 39.5 mmol) dropwise. After 5 min, the ice bath was removed, and the reaction mixture was stirred at 45° C. overnight. The reaction was precipitated in ice-water (300 mL). The solution was cooled at 0° C. for 15 minutes, then the solid was isolated by filtration and washed with water (200 mL). The solid was dried overnight under vacuum to give as an off-white solid, methyl 5-(difluoromethyl)-6-hydroxy-3-nitro-pyridine-2-carboxylate (5.47 g, 56%). $^1$H NMR (400 MHz, DMSO-d6) δ 8.41 (s, 1H), 7.19-6.75 (m, 1H), 3.94 (s, 3H) ppm. One exchangeable proton not observed in NMR. $^{19}$F NMR (377 MHz, DMSO-d6) δ−118.87 (d, J=54.5 Hz, 2F) ppm. ESI-MS m/z calc. 248.0245, found 249.1 (M+1)+; Retention time: 1.6 minutes (LC Method E).

Step 5: Methyl 6-chloro-5-(difluoromethyl)-3-nitro-pyridine-2-carboxylate

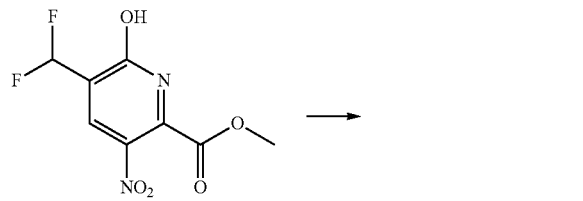

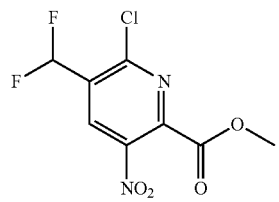

Methyl 5-(difluoromethyl)-6-hydroxy-3-nitro-pyridine-2-carboxylate (2 g, 8.06 mmol) was dissolved in a mixture of phosphoryl trichloride (6.58 g, 4 mL, 42.914 mmol) and acetonitrile (4 mL) at 0° C. (exothermic). DMF (1.888 g, 2 mL, 25.83 mmol) was added dropwise at 0° C. (exothermic). The resulting yellow milky mixture was stirred at 70° C. (pre-heated oil bath) for 4 h. More phosphoryl trichloride (3.29 g, 2 mL, 21.457 mmol) was added. The orange solution was stirred at 70° C. overnight. Cooled to 0° C. and methanol was added (30 mL). A 50% saturated solution of sodium bicarbonate (50 mL) was added dropwise at 0° C. A solution of potassium carbonate (10 g) in water (50 mL), methanol (50 mL) and ethyl acetate (150 mL) was added. The aqueous layer was separated and extracted with ethyl acetate (3×50 mL). The combined organic layers were washed with brine (50 mL), dried over anhydrous sodium sulfate, filtered and concentrated under vacuum to give an orange oil which was purified by silica gel chromatography using a gradient from 5% to 30% MTBE in heptanes to give as a yellow oil, methyl 6-chloro-5-(difluoromethyl)-3-nitro-pyridine-2-carboxylate (1.92 g, 79%). $^1$H NMR (400 MHz, Chloroform-d) δ 8.70 (s, 1H), 7.16-6.76 (m, 1H), 4.06 (s, 3H) ppm. $^{19}$F NMR (377 MHz, Chloroform-d) δ−117.39 (d, J=53.1 Hz, 2F) ppm. ESI-MS m/z calc. 265.9906, found 267.1 (M+1)$^+$; Retention time: 1.84 minutes (LC Method E).

Intermediate 21: Preparation of 2-methylhex-5-en-2-amine (hydrochloride salt)

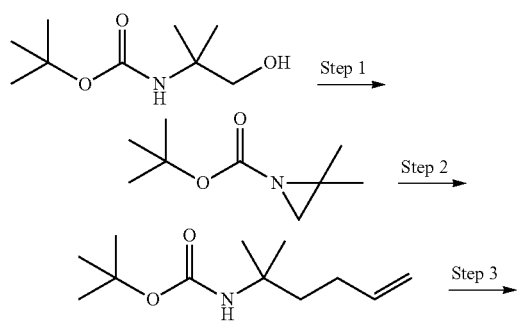

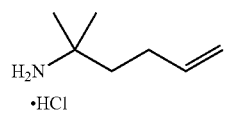

Step 1: tert-Butyl 2,2-dimethylaziridine-1-carboxylate

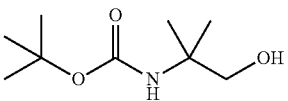

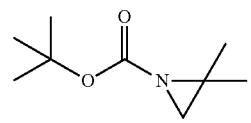

To a solution of tert-butyl N-(2-hydroxy-1,1-dimethyl-ethyl)carbamate (30 g, 155.35 mmol) in diethyl ether (750 mL) was added p-TsCl (35.6 g, 186.73 mmol) and powdered KOH (103 g, 1.5605 mol) at 0° C. The reaction temperature was raised to reflux temperature and stirred for 16 hours. Another portion of KOH (17 g, 303 mmol) was added and the reaction was refluxed for another 2 hours. The reaction was cooled to room temperature and diluted with ether (500 mL). The formed solid was removed by filtration through a glass fritted funnel and washed with more ether (100 mL). The combined ethereal filtrate was washed with water (100 mL) and brine (100 mL), dried over anhydrous magnesium sulfate, filtered and concentrated under reduced pressure to furnish as a clear oil, tert-butyl 2,2-dimethylaziridine-1-carboxylate (24.602 g, 88%). $^1$H NMR (500 MHz, Chloroform-d) δ 2.04 (s, 2H), 1.46 (s, 9H), 1.28 (s, 6H) ppm.

Step 2: tert-Butyl N-(1,1-dimethylpent-4-enyl)carbamate

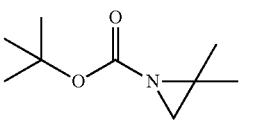

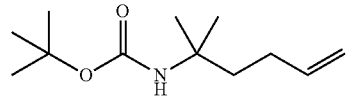

A reaction flask was charged with allyl(chloro)magnesium in THF (205 mL, 2 M, 410 mmol) and anhydrous THF (200 mL). The solution was cooled to −30° C. and copper(I) bromide (dimethyl sulfide complex) (28 g, 136.2 mmol) was added. The reaction mixture was stirred at the same temperature for 30 min, then cooled to −78° C. A solution of tert-butyl 2,2-dimethylaziridine-1-carboxylate (24.602 g, 136.49 mmol) in anhydrous THF (200 mL) was added to the reaction mixture dropwise. The reaction was stirred at the same temperature for 30 min, and then moved to a −20° C. freezer and stored for 3 hours. The reaction was quenched with a saturated aqueous ammonium chloride solution (200 mL) at 0° C. The reaction was stirred at room temperature for 10 minutes, then diluted with diethyl ether (200 mL). The solution was filtered through a pad of Celite and washed with ether (100 mL). The two layers were separated, and the aqueous layer was extracted with diethyl ether (2×200 mL). The combined organic layers were washed with brine (200 mL), dried over anhydrous magnesium sulfate and concentrated under vacuum. The residue was purified by silica gel chromatography using a gradient from 0% to 10% diethyl ether in hexanes to furnish as a light yellow liquid, tert-butyl N-(1,1-dimethylpent-4-enyl)carbamate (18.6 g, 61%). ¹H NMR (500 MHz, Chloroform-d) δ 5.82 (ddt, J=16.8, 10.2, 6.6, 6.6 Hz, 1H), 5.09-4.87 (m, 2H), 4.38 (s, 1H), 2.11-1.98 (m, 2H), 1.79-1.64 (m, 2H), 1.43 (s, 9H), 1.26 (s, 6H) ppm.

Step 3: 2-Methylhex-5-en-2-amine (hydrochloride salt)

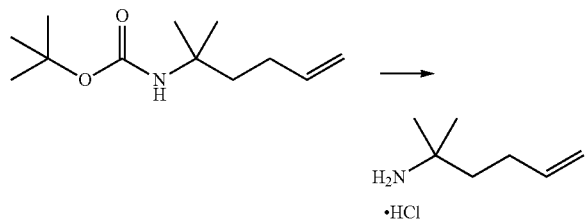

A solution of tert-butyl N-(1,1-dimethylpent-4-enyl)carbamate (26.6 g, 124.7 mmol) and HCl in diethyl ether (350 mL, 2 M, 700 mmol) was stirred at room temperature for 2 days. The solvent was removed and the residue was triturated with hexanes to furnish as a white solid, 2-methylhex-5-en-2-amine (hydrochloride salt) (15.198 g, 77%). ¹H NMR (500 MHz, DMSO-d6) δ 8.08 (s, 3H), 5.92-5.64 (m, 1H), 5.15-4.87 (m, 2H), 2.21-1.96 (m, 2H), 1.72-1.49 (m, 2H), 1.23 (s, 6H) ppm.

Preparation of Compounds 1-213 and Compounds 214 to 222

Example 1: Preparation of 20-amino-6,18-bis(trifluoromethyl)-22-oxa-3,4,16,21-tetraazatetracyclo[15.3.1.1²,⁵.0¹²,¹⁶]docosa-1(20),2,4,17(21),18-pentaen-6-ol (mixture of 4 stereoisomers) (Compound 1)

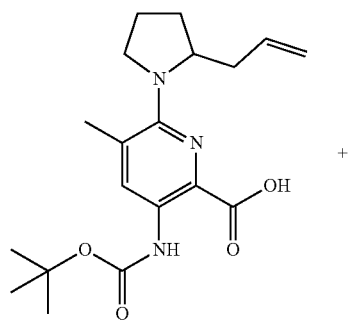

+

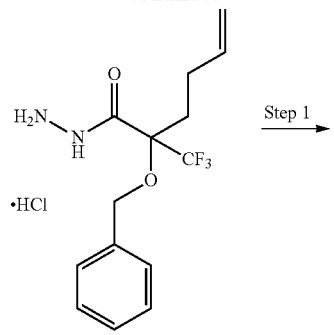

-continued

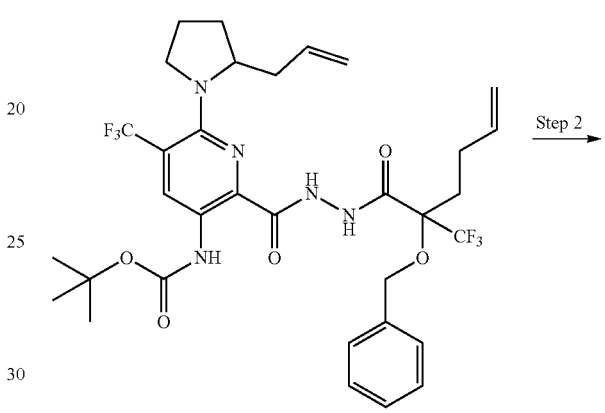

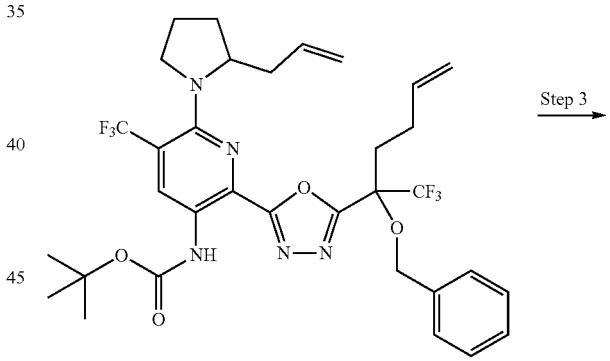

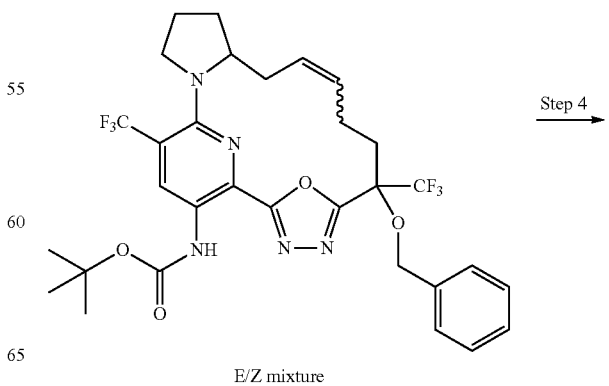

E/Z mixture

227

-continued

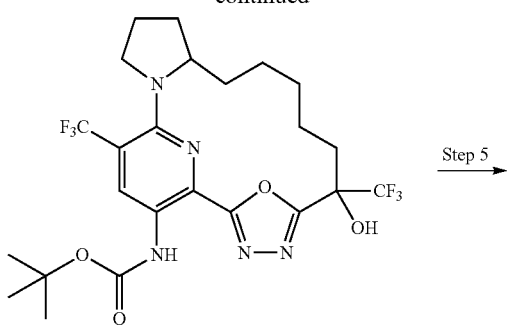

Step 5 →

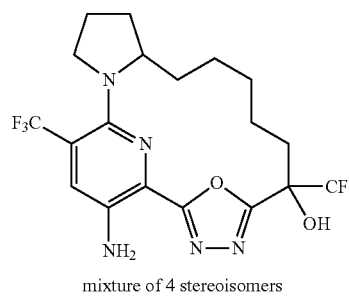

mixture of 4 stereoisomers

Step 1: tert-Butyl N-[6-(2-allylpyrrolidin-1-yl)-2-[[[2-benzyloxy-2-(trifluoromethyl)hex-5-enoyl]amino]carbamoyl]-5-(trifluoromethyl)-3-pyridyl]carbamate

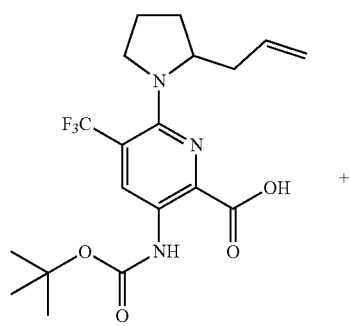 +

228

-continued

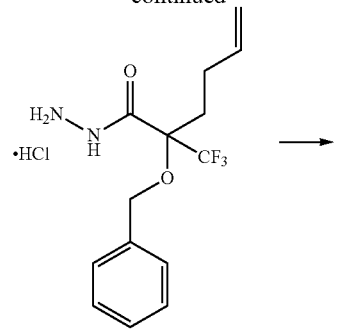

To a solution of 6-(2-allylpyrrolidin-1-yl)-3-(tert-butoxycarbonylamino)-5-(trifluoromethyl)pyridine-2-carboxylic acid (200 mg, 0.4815 mmol) in acetonitrile (5 mL) were added successively 2-benzyloxy-2-(trifluoromethyl)hex-5-enehydrazide (hydrochloride salt) (180 mg, 0.5314 mmol), 1-(3-dimethylaminopropyl)-3-ethylcarbodiimide (hydrochloride salt) (140 mg, 0.7303 mmol), 1-hydroxybenzotriazole (monohydrate) (100 mg, 0.653 mmol) and triethylamine (101.64 mg, 0.14 mL, 1.0044 mmol). The resulting mixture was stirred at room temperature overnight. The reaction mixture was diluted with ethyl acetate (50 mL) and washed with aqueous 1 N HCl (30 mL), saturated aqueous sodium bicarbonate (30 mL), brine (30 mL), dried over anhydrous sodium sulfate, filtered and concentrated. The residue was purified by silica gel chromatography using a gradient from 0% to 10% ethyl acetate in heptanes giving as yellow solid, tert-butyl N-[6-(2-allylpyrrolidin-1-yl)-2-[[[2-benzyloxy-2-(trifluoromethyl)hex-5-enoyl]amino]carbamoyl]-5-(trifluoromethyl)-3-pyridyl]carbamate (300 mg, 89%). $^1$H NMR (300 MHz, Chloroform-d) δ 1.51 (s, 9H), 1.65-1.81 (m, 2H), 1.88-2.00 (m, 1H), 2.07-2.34 (m, 5H), 2.37-2.59 (m, 2H), 3.27-3.43 (m, 1H), 3.56-3.71 (m, 1H), 4.25-4.40 (m, 1H), 4.66-4.77 (m, 1H), 4.78-4.91 (m, 1H), 4.93-5.19 (m, 4H), 5.69-5.91 (m, 2H), 7.32-7.51 (m, 5H), 9.01 (br. s., 1H), 9.16 (dd, J=18.8, 5.9 Hz, 1H), 9.85-10.01 (m, 1H), 10.05 (br. s., 1H) ppm. $^{19}$F NMR (282 MHz, Chloroform-d) δ −75.2 to −72.1 (m, 3F), −57.8 (d, J=9.2 Hz, 1F) ppm. Retention time: 2.82 minutes (LC Method B).

Step 2: tert-Butyl N-[6-(2-allylpyrrolidin-1-yl)-2-[5-[1-benzyloxy-1-(trifluoromethyl)pent-4-enyl]-1,3,4-oxadiazol-2-yl]-5-(trifluoromethyl)-3-pyridyl]carbamate

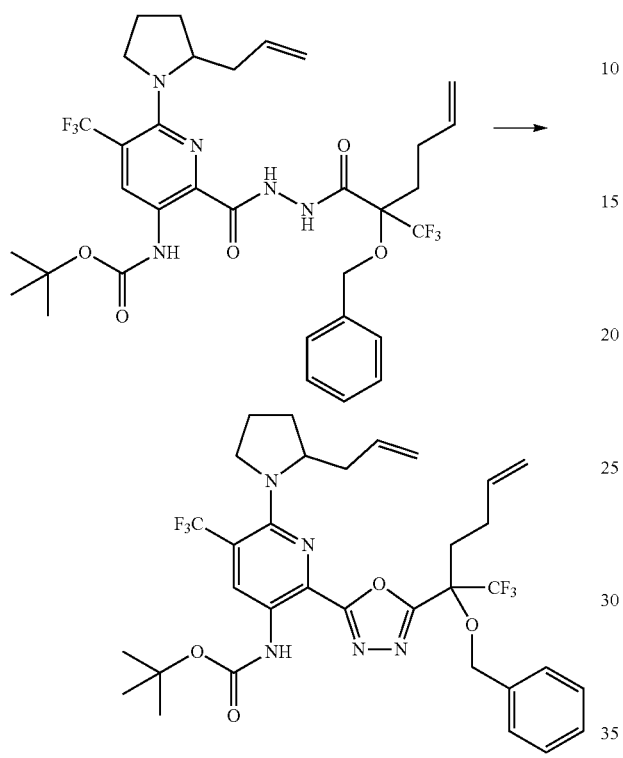

Step 3: tert-Butyl N-6-(benzyloxy)-6,18-bis(trifluoromethyl)-22-oxa-3,4,16,21-tetraazatetracyclo[15.3.1.1²,⁵.0¹²,¹⁶]docosa-1(21),2,4,9,17,19-hexaen-20-yl]carbamate (E/Z mixture)

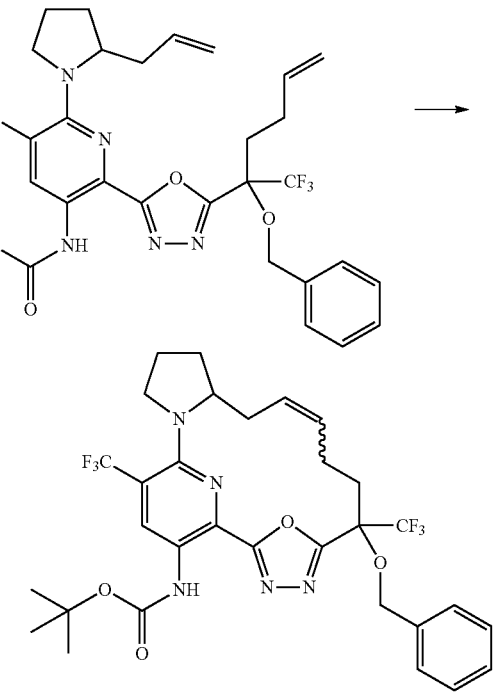

E/Z mixture

A solution of tert-butyl N-[6-(2-allylpyrrolidin-1-yl)-2-[[[2-benzyloxy-2-(trifluoromethyl)hex-5-enoyl]amino]carbamoyl]-5-(trifluoromethyl)-3-pyridyl]carbamate (2.45 g, 3.5016 mmol) and DIPEA (1.1872 g, 1.6 mL, 9.1858 mmol) in acetonitrile (50 mL) was heated at 50° C., then p-toluenesulfonyl chloride (815 mg, 4.2749 mmol) was added portion-wise at 50° C. The resultant mixture was stirred at 70° C. for 2 hours. Reaction mixture was cooled, basified with a saturated solution of sodium bicarbonate (200 mL) and extracted with ethyl acetate (3×100 mL). Combined organic layers were washed with brine (100 mL), dried over sodium sulfate, filtered and concentrated. The residue was purified by reverse phase chromatography using a gradient from 70% to 100% of acetonitrile in water containing 0.1% of formic acid giving as a yellow gummy material, tert-butyl N-[6-(2-allylpyrrolidin-1-yl)-2-[5-[1-benzyloxy-1-(trifluoromethyl)pent-4-enyl]-1,3,4-oxadiazol-2-yl]-5-(trifluoromethyl)-3-pyridyl]carbamate (2.2 g, 92%). $^1$H NMR (300 MHz, Chloroform-d) δ 1.51 (s, 9H), 1.64-1.78 (m, 2H), 1.86-2.08 (m, 2H), 2.16-2.57 (m, 6H), 3.32-3.44 (m, 1H), 3.53-3.69 (m, 1H), 4.35-4.49 (m, 1H), 4.58-4.69 (m, 1H), 4.71-4.87 (m, 1H), 4.88-5.10 (m, 4H), 5.60-5.84 (m, 2H), 7.24-7.43 (m, 5H), 8.99 (s, 1H), 9.55 (br. s., 1H) ppm. $^{19}$F NMR (282 MHz, Chloroform-d) δ −73.0 (s, 3F), −57.3 (s, 3F) ppm. ESI-MS m/z calc. 681.27496, found 682.5 (M+1)⁺; Retention time: 3.19 minutes (LC Method K).

To a degassed solution of tert-butyl N-[6-(2-allylpyrrolidin-1-yl)-2-[5-[1-benzyloxy-1-(trifluoromethyl)pent-4-enyl]-1,3,4-oxadiazol-2-yl]-5-(trifluoromethyl)-3-pyridyl]carbamate (155 mg, 0.2274 mmol) in 1,2-dichloroethane (15 mL) was added Grubbs catalyst, 2nd generation (40 mg, 0.047 mmol). The resultant mixture was stirred at 80° C. for 0.75 h. The reaction mixture was cooled to 0° C. and di(ethylene glycol) vinyl ether (125.84 mg, 0.13 mL, 0.9522 mmol) was added to quench the catalyst, then stirred at room temperature for 10 min and concentrated. The residue was purified by silica gel chromatography using a gradient from of 0% to 10% ethyl acetate in heptanes giving as a green-yellow solid, tert-butyl N-6-(benzyloxy)-6,18-bis(trifluoromethyl)-22-oxa-3,4,16,21-tetraazatetracyclo[15.3.1.1²,⁵.0¹²,¹⁶]docosa-1(21),2,4,9,17,19-hexaen-20-yl]carbamate (E/Z mixture) (125 mg, 84%). $^1$H NMR (300 MHz, Chloroform-d) δ 1.46 (s, 9H), 1.60-1.79 (m, 2H), 1.86-2.00 (m, 1H), 2.00-2.25 (m, 3H), 2.26-2.53 (m, 2H), 2.58-2.82 (m, 1H), 3.39-3.67 (m, 3H), 3.83-4.05 (m, 1H), 4.51-4.65 (m, 1H), 4.89-5.00 (m, 1H), 5.36-5.55 (m, 2H), 7.11-7.28 (m, 5H), 8.81-8.98 (m, 2H) ppm. $^{19}$F NMR (282 MHz, Chloroform-d) δ −75.0 and −74.1 (2s, 3F), −55.5 (s, 3F) ppm. ESI-MS m/z calc. 653.24365, found 654.4 (M+1)⁺; Retention time: 2.94 minutes (LC Method K).

Step 4: tert-Butyl N-[6-hydroxy-6,18-bis(trifluoromethyl)-22-oxa-3,4,16,21-tetraazatetracyclo[15.3.1.12,5.012,16]docosa-1(21),2,4,17,19-pentaen-20-yl]carbamate

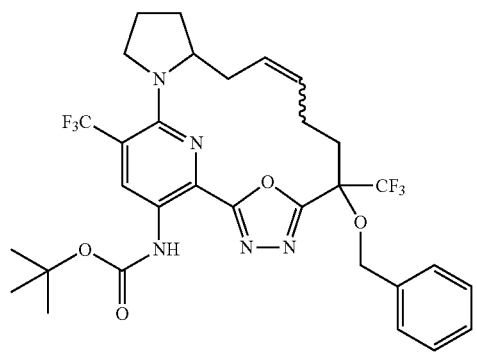

E/Z mixture

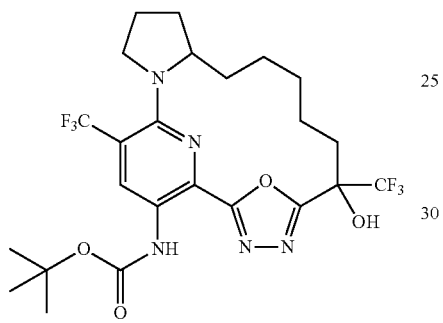

To a nitrogen degassed solution of tert-butyl N-6-(benzyloxy)-6,18-bis(trifluoromethyl)-22-oxa-3,4,16,21-tetraazatetracyclo[15.3.1.12,5.012,16]docosa-1(21),2,4,9,17,19-hexaen-20-yl]carbamate (E/Z mixture) (30 mg, 0.0459 mmol) in methanol (4 mL) was added SiliaCat Pd⁰ (73 mg, 0.24 mmol/g, 0.0175 mmol) and reaction was stirred for 64 hours under hydrogen balloon at room temperature. The reaction mixture was filtered over Celite, washed with methanol and concentrated. The residue was purified by silica gel chromatography using a gradient from 0% to 30% ethyl acetate in heptanes giving as a yellow gum, tert-butyl N-[6-hydroxy-6,18-bis(trifluoromethyl)-22-oxa-3,4,16,21-tetraazatetracyclo[15.3.1.12,5.012,16]docosa-1(21),2,4,17,19-pentaen-20-yl]carbamate (15 mg, 58%). $^1$H NMR (300 MHz, Chloroform-d) δ 1.20-1.27 (m, 2H), 1.45 (s, 9H), 1.48-1.59 (m, 5H), 1.85-1.98 (m, 1H), 1.99-2.65 (m, 4H), 3.30-3.62 (m, 3H), 3.87-4.18 (m, 2H), 8.75-8.97 (m, 2H) ppm. One exchangeable proton not observed in NMR. $^{19}$F NMR (282 MHz, Chloroform-d) δ −80.8 and −77.4 (s, 3F), −55.4 to −54.9 (m, 3F) ppm. ESI-MS m/z calc. 565.2124, found 566.4 (M+1)$^+$; Retention time: 2.73 minutes (LC Method K).

Step 5: 20-Amino-6,18-bis(trifluoromethyl)-22-oxa-3,4,16,21-tetraazatetracyclo[15.3.1.12,5.012,16]docosa-1(20),2,4,17(21),18-pentaen-6-ol (mixture of 4 stereoisomers) (Compound 1)

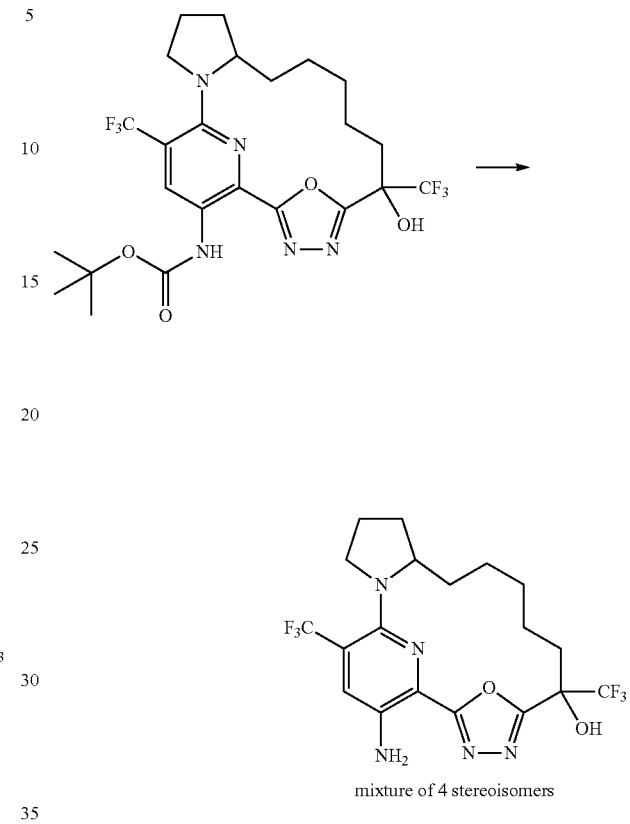

mixture of 4 stereoisomers

TFA (1.4800 g, 1 mL, 12.98 mmol) was added to tert-butyl N-[6-hydroxy-6,18-bis(trifluoromethyl)-22-oxa-3,4,16,21-tetraazatetracyclo[15.3.1.12,5.012,16]docosa-1(21),2,4,17,19-pentaen-20-yl]carbamate (30 mg, 0.053 mmol) in DCM (2 mL) at room temperature and the mixture was stirred for 2 h. The mixture was poured in saturated sodium bicarbonate solution (20 mL) and extracted with DCM (3×10 mL). The organic phases were combined, dried over anhydrous sodium sulfate, filtered and concentrated. The residue was purified by silica gel chromatography using a gradient from 0% to 30% of ethyl acetate in heptanes giving as a yellow solid, 20-amino-6,18-bis(trifluoromethyl)-22-oxa-3,4,16,21-tetraazatetracyclo[15.3.1.12,5.012,16]docosa-1(20),2,4,17(21),18-pentaen-6-ol (mixture of 4 stereoisomers) (10 mg, 39%). $^1$H NMR (300 MHz, CD$_3$OD) δ 0.80-1.01 (m, 2H), 1.13-1.36 (m, 3H), 1.42-1.68 (m, 4H), 1.71-1.87 (m, 1H), 1.91-2.08 (m, 1H), 2.12-2.29 (m, 1H), 2.36-2.75 (m, 2H), 3.31-3.47 (m, 1H), 3.52-3.75 (m, 1H), 3.86-4.23 (m, 1H), 7.62 (s, 1H) ppm. $^{19}$F NMR (282 MHz, CD$_3$OD) δ−82.0 and −78.8 (s, 3F), −58.1 (s, 3F) ppm. ESI-MS m/z calc. 465.15994, found 466.2 (M+1)$^+$; Retention time: 3.84 minutes (LC Method F).

Example 2: Preparation of 20-amino-6,18-bis(trifluoromethyl)-22-oxa-3,4,16,21-tetraazatetracyclo[15.3.1.12,5.012,16]docosa-1(20),2,4,17(21),18-pentaen-6-ol (diastereomer pair 1) (Compound 2) and 20-amino-6,18-bis(trifluoromethyl)-22-oxa-3,4,16,21-tetraazatetracyclo[15.3.1.12,5.012,16]docosa-1(20),2,4,17(21),18-pentaen-6-ol (diastereomer pair 2) (Compound 3)

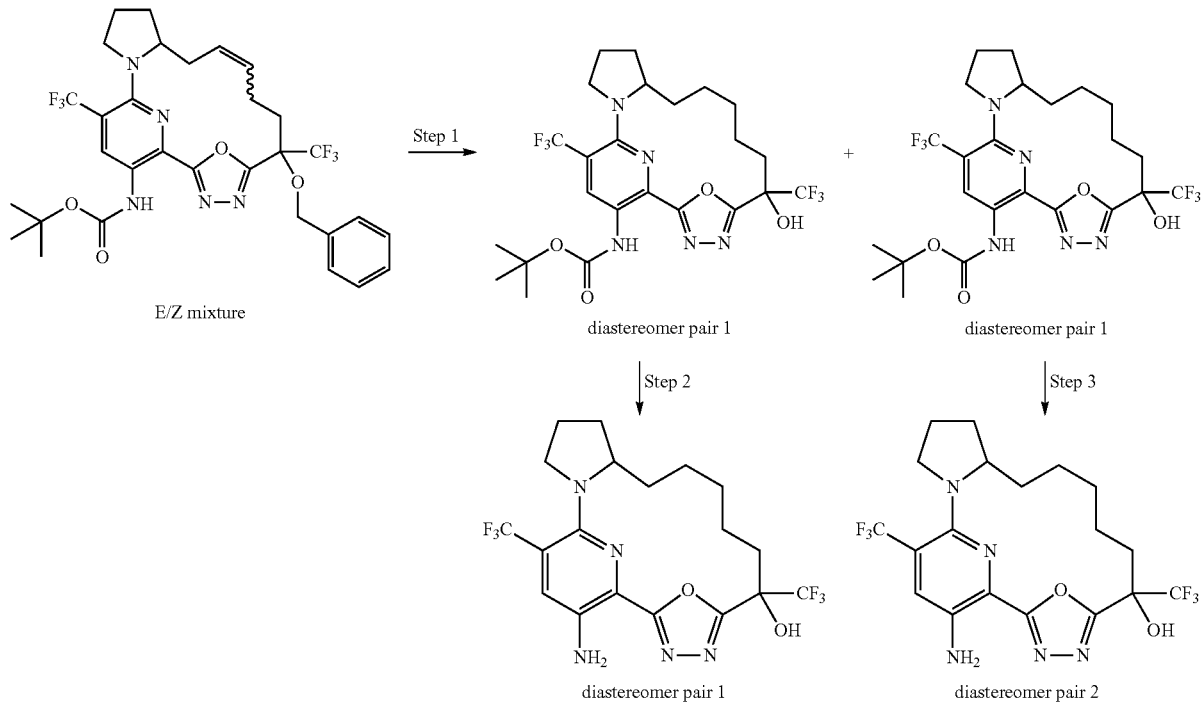

Step 1: tert-Butyl N-[6-hydroxy-6,18-bis(trifluoromethyl)-22-oxa-3,4,16,21-tetraazatetracyclo[15.3.1.12,5.012,16]docosa-1(21),2,4,17,19-pentaen-20-yl]carbamate (diastereomer pair 1) and tert-butyl N-[6-hydroxy-6,18-bis(trifluoromethyl)-22-oxa-3,4,16,21-tetraazatetracyclo[15.3.1.12,5.012,16]docosa-1(21),2,4,17,19-pentaen-20-yl]carbamate (diastereomer pair 2)

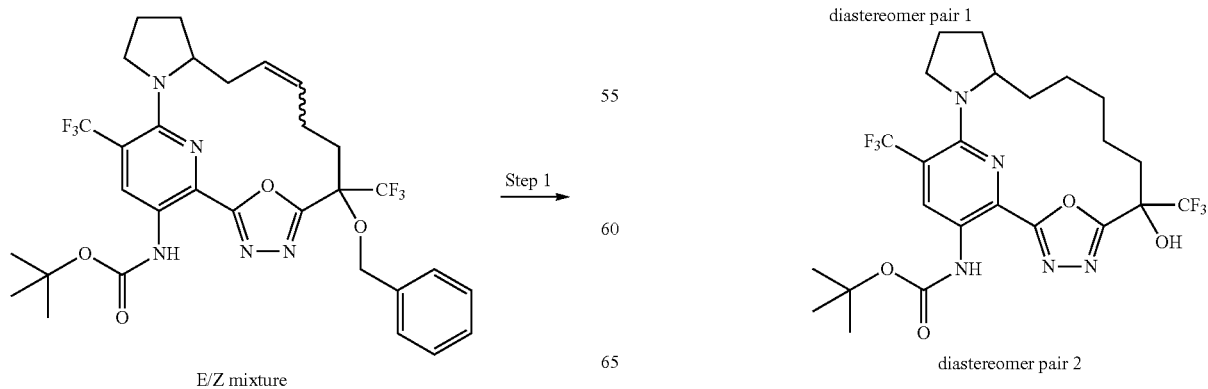

-continued

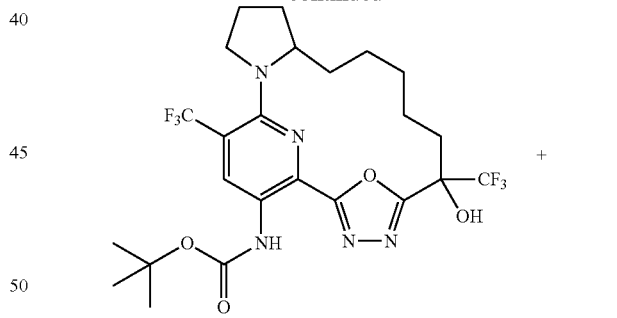

To a nitrogen degassed solution of tert-butyl N-6-(benzyloxy)-6,18-bis(trifluoromethyl)-22-oxa-3,4,16,21-tetraazatetracyclo[15.3.1.12,5.012,16]docosa-1(21),2,4,9,17,19-hexaen-20-yl]carbamate (E/Z mixture) (675 mg, 1.0327 mmol) in methanol (60 mL) was added SiliaCat Pd⁰ (1.6 g, 0.24 mmol/g, 0.384 mmol) and reaction was stirred for 24 hours under hydrogen balloon at room temperature. The reaction mixture was filtered over Celite, washed with methanol and concentrated. The residue was purified by silica gel chromatography using a gradient from 0% to 30% ethyl acetate in heptanes giving as a yellow solid and the first diastereomer pair to elute, tert-butyl N-[6-hydroxy-6,18-bis(trifluoromethyl)-22-oxa-3,4,16,21-tetraazatetracyclo[15.3.1.12,5.012,16]docosa-1(21),2,4,17,19-pentaen-20-yl]carbamate (diastereomer pair 1) (190 mg, 33%). $^1$H NMR (300 MHz, Chloroform-d) δ 0.79-0.91 (m, 1H), 0.94-1.10 (m, 1H), 1.25 (br. s., 1H), 1.41-1.68 (m, 13H), 1.70-1.84 (m, 1H), 1.85-2.07 (m, 2H), 2.08-2.27 (m, 2H), 2.28-2.44 (m, 1H), 2.54-2.74 (m, 1H), 3.40-3.71 (m, 3H), 3.94-4.14 (m, 1H), 8.80-9.10 (m, 2H) ppm. $^{19}$F NMR (282 MHz, Chloroform-d) δ−77.4 (s, 3F), −55.1 (s, 3F) ppm. ESI-MS m/z calc. 565.2124, found 566.3 (M+1)⁺; Retention time: 8.407 minutes (LC Method L).

Continued elution provided as a yellow solid and the second diastereomer pair to elute, tert-butyl N-[6-hydroxy-6,18-bis(trifluoromethyl)-22-oxa-3,4,16,21-tetraazatetracyclo[15.3.1.12,5.012,16]docosa-1(21),2,4,17,19-pentaen-20-yl]carbamate (diastereomer pair 2) (165 mg, 28%). $^1$H NMR (300 MHz, Chloroform-d) δ 0.81-0.98 (m, 2H), 1.41-1.60 (m, 13H), 1.61-1.89 (m, 3H), 1.93-2.25 (m, 3H), 2.35-2.62 (m, 2H), 3.46-3.69 (m, 3H), 3.95-4.13 (m, 1H), 8.91 (br. s., 2H) ppm. $^{19}$F NMR (282 MHz, Chloroform-d) δ−80.8 (s, 3F), −55.1 (s, 3F) ppm. ESI-MS m/z calc. 565.2124, found 566.4 (M+1)⁺; Retention time: 8.426 minutes (LC Method L).

Step 2: 20-Amino-6,18-bis(trifluoromethyl)-22-oxa-3,4,16,21-tetraazatetracyclo[15.3.1.12,5.012,16]docosa-1(20),2,4,17(21),18-pentaen-6-ol (diastereomer pair 1) (Compound 2)

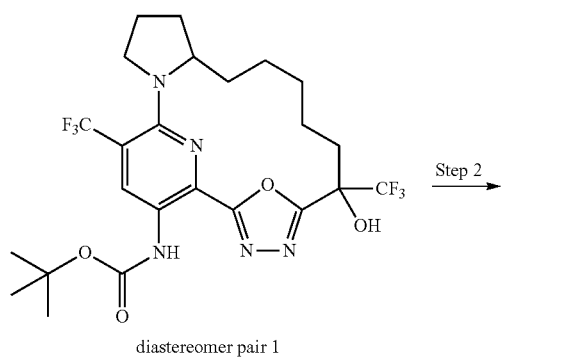

diastereomer pair 1

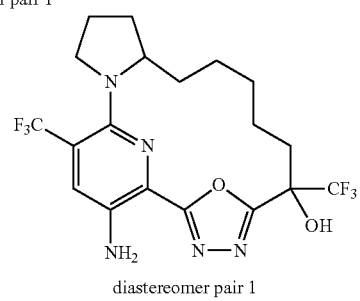

diastereomer pair 1

TFA (2.9600 g, 2 mL, 25.96 mmol) was added to tert-butyl N-[6-hydroxy-6,18-bis(trifluoromethyl)-22-oxa-3,4,16,21-tetraazatetracyclo[15.3.1.12,5.012,16]docosa-1(21),2,4,17,19-pentaen-20-yl]carbamate (diastereomer pair 1) (190 mg, 0.336 mmol) in DCM (4 mL) at room temperature and the mixture was stirred for 2 h. The mixture was poured into saturated aqueous sodium bicarbonate solution (20 mL) and extracted with DCM (3×10 mL). The organic phases were combined, dried over anhydrous sodium sulfate, filtered and concentrated. The residue was purified by silica gel chromatography using a gradient from 0% to 30% of ethyl acetate in heptanes giving as a yellow solid, 20-amino-6,18-bis(trifluoromethyl)-22-oxa-3,4,16,21-tetraazatetracyclo[15.3.1.12,5.012,16]docosa-1(20),2,4,17(21),18-pentaen-6-ol (diastereomer pair 1) (117 mg, 71%). $^1$H NMR (300 MHz, DMSO-d6) δ 0.71-0.91 (m, 1H), 1.32-1.62 (m, 6H), 1.65-1.80 (m, 1H), 1.81-2.00 (m, 2H), 2.02-2.16 (m, 1H), 2.18-2.36 (m, 1H), 2.38-2.62 (m, 2H), 3.18-3.31 (m, 1H), 3.39-3.56 (m, 1H), 3.78-3.94 (m, 1H), 6.10 (s, 2H), 7.59 (s, 1H), 7.69 (s, 1H) ppm. $^{19}$F NMR (282 MHz, DMSO-d6) δ−79.3 (s, 3F), −55.8 (s, 3F) ppm. ESI-MS m/z calc. 465.15994, found 466.2 (M+1)⁺; Retention time: 3.82 minutes (LC Method F).

Step 3: 20-Amino-6,18-bis(trifluoromethyl)-22-oxa-3,4,16,21-tetraazatetracyclo[15.3.1.12,5.012,16]docosa-1(20),2,4,17(21),18-pentaen-6-ol (diastereomer pair 2) (Compound 3)

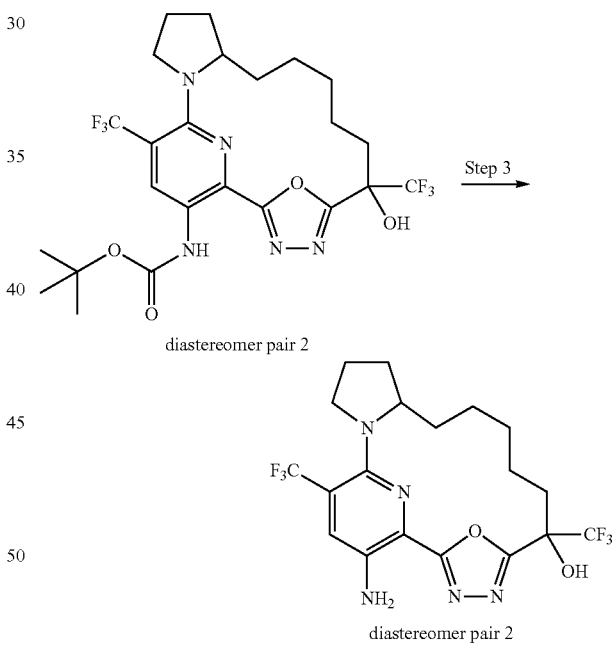

diastereomer pair 2 diastereomer pair 2

TFA (2.9600 g, 2 mL, 25.96 mmol) was added to tert-butyl N-[6-hydroxy-6,18-bis(trifluoromethyl)-22-oxa-3,4,16,21-tetraazatetracyclo[15.3.1.12,5.012,16]docosa-1(21),2,4,17,19-pentaen-20-yl]carbamate (diastereomer pair 2) (165 mg, 0.2918 mmol) in DCM (4 mL) at room temperature and the mixture was stirred for 2 h. The mixture was poured into saturated sodium bicarbonate solution (20 mL) and extracted with DCM (3×10 mL). The organic phases were combined, dried over anhydrous sodium sulfate, filtered and concentrated. The residue was purified by silica gel chromatography using a gradient from 0% to 30% of ethyl acetate in heptanes giving as a yellow solid, 20-amino-6,18-bis(trifluoromethyl)-22-oxa-3,4,16,21-tetraazatetracyclo

[15.3.1.1²,⁵.0¹²,¹⁶]docosa-1(20),2,4,17(21),18-pentaen-6-ol (diastereomer pair 2) (90 mg, 65%). ¹H NMR (300 MHz, DMSO-d6) δ 0.72-0.94 (m, 1H), 1.21-1.54 (m, 5H), 1.55-1.79 (m, 3H), 1.81-1.93 (m, 1H), 1.94-2.18 (m, 2H), 2.19-2.41 (m, 2H), 3.17-3.30 (m, 1H), 3.41-3.60 (m, 1H), 3.88-4.09 (m, 1H), 6.10 (br. s., 2H), 7.53 (s, 1H), 7.69 (s, 1H) ppm. ¹⁹F NMR (282 MHz, DMSO-d6) δ −76.5 (s, 3F), −55.9 (s, 3F) ppm. ESI-MS m/z calc. 465.15994, found 466.2 (M+1)⁺; Retention time: 3.78 minutes (LC Method F).

Example 3: Preparation of (6R,12R)-20-amino-6,18-bis(trifluoromethyl)-22-oxa-3,4,16,21-tetraazatetracyclo[15.3.1.1²,⁵.0¹²,¹⁶]docosa-1(21),2,4,17,19-pentaen-6-ol (Compound 4) and (6S,12R)-20-amino-6,18-bis(trifluoromethyl)-22-oxa-3,4,16,21-tetraazatetracyclo[15.3.1.1²,⁵.0¹²,¹⁶]docosa-1(21),2,4,17,19-pentaen-6-ol (Compound 5)

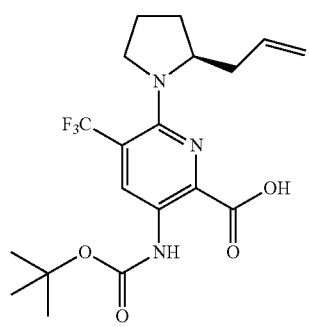

+

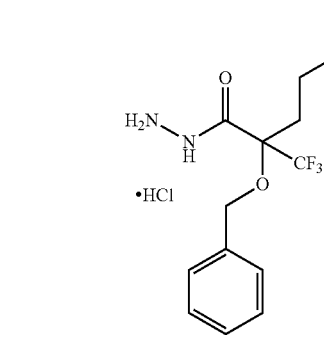

Step 1 →

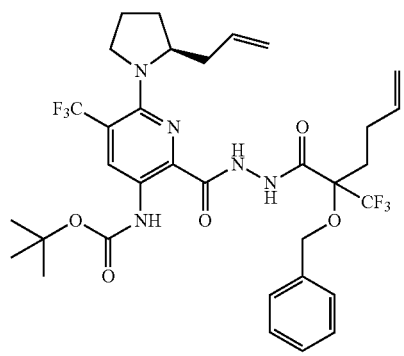

Step 2 →

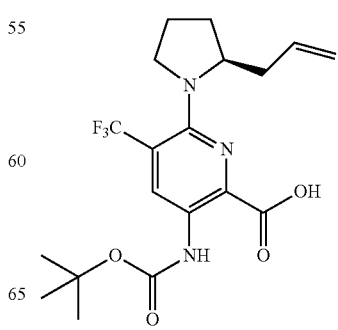

+

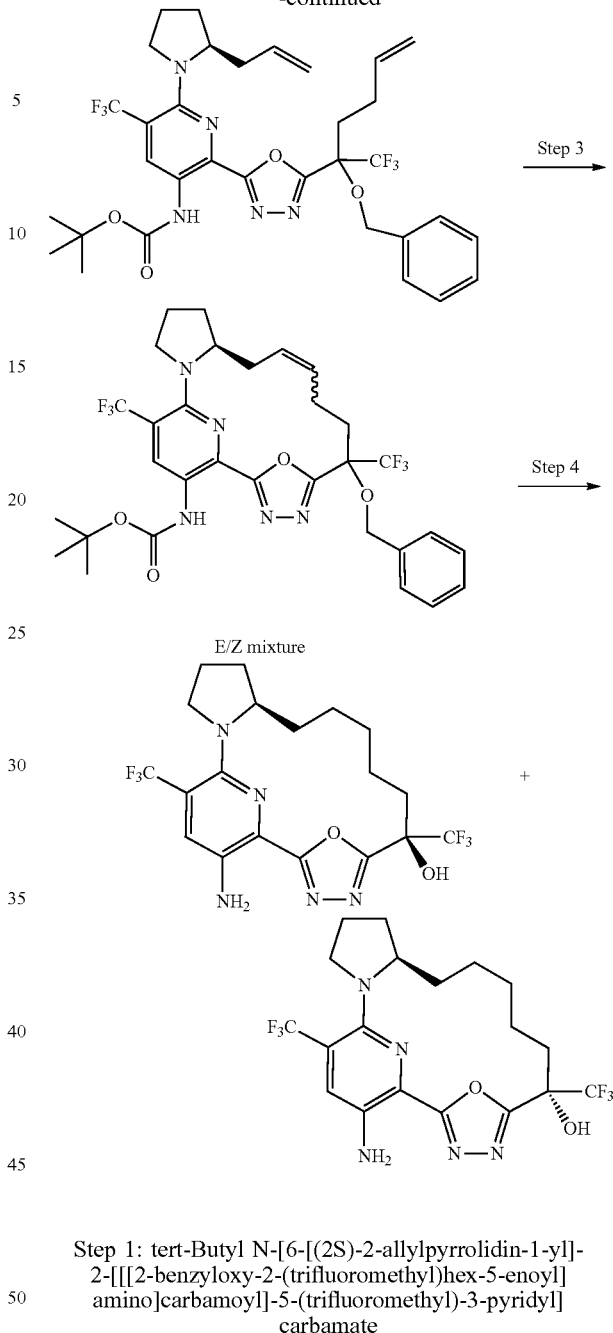

Step 1: tert-Butyl N-[6-[(2S)-2-allylpyrrolidin-1-yl]-2-[[[2-benzyloxy-2-(trifluoromethyl)hex-5-enoyl]amino]carbamoyl]-5-(trifluoromethyl)-3-pyridyl]carbamate -continued

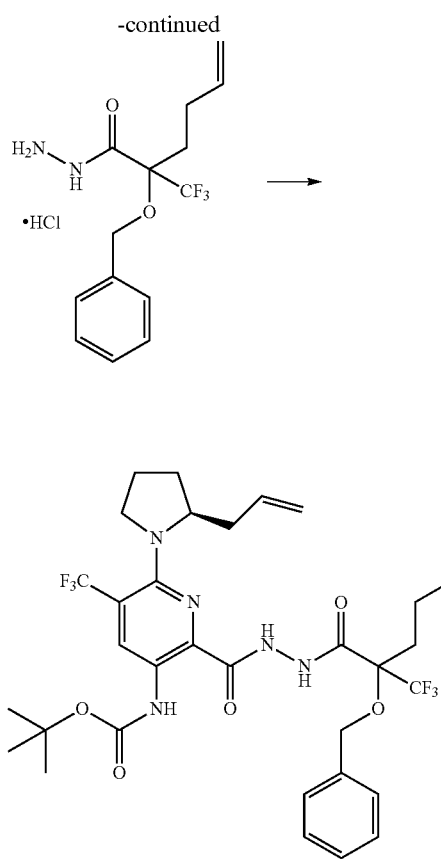

Step 2: tert-Butyl N-[6-[(2S)-2-allylpyrrolidin-1-yl]-2-[5-[1-benzyloxy-1-(trifluoromethyl)pent-4-enyl]-1,3,4-oxadiazol-2-yl]-5-(trifluoromethyl)-3-pyridyl]carbamate

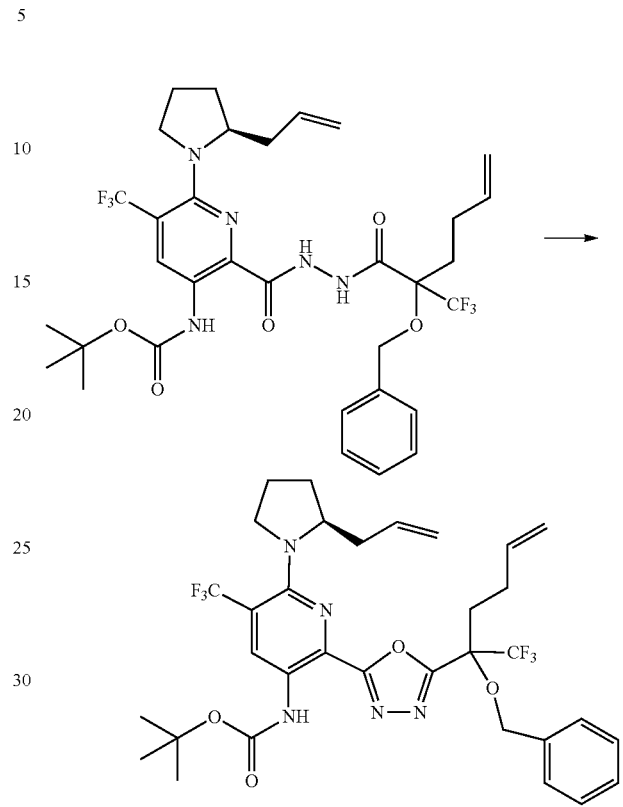

To a solution of 6-[(2S)-2-allylpyrrolidin-1-yl]-3-(tert-butoxycarbonylamino)-5-(trifluoromethyl)pyridine-2-carboxylic acid (7.8 g, 18.78 mmol) in NMP (70 mL) was added 2-benzyloxy-2-(trifluoromethyl)hex-5-enehydrazide (hydrochloride salt) (6.4 g, 18.89 mmol) and DIEA (8.5 g, 65.77 mmol) followed by HATU (10.7 g, 28.14 mmol). The reaction mixture was stirred at room temperature for 2.5 h then the mixture was diluted with water (100 mL) and extracted with ethyl acetate (3×50 mL). The organic phases were combined and dried over $MgSO_4$, filtered, and concentrated. The residue was purified by silica gel chromatography using a gradient from 0% to 5% EtOAc in hexanes giving tert-butyl N-[6-[(2S)-2-allylpyrrolidin-1-yl]-2-[[[2-benzyloxy-2-(trifluoromethyl)hex-5-enoyl]amino]carbamoyl]-5-(trifluoromethyl)-3-pyridyl]carbamate (10.2 g, 78%). $^1$H (400 MHz, Chloroform-d) δ1.52 (s, 9H), 1.67-1.79 (m, 2H), 1.95-1.97 (m, 1H), 2.14-2.29 (m, 5H), 2.43-2.53 (m, 2H), 3.34-3.38 (m, 1H), 3.61-3.67 (m, 1H), 4.31-4.36 (m, 1H), 4.71-4.75 (m, 1H), 4.84-4.87 (m, 1H), 4.99-5.14 (m, 4H), 5.75-5.88 (m, 2H), 7.38-7.43 (m, 5H), 9.01 (d, J 2.5 Hz, 1H), 9.12-9.20 (m, 1H), 9.92-9.99 (m, 1H), 10.06 (d, J 2.4 Hz, 1H) ppm. ESI-MS m/z calc. 699.2855, found 700.4 (M+1)$^+$; Retention time: 2.39 minutes (LC Method A).

tert-Butyl N-[6-[(2S)-2-allylpyrrolidin-1-yl]-2-[[[2-benzyloxy-2-(trifluoromethyl)hex-5-enoyl]amino]carbamoyl]-5-(trifluoromethyl)-3-pyridyl]carbamate (19.3 g, 27.58 mmol) was dissolved in acetonitrile (385 mL) then added DIEA (14.5 mL, 83.25 mmol) and heated to 50° C. To this yellow solution, p-toluenesulfonyl chloride (7.9 g, 41.44 mmol) was slowly added and the orange solution was heated at 70° for 6 h. Another portion of p-toluenesulfonyl chloride (0.8 g, 4.196 mmol) was added and stirred the mixture at room temperature overnight. The deep orange solution was washed with a saturated solution of sodium bicarbonate (400 mL) and the bicarbonate phase was back extracted twice with ethyl acetate (2×150 mL). The combined organic phases were washed once more with a saturated solution of sodium bicarbonate (200 mL) and brine (200 mL). The combined organic phases were dried, filtered and evaporated to give a deep orange oil. The residue was purified by silica gel chromatography using a gradient from 0% to 5% ethyl acetate and hexanes giving tert-butyl N-[6-[(2S)-2-allylpyrrolidin-1-yl]-2-[5-[1-benzyloxy-1-(trifluoromethyl)pent-4-enyl]-1,3,4-oxadiazol-2-yl]-5-(trifluoromethyl)-3-pyridyl]carbamate (16.5 g, 88%). $^1$H NMR (400 MHz, Chloroform-d) δ 9.58 (d, J=3.4 Hz, 1H), 9.02 (s, 1H), 7.48-7.20 (m, 5H), 5.75 (dddd, J=17.6, 15.4, 7.0, 4.6 Hz, 2H), 5.10-4.93 (m, 4H), 4.82 (dd, J=31.7, 10.9 Hz, 1H), 4.67 (dd, J=10.9, 6.4 Hz, 1H), 4.45 (d, J=8.0 Hz, 1H), 3.64 (q, J=8.7 Hz, 1H), 3.40 (t, J=8.4 Hz, 1H), 2.61-2.17 (m, 6H), 2.14-1.87 (m, 2H), 1.84-1.64 (m, 2H), 1.57 (s, 9H) ppm. ESI-MS m/z calc. 681.27496, found 682.0 (M+1)$^+$; Retention time: 2.52 minutes (LC Method M).

241

Step 3: tert-Butyl N-[(12S)-6-benzyloxy-6,18-bis(trifluoromethyl)-22-oxa-3,4,16,21-tetrazatetracyclo[15.3.1.12,5.012,16]docosa-1(20),2,4,9,17(21),18-hexaen-20-yl]carbamate (E/Z mixture)

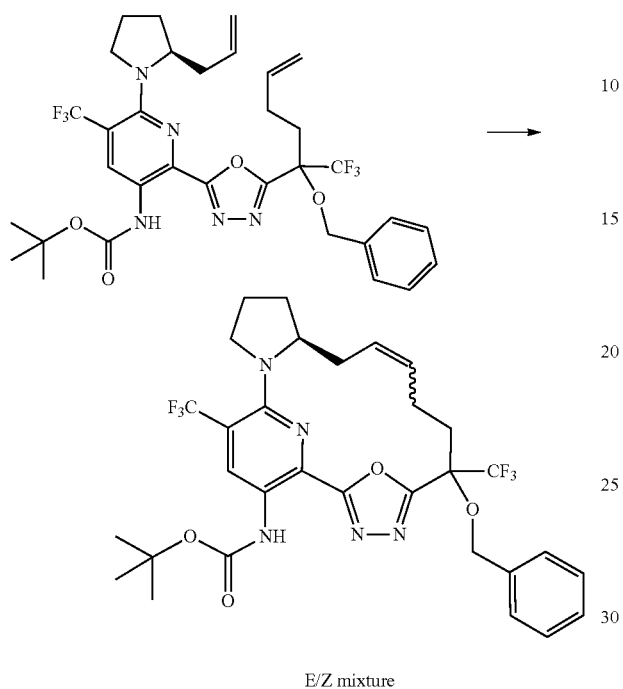

E/Z mixture

A degassed solution of tert-butyl N-[6-[(2S)-2-allylpyrrolidin-1-yl]-2-[5-[1-benzyloxy-1-(trifluoromethyl)pent-4-enyl]-1,3,4-oxadiazol-2-yl]-5-(trifluoromethyl)-3-pyridyl]carbamate (10.47 g, 14.131 mmol) in DCE (2000 mL) was heated to 50° C. under nitrogen atmosphere for 15 min. Zhan catalyst-1B (2 g, 2.722 mmol) was then added and the mixture was heated to 70° C. and kept at this temperature overnight. More Zhan catalyst-1B (0.5 g, 0.6805 mmol) was added and heating was continued for 4 h. The reaction mixture was cooled down and concentrated under reduced pressure. The residue was purified by silica gel chromatography using a gradient from 0% to 10% EtOAc in hexanes yielding as an intense yellow green foam, tert-butyl N-[(12S)-6-benzyloxy-6,18-bis(trifluoromethyl)-22-oxa-3,4,16,21-tetrazatetracyclo[15.3.1.12,5.012,16]docosa-1(20),2,4,9,17(21),18-hexaen-20-yl]carbamate (E/Z mixture) (5.87 g, 61%). $^1$H NMR (500 MHz, CDCl$_3$) δ 9.01 (s, 1H), 8.98 (d, J=6.8 Hz, 1H), 7.38-7.21 (m, 5H), 5.64-5.47 (m, 2H), 5.02 (q, J=11.3 Hz, 1H), 4.68 (q, J=11.0 Hz, 1H), 4.15-3.92 (m, 1H), 3.75-3.42 (m, 3H), 2.92-2.81 (m, 1H), 2.79-2.64 (m, 1H), 2.58-2.48 (m, 1H), 2.48-2.35 (m, 1H), 2.31-2.16 (m, 2H), 2.10-1.99 (m, 1H), 1.82-1.71 (m, 2H), 1.55 (s, 9H) ppm. ESI-MS m/z calc. 653.2437, found 654.1 (M+1)$^+$; Retention time: 4.29 minutes (LC Method G).

242

Step 4: (6R,12R)-20-Amino-6,18-bis(trifluoromethyl)-22-oxa-3,4,16,21-tetraazatetracyclo[15.3.1.12,5.012,16]docosa-1(21),2,4,17,19-pentaen-6-ol (Compound 4) and (6S,12R)-20-amino-6,18-bis(trifluoromethyl)-22-oxa-3,4,16,21-tetraazatetracyclo[15.3.1.12,5.012,16]docosa-1(21),2,4,17,19-pentaen-6-ol (Compound 5)

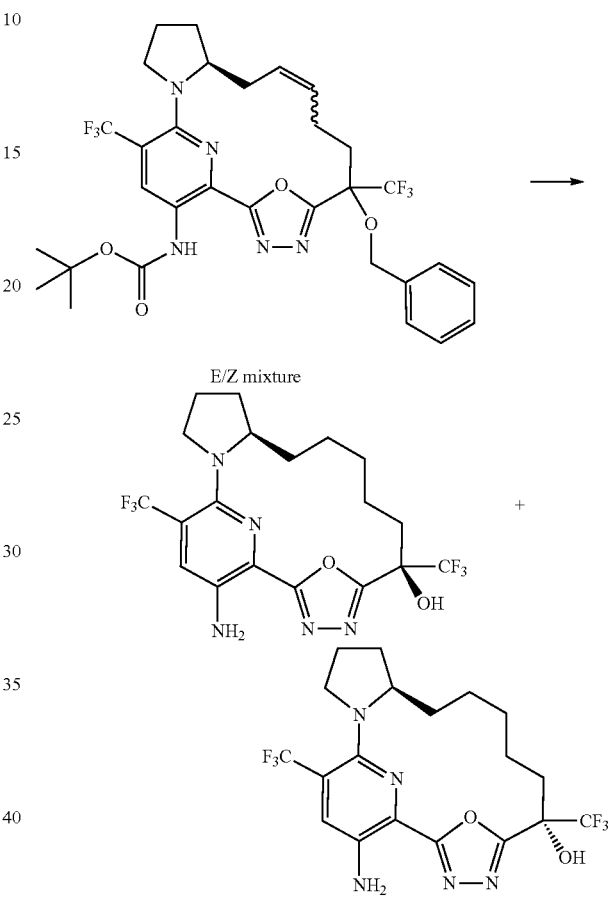

E/Z mixture

To Pd/C (250 mg of 10% w/w, 0.2349 mmol) was added tert-butyl N-[(12S)-6-benzyloxy-6,18-bis(trifluoromethyl)-22-oxa-3,4,16,21-tetrazatetracyclo[15.3.1.12,5.012,16]docosa-1(20),2,4,9,17(21),18-hexaen-20-yl]carbamate (E/Z mixture) (1.4 g, 2.142 mmol) in degassed MeOH (10 mL) and the mixture was stirred under a balloon of H$_2$ (10 mg, 4.961 mmol) for 3 days. The mixture was filtered over Celite and washed with MeOH. The filtrate was evaporated and the crude product was chromatographed on a 40 g silica gel column eluting with a gradient from 0% to 25% EtOAc in hexanes giving the N-Boc-protected product intermediate as a mixture of diastereomers. This material was next dissolved in DCM (10 mL) and TFA (1 mL, 12.98 mmol) was added. The mixture was stirred at ambient temperature for 20 h. The solvent was removed in vacuo and the crude oil was chromatographed by reverse phase column chromatography using a C$_{18}$ column eluting with a gradient from 30% to 100% acetonitrile in water affording 650 mg of a mixture of diastereomers. This mixture was subjected to chiral SFC using a ChiralPak AS-H column (250×21.2 mm, 5 μm particle size) using 10% methanol in CO$_2$ mobile phase over 6 minutes (flow rate=70 mL/min) which gave two diastereomeric products:

The first diastereomer to elute was isolated as (6R,12R)-20-amino-6,18-bis(trifluoromethyl)-22-oxa-3,4,16,21-tetraazatetracyclo[15.3.1.1.2,5.0.12,16]docosa-1(21),2,4,17,19-pentaen-6-ol (261.4 mg, 52%). ¹H NMR (400 MHz, Chloroform-d) δ 7.46 (s, 1H), 5.08 (s, 1H), 4.01 (q, J=9.8, 9.1 Hz, 2H), 3.65 (d, J=8.8 Hz, 1H), 3.51-3.38 (m, 1H), 2.57-2.40 (m, 2H), 2.18 (dtd, J=12.5, 6.3, 3.5 Hz, 1H), 2.12-1.95 (m, 2H), 1.84 (p, J=10.0, 9.5 Hz, 1H), 1.77-1.37 (m, 8H), 0.94 (s, 1H) ppm. ESI-MS m/z calc. 465.15994, found 466.1 (M+1)⁺; Retention time: 3.17 minutes (LC Method D).

The second diastereomer to elute was isolated as (6S, 12R)-20-amino-6,18-bis(trifluoromethyl)-22-oxa-3,4,16, 21-tetraazatetracyclo[15.3.1.1.2,5.0.12,16]docosa-1(21),2,4, 17,19-pentaen-6-ol (256.4 mg, 51%). ¹H NMR (400 MHz, Chloroform-d) δ 7.59 (s, 1H), 4.04 (s, 1H), 3.62 (t, J=8.6 Hz, 1H), 3.43 (s, 1H), 2.61 (s, 1H), 2.36 (t, J=12.4 Hz, 1H), 2.28-2.09 (m, 2H), 2.07-1.71 (m, 3H), 1.61 (d, J=22.0 Hz, 6H), 1.01 (s, 1H) ppm. ESI-MS m/z calc. 465.15994, found 466.0 (M+1)⁺; Retention time: 3.12 minutes (LC Method D).

Step 5: Solid Form Characterization of Amorphous Compound 4 (Neat Form)

A. X-Ray Powder Diffraction

The XRPD diffractogram for amorphous Compound 4 (neat form) produced by Step 4 was acquired using the General X-Ray Powder Diffraction (XRPD) Method and is provided in FIG. 1.

B. Thermogravimetric Analysis (TGA)

Figure 2:
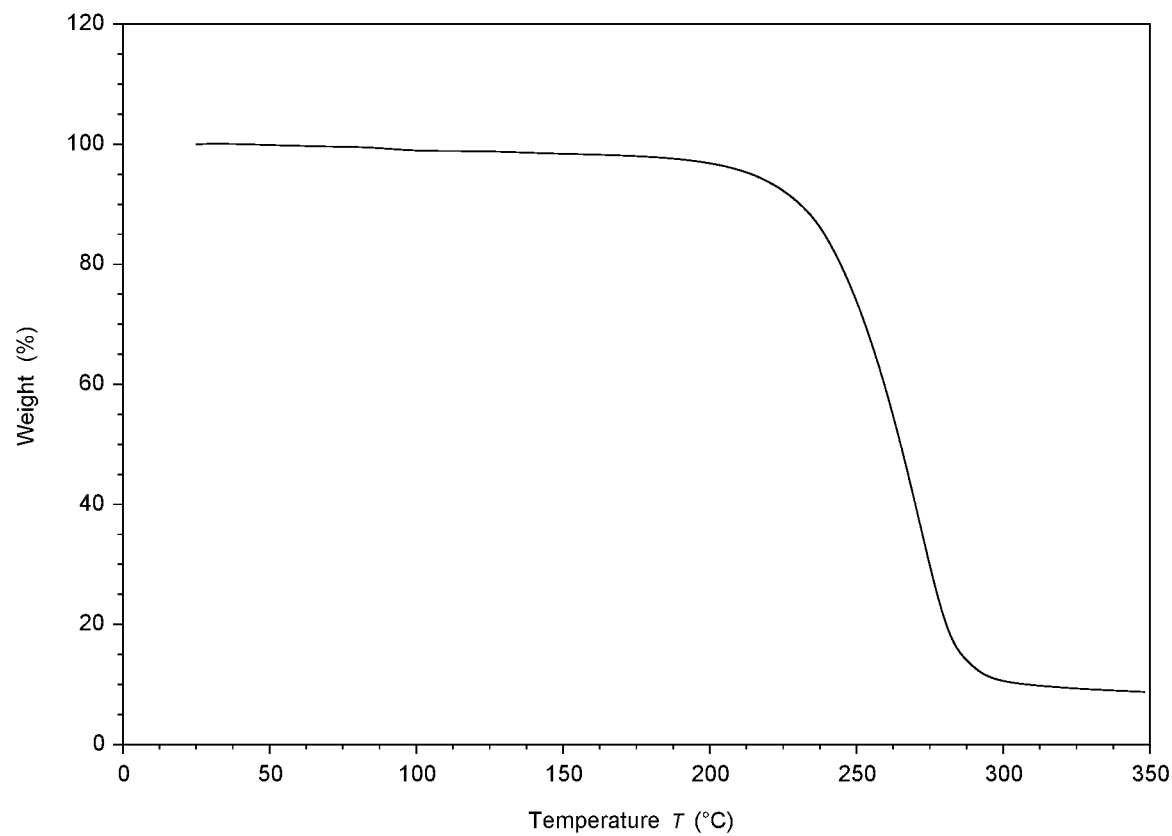
FIG. 2 provides a thermogravimetric analysis (TGA) curve for amorphous Compound 4 (neat form).

The TGA data for amorphous Compound 4 (neat form) were collected on a TA instrument Discovery series with TRIOS system. The TGA curve for amorphous Compound 4 (neat form) is provided in FIG. 2. The TGA curve shows 1.69% weight loss from −40-155° C., with a ramp of 10.00° C./min to 350.00° C.

C. Differential Scanning Calorimetry Analysis

The DSC data for amorphous Compound 4 (neat form) were collected on a TA instrument Discovery series with TRIOS system. The DSC was run using the following modulated DSC method:

1. Equilibrated at −20.00° C.,
2. Modulated by +/−1.00° C. every 60 seconds,
3. Isothermal for 5.00 min, then
4. Ramp of 2.00° C./min to 250.00° C.

Figure 3:
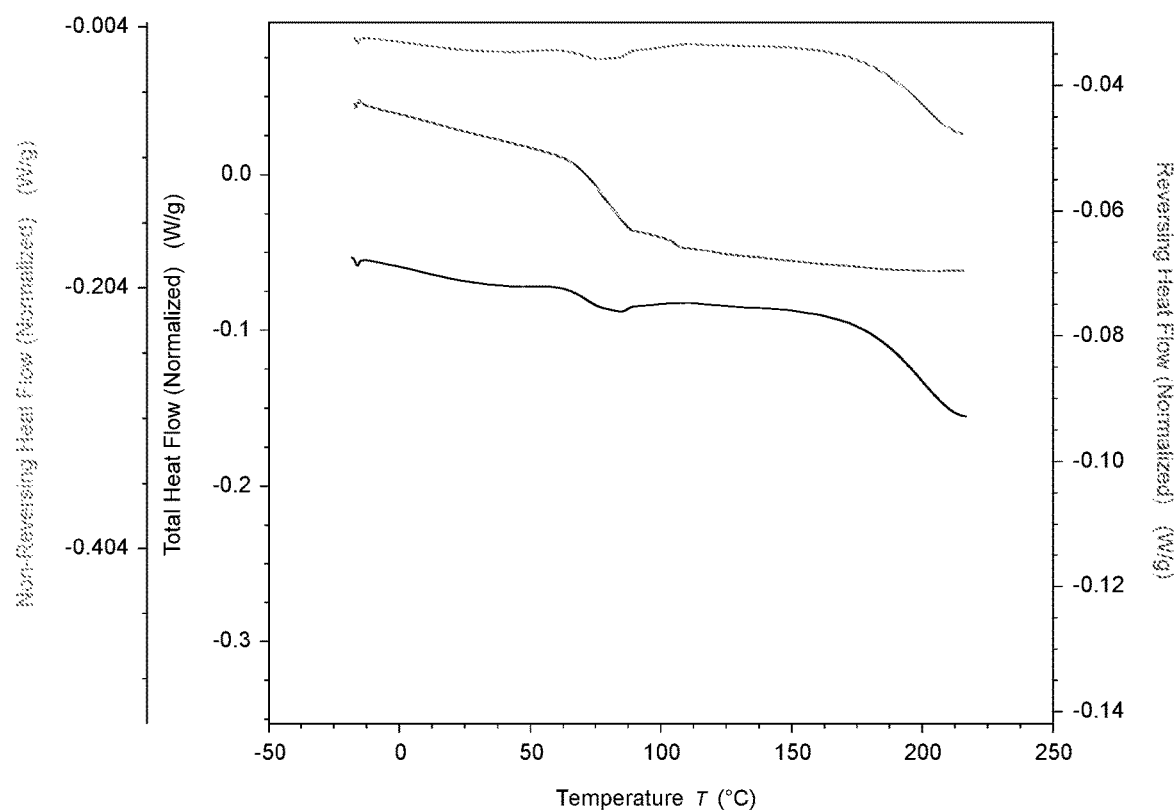
FIG. 3 provides a DSC analysis of amorphous Compound 4 (neat form).

The DSC thermogram for amorphous Compound 4 (neat form) is provided in FIG. 3. The thermogram shows a Tg midpoint at 77.6° C.

Step 6: Solid Form Characterization of Crystalline Compound 5 Form a (Neat)

A. Single Crystal X-Ray Diffraction

Single crystals of crystalline Compound 5 Form A (neat) were grown from ethanol and pentane. X-ray diffraction data were acquired at 100 K on a Bruker diffractometer equipped with Cu Kα radiation (λ=1.54178 Å) and a CCD detector. The structure was solved and refined using SHELX programs (Sheldrick, G. M., Acta Cryst., (2008) A64, 112-122) and results are summarized in Table 3 below.

TABLE 3

Single crystal elucidation of crystalline Compound 5 Form A (neat)

| Crystal System | Tetragonal |
|---|---|
| Space Group | I4₁ |
| a (Å) | 18.1053(4) |
| b (Å) | 18.1053(4) |
| c (Å) | 13.1201(3) |
| α (°) | 90 |
| β (°) | 90 |
| γ (°) | 90 |
| V (Å3) | 4300.8(2) |
| Z/Z' | 8/1 |
| Temperature | 100 K |

Example 4: Preparation of (6S,12S)-20-amino-6,18-bis(trifluoromethyl)-22-oxa-3,4,16,21-tetraazatetracyclo[15.3.1.1.2,5.0.12,16]docosa-1(21),2,4,17,19-pentaen-6-ol (Compound 6)

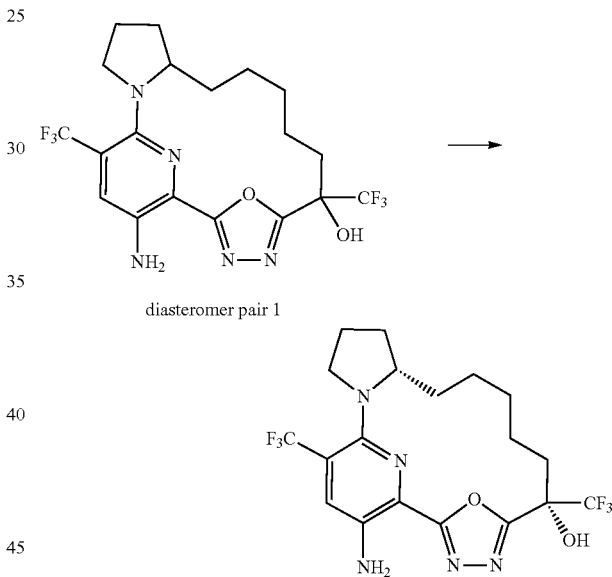

diastereomer pair 1

Step 1: (6S,12S)-20-Amino-6,18-bis(trifluoromethyl)-22-oxa-3,4,16,21-tetraazatetracyclo[15.3.1.1.2, 5.0.12,16]docosa-1(21),2,4,17,19-pentaen-6-ol (Compound 6)

20-Amino-6,18-bis(trifluoromethyl)-22-oxa-3,4,16,21-tetraazatetracyclo[15.3.1.1.2,5.0.12,16]docosa-1(20),2,4,17 (21),18-pentaen-6-ol (diastereomer pair 1) (96.7 mg, 0.2078 mmol) was subjected to chiral SFC using a ChiralPak AS-H column (250×10 mm, 5 μm particle size) using 8% methanol in CO₂ mobile phase over 6 minutes (flow rate=10 mL/min) which gave as the second single enantiomer to elute, (6S, 12S)-20-amino-6,18-bis(trifluoromethyl)-22-oxa-3,4,16,21-tetraazatetracyclo[15.3.1.1.2,5.0.12,16]docosa-1(21),2,4,17, 19-pentaen-6-ol (30.8 mg, 64%) ESI-MS m/z calc. 465.15994, found 466.0 (M+1)⁺; Retention time: 2.13 minutes (LC Method N).

245

Example 5: Preparation of (6R,12S)-20-amino-6,18-bis(trifluoromethyl)-22-oxa-3,4,16,21-tetraazatetracyclo[15.3.1.1²,⁵.0¹²,¹⁶]docosa-1(21),2,4,17,19-pentaen-6-ol (Compound 7)

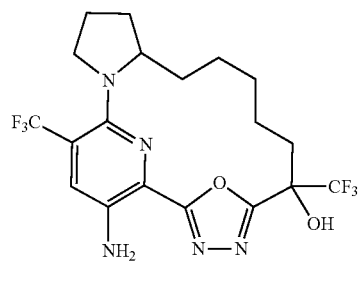

diasteromer pair 2

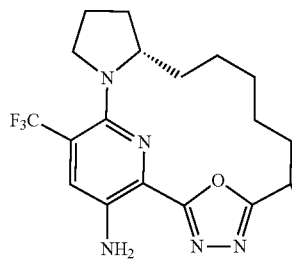

Step 1: (6R,12S)-20-Amino-6,18-bis(trifluoromethyl)-22-oxa-3,4,16,21-tetraazatetracyclo[15.3.1.1²,5.0¹²,¹⁶]docosa-1(21),2,4,17,19-pentaen-6-ol (Compound 7)

20-Amino-6,18-bis(trifluoromethyl)-22-oxa-3,4,16,21-tetraazatetracyclo[15.3.1.1²,5.0¹²,¹⁶]docosa-1(20),2,4,17(21),18-pentaen-6-ol (diastereomer pair 2) (80 mg, 0.1719 mmol) was purified by chiral SFC using a ChiralPak AS-H (250×10 mm) 5 μm column; 40° C. and 8% MeOH (no modifier) in $CO_2$ as an eluant using a flow rate 10.0 mL/min with an injection volume of 70 μL to give as the first eluting enantiomer, (6R,12S)-20-amino-6,18-bis(trifluoromethyl)-22-oxa-3,4,16,21-tetraazatetracyclo[15.3.1.1²,5.0¹²,¹⁶]docosa-1(21),2,4,17,19-pentaen-6-ol (19.9 mg, 50%). $^1$H NMR (400 MHz, DMSO-d6) δ 7.73 (s, 1H), 7.58 (d, J=2.1 Hz, 1H), 6.12 (s, 2H), 4.02 (d, J=8.2 Hz, 1H), 3.52 (t, J=8.5 Hz, 1H), 3.30 (d, J=9.0 Hz, 2H), 2.35 (ddd, J=25.1, 14.1, 6.2 Hz, 2H), 2.21-2.12 (m, 1H), 2.10-2.00 (m, 1H), 1.94 (d, J=9.0 Hz, 1H), 1.79-1.68 (m, 2H), 1.64 (s, 1H), 1.58-1.46 (m, 2H), 1.46-1.33 (m, 2H), 0.88 (q, J=5.7, 4.9 Hz, 1H) ppm. ESI-MS m/z calc. 465.15994, found 466.0 (M+1)⁺; Retention time: 2.1 minutes (LC Method A).

246

Example 6: Preparation of 16-amino-10,18-bis(trifluoromethyl)-20-oxa-2,12,13,19-tetraazatetracyclo[13.3.1.1²,5.1¹¹,¹⁴]henicosa-1(19),11,13,15,17-pentaen-10-ol (diastereomer pair 1) (Compound 8) and 16-amino-10,18-bis(trifluoromethyl)-20-oxa-2,12,13,19-tetraazatetracyclo[13.3.1.1²,5.1¹¹,¹⁴]henicosa-1(19),11,13,15,17-pentaen-10-ol (diastereomer pair 2) (Compound 9)

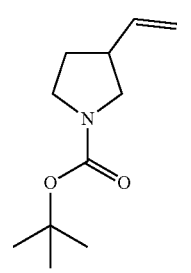

Step 1

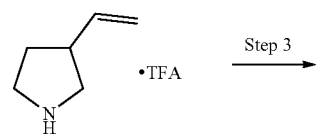

Step 2

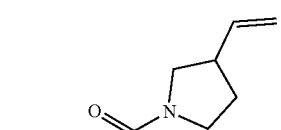

Step 3

247
-continued
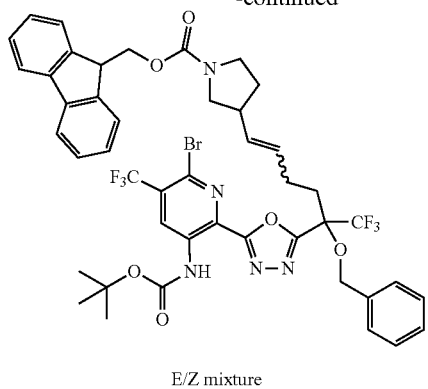
E/Z mixture
Step 5 →
248
-continued
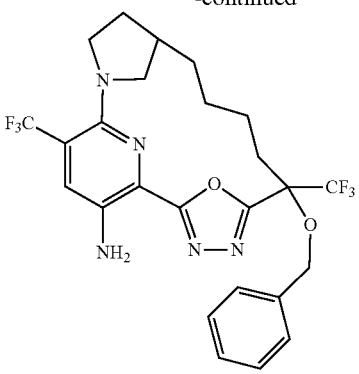
Step 9 →
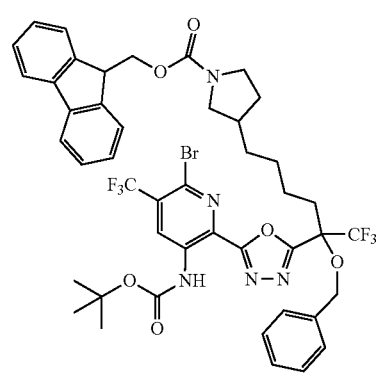
Step 6 →
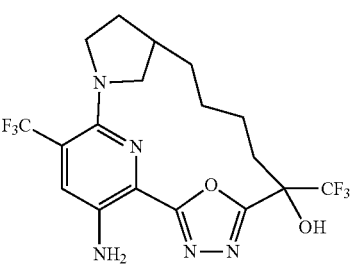
Step 10 →
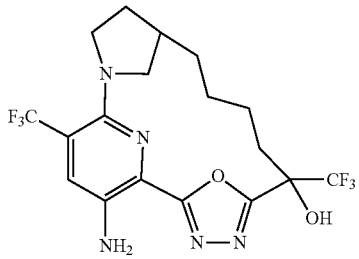
diasteromer pair 1
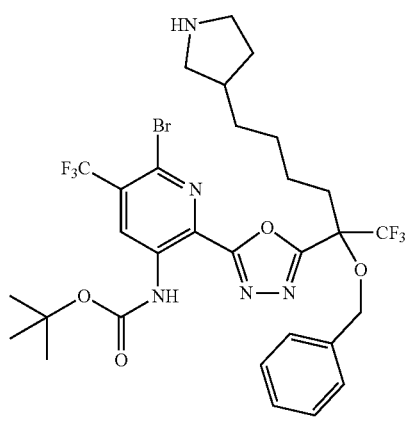
Step 7 →
diasteromer pair 2
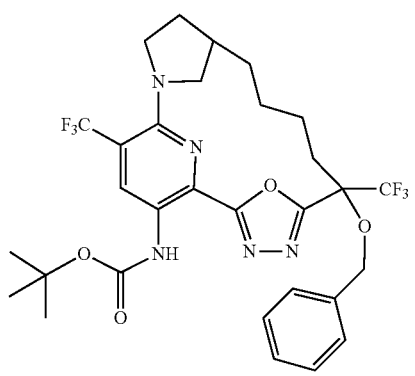
Step 8 →
Step 1: tert-Butyl 3-vinylpyrrolidine-1-carboxylate
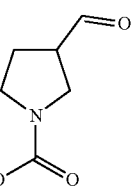
→

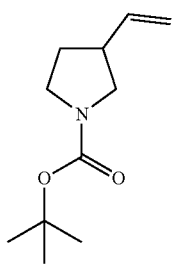

n-Butyllithium (26.6 mL of 2.5 M in hexanes, 66.5 mmol) was slowly added to a suspension of methyltriphenylphosphonium bromide (23.8 g, 66.625 mmol) in tetrahydrofuran (100 mL) at 0° C. The resulting orange solution was stirred at 0° C. for 5 minutes. A solution of tert-butyl 3-formylpyrrolidine-1-carboxylate (12.5 g, 62.736 mmol) in tetrahydrofuran (75 mL) was slowly added using an addition funnel keeping the reaction mixture at 0° C. After stirring for 15 minutes at 0° C., the reaction was warmed to room temperature over 2.5 hours. Again, the reaction mixture was cooled to 0° C. and was quenched with saturated aqueous ammonium chloride (200 mL) and extracted using diethyl ether (3×150 mL). The organic layers were combined, dried over magnesium sulfate, filtered and concentrated. The residue was purified by silica gel chromatography using a gradient from 0% to 15% EtOAc in heptanes giving as a clear liquid, tert-butyl 3-vinylpyrrolidine-1-carboxylate (10.18 g, 82%). $^1$H NMR (300 MHz, Chloroform-d) δ 1.45 (s, 9H), 1.60-1.77 (m, 1H), 1.99 (dtd, J=12.5, 6.4, 3.4 Hz, 1H), 2.69-2.85 (m, 1H), 2.96-3.12 (m, 1H), 3.19-3.36 (m, 1H), 3.38-3.63 (m, 2H), 4.97-5.15 (m, 2H), 5.76 (dt, J=17.1, 8.6 Hz, 1H) ppm. ESI-MS m/z calc. 197.14159, found 142.2 (M-$^t$Bu+1)$^+$; Retention time: 2.08 minutes (LC Method B).

Step 2: 3-Vinylpyrrolidine (trifluoroacetate Salt)

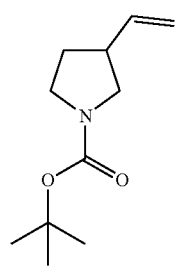

Trifluoroacetic acid (47.360 g, 32 mL, 415.35 mmol) was added slowly to tert-butyl 3-vinylpyrrolidine-1-carboxylate (8 g, 40.553 mmol) in dichloromethane (32 mL) at 0° C. The mixture was stirred for 2 hours at room temperature then concentrated. Toluene (40 mL) was added and concentrated to provide as a brown oil, 3-vinylpyrrolidine (trifluoroacetate salt) (13.3 g, 93%). $^1$H NMR (300 MHz, Chloroform-d) δ 8.87 (br. s., 2H), 5.81-5.64 (m, 1H), 5.28-5.09 (m, 2H), 3.56-3.40 (m, 2H), 3.39-3.25 (m, 1H), 3.10-2.91 (m, 2H), 2.32-2.16 (m, 1H), 1.96-1.79 (m, 1H) ppm. $^{19}$F NMR (282 MHz, Chloroform-d) δ -75.96 (s, 3F) ppm. ESI-MS m/z calc. 97.08915, found 98.2 (M+1)$^+$; Retention time: 0.33 minutes (LC Method 0).

Step 3: 9H-Fluoren-9-ylmethyl 3-vinylpyrrolidine-1-carboxylate

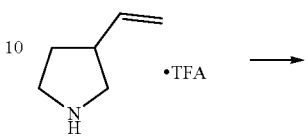

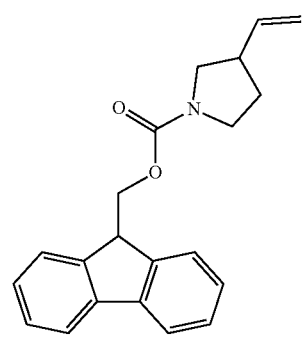

9H-Fluoren-9-ylmethyl carbonochloridate (550 mg, 2.126 mmol) was added to 3-vinylpyrrolidine (trifluoroacetate salt) (500 mg, 1.4206 mmol) and diisopropylethylamine (556.50 mg, 0.75 mL, 4.3058 mmol) in dichloromethane (20 mL) at room temperature. The solution was stirred for 2 days then water (20 mL) was added and extracted the mixture with DCM (2×20 mL). The organic phases were combined, dried over anhydrous sodium sulfate, filtered and concentrated. The residue was purified by silica gel chromatography using a gradient from 0% to 20% of ethyl acetate in heptanes giving as a clear oil, 9H-fluoren-9-ylmethyl 3-vinylpyrrolidine-1-carboxylate (458 mg, 100%). $^1$H NMR (300 MHz, DMSO-d6) δ 1.54-1.75 (m, 1H), 1.84-2.04 (m, 1H), 2.66-2.85 (m, 1H), 2.90-3.05 (m, 1H), 3.13-3.27 (m, 1H), 3.28-3.49 (m, 2H), 4.15-4.37 (m, 3H), 4.93-5.18 (m, 2H), 5.69-5.87 (m, 1H), 7.2-7.47 (m, 4H), 7.62 (d, J=7.3 Hz, 2H), 7.88 (d, J=7.6 Hz, 2H) ppm. ESI-MS m/z calc. 319.15723, found 320.2 (M+1)$^+$; Retention time: 2.36 minutes (LC Method B).

Step 4: 9H-Fluoren-9-ylmethyl 3-[5-benzyloxy-5-[5-[6-bromo-3-(tert-butoxycarbonylamino)-5-(trifluoromethyl)-2-pyridyl]-1,3,4-oxadiazol-2-yl]-6,6,6-trifluoro-hex-1-enyl]pyrrolidine-1-carboxylate (E/Z mixture)

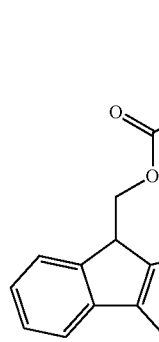

+

251

-continued

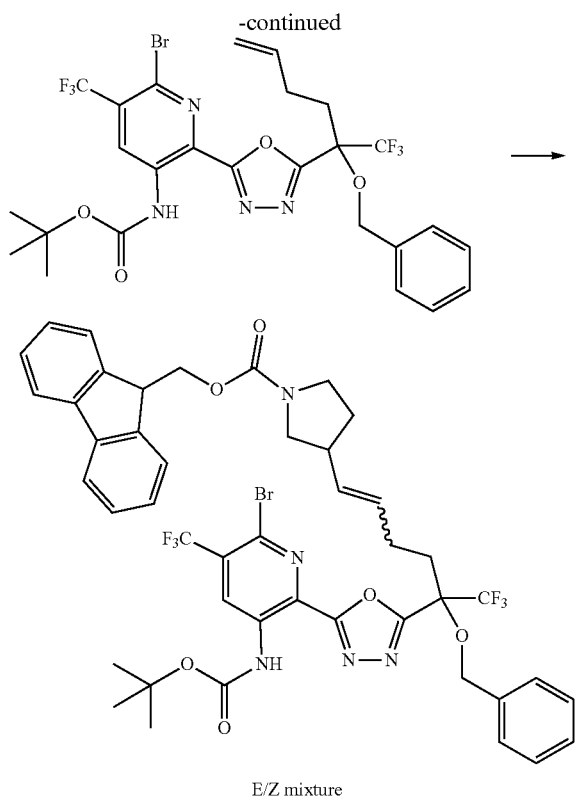

E/Z mixture

To a degassed solution of tert-butyl N-[2-[5-[1-benzyloxy-1-(trifluoromethyl)pent-4-enyl]-1,3,4-oxadiazol-2-yl]-6-bromo-5-(trifluoromethyl)-3-pyridyl]carbamate (1.63 g, 2.5023 mmol) and 9H-fluoren-9-ylmethyl 3-vinylpyrrolidine-1-carboxylate (3.6 g, 11.271 mmol) in 1,2-dichloroethane (8 mL) was added Grubbs catalyst, 2nd generation (129 mg, 0.1516 mmol). The resultant mixture was stirred at 40° C. overnight. The reaction mixture was cooled to room temperature and concentrated. The residue was purified by silica gel chromatography using a gradient from 0% to 30% ethyl acetate in heptanes giving as an off-white solid, 9H-fluoren-9-ylmethyl 3-[5-benzyloxy-5-[5-[6-bromo-3-(tert-butoxycarbonylamino)-5-(trifluoromethyl)-2-pyridyl]-1,3,4-oxadiazol-2-yl]-6,6,6-trifluoro-hex-1-enyl]pyrrolidine-1-carboxylate (E/Z mixture) (1.3 g, 47%). $^1$H NMR (300 MHz, Chloroform-d) δ 1.56 (s, 9H), 1.60-1.76 (m, 1H), 1.90-2.03 (m, 1H), 2.10-2.23 (m, 1H), 2.28-2.55 (m, 3H), 2.65-2.85 (m, 1H), 3.01-3.14 (m, 1H), 3.29-3.43 (m, 1H), 3.47-3.64 (m, 2H), 4.18-4.29 (m, 1H), 4.31-4.41 (m, 2H), 4.63-4.74 (m, 1H), 4.76-4.88 (m, 1H), 5.37-5.56 (m, 2H), 7.28-7.45 (m, 7H), 7.47-7.55 (m, 2H), 7.57-7.65 (m, 2H), 7.73-7.81 (m, 2H), 9.35 (s, 1H), 10.16-10.22 (m, 1H) ppm. $^{19}$F NMR (282 MHz, Chloroform-d) δ −72.5 (br. s., 3F), −63.8 (br. s., 3F) ppm. Retention time: 2.96 minutes (LC Method K).

252

Step 5: 9H-Fluoren-9-ylmethyl 3-[5-benzyloxy-5-[5-[6-bromo-3-(tert-butoxycarbonylamino)-5-(trifluoromethyl)-2-pyridyl]-1,3,4-oxadiazol-2-yl]-6,6,6-trifluoro-hexyl]pyrrolidine-1-carboxylate

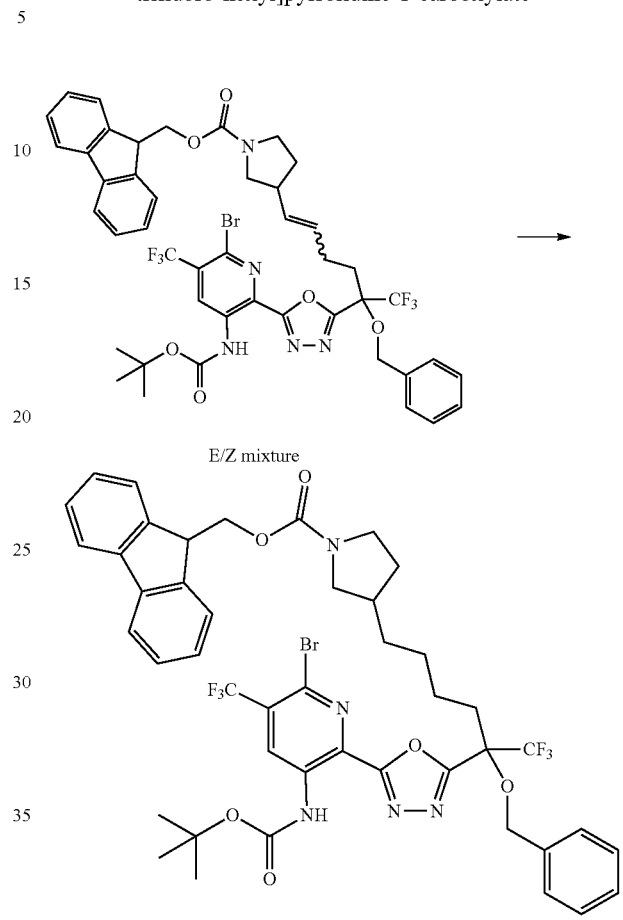

E/Z mixture

To a nitrogen degassed solution of 9H-fluoren-9-ylmethyl 3-[5-benzyloxy-5-[5-[6-bromo-3-(tert-butoxycarbonylamino)-5-(trifluoromethyl)-2-pyridyl]-1,3,4-oxadiazol-2-yl]-6,6,6-trifluoro-hex-1-enyl]pyrrolidine-1-carboxylate (E/Z mixture) (205 mg, 0.2175 mmol) in ethyl acetate (16 mL) was added palladium on carbon (46 mg, 0.0216 mmol) and the reaction was stirred for 2 h under a hydrogen balloon at room temperature. The reaction mixture was filtered over Celite, washed with ethyl acetate and the filtrate was evaporated to give as an amber gum, 9H-fluoren-9-ylmethyl 3-[5-benzyloxy-5-[5-[6-bromo-3-(tert-butoxycarbonylamino)-5-(trifluoromethyl)-2-pyridyl]-1,3,4-oxadiazol-2-yl]-6,6,6-trifluoro-hexyl]pyrrolidine-1-carboxylate (190 mg, 92%). $^1$H NMR (300 MHz, Chloroform-d) δ 1.34-1.46 (m, 4H), 1.56 (s, 9H), 1.91-2.18 (m, 3H), 2.25-2.50 (m, 3H), 2.85-2.99 (m, 1H), 3.25-3.40 (m, 1H), 3.44-3.66 (m, 3H), 4.18-4.29 (m, 1H), 4.30-4.41 (m, 2H), 4.63-4.74 (m, 1H), 4.75-4.85 (m, 1H), 7.26-7.44 (m, 7H), 7.46-7.54 (m, 2H), 7.56-7.65 (m, 2H), 7.72-7.80 (m, 2H), 9.34 (s, 1H), 10.19 (br. s., 1H) ppm. $^{19}$F NMR (282 MHz, Chloroform-d) δ −72.5 (br. s., 3F), −63.8 (br. s., 3F) ppm. Retention time: 2.97 minutes (LC Method K).

Step 6: tert-Butyl N-[2-[5-[1-benzyloxy-5-pyrrolidin-3-yl-1-(trifluoromethyl)pentyl]-1,3,4-oxadiazol-2-yl]-6-bromo-5-(trifluoromethyl)-3-pyridyl]carbamate

Step 7: tert-Butyl N-[10-(benzyloxy)-10,18-bis(trifluoromethyl)-20-oxa-2,12,13,19-tetraazatetracyclo[13.3.1.12,5.111,14]henicosa-1(18),11,13,15(19),16-pentaen-16-yl]carbamate

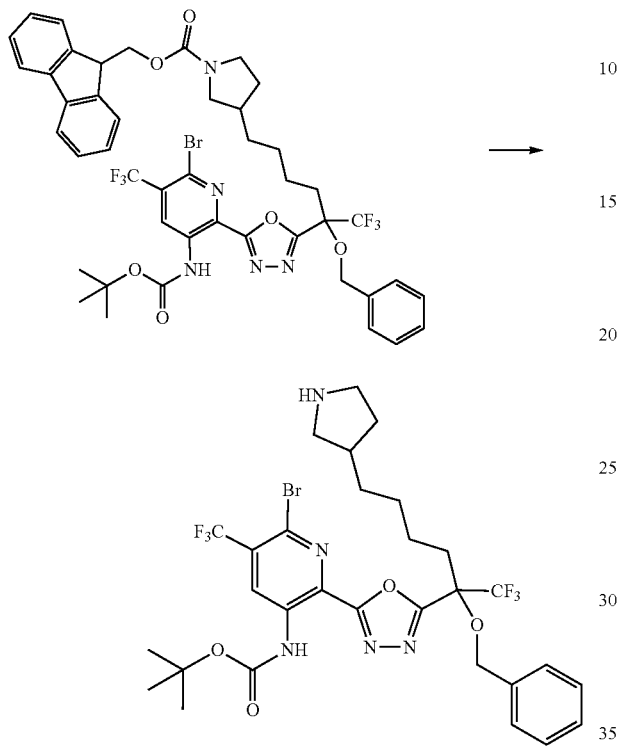

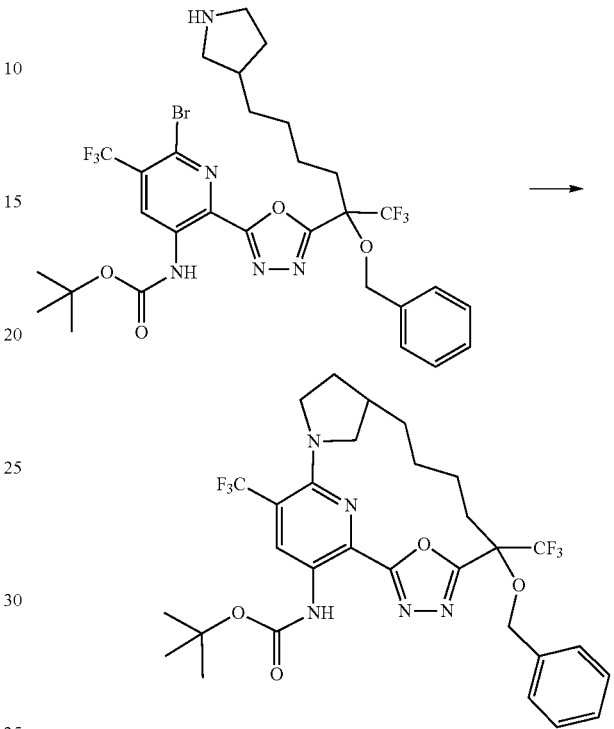

Piperidine (172.20 mg, 0.2 mL, 2.0224 mmol) was added to 9H-fluoren-9-ylmethyl 3-[5-benzyloxy-5-[5-[6-bromo-3-(tert-butoxycarbonylamino)-5-(trifluoromethyl)-2-pyridyl]-1,3,4-oxadiazol-2-yl]-6,6,6-trifluoro-hexyl]pyrrolidine-1-carboxylate (75 mg, 0.0794 mmol) in THF (5 mL) and the mixture was stirred overnight at room temperature then concentrated under reduced pressure. The residue was purified by reverse phase ($C_{18}$ column) chromatography using a gradient from 5% to 70% to 100% of methanol in water containing 0.1% formic acid giving as a clear oil, tert-butyl N-[2-[5-[1-benzyloxy-5-pyrrolidin-3-yl-1-(trifluoromethyl)pentyl]-1,3,4-oxadiazol-2-yl]-6-bromo-5-(trifluoromethyl)-3-pyridyl]carbamate (27 mg, 43%). $^{1}$H NMR (300 MHz, Chloroform-d) δ 1.31-1.47 (m, 4H), 1.49-1.71 (m, 10H), 1.96-2.25 (m, 4H), 2.26-2.44 (m, 2H), 2.62-2.74 (m, 1H), 3.07-3.19 (m, 1H), 3.22-3.42 (m, 2H), 4.64-4.73 (m, 1H), 4.74-4.83 (m, 1H), 7.29-7.44 (m, 3H), 7.44-7.53 (m, 2H), 8.42 (br. s, 1H), 9.35 (s, 1H), 10.18 (s, 1H) ppm. $^{19}$F NMR (282 MHz, Chloroform-d) δ –72.5 (br. s., 3F), –63.8 (s, 3F) ppm. ESI-MS m/z calc. 721.16986, found 722.2 (M+1)$^{+}$; Retention time: 2.01 minutes (LC Method K).

DIPEA (51.940 mg, 0.07 mL, 0.4019 mmol) was added to tert-butyl N-[2-[5-[1-benzyloxy-5-pyrrolidin-3-yl-1-(trifluoromethyl)pentyl]-1,3,4-oxadiazol-2-yl]-6-bromo-5-(trifluoromethyl)-3-pyridyl]carbamate (32 mg, 0.0443 mmol) in acetonitrile (7 mL) and the mixture was heated at 80° C. overnight. The mixture was poured in saturated sodium bicarbonate solution (50 mL) and extracted with ethyl acetate (3×50 mL). The organic phases were combined, washed with brine (50 mL), dried on anhydrous sodium sulfate, filtered and concentrated. The residue was purified by silica gel chromatography using a gradient from 0% to 10% of ethyl acetate in heptanes giving as a green-yellow gum, tert-butyl N-[10-(benzyloxy)-10,18-bis(trifluoromethyl)-20-oxa-2,12,13,19-tetraazatetracyclo[13.3.1.12, 5.111,14]henicosa-1(18),11,13,15(19),16-pentaen-16-yl]carbamate (23 mg, 79%). $^{1}$H NMR (300 MHz, Chloroform-d): δ 9.03-9.32 (m, 1H), 8.90-9.01 (m, 1H), 7.19-7.30 (m, 5H), 4.61-4.83 (m, 2H), 4.44-4.59 (m, 1H), 4.10-4.19 (m, 1H), 3.28-3.51 (m, 2H), 3.09-3.26 (m, 1H), 2.52-2.68 (m, 1H), 2.20-2.38 (m, 1H), 1.93-2.17 (m, 3H), 1.73-1.92 (m, 1H), 1.39-1.60 (m, 9H), 1.22-1.37 (m, 4H) ppm. $^{19}$F NMR (282 MHz, Chloroform-d) δ–60.41 (s, 1.5F), –60.90 (s, 1.5F), –74.03 (s, 1.5F), –74.94 (br. s., 1.5F) ppm. ESI-MS m/z calc. 641.24365, found 642.2 (M+1)$^{+}$; Retention time: 3.14 minutes (LC Method O).

255

Step 8: 10-(Benzyloxy)-10,18-bis(trifluoromethyl)-20-oxa-2,12,13,19-tetraazatetracyclo[13.3.1.12,5.111,14]henicosa-1(18),11,13,15(19),16-pentaen-16-amine

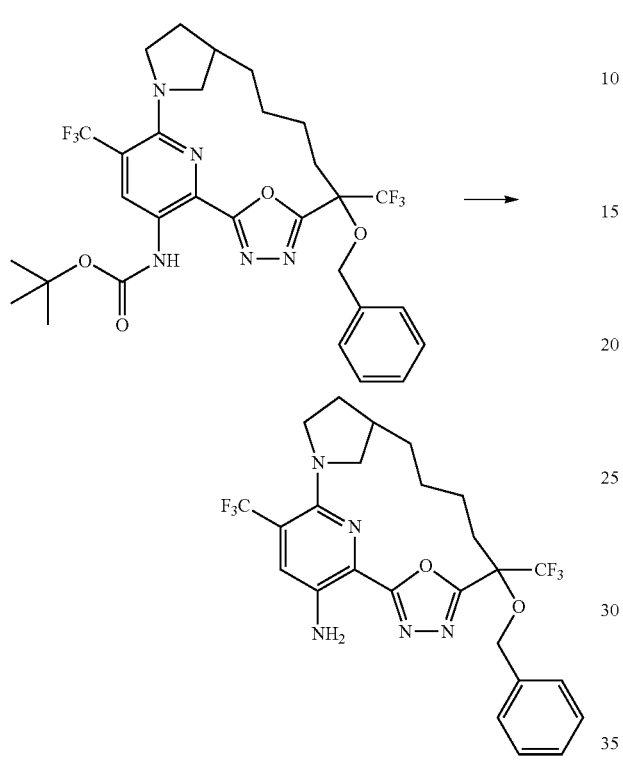

TFA (1.4800 g, 1 mL, 12.98 mmol) was added to tert-butyl N-[10-(benzyloxy)-10,18-bis(trifluoromethyl)-20-oxa-2,12,13,19-tetraazatetracyclo[13.3.1.12,5.111,14]henicosa-1(18),11,13,15(19),16-pentaen-16-yl]carbamate (60 mg, 0.0935 mmol) in DCM (2 mL) at room temperature, and the mixture was stirred for 2 h. The mixture was poured in saturated sodium bicarbonate solution (20 mL) and extracted with DCM (3×10 mL). The organic phases were combined, dried over anhydrous sodium sulfate, filtered and concentrated giving as a green-yellow-gum, 10-(benzyloxy)-10,18-bis(trifluoromethyl)-20-oxa-2,12,13,19-tetraazatetracyclo[13.3.1.12,5.111,14]henicosa-1(18),11,13,15(19),16-pentaen-16-amine (36 mg, 71%). $^1$H NMR (300 MHz, Chloroform-d) δ 7.34 (s, 1H), 7.29-7.13 (m, 5H), 5.51-5.06 (m, 2H), 4.85-4.72 (m, 1H), 4.71-4.60 (m, 1H), 4.59-4.43 (m, 1H), 3.53-3.27 (m, 1H), 3.25-2.84 (m, 2H), 2.70-2.50 (m, 1H), 2.43-2.21 (m, 1H), 2.14-1.91 (m, 3H), 1.66-1.28 (m, 6H) ppm. $^{19}$F NMR (282 MHz, Chloroform-d): 6-62.15 to −60.08 (m, 3F), −75.57 to −73.50 (m, 3F) ppm. ESI-MS m/z calc. 541.1912, found 542.1 (M+1)$^+$; Retention time: 2.65 minutes (LC Method 0).

256

Step 9: 16-Amino-10,18-bis(trifluoromethyl)-20-oxa-2,12,13,19-tetraazatetracyclo[13.3.1.12,5.111,14]henicosa-1(19),11,13,15,17-pentaen-10-ol

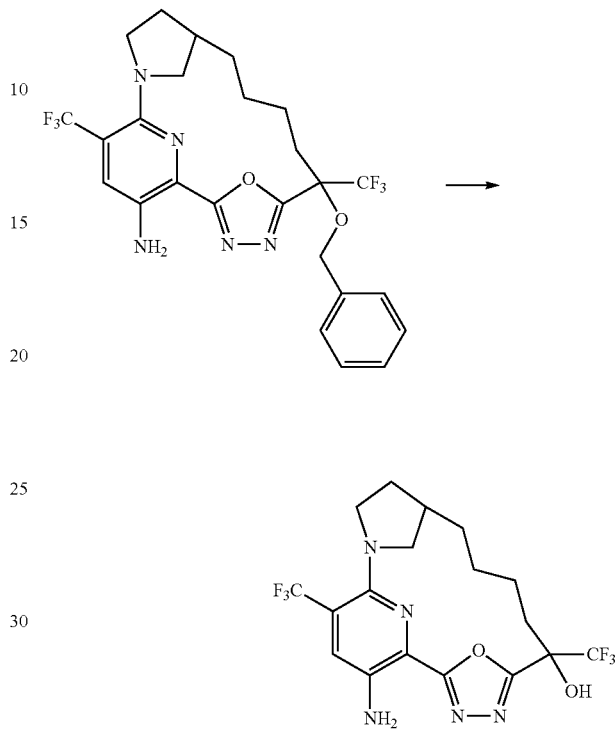

To a nitrogen degassed solution of 10-(benzyloxy)-10,18-bis(trifluoromethyl)-20-oxa-2,12,13,19-tetraazatetracyclo[13.3.1.12,5.111,14]henicosa-1(18),11,13,15(19),16-pentaen-16-amine (42 mg, 0.0776 mmol) in methanol (6 mL) was added SiliaCat Pd$^0$ (120 mg, 0.24 mmol/g, 0.0288 mmol) and the reaction was stirred for 2 days under a hydrogen balloon at room temperature. The reaction mixture was filtered over Celite, washed with methanol and the filtrate was evaporated. The residue was purified by silica gel chromatography using a gradient from 0% to 30% of ethyl acetate in heptanes giving as a yellow solid and racemic mixture of 4 stereoisomers, 16-amino-10,18-bis(trifluoromethyl)-20-oxa-2,12,13,19-tetraazatetracyclo[13.3.1.12,5.111,14]henicosa-1(19),11,13,15,17-pentaen-10-ol (17 mg, 48%). $^1$H NMR (300 MHz, DMSO-d6) δ 7.70-7.64 (m, 1H), 7.60-7.54 (m, 1H), 6.52 (br. s, 1H), 6.36 (br. s, 1H), 4.49-4.32 (m, 1H), 4.19-4.04 (m, 1H), 3.04-2.83 (m, 2H), 2.21-1.82 (m, 5H), 1.65-1.25 (m, 6H) ppm. $^{19}$F NMR (282 MHz, DMSO-d6) δ−59.86 (br. s., 1.5F), −60.32 (br. s., 1.5F), −77.43 (br. s., 1.5F), −78.51 (br. s., 1.5F) ppm. ESI-MS m/z calc. 451.1443, found 452.2 (M+1)$^+$; Retention time: 3.52 minutes (LC Method C).

Step 10: 16-Amino-10,18-bis(trifluoromethyl)-20-oxa-2,12,13,19-tetraazatetracyclo[13.3.1.1² ,⁵.1¹¹,¹⁴]henicosa-1(19),11,13,15,17-pentaen-10-ol (diastereomer pair 1) (Compound 8) and 16-amino-10,18-bis(trifluoromethyl)-20-oxa-2,12,13,19-tetraazatetracyclo[13.3.1.1² ,⁵.1¹¹,¹⁴]henicosa-1(19),11,13,15,17-pentaen-10-ol (diastereomer pair 2) (Compound 9)

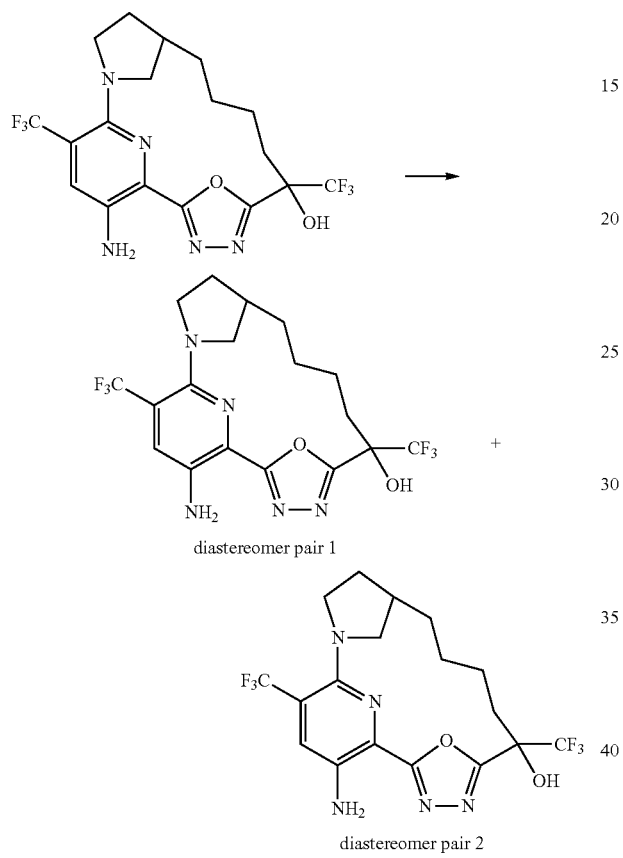

16-Amino-10,18-bis(trifluoromethyl)-20-oxa-2,12,13,19-tetraazatetracyclo[13.3.1.1² ,⁵.1¹¹,¹⁴]henicosa-1(19),11,13,15,17-pentaen-10-ol (14 mg, 0.03102 mmol), a racemic mixture of 4 stereoisomers, was purified by reverse phase preparative chromatography using a $C_{18}$ column and a gradient from 30% to 65% acetonitrile in water containing 5 mM hydrochloric acid for 30 min giving two separate pairs of diastereomers:

The first pair of diastereomers to elute was isolated as 16-amino-10,18-bis(trifluoromethyl)-20-oxa-2,12,13,19-tetraazatetracyclo[13.3.1.1² ,⁵.1¹¹,¹⁴]henicosa-1(19),11,13,15,17-pentaen-10-ol (diastereomer pair 1) (5.6 mg, 78%). ESI-MS m/z calc. 451.1443, found 452.0 (M+1)⁺; Retention time: 1.58 minutes (LC Method A).

The second pair of diastereomers to elute was isolated as 16-amino-10,18-bis(trifluoromethyl)-20-oxa-2,12,13,19-tetraazatetracyclo[13.3.1.1² ,⁵.1¹¹,¹⁴]henicosa-1(19),11,13,15,17-pentaen-10-ol (diastereomer pair 2) (1.7 mg, 24%). ESI-MS m/z calc. 451.1443, found 452.0 (M+1)⁺; Retention time: 1.62 minutes (LC Method A).

Example 7: Preparation of (6E,12R)-6,18-bis(trifluoromethyl)-22-oxa-3,4,16,21-tetraazatetracyclo[15.3.1.1² ,⁵.0¹² ,¹⁶]docosa-1(21),2,4,6,17,19-hexaen-20-amine (Compound 10)

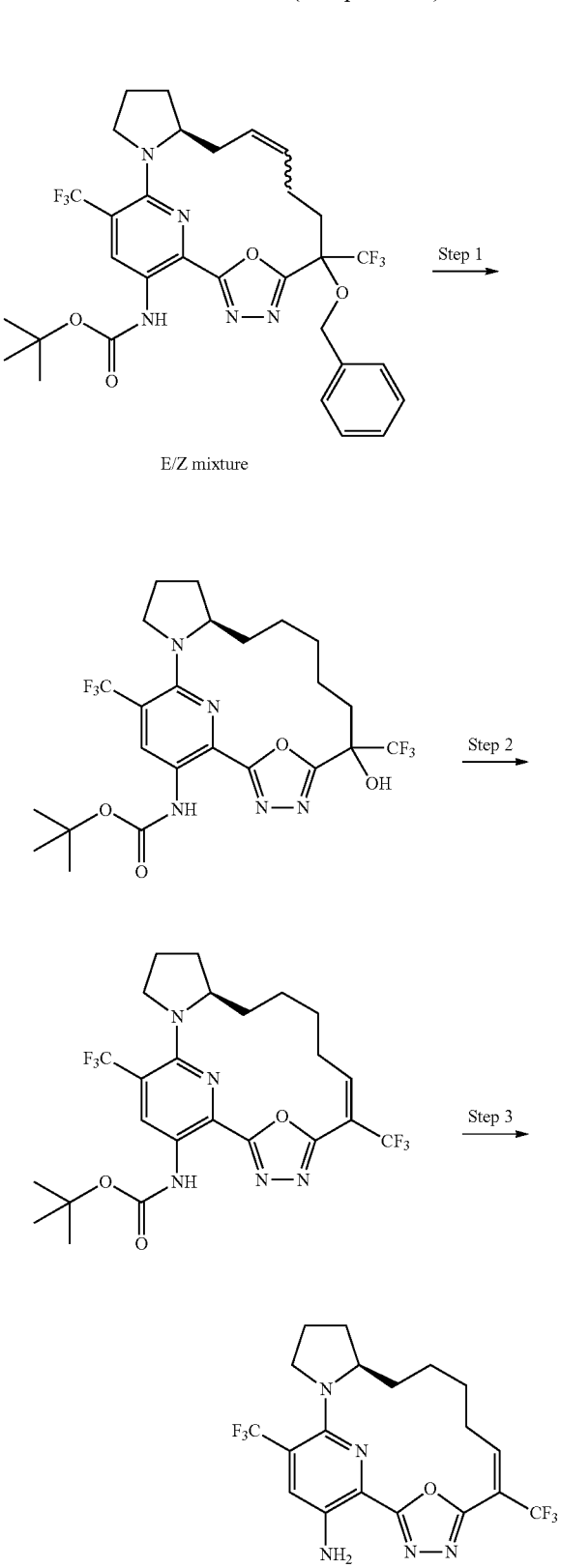

Step 1: tert-Butyl N-[(12R)-6-hydroxy-6,18-bis(trifluoromethyl)-22-oxa-3,4,16,21-tetrazatetracyclo[15.3.1.1²,⁵.0¹²,¹⁶]docosa-1(20),2,4,17(21),18-pentaen-20-yl]carbamate

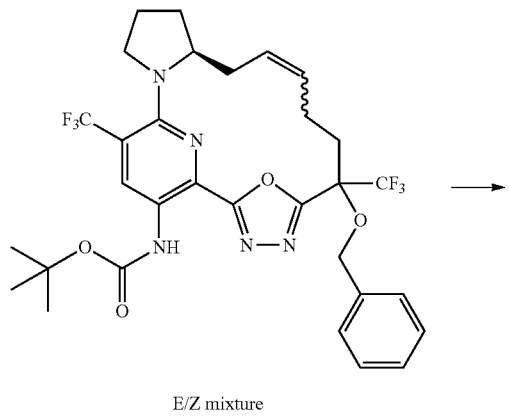

E/Z mixture

Into a solution of tert-butyl N-[(12S)-6-benzyloxy-6,18-bis(trifluoromethyl)-22-oxa-3,4,16,21-tetrazatetracyclo[15.3.1.1²,⁵.0¹²,¹⁶]docosa-1(20),2,4,9,17(21),18-hexaen-20-yl]carbamate (E/Z mixture) (6.87 g, 10.090 mmol) in MeOH (150 mL) in a hydrogenation vessel was added 10% Pd/C (2.7 g, 2.5371 mmol). The reaction mixture was purged with nitrogen three times then back-filled with hydrogen two times before it was subjected to 60 psi hydrogenation for 67 h. The reaction mixture was filtered over a bed of Celite and the filter bed was washed with MeOH (3×100 mL). The combined filtrates were concentrated by rotary evaporation yielding as a yellow solid, tert-butyl N-[(12R)-6-hydroxy-6,18-bis(trifluoromethyl)-22-oxa-3,4,16,21-tetrazatetracyclo[15.3.1.1²,⁵.0¹²,¹⁶]docosa-1(20),2,4,17(21),18-pentaen-20-yl]carbamate (5.71 g, 95%). ESI-MS m/z calc. 565.2124, found 566.5 (M+1)⁺; Retention time: 3.92 minutes. This material was used in the subsequent step without further purification (LC Method G).

Step 2: tert-Butyl N-[(6E,12R)-6,18-bis(trifluoromethyl)-22-oxa-3,4,16,21-tetraazatetracyclo[15.3.1.1²,⁵.0¹²,¹⁶]docosa-1(21),2,4,6,17,19-hexaen-20-yl]carbamate

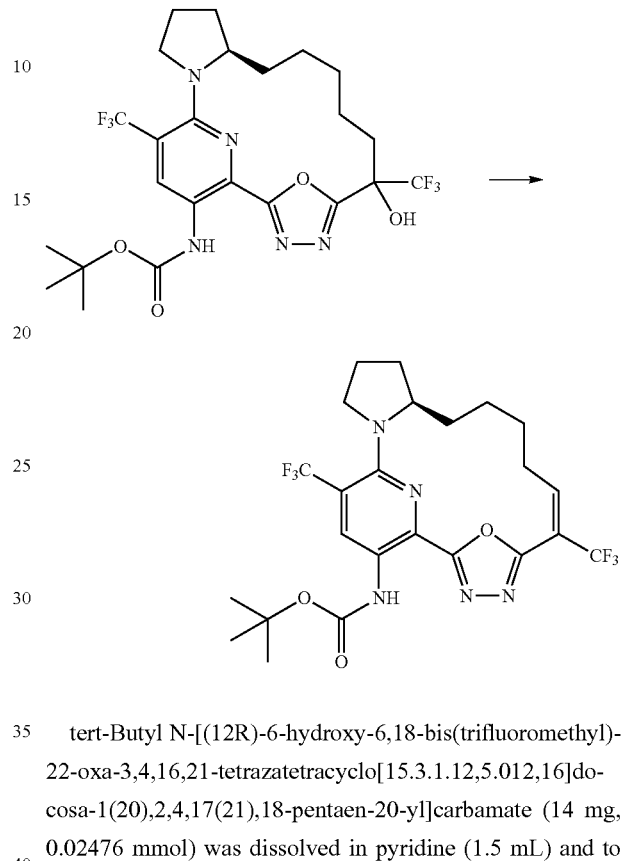

tert-Butyl N-[(12R)-6-hydroxy-6,18-bis(trifluoromethyl)-22-oxa-3,4,16,21-tetrazatetracyclo[15.3.1.1²,⁵.0¹²,¹⁶]docosa-1(20),2,4,17(21),18-pentaen-20-yl]carbamate (14 mg, 0.02476 mmol) was dissolved in pyridine (1.5 mL) and to the solution was slowly added POCl₃ (105 µL, 1.126 mmol). The mixture was sealed and heated at 50° C. for 20 h. The reaction mixture was then cooled to room temperature and diluted with methanol then filtered. The resulting material was purified by reverse-phase preparative chromatography utilizing a C₁₈ column eluting with 50% to 99% acetonitrile in water (+5 mM HCl) using a 15 minute run to afford as a yellow solid, tert-butyl N-[(6E,12R)-6,18-bis(trifluoromethyl)-22-oxa-3,4,16,21-tetraazatetracyclo[15.3.1.1²,⁵.0¹²,¹⁶]docosa-1(21),2,4,6,17,19-hexaen-20-yl]carbamate (6.4 mg, 47%). ¹H NMR (500 MHz, DMSO-d6) δ 9.13 (s, 1H), 8.69 (s, 1H), 7.41 (t, J=9.1 Hz, 1H), 4.26 (q, J=8.7 Hz, 1H), 3.59 (q, J=8.6, 8.2 Hz, 1H), 3.50-3.40 (m, 1H), 3.04 (d, J=12.4 Hz, 1H), 2.44 (t, J=12.7 Hz, 1H), 2.26-2.17 (m, 1H), 2.13-2.08 (m, 1H), 1.99 (s, 1H), 1.78 (t, J=11.1 Hz, 2H), 1.70 (d, J=11.6 Hz, 1H), 1.63-1.56 (m, 1H), 1.51 (s, 9H), 1.48 (s, 1H), 1.25 (s, 1H), 1.18-1.08 (m, 1H) ppm. ESI-MS m/z calc. 547.2018, found 548.1 (M+1)⁺; Retention time: 1.84 minutes (LC Method M).

Step 3: (6E,12R)-6,18-Bis(trifluoromethyl)-22-oxa-3,4,16,21-tetraazatetracyclo[15.3.1.12,5.012,16]docosa-1(21),2,4,6,17,19-hexaen-20-amine (Compound 10)

Example 8: Preparation of (12R)-6,18-bis(trifluoromethyl)-22-oxa-3,4,16,21-tetraazatetracyclo[15.3.1.12,5.012,16]docosa-1(21),2,4,17,19-pentaen-20-amine (enantiomer 1) (Compound 11) and (12R)-6,18-bis(trifluoromethyl)-22-oxa-3,4,16,21-tetraazatetracyclo[15.3.1.12,5.012,16]docosa-1(21),2,4,17,19-pentaen-20-amine (enantiomer 2) (Compound 12)

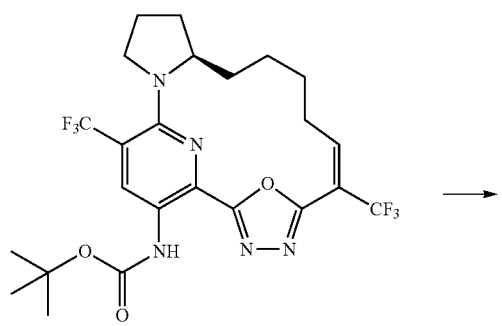

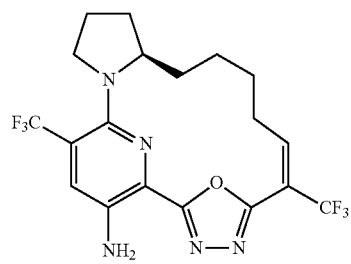

To a solution of tert-butyl N-[(6E,12R)-6,18-bis(trifluoromethyl)-22-oxa-3,4,16,21-tetraazatetracyclo[15.3.1.12,5.012,16]docosa-1(21),2,4,6,17,19-hexaen-20-yl]carbamate (17 mg, 0.03105 mmol) in DCM (0.50 mL) was slowly added TFA (0.4 mL, 5.192 mmol). The reaction mixture was stirred at room temperature for 1 h. The solvent was evaporated and the residue was purified by silica gel chromatography using DCM (15 mL) providing (6E,12R)-6,18-bis(trifluoromethyl)-22-oxa-3,4,16,21-tetraazatetracyclo[15.3.1.12,5.012,16]docosa-1(21),2,4,6,17,19-hexaen-20-amine (11 mg, 78%). $^1$H NMR (400 MHz, Chloroform-d) δ 7.43 (s, 1H), 7.16-6.96 (m, 1H), 4.59 (bs, 2H), 4.24 (q, J=7.8 Hz, 1H), 3.40 (t, J=9.1 Hz, 1H), 3.00 (qd, J=11.5, 4.2 Hz, 1H), 2.67-2.39 (m, 1H), 2.23 (dtd, J=12.5, 6.4, 3.1 Hz, 1H), 2.07 (dd, J=12.4, 6.1 Hz, 1H), 1.96 (dq, J=13.3, 4.8, 4.4 Hz, 2H), 1.81-1.66 (m, 3H), 1.64-1.48 (m, 2H), 1.26 (s, 1H), 1.15 (td, J=12.1, 6.0 Hz, 1H). ESI-MS m/z calc. 447.14938, found 448.1 (M+1)$^+$; Retention time: 0.43 minutes (LC Method M).

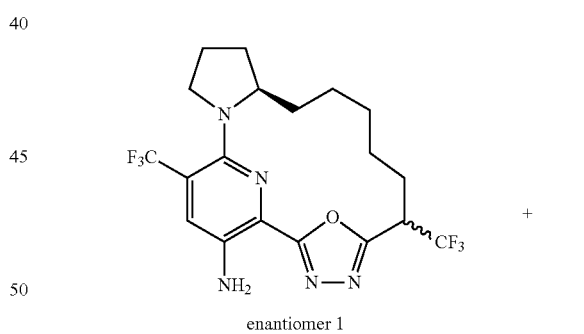

enantiomer 1

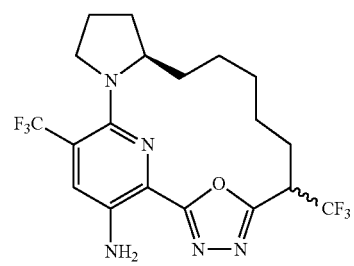

enantiomer 2

263

Step 1: tert-Butyl N-[(12R)-6,18-bis(trifluoromethyl)-22-oxa-3,4,16,21-tetraazatetracyclo[15.3.1.12,5.012,16]docosa-1(21),2,4,17,19-pentaen-20-yl]carbamate

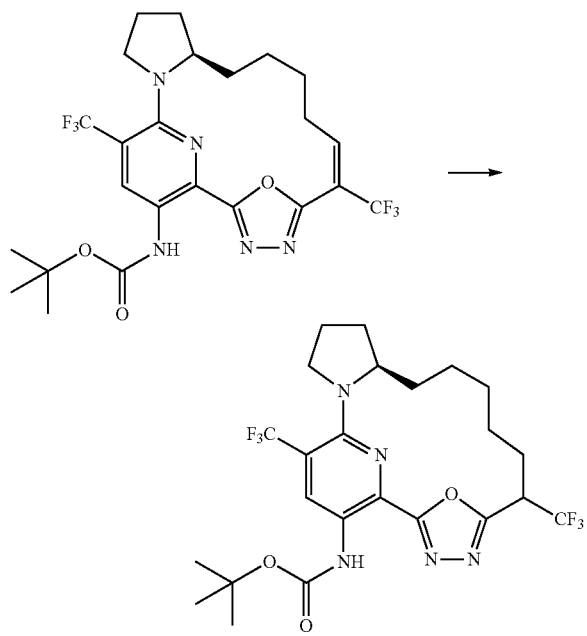

To a solution of tert-butyl N-[(6E,12R)-6,18-bis(trifluoromethyl)-22-oxa-3,4,16,21-tetraazatetracyclo[15.3.1.12,5.012,16]docosa-1(21),2,4,6,17,19-hexaen-20-yl]carbamate (17 mg, 0.03105 mmol) in MeOH (2 mL) was added PtO$_2$ (1.7 mg, 0.007486 mmol). The flask was sealed by a rubber septum. All air was evacuated and filled by nitrogen gas 3 times. Finally, all nitrogen gas was removed, and the flask was connected to a hydrogen balloon. The reaction was stirred for 90 minutes, filtered through Celite and concentrated to give tert-butyl N-[(12R)-6,18-bis(trifluoromethyl)-22-oxa-3,4,16,21-tetraazatetracyclo[15.3.1.12,5.012,16]docosa-1(21),2,4,17,19-pentaen-20-yl]carbamate (14 mg, 82%). ESI-MS m/z calc. 549.21747, found 550.2 (M+1)$^+$; Retention time: 0.88 minutes (LC Method M).

Step 2: (12R)-6,18-bis(trifluoromethyl)-22-oxa-3,4,16,21-tetraazatetracyclo[15.3.1.12,5.012,16]docosa-1(21),2,4,17,19-pentaen-20-amine (enantiomer 1) (Compound 11) and (12R)-6,18-bis(trifluoromethyl)-22-oxa-3,4,16,21-tetraazatetracyclo[15.3.1.12,5.012,16]docosa-1(21),2,4,17,19-pentaen-20-amine (enantiomer 2) (Compound 12)

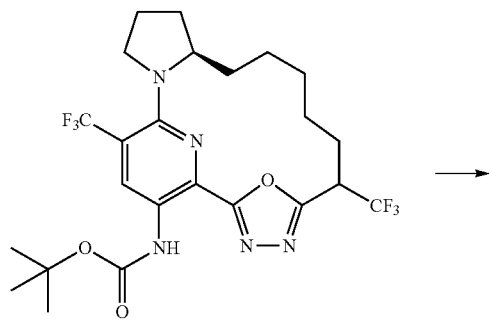

264

-continued

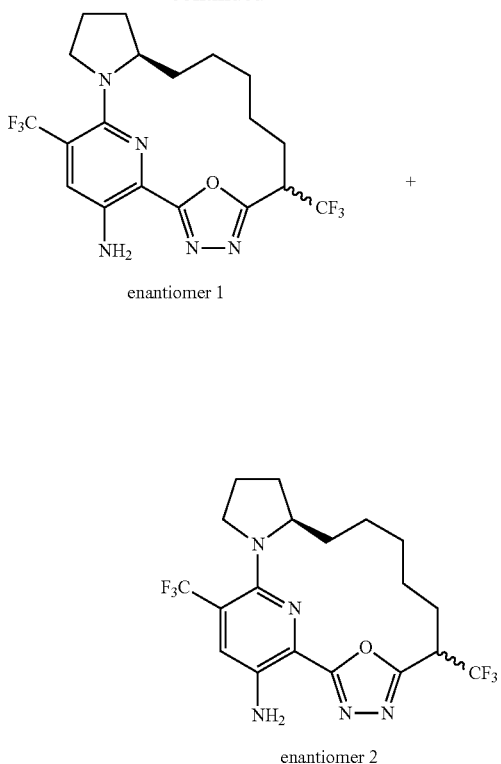

enantiomer 1

+ enantiomer 2

To a solution of tert-butyl N-[(12R)-6,18-bis(trifluoromethyl)-22-oxa-3,4,16,21-tetraazatetracyclo[15.3.1.12,5.012,16]docosa-1(21),2,4,17,19-pentaen-20-yl]carbamate (18 mg, 0.03276 mmol) in DCM (2 mL) was added TFA (1 mL, 12.98 mmol) at room temperature. The mixture was stirred for 45 minutes and concentrated. The residue, dissolved into 1 mL methanol, was subjected to preparative chiral SFC with 70 μL injections through a preparative ChiralCel ODAD column (10×250 mm, 5 μm particle) eluting with 14% MeOH in CO$_2$ giving two single enantiomers:

The first enantiomer to elute was isolated as (12R)-6,18-bis(trifluoromethyl)-22-oxa-3,4,16,21-tetraazatetracyclo[15.3.1.12,5.012,16]docosa-1(21),2,4,17,19-pentaen-20-amine (enantiomer 1) (4.2 mg, 56%). $^1$H NMR (400 MHz, Chloroform-d) δ 7.43 (s, 1H), 3.99 (d, J=8.4 Hz, 1H), 3.82 (ddd, J=11.9, 8.1, 3.0 Hz, 1H), 3.61 (t, J=8.5 Hz, 1H), 3.55 (bs, 2H), 3.43 (t, J=9.3 Hz, 1H), 2.55 (t, J=11.4 Hz, 1H), 2.39 (q, J=12.6 Hz, 1H), 2.17 (dtd, J=12.3, 6.3, 3.5 Hz, 1H), 1.98 (ddt, J=9.8, 6.8, 3.5 Hz, 2H), 1.88-1.75 (m, 1H), 1.57 (m, J=28.4, 17.2, 6.4 Hz, 7H), 0.89 (q, J=9.9, 9.2 Hz, 1H) ppm. ESI-MS m/z calc. 449.16504, found 450.1 (M+1)$^+$; Retention time: 10.21 minutes (LC Method P).

The second enantiomer to elute was isolated as (12R)-6,18-bis(trifluoromethyl)-22-oxa-3,4,16,21-tetraazatetracyclo[15.3.1.12,5.012,16]docosa-1(21),2,4,17,19-pentaen-20-amine (enantiomer 2) (5.0 mg, 65%). $^1$H NMR (400 MHz, Chloroform-d) δ 7.42 (s, 1H), 4.16 (q, J=8.7, 8.2 Hz, 1H), 4.00 (td, J=8.4, 4.4 Hz, 1H), 3.63 (q, J=8.5 Hz, 1H), 3.40 (t, J 9.3 Hz, 1H), 2.78 (bs, 2H), 2.45-2.37 (m, 1H), 2.23-2.1 (m, 3H), 2.03-1.92 (m, 1H), 1.86-1.72 (m, 3H), 1.71-1.57 (m, 2H), 1.52-1.45 (m, 3H), 1.04-0.98 (m, 1H) ppm. ESI-MS m/z calc. 449.16504, found 450.1 (M+1)$^+$; Retention time: 10.03 minutes (LC Method P).

Example 9: Preparation of (6R,12R)-20-(methylamino)-6,18-bis(trifluoromethyl)-22-oxa-3,4,16,21-tetraazatetracyclo[15.3.1.1²,⁵.0¹²,¹⁶]docosa-1(21),2,4,17,19-pentaen-6-ol (Compound 13)

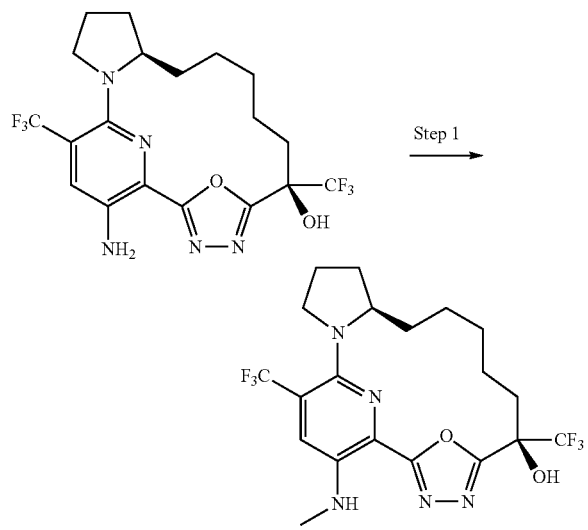

Step 1: (6R,12R)-20-(Methylamino)-6,18-bis(trifluoromethyl)-22-oxa-3,4,16,21-tetraazatetracyclo[15.3.1.1²,⁵.0¹²,¹⁶]docosa-1(21),2,4,17,19-pentaen-6-ol (Compound 13)

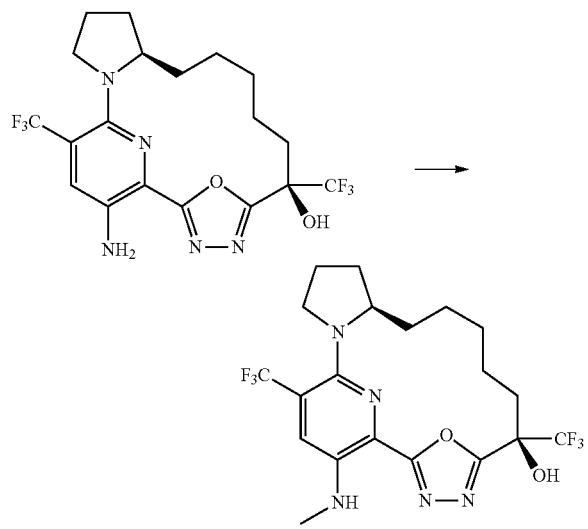

To a solution of (6R,12R)-20-amino-6,18-bis(trifluoromethyl)-22-oxa-3,4,16,21-tetraazatetracyclo[15.3.1.1²,⁵.0¹²,¹⁶]docosa-1(21),2,4,17,19-pentaen-6-ol (30 mg, 0.06446 mmol) in DMF (0.6 mL) at room temperature was added [bis(trimethylsilyl)amino]sodium (142 μL of 1 M, 0.142 mmol) and then iodomethane (71 μL of 1 M, 0.071 mmol) in THF. The mixture was stirred at room temperature for 1 h. The reaction was diluted with ether and washed with aqueous 1 M $NH_4Cl$. The organic layer was dried ($MgSO_4$), filtered and evaporated. The residue was purified by silica gel chromatography using a gradient from 10% to 35% EtOAc in hexanes (12 g column) giving as an orange solid, (6R,12R)-20-(methylamino)-6,18-bis(trifluoromethyl)-22-oxa-3,4,16,21-tetraazatetracyclo[15.3.1.1²,⁵.0¹²,¹⁶]docosa-1(21),2,4,17,19-pentaen-6-ol (13.3 mg, 43%). $^1$H NMR (400 MHz, DMSO-d6) δ 7.61 (s, 1H), 7.51 (s, 1H), 6.31 (q, J=5.4 Hz, 1H), 3.91 (q, J=8.3 Hz, 1H), 3.54 (q, J=8.7 Hz, 1H), 3.32-3.24 (m, 1H), 2.97 (d, J=4.9 Hz, 3H), 2.29 (t, J=13.0 Hz, 1H), 2.14 (s, 1H), 2.02-1.89 (m, 3H), 1.85-1.68 (m, 1H), 1.51 (d, J 24.3 Hz, 7H), 0.84 (d, J=12.2 Hz, 1H) ppm. $^{19}$F NMR (376 MHz, DMSO-d6) δ −55.43, −79.24 ppm. ESI-MS m/z calc. 479.1756, found 480.1 (M+1)$^+$; Retention time: 1.94 minutes (LC Method Q).

Example 10: Preparation of (6R,12R)-20-(ethylamino)-6,18-bis(trifluoromethyl)-22-oxa-3,4,16,21-tetraazatetracyclo[15.3.1.1²,⁵.0¹²,¹⁶]docosa-1(21),2,4,17,19-pentaen-6-ol (Compound 14)

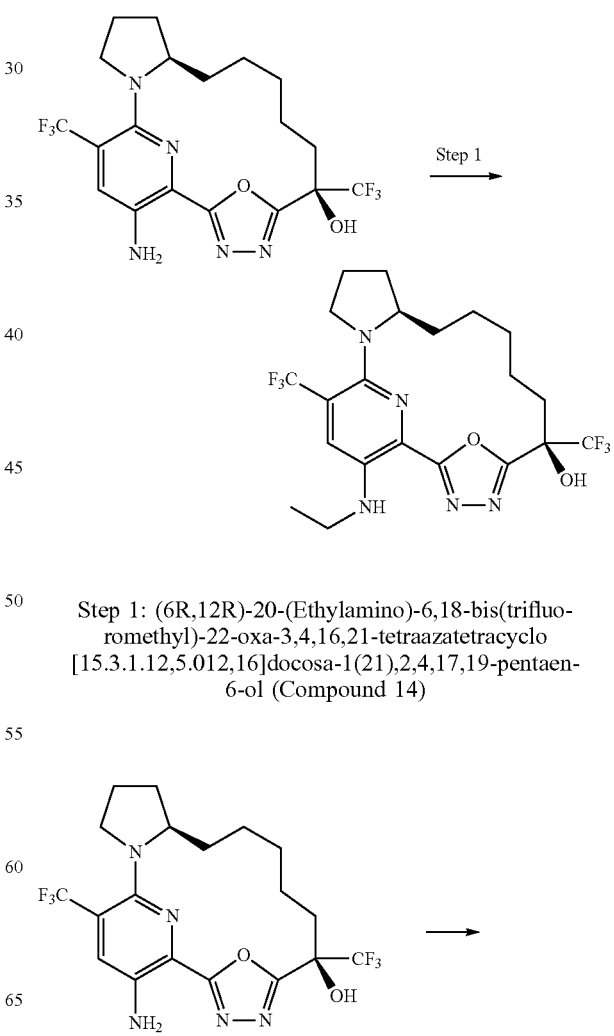

Step 1: (6R,12R)-20-(Ethylamino)-6,18-bis(trifluoromethyl)-22-oxa-3,4,16,21-tetraazatetracyclo[15.3.1.1²,⁵.0¹²,¹⁶]docosa-1(21),2,4,17,19-pentaen-6-ol (Compound 14)

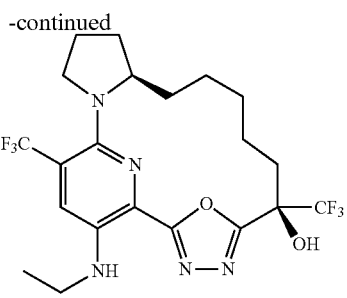

To a solution of (6R,12R)-20-amino-6,18-bis(trifluoromethyl)-22-oxa-3,4,16,21-tetraazatetracyclo[15.3.1.12,5.012,16]docosa-1(21),2,4,17,19-pentaen-6-ol (30 mg, 0.06446 mmol) in DMF (0.6 mL) at room temperature was added [bis(trimethylsilyl)amino]sodium (142 μL of 1 M, 0.142 mmol) and then bromoethane (71 μL of 1 M, 0.071 mmol) in THF. The mixture was stirred at room temperature for 1 h, diluted with ether and washed with aqueous 1 M NH$_4$Cl and the organic layer dried over MgSO$_4$, filtered and evaporated. The residue was purified by silica gel chromatography using a gradient from 10% to 35% EtOAc in hexanes (12 g column) giving as an orange solid, (6R,12R)-20-(ethylamino)-6,18-bis(trifluoromethyl)-22-oxa-3,4,16,21-tetraazatetracyclo[15.3.1.12,5.012,16]docosa-1(21),2,4,17,19-pentaen-6-ol (18.4 mg, 58%). $^1$H NMR (400 MHz, DMSO-d6) δ 7.60 (s, 1H), 7.55 (s, 1H), 6.23 (t, J=5.7 Hz, 1H), 3.98-3.85 (m, 1H), 3.54 (q, J=8.6 Hz, 1H), 3.37 (m, 3H), 2.29 (t, J=13.7 Hz, 1H), 2.14 (m, 1H), 2.03-1.88 (m, 2H), 1.83-1.70 (m, 1H), 1.65-1.36 (m, 8H), 1.22 (t, J=7.0 Hz, 3H), 0.84 (s, 1H) ppm. $^{19}$F NMR (376 MHz, DMSO-d6) δ-55.40, -79.25 ppm. ESI-MS m/z calc. 493.19125, found 494.1 (M+1)$^+$; Retention time: 2.03 minutes (LC Method Q).

Example 11: Preparation of (6S,12R)-20-(methylamino)-6,18-bis(trifluoromethyl)-22-oxa-3,4,16,21-tetraazatetracyclo[15.3.1.12,5.012,16]docosa-1(21),2,4,17,19-pentaen-6-ol (Compound 15)

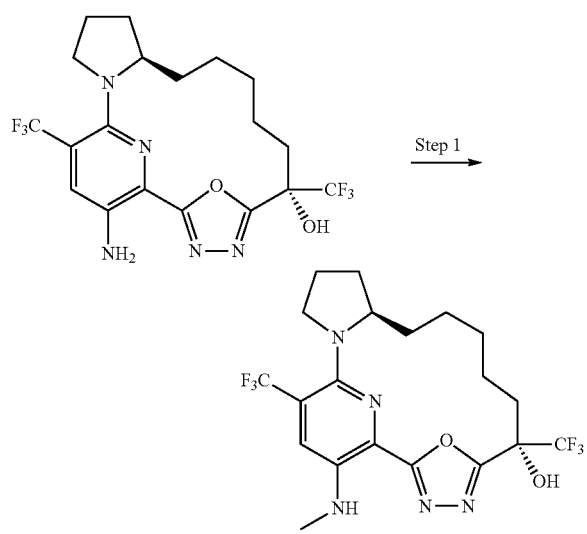

Step 1: (6S,12R)-20-(Methylamino)-6,18-bis(trifluoromethyl)-22-oxa-3,4,16,21-tetraazatetracyclo[15.3.1.12,5.012,16]docosa-1(21),2,4,17,19-pentaen-6-ol (Compound 15)

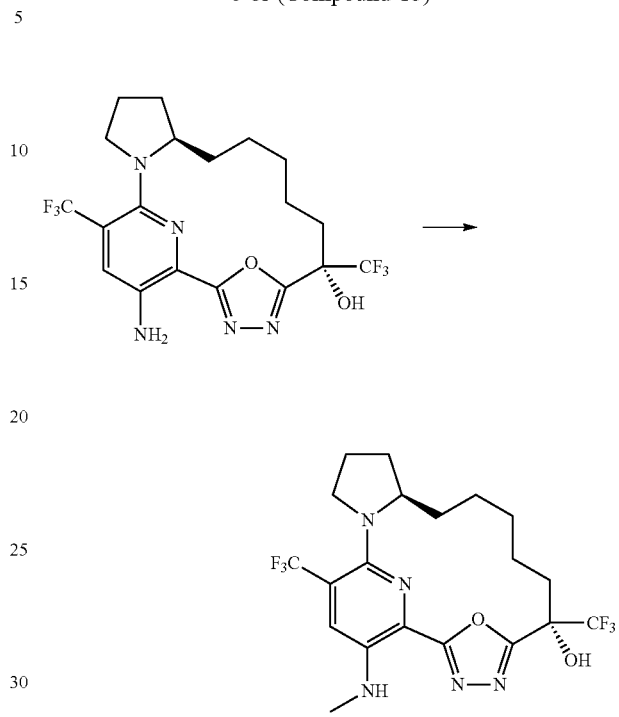

To a solution of (6S,12R)-20-amino-6,18-bis(trifluoromethyl)-22-oxa-3,4,16,21-tetraazatetracyclo[15.3.1.12,5.012,16]docosa-1(21),2,4,17,19-pentaen-6-ol (30 mg, 0.06446 mmol) in DMF (0.6 mL) at room temperature was added [bis(trimethylsilyl)amino]sodium (142 μL of 1 M, 0.142 mmol) and then iodomethane (71 μL of 1 M, 0.071 mmol) in THF. The mixture was stirred at room temperature for 1 h, diluted with ether and washed with aqueous 1 M NH$_4$Cl and the organic layer was dried (MgSO$_4$), filtered and evaporated. The residue was purified by silica gel chromatography using a gradient from 10% to 35% EtOAc in hexanes (12 g column) giving as a yellow solid, (6S,12R)-20-(methylamino)-6,18-bis(trifluoromethyl)-22-oxa-3,4,16,21-tetraazatetracyclo[15.3.1.12,5.012,16]docosa-1(21),2,4,17,19-pentaen-6-ol (15.5 mg, 50%). $^1$H NMR (400 MHz, DMSO-d6) δ 7.57 (s, 1H), 7.51 (s, 1H), 6.33 (q, J=5.0 Hz, 1H), 4.03 (q, J=7.3, 6.8 Hz, 1H), 3.55 (q, J=8.6 Hz, 1H), 3.31-3.22 (m, 1H), 2.97 (d, J=4.9 Hz, 3H), 2.44-2.25 (m, 1H), 2.17 (d, J=7.3 Hz, 1H), 2.05 (q, J=8.5 Hz, 1H), 1.93 (s, 1H), 1.82-1.62 (m, 4H), 1.49 (ddd, J=34.0, 18.0, 7.7 Hz, 5H), 0.97-0.83 (m, 1H) ppm. $^{19}$F NMR (376 MHz, DMSO-d6) δ-55.57, -76.40 ppm. ESI-MS m/z calc. 479.1756, found 480.2 (M+1)$^+$; Retention time: 1.93 minutes (LC Method Q).

Example 12: Preparation of (6S,12R)-20-(ethylamino)-6,18-bis(trifluoromethyl)-22-oxa-3,4,16,21-tetraazatetracyclo[15.3.1.1²,⁵.0¹²,¹⁶]docosa-1(21),2,4,17,19-pentaen-6-ol (Compound 16)

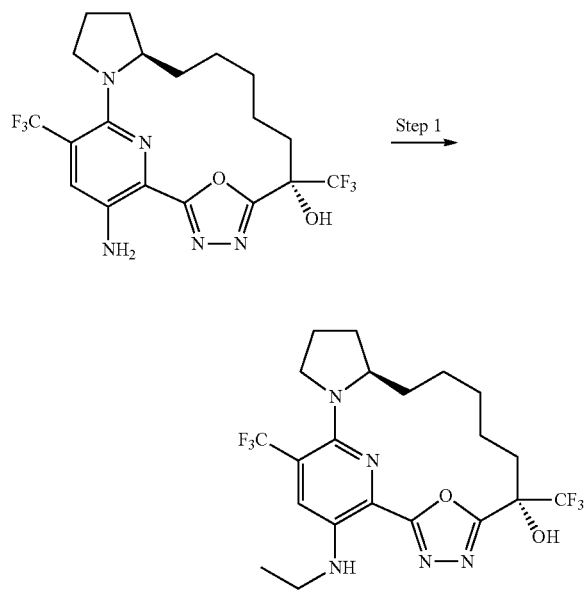

Step 1: (6S,12R)-20-(Ethylamino)-6,18-bis(trifluoromethyl)-22-oxa-3,4,16,21-tetraazatetracyclo[15.3.1.1²,⁵.0¹²,¹⁶]docosa-1(21),2,4,17,19-pentaen-6-ol (Compound 16)

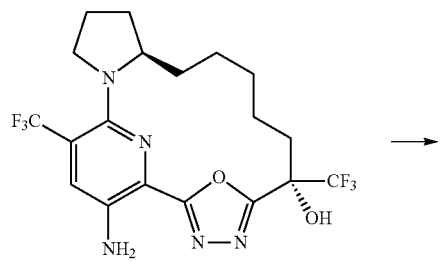

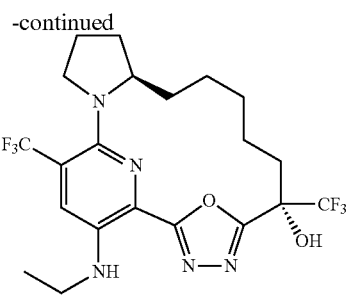

To (6S,12R)-20-amino-6,18-bis(trifluoromethyl)-22-oxa-3,4,16,21-tetraazatetracyclo[15.3.1.1²,⁵.0¹²,¹⁶]docosa-1(21),2,4,17,19-pentaen-6-ol (30 mg, 0.06446 mmol) in DMF (0.6 mL) at room temperature was added [bis(trimethylsilyl)amino]sodium (142 μL of 1 M, 0.142 mmol) and then bromoethane (71 μL of 1 M, 0.071 mmol) in THF. The mixture was stirred at room temperature for 1 h then diluted with ether and aqueous 1 M $NH_4C_1$. Separated the layers and the organic layer was dried ($MgSO_4$), filtered and evaporated. The residue was purified by silica gel chromatography (12 g column) using a gradient from 10% to 35% EtOAc in hexanes which provided as a yellow solid, (6S,12R)-20-(ethylamino)-6,18-bis(trifluoromethyl)-22-oxa-3,4,16,21-tetraazatetracyclo[15.3.1.1²,⁵.0¹²,¹⁶]docosa-1(21),2,4,17,19-pentaen-6-ol (16.6 mg, 52%). ¹H NMR (400 MHz, DMSO-d6) δ 7.55 (s, 2H), 6.24 (t, J=5.7 Hz, 1H), 4.03 (q, J=8.7 Hz, 1H), 3.55 (q, J=9.0, 8.5 Hz, 1H), 3.21-3.40 (m, 3H), 2.44-2.26 (m, 1H), 2.18 (t, J=7.2 Hz, 1H), 2.03 (td, J=13.8, 12.6, 7.4 Hz, 1H), 1.94 (d, J=11.7 Hz, 1H), 1.72 (dq, J=21.7, 13.1, 11.4 Hz, 3H), 1.47 (ddt, J=41.4, 15.4, 9.5 Hz, 6H), 1.24 (t, J=7.1 Hz, 3H), 0.91 (td, J 11.8, 6.0 Hz, 1H). ¹⁹F NMR (376 MHz, DMSO-d6) d–55.55, –76.42. ESI-MS m/z calc. 493.19125, found 494.1 (M+1)⁺; Retention time: 2.02 minutes (LC Method Q).

Example 13: Preparation of 19-amino-6,17-bis(trifluoromethyl)-21-oxa-3,4,15,20-tetraazatetracyclo[14.3.1.1²,⁵.0¹¹,¹⁵]henicosa-1(20),2,4,16,18-pentaen-6-ol (diastereomer pair 1) (Compound 17) and 19-amino-6,17-bis(trifluoromethyl)-21-oxa-3,4,15,20-tetraazatetracyclo[14.3.1.1²,⁵.0¹¹,¹⁵]henicosa-1(20),2,4,16,18-pentaen-6-ol (diastereomer pair 2) (Compound 18)

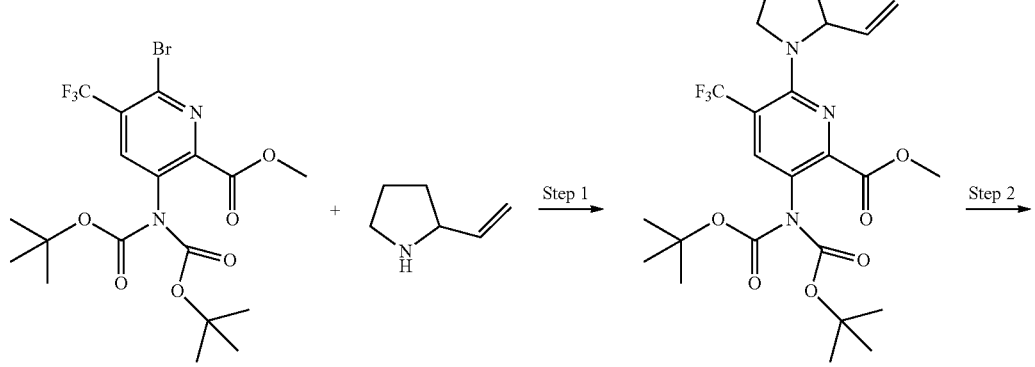

271
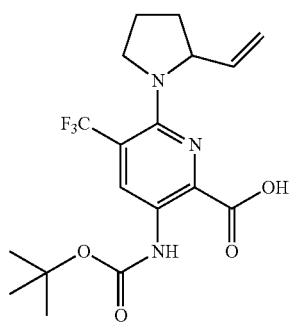
Step 3 →
-continued
272
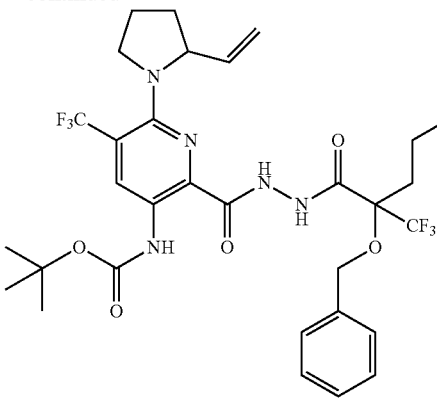
Step 4 →
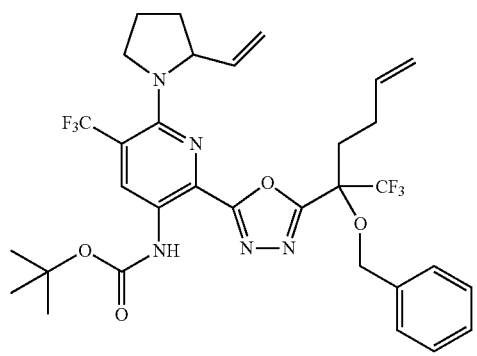
Step 5 →
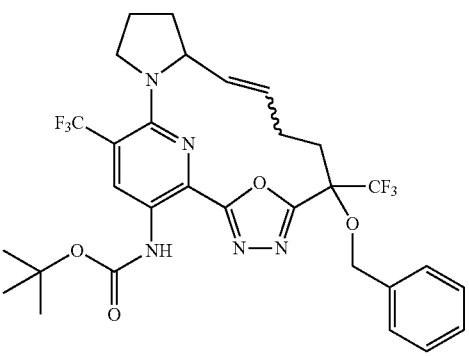
Step 6 →
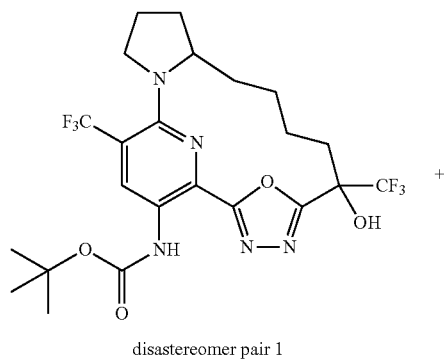
diastereomer pair 1
+
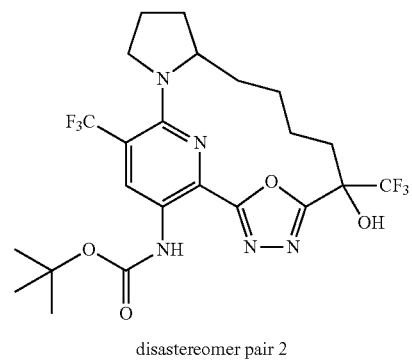
diastereomer pair 2
↓ Step 7
↓ Step 8
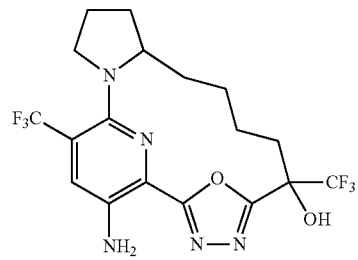
diastereomer pair 1
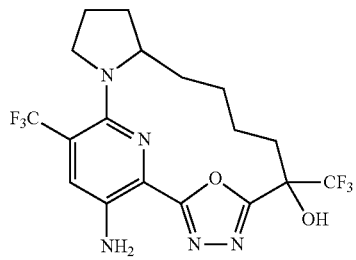
diastereomer pair 2

Step 1: Methyl 3-[bis(tert-butoxycarbonyl)amino]-5-(trifluoromethyl)-6-(2-vinylpyrrolidin-1-yl)pyridine-2-carboxylate

Step 2: 3-(tert-Butoxycarbonylamino)-5-(trifluoromethyl)-6-(2-vinylpyrrolidin-1-yl)pyridine-2-carboxylic Acid

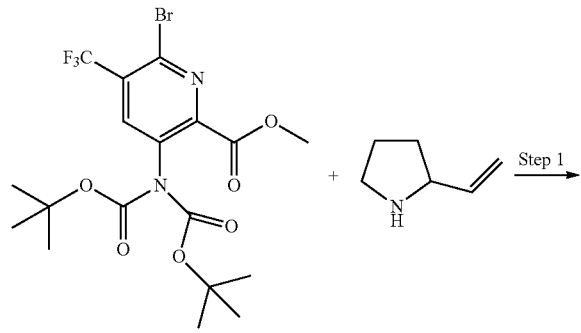

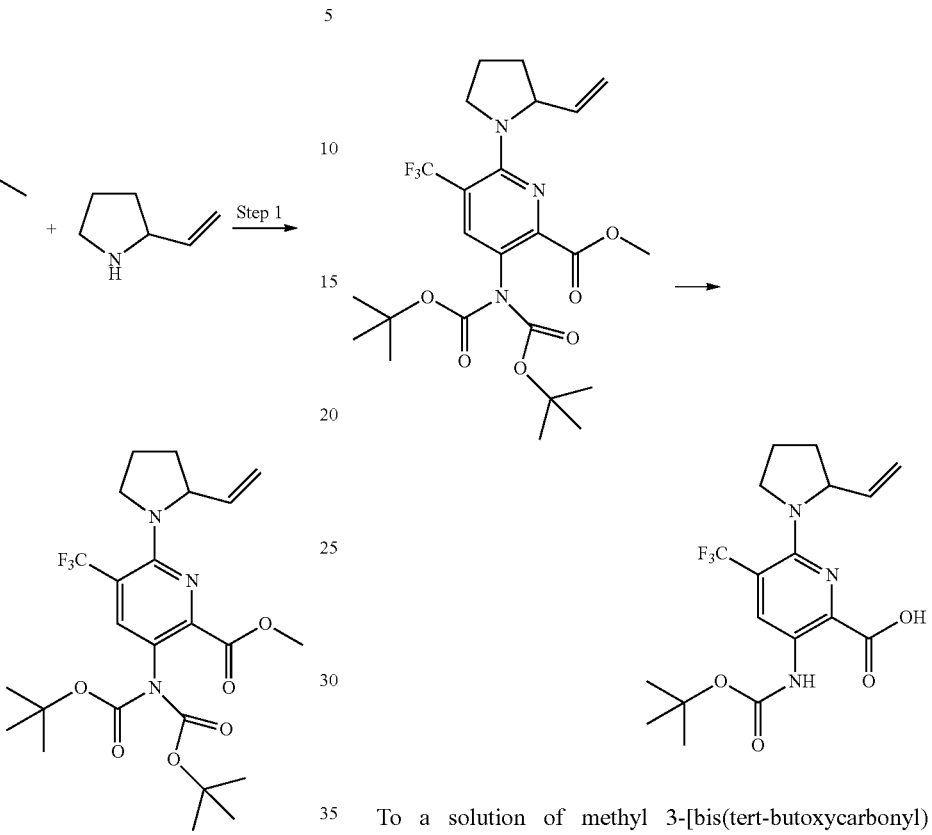

In a 250-mL sealed vessel, 2-vinylpyrrolidine (879 mg, 9.047 mmol), DIEA (4.75 mL, 27.27 mmol) and methyl 3-[bis(tert-butoxycarbonyl)amino]-6-bromo-5-(trifluoromethyl)pyridine-2-carboxylate (2.5 g, 5.007 mmol) were combined in acetonitrile (28 mL) and the mixture was heated at 80° C. for 18 hours. The reaction mixture was cooled to ambient temperature and the solvent removed in vacuo. The residue was diluted with EtOAc (50 mL) and washed brine (2×25 mL) dried over sodium sulfate, filtered and concentrated. The residue was purified by silica gel chromatography (120 gram column) using a gradient from 100% hexanes to 50% ethyl acetate in hexanes giving as a tan solid, methyl 3-[bis(tert-butoxycarbonyl)amino]-5-(trifluoromethyl)-6-(2-vinylpyrrolidin-1-yl)pyridine-2-carboxylate (1.93 g, 75%). $^1$H NMR (400 MHz, DMSO-d6) δ 8.04 (s, 1H), 5.74 (ddd, J=16.7, 10.3, 6.1 Hz, 1H), 5.16-5.06 (m, 1H), 5.03-4.90 (m, 2H), 3.79 (s, 3H), 3.65 (p, J=8.6 Hz, 1H), 3.43 (t, J=8.3 Hz, 1H), 2.14 (dq, J=11.9, 6.5 Hz, 1H), 2.02-1.92 (m, 1H), 1.90-1.78 (m, 1H), 1.71 (ddt, J=11.9, 9.2, 7.0 Hz, 1H), 1.35 (s, 18H) ppm. ESI-MS m/z calc. 515.2243, found 516.2 (M+1)$^+$; Retention time: 1.79 minutes (LC Method J).

To a solution of methyl 3-[bis(tert-butoxycarbonyl)amino]-5-(trifluoromethyl)-6-(2-vinylpyrrolidin-1-yl)pyridine-2-carboxylate (1.93 g, 3.744 mmol) in THF (20 mL), methanol (19 mL) and water (15 mL) was added anhydrous lithium hydroxide (350 mg, 14.32 mmol). The mixture was stirred at 60° C. for 4 h. THF and methanol were removed by evaporation, then 30 mL of 10% aqueous HCl was added and extracted with EtOAc (2×50 mL). The organic phases were combined, washed with brine (10 mL), dried over anhydrous sodium sulfate, filtered and concentrated under reduced pressure. The residue was purified by silica gel chromatography (80 gram column) using a gradient from 100% hexanes to 80% ethyl acetate in hexanes giving as a yellow solid, 3-(tert-butoxycarbonylamino)-5-(trifluoromethyl)-6-(2-vinylpyrrolidin-1-yl)pyridine-2-carboxylic acid (1.35 g, 90%). $^1$H NMR (400 MHz, DMSO-d6) δ 13.46 (s, 1H), 9.69 (s, 1H), 8.64 (s, 1H), 5.71 (ddd, J=16.9, 10.2, 6.5 Hz, 1H), 5.18 (ddd, J=17.1, 2.1, 1.1 Hz, 1H), 5.00-4.88 (m, 2H), 3.61 (q, J=8.5 Hz, 1H), 3.29 (s, 1H), 2.12 (dtd, J=11.2, 6.5, 3.7 Hz, 1H), 1.93 (dtd, J=13.3, 6.7, 3.2 Hz, 1H), 1.85-1.75 (m, 1H), 1.73-1.62 (m, 1H), 1.47 (s, 9H) ppm. ESI-MS m/z calc. 401.15625, found 402.2 (M+1)$^+$; Retention time: 1.72 minutes (LC Method A).

Step 3: tert-Butyl N-[2-[[[2-benzyloxy-2-(trifluoromethyl)hex-5-enoyl]amino]carbamoyl]-5-(trifluoromethyl)-6-(2-vinylpyrrolidin-1-yl)-3-pyridyl]carbamate

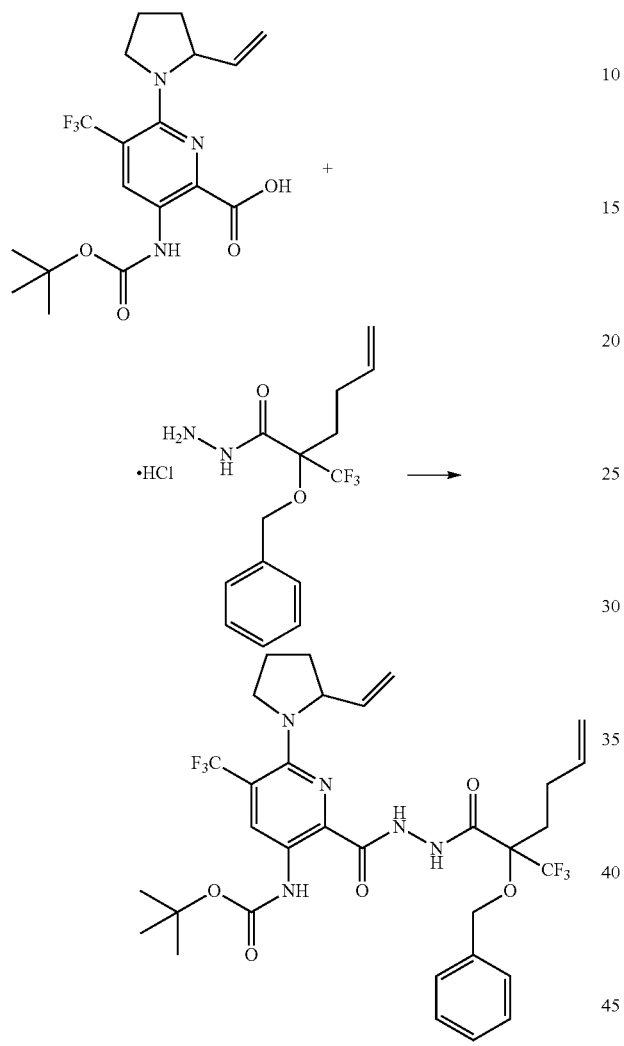

To a solution of 3-(tert-butoxycarbonylamino)-5-(trifluoromethyl)-6-(2-vinylpyrrolidin-1-yl)pyridine-2-carboxylic acid (1.3 g, 3.239 mmol) in NMP (16.5 mL) was added 2-benzyloxy-2-(trifluoromethyl)hex-5-enehydrazide (hydrochloride salt) (1.10 g, 3.247 mmol) and DIEA (2.25 mL, 12.92 mmol) followed by HATU (1.7 g, 4.471 mmol). The reaction mixture was stirred at room temperature for 18 h. The reaction was diluted with ethyl acetate and washed with a saturated aqueous sodium bicarbonate solution. The organic layer was further washed with 10% citric acid solution followed by brine. The organics were separated, dried over sodium sulfate, filtered and evaporated. The residue was purified by silica gel chromatography (80 gram column) using a gradient from 100% hexanes to 70% ethyl acetate in hexanes giving as a yellow solid, tert-butyl N-[2-[[[2-benzyloxy-2-(trifluoromethyl)hex-5-enoyl]amino]carbamoyl]-5-(trifluoromethyl)-6-(2-vinylpyrrolidin-1-yl)-3-pyridyl]carbamate (1.75 g, 79%). ESI-MS m/z calc. 685.2699, found 686.2 (M+1)+; Retention time: 2.3 minutes (LC Method J).

Step 4: tert-Butyl N-[2-[5-[1-benzyloxy-1-(trifluoromethyl)pent-4-enyl]-1,3,4-oxadiazol-2-yl]-5-(trifluoromethyl)-6-(2-vinylpyrrolidin-1-yl)-3-pyridyl]carbamate

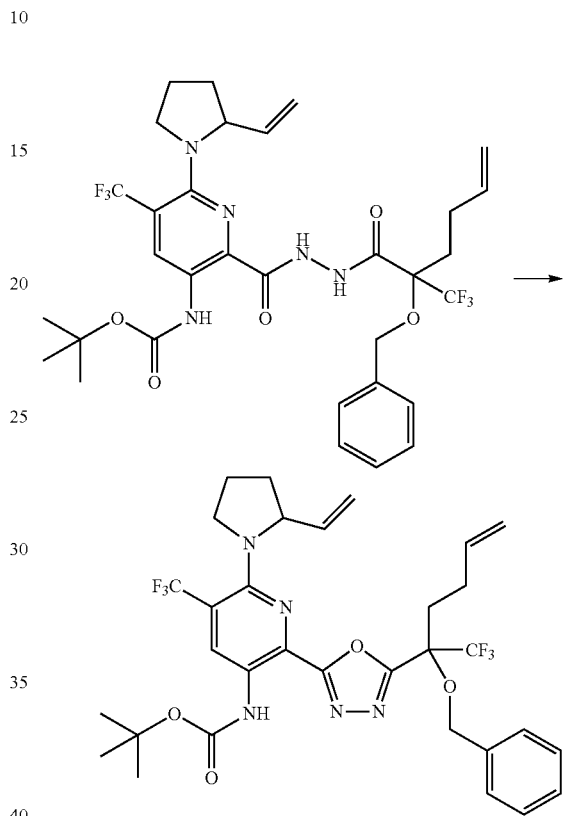

A solution of tert-butyl N-[2-[[[2-benzyloxy-2-(trifluoromethyl)hex-5-enoyl]amino]carbamoyl]-5-(trifluoromethyl)-6-(2-vinylpyrrolidin-1-yl)-3-pyridyl]carbamate (1.75 g, 2.552 mmol) and DIEA (1.55 mL, 8.899 mmol) in acetonitrile (40 mL) was heated to 50° C., then p-toluenesulfonyl chloride (760 mg, 3.986 mmol) was added in 3 portions. The resulted mixture was heated at 70° C. for 2 hours. The reaction mixture was cooled and quenched with a saturated solution of sodium bicarbonate (50 mL) and extracted with ethyl acetate. The organics were separated, dried over sodium sulfate, filtered and evaporated. The residue was purified by silica gel chromatography (80 gram column) using a gradient from 100% hexanes to 50% ethyl acetate in hexanes giving as a yellow residue, tert-butyl N-[2-[5-[1-benzyloxy-1-(trifluoromethyl)pent-4-enyl]-1,3,4-oxadiazol-2-yl]-5-(trifluoromethyl)-6-(2-vinylpyrrolidin-1-yl)-3-pyridyl]carbamate (1.69 g, 99%). $^1$H NMR (400 MHz, DMSO-d6) δ 9.49 (s, 1H), 8.65 (s, 1H), 7.45-7.31 (m, 5H), 5.86 (m, J=19.1, 16.7, 10.1, 6.4 Hz, 1H), 5.64 (m, J=17.1, 10.2, 6.9, 5.0 Hz, 1H), 5.22-5.12 (m, 1H), 5.12-4.94 (m, 2H), 4.90 (dddd, J=19.0, 10.2, 1.9, 0.8 Hz, 1H), 4.83-4.70 (m, 2H), 4.65 (dd, J=11.0, 6.9 Hz, 1H), 3.65 (q, J=8.5 Hz, 1H), 3.39 (t, J=8.7 Hz, 1H), 2.57 (m, J=15.7, 10.8, 5.7 Hz, 1H), 2.48-2.37 (m, 1H), 2.35-2.20 (m, 2H), 2.10 (dt, J=11.6, 5.8 Hz, 1H), 2.03-1.93 (m, 1H), 1.85-1.75 (m, 1H), 1.75-1.65 (m, 1H), 1.46 (s, 9H) ppm. ESI-MS m/z calc. 667.25934, found 668.2 (M+1)⁺; Retention time: 2.23 minutes (LC Method M).

Step 5: tert-Butyl N-[6-(benzyloxy)-6,17-bis(trifluoromethyl)-21-oxa-3,4,15,20-tetraazatetracyclo[14.3.1.1²,⁵.0¹¹,¹⁵]henicosa-1(20),2,4,9,16,18-hexaen-19-yl]carbamate (E/Z mixture)

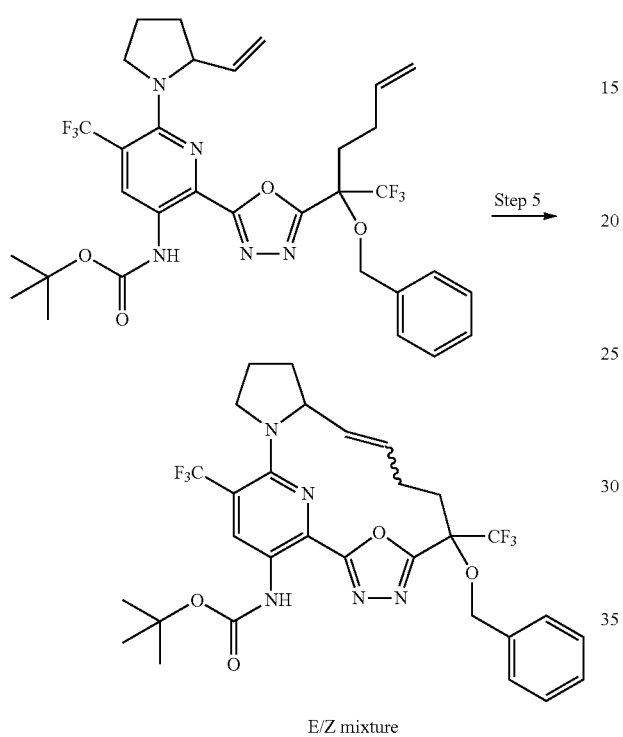

E/Z mixture

In a 150 mL round-bottom flask, a degassed solution of tert-butyl N-[2-[5-[1-benzyloxy-1-(trifluoromethyl)pent-4-enyl]-1,3,4-oxadiazol-2-yl]-5-(trifluoromethyl)-6-(2-vinylpyrrolidin-1-yl)-3-pyridyl]carbamate (1.67 g, 2.501 mmol) in DCE (400 mL) was heated to 50° C. under nitrogen atmosphere. Then, Zhan catalyst-1B (300 mg, 0.4089 mmol) was added in two portions over 10 minutes. The resulting mixture was heated at 70° C. for 2 h, then 80° C. for 3 h. Added more Zhan catalyst-1B (300 mg, 0.4089 mmol) and heated at 85° C. for additional 18 h to complete the reaction. The reaction mixture was cooled to room temperature and concentrated under reduced pressure. The residue was purified using reverse-phase preparative chromatography utilizing a C₁₈ column and a gradient from 50% to 99% of acetonitrile in water (5 mM HCl as modifier) for 15 minute giving as a yellow residue, tert-butyl N-[6-(benzyloxy)-6,17-bis(trifluoromethyl)-21-oxa-3,4,15,20-tetraazatetracyclo[14.3.1.1²,⁵.0¹¹,¹⁵]henicosa-1(20),2,4,9,16,18-hexaen-19-yl]carbamate (E/Z mixture) (45 mg, 3%). ESI-MS m/z calc. 639.228, found 640.2 (M+1)⁺; Retention time: 1.96 minutes (LC Method M).

Step 6: tert-Butyl N-[6-hydroxy-6,17-bis(trifluoromethyl)-21-oxa-3,4,15,20-tetraazatetracyclo[14.3.1.1²,⁵.0¹¹,¹⁵]henicosa-1(20),2,4,16,18-pentaen-19-yl]carbamate (diastereomer pair 1) and tert-butyl N-[6-hydroxy-6,17-bis(trifluoromethyl)-21-oxa-3,4,15,20-tetraazatetracyclo[14.3.1.1²,⁵.0¹¹,¹⁵]henicosa-1(20),2,4,16,18-pentaen-19-yl]carbamate (diastereomer pair 2)

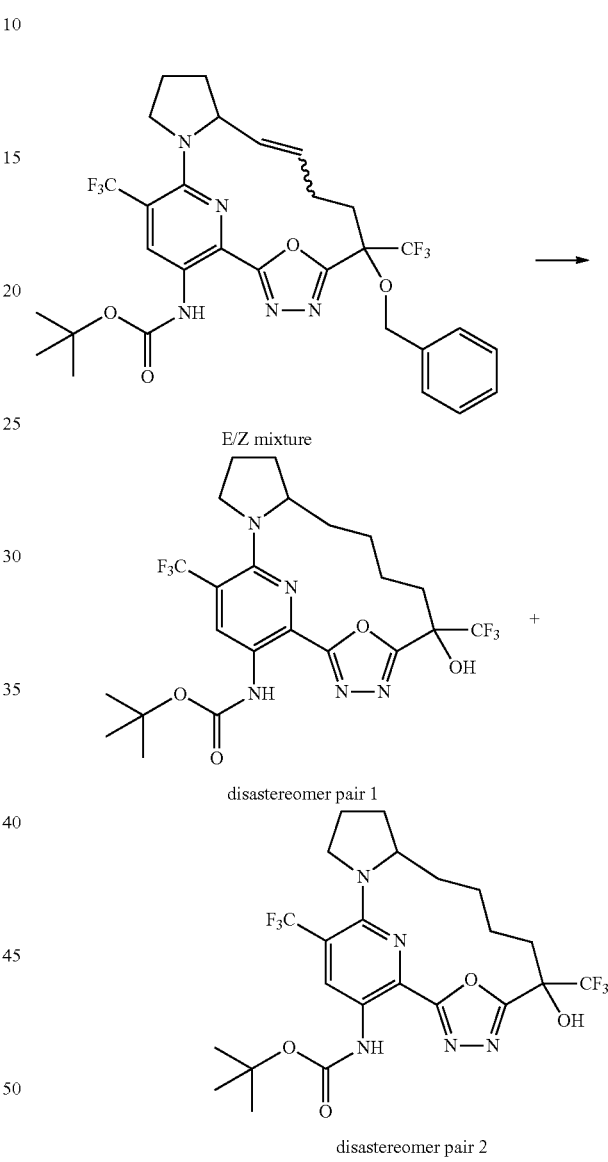

To a solution of tert-butyl N-[6-(benzyloxy)-6,17-bis(trifluoromethyl)-21-oxa-3,4,15,20-tetraazatetracyclo[14.3.1.1²,⁵.0¹¹,¹⁵]henicosa-1(20),2,4,9,16,18-hexaen-19-yl]carbamate (E/Z mixture) (45 mg, 0.07036 mmol) in AcOH (2.5 mL) was added Pd/C (9.1 mg of 10% w/w, 0.008551 mmol). The mixture was put in a Parr Shaker and degassed under vacuum and filled with nitrogen gas three times. Then, all nitrogen gas was removed, and the reactor was pressurized to 60 psi with hydrogen gas. The mixture was shaken for 17 h. After that time, the reactor was depressurized, and the reaction was filtered and concentrated under vacuum. The residue was purified by reverse-phase preparative chromatography utilizing a C₁₈ column and a gradient from 30% to 99% acetonitrile and water (5 mM HCl as modifier) for 15 minutes giving as yellow residues, two diastereomer pairs of products:

The first diastereomer pair to elute was isolated as tert-butyl N-[6-hydroxy-6,17-bis(trifluoromethyl)-21-oxa-3,4,15,20-tetraazatetracyclo[14.3.1.12,5.011,15]henicosa-1(20),2,4,16,18-pentaen-19-yl]carbamate (diastereomer pair 1) (15 mg, 77%). ESI-MS m/z calc. 551.1967, found 552.2 (M+1)⁺; Retention time: 1.88 minutes (LC Method J).

The second diastereomer pair to elute was isolated as tert-butyl N-[6-hydroxy-6,17-bis(trifluoromethyl)-21-oxa-3,4,15,20-tetraazatetracyclo[14.3.1.12,5.011,15]henicosa-1(20),2,4,16,18-pentaen-19-yl]carbamate (diastereomer pair 2) (16 mg, 82%). ESI-MS m/z calc. 551.1967, found 552.1 (M+1)⁺; Retention time: 1.95 minutes (LC Method J).

Step 7: 19-Amino-6,17-bis(trifluoromethyl)-21-oxa-3,4,15,20-tetraazatetracyclo[14.3.1.12,5.011,15]henicosa-1(20),2,4,16,18-pentaen-6-ol (diastereomer pair 1) (Compound 17)

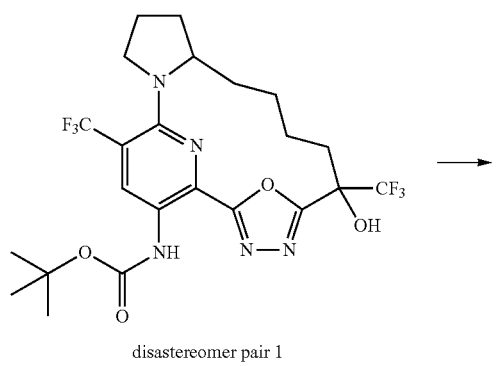

disastereomer pair 1

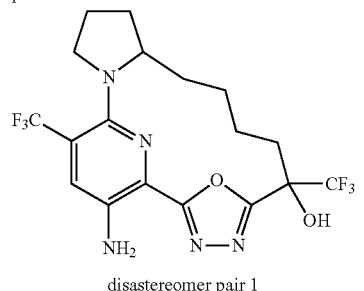

disastereomer pair 1 tert-Butyl N-[6-hydroxy-6,17-bis(trifluoromethyl)-21-oxa-3,4,15,20-tetraazatetracyclo[14.3.1.12,5.011,15]henicosa-1(20),2,4,16,18-pentaen-19-yl]carbamate (diastereomer pair 1) (15 mg, 0.0272 mmol) was dissolved in DCM (250 μL) and to the mixture was added TFA (50 μL, 0.649 mmol) and stirred the resulting solution at room temperature for 30 min. The mixture was evaporated to dryness, then diluted with ether and re-concentrated. Then, the residue was purified using reverse-phase preparative chromatography utilizing a C₁₈ column and a gradient from 10% to 99% acetonitrile in water (5 mM HCl) over a 30 minute run to afford as a yellow solid, 19-amino-6,17-bis(trifluoromethyl)-21-oxa-3,4,15,20-tetraazatetracyclo[14.3.1.12,5.011,15]henicosa-1(20),2,4,16,18-pentaen-6-ol (diastereomer pair 1) (1.4 mg, 11%). ESI-MS m/z calc. 451.1443, found 452.2 (M+1)⁺; Retention time: 1.93 minutes (LC Method A).

Step 8: 19-Amino-6,17-bis(trifluoromethyl)-21-oxa-3,4,15,20-tetraazatetracyclo[14.3.1.12,5.011,15]henicosa-1(20),2,4,16,18-pentaen-6-ol (diastereomer pair 2) (Compound 18)

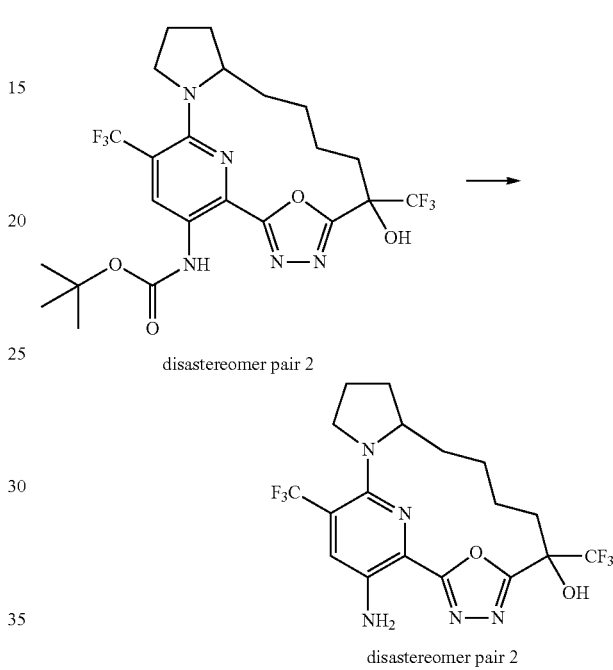

disastereomer pair 2 disastereomer pair 2 tert-Butyl N-[6-hydroxy-6,17-bis(trifluoromethyl)-21-oxa-3,4,15,20-tetraazatetracyclo[14.3.1.12,5.011,15]henicosa-1(20),2,4,16,18-pentaen-19-yl]carbamate (diastereomer pair 2) (16 mg, 0.02901 mmol) was dissolved in DCM (250 μL) and to the mixture was added TFA (50 μL, 0.649 mmol) and the mixture was stirred at room temperature for 30 min. The mixture was evaporated and the residue was purified using reverse-phase preparative chromatography utilizing a C₁₈ column and a gradient from 30% to 99% acetonitrile in water (5 mM HCl) over a 15 minute run to afford as a yellow solid, 19-amino-6,17-bis(trifluoromethyl)-21-oxa-3,4,15,20-tetraazatetracyclo[14.3.1.12,5.011,15]henicosa-1(20),2,4,16,18-pentaen-6-ol (diastereomer pair 2) (2.7 mg, 21%). ¹H NMR (400 MHz, Chloroform-d) δ 7.57 (s, 1H), 4.10 (s, 1H), 3.86 (s, 1H), 3.63 (s, 1H), 3.47 (s, 1H), 2.42-2.31 (m, 1H), 2.23 (s, 1H), 2.20-2.08 (m, 3H), 2.01 (q, J=5.9 Hz, 1H), 1.90-1.82 (m, 1H), 1.76-1.63 (m, 3H), 1.49 (d, J=7.5 Hz, 1H), 1.30-1.15 (m, 1H) ppm. Two exchangeable protons not observed. ESI-MS m/z calc. 451.1443, found 452.2 (M+1)⁺; Retention time: 2.01 minutes (LC Method A).

Example 14: Preparation of 17-amino-13-methyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (Compound 19) and 17-amino-13-methyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (Compound 20)
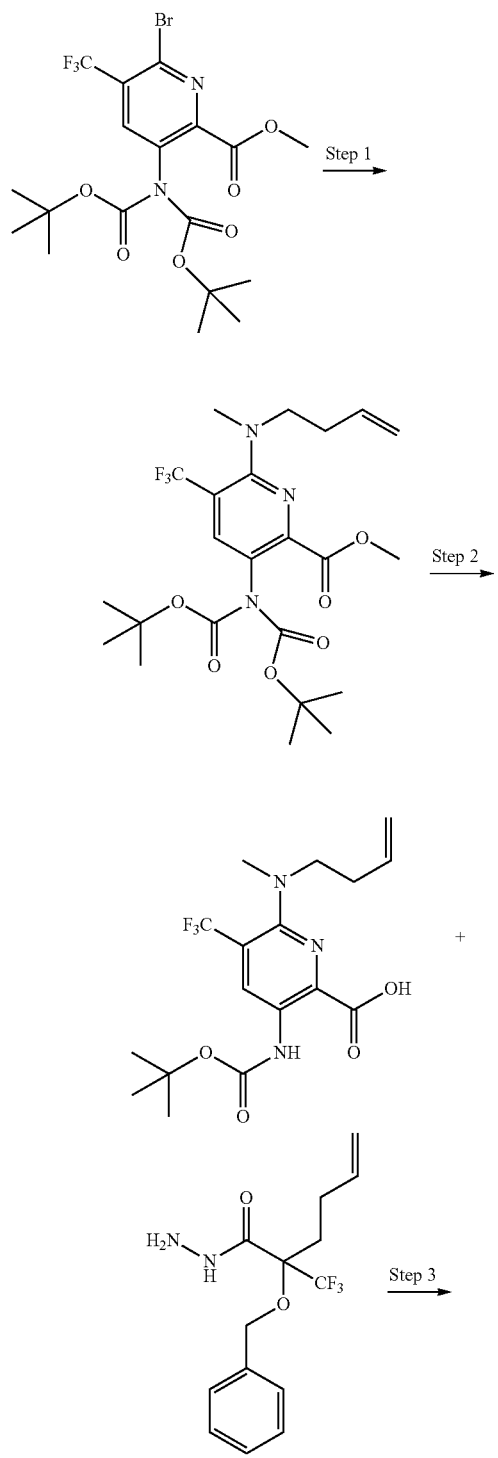
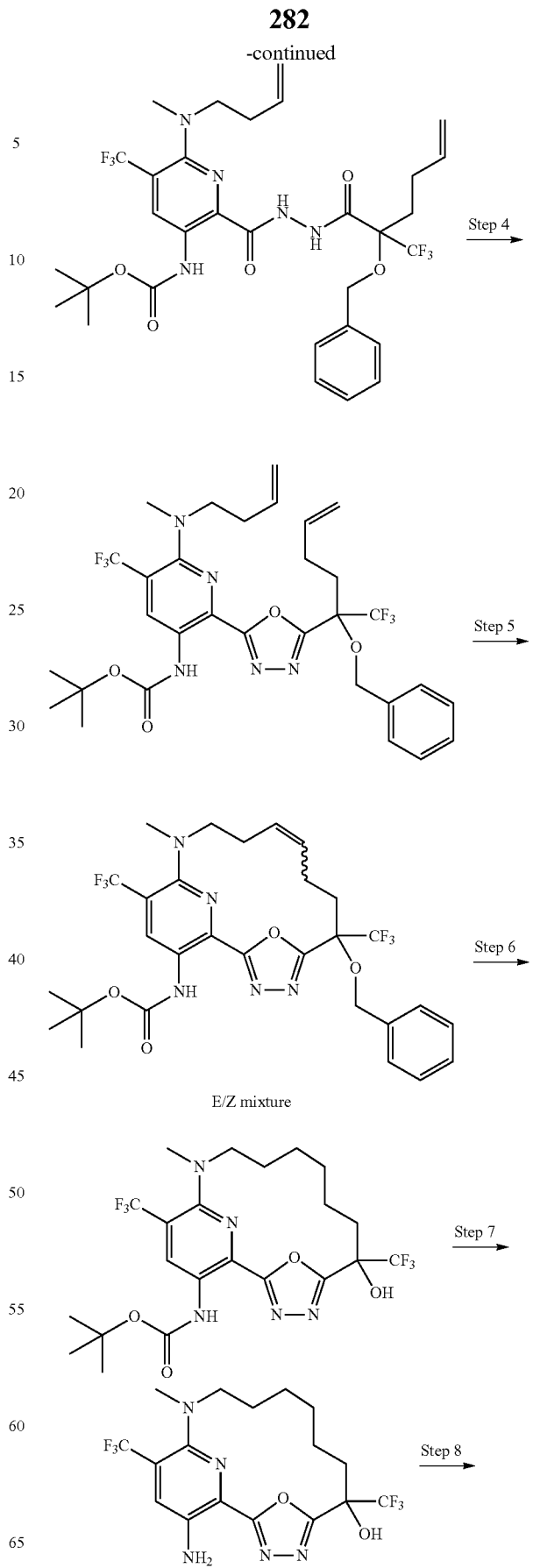

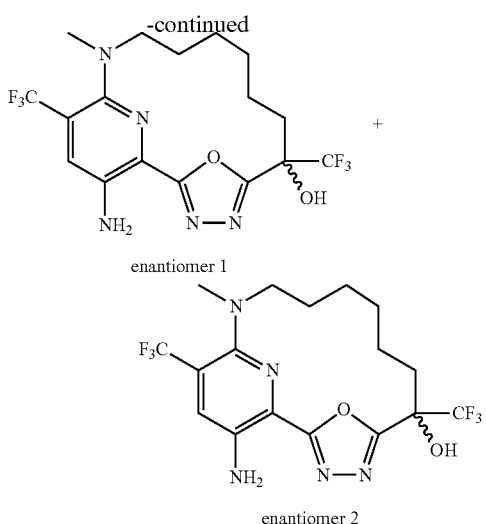

enantiomer 1 enantiomer 2

Step 1: Methyl 3-[bis(tert-butoxycarbonyl)amino]-6-[but-3-enyl(methyl)amino]-5-(trifluoromethyl)pyridine-2-carboxylate

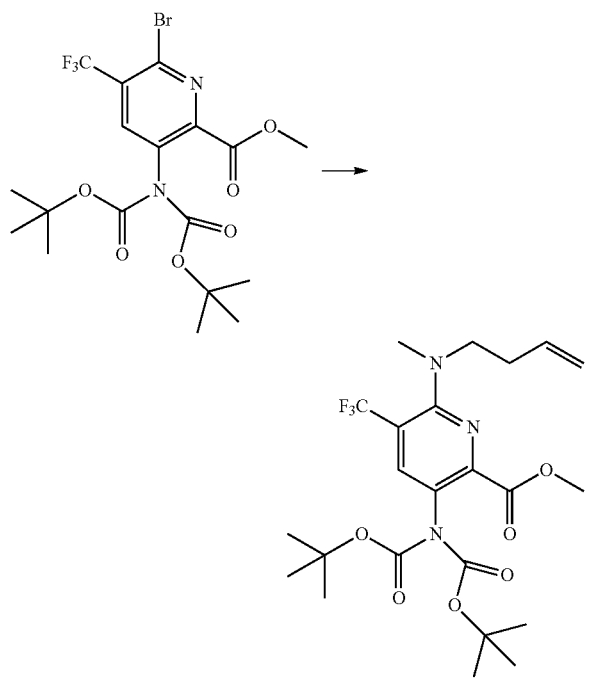

In a 5 mL sealed microwave vial, N-methylbut-3-en-1-amine (hydrochloride salt) (375 mg, 3.084 mmol), DIEA (2.001 mL, 11.49 mmol) and methyl 3-[bis(tert-butoxycarbonyl)amino]-6-bromo-5-(trifluoromethyl)pyridine-2-carboxylate (1.0 g, 2.003 mmol) were combined in acetonitrile (15 mL) and the mixture was heated to 70° C. for 18 hours. The reaction mixture was cooled to ambient temperature and the solvent was removed in vacuo. The residue was diluted with EtOAc (50 mL) and washed with brine (2×25 mL), dried over sodium sulfate, filtered and concentrated in vacuo. The residue was purified by silica gel chromatography (80 g column) using a gradient from 0% to 50% ethyl acetate in hexanes giving as a yellow oil, methyl 3-[bis(tert-butoxycarbonyl)amino]-6-[but-3-enyl(methyl)amino]-5-(trifluoromethyl)pyridine-2-carboxylate (565 mg, 56%). ESI-MS m/z calc. 503.22433, found 504.2 (M+1)+; Retention time: 1.73 minutes (LC Method J).

Step 2: 6-[But-3-enyl)methyl)amino]-3-(tert-butoxycarbonylamino)-5-(trifluoromethyl)pyridine-2-carboxylic Acid

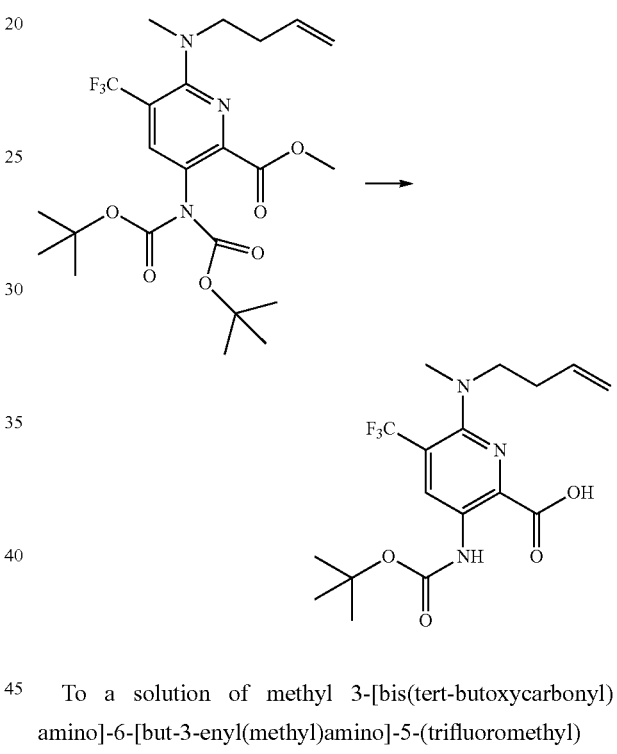

To a solution of methyl 3-[bis(tert-butoxycarbonyl)amino]-6-[but-3-enyl(methyl)amino]-5-(trifluoromethyl)pyridine-2-carboxylate (360 mg, 0.715 mmol) in THF (3.6 mL) was added methanol (3.6 mL) and water (1.8 mL). Anhydrous lithium hydroxide (327.8 mg, 13.69 mmol) was added and the mixture was heated at 60° C. for 1 h. THF and methanol were removed under reduced pressure. An aqueous 1 M HCl solution was added until the mixture was acidic, then extracted with ethyl acetate (3×75 mL). The organic phases were combined, washed with brine (75 mL), dried over anhydrous sodium sulfate, filtered and concentrated under reduced pressure to provide as a yellow solid, 6-[but-3-enyl(methyl)amino]-3-(tert-butoxycarbonylamino)-5-(trifluoromethyl)pyridine-2-carboxylic acid (270 mg, 97%). ESI-MS m/z calc. 389.15625, found 390.3 (M+1)+; Retention time: 0.7 minutes (LC Method R).

Step 3: tert-Butyl N-[2-[[[2-benzyloxy-2-(trifluoromethyl)hex-5-enoyl]amino]carbamoyl]-6-[but-3-enyl(methyl)amino]-5-(trifluoromethyl)-3-pyridyl]carbamate

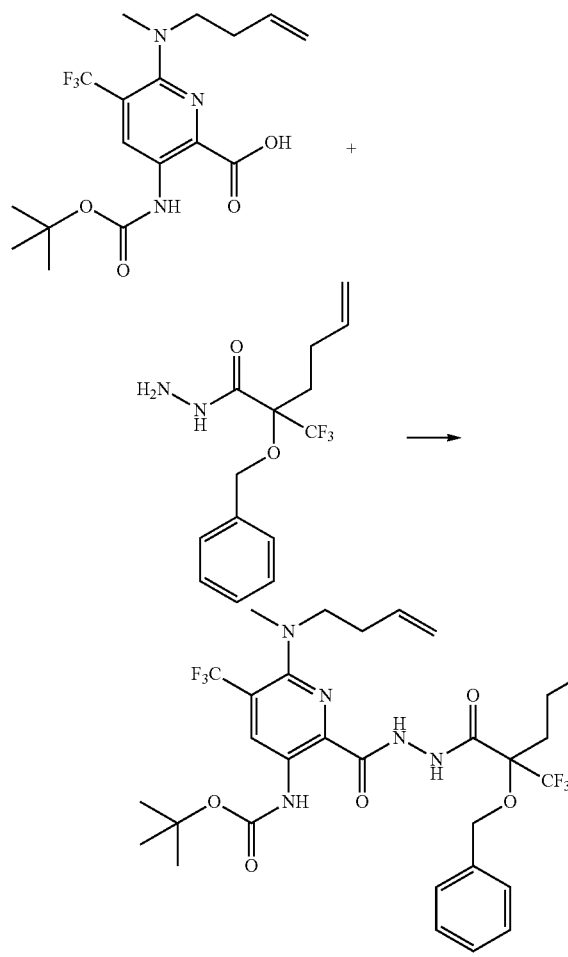

To a solution of 6-[but-3-enyl(methyl)amino]-3-(tert-butoxycarbonylamino)-5-(trifluoromethyl)pyridine-2-carboxylic acid (415 mg, 1.066 mmol) in NMP (5.5 mL) was added 2-benzyloxy-2-(trifluoromethyl)hex-5-enehydrazide (325 mg, 1.075 mmol) and DIEA (750 µL, 4.306 mmol) followed by HATU (560 mg, 1.473 mmol). The reaction mixture was stirred at room temperature for 18 h. The reaction was diluted with ethyl acetate and washed with sodium bicarbonate solution. The organic layer was further washed with 10% citric acid solution followed by brine. The organics were separated, dried over sodium sulfate, filtered and evaporated. The residue was purified by silica gel chromatography (80 g column) using a gradient from 0% to 50% ethyl acetate in hexanes giving as a yellow foam, tert-butyl N-[2-[[[2-benzyloxy-2-(trifluoromethyl)hex-5-enoyl]amino]carbamoyl]-6-[but-3-enyl(methyl)amino]-5-(trifluoromethyl)-3-pyridyl]carbamate (580 mg, 81%). $^1$H NMR (400 MHz, DMSO-d6) δ 10.54 (d, J=5.1 Hz, 2H), 10.32 (s, 1H), 8.95 (s, 1H), 7.53-7.47 (m, 2H), 7.41-7.36 (m, 2H), 7.35-7.30 (m, 1H), 5.92-5.81 (m, 1H), 5.81-5.70 (m, 1H), 5.12-5.00 (m, 3H), 4.95 (dd, J=10.2, 2.0 Hz, 1H), 4.86 (t, J=9.4 Hz, 2H), 3.36 (dd, J=8.6, 6.1 Hz, 2H), 2.87 (s, 3H), 2.33-2.28 (m, 2H), 2.26 (d, J=7.3 Hz, 2H), 2.19 (d, J=10.0 Hz, 2H), 1.48 (s, 9H) ppm. ESI-MS m/z calc. 673.2699, found 674.2 (M+1)$^+$; Retention time: 2.23 minutes (LC Method J).

Step 4: tert-Butyl N-[2-[5-[1-benzyloxy-1-(trifluoromethyl)pent-4-enyl]-1,3,4-oxadiazol-2-yl]-6-[but-3-enyl(methyl)amino]-5-(trifluoromethyl)-3-pyridyl]carbamate

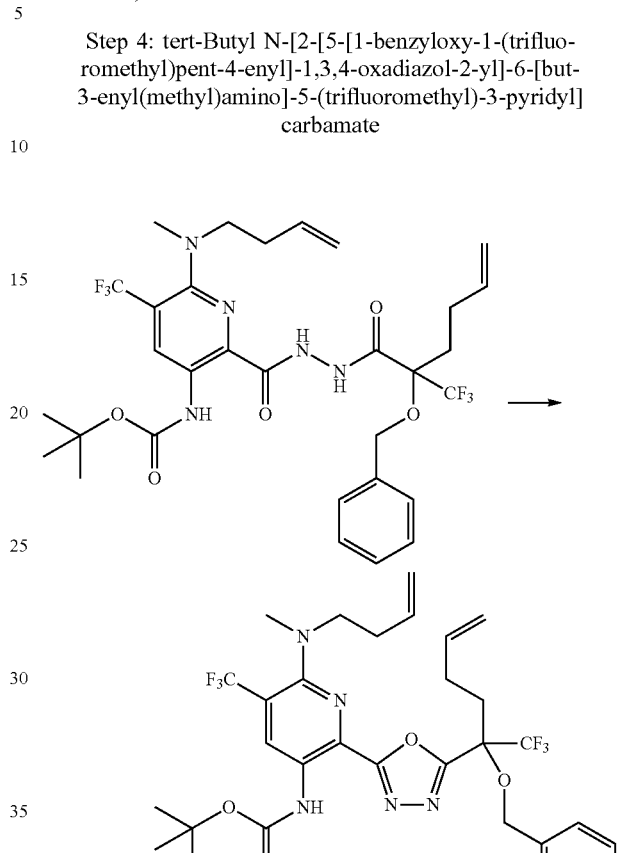

A solution of tert-butyl N-[2-[[[2-benzyloxy-2-(trifluoromethyl)hex-5-enoyl]amino]carbamoyl]-6-[but-3-enyl(methyl)amino]-5-(trifluoromethyl)-3-pyridyl]carbamate (575 mg, 0.8536 mmol) and DIEA (550 µL, 3.158 mmol) in acetonitrile (14 mL) was heated to 50° C., then p-toluenesulfonyl chloride (255 mg, 1.338 mmol) was added in 3 portions. The resulted mixture was heated at 70° C. for 3 hours. The reaction mixture was cooled and quenched with a saturated solution of sodium bicarbonate (50 mL) and extracted with ethyl acetate. The organics were separated, dried over sodium sulfate, filtered and evaporated. The residue was purified by silica gel chromatography (80 g column) using a gradient from 0% to 50% ethyl acetate in hexanes giving as a yellow residue, tert-butyl N-[2-[5-[1-benzyloxy-1-(trifluoromethyl)pent-4-enyl]-1,3,4-oxadiazol-2-yl]-6-[but-3-enyl(methyl)amino]-5-(trifluoromethyl)-3-pyridyl]carbamate (540 mg, 97%). $^1$H NMR (400 MHz, DMSO-d6) δ 9.59 (s, 1H), 8.72 (s, 1H), 7.48-7.41 (m, 2H), 7.38-7.30 (m, 3H), 5.89-5.68 (m, 2H), 5.13-4.92 (m, 4H), 4.73 (d, J=10.9 Hz, 1H), 4.65 (d, J=10.9 Hz, 1H), 3.47-3.36 (m, 2H), 2.95 (d, J=1.4 Hz, 3H), 2.44 (td, J=14.6, 13.1, 6.8 Hz, 1H), 2.38-2.23 (m, 5H), 1.47 (s, 9H) ppm. ESI-MS m/z calc. 655.25934, found 655.2 (M+1)$^+$; Retention time: 2.15 minutes (LC Method M).

287

Step 5: tert-Butyl N-[6-benzyloxy-13-methyl-6,15-bis(trifluoromethyl)-19-oxa-3,4,13,18-tetrazatricyclo[12.3.1.12,5]nonadeca-1(17),2,4,9,14(18),15-hexaen-17-yl]carbamate (E/Z mixture)

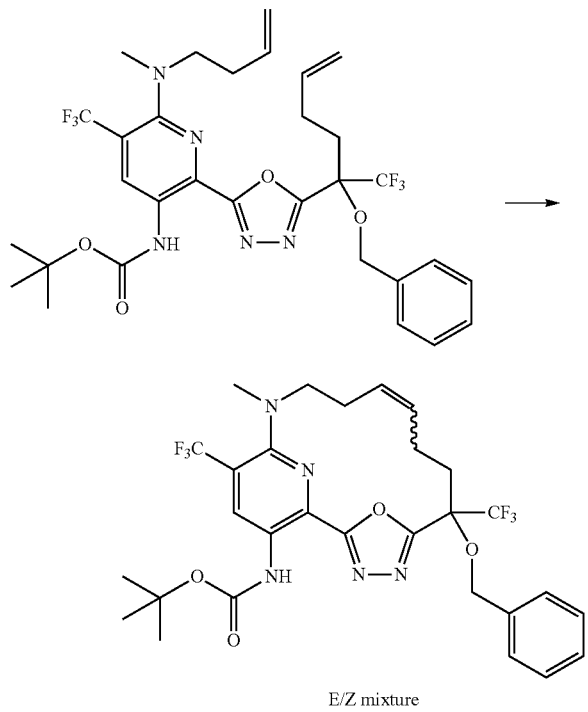

E/Z mixture

To a degassed solution of tert-butyl N-[2-[5-[1-benzyloxy-1-(trifluoromethyl)pent-4-enyl]-1,3,4-oxadiazol-2-yl]-6-[but-3-enyl(methyl)amino]-5-(trifluoromethyl)-3-pyridyl]carbamate (540 mg, 0.8236 mmol) in DCE (130 mL) was added Zhan catalyst-1B (91 mg, 0.124 mmol) in two portions over 10 minutes at 50° C. under nitrogen atmosphere. The resulting mixture was heated at 70° C. for 2 h. The reaction mixture was cooled to room temperature and concentrated under reduced pressure. The residue was purified by silica gel chromatography (80 g column) using a gradient from 0% to 30% ethyl acetate in hexanes giving as a yellow residue, tert-butyl N-[6-benzyloxy-13-methyl-6,15-bis(trifluoromethyl)-19-oxa-3,4,13,18-tetrazatricyclo[12.3.1.12,5]nonadeca-1(17),2,4,9,14(18),15-hexaen-17-yl]carbamate (E/Z mixture) (395 mg, 76%). $^1$H NMR (400 MHz, DMSO-d6) δ 9.09 (s, 1H), 8.61 (s, 1H), 7.41-7.35 (m, 1H), 7.35-7.27 (m, 4H), 5.67-5.56 (m, 1H), 5.43 (q, J=8.3 Hz, 1H), 4.76 (d, J=11.0 Hz, 1H), 4.68 (d, J=11.0 Hz, 1H), 3.45-3.33 (m, 2H), 3.10-3.02 (m, 3H), 2.62 (d, J=8.3 Hz, 2H), 2.45 (s, 2H), 2.24 (dt, J=15.6, 6.5 Hz, 2H), 1.47 (d, J=4.9 Hz, 9H) ppm. ESI-MS m/z calc. 627.228, found 628.2 (M+1)$^+$; Retention time: 1.94 minutes (LC Method M).

288

Step 6: tert-Butyl N-[6-hydroxy-13-methyl-6,15-bis(trifluoromethyl)-19-oxa-3,4,13,18-tetrazatricyclo[12.3.1.12,5]nonadeca-1(17),2,4,14(18),15-pentaen-17-yl]carbamate

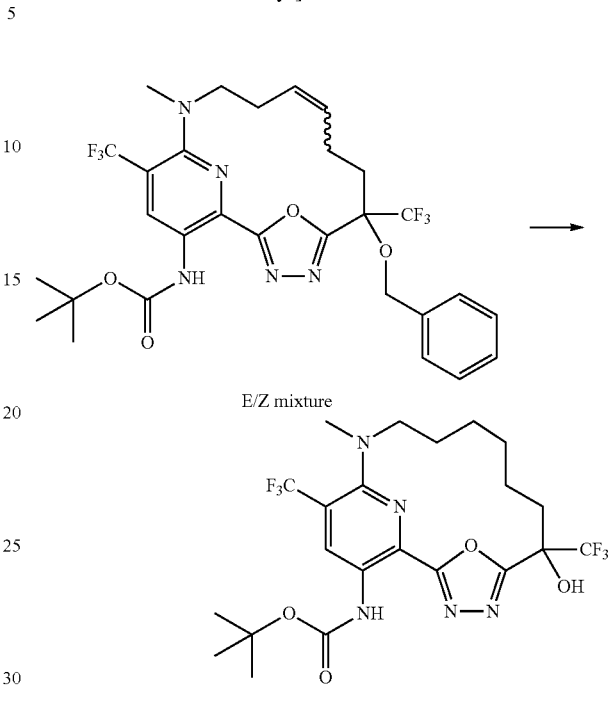

To a solution of tert-butyl N-[6-benzyloxy-13-methyl-6,15-bis(trifluoromethyl)-19-oxa-3,4,13,18-tetrazatricyclo[12.3.1.12,5]nonadeca-1(17),2,4,9,14(18),15-hexaen-17-yl]carbamate (E/Z mixture) (390 mg, 0.6214 mmol) in AcOH (22 mL) was added Pd/C (67 mg of 10% w/w, 0.06296 mmol). The mixture was degassed under vacuum and filled with nitrogen gas three times. Then, all nitrogen gas was removed, and the reactor was pressurized to 60 psi with hydrogen gas. The mixture was shaken for 4 h in a Parr shaker. The reactor was depressurized and an additional 0.2 eq Pd/C (134 mg of 10% w/w) was added. The mixture was returned to the Parr shaker and degassed under vacuum and filled with nitrogen gas three times. Then, all nitrogen gas was removed, and the reactor was pressurized to 55 psi with hydrogen gas. The mixture was shaken for 3 hours. After that time, the reactor was depressurized and an additional 0.7 eq Pd/C (465 mg of 10% w/w) was added. The mixture was returned to the Parr shaker and degassed under vacuum and filled with nitrogen gas three times. Then, all nitrogen gas was removed, and the reactor was pressurized to 45 psi with hydrogen gas. The mixture was shaken for 6 h more. After that time, the reactor was depressurized and filtered then concentrated under vacuum. EtOAc (25 mL) was added plus AcOH (5 mL), then purged the mixture under nitrogen and 1.0 equivalents of fresh Pd/C (665 mg of 10% w/w, 0.6214 mmol) was added. The mixture was put in a Parr shaker and degassed under vacuum and filled with nitrogen gas three times. Then, all nitrogen gas was removed, and the reactor was pressurized to 35 psi with hydrogen gas. The mixture was shaken for 3 h more. After that time, the reactor was depressurized and the reaction was filtered and concentrated under vacuum. The residue was purified by silica gel chromatography (40 g column) using a gradient from 0% to 30% ethyl acetate in hexanes giving as a yellow solid, tert-butyl N-[6-hydroxy-13-methyl-6,15-bis(trifluoromethyl)-19-oxa-3,4,13,18-tetrazatricyclo[12.3.1.1²,⁵]nonadeca-1(17),2,4,14(18),15-pentaen-17-yl]carbamate (209 mg, 62%). ¹H NMR (400 MHz, DMSO-d6) δ 9.10 (s, 1H), 8.53 (s, 1H), 7.65 (s, 1H), 3.44 (td, J=14.1, 13.3, 4.3 Hz, 1H), 3.34 (d, J=4.8 Hz, 1H), 3.31-3.25 (m, 1H), 3.03 (d, J=2.0 Hz, 3H), 2.15 (d, J=8.6 Hz, 2H), 1.89 (dd, J=12.1, 5.3 Hz, 1H), 1.72-1.65 (m, JH), 1.65-1.55 (m, 2H), 1.47 (s, 9H), 1.46-1.35 (m, 3H) ppm. ESI-MS m/z calc. 539.1967, found 540.2 (M+1)⁺; Retention time: 1.96 minutes (LC Method J).

Step 7: 17-Amino-13-methyl-6,15-bis(trifluoromethyl)-19-oxa-3,4,13,18-tetrazatricyclo[12.3.1.1²,⁵]nonadeca-1(18),2,4,14,16-pentaen-6-ol

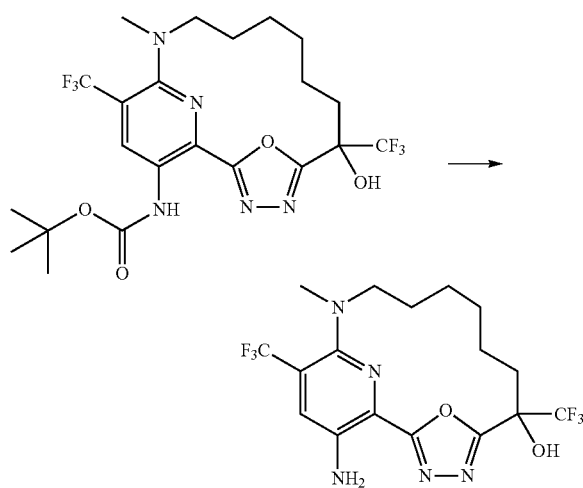

To a solution of tert-butyl N-[6-hydroxy-13-methyl-6,15-bis(trifluoromethyl)-19-oxa-3,4,13,18-tetrazatricyclo[12.3.1.1²,⁵]nonadeca-1(17),2,4,14(18),15-pentaen-17-yl]carbamate (185 mg, 0.3429 mmol) in DCM (3.0 mL) was added TFA (1.25 mL, 16.22 mmol) and stirred at room temperature for 2 hours. The mixture was evaporated and the residue was purified by reverse phase HPLC using C₁₈ column and a gradient from 1% to 99% acetonitrile in water (+5 mM HCl) over 15.0 minutes giving as a yellow solid, 17-amino-13-methyl-6,15-bis(trifluoromethyl)-19-oxa-3,4,13,18-tetrazatricyclo[12.3.1.1²,⁵]nonadeca-1(18),2,4,14,16-pentaen-6-ol (130 mg, 86%). ESI-MS m/z calc. 439.1443, found 440.2 (M+1)⁺; Retention time: 1.95 minutes (LC Method A).

Step 8: 17-Amino-13-methyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (Compound 19) and 17-amino-13-methyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (Compound 20)

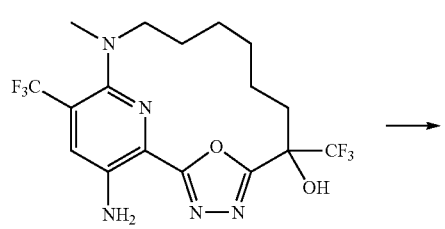

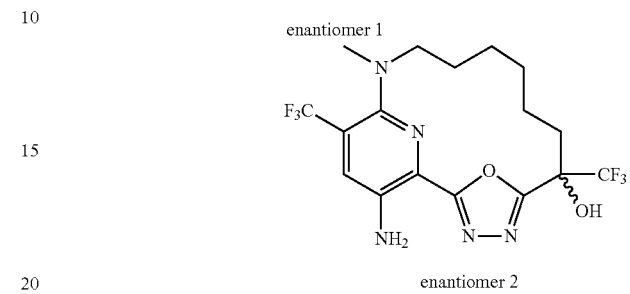

enantiomer 1 enantiomer 2

Racemic 17-amino-13-methyl-6,15-bis(trifluoromethyl)-19-oxa-3,4,13,18-tetrazatricyclo[12.3.1.1²,⁵]nonadeca-1(18),2,4,14,16-pentaen-6-ol (130 mg, 0.2959 mmol) was purified by chiral SFC using a Phenomenex LUX-4 column (250×21.2 mm, 5 μm particle size) eluting with 12% methanol/88% CO₂ with a flow rate 70.0 mL/min (injection volume of 500 μL) giving two single enantiomers:

The first enantiomer to elute was isolated as a yellow solid, 17-amino-13-methyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (45.0 mg, 69%). ¹H NMR (400 MHz, DMSO-d6) δ 7.70 (s, 1H), 7.59 (d, J=16.9 Hz, 1H), 4.97 (d, J=36.3 Hz, 2H), 3.30-3.13 (m, 2H), 2.87 (d, J=1.5 Hz, 3H), 2.14 (t, J=7.3 Hz, 2H), 1.93 (dt, J=12.6, 6.3 Hz, 1H), 1.72-1.65 (m, 1H), 1.55 (ddt, J=37.4, 14.8, 7.4 Hz, 4H), 1.40 (td, J=14.2, 12.9, 6.1 Hz, 2H) ppm. ESI-MS m/z calc. 439.1443, found 440.2 (M+1)⁺; Retention time: 2.03 minutes (LC Method A).

The second enantiomer to elute was isolated as yellow solid, 17-amino-13-methyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (44.9 mg, 68%). ¹H NMR (400 MHz, DMSO-d6) δ 7.70 (s, 1H), 7.60 (d, J=16.1 Hz, 1H), 4.86 (d, J=51.0 Hz, 2H), 3.22 (dtd, J=34.7, 13.0, 4.4 Hz, 2H), 2.87 (d, J=1.4 Hz, 3H), 2.14 (t, J=7.3 Hz, 2H), 1.94 (td, J=12.1, 5.6 Hz, 1H), 1.73-1.65 (m, 1H), 1.55 (ddt, J=37.4, 14.2, 7.3 Hz, 4H), 1.38 (dt, J=14.6, 7.7 Hz, 2H) ppm. ESI-MS m/z calc. 439.1443, found 440.2 (M+1)⁺; Retention time: 2.03 minutes (LC Method A).

Step 9: Solid Form Characterization of Amorphous Compound 19 (Neat Form)

A. X-Ray Powder Diffraction

The XRPD diffractogram for amorphous Compound 19 (neat form) was acquired using the General X-Ray Powder Diffraction (XRPD) Method and is provided in FIG. 4.

B. Thermogravimetric Analysis (TGA)

Figure 5:
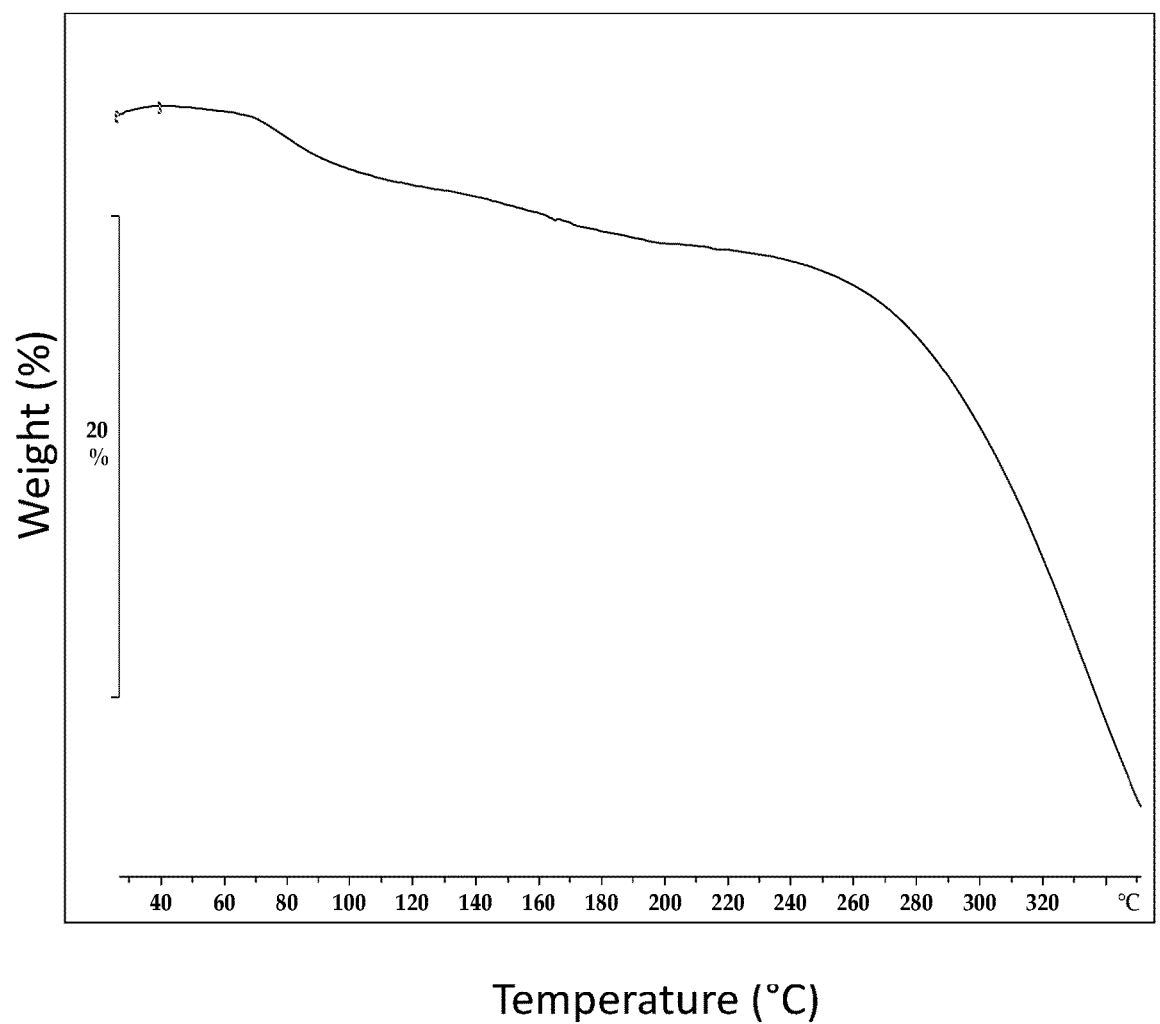
FIG. 5 provides a TGA curve for amorphous Compound 19 (neat form).

The TGA curve for amorphous Compound 19 (neat form) is provided in FIG. 5. The TGA curve shows 5.71% weight loss from ~40-198.6° C., with a ramp of 10.00° C./min to 350.00° C.

291

C. Differential Scanning calorimetry Analysis

The DSC data for amorphous Compound 19 (neat form) were collected using the following method:
1. 25° C. to 200.00° C., 10° C./min,
2. 200° C. to −20° C., −50° C./min, then
3. −20° C. to 150° C., 10° C./min.

Figure 6:
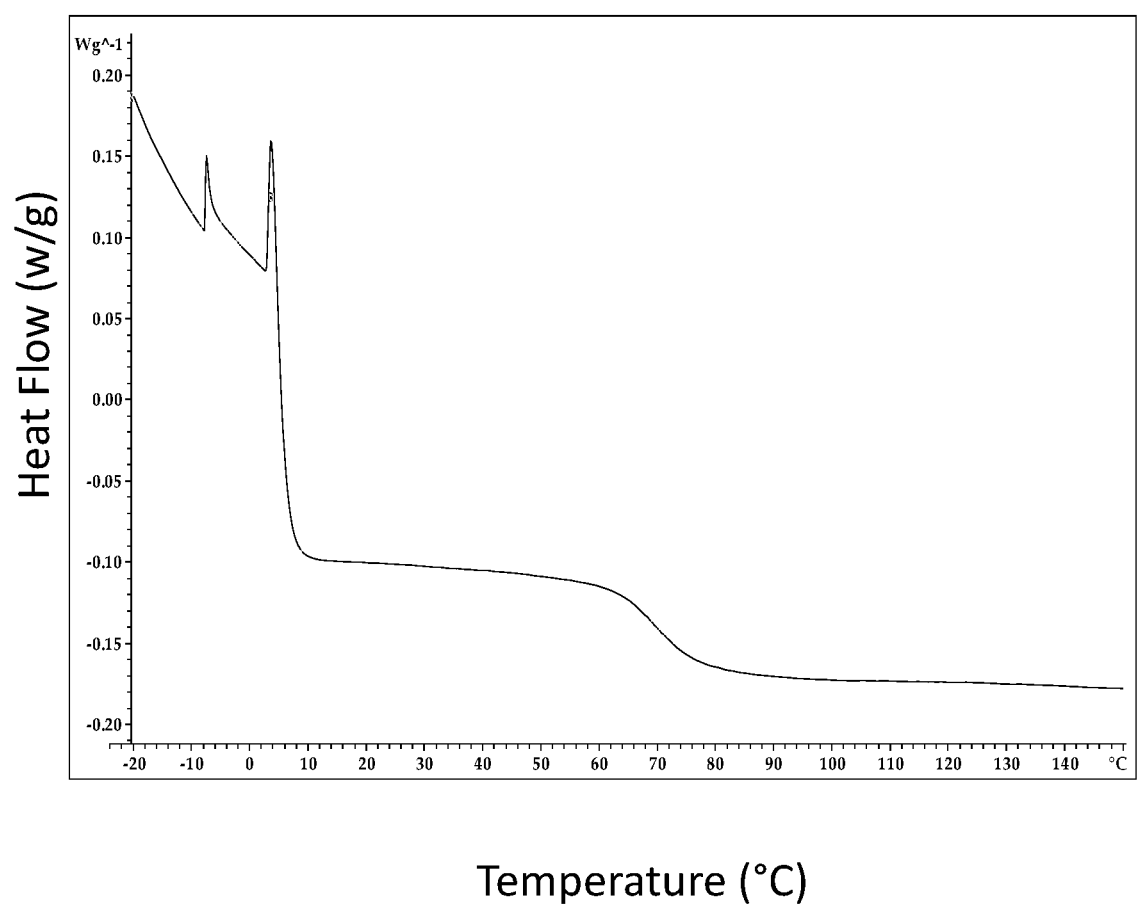
FIG. 6 provides a DSC analysis of amorphous Compound 19 (neat form).

The DSC thermogram for amorphous Compound 19 (neat form) is provided in FIG. 6. The thermogram shows a Tg midpoint at 69.6° C.

292

Example 15: Preparation of (12R)-20-amino-18-(trifluoromethyl)-22-oxa-3,4,16,21-tetraazatetracyclo[15.3.1.12,5.012,16]docosa-1(21),2,4,17,19-pentaen-6-ol (enantiomer 1) (Compound 21) and (12R)-20-amino-18-(trifluoromethyl)-22-oxa-3,4,16,21-tetraazatetracyclo[15.3.1.12,5.012,16]docosa-1(21),2,4,17,19-pentaen-6-ol (enantiomer 2) (Compound 22)

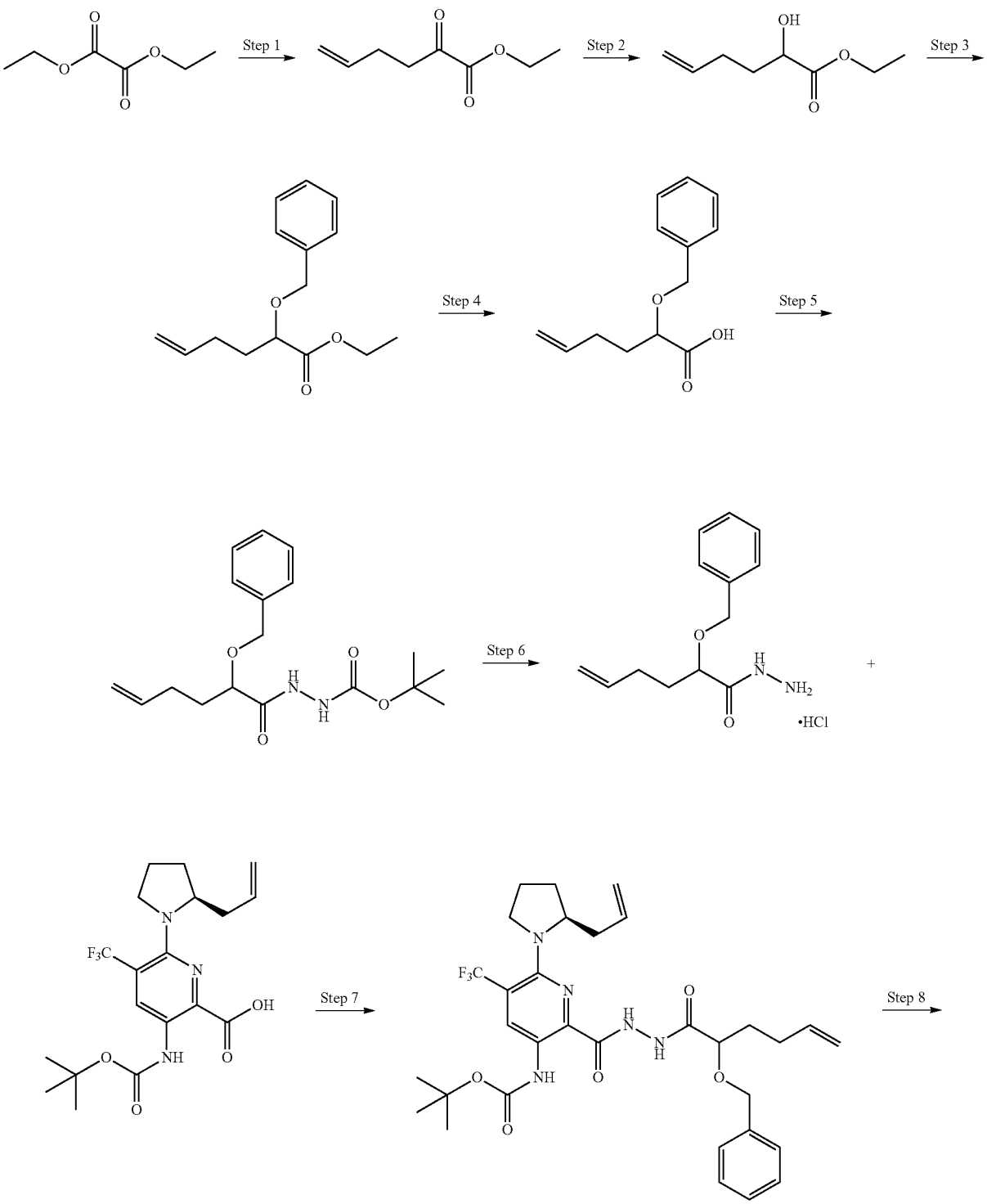

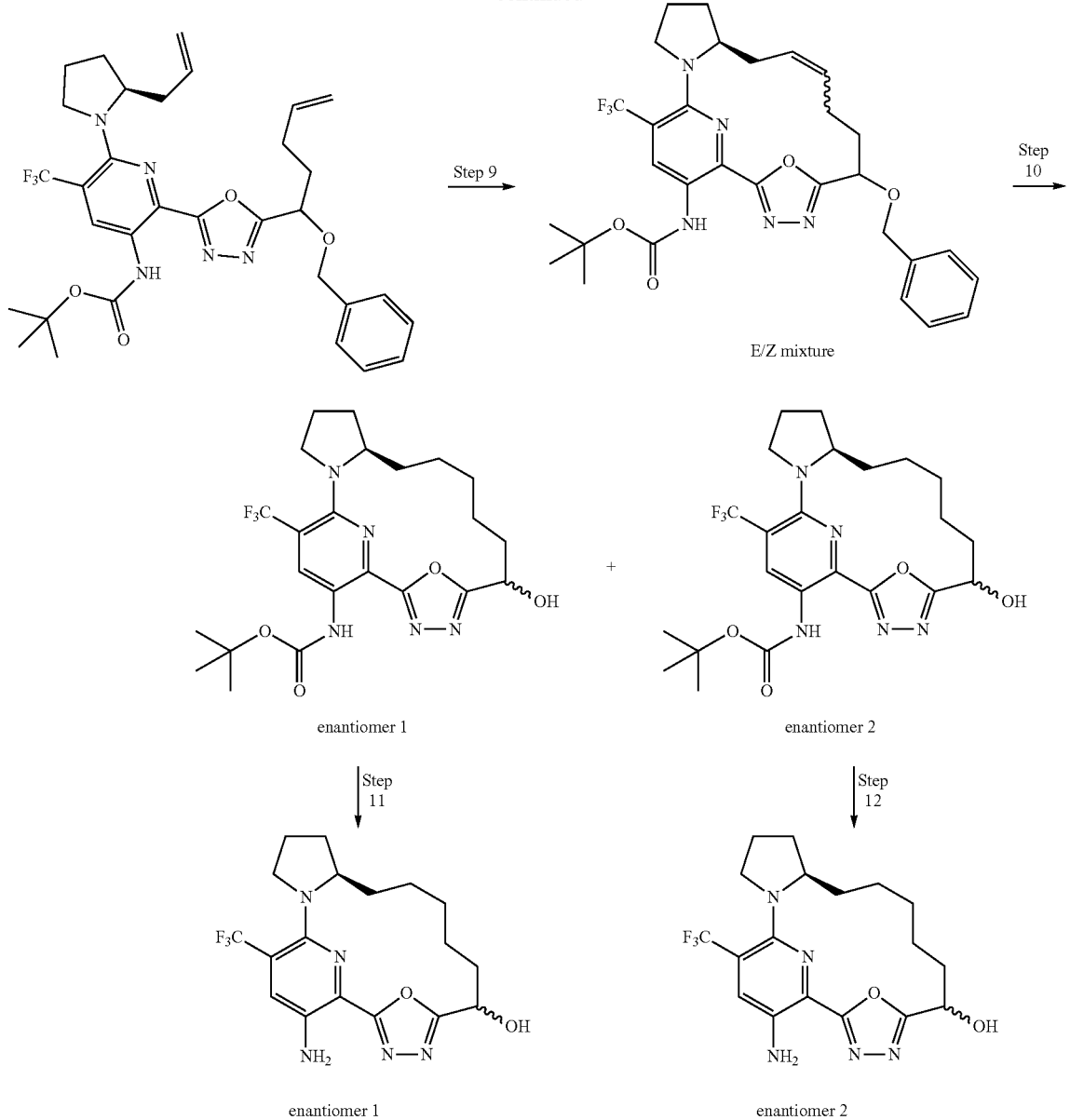

E/Z mixture enantiomer 1      enantiomer 2 enantiomer 1      enantiomer 2

Step 1: Ethyl 2-oxohex-5-enoate

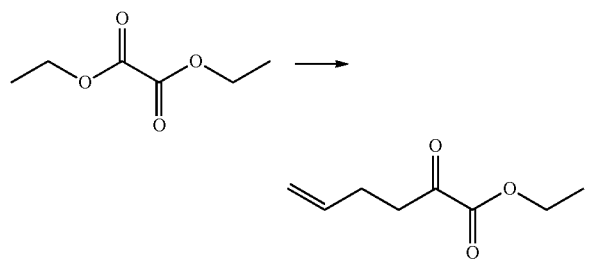

A solution of diethyl oxalate (58.5 g, 400.3 mmol) in THF (290 mL) in 2 L flask with mechanical stirring under nitrogen was cooled in a dry ice bath and bromo(but-3-enyl) magnesium (800 mL of 0.5 M, 400 mmol) was added dropwise over 1.5 h, keeping the internal temperature at −70° C. The resultant cloudy cream solution was stirred for 2 h, then quenched by addition of citric acid (400 mL of 1 M, 400 mmol) removed from the cold bath and stirred for 0.5 h. Phases were separated and organic phase was washed with saturated NaHCO$_3$ (3×250 mL) and brine (2×250 mL). The aqueous phases were back extracted once with MTBE (300 mL) and the combined organic phases were dried, filtered and evaporated. Purification by silica gel chromatography with a gradient of 0% to 100% DCM in hexanes gave as a yellow liquid, ethyl 2-oxohex-5-enoate (49 g, 78%). $^1$H NMR (400 MHz, Chloroform-d) δ 5.82 (ddt, J=16.8, 10.2, 6.5 Hz, 1H), 5.07 (dq, J=17.1, 1.6 Hz, 1H), 5.02 (dq, J=10.2, 1.4 Hz, 1H), 4.32 (q, J=7.1 Hz, 2H), 2.95 (t, J=7.3 Hz, 2H), 2.45-2.34 (m, 2H), 1.37 (t, J=7.1 Hz, 3H) ppm.

Step 2: Ethyl 2-hydroxyhex-5-enoate

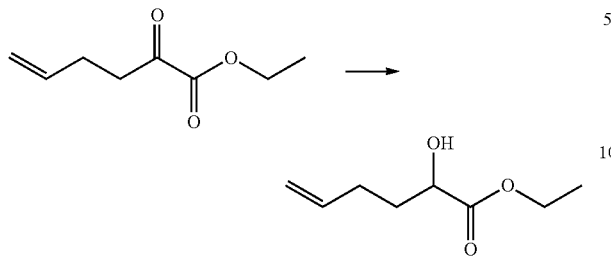

To a solution of ethyl 2-oxohex-5-enoate (12.4 g, 79.4 mmol) in dichloromethane (317.6 mL) was added sodium triacetoxyborohydride (33.66 g, 158.8 mmol) and the mixture was stirred overnight at room temperature. The reaction was carefully quenched with the addition of saturated aqueous NaHCO$_3$. The resulting layers were separated and the aqueous layer was further extracted with DCM (2×150 mL). The combined organic layers were dried over sodium sulfate, filtered and concentrated to afford as a pale-yellow oil, ethyl 2-hydroxyhex-5-enoate (12.2 g, 97%). $^1$H NMR (400 MHz, DMSO-d6) δ 5.99-5.63 (m, 1H), 5.36 (d, J=5.9 Hz, 1H), 5.21-4.76 (m, 2H), 4.09 (qd, J=7.1, 1.3 Hz, 2H), 3.99 (dt, J=7.9, 4.9 Hz, 1H), 2.08 (tdd, J=8.1, 6.6, 1.5 Hz, 2H), 1.82-1.49 (m, 2H), 1.19 (t, J=7.1 Hz, 3H) ppm.

Step 3: Ethyl 2-benzyloxyhex-5-enoate

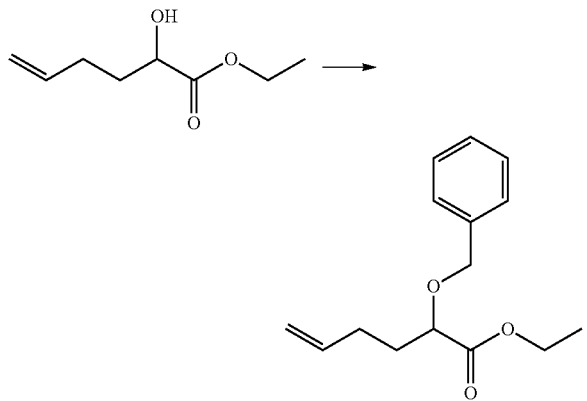

To a solution of ethyl 2-hydroxyhex-5-enoate (12.3 g, 77.75 mmol) in DMF (65.89 mL) at 0° C. was added sodium hydride (3.9 g of 60% w/w, 97.51 mmol) portion-wise. The mixture (cream suspension) was stirred at 0° C. for 30 min. To the mixture was added bromomethylbenzene (11.61 mL, 97.61 mmol) and the mixture allowed to warm to ambient temperature and stirred for 18 h. The reaction was quenched with slow addition of 200 mL of saturated aqueous NH$_4$Cl and the resulting mixture was stirred at ambient temperature for 10 min. The mixture was diluted with MTBE (415.2 mL) and the organic phase separated. The organic phase was washed with water (166.2 mL), brine (50 mL), dried over MgSO$_4$, filtered and concentrated to afford as an orange oil, ethyl 2-benzyloxyhex-5-enoate (19 g, 98%). $^1$H NMR (400 MHz, DMSO-d6) δ 7.39-7.27 (m, 5H), 6.01-5.50 (m, 1H), 5.05-4.91 (m, 2H), 4.65-4.34 (m, 2H), 4.14 (qd, J=7.1, 3.6 Hz, 2H), 3.97 (dd, J=7.2, 5.4 Hz, 1H), 2.10 (dtd, J=8.0, 6.7, 1.4 Hz, 2H), 1.74 (dtd, J=12.6, 7.1, 6.3, 3.1 Hz, 2H), 1.21 (t, J=7.1 Hz, 3H) ppm. Retention time: 0.75 minutes (LC Method S).

Step 4: 2-Benzyloxyhex-5-enoic Acid

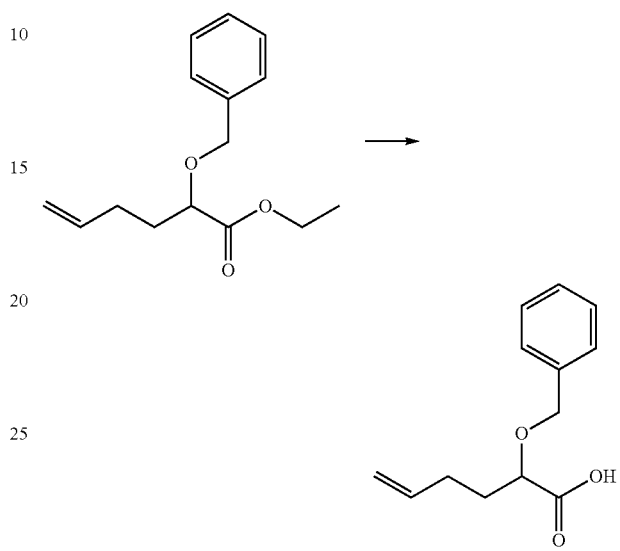

To a solution of ethyl 2-benzyloxyhex-5-enoate (19.3 g, 77.72 mmol) in MeOH (112.6 mL) and THF (38.6 mL) was added NaOH (72.2 mL of 2 M, 144.4 mmol) and the mixture stirred at ambient temperature for 6 h. The organic solvents were removed in vacuo and the residue was diluted with 1 M NaOH (25 mL) and extracted with MTBE (2×300 mL). The organic phases were back extracted once with 100 mL of 1 N NaOH and the combined aqueous phases were acidified to pH=1 with 10% aqueous HCl. The aqueous phase was extracted with ethyl acetate (2×150 mL) and the organic phases were combined and washed with brine (150 mL). The organic phase was dried over MgSO$_4$, filtered and concentrated in vacuo providing as an orange oil, 2-benzyloxyhex-5-enoic acid (13.5 g, 79%). $^1$H NMR (400 MHz, DMSO-d6) δ 12.61 (s, 1H), 7.67-6.71 (m, 5H), 5.79 (ddt, J=16.9, 10.2, 6.6 Hz, 1H), 5.07-4.81 (m, 2H), 4.49 (dd, J=103.0, 11.7 Hz, 2H), 3.88 (dd, J=7.8, 4.7 Hz, 1H), 2.18-2.04 (m, 2H), 1.75 (tqd, J=14.9, 7.3, 2.9 Hz, 2H) ppm. ESI-MS m/z calc. 220.10994, found 221.1 (M+1)$^+$; Retention time: 0.57 minutes (LC Method S).

Step 5: tert-Butyl N-(2-benzyloxyhex-5-enoylamino)carbamate

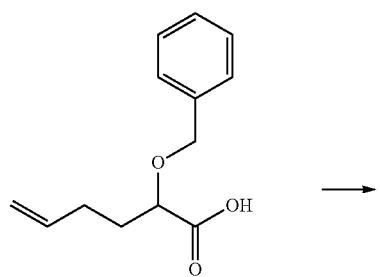

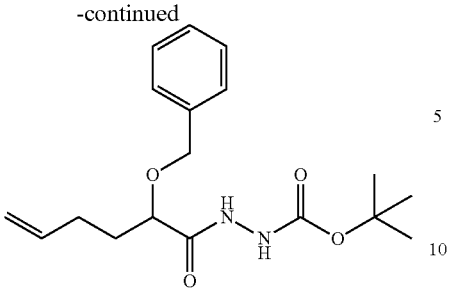

To a solution of 2-benzyloxyhex-5-enoic acid (13.5 g, 61.29 mmol) in DMF (112.2 mL) was added HATU (30.71 g, 80.77 mmol) and DIEA (22.83 mL, 131.1 mmol) and the mixture was stirred at ambient temperature for 10 min. To the mixture was added tert-butyl N-aminocarbamate (8.424 g, 63.74 mmol) (slight exotherm upon addition) and the mixture was stirred at ambient temperature for 3 h. The reaction was diluted with water and extracted with ethyl acetate (3×20 mL). The organic layers were washed with brine (25 mL), dried over MgSO$_4$, filtered and concentrated in vacuo to give an orange colored oil. The crude material was then purified on silica gel chromatography (12 gram column) using a gradient from 0% to 50% ethyl acetate in hexanes which afforded as a colorless oil, tert-butyl N-(2-benzyloxyhex-5-enoylamino)carbamate (20 g, 76%). $^1$H NMR (400 MHz, DMSO-d6) δ 9.71 (s, 1H), 8.77 (s, 1H), 7.52-7.11 (m, 5H), 5.91-5.69 (m, 1H), 5.06-4.88 (m, 2H), 4.48 (dd, J=110.1, 11.7 Hz, 2H), 3.82 (t, J=6.3 Hz, 1H), 2.69 (s, 9H), 2.22-2.01 (m, 2H), 1.81-1.62 (m, 2H) ppm.

Step 6: 2-Benzyloxyhex-5-enehydrazide (hydrochloride Salt)

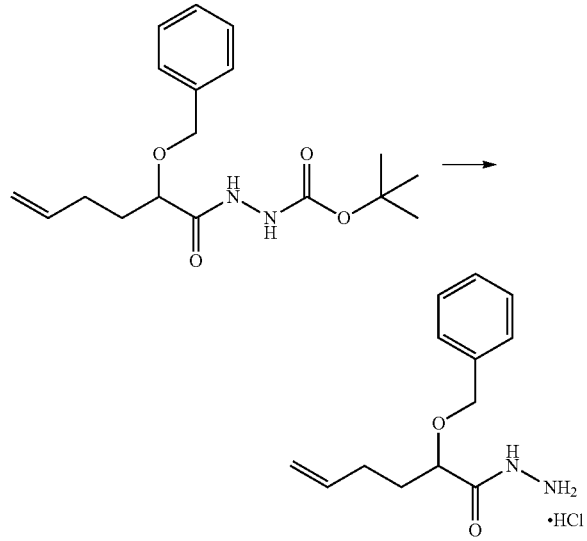

To a solution of tert-butyl N-(2-benzyloxyhex-5-enoylamino)carbamate (515 mg, 1.54 mmol) in dichloromethane (2.962 mL) was added HCl (1.782 mL of 4 M in dioxane, 7.128 mmol). The mixture was stirred at room temperature overnight, concentrated and co-evaporated with dichloromethane and heptanes to give as a white solid, 2-benzyloxyhex-5-enehydrazide (hydrochloride salt) (417 mg, 99%). $^1$H NMR (400 MHz, DMSO-d6) δ 11.04 (s, 1H), 10.20 (s, 2H), 7.43-7.26 (m, 5H), 5.79 (ddt, J=16.9, 10.3, 6.6 Hz, 1H), 5.12-4.76 (m, 2H), 4.49 (dd, J=67.3, 11.7 Hz, 2H), 4.01 (t, J=6.2 Hz, 1H), 2.15-2.00 (m, 2H), 1.75 (td, J=7.9, 6.0 Hz, 2H) ppm.

Step 7: tert-Butyl N-[6-[(2S)-2-allylpyrrolidin-1-yl]-2-[(2-benzyloxyhex-5-enoylamino)carbamoyl]-5-(trifluoromethyl)-3-pyridyl]carbamate

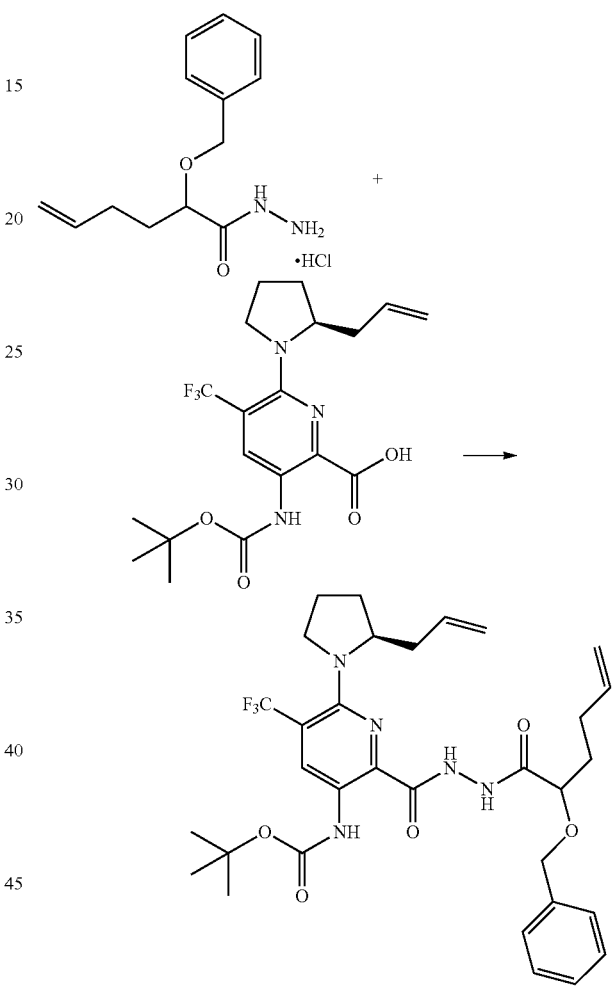

To a solution of 6-[(2S)-2-allylpyrrolidin-1-yl]-3-(tert-butoxycarbonylamino)-5-(trifluoromethyl)pyridine-2-carboxylic acid (3.5 g, 8.425 mmol) in NMP (44.87 mL) was added 2-benzyloxyhex-5-enehydrazide (hydrochloride salt) (2.313 g, 8.543 mmol), DIEA (4.457 mL, 25.59 mmol) and HATU (4.475 g, 11.77 mmol). The reaction mixture was stirred at room temperature for 3 h. The reaction was extracted with ethyl acetate (3×20 mL). The organic layers were washed with brine (20 mL), dried over sodium sulfate, filtered and evaporated. The crude material was then purified by silica gel chromatography (12 gram column) using a gradient from 0% to 70% ethyl acetate in hexanes giving as a yellow solid, tert-butyl N-[6-[(2S)-2-allylpyrrolidin-1-yl]-2-[(2-benzyloxyhex-5-enoylamino)carbamoyl]-5-(trifluoromethyl)-3-pyridyl]carbamate (2.65 g, 50%). ESI-MS m/z calc. 631.29816, found 632.5 (M+1)$^+$; Retention time: 0.76 minutes (LC Method T).

Step 8: tert-Butyl N-[6-[(2S)-2-allylpyrrolidin-1-yl]-2-[15-(1-benzyloxypent-4-enyl)-1,3,4-oxadiazol-2-yl]-5-(trifluoromethyl)-3-pyridyl]carbamate

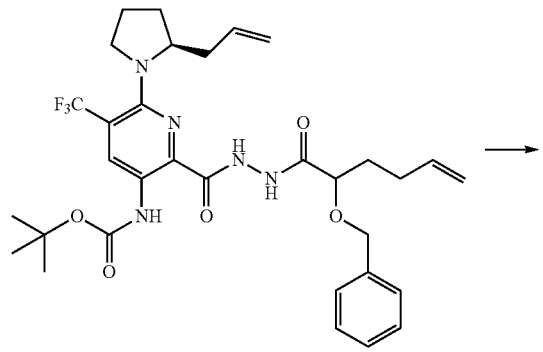

Step 9: tert-Butyl N-[(12S)-6-(benzyloxy)-18-(trifluoromethyl)-22-oxa-3,4,16,21-tetraazatetracyclo[15.3.1.12,5.012,16]docosa-1(21),2,4,9,17,19-hexaen-20-yl]carbamate (E/Z mixture)

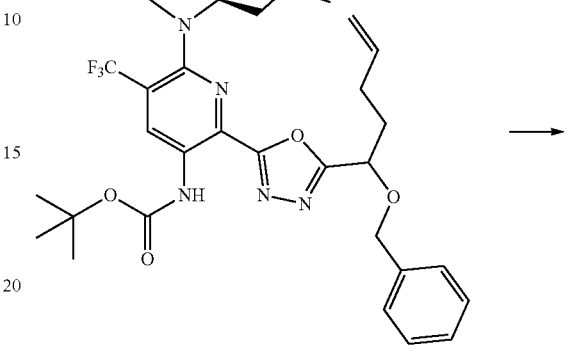

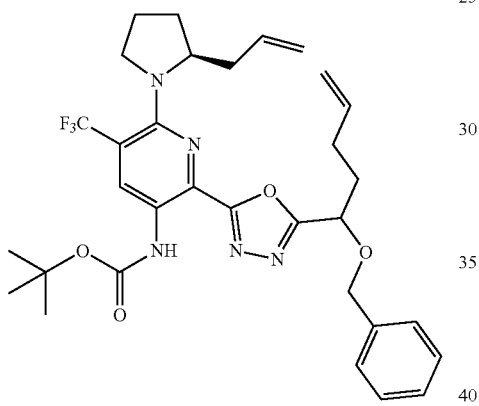

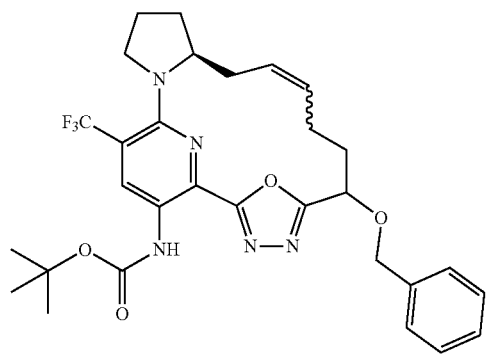

E/Z mixture

A solution of tert-butyl N-[6-[(2S)-2-allylpyrrolidin-1-yl]-2-[(2-benzyloxyhex-5-enoylamino)carbamoyl]-5-(trifluoromethyl)-3-pyridyl]carbamate (2.53 g, 4.005 mmol) and DIEA (2.425 mL, 13.92 mmol) in acetonitrile (57.84 mL) was heated to 50° C., then p-toluenesulfonyl chloride (840 mg, 4.406 mmol) was added in 2 portions. The mixture was heated at 70° C. for 2 hours. The reaction mixture was cooled and quenched with a saturated aqueous solution of sodium bicarbonate (25 mL) and extracted with ethyl acetate (3×25 mL). The combined organics were dried over sodium sulfate, filtered and evaporated. The residue was purified by silica gel chromatography (12 gram column) using a gradient from 0% to 30% ethyl acetate in hexanes to afford as a yellow semi-solid, tert-butyl N-[6-[(2S)-2-allylpyrrolidin-1-yl]-2-[5-(1-benzyloxypent-4-enyl)-1,3,4-oxadiazol-2-yl]-5-(trifluoromethyl)-3-pyridyl]carbamate (1.75 g, 71%). ESI-MS m/z calc. 613.2876, found 614.5 (M+1)+; Retention time: 0.9 minutes (LC Method T).

To a degassed solution of tert-butyl N-[6-[(2S)-2-allylpyrrolidin-1-yl]-2-[5-(1-benzyloxypent-4-enyl)-1,3,4-oxadiazol-2-yl]-5-(trifluoromethyl)-3-pyridyl]carbamate (2.0 g, 3.259 mmol) in DCE (481.2 mL) was added Zhan catalyst-1B (358.7 mg, 0.4889 mmol) at 50° C. under nitrogen atmosphere in two portions over 10 minutes. The resulting mixture was heated at 70° C. for 20 h. The reaction mixture was cooled to room temperature and concentrated under reduced pressure. The residue was purified by silica gel chromatography (24 g column) using a gradient from 0% to 30% ethyl acetate in hexanes giving as a yellow residue, tert-butyl N-[(12S)-6-(benzyloxy)-18-(trifluoromethyl)-22-oxa-3,4,16,21-tetraazatetracyclo[15.3.1.12,5.012,16]docosa-1(21),2,4,9,17,19-hexaen-20-yl]carbamate (E/Z mixture) (110 mg, 6%). ESI-MS m/z calc. 585.2563, found 586.4 (M+1)+; Retention time: 0.85 minutes (LC Method T).

Step 10: tert-Butyl N-[(12R)-6-hydroxy-18-(trifluoromethyl)-22-oxa-3,4,16,21-tetraazatetracyclo[15.3.1.1²,⁵.0¹²,¹⁶]docosa-1(21),2,4,17,19-pentaen-20-yl]carbamate (enantiomer 1) and tert-butyl N-[(12R)-6-hydroxy-18-(trifluoromethyl)-22-oxa-3,4,16,21-tetraazatetracyclo[15.3.1.1²,⁵.0¹²,¹⁶]docosa-1(21),2,4,17,19-pentaen-20-yl]carbamate (enantiomer 2)

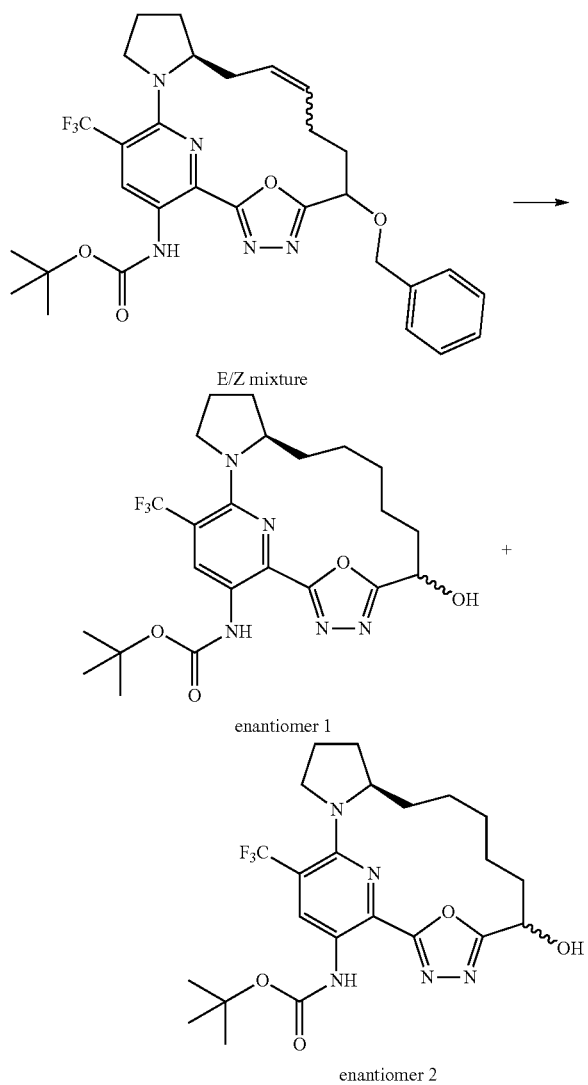

To a solution of tert-butyl N-[(12S)-6-(benzyloxy)-18-(trifluoromethyl)-22-oxa-3,4,16,21-tetraazatetracyclo[15.3.1.1²,⁵.0¹²,¹⁶]docosa-1(21),2,4,9,17,19-hexaen-20-yl]carbamate (E/Z mixture) (200 mg, 0.3415 mmol) in AcOH (5.4 mL) was added Pd/C (145.4 mg of 10% w/w, 0.1366 mmol). The mixture was shaken overnight under a hydrogen atmosphere using a Parr shaker at 45 psi. The reaction mixture was filtered through a silica plug, washing well with ethyl acetate and then the filtrate was concentrated to give a yellow residue, tert-butyl N-[(12R)-6-hydroxy-18-(trifluoromethyl)-22-oxa-3,4,16,21-tetraazatetracyclo[15.3.1.1²,⁵.0¹²,¹⁶]docosa-1(21),2,4,17,19-pentaen-20-yl]carbamate. Purification of this material by silica gel chromatography (24 g column) using a gradient from 0% to 10% ethyl acetate in hexanes over 20 minutes gave separation of the two diastereomers which were each isolated as single enantiomers:

The first enantiomer to elute was isolated as a yellow solid, tert-butyl N-[(12R)-6-hydroxy-18-(trifluoromethyl)-22-oxa-3,4,16,21-tetraazatetracyclo[15.3.1.1²,⁵.0¹²,¹⁶]docosa-1(21),2,4,17,19-pentaen-20-yl]carbamate (enantiomer 1) (50 mg, 59%). $^1$H NMR (400 MHz, Chloroform-d) δ 8.90 (s, 2H), 5.26 (dd, J=8.8, 4.2 Hz, 1H), 4.22 (ddt, J=9.8, 7.5, 3.9 Hz, 1H), 4.04-3.66 (m, 1H), 3.69-3.42 (m, 2H), 2.44-2.30 (m, 1H), 2.29-2.12 (m, 2H), 2.00 (tdd, J=6.8, 4.5, 2.7 Hz, 2H), 1.92-1.73 (m, 2H), 1.71-1.57 (m, 3H), 1.54 (s, 9H), 1.46 (qt, J=8.7, 3.8 Hz, 3H), 1.11-0.94 (m, 1H) ppm. ESI-MS m/z calc. 497.22498, found 498.42 (M+1)⁺; Retention time: 0.59 minutes (LC Method T).

The second enantiomer to elute was isolated as a yellow solid, tert-butyl N-[(12R)-6-hydroxy-18-(trifluoromethyl)-22-oxa-3,4,16,21-tetraazatetracyclo[15.3.1.1²,⁵.0¹²,¹⁶]docosa-1(21),2,4,17,19-pentaen-20-yl]carbamate (enantiomer 2) (30 mg, 35%). $^1$H NMR (400 MHz, Chloroform-d) δ 8.95 (s, 1H), 8.91 (s, 1H), 5.05 (dd, J=10.2, 3.4 Hz, 1H), 4.10-4.02 (m, 1H), 3.69-3.43 (m, 2H), 3.37-2.79 (m, 1H), 2.56 (dddd, J=10.4, 8.4, 5.9, 2.3 Hz, 1H), 2.35-2.12 (m, 2H), 1.99 (ddt, J=14.2, 6.5, 3.9 Hz, 2H), 1.86-1.45 (m, 17H), 1.05-0.90 (m, 1H) ppm. ESI-MS m/z calc. 497.22498, found 498.42 (M+1)⁺; Retention time: 0.6 minutes (LC Method T).

Step 11: (12R)-20-Amino-18-(trifluoromethyl)-22-oxa-3,4,16,21-tetraazatetracyclo[15.3.1.1²,⁵.0¹²,¹⁶]docosa-1(21),2,4,17,19-pentaen-6-ol (enantiomer 1) (Compound 21)

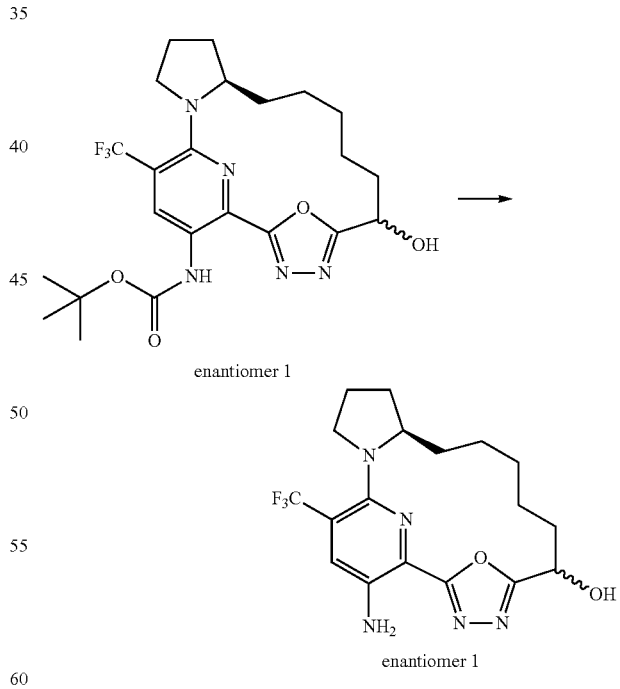

To a solution of tert-butyl N-[(12R)-6-hydroxy-18-(trifluoromethyl)-22-oxa-3,4,16,21-tetraazatetracyclo[15.3.1.1²,⁵.0¹²,¹⁶]docosa-1(21),2,4,17,19-pentaen-20-yl]carbamate (enantiomer 1) (7 mg, 0.01407 mmol) in DCM (129.8 μL) was added TFA (58.6 μL, 0.7606 mmol) and the mixture was stirred at room temperature for 2 h. The reaction was concentrated, then taken up in DCM and washed with saturated aqueous NaHCO₃ solution. The organic layer was concentrated to afford as a yellow solid, (12R)-20-amino-18-(trifluoromethyl)-22-oxa-3,4,16,21-tetraazatetracyclo[15.3.1.1²,⁵.0¹²,¹⁶]docosa-1(21),2,4,17,19-pentaen-6-ol (enantiomer 1) (4.1 mg, 73%). ¹H NMR (400 MHz, Chloroform-d) δ 7.34 (s, 1H), 5.16 (dd, J=8.7, 4.2 Hz, 1H), 4.20-4.03 (m, 1H), 3.61-3.50 (m, 1H), 3.38-3.28 (m, 1H), 2.27 (ddt, J=9.8, 5.1, 2.6 Hz, 1H), 2.22-2.09 (m, 2H), 1.90 (dqd, J=16.7, 7.1, 6.7, 3.5 Hz, 2H), 1.83-1.66 (m, 2H), 1.64-1.46 (m, 4H), 1.45-1.29 (m, 4H), 0.93 (ddt, J=17.2, 11.2, 5.5 Hz, 2H) ppm. ESI-MS m/z calc. 397.17255, found 398.3 (M+1)⁺; Retention time: 0.31 minutes (LC Method T).

Step 12: (12R)-20-Amino-18-(trifluoromethyl)-22-oxa-3,4,16,21-tetraazatetracyclo[15.3.1.1²,⁵.0¹²,¹⁶]docosa-1(21),2,4,17,19-pentaen-6-ol (enantiomer 2) (Compound 22)

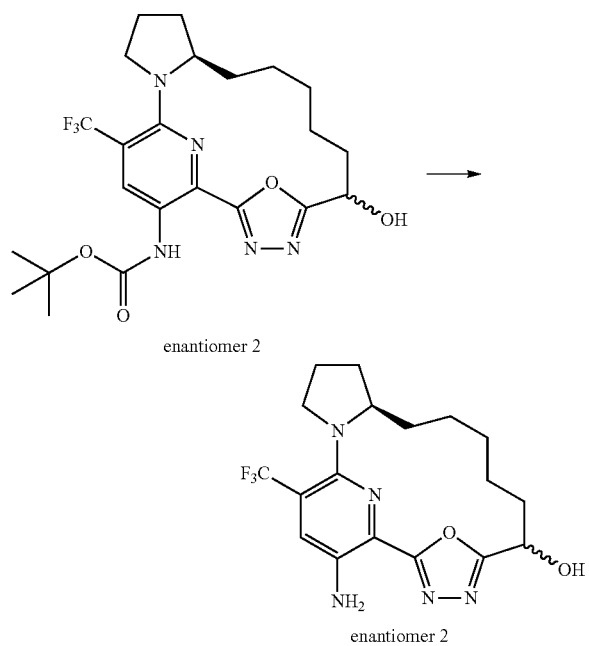

To a solution of tert-butyl N-[(12R)-6-hydroxy-18-(trifluoromethyl)-22-oxa-3,4,16,21-tetraazatetracyclo[15.3.1.1²,⁵.0¹²,¹⁶]docosa-1(21),2,4,17,19-pentaen-20-yl]carbamate (enantiomer 2) (7 mg, 0.01407 mmol) in DCM (129.8 µL) was added TFA (58.6 µL, 0.7606 mmol) and the mixture was stirred at room temperature for 2 h. The reaction was concentrated then taken up in dichloromethane and washed with saturated aqueous NaHCO₃ solution. The organic layer was concentrated to afford as a yellow solid, (12R)-20-amino-18-(trifluoromethyl)-22-oxa-3,4,16,21-tetraazatetracyclo[15.3.1.1²,⁵.0¹²,¹⁶]docosa-1(21),2,4,17,19-pentaen-6-ol (enantiomer 2) (3.0 mg, 54%). ¹H NMR (400 MHz, Chloroform-d) δ 7.19 (s, 1H), 4.97 (dd, J=10.2, 3.4 Hz, 1H), 3.96 (dd, J=7.8, 2.2 Hz, 1H), 3.66-3.46 (m, 1H), 3.42-3.26 (m, 1H), 2.58-2.39 (m, 1H), 2.26-2.03 (m, 2H), 1.91 (ddt, J=14.1, 6.5, 3.3 Hz, 2H), 1.79-1.31 (m, 8H), 0.90-0.67 (m, 4H) ppm. ESI-MS m/z calc. 397.17255, found 398.3 (M+1)⁺; Retention time: 0.31 minutes (LC Method T).

Example 16: Preparation of 21-amino-6,19-bis(trifluoromethyl)-23-oxa-3,4,17,22-tetraazatetracyclo[16.3.1.1²,⁵.0¹³,¹⁷]tricosa-1(22),2,4,18,20-pentaen-6-ol (enantiomer 1) (Compound 23), 21-amino-6,19-bis(trifluoromethyl)-23-oxa-3,4,17,22-tetraazatetracyclo[16.3.1.1²,⁵.0¹³,¹⁷]tricosa-1(22),2,4,18,20-pentaen-6-ol (enantiomer 2) (Compound 24), 21-amino-6,19-bis(trifluoromethyl)-23-oxa-3,4,17,22-tetraazatetracyclo[16.3.1.1²,⁵.0¹³,¹⁷]tricosa-1(22),2,4,18,20-pentaen-6-ol (enantiomer 3) (Compound 25), and 21-amino-6,19-bis(trifluoromethyl)-23-oxa-3,4,17,22-tetraazatetracyclo[16.3.1.1²,⁵.0¹³,¹⁷]tricosa-1(22),2,4,18,20-pentaen-6-ol (enantiomer 4) (Compound 26)

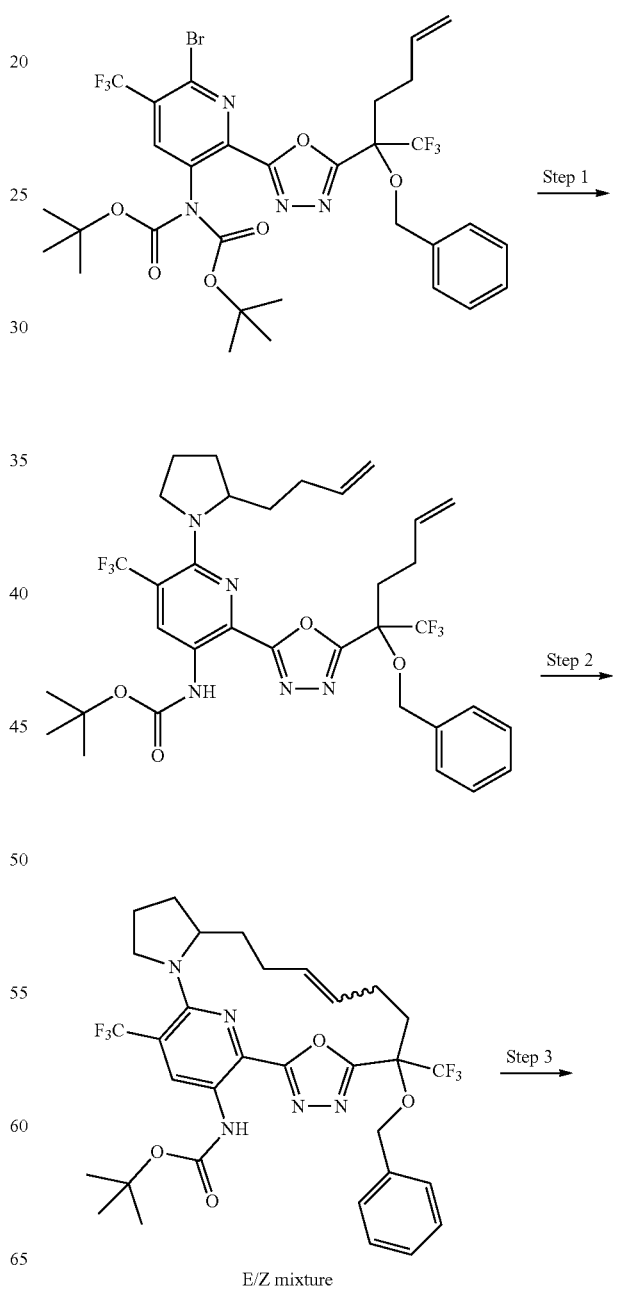

305

-continued

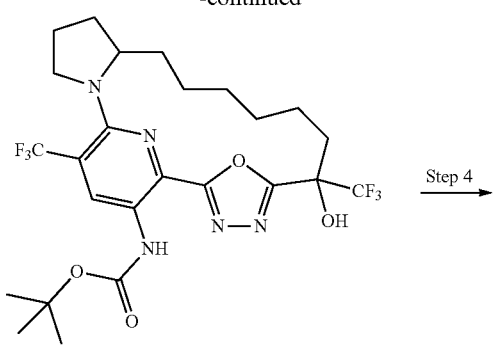

Step 4 →

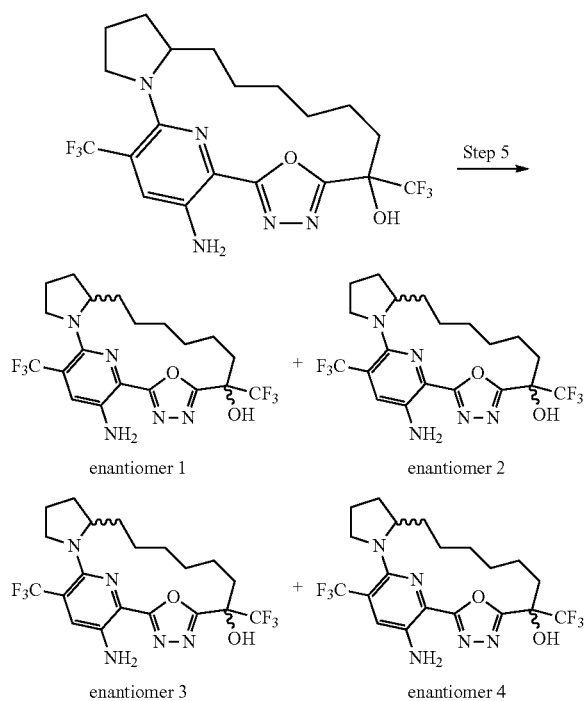

Step 1: tert-Butyl N-[2-[5-[1-benzyloxy-1-(trifluoromethyl)pent-4-enyl]-1,3,4-oxadiazol-2-yl]-6-(2-but-3-enylpyrrolidin-1-yl)-5-(trifluoromethyl)-3-pyridyl]carbamate

306

-continued

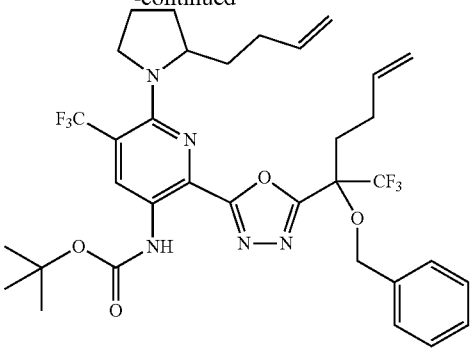

Step 5 →

To a solution of tert-butyl N-[2-[5-[1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate (250.3 mg, 0.3331 mmol) in DMSO (2 mL) was added 2-but-3-enylpyrrolidine (74 mg, 0.591 mmol) and Cs$_2$CO$_3$ (342 mg, 1.05 mmol) in a microwave vial. The reaction was heated at 120° C. for 30 min under microwave irradiation. The reaction mixture was then diluted with ethyl acetate, washed with saturated ammonium chloride solution then brine, dried over anhydrous sodium sulphate, filtered and concentrated. The resultant brown residue was purified by silica gel chromatography using a shallow gradient 0% to 30% EtOAc in hexanes giving as a colorless syrup, tert-butyl N-[2-[5-[1-benzyloxy-1-(trifluoromethyl)pent-4-enyl]-1,3,4-oxadiazol-2-yl]-6-(2-but-3-enylpyrrolidin-1-yl)-5-(trifluoromethyl)-3-pyridyl]carbamate (174 mg, 66%). ESI-MS m/z calc. 695.29065, found 696.37 (M+1)$^+$; Retention time: 1.51 minutes (LC Method U). A minor amount of the product still contained a second N-Boc protecting group, used this material directly in the ensuing step.

Step 2: tert-Butyl N-[6-(benzyloxy)-6,19-bis(trifluoromethyl)-23-oxa-3,4,17,22-tetraazatetracyclo[16.3.1.1$^{2,5}$.0$^{13,17}$]tricosa-1(22),2,4,9,18,20-hexaen-21-yl]carbamate (E/Z mixture)

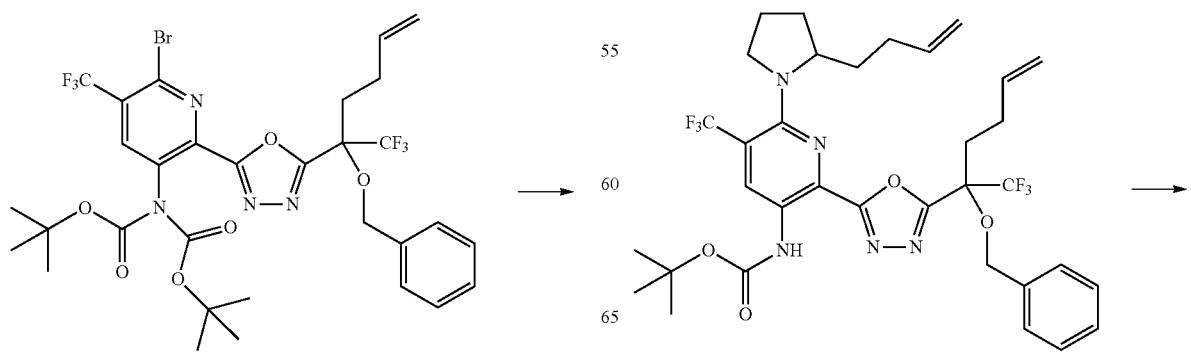

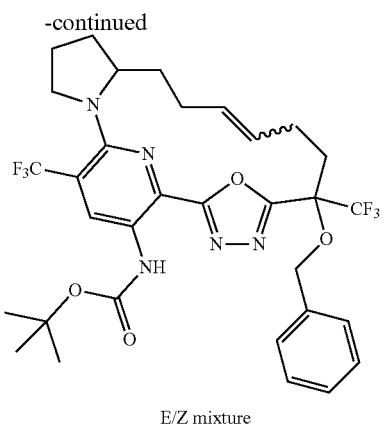

E/Z mixture

To a degassed solution of tert-butyl N-[2-[5-[1-benzyloxy-1-(trifluoromethyl)pent-4-enyl]-1,3,4-oxadiazol-2-yl]-6-(2-but-3-enylpyrrolidin-1-yl)-5-(trifluoromethyl)-3-pyridyl]carbamate (170 mg, 0.2444 mmol) (contaminated with some starting material possessing bis-N-Boc protection, see previous step) in DCE (50 mL) was added Zhan catalyst-1B (47 mg, 0.05848 mmol) and the reaction was heated at 70° C. overnight. The reaction mixture was cooled to room temperature and concentrated under reduced pressure. Diluted the mixture with 1:4 EtOAc/hexanes and filtered through Celite. The filtrate was concentrated and the resultant brown residue was purified by silica gel chromatography using a shallow gradient from 0% to 30% EtOAc in hexanes which gave as a bright yellow oil, tert-butyl N-[6-(benzyloxy)-6,19-bis(trifluoromethyl)-23-oxa-3,4,17,22-tetraazatetracyclo[16.3.1.12,5.013,17]tricosa-1(22),2,4,9,18,20-hexaen-21-yl]carbamate (E/Z mixture) (87 mg, 53%). ESI-MS m/z calc. 667.25934, found 668.38 (M+1)+; Retention time: 2.37 minutes (LC Method M).

Step 3: tert-Butyl N-[6-hydroxy-6,19-bis(trifluoromethyl)-23-oxa-3,4,17,22-tetraazatetracyclo[16.3.1.12,5.013,17]tricosa-1(22),2,4,18,20-pentaen-21-yl]carbamate

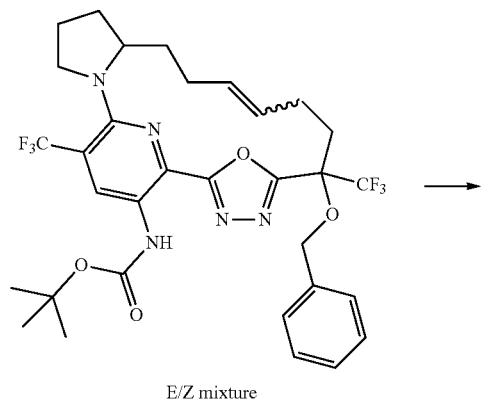

E/Z mixture

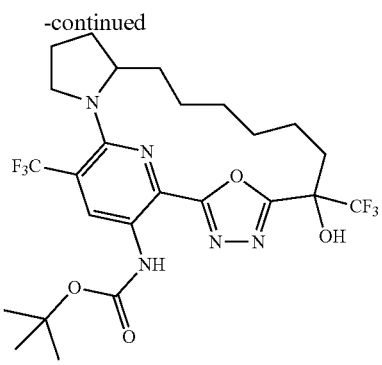

To a solution of tert-butyl N-[6-(benzyloxy)-6,19-bis(trifluoromethyl)-23-oxa-3,4,17,22-tetraazatetracyclo[16.3.1.12,5.013,17]tricosa-1(22),2,4,9,18,20-hexaen-21-yl]carbamate (E/Z mixture) (68 mg, 0.1019 mmol) in AcOH (5 mL) was added Pd/C (62 mg of 10% w/w, 0.05826 mmol, 50% water). The flask was placed on a hydrogen Parr Shaker and degassed under vacuum and filled with nitrogen gas three times. Then, all nitrogen gas was removed, and the reactor was pressurized to 50 psi with hydrogen gas and shaken for 2 days. The flask was depressurized, and the mixture was filtered through Celite and the filtrate was concentrated. The resultant brown residue was purified by silica gel chromatography using a shallow gradient from 0% to 100% EtOAc in hexanes which provided tert-butyl N-[6-hydroxy-6,19-bis(trifluoromethyl)-23-oxa-3,4,17,22-tetraazatetracyclo[16.3.1.12,5.013,17]tricosa-1(22),2,4,18,20-pentaen-21-yl]carbamate (38 mg, 64%). ESI-MS m/z calc. 579.228, found 580.4 (M+1)+; Retention time: 0.86 minutes (LC Method R).

Step 4: 21-Amino-6,19-bis(trifluoromethyl)-23-oxa-3,4,17,22-tetraazatetracyclo[16.3.1.12,5.013,17]tricosa-1(22),2,4,18,20-pentaen-6-ol

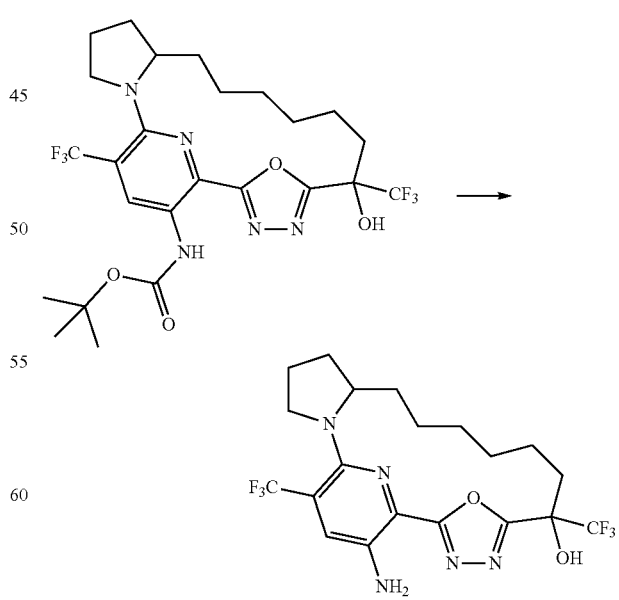

tert-Butyl N-[6-hydroxy-6,19-bis(trifluoromethyl)-23-oxa-3,4,17,22-tetraazatetracyclo[16.3.1.12,5.013,17]tricosa-1(22),2,4,18,20-pentaen-21-yl]carbamate (38 mg, 0.06557 mmol) in a pre-made solution of TFA (250 µL, 3.245 mmol) and dichloromethane (750 µL) was stirred at room temperature for about 1 h. The solvent was removed by evaporation, then diluted the residue in 1 mL of DMSO and purified by reverse phase HPLC using a gradient from 40% to 80% acetonitrile in water (+5 mM HCl) over 30 minutes giving as a yellow solid, 21-amino-6,19-bis(trifluoromethyl)-23-oxa-3,4,17,22-tetraazatetracyclo[16.3.1.12,5.013,17]tricosa-1(22),2,4,18,20-pentaen-6-ol (28 mg, 83%). $^1$H NMR (400 MHz, DMSO-d6) δ 7.75 (s, 1H), 7.62 (s, 1H), 7.48-7.35 (m, 1H), 6.38 (s, 1H), 4.16 (dt, J=43.9, 7.8 Hz, 1H), 3.54 (q, J=8.9 Hz, 2H), 3.14 (t, J=9.0 Hz, 1H), 2.38-2.25 (m, 1H), 2.16 (dd, J=14.6, 8.1 Hz, 1H), 1.97 (dd, J=8.8, 4.3 Hz, 1H), 1.94-1.79 (m, 2H), 1.73 (q, J=9.8, 8.8 Hz, 1H), 1.61 (s, 1H), 1.52-1.26 (m, 5H), 1.23-1.11 (m, 2H), 1.07-0.92 (m, 1H) ppm. ESI-MS m/z calc. 479.1756, found 480.2 (M+1)$^+$; Retention time: 0.69 minutes (LC Method R).

Step 5: 21-Amino-6,19-bis(trifluoromethyl)-23-oxa-3,4,17,22-tetraazatetracyclo[16.3.1.12,5.013,17]tricosa-1(22),2,4,18,20-pentaen-6-ol (enantiomer 1) (Compound 23), 21-amino-6,19-bis(trifluoromethyl)-23-oxa-3,4,17,22-tetraazatetracyclo[16.3.1.12,5.013,17]tricosa-1(22),2,4,18,20-pentaen-6-ol (enantiomer 2) (Compound 24), 21-amino-6,19-bis(trifluoromethyl)-23-oxa-3,4,17,22-tetraazatetracyclo[16.3.1.12,5.013,17]tricosa-1(22),2,4,18,20-pentaen-6-ol (enantiomer 3) (Compound 25), and 21-amino-6,19-bis(trifluoromethyl)-23-oxa-3,4,17,22-tetraazatetracyclo[16.3.1.12,5.013,17]tricosa-1(22),2,4,18,20-pentaen-6-ol (enantiomer 4) (Compound 26)

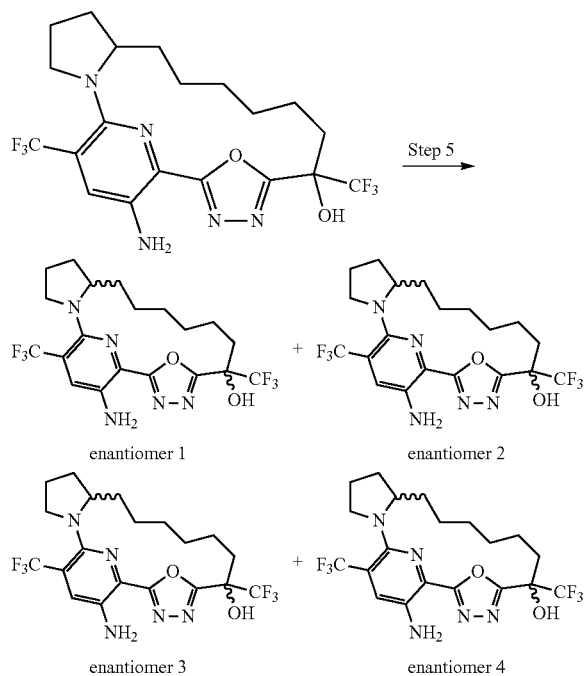

A mixture of 21-amino-6,19-bis(trifluoromethyl)-23-oxa-3,4,17,22-tetraazatetracyclo[16.3.1.12,5.013,17]tricosa-1(22),2,4,18,20-pentaen-6-ol (48.01 mg, 0.09306 mmol) was purified by normal phase SFC using a LUX-4 column (250×10 mm, 5 µm particle size) sold by Phenomenex, and a dual gradient run from 10% to 90% mobile phase B (mobile phase A=CO$_2$, mobile phase B=methanol (no modifier), flow rate of 10 mL/min with an injection volume of 70 µL). These conditions produced 4 enantiomeric products as described below:

The first enantiomer to elute was isolated as a yellow solid, 21-amino-6,19-bis(trifluoromethyl)-23-oxa-3,4,17,22-tetraazatetracyclo[16.3.1.12,5.013,17]tricosa-1(22),2,4,18,20-pentaen-6-ol (enantiomer 1) (4.8 mg, 43%). $^1$H NMR (500 MHz, DMSO-d6) δ 7.75 (s, 1H), 7.66 (s, 1H), 6.41 (s, 2H), 4.20 (t, J=8.4 Hz, 1H), 3.54 (q, J=8.3 Hz, 1H), 3.12 (t, J=9.0 Hz, 1H), 2.34-2.24 (m, 1H), 2.22-2.16 (m, 1H), 2.11 (dt, J=13.7, 8.1 Hz, 1H), 1.95-1.70 (m, 3H), 1.61 (d, J=10.6 Hz, 2H), 1.51-1.29 (m, 4H), 1.27-1.12 (m, 3H), 0.95 (s, 1H) ppm. ESI-MS m/z calc. 479.1756, found 480.1 (M+1)$^+$; Retention time: 1.87 minutes (LC Method J).

The second enantiomer to elute was isolated as a yellow solid, 21-amino-6,19-bis(trifluoromethyl)-23-oxa-3,4,17,22-tetraazatetracyclo[16.3.1.12,5.013,17]tricosa-1(22),2,4,18,20-pentaen-6-ol (enantiomer 2) (4.3 mg, 39%). $^1$H NMR (500 MHz, DMSO-d6) δ 7.75 (s, 1H), 7.66 (s, 1H), 6.41 (s, 2H), 4.21 (q, J=8.3 Hz, 1H), 3.54 (q, J=8.4 Hz, 1H), 3.12 (t, J=9.0 Hz, 1H), 2.29 (t, J=9.8 Hz, 1H), 2.22-2.15 (m, 1H), 2.11 (dt, J=14.8, 8.0 Hz, 1H), 1.94-1.80 (m, 2H), 1.79-1.70 (m, 1H), 1.61 (d, J=9.3 Hz, 2H), 1.52-1.28 (m, 4H), 1.19 (q, J=7.9, 6.7 Hz, 3H), 0.95 (s, 1H) ppm. ESI-MS m/z calc. 479.1756, found 480.2 (M+1)$^+$; Retention time: 1.87 minutes (LC Method J).

The third enantiomer to elute was isolated as a yellow solid, 21-amino-6,19-bis(trifluoromethyl)-23-oxa-3,4,17,22-tetraazatetracyclo[16.3.1.12,5.013,17]tricosa-1(22),2,4,18,20-pentaen-6-ol (enantiomer 3) (9.4 mg, 84%). $^1$H NMR (500 MHz, DMSO-d6) δ 7.75 (s, 1H), 7.66 (s, 1H), 6.39 (s, 2H), 4.09 (d, J=8.7 Hz, 1H), 3.54 (q, J=8.5 Hz, 1H), 3.21-3.08 (m, 1H), 2.31 (dt, J=15.0, 7.1 Hz, 1H), 2.21-2.12 (m, 1H), 1.97 (t, J=10.8 Hz, 2H), 1.88 (dt, J=8.3, 4.8 Hz, 2H), 1.72 (h, J=10.5, 9.6 Hz, 1H), 1.58-1.50 (m, 1H), 1.47 (dt, J=10.7, 5.3 Hz, 2H), 1.42 (s, 3H), 1.15 (d, J=15.9 Hz, 2H), 0.99 (dq, J=12.0, 6.3 Hz, 1H) ppm. ESI-MS m/z calc. 479.1756, found 480.3 (M+1)$^+$; Retention time: 1.87 minutes (LC Method J).

The fourth enantiomer to elute was isolated as a yellow solid, 21-amino-6,19-bis(trifluoromethyl)-23-oxa-3,4,17,22-tetraazatetracyclo[16.3.1.12,5.013,17]tricosa-1(22),2,4,18,20-pentaen-6-ol (enantiomer 4) (9.4 mg, 84%). $^1$H NMR (500 MHz, DMSO-d6) δ 7.76 (s, 1H), 7.66 (s, 1H), 6.40 (s, 2H), 4.10 (d, J=8.6 Hz, 1H), 3.54 (q, J=8.4 Hz, 1H), 3.15 (t, J=9.0 Hz, 1H), 2.31 (dt, J=14.9, 7.2 Hz, 1H), 2.16 (dd, J=11.7, 6.7 Hz, 1H), 1.97 (d, J=12.5 Hz, 2H), 1.88 (dt, J=8.4, 4.3 Hz, 2H), 1.80-1.65 (m, 1H), 1.54 (d, J=6.8 Hz, 1H), 1.46 (dt, J=11.9, 6.2 Hz, 2H), 1.34 (ddt, J=33.8, 12.9, 6.5 Hz, 3H), 1.16 (d, J=16.0 Hz, 2H), 1.02-0.94 (m, 1H) ppm. ESI-MS m/z calc. 479.1756, found 480.1 (M+1)$^+$; Retention time: 1.85 minutes (LC Method J).

Example 17: Preparation of 20-amino-14,14-dimethyl-6,18-bis(trifluoromethyl)-22-oxa-3,4,16,21-tetraazatetracyclo[15.3.1.1²,⁵.0¹²,¹⁶]docosa-1(21),2,4,17,19-pentaen-6-ol (enantiomer 1) (Compound 27), 20-amino-14,14-dimethyl-6,18-bis(trifluoromethyl)-22-oxa-3,4,16,21-tetraazatetracyclo[15.3.1.1², 5.0¹²,¹⁶]docosa-1(21),2,4,17,19-pentaen-6-ol (enantiomer 2) (Compound 28), 20-amino-14,14-dimethyl-6,18-bis(trifluoromethyl)-22-oxa-3,4,16,21-tetraazatetracyclo[15.3.1.1²,5.0¹²,¹⁶]docosa-1(21),2,4,17,19-pentaen-6-ol (enantiomer 3) (Compound 29) and 20-amino-14,14-dimethyl-6,18-bis(trifluoromethyl)-22-oxa-3,4,16,21-tetraazatetracyclo[15.3.1.1²,5.0¹²,¹⁶]docosa-1(21),2,4,17,19-pentaen-6-ol (enantiomer 4) (Compound 30)

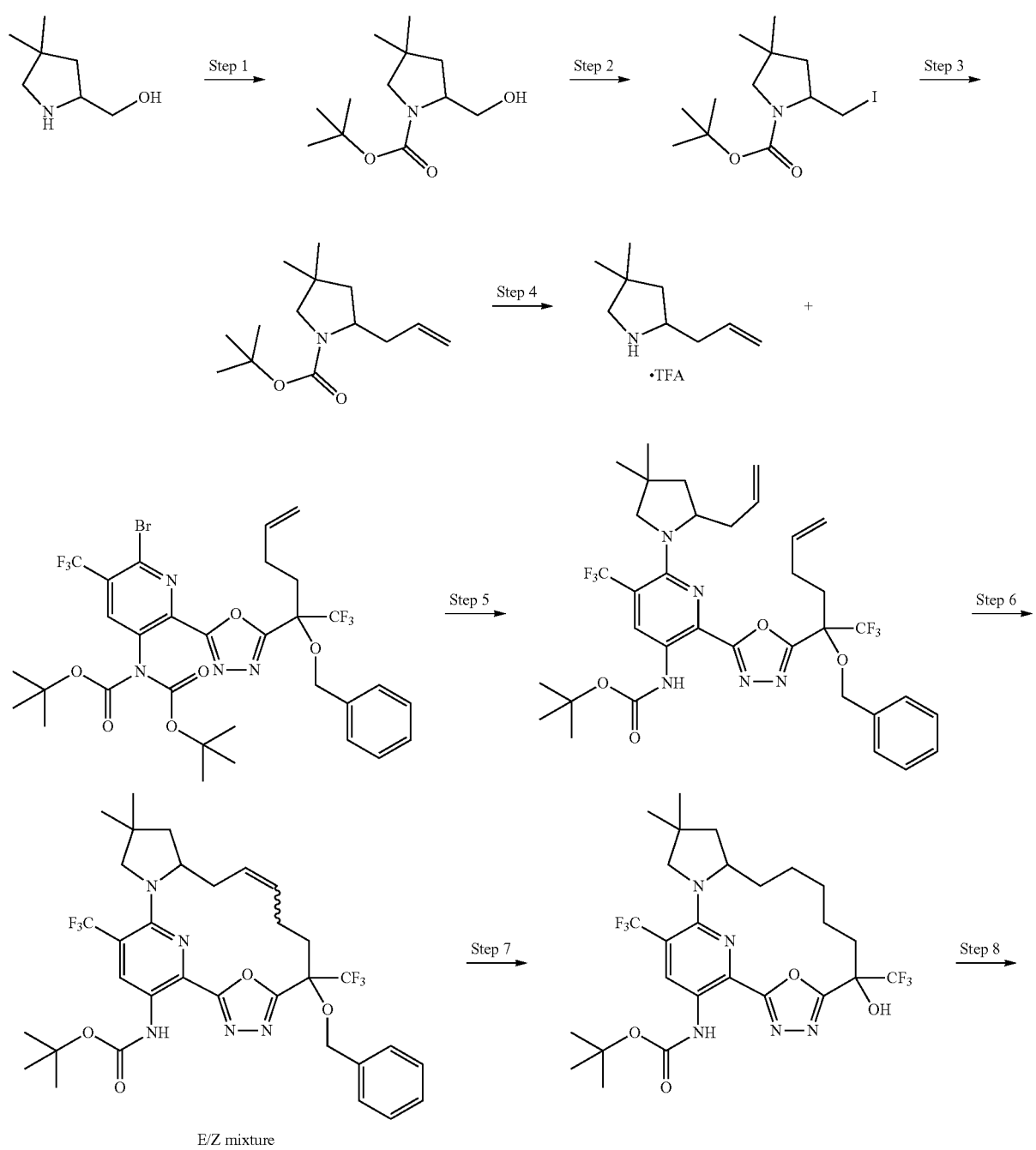

-continued

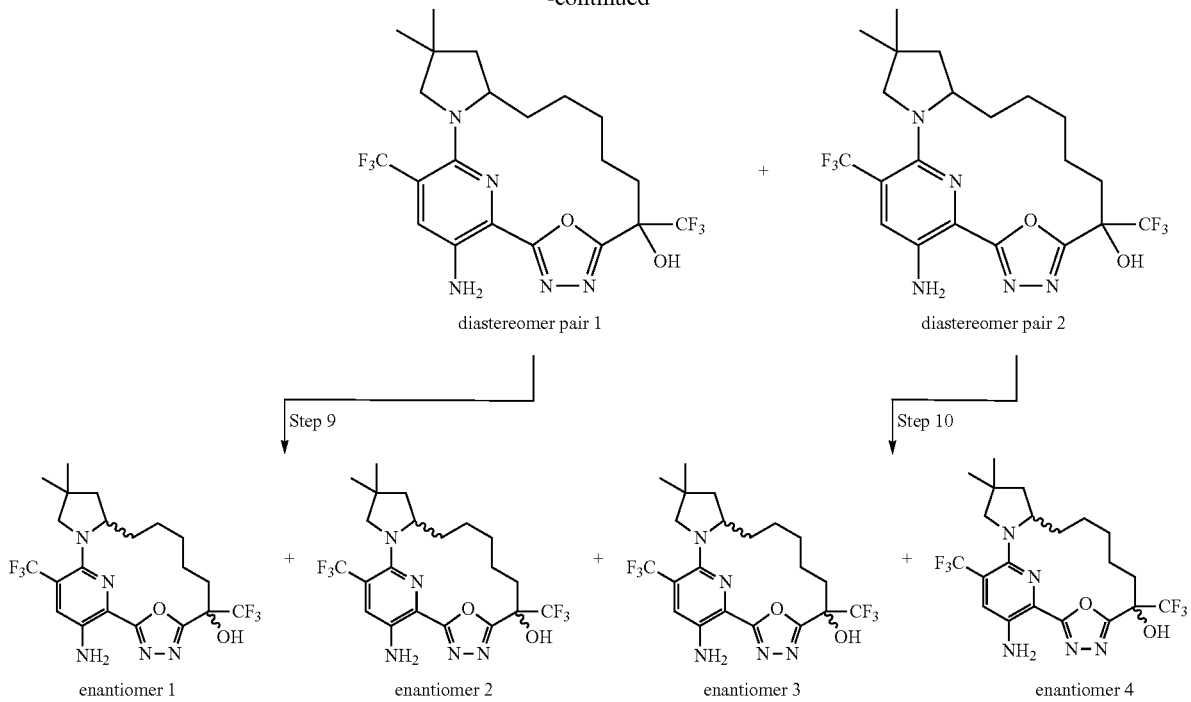

diastereomer pair 1 diastereomer pair 2

Step 9

Step 10 enantiomer 1 enantiomer 2 enantiomer 3 enantiomer 4

Step 1: tert-Butyl 2-(hydroxymethyl)-4,4-dimethyl-pyrrolidine-1-carboxylate

Step 2: tert-Butyl 2-(iodomethyl)-4,4-dimethyl-pyrrolidine-1-carboxylate

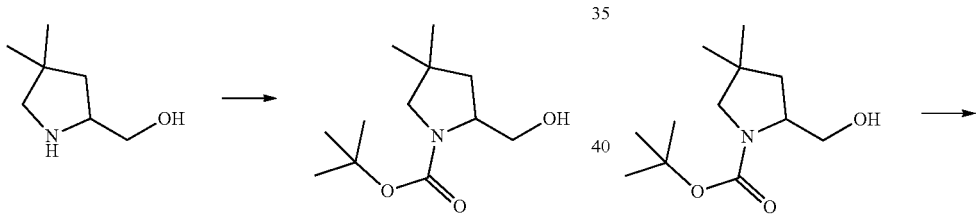

To a solution of (4,4-dimethylpyrrolidin-2-yl)methanol (3 g, 23.22 mmol) in tetrahydrofuran (40 mL) was added triethylamine (7.1148 g, 9.8 mL, 70.311 mmol) followed by di-tert-butyl dicarbonate (6 g, 27.492 mmol) at room temperature. The mixture was stirred at room temperature overnight and concentrated in vacuo. The residue was dissolved in ethyl acetate (150 mL) and then the mixture was washed with 1 N HCl (150 mL), brine (150 mL), dried over anhydrous sodium sulfate, filtered and concentrated under vacuum. The residue was purified by silica gel chromatography (120 g column) using a gradient from 0% to 30% ethyl acetate in heptanes giving as a clear oil, tert-butyl 2-(hydroxymethyl)-4,4-dimethyl-pyrrolidine-1-carboxylate (4.95 g, 92%). $^1$H NMR (300 MHz, Chloroform-d) δ 4.08-3.94 (m, 1H), 3.71-3.51 (m, 2H), 3.32 (d, J=10.9 Hz, 1H), 2.97 (d, J=10.9 Hz, 1H), 1.92-1.69 (m, 1H), 1.47 (s, 9H), 1.38-1.22 (m, 1H), 1.07 (s, 3H), 1.01 (s, 3H) ppm. One exchangeable proton not observed in NMR.

To a solution of imidazole (2.9 g, 42.599 mmol) and triphenylphosphine (6.2 g, 23.638 mmol) in 2-methyl tetrahydrofuran (75 mL) at 0° C. was added iodine (6.5 g, 25.61 mmol) portion wise over 30 min. The reaction temperature was kept at <6° C. and the mixture became a dark orange taffy which became light yellow and granular on stirring. The mixture was warmed to room temperature and a solution of tert-butyl 2-(hydroxymethyl)-4,4-dimethyl-pyrrolidine-1-carboxylate (4.9 g, 21.368 mmol) in 2-methyl tetrahydrofuran (25 mL) was added dropwise. The mixture was stirred at room temperature for 20 hours affording a light-yellow slurry. The slurry was filtered over Celite and washed with diethyl ether (75 mL) and the filtrate was concentrated in vacuo. The residue was purified by silica gel chromatography (120 g column) using a gradient from 0% to 20% ethyl acetate in heptanes giving as a light-yellow oil, tert-butyl 2-(iodomethyl)-4,4-dimethyl-pyrrolidine-1-carboxylate (6.7 g, 92%). $^1$H NMR (300 MHz, Chloroform-d) δ 3.85-3.68 (m, 1H), 3.68-3.27 (m, 3H), 3.05 (d, J=10.6 Hz, 1H), 2.05-1.83 (m, 1H), 1.59-1.44 (m, 10H), 1.11 (s, 3H), 1.00 (s, 3H) ppm. ESI-MS m/z calc. 339.0695, found 284.1 (M-55)$^+$; Retention time: 2.29 minutes (LC Method E).

Step 3: tert-Butyl 2-allyl-4,4-dimethyl-pyrrolidine-1-carboxylate

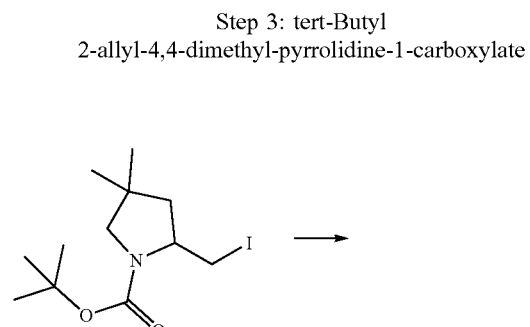

A suspension of copper iodide (4.8 g, 25.203 mmol) in degassed 2-methyl tetrahydrofuran (56 mL) was cooled to −50° C. and vinyl magnesium bromide (50 mL of 1 M, 50 mmol) in tetrahydrofuran was added dropwise keeping the reaction temperature <−40° C. Following the addition (20 min), the thick suspension was stirred for 30 minutes allowing the temperature to rise to −10° C., at which time it became a thinner black suspension. The black suspension was cooled to −60° C. and a solution of tert-butyl 2-(iodomethyl)-4,4-dimethyl-pyrrolidine-1-carboxylate (5.6 g, 16.509 mmol) in 2-methyl tetrahydrofuran (14 mL) was added dropwise keeping the reaction temperature <−50° C. The mixture was stirred for 30 min allowing the reaction temperature to rise to −15° C. The reaction was quenched with saturated ammonium chloride (25 mL) and the organic phase was separated and washed with saturated ammonium chloride (75 mL). The aqueous phase was extracted with diethyl ether (75 mL) and the combined organic phases were dried over sodium sulfate, filtered and concentrated in vacuo. The resultant light orange oil was purified by silica gel chromatography (80 g column) using a gradient from 0% to 20% dichloromethane in hexanes giving as a light yellow oil, tert-butyl 2-allyl-4,4-dimethyl-pyrrolidine-1-carboxylate (1.6 g, 40%). $^1$H NMR (300 MHz, Chloroform-d) δ 5.84-5.59 (m, 1H), 5.14-4.98 (m, 2H), 4.01-3.73 (m, 1H), 3.51-3.19 (m, 1H), 2.90 (d, J=10.6 Hz, 1H), 2.79-2.45 (m, 1H), 2.36-2.15 (m, 1H), 1.76 (ddd, J=12.6, 7.3, 1.8 Hz, 1H), 1.51-1.44 (m, 10H), 1.07 (s, 3H), 0.97 (s, 3H) ppm.

Step 4: 2-Allyl-4,4-dimethyl-pyrrolidine (trifluoroacetate salt)

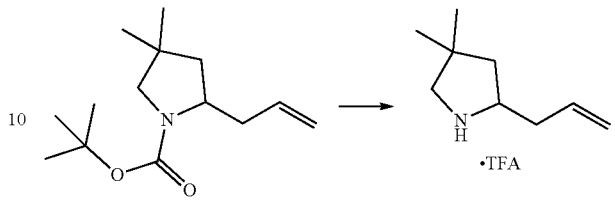

Trifluoroacetic acid (13.320 g, 9 mL, 116.82 mmol) was added over 15 minutes to a solution of tert-butyl 2-allyl-4,4-dimethyl-pyrrolidine-1-carboxylate (2.35 g, 9.8181 mmol) in dichloromethane (15 mL) at −20° C. in a cold bath. There was some exotherm, and the maximum temperature reached was −10° C. The cold bath was removed, the resulting mixture was stirred at room temperature for 2 hours and then solvents were removed under vacuum. The residue was dried under vacuum over night to provide as a dark oil, 2-allyl-4,4-dimethyl-pyrrolidine (trifluoroacetate salt) (3.4 g, 94). $^1$H NMR (300 MHz, Chloroform-d) δ 9.13 (br. s., 1H), 8.16 (br. s., 1H), 5.81-5.62 (m, 1H), 5.32-5.08 (m, 2H), 3.93-3.77 (m, 1H), 3.08 (t, J=5.4 Hz, 2H), 2.64-2.38 (m, 2H), 2.09-1.86 (m, 1H), 1.74-1.53 (m, 1H), 1.22 (s, 3H), 1.19 (s, 3H) ppm. $^{19}$F NMR (282 MHz, Chloroform-d) δ−75.94 (s, 3F) ppm. ESI-MS m/z calc. 139.1361, found 140.3 (M+1)$^+$; Retention time: 0.69 minutes (LC Method C).

Step 5: tert-Butyl N-[6-(2-allyl-4,4-dimethyl-pyrrolidin-1-yl)-2-[5-[1-benzyloxy-1-(trifluoromethyl)pent-4-enyl]-1,3,4-oxadiazol-2-yl]-5-(trifluoromethyl)-3-pyridyl]carbamate

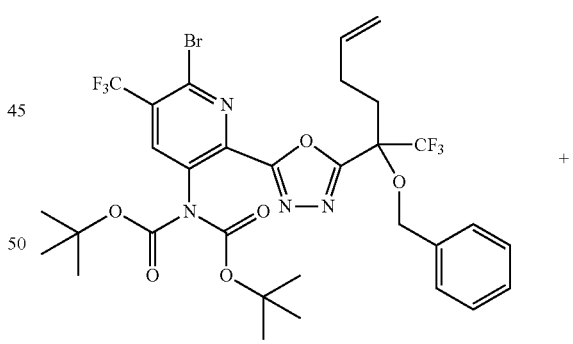

+

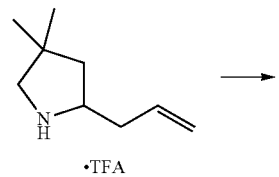

317
-continued

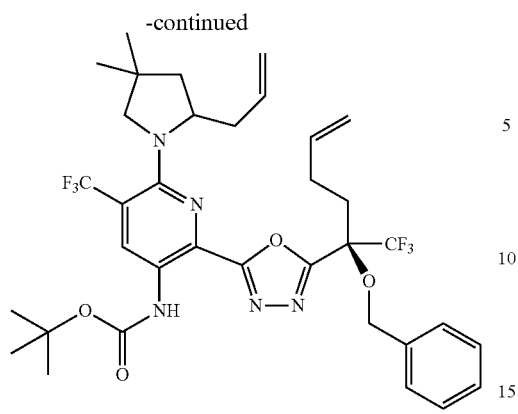

318
-continued

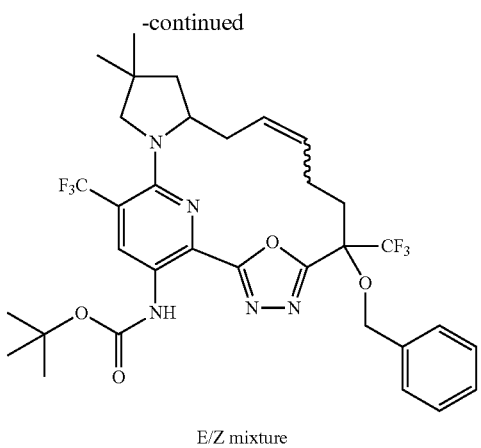

E/Z mixture

To a solution of tert-butyl N-[2-[5-[1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate (10 g, 1.331 mmol) in DMSO (5 mL) was added cesium carbonate (2.2 g, 6.752 mmol) and 2-allyl-4,4-dimethyl-pyrrolidine (trifluoroacetate salt) (685 mg, 2.705 mmol) and the reaction mixture was heated at 100° C. for 30 min in a microwave reactor. The reaction mixture was poured on crushed ice and after the ice melted, the water was decanted and the resultant pasty material was dissolved in ethyl acetate, washed with brine solution, dried over sodium sulfate, filtered and concentrated. The resultant brown residue was purified by silica gel chromatography using a gradient 0% to 30% ethyl acetate in hexanes which provided tert-butyl N-[6-(2-allyl-4,4-dimethyl-pyrrolidin-1-yl)-2-[5-[1-benzyloxy-1-(trifluoromethyl)pent-4-enyl]-1,3,4-oxadiazol-2-yl]-5-(trifluoromethyl)-3-pyridyl]carbamate (654 mg, 69%). $^1$H NMR (400 MHz, DMSO-d6) δ 9.46 (s, 1H), 8.65 (s, 1H), 7.40 (dt, J 7.6, 1.8 Hz, 2H), 7.38-7.30 (m, 3H), 5.84 (dddt, J=19.6, 16.7, 10.1, 6.4 Hz, 1H), 5.75-5.61 (m, 1H), 5.15-4.89 (m, 4H), 4.78-4.61 (m, 2H), 4.54 (d, J=8.1 Hz, 1H), 3.35 (d, J=10.3 Hz, 1H), 3.03 (d, J=9.7 Hz, 1H), 2.49-2.39 (m, 3H), 2.38-2.18 (m, 3H), 1.79 (dd, J=12.2, 6.6 Hz, 1H), 1.55 (t, J=11.5 Hz, 1H), 1.47 (s, 9H), 1.12 (s, 3H), 0.85 (d, J=2.2 Hz, 3H) ppm. ESI-MS m/z calc. 709.3063, found 710.4 (M+1)$^+$; Retention time: 2.36 minutes (LC Method M). A minor amount of the product still contained a second N-Boc protecting group, used this material directly in the ensuing step.

Step 6: tert-Butyl N-[6-(benzyloxy)-14,14-dimethyl-6,18-bis(trifluoromethyl)-22-oxa-3,4,16,21-tetraazatetracyclo[15.3.1.12,5.012,16]docosa-1(21),2,4,9,17,19-hexaen-20-yl]carbamate (E/Z Mixture)

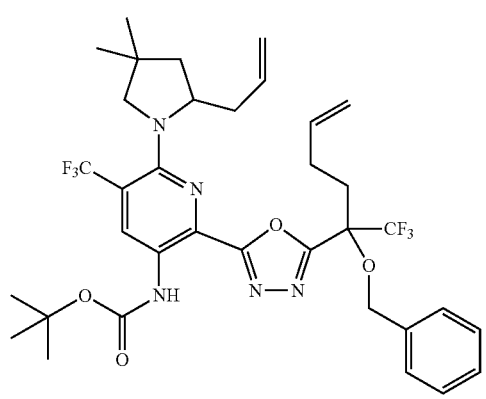

To a degassed solution of tert-butyl N-[6-(2-allyl-4,4-dimethyl-pyrrolidin-1-yl)-2-[5-[1-benzyloxy-1-(trifluoromethyl)pent-4-enyl]-1,3,4-oxadiazol-2-yl]-5-(trifluoromethyl)-3-pyridyl]carbamate (650 mg, 0.9159 mmol) (contaminated with some starting material possessing bis-N-Boc protection, see previous step) in DCE (200 mL) was added Zhan catalyst-1B (192 mg, 0.2389 mmol) and the reaction was heated at 70° C. overnight. The reaction mixture was cooled to room temperature and concentrated. Diluted the mixture with 1:4 EtOAc/hexanes and filtered through Celite. The filtrate was concentrated and the resultant brown residue was purified by silica gel chromatography using a shallow gradient from 0% to 30% ethyl acetate in hexanes giving as a bright yellow oil, tert-butyl N-[6-(benzyloxy)-14,14-dimethyl-6,18-bis(trifluoromethyl)-22-oxa-3,4,16,21-tetraazatetracyclo[15.3.1.12,5.012,16]docosa-1(21),2,4,9,17,19-hexaen-20-yl]carbamate (E/Z mixture) (420 mg, 67%). ESI-MS m/z calc. 681.27496, found 682.5 (M+1)$^+$; Retention time: 2.18 minutes (LC Method M). A minor amount of the product still contained a second N-Boc protecting group, used this material directly in the ensuing step.

Step 7: tert-Butyl N-[6-hydroxy-14,14-dimethyl-6,18-bis(trifluoromethyl)-22-oxa-3,4,16,21-tetraazatetracyclo[15.3.1.12,5.012,16]docosa-1(21),2,4,17,19-pentaen-20-yl]carbamate

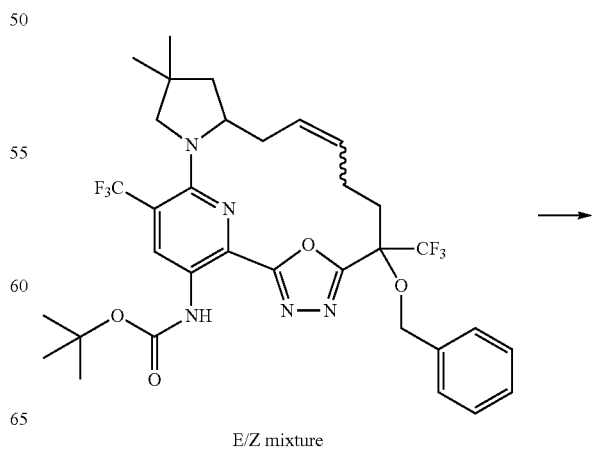

E/Z mixture

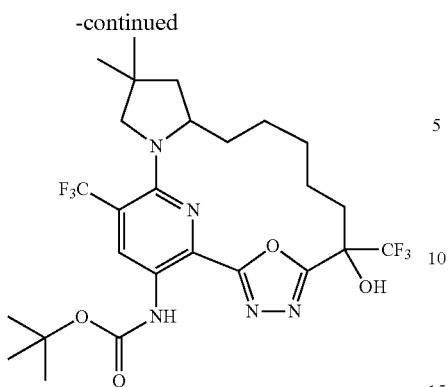

To a solution of tert-butyl N-[6-(benzyloxy)-14,14-dimethyl-6,18-bis(trifluoromethyl)-22-oxa-3,4,16,21-tetraazatetracyclo[15.3.1.12,5.012,16]docosa-1(21),2,4,9,17,19-hexaen-20-yl]carbamate (E/Z mixture) (420 mg, 0.6161 mmol) (contaminated with some starting material possessing bis-N-Boc protection, see previous step) in AcOH (5 mL) was added Pd/C (174 mg of 10% w/w, 0.1635 mmol, 50% water wet). The flask was placed on a hydrogen Parr Shaker and degassed under vacuum and filled with nitrogen gas three times. Then, all nitrogen gas was removed, and the reactor was pressurized to 40 psi of hydrogen gas and shaken overnight. The flask was depressurized and additional Pd/C (182 mg, 0.171 mmol, 10% w/w, 50% water wet) and a few drops of 1 M HCl were added. The mixture was put on the hydrogen Parr Shaker and degassed under vacuum and filled with nitrogen gas three times. Then, all nitrogen gas was removed, and the reactor was pressurized to 60 psi with hydrogen gas and shaken overnight. The flask was depressurized, and the mixture was filtered through Celite and the filtrate was concentrated. The resultant brown residue was purified by silica gel chromatography using a shallow gradient from 0% to 50% ethyl acetate in hexanes which provided tert-butyl N-[6-hydroxy-14,14-dimethyl-6,18-bis(trifluoromethyl)-22-oxa-3,4,16,21-tetraazatetracyclo[15.3.1.12,5.012,16]docosa-1(21),2,4,17,19-pentaen-20-yl]carbamate (170 mg, 46%). ESI-MS m/z calc. 593.24365, found 594.36 (M+1)⁺; Retention time: 1.92 minutes (LC Method M).

From this purification, also isolated the bis-N-Boc product, tert-butyl N-[(tert-butoxy)carbonyl]-N-[6-hydroxy-14,14-dimethyl-6,18-bis(trifluoromethyl)-22-oxa-3,4,16,21-tetraazatetracyclo[15.3.1.12,5.012,16]docosa-1(21),2,4,17,19-pentaen-20-yl]carbamate (84 mg, 20%). ESI-MS m/z calc. 693.2961, found 694.34 (M+1)⁺; Retention time: 1.74 minutes (LC Method M).

Step 8: 20-Amino-14,14-dimethyl-6,18-bis(trifluoromethyl)-22-oxa-3,4,16,21-tetraazatetracyclo[15.3.1.12,5.012,16]docosa-1(21),2,4,17,19-pentaen-6-ol (diastereomer pair 1) and 20-amino-14,14-dimethyl-6,18-bis(trifluoromethyl)-22-oxa-3,4,16,21-tetraazatetracyclo[15.3.1.12,5.012,16]docosa-1(21),2,4,17,19-pentaen-6-ol (diastereomer pair 2)

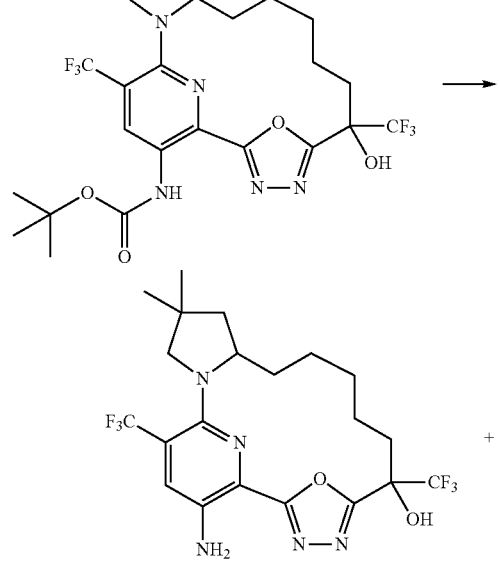

diastereomer pair 1

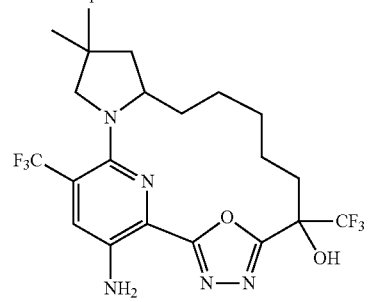

diastereomer pair 2 tert-Butyl N-[6-hydroxy-14,14-dimethyl-6,18-bis(trifluoromethyl)-22-oxa-3,4,16,21-tetraazatetracyclo[15.3.1.12,5.012,16]docosa-1(21),2,4,17,19-pentaen-20-yl]carbamate (170 mg, 0.2864 mmol) was dissolved in a pre-made solution of TFA (200 µL, 2.596 mmol) and dichloromethane (800 µL) and was stirred at room temperature for about 1 h. The solvent was removed under reduced pressure. Separately, tert-butyl N-[(tert-butoxy)carbonyl]-N-[6-hydroxy-14,14-dimethyl-6,18-bis(trifluoromethyl)-22-oxa-3,4,16,21-tetraazatetracyclo[15.3.1.12,5.012,16]docosa-1(21),2,4,17,19-pentaen-20-yl]carbamate (84 mg, 0.1211 mmol) in a pre-made solution of TFA (200 µL, 2.596 mmol) and dichloromethane (800 µL) was stirred at room temperature for about 1 h. The solvent was then removed under reduced pressure. The crude products obtained from the two reactions were combined and dissolved in 5 mL of DMSO and purified by reverse phase HPLC using a dual gradient run from 85% to 90% acetonitrile in water (+5 mM HCl) over 30 minutes which gave two separate diastereomer pairs:

The first diastereomer pair to elute was isolated as a yellow solid, 20-amino-14,14-dimethyl-6,18-bis(trifluoromethyl)-22-oxa-3,4,16,21-tetraazatetracyclo[15.3.1.12,5.012,16]docosa-1(21),2,4,17,19-pentaen-6-ol (diastereomer pair 1) (40 mg, 67%). ESI-MS m/z calc. 493.19125, found 494.3 (M+1)⁺; Retention time: 1.26 minutes (LC Method M).

The second diastereomer pair to elute was isolated as a yellow solid, 20-amino-14,14-dimethyl-6,18-bis(trifluoromethyl)-22-oxa-3,4,16,21-tetraazatetracyclo[15.3.1.12,5.012,16]docosa-1(21),2,4,17,19-pentaen-6-ol (diastereomer pair 2) (46 mg, 77%). ESI-MS m/z calc. 493.19125, found 494.1 (M+1)⁺; Retention time: 1.3 minutes (LC Method M).

Step 9: 20-Amino-14,14-dimethyl-6,18-bis(trifluoromethyl)-22-oxa-3,4,16,21-tetraazatetracyclo [15.3.1.12,5.012,16]docosa-1(21),2,4,17,19-pentaen-6-ol (enantiomer 1) (Compound 27), and 20-amino-14,14-dimethyl-6,18-bis(trifluoromethyl)-22-oxa-3, 4,16,21-tetraazatetracyclo[15.3.1.12,5.012,16] docosa-1(21),2,4,17,19-pentaen-6-ol (enantiomer 2) (Compound 28)

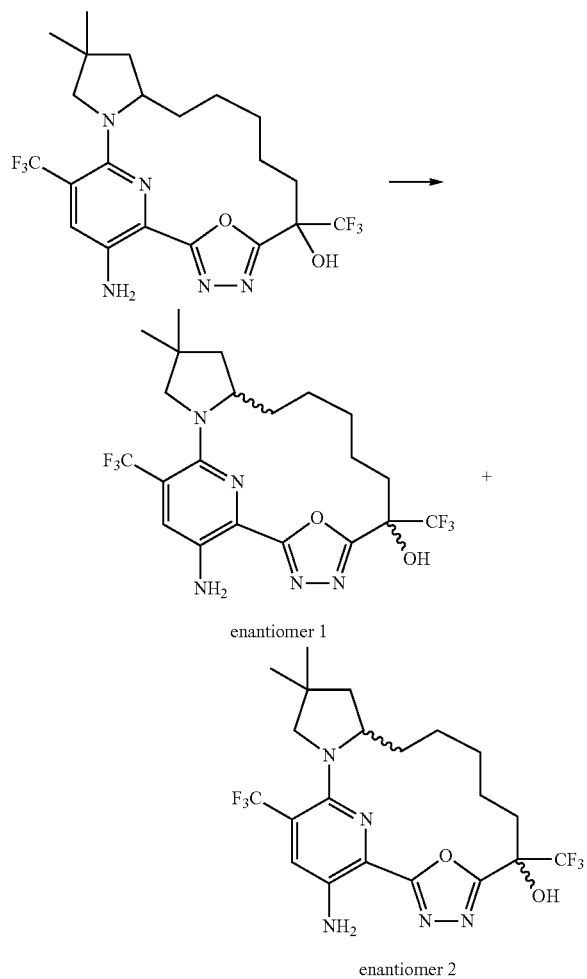

20-Amino-14,14-dimethyl-6,18-bis(trifluoromethyl)-22-oxa-3,4,16,21-tetraazatetracyclo[15.3.1.12,5.012,16]docosa-1(21),2,4,17,19-pentaen-6-ol (diastereomer pair 1) (47 mg, 0.09525 mmol) was purified by chiral SFC using normal phase and a LUX-4 column (250×10 mm, 5 μm particle size) sold by Phenomenex, and a gradient from 10% to 90% MeOH in CO₂ using a flow rate of 10 mL/min with an injection volume of 70 μL giving two single enantiomers:

The first enantiomer to elute was isolated as a bright yellow solid, 20-amino-14,14-dimethyl-6,18-bis(trifluoromethyl)-22-oxa-3,4,16,21-tetraazatetracyclo[15.3.1.12,5.012,16]docosa-1(21),2,4,17,19-pentaen-6-ol (enantiomer 1) (19.4 mg, 83%). ¹H NMR (500 MHz, DMSO-d6) δ 7.72 (s, 1H), 7.57 (s, 1H), 6.12 (s, 2H), 4.33-4.22 (m, 1H), 3.32 (d, J=9.6 Hz, 1H), 3.00 (d, J=9.6 Hz, 1H), 2.31 (dt, J=14.6, 7.3 Hz, 2H), 2.04 (ddd, J=14.5, 8.8, 5.8 Hz, 1H), 1.93 (dd, J=11.9, 6.2 Hz, 1H), 1.71 (dt, J 46.2, 8.5 Hz, 2H), 1.41 (tt, J=18.8, 7.7 Hz, 5H), 1.12 (s, 3H), 0.96-0.89 (m, 1H), 0.88 (s, 3H ppm). ESI-MS m/z calc. 493.19125, found 494.1 (M+1)⁺; Retention time: 1.26 minutes (LC Method M).

The second enantiomer to elute was isolated as a bright yellow solid, 20-amino-14,14-dimethyl-6,18-bis(trifluoromethyl)-22-oxa-3,4,16,21-tetraazatetracyclo[15.3.1.12,5.012,16]docosa-1(21),2,4,17,19-pentaen-6-ol (enantiomer 2) (17.9 mg, 76%). ¹H NMR (500 MHz, DMSO-d6) δ 7.72 (s, 1H), 7.59 (s, 1H), 6.12 (s, 2H), 4.27 (q, J=10.2 Hz, 1H), 3.32 (d, J=9.6 Hz, 1H)), 3.00 (d, J=9.6 Hz, 1H), 2.32 (dq, J=14.9, 6.6 Hz, 2H), 2.04 (ddd, J=14.5, 9.0, 6.0 Hz, 1H), 1.93 (dd, J=11.9, 6.2 Hz, 1H), 1.75 (q, J=8.8, 8.4 Hz, 1H), 1.67 (d, J=7.6 Hz, 1H), 1.52-1.31 (m, 5H), 1.12 (s, 3H), 0.93 (d, J=6.7 Hz, 1H), 0.88 (s, 3H) ppm. ESI-MS m/z calc. 493.19125, found 494.0 (M+1)⁺; Retention time: 1.25 minutes (LC Method M).

Step 10: 20-Amino-14,14-dimethyl-6,18-bis(trifluoromethyl)-22-oxa-3,4,16,21-tetraazatetracyclo [15.3.1.12,5.012,16]docosa-1(21),2,4,17,19-pentaen-6-ol (enantiomer 3) (Compound 29) and 20-amino-14,14-dimethyl-6,18-bis(trifluoromethyl)-22-oxa-3, 4,16,21-tetraazatetracyclo[15.3.1.12,5.012,16] docosa-1(21),2,4,17,19-pentaen-6-ol (enantiomer 4) (Compound 30)

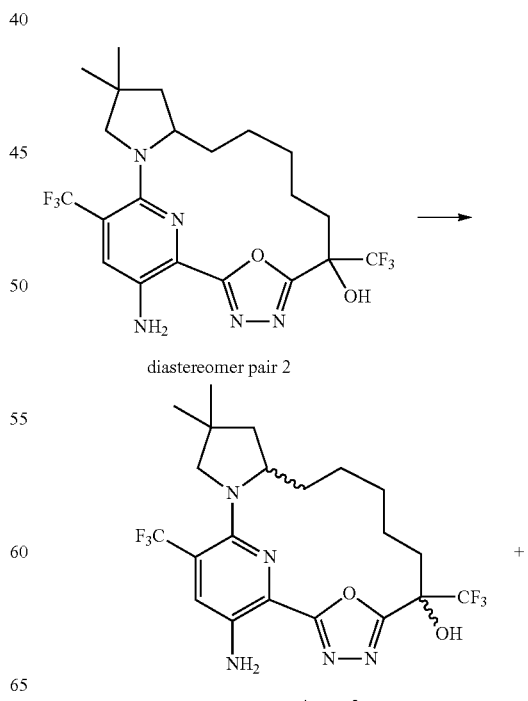

323

-continued

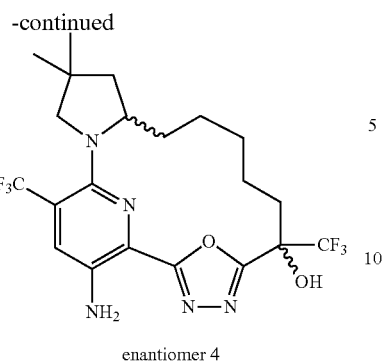

enantiomer 4

20-Amino-14,14-dimethyl-6,18-bis(trifluoromethyl)-22-oxa-3,4,16,21-tetraazatetracyclo[15.3.1.1²,⁵.0¹²,¹⁶]docosa-1(21),2,4,17,19-pentaen-6-ol (diastereomer pair 2) (46 mg, 0.09322 mmol) was purified by chiral SFC using normal phase and a LUX-4 column (250×10 mm, 5 µm particle size) sold by Phenomenex, and a gradient from 10% to 90% MeOH in $CO_2$ using a flow rate 10 mL/min with an injection volume of 70 µL giving two single enantiomers:

The first enantiomer to elute was isolated as a bright yellow solid, 20-amino-14,14-dimethyl-6,18-bis(trifluoromethyl)-22-oxa-3,4,16,21-tetraazatetracyclo[15.3.1.1²,⁵.0¹²,¹⁶]docosa-1(21),2,4,17,19-pentaen-6-ol (enantiomer 3) (14.6 mg, 63%). ¹H NMR (500 MHz, DMSO-d6) δ 7.71 (s, 1H), 6.11 (s, 2H), 4.12 (q, J=9.3 Hz, 1H), 3.31 (d, J=10.0 Hz, 2H), 3.00 (d, J=9.6 Hz, 1H), 2.45 (dt, J=12.8, 6.7 Hz, 1H), 2.25 (dq, J=9.4, 5.8, 4.7 Hz, 1H), 1.97 (dt, J=13.7, 8.7 Hz, 1H), 1.88 (dd, J=11.9, 6.2 Hz, 1H), 1.56 (t, J=7.6 Hz, 2H), 1.50-1.34 (m, 5H), 1.11 (s, 3H), 0.87 (s, 3H), 0.84 (s, 1H) ppm. ESI-MS m/z calc. 493.19125, found 494.1 (M+1)⁺; Retention time: 1.3 minutes (LC Method M).

The second enantiomer to elute was isolated as a bright yellow solid, 20-amino-14,14-dimethyl-6,18-bis(trifluoromethyl)-22-oxa-3,4,16,21-tetraazatetracyclo[15.3.1.1²,⁵.0¹²,¹⁶]docosa-1(21),2,4,17,19-pentaen-6-ol (enantiomer 4) (13.7 mg, 60%). ¹H NMR (500 MHz, DMSO-d6) δ 7.72 (s, 1H), 6.11 (s, 2H), 4.12 (q, J=9.3 Hz, 1H), 3.31 (s, 2H), 3.00 (d, J=9.6 Hz, 1H), 2.45 (d, J=12.2 Hz, 1H), 2.23 (d, J=10.9 Hz, 1H), 1.97 (dt, J=13.4, 8.5 Hz, 1H), 1.89 (dd, J=11.9, 6.2 Hz, 1H), 1.55 (s, 2H), 1.42 (q, J=12.3, 10.9 Hz, 5H), 1.11 (s, 3H), 0.88 (s, 3H), 0.82 (s, 1H) ppm. ESI-MS m/z calc. 493.19125, found 494.0 (M+1)⁺; Retention time: 1.3 minutes (LC Method M).

Example 18: Preparation of (12R)-6-(hydroxyimino)-18-(trifluoromethyl)-22-oxa-3,4,16,21-tetraazatetracyclo[15.3.1.1²,⁵.0¹²,¹⁶]docosa-1(21),2,4,17,19-pentaen-20-amine (Compound 31)

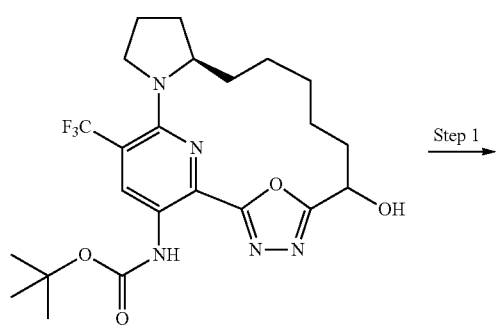

Step 1

324

-continued

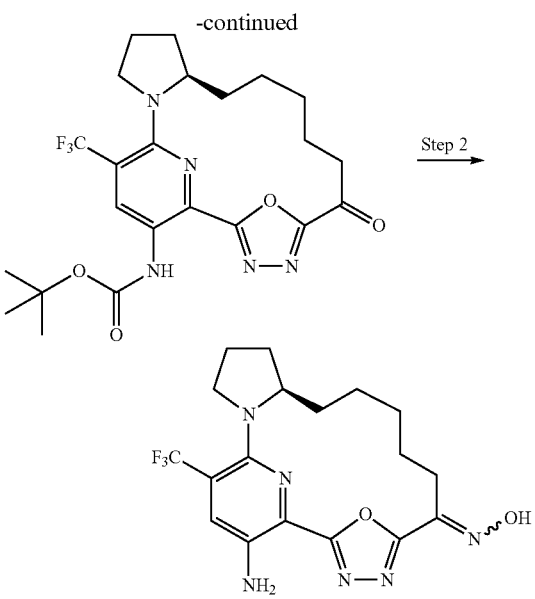

Step 2

Step 1: tert-Butyl N-[(12R)-6-oxo-18-(trifluoromethyl)-22-oxa-3,4,16,21-tetraazatetracyclo[15.3.1.1²,⁵.0¹²,¹⁶]docosa-1(21),2,4,17,19-pentaen-20-yl]carbamate

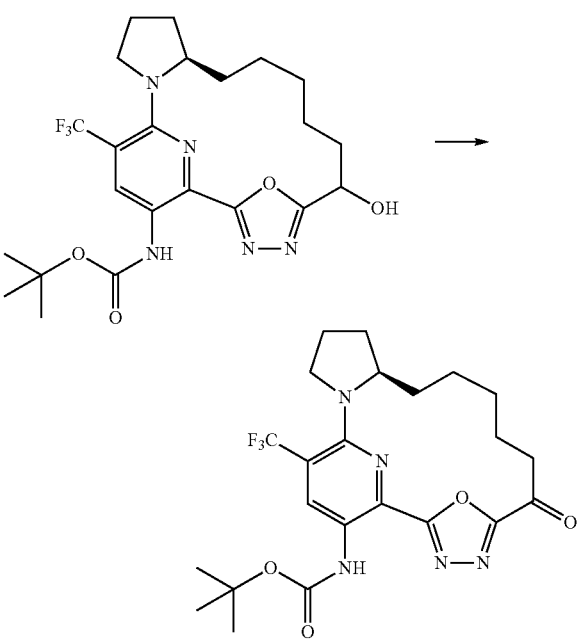

To a solution of tert-butyl N-[(12R)-6-hydroxy-18-(trifluoromethyl)-22-oxa-3,4,16,21-tetraazatetracyclo[15.3.1.1²,⁵.0¹²,¹⁶]docosa-1(21),2,4,17,19-pentaen-20-yl]carbamate (100 mg, 0.201 mmol) in DCM (1.628 mL) was added Dess-Martine periodinane (102.3 mg, 0.2412 mmol) and the reaction was stirred at room temperature for 30 min. The reaction mixture was filtered over Celite and concentrated. Purification by silica gel chromatography (12 g column) using a gradient from 0% to 30% ethyl acetate in hexanes over 10 min gave as a yellow solid, tert-butyl N-[(12R)-6-oxo-18-(trifluoromethyl)-22-oxa-3,4,16,21-tetraazatetracyclo[15.3.1.1².⁵.0¹²,¹⁶]docosa-1(21),2,4,17,19-pentaen-20-yl]carbamate (70 mg, 70%). ¹H NMR (400 MHz, Chloroform-d) δ 8.98 (s, 1H), 8.92 (s, 1H), 4.00-3.88 (m, 1H), 3.64-3.51 (m, 1H), 3.51-3.41 (m, 1H), 3.22-3.10 (m, 1H), 2.75-2.62 (m, 1H), 2.57 (td, J=11.8, 7.1 Hz, 1H), 2.20-1.88 (m, 4H), 1.83-1.56 (m, 6H), 1.48 (s, 10H) ppm. ESI-MS m/z calc. 495.20935, found 496.4 (M+1)⁺; Retention time: 0.67 minutes (LC Method T).

Step 2: (12R)-6-(Hydroxyimino)-18-(trifluoromethyl)-22-oxa-3,4,16,21-tetraazatetracyclo[15.3.1.1².⁵.0¹²,¹⁶]docosa-1(21),2,4,17,19-pentaen-20-amine (Compound 311

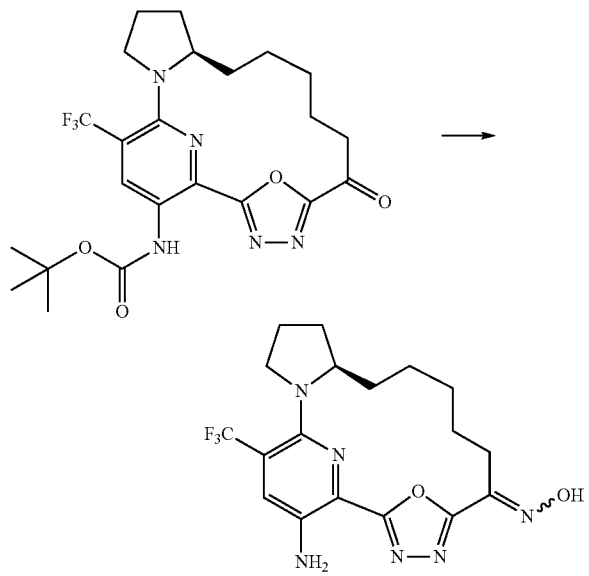

To a solution of tert-butyl N-[(12R)-6-oxo-18-(trifluoromethyl)-22-oxa-3,4,16,21-tetraazatetracyclo[15.3.1.1².⁵.0¹²,¹⁶]docosa-1(21),2,4,17,19-pentaen-20-yl]carbamate (18 mg, 0.03544 mmol) in dichloromethane (400 μL) was added TFA (27.30 μL, 0.3543 mmol) and the mixture was stirred for 2 h. The reaction mixture was concentrated, dissolved in EtOH (200 μL) and then added hydroxylamine (hydrochloride salt) (3.773 mg, 0.05429 mmol) followed by NaOAc (4.858 mg, 0.05922 mmol). The mixture was heated at 75° C. for 5 h. The reaction mixture was cooled to room temperature, filtered and purified by reverse phase HPLC using a gradient from 30% to 99% acetonitrile in water (+5 mM HCl). Combined fractions of the second eluting, and major diastereomer and evaporated. The resultant solid was dissolved in ethyl acetate and washed with saturated NaHCO₃, dried over sodium sulfate, filtered and concentrated to give as an orange solid, (12R)-6-(hydroxyimino)-18-(trifluoromethyl)-22-oxa-3,4,16,21-tetraazatetracyclo[15.3.1.1².⁵.0¹²,¹⁶]docosa-1(21),2,4,17,19-pentaen-20-amine (10 mg, 69%). ¹H NMR (400 MHz, CD₃OD) δ 7.51 (s, 1H), 3.91-3.76 (m, 1H), 3.52 (d, J=8.8 Hz, 1H), 3.28 (dd, J=17.8, 8.8 Hz, 1H), 3.20-3.08 (m, 1H), 2.52 (d, J=11.9 Hz, 1H), 2.37 (ddd, J=13.8, 9.7, 4.3 Hz, 1H), 2.20-2.01 (m, 1H), 1.88 (dd, J=6.9, 3.3 Hz, 1H), 1.85-1.61 (m, 3H), 1.60-1.29 (m, 5H), 0.95-0.84 (m, 1H) ppm. ESI-MS m/z calc. 410.16782, found 411.3 (M+1)⁺; Retention time: 1.99 minutes (LC Method A). Product is a single enantiomer with unknown stereochemistry of the oxime.

Example 19: Preparation of (11R)-19-amino-6,17-bis(trifluoromethyl)-21-oxa-3,4,15,20-tetraazatetracyclo[14.3.1.1².⁵.0¹¹,¹⁵]henicosa-1(20),2,4,16,18-pentaen-6-ol (enantiomer 1) (Compound 32) and (11R)-19-amino-6,17-bis(trifluoromethyl)-21-oxa-3,4,15,20-tetraazatetracyclo[14.3.1.1².⁵.0¹¹,¹⁵]henicosa-1(20),2,4,16,18-pentaen-6-ol (enantiomer 2) (Compound 33)

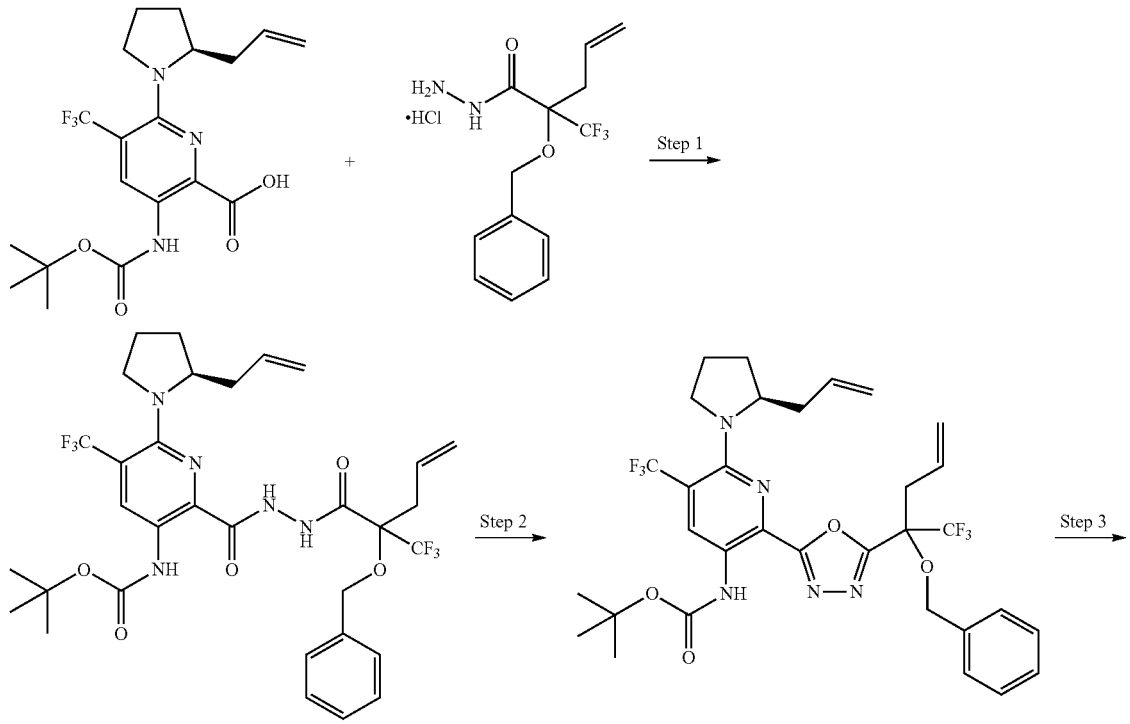

-continued
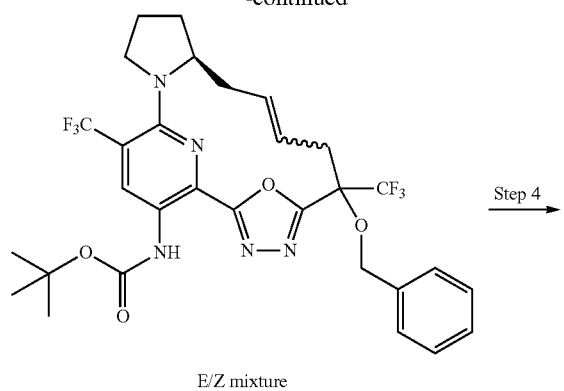
E/Z mixture
Step 4
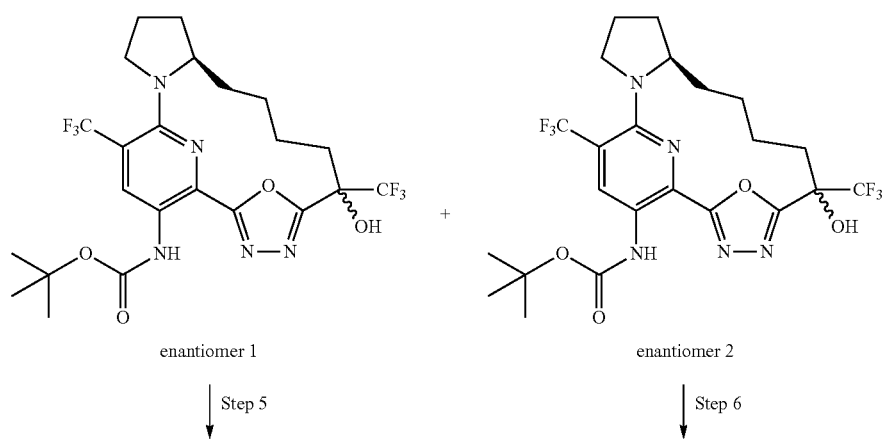
enantiomer 1 + enantiomer 2
Step 5 | Step 6
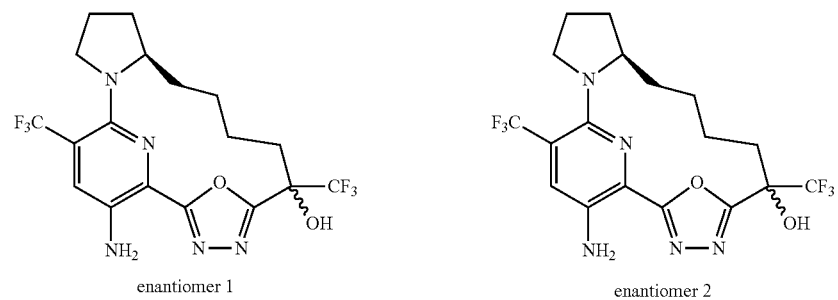
enantiomer 1 | enantiomer 2

329

Step 1: tert-Butyl N-[6-[(2S)-2-allylpyrrolidin-1-yl]-2-[[[2-benzyloxy-2-(trifluoromethyl)pent-4-enoyl]amino]carbamoyl]-5-(trifluoromethyl)-3-pyridyl]carbamate

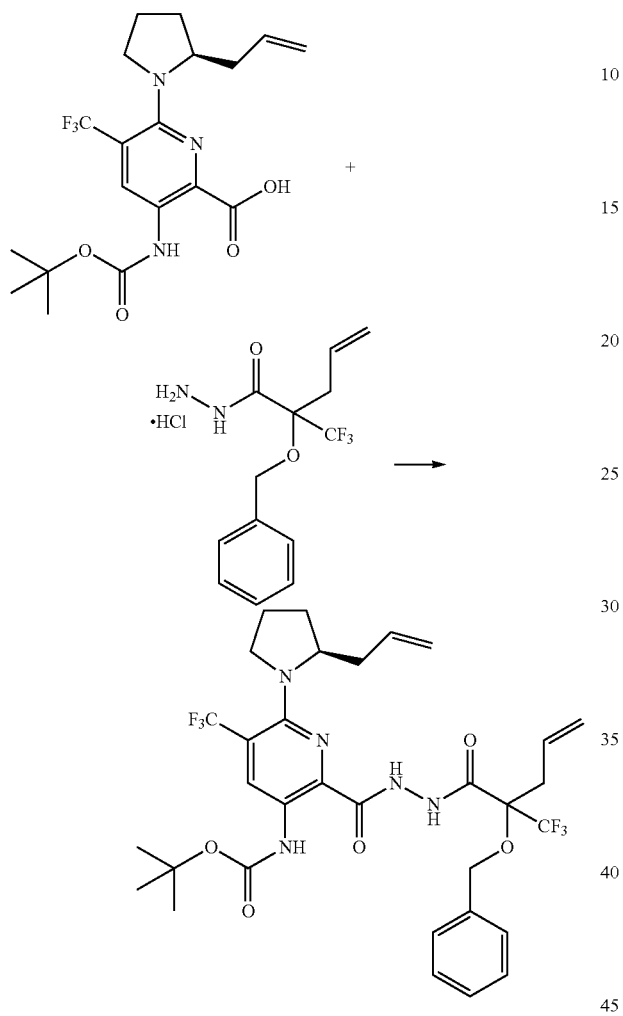

To a solution of 6-[(2S)-2-allylpyrrolidin-1-yl]-3-(tert-butoxycarbonylamino)-5-(trifluoromethyl)pyridine-2-carboxylic acid (2.3 g, 5.537 mmol) in NMP (32 mL) was added 2-benzyloxy-2-(trifluoromethyl)pent-4-enehydrazide (hydrochloride salt) (1.89 g, 5.820 mmol), DIEA (3.2 mL, 18.37 mmol) and HATU (2.59 g, 6.812 mmol). The reaction mixture was stirred at room temperature for 18 h. The reaction was diluted with ethyl acetate and washed with a saturated aqueous sodium bicarbonate solution. The organic layer was further washed with 10% citric acid solution followed by brine. The organics were separated, dried over sodium sulfate, filtered and evaporated. The residue was purified by silica gel chromatography (120 gram column) using a gradient from 100% hexanes to 50% ethyl acetate in hexanes to afford as a yellow foam, tert-butyl N-[6-[(2S)-2-allylpyrrolidin-1-yl]-2-[[[2-benzyloxy-2-(trifluoromethyl)pent-4-enoyl]amino]carbamoyl]-5-(trifluoromethyl)-3-pyridyl]carbamate (3.16 g, 83%). $^1$H NMR (400 MHz, DMSO-d6) δ 10.38 (s, 1H), 10.28 (d, J=18.9 Hz, 2H), 8.88 (s, 1H), 7.46 (d, J=7.4 Hz, 2H), 7.38 (t, J=7.4 Hz, 2H), 7.35-7.29 (m, 1H), 5.98-5.84 (m, 1H), 5.83-5.69 (m, 1H), 5.38 (d, J 17.1 Hz, 1H), 5.23 (d, J 10.3 Hz, 1H), 5.04-4.91 (m, 2H), 4.86 (s, 2H), 4.70 (ddt, J=18.2, 6.9, 3.3 Hz, 1H), 3.55 (q, J 8.6 Hz, 1H), 3.36-3.32 (m, 1H), 3.09 (dd, J=15.7, 7.5 Hz, 1H), 2.99 (d, J=15.8 Hz, 1H), 2.36-2.27 (m, 1H), 2.18 (dd, J=17.9, 4.5 Hz, 1H), 2.07-1.98 (m, 1H), 1.93 (t, J=8.9 Hz, 1H), 1.75 (dt, J 17.8, 8.3 Hz, 1H), 1.66 (dt, J 10.3, 7.4 Hz, 1H), 1.47 (s, 9H) ppm. ESI-MS m/z calc. 685.2699, found 686.2 (M+1)$^+$; Retention time: 1.91 minutes (LC Method M).

Step 2: tert-Butyl N-[6-[(2S)-2-allylpyrrolidin-1-yl]-2-[5-[1-benzyloxy-1-(trifluoromethyl)but-3-enyl]-1,3,4-oxadiazol-2-yl]-5-(trifluoromethyl)-3-pyridyl]carbamate

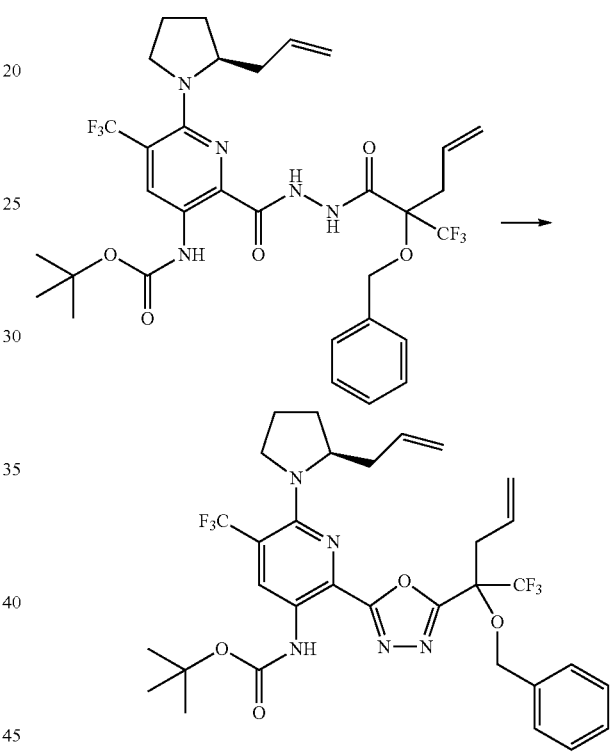

A solution of tert-butyl N-[6-[(2S)-2-allylpyrrolidin-1-yl]-2-[[[2-benzyloxy-2-(trifluoromethyl)pent-4-enoyl]amino]carbamoyl]-5-(trifluoromethyl)-3-pyridyl]carbamate (3.16 g, 4.609 mmol) and DIEA (3 mL, 17.22 mmol) in acetonitrile (100 mL) was heated at 50° C., then p-toluenesulfonyl chloride (1.4 g, 7.343 mmol) was added in one portion. The resulted mixture was heated at 70° C. for 2 hours. The reaction mixture was cooled and quenched with saturated aqueous solution of sodium bicarbonate (50 mL) and stirred for 15 minutes. The mixture was extracted with ethyl acetate (3×100 mL) and the combined organic layers were dried over sodium sulfate, filtered and evaporated. The residue was purified by silica gel chromatography (120 gram column) using a gradient from 100% hexanes to 40% ethyl acetate in hexanes to afford as a yellow foam, tert-butyl N-[6-[(2S)-2-allylpyrrolidin-1-yl]-2-[5-[1-benzyloxy-1-(trifluoromethyl)but-3-enyl]-1,3,4-oxadiazol-2-yl]-5-(trifluoromethyl)-3-pyridyl]carbamate (2.59 g, 84%). $^1$H NMR (400 MHz, DMSO-d6) δ 9.45 (s, 1H), 8.65 (d, J 3.7 Hz, 1H), 7.35 (ddd, J 21.4, 7.6, 5.2 Hz, 5H), 5.91 (ddd, J=17.5, 12.8, 7.6 Hz, 1H), 5.79-5.62 (m, 1H), 5.41-5.29 (m, 1H), 5.23 (t, J=11.8 Hz, 1H), 5.06-4.97 (m, 1H), 4.94 (d, J 10.2 Hz, 1H), 4.76 (dd, J 14.1, 10.9 Hz, 1H), 4.62 (dd, J=10.9, 6.5 Hz, 1H), 4.42-4.31 (m, 1H), 3.60-3.50 (m, 1H), 3.45-3.35 (m, 1H), 3.27 (t, J 8.2 Hz, 2H), 2.23 (t, J=11.8 Hz, 1H), 2.03 (d, J=11.3 Hz, 1H), 1.95 (s, 1H), 1.71 (ddd, J=18.8, 15.4, 8.1 Hz, 2H), 1.51-1.44 (m, 9H), 1.23 (s, 1H) ppm. ESI-MS m/z calc. 667.25934, found 668.3 (M+1)+; Retention time: 2.3 minutes (LC Method M).

Step 3: tert-Butyl N-[(11S)-6-(benzyloxy)-6,17-bis(trifluoromethyl)-21-oxa-3,4,15,20-tetraazatetracyclo[14.3.1.12,5.011,15]henicosa-1(20),2,4,8,16,18-hexaen-19-yl]carbamate (E/Z mixture)

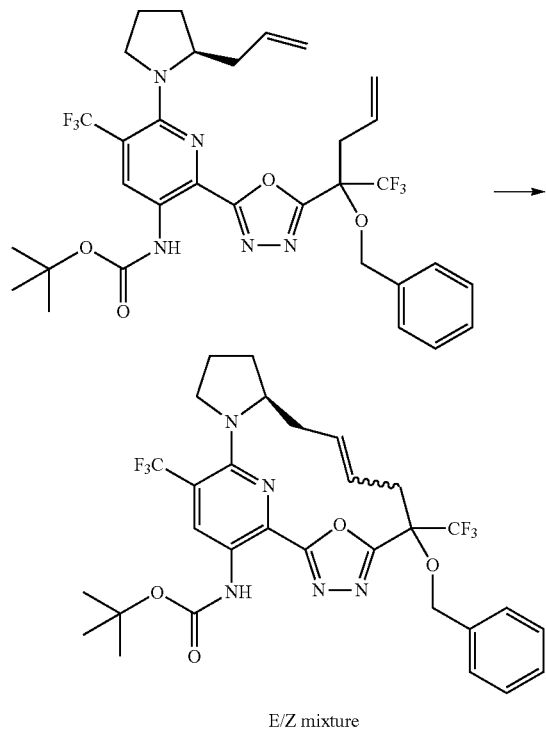

E/Z mixture

To a degassed solution of tert-butyl N-[6-[(2S)-2-allylpyrrolidin-1-yl]-2-[5-[1-benzyloxy-1-(trifluoromethyl)but-3-enyl]-1,3,4-oxadiazol-2-yl]-5-(trifluoromethyl)-3-pyridyl]carbamate (2.59 g, 3.879 mmol) in DCE (600 mL) was added Zhan catalyst-1B (465 mg, 0.6337 mmol) over 10 minutes in two portions at 50° C. under nitrogen atmosphere. The resulting mixture was heated at 70° C. for 14 hours. Again, Zhan catalyst-1B (465 mg, 0.6337 mmol) was added and the mixture was heated at 80° C. for 22 hours. The reaction mixture was cooled to room temperature and concentrated under reduced pressure. The residue was purified by silica gel chromatography (120 g column) using a gradient from 100% hexanes to 10% ethyl acetate in hexanes which gave as a bright yellow solid, tert-butyl N-[(11S)-6-(benzyloxy)-6,17-bis(trifluoromethyl)-21-oxa-3,4,15,20-tetraazatetracyclo[14.3.1.12,5.011,15]henicosa-1(20),2,4,8,16,18-hexaen-19-yl]carbamate (E/Z mixture) (160 mg, 6.5%). ESI-MS m/z calc. 639.228, found 640.2 (M+1)+; Retention time: 2.01 minutes (LC Method M).

Step 4: tert-Butyl N-[(11R)-6-hydroxy-6,17-bis(trifluoromethyl)-21-oxa-3,4,15,20-tetraazatetracyclo[14.3.1.12,5.011,15]henicosa-1(20),2,4,16,18-pentaen-19-yl]carbamate (enantiomer 1) and tert-butyl N-[(11R)-6-hydroxy-6,17-bis(trifluoromethyl)-21-oxa-3,4,15,20-tetraazatetracyclo[14.3.1.12,5.011,15]henicosa-1(20),2,4,16,18-pentaen-19-yl]carbamate (enantiomer 2)

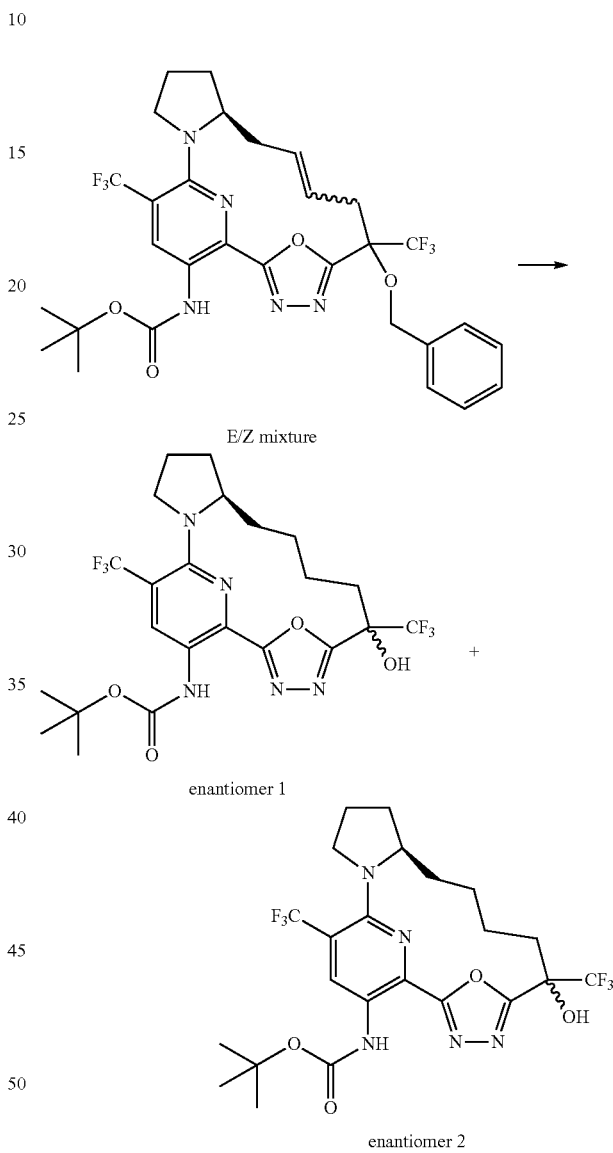

To a solution of tert-butyl N-[(11S)-6-(benzyloxy)-6,17-bis(trifluoromethyl)-21-oxa-3,4,15,20-tetraazatetracyclo[14.3.1.12,5.011,15]henicosa-1(20),2,4,8,16,18-hexaen-19-yl]carbamate (E/Z mixture) (240 mg, 0.3752 mmol) in AcOH (6 mL) and ethyl acetate (6 mL) was added Pd/C (400 mg of 10% w/w, 0.3759 mmol). The mixture was placed in a Parr shaker and degassed under vacuum and filled with nitrogen gas three times. Then, all nitrogen gas was removed, and the reactor was pressurized with hydrogen gas. The mixture was shaken at 80 psi for three hours, then at 100 psi for four more hours. The reactor was depressurized, and the reaction was filtered and concentrated. The residue was purified by silica gel chromatography (40 gram column) using a gradient from 100% hexanes to 60% ethyl acetate in hexanes giving two enantiomeric products:

The first enantiomer to elute was isolated as a yellow residue, tert-butyl N-[(11R)-6-hydroxy-6,17-bis(trifluoromethyl)-21-oxa-3,4,15,20-tetraazatetracyclo[14.3.1.12,5.011,15]henicosa-1(20),2,4,16,18-pentaen-19-yl]carbamate (enantiomer 1) (58.7 mg, 57%). ESI-MS m/z calc. 551.1967, found 552.2 (M+1)$^+$; Retention time: 1.42 minutes (LC Method M).

The second enantiomer to elute was isolated as a yellow residue, tert-butyl N-[(11R)-6-hydroxy-6,17-bis(trifluoromethyl)-21-oxa-3,4,15,20-tetraazatetracyclo[14.3.1.12,5.011,15]henicosa-1(20),2,4,16,18-pentaen-19-yl]carbamate (enantiomer 2) (58.5 mg, 57%). ESI-MS m/z calc. 551.1967, found 552.2 (M+1)$^+$; Retention time: 1.32 minutes (LC Method M).

Step 5: (11R)-19-Amino-6,17-bis(trifluoromethyl)-21-oxa-3,4,15,20-tetraazatetracyclo[14.3.1.12,5.011,15]henicosa-1(20),2,4,16,18-pentaen-6-ol (enantiomer 1) (Compound 32)

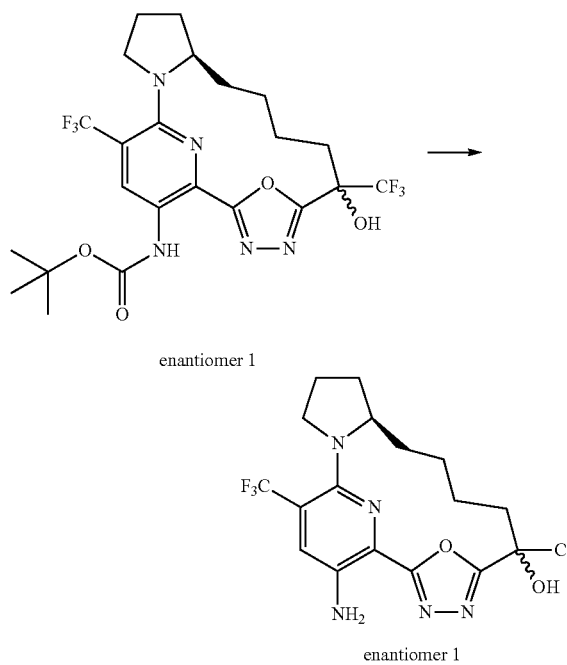

enantiomer 1

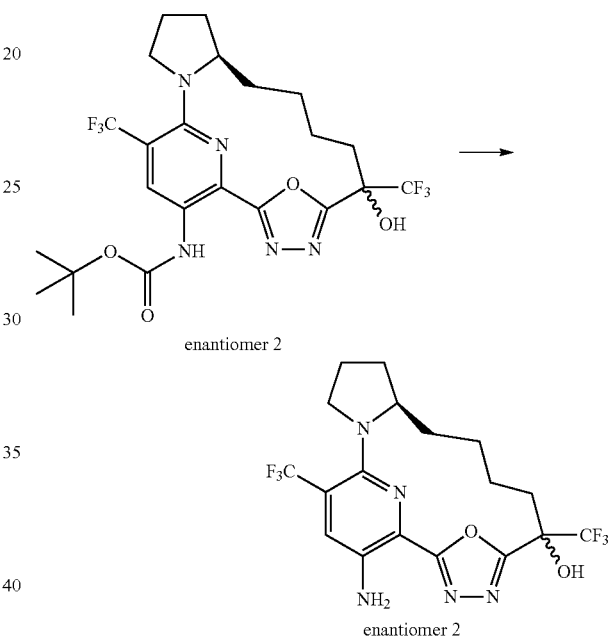

enantiomer 1

To a solution of tert-butyl N-[(11R)-6-hydroxy-6,17-bis(trifluoromethyl)-21-oxa-3,4,15,20-tetraazatetracyclo[14.3.1.12,5.011,15]henicosa-1(20),2,4,16,18-pentaen-19-yl]carbamate (enantiomer 1) (55 mg, 0.09973 mmol) in DCM (1000 µL) was added TFA (750 µL, 9.735 mmol) and the mixture was stirred at room temperature for 2 hours. The mixture was evaporated and purified by reverse phase HPLC using a gradient from 1% to 99% acetonitrile in water (+5 mM HCl) over 15.0 minutes which gave as a yellow solid, (11R)-19-amino-6,17-bis(trifluoromethyl)-21-oxa-3,4,15,20-tetraazatetracyclo[14.3.1.12,5.011,15]henicosa-1(20),2,4,16,18-pentaen-6-ol (enantiomer 1) (23.0 mg, 51%). $^1$H NMR (400 MHz, DMSO-d6) δ 7.68 (s, 1H), 7.56 (s, 1H), 5.75 (s, 2H), 3.83 (q, J=7.8 Hz, 1H), 3.51 (q, J=8.2 Hz, 2H), 2.35-2.21 (m, 2H), 2.12 (dq, J=11.6, 6.0 Hz, 1H), 2.00 (q, J=7.9 Hz, 1H), 1.96-1.88 (m, 2H), 1.84-1.72 (m, 1H), 1.69-1.50 (m, 3H), 1.48-1.36 (m, 1H), 1.16 (ddd, J=13.0, 10.0, 6.1 Hz, 1H) ppm. ESI-MS m/z calc. 451.1443, found 452.2 (M+1)$^+$; Retention time: 2.05 minutes (LC Method A).

Step 6: (11R)-19-Amino-6,17-bis(trifluoromethyl)-21-oxa-3,4,15,20-tetraazatetracyclo[14.3.1.12,5.011,15]henicosa-1(20),2,4,16,18-pentaen-6-ol (enantiomer 2) (Compound 33)

To a solution of tert-butyl N-[(11R)-6-hydroxy-6,17-bis(trifluoromethyl)-21-oxa-3,4,15,20-tetraazatetracyclo[14.3.1.12,5.011,15]henicosa-1(20),2,4,16,18-pentaen-19-yl]carbamate (enantiomer 2) (55 mg, 0.09973 mmol) in DCM (1000 µL) was added TFA (750 µL, 9.735 mmol) and the mixture was stirred at room temperature for 2 hours. The mixture was evaporated and purified by reverse phase HPLC using a gradient from 1% to 99% acetonitrile in water (+5 mM HCl) over 15.0 minutes which gave as a yellow solid, (11R)-19-amino-6,17-bis(trifluoromethyl)-21-oxa-3,4,15,20-tetraazatetracyclo[14.3.1.12,5.011,15]henicosa-1(20),2,4,16,18-pentaen-6-ol (enantiomer 2) (23.8 mg, 52%). $^1$H NMR (400 MHz, DMSO-d6) δ 7.67 (s, 1H), 7.62 (d, J=10.0 Hz, 1H), 5.59 (s, 2H), 3.97 (q, J=8.1 Hz, 1H), 3.54 (d, J=8.2 Hz, 2H), 2.41-2.32 (m, 1H), 2.15 (dt, J=11.8, 5.9 Hz, 1H), 2.04 (d, J=10.8 Hz, 1H), 1.97-1.90 (m, 1H), 1.90-1.74 (m, 2H), 1.74-1.48 (m, 4H), 1.39 (dd, J=18.2, 11.8 Hz, 1H), 1.11 (td, J=11.3, 7.0 Hz, 1H) ppm. ESI-MS m/z calc. 451.1443, found 452.2 (M+1)$^+$; Retention time: 1.98 minutes (LC Method A).

Example 20: Preparation of 17-amino-13-(2-methoxyethyl)-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (Compound 34) and 17-amino-13-(2-methoxyethyl)-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (Compound 35)
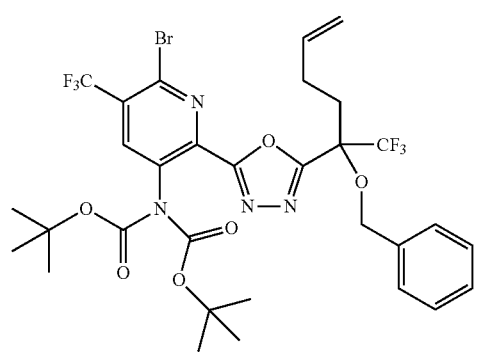
Step 1
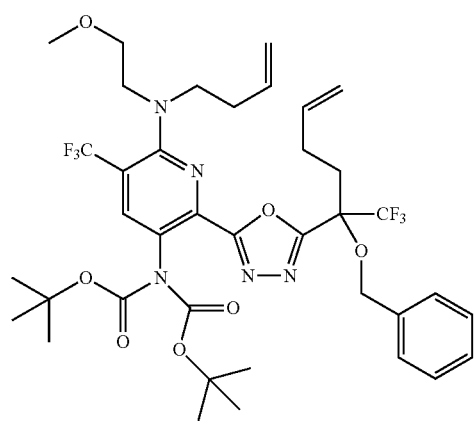
Step 2
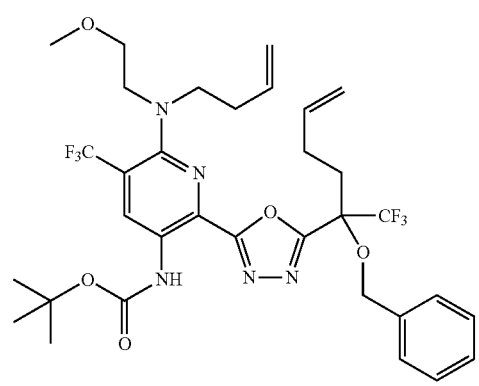
Step 3
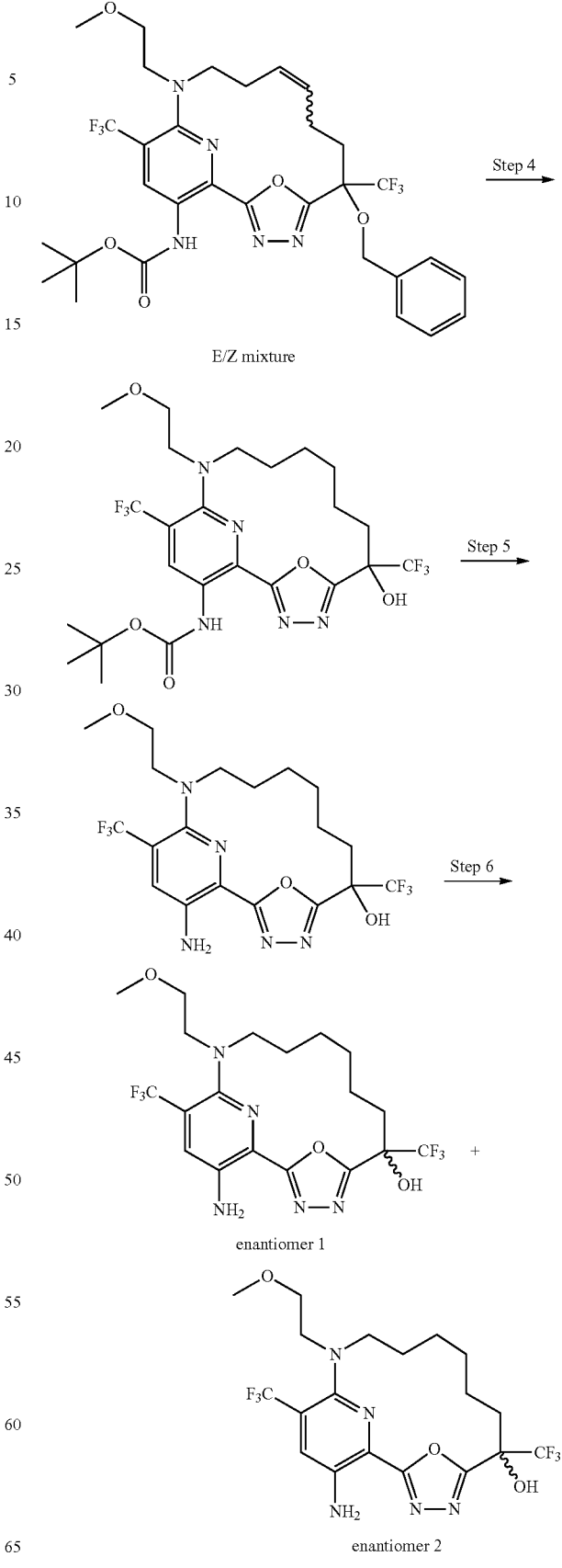

Step 1: tert-Butyl N-[2-[5-[1-benzyloxy-1-(trifluoromethyl)pent-4-enyl]-1,3,4-oxadiazol-2-yl]-6-[but-3-enyl(2-methoxyethyl)amino]-5-(trifluoromethyl)-3-pyridyl]-N-tert-butoxycarbonyl-carbamate

Step 2: tert-Butyl N-[2-[5-[1-benzyloxy-1-(trifluoromethyl)pent-4-enyl]-1,3,4-oxadiazol-2-yl]-6-[but-3-enyl(2-methoxyethyl)amino]-5-(trifluoromethyl)-3-pyridyl]carbamate

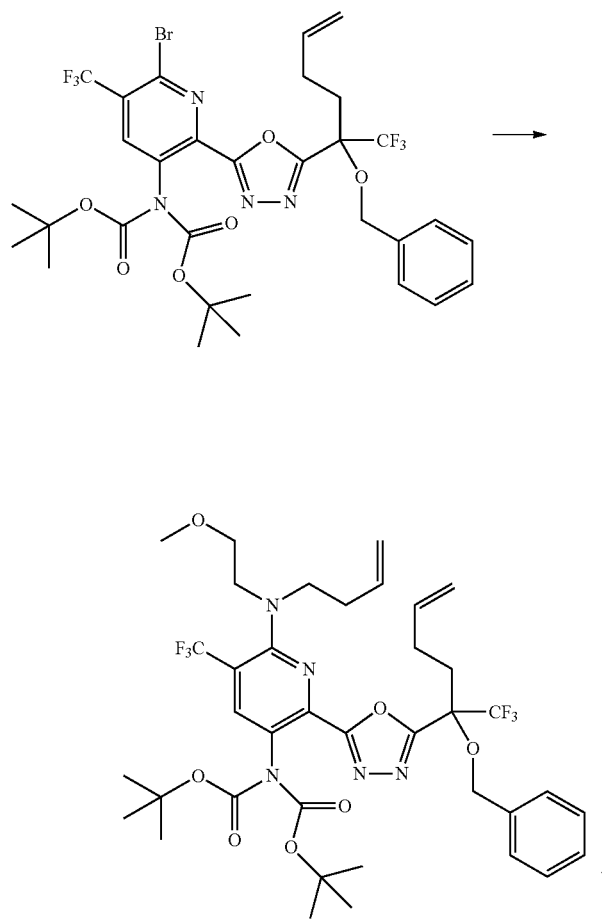

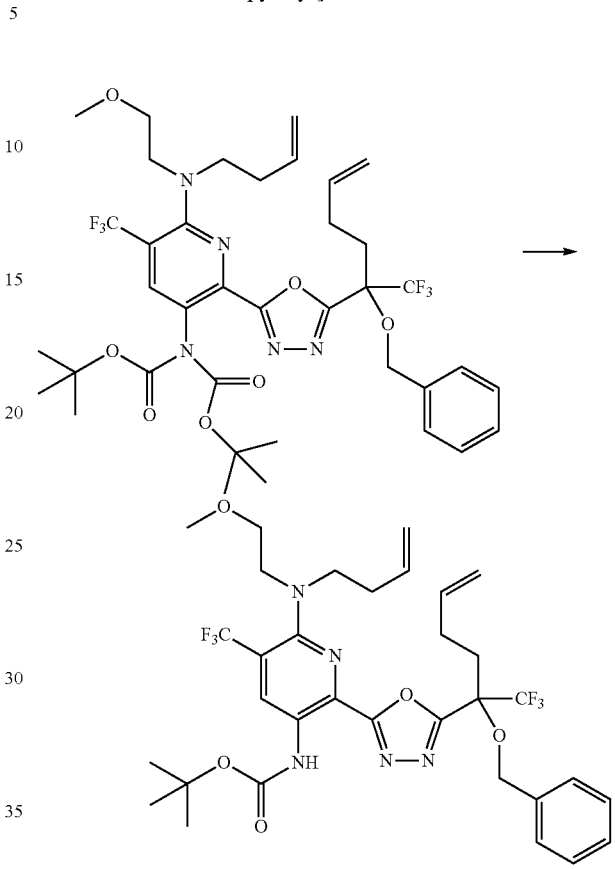

In a 250-mL sealed vessel, N-(2-methoxyethyl)but-3-en-1-amine (180 mg, 1.393 mmol), DIEA (1000 μL, 5.741 mmol) and tert-butyl N-[2-[5-[1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate (600 mg, 0.7984 mmol) were combined in acetonitrile (15 mL) and the mixture was heated at 80° C. for 36 hours. The reaction mixture was cooled to room temperature and concentrated under reduced pressure. The residue was purified by silica gel chromatography (80 gram column) using a gradient from 100% hexanes to 60% ethyl acetate in hexanes which gave as a yellow foam, tert-butyl N-[2-[5-[1-benzyloxy-1-(trifluoromethyl)pent-4-enyl]-1,3,4-oxadiazol-2-yl]-6-[but-3-enyl(2-methoxyethyl)amino]-5-(trifluoromethyl)-3-pyridyl]-N-tert-butoxycarbonyl-carbamate (269 mg, 42%). ESI-MS m/z calc. 799.33795, found 800.2 (M+1)$^+$; Retention time: 1.96 minutes (LC Method M).

To a solution of tert-butyl N-[2-[5-[1-benzyloxy-1-(trifluoromethyl)pent-4-enyl]-1,3,4-oxadiazol-2-yl]-6-[but-3-enyl(2-methoxyethyl)amino]-5-(trifluoromethyl)-3-pyridyl]-N-tert-butoxycarbonyl-carbamate (241 mg, 0.3013 mmol) in THF (2.5 mL) was added MeOH (2.5 mL) and water (2 mL) followed by lithium hydroxide (26 mg, 1.086 mmol). The mixture was stirred at 60° C. for 7 h. THF and methanol were removed under reduced pressure, 10% HCl (10 mL) was added and the product was extracted with EtOAc (2×50 mL). The organic phases were combined, washed with brine (5 mL), dried over anhydrous sodium sulfate, filtered and concentrated under reduced pressure. The residue was then purified by silica gel chromatography (40 gram column) using a gradient from 100% hexanes to 50% ethyl acetate in hexanes which provided as a yellow solid, tert-butyl N-[2-[5-[1-benzyloxy-1-(trifluoromethyl)pent-4-enyl]-1,3,4-oxadiazol-2-yl]-6-[but-3-enyl(2-methoxyethyl)amino]-5-(trifluoromethyl)-3-pyridyl]carbamate (138 mg, 65%). ESI-MS m/z calc. 699.2855, found 700.2 (M+1)$^+$; Retention time: 2.2 minutes (LC Method M).

Step 3: tert-Butyl N-[6-benzyloxy-13-(2-methoxyethyl)-6,15-bis(trifluoromethyl)-19-oxa-3,4,13,18-tetrazatricyclo[12.3.1.1 2,5]nonadeca-1(17),2,4,9,14(18),15-hexaen-17-yl]carbamate (E/Z mixture)

Step 4: tert-Butyl N-[6-hydroxy-13-(2-methoxyethyl)-6,15-bis(trifluoromethyl)-19-oxa-3,4,13,18-tetraazatricyclo[12.3.1.1 2,5]nonadeca-1(18),2,4,14,16-pentaen-17-yl]carbamate

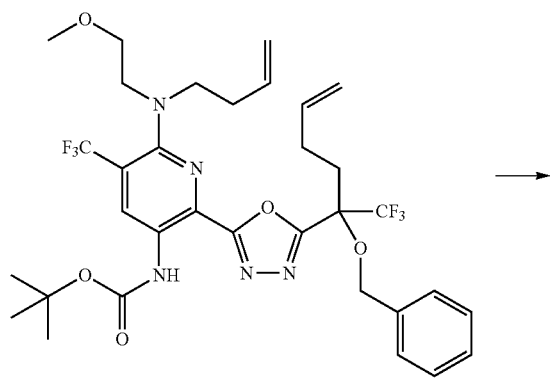

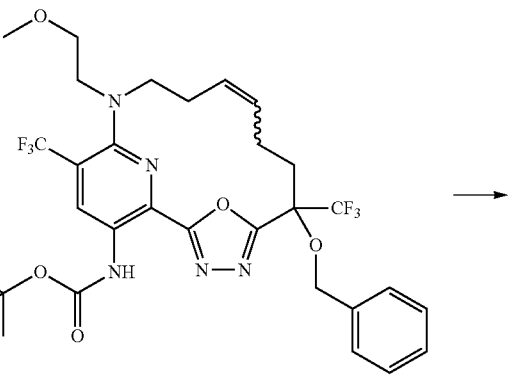

E/Z mixture

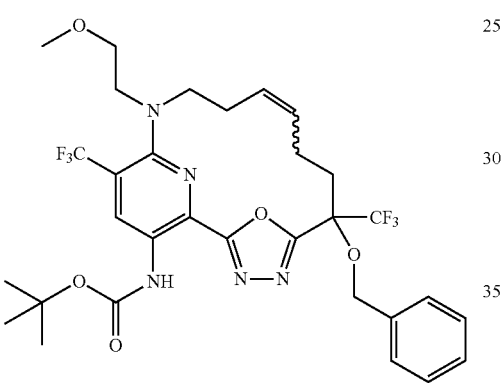

E/Z mixture

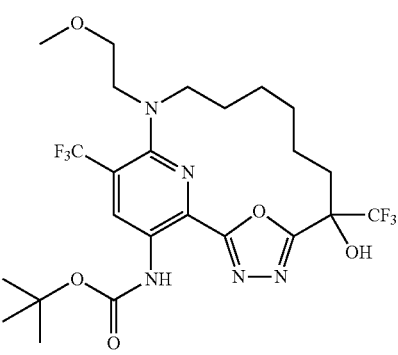

In a 500 mL round-bottom flask, a degassed solution of tert-butyl N-[2-[5-[1-benzyloxy-1-(trifluoromethyl)pent-4-enyl]-1,3,4-oxadiazol-2-yl]-6-[but-3-enyl(2-methoxyethyl)amino]-5-(trifluoromethyl)-3-pyridyl]carbamate (180 mg, 0.2573 mmol) in DCE (80 mL) was heated at 50° C. under nitrogen atmosphere. Then, Zhan catalyst-1B (35 mg, 0.04770 mmol) was added in two portions over 10 minutes. The resulting mixture was heated at 70° C. for 3 hours. The reaction mixture was cooled to room temperature and concentrated under reduced pressure. The residue was purified by silica gel chromatography (40 gram column) using a gradient from 100% hexanes to 30% ethyl acetate in hexanes to afford as a yellow residue, tert-butyl N-[6-benzyloxy-13-(2-methoxyethyl)-6,15-bis(trifluoromethyl)-19-oxa-3,4,13,18-tetrazatricyclo[12.3.1.1 2,5]nonadeca-1(17),2,4,9,14(18),15-hexaen-17-yl]carbamate (E/Z mixture) (103 mg, 60%). ESI-MS m/z calc. 671.2542, found 672.2 (M+1)$^+$; Retention time: 2.0 minutes (LC Method M).

To a solution of tert-butyl N-[6-benzyloxy-13-(2-methoxyethyl)-6,15-bis(trifluoromethyl)-19-oxa-3,4,13,18-tetrazatricyclo[12.3.1.1 2,5]nonadeca-1(17),2,4,9,14(18),15-hexaen-17-yl]carbamate (E/Z mixture) (103 mg, 0.1534 mmol) in AcOH (2.5 mL) and ethyl acetate (2.5 mL) was added Pd/C (165 mg of 10% w/w, 0.1550 mmol). The mixture was placed on a Parr shaker and degassed under vacuum and filled with nitrogen gas three times. Then, all nitrogen gas was removed, and the reactor was pressurized with hydrogen gas. The mixture was shaken at 80 psi for 3 hours and at 100 psi for 4 additional hours. The reactor was depressurized and the reaction was filtered and concentrated and placed under high vacuum for 30 minutes to afford as a yellow residue, tert-butyl N-[6-hydroxy-13-(2-methoxyethyl)-6,15-bis(trifluoromethyl)-19-oxa-3,4,13,18-tetraazatricyclo[12.3.1.1 2,5]nonadeca-1(18),2,4,14,16-pentaen-17-yl]carbamate (64 mg, 72%). ESI-MS m/z calc. 583.22296, found 584.2 (M+1)$^+$; Retention time: 1.39 minutes (LC Method J).

341

Step 5: 17-Amino-13-(2-methoxyethyl)-6,15-bis(trifluoromethyl)-19-oxa-3,4,13,18-tetraazatricyclo[12.3.1.1²,⁵]nonadeca-1(18),2,4,14,16-pentaen-6-ol

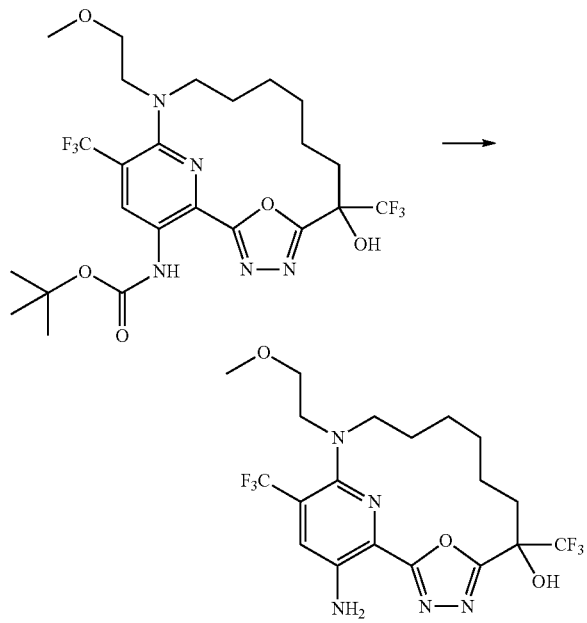

To a solution of tert-butyl N-[6-hydroxy-13-(2-methoxyethyl)-6,15-bis(trifluoromethyl)-19-oxa-3,4,13,18-tetraazatricyclo[12.3.1.1²,⁵]nonadeca-1(18),2,4,14,16-pentaen-17-yl]carbamate (64 mg, 0.1097 mmol) in DCM (1.0 mL) was added TFA (750 µL, 9.735 mmol) and the mixture was stirred at room temperature for 1 h. The mixture was evaporated, and the residue was purified by silica gel chromatography (12 gram column) using a gradient from 100% hexanes to 60% ethyl acetate in hexanes to afford as a yellow solid, 17-amino-13-(2-methoxyethyl)-6,15-bis(trifluoromethyl)-19-oxa-3,4,13,18-tetrazatricyclo[12.3.1.1²,⁵]nonadeca-1(18),2,4,14,16-pentaen-6-ol (50 mg, 94%). ESI-MS m/z calc. 483.1705, found 484.2 (M+1)⁺; Retention time: 1.35 minutes (LC Method A).

Step 6: 17-Amino-13-(2-methoxyethyl)-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (Compound 34) and 17-amino-13-(2-methoxyethyl)-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (Compound 35)

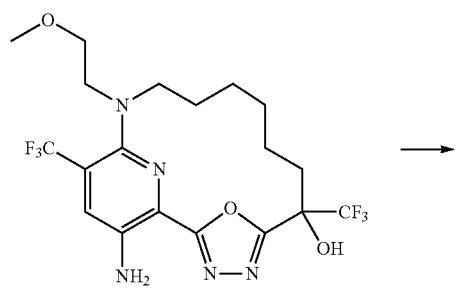

342

-continued

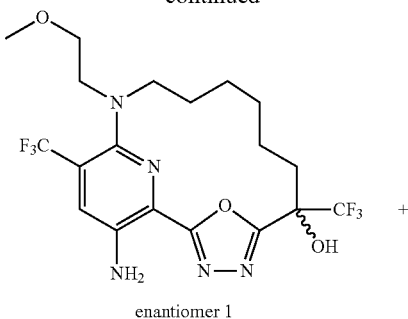

enantiomer 1

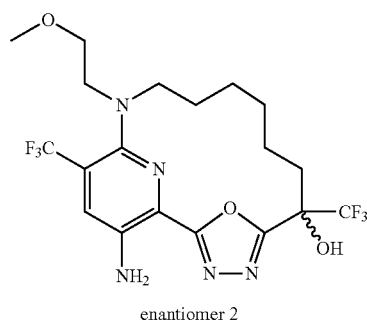

enantiomer 2

Racemic 17-amino-13-(2-methoxyethyl)-6,15-bis(trifluoromethyl)-19-oxa-3,4,13,18-tetrazatricyclo[12.3.1.1²,⁵]nonadeca-1(18),2,4,14,16-pentaen-6-ol (49 mg, 0.1014 mmol) was purified by chiral SFC using a LUX-4 column (250×21.2 mm, 5 µm particle size) sold by Phenomenex and eluting with 14% MeOH (+20 mM $NH_3$)/86% $CO_2$ which gave two single enantiomer products:

The first enantiomer to elute was further purified by reverse-phase preparative HPLC using a gradient from 1% to 99% acetonitrile in water (+5 mM HCl) over 15 minutes to afford as a yellow solid, 17-amino-13-(2-methoxyethyl)-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (13.4 mg, 54%). ¹H NMR (400 MHz, DMSO-d6) δ 7.71 (s, 1H), 7.57 (s, 1H), 6.33 (s, 2H), 3.51 (d, J=6.3 Hz, 2H), 3.30 (s, 1H), 3.29-3.23 (m, 3H), 3.22 (s, 3H), 2.14 (t, J=7.1 Hz, 2H), 1.89 (dq, J=17.4, 5.5, 4.9 Hz, 1H), 1.66-1.50 (m, 4H), 1.42 (ddd, J=28.9, 14.6, 7.3 Hz, 3H) ppm. ESI-MS m/z calc. 483.1705, found 484.2 (M+1)⁺; Retention time: 1.96 minutes (LC Method A).

The second enantiomer to elute was further purified by reverse-phase preparative HPLC using a gradient from 1% to 99% acetonitrile in water (+5 mM HCl) over 15 minutes to afford as a yellow solid, 17-amino-13-(2-methoxyethyl)-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (13.8 mg, 56%). ¹H NMR (400 MHz, DMSO-d6) δ 7.71 (s, 1H), 7.57 (s, 1H), 6.31 (s, 2H), 3.52 (t, J=6.3 Hz, 2H), 3.35-3.29 (m, 1H), 3.29-3.23 (m, 3H), 3.22 (s, 3H), 2.14 (t, J=7.2 Hz, 2H), 1.93-1.84 (m, 1H), 1.67-1.50 (m, 4H), 1.50-1.35 (m, 3H) ppm. ESI-MS m/z calc. 483.1705, found 484.2 (M+1)⁺; Retention time: 1.96 minutes (LC Method A).

Example 21: Preparation of (12R)-20-amino-18-(trifluoromethyl)-22-oxa-3,4,16,21-tetraazatetracyclo[15.3.1.12,5.012,16]docosa-1(21),2,4,17,19-pentaen-6-one (Compound 36)

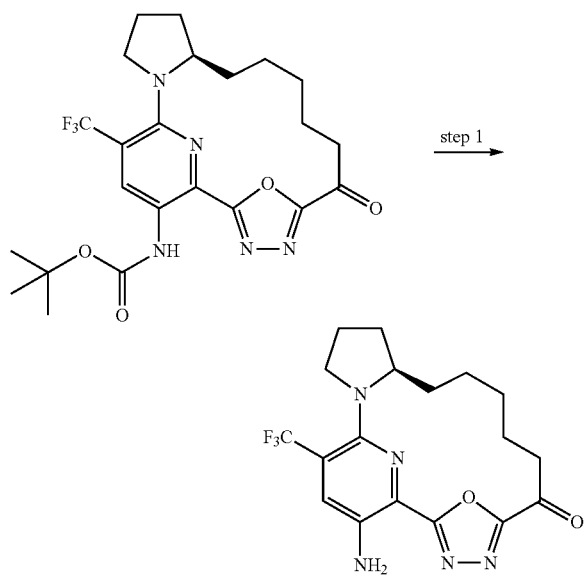

Step 1: (12R)-20-amino-18-(trifluoromethyl)-22-oxa-3,4,16,21-tetraazatetracyclo[15.3.1.12,5.012,16]docosa-1(21),2,4,17,19-pentaen-6-one (Compound 36)

A solution of tert-butyl N-[(12R)-6-oxo-18-(trifluoromethyl)-22-oxa-3,4,16,21-tetraazatetracyclo[15.3.1.12,5.012,16]docosa-1(21),2,4,17,19-pentaen-20-yl]carbamate (8 mg, 0.01615 mmol) was dissolved in dichloromethane (137 μL) and TFA (62.09 μL, 0.8059 mmol) was added. The mixture was stirred at room temperature for 2 h. The reaction was concentrated, dissolved in dichloromethane and washed with saturated NaHCO$_3$ solution. The organic layer was concentrated to give as an orange solid, (12R)-20-amino-18-(trifluoromethyl)-22-oxa-3,4,16,21-tetraazatetracyclo[15.3.1.12,5.012,16]docosa-1(21),2,4,17,19-pentaen-6-one (3 mg, 47%). $^1$H NMR (400 MHz, Chloroform-d) δ 7.49 (s, 1H), 4.00 (q, J=8.3 Hz, 1H), 3.66 (q, J=8.5 Hz, 1H), 3.48 (s, 1H), 3.28 (td, J=11.6, 2.5 Hz, 1H), 2.72 (d, J=11.9 Hz, 1H), 2.64 (dt, J=11.9, 5.9 Hz, 1H), 2.30-2.00 (m, 4H), 1.96-1.67 (m, 6H), 1.01 (d, J=11.7 Hz, 1H) ppm. ESI-MS m/z calc. 395.15692, found 396.1 (M+1)$^+$; Retention time: 1.67 minutes (LC Method A). Two exchangeable NH$_2$ protons were not observed in the $^1$H NMR.

Example 22: Preparation of 5-amino-11-hydroxy-3,11-bis(trifluoromethyl)-21-oxa-1,8,9,16,22-pentaazatetracyclo[14.2.2.12,6.17,10]docosa-2,4,6(22),7,9-pentaen-15-one (enantiomer 1) (Compound 37) and 5-amino-11-hydroxy-3,11-bis(trifluoromethyl)-21-oxa-1,8,9,16,22-pentaazatetracyclo[14.2.2.12,6.17,10]docosa-2,4,6(22),7,9-pentaen-15-one (enantiomer 2) (Compound 38)

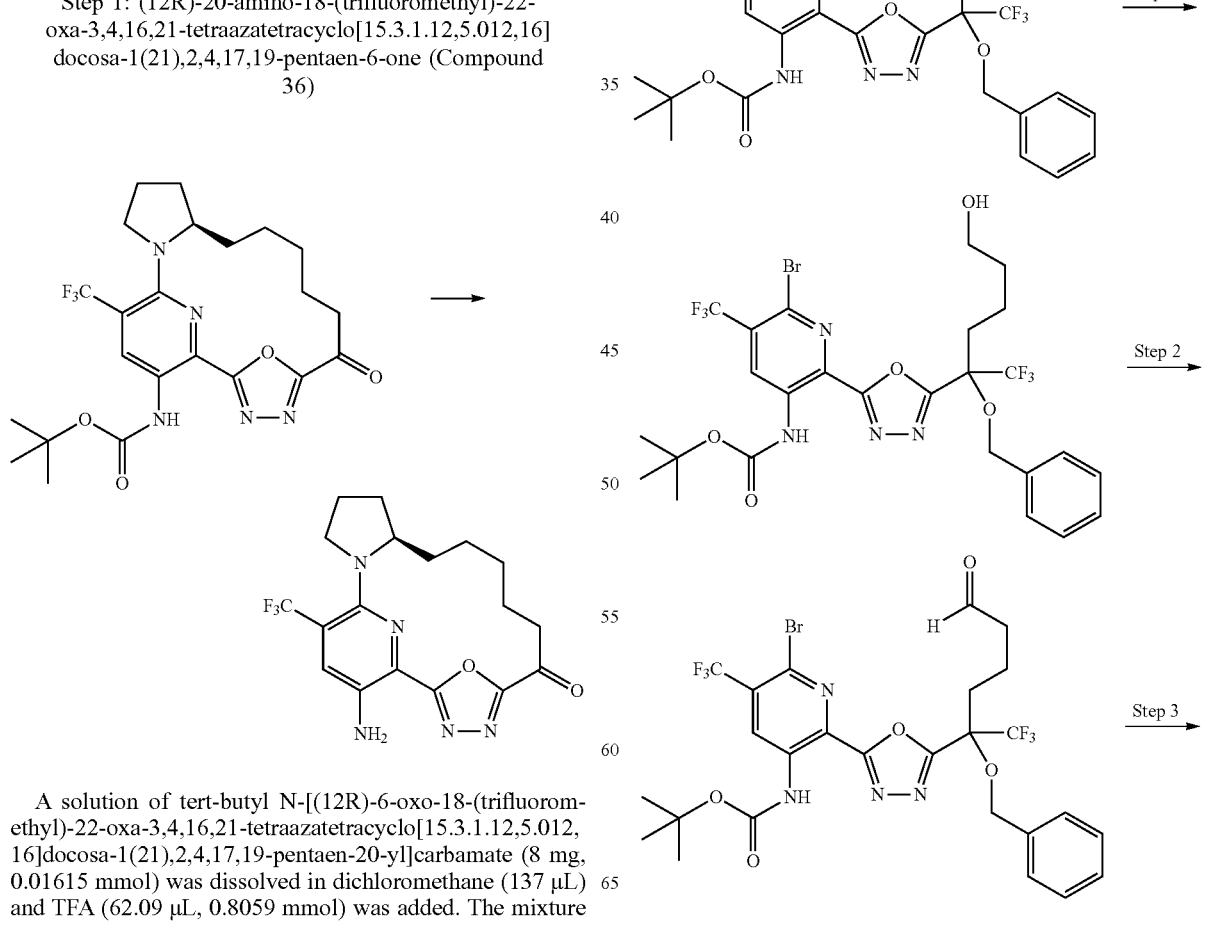

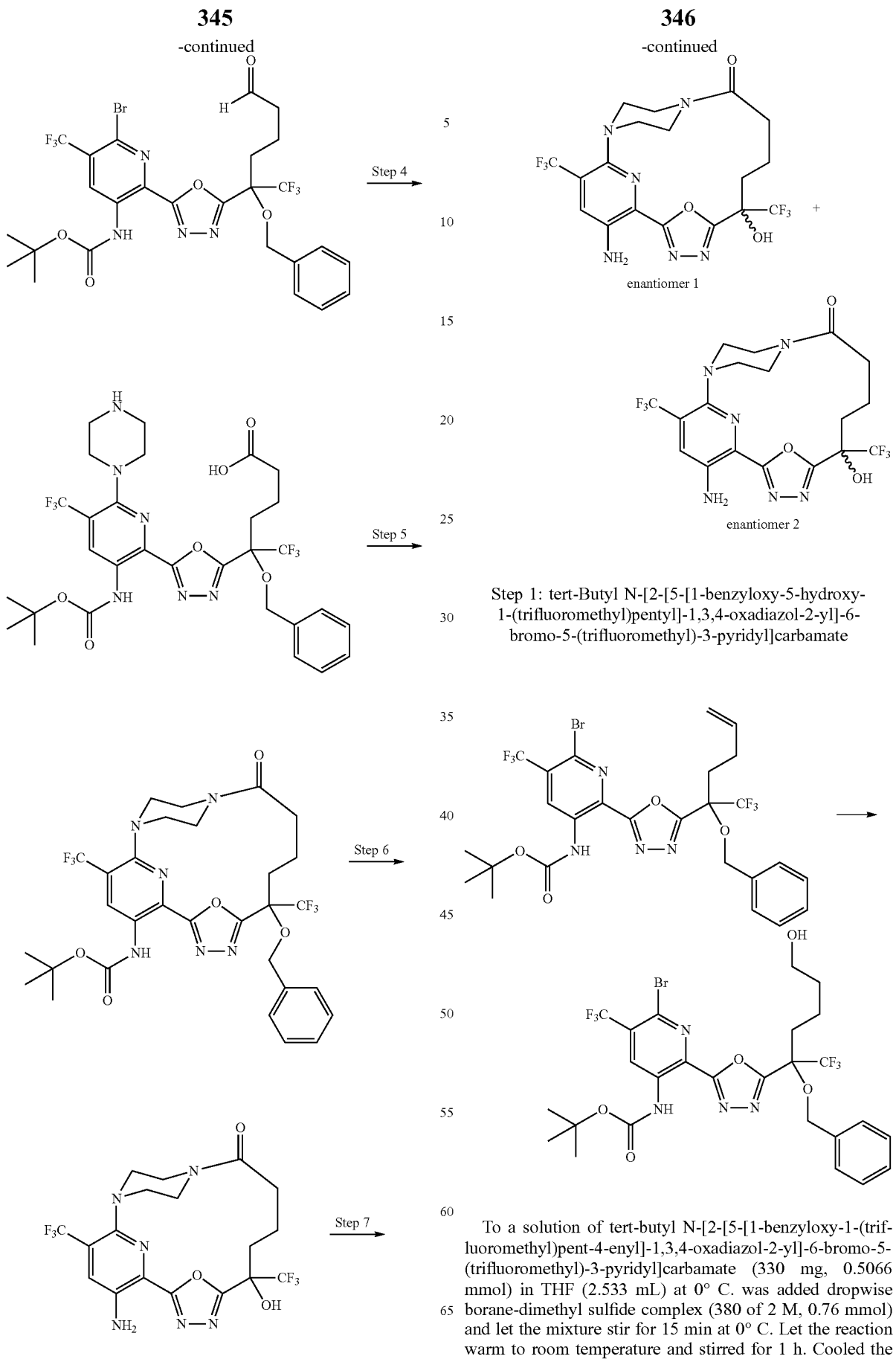

Step 1: tert-Butyl N-[2-[5-[1-benzyloxy-5-hydroxy-1-(trifluoromethyl)pentyl]-1,3,4-oxadiazol-2-yl]-6-bromo-5-(trifluoromethyl)-3-pyridyl]carbamate To a solution of tert-butyl N-[2-[5-[1-benzyloxy-1-(trifluoromethyl)pent-4-enyl]-1,3,4-oxadiazol-2-yl]-6-bromo-5-(trifluoromethyl)-3-pyridyl]carbamate (330 mg, 0.5066 mmol) in THF (2.533 mL) at 0° C. was added dropwise borane-dimethyl sulfide complex (380 of 2 M, 0.76 mmol) and let the mixture stir for 15 min at 0° C. Let the reaction warm to room temperature and stirred for 1 h. Cooled the reaction to 0° C. before quenching with NaOH (1.35 mL of 2 M, 2.7 mmol), followed by the addition of hydrogen peroxide (300 μL, 9.79 mmol). Let the mixture stir for 30 min at room temperature before extracting with ethyl acetate (2×20 mL). The organic layers were combined, washed with brine (25 mL), dried over sodium sulfate, filtered and concentrated. Purified the filtrate by silica gel chromatography, 4 g column, using a 0% to 30% ethyl acetate/hexanes to afford as a colorless semi-solid, tert-butyl N-[2-[5-[1-benzyloxy-5-hydroxy-1-(trifluoromethyl)pentyl]-1,3,4-oxadiazol-2-yl]-6-bromo-5-(trifluoromethyl)-3-pyridyl]carbamate (200 mg, 59%). ESI-MS m/z calc. 668.1069, found 670.4 (M+1)⁺; Retention time: 0.6 minutes (LC Method T).

Step 2: tert-Butyl N-[2-[5-[1-benzyloxy-5-oxo-1-(trifluoromethyl)pentyl]-1,3,4-oxadiazol-2-yl]-6-bromo-5-(trifluoromethyl)-3-pyridyl]carbamate

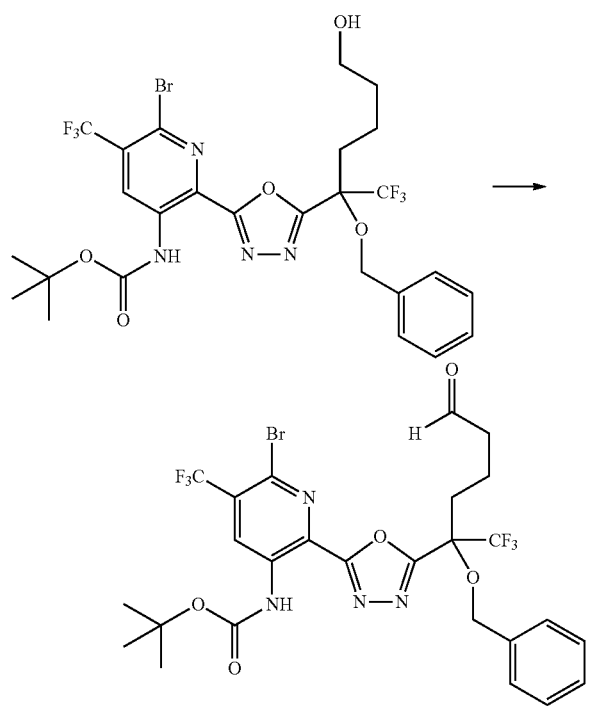

To a solution of tert-butyl N-[2-[5-[1-benzyloxy-5-hydroxy-1-(trifluoromethyl)pentyl]-1,3,4-oxadiazol-2-yl]-6-bromo-5-(trifluoromethyl)-3-pyridyl]carbamate (135 mg, 0.2017 mmol) in dichloromethane (2.0 mL) was added Dess-Martin periodinane (102.6 mg, 0.2419 mmol). The reaction was complete after 15 min. Quenched the reaction with saturated aqueous NaHCO₃. Extracted with dichloromethane (2×25 mL) then the organic layers were combined and washed with brine then dried over Na₂SO₄, filtered and concentrated. Purified the filtrate via silica gel chromatography (12 g column) using a gradient from 0% to 30% ethyl acetate/hexanes over 10 min to obtain as a white solid, tert-butyl N-[2-[5-[1-benzyloxy-5-oxo-1-(trifluoromethyl)pentyl]-1,3,4-oxadiazol-2-yl]-6-bromo-5-(trifluoromethyl)-3-pyridyl]carbamate (100 mg, 74%). ESI-MS m/z calc. 666.09125, found 667.3 (M+1)⁺; Retention time: 0.66 minutes (LC Method T).

Step 3: 5-Benzyloxy-5-[5-[6-bromo-3-(tert-butoxycarbonylamino)-5-(trifluoromethyl)-2-pyridyl]-1,3,4-oxadiazol-2-yl]-6,6,6-trifluoro-hexanoic acid

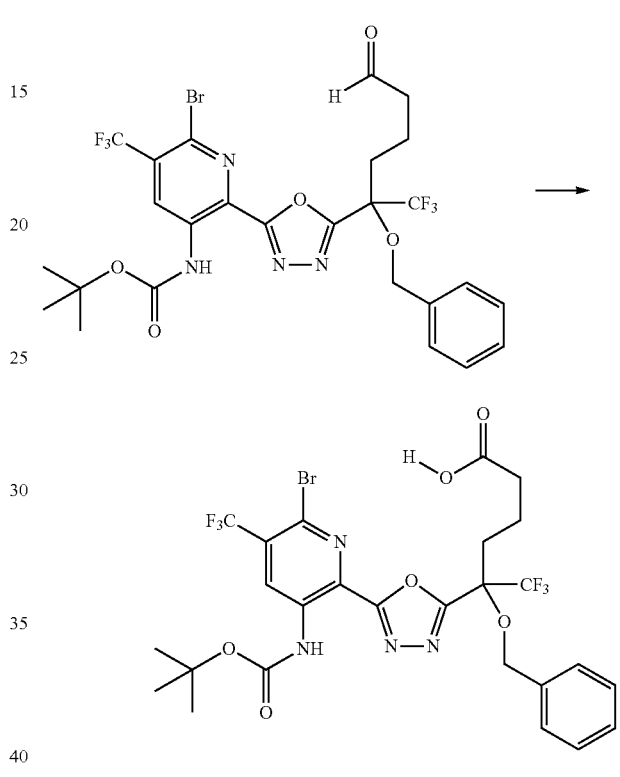

To a solution of tert-butyl N-[2-[5-[1-benzyloxy-5-oxo-1-(trifluoromethyl)pentyl]-1,3,4-oxadiazol-2-yl]-6-bromo-5-(trifluoromethyl)-3-pyridyl]carbamate (450 mg, 0.6743 mmol) and 2-methyl-2-butene (1.389 mL, 13.11 mmol) in tert-butanol (5.44 mL) was added a solution of sodium chlorite (126.3 mg, 1.396 mmol) and sodium phosphate monobasic, monohydrate (651.7 mg, 4.723 mmol) in water (5.44 mL). The reaction mixture was stirred room temperature for 2 h. The reaction mixture was partially concentrated under reduced pressure. Water (20 mL) was added and the aqueous layer was acidified with 1 N HCl until pH was ~1-2 and extracted with dichloromethane (2×50 mL). The combined organic layers were washed with brine, dried over anhydrous sodium sulfate, filtered and concentrated under reduced pressure to afford as a crude white solid, 5-benzyloxy-5-[5-[6-bromo-3-(tert-butoxycarbonylamino)-5-(trifluoromethyl)-2-pyridyl]-1,3,4-oxadiazol-2-yl]-6,6,6-trifluoro-hexanoic acid (455 mg, 99%). ESI-MS m/z calc. 682.0862, found 683.2 (M+1)⁺; Retention time: 0.57 minutes. This material was taken directly to the ensuing step without further purification (LC Method T).

349

Step 4: 5-Benzyloxy-5-[5-[3-(tert-butoxycarbonylamino)-6-piperazin-1-yl-5-(trifluoromethyl)-2-pyridyl]-1,3,4-oxadiazol-2-yl]-6,6,6-trifluorohexanoic acid

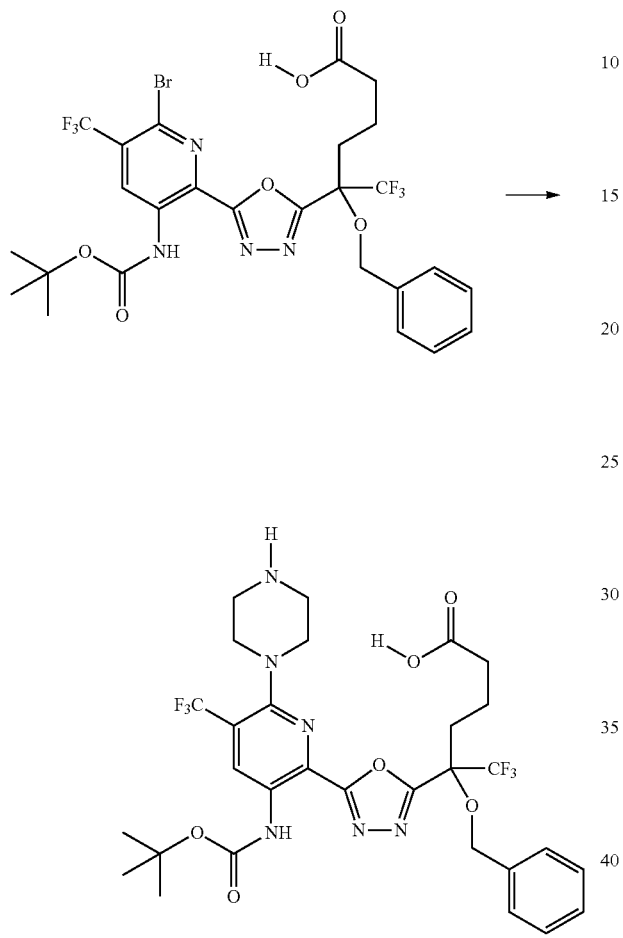

In a microwave sealed vial, 5-benzyloxy-5-[5-[6-bromo-3-(tert-butoxycarbonylamino)-5-(trifluoromethyl)-2-pyridyl]-1,3,4-oxadiazol-2-yl]-6,6,6-trifluoro-hexanoic acid (160 mg, 0.2341 mmol), diisopropylethylamine (244.7 µL, 1.405 mmol) and piperazine (100.8 mg, 1.17 mmol) were added to acetonitrile (1 mL) and the mixture was heated at 90° C. for 9 h. Diluted the reaction with water and extracted with ethyl acetate (3×15 mL). Combined the organic layers and washed with brine, dried over $Na_2SO_4$, filtered and concentrated to a yellow solid, 5-benzyloxy-5-[5-[3-(tert-butoxycarbonylamino)-6-piperazin-1-yl-5-(trifluoromethyl)-2-pyridyl]-1,3,4-oxadiazol-2-yl]-6,6,6-trifluoro-hexanoic acid (150 mg, 93%). ESI-MS m/z calc. 688.2444, found 689.3 (M+1)$^+$; Retention time: 0.69 minutes. This material was taken directly to the ensuing step without further purification (LC Method S).

350

Step 5: tert-Butyl N-[11-(benzyloxy)-15-oxo-3,11-bis(trifluoromethyl)-21-oxa-1,8,9,16,22-pentaazatetracyclo[14.2.2.12,6.17,10]docosa-2,4,6(22),7,9-pentaen-5-yl]carbamate

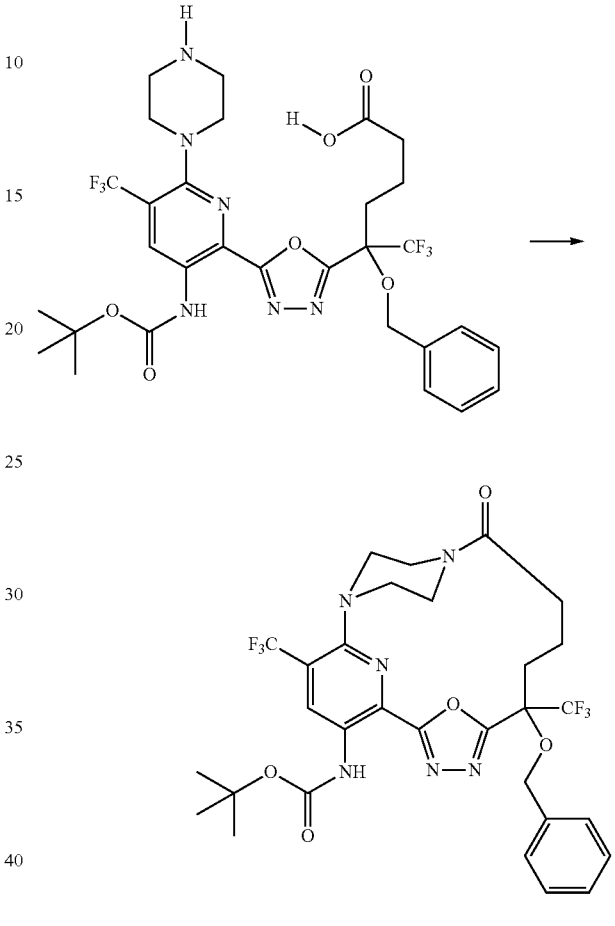

To a solution of 5-benzyloxy-5-[5-[3-(tert-butoxycarbonylamino)-6-piperazin-1-yl-5-(trifluoromethyl)-2-pyridyl]-1,3,4-oxadiazol-2-yl]-6,6,6-trifluoro-hexanoic acid (125 mg, 0.1815 mmol) in DMF (12.5 mL) was added DIEA (158.1 µL, 0.9077 mmol) followed by HATU (151.8 mg, 0.3992 mmol). The reaction mixture was stirred at room temperature for 5 min. The reaction was extracted with ethyl acetate (3×20 mL). The organic layers were washed with brine (20 mL), dried over sodium sulfate, filtered and evaporated. The crude material was then purified by silica gel chromatography using a gradient from 100% hexanes to 70% ethyl acetate in hexanes to afford as a yellow solid, tert-butyl N-[11-(benzyloxy)-15-oxo-3,11-bis(trifluoromethyl)-21-oxa-1,8,9,16,22-pentaazatetracyclo[14.2.2.12, 6.17,10]docosa-2,4,6(22),7,9-pentaen-5-yl]carbamate (115 mg, 80%). ESI-MS m/z calc. 670.2338, found 671.2 (M+1)$^+$; Retention time: 0.9 minutes (LC Method S).

Step 6: tert-Butyl N-[11-hydroxy-15-oxo-3,11-bis(trifluoromethyl)-21-oxa-1,8,9,16,22-pentaazatetracyclo[14.2.2.1²,⁶.1⁷,¹⁰]docosa-2,4,6(22),7,9-pentaen-5-yl]carbamate

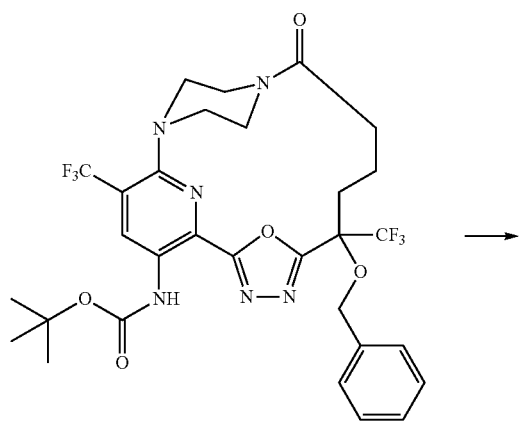

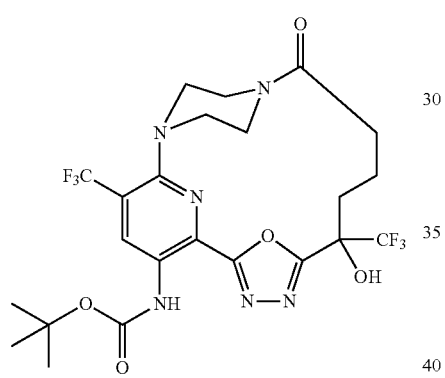

To a nitrogen flushed solution of tert-butyl N-[11-(benzyloxy)-15-oxo-3,11-bis(trifluoromethyl)-21-oxa-1,8,9,16,22-pentaazatetracyclo[14.2.2.1²,⁶.1⁷,¹⁰]docosa-2,4,6(22),7,9-pentaen-5-yl]carbamate (115 mg, 0.1458 mmol) in acetic acid (2.639 mL) was added Pd/C (53.11 mg of 10% w/w, 0.04991 mmol). The mixture was evacuated and then stirred under a hydrogen atmosphere using a hydrogen-filled balloon at room temperature for 20 h. Filtered the solution through a silica plug, washing well with ethyl acetate and then concentrated the filtrate under reduced pressure. Purified the residue by preparative reverse phase HPLC using a C$_{18}$ column with a gradient of 30% to 99% acetonitrile in water. Combined the desired fractions to obtain an off-white solid, tert-butyl N-[11-hydroxy-15-oxo-3,11-bis(trifluoromethyl)-21-oxa-1,8,9,16,22-pentaazatetracyclo[14.2.2.1²,⁶.1⁷,¹⁰]docosa-2,4,6(22),7,9-pentaen-5-yl]carbamate (25 mg, 30%). ESI-MS m/z calc. 580.1869, found 581.4 (M+1)⁺; Retention time: 0.76 minutes (LC Method S).

Step 7: 5-Amino-11-hydroxy-3,11-bis(trifluoromethyl)-21-oxa-1,8,9,16,22-pentaazatetracyclo[14.2.2.1²,⁶.1⁷,¹⁰]docosa-2,4,6(22),7,9-pentaen-15-one (enantiomer 1) (Compound 37) and 5-amino-11-hydroxy-3,11-bis(trifluoromethyl)-21-oxa-1,8,9,16,22-pentaazatetracyclo[14.2.2.1²,⁶.1⁷,¹⁰]docosa-2,4,6(22),7,9-pentaen-15-one (enantiomer 2) (Compound 38)

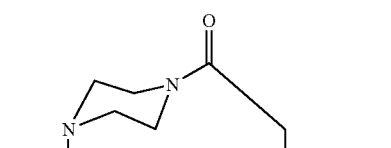

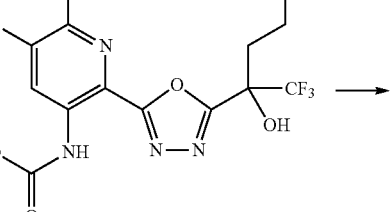

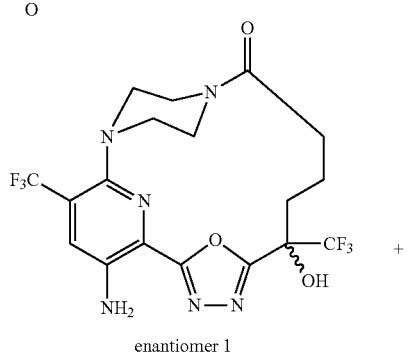
enantiomer 1

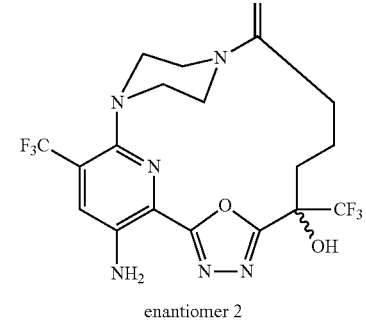
enantiomer 2 tert-Butyl N-[11-hydroxy-15-oxo-3,11-bis(trifluoromethyl)-21-oxa-1,8,9,16,22-pentaazatetracyclo[14.2.2.1²,⁶.1⁷,¹⁰]docosa-2,4,6(22),7,9-pentaen-5-yl]carbamate (20 mg, 0.03445 mmol) was dissolved in dichloromethane (342.4 µL) and to the mixture was added TFA (132.4 µL, 1.719 mmol) and the mixture was stirred at room temperature for 2 h. The reaction was concentrated in vacuo, then taken up in dichloromethane and washed with saturated aqueous NaHCO₃. The organic layer was concentrated in vacuo to afford a pale yellow solid which was subjected to chiral SFC using a ChiralPak OD column (250×10 mm, 5 µm particle size) using 18% methanol (20 mM NH₃) in CO₂ mobile phase over 5 minutes (flow rate=10 mL/min, column temperature=35° C.). These conditions produced 2 enantiomeric products as described below:

Peak 1 was concentrated to afford as a pale yellow solid, 5-amino-11-hydroxy-3,11-bis(trifluoromethyl)-21-oxa-1,8,9,16,22-pentaazatetracyclo[14.2.2.1 2,6.1 7,10]docosa-2,4,6(22),7,9-pentaen-15-one (enantiomer 1) (2.9 mg, 35%). $^1$H NMR (400 MHz, Chloroform-d) δ 7.34 (s, 1H), 5.65 (s, 2H), 4.15 (dq, J=14.8, 7.2 Hz, 1H), 3.73 (dd, J=10.7, 5.4 Hz, 1H), 3.48 (ddd, J=16.9, 10.5, 6.5 Hz, 2H), 3.32 (tq, J=13.1, 6.7, 5.8 Hz, 4H), 3.03 (dq, J=12.8, 5.7 Hz, 1H), 2.65-2.46 (m, 3H), 2.28 (t, J=7.8 Hz, 1H), 1.94-1.81 (m, 2H) ppm. ESI-MS m/z calc. 480.13446, found 481.2 (M+1)$^+$; Retention time: 1.34 minutes (LC Method A).

Peak 2 was concentrated to afford as a pale yellow solid, 5-amino-11-hydroxy-3,11-bis(trifluoromethyl)-21-oxa-1,8,9,16,22-pentaazatetracyclo[14.2.2.1 2,6.1 7,10]docosa-2,4,6(22),7,9-pentaen-15-one (enantiomer 2) (2.9 mg, 35%); $^1$H NMR (400 MHz, Chloroform-d) δ 7.34 (s, 1H), 5.61 (d, J=39.0 Hz, 2H), 4.14 (dt, J=13.6, 7.1 Hz, 1H), 3.74 (q, J=5.2 Hz, 1H), 3.52-3.25 (m, 6H), 3.02 (dt, J=12.8, 6.0 Hz, 1H), 2.64-2.47 (m, 3H), 2.34-2.24 (m, 1H), 2.00-1.86 (m, 2H) ppm. ESI-MS m/z calc. 480.13446, found 481.2 (M+1)$^+$; Retention time: 1.34 minutes (LC Method A).

Example 23: Preparation of 17-amino-13-methyl-15-methylsulfonyl-6-(trifluoromethyl)-19-oxa-3,4,13,18-tetrazatricyclo[12.3.1.1 2,5]nonadeca-1(18),2,4,14,16-pentaen-6-ol (enantiomer 1) (Compound 39) and 17-amino-13-methyl-15-methylsulfonyl-6-(trifluoromethyl)-19-oxa-3,4,13,18-tetrazatricyclo [12.3.1.1 2,5]nonadeca-1(18),2,4,14,16-pentaen-6-ol (enantiomer 2) (Compound 40)

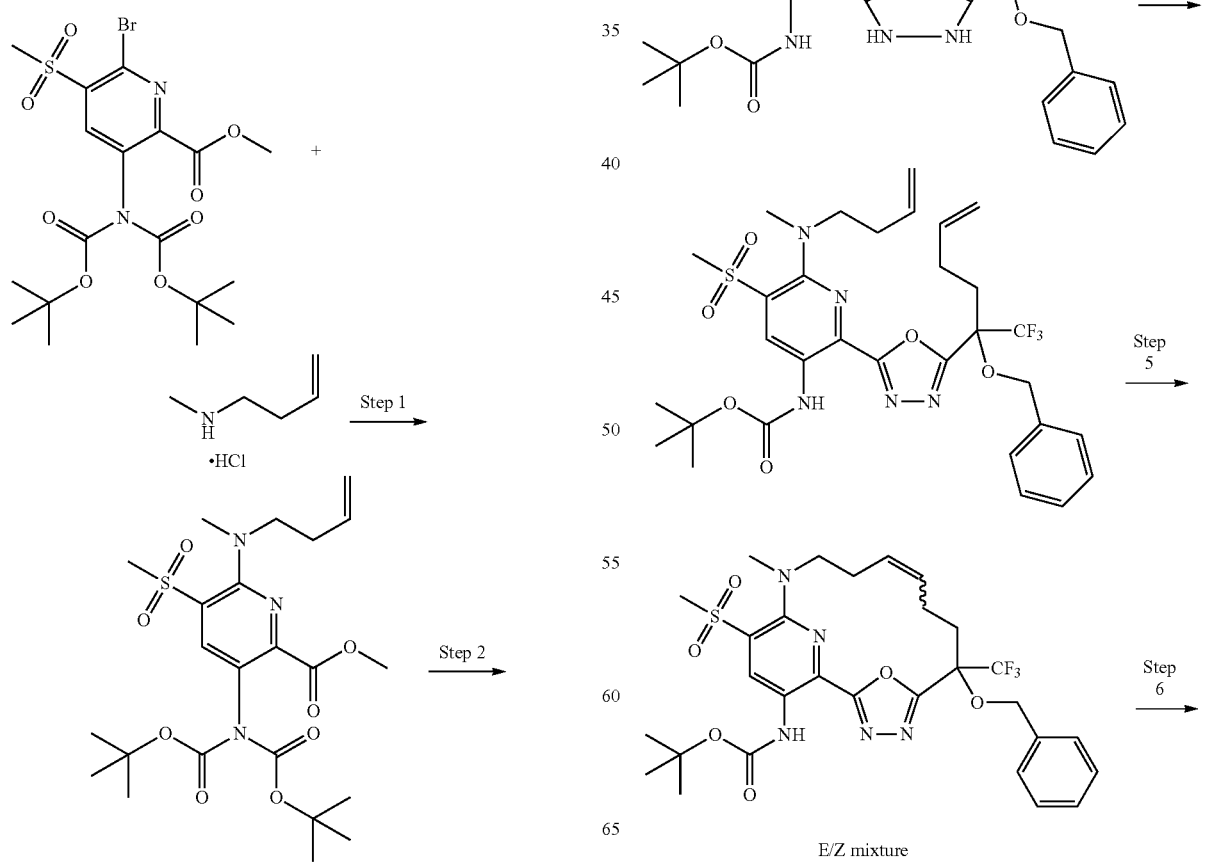

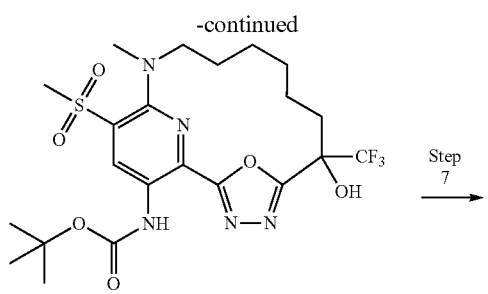

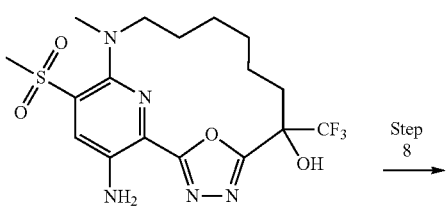

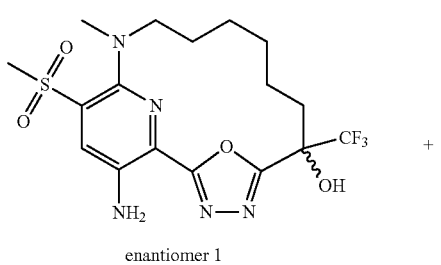

enantiomer 1

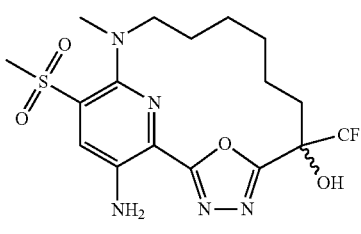

enantiomer 2

Step 1: Methyl 3-[bis(tert-butoxycarbonyl)amino]-6-[but-3-enyl)methyl)amino]-5-methylsulfonyl-pyridine-2-carboxylate

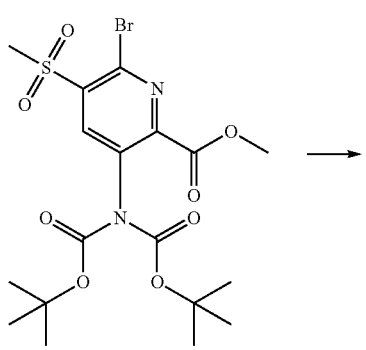

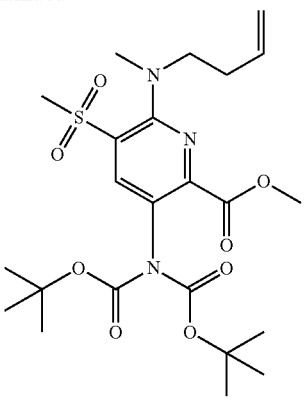

N-Methylbut-3-en-1-amine (hydrochloride salt) (370 mg, 3.043 mmol), DIEA (1.5 mL, 8.612 mmol) and methyl 3-[bis(tert-butoxycarbonyl)amino]-6-bromo-5-methylsulfonyl-pyridine-2-carboxylate (860 mg, 1.688 mmol) were combined in acetonitrile (12 mL) and the mixture was heated at 70° C. for 20 hours. The reaction mixture was cooled to ambient temperature and the solvent was removed under reduced pressure. The residue was diluted with EtOAc (50 mL) and washed with brine (2×25 mL), dried over sodium sulfate, filtered and concentrated. The residue was purified by silica gel chromatography (80 g column) using a gradient from 100% hexanes to 60% ethyl acetate in hexanes to afford as a pale yellow residue, methyl 3-[bis(tert-butoxycarbonyl)amino]-6-[but-3-enyl(methyl)amino]-5-methylsulfonyl-pyridine-2-carboxylate (820 mg, 95%). ESI-MS m/z calc. 513.2145, found 514.2 (M+1)$^+$; Retention time: 1.89 minutes (LC Method A).

Step 2: 6-[But-3-enyl)methyl)amino]-3-(tert-butoxycarbonylamino)-5-methylsulfonyl-pyridine-2-carboxylic acid

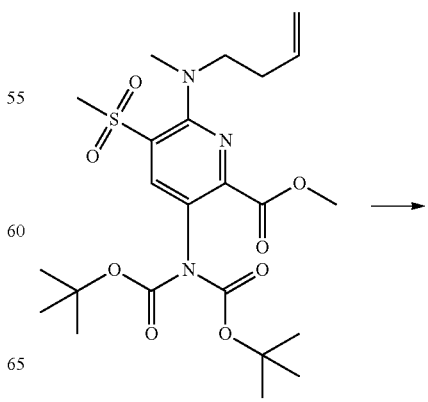

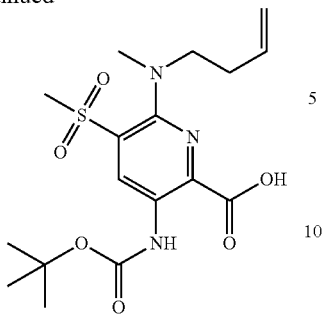

To a solution of methyl 3-[bis(tert-butoxycarbonyl)amino]-6-[but-3-enyl(methyl)amino]-5-methylsulfonyl-pyridine-2-carboxylate (810 mg, 1.577 mmol) in THF (8.5 mL) was added methanol (7.5 mL) and water (6.5 mL) followed by anhydrous lithium hydroxide (150 mg, 6.138 mmol). The mixture was stirred with heating at 65° C. for 3 h. THF and methanol were removed under reduced pressure and then 10 mL of 10% aqueous HCl was added and the product was extracted with EtOAc (2×50 mL). The organic phases were combined, washed with brine (5 mL), dried over anhydrous sodium sulfate, filtered and concentrated under reduced pressure. The crude material was then purified by silica gel chromatography (40 gram column) using a gradient from 100% hexanes to 80% ethyl acetate in hexanes which afforded as a yellow solid, 6-[but-3-enyl(methyl)amino]-3-(tert-butoxycarbonylamino)-5-methyl sulfonyl-pyridine-2-carboxylic acid (485 mg, 77%). $^1$H NMR (400 MHz, DMSO-d6) δ 13.82 (s, 1H), 10.08 (s, 1H), 9.06 (s, 1H), 5.78 (ddt, J=17.0, 10.2, 6.8 Hz, 1H), 5.05 (dq, J=17.2, 1.7 Hz, 1H), 4.97 (ddt, J=10.2, 2.4, 1.2 Hz, 1H), 3.39 (s, 3H), 3.21 (t, J=7.5 Hz, 2H), 2.81 (s, 3H), 2.30 (q, J=7.0 Hz, 2H), 1.49 (s, 9H) ppm. ESI-MS m/z calc. 399.1464, found 400.2 (M+1)$^+$; Retention time: 1.72 minutes (LC Method A).

Step 3: tert-butyl N-[2-[[[2-benzyloxy-2-(trifluoromethyl)hex-5-enoyl]amino]carbamoyl]-6-[but-3-enyl(methyl)amino]-5-methylsulfonyl-3-pyridyl]carbamate

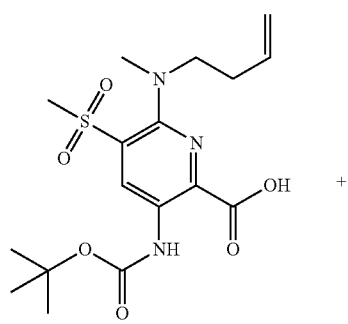 +

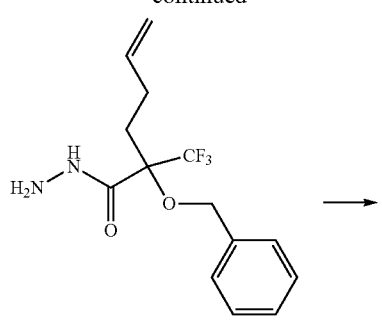

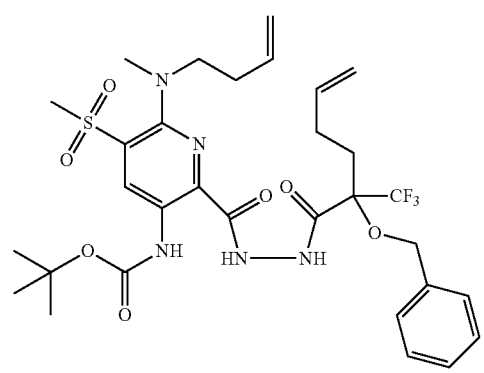

To a solution of 6-[but-3-enyl(methyl)amino]-3-(tert-butoxycarbonylamino)-5-methylsulfonyl-pyridine-2-carboxylic acid (480 mg, 1.202 mmol) in NMP (7 mL) was added 2-benzyloxy-2-(trifluoromethyl)hex-5-enehydrazide (380.9 mg, 1.260 mmol) and DIEA (850 µL, 4.880 mmol) followed by HATU (565 mg, 1.486 mmol). The reaction mixture was stirred at room temperature for 18 h. The reaction was diluted with ethyl acetate and washed with saturated aqueous sodium bicarbonate solution. The organic layer was further washed with 10% citric acid solution followed by brine. The organics were separated, dried over sodium sulfate, filtered and evaporated. The residue was purified by silica gel chromatography (80 gram column) using a gradient from 100% hexanes to 60% ethyl acetate in hexanes to afford as a yellow oil, tert-butyl N-[2-[[[2-benzyloxy-2-(trifluoromethyl)hex-5-enoyl]amino]carbamoyl]-6-[but-3-enyl(methyl)amino]-5-methylsulfonyl-3-pyridyl]carbamate (720 mg, 88%). $^1$H NMR (400 MHz, DMSO-d6) δ 10.75 (s, 1H), 10.66 (s, 1H), 10.33 (s, 1H), 9.27 (s, 1H), 7.52-7.49 (m, 2H), 7.41-7.37 (m, 2H), 7.35-7.31 (m, 1H), 5.82-5.74 (m, 1H), 5.15-5.04 (m, 2H), 5.04-4.98 (m, 2H), 4.97 (dd, J=10.1, 2.1 Hz, 1H), 4.85 (d, J 7.2 Hz, 2H), 3.41 (s, 3H), 3.27 (t, J=7.6 Hz, 2H), 2.84 (s, 3H), 2.34-2.27 (m, 4H), 2.19 (d, J=9.6 Hz, 2H), 1.49 (s, 9H) ppm. ESI-MS m/z calc. 683.2601, found 684.2 (M+1)$^+$; Retention time: 1.91 minutes (LC Method J).

Step 4: tert-Butyl N-[2-[5-[1-benzyloxy-1-(trifluoromethyl)pent-4-enyl]-1,3,4-oxadiazol-2-yl]-6-[but-3-enyl(methyl)amino]-5-methylsulfonyl-3-pyridyl]carbamate

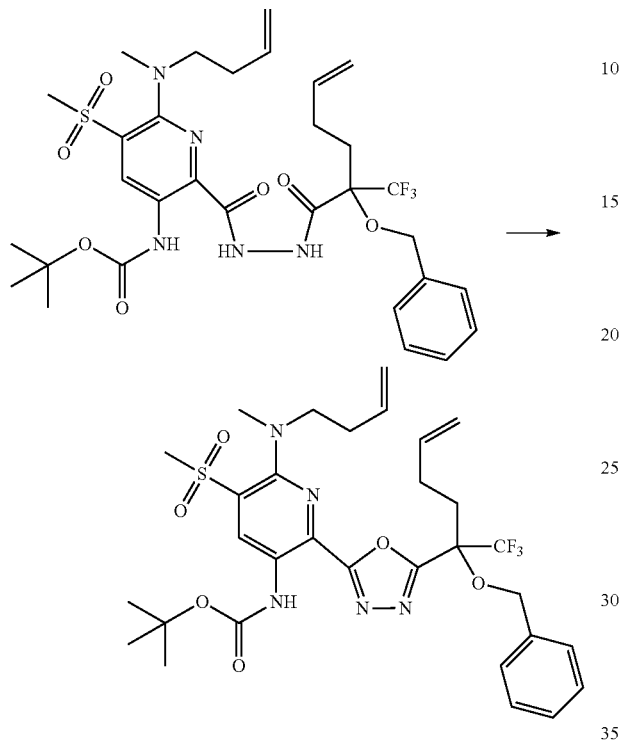

A solution of tert-butyl N-[2-[[[2-benzyloxy-2-(trifluoromethyl)hex-5-enoyl]amino]carbamoyl]-6-[but-3-enyl(methyl)amino]-5-methylsulfonyl-3-pyridyl]carbamate (720 mg, 1.053 mmol) and DIEA (750 µL, 4.306 mmol) in acetonitrile (20 mL) was heated at 50° C., then p-toluenesulfonyl chloride (320 mg, 1.678 mmol) was added in one portion. The resulting mixture was heated at 70° C. for 2 hours. The reaction mixture was cooled and quenched with a saturated aqueous solution of sodium bicarbonate (50 mL) and stirred for 15 minutes. Then the mixture was extracted with ethyl acetate (3×50 mL). The organics were combined, dried over sodium sulfate, filtered and evaporated. The residue was purified by silica gel chromatography (80 gram column) using a gradient from 100% hexanes to 50% ethyl acetate in hexanes to afford as a yellow foam, tert-butyl N-[2-[5-[1-benzyloxy-1-(trifluoromethyl)pent-4-enyl]-1,3,4-oxadiazol-2-yl]-6-[but-3-enyl(methyl)amino]-5-methylsulfonyl-3-pyridyl]carbamate (640 mg, 91%). $^1$H NMR (400 MHz, DMSO-d6) δ 9.80 (s, 1H), 9.10 (s, 1H), 7.44 (d, J=6.7 Hz, 2H), 7.39-7.30 (m, 3H), 5.91-5.72 (m, 2H), 5.10 (dd, J=17.1, 1.8 Hz, 1H), 5.07-4.98 (m, 2H), 4.96 (dd, J=10.2, 2.0 Hz, 1H), 4.74 (d, J=11.0 Hz, 1H), 4.66 (d, J=10.9 Hz, 1H), 3.42 (s, 3H), 3.29 (d, J=7.7 Hz, 2H), 2.90 (s, 3H), 2.48-2.36 (m, 2H), 2.33 (t, J=8.6 Hz, 4H), 1.50 (s, 9H) ppm. ESI-MS m/z calc. 665.2495, found 666.2 (M+1)$^+$; Retention time: 2.22 minutes (LC Method J).

Step 5: tert-Butyl N-[6-benzyloxy-13-methyl-15-methylsulfonyl-6-(trifluoromethyl)-19-oxa-3,4,13,18-tetrazatricyclo[12.3.1.1²,⁵]nonadeca-1(17),2,4,9,14(18),15-hexaen-17-yl]carbamate (E/Z Mixture)

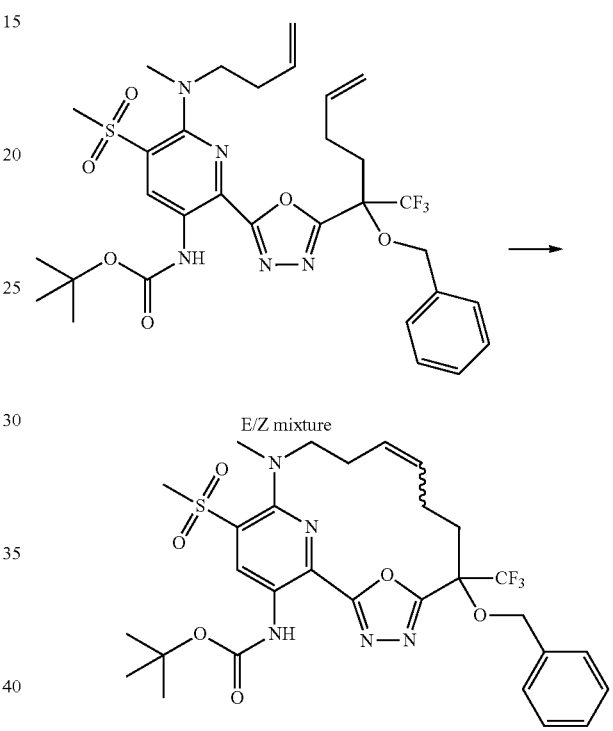

In a 500 mL round-bottom flask, a degassed solution of tert-butyl N-[2-[5-[1-benzyloxy-1-(trifluoromethyl)pent-4-enyl]-1,3,4-oxadiazol-2-yl]-6-[but-3-enyl(methyl)amino]-5-methylsulfonyl-3-pyridyl]carbamate (600 mg, 0.9013 mmol) in DCE (225 mL) was heated at 50° C. under nitrogen atmosphere. Then, Zhan catalyst-1B (212 mg, 0.2889 mmol) was added in two portions over 10 minutes. The resulting mixture was heated at 70° C. for 4 hours. Added more Zhan catalyst-1B (106 mg, 0.144 mmol) and the mixture was heated at 70° C. for 10 more hours. The reaction mixture was cooled to room temperature and concentrated under reduced pressure. The residue was purified by silica gel chromatography (80 gram column) using a gradient from 100% hexanes to 50% ethyl acetate in hexanes to afford as a yellow solid, tert-butyl N-[6-benzyloxy-13-methyl-15-methyl sulfonyl-6-(trifluoromethyl)-19-oxa-3,4,13,18-tetrazatricyclo[12.3.1.1²,⁵]nonadeca-1(17),2,4,9,14(18),15-hexaen-17-yl]carbamate (E/Z mixture) (235 mg, 41%). ESI-MS m/z calc. 637.2182, found 638.2 (M+1)$^+$; Retention time: 2.0 minutes (LC Method J).

Step 6: tert-Butyl N-[6-hydroxy-13-methyl-15-methylsulfonyl-6-(trifluoromethyl)-19-oxa-3,4,13,18-tetrazatricyclo[12.3.1.1²,⁵]nonadeca-1(17),2,4,14(18),15-pentaen-17-yl]carbamate

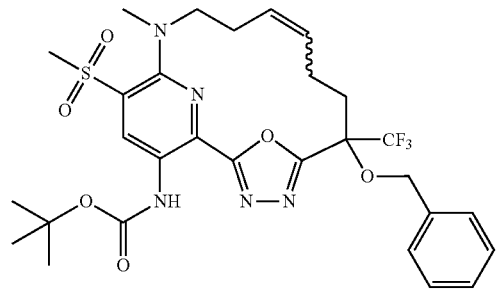

E/Z mixture

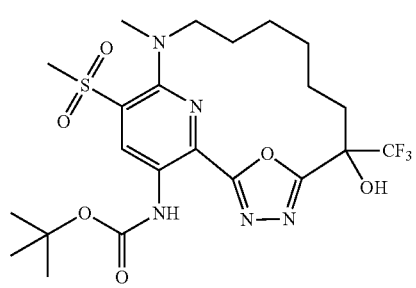

A solution of tert-butyl N-[6-benzyloxy-13-methyl-15-methylsulfonyl-6-(trifluoromethyl)-19-oxa-3,4,13,18-tetrazatricyclo[12.3.1.1²,⁵]nonadeca-1(17),2,4,9,14(18),15-hexaen-17-yl]carbamate (E/Z mixture) (235 mg, 0.3685 mmol) in AcOH (5.0 mL) and ethyl acetate (5 mL) was purged with nitrogen. Then, Pd/C (355 mg of 10% w/w, 0.3336 mmol) was added and the mixture was degassed with nitrogen for 5 minutes, then purged by a balloon filled with hydrogen gas. The mixture was stirred at 1 atm for 5 h then filtered and concentrated. The residue was purified by silica gel chromatography (40 gram column) using a gradient from 100% hexanes to 55% ethyl acetate in hexanes to afford as a yellow solid, tert-butyl N-[6-hydroxy-13-methyl-15-methylsulfonyl-6-(trifluoromethyl)-19-oxa-3,4,13,18-tetrazatricyclo[12.3.1.1²,⁵]nonadeca-1(17),2,4,14(18),15-pentaen-17-yl]carbamate (145 mg, 72%). ¹H NMR (400 MHz, DMSO-d6) δ 9.19 (s, 1H), 8.81 (s, 1H), 7.67 (s, 1H), 3.38 (s, 3H), 3.31-3.24 (m, 1H), 3.17 (s, 3H), 2.15 (d, J=9.2 Hz, 2H), 1.92 (dd, J=11.8, 6.5 Hz, 1H), 1.70 (t, J=6.1 Hz, 1H), 1.59 (s, 2H), 1.48 (s, 9H), 1.40 (s, 1H), 1.29-1.23 (m, 2H), 0.85 (dt, J=10.9, 6.6 Hz, 2H) ppm. ESI-MS m/z calc. 549.1869, found 550.1 (M+1)⁺; Retention time: 1.98 minutes (LC Method A).

Step 7: 17-Amino-13-methyl-15-methylsulfonyl-6-(trifluoromethyl)-19-oxa-3,4,13,18-tetrazatricyclo[12.3.1.1²,⁵]nonadeca-1(18),2,4,14,16-pentaen-6-ol

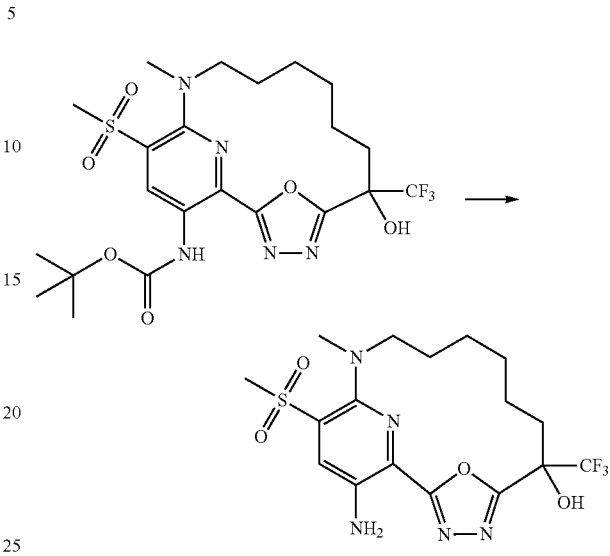

To a solution of tert-butyl N-[6-hydroxy-13-methyl-15-methylsulfonyl-6-(trifluoromethyl)-19-oxa-3,4,13,18-tetrazatricyclo[12.3.1.1²,⁵]nonadeca-1(17),2,4,14(18),15-pentaen-17-yl]carbamate (140 mg, 0.2547 mmol) in DCM (2.5 mL) was added TFA (2.0 mL, 25.96 mmol) and the mixture was stirred at room temperature for 3 hours. The mixture was evaporated to dryness, then diluted with ether and concentrated. The residue was purified by silica gel chromatography (12 gram column) using a gradient from 100% hexanes to 80% ethyl acetate in hexanes to afford as a yellow solid, 17-amino-13-methyl-15-methylsulfonyl-6-(trifluoromethyl)-19-oxa-3,4,13,18-tetrazatricyclo[12.3.1.1²,⁵]nonadeca-1(18),2,4,14,16-pentaen-6-ol (85 mg, 74%). ESI-MS m/z calc. 449.13446, found 450.2 (M+1)⁺; Retention time: 1.62 minutes (LC Method A).

Step 8: 17-Amino-13-methyl-15-methylsulfonyl-6-(trifluoromethyl)-19-oxa-3,4,13,18-tetrazatricyclo[12.3.1.1²,⁵]nonadeca-1(18),2,4,14,16-pentaen-6-ol (enantiomer 1) (Compound 39) and 17-amino-13-methyl-15-methylsulfonyl-6-(trifluoromethyl)-19-oxa-3,4,13,18-tetrazatricyclo[12.3.1.1²,⁵]nonadeca-1(18),2,4,14,16-pentaen-6-ol (enantiomer 2) (Compound 40)

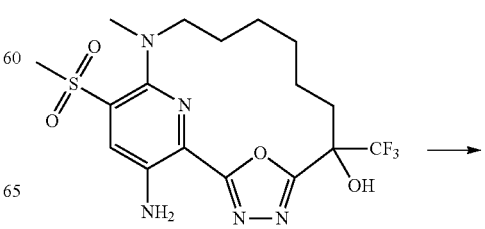

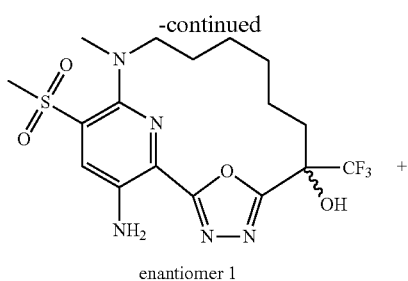

enantiomer 1

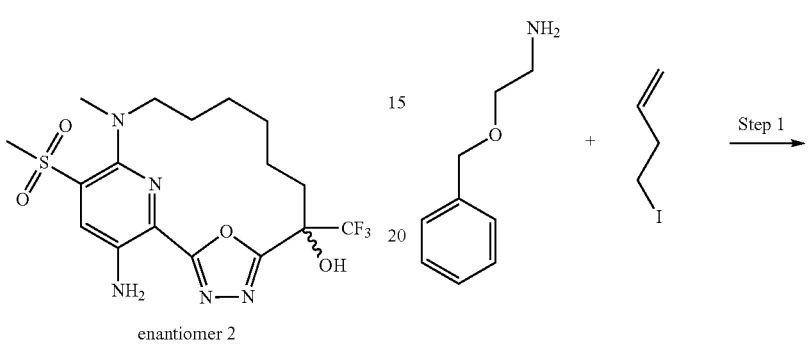

enantiomer 2

Racemic 17-amino-13-methyl-15-methylsulfonyl-6-(trifluoromethyl)-19-oxa-3,4,13,18-tetrazatricyclo[12.3.1.1²,⁵]nonadeca-1(18),2,4,14,16-pentaen-6-ol (90 mg, 0.2002 mmol) was purified by chiral SFC using a LUX-4 column (250×21.2 mm, 5 μm particle size) sold by Phenomenex and eluting with 25% MeOH (+20 mM $NH_3$)/75% $CO_2$ over 6 min which provided two single enantiomer products:

The first enantiomer to elute was further purified by reverse-phase preparative HPLC using a gradient of 1% to 99% acetonitrile in water (+5 mM HCl) over 15 minutes to give as a yellow solid, 17-amino-13-methyl-15-methylsulfonyl-6-(trifluoromethyl)-19-oxa-3,4,13,18-tetrazatricyclo[12.3.1.1²,⁵]nonadeca-1(18),2,4,14,16-pentaen-6-ol (enantiomer 1) (38.8 mg, 85%). $^1$H NMR (400 MHz, DMSO-d6) δ 7.97 (s, 1H), 7.60 (s, 1H), 6.56 (s, 2H), 3.33 (s, 3H), 3.17 (t, J=7.8 Hz, 2H), 2.93 (s, 3H), 2.12 (d, J=7.7 Hz, 2H), 1.94 (tt, J=16.5, 8.5 Hz, 1H), 1.70-1.62 (m, 1H), 1.62-1.55 (m, 2H), 1.55-1.44 (m, 2H), 1.40 (dd, J=15.3, 7.0 Hz, 2H) ppm. ESI-MS m/z calc. 449.13446, found 450.2 (M+1)$^+$; Retention time: 1.61 minutes (LC Method A).

The second enantiomer to elute was further purified by reverse-phase preparative HPLC using a gradient of 1% to 99% acetonitrile in water (+5 mM HCl) over 15 minutes to afford as a yellow solid, 17-amino-13-methyl-15-methylsulfonyl-6-(trifluoromethyl)-19-oxa-3,4,13,18-tetrazatricyclo[12.3.1.1²,⁵]nonadeca-1(18),2,4,14,16-pentaen-6-ol (enantiomer 2) (38.6 mg, 85%). $^1$H NMR (400 MHz, DMSO-d6) δ 7.97 (s, 1H), 7.60 (s, 1H), 6.56 (s, 2H), 3.33 (s, 3H), 3.17 (t, J=7.8 Hz, 2H), 2.93 (s, 3H), 2.12 (d, J=7.5 Hz, 2H), 1.95 (td, J=13.1, 7.4 Hz, 1H), 1.72-1.64 (m, 1H), 1.64-1.56 (m, 2H), 1.56-1.44 (m, 2H), 1.44-1.34 (m, 2H) ppm. ESI-MS m/z calc. 449.13446, found 450.2 (M+1)$^+$; Retention time: 1.61 minutes (LC Method A).

Example 24: Preparation of 17-amino-13-(2-hydroxyethyl)-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (Compound 41) and 17-amino-13-(2-hydroxyethyl)-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (Compound 42)

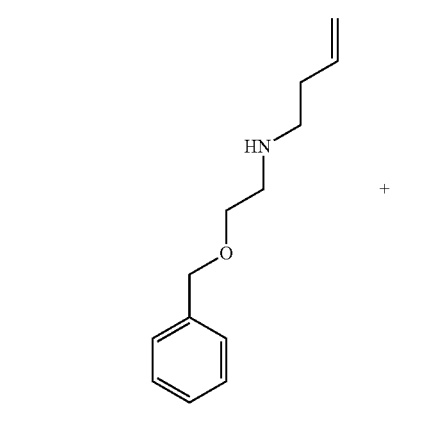

Step 1

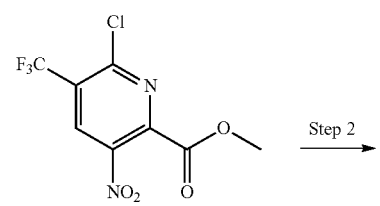

Step 2

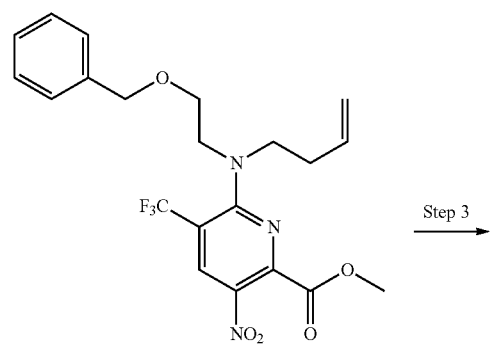

Step 3

365
-continued
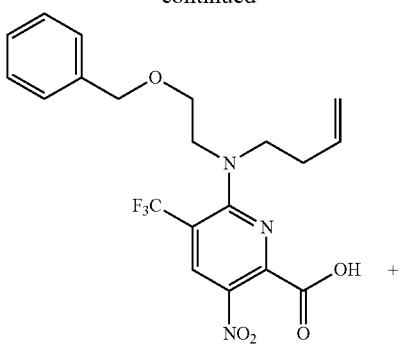
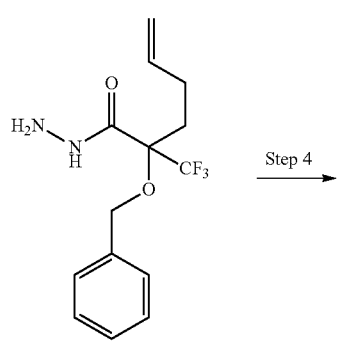
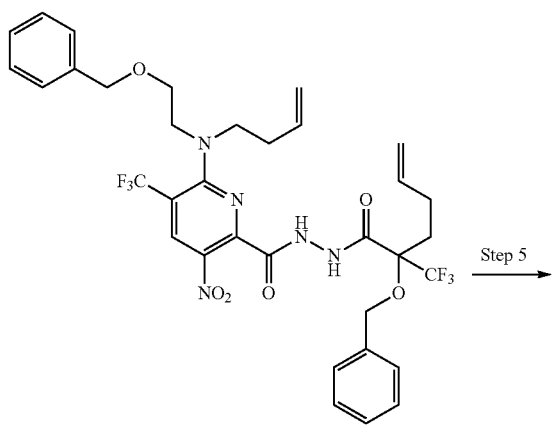
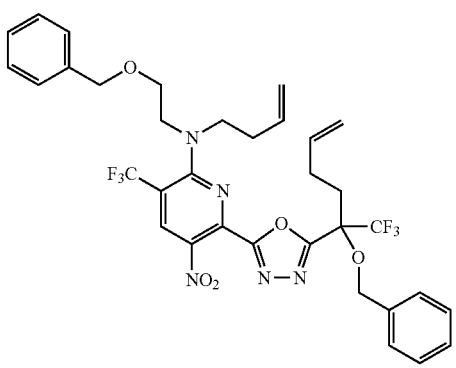
366
-continued
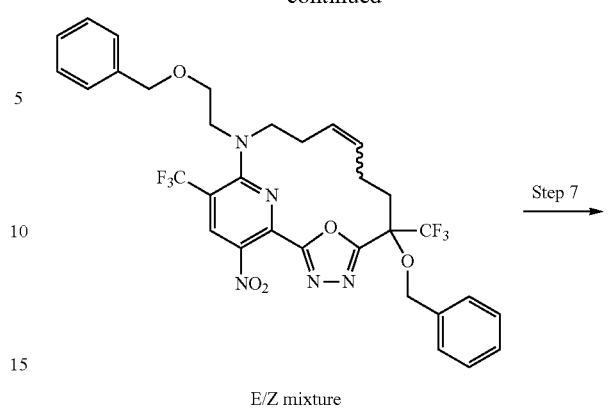
E/Z mixture
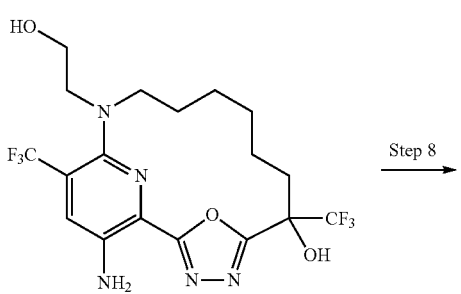
enantiomer 1
enantiomer 2
Step 1: N-(2-Benzyloxyethyl)but-3-en-1-amine
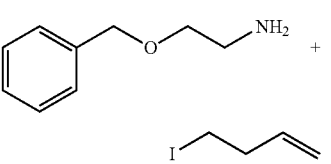

-continued

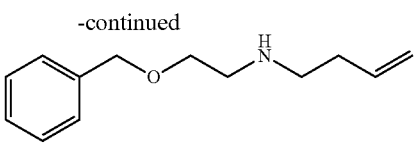

A mixture of 4-iodobut-1-ene (12.5 g, 68.68 mmol), 2-benzyloxyethanamine (12.5 g, 82.67 mmol) and DIEA (42 mL, 241.1 mmol) in acetonitrile (180 mL) was heated at 50° C. in a 500 mL sealed vessel for 90 hours. The mixture was then concentrated to a residue by rotary evaporation using no heat in the water bath and the residue was purified by silica gel chromatography (120 gram column) using a gradient from 100% hexanes to 100% ethyl acetate which afforded as a pale amber oil, N-(2-benzyloxyethyl)but-3-en-1-amine (6.69 g, 47%). $^1$H NMR (400 MHz, DMSO-d6) δ 7.39-7.24 (m, 5H), 5.79 (ddt, J=17.1, 10.2, 6.7 Hz, 1H), 5.04 (dq, J=17.2, 1.7 Hz, 1H), 4.99 (ddt, J=10.2, 2.4, 1.2 Hz, 1H), 4.47 (s, 2H), 3.49 (t, J=5.6 Hz, 2H), 2.74 (d, J=5.6 Hz, 2H), 2.71 (d, J=7.1 Hz, 1H), 2.60 (t, J=7.1 Hz, 2H), 2.17 (qt, J=7.0, 1.4 Hz, 2H) ppm. ESI-MS m/z calc. 205.14667, found 206.2 (M+1)$^+$; Retention time: 0.74 minutes (LC Method A).

Step 2: Methyl 6-[2-benzyloxyethyl(but-3-enyl) amino]-3-nitro-5-(trifluoromethyl)pyridine-2-carboxylate

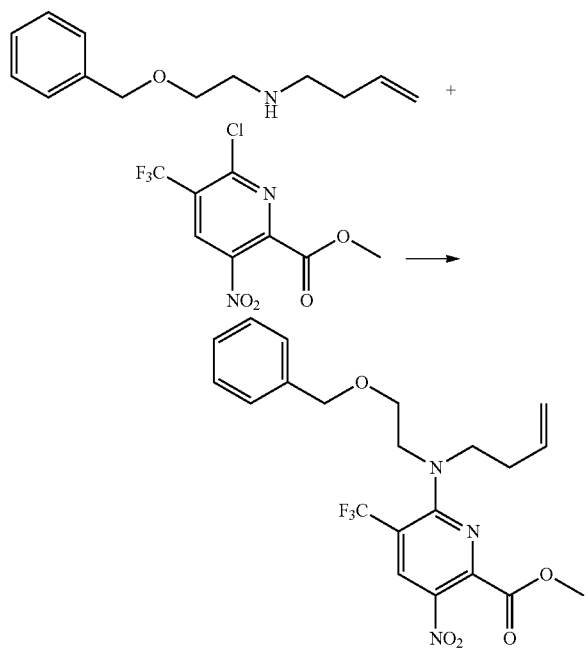

To a solution of N-(2-benzyloxyethyl)but-3-en-1-amine (3.1 g, 15.10 mmol) and methyl 6-chloro-3-nitro-5-(trifluoromethyl)pyridine-2-carboxylate (2.11 g, 7.415 mmol) in acetonitrile (41.0 mL) was added DIEA (6.5 mL, 37.32 mmol) and the mixture was stirred for 16 hours at room temperature. The reaction mixture was concentrated under reduced pressure and the residue was purified twice by silica gel chromatography (120 gram column) using a gradient from 100% hexanes to 30% ethyl acetate in hexanes in both columns to afford as a yellow residue, methyl 6-[2-benzyloxyethyl(but-3-enyl)amino]-3-nitro-5-(trifluoromethyl) pyridine-2-carboxylate (3.23 g, 96%). $^1$H NMR (400 MHz, DMSO-d6) δ 8.60 (s, 1H), 7.32-7.19 (m, 3H), 7.19-7.11 (m, 2H), 5.72 (ddt, J=17.1, 10.2, 6.8 Hz, 1H), 5.08-4.96 (m, 2H), 4.42 (s, 2H), 3.93 (s, 3H), 3.84 (t, J=5.2 Hz, 2H), 3.72 (t, J=7.1 Hz, 2H), 3.66 (t, J=5.2 Hz, 2H), 2.37 (q, J=7.1 Hz, 2H) ppm. ESI-MS m/z calc. 453.15115, found 454.2 (M+1)±; Retention time: 2.15 minutes (LC Method A).

Step 3: 6-[12-Benzyloxyethyl(but-3-enyl)amino]-3-nitro-5-(trifluoromethyl)pyridine-2-carboxylic Acid

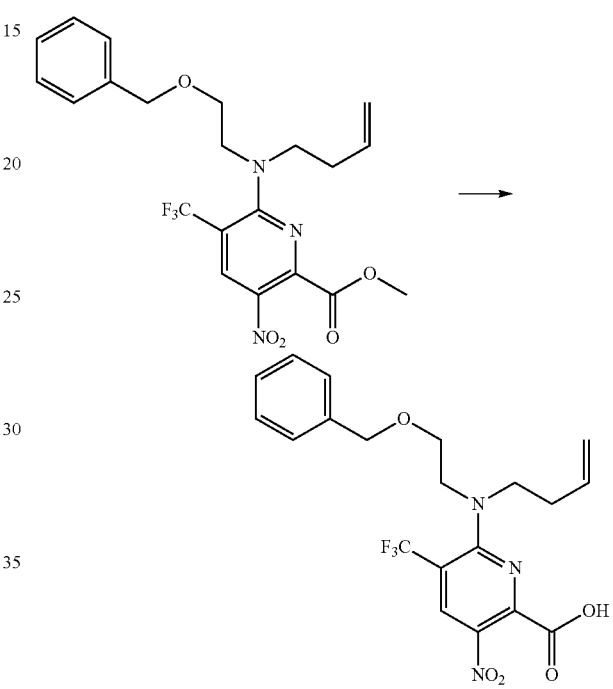

To a solution of methyl 6-[2-benzyloxyethyl(but-3-enyl) amino]-3-nitro-5-(trifluoromethyl)pyridine-2-carboxylate (3.23 g, 7.124 mmol) in THF (38 mL) was added MeOH (38 mL) and water (30 mL) followed by lithium hydroxide (737.8 mg, 30.81 mmol). The mixture was stirred with heating at 60° C. for 2 h. THF and methanol were removed under reduced pressure and 10 mL of 10% aqueous HCl was added to acidify to pH ~4 and the mixture was extracted with EtOAc (2×50 mL). The organic phases were combined, washed with brine (5 mL), dried over anhydrous sodium sulfate, filtered and concentrated under reduced pressure. The residue was purified by silica gel chromatography (120 gram column) using a gradient from 100% hexanes to 80% ethyl acetate in hexanes to afford as a yellow solid, 6-[2-benzyloxyethyl(but-3-enyl)amino]-3-nitro-5-(trifluoromethyl)pyridine-2-carboxylic acid (2.71 g, 87%). $^1$H NMR (400 MHz, DMSO-d6) δ 14.27 (s, 1H), 8.58 (s, 1H), 7.28 (dd, J=8.0, 6.1 Hz, 2H), 7.25-7.19 (m, 1H), 7.19-7.13 (m, 2H), 5.72 (ddt, J=17.1, 10.2, 6.7 Hz, 1H), 5.15-4.96 (m, 2H), 4.42 (s, 2H), 3.83 (t, J=5.2 Hz, 2H), 3.71 (t, J=7.2 Hz, 2H), 3.66 (t, J=5.2 Hz, 2H), 2.37 (q, J=7.1 Hz, 2H) ppm. ESI-MS m/z calc. 439.1355, found 440.2 (M+1)$^+$; Retention time: 1.88 minutes (LC Method A).

Step 4: 6-[12-Benzyloxyethyl(but-3-enyl)amino]-N'-[2-benzyloxy-2-(trifluoromethyl)hex-5-enoyl]-3-nitro-5-(trifluoromethyl)pyridine-2-carbohydrazide

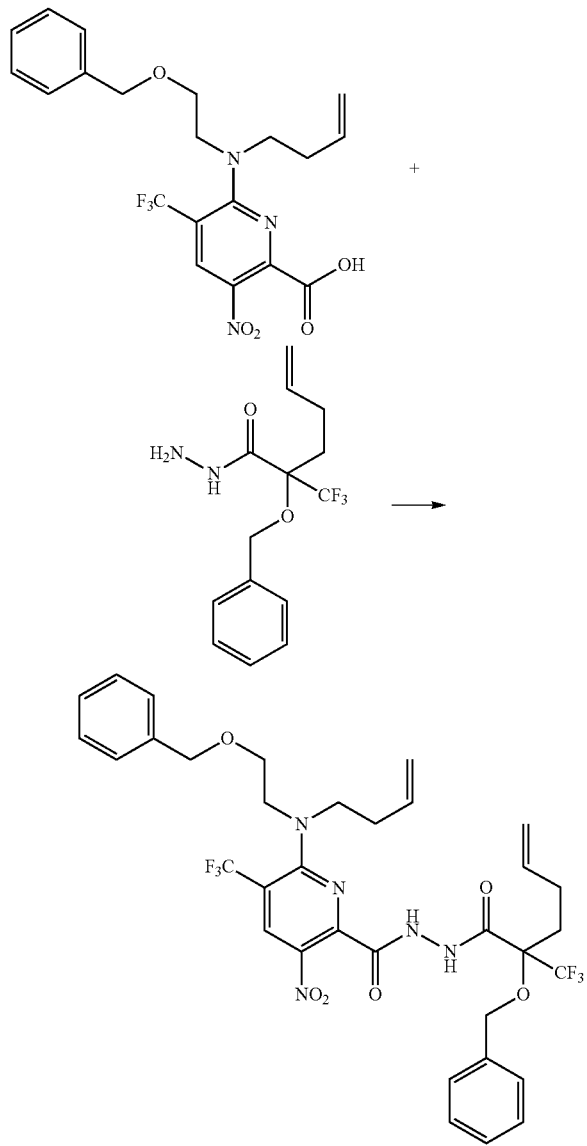

To a solution of 6-[2-benzyloxyethyl(but-3-enyl)amino]-3-nitro-5-(trifluoromethyl)pyridine-2-carboxylic acid (1.6 g, 3.641 mmol) in NMP (28 mL) was added 2-benzyloxy-2-(trifluoromethyl)hex-5-enehydrazide (1.98 g, 6.550 mmol) and DIEA (3 mL, 17.22 mmol) followed by HATU (2.9 g, 7.627 mmol). The reaction mixture was stirred at room temperature for 18 h. The reaction was diluted with ethyl acetate and washed with a saturated aqueous sodium bicarbonate solution. The organic layer was further washed with 10% citric acid solution followed by brine. The organics were separated, dried over sodium sulfate, filtered and evaporated. The residue was purified by silica gel chromatography (120 gram column) using a gradient from 100% hexanes to 60% ethyl acetate in hexanes to afford as a yellow solid, 6-[2-benzyloxyethyl(but-3-enyl)amino]-N'-[2-benzyloxy-2-(trifluoromethyl)hex-5-enoyl]-3-nitro-5-(trifluoromethyl)pyridine-2-carbohydrazide (1.0 g, 38%). ESI-MS m/z calc. 723.24915, found 724.2 (M+1)+; Retention time: 1.93 minutes (LC Method J).

Step 5: N-(2-Benzyloxyethyl)-6-[5-[1-benzyloxy-1-(trifluoromethyl)pent-4-enyl]-1,3,4-oxadiazol-2-yl]-N-but-3-enyl-5-nitro-3-(trifluoromethyl)pyridin-2-amine

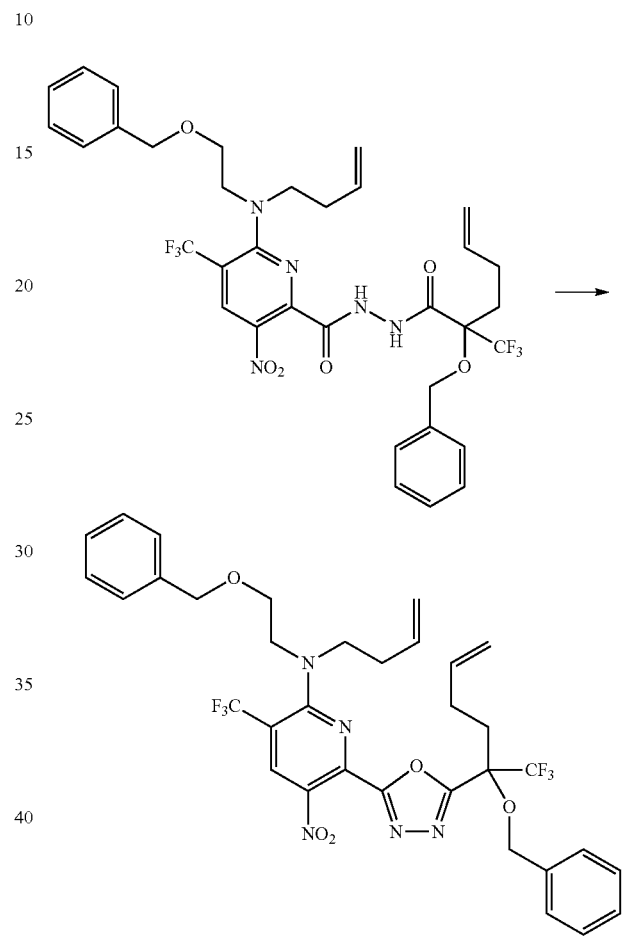

A solution of 6-[2-benzyloxyethyl(but-3-enyl)amino]-N'-[2-benzyloxy-2-(trifluoromethyl)hex-5-enoyl]-3-nitro-5-(trifluoromethyl)pyridine-2-carbohydrazide (833 mg, 1.151 mmol) and DIEA (1000 μL, 5.741 mmol) in acetonitrile (25 mL) was heated to 50° C., then p-toluenesulfonyl chloride (350 mg, 1.836 mmol) was added in one portion. The resulting mixture was heated at 70° C. for 2 hours. The reaction mixture was cooled and quenched with saturated aqueous solution of sodium bicarbonate (50 mL) and stirred for 15 minutes. The mixture was extracted with ethyl acetate (3×50 mL). The combined organic layers were dried over sodium sulfate, filtered and evaporated. The residue was purified by silica gel chromatography (80 gram column) using a gradient from 100% hexanes to 50% ethyl acetate in hexanes to afford as a yellow oil, N-(2-benzyloxyethyl)-6-[5[1-benzyloxy-1-(trifluoromethyl)pent-4-enyl]-1,3,4-oxadiazol-2-yl]-N-but-3-enyl-5-nitro-3-(trifluoromethyl)pyridin-2-amine (650 mg, 80%). $^1$H NMR (400 MHz, DMSO-d6) δ 8.73 (s, 1H), 7.40-7.27 (m, 5H), 7.27-7.16 (m, 3H), 7.17-7.09 (m, 2H), 5.84 (ddt, J=16.8, 10.2, 6.5 Hz, 1H), 5.71 (ddt, J=17.1, 10.2, 6.8 Hz, 1H), 5.10 (dq, J=17.2, 1.6 Hz, 1H), 5.05-4.94 (m, 3H), 4.76 (d, J=10.9 Hz, 1H), 4.61 (d, J=10.8 Hz, 1H), 4.40 (s, 2H), 3.85 (t, J 5.2 Hz, 2H), 3.76-3.61 (m, 4H), 2.60-2.51 (m, 2H), 2.38 (q, J=7.2 Hz, 2H), 2.31-2.18 (m, 2H) ppm. ESI-MS m/z calc. 705.2386, found 706.2 (M+1)+; Retention time: 1.79 minutes (LC Method M).

Step 6: 6-Benzyloxy-13-(2-benzyloxyethyl)-17-nitro-6,15-bis(trifluoromethyl)-19-oxa-3,4,13,18-tetrazatricyclo[12.3.1.12,5]nonadeca-1(18),2,4,9,14,16-hexaene (E/Z mixture)

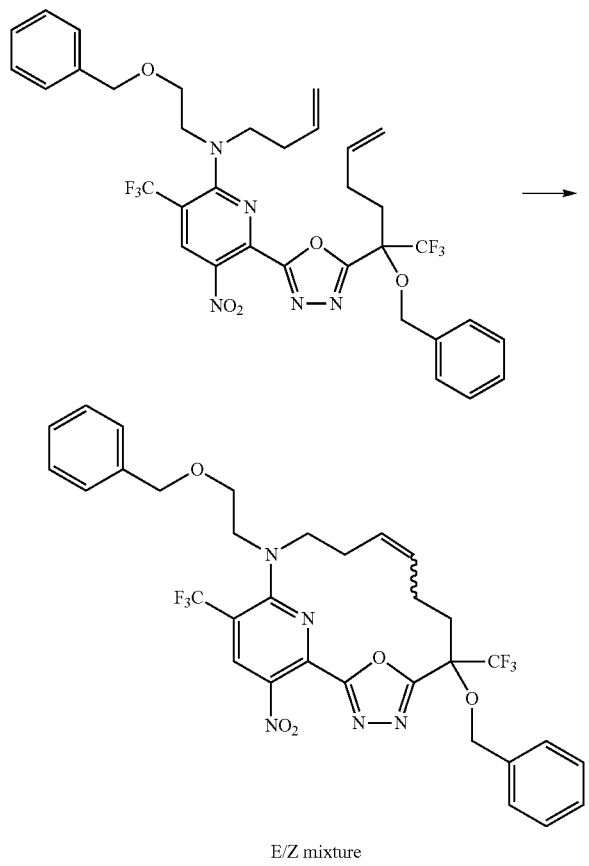

E/Z mixture

In a 500 mL round-bottom 3-neck flask, a continuously degassed solution via nitrogen line of Zhan catalyst-1B (165 mg, 0.2249 mmol) in DCE (290 mL) was heated at 50° C. and a solution of N-(2-benzyloxyethyl)-6-[5-[1-benzyloxy-1-(trifluoromethyl)pent-4-enyl]-1,3,4-oxadiazol-2-yl]-N-but-3-enyl-5-nitro-3-(trifluoromethyl)pyridin-2-amine (640 mg, 0.9070 mmol) in DCE (40 mL) was added dropwise by syringe. The resulting mixture was heated at 75° C. for 2 hours. The reaction mixture was cooled to room temperature and concentrated under reduced pressure. The residue was purified by silica gel chromatography (80 gram column) using a gradient from 100% hexanes to 50% ethyl acetate in hexanes to afford as a yellow solid, 6-benzyloxy-13-(2-benzyloxyethyl)-17-nitro-6,15-bis(trifluoromethyl)-19-oxa-3,4,13,18-tetrazatricyclo[12.3.1.12,5]nonadeca-1(18),2,4,9,14,16-hexaene (E/Z mixture) (360 mg, 59%). ESI-MS m/z calc. 677.2073, found 678.2 (M+1)+; Retention time: 1.53 minutes (LC Method M).

Step 7: 17-Amino-13-(2-hydroxyethyl)-6,15-bis(trifluoromethyl)-19-oxa-3,4,13,18-tetrazatricyclo[12.3.1.12,5]nonadeca-1(18),2,4,14,16-pentaen-6-ol

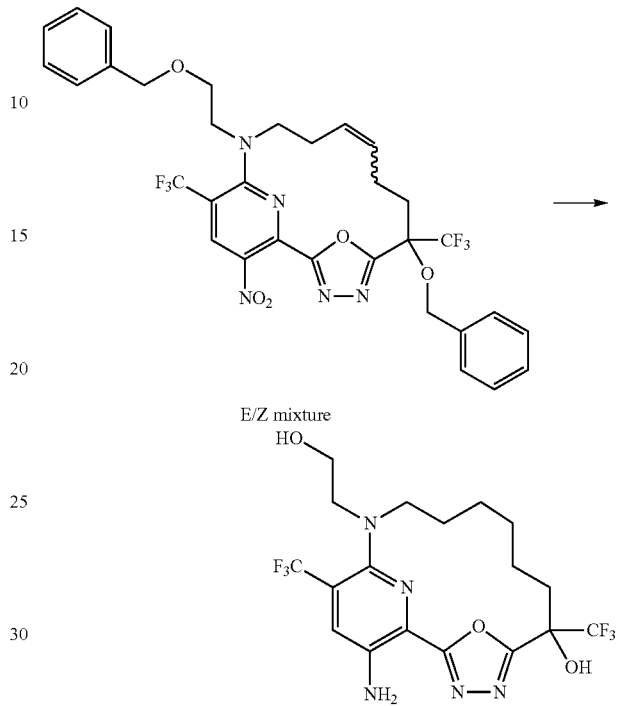

A solution of 6-benzyloxy-13-(2-benzyloxyethyl)-17-nitro-6,15-bis(trifluoromethyl)-19-oxa-3,4,13,18-tetrazatricyclo[12.3.1.12,5]nonadeca-1(18),2,4,9,14,16-hexaene (E/Z mixture) (355 mg, 0.5239 mmol) in AcOH (5.5 mL) and ethyl acetate (5.5 mL) was purged with nitrogen and Pd/C (85 mg of 10% w/w, 0.07987 mmol) was added. The mixture was degassed with nitrogen for 5 minutes, then purged by a balloon filled with hydrogen gas. The mixture was stirred at 1 atm for 1 h. Added more Pd/C (475 mg of 10% w/w, 0.4453 mmol) and stirred for 3 more hours. The reaction was filtered over a Celite plug and washed with acetonitrile and ethyl acetate and then concentrated the filtrate. The residue was purified by silica gel chromatography (40 gram column) using a gradient from 100% hexanes to 100% ethyl acetate to afford as a yellow solid, 17-amino-13-(2-hydroxyethyl)-6,15-bis(trifluoromethyl)-19-oxa-3,4,13,18-tetrazatricyclo[12.3.1.12,5]nonadeca-1(18),2,4,14,16-pentaen-6-ol (166 mg, 68%). 1H NMR (400 MHz, DMSO-d6) δ 7.70 (s, 1H), 7.56 (d, J=48.2 Hz, 1H), 4.11 (d, J=13.4 Hz, 2H), 3.58 (t, J=6.8 Hz, 2H), 3.54-3.31 (m, 1H), 3.26 (t, J=7.8 Hz, 2H), 3.17 (dq, J=14.3, 6.8 Hz, 2H), 2.14 (t, J=7.2 Hz, 2H), 1.94-1.85 (m, 1H), 1.70-1.50 (m, 4H), 1.50-1.34 (m, 3H) ppm. ESI-MS m/z calc. 469.15485, found 470.1 (M+1)+; Retention time: 1.58 minutes (LC Method A).

Step 8: 17-Amino-13-(2-hydroxyethyl)-6,15-bis(trifluoromethyl)-19-oxa-3,4,13,18-tetrazatricyclo[12.3.1.12,5]nonadeca-1(18),2,4,14,16-pentaen-6-ol (enantiomer 1) (Compound 41) and 17-amino-13-(2-hydroxyethyl)-6,15-bis(trifluoromethyl)-19-oxa-3,4,13,18-tetrazatricyclo[12.3.1.12,5]nonadeca-1(18),2,4,14,16-pentaen-6-ol (enantiomer 2) (Compound 42)

Step 9: Solid Form Characterization of Crystalline Compound 41 Form A

A. X-Ray Powder Diffraction

The XRPD diffractogram for crystalline Compound 41 Form A produced by Step 8 was acquired using the General X-Ray Powder Diffraction (XRPD) Method. The XRPD

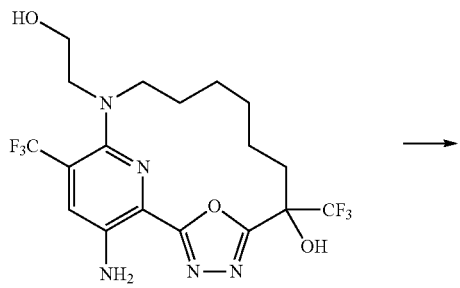

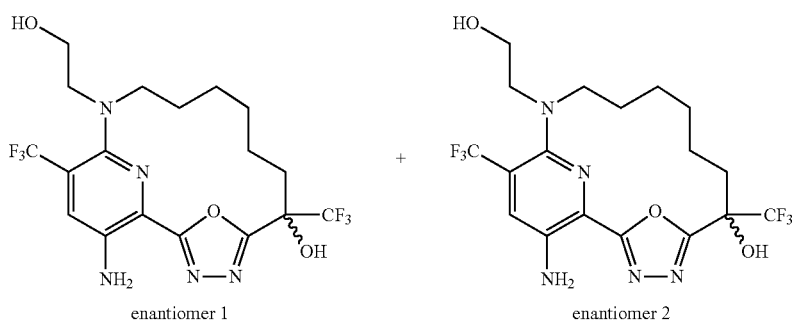

enantiomer 1      enantiomer 2

Racemic 17-amino-13-(2-hydroxyethyl)-6,15-bis(trifluoromethyl)-19-oxa-3,4,13,18-tetrazatricyclo[12.3.1.12,5]nonadeca-1(18),2,4,14,16-pentaen-6-ol (165 mg, 0.3515 mmol) was purified by chiral SFC using a LUX-4 column (250×21.2 mm, 5 μm particle size) sold by Phenomenex and eluting with 18% MeOH (+20 mM $NH_3$)/82% $CO_2$ which provided two single enantiomer products"

The first enantiomer to elute was further purified by reverse-phase preparative HPLC using a gradient of 1% to 99% acetonitrile in water (+5 mM HCl) over 15 minutes to afford as a yellow solid, 17-amino-13-(2-hydroxyethyl)-6,15-bis(trifluoromethyl)-19-oxa-3,4,13,18-tetrazatricyclo[12.3.1.12,5]nonadeca-1(18),2,4,14,16-pentaen-6-ol (enantiomer 1) (53.7 mg, 64%). $^1$H NMR (400 MHz, DMSO-d6) δ 7.70 (s, 1H), 7.57 (s, 1H), 6.29 (s, 2H), 3.58 (t, J=6.7 Hz, 3H), 3.31-3.13 (m, 4H), 2.14 (t, J=7.6 Hz, 2H), 1.90 (h, J=6.9, 4.2 Hz, 1H), 1.72-1.51 (m, 4H), 1.51-1.34 (m, 3H) ppm. ESI-MS m/z calc. 469.15485, found 470.2 (M+1)$^+$; Retention time: 1.58 minutes (LC Method A).

The second enantiomer to elute was further purified by reverse-phase preparative HPLC using a gradient of 1% to 99% acetonitrile in water (+5 mM HCl) over 15 minutes to afford as a yellow solid, 17-amino-13-(2-hydroxyethyl)-6,15-bis(trifluoromethyl)-19-oxa-3,4,13,18-tetrazatricyclo[12.3.1.12,5]nonadeca-1(18),2,4,14,16-pentaen-6-ol (enantiomer 2) (51.4 mg, 62%). $^1$H NMR (400 MHz, DMSO-d6) δ 7.70 (s, 1H), 7.57 (s, 1H), 6.33 (s, 2H), 3.58 (t, J=6.7 Hz, 3H), 3.29-3.14 (m, 4H), 2.13 (d, J=7.4 Hz, 2H), 1.95-1.84 (m, 1H), 1.69-1.49 (m, 4H), 1.48-1.27 (m, 3H) ppm. ESI-MS m/z calc. 469.15485, found 470.2 (M+1)$^+$; Retention time: 1.58 minutes (LC Method A).

diffractogram for crystalline Compound 41 Form A is provided in FIG. 7, and the XRPD data are summarized below in Table 4.

TABLE 4

XRPD signals for crystalline Compound 41 Form A

| XRPD Peak No. | Angle (degrees 2-Theta ± 0.2) | Intensity % |
| --- | --- | --- |
| 1 | 14.1607 | 100 |
| 2 | 16.5689 | 27.78 |
| 3 | 18.0078 | 52.19 |
| 4 | 19.5231 | 79.81 |
| 5 | 20.2639 | 25.32 |
| 6 | 20.6598 | 26.89 |
| 7 | 21.2483 | 67.04 |
| 8 | 22.1718 | 16.32 |
| 9 | 25.1431 | 10.6 |

B. Thermogravimetric Analysis (TGA)

Figure 8:
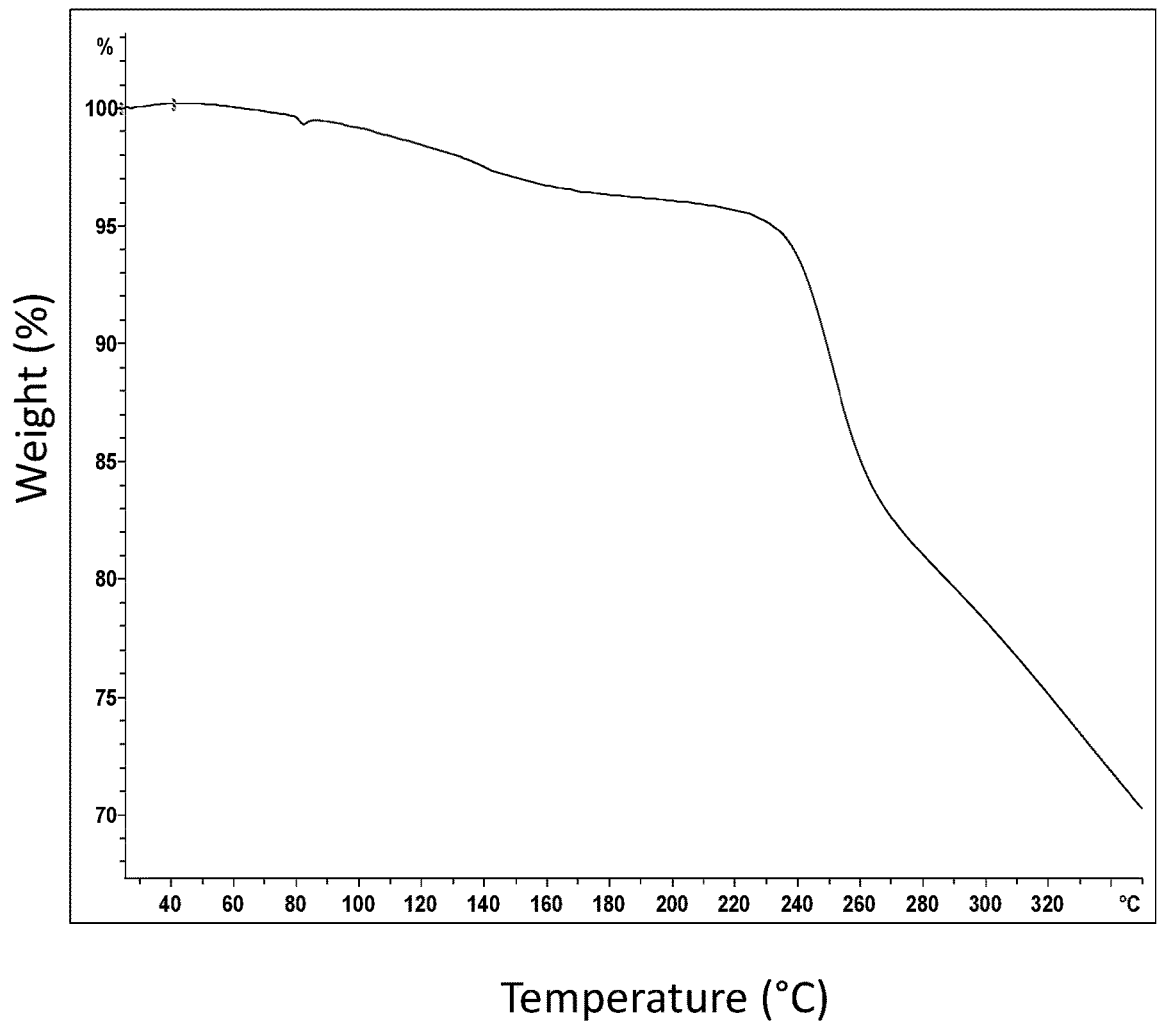
FIG. 8 provides a TGA curve for crystalline Compound 41 Form A.

The TGA curve for crystalline Compound 41 Form A is provided in FIG. 8. The TGA curve shows 3.89% weight loss from ~30-181.8° C., with a ramp of 10.00° C./min to 350.00° C.

Example 25: Preparation of 17-amino-6-hydroxy-10,13-dimethyl-6,15-bis(trifluoromethyl)-19-oxa-3,4,10,13,18-pentazatricyclo[12.3.1.1²,⁵]nonadeca-1(18),2,4,14,16-pentaen-9-one (enantiomer 1) (hydrochloride salt) (Compound 43) and 17-amino-6-hydroxy-10,13-dimethyl-6,15-bis(trifluoromethyl)-19-oxa-3,4,10,13,18-pentazatricyclo[12.3.1.1²,⁵]nonadeca-1(18),2,4,14,16-pentaen-9-one (enantiomer 2) (hydrochloride salt) (Compound 44)
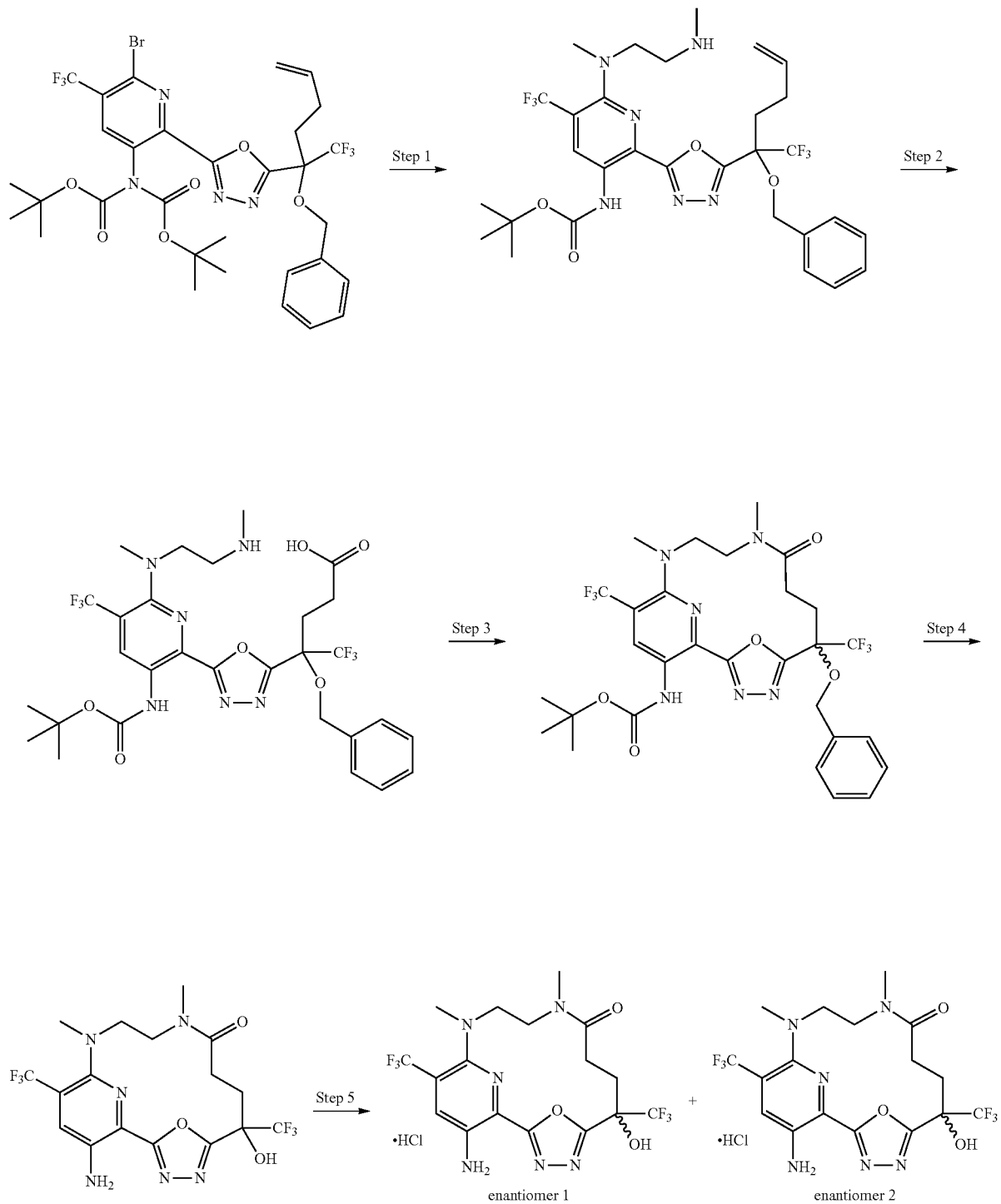

Step 1: tert-Butyl N-[2-[5-[1-benzyloxy-1-(trifluoromethyl)pent-4-enyl]-1,3,4-oxadiazol-2-yl]-6-[methyl-[2-(methylamino)ethyl]amino]-5-(trifluoromethyl)-3-pyridyl]carbamate Step 2: 4-Benzyloxy-4-[5-[3-(tert-butoxycarbonylamino)-6-[methyl-[2-(methylamino)ethyl]amino]-5-(trifluoromethyl)-2-pyridyl]-1,3,4-oxadiazol-2-yl]-5,5,5-trifluoro-pentanoic Acid

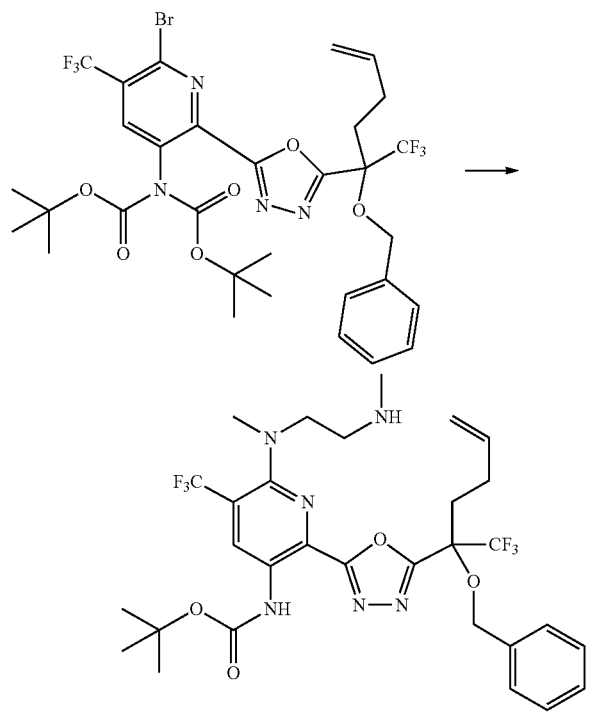

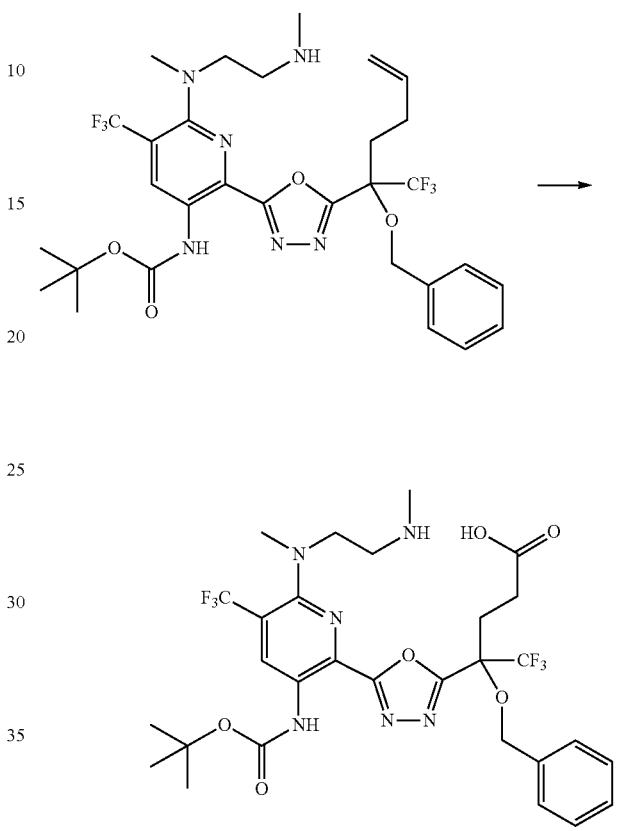

To a solution of tert-butyl N-[2-[5-[1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate (250 mg, 0.3327 mmol) in DMSO (2 mL) was added N,N'-dimethylethane-1,2-diamine (360 µL, 3.381 mmol) and the reaction mixture was stirred at 100° C. for 2 h. Then, cooled the reaction to room temperature and purified on a reverse phase $C_{18}$ column using a dual gradient run from 10% to 99% mobile phase B over 15.0 minutes (mobile phase A=$H_2O$ (5 mM HCl), mobile phase B=$CH_3CN$) to afford tert-butyl N-[2-[5-[1-benzyloxy-1-(trifluoromethyl)pent-4-enyl]-1,3,4-oxadiazol-2-yl]-6-[methyl-[2-(methylamino)ethyl]amino]-5-(trifluoromethyl)-3-pyridyl]carbamate (174 mg, 79%). $^1$H NMR (400 MHz, DMSO-d6) δ 9.67 (s, 1H), 8.90 (s, 1H), 8.75 (s, 1H), 7.44-7.32 (m, 5H), 5.87 (ddt, J=16.9, 10.2, 6.5 Hz, 1H), 5.11 (dq, J=17.1, 1.6 Hz, 1H), 5.01 (dd, J=10.3, 1.7 Hz, 1H), 4.77 (d, J=11.2 Hz, 1H), 4.66 (d, J=11.0 Hz, 1H), 3.59 (t, J=6.9 Hz, 2H), 3.52 (t, J=7.0 Hz, 2H), 3.14 (t, J 6.2 Hz, 2H), 2.96 (s, 3H), 2.50 (d, J 2.0 Hz, 3H), 2.31 (dq, J 11.0, 5.8 Hz, 2H), 1.47 (s, 9H) ppm. ESI-MS m/z calc. 658.2702, found 659.5 (M+1)$^+$; Retention time: 0.54 minutes (LC Method R).

To a solution of tert-butyl N-[2-[5-[1-benzyloxy-1-(trifluoromethyl)pent-4-enyl]-1,3,4-oxadiazol-2-yl]-6-[methyl-[2-(methylamino)ethyl]amino]-5-(trifluoromethyl)-3-pyridyl]carbamate (100 mg, 0.1518 mmol) in 3:1 mixture of dioxane (3 mL) and water (1 mL) was added a solution of osmium tetroxide (50 µL of 2.5% in 2-methyl-2-propanol, 0.03737 mmol) and sodium periodate (106 mg, 0.4956 mmol) at 0° C. The reaction was stirred at 25° C. overnight. Water (25 mL) was added and extracted with ethyl acetate. The organic layer was washed with brine, dried over $Na_2SO_4$, filtered and concentrated. The resultant brown residue was purified by silica gel column chromatography using a shallow gradient from 100% hexanes to 100% EtOAc to afford 4-benzyloxy-4-[5-[3-(tert-butoxycarbonylamino)-6-[methyl-[2-(methylamino)ethyl]amino]-5-(trifluoromethyl)-2-pyridyl]-1,3,4-oxadiazol-2-yl]-5,5,5-trifluoro-pentanoic acid (62 mg, 60%). ESI-MS m/z calc. 676.2444, found 677.3 (M+1)$^+$; Retention time: 0.44 minutes (LC Method R).

379

Step 3: tert-Butyl N-[6-benzyloxy-10,13-dimethyl-9-oxo-6,15-bis(trifluoromethyl)-19-oxa-3,4,10,13,18-pentazatricyclo[12.3.1.1²,⁵]nonadeca-1(17),2,4,14(18),15-pentaen-17-yl]carbamate

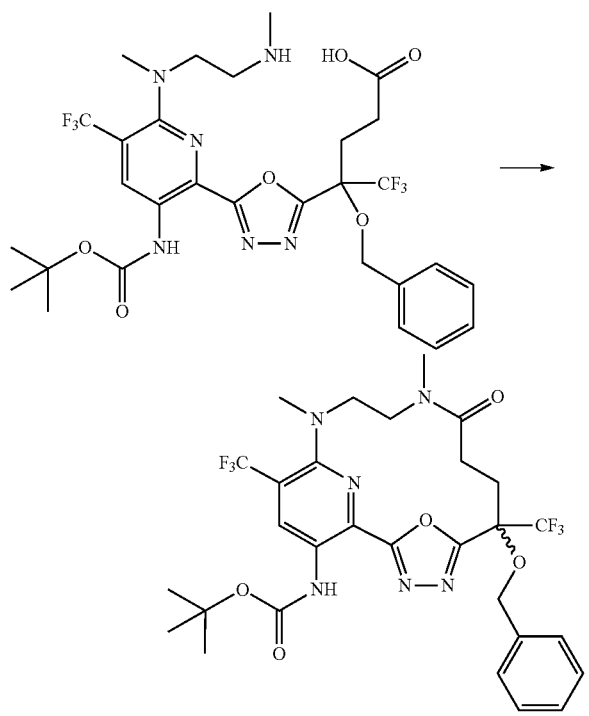

To a solution of 4-benzyloxy-4-[5-[3-(tert-butoxycarbonylamino)-6-[methyl-[2-(methylamino)ethyl]amino]-5-(trifluoromethyl)-2-pyridyl]-1,3,4-oxadiazol-2-yl]-5,5,5-trifluoro-pentanoic acid (62 mg, 0.09163 mmol) in DMF (10 mL) was added DIEA (60 µL, 0.3445 mmol) followed by HATU (65 mg, 0.1709 mmol). The reaction mixture was stirred at room temperature and after 3 h, all starting material disappeared. The mixture was diluted with water and extracted with ethyl acetate (3×). The organic phases were combined and dried over MgSO₄, filtered, and concentrated in vacuo. The resultant brown residue was purified by a reverse phase HPLC-MS method using a dual gradient run from 30% to 99% mobile phase B over 15.0 minutes (mobile phase A=H₂O (5 mM HCl), mobile phase B=CH₃CN) to afford as a brown oil, tert-butyl N-[6-benzyloxy-10,13-dimethyl-9-oxo-6,15-bis(trifluoromethyl)-19-oxa-3,4,10,13,18-pentazatricyclo[12.3.1.1²,⁵]nonadeca-1(17),2,4,14(18),15-pentaen-17-yl]carbamate (42 mg, 70%). ¹H NMR (400 MHz, DMSO-d6) δ 8.89 (s, 1H), 8.51 (d, J=16.1 Hz, 1H), 7.42-7.27 (m, 5H), 4.73 (d, J=11.2 Hz, 1H), 4.57-4.53 (m, 1H), 4.14 (s, 1H), 4.02 (d, J=13.9 Hz, 1H), 3.81 (s, 1H), 3.69 (s, 1H), 3.14 (d, J 2.2 Hz, 2H), 3.03 (d, J=40.3 Hz, 3H), 2.92-2.78 (m, 2H), 2.69-2.58 (m, 3H), 1.51-1.39 (m, 9H)

380 ppm. ESI-MS m/z calc. 658.2338, found 659.2 (M+1)⁺; Retention time: 0.74 minutes (LC Method R).

Step 4: 17-Amino-6-hydroxy-10,13-dimethyl-6,15-bis(trifluoromethyl)-19-oxa-3,4,10,13,18-pentazatricyclo[12.3.1.1²,⁵]nonadeca-1(18),2,4,14,16-pentaen-9-one

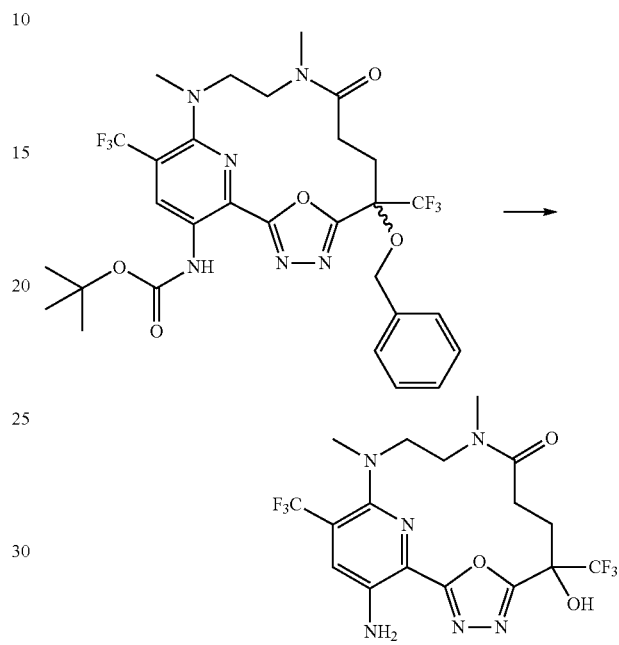

To a solution of tert-butyl N-[6-benzyloxy-10,13-dimethyl-9-oxo-6,15-bis(trifluoromethyl)-19-oxa-3,4,10,13,18-pentazatricyclo[12.3.1.1²,⁵]nonadeca-1(17),2,4,14(18),15-pentaen-17-yl]carbamate (40 mg, 0.06074 mmol) in EtOH (5 mL) was added Pd/C (35 mg of 10% w/w, 0.03289 mmol) and equipped with a 3 way stopcock and a hydrogen balloon. Subjected the reaction mixture to vacuum and backfilled with nitrogen gas three times then subjected to vacuum. Filled the flask with hydrogen gas from a balloon and stirred the mixture for 15 h. Subjected the mixture to vacuum and backfilled with nitrogen gas three times then diluted with ethyl acetate and filtered over Celite. The filtrate was concentrated and dried under vacuum to afford as brown oil, 30 mg of tert-butyl N-[6-hydroxy-10,13-dimethyl-9-oxo-6,15-bis(trifluoromethyl)-19-oxa-3,4,10,13,18-pentazatricyclo[12.3.1.1²,⁵]nonadeca-1(17),2,4,14(18),15-pentaen-17-yl]carbamate. This material was dissolved in a 1:4 mixture of a premade solution of TFA (100 µL, 1.298 mmol) and dichloromethane (400 µL) and stirred for 1 h at room temperature. The solvents were removed and dried under vacuum to afford as a brown oil, 17-amino-6-hydroxy-10,13-dimethyl-6,15-bis(trifluoromethyl)-19-oxa-3,4,10,13,18-pentazatricyclo[12.3.1.1²,⁵]nonadeca-1(18),2,4,14,16-pentaen-9-one (25 mg, 88%). ESI-MS m/z calc. 468.13446, found 469.0 (M+1)⁺; Retention time: 0.58 minutes (LC Method S).

Step 5: 17-Amino-6-hydroxy-10,13-dimethyl-6,15-bis(trifluoromethyl)-19-oxa-3,4,10,13,18-pentazatricyclo[12.3.1.12,5]nonadeca-1(18),2,4,14,16-pentaen-9-one (enantiomer 1) (hydrochloride salt) (Compound 43) and 17-amino-6-hydroxy-10,13-dimethyl-6,15-bis(trifluoromethyl)-19-oxa-3,4,10,13,18-pentazatricyclo[12.3.1.12,5]nonadeca-1(18),2,4,14,16-pentaen-9-one (enantiomer 2) (hydrochloride salt) (Compound 44)

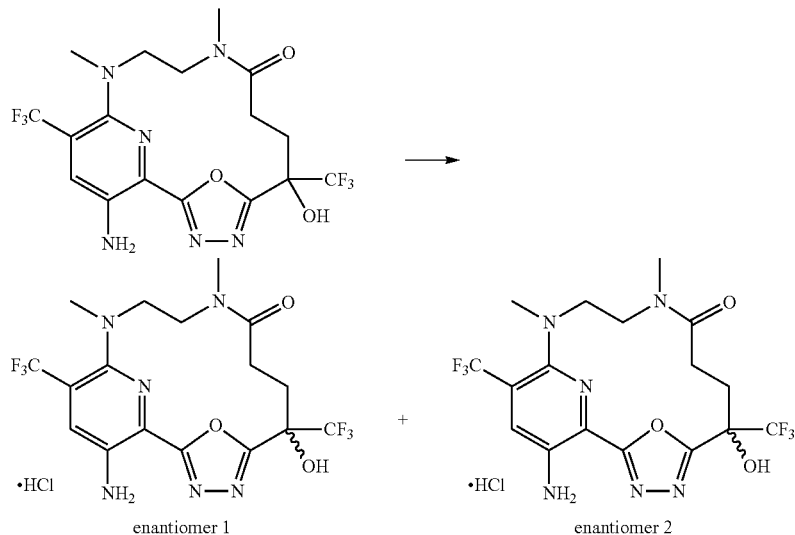

enantiomer 1      enantiomer 2

A racemic mixture of 17-amino-6-hydroxy-10,13-dimethyl-6,15-bis(trifluoromethyl)-19-oxa-3,4,10,13,18-pentazatricyclo[12.3.1.12,5]nonadeca-1(18),2,4,14,16-pentaen-9-one (20 mg, 0.0427 mmol) (~23 mg/mL in MeOH) was purified by chiral SFC using a ChiralCel OJ-3 column (250×10 mm, 5 μm particle size) using 12% methanol in $CO_2$ mobile phase over 5 minutes (flow rate=10 mL/min, column temperature=35° C.). These conditions produced 2 enantiomeric products as described below:

Peak 1 was concentrated to afford as a viscous brown oil, 17-amino-6-hydroxy-10,13-dimethyl-6,15-bis(trifluoromethyl)-19-oxa-3,4,10,13,18-pentazatricyclo[12.3.1.12,5]nonadeca-1(18),2,4,14,16-pentaen-9-one (enantiomer 1) (hydrochloride salt) (1.8 mg, 17%). $^1$H NMR (400 MHz, DMSO-d6) δ 7.74-7.66 (m, 1H), 6.43 (s, 1H), 6.17 (s, 1H), 6.07 (s, 1H), 4.01 (ddd, J=13.5, 10.0, 4.3 Hz, 2H), 3.73 (t, J=4.4 Hz, 2H), 2.98 (s, 3H), 2.78 (d, J=4.1 Hz, 2H), 2.64 (s, 3H), 2.59 (d, J=6.1 Hz, 2H) ppm. ESI-MS m/z calc. 468.13446, found 469.09 (M+1)$^+$; Retention time: 1.5 minutes (LC Method A).

Peak 2 was concentrated to afford as a viscous brown oil, 17-amino-6-hydroxy-10,13-dimethyl-6,15-bis(trifluoromethyl)-19-oxa-3,4,10,13,18-pentazatricyclo[12.3.1.12,5]nonadeca-1(18),2,4,14,16-pentaen-9-one (enantiomer 2) (hydrochloride salt) (2.3 mg, 21%). $^1$H NMR (400 MHz, DMSO-d6) δ 7.69 (d, J 2.7 Hz, 1H), 6.43 (s, 1H), 6.17 (s, 1H), 6.07 (s, 1H), 4.02 (dq, J 10.1, 6.1, 5.4 Hz, 2H), 3.71 (d, J 10.2 Hz, 2H), 2.98 (s, 3H), 2.80 (d, J 8.0 Hz, 2H), 2.63 (d, J 6.9 Hz, 3H), 2.58 (d, J 9.1 Hz, 2H) ppm. ESI-MS m/z calc. 468.13446, found 469.2 (M+1)$^+$; Retention time: 1.5 minutes (LC Method A).

Example 26: Preparation of (12R)-20-amino-6-methyl-18-(trifluoromethyl)-22-oxa-3,4,16,21-tetraazatetracyclo[15.3.1.12,5.012,16]docosa-1(21),2,4,17,19-pentaen-6-ol (enantiomer 2) (Compound 45)

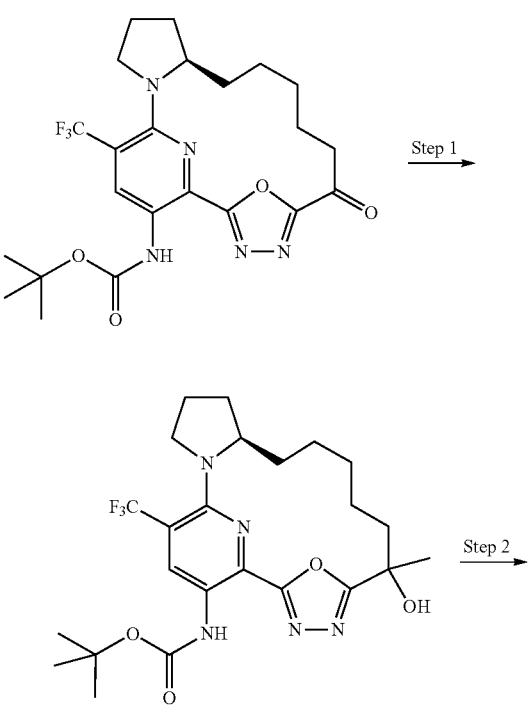

383
-continued

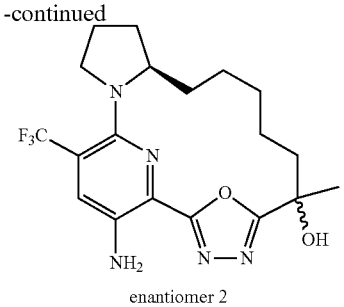

enantiomer 2

Step 1: tert-Butyl N-[(12R)-6-hydroxy-6-methyl-18-(trifluoromethyl)-22-oxa-3,4,16,21-tetraazatetracyclo[15.3.1.12,5.012,16]docosa-1(21),2,4,17,19-pentaen-20-yl]carbamate

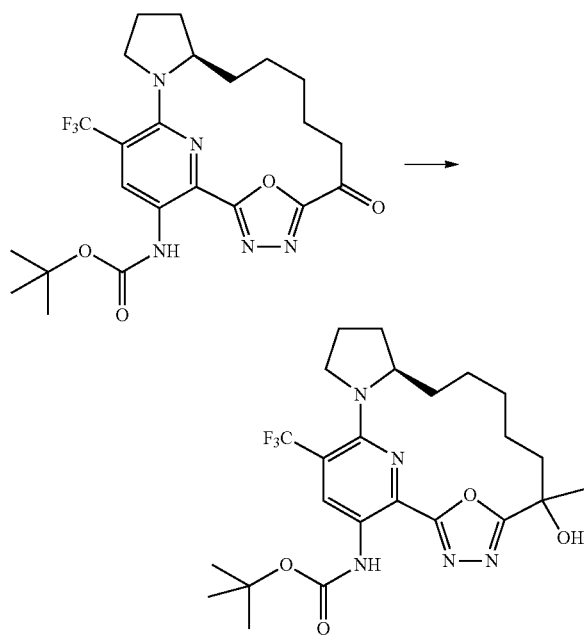

A solution of tert-butyl N-[(12R)-6-oxo-18-(trifluoromethyl)-22-oxa-3,4,16,21-tetraazatetracyclo[15.3.1.12,5.012,16]docosa-1(21),2,4,17,19-pentaen-20-yl]carbamate (30 mg, 0.06055 mmol) in THF (605.4 µL) was cooled to −78° C., then MeMgCl (60.53 µL of 3 M, 0.1816 mmol) was added dropwise under nitrogen atmosphere and stirred the resulting mixture for 30 min. Quenched the reaction with 1 M HCl and then extracted with ethyl acetate (2×30 mL). Combined the organic layers and washed with brine, dried over sodium sulfate, filtered and concentrated. The residue was purified by silica gel chromatography (12 g column) using a gradient from 0% to 40% ethyl acetate in hexanes which gave as a yellow solid, tert-butyl N-[(12R)-6-hydroxy-6-methyl-18-(trifluoromethyl)-22-oxa-3,4,16,21-tetraazatetracyclo[15.3.1.12,5.012,16]docosa-1(21),2,4,17,19-pentaen-20-yl]carbamate (20 mg, 65%). ESI-MS m/z calc. 511.24063, found 512.2 (M+1)+; Retention time: 0.82 minutes (LC Method R).

Step 2: (12R)-20-Amino-6-methyl-18-(trifluoromethyl)-22-oxa-3,4,16,21-tetraazatetracyclo[15.3.1.12,5.012,16]docosa-1(21),2,4,17,19-pentaen-6-ol (enantiomer 2) (Compound 45)

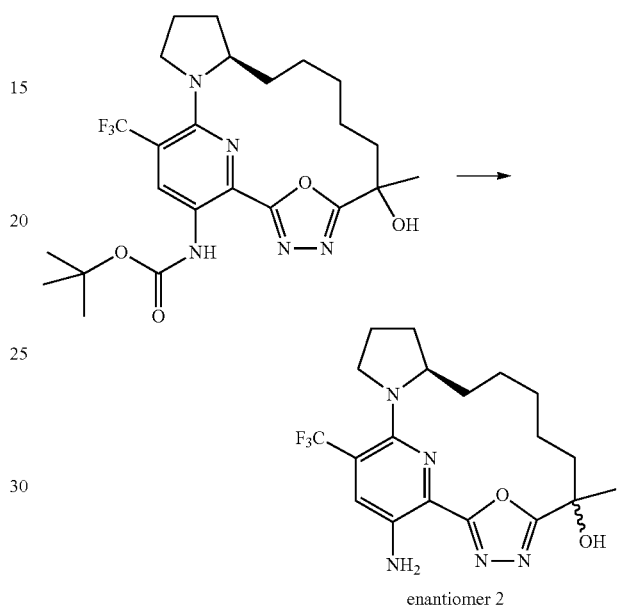

enantiomer 2

To a solution of tert-butyl N-[(12R)-6-hydroxy-6-methyl-18-(trifluoromethyl)-22-oxa-3,4,16,21-tetraazatetracyclo[15.3.1.12,5.012,16]docosa-1(21),2,4,17,19-pentaen-20-yl]carbamate (20 mg, 0.0391 mmol) in DCM (342.4 µL) was added TFA (150.3 µL, 1.951 mmol) and the reaction mixture was stirred at room temperature for 2 h. The reaction was concentrated then dissolved in DCM, washed with saturated NaHCO₃ solution and the organic layer was concentrated to give a yellow solid. This solid was purified by a normal phase SFC method using a ChiralPak IG column (250×10 mm, 5 µm particle size) using 40% methanol (+20 mM NH₃) in CO₂ mobile phase over 5 minutes (flow rate=10 mL/min, column temperature=35° C.) which gave as a yellow solid and the second enantiomer to elute, (12R)-20-amino-6-methyl-18-(trifluoromethyl)-22-oxa-3,4,16,21-tetraazatetracyclo[15.3.1.12,5.012,16]docosa-1(21),2,4,17,19-pentaen-6-ol (enantiomer 2) (1.6 mg, 10%). ¹H NMR (400 MHz, Chloroform-d) δ 7.47 (s, 1H), 4.06 (q, J=8.6 Hz, 1H), 3.68 (d, J=8.9 Hz, 1H), 3.44 (t, J=9.2 Hz, 1H), 2.64-2.50 (m, 1H), 2.23 (ddd, J=14.5, 10.6, 3.5 Hz, 2H), 2.02 (s, 2H), 1.90 (ddd, J=14.4, 10.3, 6.8 Hz, 2H), 1.81 (s, 3H), 1.73-1.62 (m, 3H), 1.62-1.43 (m, 4H) ppm. Two exchangeable NH₂ protons and one exchangeable OH proton were not observed in the proton NMR. ESI-MS m/z calc. 411.1882, found 412.2 (M+1)+; Retention time: 1.95 minutes (LC Method A).

Example 27: Preparation of ethyl 2-[17-amino-6-hydroxy-6,15-bis(trifluoromethyl)-19-oxa-3,4,13,18-tetrazatricyclo[12.3.1.1^2,5]nonadeca-1(18),2,4,14,16-pentaen-13-yl]acetate (enantiomer 1) (Compound 46) and ethyl 2-[17-amino-6-hydroxy-6,15-bis(trifluoromethyl)-19-oxa-3,4,13,18-tetrazatricyclo[12.3.1.1^2,5]nonadeca-1(18),2,4,14,16-pentaen-13-yl]acetate (enantiomer 2) (Compound 47)
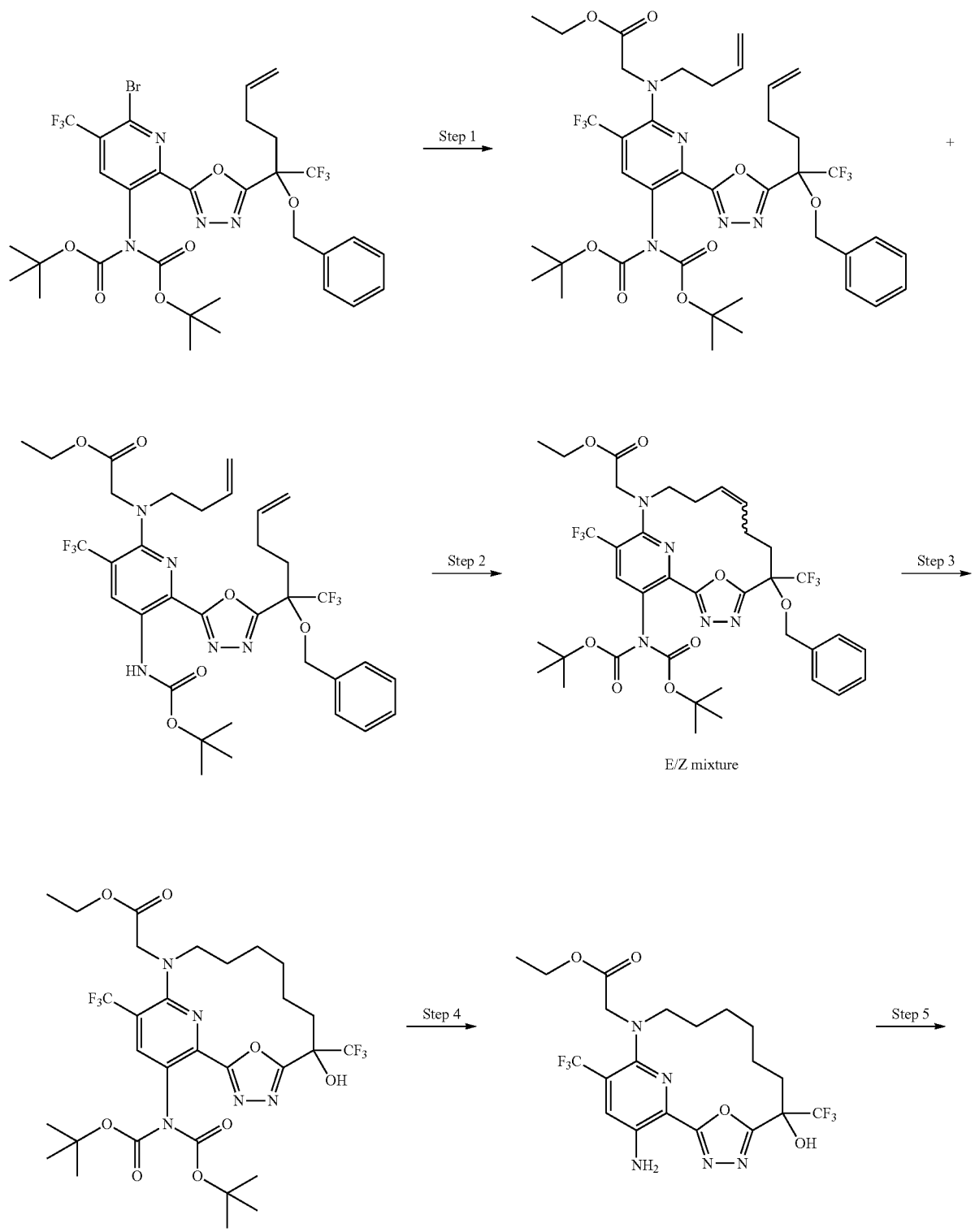
E/Z mixture

387

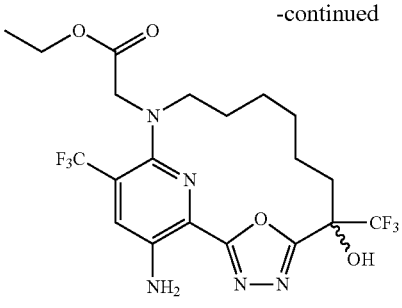

enantiomer 1

388

-continued

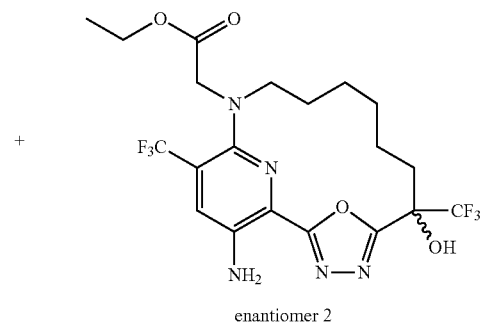

enantiomer 2

Step 1: Ethyl 2-[[6-[15-[1-benzyloxy-1-(trifluoromethyl)pent-4-enyl]-1,3,4-oxadiazol-2-yl]-5-[bis(tert-butoxycarbonyl)amino]-3-(trifluoromethyl)-2-pyridyl]-but-3-enyl-amino]acetate and ethyl 2-[[6-[5-[1-benzyloxy-1-(trifluoromethyl)pent-4-enyl]-1,3,4-oxadiazol-2-yl]-5-(tert-butoxycarbonylamino)-3-(trifluoromethyl)-2-pyridyl]-but-3-enyl-amino]acetate

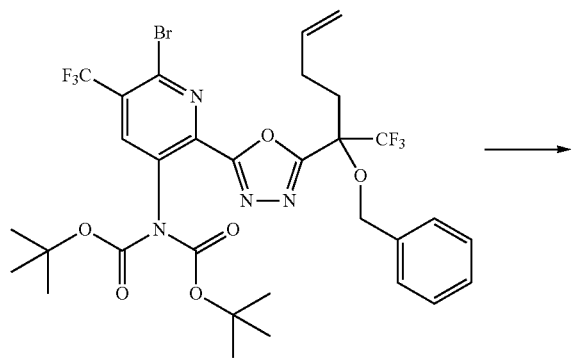

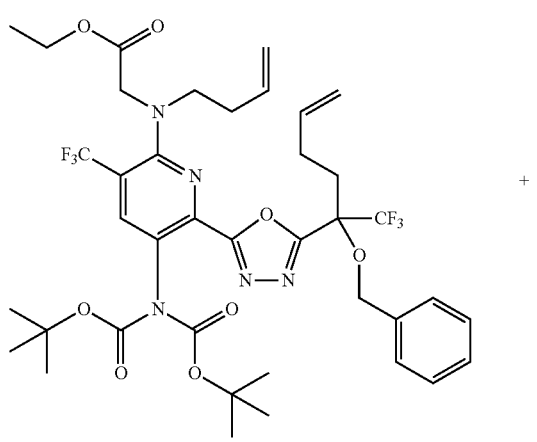

-continued

In a 250-mL sealed vessel, ethyl 2-(but-3-enylamino)acetate (1 g, 6.361 mmol), DIEA (1.5 mL, 8.612 mmol) and tert-butyl N-[2-[5-[1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate (860 mg, 1.144 mmol) were combined in acetonitrile (25 mL) and the mixture was heated at 90° C. for 48 hours. The reaction mixture was cooled to room temperature and concentrated under reduced pressure. The residue was purified by silica gel chromatography (120 gram column) using a gradient from 100% hexanes to 40% ethyl acetate in hexanes to afford as a yellow foam, ethyl 2-[[6-[5-[1-benzyloxy-1-(trifluoromethyl)pent-4-enyl]-1,3,4-oxadiazol-2-yl]-5-[bis(tert-butoxycarbonyl)amino]-3-(trifluoromethyl)-2-pyridyl]-but-3-enyl-amino]acetate (245 mg, 26%). ESI-MS m/z calc. 827.3329, found 828.2 (M+1)⁺; Retention time: 1.88 minutes (LC Method M).

Also isolated the mono-boc product from the silica gel column, ethyl 2-[[6-[5-[1-benzyloxy-1-(trifluoromethyl)pent-4-enyl]-1,3,4-oxadiazol-2-yl]-5-(tert-butoxycarbonylamino)-3-(trifluoromethyl)-2-pyridyl]-but-3-enyl-amino]acetate (116 mg, 14%). ESI-MS m/z calc. 727.28046, found 728.2 (M+1)⁺; Retention time: 2.09 minutes (LC Method M).

Step 2: Ethyl 2-[6-benzyloxy-17-[bis(tert-butoxy-carbonyl)amino]-6,15-bis(trifluoromethyl)-19-oxa-3,4,13,18-tetrazatricyclo[12.3.1.1²,⁵]nonadeca-1(18),2,4,9,14,16-hexaen-13-yl]acetate (E/Z mixture)

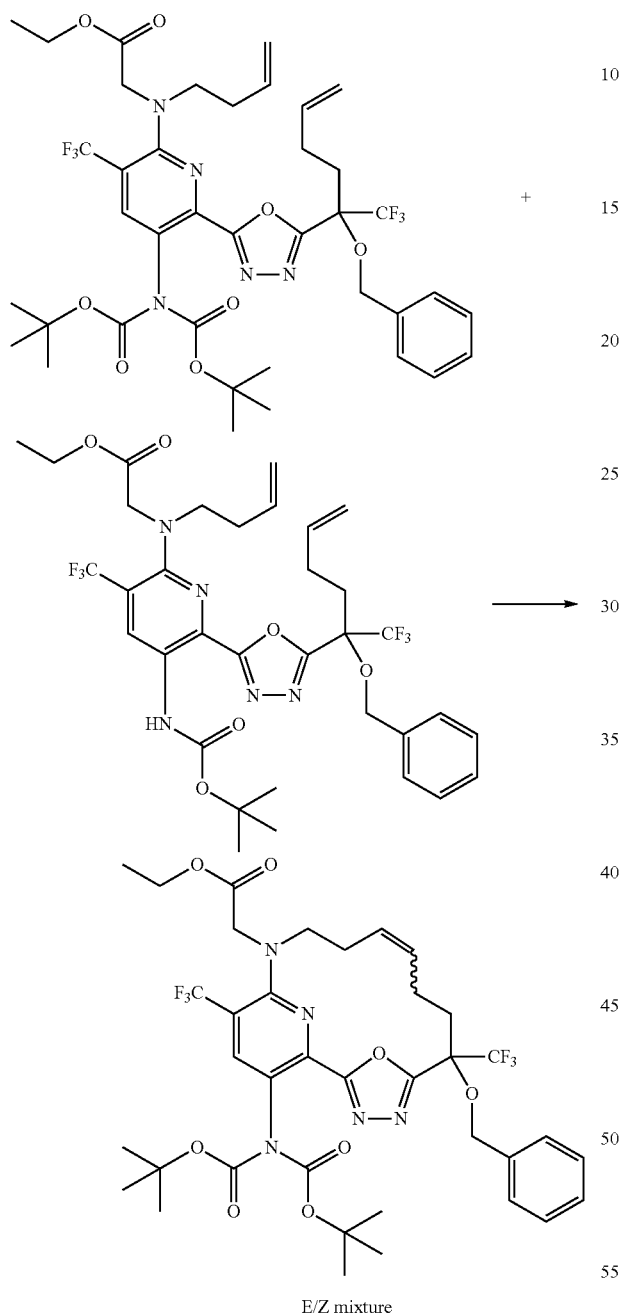

E/Z mixture

In a 500 mL round-bottom 3-neck flask, a continuously degassed solution via nitrogen line of Zhan catalyst-1B (110 mg, 0.1499 mmol) in DCE (250 mL) was heated to 50° C. under nitrogen atmosphere. Then, a solution of ethyl 2-[[6-[5-[1-benzyloxy-1-(trifluoromethyl)pent-4-enyl]-1,3,4-oxa-diazol-2-yl]-3-(trifluo-romethyl)-2-pyridyl]-but-3-enyl-amino]acetate (355 mg, 0.4288 mmol) and ethyl 2-[[6-[5-[1-benzyloxy-1-(trifluo-romethyl)pent-4-enyl]-1,3,4-oxadiazol-2-yl]-5-(tert-butoxy-carbonylamino)-3-(trifluoromethyl)-2-pyridyl]-but-3-enyl-amino]acetate (156 mg, 0.2144 mmol) in DCE (30 mL) was added dropwise via syringe. The resulting mixture was heated at 75° C. for 2 h. The reaction mixture was then cooled to room temperature and concentrated under reduced pressure. The crude material was purified by silica gel chromatography (80 gram column) using a gradient from 100% hexanes to 50% ethyl acetate in hexanes which afforded ethyl 2-[6-benzyloxy-17-[bis(tert-butoxycarbonyl)amino]-6,15-bis(trifluoromethyl)-19-oxa-3,4,13,18-tetraza-tricyclo[12.3.1.1²,⁵]nonadeca-1(18),2,4,9,14,16-hexaen-13-yl]acetate (E/Z mixture) (314 mg, 92%). $^1$H NMR (400 MHz, DMSO-d6) δ 8.31 (s, 1H), 7.39-7.25 (m, 5H), 5.61 (q, J 8.1 Hz, 1H), 5.41 (q, J=8.5 Hz, 1H), 4.76 (d, J 11.2 Hz, 1H), 4.69 (d, J 11.2 Hz, 1H), 4.41 (s, 2H), 4.13 (q, J 7.1 Hz, 2H), 3.60 (d, J=11.8 Hz, 1H), 3.49 (t, J=12.7 Hz, 1H), 2.71-2.52 (m, 3H), 2.43-2.34 (m, 1H), 2.33-2.23 (m, 1H), 1.33 (s, 9H), 1.28 (s, 9H), 1.26-1.21 (m, 1H), 1.18 (t, J 7.1 Hz, 3H) ppm. ESI-MS m/z calc. 799.3016, found 800.2 (M+1)$^+$; Retention time: 1.69 minutes (LC Method M).

Step 3: Ethyl 2-[17-[bis(tert-butoxycarbonyl)amino]-6-hydroxy-6,15-bis(trifluoromethyl)-19-oxa-3,4,13,18-tetrazatricyclo[12.3.1.1²,⁵]nonadeca-1(18),2,4,14,16-pentaen-13-yl]acetate

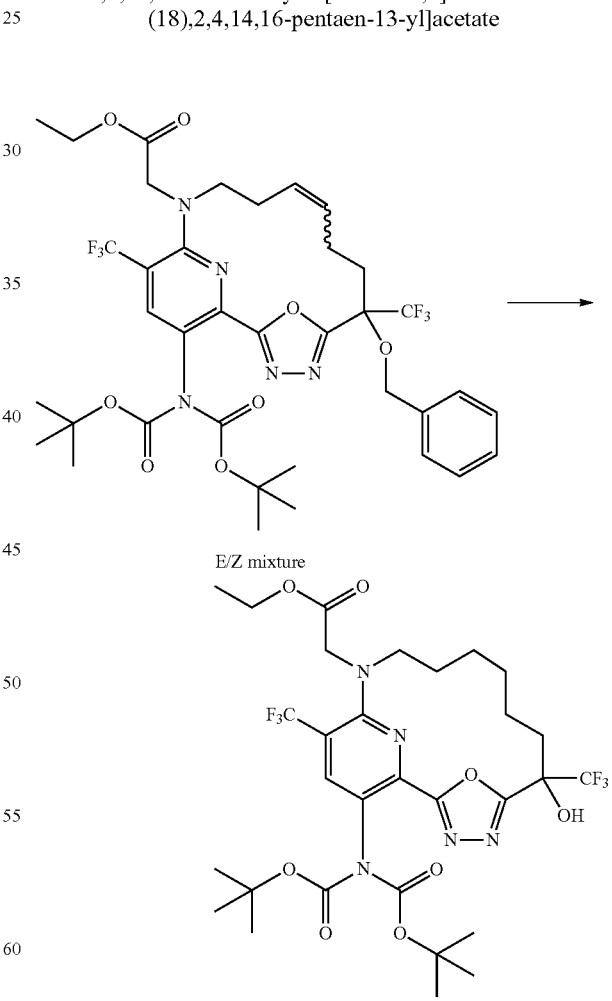

E/Z mixture

A solution of ethyl 2-[6-benzyloxy-17-[bis(tert-butoxy-carbonyl)amino]-6,15-bis(trifluoromethyl)-19-oxa-3,4,13,18-tetrazatricyclo[12.3.1.1²,⁵]nonadeca-1(18),2,4,9,14,16-hexaen-13-yl]acetate (E/Z mixture) (310 mg, 0.3876 mmol)

in AcOH (5 mL) and ethyl acetate (5 mL) was purged with nitrogen. Then Pd/C (64 mg of 10% w/w, 0.06014 mmol) was added. The mixture was degassed with nitrogen for 5 minutes, then purged by a balloon filled with hydrogen gas. The mixture was stirred at 1 atm of hydrogen for 1 h. Added more Pd/C (350 mg of 10% w/w, 0.3289 mmol) and stirred for 3 more hours. The reaction was filtered over a Celite plug washing with acetonitrile, ethyl acetate and then the filtrate was concentrated. The residue was purified by silica gel chromatography (40 gram column) using a gradient from 100% hexanes to 100% ethyl acetate to afford as a pale yellow solid, ethyl 2-[17-[bis(tert-butoxycarbonyl)amino]-6-hydroxy-6,15-bis(trifluoromethyl)-19-oxa-3,4,13,18-tetrazatricyclo[12.3.1.1 2,5]nonadeca-1(18),2,4,14,16-pentaen-13-yl]acetate (228 mg, 83%). $^1$H NMR (400 MHz, DMSO-d6) δ 8.27 (s, 1H), 7.68 (s, 1H), 4.35 (d, J=2.8 Hz, 2H), 4.11 (q, J=7.1 Hz, 2H), 3.65-3.49 (m, 2H), 2.23-2.08 (m, 2H), 1.85 (td, J=10.2, 9.2, 4.2 Hz, 1H), 1.73-1.55 (m, 3H), 1.55-1.38 (m, 4H), 1.35 (s, 9H), 1.27 (s, 9H), 1.16 (d, J=7.1 Hz, 3H) ppm. ESI-MS m/z calc. 711.27026, found 712.2 (M+1)$^+$; Retention time: 1.16 minutes (LC Method M).

Step 4: Ethyl 2-[17-amino-6-hydroxy-6,15-bis(trifluoromethyl)-19-oxa-3,4,13,18-tetrazatricyclo[12.3.1.1 2,5]nonadeca-1(18),2,4,14,16-pentaen-13-yl]acetate

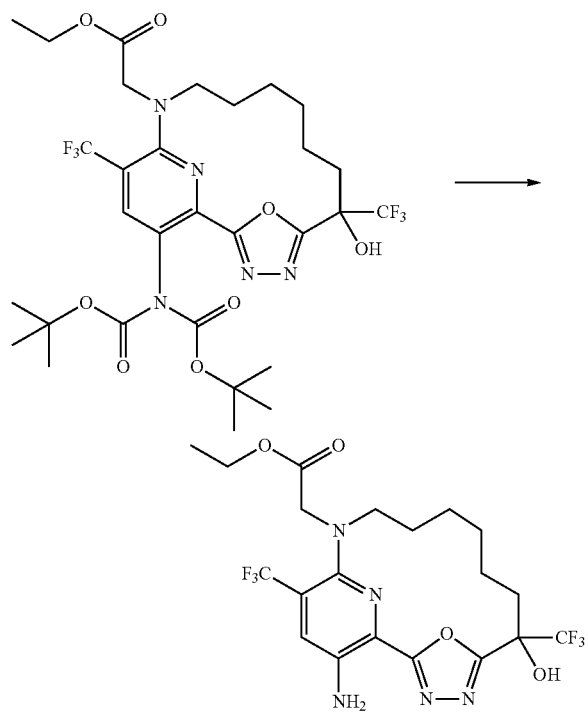

To a solution of ethyl 2-[17-[bis(tert-butoxycarbonyl)amino]-6-hydroxy-6,15-bis(trifluoromethyl)-19-oxa-3,4,13,18-tetrazatricyclo[12.3.1.1 2,5]nonadeca-1(18),2,4,14,16-pentaen-13-yl]acetate (56 mg, 0.07869 mmol) in DCM (1.5 mL) was added TFA (250 µL, 3.245 mmol) and the mixture was stirred at room temperature for 1 hour. The mixture was evaporated to dryness, then diluted with ether and concentrated. The residue was purified by silica gel chromatography (4 gram column) using a gradient from 100% hexanes to 80% ethyl acetate in hexanes to afford as a yellow solid, ethyl 2-[17-amino-6-hydroxy-6,15-bis(trifluoromethyl)-19-oxa-3,4,13,18-tetrazatricyclo[12.3.1.1 2,5]nonadeca-1(18),2,4,14,16-pentaen-13-yl]acetate (26.8 mg, 67%) ppm. ESI-MS m/z calc. 511.16544, found 512.2 (M+1)$^+$; Retention time: 1.93 minutes (LC Method A).

Step 5: Ethyl 2-[17-amino-6-hydroxy-6,15-bis(trifluoromethyl)-19-oxa-3,4,13,18-tetrazatricyclo[12.3.1.1 2,5]nonadeca-1(18),2,4,14,16-pentaen-13-yl]acetate (enantiomer 1) (Compound 46) and ethyl 2-[17-amino-6-hydroxy-6,15-bis(trifluoromethyl)-19-oxa-3,4,13,18-tetrazatricyclo[12.3.1.1 2,5]nonadeca-1(18),2,4,14,16-pentaen-13-yl]acetate (enantiomer 2) (Compound 47)

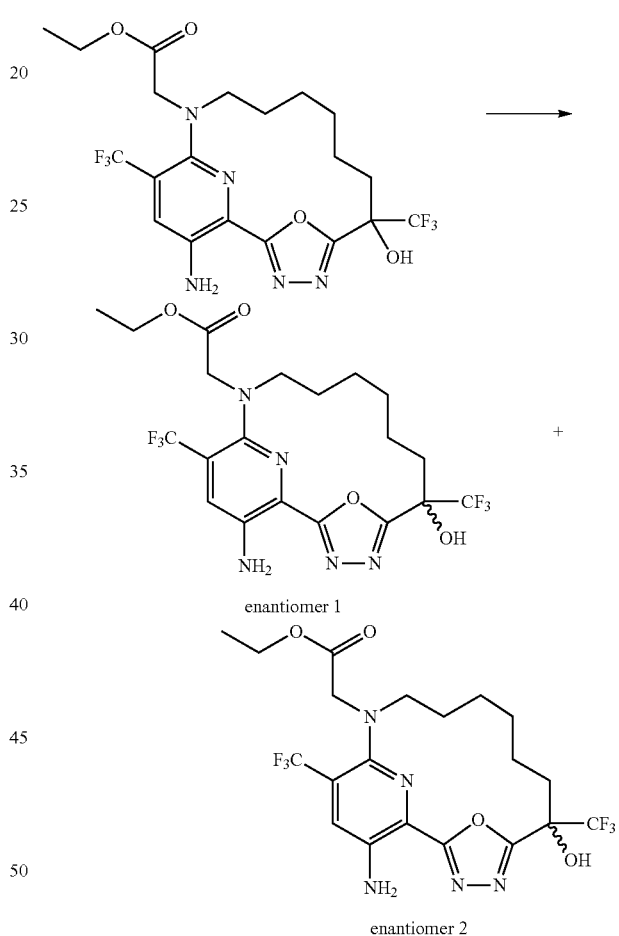

enantiomer 1 enantiomer 2

Racemic ethyl 2-[17-amino-6-hydroxy-6,15-bis(trifluoromethyl)-19-oxa-3,4,13,18-tetrazatricyclo[12.3.1.1 2,5]nonadeca-1(18),2,4,14,16-pentaen-13-yl]acetate (26.8 mg, 0.05240 mmol) was purified by chiral SFC using a LUX-4 column (250×21.2 mm, 5 µm particle size) sold by Phenomenex and eluting with 14% MeOH (+20 mM NH$_3$)/86% CO$_2$ which provided two single enantiomer products:

The first enantiomer to elute was further purified by reverse-phase preparative HPLC using a gradient from 1% to 99% acetonitrile in water (+5 mM HCl) over 15 minutes to afford as a yellow solid, ethyl 2-[17-amino-6-hydroxy-6,15-bis(trifluoromethyl)-19-oxa-3,4,13,18-tetrazatricyclo[12.3.1.1 2,5]nonadeca-1(18),2,4,14,16-pentaen-13-yl]acetate (enantiomer 1) (11.4 mg, 84%). $^1$H NMR (400 MHz, DMSO-d6) δ 7.69 (s, 1H), 7.59 (s, 1H), 6.30 (s, 2H), 4.13-4.03 (m, 4H), 3.42-3.32 (m, 2H), 2.14 (t, J=7.3 Hz, 2H), 1.91 (dt, J=12.8, 6.1 Hz, 1H), 1.59 (ddd, J=25.0, 17.2, 9.1 Hz, 4H), 1.47 (q, J=7.6, 6.1 Hz, 1H), 1.36 (q, J=8.2, 7.0 Hz, 2H), 1.14 (t, J=7.1 Hz, 3H) ppm. ESI-MS m/z calc. 511.16544, found 512.1 (M+1)$^+$; Retention time: 1.93 minutes (LC Method A).

The second enantiomer to elute was further purified by reverse-phase preparative HPLC using a gradient from 1% to 99% acetonitrile in water (+5 mM HCl) over 15 minutes to afford as a yellow solid, ethyl 2-[17-amino-6-hydroxy-6, 15-bis(trifluoromethyl)-19-oxa-3,4,13,18-tetrazatricyclo [12.3.1.1.2,5]nonadeca-1(18),2,4,14,16-pentaen-13-yl]acetate (enantiomer 2) (11.1 mg, 82%). $^1$H NMR (400 MHz, DMSO-d6) δ 7.70 (s, 1H), 7.59 (s, 1H), 6.30 (s, 2H), 4.13-4.03 (m, 4H), 3.44-3.32 (m, 2H), 2.14 (t, J=7.4 Hz, 2H), 1.98-1.86 (m, 1H), 1.59 (tt, J=16.8, 8.1 Hz, 4H), 1.50-1.43 (m, 1H), 1.43-1.32 (m, 2H), 1.14 (t, J=7.1 Hz, 3H) ppm. ESI-MS m/z calc. 511.16544, found 512.1 (M+1)$^+$; Retention time: 1.93 minutes (LC Method A).

Example 28: Preparation of 2-[17-amino-6-hydroxy-6,15-bis(trifluoromethyl)-19-oxa-3,4,13,18-tetrazatricyclo[12.3.1.1.2,5]nonadeca-1(18),2,4,14,16-pentaen-13-yl]-N-methyl-acetamide (enantiomer 1) (Compound 48) and 2-[17-amino-6-hydroxy-6,15-bis(trifluoromethyl)-19-oxa-3,4,13,18-tetrazatricyclo[12.3.1.1.2,5]nonadeca-1(18),2,4,14,16-pentaen-13-yl]-N-methyl-acetamide (enantiomer 2) (Compound 49)

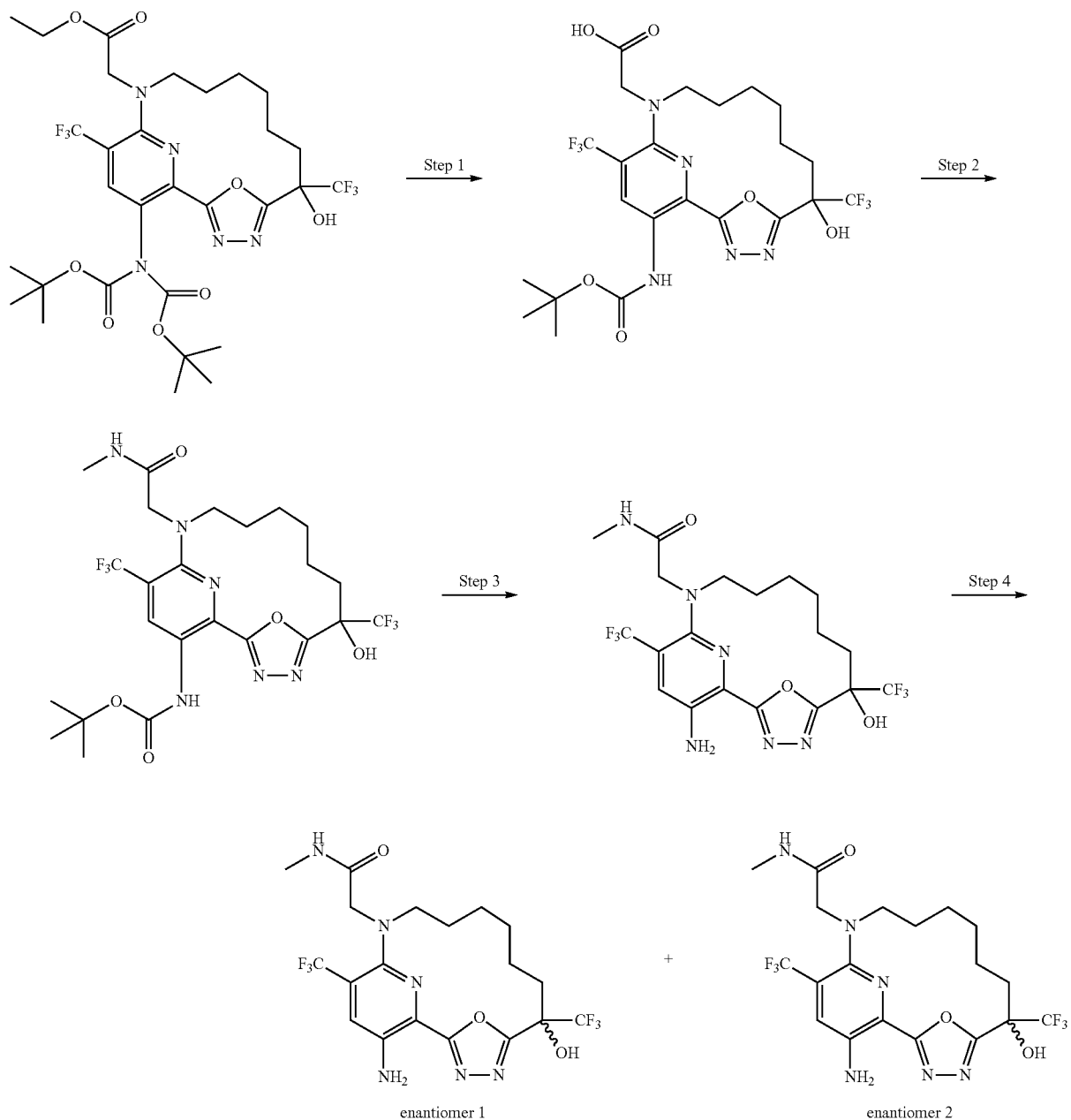

395

Step 1: 2-[17-(tert-Butoxycarbonylamino)-6-hydroxy-6,15-bis(trifluoromethyl)-19-oxa-3,4,13,18-tetrazatricyclo[12.3.1.1²,⁵]nonadeca-1(17),2,4,14(18),15-pentaen-13-yl]acetic Acid

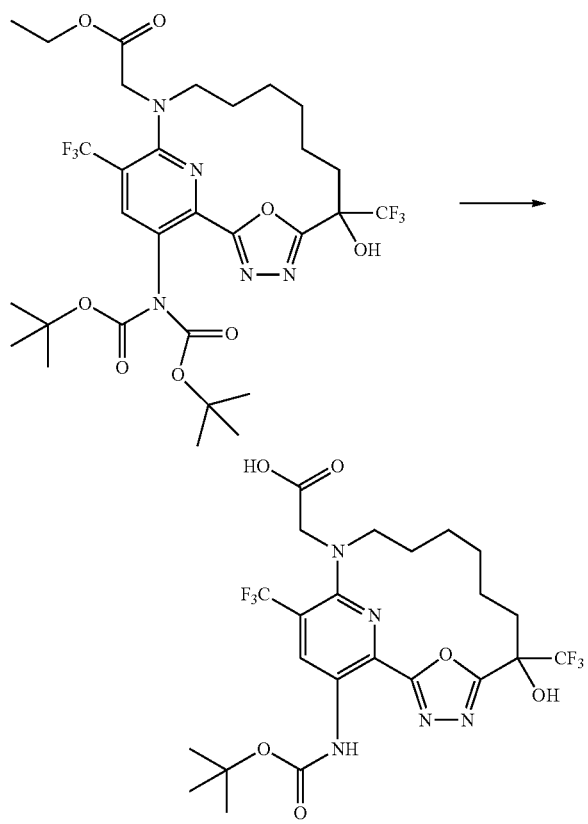

To a solution of ethyl 2-[17-[bis(tert-butoxycarbonyl)amino]-6-hydroxy-6,15-bis(trifluoromethyl)-19-oxa-3,4,13,18-tetrazatricyclo[12.3.1.1²,⁵]nonadeca-1(18),2,4,14,16-pentaen-13-yl]acetate (72 mg, 0.1012 mmol) in THF (900 μL) was added methanol (900 μL) and water (630 μL) followed by lithium hydroxide (11.3 mg, 0.4719 mmol). The mixture was stirred with heating at 65° C. f 4 h. THF and methanol were removed under reduced pressure and then 10 mL of aqueous HCl (10%) was added to acidify to pH ~4 and the product was extracted with ethyl acetate (2×5 mL). The organic phases were combined, washed with brine (1 mL), dried over anhydrous sodium sulfate, filtered and concentrated under reduced pressure. The crude material was then purified by silica gel chromatography (4 gram column) using a gradient from 100% hexanes to 80% ethyl acetate in hexanes to afford a residue which was placed under vacuum for 2 hours to produce as a yellow solid, 2-[17-(tert-butoxycarbonylamino)-6-hydroxy-6,15-bis(trifluoromethyl)-19-oxa-3,4,13,18-tetrazatricyclo[12.3.1.1²,⁵]nonadeca-1(17),2,4,14(18),15-pentaen-13-yl]acetic acid (51 mg, 86%). ESI-MS m/z calc. 583.1865, found 584.2 (M+1)⁺; Retention time: 1.41 minutes (LC Method J).

396

Step 2: tert-Butyl N-[6-hydroxy-13-[2-(methylamino)-2-oxo-ethyl]-6,15-bis(trifluoromethyl)-19-oxa-3,4,13,18-tetrazatricyclo[12.3.1.1²,⁵]nonadeca-1(17),2,4,14(18),15-pentaen-17-yl]carbamate

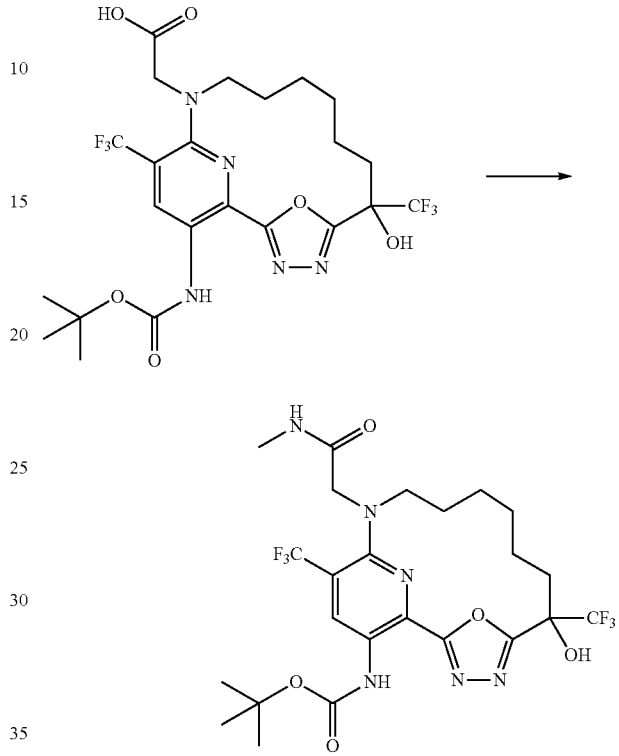

To a solution of 2-[17-(tert-butoxycarbonylamino)-6-hydroxy-6,15-bis(trifluoromethyl)-19-oxa-3,4,13,18-tetrazatricyclo[12.3.1.1²,⁵]nonadeca-1(17),2,4,14(18),15-pentaen-13-yl]acetic acid (51 mg, 0.08741 mmol) in NMP (1 mL) at room temperature was added methylamine (hydrochloride salt) (15 mg, 0.2222 mmol) and DIEA (125 μL. 0.7176 mmol) followed by HATU (42 mg, 0.1105 mmol). The reaction mixture was stirred at room temperature for 3 h. The organic material was extracted with ethyl acetate (3×5 mL). The organics were separated, dried over sodium sulfate and evaporated. The crude material was then purified by silica gel chromatography (12 gram column) using a gradient from 100% hexanes to 80% ethyl acetate in hexanes (compound elutes at 60% ethyl acetate) to afford a yellow residue which was placed under vacuum for 2 hours to produce as a pale yellow solid, tert-butyl N-[6-hydroxy-13-[2-(methylamino)-2-oxo-ethyl]-6,15-bis(trifluoromethyl)-19-oxa-3,4,13,18-tetrazatricyclo[12.3.1.1²,⁵]nonadeca-1(17),2,4,14(18),15-pentaen-17-yl]carbamate (43.7 mg, 84%). ESI-MS m/z calc. 596.2182, found 597.2 (M+1)⁺; Retention time: 1.31 minutes (LC Method M).

397

Step 3: 2-[17-Amino-6-hydroxy-6,15-bis(trifluoromethyl)-19-oxa-3,4,13,18-tetrazatricyclo[12.3.1.12,5]nonadeca-1(18),2,4,14,16-pentaen-13-yl]-N-methyl-acetamide

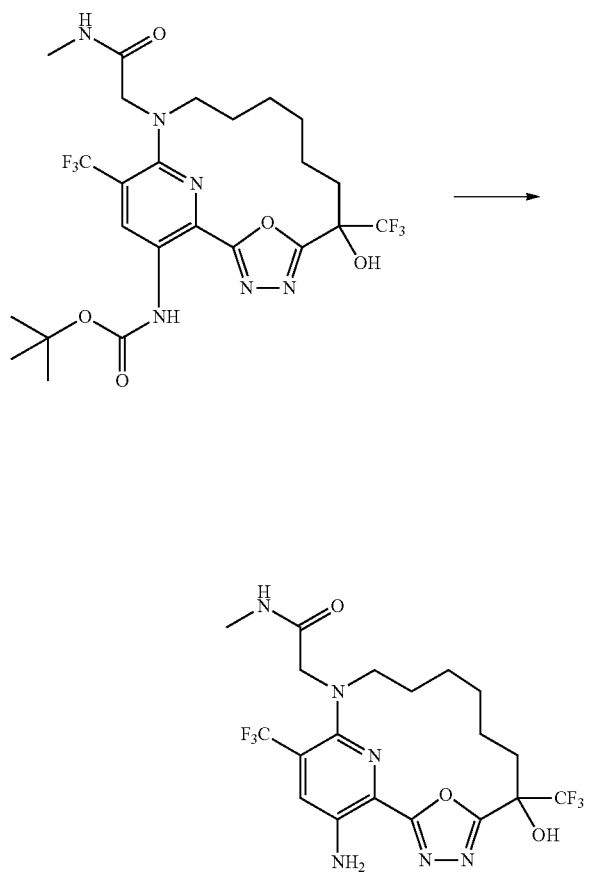

tert-butyl N-[6-hydroxy-13-[2-(methylamino)-2-oxo-ethyl]-6,15-bis(trifluoromethyl)-19-oxa-3,4,13,18-tetrazatricyclo[12.3.1.12,5]nonadeca-1(17),2,4,14(18),15-pentaen-17-yl]carbamate (43 mg, 0.07208 mmol) was dissolved in dichloromethane (2 mL) and to the mixture was added TFA (150 µL, 1.947 mmol) and the mixture was stirred at room temperature. After 1 hour, the reaction was complete. The mixture was evaporated to dryness then diluted with ether and re-concentrated. The crude material was purified by silica gel chromatography (12 gram column) using a gradient from 100% hexanes to 100% ethyl acetate (compound elutes at 85% ethyl acetate) to afford a yellow residue which was then placed under vacuum for 2 hours to afford as a yellow solid, 2-[17-amino-6-hydroxy-6,15-bis(trifluoromethyl)-19-oxa-3,4,13,18-tetrazatricyclo[12.3.1.12,5]nonadeca-1(18),2,4,14,16-pentaen-13-yl]-N-methyl-acetamide (30.6 mg, 86%). ESI-MS m/z calc. 496.16577, found 497.2 (M+1)$^+$; Retention time: 1.46 minutes (LC Method A).

398

Step 4: 2-[17-Amino-6-hydroxy-6,15-bis(trifluoromethyl)-19-oxa-3,4,13,18-tetrazatricyclo[12.3.1.12,5]nonadeca-1(18),2,4,14,16-pentaen-13-yl]-N-methyl-acetamide (enantiomer 1) (Compound 48) and 2-[17-amino-6-hydroxy-6,15-bis(trifluoromethyl)-19-oxa-3,4,13,18-tetrazatricyclo[12.3.1.12,5]nonadeca-1(18),2,4,14,16-pentaen-13-yl]-N-methyl-acetamide (enantiomer 2) (Compound 49)

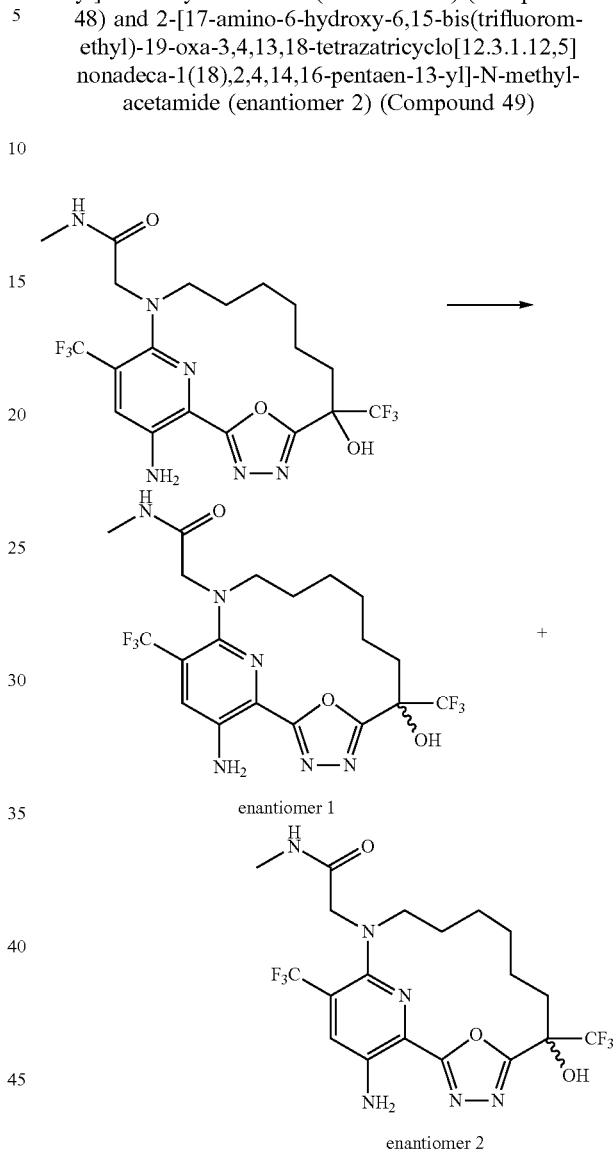

Racemic 2-[17-amino-6-hydroxy-6,15-bis(trifluoromethyl)-19-oxa-3,4,13,18-tetrazatricyclo[12.3.1.12,5]nonadeca-1(18),2,4,14,16-pentaen-13-yl]-N-methyl-acetamide (30.6 mg, 0.06164 mmol) was subjected to a normal phase SFC method using a ChiralPak IG column (250×10 mm, 5 µm particle size) using 22% methanol (20 mM NH$_3$) in CO$_2$ mobile phase over 5 minutes (flow rate=5 mL/min, column temperature=35° C.). These conditions produced 2 enantiomeric products as described below:

The first enantiomer to elute afforded as a yellow solid, 2-[17-amino-6-hydroxy-6,15-bis(trifluoromethyl)-19-oxa-3,4,13,18-tetrazatricyclo[12.3.1.12,5]nonadeca-1(18),2,4,14,16-pentaen-13-yl]-N-methyl-acetamide (enantiomer 1) (10.3 mg, 67%). $^1$H NMR (400 MHz, DMSO-d6) δ 7.73 (d, J=4.9 Hz, 1H), 7.70 (s, 1H), 7.59 (s, 1H), 6.33 (s, 2H), 3.78-3.67 (m, 2H), 3.23 (ddd, J=15.2, 11.4, 3.9 Hz, 2H), 2.62 (d, J=4.5 Hz, 3H), 2.18-2.10 (m, 2H), 1.91 (d, J=13.3 Hz, 1H), 1.58 (dq, J=19.3, 10.5, 9.3 Hz, 4H), 1.48 (d, J=7.1 Hz, 1H), 1.37 (s, 2H) ppm. ESI-MS m/z calc. 496.16577, found 497.1 (M+1)⁺; Retention time: 1.45 minutes (LC Method A).

The second enantiomer to elute afforded as a yellow solid, 2-[17-amino-6-hydroxy-6,15-bis(trifluoromethyl)-19-oxa-3,4,13,18-tetrazatricyclo[12.3.1.1²,⁵]nonadeca-1(18),2,4,14,16-pentaen-13-yl]-N-methyl-acetamide (enantiomer 2) (11.2 mg, 72%). $^1$H NMR (400 MHz, DMSO-d6) δ 7.73 (d, J=4.9 Hz, 1H), 7.70 (s, 1H), 7.60 (s, 1H), 6.33 (s, 2H), 3.78-3.67 (m, 2H), 3.23 (ddt, J=19.5, 12.8, 5.8 Hz, 2H), 2.62 (d, J=4.5 Hz, 3H), 2.14 (q, J=5.8, 4.9 Hz, 2H), 1.90 (s, 1H), 1.58 (dq, J=28.5, 11.4, 10.0 Hz, 4H), 1.48 (d, J=6.9 Hz, 1H), 1.37 (s, 2H) ppm. ESI-MS m/z calc. 496.16577, found 497.1 (M+1)⁺; Retention time: 1.45 minutes (LC Method A).

Example 29: Preparation of (12R)-20-amino-18-methyl-6-(trifluoromethyl)-22-oxa-3,4,16,21-tetraazatetracyclo[15.3.1.1²,⁵.0¹²,¹⁶]docosa-1(21),2,4,17,19-pentaen-6-ol (enantiomer 1) (Compound 50) and (12R)-20-amino-18-methyl-6-(trifluoromethyl)-22-oxa-3,4,16,21-tetraazatetracyclo[15.3.1.1²,⁵.0¹²,¹⁶]docosa-1(21),2,4,17,19-pentaen-6-ol (enantiomer 2) (Compound 51)

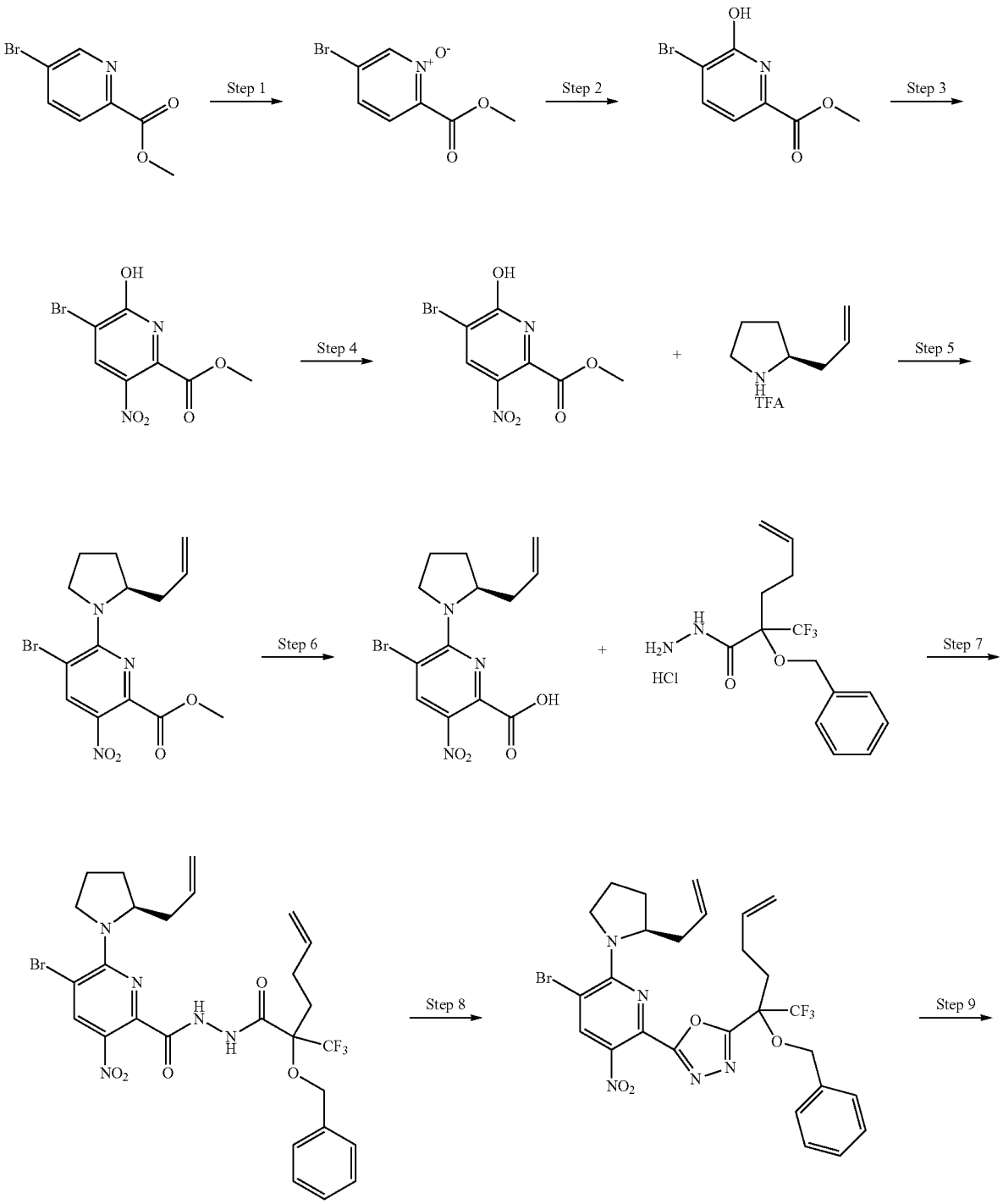

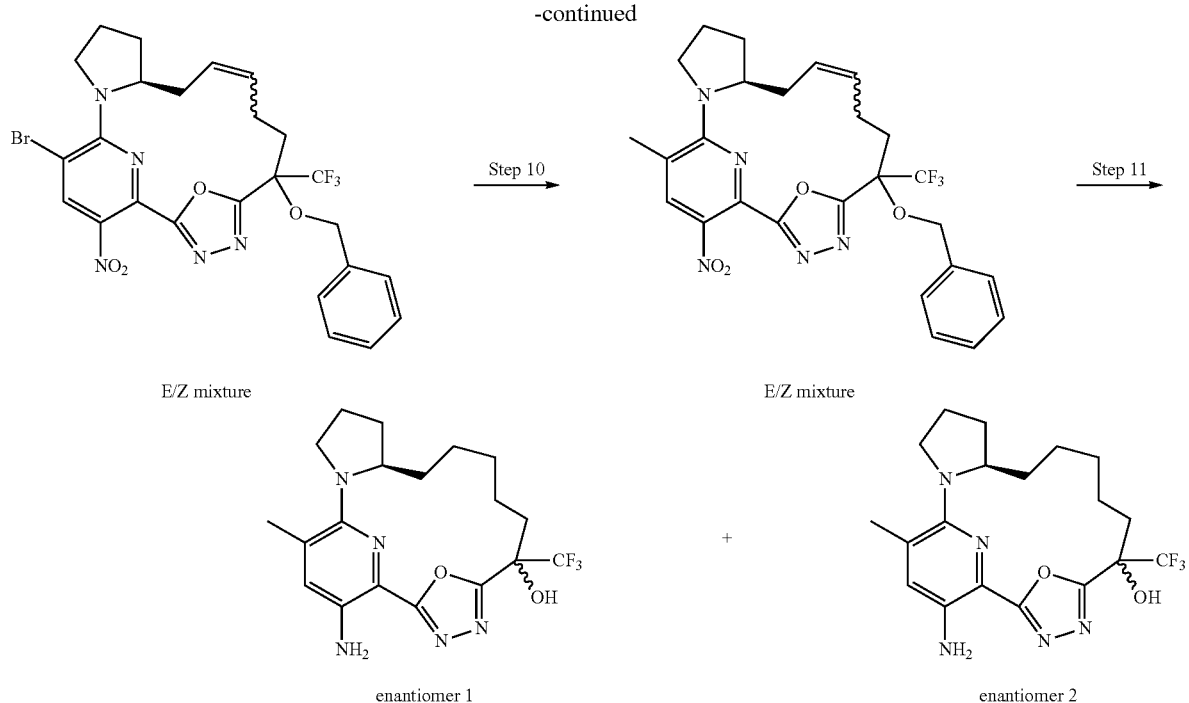

E/Z mixture      E/Z mixture enantiomer 1      enantiomer 2

Step 1: Methyl 5-bromo-1-oxido-pyridin-1-ium-2-carboxylate

Step 2: Methyl 5-bromo-6-hydroxy-pyridine-2-carboxylate

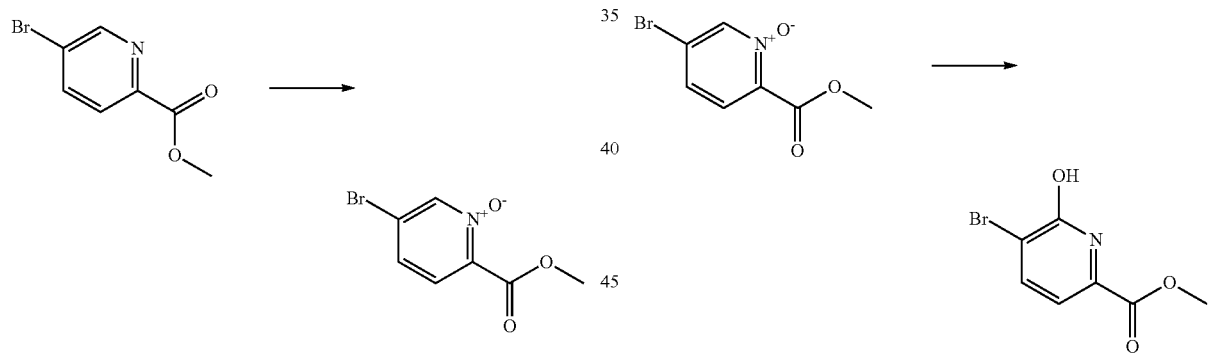

Trifluoroacetic anhydride (41.869 g, 28.1 mL, 199.35 mmol) was added dropwise to methyl 5-bromopyridine-2-carboxylate (21.5 g, 99.522 mmol) and urea hydrogen peroxide (20 g, 212.61 mmol) in acetonitrile (140 mL) at 0° C. while keeping temperature below 10° C. The mixture was warmed to room temperature and stirred overnight. The mixture was poured in a 0.5 N aqueous hydrochloric acid solution (200 mL) and extracted with DCM (2×100 mL). The organic phases were combined, dried over anhydrous sodium sulfate, filtered and concentrated under reduced pressure to afford as a yellow solid, methyl 5-bromo-1-oxido-pyridin-1-ium-2-carboxylate (26.2 g, 98%). $^1$H NMR (300 MHz, Chloroform-d) δ 8.65 (s, 1H), 7.85-7.69 (m, 2H), 4.00 (s, 3H) ppm. ESI-MS m/z calc. 230.9531, found 232.0 (M+1)$^+$; Retention time: 1.05 minutes (LC Method E).

Trifluoroacetic anhydride (298.00 g, 200 mL, 1.4188 mol) was added drop-wise to a mixture of methyl 5-bromo-1-oxido-pyridin-1-ium-2-carboxylate (40 g, 151.70 mmol) in DMF (240 mL) at 0° C., over 1 hour (temperature should be kept below 10° C.) and the mixture was stirred at room temperature overnight. Then, the mixture was concentrated under reduced pressure to remove excess of trifluoroacetic acid. The residual DMF solution was poured gradually into stirring water (1.5 L) which was cooled at 0° C., over 30 minutes. The solid precipitate was collected by filtration and then washed with water (400 mL). The solid was dried by lyophilization to provide as a white solid, methyl 5-bromo-6-hydroxy-pyridine-2-carboxylate (27.2 g, 77%). $^1$H NMR (300 MHz, Chloroform-d) δ 10.27 (br. s., 1H), 7.89 (d, J=7.3 Hz, 1H), 6.88 (d, J=7.3 Hz, 1H), 3.99 (s, 3H) ppm. ESI-MS m/z calc. 230.9531, found 232.0 (M+1)$^+$; Retention time: 1.31 minutes (LC Method E).

Step 3: Methyl 5-bromo-6-hydroxy-3-nitro-pyridine-2-carboxylate

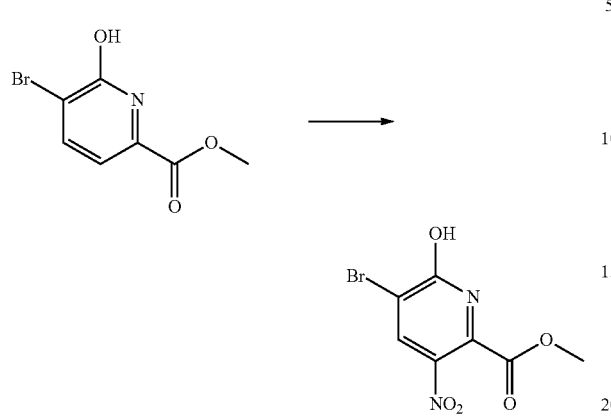

To a solution of methyl 5-bromo-6-hydroxy-pyridine-2-carboxylate (10.9 g, 46.976 mmol) in sulfuric acid (65 mL) cooled in ice bath was added nitric acid (4.2280 g, 4 mL, 46.968 mmol) dropwise. After 5 min, the ice bath was removed, and the reaction mixture was stirred at 30° C. overnight. Nitric acid (528.5 mg, 0.5 mL, 5.871 mmol) was added and the reaction mixture was stirred at 30° C. overnight. The reaction mixture cooled and added to ice-cold water (500 mL). The resulting precipitate was collected by filtration, rinsed with additional water and dried to afford as a yellow solid, methyl 5-bromo-6-hydroxy-3-nitro-pyridine-2-carboxylate (8.15 g, 58%). $^1$H NMR (300 MHz, Chloroform-d) δ 10.29-9.81 (m, 1H), 8.46 (s, 1H), 4.07 (s, 3H) ppm. ESI-MS m/z calc. 275.93817, found 277.0 (M+1)$^+$; Retention time: 1.55 minutes (LC Method E).

Step 4: Methyl 5-bromo-6-chloro-3-nitro-pyridine-2-carboxylate

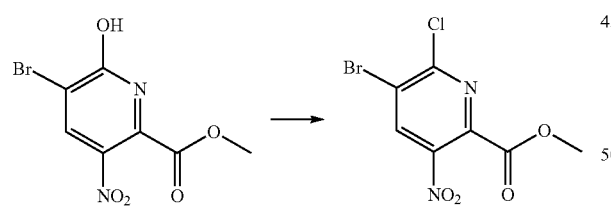

A mixture of methyl 5-bromo-6-hydroxy-3-nitro-pyridine-2-carboxylate (7.5 g, 26.802 mmol) and phenyl dichlorophosphate (32.476 g, 23 mL, 153.93 mmol) was heated at 170° C. for 90 minutes. After cooling to room temperature, the mixture was diluted with ethyl acetate (350 mL) and washed with brine (350 mL). The organic phase was dried over anhydrous sodium sulfate, filtered and concentrated under reduced pressure. The residue was purified by silica gel chromatography (330 g column) using a gradient from 0% to 20% of ethyl acetate in heptanes to afford as a yellow solid, methyl 5-bromo-6-chloro-3-nitro-pyridine-2-carboxylate (7 g, 87%). ESI-MS m/z calc. 293.9043, found 294.9 (M+1)$^+$; Retention time: 1.93 minutes (LC Method E).

Step 5: Methyl 6-[(2S)-2-allylpyrrolidin-1-yl]-5-bromo-3-nitro-pyridine-2-carboxylate

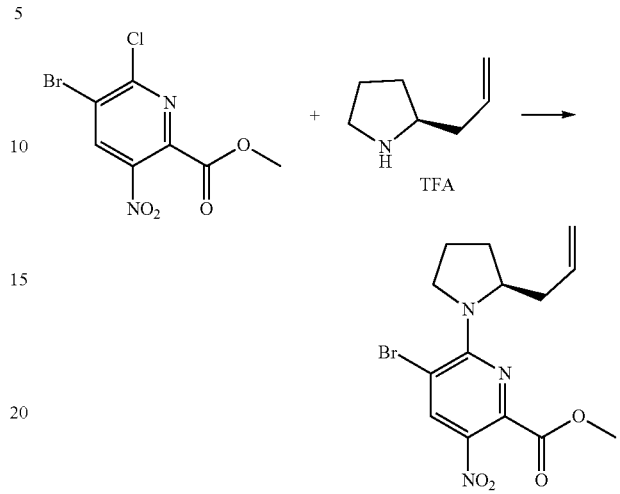

To a solution of methyl 5-bromo-6-chloro-3-nitro-pyridine-2-carboxylate (25 g, 84.61 mmol) and (2S)-2-allylpyrrolidine (trifluoroacetate salt) (31 g, 107.37 mmol) in acetonitrile (250 mL) was added DIEA (75.684 g, 102 mL, 585.59 mmol) and the mixture was refluxed for 3 h. The reaction mixture was cooled to ambient temperature and the solvent was removed in vacuo. The residue was diluted with ethyl acetate (500 mL) and washed with brine (2×200 mL), dried over sodium sulfate, filtered and concentrated in vacuo. The crude product was purified by silica gel chromatography eluting with a gradient from 0% to 35% EtOAc in hexanes to afford as a brown oil, methyl 6-[(2S)-2-allylpyrrolidin-1-yl]-5-bromo-3-nitro-pyridine-2-carboxylate (22.01 g, 69%). ESI-MS m/z calc. 369.0324, found 370.0 (M+1)$^+$; Retention time: 3.9 minutes (LC Method G).

Step 6: 6-[(2S)-2-Allylpyrrolidin-1-yl]-5-bromo-3-nitro-pyridine-2-carboxylic acid

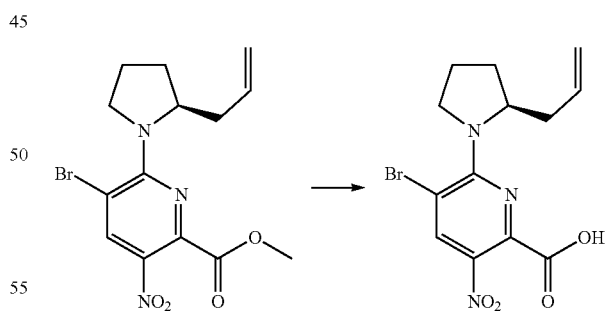

To a solution of methyl 6-[(2S)-2-allylpyrrolidin-1-yl]-5-bromo-3-nitro-pyridine-2-carboxylate (1.4 g, 3.5511 mmol) in tetrahydrofuran (7 mL) was added a solution of LiOH (400 mg, 9.5321 mmol) in water (7 mL). The resulting mixture was stirred at 50° C. for 4 hours. The solvent was evaporated then diluted with H$_2$O (50 mL) and acidified with 1 N HCl (pH 3). The mixture was extracted with EtOAc (3×50 mL) and the combined organic layers were dried over Na$_2$SO$_4$, filtered and concentrated under reduced pressure to provide as a yellow oil, 6-[(2S)-2-allylpyrrolidin-1-yl]-5- bromo-3-nitro-pyridine-2-carboxylic acid (1.34 g, 100%). ¹H NMR (300 MHz, Chloroform-d) δ 8.47 (s, 1H), 6.69-6.39 (m, 1H), 5.88-5.66 (m, 1H), 5.20-5.02 (m, 2H), 4.78-4.62 (m, 1H), 4.09-3.98 (m, 1H), 3.93-3.81 (m, 1H), 2.65-2.52 (m, 1H), 2.33-2.18 (m, 1H), 2.14-2.05 (m, 2H), 1.95-1.82 (m, 2H) ppm. ESI-MS m/z calc. 355.01675, found 356.0 (M+1)⁺; Retention time: 1.96 minutes (LC Method E).

Step 7: 6-[(2S)-2-Allylpyrrolidin-1-yl]-N'-[2-benzyloxy-2-(trifluoromethyl)hex-5-enoyl]-5-bromo-3-nitro-pyridine-2-carbohydrazide

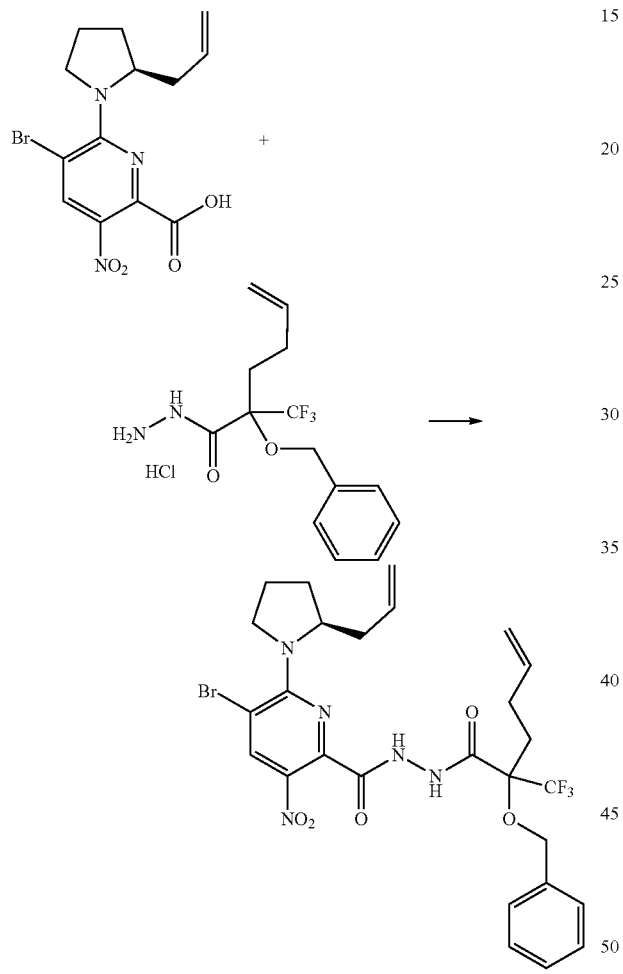

To a solution of 6-[(2S)-2-allylpyrrolidin-1-yl]-5-bromo-3-nitro-pyridine-2-carboxylic acid (5.41 g, 14.232 mmol) in CH₂Cl₂ (90 mL) at room temperature was added oxalyl chloride (2.5463 g, 1.75 mL, 20.061 mmol), followed by DMF (1.3 g, 1.3771 mL, 17.785 mmol) dropwise. The mixture was stirred at room temperature for 1 h and a solution of 2-benzyloxy-2-(trifluoromethyl)hex-5-enehydrazide (hydrochloride salt) (5.82 g, 17.181 mmol) and DIPEA (2.8938 g, 3.9 mL, 22.390 mmol) in CH₂Cl₂ (60 mL) was added dropwise over 15 min. The resulting mixture was stirred at room temperature for 20 min and more DIPEA (222.60 mg, 0.3 mL, 1.7223 mmol) was added. The mixture was stirred at room temperature for 10 min, cooled to 0° C. and 5% aq. NaHCO₃ (200 mL) was added. The two layers were separated, and the aqueous layer was extracted with CH₂Cl₂ (2×100 mL). The combined organic layers were dried over anhydrous Na₂SO₄, filtered and concentrated. The residue was purified by silica gel chromatography (120 g column) using a gradient from 0% to 30% EtOAc in heptanes to afford as a yellow foam, 6-[(2S)-2-allylpyrrolidin-1-yl]-N'-[2-benzyloxy-2-(trifluoromethyl)hex-5-enoyl]-5-bromo-3-nitro-pyridine-2-carbohydrazide (8.56 g, 94%). ¹H NMR (300 MHz, Chloroform-d) δ 9.28 (d, J=6.2 Hz, 1H), 9.03 (t, J=6.5 Hz, 1H), 8.26 (d, J=1.2 Hz, 1H), 7.59-7.28 (m, 5H), 5.92-5.63 (m, 2H), 5.19-4.94 (m, 4H), 4.89-4.77 (m, 1H), 4.75-4.68 (m, 1H), 4.66-4.51 (m, 1H), 4.09-3.93 (m, 1H), 3.85-3.71 (m, 1H), 2.62-2.35 (m, 2H), 2.32-1.95 (m, 6H), 1.91-1.73 (m, 2H) ppm. ¹⁹F NMR (282 MHz, Chloroform-d) δ−73.66 (s, 3F) ppm. ESI-MS m/z calc. 639.13043, found 640.2 (M+1)⁺; Retention time: 2.34 minutes (LC Method E).

Step 8: 2-[6-[(2S)-2-Allylpyrrolidin-1-yl]-5-bromo-3-nitro-2-pyridyl]-5-[1-benzyloxy-1-(trifluoromethyl)pent-4-enyl]-1,3,4-oxadiazole

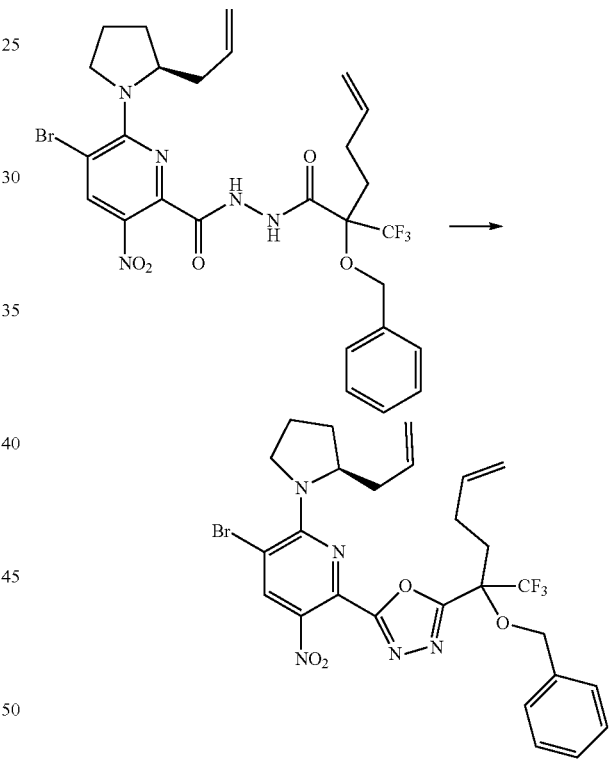

To a solution of 6-[(2S)-2-allylpyrrolidin-1-yl]-N'-[2-benzyloxy-2-(trifluoromethyl)hex-5-enoyl]-5-bromo-3-nitro-pyridine-2-carbohydrazide (13.3 g, 20.767 mmol) and diisopropylethylamine (8.0136 g, 10.8 mL, 62.004 mmol) in acetonitrile (340 mL) at 50° C. was added p-toluenesulfonyl chloride (4.15 g, 21.768 mmol) portion wise. The mixture was stirred at 70° C. for 1.5 hours and cooled to ambient temperature and concentrated. The residue was dissolved in ethyl acetate (125 mL), washed with aqueous 5% NaHCO₃ (25 mL), water (2×25 mL), brine (50 mL), dried over anhydrous sodium sulfate and filtered. The volatiles were removed by evaporation under reduced pressure and the residue was purified by silica gel chromatography (220 g column) using a gradient from 0% to 15% ethyl acetate in heptanes which gave as a red oil, 2-[6-[(2S)-2-allylpyrroli-din-1-yl]-5-bromo-3-nitro-2-pyridyl]-5-[1-benzyloxy-1-(trifluoromethyl)pent-4-enyl]-1,3,4-oxadiazole (11.54 g, 89%). $^1$H NMR (300 MHz, Chloroform-d) δ 8.56 (s, 1H), 7.49-7.27 (m, 5H), 5.91-5.58 (m, 2H), 5.23-4.89 (m, 4H), 4.79 (dd, J=10.6, 4.1 Hz, 1H), 4.72-4.54 (m, 2H), 4.13-3.95 (m, 1H), 3.94-3.76 (m, 1H), 2.69-1.62 (m, 10H) ppm. $^{19}$F NMR (282 MHz, Chloroform-d) δ −73.13 (br. s., 3F), −73.26 (s, 3F) ppm. ESI-MS m/z calc. 621.1199, found 622.2 (M+1)$^+$; Retention time: 2.69 minutes (LC Method E).

Step 9: (12S)-6-(Benzyloxy)-18-bromo-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture)

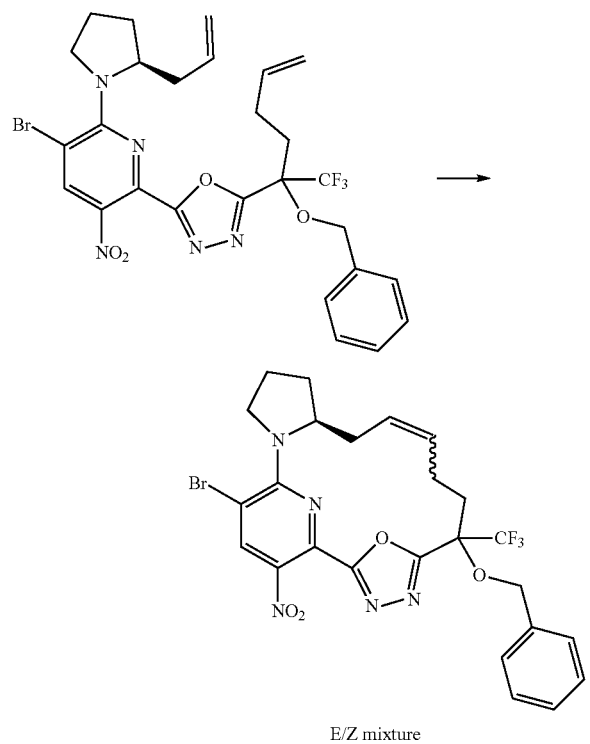

E/Z mixture

In a 1.0 L oven dried round-bottom flask, a degassed solution of 2-[6-[(2S)-2-allylpyrrolidin-1-yl]-5-bromo-3-nitro-2-pyridyl]-5-[1-benzyloxy-1-(trifluoromethyl)pent-4-enyl]-1,3,4-oxadiazole (1.9 g, 2.7259 mmol) in dichloroethane (475 mL) was heated to 50° C. under nitrogen atmosphere. Then, Zhan catalyst-1B (300 mg, 0.4089 mmol) was added in two portions over 15 minutes. The resulting mixture was heated at 70° C. for 3 hours. The mixture was cooled and concentrated under reduced pressure. The residue was purified by silica gel chromatography (80 g column) using a gradient from 0% to 20% ethyl acetate in heptanes which gave as a yellow foam, (12S)-6-(benzyloxy)-18-bromo-20-nitro-6-(trifluoromethyl)-22-oxa-3,4,16,21-tetraazatetracyclo[15.3.1.1²,⁵.0¹²,¹⁶]docosa-1(21),2,4,9,17, 19-hexaene (E/Z mixture) (1.2 g, 73%). ESI-MS m/z calc. 593.08856, found 594.1 (M+1)$^+$; Retention time: 2.48 minutes (LC Method E).

Step 10: (12S)-6-(Benzyloxy)-18-methyl-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z Mixture)

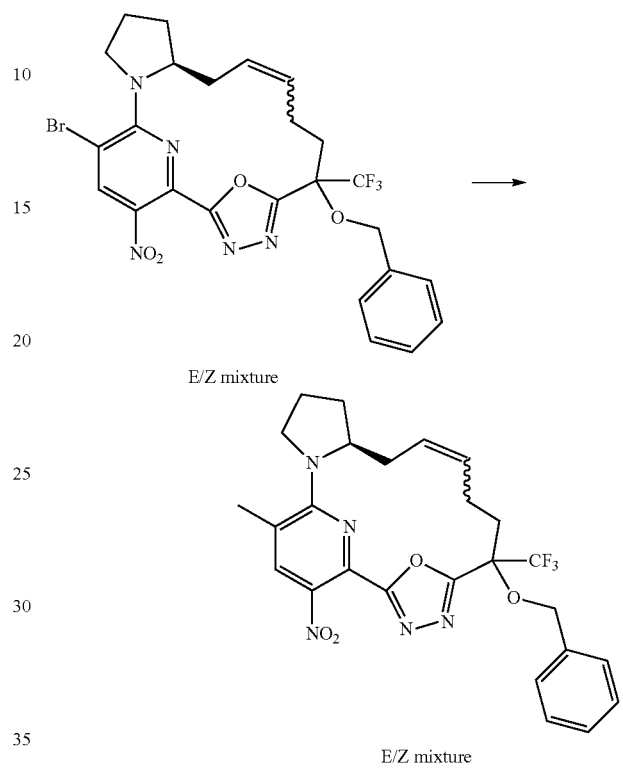

To a solution of (12S)-6-(benzyloxy)-18-bromo-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (100 mg, 0.1682 mmol) in dioxane (2 mL) was added methylboronic acid (30 mg, 0.5012 mmol), palladium (II) acetate (5 mg, 0.0223 mmol), Xantphos (30 mg, 0.0518 mmol) and potassium carbonate (70 mg, 0.5065 mmol) and the reaction mixture was purged with nitrogen for 5 minutes. The reaction mixture was stirred at 100° C. for 16 h, then filtered through pad of Celite washing with EtOAc (3×10 mL). The filtrate was concentrated under reduced pressure and purified by silica gel chromatography (24 g column) using a gradient from 0% to 25% ethyl acetate in heptane to afford as a yellow foam, (12S)-6-(benzyloxy)-18-methyl-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (62 mg, 70%). $^1$H NMR (300 MHz, Chloroform-d) δ 8.09 (s, 1H), 7.42-7.28 (m, 5H), 5.64-5.43 (m, 2H), 5.24 (d, J=10.9 Hz, 1H), 5.02-4.91 (m, 1H), 4.10-3.96 (m, 1H), 3.95-3.85 (m, 1H), 3.84-3.73 (m, 1H), 3.44-3.25 (m, 1H), 2.52 (s, 3H), 2.45-2.25 (m, 2H), 2.23-2.06 (m, 4H), 1.92-1.73 (m, 2H), 1.54-1.44 (m, 1H) ppm. $^{19}$F NMR (282 MHz, Chloroform-d) δ −73.06 (s, 3F), −73.53 (br. s., 3F) ppm. ESI-MS m/z calc. 529.19366, found 530.2 (M+1)$^+$; Retention time: 2.53 minutes (LC Method E).

Step 11: (12R)-20-Amino-18-methyl-6-(trifluoromethyl)-22-oxa-3,4,16,21-tetraazatetracyclo[15.3.1.12,5.012,16]docosa-1(21),2,4,17,19-pentaen-6-ol (enantiomer 1) (Compound 50) and (12R)-20-amino-18-methyl-6-(trifluoromethyl)-22-oxa-3,4,16,21-tetraazatetracyclo[15.3.1.12,5.012,16]docosa-1(21),2,4,17,19-pentaen-6-ol (enantiomer 2) (Compound 51)

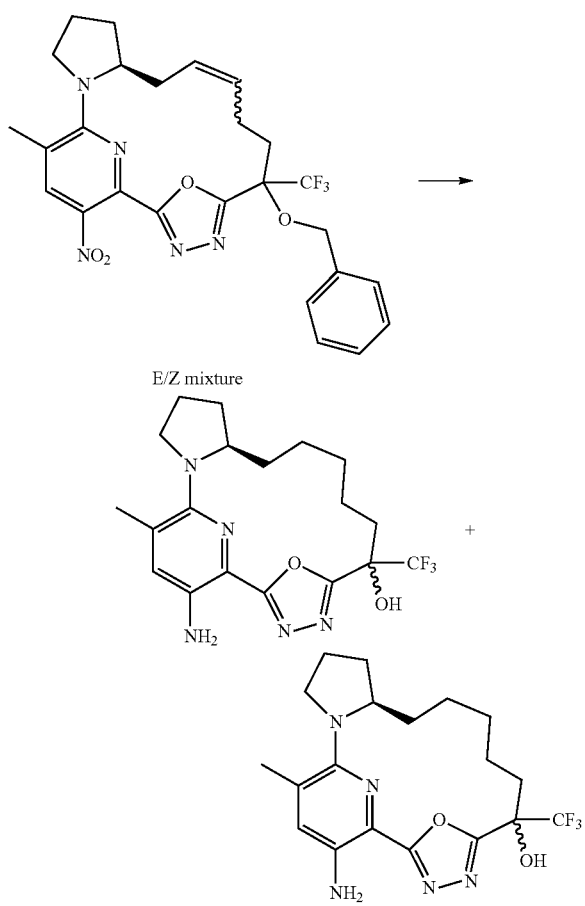

To a solution of (12S)-6-(benzyloxy)-18-methyl-20-nitro-6-(trifluoromethyl)-22-oxa-3,4,16,21-tetraazatetracyclo[15.3.1.12,5.012,16]docosa-1(21),2,4,9,17,19-hexaene (E/Z mixture) (62 mg, 0.1171 mmol) in methanol (7 mL) was added 5% palladium on carbon (37 mg, 0.0174 mmol). The resulting mixture was bubbled with hydrogen for 5 min and stirred at room temperature under hydrogen balloon for 4 hours. More 5% palladium on carbon (15 mg, 0.007 mmol) was added and the mixture was stirred for two more hours under hydrogen atmosphere. The mixture was filtered through pad of Celite washing with methanol (25 mL) and the filtrate was concentrated under reduced pressure. The residue was purified by silica gel chromatography (24 g column) using a gradient from 0% to 25% ethyl acetate in heptanes which gave as a yellow solid and as mixture of diastereomers, (12R)-20-amino-18-methyl-6-(trifluoromethyl)-22-oxa-3,4,16,21-tetraazatetracyclo[15.3.1.12,5.012,16]docosa-1(21),2,4,17,19-pentaen-6-ol (mixture of diastereomers) (8 mg, 15%). This material was further purified by chiral SFC using an OD-H column (250×21.2 mm, 5 μm particle size) sold by Chiral Technologies and eluting with a gradient from 15% to 35% MeOH (+20 mM $NH_3$) in $CO_2$ over 14.5 minutes which provided two single enantiomer products:

The first enantiomer to elute was isolated as a yellow solid, (12R)-20-amino-18-methyl-6-(trifluoromethyl)-22-oxa-3,4,16,21-tetraazatetracyclo[15.3.1.12,5.012,16]docosa-1(21),2,4,17,19-pentaen-6-ol (enantiomer 1) (3.7 mg, 56%). ESI-MS m/z calc. 411.1882, found 412.0 $(M+1)^+$; Retention time: 1.99 minutes (LC Method D).

The second enantiomer to elute was isolated as a yellow solid, (12R)-20-amino-18-methyl-6-(trifluoromethyl)-22-oxa-3,4,16,21-tetraazatetracyclo[15.3.1.12,5.012,16]docosa-1(21),2,4,17,19-pentaen-6-ol (enantiomer 2) (8.9 mg, 75%). ESI-MS m/z calc. 411.1882, found 412.0 $(M+1)^+$; Retention time: 1.90 minutes (LC Method D).

Example 30: Preparation of 17-amino-13-isopropyl-6,15-bis(trifluoromethyl)-19-oxa-3,4,13,18-tetrazatricyclo[12.3.1.12,5]nonadeca-1(18),2,4,14,16-pentaen-6-ol (enantiomer 1) (Compound 52) and 17-amino-13-isopropyl-6,15-bis(trifluoromethyl)-19-oxa-3,4,13,18-tetrazatricyclo[12.3.1.12,5]nonadeca-1(18),2,4,14,16-pentaen-6-ol (enantiomer 2) (Compound 53)

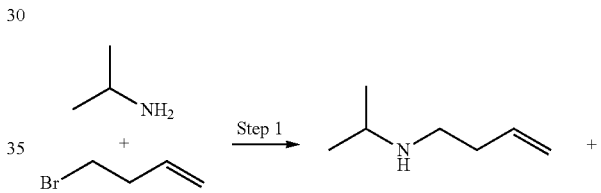

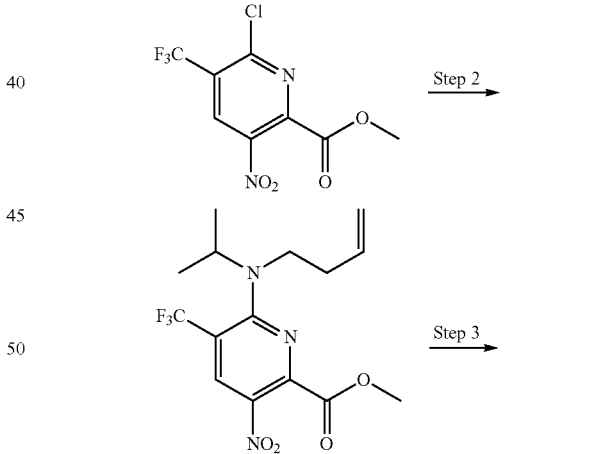

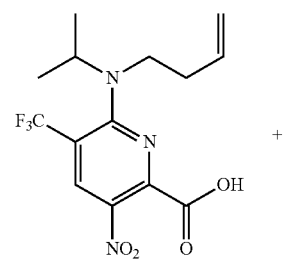

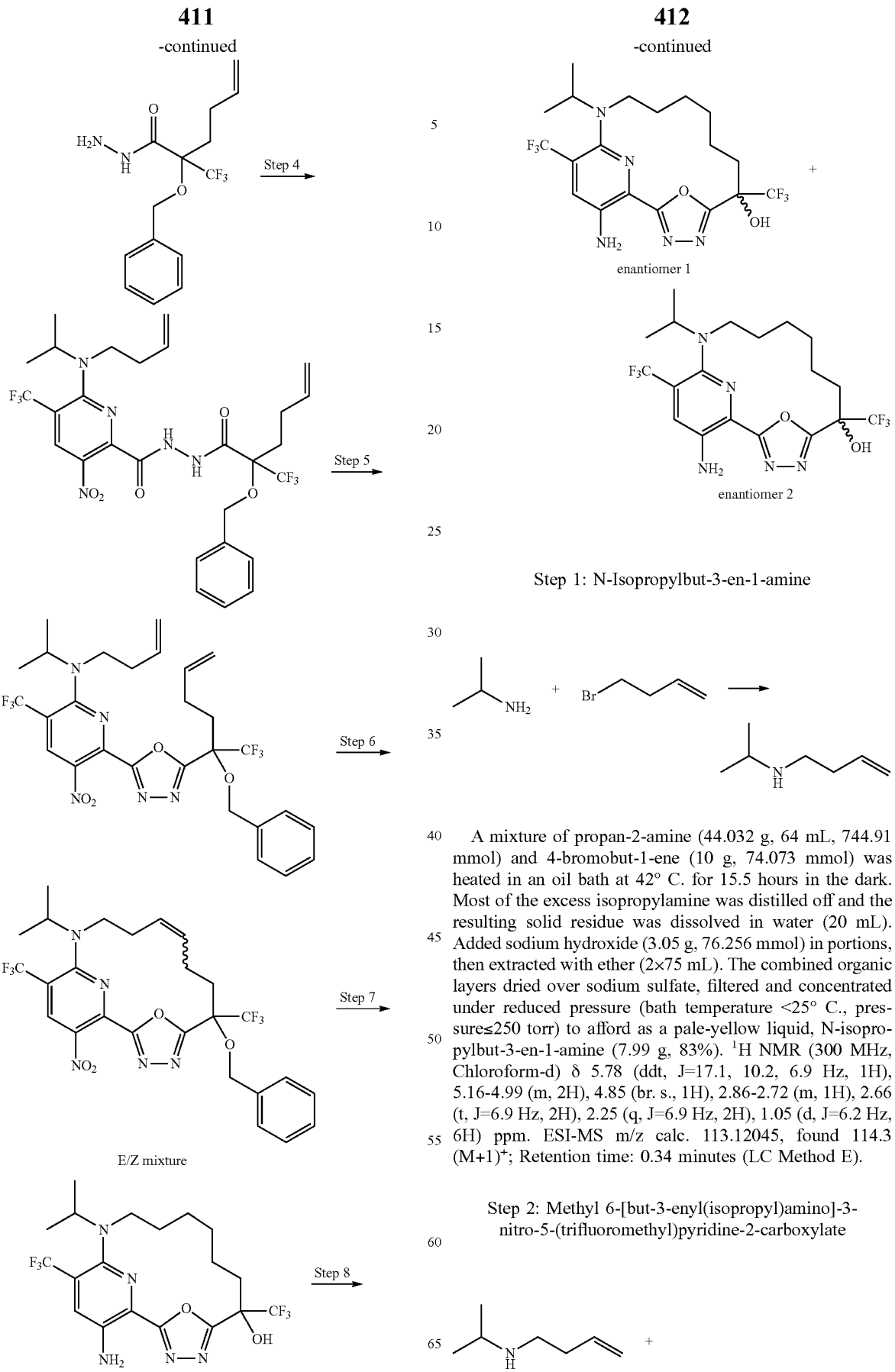

Step 1: N-Isopropylbut-3-en-1-amine

A mixture of propan-2-amine (44.032 g, 64 mL, 744.91 mmol) and 4-bromobut-1-ene (10 g, 74.073 mmol) was heated in an oil bath at 42° C. for 15.5 hours in the dark. Most of the excess isopropylamine was distilled off and the resulting solid residue was dissolved in water (20 mL). Added sodium hydroxide (3.05 g, 76.256 mmol) in portions, then extracted with ether (2×75 mL). The combined organic layers dried over sodium sulfate, filtered and concentrated under reduced pressure (bath temperature <25° C., pressure≤250 torr) to afford as a pale-yellow liquid, N-isopropylbut-3-en-1-amine (7.99 g, 83%). $^1$H NMR (300 MHz, Chloroform-d) δ 5.78 (ddt, J=17.1, 10.2, 6.9 Hz, 1H), 5.16-4.99 (m, 2H), 4.85 (br. s., 1H), 2.86-2.72 (m, 1H), 2.66 (t, J=6.9 Hz, 2H), 2.25 (q, J=6.9 Hz, 2H), 1.05 (d, J=6.2 Hz, 6H) ppm. ESI-MS m/z calc. 113.12045, found 114.3 (M+1)$^+$; Retention time: 0.34 minutes (LC Method E).

Step 2: Methyl 6-[but-3-enyl(isopropyl)amino]-3-nitro-5-(trifluoromethyl)pyridine-2-carboxylate

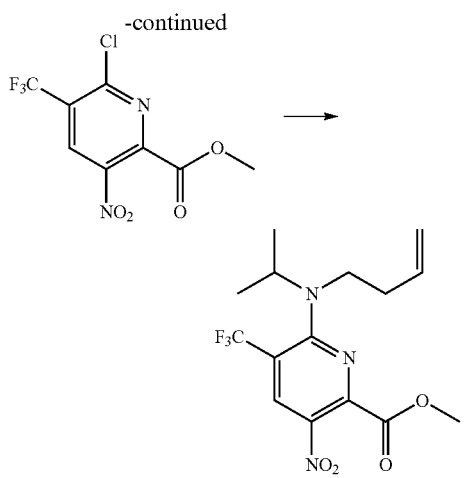

To a solution of methyl 6-chloro-3-nitro-5-(trifluoromethyl)pyridine-2-carboxylate (2 g, 7.0280 mmol) and N-isopropylbut-3-en-1-amine (1.9 g, 10.406 mmol) in acetonitrile (20 mL) was added diisopropylethylamine (2.7454 g, 3.7 mL, 21.242 mmol) and the mixture was refluxed for 1 hour. The reaction mixture was cooled to ambient temperature and the solvent was removed in vacuo. The residue was diluted with ethyl acetate (75 mL) and washed with brine (2×50 mL), dried over sodium sulfate, filtered and concentrated in vacuo. The residue was purified by silica gel chromatography (80 g column) using a gradient from 0% to 20% dichloromethane in heptane to provide as a yellow solid, methyl 6-[but-3-enyl(isopropyl)amino]-3-nitro-5-(trifluoromethyl)pyridine-2-carboxylate (1.85 g, 71%). $^1$H NMR (300 MHz, Chloroform-d) δ 8.61 (s, 1H), 5.75 (dtd, J=14.6, 9.9, 7.0 Hz, 1H), 5.15-4.94 (m, 2H), 4.29 (m, J=6.5 Hz, 1H), 4.02 (s, 3H), 3.56 (dd, J=8.2, 6.8 Hz, 2H), 2.31 (q, J=7.1 Hz, 2H), 1.27 (d, J=6.5 Hz, 6H) ppm. $^{19}$F NMR (282 MHz, Chloroform-d) δ−58.38 (s, 3F) ppm. ESI-MS m/z calc. 361.12494, found 362.1 (M+1)$^+$; Retention time: 3.58 minutes (LC Method C).

Step 3: 6-[But-3-enyl(isopropyl)amino]-3-nitro-5-(trifluoromethyl)pyridine-2-carboxylic Acid

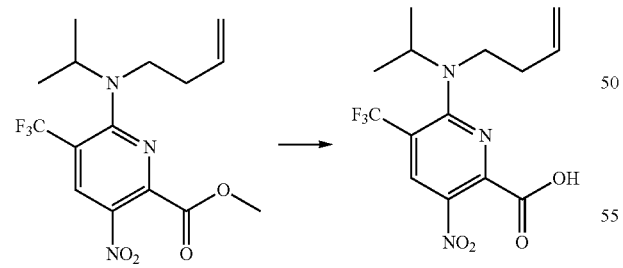

To a solution of methyl 6-[but-3-enyl(isopropyl)amino]-3-nitro-5-(trifluoromethyl)pyridine-2-carboxylate (1.75 g, 4.843 mmol) in THF (20 mL) was added MeOH (20 mL) and water (16.5 mL) followed by lithium hydroxide (500 mg, 20.88 mmol). The mixture was stirred at 60° C. for 2 h. THF and methanol were removed under reduced pressure and 10 mL HCl (10%) was added to acidify to pH ~4 and the product was extracted with EtOAc (2×50 mL). The organic phases were combined, washed with brine (5 mL), dried over anhydrous sodium sulfate, filtered and concentrated under reduced pressure. The residue was purified by silica gel chromatography (120 gram column) using a gradient from 100% hexanes to 80% ethyl acetate in hexanes to afford as a yellow solid, 6-[but-3-enyl(isopropyl)amino]-3-nitro-5-(trifluoromethyl)pyridine-2-carboxylic acid (1.13 g, 67%). $^1$H NMR (400 MHz, DMSO-d6) δ 14.25 (s, 1H), 8.64 (s, 1H), 5.76 (ddt, J=18.9, 9.5, 6.9 Hz, 1H), 5.07-4.93 (m, 2H), 4.15 (h, J=6.6 Hz, 1H), 3.55 (dd, J=8.3, 6.3 Hz, 2H), 2.26 (q, J 7.2 Hz, 2H), 1.23 (d, J=6.5 Hz, 6H) ppm. ESI-MS m/z calc. 347.10928, found 348.2 (M+1)$^+$; Retention time: 1.75 minutes (LC Method A).

Step 4: N'-[2-Benzyloxy-2-(trifluoromethyl)hex-5-enoyl]-6-[but-3-enyl(isopropyl)amino]-3-nitro-5-(trifluoromethyl)pyridine-2-carbohydrazide

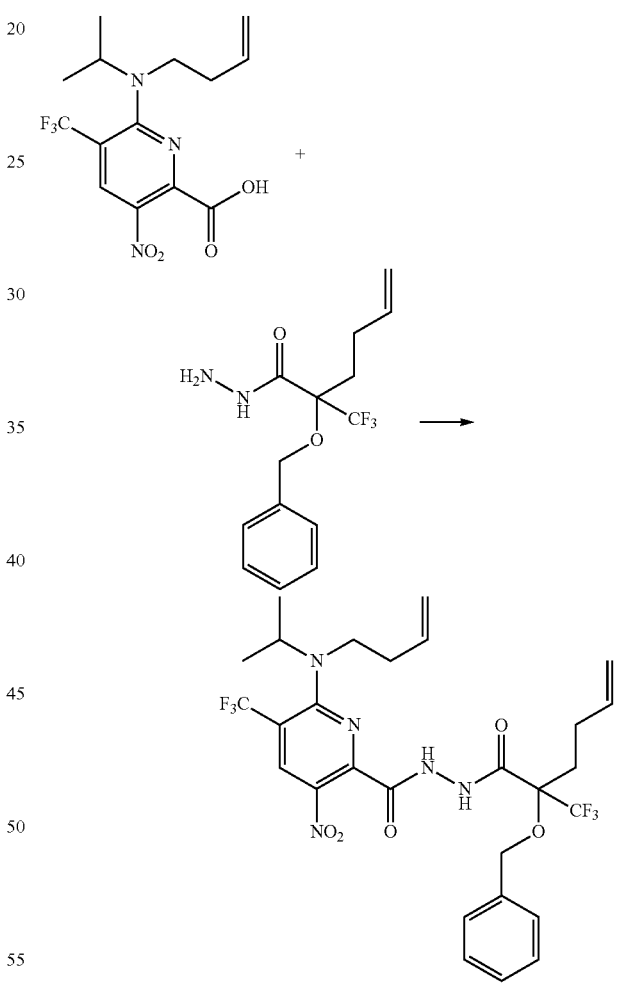

To a solution of 6-[but-3-enyl(isopropyl)amino]-3-nitro-5-(trifluoromethyl)pyridine-2-carboxylic acid (1.13 g, 3.254 mmol) in NMP (20 mL) at 0° C. was added 2-benzyloxy-2-(trifluoromethyl)hex-5-enehydrazide (1.1 g, 3.639 mmol) and DIEA (2.75 mL, 15.79 mmol) followed by HATU (1.35 g, 3.55 mmol). The reaction mixture was warmed to room temperature and stirred for 18 h. The reaction was diluted with ethyl acetate and washed with a saturated aqueous sodium bicarbonate solution. The organic layer was further washed with 10% citric acid solution followed by brine. The organics were separated, dried over sodium sulfate, filtered and evaporated. The residue was purified by silica gel chromatography (120 gram column) using a gradient from 100% hexanes to 60% ethyl acetate in to afford as a yellow foam, N-[2-benzyloxy-2-(trifluoromethyl)hex-5-enoyl]-6-[but-3-enyl(isopropyl)amino]-3-nitro-5-(trifluoromethyl)pyridine-2-carbohydrazide (1.65 g, 80%). ESI-MS m/z calc. 631.22296, found 632.2 (M+1)$^+$; Retention time: 1.82 minutes (LC Method J).

Step 5: 6-[5-[1-Benzyloxy-1-(trifluoromethyl)pent-4-enyl]-1,3,4-oxadiazol-2-yl]-N-but-3-enyl-N-isopropyl-5-nitro-3-(trifluoromethyl)pyridin-2-amine

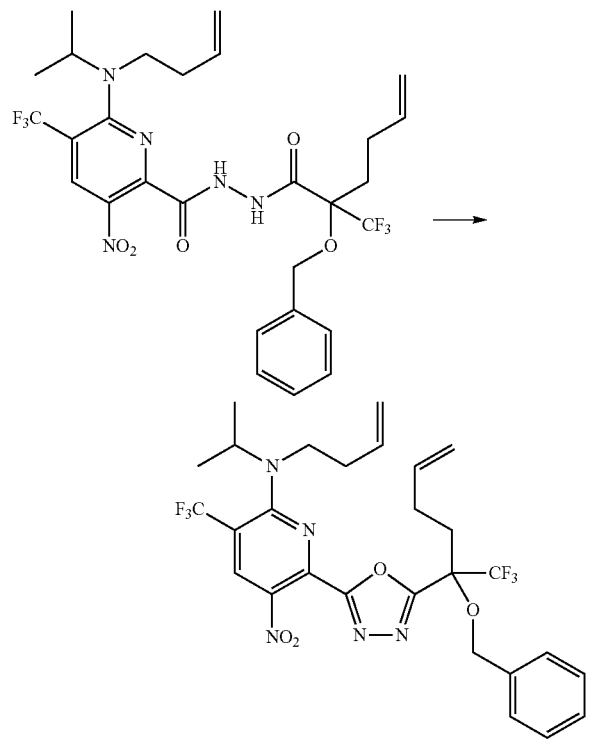

A solution of N-[2-benzyloxy-2-(trifluoromethyl)hex-5-enoyl]-6-[but-3-enyl(isopropyl)amino]-3-nitro-5-(trifluoromethyl)pyridine-2-carbohydrazide (800 mg, 1.267 mmol) and DIEA (675 µL, 3.875 mmol) in acetonitrile (24 mL) was heated at 50° C., then p-toluenesulfonyl chloride (340 mg, 1.783 mmol) was added in one portion and heated at 70° C. for 1 hour. The reaction mixture was cooled and quenched with saturated aqueous solution of sodium bicarbonate (50 mL) and stirred for 15 minutes. The organic material was extracted with ethyl acetate (3×50 mL). The organics were separated, dried over sodium sulfate, filtered and evaporated. The residue was purified by silica gel chromatography (80 gram column) using a gradient from 100% hexanes to 40% ethyl acetate in hexanes to afford as a yellow solid, 6-[5-[1-benzyloxy-1-(trifluoromethyl)pent-4-enyl]-1,3,4-oxadiazol-2-yl]-N-but-3-enyl-N-isopropyl-5-nitro-3-(trifluoromethyl)pyridin-2-amine (686 mg, 88%). $^1$H NMR (400 MHz, DMSO-d6) δ 8.79 (s, 1H), 7.40-7.30 (m, 5H), 5.85 (ddt, J=16.8, 10.3, 6.4 Hz, 1H), 5.76-5.66 (m, 1H), 5.10 (dq, J=17.1, 1.6 Hz, 1H), 5.03-4.92 (m, 3H), 4.76 (d, J 10.9 Hz, 1H), 4.61 (d, J=10.8 Hz, 1H), 4.18 (h, J=6.5 Hz, 1H), 3.56 (dd, J=8.4, 6.2 Hz, 2H), 2.60-2.51 (m, 2H), 2.27 (q, J=7.1 Hz, 3H), 2.24-2.16 (m, 1H), 1.25 (d, J=6.5 Hz, 6H) ppm. ESI-MS m/z calc. 613.2124, found 614.2 (M+1)$^+$; Retention time: 1.71 minutes (LC Method M).

Step 6: Benzyloxy-13-isopropyl-17-nitro-6,15-bis(trifluoromethyl)-19-oxa-3,4,13,18-tetrazatricyclo[12.3.1.12,5]nonadeca-1(18),2,4,9,14,16-hexaene (E/Z mixture)

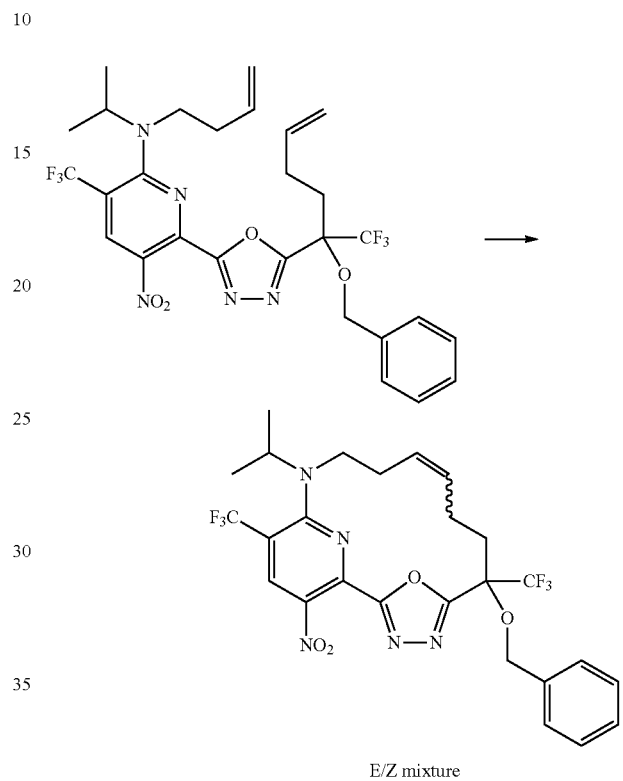

E/Z mixture

In a 1 L round-bottom 3-neck flask, a continuously degassed solution via nitrogen line of Zhan catalyst-1B (205 mg, 0.2794 mmol) in DCE (400 mL) was heated at 50° C. under nitrogen atmosphere. Then, a solution of 6-[5-[1-benzyloxy-1-(trifluoromethyl)pent-4-enyl]-1,3,4-oxadiazol-2-yl]-N-but-3-enyl-N-isopropyl-5-nitro-3-(trifluoromethyl)pyridin-2-amine (682 mg, 1.112 mmol) in DCE (40 mL) was added dropwise via syringe. The resulting mixture was heated at 75° C. for 3 hours. The reaction mixture was cooled to room temperature and concentrated under reduced pressure. The residue was purified by silica gel chromatography (80 gram column) using a gradient from 100% hexanes to 50% ethyl acetate in hexanes to afford as a yellow solid, 6-benzyloxy-13-isopropyl-17-nitro-6,15-bis(trifluoromethyl)-19-oxa-3,4,13,18-tetrazatricyclo[12.3.1.12,5]nonadeca-1(18),2,4,9,14,16-hexaene (E/Z mixture) (550 mg, 84%). $^1$H NMR (400 MHz, DMSO-d6) δ 8.77 (d, J=14.6 Hz, 1H), 7.46-7.26 (m, 5H), 5.65-5.57 (m, 1H), 5.57-5.31 (m, 1H), 4.88-4.79 (m, 2H), 4.13 (tt, J=13.0, 6.5 Hz, 1H), 3.55 (t, J=6.7 Hz, 1H), 3.43 (t, J=8.5 Hz, 1H), 2.39 (t, J=9.5 Hz, 2H), 2.33 (d, J=1.9 Hz, 1H), 2.22 (q, J=9.4, 6.5 Hz, 2H), 2.09 (d, J=16.2 Hz, 1H), 1.28 (q, J=7.0 Hz, 6H) ppm. ESI-MS m/z calc. 585.1811, found 586.2 (M+1)$^+$; Retention time: 1.46 minutes (LC Method M).

Step 7: 17-Amino-13-isopropyl-6,15-bis(trifluoromethyl)-19-oxa-3,4,13,18-tetrazatricyclo[12.3.1.1²,⁵]nonadeca-1(18),2,4,14,16-pentaen-6-ol

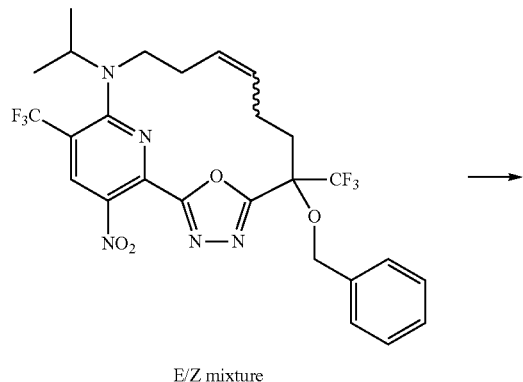

E/Z mixture

A solution of 6-benzyloxy-13-isopropyl-17-nitro-6,15-bis(trifluoromethyl)-19-oxa-3,4,13,18-tetrazatricyclo[12.3.1.1²,⁵]nonadeca-1(18),2,4,9,14,16-hexaene (E/Z mixture) (550 mg, 0.9394 mmol) in AcOH (8.5 mL) and ethyl acetate (8.5 mL) was purged with nitrogen and Pd/C (155 mg of 10% w/w, 0.1456 mmol) was added. The mixture was degassed with nitrogen for 5 minutes, then purged by a balloon filled with hydrogen gas. The mixture was stirred at 1 atm of hydrogen gas for 1 h. Added more Pd/C (850 mg of 10% w/w, 0.7987 mmol) and stirred for 3 more hours. The reaction was filtered over a Celite plug washing with acetonitrile and ethyl acetate and the filtrate was concentrated. The residue was purified by silica gel chromatography (40 gram column) using a gradient from 100% hexanes to 100% ethyl acetate to afford as a yellow solid, 17-amino-13-isopropyl-6,15-bis(trifluoromethyl)-19-oxa-3,4,13,18-tetrazatricyclo[12.3.1.1²,⁵]nonadeca-1(18),2,4,14,16-pentaen-6-ol (349 mg, 79%). $^1$H NMR (400 MHz, DMSO-d6) δ 7.72 (s, 1H), 7.55 (s, 1H), 6.34 (d, J=6.3 Hz, 2H), 3.64 (p, J=6.6 Hz, 1H), 3.17 (t, J=11.3 Hz, 1H), 3.04 (d, J=11.8 Hz, 1H), 2.12 (t, J=7.2 Hz, 2H), 1.71-1.63 (m, 1H), 1.59 (d, J=12.5 Hz, 1H), 1.54-1.37 (m, 6H), 1.09 (dd, J=9.0, 6.6 Hz, 6H) ppm. ESI-MS m/z calc. 467.1756, found 468.2 (M+1)$^+$; Retention time: 2.16 minutes (LC Method A).

Step 8: 17-Amino-13-isopropyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (Compound 52) and 17-amino-13-isopropyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (Compound 53)

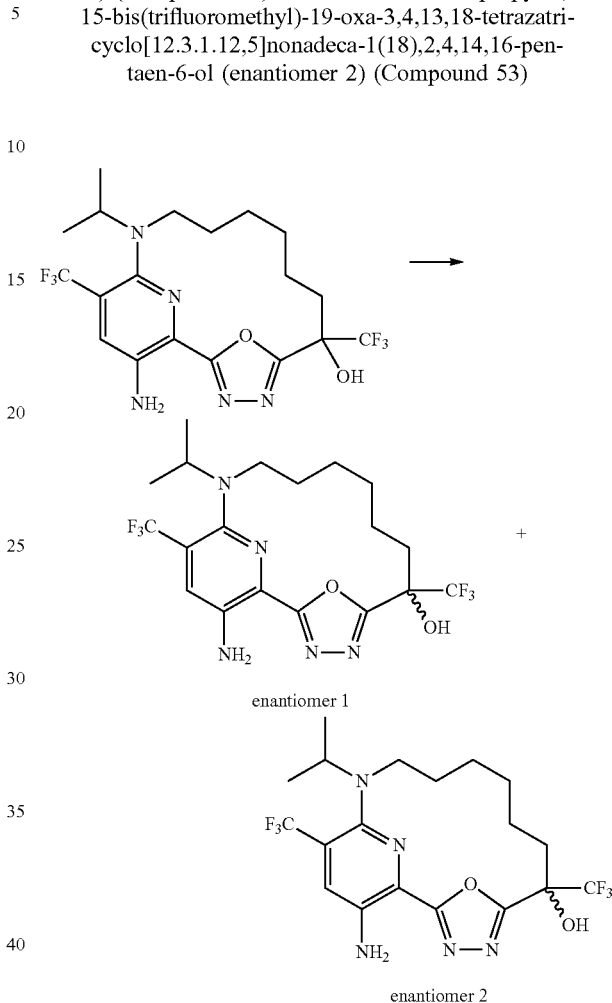

enantiomer 1 enantiomer 2

Racemic 17-amino-13-isopropyl-6,15-bis(trifluoromethyl)-19-oxa-3,4,13,18-tetrazatricyclo[12.3.1.1²,⁵]nonadeca-1(18),2,4,14,16-pentaen-6-ol (349 mg, 0.7467 mmol) was purified by chiral SFC using a LUX-4 column (250× 21.2 mm, 5 μm particle size) sold by Phenomenex and eluting with 8% MeOH (+20 mM NH$_3$)/92% CO$_2$ which provided two single enantiomer products:

The first enantiomer to elute was isolated as a yellow solid, 17-amino-13-isopropyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (129.0 mg, 73%). $^1$H NMR (400 MHz, DMSO-d6) δ 7.72 (s, 1H), 7.56 (s, 1H), 6.35 (s, 2H), 3.65 (p, J=6.6 Hz, 1H), 3.17 (t, J=10.5 Hz, 1H), 3.11-3.01 (m, 1H), 2.12 (t, J=7.1 Hz, 2H), 1.66 (d, J=11.2 Hz, 1H), 1.60-1.52 (m, 1H), 1.52-1.28 (m, 6H), 1.09 (dd, J=8.8, 6.6 Hz, 6H) ppm. ESI-MS m/z calc. 467.1756, found 468.2 (M+1)$^+$; Retention time: 2.16 minutes (LC Method A).

The second enantiomer to elute was isolated as a yellow solid, 17-amino-13-isopropyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (132.6 mg, 75%). $^1$H NMR (400 MHz, DMSO-d6) δ 7.72 (s, 1H), 7.55 (s, 1H), 6.34 (d, J=6.3 Hz, 2H), 3.64 (p, J=6.6 Hz, 1H), 3.20-3.12 (m, 1H), 3.04 (d, J=11.1 Hz, 1H), 2.12 (t, J=7.0 Hz, 2H), 1.67-1.61 (m, 1H), 1.61-1.55 (m, 1H), 1.45 (qd, J=17.8, 15.8, 8.8 Hz, 6H), 1.09 (dd, J=9.0, 6.6 Hz, 6H) ppm. ESI-MS m/z calc. 467.1756, found 468.2 (M+1)$^+$; Retention time: 2.16 minutes (LC Method A).

Step 9: Solid Form Characterization of Crystalline Compound 52 Form a (Neat)

A. X-Ray Powder Diffraction

The XRPD diffractogram for crystalline Compound 52 Form A (neat) produced by Step 8 was acquired using the General X-Ray Powder Diffraction (XRPD) Method. The XRPD diffractogram for crystalline Compound 52 Form A (neat) is provided in FIG. 9, and the XRPD data are summarized below in Table 5.

TABLE 5

XRPD signals for crystalline Compound 52 Form A (neat)

| XRPD Peak No. | Angle (degrees 2-Theta ± 0.2) | Intensity % |
| --- | --- | --- |
| 1 | 6.7649 | 77.6 |
| 2 | 12.7426 | 30.37 |
| 3 | 15.1429 | 11.8 |
| 4 | 15.467 | 12 |
| 5 | 17.2558 | 100 |
| 6 | 18.6449 | 74.23 |
| 7 | 19.1863 | 15.25 |
| 8 | 19.7446 | 10.42 |
| 9 | 20.3974 | 10.55 |
| 10 | 20.5788 | 16.53 |
| 11 | 21.4448 | 27.71 |
| 12 | 27.2406 | 14.77 |

B. Thermogravimetric Analysis (TGA)

Figure 10:
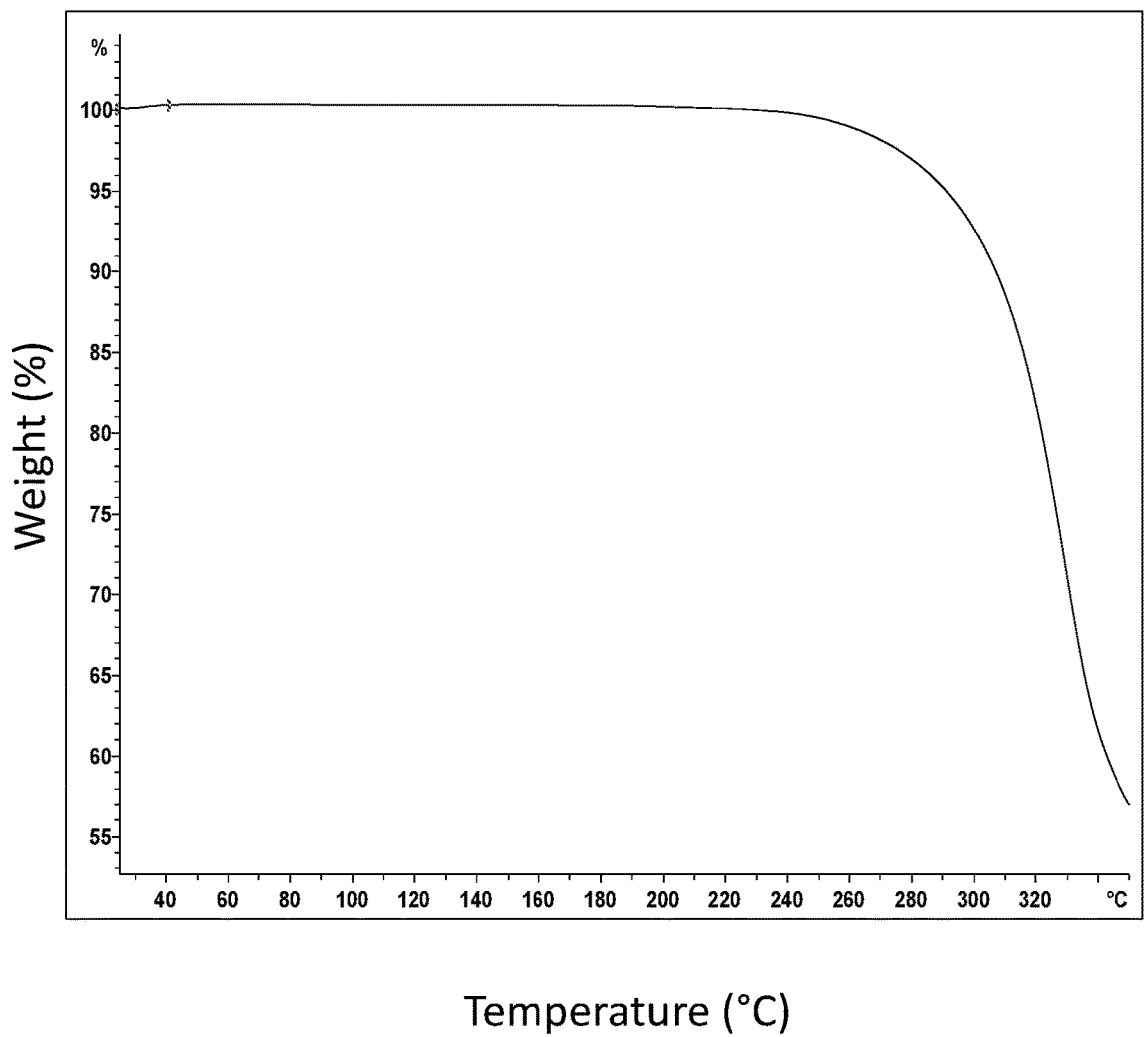
FIG. 10 provides a TGA curve for crystalline Compound 52 Form A (neat).

The TGA curve for crystalline Compound 52 Form A (neat) is provided in FIG. 10. The TGA curve shows no weight loss up to 213.9° C., with a ramp of 10.00° C./min to 350.00° C.

C. Differential Scanning Calorimetry Analysis

Figure 11:
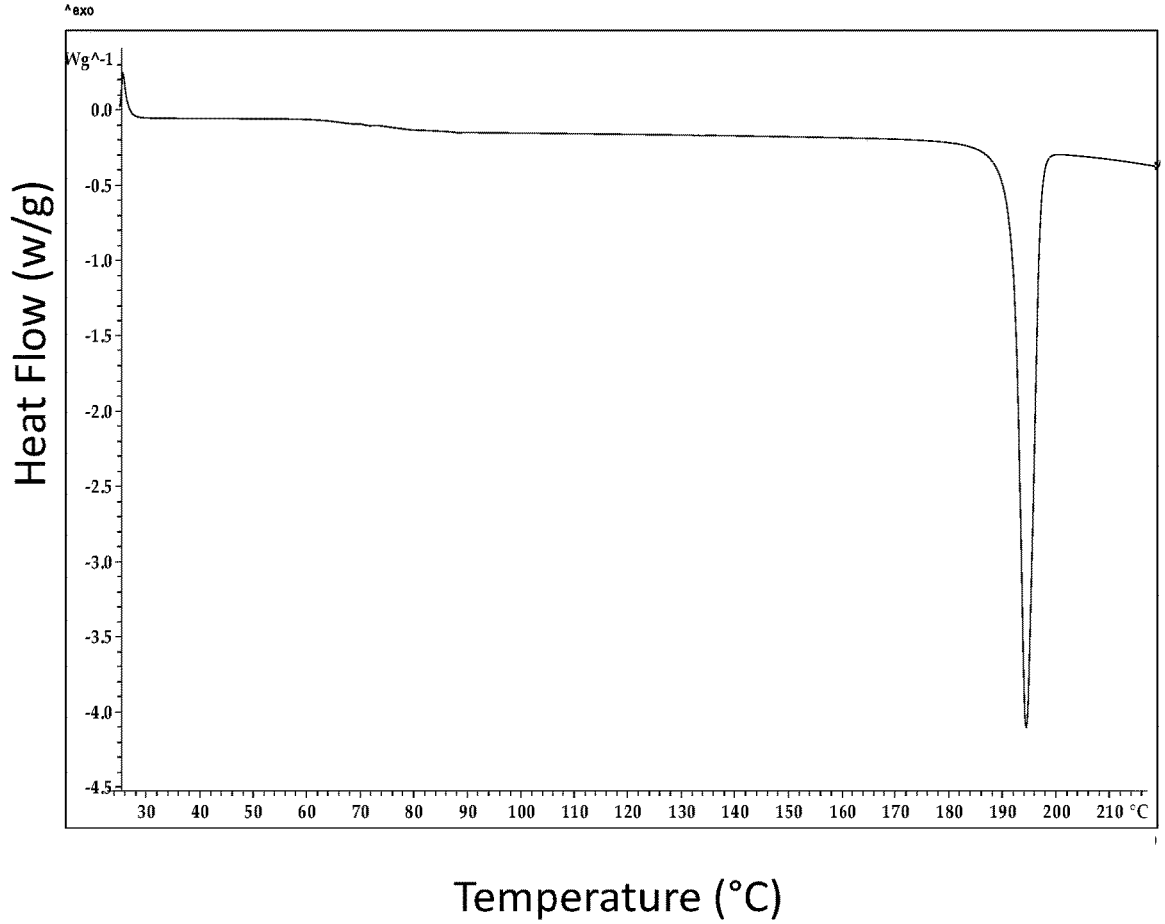
FIG. 11 provides a DSC analysis of crystalline Compound 52 Form A (neat).

The DSC data were collected with a ramp of 10.00° C./min to 220.00° C. The DSC thermogram for crystalline Compound 52 Form A (neat) is provided in FIG. 11. The thermogram shows a Tm onset of 191.94° C., with a Tm peak at 194.42° C., 78.59 J/g.

Example 31: Preparation of (12R)-21-amino-6,19-bis(trifluoromethyl)-14,23-dioxa-3,4,17,22-tetraazatetracyclo[16.3.1.1²,⁵.0¹²,¹⁷]tricosa-1(21),2,4,18(22),19-pentaen-6-ol (enantiomer 1) (Compound 54) and (12R)-21-amino-6,19-bis(trifluoromethyl)-14,23-dioxa-3,4,17,22-tetraazatetracyclo[16.3.1.1²,⁵.0¹²,¹⁷]tricosa-1(21),2,4,18(22),19-pentaen-6-ol (enantiomer 2) (Compound 55)

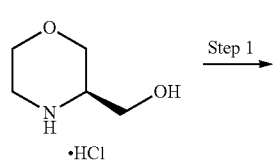

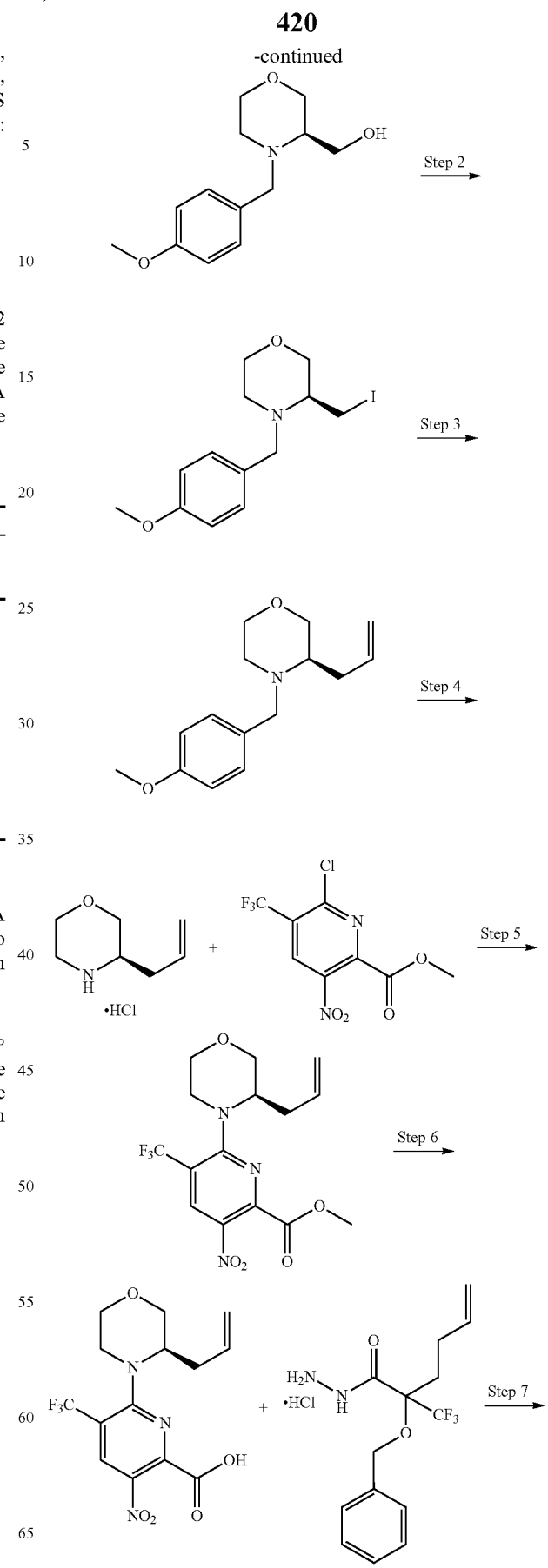

421

-continued

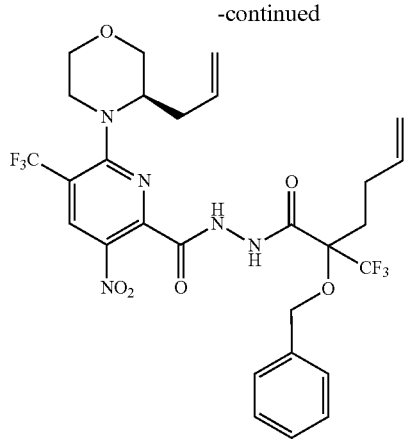

E/Z mixture

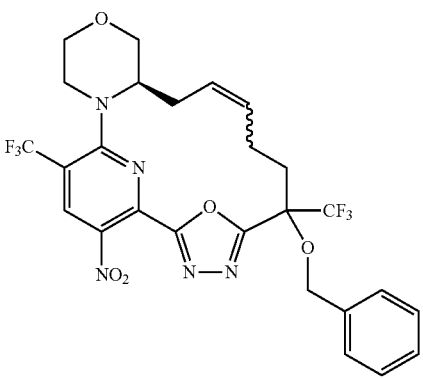

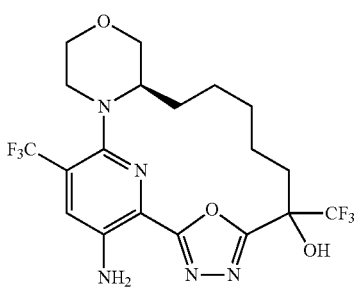

422

-continued

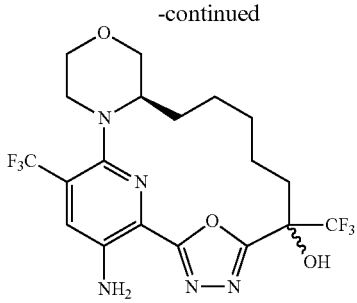

enantiomer 1 enantiomer 2

Step 1: [(3R)-4-[(4-methoxyphenyl)methyl]morpholin-3-yl]methanol


To a suspension of [(3R)-morpholin-3-yl]methanol (hydrochloride salt) (4.4 g, 28.645 mmol) in CH$_2$Cl$_2$ (400 mL) was added Et$_3$N (5.8080 g, 8 mL, 57.397 mmol) and 4-methoxybenzaldehyde (4.1 g, 30.114 mmol). The mixture was stirred at room temperature for 30 min until it became a clear solution. Then, acetic acid (2.1 g, 1.9886 mL, 34.970 mmol) and sodium triacetoxyborohydride (18.2 g, 85.873 mmol) were added and the mixture was stirred at room temperature overnight. The mixture was cooled to 0° C. and a solution of KHCO$_3$ (57 g) in water (200 mL) was added. The two layers were separated, and the aqueous layer was extracted with CH$_2$Cl$_2$ (2×200 mL). The combined organic layers were washed with 5% aqueous NaHCO$_3$ (50 mL), dried over Na$_2$SO$_4$, filtered and concentrated. The residue was purified by silica gel chromatography (120 g column) using a gradient from 0% to 5% MeOH in dichloromethane which gave as a pale-yellow oil, [(3R)-4-[(4-methoxyphenyl)methyl]morpholin-3-yl]methanol (6.45 g, 95%). $^1$H NMR (300 MHz, Chloroform-d) δ 7.25-7.16 (m, 2H), 6.93-6.80 (m, 2H), 4.06 (d, J=12.9 Hz, 1H), 3.97 (dd, J=11.4, 4.4 Hz, 1H), 3.88-3.77 (m, 4H), 3.77-3.70 (m, 1H), 3.65 (dd, J=11.4, 9.4 Hz, 1H), 3.56-3.43 (m, 2H), 3.20 (d, J=13.2 Hz, 1H), 2.72 (dt, J=11.9, 2.9 Hz, 1H), 2.63-2.46 (m, 2H), 2.31

(ddd, J=12.0, 10.0, 3.2 Hz, 1H) ppm. ESI-MS m/z calc. 237.13649, found 238.2 (M+1)⁺; Retention time: 0.69 minutes (LC Method E).

Step 2: (3S)-3-(Iodomethyl)-4-[(4-methoxyphenyl)methyl]morpholine

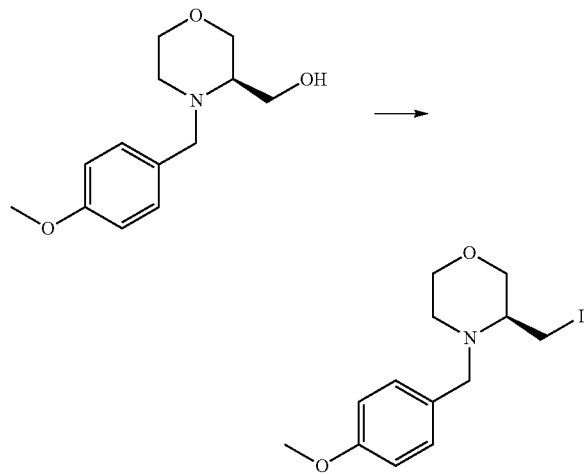

To a solution of [(3R)-4-[(4-methoxyphenyl)methyl]morpholin-3-yl]methanol (6.45 g, 27.181 mmol) in CH$_2$Cl$_2$ (250 mL) was added triphenylphosphine (8.12 g, 30.959 mmol) and imidazole (2.78 g, 40.836 mmol). The mixture was stirred at 0° C. for 5 min. Iodine (8.06 g, 31.756 mmol) was added portion wise and the mixture was stirred at 0° C. for 1 h. The mixture was concentrated to about 100 mL and purified by flash chromatography (120 g column) using a gradient from 0% to 10% MeOH in ethyl acetate which gave as a pale-yellow oil, (3S)-3-(iodomethyl)-4-[(4-methoxyphenyl)methyl]morpholine (8.76 g, 93%). ¹H NMR (300 MHz, Chloroform-d) δ 7.30-7.24 (m, 2H), 6.90-6.81 (m, 2H), 3.85 (d, J=12.9 Hz, 1H), 3.80 (s, 3H), 3.77-3.72 (m, 2H), 3.68-3.60 (m, 2H), 3.51-3.41 (m, 1H), 3.38-3.29 (m, 1H), 3.24 (d, J=12.9 Hz, 1H), 2.70-2.58 (m, 1H), 2.42-2.21 (m, 2H) ppm. ESI-MS m/z calc. 347.0382, found 348.1 (M+1)⁺; Retention time: 1.43 minutes (LC Method E).

Step 3: (3R)-3-Allyl-4-[(4-methoxyphenyl)methyl]morpholine

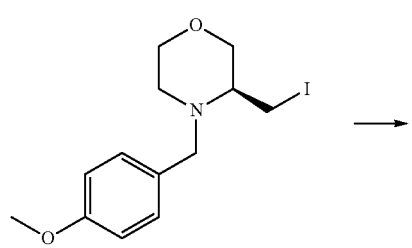

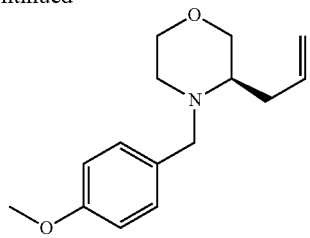

Copper(I) iodide (404 mg, 2.1213 mmol) was suspended in THF (3 mL) under nitrogen and cooled to −40° C. with stirring. Bromo(vinyl)magnesium in THF (4 mL of 1 M, 4 mmol) was slowly added over 10 minutes and the thick suspension was further stirred for 30 min, then allowed to warm to −10° C. The black suspension was cooled to −40° C. and a solution of (3S)-3-(iodomethyl)-4-[(4-methoxyphenyl)methyl]morpholine (460 mg, 1.3249 mmol) in THF (1.5 mL) was added dropwise over 20 min. The thick suspension was stirred for an additional 1 h with slow warming to 15° C. EtOAc (10 mL) and saturated NH$_4$Cl (20 mL) were added. The mixture was stirred at room temperature for 5 min. Then, 28% aqueous NH$_3$ (15 mL) was added. The mixture was extracted with EtOAc (3×30 mL). The combined organic layers were dried with Na$_2$SO$_4$, filtered and concentrated. The residue was purified by silica gel chromatography (40 g column) using a gradient from 0% to 40% EtOAc in heptanes which gave as a colorless oil, (3R)-3-allyl-4-[(4-methoxyphenyl)methyl]morpholine (265 mg, 81%). ¹H NMR (300 MHz, Chloroform-d) δ 7.23 (d, J=8.5 Hz, 2H), 6.85 (d, J=8.5 Hz, 2H), 5.83 (ddt, J=17.1, 10.1, 7.0 Hz, 1H), 5.18-5.01 (m, 2H), 4.00 (d, J=13.2 Hz, 1H), 3.80 (s, 3H), 3.76-3.64 (m, 2H), 3.62-3.52 (m, 1H), 3.46 (dd, J=11.2, 7.9 Hz, 1H), 3.14 (d, J=12.9 Hz, 1H), 2.60 (dt, J=12.0, 3.4 Hz, 1H), 2.46 (td, J=7.6, 3.7 Hz, 1H), 2.41-2.27 (m, 2H), 2.18 (ddd, J=12.0, 8.9, 3.5 Hz, 1H) ppm. ESI-MS m/z calc. 247.15723, found 248.2 (M+1)⁺; Retention time: 1.34 minutes (LC Method E).

Step 4: (3R)-3-Allylmorpholine

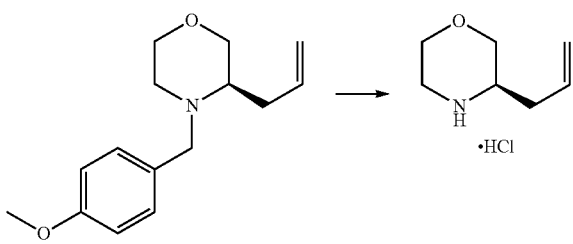

To a solution of (3R)-3-allyl-4-[(4-methoxyphenyl)methyl]morpholine (3.25 g, 13.14 mmol) in 1,2-dichloroethane (60 mL) was added 1-chloroethyl chloroformate (7.5525 g, 5.7 mL, 52.826 mmol). The mixture was stirred at 78° C. for 18 h, cooled to room temperature and concentrated to remove the solvent. The residue was dissolved in MeOH (60 mL) and heated at 80° C. for 1 h. The mixture was concentrated and co-evaporated from EtOAc (2×20 mL). The residue was suspended in 30 mL of a 1:1 mixture of EtOAc and heptane and the resultant precipitate was collected by filtration and washed with a 1:1 mixture of EtOAc and heptane to give as a white solid, (3R)-3-allylmorpholine (hydrochloride salt) (1.515 g, 70%). ¹H NMR (300 MHz, DMSO-d6) δ 9.41 (br. s., 2H), 5.87-5.69 (m, 1H), 5.23-5.09 (m, 2H), 3.93-3.82 (m, 2H), 3.68 (td, J=11.7, 2.6 Hz, 1H), 3.46 (dd, J=12.2, 10.1 Hz, 1H), 3.34-3.12 (m, 2H), 3.11-2.95 (m, 1H), 2.46-2.23 (m, 2H) ppm. ESI-MS m/z calc. 127.09972, found 128.2 (M+1)⁺; Retention time: 0.32 minutes (LC Method E).

Step 5: Methyl 6-[(3R)-3-allylmorpholin-4-yl]-3-nitro-5-(trifluoromethyl)pyridine-2-carboxylate

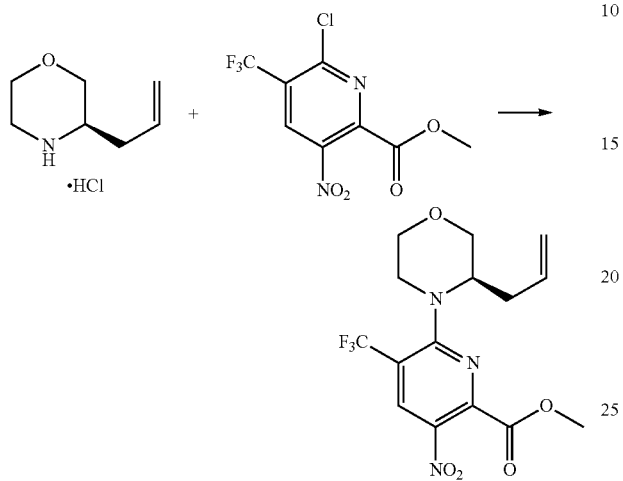

To a suspension of (3R)-3-allylmorpholine (hydrochloride salt) (1.51 g, 9.2273 mmol) in acetonitrile (22 mL) was added DIPEA (3.7100 g, 5 mL, 28.706 mmol) and methyl 6-chloro-3-nitro-5-(trifluoromethyl)pyridine-2-carboxylate (3.2 g, 11.245 mmol). The mixture was stirred at 80° C. for 1 h, cooled to ambient temperature and concentrated. The residue was dissolved in CH₂Cl₂ (100 mL) and washed with a solution of KHCO₃ (3.6 g) in water (50 mL). The aqueous layer was back-extracted with CH₂Cl₂ (50 mL). The combined organic layers were dried over anhydrous Na₂SO₄, filtered and concentrated. The residue was purified by silica gel chromatography (120 g column) using a gradient from 0% to 30% EtOAc in heptane to afford as a red oil, methyl 6-[(3R)-3-allylmorpholin-4-yl]-3-nitro-5-(trifluoromethyl)pyridine-2-carboxylate (3.64 g, 100%). ¹H NMR (300 MHz, Chloroform-d) δ 8.61 (s, 1H), 5.64 (ddt, J=17.1, 10.0, 7.3 Hz, 1H), 5.18-4.97 (m, 2H), 4.70-4.53 (m, 1H), 4.01 (s, 3H), 3.99-3.86 (m, 2H), 3.75-3.52 (m, 4H), 2.62 (t, J=7.3 Hz, 2H) ppm. ¹⁹F NMR (282 MHz, Chloroform-d) δ−57.41 (s, 3F) ppm. ESI-MS m/z calc. 375.10422, found 376.1 (M+1)⁺; Retention time: 2.12 minutes (LC Method E).

Step 6: 6-[(3R)-3-Allylmorpholin-4-yl]-3-nitro-5-(trifluoromethyl)pyridine-2-carboxylic Acid

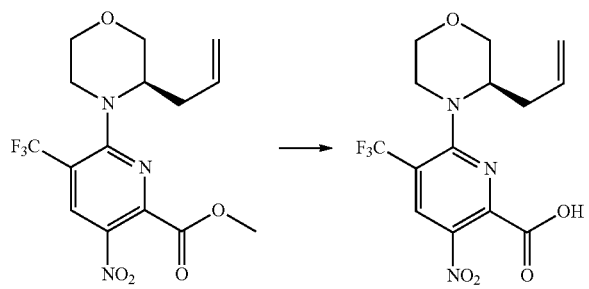 [SMILES: C=CC[C@@H]1COCCN1c1nc(C(=O)OC)c([N+](=O)[O-])cc1C(F)(F)F ; C=CC[C@@H]1COCCN1c1nc(C(=O)O)c([N+](=O)[O-])cc1C(F)(F)F]

To a solution of methyl 6-[(3R)-3-allylmorpholin-4-yl]-3-nitro-5-(trifluoromethyl)pyridine-2-carboxylate (3.6 g, 9.5923 mmol) in THF (40 mL) at 0° C. was added a solution of sodium hydroxide (762 mg, 19.051 mmol) in water (10 mL) and the mixture was stirred at room temperature overnight. The mixture was cooled to 0° C. and aqueous HCl (1 N, 18.35 mL) was added dropwise. The mixture was concentrated, and the residue was extracted with EtOAc (3×50 mL). The combined organic layers were dried over anhydrous Na₂SO₄, filtered and concentrated to give as a red foam, 6-[(3R)-3-allylmorpholin-4-yl]-3-nitro-5-(trifluoromethyl)pyridine-2-carboxylic acid (3.59 g, 99%). ¹H NMR (300 MHz, Chloroform-d) δ 8.63 (s, 1H), 6.30 (br. s., 1H), 5.66 (ddt, J=17.1, 10.0, 7.1 Hz, 1H), 5.22-4.99 (m, 2H), 4.67 (td, J=7.3, 1.8 Hz, 1H), 4.05-3.88 (m, 2H), 3.80-3.54 (m, 4H), 2.64 (t, J=7.3 Hz, 2H) ppm. ¹⁹F NMR (282 MHz, Chloroform-d) δ−57.40 (s, 3F) ppm. ESI-MS m/z calc. 361.08856, found 362.1 (M+1)⁺; Retention time: 1.82 minutes (LC Method E).

Step 7: 6-[(3R)-3-Allylmorpholin-4-yl]-N'-[2-benzyloxy-2-(trifluoromethyl)hex-5-enoyl]-3-nitro-5-(trifluoromethyl)pyridine-2-carbohydrazide

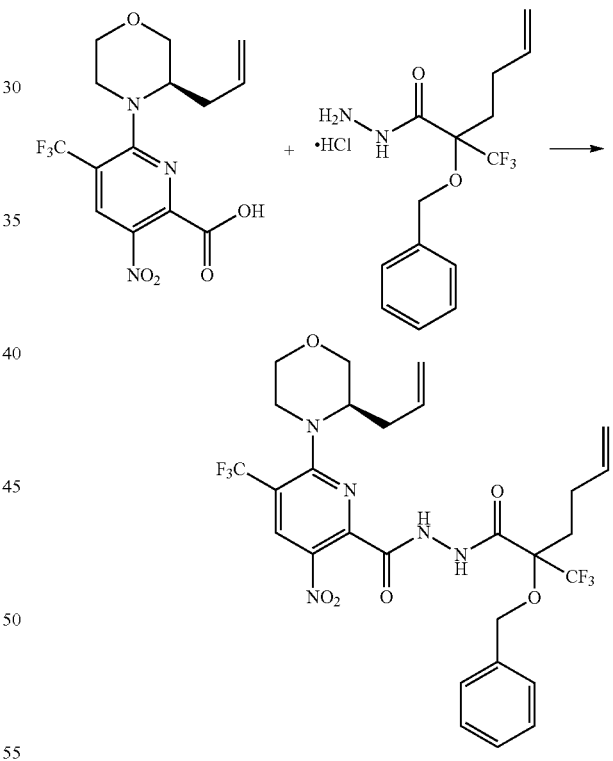

To a suspension of 6-[(3R)-3-allylmorpholin-4-yl]-3-nitro-5-(trifluoromethyl)pyridine-2-carboxylic acid (3.38 g, 9.3558 mmol) in CH₂Cl₂ (55 mL) at 0° C. was added oxalyl chloride (1.6 g, 1.0997 mL, 12.606 mmol) and DMF (690 mg, 0.7309 mL, 9.4399 mmol) dropwise. The mixture was stirred at room temperature for 1 h, followed by addition of a solution of 2-benzyloxy-2-(trifluoromethyl)hex-5-enehydrazide (hydrochloride salt) (3.7 g, 10.922 mmol) and DIPEA (1.71 g, 2.3046 mL, 13.231 mmol) in CH₂Cl₂ (40 mL) over 20 min. The mixture was stirred at room temperature for 1 h and cooled to 0° C. and 5% aqueous NaHCO₃

(100 mL) was added. The mixture was extracted with CH$_2$Cl$_2$ (3×50 mL). The combined organic layers were dried over anhydrous Na$_2$SO$_4$, filtered and concentrated. The residue was purified by silica gel chromatography (120 g column) using a gradient from 0% to 30% EtOAc in heptanes to afford as a yellow foam, 6-[(3R)-3-allylmorpholin-4-yl]-N-[2-benzyloxy-2-(trifluoromethyl)hex-5-enoyl]-3-nitro-5-(trifluoromethyl)pyridine-2-carbohydrazide (4.9 g, 81%). $^1$H NMR (300 MHz, Chloroform-d) δ 9.37-8.82 (m, 2H), 8.54-8.40 (m, 1H), 7.55-7.28 (m, 5H), 5.93-5.74 (m, 1H), 5.72-5.54 (m, 1H), 5.20-4.96 (m, 4H), 4.90-4.66 (m, 2H), 4.58-4.38 (m, 1H), 4.03-3.83 (m, 2H), 3.79-3.53 (m, 4H), 2.61 (t, J=7.2 Hz, 2H), 2.49-2.12 (m, 4H) ppm. ESI-MS m/z calc. 645.2022, found 646.2 (M+1)$^+$; Retention time: 2.25 minutes (LC Method E).

Step 8: (3R)-3-Allyl-4-[6-[5-[1-benzyloxy-1-(trifluoromethyl)pent-4-enyl]-1,3,4-oxadiazol-2-yl]-5-nitro-3-(trifluoromethyl)-2-pyridyl]morpholine

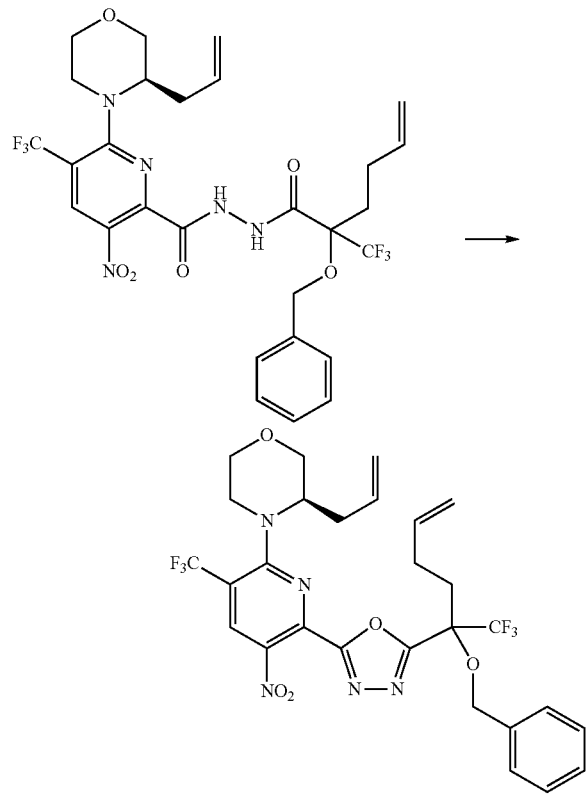

To a solution of 6-[(3R)-3-allylmorpholin-4-yl]-N'-[2-benzyloxy-2-(trifluoromethyl)hex-5-enoyl]-3-nitro-5-(trifluoromethyl)pyridine-2-carbohydrazide (340 mg, 0.5267 mmol) and DIPEA (186 mg, 0.2507 mL, 1.4391 mmol) in acetonitrile (8 mL) at 50° C. was added p-toluenesulfonyl chloride (126 mg, 0.6609 mmol) portion wise. The mixture was stirred at 70° C. for 2 h, cooled to 0° C., and diluted with EtOAc (50 mL) and 5% aqueous NaHCO$_3$ (15 mL). The two layers were separated, and the organic layer was washed with brine (5 mL), dried over anhydrous Na$_2$SO$_4$, filtered and concentrated. The residue was purified by silica gel chromatography (40 g column) using a gradient from 0% to 25% EtOAc in heptanes to afford as a yellow oil, (3R)-3-allyl-4-[6-[5-[1-benzyloxy-1-(trifluoromethyl)pent-4-enyl]-1,3,4-oxadiazol-2-yl]-5-nitro-3-(trifluoromethyl)-2-pyridyl]morpholine (272 mg, 82%). $^1$H NMR (300 MHz, Chloroform-d) δ 8.70 (s, 1H), 7.45-7.29 (m, 5H), 5.90-5.73 (m, 1H), 5.72-5.55 (m, 1H), 5.17-4.97 (m, 4H), 4.81 (dd, J 10.6, 6.2 Hz, 1H), 4.72-4.60 (m, 2H), 4.02-3.86 (m, 2H), 3.79-3.53 (m, 4H), 2.63 (t, J 7.2 Hz, 2H), 2.46 (d, J=10.0 Hz, 4H) ppm. ESI-MS m/z calc. 627.19165, found 628.2 (M+1)$^+$; Retention time: 2.45 minutes (LC Method E).

Step 9: (12R)-6-(Benzyloxy)-21-nitro-6,19-bis(trifluoromethyl)-14,23-dioxa-3,4,17,22-tetraazatetracyclo[16.3.1.12,5.012,17]tricosa-1(21),2,4,9,18(22),19-hexaene (E/Z mixture)

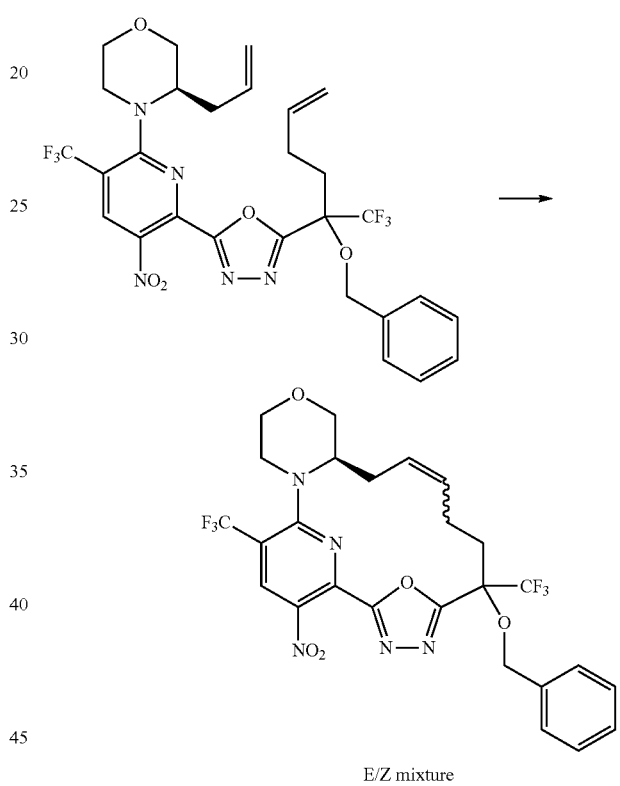

E/Z mixture

To a dried 250-mL flask under nitrogen was added DCE (25 mL) and bubbled nitrogen through the solvent for 5 min. Zhan catalyst-1B (47 mg, 0.0641 mmol) was added under flow of nitrogen. A solution of (3R)-3-allyl-4-[6-[5-[1-benzyloxy-1-(trifluoromethyl)pent-4-enyl]-1,3,4-oxadiazol-2-yl]-5-nitro-3-(trifluoromethyl)-2-pyridyl]morpholine (270 mg, 0.4303 mmol) in DCE (2 mL) was added dropwise over 1 h at 70° C. The mixture was bubbled with nitrogen and heated for 2.5 h at 70° C., then the mixture was cooled to room temperature and concentrated. The residue was purified by silica gel chromatography (40 g column) using a gradient from 0% to 20% EtOAc in heptanes which gave as a yellow oil, (12R)-6-(benzyloxy)-21-nitro-6,19-bis(trifluoromethyl)-14,23-dioxa-3,4,17,22-tetraazatetracyclo[16.3.1.12,5.012,17]tricosa-1(21),2,4,9,18(22),19-hexaene (E/Z mixture) (171 mg, 56%). $^1$H NMR (300 MHz, Chloroform-d) δ 8.68 (s, 1H), 7.41-7.26 (m, 5H), 5.69-5.43 (m, 2H), 5.13-4.88 (m, 2H), 4.12-3.86 (m, 3H), 3.82-3.56 (m, 4H), 2.83-2.52 (m, 2H), 2.52-2.31 (m, 2H), 2.28-2.15 (m, 1H), 2.14-1.98 (m, 1H) ppm. $^{19}$F NMR (282 MHz, Chloroform-d) δ −58.28 (s, 3F), −73.62 (br. s., 3F) ppm. ESI-MS m/z calc. 599.16034, found 600.2 (M+1)$^+$; Retention time: 2.37 minutes (LC Method E).

Step 10: (12R)-21-Amino-6,19-bis(trifluoromethyl)-14,23-dioxa-3,4,17,22-tetraazatetracyclo[16.3.1.12,5.012,17]tricosa-1(21),2,4,18(22),19-pentaen-6-ol

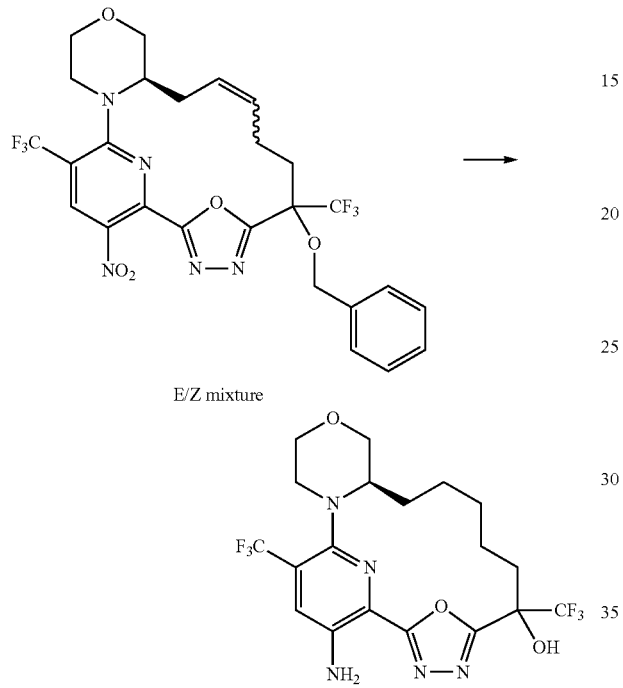

E/Z mixture

To a solution of (12R)-6-(benzyloxy)-21-nitro-6,19-bis(trifluoromethyl)-14,23-dioxa-3,4,17,22-tetraazatetracyclo[16.3.1.12,5.012,17]tricosa-1(21),2,4,9,18(22),19-hexaene (E/Z mixture) (550 mg, 0.6606 mmol) in EtOAc (10 mL) and MeOH (10 mL) was added 10% palladium on carbon (250 mg, 0.1175 mmol, 50% wet). The mixture was stirred under hydrogen balloon at room temperature for 3 days at 30° C. then at 50° C. for 4 h. The mixture was filtered through Celite washing with EtOAc. The filtrate was concentrated and purified by silica gel chromatography (80 g column) using a gradient from 0% to 15% EtOAc in dichloromethane followed by recrystallization from dichloromethane and hexanes which gave as a yellow solid, (12R)-21-amino-6,19-bis(trifluoromethyl)-14,23-dioxa-3,4,17,22-tetraazatetracyclo[16.3.1.12,5.012,17]tricosa-1(21),2,4,18(22),19-pentaen-6-ol (255 mg, 80%). $^1$H NMR (300 MHz, Chloroform-d) δ 7.41 (s, 1H), 5.37 (s, 1H), 5.32 (s, 1H), 3.90-3.68 (m, 5H), 3.47-3.09 (m, 3H), 2.62-1.94 (m, 3H), 1.90-1.60 (m, 2H), 1.58-1.40 (m, 5H) ppm. ESI-MS m/z calc. 481.15485, found 482.2 (M+1)$^+$; Retention time: 3.29 minutes (LC Method C).

Step 11: (12R)-21-Amino-6,19-bis(trifluoromethyl)-14,23-dioxa-3,4,17,22-tetraazatetracyclo[16.3.1.12,5.012,17]tricosa-1(21),2,4,18(22),19-pentaen-6-ol (enantiomer 1) (Compound 54) and (12R)-21-amino-6,19-bis(trifluoromethyl)-14,23-dioxa-3,4,17,22-tetraazatetracyclo[16.3.1.12,5.012,17]tricosa-1(21),2,4,18(22),19-pentaen-6-ol (enantiomer 2) (Compound 55)

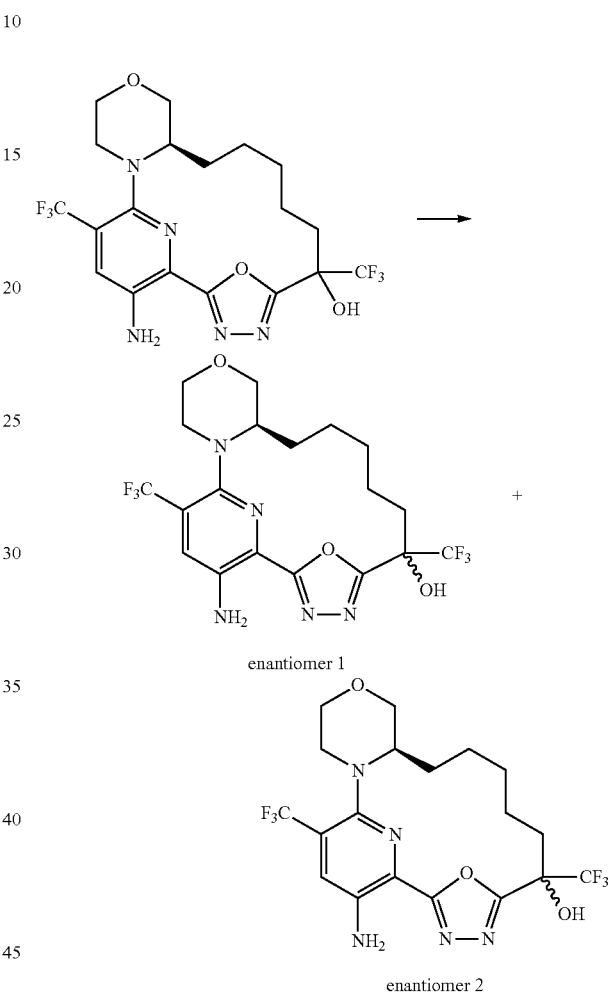

enantiomer 1 enantiomer 2

Racemic (12R)-21-amino-6,19-bis(trifluoromethyl)-14,23-dioxa-3,4,17,22-tetraazatetracyclo[16.3.1.12,5.012,17]tricosa-1(21),2,4,18(22),19-pentaen-6-ol (100 mg, 0.2075 mmol) was purified by chiral SFC using a LUX-4 column (250×21.2 mm, 5 μm particle size) sold by Phenomenex and eluting with 20% MeOH in CO$_2$ over 6 min which provided two single enantiomer products:

The first enantiomer to elute was isolated as a yellow solid, (12R)-21-amino-6,19-bis(trifluoromethyl)-14,23-dioxa-3,4,17,22-tetraazatetracyclo[16.3.1.12,5.012,17]tricosa-1(21),2,4,18(22),19-pentaen-6-ol (enantiomer 1) (54 mg, 53%). $^1$H NMR (300 MHz, Chloroform-d) δ 7.41 (s, 1H), 5.31 (s, 2H), 3.90-3.70 (m, 5H), 3.47-3.37 (m, 1H), 3.30 (ddd, J=12.8, 9.4, 3.1 Hz, 1H), 3.19-3.09 (m, 1H), 2.51-2.36 (m, 1H), 2.27 (t, J=10.4 Hz, 1H), 2.17-2.02 (m, 1H), 1.82-1.62 (m, 3H), 1.58-1.42 (m, 4H) ppm. $^{19}$F NMR (282 MHz, Chloroform-d) δ −60.26 (s, 3F), −80.82 (s, 3F) ppm. ESI-MS m/z calc. 481.15485, found 482.2 (M+1)$^+$; Retention time: 3.3 minutes (LC Method C).

The second enantiomer to elute was isolated as a yellow solid, (12R)-21-amino-6,19-bis(trifluoromethyl)-14,23-dioxa-3,4,17,22-tetraazatetracyclo[16.3.1.1²,⁵.0¹²,¹⁷]tricosa-1(21),2,4,18(22),19-pentaen-6-ol (enantiomer 2) (43 mg, 41%). ¹H NMR (300 MHz, Chloroform-d) δ 7.42 (s, 1H), 5.36 (s, 2H), 3.91-3.63 (m, 5H), 3.34 (ddd, J=13.1, 10.4, 2.9 Hz, 1H), 3.26-3.11 (m, 2H), 2.65-2.47 (m, 1H), 2.45-2.30 (m, 1H), 2.24-2.09 (m, 1H), 2.06-1.79 (m, 2H), 1.77-1.65 (m, 1H), 1.62-1.52 (m, 4H) ppm. ¹⁹F NMR (282 MHz, Chloroform-d) δ −60.58 (s, 3F), −77.24 (s, 3F) ppm. ESI-MS m/z calc. 481.1549, found 482.2 (M+1)⁺; Retention time: 3.3 minutes (LC Method C).

Example 32: Preparation of 17-amino-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (Compound 56) and 17-amino-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (Compound 57)

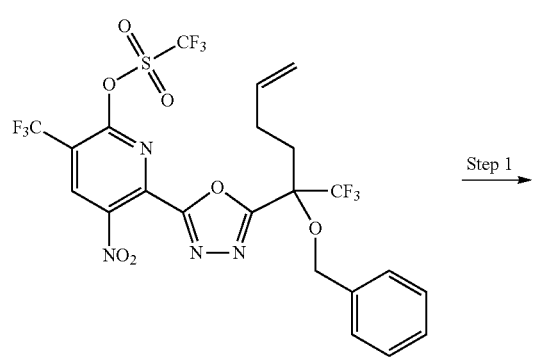

Step 1

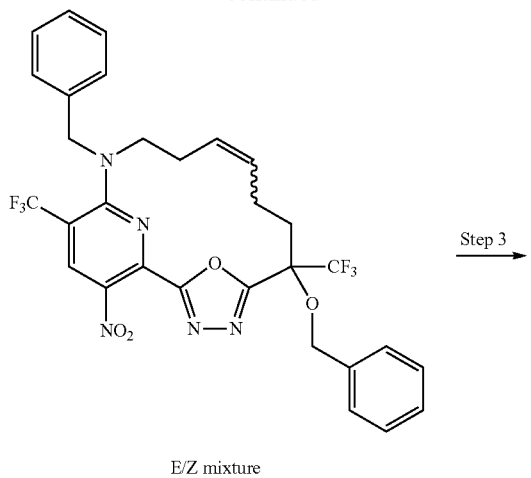

E/Z mixture

Step 3

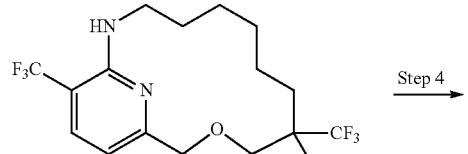

Step 4

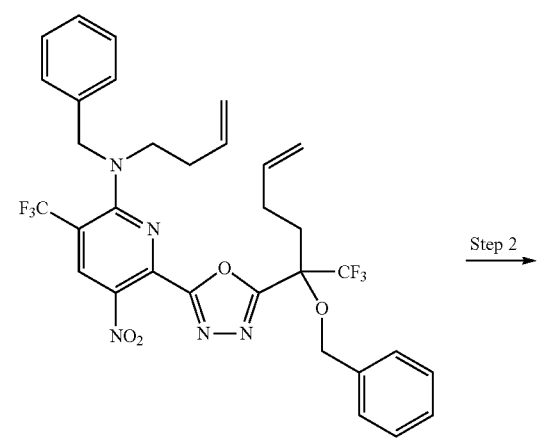

E/Z mixture

Step 2

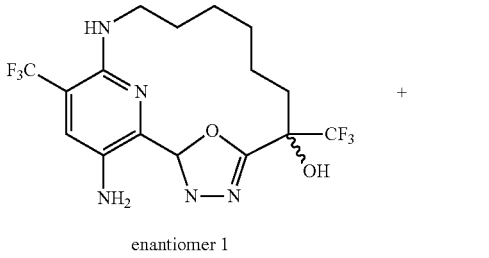

enantiomer 1

+

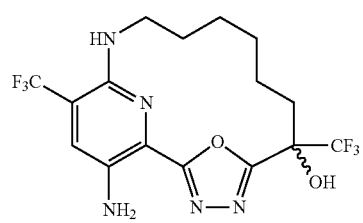

enantiomer 2

433

Step 1: N-Benzyl-6-[5-[1-benzyloxy-1-(trifluoromethyl)pent-4-enyl]-1,3,4-oxadiazol-2-yl]-N-but-3-enyl-5-nitro-3-(trifluoromethyl)pyridin-2-amine

434

Step 2: 13-Benzyl-6-benzyloxy-17-nitro-6,15-bis(trifluoromethyl)-19-oxa-3,4,13,18-tetrazatricyclo[12.3.1.1²,⁵]nonadeca-1(18),2,4,9,14,16-hexaene (E/Z mixture)

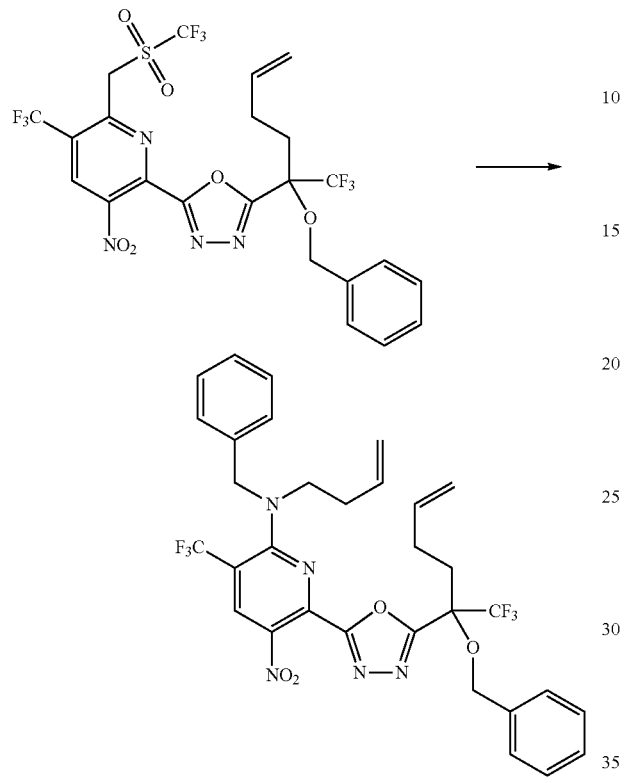

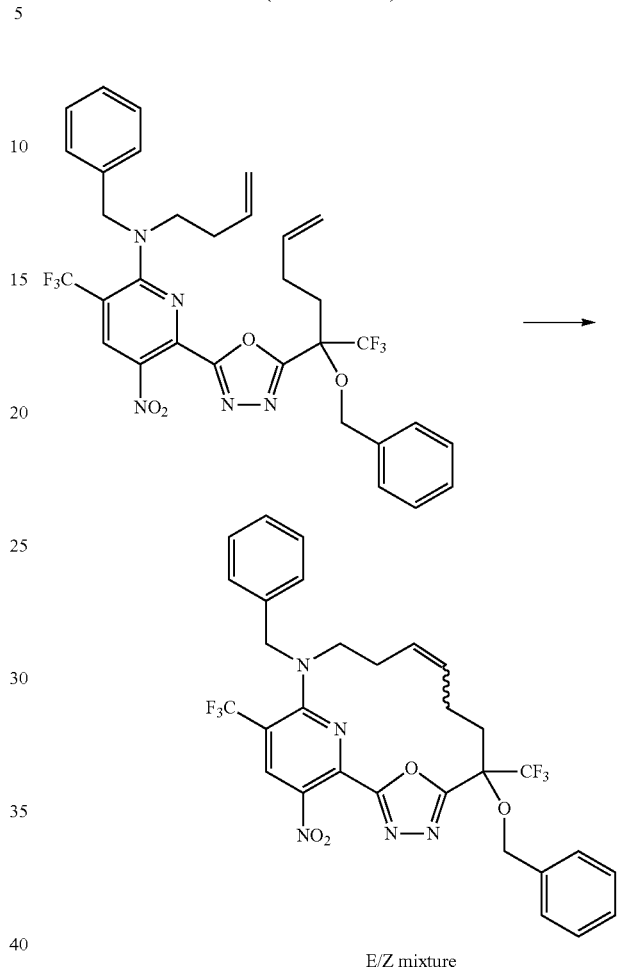

E/Z mixture

In a 100 mL flask, [6-[5-[1-benzyloxy-1-(trifluoromethyl)pent-4-enyl]-1,3,4-oxadiazol-2-yl]-5-nitro-3-(trifluoromethyl)-2-pyridyl]trifluoromethanesulfonate (200 mg, 0.3075 mmol) was dissolved in acetonitrile (6 mL) and cooled to 0° C. followed by addition of DIEA (300 µL, 1.722 mmol) and N-benzylbut-3-en-1-amine (110 mg, 0.6822 mmol) and then the mixture was stirred for 90 minutes allowing to warm to room temperature. The reaction was concentrated. The crude material was then purified by silica gel chromatography (40 gram column) using a gradient from 100% hexanes to 60% ethyl acetate in hexanes (product elutes at 22% ethyl acetate) to afford as a yellow foam, N-benzyl-6-[5[1-benzyloxy-1-(trifluoromethyl)pent-4-enyl]-1,3,4-oxadiazol-2-yl]-N-but-3-enyl-5-nitro-3-(trifluoromethyl)pyridin-2-amine (199 mg, 98%). $^1$H NMR (400 MHz, DMSO-d6) δ 8.83 (s, 1H), 7.40-7.28 (m, 9H), 7.26 (dt, J=8.3, 3.5 Hz, 1H), 5.84 (ddt, J=16.9, 10.3, 6.5 Hz, 1H), 5.67 (ddt, J=17.1, 10.3, 6.8 Hz, 1H), 5.14-4.94 (m, 4H), 4.88 (s, 2H), 4.75 (d, J=10.8 Hz, 1H), 4.60 (d, J=10.8 Hz, 1H), 3.61 (t, J=7.4 Hz, 2H), 2.54 (s, 1H), 2.45 (d, J=5.9 Hz, 1H), 2.37 (q, J=7.4 Hz, 2H), 2.31-2.13 (m, 2H) ppm. ESI-MS m/z calc. 661.2124, found 662.2 (M+1)⁺; Retention time: 1.75 minutes (LC Method M).

In a 500 mL round-bottom 3-neck flask, a continuously degassed solution via nitrogen line of Zhan catalyst-1B (55 mg, 0.07496 mmol) in DCE (150 mL) was heated to 50° C. under nitrogen atmosphere. Then, a solution of N-benzyl-6-[5-[1-benzyloxy-1-(trifluoromethyl)pent-4-enyl]-1,3,4-oxadiazol-2-yl]-N-but-3-enyl-5-nitro-3-(trifluoromethyl)pyridin-2-amine (199 mg, 0.3008 mmol) in DCE (20 mL) was added dropwise via syringe. The resulting mixture was heated at 75° C. for 3 h. The reaction mixture was then cooled to room temperature and concentrated under reduced pressure. The crude material was purified by silica gel chromatography using a gradient from 100% hexanes to 50% ethyl acetate in hexanes to afford a yellow residue which was placed under vacuum for 14 hours to produce as a pale yellow solid, 13-benzyl-6-benzyloxy-17-nitro-6,15-bis(trifluoromethyl)-19-oxa-3,4,13,18-tetrazatricyclo[12.3.1.1²,⁵]nonadeca-1(18),2,4,9,14,16-hexaene (E/Z mixture) (130 mg, 68%). $^1$H NMR (400 MHz, DMSO-d6) δ 8.79 (s, 1H), 7.43-7.30 (m, 8H), 7.29-7.25 (m, 2H), 5.55 (t, J=8.5 Hz, 1H), 5.31 (q, J=8.6 Hz, 1H), 4.86 (s, 2H), 4.82 (d, J=1.8 Hz, 2H), 3.45 (t, J=8.4 Hz, 2H), 2.49-2.25 (m, 4H), 2.24 (d, J=4.9 Hz, 2H) ppm. ESI-MS m/z calc. 633.1811, found 634.2 (M+1)⁺; Retention time: 1.49 minutes (LC Method M).

Step 3: 17-Amino-6,15-bis(trifluoromethyl)-19-oxa-3,4,13,18-tetrazatricyclo[12.3.1.1²,⁵]nonadeca-1(18),2,4,14,16-pentaen-6-ol

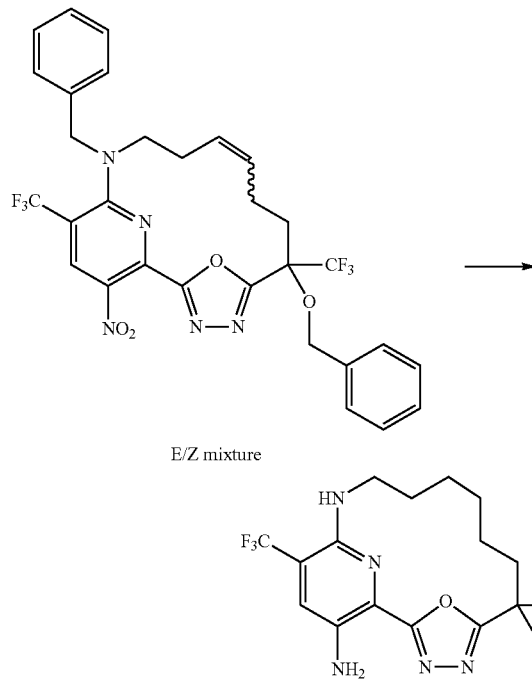

E/Z mixture

In a 250 mL flask, a solution of 13-benzyl-6-benzyloxy-17-nitro-6,15-bis(trifluoromethyl)-19-oxa-3,4,13,18-tetrazatricyclo[12.3.1.1²,⁵]nonadeca-1(18),2,4,9,14,16-hexaene (E/Z mixture) (130 mg, 0.2052 mmol) in AcOH (2 mL) and ethyl acetate (2 mL) was purged with nitrogen. Then Pd/C (35 mg of 10% w/w, 0.03289 mmol) was added. The mixture was degassed with nitrogen for 5 minutes then purged by a balloon filled with hydrogen gas. The mixture was stirred at 1 atmosphere of hydrogen for 4 h. Added additional Pd/C (approximately 185.6 mg of 10% w/w, 0.1744 mmol) and stirred for one more hour. Filtered and concentrated the mixture and subjected to a stainless steel pressure reactor with fresh Pd/C (35 mg of 10% w/w, 0.03289 mmol) and AcOH (2.008 mL) and ethyl acetate (2.008 mL). Purged the vessel with nitrogen, then flushed with hydrogen and stirred at 140 psi hydrogen for 2 hours. The reaction was filtered washing the Celite plug with excess acetonitrile and ethyl acetate and then concentrated the organic filtrate. The crude material was then purified by silica gel chromatography using a gradient from 100% hexanes to 100% ethyl acetate to afford as a yellow solid, 17-amino-6,15-bis(trifluoromethyl)-19-oxa-3,4,13,18-tetrazatricyclo[12.3.1.1²,⁵]nonadeca-1(18),2,4,14,16-pentaen-6-ol (76 mg, 87%). ESI-MS m/z calc. 425.12863, found 426.2 (M+1)⁺; Retention time: 1.78 minutes (LC Method A).

Step 4: 17-Amino-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (Compound 56) and 17-amino-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (Compound 57)

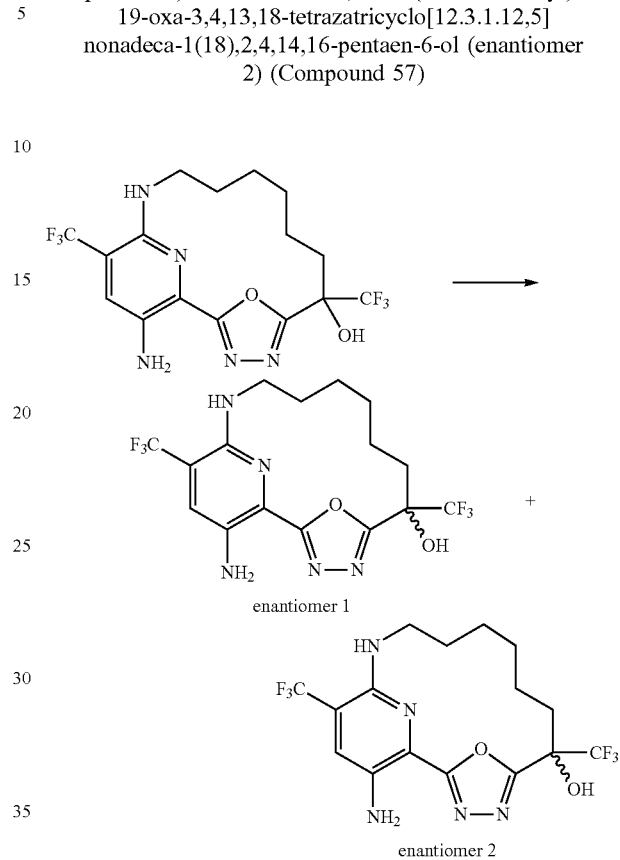

enantiomer 1 enantiomer 2

Racemic 17-amino-6,15-bis(trifluoromethyl)-19-oxa-3,4,13,18-tetrazatricyclo[12.3.1.1²,⁵]nonadeca-1(18),2,4,14,16-pentaen-6-ol (75 mg, 0.1763 mmol) was purified by chiral SFC using a Phenomenex LUX-4 column (250×10 mm, 5 μm particle size) at 40° C. eluting with 10% MeOH (+20 mM NH₃)/90% CO₂ at a flow rate of 70 mL/min with an injection volume of 500 μL giving the separation of two enantiomers:

The first enantiomer to elute was isolated as a yellow solid, 17-amino-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (23.8 mg, 63%). ¹H NMR (400 MHz, DMSO-d6) δ 7.57 (d, J=15.4 Hz, 2H), 6.29 (t, J=4.9 Hz, 1H), 5.95 (s, 2H), 3.23 (td, J=8.1, 5.3 Hz, 2H), 2.13 (dq, J=10.9, 6.6, 6.2 Hz, 2H), 1.84 (d, J=12.9 Hz, 1H), 1.67-1.60 (m, 2H), 1.59 (d, J=10.0 Hz, 2H), 1.52 (s, 1H), 1.39 (d, J=8.2 Hz, 2H) ppm. ESI-MS m/z calc. 425.12863, found 426.2 (M+1)⁺; Retention time: 1.77 minutes (LC Method A).

The second enantiomer to elute was isolated as a yellow solid, 17-amino-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (24.0 mg, 63%). ¹H NMR (400 MHz, DMSO-d6) δ 7.57 (d, J=15.4 Hz, 2H), 6.29 (t, J=5.0 Hz, 1H), 5.95 (s, 2H), 3.23 (td, J=8.2, 5.4 Hz, 2H), 2.14 (dq, J=11.6, 6.8, 6.3 Hz, 2H), 1.86 (p, J=6.9 Hz, 1H), 1.68-1.60 (m, 2H), 1.60-1.54 (m, 2H), 1.51 (d, J=14.0 Hz, 1H), 1.38 (d, J=8.9 Hz, 2H) ppm. ESI-MS m/z calc. 425.12863, found 426.2 (M+1)⁺; Retention time: 1.77 minutes (LC Method A).

Example 33: Preparation of 17-amino-13-methyl-15-(trifluoromethyl)-19-oxa-3,4,13,18-tetrazatricyclo[12.3.1.1²,⁵]nonadeca-1(18),2,4,14,16-pentaen-6-one (Compound 58)
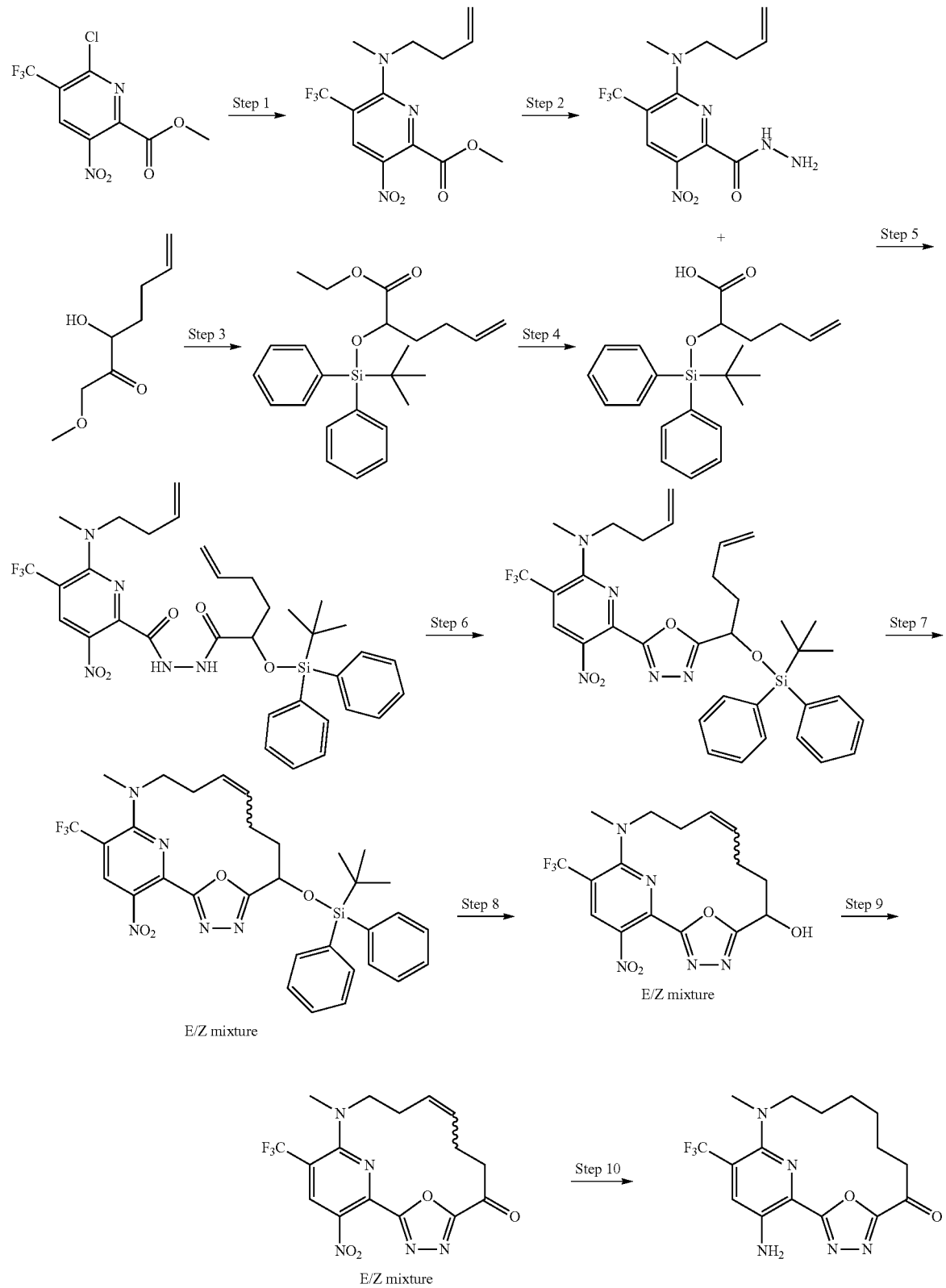

Step 1: Methyl 6-[but-3-enyl)methyl)amino]-3-nitro-5-(trifluoromethyl)pyridine-2-carboxylate

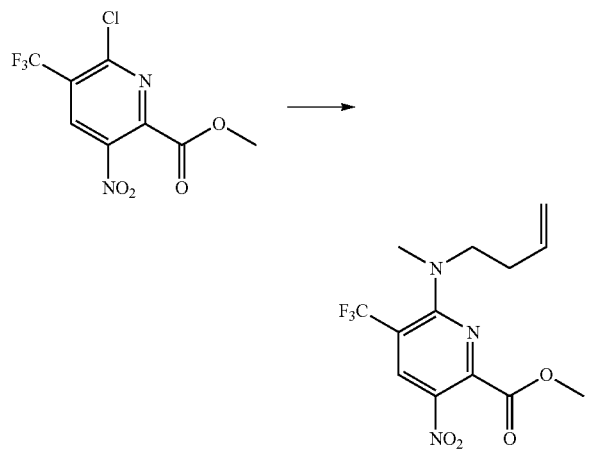

To a solution of methyl 6-chloro-3-nitro-5-(trifluoromethyl)pyridine-2-carboxylate (3.92 g, 13.77 mmol) in acetonitrile (58.8 mL) was added N-methylbut-3-en-1-amine (hydrochloride salt) (1.662 g, 13.67 mmol), DIEA (6.224 mL, 35.73 mmol) and the mixture was stirred at room temperature for 2 h. The solvent was removed in vacuo. The residue was diluted with EtOAc (50 mL) and washed with brine (2×25 mL), dried over sodium sulfate, filtered and concentrated in vacuo. The residue was purified by silica gel chromatography (40 gram column) using a gradient from 100% hexanes to 50% ethyl acetate in hexanes to afford as a yellow solid, methyl 6-[but-3-enyl(methyl)amino]-3-nitro-5-(trifluoromethyl)pyridine-2-carboxylate (3.89 g, 84%). ESI-MS m/z calc. 333.09363, found 334.1 (M+1)+; Retention time: 0.73 minutes (LC Method S).

Step 2: 6-[But-3-enyl)methyl)amino]-3-nitro-5-(trifluoromethyl)pyridine-2-carbohydrazide

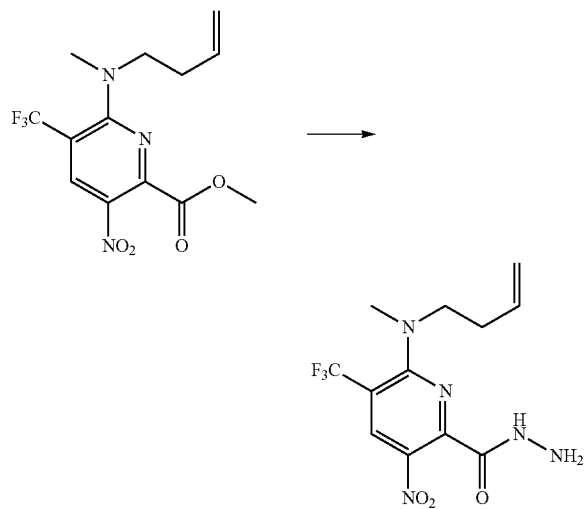

To a solution of methyl 6-[but-3-enyl(methyl)amino]-3-nitro-5-(trifluoromethyl)pyridine-2-carboxylate (4.2 g, 12.60 mmol) in ethanol (84 mL) was added hydrazine (5.932 mL, 189.0 mmol) and stirred the resulting mixture for 30 min at room temperature. Diluted the reaction mixture with water (150 mL) and extracted with DCM (3×100 mL). The combined organic layers were washed with brine, dried over $Na_2SO_4$, filtered and concentrated, then purified by silica gel chromatography (40 g column) using a gradient from 0% to 10% MeOH in dichloromethane to afford as a yellow solid, 6-[but-3-enyl(methyl)amino]-3-nitro-5-(trifluoromethyl)pyridine-2-carbohydrazide (4.05 g, 96%). ESI-MS m/z calc. 333.1049, found 334.2 (M+1)+; Retention time: 0.52 minutes (LC Method S).

Step 3: Ethyl 2-[tert-butyl(diphenyl)silyl]oxyhex-5-enoate

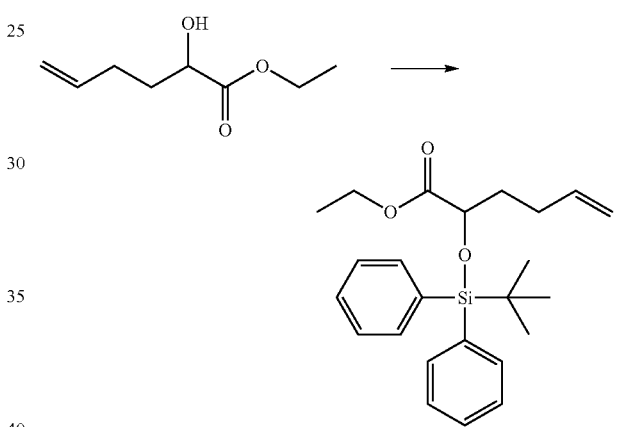

To a solution of ethyl 2-hydroxyhex-5-enoate (8 g, 48.04 mmol) in DMF (96.08 mL) under nitrogen was added imidazole (6.543 g, 96.11 mmol) and DMAP (1.467 g, 12.01 mmol), followed by the slow addition of TBDPSCl (15.0 mL, 57.68 mmol). The solution was stirred at ambient temperature overnight. The reaction was diluted with dichloromethane (150 mL), washed with saturated ammonium chloride solution (2×100 mL), brine (100 mL), dried over anhydrous sodium sulfate, filtered and concentrated under reduced pressure. Purification by silica gel chromatography (220 g column) using a gradient from 0% to 20% ethyl acetate in hexanes provided as a colorless oil, ethyl 2-[tert-butyl(diphenyl)silyl]oxyhex-5-enoate (15.6 g, 82%). $^1$H NMR (400 MHz, DMSO-d6) δ 7.68-7.54 (m, 4H), 7.52-7.28 (m, 6H), 5.72 (ddt, J=16.9, 10.2, 6.5 Hz, 1H), 5.05-4.79 (m, 2H), 4.21 (t, J=5.7 Hz, 1H), 3.88 (q, J=7.1 Hz, 2H), 2.22-1.89 (m, 2H), 1.85-1.65 (m, 2H), 1.02 (d, J=11.7 Hz, 12H) ppm. Retention time: 0.88 minutes (LC Method R).

441

Step 4: 2-[tert-Butyl(diphenyl)silyl]oxyhex-5-enoic acid

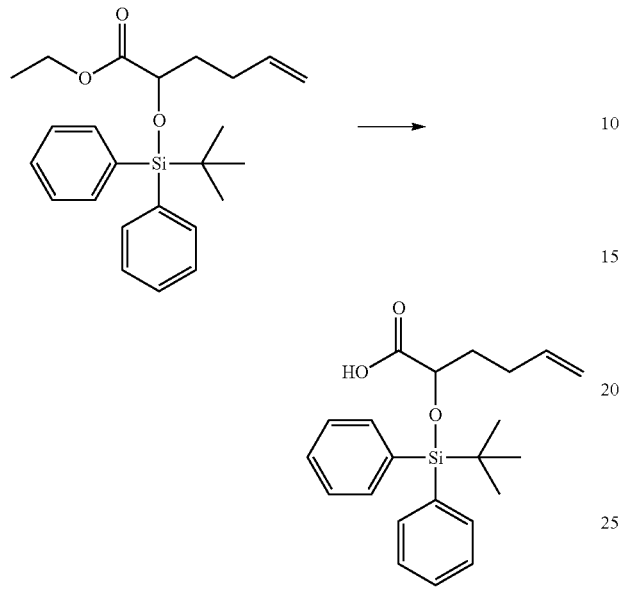

To a solution of ethyl 2-[tert-butyl(diphenyl)silyl]oxyhex-5-enoate (17 g, 42.86 mmol) in MeOH (99.16 mL) and THF (34 mL) was added NaOH (39.82 mL, 2 N, 79.64 mmol) and the mixture was stirred at ambient temperature overnight. The organic solvents were removed, and the residue was diluted with 1 N NaOH (20 mL) and extracted twice with MTBE (500 mL). The organic phases were back extracted with 1 N NaOH (1×50 mL) and the combined aqueous phases acidified to pH=1 with 10% aqueous HCl. The aqueous phase was extracted with ethyl acetate (2×100 mL) and the organic phases were washed with brine (1×100 mL). The combined ethyl acetate phases were dried over $MgSO_4$, filtered and concentrated to afford as a white solid, 2-[tert-butyl(diphenyl)silyl]oxyhex-5-enoic acid (10.2 g, 65%). $^1$H NMR (400 MHz, DMSO-d6) δ 12.22 (s, 1H), 7.66-7.56 (m, 4H), 7.52-7.35 (m, 6H), 5.75-5.62 (m, 1H), 4.94-4.83 (m, 2H), 4.16 (t, J=5.5 Hz, 1H), 2.17-2.04 (m, 2H), 1.71 (qd, J=8.8, 7.4, 3.0 Hz, 2H), 1.03 (s, 9H) ppm. Retention time: 0.86 minutes (LC Method S).

Step 5: 6-[But-3-enyl(methyl)amino]-N'-[2-[tert-butyl(diphenyl)silyl]oxyhex-5-enoyl]-3-nitro-5-(trifluoromethyl)pyridine-2-carbohydrazide

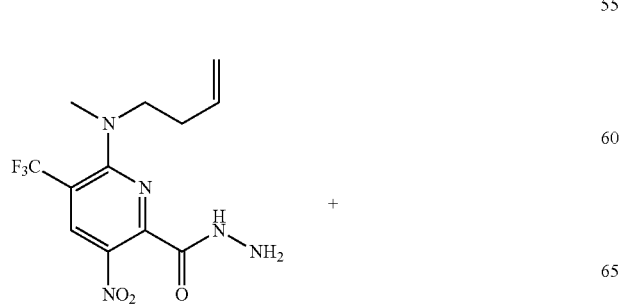

442

-continued

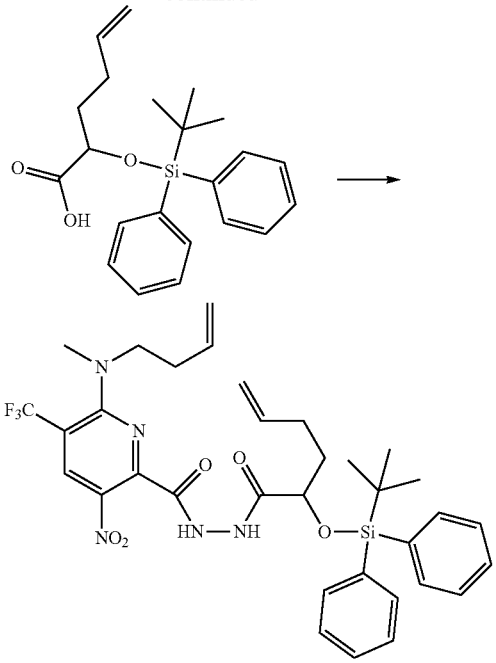

To a solution of 2-[tert-butyl(diphenyl)silyl]oxyhex-5-enoic acid (3.344 g, 9.074 mmol) and 6-[but-3-enyl(methyl)amino]-3-nitro-5-(trifluoromethyl)pyridine-2-carbohydrazide (2.88 g, 8.642 mmol) in DMF (37.01 mL) was added DIEA (4.573 mL, 26.25 mmol), followed by HATU (3.943 g, 10.37 mmol). The reaction mixture was stirred at room temperature for 3 h. The reaction was extracted with ethyl acetate (3×20 mL). The organic layers were washed with brine (20 mL), dried over sodium sulfate, and evaporated. The residue was purified by silica gel chromatography (80 gram column) using a gradient from 100% hexanes to 70% ethyl acetate in hexanes to afford as a yellow sticky solid, 6-[but-3-enyl(methyl)amino]-N'-[2-[tert-butyl(diphenyl)silyl]oxyhex-5-enoyl]-3-nitro-5-(trifluoromethyl)pyridine-2-carbohydrazide (4.5 g, 76%). ESI-MS m/z calc. 683.2751, found 684.5 (M+1)$^+$; Retention time: 0.83 minutes (LC Method R).

Step 6: N-But-3-enyl-6-[5-[1-[tert-butyl(diphenyl) silyl]oxypent-4-enyl]-1,3,4-oxadiazol-2-yl]-N-methyl-5-nitro-3-(trifluoromethyl)pyridin-2-amine

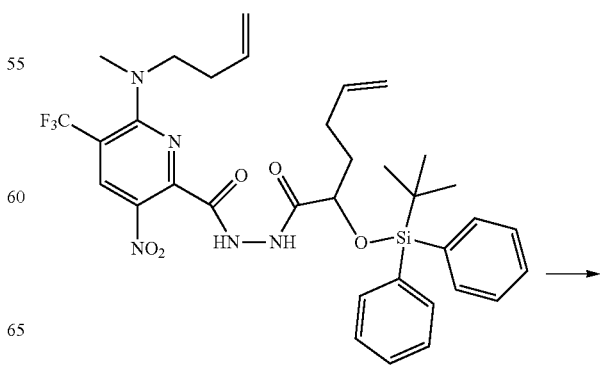

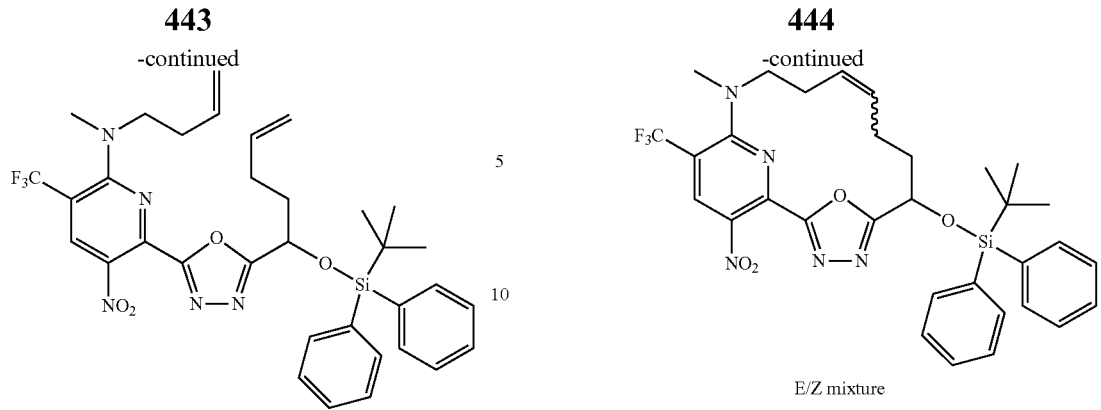

A solution of 6-[but-3-enyl(methyl)amino]-N'-[2-[tert-butyl(diphenyl)silyl]oxyhex-5-enoyl]-3-nitro-5-(trifluoromethyl)pyridine-2-carbohydrazide (5.87 g, 8.584 mmol) and DIEA (5.194 mL, 29.82 mmol) in acetonitrile (134.2 mL) was heated at 50° C., then p-toluenesulfonyl chloride (2.557 g, 13.41 mmol) was added. The resulted mixture was heated at 70° C. for 15 min. The reaction mixture was cooled to room temperature, quenched with a saturated solution of sodium bicarbonate (250 mL) and extracted with ethyl acetate (3×125 mL). The organics were separated, dried over sodium sulfate, filtered and evaporated. The residue was purified by silica gel chromatography (12 gram column) using a gradient from 100% hexanes to 30% ethyl acetate in hexanes to afford as a white foamy solid, N-but-3-enyl-6-[5[1-[tert-butyl(diphenyl)silyl]oxypent-4-enyl]-1,3,4-oxadiazol-2-yl]-N-methyl-5-nitro-3-(trifluoromethyl)pyridin-2-amine (5.61 g, 98%). ESI-MS m/z calc. 665.2645, found 666.4 (M+1)+; Retention time: 0.83 minutes (LC Method T).

Step 7: tert-Butyl-[[13-methyl-17-nitro-15-(trifluoromethyl)-19-oxa-3,4,13,18-tetrazatricyclo[12.3.1.12,5]nonadeca-1(17),2,4,9,14(18),15-hexaen-6-yl]oxy]-diphenyl-silane (E/Z Mixture)

In a 1 L round-bottom 3-neck flask, a continuously degassed solution via nitrogen line of N-but-3-enyl-6-[5[1-[tert-butyl(diphenyl)silyl]oxypent-4-enyl]-1,3,4-oxadiazol-2-yl]-N-methyl-5-nitro-3-(trifluoromethyl)pyridin-2-amine (1.2 g, 1.802 mmol) in DCE (600 mL) was heated to 50° C. under nitrogen atmosphere. Then, a solution of [1,3-bis(2,4,6-trimethylphenyl)imidazolidin-2-ylidene]-dichloro-[(2-isopropoxyphenyl)methylene]ruthenium (282.3 mg, 0.4505 mmol) in DCE (50 mL) was added via syringe. The resulting mixture was heated at 50° C. for 2 hours. The reaction mixture was cooled to room temperature and concentrated under reduced pressure. The residue was purified by silica gel chromatography (24 gram column) using a gradient from 100% hexanes to 40% ethyl acetate in hexanes to afford as an off-white solid, tert-butyl-[[13-methyl-17-nitro-15-(trifluoromethyl)-19-oxa-3,4,13,18-tetrazatricyclo[12.3.1.12,5] nonadeca-1(17),2,4,9,14(18),15-hexaen-6-yl]oxy]-diphenyl-silane (E/Z mixture) (780 mg, 68%). ESI-MS m/z calc. 637.2332, found 638.4 (M+1)+; Retention time: 0.77 minutes (LC Method T).

Step 8: 13-Methyl-17-nitro-15-(trifluoromethyl)-19-oxa-3,4,13,18-tetrazatricyclo[12.3.1.12,5]nonadeca-1(18),2,4,9,14,16-hexaen-6-ol (E/Z mixture)

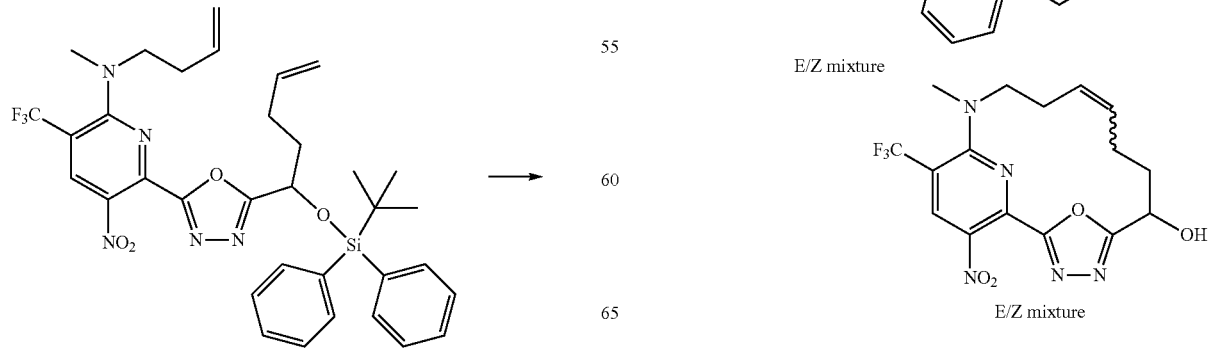

To a stirred solution of tert-butyl-[[13-methyl-17-nitro-15-(trifluoromethyl)-19-oxa-3,4,13,18-tetrazatricyclo[12.3.1.12,5]nonadeca-1(17),2,4,9,14(18),15-hexaen-6-yl]oxy]-diphenyl-silane (E/Z mixture) (490 mg, 0.7684 mmol) in THF (8.1 mL) was added TBAF (1.537 mL, 1 M, 1.537 mmol) at 0° C. The ice-bath was removed, and the reaction was stirred at room temperature for 15 min. The reaction mixture was concentrated under reduced pressure and purified by silica gel chromatography (12 g column) using a gradient from 0% hexanes to 30% EtOAc in hexanes giving as a yellow solid, 13-methyl-17-nitro-15-(trifluoromethyl)-19-oxa-3,4,13,18-tetrazatricyclo[12.3.1.12,5]nonadeca-1(18),2,4,9,14,16-hexaen-6-ol (E/Z mixture) (180 mg, 59%). ESI-MS m/z calc. 399.11545, found 400.8 (M+1)⁺; Retention time: 1.65 minutes (LC Method A).

Step 9: 13-Methyl-17-nitro-15-(trifluoromethyl)-19-oxa-3,4,13,18-tetrazatricyclo[12.3.1.12,5]nonadeca-1(18),2,4,9,14,16-hexaen-6-one (E/Z Mixture)

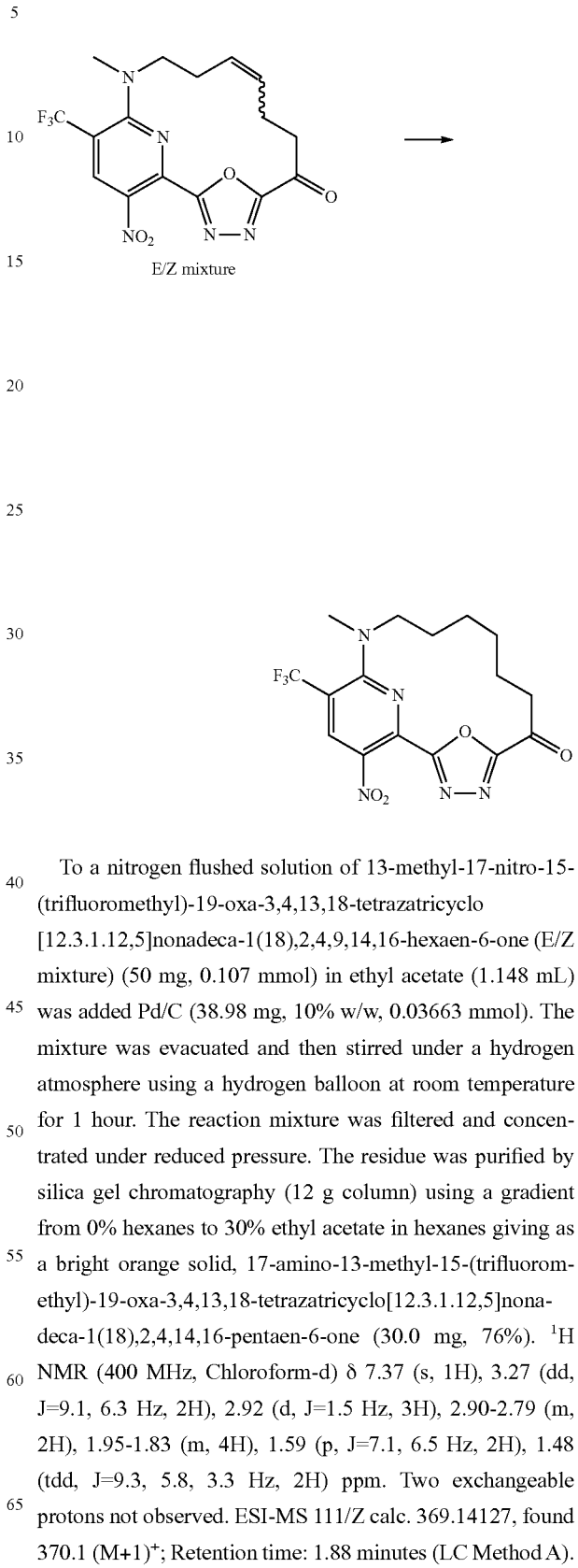

To a solution of 13-methyl-17-nitro-15-(trifluoromethyl)-19-oxa-3,4,13,18-tetrazatricyclo[12.3.1.12,5]nonadeca-1(18),2,4,9,14,16-hexaen-6-ol (E/Z mixture) (260 mg, 0.6511 mmol) in DCM (5 mL) was added DMP (359.0 mg, 0.8464 mmol) and the reaction was stirred for 30 min. Quenched the reaction with saturated NaHCO₃ and extracted with DCM (2×25 mL). Combined the organic layers, washed with brine, dried over Na₂SO₄, filtered and concentrated to afford as a yellow solid, 13-methyl-17-nitro-15-(trifluoromethyl)-19-oxa-3,4,13,18-tetrazatricyclo[12.3.1.12,5]nonadeca-1(18),2,4,9,14,16-hexaen-6-one (E/Z mixture) (260 mg, 100%). ESI-MS m/z calc. 397.0998, found 398.1 (M+1)⁺; Retention time: 0.69 minutes (LC Method S).

Step 10: 17-Amino-13-methyl-15-(trifluoromethyl)-19-oxa-3,4,13,18-tetrazatricyclo[12.3.1.12,5]nonadeca-1(18),2,4,14,16-pentaen-6-one (Compound 58)

To a nitrogen flushed solution of 13-methyl-17-nitro-15-(trifluoromethyl)-19-oxa-3,4,13,18-tetrazatricyclo[12.3.1.12,5]nonadeca-1(18),2,4,9,14,16-hexaen-6-one (E/Z mixture) (50 mg, 0.107 mmol) in ethyl acetate (1.148 mL) was added Pd/C (38.98 mg, 10% w/w, 0.03663 mmol). The mixture was evacuated and then stirred under a hydrogen atmosphere using a hydrogen balloon at room temperature for 1 hour. The reaction mixture was filtered and concentrated under reduced pressure. The residue was purified by silica gel chromatography (12 g column) using a gradient from 0% hexanes to 30% ethyl acetate in hexanes giving as a bright orange solid, 17-amino-13-methyl-15-(trifluoromethyl)-19-oxa-3,4,13,18-tetrazatricyclo[12.3.1.12,5]nonadeca-1(18),2,4,14,16-pentaen-6-one (30.0 mg, 76%). ¹H NMR (400 MHz, Chloroform-d) δ 7.37 (s, 1H), 3.27 (dd, J=9.1, 6.3 Hz, 2H), 2.92 (d, J=1.5 Hz, 3H), 2.90-2.79 (m, 2H), 1.95-1.83 (m, 4H), 1.59 (p, J=7.1, 6.5 Hz, 2H), 1.48 (tdd, J=9.3, 5.8, 3.3 Hz, 2H) ppm. Two exchangeable protons not observed. ESI-MS 111/Z calc. 369.14127, found 370.1 (M+1)⁺; Retention time: 1.88 minutes (LC Method A).

Example 34: Preparation of (6S,15R)-23-amino-8-fluoro-6,21-bis(trifluoromethyl)-26-oxa-3,4,19,24-tetraazapentacyclo[18.3.1.12,5.17,11.015,19]hexacosa-1(24),2,4,7(25),8,10,20,22-octaen-6-ol (hydrochloride salt) (Compound 59) and (6R,15R)-23-amino-8-fluoro-6,21-bis(trifluoromethyl)-26-oxa-3,4,19,24-tetraazapentacyclo[18.3.1.12,5.17,11.015,19]hexacosa-1(24),2,4,7(25),8,10,20,22-octaen-6-ol (hydrochloride salt) (Compound 60)

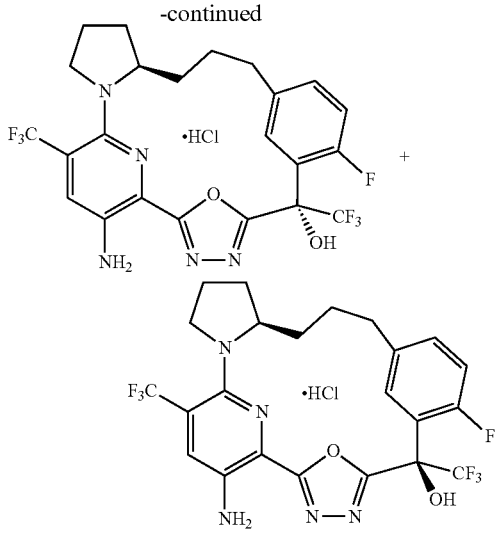

Step 1: tert-Butyl N-[6-[(2S)-2-allylpyrrolidin-1-yl]-2-[5-[2,2,2-trifluoro-1-(2-fluoro-5-iodo-phenyl)-1-hydroxy-ethyl]-1,3,4-oxadiazol-2-yl]-5-(trifluoromethyl)-3-pyridyl]carbamate

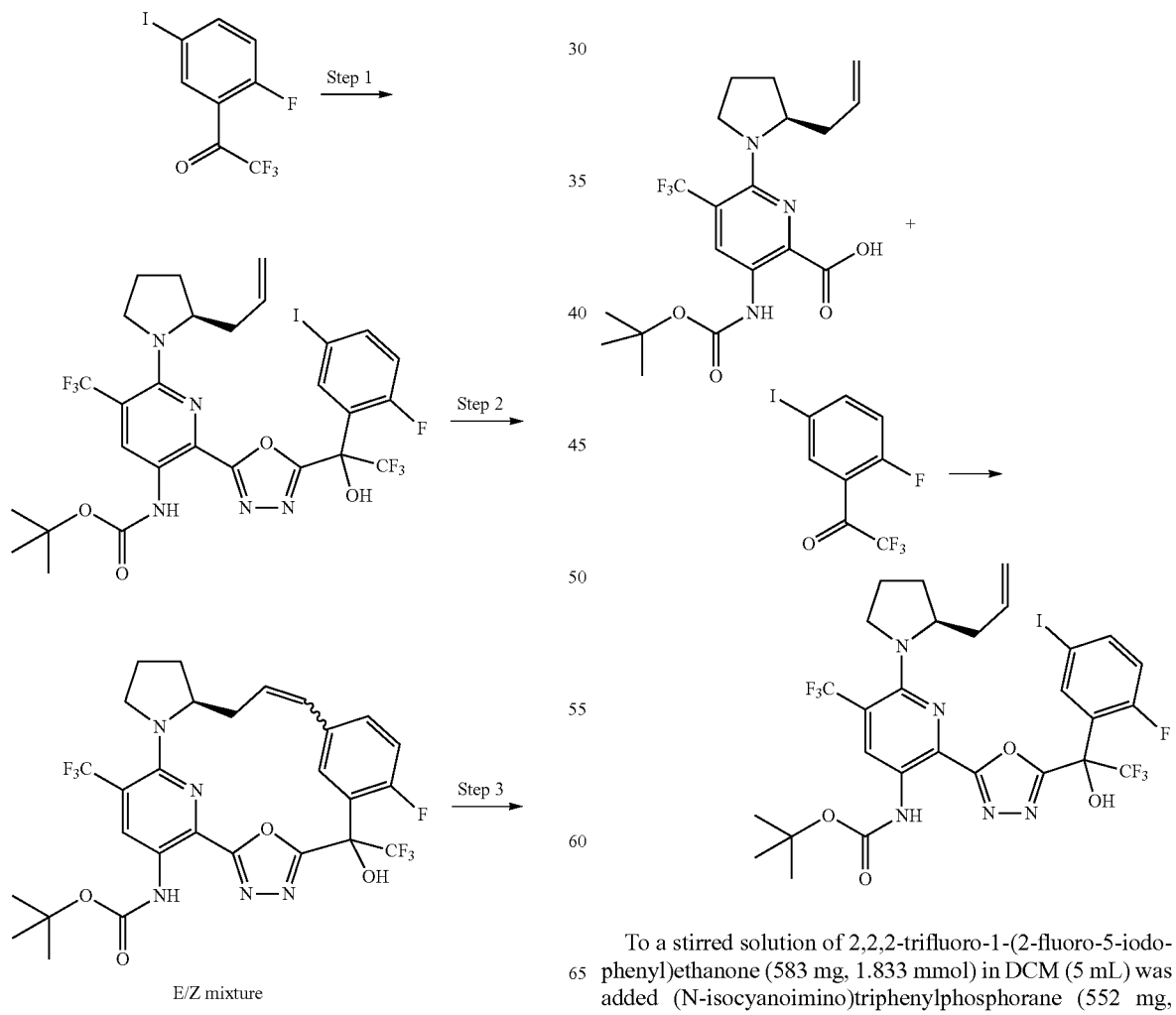

To a stirred solution of 2,2,2-trifluoro-1-(2-fluoro-5-iodo-phenyl)ethanone (583 mg, 1.833 mmol) in DCM (5 mL) was added (N-isocyanoimino)triphenylphosphorane (552 mg, 1.826 mmol) in DCM (5 mL) and stirred at room temperature for 30 min. Then, 6-[(2S)-2-allylpyrrolidin-1-yl]-3-(tert-butoxycarbonylamino)-5-(trifluoromethyl)pyridine-2-carboxylic acid (500 mg, 1.204 mmol) in DCM (5 mL) was added slowly dropwise. The mixture was stirred at room temperature overnight. The reaction mixture was concentrated and the resultant brown residue was purified by silica gel chromatography using a shallow gradient from 100% hexanes to 50% EtOAc in hexanes to afford tert-butyl N-[6-[(2S)-2-allylpyrrolidin-1-yl]-2-[5-[2,2,2-trifluoro-1-(2-fluoro-5-iodo-phenyl)-1-hydroxy-ethyl]-1,3,4-oxadiazol-2-yl]-5-(trifluoromethyl)-3-pyridyl]carbamate (582 mg, 64%). ESI-MS m/z calc. 757.0996, found 758.2 (M+1)+; Retention time: 0.66 minutes (LC Method T).

Step 2: tert-Butyl N-[(15S)-8-fluoro-6-hydroxy-6,21-bis(trifluoromethyl)-26-oxa-3,4,19,24-tetraazapentacyclo[18.3.1.12,5.17,11.015,19]hexacosa-1(24),2,4,7(25),8,10,12,20,22-nonaen-23-yl]carbamate (E/Z mixture)

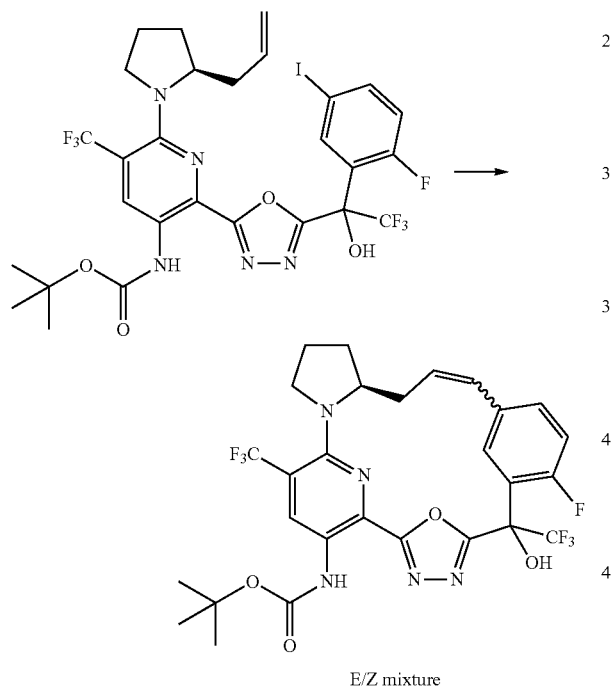

E/Z mixture

A stirred solution of tert-butyl N-[6-[(2S)-2-allylpyrrolidin-1-yl]-2-[5-[2,2,2-trifluoro-1-(2-fluoro-5-iodo-phenyl)-1-hydroxy-ethyl]-1,3,4-oxadiazol-2-yl]-5-(trifluoromethyl)-3-pyridyl]carbamate (2.0 g, 2.640 mmol) in acetonitrile (200 mL) was bubbled with $N_2$ for 5 min. Then, tris-o-tolylphosphane (167 mg, 0.5487 mmol) and Pd(OAc)$_2$ (64 mg, 0.2851 mmol) were added followed by triethylamine (2.0 mL, 14.35 mmol) and the solution was heated at 80° C. for 6 h. Cooled the mixture to room temperature, concentrated to about 5 mL volume and filtered through Celite and the filtrate was concentrated. The resultant brown residue was purified by silica gel chromatography using a shallow gradient from 100% hexanes to 50% EtOAc in hexanes to afford tert-butyl N-[(15S)-8-fluoro-6-hydroxy-6,21-bis(trifluoromethyl)-26-oxa-3,4,19,24-tetraazapentacyclo[18.3.1.12,5.17,11.015,19]hexacosa-1(24),2,4,7(25),8,10,12,20,22-nonaen-23-yl]carbamate (E/Z mixture) (1.04 g, 63%). ESI-MS m/z calc. 629.1873, found 630.3 (M+1)+; Retention time: 1.73 minutes (LC Method M).

Step 3: (6S,15R)-23-Amino-8-fluoro-6,21-bis(trifluoromethyl)-26-oxa-3,4,19,24-tetraazapentacyclo[18.3.1.12,5.17,11.015,19]hexacosa-1(24),2,4,7(25),8,10,20,22-octaen-6-ol (hydrochloride salt) (Compound 59) and (6R,15R)-23-amino-8-fluoro-6,21-bis(trifluoromethyl)-26-oxa-3,4,19,24-tetraazapentacyclo[18.3.1.12,5.17,11.015,19]hexacosa-1(24),2,4,7(25),8,10,20,22-octaen-6-ol (hydrochloride salt) (Compound 60)

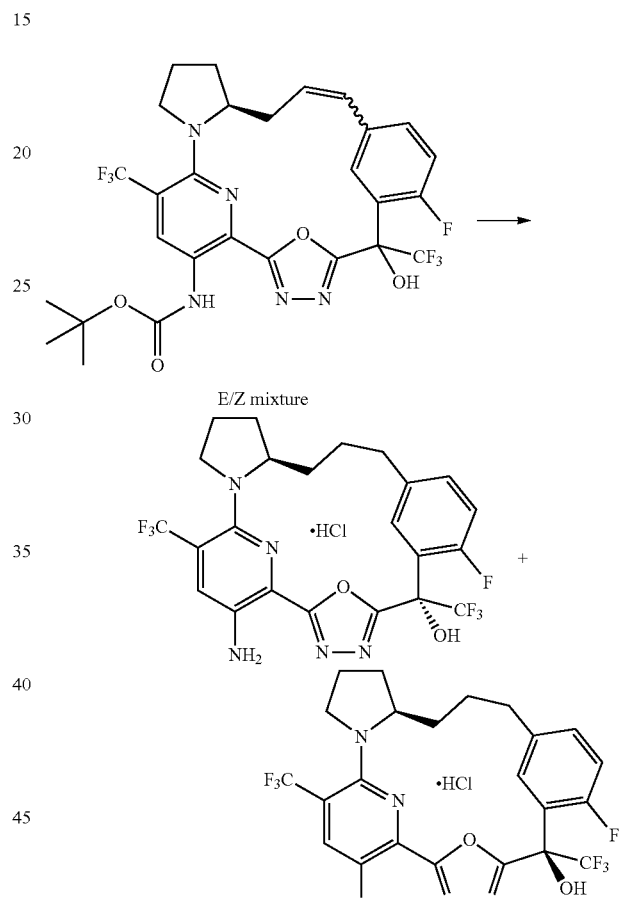

To a solution of tert-butyl N-[(15S)-8-fluoro-6-hydroxy-6,21-bis(trifluoromethyl)-26-oxa-3,4,19,24-tetraazapentacyclo[18.3.1.12,5.17,11.015,19]hexacosa-1(24),2,4,7(25),8,10,12,20,22-nonaen-23-yl]carbamate (E/Z mixture) (354 mg, 0.5623 mmol) in ethanol (5 mL) was added Pd/C (64 mg, 10% w/w, 0.06014 mmol) in a round bottom flask equipped with a $H_2$ balloon using a 3-way adaptor. Subjected to vacuum and backfilled with nitrogen gas three times then subjected to vacuum. Filled the flask with hydrogen gas and then stirred for 15 h. Subjected to vacuum and backfilled with nitrogen gas three times then diluted with ethyl acetate and filtered over Celite. The filtrate was concentrated and the residue was dissolved in 4 mL of 1:3 TFA/dichloromethane. This reaction mixture was stirred at room temperature for ~1 h and concentrated. The residue was purified by reverse phase HPLC using a gradient from 30% to 99% acetonitrile in water (+5 mM HCl) over 30 minutes giving as a yellow solid and the first enantiomer to elute, (6S,15R)-23-amino-8-fluoro-6,21-bis(trifluoromethyl)-26-oxa-3,4,19,24-tetraazapentacyclo[18.3.1.1²,⁵.1⁷,¹¹.0¹⁵,¹⁹]hexacosa-1(24),2,4,7(25),8,10,20,22-octaen-6-ol (hydrochloride salt) (9.1 mg, 39%). ¹H NMR (400 MHz, Chloroform-d) δ 7.90 (d, J=7.5 Hz, 1H), 7.42-7.35 (m, 1H), 7.22 (ddd, J=8.4, 4.6, 2.3 Hz, 1H), 7.02 (dd, J=12.5, 8.4 Hz, 1H), 4.30 (s, 1H), 3.87 (t, J=4.9 Hz, 1H), 3.66-3.57 (m, 1H), 3.31 (t, J=8.6 Hz, 1H), 2.98 (dd, J=14.6, 6.6 Hz, 1H), 2.58-2.49 (m, 1H), 2.45 (t, J=13.5 Hz, 1H), 2.16-2.08 (m, 1H), 1.95 (td, J=12.2, 11.1, 5.9 Hz, 2H), 1.69-1.59 (m, 3H), 1.04 (dd, J=12.0, 6.5 Hz, 1H) ppm. Three exchangeable protons not observed. ESI-MS m/z calc. 531.1505, found 532.1 (M+1)⁺; Retention time: 1.67 minutes (LC Method J).

The second enantiomer to elute was isolated as a yellow solid, (6R,15R)-23-amino-8-fluoro-6,21-bis(trifluoromethyl)-26-oxa-3,4,19,24-tetraazapentacyclo[18.3.1.1²,⁵.1⁷,¹¹.0¹⁵,¹⁹]hexacosa-1(24),2,4,7(25),8,10,20,22-octaen-6-ol (hydrochloride salt) (7.7 mg, 33%). ¹H NMR (400 MHz, DMSO-d6) δ 8.88 (s, 1H), 8.15 (dd, J=7.7, 2.3 Hz, 1H), 7.73 (s, 1H), 7.33 (ddd, J=8.4, 4.5, 2.3 Hz, 1H), 7.12 (dd, J=12.4, 8.4 Hz, 1H), 6.26 (s, 1H), 3.98 (dt, J=9.9, 5.3 Hz, 1H), 3.70 (br. s, 1H), 3.24 (d, J=9.0 Hz, 1H), 3.04 (d, J=15.2 Hz, 1H), 2.55 (m, 2H), 2.24 (dt, J=11.8, 5.9 Hz, 1H), 2.18-2.04 (m, 1H), 2.00-1.83 (m, 3H), 1.77-1.67 (m, 1H), 1.59 (qd, J=11.3, 6.1 Hz, 1H), 0.90-0.74 (m, 1H) ppm. ESI-MS m/z calc. 531.1505, found 532.0 (M+1)⁺; Retention time: 1.73 minutes (LC Method J).

Step 4: Solid Form Characterization of Amorphous Compound 60 (Neat Form)

A. X-Ray Powder Diffraction

The XRPD diffractogram for amorphous Compound 60 (neat form) produced by Step 3 was acquired using the General X-Ray Powder Diffraction (XRPD) Method and is provided in FIG. 12.

B. Thermogravimetric Analysis (TGA)

Figure 13:
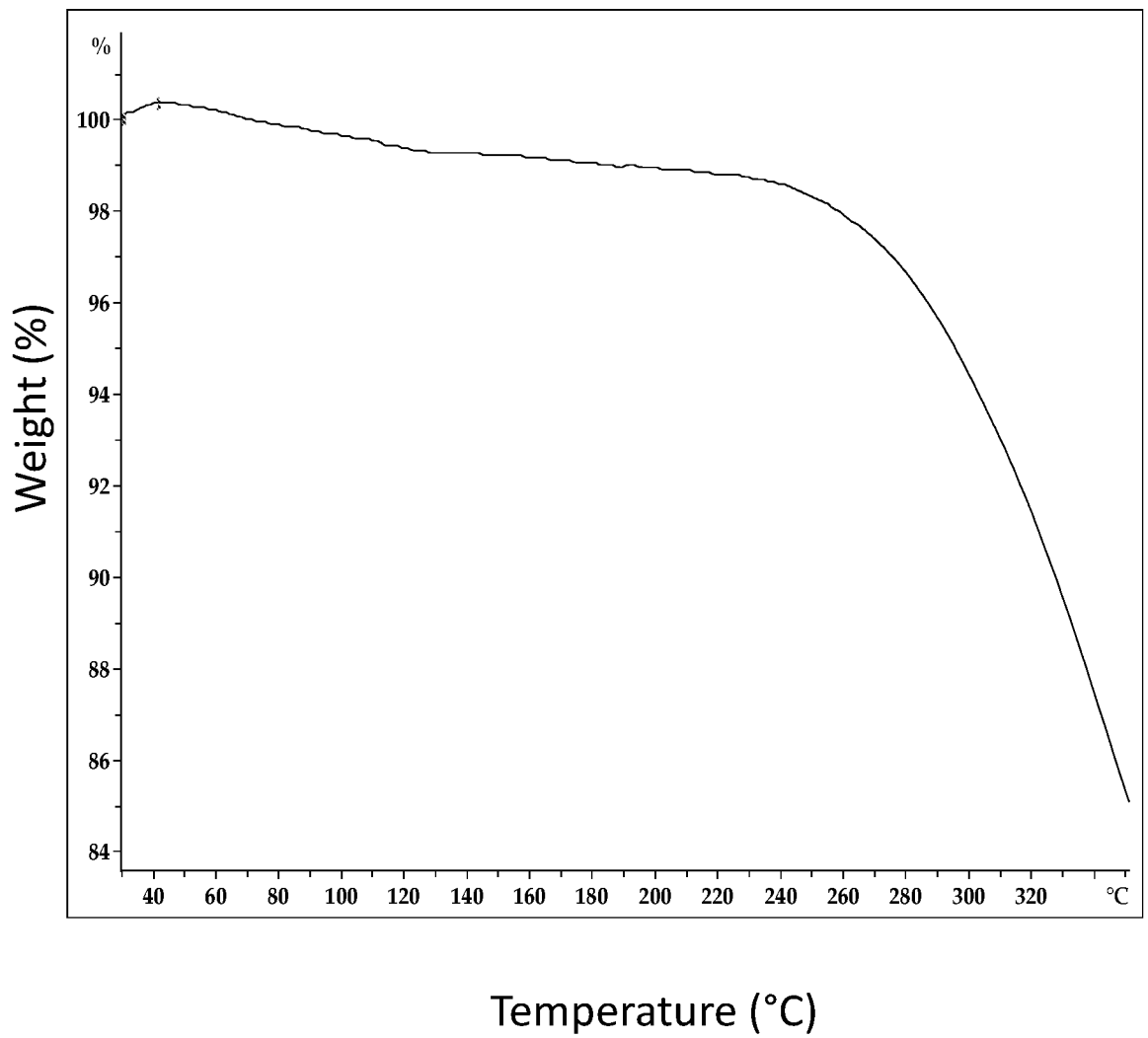
FIG. 13 provides a TGA curve for amorphous Compound 60 (neat form).

The TGA curve for amorphous Compound 60 (neat form) is provided in FIG. 13. The TGA curve shows 1.60% weight loss from 40° C. to 229.15° C., with a ramp of 10.00° C./min to 350.00° C.

C. Differential Scanning calorimetry Analysis

A neat amorphous free form of Compound 60 was generated using DSC by a heating and cooling methodology. The material was heated on the DSC pan to 240° C. and then cooled down to room temperature. Then the material was reheated to 240° C. to see the glass transition temperature of the amorphous material.

The DSC analysis was run using the following method:
1. 25.0 to 240.0° C., 10.00° C./min, N₂ 50.0 ml/min,
2. 240.0 to −20.0° C., −50.00° C./min, N₂ 50.0 ml/min, then
3. −20.0 to 240.0° C., 10.00° C./min, N₂ 50.0 ml/min.

Figure 14:
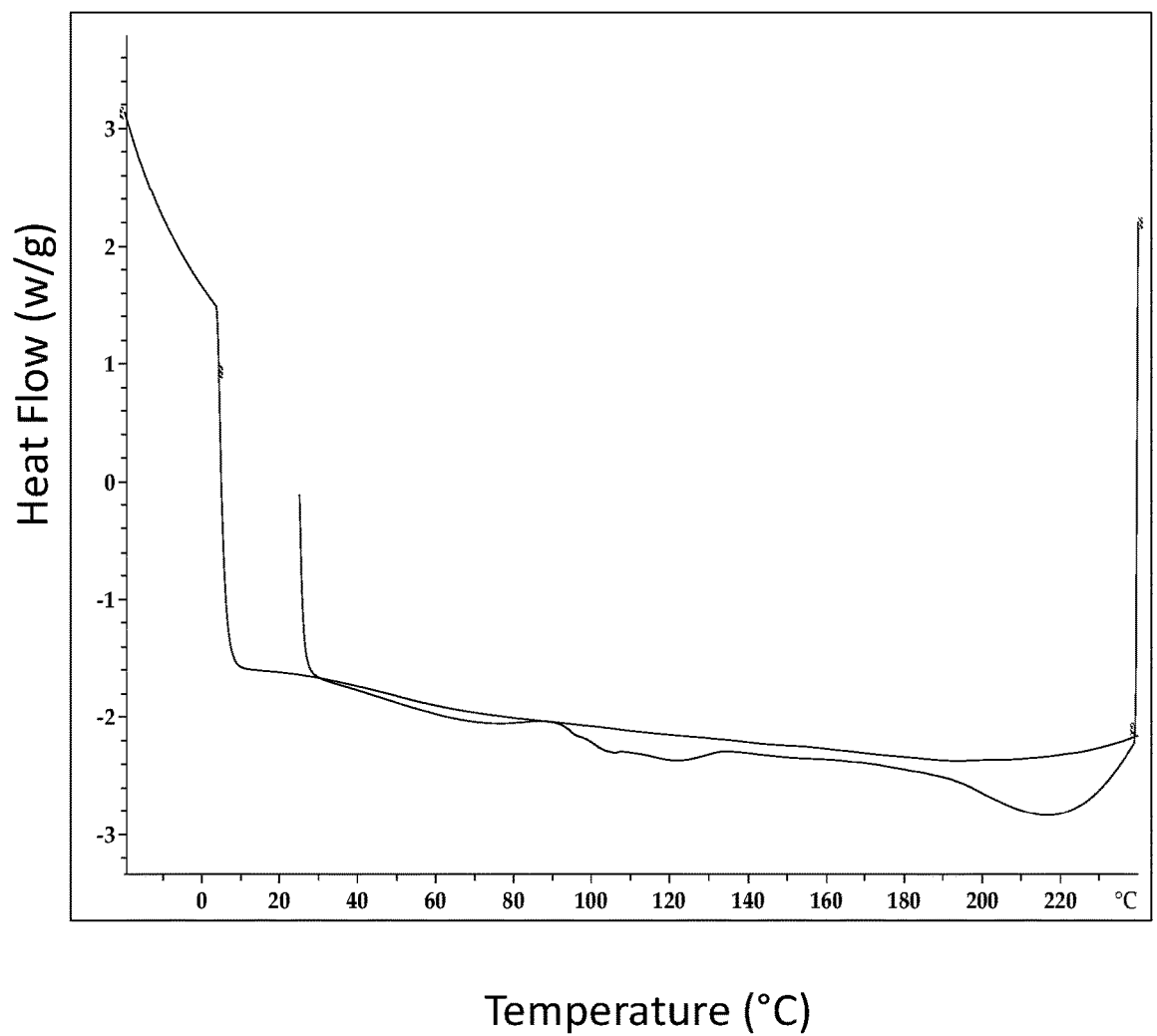
FIG. 14 provides a DSC analysis of amorphous Compound 60 (neat form).

The DSC thermogram for amorphous Compound 60 (neat form) is provided in FIG. 14. No Tg was observed.

Example 35: Preparation of 17-amino-6,13-dimethyl-15-(trifluoromethyl)-19-oxa-3,4,13,18-tetrazatricyclo[12.3.1.1²,⁵]nonadeca-1(17),2,4,14(18),15-pentaen-6-ol (enantiomer 1) (Compound 61) and 17-amino-6,13-dimethyl-15-(trifluoromethyl)-19-oxa-3,4,13,18-tetrazatricyclo[12.3.1.1²,⁵]nonadeca-1(17),2,4,14(18),15-pentaen-6-ol (enantiomer 2) (Compound 62)

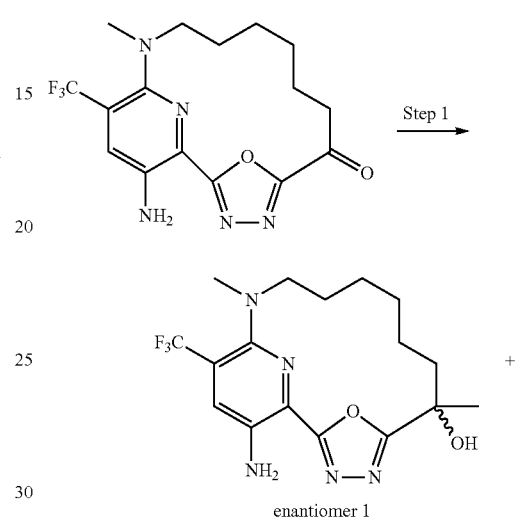

enantiomer 1

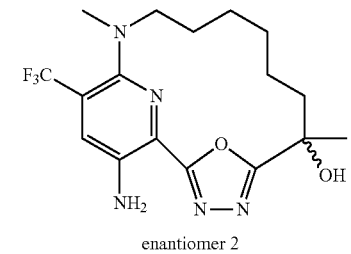

enantiomer 2

Step 1: 17-Amino-6,13-dimethyl-15-(trifluoromethyl)-19-oxa-3,4,13,18-tetrazatricyclo[12.3.1.1²,⁵] nonadeca-1(17),2,4,14(18),15-pentaen-6-ol (enantiomer 1) (Compound 61) and 17-amino-6,13-dimethyl-15-(trifluoromethyl)-19-oxa-3,4,13,18-tetrazatricyclo[12.3.1.1²,⁵]nonadeca-1(17),2,4,14 (18),15-pentaen-6-ol (enantiomer 2) (Compound 62)

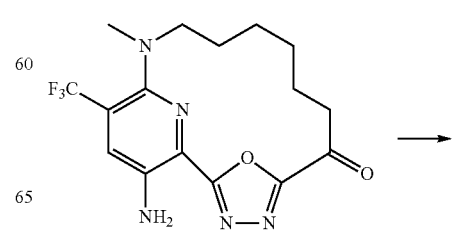

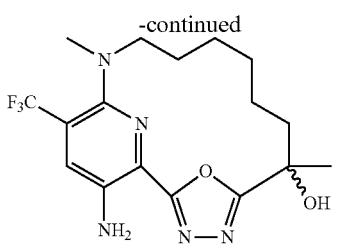

enantiomer 1


enantiomer 2

Under nitrogen, a solution of 17-amino-13-methyl-15-(trifluoromethyl)-19-oxa-3,4,13,18-tetrazatricyclo[12.3.1.1²,⁵]nonadeca-1(18),2,4,14,16-pentaen-6-one (25 mg, 0.06769 mmol) in THF (504.5 μL) was cooled to −78° C., then MeMgCl (67.70 μL of 3 M, 0.2031 mmol) was added dropwise and stirred the resulting mixture for 30 min. The reaction mixture was quenched with 1 M HCl and then extracted with EtOAc (2×30 mL). Combined organic layers were washed with brine, dried over $Na_2SO_4$, filtered and concentrated. The residue was purified by silica gel chromatography (12 g column) using a gradient from 0% to 40% ethyl acetate in hexanes to afford a racemic mixture as a yellow solid, which was further purified by normal phase SFC using an AS-H column (250×21.2 mm, 5 μm particle size) sold by Chiral Technologies (part number=20945) and eluting with a gradient of 45% to 80% MeOH (+20 mM $NH_3$) in $CO_2$ (flow rate=40 mL/min, column temperature=40° C.) which provided two single enantiomers:

The first enantiomer to elute was isolated as a yellow solid, 17-amino-6,13-dimethyl-15-(trifluoromethyl)-19-oxa-3,4,13,18-tetrazatricyclo[12.3.1.1²,⁵]nonadeca-1(17),2,4,14(18),15-pentaen-6-ol (enantiomer 1) (5 mg, 38%). ¹H NMR (400 MHz, Chloroform-d) δ 7.35 (s, 1H), 3.36-3.19 (m, 2H), 2.92 (s, 3H), 2.28 (s, 3H), 2.06 (dt, J=14.6, 7.9 Hz, 2H), 1.84 (dtd, J=28.4, 12.8, 11.3, 6.1 Hz, 4H), 1.70 (s, 3H), 1.55-1.47 (m, 2H), 1.44-1.34 (m, 2H) ppm. ESI-MS m/z calc. 385.17255, found 386.2 (M+1)⁺; Retention time: 1.78 minutes (LC Method A).

The second enantiomer to elute was isolated as a yellow solid, 17-amino-6,13-dimethyl-15-(trifluoromethyl)-19-oxa-3,4,13,18-tetrazatricyclo[12.3.1.1²,⁵]nonadeca-1(17),2,4,14(18),15-pentaen-6-ol (enantiomer 2) (5 mg, 36%). ¹H NMR (400 MHz, Chloroform-d) δ 7.53 (d, J=6.5 Hz, 1H), 3.41 (d, J=37.2 Hz, 2H), 3.04 (s, 3H), 2.76-2.30 (m, 3H), 2.26-2.07 (m, 2H), 1.98 (dd, J=14.5, 7.6 Hz, 3H), 1.79 (s, 3H), 1.66-1.41 (m, 5H) ppm. ESI-MS m/z calc. 385.17255, found 386.2 (M+1)⁺; Retention time: 1.77 minutes (LC Method A).

Example 36: Preparation of (12R)-20-amino-18-(propan-2-yl)-6-(trifluoromethyl)-22-oxa-3,4,16,21-tetraazatetracyclo[15.3.1.1²,⁵.0¹²,¹⁶]docosa-1(21),2,4,17,19-pentaen-6-ol (enantiomer 1) (Compound 63) and (12R)-20-amino-18-(propan-2-yl)-6-(trifluoromethyl)-22-oxa-3,4,16,21-tetraazatetracyclo[15.3.1.1²,⁵.0¹²,¹⁶]docosa-1(21),2,4,17,19-pentaen-6-ol (enantiomer 2) (Compound 64)

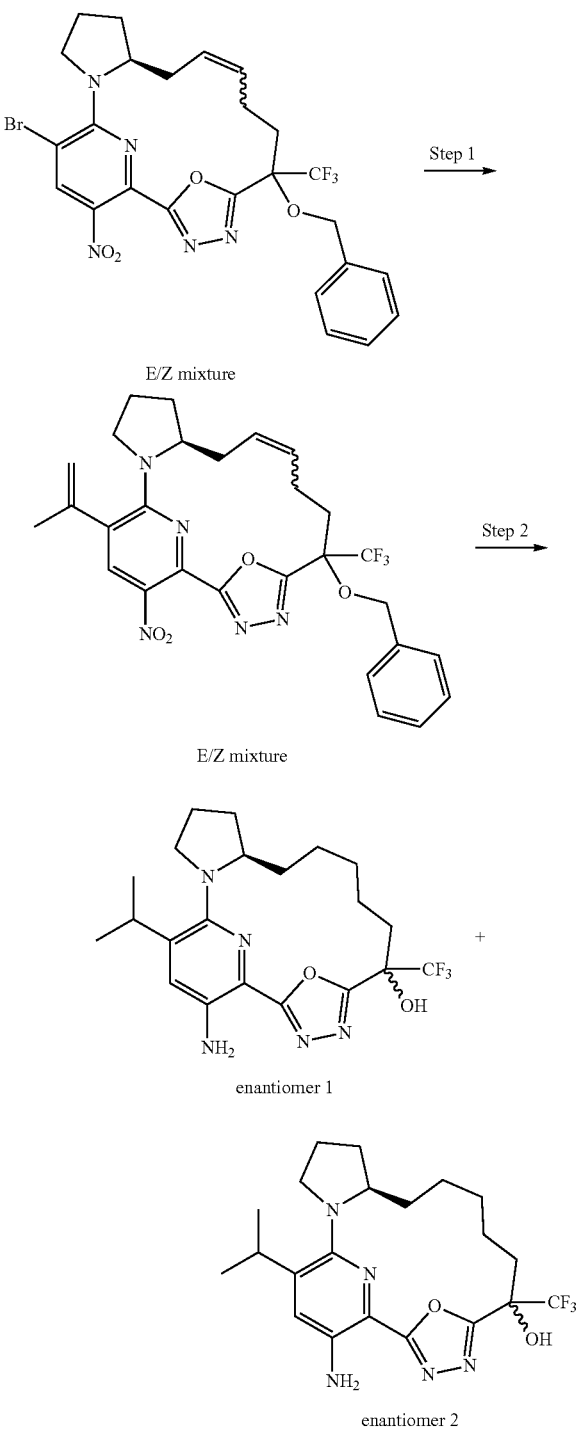

Step 1: (12S)-6-(Benzyloxy)-20-nitro-18-(prop-1-en-2-yl)-6-(trifluoromethyl)-22-oxa-3,4,16,21-tetraazatetracyclo[15.3.1.12,5.012,16]docosa-1(21),2,4,9,17,19-hexaene (E/Z Mixture)

Step 2: (12R)-20-Amino-18-(propan-2-yl)-6-(trifluoromethyl)-22-oxa-3,4,16,21-tetraazatetracyclo[15.3.1.12,5.012,16]docosa-1(21),2,4,17,19-pentaen-6-ol (enantiomer 1) (Compound 63) and (12R)-20-amino-18-(propan-2-yl)-6-(trifluoromethyl)-22-oxa-3,4,16,21-tetraazatetracyclo[15.3.1.12,5.012,16]docosa-1(21),2,4,17,19-pentaen-6-ol (enantiomer 2) (Compound 64)

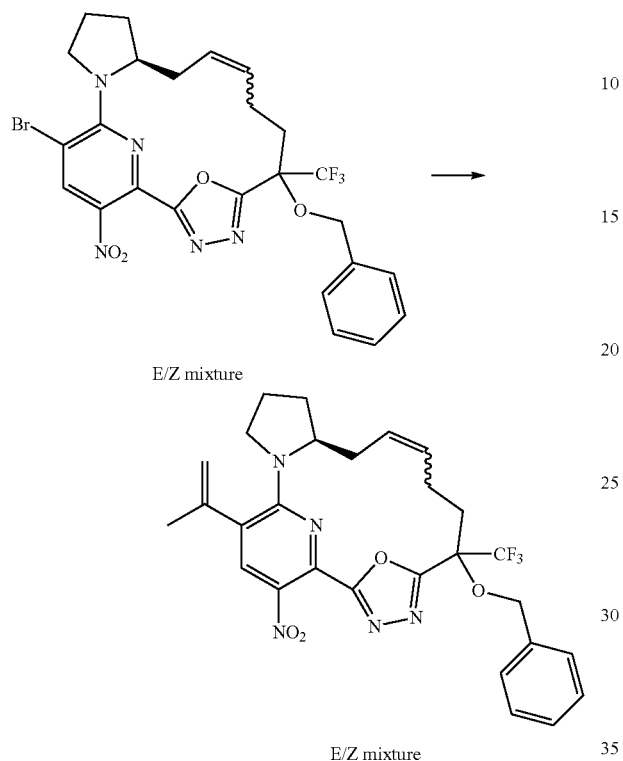

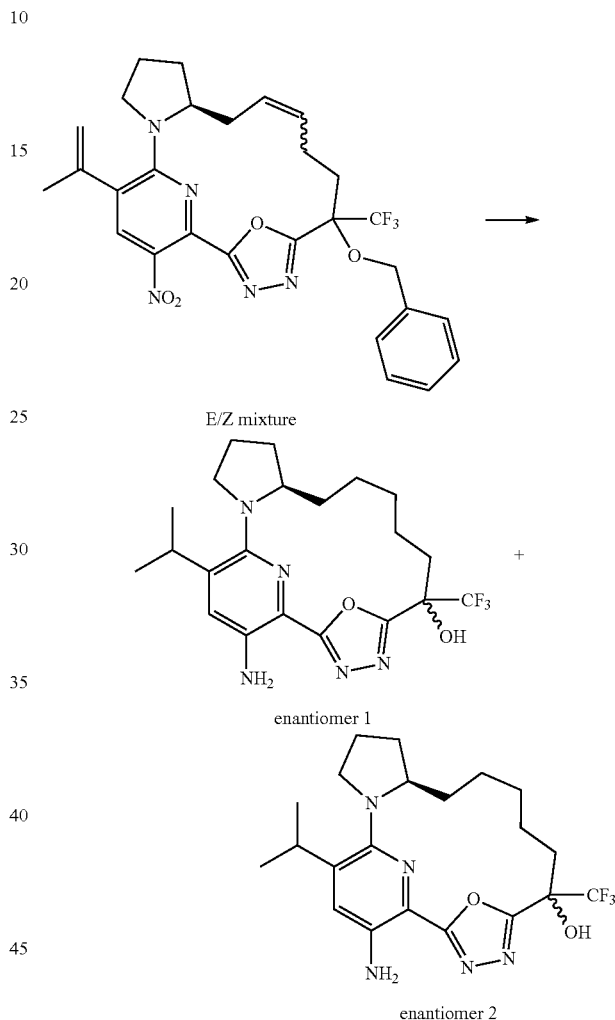

A solution of (12S)-6-(benzyloxy)-18-bromo-20-nitro-6-(trifluoromethyl)-22-oxa-3,4,16,21-tetraazatetracyclo[15.3.1.12,5.012,16]docosa-1(21),2,4,9,17,19-hexaene (330 mg, 0.5063 mmol) in toluene (14 mL) was degassed by nitrogen bubbling for 20 min. Potassium isopropenyltrifluoroborate (106 mg, 0.7163 mmol) and 1,1'-bis(diphenylphosphino)ferrocene palladium(II) chloride, complex with dichloromethane (23 mg, 0.0282 mmol) were added followed by nitrogen degassed aqueous solution of cesium carbonate (0.6 mL, 2 M, 1.2000 mmol). The reaction mixture was stirred overnight at 90° C. The reaction mixture was cooled to room temperature, filtered through a pad of Celite and rinsed with ethyl acetate (2×25 mL). The filtrate was dried over anhydrous sodium sulfate, filtered and concentrated. The residue was purified by silica gel chromatography (40 g column) using a gradient from 0% to 25% ethyl acetate in heptanes to afford as a red foam, (12S)-6-(benzyloxy)-20-nitro-18-(prop-1-en-2-yl)-6-(trifluoromethyl)-22-oxa-3,4,16,21-tetraazatetracyclo[15.3.1.12,5.012,16]docosa-1(21),2,4,9,17,19-hexaene (E/Z mixture) (210 mg, 71%). ESI-MS m/z calc. 555.20935, found 556.2 (M+1)+; Retention time: 2.56 minutes (LC Method E).

A solution of (12S)-6-(benzyloxy)-20-nitro-18-(prop-1-en-2-yl)-6-(trifluoromethyl)-22-oxa-3,4,16,21-tetraazatetracyclo[15.3.1.12,5.012,16]docosa-1(21),2,4,9,17,19-hexaene (E/Z mixture) (210 mg, 0.3591 mmol) in methanol (21 mL) was bubbled with nitrogen for 5 min and then palladium on carbon (160 mg, 0.0752 mmol) was added. The resulting mixture was bubbled with a balloon of hydrogen for 5 min and then stirred at room temperature under hydrogen overnight. The mixture was filtered through a pad of Celite and washed with methanol (25 mL) then concentrated under reduced pressure. The residue was purified by silica gel chromatography (40 g column) using a gradient from 0% to 25% ethyl acetate in heptanes giving as a yellow solid, and the first enantiomer to elute, (12R)-20-amino-18-(propan-2-yl)-6-(trifluoromethyl)-22-oxa-3,4,16,21-tetraazatetracyclo[15.3.1.12,5.012,16]docosa-1(21),2,4,17,19-pentaen-6-ol (enantiomer 1) (54 mg, 32%). 1H NMR (300 MHz, Chloroform-d) δ 7.01 (s, 1H), 5.02 (br. s., 2H), 4.03-3.80 (m, 1H), 3.79-3.58 (m, 2H), 3.35-3.20 (m, 1H), 3.15 (td, J=9.0, 3.1 Hz, 1H), 2.56-2.34 (m, 2H), 2.30-2.14 (m, 1H), 2.12-1.92 (m, 2H), 1.90-1.76 (m, 1H), 1.73-1.42 (m, 8H), 1.33 (d, J=6.8 Hz, 3H), 1.15 (d, J=6.2 Hz, 3H) ppm. ESI-MS m/z calc. 439.2195, found 440.3 (M+1)$^+$; Retention time: 3.3 minutes (LC Method C).

The second enantiomer to elute was isolated as a yellow solid, (12R)-20-amino-18-(propan-2-yl)-6-(trifluoromethyl)-22-oxa-3,4,16,21-tetraazatetracyclo[15.3.1.1.2,5.012,16]docosa-1(21),2,4,17,19-pentaen-6-ol (enantiomer 2) (29 mg, 18%). $^1$H NMR (300 MHz, Chloroform-d) δ 7.01 (s, 1H), 5.47-4.58 (m, 2H), 4.04-3.83 (m, 1H), 3.81-3.67 (m, 1H), 3.65-3.51 (m, 1H), 3.33-3.17 (m, 1H), 3.16-2.99 (m, 1H), 2.67-2.48 (m, 1H), 2.45-2.29 (m, 1H), 2.28-2.10 (m, 2H), 2.06-1.87 (m, 2H), 1.86-1.72 (m, 1H), 1.70-1.45 (m, 7H), 1.34 (d, J=6.8 Hz, 3H), 1.14 (d, J=6.5 Hz, 3H) ppm. ESI-MS m/z calc. 439.2195, found 440.3 (M+1)$^+$; Retention time: 3.22 minutes (LC Method C).

Example 37: Preparation of 17-amino-12-methyl-6,15-bis(trifluoromethyl)-19-oxa-3,4,13,18-tetrazatricyclo[12.3.1.1.2,5]nonadeca-1(18),2,4,14,16-pentaen-6-ol (enantiomer 1) (Compound 65), 17-amino-12-methyl-6,15-bis(trifluoromethyl)-19-oxa-3,4,13,18-tetrazatricyclo[12.3.1.1.2,5]nonadeca-1(18),2,4,14,16-pentaen-6-ol (enantiomer 2) (Compound 66), 17-amino-12-methyl-6,15-bis(trifluoromethyl)-19-oxa-3,4,13,18-tetrazatricyclo[12.3.1.1.2,5]nonadeca-1(18),2,4,14,16-pentaen-6-ol (enantiomer 3) (Compound 67) and 17-amino-12-methyl-6,15-bis(trifluoromethyl)-19-oxa-3,4,13,18-tetrazatricyclo[12.3.1.1.2,5]nonadeca-1(18),2,4,14,16-pentaen-6-ol (enantiomer 4) (Compound 68)

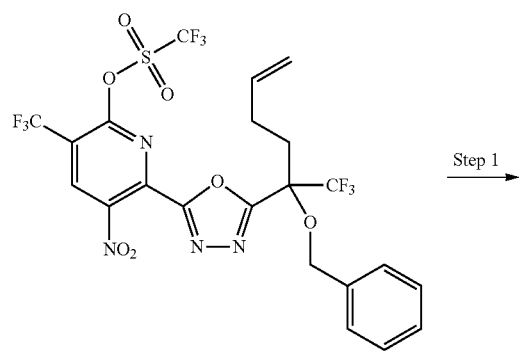

Step 1

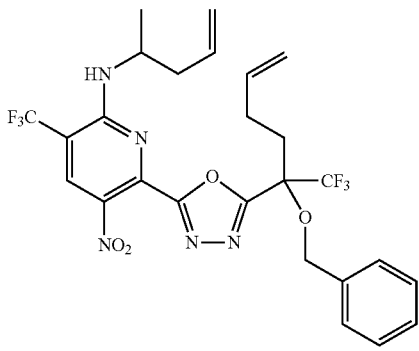

Step 2

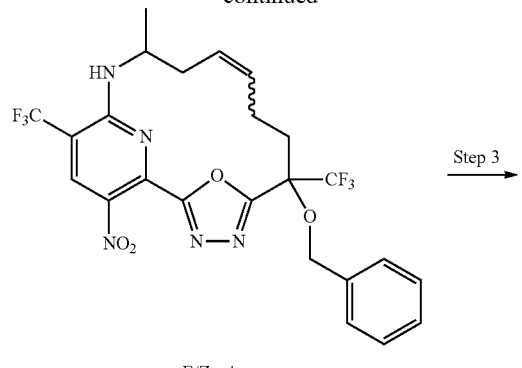

E/Z mixture

Step 3

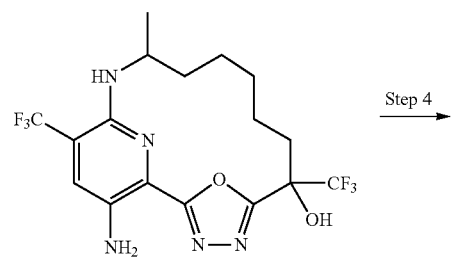

Step 4

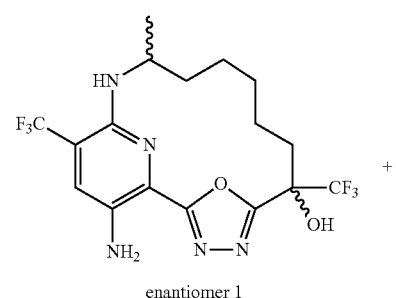

enantiomer 1

+

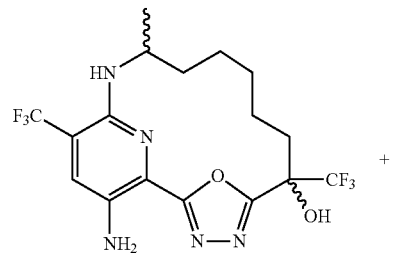

enantiomer 2

+

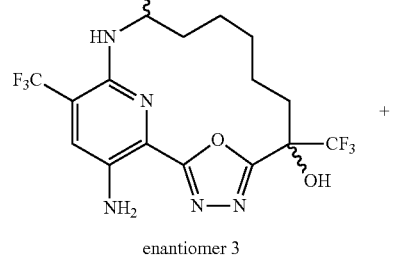

enantiomer 3

+

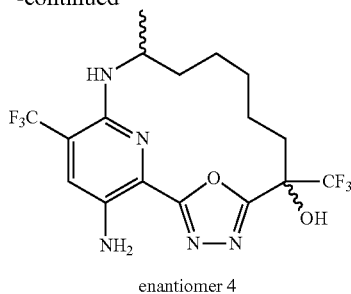

enantiomer 4

Step 1: 6-[5-[1-Benzyloxy-1-(trifluoromethyl)pent-4-enyl]-1,3,4-oxadiazol-2-yl]-N-(1-methylbut-3-enyl)-5-nitro-3-(trifluoromethyl)pyridin-2-amine

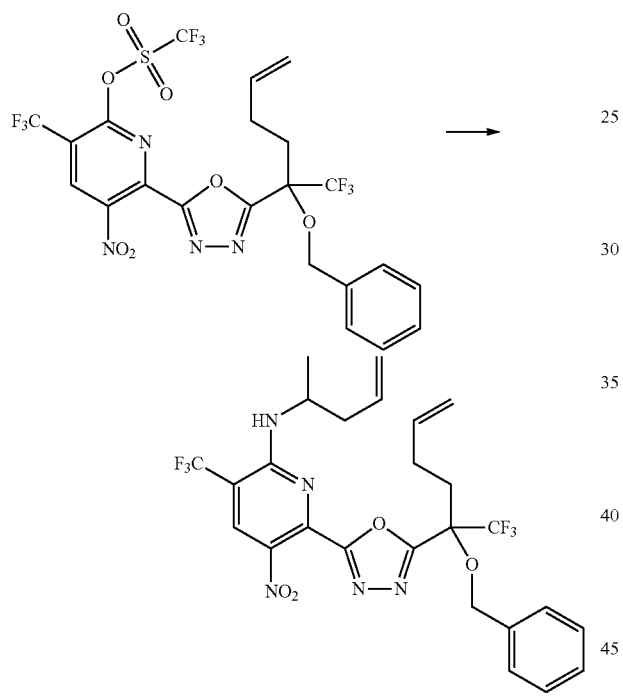

In a 40 mL sealed vial, [6-[5-[1-benzyloxy-1-(trifluoromethyl)pent-4-enyl]-1,3,4-oxadiazol-2-yl]-5-nitro-3-(trifluoromethyl)-2-pyridyl]trifluoromethanesulfonate (425 mg, 0.6534 mmol) was dissolved in acetonitrile (11 mL) at room temperature followed by addition of DIEA (750 μL, 4.306 mmol) and pent-4-en-2-amine (hydrochloride salt) (220 mg, 1.809 mmol) and then the mixture was stirred for 90 minutes. The reaction was concentrated. The crude material was then purified by silica gel chromatography using a gradient from 100% hexanes to 60% ethyl acetate to afford as a yellow foam, 6-[5-[1-benzyloxy-1-(trifluoromethyl)pent-4-enyl]-1,3,4-oxadiazol-2-yl]-N-(1-methylbut-3-enyl)-5-nitro-3-(trifluoromethyl)pyridin-2-amine (266 mg, 70%). $^1$H NMR (400 MHz, DMSO-d6) δ 8.54 (s, 1H), 7.78 (d, J=8.1 Hz, 1H), 7.38-7.31 (m, 5H), 5.85 (ddt, J=16.8, 10.2, 6.5 Hz, 1H), 5.78-5.63 (m, 1H), 5.13-4.94 (m, 4H), 4.76 (d, J=10.8 Hz, 1H), 4.60 (d, J=10.8 Hz, 1H), 4.48 (dq, J=8.2, 5.9 Hz, 1H), 2.59-2.51 (m, 2H), 2.47-2.40 (m, 1H), 2.33-2.19 (m, 3H), 1.22 (d, J=6.6 Hz, 3H) ppm. ESI-MS m/z calc. 585.1811, found 586.2 (M+1)$^+$; Retention time: 2.01 minutes (LC Method J).

Step 2: 6-Benzyloxy-12-methyl-17-nitro-6,15-bis(trifluoromethyl)-19-oxa-3,4,13,18-tetrazatricyclo[12.3.1.1²,⁵]nonadeca-1(18),2,4,9,14,16-hexaene (E/Z Mixture)

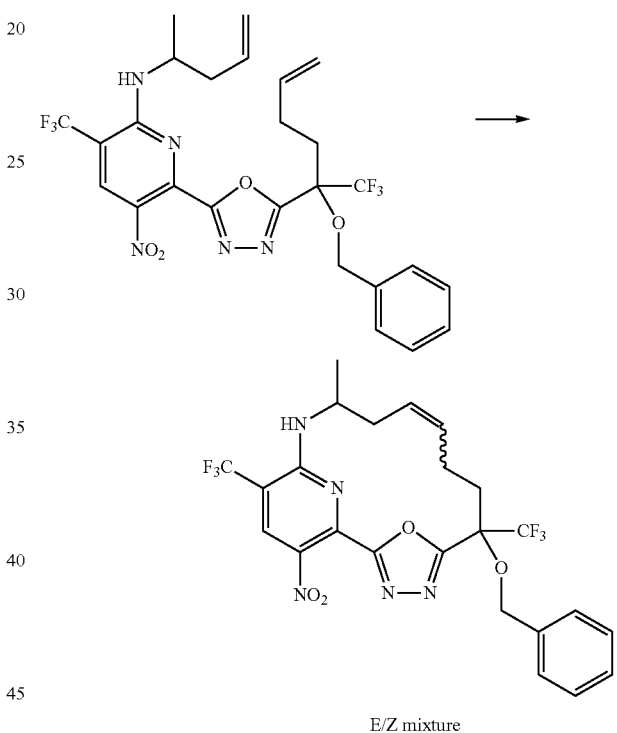

E/Z mixture

In a 500 mL round bottom flask, a continuously degassed solution via nitrogen line of Zhan catalyst-1B (82 mg, 0.1118 mmol) in DCE (200 mL) was heated at 50° C. under nitrogen atmosphere. Then, a solution of 6-[5-[1-benzyloxy-1-(trifluoromethyl)pent-4-enyl]-1,3,4-oxadiazol-2-yl]-N-(1-methylbut-3-enyl)-5-nitro-3-(trifluoromethyl)pyridin-2-amine (260 mg, 0.4441 mmol) in DCE (40 mL) was added dropwise via syringe. The resulting mixture was heated at 75° C. for 3 h. The reaction mixture was cooled to room temperature and concentrated under reduced pressure. The crude material was then purified by silica gel chromatography using a gradient from 100% hexanes to 50% ethyl acetate in hexanes to afford as a pale yellow solid, 6-benzyloxy-12-methyl-17-nitro-6,15-bis(trifluoromethyl)-19-oxa-3,4,13,18-tetrazatricyclo[12.3.1.1²,⁵]nonadeca-1(18),2,4,9,14,16-hexaene (E/Z mixture) (150 mg, 61%). ESI-MS m/z calc. 557.1498, found 558.2 (M+1)$^+$; Retention time: 1.78 minutes (LC Method J).

461

Step 3: 17-Amino-12-methyl-6,15-bis(trifluoromethyl)-19-oxa-3,4,13,18-tetrazatricyclo[12.3.1.1²,⁵]nonadeca-1(18),2,4,14,16-pentaen-6-ol

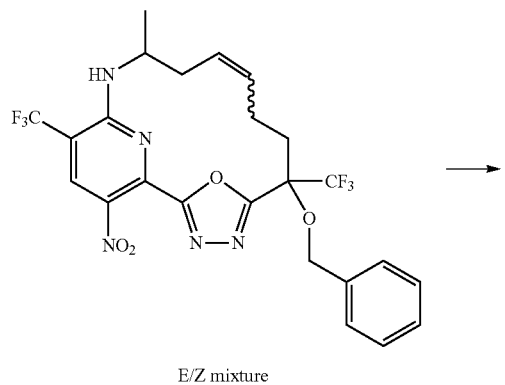

E/Z mixture

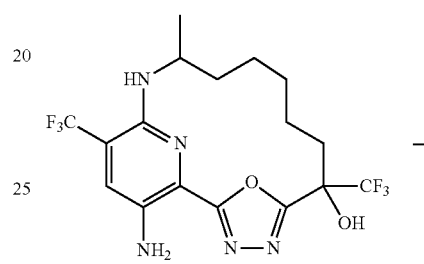

In a 250 mL round bottom flask, a solution of 6-benzyloxy-12-methyl-17-nitro-6,15-bis(trifluoromethyl)-19-oxa-3,4,13,18-tetrazatricyclo[12.3.1.1²,⁵]nonadeca-1(18),2,4,9,14,16-hexaene (E/Z mixture) (145 mg, 0.2601 mmol) in AcOH (2.5 mL) and ethyl acetate (2.5 mL) was purged with nitrogen. Then Pd/C (275 mg of 10% w/w, 0.2584 mmol) was added. The mixture was degassed with nitrogen for 5 minutes, then purged by a balloon filled with hydrogen gas. The mixture was stirred at 1 atmosphere of hydrogen for 4 h. The reaction was filtered and washed the Celite plug with excess acetonitrile and ethyl acetate then concentrated the filtrate. The crude material was then purified by silica gel chromatography using a gradient from 100% hexanes to 70% ethyl acetate in hexanes to afford as a yellow solid and mixture of 4 stereoisomers, 17-amino-12-methyl-6,15-bis(trifluoromethyl)-19-oxa-3,4,13,18-tetrazatricyclo[12.3.1.1²,⁵]nonadeca-1(18),2,4,14,16-pentaen-6-ol (95 mg, 83%). ESI-MS m/z calc. 439.1443, found 440.2 (M+1)⁺; Retention time: 1.34 minutes (LC Method A).

462

Step 4: 17-Amino-12-methyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (Compound 65), 17-amino-12-methyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (Compound 66), 17-amino-12-methyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 3) (Compound 67) and 17-amino-12-methyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 4) (Compound 68)

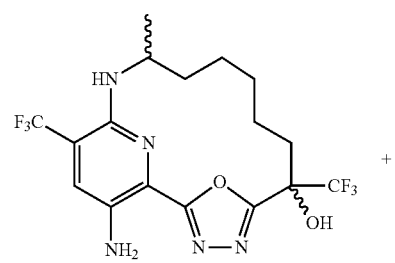

enantiomer 1 enantiomer 2

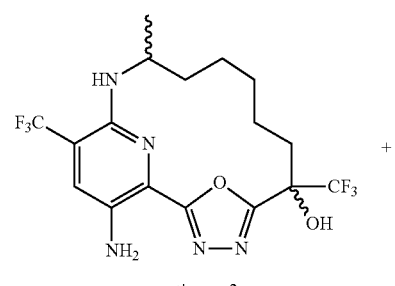

enantiomer 3

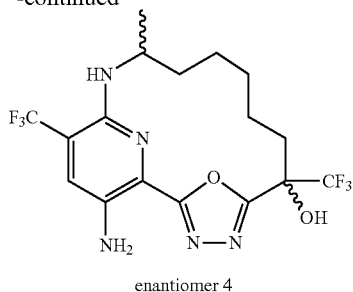

enantiomer 4

Racemic 17-amino-12-methyl-6,15-bis(trifluoromethyl)-19-oxa-3,4,13,18-tetrazatricyclo[12.3.1.12,5]nonadeca-1(18),2,4,14,16-pentaen-6-ol (93 mg, 0.2117 mmol) was purified by chiral SFC using a Phenomenex LUX-4 column (250×21.2 mm, 5 μm particle size) at 40° C. eluting with 10% MeOH (+20 mM $NH_3$)/90% $CO_2$ using a flow rate of 70 mL/min with an injection volume of 500 μL which gave the separation of four enantiomers:

The first enantiomer to elute was isolated as a yellow solid, 17-amino-12-methyl-6,15-bis(trifluoromethyl)-19-oxa-3,4,13,18-tetrazatricyclo[12.3.1.12,5]nonadeca-1(18),2,4,14,16-pentaen-6-ol (enantiomer 1) (18.8 mg, 80%). $^1$H NMR (400 MHz, DMSO-d6) δ 7.59 (d, J=15.2 Hz, 2H), 6.01 (s, 2H), 5.10 (d, J=4.5 Hz, 1H), 3.69-3.59 (m, 1H), 2.29-2.18 (m, 1H), 2.01 (ddd, J=13.9, 10.7, 7.0 Hz, 1H), 1.61 (d, J=9.8 Hz, 2H), 1.50 (d, J=9.2 Hz, 3H), 1.44 (d, J=9.1 Hz, 2H), 1.24 (d, J=6.7 Hz, 3H), 0.84 (td, J=14.7, 11.1, 6.0 Hz, 1H) ppm. ESI-MS m/z calc. 439.1443, found 440.2 (M+1)$^+$; Retention time: 1.98 minutes (LC Method A).

The second enantiomer to elute was isolated as a yellow solid, 17-amino-12-methyl-6,15-bis(trifluoromethyl)-19-oxa-3,4,13,18-tetrazatricyclo[12.3.1.12,5]nonadeca-1(18),2,4,14,16-pentaen-6-ol (enantiomer 2) (16.0 mg, 68%). $^1$H NMR (400 MHz, DMSO-d6) δ 7.61 (s, 1H), 7.55 (s, 1H), 6.00 (d, J=7.6 Hz, 2H), 5.13 (d, J=4.9 Hz, 1H), 3.78-3.65 (m, 1H), 2.43-2.26 (m, 2H), 2.07-1.99 (m, 1H), 1.69 (s, 2H), 1.43 (s, 4H), 1.24 (d, J=6.7 Hz, 3H), 0.90 (ddt, J=18.2, 12.2, 5.9 Hz, 1H) ppm. ESI-MS m/z calc. 439.1443, found 440.2 (M+1)$^+$; Retention time: 1.95 minutes (LC Method A).

The third enantiomer to elute was isolated as a yellow solid, 17-amino-12-methyl-6,15-bis(trifluoromethyl)-19-oxa-3,4,13,18-tetrazatricyclo[12.3.1.12,5]nonadeca-1(18),2,4,14,16-pentaen-6-ol (enantiomer 3) (18.3 mg, 78%). $^1$H NMR (400 MHz, DMSO-d6) δ 7.59 (d, J=15.1 Hz, 2H), 6.00 (d, J=7.6 Hz, 2H), 5.10 (d, J=4.6 Hz, 1H), 3.67-3.59 (m, 1H), 2.47 (s, 1H), 2.28-2.19 (m, 1H), 2.00 (ddd, J=13.8, 8.8, 5.7 Hz, 1H), 1.66-1.57 (m, 2H), 1.53-1.50 (m, 1H), 1.44 (d, J=11.0 Hz, 3H), 1.24 (d, J=6.7 Hz, 3H), 0.89-0.81 (m, 1H) ppm. ESI-MS m/z calc. 439.1443, found 440.2 (M+1)$^+$; Retention time: 1.98 minutes (LC Method A).

The fourth enantiomer to elute was isolated as a yellow solid, 17-amino-12-methyl-6,15-bis(trifluoromethyl)-19-oxa-3,4,13,18-tetrazatricyclo[12.3.1.12,5]nonadeca-1(18),2,4,14,16-pentaen-6-ol (enantiomer 4) (16.4 mg, 70%). $^1$H NMR (400 MHz, DMSO-d6) δ 7.61 (s, 1H), 7.55 (s, 1H), 6.00 (d, J=7.8 Hz, 2H), 5.13 (d, J=4.9 Hz, 1H), 3.76-3.67 (m, 1H), 2.42-2.26 (m, 2H), 2.08 (s, 2H), 1.71-1.67 (m, 1H), 1.49-1.38 (m, 4H), 1.24 (d, J=6.7 Hz, 3H), 0.96-0.86 (m, 1H) ppm. ESI-MS m/z calc. 439.1443, found 440.2 (M+1)$^+$; Retention time: 1.95 minutes (LC Method A).

Example 38: Preparation of (15R)-23-amino-6,21-bis(trifluoromethyl)-26-oxa-3,4,19,24-tetraazapentacyclo[18.3.1.12,5.17,11.015,19]hexacosa-1(24),2,4,7(25),8,10,20,22-octaen-6-ol (hydrochloride salt) (enantiomer 1) (Compound 69) and (15R)-23-amino-6,21-bis(trifluoromethyl)-26-oxa-3,4,19,24-tetraazapentacyclo[18.3.1.12,5.17,11.015,19]hexacosa-1(24),2,4,7(25),8,10,20,22-octaen-6-ol (enantiomer 2) (Compound 70)

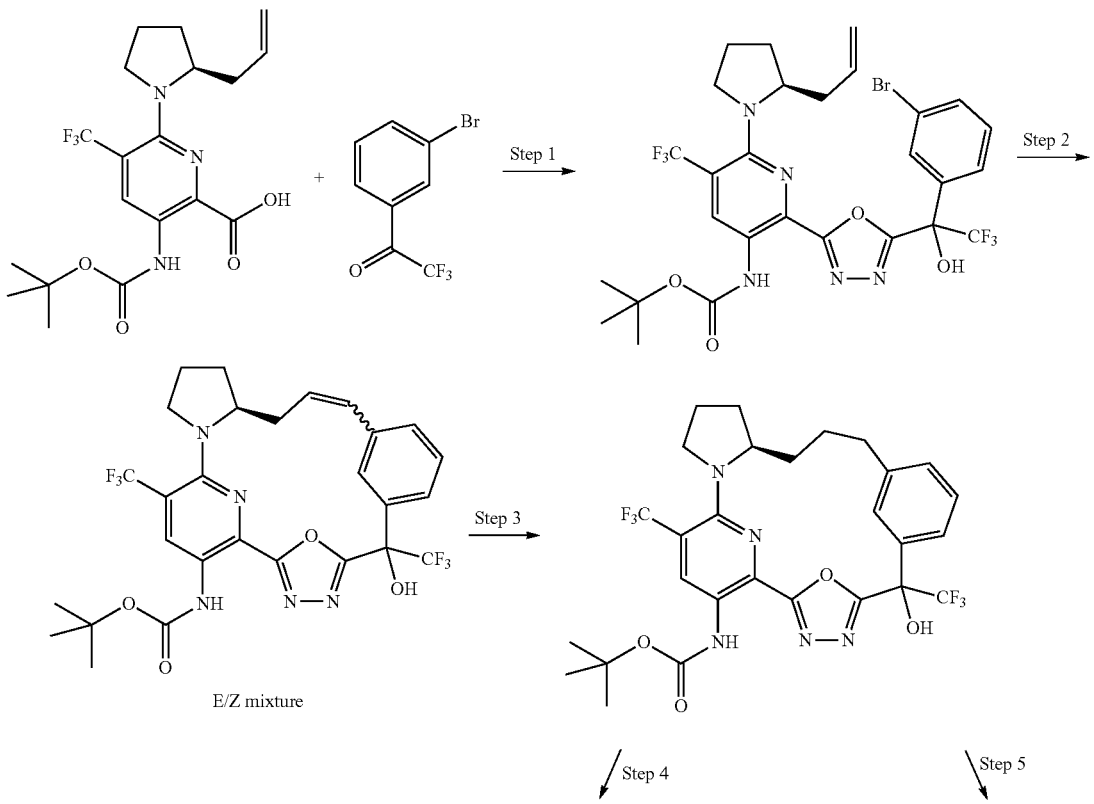

-continued

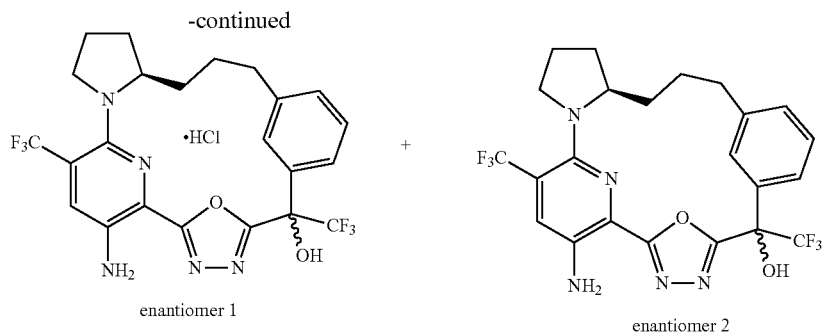

enantiomer 1 + enantiomer 2

Step 1: tert-Butyl N-[6-[(2S)-2-allylpyrrolidin-1-yl]-2-[5-[1-(3-bromophenyl)-2,2,2-trifluoro-1-hydroxy-ethyl]-1,3,4-oxadiazol-2-yl]-5-(trifluoromethyl)-3-pyridyl]carbamate

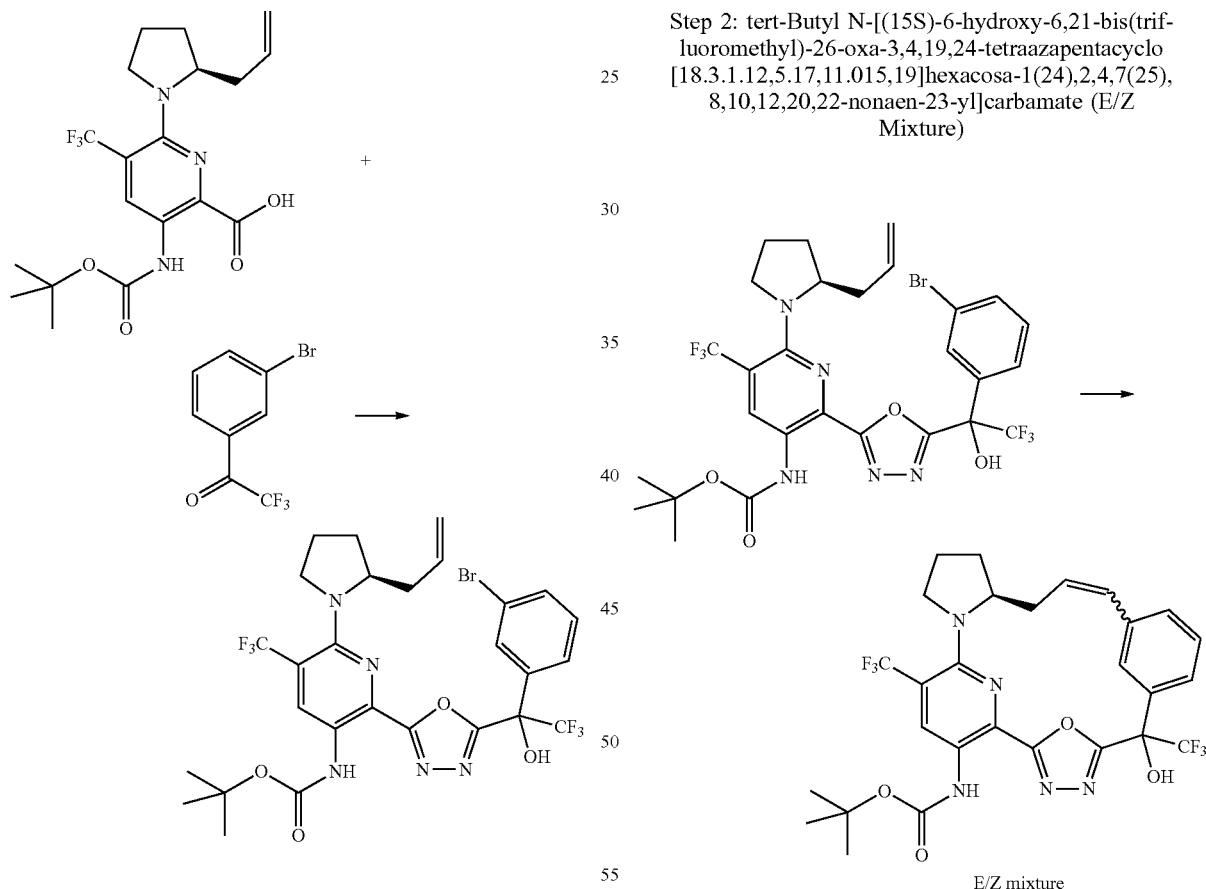

To a stirred solution of (N-isocyanoimino)triphenylphosphorane (4.843 g, 16.02 mmol) and 1-(3-bromophenyl)-2,2,2-trifluoro-ethanone (4.053 g, 16.02 mmol) in DMF (79.83 mL) was added 6-[(2S)-2-allylpyrrolidin-1-yl]-3-(tert-butoxycarbonylamino)-5-(trifluoromethyl)pyridine-2-carboxylic acid (3.2453 g, 6.406 mmol). The mixture was capped and stirred at room temperature for 15 min. Diluted the mixture with EtOAc and washed with saturated NaHCO₃ (1×), saturated NH₄Cl (1×) and brine (1×). Dried the organic layer over sodium sulfate, filtered and concentrated to an orange oil which was purified by silica gel chromatography using a shallow gradient from 100% hexanes to 100% ethyl acetate giving as a yellow/orange syrup, tert-butyl N-[6-[(2S)-2-allylpyrrolidin-1-yl]-2-[5-[1-(3-bromophenyl)-2,2,2-trifluoro-1-hydroxy-ethyl]-1,3,4-oxadiazol-2-yl]-5-(trifluoromethyl)-3-pyridyl]carbamate (4.4 g, 99%). ESI-MS m/z calc. 691.12286, found 692.2 (M+1)⁺; Retention time: 0.82 minutes (LC Method T).

Step 2: tert-Butyl N-[(15S)-6-hydroxy-6,21-bis(trifluoromethyl)-26-oxa-3,4,19,24-tetraazapentacyclo[18.3.1.1²,⁵.1⁷,¹¹.0¹⁵,¹⁹]hexacosa-1(24),2,4,7(25),8,10,12,20,22-nonaen-23-yl]carbamate (E/Z Mixture)

To a stirred solution of tert-butyl N-[6-[(2S)-2-allylpyrrolidin-1-yl]-2-[5-[1-(3-bromophenyl)-2,2,2-trifluoro-1-hydroxy-ethyl]-1,3,4-oxadiazol-2-yl]-5-(trifluoromethyl)-3-pyridyl]carbamate (4.4 g, 6.354 mmol) in degassed NMP (264 mL) in a round bottom flask outfitted with a reflux condenser was added diacetoxypalladium (427.9 mg, 1.906 mmol) followed by tris-o-tolylphosphane (1.16 g, 3.811 mmol) and TEA (708.4 µL, 5.083 mmol) and the solution was bubbled with N₂ for 5 min then heated in an oil bath at 140° C. for 100 min. Added diacetoxypalladium (142.7 mg, 0.6356 mmol) followed by tris-o-tolylphosphane (386.8 mg, 1.271 mmol) and continued stirring at 140° C. for 15 min then added TEA (221.3 µL, 1.588 mmol) and stirred at 140° C. for 15 min, then cooled to room temperature and concentrated. Diluted the residue with EtOAc and washed with saturated NaHCO₃(1×), saturated NH₄Cl (1×), water (1×) and brine (1×) then dried over MgSO₄, filtered over Celite and concentrated the filtrate. The residue was purified by silica gel chromatography using a shallow gradient from 100% hexanes to 100% ethyl acetate giving as a yellow/orange foam, tert-butyl N-[(15S)-6-hydroxy-6,21-bis(trifluoromethyl)-26-oxa-3,4,19,24-tetraazapentacyclo [18.3.1.12,5.17,11.015,19]hexacosa-1(24),2,4,7(25),8,10,12,20,22-nonaen-23-yl]carbamate (E/Z mixture) (1.62 g, 35%). ESI-MS m/z calc. 611.1967, found 612.2 (M+1)⁺; Retention time: 0.64 minutes (LC Method T).

Step 3: tert-Butyl N-[(15R)-6-hydroxy-6,21-bis(trifluoromethyl)-26-oxa-3,4,19,24-tetraazapentacyclo [18.3.1.12,5.17,11.015,19]hexacosa-1(24),2,4,7(25),8,10,20,22-octaen-23-yl]carbamate

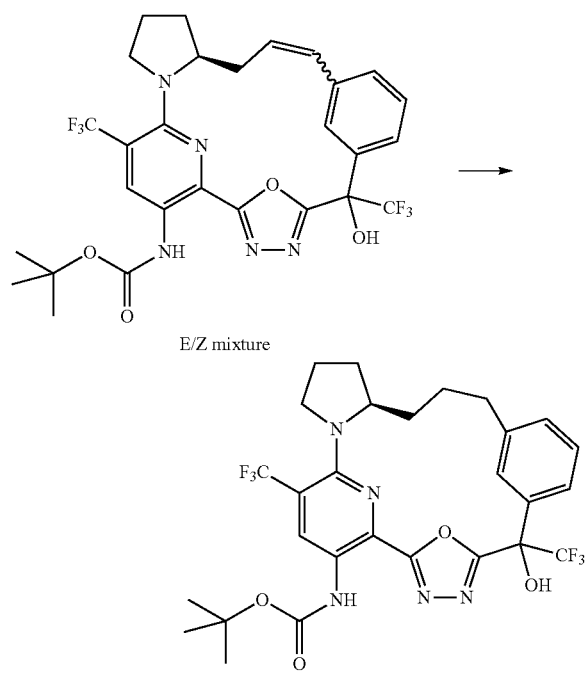

E/Z mixture

To a solution of tert-butyl N-[(15S)-6-hydroxy-6,21-bis (trifluoromethyl)-26-oxa-3,4,19,24-tetraazapentacyclo [18.3.1.12,5.17,11.015,19]hexacosa-1(24),2,4,7(25),8,10,12,20,22-nonaen-23-yl]carbamate (E/Z mixture) (30.7 mg, 0.04418 mmol) in ethanol (1.689 mL) was added Pd/C (25.03 mg of 10% w/w, 0.02352 mmol) and hydrogen was bubbled through the solution for 5 min then the flask was capped with a hydrogen balloon and stirred for 16 h. Bubbled nitrogen through the solution for 5 min then filtered over Celite washing with methanol giving a yellow solution which was concentrated to give the product as a yellow solid and mixture of diastereomers, tert-butyl N-[(15R)-6-hydroxy-6,21-bis(trifluoromethyl)-26-oxa-3,4,19,24-tetraazapentacyclo[18.3.1.12,5.17,11.015,19]hexacosa-1(24),2,4,7 (25),8,10,20,22-octaen-23-yl]carbamate (29.9 mg, 100%). ESI-MS m/z calc. 613.2124, found 614.4 (M+1)⁺; Retention time: 0.75 minutes (LC Method T).

Step 4: (15R)-23-Amino-6,21-bis(trifluoromethyl)-26-oxa-3,4,19,24-tetraazapentacyclo[18.3.1.12,5.17, 11.015,19]hexacosa-1(24),2,4,7(25),8,10,20,22-octaen-6-ol (hydrochloride salt) (enantiomer 1) (Compound 69)

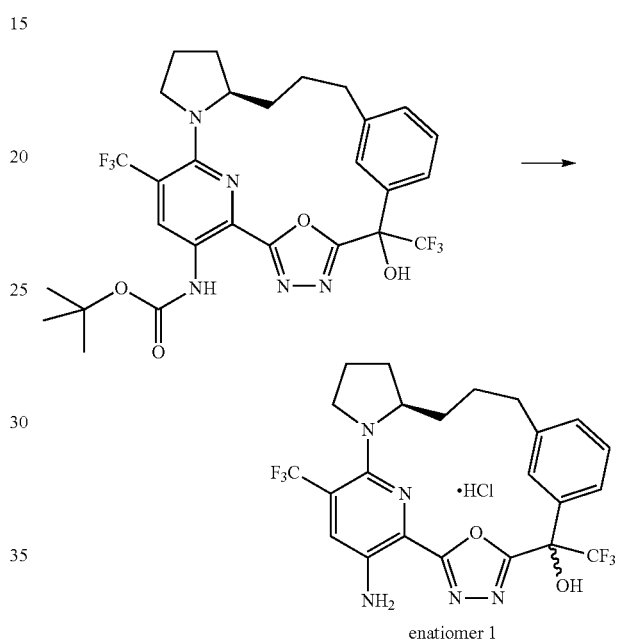

enatiomer 1

To a solution of tert-butyl N-[(15R)-6-hydroxy-6,21-bis (trifluoromethyl)-26-oxa-3,4,19,24-tetraazapentacyclo [18.3.1.12,5.17,11.015,19]hexacosa-1(24),2,4,7(25),8,10,20,22-octaen-23-yl]carbamate (29.9 mg, 0.04415 mmol) in DCM (541.8 µL) was added TFA (204.2 µL, 2.65 mmol). The mixture was stirred at ambient temperature for 4 h then removed volatiles by rotary evaporation, dissolved in DMSO, filtered and purified by reverse phase HPLC using a gradient from 40% to 80% acetonitrile in water (+5 mM HCl) over 15.0 minutes giving as a yellow solid and the first single enantiomer to elute, (15R)-23-amino-6,21-bis(trifluoromethyl)-26-oxa-3,4,19,24-tetraazapentacyclo[18.3.1.12, 5.17,11.015,19]hexacosa-1(24),2,4,7(25),8,10,20,22-octaen-6-ol (hydrochloride salt) (enantiomer 1) (6.5 mg, 51%). ¹H NMR (500 MHz, DMSO-d6) δ 8.60 (s, 1H), 8.00 (s, 1H), 7.68 (s, 1H), 7.33 (d, J 8.1 Hz, 1H), 7.27 (t, J=7.6 Hz, 1H), 7.22 (d, J=7.6 Hz, 1H), 6.22 (s, 2H), 3.94-3.84 (m, 1H), 3.50 (d, J=8.1 Hz, 1H), 3.18 (s, 1H), 2.98 (dd, J=14.2, 5.9 Hz, 1H), 2.51 (s, 1H), 2.28 (td, J=11.8, 9.6, 5.6 Hz, 1H), 2.18-2.11 (m, 1H), 1.87 (dq, J=12.4, 6.2 Hz, 2H), 1.84-1.74 (m, 1H), 1.69-1.59 (m, 1H), 1.53 (dd, J 11.5, 6.4 Hz, 1H), 0.83 (dd, J 11.2, 5.9 Hz, 1H) ppm. ESI-MS m/z calc. 513.16, found 514.1 (M+1)⁺; Retention time: 1.06 minutes (LC Method M).

469

Step 5: (15R)-23-Amino-6,21-bis(trifluoromethyl)-26-oxa-3,4,19,24-tetraazapentacyclo[18.3.1.1²,⁵.1⁷,¹¹.0¹⁵,¹⁹]hexacosa-1(24),2,4,7(25),8,10,20,22-octaen-6-ol (enantiomer 2) (Compound 70)

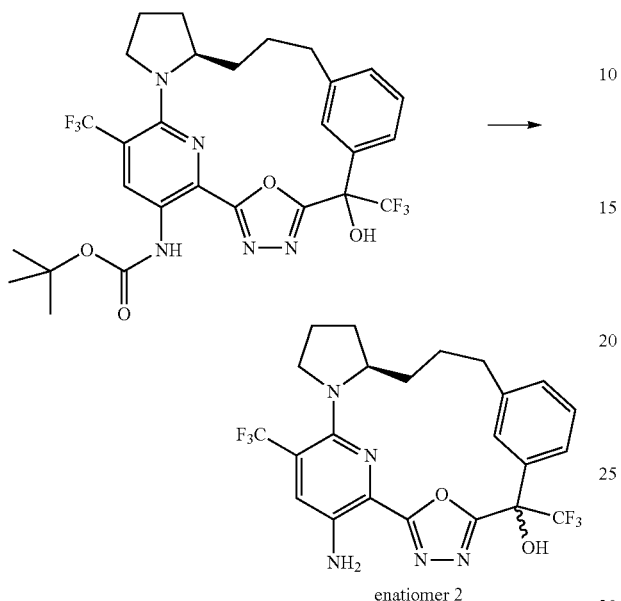

To a solution of tert-butyl N-[(15R)-6-hydroxy-6,21-bis(trifluoromethyl)-26-oxa-3,4,19,24-tetraazapentacyclo[18.3.1.1²,⁵.1⁷,¹¹.0¹⁵,¹⁹]hexacosa-1(24),2,4,7(25),8,10,20,22-octaen-23-yl]carbamate (1.1 g, 1.149 mmol) in dichloromethane (5 mL) was added TFA (15 mL, 194.7 mmol). The mixture was stirred at ambient temperature for 15 minutes then removed the volatiles by rotary evaporation without heating and quenched the residual acid by the addition of saturated aqueous NaHCO₃. This mixture was extracted with EtOAc (2×), the organic layers were combined, dried over MgSO₄, and filtered, and the filtrate was concentrated to a yellow foam which was purified by reverse phase chromatography on a 275 g C₁₈ column eluting with a gradient from 50% to 100% acetonitrile in water, which gave the product still containing some impurities as the second single enantiomer to elute. Impure fractions were combined and again purified by reverse phase chromatography on a 100 g C₁₈ column eluting with a gradient from 50% to 100% acetonitrile in water giving pure product which was combined with the pure product from the first column and concentrated to give as a yellow solid, (15R)-23-amino-6,21-bis(trifluoromethyl)-26-oxa-3,4,19,24-tetraazapentacyclo[18.3.1.1²,⁵.1⁷,¹¹.0¹⁵,¹⁹]hexacosa-1(24),2,4,7(25),8,10,20,22-octaen-6-ol (enantiomer 2) (234 mg, 79%) ¹H NMR (400 MHz, DMSO-d6) δ 8.70 (s, 1H), 7.93 (s, 1H), 7.70 (s, 1H), 7.63 (d, J=7.8 Hz, 1H), 7.38 (t, J=7.7 Hz, 1H), 7.28 (d, J=7.7 Hz, 1H), 6.23 (s, 2H), 4.16 (dt, J=10.6, 5.3 Hz, 1H), 3.60-3.48 (m, 1H), 3.23 (t, J=9.0 Hz, 1H), 2.90 (dd, J=15.9, 8.0 Hz, 1H), 2.75-2.65 (m, 1H), 2.40 (dt, J=10.9, 5.6 Hz, 1H), 2.22 (dt, J=11.9, 6.0 Hz, 1H), 1.92 (dd, J=12.8, 6.8 Hz, 2H), 1.83-1.67 (m, 2H), 1.58 (dt, J=11.6, 5.8 Hz, 1H), 0.85 (dt, J=16.2, 6.1 Hz, 1H), one exchangeable proton not observe. ESI-MS m/z calc. 513.16, found 514.0 (M+1)⁺; Retention time: 2.34 minutes (LC Method A).

470

Step 6: Solid Form Characterization of Amorphous Compound 70 (Neat Form)

A. X-Ray Powder Diffraction

The XRPD diffractogram for amorphous Compound 70 (neat form) produced by Step 5 was acquired using the General X-Ray Powder Diffraction (XRPD) Method and is provided in FIG. 15.

Example 39: Preparation of (12R)-20-amino-6-(trifluoromethyl)-22-oxa-3,4,16,21-tetraazatetracyclo[15.3.1.1²,⁵.0¹²,¹⁶]docosa-1(21),2,4,17,19-pentaen-6-ol (enantiomer 1) (Compound 71) and (12R)-20-amino-6-(trifluoromethyl)-22-oxa-3,4,16,21-tetraazatetracyclo[15.3.1.1²,⁵.0¹²,¹⁶]docosa-1(21),2,4,17,19-pentaen-6-ol (enantiomer 2) (Compound 72)

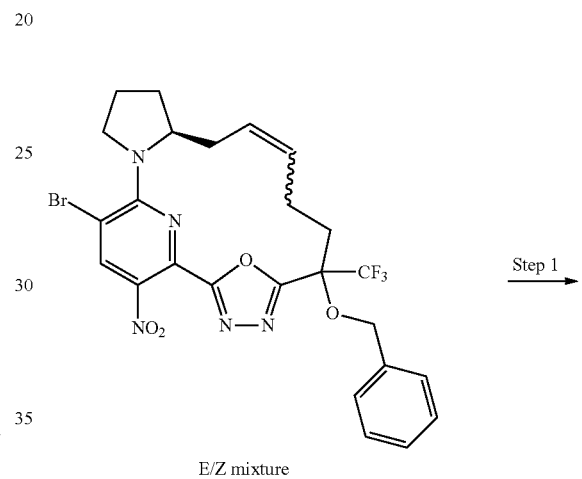

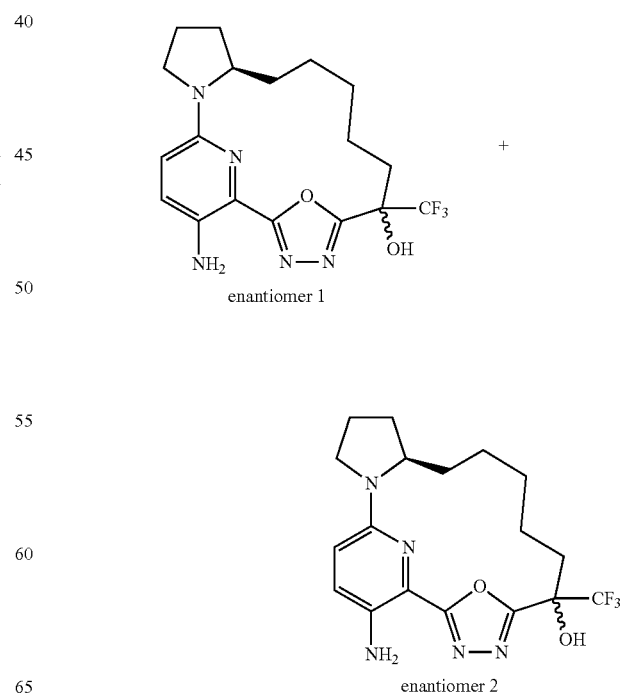

Step 1: (12R)-20-Amino-6-(trifluoromethyl)-22-oxa-3,4,16,21-tetraazatetracyclo[15.3.1.12,5.012,16]docosa-1(21),2,4,17,19-pentaen-6-ol (enantiomer 1) (Compound 71) and (12R)-20-amino-6-(trifluoromethyl)-22-oxa-3,4,16,21-tetraazatetracyclo[15.3.1.12,5.012,16]docosa-1(21),2,4,17,19-pentaen-6-ol (enantiomer 2) (Compound 72)

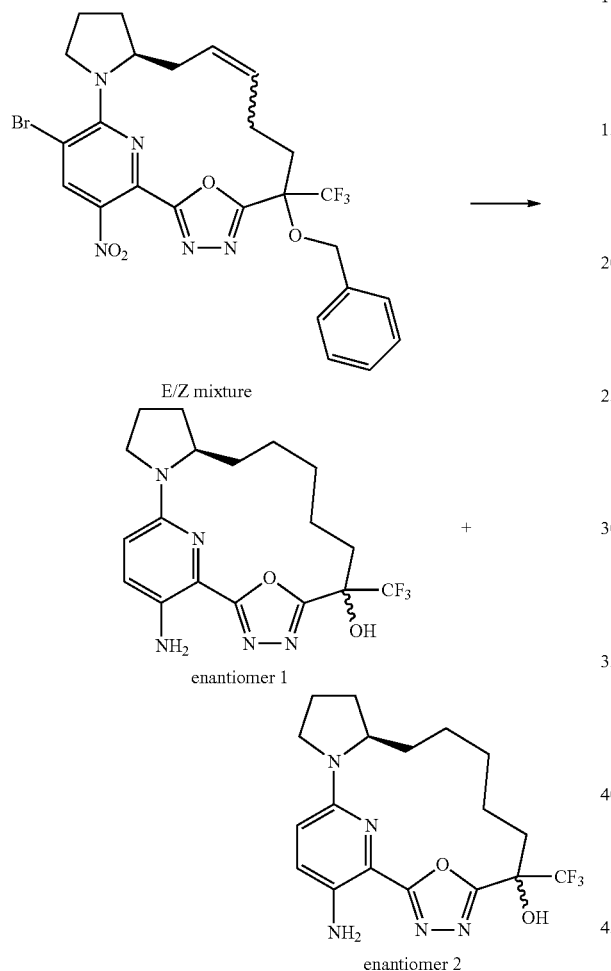

E/Z mixture enantiomer 1 enantiomer 2

A solution of (12S)-6-(benzyloxy)-18-bromo-20-nitro-6-(trifluoromethyl)-22-oxa-3,4,16,21-tetraazatetracyclo[15.3.1.12,5.012,16]docosa-1(21),2,4,9,17,19-hexaene (E/Z mixture) (300 mg, 0.4396 mmol) in methanol (15 mL) was bubbled with nitrogen for 5 min and then triethylamine (217.8 mg, 0.3 mL, 2.1524 mmol) was added followed by palladium on carbon (325 mg, 0.1527 mmol). The resulting mixture was bubbled with a balloon of hydrogen for 5 min and then stirred at room temperature under hydrogen for 5 hours. The mixture was filtered through a pad of Celite, washed with methanol (40 mL) and concentrated the filtrate under reduced pressure. The residue was purified by silica gel chromatography (40 g column) using a gradient from 0% to 30% ethyl acetate in heptanes giving as an orange solid and the first diastereomer to elute, (12R)-20-amino-6-(trifluoromethyl)-22-oxa-3,4,16,21-tetraazatetracyclo[15.3.1.12,5.012,16]docosa-1(21),2,4,17,19-pentaen-6-ol (enantiomer 1) (90 mg, 49%). $^1$H NMR (300 MHz, Chloroform-d) δ 7.06 (d, J=8.8 Hz, 1H), 6.51 (d, J=8.8 Hz, 1H), 5.30-4.06 (m, 2H), 3.97-3.81 (m, 1H), 3.54-3.37 (m, 1H), 3.30-3.11 (m, 1H), 2.73-2.54 (m, 1H), 2.50-2.35 (m, 1H), 2.31-1.84 (m, 5H), 1.82-1.48 (m, 7H), 1.02-0.79 (m, 1H) ppm. ESI-MS m/z calc. 397.1726, found 398.2 (M+1)$^+$; Retention time: 3.22 minutes (LC Method C).

The second diastereomer to elute was isolated as an orange solid, (12R)-20-amino-6-(trifluoromethyl)-22-oxa-3,4,16,21-tetraazatetracyclo[15.3.1.12,5.012,16]docosa-1(21),2,4,17,19-pentaen-6-ol (enantiomer 2) (60 mg, 33.9%). $^1$H NMR (300 MHz, Chloroform-d) δ 7.08 (d, J=8.8 Hz, 1H), 6.53 (d, J=8.8 Hz, 1H), 4.85 (br. s., 2H), 4.00-3.87 (m, 1H), 3.54-3.36 (m, 1H), 3.26-3.07 (m, 1H), 2.75-2.55 (m, 1H), 2.36-2.12 (m, 3H), 2.11-1.92 (m, 3H), 1.84-1.75 (m, 1H), 1.73-1.34 (m, 6H), 1.10-0.95 (m, 1H) ppm. ESI-MS m/z calc. 397.1726, found 398.2 (M+1)$^+$; Retention time: 3.22 minutes (LC Method C).

Example 40: Preparation of 17-amino-13-cyclobutyl-6,15-bis(trifluoromethyl)-19-oxa-3,4,13,18-tetrazatricyclo[12.3.1.12,5]nonadeca-1(18),2,4,14,16-pentaen-6-ol (enantiomer 1) (Compound 73) and 17-amino-13-cyclobutyl-6,15-bis(trifluoromethyl)-19-oxa-3,4,13,18-tetrazatricyclo[12.3.1.12,5]nonadeca-1(18),2,4,14,16-pentaen-6-ol (enantiomer 2) (Compound 74)

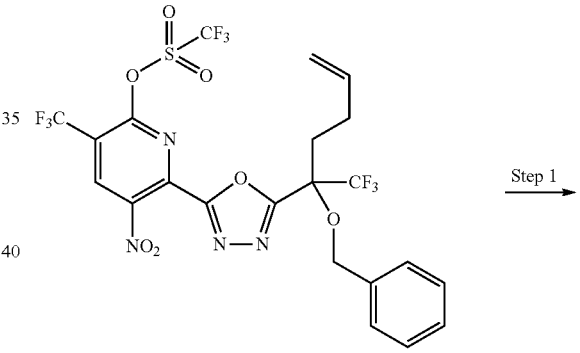

Step 1

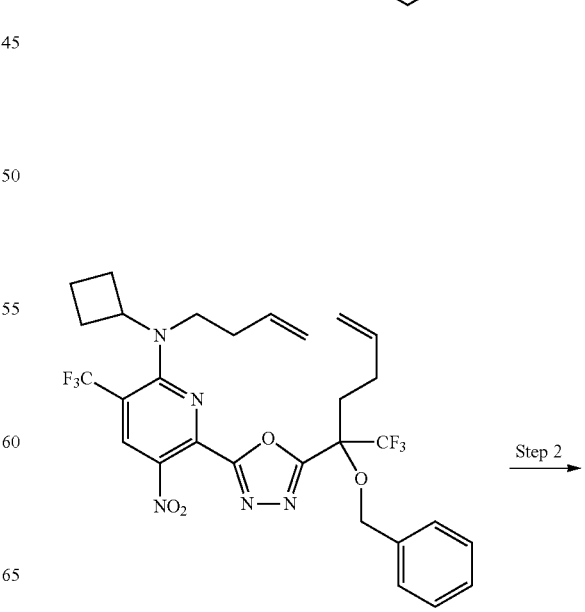

Step 2

473
-continued

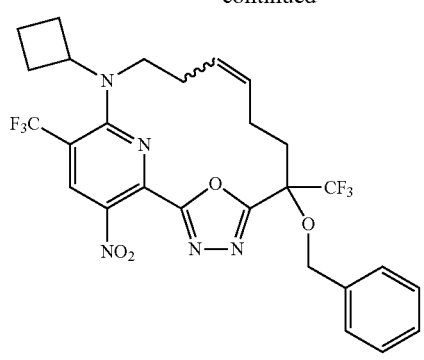

E/Z mixture

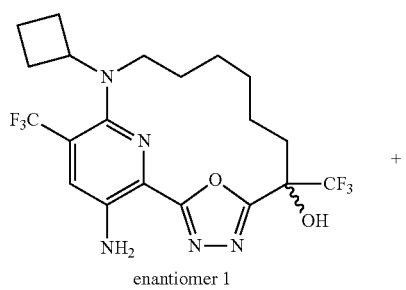

enantiomer 1

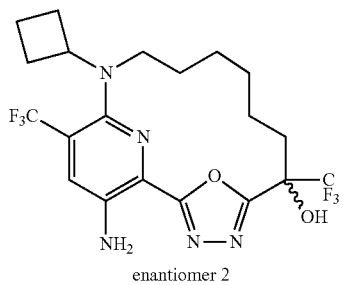

enantiomer 2

Step 1: 6-[5-[1-Benzyloxy-1-(trifluoromethyl)pent-4-enyl]-1,3,4-oxadiazol-2-yl]-N-but-3-enyl-N-cyclobutyl-5-nitro-3-(trifluoromethyl)pyridin-2-amine

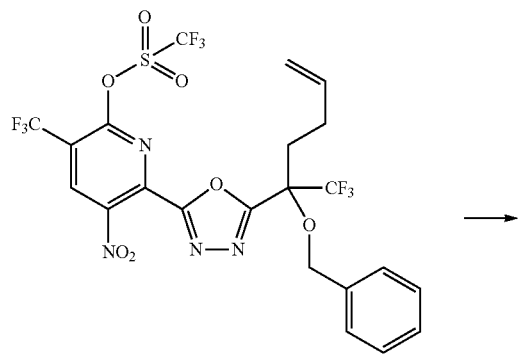

474
-continued

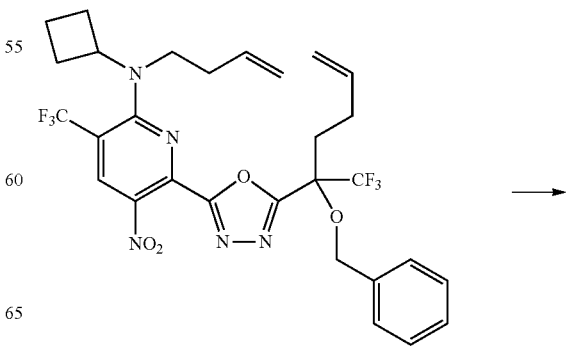

To a mixture of [6-[5-[1-benzyloxy-1-(trifluoromethyl)pent-4-enyl]-1,3,4-oxadiazol-2-yl]-5-nitro-3-(trifluoromethyl)-2-pyridyl] trifluoromethanesulfonate (300 mg, 0.4612 mmol) in THF (6 mL) was added N-but-3-enylcyclobutanamine (296 µL, 1.844 mmol) and diisopropyl ethylamine (241 µL, 1.384 mmol) and the mixture stirred at 50° C. for 30 min. The mixture was diluted with EtOAc, washed with water then brine, dried (MgSO$_4$), filtered and evaporated. The residue was purified by silica gel chromatography (0% to 10% EtOAc in hexanes over 15 min) to provide 6-[5-[1-benzyloxy-1-(trifluoromethyl)pent-4-enyl]-1,3,4-oxadiazol-2-yl]-N-but-3-enyl-N-cyclobutyl-5-nitro-3-(trifluoromethyl)pyridin-2-amine (127 mg, 44%). $^1$H NMR (400 MHz, Chloroform-d) δ 8.66 (s, 1H), 7.45-7.29 (m, 5H), 5.80 (ddt, J=16.6, 10.2, 6.3 Hz, 1H), 5.64 (ddt, J=17.1, 10.3, 6.9 Hz, 1H), 5.14-4.95 (m, 5H), 4.81 (d, J=10.6 Hz, 1H), 4.65 (d, J=10.6 Hz, 1H), 4.33 (p, J=8.2 Hz, 1H), 3.74-3.64 (m, 2H), 2.59-2.44 (m, 2H), 2.42-2.20 (m, 5H), 2.20-2.07 (m, 2H), 1.80-1.62 (m, 2H) ppm; $^{19}$F NMR (376 MHz, Chloroform-d) δ −58.50, −73.15 ppm. ESI-MS m/z calc. 625.2124, found 626.2 (M+1)$^+$; Retention time: 0.61 minutes (LC Method T).

Step 2: 6-Benzyloxy-13-cyclobutyl-17-nitro-6,15-bis(trifluoromethyl)-19-oxa-3,4,13,18-tetrazatricyclo[12.3.1.1²,⁵]nonadeca-1(17),2,4,9,14(18),15-hexaene (E/Z mixture)

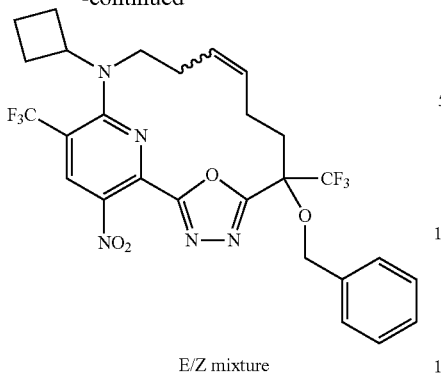

E/Z mixture

To a solution of benzylidene-[1,3-bis(2,4,6-trimethylphenyl)imidazolidin-2-ylidene]-dichloro-ruthenium; tricyclohexylphosphane (25 mg, 0.02945 mmol) in toluene (9 mL) at 120° C. with nitrogen bubbling was added dropwise a solution of 6-[5-[1-benzyloxy-1-(trifluoromethyl)pent-4-enyl]-1,3,4-oxadiazol-2-yl]-N-but-3-enyl-N-cyclobutyl-5-nitro-3-(trifluoromethyl)pyridin-2-amine (121 mg, 0.1934 mmol) in toluene (9 mL) and the mixture stirred at 120° C. with nitrogen bubbling for 1 h. The solvent was evaporated and the residue was purified by silica gel chromatography (0% to 20% EtOAc in hexanes over 15 min) to provide 6-benzyloxy-13-cyclobutyl-17-nitro-6,15-bis(trifluoromethyl)-19-oxa-3,4,13,18-tetrazatricyclo[12.3.1.12,5]nonadeca-1(17),2,4,9,14(18),15-hexaene (E/Z mixture) (45 mg, 35%). ESI-MS m/z calc. 597.1811, found 598.1 (M+1)⁺; Retention time: 0.54 minutes (LC Method T).

Step 3: 17-Amino-13-cyclobutyl-6,15-bis(trifluoromethyl)-19-oxa-3,4,13,18-tetrazatricyclo [12.3.1.12,5]nonadeca-1(18),2,4,14,16-pentaen-6-ol (enantiomer 1) (Compound 73) and 17-amino-13-cyclobutyl-6,15-bis(trifluoromethyl)-19-oxa-3,4,13,18-tetrazatricyclo[12.3.1.12,5]nonadeca-1(18),2,4,14,16-pentaen-6-ol (enantiomer 2) (Compound 74)

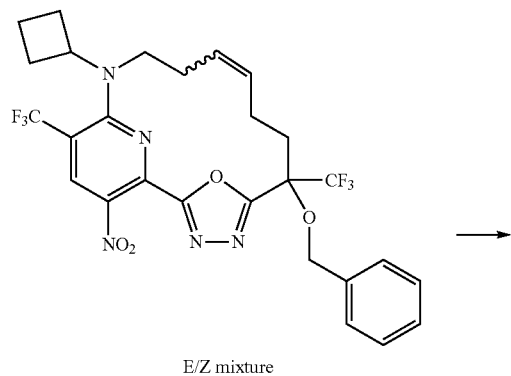

E/Z mixture

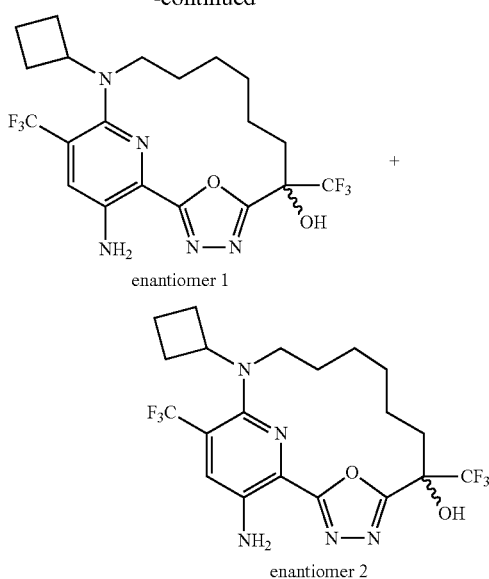

enantiomer 1 enantiomer 2

A mixture of 6-benzyloxy-13-cyclobutyl-17-nitro-6,15-bis(trifluoromethyl)-19-oxa-3,4,13,18-tetrazatricyclo [12.3.1.12,5]nonadeca-1(17),2,4,9,14(18),15-hexaene (E/Z mixture) (45 mg, 0.06778 mmol) and Pd/C (22 mg of 10% w/w, 0.02067 mmol) in acetic acid (700 μL) was stirred at room temperature under hydrogen (200 psi in a stainless steel pressure vessel) for 24 h. Then, the mixture was filtered and the filtrate was evaporated. The residue was purified by silica gel chromatography using a gradient from 0% to 35% EtOAc in hexanes over 15 min to provide racemic 6-benzyloxy-13-cyclobutyl-6,15-bis(trifluoromethyl)-19-oxa-3,4,13,18-tetrazatricyclo[12.3.1.12,5]nonadeca-1(17),2,4,14 (18),15-pentaen-17-amine. This racemic material was dissolved into acetonitrile at 20 mg/mL and the enantiomers were separated by chiral SFC using an AS-3 column (250× 21.2 mm, 5 μm particle size) using a gradient from 5% to 15% methanol (5 mM NH₃) in CO₂ mobile phase over 10 min. These conditions produced 2 enantiomeric products as described below:

Peak 1 was concentrated to afford as a yellow solid, 17-amino-13-cyclobutyl-6,15-bis(trifluoromethyl)-19-oxa-3,4,13,18-tetrazatricyclo[12.3.1.12,5]nonadeca-1(18),2,4, 14,16-pentaen-6-ol (enantiomer 1) (6.7 mg, 21%). ¹H NMR (400 MHz, Chloroform-d) δ 7.38 (s, 1H), 5.13 (s, 2H), 4.07 (tt, J=9.5, 7.3 Hz, 1H), 3.90 (s, 1H), 3.49-3.26 (m, 2H), 2.43-2.23 (m, 3H), 2.21-2.04 (m, 4H), 1.76 (td, J=12.4, 5.3 Hz, 1H), 1.62 (d, J=9.6 Hz, 2H), 1.53 (s, 6H) ppm. ¹⁹F NMR (376 MHz, Chloroform-d) δ−58.82, −79.80 ppm. ESI-MS m/z calc. 479.1756, found 480.1 (M+1)⁺; Retention time: 1.82 minutes (LC Method Q). Peak 2 was concentrated to afford as a yellow solid, 17-amino-13-cyclobutyl-6,15-bis (trifluoromethyl)-19-oxa-3,4,13,18-tetrazatricyclo [12.3.1.12,5]nonadeca-1(18),2,4,14,16-pentaen-6-ol (enantiomer 2) (6.5 mg, 20%). ¹H NMR (400 MHz, Chloroform-d) δ 7.39 (s, 1H), 5.13 (s, 2H), 4.07 (tt, J=9.6, 7.3 Hz, 1H), 3.88 (s, 1H), 3.46-3.28 (m, 2H), 2.43-2.23 (m, 3H), 2.21-2.03 (m, 4H), 1.76 (td, J=12.4, 5.2 Hz, 1H), 1.68-1.41 (m, 8H) ppm. ¹⁹F NMR (376 MHz, Chloroform-d) δ−58.82, −79.80 ppm. ESI-MS m/z calc. 479.1756, found 480.1 (M+1)⁺; Retention time: 1.83 minutes (LC Method Q).

Example 41: Preparation of 17-amino-13-methyl-15-(trifluoromethyl)-19-oxa-3,4,13,18-tetrazatricyclo[12.3.1.1²,⁵]nonadeca-1(18),2,4,9,14,16-hexaen-6-one (E/Z mixture) (Compound 75)

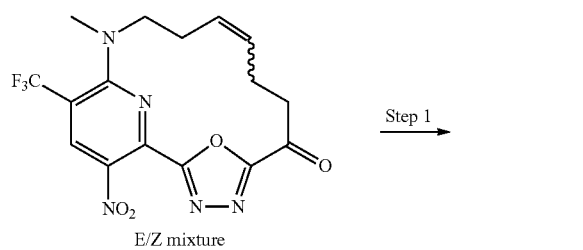

Step 1: 17-Amino-13-methyl-15-(trifluoromethyl)-19-oxa-3,4,13,18-tetrazatricyclo[12.3.1.1²,⁵]nonadeca-1(18),2,4,9,14,16-hexaen-6-one (E/Z mixture) (Compound 75)

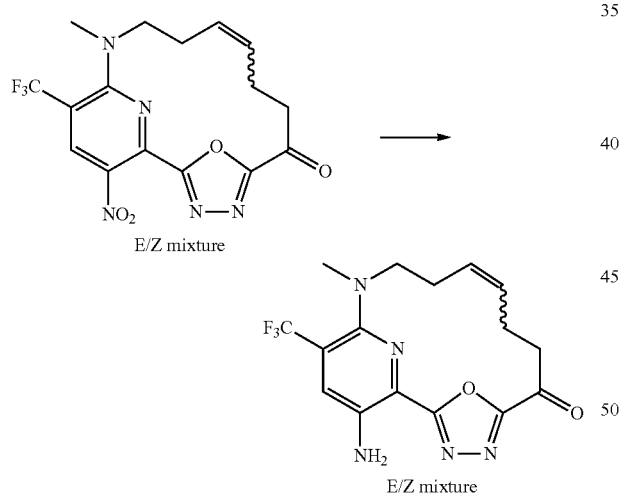

A mixture of 13-methyl-17-nitro-15-(trifluoromethyl)-19-oxa-3,4,13,18-tetrazatricyclo[12.3.1.1²,⁵]nonadeca-1(18),2,4,9,14,16-hexaen-6-one (E/Z mixture) (250 mg, 0.6292 mmol) and tin(II) chloride dihydrate (568 mg, 2.517 mmol) in ethyl acetate (6.292 mL) was stirred at 55° C. for 30 min then diluted with EtOAc and 2 N NaOH was added to the mixture until the mixture become viscous. Filtered the mixture through Celite and the filtrate was washed with brine, dried over MgSO₄, filtered and evaporated. The residue was purified by silica gel chromatography (12 g column) using a gradient from 0% to 30% ethyl acetate in hexanes to afford as an orange solid, 17-amino-13-methyl-15-(trifluoromethyl)-19-oxa-3,4,13,18-tetrazatricyclo[12.3.1.1²,⁵]nonadeca-1(18),2,4,9,14,16-hexaen-6-one (E/Z mixture) (185 mg, 80%). ¹H NMR (400 MHz, Chloroform-d) δ 7.37 (s, 1H), 5.67-5.51 (m, 1H), 5.46-5.31 (m, 1H), 3.37-3.26 (m, 2H), 2.97 (d, J=1.9 Hz, 3H), 2.92-2.83 (m, 2H), 2.66 (dq, J=16.5, 8.4, 7.9 Hz, 4H) ppm. Two exchangeable protons not observed. ESI-MS m/z calc. 367.1256, found 368.2 (M+1)⁺; Retention time: 0.76 minutes (LC Method S).

Example 42: Preparation of 17-amino-13-methyl-6-phenyl-15-(trifluoromethyl)-19-oxa-3,4,13,18-tetrazatricyclo[12.3.1.1²,⁵]nonadeca-1(18),2,4,14,16-pentaen-6-ol (enantiomer 1) (Compound 76) and 17-amino-13-methyl-6-phenyl-15-(trifluoromethyl)-19-oxa-3,4,13,18-tetrazatricyclo[12.3.1.1²,⁵]nonadeca-1(18),2,4,14,16-pentaen-6-ol (enantiomer 2) (Compound 77)

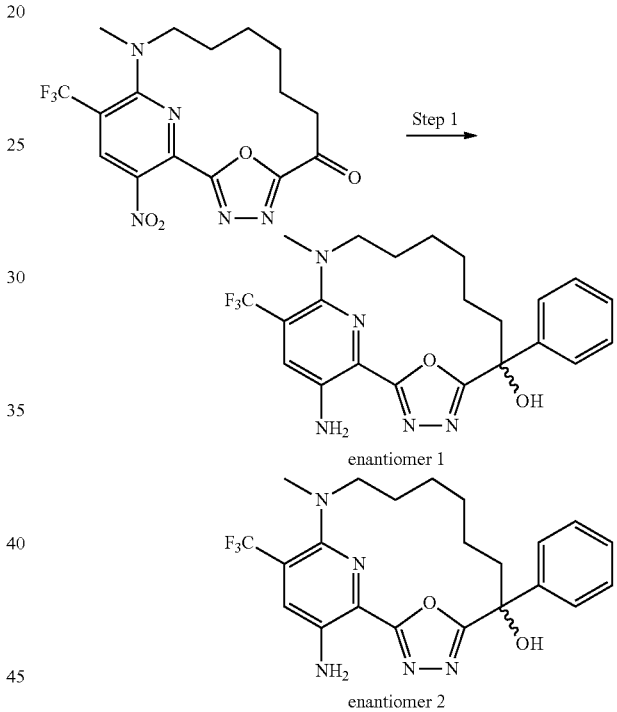

Step 1: 17-Amino-13-methyl-6-phenyl-15-(trifluoromethyl)-19-oxa-3,4,13,18-tetrazatricyclo[12.3.1.1²,⁵]nonadeca-1(18),2,4,14,16-pentaen-6-ol (enantiomer 1) (Compound 76) and 17-amino-13-methyl-6-phenyl-15-(trifluoromethyl)-19-oxa-3,4,13,18-tetrazatricyclo[12.3.1.1²,⁵]nonadeca-1(18),2,4,14,16-pentaen-6-ol (enantiomer 2) (Compound 77)

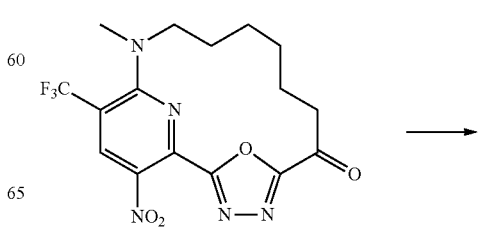

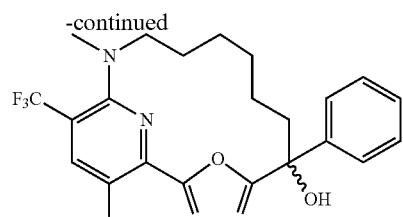

enantiomer 1

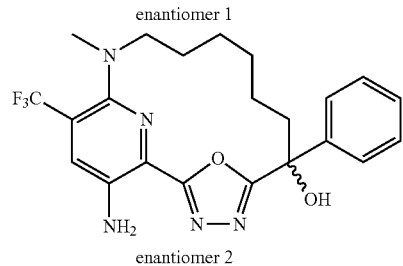

enantiomer 2

Under nitrogen, a solution of 17-amino-13-methyl-15-(trifluoromethyl)-19-oxa-3,4,13,18-tetrazatricyclo[12.3.1.1².⁵]nonadeca-1(18),2,4,14,16-pentaen-6-one (19 mg, 0.05144 mmol) in THF (383.4 µL) was cooled at 0° C., then bromo(phenyl)magnesium (113.2 µL, 1 M, 0.1132 mmol) was added dropwise and the mixture was stirred for 30 min at 0° C. The reaction mixture was quenched with water and 1 N HCl, extracted with ethyl acetate (2×15 mL) and the combined organic layers were washed with brine, dried over MgSO$_4$, filtered and concentrated. Purified the residue by silica gel chromatography (12 g column) using a gradient from 0% to 30% ethyl acetate in hexanes giving a racemic mixture as a yellow solid. This racemic material was then purified by chiral SFC using an OD-H column (250×21.2 mm, 5 µm particle size) sold by Chiral Technologies and eluting with a gradient from 50% to 80% MeOH (+20 mM NH$_3$) in CO$_2$ over 14.5 minutes which provided two single enantiomers:

The first enantiomer to elute was isolated as a yellow solid, 17-amino-13-methyl-6-phenyl-15-(trifluoromethyl)-19-oxa-3,4,13,18-tetrazatricyclo[12.3.1.1²,⁵]nonadeca-1(18),2,4,14,16-pentaen-6-ol (enantiomer 1) (4 mg, 16%). ¹H NMR (400 MHz, CD$_3$OD) δ 7.50 (s, 1H), 7.31-7.15 (m, 5H), 2.95-2.82 (m, 3H), 2.26-2.07 (m, 2H), 1.96-1.77 (m, 2H), 1.71-1.08 (m, 8H) ppm. ESI-MS m/z calc. 447.1882, found 448.3 (M+1)⁺; Retention time: 2.15 minutes (LC Method A).

The second enantiomer to elute was isolated as a yellow solid, 17-amino-13-methyl-6-phenyl-15-(trifluoromethyl)-19-oxa-3,4,13,18-tetrazatricyclo[12.3.1.1²,⁵]nonadeca-1(18),2,4,14,16-pentaen-6-ol (enantiomer 2) (4 mg, 16%). ¹H NMR (400 MHz, CD$_3$OD) δ 7.50 (s, 1H), 7.29-7.18 (m, 5H), 2.91-2.81 (m, 3H), 2.26-2.08 (m, 2H), 1.92-1.81 (m, 2H), 1.71-1.20 (m, 8H) ppm. ESI-MS m/z calc. 447.1882, found 448.3 (M+1)⁺; Retention time: 2.15 minutes (LC Method A).

Example 43: Preparation of 17-amino-6-cyclopropyl-13-methyl-15-(trifluoromethyl)-19-oxa-3,4,13,18-tetrazatricyclo[12.3.1.1².⁵]nonadeca-1(18),2,4,14,16-pentaen-6-ol (enantiomer 1) (Compound 78) and 17-amino-6-cyclopropyl-13-methyl-15-(trifluoromethyl)-19-oxa-3,4,13,18-tetrazatricyclo[12.3.1.1².⁵]nonadeca-1(18),2,4,14,16-pentaen-6-ol (enantiomer 2) (Compound 79)

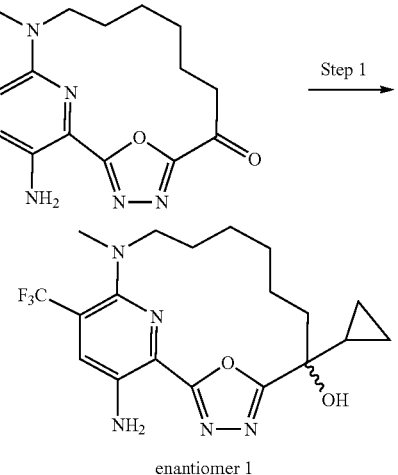

enantiomer 1

enantiomer 2

Step 1: 17-Amino-6-cyclopropyl-13-methyl-15-(trifluoromethyl)-19-oxa-3,4,13,18-tetrazatricyclo[12.3.1.1².⁵]nonadeca-1(18),2,4,14,16-pentaen-6-ol (enantiomer 1) (Compound 78) and 17-amino-6-cyclopropyl-13-methyl-15-(trifluoromethyl)-19-oxa-3,4,13,18-tetrazatricyclo[12.3.1.1².⁵]nonadeca-1(18),2,4,14,16-pentaen-6-ol (enantiomer 2) (Compound 79)

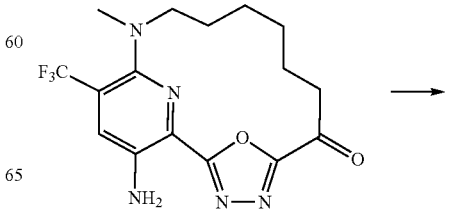

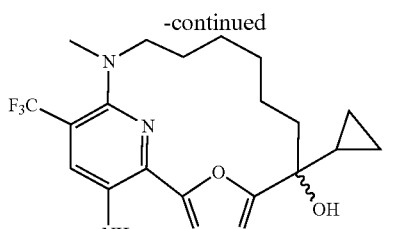

enantiomer 1

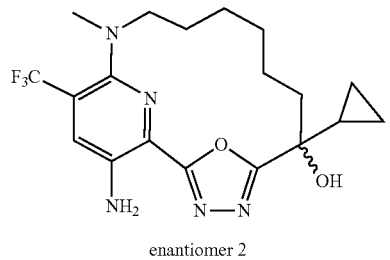

enantiomer 2

Under nitrogen, a solution of 17-amino-13-methyl-15-(trifluoromethyl)-19-oxa-3,4,13,18-tetrazatricyclo[12.3.1.1²,⁵]nonadeca-1(18),2,4,14,16-pentaen-6-one (30 mg, 0.08123 mmol) in THF (605.4 µL) was cooled at 0° C., then bromo(cyclopropyl)magnesium (178.7 µl M, 0.1787 mmol) was added dropwise and stirred for 30 min at 0° C. The reaction mixture was quenched with water and 1 N HCl, extracted with ethyl acetate (2×15 mL), washed with brine, dried over MgSO₄, filtered and concentrated. Purification by silica gel chromatography (12 g column) using a gradient from 0% to 30% ethyl acetate in hexanes gave a racemic mixture which was separated by chiral SFC using an OD-H column (250×21.2 mm, 5 µm particle size) sold by Chiral Technologies, eluting with 5% to 15% MeOH (+20 mM NH₃) in CO₂ over 14.5 minutes which provided two single enantiomers:

The first enantiomer to elute was isolated as a yellow solid, 17-amino-6-cyclopropyl-13-methyl-15-(trifluoromethyl)-19-oxa-3,4,13,18-tetrazatricyclo[12.3.1.1²,⁵]nonadeca-1(18),2,4,14,16-pentaen-6-ol (enantiomer 1) (3 mg, 9%). ¹H NMR (400 MHz, CD₃OD) δ 7.48 (s, 1H), 2.85 (s, 3H), 1.97 (td, J=9.4, 5.3 Hz, 2H), 1.83 (dd, J=11.5, 5.9 Hz, 2H), 1.71-1.32 (m, 7H), 1.29-1.18 (m, 2H), 0.63 (dtd, J=9.4, 5.4, 3.7 Hz, 1H), 0.52-0.36 (m, 3H) ppm. ESI-MS m/z calc. 411.1882, found 412.3 (M+1)⁺; Retention time: 2.02 minutes (LC Method A).

The second enantiomer to elute was isolated as a yellow solid, 17-amino-6-cyclopropyl-13-methyl-15-(trifluoromethyl)-19-oxa-3,4,13,18-tetrazatricyclo[12.3.1.1²,⁵]nonadeca-1(18),2,4,14,16-pentaen-6-ol (enantiomer 2) (3 mg, 9%). ¹H NMR (400 MHz, CD₃OD) δ 7.49 (s, 1H), 2.86 (s, 3H), 1.98 (td, J=9.3, 5.3 Hz, 2H), 1.89-1.74 (m, 2H), 1.69-1.45 (m, 4H), 1.44-1.33 (m, 2H), 1.32-1.05 (m, 3H), 0.68-0.59 (m, 1H), 0.55-0.35 (m, 3H) ppm. ESI-MS m/z calc. 411.1882, found 412.3 (M+1)⁺; Retention time: 2.02 minutes (LC Method A).

Example 44: Preparation of (12R)-20-amino-6-hydroxy-6-(trifluoromethyl)-22-oxa-3,4,16,21-tetraazatetracyclo[15.3.1.1²,⁵.0¹²,¹⁶]docosa-1(21),2,4,17,19-pentaene-18-carbonitrile (enantiomer 1) (Compound 80) and (12R)-20-amino-6-hydroxy-6-(trifluoromethyl)-22-oxa-3,4,16,21-tetraazatetracyclo[15.3.1.1²,⁵.0¹²,¹⁶]docosa-1(21),2,4,17,19-pentaene-18-carbonitrile (enantiomer 2) (Compound 81)

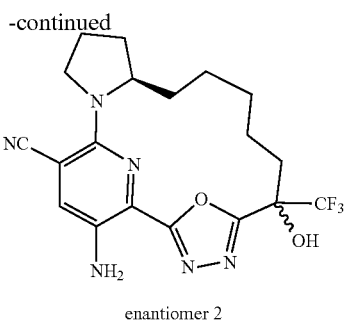

enantiomer 2

Step 1: (12S)-6-(Benzyloxy)-20-nitro-6-(trifluoromethyl)-22-oxa-3,4,16,21-tetraazatetracyclo[15.3.1.12,5.012,16]docosa-1(21),2,4,9,17,19-hexaene-18-carbonitrile (E/Z mixture)

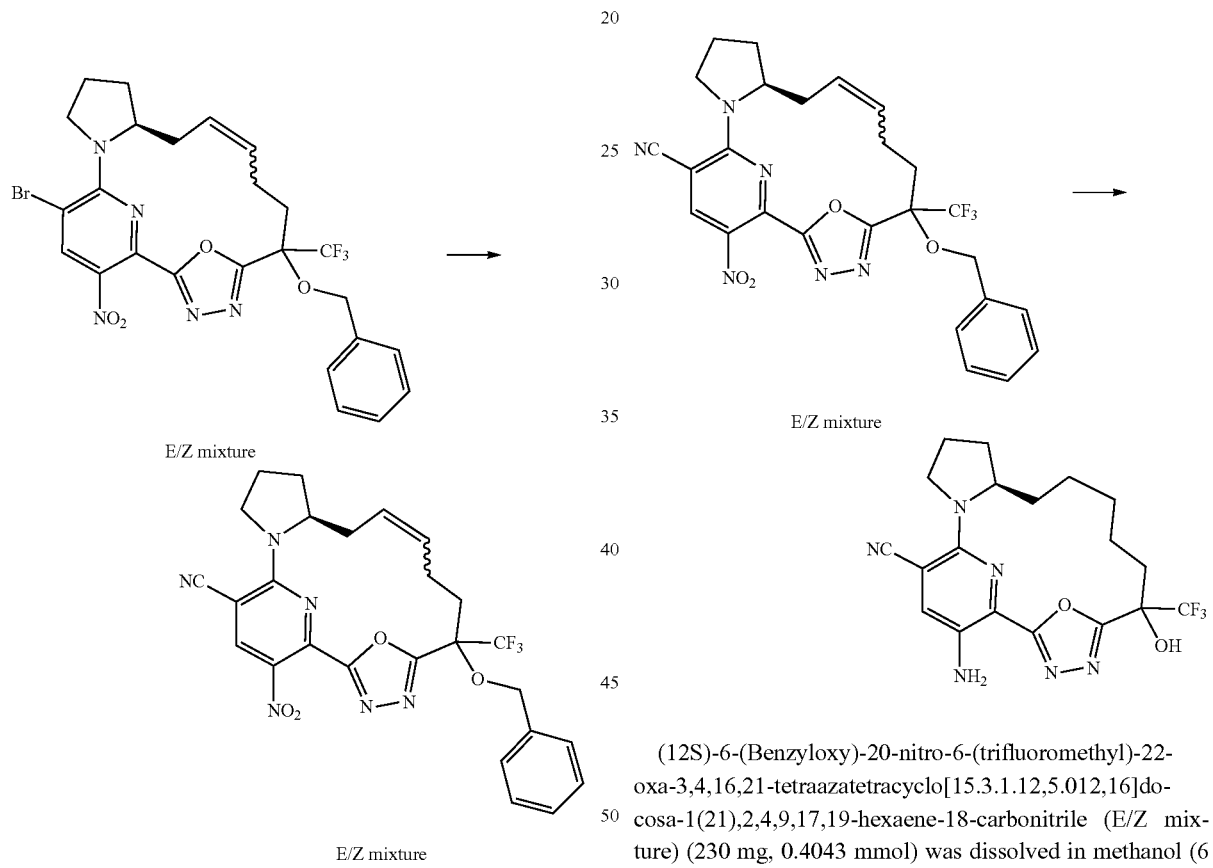

E/Z mixture

A solution of (12S)-6-(benzyloxy)-18-bromo-20-nitro-6-(trifluoromethyl)-22-oxa-3,4,16,21-tetraazatetracyclo[15.3.1.12,5.012,16]docosa-1(21),2,4,9,17,19-hexaene (E/Z mixture) (400 mg, 0.6662 mmol) in DMF (6 mL) in a microwave vial was degassed with nitrogen for 5 minutes and then copper(I) cyanide (298 mg, 3.3273 mmol) was added. The resulting suspension was stirred under nitrogen at 90° C. overnight. The mixture was cooled to room temperature and then diluted with EtOAc (75 mL) and filtered through a pad of Celite. The filtrate was washed with an aqueous solution of NH₄OH (10% v/v, 3×20 mL). The organic layer was washed with brine (2×30 mL), dried over sodium sulfate, filtered and concentrated under reduced pressure. The residue was purified by silica gel chromatography (12 g column) using a gradient from 0% to 20% ethyl acetate in heptane to afford as a yellow solid, (12S)-6-(benzyloxy)-20-nitro-6-(trifluoromethyl)-22-oxa-3,4,16,21-tetraazatetracyclo[15.3.1.12,5.012,16]docosa-1(21),2,4,9,17,19-hexaene-18-carbonitrile (E/Z mixture) (310 mg, 86%). $^1$H NMR (300 MHz, Chloroform-d) δ 8.71-8.54 (m, 1H), 7.48-7.20 (m, 5H), 5.69-5.36 (m, 2H), 5.22 (d, J=11.2 Hz, 1H), 5.04-4.89 (m, 1H), 4.31-3.90 (m, 3H), 3.34-3.10 (m, 1H), 2.55-1.87 (m, 8H), 1.72-1.60 (m, 1H) ppm. ESI-MS m/z calc. 540.1733, found 541.0 (M+1)$^+$; Retention time: 2.4 minutes (LC Method E).

Step 2: (12R)-20-Amino-6-hydroxy-6-(trifluoromethyl)-22-oxa-3,4,16,21-tetraazatetracyclo[15.3.1.12,5.012,16]docosa-1(21),2,4,17,19-pentaene-18-carbonitrile (12S)-6-(Benzyloxy)-20-nitro-6-(trifluoromethyl)-22-oxa-3,4,16,21-tetraazatetracyclo[15.3.1.12,5.012,16]docosa-1(21),2,4,9,17,19-hexaene-18-carbonitrile (E/Z mixture) (230 mg, 0.4043 mmol) was dissolved in methanol (6 mL). The mixture was bubbled with nitrogen for 5 min and then 10% palladium on carbon (260 mg, 0.1222 mmol) was added. The resulting mixture was bubbled with a balloon of hydrogen for 5 min and then stirred at room temperature under hydrogen overnight. The mixture was filtered through a pad of Celite washing with methanol (25 mL). The resulting filtrate was concentrated under reduced pressure to provide as a red solid and mixture of diastereoisomers, (12R)-20-amino-6-hydroxy-6-(trifluoromethyl)-22-oxa-3,4,16,21-tetraazatetracyclo[15.3.1.12,5.012,16]docosa-1(21),2,4,17,19-pentaene-18-carbonitrile (130 mg, 76%). ESI-MS m/z calc. 422.16782, found 423.2 (M+1)$^+$; Retention time: 2.14 minutes (LC Method E).

Step 3: (12R)-20-Amino-6-hydroxy-6-(trifluoromethyl)-22-oxa-3,4,16,21-tetraazatetracyclo[15.3.1.1 2,5.0 12,16]docosa-1(21),2,4,17,19-pentaene-18-carbonitrile (enantiomer 1) (Compound 80) and (12R)-20-amino-6-hydroxy-6-(trifluoromethyl)-22-oxa-3,4, 16,21-tetraazatetracyclo[15.3.1.1 2,5.0 12,16]docosa-1(21),2,4,17,19-pentaene-18-carbonitrile (enantiomer 2) (Compound 81)

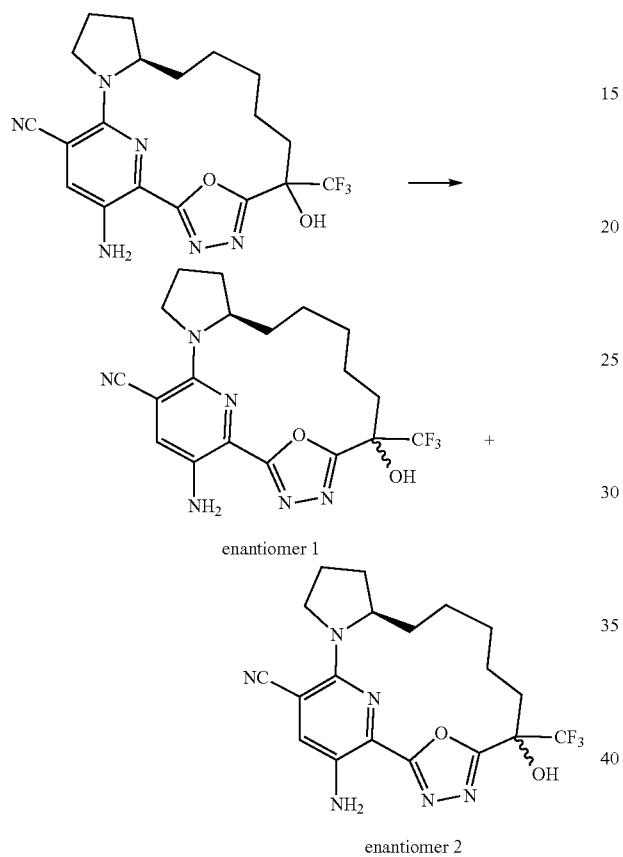

enantiomer 1 enantiomer 2

A diastereomeric mixture of (12R)-20-amino-6-hydroxy-6-(trifluoromethyl)-22-oxa-3,4,16,21-tetraazatetracyclo [15.3.1.1 2,5.0 12,16]docosa-1(21),2,4,17,19-pentaene-18-carbonitrile (162 mg, 0.3835 mmol) was purified by chiral SFC using a Lux Cellulose-5 column (250×21.2 mm, 5 μm particle size) eluting with 40% MeOH in 60% $CO_2$ which provided two single enantiomers:

The first diastereomer to elute was isolated as an orange solid, (12R)-20-amino-6-hydroxy-6-(trifluoromethyl)-22-oxa-3,4,16,21-tetraazatetracyclo[15.3.1.1 2,5.0 12,16]docosa-1(21),2,4,17,19-pentaene-18-carbonitrile (enantiomer 1) (47 mg, 28%). $^1$H NMR (300 MHz, Chloroform-d) δ 7.34 (br. s., 1H), 4.25-3.85 (m, 3H), 3.83-3.71 (m, 1H), 2.58-2.38 (m, 2H), 2.19-1.90 (m, 5H), 1.79-1.65 (m, 2H), 1.64-1.37 (m, 6H), 0.97-0.82 (m, 1H) ppm. $^{19}$F NMR (282 MHz, Chloroform-d) δ −80.74 (s, 3F) ppm. ESI-MS m/z calc. 422.1678, found 423.2 (M+1)$^+$; Retention time: 3.29 minutes (LC Method C).

The second enantiomer to elute was isolated as an orange solid, (12R)-20-amino-6-hydroxy-6-(trifluoromethyl)-22-oxa-3,4,16,21-tetraazatetracyclo[15.3.1.1 2,5.0 12,16]docosa-1(21),2,4,17,19-pentaene-18-carbonitrile (enantiomer 2) (35 mg, 21%). $^1$H NMR (300 MHz, Chloroform-d) δ 7.35 (s, 1H), 4.98 (br. s., 2H), 4.07-3.88 (m, 2H), 3.85-3.64 (m, 2H), 2.68-2.49 (m, 1H), 2.41-2.15 (m, 2H), 2.14-1.88 (m, 4H), 1.81-1.69 (m, 1H), 1.67-1.50 (m, 5H), 1.09-0.93 (m, 1H) ppm. ESI-MS m/z calc. 422.1678, found 423.2 (M+1)$^+$; Retention time: 3.28 minutes (LC Method C).

Example 45: Preparation of (15R)-23-amino-6,21-bis(trifluoromethyl)-26-oxa-3,4,19,24,25-pentaazapentacyclo[18.3.1.1 2,5.1 7,11.0 15,19]hexacosa-1(24),2,4,7(25),8,10,20,22-octaen-6-ol (hydrochloride salt) (enantiomer 1) (Compound 82) and (15R)-23-amino-6,21-bis(trifluoromethyl)-26-oxa-3,4,19,24,25-pentaazapentacyclo[18.3.1.1 2,5.1 7,11.0 15,19] hexacosa-1(24),2,4,7(25),8,10,20,22-octaen-6-ol (hydrochloride salt) (enantiomer 2) (Compound 83)

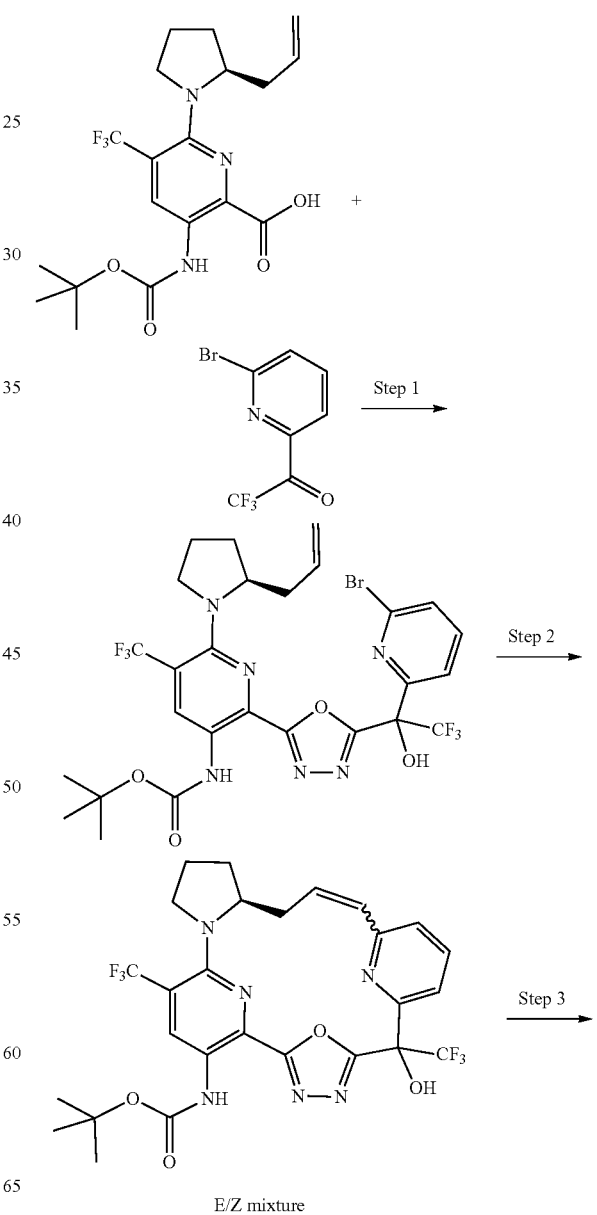

E/Z mixture

-continued

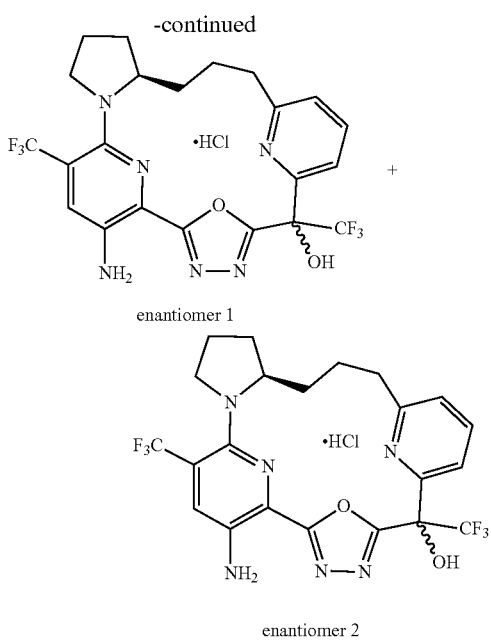

enantiomer 1 enantiomer 2

Step 1: tert-Butyl N-[6-[(2S)-2-allylpyrrolidin-1-yl]-2-[5-[1-(6-bromo-2-pyridyl)-2,2,2-trifluoro-1-hydroxy-ethyl]-1,3,4-oxadiazol-2-yl]-5-(trifluoromethyl)-3-pyridyl]carbamate A mixture of 1-(6-bromo-2-pyridyl)-2,2,2-trifluoro-ethanone (146.8 mg, 0.5779 mmol) and (N-isocyanoimino)triphenylphosphorane (174.7 mg, 0.5779 mmol) in DCM (2 mL) was stirred at room temperature for 30 min. Then, 6-[(2S)-2-allylpyrrolidin-1-yl]-3-(tert-butoxycarbonylamino)-5-(trifluoromethyl)pyridine-2-carboxylic acid (300 mg, 0.7222 mmol) was added in DCM (2 mL) dropwise. The mixture was stirred at room temperature overnight. The mixture was then diluted with EtOAc (50 mL), washed with water and brine consecutively, then dried over sodium sulfate, filtered and concentrated. The resultant brown residue was purified by silica gel chromatography using a shallow gradient from 100% hexanes to 100% EtOAc to afford as a yellow solid, tert-butyl N-[6-[(2S)-2-allylpyrrolidin-1-yl]-2-[5-[1-(6-bromo-2-pyridyl)-2,2,2-trifluoro-1-hydroxy-ethyl]-1,3,4-oxadiazol-2-yl]-5-(trifluoromethyl)-3-pyridyl]carbamate (107 mg, 21%). $^1$H NMR (400 MHz, DMSO-d6) δ 9.43 (d, J=16.4 Hz, 1H), 8.99 (d, J=9.6 Hz, 1H), 8.67 (d, J=8.6 Hz, 1H), 8.05-7.94 (m, 2H), 7.85-7.75 (m, 1H), 5.55-5.39 (m, 1H), 4.96-4.78 (m, 2H), 4.20 (ddd, J=15.2, 10.7, 6.3 Hz, 1H), 3.53 (d, J=9.0 Hz, 1H), 3.35 (s, 1H), 2.33 (s, 1H), 2.09 (dd, J=13.8, 6.9 Hz, 1H), 2.01 (d, J=7.2 Hz, 1H), 1.92 (s, 1H), 1.72 (s, 1H), 1.64-1.58 (m, 1H), 1.48 (d, J=2.5 Hz, 9H) ppm. ESI-MS m/z calc. 692.11816, found 693.15 (M+1)$^+$; Retention time: 0.67 minutes (LC Method T).

Step 2: tert-Butyl N-[(15S)-6-hydroxy-6,21-bis(trifluoromethyl)-26-oxa-3,4,19,24,25-pentaazapentacyclo[18.3.1.12,5.17,11.015,19]hexacosa-1(24),2,4,7(25),8,10,12,20,22-nonaen-23-yl]carbamate (E/Z Mixture)

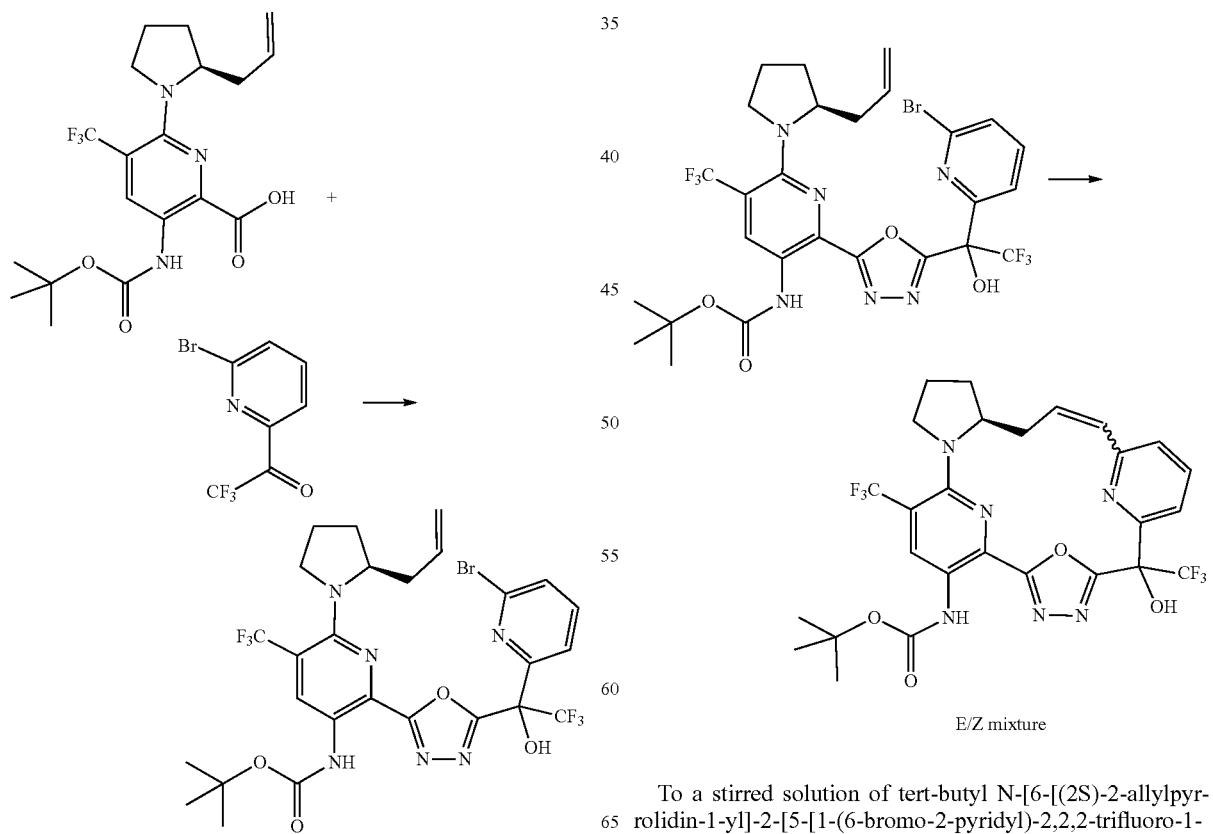

E/Z mixture

To a stirred solution of tert-butyl N-[6-[(2S)-2-allylpyrrolidin-1-yl]-2-[5-[1-(6-bromo-2-pyridyl)-2,2,2-trifluoro-1-hydroxy-ethyl]-1,3,4-oxadiazol-2-yl]-5-(trifluoromethyl)-3-pyridyl]carbamate (60 mg, 0.08653 mmol) in acetonitrile (8 mL) was added palladium(II) acetate (6 mg, 0.02672 mmol) followed by tris-o-tolylphosphane (16 mg, 0.05257 mmol) and triethylamine (100 μL, 0.7175 mmol) and the solution was bubbled with $N_2$ for 1 min. Heated the mixture with microwave irradiation at 150° C. for 1 h. Cooled the mixture to room temperature then diluted with EtOAc and washed with saturated $NH_4Cl$ (1×) and brine (1×) then dried over sodium sulfate, filtered and concentrated to a yellow oil which was dissolved in DMSO and purified by using a reverse phase HPLC using a gradient from 40% to 80% acetonitrile in water (+5 mM HCl) over 15.0 minutes which gave as a yellow solid, tert-butyl N-[(15S)-6-hydroxy-6,21-bis(trifluoromethyl)-26-oxa-3,4,19,24,25-pentaazapentacyclo[18.3.1.1²,⁵.1⁷,¹¹.0¹⁵,¹⁹]hexacosa-1(24),2,4,7(25),8,10,12,20,22-nonaen-23-yl]carbamate (E/Z mixture) (27 mg, 51%). ESI-MS m/z calc. 612.19196, found 613.2 $(M+1)^+$; Retention time: 0.59 minutes (LC Method T).

Step 3: (15R)-23-Amino-6,21-bis(trifluoromethyl)-26-oxa-3,4,19,24,25-pentaazapentacyclo[18.3.1.1²,5.17,11.015,19]hexacosa-1(24),2,4,7(25),8,10,20,22-octaen-6-ol (hydrochloride salt) (enantiomer 1) (Compound 82) and (15R)-23-Amino-6,21-bis(trifluoromethyl)-26-oxa-3,4,19,24,25-pentaazapentacyclo[18.3.1.1²,5.17,11.015,19]hexacosa-1(24),2,4,7(25),8,10,20,22-octaen-6-ol (hydrochloride salt) (enantiomer 2) (Compound 83)

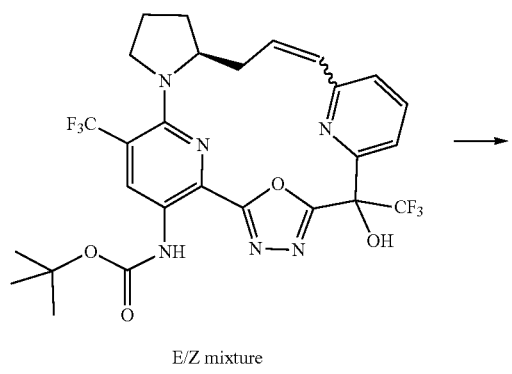

E/Z mixture

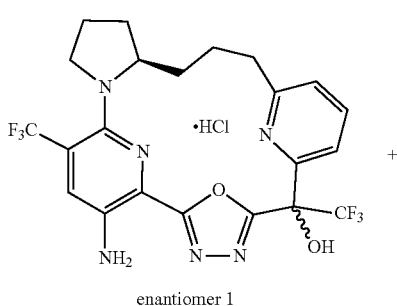

enantiomer 1

+

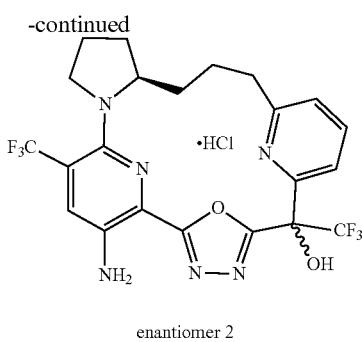

enantiomer 2

To a solution of tert-butyl N-[(15S)-6-hydroxy-6,21-bis(trifluoromethyl)-26-oxa-3,4,19,24,25-pentaazapentacyclo[18.3.1.1²,5.17,11.015,19]hexacosa-1(24),2,4,7(25),8,10,12,20,22-nonaen-23-yl]carbamate (E/Z mixture) (27 mg, 0.04408 mmol) in ethanol (5 mL) was added palladium on carbon (12 mg, 10% w/w, 0.01128 mmol) in a round bottom flask equipped with a hydrogen balloon using a 3-way adaptor. Subjected the mixture to vacuum and backfilled with nitrogen gas three times then subjected to vacuum. Filled the flask with hydrogen gas then stirred the mixture for 15 hours. Subjected the mixture to vacuum and backfilled with nitrogen gas three times then diluted with ethyl acetate and filtered over Celite. The filtrate was concentrated and dissolved in 400 μL of a 1:3 TFA/dichloromethane mixture. Stirred the reaction for about 1 h and the solvents were evaporated. The resultant residue was dissolved in 2 mL of MeOH and purified by reverse phase HPLC using a gradient from 30% to 99% acetonitrile in water (+5 mM HCl) over 30 minutes giving two diastereomeric products:

The first diastereomer to elute was isolated as a yellow amorphous solid, (15R)-23-amino-6,21-bis(trifluoromethyl)-26-oxa-3,4,19,24,25-pentaazapentacyclo[18.3.1.1²,5.17,11.015,19]hexacosa-1(24),2,4,7(25),8,10,20,22-octaen-6-ol (hydrochloride salt) (enantiomer 1) (5.1 mg, 40%). $^1H$ NMR (500 MHz, DMSO-d6) δ 8.79 (s, 2H), 7.75 (t, J=7.8 Hz, 1H), 7.68 (s, 1H), 7.59 (d, J=7.8 Hz, 1H), 7.24 (d, J=7.7 Hz, 1H), 3.93 (tdd, J=9.8, 5.9, 3.0 Hz, 1H), 3.49 (q, J=8.8 Hz, 1H), 3.23 (t, J=9.0 Hz, 1H), 3.10-3.00 (m, 1H), 2.74-2.67 (m, 1H), 2.43 (dd, J=14.2, 10.6 Hz, 1H), 2.23 (dqd, J=19.9, 7.3, 2.7 Hz, 2H), 1.90 (dt, J=12.6, 6.6 Hz, 1H), 1.69 (dtd, J=28.3, 11.9, 7.9 Hz, 2H), 1.58-1.50 (m, 1H), 0.82 (qd, J=11.5, 4.6 Hz, 1H) ppm. One exchangeable proton peak not observed and assumed to overlap with DMSO peak in NMR. ESI-MS m/z calc. 514.1552, found 515.1 $(M+1)^+$; Retention time: 1.76 minutes (LC Method J).

The second enantiomer to elute was isolated as a yellow amorphous solid, (15R)-23-amino-6,21-bis(trifluoromethyl)-26-oxa-3,4,19,24,25-pentaazapentacyclo[18.3.1.1²,5.17,11.015,19]hexacosa-1(24),2,4,7(25),8,10,20,22-octaen-6-ol (hydrochloride salt) (enantiomer 2) (6.7 mg, 55%). $^1H$ NMR (400 MHz, DMSO-d6) δ 8.27 (s, 2H), 7.83 (t, J=7.8 Hz, 1H), 7.66 (s, 1H), 7.51 (d, J=7.8 Hz, 1H), 7.41 (d, J=7.7 Hz, 1H), 3.75 (d, J=5.6 Hz, 1H), 3.48 (d, J=8.2 Hz, 1H), 3.20-3.13 (m, 1H), 3.13-3.06 (m, 1H), 2.69-2.57 (m, 3H), 2.17-2.03 (m, 2H), 1.87 (q, J=9.1, 6.1 Hz, 2H), 1.55 (dtd, J=28.5, 12.1, 11.4, 3.9 Hz, 2H), 0.94 (tt, J=10.8, 5.5 Hz, 1H) ppm. ESI-MS m/z calc. 514.1552, found 515.1 $(M+1)^+$; Retention time: 1.82 minutes (LC Method J).

Example 46: Preparation of (15R)-23-amino-6,21-bis(trifluoromethyl)-26-oxa-3,4,8,19,24-pentaazapentacyclo[18.3.1.1<sup>2,5</sup>.1<sup>7,11</sup>.0<sup>15,19</sup>]hexacosa-1(24),2,4,7(25),8,10,20,22-octaen-6-ol (isomer 1) (hydrochloride salt) (Compound 84), (15R)-23-amino-6,21-bis(trifluoromethyl)-26-oxa-3,4,8,19,24-pentaazapentacyclo[18.3.1.1<sup>2,5</sup>.1<sup>7,11</sup>.0<sup>15,19</sup>]hexacosa-1(24),2,4,7(25),8,10,20,22-octaen-6-ol (isomer 2) (hydrochloride salt) (Compound 85), (15R)-23-amino-6,21-bis(trifluoromethyl)-26-oxa-3,4,8,19,24-pentaazapentacyclo[18.3.1.1<sup>2,5</sup>.1<sup>7,11</sup>.0<sup>15,19</sup>]hexacosa-1(24),2,4,7(25),8,10,20,22-octaen-6-ol (isomer 3) (hydrochloride salt) (Compound 86) and (15R)-23-amino-6,21-bis(trifluoromethyl)-26-oxa-3,4,8,19,24-pentaazapentacyclo[18.3.1.1<sup>2,5</sup>.1<sup>7,11</sup>.0<sup>15,19</sup>]hexacosa-1(24),2,4,7(25),8,10,20,22-octaen-6-ol (isomer 4) (hydrochloride salt) (Compound 87)

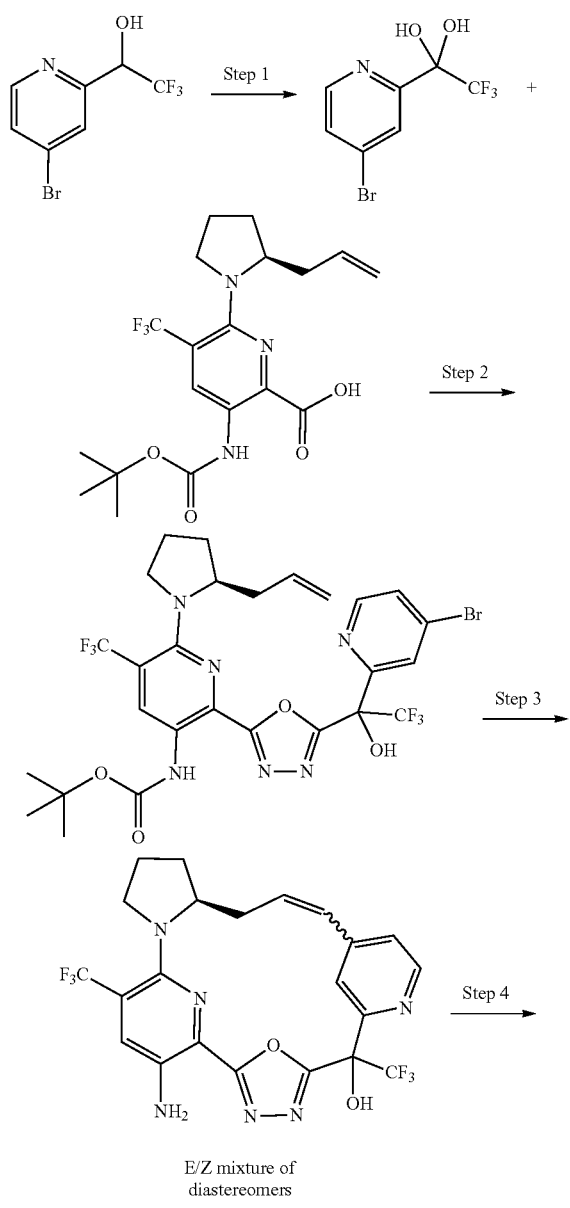

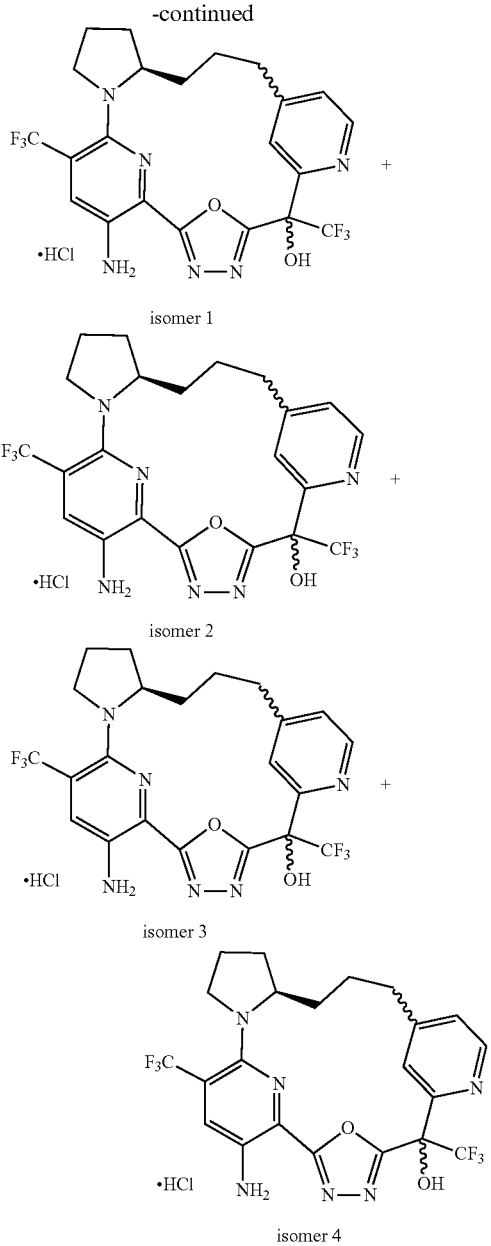

Step 1: 1-(4-Bromo-2-pyridyl)-2,2,2-trifluoro-ethane-1,1-diol

Dess-Martin periodinane (14.2 g, 33.48 mmol) was added in portions to a stirred solution of 1-(4-bromo-2-pyridyl)-2,2,2-trifluoro-ethanol (7.095 g, 27.71 mmol) in DCM (100 mL) at 0° C. and the reaction was allowed to warm to ambient temperature over 18 hours. The reaction mixture was quenched by the addition of 1:1 saturated aqueous NaHCO₃/sodium thiosulfate (20 mL), stirred for 10 minutes and the layers separated. The aqueous layer was extracted with DCM (3×) and the combined organic extracts were washed with 1:1 saturated aqueous NaHCO₃/sodium thiosulfate (3×50 mL) and brine (once), dried the mixture by passing through a phase separation cartridge, filtered and concentrated in vacuo. Attempted to dissolve the residue in DCM, however, a white insoluble solid crashed out which was filtered and the filtrate was concentrated in vacuo to give a pale-yellow oil. The oil was purified by silica chromatography eluting with a gradient from 0% to 30% EtOAc in heptane. Relevant fractions were combined and evaporated to dryness to give, 1-(4-bromo-2-pyridyl)-2,2,2-trifluoroethane-1,1-diol (7.5 g, 100%) ¹H NMR (500 MHz, DMSO-d6) δ 8.54 (d, J=5.3 Hz, 1H), 7.90 (d, J=1.8 Hz, 1H), 7.79 (dd, J=5.3, 1.9 Hz, 1H), 7.72 (s, 2H) ppm. ESI-MS m/z calc. 270.9456, found 271.8 (M+1)⁺; Retention time: 0.6 minutes (LC Method V).

Step 2: tert-Butyl N-[6-[(2S)-2-allylpyrrolidin-1-yl]-2-[5-[1-(4-bromo-2-pyridyl)-2,2,2-trifluoro-1-hydroxy-ethyl]-1,3,4-oxadiazol-2-yl]-5-(trifluoromethyl)-3-pyridyl]carbamate

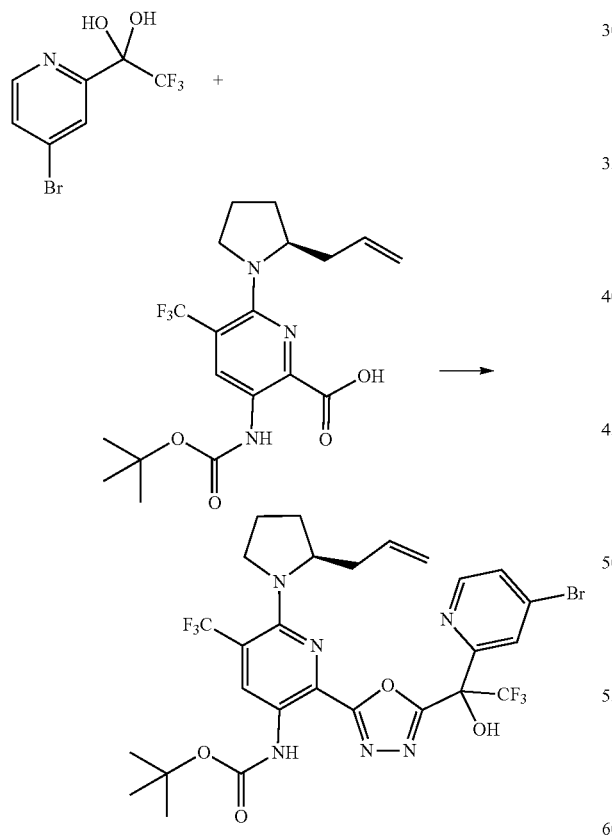

To a stirring solution of 1-(4-bromo-2-pyridyl)-2,2,2-trifluoro-ethane-1,1-diol (344.1 mg, 1.265 mmol) and 6-[(2S)-2-allylpyrrolidin-1-yl]-3-(tert-butoxycarbonylamino)-5-(trifluoromethyl)pyridine-2-carboxylic acid (300 mg, 0.6326 mmol) in DMF (5.256 mL) under nitrogen atmosphere at 75° C. was added (N-isocyanoimino)triphenylphosphorane (382.4 mg, 1.265 mmol) and the resulting mixture was capped and stirred 15 minutes then cooled to room temperature. Diluted the mixture with EtOAc and washed once with saturated aqueous NaHCO₃, once with saturated aqueous NH₄Cl and once with brine. Dried the organic layer over sodium sulfate, filtered and concentrated to an orange oil which was purified by silica gel chromatography using a shallow gradient from 100% hexanes to 100% EtOAc giving the product contaminated mostly with a MW=439 side-product. This material was further purified by silica gel chromatography using a shallow gradient from 100% DCM to 20% MeOH in DCM giving tert-butyl N-[6-[(2S)-2-allylpyrrolidin-1-yl]-2-[5-[1-(4-bromo-2-pyridyl)-2,2,2-trifluoro-1-hydroxy-ethyl]-1,3,4-oxadiazol-2-yl]-5-(trifluoromethyl)-3-pyridyl]carbamate (259.8 mg, 59%). ¹H NMR (400 MHz, Chloroform-d) δ 9.56 (s, 1H), 9.02 (s, 1H), 8.51 (dd, J=5.3, 3.2 Hz, 1H), 8.15-8.08 (m, 1H), 7.70 (td, J=5.4, 1.7 Hz, 1H), 7.10 (d, J=5.5 Hz, 1H), 5.89-5.70 (m, 1H), 5.12-4.96 (m, 2H), 4.50-4.40 (m, 1H), 3.64 (dd, J=9.6, 6.7 Hz, 1H), 3.40 (t, J=8.2 Hz, 1H), 2.68-2.51 (m, 1H), 2.29-2.14 (m, 1H), 2.14-2.03 (m, 1H), 1.97 (ddt, J=11.3, 5.5, 2.7 Hz, 1H), 1.81-1.66 (m, 2H), 1.54 (d, J=1.4 Hz, 9H) ppm. ESI-MS m/z calc. 692.11816, found 693.4 (M+1)⁺; Retention time: 0.79 minutes (LC Method T).

Step 3: (15S)-23-Amino-6,21-bis(trifluoromethyl)-26-oxa-3,4,8,19,24-pentaazapentacyclo[18.3.1.1²,⁵.1⁷,¹¹.0¹⁵,¹⁹]hexacosa-1(24),2,4,7(25),8,10,12,20,22-nonaen-6-ol

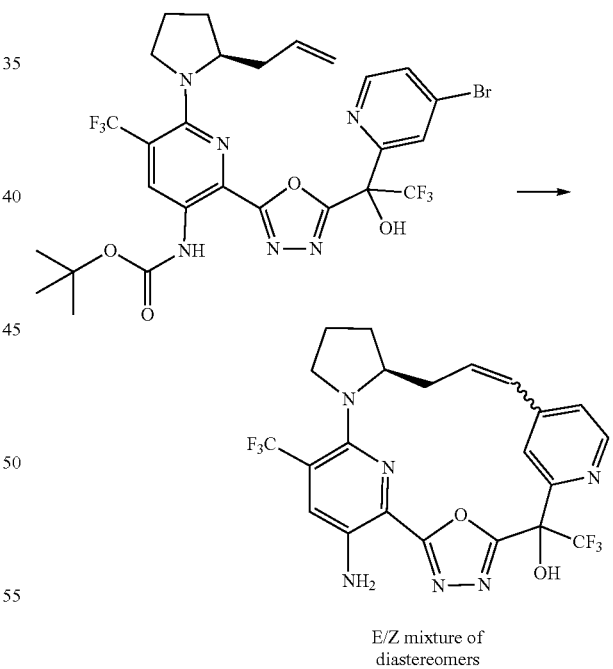

E/Z mixture of diastereomers

To a stirred solution of tert-butyl N-[6-[(2S)-2-allylpyrrolidin-1-yl]-2-[5-[1-(4-bromo-2-pyridyl)-2,2,2-trifluoro-1-hydroxy-ethyl]-1,3,4-oxadiazol-2-yl]-5-(trifluoromethyl)-3-pyridyl]carbamate (288.7 mg, 0.4163 mmol) in acetonitrile (17.32 mL) was added diacetoxypalladium (28.04 mg, 0.1249 mmol) followed by tris-o-tolylphosphane (76.03 mg, 0.2498 mmol) and triethylamine (46.42 μL, 0.333 mmol) and the solution was bubbled with nitrogen for 1 min then heated by microwave irradiation at 150° C. for 2 h. Cooled the mixture to room temperature then diluted with EtOAc and washed once with saturated aqueous NH₄Cl and once with brine then dried over sodium sulfate, filtered and concentrated to a yellow oil. This oil was dissolved in DCM/MeOH, stirred with Celite for 5 minutes then filtered over a pad of Celite eluting with MeOH. The filtrate was concentrated to a yellow foam which was dissolved in DCM (3 mL) and stirred at room temperature. TFA (1.282 mL, 16.64 mmol) was added and the resulting solution was stirred at room temperature for 4 h. Concentrated the solution to a residue by rotary evaporation then dissolved in DMSO, filtered and purified by reverse phase HPLC using a Luna $C_{18}$ column (75×30 mm, 5 µm particle size) sold by Phenomenex (pn: 00C-4252-U0-AX) and a dual gradient run from 50% to 99% mobile phase B over 15.0 minutes (mobile phase A=H₂O (5 mM HCl), mobile phase B=acetonitrile, flow rate=50 mL/min, injection volume=950 µL and column temperature=25° C.) giving as a light yellow solid, (15S)-23-amino-6,21-bis(trifluoromethyl)-26-oxa-3,4,8,19,24-pentaazapentacyclo[18.3.1.12,5.17,11.015,19]hexacosa-1(24),2,4,7(25),8,10,12,20,22-nonaen-6-ol (E/Z mixture of diastereomers) (94.1 mg, 44%). ESI-MS m/z calc. 512.1395, found 513.3 (M+1)⁺; Retention time: 0.46 minutes (LC Method T).

Step 4: (15R)-23-Amino-6,21-bis(trifluoromethyl)-26-oxa-3,4,8,19,24-pentaazapentacyclo[18.3.1.12,5.17,11.015,19]hexacosa-1(24),2,4,7(25),8,10,20,22-octaen-6-ol (isomer 1) (hydrochloride salt) (Compound 84), (15R)-23-amino-6,21-bis(trifluoromethyl)-26-oxa-3,4,8,19,24-pentaazapentacyclo[18.3.1.12,5.17,11.015,19]hexacosa-1(24),2,4,7(25),8,10,20,22-octaen-6-ol (isomer 2) (hydrochloride salt) (Compound 85), (15R)-23-amino-6,21-bis(trifluoromethyl)-26-oxa-3,4,8,19,24-pentaazapentacyclo[18.3.1.12,5.17,11.015,19]hexacosa-1(24),2,4,7(25),8,10,20,22-octaen-6-ol (isomer 3) (hydrochloride salt) (Compound 86), and (15R)-23-amino-6,21-bis(trifluoromethyl)-26-oxa-3,4,8,19,24-pentaazapentacyclo[18.3.1.12,5.17,11.015,19]hexacosa-1(24),2,4,7(25),8,10,20,22-octaen-6-ol (isomer 4) (hydrochloride salt) (Compound 87)

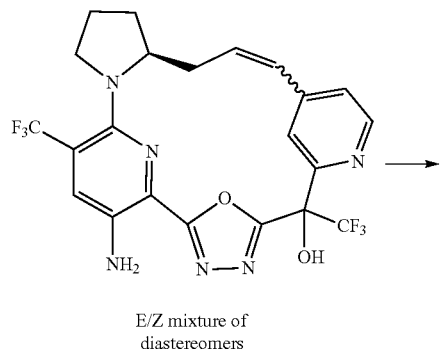

E/Z mixture of diastereomers

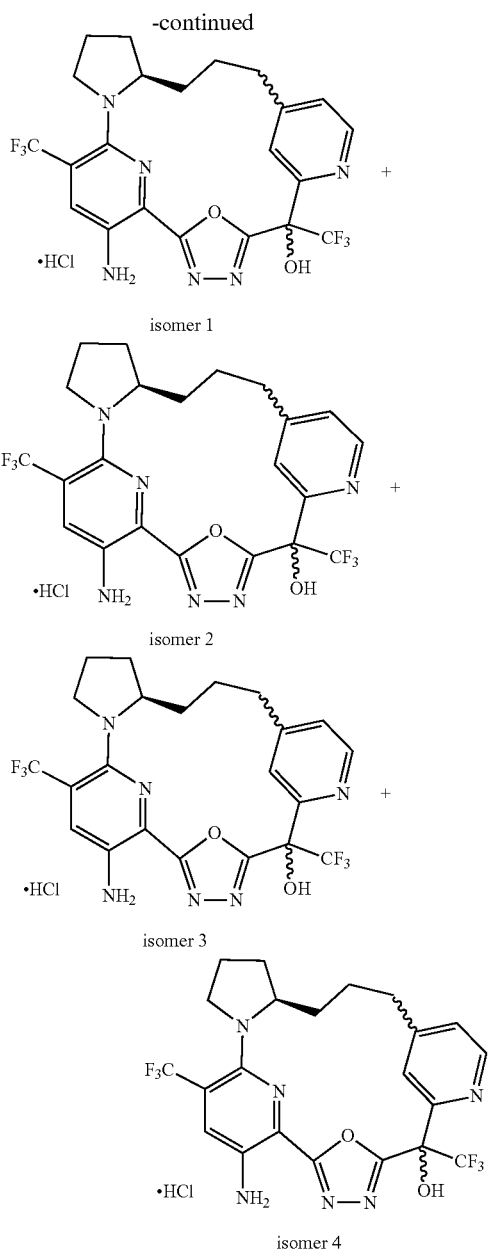

isomer 1 isomer 2 isomer 3 isomer 4

To a solution of (15S)-23-amino-6,21-bis(trifluoromethyl)-26-oxa-3,4,8,19,24-pentaazapentacyclo[18.3.1.12,5.17,11.015,19]hexacosa-1(24),2,4,7(25),8,10,12,20,22-nonaen-6-ol (E/Z mixture of diastereomers) (94 mg, 0.1834 mmol) in ethanol (5.875 mL) was added palladium on carbon (58.55 mg of 10% w/w, 0.05502 mmol) and hydrogen was bubbled through the solution for 5 min then the flask was capped with a hydrogen balloon and stirred for 4 h. Bubbled nitrogen through the solution for 5 min then filtered over Celite eluting with methanol giving a yellow solution which was concentrated to give a yellow solid which was dissolved in DMSO, filtered and purified by reverse phase HPLC using a Luna Cis column (75×30 mm, 5 µm particle size) sold by Phenomenex (pn: 00C-4252-U0-AX) and a dual gradient run from 50% to 99% mobile phase B over 15.0 minutes (mobile phase A=H₂O (5 mM HCl), mobile phase B=acetonitrile, flow rate=50 mL/min, injection volume=950 µL and column temperature=25° C.) to give 4 isomeric products all as yellow foams:

Peak 1: (15R)-23-amino-6,21-bis(trifluoromethyl)-26-oxa-3,4,8,19,24-pentaazapentacyclo[18.3.1.1²,⁵.1⁷,¹¹.0¹⁵,¹⁹]hexacosa-1(24),2,4,7(25),8,10,20,22-octaen-6-ol (isomer 1) (hydrochloride salt) (5.4 mg, 4%). ESI-MS m/z calc. 514.1552, found 515.4 (M+1)⁺; Retention time: 0.78 minutes (LC Method M).

Peak 2: (15R)-23-amino-6,21-bis(trifluoromethyl)-26-oxa-3,4,8,19,24-pentaazapentacyclo[18.3.1.1²,⁵.1⁷,¹¹.0¹⁵,¹⁹]hexacosa-1(24),2,4,7(25),8,10,20,22-octaen-6-ol (isomer 2) (hydrochloride salt) (31.9 mg, 24%). ESI-MS m/z calc. 514.1552, found 515.4 (M+1)⁺; Retention time: 0.85 minutes (LC Method M).

Peak 3: (15R)-23-amino-6,21-bis(trifluoromethyl)-26-oxa-3,4,8,19,24-pentaazapentacyclo[18.3.1.1²,⁵.1⁷,¹¹.0¹⁵,¹⁹]hexacosa-1(24),2,4,7(25),8,10,20,22-octaen-6-ol (isomer 3) (hydrochloride salt) (5.8 mg, 5%). ESI-MS m/z calc. 514.1552, found 515.4 (M+1)⁺; Retention time: 0.98 minutes (LC Method M).

Peak 4: (15R)-23-amino-6,21-bis(trifluoromethyl)-26-oxa-3,4,8,19,24-pentaazapentacyclo[18.3.1.1²,⁵.1⁷,¹¹.0¹⁵,¹⁹]hexacosa-1(24),2,4,7(25),8,10,20,22-octaen-6-ol (isomer 4) (hydrochloride salt) (22.1 mg, 16%). ESI-MS m/z calc. 514.1552, found 515.4 (M+1)⁺; Retention time: 1.06 minutes (LC Method M).

Each product is assumed to be a single diastereomer/atropisomer combination.

Example 47: Preparation of (12R)-20-amino-6-(oxan-4-yl)-18-(trifluoromethyl)-22-oxa-3,4,16,21-tetraazatetracyclo[15.3.1.1²,⁵.0¹²,¹⁶]docosa-1(20),2,4,17(21),18-pentaen-6-ol (enantiomer 1) (Compound 88) and (12R)-20-amino-6-(oxan-4-yl)-18-(trifluoromethyl)-22-oxa-3,4,16,21-tetraazatetracyclo[15.3.1.1²,⁵.0¹²,¹⁶]docosa-1(20),2,4,17(21),18-pentaen-6-ol (enantiomer 2) (Compound 89)

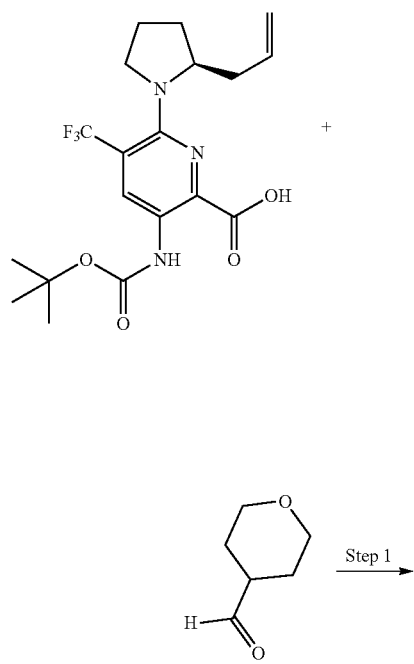

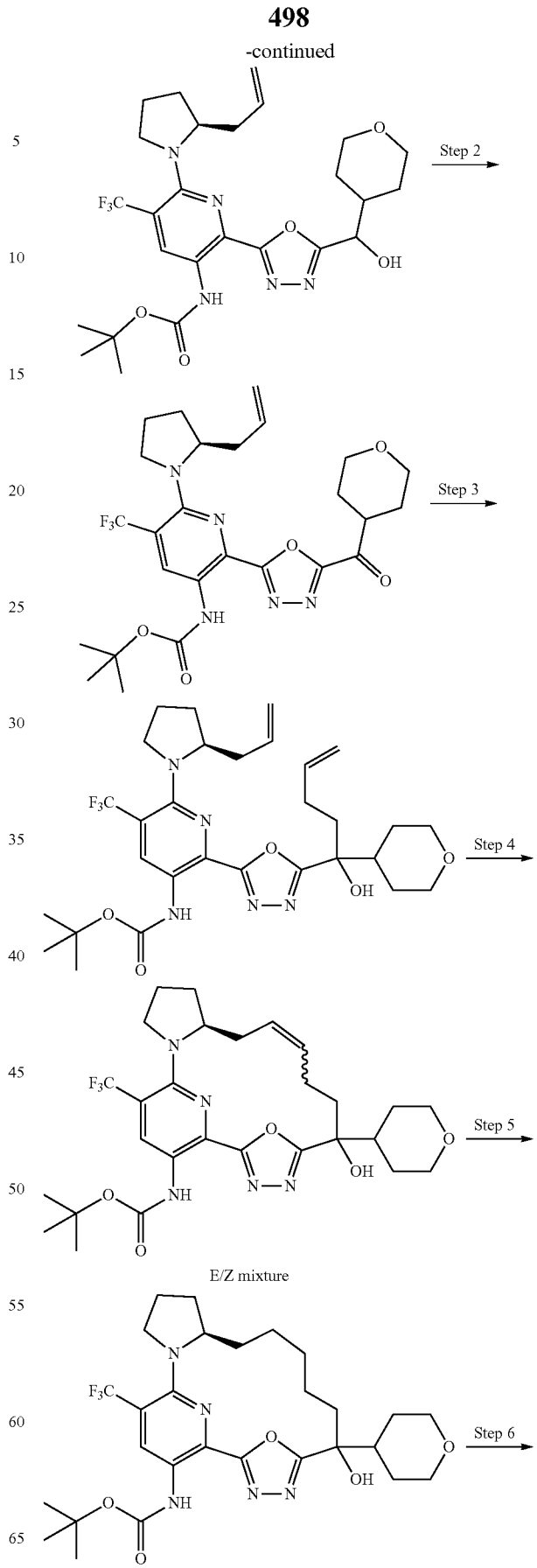

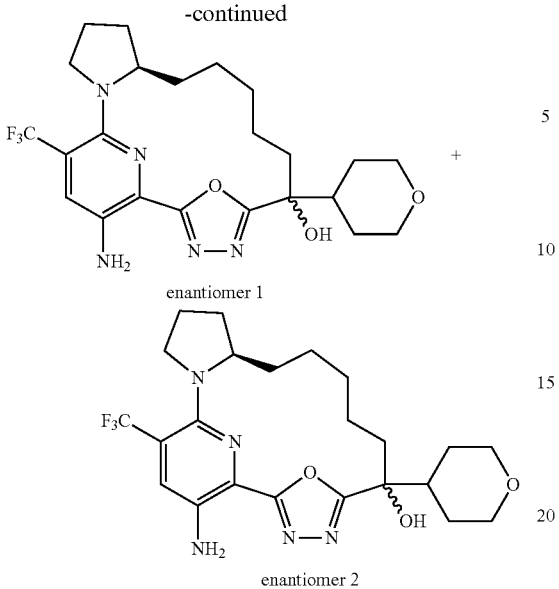

enantiomer 1 enantiomer 2

Step 1: tert-Butyl N-[6-[(2S)-2-allylpyrrolidin-1-yl]-2-[5-[hydroxy(tetrahydropyran-4-yl)methyl]-1,3,4-oxadiazol-2-yl]-5-(trifluoromethyl)-3-pyridyl]carbamate

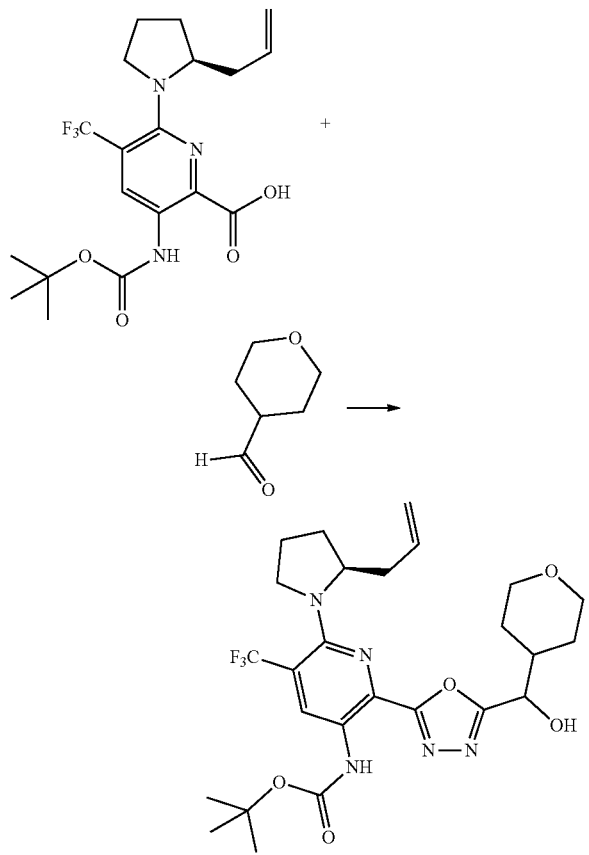

To a solution of tetrahydropyran-4-carbaldehyde (197.8 mg, 1.733 mmol) in DCM (1.872 mL) was added 6-[(2S)-2-allylpyrrolidin-1-yl]-3-(tert-butoxycarbonylamino)-5-(trifluoromethyl)pyridine-2-carboxylic acid (180 mg, 0.4333 mmol), followed by N-isocyanoimino)triphenylphosphorane (131 mg, 0.4333 mmol) and the mixture was stirred overnight at room temperature. The reaction mixture was concentrated and purified by chromatography (12 g amine column) using a gradient from 0% to 30% ethyl acetate in hexanes giving as a yellow solid, tert-butyl N-[6-[(2S)-2-allylpyrrolidin-1-yl]-2-[5-[hydroxy(tetrahydropyran-4-yl)methyl]-1,3,4-oxadiazol-2-yl]-5-(trifluoromethyl)-3-pyridyl]carbamate (150 mg, 63%). ESI-MS m/z calc. 553.2512, found 554.4 (M+1)$^+$; Retention time: 0.72 minutes (LC Method R).

Step 2: tert-Butyl N-[6-[(2S)-2-allylpyrrolidin-1-yl]-2-[5-(tetrahydropyran-4-carbonyl)-1,3,4-oxadiazol-2-yl]-5-(trifluoromethyl)-3-pyridyl]carbamate

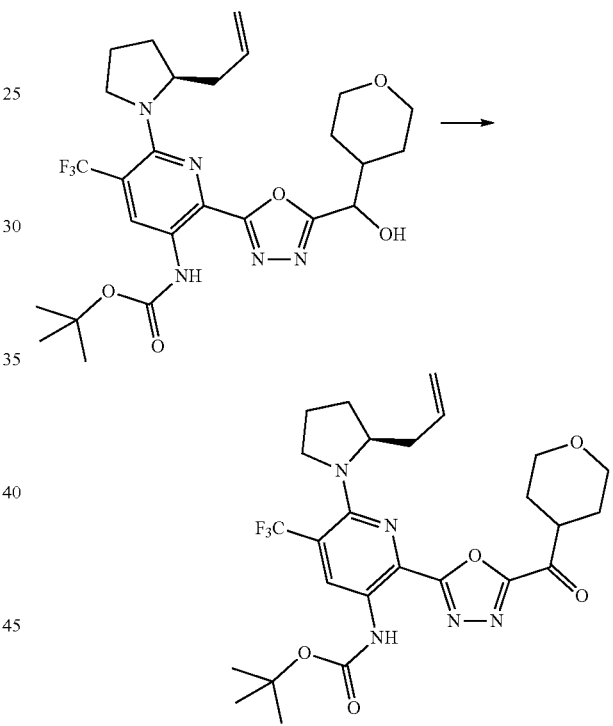

To a solution of tert-butyl N-[6-[(2S)-2-allylpyrrolidin-1-yl]-2-[5-[hydroxy(tetrahydropyran-4-yl)methyl]-1,3,4-oxadiazol-2-yl]-5-(trifluoromethyl)-3-pyridyl]carbamate (150 mg, 0.2710 mmol) in DCM (2.076 mL) was added DMP (127.8 mg, 0.3013 mmol). The reaction mixture was stirred at room temperature for 15 minutes and quenched with saturated aqueous NaHCO$_3$. Extracted with DCM (2×25 mL), combined the organic layers, washed with brine, dried over Na$_2$SO$_4$, filtered and concentrated. The residue was purified by silica gel chromatography using a gradient from 0% to 20% ethyl acetate in hexanes to afford as a yellow solid, tert-butyl N-[6-[(2S)-2-allylpyrrolidin-1-yl]-2-[5-(tetrahydropyran-4-carbonyl)-1,3,4-oxadiazol-2-yl]-5-(trifluoromethyl)-3-pyridyl]carbamate (110 mg, 74%). ESI-MS m/z calc. 551.23553, found 552.4 (M+1)$^+$; Retention time: 0.88 minutes (LC Method R).

501

Step 3: tert-Butyl N-[6-[(2S)-2-allylpyrrolidin-1-yl]-2-[5-(1-hydroxy-1-tetrahydropyran-4-yl-pent-4-enyl)-1,3,4-oxadiazol-2-yl]-5-(trifluoromethyl)-3-pyridyl]carbamate

502

Step 4: tert-Butyl N-[(12S)-6-hydroxy-6-(oxan-4-yl)-18-(trifluoromethyl)-22-oxa-3,4,16,21-tetraazatetracyclo[15.3.1.12,5.012,16]docosa-1(20),2,4,9,17(21),18-hexaen-20-yl]carbamate (E/Z Mixture)

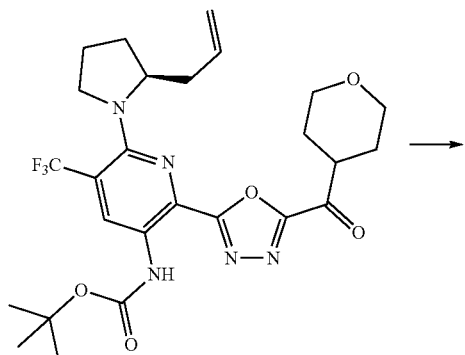

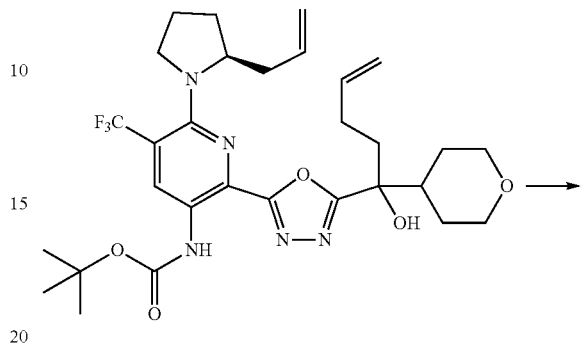

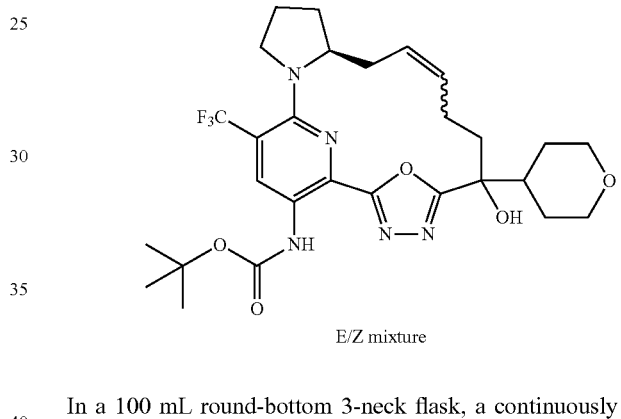

E/Z mixture

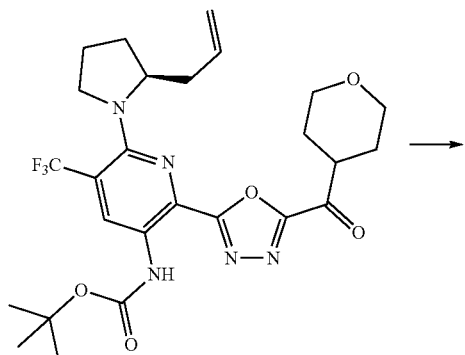

To an ice-bath cooled solution of tert-butyl N-[6-[(2S)-2-allylpyrrolidin-1-yl]-2-[5-(tetrahydropyran-4-carbonyl)-1,3,4-oxadiazol-2-yl]-5-(trifluoromethyl)-3-pyridyl]carbamate (56 mg, 0.1015 mmol) in THF (1.3 mL) was added bromo(but-3-enyl)magnesium (670 μL, 0.5 M, 0.3350 mmol) dropwise. The solution was stirred for 20 min then quenched by the addition of aqueous citric acid (101.4 μl M, 0.1014 mmol) while still in the ice bath. Extracted the mixture with ethyl acetate (2×15 mL), combined the organic layers, washed with brine, dried over Na$_2$SO$_4$, filtered and concentrated. Purified the residue by silica gel chromatography (12 g column) using a gradient from 0% to 30% ethyl acetate in hexanes which gave as a yellow solid, tert-butyl N-[6-[(2S)-2-allylpyrrolidin-1-yl]-2-[5-(1-hydroxy-1-tetrahydropyran-4-yl-pent-4-enyl)-1,3,4-oxadiazol-2-yl]-5-(trifluoromethyl)-3-pyridyl]carbamate (20 mg, 32%). ESI-MS m/z calc. 607.29816, found 608.5 (M+1)$^+$; Retention time: 0.88 minutes (LC Method R).

In a 100 mL round-bottom 3-neck flask, a continuously degassed solution via nitrogen line of tert-butyl N-[6-[(2S)-2-allylpyrrolidin-1-yl]-2-[5-(1-hydroxy-1-tetrahydropyran-4-yl-pent-4-enyl)-1,3,4-oxadiazol-2-yl]-5-(trifluoromethyl)-3-pyridyl]carbamate (35 mg, 0.05760 mmol) in DCE (17.5 mL) was heated at 50° C. under nitrogen atmosphere. Then, a solution of [1,3-bis(2,4,6-trimethylphenyl)imidazolidin-2-ylidene]-dichloro-[(2-isopropoxyphenyl)methylene]ruthenium (8.9 mg, 0.0142 mmol) in DCE (50 mL) was added via syringe. The resulting mixture was heated at 60° C. for 2 h. The reaction mixture was cooled to room temperature and concentrated under reduced pressure. The residue was purified by silica gel chromatography (24 g column) using a gradient from 100% hexanes to 40% ethyl acetate in hexanes to afford as a yellow semi-solid, tert-butyl N-[(12S)-6-hydroxy-6-(oxan-4-yl)-18-(trifluoromethyl)-22-oxa-3,4,16,21-tetraazatetracyclo[15.3.1.12,5.012,16]docosa-1(20),2,4,9,17(21),18-hexaen-20-yl]carbamate (E/Z mixture) (25 mg, 75%). ESI-MS m/z calc. 579.26685, found 580.48 (M+1)$^+$; Retention time: 0.74 minutes (LC Method R).

Step 5: tert-Butyl N-[(12R)-6-hydroxy-6-(oxan-4-yl)-18-(trifluoromethyl)-22-oxa-3,4,16,21-tetraazatetracyclo[15.3.1.1²,⁵.0¹²,¹⁶]docosa-1(20),2,4,17(21),18-pentaen-20-yl]carbamate

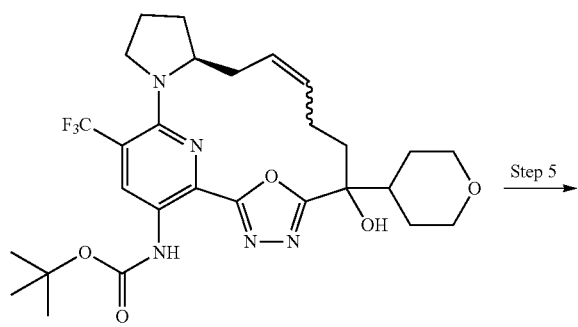

E/Z mixture

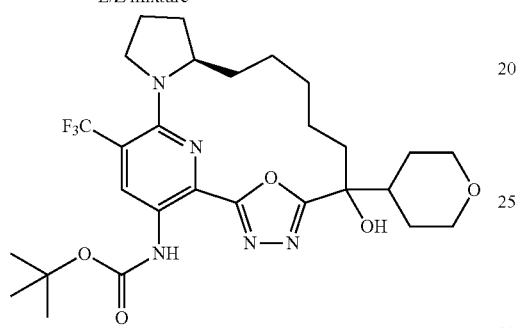

To a solution of tert-butyl N-[(12S)-6-hydroxy-6-(oxan-4-yl)-18-(trifluoromethyl)-22-oxa-3,4,16,21-tetraazatetracyclo[15.3.1.1²,⁵.0¹²,¹⁶]docosa-1(20),2,4,9,17(21),18-hexaen-20-yl]carbamate (E/Z mixture) (22 mg, 0.03796 mmol) in AcOH (594 µL) was added Pd/C (16 mg, 10% w/w, 0.01503 mmol). The mixture was flushed with nitrogen, evacuated and stirred for 4 h under a hydrogen balloon. The reaction mixture was filtered through a silica plug, washing well with ethyl acetate and then the filtrate was concentrated to provide as a yellow solid, tert-butyl N-[(12R)-6-hydroxy-6-(oxan-4-yl)-18-(trifluoromethyl)-22-oxa-3,4,16,21-tetraazatetracyclo[15.3.1.1²,⁵.0¹²,¹⁶]docosa-1(20),2,4,17(21),18-pentaen-20-yl]carbamate (18 mg, 82%). ESI-MS m/z calc. 581.28253, found 582.5 (M+1)⁺; Retention time: 0.85 minutes (LC Method R).

Step 6: (12R)-20-Amino-6-(oxan-4-yl)-18-(trifluoromethyl)-22-oxa-3,4,16,21-tetraazatetracyclo[15.3.1.1²,⁵.0¹²,¹⁶]docosa-1(20),2,4,17(21),18-pentaen-6-ol (enantiomer 1) (Compound 88) and (12R)-20-amino-6-(oxan-4-yl)-18-(trifluoromethyl)-22-oxa-3,4,16,21-tetraazatetracyclo[15.3.1.1²,⁵.0¹²,¹⁶]docosa-1(20),2,4,17(21),18-pentaen-6-ol (enantiomer 2) (Compound 89)

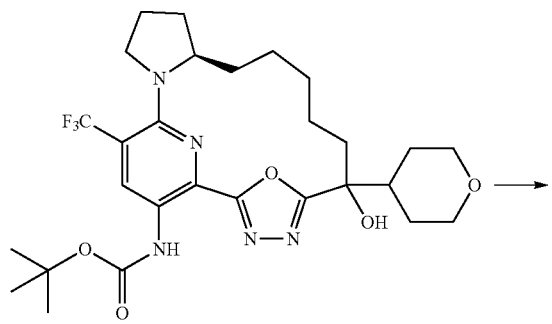

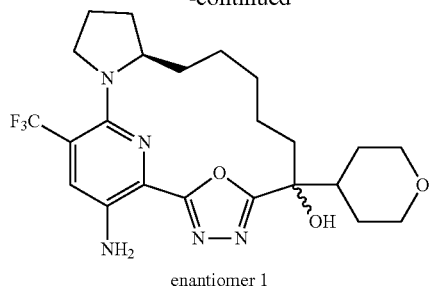

enantiomer 1

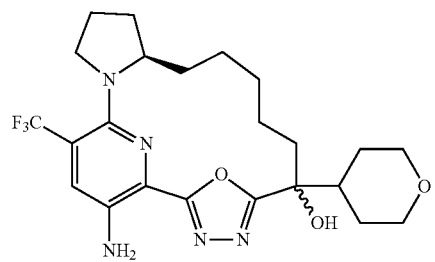

enantiomer 2

To a solution of tert-butyl N-[(12R)-6-hydroxy-6-(oxan-4-yl)-18-(trifluoromethyl)-22-oxa-3,4,16,21-tetraazatetracyclo[15.3.1.1²,⁵.0¹²,¹⁶]docosa-1(20),2,4,17(21),18-pentaen-20-yl]carbamate (15.00 mg, 0.02579 mmol) in DCM (308.2 µL) was added TFA (119.1 µL, 1.546 mmol) and the mixture was stirred at room temperature for 2 h. The reaction mixture was concentrated, then purified by chiral SFC using an OD-H column (250×21.2 mm, 5 µm particle size) sold by Chiral Technologies and eluting with a gradient from 5% to 15% MeOH (+20 mM NH₃) in CO₂ which provided two single diastereomeric products:

The first diastereomer to elute was isolated as a yellow solid, (12R)-20-amino-6-(oxan-4-yl)-18-(trifluoromethyl)-22-oxa-3,4,16,21-tetraazatetracyclo[15.3.1.1²,⁵.0¹²,¹⁶]docosa-1(20),2,4,17(21),18-pentaen-6-ol (enantiomer 1) (4 mg, 32%). ¹H NMR (400 MHz, CD₃OD) δ 7.49 (s, 1H), 4.14-4.00 (m, 1H), 3.89 (dd, J=10.6, 5.1 Hz, 2H), 3.52 (q, J=8.6 Hz, 1H), 3.37-3.22 (m, 3H), 2.48 (dtt, J=9.1, 6.0, 2.9 Hz, 1H), 2.12 (ddt, J=12.1, 6.3, 3.2 Hz, 1H), 2.05-1.25 (m, 16H), 0.90 (ddd, J=12.2, 10.5, 5.5 Hz, 1H) ppm. ESI-MS m/z calc. 481.23007, found 482.4 (M+1)⁺; Retention time: 3.02 minutes (LC Method A).

The second diastereomer to elute was isolated as a yellow solid, (12R)-20-amino-6-(oxan-4-yl)-18-(trifluoromethyl)-22-oxa-3,4,16,21-tetraazatetracyclo[15.3.1.1²,⁵.0¹²,¹⁶]docosa-1(20),2,4,17(21),18-pentaen-6-ol (enantiomer 2) (4 mg, 32%). ¹H NMR (400 MHz, CD₃OD) δ 7.49 (s, 1H), 4.16-4.02 (m, 1H), 3.89 (dd, J=10.6, 5.1 Hz, 2H), 3.52 (q, J=8.6 Hz, 1H), 3.39-3.21 (m, 5H), 2.48 (dtt, J=9.1, 6.0, 2.9 Hz, 1H), 2.12 (ddt, J=12.1, 6.3, 3.2 Hz, 1H), 2.06-1.29 (m, 14H), 0.90 (ddd, J=12.2, 10.5, 5.5 Hz, 1H) ppm. ESI-MS m/z calc. 481.23007, found 482.4 (M+1)⁺; Retention time: 2.03 minutes (LC Method A).

Example 48: Preparation of (12R)-20-amino-18-cyclopropyl-6-(trifluoromethyl)-22-oxa-3,4,16,21-tetraazatetracyclo[15.3.1.12,5.012,16]docosa-1(20),2,4,17(21),18-pentaen-6-ol (enantiomer 1) (Compound 90) and (12R)-20-amino-18-cyclopropyl-6-(trifluoromethyl)-22-oxa-3,4,16,21-tetraazatetracyclo[15.3.1.12,5.012,16]docosa-1(20),2,4,17(21),18-pentaen-6-ol (enantiomer 2) (Compound 91)

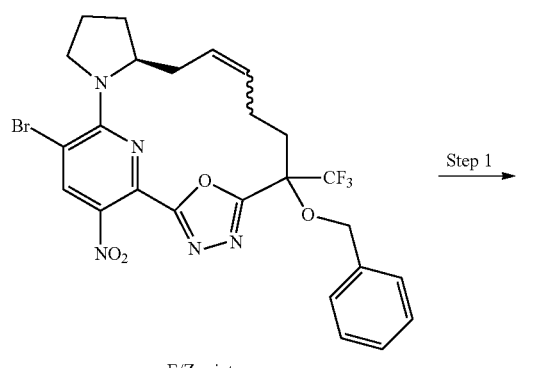

E/Z mixture

Step 1 →

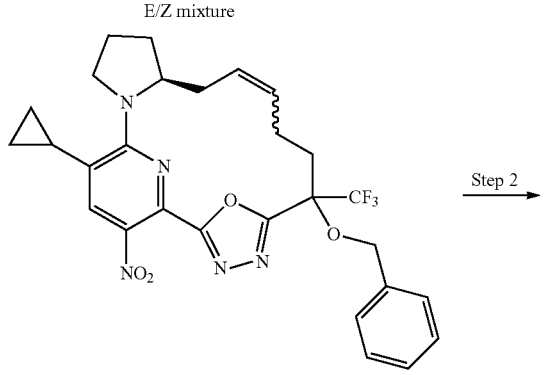

E/Z mixture

Step 2 →

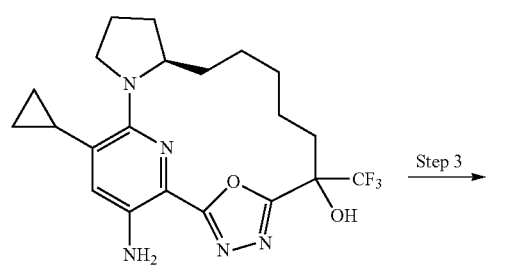

Step 3 →

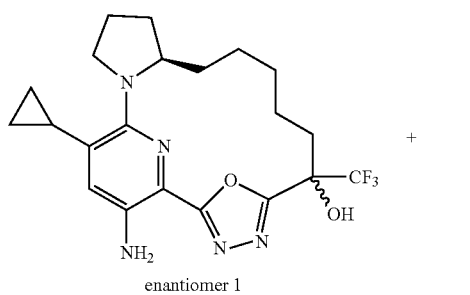

enantiomer 1

+

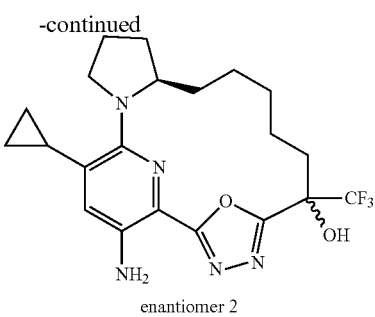

enantiomer 2

Step 1: (12S)-6-(Benzyloxy)-18-cyclopropyl-20-nitro-6-(trifluoromethyl)-22-oxa-3,4,16,21-tetraazatetracyclo[15.3.1.12,5.012,16]docosa-1(21),2,4,9,17,19-hexaene (E/Z Mixture)

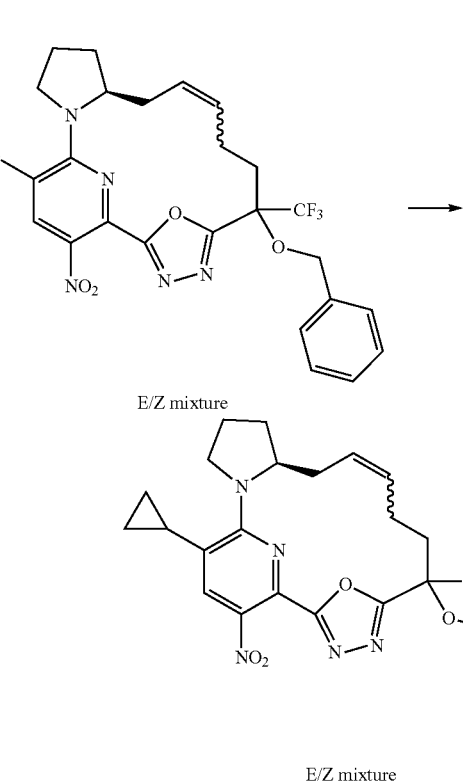

E/Z mixture

A solution of (12S)-6-(benzyloxy)-18-bromo-20-nitro-6-(trifluoromethyl)-22-oxa-3,4,16,21-tetraazatetracyclo [15.3.1.12,5.012,16]docosa-1(21),2,4,9,17,19-hexaene (E/Z mixture) (100 mg, 0.1465 mmol) in toluene (2.0 mL) and water (0.2 mL) was degassed by bubbling with nitrogen gas for 10 minutes. To this mixture was added potassium phosphate (96 mg, 0.4523 mmol), tricyclohexylphosphine tetrafluoroborate (11.4 mg, 0.0310 mmol), palladium(II) acetate (3.3 mg, 0.0147 mmol) and cyclopropylboronic acid (33 mg, 0.3842 mmol), then the vial was capped and heated in an oil bath set at 100° C. for 21 hours. The reaction mixture was cooled to room temperature and filtered through Celite washing with ethyl acetate (15 mL). Transferred the filtrate to a 60 mL separation funnel with saturated aqueous sodium bicarbonate (30 mL) and extracted with ethyl acetate (2×20 mL). The combined organic layers were washed with brine (~15 mL), dried over sodium sulfate, filtered and concentrated under reduced pressure. The residue was purified by silica gel chromatography (4 g column) using a gradient from 0% to 20% ethyl acetate in heptanes giving as an amber oil, (12S)-6-(benzyloxy)-18-cyclopropyl-20-nitro-6-(trifluoromethyl)-22-oxa-3,4,16,21-tetraazatetracyclo[15.3.1.12,5.012,16]docosa-1(21),2,4,9,17,19-hexaene (E/Z mixture) (69 mg, 85%). ESI-MS m/z calc. 555.20935, found 556.2 (M+1)+; Retention time: 2.47 minutes (LC Method W).

Step 2: (12R)-20-Amino-18-cyclopropyl-6-(trifluoromethyl)-22-oxa-3,4,16,21-tetraazatetracyclo[15.3.1.12,5.012,16]docosa-1(20),2,4,17(21),18-pentaen-6-ol

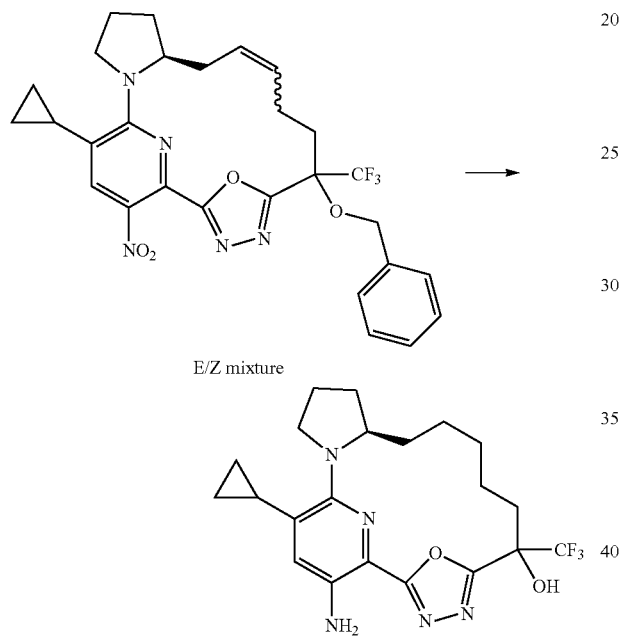

E/Z mixture

A solution of (12S)-6-(benzyloxy)-18-cyclopropyl-20-nitro-6-(trifluoromethyl)-22-oxa-3,4,16,21-tetraazatetracyclo[15.3.1.12,5.012,16]docosa-1(21),2,4,9,17,19-hexaene (E/Z mixture) (104 mg, 0.1872 mmol) in methanol (6 mL) was purged under nitrogen gas four times. Added 10% palladium on carbon (132 mg, 0.062 mmol) then purged three times under hydrogen gas. The reaction was then left to stir vigorously at room temperature for 6.5 h. Added more 10% palladium on carbon (131 mg, 0.0615 mmol) and stirred for additional 6.5 h. After purging under nitrogen gas, the reaction mixture was filtered over Celite washing with methanol (40 mL). The filtrate was concentrated under reduced pressure to afford as a fluorescent yellow foamy solid, (12R)-20-amino-18-cyclopropyl-6-(trifluoromethyl)-22-oxa-3,4,16,21-tetraazatetracyclo[15.3.1.12,5.012,16]docosa-1(20),2,4,17(21),18-pentaen-6-ol (75 mg, 82%). ESI-MS m/z calc. 437.20386, found 438.2 (M+1)+; Retention time: 2.17 minutes (LC Method E).

Step 3: (12R)-20-Amino-18-cyclopropyl-6-(trifluoromethyl)-22-oxa-3,4,16,21-tetraazatetracyclo[15.3.1.12,5.012,16]docosa-1(20),2,4,17(21),18-pentaen-6-ol (enantiomer 1) (Compound 90) and (12R)-20-amino-18-cyclopropyl-6-(trifluoromethyl)-22-oxa-3,4,16,21-tetraazatetracyclo[15.3.1.12,5.012,16]docosa-1(20),2,4,17(21),18-pentaen-6-ol (enantiomer 2) (Compound 91)

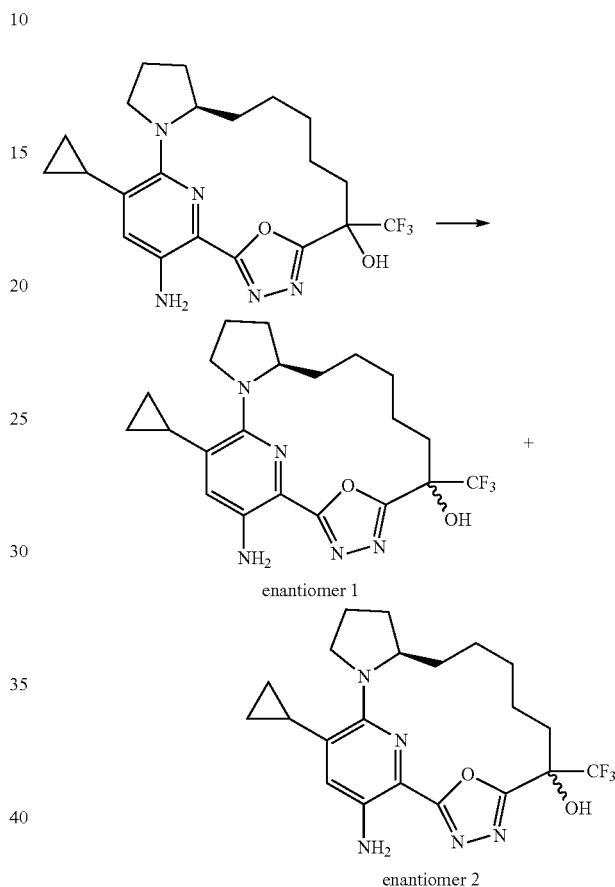

enantiomer 1 enantiomer 2

Racemic (12R)-20-Amino-18-cyclopropyl-6-(trifluoromethyl)-22-oxa-3,4,16,21-tetraazatetracyclo[15.3.1.12,5.012,16]docosa-1(20),2,4,17(21),18-pentaen-6-ol (97 mg, 0.2217 mmol) was purified by chiral SFC using an OD-H column (250×21.2 mm, 5 μm particle size) sold by Chiral Technologies eluting with a gradient from 10% to 25% MeOH (+20 mM NH₃) in CO₂ which provided two diastereomeric products:

The first diastereomer to elute was isolated as a yellow solid, (12R)-20-amino-18-cyclopropyl-6-(trifluoromethyl)-22-oxa-3,4,16,21-tetraazatetracyclo[15.3.1.12,5.012,16]docosa-1(20),2,4,17(21),18-pentaen-6-ol (enantiomer 1) (28.9 mg, 59%). ¹H NMR (400 MHz, DMSO-d6) δ 7.51 (s, 1H), 6.89 (s, 1H), 5.82 (s, 2H), 3.87 (q, J=8.0 Hz, 1H), 3.76 (d, J=7.9 Hz, 1H), 3.39 (s, 3H), 2.27 (d, J=11.4 Hz, 1H), 2.12 (d, J=7.9 Hz, 1H), 2.03-1.83 (m, 3H), 1.80-1.67 (m, 1H), 1.49 (t, J=12.4 Hz, 6H), 1.07 (q, J=9.7, 7.6 Hz, 1H), 0.99-0.88 (m, 1H), 0.87-0.69 (m, 2H), 0.62 (dd, J=9.6, 5.5 Hz, 1H) ppm. ESI-MS m/z calc. 437.20386, found 438.0 (M+1)+; Retention time: 2.1 minutes (LC Method D).

The second diastereomer to elute was isolated as a yellow solid, (12R)-20-amino-18-cyclopropyl-6-(trifluoromethyl)-22-oxa-3,4,16,21-tetraazatetracyclo[15.3.1.12,5.012,16]docosa-1(20),2,4,17(21),18-pentaen-6-ol (enantiomer 2) (29.0 mg, 60%). $^1$H NMR (400 MHz, DMSO-d6) δ 7.48 (s, 1H), 6.89 (s, 1H), 5.82 (s, 2H), 4.11-3.72 (m, 2H), 3.36 (dd, J=9.0, 3.7 Hz, 1H), 2.43-2.23 (m, 2H), 2.15 (dddd, J=11.7, 9.0, 5.9, 2.6 Hz, 1H), 2.10-1.94 (m, 2H), 1.90 (ddt, J=10.9, 7.2, 3.6 Hz, 1H), 1.83-1.58 (m, 3H), 1.58-1.28 (m, 5H), 1.09 (tdd, J=9.2, 5.9, 3.8 Hz, 1H), 1.01-0.81 (m, 2H), 0.81-0.68 (m, 1H), 0.62 (dtd, J=9.3, 5.8, 3.9 Hz, 1H) ppm. ESI-MS m/z calc. 437.20386, found 438.0 (M+1)$^+$; Retention time: 2.1 minutes (LC Method D).

Example 49: Preparation of (15R)-23-amino-8-methoxy-6,21-bis(trifluoromethyl)-26-oxa-3,4,19,24-tetraazapentacyclo[18.3.1.1²,⁵.1⁷,¹¹.0¹⁵,¹⁹] hexacosa-1(24),2,4,7(25),8,10,20,22-octaen-6-ol (enantiomer 1) (Compound 92) and (15R)-23-amino-8-methoxy-6,21-bis(trifluoromethyl)-26-oxa-3,4,19,24-tetraazapentacyclo[18.3.1.1²,⁵.1⁷,¹¹.0¹⁵,19]hexacosa-1(24),2,4,7(25),8,10,20,22-octaen-6-ol (enantiomer 2) (Compound 93)

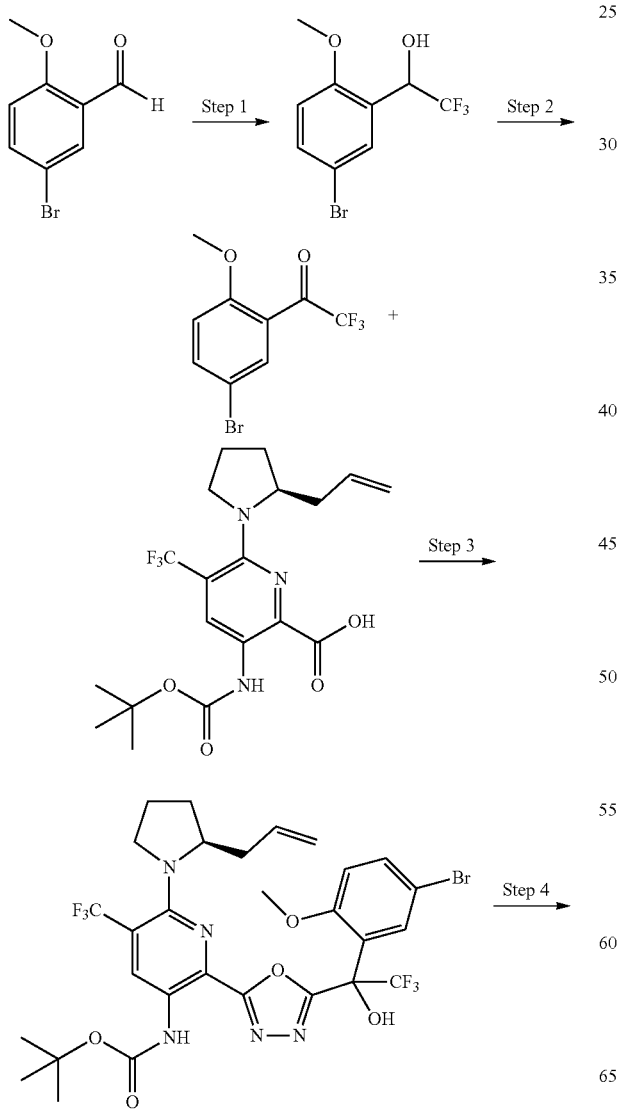

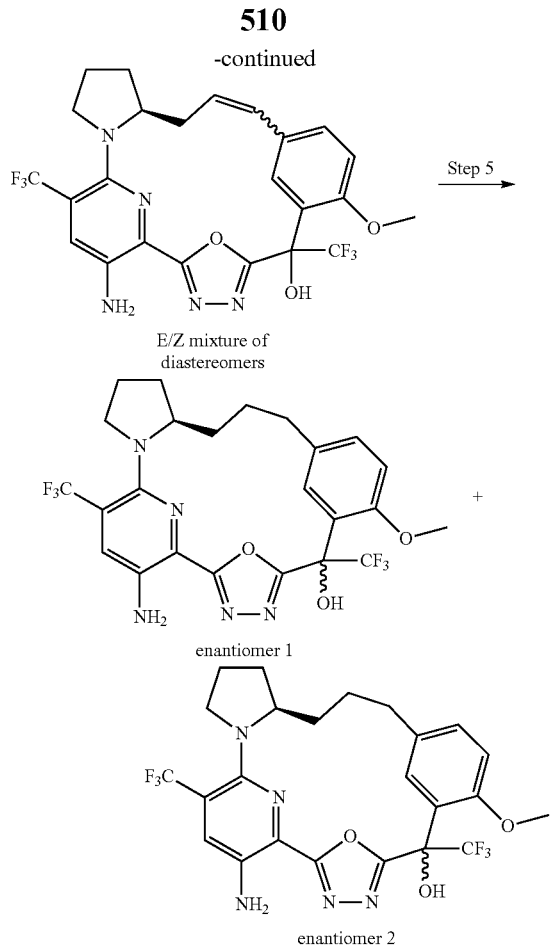

Step 1: 1-(5-Bromo-2-methoxy-phenyl)-2,2,2-trifluoro-ethanol

To an ice-cold solution of 5-bromo-2-methoxybenzaldehyde (12.0 g, 55.8 mmol) and Me$_3$SiCF$_3$ (9.9 mL, 67 mmol) in 140 mL of THF was added 22.9 mL of "Bu$_4$NF·H$_2$O (1.0 M in THF, 22.9 mmol). The golden solution was warmed to ambient temperature and stirred for 10 h. A 4.4 M aqueous solution of HCl (25.8 mL, 111.6 mmol) was slowly added. The mixture was stirred for 1 h then diluted with 30 mL of EtOAc, and solid Na$_2$CO$_3$ was cautiously added. Once effervescence had ceased, the solution was dried over MgSO$_4$, filtered and concentrated under reduced pressure to an orange oily residue. Purification of this material by chromatography on silica gel (gradient elution, 10:1 to 4:1 hexanes/EtOAc) yielded as a colorless oil, 1-(5-bromo-2-methoxy-phenyl)-2,2,2-trifluoro-ethanol (4.8 g, 30%). $^1$H NMR (400 MHz, CDCl$_3$) δ 7.47 (d, J=2.3 Hz, 1H), 7.38 (dd, J=8.8, 2.5 Hz, 1H), 6.74 (d, J=8.8 Hz, 1H), 5.22 (q, J=6.8 Hz, 1H), 3.77 (s, 3H) ppm. One exchangeable proton not observed in NMR.

Step 2: 1-(5-Bromo-2-methoxy-phenyl)-2,2,2-trifluoro-ethanone

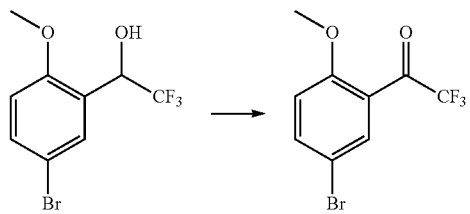

To a solution of 1-(5-bromo-2-methoxy-phenyl)-2,2,2-trifluoro-ethanol (4.8 g, 16.84 mmol) in DCM (168.4 mL) was added TEMPO (approximately 131.6 mg, 0.842 mmol) followed by PhI(OAc)₂ (approximately 10.85 g, 33.68 mmol). The reaction was stirred overnight at room temperature, then quenched with 125 mL of 1 M sodium thiosulfate solution. The mixture was separated and the aqueous layer was extracted three times with dichloromethane. The combined organics were combined and concentrated to dryness. The crude material was purified via silica chromatography eluting with a gradient from 0% to 30% EtOAc in heptane. Pure fractions were combined and concentrated to give 1-(5-bromo-2-methoxy-phenyl)-2,2,2-trifluoro-ethanone (3.8 g, 80%) which was used directly in the next step.

Step 3: tert-Butyl N-[6-[(2S)-2-allylpyrrolidin-1-yl]-2-[5-[1-(5-bromo-2-methoxy-phenyl)-2,2,2-trifluoro-1-hydroxy-ethyl]-1,3,4-oxadiazol-2-yl]-5-(trifluoromethyl)-3-pyridyl]carbamate

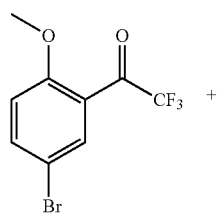

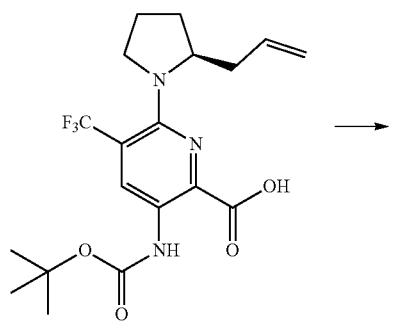

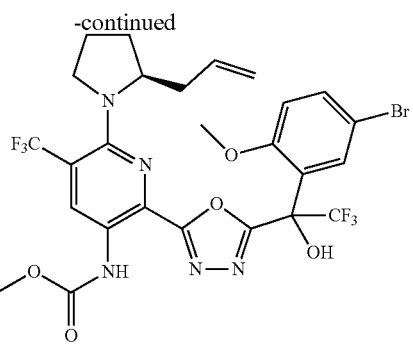

To a stirring solution of 1-(5-bromo-2-methoxy-phenyl)-2,2,2-trifluoro-ethanone (298.3 mg, 1.054 mmol) and 6-[(2S)-2-allylpyrrolidin-1-yl]-3-(tert-butoxycarbonylamino)-5-(trifluoromethyl)pyridine-2-carboxylic acid (250 mg, 0.5272 mmol) in DMF (4.38 mL) under nitrogen atmosphere at 75° C. was added (N-isocyanoimino)triphenylphosphorane (378.6 mg, 1.252 mmol) and the resulting mixture was capped and stirred 15 minutes then cooled to room temperature. Diluted the mixture with EtOAc and washed once with saturated aqueous NaHCO₃, then once with saturated aqueous NH₄Cl and once with brine. Dried the organic layer over sodium sulfate, filtered and concentrated to an orange oil. The crude orange oil was purified by reverse phase HPLC using a Luna C₁₈ column (75×30 mm, 5 μm particle size) sold by Phenomenex (pn: 00C-4252-U0-AX) and a dual gradient run from 50% to 99% mobile phase B over 15.0 minutes (mobile phase A=H₂O (5 mM HCl), mobile phase B=acetonitrile, flow rate=50 mL/min, injection volume=950 μL and column temperature=25° C.) giving as a yellow solid, tert-butyl N-[6-[(2S)-2-allylpyrrolidin-1-yl]-2-[5-[1-(5-bromo-2-methoxy-phenyl)-2,2,2-trifluoro-1-hydroxy-ethyl]-1,3,4-oxadiazol-2-yl]-5-(trifluoromethyl)-3-pyridyl]carbamate (230.7 mg, 61%). ESI-MS m/z calc. 721.1334, found 724.4 (M+1)⁺; Retention time: 0.76 minutes (LC Method T).

Step 4: (15S)-23-amino-8-methoxy-6,21-bis(trifluoromethyl)-26-oxa-3,4,19,24-tetraazapentacyclo[18.3.1.1²,⁵.1⁷,¹¹.0¹⁵,¹⁹]hexacosa-1(24),2,4,7(25),8,10,12,20,22-nonaen-6-ol (E/Z mixture of diastereomers)

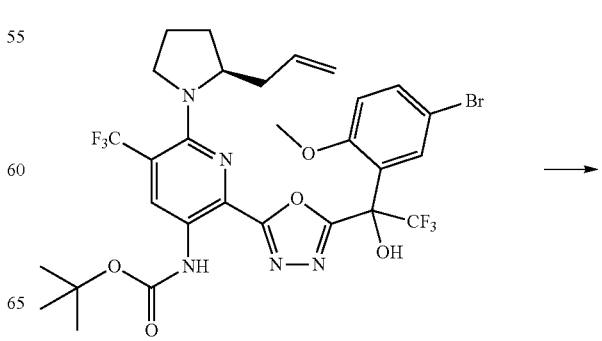

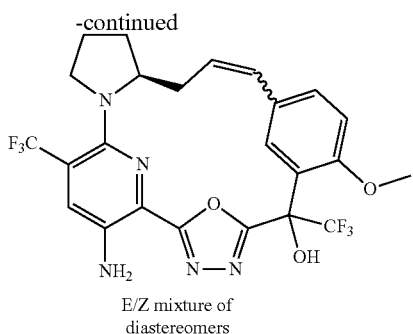

E/Z mixture of
diastereomers

To a stirred solution of tert-butyl N-[6-[(2S)-2-allylpyrrolidin-1-yl]-2-[5-[1-(5-bromo-2-methoxy-phenyl)-2,2,2-trifluoro-1-hydroxy-ethyl]-1,3,4-oxadiazol-2-yl]-5-(trifluoromethyl)-3-pyridyl]carbamate (229.6 mg, 0.3178 mmol) in acetonitrile (13.78 mL) was added diacetoxypalladium (21.4 mg, 0.09532 mmol) followed by tris-o-tolylphosphane (58.04 mg, 0.1907 mmol) and triethylamine (35.43 µL, 0.2542 mmol) and the solution was bubbled with $N_2$ for 1 min then heated by microwave irradiation at 150° C. for 2 h. Cooled the mixture to room temperature then stirred with Celite for 5 minutes and filtered over Celite eluting with EtOAc. Washed the filtrate once with saturated aqueous $NH_4Cl$ and once with brine then dried over sodium sulfate, filtered and concentrated to a yellow solid which was dissolved in DCM (2.386 mL) and stirred at room temperature. TFA (979.1 µL, 12.71 mmol) was added and the resulting solution was stirred at room temperature for 1 h. Diluted the mixture with DCM and washed with 1 N $NaHCO_3$ (caution: gas evolution), then back-extracted the aqueous phase twice with DCM. Combined the organic layers, dried over $MgSO_4$, filtered and concentrated to an orange syrup. The orange crude material was purified by silica gel chromatography using a shallow gradient from 100% hexanes to 100% EtOAc giving (15S)-23-amino-8-methoxy-6,21-bis(trifluoromethyl)-26-oxa-3,4,19,24-tetraazapentacyclo[18.3.1.12,5.17,11.015,19]hexacosa-1(24),2,4,7(25),8,10,12,20,22-nonaen-6-ol (E/Z mixture of diastereomers) (55.5 mg, 32%). ESI-MS m/z calc. 541.15485, found 542.4 (M+1)$^+$; Retention time: 0.55 minutes (LC Method T).

Step 5: (15R)-23-Amino-8-methoxy-6,21-bis(trifluoromethyl)-26-oxa-3,4,19,24-tetraazapentacyclo[18.3.1.12,5.17,11.015,19]hexacosa-1(24),2,4,7(25),8,10,20,22-octaen-6-ol (enantiomer 1) (Compound 92) and (15R)-23-amino-8-methoxy-6,21-bis(trifluoromethyl)-26-oxa-3,4,19,24-tetraazapentacyclo[18.3.1.12,5.17,11.015,19]hexacosa-1(24),2,4,7(25),8,10,20,22-octaen-6-ol (enantiomer 2) (Compound 93)

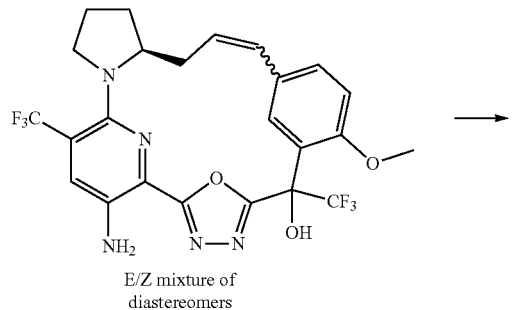

E/Z mixture of
diastereomers

→

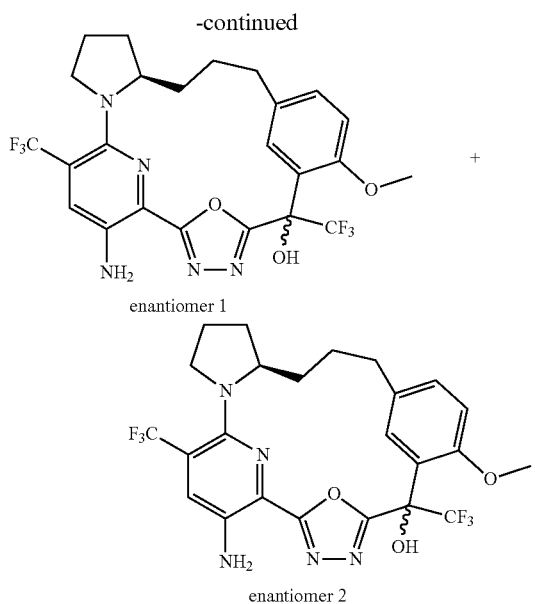

enantiomer 1

+ enantiomer 2

To a solution of (15S)-23-amino-8-methoxy-6,21-bis(trifluoromethyl)-26-oxa-3,4,19,24-tetraazapentacyclo[18.3.1.12,5.17,11.015,19]hexacosa-1(24),2,4,7(25),8,10,12,20,22-nonaen-6-ol (E/Z mixture of diastereomers) (55.5 mg, 0.1025 mmol) in ethanol (3.469 mL) was added palladium on carbon (32.72 mg of 10% w/w, 0.03075 mmol) and hydrogen was bubbled through the solution for 5 min then the flask was capped with a hydrogen balloon and stirred for 1 h. Added palladium on carbon (32.72 mg of 10% w/w, 0.03075 mmol) and continued stirring under hydrogen for 1 h. Added palladium on carbon (32.72 mg of 10% w/w, 0.03075 mmol) then stirred under 100 psi pressure of hydrogen for 50 minutes. Released pressure and backfilled with nitrogen then added Celite and stirred for 5 min then filtered over a pad of Celite eluting with methanol. The filtrate was concentrated, dissolved in DMSO then filtered. The material was purified by reverse phase HPLC using a Luna $C_{18}$ column (75×30 mm, 5 µm particle size) sold by Phenomenex (pn: 00C-4252-U0-AX) and a dual gradient run from 50% to 99% mobile phase B over 15.0 minutes (mobile phase A=$H_2O$ (5 mM HCl), mobile phase B=acetonitrile, flow rate=50 mL/min, injection volume=950 µL and column temperature=25° C.) giving two product peaks:

Peak 1 was still contaminated with a MW=541 impurity so it was further purified by silica gel chromatography using a shallow gradient from 100% hexanes to 100% EtOAc to give as a yellow solid, (15R)-23-amino-8-methoxy-6,21-bis(trifluoromethyl)-26-oxa-3,4,19,24-tetraazapentacyclo[18.3.1.12,5.17,11.015,19]hexacosa-1(24),2,4,7(25),8,10,20,22-octaen-6-ol (enantiomer 1) (6.2 mg, 17%). $^1$H NMR (400 MHz, DMSO-d6) δ 8.35 (s, 1H), 8.04 (d, J=2.2 Hz, 1H), 7.64 (s, 1H), 7.13 (dd, J=8.3, 2.2 Hz, 1H), 6.85 (d, J=8.3 Hz, 1H), 6.14 (s, 2H), 3.89-3.78 (m, 1H), 3.60 (s, 3H), 3.47 (d, J=8.1 Hz, 1H), 3.17 (t, J=8.9 Hz, 1H), 2.97 (d, J=14.6 Hz, 1H), 2.44-2.36 (m, 1H), 2.16 (dt, J=11.7, 5.6 Hz, 1H), 1.97-1.90 (m, 1H), 1.89-1.82 (m, 2H), 1.79 (d, J=6.6 Hz, 1H), 1.60 (t, J=10.3 Hz, 1H), 1.52 (dt, J=11.3, 5.5 Hz, 1H), 0.70 (dd, J=10.8, 5.2 Hz, 1H) ppm. ESI-MS m/z calc. 543.17053, found 544.4 (M+1)$^+$; Retention time: 1.09 minutes (LC Method M).

Peak 2 was isolated as a yellow solid, (15R)-23-amino-8-methoxy-6,21-bis(trifluoromethyl)-26-oxa-3,4,19,24-tetraazapentacyclo[18.3.1.1.2,5.17,11.015,19]hexacosa-1(24),2,4,7(25),8,10,20,22-octaen-6-ol (enantiomer 2) (4.7 mg, 12%). ¹H NMR (400 MHz, Chloroform-d) δ 7.66 (s, 1H), 7.64 (s, 1H), 7.61 (s, 1H), 7.20 (dd, J=8.5, 2.1 Hz, 1H), 6.98 (d, J=8.5 Hz, 1H), 6.14 (s, 2H), 3.82 (dt, J=9.5, 5.0 Hz, 1H), 3.71 (s, 3H), 3.47 (q, J=9.3, 8.7 Hz, 1H), 3.18 (t, J=8.8 Hz, 1H), 2.97-2.89 (m, 1H), 2.45 (d, J=3.0 Hz, 1H), 2.15 (dt, J=12.0, 5.9 Hz, 1H), 1.96 (dt, J=7.9, 4.0 Hz, 1H), 1.85 (q, J=5.9 Hz, 2H), 1.66 (t, J=12.5 Hz, 2H), 1.52 (dt, J=11.2, 5.7 Hz, 1H), 0.73 (dq, J=11.1, 6.0 Hz, 1H) ppm. ESI-MS m/z calc. 543.17053, found 544.4 (M+1)⁺; Retention time: 1.28 minutes (LC Method M).

Example 50: Preparation of ethyl 17-amino-6-hydroxy-6,15-bis(trifluoromethyl)-19-oxa-3,4,13,18-tetrazatricyclo[12.3.1.1.2,5]nonadeca-1(18),2,4,14,16-pentaene-12-carboxylate (enantiomer 1) (Compound 94), ethyl 17-amino-6-hydroxy-6,15-bis(trifluoromethyl)-19-oxa-3,4,13,18-tetrazatricyclo[12.3.1.1.2,5]nonadeca-1(18),2,4,14,16-pentaene-12-carboxylate (enantiomer 2) (Compound 95), ethyl 17-amino-6-hydroxy-6,15-bis(trifluoromethyl)-19-oxa-3,4,13,18-tetrazatricyclo[12.3.1.1.2,5]nonadeca-1(18),2,4,14,16-pentaene-12-carboxylate (enantiomer 3) (Compound 96) and ethyl 17-amino-6-hydroxy-6,15-bis(trifluoromethyl)-19-oxa-3,4,13,18-tetrazatricyclo[12.3.1.1.2,5]nonadeca-1(18),2,4,14,16-pentaene-12-carboxylate (enantiomer 4) (Compound 97)

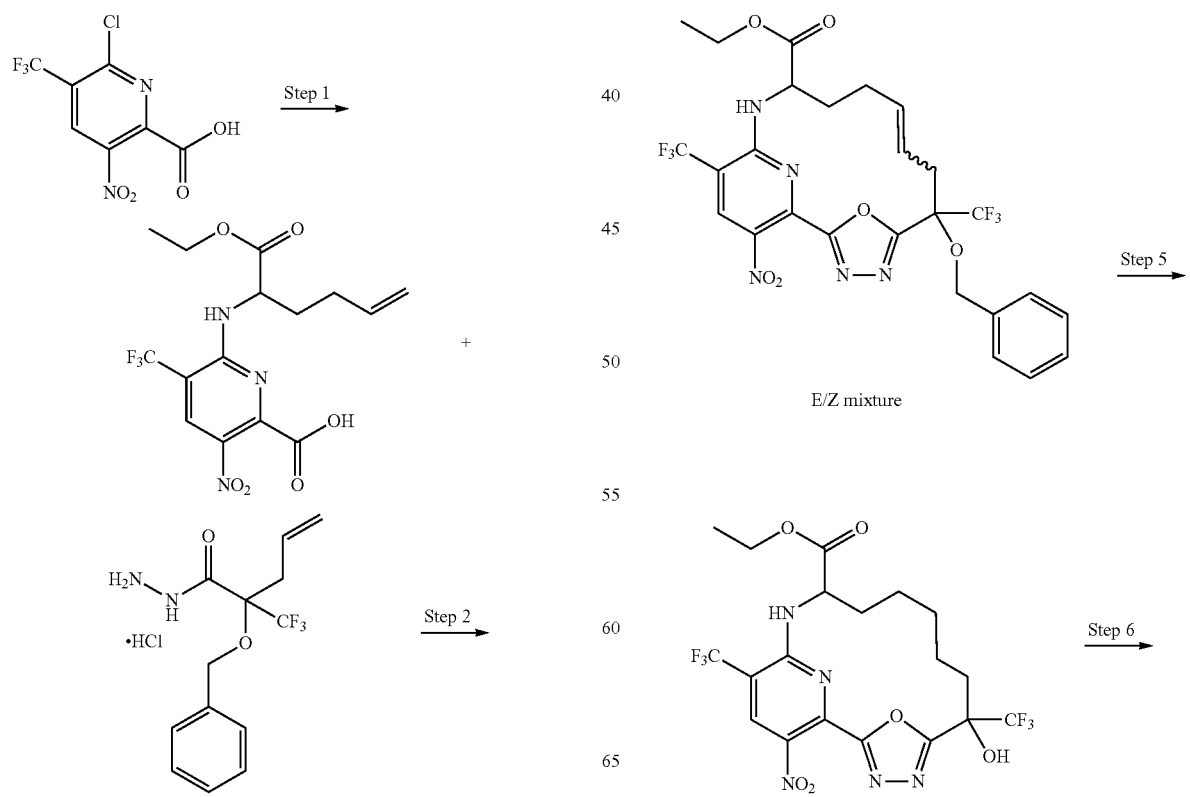

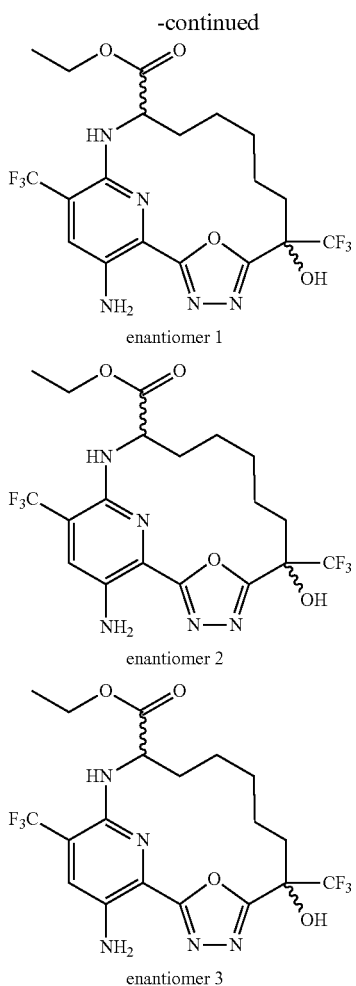

enantiomer 1 enantiomer 2 enantiomer 3 enantiomer 4

Step 1: 6-(1-Ethoxycarbonylpent-4-enylamino)-3-nitro-5-(trifluoromethyl)pyridine-2-carboxylic Acid

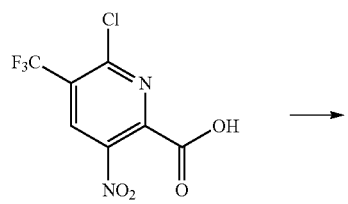

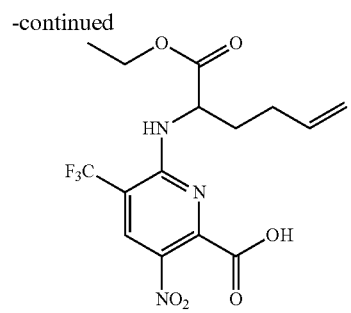

In a 20 mL sealed vial, 6-chloro-3-nitro-5-(trifluoromethyl)pyridine-2-carboxylic acid (725 mg, 2.68 mmol) was dissolved in acetonitrile (7.25 mL) and DMSO (7.25 mL) at room temperature followed by addition of DIEA (2.75 mL, 15.79 mmol) and ethyl 2-aminohex-5-enoate (850 mg, 5.407 mmol) and then the mixture was stirred for 18 h. The reaction was concentrated and the crude material was then purified by silica gel chromatography using a gradient from 100% hexanes to 100% ethyl acetate followed by 100% DCM to 20% methanol in DCM to afford as a dark orange foam, 6-(1-ethoxycarbonylpent-4-enylamino)-3-nitro-5-(trifluoromethyl)pyridine-2-carboxylic acid (757 mg, 72%). $^1$H NMR (400 MHz, DMSO-d6) δ 14.20 (s, 1H), 8.51 (s, 1H), 8.07 (d, J=7.1 Hz, 1H), 5.80 (ddt, J=16.6, 10.4, 6.1 Hz, 1H), 5.04-4.93 (m, 2H), 4.64 (ddd, J=9.1, 7.0, 4.2 Hz, 1H), 4.09 (qd, J 7.1, 2.3 Hz, 2H), 2.19-2.08 (m, 2H), 2.08-1.91 (m, 2H), 1.15 (t, J 7.1 Hz, 3H) ppm. ESI-MS m/z calc. 391.09912, found 392.2 (M+1)$^+$; Retention time: 1.53 minutes (LC Method A).

Step 2: Ethyl 2-[[6-[[[2-benzyloxy-2-(trifluoromethyl)pent-4-enoyl]amino]carbamoyl]-5-nitro-3-(trifluoromethyl)-2-pyridyl]amino]hex-5-enoate

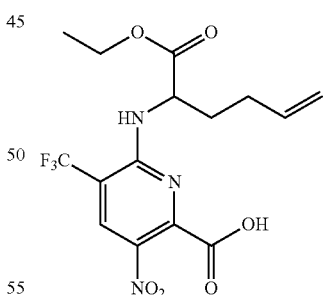

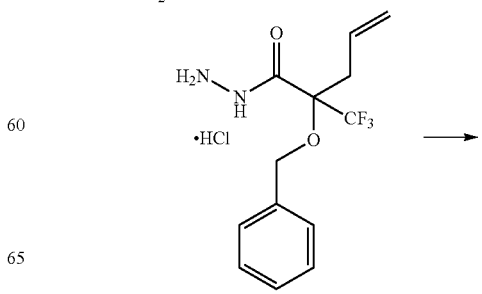

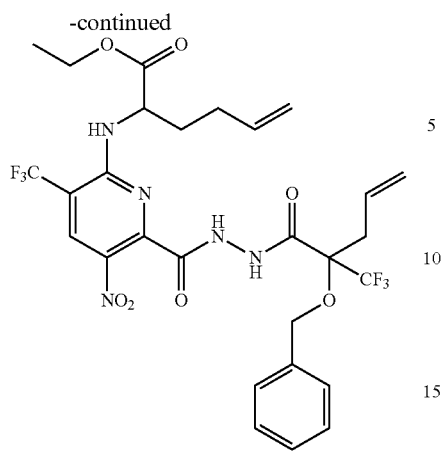

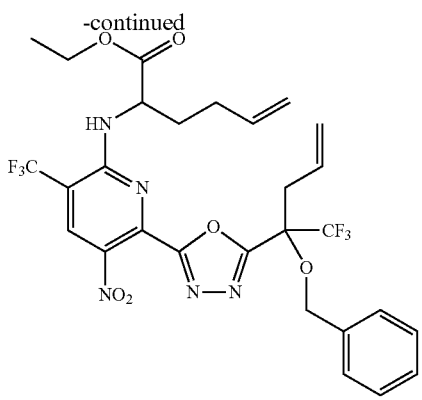

To a solution of 6-(1-ethoxycarbonylpent-4-enylamino)-3-nitro-5-(trifluoromethyl)pyridine-2-carboxylic acid (52 mg, 0.1329 mmol) in NMP (3.5 mL) cooled to 0° C. was added 2-benzyloxy-2-(trifluoromethyl)pent-4-enehydrazide (hydrochloride salt) (53 mg, 0.1632 mmol) followed by HATU (65 mg, 0.1709 mmol). Then, DIEA (150 µL, 0.8612 mmol) was added and the reaction mixture was stirred allowing to warm to room temperature for 18 h. The reaction was diluted with ethyl acetate and washed with brine. The organic layer was further washed with 10% citric acid solution followed by brine. The organics were separated, dried over sodium sulfate, filtered and evaporated. The crude material was then purified by silica gel chromatography using a gradient from 100% DCM to 20% methanol in DCM to afford as a yellow foam, ethyl 2-[[6-[[[2-benzyloxy-2-(trifluoromethyl)pent-4-enoyl]amino]carbamoyl]-5-nitro-3-(trifluoromethyl)-2-pyridyl]amino]hex-5-enoate (42.6 mg, 48%). ESI-MS m/z calc. 661.19714, found 662.2 (M+1)$^+$; Retention time: 1.57 minutes (LC Method J).

Step 3: Ethyl 2-[[6-[5-[1-benzyloxy-1-(trifluoromethyl)but-3-enyl]-1,3,4-oxadiazol-2-yl]-5-nitro-3-(trifluoromethyl)-2-pyridyl]amino]hex-5-enoate A solution of ethyl 2-[[6-[[[2-benzyloxy-2-(trifluoromethyl)pent-4-enoyl]amino]carbamoyl]-5-nitro-3-(trifluoromethyl)-2-pyridyl]amino]hex-5-enoate (573 mg, 0.8661 mmol) and DIEA (500 µL, 2.871 mmol) in acetonitrile (18 mL) was heated to 50° C., then p-toluenesulfonyl chloride (250 mg, 1.311 mmol) was added in one portion. The resulted mixture was heated at 70° C. for 90 minutes. The reaction mixture was cooled and quenched with a saturated aqueous solution of sodium bicarbonate (50 mL) and stirred for 15 minutes. Then the organic material was extracted with ethyl acetate (3×50 mL). The organics were dried over sodium sulfate, filtered and evaporated. The crude material was then purified by silica gel chromatography using a gradient from 100% hexanes to 40% ethyl acetate in hexanes to afford as a yellow solid, ethyl 2-[[6-[5-[1-benzyloxy-1-(trifluoromethyl)but-3-enyl]-1,3,4-oxadiazol-2-yl]-5-nitro-3-(trifluoromethyl)-2-pyridyl]amino]hex-5-enoate (400 mg, 72%). $^1$H NMR (400 MHz, DMSO-d6) δ 8.64 (s, 1H), 8.31 (t, J=7.3 Hz, 1H), 7.35 (d, J=3.5 Hz, 5H), 5.94-5.72 (m, 2H), 5.38 (dt, J=17.1, 1.6 Hz, 1H), 5.25 (dt, J=10.4, 1.5 Hz, 1H), 4.99-4.89 (m, 2H), 4.80 (d, J=10.6 Hz, 1H), 4.63 (td, J=9.4, 8.9, 2.7 Hz, 1H), 4.53 (dd, J=10.5, 1.6 Hz, 1H), 4.02 (q, J=7.1 Hz, 2H), 3.31 (s, 1H), 2.49-2.45 (m, 1H), 2.10 (td, J=9.4, 7.7, 4.9 Hz, 3H), 2.03-1.94 (m, 1H), 1.04 (td, J=7.1, 2.2 Hz, 3H) ppm. ESI-MS m/z calc. 643.1865, found 644.2 (M+1)$^+$; Retention time: 1.92 minutes (LC Method J).

Step 4: Ethyl 6-benzyloxy-17-nitro-6,15-bis(trifluoromethyl)-19-oxa-3,4,13,18-tetrazatricyclo[12.3.1.1²,⁵]nonadeca-1(18),2,4,8,14,16-hexaene-12-carboxylate (E/Z mixture)

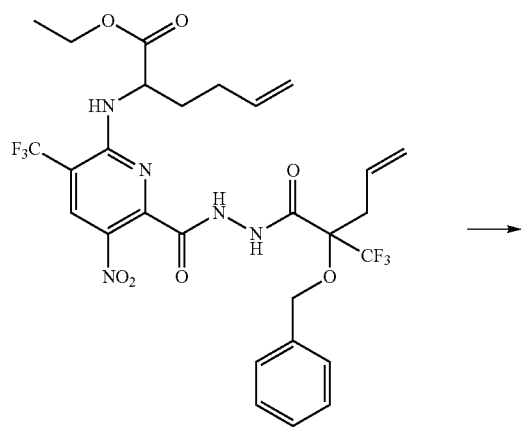

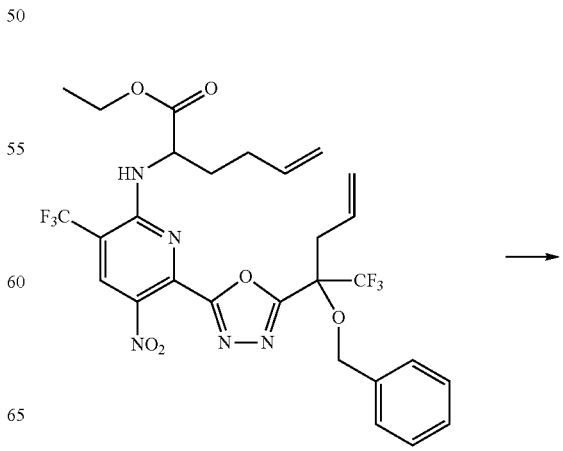

-continued

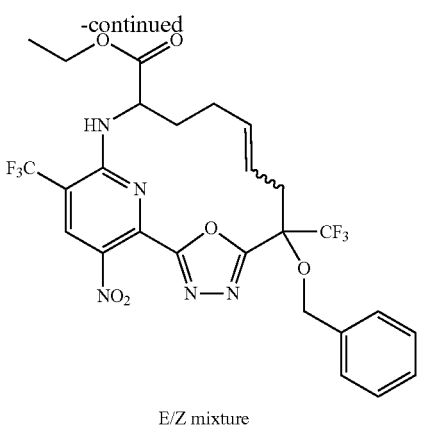

E/Z mixture

In a 250 mL round bottom flask, a continuously degassed solution via nitrogen line of Zhan 1B (110 mg, 0.1499 mmol) was dissolved in DCE (200 mL) and the mixture was heated to 50° C. under nitrogen atmosphere. Then, a solution of ethyl 2-[[6-[5-[1-benzyloxy-1-(trifluoromethyl)but-3-enyl]-1,3,4-oxadiazol-2-yl]-5-nitro-3-(trifluoromethyl)-2-pyridyl]amino]hex-5-enoate (400 mg, 0.6216 mmol) in DCE (10 mL) was added via syringe. The resulting mixture was heated at 75° C. for 2 hrs. The residue was concentrated and purified by silica gel chromatography using a gradient from 100% hexanes to 50% ethyl acetate in hexanes to afford as an off-white solid, ethyl 6-benzyloxy-17-nitro-6,15-bis(trifluoromethyl)-19-oxa-3,4,13,18-tetrazatricyclo[12.3.1.1 2,5]nonadeca-1(18),2,4,8,14,16-hexaene-12-carboxylate (E/Z mixture) (315 mg, 82%). ESI-MS m/z calc. 615.1553, found 616.2 (M+1)⁺; Retention time: 1.82 minutes (LC Method J).

Step 5: Ethyl 17-amino-6-hydroxy-6,15-bis(trifluoromethyl)-19-oxa-3,4,13,18-tetrazatricyclo[12.3.1.1 2,5]nonadeca-1(18),2,4,14,16-pentaene-12-carboxylate

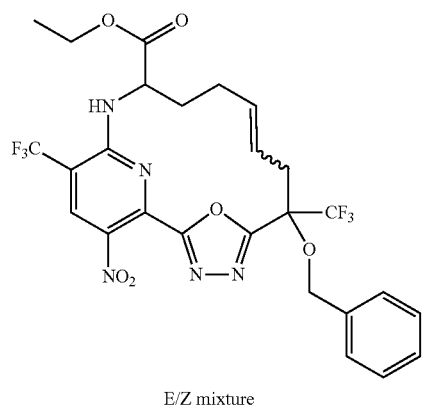

E/Z mixture

-continued

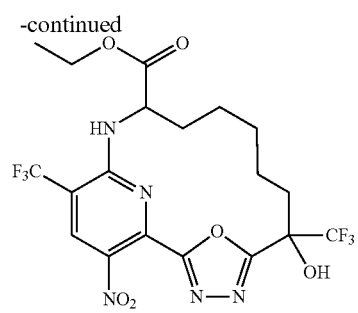

In a 50 mL round bottom flask, a solution of ethyl 6-benzyloxy-17-nitro-6,15-bis(trifluoromethyl)-19-oxa-3,4,13,18-tetrazatricyclo[12.3.1.1 2,5]nonadeca-1(18),2,4,8,14,16-hexaene-12-carboxylate (E/Z mixture) (45 mg, 0.07311 mmol) in AcOH (780 μL) and ethyl acetate (800 μL) was purged with nitrogen. Then Pd/C (78 mg of 10% w/w, 0.07329 mmol) was added. The mixture was degassed with nitrogen then purged by a balloon filled with hydrogen gas. The mixture was stirred at 1 atmosphere of hydrogen for 4 h. The reaction was filtered and the material was purified by silica gel chromatography using a gradient from 100% hexanes to 70% ethyl acetate in hexanes to afford as a yellow solid, ethyl 17-amino-6-hydroxy-6,15-bis(trifluoromethyl)-19-oxa-3,4,13,18-tetrazatricyclo[12.3.1.1 2,5]nonadeca-1(18),2,4,14,16-pentaene-12-carboxylate (32 mg, 88%). ¹H NMR (400 MHz, DMSO-d6) δ 7.68 (d, J=1.7 Hz, 1H), 7.58 (d, J=3.4 Hz, 1H), 6.15 (d, J=6.7 Hz, 2H), 5.60 (t, J=5.1 Hz, 1H), 4.45-4.29 (m, 1H), 4.22 (dddd, J=17.9, 10.8, 7.1, 3.7 Hz, 2H), 2.29 (ddt, J=24.4, 14.2, 8.1 Hz, 2H), 2.14-2.02 (m, 1H), 1.81 (dt, J=13.9, 7.7 Hz, 1H), 1.62 (s, 3H), 1.43 (dt, J=20.9, 7.9 Hz, 3H), 1.25 (t, J=7.1 Hz, 3H) ppm. ESI-MS m/z calc. 497.14978, found 498.2 (M+1)⁺; Retention time: 1.32 minutes (LC Method J).

Step 6: Ethyl 17-amino-6-hydroxy-6,15-bis(trifluoromethyl)-19-oxa-3,4,13,18-tetrazatricyclo[12.3.1.1 2,5]nonadeca-1(18),2,4,14,16-pentaene-12-carboxylate (enantiomer 1) (Compound 94), ethyl 17-amino-6-hydroxy-6,15-bis(trifluoromethyl)-19-oxa-3,4,13,18-tetrazatricyclo[12.3.1.1 2,5]nonadeca-1(18),2,4,14,16-pentaene-12-carboxylate (enantiomer 2) (Compound 95), ethyl 17-amino-6-hydroxy-6,15-bis(trifluoromethyl)-19-oxa-3,4,13,18-tetrazatricyclo[12.3.1.1 2,5]nonadeca-1(18),2,4,14,16-pentaene-12-carboxylate (enantiomer 3) (Compound 96), and ethyl 17-amino-6-hydroxy-6,15-bis(trifluoromethyl)-19-oxa-3,4,13,18-tetrazatricyclo[12.3.1.1 2,5]nonadeca-1(18),2,4,14,16-pentaene-12-carboxylate (enantiomer 4) (Compound 97)

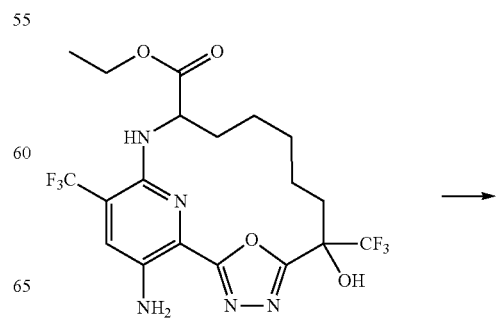

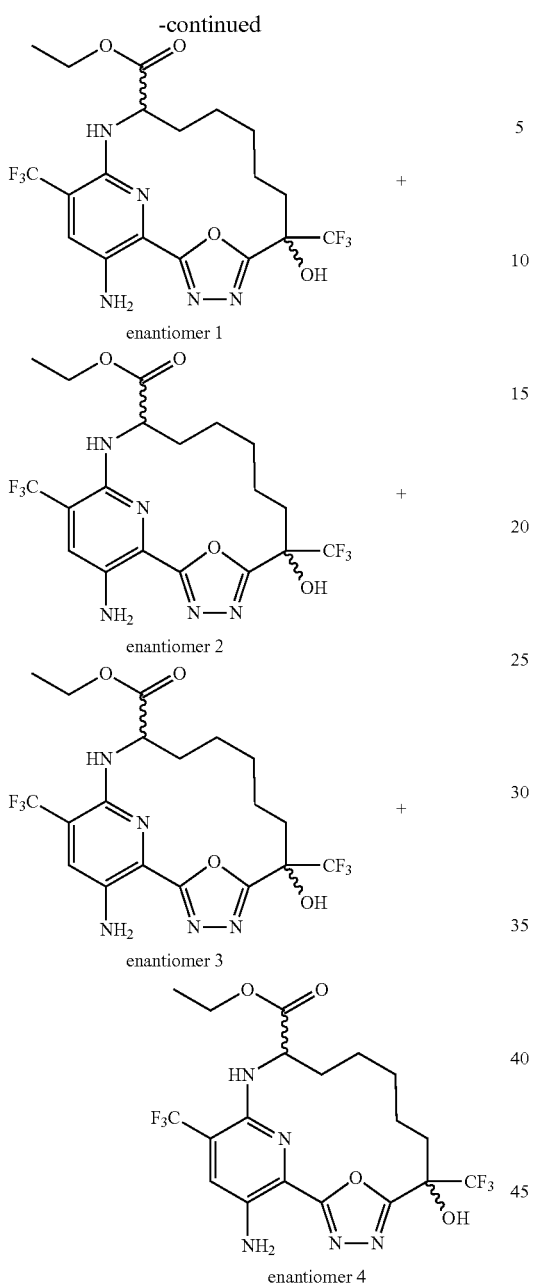

enantiomer 1 enantiomer 2 enantiomer 3 enantiomer 4

Racemic ethyl 17-amino-6-hydroxy-6,15-bis(trifluoromethyl)-19-oxa-3,4,13,18-tetrazatricyclo[12.3.1.1²,⁵]nonadeca-1(18),2,4,14,16-pentaene-12-carboxylate (32 mg, 0.06434 mmol) was purified to isolate three separate fractions (enantiomer 1, enantiomers 2 & 3 eluting together, and enantiomer 4) by normal phase SFC using an IC column (250×10 mm, 5 μm particle size) sold by Chiral Technologies (pn: 83445) and an isocratic run of 12% MeOH [+20 mM $NH_3$]/88% $CO_2$ at a flow rate of 10 mL/min (injection volume=70 μL of a 22 mg/mL concentration in MeOH with no modifier, column temperature=40° C.). Then enantiomers 2 & 3 were separated by normal phase SFC using a LUX-4 column (250×10 mm, 5 μm particle size) sold by Phenomenex (pn: 00G-4491-PO-AX) and an isocratic run of 10% MeOH [+20 mM $NH_3$]/90% $CO_2$ at a flow rate of 10 mL/min (injection volume=70 μL of a 12 mg/mL concentration in MeOH with no modifier, column temperature=40° C.). The four individual enantiomers were isolated from these two SFC purifications:

Enantiomer 1: Yellow solid, ethyl 17-amino-6-hydroxy-6,15-bis(trifluoromethyl)-19-oxa-3,4,13,18-tetrazatricyclo[12.3.1.1²,⁵]nonadeca-1(18),2,4,14,16-pentaene-12-carboxylate (enantiomer 1) (3.1 mg, 38%). ¹H NMR (400 MHz, Chloroform-d) δ 7.34 (s, 1H), 5.77-5.63 (m, 1H), 4.43 (dd, J=9.4, 3.9 Hz, 1H), 4.30 (qd, J=7.1, 5.2 Hz, 2H), 3.74 (d, J=51.8 Hz, 2H), 3.50 (s, 1H), 2.50-2.40 (m, 2H), 2.21-2.12 (m, 1H), 1.85 (ddt, J=10.4, 6.9, 3.6 Hz, 1H), 1.77-1.65 (m, 3H), 1.53-1.40 (m, 3H), 1.36 (t, J=7.1 Hz, 3H) ppm. ESI-MS m/z calc. 497.14978, found 498.1 (M+1)⁺; Retention time: 1.92 minutes (LC Method A).

Enantiomer 2: Yellow solid, ethyl 17-amino-6-hydroxy-6,15-bis(trifluoromethyl)-19-oxa-3,4,13,18-tetrazatricyclo[12.3.1.1²,⁵]nonadeca-1(18),2,4,14,16-pentaene-12-carboxylate (enantiomer 2) (1.2 mg, 15%). ESI-MS m/z calc. 497.14978, found 498.2 (M+1)⁺; Retention time: 1.93 minutes (LC Method A).

Enantiomer 3: Yellow solid, ethyl 17-amino-6-hydroxy-6,15-bis(trifluoromethyl)-19-oxa-3,4,13,18-tetrazatricyclo[12.3.1.1²,⁵]nonadeca-1(18),2,4,14,16-pentaene-12-carboxylate (enantiomer 3) (1.5 mg, 19%). ESI-MS m/z calc. 497.14978, found 498.1 (M+1)⁺; Retention time: 1.92 minutes (LC Method A).

Enantiomer 4: Yellow solid, ethyl 17-amino-6-hydroxy-6,15-bis(trifluoromethyl)-19-oxa-3,4,13,18-tetrazatricyclo[12.3.1.1²,⁵]nonadeca-1(18),2,4,14,16-pentaene-12-carboxylate (enantiomer 4) (3.1 mg, 38%). ¹H NMR (400 MHz, Chloroform-d) δ 7.42-7.32 (m, 1H), 5.65 (d, J=3.9 Hz, 1H), 5.07 (s, 2H), 4.39 (dt, J=9.7, 3.5 Hz, 1H), 4.34-4.22 (m, 2H), 3.77 (s, 1H), 2.51 (ddt, J=10.5, 7.4, 3.1 Hz, 1H), 2.36 (t, J=12.4 Hz, 1H), 2.30-2.20 (m, 1H), 2.03-1.89 (m, 1H), 1.75 (ddt, J=17.9, 12.0, 6.0 Hz, 3H), 1.58-1.45 (m, 3H), 1.34 (t, J=7.1 Hz, 3H) ppm. ESI-MS m/z calc. 497.14978, found 498.1 (M+1)⁺; Retention time: 1.93 minutes (LC Method A).

Example 51: Preparation of (12R)-20-amino-18-(dimethylphosphoryl)-6-(trifluoromethyl)-22-oxa-3,4,16,21-tetraazatetracyclo[15.3.1.1²,⁵.0¹²,¹⁶]docosa-1(21),2,4,17,19-pentaen-6-ol (enantiomer 1) (Compound 98) and (12R)-20-amino-18-(dimethylphosphoryl)-6-(trifluoromethyl)-22-oxa-3,4,16,21-tetraazatetracyclo[15.3.1.1²,⁵.0¹²,¹⁶]docosa-1(21),2,4,17,19-pentaen-6-ol (enantiomer 2) (Compound 99)

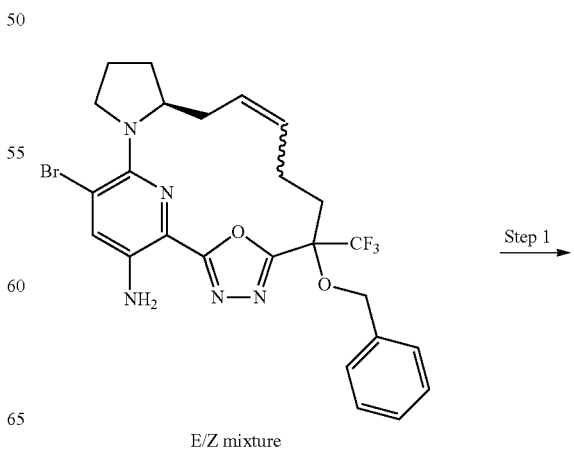

E/Z mixture

Step 1 →

525

-continued

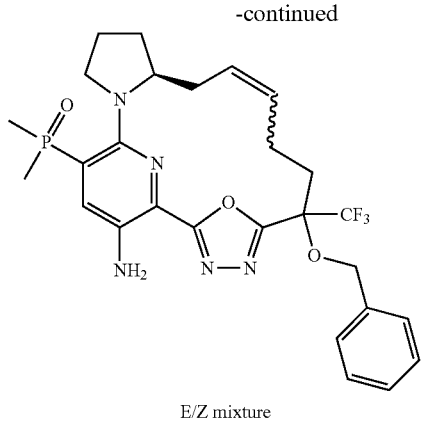

E/Z mixture

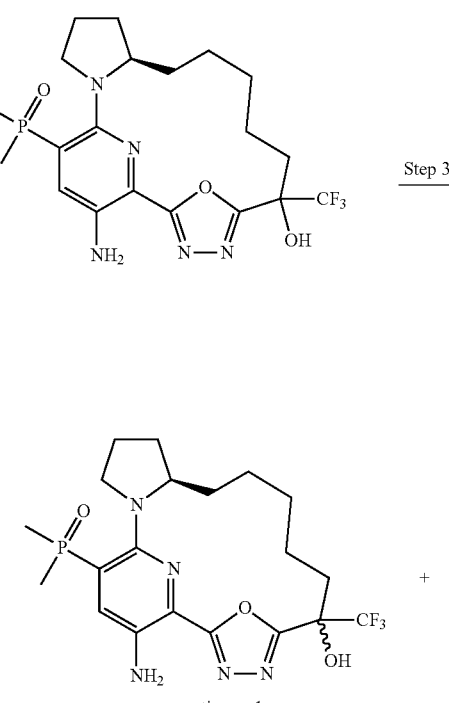

Step 3 enantiomer 1

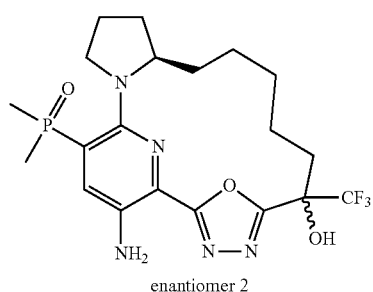

enantiomer 2

526

Step 1: (12S)-6-(Benzyloxy)-18-(dimethylphosphoryl)-20-amino-6-(trifluoromethyl)-22-oxa-3,4,16,21-tetraazatetracyclo[15.3.1.12,5.012,16]docosa-1(21),2,4,9,17,19-hexaene (E/Z Mixture)

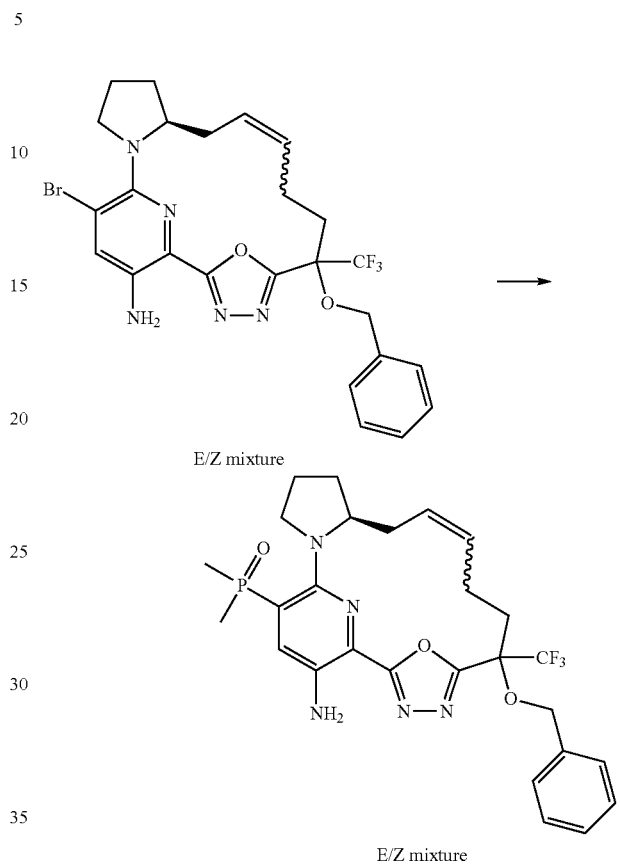

To a suspension of (12S)-6-(benzyloxy)-18-bromo-6-(trifluoromethyl)-22-oxa-3,4,16,21-tetraazatetracyclo[15.3.1.12,5.012,16]docosa-1(21),2,4,9,17,19-hexaen-20-amine (E/Z mixture) (120 mg, 0.2126 mmol), dimethylphosphine oxide (50 mg, 0.6406 mmol), Xantphos (13 mg, 0.0225 mmol) and potassium phosphate tribasic (160 mg, 0.7538 mmol) in degassed N,N-dimethylformamide (2 mL) was added palladium(II) acetate (5 mg, 0.0223 mmol). The mixture was heated to 120° C. overnight. After cooling to room temperature, the mixture was diluted with ethyl acetate (10 mL) and filtered through Celite. The filtrate was concentrated under reduced pressure and diluted with dimethyl sulfoxide (3 mL). The resulting mixture was purified by reverse phase HPLC using a gradient from 5% to 90% acetonitrile in water (+0.1% formic acid) giving as a yellow foam, (12S)-6-(benzyloxy)-18-(dimethylphosphoryl)-20-amino-6-(trifluoromethyl)-22-oxa-3,4,16,21-tetraazatetracyclo[15.3.1.12,5.012,16]docosa-1(21),2,4,9,17,19-hexaene (E/Z mixture) (20 mg, 17%). ESI-MS m/z calc. 561.2117, found 562.2 (M+1)⁺; Retention time: 2.32 minutes (LC Method W).

Step 2: (12R)-20-Amino-18-(dimethylphosphoryl)-6-(trifluoromethyl)-22-oxa-3,4,16,21-tetraazatetracyclo[15.3.1.1²,⁵.0¹²,¹⁶]docosa-1(21),2,4,17,19-pentaen-6-ol

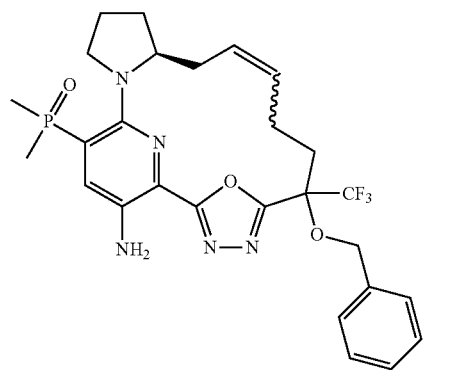

E/Z mixture

A solution of (12S)-6-(benzyloxy)-18-(dimethylphosphoryl)-20-amino-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (20 mg, 0.0338 mmol) in methanol (1 mL) was bubbled with nitrogen for 5 min and then 5% palladium on carbon (22 mg, 0.0103 mmol) was added. The resulting mixture was bubbled with a balloon of hydrogen for 5 min and then stirred at room temperature under hydrogen overnight. The mixture was filtered through a pad of Celite washing with methanol (25 mL) and the filtrate was concentrated under reduced pressure. The resulting mixture was purified by reverse phase HPLC using a gradient from 5% to 95% acetonitrile in water (+0.1% formic acid) giving as a yellow solid, (12R)-20-amino-18-(dimethylphosphoryl)-6-(trifluoromethyl)-22-oxa-3,4,16,21-tetraazatetracyclo[15.3.1.1²,⁵.0¹²,¹⁶]docosa-1(21),2,4,17,19-pentaen-6-ol (9 mg, 50%). ESI-MS m/z calc. 473.1804, found 474.2 (M+1)⁺; Retention time: 3.08 minutes (LC Method C).

Step 3: (12R)-20-Amino-18-(dimethylphosphoryl)-6-(trifluoromethyl)-22-oxa-3,4,16,21-tetraazatetracyclo[15.3.1.1²,⁵.0¹²,¹⁶]docosa-1(21),2,4,17,19-pentaen-6-ol (enantiomer 1) (Compound 98) and (12R)-20-amino-18-(dimethylphosphoryl)-6-(trifluoromethyl)-22-oxa-3,4,16,21-tetraazatetracyclo[15.3.1.1²,⁵.0¹²,¹⁶]docosa-1(21),2,4,17,19-pentaen-6-ol (enantiomer 2) (Compound 99)

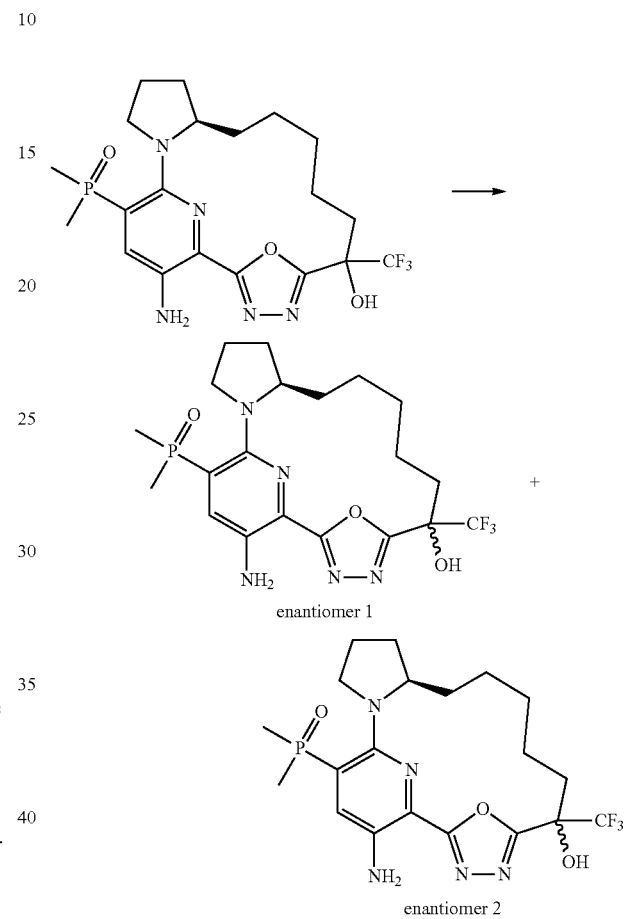

(12R)-20-Amino-18-(dimethylphosphoryl)-6-(trifluoromethyl)-22-oxa-3,4,16,21-tetraazatetracyclo[15.3.1.1²,⁵.0¹²,¹⁶]docosa-1(21),2,4,17,19-pentaen-6-ol (8.2 mg, 0.01732 mmol) was purified by SFC using a LUX-4 column (250×21.2 mm, 5 μm particle size) sold by Phenomenex and eluting with a gradient from 30% to 50% MeOH (+20 mM NH₃) in CO₂ which provided two single enantiomer products:

The first enantiomer to elute was isolated as a yellow solid, (12R)-20-amino-18-(dimethylphosphoryl)-6-(trifluoromethyl)-22-oxa-3,4,16,21-tetraazatetracyclo[15.3.1.12, 5.0¹²,¹⁶]docosa-1(21),2,4,17,19-pentaen-6-ol (enantiomer 1) (2.7 mg, 33%). ESI-MS m/z calc. 473.18036, found 474.0 (M+1)⁺; Retention time: 2.33 minutes (LC Method A).

The second enantiomer to elute was isolated as a yellow solid, (12R)-20-amino-18-(dimethylphosphoryl)-6-(trifluoromethyl)-22-oxa-3,4,16,21-tetraazatetracyclo[15.3.1.12, 5.0¹²,¹⁶]docosa-1(21),2,4,17,19-pentaen-6-ol (enantiomer 2) (0.9 mg, 11%). ESI-MS m/z calc. 473.18036, found 474.0 (M+1)⁺; Retention time: 2.31 minutes (LC Method A).

Example 52: Preparation of (12R)-20-amino-6-(hydroxymethyl)-18-(trifluoromethyl)-22-oxa-3,4,16,21-tetraazatetracyclo[15.3.1.1²,⁵.0¹²,¹⁶]docosa-1(20),2,4,17(21),18-pentaen-6-ol (enantiomer 1) (Compound 100) and (12R)-20-amino-6-(hydroxymethyl)-18-(trifluoromethyl)-22-oxa-3,4,16,21-tetraazatetracyclo[15.3.1.1²,⁵.0¹²,¹⁶]docosa-1(20),2,4,17(21),18-pentaen-6-ol (enantiomer 2) (Compound 101)
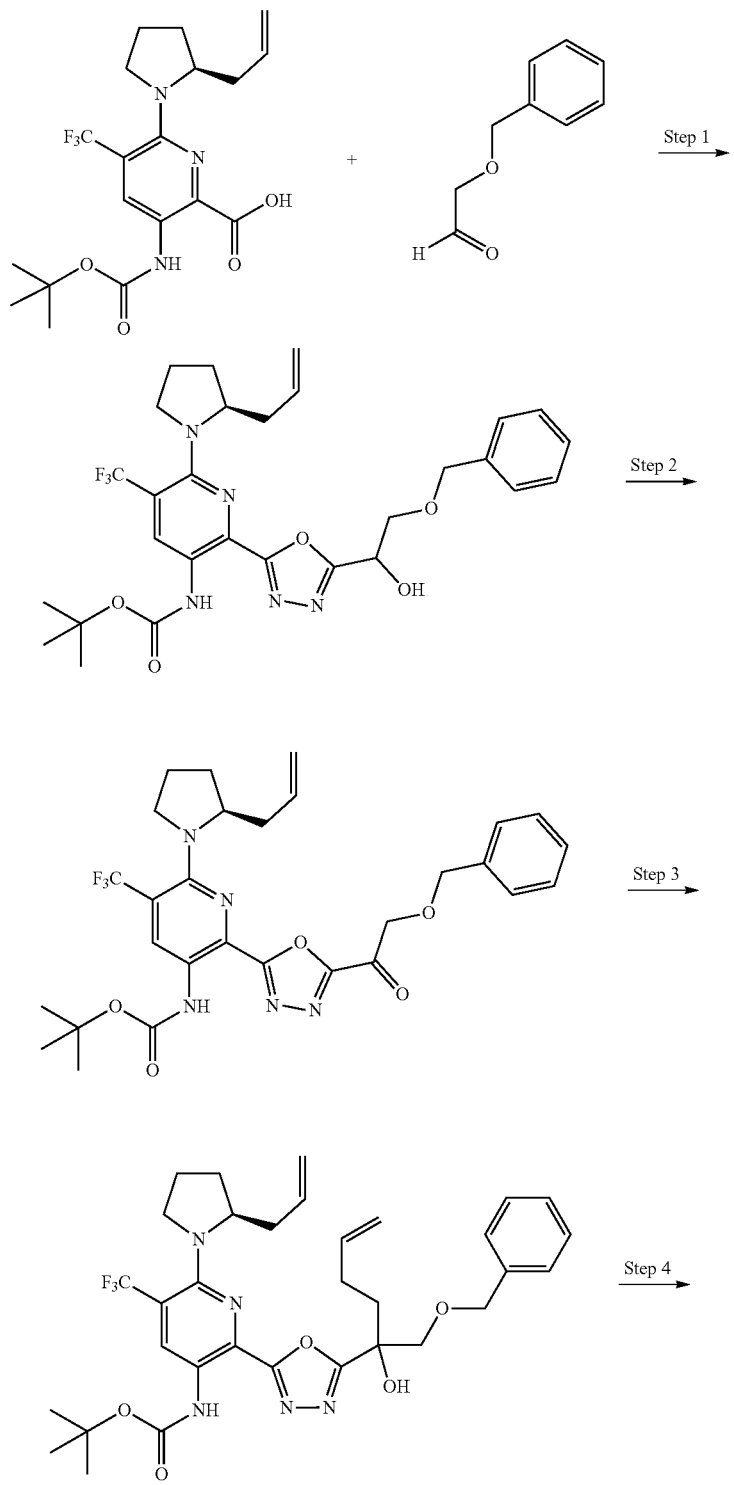

531
532
-continued
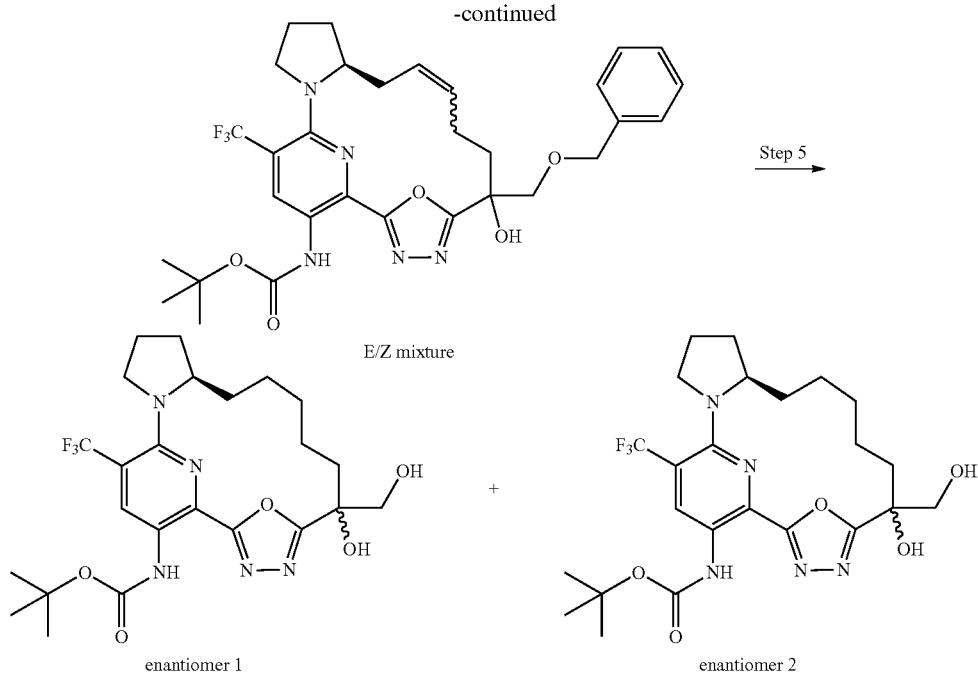
E/Z mixture
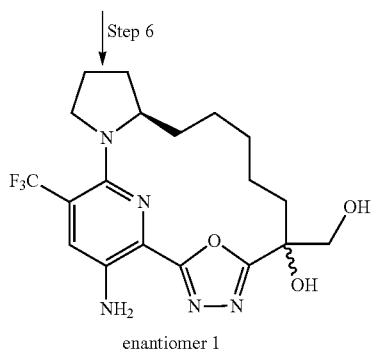
enantiomer 1
+
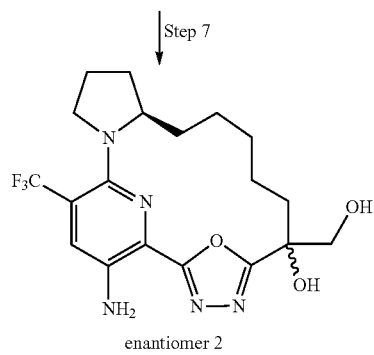
enantiomer 2
Step 6 ↓
Step 7 ↓
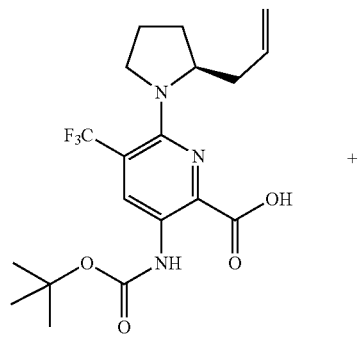
enantiomer 1
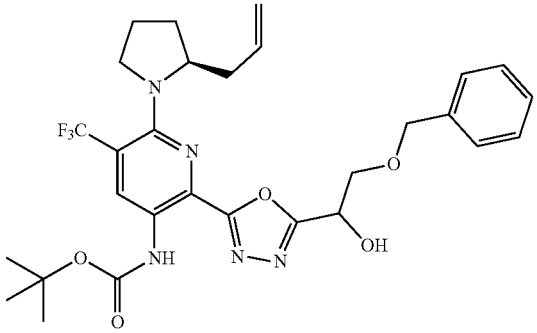
enantiomer 2
Step 1: tert-Butyl N-[6-[(2S)-2-allylpyrrolidin-1-yl]-2-[5-(2-benzyloxy-1-hydroxy-ethyl)-1,3,4-oxadiazol-2-yl]-5-(trifluoromethyl)-3-pyridyl]carbamate
-continued
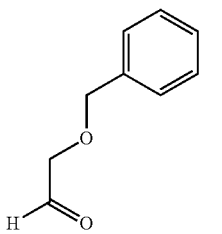
Step 1

To a solution of 2-benzyloxyacetaldehyde (355.7 µL, 2.532 mmol) in DCM (2.735 mL) was added 6-[(2S)-2-allylpyrrolidin-1-yl]-3-(tert-butoxycarbonylamino)-5-(trifluoromethyl)pyridine-2-carboxylic acid (263 mg, 0.6331 mmol), followed by N-isocyanoimino)triphenylphosphorane (191.4 mg, 0.6331 mmol) and the mixture was stirred overnight at room temperature. The reaction mixture was concentrated and purified by silica gel chromatography (12 g column) using a gradient from 0% to 30% EtOAc in hexanes giving as a yellow solid, tert-butyl N-[6-[(2S)-2-allylpyrrolidin-1-yl]-2-[5-(2-benzyloxy-1-hydroxy-ethyl)-1,3,4-oxadiazol-2-yl]-5-(trifluoromethyl)-3-pyridyl]carbamate (300 mg, 80%). ESI-MS m/z calc. 589.2512, found 590.4 (M+1)$^+$; Retention time: 0.87 minutes (LC Method R).

Step 2: tert-Butyl N-(2-{5-[2-(benzyloxy)acetyl]-1,3,4-oxadiazol-2-yl}-6-[(2S)-2-(prop-2-en-1-yl)pyrrolidin-1-yl]-5-(trifluoromethyl)pyridin-3-yl)carbamate

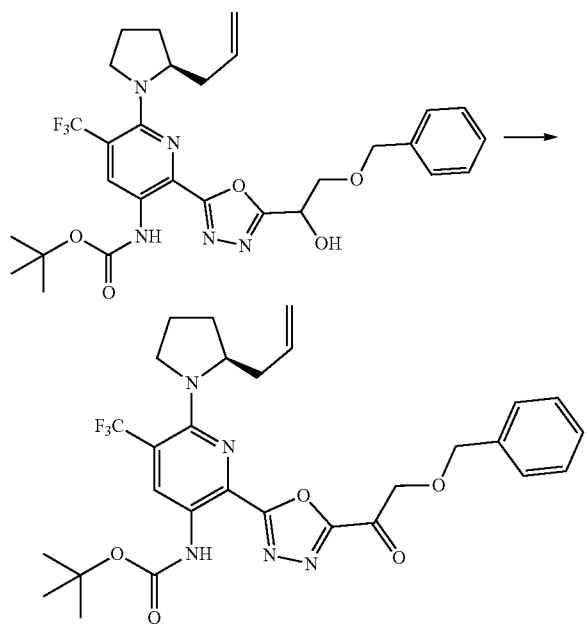

To a solution of tert-butyl N-[6-[(2S)-2-allylpyrrolidin-1-yl]-2-[5-(2-benzyloxy-1-hydroxy-ethyl)-1,3,4-oxadiazol-2-yl]-5-(trifluoromethyl)-3-pyridyl]carbamate (270 mg, 0.3892 mmol) in DCM (3.176 mL) was added DMP (215.9 mg, 0.509 mmol) and the mixture was stirred for 15 min. The reaction was quenched with saturated aqueous NaHCO$_3$ and extracted with DCM (2×25 mL). Combined organic layers were washed with brine, dried over Na$_2$SO$_4$, filtered and concentrated. Purification by silica gel chromatography (12 g column) using a gradient from 0% to 20% ethyl acetate in hexanes gave as an orange solid, tert-butyl N-(2-{5-[2-(benzyloxy)acetyl]-1,3,4-oxadiazol-2-yl}-6-[(2S)-2-(prop-2-en-1-yl)pyrrolidin-1-yl]-5-(trifluoromethyl)pyridin-3-yl) carbamate (180 mg, 79%). ESI-MS m/z calc. 587.23553, found 588.4 (M+1)$^+$; Retention time: 0.92 minutes (LC Method R).

Step 3: tert-Butyl N-[6-[(2S)-2-allylpyrrolidin-1-yl]-2-[5-[1-(benzyloxymethyl)-1-hydroxy-pent-4-enyl]-1,3,4-oxadiazol-2-yl]-5-(trifluoromethyl)-3-pyridyl]carbamate

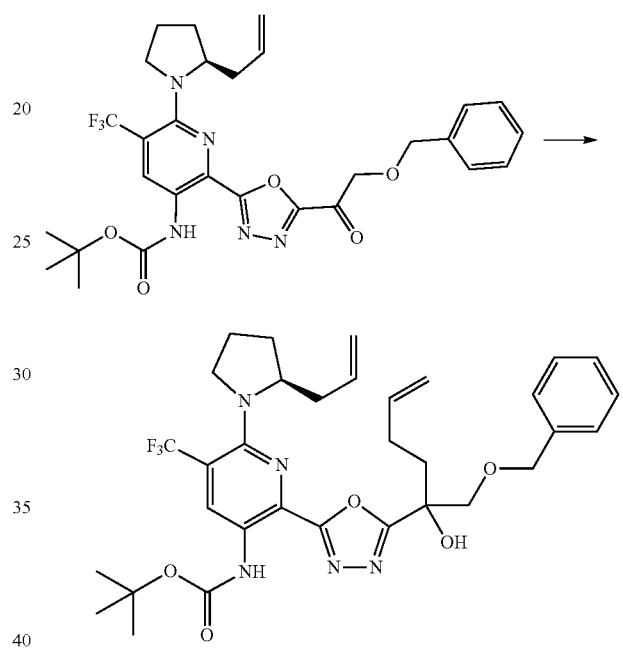

A solution of tert-butyl N-(2-{5-[2-(benzyloxy)acetyl]-1,3,4-oxadiazol-2-yl}-6-[(2S)-2-(prop-2-en-1-yl)pyrrolidin-1-yl]-5-(trifluoromethyl)pyridin-3-yl)carbamate (180 mg, 0.3063 mmol) in THF (4.0 mL) was cooled in an ice-bath and bromo(but-3-enyl)magnesium (2.02 mL of 0.5 M, 1.010 mmol) was added dropwise and the solution was stirred for 20 minutes. The reaction was quenched by the addition of citric acid (306 µl M, 0.306 mmol) while still in the ice bath, and extracted with ethyl acetate (2×15 mL). Combined organic layers were washed with brine, dried over Na$_2$SO$_4$, filtered and concentrated. Purification by silica gel chromatography (12 g column) using a gradient from 0% to 30% EtOAc in hexanes gave as a yellow solid, tert-butyl N-[6-[(2S)-2-allylpyrrolidin-1-yl]-2-[5-[1-(benzyloxymethyl)-1-hydroxy-pent-4-enyl]-1,3,4-oxadiazol-2-yl]-5-(trifluoromethyl)-3-pyridyl]carbamate (60 mg, 30%). ESI-MS m/z calc. 643.29816, found 644.5 (M+1)$^+$; Retention time: 0.83 minutes (LC Method T).

Step 4: tert-Butyl N-[(12S)-6-[(benzyloxy)methyl]-6-hydroxy-18-(trifluoromethyl)-22-oxa-3,4,16,21-tetraazatetracyclo[15.3.1.1²,⁵.0¹²,¹⁶]docosa-1(20),2,4,9,17(21),18-hexaen-20-yl]carbamate (E/Z mixture)

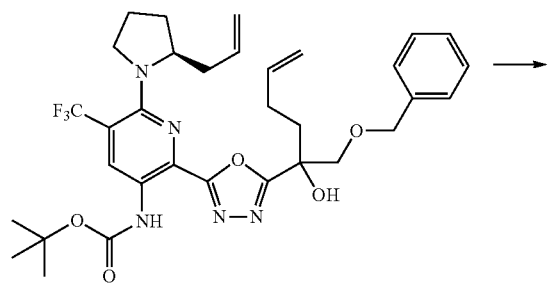

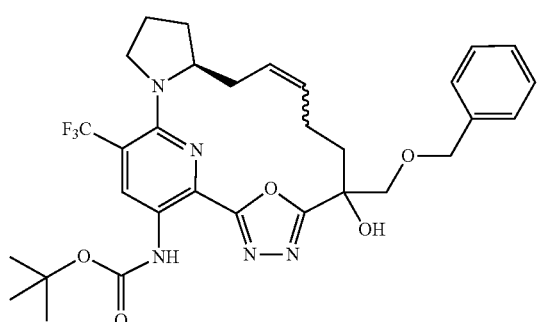

E/Z mixture

In a 100 mL round-bottom 3-neck flask, a continuously degassed solution via nitrogen line of tert-butyl N-[6-[(2S)-2-allylpyrrolidin-1-yl]-2-[5-[1-(benzyloxymethyl)-1-hydroxy-pent-4-enyl]-1,3,4-oxadiazol-2-yl]-5-(trifluoromethyl)-3-pyridyl]carbamate (60 mg, 0.09321 mmol) in DCE (30.0 mL) was heated to 50° C. under nitrogen atmosphere. Then, a solution of [1,3-bis(2,4,6-trimethylphenyl)imidazolidin-2-ylidene]-dichloro-[(2-isopropoxyphenyl)methylene]ruthenium (14.40 mg, 0.02298 mmol) in DCE (5 mL) was added via syringe. The resulting mixture was heated at 60° C. for 2 h. The reaction mixture was cooled to room temperature and concentrated under reduced pressure. The residue was then purified by silica gel chromatography (24 gram column) using a gradient from 100% hexanes to 40% ethyl acetate in hexanes to afford as a yellow semi-solid, tert-butyl N-[(12S)-6-[(benzyloxy)methyl]-6-hydroxy-18-(trifluoromethyl)-22-oxa-3,4,16,21-tetraazatetracyclo[15.3.1.1²,⁵.0¹²,¹⁶]docosa-1(20),2,4,9,17(21),18-hexaen-20-yl]carbamate (E/Z mixture) (22 mg, 38%). ESI-MS m/z calc. 615.26685, found 616.5 (M+1)⁺; Retention time: 0.74 minutes (LC Method T).

Step 5: tert-Butyl N-[(12R)-6-hydroxy-6-(hydroxymethyl)-18-(trifluoromethyl)-22-oxa-3,4,16,21-tetraazatetracyclo[15.3.1.1²,⁵.0¹²,¹⁶]docosa-1(20),2,4,17(21),18-pentaen-20-yl]carbamate (enantiomer 1) and tert-butyl N-[(12R)-6-hydroxy-6-(hydroxymethyl)-18-(trifluoromethyl)-22-oxa-3,4,16,21-tetraazatetracyclo[15.3.1.1²,⁵.0¹²,¹⁶]docosa-1(20),2,4,17(21),18-pentaen-20-yl]carbamate (enantiomer 2)

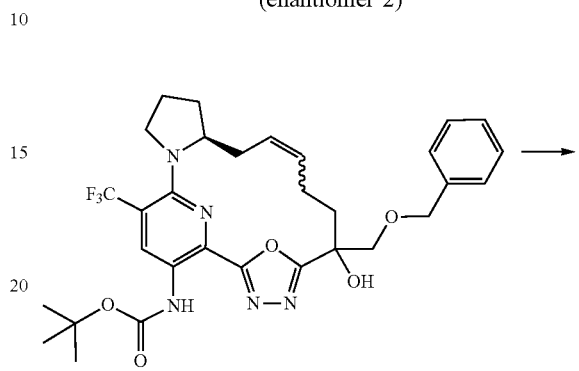

E/Z mixture

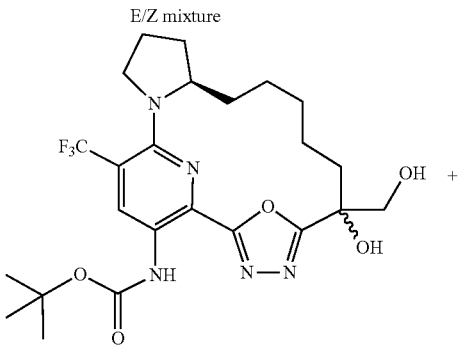

enantiomer 1

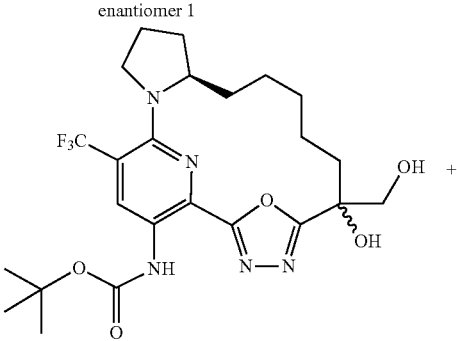

enantiomer 2

To a solution of tert-butyl N-[(12S)-6-[(benzyloxy)methyl]-6-hydroxy-18-(trifluoromethyl)-22-oxa-3,4,16,21-tetraazatetracyclo[15.3.1.1²,⁵.0¹²,¹⁶]docosa-1(20),2,4,9,17(21),18-hexaen-20-yl]carbamate (E/Z mixture) (25 mg, 0.04061 mmol) in AcOH (432.0 µL) was added Pd/C (11.07 mg, 10% w/w, 0.0104 mmol). The mixture was stirred under a hydrogen balloon at room temperature for 4 h. The reaction mixture was filtered through Celite, washing well with ethyl acetate and then the filtrate was concentrated. Purification by silica gel chromatography (12 g column) using a gradient from 0% to 20% EtOAc in hexanes over 20 minutes gave two diastereomeric products:

The first diastereomer to elute was isolated as a yellow solid, tert-butyl N-[(12R)-6-hydroxy-6-(hydroxymethyl)-

18-(trifluoromethyl)-22-oxa-3,4,16,21-tetraazatetracyclo[15.3.1.1²,⁵.0¹²,¹⁶]docosa-1(20),2,4,17(21),18-pentaen-20-yl]carbamate (enantiomer 1) (9 mg, 42%). ESI-MS m/z calc. 527.23553, found 528.4 (M+1)⁺; Retention time: 0.67 minutes (LC Method R).

The second enantiomer to elute was isolated as a yellow solid, tert-butyl N-[(12R)-6-hydroxy-6-(hydroxymethyl)-18-(trifluoromethyl)-22-oxa-3,4,16,21-tetraazatetracyclo[15.3.1.1²,⁵.0¹²,¹⁶]docosa-1(20),2,4,17(21),18-pentaen-20-yl]carbamate (enantiomer 2) (9 mg, 42%). ESI-MS m/z calc. 527.23553, found 528.4 (M+1)⁺; Retention time: 0.66 minutes (LC Method R).

Step 6: (12R)-20-Amino-6-(hydroxymethyl)-18-(trifluoromethyl)-22-oxa-3,4,16,21-tetraazatetracyclo[15.3.1.1²,⁵.0¹²,¹⁶]docosa-1(20),2,4,17(21),18-pentaen-6-ol (enantiomer 1) (Compound 100)

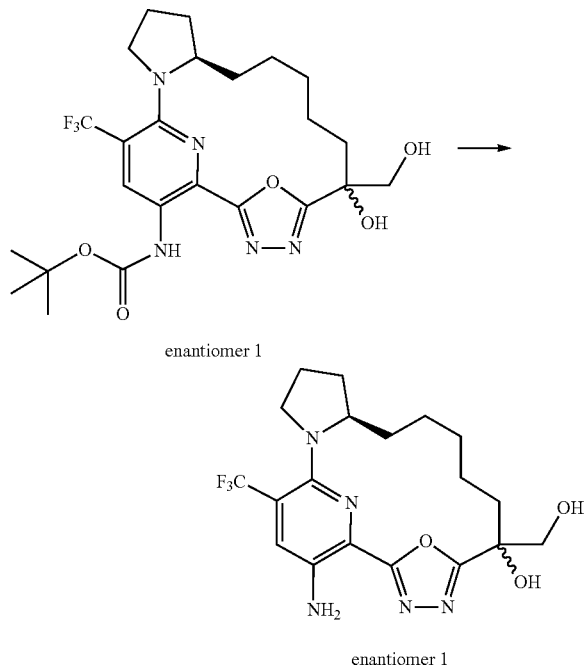

enantiomer 1 enantiomer 1

To a solution of tert-butyl N-[(12R)-6-hydroxy-6-(hydroxymethyl)-18-(trifluoromethyl)-22-oxa-3,4,16,21-tetraazatetracyclo[15.3.1.1²,⁵.0¹²,¹⁶]docosa-1(20),2,4,17(21),18-pentaen-20-yl]carbamate (enantiomer 1) (9 mg, 0.01706 mmol) in DCM (82.2 μL) was added TFA (35.01 μL, 0.4544 mmol) and the mixture was stirred at room temperature for 20 min. The reaction mixture was concentrated, diluted with ethyl acetate and washed with saturated aqueous NaHCO₃. The organic layer was separated and dried over Na₂SO₄, filtered and concentrated to afford as a yellow solid, (12R)-20-amino-6-(hydroxymethyl)-18-(trifluoromethyl)-22-oxa-3,4,16,21-tetraazatetracyclo[15.3.1.1²,⁵.0¹²,¹⁶]docosa-1(20),2,4,17(21),18-pentaen-6-ol (enantiomer 1) (5 mg, 65%). ¹H NMR (400 MHz, CD₃OD) δ 7.67 (s, 1H), 4.20-4.12 (m, 1H), 3.91 (dd, J=94.4, 11.6 Hz, 2H), 3.70-3.60 (m, 1H), 3.42 (s, 1H), 2.58 (s, 1H), 2.30-2.19 (m, 2H), 2.03-1.94 (m, 2H), 1.88-1.80 (m, 1H), 1.71-1.60 (m, 3H), 1.59-1.48 (m, 3H), 1.03-0.87 (m, 2H) ppm. ESI-MS m/z calc. 427.18314, found 428.3 (M+1)⁺; Retention time: 1.76 minutes (LC Method A).

Step 7: (12R)-20-Amino-6-(hydroxymethyl)-18-(trifluoromethyl)-22-oxa-3,4,16,21-tetraazatetracyclo[15.3.1.1²,⁵.0¹²,¹⁶]docosa-1(20),2,4,17(21),18-pentaen-6-ol (enantiomer 2) (Compound 101)

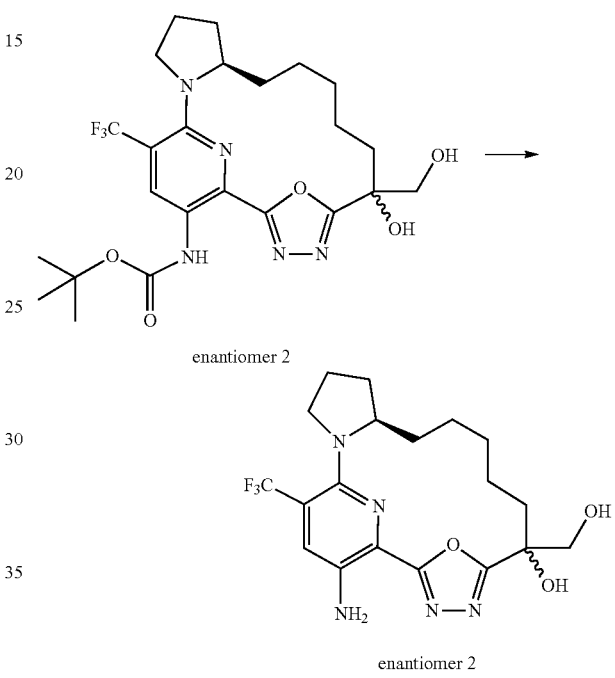

enantiomer 2 enantiomer 2

To a solution of tert-butyl N-[(12R)-6-hydroxy-6-(hydroxymethyl)-18-(trifluoromethyl)-22-oxa-3,4,16,21-tetraazatetracyclo[15.3.1.1²,⁵.0¹²,¹⁶]docosa-1(20),2,4,17(21),18-pentaen-20-yl]carbamate (enantiomer 2) (8.5 mg, 0.01611 mmol) in DCM (174.7 μL) was added TFA (74.39 μL, 0.9656 mmol) and the mixture was stirred at room temperature for 20 min. The reaction mixture was concentrated, diluted with ethyl acetate and washed with saturated aqueous NaHCO₃. The organic layer was dried over Na₂SO₄, filtered and concentrated to afford as a yellow solid, (12R)-20-amino-6-(hydroxymethyl)-18-(trifluoromethyl)-22-oxa-3,4,16,21-tetraazatetracyclo[15.3.1.1²,⁵.0¹²,¹⁶]docosa-1(20),2,4,17(21),18-pentaen-6-ol (enantiomer 2) (5 mg, 69%). ¹H NMR (400 MHz, CD₃OD) δ 7.70 (s, 1H), 4.11 (t, J=7.1 Hz, 1H), 3.89 (dd, J=79.9, 10.7 Hz, 2H), 3.65 (s, 1H), 3.43 (d, J=9.3 Hz, 1H), 2.66 (d, J=10.2 Hz, 1H), 2.43 (dd, J=12.5, 10.1 Hz, 1H), 2.31-2.16 (m, 1H), 2.02 (ddt, J=10.0, 6.7, 3.3 Hz, 1H), 1.92-1.71 (m, 3H), 1.70-1.58 (m, 5H), 0.95 (td, J=11.3, 9.4, 5.1 Hz, 2H) ppm. ESI-MS m/z calc. 427.18314, found 428.3 (M+1)⁺; Retention time: 1.74 minutes (LC Method A).

539

Example 53: Preparation of 17-amino-12-(hydroxymethyl)-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (Compound 102), 17-amino-12-(hydroxymethyl)-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (Compound 103), 17-amino-12-(hydroxymethyl)-6,15-bis(trifluoromethyl)-19-oxa-3,4,13,18-tetrazatricyclo[12.3.1.1²,⁵]nonadeca-1(18),2,4,14,16-pentaen-6-ol (enantiomer 3) (Compound 104) and 17-amino-12-(hydroxymethyl)-6,15-bis(trifluoromethyl)-19-oxa-3,4,13,18-tetrazatricyclo[12.3.1.1²,⁵]nonadeca-1(18),2,4,14,16-pentaen-6-ol (enantiomer 4) (Compound 105)

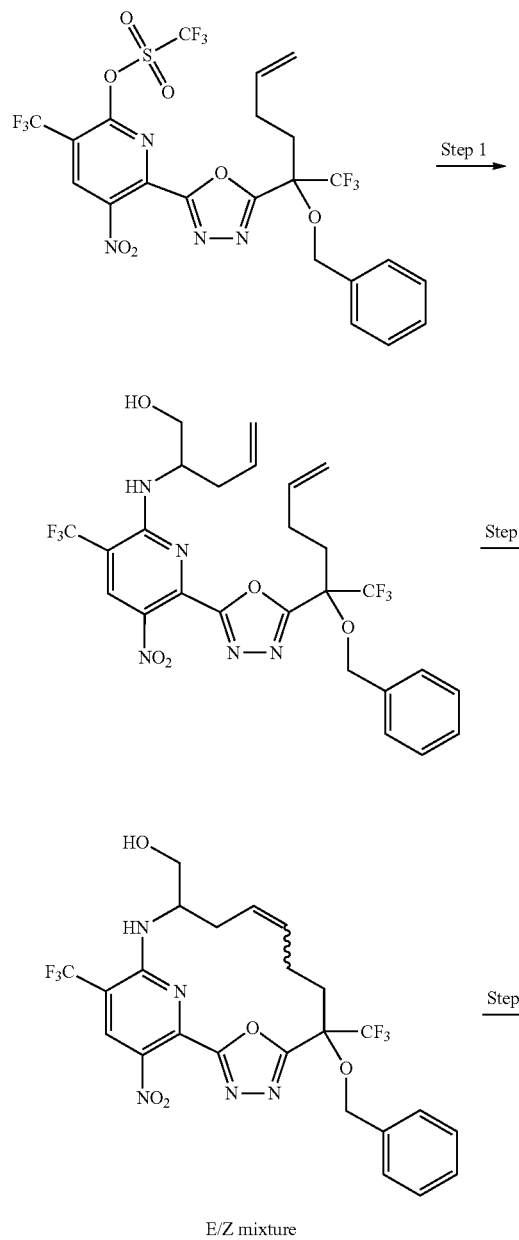

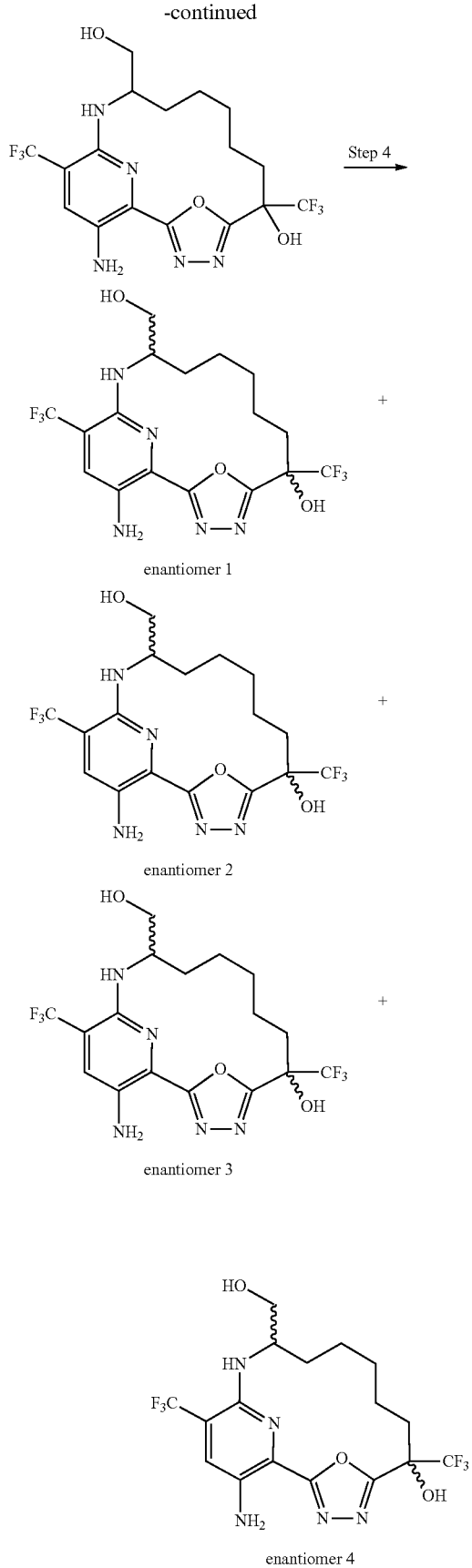

Step 1: 2-[[6-[5-[1-Benzyloxy-1-(trifluoromethyl)pent-4-enyl]-1,3,4-oxadiazol-2-yl]-5-nitro-3-(trifluoromethyl)-2-pyridyl]amino]pent-4-en-1-ol

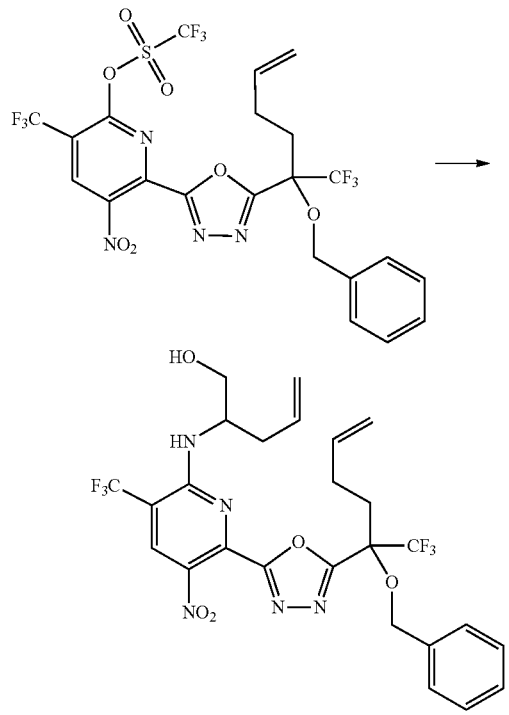

In a 20 mL vial, [6-[5-[1-benzyloxy-1-(trifluoromethyl)pent-4-enyl]-1,3,4-oxadiazol-2-yl]-5-nitro-3-(trifluoromethyl)-2-pyridyl] trifluoromethanesulfonate (350 mg, 0.5381 mmol) was dissolved in acetonitrile (6 mL) at room temperature followed by addition of 2-aminopent-4-en-1-ol (hydrochloride salt) (225 mg, 1.635 mmol) then DIEA (500 μL, 2.871 mmol) and then the mixture was stirred for 16 hours. The mixture was diluted with ethyl acetate, washed with water and brine, dried over sodium sulfate, filtered and evaporated. The material was purified on silica gel chromatography (80 gram column) using a gradient from 100% hexanes to 70% ethyl acetate in hexanes to afford as a yellow solid, 2-[[6-[5-[1-benzyloxy-1-(trifluoromethyl)pent-4-enyl]-1,3,4-oxadiazol-2-yl]-5-nitro-3-(trifluoromethyl)-2-pyridyl]amino]pent-4-en-1-ol (180 mg, 56%). $^1$H NMR (400 MHz, DMSO-d6) δ 8.56 (s, 1H), 7.51 (d, J=7.9 Hz, 1H), 7.43-7.28 (m, 5H), 5.85 (ddt, J=16.8, 10.2, 6.5 Hz, 1H), 5.78-5.63 (m, 1H), 5.10 (dq, J=17.2, 1.7 Hz, 1H), 5.05-4.97 (m, 2H), 4.92 (ddd, J=10.4, 8.1, 3.5 Hz, 2H), 4.76 (dd, J=11.0, 1.5 Hz, 1H), 4.60 (d, J=10.7 Hz, 1H), 4.44 (s, 1H), 3.55 (dtd, J=16.3, 11.0, 5.6 Hz, 2H), 2.58-2.51 (m, 2H), 2.38 (t, J=6.7 Hz, 2H), 2.30-2.17 (m, 2H) ppm. ESI-MS m/z calc. 601.17596, found 602.2 (M+1)$^+$; Retention time: 1.69 minutes. The O-linked regioisomeric side-product eluted later (LC Method J).

Step 2: [6-Benzyloxy-17-nitro-6,15-bis(trifluoromethyl)-19-oxa-3,4,13,18-tetrazatricyclo[12.3.1.12,5]nonadeca-1(17),2,4,9,14(18),15-hexaen-12-yl]methanol

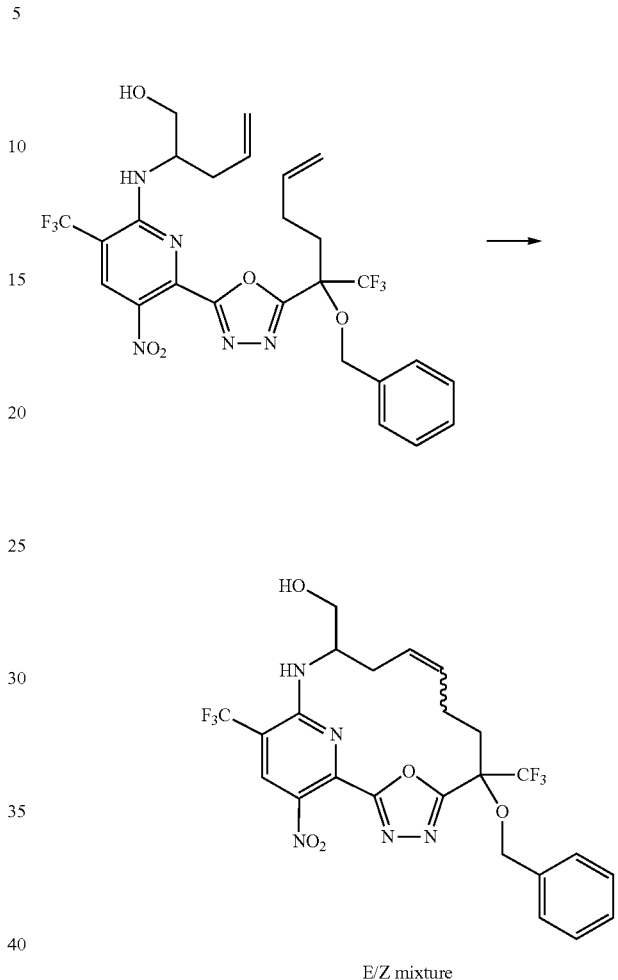

E/Z mixture

In a 150 mL flask, 0.25 eq of Zhan catalyst-1B, dichloro[1,3-bis(2,4,6-trimethylphenyl)-2-imidazolidinylidene][[5-[(dimethylamino)sulfonyl]-2-(1-methylethoxy-0)phenyl]methylene-C]ruthenium(II) (53 mg, 0.07223 mmol) was dissolved in DCE (100 mL). Then, a solution of 2-[[6-[5-[1-benzyloxy-1-(trifluoromethyl)pent-4-enyl]-1,3,4-oxadiazol-2-yl]-5-nitro-3-(trifluoromethyl)-2-pyridyl]amino]pent-4-en-1-ol (190 mg, 0.3159 mmol) in DCE (5 mL) was added via syringe. The resulting mixture was heated to 70° C. for 2 h. The residue was concentrated and purified by silica gel chromatography (40 gram column) using a gradient from 100% hexanes to 75% ethyl acetate in hexanes to afford as a tan solid, [6-benzyloxy-17-nitro-6,15-bis(trifluoromethyl)-19-oxa-3,4,13,18-tetrazatricyclo[12.3.1.12,5]nonadeca-1(17),2,4,9,14(18),15-hexaen-12-yl]methanol (58 mg, 32%). ESI-MS m/z calc. 573.1447, found 574.0 (M+1)$^+$; Retention time: 1.4 minutes (LC Method J).

Step 3: 17-Amino-12-(hydroxymethyl)-6,15-bis (trifluoromethyl)-19-oxa-3,4,13,18-tetrazatricyclo [12.3.1.1²,⁵]nonadeca-1(18),2,4,14,16-pentaen-6-ol

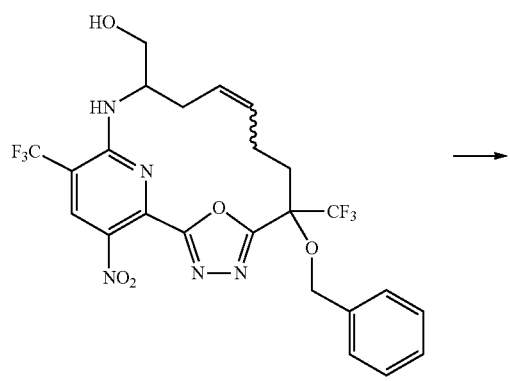

E/Z mixture

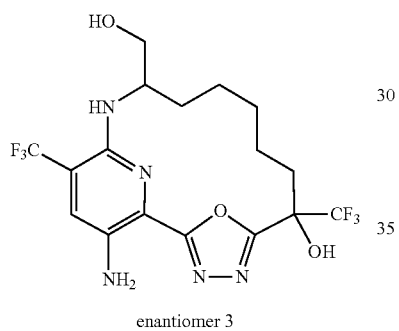

enantiomer 3

In a 50 mL round bottom flask, a solution of [6-benzyloxy-17-nitro-6,15-bis(trifluoromethyl)-19-oxa-3,4,13,18-tetrazatricyclo[12.3.1.1²,⁵]nonadeca-1(17),2,4,9,14(18),15-hexaen-12-yl]methanol (58 mg, 0.1011 mmol) in ethyl acetate (4 mL) was purged with nitrogen. Then Pd/C (110 mg of 10% w/w, 0.1034 mmol) was added. The mixture was degassed with nitrogen then purged by a balloon filled with hydrogen gas. The mixture was stirred at 1 atm of hydrogen for 6 h. The reaction was filtered and the material was purified by silica gel chromatography (12 gram column) using a gradient from 100% hexanes to 70% ethyl acetate in hexanes to afford two peaks that were not fully separable. Therefore, the combined mixture of 4 stereoisomers was concentrated together giving a yellow solid, 17-amino-12-(hydroxymethyl)-6,15-bis(trifluoromethyl)-19-oxa-3,4,13, 18-tetrazatricyclo[12.3.1.1²,⁵]nonadeca-1(18),2,4,14,16-pentaen-6-ol (34.5 mg, 75%). ESI-MS m/z calc. 455.13922, found 456.2 (M+1)⁺; Retention time: 1.46 minutes (LC Method A).

Step 4: 17-Amino-12-(hydroxymethyl)-6,15-bis (trifluoromethyl)-19-oxa-3,4,13,18-tetrazatricyclo [12.3.1.1²,⁵]nonadeca-1(18),2,4,14,16-pentaen-6-ol (enantiomer 1) (Compound 102), 17-amino-12-(hydroxymethyl)-6,15-bis(trifluoromethyl)-19-oxa-3, 4,13,18-tetrazatricyclo[12.3.1.1²,⁵]nonadeca-1(18), 2,4,14,16-pentaen-6-ol (enantiomer 2) (Compound 103), 17-amino-12-(hydroxymethyl)-6,15-bis(trifluoromethyl)-19-oxa-3,4,13,18-tetrazatricyclo [12.3.1.1²,⁵]nonadeca-1(18),2,4,14,16-pentaen-6-ol (enantiomer 3) (Compound 104), and 17-amino-12-(hydroxymethyl)-6,15-bis(trifluoromethyl)-19-oxa-3, 4,13,18-tetrazatricyclo[12.3.1.1²,⁵]nonadeca-1(18), 2,4,14,16-pentaen-6-ol (enantiomer 4) (Compound 105)

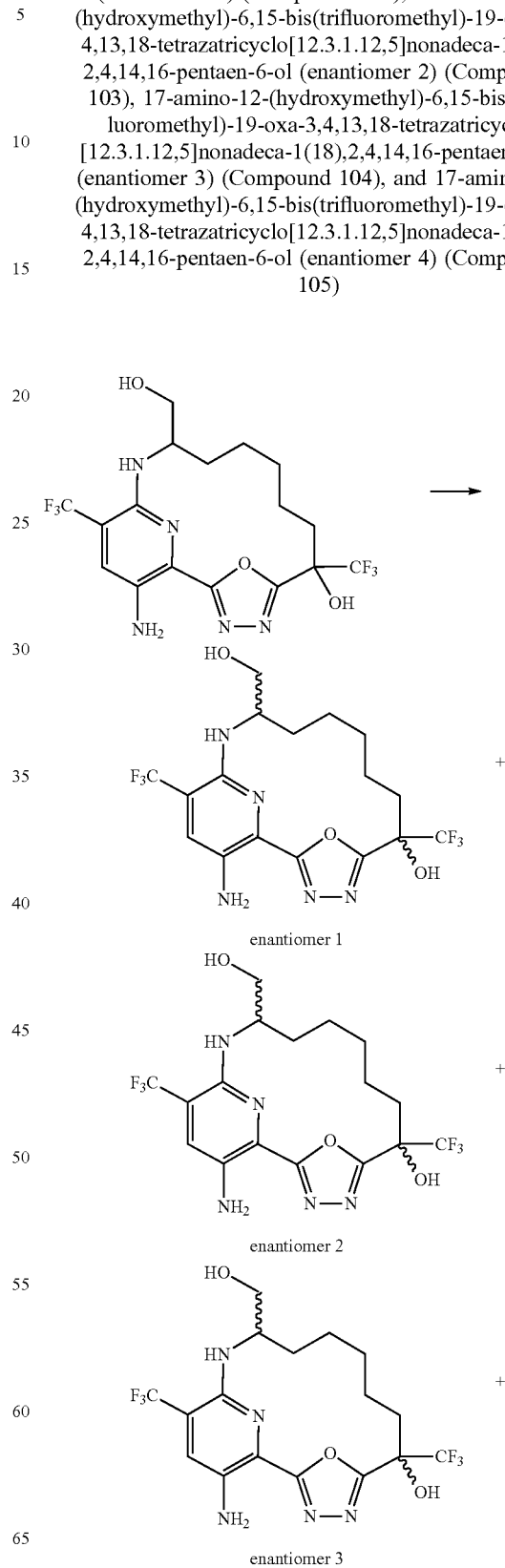

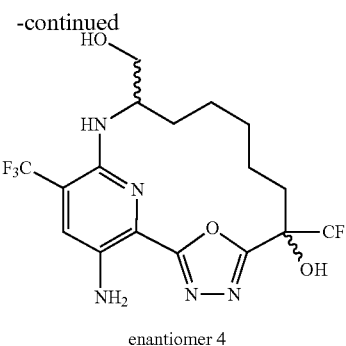

enantiomer 4

Racemic 17-amino-12-(hydroxymethyl)-6,15-bis(trifluoromethyl)-19-oxa-3,4,13,18-tetrazatricyclo[12.3.1.1²,⁵]nonadeca-1(18),2,4,14,16-pentaen-6-ol (31 mg, 0.06808 mmol) was subjected to two separate SFC purifications to resolve all four single enantiomers. The first preparative separation utilized a normal phase SFC method using an Phenomenex LUX-4 (250×10 mm, 5 μm particle size) sold by Phenomenex (pn: 00G-4491-PO-AX) and an isocratic run of 12% MeOH [+20 mM NH₃]/88% CO₂ (flow rate=10 mL/min, injection volume=70 μL of a 22 mg/mL concentration in MeOH with no modifier and column temperature=35° C.) resolving enantiomer 1 (co-eluting with an impurity), enantiomer 2, enantiomer 3 and enantiomer 4. The second preparative normal phase SFC separation utilized a ChiralCel OJ column (250×10 mm, 5 μm particle size) sold by ChiralCel (pn: 17335) and an isocratic run of 10% MeOH [+20 mM NH₃]/90% CO₂ (flow rate=10 mL/min, injection volume=70 μL of a 12 mg/mL concentration in MeOH with no modifier and column temperature=35° C.) resolving enantiomer 1. The purification conditions above led to the isolation of all four single enantiomers described below:

Enantiomer 1 was isolated as a yellow solid, 17-amino-12-(hydroxymethyl)-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (0.9 mg, 12%). ESI-MS m/z calc. 455.13922, found 456.2 (M+1)⁺; Retention time: 1.41 minutes (LC Method A).

Enantiomer 2 was isolated as a yellow solid, 17-amino-12-(hydroxymethyl)-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (1.7 mg, 22%). ¹H NMR (400 MHz, CD₃OD) δ 7.53 (s, 1H), 5.26 (s, 1H), 3.85 (dd, J=11.0, 3.3 Hz, 1H), 3.73 (td, J=7.1, 3.5 Hz, 1H), 3.61 (ddd, J=11.1, 7.4, 2.1 Hz, 1H), 2.50-2.43 (m, 1H), 2.38 (d, J=12.9 Hz, 1H), 2.14 (ddd, J=14.7, 9.9, 6.3 Hz, 1H), 1.87-1.71 (m, 2H), 1.64 (q, J=8.1, 7.3 Hz, 1H), 1.59-1.45 (m, 3H), 1.29 (s, 1H), 1.19-1.11 (m, 1H), 0.91 (dd, J=16.8, 10.6 Hz, 1H) ppm. ESI-MS m/z calc. 455.13922, found 456.2 (M+1)⁺; Retention time: 1.51 minutes (LC Method A).

Enantiomer 3 was isolated as a yellow solid, 17-amino-12-(hydroxymethyl)-6,15-bis(trifluoromethyl)-19-oxa-3,4,13,18-tetrazatricyclo[12.3.1.1²,⁵]nonadeca-1(18),2,4,14,16-pentaen-6-ol (enantiomer 3) (2.2 mg, 28%). ¹H NMR (400 MHz, CD₃OD) δ 7.53 (d, J=0.8 Hz, 1H), 5.27 (s, 1H), 3.86 (dd, J=10.9, 3.1 Hz, 1H), 3.70-3.63 (m, 1H), 3.60 (ddd, J=10.9, 7.7, 2.0 Hz, 1H), 2.52 (td, J=10.8, 9.7, 4.4 Hz, 1H), 2.45-2.35 (m, 1H), 2.13-2.03 (m, 1H), 1.69 (dt, J=9.8, 4.8 Hz, 2H), 1.60 (d, J=6.2 Hz, 3H), 1.56-1.49 (m, 1H), 1.29 (s, 1H), 1.06 (d, J=10.4 Hz, 1H), 0.97-0.80 (m, 1H) ppm. ESI-MS m/z calc. 455.13922, found 456.2 (M+1)⁺; Retention time: 1.42 minutes (LC Method A).

Enantiomer 4 was isolated as a yellow solid, 17-amino-12-(hydroxymethyl)-6,15-bis(trifluoromethyl)-19-oxa-3,4,13,18-tetrazatricyclo[12.3.1.1²,⁵]nonadeca-1(18),2,4,14,16-pentaen-6-ol (enantiomer 4) (1.9 mg, 24%). ¹H NMR (400 MHz, Chloroform-d) δ 7.33 (s, 1H), 5.09 (s, 2H), 3.96 (d, J=7.5 Hz, 1H), 3.71 (d, J=8.0 Hz, 2H), 2.52 (dt, J=14.4, 7.7 Hz, 1H), 2.33 (t, J=12.3 Hz, 1H), 2.29-2.18 (m, 1H), 1.99 (d, J=10.5 Hz, 1H), 1.62 (d, J 7.4 Hz, 2H), 1.56-1.50 (m, 2H), 1.26 (s, 2H), 1.21 (d, J=6.1 Hz, 1H), 1.15 (dd, J=14.0, 7.3 Hz, 1H), 0.92-0.82 (m, 1H) ppm. ESI-MS m/z calc. 455.13922, found 456.2 (M+1)⁺; Retention time: 1.52 minutes (LC Method A).

Example 54: Preparation of 18-amino-6-hydroxy-6,16-bis(trifluoromethyl)-20-oxa-3,4,14,19-tetrazatricyclo[13.3.1.1²,⁵]icosa-1(19),2,4,15,17-pentaen-13-one (enantiomer 1) (Compound 106) and 18-amino-6-hydroxy-6,16-bis(trifluoromethyl)-20-oxa-3,4,14,19-tetrazatricyclo[13.3.1.1²,⁵]icosa-1(19),2,4,15,17-pentaen-13-one (enantiomer 2) (Compound 107)

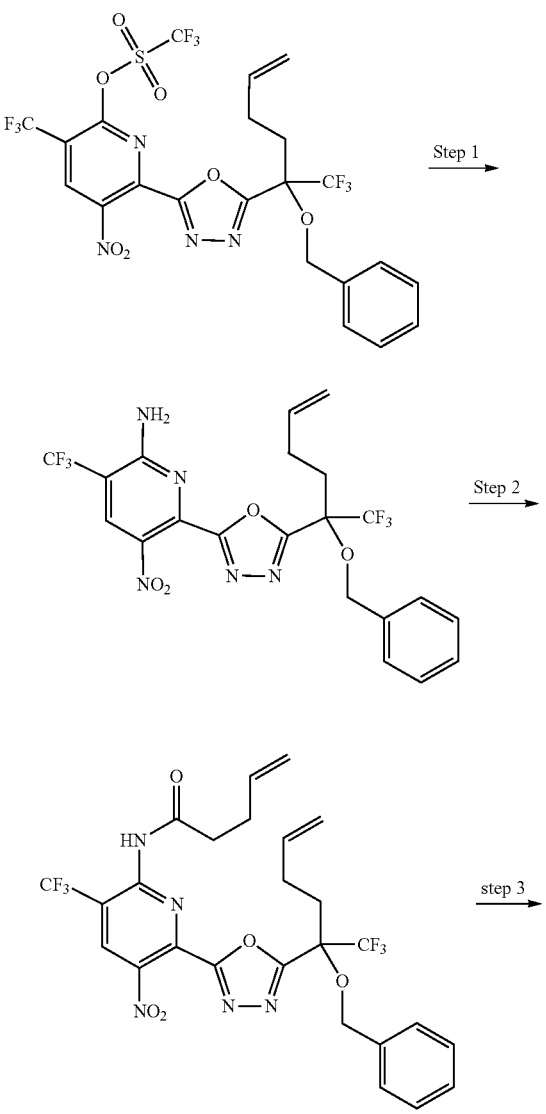

547

-continued

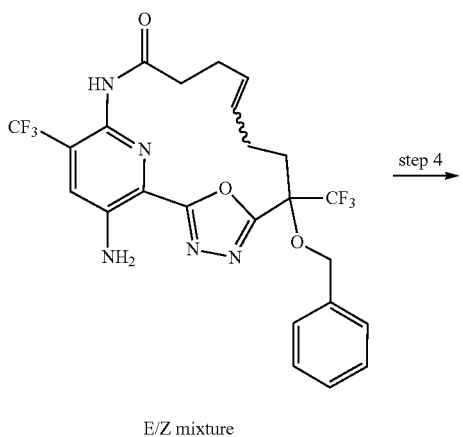

E/Z mixture

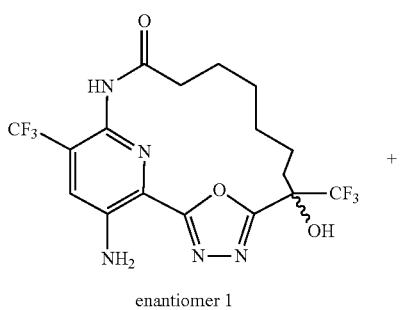

enantiomer 1

+

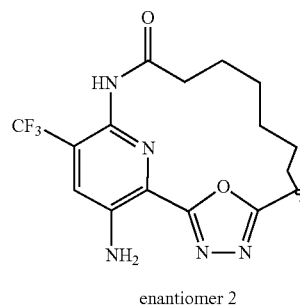

enantiomer 2

Step 1: 6-[5-[1-Benzyloxy-1-(trifluoromethyl)pent-4-enyl]-1,3,4-oxadiazol-2-yl]-5-nitro-3-(trifluoromethyl)pyridin-2-amine

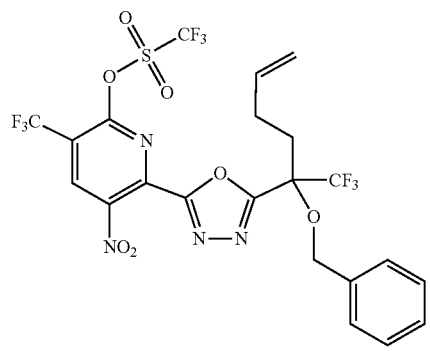

548

-continued

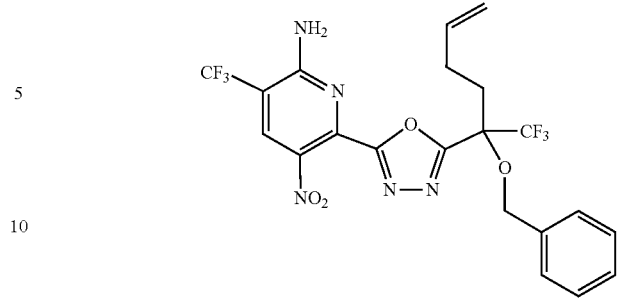

To a mixture of [6-[5-[1-benzyloxy-1-(trifluoromethyl)pent-4-enyl]-1,3,4-oxadiazol-2-yl]-5-nitro-3-(trifluoromethyl)-2-pyridyl] trifluoromethanesulfonate (6 mg, 0.009225 mmol) in dioxane was added ammonia (184 μL of 0.5 M, 0.092 mmol) followed by THF (0.4 mL) and the mixture was stirred at 50° C. for 90 min. The mixture was diluted with EtOAc, washed with water then brine, dried (MgSO$_4$), filtered and evaporated to provide 6-[5-[1-benzyloxy-1-(trifluoromethyl)pent-4-enyl]-1,3,4-oxadiazol-2-yl]-5-nitro-3-(trifluoromethyl)pyridin-2-amine (4.3 mg, 90%). $^1$H NMR (400 MHz, Chloroform-d) δ 8.63 (s, 1H), 8.33 (s, 2H), 7.42-7.29 (m, 5H), 5.92 (s, 1H), 5.79 (ddd, J=20.3, 10.1, 3.7 Hz, 1H), 5.15-4.94 (m, 1H), 4.80 (d, J=10.6 Hz, 1H), 4.73-4.56 (m, 1H), 2.65-2.04 (m, 4H) ppm; $^{19}$F NMR (376 MHz, Chloroform-d) δ −64.72, −73.14 ppm. ESI-MS m/z calc. 517.11847, found 518.1 (M+1)$^+$; Retention time: 0.75 minutes (LC Method S).

Step 2: N-[6-[5-[1-Benzyloxy-1-(trifluoromethyl)pent-4-enyl]-1,3,4-oxadiazol-2-yl]-5-nitro-3-(trifluoromethyl)-2-pyridyl]pent-4-enamide

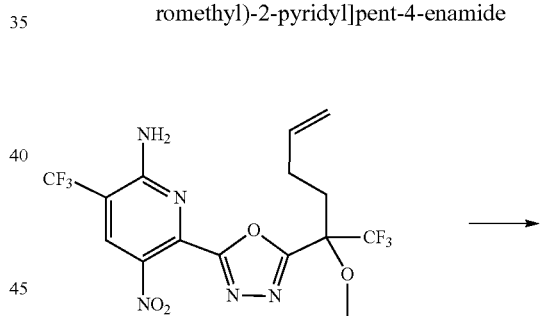

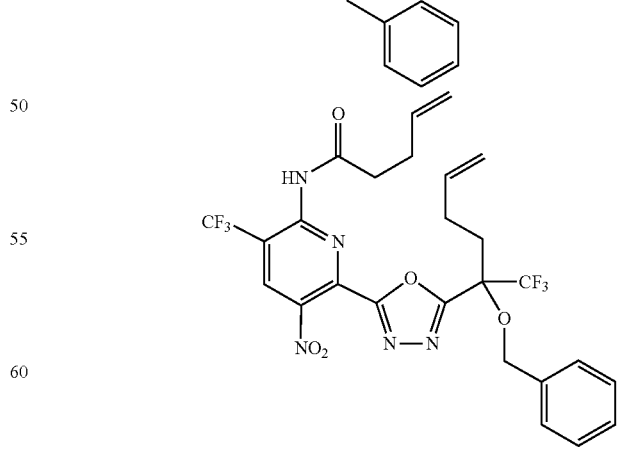

In dichloromethane (1.2 mL) was added 6-[5-[1-benzyloxy-1-(trifluoromethyl)pent-4-enyl]-1,3,4-oxadiazol-2-yl]-5-nitro-3-(trifluoromethyl)pyridin-2-amine (59 mg, 0.114 mmol), DIPEA (60 µL, 0.3445 mmol) and DMAP (114 µL of 0.25 M, 0.0285 mmol). To this mixture was added pent-4-enoyl chloride (131 µL of 1 M, 0.131 mmol) as a solution in DCM with ice bath cooling. Then, the solution was stirred at room temperature for 30 min and the mixture was washed with aqueous 1 M NaHCO$_3$, aqueous 0.5 M HCl, water and brine then dried (MgSO$_4$), filtered and evaporated. The crude residue was purified by silica gel chromatography (4 g column, gradient from 0% to 25% EtOAc in hexanes over 15 min) to provide N-[6-[5-[1-benzyloxy-1-(trifluoromethyl)pent-4-enyl]-1,3,4-oxadiazol-2-yl]-5-nitro-3-(trifluoromethyl)-2-pyridyl]pent-4-enamide (69.5 mg, quant.). $^1$H NMR (400 MHz, Chloroform-d) δ 8.68 (s, 1H), 7.99 (s, 1H), 7.43-7.28 (m, 5H), 6.00-5.73 (m, 2H), 5.17-4.97 (m, 4H), 4.84 (d, J=10.7 Hz, 1H), 4.65 (d, J=10.6 Hz, 1H), 2.99 (t, J 7.3 Hz, 2H), 2.61-2.12 (m, 6H) ppm; $^{19}$F NMR (376 MHz, Chloroform-d) δ−62.60, −73.06 ppm. ESI-MS m/z calc. 599.16034, found 600.2 (M+1)$^+$; Retention time: 1.78 minutes (LC Method Q).

Step 3: 6-Benzyloxy-18-nitro-6,16-bis(trifluoromethyl)-20-oxa-3,4,14,19-tetrazatricyclo[13.3.1.12,5]icosa-1(18),2,4,9,15(19),16-hexaen-13-one (E/Z Mixture)

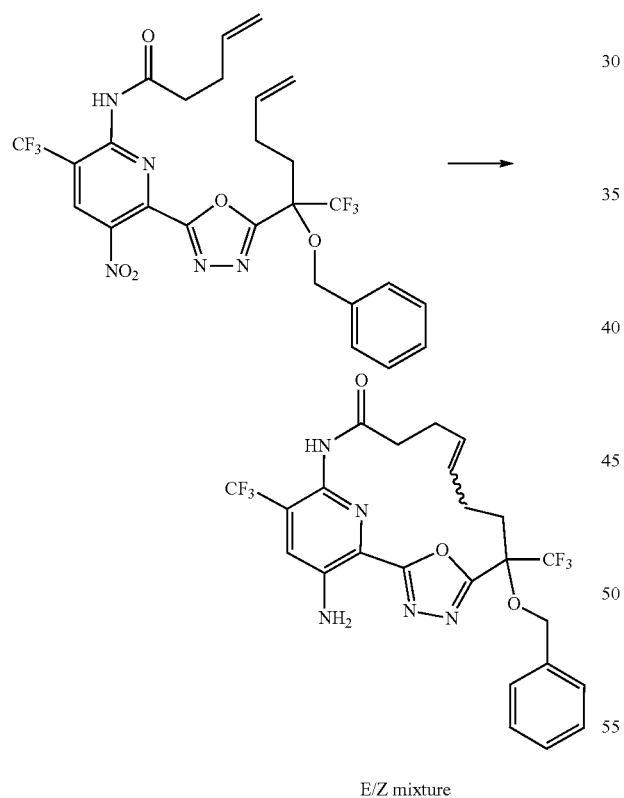

E/Z mixture

In a sealed 20 mL vial, a solution of N-[6-[5-[1-benzyloxy-1-(trifluoromethyl)pent-4-enyl]-1,3,4-oxadiazol-2-yl]-5-nitro-3-(trifluoromethyl)-2-pyridyl]pent-4-enamide (55 mg, 0.09175 mmol) and 1,3-bis(o-tolyl)-4,5-dihydroimidazole; dichloro-[(2-isopropoxyphenyl)methylene]ruthenium (8 mg, 0.01402 mmol) in toluene (8 mL) was bubbled with N$_2$ for 1 min and then was heated at 120° C. for 45 min and then the solvent was evaporated. The residue was purified by silica gel chromatography (12 g column, 0% to 25% EtOAc in hexanes over 15 min) to provide 6-benzyloxy-18-nitro-6,16-bis(trifluoromethyl)-20-oxa-3,4,14,19-tetrazatricyclo [13.3.1.12,5]icosa-1(18),2,4,9,15(19),16-hexaen-13-one (E/Z mixture) (32.6 mg, 62%). ESI-MS m/z calc. 571.129, found 572.1 (M+1)$^+$; Retention time: 0.74 minutes (LC Method S).

Step 4: 18-Amino-6-hydroxy-6,16-bis(trifluoromethyl)-20-oxa-3,4,14,19-tetrazatricyclo[13.3.1.12,5] icosa-1(19),2,4,15,17-pentaen-13-one (enantiomer 1) (Compound 106) and 18-amino-6-hydroxy-6,16-bis(trifluoromethyl)-20-oxa-3,4,14,19-tetrazatricyclo [13.3.1.12,5]icosa-1(19),2,4,15,17-pentaen-13-one (enantiomer 2) (Compound 107)

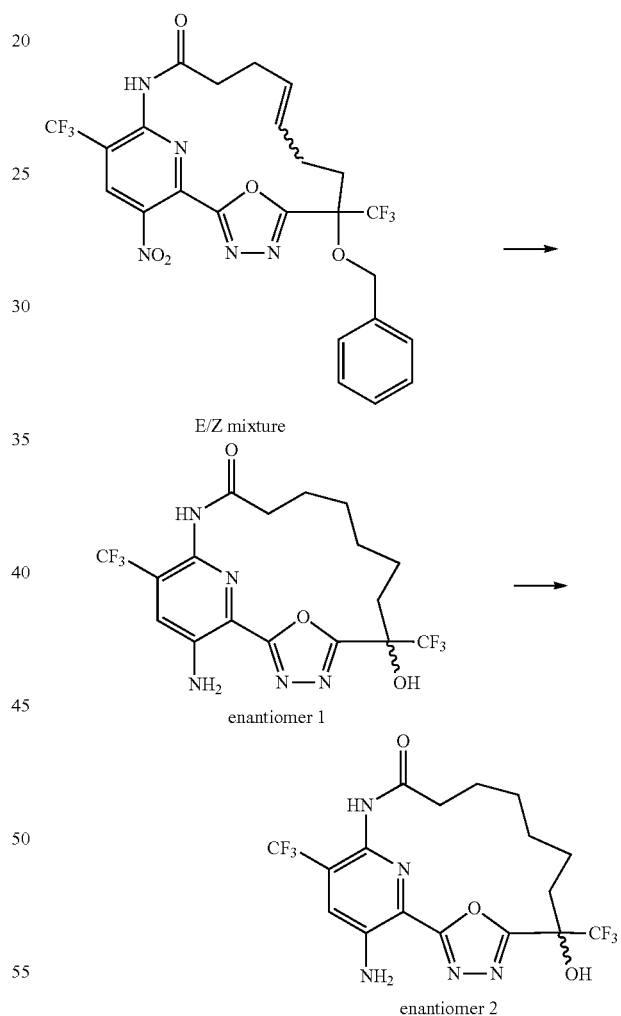

A mixture of 6-benzyloxy-18-nitro-6,16-bis(trifluoromethyl)-20-oxa-3,4,14,19-tetrazatricyclo[13.3.1.12,5]icosa-1 (18),2,4,9,15(19),16-hexaen-13-one (E/Z mixture) (32.6 mg, 0.05705 mmol) and palladium on carbon (18 mg of 10% w/w, 0.01691 mmol) in AcOH (700 µL) was stirred at room temperature under 200 psi hydrogen in a stainless steel pressure vessel for 18 h. Then, the mixture was filtered and evaporated. The residue was purified by silica gel chromatography (4 g column, 0% to 35% EtOAc in hexanes over 15 min) to provide racemic 18-amino-6-hydroxy-6,16-bis(trifluoromethyl)-20-oxa-3,4,14,19-tetrazatricyclo[13.3.1.1²,⁵]icosa-1(19),2,4,15,17-pentaen-13-one. This material was dissolved in 1:1 acetonitrile/methanol and purified by preparative SFC eluting with a gradient of methanol (5 mM NH$_3$) in CO$_2$ (20% to 45% over 10 min) through a 21.2×250 mm LUX-4 column (5 μm particle size) providing two single enantiomer products:

The first enantiomer to elute was isolated as a white crystalline solid, 18-amino-6-hydroxy-6,16-bis(trifluoromethyl)-20-oxa-3,4,14,19-tetrazatricyclo[13.3.1.1²,⁵]icosa-1(19),2,4,15,17-pentaen-13-one (enantiomer 1) (6.9 mg, 27%). $^1$H NMR (400 MHz, Chloroform-d) δ 7.51 (s, 2H), 5.92 (s, 2H), 3.90 (s, 1H), 2.69-2.48 (m, 2H), 2.30 (td, J 13.1, 11.7, 4.1 Hz, 1H), 2.19 (dq, J 15.1, 6.1, 4.9 Hz, 2H), 2.02-1.77 (m, 2H), 1.56-1.32 (m, 4H), 0.99-0.78 (m, 1H) ppm. $^{19}$F NMR (376 MHz, Chloroform-d) δ−62.85, −79.25 ppm. ESI-MS m/z calc. 453.12357, found 454.1 (M+1)$^+$; Retention time: 1.07 minutes (LC Method Q).

The second enantiomer to elute was isolated as a white crystalline solid, 18-amino-6-hydroxy-6,16-bis(trifluoromethyl)-20-oxa-3,4,14,19-tetrazatricyclo[13.3.1.1²,⁵]icosa-1(19),2,4,15,17-pentaen-13-one (enantiomer 2) (7.2 mg, 28%). $^1$H NMR (400 MHz, Chloroform-d) δ 7.54 (s, 1H), 7.51 (s, 1H), 5.94 (s, 2H), 4.10 (s, 1H), 2.57 (dtd, J=24.0, 12.0, 5.5 Hz, 2H), 2.30 (td, J=13.1, 11.9, 3.3 Hz, 1H), 2.23-2.12 (m, 2H), 1.92 (d, J=32.4 Hz, 1H), 1.72-1.30 (m, 6H) ppm. $^{19}$F NMR (376 MHz, Chloroform-d) δ−62.85, −79.25 ppm. ESI-MS m/z calc. 453.12357, found 454.1 (M+1)$^+$; Retention time: 1.07 minutes (LC Method Q).

Example 55: Preparation of 17-amino-6-hydroxy-6,15-bis(trifluoromethyl)-19-oxa-3,4,13,18-tetrazatricyclo[12.3.1.1²,⁵]nonadeca-1(18),2,4,14,16-pentaen-12-one (enantiomer 1) (Compound 108) and 17-amino-6-hydroxy-6,15-bis(trifluoromethyl)-19-oxa-3,4,13,18-tetrazatricyclo[12.3.1.1²,⁵]nonadeca-1(18),2,4,14,16-pentaen-12-one (enantiomer 2) (Compound 109)

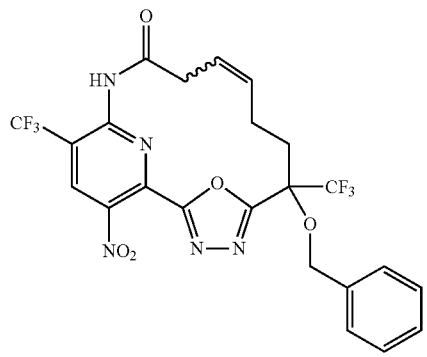

isomer 1

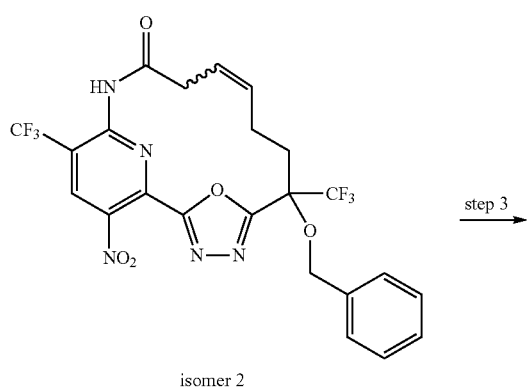

isomer 2 step 3 →

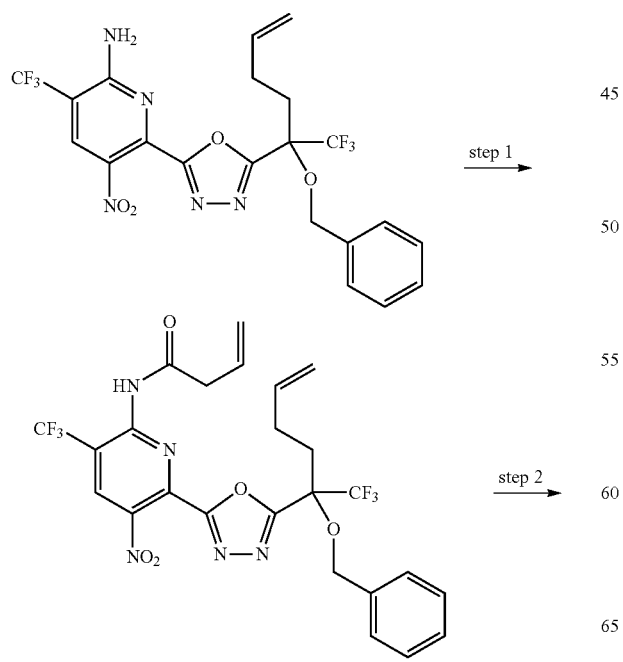

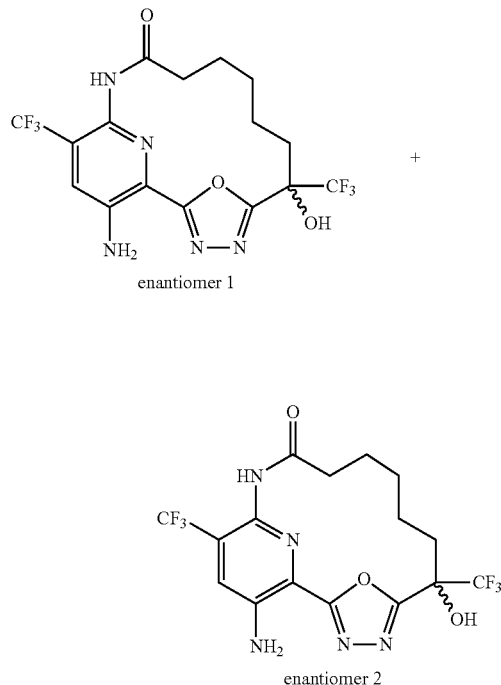

Step 1: N-[6-[5-[1-Benzyloxy-1-(trifluoromethyl)pent-4-enyl]-1,3,4-oxadiazol-2-yl]-5-nitro-3-(trifluoromethyl)-2-pyridyl]but-3-enamide

Step 2: 6-Benzyloxy-17-nitro-6,15-bis(trifluoromethyl)-19-oxa-3,4,13,18-tetrazatricyclo[12.3.1.12,5]nonadeca-1(17),2,4,9,14(18),15-hexaen-12-one (isomer 1) and 6-benzyloxy-17-nitro-6,15-bis(trifluoromethyl)-19-oxa-3,4,13,18-tetrazatricyclo[12.3.1.12,5]nonadeca-1(17),2,4,9,14(18),15-hexaen-12-one (isomer 2)

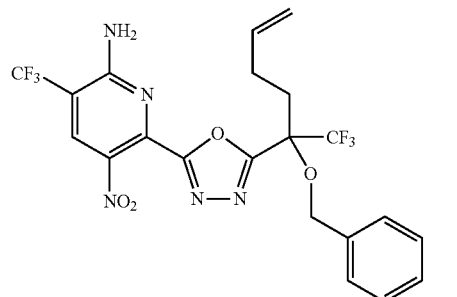

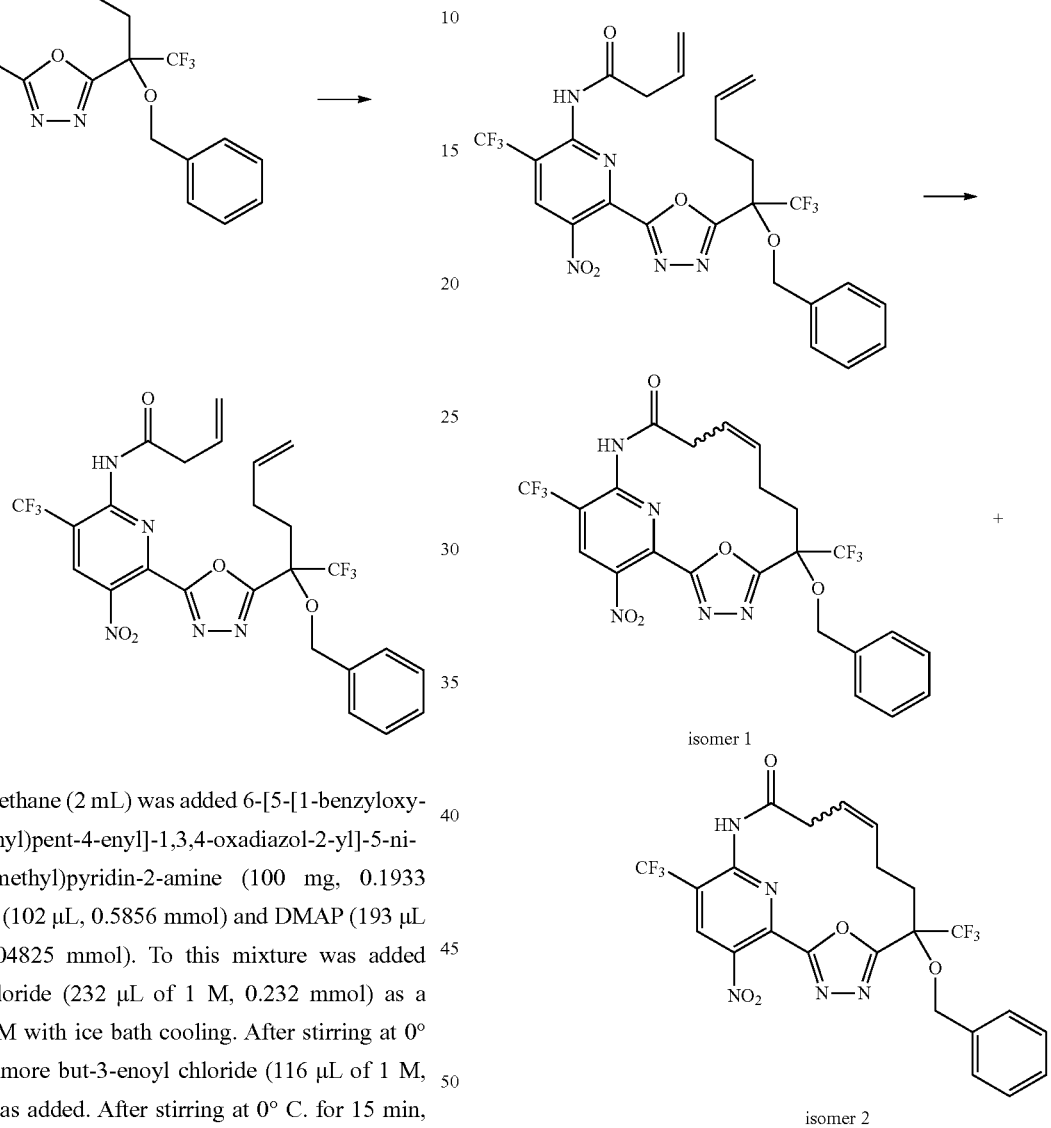

isomer 1 isomer 2

In dichloromethane (2 mL) was added 6-[5-[1-benzyloxy-1-(trifluoromethyl)pent-4-enyl]-1,3,4-oxadiazol-2-yl]-5-nitro-3-(trifluoromethyl)pyridin-2-amine (100 mg, 0.1933 mmol), DIPEA (102 µL, 0.5856 mmol) and DMAP (193 µL of 0.25 M, 0.04825 mmol). To this mixture was added but-3-enoyl chloride (232 µL of 1 M, 0.232 mmol) as a solution in DCM with ice bath cooling. After stirring at 0° C. for 15 min, more but-3-enoyl chloride (116 µL of 1 M, 0.116 mmol) was added. After stirring at 0° C. for 15 min, more but-3-enoyl chloride (145 µL of 1 M, 0.145 mmol) was added. After stirring at 0° C. a further 15 min, the mixture was diluted with DCM and washed with aqueous 1 M NaHCO$_3$, aqueous 0.5 M HCl, water and brine then dried (MgSO$_4$), filtered and evaporated. The residue was purified by silica gel chromatography (4 g column, 0% to 25% EtOAc in hexanes over 15 min) to provide N-[6-[5-[1-benzyloxy-1-(trifluoromethyl)pent-4-enyl]-1,3,4-oxadiazol-2-yl]-5-nitro-3-(trifluoromethyl)-2-pyridyl]but-3-enamide (24 mg, 21%). ESI-MS m/z calc. 585.1447, found 586.2 (M+1)$^+$; Retention time: 1.53 minutes (LC Method J).

In a sealed 20 mL vial, a solution of N-[6-[5-[1-benzyloxy-1-(trifluoromethyl)pent-4-enyl]-1,3,4-oxadiazol-2-yl]-5-nitro-3-(trifluoromethyl)-2-pyridyl]but-3-enamide (23.4 mg, 0.03997 mmol) and 1,3-bis(o-tolyl)-4,5-dihydroimidazole; dichloro-[(2-isopropoxyphenyl)methylene]ruthenium (4.5 mg, 0.007888 mmol) in toluene (3.5 mL) was bubbled with N$_2$ for 1 min and then was heated at 120° C. for 45 min. More catalyst, 1,3-bis(o-tolyl)-4,5-dihydroimidazole; dichloro-[(2-isopropoxyphenyl)methylene]ruthenium (4.5 mg, 0.007888 mmol), was added and heated at 120° C. for 30 min and then the solvent was evaporated. The residue was purified by silica gel chromatography (12 g column, 0% to 20% EtOAc in hexanes over 20 min) to provide two isomeric products.

The first isomer to elute was isolated as 6-benzyloxy-17-nitro-6,15-bis(trifluoromethyl)-19-oxa-3,4,13,18-tetrazatricyclo[12.3.1.1²,⁵]nonadeca-1(17),2,4,9,14(18),15-hexaen-12-one (isomer 1) (6.6 mg, 15%) ESI-MS m/z calc. 557.1134, found 558.0 (M+1)⁺; Retention time: 1.35 minutes (LC Method J).

The second isomer to elute was isolated as 6-benzyloxy-17-nitro-6,15-bis(trifluoromethyl)-19-oxa-3,4,13,18-tetrazatricyclo[12.3.1.1²,⁵]nonadeca-1(17),2,4,9,14(18),15-hexaen-12-one (isomer 2) (2.4 mg, 8%) ESI-MS m/z calc. 557.1134, found 558.1 (M+1)⁺; Retention time: 1.29 minutes (LC Method J).

Step 3: 17-amino-6-hydroxy-6,15-bis(trifluoromethyl)-19-oxa-3,4,13,18-tetrazatricyclo[12.3.1.1²,⁵]nonadeca-1(18),2,4,14,16-pentaen-12-one (enantiomer 1) (Compound 108) and 17-amino-6-hydroxy-6,15-bis(trifluoromethyl)-19-oxa-3,4,13,18-tetrazatricyclo[12.3.1.1²,⁵]nonadeca-1(18),2,4,14,16-pentaen-12-one (enantiomer 2) (Compound 109)

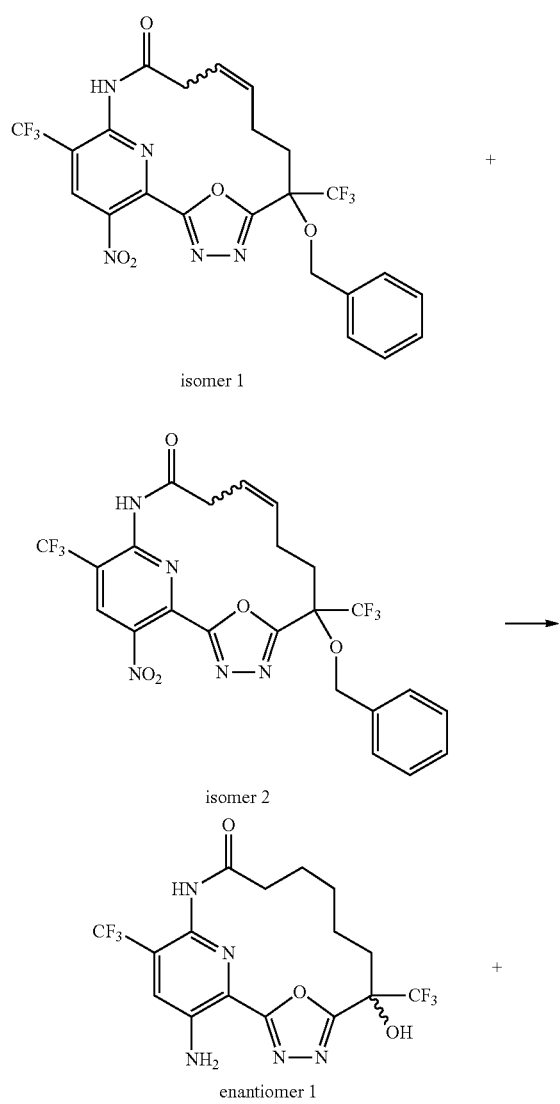

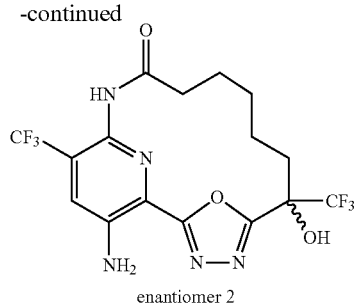

Reaction 1: 6-Benzyloxy-17-nitro-6,15-bis(trifluoromethyl)-19-oxa-3,4,13,18-tetrazatricyclo[12.3.1.1²,⁵]nonadeca-1(17),2,4,9,14(18),15-hexaen-12-one (isomer 1) (6.6 mg, 0.006157 mmol) and palladium on carbon (3.2 mg of 10% w/w, 0.003007 mmol) were added to AcOH (200 μL) and the mixture was stirred at room temperature under 200 psi $H_2$ in a stainless steel pressure vessel for 18 h. Then, the mixture was filtered and the filtrate was evaporated.

Reaction 2: 6-Benzyloxy-17-nitro-6,15-bis(trifluoromethyl)-19-oxa-3,4,13,18-tetrazatricyclo[12.3.1.1²,⁵]nonadeca-1(17),2,4,9,14(18),15-hexaen-12-one (isomer 2) (2.4 mg, 0.003014 mmol) and palladium on carbon (3.2 mg of 10% w/w, 0.003007 mmol) were added to AcOH (200 μL) and the mixture was stirred at room temperature under 200 psi $H_2$ in a stainless steel pressure vessel for 18 h. Then, the mixture was filtered and the filtrate was evaporated.

The crude products from reaction 1 and reaction 2 were combined and the resulting residue was purified by silica gel chromatography (4 g column, 0% to 35% EtOAc in hexanes over 20 min) to provide 2.4 mg of racemic 17-amino-6-hydroxy-6,15-bis(trifluoromethyl)-19-oxa-3,4,13,18-tetrazatricyclo[12.3.1.1²,⁵]nonadeca-1(18),2,4,14,16-pentaen-12-one. This material was dissolved in 1:1 acetonitrile/methanol and purified by preparative SFC eluting with a gradient of methanol (5 mM $NH_3$) in $CO_2$ (20% to 45% over 10 min) through a 21.2×250 mm LUX-4 column (5 μm particle size) providing two single enantiomer products:

The first enantiomer to elute was isolated as a white solid, 17-amino-6-hydroxy-6,15-bis(trifluoromethyl)-19-oxa-3,4,13,18-tetrazatricyclo[12.3.1.1²,⁵]nonadeca-1(18),2,4,14,16-pentaen-12-one (enantiomer 1) (1.1 mg, 41%). ¹H NMR (400 MHz, Chloroform-d) δ 7.61 (s, 1H), 7.49 (s, 1H), 5.63 (s, 2H), 3.91-3.32 (m, 1H), 2.89 (td, J=11.9, 3.9 Hz, 1H), 2.41 (dtd, J=14.5, 11.2, 9.8, 4.8 Hz, 2H), 2.23 (ddt, J=16.3, 12.9, 7.7 Hz, 2H), 2.04 (q, J=4.2 Hz, 1H), 1.87-1.71 (m, 1H), 1.65 (d, J=24.3 Hz, 1H), 1.48 (s, 1H), 0.87 (dd, J=11.5, 4.4 Hz, 1H) ppm. ¹⁹F NMR (376 MHz, Chloroform-d) δ−62.71, −79.79 ppm. ESI-MS m/z calc. 439.1079, found 440.1 (M+1)⁺; Retention time: 1.02 minutes (LC Method Q).

The second enantiomer to elute was isolated as a white solid, 17-amino-6-hydroxy-6,15-bis(trifluoromethyl)-19-oxa-3,4,13,18-tetrazatricyclo[12.3.1.1²,⁵]nonadeca-1(18),2,4,14,16-pentaen-12-one (enantiomer 2) (1.2 mg, 44%). ¹H NMR (400 MHz, Chloroform-d) δ 7.61 (s, 1H), 7.49 (s, 1H), 5.63 (s, 2H), 3.65 (s, 1H), 2.99-2.81 (m, 1H), 2.41 (ddt, J=19.2, 9.8, 4.8 Hz, 2H), 2.23 (ddt, J=16.5, 12.9, 7.7 Hz, 2H), 2.12-1.96 (m, 1H), 1.84-1.71 (m, 1H), 1.66-1.60 (m, 1H), 1.50-1.35 (m, 1H), 0.95-0.74 (m, 1H) ppm. ¹⁹F NMR (376 MHz, Chloroform-d) δ−62.71, −79.79 ppm. ESI-MS m/z calc. 439.1079, found 440.2 (M+1)⁺; Retention time: 1.01 minutes (LC Method Q).

Example 56: Preparation of 20-amino-6-hydroxy-6,
18-bis(trifluoromethyl)-22-oxa-15λ6-thia-3,4,16,21-
tetraazatetracyclo[15.3.1.1²,⁵.0¹²,¹⁶]docosa-1(21),
2,4,17,19-pentaene-15,15-dione (enantiomer 1)
(Compound 110), 20-amino-6-hydroxy-6,18-bis
(trifluoromethyl)-22-oxa-15λ6-thia-3,4,16,21-tet-
raazatetracyclo[15.3.1.1²,⁵.0¹²,¹⁶]docosa-1(21),2,4,
17,19-pentaene-15,15-dione (enantiomer 2)
(Compound 111), 20-amino-6-hydroxy-6,18-bis
(trifluoromethyl)-22-oxa-15λ6-thia-3,4,16,21-tet-
raazatetracyclo[15.3.1.1²,⁵.0¹²,¹⁶]docosa-1(21),2,4,
17,19-pentaene-15,15-dione (enantiomer 3)
(Compound 112), and 20-amino-6-hydroxy-6,18-bis
(trifluoromethyl)-22-oxa-15λ6-thia-3,4,16,21-tet-
raazatetracyclo[15.3.1.1²,⁵.0¹²,¹⁶]docosa-1(21),2,4,
17,19-pentaene-15,15-dione (enantiomer 4)
(Compound 113)

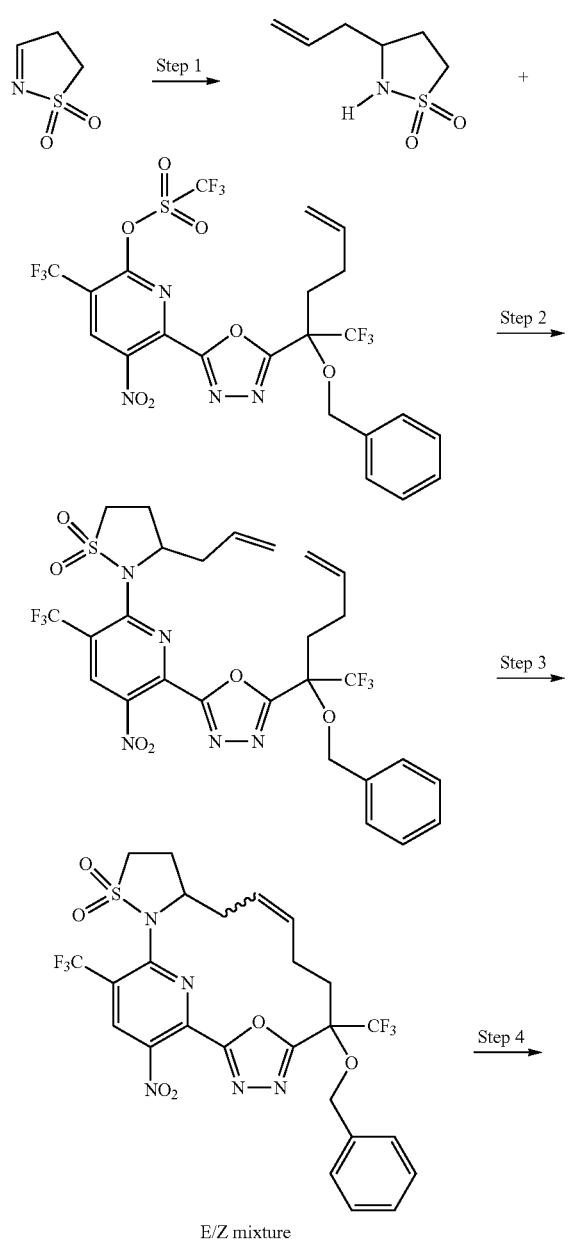

E/Z mixture

-continued

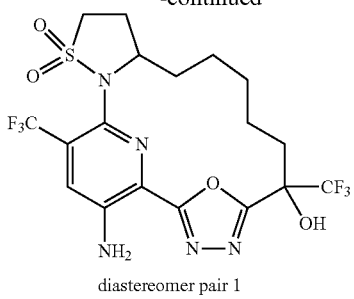

diastereomer pair 1

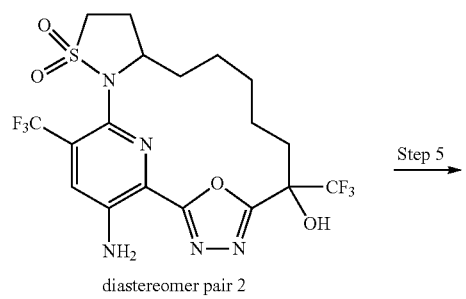

diastereomer pair 2

Step 5

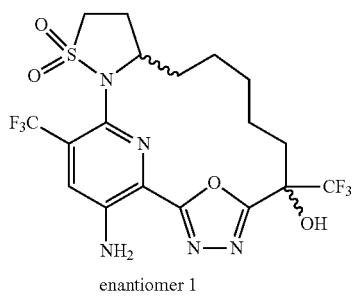

enantiomer 1

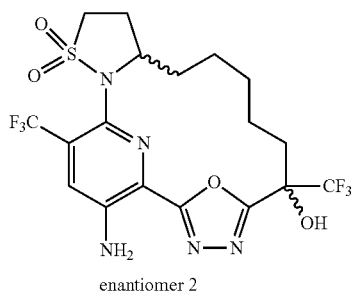

enantiomer 2

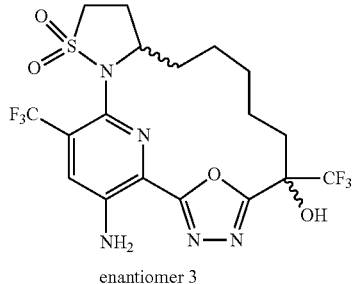

enantiomer 3

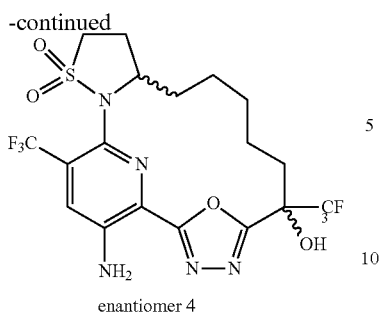

enantiomer 4

Step 1: 3-Allyl-1,2-thiazolidine 1,1-dioxide

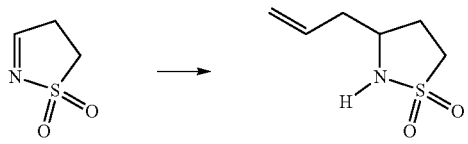

4,5-Dihydroisothiazole 1,1-dioxide (150 mg, 1.1331 mmol) was dissolved in tetrahydrofuran (7.5 mL). The mixture was cooled to 0° C. and then allyl(chloro)magnesium (3 mL of 2 M in tetrahydrofuran, 6 mmol) was added at 0° C. under nitrogen atmosphere. The resulting mixture was stirred at room temperature for 3 h. Upon consumption of the imine intermediate (TLC/stain $KMnO_4$) the reaction was cooled at 0° C. and then was quenched with $NH_4Cl$ saturated (20 mL). The resulting mixture was stirred for 10 minutes and then extracted with ethyl acetate (3×20 mL). The combined organic layers were dried with sodium sulfate, filtered and concentrated under reduced pressure. The crude material was purified by silica gel chromatography using a gradient of 0% to 30% ethyl acetate in dichloromethane to provide as a light-yellow oil, 3-allyl-1,2-thiazolidine 1,1-dioxide (90 mg, 49%). $^1$H NMR (300 MHz, $CDCl_3$) δ 5.88-5.67 (m, 1H), 5.27-5.14 (m, 2H), 4.22 (br s., 1H), 3.78-3.60 (m, 1H), 3.29-3.06 (m, 2H), 2.62-2.45 (m, 1H), 2.38 (t, J=6.8 Hz, 2H), 2.14 (dq, J=13.5, 8.6 Hz, 1H) ppm. ESI-MS m/z calc. 161.051, found 162.1 (M+1)$^+$; Retention time: 0.89 minutes (LC Method E).

Step 2: 3-Allyl-2-[6-[5-[1-benzyloxy-1-(trifluoromethyl)pent-4-enyl]-1,3,4-oxadiazol-2-yl]-5-nitro-3-(trifluoromethyl)-2-pyridyl]-1,2-thiazolidine 1,1-dioxide

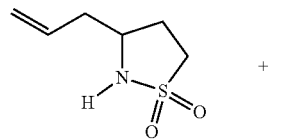 +

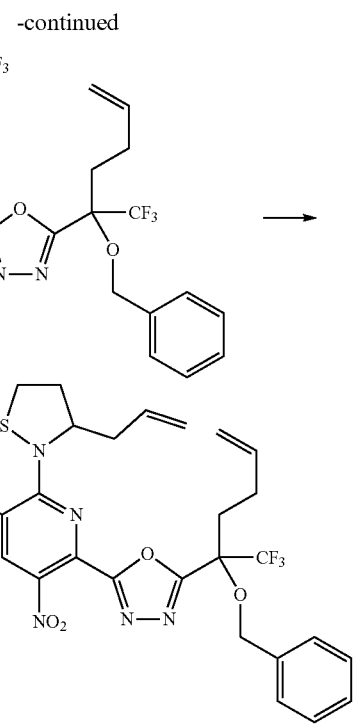

Sodium hydride (60% in mineral oil, 142 mg, 3.5503 mmol) was added to 3-allyl-1,2-thiazolidine 1,1-dioxide (620 mg, 3.8456 mmol) in DMF (21 mL) at 0° C. and the mixture was stirred at room temperature for 30 min. The suspension was cooled to 0° C. and [6-[5-[1-benzyloxy-1-(trifluoromethyl)pent-4-enyl]-1,3,4-oxadiazol-2-yl]-5-nitro-3-(trifluoromethyl)-2-pyridyl] trifluoromethanesulfonate (2.1 g, 3.2286 mmol) in DMF (13 mL) was added and the mixture stirred for 30 minutes at 0° C. Water (40 mL) and ethyl acetate (30 mL) were added and the phases were separated. The aqueous phase was extracted with ethyl acetate (2×30 mL). The organic phases were combined, washed with water (50 mL) and brine (50 mL), dried over anhydrous sodium sulfate, filtered and concentrated under reduced pressure. The resulting residue was purified by silica-gel chromatography (80 g column) eluting from 0% to 40% ethyl acetate in heptane to afford as a yellow gum, 3-allyl-2-[6-[5-[1-benzyloxy-1-(trifluoromethyl)pent-4-enyl]-1,3,4-oxadiazol-2-yl]-5-nitro-3-(trifluoromethyl)-2-pyridyl]-1,2-thiazolidine 1,1-dioxide (1.4 g, 65%). NMR (300 MHz, $CDCl_3$) δ 8.76 (s, 1H), 7.43-7.29 (m, 5H), 5.89-5.55 (m, 2H), 5.15-4.95 (m, 4H), 4.89-4.80 (m, 1H), 4.69-4.61 (m, 1H), 3.49-3.38 (m, 1H), 3.17-3.01 (m, 1H), 2.73-2.59 (m, 1H), 2.58-2.16 (m, 8H) ppm. $^{19}$F NMR (282 MHz, $CDCl_3$) δ −59.63 (s, 3F), −73.09 (br. s., 3F) ppm. ESI-MS m/z calc. 661.143, found 662.2 (M+1)$^+$; Retention time: 2.32 minutes (LC Method E).

Step 3: 6-Benzyloxy-20-nitro-6,18-bis(trifluoromethyl)-22-oxa-15λ6-thia-3,4,16,21-tetrazatetracyclo [15.3.1.1²,⁵.0¹²,¹⁶]docosa-1(20),2,4,9,17(21),18-hexaene 15,15-dioxide (E/Z mixture)

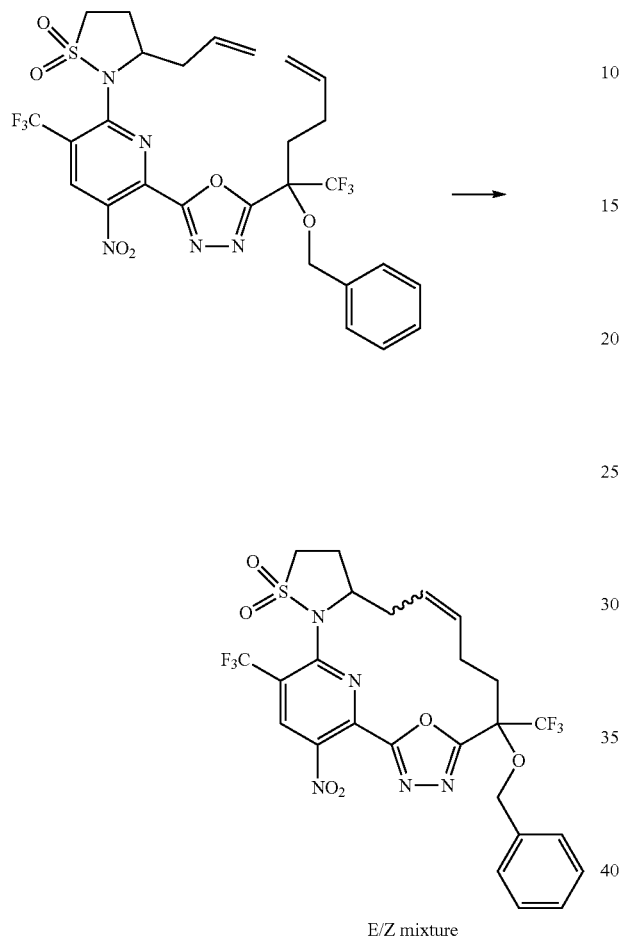

E/Z mixture

Zhan catalyst-1B (133 mg, 0.1813 mmol) in dichloroethane (168 mL) was degassed by bubbling nitrogen and heated to 60° C. Then, 3-allyl-2-[6-[5-[1-benzyloxy-1-(trifluoromethyl)pent-4-enyl]-1,3,4-oxadiazol-2-yl]-5-nitro-3-(trifluoromethyl)-2-pyridyl]-1,2-thiazolidine 1,1-dioxide (1.05 g, 1.5871 mmol) in dichloroethane (168 mL) was added dropwise over 1 h. The resulting mixture was heated to 75° C. and stirred for 5 h. The mixture was cooled down and concentrated under reduced pressure. The residue was purified by silica gel chromatography using a gradient from 0% to 40% ethyl acetate in heptane to afford as a green solid, 6-benzyloxy-20-nitro-6,18-bis(trifluoromethyl)-22-oxa-15λ6-thia-3,4,16,21-tetrazatetracyclo[15.3.1.1²,⁵.0¹²,¹⁶] docosa-1(20),2,4,9,17(21),18-hexaene 15,15-dioxide (E/Z mixture) (195 mg, 19%). ESI-MS m/z calc. 633.1117, found 634.2 (M+1)⁺; Retention time: 2.3 minutes (LC Method E).

Step 4: 20-Amino-6-hydroxy-6,18-bis(trifluoromethyl)-22-oxa-15λ6-thia-3,4,16,21-tetraazatetracyclo [15.3.1.1²,⁵.0¹²,¹⁶]docosa-1(21),2,4,17,19-pentaene-15,15-dione (diastereomer pair 1) and 20-amino-6-hydroxy-6,18-bis(trifluoromethyl)-22-oxa-15λ6-thia-3,4,16,21-tetraazatetracyclo [15.3.1.1²,⁵.0¹²,¹⁶]docosa-1(21),2,4,17,19-pentaene-15,15-dione (diastereomer pair 2)

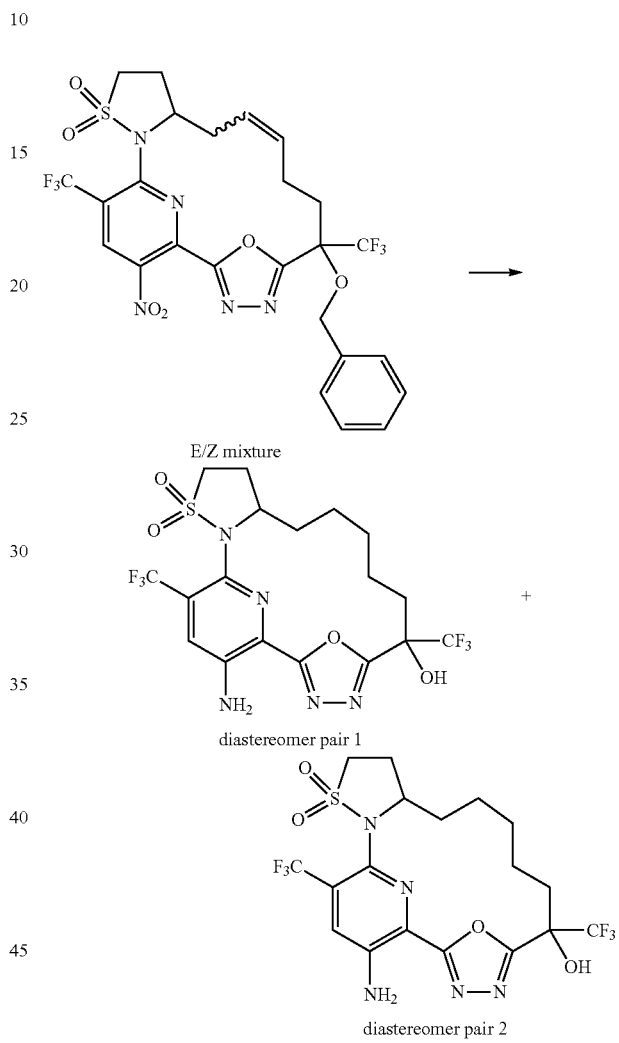

6-Benzyloxy-20-nitro-6,18-bis(trifluoromethyl)-22-oxa-15λ6-thia-3,4,16,21-tetrazatetracyclo[15.3.1.1²,⁵.0¹²,¹⁶] docosa-1(20),2,4,9,17(21),18-hexaene 15,15-dioxide (E/Z mixture) (30 mg, 0.0426 mmol) was dissolved in methanol (3 mL). The mixture was bubbled with nitrogen for 5 min and then palladium on carbon (10%, wet) (20 mg, 0.0094 mmol) was added. The resulting mixture was bubbled with a balloon of hydrogen for 5 min and then stirred at room temperature under hydrogen overnight. The mixture was filtered through a pad of Celite and washed with methanol (25 mL) then concentrated under reduced pressure. The residue was purified by silica gel chromatography (4 g column) eluting from 0% to 80% ethyl acetate in heptane to afford two different diastereomeric products:

The first product to elute was isolated as a yellow solid, 20-amino-6-hydroxy-6,18-bis(trifluoromethyl)-22-oxa-15λ6-thia-3,4,16,21-tetraazatetracyclo[15.3.1.1²,⁵.0¹²,¹⁶]

docosa-1(21),2,4,17,19-pentaene-15,15-dione (diastereomer pair 1) (4 mg, 18%). ¹H NMR (300 MHz, CD₃OD) δ 7.72 (s, 1H), 4.69-4.52 (m, 1H), 3.46-3.35 (m, 1H), 3.28-3.18 (m, 2H), 2.72-2.55 (m, 1H), 2.36-2.17 (m, 2H), 2.14-2.02 (m, 1H), 1.97-1.68 (m, 3H), 1.66-1.44 (m, 4H) ppm. ¹⁹F NMR (282 MHz, CD₃OD) δ −60.96 (s, 3F), −81.11 (s, 3F) ppm. ESI-MS m/z calc. 515.1062, found 516.1 (M+1)⁺; Retention time: 1.9 minutes (LC Method E).

The second product to elute was isolated as a yellow solid, 20-amino-6-hydroxy-6,18-bis(trifluoromethyl)-22-oxa-15λ6-thia-3,4,16,21-tetraazatetracyclo[15.3.1.1²,⁵.0¹²,¹⁶] docosa-1(21),2,4,17,19-pentaene-15,15-dione (diastereomer pair 2) (4 mg, 18%). ¹H NMR (300 MHz, CDCl₃) δ 7.45 (s, 1H), 5.68 (br s, 2H), 4.70-4.56 (m, 1H), 4.49-4.37 (m, 1H), 3.66-3.57 (m, 1H), 3.38-3.04 (m, 3H), 2.62-1.99 (m, 6H), 1.94-1.59 (m, 4H) ppm. ¹⁹F NMR (282 MHz, CDCl₃) δ −59.90 (s, 3F), −78.75 (s, 3F) ppm. ESI-MS m/z calc. 515.1062, found 516.1 (M+1)⁺; Retention time: 1.9 minutes (LC Method E).

Step 5: 20-Amino-6-hydroxy-6,18-bis(trifluoromethyl)-22-oxa-15λ6-thia-3,4,16,21-tetraazatetracyclo [15.3.1.1²,⁵.0¹²,¹⁶]docosa-1(21),2,4,17,19-pentaene-15,15-dione (enantiomer 1) (Compound 110), 20-amino-6-hydroxy-6,18-bis(trifluoromethyl)-22-oxa-15λ6-thia-3,4,16,21-tetraazatetracyclo [15.3.1.1²,⁵.0¹²,¹⁶]docosa-1(21),2,4,17,19-pentaene-15,15-dione (enantiomer 2) (Compound 111), 20-amino-6-hydroxy-6,18-bis(trifluoromethyl)-22-oxa-15λ6-thia-3,4,16,21-tetraazatetracyclo [15.3.1.1²,⁵.0¹²,¹⁶]docosa-1(21),2,4,17,19-pentaene-15,15-dione (enantiomer 3) (Compound 112), and 20-amino-6-hydroxy-6,18-bis(trifluoromethyl)-22-oxa-15λ6-thia-3,4,16,21-tetraazatetracyclo [15.3.1.1²,⁵.0¹²,¹⁶]docosa-1(21),2,4,17,19-pentaene-15,15-dione (enantiomer 4) (Compound 113)

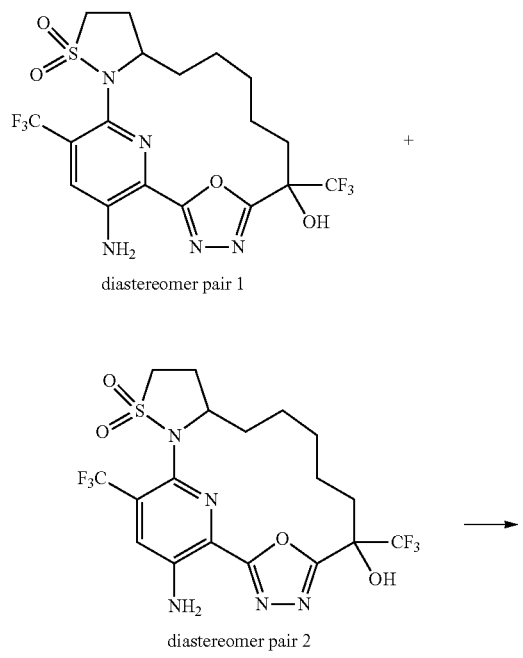

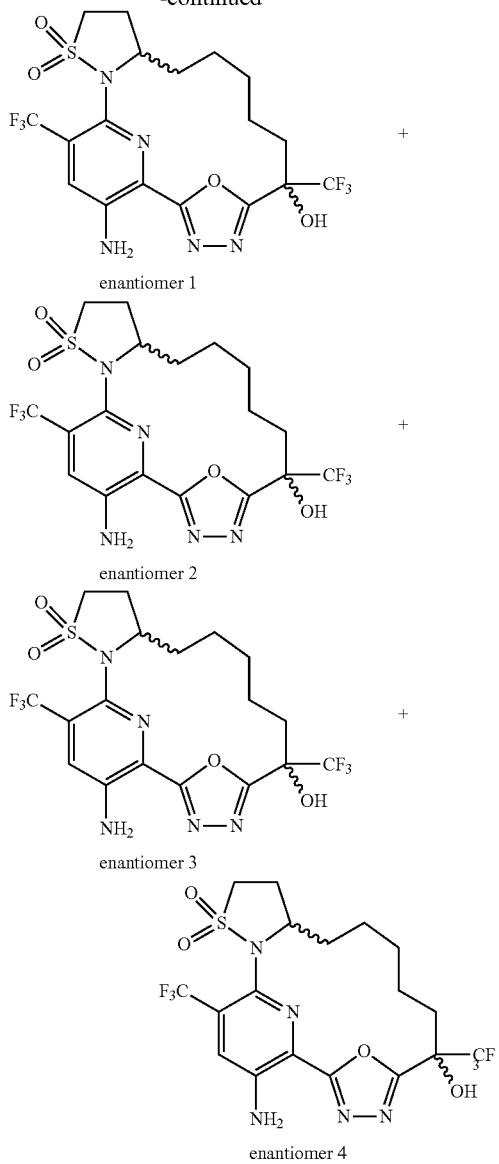

A mixture of 20-amino-6-hydroxy-6,18-bis(trifluoromethyl)-22-oxa-15λ6-thia-3,4,16,21-tetraazatetracyclo [15.3.1.1²,⁵.0¹²,¹⁶]docosa-1(21),2,4,17,19-pentaene-15,15-dione (diastereomer pair 1) and 20-amino-6-hydroxy-6,18-bis(trifluoromethyl)-22-oxa-15λ6-thia-3,4,16,21-tetraazatetracyclo[15.3.1.1²,⁵.0¹²,¹⁶]docosa-1(21),2,4,17,19-pentaene-15,15-dione (diastereomer pair 2) (121 mg, 0.235 mmol) was purified by silica gel column chromatography (12 g column) eluting from 0% to 20% then to 60% of ethyl acetate in heptanes followed by purification of the mixed fractions again by silica gel column chromatography (12 g column) eluting from 0% to 20% to 60% of ethyl acetate in heptanes to afford two diastereomer pair products.

The first diastereomer pair was purified to separate the enantiomers by chiral SFC (cellulose 5 column; 20% methanol in CO₂; flow=75 mL/min; 40° C.) to afford two products as single enantiomers.

The first enantiomer was isolated as an off-white solid, 20-amino-6-hydroxy-6,18-bis(trifluoromethyl)-22-oxa-15λ6-thia-3,4,16,21-tetraazatetracyclo[15.3.1.1²,⁵.0¹²,¹⁶]

docosa-1(21),2,4,17,19-pentaene-15,15-dione (enantiomer 1) (14 mg, 11%). $^1$H NMR (300 MHz, DMSO-d6) δ 7.79 (s, 1H), 7.66 (s, 1H), 6.96 (br. s, 2H), 4.52-4.38 (m, 1H), 3.54-3.41 (m, 1H), 3.27-3.18 (m, 1H), 2.21-2.05 (m, 2H), 2.02-1.88 (m, 1H), 1.79-1.67 (m, 2H), 1.63-1.37 (m, 4H), 1.27-1.02 (m, 3H) ppm. $^{19}$F NMR (282 MHz, DMSO-d6) δ −58.50 (s, 3F), −78.49 (s, 3F) ppm. ESI-MS m/z calc. 515.1062, found 516.1 (M+1)$^+$; Retention time: 2.93 minutes (LC Method C).

The second enantiomer was isolated as an off-white solid, 20-amino-6-hydroxy-6,18-bis(trifluoromethyl)-22-oxa-15λ6-thia-3,4,16,21-tetraazatetracyclo[15.3.1.1 2,5.0 12,16]docosa-1(21),2,4,17,19-pentaene-15,15-dione (enantiomer 2) (12 mg, 10%). $^1$H NMR (300 MHz, DMSO-d6) δ 7.79 (s, 1H), 7.66 (s, 1H), 6.96 (br. s., 2H), 4.52-4.38 (m, 1H), 3.53-3.41 (m, 1H), 3.27-3.18 (m, 1H), 2.20-2.08 (m, 2H), 2.03-1.90 (m, 1H), 1.78-1.67 (m, 2H), 1.63-1.37 (m, 4H), 1.25-1.03 (m, 3H) ppm. $^{19}$F NMR (282 MHz, DMSO-d6) δ −58.50 (s, 3F), −78.49 (s, 3F) ppm. ESI-MS m/z calc. 515.1062, found 516.1 (M+1)$^+$; Retention time: 2.93 minutes (LC Method C).

The second diastereomer pair was purified to separate the enantiomers by chiral SFC (amylose 1 column; 10% methanol in CO$_2$; flow=75 mL/min; 40° C.) to afford two products as single enantiomers.

The first enantiomer was isolated as an off-white solid, 20-amino-6-hydroxy-6,18-bis(trifluoromethyl)-22-oxa-15λ6-thia-3,4,16,21-tetraazatetracyclo[15.3.1.1 2,5.0 12,16]docosa-1(21),2,4,17,19-pentaene-15,15-dione (enantiomer 3) (12 mg, 9%). $^1$H NMR (300 MHz, DMSO-d6) δ 7.78 (s, 1H), 7.61 (s, 1H), 6.87 (br. s., 2H), 4.72-4.58 (m, 1H), 3.58-3.46 (m, 1H), 3.26-3.20 (m, 1H), 2.69-2.56 (m, 1H), 2.18-2.01 (m, 3H), 1.70-1.57 (m, 2H), 1.53-1.40 (m, 3H), 1.36-1.19 (m, 3H) ppm. $^{19}$F NMR (282 MHz, DMSO-d6) δ −58.16 (s, 3F), −77.49 (s, 3F) ppm. ESI-MS m/z calc. 515.1062, found 516.1 (M+1)$^+$; Retention time: 2.93 minutes (LC Method C).

The second enantiomer was isolated as an off-white solid, 20-amino-6-hydroxy-6,18-bis(trifluoromethyl)-22-oxa-15λ6-thia-3,4,16,21-tetraazatetracyclo[15.3.1.1 2,5.0 12,16]docosa-1(21),2,4,17,19-pentaene-15,15-dione (enantiomer 4) (10 mg, 8%). $^1$H NMR (300 MHz, DMSO-d6) δ 7.78 (s, 1H), 7.61 (s, 1H), 6.87 (br. s., 2H), 4.72-4.58 (m, 1H), 3.59-3.46 (m, 1H), 3.26-3.19 (m, 1H), 2.68-2.57 (m, 1H), 2.16-2.00 (m, 3H), 1.72-1.57 (m, 2H), 1.54-1.40 (m, 3H), 1.36-1.19 (m, 3H) ppm. $^{19}$F NMR (282 MHz, DMSO-d6) δ −58.16 (s, 3F), −77.49 (s, 3F) ppm. ESI-MS m/z calc. 515.1062, found 516.1 (M+1)$^+$; Retention time: 2.93 minutes (LC Method C).

Example 57: Preparation of (12R)-20-amino-18-methoxy-6-(trifluoromethyl)-22-oxa-3,4,16,21-tetraazatetracyclo[15.3.1.1 2,5.0 12,16]docosa-1(20),2,4,17(21),18-pentaen-6-ol (enantiomer 1) (Compound 114) and (12R)-20-amino-18-methoxy-6-(trifluoromethyl)-22-oxa-3,4,16,21-tetraazatetracyclo[15.3.1.1 2,5.0 12,16]docosa-1(20),2,4,17(21),18-pentaen-6-ol (enantiomer 2) (Compound 115)

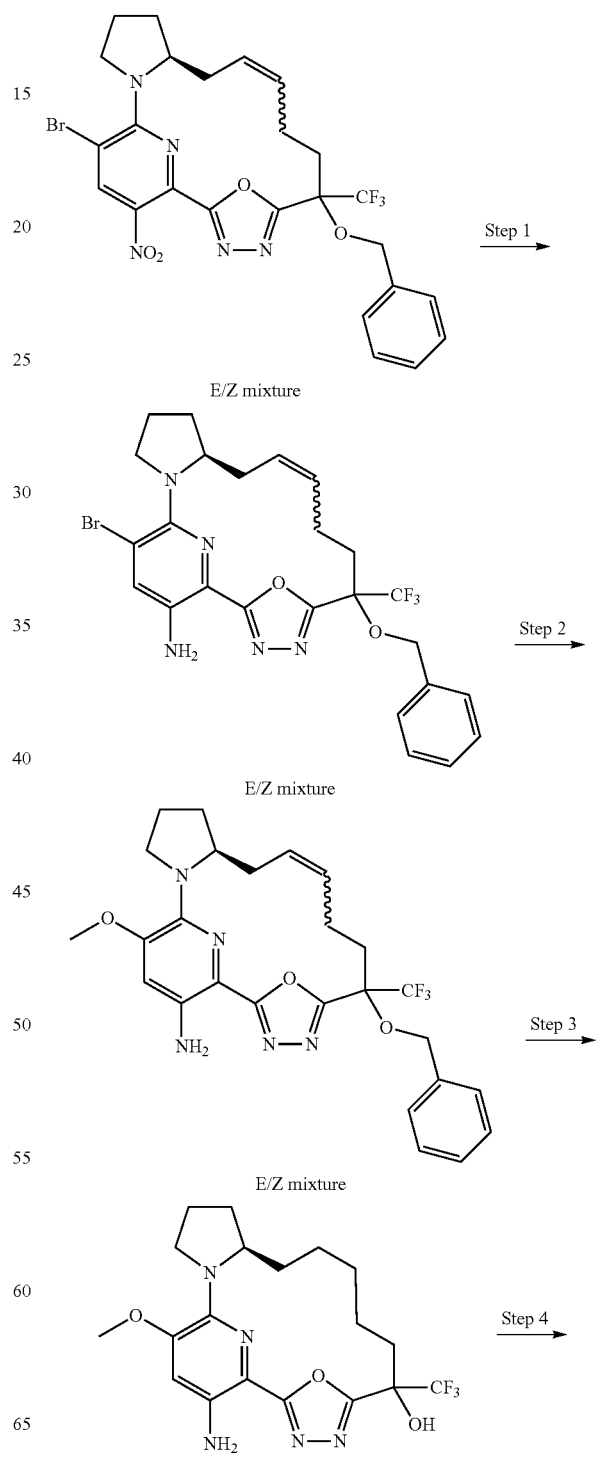

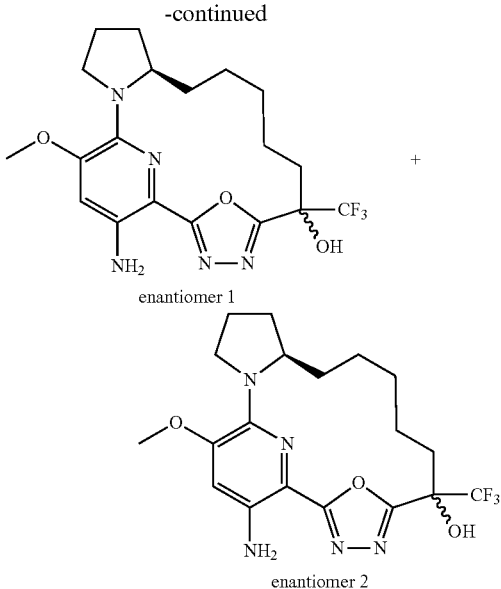

enantiomer 1 enantiomer 2

Step 1: (12S)-6-(Benzyloxy)-18-bromo-6-(trifluoromethyl)-22-oxa-3,4,16,21-tetraazatetracyclo[15.3.1.1 2,5.0 12,16]docosa-1(21),2,4,9,17,19-hexaen-20-amine (E/Z mixture)

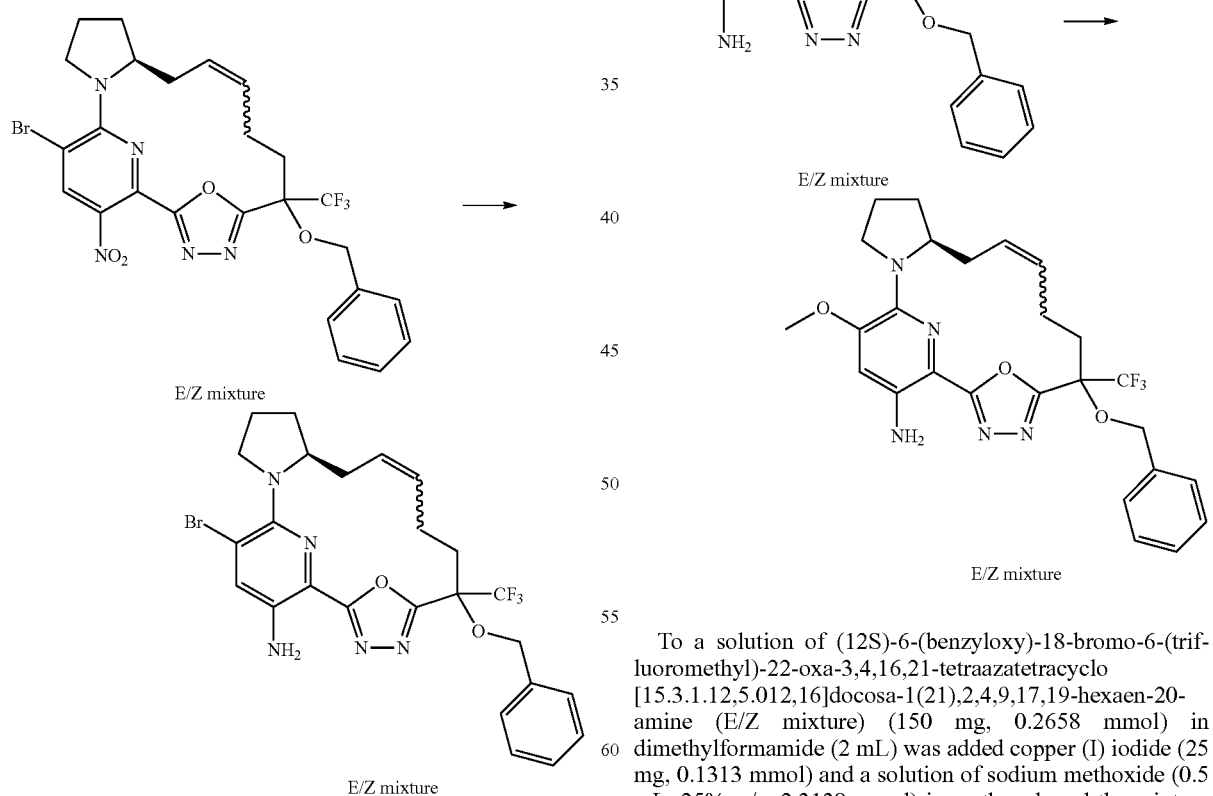

E/Z mixture

E/Z mixture

E/Z mixture

E/Z mixture

To a solution of (12S)-6-(benzyloxy)-18-bromo-20-nitro-6-(trifluoromethyl)-22-oxa-3,4,16,21-tetraazatetracyclo[15.3.1.1 2,5.0 12,16]docosa-1(21),2,4,9,17,19-hexaene (E/Z mixture) (1.7 g, 2.4282 mmol) in ethanol (68 mL) and water (17 mL) was added iron (1.6 g, 28.651 mmol) and ammonium chloride (170 mg, 3.1781 mmol) at room temperature. The mixture was heated at 80° C. for 2 hours, then cooled to room temperature. The reaction was filtered over Celite, the filtrate was diluted with saturated aqueous $NH_4Cl$ solution (50 mL) and water (50 mL). Extracted with EtOAc (3×50 mL) and the combined organic layers were dried over anhydrous $Na_2SO_4$, filtered and concentrated. The residue was purified by silica gel chromatography (40 g column) using a gradient from 0% to 20% ethyl acetate in heptane giving as a yellow foam, (12S)-6-(benzyloxy)-18-bromo-6-(trifluoromethyl)-22-oxa-3,4,16,21-tetraazatetracyclo[15.3.1.1 2,5.0 12,16]docosa-1(21),2,4,9,17,19-hexaen-20-amine (E/Z mixture) (1.1 g, 80%). ESI-MS m/z calc. 563.1144, found 564.1 (M+1)$^+$; Retention time: 2.55 minutes (LC Method E).

Step 2: (12S)-6-(Benzyloxy)-18-methoxy-6-(trifluoromethyl)-22-oxa-3,4,16,21-tetraazatetracyclo[15.3.1.1 2,5.0 12,16]docosa-1(21),2,4,9,17,19-hexaen-20-amine (E/Z mixture)

To a solution of (12S)-6-(benzyloxy)-18-bromo-6-(trifluoromethyl)-22-oxa-3,4,16,21-tetraazatetracyclo[15.3.1.1 2,5.0 12,16]docosa-1(21),2,4,9,17,19-hexaen-20-amine (E/Z mixture) (150 mg, 0.2658 mmol) in dimethylformamide (2 mL) was added copper (I) iodide (25 mg, 0.1313 mmol) and a solution of sodium methoxide (0.5 mL, 25% w/v, 2.3138 mmol) in methanol, and the mixture was stirred at 105° C. for 4 hours. The mixture was cooled to room temperature and diluted with water (25 mL) and filtered over Celite. The filtrate was extracted with ethyl acetate (2×25 mL) and the combined organic layers were washed with brine (2×25 mL), dried over sodium sulfate, filtered and concentrated under reduced pressure. The resulting residue was purified by silica gel chromatography (40 g column) using a gradient from 0% to 25% ethyl acetate in heptane giving as a red solid, (12S)-6-(benzyloxy)-18-methoxy-6-(trifluoromethyl)-22-oxa-3,4,16,21-tetraazatetracyclo[15.3.1.12,5.012,16]docosa-1(21),2,4,9,17,19-hexaen-20-amine (E/Z mixture) (55 mg, 38%). $^1$H NMR (300 MHz, Chloroform-d) δ 7.51-7.26 (m, 5H), 6.49 (s, 1H), 5.66-5.46 (m, 2H), 5.21-4.91 (m, 3H), 4.75-4.60 (m, 1H), 4.02-3.89 (m, 1H), 3.86 (s, 3H), 3.82-3.73 (m, 1H), 3.72-3.54 (m, 1H), 3.47-3.32 (m, 1H), 3.10-2.88 (m, 1H), 2.59-2.39 (m, 1H), 2.35-2.10 (m, 3H), 2.06-1.90 (m, 1H), 1.87-1.67 (m, 2H), 1.57-1.41 (m, 1H) ppm. $^{19}$F NMR (282 MHz, Chloroform-d) δ −75.31 (s, 3F) ppm. ESI-MS m/z calc. 515.2144, found 516.3 (M+1)$^+$; Retention time: 2.57 minutes (LC Method E).

Step 3: (12R)-20-Amino-18-methoxy-6-(trifluoromethyl)-22-oxa-3,4,16,21-tetraazatetracyclo[15.3.1.12,5.012,16]docosa-1(20),2,4,17(21),18-pentaen-6-ol

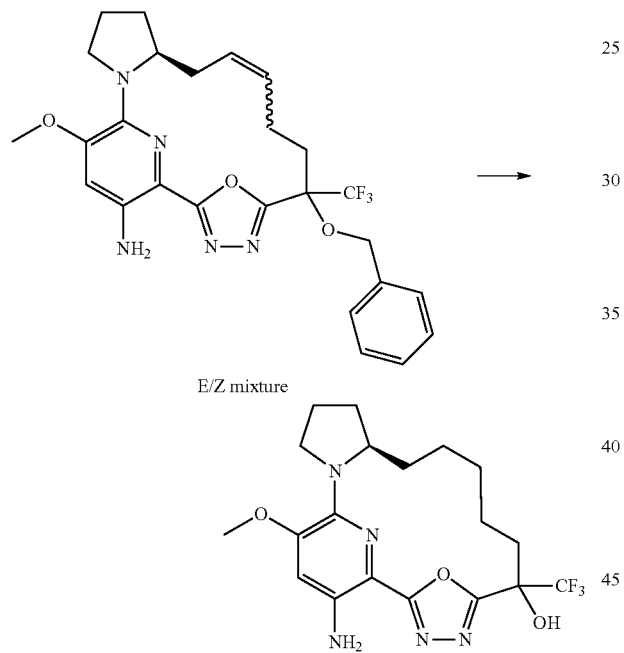

E/Z mixture

A solution of (12S)-6-(benzyloxy)-18-methoxy-6-(trifluoromethyl)-22-oxa-3,4,16,21-tetraazatetracyclo[15.3.1.12,5.012,16]docosa-1(21),2,4,9,17,19-hexaen-20-amine (E/Z mixture) (50 mg, 0.097 mmol) in methanol (5 mL) was bubbled with nitrogen for 5 min and then 10% palladium on carbon (90 mg, 0.0423 mmol) was added. The resulting mixture was bubbled with a balloon of hydrogen for 5 min and then stirred at room temperature under hydrogen overnight. The mixture was filtered through a pad of Celite and washed with methanol (25 mL). The resulting filtrate was concentrated under reduced pressure. The residue was dissolved in dimethyl sulfoxide (2 mL) and then was purified by reverse phase HPLC using a gradient from 5% to 95% acetonitrile in water (+0.1% formic acid) giving as a dark-green solid and mixture of diastereomers, (12R)-20-amino-18-methoxy-6-(trifluoromethyl)-22-oxa-3,4,16,21-tetraazatetracyclo[15.3.1.12,5.012,16]docosa-1(20),2,4,17(21),18-pentaen-6-ol (30 mg, 60%). $^1$H NMR (300 MHz, Chloroform-d) δ 6.46 (br. s., 1H), 5.26-4.82 (m, 2H), 3.97-3.75 (m, 4H), 3.45-3.30 (m, 1H), 2.75-2.31 (m, 2H), 2.30-1.89 (m, 4H), 1.84-1.45 (m, 8H), 1.37-1.27 (m, 1H), 0.97-0.81 (m, 1H) ppm. $^{19}$F NMR (282 MHz, Chloroform-d) δ −77.28 (br. s., 3F, minor diastereomer), −80.82 (br. s., 3F, major diastereomer) ppm. ESI-MS m/z calc. 427.1831, found 428.2 (M+1)$^+$; Retention time: 3.12 minutes (LC Method X).

Step 4: (12R)-20-Amino-18-methoxy-6-(trifluoromethyl)-22-oxa-3,4,16,21-tetraazatetracyclo[15.3.1.12,5.012,16]docosa-1(20),2,4,17(21),18-pentaen-6-ol (enantiomer 1) (Compound 114) and (12R)-20-amino-18-methoxy-6-(trifluoromethyl)-22-oxa-3,4,16,21-tetraazatetracyclo[15.3.1.12,5.012,16]docosa-1(20),2,4,17(21),18-pentaen-6-ol (enantiomer 2) (Compound 115)

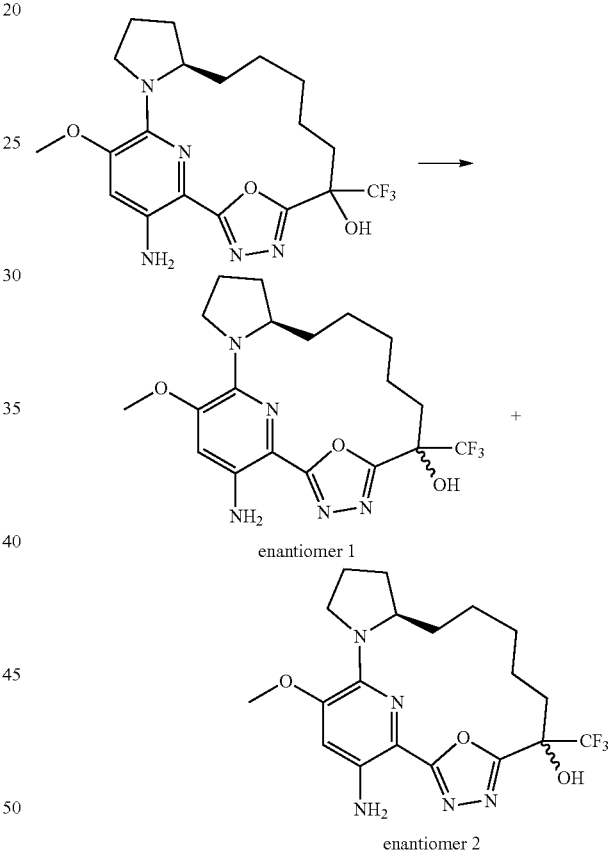

enantiomer 1 enantiomer 2

(12R)-20-Amino-18-methoxy-6-(trifluoromethyl)-22-oxa-3,4,16,21-tetraazatetracyclo[15.3.1.12,5.012,16]docosa-1(20),2,4,17(21),18-pentaen-6-ol (29 mg, 0.06785 mmol) was purified by SFC using a LUX-4 column (250× 21.2 mm, 5 μm particle size) sold by Phenomenex and a dual gradient run from 15% to 40% MeOH (+20 mM NH$_3$) in CO$_2$ over 14.5 minutes giving two single enantiomer products:

The first enantiomer to elute was isolated as a yellow solid, (12R)-20-amino-18-methoxy-6-(trifluoromethyl)-22-oxa-3,4,16,21-tetraazatetracyclo[15.3.1.12,5.012,16]docosa-1(20),2,4,17(21),18-pentaen-6-ol (enantiomer 1) (9.2 mg, 62%). ESI-MS m/z calc. 427.18314, found 428.0 (M+1)$^+$; Retention time: 1.96 minutes (LC Method D).

The second enantiomer to elute was isolated as a yellow solid, (12R)-20-amino-18-methoxy-6-(trifluoromethyl)-22-oxa-3,4,16,21-tetraazatetracyclo[15.3.1.1²,⁵.0¹²,¹⁶]docosa-1(20),2,4,17(21),18-pentaen-6-ol (enantiomer 2) (5.4 mg, 37%). ESI-MS m/z calc. 427.18314, found 428.0 (M+1)⁺; Retention time: 1.86 minutes (LC Method D).

Example 58: Preparation of (12R)-21-amino-6-hydroxy-6,19-bis(trifluoromethyl)-14,23-dioxa-3,4,17,22-tetraazatetracyclo[16.3.1.1²,⁵.0¹²,¹⁷]tricosa-1(21),2,4,18(22),19-pentaen-16-one (enantiomer 1) (Compound 116) and (12R)-21-amino-6-hydroxy-6,19-bis(trifluoromethyl)-14,23-dioxa-3,4,17,22-tetraazatetracyclo[16.3.1.1²,⁵.0¹²,¹⁷]tricosa-1(21),2,4,18(22),19-pentaen-16-one (enantiomer 2) (Compound 117)

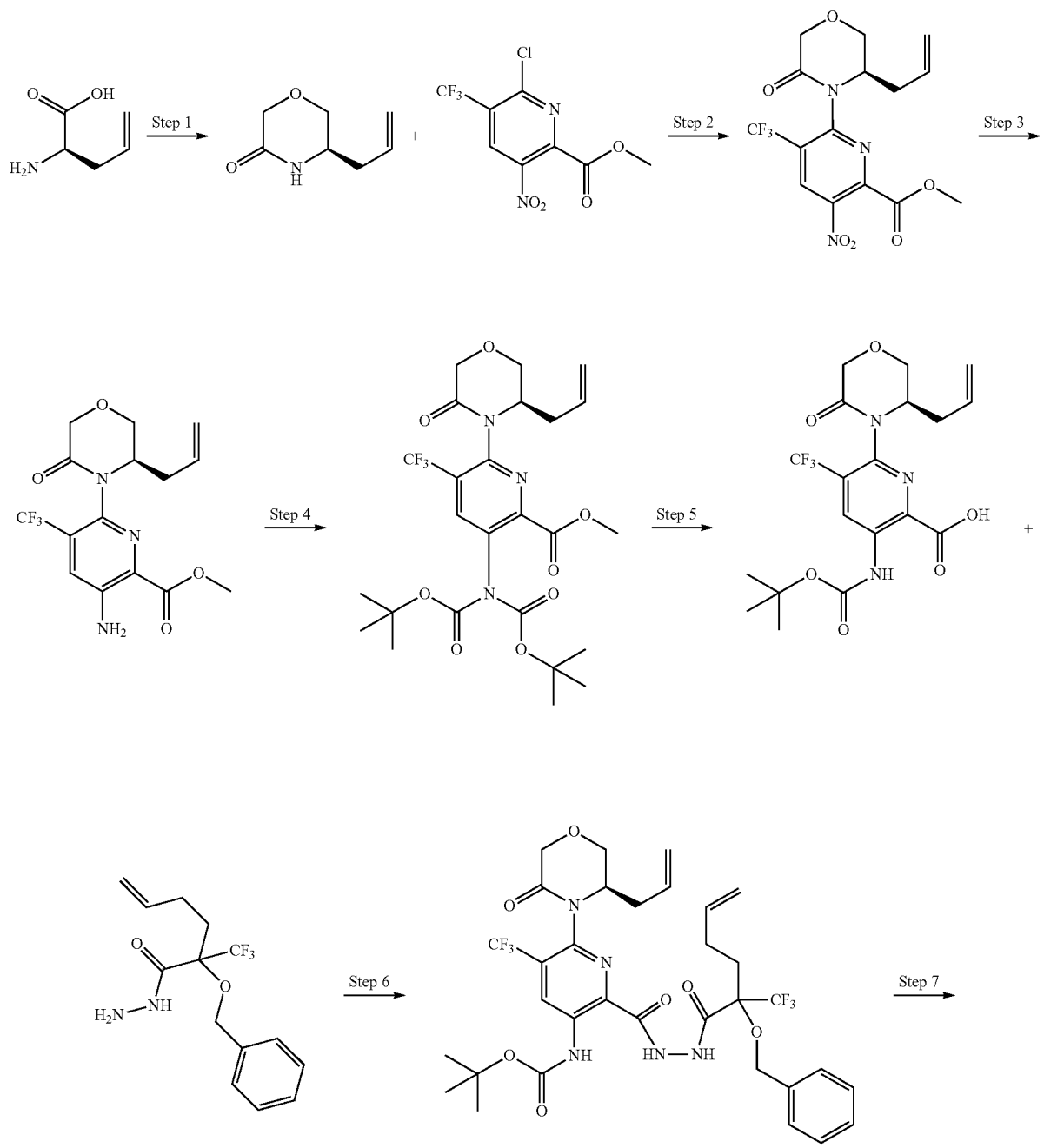

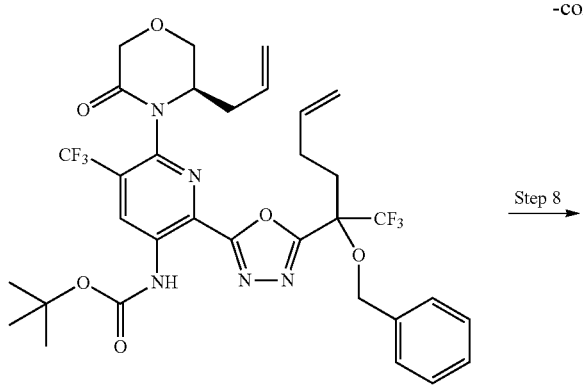

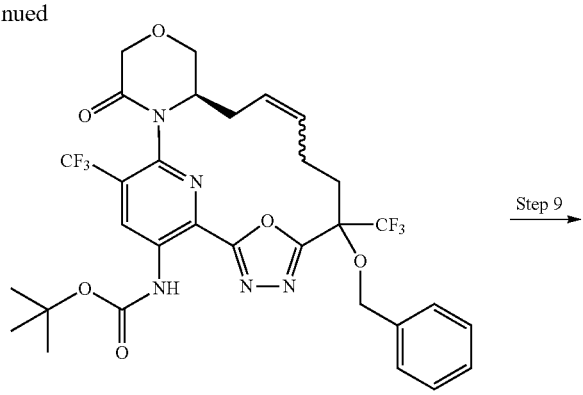

E/Z mixture

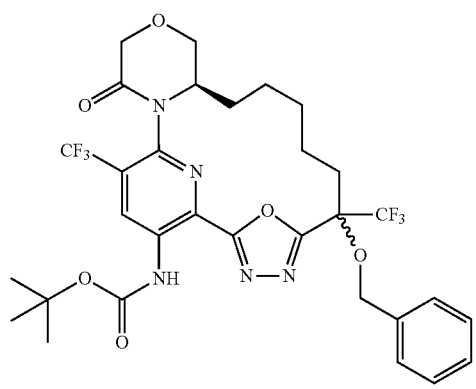

enantiomer 1

+

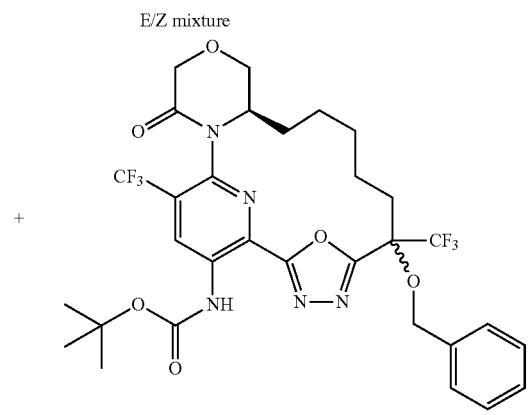

enantiomer 2

|Step 10

|Step 11

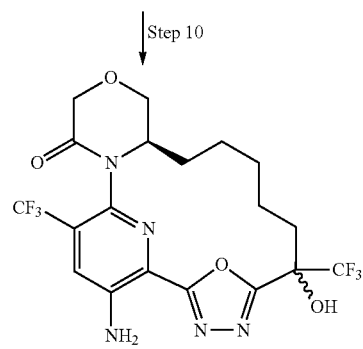

enantiomer 1

+

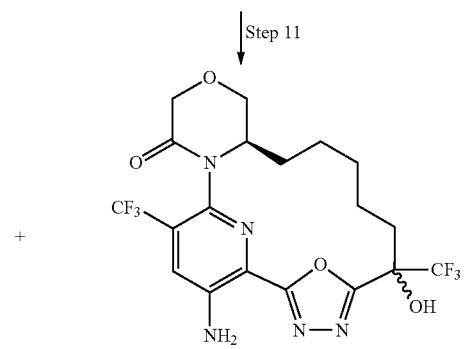

enantiomer 2

Step 1: (5R)-5-Allylmorpholin-3-one

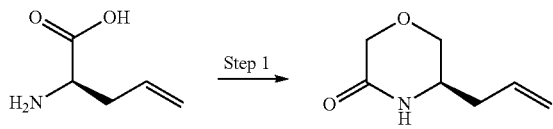

Part A: To a suspension of (2R)-2-aminopent-4-enoic acid (3.97 g, 34.483 mmol) in THF (150 mL) at 0° C. was added LiAlH$_4$ in THF (46 mL, 1 M, 46 mmol) dropwise over 60 min, keeping the internal temperature at 0 to 5° C. The mixture was stirred at room temperature overnight. The mixture was diluted with THF (200 mL) and cooled to 0° C. then quenched with 1.82 mL of water, 1.82 mL of 25% aq. NaOH and 5.46 mL of water. The mixture was stirred at room temperature for 1 h, filtered and washed with THF, and the filtrate was kept. The resultant solid was suspended in THF (200 mL) and heated at reflux for 1 h, cooled to room temperature, then filtered. All combined filtrates were concentrated to give as a pale-yellow oil, (2R)-2-aminopent-4-en-1-ol (4.25 g, 100%). $^1$H NMR (300 MHz, Chloroform-d) δ 5.93-5.63 (m, 1H), 5.22-5.00 (m, 2H), 3.60 (dd, J=10.6, 3.8 Hz, 1H), 3.32 (dd, J=10.6, 7.6 Hz, 1H), 2.99-2.85 (m, 1H), 2.30-2.15 (m, 1H), 2.11-1.94 (m, 1H), 1.92-1.73 (m, 3H) ppm. ESI-MS m/z calc. 101.08406, found 102.3 (M+1)$^+$; Retention time: 0.27 minutes (LC Method E).

Part B: To a solution of (2R)-2-aminopent-4-en-1-ol (3.48 g, 34.405 mmol) and Et$_3$N (19.602 g, 27 mL, 193.71 mmol) in CH$_2$Cl$_2$ (50 mL) at −78° C. was added 2-chloroacetyl chloride (10 g, 88.54 mmol) dropwise and the mixture was warmed to room temperature over 1 h. The mixture was diluted with $CH_2Cl_2$ (100 mL) and water (100 mL). The two layers were separated, and the aqueous layer was extracted with $CH_2Cl_2$ (2×50 mL). The combined organic layer was washed with 5% aq. $NaHCO_3$ (50 mL), dried over $Na_2SO_4$, filtered and concentrated. The residue was purified by silica gel chromatography using a gradient from of 0% to 50% ethyl acetate in heptane to afford as a white solid, [(2R)-2-[(2-chloroacetyl)amino]pent-4-enyl] 2-chloroacetate (2.23 g, 26%). $^1$H NMR (300 MHz, Chloroform-d) δ 6.62 (d, J=5.9 Hz, 1H), 5.88-5.65 (m, 1H), 5.27-5.08 (m, 2H), 4.39-4.18 (m, 3H), 4.09 (s, 2H), 4.05 (s, 2H), 2.45-2.28 (m, 2H) ppm. ESI-MS m/z calc. 253.02725, found 254.1 (M+1)$^+$; Retention time: 1.62 minutes (LC Method E).

Part C: To a solution of [(2R)-2-[(2-chloroacetyl)amino]pent-4-enyl] 2-chloroacetate (2.23 g, 8.7757 mmol) in acetone (50 mL) was added a solution of $Na_2CO_3$ (1.39 g, 13.115 mmol) in water (30 mL). The mixture was stirred at room temperature overnight and concentrated to remove acetone. The residue was extracted with EtOAc (4×40 mL) and the combined organic layers were dried over $Na_2SO_4$, filtered and concentrated. The residue was purified by silica gel chromatography using 100% ethyl acetate to afford as a colorless oil, 2-chloro-N'-[(1R)-1-(hydroxymethyl)but-3-enyl]acetamide (1.55 g, 99%). $^1$H NMR (300 MHz, Chloroform-d) δ 6.78 (br. s., 1H), 5.79 (ddt, J=17.1, 10.1, 7.3 Hz, 1H), 5.29-5.05 (m, 2H), 4.08-3.97 (m, 3H), 3.77-3.65 (m, 2H), 2.46-2.28 (m, 3H) ppm. ESI-MS m/z calc. 177.05565, found 178.1 (M+1)$^+$; Retention time: 0.95 minutes (LC Method E).

Part D: To a solution of 2-chloro-N'-[(1R)-1-(hydroxymethyl)but-3-enyl]acetamide (1.46 g, 8.2194 mmol) in THF (60 mL) at 0° C. was added 60% NaH in mineral oil (380 mg, 9.5009 mmol). The mixture was stirred at room temperature for 10 min and quenched with saturated aqueous $NH_4Cl$ (10 mL). The mixture was concentrated to remove THF and extracted with $CH_2Cl_2$ (3×20 mL). The combined organic layers were dried over $Na_2SO_4$, filtered and concentrated. The residue was purified by silica gel chromatography eluting with 100% EtOAc to afford as a white solid, (5R)-5-allylmorpholin-3-one (806 mg, 69%). $^1$H NMR (300 MHz, Chloroform-d) δ 6.22 (br. s., 1H), 5.72 (dddd, J=16.8, 10.4, 8.1, 6.3 Hz, 1H), 5.30-5.13 (m, 2H), 4.27-4.05 (m, 2H), 3.92 (dd, J=11.4, 3.8 Hz, 1H), 3.67-3.54 (m, 1H), 3.52-3.41 (m, 1H), 2.41-2.27 (m, 1H), 2.23-2.09 (m, 1H) ppm. ESI-MS m/z calc. 141.07898, found 142.2 (M+1)$^+$; Retention time: 0.83 minutes (LC Method E).

Step 2: Methyl 6-[(3R)-3-allyl-5-oxo-morpholin-4-yl]-3-nitro-5-(trifluoromethyl)pyridine-2-carboxylate

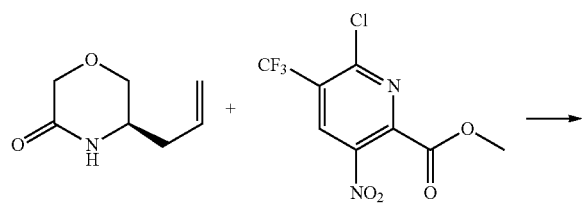

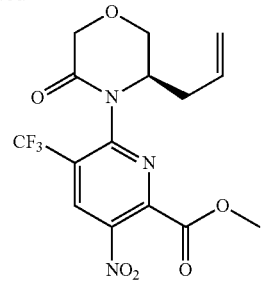

To a mixture of methyl 6-chloro-3-nitro-5-(trifluoromethyl)pyridine-2-carboxylate (1.34 g, 4.7087 mmol), (5R)-5-allylmorpholin-3-one (666 mg, 4.7178 mmol), $Cs_2CO_3$ (1.84 g, 5.6473 mmol), Xantphos (546 mg, 0.9436 mmol) and $Pd_2dba_3$ (432 mg, 0.4718 mmol) under nitrogen was added 1,4-dioxane (20 mL). The mixture was bubbled with nitrogen for 5 min then stirred under nitrogen at 80° C. for 5.5 h. A solution of methyl 6-chloro-3-nitro-5-(trifluoromethyl)pyridine-2-carboxylate (1.2 g, 4.2168 mmol) in 1,4-dioxane (10 mL) was added dropwise over 15 h. After addition, the mixture was stirred at 80° C. for 4 h and cooled to room temperature. Water (30 mL) was added and the mixture was extracted with EtOAc (3×50 mL). The combined organic layers were dried over $Na_2SO_4$, filtered and concentrated. The residue was purified by silica gel chromatography using a gradient from of 0% to 25% ethyl acetate in heptane to afford as a pale-yellow oil, methyl 6-[(3R)-3-allyl-5-oxo-morpholin-4-yl]-3-nitro-5-(trifluoromethyl)pyridine-2-carboxylate (760 mg, 41%). $^1$H NMR (300 MHz, Chloroform-d) δ 8.75 (s, 1H), 5.71-5.41 (m, 1H), 5.20-4.94 (m, 2H), 4.84-4.56 (m, 1H), 4.52-4.37 (m, 1H), 4.34-4.18 (m, 1H), 4.05 (s, 3H), 4.03-3.93 (m, 2H), 2.80-2.08 (m, 2H) ppm. $^{19}$F NMR (282 MHz, Chloroform-d) δ−61.08 to −62.72 (m, 3F) ppm. ESI-MS m/z calc. 389.08347, found 390.1 (M+1)$^+$; Retention time: 1.97 minutes (LC Method E).

Step 3: Methyl 6-[(3R)-3-allyl-5-oxo-morpholin-4-yl]-3-amino-5-(trifluoromethyl)pyridine-2-carboxylate

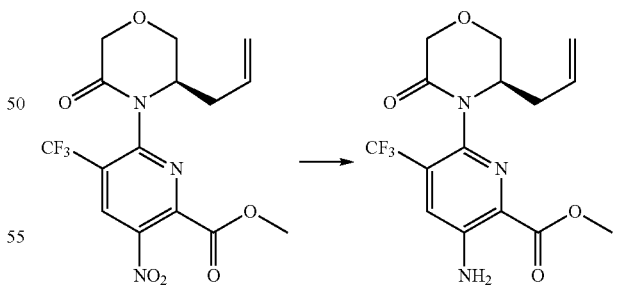

A mixture of methyl 6-[(3R)-3-allyl-5-oxo-morpholin-4-yl]-3-nitro-5-(trifluoromethyl)pyridine-2-carboxylate (114 mg, 0.2928 mmol), $NH_4Cl$ (20 mg, 0.3739 mmol) and iron (166 mg, 2.9725 mmol) in EtOH (5 mL) and $H_2O$ (1 mL) was heated under nitrogen at 80° C. for 2 h and then cooled to room temperature. EtOAc (30 mL) and 28% aq. $NH_3$ were added with stirring. The two layers were separated, and the aqueous layer was extracted with EtOAc (3×30 mL). The combined organic layers were dried over $Na_2SO_4$, filtered and concentrated. The residue was purified by silica gel chromatography using a gradient from of 50% to 80% ethyl acetate in heptane to afford as a white solid, methyl 6-[(3R)-3-allyl-5-oxo-morpholin-4-yl]-3-amino-5-(trifluoromethyl)pyridine-2-carboxylate (80 mg, 76%). ¹H NMR (300 MHz, Chloroform-d) δ 7.38-7.27 (m, 1H), 6.38-5.98 (m, 2H), 5.77-5.47 (m, 1H), 5.24-4.99 (m, 2H), 4.42-4.27 (m, 2H), 4.26-3.43 (m, 6H), 2.99-2.10 (m, 2H) ppm. ¹⁹F NMR (282 MHz, Chloroform-d) δ –61.14 to –63.58 (m, 3F) ppm. ESI-MS m/z calc. 359.10928, found 360.2 (M+1)⁺; Retention time: 1.78 minutes (LC Method E).

Step 4: Methyl 6-[(3R)-3-allyl-5-oxo-morpholin-4-yl]-3-[bis(tert-butoxycarbonyl)amino]-5-(trifluoromethyl)pyridine-2-carboxylate

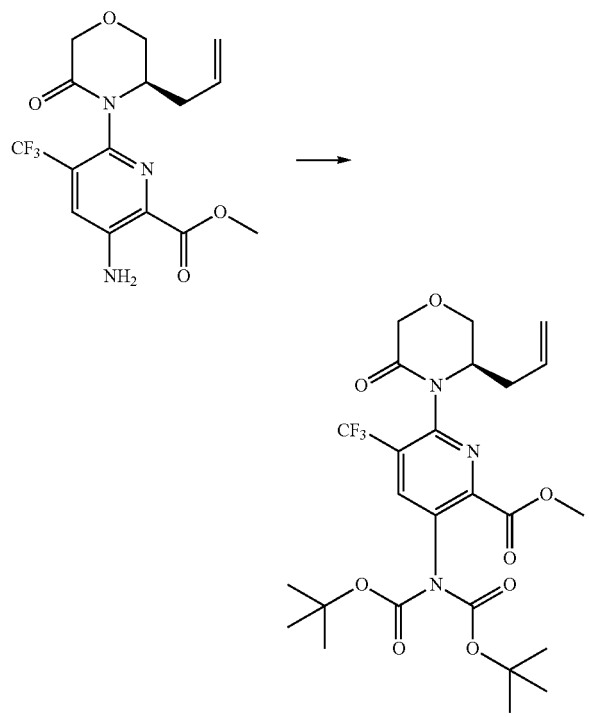

To a solution of methyl 6-[(3R)-3-allyl-5-oxo-morpholin-4-yl]-3-amino-5-(trifluoromethyl)pyridine-2-carboxylate (40 mg, 0.1113 mmol) in CH₂Cl₂ (1.5 mL) was added di-tert-butyl dicarbonate (62 mg, 0.2841 mmol) and DMAP (3.5 mg, 0.0286 mmol). The mixture was stirred at room temperature overnight and the solvent was removed under reduced pressure. The residue was purified by silica gel chromatography using a gradient from 0% to 50% ethyl acetate in heptane to afford as an oil, methyl 6-[(3R)-3-allyl-5-oxo-morpholin-4-yl]-3-[bis(tert-butoxycarbonyl)amino]-5-(trifluoromethyl)pyridine-2-carboxylate (62 mg, 100%). ¹H NMR (300 MHz, Chloroform-d) δ 8.03-7.82 (m, 1H), 5.79-5.41 (m, 1H), 5.24-4.91 (m, 2H), 4.68-4.16 (m, 2H), 4.07-3.50 (m, 6H), 2.97-2.12 (m, 2H), 1.42 (s, 18H) ppm. ¹⁹F NMR (282 MHz, Chloroform-d) δ –61.07 to –62.72 (m, 3F) ppm. ESI-MS m/z calc. 559.2142, found 582.2 (M+Na)⁺; Retention time: 2.22 minutes (LC Method E).

Step 5: 6-[(3R)-3-Allyl-5-oxo-morpholin-4-yl]-3-(tert-butoxycarbonylamino)-5-(trifluoromethyl)pyridine-2-carboxylic Acid

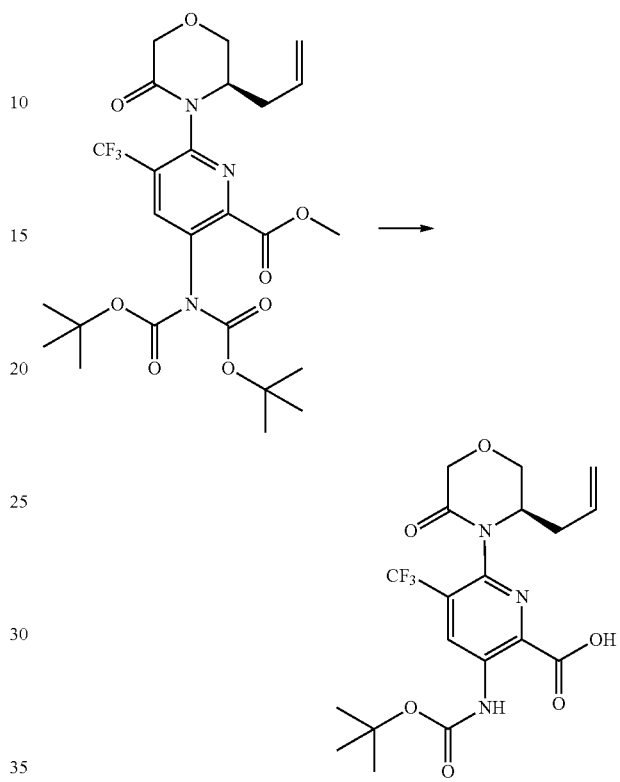

Part A: A mixture of methyl 6-[(3R)-3-allyl-5-oxo-morpholin-4-yl]-3-[bis(tert-butoxycarbonyl)amino]-5-(trifluoromethyl)pyridine-2-carboxylate (900 mg, 1.6085 mmol) and silica gel (15 g, 249.65 mmol) in EtOAc (100 mL) under nitrogen was heated at 80° C. for 4 h and at 70° C. overnight. The mixture was concentrated and purified by silica gel chromatography using a gradient from 0% to 50% ethyl acetate in heptanes to afford as a white foam, methyl 6-[(3R)-3-allyl-5-oxo-morpholin-4-yl]-3-(tert-butoxycarbonylamino)-5-(trifluoromethyl)pyridine-2-carboxylate (653 mg, 88%). ¹H NMR (300 MHz, Chloroform-d) δ 10.36-10.12 (m, 1H), 9.41-9.25 (m, 1H), 5.81-5.45 (m, 1H), 5.26-4.96 (m, 2H), 4.49-4.23 (m, 2H), 4.08-3.49 (m, 6H), 2.91-2.11 (m, 2H), 1.54 (s, 9H) ppm. ¹⁹F NMR (282 MHz, Chloroform-d) δ –61.17 to –62.94 (m, 3F) ppm. ESI-MS m/z calc. 459.1617, found 460.2 (M+1)⁺; Retention time: 2.23 minutes (LC Method E).

Part B: To a solution of methyl 6-[(3R)-3-allyl-5-oxo-morpholin-4-yl]-3-(tert-butoxycarbonylamino)-5-(trifluoromethyl)pyridine-2-carboxylate (50 mg, 0.1088 mmol) in THF (2 mL) at 0° C. was added a solution of NaOH (9.9 mg, 0.2475 mmol) in H₂O (0.5 mL). The mixture was stirred at room temperature for 2 h and cooled to 0° C. Acidified with 1 N aq. HCl (238 mg) and concentrated to remove THF. The residue was extracted with EtOAc (3×20 mL), combined organic layers were dried with Na₂SO₄, filtered and concentrated to give as a colorless oil, 6-[(3R)-3-allyl-5-oxo-morpholin-4-yl]-3-(tert-butoxycarbonylamino)-5-(trifluoromethyl)pyridine-2-carboxylic acid (48 mg, 99%). ¹H NMR (300 MHz, Chloroform-d) δ 10.46-10.15 (m, 1H), 9.55-9.37 (m, 1H), 5.75-5.41 (m, 1H), 5.24-4.98 (m, 2H), 4.48-4.20 (m, 2H), 4.07-3.88 (m, 2H), 3.80-3.56 (m, 1H), 2.83-2.09 (m, 2H), 1.55 (s, 9H) ppm. One exchangeable proton not observed. $^{19}$F NMR (282 MHz, Chloroform-d) δ −61.03 to −62.82 (m, 3F) ppm. ESI-MS m/z calc. 445.14606, found 468.1 (M+Na)$^+$; Retention time: 2.13 minutes (LC Method E).

Step 6: tert-Butyl N-[6-[(3R)-3-allyl-5-oxo-morpholin-4-yl]-2-[[[2-benzyloxy-2-(trifluoromethyl)hex-5-enoyl]amino]carbamoyl]-5-(trifluoromethyl)-3-pyridyl]carbamate

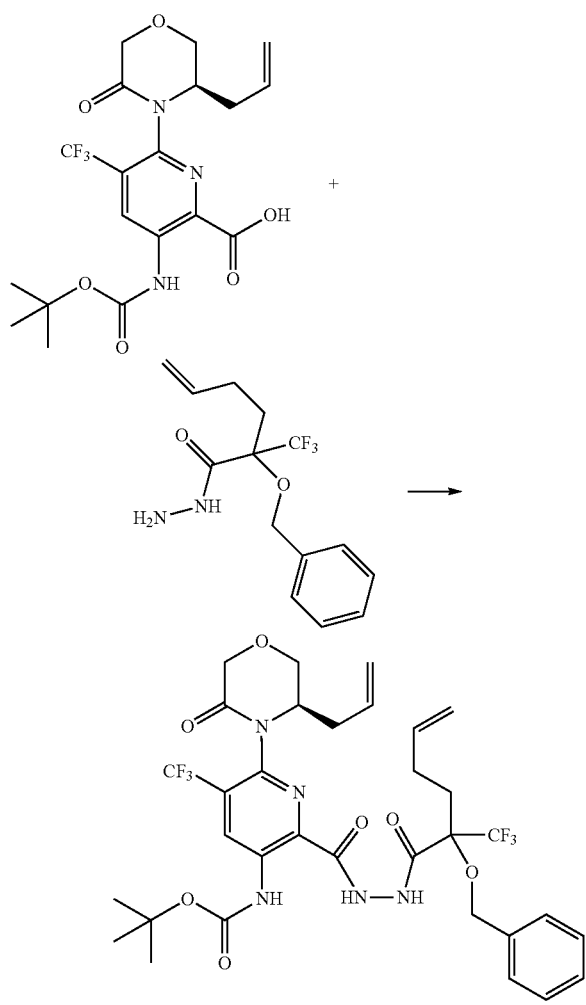

To a solution of 6-[(3R)-3-allyl-5-oxo-morpholin-4-yl]-3-(tert-butoxycarbonylamino)-5-(trifluoromethyl)pyridine-2-carboxylic acid (632 mg, 1.419 mmol) in CH$_2$Cl$_2$ (25 mL) at 0° C. was added 2-benzyloxy-2-(trifluoromethyl)hex-5-enehydrazide (536 mg, 1.7731 mmol), EDCI (hydrochloride salt) (390 mg, 2.0344 mmol), 1-hydroxybenzotriazole (hydrate) (55 mg, 0.3592 mmol) and DIPEA (150 mg, 1.1606 mmol) and the mixture was stirred at room temperature overnight. The mixture was treated with 5% aq. NaHCO$_3$(10 mL) and extracted with CH$_2$Cl$_2$ (3×30 mL). The combined organic layers were dried over Na$_2$SO$_4$, filtered and concentrated. The residue was purified by silica gel chromatography using a gradient from 0% to 40% ethyl acetate in heptanes to afford as a pale yellow oil, tert-butyl N-[6-[(3R)-3-allyl-5-oxo-morpholin-4-yl]-2-[[[2-benzyloxy-2-(trifluoromethyl)hex-5-enoyl]amino]carbamoyl]-5-(trifluoromethyl)-3-pyridyl]carbamate (966 mg, 93%). $^1$H NMR (300 MHz, Chloroform-d) δ 10.83-10.58 (m, 1H), 9.83 (br. s., 1H), 9.43-9.31 (m, 1H), 9.10 (br. s., 1H), 7.53-7.28 (m, 5H), 5.96-5.43 (m, 2H), 5.22-4.97 (m, 4H), 4.92-4.67 (m, 2H), 4.44-4.19 (m, 2H), 4.06-3.55 (m, 3H), 2.77-2.10 (m, 6H), 1.53 (s, 9H) ppm. Retention time: 2.47 minutes (LC Method E).

Step 7: tert-Butyl N-[6-[(3R)-3-allyl-5-oxo-morpholin-4-yl]-2-[5-[1-benzyloxy-1-(trifluoromethyl)pent-4-enyl]-1,3,4-oxadiazol-2-yl]-5-(trifluoromethyl)-3-pyridyl]carbamate

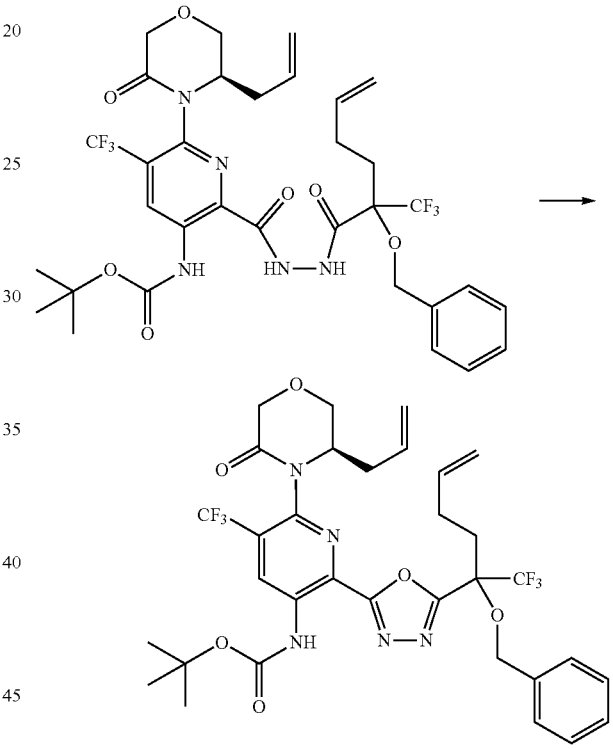

To a solution of tert-butyl N-[6-[(3R)-3-allyl-5-oxo-morpholin-4-yl]-2-[[[2-benzyloxy-2-(trifluoromethyl)hex-5-enoyl]amino]carbamoyl]-5-(trifluoromethyl)-3-pyridyl]carbamate (906 mg, 1.2417 mmol) in CH$_2$Cl$_2$ (30 mL) at 0° C. was added DIPEA (1.2614 g, 1.7 mL, 9.7599 mmol), followed by trifluoromethanesulfonic anhydride (550 mg, 1.9494 mmol) dropwise. The mixture was stirred at 0° C. for 20 min and then morpholine (120 mg) was added to quench excess trifluoromethanesulfonic anhydride and stirred the resulting mixture for 2 min. The reaction was quenched with 5% aq. NaHCO$_3$(10 mL) and extracted with CH$_2$Cl$_2$ (3×30 mL). The combined organic layers were dried with Na$_2$SO$_4$, filtered and concentrated. The residue was purified by silica gel chromatography using a gradient from 0% to 20% ethyl acetate in heptanes to afford as a colorless oil, tert-butyl N-[6-[(3R)-3-allyl-5-oxo-morpholin-4-yl]-2-[5-[1-benzyloxy-1-(trifluoromethyl)pent-4-enyl]-1,3,4-oxadiazol-2-yl]-5-(trifluoromethyl)-3-pyridyl]carbamate (694 mg, 79%). $^1$H NMR (300 MHz, Chloroform-d) δ 10.31-10.13 (m, 1H), 9.49-9.33 (m, 1H), 7.46-7.26 (m, 5H), 5.88-5.32 (m, 2H), 5.21-4.93 (m, 4H), 4.91-4.63 (m, 2H), 4.43-4.25 (m, 2H), 4.09-3.52 (m, 3H), 2.93-2.08 (m, 6H), 1.57 (s, 9H) ppm. Retention time: 2.62 minutes (LC Method E).

Step 8: tert-Butyl N-[(12R)-6-(benzyloxy)-16-oxo-6,19-bis(trifluoromethyl)-14,23-dioxa-3,4,17,22-tetraazatetracyclo[16.3.1.12,5.012,17]tricosa-1(21),2,4,9,18(22),19-hexaen-21-yl]carbamate (E/Z mixture)

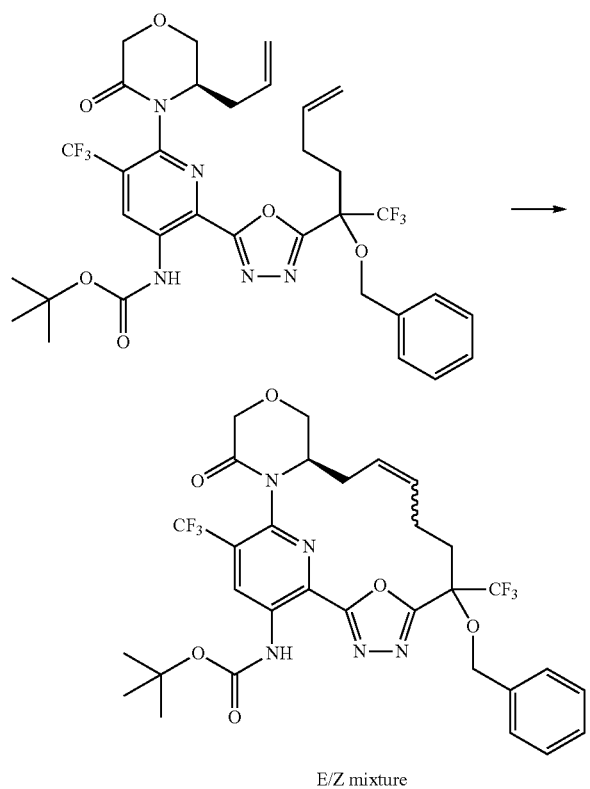

E/Z mixture

A dried 1 L flask was charged with Zhan catalyst-1B (100 mg, 0.1363 mmol). Air was replaced with nitrogen through vacuum 3 times. DCE (260 mL) was added by cannula. The mixture was bubbled with nitrogen for 10 min and heated to 75° C. A solution of tert-butyl N-[6-[(3R)-3-allyl-5-oxo-morpholin-4-yl]-2-[5-[1-benzyloxy-1-(trifluoromethyl)pent-4-enyl]-1,3,4-oxadiazol-2-yl]-5-(trifluoromethyl)-3-pyridyl]carbamate (692 mg, 0.9724 mmol) in DCE (30 mL) was added dropwise over 2.5 h. During addition, the mixture was bubbled with nitrogen for 5 min every 40 min. After the addition was complete, the mixture was bubbled with nitrogen for 15 min. The mixture was then stirred at 75° C. for 1.5 h, cooled to room temperature and concentrated. The residue was purified by silica gel chromatography using a gradient from 0% to 25% ethyl acetate in heptanes to afford as a colorless oil, tert-butyl N-[(12R)-6-(benzyloxy)-16-oxo-6,19-bis(trifluoromethyl)-14,23-dioxa-3,4,17,22-tetraazatetracyclo[16.3.1.12,5.012,17]tricosa-1(21),2,4,9,18(22),19-hexaen-21-yl]carbamate (E/Z mixture) (483 mg, 73%). This material was taken directly to the ensuing step.

Step 9: tert-Butyl N-[(12R)-6-(benzyloxy)-16-oxo-6,19-bis(trifluoromethyl)-14,23-dioxa-3,4,17,22-tetraazatetracyclo[16.3.1.12,5.012,17]tricosa-1(21),2,4,18(22),19-pentaen-21-yl]carbamate (enantiomer 1) and tert-butyl N-[(12R)-6-(benzyloxy)-16-oxo-6,19-bis(trifluoromethyl)-14,23-dioxa-3,4,17,22-tetraazatetracyclo[16.3.1.12,5.012,17]tricosa-1(21),2,4,18(22),19-pentaen-21-yl]carbamate (enantiomer 2)

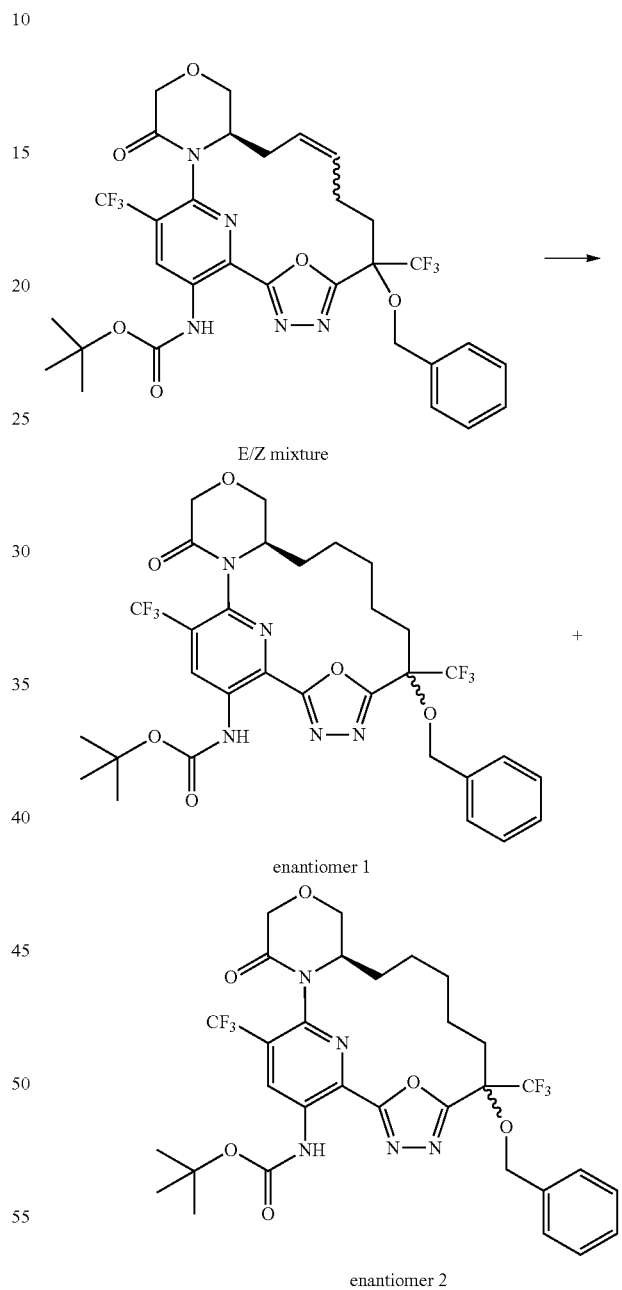

E/Z mixture enantiomer 1 enantiomer 2

To a solution of tert-butyl N-[(12R)-6-(benzyloxy)-16-oxo-6,19-bis(trifluoromethyl)-14,23-dioxa-3,4,17,22-tetraazatetracyclo[16.3.1.12,5.012,17]tricosa-1(21),2,4,9,18 (22),19-hexaen-21-yl]carbamate (E/Z mixture) (483 mg, 0.7066 mmol) in EtOAc (15 mL) and MeOH (15 mL) at 0° C. was added 10% palladium on carbon (120 mg, 50% wet, 0.0564 mmol). The mixture was stirred under hydrogen balloon at 10° C. to 15° C. for 4 h, filtered through Celite and washed with EtOAc. The filtrate was concentrated and the residue was purified by silica gel chromatography using a gradient from 0% to 20% ethyl acetate in heptanes giving two diastereomeric products:

The first diastereomer to elute was isolated as a colorless oil, tert-butyl N-[(12R)-6-(benzyloxy)-16-oxo-6,19-bis(trifluoromethyl)-14,23-dioxa-3,4,17,22-tetraazatetracyclo[16.3.1.1²,⁵.0¹²,¹⁷]tricosa-1(21),2,4,18(22),19-pentaen-21-yl]carbamate (enantiomer 1) (259 mg, 48%). $^1$H NMR (300 MHz, Chloroform-d) δ 9.61 (s, 1H), 9.29 (s, 1H), 7.34-7.22 (m, 5H), 4.90 (d, J=11.2 Hz, 1H), 4.72 (d, J=11.2 Hz, 1H), 4.40-4.25 (m, 2H), 4.06-3.92 (m, 2H), 3.70 (d, J=6.2 Hz, 1H), 2.66-2.37 (m, 2H), 2.12-1.95 (m, 2H), 1.91-1.70 (m, 3H), 1.56 (s, 9H), 1.42-1.30 (m, 3H) ppm. $^{19}$F NMR (282 MHz, Chloroform-d) δ −62.31 (s, 3F), −74.51 (s, 3F) ppm. ESI-MS m/z calc. 685.2335, found 630.2 (M-55)$^+$; Retention time: 2.58 minutes (LC Method E).

The second enantiomer to elute was isolated as a white solid, tert-butyl N-[(12R)-6-(benzyloxy)-16-oxo-6,19-bis(trifluoromethyl)-14,23-dioxa-3,4,17,22-tetraazatetracyclo[16.3.1.1²,⁵.0¹²,¹⁷]tricosa-1(21),2,4,18(22),19-pentaen-21-yl]carbamate (enantiomer 2) (201 mg, 41%). $^1$H NMR (300 MHz, Chloroform-d) δ 9.47 (s, 1H), 9.27 (s, 1H), 7.39-7.26 (m, 5H), 4.94-4.82 (m, 1H), 4.82-4.69 (m, 1H), 4.36-4.26 (m, 2H), 4.08-3.94 (m, 2H), 3.66 (d, J=7.0 Hz, 1H), 2.60-2.20 (m, 3H), 2.15-1.64 (m, 4H), 1.56 (s, 9H), 1.39-1.27 (m, 3H) ppm. $^{19}$F NMR (282 MHz, Chloroform-d) δ −62.39 (s, 3F), −74.40 (s, 3F) ppm. ESI-MS m/z calc. 685.2335, found 630.2 (M-55)$^+$; Retention time: 2.55 minutes (LC Method E).

Step 10: (12R)-21-Amino-6-hydroxy-6,19-bis(trifluoromethyl)-14,23-dioxa-3,4,17,22-tetraazatetracyclo[16.3.1.1²,⁵.0¹²,¹⁷]tricosa-1(21),2,4,18(22),19-pentaen-16-one (enantiomer 1) (Compound 116)

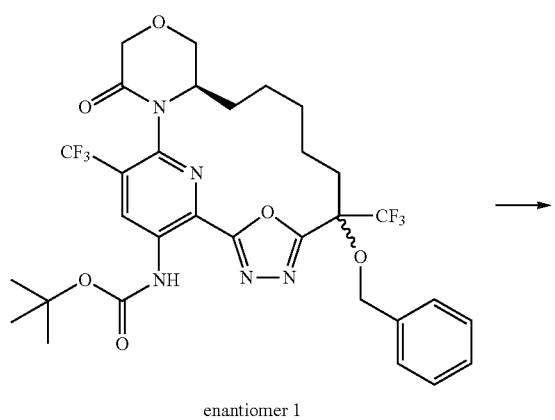

enantiomer 1

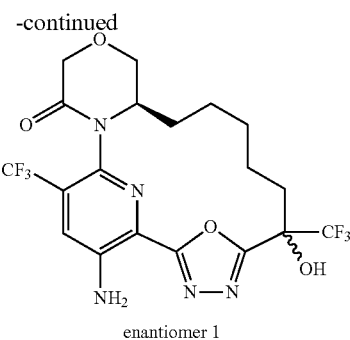

enantiomer 1

Part A: To a solution of tert-butyl N-[(12R)-6-(benzyloxy)-16-oxo-6,19-bis(trifluoromethyl)-14,23-dioxa-3,4,17,22-tetraazatetracyclo[16.3.1.1²,⁵.0¹²,¹⁷]tricosa-1(21),2,4,18(22),19-pentaen-21-yl]carbamate (enantiomer 1) (259 mg, 0.34 mmol) in EtOAc (4 mL) and MeOH (4 mL) was added 10% palladium on carbon (123 mg, 50% wet, 0.0578 mmol). The mixture was stirred at 30° C. to 50° C. under hydrogen balloon for 5 h and at room temperature overnight. Again, 10% palladium on carbon (150 mg, 50% wet, 0.0705 mmol) was added and the mixture was stirred at 30° C. to 50° C. for 6 h and at room temperature overnight. The reaction mixture was filtered through Celite and washed with EtOAc. The filtrate was concentrated and the residue was purified by silica gel chromatography using a gradient from 0% to 35% ethyl acetate in heptanes giving as a white solid, tert-butyl N-[(12R)-6-hydroxy-16-oxo-6,19-bis(trifluoromethyl)-14,23-dioxa-3,4,17,22-tetraazatetracyclo[16.3.1.1²,⁵.0¹²,¹⁷]tricosa-1(21),2,4,18(22),19-pentaen-21-yl]carbamate (enantiomer 1) (178 mg, 88%). $^1$H NMR (300 MHz, Chloroform-d) δ 9.34-9.16 (m, 2H), 4.42-4.21 (m, 2H), 4.08-3.89 (m, 2H), 3.86-3.64 (m, 2H), 2.74 (t, J=12.3 Hz, 1H), 2.33-2.12 (m, 2H), 2.01-1.68 (m, 4H), 1.56 (s, 9H), 1.53-1.29 (m, 3H) ppm. $^{19}$F NMR (282 MHz, Chloroform-d) δ −62.24 (s, 3F), −80.04 (s, 3F) ppm. ESI-MS m/z calc. 595.1865, found 596.2 (M+1)$^+$; Retention time: 2.29 minutes (LC Method E).

Part B: To a solution of tert-butyl N-[(12R)-6-hydroxy-16-oxo-6,19-bis(trifluoromethyl)-14,23-dioxa-3,4,17,22-tetraazatetracyclo[16.3.1.1²,⁵.0¹²,¹⁷]tricosa-1(21),2,4,18(22),19-pentaen-21-yl]carbamate (enantiomer 1) (178 mg, 0.2989 mmol) in CH$_2$Cl$_2$ (4 mL) at 0° C. was added TFA (1.4800 g, 1 mL, 12.98 mmol) dropwise. The mixture was stirred at room temperature for 2 h, concentrated and then co-evaporated with a 1:2 mixture of MeOH and EtOAc (3×2 mL). The residue was purified by silica gel chromatography using a gradient from 0% to 60% ethyl acetate in heptanes to afford as a white solid, (12R)-21-amino-6-hydroxy-6,19-bis(trifluoromethyl)-14,23-dioxa-3,4,17,22-tetraazatetracyclo[16.3.1.1²,⁵.0¹²,¹⁷]tricosa-1(21),2,4,18(22),19-pentaen-16-one (enantiomer 1) (132 mg, 89%). $^1$H NMR (300 MHz, Chloroform-d) δ 7.31 (s, 1H), 5.86 (s, 2H), 5.43 (s, 1H), 4.46-4.22 (m, 2H), 4.07-3.87 (m, 2H), 3.80-3.63 (m, 1H), 2.52-2.21 (m, 2H), 2.03-1.51 (m, 7H), 1.41-1.32 (m, 1H) ppm. $^{19}$F NMR (282 MHz, Chloroform-d) δ −62.66 (s, 3F), −79.06 (s, 3F) ppm. ESI-MS m/z calc. 495.13412, found 496.2 (M+1)$^+$; Retention time: 1.96 minutes (LC Method E).

Step 11: (12R)-21-Amino-6-hydroxy-6,19-bis(trifluoromethyl)-14,23-dioxa-3,4,17,22-tetraazatetracyclo[16.3.1.1²,⁵.0¹²,¹⁷]tricosa-1(21),2,4,18(22),19-pentaen-16-one (enantiomer 2) (Compound 117)

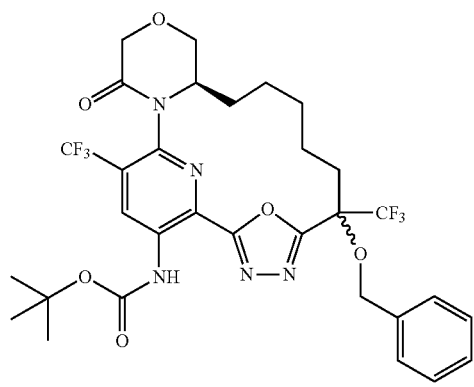

enantiomer 2

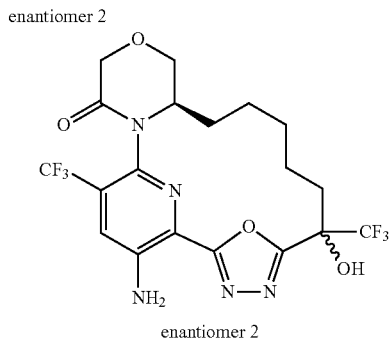

enantiomer 2

Part A: To a solution of tert-butyl N-[(12R)-6-(benzyloxy)-16-oxo-6,19-bis(trifluoromethyl)-14,23-dioxa-3,4,17,22-tetraazatetracyclo[16.3.1.1²,⁵.0¹²,¹⁷]tricosa-1(21),2,4,18(22),19-pentaen-21-yl]carbamate (enantiomer 2) (209 mg, 0.3048 mmol) in EtOAc (4 mL) and MeOH (4 mL) was added 10% palladium on carbon (150 mg, 50% wet, 0.0705 mmol). The mixture was stirred under hydrogen balloon at 30° C. to 50° C. for 5 h and at room temperature overnight. The mixture was filtered through Celite and washed with EtOAc. The filtrate was concentrated, and the residue was purified by silica gel chromatography (24 g column) using a gradient from 0% to 40% ethyl acetate in heptanes giving as a white solid, tert-butyl N-[(12R)-6-hydroxy-16-oxo-6,19-bis(trifluoromethyl)-14,23-dioxa-3,4,17,22-tetraazatetracyclo[16.3.1.1²,⁵.0¹²,¹⁷]tricosa-1(21),2,4,18(22),19-pentaen-21-yl]carbamate (enantiomer 2) (148 mg, 82%). ¹H NMR (300 MHz, Chloroform-d) δ 9.36 (s, 1H), 9.27 (s, 1H), 4.33 (s, 2H), 4.05-3.92 (m, 3H), 3.68-3.54 (m, 1H), 2.52-2.12 (m, 3H), 2.01-1.73 (m, 3H), 1.68-1.61 (m, 1H), 1.57 (s, 9H), 1.51-1.37 (m, 3H) ppm. ¹⁹F NMR (282 MHz, Chloroform-d) δ −62.46 (s, 3F), −78.66 (s, 3F) ppm. ESI-MS m/z calc. 595.1866, found 540.3 (M−55)⁺; Retention time: 2.21 minutes (LC Method E).

Part B: To a solution of tert-butyl N-[(12R)-6-hydroxy-16-oxo-6,19-bis(trifluoromethyl)-14,23-dioxa-3,4,17,22-tetraazatetracyclo[16.3.1.1²,⁵.0¹²,¹⁷]tricosa-1(21),2,4,18 (22),19-pentaen-21-yl]carbamate (enantiomer 2) (148 mg, 0.2485 mmol) in CH₂Cl₂ (3 mL) at 0° C. was added TFA (1.4800 g, 1 mL, 12.98 mmol). The mixture was stirred at room temperature for 2 h and concentrated then co-evaporated with a 1:3 mixture of MeOH and EtOAc (3×4 mL).

The residue was purified by silica gel chromatography using a gradient from 0% to 60% ethyl acetate in heptanes and the product was lyophilized from CH₃CN (1 mL) and H₂O (2 mL) to give as a white solid, (12R)-21-amino-6-hydroxy-6,19-bis(trifluoromethyl)-14,23-dioxa-3,4,17,22-tetraazatetracyclo[16.3.1.1²,⁵.0¹²,¹⁷]tricosa-1(21),2,4,18(22),19-pentaen-16-one (enantiomer 2) (101 mg, 81%). ¹H NMR (300 MHz, DMSO-d6) δ 7.78 (s, 1H), 7.63 (s, 1H), 6.94 (br. s., 2H), 4.18 (s, 2H), 4.02-3.82 (m, 2H), 3.72-3.53 (m, 1H), 2.32-1.93 (m, 3H), 1.88-1.52 (m, 4H), 1.43-1.20 (m, 3H) ppm. ¹⁹F NMR (282 MHz, DMSO-d6) δ −61.51 (s, 3F), −78.17 (s, 3F) ppm. ESI-MS m/z calc. 495.1341, found 496.3 (M+1)⁺; Retention time: 2.72 minutes (LC Method E).

Example 59: Preparation of (12R)-20-amino-18-phenyl-6-(trifluoromethyl)-22-oxa-3,4,16,21-tetraazatetracyclo[15.3.1.1²,⁵.0¹²,¹⁶]docosa-1(21),2,4,17,19-pentaen-6-ol (mixture of diastereomers) (Compound 118)

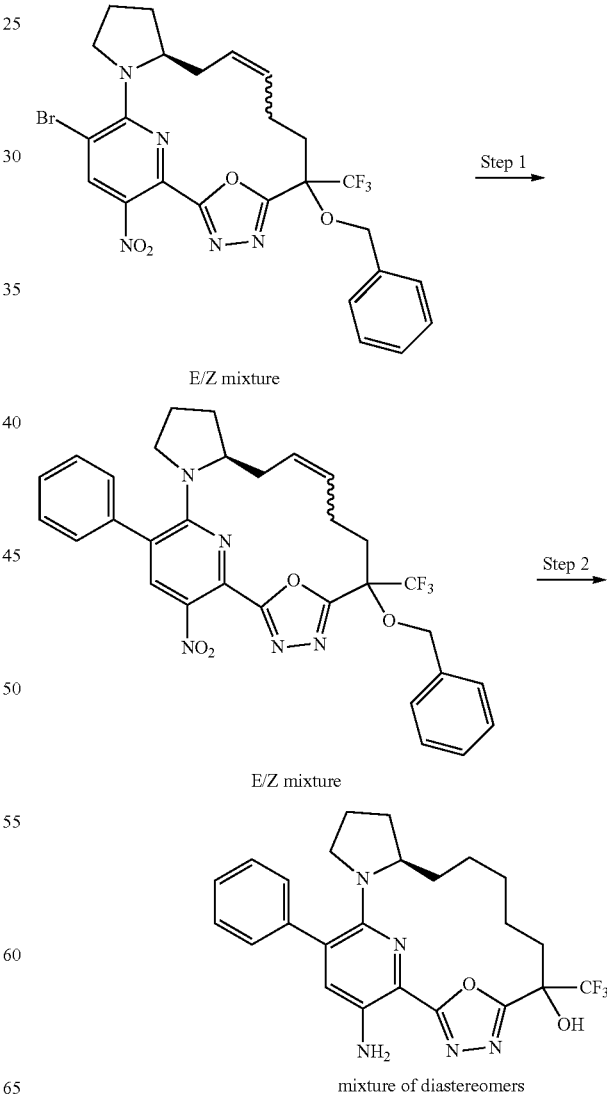

Step 1: (12S)-6-(Benzyloxy)-20-nitro-18-phenyl-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture)

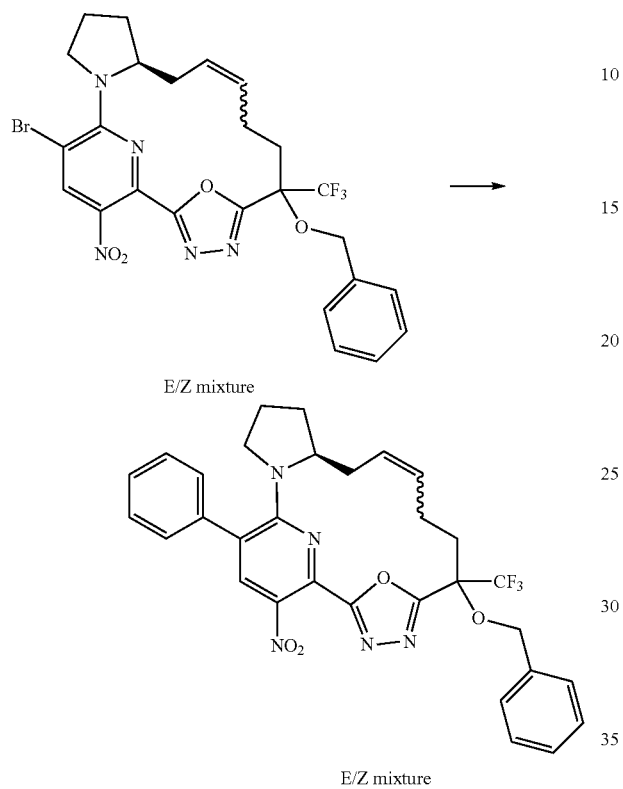

E/Z mixture

A pressure tube was charged with (12S)-6-(benzyloxy)-18-bromo-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (150 mg, 0.2524 mmol), phenylboronic acid pinacol ester (67 mg, 0.3283 mmol), cesium carbonate (198 mg, 0.6077 mmol) and toluene (6 mL). The mixture was bubbled with nitrogen for 5 min. Pd(dppf)Cl$_2$ (13 mg, 0.0159 mmol) was added. The mixture was bubbled with nitrogen for 3 min and the tube was sealed. The mixture was heated at 100° C. overnight, cooled to room temperature and treated with water (10 mL). The mixture was extracted with EtOAc (3×20 mL). The combined organic layers were dried over Na$_2$SO$_4$, filtered and concentrated. The residue was purified by silica gel chromatography (24 g column) using a gradient from 0% to 15% ethyl acetate in heptane giving as a yellow solid, (12S)-6-(benzyloxy)-20-nitro-18-phenyl-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (149 mg, 100%). $^1$H NMR (300 MHz, Chloroform-d) δ 8.26 (s, 1H), 7.53-7.27 (m, 10H), 5.65-5.39 (m, 2H), 5.35-4.91 (m, 2H), 4.08-3.93 (m, 1H), 3.65-3.48 (m, 1H), 2.98-2.71 (m, 2H), 2.59-2.06 (m, 6H), 1.89-1.77 (m, 1H), 1.76-1.61 (m, 2H) ppm. $^{19}$F NMR (282 MHz, Chloroform-d) δ −72.83 to −73.65 (m, 3F) ppm. ESI-MS m/z calc. 591.2093, found 592.3 (M+1)$^+$; Retention time: 2.7 minutes (LC Method E).

Step 2: (12R)-20-Amino-18-phenyl-6-(trifluoromethyl)-22-oxa-3,4,16,21-tetraazatetracyclo[15.3.1.1²,⁵.0¹²,¹⁶]docosa-1(21),2,4,17,19-pentaen-6-ol (mixture of diastereomers) (Compound 118)

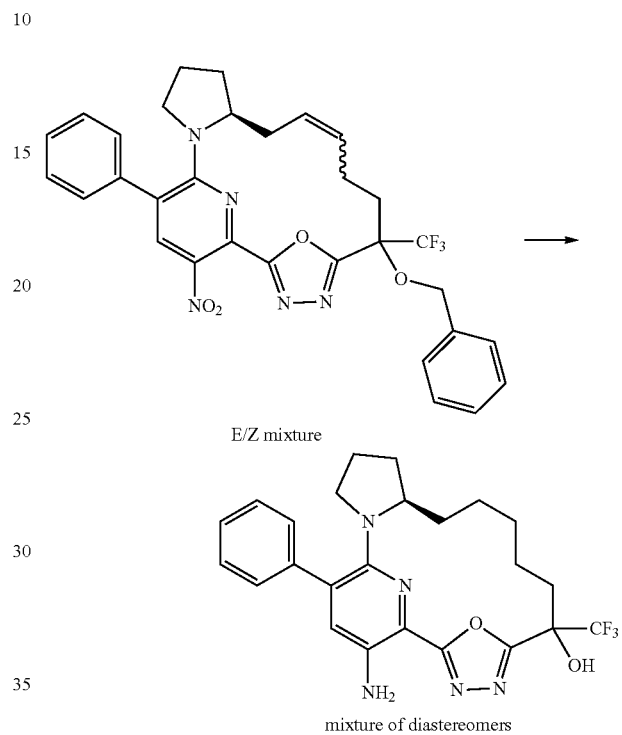

mixture of diastereomers

To a solution of (12S)-6-(benzyloxy)-20-nitro-18-phenyl-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (149 mg, 0.2519 mmol) in EtOAc (4 mL) and MeOH (4 mL) was added 10% palladium on carbon (107 mg, 50% wet, 0.0503 mmol). The mixture was stirred under hydrogen balloon at 30° C. to 50° C. for 4 h and at room temperature overnight. The mixture was filtered through Celite and washed with EtOAc. The filtrate was concentrated, and the residue was purified by silica gel chromatography (24 g column) using a gradient from 0% to 40% ethyl acetate in heptanes giving as a yellow solid and mixture of diastereomers, (12R)-20-amino-18-phenyl-6-(trifluoromethyl)-22-oxa-3,4,16,21-tetraazatetracyclo[15.3.1.1²,⁵.0¹²,¹⁶]docosa-1(21),2,4,17,19-pentaen-6-ol (mixture of diastereomers) (91 mg, 75%). $^1$H NMR (300 MHz, DMSO-d6) δ 7.55-7.49 (m, 1H), 7.48-7.31 (m, 5H), 7.18-7.14 (m, 1H), 5.93 (s, 2H), 3.98-3.65 (m, 1H), 2.78-2.54 (m, 2H), 2.34-2.20 (m, 1H), 2.13-1.93 (m, 2H), 1.84-1.27 (m, 10H), 1.02-0.70 (m, 1H) ppm. $^{19}$F NMR (282 MHz, DMSO-d6) δ−76.08 to −79.41 (m, 3F) ppm. ESI-MS m/z calc. 473.2039, found 474.2 (M+1)$^+$; Retention time: 3.96 minutes (LC Method E).

Example 60: Preparation of 17-amino-12-phenyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (Compound 119), 17-amino-12-phenyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (Compound 120), 17-amino-12-phenyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 3) (Compound 121) and 17-amino-12-phenyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 4) (Compound 122)

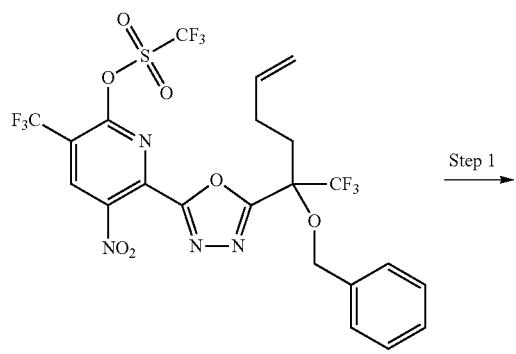

Step 1

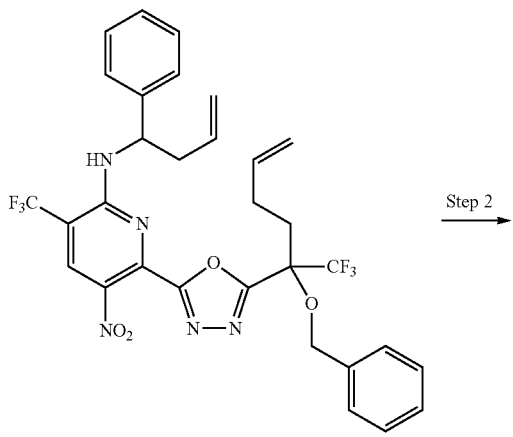

Step 2

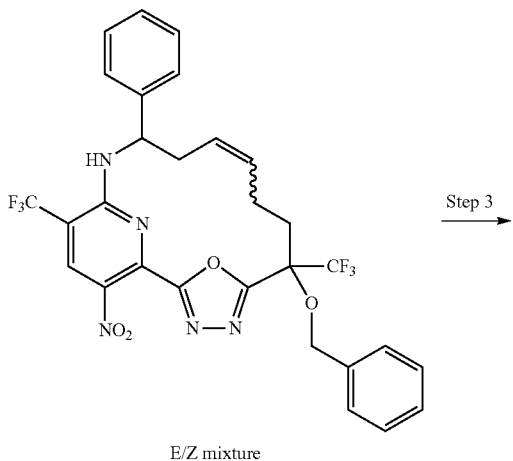

E/Z mixture

Step 3

-continued

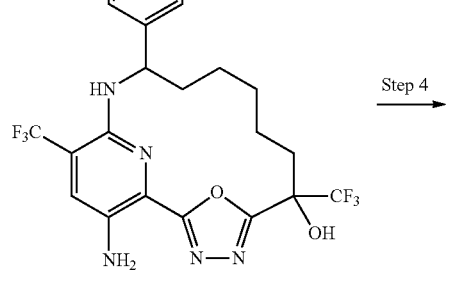

Step 4

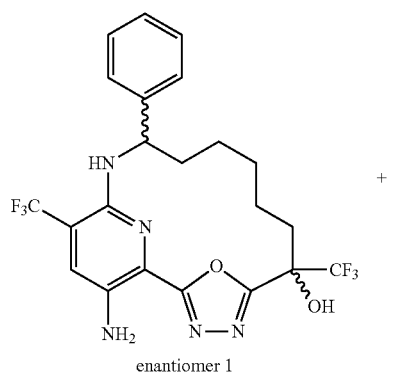

enantiomer 1

+

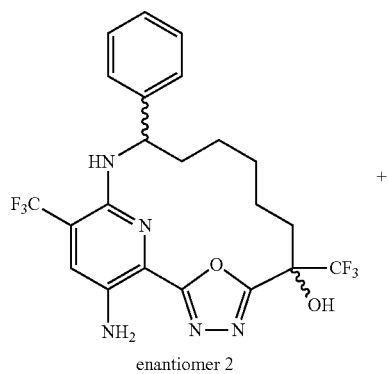

enantiomer 2

+

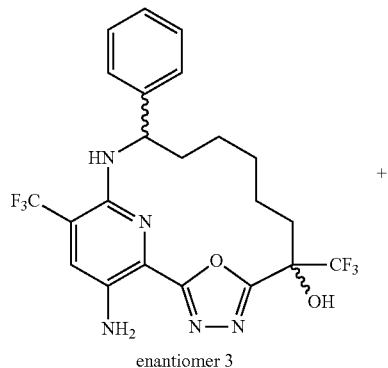

enantiomer 3

591

-continued

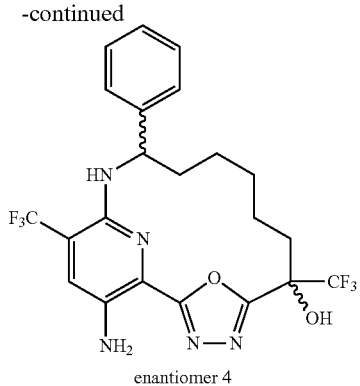

enantiomer 4

Step 1: 6-[5-[1-Benzyloxy-1-(trifluoromethyl)pent-4-enyl]-1,3,4-oxadiazol-2-yl]-5-nitro-N-(1-phenylbut-3-enyl)-3-(trifluoromethyl)pyridin-2-amine To a solution of [6-[5-[1-benzyloxy-1-(trifluoromethyl)pent-4-enyl]-1,3,4-oxadiazol-2-yl]-5-nitro-3-(trifluoromethyl)-2-pyridyl] trifluoromethanesulfonate (600 mg, 0.9225 mmol) in acetonitrile (8 mL) was added 1-phenylbut-3-en-1-amine (410 mg, 2.785 mmol) and DIEA (850 μL, 4.88 mmol) and the mixture was stirred for 120 minutes at room temperature. The reaction was concentrated and the residue was purified by silica gel chromatography (80 gram column) using a gradient from 100% hexanes to 100% ethyl acetate to afford as a yellow foam, 6-[5-[1-benzyloxy-1-(trifluoromethyl)pent-4-enyl]-1,3,4-oxadiazol-2-yl]-5-nitro-N-(1-phenylbut-3-enyl)-3-(trifluoromethyl)pyridin-2-amine (459 mg, 77%). $^1$H NMR (400 MHz, DMSO-d6) δ 8.54 (s, 1H), 8.30 (dd, J=7.8, 3.2 Hz, 1H), 7.42-7.31 (m, 7H), 7.26-7.21 (m, 2H), 7.2-7.15 (m, 1H), 5.91-5.80 (m, 1H), 5.79-5.67 (m, 1H), 5.45-5.33 (m, 1H), 5.17-5.06 (m, 2H), 5.02 (ddd, J=10.3, 5.5, 2.0 Hz, 2H), 4.77 (d, J=10.8 Hz, 1H), 4.60 (dd, J=10.8, 8.0 Hz, 1H), 2.94 (ddd, J=14.3, 9.2, 7.1 Hz, 1H), 2.58 (ddd, J=25.3, 11.9, 4.7 Hz, 3H), 2.35-2.17 (m, 2H) ppm. ESI-MS m/z calc. 647.1967, found 648.2 (M+1)$^+$; Retention time: 2.08 minutes (LC Method J).

Step 2: 6-Benzyloxy-17-nitro-12-phenyl-6,15-bis(trifluoromethyl)-19-oxa-3,4,13,18-tetrazatricyclo[12.3.1.1²,⁵]nonadeca-1(17),2,4,9,14(18),15-hexaene (E/Z mixture)

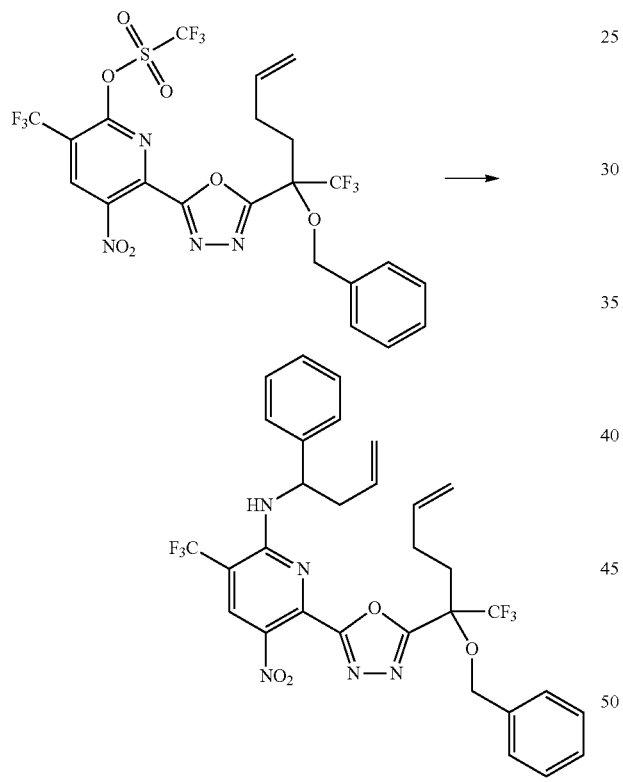

E/Z mixture

In a 500 mL 3-neck flask, benzylidene-[1,3-bis(2,4,6-trimethylphenyl)imidazolidin-2-ylidene]-dichloro-ruthenium; tricyclohexylphosphane (125 mg, 0.1472 mmol) was dissolved in toluene (135 mL). Then, a solution of 6-[5-[1-benzyloxy-1-(trifluoromethyl)pent-4-enyl]-1,3,4-oxadiazol-2-yl]-5-nitro-N-(1-phenylbut-3-enyl)-3-(trifluoromethyl)pyridin-2-amine (380 mg, 0.5868 mmol) in toluene (5 mL) was added via syringe. The resulting mixture was heated at 110° C. for 30 mins. The reaction mixture was cooled and concentrated under reduced pressure. The residue was purified by silica gel chromatography (40 gram column) using a gradient from 100% hexanes to 75% ethyl acetate in hexanes to afford as a tan oil, 6-benzyloxy-17-nitro-12-phenyl-6,15-bis(trifluoromethyl)-19-oxa-3,4,13,18-tetrazatricyclo[12.3.1.1²,⁵]nonadeca-1(17),2,4,9,14(18),15-hexaene (E/Z mixture) (147 mg, 40%). ESI-MS m/z calc. 619.1654, found 620.2 (M+1)⁺; Retention time: 1.39 minutes (LC Method J).

Step 3: 17-Amino-12-phenyl-6,15-bis(trifluoromethyl)-19-oxa-3,4,13,18-tetrazatricyclo[12.3.1.1².⁵]nonadeca-1(18),2,4,14,16-pentaen-6-ol

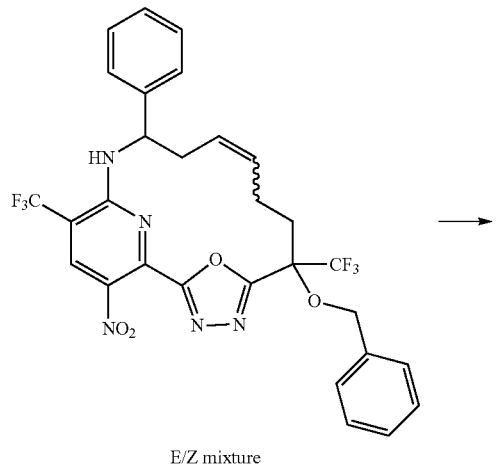

E/Z mixture

In a 100 mL round bottom flask, a solution of 6-benzyloxy-17-nitro-12-phenyl-6,15-bis(trifluoromethyl)-19-oxa-3,4,13,18-tetrazatricyclo[12.3.1.1².⁵]nonadeca-1(17),2,4,9,14(18),15-hexaene (E/Z mixture) (147 mg, 0.2373 mmol) in ethyl acetate (8 mL) and AcOH (2 mL) was purged with nitrogen. Then Pd/C (250 mg, 10% w/w, 0.2349 mmol) was added. The mixture was degassed with nitrogen then purged by a balloon filled with hydrogen gas. The mixture was stirred at 1 atm of hydrogen gas for 7 h. The reaction was filtered, and the filtrate was purified by reverse phase preparative HPLC using a mobile gradient run of 1% to 99% acetonitrile in water (+5 mM HCl) over 30 minutes which gave as a yellow solid, 17-amino-12-phenyl-6,15-bis(trifluoromethyl)-19-oxa-3,4,13,18-tetrazatricyclo[12.3.1.1².⁵]nonadeca-1(18),2,4,14,16-pentaen-6-ol (50 mg, 42%). NMR (400 MHz, DMSO-d6) δ 7.67 (s, 1H), 7.59 (d, J=5.3 Hz, 1H), 7.47 (t, J=6.6 Hz, 2H), 7.43-7.38 (m, 2H), 7.34 (t, J=7.2 Hz, 1H), 6.14 (s, 2H), 4.81 (dd, J=24.4, 3.9 Hz, 1H), 4.70 (dd, J=29.0, 10.3 Hz, 1H), 2.81 (d, J=54.8 Hz, 1H), 2.27 (t, J=12.5 Hz, 1H), 2.07 (s, 1H), 1.82-1.57 (m, 2H), 1.50 (s, 1H), 1.40 (s, 2H), 1.26 (d, J=24.2 Hz, 1H), 1.15 (s, 1H) ppm. ESI-MS m/z calc. 501.15994, found 502.2 (M+1)⁺; Retention time: 2.12 minutes (LC Method J).

Step 4: 17-Amino-12-phenyl-6,15-bis(trifluoromethyl)-19-oxa-3,4,13,18-tetrazatricyclo[12.3.1.1².⁵]nonadeca-1(18),2,4,14,16-pentaen-6-ol (enantiomer 1) (Compound 119), 17-amino-12-phenyl-6,15-bis(trifluoromethyl)-19-oxa-3,4,13,18-tetrazatricyclo[12.3.1.1².⁵]nonadeca-1(18),2,4,14,16-pentaen-6-ol (enantiomer 2) (Compound 120), 17-amino-12-phenyl-6,15-bis(trifluoromethyl)-19-oxa-3,4,13,18-tetrazatricyclo[12.3.1.1².⁵]nonadeca-1(18),2,4,14,16-pentaen-6-ol (enantiomer 3) (Compound 121) and 17-amino-12-phenyl-6,15-bis(trifluoromethyl)-19-oxa-3,4,13,18-tetrazatricyclo[12.3.1.1².⁵]nonadeca-1(18),2,4,14,16-pentaen-6-ol (enantiomer 4) (Compound 122)

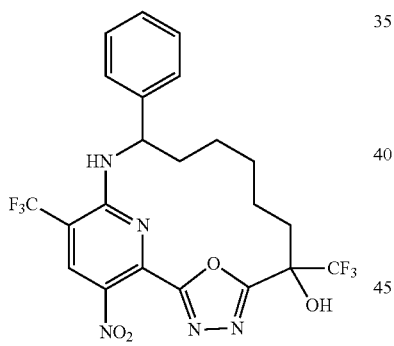

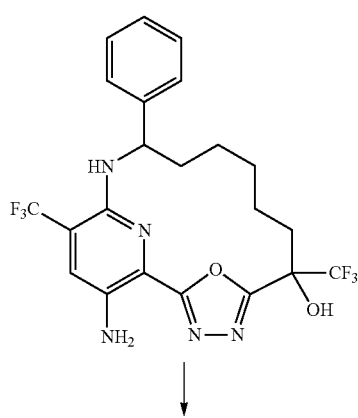

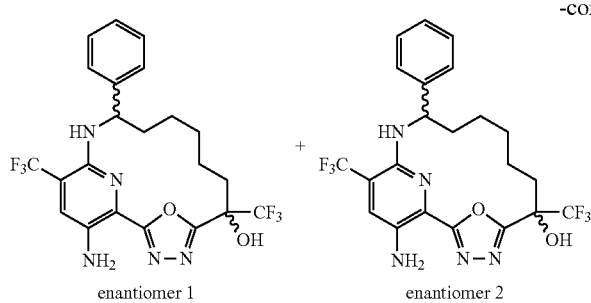
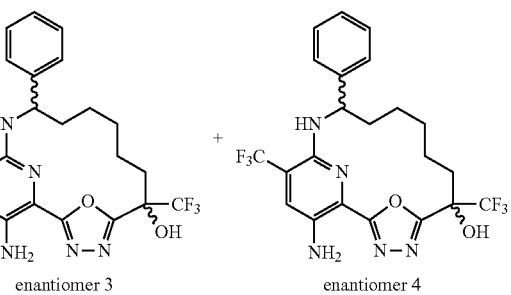

enantiomer 1     enantiomer 2     enantiomer 3     enantiomer 4

17-Amino-12-phenyl-6,15-bis(trifluoromethyl)-19-oxa-3,4,13,18-tetrazatricyclo[12.3.1.12,5]nonadeca-1(18),2,4,14,16-pentaen-6-ol (50 mg, 0.09972 mmol) was purified by SFC using a Lux-4 column (250×21.2 mm, 5 μm particle size) sold by Phenomenex and eluting with a dual gradient run from 5% to 80% MeOH (+20 mM $NH_3$) in $CO_2$ to give 4 isomeric products:

The first enantiomer to elute was isolated as a yellow solid, 17-amino-12-phenyl-6,15-bis(trifluoromethyl)-19-oxa-3,4,13,18-tetrazatricyclo[12.3.1.12,5]nonadeca-1(18),2,4,14,16-pentaen-6-ol (enantiomer 1) (6.6 mg, 52%). $^1$H NMR (400 MHz, DMSO-d6) δ 8.37 (s, 1H), 7.67 (s, 1H), 7.48 (d, J=7.2 Hz, 2H), 7.41 (t, J=7.4 Hz, 2H), 7.36-7.31 (m, 1H), 6.14 (s, 2H), 4.78 (d, J=3.6 Hz, 1H), 4.67 (dt, J=10.6, 2.9 Hz, 1H), 2.91-2.83 (m, 1H), 2.27 (t, J=12.4 Hz, 1H), 2.08-1.99 (m, 1H), 1.73 (d, J=10.5 Hz, 1H), 1.56 (ddd, J=26.6, 13.0, 6.8 Hz, 2H), 1.39 (d, J=8.3 Hz, 2H), 1.35-1.29 (m, 1H), 1.13 (d, J=11.6 Hz, 1H) ppm. ESI-MS m/z calc. 501.15994, found 502.2 (M+1)$^+$; Retention time: 2.12 minutes (LC Method A).

The second enantiomer to elute was isolated as a yellow solid, 17-amino-12-phenyl-6,15-bis(trifluoromethyl)-19-oxa-3,4,13,18-tetrazatricyclo[12.3.1.12,5]nonadeca-1(18),2,4,14,16-pentaen-6-ol (enantiomer 2) (4.8 mg, 38%). $^1$H NMR (400 MHz, DMSO-d6) δ 8.36 (s, 1H), 7.67 (s, 1H), 7.47 (d, J=7.0 Hz, 2H), 7.41 (dd, J=8.4, 6.4 Hz, 2H), 7.37-7.31 (m, 1H), 6.14 (s, 2H), 4.84 (d, J=4.1 Hz, 1H), 4.74 (dt, J=10.9, 3.2 Hz, 1H), 2.78-2.69 (m, 1H), 2.34 (t, J=10.9 Hz, 1H), 2.09 (ddd, J=14.6, 8.9, 6.0 Hz, 1H), 1.81 (d, J=9.6 Hz, 1H), 1.70 (dd, J=14.4, 7.7 Hz, 1H), 1.52-1.37 (m, 3H), 1.27 (dd, J=16.0, 8.6 Hz, 1H), 1.13 (dd, J=13.8, 6.8 Hz, 1H) ppm. ESI-MS m/z calc. 501.15994, found 502.2 (M+1)$^+$; Retention time: 2.12 minutes (LC Method A).

The third enantiomer to elute was isolated as a yellow solid, 17-amino-12-phenyl-6,15-bis(trifluoromethyl)-19-oxa-3,4,13,18-tetrazatricyclo[12.3.1.12,5]nonadeca-1(18),2,4,14,16-pentaen-6-ol (enantiomer 3) (6.4 mg, 50%). $^1$H NMR (400 MHz, DMSO-d6) δ 8.39 (s, 1H), 7.67 (s, 1H), 7.48 (d, J=7.5 Hz, 2H), 7.41 (t, J=7.4 Hz, 2H), 7.34 (t, J=7.2 Hz, 1H), 6.14 (s, 2H), 4.78 (d, J=3.6 Hz, 1H), 4.66 (dd, J=8.6, 5.4 Hz, 1H), 2.86 (d, J=12.2 Hz, 1H), 2.27 (t, J=12.4 Hz, 1H), 2.08-1.99 (m, 1H), 1.74 (s, 1H), 1.59 (q, J=6.0 Hz, 1H), 1.53 (d, J=20.4 Hz, 1H), 1.38 (d, J=18.7 Hz, 2H), 1.31 (d, J=7.6 Hz, 1H), 1.12 (d, J=15.1 Hz, 1H) ppm. ESI-MS m/z calc. 501.15994, found 502.2 (M+1)$^+$; Retention time: 2.12 minutes (LC Method A).

The fourth enantiomer to elute was isolated as a yellow solid, 17-amino-12-phenyl-6,15-bis(trifluoromethyl)-19-oxa-3,4,13,18-tetrazatricyclo[12.3.1.12,5]nonadeca-1(18),2,4,14,16-pentaen-6-ol (enantiomer 4) (7.0 mg, 55%). $^1$H NMR (400 MHz, DMSO-d6) δ 8.42 (s, 1H), 7.67 (s, 1H), 7.47 (d, J=7.1 Hz, 2H), 7.41 (t, J=7.4 Hz, 2H), 7.34 (dd, J=8.4, 6.0 Hz, 1H), 6.14 (s, 2H), 4.83 (d, J=4.1 Hz, 1H), 4.74 (dt, J=10.8, 3.2 Hz, 1H), 2.75 (q, J=9.4, 8.9 Hz, 1H), 2.38-2.27 (m, 1H), 2.09 (ddd, J=14.9, 8.9, 5.9 Hz, 1H), 1.82 (dt, J=12.0, 4.6 Hz, 1H), 1.69 (dt, J=14.7, 7.5 Hz, 1H), 1.49 (dq, J=11.5, 6.2 Hz, 1H), 1.45-1.34 (m, 2H), 1.27 (dd, J=16.0, 8.2 Hz, 1H), 1.13 (dt, J=14.1, 8.1 Hz, 1H) ppm. ESI-MS m/z calc. 501.15994, found 502.2 (M+1)$^+$; Retention time: 2.12 minutes (LC Method A).

Example 61: Preparation of (12R)-20-amino-18-(oxan-4-yl)-6-(trifluoromethyl)-22-oxa-3,4,16,21-tetraazatetracyclo[15.3.1.12,5.012,16]docosa-1(21),2,4,17,19-pentaen-6-ol (mixture of diastereomers) (Compound 123)

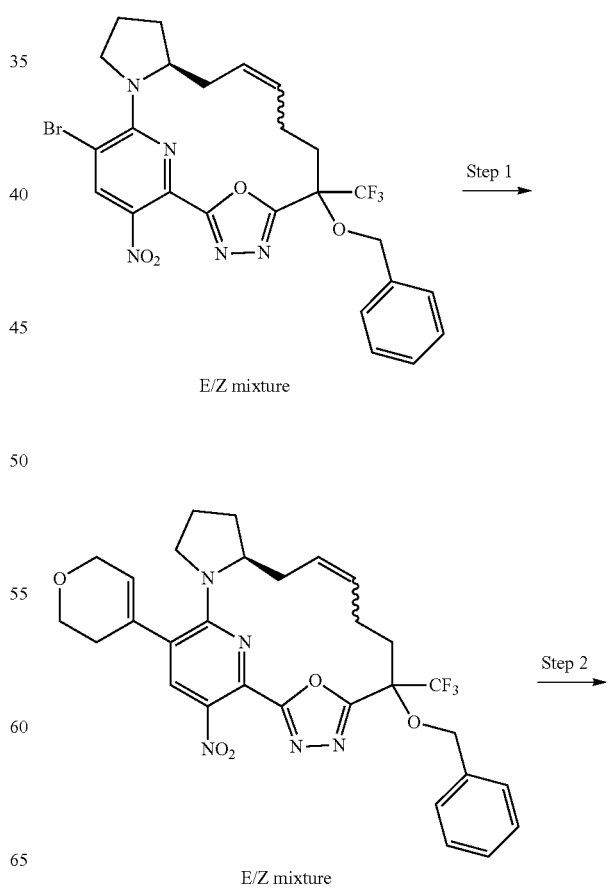

E/Z mixture

Step 1 →

E/Z mixture

Step 2 →

-continued

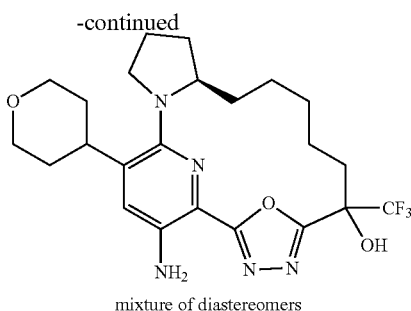

mixture of diastereomers

Step 1: (12S)-6-(Benzyloxy)-18-(3,6-dihydro-2H-pyran-4-yl)-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture)

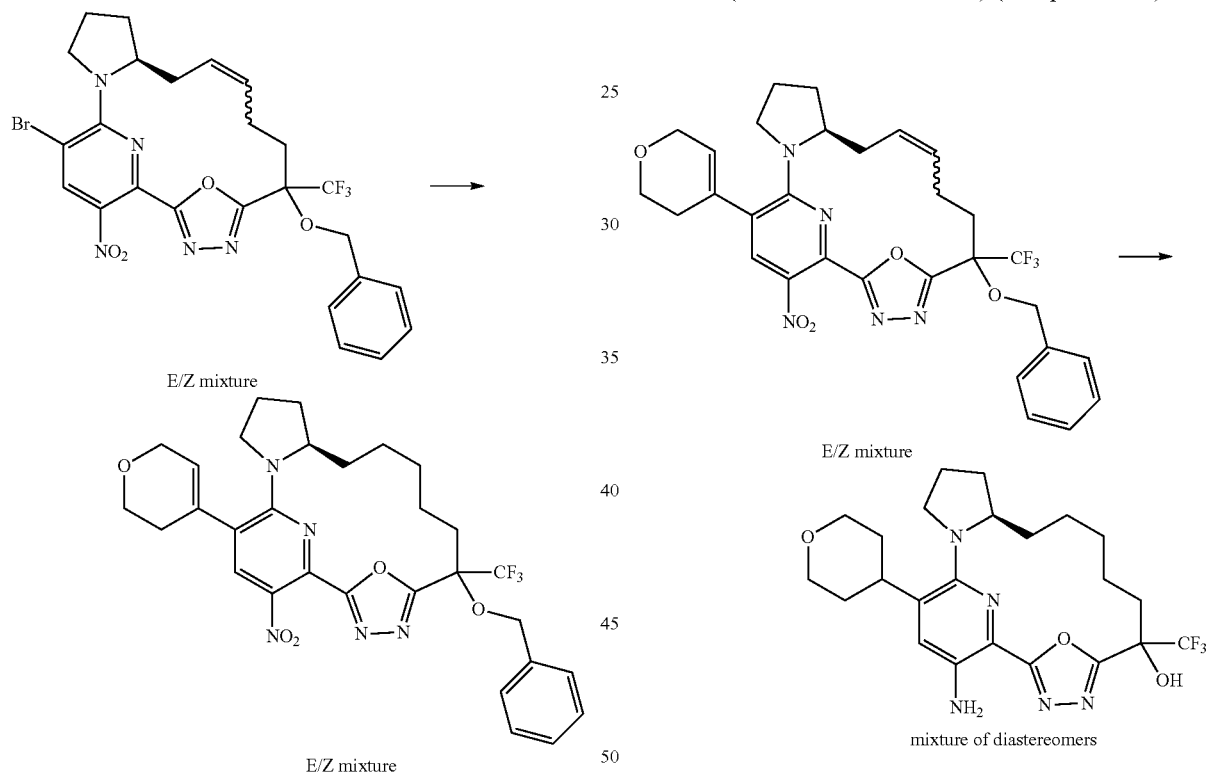

A solution of (12S)-6-(benzyloxy)-18-bromo-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (200 mg, 0.3365 mmol) in toluene (8 mL) was degassed by bubbling nitrogen for 15 minutes. 2-(3,6-Dihydro-2H-pyran-4-yl)-4,4,5,5-tetramethyl-1,3,2-dioxaborolane (107 mg, 0.5093 mmol) and 1,1'-bis(diphenylphosphino)ferrocene palladium(II) chloride, complex with dichloromethane (30 mg, 0.0367 mmol) were added followed by the addition of a degassed aqueous solution of cesium carbonate (0.45 mL, 2 M, 0.9 mmol) under nitrogen. The reaction mixture was stirred overnight at 90° C. After cooling to room temperature, the reaction mixture was diluted with ethyl acetate (30 mL) filtered through a pad of Celite and rinsed with ethyl acetate (2×20 mL). The filtrate was dried over anhydrous sodium sulfate, filtered and concentrated. The residue was purified by reverse phase HPLC using a gradient from 0% to 95% acetonitrile in water (+0.1% formic acid) over 30 minutes giving as a red foam, (12S)-6-(benzyloxy)-18-(3,6-dihydro-2H-pyran-4-yl)-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (152 mg, 76%). $^1$H NMR (300 MHz, Chloroform-d) δ 8.13 (s, 1H), 7.43-7.28 (m, 5H), 5.90-5.77 (m, 1H), 5.67-5.38 (m, 2H), 5.32 (d, J=10.9 Hz, 1H), 5.03-4.91 (m, 1H), 4.46-4.23 (m, 2H), 4.06-3.85 (m, 3H), 3.66-3.34 (m, 3H), 2.57-2.00 (m, 8H), 1.90-1.66 (m, 2H), 1.56-1.46 (m, 1H) ppm. $^{19}$F NMR (282 MHz, Chloroform-d) δ −72.96 (s, 3F), −73.62 (s, 3F) ppm. ESI-MS m/z calc. 597.2199, found 598.2 (M+1)$^+$; Retention time: 2.56 minutes (LC Method E).

Step 2: (12R)-20-Amino-18-(oxan-4-yl)-6-(trifluoromethyl)-22-oxa-3,4,16,21-tetraazatetracyclo[15.3.1.1²,⁵.0¹²,¹⁶]docosa-1(21),2,4,17,19-pentaen-6-ol (mixture of diastereomers) (Compound 123)

(12S)-6-(Benzyloxy)-18-(3,6-dihydro-2H-pyran-4-yl)-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (150 mg, 0.251 mmol) was dissolved in methanol (15 mL). The mixture was bubbled with nitrogen for 5 min and then palladium on carbon (160 mg, 5 w/w, 0.0752 mmol) was added. The resulting mixture was bubbled with a balloon of hydrogen for 5 min and stirred at room temperature under hydrogen for overnight. The mixture was filtered through a pad of Celite and washed with methanol (25 mL) and concentrated under reduced pressure. The resulting residue was purified by reverse phase HPLC using a gradient from 5% to 90% acetonitrile in water (+0.1% formic acid) giving as a light-yellow solid, (12R)-20-amino-18-(oxan-4-yl)-6-(trifluoromethyl)-22-oxa-3,4,16,21-tetraazatetracyclo[15.3.1.1²,⁵.0¹²,¹⁶]docosa-1(21), 2,4,17,19-pentaen-6-ol (mixture of diastereomers) (78 mg, 64%). $^{1}$H NMR (300 MHz, Chloroform-d) δ 7.00 (s, 1H), 5.42-4.68 (m, 2H), 4.22-4.10 (m, 1H), 4.05 (dd, J=11.4, 3.5 Hz, 1H), 3.99-3.81 (m, 1H), 3.79-3.66 (m, 1H), 3.61-3.46 (m, 2H), 3.19-2.99 (m, 2H), 2.62-2.30 (m, 2H), 2.27-2.18 (m, 1H), 2.12-1.92 (m, 2H), 1.91-1.72 (m, 4H), 1.66-1.45 (m, 9H), 1.02-0.75 (m, 1H) ppm. $^{19}$F NMR (282 MHz, Chloroform-d) δ −77.42 (br. s., 3F, minor diastereomer), −80.82 (br. s., 3F, major diastereomer) ppm. ESI-MS m/z calc. 481.2301, found 482.3 (M+1)$^{+}$; Retention time: 3.14 minutes (LC Method C).

Example 62: Preparation of (12R)-20-amino-18-(pyridin-3-yl)-6-(trifluoromethyl)-22-oxa-3,4,16,21-tetraazatetracyclo[15.3.1.12,5.012,16]docosa-1(21), 2,4,17,19-pentaen-6-ol (mixture of diastereomers) (Compound 124)

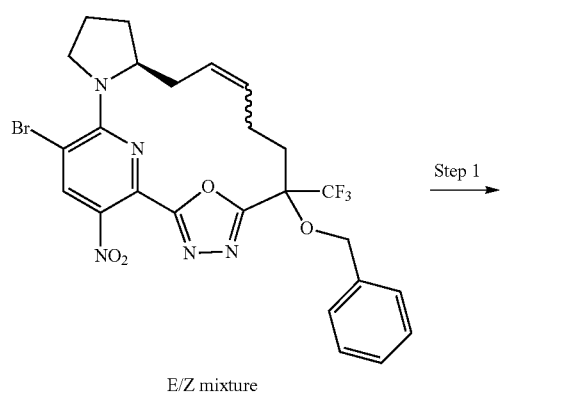

E/Z mixture

Step 1

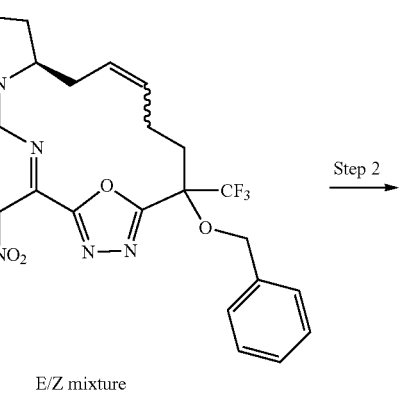

E/Z mixture

Step 2

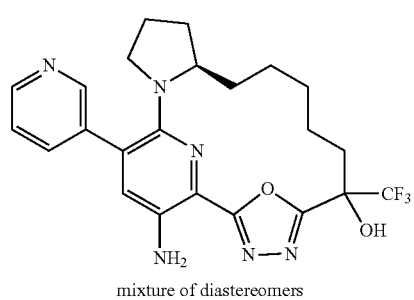

mixture of diastereomers

Step 1: (12S)-6-(Benzyloxy)-20-nitro-18-(pyridin-3-yl)-6-(trifluoromethyl)-22-oxa-3,4,16,21-tetraazatetracyclo[15.3.1.12,5.012,16]docosa-1(21),2,4,9,17,19-hexaene (E/Z Mixture)

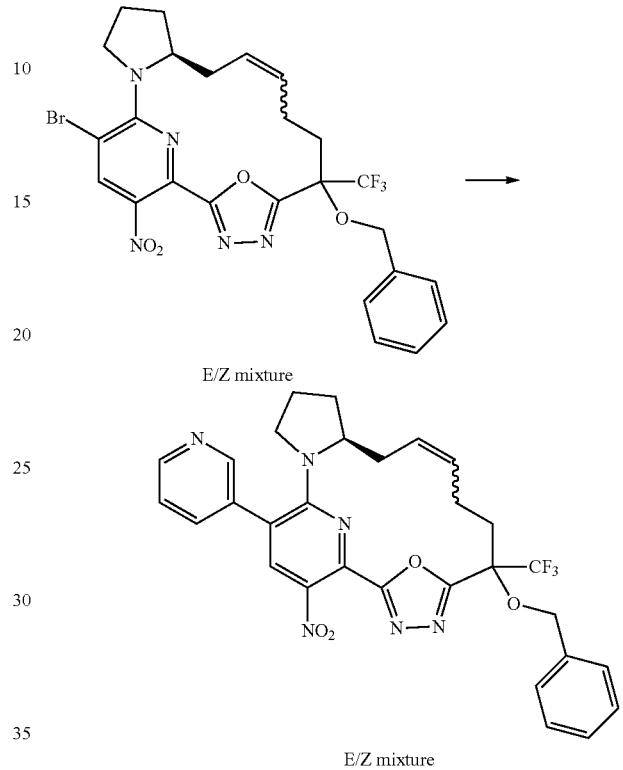

E/Z mixture

E/Z mixture

A solution of (12S)-6-(benzyloxy)-18-bromo-20-nitro-6-(trifluoromethyl)-22-oxa-3,4,16,21-tetraazatetracyclo [15.3.1.12,5.012,16]docosa-1(21),2,4,9,17,19-hexaene (E/Z mixture) (200 mg, 0.3365 mmol) in toluene (8 mL) was degassed by nitrogen bubbling for 15 min. 3-Pyridylboronic acid (60 mg, 0.4881 mmol) and 1,1'-bis(diphenylphosphino) ferrocene palladium(II) chloride, complex with dichloromethane (30 mg, 0.0367 mmol) were added followed by the addition of a degassed aqueous solution of cesium carbonate (450 μL, 2 M, 0.9 mmol) under nitrogen. The reaction mixture was stirred overnight at 90° C. After cooling to room temperature, the reaction mixture was diluted with ethyl acetate (25 mL), filtered through a pad of Celite and rinsed with ethyl acetate (2×15 mL). The filtrate was dried over anhydrous sodium sulfate, filtered and concentrated. The resulting mixture was purified by reverse phase HPLC using a gradient from 0% to 95% acetonitrile in water (+0.1% formic acid) giving as a red foam, (12S)-6-(benzyloxy)-20-nitro-18-(pyridin-3-yl)-6-(trifluoromethyl)-22-oxa-3,4,16,21-tetraazatetracyclo[15.3.1.12,5.012, 16]docosa-1(21),2,4,9,17,19-hexaene (E/Z mixture) (190 mg, 95%). $^{1}$H NMR (300 MHz, Chloroform-d) δ 8.78-8.59 (m, 2H), 8.29 (s, 1H), 7.78-7.68 (m, 1H), 7.54-7.27 (m, 6H), 5.67-5.40 (m, 2H), 5.32 (d, J=10.9 Hz, 1H), 5.04-4.89 (m, 1H), 4.12-3.96 (m, 1H), 3.63-3.47 (m, 1H), 3.01-2.83 (m, 1H), 2.82-2.70 (m, 1H), 2.54-2.11 (m, 5H), 1.95-1.82 (m, 1H), 1.78-1.61 (m, 3H) ppm. $^{19}$F NMR (282 MHz, Chloroform-d) δ −72.95 (br. s., 3F), −73.60 (br. s., 3F) ppm.

601

ESI-MS m/z calc. 592.2046, found 593.3 (M+1)+; Retention time: 2.32 minutes (LC Method E).

Step 2: (12R)-20-Amino-18-(pyridin-3-yl)-6-(trifluoromethyl)-22-oxa-3,4,16,21-tetraazatetracyclo[15.3.1.1².⁵.0¹²,¹⁶]docosa-1(21),2,4,17,19-pentaen-6-ol (mixture of diastereomers) (Compound 124)

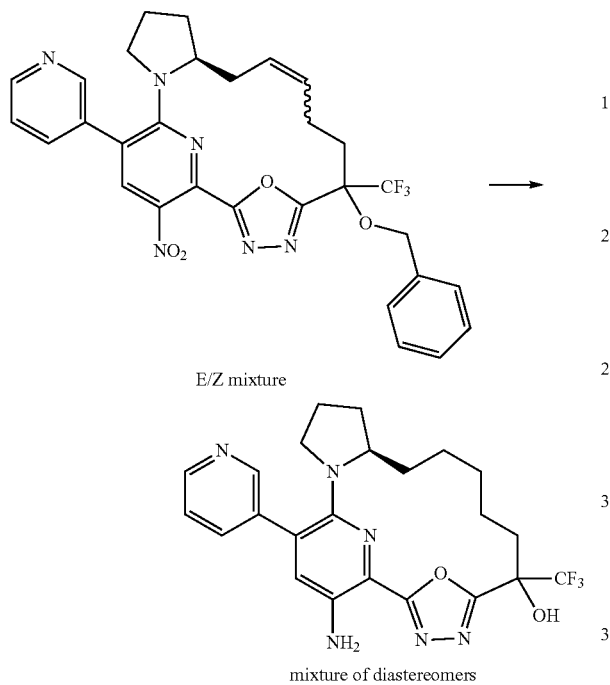

E/Z mixture mixture of diastereomers (12S)-6-(Benzyloxy)-20-nitro-18-(pyridin-3-yl)-6-(trifluoromethyl)-22-oxa-3,4,16,21-tetraazatetracyclo[15.3.1.1².⁵.0¹²,¹⁶]docosa-1(21),2,4,9,17,19-hexaene (E/Z mixture) (190 mg, 0.3206 mmol) was dissolved in methanol (19 mL). The mixture was bubbled with nitrogen for 5 min and then palladium on carbon (275 mg, 5 w/w, 0.1292 mmol) was added. The resulting mixture was bubbled with a balloon of hydrogen for 5 min and the mixture was stirred at room temperature under hydrogen for overnight. The mixture was filtered through a pad of Celite and washed with methanol (25 mL) and concentrated under reduced pressure. The resulting residue was purified by reverse phase HPLC using a gradient from 5% to 90% acetonitrile in water (+0.1% formic acid) giving as a yellow solid, (12R)-20-amino-18-(pyridin-3-yl)-6-(trifluoromethyl)-22-oxa-3,4,16,21-tetraazatetracyclo[15.3.1.1².⁵.0¹²,¹⁶]docosa-1(21),2,4,17,19-pentaen-6-ol (mixture of diastereomers) (45 mg, 29%). ¹H NMR (300 MHz, Chloroform-d) δ 8.94-8.43 (m, 2H), 7.89-7.64 (m, 1H), 7.50-7.30 (m, 1H), 7.18-6.90 (m, 1H), 5.26-4.67 (m, 2H), 4.05-3.77 (m, 1H), 2.98-2.69 (m, 2H), 2.64-2.49 (m, 1H), 2.39-2.00 (m, 3H), 1.81-1.37 (m, 10H), 1.11-0.79 (m, 1H) ppm. ¹⁹F NMR (282 MHz, Chloroform-d) δ−77.34 (br. s., 3F, major diastereoisomer),

602

−80.73 (br. s., 3F, minor diastereoisomer) ppm. ESI-MS m/z calc. 474.1991, found 475.2 (M+1)+; Retention time: 3.08 minutes (LC Method C).

Example 63: Preparation of (12R)-20-amino-18-(pyridin-4-yl)-6-(trifluoromethyl)-22-oxa-3,4,16,21-tetraazatetracyclo[15.3.1.1².⁵.0¹²,¹⁶]docosa-1(21),2,4,17,19-pentaen-6-ol (mixture of diastereomers) (Compound 125)

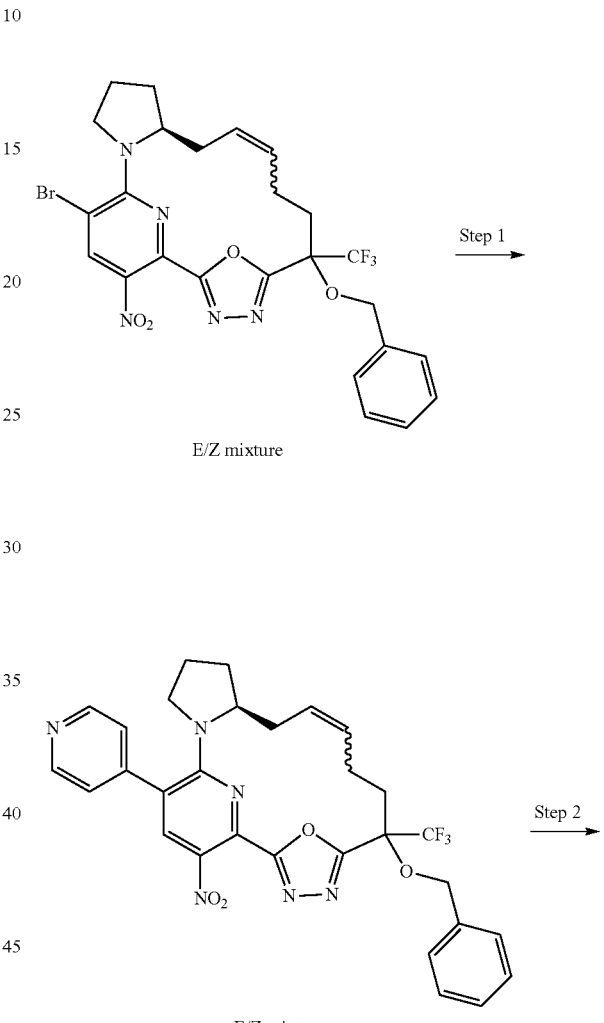

E/Z mixture

Step 1

E/Z mixture

Step 2

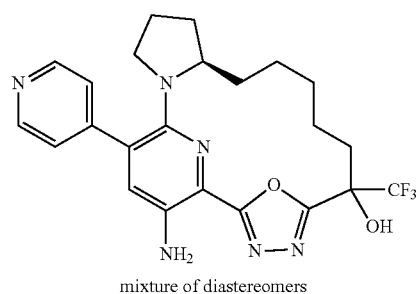

mixture of diastereomers

Step 1: (12S)-6-(Benzyloxy)-20-nitro-18-(pyridin-4-yl)-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture)

Step 2: (12R)-20-Amino-18-(pyridin-4-yl)-6-(trifluoromethyl)-22-oxa-3,4,16,21-tetraazatetracyclo[15.3.1.1²,⁵.0¹²,¹⁶]docosa-1(21),2,4,17,19-pentaen-6-ol (Mixture of Diastereomers) (Compound 125)

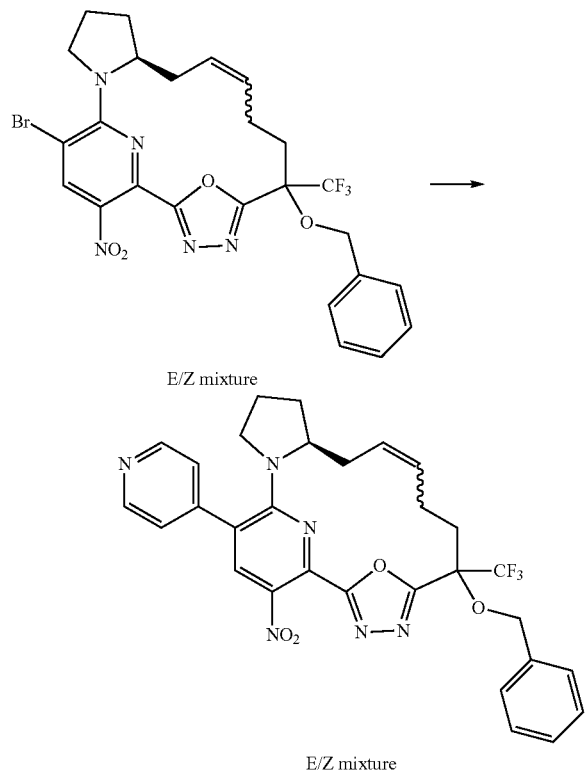

E/Z mixture

E/Z mixture

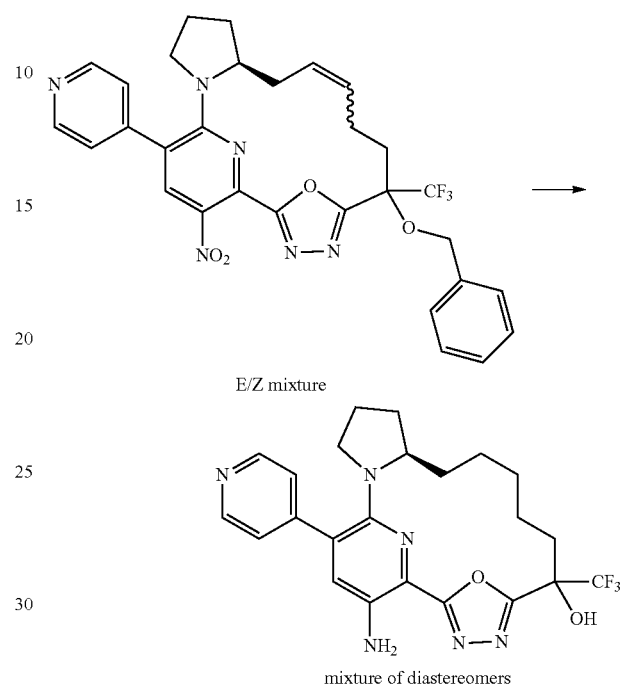

E/Z mixture mixture of diastereomers

A solution of (12S)-6-(benzyloxy)-18-bromo-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (200 mg, 0.3365 mmol) in toluene (8 mL) was degassed by nitrogen bubbling for 15 min. 4-Pyridylboronic acid (60 mg, 0.4881 mmol) and 1,1'-bis(diphenylphosphino)ferrocene palladium(II) chloride, complex with dichloromethane (30 mg, 0.0367 mmol) were added followed by a nitrogen degassed aqueous solution of cesium carbonate (450 µL, 2 M, 0.9 mmol). The reaction mixture was stirred overnight at 90° C. After cooling to room temperature, the reaction mixture was filtered through a pad of Celite and rinsed with ethyl acetate (2×25 mL). The filtrate was dried over anhydrous sodium sulfate, filtered and concentrated. The resulting mixture was purified by reverse phase HPLC using a gradient from 0% to 90% acetonitrile in water (+0.1% formic acid) giving as a yellow foam, (12S)-6-(benzyloxy)-20-nitro-18-(pyridin-4-yl)-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (180 mg, 90%). $^1$H NMR (300 MHz, Chloroform-d) δ 8.75 (br. s., 2H), 8.33 (s, 1H), 7.50-7.28 (m, 7H), 5.68-5.44 (m, 2H), 5.34 (d, J=10.9 Hz, 1H), 5.05-4.90 (m, 1H), 4.12-3.96 (m, 1H), 3.66-3.48 (m, 1H), 3.05-2.88 (m, 1H), 2.79-2.63 (m, 1H), 2.54-2.13 (m, 5H), 1.97-1.83 (m, 1H), 1.81-1.55 (m, 3H) ppm. $^{19}$F NMR (282 MHz, Chloroform-d) δ−72.92 (br. s., 3F), −73.61 (br. s., 3F) ppm. ESI-MS m/z calc. 592.2046, found 593.3 (M+1)$^+$; Retention time: 2.32 minutes (LC Method E).

(12S)-6-(Benzyloxy)-20-nitro-18-(pyridin-4-yl)-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (180 mg, 0.3038 mmol) was dissolved in methanol (18 mL). The mixture was bubbled with nitrogen for 5 min and then palladium on carbon (194 mg, 5 w/w, 0.0911 mmol) was added. The resulting mixture was bubbled with a balloon of hydrogen for 5 min and then the mixture was stirred at room temperature under hydrogen for overnight. The mixture was filtered through a pad of Celite, washed with methanol (25 mL) and the filtrate was concentrated under reduced pressure. The residue was purified by reverse phase HPLC using a gradient from 0% to 95% acetonitrile in water (+0.1% formic acid) giving as an orange solid, (12R)-20-amino-18-(pyridin-4-yl)-6-(trifluoromethyl)-22-oxa-3,4,16,21-tetraazatetracyclo[15.3.1.1²,⁵.0¹²,¹⁶]docosa-1(21),2,4,17,19-pentaen-6-ol (mixture of diastereomers) (60 mg, 41%). $^1$H NMR (300 MHz, Chloroform-d) δ 8.66 (br. s., 2H), 7.48-7.32 (m, 2H), 7.14-6.98 (m, 1H), 5.52-4.47 (m, 2H), 4.05-3.78 (m, 1H), 2.97-2.78 (m, 1H), 2.76-2.58 (m, 1H), 2.57-2.33 (m, 2H), 2.32-1.88 (m, 3H), 1.80-1.44 (m, 9H), 1.02-0.85 (m, 1H) ppm. $^{19}$F NMR (282 MHz, Chloroform-d) δ−77.32 (br. s., 3F, minor diastereomer), −80.70 (br. s., 3F, major diastereomer) ppm. ESI-MS m/z calc. 474.1991, found 475.2 (M+1)$^+$; Retention time: 2.76 minutes (LC Method C).

Example 64: Preparation of (12R)-20-amino-18-(oxolan-3-yl)-6-(trifluoromethyl)-22-oxa-3,4,16,21-tetraazatetracyclo[15.3.1.1²,⁵.0¹²,¹⁶]docosa-1(21),2,4,17,19-pentaen-6-ol (mixture of diastereomers) (Compound 126)

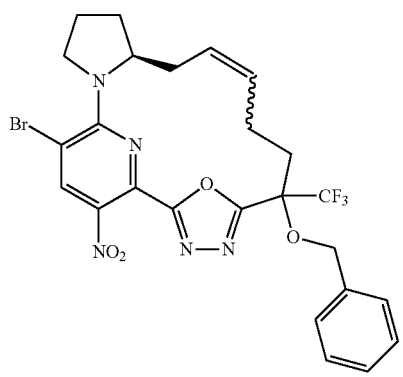

E/Z mixture

↓ Step 1

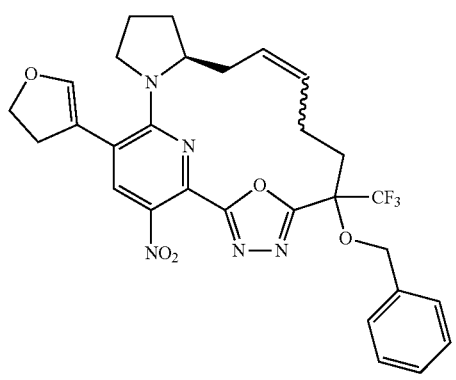

E/Z mixture

↓ Step 2

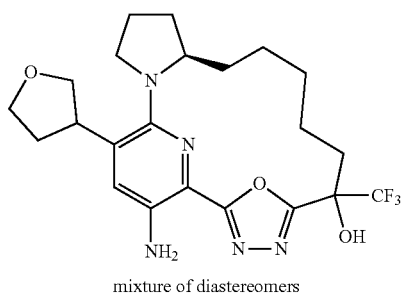

mixture of diastereomers

Step 1: (12S)-6-(Benzyloxy)-18-(2,5-dihydrofuran-3-yl)-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z Mixture)

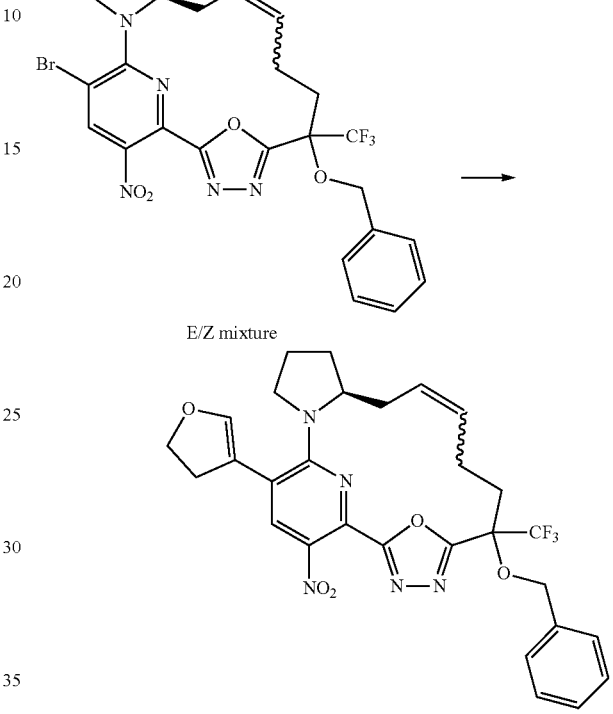

E/Z mixture

A pressure tube was charged with (12S)-6-(benzyloxy)-18-bromo-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (100 mg, 0.1682 mmol), 2-(2,5-dihydrofuran-3-yl)-4,4,5,5-tetramethyl-1,3,2-dioxaborolane (50 mg, 0.255 mmol), cesium carbonate (132 mg, 0.4051 mmol), Pd(dppf)Cl$_2$ (12 mg, 0.0147 mmol), toluene (3 mL) and H$_2$O (0.2 mL). The mixture was bubbled with nitrogen for 3 min and sealed. The reaction mixture was stirred at 90° C. for 22 h, cooled to room temperature and treated with brine (5 mL). The mixture was extracted with EtOAc (320 mL) and the organic layer was dried with Na$_2$SO$_4$, filtered and concentrated. The residue was purified by silica gel chromatography (24 g column) using a gradient from 0% to 50% ethyl acetate in heptane to afford as a yellow solid, (12S)-6-(benzyloxy)-18-(2,5-dihydrofuran-3-yl)-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (98 mg, 100%). $^1$H NMR (300 MHz, Chloroform-d) δ 8.16 (s, 1H), 7.40-7.27 (m, 5H), 5.97-5.88 (m, 1H), 5.63-5.41 (m, 2H), 5.36-4.69 (m, 6H), 4.07-3.92 (m, 1H), 3.62-3.34 (m, 2H), 3.33-3.18 (m, 1H), 2.46-2.06 (m, 6H), 1.88-1.68 (m, 2H), 1.56-1.46 (m, 1H) ppm. $^{19}$F NMR (282 MHz, Chloroform-d) δ −72.79 to −73.78 (m, 3F) ppm. ESI-MS m/z calc. 583.2043, found 584.2 (M+1)$^+$; Retention time: 2.5 minutes (LC Method E).

Step 2: (12R)-20-Amino-18-(oxolan-3-yl)-6-(trifluoromethyl)-22-oxa-3,4,16,21-tetraazatetracyclo[15.3.1.1²,⁵.0¹²,¹⁶]docosa-1(21),2,4,17,19-pentaen-6-ol (mixture of diastereomers) (Compound 126)

Example 65: Preparation of (12R)-20-amino-18-(1-methyl-1H-pyrazol-4-yl)-6-(trifluoromethyl)-22-oxa-3,4,16,21-tetraazatetracyclo[15.3.1.1²,⁵.0¹²,¹⁶]docosa-1(21),2,4,17,19-pentaen-6-ol (mixture of diastereomers) (Compound 127)

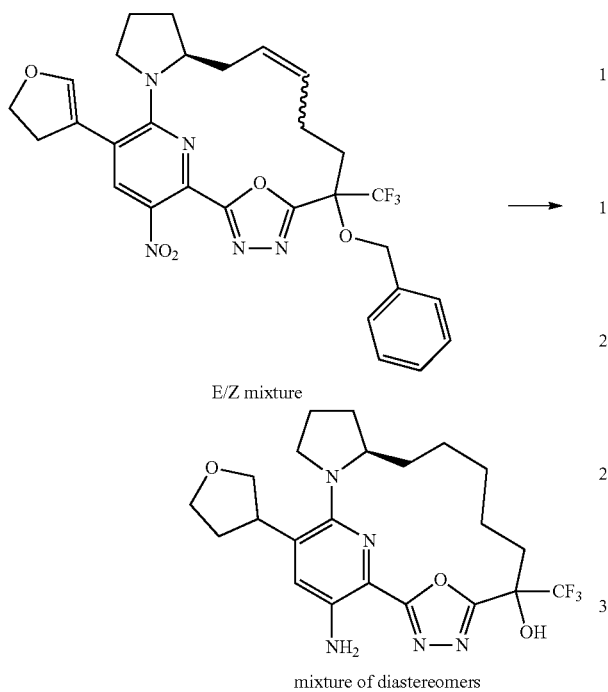

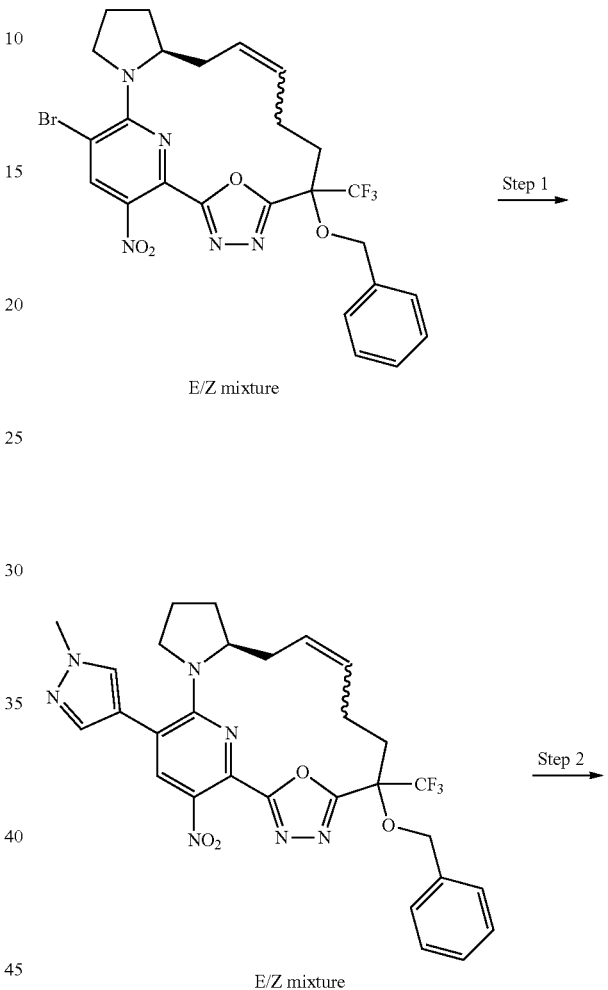

A mixture of (12S)-6-(benzyloxy)-18-(2,5-dihydrofuran-3-yl)-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (98 mg, 0.1679 mmol), 10% palladium on carbon (100 mg, 50% wet 0.047 mmol), EtOAc (4 mL) and MeOH (4 mL) was stirred under a hydrogen balloon at 30° C. to 50° C. for 5 h and then at room temperature overnight. The mixture was filtered through Celite and washed with EtOAc. The filtrate was concentrated, and the residue was purified by flash chromatography (24 g column) using a gradient from 20% to 50% ethyl acetate in heptane to give as a yellow solid, (12R)-20-amino-18-(oxolan-3-yl)-6-(trifluoromethyl)-22-oxa-3,4,16,21-tetraazatetracyclo[15.3.1.1²,⁵.0¹²,¹⁶]docosa-1(21),2,4,17,19-pentaen-6-ol (mixture of diastereomers) (29 mg, 35%). $^1$H NMR (300 MHz, DMSO-d6) δ 7.57-7.46 (m, 1H), 7.33-7.21 (m, 1H), 6.10-5.85 (m, 2H), 4.13-3.87 (m, 2H), 3.85-3.67 (m, 3H), 3.61-3.48 (m, 2H), 3.14-2.96 (m, 1H), 2.47-1.60 (m, 9H), 1.58-1.32 (m, 6H), 0.93-0.73 (m, 1H) ppm. $^{19}$F NMR (282 MHz, DMSO-d6) δ −76.50 (s, 3F, minor diastereomers), −79.35 (s, 3F, major diastereomers) ppm. ESI-MS m/z calc. 467.2144, found 468.1 (M+1)$^+$; Retention time: 3.23 minutes (LC Method C).

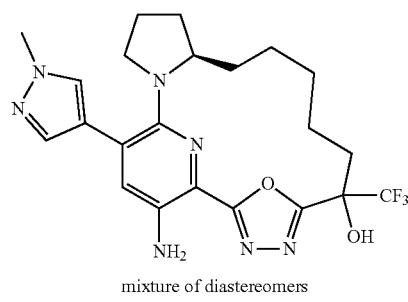

Step 1: (12S)-6-(Benzyloxy)-18-(1-methyl-1H-pyrazol-4-yl)-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z Mixture)

Step 2: (12R)-20-Amino-18-(1-methyl-1H-pyrazol-4-yl)-6-(trifluoromethyl)-22-oxa-3,4,16,21-tetraazatetracyclo[15.3.1.1²,⁵.0¹²,¹⁶]docosa-1(21),2,4,17,19-pentaen-6-ol (Mixture of Diastereomers) (Compound 127)

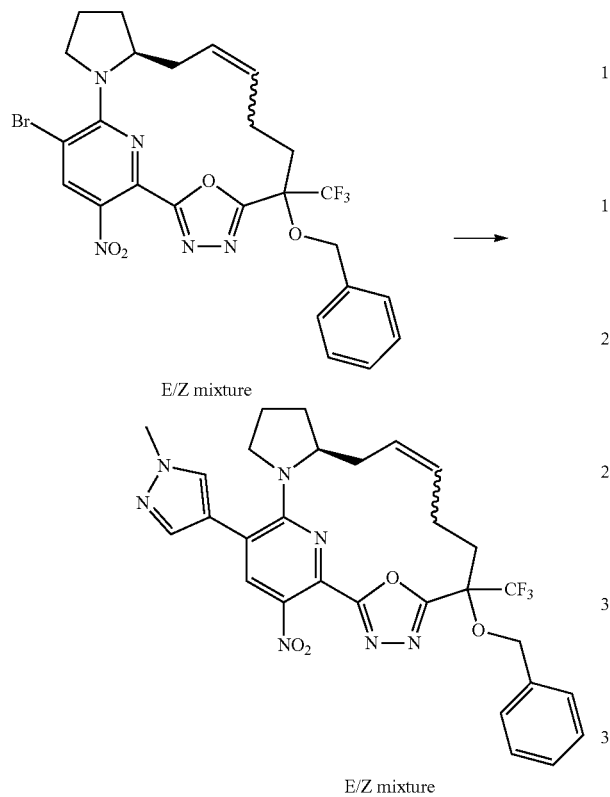

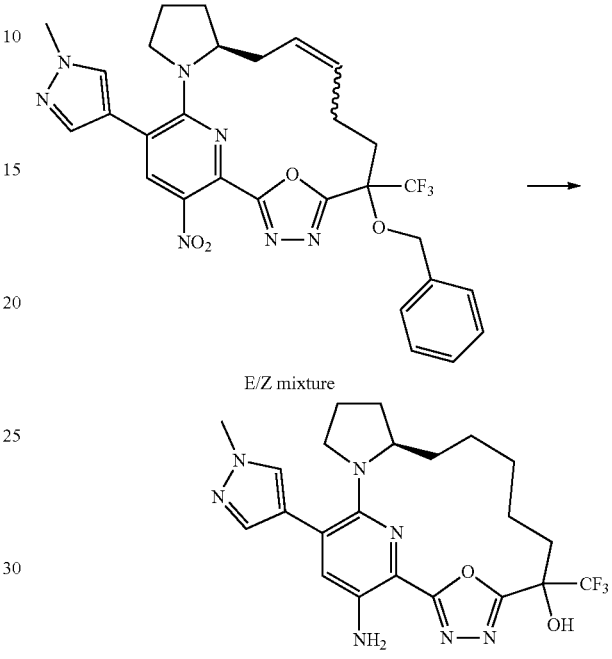

A solution of (12S)-6-(benzyloxy)-18-bromo-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (200 mg, 0.3365 mmol) in toluene (8 mL) and cesium carbonate (0.45 mL, 2 M in water, 0.9 mmol) was degassed by nitrogen bubbling for 20 min. 1-Methyl-4-(4,4,5,5-tetramethyl-1,3,2-dioxaborolan-2-yl)pyrazole (105 mg, 0.5046 mmol) and Pd(dppf)Cl$_2$ (28 mg, 0.0343 mmol) were added. The reaction mixture was stirred overnight at 90° C. After cooling to room temperature, the reaction mixture was filtered through a pad of Celite and rinsed with ethyl acetate (2×25 mL). The filtrate was dried over anhydrous sodium sulfate, filtered and concentrated. The residue was purified by reverse phase HPLC using a gradient from 5% to 100% acetonitrile in water (+0.1% formic acid) giving as a yellow solid, (12S)-6-(benzyloxy)-18-(1-methyl-1H-pyrazol-4-yl)-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (110 mg, 55%). $^1$H NMR (300 MHz, Chloroform-d) δ 8.19 (s, 1H), 7.55 (s, 1H), 7.52-7.47 (m, 1H), 7.42-7.27 (m, 5H), 5.60-5.41 (m, 2H), 5.33-4.90 (m, 2H), 4.05-3.93 (m, 4H), 3.55-3.40 (m, 1H), 3.24-3.07 (m, 1H), 3.05-2.90 (m, 1H), 2.50-2.02 (m, 5H), 1.99-1.82 (m, 1H), 1.79-1.59 (m, 2H), 1.49-1.26 (m, 1H) ppm. $^{19}$F NMR (282 MHz, Chloroform-d) δ −72.98 (s, 3F) (minor diastereoisomer), −73.62 (s, 3F) (major diastereoisomer) ppm. ESI-MS m/z calc. 595.2155, found 596.2 (M+1)$^+$; Retention time: 2.44 minutes (LC Method E).

(12S)-6-(Benzyloxy)-18-(1-methyl-1H-pyrazol-4-yl)-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (100 mg, 0.1679 mmol) was dissolved in methanol (5 mL). The mixture was bubbled with nitrogen for 5 min and then 10% palladium on carbon (20 mg, 0.0094 mmol) was added. The resulting mixture was bubbled with a balloon of hydrogen for 5 min and then stirred at room temperature under hydrogen for 3 days. The mixture was filtered through a pad of Celite and washed with methanol (25 mL) and the filtrate was concentrated under reduced pressure. The residue was purified by reverse phase HPLC using a gradient from 5% to 100% acetonitrile in water (+0.1% formic acid) giving as a yellow solid, (12R)-20-amino-18-(1-methyl-1H-pyrazol-4-yl)-6-(trifluoromethyl)-22-oxa-3,4,16,21-tetraazatetracyclo[15.3.1.1²,⁵.0¹²,¹⁶]docosa-1(21),2,4,17,19-pentaen-6-ol (mixture of diastereomers) (34 mg, 42%). $^1$H NMR (400 MHz, Chloroform-d) δ 7.70-7.61 (m, 1H), 7.59-7.49 (m, 1H), 7.09-6.97 (m, 1H), 5.04 (br. s, 2H), 4.16-3.82 (m, 4H), 3.21 (br. s, 1H), 2.81-2.01 (m, 5H), 1.88-1.77 (m, 1H), 1.75-1.44 (m, 9H), 1.09-0.87 (m, 1H) ppm. $^{19}$F NMR (282 MHz, Chloroform-d) δ −77.40 (s, 3F) (minor diastereomer), −80.72 (s, 3F) (major diastereomer) ppm. ESI-MS m/z calc. 477.21, found 478.1 (M+1)$^+$; Retention time: 3.26 minutes (LC Method C).

Example 66: Preparation of (12R)-20-amino-18-(1H-pyrazol-4-yl)-6-(trifluoromethyl)-22-oxa-3,4,16,21-tetraazatetracyclo[15.3.1.1²,⁵.0¹²,¹⁶]docosa-1(21),2,4,17,19-pentaen-6-ol (mixture of diastereomers) (Compound 128)

Step 1: (12S)-6-(Benzyloxy)-20-nitro-18-(1H-pyrazol-4-yl)-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z Mixture)

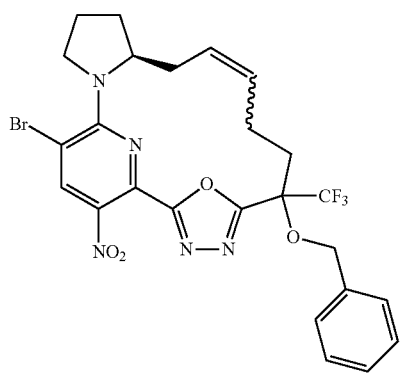

E/Z mixture

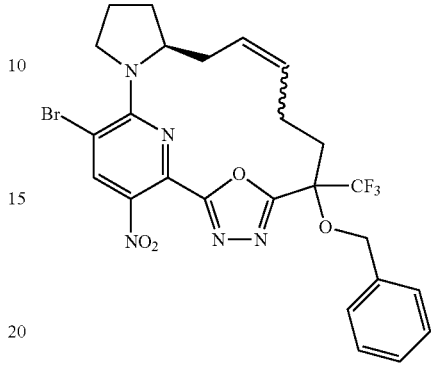

E/Z mixture

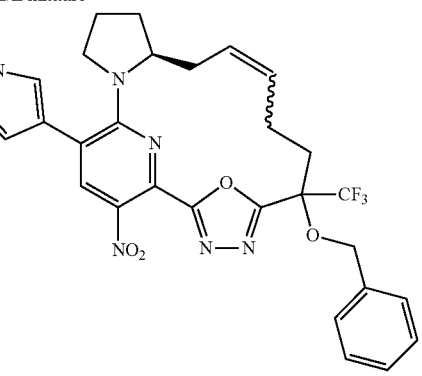

E/Z mixture

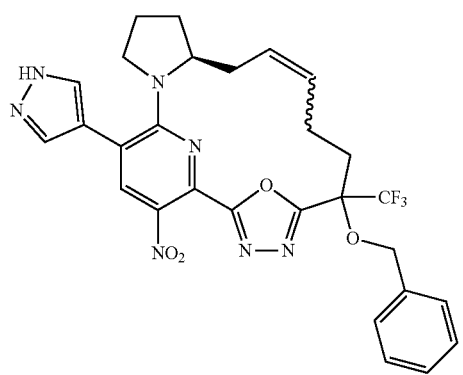

E/Z mixture

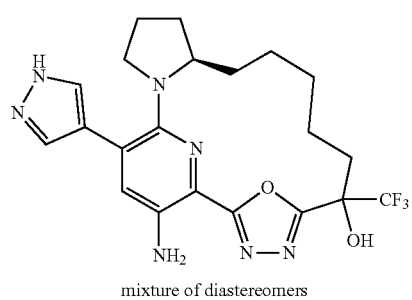

mixture of diastereomers

In a sealed tube, a solution of (12S)-6-(benzyloxy)-18-bromo-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (200 mg, 0.3365 mmol) in dioxane (8 mL), water (1.5 mL) and cesium carbonate (0.5 mL, 2 M, 1 mmol) was degassed by nitrogen bubbling for 20 min and 4-(4,4,5,5-tetramethyl-1,3,2-dioxaborolan-2-yl)-1H-pyrazole (98 mg, 0.5051 mmol) and Pd(dppf)Cl$_2$ (28 mg, 0.0343 mmol) were added. The reaction mixture was stirred overnight at 120° C. After cooling to room temperature, the reaction mixture was filtered through a pad of Celite and rinsed with ethyl acetate (2×25 mL). The filtrate was dried over anhydrous sodium sulfate, filtered and concentrated. The resulting residue was purified by reverse phase HPLC using a gradient from 5% to 100% acetonitrile in water (+0.1% formic acid) giving as a yellow solid, (12S)-6-(benzyloxy)-20-nitro-18-(1H-pyrazol-4-yl)-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (18 mg, 9%). $^1$H NMR (300 MHz, Chloroform-d) δ 8.27-8.18 (m, 1H), 7.76-7.67 (m, 2H), 7.42-7.28 (m, 5H), 5.63-5.43 (m, 2H), 5.33-4.90 (m, 2H), 4.08-3.93 (m, 1H), 3.57-3.40 (m, 1H), 3.17-3.03 (m, 1H), 3.02-2.89 (m, 1H), 2.50-1.44 (m, 10H) ppm. $^{19}$F NMR (282 MHz, Chloroform-d) δ −72.98 (s, 3F) (minor diastereomer), −73.60 (s, 3F) (major diastereomer) ppm. ESI-MS m/z calc. 581.1998, found 582.2 (M+1)$^+$; Retention time: 2.35 minutes (LC Method E).

Step 2: (12R)-20-Amino-18-(1H-pyrazol-4-yl)-6-(trifluoromethyl)-22-oxa-3,4,16,21-tetraazatetracyclo[15.3.1.1²,⁵.0¹²,¹⁶]docosa-1(21),2,4,17,19-pentaen-6-ol (Mixture of Diastereomers) (Compound 128)

Example 67: Preparation of (12R)-20-amino-18-cyclohexyl-6-(trifluoromethyl)-22-oxa-3,4,16,21-tetraazatetracyclo[15.3.1.1²,⁵.0¹²,¹⁶]docosa-1(21),2,4,17,19-pentaen-6-ol (Mixture of Diastereomers) (Compound 129)

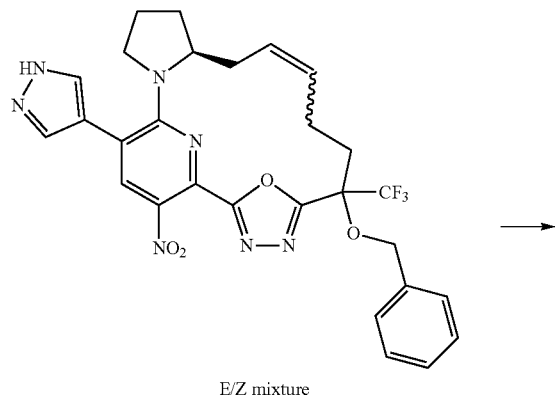

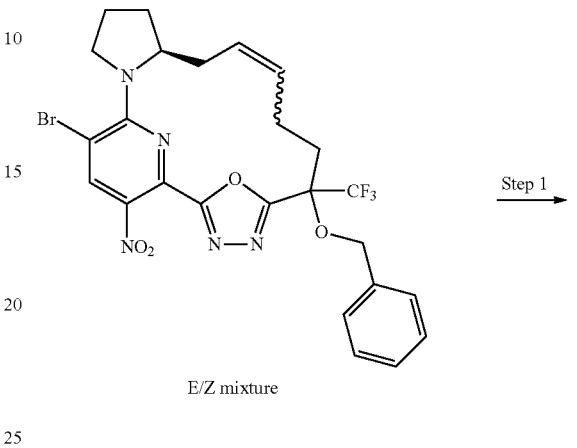

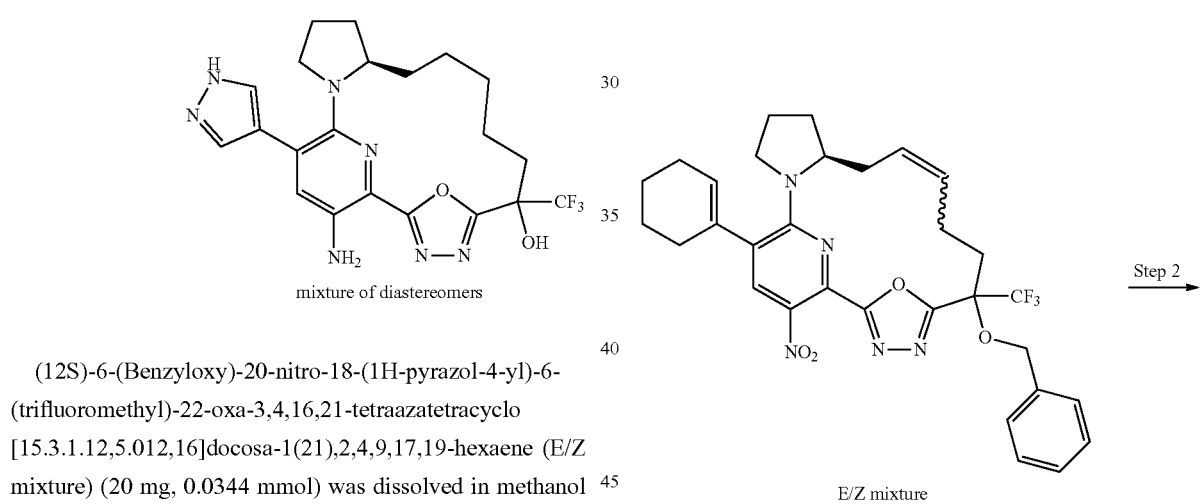

(12S)-6-(Benzyloxy)-20-nitro-18-(1H-pyrazol-4-yl)-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (20 mg, 0.0344 mmol) was dissolved in methanol (3 mL). The mixture was bubbled with nitrogen for 5 min and then 10% palladium on carbon (4 mg, 0.0019 mmol) was added. The resulting mixture was bubbled with a balloon of hydrogen for 5 min and then stirred at room temperature under hydrogen overnight. The mixture was filtered through a pad of Celite and washed with methanol (25 mL) and the filtrate was concentrated under reduced pressure. The residue was purified by reverse phase HPLC using a gradient from 5% to 100% acetonitrile in water (+0.1% formic acid) giving as a yellow solid, (12R)-20-amino-18-(1H-pyrazol-4-yl)-6-(trifluoromethyl)-22-oxa-3,4,16,21-tetraazatetracyclo[15.3.1.1²,⁵.0¹²,¹⁶]docosa-1(21),2,4,17,19-pentaen-6-ol (mixture of diastereomers) (3 mg, 14%). ESI-MS m/z calc. 463.1944, found 464.2 (M+1)⁺; Retention time: 3.11 minutes (LC Method C).

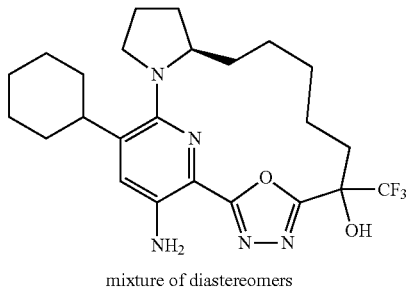

mixture of diastereomers

Step 1: (12S)-6-(Benzyloxy)-18-(cyclohex-1-en-1-yl)-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture)

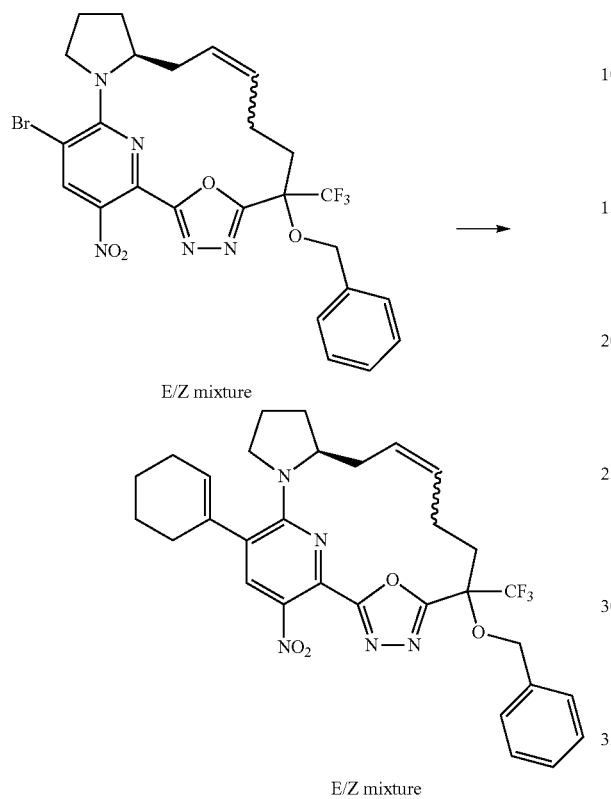

E/Z mixture

E/Z mixture

In a sealed tube, a solution of (12S)-6-(benzyloxy)-18-bromo-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (200 mg, 0.3365 mmol) in toluene (8 mL) and cesium carbonate (0.5 mL, 2 M, 1 mmol) was degassed by nitrogen bubbling for 20 min and cyclohexen-1-ylboronic acid (64 mg, 0.5081 mmol) and Pd(dppf)Cl$_2$ (28 mg, 0.0343 mmol) were added. The reaction mixture was stirred overnight at 90° C. After cooling to room temperature, the reaction mixture was filtered through a pad of Celite and rinsed with ethyl acetate (2×25 mL). The filtrate was dried over anhydrous sodium sulfate, filtered and concentrated. The resulting residue was purified by reverse phase HPLC using a gradient from 5% to 100% acetonitrile in water (+0.1% formic acid) giving as a yellow solid, (12S)-6-(benzyloxy)-18-(cyclohex-1-en-1-yl)-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (136 mg, 68%). $^1$H NMR (300 MHz, Chloroform-d) δ 8.05 (s, 1H), 7.50-7.26 (m, 5H), 5.78 (br. s., 1H), 5.60-5.42 (m, 2H), 5.34-4.86 (m, 2H), 4.05-3.89 (m, 1H), 3.57-3.37 (m, 2H), 2.48-1.95 (m, 9H), 1.87-1.45 (m, 9H) ppm. $^{19}$F NMR (282 MHz, Chloroform-d) δ −72.98 (s, 3F) (minor diastereomer), −73.61 (s, 3F) (major diastereomer) ppm. Retention time: 2.89 minutes (LC Method E).

Step 2: (12R)-20-Amino-18-cyclohexyl-6-(trifluoromethyl)-22-oxa-3,4,16,21-tetraazatetracyclo[15.3.1.1²,⁵.0¹²,¹⁶]docosa-1(21),2,4,17,19-pentaen-6-ol (mixture of diastereomers) (Compound 129)

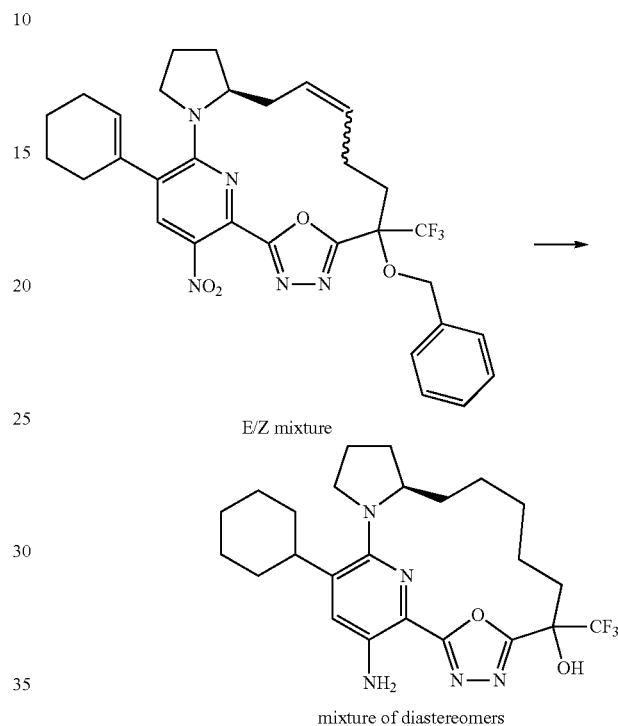

E/Z mixture mixture of diastereomers (12S)-6-(Benzyloxy)-18-(cyclohex-1-en-1-yl)-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (136 mg, 0.2283 mmol) was dissolved in methanol (5 mL). The mixture was bubbled with nitrogen for 5 min and then 10% palladium on carbon (25 mg, 0.0117 mmol) was added. The resulting mixture was bubbled with a balloon of hydrogen for 5 min and then stirred at room temperature under 1 atmosphere of hydrogen overnight. The mixture was filtered through a pad of Celite, washed with methanol (25 mL) and the filtrate was concentrated under reduced pressure. The residue was purified by reverse phase HPLC using a gradient from 5% to 100% acetonitrile in water (+0.1% formic acid) giving as a yellow solid, (12R)-20-amino-18-cyclohexyl-6-(trifluoromethyl)-22-oxa-3,4,16,21-tetraazatetracyclo[15.3.1.1²,⁵.0¹²,¹⁶]docosa-1(21),2,4,17,19-pentaen-6-ol (mixture of diastereomers) (49 mg, 44%). $^1$H NMR (300 MHz, DMSO-d6) δ 7.52 (br. s, 1H), 7.21 (s, 1H), 5.93 (br. s., 2H), 3.94-3.64 (m, 2H), 3.14-3.01 (m, 1H), 2.83-2.69 (m, 1H), 2.48-2.23 (m, 2H), 2.22-2.07 (m, 1H), 2.04-1.83 (m, 4H), 1.81-1.70 (m, 4H), 1.65-1.09 (m, 12H), 0.94-0.74 (m, 1H) ppm. $^{19}$F NMR (282 MHz, DMSO-d6) δ−76.47 (s, 3F) (minor diastereomer), −79.36 (s, 3F) (major diastereomer) ppm. ESI-MS m/z calc. 479.2508, found 480.3 (M+1)$^+$; Retention time: 3.82 minutes (LC Method C).

Example 68: Preparation of (15R)-23-amino-10-fluoro-6,21-bis(trifluoromethyl)-26-oxa-3,4,19,24-tetraazapentacyclo[18.3.1.1²,⁵.1⁷,¹¹.0¹⁵,¹⁹]hexacosa-1(24),2,4,7,9,11(25),20,22-octaen-6-ol (enantiomer 1) (hydrochloride salt) (Compound 130) and (15R)-23-amino-10-fluoro-6,21-bis(trifluoromethyl)-26-oxa-3,4,19,24-tetraazapentacyclo[18.3.1.1²,⁵.1⁷,¹¹.0¹⁵,¹⁹]hexacosa-1(24),2,4,7,9,11(25),20,22-octaen-6-ol (enantiomer 2) (hydrochloride salt) (Compound 131)

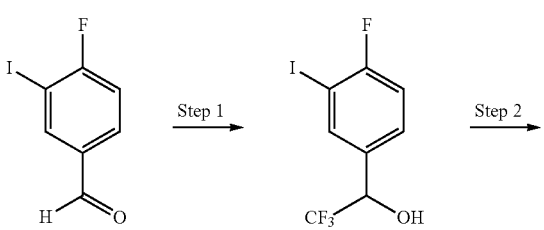

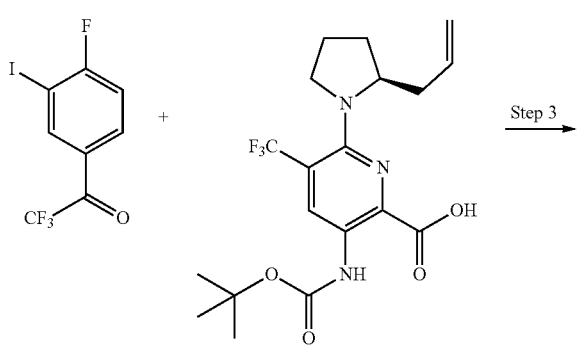

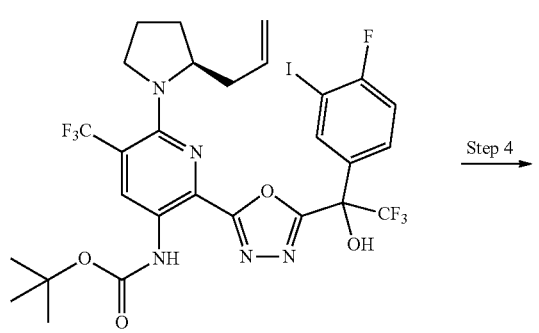

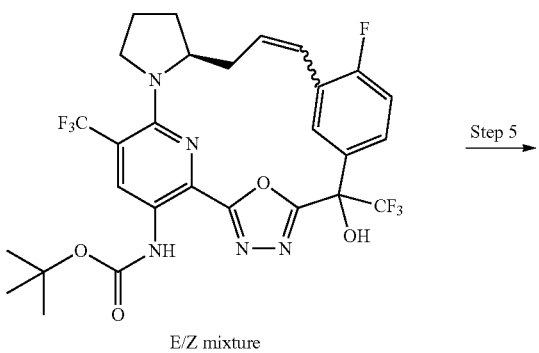

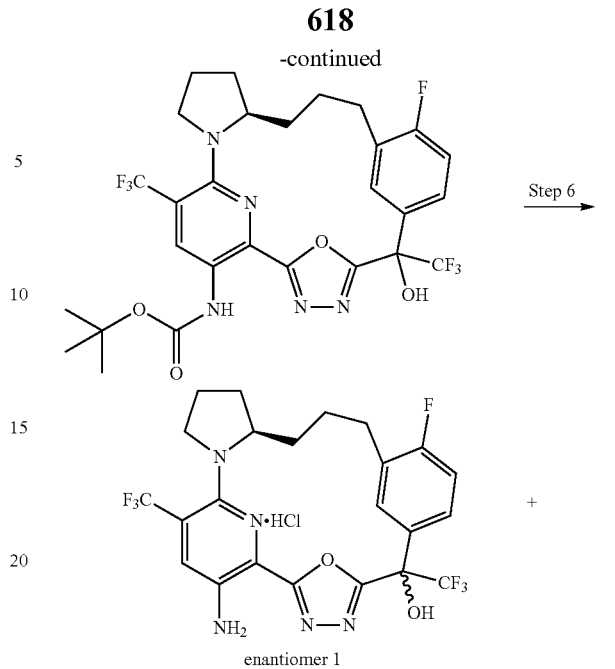

Step 1:
2,2,2-Trifluoro-1-(4-fluoro-3-iodo-phenyl)ethanol

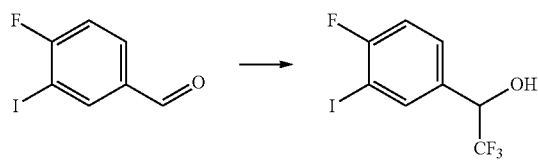 [SMILES: O=Cc1ccc(F)c(I)c1 ; OC(c1ccc(F)c(I)c1)C(F)(F)F]

A vial was charged with 4-fluoro-3-iodo-benzaldehyde (1.5 g, 5.9998 mmol) and TMSCF₃ (1.1544 g, 1.2 mL, 8.1184 mmol) in THF (6 mL) then cooled to 0° C. After 10 min, TBAF (0.06 mL, 1 M in THF, 0.06 mmol) was added dropwise maintaining the temperature at <5° C. The reaction was stirred for 10 min, then warmed to room temperature and stirred overnight. The reaction was then cooled to 0° C. and water (0.75 mL, 41.631 mmol) was added, followed by the dropwise addition of TBAF (0.66 mL, 1 M in THF, 0.66 mmol) at the same temperature. The reaction was stirred at 0° C. for 10 min, then warmed to room temperature and stirred for 3 h. The reaction was poured into water (100 mL) and DCM (100 mL), then the organic layer was separated, dried over anhydrous sodium sulfate, filtered and concentrated under reduced pressure giving as a brown oil, 2,2,2-trifluoro-1-(4-fluoro-3-iodo-phenyl)ethanol (2 g, 99%). ¹H NMR (500 MHz, Chloroform-d) δ 7.88 (dd, J=6.0, 2.2 Hz, 1H), 7.48-7.36 (m, 1H), 7.14-6.99 (m, 1H), 5.01-4.87 (m, 1H), 3.15 (s, 1H) ppm.

Step 2:
2,2,2-Trifluoro-1-(4-fluoro-3-iodo-phenyl)ethanone

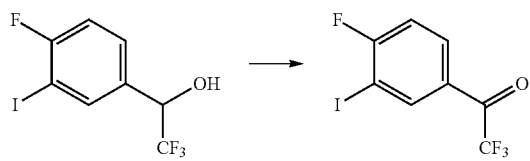 [SMILES: OC(c1ccc(F)c(I)c1)C(F)(F)F ; O=C(c1ccc(F)c(I)c1)C(F)(F)F]

To a solution of 2,2,2-trifluoro-1-(4-fluoro-3-iodo-phenyl)ethanol (2 g, 5.9371 mmol) in DCM (40 mL) was added Dess-Martin periodinane (4 g, 9.4308 mmol) at room temperature. The reaction was stirred at the same temperature for 3 h. The reaction was quenched with 200 mL of 10% sodium thiosulfate solution. The organic layer was separated and washed with saturated NaHCO₃ solution (200 mL), then with brine (200 mL). The organics were dried over Na₂SO₄, filtered, and concentrated under reduced pressure. The residue was purified y silica gel chromatography (40 g column) using a gradient from 0% to 10% diethyl ether in hexanes giving as an amber liquid, 2,2,2-trifluoro-1-(4-fluoro-3-iodo-phenyl)ethanone (1.485 g, 75%). ¹H NMR (500 MHz, DMSO-d6) δ 8.38 (dd, J=6.0, 2.3 Hz, 1H), 8.14-8.06 (m, 1H), 7.55 (dd, J=8.7, 7.8 Hz, 1H) ppm. ESI-MS m/z calc. 317.9165, found 318.9 (M+1)⁺; Retention time: 2.14 minutes (LC Method H).

Step 3: tert-Butyl N-[6-[(2S)-2-allylpyrrolidin-1-yl]-2-[5-[2,2,2-trifluoro-1-(4-fluoro-3-iodo-phenyl)-1-hydroxy-ethyl]-1,3,4-oxadiazol-2-yl]-5-(trifluoromethyl)-3-pyridyl]carbamate

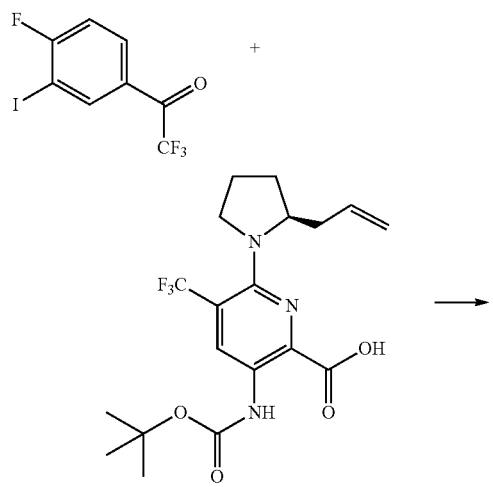

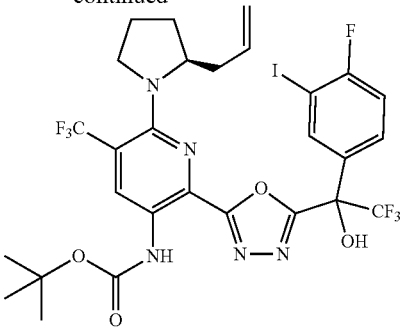

To a stirred solution of 2,2,2-trifluoro-1-(4-fluoro-3-iodo-phenyl)ethanone (587 mg, 1.846 mmol) and 6-[(2S)-2-allylpyrrolidin-1-yl]-3-(tert-butoxycarbonylamino)-5-(trifluoromethyl)pyridine-2-carboxylic acid (500 mg, 1.204 mmol) in DMF (5 mL) was added (N-isocyanoimino)triphenylphosphorane (568 mg, 1.879 mmol) all at once. The mixture was stirred at room temperature for 1 h. Then the mixture was diluted with EtOAc (50 mL), washed with water then brine, dried over sodium sulfate, filtered and concentrated. The resultant brown residue was purified by silica gel chromatography using a shallow gradient from 100% hexanes to 50% EtOAc in hexanes giving as a yellow solid, tert-butyl N-[6-[(2S)-2-allylpyrrolidin-1-yl]-2-[5-[2,2,2-trifluoro-1-(4-fluoro-3-iodo-phenyl)-1-hydroxy-ethyl]-1,3,4-oxadiazol-2-yl]-5-(trifluoromethyl)-3-pyridyl]carbamate (580 mg, 64%). ¹H NMR (400 MHz, DMSO-d6) δ 9.46 (d, J=10.8 Hz, 1H), 8.87 (d, J=8.7 Hz, 1H), 8.67 (d, J=16.3 Hz, 1H), 8.06 (dd, J=5.9, 2.3 Hz, 1H), 7.60 (dddd, J=29.6, 7.4, 4.7, 2.4 Hz, 1H), 7.36 (dt, J=19.0, 8.3 Hz, 1H), 5.55 (dddt, J=50.3, 17.5, 10.7, 7.2 Hz, 1H), 5.04-4.93 (m, 1H), 4.89-4.80 (m, 1H), 4.26 (dtd, J=15.0, 8.4, 4.1 Hz, 1H), 3.58-3.49 (m, 1H), 3.36 (d, J=8.9 Hz, 1H), 2.37 (tdd, J=12.2, 7.9, 2.5 Hz, 1H), 2.12 (dt, J=13.3, 7.9 Hz, 1H), 2.03-1.91 (m, 2H), 1.75-1.59 (m, 2H), 1.48 (d, J=3.2 Hz, 9H) ppm. ESI-MS m/z calc. 757.0996, found 758.0 (M+1)⁺; Retention time: 2.34 minutes (LC Method J).

Step 4: tert-Butyl N-[(15S)-10-fluoro-6-hydroxy-6,21-bis(trifluoromethyl)-26-oxa-3,4,19,24-tetraazapentacyclo[18.3.1.1²,⁵.1⁷,¹¹.0¹⁵,¹⁹]hexacosa-1(24),2,4,7(25),8,10,12,20,22-nonaen-23-yl]carbamate (E/Z mixture)

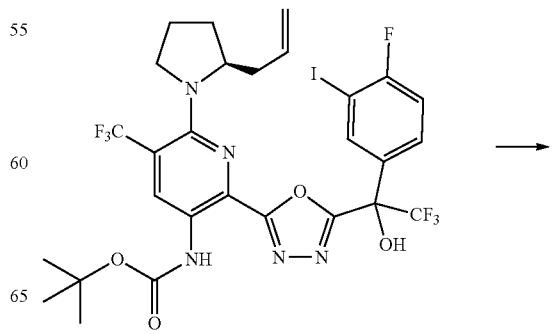

621

-continued

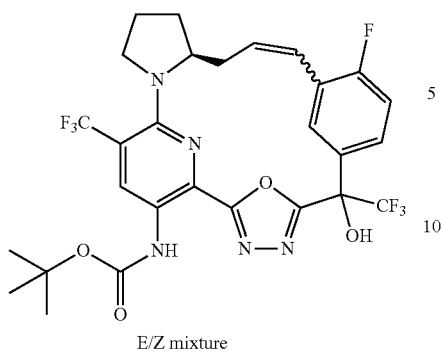

E/Z mixture

To a stirred solution of tert-butyl N-[6-[(2S)-2-allylpyrrolidin-1-yl]-2-[5-[2,2,2-trifluoro-1-(4-fluoro-3-iodo-phenyl)-1-hydroxy-ethyl]-1,3,4-oxadiazol-2-yl]-5-(trifluoromethyl)-3-pyridyl]carbamate (575 mg, 0.7591 mmol) in acetonitrile (70 mL) was added palladium(II) acetate (19 mg, 0.08463 mmol) followed by tris(o-tolyl)phosphane (52 mg, 0.1708 mmol) and triethylamine (550 µL, 3.946 mmol) and the solution was bubbled with N₂ for 2 min then heated at 80° C. for 22 h. Cooled the mixture to room temperature, concentrated to about 5 mL volume and filtered through Celite and filtrate was concentrated. The resultant brown residue was purified by silica gel chromatography using a shallow gradient 100% hexanes to 50% ethyl acetate in hexanes giving as a yellow solid, tert-butyl N-[(15S)-10-fluoro-6-hydroxy-6,21-bis(trifluoromethyl)-26-oxa-3,4,19,24-tetraazapentacyclo[18.3.1.1²,⁵.1⁷,¹¹.0¹⁵,¹⁹]hexacosa-1(24),2,4,7(25),8,10,12,20,22-nonaen-23-yl]carbamate (E/Z mixture) (162 mg, 34%). ESI-MS m/z calc. 629.1873, found 630.1 (M+1)⁺; Retention time: 1.7 minutes (LC Method M).

Step 5: tert-Butyl N-[(15R)-10-fluoro-6-hydroxy-6,21-bis(trifluoromethyl)-26-oxa-3,4,19,24-tetraazapentacyclo[18.3.1.1²,⁵.1⁷,¹¹.0¹⁵,¹⁹]hexacosa-1(24),2,4,7(25),8,10,20,22-octaen-23-yl]carbamate

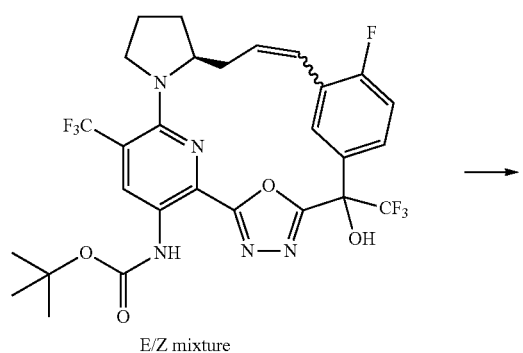

E/Z mixture

622

-continued

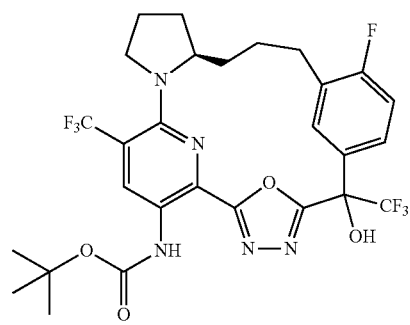

To a solution of tert-butyl N-[(15S)-10-fluoro-6-hydroxy-6,21-bis(trifluoromethyl)-26-oxa-3,4,19,24-tetraazapentacyclo[18.3.1.1²,⁵.1⁷,¹¹.0¹⁵,¹⁹]hexacosa-1(24),2,4,7(25),8,10,12,20,22-nonaen-23-yl]carbamate (E/Z mixture) (160 mg, 0.2542 mmol) in ethyl acetate (5 mL) was added Pd/C (32 mg, 10% w/w, 0.03007 mmol) in a round bottom flask equipped with a H₂ balloon using a 3-way adaptor. Subjected to vacuum and backfilled with nitrogen gas three times then subjected to vacuum. Filled the flask with hydrogen gas then stirred the mixture for 15 hours. Subjected to vacuum and backfilled with nitrogen gas three times then diluted with ethyl acetate and filtered over Celite. The filtrate was concentrated and dried to give as a yellow solid, tert-butyl N-[(15R)-10-fluoro-6-hydroxy-6,21-bis(trifluoromethyl)-26-oxa-3,4,19,24-tetraazapentacyclo[18.3.1.1²,⁵.1⁷,¹¹.0¹⁵,¹⁹]hexacosa-1(24),2,4,7(25),8,10,20,22-octaen-23-yl]carbamate (160 mg, 100%). ESI-MS m/z calc. 631.20294, found 632.0 (M+1)⁺; Retention time: 1.83 minutes (LC Method M).

Step 6: (15R)-23-Amino-10-fluoro-6,21-bis(trifluoromethyl)-26-oxa-3,4,19,24-tetraazapentacyclo[18.3.1.1²,⁵.1⁷,¹¹.0¹⁵,¹⁹]hexacosa-1(24),2,4,7,9,11(25),20,22-octaen-6-ol (enantiomer 1) (hydrochloride salt) (Compound 130) and (15R)-23-amino-10-fluoro-6,21-bis(trifluoromethyl)-26-oxa-3,4,19,24-tetraazapentacyclo[18.3.1.1²,⁵.1⁷,¹¹.0¹⁵,¹⁹]hexacosa-1(24),2,4,7,9,11(25),20,22-octaen-6-ol (enantiomer 2) (hydrochloride salt) (Compound 131)

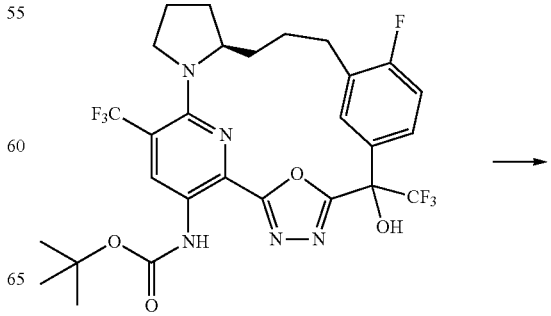

-continued

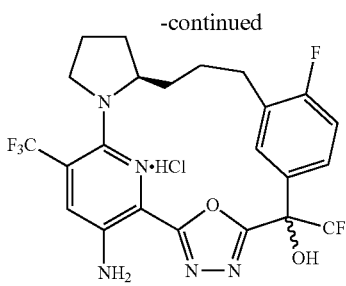
enantiomer 1

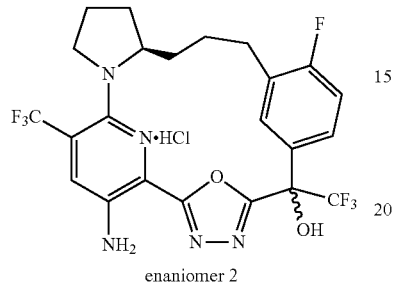
enantiomer 2

A solution of tert-butyl N-[(15R)-10-fluoro-6-hydroxy-6,21-bis(trifluoromethyl)-26-oxa-3,4,19,24-tetraazapentacyclo[18.3.1.1²,⁵.1⁷,¹¹.0¹⁵,¹⁹]hexacosa-1(24),2,4,7(25),8,10,20,22-octaen-23-yl]carbamate (150 mg, 0.2375 mmol) in a pre-made solution of TFA (500 μL, 6.49 mmol) and dichloromethane (2 mL) was stirred at room temperature for about 1 h. Solvents were removed, and the residue was purified by reverse phase HPLC using a gradient from 50% to 99% acetonitrile in water (+5 mM HCl) over 30 minutes giving two diastereomeric products:

The first diastereomer to elute was isolated as a yellow solid, (15R)-23-amino-10-fluoro-6,21-bis(trifluoromethyl)-26-oxa-3,4,19,24-tetraazapentacyclo[18.3.1.1$^{2,5}$.1$^{7,11}$.0$^{15,19}$]hexacosa-1(24),2,4,7,9,11(25),20,22-octaen-6-ol (enantiomer 1) (hydrochloride salt) (50.1 mg, 74%). $^1$H NMR (400 MHz, DMSO-d6) δ 8.67 (s, 1H), 8.05 (dd, J=7.3, 2.5 Hz, 1H), 7.69 (s, 1H), 7.42 (t, J=7.3 Hz, 1H), 7.20-7.12 (m, 1H), 6.24 (s, 2H), 3.90 (dq, J=10.5, 5.1 Hz, 1H), 3.52 (q, J=8.7 Hz, 1H), 3.19 (t, J=8.9 Hz, 1H), 2.85 (dd, J=15.6, 6.2 Hz, 1H), 2.62 (dd, J=15.1, 12.1 Hz, 1H), 2.40-2.32 (m, 1H), 2.15 (dt, J=12.1, 6.0 Hz, 1H), 1.90 (dt, J=12.2, 6.8 Hz, 2H), 1.77-1.62 (m, 2H), 1.55 (qd, J=11.2, 6.2 Hz, 1H), 0.91 (qd, J=10.8, 6.1 Hz, 1H) ppm. ESI-MS m/z calc. 531.1505, found 532.1 (M+1)$^+$; Retention time: 1.75 minutes (LC Method J).

The second diastereomer to elute was isolated as a yellow solid, (15R)-23-amino-10-fluoro-6,21-bis(trifluoromethyl)-26-oxa-3,4,19,24-tetraazapentacyclo[18.3.1.1$^{2,5}$.1$^{7,11}$.0$^{15,19}$]hexacosa-1(24),2,4,7,9,11(25),20,22-octaen-6-ol (enantiomer 2) (hydrochloride salt) (24.2 mg, 36%). $^1$H NMR (400 MHz, DMSO-d6) δ 8.84 (s, 1H), 8.01 (d, J=6.9 Hz, 1H), 7.74-7.66 (m, 2H), 7.29-7.23 (m, 1H), 6.25 (s, 2H), 4.16 (dt, J=10.7, 5.4 Hz, 1H), 3.55 (q, J=9.0 Hz, 1H), 3.23 (d, J=9.0 Hz, 1H), 2.77 (d, J=8.1 Hz, 2H), 2.23 (dt, J=11.7, 5.7 Hz, 1H), 1.92 (q, J=5.9 Hz, 1H), 1.84 (s, 2H), 1.75 (t, J=9.0 Hz, 1H), 1.60 (td, J=11.5, 6.3 Hz, 1H), 1.25-1.11 (m, 1H), 0.90 (d, J=12.3 Hz, 1H) ppm. ESI-MS m/z calc. 531.1505, found 532.0 (M+1)$^+$; Retention time: 1.87 minutes (LC Method J).

Example 69: Preparation of (12R)-20-amino-18-(pyridin-2-yl)-6-(trifluoromethyl)-22-oxa-3,4,16,21-tetraazatetracyclo[15.3.1.1²,⁵.0¹²,¹⁶]docosa-1(21),2,4,17,19-pentaen-6-ol (mixture of diastereomers) (Compound 132)

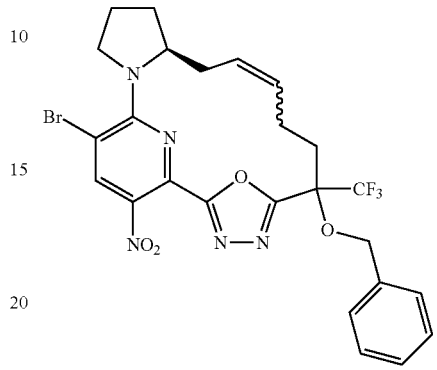
E/Z mixture

Step 1

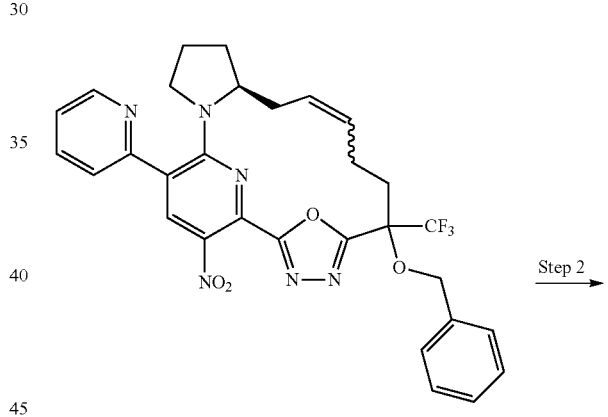
E/Z mixture

Step 2

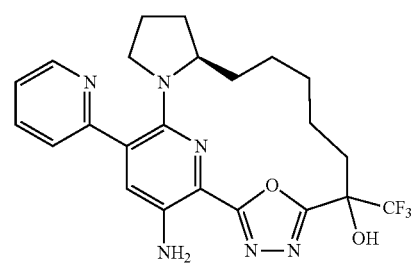
mixture of diastereomers

Step 1: (12S)-6-(Benzyloxy)-20-nitro-18-(pyridin-2-yl)-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture)

Step 2: (12R)-20-Amino-18-(pyridin-2-yl)-6-(trifluoromethyl)-22-oxa-3,4,16,21-tetraazatetracyclo[15.3.1.1²,⁵.0¹²,¹⁶]docosa-1(21),2,4,17,19-pentaen-6-ol (mixture of diastereomers) (Compound 132)

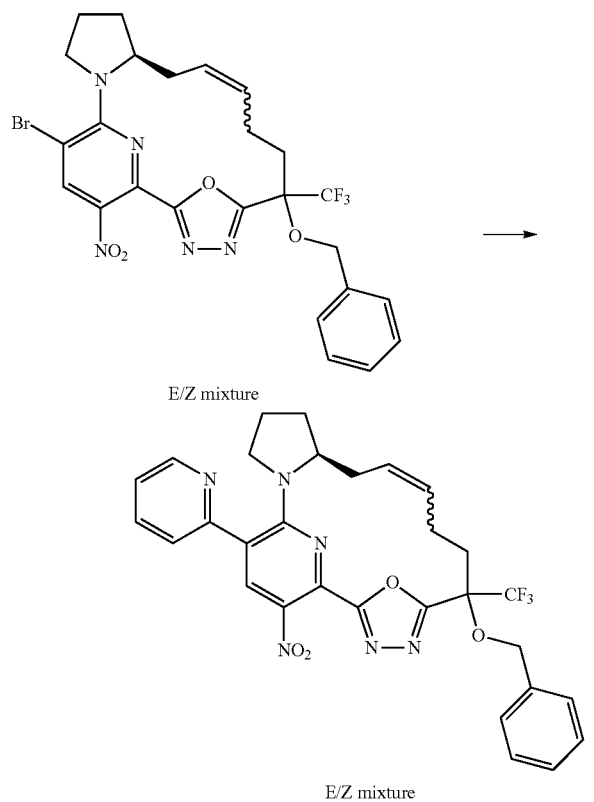

E/Z mixture

E/Z mixture

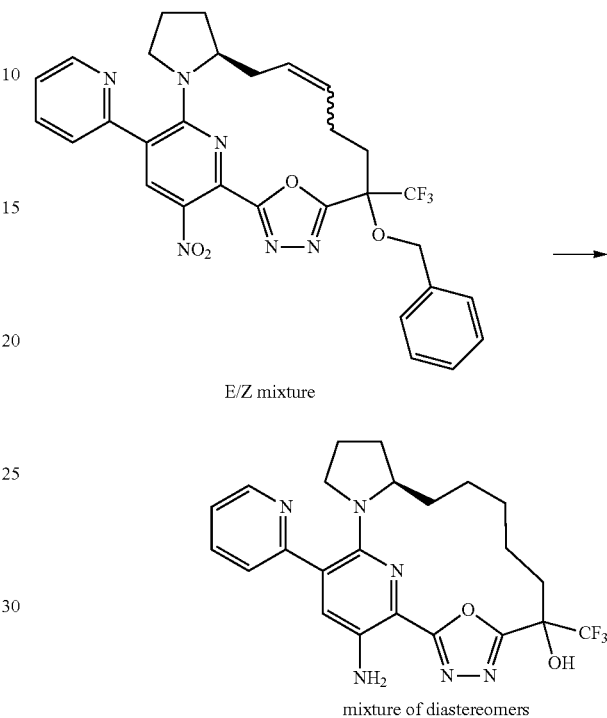

E/Z mixture mixture of diastereomers

A microwave vial was charged with (12S)-6-(benzyloxy)-18-bromo-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (160 mg, 0.2692 mmol), tributyl(2-pyridyl)stannane (160 mg, 0.4346 mmol), Pd(PPh₃)₄ (40 mg, 0.0346 mmol) and toluene (2 mL). The tube was flushed with nitrogen and sealed. The mixture was stirred at 126° C. for 21 h, cooled to room temperature and concentrated. The residue was purified by silica gel chromatography (24 g column) using a gradient from 0% to 60% ethyl acetate in heptane giving as a yellow solid, (12S)-6-(benzyloxy)-20-nitro-18-(pyridin-2-yl)-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (80 mg, 50%). ¹H NMR (300 MHz, Chloroform-d) δ 8.71 (d, J=4.1 Hz, 1H), 8.48 (s, 1H), 7.81 (td, J=7.7, 1.6 Hz, 1H), 7.47-7.27 (m, 7H), 5.63-5.41 (m, 2H), 5.35-4.87 (m, 2H), 4.09-3.96 (m, 1H), 3.66-3.48 (m, 1H), 3.03-2.87 (m, 1H), 2.72 (ddd, J=10.7, 7.3, 2.8 Hz, 1H), 2.52-2.08 (dd, J=5.4, 3.4 Hz, 5H), 1.92-1.61 (m, 4H) ppm. ¹⁹F NMR (282 MHz, Chloroform-d) δ −72.22 to −73.82 (m, 3F) ppm. ESI-MS m/z calc. 592.2046, found 593.0 (M+1)⁺; Retention time: 2.46 minutes (LC Method E).

A mixture of (12S)-6-(benzyloxy)-20-nitro-18-(pyridin-2-yl)-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (86 mg, 0.1451 mmol), 10% palladium on carbon (60 mg, 0.0282 mmol), EtOAc (3 mL) and MeOH (1 mL) was placed under a hydrogen balloon at room temperature for 3 days then at 50° C. for 5 h. The mixture was filtered through Celite and washed with EtOAc. The filtrate was concentrated and purified by reverse phase HPLC using a gradient from 50% to 90% acetonitrile in water (+0.1% formic acid) giving as a yellow-orange solid, (12R)-20-amino-18-(pyridin-2-yl)-6-(trifluoromethyl)-22-oxa-3,4,16,21-tetraazatetracyclo[15.3.1.1²,⁵.0¹²,¹⁶]docosa-1(21),2,4,17,19-pentaen-6-ol (mixture of diastereomers) (22 mg, 31%). ¹H NMR (300 MHz, DMSO-d6) δ 8.65 (d, J=4.4 Hz, 1H), 7.85 (t, J=7.8 Hz, 1H), 7.57-7.45 (m, 2H), 7.44-7.30 (m, 2H), 5.95 (br. s., 2H), 3.97-3.74 (m, 1H), 2.82-2.68 (m, 1H), 2.43-1.92 (m, 5H), 1.85-1.29 (m, 9H), 1.05-0.81 (m, 1H) ppm. ¹⁹F NMR (282 MHz, DMSO-d6) δ −76.34 (s, 3F, major diastereomer), −79.21 (s, 3F, minor diastereomer) ppm. ESI-MS m/z calc. 474.1991, found 475.1 (M+1)⁺; Retention time: 3.18 minutes (LC Method C).

Example 70: Preparation of (12R)-20-amino-18-(benzenesulfonyl)-6-(trifluoromethyl)-22-oxa-3,4,16,21-tetraazatetracyclo[15.3.1.1²,⁵.0¹²,¹⁶]docosa-1(20),2,4,17(21),18-pentaen-6-ol (Compound 133)
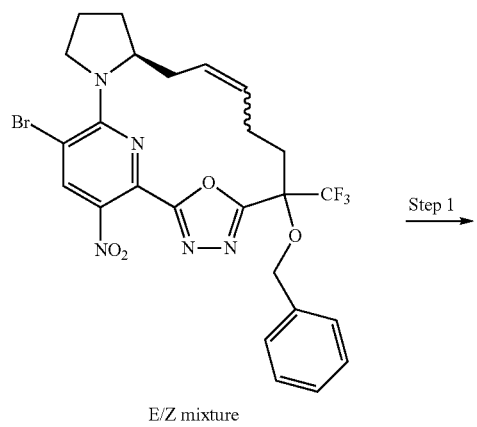
E/Z mixture
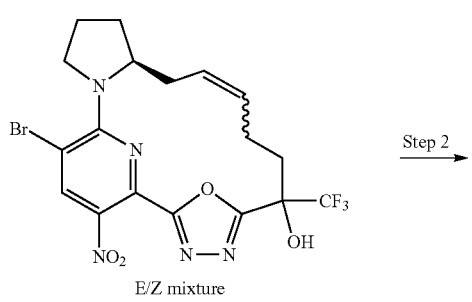
E/Z mixture
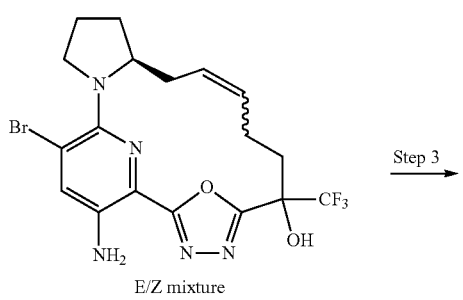
E/Z mixture
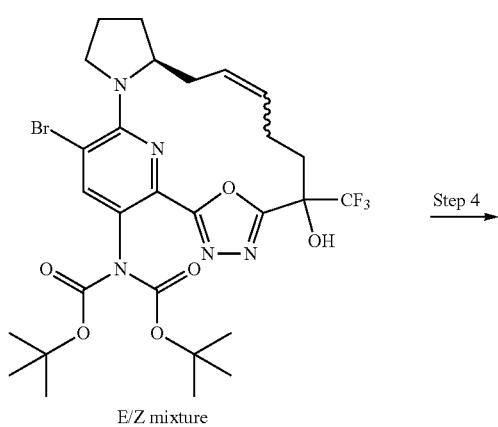
E/Z mixture
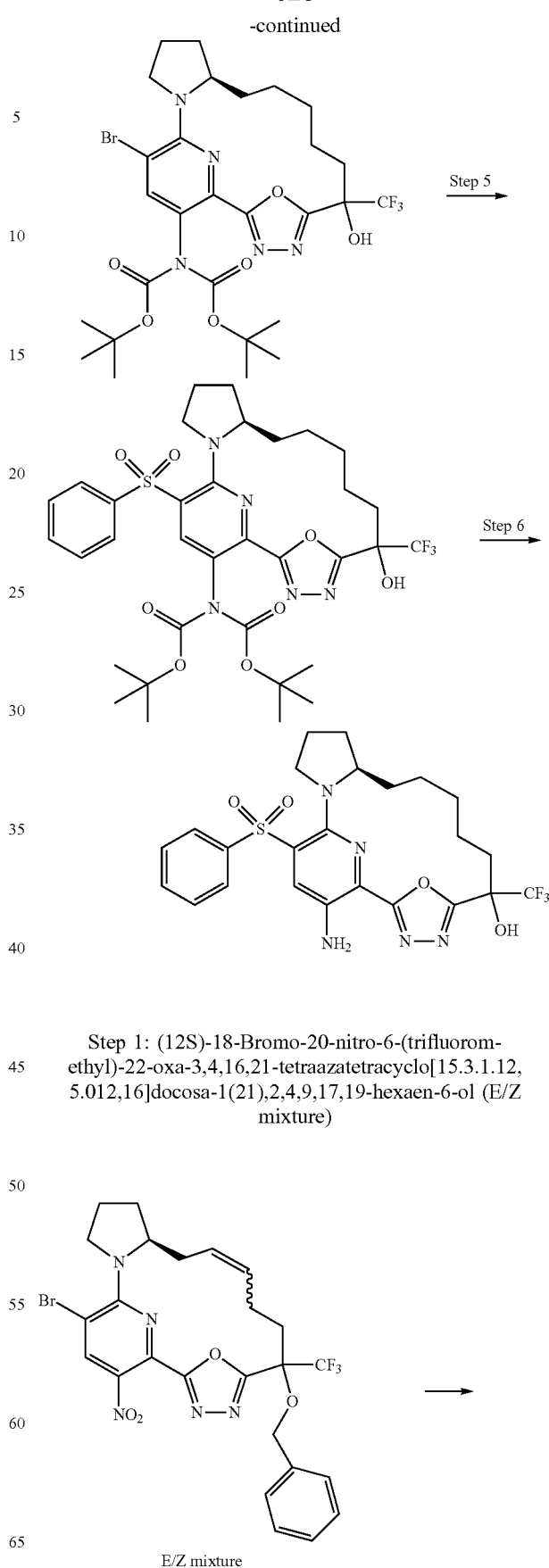
Step 1: (12S)-18-Bromo-20-nitro-6-(trifluoromethyl)-22-oxa-3,4,16,21-tetraazatetracyclo[15.3.1.1²,5.0¹²,¹⁶]docosa-1(21),2,4,9,17,19-hexaen-6-ol (E/Z mixture)

629

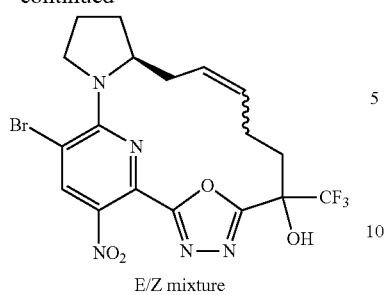

E/Z mixture

-continued

To a solution of (12S)-6-(benzyloxy)-18-bromo-20-nitro-6-(trifluoromethyl)-22-oxa-3,4,16,21-tetraazatetracyclo[15.3.1.12,5.012,16]docosa-1(21),2,4,9,17,19-hexaene (E/Z mixture) (1 g, 1.6824 mmol) in dichloromethane (40 mL) was added titanium(IV) chloride (3.1832 g, 1.84 mL, 16.782 mmol) dropwise at 0° C. under nitrogen. The cold bath was removed then the reaction mixture was stirred at room temperature overnight. The reaction mixture was diluted with dichloromethane (150 mL), cooled to 0° C. and then saturated sodium bicarbonate solution (100 mL) was added slowly. The resulting mixture was stirred vigorously for 15 min at 0° C. and then phases were separated. The aqueous phase was extracted with dichloromethane (3×100 mL). All organic layers were combined and washed with brine (100 mL). The organic layer was dried over sodium sulfate, filtered, concentrated. The residue was purified by silica gel chromatography using a gradient from 0% to 10% of dichloromethane in ethyl acetate to afford as a brown solid, (12S)-18-bromo-20-nitro-6-(trifluoromethyl)-22-oxa-3,4,16,21-tetraazatetracyclo[15.3.1.12,5.012,16]docosa-1(21),2,4,9,17,19-hexaen-6-ol (E/Z mixture) (674 mg, 79%). $^1$H NMR (300 MHz, Chloroform-d) δ 8.54-8.40 (m, 1H), 7.34-7.20 (m, 1H), 5.63-5.27 (m, 2H), 4.06-3.75 (m, 3H), 3.38-3.01 (m, 1H), 2.33-1.54 (m, 9H) ppm. $^{19}$F NMR (282 MHz, Chloroform-d) δ −80.14 (br. s., 3F), −80.37 (br. s., 3F) ppm. ESI-MS m/z calc. 503.0416, found 503.9 (M+1)$^+$; Retention time: 2.3 minutes (LC Method E).

Step 2: (12S)-20-Amino-18-bromo-6-(trifluoromethyl)-22-oxa-3,4,16,21-tetraazatetracyclo[15.3.1.12,5.012,16]docosa-1(21),2,4,9,17,19-hexaen-6-ol (E/Z mixture)

630

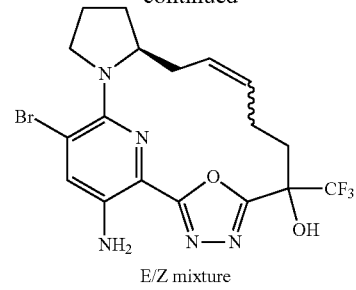

E/Z mixture

-continued

To a solution of (12S)-18-bromo-20-nitro-6-(trifluoromethyl)-22-oxa-3,4,16,21-tetraazatetracyclo[15.3.1.12,5.012,16]docosa-1(21),2,4,9,17,19-hexaen-6-ol (E/Z mixture) (193 mg, 0.3827 mmol) in ethanol (8 mL) and water (2 mL) was added iron (86 mg, 1.54 mmol) and ammonium chloride (62 mg, 1.1591 mmol). The reaction was stirred at 100° C. for 1.5 hours. The dark solution was cooled to room temperature and filtered over Celite washing with dichloromethane (100 mL). The filtrate was concentrated under reduced pressure. Water (20 mL) was added and the resulting mixture was extracted with dichloromethane (2×50 mL). The combined organic layers were dried over anhydrous sodium sulfate, filtered and concentrated under reduced pressure. The resulting material was dried under vacuum to provide as a yellow oil, (12S)-20-amino-18-bromo-6-(trifluoromethyl)-22-oxa-3,4,16,21-tetraazatetracyclo[15.3.1.12,5.012,16]docosa-1(21),2,4,9,17,19-hexaen-6-ol (E/Z mixture) (180 mg, 99%). $^1$H NMR (300 MHz, Chloroform-d) δ 7.39 (d, J=2.1 Hz, 1H), 5.65-5.43 (m, 2H), 4.92 (br. s., 2H), 4.09-3.94 (m, 1H), 3.90-3.74 (m, 1H), 3.65-3.42 (m, 2H), 3.39-3.25 (m, 1H), 2.98-2.75 (m, 1H), 2.56-1.93 (m, 6H), 1.80-1.67 (m, 1H), 1.55-1.39 (m, 1H) ppm. $^{19}$F NMR (282 MHz, Chloroform-d) δ−77.58 (s, 3F), −80.75 (s, 3F) ppm. ESI-MS m/z calc. 473.0674, found 473.9 (M+1)$^+$; Retention time: 2.31 minutes (LC Method E).

Step 3: tert-Butyl N-[(12S)-18-bromo-6-hydroxy-6-(trifluoromethyl)-22-oxa-3,4,16,21-tetraazatetracyclo[15.3.1.12,5.012,16]docosa-1(21),2,4,9,17,19-hexaen-20-yl]-N-[(tert-butoxy)carbonyl]carbamate (E/Z mixture)

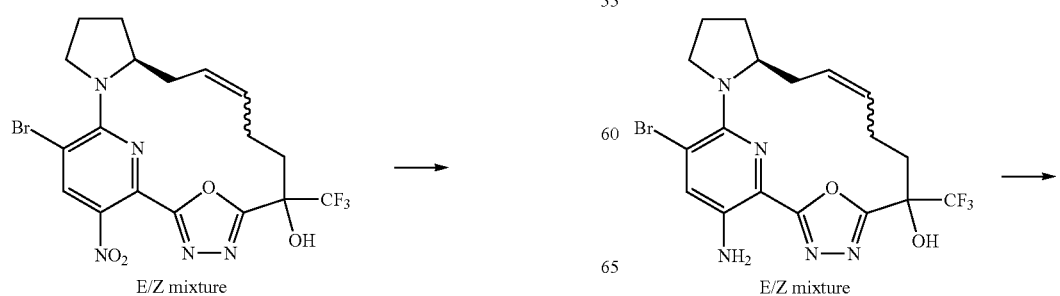

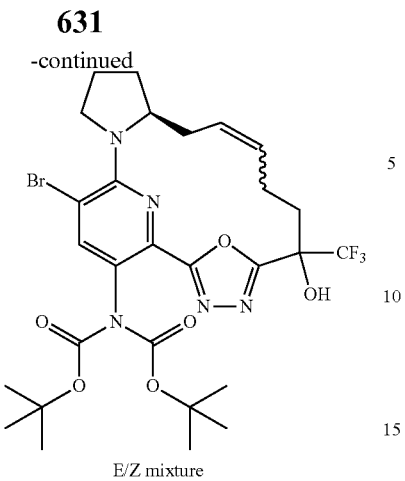

E/Z mixture

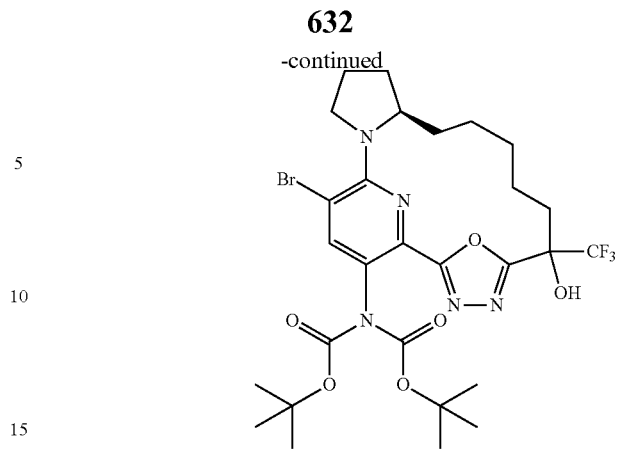

A mixture of (12S)-20-amino-18-bromo-6-(trifluoromethyl)-22-oxa-3,4,16,21-tetraazatetracyclo[15.3.1.12,5.012,16]docosa-1(21),2,4,9,17,19-hexaen-6-ol (E/Z mixture) (2 g, 3.4115 mmol), di-tert-butyl dicarbonate (3.69 g, 16.907 mmol), diisopropylethylamine (2.1295 g, 2.87 mL, 16.477 mmol), DMAP (76 mg, 0.6221 mmol) and dichloromethane (90 mL) was stirred at room temperature for 3 days. The reaction was concentrated and the residue was purified by silica gel chromatography using a gradient from 0% to 30% ethyl acetate in heptanes to afford as a beige solid, tert-butyl N-[(12S)-18-bromo-6-hydroxy-6-(trifluoromethyl)-22-oxa-3,4,16,21-tetraazatetracyclo[15.3.1.12,5.012,16]docosa-1(21),2,4,9,17,19-hexaen-20-yl]-N-[(tert-butoxy)carbonyl]carbamate (E/Z mixture) (2.21 g, 96%). ESI-MS m/z calc. 673.1723, found 618.2 (M-55)+; Retention time: 2.59 minutes (LC Method Y).

A solution of tert-butyl N-[(12S)-18-bromo-6-hydroxy-6-(trifluoromethyl)-22-oxa-3,4,16,21-tetraazatetracyclo[15.3.1.12,5.012,16]docosa-1(21),2,4,9,17,19-hexaen-20-yl]-N-[(tert-butoxy)carbonyl]carbamate (E/Z mixture) (294 mg, 0.4359 mmol) in ethyl acetate (15 mL) was put under nitrogen atmosphere. Added rhodium on alumina (89 mg, 5% w/w, 0.0432 mmol) then the reaction was stirred under hydrogen (balloon) atmosphere for 1.5 hours. The reaction was put under nitrogen atmosphere then filtered through Celite and concentrated to give as a yellow oil, tert-butyl N-[(12R)-18-bromo-6-hydroxy-6-(trifluoromethyl)-22-oxa-3,4,16,21-tetraazatetracyclo[15.3.1.12,5.012,16]docosa-1(21),2,4,17,19-pentaen-20-yl]-N-[(tert-butoxy)carbonyl]carbamate (280 mg, 95%). $^1$H NMR (300 MHz, Chloroform-d) δ 7.68-7.63 (m, 1H), 4.07-3.90 (m, 2H), 3.86-3.75 (m, 1H), 2.83-2.57 (m, 1H), 2.45-2.27 (m, 1H), 2.22-2.08 (m, 2H), 2.01-1.94 (m, 1H), 1.52-1.32 (m, 28H) ppm. $^{19}$F NMR (282 MHz, Chloroform-d) δ −74.85 (br. s., 3F), −77.76 (s, 3F) ppm. Retention time: 2.99 minutes (LC Method E).

Step 4: tert-Butyl N-[(12R)-18-bromo-6-hydroxy-6-(trifluoromethyl)-22-oxa-3,4,16,21-tetraazatetracyclo[15.3.1.12,5.012,16]docosa-1(21),2,4,17,19-pentaen-20-yl]-N-[(tert-butoxy)carbonyl]carbamate Step 5: tert-Butyl N-[(12R)-18-(benzenesulfonyl)-6-hydroxy-6-(trifluoromethyl)-22-oxa-3,4,16,21-tetraazatetracyclo[15.3.1.12,5.012,16]docosa-1(21),2,4,17,19-pentaen-20-yl]-N-[(tert-butoxy)carbonyl]carbamate

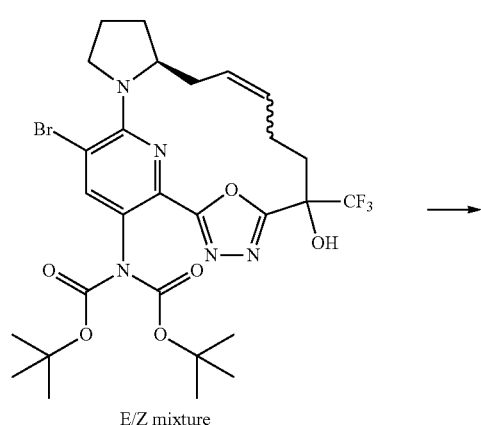

E/Z mixture

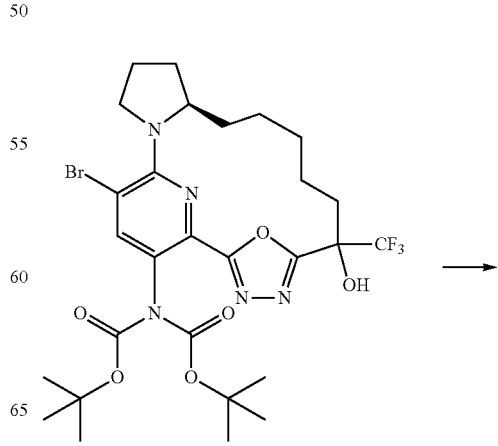

633

-continued

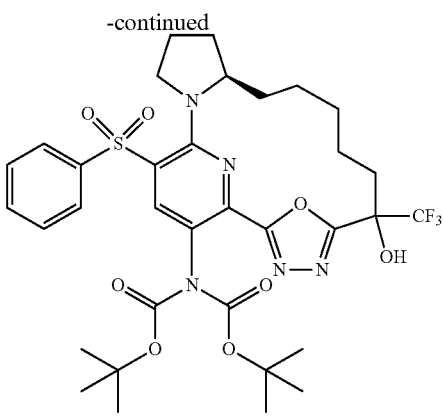

A pressure tube was charged with tert-butyl N-[(12R)-18-bromo-6-hydroxy-6-(trifluoromethyl)-22-oxa-3,4,16,21-tetraazatetracyclo[15.3.1.12,5.012,16]docosa-1(21),2,4,17,19-pentaen-20-yl]-N-[(tert-butoxy)carbonyl]carbamate (69 mg, 0.102 mmol), sodium benzenesulfinate (47 mg, 0.2863 mmol), CuI (24 mg, 0.126 mmol), L-proline (0.7 mg, 0.0061 mmol) and DMSO (0.8 mL). The tube was flushed with nitrogen for 2 min and sealed. The mixture was stirred at 112° C. for 2.5 h, cooled to room temperature and added to 28% aqueous $NH_3$ (6 mL). The mixture was extracted with MTBE (3×20 mL) and the combined organic layers were washed with 28% aqueous $NH_3$ (4 mL), dried over $Na_2SO_4$, filtered and concentrated to give as a yellow oil, tert-butyl N-[(12R)-18-(benzenesulfonyl)-6-hydroxy-6-(trifluoromethyl)-22-oxa-3,4,16,21-tetraazatetracyclo[15.3.1.12,5.012,16]docosa-1(21),2,4,17,19-pentaen-20-yl]-N-[(tert-butoxy)carbonyl]carbamate (80 mg, quant.), which was used directly in the next step without further purification.

Step 6: (12R)-20-Amino-18-(benzenesulfonyl)-6-(trifluoromethyl)-22-oxa-3,4,16,21-tetraazatetracyclo[15.3.1.12,5.012,16]docosa-1(20),2,4,17(21),18-pentaen-6-ol (Compound 133)

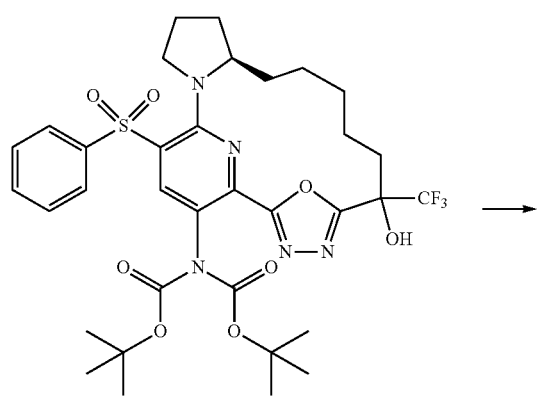

634

-continued

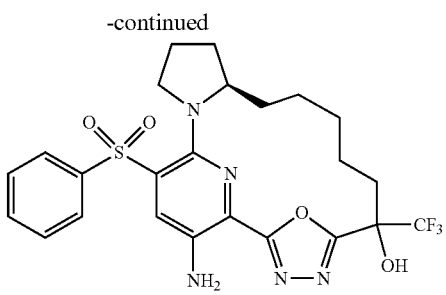

To a solution of tert-butyl N-[(12R)-18-(benzenesulfonyl)-6-hydroxy-6-(trifluoromethyl)-22-oxa-3,4,16,21-tetraazatetracyclo[15.3.1.12,5.012,16]docosa-1(21),2,4,17,19-pentaen-20-yl]-N-[(tert-butoxy)carbonyl]carbamate (75 mg, 0.1019 mmol) in $CH_2Cl_2$ (2 mL) was added TFA (2.9600 g, 2 mL, 25.96 mmol). The mixture was stirred at room temperature for 30 min and concentrated then co-evaporated with MeOH (3×3 mL). The residue was partitioned between $CH_2Cl_2$ (20 mL) and 5% aqueous $NaHCO_3$ (15 mL). The two layers was separated, and the aqueous layer was extracted with $CH_2Cl_2$ (2×20 mL). The combined organic layers were dried over $Na_2SO_4$, filtered and concentrated. The residue was purified by silica gel chromatography using a gradient from 0% to 20% ethyl acetate in heptanes and the product was lyophilized from $CH_3CN$ (1 mL) and $H_2O$ (2 mL) to afford as a yellow solid and mixture of diastereomers, (12R)-20-amino-18-(benzenesulfonyl)-6-(trifluoromethyl)-22-oxa-3,4,16,21-tetraazatetracyclo[15.3.1.12,5.012,16]docosa-1(20),2,4,17(21),18-pentaen-6-ol (30 mg, 55%). $^1$H NMR (300 MHz, DMSO-d6) δ 8.08-7.99 (m, 1H), 7.86-7.77 (m, 2H), 7.76-7.68 (m, 1H), 7.67-7.52 (m, 3H), 6.41-6.23 (m, 2H), 3.93-3.69 (m, 2H), 3.09-2.92 (m, 1H), 2.23-1.74 (m, 5H), 1.66-1.18 (m, 8H), 0.50-0.33 (m, 1H) ppm. ESI-MS m/z calc. 537.1658, found 537.9 (M+1)$^+$; Retention time: 3.54 minutes (LC Method C).

Example 71: Preparation of (16R)-24-amino-22-(trifluoromethyl)-26-oxa-3,4,20,25-tetraazapentacyclo[19.3.1.12,5.06,11.016,20]hexacosa-1(25),2,4,6(11),7,9,21,23-octaen-7-ol (Compound 134)

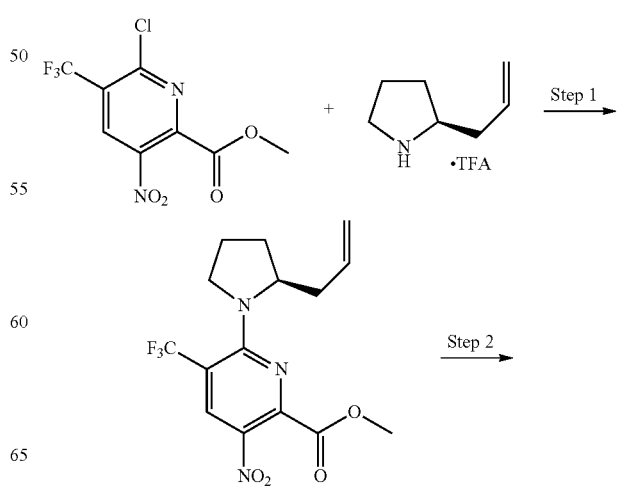

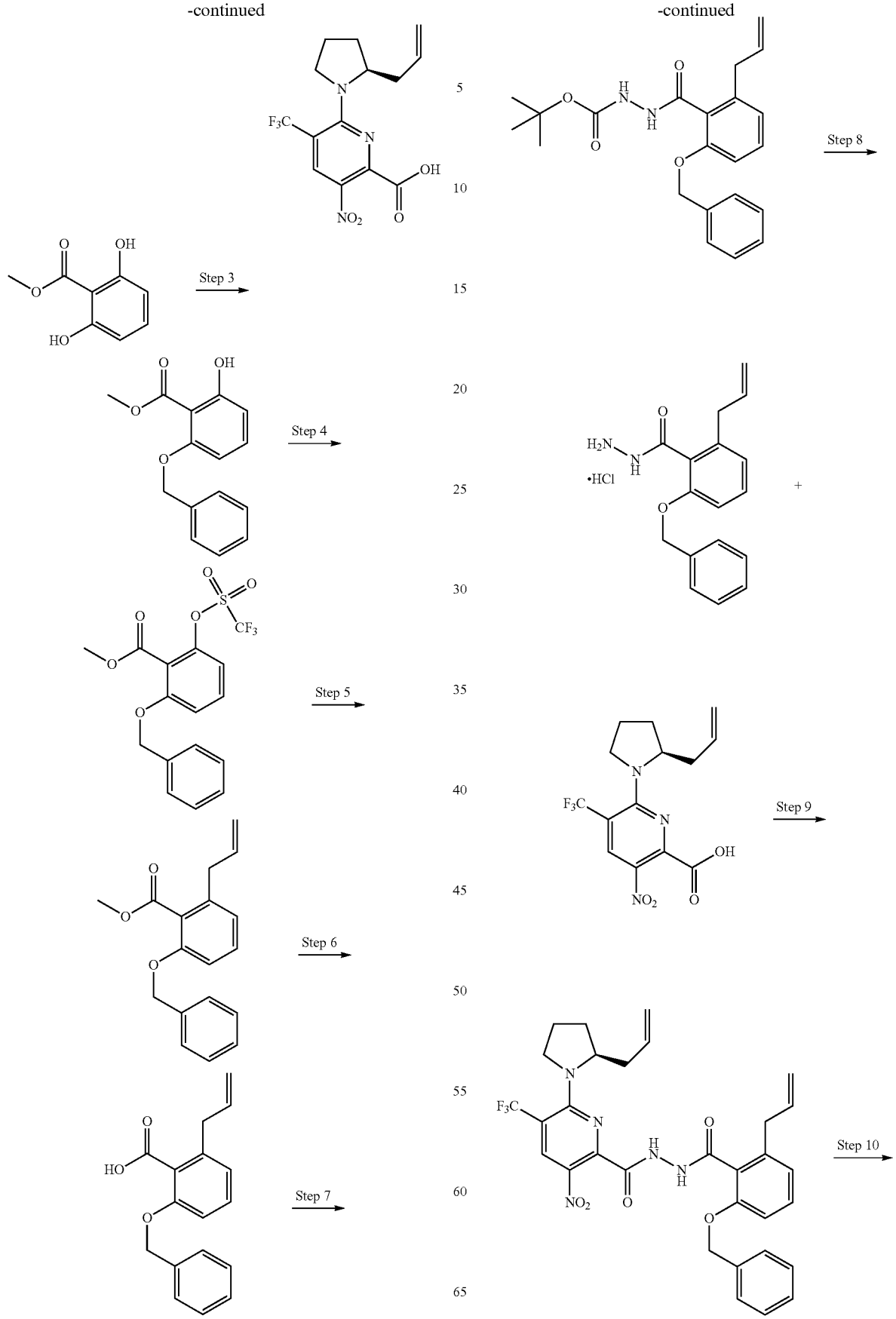

637
-continued

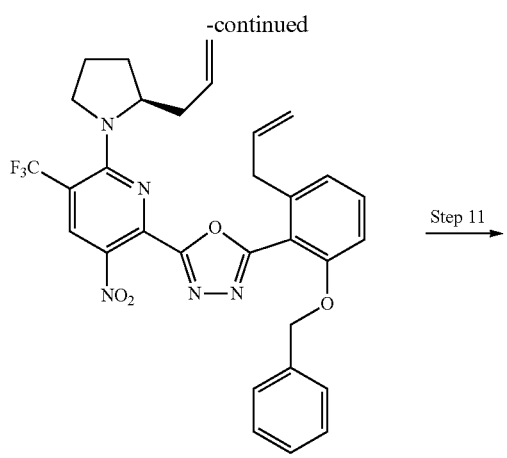

E/Z mixture

Step 1: Methyl 6-[(2S)-2-allylpyrrolidin-1-yl]-3-nitro-5-(trifluoromethyl)pyridine-2-carboxylate

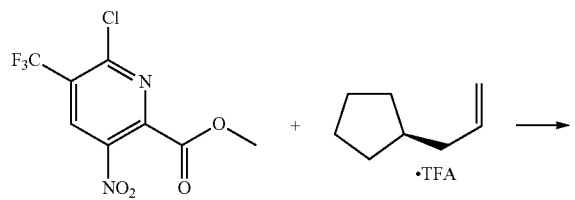

638
-continued

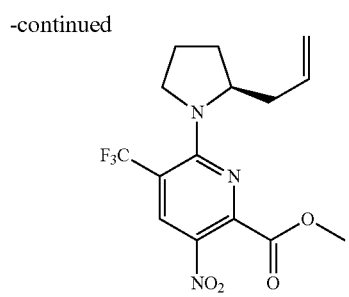

To a solution of methyl 6-chloro-3-nitro-5-(trifluoromethyl)pyridine-2-carboxylate (1 g, 3.514 mmol) and (2S)-2-allylpyrrolidine (trifluoroacetate salt) (1 g, 4.4403 mmol) in acetonitrile (10 mL) was added diisopropylethylamine (2.3002 g, 3.1 mL, 17.797 mmol) and the mixture was refluxed for 2 h. The reaction mixture was cooled to ambient temperature and the solvent was removed in vacuo. The residue was diluted with ethyl acetate (50 mL) and washed with brine (2×25 mL), dried over sodium sulfate, filtered and concentrated in vacuo. The residue was purified by silica gel column chromatography eluting with a gradient from 0% to 20% of ethyl acetate in heptanes to afford as a yellow oil, methyl 6-[(2S)-2-allylpyrrolidin-1-yl]-3-nitro-5-(trifluoromethyl)pyridine-2-carboxylate (1.3 g, 100%). $^1$H NMR (300 MHz, CDCl$_3$) δ 8.62 (s, 1H), 5.79-5.58 (m, 1H), 5.14-4.97 (m, 2H), 4.72-4.59 (m, 1H), 4.01 (s, 3H), 3.73-3.57 (m, 2H), 2.63-2.47 (m, 1H), 2.43-2.26 (m, 1H), 2.17-1.99 (m, 2H), 1.94-1.75 (m, 2H) ppm. $^{19}$F NMR (282 MHz, CDCl$_3$) δ−54.66 (s, 3F) ppm. ESI-MS m/z calc. 359.1093, found 360.1 (M+1)$^+$; Retention time: 2.29 minutes (LC Method E).

Step 2: 6-[(2S)-2-Allylpyrrolidin-1-yl]-3-nitro-5-(trifluoromethyl)pyridine-2-carboxylic Acid

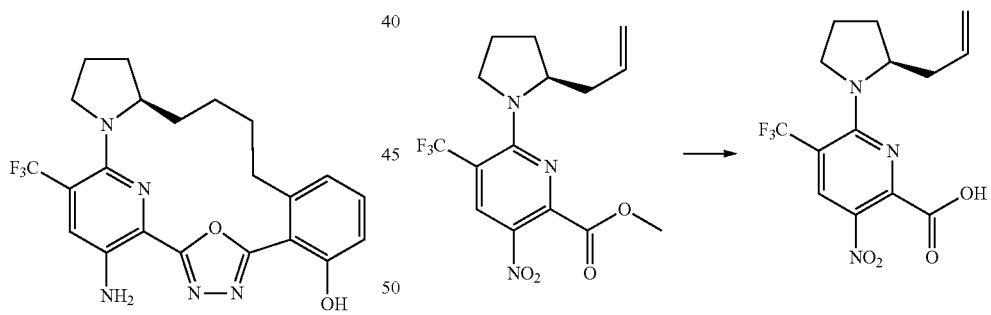

To a solution of methyl 6-[(2S)-2-allylpyrrolidin-1-yl]-3-nitro-5-(trifluoromethyl)pyridine-2-carboxylate (22 g, 61.23 mmol) in THF (220 mL) was added methanol (220 mL) and water (110 mL). Anhydrous lithium hydroxide (21.99 g, 918.2 mmol) was added and stirred at room temperature for 0.5 h. THF and methanol were removed under reduced pressure. An aqueous 3 M HCl solution was added until the mixture was acidic, then extracted the aqueous layer with ethyl acetate (3×200 mL). The organic phases were combined, washed with brine (200 mL), dried over anhydrous sodium sulfate, filtered and concentrated under reduced pressure to afford as a yellow solid, 6-[(2S)-2-allylpyrrolidin-1-yl]-3-nitro-5-(trifluoromethyl)pyridine-2-carboxylic acid (19.7 g, 93%). ESI-MS m/z calc. 345.09363, found 346.06 (M+1)$^+$; Retention time: 0.67 minutes (LC Method R).

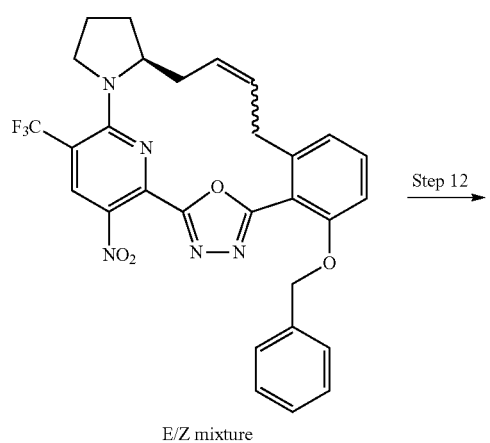

Step 3: Methyl 2-benzyloxy-6-hydroxy-benzoate

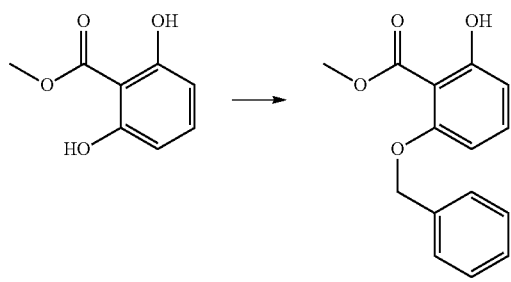 [SMILES: COC(=O)c1c(O)cccc1O ; COC(=O)c1c(O)cccc1OCc1ccccc1]

A mixture of methyl 2,6-dihydroxybenzoate (1.68 g, 9.9913 mmol), potassium carbonate (2.76 g, 19.97 mmol) and bromomethylbenzene (1.8694 g, 1.3 mL, 10.93 mmol) in acetonitrile (30 mL) was heated in an oil bath at 60° C. for 23 hours. Once cooled to room temperature, the reaction mixture was filtered over Celite, washed with ethyl acetate and concentrated under reduced pressure. The residue was transferred to a 250 mL separatory funnel with water (75 mL) and small amount of 1 N aqueous HCl (to reach a pH of about 1 to 2) and extracted with ethyl acetate (2×100 mL). The combined organic layer was washed with brine (50 mL), dried over sodium sulfate, filtered and concentrated under reduced pressure. The residue was purified by silica gel chromatography (120 g column) using a gradient from 0% to 20% ethyl acetate in heptanes giving as a white solid, methyl 2-benzyloxy-6-hydroxy-benzoate (478 mg, 18%). $^1$H NMR (300 MHz, Chloroform-d) δ 11.52 (s, 1H), 7.54-7.46 (m, 2H), 7.45-7.29 (m, 4H), 6.63 (dd, J=8.4, 1.0 Hz, 1H), 6.50 (d, J 7.6 Hz, 1H), 5.14 (s, 2H), 3.96 (s, 3H) ppm. ESI-MS m/z calc. 258.0892, found 257.2 (M−1)$^-$; Retention time: 2.06 minutes (LC Method E).

Step 4: Methyl 2-benzyloxy-6-(trifluoromethylsulfonyloxy)benzoate

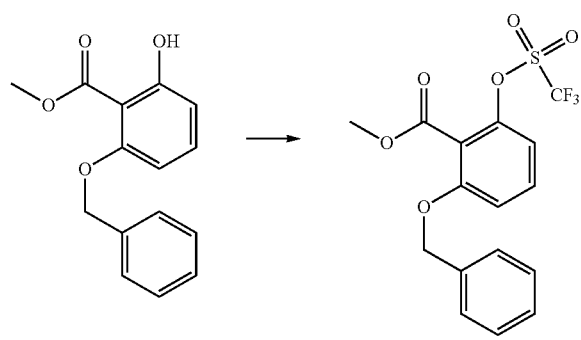 [SMILES: COC(=O)c1c(O)cccc1OCc1ccccc1 ; COC(=O)c1c(OCc2ccccc2)cccc1OS(=O)(=O)C(F)(F)F]

Trifluoromethylsulfonyl trifluoromethanesulfonate (7.3788 g, 4.4 mL, 26.153 mmol) was added slowly to methyl 2-benzyloxy-6-hydroxy-benzoate (5.45 g, 19.941 mmol) and pyridine (3.2274 g, 3.3 mL, 40.802 mmol) in DCM (50 mL) at 0° C. The mixture was stirred at room temperature for 2 h then poured into saturated sodium bicarbonate solution (100 mL) and extracted with DCM (3×50 mL). The organic phases were combined, dried over anhydrous sodium sulfate, filtered and concentrated under reduced pressure. The residue was purified by silica gel chromatography (120 g column) using a gradient from 0% to 20% of ethyl acetate in heptanes giving as a clear oil, methyl 2-benzyloxy-6-(trifluoromethylsulfonyloxy)benzoate (7.45 g, 93%). $^1$H NMR (300 MHz, Chloroform-d) δ 7.47-7.29 (m, 6H), 7.05-6.89 (m, 2H), 5.17 (s, 2H), 3.94 (s, 3H) ppm. $^{19}$F NMR (282 MHz, Chloroform-d) δ−73.76 (s, 3F) ppm. ESI-MS m/z calc. 390.0385, found 413.0 (M+Na)$^+$; Retention time: 2.24 minutes (LC Method E).

Step 5: Methyl 2-allyl-6-benzyloxy-benzoate

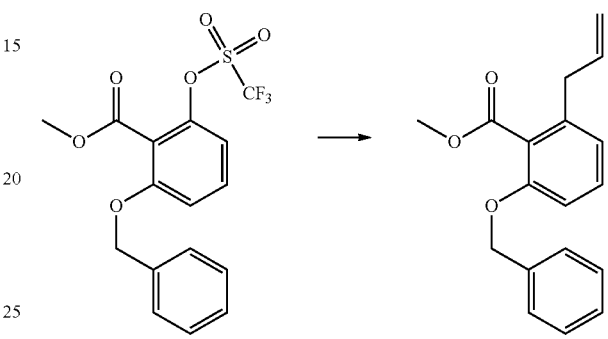

To a solution of tetrakis(triphenylphosphine)palladium(0) (1.1 g, 0.9519 mmol) and lithium chloride (2.35 g, 55.432 mmol) in degassed dry THF (35 mL) at room temperature was added a solution of methyl 2-benzyloxy-6-(trifluoromethylsulfonyloxy)benzoate (7.45 g, 18.514 mmol) in degassed dry THF (25 mL) and allyl(tributyl)stannane (6.75 g, 20.385 mmol). The resulting reaction mixture was refluxed overnight. The reaction mixture was cooled to room temperature and diluted with MTBE (300 mL). The resulting solution was washed with water (300 mL), 10% aqueous ammonium hydroxide solution (100 mL) and brine (200 mL). The solvent was evaporated under reduced pressure and the residue was purified by silica gel chromatography (120 g column) using a gradient from 0% to 5% of ethyl acetate in heptanes giving as a clear oil, methyl 2-allyl-6-benzyloxy-benzoate (5.4 g, 100%). $^1$H NMR (300 MHz, Chloroform-d) δ 7.44-7.18 (m, 6H), 6.90-6.78 (m, 2H), 6.01-5.81 (m, 1H), 5.16-4.99 (m, 4H), 3.88 (s, 3H), 3.38 (d, J=6.8 Hz, 2H) ppm. ESI-MS m/z calc. 282.1256, found 305.1 (M+Na)$^+$; Retention time: 2.2 minutes (LC Method E).

Step 6: 2-Allyl-6-benzyloxy-benzoic Acid

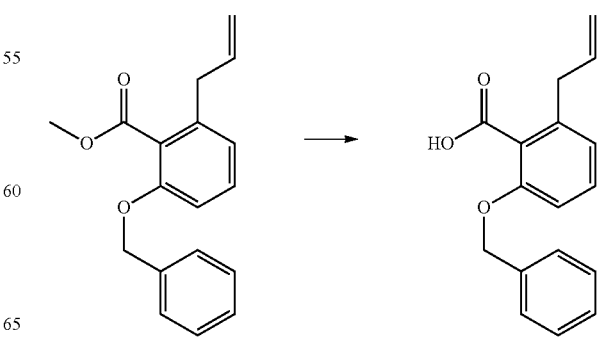

Potassium hydroxide solution (10.6 mL of 5 M, 53 mmol) was added to methyl 2-allyl-6-benzyloxy-benzoate (3 g, 10.626 mmol) in THF (25 mL) and ethanol (25 mL) at room temperature. The mixture was stirred for 4 days at 50° C. then 4 days at 60° C. The mixture was poured in water (250 mL) and washed with MTBE (2×100 mL). The aqueous phase was acidified to pH=2 using 3 N HCl solution and was extracted with MTBE (3×100 mL). The organic phases were combined, washed with brine (100 mL), dried over anhydrous sodium sulfate, filtered and concentrated under reduced pressure giving as an orange gum, 2-allyl-6-benzyloxy-benzoic acid (2.44 g, 83%). ESI-MS m/z calc. 268.1099, found 269.1 (M+1)$^+$; Retention time: 1.98 minutes (LC Method E).

Step 7: tert-Butyl N-[(2-allyl-6-benzyloxy-benzoyl)amino]carbamate

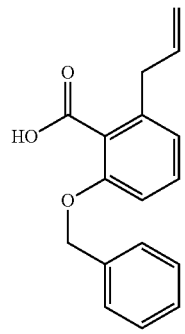

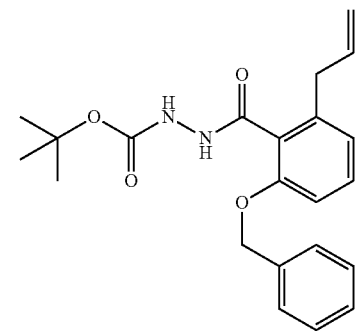

To a solution of 2-allyl-6-benzyloxy-benzoic acid (2.4 g, 8.945 mmol) in DMF (25 mL) was added triethylamine (1.8876 g, 2.6 mL, 18.654 mmol) and HATU (4.75 g, 12.492 mmol). The mixture was stirred for 10 min. Then, tert-butyl N-aminocarbamate (1.5 g, 11.35 mmol) was added. The mixture was stirred at room temperature overnight then diluted with water (200 mL) and extracted with ethyl acetate (3×50 mL). The combined organic layer was washed with aqueous saturated sodium bicarbonate solution (100 mL), water (100 mL) and brine (100 mL). The organic layer was concentrated by evaporation under reduced pressure and then purified by silica gel chromatography (80 g column) using a gradient from 0% to 40% of ethyl acetate in heptanes giving as a white solid, tert-butyl N-[(2-allyl-6-benzyloxy-benzoyl)amino]carbamate (2.89 g, 73%). $^1$H NMR (300 MHz, Chloroform-d) δ 7.54-7.46 (m, 1H), 7.44-7.28 (m, 6H), 6.93-6.77 (m, 2H), 6.72-6.58 (m, 1H), 6.33-5.91 (m, 1H), 5.18-5.01 (m, 4H), 3.56-3.48 (m, 1H), 1.90-1.87 (m, 1H), 1.50 (d, J=2.3 Hz, 9H) ppm. ESI-MS m/z calc. 382.1893, found 405.1 (M+Na)$^+$; Retention time: 2.09 minutes (LC Method E).

Step 8: 2-Allyl-6-benzyloxy-benzohydrazide (Hydrochloride Salt)

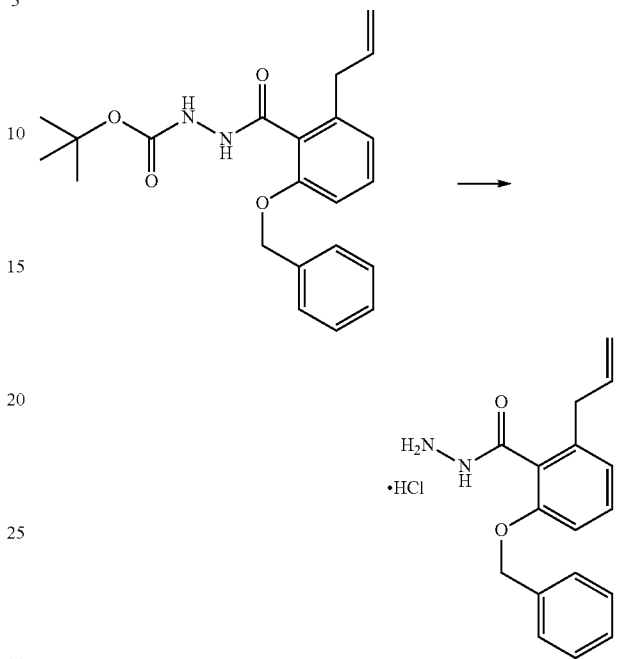

To a solution of tert-butyl N-[(2-allyl-6-benzyloxy-benzoyl)amino]carbamate (2.89 g, 6.559 mmol) in CH$_2$Cl$_2$ (15 mL) was added HCl in Et$_2$O (15 mL of 2 M, 30 mmol). The mixture was stirred for 6 h at room temperature. Again, HCl in Et$_2$O (5 mL of 2 M, 10 mmol) was added and the mixture was stirred at room temperature overnight then diluted with heptanes (120 mL) and concentrated. The residue was triturated in diethyl ether, filtered and dried to give as a white solid, 2-allyl-6-benzyloxy-benzohydrazide (hydrochloride salt) (2.05 g, 98%). $^1$H NMR (300 MHz, DMSO-d6) δ 11.40 (d, J=6.8 Hz, 1H), 10.67 (br. s, 2H), 7.47-7.27 (m, 6H), 7.06-6.96 (m, 1H), 6.91-6.80 (m, 1H), 6.42-6.32 (m, 1H), 6.00-5.73 (m, 1H), 5.22-4.96 (m, 4H), 3.29 (d, J=6.8 Hz, 1H), 1.83 (d, J=4.4 Hz, 1H) ppm. ESI-MS m/z calc. 282.1368, found 283.1 (M+1)$^+$; Retention time: 1.78 minutes (LC Method E).

Step 9: N'-(2-Allyl-6-benzyloxy-benzoyl)-6-[(2S)-2-allylpyrrolidin-1-yl]-3-nitro-5-(trifluoromethyl)pyridine-2-carbohydrazide

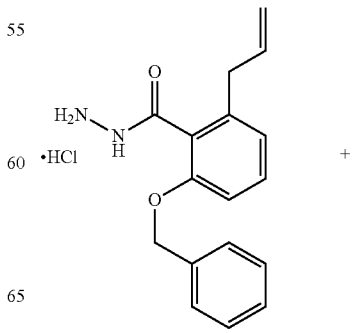 +

Step 10: 2-(2-Allyl-6-benzyloxy-phenyl)-5-[6-[(2S)-2-allylpyrrolidin-1-yl]-3-nitro-5-(trifluoromethyl)-2-pyridyl]-1,3,4-oxadiazole

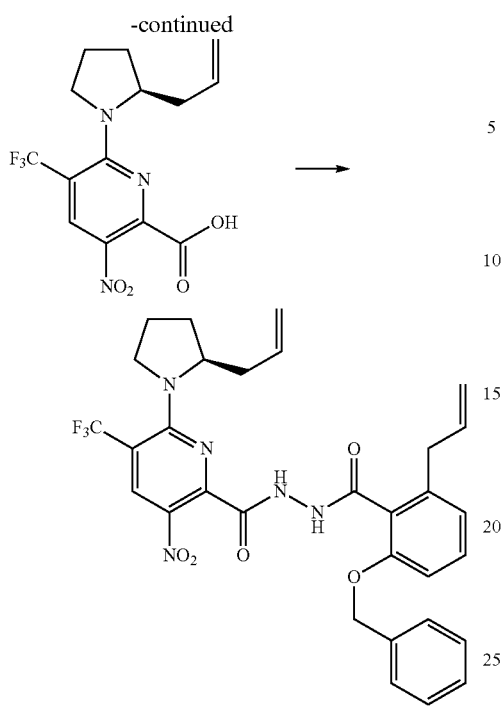

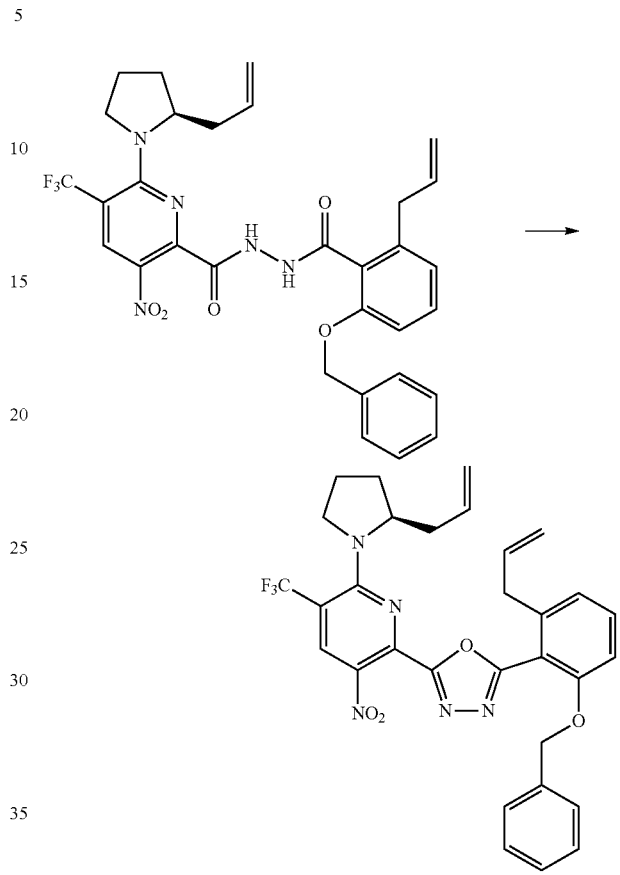

To a suspension of 6-[(2S)-2-allylpyrrolidin-1-yl]-3-nitro-5-(trifluoromethyl)pyridine-2-carboxylic acid (730 mg, 2.1143 mmol) in dichloromethane (20 mL) at 0° C. was added oxalyl chloride (390 mg, 0.26 mL, 3.0727 mmol) and DMF (188.80 mg, 0.2 mL, 2.583 mmol) dropwise. The mixture was stirred at room temperature for 1 h, followed by addition of a solution of 2-allyl-6-benzyloxy-benzohydrazide (hydrochloride salt) (810 mg, 2.5408 mmol) and DIPEA (497.14 mg, 0.67 mL, 3.8466 mmol) in dichloromethane (13 mL), dropwise. The mixture was stirred at room temperature for 1 hour and saturated aqueous sodium bicarbonate (200 mL) was added. The mixture was extracted with DCM (3×100 mL). The combined organic layers were dried over sodium sulfate, filtered and concentrated. The residue was purified by silica gel chromatography (40 g column) using a gradient from 0% to 40% of ethyl acetate in heptanes giving as a yellow solid, N-(2-allyl-6-benzyloxy-benzoyl)-6-[(2S)-2-allylpyrrolidin-1-yl]-3-nitro-5-(trifluoromethyl)pyridine-2-carbohydrazide (1.16 g, 89%). $^1$H NMR (300 MHz, Chloroform-d) δ 9.56-9.38 (m, 1H), 8.96-8.77 (m, 1H), 8.49 (s, 1H), 7.48-7.28 (m, 5H), 7.20-6.50 (m, 3H), 6.37-5.90 (m, 1H), 5.87-5.65 (m, 1H), 5.24-4.97 (m, 5H), 4.79-4.57 (m, 1H), 3.79-3.58 (m, 2H), 3.50 (d, J=6.5 Hz, 1H), 2.70-2.51 (m, 1H), 2.45-2.26 (m, 1H), 2.20-1.99 (m, 2H), 1.97-1.73 (m, 4H) ppm. $^{19}$F NMR (282 MHz, Chloroform-d) δ −54.77 (s, 3F) ppm. ESI-MS m/z calc. 609.2199, found 610.0 (M+1)$^+$; Retention time: 2.33 minutes (LC Method E).

To a solution of N'-(2-allyl-6-benzyloxy-benzoyl)-6-[(2S)-2-allylpyrrolidin-1-yl]-3-nitro-5-(trifluoromethyl)pyridine-2-carbohydrazide (1.16 g, 1.9029 mmol) and diisopropylethylamine (742 mg, 1.0 mL, 5.7411 mmol) in acetonitrile (20 mL) at 50° C. was added p-toluenesulfonyl chloride (381 mg, 1.9985 mmol) portion-wise. The mixture was stirred at 70° C. for 3.5 hours. Then, the reaction mixture was cooled, concentrated and the residue was dissolved in ethyl acetate (125 mL). The organic layer was washed with 5% aqueous sodium bicarbonate (25 mL), water (2×25 mL) and brine (50 mL), dried over anhydrous sodium sulfate and filtered. The volatiles were removed by evaporation under reduced pressure and the residue was purified by silica gel chromatography (40 g column) using a gradient from 0% to 20% of ethyl acetate in heptanes giving as a yellow gum, 2-(2-allyl-6-benzyloxy-phenyl)-5-[6-[(2S)-2-allylpyrrolidin-1-yl]-3-nitro-5-(trifluoromethyl)-2-pyridyl]-1,3,4-oxadiazole (680 mg, 57%). $^1$H NMR (300 MHz, Chloroform-d) δ 8.69 (d, J 2.6 Hz, 1H), 7.38 (dd, J 7.9, 3.2 Hz, 1H), 7.33-7.18 (m, 5H), 7.01-6.82 (m, 2H), 6.49-6.18 (m, 1H), 5.72-5.52 (m, 1H), 5.13 (s, 2H), 5.08-4.91 (m, 3H), 4.71-4.58 (m, 1H), 3.76-3.58 (m, 2H), 3.55-3.45 (m, 1H), 2.54-2.42 (m, 1H), 2.40-2.29 (m, 1H), 2.15-1.98 (m, 2H), 1.93-1.73 (m, 4H) ppm. $^{19}$F NMR (282 MHz, Chloroform-d) δ −54.68 (s, 3F) ppm. ESI-MS m/z calc. 591.2093, found 592.0 (M+1)$^+$; Retention time: 2.61 minutes (LC Method E).

Step 11: (16S)-7-(Benzyloxy)-24-nitro-22-(trifluoromethyl)-26-oxa-3,4,20,25-tetraazapentacyclo[19.3.1.12,5.06,11.016,20]hexacosa-1(25),2,4,6(11),7,9,13,21,23-nonaene (E/Z Mixture)

Step 12: (16R)-24-Amino-22-(trifluoromethyl)-26-oxa-3,4,20,25-tetraazapentacyclo[19.3.1.12,5.06,11.016,20]hexacosa-1(25),2,4,6(11),7,9,21,23-octaen-7-ol (Compound 134)

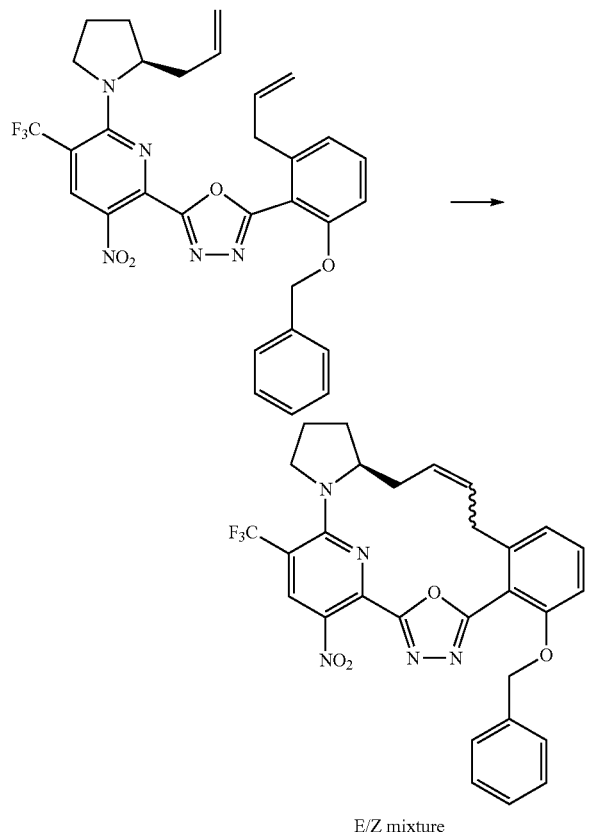

E/Z mixture

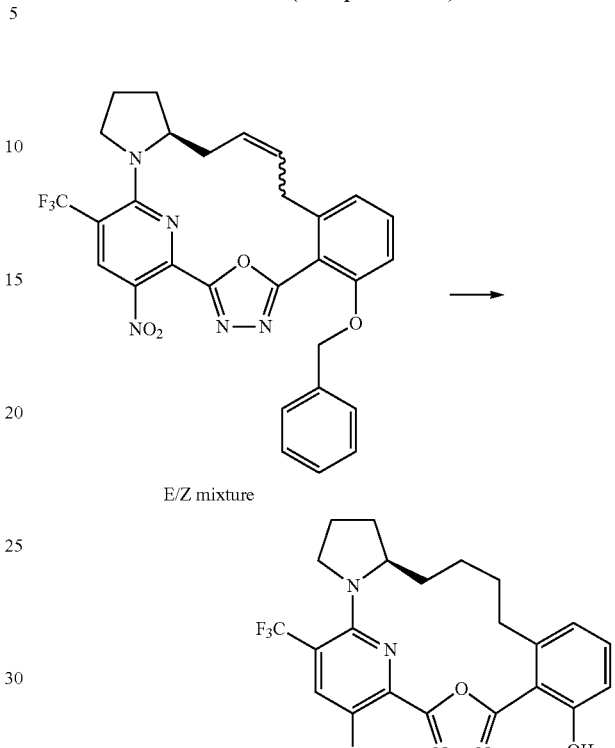

E/Z mixture

A degassed solution of 2-(2-allyl-6-benzyloxy-phenyl)-5-[6-[(2S)-2-allylpyrrolidin-1-yl]-3-nitro-5-(trifluoromethyl)-2-pyridyl]-1,3,4-oxadiazole (300 mg, 0.5071 mmol) in dichloroethane (70 mL) was heated to 50° C. under nitrogen atmosphere. Then, Zhan catalyst-1B (45 mg, 0.0613 mmol) was added in two portions over 15 minutes. The resulting mixture was heated at 70° C. for 5 hours. The mixture was cooled and concentrated under reduced pressure. The residue was purified by silica gel chromatography (12 g column) using a gradient from 0% to 40% ethyl acetate in heptanes giving as a yellow solid, (16S)-7-(benzyloxy)-24-nitro-22-(trifluoromethyl)-26-oxa-3,4,20,25-tetraazapentacyclo[19.3.1.12,5.06,11.016,20]hexacosa-1(25),2,4,6(11),7,9,13,21,23-nonaene (E/Z mixture) (77 mg, 26%). $^1$H NMR (300 MHz, Chloroform-d) δ 8.74-8.63 (m, 1H), 7.49-7.28 (m, 6H), 7.15-6.89 (m, 2H), 5.90-5.33 (m, 2H), 5.30-5.07 (m, 2H), 4.46-4.12 (m, 1H), 3.79-3.33 (m, 3H), 3.26-2.88 (m, 1H), 2.30-1.62 (m, 6H) ppm. $^{19}$F NMR (282 MHz, Chloroform-d) δ−53.50 to −53.77 (m, 3F) ppm. Retention time: 2.53 minutes (LC Method E).

(16S)-7-(Benzyloxy)-24-nitro-22-(trifluoromethyl)-26-oxa-3,4,20,25-tetraazapentacyclo[19.3.1.12,5.06,11.016,20]hexacosa-1(25),2,4,6(11),7,9,13,21,23-nonaene (E/Z mixture) (70 mg, 0.1242 mmol) was dissolved in methanol (5 mL). The mixture was bubbled with nitrogen for 5 min and then palladium on carbon (10% wet, 30 mg, 0.0141 mmol) was added. The resulting mixture was bubbled with a balloon of hydrogen for 5 min and then stirred at room temperature under hydrogen overnight. The mixture was filtered through a pad of Celite and washed with methanol (25 mL) and concentrated under reduced pressure. The residue was purified by silica gel chromatography (12 g column) using a gradient from 0% to 20% ethyl acetate in heptanes giving as a yellow solid, (16R)-24-amino-22-(trifluoromethyl)-26-oxa-3,4,20,25-tetraazapentacyclo[19.3.1.12,5.06,11.016,20]hexacosa-1(25),2,4,6(11),7,9,21,23-octaen-7-ol (43 mg, 74%). $^1$H NMR (300 MHz, DMSO-d6) δ 10.46 (s, 1H), 7.70 (s, 1H), 7.45-7.31 (m, 1H), 7.01-6.86 (m, 2H), 6.16 (s, 2H), 4.24-4.05 (m, 1H), 3.61-3.50 (m, 1H), 3.21-3.06 (m, 2H), 2.42-2.30 (m, 2H), 2.28-2.11 (m, 2H), 1.98-1.81 (m, 1H), 1.74-1.45 (m, 5H), 1.12-0.99 (m, 1H) ppm. $^{19}$F NMR (282 MHz, DMSO-d6) δ−55.68 (s, 3F) ppm. ESI-MS m/z calc. 445.1726, found 446.0 (M+1)$^+$; Retention time: 4.35 minutes (LC Method C).

Example 72: Preparation of 23-amino-8-fluoro-17, 17-dimethyl-6,21-bis(trifluoromethyl)-26-oxa-3,4, 19,24-tetraazapentacyclo[18.3.1.1<sup>2,5</sup>.1<sup>7,11</sup>.0<sup>15,19</sup>] hexacosa-1(24),2,4,7(25),8,10,20,22-octaen-6-ol (diastereomer pair 1) (hydrochloride salt) (Compound 135) and 23-amino-8-fluoro-17,17-dimethyl-6,21-bis(trifluoromethyl)-26-oxa-3,4,19,24-tetraaza-pentacyclo[18.3.1.1<sup>2,5</sup>.1<sup>7,11</sup>.0<sup>15,19</sup>]hexacosa-1 (24),2,4,7(25),8,10,20,22-octaen-6-ol (diastereomer pair 2) (hydrochloride salt) (Compound 136)

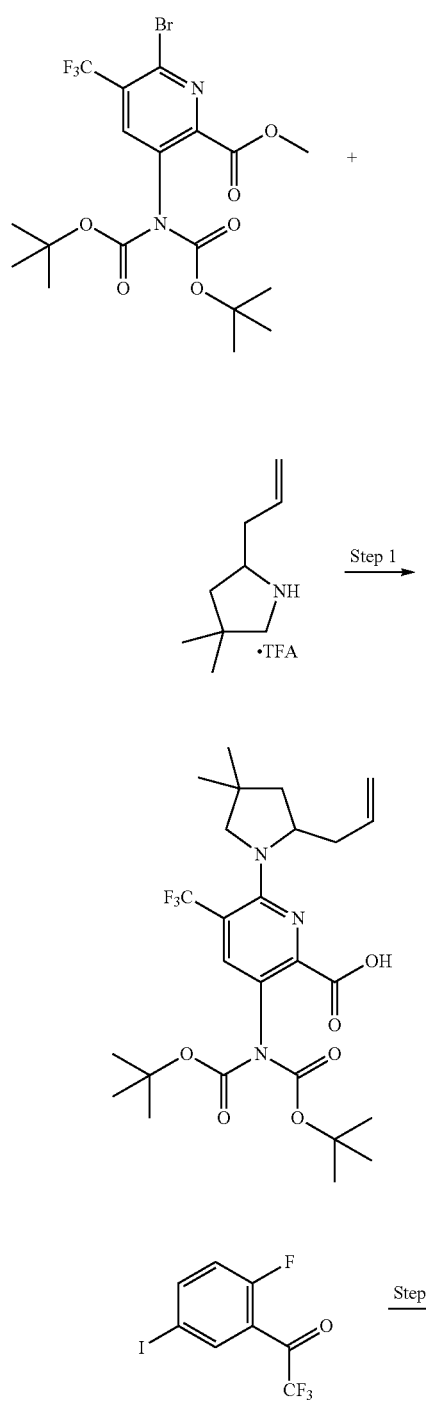

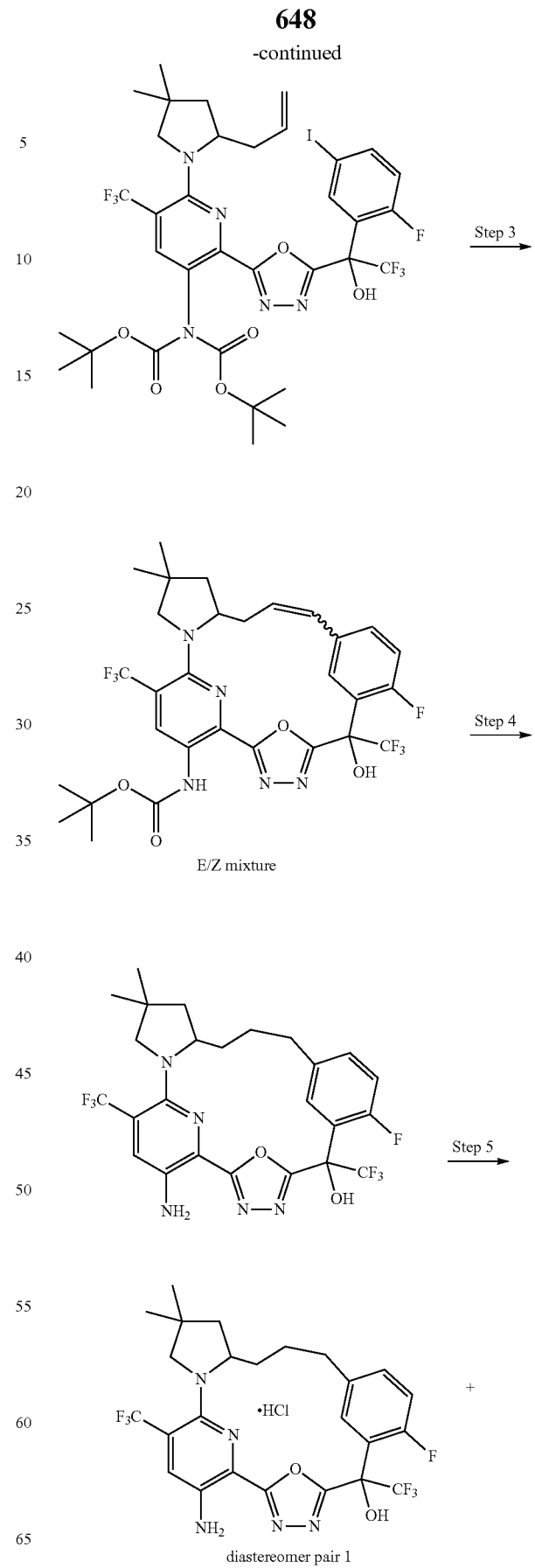

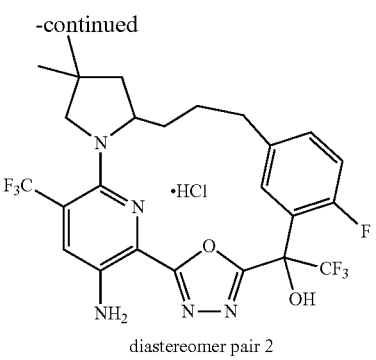

diastereomer pair 2

Step 1: 6-(2-Allyl-4,4-dimethyl-pyrrolidin-1-yl)-3-[bis(tert-butoxycarbonyl)amino]-5-(trifluoromethyl)pyridine-2-carboxylic Acid

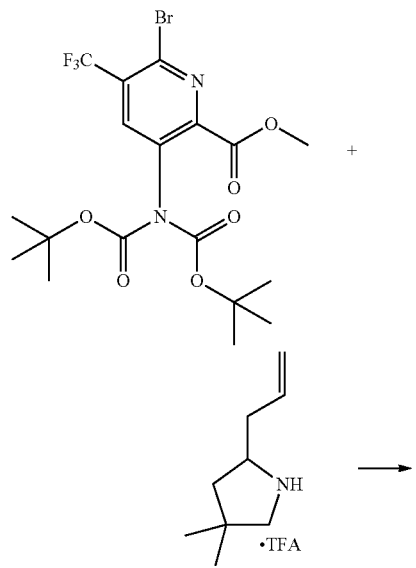

In a 5-mL sealed microwave vial, methyl 3-[bis(tert-butoxycarbonyl)amino]-6-bromo-5-(trifluoromethyl)pyridine-2-carboxylate (1.2 g, 2.403 mmol) and 2-allyl-4,4-dimethyl-pyrrolidine (trifluoroacetate salt) (876 mg, 3.459 mmol) and DIEA (2 mL, 11.48 mmol) were combined in acetonitrile (10 mL) and the mixture was heated at 70° C. for 18 hours. The reaction mixture was cooled to ambient temperature and the solvent removed. The resultant brown residue was dissolved in ethyl acetate and washed with saturated ammonium chloride solution, followed by brine. The organics were separated, dried over sodium sulfate, filtered and evaporated. The resultant brown residue was purified by silica gel chromatography using a gradient from 100% hexanes to 50% ethyl acetate in hexanes to afford methyl 6-(2-allyl-4,4-dimethyl-pyrrolidin-1-yl)-3-[bis(tert-butoxycarbonyl)amino]-5-(trifluoromethyl)pyridine-2-carboxylate (830 mg, 62%). ESI-MS m/z calc. 557.27124, found 558.3 (M+1)+; Retention time: 0.8 minutes (LC Method R).

The material described above, methyl 6-(2-allyl-4,4-dimethyl-pyrrolidin-1-yl)-3-[bis(tert-butoxycarbonyl)amino]-5-(trifluoromethyl)pyridine-2-carboxylate, was dissolved in 1:1 mixture of THF (4 mL) and MeOH (4 mL) and LiOH (8 mL, 1 M, 8 mmol) was added. The mixture was stirred at room temperature for 4 h. THF and MeOH was removed under reduced pressure. To the residue, water (5 mL) was added and cooled the resulting mixture to 0° C. The solution was acidified with HCl (8 mL, 1 M, 8 mmol) and extracted with ethyl acetate (3×50 mL). The combined organic layers were washed with brine (25 mL), dried over anhydrous sodium sulfate, filtered and concentrated under reduced pressure to afford 6-(2-allyl-4,4-dimethyl-pyrrolidin-1-yl)-3-[bis(tert-butoxycarbonyl)amino]-5-(trifluoromethyl)pyridine-2-carboxylic acid (530 mg, 41%). ESI-MS m/z calc. 543.2556, found 444.2 (M-100 (Boc))+; Retention time: 0.8 minutes (LC Method R).

Step 2: tert-Butyl N-[6-(2-allyl-4,4-dimethyl-pyrrolidin-1-yl)-2-[5-[2,2,2-trifluoro-1-(2-fluoro-5-iodo-phenyl)-1-hydroxy-ethyl]-1,3,4-oxadiazol-2-yl]-5-(trifluoromethyl)-3-pyridyl]-N-tert-butoxycarbonyl-carbamate

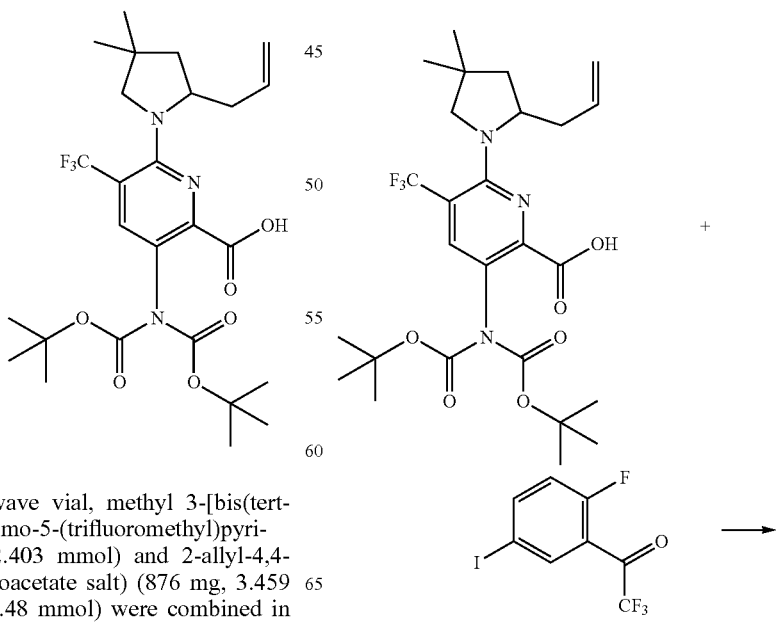

651

-continued

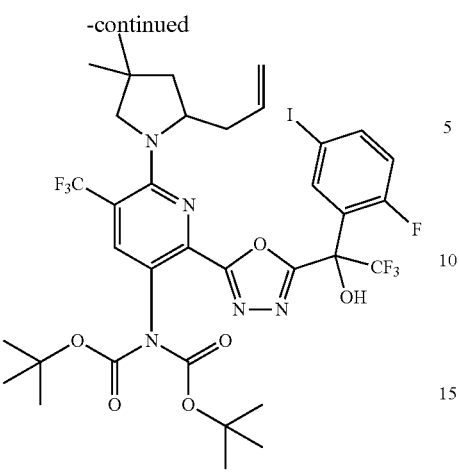

To a stirred solution of 6-(2-allyl-4,4-dimethyl-pyrrolidin-1-yl)-3-[bis(tert-butoxycarbonyl)amino]-5-(trifluoromethyl)pyridine-2-carboxylic acid (500 mg, 0.9198 mmol) and 2,2,2-trifluoro-1-(2-fluoro-5-iodo-phenyl)ethanone (457 mg, 1.437 mmol) in DMF (5 mL) was added (N-isocyanoimino)triphenylphosphorane (432 mg, 1.429 mmol) and the mixture was stirred at room temperature overnight. Then the mixture was diluted with EtOAc (50 mL), washed with water and brine, dried over sodium sulfate, filtered and concentrated. The resultant brown residue was purified by silica gel chromatography using a shallow gradient 100% hexanes to 100% ethyl acetate giving as bright yellow viscous oil, tert-butyl N-[6-(2-allyl-4,4-dimethyl-pyrrolidin-1-yl)-2-[5-[2,2,2-trifluoro-1-(2-fluoro-5-iodo-phenyl)-1-hydroxy-ethyl]-1,3,4-oxadiazol-2-yl]-5-(trifluoromethyl)-3-pyridyl]-N-tert-butoxycarbonyl-carbamate (512 mg, 63%). $^1$H NMR (400 MHz, Chloroform-d) δ 9.52 (d, J 21.6 Hz, 1H), 8.96 (s, 1H), 8.21 (td, J 7.4, 2.3 Hz, 1H), 7.78 (tdd, J 8.6, 4.6, 2.3 Hz, 1H), 6.85 (td, J=11.6, 8.7 Hz, 1H), 5.63-5.41 (m, 1H), 4.97-4.80 (m, 2H), 4.52-4.37 (m, 2H), 3.37 (d, J 10.2 Hz, 1H), 3.02 (s, 1H), 2.54-2.35 (m, 1H), 2.12 (dq, J 21.7, 7.6 Hz, 1H), 1.75 (dd, J=12.4, 6.9 Hz, 1H), 1.59 (s, 9H), 1.53 (s, 9H), 1.11 (d, J=3.9 Hz, 3H), 0.85 (d, J=5.8 Hz, 3H) ppm. ESI-MS m/z calc. 885.18335, found 786.1 (M-100 (Boc))$^+$; Retention time: 2.03 and 2.06, diastereomeric mixture (LC Method M).

Step 3: tert-Butyl N-18-fluoro-6-hydroxy-17,17-dimethyl-6,21-bis(trifluoromethyl)-26-oxa-3,4,19,24-tetraazapentacyclo[18.3.1.1$^{2,5}$.1$^{7,11}$.0$^{15,19}$]hexacosa-1(24),2,4,7(25),8,10,12,20,22-nonaen-23-yl]carbamate (E/Z mixture)

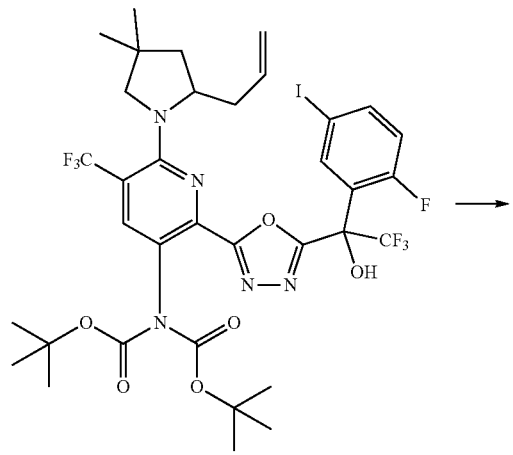

652

-continued

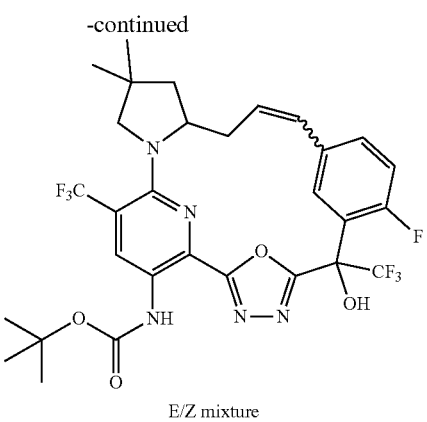

E/Z mixture

To a stirred solution of tert-butyl N-[6-(2-allyl-4,4-dimethyl-pyrrolidin-1-yl)-2-[5-[2,2,2-trifluoro-1-(2-fluoro-5-iodo-phenyl)-1-hydroxy-ethyl]-1,3,4-oxadiazol-2-yl]-5-(trifluoromethyl)-3-pyridyl]-N-tert-butoxycarbonyl-carbamate (500 mg, 0.5646 mmol) in acetonitrile (80 mL) was added palladium(II) acetate (18 mg, 0.08017 mmol) and tris(o-tolyl)phosphine (47 mg, 0.1544 mmol) followed by triethylamine (500 µL, 3.587 mmol) and the solution was bubbled with N$_2$ for 1 min then heated at 80° C. for 22 h. The reaction mixture was cooled to room temperature, concentrated to about 5 mL volume and filtered through Celite and filtrate was concentrated. The resultant brown residue was purified by silica gel chromatography using a shallow gradient from 100% hexanes to 100% ethyl acetate giving as a yellow solid, tert-butyl N-[8-fluoro-6-hydroxy-17,17-dimethyl-6,21-bis(trifluoromethyl)-26-oxa-3,4,19,24-tetraazapentacyclo[18.3.1.1$^{2,5}$.1$^{7,11}$.0$^{15,19}$]hexacosa-1(24),2,4,7(25),8,10,12,20,22-nonaen-23-yl]carbamate (E/Z mixture) (216 mg, 58%). ESI-MS m/z calc. 657.2186, found 658.2 (M+1)$^+$; Retention time: 1.93 minutes (LC Method M).

Step 4: 23-Amino-8-fluoro-17,17-dimethyl-6,21-bis(trifluoromethyl)-26-oxa-3,4,19,24-tetraazapentacyclo[18.3.1.1$^{2,5}$.1$^{7,11}$.0$^{15,19}$]hexacosa-1(24),2,4,7(25),8,10,20,22-octaen-6-ol

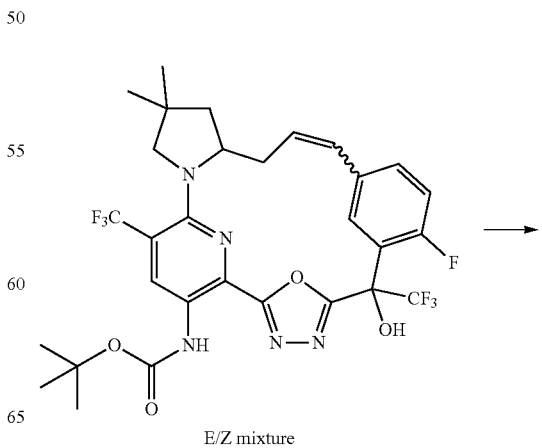

E/Z mixture

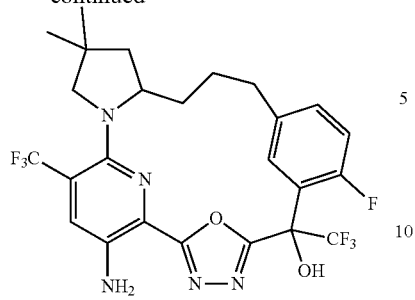

To a solution of tert-butyl N-[8-fluoro-6-hydroxy-17,17-dimethyl-6,21-bis(trifluoromethyl)-26-oxa-3,4,19,24-tetraazapentacyclo[18.3.1.1²,⁵.1⁷,¹¹.0¹⁵,¹⁹]hexacosa-1(24),2,4,7(25),8,10,12,20,22-nonaen-23-yl]carbamate (E/Z mixture) (500 mg, 0.7604 mmol) in ethanol (10 mL) was added Pd/C (157 mg, 10% w/w, 0.1475 mmol) in a flask equipped with a $H_2$ balloon using a 3 way adaptor. Subjected the vessel to vacuum and backfilled with nitrogen gas three times then subjected to vacuum. Filled the flask with hydrogen gas then stirred the mixture for 15 hours. Subjected to vacuum and backfilled with nitrogen gas three times then diluted with ethyl acetate and filtered over Celite. The filtrate was concentrated and the resulting residue was dissolved in in a pre-made solution of TFA (2 mL, 25.96 mmol) and dichloromethane (6 mL) and the reaction mixture was stirred at room temperature for about 1 h. Solvents were removed, and the residue was purified by reverse phase HPLC using a gradient from 50% to 99% acetonitrile in water (+5 mM HCl) over 15.0 minutes which gave as a yellow solid and mixture of 4 stereoisomers, 23-amino-8-fluoro-17,17-dimethyl-6,21-bis(trifluoromethyl)-26-oxa-3,4,19,24-tetraazapentacyclo[18.3.1.1²,⁵.1⁷,¹¹.0¹⁵,¹⁹]hexacosa-1(24),2,4,7(25),8,10,20,22-octaen-6-ol (127 mg, 30%). ESI-MS m/z calc. 559.1818, found 560.0 (M+1)⁺; Retention time: 1.91 minutes (LC Method J).

Step 5: 23-Amino-8-fluoro-17,17-dimethyl-6,21-bis(trifluoromethyl)-26-oxa-3,4,19,24-tetraazapentacyclo[18.3.1.1²,⁵.1⁷,¹¹.0¹⁵,¹⁹]hexacosa-1(24),2,4,7(25),8,10,20,22-octaen-6-ol (diastereomer pair 1) (hydrochloride salt) (Compound 135) and 23-amino-8-fluoro-17,17-dimethyl-6,21-bis(trifluoromethyl)-26-oxa-3,4,19,24-tetraazapentacyclo[18.3.1.1²,⁵.1⁷,¹¹.0¹⁵,¹⁹]hexacosa-1(24),2,4,7(25),8,10,20,22-octaen-6-ol (diastereomer pair 2) (Hydrochloride Salt) (Compound 136)

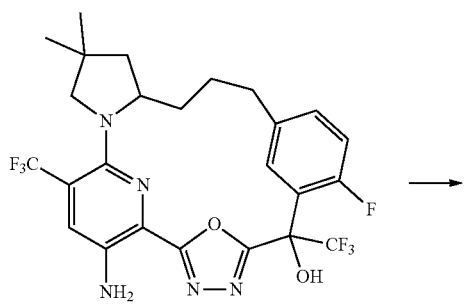

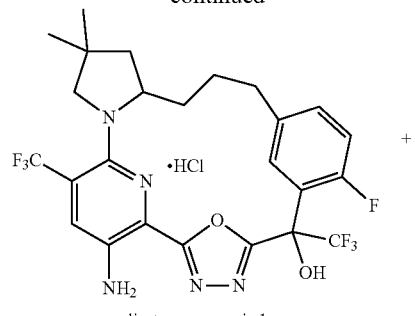

diastereomer pair 1

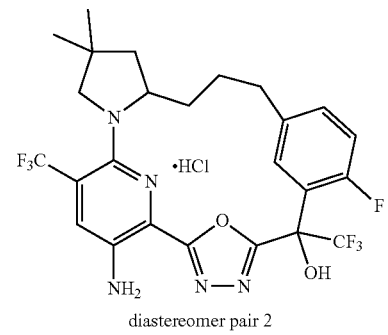

diastereomer pair 2

23-Amino-8-fluoro-17,17-dimethyl-6,21-bis(trifluoromethyl)-26-oxa-3,4,19,24-tetraazapentacyclo[18.3.1.1²,⁵.1⁷,¹¹.0¹⁵,¹⁹]hexacosa-1(24),2,4,7(25),8,10,20,22-octaen-6-ol (80 mg, 0.143 mmol) was purified by reverse phase HPLC using a gradient from 40% to 85% acetonitrile in water (+5 mM HCl) over 30 minutes which gave the separation of two diastereomer pairs:

The first diastereomer pair to elute was isolated as a yellow solid, 23-amino-8-fluoro-17,17-dimethyl-6,21-bis(trifluoromethyl)-26-oxa-3,4,19,24-tetraazapentacyclo[18.3.1.1²,⁵.1⁷,¹¹.0¹⁵,¹⁹]hexacosa-1(24),2,4,7(25),8,10,20,22-octaen-6-ol (diastereomer pair 1) (hydrochloride salt) (1.8 mg, 4%). ESI-MS m/z calc. 559.1818, found 560.5 (M+1)⁺; Retention time: 1.79 minutes (LC Method J).

The second diastereomer pair to elute was isolated as a yellow solid, 23-amino-8-fluoro-17,17-dimethyl-6,21-bis(trifluoromethyl)-26-oxa-3,4,19,24-tetraazapentacyclo[18.3.1.1²,⁵.1⁷,¹¹.0¹⁵,¹⁹]hexacosa-1(24),2,4,7(25),8,10,20,22-octaen-6-ol (diastereomer pair 2) (hydrochloride salt) (3.2 mg, 8%). ¹H NMR (400 MHz, DMSO-d6) δ 8.53 (s, 1H), 7.73 (d, J=7.6 Hz, 1H), 7.68 (s, 1H), 7.30 (d, J=8.9 Hz, 1H), 7.13 (dd, J 12.6, 8.4 Hz, 1H), 6.15 (s, 2H), 4.22-4.11 (m, 1H), 3.28 (s, 1H), 2.88 (t, J=12.1 Hz, 2H), 2.58 (s, 1H), 2.11 (d, J=9.0 Hz, 1H), 1.88 (dd, J=12.0, 6.2 Hz, 1H), 1.72 (d, J=32.5 Hz, 2H), 1.46 (t, J=11.5 Hz, 1H), 1.10 (s, 3H), 0.96-0.86 (m, 1H), 0.83 (s, 3H) ppm. ESI-MS m/z calc. 559.1818, found 560.11 (M+1)⁺; Retention time: 1.85 minutes (LC Method J).

Example 73: Preparation of (12R)-20-amino-18-benzyl-6-(trifluoromethyl)-22-oxa-3,4,16,21-tetraazatetracyclo[15.3.1.1²,⁵.0¹²,¹⁶]docosa-1(21),2,4,17,19-pentaen-6-ol (Compound 137)

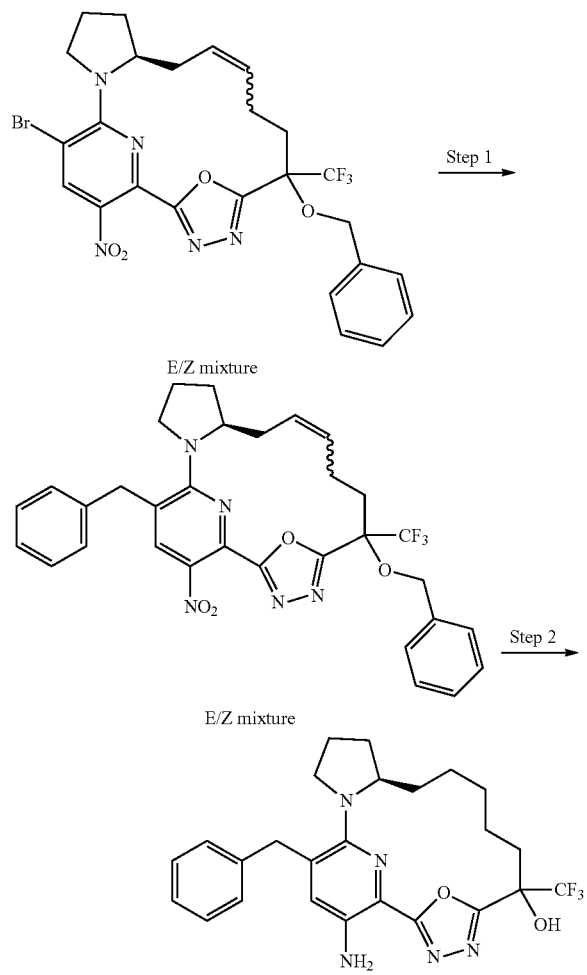

Step 1: (12S)-18-Benzyl-6-(benzyloxy)-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture)

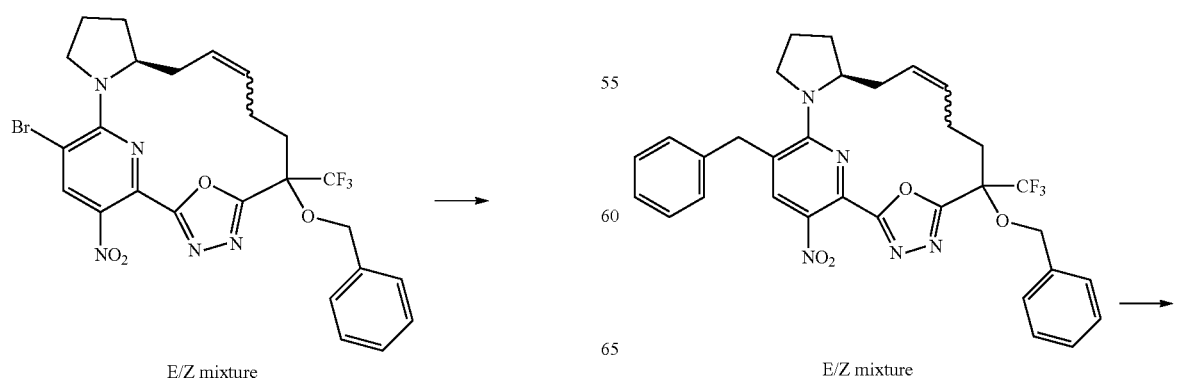

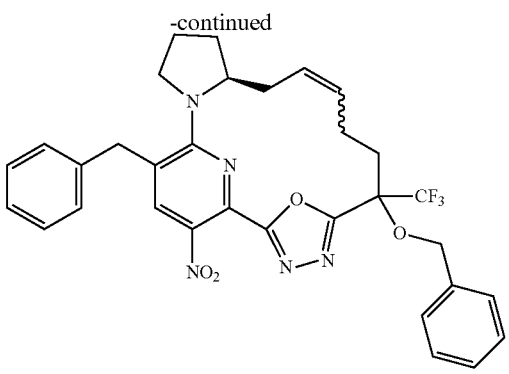

A solution of (12S)-6-(benzyloxy)-18-bromo-20-nitro-6-(trifluoromethyl)-22-oxa-3,4,16,21-tetraazatetracyclo [15.3.1.1²,⁵.0¹²,¹⁶]docosa-1(21),2,4,9,17,19-hexaene (E/Z mixture) (55 mg, 0.0925 mmol) in tetrahydrofuran (3 mL) was degassed by bubbling with nitrogen for 15 minutes. 2-Benzyl-4,4,5,5-tetramethyl-1,3,2-dioxaborolane (60 mg, 0.2751 mmol) and 1,1'-bis(diphenylphosphino)ferrocene palladium(II) chloride, complex with dichloromethane (12 mg, 0.0147 mmol) were added followed by the addition of a degassed aqueous solution of cesium carbonate (120 µL, 2 M, 0.24 mmol) under nitrogen. The reaction mixture was heated overnight at 90° C. After cooling to room temperature, the reaction mixture was diluted with ethyl acetate (15 mL) and filtered through a pad of Celite washing with ethyl acetate (2×15 mL). The filtrate was dried over anhydrous sodium sulfate, filtered and concentrated. The resulting mixture was purified by reverse phase HPLC using a gradient from 0% to 95% acetonitrile in water (+0.1% formic acid) which gave as a brown foam, (12S)-18-benzyl-6-(benzyloxy)-20-nitro-6-(trifluoromethyl)-22-oxa-3,4,16,21-tetraazatetracyclo[15.3.1.1²,⁵.0¹²,¹⁶]docosa-1(21),2,4,9, 17,19-hexaene (E/Z mixture) (50 mg, 89%). ¹H NMR (300 MHz, Chloroform-d) δ 8.03 (s, 1H), 7.48-7.28 (m, 8H), 7.08 (d, J=6.8 Hz, 2H), 5.66-5.35 (m, 2H), 5.33-5.14 (m, 1H), 5.03-4.89 (m, 1H), 4.29-4.16 (m, 2H), 4.13-4.02 (m, 1H), 3.83-3.59 (m, 2H), 3.48-3.23 (m, 1H), 2.54-2.21 (m, 2H), 2.19-1.90 (m, 4H), 1.84-1.60 (m, 2H), 1.55-1.43 (m, 1H) ppm. ¹⁹F NMR (282 MHz, Chloroform-d) δ −73.02 (s, 3F), −73.54 (s, 3F) ppm. ESI-MS m/z calc. 605.225, found 606.3 (M+1)⁺; Retention time: 2.65 minutes (LC Method E).

Step 2: (12R)-20-Amino-18-benzyl-6-(trifluoromethyl)-22-oxa-3,4,16,21-tetraazatetracyclo[15.3.1.1²,⁵.0¹²,¹⁶]docosa-1(21),2,4,17,19-pentaen-6-ol (Compound 137)

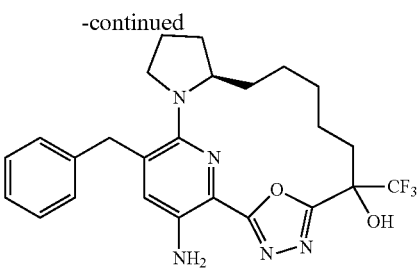

A solution of (12S)-18-benzyl-6-(benzyloxy)-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene (E/Z mixture) (50 mg, 0.0826 mmol) in methanol (5 mL) was bubbled with nitrogen for 5 minutes and then palladium on carbon (88 mg, 5% w/w, 0.0413 mmol) was added. Hydrogen was then bubbled with a balloon through the reaction for 5 minutes and the reaction mixture was stirred at room temperature under hydrogen overnight. The mixture was filtered through a pad of Celite, washed with methanol (25 mL) and concentrated under reduced pressure. The residue was purified by reverse phase HPLC using a gradient from 5% to 95% acetonitrile in water (+0.1% formic acid) giving as a yellow solid and mixture of diastereomers, (12R)-20-amino-18-benzyl-6-(trifluoromethyl)-22-oxa-3,4,16,21-tetraazatetracyclo[15.3.1.1²,⁵.0¹²,¹⁶]docosa-1(21),2,4,17,19-pentaen-6-ol (21 mg, 52%). ¹H NMR (300 MHz, Chloroform-d) δ 7.35-7.19 (m, 3H), 7.09 (d, J=6.5 Hz, 2H), 6.61 (br. s., 1H), 5.52-4.38 (m, 2H), 4.18-3.78 (m, 3H), 3.75-3.57 (m, 1H), 3.27-3.01 (m, 1H), 2.62-2.22 (m, 2H), 2.20-2.09 (m, 1H), 2.04-1.80 (m, 2H), 1.78-1.29 (m, 9H), 1.04-0.63 (m, 1H) ppm. ESI-MS m/z calc. 487.2195, found 488.2 (M+1)⁺; Retention time: 3.79 minutes (LC Method C).

Example 74: Preparation of (6R,15S)-23-amino-8-fluoro-6,21-bis(trifluoromethyl)-26-oxa-3,4,19,24-tetraazapentacyclo[18.3.1.1²,⁵.1⁷,¹¹.0¹⁵,¹⁹]hexacosa-1(24),2,4,7(25),8,10,12,20,22-nonaen-6-ol (E/Z mixture) (hydrochloride salt) (Compound 138) and (6S,15S)-23-amino-8-fluoro-6,21-bis(trifluoromethyl)-26-oxa-3,4,19,24-tetraazapentacyclo[18.3.1.1²,⁵.1⁷,¹¹.0¹⁵,¹⁹]hexacosa-1(24),2,4,7(25),8,10,12,20,22-nonaen-6-ol (E/Z mixture) (hydrochloride salt) (Compound 139)

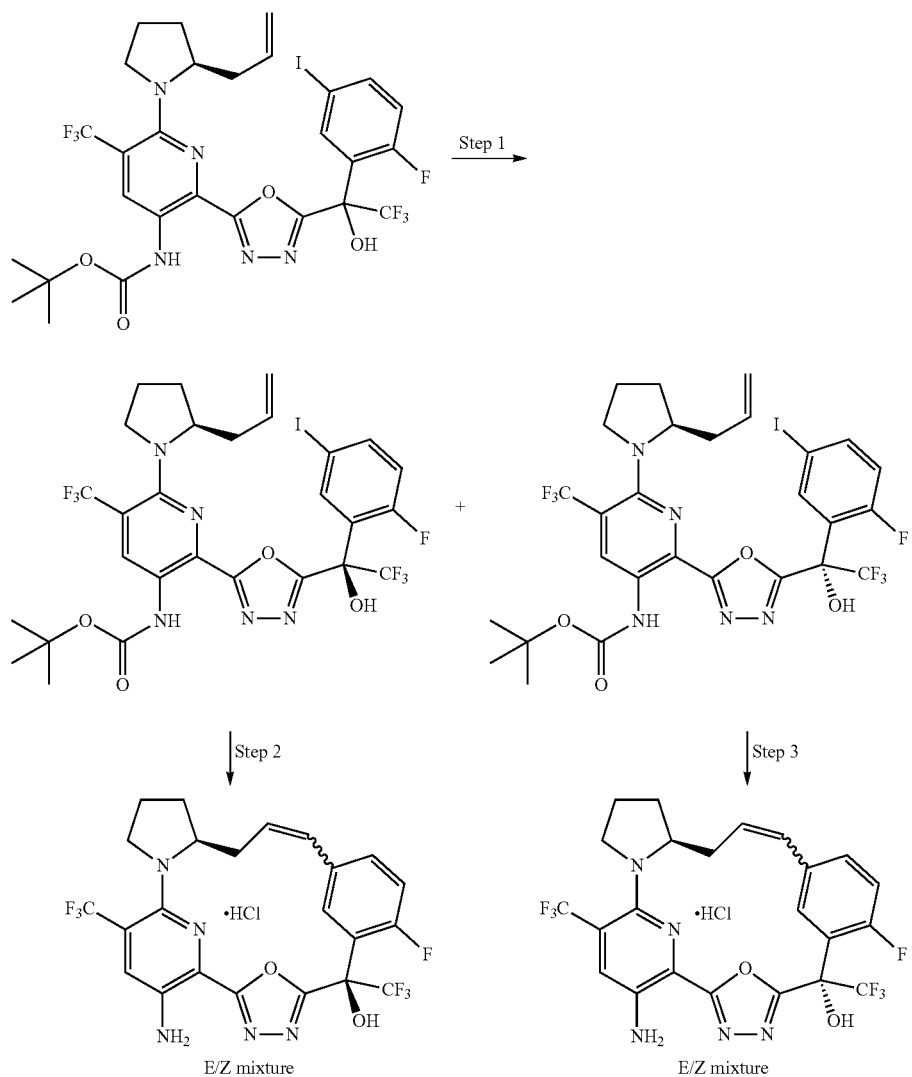

Step 1: tert-Butyl N-[6-[(2S)-2-allylpyrrolidin-1-yl]-2-[5-[(1R)-2,2,2-trifluoro-1-(2-fluoro-5-iodo-phenyl)-1-hydroxy-ethyl]-1,3,4-oxadiazol-2-yl]-5-(trifluoromethyl)-3-pyridyl]carbamate and tert-butyl N-[6-[(2S)-2-allylpyrrolidin-1-yl]-2-[5-[(1S)-2,2,2-trifluoro-1-(2-fluoro-5-iodo-phenyl)-1-hydroxy-ethyl]-1,3,4-oxadiazol-2-yl]-5-(trifluoromethyl)-3-pyridyl]carbamate

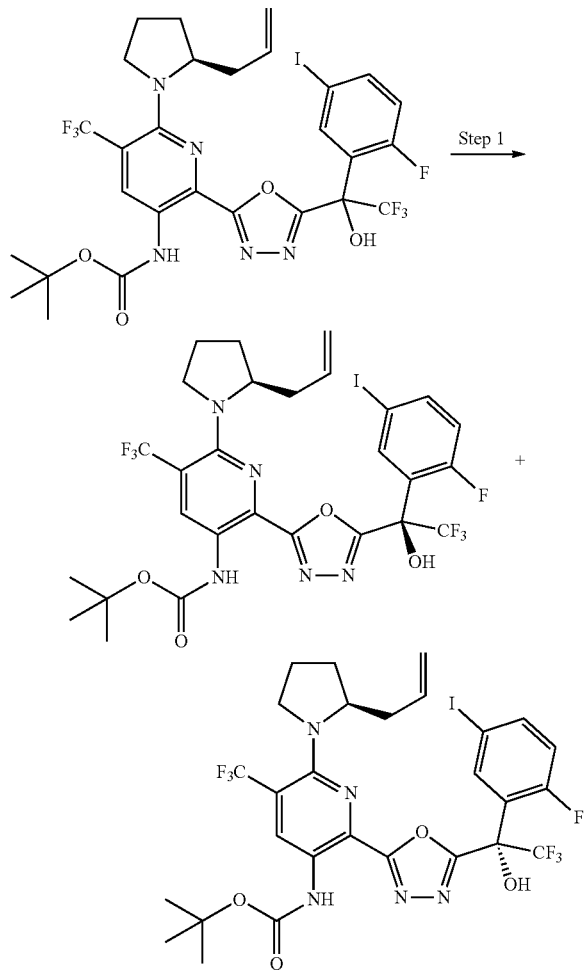

tert-Butyl N-[6-[(2S)-2-allylpyrrolidin-1-yl]-2-[5-[2,2,2-trifluoro-1-(2-fluoro-5-iodo-phenyl)-1-hydroxy-ethyl]-1,3,4-oxadiazol-2-yl]-5-(trifluoromethyl)-3-pyridyl]carbamate (200 mg, 0.264 mmol) was dissolved in methanol (6 mL) and purified by reverse phase HPLC using a $C_{18}$ column and a gradient from 70% to 99% acetonitrile in water (+5 mM HCl) over 20 minutes giving two diastereomeric products:

The first diastereomer to elute was isolated as a yellow solid, tert-butyl N-[6-[(2S)-2-allylpyrrolidin-1-yl]-2-[5-[(1R)-2,2,2-trifluoro-1-(2-fluoro-5-iodo-phenyl)-1-hydroxy-ethyl]-1,3,4-oxadiazol-2-yl]-5-(trifluoromethyl)-3-pyridyl]carbamate (78 mg, 78%). $^1$H NMR (400 MHz, DMSO-d6) δ 9.38 (s, 1H), 9.05 (s, 1H), 8.67 (s, 1H), 8.18 (dd, J=7.1, 2.3 Hz, 1H), 7.96 (ddd, J=8.6, 4.6, 2.3 Hz, 1H), 7.15 (dd, J=11.4, 8.6 Hz, 1H), 5.40 (ddt, J=14.3, 10.9, 7.2 Hz, 1H), 5.01-4.86 (m, 2H), 4.34 (d, J=4.4 Hz, 1H), 4.04 (dt, J=11.0, 8.4 Hz, 1H), 3.77 (m, J=6.1, 4.2 Hz, 1H), 3.53 (q, J=8.0, 7.2 Hz, 1H), 3.44 (qd, J=7.0, 5.0 Hz, 1H), 2.03-1.88 (m, 2H), 1.73-1.58 (m, 2H), 1.49 (s, 9H) ppm. ESI-MS m/z calc. 757.0996, found 758.4 (M+1)$^+$; Retention time: 1.96 minutes (LC Method M).

The second diastereomer to elute was isolated as a yellow solid, tert-butyl N-[6-[(2S)-2-allylpyrrolidin-1-yl]-2-[5-[(1S)-2,2,2-trifluoro-1-(2-fluoro-5-iodo-phenyl)-1-hydroxy-ethyl]-1,3,4-oxadiazol-2-yl]-5-(trifluoromethyl)-3-pyridyl]carbamate (67 mg, 60%). $^1$H NMR (400 MHz, DMSO-d6) δ 9.45 (s, 1H), 9.10 (s, 1H), 8.69 (s, 1H), 8.18 (dd, J=7.1, 2.3 Hz, 1H), 7.91 (ddd, J=8.7, 4.6, 2.3 Hz, 1H), 7.07 (dd, J=11.4, 8.6 Hz, 1H), 5.37 (ddt, J=17.2, 10.2, 7.1 Hz, 1H), 4.90-4.77 (m, 2H), 4.34 (t, J=5.1 Hz, 1H), 4.26-4.11 (m, 1H), 3.53 (q, J=9.0 Hz, 1H), 3.44 (qd, J=7.0, 5.0 Hz, 2H), 2.36-2.27 (m, 1H), 1.98-1.89 (m, 1H), 1.76-1.52 (m, 2H), 1.49 (s, 9H) ppm. ESI-MS m/z calc. 757.0996, found 758.2 (M+1)$^+$; Retention time: 1.98 minutes (LC Method M).

Step 2: (6R,15S)-23-Amino-8-fluoro-6,21-bis(trifluoromethyl)-26-oxa-3,4,19,24-tetraazapentacyclo[18.3.1.1$^{2,5}$.1$^{7,11}$.0$^{15,19}$]hexacosa-1(24),2,4,7(25),8,10,12,20,22-nonaen-6-ol (E/Z mixture) (hydrochloride salt) (Compound 138)

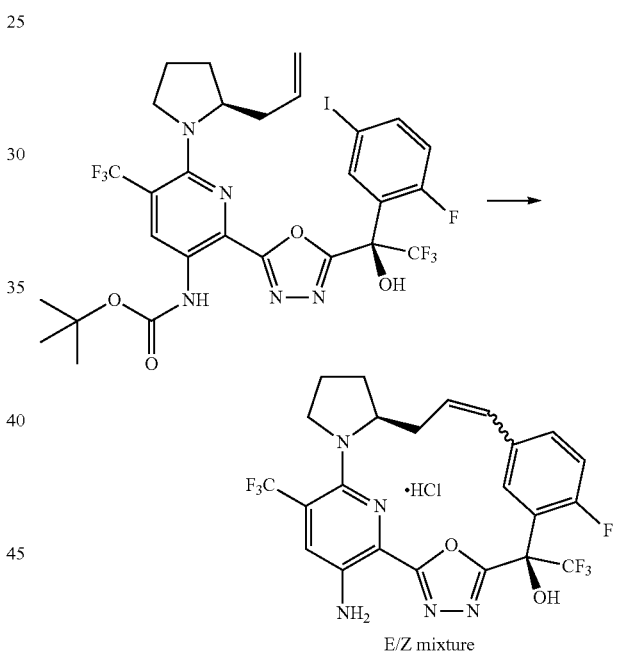

E/Z mixture

Part A: To a stirred solution of tert-butyl N-[6-[(2S)-2-allylpyrrolidin-1-yl]-2-[5-[(1R)-2,2,2-trifluoro-1-(2-fluoro-5-iodo-phenyl)-1-hydroxy-ethyl]-1,3,4-oxadiazol-2-yl]-5-(trifluoromethyl)-3-pyridyl]carbamate (180 mg, 0.2376 mmol) in acetonitrile (25 mL) was added palladium(II) acetate (5.947 mg, 0.02649 mmol) followed by tris(o-tolyl)phosphine (18 mg, 0.05914 mmol) and triethylamine (300 µL, 1.251 mmol) and the solution was bubbled with $N_2$ for 2 min, then heated at 80° C. for 22 h. The reaction mixture was cooled to room temperature, concentrated to about 5 mL volume and the resultant brown residue was purified by silica gel chromatography using a shallow gradient from 100% hexanes to 50% ethyl acetate in hexanes giving as a yellow solid, tert-butyl N-[(6R,15S)-8-fluoro-6-hydroxy-6,21-bis(trifluoromethyl)-26-oxa-3,4,19,24-tetraazapentacyclo[18.3.1.1$^{2,5}$.1$^{7,11}$.0$^{15,19}$]hexacosa-1(24),2,4,7(25),8,10,12,20,22-nonaen-23-yl]carbamate (E/Z mixture) (87 mg, 58%). ESI-MS m/z calc. 629.1873, found 630.2 (M+1)⁺; Retention time: 1.68 minutes (LC Method M).

Part B: tert-Butyl N-[(6R,15S)-8-fluoro-6-hydroxy-6,21-bis(trifluoromethyl)-26-oxa-3,4,19,24-tetraazapentacyclo[18.3.1.1$^{2,5}$.1$^{7,11}$.0$^{15,19}$]hexacosa-1(24),2,4,7(25),8,10,12,20,22-nonaen-23-yl]carbamate (E/Z mixture) (25 mg, 0.03971 mmol) was dissolved in a pre-made solution of TFA (100 µL, 1.298 mmol) and dichloromethane (400 µL) and the reaction mixture was stirred at room temperature for about 1 h. Solvents were removed, and the residue was purified by reverse phase HPLC using a gradient from 0% to 99% acetonitrile in water (+5 mM HCl) over 15 minutes giving as a yellow solid, (6R,15S)-23-amino-8-fluoro-6,21-bis(trifluoromethyl)-26-oxa-3,4,19,24-tetraazapentacyclo[18.3.1.1$^{2,5}$.1$^{7,11}$.0$^{15,19}$]hexacosa-1(24),2,4,7(25),8,10,12,20,22-nonaen-6-ol (E/Z mixture) (hydrochloride salt) (8.2 mg, 36%). $^1$H NMR (400 MHz, DMSO-d6) δ 8.63 (s, 1H), 8.15-8.04 (m, 1H), 7.76 (d, J=27.5 Hz, 1H), 7.33 (d, J=7.4 Hz, 1H), 7.23 (ddd, J=25.4, 12.6, 8.4 Hz, 1H), 6.53 (d, J=12.1 Hz, 0.5 H), 6.39 (s, 1H), 6.22 (s, 1H), 5.83 (td, J=12.1, 5.2 Hz, 0.5 H), 5.71-5.54 (m, 1H), 4.66 (d, J=10.0 Hz, 0.5 H), 3.99 (t, J=5.4 Hz, 0.5 H), 3.63 (tt, J=17.3, 7.8 Hz, 2H), 3.23 (dd, J=16.5, 8.5 Hz, 2H), 2.26-2.12 (m, 1H), 1.92 (s, 1H), 1.71 (t, J=10.7 Hz, 1H), 1.58 (s, 1H) ppm. ESI-MS m/z calc. 529.1349, found 530.0 (M+1)⁺; Retention time: 1.78 minutes (LC Method J).

Step 3: (6S,15S)-23-Amino-8-fluoro-6,21-bis(trifluoromethyl)-26-oxa-3,4,19,24-tetraazapentacyclo[18.3.1.1$^{2,5}$.1$^{7,11}$.0$^{15,19}$]hexacosa-1(24),2,4,7(25),8,10,12,20,22-nonaen-6-ol (E/Z mixture) (hydrochloride salt) (Compound 139)

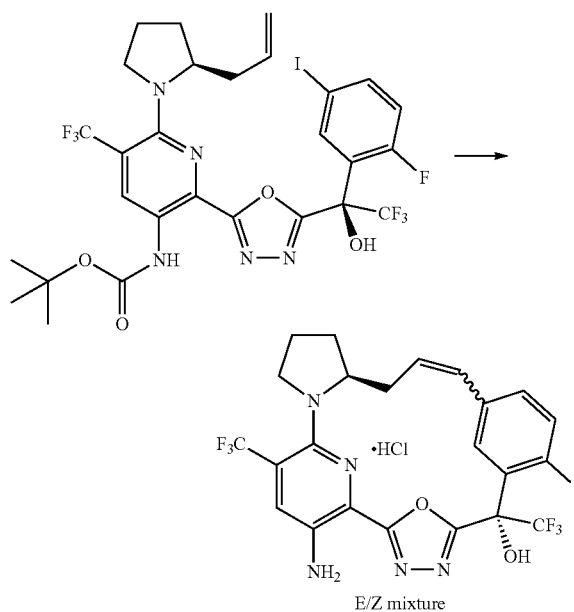

Part A: To a stirred solution of tert-butyl N-[6-[(2S)-2-allylpyrrolidin-1-yl]-2-[5-[(1S)-2,2,2-trifluoro-1-(2-fluoro-5-iodo-phenyl)-1-hydroxy-ethyl]-1,3,4-oxadiazol-2-yl]-5-(trifluoromethyl)-3-pyridyl]carbamate (180 mg, 0.2376 mmol) in acetonitrile (25 mL) was added palladium(II) acetate (8 mg, 0.03563 mmol) followed by tris(o-tolyl)phosphine (17 mg, 0.05585 mmol) and triethylamine (200 µL, 0.435 mmol) and the solution was bubbled with N₂ for 2 min, then heated at 80° C. for 22 h. The reaction mixture was cooled to room temperature, concentrated to about 5 mL volume and the resultant brown residue was purified by silica gel chromatography using a shallow gradient 100% hexanes to 50% ethyl acetate in hexanes giving as a yellow solid, tert-butyl N-[(6S,15S)-8-fluoro-6-hydroxy-6,21-bis(trifluoromethyl)-26-oxa-3,4,19,24-tetraazapentacyclo[18.3.1.1$^{2,5}$.1$^{7,11}$.0$^{15,19}$]hexacosa-1(24),2,4,7(25),8,10,12,20,22-nonaen-23-yl]carbamate (E/Z mixture) (84 mg, 56%). ESI-MS m/z calc. 629.1873, found 630.2 (M+1)⁺; Retention time: 1.68 minutes (LC Method M).

Part B: tert-Butyl N-[(6S,15S)-8-fluoro-6-hydroxy-6,21-bis(trifluoromethyl)-26-oxa-3,4,19,24-tetraazapentacyclo[18.3.1.1$^{2,5}$.1$^{7,11}$.0$^{15,19}$]hexacosa-1(24),2,4,7(25),8,10,12,20,22-nonaen-23-yl]carbamate (E/Z mixture) (25 mg, 0.03971 mmol) was dissolved in a pre-made solution of TFA (100 µL, 1.298 mmol) and dichloromethane (400 µL) and the reaction mixture was stirred at room temperature for about 1 h. Solvents were removed, and the residue was purified by reverse phase HPLC using a gradient from 0% to 99% acetonitrile in water (+5 mM HCl) over 15 minutes giving as a yellow solid, (6S,15S)-23-amino-8-fluoro-6,21-bis(trifluoromethyl)-26-oxa-3,4,19,24-tetraazapentacyclo[18.3.1.1$^{2,5}$.1$^{7,11}$.0$^{15,19}$]hexacosa-1(24),2,4,7(25),8,10,12,20,22-nonaen-6-ol (E/Z mixture) (hydrochloride salt) (6.2 mg, 28%). $^1$H NMR (400 MHz, DMSO-d6) δ 8.64 (s, 1H), 7.91 (dd, J=7.8, 2.2 Hz, 1H), 7.74 (s, 1H), 7.30 (ddd, J=8.3, 4.4, 2.3 Hz, 1H), 7.13 (dd, J=12.5, 8.3 Hz, 1H), 6.29 (s, 2H), 5.85-5.77 (m, 1H), 5.71 (dd, J=16.1, 4.2 Hz, 1H), 4.54-4.34 (m, 1H), 3.57 (s, 1H), 3.41-3.34 (m, 1H), 3.30-3.22 (m, 2H), 2.21-2.09 (m, 1H), 1.92 (d, J=8.4 Hz, 1H), 1.84-1.63 (m, 2H) ppm. ESI-MS m/z calc. 529.1349, found 530.0 (M+1)⁺; Retention time: 1.78 minutes (LC Method J).

Example 75: Preparation of (12R)-20-amino-18-(benzenesulfonyl)-6-(trifluoromethyl)-22-oxa-3,4,16,21-tetraazatetracyclo[15.3.1.1$^{2,5}$.0$^{12,16}$]docosa-1(20),2,4,17(21),18-pentaen-6-ol (enantiomer 1) (hydrochloride salt) (Compound 140) and (12R)-20-amino-18-(benzenesulfonyl)-6-(trifluoromethyl)-22-oxa-3,4,16,21-tetraazatetracyclo[15.3.1.1$^{2,5}$.0$^{12,16}$]docosa-1(20),2,4,17(21),18-pentaen-6-ol (enantiomer 2) (hydrochloride salt) (Compound 141)

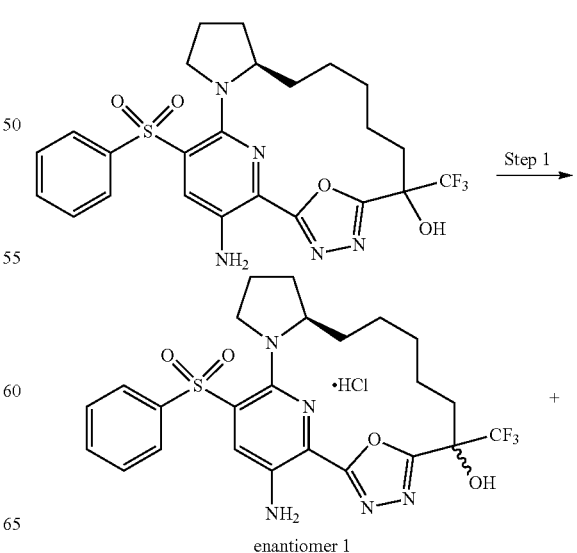

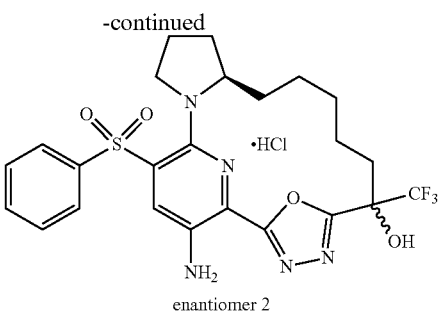

enantiomer 2

Step 1: (12R)-20-Amino-18-(benzenesulfonyl)-6-(trifluoromethyl)-22-oxa-3,4,16,21-tetraazatetracyclo[15.3.1.1².⁵.0¹².¹⁶]docosa-1(20),2,4,17(21),18-pentaen-6-ol (enantiomer 1) (hydrochloride salt) (Compound 140) and (12R)-20-amino-18-(benzenesulfonyl)-6-(trifluoromethyl)-22-oxa-3,4,16,21-tetraazatetracyclo[15.3.1.1².⁵.0¹².¹⁶]docosa-1(20),2,4,17(21),18-pentaen-6-ol (enantiomer 2) (hydrochloride salt) (Compound 141)

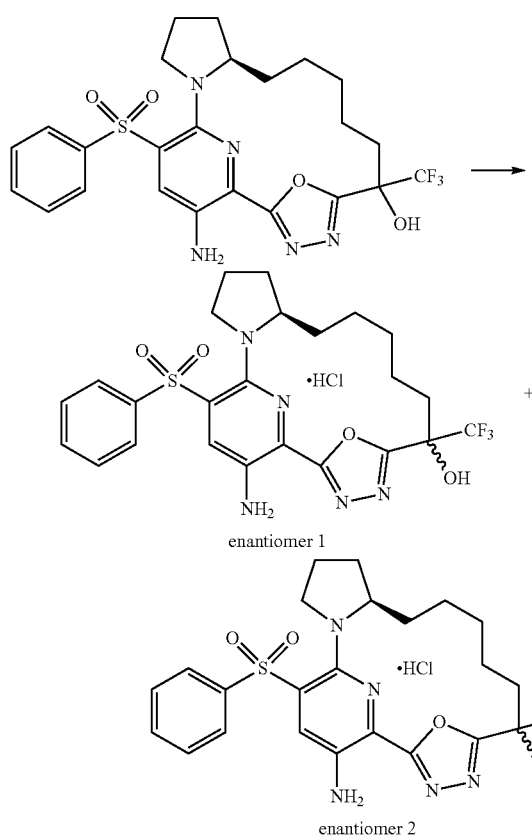

(12R)-20-Amino-18-(benzenesulfonyl)-6-(trifluoromethyl)-22-oxa-3,4,16,21-tetraazatetracyclo[15.3.1.1².⁵.0¹².¹⁶]docosa-1(20),2,4,17(21),18-pentaen-6-ol (17 mg, 0.03162 mmol) was dissolved in MeOH (2 mL) and purified by reverse phase HPLC using a gradient from 30% to 99% acetonitrile in water (+5 mM HCl) over 30 minutes which gave two diastereomeric products:

The first diastereomer to elute was isolated as an orange amorphous solid, (12R)-20-amino-18-(benzenesulfonyl)-6-(trifluoromethyl)-22-oxa-3,4,16,21-tetraazatetracyclo[15.3.1.1².⁵.0¹².¹⁶]docosa-1(20),2,4,17(21),18-pentaen-6-ol (enantiomer 1) (hydrochloride salt) (7.2 mg, 79%). $^1$H NMR (400 MHz, DMSO-d6) δ 8.04 (s, 1H), 7.81 (d, J=7.8 Hz, 2H), 7.72 (t, J=7.4 Hz, 1H), 7.60 (t, J=7.6 Hz, 2H), 3.89-3.76 (m, 2H), 2.98 (dt, J=9.1, 4.5 Hz, 1H), 2.20 (q, J=7.0, 6.5 Hz, 1H), 2.03 (q, J=8.5, 8.0 Hz, 2H), 1.91-1.76 (m, 2H), 1.60 (dddd, J=36.7, 29.0, 14.5, 7.0 Hz, 3H), 1.42-1.33 (m, 2H), 1.26 (h, J=9.5, 8.2 Hz, 3H), 0.42 (dp, J=10.7, 5.2 Hz, 1H) ppm. Three exchangeable protons were not observed. ESI-MS m/z calc. 537.1658, found 538.2 (M+1)$^+$; Retention time: 1.37 minutes (LC Method J).

The second diastereomer to elute was isolated as an orange amorphous solid, (12R)-20-amino-18-(benzenesulfonyl)-6-(trifluoromethyl)-22-oxa-3,4,16,21-tetraazatetracyclo[15.3.1.1².⁵.0¹².¹⁶]docosa-1(20),2,4,17(21),18-pentaen-6-ol (enantiomer 2) (hydrochloride salt) (7.4 mg, 82%). $^1$H NMR (400 MHz, DMSO-d6) δ 8.02 (s, 1H), 7.81 (d, J=7.7 Hz, 2H), 7.72 (t, J=7.4 Hz, 1H), 7.61 (t, J=7.6 Hz, 2H), 3.76 (d, J=8.4 Hz, 2H), 3.02 (td, J=9.1, 3.7 Hz, 1H), 2.18 (t, J=12.1 Hz, 1H), 2.09 (t, J=5.7 Hz, 1H), 1.99 (d, J=10.2 Hz, 2H), 1.83-1.73 (m, 1H), 1.59 (q, J=10.0 Hz, 1H), 1.41 (ddd, J=29.4, 23.4, 7.4 Hz, 6H), 1.26 (dd, J=12.1, 4.0 Hz, 1H), 0.42 (d, J=11.4 Hz, 1H) ppm. Three exchangeable protons were not observed. ESI-MS m/z calc. 537.1658, found 538.2 (M+1)$^+$; Retention time: 1.48 minutes (LC Method J).

Example 76: Preparation of (12R)-20-Amino-6-hydroxy-6-(trifluoromethyl)-22-oxa-3,4,16,21-tetraazatetracyclo[15.3.1.1².⁵.0¹².¹⁶]docosa-1(21),2,4,17,19-pentaene-18-carboxamide (Compound 142)

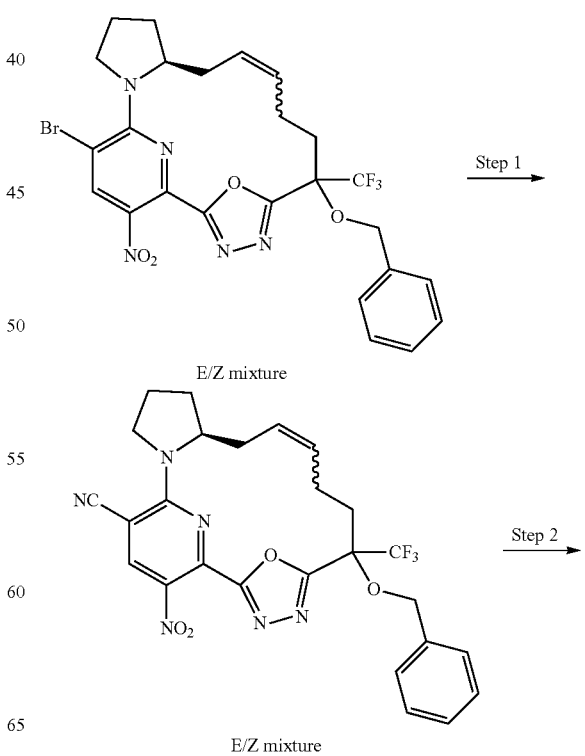

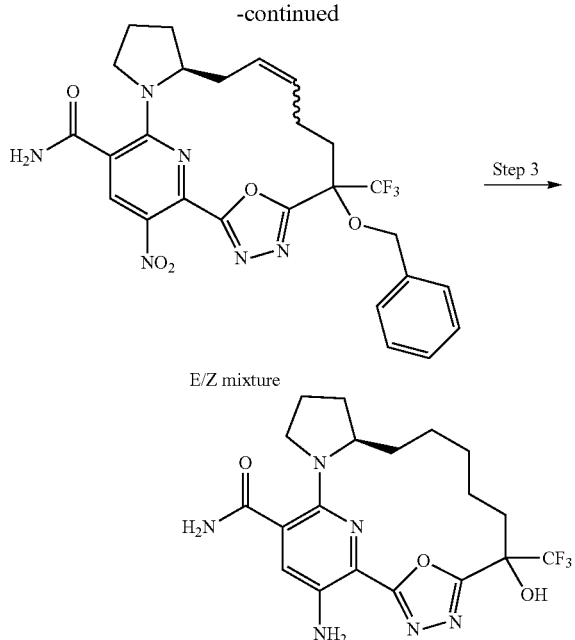

E/Z mixture

Step 1: (12S)-6-(Benzyloxy)-20-nitro-6-(trifluoromethyl)-22-oxa-3,4,16,21-tetraazatetracyclo[15.3.1.12,5.012,16]docosa-1(21),2,4,9,17,19-hexaene-18-carbonitrile (E/Z mixture)

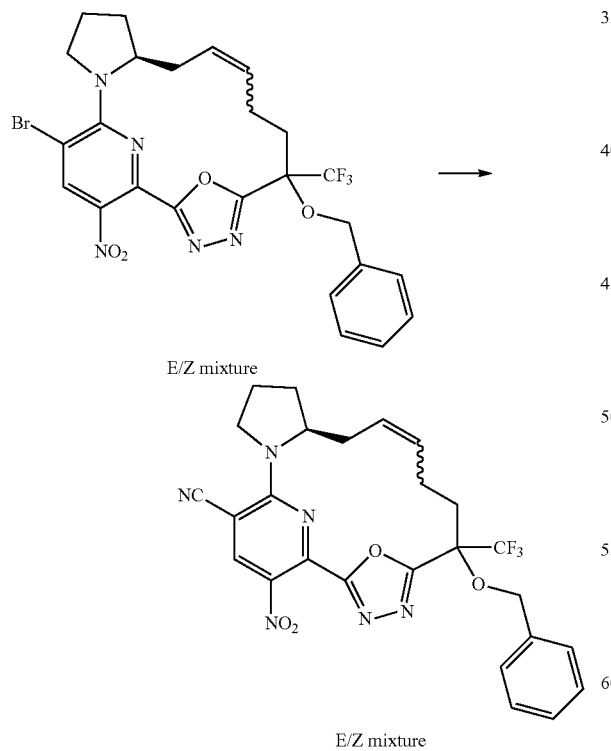

E/Z mixture

A solution of (12S)-6-(benzyloxy)-18-bromo-20-nitro-6-(trifluoromethyl)-22-oxa-3,4,16,21-tetraazatetracyclo[15.3.1.12,5.012,16]docosa-1(21),2,4,9,17,19-hexaene (E/Z mixture) (330 mg, 0.5496 mmol) in DMF (5 mL) in a microwave vial was degassed with nitrogen for 5 minutes, and cyanocopper (349 mg, 3.8967 mmol) was added. The resulting suspension was stirred under nitrogen at 90° C. overnight. The mixture was cooled to room temperature, diluted with water (25 mL) and filtered through a pad of Celite. The filtrate was extracted with ethyl acetate (3×20 mL) and the combined organic layers were washed with brine (2×30 mL), dried over sodium sulfate, filtered and concentrated under reduced pressure. The residue was purified by silica gel chromatography (24 g column) using a gradient from 0% to 25% ethyl acetate in heptanes giving as a yellow solid, (12S)-6-(benzyloxy)-20-nitro-6-(trifluoromethyl)-22-oxa-3,4,16,21-tetraazatetracyclo[15.3.1.12,5.012,16]docosa-1(21),2,4,9,17,19-hexaene-18-carbonitrile (E/Z mixture) (182 mg, 61%). $^1$H NMR (300 MHz, Chloroform-d) δ 8.62 (s, 1H), 7.46-7.27 (m, 5H), 5.71-5.34 (m, 2H), 5.30-5.16 (m, 1H), 5.08-4.87 (m, 1H), 4.30-3.89 (m, 3H), 3.39-3.10 (m, 1H), 2.57-1.84 (m, 8H), 1.79-1.46 (m, 1H) ppm. $^{19}$F NMR (282 MHz, Chloroform-d) δ −73.07 (s, 3F), −73.59 (s, 3F) ppm. ESI-MS m/z calc. 540.1733, found 541.2 (M+1)$^+$; Retention time: 2.44 minutes (LC Method E).

Step 2: (12S)-6-(Benzyloxy)-20-nitro-6-(trifluoromethyl)-22-oxa-3,4,16,21-tetraazatetracyclo[15.3.1.12, 5.012,16]docosa-1(21),2,4,9,17,19-hexaene-18-carboxamide (E/Z mixture)

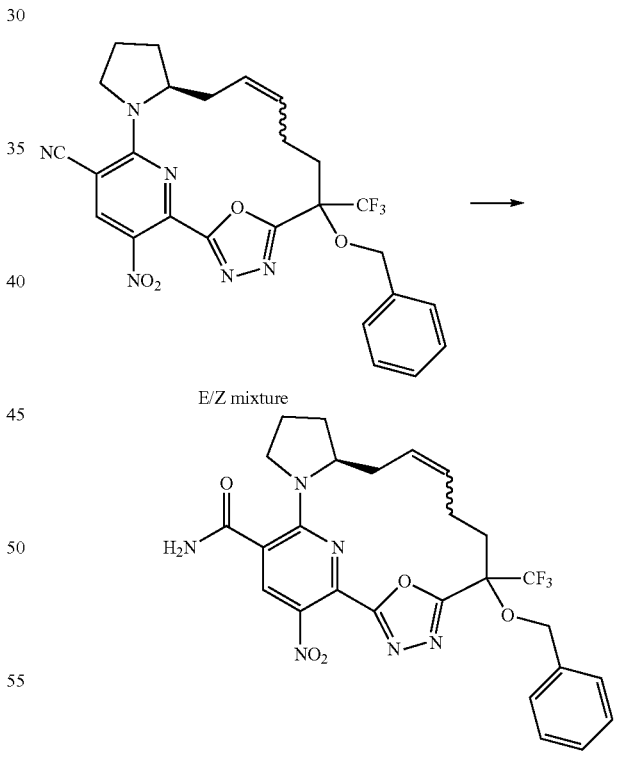

E/Z mixture

To a solution of (12S)-6-(benzyloxy)-20-nitro-6-(trifluoromethyl)-22-oxa-3,4,16,21-tetraazatetracyclo[15.3.1.12, 5.012,16]docosa-1(21),2,4,9,17,19-hexaene-18-carbonitrile (E/Z mixture) (50 mg, 0.0925 mmol) in EtOH (4.5 mL) and water (0.5 mL) was added Ghaffar-Parkins catalyst (PtHiPMe$_2$OH) (2 mg, 0.0047 mmol). The reaction was heated at 70° C. for 4 hours and cooled to room temperature.

The reaction was concentrated and the residue was purified by silica gel chromatography (4 g column) using a gradient from 0% to 60% ethyl acetate in heptanes which afforded (12S)-6-(benzyloxy)-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene-18-carboxamide (E/Z mixture) (32 mg, 62%). ¹H NMR (300 MHz, Chloroform-d) δ 8.44-8.27 (m, 1H), 7.52-7.20 (m, 5H), 6.89-6.60 (m, 1H), 5.76 (br. s., 1H), 5.64-5.31 (m, 2H), 5.28-5.09 (m, 1H), 5.01-4.81 (m, 1H), 3.99 (d, J=6.8 Hz, 1H), 3.83-3.57 (m, 1H), 3.52-3.14 (m, 2H), 2.64-1.68 (m, 8H), 1.16-0.98 (m, 1H) ppm. ¹⁹F NMR (282 MHz, Chloroform-d) δ−72.96 (br. s., 3F), −73.46 (br. s., 3F) ppm. ESI-MS m/z calc. 558.18384, found 559.0 (M+1)⁺; Retention time: 2.21 minutes (LC Method E).

Step 3: (12R)-20-Amino-6-hydroxy-6-(trifluoromethyl)-22-oxa-3,4,16,21-tetraazatetracyclo[15.3.1.1²,⁵.0¹²,¹⁶]docosa-1(21),2,4,17,19-pentaene-18-carboxamide (Compound 142)

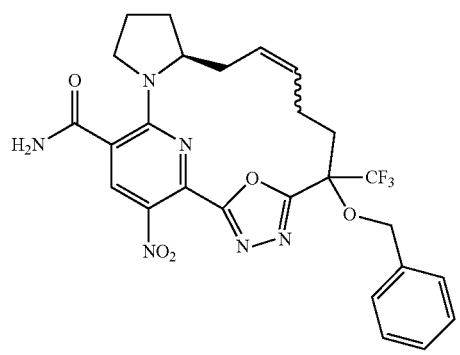

E/Z mixture

A solution of (12S)-6-(benzyloxy)-20-nitro-6-(trifluoromethyl)-22-oxa-3,4,16,21-tetraazatetracyclo[15.3.1.1²,⁵.0¹²,¹⁶]docosa-1(21),2,4,9,17,19-hexaene-18-carboxamide (E/Z mixture) (32 mg, 0.0573 mmol) in methanol (5 mL) was put under nitrogen atmosphere and palladium on carbon (30 mg, 5% w/w, 0.0141 mmol) was added. The reaction was put under hydrogen atmosphere and stirred overnight. The reaction was put under nitrogen atmosphere and filtered through Celite. The filtrate was concentrated and the residue was purified by silica gel chromatography (12 g column) using a gradient from 40% to 100% ethyl acetate in heptanes. The residue was further purified by reverse phase HPLC using a gradient from 30% to 50% acetonitrile in water (+10 mM NH₄HCO₃) over 19 minutes giving as a yellow solid and mixture of diastereomers, (12R)-20-amino-6-hydroxy-6-(trifluoromethyl)-22-oxa-3,4,16,21-tetraazatetracyclo[15.3.1.1²,⁵.0¹²,¹⁶]docosa-1(21),2,4,17,19-pentaene-18-carboxamide (11 mg, 43%). ¹H NMR (300 MHz, Chloroform-d) δ 7.63-7.37 (m, 1H), 6.97-6.59 (m, 1H), 6.28-5.82 (m, 1H), 5.08 (br. s., 2H), 4.52-4.11 (m, 1H), 4.04-3.80 (m, 1H), 3.79-3.56 (m, 1H), 3.13-2.86 (m, 1H), 2.75-1.32 (m, 12H), 1.18-0.77 (m, 2H) ppm. ¹⁹F NMR (282 MHz, Chloroform-d) δ−77.35 (br. s., 3F, minor diastereomer), −80.65 (s, 3F, major diastereomer) ppm. ESI-MS m/z calc. 440.17838, found 441.0 (M+1)⁺; Retention time: 2.72 minutes (LC Method C).

Example 77: Preparation of (12R)-20-amino-18-[4-(trifluoromethoxy)benzenesulfonyl]-6-(trifluoromethyl)-22-oxa-3,4,16,21-tetraazatetracyclo[15.3.1.1²,⁵.0¹²,¹⁶]docosa-1(20),2,4,17(21),18-pentaen-6-ol (Compound 143)

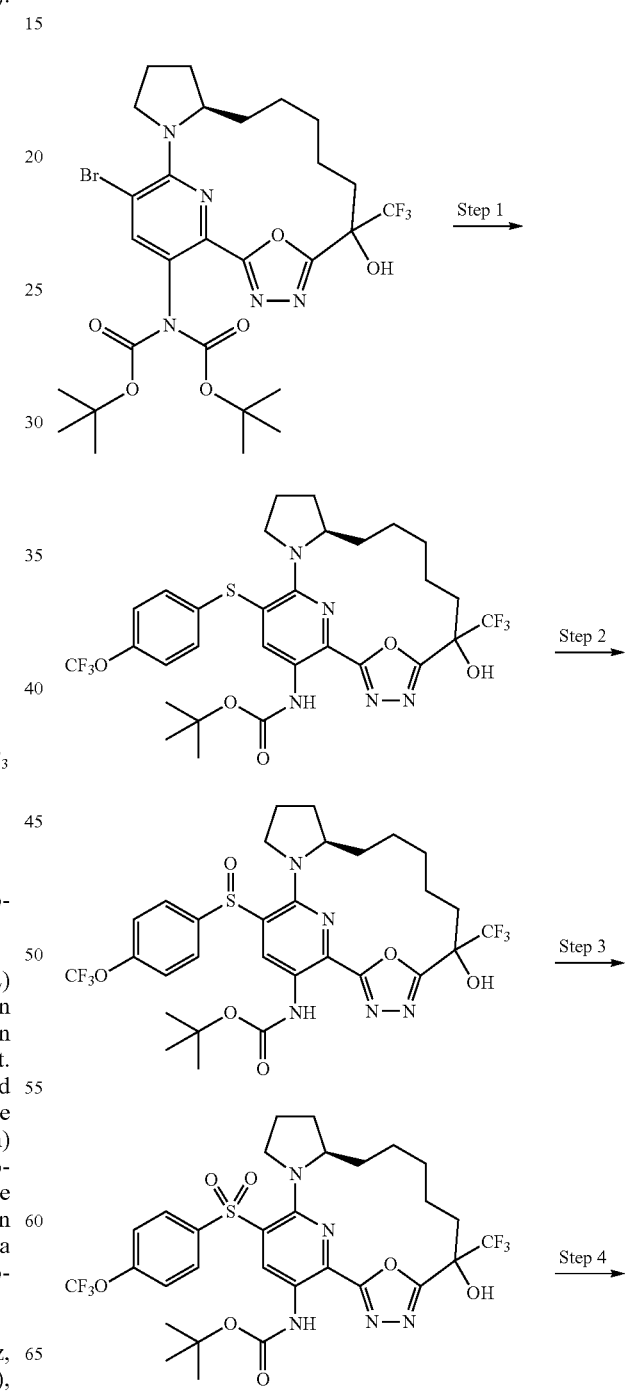

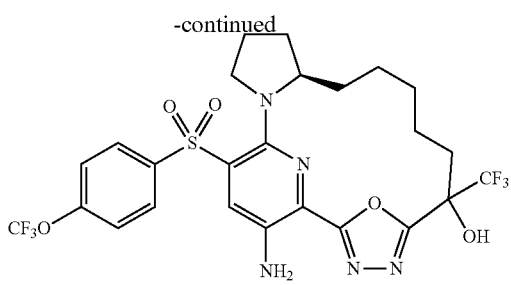

Step 1: tert-Butyl N-[(12R)-6-hydroxy-18-{[4-(trifluoromethoxy)phenyl]sulfanyl}-6-(trifluoromethyl)-22-oxa-3,4,16,21-tetraazatetracyclo[15.3.1.12,5.012,16]docosa-1(21),2,4,17,19-pentaen-20-yl]carbamate

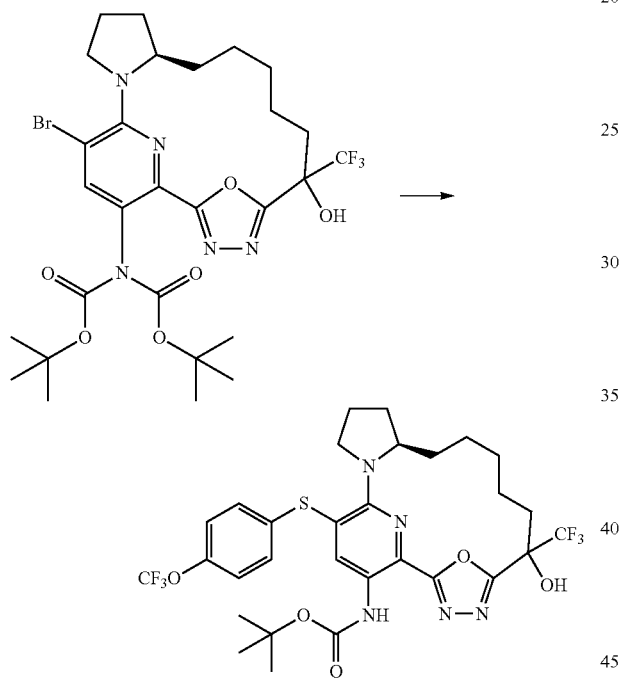

To a solution of tert-butyl N-[(12R)-18-bromo-6-hydroxy-6-(trifluoromethyl)-22-oxa-3,4,16,21-tetraazatetracyclo[15.3.1.12,5.012,16]docosa-1(21),2,4,17,19-pentaen-20-yl]-N-[(tert-butoxy)carbonyl]carbamate (100 mg, 0.1478 mmol) in dioxane (2 mL) was added cesium carbonate (100 mg, 0.3069 mmol) and the mixture was degassed for 10 minutes with nitrogen. 4-(Trifluoromethoxy) benzenethiol (70 mg, 0.3605 mmol) was added to the reaction mixture and degassed the mixture again for 5 minutes with nitrogen. Xantphos (18 mg, 0.0311 mmol) and then $Pd_2(dba)_3$ (14 mg, 0.0153 mmol) were added to the reaction mixture, then degassed for 2 minutes with nitrogen and heated the mixture overnight at 100° C. The reaction mixture was cooled to room temperature and water (25 mL) was added. This mixture was extracted with dichloromethane (2×25 mL) and the combined organic layers were dried over sodium sulfate, filtered and the solvent was evaporated. The residue was purified by silica gel chromatography using a gradient from 0% to 10% ethyl acetate in heptanes. The residue was further purified by reverse phase HPLC using a gradient from 5% to 100% acetonitrile in water (+0.1% formic acid) over 30 minutes giving as a yellow foam, tert-butyl N-[(12R)-6-hydroxy-18-{[4-(trifluoromethoxy)phenyl]sulfanyl}-6-(trifluoromethyl)-22-oxa-3,4,16,21-tetraazatetracyclo [15.3.1.12,5.012,16]docosa-1(21),2,4,17,19-pentaen-20-yl] carbamate (48 mg, 47%). Retention time: 2.97 minutes (LC Method W).

Step 2: tert-Butyl N-[(12R)-6-hydroxy-18-[4-(trifluoromethoxy)benzenesulfinyl]-6-(trifluoromethyl)-22-oxa-3,4,16,21-tetraazatetracyclo[15.3.1.12,5.012,16]docosa-1(21),2,4,17,19-pentaen-20-yl]carbamate

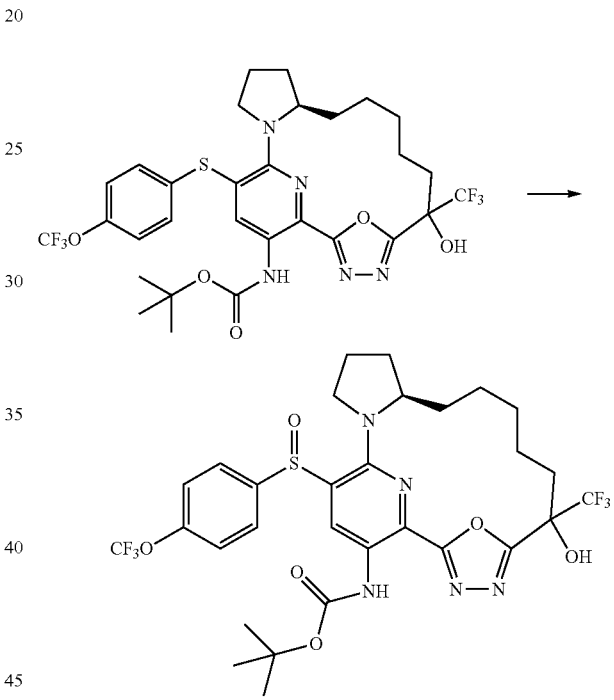

To a solution of tert-butyl N-[(12R)-6-hydroxy-18-{[4-(trifluoromethoxy)phenyl]sulfanyl}-6-(trifluoromethyl)-22-oxa-3,4,16,21-tetraazatetracyclo[15.3.1.12,5.012,16]docosa-1(21),2,4,17,19-pentaen-20-yl]carbamate (20 mg, 0.029 mmol) in dichloromethane (1 mL) was added 3-chloroperbenzoic acid (7 mg, 0.0312 mmol) at 0° C. under nitrogen and the resulting mixture was stirred at 0° C. for under nitrogen for 1 hour. The mixture was quenched with an aqueous solution of sodium bicarbonate (15 mL) at 0° C. The mixture was extracted with dichloromethane (2×15 mL). The combined organic layers were dried over sodium sulfate, filtered and concentrated. The residue was purified by silica gel chromatography using a gradient from 0% to 30% ethyl acetate in heptanes to afford as a yellow solid, tert-butyl N-[(12R)-6-hydroxy-18-[4-(trifluoromethoxy) benzenesulfinyl]-6-(trifluoromethyl)-22-oxa-3,4,16,21-tetraazatetracyclo[15.3.1.12,5.012,16]docosa-1(21),2,4,17,19-pentaen-20-yl]carbamate (19 mg, 93%). Retention time: 2.53 minutes (LC Method W).

Step 3: tert-Butyl N-[(12R)-6-hydroxy-18-[4-(trifluoromethoxy)benzenesulfinyl]-6-(trifluoromethyl)-22-oxa-3,4,16,21-tetraazatetracyclo[15.3.1.1²,⁵.0¹²,¹⁶]docosa-1(21),2,4,17,19-pentaen-20-yl]carbamate Step 4: (12R)-20-Amino-18-[4-(trifluoromethoxy)benzenesulfonyl]-6-(trifluoromethyl)-22-oxa-3,4,16,21-tetraazatetracyclo[15.3.1.1²,⁵.0¹²,¹⁶]docosa-1(20),2,4,17(21),18-pentaen-6-ol (Compound 143)

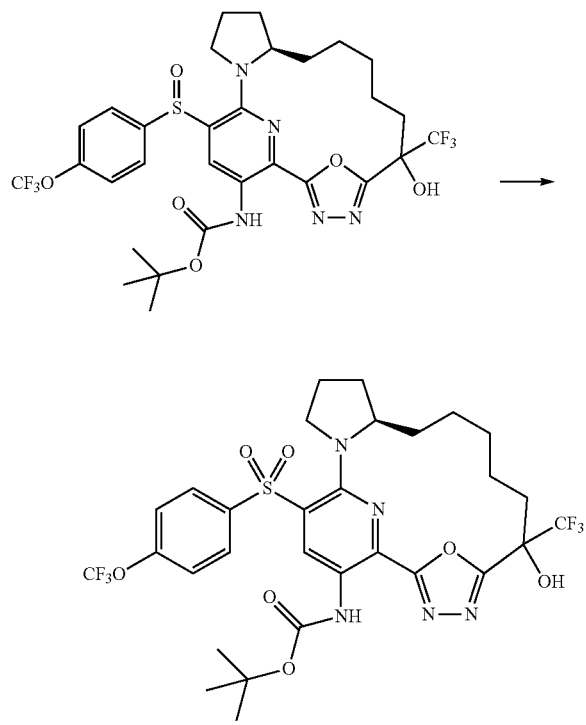

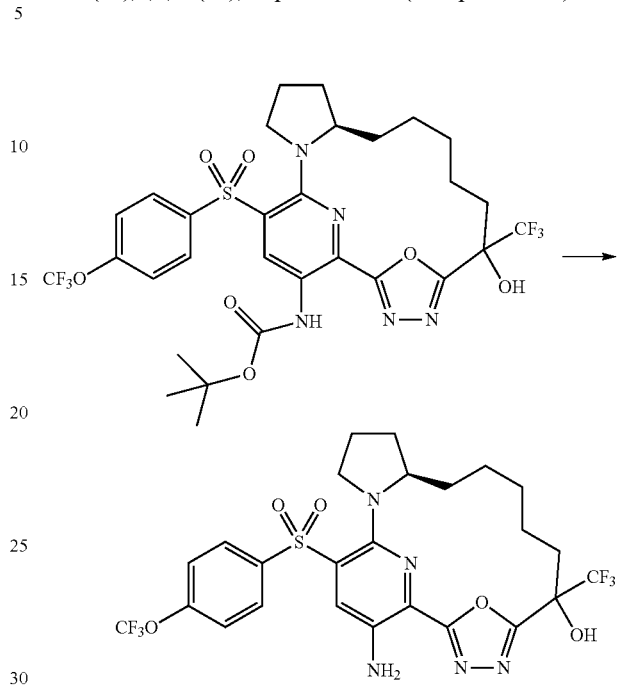

To a solution of tert-butyl N-[(12R)-6-hydroxy-18-[4-(trifluoromethoxy)benzenesulfinyl]-6-(trifluoromethyl)-22-oxa-3,4,16,21-tetraazatetracyclo[15.3.1.1²,⁵.0¹²,¹⁶]docosa-1(21),2,4,17,19-pentaen-20-yl]carbamate (55 mg, 0.0779 mmol) in dichloromethane (3 mL) was added 3-chloroperbenzoic acid (18 mg, 0.0803 mmol) at 0° C. under nitrogen and then the resulting mixture was stirred at room temperature for 2 hours. The mixture was quenched with an aqueous solution of sodium bicarbonate (15 mL). The mixture was extracted with dichloromethane (2×15 mL). The combined organic layers were dried over sodium sulfate, filtered and concentrated. The residue was purified by silica gel chromatography using a gradient from 0% to 5% methanol in dichloromethane. The residue was further purified by reverse phase HPLC using a gradient from 5% to 90% acetonitrile in water (+0.1% formic acid) giving as a yellow foam, tert-butyl N-[(12R)-6-hydroxy-18-[4-(trifluoromethoxy)benzenesulfonyl]-6-(trifluoromethyl)-22-oxa-3,4,16,21-tetraazatetracyclo[15.3.1.1²,⁵.0¹²,¹⁶]docosa-1(21),2,4,17,19-pentaen-20-yl]carbamate (43 mg, 55%). ESI-MS m/z calc. 721.2005, found 722.0 (M+1)⁺; Retention time: 1.8 minutes (LC Method Z).

A solution of tert-butyl N-[(12R)-6-hydroxy-18-[4-(trifluoromethoxy)benzenesulfonyl]-6-(trifluoromethyl)-22-oxa-3,4,16,21-tetraazatetracyclo[15.3.1.1²,⁵.0¹²,¹⁶]docosa-1(21),2,4,17,19-pentaen-20-yl]carbamate (10 mg, 0.0139 mmol) in a pre-made solution of TFA (0.5 mL) and dichloromethane (0.5 mL) was stirred at room temperature for 1 hour. The mixture was quenched with aqueous sodium bicarbonate (15 mL) with a slow addition at room temperature and then it was extracted with dichloromethane (2×15 mL). The combined organic layers were dried over sodium sulfate, filtered and concentrated. The residue was purified by silica gel chromatography (4 g column) using a gradient from 0% to 5% methanol in dichloromethane giving as a pale yellow solid and mixture of diastereomers, (12R)-20-amino-18-[4-(trifluoromethoxy)benzenesulfonyl]-6-(trifluoromethyl)-22-oxa-3,4,16,21-tetraazatetracyclo[15.3.1.1²,⁵.0¹²,¹⁶]docosa-1(20),2,4,17(21),18-pentaen-6-ol (7 mg, 53%). ¹H NMR (300 MHz, Chloroform-d) δ 8.11 (br. s., 1H), 8.05 (d, J=8.5 Hz, 2H), 7.16 (d, J=7.6 Hz, 2H), 6.46-5.84 (m, 2H), 4.86-4.03 (m, 2H), 3.74-3.64 (m, 1H), 2.76-2.50 (m, 1H), 2.35-2.14 (m, 4H), 1.90-1.42 (m, 9H), 0.95-0.83 (m, 1H) ppm. ¹⁹F NMR (282 MHz, Chloroform-d) δ −57.76 (br. s., 3F, —OCF₃ of both diastereomers), −77.56 (br. s., 3F, minor diastereomer), −80.53 (s, 3F, major diastereomer) ppm. ESI-MS m/z calc. 621.1481, found 620.0 (M−1)⁺; Retention time: 3.08 minutes (LC Method AA).

Example 78: Preparation of (12R)-20-amino-18-bromo-6-(trifluoromethyl)-22-oxa-3,4,16,21-tetraazatetracyclo[15.3.1.1²,⁵.0¹²,¹⁶]docosa-1(21),2,4,17,19-pentaen-6-ol (Compound 144)

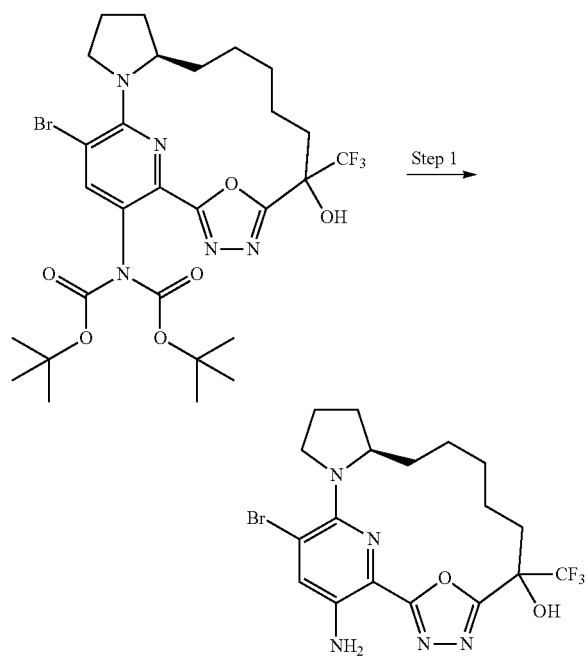

Step 1: (12R)-20-Amino-18-bromo-6-(trifluoromethyl)-22-oxa-3,4,16,21-tetraazatetracyclo[15.3.1.1²,⁵.0¹²,¹⁶]docosa-1(21),2,4,17,19-pentaen-6-ol (Compound 144)

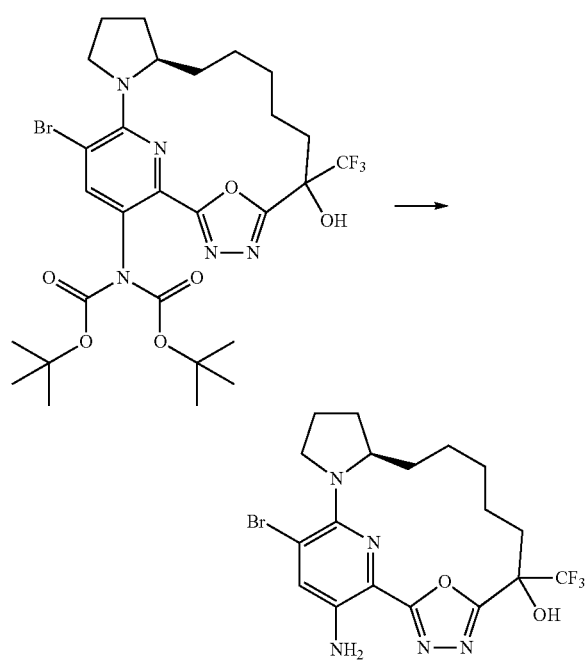

A solution of tert-butyl N-[(12R)-18-bromo-6-hydroxy-6-(trifluoromethyl)-22-oxa-3,4,16,21-tetraazatetracyclo[15.3.1.1²,⁵.0¹²,¹⁶]docosa-1(21),2,4,17,19-pentaen-20-yl]-N-[(tert-butoxy)carbonyl]carbamate (25 mg, 0.037 mmol) in 1:1 mixture of trifluoroacetic acid (0.5 mL) and dichloromethane (0.5 mL) was stirred at room temperature for 2 hours. The mixture was quenched with aqueous sodium bicarbonate (15 mL) with slow addition and then it was extracted with dichloromethane (2×15 mL). Combined organic layers then dried over sodium sulfate, filtered and concentrated. The residue was purified by silica gel chromatography (4 g column) using a gradient from 0% to 25% ethyl acetate in heptanes giving as a yellow solid, (12R)-20-amino-18-bromo-6-(trifluoromethyl)-22-oxa-3,4,16,21-tetraazatetracyclo[15.3.1.1²,⁵.0¹²,¹⁶]docosa-1(21),2,4,17,19-pentaen-6-ol (12 mg, 68%). $^1$H NMR (400 MHz, DMSO-d6) δ 7.63-7.61 (m, 1H), 4.04-3.82 (m, 2H), 3.80-3.39 (m, 3H), 3.36-3.26 (m, 1H), 2.45-2.19 (m, 2H), 2.19-2.09 (m, 1H), 2.07-1.84 (m, 2H), 1.79-1.66 (m, 1H), 1.65-1.29 (m, 7H), 0.93-0.77 (m, 1H) ppm. $^{19}$F NMR (377 MHz, DMSO-d6) δ −76.40 (s, 3F, minor diastereomer), −79.30 (s, 3F, major diastereomer) ppm. ESI-MS m/z calc. 475.08307, found 476.1 (M+1)$^+$; Retention time: 4.93 minutes (LC Method AA).

Example 79: Preparation of (12R)-20-amino-18-[4-(trifluoromethoxy)benzenesulfinyl]-6-(trifluoromethyl)-22-oxa-3,4,16,21-tetraazatetracyclo[15.3.1.1²,⁵.0¹²,¹⁶]docosa-1(21),2,4,17,19-pentaen-6-ol (Compound 145)

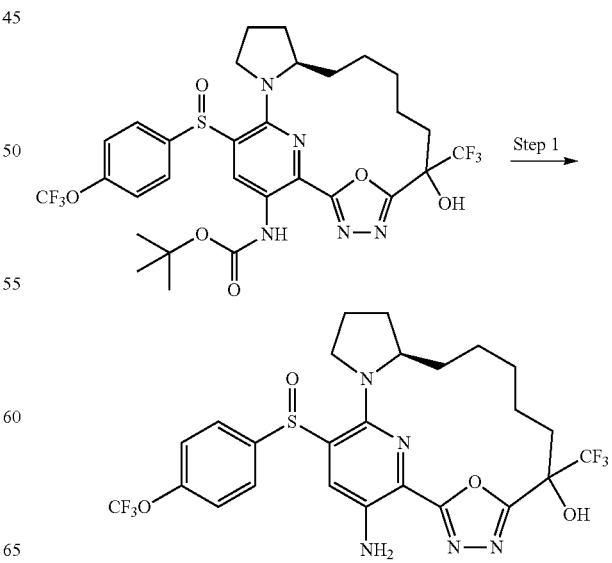

Step 1: (12R)-20-Amino-18-[4-(trifluoromethoxy)benzenesulfinyl]-6-(trifluoromethyl)-22-oxa-3,4,16,21-tetraazatetracyclo[15.3.1.1²,⁵.0¹²,¹⁶]docosa-1(21),2,4,17,19-pentaen-6-ol (Compound 145)

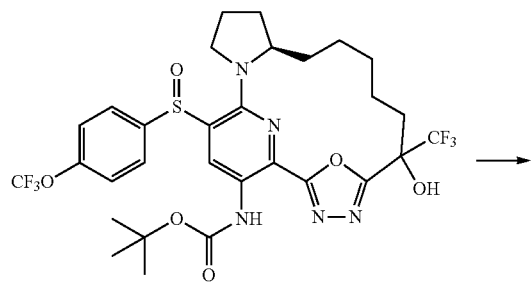

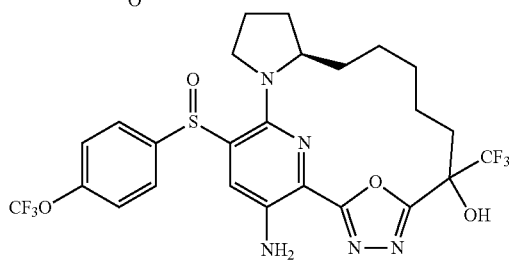

A solution of tert-butyl N-[(12R)-6-hydroxy-1844-(trifluoromethoxy)benzenesulfinyl]-6-(trifluoromethyl)-22-oxa-3,4,16,21-tetraazatetracyclo[15.3.1.1²,⁵.0¹²,¹⁶]docosa-1(21),2,4,17,19-pentaen-20-yl]carbamate (17 mg, 0.0241 mmol) in a 1:1 mixture of trifluoroacetic acid (0.5 mL) and dichloromethane (0.5 mL) was stirred at room temperature for 2 hours. The mixture was quenched with an aqueous sodium bicarbonate solution (15 mL) with slow addition and then it was extracted with dichloromethane (2×15 mL). Combined organic layers were dried over sodium sulfate, filtered and concentrated. The residue was purified by silica gel chromatography using a gradient from 0% to 40% ethyl acetate in heptanes giving as a light orange solid and mixture of diastereomers, (12R)-20-amino-18-[4-(trifluoromethoxy)benzenesulfinyl]-6-(trifluoromethyl)-22-oxa-3,4,16,21-tetraazatetracyclo[15.3.1.1²,⁵.0¹²,¹⁶]docosa-1(21),2,4,17,19-pentaen-6-ol (11 mg, 75%). ESI-MS m/z calc. 605.15314, found 606.2 (M+1)⁺; Retention time: 4.8 minutes (LC Method AA).

Example 80: Preparation of (12R)-20-amino-18-{[4-(trifluoromethoxy)phenyl]sulfanyl}-6-(trifluoromethyl)-22-oxa-3,4,16,21-tetraazatetracyclo[15.3.1.1²,⁵.0¹²,¹⁶]docosa-1(21),2,4,17,19-pentaen-6-ol (Compound 146)

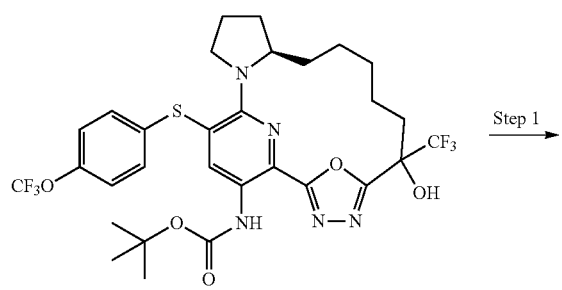

Step 1: (12R)-20-Amino-18-{[4-(trifluoromethoxy)phenyl]sulfanyl}-6-(trifluoromethyl)-22-oxa-3,4,16,21-tetraazatetracyclo[15.3.1.1²,⁵.0¹²,¹⁶]docosa-1(21),2,4,17,19-pentaen-6-ol (Compound 146)

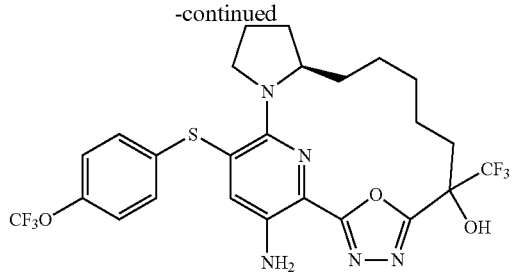

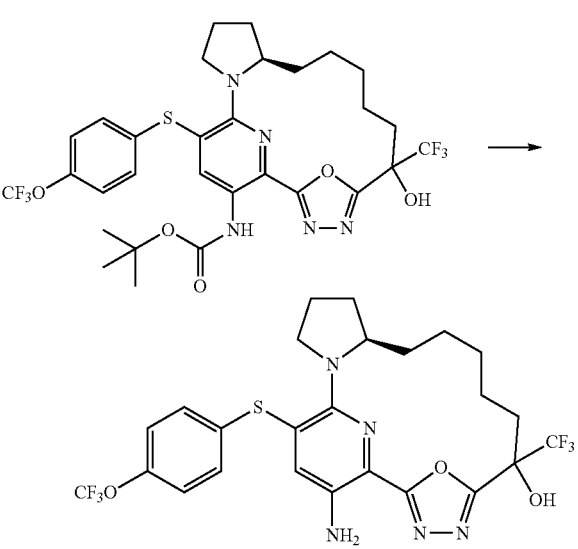

A solution of tert-butyl N-[(12R)-6-hydroxy-18-{[4-(trifluoromethoxy)phenyl]sulfanyl}-6-(trifluoromethyl)-22-oxa-3,4,16,21-tetraazatetracyclo[15.3.1.1²,⁵.0¹²,¹⁶]docosa-1(21),2,4,17,19-pentaen-20-yl]carbamate (26 mg, 0.0377 mmol) in a 1:1 mixture of trifluoroacetic acid (0.5 mL) and dichloromethane (0.5 mL) was stirred at room temperature for 2 hours. The mixture was quenched with an aqueous sodium bicarbonate solution (15 mL) with slow addition and then it was extracted with dichloromethane (2×15 mL). Combined organic layers were dried over sodium sulfate, filtered and concentrated. The residue was purified by silica gel chromatography using a gradient from 0% to 25% ethyl acetate in heptanes giving as a yellow solid, (12R)-20-amino-18-{[4-(trifluoromethoxy)phenyl]sulfanyl}-6-(trifluoromethyl)-22-oxa-3,4,16,21-tetraazatetracyclo[15.3.1.1²,⁵.0¹²,¹⁶]docosa-1(21),2,4,17,19-pentaen-6-ol (15 mg, 67%). ¹H NMR (400 MHz, DMSO-d6) δ 7.65-7.45 (m, 1H), 7.44-7.35 (m, 4H), 7.2-7.09 (m, 1H), 4.08-3.57 (m, 3H), 3.39-3.20 (m, 1H), 2.40-2.19 (m, 2H), 2.16-1.91 (m, 2H), 1.89-1.79 (m, 1H), 1.77-1.58 (m, 2H), 1.55-1.33 (m, 5H), 1.30-1.18 (m, 2H), 0.85-0.71 (m, 1H) ppm. ¹⁹F NMR (377 MHz, DMSO-d6) δ −56.84 to −56.86 (m, 3F, —CF₃ of both diastereomers), −76.38 (br s, 3F, minor diastereomer), −79.27 (br s, 3F, major diastereomer) ppm. ESI-MS m/z calc. 589.1582, found 590.2 (M+1)⁺; Retention time: 5.43 minutes (LC Method AA).

Example 81: Preparation of (12S)-20-amino-6,18-bis(trifluoromethyl)-10,22-dioxa-3,4,16,21-tetraaza-tetracyclo[15.3.1.1²,⁵.0¹²,¹⁶]docosa-1(21),2,4,17,19-pentaen-6-ol (Compound 147)
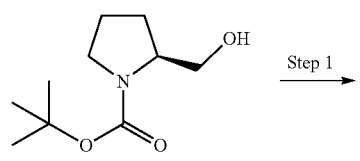
Step 1 →
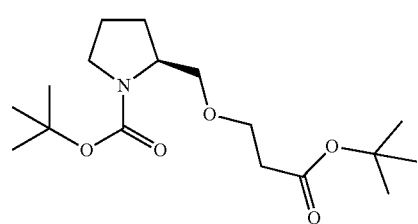
Step 2 →
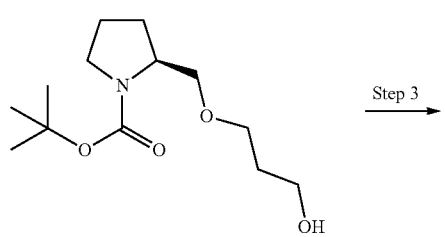
Step 3 →
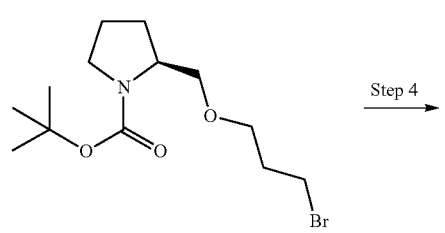
Step 4 →
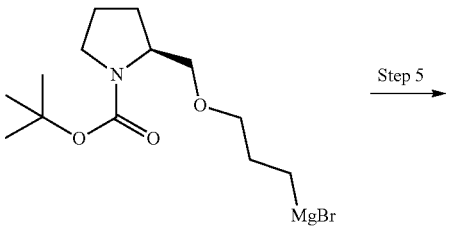
Step 5 →
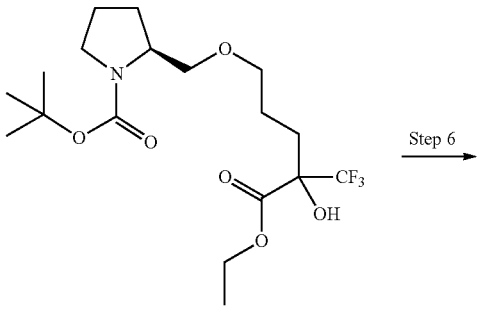
Step 6 →
-continued
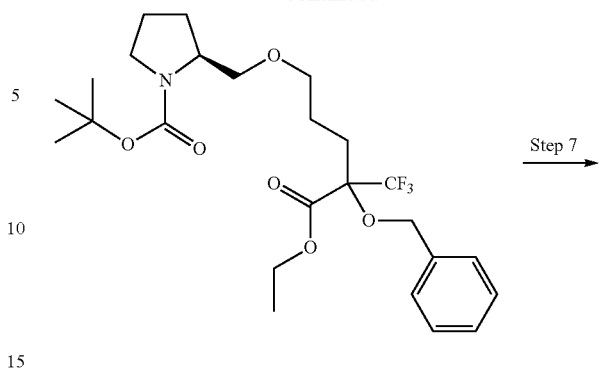
Step 7 →
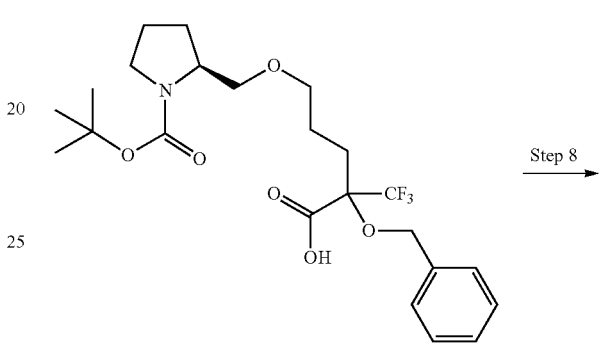
Step 8 →
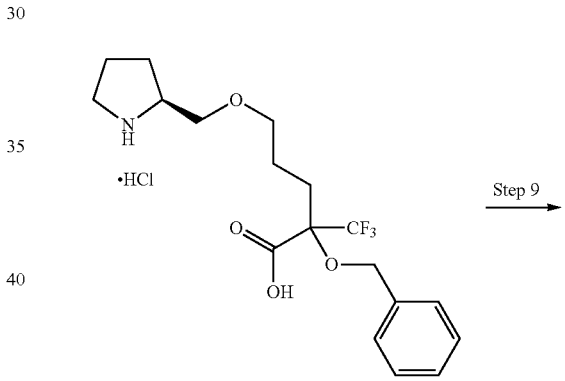
Step 9 →
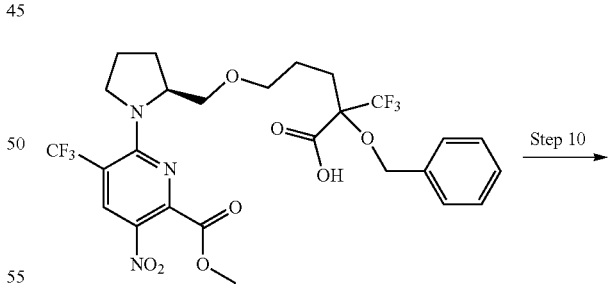
Step 10 →
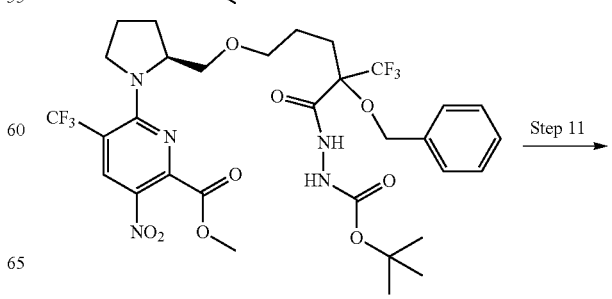
Step 11 →

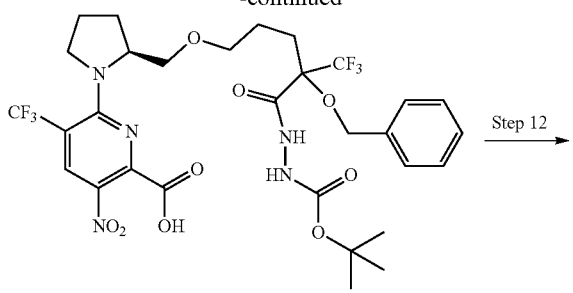

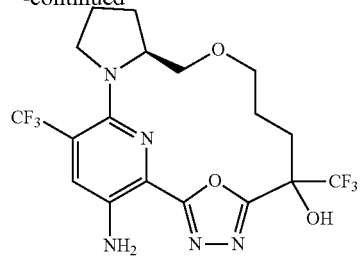

Step 1: tert-Butyl (2S)-2-[(3-tert-butoxy-3-oxo-propoxy)methyl]pyrrolidine-1-carboxylate

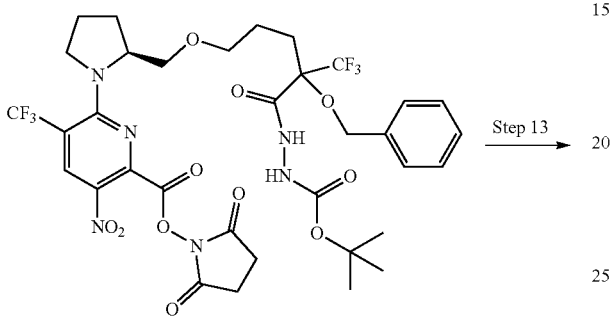

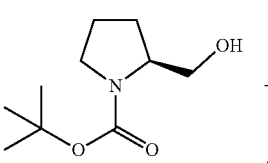

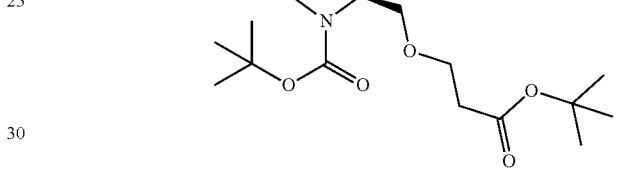

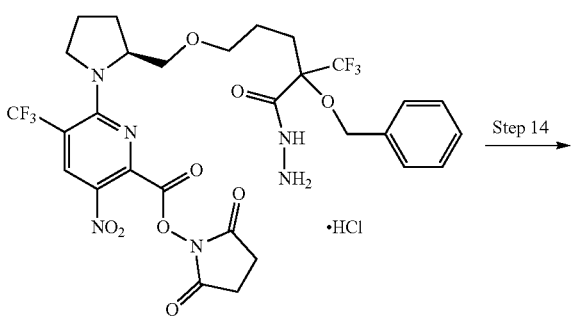

A solution of tert-butyl (2S)-2-(hydroxymethyl)pyrrolidine-1-carboxylate (4.03 g, 20.024 mmol) in acetonitrile (50 mL) was treated successively with tert-butyl prop-2-enoate (13.125 g, 15 mL, 102.4 mmol) and an aqueous solution of benzyltrimethylammonium hydroxide (1.952 g, 40% w/w, 4.6685 mmol) and stirred at room temperature. After 3 hours, the reaction mixture was transferred to a 1.0 L separatory funnel with water (250 mL) and extracted with MTBE (3×250 mL). The combined organic layers were washed with brine (150 mL), dried over sodium sulfate, filtered and concentrated under reduced pressure. The residue was purified by silica gel chromatography using a gradient from 0% to 25% ethyl acetate in heptanes to afford as a colorless oil, tert-butyl (2S)-2-[(3-tert-butoxy-3-oxo-propoxy)methyl]pyrrolidine-1-carboxylate (5.88 g, 89%). $^1$H NMR (300 MHz, DMSO-d6) δ 3.75 (br. s., 1H), 3.67-3.48 (m, 2H), 3.42 (d, J=9.1 Hz, 1H), 3.26 (dd, J=9.1, 7.6 Hz, 1H), 3.22-3.12 (m, 2H), 2.40 (t, J=5.9 Hz, 2H), 1.91-1.66 (m, 4H), 1.39 (s, 18H) ppm. ESI-MS m/z calc. 329.2202, found 352.2 (M+23)$^+$; Retention time: 2.23 minutes (LC Method E).

Step 2: tert-Butyl (2S)-2-(3-hydroxypropoxymethyl)pyrrolidine-1-carboxylate

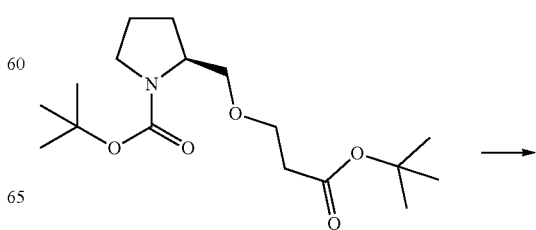

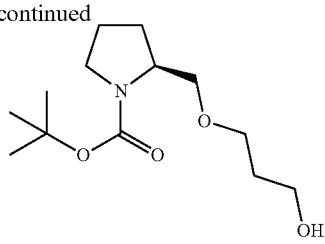

A solution of tert-butyl (2S)-2-[(3-tert-butoxy-3-oxo-propoxy)methyl]pyrrolidine-1-carboxylate (362 mg, 1.0989 mmol) in THF (6 mL) was cooled in an ice-bath and treated slowly with a dichloromethane solution of diisobutylaluminum hydride (3.4 mL of 1 M, 3.4 mmol). After 20 minutes, the flask was removed from the ice-bath and the mixture was stirred at room temperature for about 2 hours. Cooled again in an ice-bath and the reaction was quenched slowly with an aqueous solution of Rochelle's salt (20 mL). Added some MTBE (25 mL) and stirred vigorously at room temperature for 1 hour. Transferred to a 125 mL separatory funnel and the layers were separated. The aqueous layer was then extracted again with MTBE (2×25 mL). The combined organic layers were washed with brine (25 mL), dried over sodium sulfate, filtered and concentrated under reduced pressure. The residue was purified by silica gel chromatography using a gradient from 0% to 70% ethyl acetate in heptanes to afford as a colorless oil, tert-butyl (2S)-2-(3-hydroxypropoxymethyl)pyrrolidine-1-carboxylate (191 mg, 67%). $^1$H NMR (300 MHz, Chloroform-d) δ 4.01-3.89 (m, 1H), 3.76 (t, J=5.6 Hz, 2H), 3.65 (t, J=5.7 Hz, 2H), 3.57 (dd, J=9.5, 4.0 Hz, 1H), 3.42-3.28 (m, 3H), 2.27 (br. s., 1H), 1.98-1.75 (m, 6H), 1.47 (s, 9H) ppm. ESI-MS m/z calc. 259.1784, found 282.2 (M+23)$^+$; Retention time: 1.71 minutes (LC Method E).

Step 3: tert-Butyl (2S)-2-(3-bromopropoxymethyl)pyrrolidine-1-carboxylate

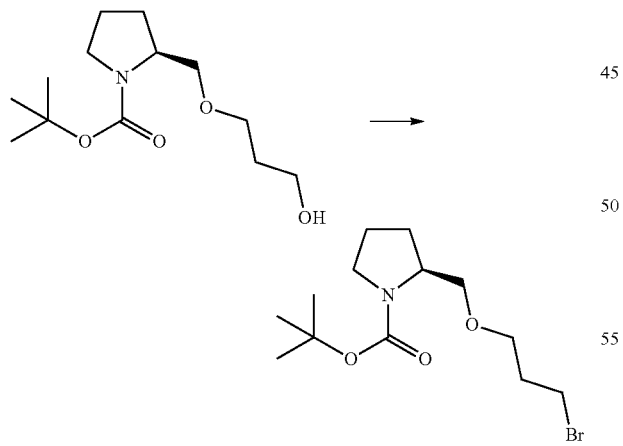

A solution of tert-butyl (2S)-2-(3-hydroxypropoxymethyl)pyrrolidine-1-carboxylate (191 mg, 0.7365 mmol) and triphenylphosphine (215 mg, 0.8197 mmol) in dichloromethane (4 mL) was cooled in an ice-bath and treated with carbon tetrabromide (272 mg, 0.8202 mmol). The reaction was left to gradually warm to room temperature while maintaining in the cold bath over a period of 4 hours, then stirred overnight (16 h) at room temperature. The crude reaction mixture was then treated with silica gel and concentrated under reduced pressure. Purified by silica gel chromatography using a gradient from 0% to 15% ethyl acetate in heptanes to afford as a clear colorless oil, tert-butyl (2S)-2-(3-bromopropoxymethyl)pyrrolidine-1-carboxylate (172 mg, 70%). $^1$H NMR (300 MHz, Chloroform-d) δ 4.02-3.81 (m, 1H), 3.68-3.44 (m, 5H), 3.42-3.19 (m, 3H), 2.09 (quin, J 6.2 Hz, 2H), 1.97-1.77 (m, 4H), 1.47 (s, 9H) ppm. ESI-MS m/z calc. 321.094, found 344.1 (M+23)$^+$; Retention time: 2.2 minutes (LC Method E).

Step 4: Bromo-[3-[[(2S)-1-tert-butoxycarbonylpyrrolidin-2-yl]methoxy]propyl]magnesium

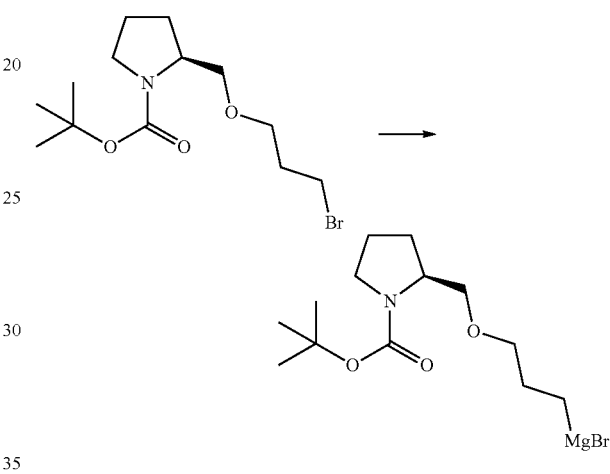

A two-neck 10-mL flask was flame dried under nitrogen and charged with magnesium (132 mg, 5.431 mmol). Magnesium in the flask was activated under nitrogen by heating with a heat gun. After cooling, iodine (1 mg, 0.0039 mmol) was added followed by the dropwise addition of a solution of tert-butyl (2S)-2-(3-bromopropoxymethyl)pyrrolidine-1-carboxylate (500 mg, 1.5516 mmol) in tetrahydrofuran (3 mL) in such a way that the reaction mixture was continuously boiling. After the addition, the dark reaction mixture was stirred at room temperature for 1 h. Stirring was stopped to let any fine particles settle. The resultant bromo-[3-[[(2S)-1-tert-butoxycarbonylpyrrolidin-2-yl]methoxy]propyl]magnesium was used directly as a solution in THF for the next step.

Step 5: tert-Butyl (2S)-2-[(4-ethoxycarbonyl-5,5,5-trifluoro-4-hydroxy-pentoxy)methyl]pyrrolidine-1-carboxylate

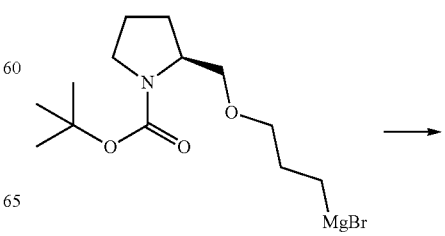

683

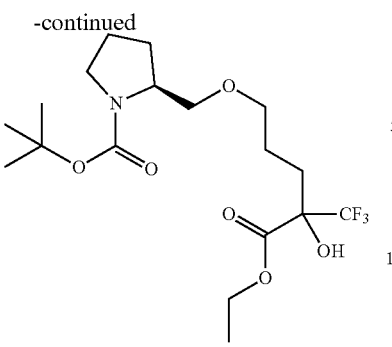

To a solution of ethyl 3,3,3-trifluoro-2-oxo-propanoate (384.90 mg, 0.4 mL, 1.6972 mmol) in diethyl ether (6 mL) at −78° C. was added a THF solution of bromo-[3-[[(2S)-1-tert-butoxycarbonylpyrrolidin-2-yl]methoxy]propyl]magnesium (3 mL of 0.517 M, 1.551 mmol) dropwise over a period of 5 minutes. The mixture was stirred at −78° C. The dry ice-acetone bath was removed after 1 hour. The reaction mixture was allowed to warm up slowly to −30° C. over 30 minutes. To the reaction mixture, was added a solution of saturated aqueous NH$_4$Cl (2 mL) and crushed ice (10 g). The two layers were separated. The organic layer was concentrated and the residue was combined with the aqueous phase and extracted with MTBE (3×60 mL). The combined organic layers were washed with brine (2×20 mL) and dried over anhydrous sodium sulfate. The mixture was filtered and concentrated to give as 730 mg of a light yellow crude oil. Purification by silica gel chromatography using a gradient from 0% to 30% ethyl acetate in heptanes afforded as a colorless oil, tert-butyl (2S)-2-[(4-ethoxycarbonyl-5,5,5-trifluoro-4-hydroxy-pentoxy)methyl]pyrrolidine-1-carboxylate (380 mg, 46%). $^1$H NMR (300 MHz, CDCl$_3$) δ 4.41-4.29 (m, 2H), 4.17-4.00 (m, 1H), 3.99-3.80 (m, 1H), 3.64-3.19 (m, 6H), 2.20-2.06 (m, 1H), 2.00-1.65 (m, 6H), 1.47 (s, 9H), 1.35 (t, J=7.0 Hz, 3H) ppm. One exchangeable proton not observed in NMR. $^{19}$F NMR (282 MHz, Chloroform-d) δ−78.57 (s, 3F) ppm. ESI-MS m/z calc. 413.2025, found 436.2 (M+23)$^+$; Retention time: 2.17 minutes (LC Method E).

Step 6: tert-Butyl (2S)-2-[(4-benzyloxy-4-ethoxycarbonyl-5,5,5-trifluoro-pentoxy)methyl]pyrrolidine-1-carboxylate

684

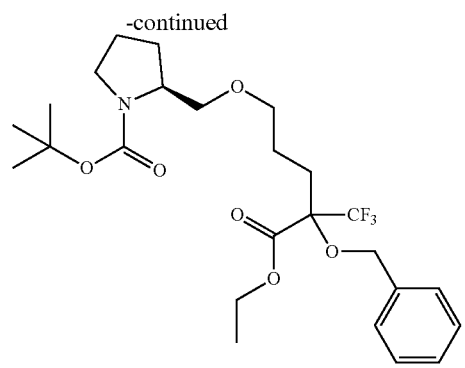

To a solution of tert-butyl (2S)-2-[(4-ethoxycarbonyl-5,5,5-trifluoro-4-hydroxy-pentoxy)methyl]pyrrolidine-1-carboxylate (380 mg, 0.7905 mmol) in DMF (4 mL) at 0° C. was added sodium hydride (45 mg, 60% dispersion in mineral oil, 1.1251 mmol) portion wise, keeping the temperature below 10° C. during the addition. After stirring for 30 minutes in an ice-water bath, bromomethyl benzene (201.32 mg, 0.14 mL, 1.1771 mmol) was added dropwise, then the reaction was warmed gradually to room temperature and stirred for 20 hours. Ammonium chloride (72 mg, 1.346 mmol) was added as a solid at 0° C. and the mixture was stirred for 10 minutes, then 15 mL of a 1:3 solution of heptanes/MTBE as well as water (5 mL) were added. The mixture was transferred to an extraction funnel rinsing with heptanes/MTBE (1:3, 40 mL) and water (20 mL). The organic layer was separated, and the aqueous phase extracted again with the heptanes/MTBE solution (1:3, 2×60 mL). The combined organic layers were washed with water (1×20 mL), brine (2×20 mL) then dried over anhydrous Na$_2$SO$_4$, filtered and concentrated under reduced pressure. The residue was purified by silica gel chromatography using a gradient from 0% to 30% of ethyl acetate in heptanes to afford as a colorless oil, tert-butyl (2S)-2-[(4-benzyloxy-4-ethoxycarbonyl-5,5,5-trifluoro-pentoxy)methyl]pyrrolidine-1-carboxylate (365 mg, 87%). $^1$H NMR (300 MHz, Chloroform-d) δ 7.46-7.28 (m, 5H), 4.82 (d, J=10.6 Hz, 1H), 4.64 (d, J=10.6 Hz, 1H), 4.34 (q, J=7.1 Hz, 2H), 3.99-3.76 (m, 1H), 3.58-3.47 (m, 1H), 3.43 (t, J=6.0 Hz, 2H), 3.38-3.16 (m, 3H), 2.18-1.97 (m, 2H), 1.96-1.73 (m, 5H), 1.69-1.59 (m, 1H), 1.46 (s, 9H), 1.34 (t, J=7.0 Hz, 3H) ppm. $^{19}$F NMR (282 MHz, Chloroform-d) δ−70.43 to −70.82 (m, 3F) ppm. ESI-MS m/z calc. 503.2495, found 526.3 (M+23)$^+$; Retention time: 2.55 minutes (LC Method E).

Step 7: 2-Benzyloxy-5-[[(2S)-1-tert-butoxycarbonylpyrrolidin-2-yl]methoxy]-2-(trifluoromethyl)pentanoic Acid

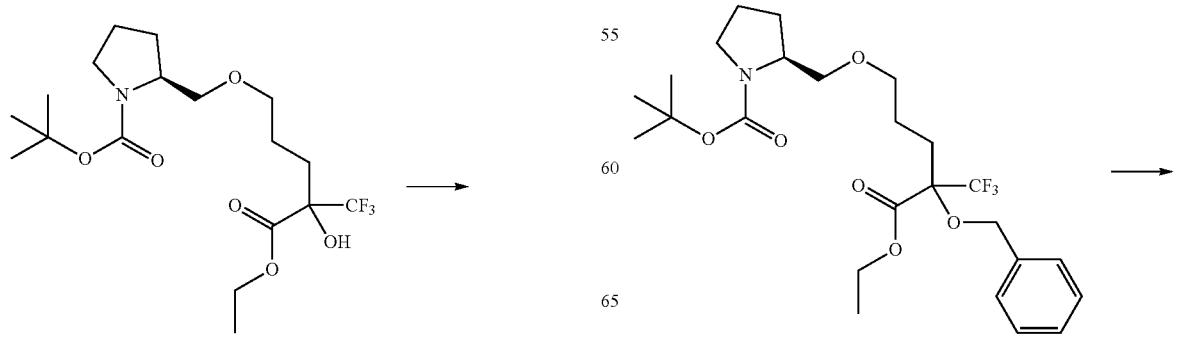

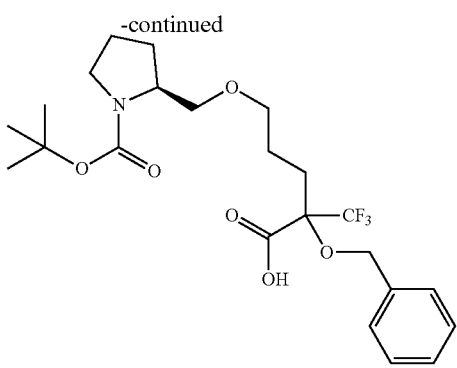

To a solution of tert-butyl (2S)-2-[(4-benzyloxy-4-ethoxycarbonyl-5,5,5-trifluoro-pentoxy)methyl]pyrrolidine-1-carboxylate (0.75 g, 1.4254 mmol) in methanol (6.5 mL) was added a solution of sodium hydroxide (110 mg, 2.7502 mmol) in water (2 mL) and the mixture was stirred at 40° C. overnight. The mixture was concentrated under reduced pressure to remove most of the methanol. Water (30 mL) was added and the mixture was extracted with Et$_2$O (2×80 mL). The organic layers were combined and washed with water (2×30 mL) and the combined aqueous phases were treated with 1 N aqueous HCl (2.9 mL) and then extracted with DCM (3×100 mL). The combined organic layers were dried with Na$_2$SO$_4$, filtered and concentrated to give as a colorless thick oil, 2-benzyloxy-5-[[(2S)-1-tert-butoxycarbonylpyrrolidin-2-yl]methoxy]-2-(trifluoromethyl)pentanoic acid (657 mg, 95%). ESI-MS m/z calc. 475.2182, found 498.2 (M+23)$^+$; Retention time: 2.25 minutes (LC Method E).

Step 8: 2-Benzyloxy-5-[[(2S)-pyrrolidin-2-yl]methoxy]-2-(trifluoromethyl)pentanoic acid (hydrochloride salt)

A hydrochloric acid (12 mL, 4 M, 48 mmol) solution in 1,4-dioxane was added dropwise at 0° C. to a stirring solution of 2-benzyloxy-5-[[(2S)-1-tert-butoxycarbonylpyrrolidin-2-yl]methoxy]-2-(trifluoromethyl)pentanoic acid (1.787 g, 3.7544 mmol) in 1,4-dioxane (20 mL). The cooling bath was removed 5 minutes after the addition and the reaction mixture was stirred at room temperature for 23 h. The volatiles were removed by evaporation under reduced pressure. The solid was dissolved in dichloromethane (30 mL) and then concentrated under reduced pressure and dried under vacuum to give as a light yellow foam, 2-benzyloxy-5-[[(2S)-pyrrolidin-2-yl]methoxy]-2-(trifluoromethyl)pentanoic acid (hydrochloride salt) (1.58 g, 98%). $^1$H NMR (400 MHz, DMSO-d6) δ 14.26 (br s, 1H), 9.28 (br s, 1H), 8.66 (br s, 1H), 7.48-7.26 (m, 5H), 4.77 (d, J=10.9 Hz, 1H), 4.60 (d, J=10.9 Hz, 1H), 3.69-3.59 (m, 1H), 3.58-3.53 (m, 1H), 3.52-3.40 (m, 3H), 3.18-3.03 (m, 2H), 2.15-1.77 (m, 5H), 1.76-1.49 (m, 3H) ppm. ESI-MS m/z calc. 375.16574, found 376.2 (M+1)$^+$; Retention time: 1.4 minutes (LC Method Z).

Step 9: 2-Benzyloxy-5-[[(2S)-1-[6-methoxycarbonyl-5-nitro-3-(trifluoromethyl)-2-pyridyl]pyrrolidin-2-yl]methoxy]-2-(trifluoromethyl)pentanoic acid

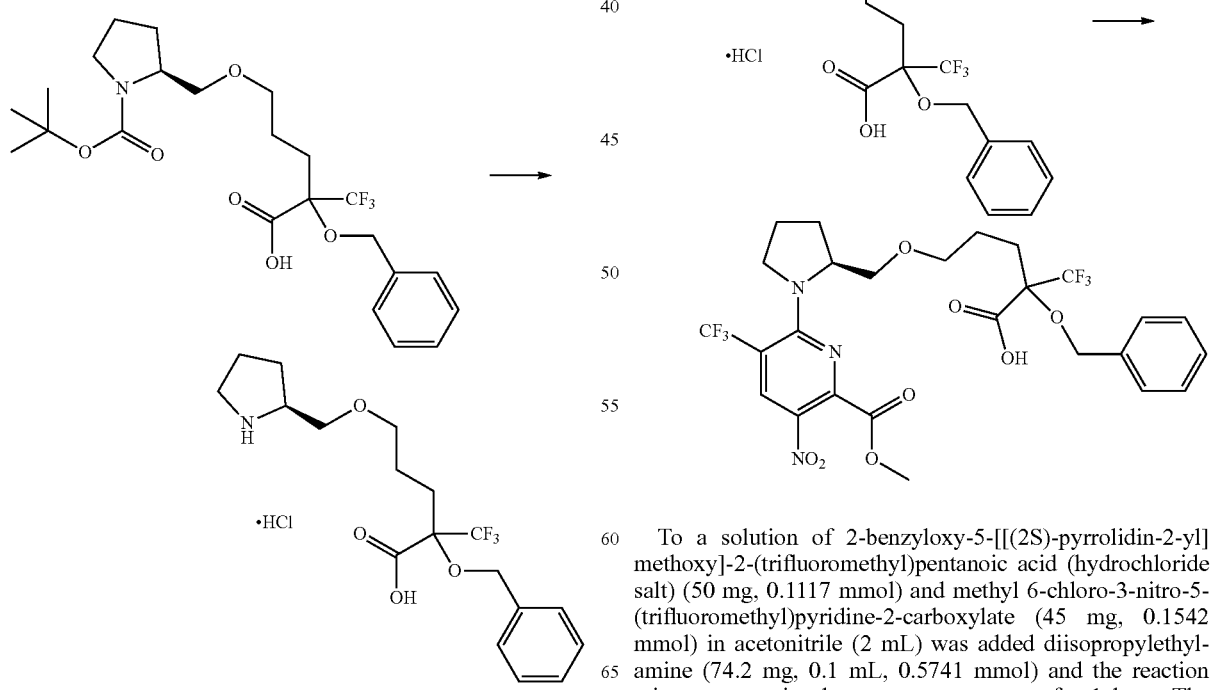

To a solution of 2-benzyloxy-5-[[(2S)-pyrrolidin-2-yl]methoxy]-2-(trifluoromethyl)pentanoic acid (hydrochloride salt) (50 mg, 0.1117 mmol) and methyl 6-chloro-3-nitro-5-(trifluoromethyl)pyridine-2-carboxylate (45 mg, 0.1542 mmol) in acetonitrile (2 mL) was added diisopropylethylamine (74.2 mg, 0.1 mL, 0.5741 mmol) and the reaction mixture was stirred at room temperature for 1 hour. The solvent was removed under reduced pressure, then diluted with ethyl acetate (70 mL) and transferred to an extraction funnel with 30 mL water. The mixture was extracted with ethyl acetate (3×70 mL). The combined organic layers were washed with 0.5 N aqueous hydrochloric acid (2×10 mL) and brine (2×25 mL), dried over sodium sulfate, filtered and concentrated. The residue was purified by silica gel chromatography using a gradient from 0% to 10% methanol in dichloromethane giving as a light yellow solid, 2-benzyloxy-5-[[(2S)-1-[6-methoxycarbonyl-5-nitro-3-(trifluoromethyl)-2-pyridyl]pyrrolidin-2-yl]methoxy]-2-(trifluoromethyl)pentanoic acid (53 mg, 75%). $^1$H NMR (300 MHz, Chloroform-d) δ 8.66-8.52 (m, 1H), 7.43-7.19 (m, 5H), 4.82-4.69 (m, 2H), 4.63-4.53 (m, 1H), 4.06-3.89 (m, 3H), 3.73-3.29 (m, 6H), 2.14-1.92 (m, 5H), 1.91-1.76 (m, 1H), 1.72-1.53 (m, 2H). One exchangeable proton not observed in NMR ppm. $^{19}$F NMR (282 MHz, Chloroform-d) δ −54.31 to −54.66 (m, 3F), −71.70 (s, 3F) ppm. ESI-MS m/z calc. 623.1702, found 646.0 (M+23)$^+$; Retention time: 2.34 minutes (LC Method E).

Step 10: Methyl 6-[(2S)-2-[[4-benzyloxy-4-[(tert-butoxycarbonylamino)carbamoyl]-5,5,5-trifluoro-pentoxy]methyl]pyrrolidin-1-yl]-3-nitro-5-(trifluoromethyl)pyridine-2-carboxylate

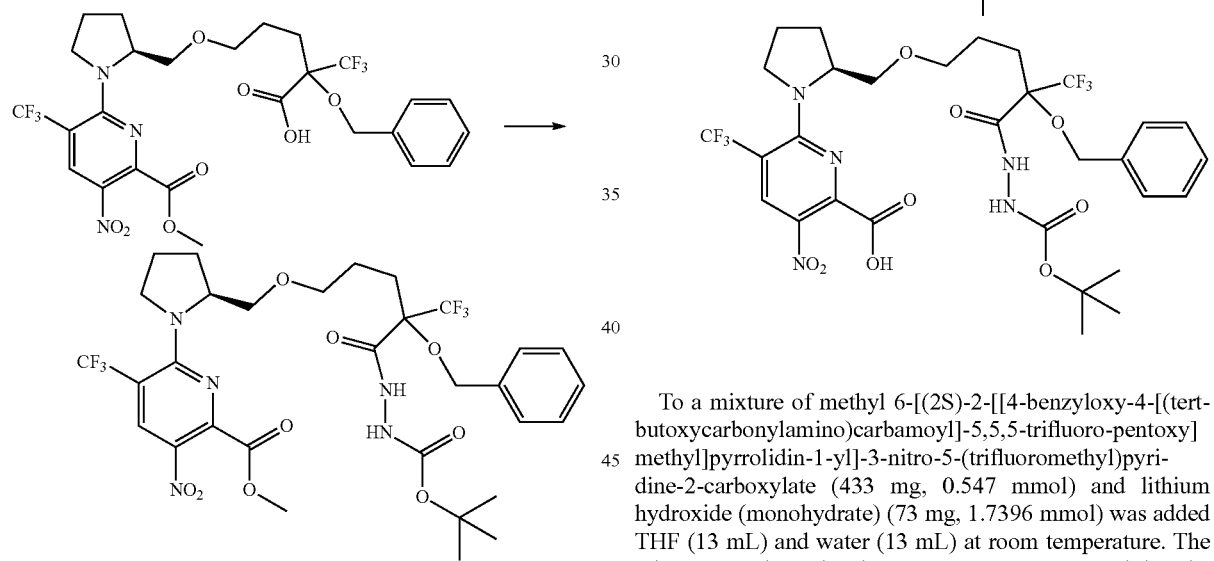

To a solution of 2-benzyloxy-5-[[(2S)-1-[6-methoxycarbonyl-5-nitro-3-(trifluoromethyl)-2-pyridyl]pyrrolidin-2-yl]methoxy]-2-(trifluoromethyl)pentanoic acid (53 mg, 0.0839 mmol) in DMF (1.5 mL) was added triethylamine (18.15 mg, 0.025 mL, 0.1794 mmol) and HATU (44 mg, 0.1157 mmol). The mixture was stirred for 10 min and tert-butyl N-aminocarbamate (14 mg, 0.1059 mmol) was added and the mixture was stirred at room temperature overnight. The mixture was diluted with cold water and extracted with ethyl acetate (3×40 mL), then washed with aqueous saturated NaHCO$_3$ solution (2×10 mL), water (1×10 mL) and brine (3×10 mL). The organic layer was concentrated under reduced pressure. The residue was purified by silica gel chromatography using a gradient from 0% to 40% ethyl acetate in heptanes to give as a light yellow solid, methyl 6-[(2S)-2-[[4-benzyloxy-4-[(tert-butoxycarbonylamino)carbamoyl]-5,5,5-trifluoro-pentoxy]methyl]pyrrolidin-1-yl]-3-nitro-5-(trifluoromethyl)pyridine-2-carboxylate (52 mg, 83%). $^1$H NMR (300 MHz, Chloroform-d) δ 8.66-8.53 (m, 1H), 8.33 (d, J=3.2 Hz, 1H), 7.47-7.28 (m, 5H), 6.32 (br. s, 1H), 4.90-4.78 (m, 1H), 4.78-4.56 (m, 2H), 4.05-3.92 (m, 3H), 3.72-3.33 (m, 6H), 2.32-2.17 (m, 2H), 2.13-1.99 (m, 3H), 1.93-1.79 (m, 1H), 1.73-1.63 (m, 2H), 1.49-1.42 (m, 9H) ppm. ESI-MS m/z calc. 737.2496, found 736.2 (M−1)$^−$; Retention time: 2.41 minutes (LC Method E).

Step 11: 6-[(2S)-2-[[4-Benzyloxy-4-[(tert-butoxycarbonylamino)carbamoyl]-5,5,5-trifluoro-pentoxy]methyl]pyrrolidin-1-yl]-3-nitro-5-(trifluoromethyl)pyridine-2-carboxylic Acid

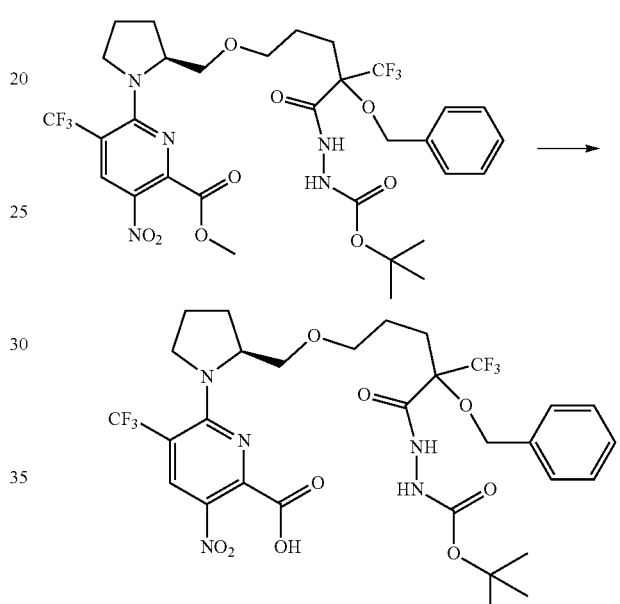

To a mixture of methyl 6-[(2S)-2-[[4-benzyloxy-4-[(tert-butoxycarbonylamino)carbamoyl]-5,5,5-trifluoro-pentoxy]methyl]pyrrolidin-1-yl]-3-nitro-5-(trifluoromethyl)pyridine-2-carboxylate (433 mg, 0.547 mmol) and lithium hydroxide (monohydrate) (73 mg, 1.7396 mmol) was added THF (13 mL) and water (13 mL) at room temperature. The mixture was then stirred at room temperature overnight. The reaction mixture was concentrated by evaporation under reduced pressure and then transferred to a separatory funnel rinsing with water (25 mL) and DCM (40 mL). The pH was adjusted to 2 with a 1 M aqueous solution of hydrochloric acid. The mixture was extracted with DCM (3×60 mL). The combined organic layers were washed with water (10 mL), brine (10 mL) and dried over sodium sulfate, filtered and concentrated under reduced pressure to give as a yellow foam, 6-[(2S)-2-[[4-benzyloxy-4-[(tert-butoxycarbonylamino)carbamoyl]-5,5,5-trifluoro-pentoxy]methyl]pyrrolidin-1-yl]-3-nitro-5-(trifluoromethyl)pyridine-2-carboxylic acid (410 mg, 98%). $^1$H NMR (300 MHz, Chloroform-d) δ 8.77-8.52 (m, 2H), 7.44-7.27 (m, 5H), 6.65 (br. s, 1H), 4.88-4.56 (m, 3H), 3.79-3.36 (m, 6H), 2.18-1.84 (m, 6H), 1.80-1.61 (m, 2H), 1.54-1.43 (m, 9H) ppm. One exchangeable proton not observed in NMR. Retention time: 2.31 minutes (LC Method E).

689

Step 12: (2,5-Dioxopyrrolidin-1-yl) 6-[(2S)-2-[[4-benzyloxy-4-[(tert-butoxycarbonylamino)carbamoyl]-5,5,5-trifluoro-pentoxy]methyl]pyrrolidin-1-yl]-3-nitro-5-(trifluoromethyl)pyridine-2-carboxylate

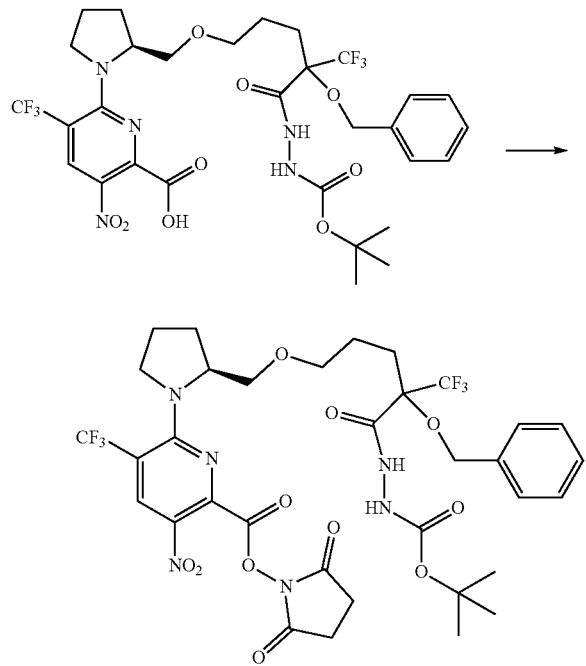

To a solution of 6-[(2S)-2-[[4-benzyloxy-4-[(tert-butoxycarbonylamino)carbamoyl]-5,5,5-trifluoro-pentoxy]methyl]pyrrolidin-1-yl]-3-nitro-5-(trifluoromethyl)pyridine-2-carboxylic acid (410 mg, 0.5383 mmol) in $CH_2Cl_2$ (3.6 mL) was added N-hydroxysuccinimide (69 mg, 0.5995 mmol) and DCC (114 mg, 0.5525 mmol). The mixture was stirred for 2 h at 0° C. and then allowed to stirred overnight at room temperature. The reaction mixture was cooled to 0° C. and the formed precipitate was filtered off and rinsed with diethyl ether and the solid was discarded, then the filtrate was concentrated. The residue was purified by silica gel chromatography using a gradient from 0% to 20% ethyl acetate in dichloromethane giving as a light yellow foam, (2,5-dioxopyrrolidin-1-yl) 6-[(2S)-2-[[4-benzyloxy-4-[(tert-butoxycarbonylamino)carbamoyl]-5,5,5-trifluoro-pentoxy]methyl]pyrrolidin-1-yl]-3-nitro-5-(trifluoromethyl)pyridine-2-carboxylate (400 mg, 85%). $^1$H NMR (300 MHz, Chloroform-d) δ 8.69-8.58 (m, 1H), 8.36-8.27 (m, 1H), 7.46-7.29 (m, 5H), 6.28 (br. s, 1H), 4.93-4.78 (m, 1H), 4.78-4.60 (m, 2H), 3.76-3.38 (m, 6H), 2.89 (s, 4H), 2.32-2.18 (m, 2H), 2.17-2.06 (m, 3H), 1.97-1.84 (m, 1H), 1.75-1.61 (m, 2H), 1.45 (s, 9H) ppm. Retention time: 2.30 minutes (LC Method E).

690

Step 13: (2,5-Dioxopyrrolidin-1-yl) 6-[(2S)-2-[[4-benzyloxy-5,5,5-trifluoro-4-(hydrazinecarbonyl)pentoxy]methyl]pyrrolidin-1-yl]-3-nitro-5-(trifluoromethyl)pyridine-2-carboxylate (hydrochloride salt)

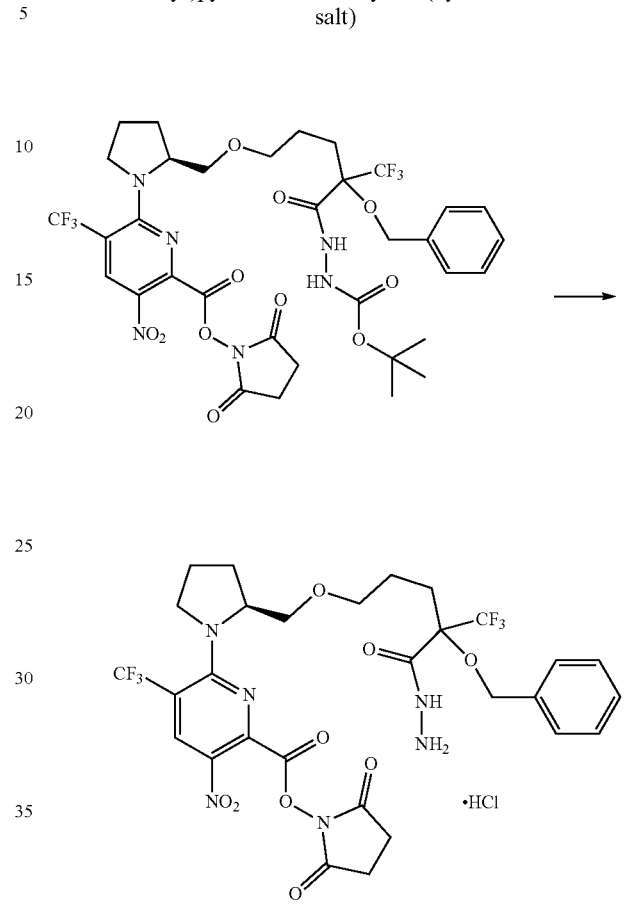

To a solution of (2,5-dioxopyrrolidin-1-yl) 6-[(2S)-2-[[4-benzyloxy-4-[(tert-butoxycarbonylamino)carbamoyl]-5,5,5-trifluoro-pentoxy]methyl]pyrrolidin-1-yl]-3-nitro-5-(trifluoromethyl)pyridine-2-carboxylate (849 mg, 0.9631 mmol) in 1,4-dioxane (34 mL) was dropwise added hydrochloric acid (11 mL, 4 M in dioxane, 44 mmol). The mixture was stirred over 20 h in an oil bath at 32° C. The volatiles were removed under reduced pressure. The residue was evaporated from 1,2-dichloroethane (2×15 mL) and dried under vacuum giving as a light yellow oil, (2,5-dioxopyrrolidin-1-yl) 6-[(2S)-2-[[4-benzyloxy-5,5,5-trifluoro-4-(hydrazinecarbonyl)pentoxy]methyl]pyrrolidin-1-yl]-3-nitro-5-(trifluoromethyl)pyridine-2-carboxylate (hydrochloride salt) (828 mg, 100%). $^1$H NMR (400 MHz, Chloroform-d) δ 8.66-8.53 (m, 1H), 7.45-7.26 (m, 5H), 4.95-4.52 (m, 3H), 3.85-3.33 (m, 7H), 2.94-2.52 (m, 4H), 2.31-1.76 (m, 6H), 1.69-1.47 (m, 2H) ppm. Three exchangeable protons not observed in NMR. ESI-MS m/z calc. 720.1979, found 721.2 (M+1)$^+$; Retention time: 1.9 minutes (LC Method Z).

Step 14: (6S)-12-Benzyloxy-18-nitro-12,20-bis(trifluoromethyl)-8-oxa-2,14,15,21-tetrazatricyclo[15.3.1.02,6]henicosa-1(21),17,19-triene-13,16-dione

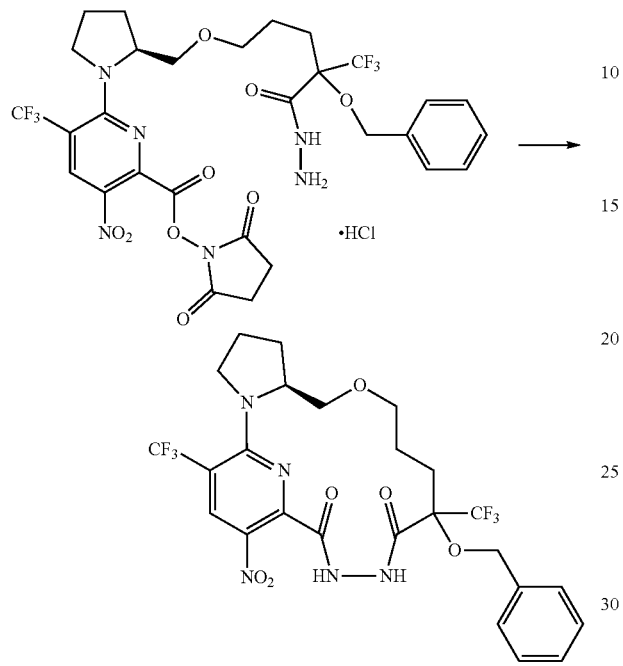

To a suspension of ((2,5-dioxopyrrolidin-1-yl) 6-[(2S)-2-[[4-benzyloxy-5,5,5-trifluoro-4-(hydrazinecarbonyl)pentoxy]methyl]pyrrolidin-1-yl]-3-nitro-5-(trifluoromethyl)pyridine-2-carboxylate (hydrochloride salt) (828 mg, 0.9625 mmol) in 1,2-dichloroethane (140 mL) was added dropwise triethylamine (943.8 mg, 1.3 mL, 9.327 mmol) over 1 minute. The mixture was then stirred at 70° C. for 2 hours. The mixture was cooled, and volatiles were removed under reduced pressure. The residue was purified by silica gel chromatography using a gradient from 0% to 40% ethyl acetate in heptanes giving as a light yellow solid, (6S)-12-benzyloxy-18-nitro-12,20-bis(trifluoromethyl)-8-oxa-2,14,15,21-tetrazatricyclo[15.3.1.02,6]henicosa-1(21),17,19-triene-13,16-dione (364 mg, 61%). $^1$H NMR (400 MHz, Chloroform-d) δ 8.78-8.48 (m, 1H), 8.30-8.13 (m, 1H), 7.48-7.28 (m, 3H), 7.23-7.01 (m, 2H), 4.81-4.53 (m, 2H), 4.39-4.23 (m, 1H), 4.02-3.08 (m, 6H), 2.25-1.78 (m, 5H), 1.53-1.29 (m, 1H), 1.00-0.87 (m, 1H), 0.77-0.51 (m, 1H) ppm. One exchangeable proton not observed in NMR. $^{19}$F NMR (400 MHz, Chloroform-d) δ −54.07 (s, 3F, Ar—CF$_3$ of minor diastereomer), −59.20 (s, 3F, Ar—CF$_3$ of major diastereomer), −73.96 (s, 3F, Alk-CF$_3$ of minor diastereomer), −74.09 (s, 3F, Alk-CF$_3$ of major diastereomer) ppm. ESI-MS m/z calc. 605.1709, found 606.2 (M+1)$^+$; Retention time: 1.93 minutes (LC Method Z).

Step 15: (12S)-6-(Benzyloxy)-20-nitro-6,18-bis(trifluoromethyl)-10,22-dioxa-3,4,16,21-tetraazatetracyclo[15.3.1.12,5.012,16]docosa-1(21),2,4,17,19-pentaene

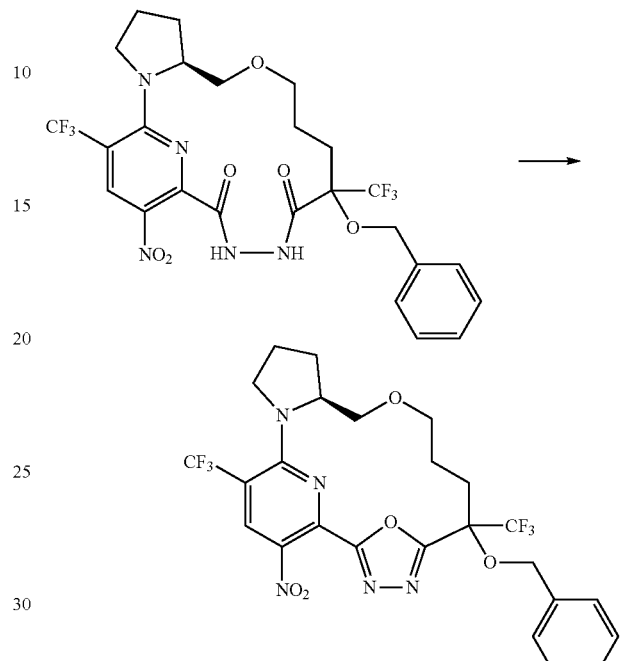

To a solution of (6S)-12-benzyloxy-18-nitro-12,20-bis(trifluoromethyl)-8-oxa-2,14,15,21-tetrazatricyclo[15.3.1.02,6]henicosa-1(21),17,19-triene-13,16-dione (17 mg, 0.0275 mmol) in acetonitrile (2 mL) and N,N-diisopropylethylamine (14.692 mg, 0.02 mL, 0.1125 mmol) at 0° C. was added 4-methylbenzenesulfonyl chloride (7 mg, 0.036 mmol). The mixture was then stirred for 2 h at 50° C., then at 70° C. for 24 hours. The reaction mixture was cooled to room temperature and concentrated under reduced pressure. The residue was dissolved in ethyl acetate (80 mL) and the organic layer was washed with an aqueous solution of 5% sodium bicarbonate (2×15 mL), water (2×15 mL), brine (15 mL), then dried over anhydrous sodium sulfate, filtered and concentrated. The residue was purified by silica gel chromatography using a gradient from 0% to 40% ethyl acetate in heptanes to afford (12S)-6-(benzyloxy)-20-nitro-6,18-bis(trifluoromethyl)-10,22-dioxa-3,4,16,21-tetraazatetracyclo[15.3.1.12,5.012,16]docosa-1(21),2,4,17,19-pentaene (9 mg, 55%). $^1$H NMR (300 MHz, Chloroform-d) δ 8.72-8.66 (m, 1H), 7.41-7.23 (m, 5H), 5.34-4.62 (m, 2H), 4.55-4.44 (m, 1H), 4.10-4.02 (m, 1H), 3.81-3.55 (m, 3H), 3.50-3.38 (m, 1H), 3.07-2.97 (m, 1H), 2.94-2.62 (m, 1H), 2.35-2.22 (m, 1H), 2.21-2.00 (m, 4H), 1.69-1.59 (m, 1H), 1.55-1.46 (m, 1H) ppm. $^{19}$F NMR (282 MHz, Chloroform-d) δ −53.19 (s, 3F, Ar—CF$_3$ of minor diastereomer), −53.26 (s, 3F, Ar—CF$_3$ of major diastereomer), −72.58 (s, 3F, Alk-CF$_3$ of minor diastereomer), −72.79 (s, 3F, Alk-CF$_3$ of major diastereomer) ppm. ESI-MS m/z calc. 587.16034, found 588.2 (M+1)$^+$; Retention time: 2.12 minutes (LC Method Z).

Step 16: (12S)-20-Amino-6,18-bis(trifluoromethyl)-10,22-dioxa-3,4,16,21-tetraazatetracyclo[15.3.1.1²,⁵.0¹²,¹⁶]docosa-1(21),2,4,17,19-pentaen-6-ol (Compound 147)

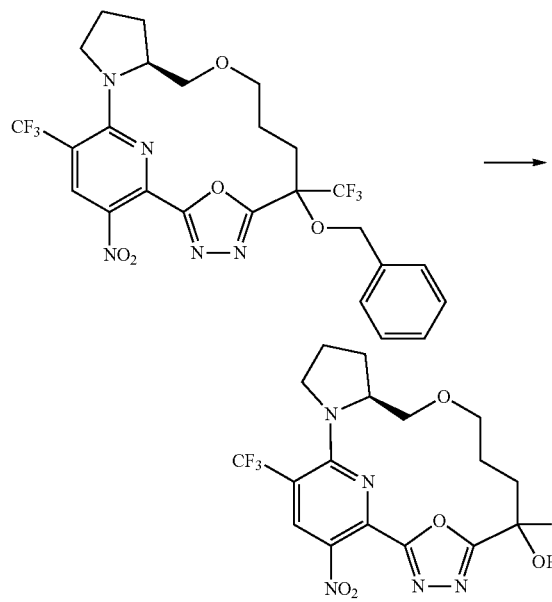

(12S)-6-(Benzyloxy)-20-nitro-6,18-bis(trifluoromethyl)-10,22-dioxa-3,4,16,21-tetraazatetracyclo[15.3.1.1²,⁵.0¹²,¹⁶]docosa-1(21),2,4,17,19-pentaene (9 mg, 0.0151 mmol) was dissolved in anhydrous methanol (2 mL). Nitrogen was bubbled into the mixture for 5 minutes and then palladium on carbon (17 mg, 5% w/w, 0.008 mmol) was added. Hydrogen was then bubbled with a balloon for 5 minutes and the reaction mixture was stirred at room temperature under hydrogen overnight. The hydrogen balloon was replaced with nitrogen, and the mixture purged with nitrogen using a needle exit. The mixture was filtered through a pad of Celite, washing with methanol (5 mL), and the filtrate was concentrated under reduced pressure. The residue was purified by silica gel chromatography using a gradient from 0% to 30% ethyl acetate in dichloromethane giving a light yellow foam which was lyophilized from acetonitrile/water to give as a yellow solid, (12S)-20-amino-6,18-bis(trifluoromethyl)-10,22-dioxa-3,4,16,21-tetraazatetracyclo[15.3.1.1²,⁵.0¹²,¹⁶]docosa-1(21),2,4,17,19-pentaen-6-ol (4.8 mg, 63%). $^1$H NMR (400 MHz, Chloroform-d) δ 7.64-7.41 (m, 1H), 4.47-4.08 (m, 2H), 3.87-3.36 (m, 4H), 3.06-2.68 (m, 2H), 2.29-1.99 (m, 3H), 1.98-1.83 (m, 2H), 1.66-1.54 (m, 1H), 1.38-1.28 (m, 1H), 0.96-0.80 (m, 1H) ppm. Two exchangeable protons not observed in NMR or masked by a solvent peak. $^{19}$F NMR (377 MHz, Chloroform-d) δ −54.52 to −56.24 (m, 3F, —CF$_3$ of both diastereomers), −76.97 (s, 3F, major diastereomer), −81.17 (s, 3F, minor diastereomer) ppm. ESI-MS m/z calc. 467.13922, found 468.2 (M+1)$^+$; Retention time: 4.37 minutes (LC Method AA).

Example 82: Preparation of 17-amino-6-hydroxy-N,N-dimethyl-6,15-bis(trifluoromethyl)-19-oxa-3,4,13,18-tetrazatricyclo[12.3.1.1²,⁵]nonadeca-1(18),2,4,14,16-pentaene-12-carboxamide (enantiomer 1) (Compound 148), 17-amino-6-hydroxy-N,N-dimethyl-6,15-bis(trifluoromethyl)-19-oxa-3,4,13,18-tetrazatricyclo[12.3.1.1²,⁵]nonadeca-1(18),2,4,14,16-pentaene-12-carboxamide (enantiomer 2) (Compound 149), 17-amino-6-hydroxy-N,N-dimethyl-6,15-bis(trifluoromethyl)-19-oxa-3,4,13,18-tetrazatricyclo[12.3.1.1²,⁵]nonadeca-1(18),2,4,14,16-pentaene-12-carboxamide (enantiomer 3) (Compound 150) and 17-amino-6-hydroxy-N,N-dimethyl-6,15-bis(trifluoromethyl)-19-oxa-3,4,13,18-tetrazatricyclo[12.3.1.1²,⁵]nonadeca-1(18),2,4,14,16-pentaene-12-carboxamide (enantiomer 4) (Compound 151)

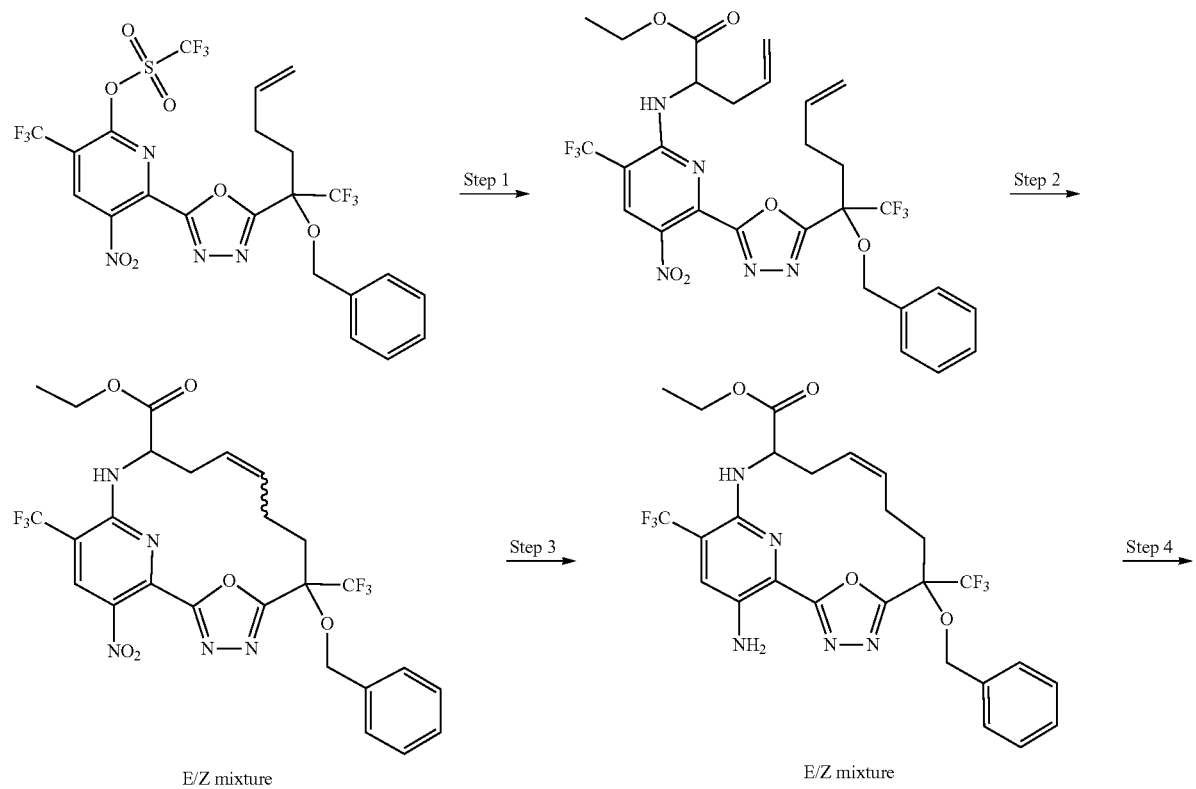

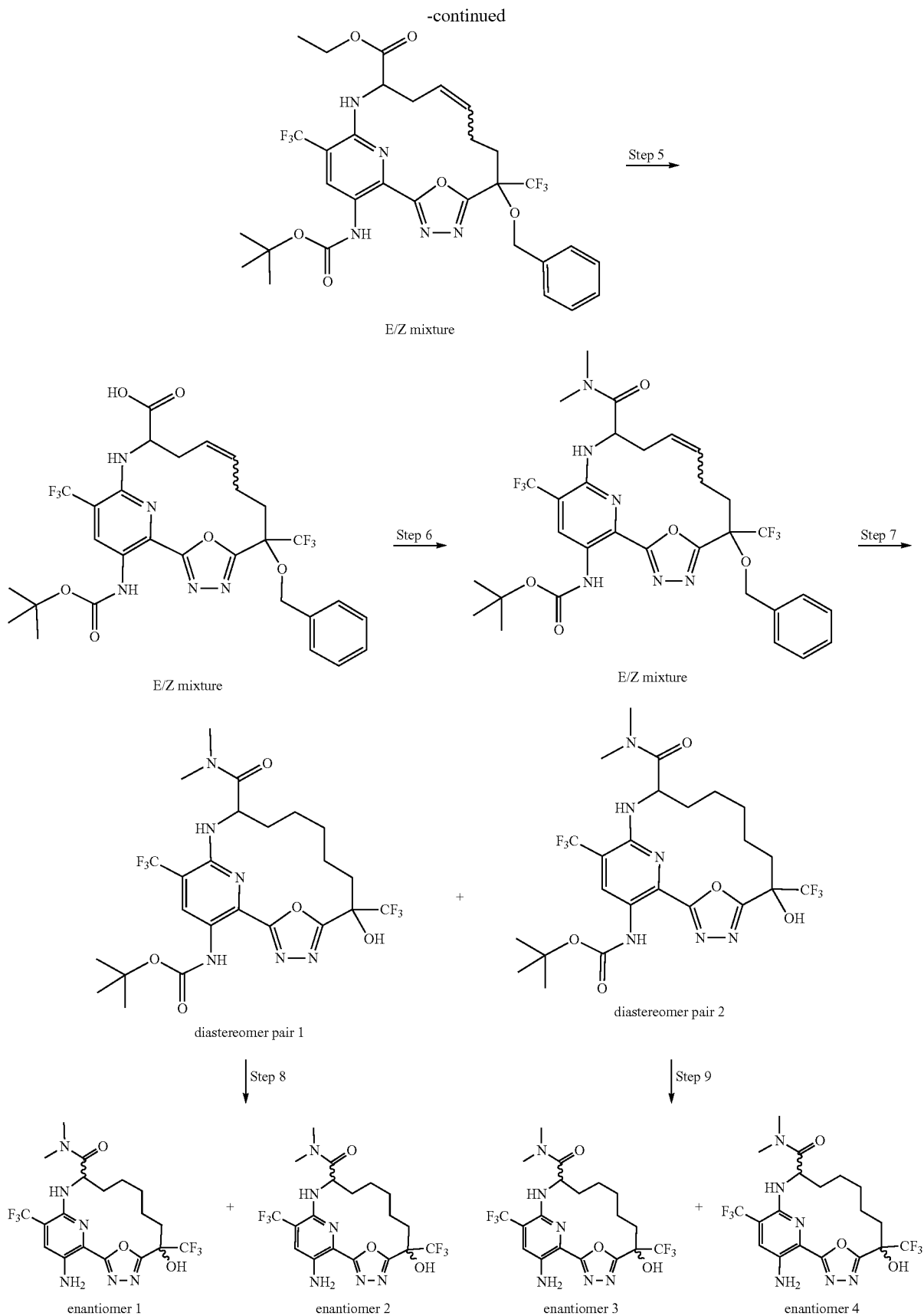
-continued

Step 1: Ethyl 2-[[6-[5-[1-Benzyloxy-1-(trifluoromethyl)pent-4-enyl]-1,3,4-oxadiazol-2-yl]-5-nitro-3-(trifluoromethyl)-2-pyridyl]amino]pent-4-enoate Step 2: Ethyl-6-benzyloxy-17-nitro-6,15-bis(trifluoromethyl)-19-oxa-3,4,13,18-tetrazatricyclo [12.3.1.12,5]nonadeca-1(18),2,4,9,14,16-hexaene-12-carboxylate (E/Z mixture)

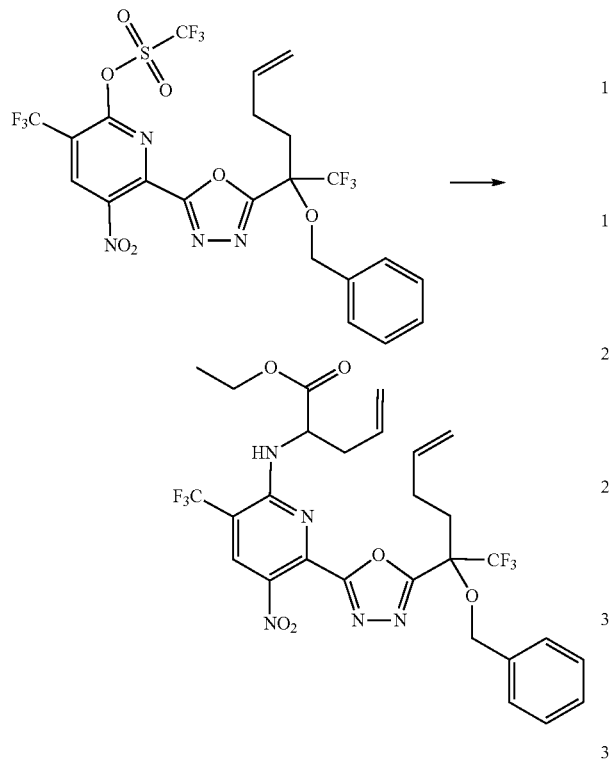

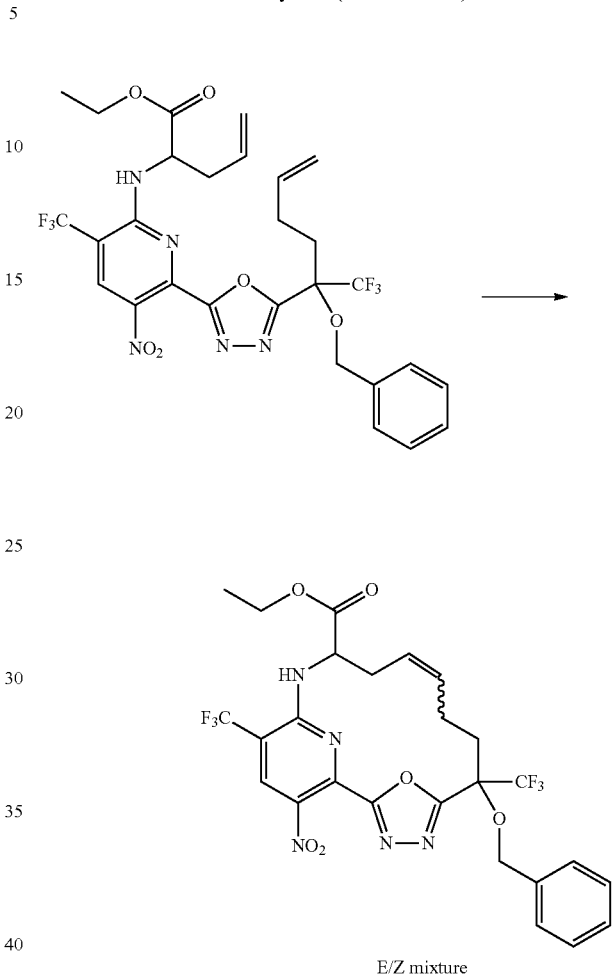

E/Z mixture

In a 20 mL microwave vial [6-[5-[1-benzyloxy-1-(trifluoromethyl)pent-4-enyl]-1,3,4-oxadiazol-2-yl]-5-nitro-3-(trifluoromethyl)-2-pyridyl] trifluoromethanesulfonate (1.35 g, 2.076 mmol) was dissolved in acetonitrile (10 mL) at room temperature followed by addition of ethyl 2-aminopent-4-enoate (900 mg, 6.286 mmol) then DIEA (1.75 mL, 10.05 mmol) and then the mixture was stirred for 16 hours. The mixture was concentrated and the residue was purified by silica gel chromatography (120 gram column) using a gradient from 100% hexanes to 70% ethyl acetate in hexanes to afford as a pale yellow solid, ethyl 2-[[6-[5-[1-benzyloxy-1-(trifluoromethyl)pent-4-enyl]-1,3,4-oxadiazol-2-yl]-5-nitro-3-(trifluoromethyl)-2-pyridyl]amino]pent-4-enoate (900 mg, 67%). $^1$H NMR (400 MHz, DMSO-d6) δ 8.64 (s, 1H), 8.14 (t, J=6.9 Hz, 1H), 7.40-7.24 (m, 5H), 5.81 (dddt, J=40.2, 17.2, 10.2, 6.7 Hz, 2H), 5.16-4.98 (m, 4H), 4.76 (d, J=10.7 Hz, 1H), 4.69 (dddd, J=9.1, 7.2, 5.3, 1.9 Hz, 1H), 4.59 (dd, J=10.7, 2.0 Hz, 1H), 4.03 (q, J=7.1 Hz, 2H), 2.82-2.63 (m, 2H), 2.55 (dd, J=12.4, 7.4 Hz, 1H), 2.47 (s, 1H), 2.34-2.15 (m, 2H), 1.04 (t, J=7.1 Hz, 3H) ppm. ESI-MS m/z calc. 643.1865, found 644.2 (M+1)$^+$; Retention time: 2.05 minutes (LC Method J).

In a 1 L 3-neck flask, a continuously degassed solution via nitrogen line of Zhan catalyst-1B (250 mg, 0.3407 mmol) in 1,2-dichloroethane (400 mL) and was heated to 50° C. under nitrogen atmosphere. Then, a solution of ethyl 2-[[6-[5-[1-benzyloxy-1-(trifluoromethyl)pent-4-enyl]-1,3,4-oxadiazol-2-yl]-5-nitro-3-(trifluoromethyl)-2-pyridyl]amino]pent-4-enoate (900 mg, 1.399 mmol) in 1,2-dichloroethane (10 mL) was added via syringe. The resulting mixture was heated at 75° C. for 2 h. The residue was concentrated and purified by silica gel chromatography (80 gram column) using a gradient from 100% hexanes to 50% ethyl acetate in hexanes to afford as an off-white solid, ethyl-6-benzyloxy-17-nitro-6, 15-bis(trifluoromethyl)-19-oxa-3,4,13,18-tetrazatricyclo [12.3.1.12,5]nonadeca-1(18),2,4,9,14,16-hexaene-12-carboxylate (E/Z mixture) (310 mg, 36%). ESI-MS m/z calc. 615.1553, found 616.0 (M+1)$^+$; Retention time: 1.82 minutes (LC Method J).

Step 3: Ethyl-17-amino-6-benzyloxy-6,15-bis(trifluoromethyl)-19-oxa-3,4,13,18-tetrazatricyclo[12.3.1.1²,⁵]nonadeca-1(18),2,4,9,14,16-hexaene-12-carboxylate (E/Z Mixture)

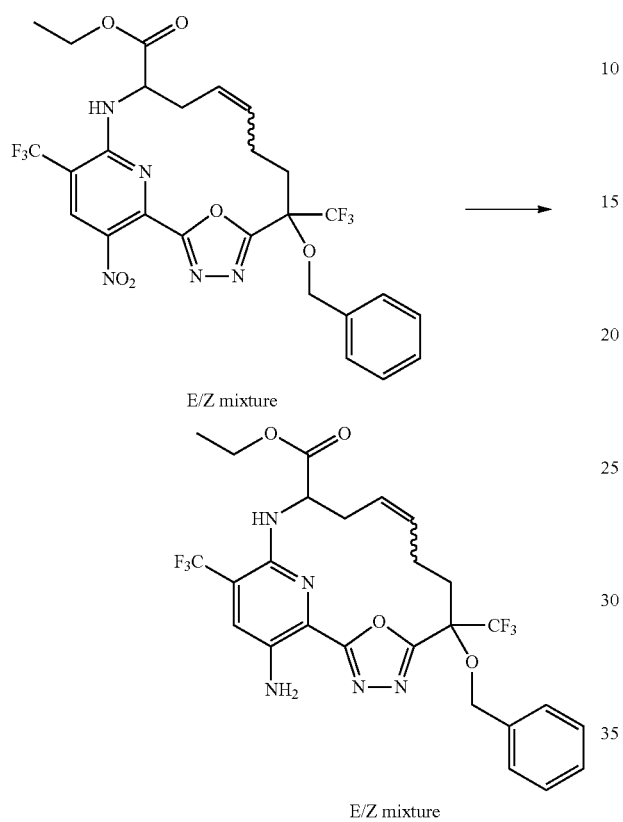

E/Z mixture

E/Z mixture

Step 4: Ethyl-6-benzyloxy-17-(tert-butoxycarbonylamino)-6,15-bis(trifluoromethyl)-19-oxa-3,4,13,18-tetrazatricyclo[12.3.1.1²,⁵]nonadeca-1(18),2,4,9,14,16-hexaene-12-carboxylate (E/Z Mixture)

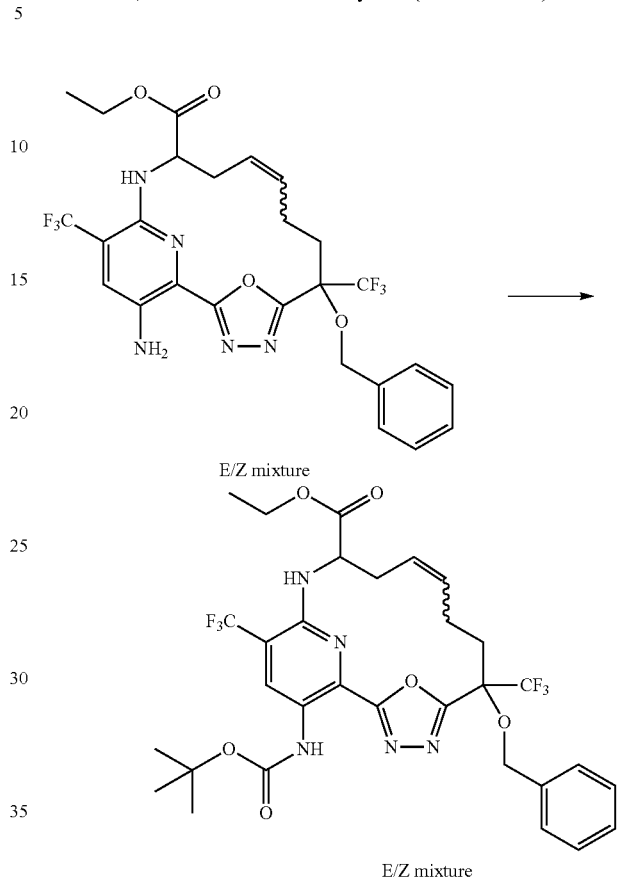

E/Z mixture

E/Z mixture

A mixture of ethyl-6-benzyloxy-17-nitro-6,15-bis(trifluoromethyl)-19-oxa-3,4,13,18-tetrazatricyclo[12.3.1.1²,⁵]nonadeca-1(18),2,4,9,14,16-hexaene-12-carboxylate (E/Z mixture) (160 mg, 0.26 mmol), and tin(II) chloride dihydrate (235 mg, 1.041 mmol) in ethyl acetate (7 mL) was stirred at 55° C. for 90 min. After 30 min, additional tin(II) chloride dihydrate (235 mg, 1.041 mmol) was added. The mixture was diluted with EtOAc and 2 N NaOH was added to the mixture until it became viscous, then filtered through Celite. The filtrate was washed with brine, dried over sodium sulfate, filtered and evaporated. Then, the mixture was purified by silica gel chromatography (12 gram column) using a gradient from 100% hexanes to 30% ethyl acetate in hexanes to afford as a yellow solid, ethyl-17-amino-6-benzyloxy-6,15-bis(trifluoromethyl)-19-oxa-3,4,13,18-tetrazatricyclo[12.3.1.1²,⁵]nonadeca-1(18),2,4,9,14,16-hexaene-12-carboxylate (E/Z mixture) (125 mg, 82%). ESI-MS m/z calc. 585.1811, found 586.2 (M+1)⁺; Retention time: 1.96 minutes (LC Method J).

To a solution of ethyl-17-amino-6-benzyloxy-6,15-bis(trifluoromethyl)-19-oxa-3,4,13,18-tetrazatricyclo[12.3.1.1²,⁵]nonadeca-1(18),2,4,9,14,16-hexaene-12-carboxylate (E/Z mixture) (125 mg, 0.2135 mmol) in dioxane (6 mL) was added di-tert-butyl dicarbonate (175 mg, 0.8018 mmol), triethylamine (220 µL, 1.578 mmol) and DMAP (3.5 mg, 0.02865 mmol) and the reaction mixture was stirred for 3 h. The mixture was diluted with water and extracted with ethyl acetate. The organic layer was washed with water (5 mL), saturated aqueous sodium bicarbonate (5 mL) and brine (5 mL), then dried over sodium sulfate, filtered and concentrated. The residue was purified by silica gel chromatography (24 gram column) using a shallow gradient from 100% hexanes to 40% EtOAc in hexanes giving as a bright yellow foam, ethyl-6-benzyloxy-17-(tert-butoxycarbonylamino)-6,15-bis(trifluoromethyl)-19-oxa-3,4,13,18-tetrazatricyclo[12.3.1.1²,⁵]nonadeca-1(18),2,4,9,14,16-hexaene-12-carboxylate (E/Z mixture) (110 mg, 75%). ESI-MS m/z calc. 685.2335, found 686.2 (M+1)⁺; Retention time: 2.29 minutes. This product was contaminated with a small amount of bis-Boc protected byproduct (ESI-MS m/z calc. 785.28595, found 786.2 (M+1)⁺; Retention time: 2.37 minutes (LC Method J).

701

Step 5: 6-Benzyloxy-17-(tert-butoxycarbonylamino)-6,15-bis(trifluoromethyl)-19-oxa-3,4,13,18-tetrazatricyclo[12.3.1.1²,⁵]nonadeca-1(17),2,4,9,14(18),15-hexaene-12-carboxylic Acid (E/Z Mixture)

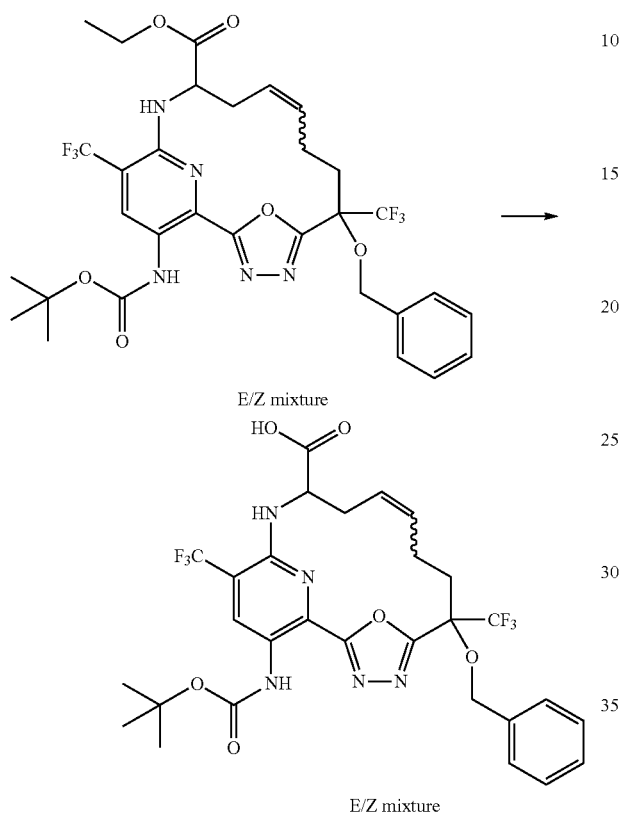

E/Z mixture

E/Z mixture

To a solution of ethyl-6-benzyloxy-17-(tert-butoxycarbonylamino)-6,15-bis(trifluoromethyl)-19-oxa-3,4,13,18-tetrazatricyclo[12.3.1.1²,⁵]nonadeca-1(18),2,4,9,14,16-hexaene-12-carboxylate (E/Z mixture) (135 mg, 0.1969 mmol) (contaminated with a small amount of the analogous bis-Boc protected compound carried over from the previous step) in THF (2 mL) was added MeOH (2 mL) and H$_2$O (3 mL) followed by lithium hydroxide (30 mg, 1.253 mmol). The mixture was stirred at 65° C. for 2 h. THF and methanol were removed under reduced pressure and then aqueous 10% HCl (10 mL) was added to acidify to pH ~4 and the product was extracted with EtOAc (2×150 mL). The organic phases were combined, washed with brine (100 mL), dried over anhydrous sodium sulfate, filtered and concentrated under reduced pressure. The residue was purified by silica gel chromatography (12 gram column) using a gradient from 100% hexanes to 80% ethyl acetate in hexanes to afford as a yellow solid, 6-benzyloxy-17-(tert-butoxycarbonylamino)-6,15-bis(trifluoromethyl)-19-oxa-3,4,13,18-tetrazatricyclo[12.3.1.1²,⁵]nonadeca-1(17),2,4,9,14(18),15-hexaene-12-carboxylic acid (E/Z mixture) (61 mg, 47%). ESI-MS m/z calc. 657.2022, found 658.2 (M+1)⁺; Retention time: 2.03 minutes (LC Method J).

702

Step 6: tert-Butyl N-[6-benzyloxy-12-(dimethylcarbamoyl)-6,15-bis(trifluoromethyl)-19-oxa-3,4,13,18-tetrazatricyclo[12.3.1.1²,⁵]nonadeca-1(17),2,4,9,14(18),15-hexaen-17-yl]carbamate (E/Z Mixture)

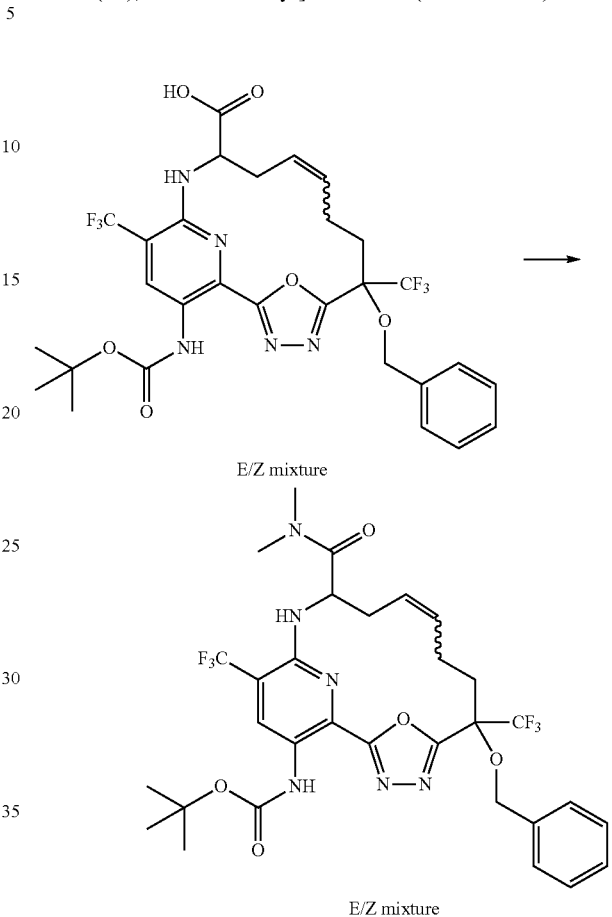

E/Z mixture

E/Z mixture

To a solution of 6-benzyloxy-17-(tert-butoxycarbonylamino)-6,15-bis(trifluoromethyl)-19-oxa-3,4,13,18-tetrazatricyclo[12.3.1.1²,⁵]nonadeca-1(17),2,4,9,14(18),15-hexaene-12-carboxylic acid (E/Z mixture) (61 mg, 0.09277 mmol) in NMP (2.0 mL) at room temperature was added N-methylmethanamine (hydrochloride salt) (38 mg, 0.466 mmol) and DIEA (250 μL, 1.435 mmol), followed by HATU (55 mg, 0.1446 mmol). The reaction mixture was stirred at room temperature for 3 h. The organic material was extracted with ethyl acetate (3×5 mL). The organics were dried over sodium sulfate, filtered and evaporated. The residue was purified by silica gel chromatography (4 gram column) using a gradient from 100% hexanes to 50% ethyl acetate in hexanes to afford as a pale yellow solid, tert-butyl N-[6-benzyloxy-12-(dimethylcarbamoyl)-6,15-bis(trifluoromethyl)-19-oxa-3,4,13,18-tetrazatricyclo[12.3.1.1²,⁵]nonadeca-1(17),2,4,9,14(18),15-hexaen-17-yl]carbamate (E/Z mixture) (49 mg, 77%). ESI-MS m/z calc. 684.2495, found 685.2 (M+1)⁺; Retention time: 2.15 minutes (LC Method J).

Step 7: tert-Butyl N-[12-(dimethylcarbamoyl)-6-hydroxy-6,15-bis(trifluoromethyl)-19-oxa-3,4,13,18-tetrazatricyclo[12.3.1.1²,⁵]nonadeca-1(18),2,4,14,16-pentaen-17-yl]carbamate (diastereomer pair 1) and tert-butyl N-[12-(dimethylcarbamoyl)-6-hydroxy-6,15-bis(trifluoromethyl)-19-oxa-3,4,13,18-tetrazatricyclo[12.3.1.1²,⁵]nonadeca-1(18),2,4,14,16-pentaen-17-yl]carbamate (diastereomer pair 2)

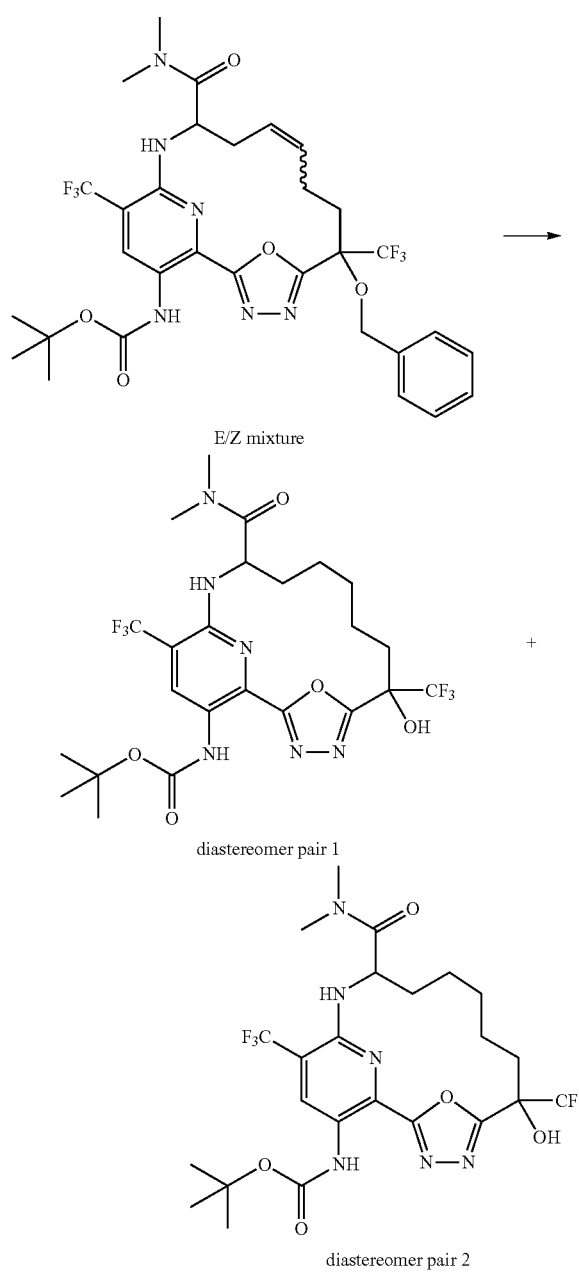

In a 100 mL round bottom flask, a solution of tert-butyl N-[6-benzyloxy-12-(dimethylcarbamoyl)-6,15-bis(trifluoromethyl)-19-oxa-3,4,13,18-tetrazatricyclo[12.3.1.1²,⁵]nonadeca-1(17),2,4,9,14(18),15-hexaen-17-yl]carbamate (E/Z mixture) (39 mg, 0.05697 mmol) in AcOH (1 mL) and ethyl acetate (1 mL) was purged with nitrogen. Then Pd/C (65 mg, 10% w/w, 0.06108 mmol) was added. The mixture was degassed with nitrogen then purged by a balloon filled with hydrogen gas. The mixture was stirred at 1 atm of hydrogen for 2 h. The mixture was filtered through Celite, washing with excess ethyl acetate and the filtrate was concentrated. The residue was purified by reverse phase HPLC using a gradient from 30% to 99% acetonitrile in water (+5 mM HCl) over 15 minutes giving the separation of two diastereomer pairs:

The first diastereomer pair to elute was isolated as a yellow solid, tert-butyl N-[12-(dimethylcarbamoyl)-6-hydroxy-6,15-bis(trifluoromethyl)-19-oxa-3,4,13,18-tetrazatricyclo[12.3.1.1²,⁵]nonadeca-1(18),2,4,14,16-pentaen-17-yl]carbamate (diastereomer pair 1) (8.7 mg, 51%). ESI-MS m/z calc. 596.2182, found 597.2 (M+1)⁺; Retention time: 1.53 minutes (LC Method J).

The second diastereomer pair to elute was isolated as a yellow solid, tert-butyl N-[12-(dimethylcarbamoyl)-6-hydroxy-6,15-bis(trifluoromethyl)-19-oxa-3,4,13,18-tetrazatricyclo[12.3.1.1²,⁵]nonadeca-1(18),2,4,14,16-pentaen-17-yl]carbamate (diastereomer pair 2) (6.7 mg, 39%). ESI-MS m/z calc. 596.2182, found 597.2 (M+1)⁺; Retention time: 1.61 minutes (LC Method J).

Step 8: 17-Amino-6-hydroxy-N,N-dimethyl-6,15-bis(trifluoromethyl)-19-oxa-3,4,13,18-tetrazatricyclo[12.3.1.1²,⁵]nonadeca-1(18),2,4,14,16-pentaene-12-carboxamide (enantiomer 1) (Compound 148) and 17-amino-6-hydroxy-N,N-dimethyl-6,15-bis(trifluoromethyl)-19-oxa-3,4,13,18-tetrazatricyclo[12.3.1.1²,⁵]nonadeca-1(18),2,4,14,16-pentaene-12-carboxamide (enantiomer 2) (Compound 149)

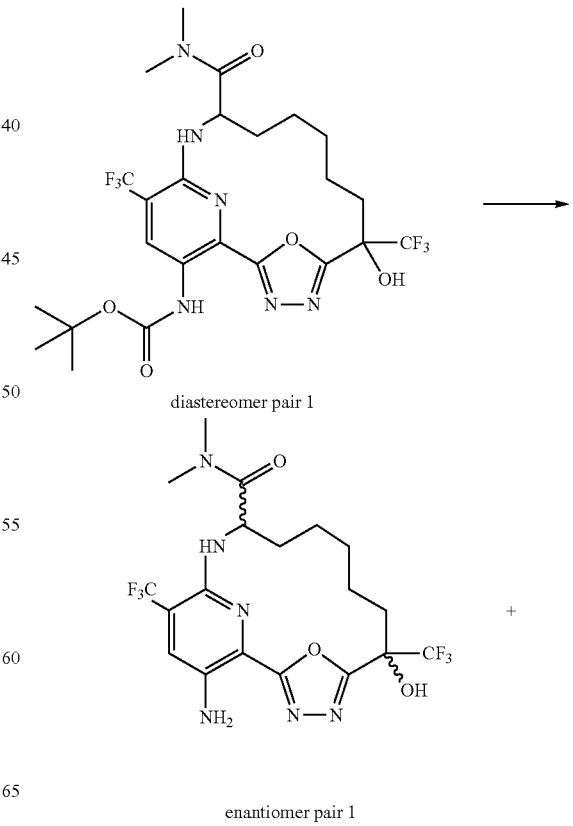

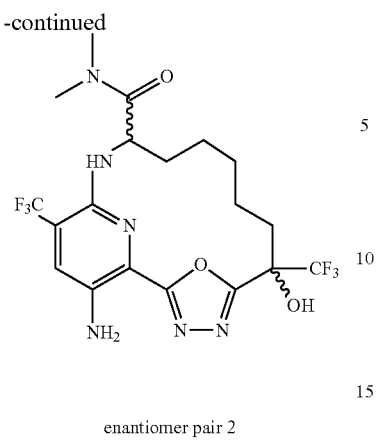

enantiomer pair 2

To a solution of tert-butyl N-[12-(dimethylcarbamoyl)-6-hydroxy-6,15-bis(trifluoromethyl)-19-oxa-3,4,13,18-tetrazatricyclo[12.3.1.12,5]nonadeca-1(18),2,4,14,16-pentaen-17-yl]carbamate (diastereomer pair 1) (8.7 mg, 0.01458 mmol) in DCM (750 μL) was added TFA (100 μL, 1.298 mmol) and the reaction mixture was stirred at room temperature for 45 min. The mixture was concentrated and purified by reverse phase HPLC using a gradient from 1% to 99% acetonitrile in water (+5 mM HCl) over 15 min giving a diastereomer pair of the products. This mixture was purified by chiral SFC using a ChiralPak IG column (250× 10 mm, 5 μm particle size) eluting with 14% MeOH (+20 mM NH$_3$)/86% CO$_2$ at a flow rate of 10 mL/min which provided two single enantiomer products:

The first enantiomer to elute was isolated as a yellow solid, 17-amino-6-hydroxy-N,N-dimethyl-6,15-bis(trifluoromethyl)-19-oxa-3,4,13,18-tetrazatricyclo[12.3.1.12,5]nonadeca-1(18),2,4,14,16-pentaene-12-carboxamide (enantiomer 1) (2.1 mg, 55%). $^1$H NMR (400 MHz, Chloroform-d) δ 7.33 (s, 1H), 5.80 (d, J=6.0 Hz, 1H), 5.12 (s, 2H), 4.96 (q, J=5.7 Hz, 1H), 3.58 (s, 1H), 3.13 (s, 3H), 3.04 (s, 3H), 2.38-2.29 (m, 1H), 2.28-2.16 (m, 2H), 2.04 (s, 1H), 1.77 (dt, J=13.5, 6.6 Hz, 1H), 1.60 (d, J=6.0 Hz, 2H), 1.54-1.48 (m, 2H), 1.44-1.37 (m, 1H) ppm. ESI-MS m/z calc. 496.16577, found 497.2 (M+1)$^+$; Retention time: 1.56 minutes (LC Method A).

The second enantiomer to elute was isolated as a yellow solid, 17-amino-6-hydroxy-N,N-dimethyl-6,15-bis(trifluoromethyl)-19-oxa-3,4,13,18-tetrazatricyclo[12.3.1.12,5]nonadeca-1(18),2,4,14,16-pentaene-12-carboxamide (enantiomer 2) (1.1 mg, 30%). ESI-MS m/z calc. 496.16577, found 497.2 (M+1)$^+$; Retention time: 1.56 minutes (LC Method A).

Step 9: 17-Amino-6-hydroxy-N,N-dimethyl-6,15-bis(trifluoromethyl)-19-oxa-3,4,13,18-tetrazatricyclo[12.3.1.12,5]nonadeca-1(18),2,4,14,16-pentaene-12-carboxamide (enantiomer 3) (Compound 150) and 17-amino-6-hydroxy-N,N-dimethyl-6,15-bis(trifluoromethyl)-19-oxa-3,4,13,18-tetrazatricyclo[12.3.1.12,5]nonadeca-1(18),2,4,14,16-pentaene-12-carboxamide (enantiomer 4) (Compound 151)

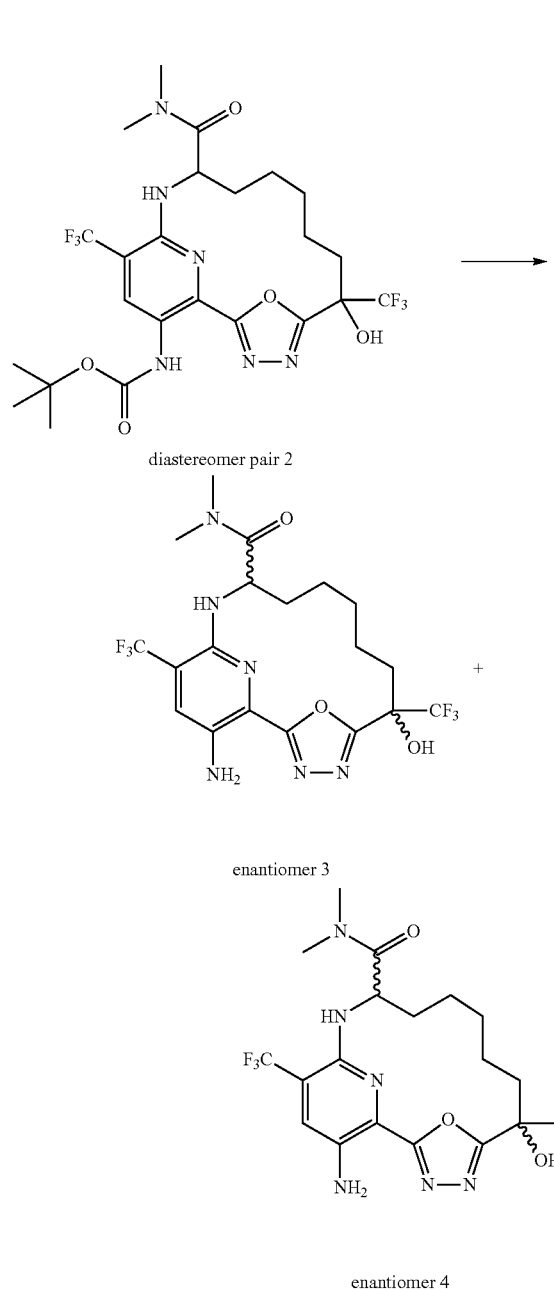

To a solution of tert-butyl N-[12-(dimethylcarbamoyl)-6-hydroxy-6,15-bis(trifluoromethyl)-19-oxa-3,4,13,18-tetrazatricyclo[12.3.1.12,5]nonadeca-1(18),2,4,14,16-pentaen-17-yl]carbamate (diastereomer pair 2) (9.1 mg, 0.01526 mmol) in DCM (750 μL) was added TFA (100 μL, 1.298 mmol) and the reaction mixture was stirred at room temperature for 45 minutes. The mixture was concentrated and purified by reverse phase HPLC using a gradient from 1% to 99% acetonitrile in water (+5 mM HCl) over 15 min giving a diastereomer pair of the products. This mixture was purified by chiral SFC using a ChiralPak IG column (250× 10 mm, 5 μm particle size) eluting with 14% MeOH (+20 mM NH₃)/86% CO₂ at a flow rate of 10 mL/min which provided two single enantiomer products:

The first enantiomer to elute was isolated as a yellow solid, 17-amino-6-hydroxy-N,N-dimethyl-6,15-bis(trifluoromethyl)-19-oxa-3,4,13,18-tetrazatricyclo[12.3.1.1²,⁵]nonadeca-1(18),2,4,14,16-pentaene-12-carboxamide (enantiomer 3) (1.7 mg, 44%). ¹H NMR (400 MHz, Chloroform-d) δ 7.34 (s, 1H), 5.71 (d, J=6.0 Hz, 1H), 5.05 (s, 2H), 4.97 (q, J=6.2 Hz, 1H), 3.59 (s, 1H), 3.08 (s, 3H), 3.03 (s, 3H), 2.41 (dt, J=15.4, 8.0 Hz, 1H), 2.27 (dt, J=11.9, 6.1 Hz, 1H), 2.20 (s, 1H), 2.04 (s, 1H), 1.82 (s, 1H), 1.65 (dd, J=12.5, 6.2 Hz, 2H), 1.51 (s, 2H), 1.26 (s, 1H) ppm. ESI-MS m/z calc. 496.16577, found 497.2 (M+1)⁺; Retention time: 1.59 minutes (LC Method A).

The second enantiomer to elute was isolated as a yellow solid, 17-amino-6-hydroxy-N,N-dimethyl-6,15-bis(trifluoromethyl)-19-oxa-3,4,13,18-tetrazatricyclo[12.3.1.1²,⁵]nonadeca-1(18),2,4,14,16-pentaene-12-carboxamide (enantiomer 4) (1.5 mg, 39%). ESI-MS m/z calc. 496.16577, found 497.2 (M+1)⁺; Retention time: 1.59 minutes (LC Method A).

Example 83: Preparation of (12R)-20-amino-18-[4-(trifluoromethoxy)benzenesulfonyl]-6-(trifluoromethyl)-22-oxa-3,4,16,21-tetraazatetracyclo[15.3.1.1²,⁵.0¹²,¹⁶]docosa-1(20),2,4,17(21),18-pentaen-6-ol (enantiomer 1) (hydrochloride salt) (Compound 152) and (12R)-20-amino-18-[4-(trifluoromethoxy)benzenesulfonyl]-6-(trifluoromethyl)-22-oxa-3,4,16,21-tetraazatetracyclo[15.3.1.1²,⁵.0¹²,¹⁶]docosa-1(20),2,4,17(21),18-pentaen-6-ol (enantiomer 2) (hydrochloride salt) (Compound 153)

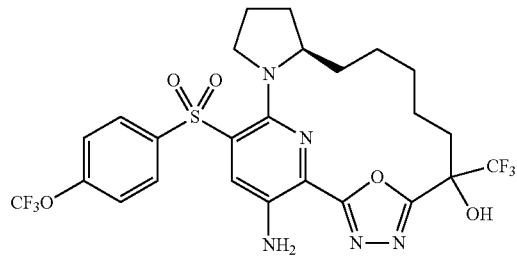

Step 1

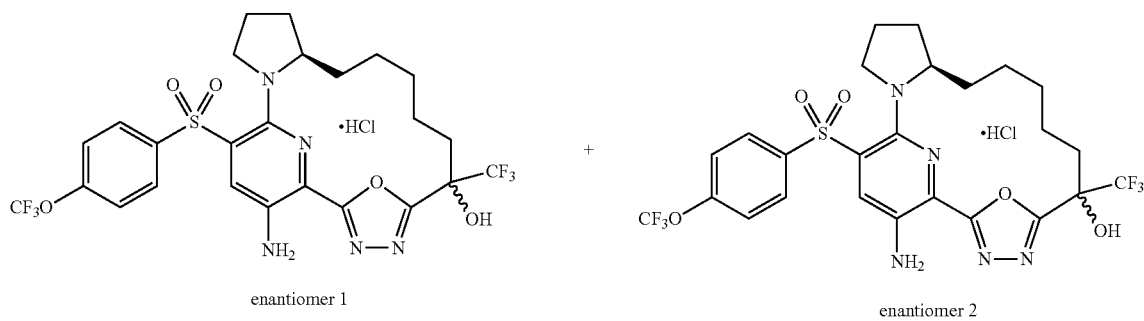

enantiomer 1 enantiomer 2

Step 1: (12R)-20-Amino-18-[4-(trifluoromethoxy)benzenesulfonyl]-6-(trifluoromethyl)-22-oxa-3,4,16,21-tetraazatetracyclo[15.3.1.1²,⁵.0¹²,¹⁶]docosa-1(20),2,4,17(21),18-pentaen-6-ol (enantiomer 1) (hydrochloride salt) (Compound 152) and (12R)-20-amino-18-[4-(trifluoromethoxy)benzenesulfonyl]-6-(trifluoromethyl)-22-oxa-3,4,16,21-tetraazatetracyclo[15.3.1.1²,⁵.0¹²,¹⁶]docosa-1(20),2,4,17(21),18-pentaen-6-ol (enantiomer 2) (hydrochloride salt) (Compound 153)

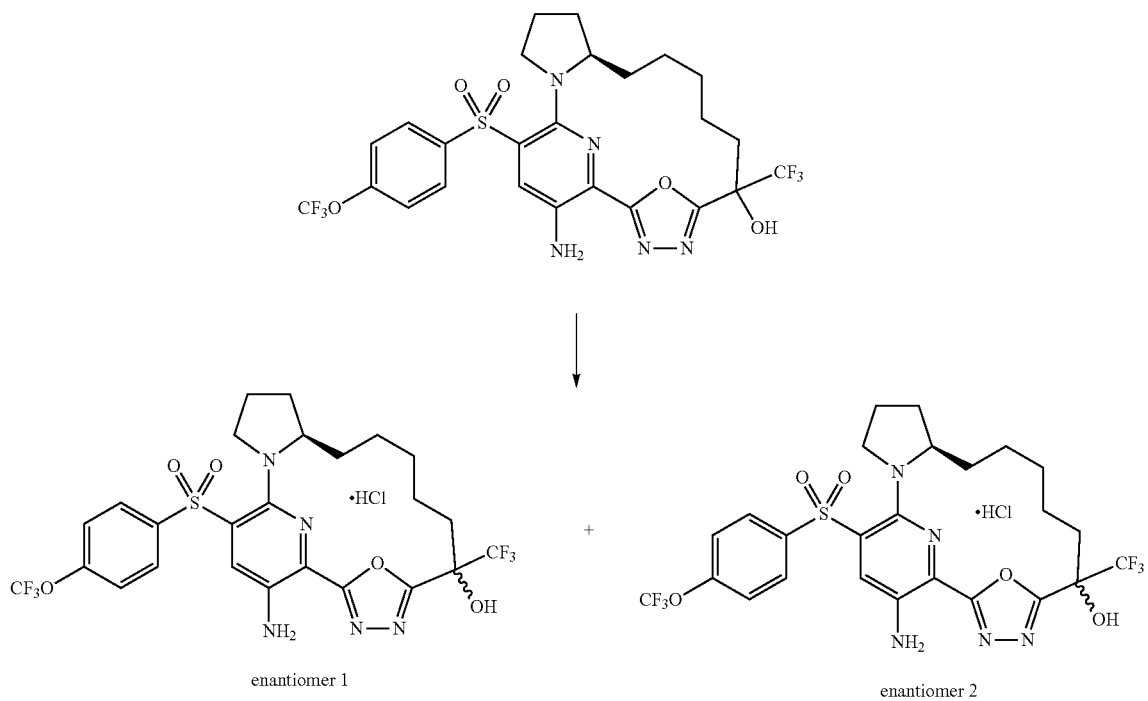

(12R)-20-Amino-18-[4-(trifluoromethoxy)benzenesulfonyl]-6-(trifluoromethyl)-22-oxa-3,4,16,21-tetraazatetracyclo[15.3.1.1²,⁵.0¹²,¹⁶]docosa-1(20),2,4,17(21),18-pentaen-6-ol (15 mg, 0.02413 mmol) was purified by reverse phase HPLC using a gradient from 30% to 99% acetonitrile in water (+5 mM HCl) over 30 minutes which gave two single diastereomeric products:

The first diastereomer to elute was isolated as a yellow solid, (12R)-20-amino-18-[4-(trifluoromethoxy)benzenesulfonyl]-6-(trifluoromethyl)-22-oxa-3,4,16,21-tetraazatetracyclo[15.3.1.1²,⁵.0¹²,¹⁶]docosa-1(20),2,4,17(21),18-pentaen-6-ol (enantiomer 1) (hydrochloride salt) (5.8 mg, 69%). $^1$H NMR (400 MHz, Chloroform-d) δ 8.15-8.11 (m, 1H), 8.05 (dt, J=8.7, 2.6 Hz, 2H), 7.41-7.36 (m, 2H), 7.35-7.33 (m, 1H), 5.30 (s, 1H), 4.86 (s, 1H), 4.02 (d, J=11.1 Hz, 1H), 2.80 (s, 1H), 2.55 (s, 1H), 2.47-2.22 (m, 4H), 2.10 (s, 1H), 1.67 (s, 5H), 1.50 (d, J=13.3 Hz, 3H) ppm. One exchangeable proton not observed or masked by solvent peak. ESI-MS m/z calc. 621.1481, found 622.3 (M+1)⁺; Retention time: 1.26 minutes (LC Method A).

The second diastereomer to elute was isolated as a yellow solid, (12R)-20-amino-18-[4-(trifluoromethoxy)benzenesulfonyl]-6-(trifluoromethyl)-22-oxa-3,4,16,21-tetraazatetracyclo[15.3.1.1²,⁵.0¹²,¹⁶]docosa-1(20),2,4,17(21),18-pentaen-6-ol (enantiomer 2) (hydrochloride salt) (2.4 mg, 28%). $^1$H NMR (400 MHz, Chloroform-d) δ 8.20 (d, J=9.7 Hz, 1H), 8.04 (t, J=9.0 Hz, 2H), 7.32 (dd, J=13.5, 8.2 Hz, 3H), 5.26 (s, 1H), 5.02 (s, 1H), 4.07 (s, 1H), 3.38 (d, J=9.8 Hz, 2H), 2.60 (d, J=36.9 Hz, 1H), 2.35 (d, J=37.6 Hz, 2H), 2.22-2.04 (m, 1H), 1.76-1.43 (m, 8H) ppm. Two exchangeable protons not observed or masked by solvent peak. ESI-MS m/z calc. 621.1481, found 622.4 (M+1)⁺; Retention time: 1.4 minutes (LC Method A).

Example 84: Preparation of [(6R)-17-amino-6-hydroxy-6,15-bis(trifluoromethyl)-19-oxa-3,4,13,18-tetrazatricyclo[12.3.1.1²,⁵]nonadeca-1(18),2,4,14,16-pentaen-12-yl]-pyrrolidin-1-yl-methanone (Compound 154)

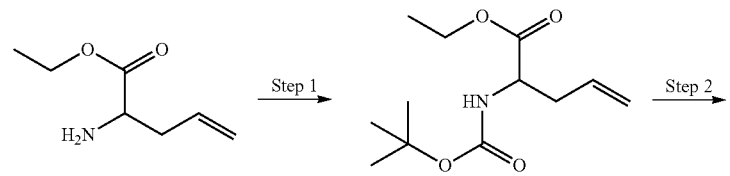

711 712
-continued
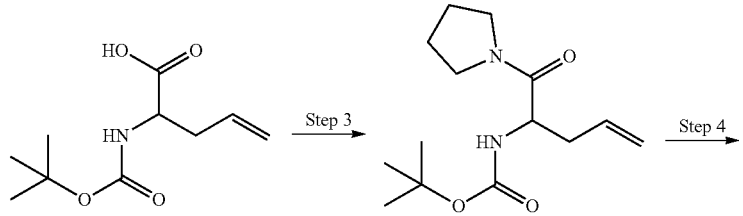
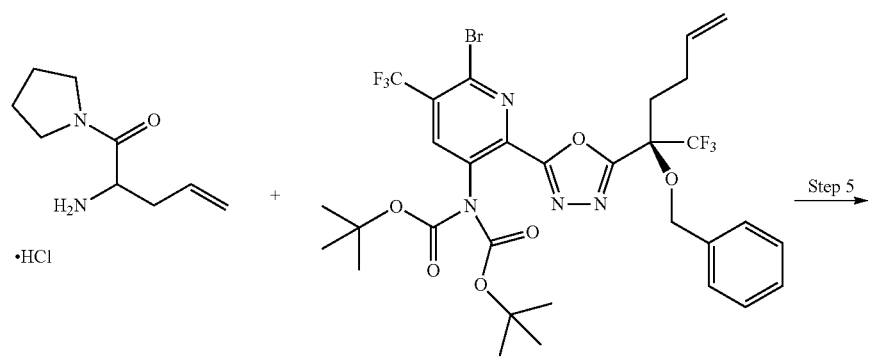
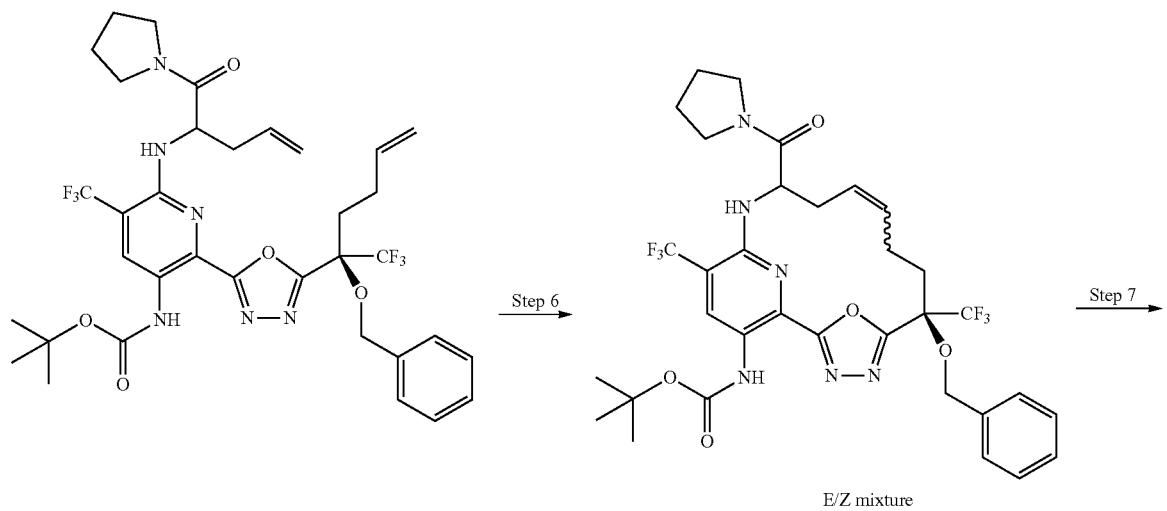
E/Z mixture

713

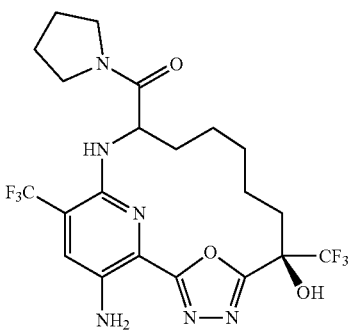

E/Z mixture

Step 8 →

714

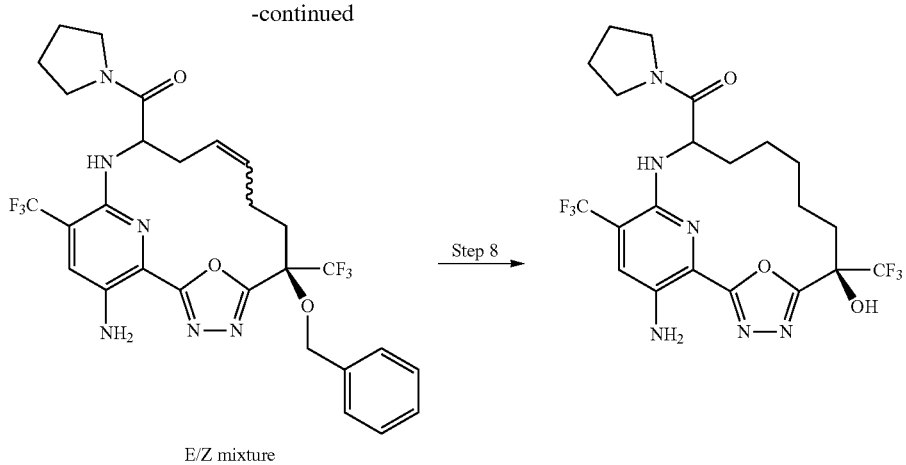

Step 1: Ethyl 2-(tert-butoxycarbonylamino)pent-4-enoate

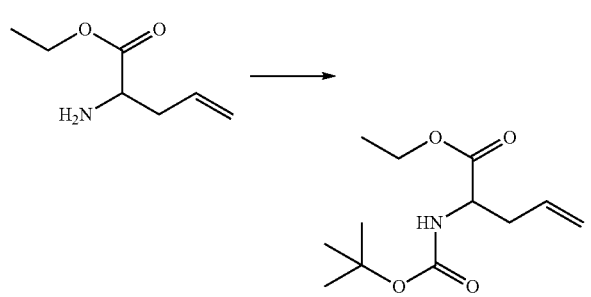

To a solution of ethyl 2-aminopent-4-enoate (1.3 g, 9.079 mmol) dissolved in dioxane (7.5 mL) was added di-tert-butyl dicarbonate (2.5 g, 11.45 mmol) and triethylamine (4.5 mL, 32.29 mmol) and the reaction mixture was stirred for 16 h at room temperature. The dioxane was evaporated to half volume and water was added. This mixture was extracted with ethyl acetate and the combined organics were washed with brine, dried over sodium sulfate, filtered and concentrated. The resultant residue was purified by silica gel chromatography (440 gram column) using a shallow gradient of 100% hexanes to 100% EtOAc to afford as a clear oil, ethyl 2-(tert-butoxycarbonylamino)pent-4-enoate (1.68 g, 76%). $^1$H NMR (400 MHz, DMSO-d6) δ 7.21 (d, J=7.8 Hz, 1H), 5.76 (ddt, J=17.1, 10.1, 6.9 Hz, 1H), 5.12-5.01 (m, 2H), 4.12-4.02 (m, 2H), 3.97 (td, J=8.2, 5.6 Hz, 1H), 2.35 (tt, J=14.4, 7.2 Hz, 2H), 1.38 (s, 9H), 1.17 (t, J=7.1 Hz, 3H) ppm. ESI-MS m/z calc. 243.14706, found 244.1 (M+1)+; Retention time: 1.56 minutes (LC Method A).

Step 2: 2-(tert-Butoxycarbonylamino)pent-4-enoic Acid

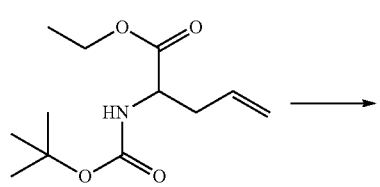

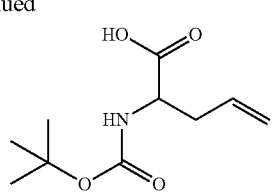

To a solution of ethyl 2-(tert-butoxycarbonylamino)pent-4-enoate (1.68 g, 6.905 mmol) in THF (25 mL) was added MeOH (25 mL) and H$_2$O (35 mL) followed by lithium hydroxide (990 mg, 41.34 mmol). The mixture was stirred at room temperature for 2 h. THF and methanol were removed under reduced pressure and then 10% aqueous HCl (10 mL) was added to acidify to pH ~4 and the product was extracted by EtOAc (2×150 mL). The organic phases were combined, washed with brine (100 mL), dried over anhydrous sodium sulfate, filtered and concentrated under reduced pressure. The residue was then purified by silica gel chromatography (24 gram column) using a shallow gradient from 100% hexanes to 100% ethyl acetate to afford as a viscous oil, 2-(tert-butoxycarbonylamino)pent-4-enoic acid (1.48 g, 100%). $^1$H NMR (400 MHz, DMSO-d6) δ 12.38 (s, 1H), 7.03 (d, J=8.1 Hz, 1H), 5.89-5.58 (m, 1H), 5.09 (dd, J=17.2, 2.0 Hz, 1H), 5.03 (dd, J=10.2, 2.1 Hz, 1H), 3.93 (td, J=8.6, 5.1 Hz, 1H), 2.47-2.25 (m, 2H), 1.38 (s, 9H) ppm. ESI-MS m/z calc. 215.11575, found 216.2 (M+1)+; Retention time: 1.11 minutes (LC Method A).

Step 3: tert-Butyl N-[1-(pyrrolidine-1-carbonyl)but-3-enyl]carbamate

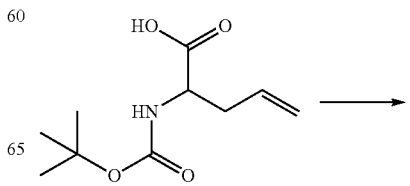

715
-continued

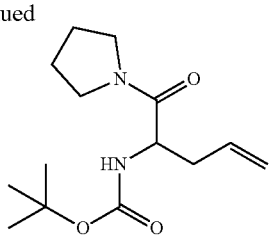

To a solution of 2-(tert-butoxycarbonylamino)pent-4-enoic acid (1.35 g, 6.272 mmol) in THF (48 mL) and NMP (48 mL) at room temperature was added pyrrolidine (1.85 mL, 22.16 mmol) and DIEA (6.5 mL, 37.32 mmol) followed by HATU (3.69 g, 9.705 mmol). The reaction mixture was stirred at room temperature for 16 h. The reaction mixture was then diluted with water, citric acid solution and extracted with ethyl acetate (2×50 mL). The organics were combined, dried over sodium sulfate, filtered and evaporated. The residue was purified by silica gel chromatography (80 gram column) using a shallow gradient from 100% hexanes to 100% ethyl acetate which afforded as a white solid, tert-butyl N-[1-(pyrrolidine-1-carbonyl)but-3-enyl] carbamate (1.45 g, 86%). $^1$H NMR (400 MHz, DMSO-d6) δ 6.90 (d, J 8.2 Hz, 1H), 5.74 (ddt, J=17.1, 10.1, 7.0 Hz, 1H), 5.09 (dd, J=17.2, 2.0 Hz, 1H), 5.01 (dd, J=10.1, 2.2 Hz, 1H), 4.20 (td, J=8.3, 5.6 Hz, 1H), 3.52 (dt, J=10.1, 6.8 Hz, 1H), 3.41 (dt, J=10.0, 6.8 Hz, 1H), 3.25 (td, J=13.5, 12.0, 7.2 Hz, 2H), 2.32 (dt, J=13.1, 6.2 Hz, 1H), 2.22 (dd, J=14.3, 7.6 Hz, 1H), 1.87 (p, J=6.7 Hz, 2H), 1.81-1.71 (m, 2H), 1.36 (s, 9H) ppm. ESI-MS m/z calc. 268.17868, found 269.2 (M+1)$^+$; Retention time: 1.3 minutes (LC Method A).

Step 4: 2-Amino-1-pyrrolidin-1-yl-pent-4-en-1-one (hydrochloride salt)

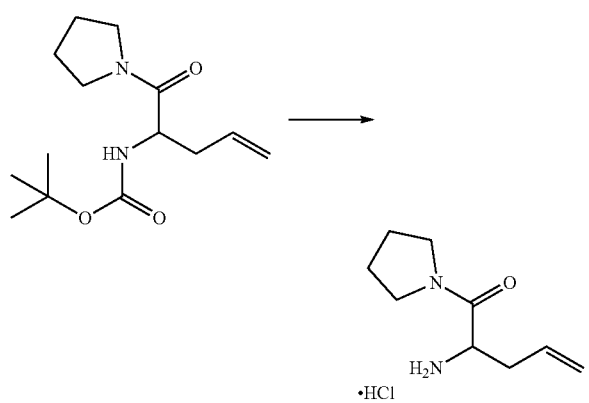 [SMILES: C=CCC(NC(=O)OC(C)(C)C)C(=O)N1CCCC1 ; C=CCC(N)C(=O)N1CCCC1 ; Cl]

To a solution of tert-butyl N-[1-(pyrrolidine-1-carbonyl) but-3-enyl]carbamate (1.45 g, 5.403 mmol) in DCM (20 mL) was added HCl (4 N in dioxane, 7 mL, 28 mmol) and stirred at room temperature for 1 h. The mixture was evaporated to dryness, then diluted with ether and concentrated. The residue was placed vacuum overnight to afford as an off-white solid, 2-amino-1-pyrrolidin-1-yl-pent-4-en-1-one (hydrochloride salt) (750 mg, 68%). ESI-MS m/z calc. 168.12627, found 169.2 (M+1)$^+$; Retention time: 0.52 minutes (LC Method A).

716

Step 5: tert-Butyl N-[2-[5-[(1R)-1-benzyloxy-1-(trifluoromethyl)pent-4-enyl]-1,3,4-oxadiazol-2-yl]-6-[1-(pyrrolidine-1-carbonyl)but-3-enylamino]-5-(trifluoromethyl)-3-pyridyl]carbamate

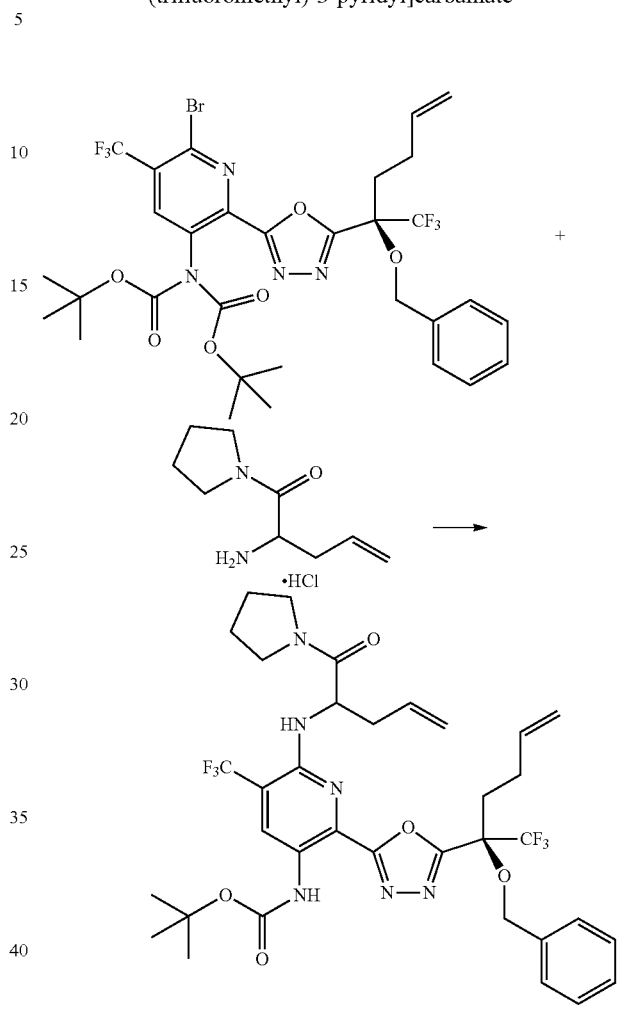

In a 20-mL microwave vessel, 2-amino-1-pyrrolidin-1-yl-pent-4-en-1-one (hydrochloride salt) (550 mg, 2.687 mmol), DIEA (900 μL, 5.167 mmol) and tert-butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate (700 mg, 0.9315 mmol) were combined in acetonitrile (12 mL) and DMSO (3.5 mL) and the mixture was heated at 90° C. for 14 h. Then, heated at 105° C. for additional 24 hours. The reaction mixture was cooled to room temperature and concentrated under reduced pressure. The residue was purified by silica gel chromatography (40 gram column) using a gradient from 100% hexanes to 40% ethyl acetate in hexanes which produced as a yellow solid, tert-butyl N-[2-[5-[(1R)-1-benzyloxy-1-(trifluoromethyl)pent-4-enyl]-1,3,4-oxadiazol-2-yl]-6-[1-(pyrrolidine-1-carbonyl)but-3-enylamino]-5-(trifluoromethyl)-3-pyridyl]carbamate (159 mg, 23%). ESI-MS m/z calc. 738.29645, found 739.2 (M+1)$^+$; Retention time: 1.91 minutes (LC Method M).

Step 6: tert-Butyl N-[(6R)-6-benzyloxy-12-(pyrrolidine-1-carbonyl)-6,15-bis(trifluoromethyl)-19-oxa-3,4,13,18-tetrazatricyclo[12.3.1.1²,⁵]nonadeca-1(17),2,4,9,14(18),15-hexaen-17-yl]carbamate (E/Z Mixture)

Step 7: [(6R)-17-Amino-6-benzyloxy-6,15-bis(trifluoromethyl)-19-oxa-3,4,13,18-tetrazatricyclo[12.3.1.1²,⁵]nonadeca-1(17),2,4,9,14(18),15-hexaen-12-yl]-pyrrolidin-1-yl-methanone (E/Z Mixture)

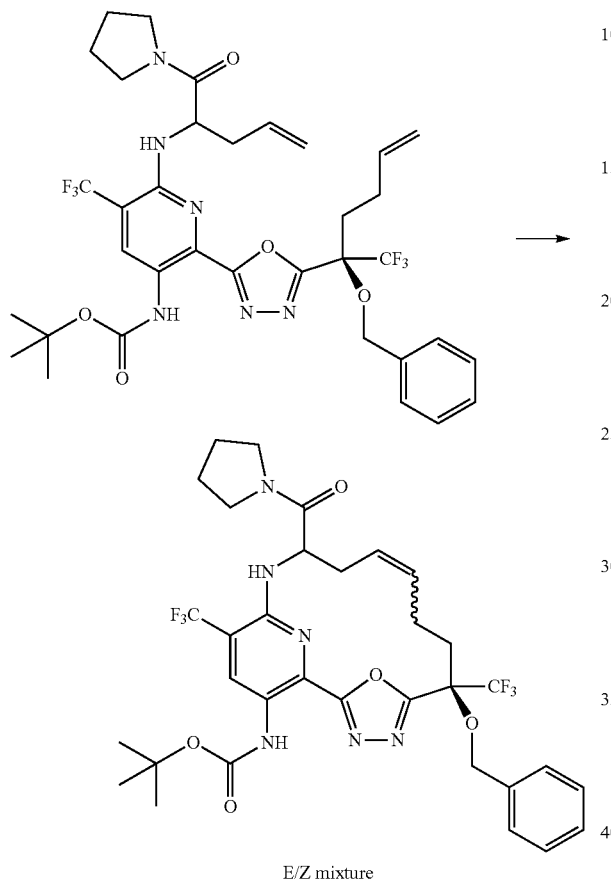

E/Z mixture

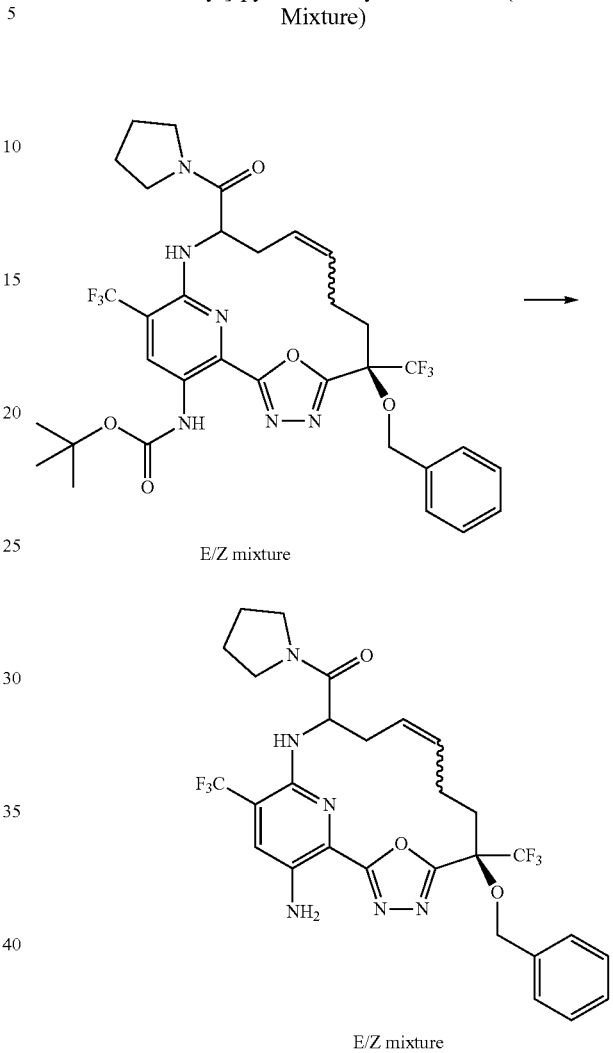

E/Z mixture

In a 500 mL 3-neck flask, a continuously degassed solution via nitrogen line of Zhan catalyst-1B (40 mg, 0.05451 mmol) in 1,2-dichloroethane (100 mL) was heated to 50° C. under nitrogen atmosphere. Then, a solution of tert-butyl N-[2-[5-[(1R)-1-benzyloxy-1-(trifluoromethyl)pent-4-enyl]-1,3,4-oxadiazol-2-yl]-6-[1-(pyrrolidine-1-carbonyl)but-3-enylamino]-5-(trifluoromethyl)-3-pyridyl]carbamate (155 mg, 0.2098 mmol) in 1,2-dichloroethane (50 mL) was added via syringe. The resulting mixture was heated at 75° C. for 2 h. The mixture was concentrated and then purified by silica gel chromatography (24 gram column) using a gradient from 100% hexanes to 60% ethyl acetate in hexanes to afford as a light yellow solid, tert-butyl N-[(6R)-6-benzyloxy-12-(pyrrolidine-1-carbonyl)-6,15-bis(trifluoromethyl)-19-oxa-3,4,13,18-tetrazatricyclo[12.3.1.1²,⁵]nonadeca-1(17),2,4,9,14(18),15-hexaen-17-yl]carbamate (E/Z mixture) (98 mg, 66%). ESI-MS m/z calc. 710.26514, found 711.2 (M+1)⁺; Retention time: 1.62 minutes (LC Method M).

TFA (750 µL, 9.735 mmol) was added to a solution of tert-butyl N-[(6R)-6-benzyloxy-12-(pyrrolidine-1-carbonyl)-6,15-bis(trifluoromethyl)-19-oxa-3,4,13,18-tetrazatricyclo[12.3.1.1²,⁵]nonadeca-1(17),2,4,9,14(18),15-hexaen-17-yl]carbamate (E/Z mixture) (98 mg, 0.138 mmol) in 1,2-dichloroethane (100 mL) and the resulting mixture was stirred for 20 minutes. The reaction mixture was concentrated to dryness then diluted with hexanes and DCM and concentrated again then dried under vacuum overnight to afford as a light green solid, [(6R)-17-amino-6-benzyloxy-6,15-bis(trifluoromethyl)-19-oxa-3,4,13,18-tetrazatricyclo[12.3.1.1²,⁵]nonadeca-1(17),2,4,9,14(18),15-hexaen-12-yl]-pyrrolidin-1-yl-methanone (E/Z mixture) (105 mg, 82%). ESI-MS m/z calc. 610.2127, found 611.0 (M+1)⁺; Retention time: 1.67 minutes (LC Method J).

719

Step 8: [(6R)-17-Amino-6-hydroxy-6,15-bis(trifluoromethyl)-19-oxa-3,4,13,18-tetrazatricyclo[12.3.1.1²,⁵]nonadeca-1(18),2,4,14,16-pentaen-12-yl]-pyrrolidin-1-yl-methanone (Compound 154)

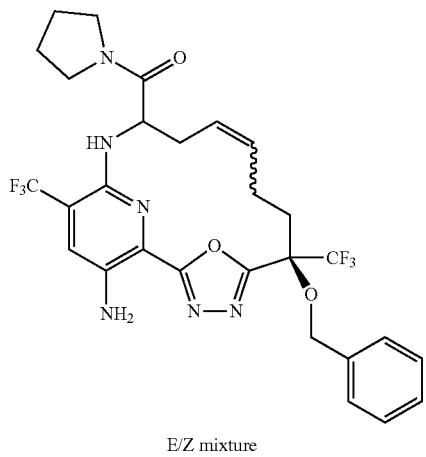

E/Z mixture

In a 50 mL round bottom flask, a solution of [(6R)-17-amino-6-benzyloxy-6,15-bis(trifluoromethyl)-19-oxa-3,4,13,18-tetrazatricyclo[12.3.1.1²,⁵]nonadeca-1(17),2,4,9,14(18),15-hexaen-12-yl]-pyrrolidin-1-yl-methanone (E/Z mixture) (98 mg, 0.1605 mmol) in AcOH (2.5 mL) and ethyl acetate (5 mL) was purged with nitrogen. Then, Pd/C (185 mg, 10% w/w, 0.1738 mmol) was added. The mixture was degassed with nitrogen then purged by a balloon filled with hydrogen gas. The mixture was stirred at 1 atm of hydrogen for 5 h. The mixture was filtered through Celite, washing with excess ethyl acetate and the filtrate was concentrated. The residue was purified by silica gel chromatography (12 gram column) using a gradient from 100% hexanes to 100% ethyl acetate to afford as a yellow solid, [(6R)-17-amino-6-hydroxy-6,15-bis(trifluoromethyl)-19-oxa-3,4,13,18-tetrazatricyclo[12.3.1.1²,⁵]nonadeca-1(18),2,4,14,16-pentaen-12-yl]-pyrrolidin-1-yl-methanone (48.3 mg, 58%). ESI-MS m/z calc. 522.1814, found 523.1 (M+1)⁺; Retention time: 1.68 minutes (LC Method A).

720

Example 85: Preparation of (6R)-17-amino-6-hydroxy-6,15-bis(trifluoromethyl)-19-oxa-3,4,13,18-tetrazatricyclo[12.3.1.1²,⁵]nonadeca-1(18),2,4,14,16-pentaene-12-carboxylic acid (enantiomer 1) (Compound 155) and (6R)-17-amino-6-hydroxy-6,15-bis(trifluoromethyl)-19-oxa-3,4,13,18-tetrazatricyclo[12.3.1.1²,⁵]nonadeca-1(18),2,4,14,16-pentaene-12-carboxylic acid (enantiomer 2) (Compound 156)

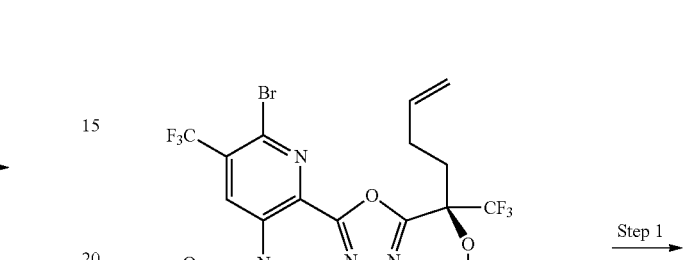

Step 1 →

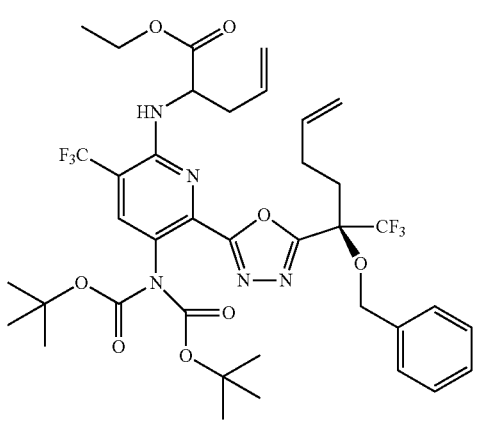

+

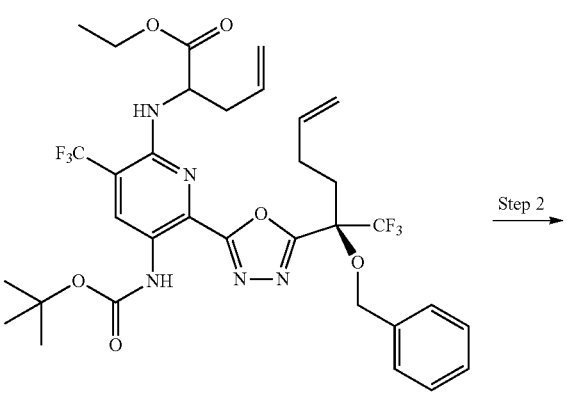

Step 2 →

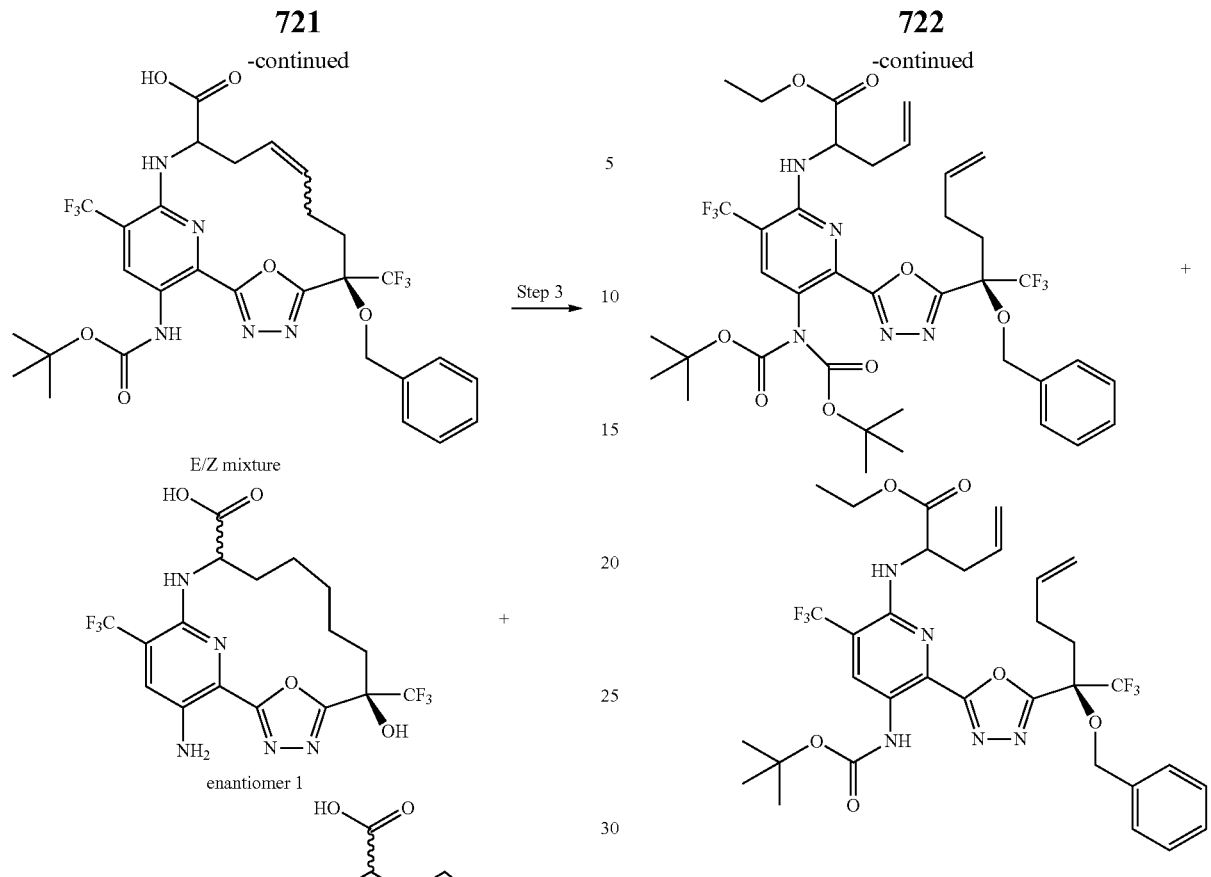

Step 1: Ethyl 2-[[6-[5-[(1R)-1-benzyloxy-1-(trifluoromethyl)pent-4-enyl]-1,3,4-oxadiazol-2-yl]-5-[bis(tert-butoxycarbonyl)amino]-3-(trifluoromethyl)-2-pyridyl]amino]pent-4-enoate and ethyl 2-[[6-[5-[(1R)-1-benzyloxy-1-(trifluoromethyl)pent-4-enyl]-1,3,4-oxadiazol-2-yl]-5-(tert-butoxycarbonylamino)-3-(trifluoromethyl)-2-pyridyl]amino]pent-4-enoate

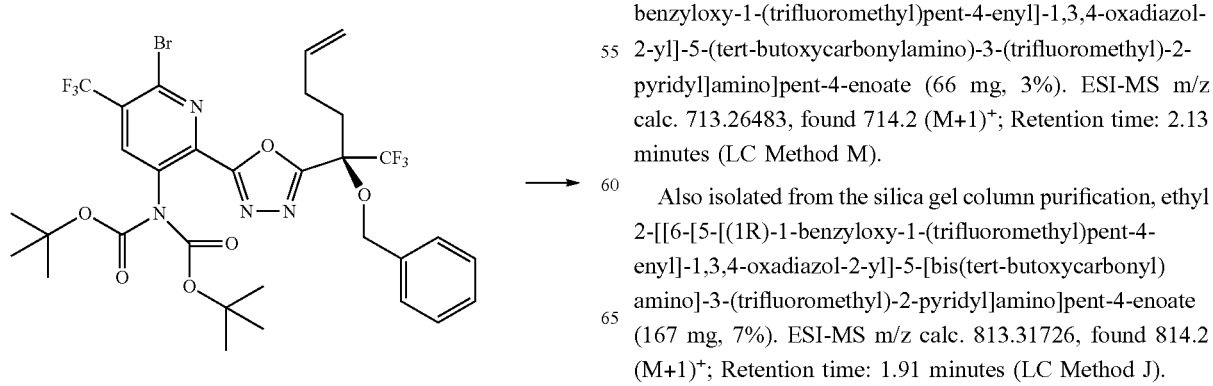

A mixture of tert-butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate (2.1 g, 2.794 mmol), ethyl 2-aminopent-4-enoate (1.2 g, 8.381 mmol), (1E,4E)-1,5-diphenylpenta-1,4-dien-3-one; palladium (128 mg, 0.1398 mmol), Xantphos (165 mg, 0.2852 mmol) and cesium carbonate (3.7 g, 11.36 mmol) in dioxane (32 mL) was degassed by bubbling nitrogen for 1 min then sealed and stirred at 95° C. for 16 h. The reaction was filtered and diluted with ethyl acetate, then washed with water and brine and the organic layer was then dried over sodium sulfate, filtered and evaporated. The crude material was then purified by silica gel chromatography using a gradient from 100% hexanes to 50% ethyl acetate in hexanes to produce as a light yellow solid, ethyl 2-[[6-[5-[(1R)-1-benzyloxy-1-(trifluoromethyl)pent-4-enyl]-1,3,4-oxadiazol-2-yl]-5-(tert-butoxycarbonylamino)-3-(trifluoromethyl)-2-pyridyl]amino]pent-4-enoate (66 mg, 3%). ESI-MS m/z calc. 713.26483, found 714.2 (M+1)$^+$; Retention time: 2.13 minutes (LC Method M).

Also isolated from the silica gel column purification, ethyl 2-[[6-[5-[(1R)-1-benzyloxy-1-(trifluoromethyl)pent-4-enyl]-1,3,4-oxadiazol-2-yl]-5-[bis(tert-butoxycarbonyl)amino]-3-(trifluoromethyl)-2-pyridyl]amino]pent-4-enoate (167 mg, 7%). ESI-MS m/z calc. 813.31726, found 814.2 (M+1)$^+$; Retention time: 1.91 minutes (LC Method J).

Step 2: (6R)-6-benzyloxy-17-(tert-butoxycarbonylamino)-6,15-bis(trifluoromethyl)-19-oxa-3,4,13,18-tetrazatricyclo[12.3.1.12,5]nonadeca-1(17),2,4,9,14(18),15-hexaene-12-carboxylic Acid (E/Z Mixture)

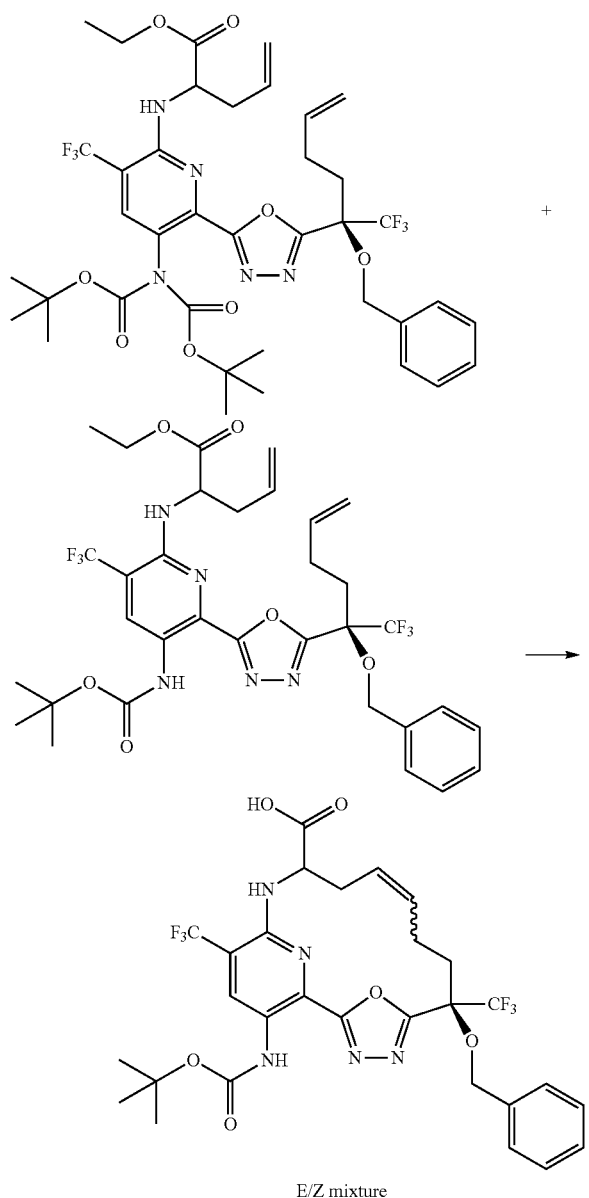

E/Z mixture

In a 500 mL 3-neck flask, a continuously degassed solution via nitrogen line of 0.25 eq Zhan catalyst-1B (52 mg, 0.07087 mmol) was dissolved in DCE (150 mL) and was heated to 50° C. under nitrogen atmosphere. Then, a solution of ethyl 2-[[6-[5-[(1R)-1-benzyloxy-1-(trifluoromethyl)pent-4-enyl]-1,3,4-oxadiazol-2-yl]-5-[bis(tert-butoxycarbonyl)amino]-3-(trifluoromethyl)-2-pyridyl]amino]pent-4-enoate (167 mg, 0.2052 mmol) combined with ethyl 2-[[6-[5-[(1R)-1-benzyloxy-1-(trifluoromethyl)pent-4-enyl]-1,3,4-oxadiazol-2-yl]-5-(tert-butoxycarbonylamino)-3-(trifluoromethyl)-2-pyridyl]amino]pent-4-enoate (66 mg, 0.09248 mmol) in DCE (150 mL) was added via syringe. The resulting mixture was heated to 75° C. for 2 h. The mixture was concentrated and the residue was purified by silica gel chromatography (80 gram column) using a gradient from 100% hexanes to 50% ethyl acetate in hexanes to afford as an off-white solid, 149 mg of a mixture of ethyl (6R)-6-benzyloxy-17-[bis(tert-butoxycarbonyl)amino]-6,15-bis(trifluoromethyl)-19-oxa-3,4,13,18-tetrazatricyclo[12.3.1.12,5]nonadeca-1(18),2,4,9,14,16-hexaene-12-carboxylate and (6R)-6-benzyloxy-17-(tert-butoxycarbonylamino)-6,15-bis(trifluoromethyl)-19-oxa-3,4,13,18-tetrazatricyclo[12.3.1.12,5]nonadeca-1(18),2,4,9,14,16-hexaene-12-carboxylate. To a solution of this mixture in THF (2.5 mL) was added MeOH (2.5 mL), and $H_2O$ (2.5 mL) followed by lithium hydroxide (45 mg, 1.879 mmol). The mixture was stirred at 50° C. for 4 h. THF and methanol were removed under reduced pressure and then 5 mL of 10% aqueous HCl was added to acidify to pH ~4 and the product was extracted with EtOAc (2×25 mL). The organic phases were combined, washed with brine (25 mL), dried over anhydrous sodium sulfate, filtered and concentrated under reduced pressure. The crude material was then purified by silica gel chromatography (24 gram column) using a gradient from 100% hexanes to 80% ethyl acetate in hexanes to afford as a yellow solid, (6R)-6-benzyloxy-17-(tert-butoxycarbonylamino)-6,15-bis(trifluoromethyl)-19-oxa-3,4,13,18-tetrazatricyclo[12.3.1.12,5]nonadeca-1(17),2,4,9,14(18),15-hexaene-12-carboxylic acid (E/Z mixture) (63.3 mg, 21%, 80% purity), ESI-MS m/z calc. 657.2022, found 658.2 $(M+1)^+$; Retention time: 2.03 minutes (LC Method J).

Step 3: (6R)-17-Amino-6-hydroxy-6,15-bis(trifluoromethyl)-19-oxa-3,4,13,18-tetrazatricyclo[12.3.1.12,5]nonadeca-1(18),2,4,14,16-pentaene-12-carboxylic acid (enantiomer 1) (Compound 155) and (6R)-17-amino-6-hydroxy-6,15-bis(trifluoromethyl)-19-oxa-3,4,13,18-tetrazatricyclo[12.3.1.12,5]nonadeca-1(18),2,4,14,16-pentaene-12-carboxylic acid (enantiomer 2) (Compound 156)

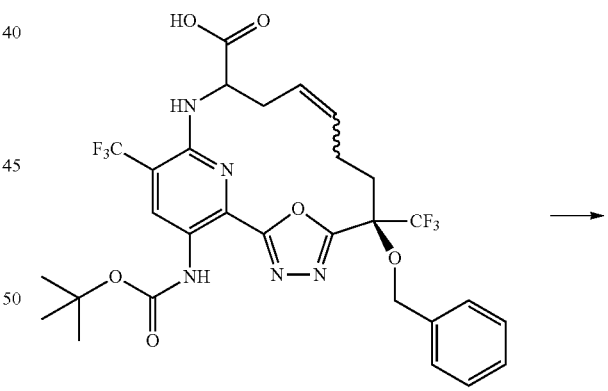

E/Z mixture

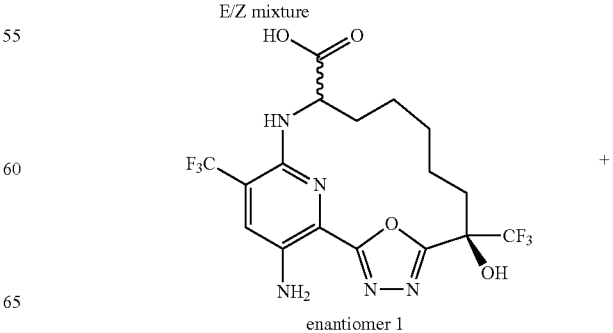

enantiomer 1

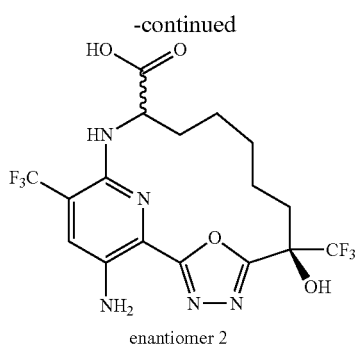

enantiomer 2

To a solution of (6R)-6-benzyloxy-17-(tert-butoxycarbonylamino)-6,15-bis(trifluoromethyl)-19-oxa-3,4,13,18-tetrazatricyclo[12.3.1.1^2,5]nonadeca-1(17),2,4,9,14(18),15-hexaene-12-carboxylic acid (E/Z mixture) (20 mg, 0.03042 mmol) in AcOH (540 µL) was added Pd/C (12.95 mg, 10% w/w, 0.01217 mmol). The mixture was stirred at room temperature for 3 h under a hydrogen filled balloon. The reaction mixture was filtered through a silica plug, washing well with ethyl acetate and then the filtrate was concentrated. To the residue was added TFA (500 µL) and this mixture was stirred for 3 min at room temperature. The mixture was concentrated and purified by reverse phase HPLC using a gradient from 1% to 99% acetonitrile in water (+5 mM HCl) which gave two enantiomeric products:

The first enantiomer to elute was isolated as a yellow solid, (6R)-17-amino-6-hydroxy-6,15-bis(trifluoromethyl)-19-oxa-3,4,13,18-tetrazatricyclo[12.3.1.1^2,5]nonadeca-1(18),2,4,14,16-pentaene-12-carboxylic acid (enantiomer 1) (5 mg, 43%). $^1$H NMR (400 MHz, CD$_3$OD) δ 7.57 (s, 1H), 4.34 (dd, J=9.4, 3.1 Hz, 1H), 2.58-2.44 (m, 1H), 2.44-2.34 (m, 1H), 2.14 (dt, J=13.7, 8.0 Hz, 1H), 1.95-1.86 (m, 1H), 1.79 (d, J=9.0 Hz, 1H), 1.69 (d, J=6.9 Hz, 2H), 1.55 (d, J=9.4 Hz, 1H), 1.49-1.39 (m, 1H), 1.36-1.29 (m, 1H) ppm. ESI-MS m/z calc. 469.11847, found 470.05 (M+1)$^+$; Retention time: 1.29 minutes (LC Method A).

The second enantiomer to elute was collected as a yellow solid, (6R)-17-amino-6-hydroxy-6,15-bis(trifluoromethyl)-19-oxa-3,4,13,18-tetrazatricyclo[12.3.1.1^2,5]nonadeca-1(18),2,4,14,16-pentaene-12-carboxylic acid (enantiomer 2) (4 mg, 28%). $^1$H NMR (400 MHz, CD$_3$OD) δ 7.57 (s, 1H), 4.43 (dd, J=9.2, 3.6 Hz, 1H), 2.51-2.32 (m, 2H), 2.19 (ddd, J=14.8, 9.3, 6.4 Hz, 1H), 1.97-1.67 (m, 4H), 1.61-1.55 (m, 1H), 1.48 (t, J=6.6 Hz, 1H), 1.33 (d, J=6.2 Hz, 1H) ppm. ESI-MS m/z calc. 469.11847, found 470.02 (M+1)$^+$; Retention time: 1.39 minutes (LC Method A).

Example 86: Preparation of [(6R)-17-amino-6-hydroxy-6,15-bis(trifluoromethyl)-19-oxa-3,4,13,18-tetrazatricyclo[12.3.1.1^2,5]nonadeca-1(18),2,4,14,16-pentaen-12-yl]-pyrrolidin-1-yl-methanone (enantiomer 1) (Compound 157) and [(6R)-17-amino-6-hydroxy-6,15-bis(trifluoromethyl)-19-oxa-3,4,13,18-tetrazatricyclo[12.3.1.1^2,5]nonadeca-1(18),2,4,14,16-pentaen-12-yl]-pyrrolidin-1-yl-methanone (enantiomer 2) (Compound 158)

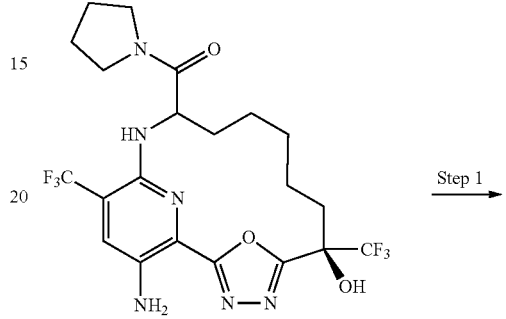

Step 1

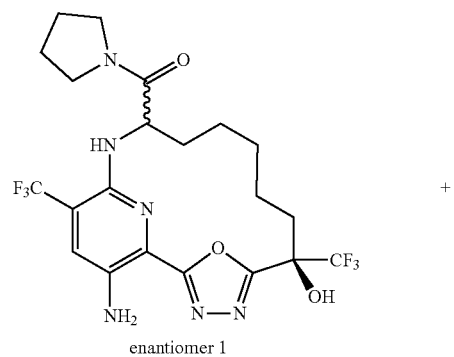

enantiomer 1

+

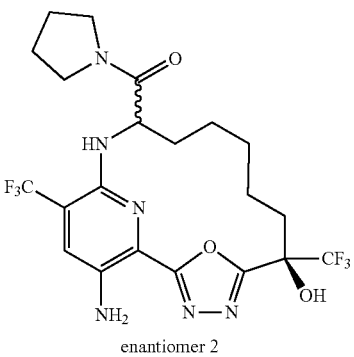

enantiomer 2

Step 1: [(6R)-17-Amino-6-hydroxy-6,15-bis(trifluoromethyl)-19-oxa-3,4,13,18-tetrazatricyclo[12.3.1.1²,⁵]nonadeca-1(18),2,4,14,16-pentaen-12-yl]-pyrrolidin-1-yl-methanone (enantiomer 1) (Compound 157) and [(6R)-17-amino-6-hydroxy-6,15-bis(trifluoromethyl)-19-oxa-3,4,13,18-tetrazatricyclo[12.3.1.1²,⁵]nonadeca-1(18),2,4,14,16-pentaen-12-yl]-pyrrolidin-1-yl-methanone (enantiomer 2) (Compound 158)

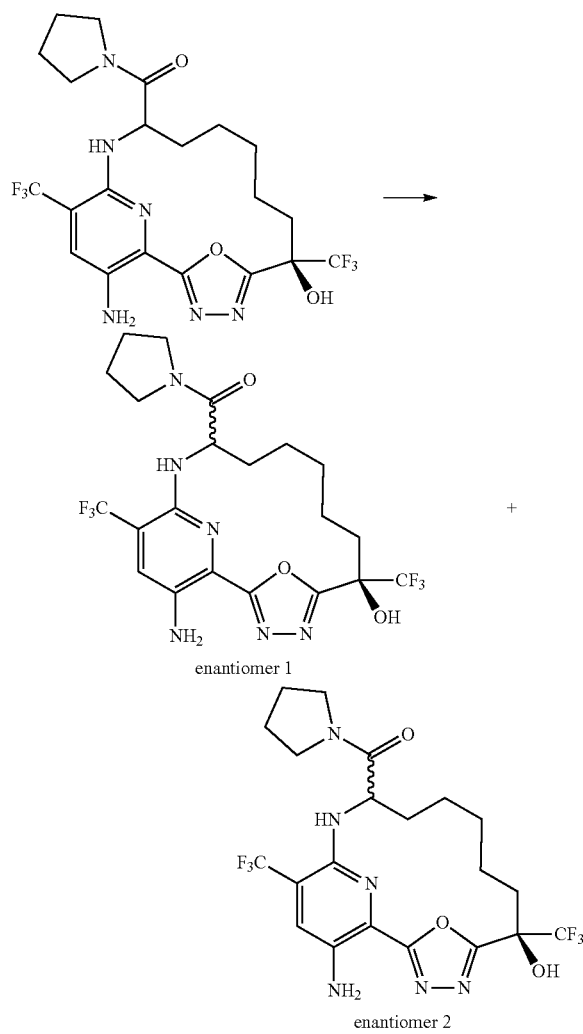

enantiomer 1 enantiomer 2

[(6R)-17-Amino-6-hydroxy-6,15-bis(trifluoromethyl)-19-oxa-3,4,13,18-tetrazatricyclo[12.3.1.1²,⁵]nonadeca-1(18),2,4,14,16-pentaen-12-yl]-pyrrolidin-1-yl-methanone (42 mg, 0.08039 mmol) was purified by chiral SFC using a ChiralPak IC column (250×21.2 mm, 5 μm particle size) eluting with 14% MeOH (+20 mM NH₃)/86% CO₂ at a flow rate of 70 mL/min which provided two single enantiomer products:

The first enantiomer to elute was isolated as a yellow solid and was further purified by reverse phase HPLC using a gradient from 1% to 99% acetonitrile in water (+5 mM HCl) over 15 minutes giving as a yellow solid, [(6R)-17-amino-6-hydroxy-6,15-bis(trifluoromethyl)-19-oxa-3,4,13,18-tetrazatricyclo[12.3.1.1²,⁵]nonadeca-1(18),2,4,14,16-pentaen-12-yl]-pyrrolidin-1-yl-methanone (enantiomer 1) (7.7 mg, 36%). ESI-MS m/z calc. 522.1814, found 523.0 (M+1)⁺; Retention time: 1.68 minutes (LC Method A).

The second enantiomer to elute was further purified by reverse phase HPLC using a gradient from 1% to 99% acetonitrile in water (+5 mM HCl) over 15 minutes which gave as a yellow solid, [(6R)-17-amino-6-hydroxy-6,15-bis(trifluoromethyl)-19-oxa-3,4,13,18-tetrazatricyclo[12.3.1.1²,⁵]nonadeca-1(18),2,4,14,16-pentaen-12-yl]-pyrrolidin-1-yl-methanone (enantiomer 2) (5.3 mg, 25%). ¹H NMR (400 MHz, Chloroform-d) δ 7.33 (s, 1H), 5.65 (s, 1H), 5.07 (s, 1H), 4.77 (d, J=6.0 Hz, 1H), 3.61-3.45 (m, 4H), 2.41 (dt, J=15.4, 8.1 Hz, 1H), 2.30 (dd, J=13.2, 6.8 Hz, 1H), 2.21 (s, 1H), 1.95 (ddd, J=27.7, 12.5, 6.3 Hz, 4H), 1.88-1.83 (m, 1H), 1.67 (dd, J=12.7, 5.9 Hz, 3H), 1.55 (q, J=9.1, 6.7 Hz, 3H) ppm. Exchangeable aryl NH₂ protons not observed in NMR. ESI-MS m/z calc. 522.1814, found 523.0 (M+1)⁺; Retention time: 1.69 minutes (LC Method A).

Example 87: Preparation of (12R)-20-amino-19-methoxy-6-(trifluoromethyl)-22-oxa-3,4,16,21-tetrazatetracyclo[15.3.1.1²,⁵.0¹²,¹⁶]docosa-1(21),2,4,17,19-pentaen-6-ol (enantiomer 1) (hydrochloride salt) (Compound 159) and (12R)-20-amino-19-methoxy-6-(trifluoromethyl)-22-oxa-3,4,16,21-tetrazatetracyclo[15.3.1.1²,⁵.0¹²,¹⁶]docosa-1(21),2,4,17,19-pentaen-6-ol (enantiomer 2) (hydrochloride salt) (Compound 160)

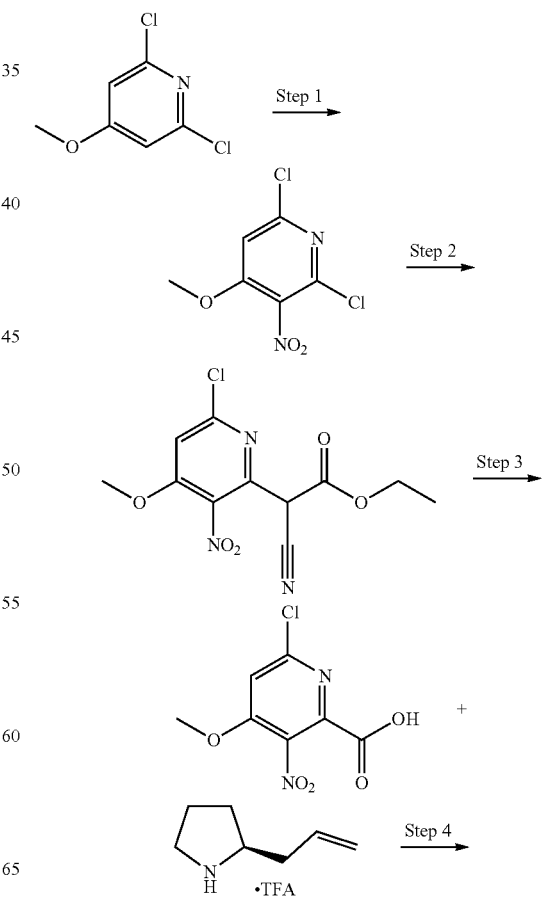

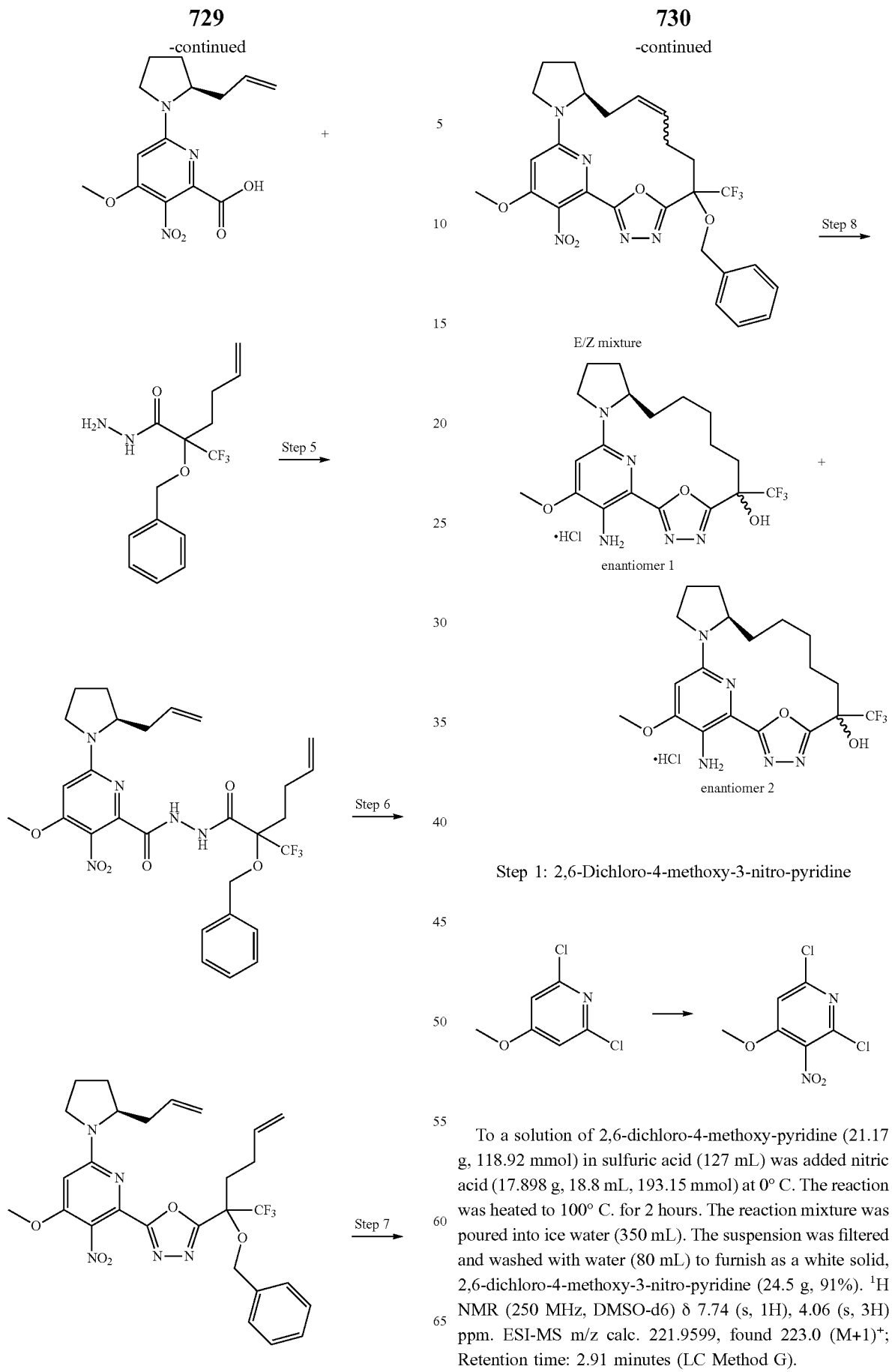

E/Z mixture enantiomer 1 enantiomer 2

Step 1: 2,6-Dichloro-4-methoxy-3-nitro-pyridine

To a solution of 2,6-dichloro-4-methoxy-pyridine (21.17 g, 118.92 mmol) in sulfuric acid (127 mL) was added nitric acid (17.898 g, 18.8 mL, 193.15 mmol) at 0° C. The reaction was heated to 100° C. for 2 hours. The reaction mixture was poured into ice water (350 mL). The suspension was filtered and washed with water (80 mL) to furnish as a white solid, 2,6-dichloro-4-methoxy-3-nitro-pyridine (24.5 g, 91%). $^1$H NMR (250 MHz, DMSO-d6) δ 7.74 (s, 1H), 4.06 (s, 3H) ppm. ESI-MS m/z calc. 221.9599, found 223.0 (M+1)$^+$; Retention time: 2.91 minutes (LC Method G).

Step 2: Ethyl 2-(6-chloro-4-methoxy-3-nitro-2-pyridyl)-2-cyano-acetate

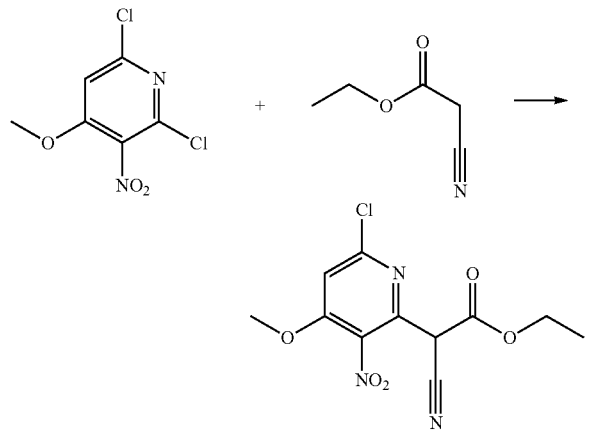

To a solution of 2,6-dichloro-4-methoxy-3-nitro-pyridine (208 mg, 0.914 mmol) and CsCO₃ (446.6 mg, 1.3707 mmol) in DMF (9 mL) was added ethyl 2-cyanoacetate (119.78 mg, 113 μL, 1.0589 mmol). The reaction mixture was stirred at room temperature overnight. Water (20 mL) and aqueous HCl (2 M, 7 mL) were added to reaction mixture, then extracted with EtOAc (3×20 mL). The combined organic layers were washed with water (2×15 mL) then brine (20 mL), dried over Na₂SO₄, filtered and concentrated in vacuo. The crude product was purified by silica gel chromatography (dry loaded on 25 g SiO₂ with minimal DCM) and eluted with a gradient from 0% to 100% EtOAc in hexanes) to afford as a dark yellow oil, ethyl 2-(6-chloro-4-methoxy-3-nitro-2-pyridyl)-2-cyano-acetate (153.8 mg, 56%). ¹H NMR (250 MHz, CDCl₃) δ 7.10 (s, 1H), 5.24 (s, 1H), 4.37-4.26 (m, 2H), 4.05 (s, 3H), 1.33 (s, 3H) ppm. ESI-MS m/z calc. 299.0309, found 300.4 (M+1)⁺; Retention time: 2.85 minutes (LC Method G).

Step 3: 6-Chloro-4-methoxy-3-nitro-pyridine-2-carboxylic Acid

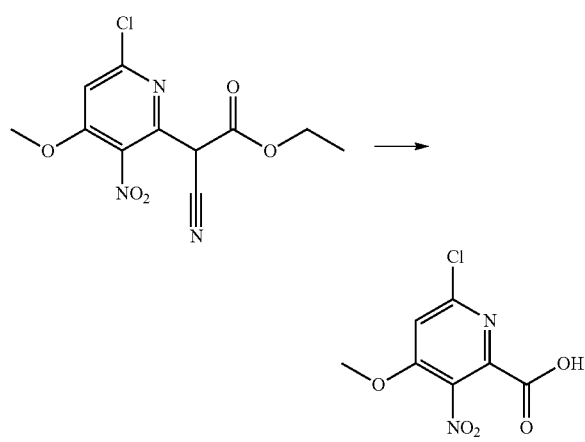

To a mixture of ethyl 2-(6-chloro-4-methoxy-3-nitro-2-pyridyl)-2-cyano-acetate (50.7 mg, 0.1658 mmol) in water (0.3 mL) and DMSO (0.1 mL) was added NaOAc (33.8 mg, 0.412 mmol). The reaction mixture was stirred at 60° C., and H₂O₂ (3.4015 g, 0.1 mL of 30% w/w, 30 mmol) was added dropwise. The reaction mixture was stirred at 60° C. for 1 hour.

The reaction mixture was cooled to room temperature and aqueous HCl (0.5 M, 5 mL) was added then extracted with EtOAc (3×5 mL). The combined organic layers were washed with water (2×5 mL), brine (10 mL), dried over Na₂SO₄, filtered and concentrated in vacuo. The crude product was purified by silica gel chromatography (loaded onto 12 g SiO₂ with minimal DCM) and eluted with a gradient from 0% to 15% MeOH in DCM afford as a light yellow solid, 6-chloro-4-methoxy-3-nitro-pyridine-2-carboxylic acid (22.8 mg, 59%). ¹H NMR (500 MHz, DMSO-d6) δ 7.44 (s, 1H), 3.97 (s, 3H) ppm. ESI-MS m/z calc. 231.9887, found 233.3 (M+1)⁺; Retention time: 1.75 minutes (LC Method G).

Step 4: 6-[(2S)-2-Allylpyrrolidin-1-yl]-4-methoxy-3-nitro-pyridine-2-carboxylic Acid

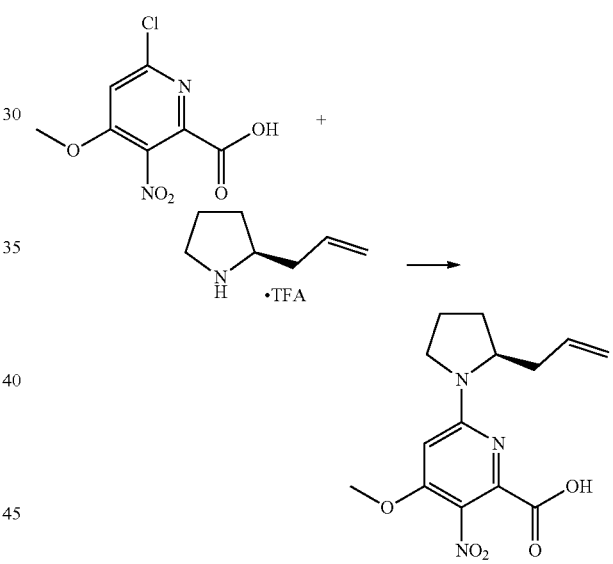

To a solution of 6-chloro-4-methoxy-3-nitro-pyridine-2-carboxylic acid (0.4 g, 1.7199 mmol) and (2S)-2-allylpyrrolidine (trifluoroacetate salt) (0.8 g, 3.5523 mmol) in DMF (45 mL) was added potassium carbonate (1.23 g, 8.8998 mmol) and the mixture was stirred and heated at 110° C. overnight. After cooling to room temperature, the reaction mixture was diluted with 100 mL of water. The mixture was washed with DCM (3×100 mL). The bright yellow aqueous solution was then acidified to pH=3 with 1 N aqueous HCl solution (20 mL). The solution was extracted with DCM (3×100 mL). The combined organic solutions were washed with brine, dried over anhydrous sodium sulfate, filtered and the filtrate was evaporated. The residue was dried in vacuo yielding as a brown oil, 6-[(2S)-2-allylpyrrolidin-1-yl]-4-methoxy-3-nitro-pyridine-2-carboxylic acid (0.84 g, 64%). ESI-MS m/z calc. 307.11682, found 308.5 (M+1)⁺; Retention time: 2.44 minutes (LC Method G). This material was used in the next step without further purification.

Step 5: 6-[(2S)-2-Allylpyrrolidin-1-yl]-N'-[2-benzy-loxy-2-(trifluoromethyl)hex-5-enoyl]-4-methoxy-3-nitro-pyridine-2-carbohydrazide

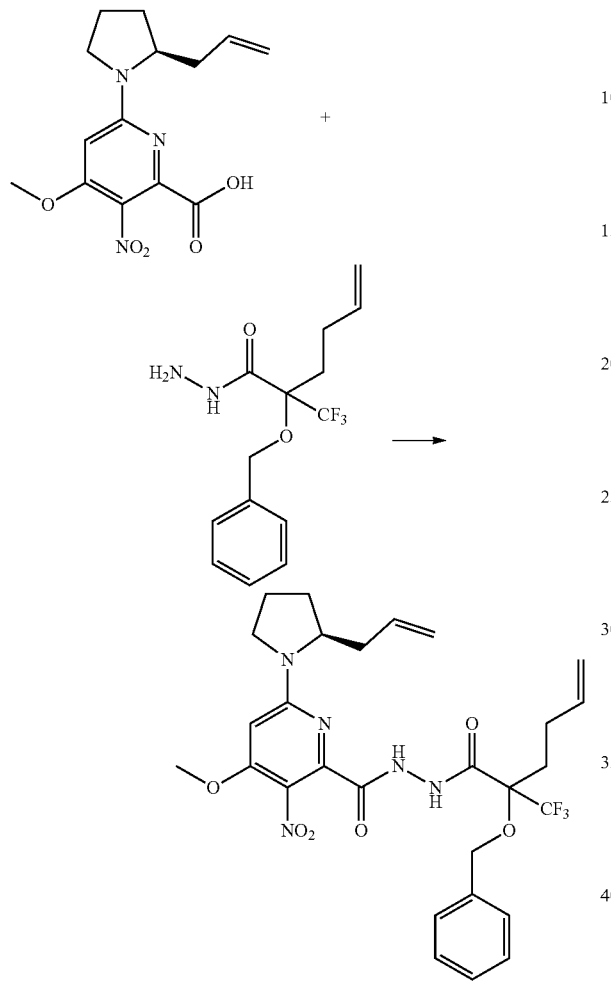

Step 6: 2-[6-[(2S)-2-Allylpyrrolidin-1-yl]-4-methoxy-3-nitro-2-pyridyl]-5-[1-benzyloxy-1-(trifluoromethyl)pent-4-enyl]-1,3,4-oxadiazole

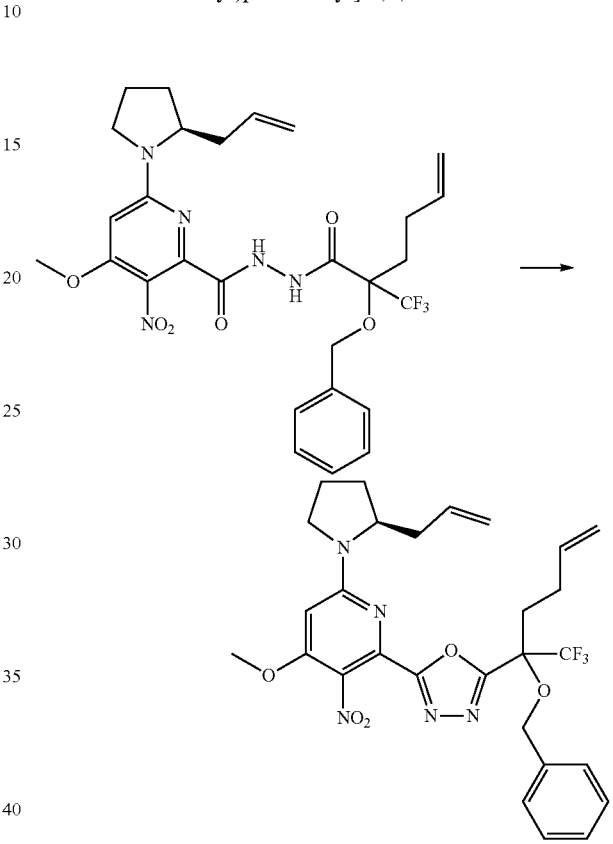

Into a solution of 6-[(2S)-2-allylpyrrolidin-1-yl]-4-methoxy-3-nitro-pyridine-2-carboxylic acid (3.55 g, 7.649 mmol) in EtOAc (130 mL) was added 2-benzyloxy-2-(trifluoromethyl)hex-5-enehydrazide (hydrochloride salt) (3.93 g, 11.601 mmol) and pyridine (3.7164 g, 3.8 mL, 46.984 mmol) and the solution turned cloudy. Propylphosphonic anhydride solution in EtOAc (9.6218 g, 9.0007 mL of 50 w/w, 15.12 mmol) was then added and the mixture was heated at 50° C. for 2 h. The reaction mixture was cooled down to room temperature and was quenched with 1 M aqueous NaHCO₃ solution (250 mL) by stirring for 15 min. The layers were separated and the aqueous layer was extracted with EtOAc (2×200 mL). The combined organic layers were washed with brine (300 mL), dried (Na₂SO₄), filtered and evaporated. The oily residue was dry loaded onto silica and purified by silica gel column chromatography (220 g column, 0% to 40% EtOAc in hexanes) yielding as a foamy yellow solid, 6-[(2S)-2-Allylpyrrolidin-1-yl]-N'-[2-benzyloxy-2-(trifluoromethyl)hex-5-enoyl]-4-methoxy-3-nitro-pyridine-2-carbohydrazide (2.3 g, 50%). $^1$H NMR (500 MHz, CDCl₃) δ 10.07-9.99 (m, 1H), 9.40-9.31 (m, 1H), 7.43-7.32 (m, 5H), 5.92 (s, 1H), 5.87-5.75 (m, 2H), 5.16- 4.99 (m, 4H), 4.81 (d, J 10.5 Hz, 1H), 4.68 (d, J 10.6 Hz, 1H), 4.19 (s, 1H), 3.90 (s, 3H), 3.56 (s, 1H), 3.40 (s, 1H), 2.58-2.37 (m, 2H), 2.29-1.90 (m, 8H) ppm. ESI-MS m/z calc. 591.2305, found 592.5 (M+1)⁺; Retention time: 3.4 minutes (LC Method G).

To a solution of 6-[(2S)-2-allylpyrrolidin-1-yl]-N'-[2-benzyloxy-2-(trifluoromethyl)hex-5-enoyl]-4-methoxy-3-nitro-pyridine-2-carbohydrazide (0.4 g, 0.4402 mmol) and DIEA (296.80 mg, 0.4 mL, 2.2964 mmol) in acetonitrile (20 mL) at 50° C. was added tosyl chloride (0.14 g, 0.7343 mmol). The temperature was raised to 70° C. and the mixture was stirred at this temperature overnight. More tosyl chloride (0.14 g, 0.7343 mmol) and DIEA (296.80 mg, 0.4 mL, 2.2964 mmol) were added and heating was continued for 6 h. Additional tosyl chloride (0.42 g, 2.203 mmol) and DIEA (890.40 mg, 1.2 mL, 6.8893 mmol) were added and heating was continued overnight. After cooling to room temperature, the reaction mixture was concentrated. The residue was dissolved in ethyl acetate (100 mL). The organic layer was washed with aqueous 5% NaHCO₃ (100 mL), water (2×100 mL) and brine (100 mL), dried over anhydrous sodium sulfate, filtered and concentrated in vacuo. The crude product was purified by flash chromatography (crude dry-loaded onto an 25 g column eluting from 0% to 40% EtOAc in hexanes) yielding as a yellow green solid, 2-[6-[(2S)-2-allylpyrrolidin-1-yl]-4-methoxy-3-nitro-2-pyridyl]-5-[1-benzyloxy-1-(trifluoromethyl)pent-4-enyl]-1,3,4-oxadiazole (0.23 g, 89%). ESI-MS m/z calc. 573.2199, found 574.5 (M+1)⁺; Retention time: 3.87 minutes (LC Method G).

Step 7: (12S)-6-benzyloxy-19-methoxy-20-nitro-6-(trifluoromethyl)-22-oxa-3,4,16,21-tetrazatetracyclo[15.3.1.12,5.012,16]docosa-1(21),2,4,9,17,19-hexaene (E/Z mixture)

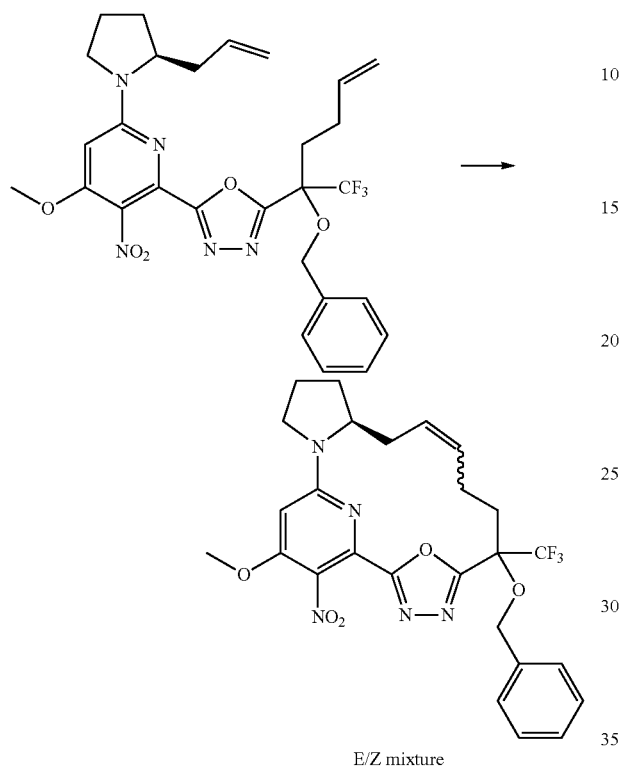

E/Z mixture

To a degassed solution of 2-[6-[(2S)-2-Allylpyrrolidin-1-yl]-4-methoxy-3-nitro-2-pyridyl]-5-[1-benzyloxy-1-(trifluoromethyl)pent-4-enyl]-1,3,4-oxadiazole (1 g, 1.7116 mmol) in DCE (250 mL) at 50° C. under nitrogen atmosphere was added Zhan catalyst-1B (200 mg, 0.2722 mmol). The resulting mixture was heated to 70° C. and stirred for 5 h. The reaction mixture was cooled down and concentrated under reduced pressure. The residue was purified by silica gel column chromatography (dry-loaded onto 25 g of silica gel, and eluted with a gradient from 0% to 40% EtOAc in hexanes) yielding as a green solid, (12S)-6-benzyloxy-19-methoxy-20-nitro-6-(trifluoromethyl)-22-oxa-3,4,16,21-tetrazatetracyclo[15.3.1.12,5.012,16]docosa-1(21),2,4,9,17,19-hexaene (E/Z mixture) (320 mg, 29%). $^1$H NMR (500 MHz, DMSO-d6) δ 7.40-7.21 (m, 5H), 6.33 (s, 1H), 5.70-5.36 (m, 2H), 4.70 (d, J=11.2 Hz, 1H), 4.60 (d, J=11.1 Hz, 1H), 4.00 (s, 3H), 3.95-3.85 (m, 1H), 3.53 (t, J=7.7 Hz, 1H), 3.38 (t, J=10.3 Hz, 2H), 2.45-2.34 (m, 2H), 2.17-1.90 (m, 6H), 1.62-1.49 (m, 1H) ppm. ESI-MS m/z calc. 545.1886, found 546.1 (M+1)$^+$; Retention time: 3.46 minutes (LC Method H).

Step 8: (12R)-20-Amino-19-methoxy-6-(trifluoromethyl)-22-oxa-3,4,16,21-tetrazatetracyclo[15.3.1.12,5.012,16]docosa-1(21),2,4,17,19-pentaen-6-ol (enantiomer 1) (hydrochloride salt) (Compound 159) and (12R)-20-amino-19-methoxy-6-(trifluoromethyl)-22-oxa-3,4,16,21-tetrazatetracyclo[15.3.1.12,5.012,16]docosa-1(21),2,4,17,19-pentaen-6-ol (enantiomer 2) (hydrochloride salt) (Compound 160)

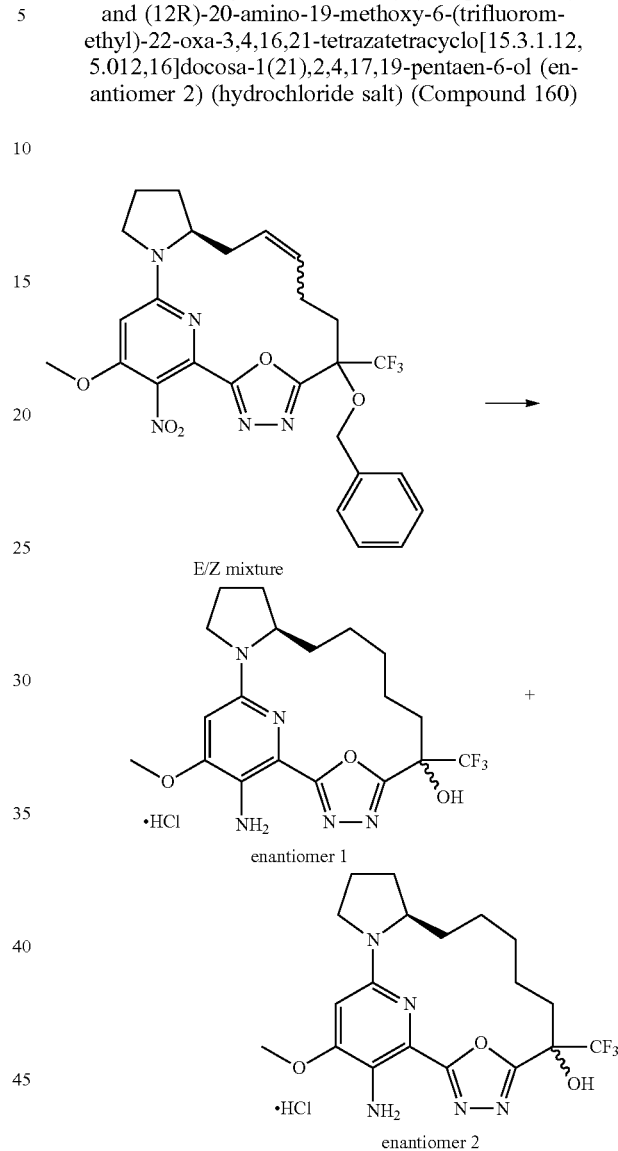

To a solution of (12S)-6-benzyloxy-19-methoxy-20-nitro-6-(trifluoromethyl)-22-oxa-3,4,16,21-tetrazatetracyclo[15.3.1.12,5.012,16]docosa-1(21),2,4,9,17,19-hexaene (E/Z mixture) (226 mg, 0.3503 mmol) in MeOH (15 mL) was added palladium on carbon (226 mg, 0.2124 mmol). The flask was filled with nitrogen, evacuated, and back-filled with hydrogen. This was repeated three times. The mixture was hydrogenated at 60 psi for 2 days. The mixture was filtered over a pad of Celite and the filter cake was washed with MeOH (2×100 mL). The combined filtrate was evaporated then was purified by HPLC using a gradient from 15% to 75% acetonitrile in water (+5 mM HCl) over 30 min with a flow rate of 30 mL/min yielding two diastereomeric products:

The first diastereomer to elute was isolated as (12R)-20-amino-19-methoxy-6-(trifluoromethyl)-22-oxa-3,4,16,21-tetrazatetracyclo[15.3.1.12,5.012,16]docosa-1(21),2,4,17,19-pentaen-6-ol (enantiomer 1) (hydrochloride salt) (10.6 mg, 6%). ¹H NMR (500 MHz, DMSO-d6) δ 7.52 (br, 2H), 6.28 (s, 1H), 3.94 (s, 3H), 3.85 (s, 1H), 3.51-3.37 (m, 2H), 3.29-3.13 (m, 1H), 2.20-1.84 (m, 6H), 1.80-1.65 (m, 2H), 1.65-1.52 (m, 2H), 1.50-1.34 (m, 3H), 0.98-0.81 (m, 1H) ppm. ESI-MS m/z calc. 427.1831, found 428.2 (M+1)⁺; Retention time: 2.0 minutes (LC Method H).

The second diastereomer to elute was isolated as (12R)-20-amino-19-methoxy-6-(trifluoromethyl)-22-oxa-3,4,16,21-tetrazatetracyclo[15.3.1.1²,⁵.0¹²,¹⁶]docosa-1(21),2,4,17,19-pentaen-6-ol (enantiomer 2) (hydrochloride salt) (21.3 mg, 12%). ¹H NMR (500 MHz, DMSO-d6) δ 7.52 (br, 2H), 6.21 (s, 1H), 4.05-3.78 (m, 4H, OH and CH₃), 3.47 (m, 2H), 3.20 (m, 1H), 2.27 (t, J=11.5 Hz, 1H), 2.14-2.04 (m, 1H), 2.04-1.64 (m, 7H), 1.54-1.28 (m, 4H), 1.03-0.80 (m, 1H) ppm. ESI-MS m/z calc. 427.1831, found 428.2 (M+1)⁺; Retention time: 2.0 minutes (LC Method H).

Example 88: Preparation of (12R)-20-amino-18-methanesulfonyl-6-(trifluoromethyl)-22-oxa-3,4,16,21-tetraazatetracyclo[15.3.1.1²,⁵.0¹²,¹⁶]docosa-1(21),2,4,17,19-pentaen-6-ol (enantiomer 1) (Compound 161) and (12R)-20-amino-18-methanesulfonyl-6-(trifluoromethyl)-22-oxa-3,4,16,21-tetraazatetracyclo[15.3.1.1²,⁵.0¹²,¹⁶]docosa-1(21),2,4,17,19-pentaen-6-ol (enantiomer 2) (Compound 162)

Step 1: tert-Butyl N-[(tert-butoxy)carbonyl]-N-1 (12R)-6-hydroxy-18-methanesulfonyl-6-(trifluoromethyl)-22-oxa-3,4,16,21-tetraazatetracyclo[15.3.1.1²,⁵.0¹²,¹⁶]docosa-1(21),2,4,17,19-pentaen-20-yl] carbamate

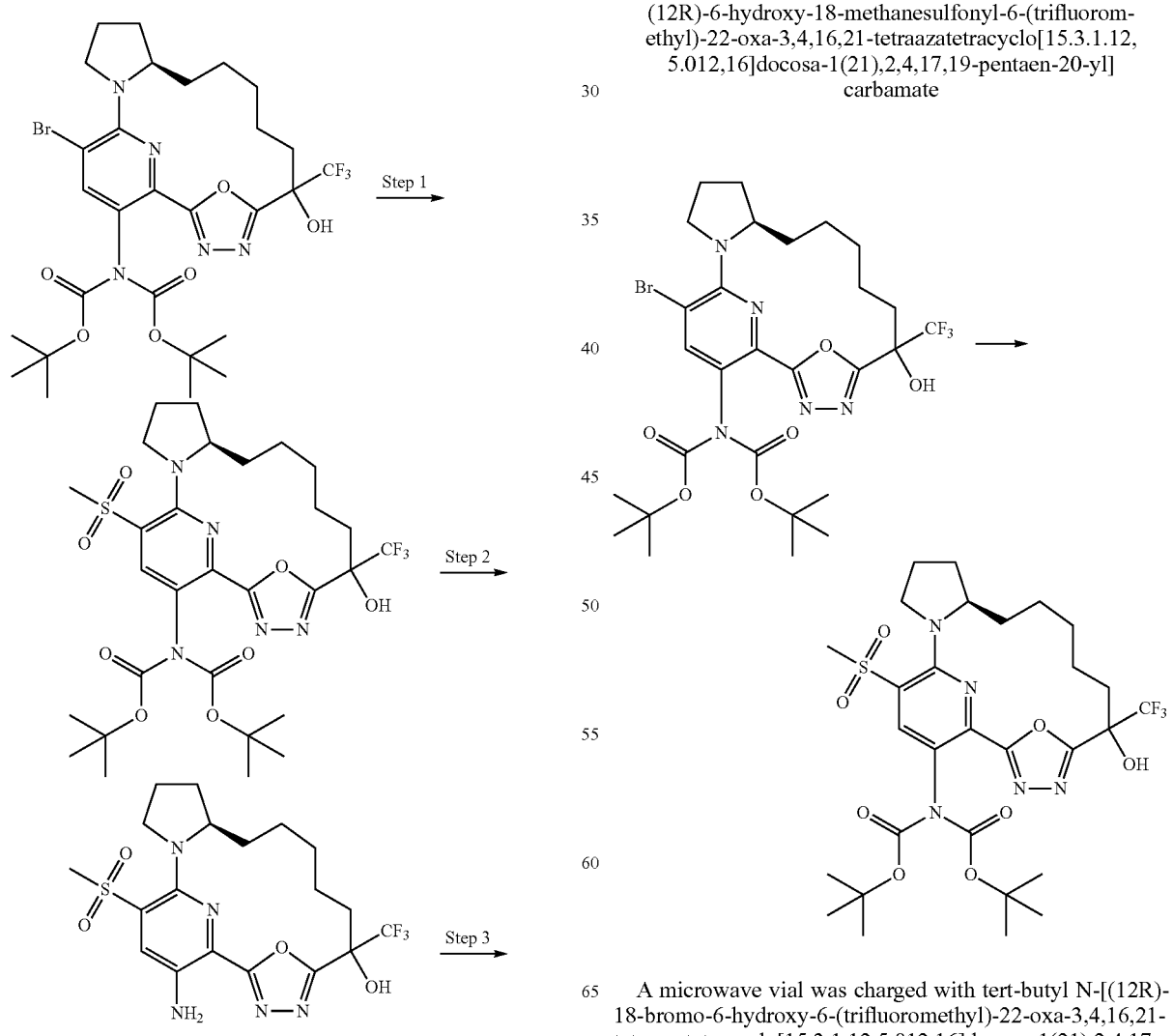

A microwave vial was charged with tert-butyl N-[(12R)-18-bromo-6-hydroxy-6-(trifluoromethyl)-22-oxa-3,4,16,21-tetraazatetracyclo[15.3.1.1²,⁵.0¹²,¹⁶]docosa-1(21),2,4,17, 19-pentaen-20-yl]-N-[(tert-butoxy)carbonyl]carbamate (100 mg, 0.1478 mmol), sodium methanesulfinate (46 mg, 0.4506 mmol), copper(I) iodide (33 mg, 0.1733 mmol), L-proline (1.3 mg, 0.0113 mmol) and DMSO (1.2 mL). The tube was flushed with nitrogen for 2 min and sealed. The mixture was stirred at 112° C. for 3 h, cooled to room temperature and then added 28% aqueous $NH_3$ (2 mL) and water (10 mL). The mixture was extracted with MTBE (3×20 mL). The combined organic layers were dried with sodium sulfate, filtered and concentrated. The residue was purified by silica gel chromatography (12 g column) using a gradient from 0% to 30% of ethyl acetate in heptanes to afford as a yellow oil, tert-butyl N-[(tert-butoxy)carbonyl]-N-[(12R)-6-hydroxy-18-methanesulfonyl-6-(trifluoromethyl)-22-oxa-3,4,16,21-tetraazatetracyclo[15.3.1.12,5.012,16]docosa-1(21),2,4,17,19-pentaen-20-yl]carbamate (48 mg, 48%). ESI-MS m/z calc. 675.255, found 676.2 (M+1)$^+$; Retention time: 1.99 minutes (LC Method Y). Product was contaminated with a small amount of the mono-Boc protected analogous product.

Step 2: (12R)-20-Amino-18-methanesulfonyl-6-(trifluoromethyl)-22-oxa-3,4,16,21-tetraazatetracyclo[15.3.1.12,5.012,16]docosa-1(21),2,4,17,19-pentaen-6-ol

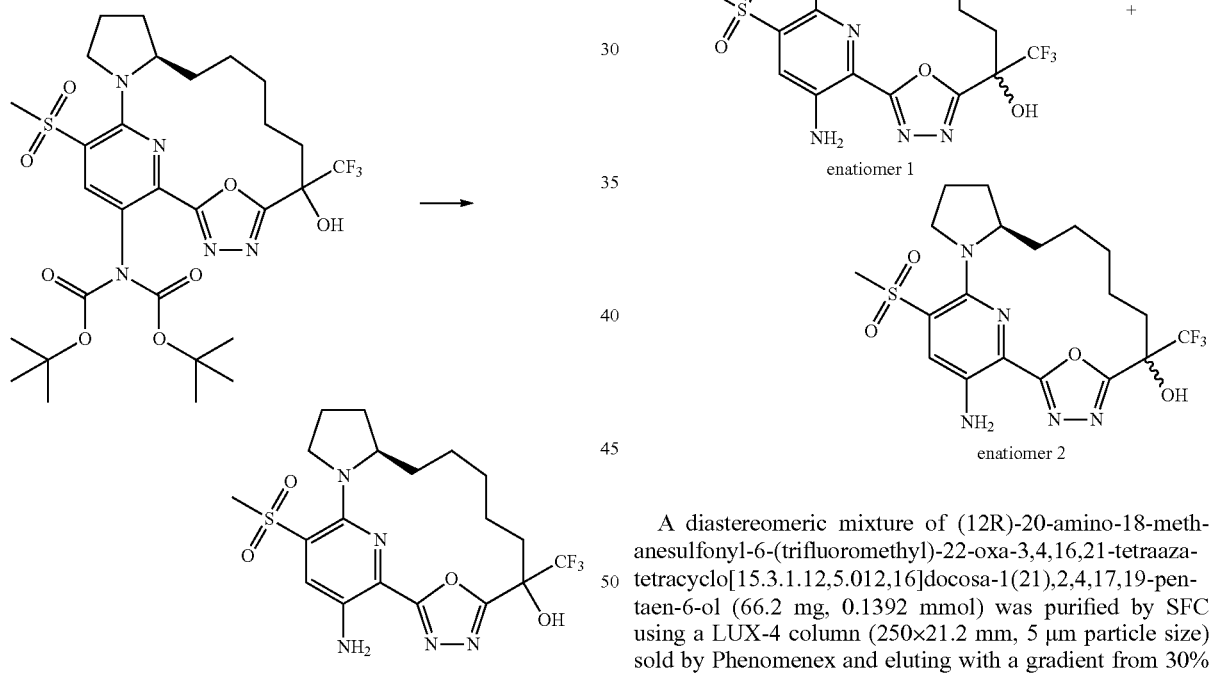

To a solution of tert-butyl N-[(tert-butoxy)carbonyl]-N-[(12R)-6-hydroxy-18-methanesulfonyl-6-(trifluoromethyl)-22-oxa-3,4,16,21-tetraazatetracyclo[15.3.1.12,5.012,16]docosa-1(21),2,4,17,19-pentaen-20-yl]carbamate (74 mg, 0.1095 mmol) in dichloromethane (3 mL) was added TFA (4.44 g, 3 mL, 38.94 mmol) and the reaction mixture was stirred at room temperature for 3 h. The material was concentrated and the residue was purified by silica gel chromatography (12 g column) using a gradient from 20% to 50% ethyl acetate in heptanes giving as a yellow oil, (12R)-20-amino-18-methanesulfonyl-6-(trifluoromethyl)-22-oxa-3,4,16,21-tetraazatetracyclo[15.3.1.12,5.012,16]docosa-1(21),2,4,17,19-pentaen-6-ol (40 mg, 77%). ESI-MS m/z calc. 475.15012, found 476.2 (M+1)$^+$; Retention time: 1.89 minutes (LC Method Z).

Step 3: (12R)-20-Amino-18-methanesulfonyl-6-(trifluoromethyl)-22-oxa-3,4,16,21-tetraazatetracyclo[15.3.1.12,5.012,16]docosa-1(21),2,4,17,19-pentaen-6-ol (enantiomer 1) (Compound 161) and (12R)-20-Amino-18-methanesulfonyl-6-(trifluoromethyl)-22-oxa-3,4,16,21-tetraazatetracyclo[15.3.1.12,5.012,16]docosa-1(21),2,4,17,19-pentaen-6-ol (enantiomer 2) (Compound 162)

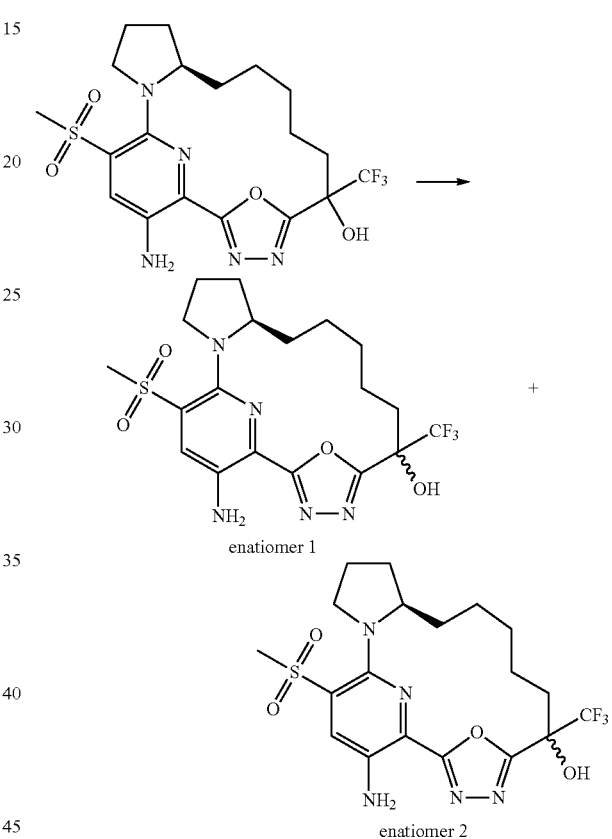

A diastereomeric mixture of (12R)-20-amino-18-methanesulfonyl-6-(trifluoromethyl)-22-oxa-3,4,16,21-tetraazatetracyclo[15.3.1.12,5.012,16]docosa-1(21),2,4,17,19-pentaen-6-ol (66.2 mg, 0.1392 mmol) was purified by SFC using a LUX-4 column (250×21.2 mm, 5 μm particle size) sold by Phenomenex and eluting with a gradient from 30% to 45% MeOH (+20 mM $NH_3$) in $CO_2$ which provided two single enantiomer products:

The first enantiomer to elute was isolated as a yellow solid, (12R)-20-amino-18-methanesulfonyl-6-(trifluoromethyl)-22-oxa-3,4,16,21-tetraazatetracyclo[15.3.1.12,5.012,16]docosa-1(21),2,4,17,19-pentaen-6-ol (enantiomer 1) (25.3 mg, 76%). $^1$H NMR (400 MHz, DMSO-d6) δ 7.99 (s, 1H), 7.59 (s, 1H), 6.31 (s, 2H), 3.88 (p, J=7.7 Hz, 2H), 3.33 (s, 3H), 3.30-3.24 (m, 1H), 2.35 (d, J=13.0 Hz, 1H), 2.30-2.20 (m, 1H), 2.14 (dt, J=12.9, 7.4 Hz, 1H), 2.06-1.94 (m, 1H), 1.94-1.84 (m, 1H), 1.79-1.67 (m, 1H), 1.63-1.37 (m, 7H), 0.95-0.78 (m, 1H) ppm. ESI-MS m/z calc. 475.15012, found 476.0 (M+1)$^+$; Retention time: 2.43 minutes (LC Method D).

The second enantiomer to elute was isolated as a yellow solid, (12R)-20-amino-18-methanesulfonyl-6-(trifluoromethyl)-22-oxa-3,4,16,21-tetraazatetracyclo[15.3.1.12,5.012,16]docosa-1(21),2,4,17,19-pentaen-6-ol (enantiomer 2) (17.3 mg, 52%). $^{1}$H NMR (400 MHz, DMSO-d6) δ 7.99 (s, 1H), 7.57 (s, 1H), 6.33 (d, J=6.5 Hz, 2H), 4.02 (q, J=8.1 Hz, 1H), 3.88 (q, J=7.9 Hz, 1H), 3.32 (s, 3H), 3.22 (dd, J=18.3, 3.9 Hz, 1H), 2.30-2.13 (m, 3H), 2.11-1.99 (m, 1H), 1.97-1.84 (m, 1H), 1.75 (dq, J=19.5, 11.3, 9.2 Hz, 2H), 1.53 (ddd, J=29.0, 16.3, 7.5 Hz, 4H), 1.43-1.30 (m, 2H), 0.95 (dt, J=10.7, 5.4 Hz, 1H) ppm. ESI-MS m/z calc. 475.15012, found 476.0 (M+1)$^{+}$; Retention time: 2.31 minutes (LC Method D).

Example 89: Preparation of (6R)-17-amino-12,12-dimethyl-6,15-bis(trifluoromethyl)-19-oxa-3,4,13,18-tetrazatricyclo[12.3.1.12,5]nonadeca-1(18),2,4,14,16-pentaen-6-ol (Compound 163) and (6R)-12,12-dimethyl-6,15-bis(trifluoromethyl)-19-oxa-3,4,13,18-tetrazatricyclo[12.3.1.12,5]nonadeca-1(18),2,4,14,16-pentaene-6,17-diol (Compound 164)

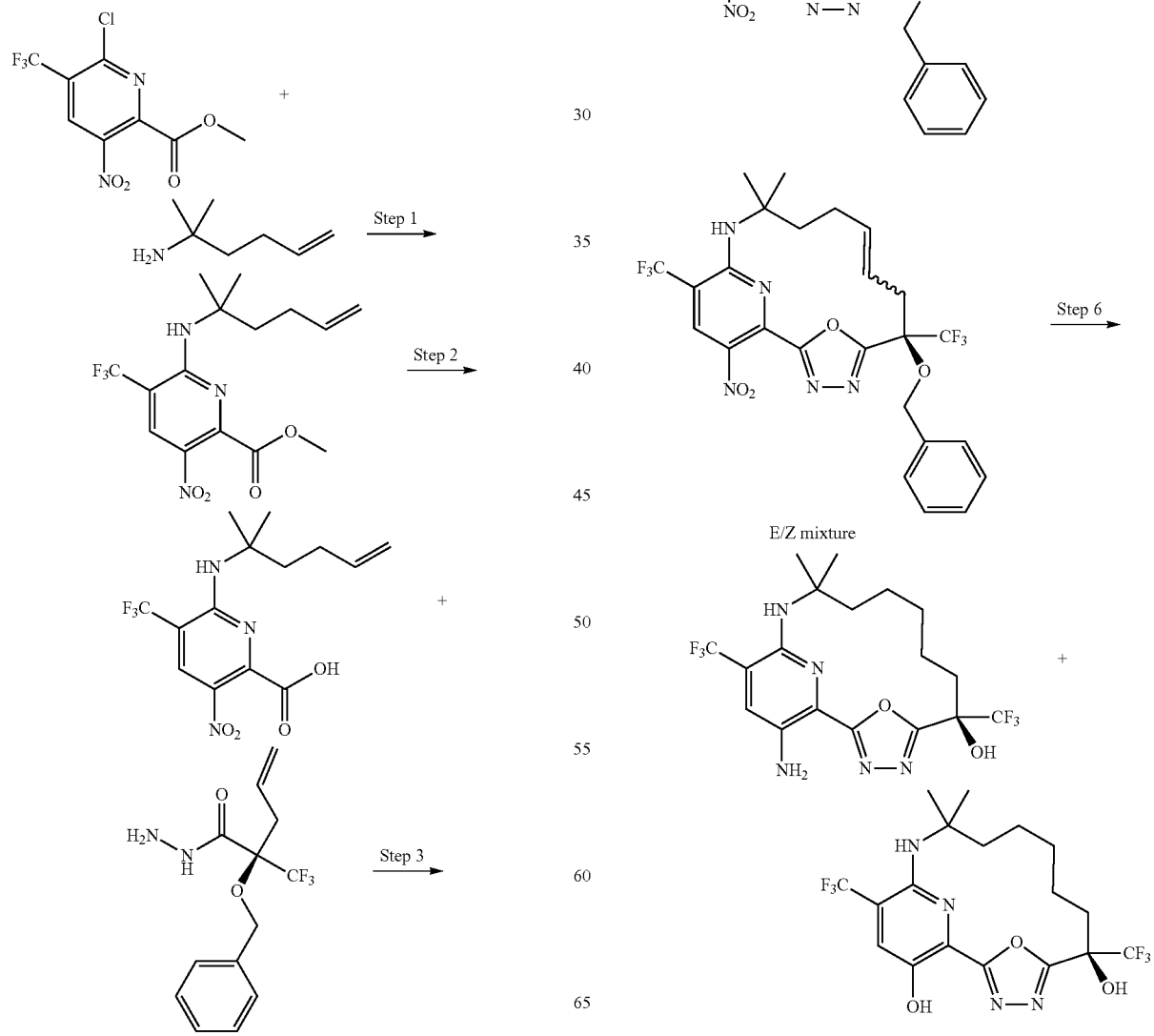

Step 1: Methyl 6-(1,1-dimethylpent-4-enylamino)-3-nitro-5-(trifluoromethyl)pyridine-2-carboxylate

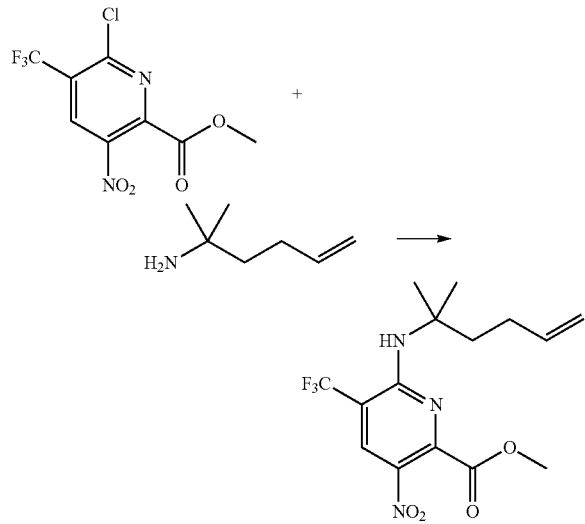

2-Methylhex-5-en-2-amine (hydrochloride salt) (69.4 g, 463.7 mmol) was suspended in acetonitrile (960 mL) and treated with DIEA (220 mL, 1.263 mol). To the formed brown solution was added methyl 6-chloro-3-nitro-5-(trifluoromethyl)pyridine-2-carboxylate (120 g, 421.7 mmol) in one portion. The orange solution was slowly heated to 65° C. over 2.5 h (Note: reaction shows exotherm on heating). The deep orange solution was evaporated at 40° C. and to the residue was added with MTBE (1 L) and water (1 L) and the layers were separated. The deep orange organic phase was washed with a 1:1 solution of saturated aqueous NH₄Cl/water mixture (2×600 mL), once with brine (400 mL) and the organic phase was dried, filtered and evaporated to give methyl 6-(1,1-dimethylpent-4-enylamino)-3-nitro-5-(trifluoromethyl)pyridine-2-carboxylate (152.7 g, 100%). ESI-MS m/z calc. 361.12494, found 362.0 (M+1)⁺; Retention time: 3.02 minutes (LC Method D).

Step 2: 6-(1,1-Dimethylpent-4-enylamino)-3-nitro-5-(trifluoromethyl)pyridine-2-carboxylic Acid

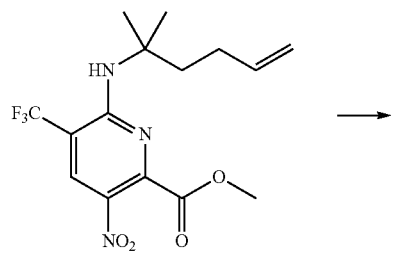

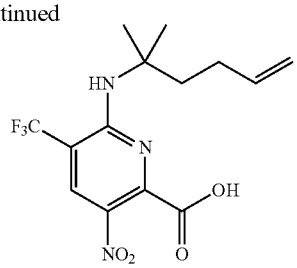

Methyl 6-(1,1-dimethylpent-4-enylamino)-3-nitro-5-(trifluoromethyl)pyridine-2-carboxylate (152.4 g, 421.7 mmol) was dissolved in methanol (750 mL) and treated with NaOH (750 mL of 2 M, 1.500 mol) under stirring (added all at once giving a slight exotherm from 30° C. to 40° C.). The solution was stirred at room temperate for 18 h. The deep red solution was concentrated under reduced pressure at 42° C. and the resulting orange red solution was treated with toluene (1 L). The emulsion was stirred in an ice bath and acidified to pH=1 by addition of HCl (260 mL of 6 M, 1.560 mol) keeping the internal temperature below 15° C. The phases were separated and the organic phase was washed twice with water (2×500 mL) and once with brine (400 mL). The organic phase was dried over MgSO₄, filtered, evaporated and dried under vacuum to give 137 g of a deep orange mass of solid. This material was evaporated from acetonitrile (~1 L, to remove residual toluene) and dissolved in acetonitrile (600 mL) and warmed to ~60° C. To the deep red hot solution was added N-cyclohexylcyclohexanamine (79 mL, 396.5 mmol) under stirring (exotherm noted from 60° C. to 70° C.) and the hot solution was seeded. The material became a solid mass at an internal temperature of ~60° C., which could be stirred magnetically after breaking up. The thick suspension was stirred in the cooling hot water bath overnight and then in an ice bath for 3 h. The solid was collected by filtration, washed with cold acetonitrile until the filtrate was colorless and dried over the weekend to give 6-(1,1-dimethylpent-4-enylamino)-3-nitro-5-(trifluoromethyl)pyridine-2-carboxylic acid (dicyclohexylamine salt) (172 g, 77%) as a yellow solid. This salt was suspended in MTBE (1 L) and treated with citric acid (1.2 L of 1 M, 1.200 mol). The mixture was stirred and the phases were separated. The organic phase was washed twice more with 1 M citric acid (2×400 mL) and 4 times with 0.5 M KHSO₄ (4×400 mL). The organic phase was then washed once with brine (200 mL), dried, filtered and evaporated to give 6-(1,1-dimethylpent-4-enylamino)-3-nitro-5-(trifluoromethyl)pyridine-2-carboxylic acid (113.4 g, 77%) as a yellow orange oil, which crystallized upon standing. ¹H NMR (400 MHz, DMSO-d6) δ 14.21 (s, 1H), 8.46 (s, 1H), 6.20-6.00 (m, 1H), 5.82-5.57 (m, 1H), 5.13-4.74 (m, 2H), 1.97 (d, J=2.9 Hz, 4H), 1.45 (s, 6H) ppm. ESI-MS m/z calc. 347.10928, found 348.0 (M+1)⁺; Retention time: 2.49 minutes (LC Method D).

Step 3: N'-[(2R)-2-Benzyloxy-2-(trifluoromethyl)pent-4-enoyl]-6-(1,1-dimethylpent-4-enylamino)-3-nitro-5-(trifluoromethyl)pyridine-2-carbohydrazide

Step 4: 6-[5-[(1R)-1-Benzyloxy-1-(trifluoromethyl)but-3-enyl]-1,3,4-oxadiazol-2-yl]-N-(1,1-dimethylpent-4-enyl)-5-nitro-3-(trifluoromethyl)pyridin-2-amine

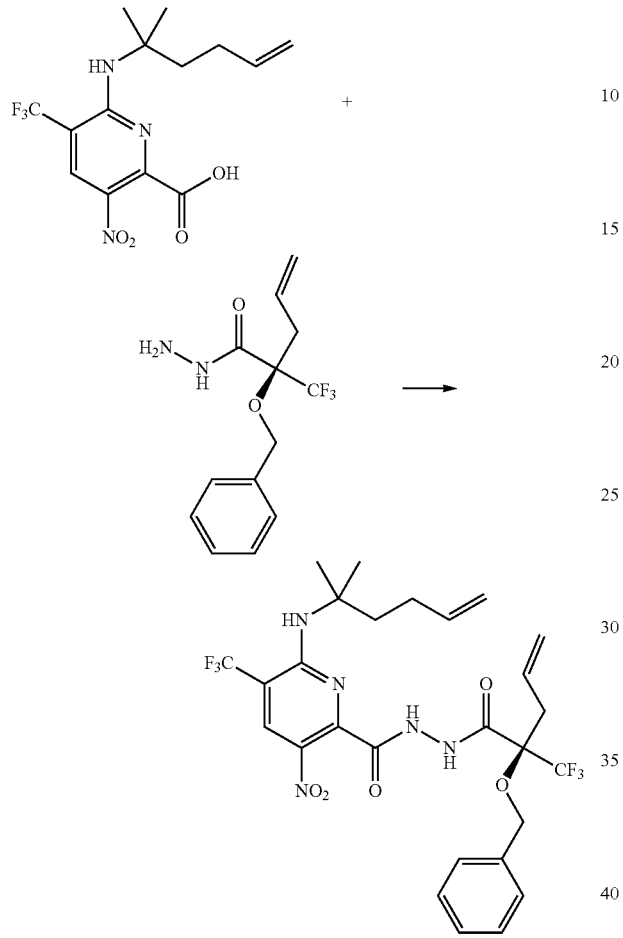

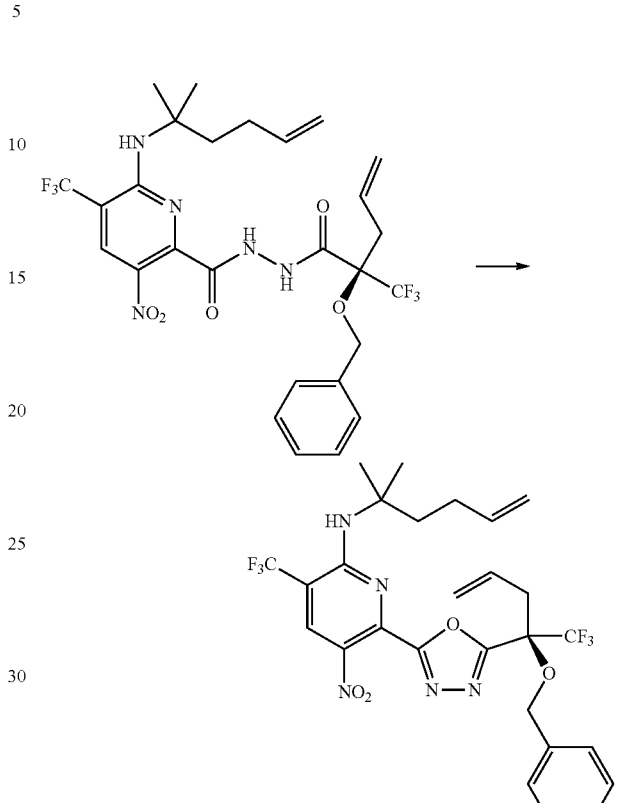

6-(1,1-Dimethylpent-4-enylamino)-3-nitro-5-(trifluoromethyl)pyridine-2-carboxylic acid (100 g, 285.1 mmol) and (2R)-2-benzyloxy-2-(trifluoromethyl)pent-4-enehydrazide (86.3 g, 299.4 mmol) were dissolved in DMF (600 mL) and cooled in an ice bath. At an internal temperature of 3.1° C., HATU (114 g, 299.8 mmol) was added in one portion (no exotherm observed). Then, DIEA (100 mL, 574.1 mmol) was slowly added over 0.5 h (exothermic) keeping the internal temperate between 3 and 10° C. After the addition, the ice bath was removed and the reaction was stirred for another 0.5 h allowing it to warm to room temperature. The orange solution was added to a stirred solution of ice and water (3 L) and MTBE (1 L). The mixture was stirred for 10 minutes and the phases were separated. The organic phase was washed twice with water (2×1 L), 0.2 M KHSO₄ (3×1 L) and once with brine (250 mL). The organic phase was dried, filtered and evaporated to give as an orange mass, N'-[(2R)-2-benzyloxy-2-(trifluoromethyl)pent-4-enoyl]-6-(1,1-dimethylpent-4-enylamino)-3-nitro-5-(trifluoromethyl)pyridine-2-carbohydrazide (181 g, quantitative yield). ESI-MS m/z calc. 617.2073, found 618.0 (M+1)⁺; Retention time: 3.25 minutes (LC Method D). This material was used directly in the next step.

N'-[(2R)-2-Benzyloxy-2-(trifluoromethyl)pent-4-enoyl]-6-(1,1-dimethylpent-4-enylamino)-3-nitro-5-(trifluoromethyl)pyridine-2-carbohydrazide (176.1 g, 285.2 mmol) was dissolved in acetonitrile (1.4 L) and heated to 55° C. The yellow orange solution was treated with DIEA (124 mL, 711.9 mmol) followed by portion-wise addition of tosyl chloride (54.4 g, 285.3 mmol) over 15 min (exothermic, internal temperature kept between 55° C. and 60° C. by removing the heating mantel and slow addition) and the reaction was stirred at 55-60° C. for 45 min. The reaction solution was concentrated under reduced pressure at 40° C. and the residue was extracted with MTBE/heptane 1:1 (1.4 L) and water (1.4 L). The organic phase was washed once more with water (1.5 L), twice with 0.2 M KHSO₄ (2×1 L) and once with brine (0.5 L). The organic phase was dried, filtered and evaporated to give 172 g of an orange oil which was dissolved in 100 mL of toluene and 300 mL of heptane. The solution was loaded onto a 3 kg silica column (column volume=4800 mL, flow rate=900 mL/min). Eluted with 100% hexanes for 1 min, then programmed an initial gradient of 0% to 10% ethyl acetate in hexanes over 106 min (2 column volumes). The product started eluting at ~4% ethyl acetate, so 4.3% ethyl acetate was held isocratically until the product finished eluting to give 6-[5-[(1R)-1-benzyloxy-1-(trifluoromethyl)but-3-enyl]-1,3,4-oxadiazol-2-yl]-N-(1,1-dimethylpent-4-enyl)-5-nitro-3-(trifluoromethyl)pyridin-2-amine (139.1 g, 80%). ¹H NMR (400 MHz, Chloroform-d) δ 8.51 (s, 1H), 7.40-7.27 (m, 5H), 6.03-5.87 (m, 1H), 5.80-5.66 (m, 1H), 5.58 (s, 1H), 5.31-5.16 (m, 2H), 5.03-4.95 (m, 1H), 4.95-4.89 (m, 1H), 4.81 (d, J=10.5 Hz, 1H), 4.64 (d, J=10.5 Hz, 1H), 3.28-3.13 (m, 2H), 2.08-1.99 (m, 2H), 1.99-1.89 (m, 2H), 1.47 (s, 6H) ppm. ESI-MS m/z calc. 599.1967, found 600.0 (M+1)⁺; Retention time: 3.71 minutes (LC Method D).

Step 5: (6R)-6-Benzyloxy-12,12-dimethyl-17-nitro-6,15-bis(trifluoromethyl)-19-oxa-3,4,13,18-tetrazatricyclo[12.3.1.12,5]nonadeca-1(18),2,4,8,14,16-hexaene (E/Z mixture)

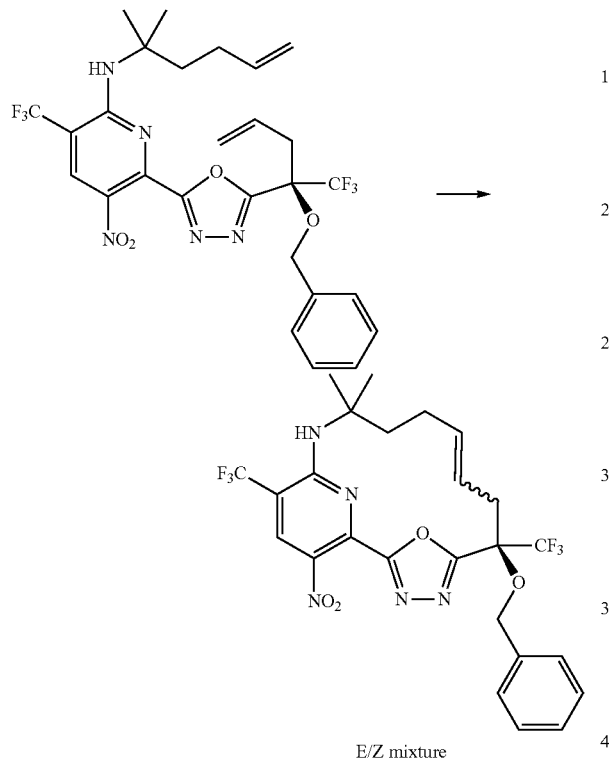

E/Z mixture

This reaction was run in three, 46.3 g batches in parallel, each in a 12 L, 3-neck round bottom flask. The experimental below describes one of these batches.

Attached a sparging tube, reflux condenser with gas bubbler & overhead stirrer to a 12 L vessel placed in heat blanket. Dissolved 6-[5-[(1R)-1-benzyloxy-1-(trifluoromethyl)but-3-enyl]-1,3,4-oxadiazol-2-yl]-N-(1,1-dimethylpent-4-enyl)-5-nitro-3-(trifluoromethyl)pyridin-2-amine (46.3 g, 76.22 mmol) in DCE (8.23 L). Sparged the system with a heavy stream of nitrogen gas. Set the heat blanket for 50° C. When the vessel reached 53° C., added dichloro[1,3-bis(2,4,6-trimethylphenyl)-2-imidazolidinylidene][[5-[(dimethylamino)sulfonyl]-2-(1-methylethoxy-O)phenyl]methylene-C]ruthenium(II) (Zhan catalyst-1B, 11.2 g, 15.26 mmol) all at once. Rinsed the catalyst container with DCE and added the rinse to the reaction. On completion of catalyst addition, increased the blanket temperature to 73° C. Once internal temperature reached 72° C., continued stirring for 2 h 28 min then decreased the heat blanket temperature to 45° C. After 2 h 27 min, internal temperature reached 50° C. After 15 min, added solid 2-sulfanylpyridine-3-carboxylic acid (12 g, 77.33 mmol) and triethylamine (11 mL, 78.92 mmol). Stirred for 12 h then allowed the mixture to cool to room temperature. Added 100 g of SiO₂ and 10 g of activated carbon (20-40 mesh, granular) to the reaction.

Stirred for 1 h then filtered over Celite and evaporated the filtrate giving the crude product mixture. Combined the material from all three parallel reactions to give 71.2 g of crude product mixture. This material was purified on two separate 3 kg silica gel columns using a gradient from 100% hexanes to 10% ethyl acetate in hexanes over 110 min followed by a gradient from 10% ethyl acetate in hexanes to 100% ethyl acetate over 10 minutes. After combining the two separate purified batches, obtained (6R)-6-benzyloxy-12,12-dimethyl-17-nitro-6,15-bis(trifluoromethyl)-19-oxa-3,4,13,18-tetrazatricyclo[12.3.1.12,5]nonadeca-1(18),2,4,8,14,16-hexaene (E/Z mixture) (51.88 g, 40%). ¹H NMR (400 MHz, DMSO-d6) δ 8.55 (d, J=0.8 Hz, 1H), 7.49-7.21 (m, 5H), 6.58 (s, 1H), 5.79 (dt, J=13.7, 6.5 Hz, 1H), 5.58 (ddd, J=15.0, 8.8, 5.6 Hz, 1H), 4.83 (d, J=11.1 Hz, 1H), 4.55 (d, J=11.1 Hz, 1H), 3.13 (dd, J=14.2, 5.4 Hz, 1H), 2.77 (dd, J=14.3, 8.8 Hz, 1H), 2.38-2.24 (m, 1H), 2.14-1.93 (m, 3H), 1.58-1.32 (m, 6H) ppm. ESI-MS m/z calc. 571.1654, found 572.1 (M+1)⁺; Retention times: 3.46 minutes and 3.49 minutes (LC Method D). Product formed as a 3:1 mixture of double bond isomers.

Step 6: (6R)-17-Amino-12,12-dimethyl-6,15-bis(trifluoromethyl)-19-oxa-3,4,13,18-tetrazatricyclo[12.3.1.12,5]nonadeca-1(18),2,4,14,16-pentaen-6-ol (Compound 163) and (6R)-12,12-dimethyl-6,15-bis(trifluoromethyl)-19-oxa-3,4,13,18-tetrazatricyclo[12.3.1.12,5]nonadeca-1(18),2,4,14,16-pentaene-6,17-diol (Compound 164)

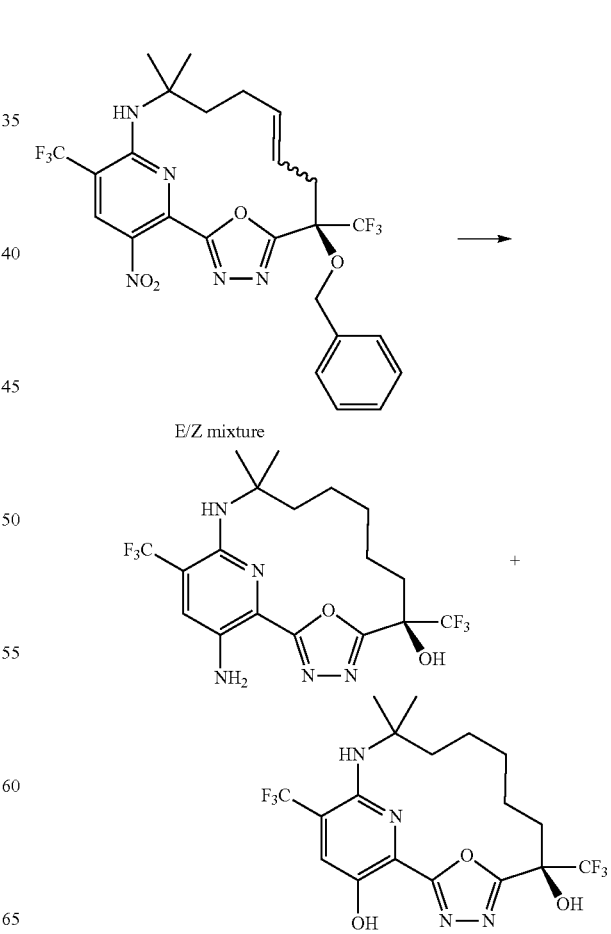

(6R)-6-Benzyloxy-12,12-dimethyl-17-nitro-6,15-bis(trifluoromethyl)-19-oxa-3,4,13,18-tetrazatricyclo[12.3.1.12,5]nonadeca-1(18),2,4,8,14,16-hexaene (E/Z mixture) (50.8 g, 88.89 mmol) was dissolved in 250 mL of ethanol and partially concentrated by rotary evaporation with 28° C. water bath to remove any residual solvents then dissolved in further ethanol (720 mL) in a 5 L flask. Degassed the solution using 5 cycles of house vacuum with nitrogen gas backfill. Added dihydroxypalladium (15.2 g of 10% w/w, 10.824 mmol) to the substrate solution under nitrogen. Repeated house vacuum with hydrogen backfill for 6 cycles to replace nitrogen atmosphere with hydrogen. Finally kept the vessel under 1 atmosphere of hydrogen using a balloon. Stirred this mixture vigorously with a magnetic stirrer overnight then removed the hydrogen balloon. Filtered the mixture through 70 g of Celite on a medium-fritted funnel. Concentrated the green filtrate solution by rotary evaporation with a 28° C. water bath. Obtained 42.65 g of crude product as a yellow solid of which 41.5 g was purified by reverse-phase chromatography (dissolved in 125 mL of methanol and 2.55 mL DMF (2% DMF/methanol solution) and loaded onto a 3.8 kg $C_{18}$ column (column volume=3.3 L, flow rate=375 mL/min). Programmed an initial gradient of 40% to 70% acetonitrile in water over 176 minutes (20 column volumes), then brought the eluent to 100% acetonitrile over the following ~20 min). Mixed and pure fractions were isolated from the column. Pure fractions were concentrated to give as a yellow solid, (6R)-17-amino-12,12-dimethyl-6,15-bis(trifluoromethyl)-19-oxa-3,4,13,18-tetrazatricyclo[12.3.1.12,5]nonadeca-1(18),2,4,14,16-pentaen-6-ol (28.17 g, 70%). This material was combined with several smaller batches (80 mg, 340 mg, 360 mg, 1.46 g and 1.63 g) made by similar methods as a solution in acetonitrile which was then concentrated to give a yellow solid. This solid was dissolved in dichloromethane and heptane was added then the solution was concentrated under vacuum in the dark at 40° C. overnight, which gave 31.95 g of (6R)-17-amino-12,12-dimethyl-6,15-bis(trifluoromethyl)-19-oxa-3,4,13,18-tetrazatricyclo[12.3.1.12,5]nonadeca-1(18),2,4,14,16-pentaen-6-ol. $^1$H NMR (400 MHz, DMSO-d6) δ 7.61 (s, 1H), 7.59 (s, 1H), 5.96 (s, 2H), 4.64 (s, 1H), 2.90-2.71 (m, 1H), 2.30-2.15 (m, 1H), 2.15-1.98 (m, 1H), 1.91-1.74 (m, 1H), 1.73-1.57 (m, 1H), 1.56-1.38 (m, 5H), 1.36 (s, 3H), 1.31 (s, 3H). ESI-MS m/z calc. 453.15994, found 454.2 (M+1)$^+$; Retention time: 3.03 minutes (LC Method D).

One mixed fraction from the reverse-phase purification described above contained an impurity showing a mass one unit greater than the intended product described above. This fraction was concentrated and the residue was dissolved in 3.6 mL of methanol, then purified by reverse-phase prep HPLC through a $C_{18}$ column using a gradient from 1-99% acetonitrile in water (+ HCl modifier) giving as a yellow solid, (6R)-12,12-dimethyl-6,15-bis(trifluoromethyl)-19-oxa-3,4,13,18-tetrazatricyclo[12.3.1.12,5]nonadeca-1(18),2,4,14,16-pentaene-6,17-diol (105 mg, 0.003%). $^1$H NMR (400 MHz, DMSO-d6) δ 10.43 (s, 1H), 7.64 (s, 1H), 7.57 (s, 1H), 4.85 (s, 1H), 2.91-2.74 (m, 1H), 2.30-2.15 (m, 1H), 2.10-1.96 (m, 1H), 1.85-1.68 (m, 1H), 1.68-1.54 (m, 1H), 1.53-1.37 (m, 5H), 1.36 (s, 3H), 1.31 (s, 3H) ppm. ESI-MS m/z calc. 454.14395, found 455.2 (M+1)$^+$; Retention time: 2.87 minutes (LC Method D).

Step 7: Solid Form Characterization of Crystalline Compound 163 Form a (Neat)

A. X-Ray Powder Diffraction

The XRPD diffractogram for crystalline Compound 163 Form A (neat) produced by Step 6 and recrystallized from EtOH was acquired using the General X-Ray Powder Diffraction (XRPD) Method. The XRPD diffractogram for crystalline Compound 163 Form A (neat) is provided in FIG. 16, and the XRPD data are summarized below in Table 6.

TABLE 6

XRPD signals for crystalline Compound 163 Form A (neat)

| XRPD Peak No. | Angle (degrees 2-Theta ± 0.2) | Intensity % |
| --- | --- | --- |
| 1 | 7.4271 | 100 |
| 2 | 8.4377 | 7.56 |
| 3 | 14.1039 | 4.84 |
| 4 | 14.5744 | 2.53 |
| 5 | 14.962 | 7.2 |
| 6 | 16.9424 | 2.49 |
| 7 | 19.0503 | 5.71 |
| 8 | 19.9711 | 2.4 |
| 9 | 22.4778 | 2.31 |
| 10 | 25.5622 | 2.19 |
| 11 | 25.7502 | 3.64 |

B. Differential Scanning Calorimetry Analysis

Figure 17:
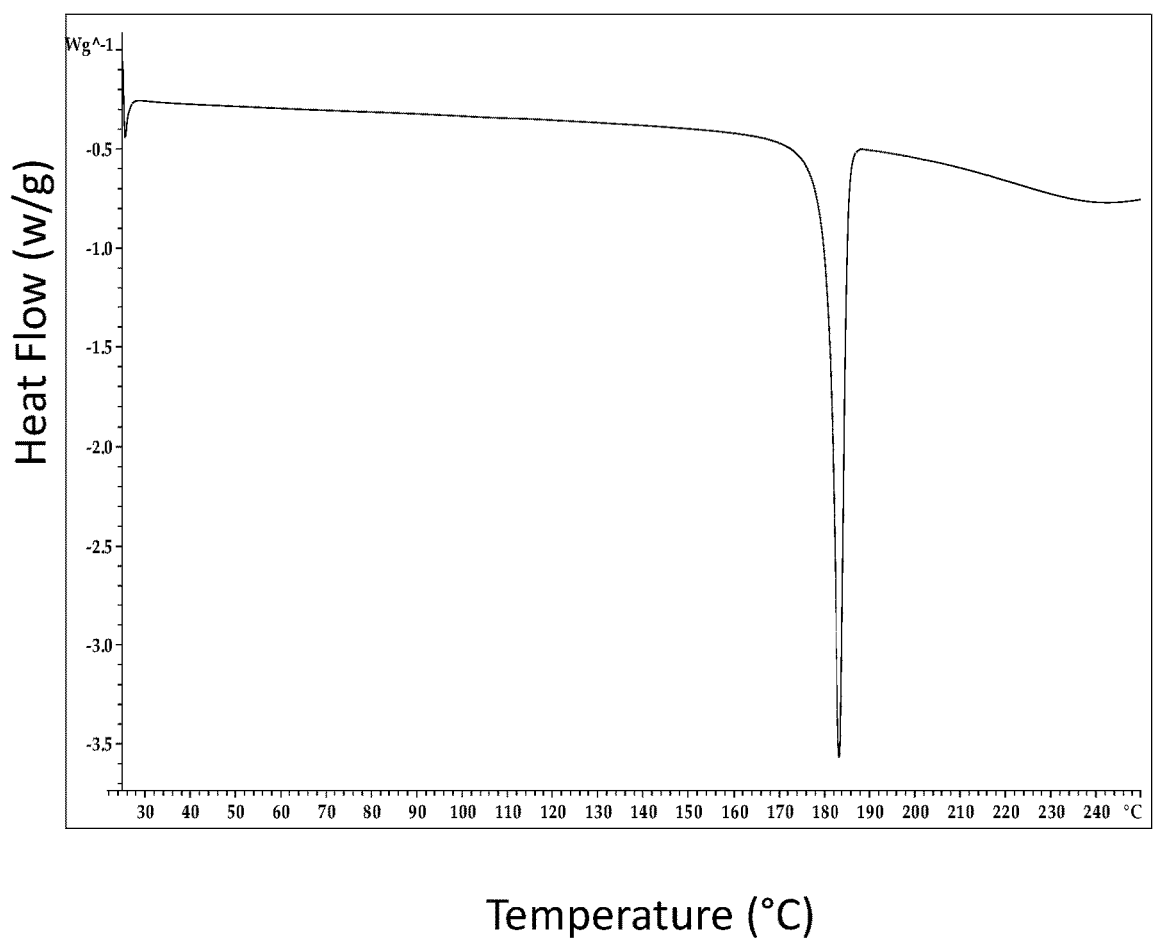
FIG. 17 provides a DSC analysis of crystalline Compound 163 Form A (neat).

The DSC data were collected with a ramp of 10.00° C./min to 250.00° C. The DSC thermogram for crystalline Compound 163 Form A (neat) produced by Step 6 is provided in FIG. 17. The thermogram shows a Tm onset of 180.8° C., with a Tm peak at 183.18° C., 62.32 J/g.

Example 90: Preparation of (6S)-17-amino-12,12-dimethyl-6,15-bis(trifluoromethyl)-19-oxa-3,4,13,18-tetrazatricyclo[12.3.1.12,5]nonadeca-1(18),2,4,14,16-pentaen-6-ol (Compound 165)

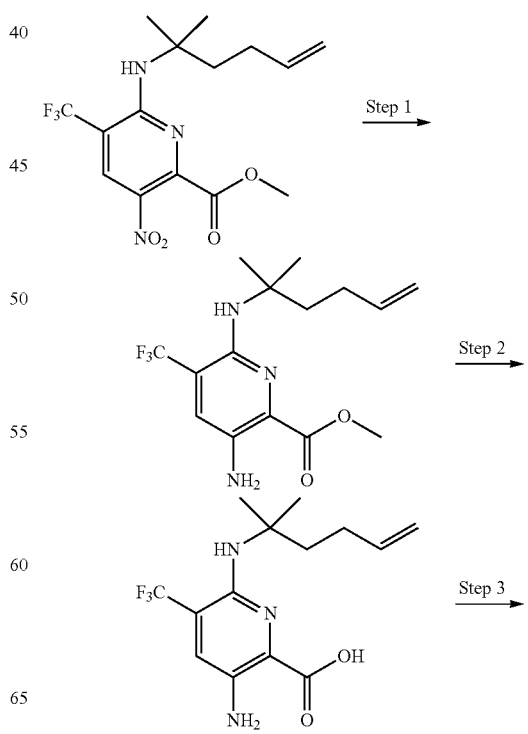

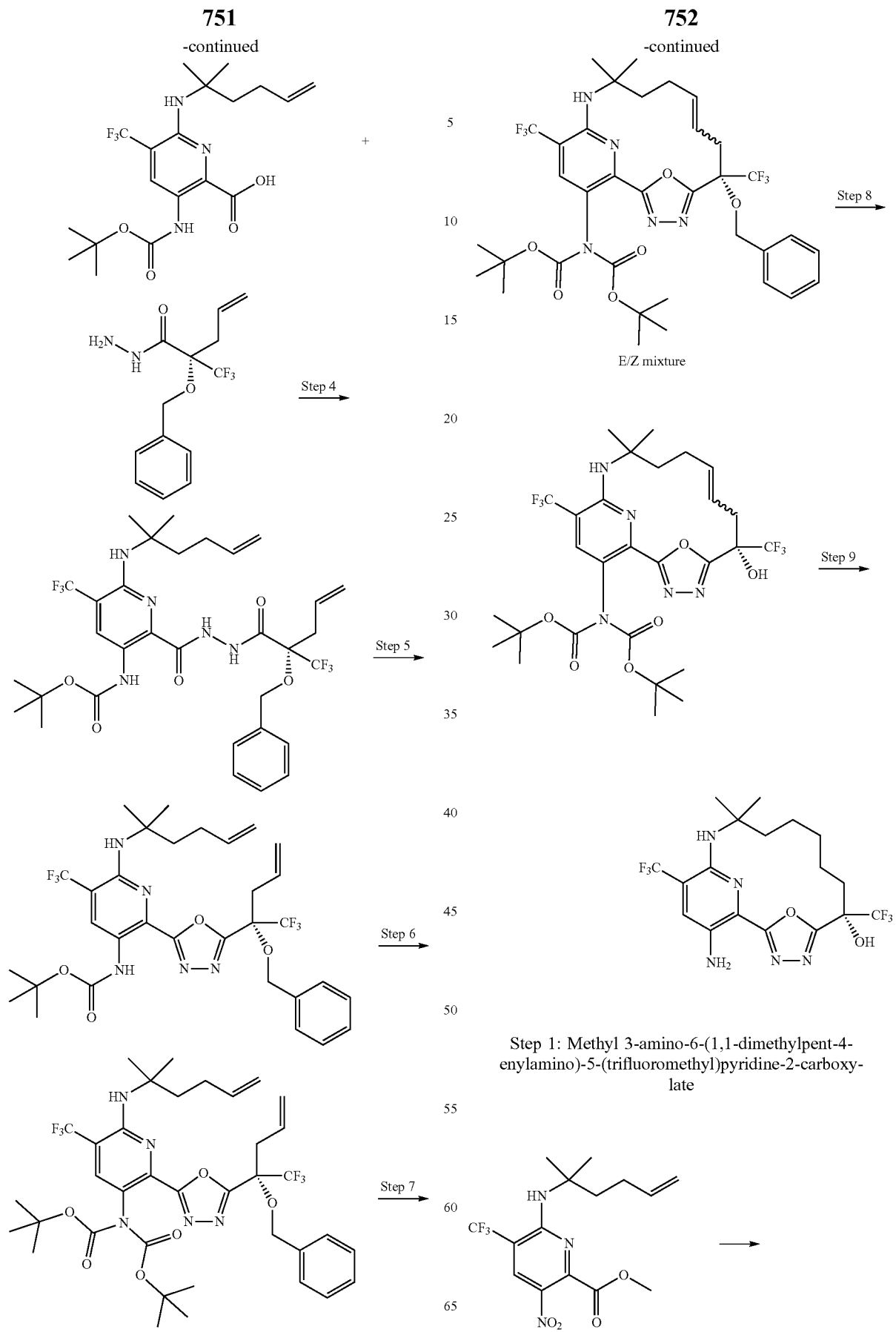
Step 1: Methyl 3-amino-6-(1,1-dimethylpent-4-enylamino)-5-(trifluoromethyl)pyridine-2-carboxylate -continued

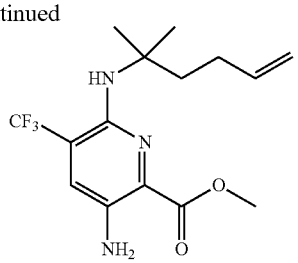

Charged a 2 L, 3-neck round bottom flask with methyl 6-(1,1-dimethylpent-4-enylamino)-3-nitro-5-(trifluoromethyl)pyridine-2-carboxylate (28.4 g, 78.6 mmol) and dissolved the dark red oil in ethanol (140 mL) and THF (140 mL). Placed the reaction vessel in a water bath. Attached a 500 mL addition funnel to the flask. Dissolved sodium dithionite (disodium salt) (50 g, 287.2 mmol) in water (330 mL) and added the aqueous solution to the addition funnel. The sodium dithionite solution was added slowly to the substrate solution at such a rate that internal temperature was maintained at or below 28° C. During the addition, precipitation occurred, and the reaction mixture began to turn lighter in color, from dark burgundy to orange. The addition was complete after ~1 h. The reaction mixture turned from heterogeneous to homogeneous by the time addition was completed. Diluted the orange reaction solution with 2-methyltetrahydrofuran (600 mL) and stirred for 20 min. Added 200 mL of brine and continued stirring. Separated the phases and washed the organics with 1 M aqueous HCl (3×200 mL). Finally, washed with brine (1×200 mL) then dried the organics over MgSO$_4$, filtered and concentrated under reduced pressure and further dried under vacuum to yield methyl 3-amino-6-(1,1-dimethylpent-4-enylamino)-5-(trifluoromethyl)pyridine-2-carboxylate (24.59 g, 92%). $^1$H NMR (400 MHz, CDCl$_3$) δ 7.25 (d, J=0.8 Hz, 1H), 5.92-5.68 (m, 1H), 5.51 (s, 2H), 5.07-4.80 (m, 2H), 4.29 (s, 1H), 3.91 (s, 3H), 2.07-1.94 (m, 4H), 1.42 (s, 6H) ppm. ESI-MS m/z calc. 331.15076, found 332.2 (M+1)$^+$; Retention time: 2.96 minutes (LC Method D).

Step 2: 3-Amino-6-(1,1-dimethylpent-4-enylamino)-5-(trifluoromethyl)pyridine-2-carboxylic acid

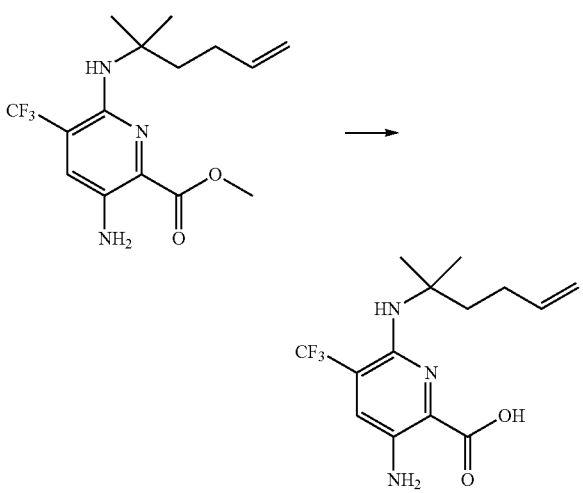

Charged a 500 mL, 2-neck round bottom flask with methyl 3-amino-6-(1,1-dimethylpent-4-enylamino)-5-(trifluoromethyl)pyridine-2-carboxylate (23.6 g, 71.23 mmol) and THF (120 mL) and stirred to dissolve. Attached a 125 mL addition funnel and heat blanket. Dissolved potassium hydroxide (21 g, 374.3 mmol) in water (120 mL) and added this aqueous solution to the addition funnel. The aqueous KOH solution was added to the substrate over 12 min (internal temperature increased from 19° C. to 27° C. during addition). The internal temp was maintained between 45° C. to 50° C. Stirred vigorously under N$_2$ with an air-cooled reflux condenser. The heating was stopped after about 5 h and the reaction was allowed to cool to ambient temperature. Placed the reaction mixture in a 500 mL separatory funnel and separated the phases. Placed the organic phase in a 500 mL flask and concentrated to remove most of the THF. Re-dissolved the crude residue in 300 mL of isopropyl acetate. Washed the organic solution with 1 M aqueous HCl (1×200 mL) and brine (1×100 mL). The organic layer was dried, filtered and concentrated under reduced pressure and further dried under vacuum to yield as an orange solid, 3-amino-6-(1,1-dimethylpent-4-enylamino)-5-(trifluoromethyl)pyridine-2-carboxylic acid (21.47 g, 95%). $^1$H NMR (400 MHz, DMSO-d6) δ 8.26 (s, 3H), 7.49 (s, 1H), 5.89-5.61 (m, 1H), 5.05-4.75 (m, 2H), 4.24 (s, 1H), 1.94 (s, 4H), 1.37 (s, 6H) ppm. ESI-MS m/z calc. 317.1351, found 318.2 (M+1)$^+$; Retention time: 2.58 minutes (LC Method D).

Step 3: 3-(tert-Butoxycarbonylamino)-6-(1,1-dimethylpent-4-enylamino)-5-(trifluoromethyl)pyridine-2-carboxylic Acid

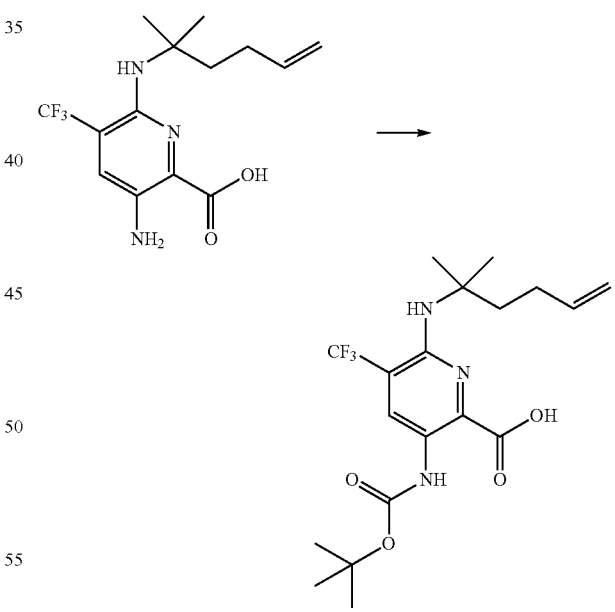

Dissolved 3-amino-6-(1,1-dimethylpent-4-enylamino)-5-(trifluoromethyl)pyridine-2-carboxylic acid (12.4 g, 39.08 mmol) in THF (100 mL). Stirred the solution under N$_2$ atmosphere. Dissolved di-tert-butyl dicarbonate (10 mL, 43.53 mmol) in THF (20 mL) and added this solution via syringe to the reaction solution. Next, added triethylamine (8.01 g, 79.16 mmol) to the reaction solution via syringe over 15 minutes After 17 h, the reaction was concentrated under reduced pressure to remove THF. Re-dissolved the crude product in 200 mL of isopropyl acetate. Placed the solution in a 500 mL separatory funnel and washed organic solution with 1 M aqueous HCl (1×80 mL, 1×20 mL) and brine (30 mL). Dried the organics over Na₂SO₄, filtered and concentrated under reduced pressure and further dried under high vacuum to yield as a dark red oil, 3-(tert-butoxycarbonylamino)-6-(1,1-dimethylpent-4-enylamino)-5-(trifluoromethyl)pyridine-2-carboxylic acid (16.3 g, 99%). ¹H NMR (400 MHz, DMSO-d6) δ 13.59 (s, 1H), 9.62 (s, 1H), 8.52 (s, 1H), 5.87-5.63 (m, 1H), 5.00-4.85 (m, 2H), 4.82-4.76 (m, 1H), 1.97 (s, 4H), 1.46 (s, 9H), 1.41 (s, 6H) ppm. ESI-MS m/z calc. 417.18753, found 418.4 (M+1)⁺; Retention time: 3.42 minutes (LC Method D).

Step 4: tert-Butyl N-[2-[[[(2S)-2-benzyloxy-2-(trifluoromethyl)pent-4-enoyl]amino]carbamoyl]-6-(1,1-dimethylpent-4-enylamino)-5-(trifluoromethyl)-3-pyridyl]carbamate

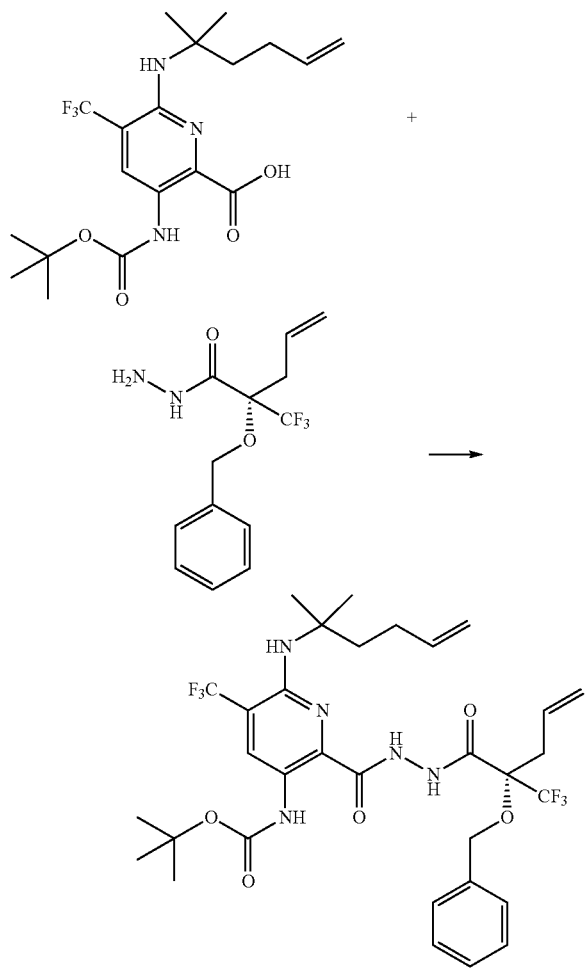

To a stirred solution of 3-(tert-butoxycarbonylamino)-6-(1,1-dimethylpent-4-enylamino)-5-(trifluoromethyl)pyridine-2-carboxylic acid (16.3 g, 38.66 mmol) and (2S)-2-benzyloxy-2-(trifluoromethyl)pent-4-enehydrazide (12.4 g, 43.02 mmol) in 2-methyltetrahydrofuran (200 mL) was added solid 2-chloro-4,6-dimethoxy-1,3,5-triazine (8 g, 45.57 mmol) under N₂ atmosphere. A solution of 4-methylmorpholine (5.24 g, 50.77 mmol) in 2-methyltetrahydrofuran (50 mL) was gradually added to the reaction mixture over an hour and the reaction was stirred for 2 h at room temperature. The reaction mixture was diluted with isopropyl acetate (250 mL), washed with water (1×50 mL), a saturated aqueous solution of NaHCO₃ (2×100 mL) and with brine (1×30 mL). The organic layer was dried over Na₂SO₄, filtered and concentrated under reduced pressure. The residue was purified by silica gel chromatography (220 g column) to afford tert-butyl N-[2-[[[(2S)-2-benzyloxy-2-(trifluoromethyl)pent-4-enoyl]amino]carbamoyl]-6-(1,1-dimethylpent-4-enylamino)-5-(trifluoromethyl)-3-pyridyl]carbamate (21.92 g, 82%). ¹H NMR (400 MHz, DMSO-d6) δ 10.53 (s, 1H), 9.95 (s, 1H), 9.63 (s, 1H), 8.75 (s, 1H), 7.51-7.42 (m, 2H), 7.42-7.27 (m, 3H), 5.99-5.68 (m, 2H), 5.45-5.12 (m, 2H), 5.03-4.87 (m, 2H), 4.88-4.84 (m, 3H), 3.22-2.85 (m, 2H), 2.13-1.79 (m, 4H), 1.46 (s, 9H), 1.42 (s, 6H) ppm. ESI-MS m/z calc. 687.2855, found 688.5 (M+1)⁺; Retention time: 0.82 minutes (LC Method D).

Step 5: tert-Butyl N-[2-[5-[(1S)-1-benzyloxy-1-(trifluoromethyl)but-3-enyl]-1,3,4-oxadiazol-2-yl]-6-(1,1-dimethylpent-4-enylamino)-5-(trifluoromethyl)-3-pyridyl]carbamate

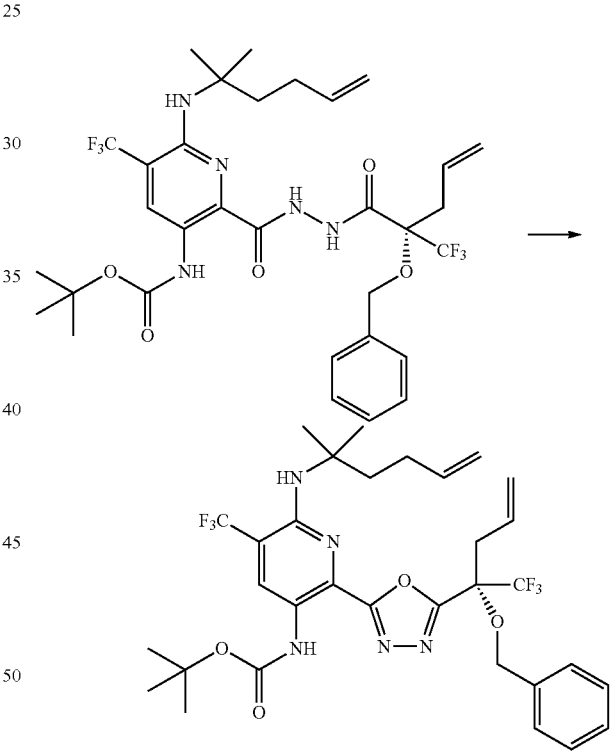

To a solution of tert-butyl N-[2-[[[(2S)-2-benzyloxy-2-(trifluoromethyl)pent-4-enoyl]amino]carbamoyl]-6-(1,1-dimethylpent-4-enylamino)-5-(trifluoromethyl)-3-pyridyl]carbamate (14 g, 20.36 mmol) in acetonitrile (120 mL) was added DIEA (7.94 g, 61.43 mmol) and heated the solution to 50° C. A solution of p-TsCl (4.33 g, 22.71 mmol) in acetonitrile (50 mL) was added slowly dropwise through an addition funnel over about 1 h. The resultant dark brown solution was heated for 6.5 h. Again, p-TsCl (~1 g, in 3 portions with an interval of 6 h) was added while heating at 50° C. The reaction mixture was cooled to room temperature, diluted with isopropyl acetate (250 mL) and a saturated aqueous solution of NaHCO₃ (50 mL) was added slowly while stirring. The mixture was stirred for 10 minutes, and the layers were separated. The organic layer was washed with an aqueous saturated solution of NaHCO$_3$ (1×50 mL) and brine (1×50 mL) then dried over Na$_2$SO$_4$, filtered and concentrated under reduced pressure to obtain as a dark burgundy oil, tert-butyl N-[2-[5-[(1S)-1-benzyloxy-1-(trifluoromethyl)but-3-enyl]-1,3,4-oxadiazol-2-yl]-6-(1,1-dimethylpent-4-enylamino)-5-(trifluoromethyl)-3-pyridyl]carbamate (16.4 g, quant.). $^1$H NMR (400 MHz, DMSO-d6) δ 9.35 (s, 1H), 8.55 (s, 1H), 7.43-7.28 (m, 5H), 6.03-5.82 (m, 1H), 5.80-5.62 (m, 1H), 5.41-5.29 (m, 1H), 5.22 (dd, J=10.3, 1.8 Hz, 1H), 5.05-4.88 (m, 2H), 4.89-4.83 (m, 1H), 4.84-4.73 (m, 2H), 4.63 (d, J=10.9 Hz, 1H), 3.27 (d, J=7.1 Hz, 2H), 1.98 (s, 3H), 1.47 (s, 9H), 1.18 (s, 3H), 1.17 (s, 3H) ppm. ESI-MS m/z calc. 669.27496, found 670.6 (M+1)$^+$; Retention time: 1.36 minutes (LC Method D).

Step 6: tert-Butyl N-[2-[5-[(1S)-1-benzyloxy-1-(trifluoromethyl)but-3-enyl]-1,3,4-oxadiazol-2-yl]-6-(1,1-dimethylpent-4-enylamino)-5-(trifluoromethyl)-3-pyridyl]-N-tert-butoxycarbonyl-carbamate

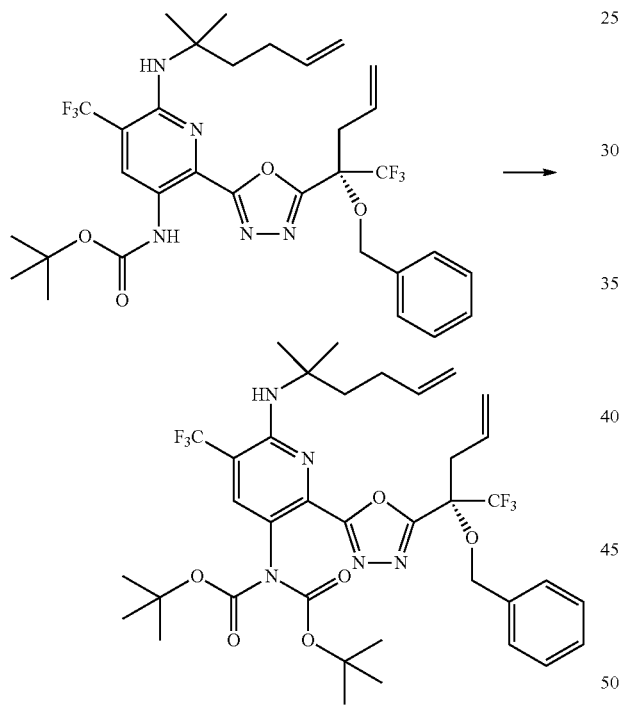

To a solution of tert-butyl N-[2-[5-[(1S)-1-benzyloxy-1-(trifluoromethyl)but-3-enyl]-1,3,4-oxadiazol-2-yl]-6-(1,1-dimethylpent-4-enylamino)-5-(trifluoromethyl)-3-pyridyl]carbamate (13 g, 19.41 mmol) in acetonitrile (100 mL) was added DMAP (473 mg, 3.872 mmol) and the mixture was stirred at room temperature to make it homogeneous solution. A solution of di-tert-butyl dicarbonate (5.51 g, 25.25 mmol) in acetonitrile (20 mL) was added slowly and the reaction mixture was stirred for 40 minutes. The mixture was concentrated under reduced pressure to remove CH$_3$CN, then azeotroped with toluene to remove residual $^t$BuOH. The resulting material was dissolved in a 1:1 mixture of dichloromethane/toluene (40 mL) and filtered through a fritted funnel to remove residual solids. The filtrate was concentrated and the residue was purified by silica gel chromatography using a gradient from 100% hexanes to 50% ethyl acetate in hexanes giving as an orange syrup, tert-butyl N-[2-[5-[(1S)-1-benzyloxy-1-(trifluoromethyl)but-3-enyl]-1,3,4-oxadiazol-2-yl]-6-(1,1-dimethylpent-4-enylamino)-5-(trifluoromethyl)-3-pyridyl]-N-tert-butoxycarbonyl-carbamate (12 g, 80%). $^1$H NMR (400 MHz, Chloroform-d) δ 7.58 (s, 1H), 7.42-7.26 (m, 5H), 6.01-5.82 (m, 1H), 5.82-5.60 (m, 1H), 5.27-5.11 (m, 2H), 5.00-4.83 (m, 3H), 4.71 (dd, J=73.3, 10.6 Hz, 2H), 3.18 (d, J=7.0, 2.1 Hz, 2H), 2.04-1.95 (m, 4H), 1.46 (s, 6H), 1.41 (d, J=3.6 Hz, 18H) ppm. ESI-MS m/z calc. 769.3274, found 670.6 (M+1−Boc)$^+$; Retention time: 0.44 minutes (LC Method S).

Step 7: tert-Butyl N-[(6S)-6-benzyloxy-12,12-dimethyl-6,15-bis(trifluoromethyl)-19-oxa-3,4,13,18-tetrazatricyclo[12.3.1.1$^{2,5}$]nonadeca-1(18),2,4,8,14,16-hexaen-17-yl]-N-tert-butoxycarbonyl-carbamate (E/Z Mixture)

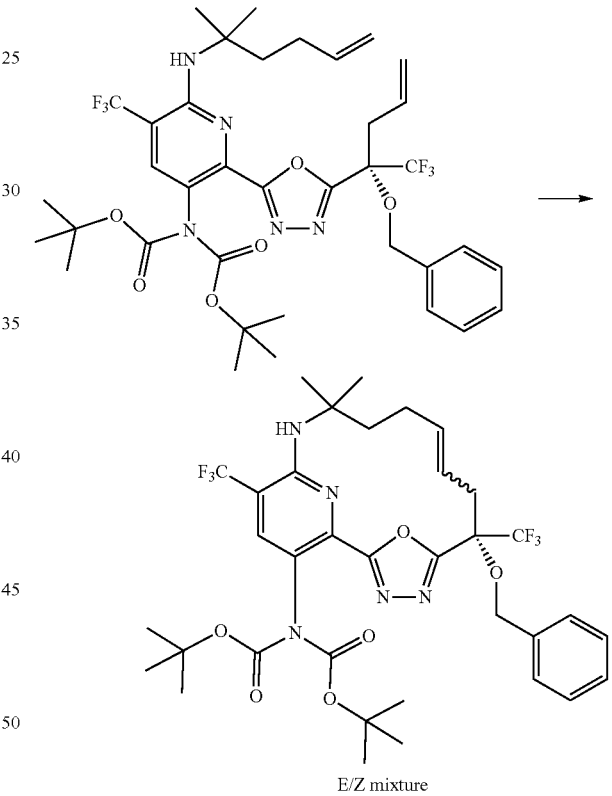

E/Z mixture

A stirring solution of tert-butyl N-[2-[5-[(1S)-1-benzyloxy-1-(trifluoromethyl)but-3-enyl]-1,3,4-oxadiazol-2-yl]-6-(1,1-dimethylpent-4-enylamino)-5-(trifluoromethyl)-3-pyridyl]-N-tert-butoxycarbonyl-carbamate (18 g, 23.38 mmol) in toluene (2.7 L) was sparged vigorously with N$_2$ then began heating the solution to 70° C. When the internal temperature reached 50° C., Zhan catalyst-1B (2.6 g, 3.543 mmol) was added and heated the mixture for 3 hours at 70° C. The reaction vessel was cooled to ambient temperature and 2-sulfanylpyridine-3-carboxylic acid (2.23 g, 14.37 mmol) was added followed by triethylamine (2 mL, 14.35 mmol). The mixture was stirred at ambient temperature overnight and silica gel (40 g, 230 to 400 mesh) was added.

Stirred the mixture for 20 minutes at ambient temperature and then filtered through a pad of Celite. Rinsed the filter cake with 200 mL EtOAc and the filtrate was concentrated under reduced pressure. The residue was purified by silica gel chromatography using a gradient from 100% hexanes to 25% EtOAc in hexanes over 40 min giving as a colorless oil, tert-butyl N-[(6S)-6-benzyloxy-12,12-dimethyl-6,15-bis(trifluoromethyl)-19-oxa-3,4,13,18-tetrazatricyclo[12.3.1.12,5]nonadeca-1(18),2,4,8,14,16-hexaen-17-yl]-N-tert-butoxycarbonyl-carbamate (E/Z mixture) (11.87 g, 62%). $^1$H NMR (400 MHz, DMSO-d6) δ 8.12 (s, 1H), 7.37-7.30 (m, 5H), 6.00 (dt, J=15.0, 7.4 Hz, 1H), 5.62-5.54 (m, 1H), 5.55-5.17 (m, 1H), 4.81 (d, J=11.2 Hz, 1H), 4.42 (d, J=11.2 Hz, 1H), 3.31-3.18 (m, 1H), 2.84 (dd, J=14.3, 7.6 Hz, 1H), 2.42-2.29 (m, 1H), 2.25 (dt, J=12.9, 5.4 Hz, 1H), 2.18-2.01 (m, 2H), 1.51 (s, 3H), 1.40 (s, 3H), 1.28 (s, 9H), 1.22 (s, 9H) ppm. ESI-MS m/z calc. 741.2961, found 742.6 (M+1)$^+$; Retention time: 3.84 minutes (LC Method D).

Step 8: tert-Butyl N-tert-butoxycarbonyl-N-[(6S)-6-hydroxy-12,12-dimethyl-6,15-bis(trifluoromethyl)-19-oxa-3,4,13,18-tetrazatricyclo[12.3.1.12,5]nonadeca-1(18),2,4,14,16-pentaen-17-yl]carbamate

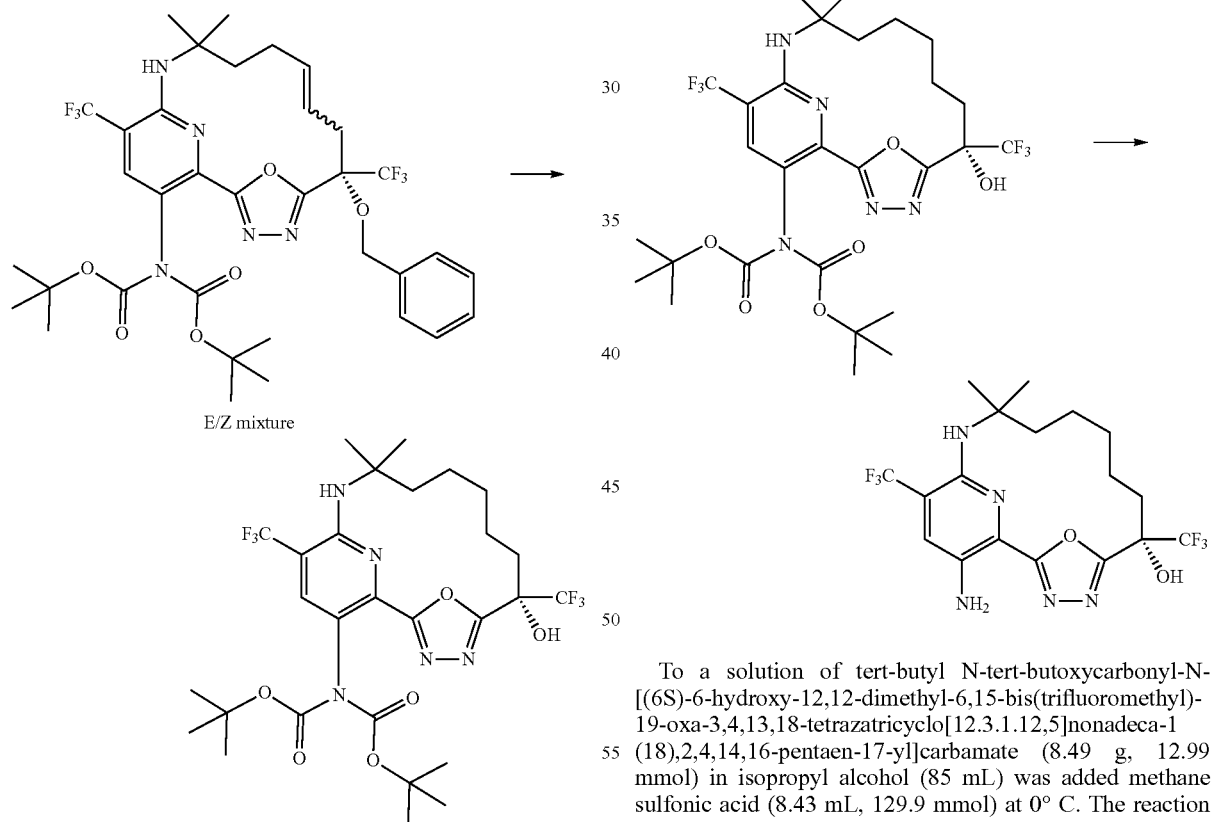

E/Z mixture

A solution of tert-butyl N-[(6S)-6-benzyloxy-12,12-dimethyl-6,15-bis(trifluoromethyl)-19-oxa-3,4,13,18-tetrazatricyclo[12.3.1.12,5]nonadeca-1(18),2,4,8,14,16-hexaen-17-yl]-N-tert-butoxycarbonyl-carbamate (E/Z mixture) (10.85 g, 14.63 mmol) in ethanol (160 mL) was degassed to remove air with 5 cycles of vacuum, N$_2$ backfill and then left the flask under N$_2$. Palladium on carbon (4.3 g, 5 w/w, 2.02 mmol) and ammonia (2.12 mL of 7 M, 14.84 mmol) were added and repeated degassing then left under N$_2$ atmosphere. The reaction mixture was stirred overnight under 1 atm of hydrogen pressure using a hydrogen gas bag and needle to vent. Replaced the hydrogen atmosphere with N$_2$ and filtered the mixture through a Celite pad rinsing the filter cake thoroughly with EtOH (200 mL). The filtrate was concentrated under reduced pressure to afford as a colorless oil, tert-butyl N-tert-butoxycarbonyl-N-[(6S)-6-hydroxy-12,12-dimethyl-6,15-bis(trifluoromethyl)-19-oxa-3,4,13,18-tetrazatricyclo[12.3.1.12,5]nonadeca-1(18),2,4,14,16-pentaen-17-yl]carbamate (9.35 g, 88%). $^1$H NMR (400 MHz, Chloroform-d) δ 7.60 (s, 1H), 5.01 (s, 1H), 3.93 (s, 1H), 3.29-3.03 (m, 1H), 2.46-2.36 (m, 1H), 2.11-1.97 (m, 1H), 1.95-1.60 (m, 2H), 1.58-1.39 (m, 25H), 1.39 (s, 2H), 1.34-1.17 (m, 2H) ppm. ESI-MS m/z calc. 653.26483, found 654.4 (M+1)$^+$; Retention time: 3.41 minutes (LC Method D).

Step 9: (6S)-17-Amino-12,12-dimethyl-6,15-bis(trifluoromethyl)-19-oxa-3,4,13,18-tetrazatricyclo[12.3.1.12,5]nonadeca-1(18),2,4,14,16-pentaen-6-ol (Compound 165)

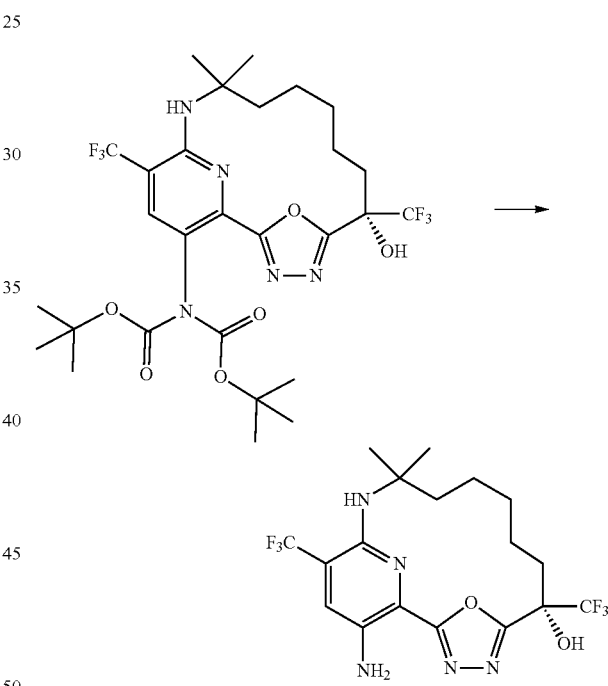

To a solution of tert-butyl N-tert-butoxycarbonyl-N-[(6S)-6-hydroxy-12,12-dimethyl-6,15-bis(trifluoromethyl)-19-oxa-3,4,13,18-tetrazatricyclo[12.3.1.12,5]nonadeca-1(18),2,4,14,16-pentaen-17-yl]carbamate (8.49 g, 12.99 mmol) in isopropyl alcohol (85 mL) was added methane sulfonic acid (8.43 mL, 129.9 mmol) at 0° C. The reaction mixture was slowly warmed to ambient temperature and stirred at ambient temperature over 3 days. Diluted the reaction mixture with ethyl acetate (250 mL), washed with a saturated aqueous solution of NaHCO$_3$(3×50 mL) and brine (60 mL) then dried over Na$_2$SO$_4$, filtered and concentrated under reduced pressure. The residue was purified by silica gel chromatography (750 g column) using a shallow gradient from 100% hexanes to 90% EtOAc in hexanes giving as a bright yellow solid, (6S)-17-amino-12,12-dimethyl-6,15-bis(trifluoromethyl)-19-oxa-3,4,13,18-tetrazatricyclo[12.3.1.1²,⁵]nonadeca-1(18),2,4,14,16-pentaen-6-ol (2.48 g, 42%). ¹H NMR (400 MHz, DMSO-d6) δ 7.61 (s, 1H), 7.59 (s, 1H), 5.96 (s, 2H), 4.64 (s, 1H), 2.91-2.71 (m, 1H), 2.30-2.15 (m, 1H), 2.15-1.97 (m, 1H), 1.92-1.74 (m, 1H), 1.73-1.57 (m, 1H), 1.55-1.38 (m, 5H), 1.36 (s, 3H), 1.31 (s, 3H) ppm. ESI-MS m/z calc. 453.15994, found 454.3 (M+1)$^+$; Retention time: 2.99 minutes (LC Method D).
Example 91: Preparation of (6R)-17-amino-12-(2-pyridyl)-6,15-bis(trifluoromethyl)-19-oxa-3,4,13,18-tetrazatricyclo[12.3.1.1²,⁵]nonadeca-1(18),2,4,14,16-pentaen-6-ol (hydrochloride salt) (Compound 166)
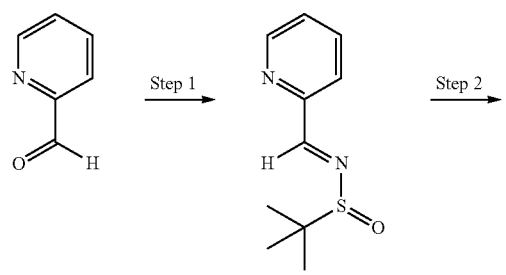
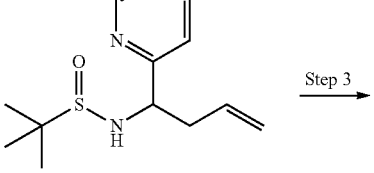
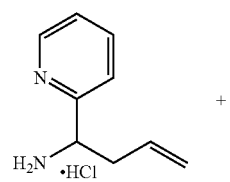
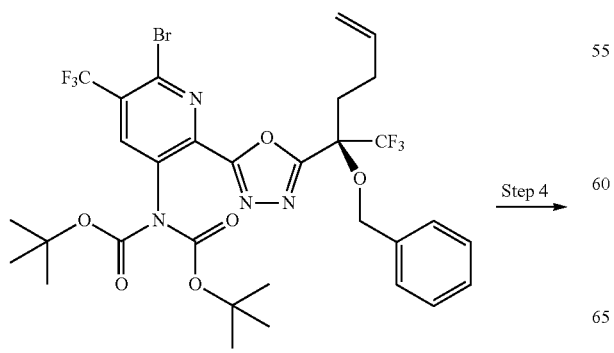
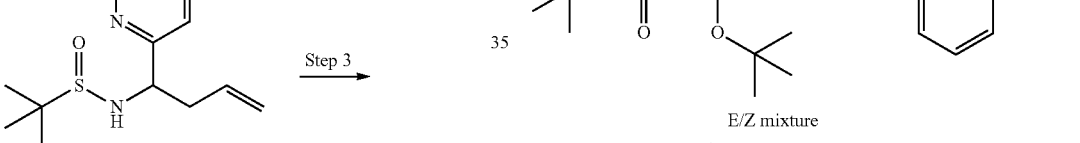
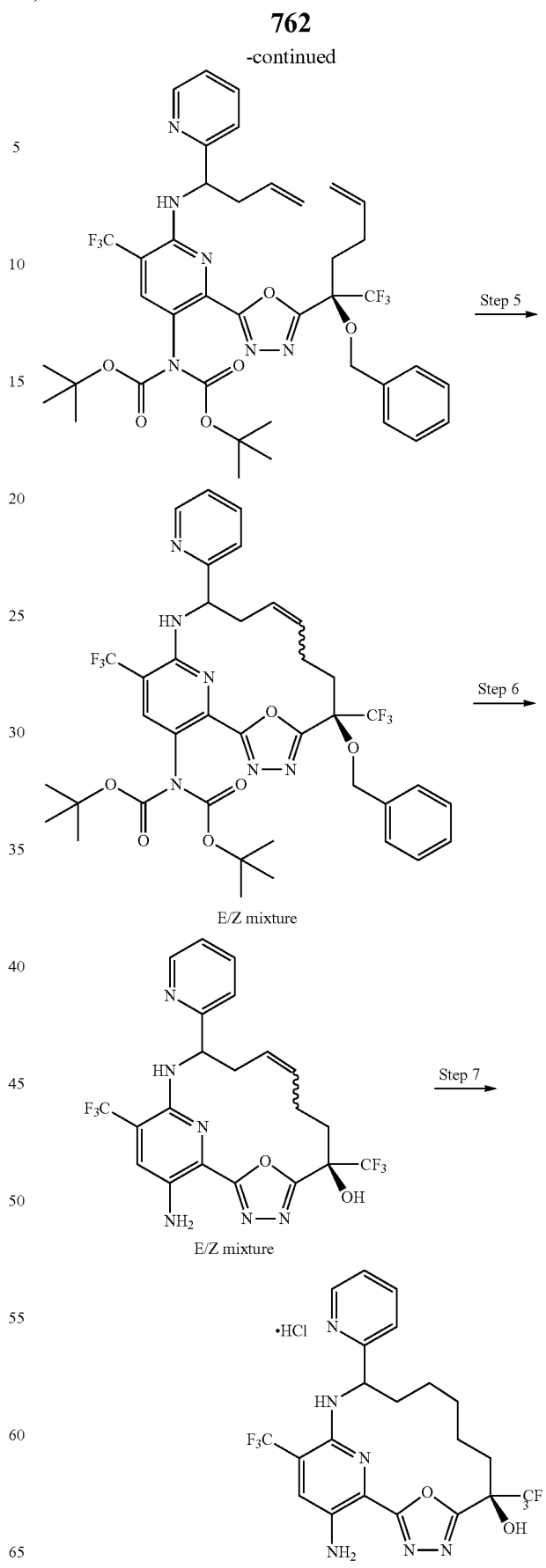

Step 1: (E)-2-Methyl-N-(2-pyridylmethylene)propane-2-sulfinamide

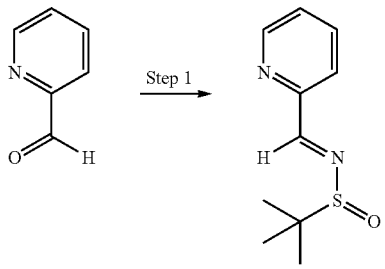

To a solution of pyridine-2-carbaldehyde (10 g, 93.362 mmol) in dichloromethane (125 mL) was added magnesium sulfate (52 g, 432.01 mmol), pyridinium p-toluenesulfonate (780 mg, 3.1038 mmol) and 2-methylpropane-2-sulfinamide (7.5 g, 61.881 mmol) and the reaction was stirred overnight at room temperature. The reaction mixture was filtered through Celite washing with dichloromethane (50 mL). The filtrate was evaporated under reduced pressure. The residue was purified by silica gel chromatography (330 g column) using a gradient from 0% to 35% ethyl acetate in dichloromethane which gave as a brown oil, (E)-2-methyl-N-(2-pyridylmethylene)propane-2-sulfinamide (9.2 g, 71%). $^1$H NMR (400 MHz, Chloroform-d) δ 8.81-8.72 (m, 1H), 8.70 (s, 1H), 8.01 (d, J=7.8 Hz, 1H), 7.81 (td, J=7.7, 1.7 Hz, 1H), 7.39 (ddd, J=7.6, 4.9, 1.2 Hz, 1H), 1.28 (s, 9H) ppm. ESI-MS m/z calc. 210.0827, found 211.2 (M+1)$^+$; Retention time: 1.51 minutes (LC Method Z).

Step 2: 2-Methyl-N-[1-(2-pyridyl)but-3-enyl]propane-2-sulfinamide

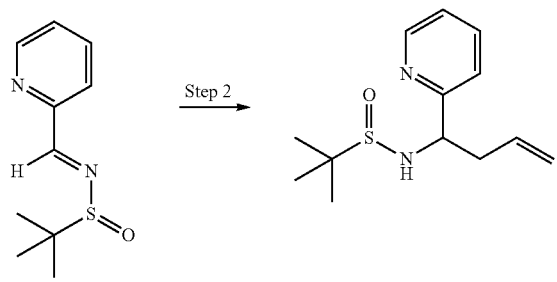 [SMILES: CC(C)(C)S(=O)/N=C/c1ccccn1 ; C=CCC(NS(=O)C(C)(C)C)c1ccccn1]

To a cooled solution of (E)-2-methyl-N-(2-pyridylmethylene)propane-2-sulfinamide (10 g, 47.552 mmol) in tetrahydrofuran (182 mL) at −78° C. was added allyl(bromo)magnesium (80 mL, 1 M in diethyl ether, 80 mmol) dropwise. The reaction was held at −78° C. until complete consumption of starting material was observed by HPLC analysis. The reaction was quenched slowly with saturated ammonium chloride (100 mL) then extracted with dichloromethane (2×50 mL). The combined organic layers were washed with brine (50 mL), dried over sodium sulfate, filtered and the solvent removed under reduced pressure. The residue was purified by silica gel chromatography (220 g column) using a gradient from 0% to 5% methanol in dichloromethane giving as a light yellow solid, 2-methyl-N-[1-(2-pyridyl)but-3-enyl]propane-2-sulfinamide (7.5 g, 62%). $^1$H NMR (400 MHz, Chloroform-d) δ 8.67-8.41 (m, 1H), 7.65 (td, J=7.7, 1.7 Hz, 1H), 7.31-7.28 (m, 1H), 7.18 (ddd, J=7.6, 4.9, 1.0 Hz, 1H), 5.92-5.51 (m, 1H), 5.19-4.98 (m, 2H), 4.84 (br d, J=6.8 Hz, 1H), 4.65-4.35 (m, 1H), 2.86-2.49 (m, 2H), 1.33-1.06 (m, 9H) ppm. ESI-MS m/z calc. 252.1296, found 253.2 (M+1)$^+$; Retention time: 1.35 minutes (LC Method Z).

Step 3: 1-(2-Pyridyl)but-3-en-1-amine (Hydrochloride Salt)

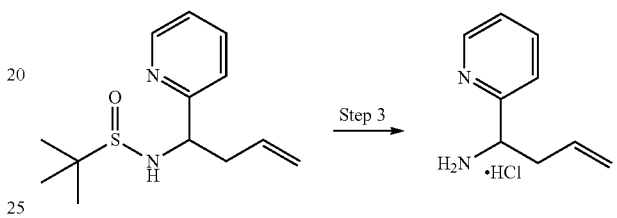

To a solution of 2-methyl-N-[1-(2-pyridyl)but-3-enyl]propane-2-sulfinamide (7 g, 27.736 mmol) in methanol (60 mL) was added hydrochloric acid (70 mL, 2 M in diethyl ether, 140 mmol) dropwise at room temperature and the resulting mixture was stirred for 1 hour at room temperature. The mixture was cooled to 0° C., then diethyl ether (100 mL) was added and stirred for 45 minutes. The resulting precipitate was filtered, washed with diethyl ether (75 mL) and the solid was dried under vacuum to give as an off-white solid, 1-(2-pyridyl)but-3-en-1-amine (hydrochloride salt) (4.75 g, 90%). $^1$H NMR (400 MHz, DMSO-d6) δ 9.06-8.77 (m, 3H), 8.75-8.58 (m, 1H), 8.14-7.90 (m, 1H), 7.84-7.64 (m, 1H), 7.60-7.39 (m, 1H), 5.79-5.49 (m, 1H), 5.08-4.85 (m, 2H), 4.65-4.52 (m, 1H), 2.88-2.75 (m, 1H), 2.73-2.57 (m, 1H) ppm. ESI-MS m/z calc. 148.1, found 149.2 (M+1)$^+$; Retention time: 2.02 minutes (LC Method BB).

Step 4: tert-Butyl N-[2-[5-[(1R)-1-benzyloxy-1-(trifluoromethyl)pent-4-enyl]-1,3,4-oxadiazol-2-yl]-6-[1-(2-pyridyl)but-3-enylamino]-5-(trifluoromethyl)-3-pyridyl]-N-tert-butoxycarbonyl-carbamate

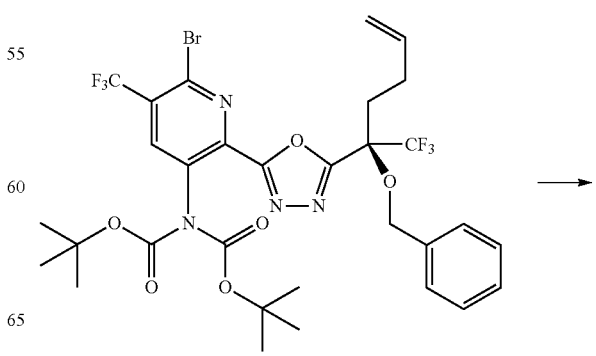

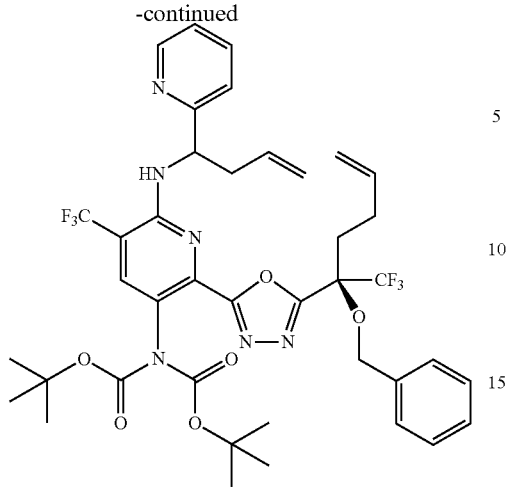

In a 100-mL nitrogen purged vessel, 1-(2-pyridyl)but-3-en-1-amine (hydrochloride salt) (760 mg, 4.116 mmol), DIEA (1.5 mL, 8.612 mmol), 3 Å molecular sieves and tert-butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate (1 g, 1.331 mmol) were combined in DMSO (20 mL). The mixture was degassed by bubbling nitrogen through the solution for 5 minutes, then the vessel was capped, and the mixture was heated at 90° C. for 16 h. The reaction mixture was cooled to room temperature and concentrated under reduced pressure. The material was then diluted with water and ethyl acetate (50 mL) was added. Then citric acid solution was added and the resulting mixture was extracted with ethyl acetate (2×50 mL). The organics were combined, dried over sodium sulfate, filtered and evaporated. The residue was purified by silica gel chromatography (80 gram column) using a shallow gradient from 100% hexanes to 100% ethyl acetate which produced as a yellow solid, tert-butyl N-[2-[5-[(1R)-1-benzyloxy-1-(trifluoromethyl)pent-4-enyl]-1,3,4-oxadiazol-2-yl]-6-[1-(2-pyridyl)but-3-enylamino]-5-(trifluoromethyl)-3-pyridyl]-N-tert-butoxycarbonyl-carbamate (98 mg, 9%). ESI-MS m/z calc. 818.32263, found 819.0 (M+1)$^+$; Retention time: 1.94 minutes (LC Method J).

Step 5: tert-Butyl N-[(6R)-6-benzyloxy-12-(2-pyridyl)-6,15-bis(trifluoromethyl)-19-oxa-3,4,13,18-tetrazatricyclo[12.3.1.1²,⁵]nonadeca-1(17),2,4,9,14(18),15-hexaen-17-yl]-N-tert-butoxycarbonyl-carbamate (E/Z Mixture)

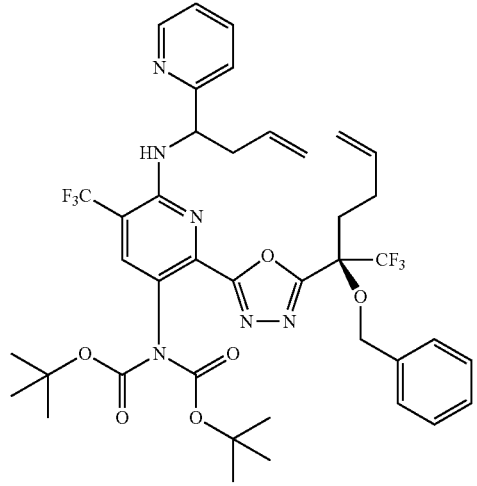

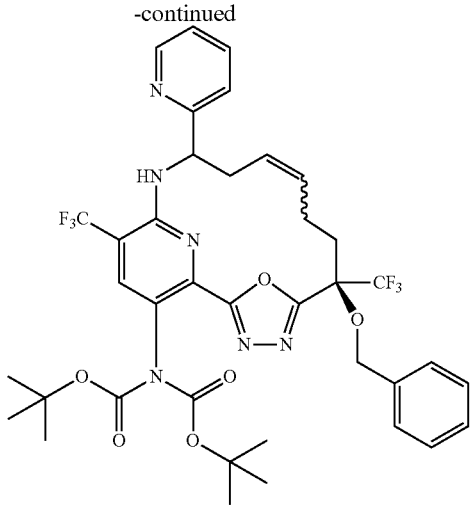

E/Z mixture

In a 100 mL 3-neck flask, a continuously degassed solution via nitrogen line of Zhan catalyst-1B (23 mg, 0.03135 mmol) was dissolved in 1,2-dichloroethane (75 mL) and the mixture was heated to 50° C. under nitrogen atmosphere. Then, a solution of tert-butyl N-[2-[5-[(1R)-1-benzyloxy-1-(trifluoromethyl)pent-4-enyl]-1,3,4-oxadiazol-2-yl]-6-[1-(2-pyridyl)but-3-enylamino]-5-(trifluoromethyl)-3-pyridyl]-N-tert-butoxycarbonyl-carbamate (98 mg, 0.1197 mmol) in 1,2-dichloroethane (5 mL) was added via syringe. The resulting mixture was heated at 85° C. for 12 h. The reaction mixture was cooled to room temperature and concentrated under reduced pressure. The residue was purified by silica gel chromatography (12 g column) using a gradient from 100% hexanes to 40% ethyl acetate in hexanes which afforded tert-butyl N-[(6R)-6-benzyloxy-12-(2-pyridyl)-6,15-bis(trifluoromethyl)-19-oxa-3,4,13,18-tetrazatricyclo[12.3.1.1²,⁵]nonadeca-1(17),2,4,9,14(18),15-hexaen-17-yl]-N-tert-butoxycarbonyl-carbamate (E/Z mixture) (23 mg, 24%). ESI-MS m/z calc. 790.2914, found 791.2 (M+1)$^+$; Retention time: 1.82 minutes (LC Method J).

Step 6: (6R)-17-Amino-12-(2-pyridyl)-6,15-bis(trifluoromethyl)-19-oxa-3,4,13,18-tetrazatricyclo[12.3.1.1²,⁵]nonadeca-1(18),2,4,9,14,16-hexaen-6-ol (E/Z Mixture)

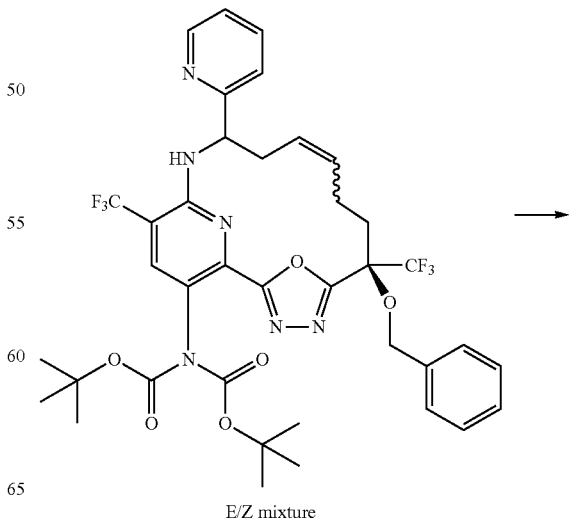

E/Z mixture

-continued

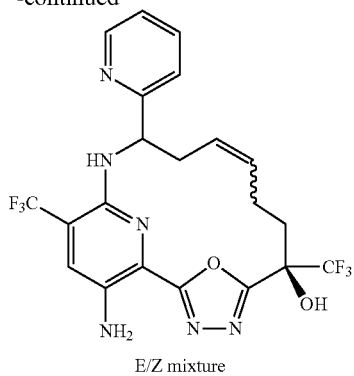

E/Z mixture

To tert-butyl N-[(6R)-6-benzyloxy-12-(2-pyridyl)-6,15-bis(trifluoromethyl)-19-oxa-3,4,13,18-tetrazatricyclo[12.3.1.12,5]nonadeca-1(17),2,4,9,14(18),15-hexaen-17-yl]-N-tert-butoxycarbonyl-carbamate (E/Z mixture) (23 mg, 0.02909 mmol) was added TFA (3.0 mL, 38.94 mmol) and the reaction was stirred at room temperature for 2 h followed by heating at 60° C. for 2 h. Solvents were evaporated, then diluted the residue with DCM and re-concentrated and then dried the residue under vacuum for 1 h to produce as a crude yellow solid, (6R)-17-amino-12-(2-pyridyl)-6,15-bis(trifluoromethyl)-19-oxa-3,4,13,18-tetrazatricyclo[12.3.1.12,5]nonadeca-1(18),2,4,9,14,16-hexaen-6-ol (E/Z mixture) (10 mg, 69%). ESI-MS m/z calc. 500.13956, found 501.0 (M+1)$^+$; Retention time: 1.14 minutes (LC Method J). This material was taken directly to the ensuing step.

Step 7: (6R)-17-Amino-12-(2-pyridyl)-6,15-bis(trifluoromethyl)-19-oxa-3,4,13,18-tetrazatricyclo[12.3.1.12,5]nonadeca-1(18),2,4,14,16-pentaen-6-ol (Hydrochloride Salt) (Compound 166)

In a 50 mL round bottom flask, a solution of (6R)-17-amino-12-(2-pyridyl)-6,15-bis(trifluoromethyl)-19-oxa-3,4,13,18-tetrazatricyclo[12.3.1.12,5]nonadeca-1(18),2,4,9,14,16-hexaen-6-ol (E/Z mixture) (10 mg, 0.01998 mmol) in ethyl acetate (500 µL) was purged with nitrogen. Then Pd/C (8 mg, 10% w/w, 0.007517 mmol) was added. The mixture was degassed with nitrogen then purged by a balloon filled with hydrogen gas. The mixture was stirred at 1 atm of hydrogen for 1 h. The reaction was then filtered and concentrated. The residue was purified by silica gel chromatography (4 g column) using a gradient from 100% hexanes to 70% ethyl acetate in hexanes followed by reverse phase HPLC using a gradient from 1% to 99% acetonitrile in water (+5 mM HCl) over 15 minutes giving as a yellow solid and mixture of diastereomers, (6R)-17-amino-12-(2-pyridyl)-6,15-bis(trifluoromethyl)-19-oxa-3,4,13,18-tetrazatricyclo[12.3.1.12,5]nonadeca-1(18),2,4,14,16-pentaen-6-ol (hydrochloride salt) (3.16 mg, 29%). $^1$H NMR (400 MHz, DMSO-d6) δ 8.66 (d, J=4.9 Hz, 1H), 7.86 (s, 2H), 7.68 (s, 2H), 7.61 (s, 1H), 7.49 (d, J=9.2 Hz, 1H), 7.40 (s, 2H), 6.12 (s, 1H), 4.93 (s, 1H), 2.73 (s, 1H), 1.62 (s, 1H), 1.46 (d, J=9.9 Hz, 4H), 1.25 (d, J=16.5 Hz, 4H) ppm. ESI-MS m/z calc. 502.15518, found 503.2 (M+1)$^+$; Retention time: 1.76 minutes (LC Method A).

Example 92: Preparation of (12S)-20-amino-6,18-bis(trifluoromethyl)-10,22-dioxa-3,4,16,21-tetraazatetracyclo[15.3.1.12,5.012,16]docosa-1(21),2,4,17,19-pentaen-6-ol (enantiomer 1) (Compound 167) and (12S)-20-amino-6,18-bis(trifluoromethyl)-10,22-dioxa-3,4,16,21-tetraazatetracyclo[15.3.1.12,5.012,16]docosa-1(21),2,4,17,19-pentaen-6-ol (enantiomer 2) (Compound 168)

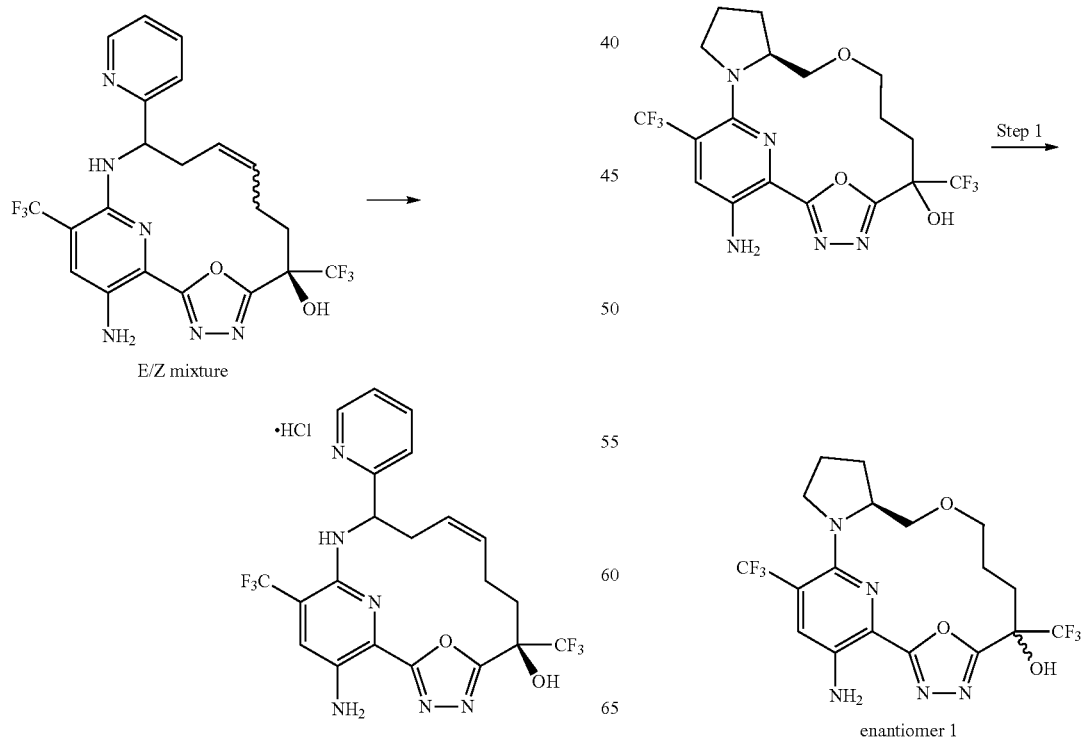

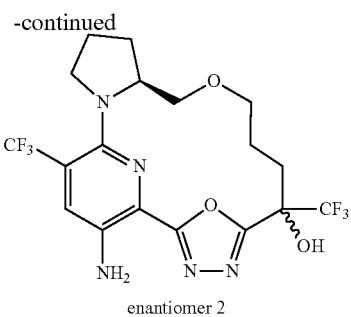

enantiomer 2

Step 1: (12S)-20-Amino-6,18-bis(trifluoromethyl)-10,22-dioxa-3,4,16,21-tetraazatetracyclo[15.3.1.1²,⁵.0¹²,¹⁶]docosa-1(21),2,4,17,19-pentaen-6-ol (enantiomer 1) (Compound 167) and (12S)-20-amino-6,18-bis(trifluoromethyl)-10,22-dioxa-3,4,16,21-tetraazatetracyclo[15.3.1.1²,⁵.0¹²,¹⁶]docosa-1(21),2,4,17,19-pentaen-6-ol (enantiomer 2) (Compound 168)

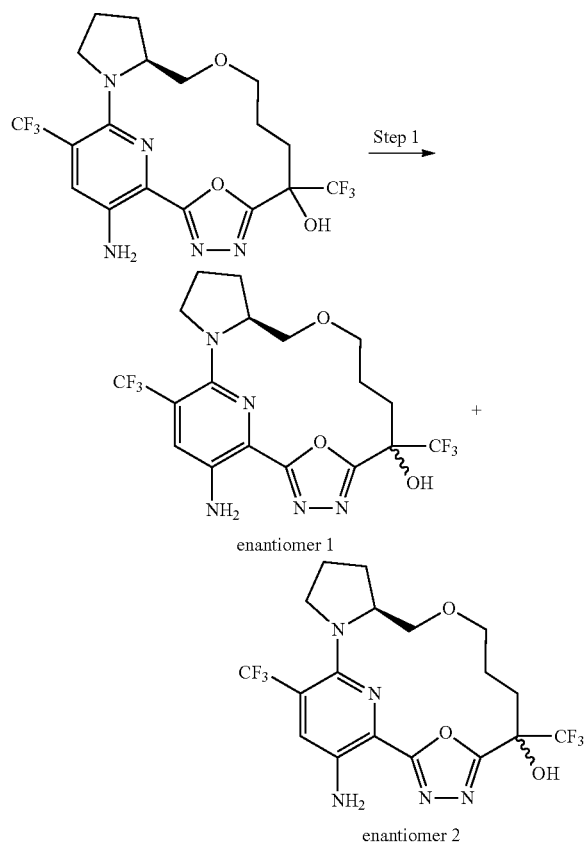

(12S)-20-Amino-6,18-bis(trifluoromethyl)-10,22-dioxa-3,4,16,21-tetraazatetracyclo[15.3.1.1²,⁵.0¹²,¹⁶]docosa-1(21),2,4,17,19-pentaen-6-ol (250 mg, 0.5349 mmol) was purified by chiral SFC using a LUX-4 column (250×21.2 mm, 5 µm particle size) eluting with 12% MeOH (+20 mM NH₃)/88% CO₂ giving two single enantiomer products.

The first enantiomer to elute was isolated as a yellow solid, (12S)-20-amino-6,18-bis(trifluoromethyl)-10,22-dioxa-3,4,16,21-tetraazatetracyclo[15.3.1.1²,⁵.0¹²,¹⁶]docosa-1(21),2,4,17,19-pentaen-6-ol (enantiomer 1) (65.5 mg, 52%). ¹H NMR (400 MHz, Chloroform-d) δ 7.50 (s, 1H), 4.43-4.36 (m, 1H), 4.14 (d, J=7.3 Hz, 1H), 4.00-3.24 (m, 5H), 3.02-2.73 (m, 2H), 2.37-1.75 (m, 4H), 1.61 (s, 2H), 1.26 (s, 2H), 1.01-0.71 (m, 1H) ppm. ESI-MS m/z calc. 467.13922, found 468.1 (M+1)⁺; Retention time: 1.84 minutes (LC Method A).

The second enantiomer to elute was isolated as a yellow solid, (12S)-20-amino-6,18-bis(trifluoromethyl)-10,22-dioxa-3,4,16,21-tetraazatetracyclo[15.3.1.1²,⁵.0¹²,¹⁶]docosa-1(21),2,4,17,19-pentaen-6-ol (enantiomer 2) (105.5 mg, 84%). ¹H NMR (400 MHz, Chloroform-d) δ 7.56 (s, 1H), 4.35 (d, J=8.0 Hz, 2H), 3.79 (t, J=11.3 Hz, 1H), 3.70-3.38 (m, 3H), 2.99 (s, 1H), 2.77 (t, J=12.7 Hz, 1H), 2.38-1.78 (m, 6H), 1.58 (s, 1H), 1.25 (s, 3H) ppm. ESI-MS m/z calc. 467.13922, found 468.1 (M+1)⁺; Retention time: 1.78 minutes (LC Method A).

Example 93: Preparation of methyl (12R)-20-amino-6-hydroxy-6-(trifluoromethyl)-22-oxa-3,4,16,21-tetraazatetracyclo[15.3.1.1²,⁵.0¹²,¹⁶]docosa-1(21),2,4,17,19-pentaene-18-carboxylate (enantiomer 1) (Compound 169) and methyl (12R)-20-amino-6-hydroxy-6-(trifluoromethyl)-22-oxa-3,4,16,21-tetraazatetracyclo[15.3.1.1²,⁵.0¹²,¹⁶]docosa-1(21),2,4,17,19-pentaene-18-carboxylate (enantiomer 2) (Compound 170)

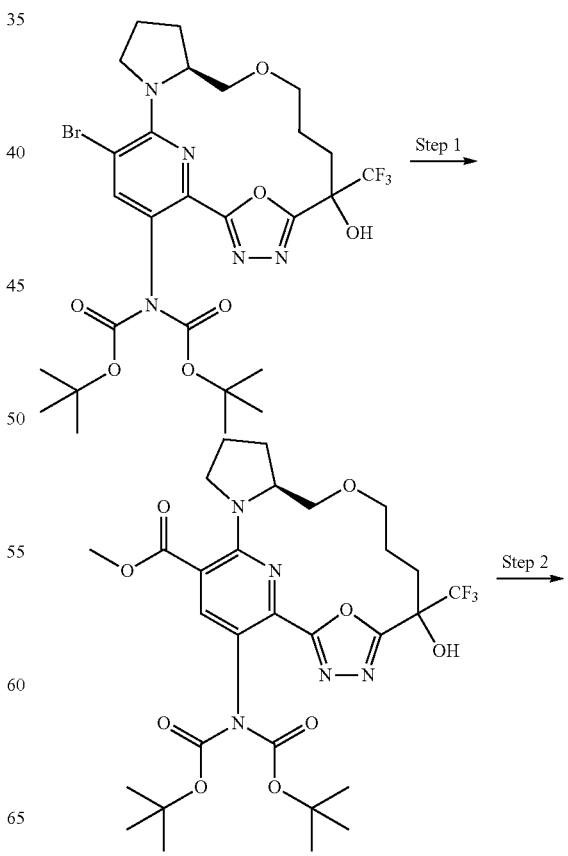

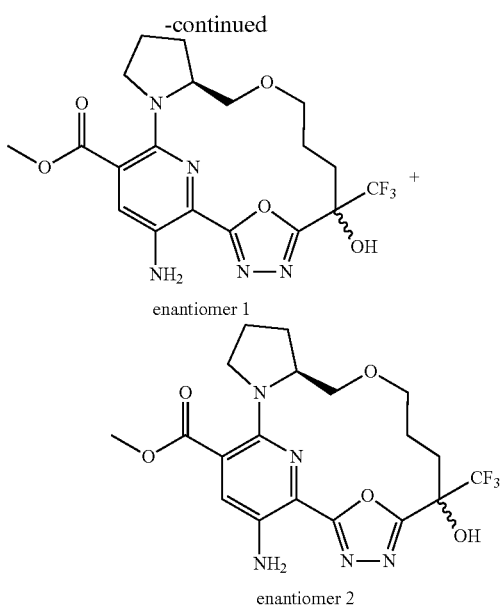

enantiomer 1 enantiomer 2

Step 1: Methyl (12R)-20-{bis[(tert-butoxy)carbonyl]amino}-6-hydroxy-6-(trifluoromethyl)-22-oxa-3,4,16,21-tetraazatetracyclo[15.3.1.1²,⁵.0¹²,¹⁶]docosa-1(21),2,4,17,19-pentaene-18-carboxylate

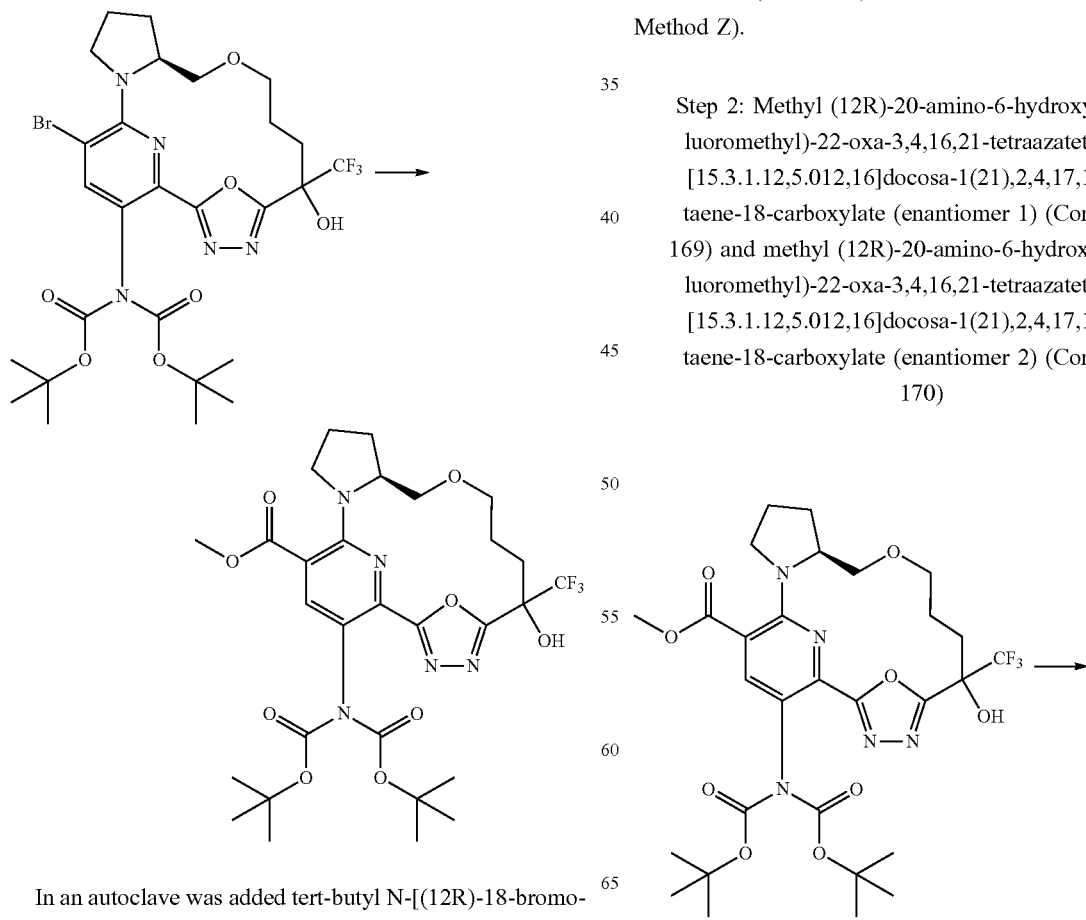

In an autoclave was added tert-butyl N-[(12R)-18-bromo-6-hydroxy-6-(trifluoromethyl)-22-oxa-3,4,16,21-tetraazatetracyclo[15.3.1.1²,⁵.0¹²,¹⁶]docosa-1(21),2,4,17,19-pentaen-20-yl]-N-[(tert-butoxy)carbonyl]carbamate (200 mg, 0.2956 mmol), methanol (5 mL), triethylamine (72.6 mg, 0.1 mL, 0.7175 mmol) and [1,1'-bis(diphenylphosphino)ferrocene]dichloropalladium(II) (6 mg, 0.0082 mmol). The autoclave was purged with nitrogen, then with carbon monoxide. The mixture was heated at 130° C. and the carbon monoxide pressure was adjusted to 120 psi. The mixture was stirred for 3 h at 130° C., then cooled to 25° C. The mixture was purged with nitrogen and concentrated under vacuum. The resulting solid was diluted with ethyl acetate (50 mL) then water (20 mL) and sodium carbonate (1.5 g) were added and the mixture was vigorously stirred for 20 minutes. The layers were separated and the organic layer was washed with water (10 mL) and brine (10 mL) then dried over sodium sulfate, filtered and concentrated under reduced pressure giving as a crude brown solid, methyl (12R)-20-{bis[(tert-butoxy)carbonyl]amino}-6-hydroxy-6-(trifluoromethyl)-22-oxa-3,4,16,21-tetraazatetracyclo[15.3.1.1²,⁵.0¹²,¹⁶]docosa-1(21),2,4,17,19-pentaene-18-carboxylate (189 mg) which was used directly in the next step. ESI-MS m/z calc. 655.2829, found 556.4 (M+H-Boc)⁺; Retention time: 2.15 minutes (LC Method Z).

Step 2: Methyl (12R)-20-amino-6-hydroxy-6-(trifluoromethyl)-22-oxa-3,4,16,21-tetraazatetracyclo[15.3.1.1²,⁵.0¹²,¹⁶]docosa-1(21),2,4,17,19-pentaene-18-carboxylate (enantiomer 1) (Compound 169) and methyl (12R)-20-amino-6-hydroxy-6-(trifluoromethyl)-22-oxa-3,4,16,21-tetraazatetracyclo[15.3.1.1²,⁵.0¹²,¹⁶]docosa-1(21),2,4,17,19-pentaene-18-carboxylate (enantiomer 2) (Compound 170)

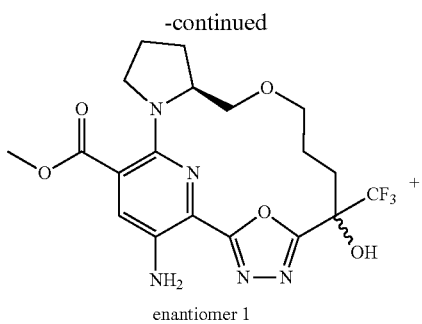

enantiomer 1

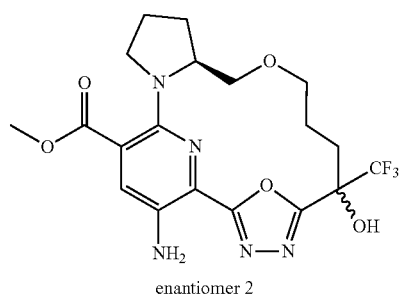

enantiomer 2

To a solution of methyl (12R)-20-{bis[(tert-butoxy)carbonyl]amino}-6-hydroxy-6-(trifluoromethyl)-22-oxa-3,4,16,21-tetraazatetracyclo[15.3.1.12,5.012,16]docosa-1(21),2,4,17,19-pentaene-18-carboxylate (189 mg, 0.2883 mmol) in dichloromethane (3 mL) was added TFA (4.44 g, 3 mL, 38.94 mmol) and the reaction mixture was stirred at room temperature for 3 hours. The mixture was concentrated, and the residue was purified by reverse phase HPLC using a gradient from 50% to 60% acetonitrile in water (+0.1% formic acid) over 16 min which gave the separation of two diastereomeric products:

The first diastereomer to elute was isolated as a yellow solid, methyl (12R)-20-amino-6-hydroxy-6-(trifluoromethyl)-22-oxa-3,4,16,21-tetraazatetracyclo[15.3.1.12,5.012,16]docosa-1(21),2,4,17,19-pentaene-18-carboxylate (enantiomer 1) (11 mg, 8%). $^1$H NMR (400 MHz, Chloroform-d) δ 7.49 (s, 1H), 4.92 (br. s, 2H), 3.92 (s, 3H), 3.61-3.45 (m, 2H), 2.93-2.77 (m, 2H), 2.38-2.17 (m, 3H), 2.16-2.01 (m, 1H), 2.01-1.90 (m, 1H), 1.76-1.47 (m, 8H), 1.15-1.02 (m, 1H) ppm. $^{19}$F NMR (377 MHz, Chloroform-d) δ −77.36 (s, 3F) ppm. ESI-MS m/z calc. 455.178, found 456.2 (M+1)$^+$; Retention time: 4.4 minutes (LC Method AA).

The second diastereomer to elute was isolated as a yellow solid, methyl (12R)-20-amino-6-hydroxy-6-(trifluoromethyl)-22-oxa-3,4,16,21-tetraazatetracyclo[15.3.1.12,5.012,16]docosa-1(21),2,4,17,19-pentaene-18-carboxylate (enantiomer 2) (11 mg, 8%). $^1$H NMR (400 MHz, Chloroform-d) δ 7.37 (s, 1H), 4.84 (br s, 2H), 4.11 (br s, 1H), 3.92 (s, 3H), 3.55-3.41 (m, 1H), 2.92 (br t, J=8.1 Hz, 1H), 2.72 (br t, J=11.2 Hz, 1H), 2.44 (br t, J=12.8 Hz, 1H), 2.29-2.18 (m, 1H), 2.17-2.05 (m, 1H), 2.02-1.90 (m, 1H), 1.85-1.41 (m, 9H), 1.07-0.91 (m, 1H) ppm. $^{19}$F NMR (377 MHz, Chloroform-d) δ −80.68 (s, 3F) ppm. ESI-MS m/z calc. 455.17804, found 456.2 (M+1)$^+$; Retention time: 4.55 minutes (LC Method AA).

Example 94: Preparation of 17-amino-11,11-dimethyl-6,15-bis(trifluoromethyl)-19-oxa-3,4,13,18-tetrazatricyclo[12.3.1.12,5]nonadeca-1(18),2,4,14,16-pentaen-6-ol (enantiomer 1) (Compound 171) and 17-amino-11,11-dimethyl-6,15-bis(trifluoromethyl)-19-oxa-3,4,13,18-tetrazatricyclo[12.3.1.12,5] nonadeca-1(18),2,4,14,16-pentaen-6-ol (enantiomer 2) (Compound 172)

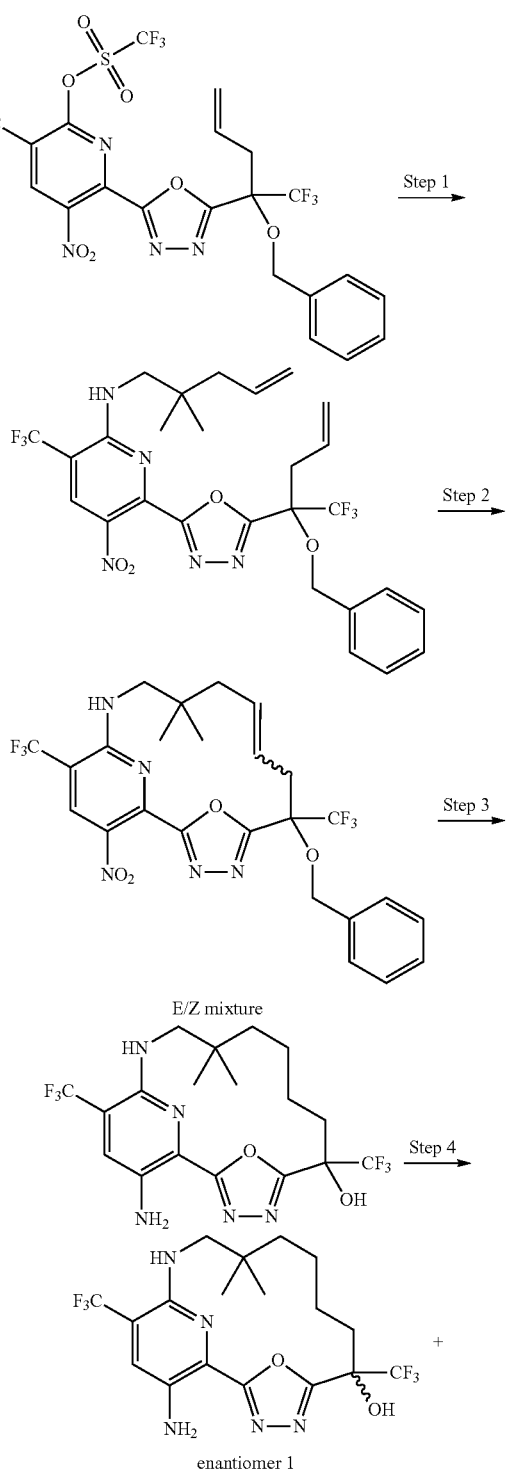

enantiomer 1

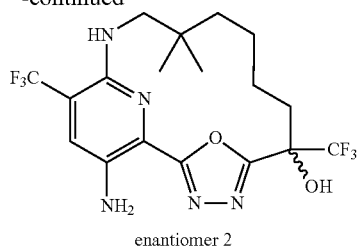

enantiomer 2

Step 1: 6-[5-[1-Benzyloxy-1-(trifluoromethyl)but-3-enyl]-1,3,4-oxadiazol-2-yl]-N-(2,2-dimethylpent-4-enyl)-5-nitro-3-(trifluoromethyl)pyridin-2-amine

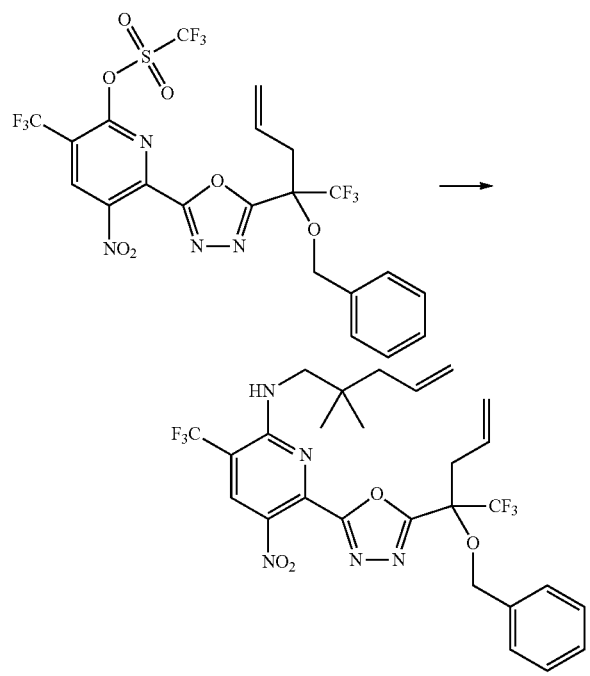

In a 150 mL sealed vial, [6-[5-[1-benzyloxy-1-(trifluoromethyl)but-3-enyl]-1,3,4-oxadiazol-2-yl]-5-nitro-3-(trifluoromethyl)-2-pyridyl] trifluoromethanesulfonate (900 mg, 1.414 mmol) was dissolved in acetonitrile (35 mL) at room temperature and 2,2-dimethylpent-4-en-1-amine (hydrochloride salt) (675 mg, 4.51 mmol) was added followed by DIEA (1.75 mL, 10.05 mmol). The reaction mixture was heated at 80° C. for 16 h then cooled to room temperature. The mixture was concentrated and the residue was purified by silica gel chromatography (80 gram column) using a gradient from 100% hexanes to 70% ethyl acetate in hexanes giving as a dark orange foam, 6-[5-[1-benzyloxy-1-(trifluoromethyl)but-3-enyl]-1,3,4-oxadiazol-2-yl]-N-(2,2-dimethylpent-4-enyl)-5-nitro-3-(trifluoromethyl)pyridin-2-amine (570 mg, 67%). $^1$H NMR (400 MHz, DMSO-d6) δ 8.55 (s, 1H), 8.02 (t, J=6.3 Hz, 1H), 7.37-7.30 (m, 5H), 5.97-5.72 (m, 2H), 5.38 (dd, J=17.0, 1.8 Hz, 1H), 5.25 (dd, J=10.3, 1.8 Hz, 1H), 4.99-4.89 (m, 2H), 4.80 (d, J=10.7 Hz, 1H), 4.55 (d, J=10.6 Hz, 1H), 3.47 (d, J=6.1 Hz, 2H), 2.63-2.49 (m, 2H), 1.92 (d, J=7.4 Hz, 2H), 0.81 (s, 6H) ppm. ESI-MS m/z calc. 599.1967, found 600.2 (M+1)$^+$; Retention time: 1.72 minutes (LC Method M).

Step 2: 6-Benzyloxy-11,11-dimethyl-17-nitro-6,15-bis(trifluoromethyl)-19-oxa-3,4,13,18-tetrazatricyclo[12.3.1.1$^{2,5}$]nonadeca-1(18),2,4,8,14,16-hexaene (E/Z mixture)

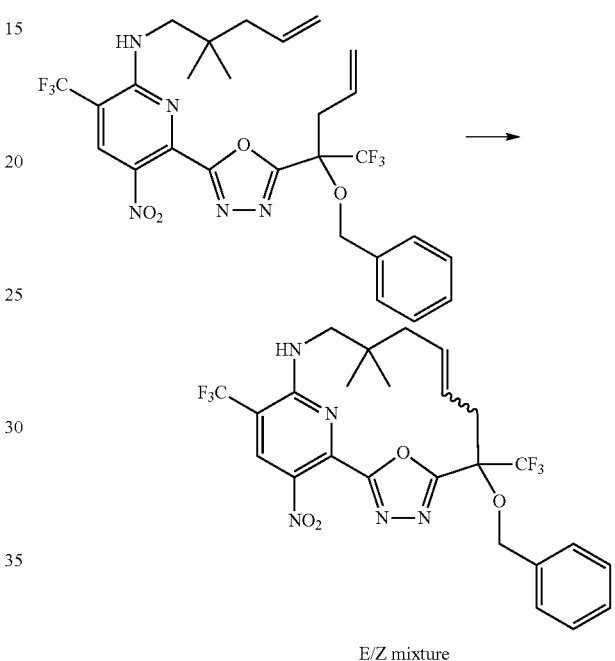

E/Z mixture

In a 1 L, 3-neck flask, a continuously degassed solution via nitrogen line of Zhan catalyst-1B (180 mg, 0.2453 mmol) in DCE (400 mL) was heated to 50° C. under nitrogen atmosphere. Then, a solution of 6-[5-[1-benzyloxy-1-(trifluoromethyl)but-3-enyl]-1,3,4-oxadiazol-2-yl]-N-(2,2-dimethylpent-4-enyl)-5-nitro-3-(trifluoromethyl)pyridin-2-amine (570 mg, 0.9508 mmol) in DCE (75 mL) was added via syringe. The resulting mixture was heated at 80° C. for 16 h. Then, the heating bath was removed and the reaction mixture was cooled to room temperature. A solution of ethyl buta-2,3-dienoate (450 µL, 3.877 mmol) in DCM (28 mL) was added and the mixture was stirred at room temperature for an hour. The solvent was evaporated and the residue was purified by silica gel chromatography (80 gram column) using a gradient from 100% hexanes to 40% ethyl acetate in hexanes to afford as a light yellow solid, 6-benzyloxy-11,11-dimethyl-17-nitro-6,15-bis(trifluoromethyl)-19-oxa-3,4,13,18-tetrazatricyclo[12.3.1.1$^{2,5}$]nonadeca-1(18),2,4,8,14,16-hexaene (E/Z mixture) (112 mg, 14%). ESI-MS m/z calc. 571.1654, found 572.2 (M+1)$^+$; Retention time: 1.46 minutes (LC Method M).

Step 3: 17-Amino-11,11-dimethyl-6,15-bis(trifluoromethyl)-19-oxa-3,4,13,18-tetrazatricyclo[12.3.1.1²,⁵]nonadeca-1(18),2,4,14,16-pentaen-6-ol

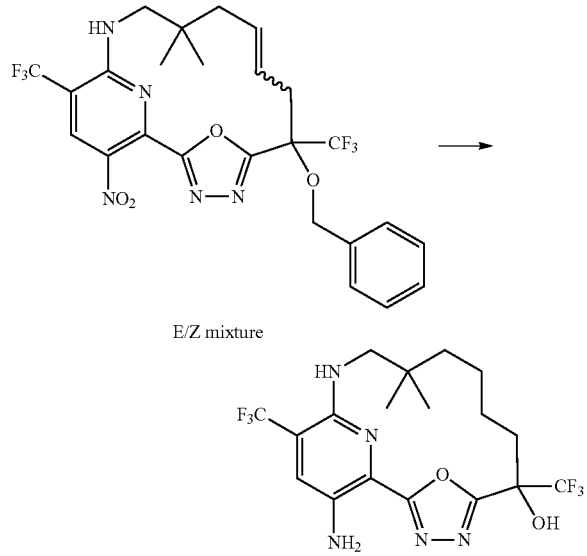

In a stainless steel pressure vessel, a solution of 6-benzyloxy-11,11-dimethyl-17-nitro-6,15-bis(trifluoromethyl)-19-oxa-3,4,13,18-tetrazatricyclo[12.3.1.1²,⁵]nonadeca-1(18),2,4,8,14,16-hexaene (E/Z mixture) (112 mg, 0.1372 mmol) in AcOH (3 mL) was purged with nitrogen. Then Pd/C (150 mg of 10% w/w, 0.141 mmol) was added. The mixture was degassed with nitrogen then subjected to vacuum (3×) then purged with hydrogen gas and stirred at 240 psi of hydrogen for 16 h. The reaction was filtered, and the filtrate was concentrated under reduced pressure. The residue was purified by reverse phase HPLC using a gradient from 1% to 99% acetonitrile in water (+5 mM HCl) over 15 min giving as a yellow solid, 17-amino-11,11-dimethyl-6,15-bis(trifluoromethyl)-19-oxa-3,4,13,18-tetrazatricyclo[12.3.1.1²,⁵]nonadeca-1(18),2,4,14,16-pentaen-6-ol (21 mg, 34%). ESI-MS m/z calc. 453.15994, found 454.2 (M+1)⁺; Retention time: 2.02 minutes (LC Method A).

Step 4: 17-Amino-11,11-dimethyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (Compound 171) and 17-amino-11,11-dimethyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (Compound 172)

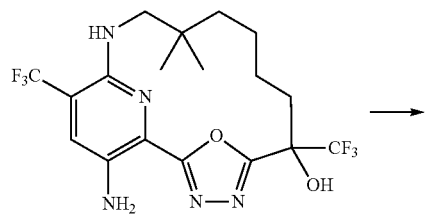

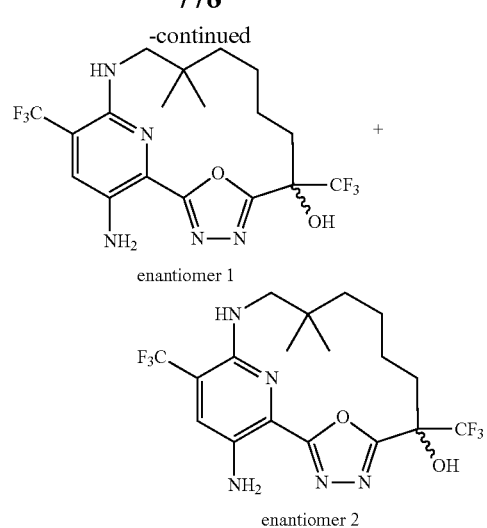

17-Amino-11,11-dimethyl-6,15-bis(trifluoromethyl)-19-oxa-3,4,13,18-tetrazatricyclo[12.3.1.1²,⁵]nonadeca-1(18),2,4,14,16-pentaen-6-ol (21 mg, 0.04632 mmol) was purified by SFC using an OJ column (250×4.6 mm, 5 μm particle size) eluting with 8% MeOH (+20 mM NH₃) in CO₂ which gave two single enantiomer products:

The first enantiomer to elute was isolated as a yellow solid, 17-amino-11,11-dimethyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (4.6 mg, 43%). ¹H NMR (400 MHz, Chloroform-d) δ 7.27 (s, 1H), 5.10 (s, 2H), 4.72 (t, J=6.7 Hz, 1H), 3.77 (s, 1H), 3.66 (s, 1H), 3.03 (s, 1H), 2.42-2.32 (m, 1H), 2.20 (dt, J=15.0, 5.0 Hz, 1H), 2.03-1.96 (m, 1H), 1.77 (s, 1H), 1.50-1.38 (m, 1H), 1.26-1.17 (m, 2H), 0.91 (s, 6H) ppm. One exchangeable proton not observed in the NMR. ESI-MS m/z calc. 453.15994, found 454.2 (M+1)⁺; Retention time: 2.02 minutes (LC Method A).

The later eluting enantiomer was isolated as a yellow solid, 17-amino-11,11-dimethyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (4.5 mg, 42%). ¹H NMR (400 MHz, Chloroform-d) δ 7.29 (s, 1H), 5.09 (s, 2H), 4.80-4.65 (m, 1H), 3.64 (s, 2H), 3.01 (d, J=14.3 Hz, 1H), 2.38 (dt, J=14.7, 8.3 Hz, 1H), 2.21 (dt, J=14.9, 5.0 Hz, 1H), 2.04-1.97 (m, 1H), 1.77 (d, J=15.4 Hz, 1H), 1.50-1.39 (m, 1H), 1.26-1.17 (m, 2H), 0.91 (s, 6H) ppm. One exchangeable proton not observed in the NMR. ESI-MS m/z calc. 453.15994, found 454.2 (M+1)⁺; Retention time: 2.02 minutes (LC Method A).

Example 95: Preparation of (6R)-17-amino-6,15-bis(trifluoromethyl)spiro[19-oxa-3,4,13,18-tetrazatricyclo[12.3.1.1²,⁵]nonadeca-1(18),2,4,14,16-pentaene-12,1'-cyclobutane]-6-ol (Compound 173)

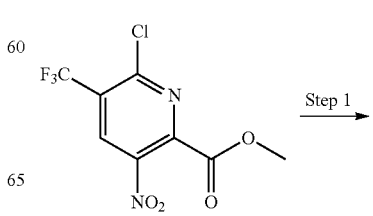

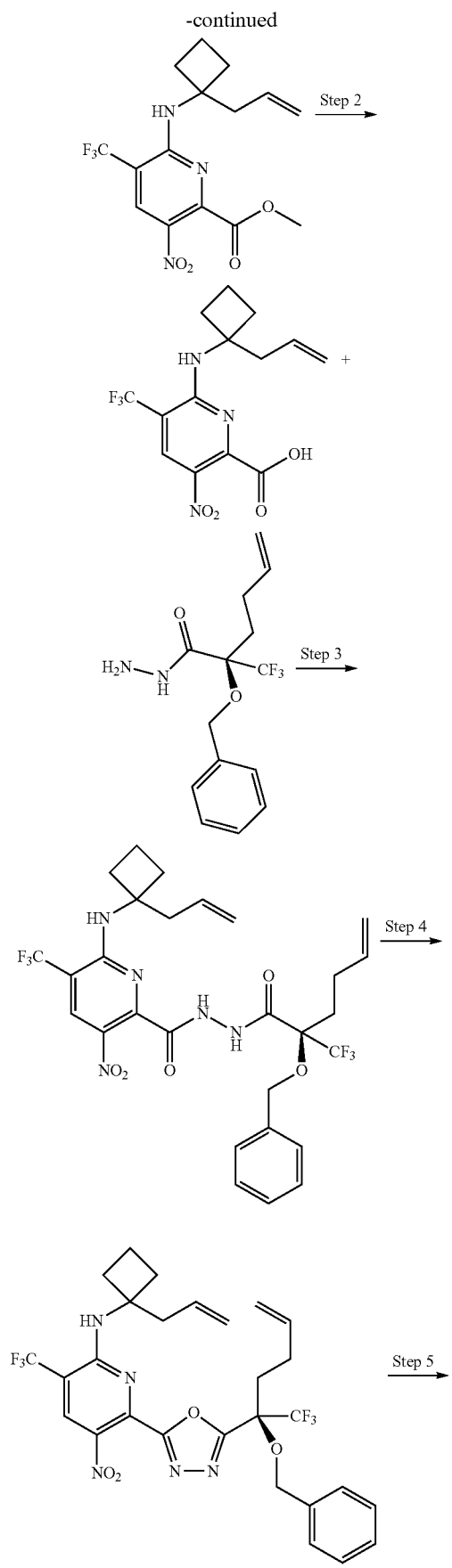

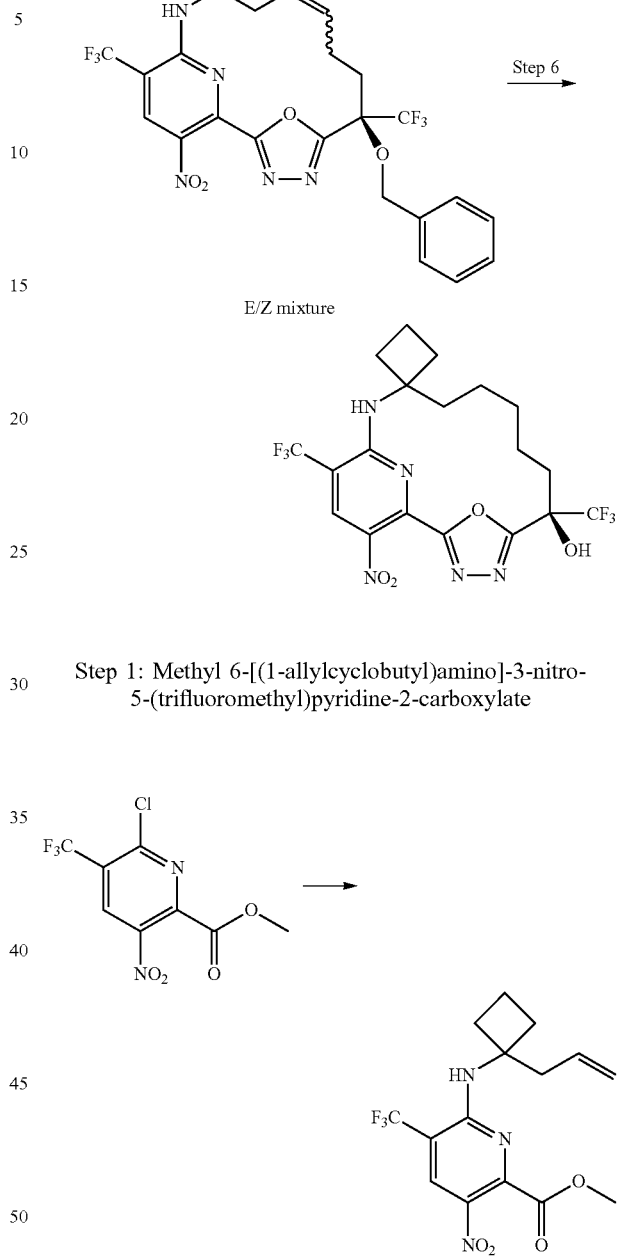

Step 1: Methyl 6-[(1-allylcyclobutyl)amino]-3-nitro-5-(trifluoromethyl)pyridine-2-carboxylate In a 125 mL sealed vessel, 1-allylcyclobutanamine (hydrochloride salt) (673 mg, 3.655 mmol), DIEA (3.0 mL, 17.22 mmol) and methyl 6-chloro-3-nitro-5-(trifluoromethyl)pyridine-2-carboxylate (1.1 g, 3.479 mmol) were combined in acetonitrile (20 mL) and the mixture was heated at 80° C. for 1 h. The reaction mixture was cooled to ambient temperature and concentrated under reduced pressure. The residue was diluted with ethyl acetate (50 mL) and washed with brine (2×25 mL), dried over sodium sulfate, filtered and concentrated. The residue was purified by silica gel chromatography (80 gram column) using a gradient from 100% hexanes to 30% ethyl acetate in hexanes to afford as a pale yellow solid, methyl 6-[(1-allylcyclobutyl)amino]-3-nitro-5-(trifluoromethyl)pyridine-2-carboxylate (1.15 g, 92%). $^1$H NMR (400 MHz, DMSO-d6) δ 8.42 (d, J=0.8 Hz, 1H), 7.88 (s, 1H), 5.78 (ddt, J=17.3, 10.2, 7.1 Hz, 1H), 5.08-4.94 (m, 2H), 3.91 (s, 3H), 2.69 (dt, J 7.2, 1.3 Hz, 2H), 2.30 (qd, J=9.7, 2.7 Hz, 2H), 2.20-2.09 (m, 2H), 1.77 (dtd, J=9.7, 7.5, 6.9, 4.5 Hz, 2H) ppm. ESI-MS m/z calc. 359.10928, found 360.2 (M+1)⁺; Retention time: 1.98 minutes (LC Method A).

Step 2: 6-[(1-Allylcyclobutyl)amino]-3-nitro-5-(trifluoromethyl)pyridine-2-carboxylic Acid

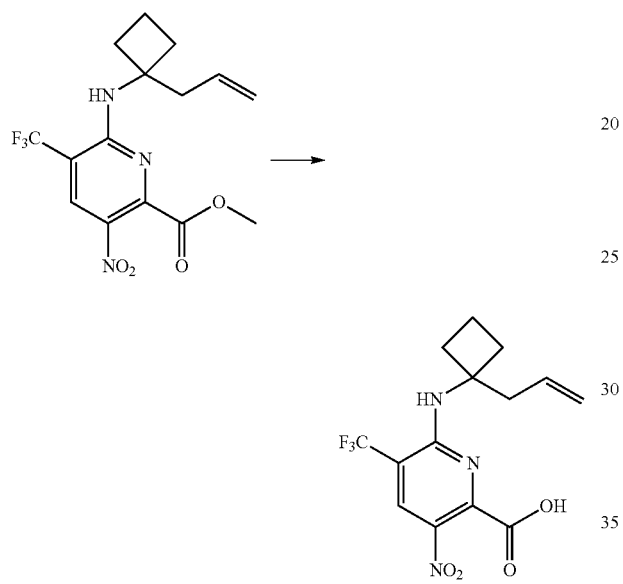

To a solution of methyl 6-[(1-allylcyclobutyl)amino]-3-nitro-5-(trifluoromethyl)pyridine-2-carboxylate (1.15 g, 3.201 mmol) in THF (20 mL), methanol (20 mL) and water (10 mL) was added lithium hydroxide (1.17 g, 48.86 mmol) and the mixture was stirred at room temperature for 1 h. THF and methanol were removed under reduced pressure. An aqueous 3 M HCl solution was added until the mixture was acidic, then extracted with ethyl acetate (3×50 mL). The organic phases were combined, washed with brine (50 mL), dried over anhydrous sodium sulfate, filtered and concentrated under reduced pressure. The residue was then placed under vacuum for 16 h to afford as a pale yellow solid, 6-[(1-allylcyclobutyl)amino]-3-nitro-5-(trifluoromethyl)pyridine-2-carboxylic acid (1.04 g, 94%). ¹H NMR (400 MHz, DMSO-d6) δ 14.06 (s, 1H), 8.41 (s, 1H), 7.73 (s, 1H), 5.79 (ddt, J 17.3, 10.2, 7.1 Hz, 1H), 5.16-4.86 (m, 2H), 2.71 (d, J=7.1 Hz, 2H), 2.31 (qd, J=9.7, 2.7 Hz, 2H), 2.21-2.10 (m, 2H), 1.84-1.71 (m, 2H) ppm. ESI-MS m/z calc. 345.09363, found 346.2 (M+1)⁺; Retention time: 1.61 minutes (LC Method A).

Step 3: 6-[(1-Allylcyclobutyl)amino]-N'-[(2R)-2-benzyloxy-2-(trifluoromethyl)hex-5-enoyl]-3-nitro-5-(trifluoromethyl)pyridine-2-carbohydrazide

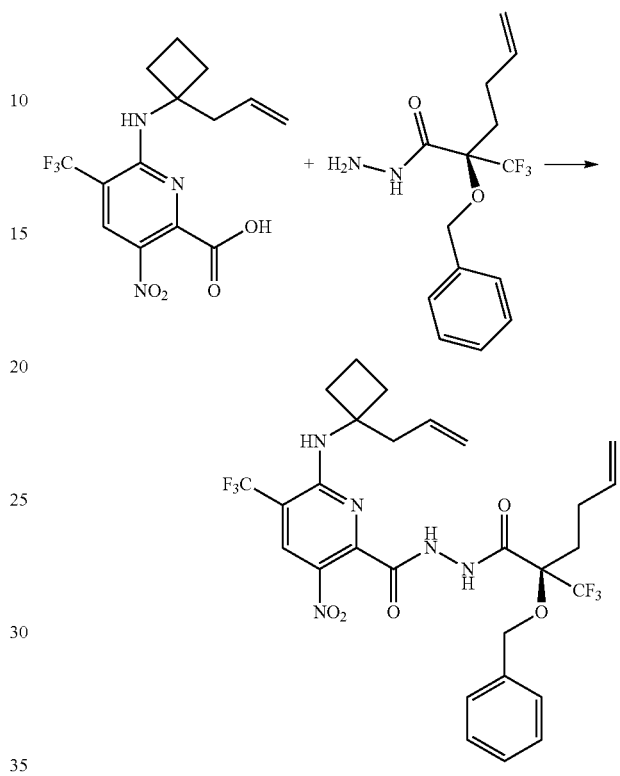

To a solution of 6-[(1-allylcyclobutyl)amino]-3-nitro-5-(trifluoromethyl)pyridine-2-carboxylic acid (875 mg, 2.534 mmol) in DMF (20 mL) was added DIEA (2 mL, 11.48 mmol) and HATU (955 mg, 2.512 mmol). The reaction mixture was stirred at room temperature for 10 min then added dropwise (2R)-2-benzyloxy-2-(trifluoromethyl)hex-5-enehydrazide (845 mg, 2.795 mmol) dissolved in DMF (5 mL) and the reaction mixture was stirred at room temperature for 2 h. The reaction was diluted with ethyl acetate and washed with brine. The organic layer was further washed with 10% citric acid solution followed by brine. The organics were separated, dried over sodium sulfate, filtered and evaporated. The residue was purified by silica gel chromatography (80 gram column) using a gradient from 100% dichloromethane to 15% methanol in dichloromethane to afford as a yellow foam, 6-[(1-allylcyclobutyl)amino]-N'-[(2R)-2-benzyloxy-2-(trifluoromethyl)hex-5-enoyl]-3-nitro-5-(trifluoromethyl)pyridine-2-carbohydrazide (1.2 g, 75%). ¹H NMR (400 MHz, DMSO-d6) δ 10.51 (d, J=1.3 Hz, 1H), 10.39 (d, J=1.3 Hz, 1H), 8.42 (s, 1H), 7.65 (s, 1H), 7.54-7.45 (m, 2H), 7.41-7.30 (m, 3H), 5.92-5.73 (m, 2H), 5.10-5.04 (m, 2H), 5.03-4.98 (m, 2H), 4.84 (q, J=11.4 Hz, 2H), 2.74 (d, J=7.2 Hz, 2H), 2.36-2.17 (m, 8H), 1.82-1.70 (m, 2H) ppm. ESI-MS m/z calc. 629.2073, found 630.2 (M+1)⁺; Retention time: 1.74 minutes (LC Method J).

Step 4: N-(1-Allylcyclobutyl)-6-[5-[(1R)-1-benzyloxy-1-(trifluoromethyl)pent-4-enyl]-1,3,4-oxadiazol-2-yl]-5-nitro-3-(trifluoromethyl)pyridin-2-amine

Step 5: (6R)-6-Benzyloxy-17-nitro-6,15-bis(trifluoromethyl)spiro[19-oxa-3,4,13,18-tetrazatricyclo[12.3.1.1²,⁵]nonadeca-1(18),2,4,9,14,16-hexaene-12,1'-cyclobutane] (E/Z Mixture)

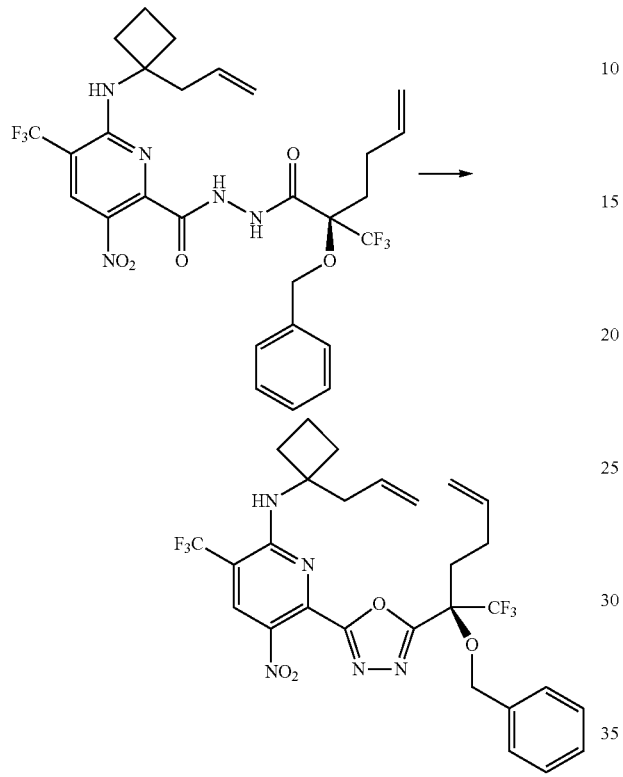

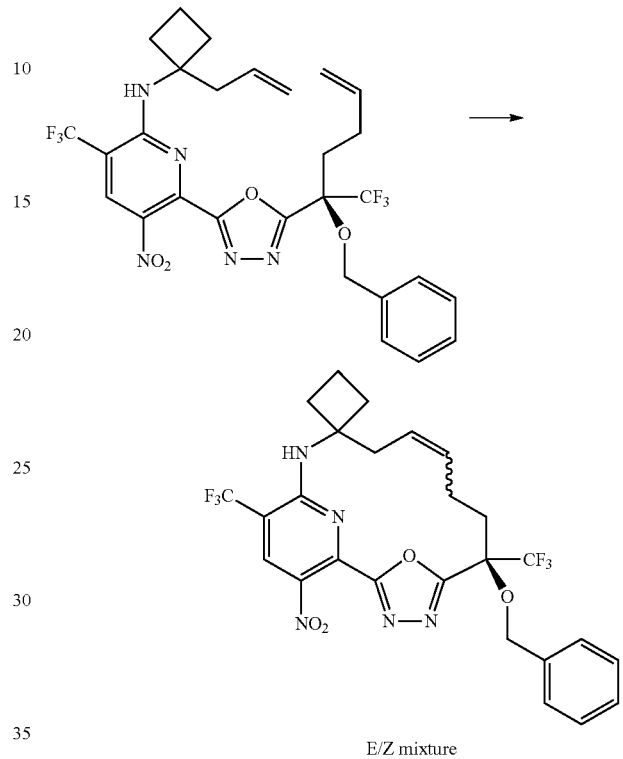

E/Z mixture

A solution of 6-[(1-allylcyclobutyl)amino]-N'-[(2R)-2-benzyloxy-2-(trifluoromethyl)hex-5-enoyl]-3-nitro-5-(trifluoromethyl)pyridine-2-carbohydrazide (1.2 g, 1.906 mmol) and DIEA (1.1 mL, 6.315 mmol) in acetonitrile (23 mL) was heated to 60° C., then p-toluenesulfonyl chloride (440 mg, 2.308 mmol) was added. The resulting mixture was stirred at 60° C. for 90 min. The reaction mixture was cooled and quenched with a saturated solution of sodium bicarbonate (100 mL) and extracted with ethyl acetate (3×100 mL). The organics were combined, dried over sodium sulfate, filtered and evaporated. The residue was purified by silica gel chromatography (80 gram column) using a gradient from 100% hexanes to 30% ethyl acetate in hexanes to afford N-(1-allylcyclobutyl)-6-[5-[(1R)-1-benzyloxy-1-(trifluoromethyl)pent-4-enyl]-1,3,4-oxadiazol-2-yl]-5-nitro-3-(trifluoromethyl)pyridin-2-amine (1.02 g, 87%). $^1$H NMR (400 MHz, DMSO-d6) δ 8.52 (s, 1H), 7.96 (s, 1H), 7.39-7.29 (m, 5H), 5.81 (dddt, J=30.8, 17.3, 10.2, 6.8 Hz, 2H), 5.10 (dq, J=17.2, 1.6 Hz, 1H), 5.04-4.90 (m, 3H), 4.76 (d, J=10.8 Hz, 1H), 4.59 (d, J=10.8 Hz, 1H), 2.65 (d, J=7.2 Hz, 2H), 2.62-2.51 (m, 2H), 2.28 (pd, J=11.0, 10.0, 3.9 Hz, 4H), 2.10 (ddt, J=12.2, 7.6, 3.8 Hz, 2H), 1.76-1.65 (m, 2H) ppm. ESI-MS m/z calc. 611.1967, found 612.2 (M+1)$^+$; Retention time: 1.66 minutes (LC Method M).

In a 1 L, 3-neck flask, a continuously degassed solution via nitrogen line of Zhan catalyst-1B (350 mg, 0.477 mmol) was dissolved in DCE (450 mL) and the mixture was heated to 50° C. under nitrogen atmosphere. Then, a solution of N-(1-allylcyclobutyl)-6-[5-[(1R)-1-benzyloxy-1-(trifluoromethyl)pent-4-enyl]-1,3,4-oxadiazol-2-yl]-5-nitro-3-(trifluoromethyl)pyridin-2-amine (1 g, 1.635 mmol) in DCE (50 mL) was added via syringe. The resulting mixture was heated at 85° C. for 5 hours then concentrated. The residue was purified by silica gel chromatography (120 gram column) using a gradient from 100% hexanes to 40% ethyl acetate in hexanes to produce as a pale yellow residue, (6R)-6-benzyloxy-17-nitro-6,15-bis(trifluoromethyl)spiro[19-oxa-3,4,13,18-tetrazatricyclo[12.3.1.1²,⁵]nonadeca-1(18),2,4,9,14,16-hexaene-12,1'-cyclobutane] (E/Z mixture) (650 mg, 68%). $^1$H NMR (400 MHz, DMSO-d6) δ 8.54 (s, 1H), 8.07 (s, 1H), 7.35 (d, J=4.6 Hz, 4H), 7.33-7.28 (m, 1H), 5.89-5.79 (m, 1H), 5.79-5.68 (m, 1H), 4.86 (s, 2H), 2.73 (t, J=10.8 Hz, 1H), 2.57-2.53 (m, 1H), 2.37-2.27 (m, 4H), 2.27-2.10 (m, 4H), 1.74 (td, J=9.9, 9.3, 4.3 Hz, 1H), 1.61 (q, J=9.4 Hz, 1H) ppm. ESI-MS m/z calc. 583.1654, found 584.2 (M+1)$^+$; Retention time: 1.35 minutes (LC Method M).

Step 6: (6R)-17-Amino-6,15-bis(trifluoromethyl)spiro[19-oxa-3,4,13,18-tetrazatricyclo[12.3.1.1²,⁵]nonadeca-1(18),2,4,14,16-pentaene-12,1'-cyclobutane]-6-ol (Compound 173)

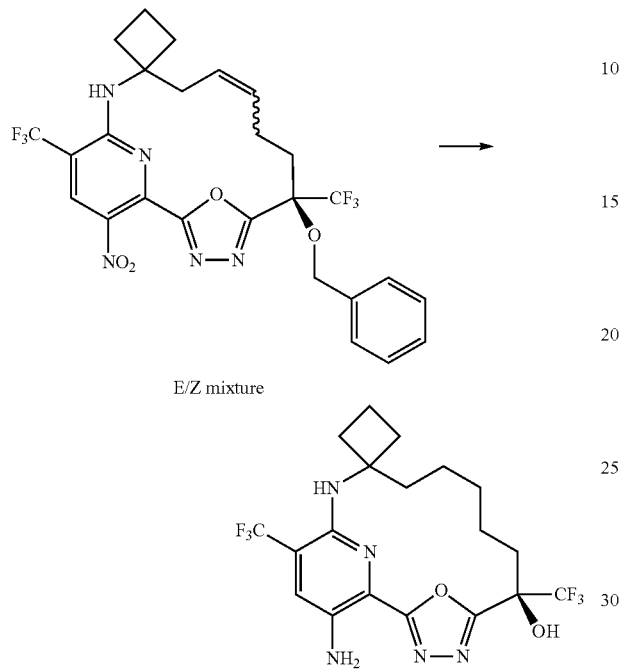

E/Z mixture

In a 250 mL round bottom flask, a solution of (6R)-6-benzyloxy-17-nitro-6,15-bis(trifluoromethyl)spiro[19-oxa-3,4,13,18-tetrazatricyclo[12.3.1.1²,⁵]nonadeca-1(18),2,4,9,14,16-hexaene-12,1'-cyclobutane] (E/Z mixture) (630 mg, 1.08 mmol) in AcOH (14 mL) and ethyl acetate (5 mL) was purged with nitrogen. Then Pd/C (1.15 g of 10% w/w, 1.081 mmol) was added. The mixture was degassed with nitrogen then subjected to vacuum (3×) then purged with hydrogen gas via a continuous needle through the solution and the mixture was stirred at 1 atm of hydrogen for 3 h. The reaction was filtered, and the material was purified by silica gel chromatography (80 g column) using a gradient from 100% hexanes to 70% ethyl acetate in hexanes which afforded a yellow solid. This material was further purified by reverse phase HPLC using a gradient from 30% to 99% acetonitrile in water (+5 mM HCl) over 15 min giving as a yellow solid, (6R)-17-amino-6,15-bis(trifluoromethyl)spiro[19-oxa-3,4,13,18-tetrazatricyclo[12.3.1.1²,⁵]nonadeca-1(18),2,4,14,16-pentaene-12,1'-cyclobutane]-6-ol (381.6 mg, 75%), ¹H NMR (400 MHz, DMSO-d6) δ 7.58 (d, J=6.6 Hz, 2H), 5.95 (s, 2H), 5.48 (s, 1H), 2.44-2.33 (m, 2H), 2.32-2.21 (m, 2H), 2.15-2.04 (m, 2H), 2.02-1.82 (m, 2H), 1.82-1.60 (m, 5H), 1.57-1.41 (m, 3H) ppm. ESI-MS m/z calc. 465.15994, found 466.2 (M+1)⁺; Retention time: 2.13 minutes (LC Method A).

Step 7: Solid Form Characterization of Amorphous Compound 173 (Neat Form) and Crystalline Compound 173 Form a (Neat)

A. X-Ray Powder Diffraction

The XRPD diffractogram for amorphous Compound 173 (neat form) produced by Step 6 was acquired using the General X-Ray Powder Diffraction (XRPD) Method. The XRPD diffractogram for amorphous Compound 173 (neat form) is provided in FIG. 18.

B. Thermogravimetric Analysis (TGA)

Figure 19:
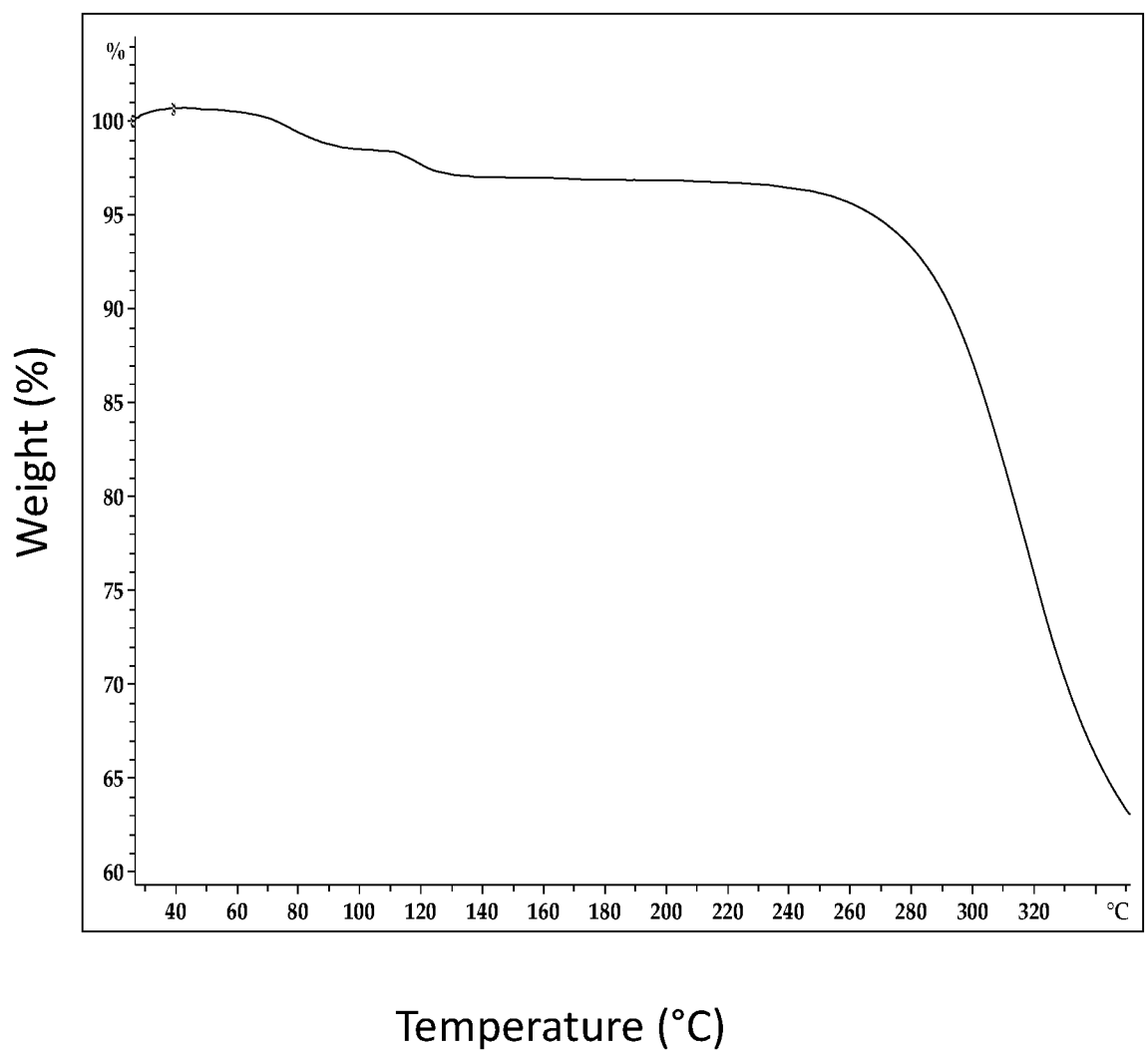
FIG. 19 provides a TGA curve for amorphous Compound 173 (neat form).

The TGA curve for amorphous Compound 173 (neat form) produced by Step 6 is provided in FIG. 19. The TGA curve shows 3.98% weight loss from 39° C. to 224.6° C., with a ramp of 10.00° C./min to 350.00° C.

C. Differential Scanning calorimetry Analysis

The DSC analysis was run using the following modulated DSC method:
1. Equilibrated at −20.00° C.,
2. Modulated by +/−1.00° C. every 60 seconds,
3. Isothermal for 5.00 min, then
4. Ramp of 2.00° C./min to 250.00° C.

Figure 20:
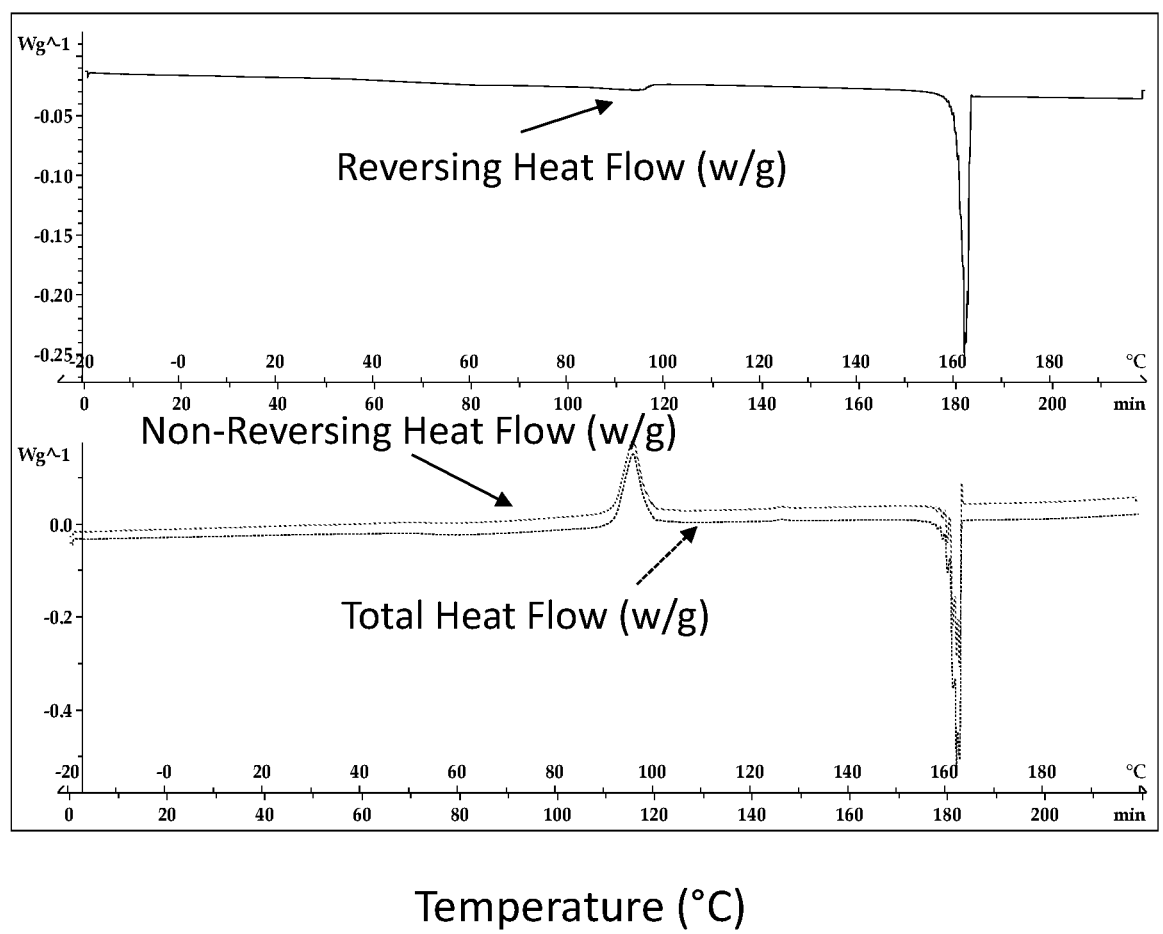
FIG. 20 provides a DSC analysis of amorphous Compound 173 (neat form).

The DSC thermogram for amorphous Compound 173 (neat form) produced by Step 6 is provided in FIG. 20. The thermogram shows recrystallization at 96.3° C. and melting at 161.53° C., 59.89 J/g. No Tg was observed.

D. Single Crystal X-Ray Diffraction

Single crystals of crystalline Compound 173 Form A (neat) were grown from dichloromethane and hexanes. X-ray diffraction data were acquired at 150 K on a Bruker diffractometer equipped with Cu Kα radiation (λ=1.54178 Å) and a CPAD detector. The structure was solved and refined using SHELX programs (Sheldrick, G. M., Acta Cryst., (2008) A64, 112-122) and results are summarized in Table 7 below.

TABLE 7

| Single crystal elucidation of crystalline Compound 173 Form A (neat) | |
|---|---|
| Crystal System | Triclinic |
| Space Group | P1 |
| a (Å) | 6.7418(4) |
| b (Å) | 11.9477(7) |
| c (Å) | 13.0827(7) |
| α (°) | 76.0210(10) |
| β (°) | 82.2150(10) |
| γ (°) | 85.4220(10) |
| V (Å3) | 1011.95(10) |
| Z/Z' | 1/2 |
| Temperature | 150 K |

Example 96: Preparation of (6R)-17-amino-12-(hydroxymethyl)-12-methyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (Compound 174) and (6R)-17-amino-12-(hydroxymethyl)-12-methyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (Compound 175)

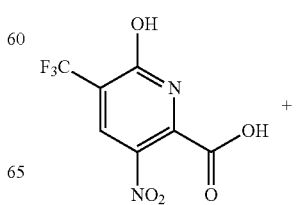

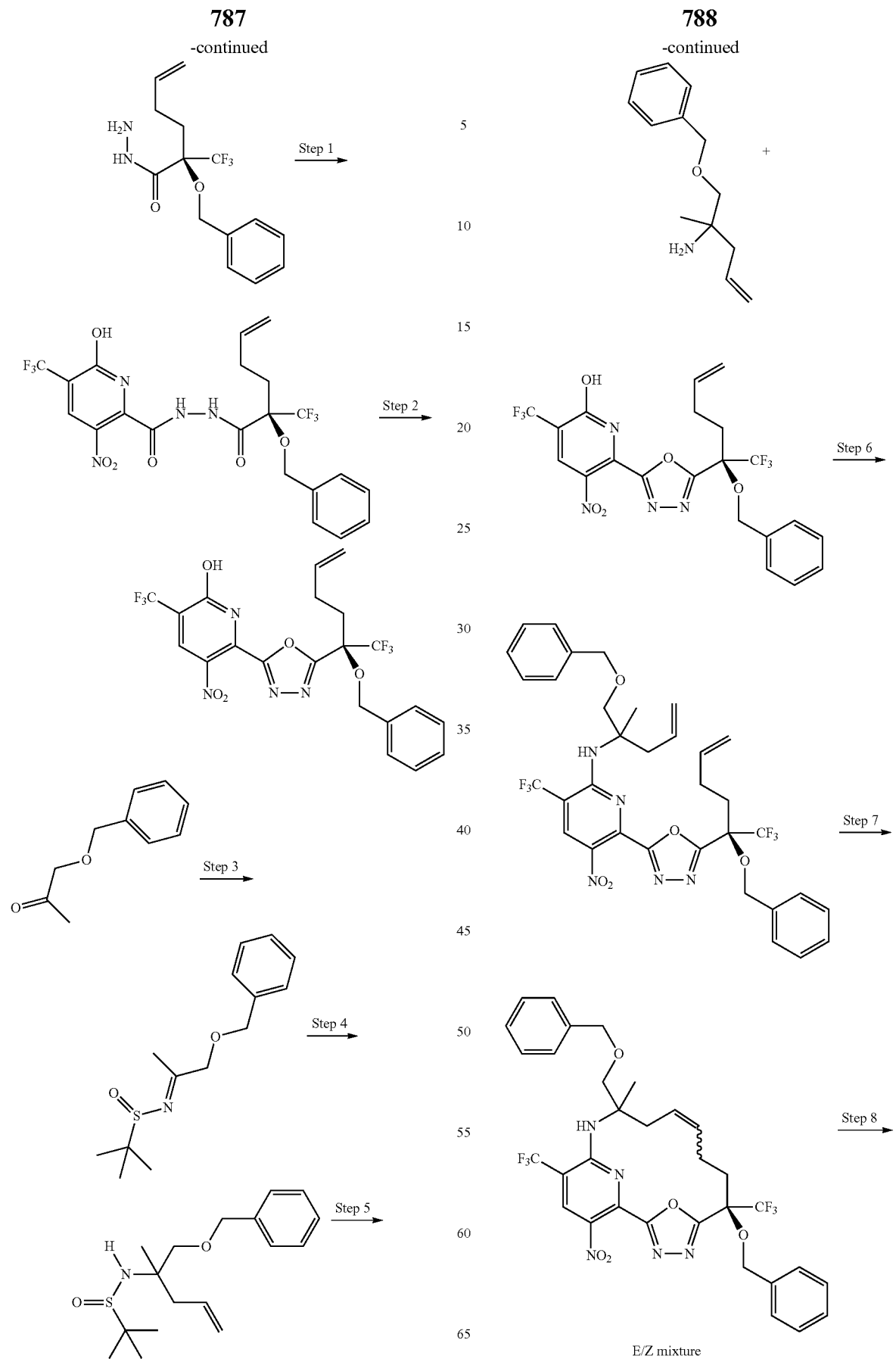

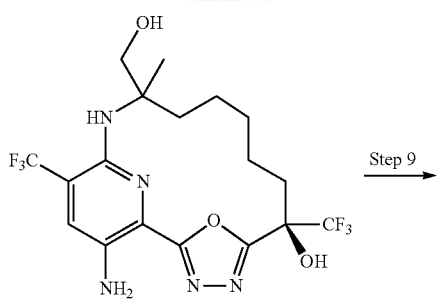

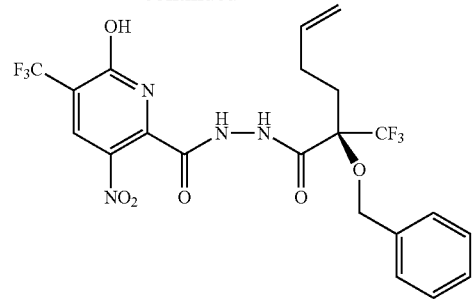

1,1'-Carbonyldiimidazole (1.35 g, 8.3257 mmol) was added to a colorless solution of 6-hydroxy-3-nitro-5-(trifluoromethyl)pyridine-2-carboxylic acid (2 g, 7.8856 mmol) in acetonitrile (20 mL) and DMF (4 mL) at room temperature. The mixture was stirred for 0.5 h at room temperature, then (2R)-2-benzyloxy-2-(trifluoromethyl)hex-5-enehydrazide (2.42 g, 7.7253 mmol) in acetonitrile (10 mL) was added dropwise. The mixture was stirred at room temperature overnight, gently heated at 40° C. for 20 h, then cooled back to room temperature and quenched with water and 2-methyltetrahydrofuran. The mixture was extracted with 2-methyltetrahydrofuran (3×200 mL). The combined organic layers were washed with a 0.5 N aqueous solution of HCl (2×120 mL), dried over anhydrous sodium sulfate, filtered and concentrated by evaporation under reduced pressure to give as a yellow oil, N'-[(2R)-2-benzyloxy-2-(trifluoromethyl)hex-5-enoyl]-6-hydroxy-3-nitro-5-(trifluoromethyl)pyridine-2-carbohydrazide (4.8 g, 94%). The product was used without purification in the ensuing step.

Step 2: 6-[5-[(1R)-1-benzyloxy-1-(trifluoromethyl)pent-4-enyl]-1,3,4-oxadiazol-2-yl]-5-nitro-3-(trifluoromethyl)pyridin-2-ol

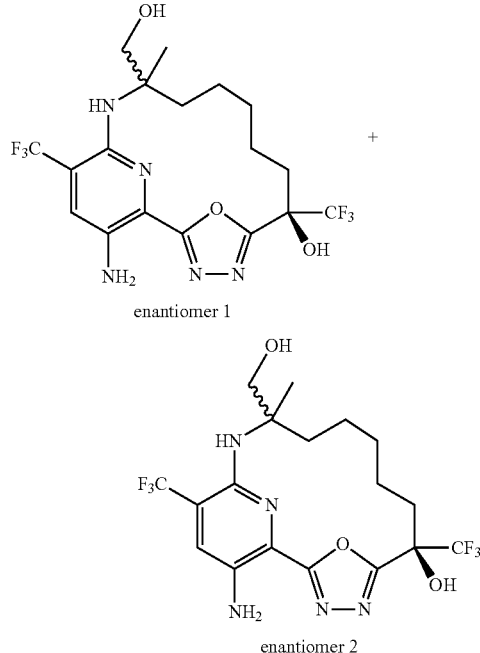

Step 1: N'-[(2R)-2-benzyloxy-2-(trifluoromethyl)hex-5-enoyl]-6-hydroxy-3-nitro-5-(trifluoromethyl)pyridine-2-carbohydrazide

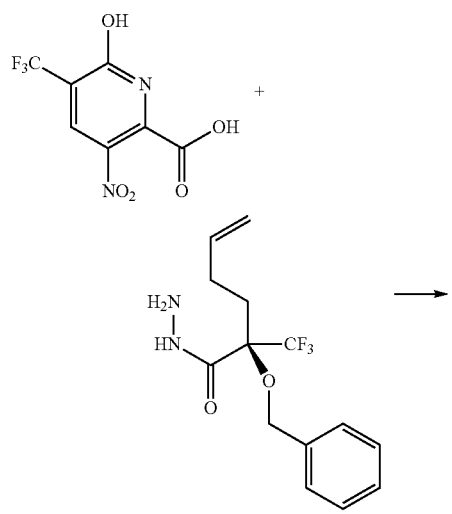

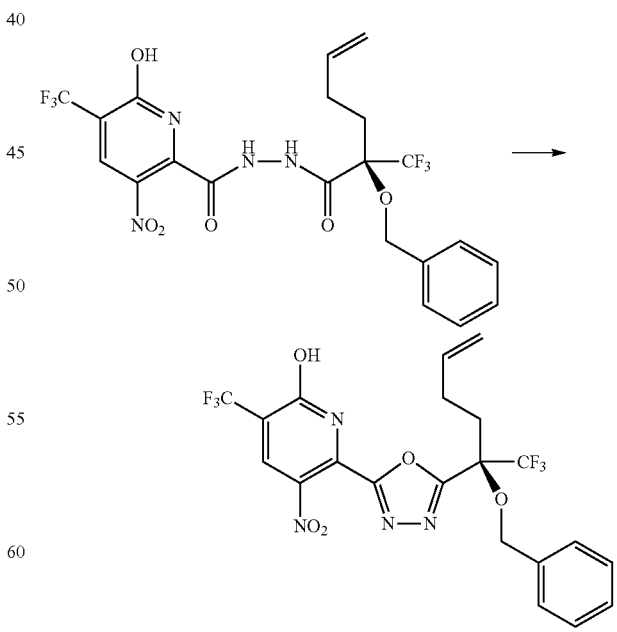

To a solution of N-[(2R)-2-benzyloxy-2-(trifluoromethyl)hex-5-enoyl]-6-hydroxy-3-nitro-5-(trifluoromethyl)pyridine-2-carbohydrazide (6.47 g, 8.4557 mmol) and N,N- diisopropylethylamine (5.8618 g, 7.9 mL, 45.355 mmol) in acetonitrile (200 mL) at 0° C. was added 4-methylbenzenesulfonyl chloride (3.71 g, 19.46 mmol) in portions. After the addition, the cooling bath was removed and the reaction was stirred at 26° C. over 44 h. The volatiles were removed by evaporation under reduced pressure. The residue was taken up in ethyl acetate (180 mL) and washed with a 0.5 N aqueous solution of hydrochloric acid (3×25 ml) and brine (2×15 ml). The organic layer was dried over anhydrous sodium sulphate, filtered and concentrated by evaporation under reduced pressure giving as brown sticky residue, 6-[5-[(1R)-1-benzyloxy-1-(trifluoromethyl)pent-4-enyl]-1,3,4-oxadiazol-2-yl]-5-nitro-3-(trifluoromethyl)pyridin-2-ol (6.67 g, 70%). ESI-MS m/z calc. 518.1025, found 519.1 (M+1)$^+$; Retention time: 3.1 minutes (LC Method BB).

Step 3: (E)-N-(1-(Benzyloxy)propan-2-ylidene)-2-methylpropane-2-sulfinamide

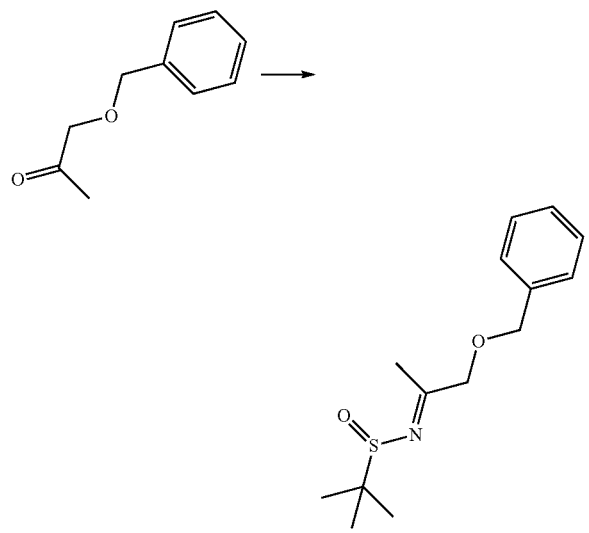

To solution of 1-benzyloxypropan-2-one (9.5 g, 52.07 mmol) and 2-methylpropane-2-sulfinamide (6.7 g, 55.28 mmol) in THF (140 mL) was added Ti(OEt)$_4$ (30.464 g, 28 mL, 133.55 mmol). The reaction mixture was stirred at 70° C. for 4 hours. The reaction mixture was cooled to room temperature and poured into brine (300 mL). The resulting suspension was filtered through Celite, and the filter cake was washed with EtOAc (300 mL). The organic layer was separated, and the aqueous layer was extracted with EtOAc (2×200 mL). The combined organic layers were washed with brine (350 mL), dried over sodium sulfate, filtered and concentrated. The residue was purified by silica gel chromatography using a gradient from 0% to 45% ethyl acetate in hexanes to furnish as a yellow oil, (E)-N-(1-(benzyloxy)propan-2-ylidene)-2-methylpropane-2-sulfinamide (6.85 g, 42%). ESI-MS m/z calc. 267.1293, found 268.2 (M+1)$^+$; Retention time: 2.56 minutes (LC Method G).

Step 4: N-[1-(Benzyloxymethyl)-1-methyl-but-3-enyl]-2-methyl-propane-2-sulfinamide

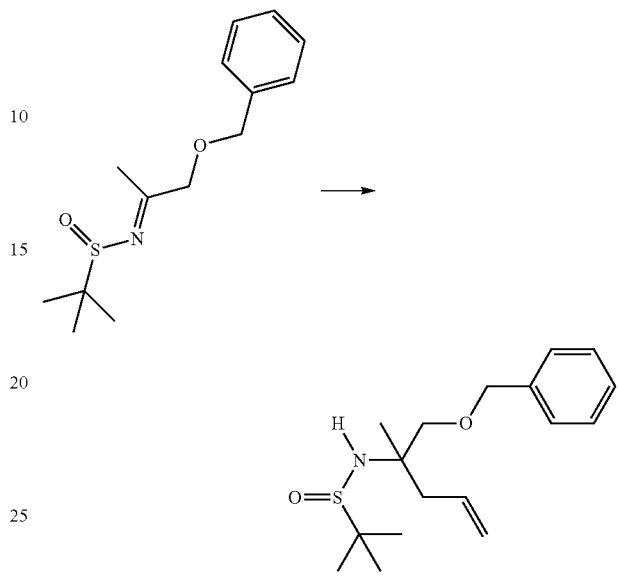

To a solution of (E)-N-(1-(benzyloxy)propan-2-ylidene)-2-methylpropane-2-sulfinamide (5.3 g, 18.236 mmol) in toluene (120 mL) at −78° C. was added allyl(bromo)magnesium (26.8 mL of 1 M, 26.8 mmol) slowly. The reaction mixture was stirred for 2 h at −78° C. The reaction was quenched with saturated NH$_4$Cl (200 mL) and warmed to room temperature. The organic layer was separated and the aqueous layer was extracted with EtOAc (3×200 mL). The combined organic layers were dried over sodium sulfate, filtered and concentrated under vacuum. The residue was purified by silica gel chromatography using a gradient from 0% to 50% ethyl acetate in hexanes giving as a light-yellow oil, N-[1-(benzyloxymethyl)-1-methyl-but-3-enyl]-2-methyl-propane-2-sulfinamide (5.32 g, 80%). ESI-MS m/z calc. 309.1762, found 310.5 (M+1)$^+$; Retention time: 3.31 minutes (LC Method G).

Step 5: 1-Benzyloxy-2-methyl-pent-4-en-2-amine

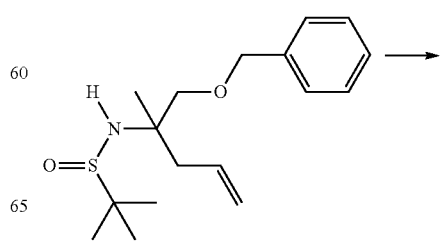

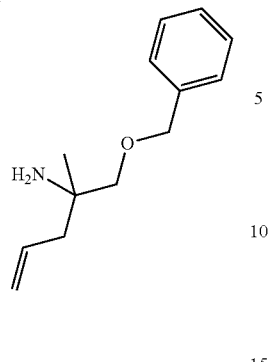

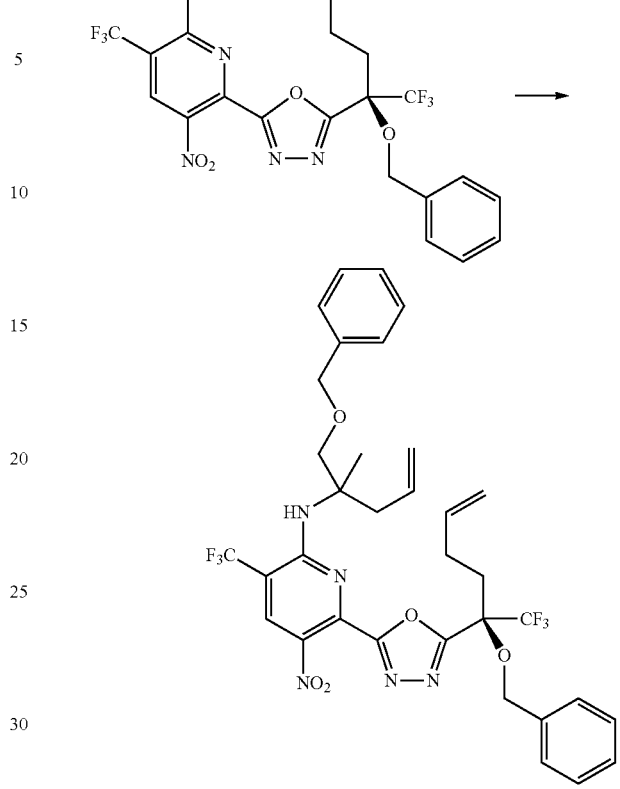

To a solution of N-[1-(benzyloxymethyl)-1-methyl-but-3-enyl]-2-methyl-propane-2-sulfinamide (5.32 g, 14.612 mmol) in 1,4-dioxane (85 mL) was added HCl in diethyl ether (42 mL of 2 M, 84 mmol), and then stirred the mixture at room temperature for 1 hour. The solvent was evaporated under vacuum. The residue was diluted with EtOAc (150 mL) and saturated NaHCO$_3$ (150 mL). The organic layer was separated and the aqueous layer was extracted with ethyl acetate (2×150 mL). The combined organic layers were dried over anhydrous sodium sulfate, filtered and concentrated under vacuum. The residue was purified by silica gel chromatography using a gradient from 0% to 10% MeOH in DCM giving as a light brown oil, 1-benzyloxy-2-methyl-pent-4-en-2-amine (1.9749 g, 63%). $^1$H NMR (500 MHz, DMSO-d6) δ 7.38-7.29 (m, 4H), 7.30-7.23 (m, 1H), 5.86-5.76 (m, 1H), 5.02 (s, 1H), 4.99 (d, J=7.8 Hz, 1H), 4.47 (s, 2H), 3.13 (s, 2H), 2.08 (d, J=7.4 Hz, 2H), 1.61 (s, 2H), 0.94 (s, 3H) ppm. ESI-MS m/z calc. 205.1467, found 206.2 (M+1)$^+$; Retention time: 1.49 minutes (LC Method H).

Step 6: N-[1-(Benzyloxymethyl)-1-methyl-but-3-enyl]-6-[5-[(1R)-1-benzyloxy-1-(trifluoromethyl)pent-4-enyl]-1,3,4-oxadiazol-2-yl]-5-nitro-3-(trifluoromethyl)pyridin-2-amine

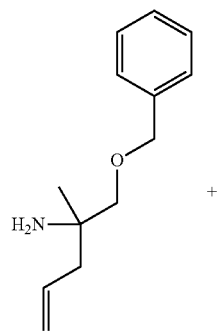

+

To a 0° C. solution of 6-[5-[(1R)-1-benzyloxy-1-(trifluoromethyl)pent-4-enyl]-1,3,4-oxadiazol-2-yl]-5-nitro-3-(trifluoromethyl)pyridin-2-ol (300 mg, 0.5084 mmol) in dichloromethane (5 mL) was added DIPEA (200.34 mg, 0.27 mL, 1.5501 mmol) followed by trifluoromethylsulfonyl trifluoromethanesulfonate (184.47 mg, 0.11 mL, 0.6538 mmol). The ice bath was removed after 20 min and the reaction was stirred at room temperature for 40 minutes. The mixture was cooled again to 0° C. To the mixture was added 1-benzyloxy-2-methyl-pent-4-en-2-amine (125 mg, 0.6089 mmol) in dichloromethane (0.5 mL) and DIPEA (200.34 mg, 0.27 mL, 1.5501 mmol). The ice bath was removed after 20 min and the reaction was stirred at room temperature overnight. The reaction mixture was concentrated under reduced pressure and the residue was purified by silica gel chromatography using a gradient from 0% to 20% ethyl acetate in heptanes giving as an orange oil, N-[1-(benzyloxymethyl)-1-methyl-but-3-enyl]-6-[5-[(1R)-1-benzyloxy-1-(trifluoromethyl)pent-4-enyl]-1,3,4-oxadiazol-2-yl]-5-nitro-3-(trifluoromethyl)pyridin-2-amine (78 mg, 20%). $^1$H NMR (400 MHz, Chloroform-d) δ 8.47 (s, 1H), 7.43-7.23 (m, 10H), 6.26 (br s, 1H), 5.86-5.69 (m, 2H), 5.13-4.96 (m, 4H), 4.84 (d, J=10.5 Hz, 1H), 4.66 (d, J=10.5 Hz, 1H), 4.57-4.45 (m, 2H), 3.66-3.53 (m, 2H), 2.74-2.17 (m, 6H), 1.48 (s, 3H) ppm. $^{19}$F NMR (377 MHz, Chloroform-d) δ −64.68 (s, 3F), −73.15 (s, 3F) ppm. ESI-MS m/z calc. 705.2386, found 706.3 (M+1)$^+$; Retention time: 4.54 minutes (LC Method BB).

Step 7: (6R)-6-Benzyloxy-12-(benzyloxymethyl)-12-methyl-17-nitro-6,15-bis(trifluoromethyl)-19-oxa-3,4,13,18-tetrazatricyclo[12.3.1.1²,⁵]nonadeca-1(18),2,4,9,14,16-hexaene (E/Z mixture)

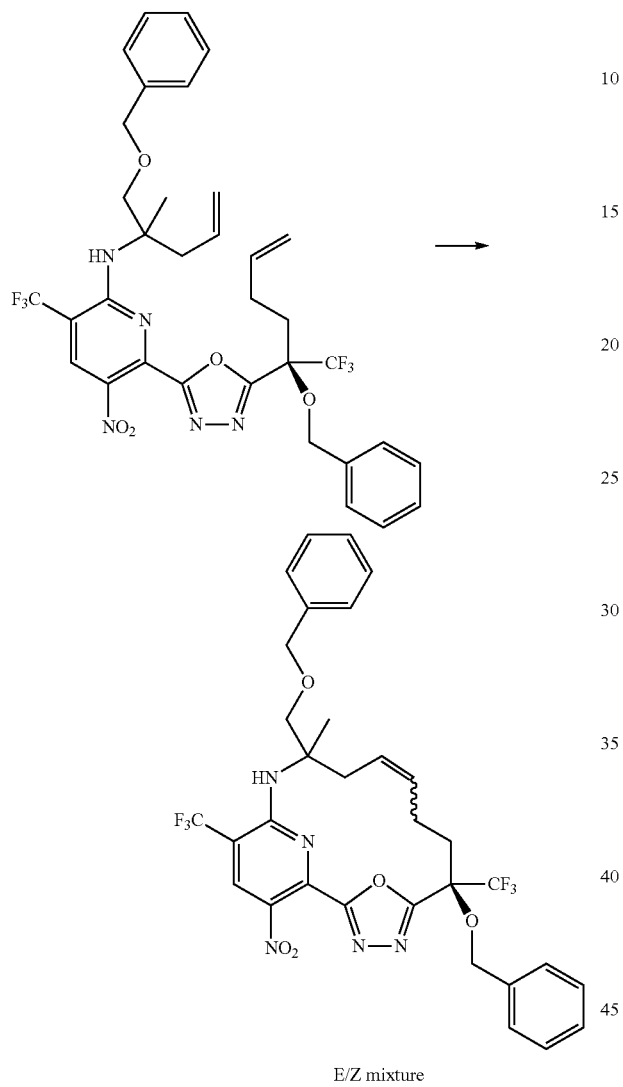

E/Z mixture

To a solution of N-[1-(benzyloxymethyl)-1-methyl-but-3-enyl]-6-[5-[(1R)-1-benzyloxy-1-(trifluoromethyl)pent-4-enyl]-1,3,4-oxadiazol-2-yl]-5-nitro-3-(trifluoromethyl)pyridin-2-amine (248 mg, 0.3393 mmol) in 1,2-dichloroethane (120 mL) was degassed with nitrogen gas for 20 minutes. To the solution at 60° C. was added the first portion of Zhan catalyst-1B (15 mg, 0.0204 mmol) and the reaction was stirred at this temperature for 40 minutes. Then, an equal amount of Zhan catalyst-1B (15 mg, 0.0204 mmol) was added and stirring continued at 60° C. for 2.5 hours. Once cooled to room temperature, the catalyst was quenched with ~5 to 6 drops of DMSO and the reaction was concentrated under reduced pressure. The residue was purified by silica gel chromatography using a gradient from 0% to 90% ethyl acetate in heptanes giving as a light yellow foam, (6R)-6-benzyloxy-12-(benzyloxymethyl)-12-methyl-17-nitro-6,15-bis(trifluoromethyl)-19-oxa-3,4,13,18-tetrazatricyclo[12.3.1.1²,⁵]nonadeca-1(18),2,4,9,14,16-hexaene (E/Z mixture) (174 mg, 75%). $^{1}$H NMR (400 MHz, Chloroform-d) δ 8.54-8.48 (m, 1H), 7.40-7.21 (m, 10H), 6.49-6.14 (m, 1H), 5.65-5.53 (m, 1H), 5.42-5.29 (m, 1H), 5.26-5.12 (m, 1H), 4.97 (d, J=11.2 Hz, 1H), 4.69-4.60 (m, 1H), 4.59-4.43 (m, 1H), 3.78-3.62 (m, 1H), 3.62-3.28 (m, 2H), 2.71-2.08 (m, 5H), 1.44-1.39 (m, 3H) ppm. $^{19}$F NMR (377 MHz, Chloroform-d) δ −64.15 to −64.22 (m, 3F), −73.15 to −73.40 (m, 3F) ppm. ESI-MS m/z calc. 677.2073, found 678.2 (M+1)$^{+}$; Retention time: 4.3 minutes (LC Method C).

Step 8: (6R)-17-amino-12-(hydroxymethyl)-12-methyl-6,15-bis(trifluoromethyl)-19-oxa-3,4,13,18-tetrazatricyclo[12.3.1.1²,⁵]nonadeca-1(18),2,4,14,16-pentaen-6-ol

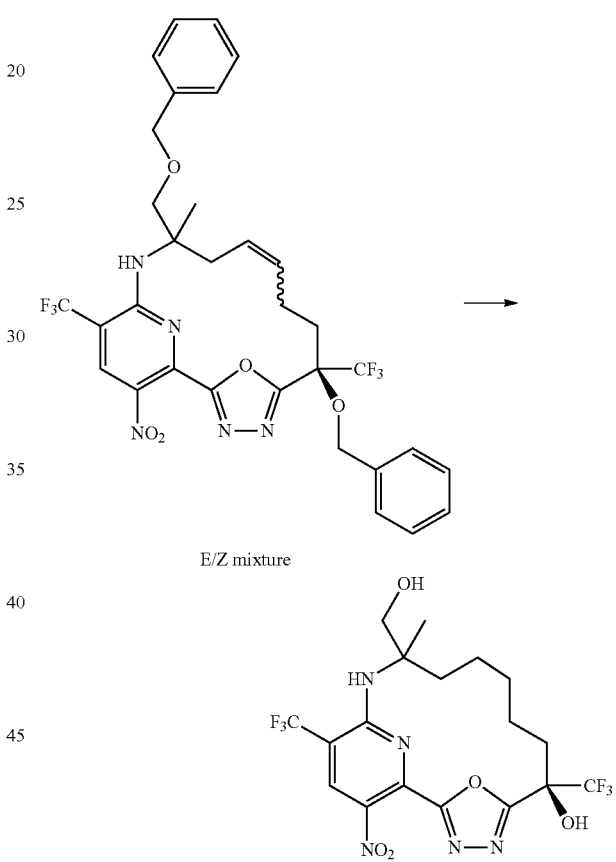

(6R)-6-benzyloxy-12-(benzyloxymethyl)-12-methyl-17-nitro-6,15-bis(trifluoromethyl)-19-oxa-3,4,13,18-tetrazatricyclo[12.3.1.1²,⁵]nonadeca-1(18),2,4,9,14,16-hexaene (E/Z mixture) (174 mg, 0.2542 mmol) was dissolved in anhydrous methanol (8.7 mL). Nitrogen gas was bubbled into the mixture for 5 minutes and then palladium on carbon (165 mg, 5 w/w, 0.0775 mmol) was added. Hydrogen was then bubbled into the mixture with a balloon for 5 minutes and the reaction mixture was stirred at room temperature under hydrogen overnight. The hydrogen balloon was replaced with nitrogen, and the mixture purged with nitrogen using a needle exit. The mixture was filtered through a pad of Celite, washed with ethyl acetate (15 mL) and concentrated under reduced pressure. The residue was purified by silica gel chromatography using a gradient from of 0% to 40% ethyl acetate in heptanes giving as a light yellow foam, (6R)-17- amino-12-(hydroxymethyl)-12-methyl-6,15-bis(trifluoromethyl)-19-oxa-3,4,13,18-tetrazatricyclo[12.3.1.12,5]nonadeca-1(18),2,4,14,16-pentaen-6-ol (68 mg, 56%). ESI-MS m/z calc. 469.1549, found 470.1 (M+1)+; Retention time: 3.04 minutes (LC Method C).

Step 9: (6R)-17-Amino-12-(hydroxymethyl)-12-methyl-6,15-bis(trifluoromethyl)-19-oxa-3,4,13,18-tetrazatricyclo[12.3.1.12,5]nonadeca-1(18),2,4,14,16-pentaen-6-ol (enantiomer 1) (Compound 174) and (6R)-17-amino-12-(hydroxymethyl)-12-methyl-6,15-bis(trifluoromethyl)-19-oxa-3,4,13,18-tetrazatricyclo[12.3.1.12,5]nonadeca-1(18),2,4,14,16-pentaen-6-ol (enantiomer 2) (Compound 175)

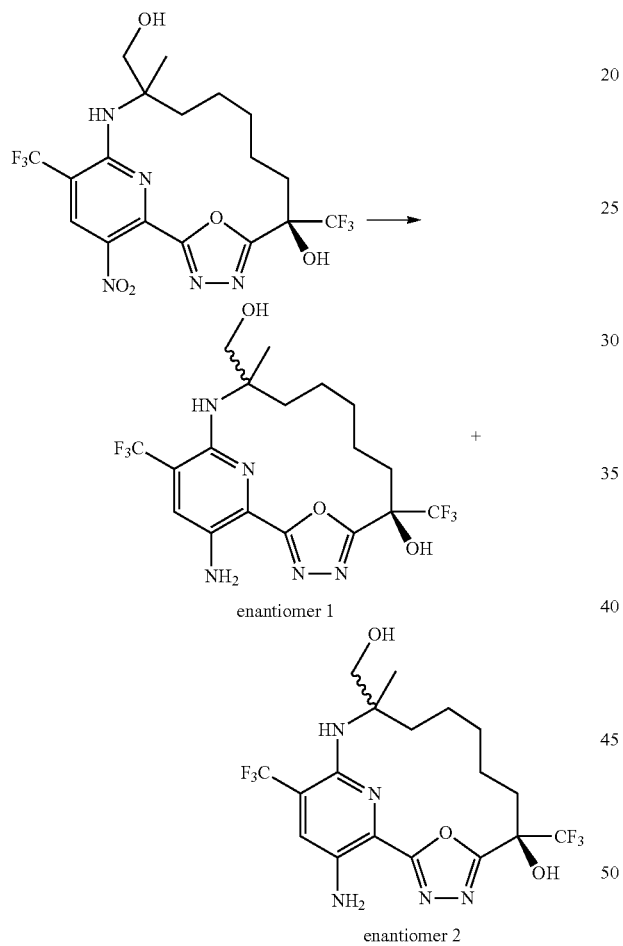

enantiomer 1 enantiomer 2

The diastereomeric mixture of (6R)-17-amino-12-(hydroxymethyl)-12-methyl-6,15-bis(trifluoromethyl)-19-oxa-3,4,13,18-tetrazatricyclo[12.3.1.12,5]nonadeca-1(18),2,4,14,16-pentaen-6-ol (59.3 mg, 0.1249 mmol) was separated by SFC on a Cellulose 1 column (21.2 mm×250 mm, 5 μm particle size) at 40° C., eluting with 10% methanol in $CO_2$ at 75 mL/min flow giving two individual enantiomers:

The first enantiomer to elute was isolated as a yellow fluffy solid, (6R)-17-amino-12-(hydroxymethyl)-12-methyl-6,15-bis(trifluoromethyl)-19-oxa-3,4,13,18-tetrazatricyclo[12.3.1.12,5]nonadeca-1(18),2,4,14,16-pentaen-6-ol (enantiomer 1) (21 mg, 35%). $^1$H NMR (400 MHz, DMSO-d6) δ 7.62-7.56 (m, 2H), 5.98 (s, 2H), 5.12 (s, 1H), 5.10 (t, J=5.0 Hz, 1H), 3.51 (dd, J=10.5, 5.6 Hz, 1H), 3.36 (dd, J=10.4, 4.8 Hz, 1H), 2.94-2.82 (m, 1H), 2.38-2.26 (m, 1H), 2.08-1.96 (m, 1H), 1.75-1.60 (m, 2H), 1.60-1.49 (m, 2H), 1.46-1.32 (m, 3H), 1.30 (s, 3H) ppm. $^{19}$F NMR (377 MHz, DMSO-d6) δ −62.72 (s, 3F), −76.81 (s, 3F) ppm. ESI-MS m/z calc. 469.1549, found 470.1 (M+1)+; Retention time: 2.98 minutes (LC Method C).

The second enantiomer to elute was isolated as a yellow fluffy solid, (6R)-17-amino-12-(hydroxymethyl)-12-methyl-6,15-bis(trifluoromethyl)-19-oxa-3,4,13,18-tetrazatricyclo[12.3.1.12,5]nonadeca-1(18),2,4,14,16-pentaen-6-ol (enantiomer 2) (30 mg, 51%). $^1$H NMR (400 MHz, DMSO-d6) δ 7.62 (s, 1H), 7.59 (s, 1H), 5.95 (s, 2H), 5.26 (s, 1H), 5.19 (t, J=5.0 Hz, 1H), 3.38 (d, J=5.1 Hz, 2H), 2.43-2.15 (m, 1H), 1.99-1.85 (m, 1H), 1.73-1.57 (m, 1H), 1.55-1.26 (m, 9H), 1.22-1.12 (m, 1H) ppm. $^{19}$F NMR (377 MHz, DMSO-d6) δ −62.78 (s, 3F), −79.04 (s, 3F) ppm. ESI-MS m/z calc. 469.1549, found 470.1 (M+1)+; Retention time: 3.04 minutes (LC Method C).

Step 10: Solid Form Characterization of Crystalline Compound 175 Form a (Neat)

A. Single Crystal X-Ray Diffraction

Single crystals of crystalline Compound 175 Form A (neat) were grown from dichloromethane and hexanes. X-ray diffraction data were acquired at 100 K on a Bruker diffractometer equipped with Cu Kα radiation (λ=1.54178 Å) and a CPAD detector. The structure was solved and refined using SHELX programs (Sheldrick, G. M., Acta Cryst., (2008) A64, 112-122) and results are summarized in Table 8 below.

TABLE 8

| Single crystal elucidation of crystalline Compound 175 Form A (neat) | |
|---|---|
| Crystal System | Orthorhombic |
| Space Group | $P2_12_12_1$ |
| a (Å) | 9.7635(2) |
| b (Å) | 10.0499(2) |
| c (Å) | 20.5163(5) |
| α (°) | 90 |
| β (°) | 90 |
| γ (°) | 90 |
| V (Å3) | 2013.10(8) |
| Z/Z' | 4/1 |
| Temperature | 100 K |

Example 97: Preparation of (6R)-17-amino-12,12-bis(trideuteriomethyl)-6,15-bis(trifluoromethyl)-19-oxa-3,4,13,18-tetrazatricyclo[12.3.1.12,5]nonadeca-1(18),2,4,14,16-pentaen-6-ol (Compound 176)

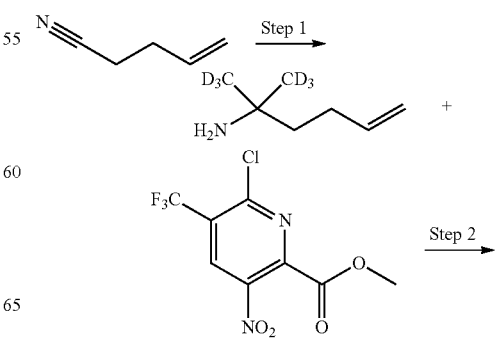

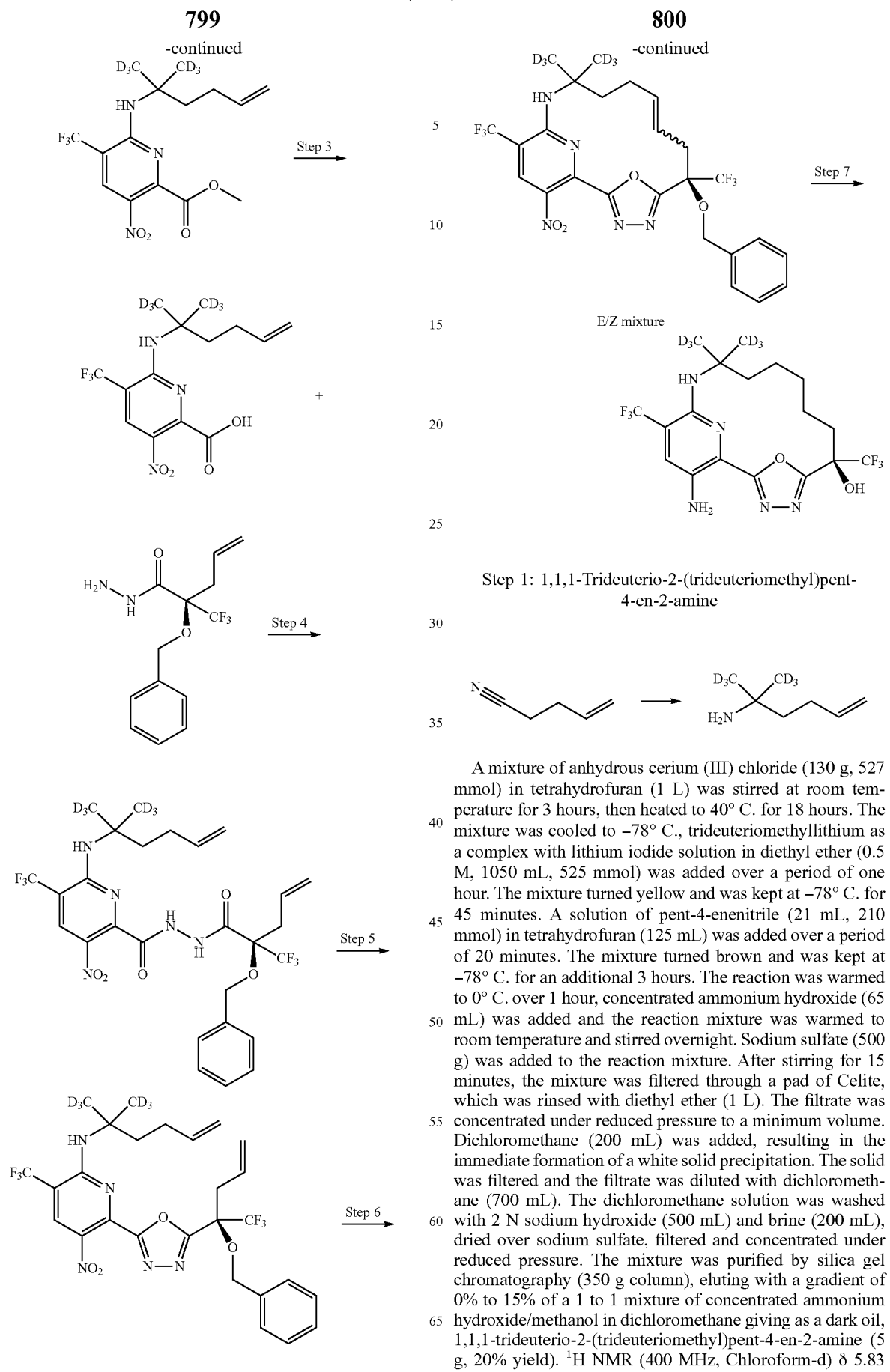

Step 1: 1,1,1-Trideuterio-2-(trideuteriomethyl)pent-4-en-2-amine

A mixture of anhydrous cerium (III) chloride (130 g, 527 mmol) in tetrahydrofuran (1 L) was stirred at room temperature for 3 hours, then heated to 40° C. for 18 hours. The mixture was cooled to −78° C., trideuteriomethyllithium as a complex with lithium iodide solution in diethyl ether (0.5 M, 1050 mL, 525 mmol) was added over a period of one hour. The mixture turned yellow and was kept at −78° C. for 45 minutes. A solution of pent-4-enenitrile (21 mL, 210 mmol) in tetrahydrofuran (125 mL) was added over a period of 20 minutes. The mixture turned brown and was kept at −78° C. for an additional 3 hours. The reaction was warmed to 0° C. over 1 hour, concentrated ammonium hydroxide (65 mL) was added and the reaction mixture was warmed to room temperature and stirred overnight. Sodium sulfate (500 g) was added to the reaction mixture. After stirring for 15 minutes, the mixture was filtered through a pad of Celite, which was rinsed with diethyl ether (1 L). The filtrate was concentrated under reduced pressure to a minimum volume. Dichloromethane (200 mL) was added, resulting in the immediate formation of a white solid precipitation. The solid was filtered and the filtrate was diluted with dichloromethane (700 mL). The dichloromethane solution was washed with 2 N sodium hydroxide (500 mL) and brine (200 mL), dried over sodium sulfate, filtered and concentrated under reduced pressure. The mixture was purified by silica gel chromatography (350 g column), eluting with a gradient of 0% to 15% of a 1 to 1 mixture of concentrated ammonium hydroxide/methanol in dichloromethane giving as a dark oil, 1,1,1-trideuterio-2-(trideuteriomethyl)pent-4-en-2-amine (5 g, 20% yield). $^1$H NMR (400 MHz, Chloroform-d) δ 5.83

(tdd, J=6.5, 10.3, 17.0 Hz, 1H), 5.02 (qd, J=1.7, 17.1 Hz, 1H), 4.97-4.89 (m, 1H), 2.14-2.03 (m, 2H), 1.47-1.40 (m, 2H), 1.27 (br s, 2H) ppm. $^2$H NMR (61.4 MHz, Chloroform) δ 1.07 (s, 6D) ppm. ESI-MS m/z calc. 119.24, found 120.2 (M+H)$^+$; Retention time: 1.1 minutes (LC Method CC).

Step 2: Methyl 6-[1,1-bis(trideuteriomethyl)but-3-enylamino]-3-nitro-5-(trifluoromethyl)pyridine-2-carboxylate

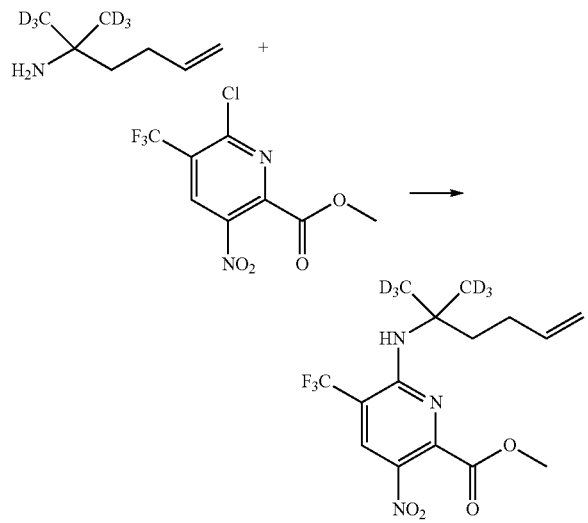

In a 500 mL sealed vessel, 1,1,1-trideuterio-2-(trideuteriomethyl)pent-4-en-2-amine (8.8 g, 66.42 mmol, DIEA (22.75 mL, 130.24 mmol) and methyl 6-chloro-3-nitro-5-(trifluoromethyl)pyridine-2-carboxylate (18.53 g, 65.12 mmol) were combined in acetonitrile (148 mL) and the mixture was heated at 70° C. for 110 minutes. The reaction mixture was cooled to ambient temperature and the solvent was removed in vacuo. The residue was diluted with ethyl acetate (50 mL) and washed with brine (2×25 mL), dried over sodium sulfate, filtered and concentrated. The residue was purified by silica gel chromatography using a gradient from 0% to 5% ethyl acetate in hexanes giving as red brown oil, methyl 6-[1,1-bis(trideuteriomethyl)but-3-enylamino]-3-nitro-5-(trifluoromethyl)pyridine-2-carboxylate (18.77 g, 78%). ESI-MS m/z calc. 367.16, found 368.267 (M+1)$^+$; Retention time: 2.91 minutes (LC Method D).

Step 3: 6-[1,1-Bis(trideuteriomethyl)but-3-enylamino]-3-nitro-5-(trifluoromethyl)pyridine-2-carboxylic Acid

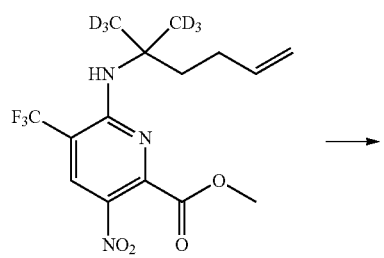

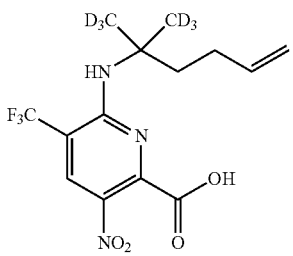

To a solution of methyl 6-[1,1-bis(trideuteriomethyl)but-3-enylamino]-3-nitro-5-(trifluoromethyl)pyridine-2-carboxylate (18.77 g, 51.1 mmol) in methanol (93.85 mL) was added aqueous NaOH (120.87 mL, 2 M, 241.74 mmol). After stirring for 8 h, methanol was removed under reduced pressure. The mixture was cooled in an ice bath and 6 M HCl solution (50 mL) was added, then extracted with MTBE (120 mL). The organic phases were combined, washed with water (3×50 mL,) brine, dried over anhydrous sodium sulfate, filtered and concentrated under reduced pressure giving as a beige solid, 6-[1,1-bis(trideuteriomethyl)but-3-enylamino]-3-nitro-5-(trifluoromethyl)pyridine-2-carboxylic acid (17.57, 97%). ESI-MS m/z calc. 353.15, found 354.207 (M+1)$^+$; Retention time: 2.395 minutes (LC Method D).

Step 4: N'-[(2R)-2-Benzyloxy-2-(trifluoromethyl)hex-5-enoyl]-6-[1,1-bis(trideuteriomethyl)but-3-enylamino]-3-nitro-5-(trifluoromethyl)pyridine-2-carbohydrazide

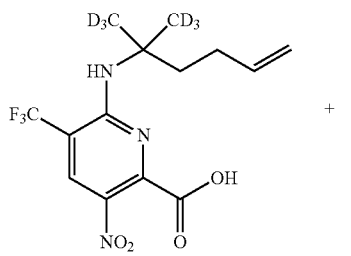

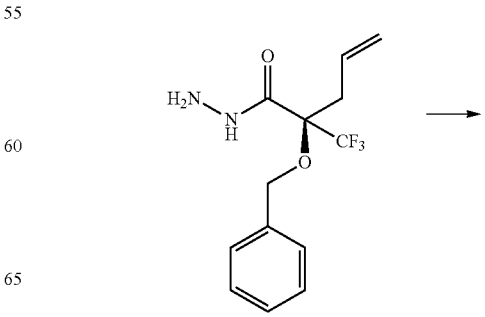

803
-continued

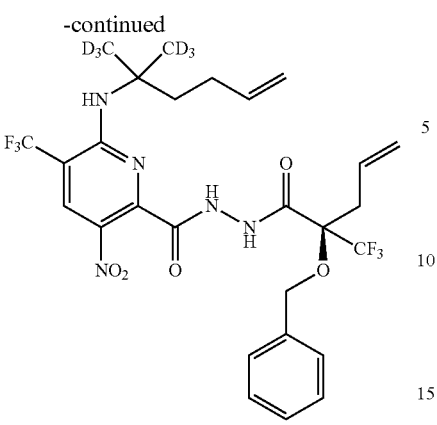

To a solution of 6-[1,1-bis(trideuteriomethyl)but-3-enylamino]-3-nitro-5-(trifluoromethyl)pyridine-2-carboxylic acid (17.57 g, 49.73 mmol) and (2R)-2-(benzyloxy)-2-(trifluoromethyl) pent-4-enehydrazide (15.05 g, 52.21 mmol) in DMF (105.42 mL) was added HATU (19.85 g, 52.21 mmol) at an internal temperature of 4.9° C. in one portion. Then DIEA (17.32 mL, 99.453 mmol) was added dropwise keeping the internal temperature below 10° C. The reaction mixture was stirred at room temperature for 2 h. The reaction mixture was added to a stirred solution of cold water (527.1 mL) and MTBE (175.7 mL). The mixture was stirred for 10 min and phases were separated. The organic layer was washed with water (2×175 mL), 0.2 M KHSO$_4$ (3×175 mL) and brine (44 mL). The organic layer was dried over Na$_2$SO$_4$, filtered, evaporated and dried to give as a red viscous oil, N'-[(2R)-2-benzyloxy-2-(trifluoromethyl)hex-5-enoyl]-6-[1,1-bis(trideuteriomethyl)but-3-enylamino]-3-nitro-5-(trifluoromethyl)pyridine-2-carbohydrazide (32.7 g, 100%) which was used directly in the next step without further purification. ESI-MS m/z calc. 623.24, found 624.422 (M+1)$^+$; Retention time: 3.158 minutes (LC Method D).

Step 5: 6-[5-[(1R)-1-Benzyloxy-1-(trifluoromethyl)pent-4-enyl]-1,3,4-oxadiazol-2-yl]-N-[1,1-bis(trideuteriomethyl)but-3-enyl]-5-nitro-3-(trifluoromethyl)pyridin-2-amine

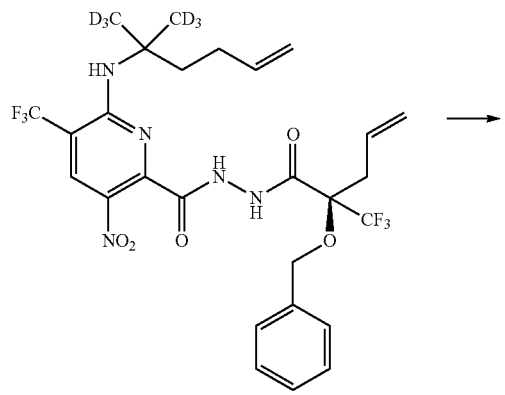

804
-continued

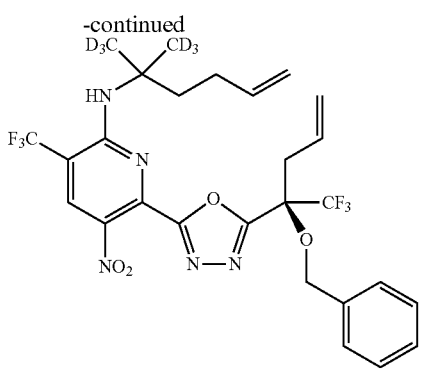

To a solution of N-[(2R)-2-benzyloxy-2-(trifluoromethyl)hex-5-enoyl]-6-[1,1-bis(trideuteriomethyl)but-3-enylamino]-3-nitro-5-(trifluoromethyl)pyridine-2-carbohydrazide (31.01 g, 49.73 mmol) and DIEA (17.32 mL, 99.45 mmol) in CH$_3$CN (248.07 mL) was added p-toluenesulfonyl chloride (10.43 g, 54.7 mmol) portion-wise, keeping the temperature below 50° C. The mixture was heated at 60° C. for 30 min and then the reaction mixture was cooled to ambient temperature. Most of the solvents were removed under reduced pressure and partitioned the remaining material between MTBE (250 mL) and water (250 mL). The phases were separated, the organic layer was washed with water (250 mL), 0.2 M KHSO$_4$ (2×150 mL), brine (75 mL) then dried over Na$_2$SO$_4$, filtered and concentrated. The residue was purified by silica gel chromatography using a gradient from 0% to 10% ethyl acetate in hexanes giving as a red oil, 6-[5-[(1R)-1-benzyloxy-1-(trifluoromethyl)pent-4-enyl]-1,3,4-oxadiazol-2-yl]-N-[1,1-bis(trideuteriomethyl)but-3-enyl]-5-nitro-3-(trifluoromethyl)pyridin-2-amine (24.65 g, 82%). ESI-MS m/z calc. 605.23, found 606.357 (M+1)$^+$; Retention time: 3.60 minutes (LC Method D).

Step 6: (6R)-6-Benzyloxy-17-nitro-12,12-bis(trideuteriomethyl)-6,15-bis(trifluoromethyl)-19-oxa-3,4,13,18-tetrazatricyclo[12.3.1.1$^{2,5}$]nonadeca-1(18),2,4,9,14,16-hexaene (E/Z mixture)

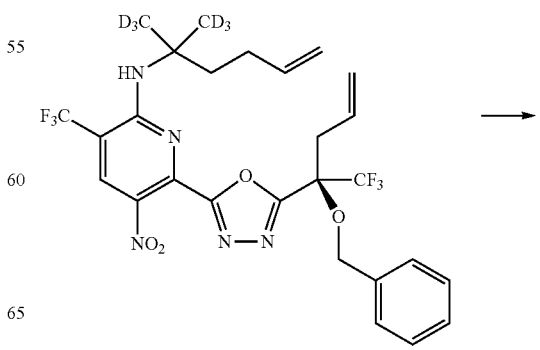

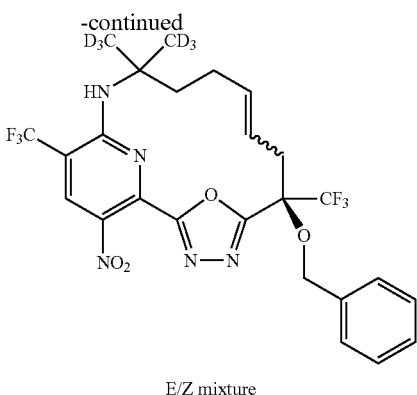

E/Z mixture

In a 5 L 3-neck flask, a continuously nitrogen degassed solution of 6-[5-[(1R)-1-benzyloxy-1-(trifluoromethyl)pent-4-enyl]-1,3,4-oxadiazol-2-yl]-N-[1,1-bis(trideuteriomethyl)but-3-enyl]-5-nitro-3-(trifluoromethyl)pyridin-2-amine (21.17 g, 34.96 mmol) and Zhan catalyst-1B (6.41 g, 8.74 mmol) in DCE (3.18 L) was heated at 75° C. under nitrogen atmosphere for 3 h. 2-Sulfanylpyridine-3-carboxylic acid (5.56 g, 35.83 mmol) and triethylamine (5.1 mL, 36.252 mmol) was added to the reaction mixture, continued stirring at 45° C. under $N_2$ overnight. The reaction mixture was cooled to ambient temperature then 45 g $SiO_2$ (230-400 mesh) was added and the mixture was stirred for 1 h. The reaction mixture was filtered over Celite and the filtrate was concentrated under reduced pressure. The residue was purified by silica gel chromatography using a gradient from 0% to 10% EtOAc in hexanes giving (6R)-6-benzyloxy-17-nitro-12,12-bis(trideuteriomethyl)-6,15-bis(trifluoromethyl)-19-oxa-3,4,13,18-tetrazatricyclo[12.3.1.12,5]nonadeca-1(18),2,4,9,14,16-hexaene (E/Z mixture) (7.64 g, 37.8%). ESI-MS m/z calc. 577.20, found 578.335 (M+1)⁺; Retention time: 3.36-3.38 minutes (LC Method D).

Step 7: (6R)-17-Amino-12,12-bis(trideuteriomethyl)-6,15-bis(trifluoromethyl)-19-oxa-3,4,13,18-tetrazatricyclo[12.3.1.12,5]nonadeca-1(18),2,4,14,16-pentaen-6-ol (Compound 176)

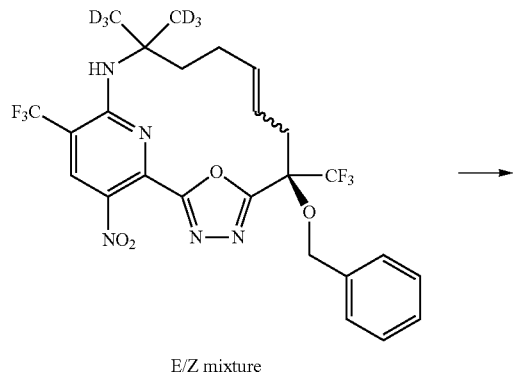

E/Z mixture

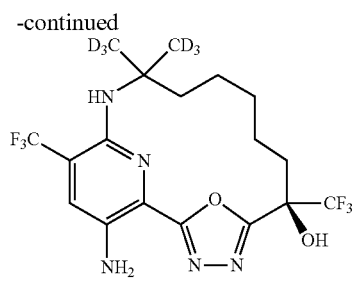

To a solution of (6R)-6-benzyloxy-17-nitro-12,12-bis(trideuteriomethyl)-6,15-bis(trifluoromethyl)-19-oxa-3,4,13,18-tetrazatricyclo[12.3.1.12,5]nonadeca-1(18),2,4,9,14,16-hexaene (E/Z mixture) (6.47 g, 11.2 mmol) in EtOH (97.05 mL) and EtOAc (32.35 mL) was added palladium on carbon (1.908 g, 5 w/w %, 0.896 mmol). Degassed the stirring solution with vacuum/nitrogen gas backfill 5 times, then vacuum/hydrogen balloon 5 times. Ammonia solution in methanol (1.6 mL, 7 M, 11.203 mmol) was added under hydrogen atmosphere. The reaction mixture was stirred at ambient under hydrogen atmosphere overnight. The reaction mixture was filtered through Celite. The filtrate was concentrated under reduced pressure and the residue was treated with heptane and concentrated. To the resultant solid, DCM/heptane (3 mL/18 mL) was added. The formed solid was collected and dried under vacuum oven at 40° C. overnight with $N_2$ bleed to give as a bright yellow solid, (6R)-17-amino-12,12-bis(trideuteriomethyl)-6,15-bis(trifluoromethyl)-19-oxa-3,4,13,18-tetrazatricyclo[12.3.1.12,5]nonadeca-1(18),2,4,14,16-pentaen-6-ol (5.26 g, 85%). ¹H NMR (400 MHz, DMSO-d6) δ 7.60 (d, J=8.3 Hz, 2H), 5.96 (s, 2H), 4.64 (s, 1H), 2.80 (dt, J=14.5, 7.5 Hz, 1H), 2.29-2.15 (m, 1H), 2.06 (t, J=12.4 Hz, 1H), 1.88-1.75 (m, 1H), 1.65 (dd, J=12.6, 8.0 Hz, 1H), 1.55-1.36 (m, 5H) ppm. ESI-MS m/z calc. 459.20, found 460.339 (M+1)⁺; Retention time: 2.918 minutes (LC Method D).

Example 98: Preparation of (6R)-17-amino-6,15-bis(trifluoromethyl)spiro[19-oxa-3,4,13,18-tetrazatricyclo[12.3.1.12,5]nonadeca-1(18),2,4,14,16-pentaene-12,1'-cyclopentane]-6-ol (Compound 177)

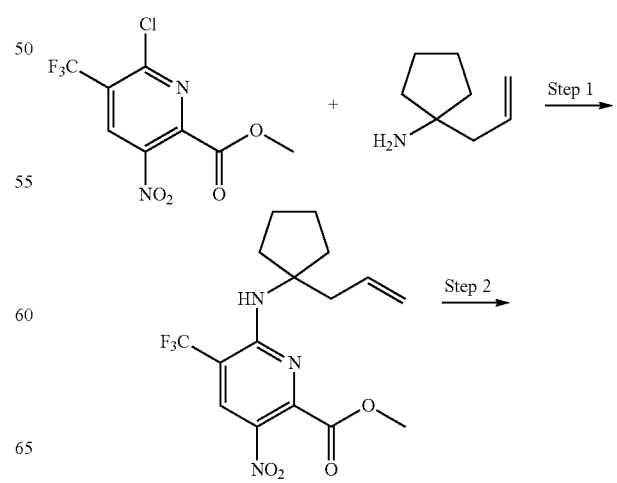

807
-continued

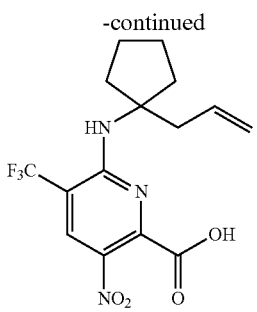

+

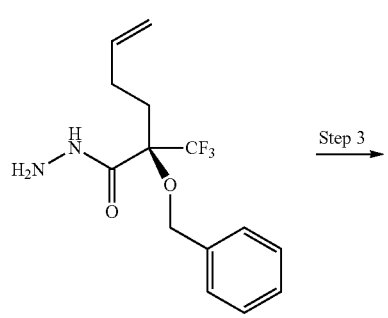

Step 3 →

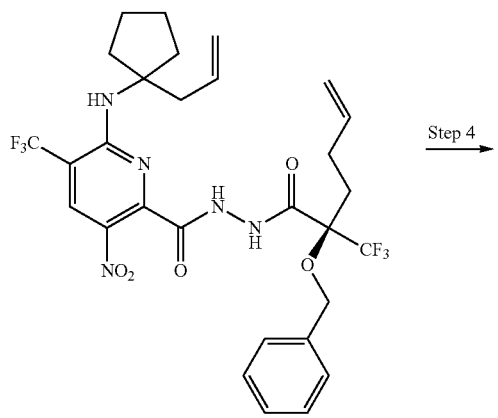

Step 5 →

808
-continued

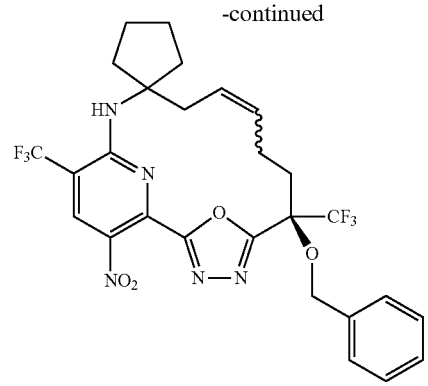

E/Z mixture

Step 6 →

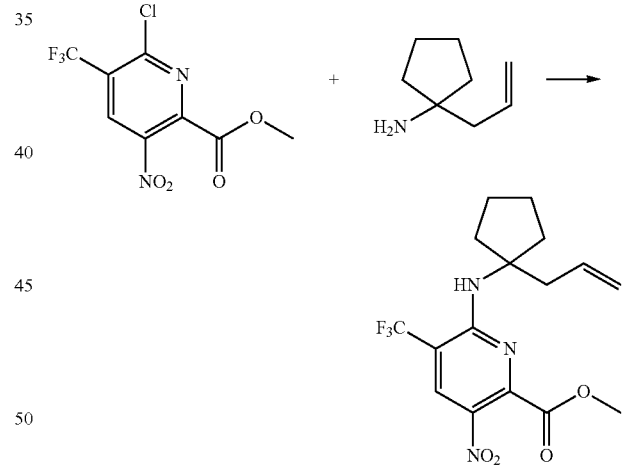

Step 1: Methyl 6-[(1-allylcyclopentyl)amino]-3-nitro-5-(trifluoromethyl)pyridine-2-carboxylate

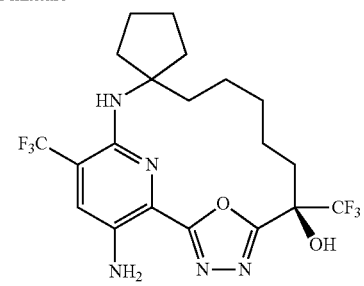

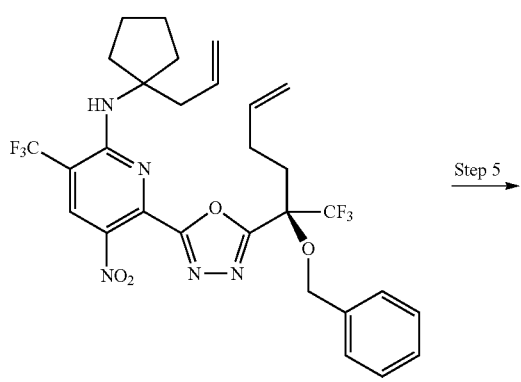

In a 125 mL sealed vessel, 1-allylcyclopentanamine (460 mg, 3.674 mmol), DIEA (3 mL, 17.22 mmol) and methyl 6-chloro-3-nitro-5-(trifluoromethyl)pyridine-2-carboxylate (1.1 g, 3.479 mmol) were combined in acetonitrile (20 mL) and the mixture was heated at 75° C. for 2 hours. The reaction mixture was cooled to ambient temperature and the solvent removed in vacuo. The residue was diluted with ethyl acetate (50 mL) and washed with brine (2×25 mL), dried over sodium sulfate, filtered and concentrated in vacuo. The residue was purified by silica gel column chromatography (80 gram column) using a gradient from 100% hexanes to 30% ethyl acetate in hexanes to afford as a pale yellow solid, methyl 6-[(1-allylcyclopentyl)amino]-3-nitro-5-(trifluoromethyl)pyridine-2-carboxylate (1.19 g, 92%). $^1$H NMR (400 MHz, DMSO-d6) δ 8.47 (d, J=0.8 Hz, 1H), 6.45 (s, 1H), 5.84-5.69 (m, 1H), 5.06-4.99 (m, 1H), 4.95 (ddt, J=17.0, 2.5, 1.4 Hz, 1H), 3.94 (s, 3H), 2.68 (dt, J=7.3, 1.2 Hz, 2H), 2.17-2.06 (m, 2H), 1.86-1.74 (m, 2H), 1.72-1.58 (m, 4H) ppm. ESI-MS m/z calc. 373.12494, found 374.2 (M+1)⁺; Retention time: 1.55 minutes (LC Method J).

Step 2: 6-[(1-Allylcyclopentyl)amino]-3-nitro-5-(trifluoromethyl)pyridine-2-carboxylic Acid

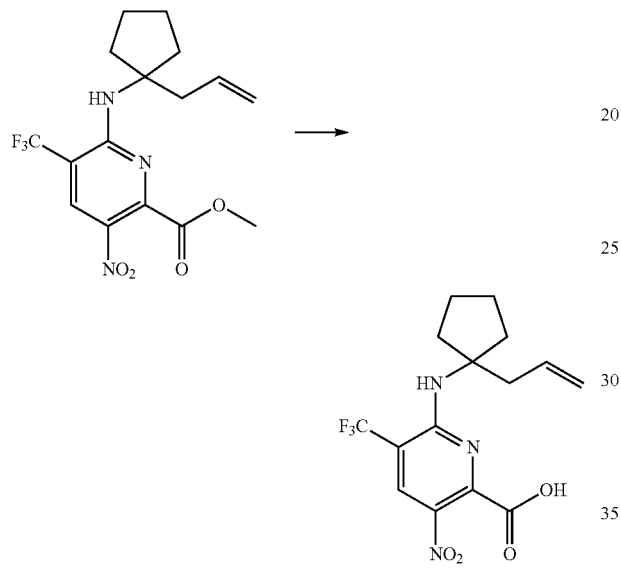

To a solution of methyl 6-[(1-allylcyclopentyl)amino]-3-nitro-5-(trifluoromethyl)pyridine-2-carboxylate (1.19 g, 3.188 mmol) in THF (12 mL) was added methanol (12 mL) and water (5 mL). Anhydrous lithium hydroxide (1.3 g, 54.28 mmol) was added and stirred at room temperature for 90 min. THF and methanol were removed under reduced pressure then 3M HCl solution was added until acidic. Extracted the aqueous layer with ethyl acetate (3×50 mL). The organic phases were combined, washed with brine (50 mL), dried over anhydrous sodium sulfate, filtered and concentrated under reduced pressure then dried under vacuum overnight to afford as a pale yellow gum, 6-[(1-allylcyclopentyl)amino]-3-nitro-5-(trifluoromethyl)pyridine-2-carboxylic acid (1.02 g, 89%). ¹H NMR (400 MHz, DMSO-d6) δ 14.22 (s, 1H), 8.45 (s, 1H), 6.36 (s, 1H), 5.84-5.69 (m, 1H), 5.02 (dd, J=10.2, 2.4 Hz, 1H), 4.99-4.92 (m, 1H), 2.69 (dd, J=7.0, 1.3 Hz, 2H), 2.19-2.07 (m, 2H), 1.85-1.74 (m, 2H), 1.73-1.58 (m, 4H) ppm. ESI-MS m/z calc. 359.10928, found 360.2 (M+1)⁺; Retention time: 1.78 minutes (LC Method A).

Step 3: 6-[(1-Allylcyclopentyl)amino]-N'-[(2R)-2-benzyloxy-2-(trifluoromethyl)hex-5-enoyl]-3-nitro-5-(trifluoromethyl)pyridine-2-carbohydrazide

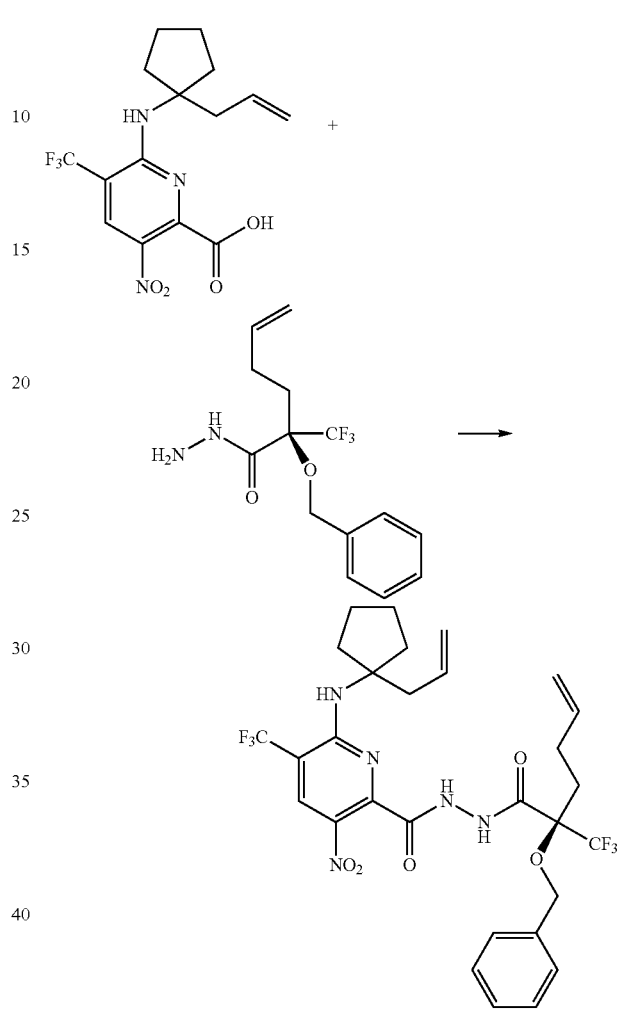

To a solution of 6-[(1-allylcyclopentyl)amino]-3-nitro-5-(trifluoromethyl)pyridine-2-carboxylic acid (250 mg, 0.6958 mmol) in DMF (6 mL) was added DIEA (550 µL, 3.158 mmol) and HATU (263 mg, 0.6917 mmol). The reaction mixture was stirred at room temperature for 10 minutes then added dropwise (2R)-2-benzyloxy-2-(trifluoromethyl)hex-5-enehydrazide (212.0 mg, 0.7013 mmol) dissolved in DMF (1.5 mL) and the reaction mixture was stirred at room temperature for 1 h. The reaction was diluted with ethyl acetate and washed with brine. The organic layer was further washed with 10% citric acid solution followed by brine. The organics were separated, dried over sodium sulfate, filtered and evaporated. The crude material was then purified by silica gel chromatography (40 gram column) using a gradient from 100% dichloromethane to 15% methanol in dichloromethane (product elutes at 5% methanol in dichloromethane) and concentrated the desired material which was then placed under vacuum for 4 hours to afford as a pale yellow foam, 6-[(1-allylcyclopentyl)amino]-N'-[(2R)-2-benzyloxy-2-(trifluoromethyl)hex-5-enoyl]-3-nitro-5-(trifluoromethyl)pyridine-2-carbohydrazide (399.7 mg,

811

89%). ESI-MS m/z calc. 643.22296, found 644.2 (M+1)⁺; Retention time: 1.88 minutes (LC Method J).

Step 4: N-(1-Allylcyclopentyl)-6-[5-[(1R)-1-benzyloxy-1-(trifluoromethyl)pent-4-enyl]-1,3,4-oxadiazol-2-yl]-5-nitro-3-(trifluoromethyl)pyridin-2-amine

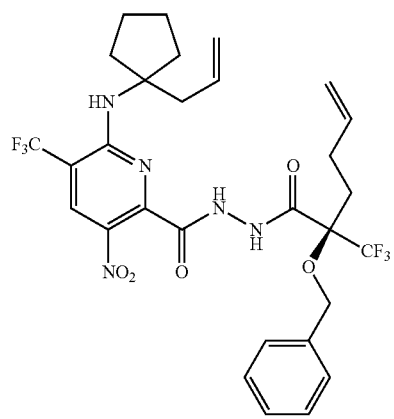

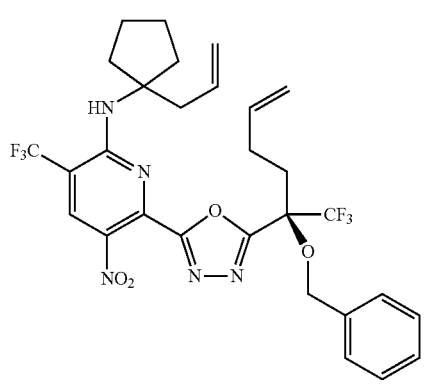

Into a solution of 6-[(1-allylcyclopentyl)amino]-N'-[(2R)-2-benzyloxy-2-(trifluoromethyl)hex-5-enoyl]-3-nitro-5-(trifluoromethyl)pyridine-2-carbohydrazide (330.1 mg, 0.5129 mmol) and DIEA (330.19 mg, 445 µL, 2.5548 mmol) in acetonitrile (8 mL) was added tosyl chloride (122.3 mg, 0.6415 mmol). The reaction was stirred at 70° C. for 2 hours. The solvent was removed under vacuum. The residue was directly loaded onto a silica gel column and purified by silica gel chromatography using a 0% to 20% ethyl acetate in hexanes gradient to furnish as a yellow gel, N-(1-allylcyclopentyl)-6-[5-[(1R)-1-benzyloxy-1-(trifluoromethyl)pent-4-enyl]-1,3,4-oxadiazol-2-yl]-5-nitro-3-(trifluoromethyl)pyridin-2-amine (318.5 mg, 99%). ESI-MS m/z calc. 625.2124, found 626.4 (M+1)⁺; Retention time: 4.55 minutes (LC Method G).

812

Step 5: (6R)-6-benzyloxy-17-nitro-6,15-bis(trifluoromethyl)spiro[19-oxa-3,4,13,18-tetrazatricyclo[12.3.1.1²,⁵]nonadeca-1(17),2,4,9,14(18),15-hexaene-12,1'-cyclopentane](E/Z Mixture)

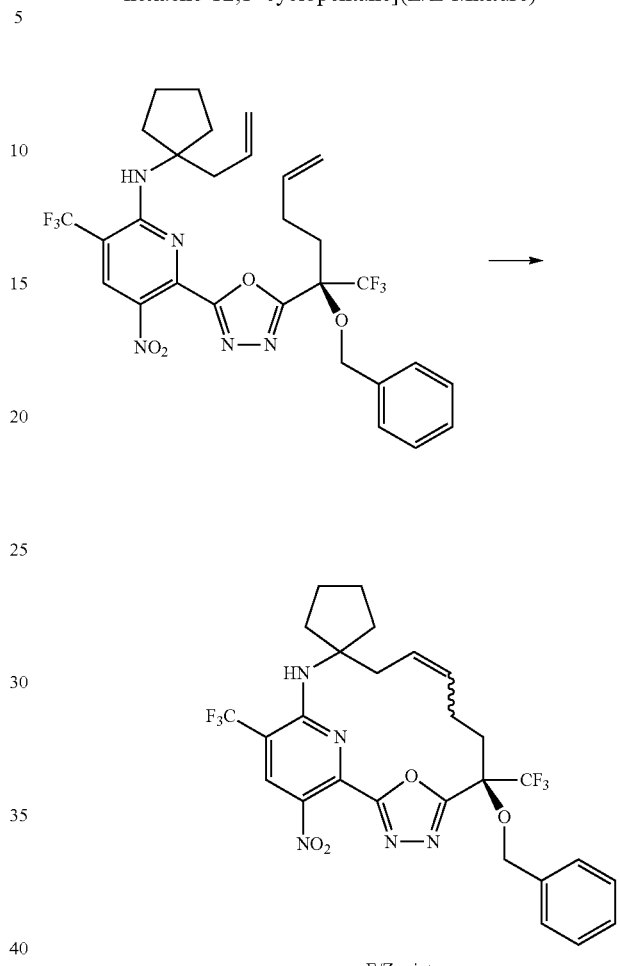

E/Z mixture

To a solution of N-(1-allylcyclopentyl)-6-[5-[(1R)-1-benzyloxy-1-(trifluoromethyl)pent-4-enyl]-1,3,4-oxadiazol-2-yl]-5-nitro-3-(trifluoromethyl)pyridin-2-amine (315.1 mg, 0.5037 mmol) in DCE (80 mL) at 50° C. under nitrogen atmosphere was added Zhan catalyst-1B (155.3 mg, 0.2114 mmol) and then bubbled with nitrogen for 1 minute. The resulting mixture was heated at 70° C. for 2.5 h. The reaction mixture was cooled down and concentrated under reduced pressure. The residue was purified by column chromatography (24 g silica gel column) and eluted with a gradient from 0% to 25% ethyl acetate in hexanes) to afford as pale yellow oil, (6R)-6-benzyloxy-17-nitro-6,15-bis(trifluoromethyl)spiro[19-oxa-3,4,13,18-tetrazatricyclo[12.3.1.1²,⁵] nonadeca-1(17),2,4,9,14(18),15-hexaene-12,1'-cyclopentane] (E/Z mixture) (82.3 mg, 27%). ESI-MS m/z calc. 597.1811, found 598.3 (M+1)⁺; Retention time: 4.4 minutes (LC Method G).

Step 6: (6R)-17-amino-6,15-bis(trifluoromethyl) spiro[19-oxa-3,4,13,18-tetrazatricyclo[12.3.1.12,5] nonadeca-1(18),2,4,14,16-pentaene-12,1'-cyclopentane]-6-ol (Compound 177)

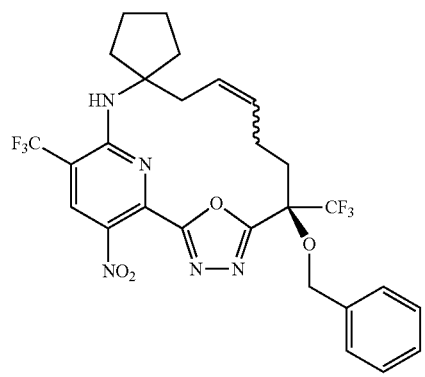

E/Z mixture

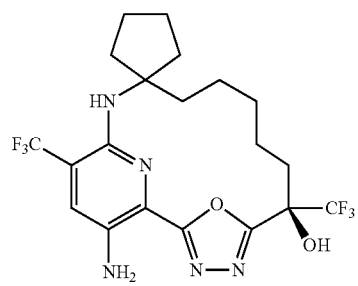

Into a solution of (6R)-6-benzyloxy-17-nitro-6,15-bis(trifluoromethyl)spiro[19-oxa-3,4,13,18-tetrazatricyclo[12.3.1.12,5]nonadeca-1(17),2,4,9,14(18),15-hexaene-12,1'-cyclopentane] (E/Z mixture) (82.3 mg, 0.1377 mmol) in ethyl acetate (8 mL) was added Pd/C (120 mg, 10% w/w, 0.1128 mmol). The reaction mixture was degassed with nitrogen and back-filled with hydrogen three times. The reaction mixture was stirred at room temperature for 40 hours. The catalyst was removed by filtration through a pad of Celite and washed with ethyl acetate (30 mL) then concentrated under vacuum. The residue was purified by silica gel chromatography using a gradient from 0% to 50% ethyl acetate in hexane to furnish as light yellow powder, (6R)-17-amino-6,15-bis(trifluoromethyl)spiro[19-oxa-3,4,13,18-tetrazatricyclo[12.3.1.12,5]nonadeca-1(18),2,4,14,16-pentaene-12,1'-cyclopentane]-6-ol (51.5 mg, 75%). $^1$H NMR (500 MHz, DMSO-d6) δ 7.58 (s, 2H), 5.97 (s, 2H), 4.68 (s, 1H), 2.69-2.60 (m, 1H), 2.19 (t, J=12.8, 12.8 Hz, 1H), 2.14-2.06 (m, 1H), 2.03-1.94 (m, 1H), 1.91-1.72 (m, 4H), 1.68-1.38 (m, 10H) ppm. ESI-MS m/z calc. 479.1756, found 480.1 (M+1)$^+$; Retention time: 3.86 minutes (LC Method H).

Example 99: Preparation of (6R)-17-amino-12-isopropyl-6,15-bis(trifluoromethyl)-19-oxa-3,4,13,18-tetrazatricyclo[12.3.1.12,5]nonadeca-1(18),2,4,14,16-pentaen-6-ol (enantiomer 1) (Compound 178) and (6R)-17-amino-12-isopropyl-6,15-bis(trifluoromethyl)-19-oxa-3,4,13,18-tetrazatricyclo[12.3.1.12,5]nonadeca-1(18),2,4,14,16-pentaen-6-ol (enantiomer 2) (Compound 179)

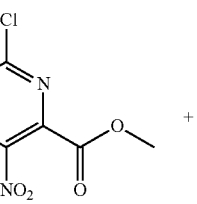

+

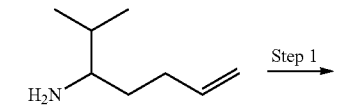

Step 1

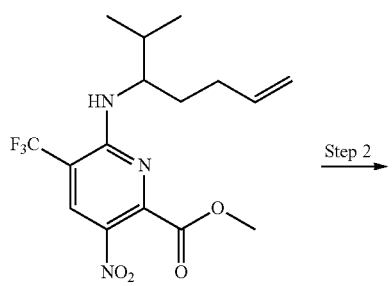

Step 2

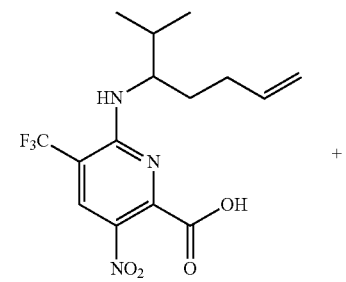

+

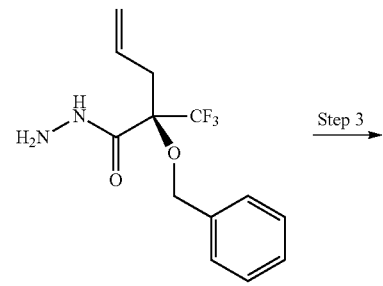

Step 3

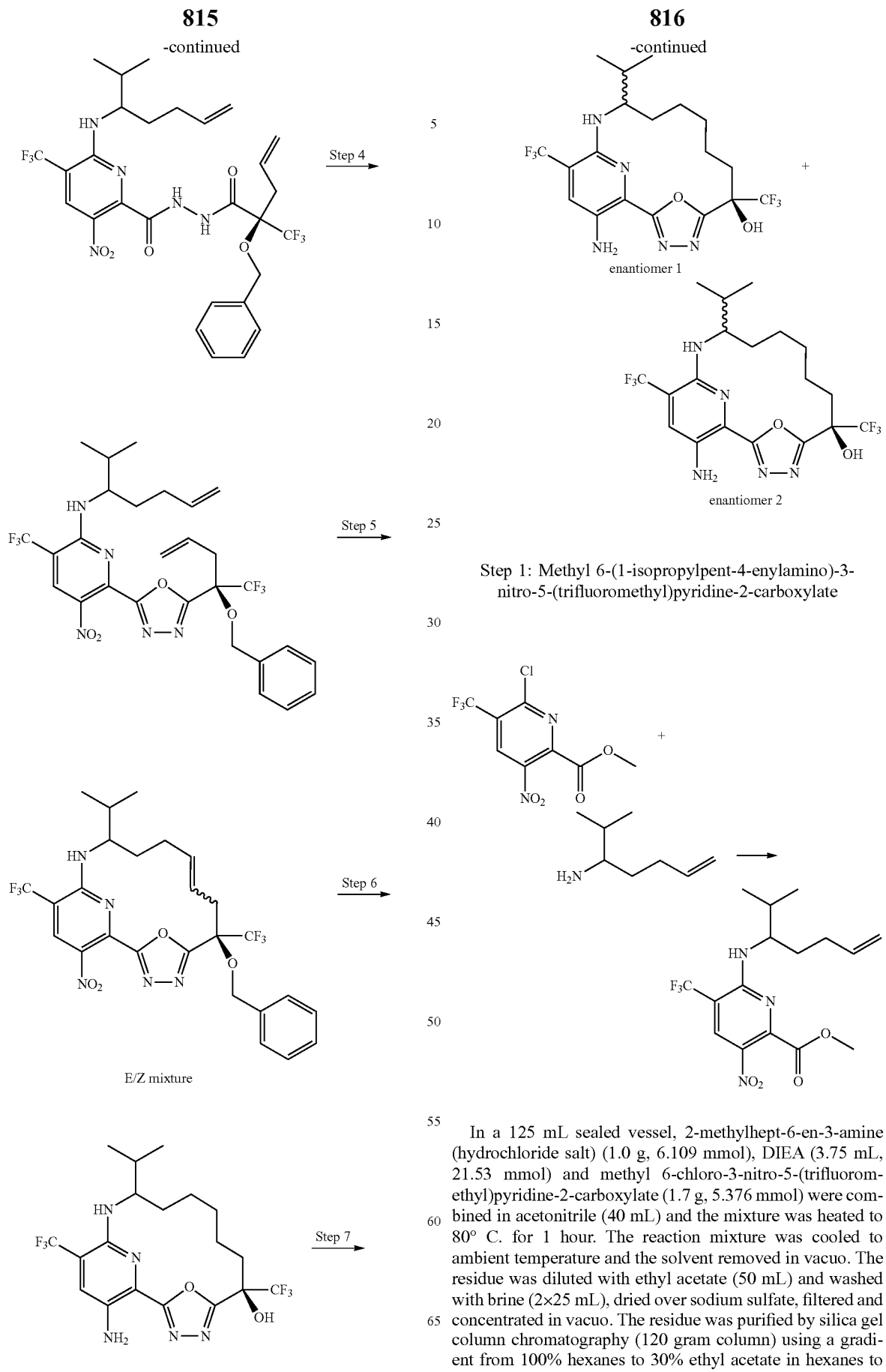

Step 1: Methyl 6-(1-isopropylpent-4-enylamino)-3-nitro-5-(trifluoromethyl)pyridine-2-carboxylate In a 125 mL sealed vessel, 2-methylhept-6-en-3-amine (hydrochloride salt) (1.0 g, 6.109 mmol), DIEA (3.75 mL, 21.53 mmol) and methyl 6-chloro-3-nitro-5-(trifluoromethyl)pyridine-2-carboxylate (1.7 g, 5.376 mmol) were combined in acetonitrile (40 mL) and the mixture was heated to 80° C. for 1 hour. The reaction mixture was cooled to ambient temperature and the solvent removed in vacuo. The residue was diluted with ethyl acetate (50 mL) and washed with brine (2×25 mL), dried over sodium sulfate, filtered and concentrated in vacuo. The residue was purified by silica gel column chromatography (120 gram column) using a gradient from 100% hexanes to 30% ethyl acetate in hexanes to afford as a pale yellow oil methyl 6-(1-isopropylpent-4-enylamino)-3-nitro-5-(trifluoromethyl)pyridine-2-carboxylate (2.0 g, 99%). ¹H NMR (400 MHz, DMSO-d6) δ 8.44 (s, 1H), 7.55 (d, J=8.7 Hz, 1H), 5.81-5.73 (m, 1H), 4.96-4.90 (m, 1H), 4.88 (q, J=1.5, 1.1 Hz, 1H), 4.29-4.17 (m, 1H), 3.92 (s, 3H), 2.06-1.97 (m, 1H), 1.97-1.85 (m, 2H), 1.85-1.75 (m, 1H), 1.72-1.63 (m, 1H), 0.89 (d, J=6.8 Hz, 3H), 0.82 (d, J=6.7 Hz, 3H) ppm. ESI-MS m/z calc. 375.1406, found 376.2 (M+1)⁺; Retention time: 2.11 minutes (LC Method A).

Step 2: 6-(1-Isopropylpent-4-enylamino)-3-nitro-5-(trifluoromethyl)pyridine-2-carboxylic Acid

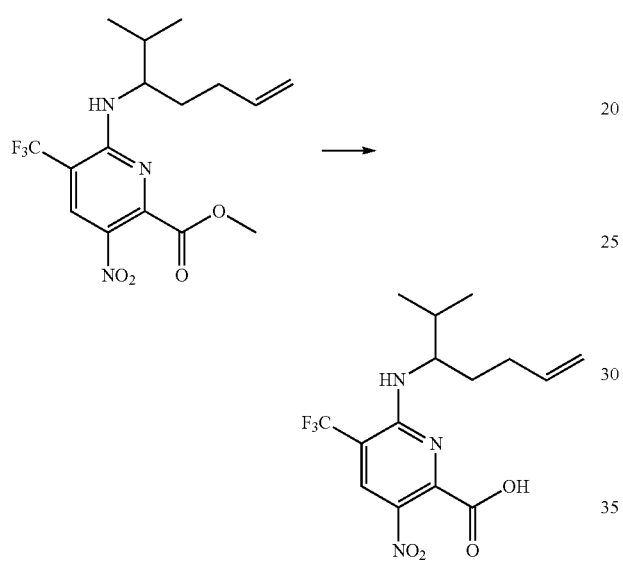

To a solution of methyl 6-(1-isopropylpent-4-enylamino)-3-nitro-5-(trifluoromethyl)pyridine-2-carboxylate (1.75 g, 4.662 mmol) in THF (17 mL) was added methanol (17 mL) and water (8.5 mL). Anhydrous lithium hydroxide (1.7 g, 70.99 mmol) was added and stirred at room temperature for 2 h. THF and methanol were removed under reduced pressure. A 3 M HCl solution was added until the mixture was acidic, then extracted the aqueous layer with ethyl acetate (3×100 mL). The organic phases were combined, washed with brine (100 mL), then dried over anhydrous sodium sulfate. The mixture was filtered and concentrated under reduced pressure. The residue was purified by silica gel column chromatography (120 gram column) using a gradient from 100% hexanes to 50% ethyl acetate in hexanes to afford as a pale yellow solid, 6-(1-isopropylpent-4-enylamino)-3-nitro-5-(trifluoromethyl)pyridine-2-carboxylic acid (1 g, 59%). ¹H NMR (400 MHz, DMSO-d6) δ 14.12 (s, 1H), 8.42 (s, 1H), 7.43 (d, J=8.7 Hz, 1H), 5.78 (ddt, J=16.9, 10.2, 6.6 Hz, 1H), 4.97-4.85 (m, 2H), 4.30-4.18 (m, 1H), 2.06-1.85 (m, 3H), 1.85-1.63 (m, 2H), 0.89 (d, J=6.7 Hz, 3H), 0.83 (d, J=6.7 Hz, 3H) ppm. ESI-MS m/z calc. 361.12494, found 362.2 (M+1)⁺; Retention time: 1.77 minutes (LC Method A).

Step 3: N'-[(2R)-2-Benzyloxy-2-(trifluoromethyl)pent-4-enoyl]-6-(1-isopropylpent-4-enylamino)-3-nitro-5-(trifluoromethyl)pyridine-2-carbohydrazide

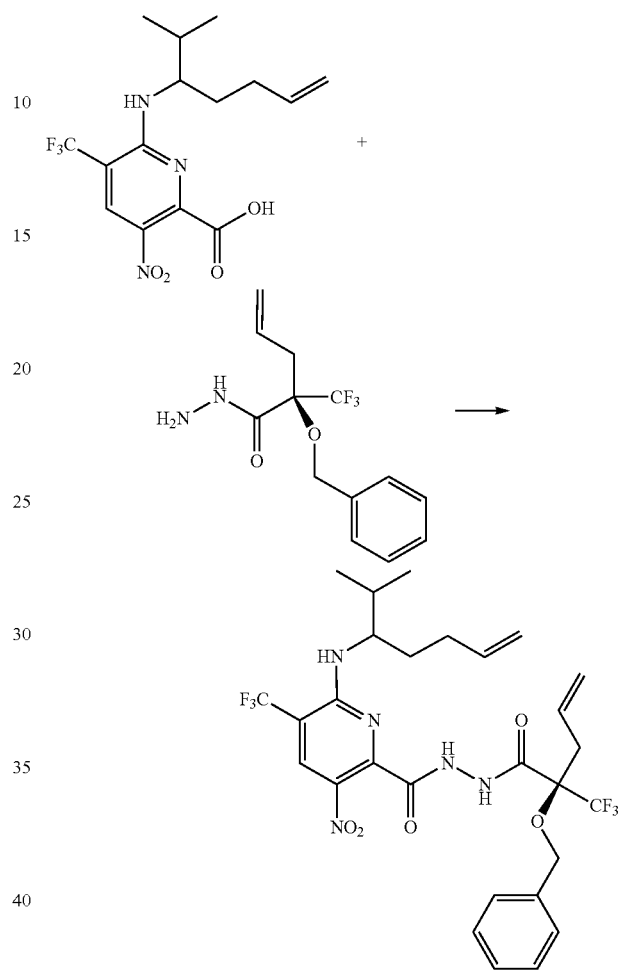

To a solution of 6-(1-isopropylpent-4-enylamino)-3-nitro-5-(trifluoromethyl)pyridine-2-carboxylic acid (300 mg, 0.828 mmol), (2R)-2-benzyloxy-2-(trifluoromethyl)pent-4-enehydrazide (290 mg, 1.006 mmol) and pyridine (342.3 mg, 0.35 mL, 4.3274 mmol) in EtOAc (3 mL) was added propylphosphonic anhydride solution in ethyl acetate (600 mg, 50% w/w, 0.9429 mmol) and the reaction mixture was stirred at 50° C. for 4 h. The reaction was allowed to cool to room temperature, diluted with ethyl acetate (25 mL), washed with 10% aqueous ammonium chloride, brine, dried over sodium sulfate, filtered and concentrated in vacuo. The resulting yellow oil was purified by silica gel chromatography (40 g column, loaded using DCM, eluted with 20% ethyl acetate in hexanes). The desired product fractions were combined and concentrated in vacuo to give N-[(2R)-2-benzyloxy-2-(trifluoromethyl)pent-4-enoyl]-6-(1-isopropylpent-4-enylamino)-3-nitro-5-(trifluoromethyl)pyridine-2-carbohydrazide (510 mg, 93%) as a white solid. ESI-MS m/z calc. 631.2229, found 632.5 (M+1)⁺; Retention time: 7.51 minutes (LC Method DD).

Step 4: 6-[5-[(1R)-1-Benzyloxy-1-(trifluoromethyl)but-3-enyl]-1,3,4-oxadiazol-2-yl]-N-(1-isopropylpent-4-enyl)-5-nitro-3-(trifluoromethyl)pyridin-2-amine

Step 5: (6R)-6-Benzyloxy-12-isopropyl-17-nitro-6,15-bis(trifluoromethyl)-19-oxa-3,4,13,18-tetrazatricyclo[12.3.1.12,5]nonadeca-1(18),2,4,8,14,16-hexaene (E/Z mixture)

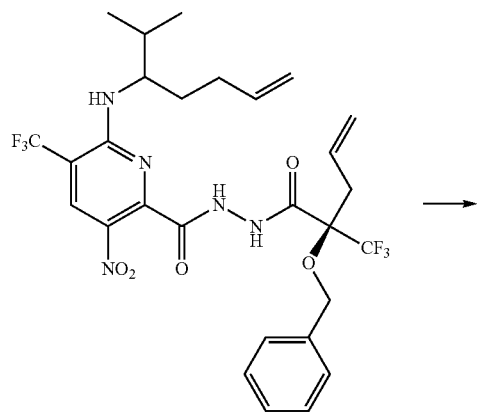

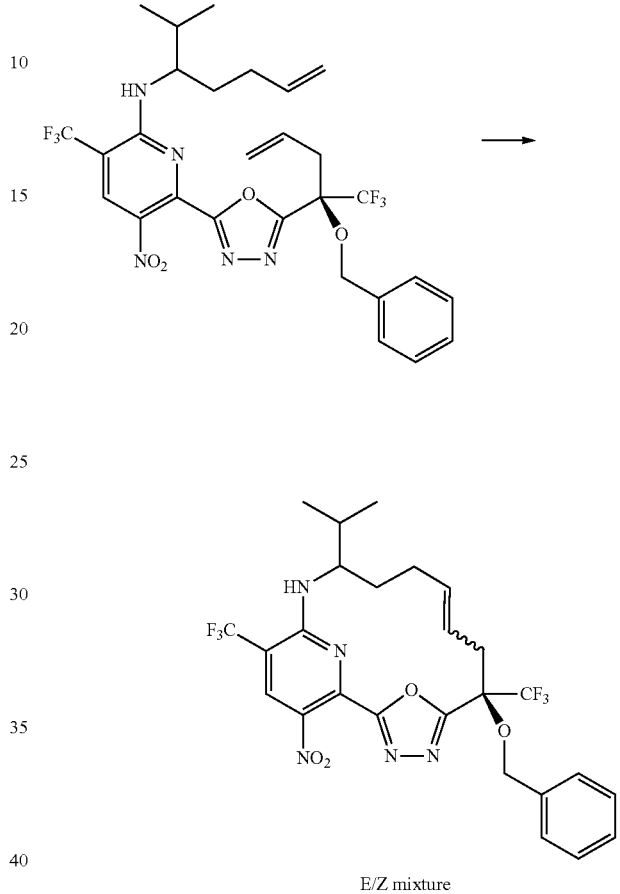

E/Z mixture

To a stirred solution of N'-[(2R)-2-benzyloxy-2-(trifluoromethyl)pent-4-enoyl]-6-(1-isopropylpent-4-enylamino)-3-nitro-5-(trifluoromethyl)pyridine-2-carbohydrazide (510 mg, 0.7424 mmol) and DIEA (296.8 mg, 0.4 mL, 2.2964 mmol) in acetonitrile (10 mL) was added tosyl chloride (200 mg, 1.0491 mmol) at 50° C. The reaction mixture was heated to 70° C. and stirred for 2 h. The reaction mixture was diluted with ethyl acetate (25 mL). The organic layer was washed with brine, dried over sodium sulfate, filtered and concentrated in vacuo. The resulting brown viscous oil was purified by silica gel chromatography (40 g column, loaded in DCM, eluted with 5% ethyl acetate in hexanes). The desired product fractions were combined and concentrated in vacuo to give as a pale yellow oil, 6-[5-[(1R)-1-benzyloxy-1-(trifluoromethyl)but-3-enyl]-1,3,4-oxadiazol-2-yl]-N-(1-isopropylpent-4-enyl)-5-nitro-3-(trifluoromethyl)pyridin-2-amine (398 mg, 85%). ESI-MS m/z calc. 613.2124, found 614.3 (M+1)$^+$; Retention time: 8.38 minutes (LC Method DD).

A solution of 6-[5-[(1R)-1-benzyloxy-1-(trifluoromethyl)but-3-enyl]-1,3,4-oxadiazol-2-yl]-N-(1-isopropylpent-4-enyl)-5-nitro-3-(trifluoromethyl)pyridin-2-amine (398 mg, 0.6162 mmol) in DCE (40 mL) was bubbled with nitrogen for fifteen minutes followed by the addition of Zhan catalyst-1B (120 mg, 0.1633 mmol). The reaction mixture was heated to 70° C. and stirred overnight. The reaction mixture was concentrated in vacuo and purified by silica gel chromatography (40 g column, loaded in DCM, eluted with 5% ethyl acetate in hexanes). The desired product fractions were combined and concentrated in vacuo to give as a pale yellow sticky solid, (6R)-6-benzyloxy-12-isopropyl-17-nitro-6,15-bis(trifluoromethyl)-19-oxa-3,4,13,18-tetrazatricyclo[12.3.1.12,5]nonadeca-1(18),2,4,8,14,16-hexaene (E/Z mixture) (180 mg, 47%). ESI-MS m/z calc. 585.1811, found 586.7 (M+1)$^+$; Retention time: 8.17 minutes (LC Method DD).

Step 6: (6R)-17-Amino-12-isopropyl-6,15-bis(trifluoromethyl)-19-oxa-3,4,13,18-tetrazatricyclo[12.3.1.1²,⁵]nonadeca-1(18),2,4,14,16-pentaen-6-ol

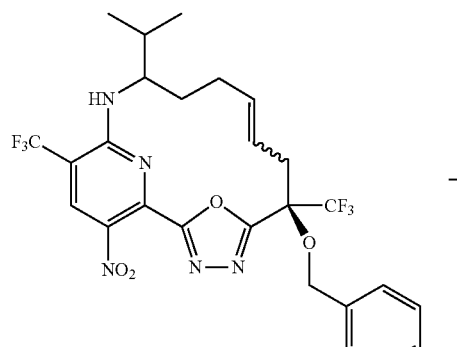

E/Z mixture

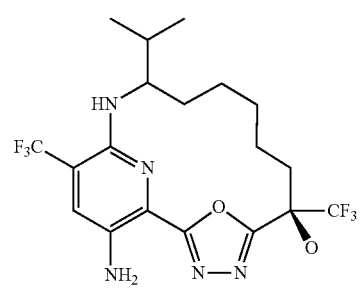

A flask with a mixture of (6R)-6-benzyloxy-12-isopropyl-17-nitro-6,15-bis(trifluoromethyl)-19-oxa-3,4,13,18-tetrazatricyclo[12.3.1.1²,⁵]nonadeca-1(18),2,4,8,14,16-hexaene (E/Z mixture) (180 mg, 0.3013 mmol) and Pd/C (210 mg, 10% w/w, 0.1973 mmol) in EtOH (10 mL) was purged with nitrogen and evacuated. The flask was fitted with a balloon of hydrogen (0.6074 mg, 6.7489 mL, 0.3013 mmol) and evacuated. Another balloon of hydrogen (0.6074 mg, 6.7489 mL, 0.3013 mmol) was fitted and the reaction mixture was stirred at room temperature for 20 h. The reaction mixture was filtered over Celite. The cake was washed with methanol. The filtrate was concentrated in vacuo and the resulting fluorescent green oil was purified by silica gel chromatography (40 g column, loaded with DCM, eluted with 20% ethyl acetate in hexanes). The desired product fractions were combined and concentrated in vacuo to give as a bright yellow solid, (6R)-17-amino-12-isopropyl-6,15-bis(trifluoromethyl)-19-oxa-3,4,13,18-tetrazatricyclo[12.3.1.1²,⁵]nonadeca-1(18),2,4,14,16-pentaen-6-ol (80 mg, 56%). ESI-MS m/z calc. 467.1756, found 468.3 (M+1)⁺; Retention time: 7.66 minutes (LC Method DD).

Step 7: (6R)-17-Amino-12-isopropyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (Compound 178) and (6R)-17-amino-12-isopropyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (Compound 179)

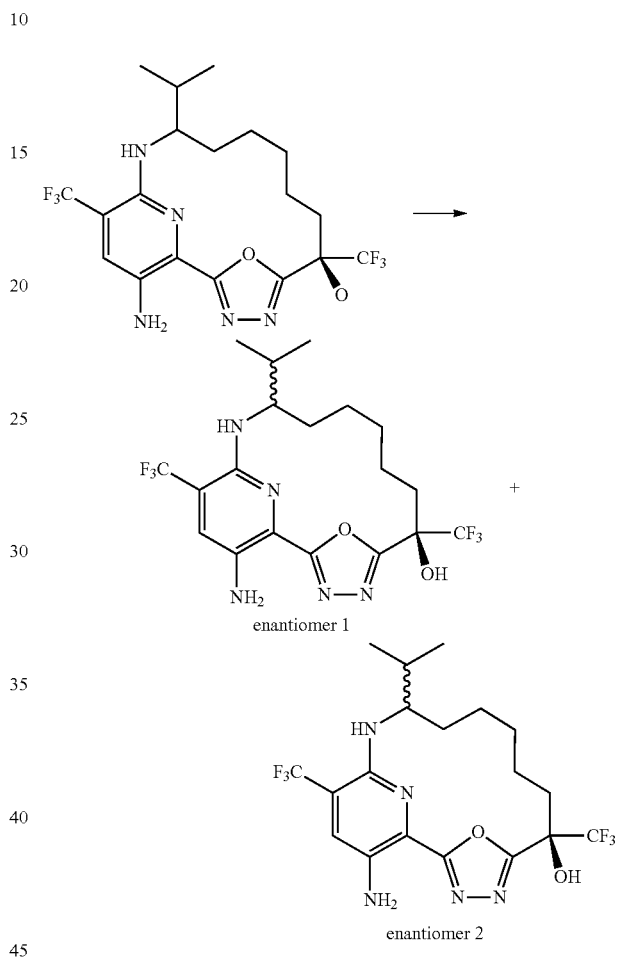

The two diastereomers of (6R)-17-amino-12-isopropyl-6,15-bis(trifluoromethyl)-19-oxa-3,4,13,18-tetrazatricyclo[12.3.1.1²,⁵]nonadeca-1(18),2,4,14,16-pentaen-6-ol (78 mg, 0.1669 mmol) were separated by chiral supercritical fluid chromatography (cellulose 4 column; 10% ethanol (containing 0.1% diethylamine) in $CO_2$; flow=4 mL/min; 100 bar; 40° C.). Fractions containing each diastereomer were then concentrated under reduced pressure to give two isolated peaks.

Peak 1: The material obtained from peak 1 was further purified by silica gel chromatography (24 g column, eluting with a gradient from 20% to 30% EtOAc/dichloromethane) and freeze dried to afford as a yellow solid, (6R)-17-amino-12-isopropyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (34 mg, 43%). $^1$H NMR (400 MHz, DMSO-d6) δ 7.63 (s, 1H), 7.57 (s, 1H), 6.05 (s, 2H), 4.51 (d, J=4.9 Hz, 1H), 3.59-3.50 (m, 1H), 2.27-2.14 (m, 2H), 2.11-1.94 (m, 2H), 1.68-1.55 (m, 3H), 1.53-1.37 (m, 3H), 1.25-1.14 (m, 1H), 0.97 (d, J=6.8 Hz, 3H), 0.91 (d, J=6.8 Hz, 3H) ppm. $^{19}$F NMR (377 MHz, DMSO-d6) δ−62.69 (s, 3F), −79.09 (s, 3F) ppm. ESI-MS m/z calc. 467.1756, found 468.0 (M+1)⁺; Retention time: 3.64 minutes (LC Method C).

Peak 2: The material obtained from peak 2 was further purified by silica gel chromatography (24 g column, eluting with a gradient from 20% to 30% EtOAc/dichloromethane) and freeze dried to afford as a yellow solid, (6R)-17-amino-12-isopropyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (26 mg, 33%). ¹H NMR (400 MHz, DMSO-d6) δ 7.63 (s, 1H), 7.56 (s, 1H), 6.03 (s, 2H), 4.55 (d, J=5.6 Hz, 1H), 3.69-3.61 (m, 1H), 2.34-2.24 (m, 1H), 2.14-1.95 (m, 3H), 1.85-1.73 (m, 1H), 1.62-1.34 (m, 5H), 1.31-1.21 (m, 1H), 0.97 (d, J=6.8 Hz, 3H), 0.91 (d, J=7.1 Hz, 3H) ppm. ¹⁹F NMR (377 MHz, DMSO-d6) δ−62.69 (s, 3F), −76.49 (s, 3F) ppm. ESI-MS m/z calc. 467.1756, found 468.0 (M+1)⁺; Retention time: 3.61 minutes (LC Method C).

Example 100: Preparation of (6R)-17-amino-12-benzyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (Compound 180) and (6R)-17-amino-12-benzyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (Compound 181)

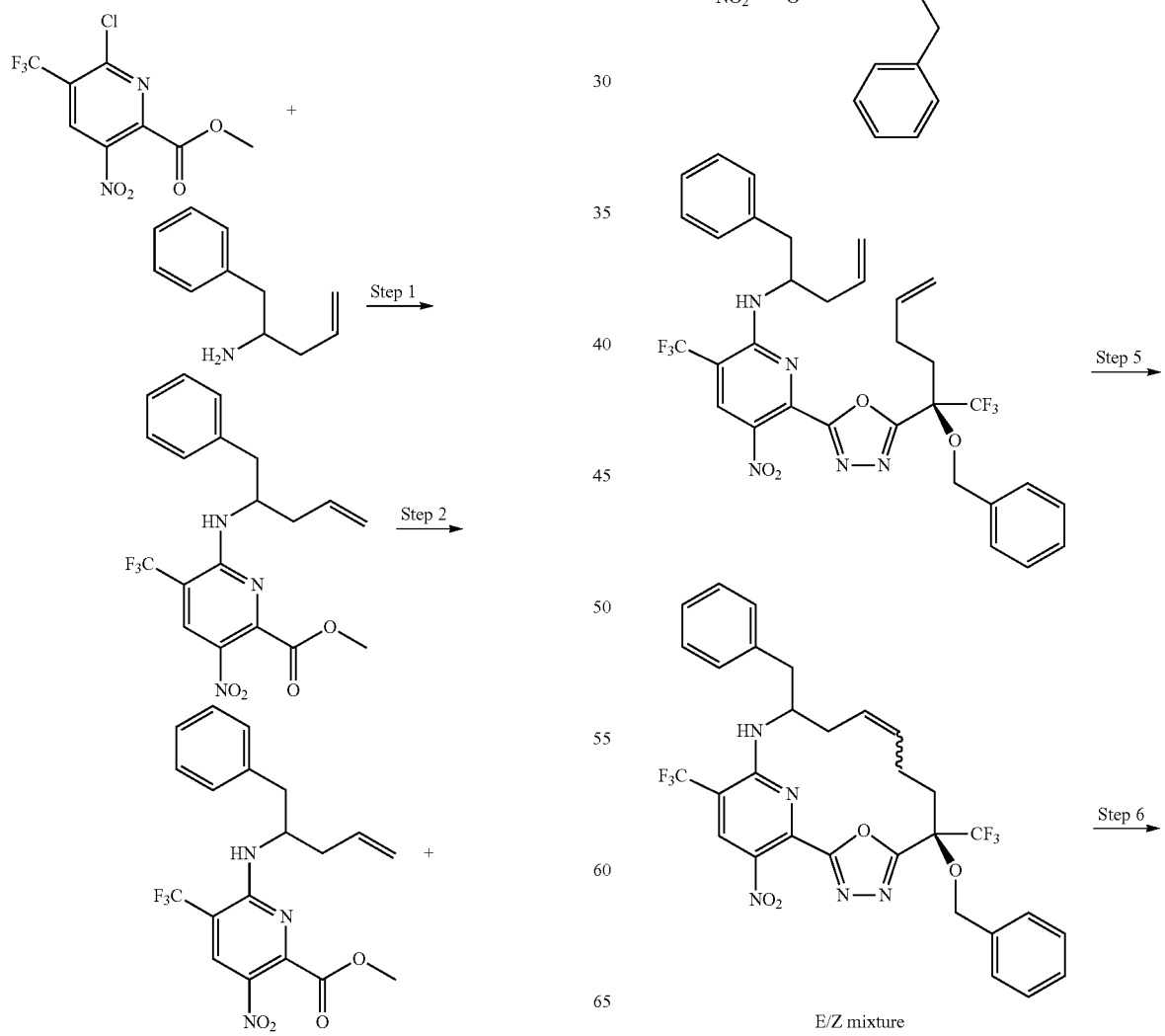

-continued

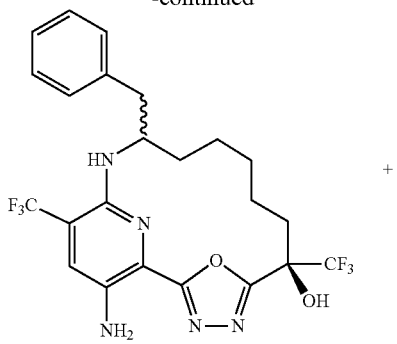

enantiomer 1

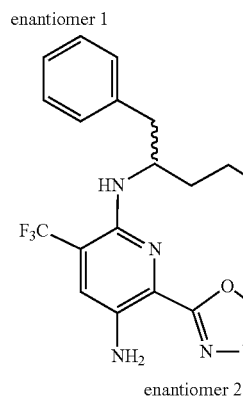

enantiomer 2

Step 1: Methyl 6-(1-benzylbut-3-enylamino)-3-nitro-5-(trifluoromethyl)pyridine-2-carboxylate

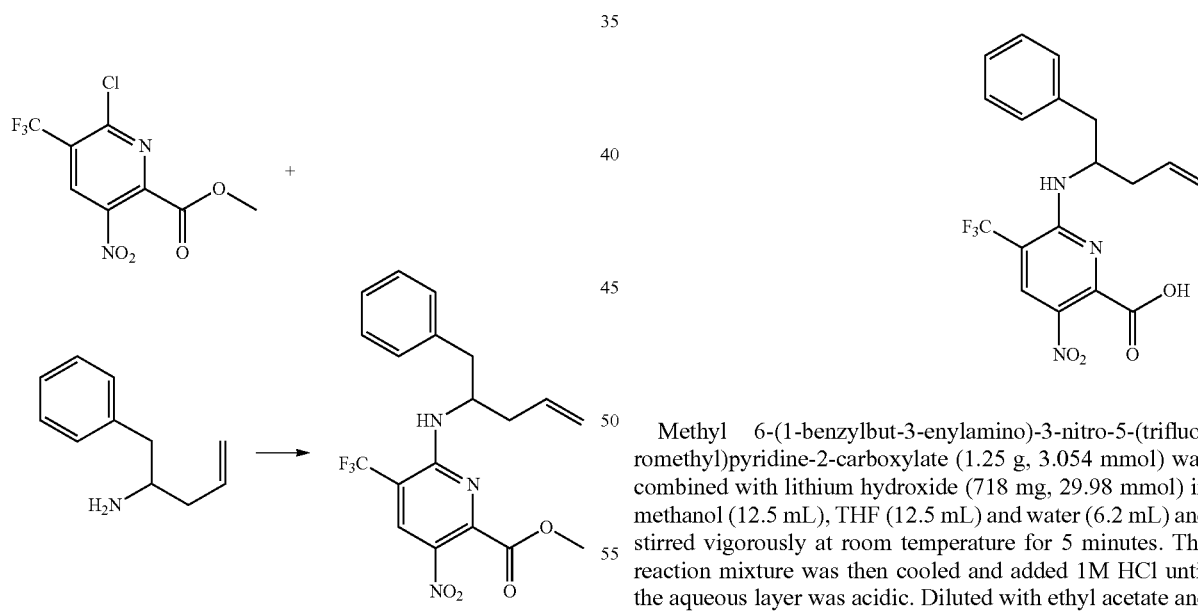

In a 125 mL sealed vessel, 1-phenylpent-4-en-2-amine (690 mg, 4.279 mmol), DIEA (2 mL, 11.48 mmol) and methyl 6-chloro-3-nitro-5-(trifluoromethyl)pyridine-2-carboxylate (1.1 g, 3.479 mmol) were combined in acetonitrile (28 mL) and the mixture was heated at 80° C. for 15 minutes. The reaction mixture was cooled to ambient temperature and the solvent was removed in vacuo. The residue was diluted with ethyl acetate (50 mL) and washed with brine (2×25 mL), dried over sodium sulfate, filtered and concentrated in vacuo. The residue was purified by silica gel column chromatography (40 gram column) using a gradient from 100% hexanes to 30% ethyl acetate in hexanes to afford as a white solid, methyl 6-(1-benzylbut-3-enylamino)-3-nitro-5-(trifluoromethyl)pyridine-2-carboxylate (1.25 g, 88%). ESI-MS m/z calc. 409.12494, found 410.53 (M+1)$^+$; Retention time: 0.78 minutes (LC Method S).

Step 2: 6-(1-Benzylbut-3-enylamino)-3-nitro-5-(trifluoromethyl)pyridine-2-carboxylic Acid

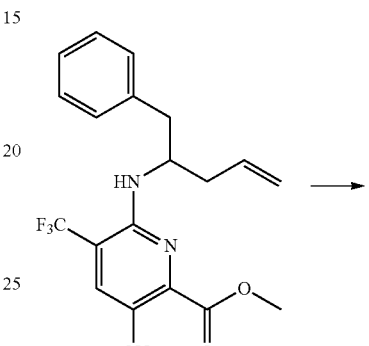

Methyl 6-(1-benzylbut-3-enylamino)-3-nitro-5-(trifluoromethyl)pyridine-2-carboxylate (1.25 g, 3.054 mmol) was combined with lithium hydroxide (718 mg, 29.98 mmol) in methanol (12.5 mL), THF (12.5 mL) and water (6.2 mL) and stirred vigorously at room temperature for 5 minutes. The reaction mixture was then cooled and added 1M HCl until the aqueous layer was acidic. Diluted with ethyl acetate and the layers were separated.

The aqueous layer was extracted with additional ethyl acetate (2×15 mL). The combined organics were washed with brine, dried over sodium sulfate, filtered and concentrated without further purification to afford as a sticky pale yellow solid, 6-(1-benzylbut-3-enylamino)-3-nitro-5-(trifluoromethyl)pyridine-2-carboxylic acid (1.2 g, 99%). ESI-MS m/z calc. 395.10928, found 396.16 (M+1)$^+$; Retention time: 0.69 minutes. This material was used directly in the ensuing step (LC Method S).

Step 3: 6-(1-Benzylbut-3-enylamino)-N'-[(2R)-2-benzyloxy-2-(trifluoromethyl)hex-5-enoyl]-3-nitro-5-(trifluoromethyl)pyridine-2-carbohydrazide

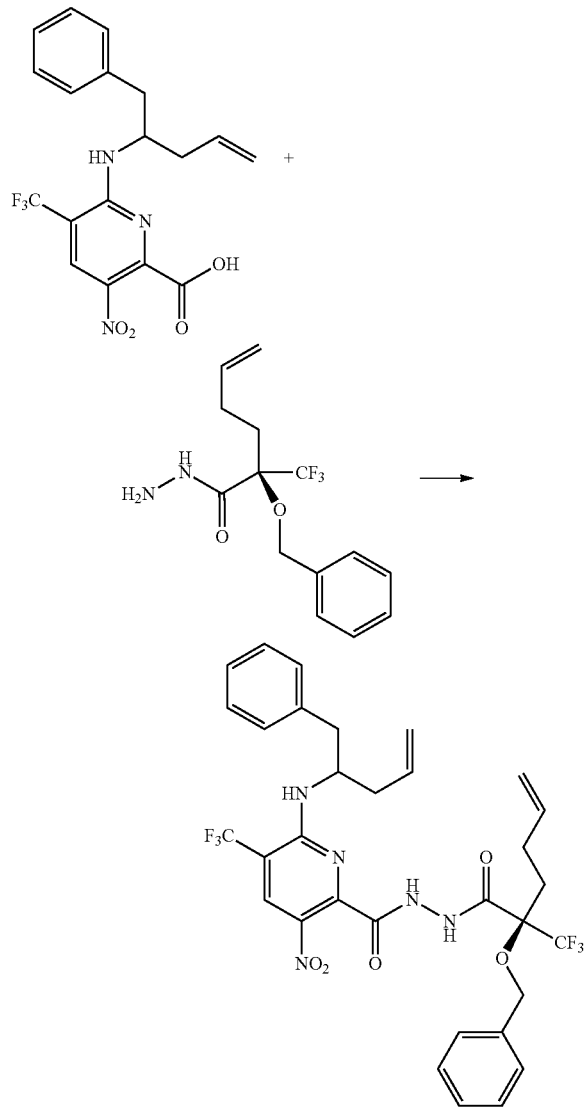

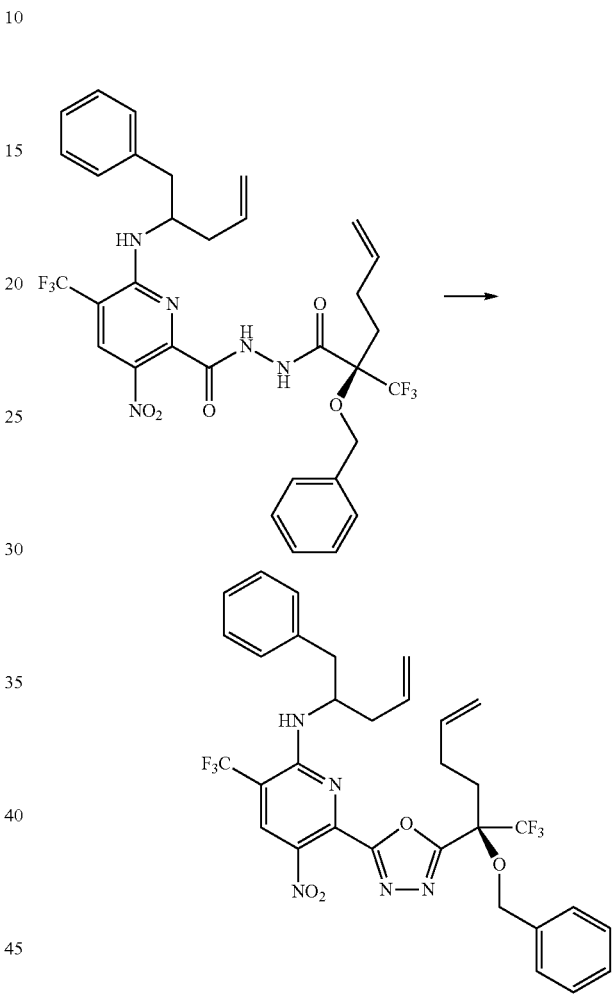

To a solution of 6-(1-benzylbut-3-enylamino)-3-nitro-5-(trifluoromethyl)pyridine-2-carboxylic acid (375 mg, 0.9486 mmol) in DMF (14 mL) was added DIEA (660 µL, 3.789 mmol) and HATU (360 mg, 0.9468 mmol). The reaction mixture was stirred at room temperature for 10 minutes then added (2R)-2-benzyloxy-2-(trifluoromethyl)hex-5-enehydrazide (320 mg, 1.059 mmol) in DMF (3 mL), dropwise. Let the reaction stir at room temperature for 1 hour. Diluted the reaction with brine and water and let stir for 5 minutes. The reaction was extracted with ethyl acetate (3×20 mL). The organic layers were washed with brine (20 mL), dried over sodium sulfate, filtered and evaporated. The crude material was then purified by silica gel chromatography (12 gram column) using a gradient from 100% hexanes to 70% ethyl acetate in hexanes to afford as a white solid, 6-(1-benzylbut-3-enylamino)-N'-[(2R)-2-benzyloxy-2-(trifluoromethyl)hex-5-enoyl]-3-nitro-5-(trifluoromethyl)pyridine-2-carbohydrazide (522 mg, 81%). ESI-MS m/z calc. 679.22296, found 680.55 (M+1)$^+$; Retention time: 0.67 minutes (LC Method R).

Step 4: N-(1-benzylbut-3-enyl)-6-[5-[(1R)-1-benzyloxy-1-(trifluoromethyl)pent-4-enyl]-1,3,4-oxadiazol-2-yl]-5-nitro-3-(trifluoromethyl)pyridin-2-amine A solution of 6-(1-benzylbut-3-enylamino)-N'-[(2R)-2-benzyloxy-2-(trifluoromethyl)hex-5-enoyl]-3-nitro-5-(trifluoromethyl)pyridine-2-carbohydrazide (520 mg, 0.7651 mmol) and DIEA (460 µL, 2.641 mmol) in acetonitrile (10 mL) was heated to 60° C., then p-toluenesulfonyl chloride (166 mg, 0.8707 mmol) was added. The resulted mixture was stirred at 60° C. for 15 minutes. The reaction mixture was cooled and quenched with a saturated solution of sodium bicarbonate. Extracted with ethyl acetate (3×40 mL). The organics were separated, dried over sodium sulfate, filtered and evaporated. The crude material was then purified by silica gel chromatography (24 g column) using a gradient from 100% hexanes to 40% ethyl acetate in hexanes to afford as a yellow semi-solid, N-(1-benzylbut-3-enyl)-6-[5-[(1R)-1-benzyloxy-1-(trifluoromethyl)pent-4-enyl]-1,3,4-oxadiazol-2-yl]-5-nitro-3-(trifluoromethyl)pyridin-2-amine (425 mg, 84%). ESI-MS m/z calc. 661.2124, found 662.6 (M+1)$^+$; Retention time: 0.82 minutes (LC Method R).

829

Step 5: (6R)-12-Benzyl-6-benzyloxy-17-nitro-6,15-bis(trifluoromethyl)-19-oxa-3,4,13,18-tetrazatricyclo[12.3.1.1²,⁵]nonadeca-1(18),2,4,9,14,16-hexaene (E/Z Mixture)

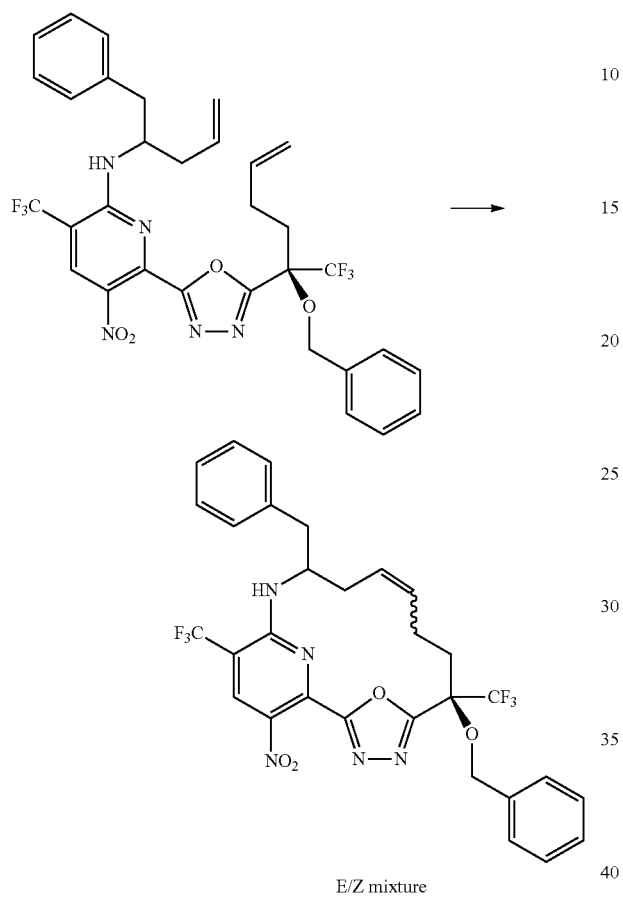

E/Z mixture

Nitrogen was bubbled through a light yellow solution of N-(1-benzylbut-3-enyl)-6-[5-[(1R)-1-benzyloxy-1-(trifluoromethyl)pent-4-enyl]-1,3,4-oxadiazol-2-yl]-5-nitro-3-(trifluoromethyl)pyridin-2-amine (425 mg, 0.6424 mmol) in DCE (70 mL) overnight. Zhan catalyst-1B (95 mg, 0.1295 mmol) was then added in three portions, the first at room temperature and nitrogen was bubbled for 5 min. Then the light green solution was stirred at 75° C. (pre-heated oil bath) for 2 h, while the two other portions were added each 30 min apart. The brown solution was cooled to room temperature, then DMSO (10 drops) was added to quench the catalyst. The solvent was removed under vacuum and the residue was dry-packed on silica gel with dichloromethane. Purified by chromatography on a 24 g silica column (1% to 40% MTBE/heptanes) to give (6R)-12-benzyl-6-benzyloxy-17-nitro-6,15-bis(trifluoromethyl)-19-oxa-3,4,13,18-tetrazatricyclo[12.3.1.1²,⁵]nonadeca-1(18),2,4,9,14,16-hexaene (E/Z mixture) (76 mg, 19%) as a light yellow oil. This material was carried directly to the ensuing step.

830

Step 6: (6R)-17-amino-12-benzyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (Compound 180) and (6R)-17-amino-12-benzyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (Compound 181)

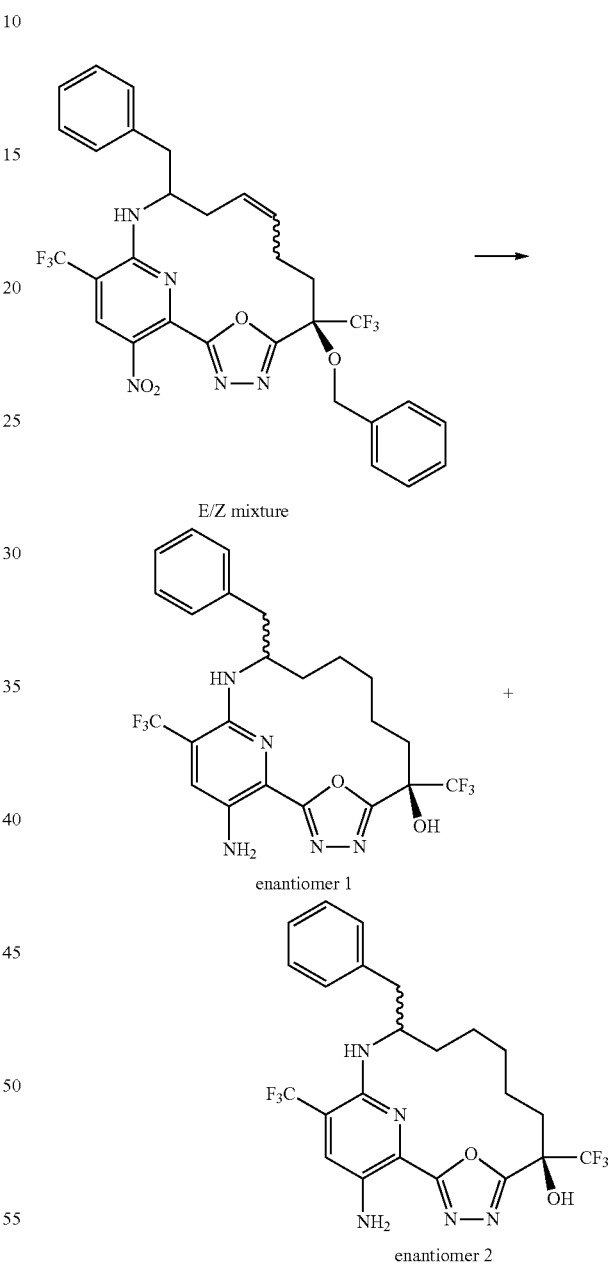

Palladium on carbon (30 mg, 10% w/w, 0.0282 mmol) was added to a degassed solution of (6R)-12-benzyl-6-benzyloxy-17-nitro-6,15-bis(trifluoromethyl)-19-oxa-3,4,13,18-tetrazatricyclo[12.3.1.1²,⁵]nonadeca-1(18),2,4,9,14,16-hexaene (E/Z mixture) (75 mg, 0.0829 mmol) in methanol (8 mL) at room temperature. The black suspension was purged with nitrogen for 5 min, then hydrogen was bubbled through the suspension for 5 min. Then the mixture was stirred at room temperature overnight under a hydrogen atmosphere. The black suspension was filtrated over Celite and concentrated under vacuum to give a fluorescent yellow oil (59 mg). Purification of this oil by chromatography on a 12 g silica column (1% to 40% MTBE/heptanes) gave a yellow solid (48 mg). Further purified by chromatography on a 15 g C$_{18}$ column (5% to 95% acetonitrile/0.02% HCl in water) to give a yellow solid (22 mg). Purification of this solid by SFC (cellulose 3 column; 30% methanol in CO$_2$; flow=4 mL/min; 100 bar; 40° C.) separated the two diastereoisomers.

The first peak to elute was isolated as a yellow solid, (6R)-17-amino-12-benzyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (10.35 mg, 23%). $^1$H NMR (400 MHz, DMSO-d6) δ 7.58 (s, 1H), 7.53 (br. s, 1H), 7.31-7.24 (m, 4H), 7.2-7.15 (m, 1H), 6.00 (s, 2H), 4.98 (d, J=4.2 Hz, 1H), 3.80-3.61 (m, 1H), 3.07 (dd, J=13.9, 2.9 Hz, 1H), 2.75 (dd, J=13.9, 10.8 Hz, 1H), 2.55-2.41 (m, 1H), 2.36-2.21 (m, 1H), 2.11-1.96 (m, 1H), 1.75-1.41 (m, 6H), 1.16-1.00 (m, 1H) ppm. $^{19}$F NMR (377 MHz, DMSO-d6) δ−62.70 (s, 3F), −79.11 (s, 3F) ppm. ESI-MS m/z calc. 515.1756, found 516.0 (M+1)$^+$; Retention time: 3.57 minutes (LC Method C).

The second peak to elute was isolated as a yellow solid, (6R)-17-amino-12-benzyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (8.02 mg, 19%). $^1$H NMR (400 MHz, DMSO-d6) δ 7.55 (s, 1H), 7.54 (br. s, 1H), 7.28-7.26 (m, 4H), 7.2-7.13 (m, 1H), 5.99 (s, 2H), 5.06 (d, J=4.8 Hz, 1H), 3.88-3.66 (m, 1H), 3.06 (dd, J=13.9, 3.1 Hz, 1H), 2.77 (dd, J=13.9, 10.8 Hz, 1H), 2.43-2.30 (m, 2H), 2.13-2.01 (m, 1H), 1.83-1.40 (m, 6H), 1.21-1.09 (m, 1H) ppm. $^{19}$F NMR (377 MHz, DMSO-d6) δ−62.67 (s, 3F), −76.35 (s, 3F) ppm. ESI-MS m/z calc. 515.1756, found 516.0 (M+1)+; Retention time: 3.59 minutes (LC Method C).

Example 101: Preparation of (6R)-17-amino-12-(4-fluorophenyl)-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (Compound 182) and (6R)-17-amino-12-(4-fluorophenyl)-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (Compound 183)

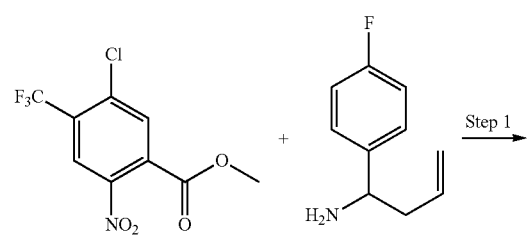

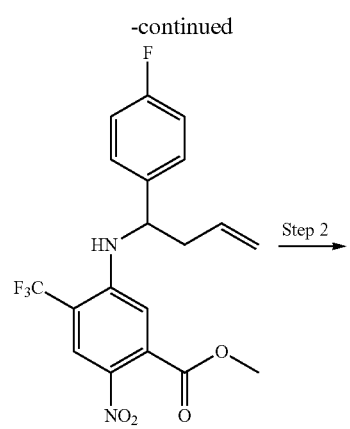

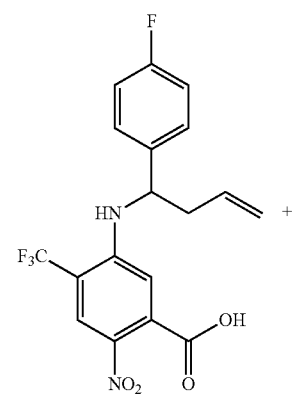

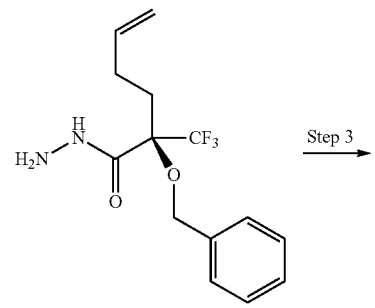

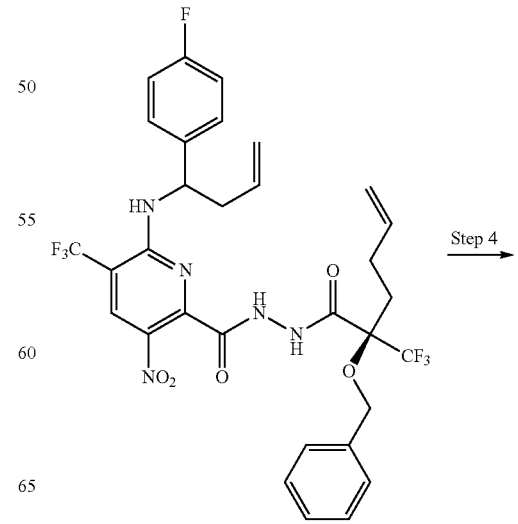

833

-continued

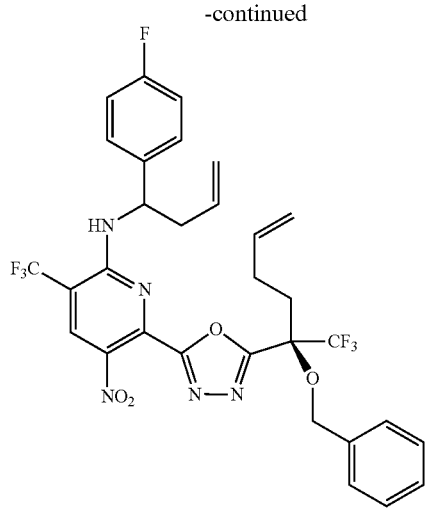

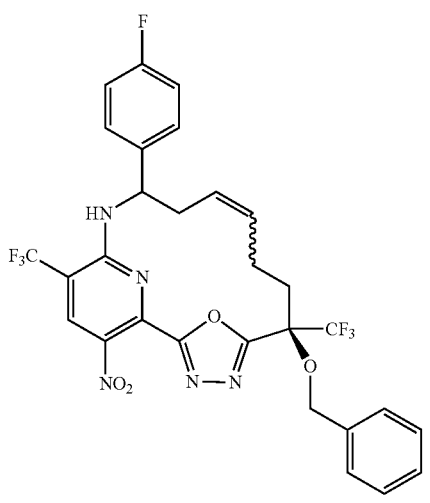
E/Z mixture

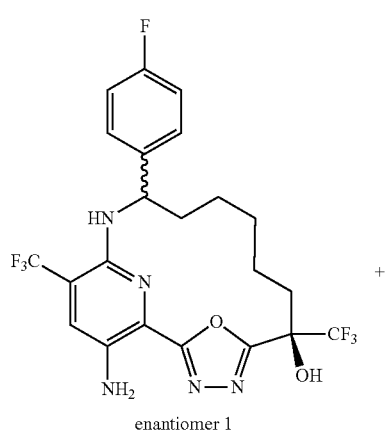
enantiomer 1

+

834

-continued

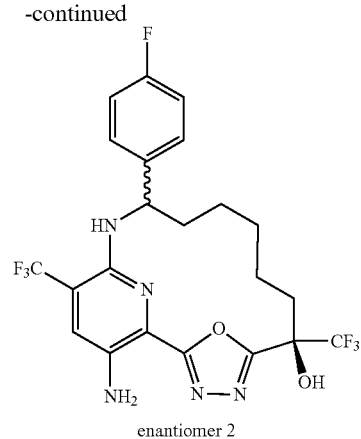
enantiomer 2

Step 1: Methyl 6-[1-(4-fluorophenyl)but-3-enylamino]-3-nitro-5-(trifluoromethyl)pyridine-2-carboxylate

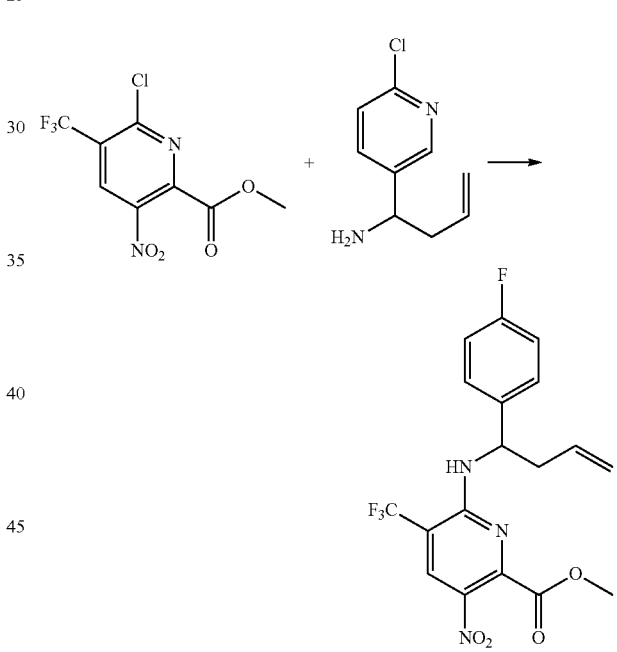

In a flask, 1-(4-fluorophenyl)but-3-en-1-amine (515 mg, 3.117 mmol), DIEA (1.5 mL, 8.612 mmol) and methyl 6-chloro-3-nitro-5-(trifluoromethyl)pyridine-2-carboxylate (800 mg, 2.53 mmol) were combined in acetonitrile (20 mL) and the mixture was heated at 80° C. for 15 minutes. The reaction mixture was cooled to ambient temperature and the solvent removed in vacuo. The residue was diluted with ethyl acetate (50 mL) and washed with brine (2×25 mL), dried over sodium sulfate, filtered and concentrated in vacuo. The residue was purified by silica gel column chromatography (40 gram column) using a gradient from 100% hexanes to 30% ethyl acetate in hexanes to afford as a white solid, methyl 6-[1-(4-fluorophenyl)but-3-enylamino]-3-nitro-5-(trifluoromethyl)pyridine-2-carboxylate (980 mg, 94%). ESI-MS m/z calc. 413.09988, found 414.09 (M+1)+; Retention time: 0.76 minutes (LC Method S).

Step 2: 6-[1-(4-Fluorophenyl)but-3-enylamino]-3-nitro-5-(trifluoromethyl)pyridine-2-carboxylic Acid

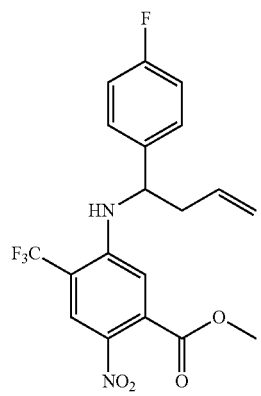

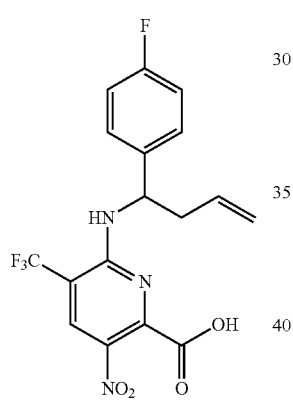

Methyl 6-[1-(4-fluorophenyl)but-3-enylamino]-3-nitro-5-(trifluoromethyl)pyridine-2-carboxylate (980 mg, 2.371 mmol) was combined with lithium hydroxide (555 mg, 23.18 mmol) in methanol (10 mL), THF (10 mL) and water (5 mL) and stirred vigorously at room temperature for 5 minutes. The reaction mixture was then cooled and added 1 M HCl until aqueous layer was acidic. Diluted with ethyl acetate and the resulting layers were separated and the aqueous later was extracted an additional two times with ethyl acetate (15 mL). The combined organics were washed with brine, dried over sodium sulfate and concentrated without further purification to afford as an orange solid, 6-[1-(4-fluorophenyl)but-3-enylamino]-3-nitro-5-(trifluoromethyl)pyridine-2-carboxylic acid (940 mg, 99%). ESI-MS m/z calc. 399.08423, found 400.8 (M+1)$^+$; Retention time: 0.67 minutes (LC Method S).

Step 3: N'-[(2R)-2-benzyloxy-2-(trifluoromethyl)hex-5-enoyl]-6-[1-(4-fluorophenyl)but-3-enylamino]-3-nitro-5-(trifluoromethyl)pyridine-2-carbohydrazide

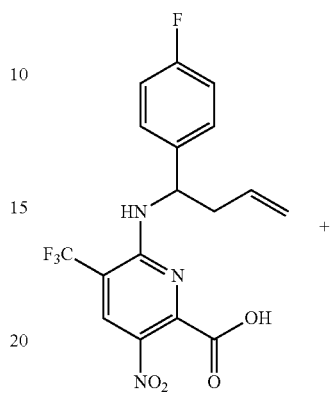

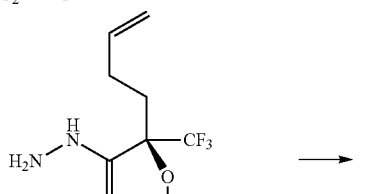

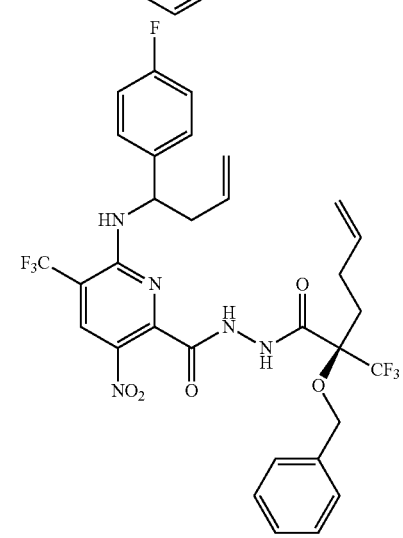

To a solution of 6-[1-(4-fluorophenyl)but-3-enylamino]-3-nitro-5-(trifluoromethyl)pyridine-2-carboxylic acid (412 mg, 1.032 mmol) in DMF (16 mL) was added DIEA (720 μL, 4.134 mmol) and HATU (392 mg, 1.031 mmol). The reaction mixture was stirred at room temperature for 10 minutes then added (2R)-2-benzyloxy-2-(trifluoromethyl)hex-5-enehydrazide (350 mg, 1.158 mmol) in DMF (4 mL) dropwise. Let the reaction stir at room temperature for 30 minutes. Diluted the reaction with brine and water and let stir for 5 minutes. The reaction was extracted with ethyl acetate (3×20 mL). The organic layers were washed with brine (20 mL), dried over sodium sulfate, filtered and evaporated. The crude material was then purified by silica gel chromatography (24 gram column) using a gradient from 100% hexanes to 70% ethyl acetate in hexanes to afford as an off-white solid, N'-[(2R)-2-benzyloxy-2-(trifluoromethyl)hex-5-enoyl]-6-[1-(4-fluorophenyl)but-3-enylamino]-3-nitro-5-(trifluoromethyl)pyridine-2-carbohydrazide (624 mg, 88%). ESI-MS m/z calc. 683.1979, found 684.59 (M+1)⁺; Retention time: 0.83 minutes (LC Method S).

Step 4: 6-[5-[(1R)-1-Benzyloxy-1-(trifluoromethyl)pent-4-enyl]-1,3,4-oxadiazol-2-yl]-N-[1-(4-fluorophenyl)but-3-enyl]-5-nitro-3-(trifluoromethyl)pyridin-2-amine

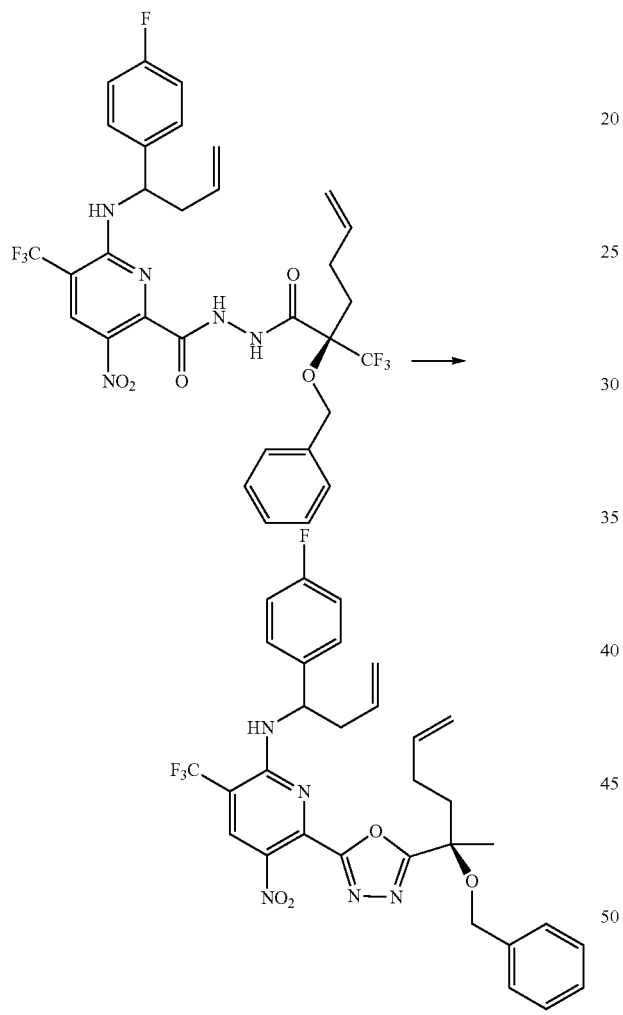

A solution of N-[(2R)-2-benzyloxy-2-(trifluoromethyl)hex-5-enoyl]-6-[1-(4-fluorophenyl)but-3-enylamino]-3-nitro-5-(trifluoromethyl)pyridine-2-carbohydrazide (624 mg, 0.9129 mmol) and DIEA (550 μL, 3.158 mmol) in acetonitrile (13 mL) was heated to 60° C., then p-toluenesulfonyl chloride (198 mg, 1.039 mmol) was added. The resulted mixture was stirred at 60° C. for 15 minutes. The reaction mixture was cooled and quenched with a saturated solution of sodium bicarbonate. Extracted with ethyl acetate (3×40 mL). The organics were separated, dried over sodium sulfate, filtered and evaporated. The crude material was then purified by silica gel chromatography (24 g gold column) using a gradient from 100% hexanes to 40% ethyl acetate in hexanes to afford as a yellow semi-solid, 6-[5-[(1R)-1-benzyloxy-1-(trifluoromethyl)pent-4-enyl]-1,3,4-oxadiazol-2-yl]-N-[1-(4-fluorophenyl)but-3-enyl]-5-nitro-3-(trifluoromethyl)pyridin-2-amine (526 mg, 87%). ESI-MS m/z calc. 665.1873, found 666.5 (M+1)⁺; Retention time: 0.82 minutes (LC Method R).

Step 5: (6R)-6-Benzyloxy-12-(4-fluorophenyl)-17-nitro-6,15-bis(trifluoromethyl)-19-oxa-3,4,13,18-tetrazatricyclo[12.3.1.1²,⁵]nonadeca-1(17),2,4,9,14(18),15-hexaene (E/Z mixture)

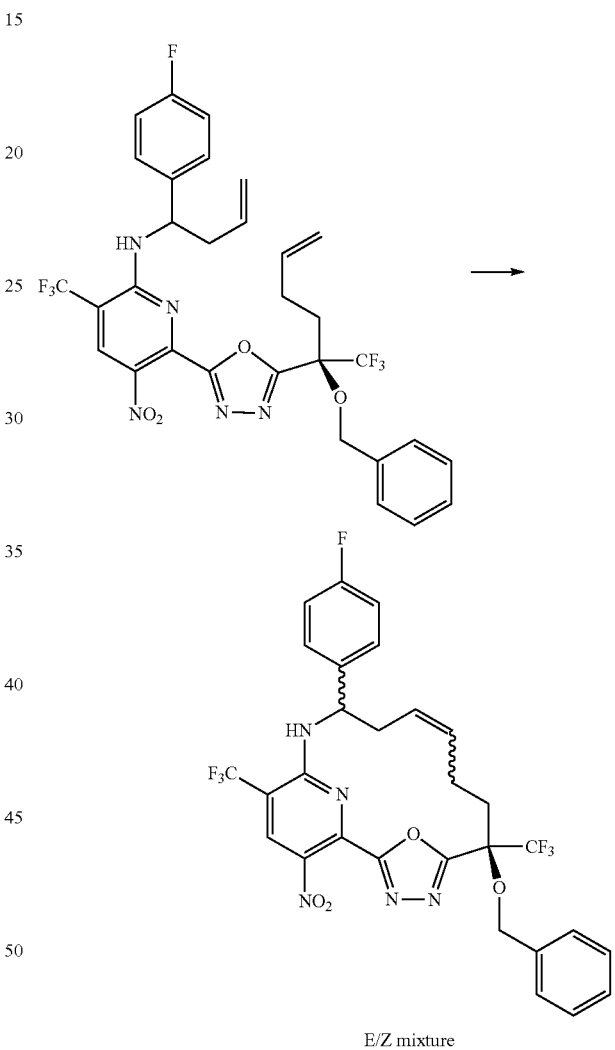

E/Z mixture

A stirring solution of 6-[5-[(1R)-1-benzyloxy-1-(trifluoromethyl)pent-4-enyl]-1,3,4-oxadiazol-2-yl]-N-[1-(4-fluorophenyl)but-3-enyl]-5-nitro-3-(trifluoromethyl)pyridin-2-amine (500 mg, 0.7512 mmol) in 1,2-dichloroethane (224 mL) was degassed by bubbling with nitrogen gas for 20 hours. To the solution at 65° C. was added Zhan catalyst-1B (25 mg, 0.0341 mmol), then the reaction was stirred at this temperature for 30 minutes. Then, an equal amount of Zhan catalyst-1B (25 mg, 0.0341 mmol) was added and stirring continued at 65° C. for 30 minutes. Then, an equal amount of Zhan catalyst-1B (25 mg, 0.0341 mmol) was added and stirring was continued at 65° C. for 2 hours. Once cooled at room temperature, the catalyst was quenched with a few drops of DMSO (about 5-6) and the reaction was concentrated under reduced pressure. The residue was purified by silica gel chromatography on a 40 g column, eluting from 0% to 90% ethyl acetate in heptanes, to afford (6R)-6-benzyloxy-12-(4-fluorophenyl)-17-nitro-6,15-bis(trifluoromethyl)-19-oxa-3,4,13,18-tetrazatricyclo[12.3.1.12,5]nonadeca-1(17),2,4,9,14(18),15-hexaene (E/Z mixture) (235 mg, 41%) as off-white foam. ESI-MS m/z calc. 637.156, found 638.1 (M+1)$^+$; Retention time: 2.59 minutes (LC Method E). Product was difficult to separate from the starting material and was used directly in the ensuing step at ~83% purity.

Step 6: (6R)-17-amino-12-(4-fluorophenyl)-6,15-bis(trifluoromethyl)-19-oxa-3,4,13,18-tetrazatricyclo[12.3.1.12,5]nonadeca-1(18),2,4,14,16-pentaen-6-ol (enantiomer 1) (Compound 182) and (6R)-17-amino-12-(4-fluorophenyl)-6,15-bis(trifluoromethyl)-19-oxa-3,4,13,18-tetrazatricyclo[12.3.1.12,5]nonadeca-1(18),2,4,14,16-pentaen-6-ol (enantiomer 2) (Compound 183)

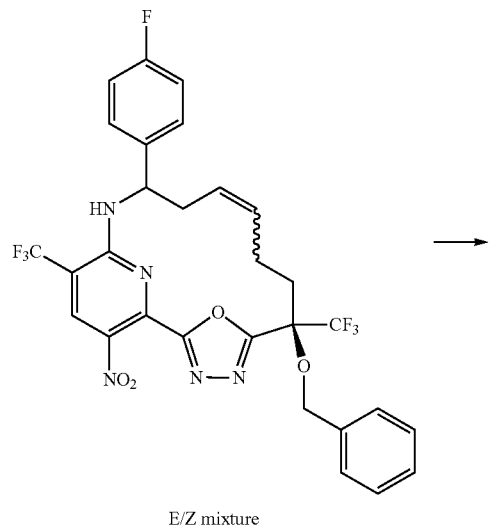

E/Z mixture

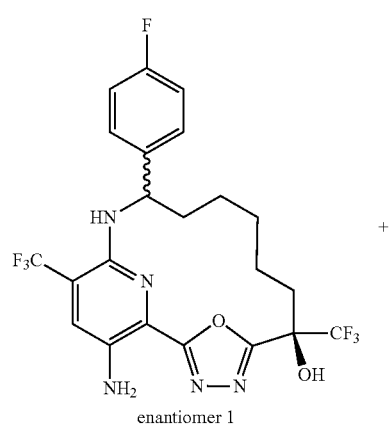

enantiomer 1

+

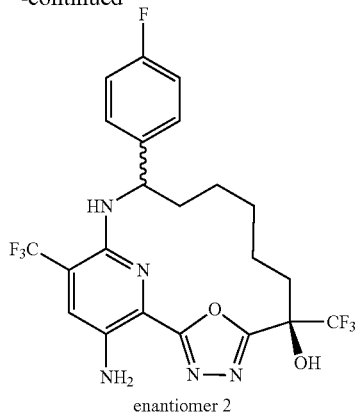

enantiomer 2

(6R)-6-Benzyloxy-12-(4-fluorophenyl)-17-nitro-6,15-bis(trifluoromethyl)-19-oxa-3,4,13,18-tetrazatricyclo[12.3.1.12,5]nonadeca-1(17),2,4,9,14(18),15-hexaene (E/Z mixture) (240 mg, 0.3765 mmol) was dissolved in anhydrous methanol (12 mL). Nitrogen was bubbled into the mixture for 5 minutes and then palladium on carbon (245 mg, 5% w/w, 0.1151 mmol) was added. Hydrogen was then bubbled with a balloon for 5 minutes and the reaction mixture was stirred at room temperature under hydrogen overnight. The hydrogen balloon was replaced by one with nitrogen and then the system was opened to air and the reaction mixture was filtered through a pad of Celite, washing the filter cake with ethyl acetate (3×5 mL) and the filtrate was concentrated by evaporation under reduced pressure. The residue was dry loaded on 10 g of silica gel and purified by chromatography on a 24 g silica gel column eluting with ethyl acetate (0-30%) in heptanes to give a yellow foam solid (135 mg, 97.5% purity by LCMS, 67.3% yield). This product purified by chiral SFC (cellulose 4 column; 10% methanol in CO$_2$; flow=3 mL/min; 100 bar; 40° C.) to separate the two diastereoisomers. The first peak isolated was (6R)-17-amino-12-(4-fluorophenyl)-6,15-bis(trifluoromethyl)-19-oxa-3,4,13,18-tetrazatricyclo[12.3.1.12,5]nonadeca-1(18),2,4,14,16-pentaen-6-ol (enantiomer 1) (54 mg, 27%) as a yellow solid foam. $^1$H NMR (400 MHz, DMSO-d6) δ 7.66 (s, 1H), 7.60 (s, 1H), 7.57-7.50 (m, 2H), 7.27-7.14 (m, 2H), 6.14 (s, 2H), 4.84 (d, J=3.9 Hz, 1H), 4.76-4.61 (m, 1H), 2.92-2.80 (m, 1H), 2.32-2.21 (m, 1H), 2.07-1.97 (m, 1H), 1.80-1.66 (m, 1H), 1.65-1.20 (m, 5H), 1.19-1.06 (m, 1H) ppm. $^{19}$F NMR (377 MHz, DMSO-d6) δ −62.26 (s, 3F), −79.09 (s, 3F), −114.87 to −114.98 (m, 1F) ppm. ESI-MS m/z calc. 519.1505, found 520.1 (M+1)$^+$; Retention time: 3.73 minutes (LC Method C).

The second isolated diastereoisomer was (6R)-17-amino-12-(4-fluorophenyl)-6,15-bis(trifluoromethyl)-19-oxa-3,4,13,18-tetrazatricyclo[12.3.1.12,5]nonadeca-1(18),2,4,14,16-pentaen-6-ol (44 mg, 22%) as yellow solid foam. $^1$H NMR (400 MHz, DMSO-d6) δ 7.66 (s, 1H), 7.58 (s, 1H), 7.56-7.47 (m, 2H), 7.29-7.15 (m, 2H), 6.13 (s, 2H), 4.91 (d, J=4.2 Hz, 1H), 4.82-4.69 (m, 1H), 2.79-2.65 (m, 1H), 2.40-2.25 (m, 1H), 2.15-2.00 (m, 1H), 1.87-1.75 (m, 1H), 1.74-1.62 (m, 1H), 1.54-1.32 (m, 3H), 1.31-1.18 (m, 1H), 1.18-1.05 (m, 1H) ppm. $^{19}$F NMR (377 MHz, DMSO-d6) δ −62.23 (s, 3F), −76.30 (s, 3F), −114.88 to −115.03 (m, 1F) ppm. ESI-MS m/z calc. 519.1505, found 520.1 (M+1)$^+$; Retention time: 3.76 minutes (LC Method C).

Example 102: Preparation of (6R)-17-amino-12-oxazol-2-yl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (Compound 184) and (6R)-17-amino-12-oxazol-2-yl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (Compound 185)
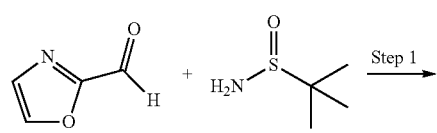
Step 1
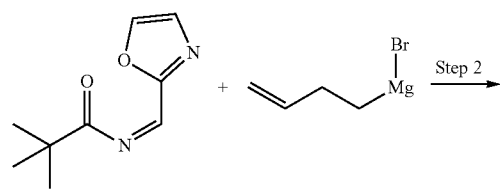
Step 2
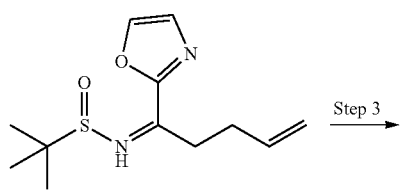
Step 3
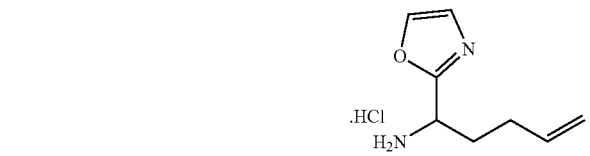
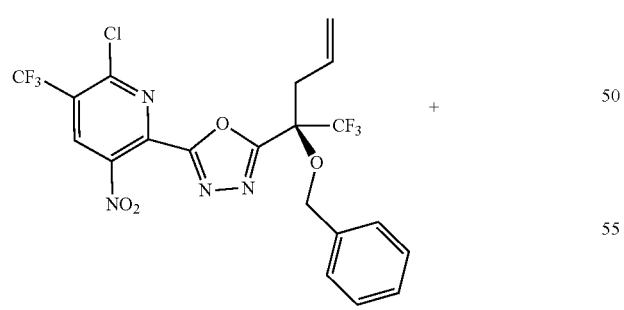
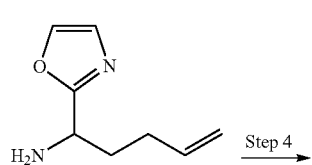
Step 4
-continued
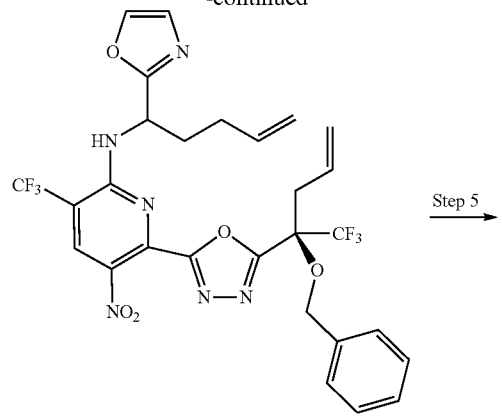
Step 5
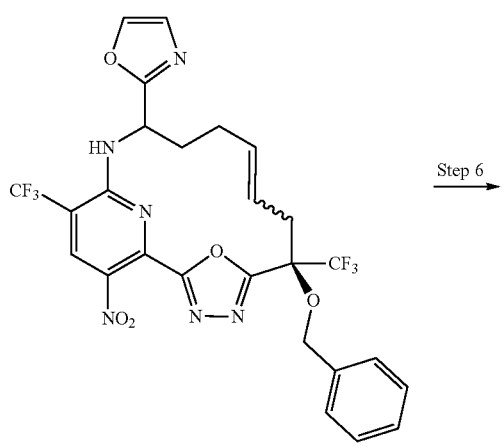
Step 6
E/Z mixture
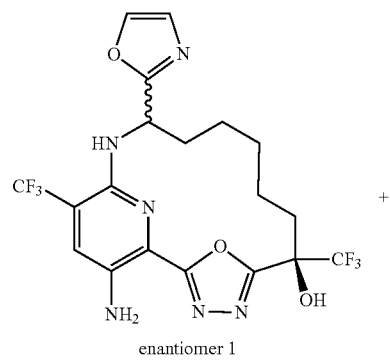
enantiomer 1
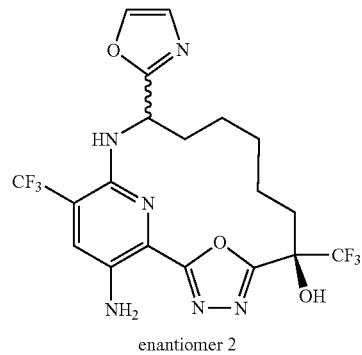
enantiomer 2

Step 1: (Z)-2-Methyl-N-(oxazol-2-ylmethylene)propane-2-sulfinamide

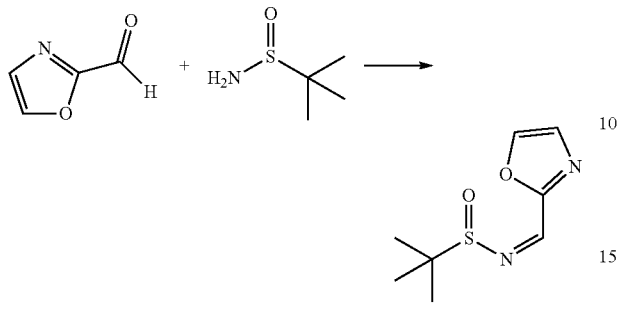

To a solution of oxazole-2-carbaldehyde (10 g, 103.02 mmol) in dichloromethane (250 mL) was added magnesium sulfate (74 g, 614.78 mmol), pyridinium p-toluenesulfonate (1.3 g, 5.1731 mmol) and 2-methylpropane-2-sulfinamide (16.5 g, 136.14 mmol) and the reaction was stirred overnight at room temperature. The reaction mixture was filtered through diatomaceous earth and washed with dichloromethane (150 mL). The solvent was removed under reduced pressure. The crude mixture was purified by silica gel column chromatography (300 g column, ethyl acetate in dichloromethane 0% to 30%) to yield as an oil which crystallized on standing to give a light yellow solid, (Z)-2-methyl-N-(oxazol-2-ylmethylene)propane-2-sulfinamide (13.2 g, 64%). $^1$H NMR (400 MHz, CDCl$_3$) δ 8.51 (s, 1H), 7.84 (s, 1H), 7.41 (s, 1H), 1.28 (s, 9H) ppm. ESI-MS m/z calc. 200.0619, found 201.4 (M+1)$^+$; Retention time: 1.46 minutes (LC Method Z).

Step 2: 2-Methyl-N-(1-oxazol-2-ylpent-4-enyl)propane-2-sulfinamide

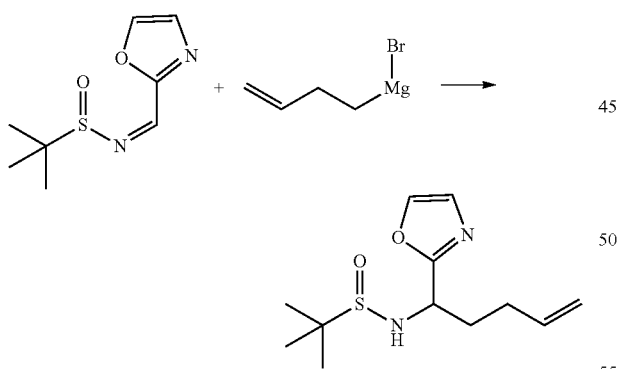

To a cooled solution of (Z)-2-methyl-N-(oxazol-2-ylmethylene)propane-2-sulfinamide (500 mg, 2.4968 mmol) in tetrahydrofuran (10 mL) at −78° C. was added trimethylaluminum (2.5 mL of 2 M, 5 mmol) in heptanes dropwise. The mixture was stirred for 30 minutes at −78° C. and then bromo(but-3-enyl)magnesium (7.5 mL of 0.5 M, 3.75 mmol) in diethyl ether was added dropwise. The reaction was held at −78° C. until complete consumption of starting material was observed by HPLC analysis. The reaction was quenched slowly with saturated ammonium chloride (25 mL), extracted ethyl acetate (2×25 mL), washed with brine (25 mL), dried over sodium sulfate and the solvent was removed under reduced pressure to yield as a crude brownish oil, sulfinamide 2-methyl-N-(1-oxazol-2-ylpent-4-enyl)propane-2-sulfinamide (450 mg, 70%). ESI-MS m/z calc. 256.1245, found 257.4 (M+1)$^+$; Retention time: 1.57 minutes (LC Method Z).

Step 3: 1-Oxazol-2-ylpent-4-en-1-amine (Hydrochloride Salt)

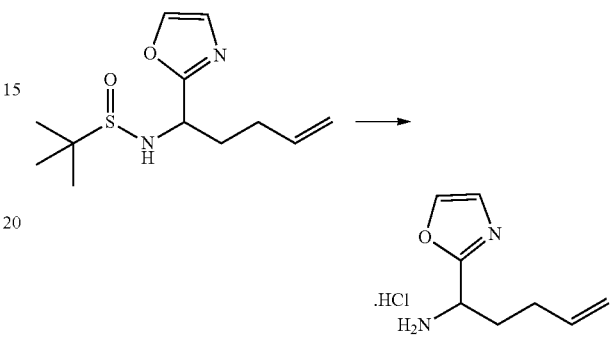

To a solution of 2-methyl-N-(1-oxazol-2-ylpent-4-enyl)propane-2-sulfinamide (1.01 g, 3.9397 mmol) in methanol (10 mL) was added hydrochloric acid (10 mL of 2 M, 20 mmol) in diethyl ether dropwise at room temperature and the mixture was stirred for 1 hour at room temperature. The solvent was removed under vacuum and then the resulting grey solid was suspended in diethyl ether/methanol 9/1 (50 mL), then stirred at 0° C. for 1 hour. The grey suspension was filtered, washed with diethyl ether (25 mL) and dried under vacuum to give as a light yellow powder, 1-oxazol-2-ylpent-4-en-1-amine (hydrochloride salt) (700 mg, 94%). $^1$H NMR (400 MHz, DMSO-d6) δ 8.95 (br s, 3H), 8.24 (d, J=0.7 Hz, 1H), 7.33 (s, 1H), 5.83-5.65 (m, 1H), 5.09-4.91 (m, 2H), 4.52 (br s, 1H), 2.12-1.97 (m, 4H) ppm. ESI-MS m/z calc. 152.095, found 153.1 (M+1)$^+$; Retention time: 2.11 minutes (LC Method BB).

Step 4: 6-[5-[(1R)-1-benzyloxy-1-(trifluoromethyl)but-3-enyl]-1,3,4-oxadiazol-2-yl]-5-nitro-N-(1-oxazol-2-ylpent-4-enyl)-3-(trifluoromethyl)pyridin-2-amine

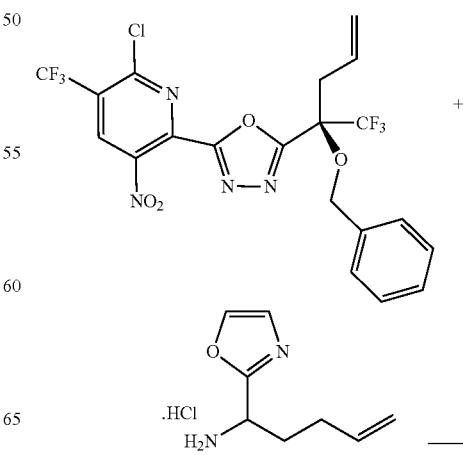

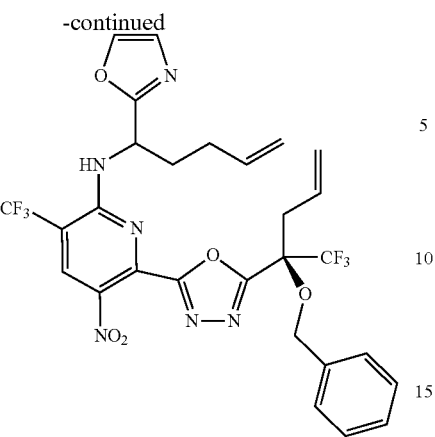

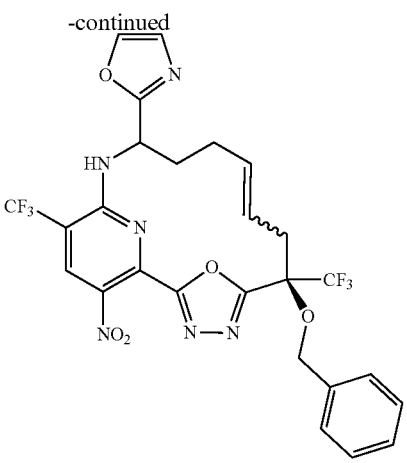

E/Z mixture

To a solution of 2-[(1R)-1-benzyloxy-1-(trifluoromethyl)but-3-enyl]-5-[6-chloro-3-nitro-5-(trifluoromethyl)-2-pyridyl]-1,3,4-oxadiazole (420 mg, 0.8034 mmol) and 1-oxazol-2-ylpent-4-en-1-amine (hydrochloride salt) (170 mg, 0.9011 mmol) in acetonitrile (8.4 mL) was added diisopropylamine (404.32 mg, 560 μL, 3.9957 mmol) at room temperature. The mixture was refluxed for 2 hours. The reaction mixture was cooled to ambient temperature and the solvent was removed in vacuo. The residue was diluted with ethyl acetate (50 mL) and washed with brine (2×50 mL), dried over sodium sulfate, filtered and concentrated in vacuo. The crude product was purified by silica gel column chromatography (40 g column, gradient of heptane in dichloromethane, 0% to 20%). The desired fractions were collected and the solvent was concentrated under reduced pressure to afford as a brownish oil and mixture of two diastereoisomers, 6-[5-[(1R)-1-benzyloxy-1-(trifluoromethyl)but-3-enyl]-1,3,4-oxadiazol-2-yl]-5-nitro-N-(1-oxazol-2-ylpent-4-enyl)-3-(trifluoromethyl)pyridin-2-amine (370 mg, 72%). $^1$H NMR (400 MHz, DMSO-d6) δ 8.63 (s, 1H), 8.58 (dd, J=7.5, 6.2 Hz, 1H), 8.00 (s, 1H), 7.49-7.22 (m, 5H), 7.13 (s, 1H), 5.96-5.69 (m, 2H), 5.63-5.49 (m, 1H), 5.36 (dd, J=17.0, 0.9 Hz, 1H), 5.23 (dd, J=10.3, 1.5 Hz, 1H), 4.95-4.85 (m, 2H), 4.78 (d, J=10.8 Hz, 1H), 4.53 (dd, J=10.6, 8.4 Hz, 1H), 3.32-3.25 (m, 2H), 2.31-2.16 (m, 2H), 2.16-1.97 (m, 2H) ppm. ESI-MS m/z calc. 638.1712, found 639.1 (M+1)$^+$; Retention time: 2.43 minutes (LC Method E).

Step 5: (6R)-6-benzyloxy-17-nitro-12-oxazol-2-yl-6,15-bis(trifluoromethyl)-19-oxa-3,4,13,18-tetrazatricyclo[12.3.1.12,5]nonadeca-1(17),2,4,8,14(18),15-hexaene (E/Z Mixture)

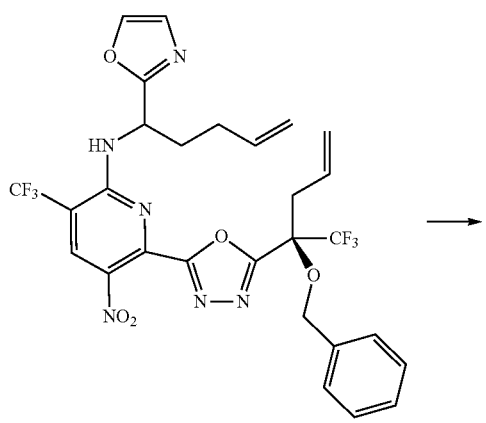

In a 500 mL oven dried round-bottom flask, a degassed solution of 6-[5-[(1R)-1-benzyloxy-1-(trifluoromethyl)but-3-enyl]-1,3,4-oxadiazol-2-yl]-5-nitro-N-(1-oxazol-2-ylpent-4-enyl)-3-(trifluoromethyl)pyridin-2-amine (370 mg, 0.5795 mmol) in dichloroethane (200 mL) was heated to 70° C. under nitrogen atmosphere. Then, Zhan catalyst-1B (52 mg, 0.0709 mmol) was added in two portions over 15 minutes. The resulting mixture was heated to 70° C. and stirred for 4 hours. The mixture was cooled down and concentrated under reduced pressure. The crude product was purified by silica gel column chromatography (12 g column, isocratic run of 2% of ethyl acetate in dichloromethane). The desired fractions were collected and the solvent was concentrated under reduced pressure to afford as a light yellow foam and mixture two diastereoisomers, (6R)-6-benzyloxy-17-nitro-12-oxazol-2-yl-6,15-bis(trifluoromethyl)-19-oxa-3,4,13,18-tetrazatricyclo[12.3.1.12,5]nonadeca-1(17),2,4,8,14(18),15-hexaene (E/Z mixture) (162 mg, 46%). $^1$H NMR (400 MHz, DMSO-d6) δ 8.70-8.56 (m, 2H), 8.22-8.16 (m, 1H), 7.39-7.22 (m, 6H), 6.03-5.78 (m, 1H), 5.75-5.47 (m, 2H), 4.87-4.45 (m, 2H), 3.31-3.11 (m, 1H), 2.94-2.75 (m, 1H), 2.41-2.04 (m, 3H), 1.98-1.74 (m, 1H) ppm. $^{19}$F NMR (377 MHz, DMSO-d6) δ−62.83 (s, 3F), −62.92 (s, 3F), −73.60 (s, 3F), −73.70 (s, 3F) ppm. ESI-MS m/z calc. 610.1399, found 611.1 (M+1)$^+$; Retention time: 2.52 minutes (LC Method E).

Step 6: (6R)-17-amino-12-oxazol-2-yl-6,15-bis(trifluoromethyl)-19-oxa-3,4,13,18-tetrazatricyclo[12.3.1.12,5]nonadeca-1(18),2,4,14,16-pentaen-6-ol (enantiomer 1) (Compound 184) and (6R)-17-amino-12-oxazol-2-yl-6,15-bis(trifluoromethyl)-19-oxa-3,4,13,18-tetrazatricyclo[12.3.1.12,5]nonadeca-1(18),2,4,14,16-pentaen-6-ol (enantiomer 2) (Compound 185)

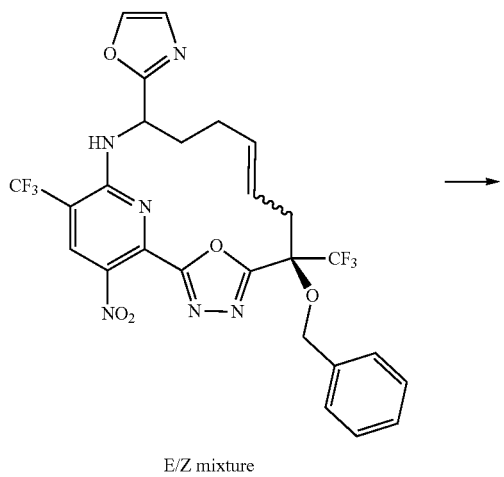

E/Z mixture (6R)-6-benzyloxy-17-nitro-12-oxazol-2-yl-6,15-bis(trifluoromethyl)-19-oxa-3,4,13,18-tetrazatricyclo[12.3.1.12,5]nonadeca-1(17),2,4,8,14(18),15-hexaene (E/Z mixture) (160 mg, 0.2621 mmol) was dissolved in methanol (10 mL). The mixture was bubbled with nitrogen for 5 min and then palladium on carbon (170 mg, 5 w/w, 0.0799 mmol) was added. The resulting mixture was bubbled with a balloon of hydrogen for 5 min and then the mixture was stirred at room temperature under hydrogen atmosphere overnight. The mixture was filtered through a pad of Celite and washed with methanol (25 mL) and concentrated under reduced pressure. The resulting mixture was purified by reverse phase $C_{18}$ chromatography (15.5 g column, gradient from 5% to 95% of acetonitrile (0.1% formic acid) in water (0.1% formic acid))) to provide a mixture of two diastereoisomers. These diastereomers were separated by chiral SFC on a Cellulose 1 column (21.2 mm×250 mm, 5 μm particle size) at 40° C., eluting with 10% methanol in $CO_2$ at 4 mL/min flow which afforded two individual enantiomers:

The first enantiomer to elute was isolated as a yellow oil, (6R)-17-amino-12-oxazol-2-yl-6,15-bis(trifluoromethyl)-19-oxa-3,4,13,18-tetrazatricyclo[12.3.1.12,5]nonadeca-1(18),2,4,14,16-pentaen-6-ol (enantiomer 1) (17 mg, 13%). $^1$H NMR (400 MHz, DMSO-d6) δ 8.13 (d, J=0.7 Hz, 1H), 7.69 (s, 1H), 7.58 (s, 1H), 7.25 (d, J=1.0 Hz, 1H), 6.16 (s, 2H), 5.99 (d, J=4.9 Hz, 1H), 5.08-4.97 (m, 1H), 2.38-2.26 (m, 1H), 2.16-2.04 (m, 1H), 1.87-1.68 (m, 2H), 1.68-1.34 (m, 6H) ppm. $^{19}$F NMR (377 MHz, DMSO-d6) δ −62.35 (s, 3F), −76.50 (s, 3F) ppm. ESI-MS m/z calc. 492.1345, found 492.9 (M+1)$^+$; Retention time: 3.1 minutes (LC Method C).

The second enantiomer to elute was isolated as a yellow oil, (6R)-17-amino-12-oxazol-2-yl-6,15-bis(trifluoromethyl)-19-oxa-3,4,13,18-tetrazatricyclo[12.3.1.12,5]nonadeca-1(18),2,4,14,16-pentaen-6-ol (enantiomer 2) (18 mg, 14%). $^1$H NMR (400 MHz, DMSO-d6) δ 8.14 (s, 1H), 7.69 (s, 1H), 7.59 (s, 1H), 7.26 (s, 1H), 6.17 (s, 2H), 5.98 (d, J=4.2 Hz, 1H), 4.99-4.88 (m, 1H), 2.72-2.59 (m, 1H), 2.34-2.19 (m, 1H), 2.13-2.00 (m, 1H), 1.77-1.67 (m, 1H), 1.66-1.45 (m, 6H) ppm. $^{19}$F NMR (377 MHz, DMSO-d6) δ −62.39 (s, 3F), −79.05 (s, 3F) ppm. ESI-MS m/z calc. 492.1345, found 492.9 (M+1)$^+$; Retention time: 3.08 minutes (LC Method C).

Example 103: Preparation of (6R)-17-amino-11,11-dimethyl-6,15-bis(trifluoromethyl)-10,19-dioxa-3,4,13,18-tetrazatricyclo[12.3.1.12,5]nonadeca-1(17),2,4,14(18),15-pentaen-6-ol (Compound 186)

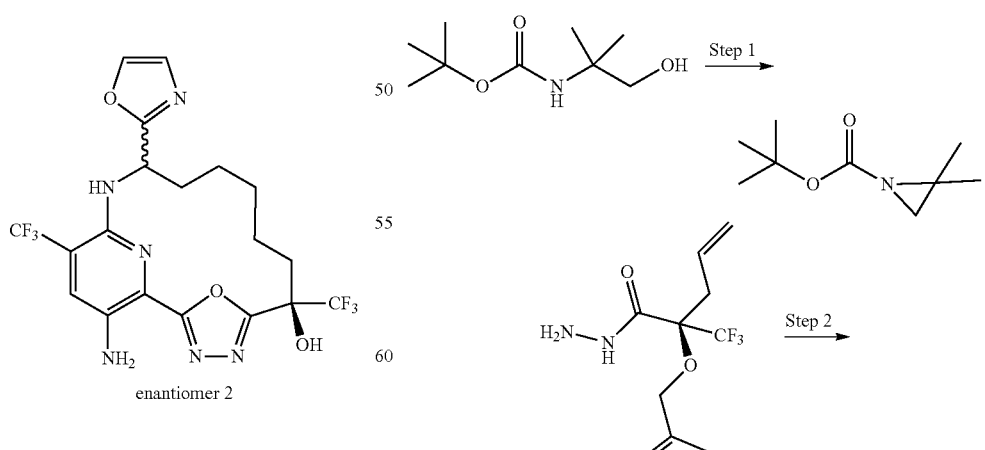

849
-continued
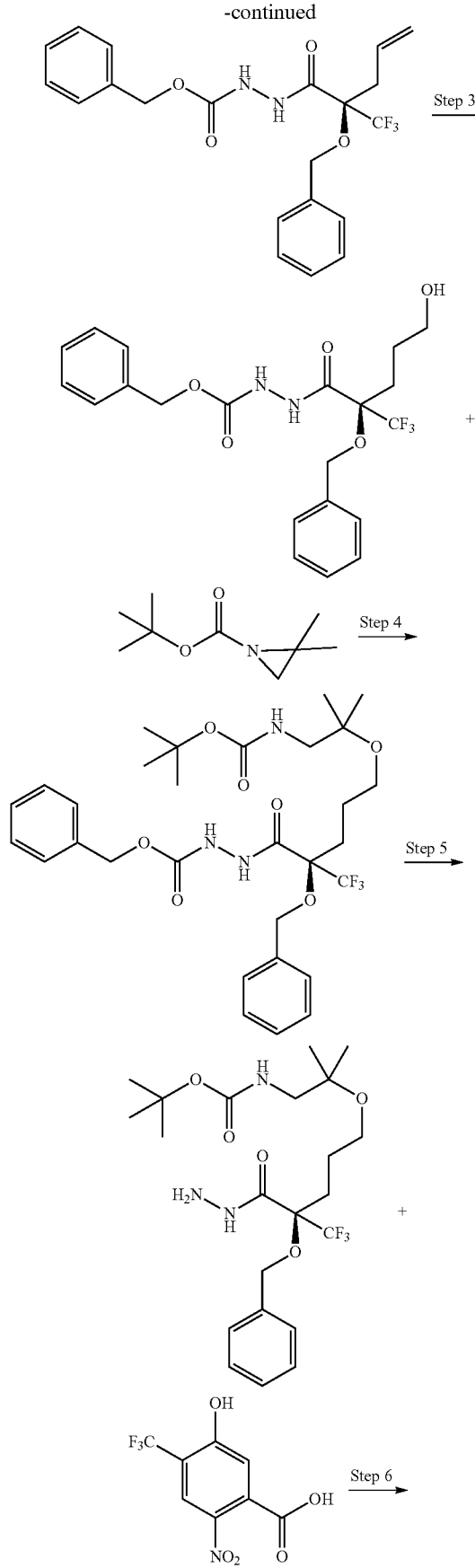
850
-continued
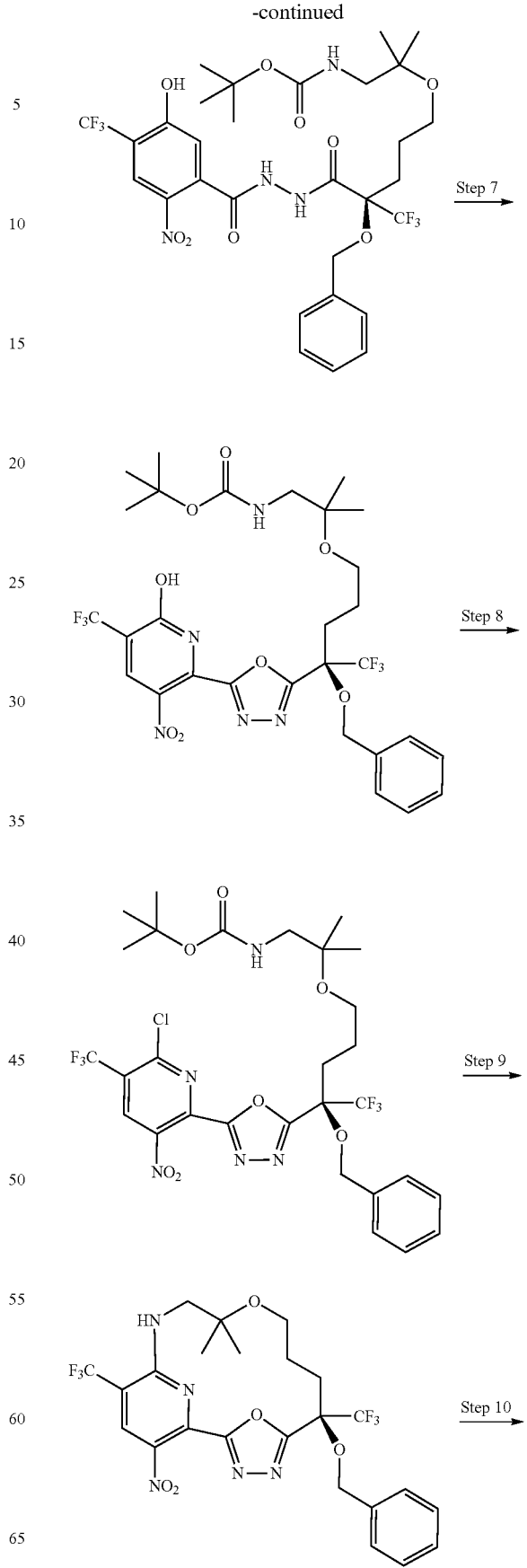

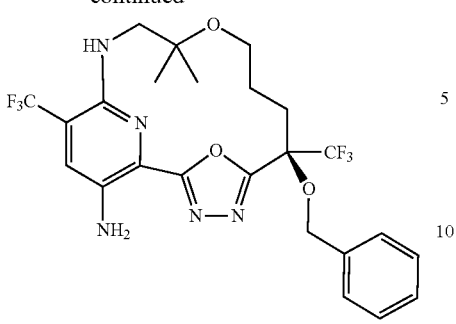

Step 1: tert-Butyl 2,2-dimethylaziridine-1-carboxylate

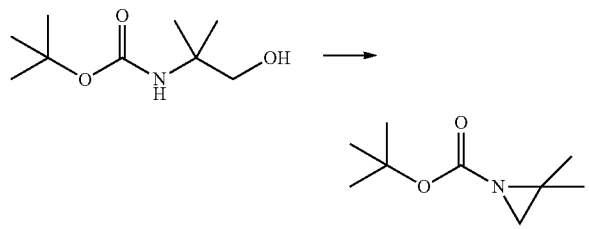

Into a solution of tert-butyl N-(2-hydroxy-1,1-dimethylethyl)carbamate (5.010 g, 25.943 mmol) in diethyl ether (100 mL) was added p-TsCl (5.959 g, 31.257 mmol). The solution was cooled in an ice bath. Potassium hydroxide (17.302 g, 262.13 mmol) was added to the reaction mixture in several batches. The reaction was then heated to reflux and stirred for 1 hour. A large amount of white precipitate was formed. The reaction mixture was cooled to room temperature and diluted with diethyl ether (100 mL). The mixture was poured into ice water (100 mL). Two layers were separated and the organic layer was washed with brine (100 mL), dried over anhydrous sodium sulfate, filtered and concentrated (35° C. bath temperature, 110 Torr vacuum) to furnish as a clear liquid, tert-butyl 2,2-dimethylaziridine-1-carboxylate (4.49 g, 94%). $^1$H NMR (500 MHz, Chloroform-d) δ 2.03 (s, 2H), 1.45 (s, 9H), 1.27 (s, 6H) ppm.

Step 2: Benzyl N-[[(2R)-2-benzyloxy-2-(trifluoromethyl)pent-4-enoyl]amino]carbamate

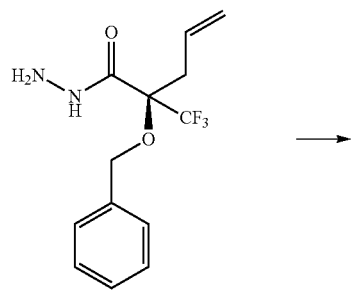

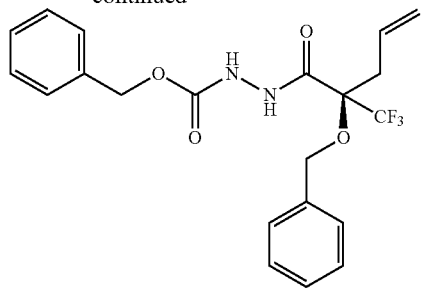

To a solution of (2R)-2-benzyloxy-2-(trifluoromethyl)pent-4-enehydrazide (4.914 g, 17.047 mmol) and NaHCO$_3$ (4.31 g, 51.305 mmol) in dioxane (50 mL) and water (50 mL) was added benzyl chloroformate (8.7235 g, 7.3 mL, 51.136 mmol) at 0° C. The reaction mixture was stirred in an ice bath for 1 hour and at room temperature overnight. Two layers were separated, and the aqueous layer was extracted with ethyl acetate (3×50 mL). The combined organic layers were concentrated under vacuum. The residue was purified by silica gel chromatography using a gradient from 0% to 60% ether in hexane to furnish as a clear gel, benzyl N-[[(2R)-2-benzyloxy-2-(trifluoromethyl)pent-4-enoyl]amino]carbamate (9.2 g, 100%). ESI-MS m/z calc. 422.1453, found 423.1 (M+1)$^+$; Retention time: 3.43 minutes (LC Method G).

Step 3: Benzyl N-[[(2R)-2-benzyloxy-5-hydroxy-2-(trifluoromethyl)pentanoyl]amino]carbamate

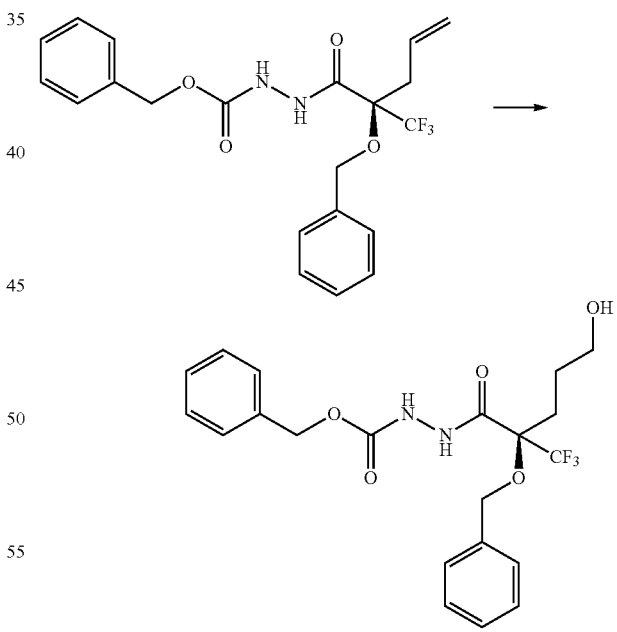

Into a solution of benzyl N-[[(2R)-2-benzyloxy-2-(trifluoromethyl)pent-4-enoyl]amino]carbamate (9.2 g, 16.989 mmol) in anhydrous THF (100 mL) was added 9-borabicyclo[3.3.1]nonane (170 mL of 0.5 M in THF, 85 mmol) dropwise at room temperature. The reaction was stirred at room temperature for 1 hour. The reaction was cooled to 0° C. An aqueous solution of 1 N NaOH (85 mL, 85 mmol) and H$_2$O$_2$ (6.66 g, 20 mL of 30% w/w, 58.739 mmol) was added to the reaction mixture. The reaction was stirred at room temperature for 0.5 h. The reaction was diluted with ethyl acetate (200 mL) and washed with saturated sodium thiosulfate (50 mL) and brine (50 mL). The organic solution was dried over anhydrous magnesium sulfate, filtered and concentrated under vacuum. The residue was purified by silica gel chromatography using a gradient from 0% to 60% ethyl acetate in hexane to furnish as a white foam, benzyl N-[[(2R)-2-benzyloxy-5-hydroxy-2-(trifluoromethyl)pentanoyl]amino]carbamate (6.405 g, 86%). ESI-MS m/z calc. 440.1559, found 441.2 (M+1)+; Retention time: 2.95 minutes (LC Method G).

Step 4: tert-Butyl N-[2-[(4R)-4-benzyloxy-4-(benzyloxycarbonylaminocarbamoyl)-5,5,5-trifluoropentoxy]-2-methyl-propyl]carbamate

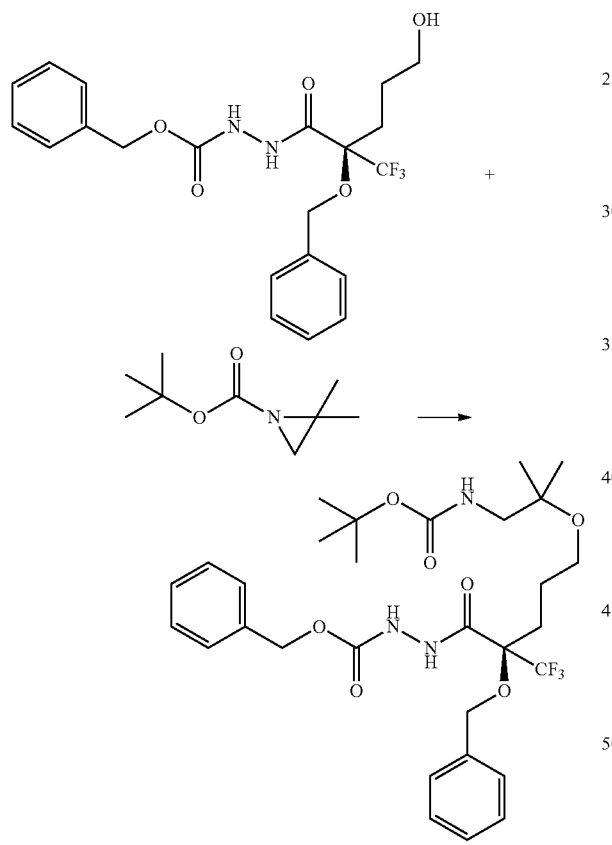

A reaction vial was charged with benzyl N-[[(2R)-2-benzyloxy-5-hydroxy-2-(trifluoromethyl)pentanoyl]amino]carbamate (6.405 g, 14.543 mmol) and tert-butyl 2,2-dimethylaziridine-1-carboxylate (21.2 g, 123.81 mmol). The reaction was heated to 80° C. and stirred for 14 hours. The reaction was cooled to room temperature and directly purified by silica gel chromatography using 0% to 40% ethyl acetate in hexanes giving as a clear liquid tert-butyl N-[2-[(4R)-4-benzyloxy-4-(benzyloxycarbonylaminocarbamoyl)-5,5,5-trifluoro-pentoxy]-2-methyl-propyl]carbamate (2.868 g, 32%). ESI-MS m/z calc. 611.2818, found 612.4 (M+1)+; Retention time: 3.72 minutes (LC Method G).

Step 5: tert-Butyl N-[2-[(4R)-4-benzyloxy-5,5,5-trifluoro-4-(hydrazinecarbonyl)pentoxy]-2-methyl-propyl]carbamate

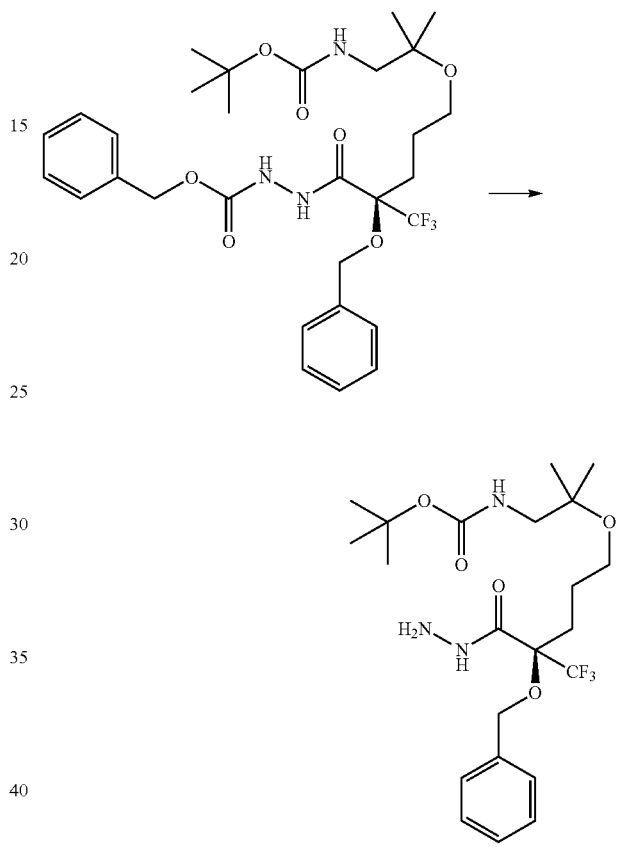

Into a solution of tert-butyl N-[2-[(4R)-4-benzyloxy-4-(benzyloxycarbonylaminocarbamoyl)-5,5,5-trifluoro-pentoxy]-2-methyl-propyl]carbamate (1.912 g, 3.126 mmol) in ethyl acetate (100 mL) was added 10% Pd/C (630 mg, 10% w/w, 0.592 mmol). The reaction was stirred under 1 atmosphere of hydrogen (hydrogen balloon) for 3 hours. The catalyst was removed by filtration. The filtrate was concentrated under vacuum and the residue was purified by silica gel chromatography using a gradient from 0% to 60% ethyl acetate in hexanes giving as a clear gel, tert-butyl N-[2-[(4R)-4-benzyloxy-5,5,5-trifluoro-4-(hydrazinecarbonyl)pentoxy]-2-methyl-propyl]carbamate (1.083 g, 73%). $^1$H NMR (500 MHz, Chloroform-d) δ 7.95 (s, 1H), 7.51-7.31 (m, 5H), 4.81 (s, 1H), 4.75 (d, J=10.3 Hz, 1H), 4.66 (d, J=10.4 Hz, 1H), 3.88 (s, 2H), 3.45-3.37 (m, 1H), 3.37-3.27 (m, 1H), 3.13 (d, J=5.9 Hz, 2H), 2.43-2.15 (m, 2H), 1.65-1.36 (m, 11H), 1.15 (s, 6H) ppm. ESI-MS m/z calc. 477.2451, found 478.2 (M+1)+; Retention time: 3.07 minutes (LC Method G).

Step 6: tert-Butyl N-[2-[(4R)-4-benzyloxy-5,5,5-trifluoro-4-[[[6-hydroxy-3-nitro-5-(trifluoromethyl)pyridine-2-carbonyl]amino]carbamoyl]pentoxy]-2-methyl-propyl]carbamate

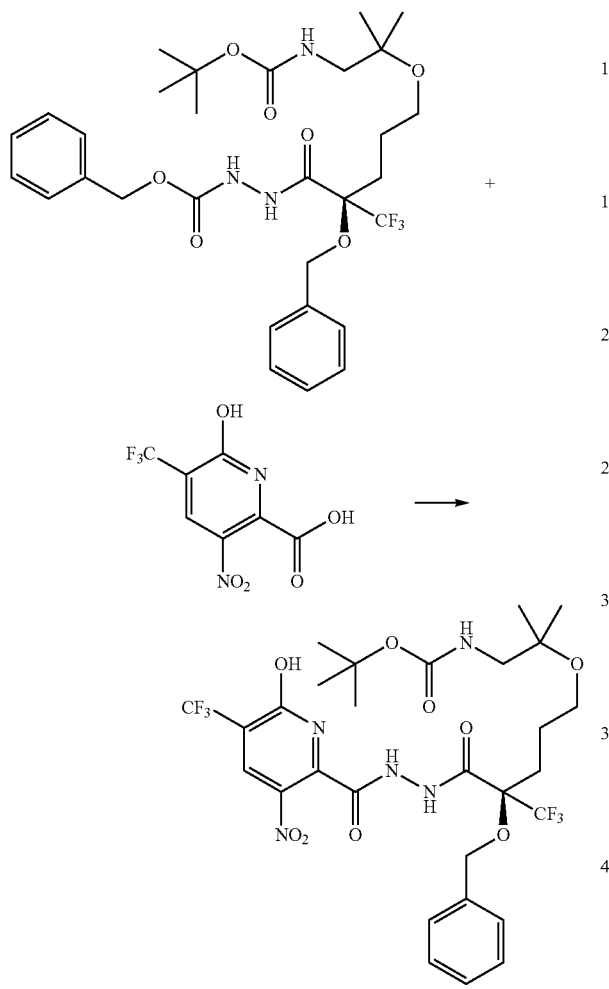

To a solution of tert-butyl N-[2-[(4R)-4-benzyloxy-5,5,5-trifluoro-4-(hydrazinecarbonyl)pentoxy]-2-methyl-propyl]carbamate (147.5 mg, 0.3089 mmol) and 6-hydroxy-3-nitro-5-(trifluoromethyl)pyridine-2-carboxylic acid (92 mg, 0.3649 mmol) in anhydrous DMF (4.5 mL) was added TEA (312.18 mg, 0.43 mL, 3.0851 mmol) followed by propylphosphonic anhydride solution (197.76 mg, 0.37 mL of 50 w/w, 0.3108 mmol) in ethyl acetate. The reaction was stirred at room temperature for 2 h. The reaction was diluted with ethyl acetate (50 mL) and washed with 1 N HCl (10 mL), brine (3×20 mL), dried over anhydrous sodium sulfate and concentrated under vacuum. The residue was purified by silica gel chromatography using a gradient from 0% to 50% acetone in hexane to furnish as a yellow gel, tert-butyl N-[2-[(4R)-4-benzyloxy-5,5,5-trifluoro-4-[[[6-hydroxy-3-nitro-5-(trifluoromethyl)pyridine-2-carbonyl]amino]carbamoyl]pentoxy]-2-methyl-propyl]carbamate (201 mg, 91%). ESI-MS m/z calc. 711.2339, found 712.6 (M+1)$^+$; Retention time: 3.56 minutes (LC Method G).

Step 7: tert-Butyl N-[2-[(4R)-4-benzyloxy-5,5,5-trifluoro-4-[5-[6-hydroxy-3-nitro-5-(trifluoromethyl)-2-pyridyl]-1,3,4-oxadiazol-2-yl]pentoxy]-2-methyl-propyl]carbamate

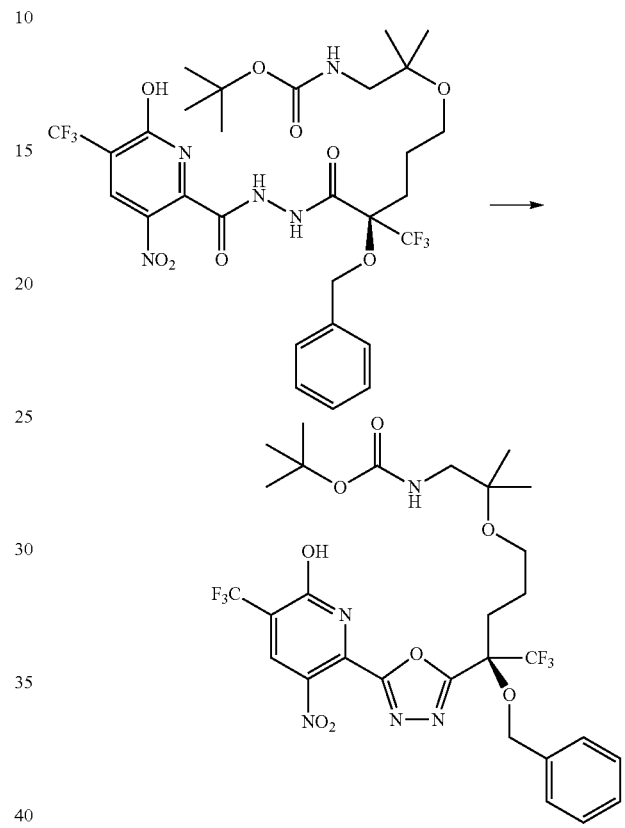

Into a solution of tert-butyl N-[2-[(4R)-4-benzyloxy-5,5,5-trifluoro-4-[[[6-hydroxy-3-nitro-5-(trifluoromethyl)pyridine-2-carbonyl]amino]carbamoyl]pentoxy]-2-methyl-propyl]carbamate (201 mg, 0.2825 mmol) and DIEA (363.58 mg, 0.49 mL, 2.8132 mmol) in acetonitrile (4 mL) was added p-TsCl (59 mg, 0.3095 mmol). The reaction was stirred at room temperature for 2 h. The reaction was diluted with ethyl acetate (50 mL) and washed with saturated aqueous ammonium chloride (2×10 mL) and brine (10 mL). The organic solution was dried over anhydrous sodium sulfate, filtered and concentrated under vacuum. The residue was purified by silica gel chromatography using a gradient from 0% to 100% ethyl acetate in hexane to furnish as a brown solid, tert-butyl N-[2-[(4R)-4-benzyloxy-5,5,5-trifluoro-4-[5-[6-hydroxy-3-nitro-5-(trifluoromethyl)-2-pyridyl]-1,3,4-oxadiazol-2-yl]pentoxy]-2-methyl-propyl]carbamate (86.6 mg, 41%). ESI-MS m/z calc. 693.2233, found 694.4 (M+1)$^+$; Retention time: 3.84 minutes (LC Method G).

Step 8: tert-Butyl N-[2-[(4R)-4-benzyloxy-4-[5-[6-chloro-3-nitro-5-(trifluoromethyl)-2-pyridyl]-1,3,4-oxadiazol-2-yl]-5,5,5-trifluoro-pentoxy]-2-methyl-propyl]carbamate Step 9: (6R)-6-Benzyloxy-11,11-dimethyl-17-nitro-6,15-bis(trifluoromethyl)-10,19-dioxa-3,4,13,18-tetrazatricyclo[12.3.1.12,5]nonadeca-1(17),2,4,14(18),15-pentaene

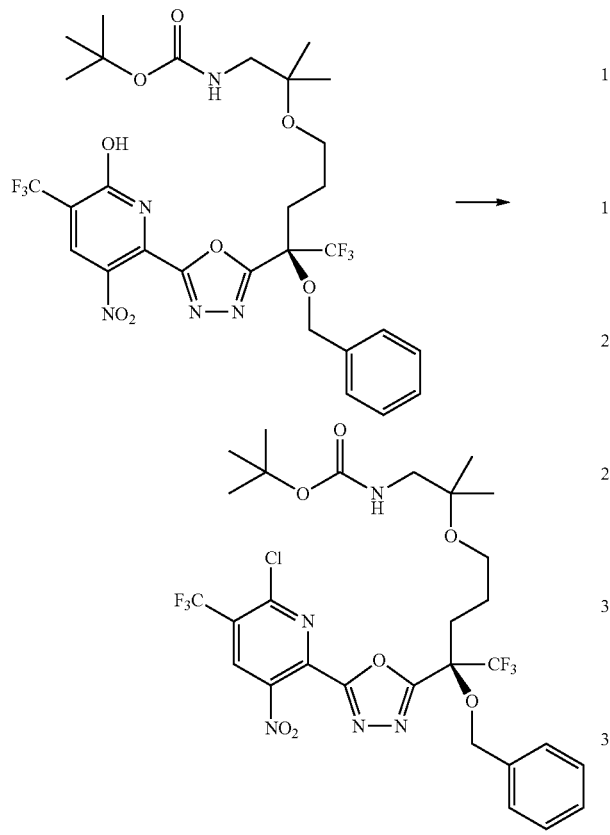
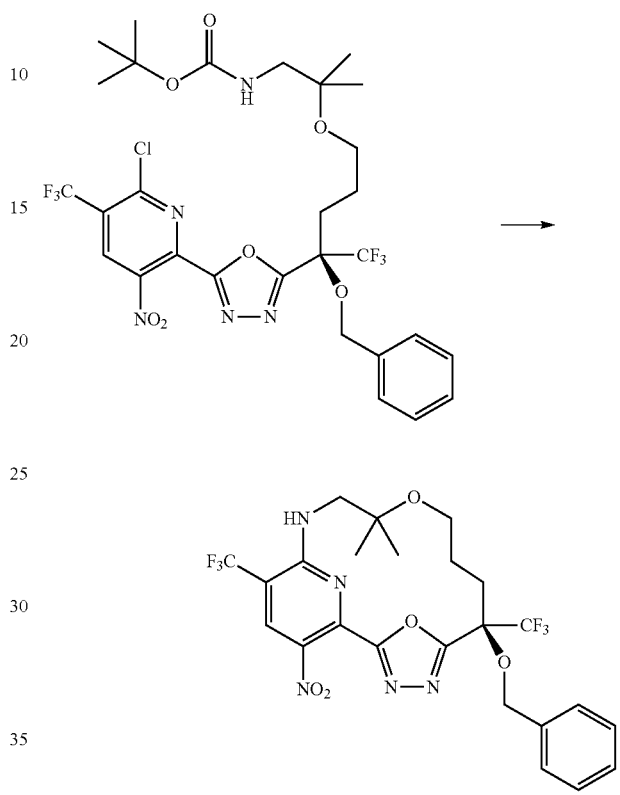

Into a solution of tert-butyl N-[2-[(4R)-4-benzyloxy-5,5,5-trifluoro-4-[5-[6-hydroxy-3-nitro-5-(trifluoromethyl)-2-pyridyl]-1,3,4-oxadiazol-2-yl]pentoxy]-2-methyl-propyl]carbamate (86.6 mg, 0.1149 mmol) in anhydrous THF (1 mL) was added triphenylphosphine (122 mg, 0.4651 mmol) followed by 2,2,2-trichloroacetonitrile (33.120 mg, 0.023 mL, 0.2294 mmol) dropwise at 0° C. The reaction was stirred at room temperature for 2 h. The reaction was diluted with ethyl acetate (50 mL) and washed with brine (15 mL). The organic layer was dried over anhydrous sodium sulfate and concentrated under vacuum. The residue was purified by silica gel chromatography using a gradient from 0% to 30% ethyl acetate in hexane to furnish as a yellow gel tert-Butyl N-[2-[(4R)-4-benzyloxy-4-[5-[6-chloro-3-nitro-5-(trifluoromethyl)-2-pyridyl]-1,3,4-oxadiazol-2-yl]-5,5,5-trifluoro-pentoxy]-2-methyl-propyl]carbamate (21.3 mg, 26%). $^1$H NMR (500 MHz, Chloroform-d) δ 8.70 (s, 1H), 7.46-7.39 (m, 2H), 7.39-7.33 (m, 2H), 7.33-7.28 (m, 1H), 4.82 (d, J=10.7 Hz, 1H), 4.78 (s, 1H), 4.63 (d, J=10.6 Hz, 1H), 3.42-3.30 (m, 2H), 3.11 (d, J=6.0 Hz, 2H), 2.55-2.38 (m, 2H), 1.87-1.77 (m, 1H), 1.77-1.65 (m, 1H), 1.42 (s, 9H), 1.13 (s, 6H) ppm. ESI-MS m/z calc. 711.1894, found 712.6 (M+1)$^+$; Retention time: 4.12 minutes (LC Method G).

Into a solution of tert-Butyl N-[2-[(4R)-4-benzyloxy-4-[5-[6-chloro-3-nitro-5-(trifluoromethyl)-2-pyridyl]-1,3,4-oxadiazol-2-yl]-5,5,5-trifluoro-pentoxy]-2-methyl-propyl] carbamate (21.3 mg, 0.0299 mmol) in anhydrous DCM (1 mL) was added TFA (740 mg, 0.5 mL, 6.4899 mmol) at room temperature. The reaction was stirred at room temperature for 1 hour. The reaction was diluted with DCM (30 mL) and washed with saturated aqueous sodium bicarbonate (20 mL) and brine (20 mL). The organic phase was dried over anhydrous sodium sulfate. The drying reagent was filtered off. DIEA (14.840 mg, 0.02 mL, 0.1148 mmol) was added to the DCM solution and the reaction was stirred at room temperature for 1 hour. All of the volatiles were removed under vacuum to furnish as a yellow gel, (6R)-6-benzyloxy-11,11-dimethyl-17-nitro-6,15-bis(trifluoromethyl)-10,19-dioxa-3,4,13,18-tetrazatricyclo[12.3.1.12,5] nonadeca-1(17),2,4,14(18),15-pentaene (18 mg, 99%). ESI-MS m/z calc. 575.1603, found 576.4 (M+1)$^+$; Retention time: 3.8 minutes. The crude product was used in the next step reaction without purification (LC Method G).

Step 10: (6R)-17-Amino-11,11-dimethyl-6,15-bis(trifluoromethyl)-10,19-dioxa-3,4,13,18-tetrazatricyclo[12.3.1.1²,⁵]nonadeca-1(17),2,4,14(18),15-pentaen-6-ol (Compound 186)

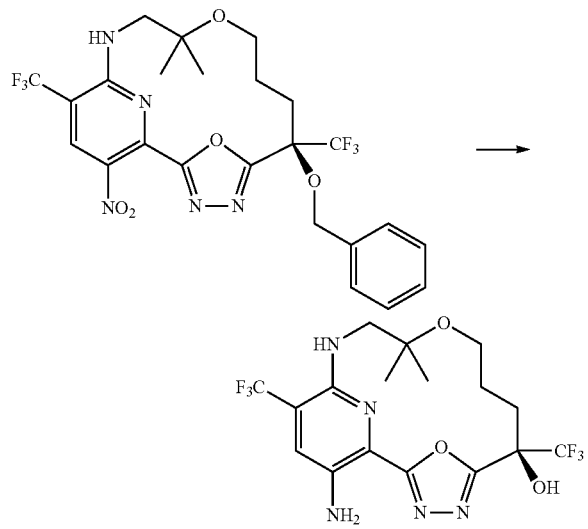

Into a solution of (6R)-6-benzyloxy-11,11-dimethyl-17-nitro-6,15-bis(trifluoromethyl)-10,19-dioxa-3,4,13,18-tetrazatricyclo[12.3.1.1²,⁵]nonadeca-1(17),2,4,14(18),15-pentaene (18 mg, 0.0297 mmol) in ethanol (5 mL) was added 10% Pd/C (20 mg, 10% w/w, 0.0188 mmol). The reaction was stirred under 1 atmosphere of hydrogen gas for 3 days. The catalyst was removed by filtration through a pad of Celite and the filtrate was evaporated. The residue was directly purified by silica gel chromatography using a gradient from 0% to 100% ethyl acetate in hexane to furnish as a yellow solid, (6R)-17-Amino-11,11-dimethyl-6,15-bis(trifluoromethyl)-10,19-dioxa-3,4,13,18-tetrazatricyclo[12.3.1.1²,⁵]nonadeca-1(17),2,4,14(18),15-pentaen-6-ol (7.3 mg, 53%). $^1$H NMR (500 MHz, Chloroform-d) δ 7.29 (s, 1H), 4.80 (s, 1H), 4.09 (s, 1H), 3.75 (q, J=7.6, 7.6, 7.5 Hz, 1H), 3.69-3.55 (m, 2H), 3.18 (s, 1H), 2.53-2.36 (m, 1H), 2.36-2.17 (m, 1H), 1.96-1.77 (m, 1H), 1.45-1.35 (m, 1H), 1.25 (s, 3H), 1.18 (s, 3H) ppm. Two exchangeable protons not observed in NMR. ESI-MS m/z calc. 455.1392, found 456.4 (M+1)$^+$; Retention time: 1.79 minutes (LC Method H).

Example 104: Preparation of (6R,8R)-17-amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,8-diol (Compound 187), (6R,8S)-17-amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,8-diol (Compound 188), (6R)-17-amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,9-diol (enantiomer 1) (Compound 189) and (6R)-17-amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,9-diol (enantiomer 2) (Compound 190)

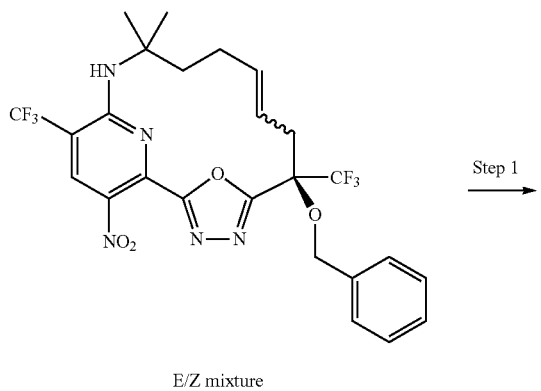

E/Z mixture

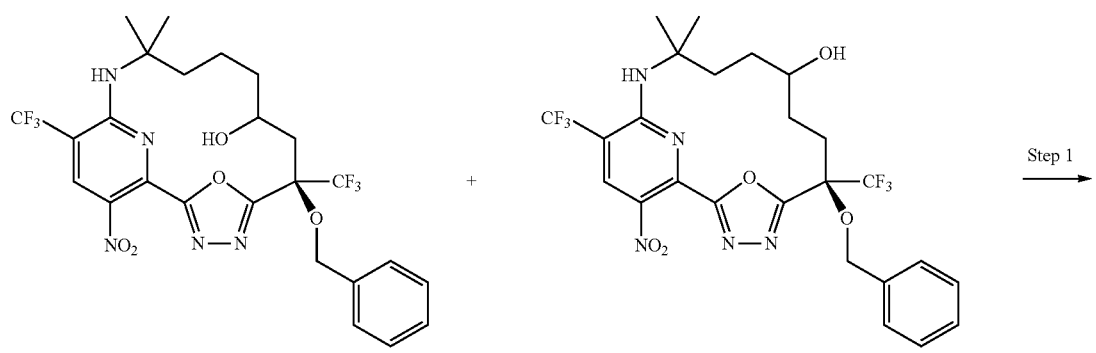

mixture of regioisomeric diastereomers

861    -continued    862
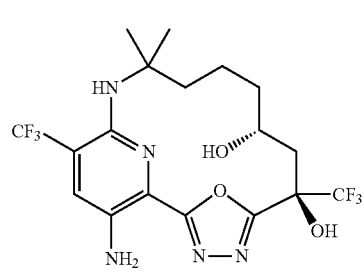 + 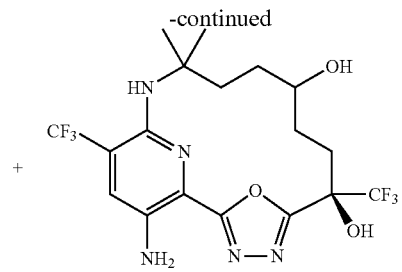 + 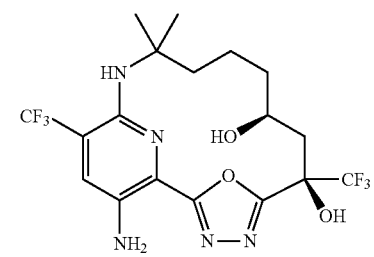
mixture of diastereomers
↓ Step 3
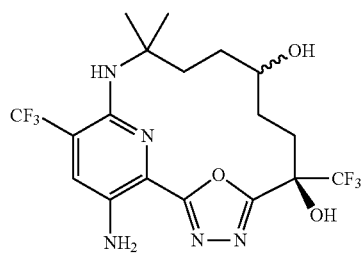 + 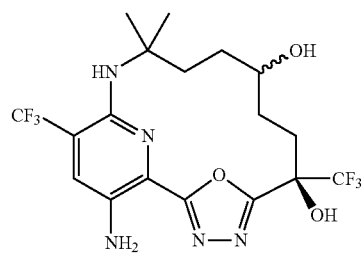
enantiomer 1    enantiomer 2
Step 1: (6R)-6-Benzyloxy-12,12-dimethyl-17-nitro-6,15-bis(trifluoromethyl)-19-oxa-3,4,13,18-tetrazatricyclo[12.3.1.12,5]nonadeca-1(18),2,4,14,16-pentaen-8-ol and (6R)-6-benzyloxy-12,12-dimethyl-17-nitro-6,15-bis(trifluoromethyl)-19-oxa-3,4,13,18-tetrazatricyclo[12.3.1.12,5]nonadeca-1(18),2,4,14,16-pentaen-9-ol (mixture of Regioisomeric Diastereomers)
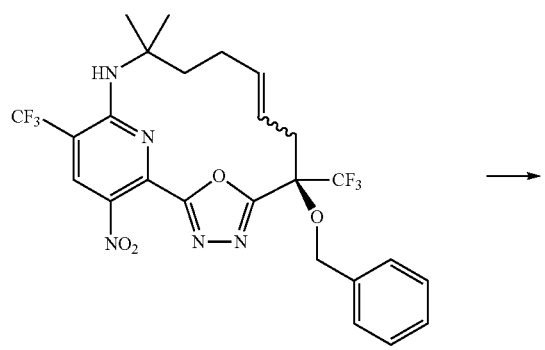
E/Z mixture

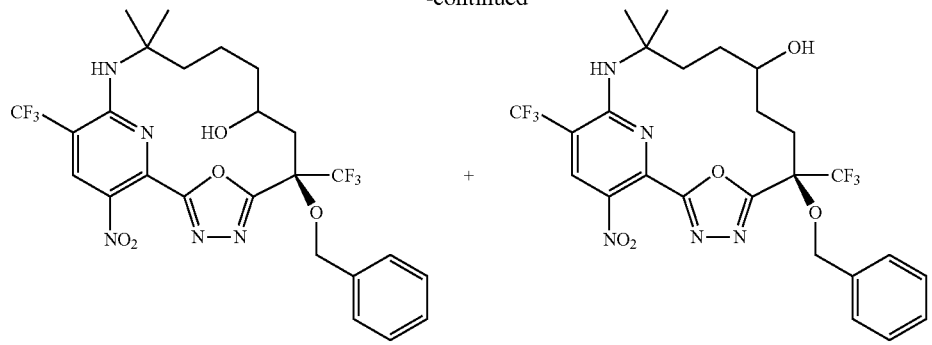

mixture of regioisomeric diasteremers

A solution of (6R)-6-benzyloxy-12,12-dimethyl-17-nitro-6,15-bis(trifluoromethyl)-19-oxa-3,4,13,18-tetrazatricyclo[12.3.1.12,5]nonadeca-1(18),2,4,8,14,16-hexaene (E/Z mixture) (200 mg, 0.35 mmol) in borane tetrahydrofuran complex (2.5 mL, 1 M solution in THF, 2.5 mmol) was stirred at 0° C. for 30 min. Water (1.3 mL) was added dropwise at 0° C. (exothermic). A solution of aqueous sodium hydroxide (0.4 mL, 2 M, 0.8 mmol) and hydrogen peroxide in water (524.48 mg, 1.35 mL, 5.3967 mmol) was added at 0° C. The mixture was stirred for 15 min at room temperature, then extracted with ethyl acetate (3×10 mL). The organic layer was dried over sodium sulfate, filtered and concentrated under vacuum to give a as a yellow solid and regioisomeric mixture of diastereomers, (6R)-6-benzyloxy-12,12-dimethyl-17-nitro-6,15-bis(trifluoromethyl)-19-oxa-3,4,13,18-tetrazatricyclo[12.3.1.12,5]nonadeca-1(18),2,4,14,16-pentaen-8-ol and (6R)-6-benzyloxy-12,12-dimethyl-17-nitro-6,15-bis(trifluoromethyl)-19-oxa-3,4,13,18-tetrazatricyclo[12.3.1.12,5]nonadeca-1(18),2,4,14,16-pentaen-9-ol (mixture of regioisomeric diastereomers) (305 mg, 67%). ESI-MS m/z calc. 589.176, found 589.9 (M+1)$^+$; Retention time: 2.26 minutes (LC Method C).

Step 2: (6R,8R)-17-Amino-12,12-dimethyl-6,15-bis(trifluoromethyl)-19-oxa-3,4,13,18-tetrazatricyclo[12.3.1.12,5]nonadeca-1(18),2,4,14,16-pentaene-6,8-diol (Compound 187), (6R)-17-amino-12,12-dimethyl-6,15-bis(trifluoromethyl)-19-oxa-3,4,13,18-tetrazatricyclo[12.3.1.12,5]nonadeca-1(18),2,4,14,16-pentaene-6,9-diol (mixture of diastereomers) and (6R,8S)-17-Amino-12,12-dimethyl-6,15-bis(trifluoromethyl)-19-oxa-3,4,13,18-tetrazatricyclo[12.3.1.12,5]nonadeca-1(18),2,4,14,16-pentaene-6,8-diol (Compound 188)

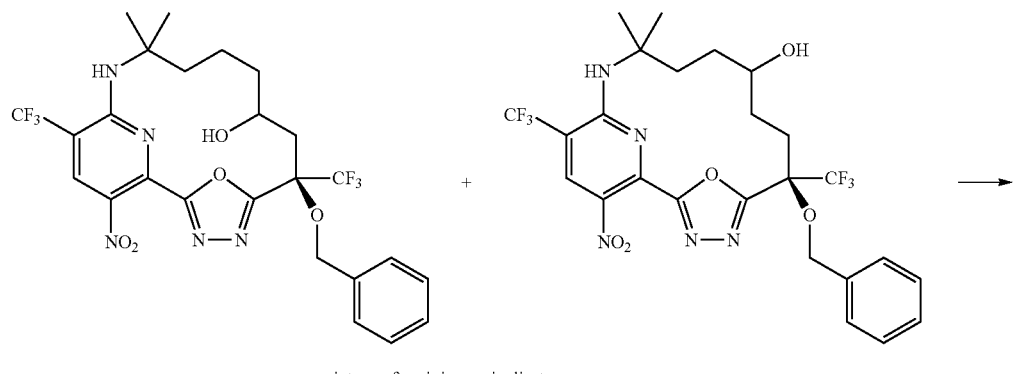

mixture of regioisomeric diastereomers

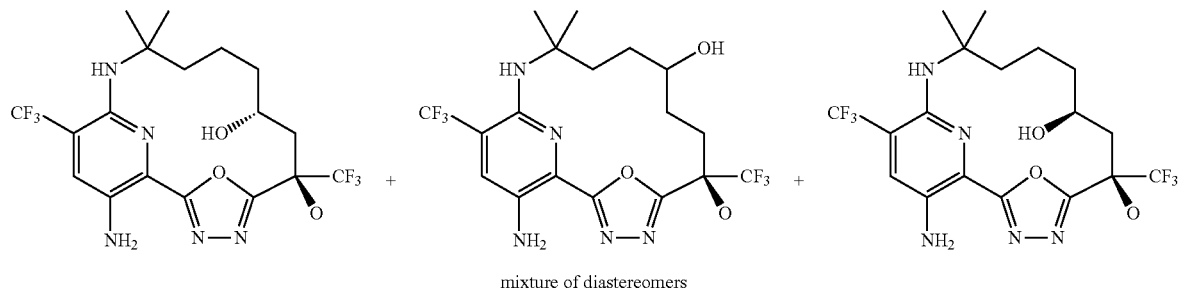

mixture of diastereomers

To a degassed solution of a mixture of (6R)-6-benzyloxy-12,12-dimethyl-17-nitro-6,15-bis(trifluoromethyl)-19-oxa-3,4,13,18-tetrazatricyclo[12.3.1.1²,⁵]nonadeca-1(18),2,4,14,16-pentaen-8-ol and (6R)-6-benzyloxy-12,12-dimethyl-17-nitro-6,15-bis(trifluoromethyl)-19-oxa-3,4,13,18-tetrazatricyclo[12.3.1.1²,⁵]nonadeca-1(18),2,4,14,16-pentaen-9-ol (mixture of regioisomeric diastereomers) (200 mg, 0.2701 mmol) in methanol (6 mL) at room temperature was added 10% palladium on carbon (60 mg, 0.5638 mmol). The black suspension was purged with nitrogen for 5 min, then hydrogen was bubbled through the suspension for 5 min. Then, the mixture was stirred at room temperature overnight under hydrogen atmosphere. The black suspension was purged with nitrogen, then filtered over Celite which was washed with DCM (3×10 mL) and the filtrate was concentrated under vacuum. Purification by reverse phase HPLC (column 1) (50 g $C_{18}$ column) using a gradient from 1% to 85% acetonitrile in water (+0.02% HCl) gave three products:

The first regioisomer/enantiomer to elute from column 1 was still contaminated with impurities and was further purified by reverse phase HPLC (column 2) (50 g $C_{18}$ column) using a gradient from 1% to 85% acetonitrile in water (+0.02% HCl) which gave as a yellow solid, (6R,8R)-17-amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,8-diol (4.4 mg, 34%). ESI-MS m/z calc. 469.15485, found 470.2 (M+1)⁺; Retention time: 2.85 minutes (LC Method C).

The second product peak to elute from column 1 was further purified by reverse phase HPLC (column 3) (15 g, $C_{18}$ column) using a gradient from 5% to 80% acetonitrile in water (+0.02% HCl) which gave 14.5 mg of a yellow solid and inseparable mixture of (6R)-17-amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,9-diol (mixture of diastereomers). This material was taken directly to the ensuing step.

The third regioisomer/enantiomer to elute from column 1 was isolated as a yellow solid, (6R,8S)-17-amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,8-diol (66 mg, 52%). ¹H NMR (400 MHz, CD₃OD) δ 7.50 (s, 1H), 4.40 (td, J=9.2, 4.9 Hz, 1H), 3.54 (td, J=12.5, 4.5 Hz, 1H), 2.66 (d, J=14.5 Hz, 1H), 2.11 (dd, J=14.8, 10.0 Hz, 1H), 1.77-1.46 (m, 4H), 1.43 (s, 3H), 1.41-1.35 (m, 1H), 1.31 (s, 3H) ppm. ¹⁹F NMR (377 MHz, Chloroform-d) δ −63.87 (s, 3F), −81.07 (s, 3F) ppm. ESI-MS m/z calc. 469.1549, found 470.0 (M+1)⁺; Retention time: 3.21 minutes (LC Method C).

Step 3: (6R)-17-Amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,9-diol (enantiomer 1) (Compound 189) and (6R)-17-amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,9-diol (Enantiomer 2) (Compound 190)

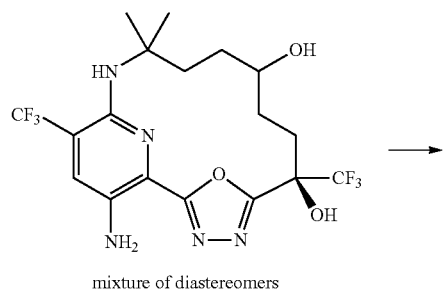

mixture of diastereomers

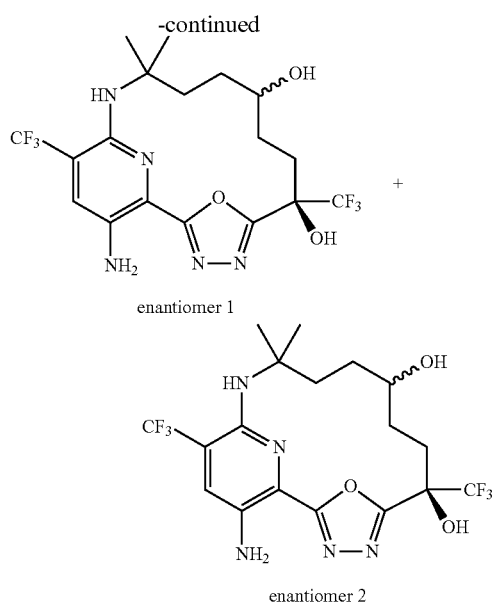

enantiomer 1 enantiomer 2

A diastereomeric mixture of (6R)-17-amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,9-diol (mixture of diastereomers) (38 mg, 0.0672 mmol) was purified by SFC using a Lux Cellulose 1 column (150×21.2 mm, 5 μm particle size) eluting with 7% MeOH in CO₂ which provided two diastereomeric products:

The first enantiomer to elute was isolated as a yellow solid, (6R)-17-amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,9-diol (enantiomer 1) (18.9 mg, 60%). ¹H NMR (400 MHz, CD₃OD) δ 7.43 (s, 1H), 4.96-4.77 (m, 1H), 3.40 (t, J=12.0 Hz, 1H), 2.56 (dd, J=13.4, 5.1 Hz, 1H), 2.28-2.13 (m, 1H), 2.21 (dd, J=13.4, 9.8 Hz, 1H), 1.97-1.83 (m, 1H), 1.66-1.47 (m, 5H), 1.46-1.35 (m, 1H), 1.26 (s, 3H) ppm. ¹⁹F NMR (377 MHz, CD₃OD) δ −65.52 (s, 3F), −79.65 (s, 3F) ppm. ESI-MS m/z calc. 469.1549, found 470.2 (M+1)⁺; Retention time: 3.11 minutes (LC Method C).

The second enantiomer to elute was isolated as a yellow solid, (6R)-17-amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,9-diol (enantiomer 2) (10.3 mg, 32%). ¹H NMR (400 MHz, CD₃OD) δ 7.43 (s, 1H), 4.78-4.65 (m, 1H), 3.40 (t, J=12.5 Hz, 1H), 3.02 (dd, J=14.1, 6.2 Hz, 1H), 2.21-2.08 (m, 1H), 2.08-1.98 (m, 1H), 1.96-1.80 (m, 1H), 1.66-1.36 (m, 6H), 1.26 (s, 3H) ppm. ¹⁹F NMR (377 MHz, CD₃OD) δ −65.54 (s, 3F), −82.01 (s, 3F) ppm. ESI-MS m/z calc. 469.1549, found 470.2 (M+1)⁺; Retention time: 3.14 minutes (LC Method C).

Step 4: Solid Form Characterization of Crystalline Compound 188 Dichloromethane Solvate Form A A. Single Crystal X-Ray Diffraction Single crystals of crystalline Compound 188 dichloromethane solvate Form A were grown from dichloromethane. X-ray diffraction data were acquired at 100 K on a Bruker diffractometer equipped with Cu Kα radiation (λ=1.54178 Å) and a CPAD detector. The structure was solved and refined using SHELX programs (Sheldrick, G.

M., Acta Cryst., (2008) A64, 112-122) and results are summarized in Table 9 below.

TABLE 9

Single crystal elucidation of crystalline Compound 188 dichloromethane solvate Form A

| Crystal System | Monoclinic |
|---|---|
| Space Group | P2$_1$ |
| a (Å) | 16.1454(10) |
| b (Å) | 13.2069(7) |
| c (Å) | 23.1642(15) |
| α (°) | 90 |
| β (°) | 99.687(2) |
| γ (°) | 90 |
| V (Å3) | 4868.9(5) |
| Z/Z' | 2/4 |
| Temperature | 100 K |

Example 105: Preparation of (6R)-17-amino-12-cyclopropyl-6,15-bis(trifluoromethyl)-19-oxa-3,4,13,18-tetrazatricyclo[12.3.1.1$^{2,5}$]nonadeca-1(18),2,4,14,16-pentaen-6-ol (enantiomer 1) (Compound 191) and (6R)-17-amino-12-cyclopropyl-6,15-bis(trifluoromethyl)-19-oxa-3,4,13,18-tetrazatricyclo[12.3.1.1$^{2,5}$]nonadeca-1(18),2,4,14,16-pentaen-6-ol (enantiomer 2) (Compound 192)

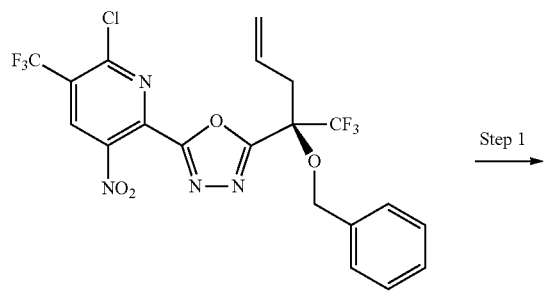

Step 1

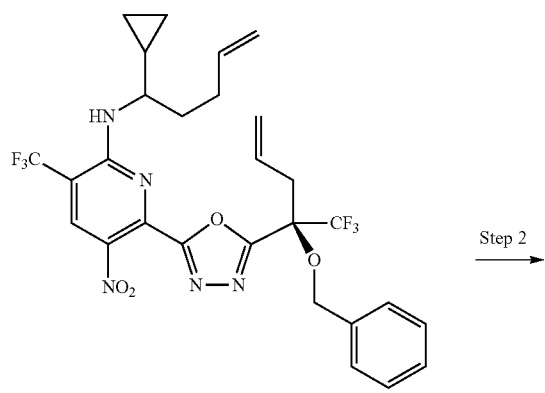

Step 2

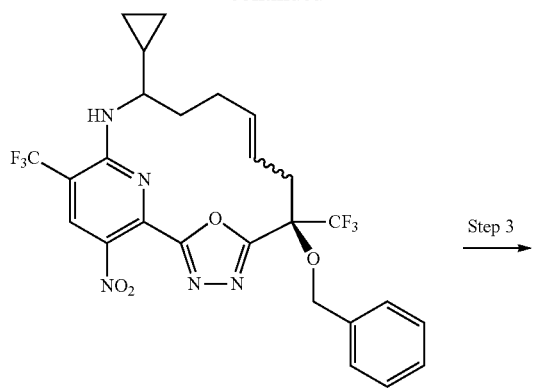

E/Z mixture

Step 3

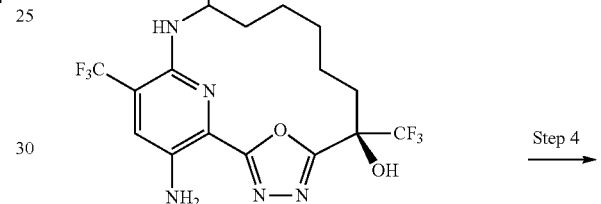

Step 4

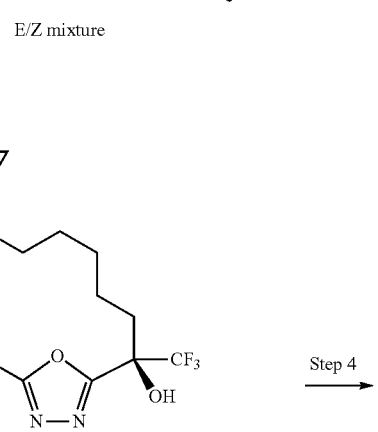

enantiomer 1

+

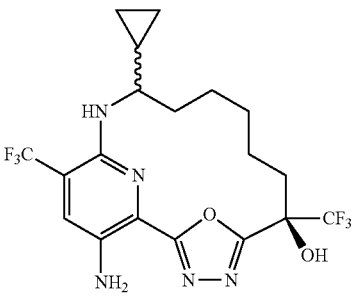

enantiomer 2

Step 1: 6-[5-[(1R)-1-Benzyloxy-1-(trifluoromethyl)but-3-enyl]-1,3,4-oxadiazol-2-yl]-N-(1-cyclopropylpent-4-enyl)-5-nitro-3-(trifluoromethyl)pyridin-2-amine Step 2: (6R)-6-Benzyloxy-12-cyclopropyl-17-nitro-6,15-bis(trifluoromethyl)-19-oxa-3,4,13,18-tetrazatricyclo[12.3.1.12,5]nonadeca-1(17),2,4,8,14(18),15-hexaene

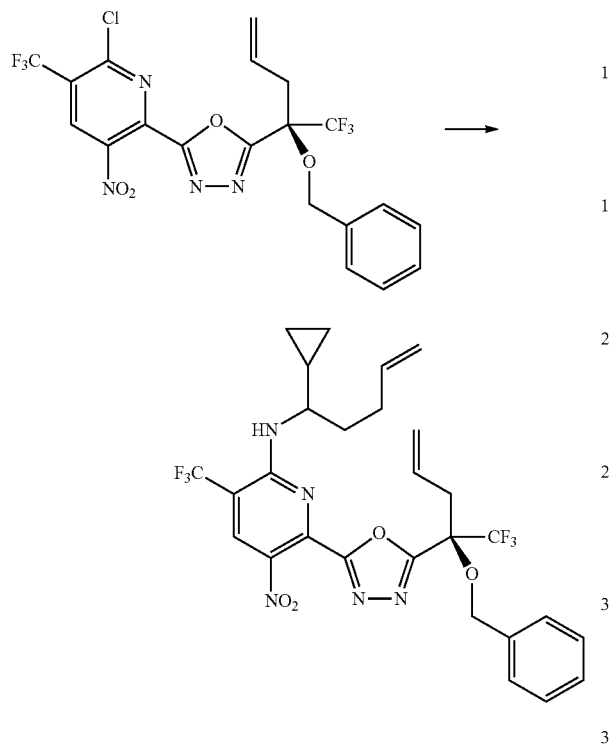

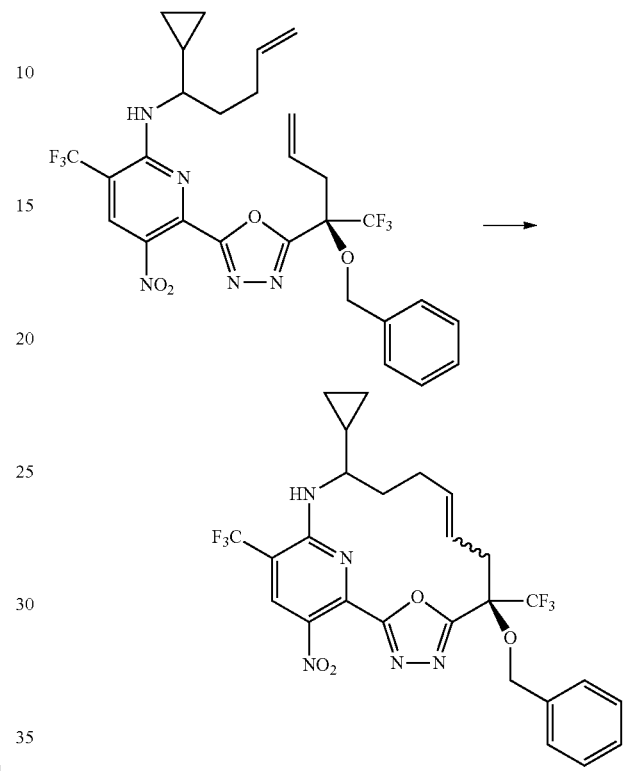

E/Z mixture

To a solution of 2-[(1R)-1-benzyloxy-1-(trifluoromethyl)but-3-enyl]-5-[6-chloro-3-nitro-5-(trifluoromethyl)-2-pyridyl]-1,3,4-oxadiazole (158 mg, 0.3022 mmol) in acetonitrile (6 mL) was added N,N-diisopropylethylamine (150 mg, 0.2022 mL, 1.1606 mmol), followed by a solution 1-cyclopropylpent-4-en-1-amine (50 mg, 0.3993 mmol) in acetonitrile (1 mL). The mixture was stirred at 30° C. for 2 h and cooled to room temperature. The mixture was dry loaded on silica gel (about 1 g) and purified by flash chromatography (24 g silica gel, eluting 10% to 30% ethyl acetate in heptanes) to afford 6-[5-[(1R)-1-benzyloxy-1-(trifluoromethyl)but-3-enyl]-1,3,4-oxadiazol-2-yl]-N-(1-cyclopropylpent-4-enyl)-5-nitro-3-(trifluoromethyl)pyridin-2-amine (183 mg, 99%) as a colorless oil. $^1$H NMR (400 MHz, CDCl$_3$) δ 8.57 (s, 1H), 7.42-7.30 (m, 5H), 6.05-5.91 (m, 1H), 5.84-5.70 (m, 2H), 5.35-5.21 (m, 2H), 5.05-4.92 (m, 2H), 4.82 (d, J=10.3 Hz, 1H), 4.65 (dd, J=10.4, 3.3 Hz, 1H), 3.84-3.73 (m, 1H), 3.31-3.17 (m, 2H), 2.23-2.12 (m, 2H), 1.93-1.76 (m, 2H), 1.02-0.89 (m, 1H), 0.68-0.59 (m, 1H), 0.57-0.48 (m, 1H), 0.45-0.28 (m, 2H) ppm. $^{19}$F NMR (377 MHz, CDCl$_3$) δ−64.59 (s, 3F), −73.44 to −73.58 (m, 3F) ppm. NMR shows a 1:1 mixture of diastereomers. The product did not ionize on LCMS. Retention time: 2.41 minutes (LC Method E).

A dried 250 mL flask was charged with 1,2-dichloroethane (100 mL). The solvent was bubbled with nitrogen for 30 min. Zhan catalyst-1B (27 mg, 0.0368 mmol) was added under gentle flow of nitrogen. The mixture was bubbled with nitrogen for 10 min and heated to 66° C. A nitrogen-bubbled solution of 6-[5-[(1R)-1-benzyloxy-1-(trifluoromethyl)but-3-enyl]-1,3,4-oxadiazol-2-yl]-N-(1-cyclopropylpent-4-enyl)-5-nitro-3-(trifluoromethyl)pyridin-2-amine (183 mg, 0.2992 mmol) in 1,2-dichloroethane (20 mL) was added dropwise over 1 h. After addition was finished, the mixture was bubbled with nitrogen for 6 min. The mixture was continued to stir at 66° C. for 0.5 h, cooled to room temperature then 5 drops of DMSO were added to quench the catalyst. The mixture was concentrated on silica gel (3 g) and purified by flash chromatography (40 g silica gel, eluting 5% to 25% ethyl acetate in heptanes) to afford (6R)-6-benzyloxy-12-cyclopropyl-17-nitro-6,15-bis(trifluoromethyl)-19-oxa-3,4,13,18-tetrazatricyclo[12.3.1.12,5]nonadeca-1(17),2,4,8,14(18),15-hexaene (132 mg, 76%) as a pale-yellow oil. $^1$H NMR (400 MHz, CDCl$_3$) δ 8.52-8.43 (m, 1H), 7.45-7.28 (m, 5H), 5.95-5.69 (m, 2H), 5.63-5.38 (m, 1H), 5.02-4.85 (m, 1H), 4.72-4.51 (m, 1H), 3.45-3.27 (m, 1H), 3.19-2.63 (m, 2H), 2.49-2.15 (m, 2H), 2.13-1.89 (m, 1H), 1.80-1.65 (m, 1H), 1.19-0.92 (m, 2H), 0.69-0.44 (m, 2H), 0.34-0.17 (m, 1H) ppm. $^{19}$F NMR (377 MHz, CDCl$_3$) δ−63.83 to −64.98 (m, 3F), −72.69 to −74.13 (m, 3F) ppm.

871

Step 3: (6R)-17-Amino-12-cyclopropyl-6,15-bis
(trifluoromethyl)-19-oxa-3,4,13,18-tetrazatricyclo
[12.3.1.12,5]nonadeca-1(18),2,4,14,16-pentaen-6-ol

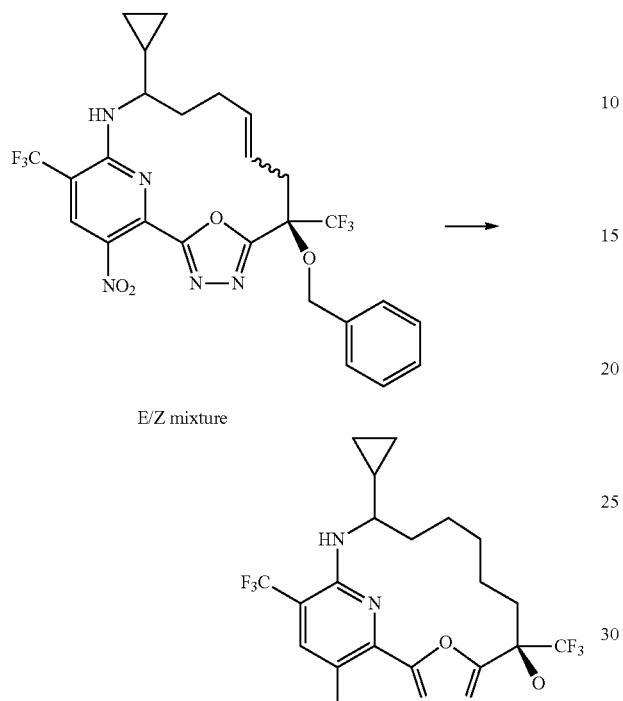

E/Z mixture

A mixture of (6R)-6-benzyloxy-12-cyclopropyl-17-nitro-6,15-bis(trifluoromethyl)-19-oxa-3,4,13,18-tetrazatricyclo[12.3.1.12,5]nonadeca-1(17),2,4,8,14(18),15-hexaene (132 mg, 0.2262 mmol), 10% palladium on carbon (50% wet) (41 mg, 0.0193 mmol) and methanol (6 mL) was stirred under hydrogen atmosphere (balloon) at room temperature overnight. The mixture was filtered through diatomaceous earth and washed with ethyl acetate. The filtrate was concentrated and the residue hydrogenated again with 10% palladium on carbon (51 mg, 0.024 mmol) and methanol (6 mL) under hydrogen atmosphere (balloon) at room temperature overnight. The mixture was filtered through diatomaceous earth and washed with ethyl acetate. The filtrate was concentrated and purified by flash chromatography (40 g column, eluting 10% to 30% ethyl acetate in heptanes) to afford (6R)-17-amino-12-cyclopropyl-6,15-bis(trifluoromethyl)-19-oxa-3,4,13,18-tetrazatricyclo[12.3.1.12,5]nonadeca-1(18),2,4,14,16-pentaen-6-ol (100 mg, 95%) as a pale-yellow oil. $^1$H NMR (400 MHz, CDCl$_3$) δ 7.33-7.29 (m, 1H), 4.81 (d, J=15.2 Hz, 1H), 3.93 (br. s, 1H), 2.85-2.60 (m, 2H), 2.48-1.98 (m, 3H), 1.87-1.46 (m, 7H), 1.39-1.31 (m, 1H), 1.04-0.92 (m, 1H), 0.78-0.68 (m, 1H), 0.56-0.40 (m, 2H), 0.24-0.10 (m, 1H) ppm. $^{19}$F NMR (377 MHz, CDCl$_3$) δ−64.12 (s, 3F), −76.49 to −81.49 (m, 3F) ppm. ESI-MS m/z calc. 465.1599, found 466.0 (M+1)$^+$; Retention time: 3.49 minutes (LC Method C).

872

Step 4: (6R)-17-Amino-12-cyclopropyl-6,15-bis
(trifluoromethyl)-19-oxa-3,4,13,18-tetrazatricyclo
[12.3.1.12,5]nonadeca-1(18),2,4,14,16-pentaen-6-ol
(enantiomer 1) (Compound 191) and (6R)-17-amino-12-cyclopropyl-6,15-bis(trifluoromethyl)-19-oxa-3,4,13,18-tetrazatricyclo[12.3.1.12,5]nonadeca-1(18),2,4,14,16-pentaen-6-ol (enantiomer 2)
(Compound 192)

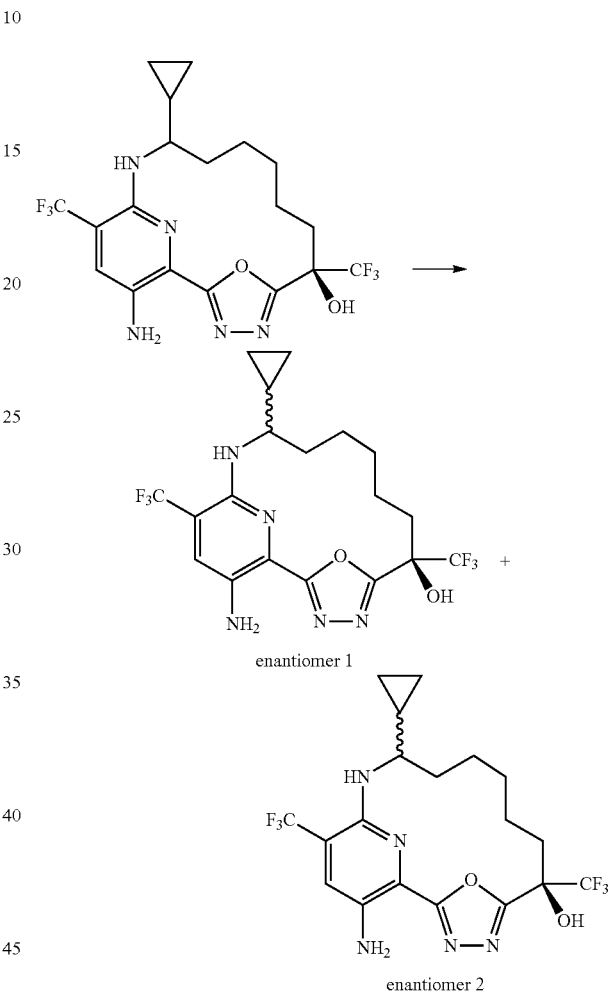

enantiomer 1 enantiomer 2

The two diastereomers of (6R)-17-amino-12-cyclopropyl-6,15-bis(trifluoromethyl)-19-oxa-3,4,13,18-tetrazatricyclo[12.3.1.12,5]nonadeca-1(18),2,4,14,16-pentaen-6-ol (130 mg, 0.2793 mmol) were separated by a chiral SFC method using an Amylose 1 column with 8% methanol in CO$_2$ mobile phase (flow rate=4 mL/min, column temperature=40° C.). Fractions containing each diastereomer were then concentrated under reduced pressure and freeze-dried (acetonitrile/water mixture) to afford two diastereomers.

The first diastereomer to elute was isolated as a pale-yellow solid, (6R)-17-amino-12-cyclopropyl-6,15-bis(trifluoromethyl)-19-oxa-3,4,13,18-tetrazatricyclo[12.3.1.12,5] nonadeca-1(18),2,4,14,16-pentaen-6-ol (enantiomer 1) (31 mg, 24%). $^1$H NMR (400 MHz, DMSO-d6) δ 7.62 (s, 1H), 7.54 (s, 1H), 6.02 (s, 2H), 5.07 (d, J=3.4 Hz, 1H), 2.89-2.80 (m, 1H), 2.49-2.41 (m, 1H), 2.35-2.23 (m, 1H), 2.13-2.02 (m, 1H), 1.79-1.58 (m, 3H), 1.56-1.36 (m, 3H), 1.34-1.21 (m, 1H), 1.09-0.97 (m, 1H), 0.73-0.63 (m, 1H), 0.48-0.33 (m, 2H), 0.14-0.04 (m, 1H) ppm. $^{19}$F NMR (377 MHz, DMSO-d6) δ −62.73 (s, 3F), −76.29 (s, 3F) ppm. ESI-MS m/z calc. 465.1599, found 466.0 (M+1)⁺; Retention time: 3.49 minutes (LC Method C).

The second diastereomer to elute was isolated as a pale-yellow solid, (6R)-17-amino-12-cyclopropyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (28 mg, 21%). ¹H NMR (400 MHz, DMSO-d6) δ 7.62 (s, 1H), 7.57 (s, 1H), 6.03 (s, 2H), 4.99 (d, J=2.9 Hz, 1H), 2.81-2.71 (m, 1H), 2.63-2.53 (m, 1H), 2.27-2.15 (m, 1H), 2.07-1.94 (m, 1H), 1.71-1.39 (m, 6H), 1.23-1.13 (m, 1H), 1.08-0.96 (m, 1H), 0.71-0.60 (m, 1H), 0.48-0.36 (m, 2H), 0.15-0.05 (m, 1H) ppm. ¹⁹F NMR (377 MHz, DMSO-d6) δ −62.73 (s, 3F), −79.14 (s, 3F) ppm. ESI-MS m/z calc. 465.1599, found 466.0 (M+1)⁺; Retention time: 3.5 minutes (LC Method C.

Example 106: Preparation of (6R)-17-amino-6,15-bis(trifluoromethyl)spiro[19-oxa-3,4,13,18-tetrazatricyclo[12.3.1.1²,⁵]nonadeca-1(18),2,4,14,16-pentaene-12,1'-cyclohexane]-6-ol (Compound 193)

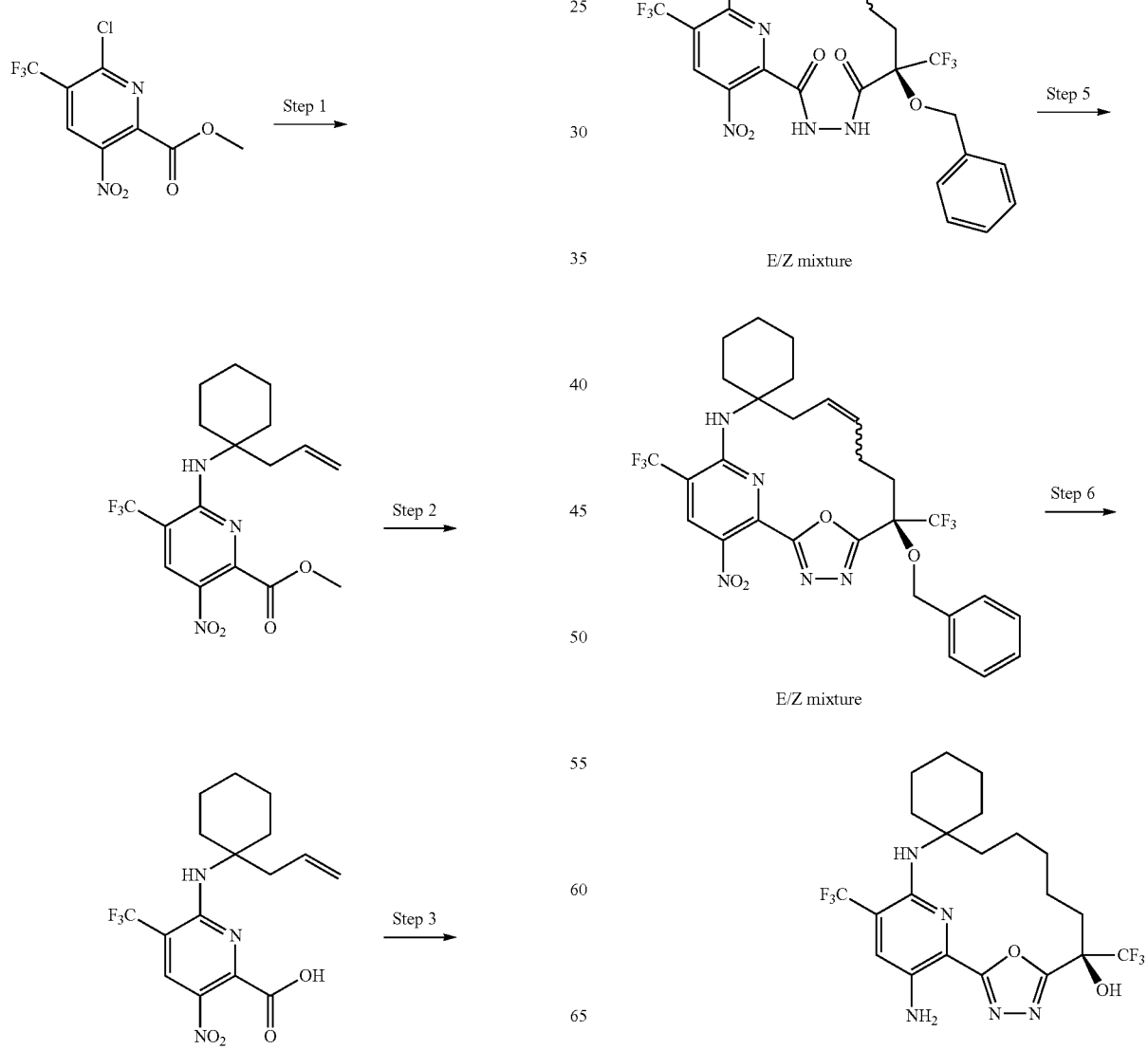

Step 1: Methyl 6-[(1-allylcyclohexyl)amino]-3-nitro-5-(trifluoromethyl)pyridine-2-carboxylate

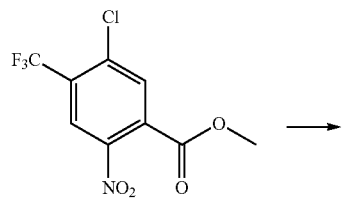

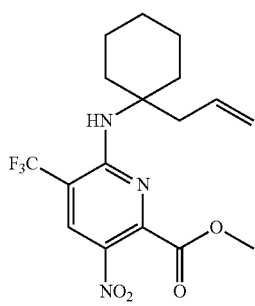

In a flask, 1-allylcyclohexanamine (515 mg, 3.699 mmol), DIEA (1.7 mL, 9.76 mmol) and methyl 6-chloro-3-nitro-5-(trifluoromethyl)pyridine-2-carboxylate (950 mg, 3.004 mmol) were combined in acetonitrile (23 mL) and the mixture was heated to 80° C. for 15 minutes. The reaction mixture was cooled to ambient temperature and the solvent was removed in vacuo. The residue was diluted with ethyl acetate (50 mL) and washed with brine (2×25 mL), dried over sodium sulfate, filtered and concentrated in vacuo. The residue was purified by silica gel column chromatography (40 gram column) using a gradient from 100% hexanes to 30% ethyl acetate in hexanes to afford as a white solid, methyl 6-[(1-allylcyclohexyl)amino]-3-nitro-5-(trifluoromethyl)pyridine-2-carboxylate (899 mg, 77%). ESI-MS m/z calc. 387.1406, found 388.53 (M+1)$^+$; Retention time: 0.83 minutes (LC Method S).

Step 2: 6-[(1-Allylcyclohexyl)amino]-3-nitro-5-(trifluoromethyl)pyridine-2-carboxylic Acid

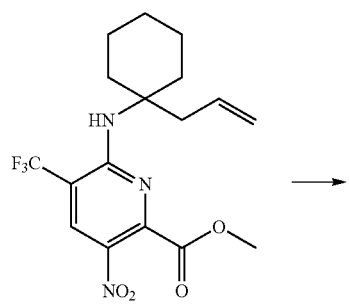

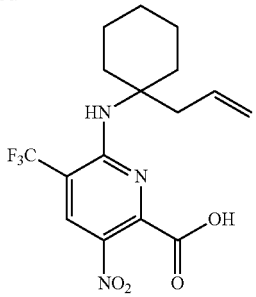

Methyl 6-[(1-allylcyclohexyl)amino]-3-nitro-5-(trifluoromethyl)pyridine-2-carboxylate (899 mg, 2.321 mmol) was combined with LiOH (500 mg, 20.88 mmol) in MeOH (9 mL), THF (9 mL) and water (4.5 mL) and stirred vigorously at room temperature for 5 minutes. The reaction mixture was then cooled and added 1 M HCl until the aqueous layer was acidic. Diluted with ethyl acetate and the layers were separated and the aqueous was extracted additional ethyl acetate (2×15 mL). The combined organics were washed with brine, dried over sodium sulfate, filtered and concentrated without further purification to afford as an off-white solid, 6-[(1-allylcyclohexyl)amino]-3-nitro-5-(trifluoromethyl)pyridine-2-carboxylic acid (860 mg, 99%). ESI-MS m/z calc. 373.12494, found 374.1 (M+1)$^+$; Retention time: 0.74 minutes (LC Method S).

Step 3: 6-[(1-Allylcyclohexyl)amino]-N'-[(2R)-2-benzyloxy-2-(trifluoromethyl)hex-5-enoyl]-3-nitro-5-(trifluoromethyl)pyridine-2-carbohydrazide

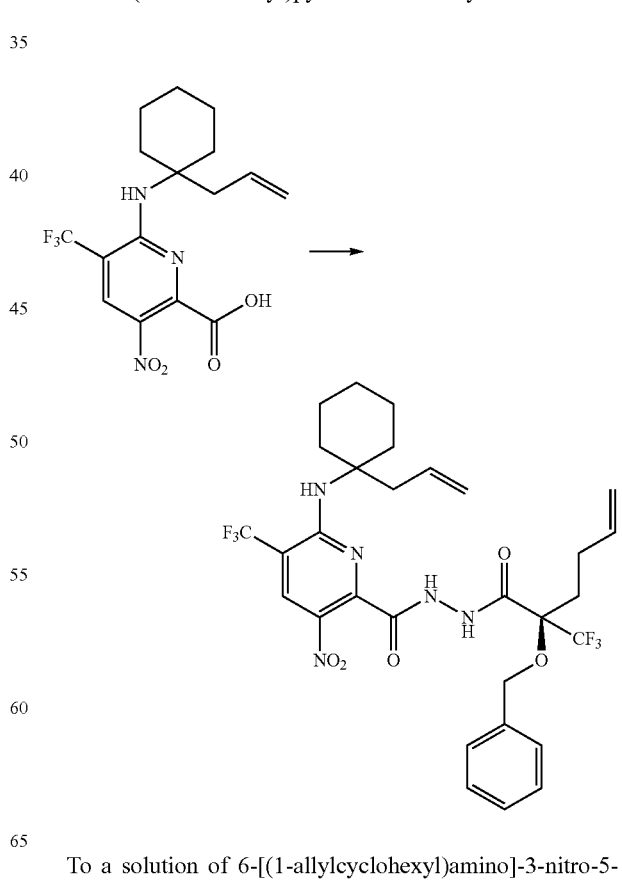

To a solution of 6-[(1-allylcyclohexyl)amino]-3-nitro-(trifluoromethyl)pyridine-2-carboxylic acid (390 mg, 1.045 mmol) in DMF (14.5 mL) was added DIEA (720 μL, 4.134 mmol) and HATU (397 mg, 1.044 mmol). The reaction mixture was stirred at room temperature for 10 minutes then added (2R)-2-benzyloxy-2-(trifluoromethyl)hex-5-enehydrazide (352 mg, 1.164 mmol) in DMF (3 mL) dropwise. Let the reaction stir at room temperature for 10 minutes. Diluted the reaction with brine and water and let stir for 5 minutes. The reaction was extracted with ethyl acetate (3×20 mL). The organic layers were washed with brine (20 mL), dried over sodium sulfate, filtered and evaporated. The crude material was then purified over silica gel chromatography (12 gram column) using a gradient from 100% hexanes to 70% ethyl acetate in hexanes to afford as a sticky light orange solid, 6-[(1-allylcyclohexyl)amino]-N'-[(2R)-2-benzyloxy-2-(trifluoromethyl)hex-5-enoyl]-3-nitro-5-(trifluoromethyl)pyridine-2-carbohydrazide (575 mg, 84%). ESI-MS m/z calc. 657.2386, found 658.3 (M+1)$^+$; Retention time: 0.76 minutes (LC Method R).

Step 4: (9R)-9-Benzyloxy-15-nitro-9,17-bis(trifluoromethyl)spiro[2,11,12,18-tetrazabicyclo[12.3.1] octadeca-1(18),5,14,16-tetraene-3,1'-cyclohexane]-10,13-dione (E/Z Mixture)

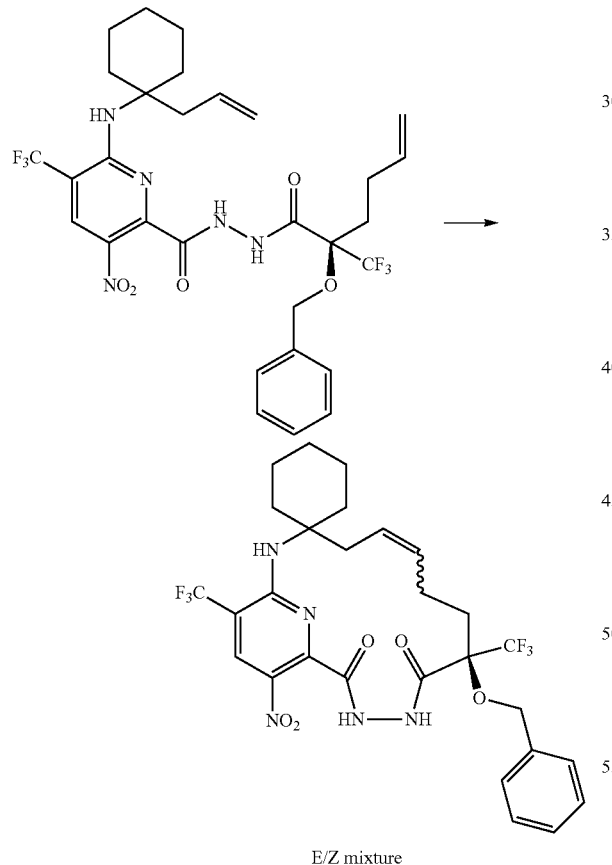

E/Z mixture

Nitrogen was bubbled through a light yellow solution of 6-[(1-allylcyclohexyl)amino]-N'-[(2R)-2-benzyloxy-2-(trifluoromethyl)hex-5-enoyl]-3-nitro-5-(trifluoromethyl)pyridine-2-carbohydrazide (575 mg, 0.899 mmol) in DCE (180 mL) overnight. Zhan catalyst-1B (130 mg, 0.1772 mmol) was then added in three portions, the first at room temperature and nitrogen was bubbled for 3 min. Then the light green solution was stirred at 60° C. (pre-heated oil bath), while the two other portions were added each 30 minutes apart. The mixture was stirred at 60° C. for 1 h after the last addition of catalyst. The brown solution was cooled to room temperature then DMSO (10 drops) was added to quench the catalyst. The solvent was removed under vacuum and the residue purified by normal phase chromatography over a 24 g silica column (1% to 40% MTBE in heptanes) to give as a light yellow oil, (9R)-9-benzyloxy-15-nitro-9,17-bis(trifluoromethyl)spiro[2,11,12,18-tetrazabicyclo[12.3.1]octadeca-1(18),5,14,16-tetraene-3,1'-cyclohexane]-10,13-dione (E/Z mixture) (446 mg, 70%). $^1$H NMR (400 MHz, CDCl$_3$) δ 8.57 (s, 1H), 7.93 (s, 1H), 7.49-7.29 (m, 4H), 7.09-6.98 (m, 2H), 5.70-5.41 (m, 2H), 5.18 (br. s., 1H), 4.63 (d, J=9.7 Hz, 1H), 4.37 (d, J=10.4 Hz, 1H), 3.27 (dd, J=14.2, 10.9 Hz, 1H), 2.88 (d, J=13.9 Hz, 1H), 2.32-2.15 (m, 1H), 2.09-1.97 (m, 1H), 1.91 (dd, J=14.2, 5.1 Hz, 1H), 1.79-1.47 (m, 4H), 1.45-1.12 (m, 7H) ppm. ESI-MS m/z calc. 629.2073, found 629.9 (M+1)$^+$; Retention time: 3.64 minutes (LC Method C).

Step 5: (6R)-6-Benzyloxy-17-nitro-6,15-bis(trifluoromethyl)spiro[19-oxa-3,4,13,18-tetrazatricyclo [12.3.1.1²,⁵]nonadeca-1(17),2,4,9,14(18),15-hexaene-12,1'-cyclohexane](E/Z Mixture)

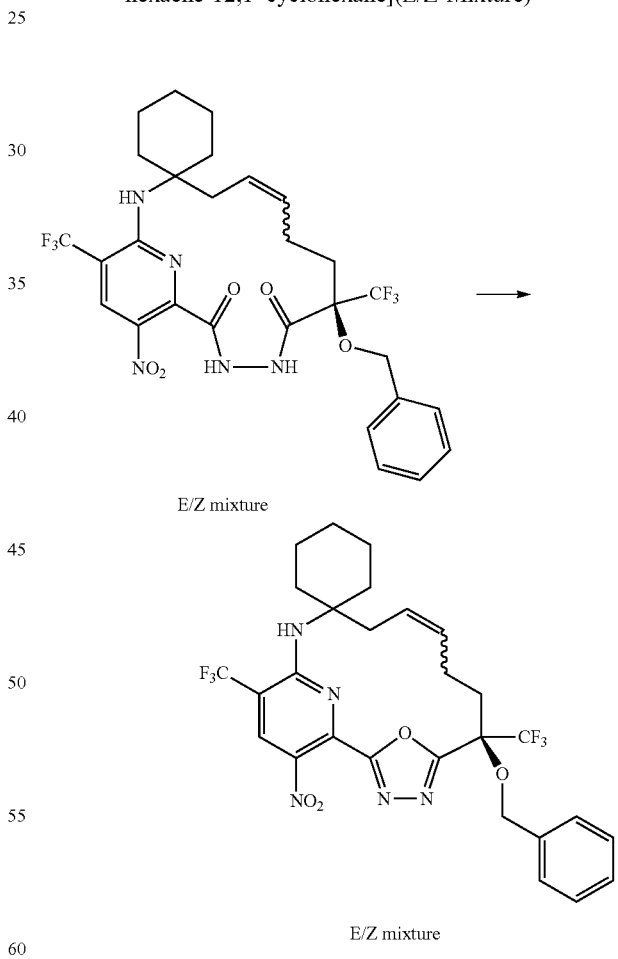

E/Z mixture

A solution of (9R)-9-benzyloxy-15-nitro-9,17-bis(trifluoromethyl)spiro[2,11,12,18-tetrazabicyclo[12.3.1]octadeca-1 (18),5,14,16-tetraene-3,1'-cyclohexane]-10,13-dione (E/Z mixture) (260 mg, 0.3717 mmol) and 1,4-diazabicyclo [2.2.2]octane (60 mg, 0.5349 mmol) in DCM (3.6 mL) was treated with a solution of 25% 2-chloro-1,3-dimethyl-4,5- dihydroimidazol-1-ium; chloride (73 mg, 0.4318 mmol) in DCM (2.6 mL) at room temperature. The formation of the imidazolium intermediate was completed in 10 min. The DCM was evaporated and the residue was dissolved in toluene (8 mL). The mixture was stirred at 100° C. overnight. The dark mixture was quenched with water (3 mL) and extracted with MTBE (3×10 mL). The organic layer was dried over sodium sulfate, filtrated and concentrated under vacuum to give as a crude brown oil, (6R)-6-benzyloxy-17-nitro-6,15-bis(trifluoromethyl)spiro[19-oxa-3,4,13,18-tetrazatricyclo[12.3.1.12,5]nonadeca-1(17),2,4,9,14(18),15-hexaene-12,1'-cyclohexane] (E/Z mixture) (320 mg, 115%, material is crude and contains impurities). ESI-MS m/z calc. 611.1967, found 612.2 (M+1)$^+$; Retention time: 4.4 minutes. Took this material directly to the ensuing step (LC Method BB).

Step 6: (6R)-17-Amino-6,15-bis(trifluoromethyl) spiro[19-oxa-3,4,13,18-tetrazatricyclo[12.3.1.12,5] nonadeca-1(18),2,4,14,16-pentaene-12,1'-cyclohexane]-6-ol (Compound 193)

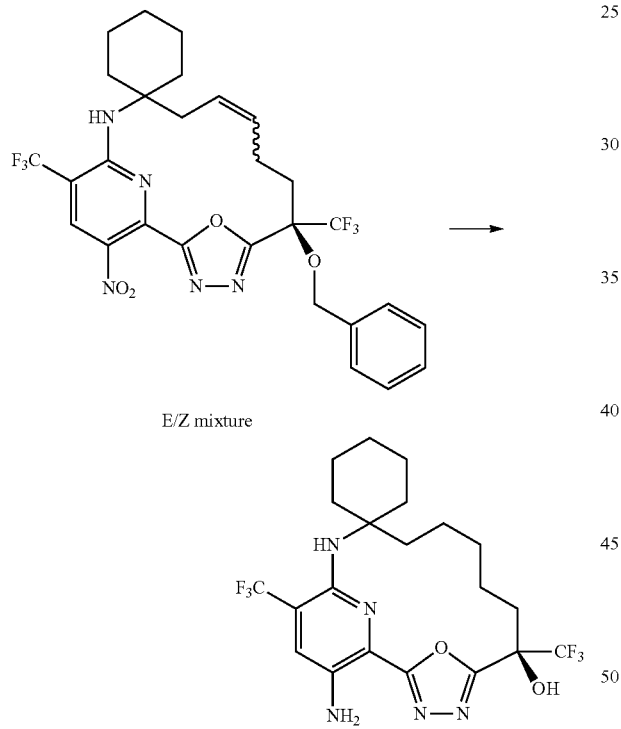

E/Z mixture

Palladium on carbon (10 mg, 0.0094 mmol) was added to a degassed brown solution of crude (6R)-6-benzyloxy-17-nitro-6,15-bis(trifluoromethyl)spiro[19-oxa-3,4,13,18-tetrazatricyclo[12.3.1.12,5]nonadeca-1(17),2,4,9,14(18),15-hexaene-12,1'-cyclohexane] (E/Z mixture) (40 mg, 0.0515 mmol) in methanol (2 mL) at room temperature. Nitrogen was bubbled through the black mixture, then hydrogen (1 atmosphere) was bubbled through the mixture for 5 min. The mixture was stirred under hydrogen atmosphere at room temperature overnight. The black suspension was then purged with nitrogen for 5 min and then was filtered over Celite. The cake was washed with DCM (3×10 mL). The fluorescent yellow filtrate was concentrated under vacuum to give a crude yellow solid. A second lot of the crude product made in a similar fashion was combined with this lot to give crude (6R)-17-amino-6,15-bis(trifluoromethyl)spiro[19-oxa-3,4,13,18-tetrazatricyclo[12.3.1.12,5]nonadeca-1(18), 2,4,14,16-pentaene-12,1'-cyclohexane]-6-ol (242 mg, 0.4071 mmol) which was then purified by reverse phase chromatography over a 50 g $C_{18}$ column (5% to 85% acetonitrile/0.02% HCl in water) to afford as a yellow solid, (6R)-17-amino-6,15-bis(trifluoromethyl)spiro[19-oxa-3,4,13,18-tetrazatricyclo[12.3.1.12,5]nonadeca-1(18),2,4,14,16-pentaene-12,1'-cyclohexane]-6-ol (162 mg, 79%). $^1$H NMR (400 MHz, CD$_3$OD) δ 7.54 (s, 1H), 3.10-2.89 (m, 1H), 2.46-2.28 (m, 2H), 2.18-2.05 (m, 1H), 1.94-1.84 (m, 1H), 1.83-1.44 (m, 13H), 1.44-1.33 (m, 1H), 1.30-1.17 (m, 1H) ppm. $^{19}$F NMR (377 MHz, CD$_3$OD) δ −65.27 (s, 3F), −80.95 (s, 3F) ppm. ESI-MS m/z calc. 493.1912, found 494.0 (M+1)$^+$; Retention time: 3.77 minutes (LC Method C).

Example 107: Preparation of 17-amino-12,12-dimethyl-6,15-bis(trifluoromethyl)-19-oxa-3,4,13,18-tetrazatricyclo[12.3.1.12,5]nonadeca-1(18),2,4,14,16-pentaene-6,7-diol (enantiomer 1, cis diol) (Compound 194) and 17-amino-12,12-dimethyl-6, 15-bis(trifluoromethyl)-19-oxa-3,4,13,18-tetrazatricyclo[12.3.1.12,5]nonadeca-1(18),2,4,14,16-pentaene-6,7-diol (enantiomer 2, cis diol) (Compound 195)

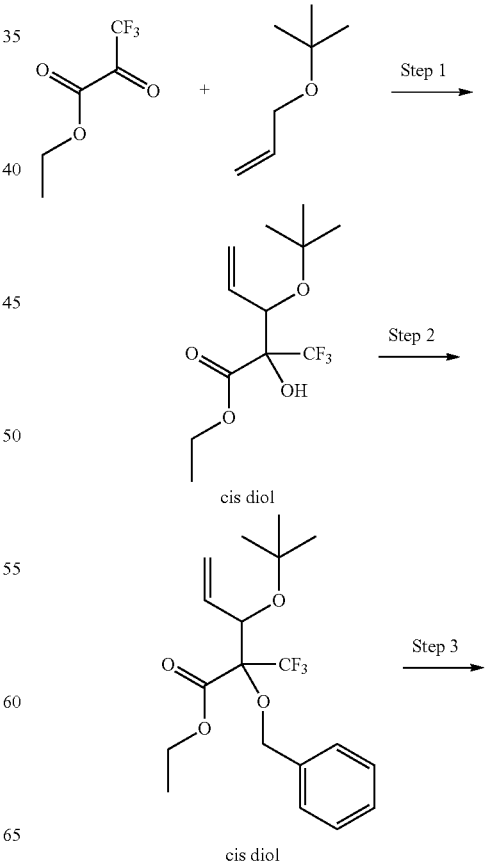

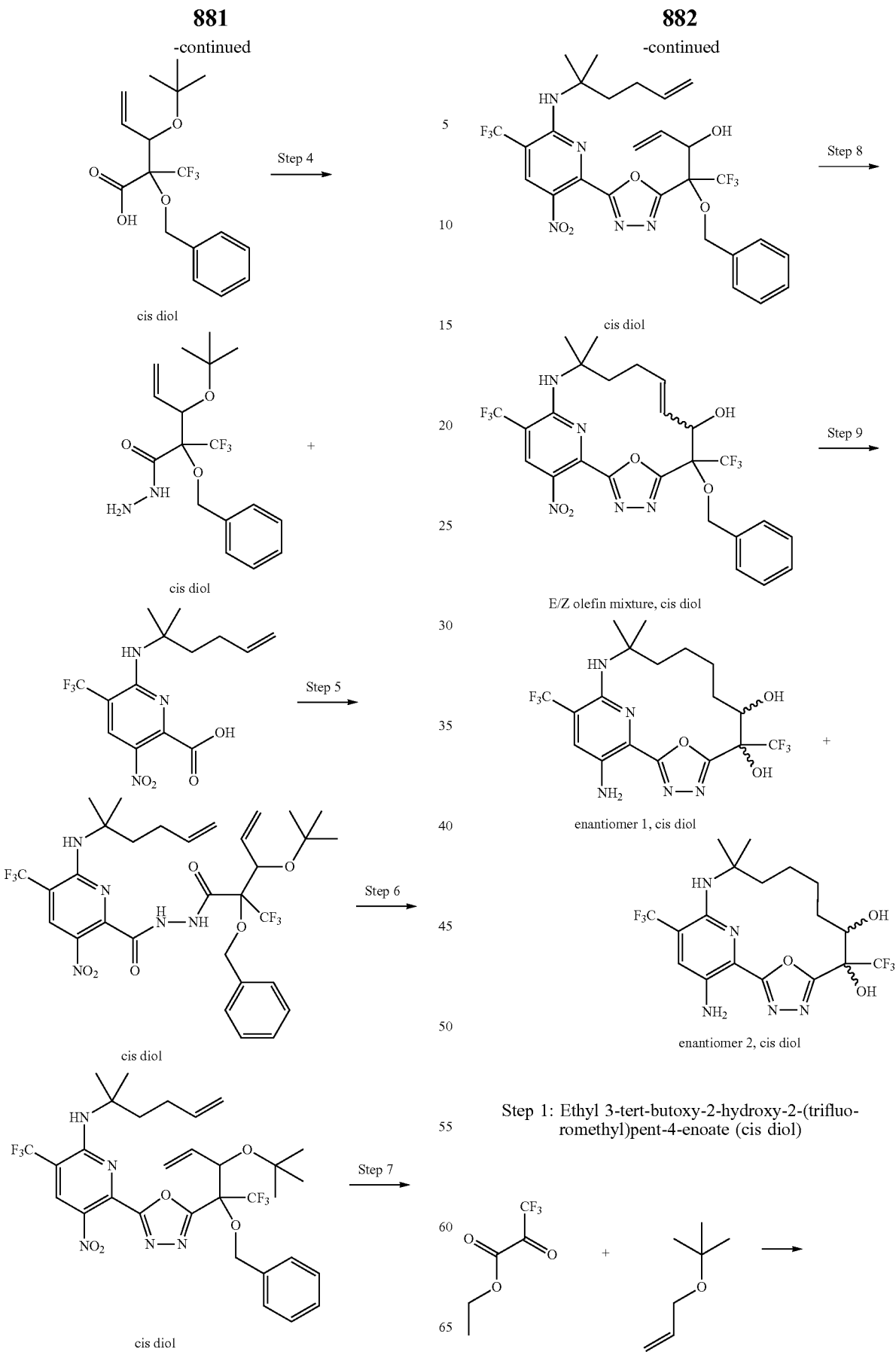
Step 1: Ethyl 3-tert-butoxy-2-hydroxy-2-(trifluoromethyl)pent-4-enoate (cis diol)

-continued

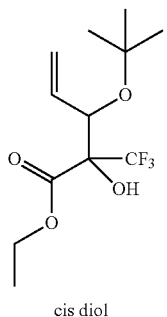

cis diol

A flame-dried flask was charged with 2-allyloxy-2-methylpropane (359 mg, 2.7982 mmol), THF (6.5 mL) and TMEDA (286.75 mg, 0.37 mL, 2.4676 mmol). The flask was then cooled in a dry ice-acetone bath and treated dropwise with a cyclohexane solution of sec-butyllithium (1.76 mL of 1.4 M, 2.464 mmol). After 45 minutes, added trimethylaluminum (1.23 mL of 2 M heptane solution, 2.46 mmol) and the reaction was stirred for another 45 minutes. Added ethyl 3,3,3-trifluoro-2-oxo-propanoate (333.58 mg, 0.26 mL, 1.9612 mmol) and the reaction was stirred for another 4 hours in the cold bath. The reaction was quenched with 1 N aqueous HCl (about 40 mL) and stirred vigorously at room temperature for few minutes. The mixture was extracted with diethyl ether (1×40 mL, 2×20 mL). The combined organic layers were washed with brine (2×20 mL), dried over sodium sulfate, filtered and concentrated under reduced pressure. The residue was purified by silica gel chromatography (40 g column) eluting from 0% to 20% ethyl acetate in heptanes giving as a colorless oil and the major, racemic cis isomer, ethyl 3-tert-butoxy-2-hydroxy-2-(trifluoromethyl)pent-4-enoate (cis diol) (341 mg, 57%). $^1$H NMR (400 MHz, Chloroform-d) δ 5.87 (ddd, J=17.6, 10.0, 8.1 Hz, 1H), 5.31-5.20 (m, 2H), 4.55 (d, J=8.1 Hz, 1H), 4.38-4.23 (m, 2H), 3.85 (s, 1H), 1.33 (t, J=7.2 Hz, 3H), 1.23 (s, 9H) ppm. $^{19}$F NMR (377 MHz, Chloroform-d) δ−73.35 (s, 3F) ppm. This product was contaminated with ~6.5% of the racemic trans diol isomer.

Step 2: Ethyl 2-benzyloxy-3-tert-butoxy-2-(trifluoromethyl)pent-4-enoate (cis diol)

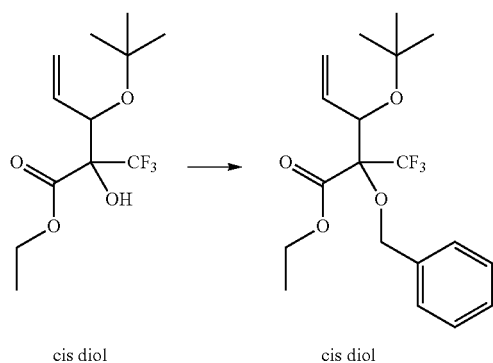 [SMILES: C=CC(OC(C)(C)C)C(O)(C(=O)OCC)C(F)(F)F ; C=CC(OC(C)(C)C)C(OCc1ccccc1)(C(=O)OCC)C(F)(F)F]

cis diol                cis diol

A solution of ethyl 3-tert-butoxy-2-hydroxy-2-(trifluoromethyl)pent-4-enoate (cis diol) (3.24 g, 11.398 mmol) in DMF (50 mL) was cooled in an ice bath and treated with sodium hydride (563 mg, 60% w/w in mineral oil, 14.076 mmol). After 40 minutes, bromomethylbenzene (2.6459 g, 1.84 mL, 15.47 mmol) was added and the reaction was gradually warmed to room temperature and stirred overnight. To the reaction mixture, water (450 mL) was added and the aqueous layer was extracted with MTBE (4×150 mL). The combined organic layers were washed with water (2×150 mL), brine (150 mL), dried over sodium sulfate, filtered and concentrated under reduced pressure. The residue was purified by silica gel chromatography (220 g column) eluting from 0% to 20% ethyl acetate in heptanes giving as a colorless oil, ethyl 2-benzyloxy-3-tert-butoxy-2-(trifluoromethyl)pent-4-enoate (cis diol) (3.86 g, 83%). $^1$H NMR (400 MHz, Chloroform-d) δ 7.46-7.41 (m, 2H), 7.39-7.32 (m, 2H), 7.32-7.28 (m, 1H), 5.98 (ddd, J=17.9, 9.3, 8.6 Hz, 1H), 5.27-5.22 (m, 1H), 5.21 (s, 1H), 4.92-4.85 (m, 1H), 4.79-4.73 (m, 1H), 4.59 (d, J=8.1 Hz, 1H), 4.28 (q, J=7.1 Hz, 2H), 1.32 (t, J=7.1 Hz, 3H), 1.20 (s, 9H) ppm. $^{19}$F NMR (377 MHz, Chloroform-d) δ −65.50 (s, 3F) ppm. ESI-MS m/z calc. 374.1705, found 397.2 (M+Na)$^+$; Retention time: 2.45 minutes (LC Method E).

Step 3: 2-Benzyloxy-3-tert-butoxy-2-(trifluoromethyl)pent-4-enoic acid (cis diol)

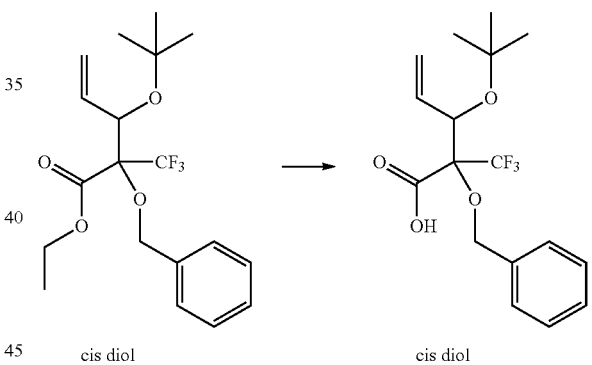

cis diol                cis diol

A solution of sodium hydroxide (1.13 g, 28.252 mmol) in water (10 mL) was added to a solution of ethyl 2-benzyloxy-3-tert-butoxy-2-(trifluoromethyl)pent-4-enoate (cis diol) (3.4 g, 8.6908 mmol) in methanol (30 mL) and the mixture was stirred at 70° C. for 4 days. The reaction mixture was cooled to room temperature and concentrated under reduced pressure to remove most of the methanol. Added water (100 mL) and acidified to pH=2 with 1 N aqueous HCl. The aqueous layer was extracted with ethyl acetate (3×100 mL). The combined organic layers was washed with water (100 mL), brine (100 mL), dried over sodium sulfate, filtered and concentrated under reduced pressure giving as a yellow oil, 2-benzyloxy-3-tert-butoxy-2-(trifluoromethyl)pent-4-enoic acid (cis diol) (3.29 g, 97%). $^1$H NMR (400 MHz, DMSO-d6) δ 14.11 (br. s., 1H), 7.45-7.26 (m, 5H), 5.86 (ddd, J=17.6, 10.0, 8.1 Hz, 1H), 5.34-5.20 (m, 2H), 4.88 (d, J=11.2 Hz, 1H), 4.67-4.56 (m, 2H), 1.15 (s, 9H) ppm. $^{19}$F NMR (377 MHz, DMSO-d6) δ−64.77 (s, 3F) ppm. Retention time: 2.15 minutes (LC Method E).

Step 4: 2-Benzyloxy-3-tert-butoxy-2-(trifluoromethyl)pent-4-enehydrazide (cis diol)

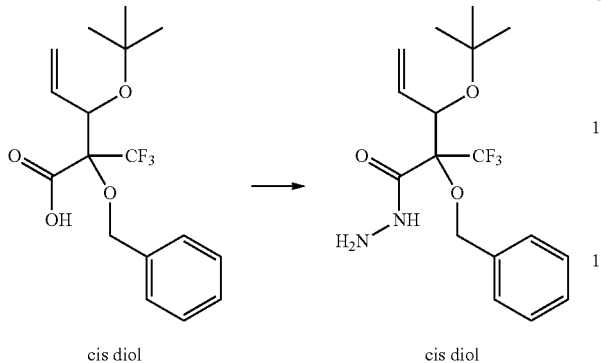

cis diol → cis diol

A solution of 2-benzyloxy-3-tert-butoxy-2-(trifluoromethyl)pent-4-enoic acid (cis diol) (3.29 g, 8.4354 mmol) and triethylamine (2.5410 g, 3.5 mL, 25.111 mmol) in DMF (50 mL) was treated with HATU (6.46 g, 16.99 mmol) and the mixture was stirred at room temperature for 20 minutes. Cooled in an ice bath and added hydrazine hydrate (6.708 g, 10 mL, 87.099 mmol). After about 10 minutes, the ice bath was removed and the reaction was stirred at room temperature for about 18 hours. To the reaction mixture, water (450 mL) was added and the aqueous layer was extracted with ethyl acetate (4×150 mL). The combined organic layers washed with water (2×250 mL), brine (200 mL), dried over sodium sulfate, filtered and concentrated under reduced pressure. The residue was purified by silica gel chromatography (220 g column) eluting from 0% to 50% ethyl acetate in heptanes giving as a colorless oil, 2-benzyloxy-3-tert-butoxy-2-(trifluoromethyl)pent-4-enehydrazide (cis diol) (2.836 g, 91%). $^1$H NMR (400 MHz, DMSO-d6) δ 9.08 (br. s., 1H), 7.45-7.25 (m, 5H), 5.81 (ddd, J=17.4, 10.5, 7.1 Hz, 1H), 5.27 (d, J=17.1 Hz, 1H), 5.21 (d, J=10.5 Hz, 1H), 5.11-4.99 (m, 2H), 4.90 (d, J=7.3 Hz, 1H), 4.36 (d, J=4.4 Hz, 2H), 1.18 (s, 9H) ppm. $^{19}$F NMR (377 MHz, DMSO-d6) δ−67.28 (s, 3F) ppm. ESI-MS m/z calc. 360.1661, found 305.1 (M-55)$^+$; Retention time: 2.13 minutes (LC Method E).

Step 5: N'-[2-Benzyloxy-3-tert-butoxy-2-(trifluoromethyl)pent-4-enoyl]-6-(1,1-dimethylpent-4-enylamino)-3-nitro-5-(trifluoromethyl)pyridine-2-carbohydrazide (cis diol)

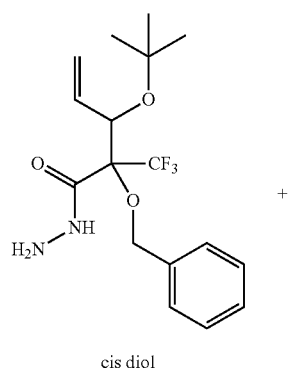

cis diol

+

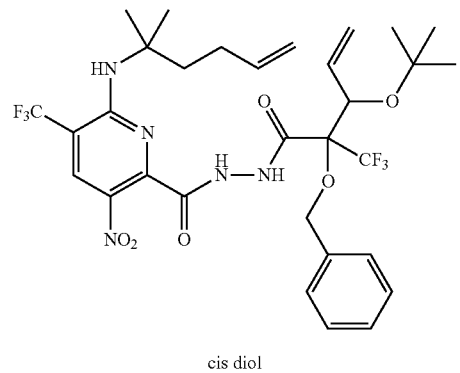

-continued cis diol

A solution of 6-(1,1-dimethylpent-4-enylamino)-3-nitro-5-(trifluoromethyl)pyridine-2-carboxylic acid (775 mg, 2.2316 mmol) and 2-benzyloxy-3-tert-butoxy-2-(trifluoromethyl)pent-4-enehydrazide (cis diol) (750 mg, 2.025 mmol) in DMF (15 mL) was cooled in an ice bath and treated successively with HATU (933 mg, 2.4538 mmol) and DIPEA (534.24 mg, 0.72 mL, 4.1336 mmol). After 5 minutes, the ice bath was removed and the reaction was stirred at room temperature overnight. To the reaction mixture, water (100 mL) was added and the aqueous layer was extracted with ethyl acetate (3×50 mL). The combined organic layers were washed with water (2×50 mL), brine (50 mL), dried over sodium sulfate, filtered and concentrated under reduced pressure. The residue was purified by silica gel chromatography (40 g column) eluting from 0% to 20% of ethyl acetate in heptanes giving as a thick amber oil, N-[2-benzyloxy-3-tert-butoxy-2-(trifluoromethyl)pent-4-enoyl]-6-(1,1-dimethylpent-4-enylamino)-3-nitro-5-(trifluoromethyl)pyridine-2-carbohydrazide (cis diol) (1.136 g, 81%). $^1$H NMR (400 MHz, Chloroform-d) δ 9.61 (d, J 6.6 Hz, 1H), 8.89 (d, J 6.1 Hz, 1H), 8.30 (s, 1H), 7.49-7.31 (m, 5H), 6.02-5.88 (m, 1H), 5.85-5.70 (m, 1H), 5.50-5.29 (m, 3H), 5.27-5.12 (m, 2H), 5.09-4.91 (m, 3H), 2.13-1.93 (m, 4H), 1.56 (s, 3H), 1.52 (s, 3H), 1.27 (s, 9H) ppm. $^{19}$F NMR (377 MHz, Chloroform-d) δ−64.51 (s, 3F), −68.75 (s, 3F) ppm. ESI-MS m/z calc. 689.2648, found 634.2 (M-55)$^+$; Retention time: 2.59 minutes (LC Method E).

Step 6: 6-[5-[1-Benzyloxy-2-tert-butoxy-1-(trifluoromethyl)but-3-enyl]-1,3,4-oxadiazol-2-yl]-N-(1,1-dimethylpent-4-enyl)-5-nitro-3-(trifluoromethyl)pyridin-2-amine (cis diol)

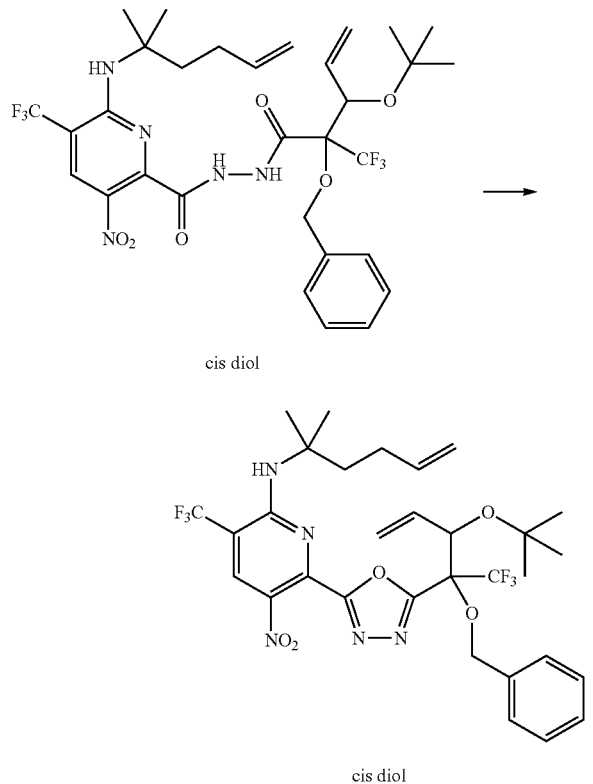

cis diol cis diol

A solution of N-2-benzyloxy-3-tert-butoxy-2-(trifluoromethyl)pent-4-enoyl]-6-(1,1-dimethylpent-4-enylamino)-3-nitro-5-(trifluoromethyl)pyridine-2-carbohydrazide (cis diol) (335 mg, 0.4858 mmol) and DIPEA (222.60 mg, 0.3 mL, 1.7223 mmol) in acetonitrile (8 mL) was heated to 60° C., then p-toluenesulfonyl chloride (106 mg, 0.556 mmol) was added. The resulting mixture was stirred at 60° C. for 90 minutes. The reaction mixture was cooled, and the solution was concentrated to ¼ volume and quenched with an aqueous saturated solution of sodium bicarbonate (5 mL) and then extracted with ethyl acetate (3×30 mL). The organics were separated, dried over sodium sulfate, filtered and evaporated. The residue was purified by silica gel chromatography (40 g column) eluting from 0% to 20% with ethyl acetate in heptanes giving as a pale yellow oil, 6-[5-[1-benzyloxy-2-tert-butoxy-1-(trifluoromethyl)but-3-enyl]-1,3,4-oxadiazol-2-yl]-N-(1,1-dimethylpent-4-enyl)-5-nitro-3-(trifluoromethyl)pyridin-2-amine (cis diol) (312 mg, 96%). $^1$H NMR (400 MHz, Chloroform-d) δ 8.52 (s, 1H), 7.49-7.28 (m, 5H), 6.02 (ddd, J=17.5, 9.7, 8.1 Hz, 1H), 5.83-5.67 (m, 1H), 5.57 (br. s., 1H), 5.36-5.18 (m, 2H), 5.08-4.67 (m, 5H), 2.14-1.89 (m, 4H), 1.56 (s, 3H), 1.49 (s, 3H), 1.11 (s, 9H) ppm. $^{19}$F NMR (377 MHz, Chloroform-d) δ−64.58 (s, 3F), −66.62 (s, 3F) ppm. ESI-MS m/z calc. 671.2542, found 616.2 (M-55)⁺; Retention time: 4.53 minutes (LC Method BB).

Step 7: 4-Benzyloxy-4-[5-[6-(1,1-dimethylpent-4-enylamino)-3-nitro-5-(trifluoromethyl)-2-pyridyl]-1,3,4-oxadiazol-2-yl]-5,5,5-trifluoro-pent-1-en-3-ol (cis diol)

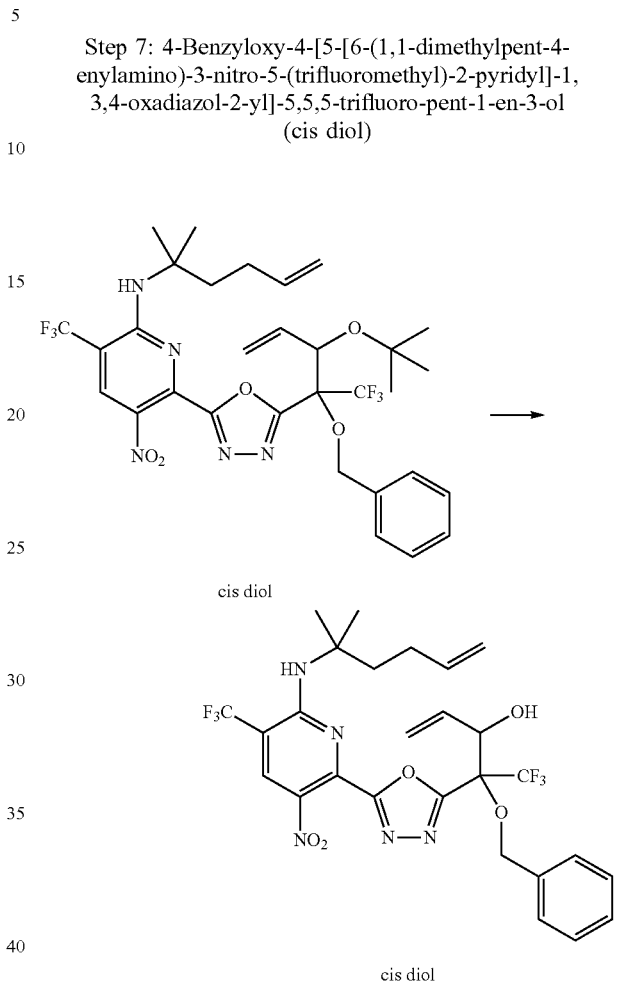

cis diol cis diol

A solution of 6-[5-[1-benzyloxy-2-tert-butoxy-1-(trifluoromethyl)but-3-enyl]-1,3,4-oxadiazol-2-yl]-N-(1,1-dimethylpent-4-enyl)-5-nitro-3-(trifluoromethyl)pyridin-2-amine (cis diol) (1.4 g, 2.0845 mmol) in dichloromethane (14 mL) and TFA (10.360 g, 7 mL, 90.859 mmol) was stirred at room temperature for 1 hour. The reaction was concentrated under reduced pressure and the residue was diluted with dichloromethane (50 mL) and washed with saturated aqueous sodium bicarbonate (25 mL), brine, dried over sodium sulfate, filtered and concentrated under reduced pressure. The residue was purified by silica gel chromatography (40 g column) eluting from 0% to 30% ethyl acetate in heptanes giving as a yellow oil, 4-benzyloxy-4-[5-[6-(1,1-dimethylpent-4-enylamino)-3-nitro-5-(trifluoromethyl)-2-pyridyl]-1,3,4-oxadiazol-2-yl]-5,5,5-trifluoro-pent-1-en-3-ol (cis diol) (1.05 g, 82%). $^1$H NMR (400 MHz, DMSO-d6) δ 8.58 (s, 1H), 7.55-7.21 (m, 5H), 6.24 (s, 1H), 6.00 (ddd, J=17.1, 10.3, 6.6 Hz, 1H), 5.75-5.65 (m, 1H), 5.33-5.17 (m, 2H), 4.99-4.74 (m, 5H), 4.52-4.10 (m, 1H), 2.05-1.82 (m, 4H), 1.43 (s, 6H) ppm. $^{19}$F NMR (377 MHz, DMSO-d6) δ−62.79 (s, 3F), −67.37 (s, 3F) ppm. ESI-MS m/z calc. 615.1916, found 616.03 (M+1)⁺; Retention time: 4.07 minutes (LC Method BB).

Step 8: 6-Benzyloxy-12,12-dimethyl-17-nitro-6,15-bis(trifluoromethyl)-19-oxa-3,4,13,18-tetrazatricyclo[12.3.1.1²,⁵]nonadeca-1(18),2,4,8,14,16-hexaen-7-ol (E/Z olefin mixture, cis diol)

Step 9: 17-Amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,7-diol (enantiomer 1, cis diol) (Compound 194) and 17-amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,7-diol (enantiomer 2, cis diol) (Compound 195)

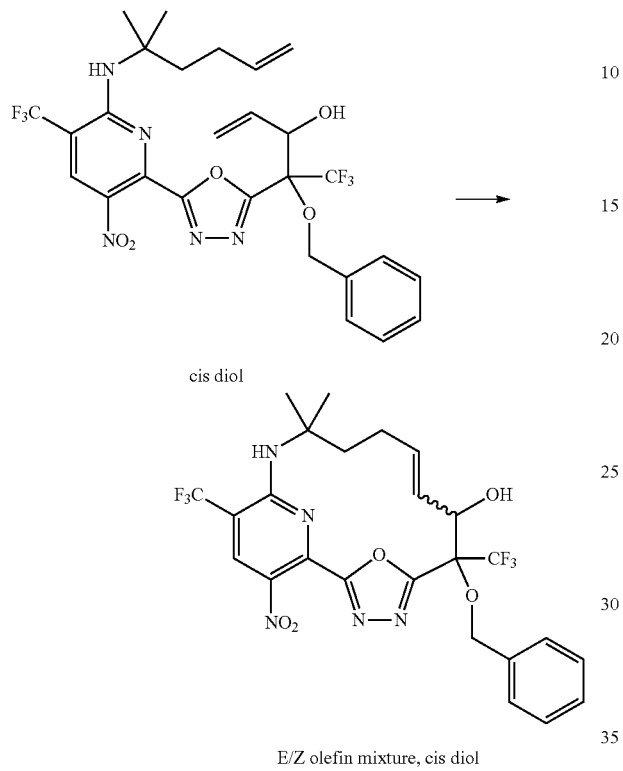

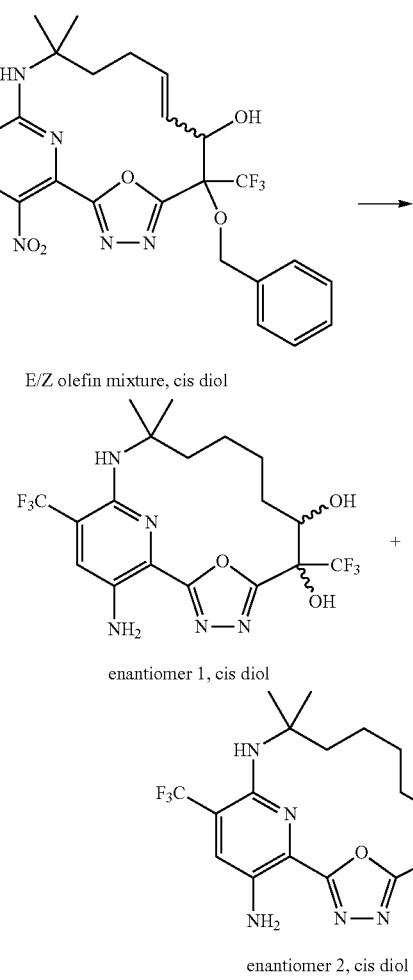

In a 250 mL of oven dried round-bottom flask, a degassed solution of 4-benzyloxy-4-[5-[6-(1,1-dimethylpent-4-enylamino)-3-nitro-5-(trifluoromethyl)-2-pyridyl]-1,3,4-oxadiazol-2-yl]-5,5,5-trifluoro-pent-1-en-3-ol (cis diol) (150 mg, 0.2437 mmol) was heated to 70° C. under nitrogen atmosphere. Then, Zhan catalyst-1B (30 mg, 0.0409 mmol) was added in two portions over 15 minutes. The resulting mixture was heated to 70° C. and stirred for 4 hours. The mixture was cooled and concentrated under reduced pressure. The residue was purified by reverse-phase chromatography on a 50 g $C_{18}$ column, eluting from 5% to 90% acetonitrile in water (containing 0.1% formic acid) giving as an off-white solid, 6-benzyloxy-12,12-dimethyl-17-nitro-6,15-bis(trifluoromethyl)-19-oxa-3,4,13,18-tetrazatricyclo[12.3.1.1²,⁵]nonadeca-1(18),2,4,8,14,16-hexaen-7-ol (E/Z olefin mixture, cis diol) (70 mg, 49%). $^1$H NMR (400 MHz, DMSO-d6) δ 8.55 (s, 1H), 7.50-7.43 (m, 2H), 7.40-7.28 (m, 3H), 6.59 (s, 1H), 6.03 (d, J=7.3 Hz, 1H), 5.77-5.57 (m, 2H), 4.85 (d, J=11.2 Hz, 1H), 4.71 (d, J=11.0 Hz, 1H), 4.42 (t, J=7.5 Hz, 1H), 2.39-2.25 (m, 1H), 2.14-1.95 (m, 3H), 1.50 (s, 3H), 1.39 (s, 3H) ppm. $^{19}$F NMR (377 MHz, DMSO-d6) δ -62.43 (s, 3F), -66.71 (s, 3F) ppm. ESI-MS m/z calc. 587.1603, found 588.2 (M+1)⁺; Retention time: 3.78 minutes (LC Method BB).

A solution of 6-benzyloxy-12,12-dimethyl-17-nitro-6,15-bis(trifluoromethyl)-19-oxa-3,4,13,18-tetrazatricyclo[12.3.1.1²,⁵]nonadeca-1(18),2,4,8,14,16-hexaen-7-ol (E/Z olefin mixture, cis diol) (46 mg, 0.0776 mmol) in methanol (2.5 mL) was purged three times under nitrogen atmosphere and vacuum sequentially. Added 10 wt. % palladium on carbon (45 mg, 0.0211 mmol) then purged twice under hydrogen atmosphere and vacuum sequentially and the reaction was left to stir at room temperature under hydrogen atmosphere for 17 hours. The reaction was purged under nitrogen atmosphere and the mixture was filtered over a pad of Celite and washed with methanol. Concentrated the mixture under reduced pressure and the residue was purified by silica gel chromatography (24 g column) eluting from 0% to 40% ethyl acetate in heptanes giving 27 mg of a yellow solid. Purification by SFC (sample dissolved 18 mg/mL in methanol) using a Phenomenex Lux i-Cellulose (250×21.2 mm, 5 µM column), using a gradient of 10% MeOH (0.1% diethylamine)/90% $CO_2$ with a flow of 75 mL/min giving two enantiomers:

The first enantiomer to elute was isolated as an intense yellow solid, 17-amino-12,12-dimethyl-6,15-bis(trifluoromethyl)-19-oxa-3,4,13,18-tetrazatricyclo[12.3.1.1.2,5]nonadeca-1(18),2,4,14,16-pentaene-6,7-diol (enantiomer 1, cis diol) (10.2 mg, 27%). $^1$H NMR (400 MHz, DMSO-d6) δ 7.57 (s, 1H), 7.51 (s, 1H), 5.91 (s, 2H), 5.37 (d, J=8.6 Hz, 1H), 4.65 (s, 1H), 4.37 (t, J=9.9 Hz, 1H), 1.84-1.62 (m, 2H), 1.50-1.10 (m, 12H) ppm. $^{19}$F NMR (377 MHz, DMSO-d6) δ−62.31 (s, 3F), −73.66 (s, 3F) ppm. ESI-MS m/z calc. 469.1549, found 470.2 (M+1)$^+$; Retention time: 3.47 minutes (LC Method BB).

The second enantiomer to elute was isolated as an intense yellow solid, 17-amino-12,12-dimethyl-6,15-bis(trifluoromethyl)-19-oxa-3,4,13,18-tetrazatricyclo[12.3.1.1.2,5]nonadeca-1(18),2,4,14,16-pentaene-6,7-diol (enantiomer 2, cis diol) (10.2 mg, 27%). $^1$H NMR (400 MHz, DMSO-d6) δ 7.57 (s, 1H), 7.52 (s, 1H), 5.91 (br. s., 2H), 5.37 (d, J=6.4 Hz, 1H), 4.65 (s, 1H), 4.44-4.31 (m, 1H), 1.85-1.61 (m, 2H), 1.49-1.11 (m, 12H) ppm. $^{19}$F NMR (377 MHz, DMSO-d6) δ−62.32 (s, 3F), −73.66 (s, 3F) ppm. ESI-MS m/z calc. 469.1549, found 470.2 (M+1)$^+$; Retention time: 3.47 minutes (LC Method BB).

Example 108: Preparation of 17-amino-12,12-dimethyl-6,15-bis(trifluoromethyl)-8,19-dioxa-3,4,13,18-tetrazatricyclo[12.3.1.1.2,5]nonadeca-1(18),2,4,14,16-pentaen-6-ol (Compound 196)

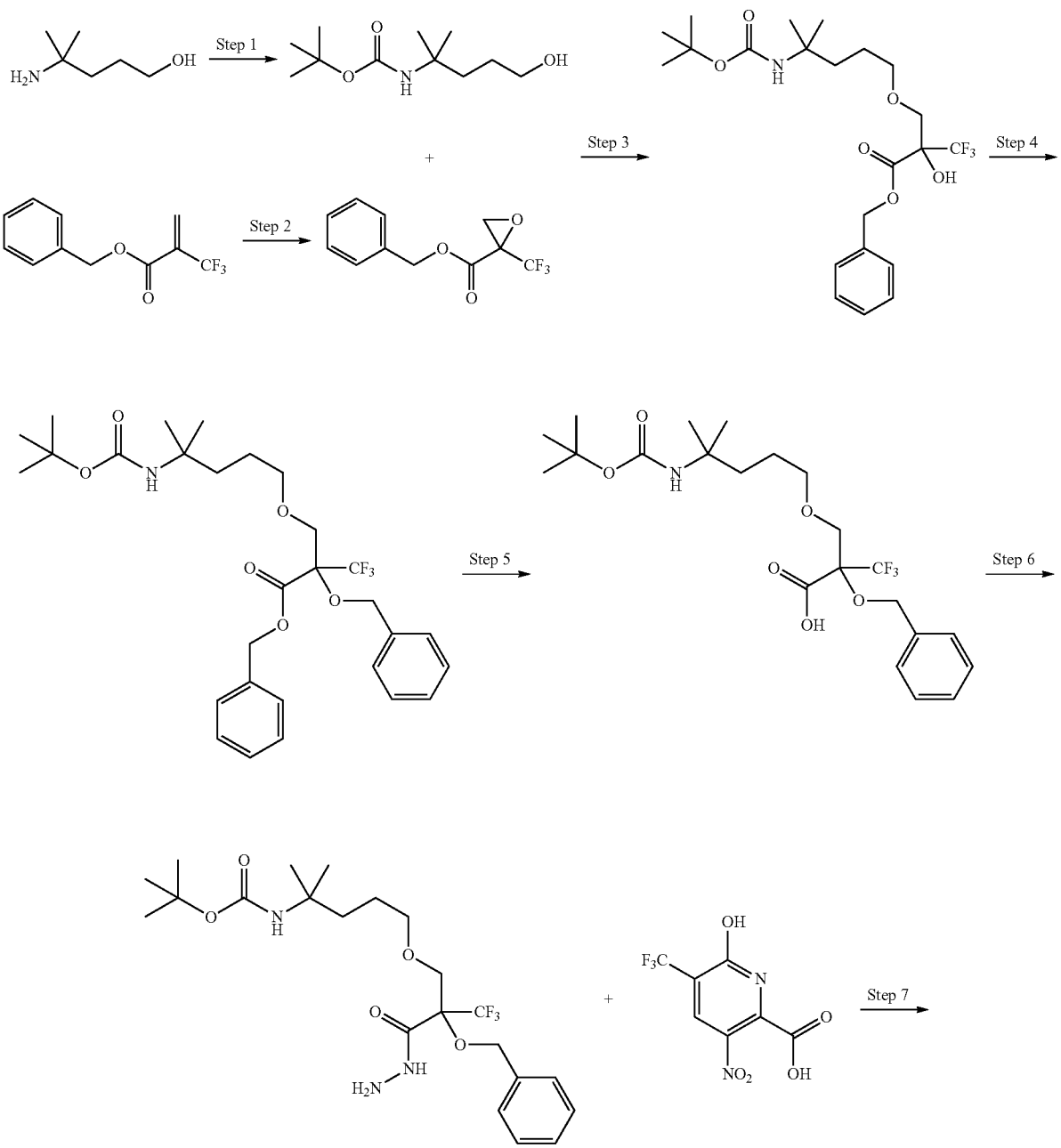

893

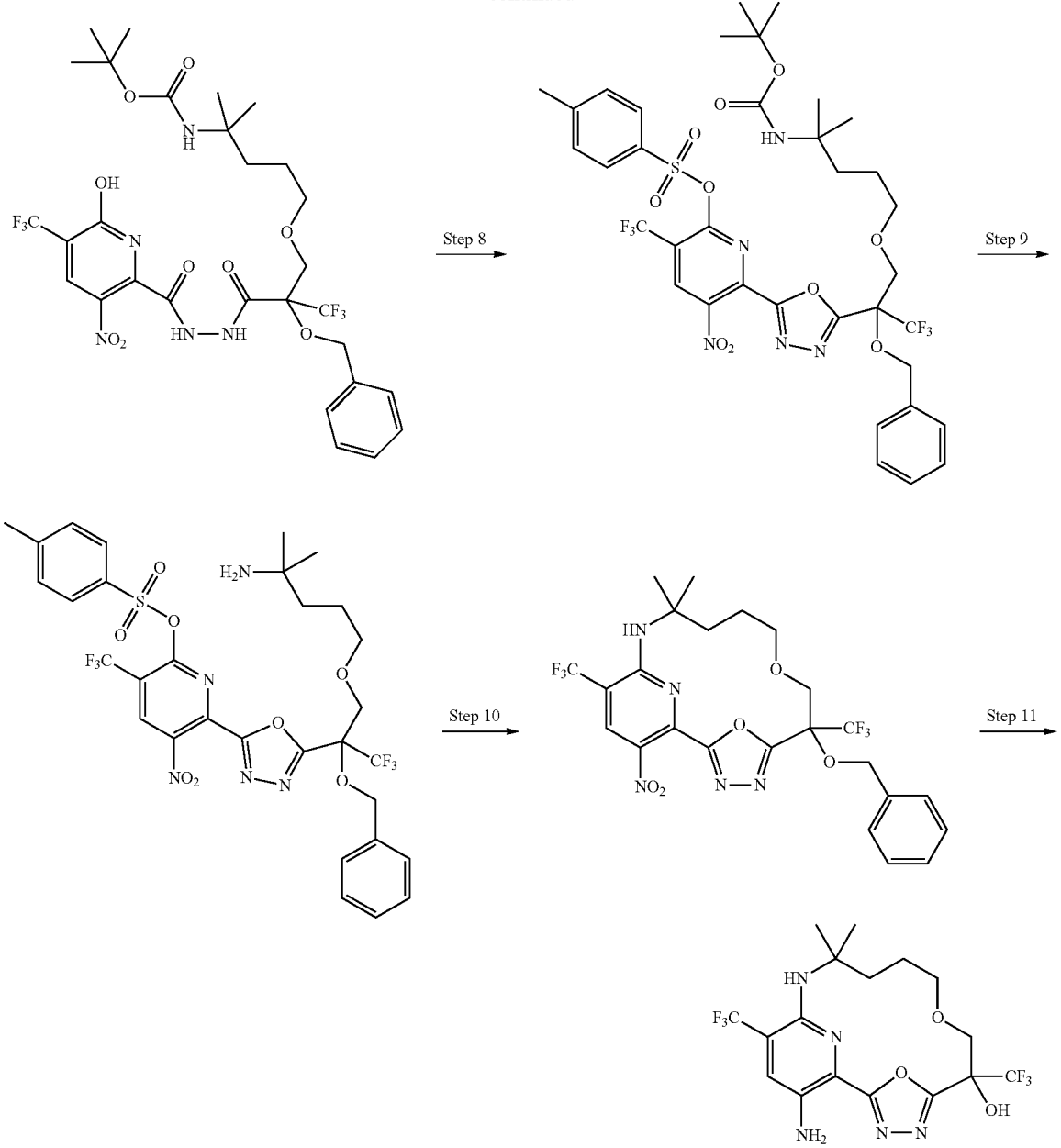

-continued

Step 1: tert-Butyl N-(4-hydroxy-1,1-dimethyl-butyl)carbamate

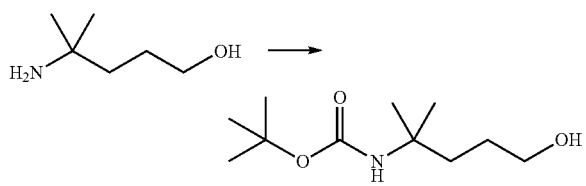

4-Amino-4-methyl-pentan-1-ol (8 g, 64.853 mmol) was dissolved in THF (160 mL) and sodium bicarbonate (20 g, 238.08 mmol) was added to it followed by the addition of di-tert-butyl dicarbonate (21.5 g, 22.632 mL, 98.512 mmol). The reaction mixture was stirred at room temperature for 5 h. The reaction was then diluted with water (300 mL) and EtOAc (400 ml). The aqueous layer was extracted with EtOAc (2×200 mL). The combined organic layers were washed with brine (200 ml), dried over anhydrous sodium sulfate, filtered and concentrated. The residue was purified by silica gel chromatography using a gradient from 0% to 50% acetone in hexanes giving as a white wax, tert-butyl N-(4-hydroxy-1,1-dimethyl-butyl)carbamate (13.7 g, 92%). $^1$H NMR(500 MHz, Chloroform-d) δ 4.47 (s, 1H), 3.62 (t, J=6.5 Hz, 2H), 1.82 (s, 1H), 1.75-1.65 (m, 2H), 1.61-1.48 (m, 2H), 1.41 (s, 9H), 1.24 (s, 6H) ppm. ESI-MS m/z calc. 217.1678, found 218.4 (M+1)$^+$; Retention time: 2.26 minutes (LC Method G).

Step 2: Benzyl 2-(trifluoromethyl)oxirane-2-carboxylate

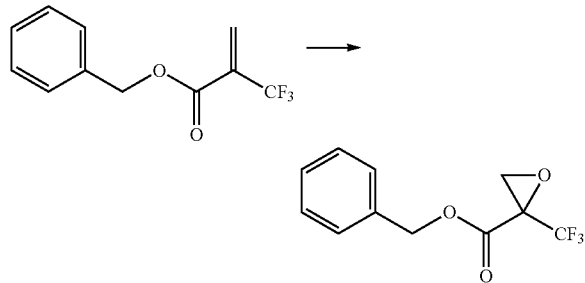

To a solution of benzyl 2-(trifluoromethyl)prop-2-enoate (25.5 g, 110.78 mmol) in dioxane (550 mL) and water (110 mL) was added sodium bicarbonate (47 g, 559.48 mmol) at 0° C. To this mixture, oxone (68.5 g, 222.85 mmol) was added portion-wise with vigorous stirring over 80 min. The reaction was stirred at 0° C. for additional 20 min then warmed to room temperature and stirred for another 1.5 h. The reaction was then diluted with EtOAc (500 mL) and water (500 mL), extracted with EtOAc (2×300 mL). Combined the organic layers then washed with brine (300 mL), dried over anhydrous sodium sulfate, filtered and concentrated. The residue was purified by silica gel chromatography using a gradient from 0% to 50% EtOAc in hexanes giving as a colorless oil, benzyl 2-(trifluoromethyl)oxirane-2-carboxylate (24 g, 81%). $^1$H NMR (500 MHz, Chloroform-d) δ 7.43-7.32 (m, 5H), 5.49-5.10 (m, 2H), 3.28-3.24 (m, 1H), 3.23-3.18 (m, 1H) ppm. Retention time: 3.1 minutes (LC Method G).

Step 3: Benzyl 2-[[4-(tert-butoxycarbonylamino)-4-methyl-pentoxy]methyl]-3,3,3-trifluoro-2-hydroxy-propanoate

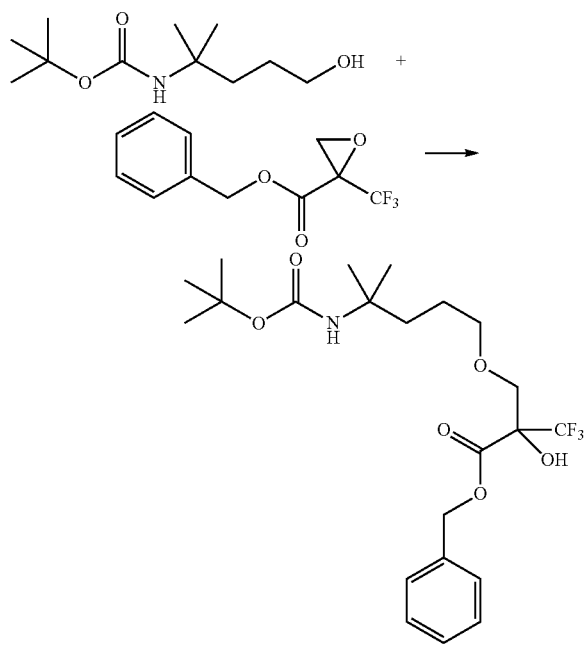

To a solution of benzyl 2-(trifluoromethyl)oxirane-2-carboxylate (5 g, 19.904 mmol) in anhydrous acetonitrile (21.5 mL) was added tert-butyl N-(4-hydroxy-1,1-dimethyl-butyl) carbamate (5.05 g, 22.077 mmol) and magnesium perchlorate (2.22 g, 9.946 mmol) and the mixture was heated at 75° C. for 21 h. The reaction was cooled to room temperature and diluted with EtOAc (50 mL) and water (25 mL). The aqueous layer was extracted with EtOAc (3×100 mL). The combined organic layers were washed with brine (50 mL), dried over anhydrous sodium sulfate, filtered and concentrated. The residue was purified by silica gel chromatography using a gradient from 0% to 30% acetone in hexanes giving as a colorless oil, benzyl 2-[[4-(tert-butoxycarbonylamino)-4-methyl-pentoxy]methyl]-3,3,3-trifluoro-2-hydroxy-propanoate (1.5 g, 16%). $^1$H NMR (500 MHz, Chloroform-d) δ 7.48-7.30 (m, 5H), 5.51-4.90 (m, 2H), 4.44 (br. s, 1H), 4.05 (br. s, 1H), 3.95 (d, J=9.8 Hz, 1H), 3.72 (d, J 9.8 Hz, 1H), 3.56-3.44 (m, 1H), 3.43-3.34 (m, 1H), 1.61-1.53 (m, 2H), 1.52-1.45 (m, 2H), 1.42 (s, 9H), 1.22 (d, J 3.3 Hz, 6H) ppm. ESI-MS m/z calc. 463.21817, found 464.2 (M+1)$^+$; Retention time: 3.81 minutes (LC Method G).

Step 4: Benzyl 2-benzyloxy-2-[[4-(tert-butoxycarbonylamino)-4-methyl-pentoxy]methyl]-3,3,3-trifluoro-propanoate

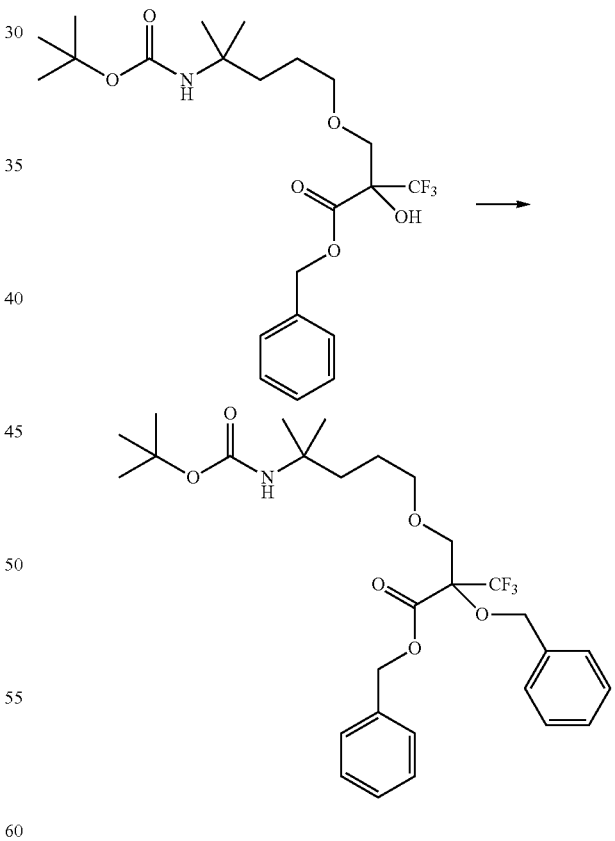

An oven dried flask was charged with NaH (730 mg, 60% w/w, 18.252 mmol) under argon, washed with hexanes (3×10 mL) and DMF (8 mL) was added. The suspension was cooled to 0° C., benzyl 2-[[4-(tert-butoxycarbonylamino)-4-methyl-pentoxy]methyl]-3,3,3-trifluoro-2-hydroxy-propanoate (3.1 g, 6.0196 mmol) in DMF (2.5 mL) was added dropwise (over 2 min). The reaction was stirred at the same temperature for 30 minutes, then bromomethylbenzene (2.3824 g, 1.7 mL, 13.651 mmol) and TBAI (241 mg, 0.6525 mmol) were added. The reaction was stirred at 0° C. for 7 h then slowly warmed to room temperature and stirred for 13 h. The reaction was quenched with saturated ammonium chloride (25 mL) at 0° C. and extracted with ethyl acetate (3×100 mL). The combined organic layers washed with brine (80 mL), dried over anhydrous magnesium sulfate, filtered and concentrated. The residue was purified by silica gel chromatography (120 g column) using a gradient from 0% to 20% diethyl ether in hexanes giving as a colorless oil, benzyl 2-benzyloxy-2-[[4-(tert-butoxycarbonylamino)-4-methyl-pentoxy]methyl]-3,3,3-trifluoro-propanoate (1.7 g, 49%). $^1$H NMR (500 MHz, Chloroform-d) δ 7.38-7.27 (m, 10H), 5.31 (s, 2H), 4.80 (s, 2H), 4.35 (s, 1H), 4.01 (d, J=10.5 Hz, 1H), 3.90 (d, J=10.5 Hz, 1H), 3.50-3.26 (m, 2H), 1.61-1.55 (m, 2H), 1.52-1.44 (m, 2H), 1.41 (s, 9H), 1.21 (s, 6H) ppm. ESI-MS m/z calc. 553.26514, found 554.5 (M+1)$^+$; Retention time: 3.64 minutes (LC Method H).

Step 5: 2-Benzyloxy-2-[[4-(tert-butoxycarbonylamino)-4-methyl-pentoxy]methyl]-3,3,3-trifluoro-propanoic Acid

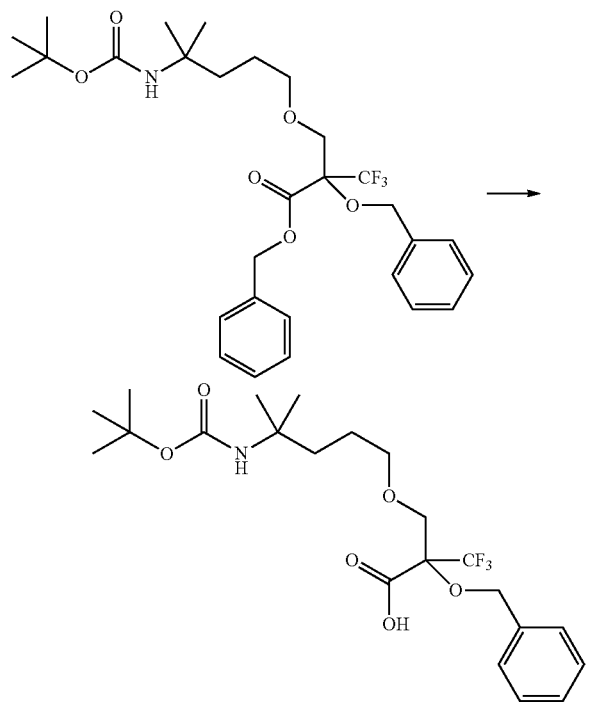

To a solution of benzyl 2-benzyloxy-2-[[4-(tert-butoxycarbonylamino)-4-methyl-pentoxy]methyl]-3,3,3-trifluoro-propanoate (2.4 g, 4.3352 mmol) in THF (7.2 mL) was added LiOH (913 mg, 21.757 mmol) followed by H$_2$O (2.4 mL) and MeOH (2.4 mL) and the reaction was stirred 5 h at room temperature. The mixture was diluted with TBME (50 mL), washed with water (25 mL), HCl (26 mL of 1 M, 26 mmol), water (50 mL), brine (2×50 mL), dried over Na$_2$SO$_4$, filtered and concentrated to provide as a pale yellow oil, 2-benzyloxy-2-[[4-(tert-butoxycarbonylamino)-4-methyl-pentoxy]methyl]-3,3,3-trifluoro-propanoic acid (2.115 g, 100%). $^1$H NMR (500 MHz, Chloroform-d) δ 7.43-7.29 (m, 5H), 4.87 (s, 2H), 4.71 (s, 1H), 4.05 (d, J 10.3 Hz, 1H), 3.97 (d, J=9.4 Hz, 1H), 3.52 (dd, J 11.2, 5.5 Hz, 2H), 1.75-1.50 (m, 4H), 1.43 (s, 9H), 1.24 (s, 6H) ppm. Acidic proton not observed in the field of the proton NMR. ESI-MS m/z calc. 463.21817, found 464.5 (M+1)$^+$; Retention time: 6.37 minutes (LC Method DD).

Step 6: tert-Butyl N-[4-[2-benzyloxy-3,3,3-trifluoro-2-(hydrazinecarbonyl)propoxy]-1,1-dimethyl-butyl] carbamate

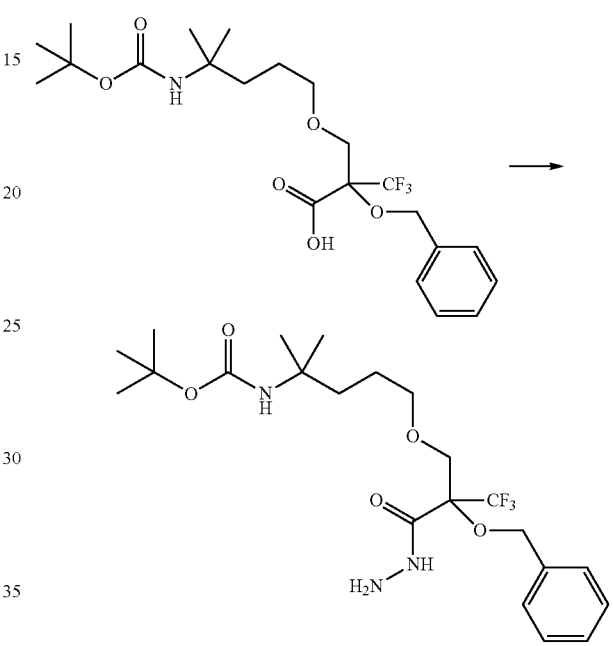

To a solution of 2-benzyloxy-2-[[4-(tert-butoxycarbonylamino)-4-methyl-pentoxy]methyl]-3,3,3-trifluoro-propanoic acid (2 g, 4.0994 mmol) in DMF (17.8 mL) was added HATU (2.34 g, 6.1542 mmol) and Et$_3$N (1.2342 g, 1.7 mL, 12.197 mmol) at room temperature and the resulting yellow solution was stirred for 42 min, cooled to 0° C., then added hydrazine (3.0630 g, 3 mL, 95.584 mmol) dropwise over 10 min. The reaction mixture was stirred at 0° C. for 45 min and warmed to room temperature. The reaction was quenched with NH$_4$Cl solution (40 mL), extracted with EtOAc (3×40 mL), washed with water (100 mL), brine (100 mL), dried over Na$_2$SO$_4$, filtered and concentrated. The residue was purified by silica gel chromatography (80 g column) using a gradient from 0% to 30% EtOAc in hexanes over 45 minutes giving as a colorless oil, tert-butyl N-[4-[2-benzyloxy-3,3,3-trifluoro-2-(hydrazinecarbonyl)propoxy]-1,1-dimethyl-butyl]carbamate (564.2 mg, 27%). $^1$H NMR (500 MHz, Chloroform-d) δ 7.99 (s, 1H), 7.43-7.31 (m, 5H), 4.88-4.79 (m, 2H), 4.42 (s, 1H), 4.17 (d, J=10.9 Hz, 1H), 4.08 (d, J=10.7 Hz, 1H), 3.92 (d, J=4.5 Hz, 2H), 3.56-3.49 (m, 2H), 1.70 (s, 1H), 1.66-1.61 (m, 1H), 1.41 (s, 9H), 1.24 (d, J=4.8 Hz, 6H) ppm. Two exchangeable protons not observed in $^1$H NMR. ESI-MS m/z calc. 477.24506, found 478.6 (M+1)$^+$; Retention time: 5.5 minutes (LC Method DD).

899

Step 7: tert-Butyl N-[4-[2-benzyloxy-3,3,3-trifluoro-2-[[[6-hydroxy-3-nitro-5-(trifluoromethyl)pyridine-2-carbonyl]amino]carbamoyl]propoxy]-1,1-dimethyl-butyl]carbamate

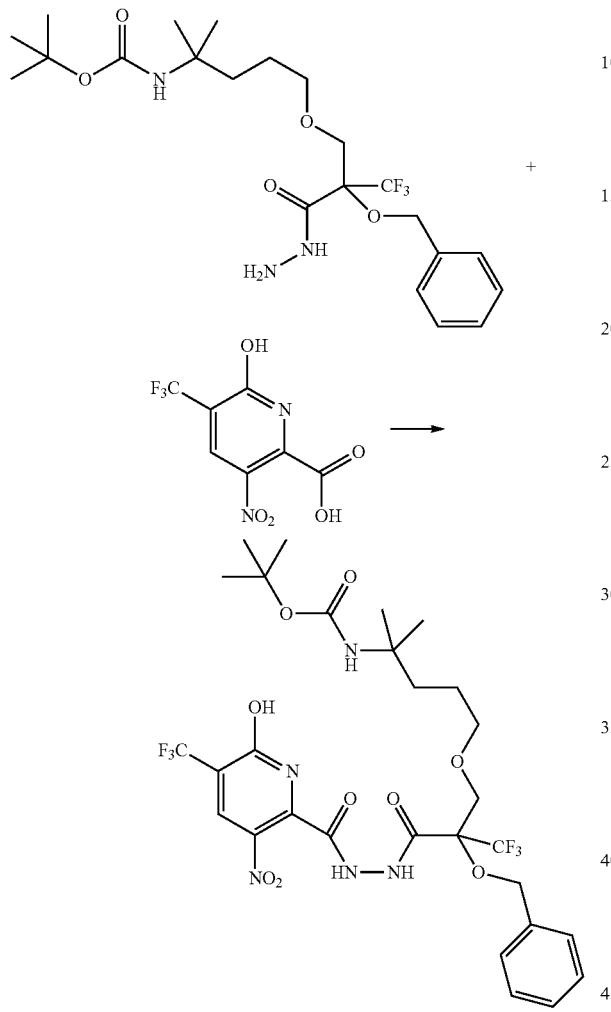

To a solution of tert-butyl N-[4-[2-benzyloxy-3,3,3-trifluoro-2-(hydrazinecarbonyl)propoxy]-1,1-dimethyl-butyl]carbamate (564.2 mg, 1.1815 mmol) in EtOAc (5 mL) was added pyridine (547.68 mg, 0.56 mL, 6.9239 mmol), 6-hydroxy-3-nitro-5-(trifluoromethyl)pyridine-2-carboxylic acid (313 mg, 1.2416 mmol) and T$_3$P (1.25 g, 1.9643 mmol) and the reaction mixture was stirred for 6 h at room temperature. The reaction was quenched with NH$_4$Cl (40 mL) and extracted with EtOAc (3×40 mL). The combined organic layers were washed with water (100 mL) and brine (100 mL), dried over Na$_2$SO$_4$, filtered and concentrated in vacuo. The residue was purified by silica gel chromatography (40 g column) using a gradient from 0% to 100% EtOAc in hexanes giving as a yellow glassy material, tert-butyl N-[4-[2-benzyloxy-3,3,3-trifluoro-2-[[[6-hydroxy-3-nitro-5-(trifluoromethyl)pyridine-2-carbonyl]amino]carbamoyl]propoxy]-1,1-dimethyl-butyl]carbamate (300 mg, 34%). ESI-MS m/z calc. 711.2339, found 712.6 (M+1)$^+$; Retention time: 6.87 minutes (LC Method DD).

900

Step 8: [6-[5-[1-Benzyloxy-1-[[4-(tert-butoxycarbonylamino)-4-methyl-pentoxy]methyl]-2,2,2-trifluoro-ethyl]-1,3,4-oxadiazol-2-yl]-5-nitro-3-(trifluoromethyl)-2-pyridyl]4-methylbenzenesulfonate

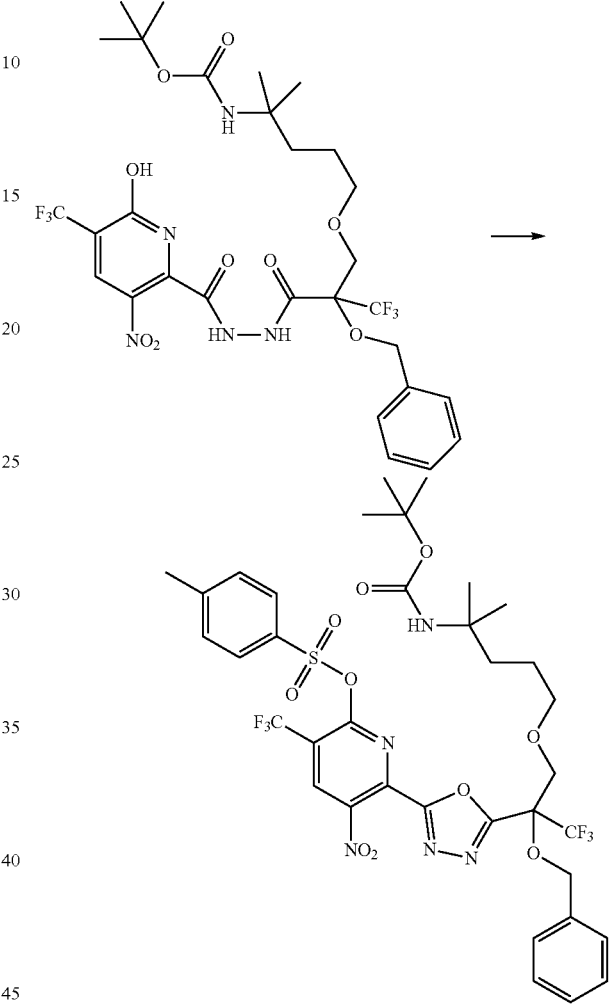

To a solution of tert-butyl N-[4-[2-benzyloxy-3,3,3-trifluoro-2-[[[6-hydroxy-3-nitro-5-(trifluoromethyl)pyridine-2-carbonyl]amino]carbamoyl]propoxy]-1,1-dimethyl-butyl]carbamate (142 mg, 0.1995 mmol) in CH$_3$CN (2.15 mL) was added DIPEA (133.56 mg, 0.180 mL, 1.0334 mmol) then p-TsCl (115 mg, 0.6032 mmol) and the mixture was stirred for 50 h at room temperature. The reaction mixture was quenched with NH$_4$Cl solution (15 mL) and extracted with EtOAc (3×30 mL). The combined organic layers were washed with NaHCO$_3$(20 mL), brine, dried over Na$_2$SO$_4$, filtered and concentrated. The residue was purified by silica gel chromatography (40 g column) using a gradient from 0% to 30% EtOAc in hexanes giving as a pale yellow solid [6-[5-[1-benzyloxy-1-[[4-(tert-butoxycarbonylamino)-4-methyl-pentoxy]methyl]-2,2,2-trifluoro-ethyl]-1,3,4-oxadiazol-2-yl]-5-nitro-3-(trifluoromethyl)-2-pyridyl]4-methyl-benzenesulfonate (124 mg, 70%). $^1$H NMR (500 MHz, Chloroform-d) δ 8.60 (s, 1H), 8.08 (d, J=8.4 Hz, 2H), 7.41-7.27 (m, 7H), 4.88 (d, J=10.8 Hz, 1H), 4.82 (d, J=10.8 Hz, 1H), 4.37 (s, 1H), 4.35-4.28 (m, 2H), 3.57 (t, J=6.2 Hz, 2H), 2.39 (s, 3H), 1.66-1.60 (m, 2H), 1.59-1.52 (m, 2H), 1.39 (s, 9H), 1.20 (s, 6H) ppm. ESI-MS m/z calc. 847.2322, found 848.6 (M+1)⁺; Retention time: 8.48 minutes (LC Method DD).

Step 9: [6-[5-[1-[(4-Amino-4-methyl-pentoxy)methyl]-1-benzyloxy-2,2,2-trifluoro-ethyl]-1,3,4-oxadiazol-2-yl]-5-nitro-3-(trifluoromethyl)-2-pyridyl]4-methylbenzenesulfonate

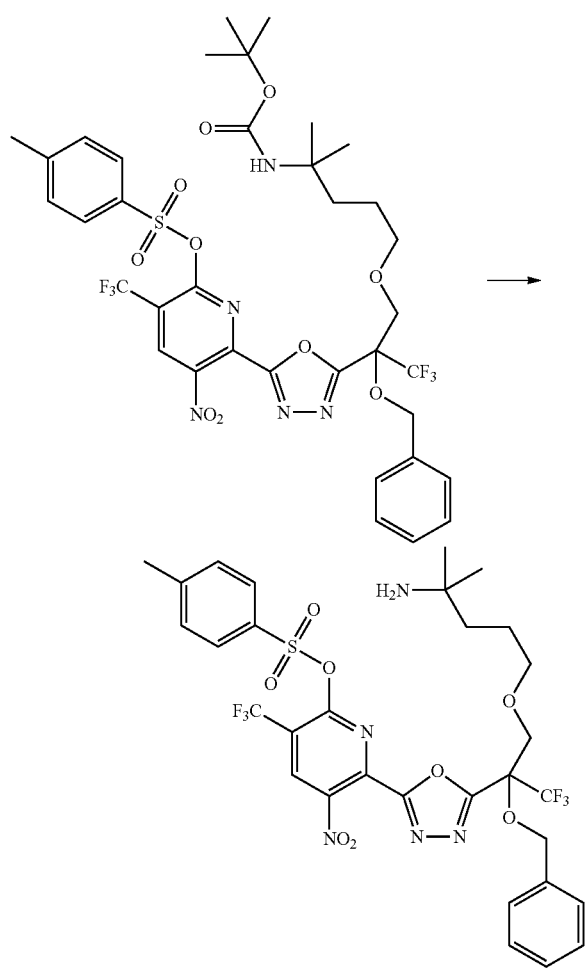

To a solution of [6-[5-[1-benzyloxy-1-[[4-(tert-butoxycarbonylamino)-4-methyl-pentoxy]methyl]-2,2,2-trifluoro-ethyl]-1,3,4-oxadiazol-2-yl]-5-nitro-3-(trifluoromethyl)-2-pyridyl] 4-methylbenzenesulfonate (25 mg, 0.0295 mmol) in DCM was added TFA (740 mg, 0.5 mL, 6.4899 mmol) and the mixture was stirred for 30 min at room temperature. The reaction mixture was diluted with DCM (20 mL), quenched with NaHCO₃(20 mL), washed with brine (20 mL), dried over K₂CO₃ and filtered to provide [6-[5-[1-[(4-amino-4-methyl-pentoxy)methyl]-1-benzyloxy-2,2,2-trifluoro-ethyl]-1,3,4-oxadiazol-2-yl]-5-nitro-3-(trifluoromethyl)-2-pyridyl] 4-methylbenzenesulfonate (22 mg, 99%) which was used directly in the next reaction. ESI-MS m/z calc. 747.1798, found 748.5 (M+1)⁺; Retention time: 6.05 minutes (LC Method DD).

Step 10: 6-Benzyloxy-12,12-dimethyl-17-nitro-6,15-bis(trifluoromethyl)-8,19-dioxa-3,4,13,18-tetrazatricyclo[12.3.1.12,5]nonadeca-1(18),2,4,14,16-pentaene

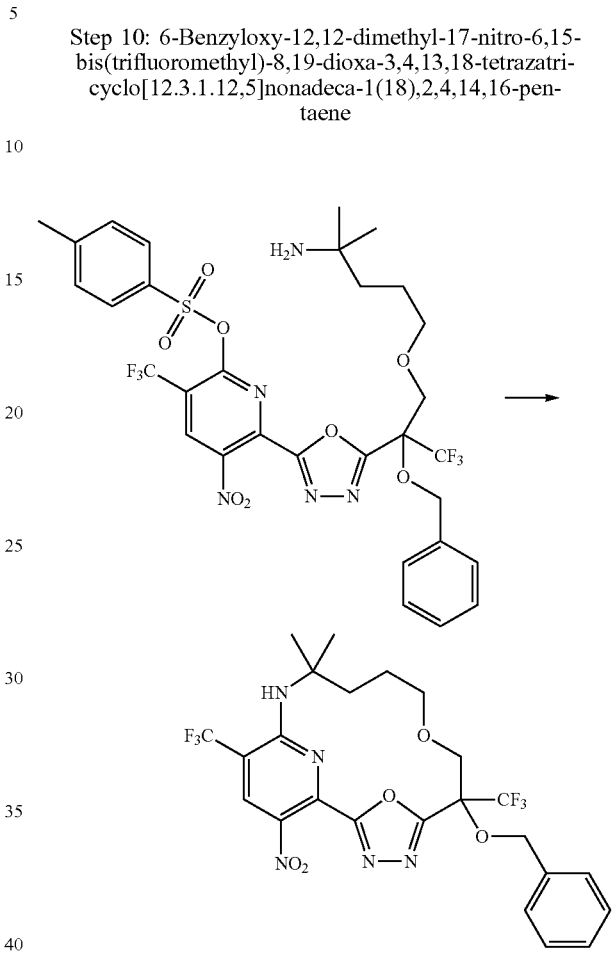

To a solution of [6-[5-[1-[(4-amino-4-methyl-pentoxy)methyl]-1-benzyloxy-2,2,2-trifluoro-ethyl]-1,3,4-oxadiazol-2-yl]-5-nitro-3-(trifluoromethyl)-2-pyridyl] 4-methylbenzenesulfonate (22 mg, 0.0294 mmol) in DCM (20 mL) was added DIPEA (74.200 mg, 0.100 mL, 0.5741 mmol) and the mixture was stirred for 1 h. The volatiles were removed in vacuo and the residue was purified by silica gel chromatography using a gradient from 0% to 20% EtOAc in hexanes giving as an amber oil, 6-benzyloxy-12,12-dimethyl-17-nitro-6,15-bis(trifluoromethyl)-8,19-dioxa-3,4,13,18-tetrazatricyclo[12.3.1.12,5]nonadeca-1(18),2,4,14,16-pentaene (8 mg, 45%). ¹H NMR (500 MHz, Chloroform-d) δ 8.52 (d, J=0.7 Hz, 1H), 7.42-7.25 (m, 5H), 5.56 (s, 1H), 4.94 (d, J=11.3 Hz, 1H), 4.82 (d, J=11.3 Hz, 1H), 4.16 (d, J=10.1 Hz, 1H), 4.08 (dd, J=10.1, 1.2 Hz, 1H), 3.62-3.54 (m, 1H), 3.45-3.36 (m, 1H), 2.64-2.54 (m, 1H), 2.37-2.27 (m, 1H), 1.64-1.49 (m, 2H), 1.40 (s, 6H) ppm. ESI-MS m/z calc. 575.16034, found 576.4 (M+1)⁺; Retention time: 7.66 minutes (LC Method DD).

903

Step 11: 17-Amino-12,12-dimethyl-6,15-bis(trifluoromethyl)-8,19-dioxa-3,4,13,18-tetrazatricyclo[12.3.1.12,5]nonadeca-1(18),2,4,14,16-pentaen-6-ol (Compound 196)

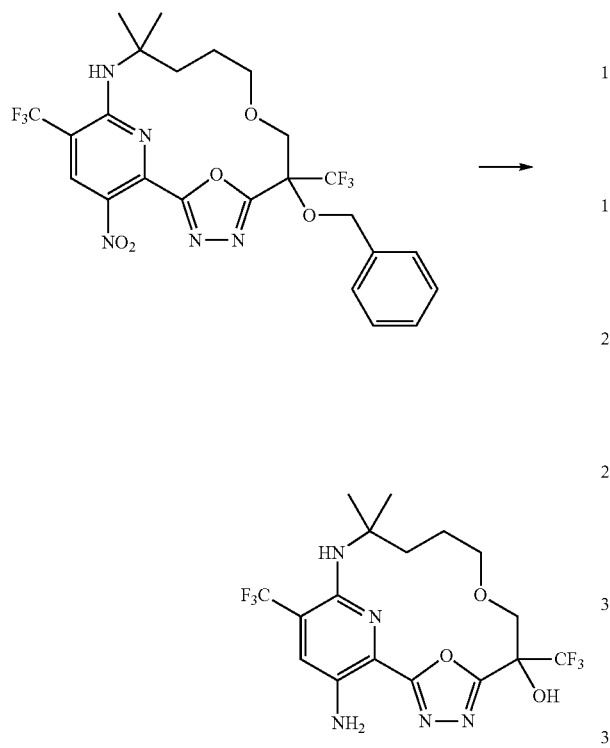

To a solution of 6-benzyloxy-12,12-dimethyl-17-nitro-6,15-bis(trifluoromethyl)-8,19-dioxa-3,4,13,18-tetrazatricyclo[12.3.1.12,5]nonadeca-1(18),2,4,14,16-pentaene (10 mg, 0.0174 mmol) in EtOH (3.1 mL) under nitrogen, was added Pd/C (7 mg, 10% w/w, 0.0066 mmol) then purged with hydrogen gas for 1 min and stirred under 1 atm hydrogen gas for 5.5 h at room temperature. The reaction mixture was backfilled with nitrogen and diluted with EtOH (20 mL), filtered through a pad of Celite and rinsed with EtOH (3×20 mL) and the filtrate concentrated. The residue was purified by reverse phase $C_{18}$ (15.5 g column), using a mobile phase of 0% to 95% acetonitrile in water (0.1% formic acid) giving as a yellow solid, 17-amino-12,12-dimethyl-6,15-bis(trifluoromethyl)-8,19-dioxa-3,4,13,18-tetrazatricyclo[12.3.1.12,5]nonadeca-1(18),2,4,14,16-pentaen-6-ol (7 mg, 76%). $^1$H NMR (400 MHz, $CD_3OD$) δ 7.47 (s, 1H), 4.08 (d, J=9.5 Hz, 1H), 3.87 (d, J=9.5 Hz, 1H), 3.75-3.64 (m, 1H), 3.61-3.49 (m, 1H), 3.07-2.90 (m, 1H), 2.46-2.31 (m, 1H), 1.83-1.60 (m, 2H), 1.39 (s, 3H), 1.34 (s, 3H) ppm. $^{19}$F NMR (377 MHz, $CD_3OD$) δ −65.22 (s, 3F), −78.99 (s, 3F) ppm. ESI-MS m/z calc. 455.1392, found 456.2 (M+1)$^+$; Retention time: 3.19 minutes (LC Method C).

904

Example 109: Preparation of 17-amino-12,12-dimethyl-6,15-bis(trifluoromethyl)-8,19-dioxa-3,4,13,18-tetrazatricyclo[12.3.1.12,5]nonadeca-1(18),2,4,14,16-pentaen-6-ol (enantiomer 1) (Compound 197) and 17-amino-12,12-dimethyl-6,15-bis(trifluoromethyl)-8,19-dioxa-3,4,13,18-tetrazatricyclo[12.3.1.12,5]nonadeca-1(18),2,4,14,16-pentaen-6-ol (enantiomer 2) (Compound 198)

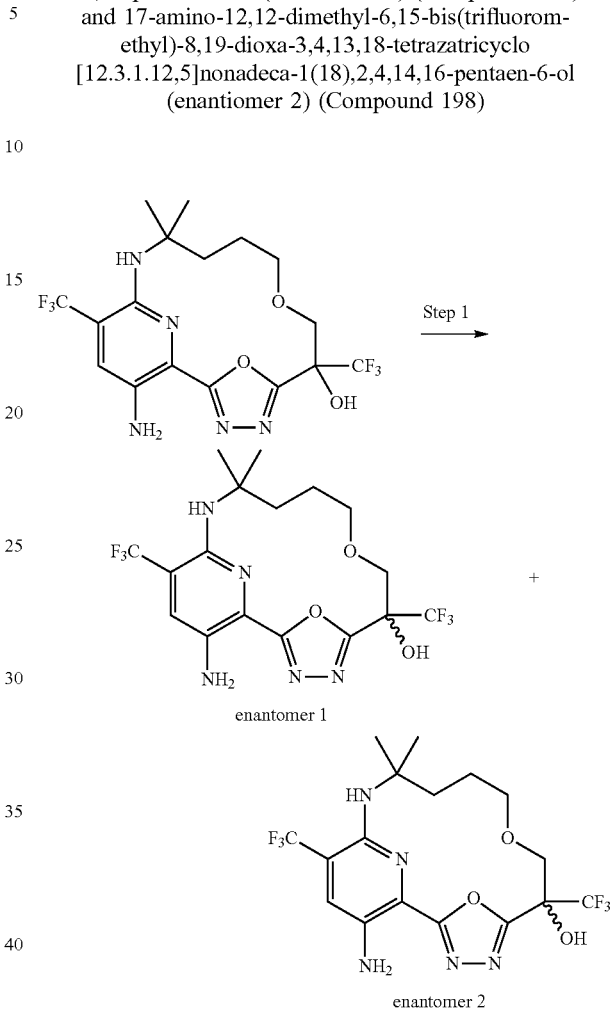

Step 1: 17-Amino-12,12-dimethyl-6,15-bis(trifluoromethyl)-8,19-dioxa-3,4,13,18-tetrazatricyclo[12.3.1.12,5]nonadeca-1(18),2,4,14,16-pentaen-6-ol (enantiomer 1) (Compound 197) and 17-amino-12,12-dimethyl-6,15-bis(trifluoromethyl)-8,19-dioxa-3,4,13,18-tetrazatricyclo[12.3.1.12,5]nonadeca-1(18),2,4,14,16-pentaen-6-ol (enantiomer 2) (Compound 198)

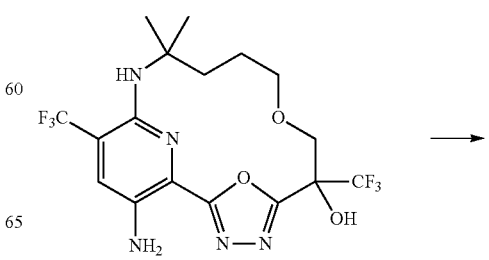

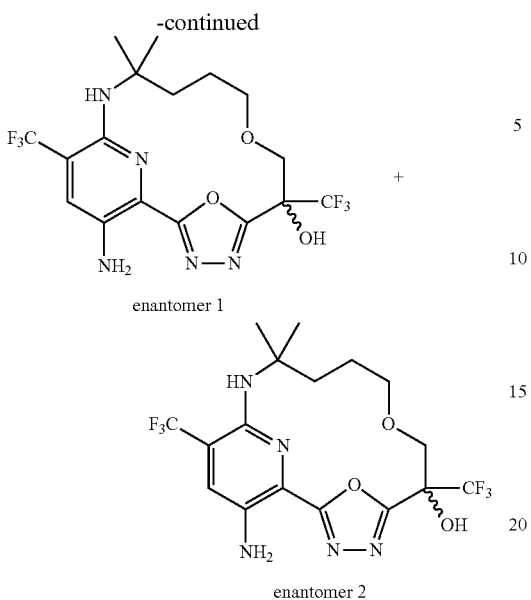

enantomer 1 enantomer 2

Racemic 17-amino-12,12-dimethyl-6,15-bis(trifluoromethyl)-8,19-dioxa-3,4,13,18-tetrazatricyclo[12.3.1.12,5]nonadeca-1(18),2,4,14,16-pentaen-6-ol (10 mg, 0.02196 mmol) was purified by chiral SFC using an AS-H column (250×10 mm, 5 μm particle size) sold by Chiral Technologies and eluting with 8% MeOH (+20 mM $NH_3$) in $CO_2$ which provided two single enantiomer products:

The first enantiomer to elute was isolated as a yellow solid, 17-amino-12,12-dimethyl-6,15-bis(trifluoromethyl)-8,19-dioxa-3,4,13,18-tetrazatricyclo[12.3.1.12,5]nonadeca-1(18),2,4,14,16-pentaen-6-ol (enantiomer 1) (3.3 mg, 65%). $^1$H NMR (400 MHz, Chloroform-d) δ 7.27 (s, 1H), 4.90 (s, 2H), 4.43 (s, 1H), 4.11 (d, J 9.4 Hz, 2H), 3.85 (dd, J=9.5, 1.2 Hz, 1H), 3.67 (ddd, J=9.3, 6.0, 3.2 Hz, 1H), 3.59 (td, J 9.6, 9.1, 2.8 Hz, 1H), 3.03 (ddd, J 13.0, 10.6, 4.6 Hz, 1H), 2.27 (ddd, J 13.3, 10.5, 6.1 Hz, 1H), 1.83-1.71 (m, 1H), 1.67 (dtd, J=11.1, 6.0, 2.7 Hz, 1H), 1.39 (s, 3H), 1.32 (s, 3H) ppm. ESI-MS m/z calc. 455.13922, found 456.2 (M+1)$^+$; Retention time: 1.85 minutes (LC Method A).

The second enantiomer to elute was isolated as a yellow solid, 17-amino-12,12-dimethyl-6,15-bis(trifluoromethyl)-8,19-dioxa-3,4,13,18-tetrazatricyclo[12.3.1.12,5]nonadeca-1(18),2,4,14,16-pentaen-6-ol (enantiomer 2) (4.1 mg, 81%). $^1$H NMR (400 MHz, Chloroform-d) δ 7.26 (s, 1H), 4.89 (s, 2H), 4.43 (s, 1H), 4.11 (d, J 9.5 Hz, 2H), 3.85 (dd, J=9.5, 1.4 Hz, 1H), 3.67 (ddd, J=9.3, 6.1, 3.2 Hz, 1H), 3.59 (td, J 9.4, 9.0, 2.8 Hz, 1H), 3.03 (ddd, J=13.2, 10.7, 4.6 Hz, 1H), 2.27 (ddd, J=13.2, 10.5, 6.1 Hz, 1H), 1.74 (ddd, J=10.4, 6.7, 3.3 Hz, 1H), 1.66 (ddd, J=11.4, 6.1, 3.0 Hz, 1H), 1.39 (s, 3H), 1.32 (s, 3H) ppm. ESI-MS m/z calc. 455.13922, found 456.2 (M+1)$^+$; Retention time: 1.85 minutes (LC Method A).

Example 110: Preparation of 17-amino-12,12-dimethyl-6,15-bis(trifluoromethyl)-10,19-dioxa-3,4,13,18-tetrazatricyclo[12.3.1.12,5]nonadeca-1(18),2,4,14,16-pentaen-6-ol (enantiomer 1) (Compound 199) and 17-amino-12,12-dimethyl-6,15-bis(trifluoromethyl)-10,19-dioxa-3,4,13,18-tetrazatricyclo[12.3.1.12,5]nonadeca-1(18),2,4,14,16-pentaen-6-ol (enantiomer 2) (Compound 200)

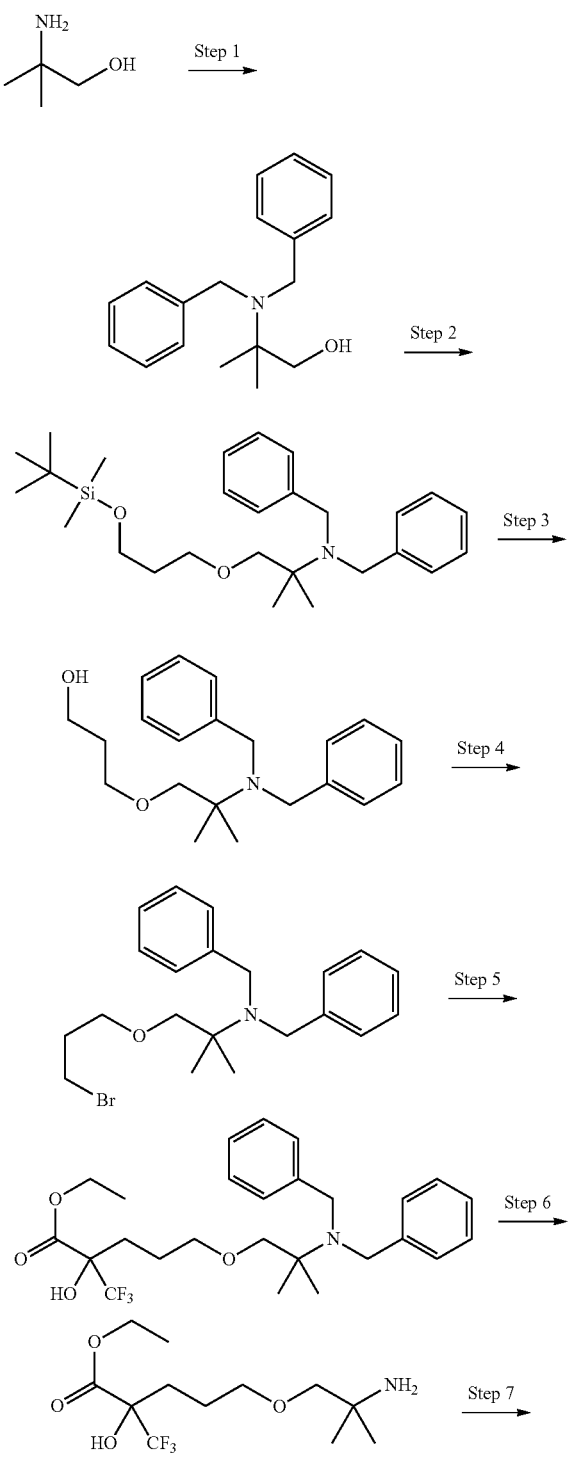

907
908
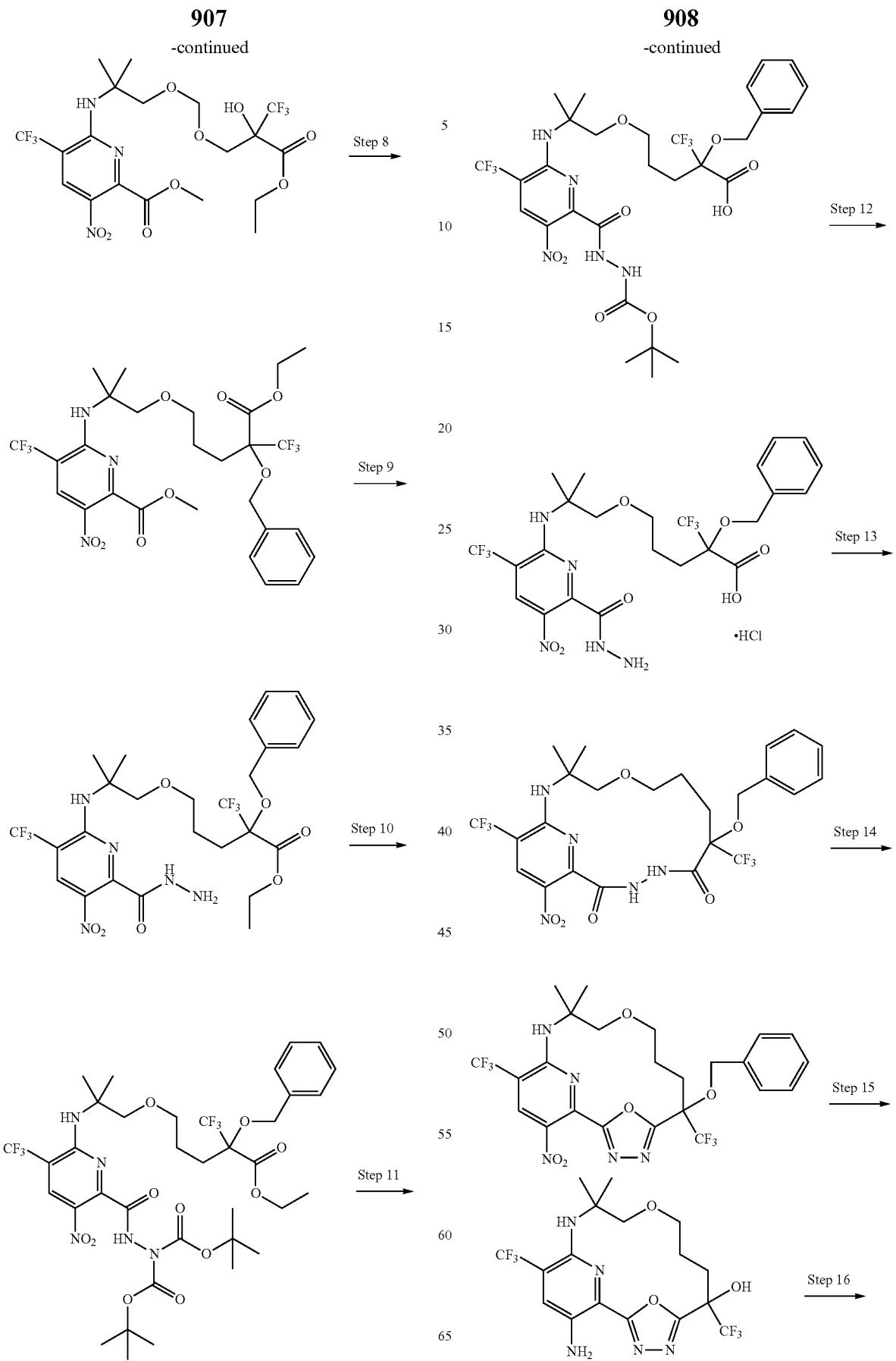

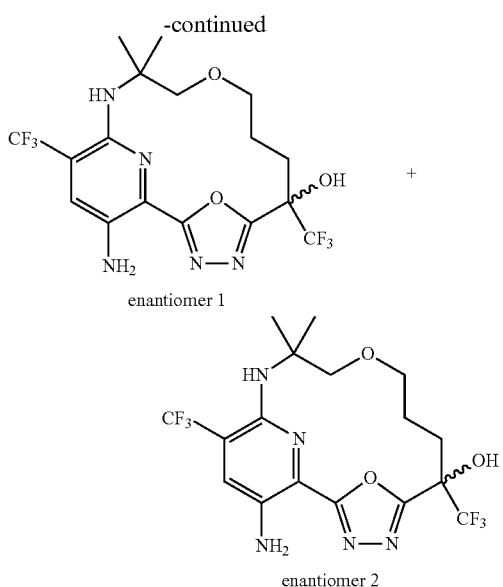

enantiomer 1 enantiomer 2

Step 1: 2-(Dibenzylamino)-2-methyl-propan-1-ol

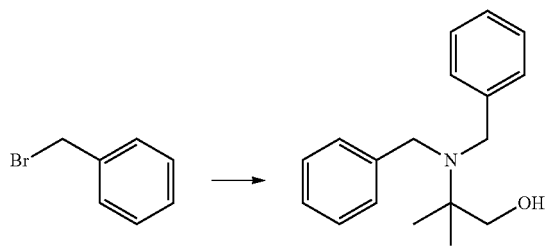 [SMILES: BrCc1ccccc1 ; CC(C)(CO)N(Cc1ccccc1)Cc1ccccc1]

To a solution of 2-amino-2-methyl-propan-1-ol (20.548 g, 22 mL, 230.52 mmol) in a mixture of acetone (250 mL) and water (50 mL) was added potassium carbonate (64 g, 463.08 mmol) followed by bromomethylbenzene (79.200 g, 55 mL, 463.07 mmol) and the reaction was heated at reflux for 72 h. The reaction was cooled to room temperature and concentrated in vacuo. The residue was partitioned between dichloromethane (400 mL) and water (500 mL), the organic layer was collected, washed with water (500 mL), brine (500 mL), dried over sodium sulfate, filtered and concentrated in vacuo. The residue was purified by silica gel chromatography using a gradient from 0% to 5% methanol in dichloromethane to afford as a white solid, 2-(dibenzylamino)-2-methyl-propan-1-ol (34 g, 55%); $^1$H NMR (400 MHz, DMSO-d6) δ 7.26 (d, J=6.8 Hz, 4H), 7.17 (t, J=7.5 Hz, 4H), 7.11-7.03 (m, 2H), 4.43 (t, J=5.4 Hz, 1H), 3.75 (s, 4H), 3.37 (d, J=5.4 Hz, 2H), 1.03 (s, 6H) ppm. ESI-MS m/z calc. 269.178, found 270.2 (M+1)$^+$; Retention time: 1.51 minutes (LC Method E).

Step 2: N,N-Dibenzyl-1-[3-[tert-butyl(dimethyl)silyl]oxypropoxy]-2-methyl-propan-2-amine

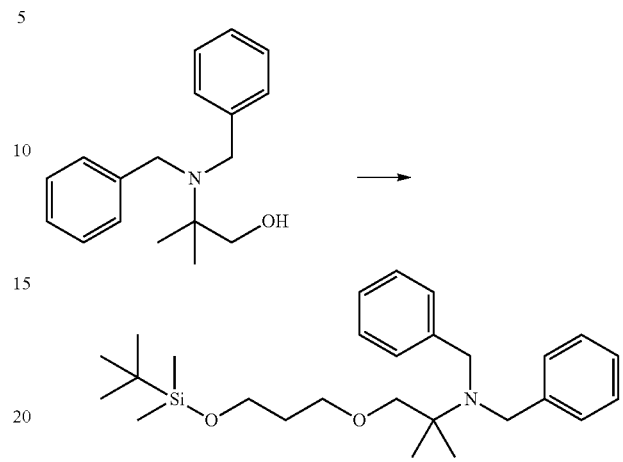

To a solution of 2-(dibenzylamino)-2-methyl-propan-1-ol (20 g, 74.244 mmol) in dimethylformamide (105 mL) at 0° C. was added sodium hydride (60% w/w) (4.1 g, 102.51 mmol) portion-wise. After stirring at 0° C. for 30 min, 3-bromopropoxy-tert-butyl-dimethyl-silane (24.046 g, 22 mL, 94.949 mmol) was added to the above solution. To dilute the mixture, dimethylformamide (21 mL) was added. The reaction mixture was stirred overnight at room temperature and quenched with saturated ammonium chloride (200 mL). The mixture was extracted with ethyl acetate (2×200 mL) then combined organics were washed with water (2×200 mL) and brine (200 mL). The organic layer was dried over sodium sulfate, filtered and concentrated. The crude product was purified by silica gel chromatography using a gradient from 0% to 15% ethyl acetate in heptanes to provide as a colorless oil, N,N-dibenzyl-1-[3-[tert-butyl(dimethyl)silyl]oxypropoxy]-2-methyl-propan-2-amine (16.4 g, 50%). $^1$H NMR (400 MHz, DMSO-d6) δ 7.25 (d, J=7.1 Hz, 4H), 7.16 (t, J=7.5 Hz, 4H), 7.11-6.98 (m, 2H), 3.76 (s, 4H), 3.68 (t, J=6.4 Hz, 2H), 3.38 (t, J=6.1 Hz, 2H), 3.34 (s, 2H), 1.69 (quin, J=6.2 Hz, 2H), 1.06 (s, 6H), 0.86 (s, 9H), 0.03 (s, 6H) ppm. ESI-MS m/z calc. 441.3063, found 442.3 (M+1)$^+$; Retention time: 2.17 minutes (LC Method E).

Step 3: 3-[2-(Dibenzylamino)-2-methyl-propoxy]propan-1-ol

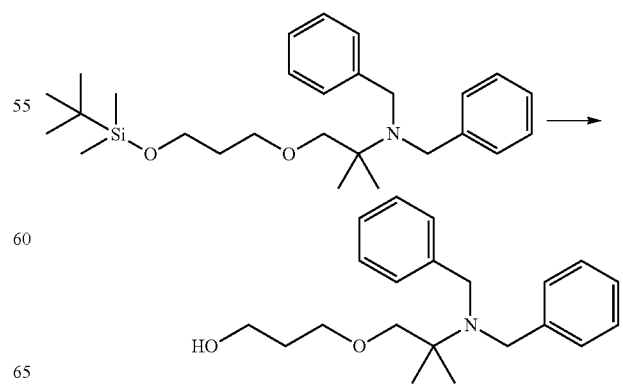

To a solution of N,N-dibenzyl-1-[3-[tert-butyl(dimethyl) silyl]oxypropoxy]-2-methyl-propan-2-amine (16.3 g, 36.901 mmol) in dry tetrahydrofuran (163 mL) was added tetrabutylammonium fluoride (1.0 M in THF) (60 mL of 1 M, 60 mmol) under nitrogen at 0° C. After stirring for 1 h at 0° C., the cold bath was removed. The mixture was stirred at room temperature for overnight then saturated aqueous ammonium chloride solution (100 mL) was added to quench the reaction. After separation, the aqueous phase was extracted with diethyl ether (2×75 mL). The combined organic solutions were washed with brine (100 mL), dried over sodium sulfate, filtered, concentrated, and the residue was purified by silica gel chromatography using a gradient from 5% to 40% ethyl acetate in heptanes to provide as a colorless oil, 3-[2-(dibenzylamino)-2-methyl-propoxy]propan-1-ol (8.25 g, 68%). $^1$H NMR (400 MHz, DMSO-d6) δ 7.26 (d, J=7.1 Hz, 4H), 7.17 (t, J=7.5 Hz, 4H), 7.10-7.04 (m, 2H), 4.38 (t, J=5.0 Hz, 1H), 3.76 (s, 4H), 3.53-3.45 (m, 2H), 3.38 (t, J=6.2 Hz, 2H), 3.34 (s, 2H), 1.66 (quin, J=6.4 Hz, 2H), 1.06 (s, 6H) ppm. ESI-MS m/z calc. 327.2198, found 328.2 (M+1)$^+$; Retention time: 1.55 minutes (LC Method E).

Step 4: N,N-Dibenzyl-1-(3-bromopropoxy)-2-methyl-propan-2-amine

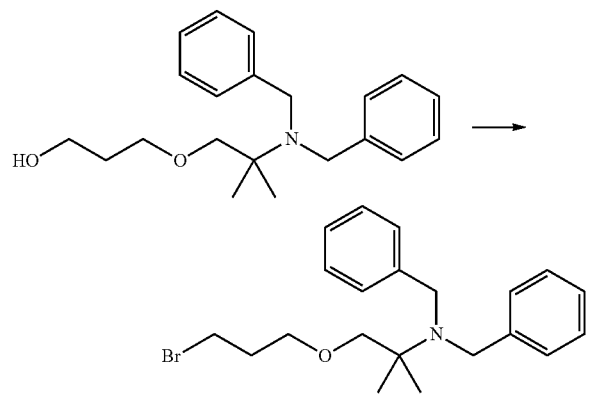

To a stirring solution of 3-[2-(dibenzylamino)-2-methyl-propoxy]propan-1-ol (8.2 g, 25.041 mmol) in anhydrous dichloromethane (250 mL) at 0° C. were added successively carbon tetrabromide (10 g, 30.154 mmol) and triphenylphosphine (9 g, 34.314 mmol). The reaction was stirred at 0° C. for 3 h and then overnight at room temperature. The mixture was evaporated under reduced pressure and then was purified by silica gel chromatography using a gradient from 0% to 10% ethyl acetate in heptanes to provide as a colorless oil, N,N-dibenzyl-1-(3-bromopropoxy)-2-methyl-propan-2-amine (6.8 g, 70%). $^1$H NMR (400 MHz, DMSO-d6) δ 7.26 (d, J=7.1 Hz, 4H), 7.17 (t, J=7.3 Hz, 4H), 7.11-7.01 (m, 2H), 3.76 (s, 4H), 3.59 (t, J=6.5 Hz, 2H), 3.43 (t, J=5.9 Hz, 2H), 3.37 (s, 2H), 2.03 (quin, J=6.2 Hz, 2H), 1.07 (s, 6H) ppm. ESI-MS m/z calc. 389.1354, found 390.2 (M+1)$^+$; Retention time: 1.79 minutes (LC Method E).

Step 5: Ethyl 5-[2-(dibenzylamino)-2-methyl-propoxy]-2-hydroxy-2-(trifluoromethyl)pentanoate

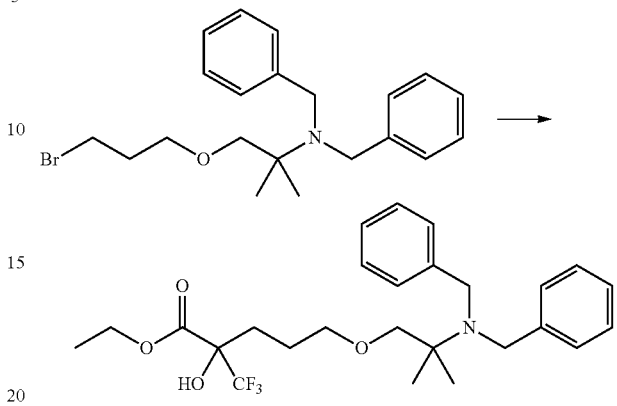

A dried 5-mL two-neck flask equipped with a reflux condenser under nitrogen was charged with magnesium (640 mg, 26.332 mmol) and iodine (166 mg, 0.654 mmol) and was stirred neat at room temperature for 10 minutes. Then, N,N-dibenzyl-1-(3-bromopropoxy)-2-methyl-propan-2-amine (5.1 g, 13.065 mmol) in diethyl ether (7.5 mL) was added dropwise. The mixture was heated at 40° C. for 10 minutes and then at 30° C. for 1 hour. The resulting mixture was cooled to room temperature then diethyl ether (7.5 mL) was added. The mixture was added dropwise to a cooled solution of ethyl 3,3,3-trifluoro-2-oxo-propanoate (2.4377 g, 1.9 mL, 14.332 mmol) in tetrahydrofuran (51 mL) at −78° C. The mixture was stirred at −78° C. for 10 minutes. The dry ice-acetone cooling bath was removed. The reaction mixture was allowed to warm up slowly to room temperature and stirred for 1 h. The reaction mixture was cooled to 0° C. and then it was quenched with a saturated ammonium chloride solution (250 mL). The resulting mixture was extracted with diethyl ether (2×250 mL). The combined organic phases were washed with brine (250 mL), dried over sodium sulfate, filtered and concentrated under vacuum. The crude residue was purified by silica gel chromatography using a gradient from 0% to 10% ethyl acetate in heptanes to provide as a colorless oil, ethyl 5-[2-(dibenzylamino)-2-methyl-propoxy]-2-hydroxy-2-(trifluoromethyl)pentanoate (3.23 g, 51%). $^1$H NMR (400 MHz, DMSO-d6) δ 7.26 (d, J=7.3 Hz, 4H), 7.16 (t, J=7.5 Hz, 4H), 7.11-6.99 (m, 2H), 6.81 (s, 1H), 4.23 (q, J=7.1 Hz, 2H), 3.76 (s, 4H), 3.41-3.25 (m, 4H), 2.08 (td, J=12.8, 4.3 Hz, 1H), 1.84 (td, J=12.8, 4.4 Hz, 1H), 1.75-1.60 (m, 1H), 1.44-1.30 (m, 1H), 1.21 (t, J=7.1 Hz, 3H), 1.05 (s, 6H) ppm. $^{19}$F NMR (377 MHz, DMSO-d6) δ−76.77 (s, 3F) ppm. ESI-MS m/z calc. 481.244, found 482.2 (M+1)$^+$; Retention time: 1.83 minutes (LC Method E).

Step 6: Ethyl 5-(2-amino-2-methyl-propoxy)-2-hydroxy-2-(trifluoromethyl)pentanoate

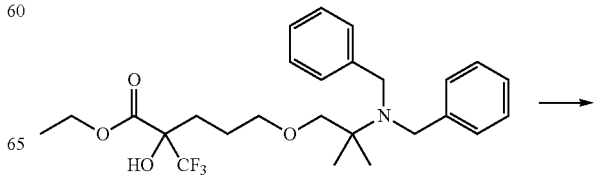

-continued

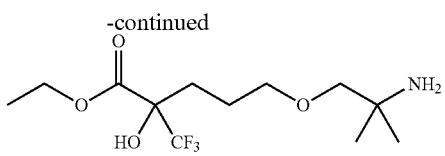

A solution of ethyl 5-[2-(dibenzylamino)-2-methyl-propoxy]-2-hydroxy-2-(trifluoromethyl)pentanoate (3.4 g, 7.0606 mmol) in ethanol (102 mL) was degassed with nitrogen for 15 minutes and then 20% palladium hydroxide on carbon (500 mg, 20% w/w, 0.7121 mmol) was added. Nitrogen was bubbled into the mixture for 10 minutes and then hydrogen was bubbled into the mixture for 15 minutes. The mixture was stirred at room temperature under a balloon of hydrogen for 18 h and then filtered. The solvent was removed under reduced pressure to provide as a colorless thick oil, ethyl 5-(2-amino-2-methyl-propoxy)-2-hydroxy-2-(trifluoromethyl)pentanoate (2.09 g, 98%). $^1$H NMR (400 MHz, CDCl$_3$) δ 4.43-4.29 (m, 2H), 3.54-3.42 (m, 2H), 3.16 (s, 2H), 2.72-2.20 (m, 2H), 2.20-2.04 (m, 2H), 1.96 (ddd, J=13.9, 10.6, 5.3 Hz, 1H), 1.78 (ddt, J=19.3, 11.1, 5.6 Hz, 1H), 1.55-1.40 (m, 1H), 1.35 (t, J=7.1 Hz, 3H), 1.10 (s, 3H), 1.10 (s, 3H) ppm. $^{19}$F NMR (377 MHz, CDCl$_3$) δ −78.50 (s, 3F) ppm. ESI-MS m/z calc. 301.1501, found 302.2 (M+1)$^+$; Retention time: 1.44 minutes (LC Method E).

Step 7: Methyl 6-[[2-(4-ethoxycarbonyl-5,5,5-trifluoro-4-hydroxy-pentoxy)-1,1-dimethyl-ethyl]amino]-3-nitro-5-(trifluoromethyl)pyridine-2-carboxylate

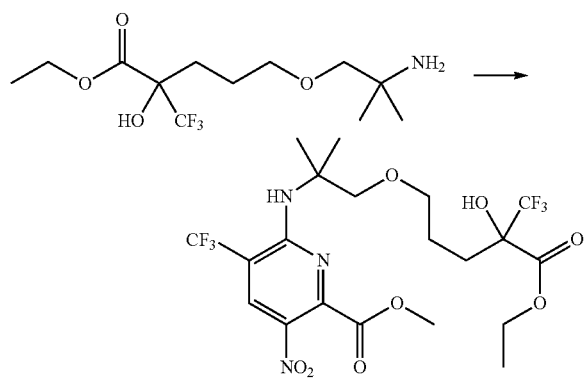

To a room temperature stirring solution of methyl 6-chloro-3-nitro-5-(trifluoromethyl)pyridine-2-carboxylate (1.8 g, 6.3252 mmol) and ethyl 5-(2-amino-2-methyl-propoxy)-2-hydroxy-2-(trifluoromethyl)pentanoate (2.05 g, 6.8038 mmol) in acetonitrile (25 mL) was added dropwise diisopropylethylamine (4.0810 g, 5.5 mL, 31.576 mmol). The resulting mixture was heated at 70° C. for 3 h. The solvent was removed by evaporation under reduced pressure then diluted with ethyl acetate (100 mL) and transferred to an extraction funnel with 150 mL of water. Phases were separated and then the aqueous phase was extracted with ethyl acetate (2×100 mL). The combined organic layers were washed with brine (150 mL), dried over sodium sulfate, filtered and concentrated in vacuo. The crude product was purified by silica gel chromatography using a gradient from 0% to 20% ethyl acetate in heptanes to provide as a brownish oil, methyl 6-[[2-(4-ethoxycarbonyl-5,5,5-trifluoro-4-hydroxy-pentoxy)-1,1-dimethyl-ethyl]amino]-3-nitro-5-(trifluoromethyl)pyridine-2-carboxylate (3.15 g, 91%). $^1$H NMR (400 MHz, DMSO-d6) δ 8.48 (s, 1H), 6.78 (s, 1H), 6.45 (s, 1H), 4.22 (q, J=7.1 Hz, 2H), 3.94 (s, 3H), 3.60-3.39 (m, 4H), 2.03-1.87 (m, 1H), 1.78-1.60 (m, 2H), 1.43 (s, 6H), 1.40-1.30 (m, 1H), 1.20 (t, J=7.1 Hz, 3H) ppm. $^{19}$F NMR (377 MHz, DMSO-d6) δ −63.57 (s, 3F), −76.95 (s, 3F) ppm. ESI-MS m/z calc. 549.1546, found 550.1 (M+1)$^+$; Retention time: 2.29 minutes (LC Method E).

Step 8: Methyl 6-[[2-(4-benzyloxy-4-ethoxycarbonyl-5,5,5-trifluoro-pentoxy)-1,1-dimethyl-ethyl]amino]-3-nitro-5-(trifluoromethyl)pyridine-2-carboxylate

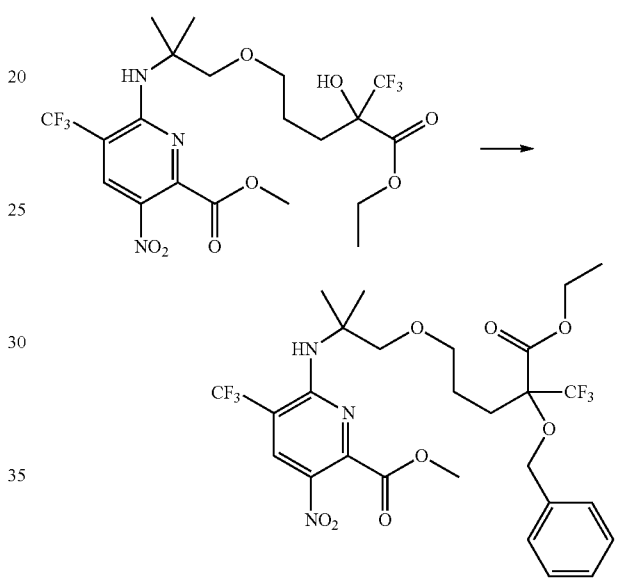

To a solution of methyl 6-[[2-(4-ethoxycarbonyl-5,5,5-trifluoro-4-hydroxy-pentoxy)-1,1-dimethyl-ethyl]amino]-3-nitro-5-(trifluoromethyl)pyridine-2-carboxylate (3.1 g, 5.6423 mmol) in DMF (31 mL) at 0° C. was added sodium hydride (460 mg, 11.501 mmol) as a 60% dispersion in mineral oil, portion-wise, not allowing the temperature to rise above 10° C. during the addition. After stirring for 30 minutes in an ice/ice water bath, bromomethylbenzene (1.5818 g, 1.1 mL, 9.2485 mmol) was added dropwise, then the reaction was allowed to warm up gradually to room temperature in the ice bath over 2 h. Ammonium chloride (910 mg, 17.012 mmol) was added as a solid at 0° C. The mixture was stirred for 10 minutes, then MTBE/heptanes (3:1, 100 mL) was added followed by water (100 mL). The mixture was transferred to an extraction funnel rinsing with MTBE/heptanes (3:1, 100 mL) and water (100 mL). The organic layer was separated and the aqueous phase was extracted with MTBE/heptanes (3:1, 2×100 mL). The combined organic layers were washed with water (150 mL) and brine (2×100 mL) and dried over anhydrous sodium sulfate. The mixture was filtered and concentrated under reduced pressure. The residue was purified by silica gel chromatography using a gradient from 0% to 20% of ethyl acetate in heptanes to afford as a colorless oil, methyl 6-[[2-(4-benzyloxy-4-ethoxycarbonyl-5,5,5-trifluoro-pentoxy)-1,1-dimethyl-ethyl]amino]-3-nitro-5-(trifluoromethyl)pyridine-2-carboxylate (3.25 g, 90%). $^1$H NMR (400 MHz, DMSO-d6)

δ 8.47 (s, 1H), 7.44-7.26 (m, 5H), 6.45 (s, 1H), 4.70 (d, J=10.8 Hz, 1H), 4.62-4.57 (m, 1H), 4.29 (q, J=7.1 Hz, 2H), 3.93 (s, 3H), 3.58-3.41 (m, 4H), 2.11-1.97 (m, 2H), 1.76-1.63 (m, 1H), 1.62-1.49 (m, 1H), 1.42 (s, 6H), 1.23 (t, J=7.1 Hz, 3H) ppm. $^{19}$F NMR (377 MHz, DMSO-d6) δ −63.54 (s, 3F), −70.73 (s, 3F) ppm. ESI-MS m/z calc. 639.2015, found 640.2 (M+1)$^+$; Retention time: 2.58 minutes (LC Method E).

Step 9: Ethyl 2-benzyloxy-5-[2-[[6-(hydrazinecarbonyl)-5-nitro-3-(trifluoromethyl)-2-pyridyl]amino]-2-methyl-propoxy]-2-(trifluoromethyl)pentanoate

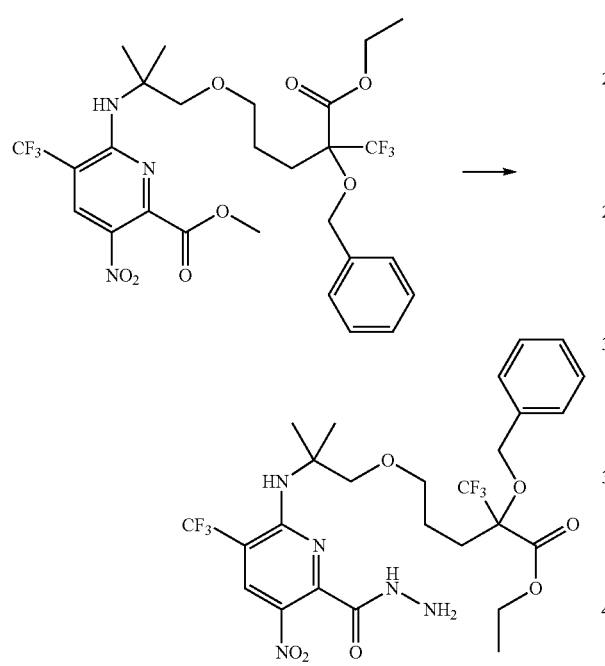

Methyl 6-[[2-(4-benzyloxy-4-ethoxycarbonyl-5,5,5-trifluoro-pentoxy)-1,1-dimethyl-ethyl]amino]-3-nitro-5-(trifluoromethyl)pyridine-2-carboxylate (3.2 g, 5.0036 mmol) was dissolved in methanol (60 mL) and then hydrazine monohydrate (2.0580 g, 2 mL, 41.110 mmol) was added. The resulting mixture was heated to 80° C. overnight. The solvent was removed under reduced pressure and then the mixture was dissolved in ethyl acetate (50 mL). The resulting mixture was washed with water (100 mL), brine (100 mL), dried over sodium sulfate, filtered and concentrated under vacuum to provide as a brownish thick crude oil, ethyl 2-benzyloxy-5-[2-[[6-(hydrazinecarbonyl)-5-nitro-3-(trifluoromethyl)-2-pyridyl]amino]-2-methyl-propoxy]-2-(trifluoromethyl)pentanoate (3.15 g, 98%). ESI-MS m/z calc. 639.2128, found 640.2 (M+1)$^+$; Retention time: 2.29 minutes. This material was used directly in the ensuing step (LC Method E).

Step 10: Ethyl 2-benzyloxy-5-[2-[[6-[[bis(tert-butoxycarbonyl)amino]carbamoyl]-5-nitro-3-(trifluoromethyl)-2-pyridyl]amino]-2-methyl-propoxy]-2-(trifluoromethyl)pentanoate

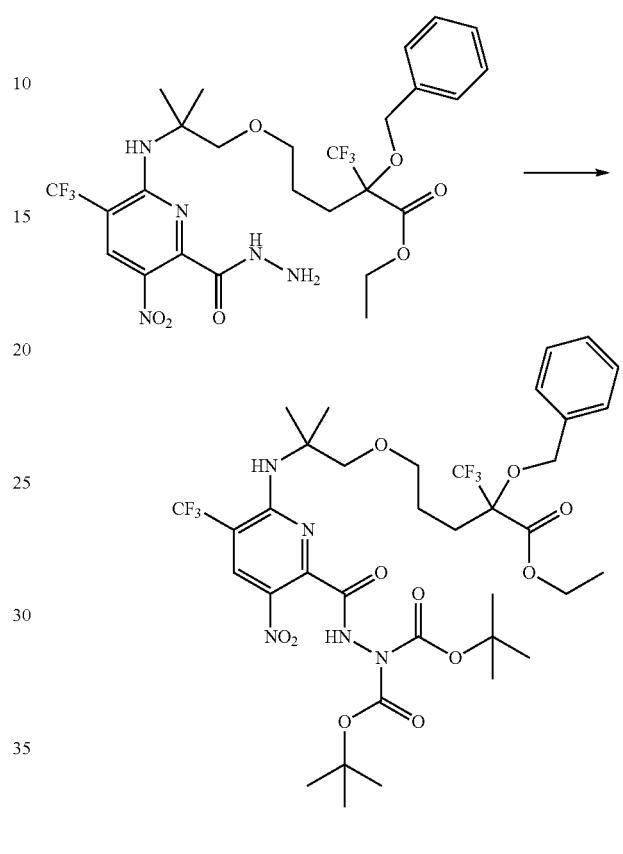

To a mixture of ethyl 2-benzyloxy-5-[2-[[6-(hydrazinecarbonyl)-5-nitro-3-(trifluoromethyl)-2-pyridyl]amino]-2-methyl-propoxy]-2-(trifluoromethyl)pentanoate (3.1 g, 4.8472 mmol) and tert-butoxycarbonyl tert-butyl carbonate (2.65 g, 12.142 mmol) in dichloromethane (110 mL) was added diisopropylethylamine (1.5582 g, 2.1 mL, 12.056 mmol) followed by 4-(dimethylamino)pyridine (60 mg, 0.4911 mmol). The resulting mixture was stirred at room temperature overnight. The resulting mixture was dissolved in dichloromethane and pre-adsorbed on silica-gel under reduced pressure. Purification by silica gel chromatography using a gradient from 0% to 15% ethyl acetate in heptanes provided as a brownish oil, ethyl 2-benzyloxy-5-[2-[[6-[[bis(tert-butoxycarbonyl)amino]carbamoyl]-5-nitro-3-(trifluoromethyl)-2-pyridyl]amino]-2-methyl-propoxy]-2-(trifluoromethyl)pentanoate (2.16 g, 53%). $^1$H NMR (400 MHz, DMSO-d6) δ 8.55 (s, 1H), 7.53-7.19 (m, 5H), 6.47 (br. s., 1H), 4.75-4.67 (m, 1H), 4.64-4.54 (m, 1H), 4.28 (q, J=7.1 Hz, 2H), 3.58-3.39 (m, 4H), 2.13-1.97 (m, 2H), 1.76-1.52 (m, 3H), 1.48 (s, 18H), 1.41 (s, 6H), 1.24-1.21 (m, 3H) ppm. $^{19}$F NMR (377 MHz, DMSO-d6) δ −63.15 (br. s., 3F), −70.64 to −70.77 (m, 3F) ppm; ESI-MS m/z calc. 839.3176, found 784.3 (M-55)$^+$; Retention time: 4.62 minutes (LC Method BB).

Step 11: 2-Benzyloxy-5-[2-[[6-[(tert-butoxycarbonylamino)carbamoyl]-5-nitro-3-(trifluoromethyl)-2-pyridyl]amino]-2-methyl-propoxy]-2-(trifluoromethyl)pentanoic acid

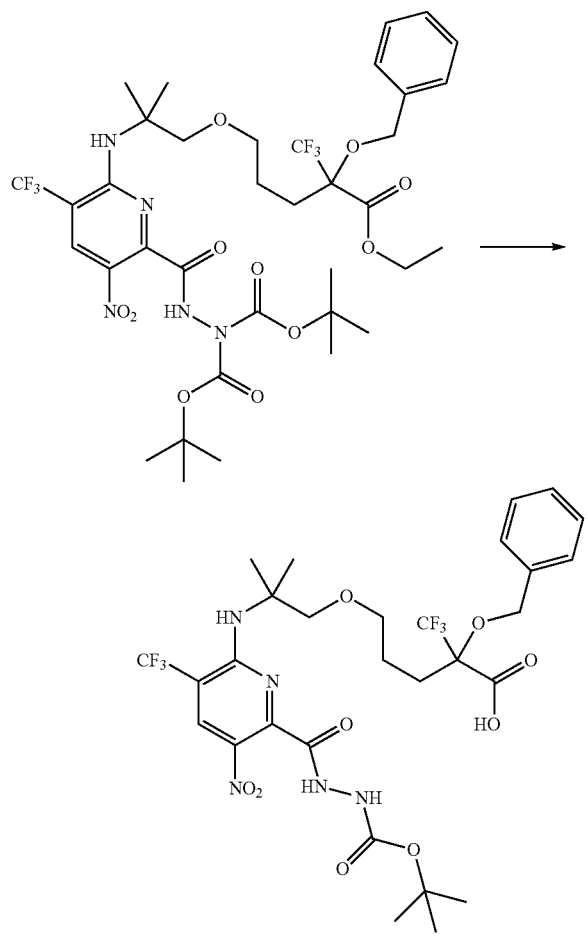

A solution of sodium hydroxide (300 mg, 7.5005 mmol) in water (10 mL) was added to a solution of ethyl 2-benzyloxy-5-[2-[[6-[[bis(tert-butoxycarbonyl)amino]carbamoyl]-5-nitro-3-(trifluoromethyl)-2-pyridyl]amino]-2-methyl-propoxy]-2-(trifluoromethyl)pentanoate (2.1 g, 2.4596 mmol) in methanol (40 mL). The reaction was heated at 50° C. overnight. The reaction was concentrated to remove methanol and the crude material was diluted into water (75 mL) and then washed with heptanes (75 mL) and MTBE (75 mL). The aqueous solution was acidified to pH=2 with a 3 N aqueous hydrochloric acid solution. The aqueous mixture was extracted with dichloromethane (4×50 mL) and the combined organic layers were dried over sodium sulfate. The solution was filtered and concentrated to give as a brownish oil, 2-benzyloxy-5-[2-[[6-[(tert-butoxycarbonylamino)carbamoyl]-5-nitro-3-(trifluoromethyl)-2-pyridyl]amino]-2-methyl-propoxy]-2-(trifluoromethyl)pentanoic acid (1.58 g, 90%). ESI-MS m/z calc. 711.2339, found 656.1 (M-55)$^+$; Retention time: 2.23 minutes (LC Method E).

Step 12: 2-Benzyloxy-5-[2-[[6-(hydrazinecarbonyl)-5-nitro-3-(trifluoromethyl)-2-pyridyl]amino]-2-methyl-propoxy]-2-(trifluoromethyl)pentanoic acid (hydrochloride Salt)

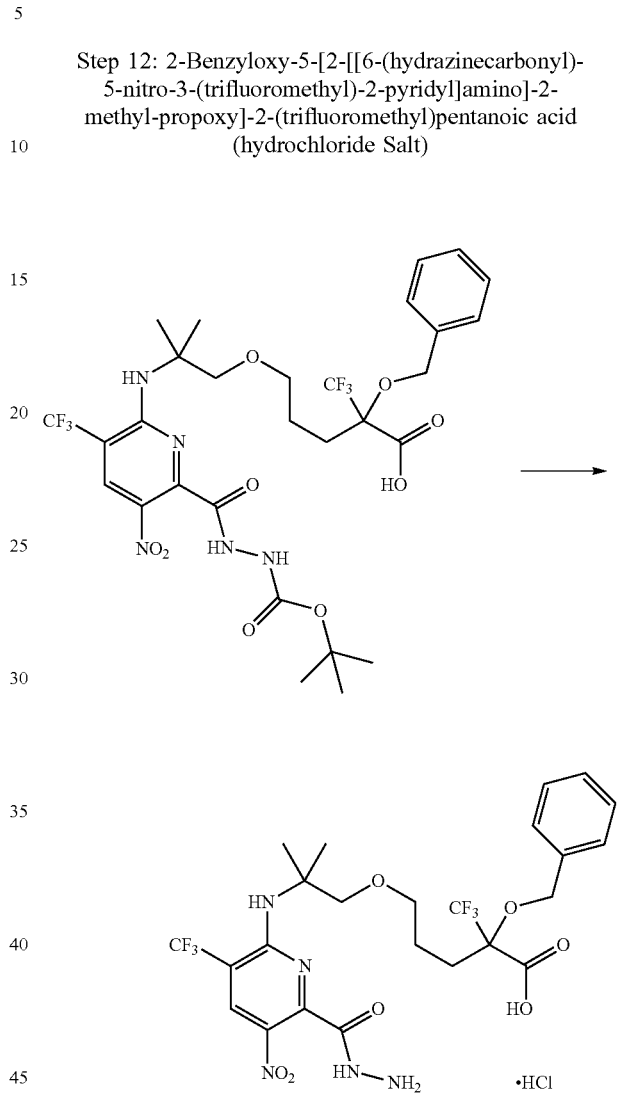

2-Benzyloxy-5-[2-[[6-[(tert-butoxycarbonylamino)carbamoyl]-5-nitro-3-(trifluoromethyl)-2-pyridyl]amino]-2-methyl-propoxy]-2-(trifluoromethyl)pentanoic acid (350 mg, 0.4918 mmol) was dissolved in dioxane (9 mL) and then hydrochloric acid (3.5 mL of 4 M in dioxane, 14 mmol) was added dropwise at room temperature. The resulting mixture was stirred at room temperature for 48 h. The mixture was concentrated under vacuum to afford as a crude light yellow foam, 2-benzyloxy-5-[2-[[6-(hydrazinecarbonyl)-5-nitro-3-(trifluoromethyl)-2-pyridyl]amino]-2-methyl-propoxy]-2-(trifluoromethyl)pentanoic acid (hydrochloride salt) (318 mg, 100%). ESI-MS m/z calc. 611.1815, found 612.0 (M+1)$^+$; Retention time: 1.88 minutes (LC Method Z). This material was used directly in the next step.

919

Step 13: 9-Benzyloxy-3,3-dimethyl-15-nitro-9,17-bis(trifluoromethyl)-5-oxa-2,11,12,18-tetrazabicyclo[12.3.1]octadeca-1(17),14(18),15-triene-10,13-dione

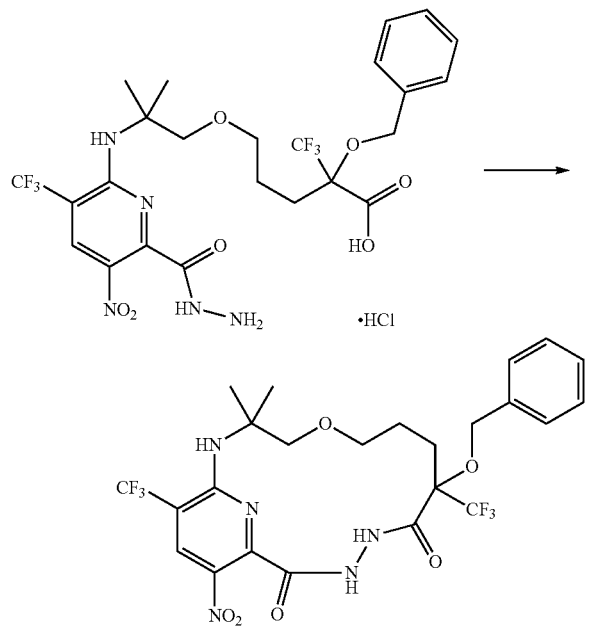

To a room temperature stirring solution of 2-benzyloxy-5-[2-[[6-(hydrazinecarbonyl)-5-nitro-3-(trifluoromethyl)-2-pyridyl]amino]-2-methyl-propoxy]-2-(trifluoromethyl)pentanoic acid (hydrochloride salt) (360 mg, 0.5556 mmol) in dimethylformamide (DMF) (200 mL) was added BOP (300 mg, 0.6783 mmol) and HOBt (115 mg, 0.8511 mmol) followed by diisopropylethylamine (371 mg, 0.5 mL, 2.8706 mmol). The resulting mixture was stirred at room temperature for 24 h. The solvent was removed under vacuum at 50° C. The residue was dry-loaded on silica gel and purified by silica gel chromatography using a gradient from 0% to 25% ethyl acetate in dichloromethane to provide as a clear thick oil, 9-benzyloxy-3,3-dimethyl-15-nitro-9,17-bis(trifluoromethyl)-5-oxa-2,11,12,18-tetrazabicyclo[12.3.1]octadeca-1(17),14(18),15-triene-10,13-dione (92 mg, 28%). ESI-MS m/z calc. 593.1709, found 594.0 (M+1)$^+$; Retention time: 1.94 minutes (LC Method Z).

Step 14: 6-Benzyloxy-12,12-dimethyl-17-nitro-6,15-bis(trifluoromethyl)-10,19-dioxa-3,4,13,18-tetrazatricyclo[12.3.1.1$^{2,5}$]nonadeca-1(18),2,4,14,16-pentaene

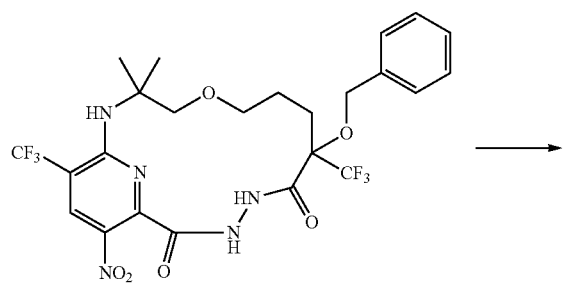

920

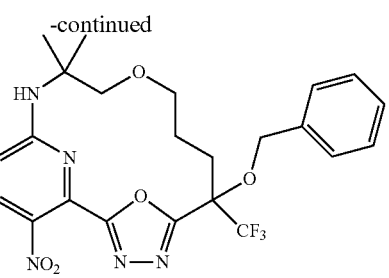

To a solution of 9-benzyloxy-3,3-dimethyl-15-nitro-9,17-bis(trifluoromethyl)-5-oxa-2,11,12,18-tetrazabicyclo[12.3.1]octadeca-1(17),14(18),15-triene-10,13-dione (90 mg, 0.1516 mmol) and N,N-diisopropylethylamine (148.40 mg, 200 μL, 1.1482 mmol) in acetonitrile (25 mL) at room temperature was added 4-methylbenzenesulfonyl chloride (40 mg, 0.2098 mmol). The mixture was then heated to 70° C. and stirred for 2 h at this temperature. The reaction mixture was then cooled and concentrated by evaporation under reduced pressure. The residue was dissolved in ethyl acetate (25 mL). This solution was washed with an aqueous solution of 5% sodium bicarbonate (2×25 mL) and brine (25 mL) then dried over anhydrous sodium sulfate and filtered. The volatiles were removed by evaporation under reduced pressure. The residue was dry-loaded on silica gel and purified by silica gel chromatography using a gradient from 0% to 15% ethyl acetate in heptanes to give as a clear thick oil, 6-benzyloxy-12,12-dimethyl-17-nitro-6,15-bis(trifluoromethyl)-10,19-dioxa-3,4,13,18-tetrazatricyclo[12.3.1.1$^{2,5}$]nonadeca-1(18),2,4,14,16-pentaene (47 mg, 54%). $^1$H NMR (400 MHz, CDCl$_3$) δ 8.46 (s, 1H), 7.34-7.18 (m, 5H), 5.39 (br. s., 1H), 5.13 (d, J=11.0 Hz, 1H), 4.89 (d, J=11.2 Hz, 1H), 4.01 (d, J=8.1 Hz, 1H), 3.56-3.44 (m, 3H), 2.56-2.32 (m, 2H), 1.61-1.51 (m, 2H), 1.51 (s, 3H), 1.46 (s, 3H) ppm. $^{19}$F NMR (377 MHz, CDCl$_3$) δ −63.91 (s, 3F), −73.26 (s, 3F) ppm. ESI-MS m/z calc. 575.1603, found 576.0 (M+1)$^+$; Retention time: 2.14 minutes (LC Method Z).

Step 15: 17-Amino-12,12-dimethyl-6,15-bis(trifluoromethyl)-10,19-dioxa-3,4,13,18-tetrazatricyclo[12.3.1.1$^{2,5}$]nonadeca-1(18),2,4,14,16-pentaen-6-ol

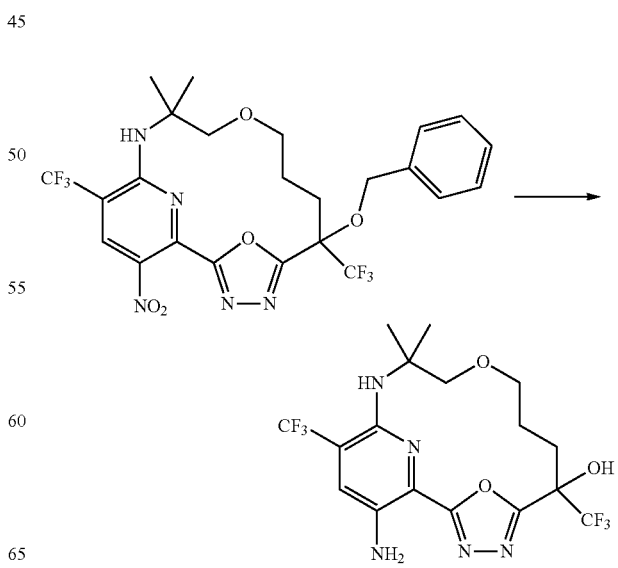

6-Benzyloxy-12,12-dimethyl-17-nitro-6,15-bis(trifluoromethyl)-10,19-dioxa-3,4,13,18-tetrazatricyclo[12.3.1.12,5]nonadeca-1(18),2,4,14,16-pentaene (52 mg, 0.0904 mmol) was dissolved in methanol (3 mL). The mixture was bubbled with nitrogen for 5 min and then palladium on carbon (35 mg, 5% w/w, 0.0164 mmol) was added. The resulting mixture was bubbled with a balloon of hydrogen for 5 min and then the mixture was stirred at room temperature under hydrogen overnight. The reaction mixture was filtered using a syringe micro filter washing with methanol (10 mL) and the resulting solution was concentrated under reduced pressure. The residue was solubilized again in methanol (3 mL). Nitrogen was bubbled into the mixture for 5 minutes and then palladium on carbon (35 mg, 5% w/w, 0.0164 mmol) was added. Hydrogen was then bubbled with a balloon into the mixture for 5 minutes and the reaction mixture was then stirred at room temperature under hydrogen for 6 h. The reaction mixture was filtered using a syringe micro filter washing with methanol (5 mL) and the resulting solution was concentrated under reduced pressure. The residue was purified by silica gel chromatography using a gradient from 0% to 30% ethyl acetate in heptanes followed by reverse phase chromatography eluting with 0% to 70% acetonitrile in 0.1% aqueous $NH_4HCO_3$ to provide as a yellow oil, 17-amino-12,12-dimethyl-6,15-bis(trifluoromethyl)-10,19-dioxa-3,4,13,18-tetrazatricyclo[12.3.1.12,5]nonadeca-1(18),2,4,14,16-pentaen-6-ol (25 mg, 60%). $^1$H NMR (400 MHz, $CD_3OD$) δ 7.49 (s, 1H), 4.66 (d, J=7.8 Hz, 1H), 3.75-3.57 (m, 2H), 3.38 (d, J=7.8 Hz, 1H), 2.70-2.55 (m, 1H), 2.20 (td, J=13.0, 5.6 Hz, 1H), 1.90-1.76 (m, 1H), 1.75-1.64 (m, 1H), 1.54 (s, 3H), 1.41 (s, 3H) ppm. $^{19}$F NMR (377 MHz, $CD_3OD$) δ −65.19 (s, 3F), −81.21 (br. s., 3F) ppm. ESI-MS m/z calc. 455.1392, found 456.1 $(M+1)^+$; Retention time: 3.52 minutes (LC Method BB).

Step 16: 17-Amino-12,12-dimethyl-6,15-bis(trifluoromethyl)-10,19-dioxa-3,4,13,18-tetrazatricyclo[12.3.1.12,5]nonadeca-1(18),2,4,14,16-pentaen-6-ol (enantiomer 1) (Compound 199) and 17-amino-12,12-dimethyl-6,15-bis(trifluoromethyl)-10,19-dioxa-3,4,13,18-tetrazatricyclo[12.3.1.12,5]nonadeca-1(18),2,4,14,16-pentaen-6-ol (enantiomer 2) (Compound 200)

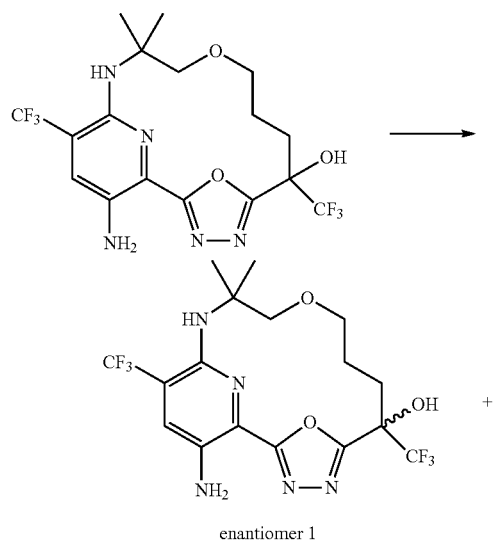

enantiomer 1

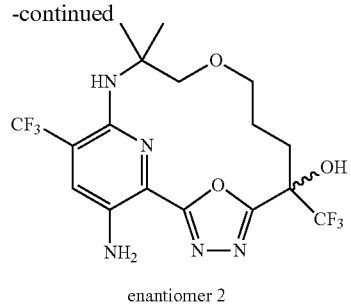

enantiomer 2

Racemic 17-amino-12,12-dimethyl-6,15-bis(trifluoromethyl)-10,19-dioxa-3,4,13,18-tetrazatricyclo[12.3.1.12,5]nonadeca-1(18),2,4,14,16-pentaen-6-ol (13.0 mg, 0.02855 mmol was purified by chiral normal phase SFC using a ChiralPak AS column (250×10 mm; 5 μm) at 50° C. eluting with 8% MeOH (+20 mM $NH_3$) in $CO_2$ at a 10 mL/min flow (concentration of the sample was 20.6 mg/mL in methanol, injection volume=70 μL with an outlet pressure of 152 bar and detection wavelength of 229 nm) which gave the separation of two single enantiomers:

The first enantiomer to elute was isolated as a yellow solid, 17-amino-12,12-dimethyl-6,15-bis(trifluoromethyl)-10,19-dioxa-3,4,13,18-tetrazatricyclo[12.3.1.12,5]nonadeca-1(18),2,4,14,16-pentaen-6-ol (enantiomer 1) (4.6 mg, 70%). $^1$H NMR (400 MHz, Chloroform-d) δ 7.27 (s, 1H), 4.81 (s, 2H), 4.67 (d, J=7.8 Hz, 1H), 4.38 (s, 1H), 3.95 (s, 1H), 3.71 (ddd, J=12.2, 9.5, 4.4 Hz, 1H), 3.54 (dt, J=12.3, 3.8 Hz, 1H), 3.20 (d, J=7.8 Hz, 1H), 2.76-2.64 (m, 1H), 2.27-2.15 (m, 1H), 1.73 (ddt, J=14.9, 10.3, 4.5 Hz, 2H), 1.58 (s, 3H), 1.40 (s, 3H) ppm. ESI-MS m/z calc. 455.13922, found 456.2 $(M+1)^+$; Retention time: 1.63 minutes (LC Method A).

The second enantiomer to elute was isolated as a yellow solid, 17-amino-12,12-dimethyl-6,15-bis(trifluoromethyl)-10,19-dioxa-3,4,13,18-tetrazatricyclo[12.3.1.12,5]nonadeca-1(18),2,4,14,16-pentaen-6-ol (enantiomer 2) (4.2 mg, 64%). $^1$H NMR (400 MHz, Chloroform-d) δ 7.27 (s, 1H), 4.81 (s, 2H), 4.66 (d, J=7.8 Hz, 1H), 4.38 (s, 1H), 3.92 (s, 1H), 3.71 (ddd, J=12.3, 9.8, 4.3 Hz, 1H), 3.54 (dt, J=12.3, 3.8 Hz, 1H), 3.20 (d, J=7.8 Hz, 1H), 2.76-2.64 (m, 1H), 2.27-2.15 (m, 1H), 1.80-1.68 (m, 2H), 1.58 (s, 3H), 1.40 (s, 3H) ppm. ESI-MS m/z calc. 455.13922, found 456.2 $(M+1)^+$; Retention time: 1.64 minutes (LC Method A).

Example 111: Preparation of (6R)-17-amino-12-pyrimidin-2-yl-6,15-bis(trifluoromethyl)-19-oxa-3,4,13,18-tetrazatricyclo[12.3.1.12,5]nonadeca-1(18),2,4,14,16-pentaen-6-ol (enantiomer 1) (Compound 201) and (6R)-17-amino-12-pyrimidin-2-yl-6,15-bis(trifluoromethyl)-19-oxa-3,4,13,18-tetrazatricyclo[12.3.1.12,5]nonadeca-1(18),2,4,14,16-pentaen-6-ol (enantiomer 2) (Compound 202)

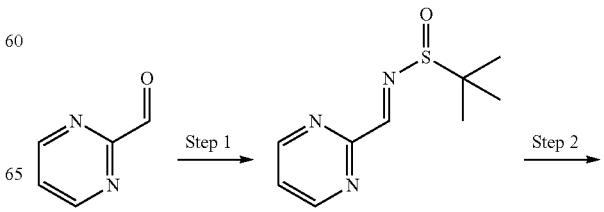

923
-continued
924
-continued
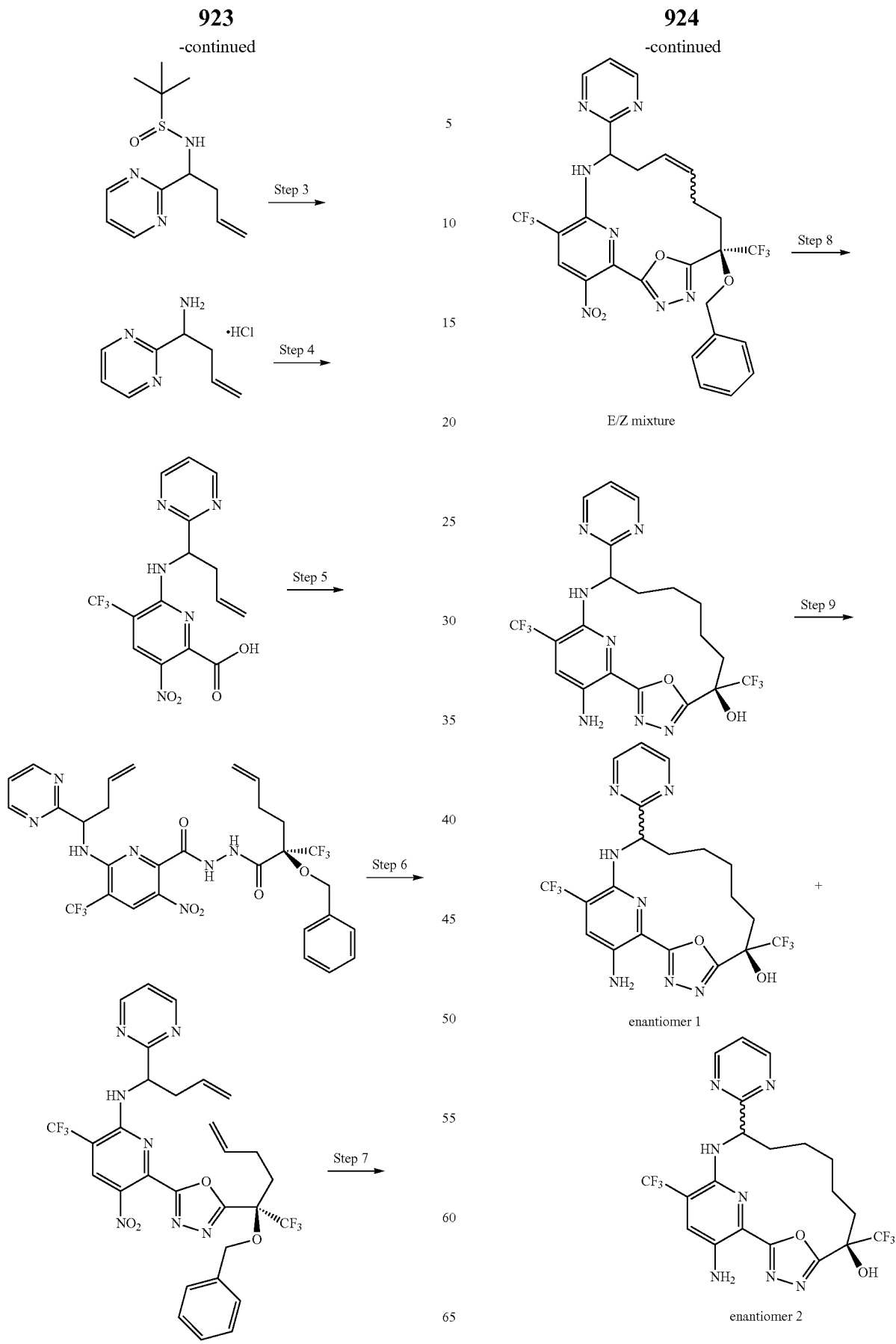

Step 1: (E)-2-Methyl-N-(pyrimidin-2-ylmethylene)propane-2-sulfinamide

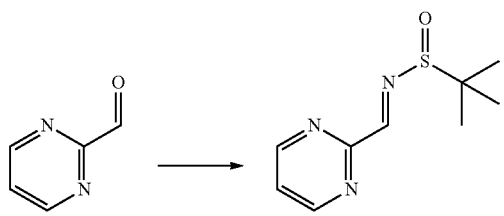

A mixture of pyrimidine-2-carbaldehyde (10 g, 92.509 mmol), 2-methylpropane-2-sulfinamide (11.3 g, 93.234 mmol) and potassium bisulfate (13 g, 95.470 mmol) in toluene (50 mL) was heated at 50° C. overnight. After decanting the solution, the solid residue was washed 3 times with dichloromethane, the washings combined with the decanted solution and solvents were evaporated in vacuo. The crude mixture was purified by silica gel chromatography using a gradient from 0% to 30% ethyl acetate in dichloromethane to yield as an off-white solid, (E)-2-methyl-N-(pyrimidin-2-ylmethylene)propane-2-sulfinamide (7.85 g, 40%). $^1$H NMR (400 MHz, CDCl$_3$) δ 8.93 (d, J=4.9 Hz, 2H), 8.72 (s, 1H), 7.38 (t, J=4.9 Hz, 1H), 1.30 (s, 9H) ppm. ESI-MS m/z calc. 211.0779, found 212.2 (M+1)$^+$; Retention time: 1.31 minutes (LC Method Z).

Step 2: 2-Methyl-N-(1-pyrimidin-2-ylbut-3-enyl)propane-2-sulfinamide

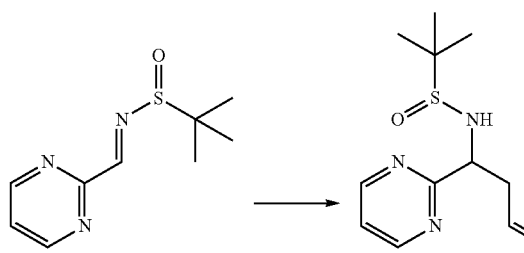

To a cooled solution of (E)-2-methyl-N-(pyrimidin-2-ylmethylene)propane-2-sulfinamide (2 g, 9.4659 mmol) in tetrahydrofuran (40 mL) at −78° C. was added trimethylaluminum (14 mL of 2 M, 28 mmol) in heptanes dropwise. The mixture was stirred for 10 minutes at −78° C. and then allyl(bromo)magnesium (14 mL of 1 M in diethyl ether, 14 mmol) was added dropwise. The reaction was held at −78° C. until complete consumption of starting material was observed by HPLC analysis. The reaction was quenched slowly with saturated aqueous ammonium chloride (150 mL) at −78° C. The cold bath was removed and then the mixture was then stirred vigorously at room temperature for 30 minutes. The mixture was extracted with ethyl acetate (2×100 mL), washed with brine (200 mL), dried over sodium sulfate, filtered and the solvent removed under reduced pressure. The crude residue was purified by silica gel chromatography using a gradient from 0% to 5% methanol in dichloromethane to afford as a light yellow oil, 2-methyl-N-(1-pyrimidin-2-ylbut-3-enyl)propane-2-sulfinamide (1.67 g, 70%). $^1$H NMR (400 MHz, CDCl$_3$) δ 8.71 (d, J=4.9 Hz, 2H), 7.18 (t, J=4.9 Hz, 1H), 5.74 (ddt, J=17.0, 10.3, 7.0 Hz, 1H), 5.10-4.99 (m, 2H), 4.96 (br d, J=7.3 Hz, 1H), 4.72-4.65 (m, 1H), 2.84-2.59 (m, 2H), 1.29 (s, 9H) ppm. ESI-MS m/z calc. 253.1249, found 254.2 (M+1)$^+$; Retention time: 1.49 minutes (LC Method Z).

Step 3: 1-Pyrimidin-2-ylbut-3-en-1-amine (Hydrochloride Salt)

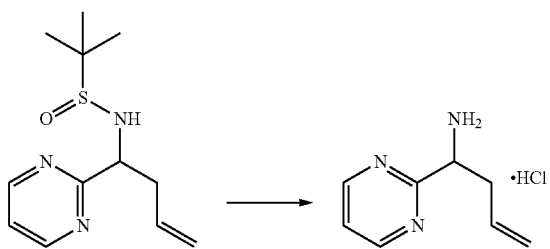 [SMILES: C=CCC(NS(=O)C(C)(C)C)c1ncccn1 ; C=CCC(N)c1ncccn1 ; Cl]

To a solution of 2-methyl-N-(1-pyrimidin-2-ylbut-3-enyl)propane-2-sulfinamide (2 g, 7.8938 mmol) in methanol (19 mL) was added hydrochloric acid (19 mL of 2 M in diethyl ether, 38 mmol) dropwise at room temperature and then the resulting mixture was stirred for 1 hour at room temperature. The mixture was cooled to 0° C., then diethyl ether (75 mL) was added and the resulting pink suspension was stirred at this temperature for 30 minutes. The resulting precipitate was filtered and washed with diethyl ether (50 mL) to give as a pinkish powder, 1-pyrimidin-2-ylbut-3-en-1-amine (hydrochloride salt) (1.45 g, 96%). $^1$H NMR (400 MHz, DMSO-d6) δ 8.89 (d, J=5.1 Hz, 2H), 8.87-8.74 (m, 3H), 7.53 (t, J=4.9 Hz, 1H), 5.71 (ddt, J=17.0, 10.1, 7.1 Hz, 1H), 5.08-4.96 (m, 2H), 4.53-4.37 (m, 1H), 2.87-2.66 (m, 2H) ppm. ESI-MS m/z calc. 149.0953, found 150.1 (M+1)$^+$; Retention time: 1.74 minutes (LC Method BB).

Step 4: 3-Nitro-6-(1-pyrimidin-2-ylbut-3-enylamino)-5-(trifluoromethyl)pyridine-2-carboxylic Acid

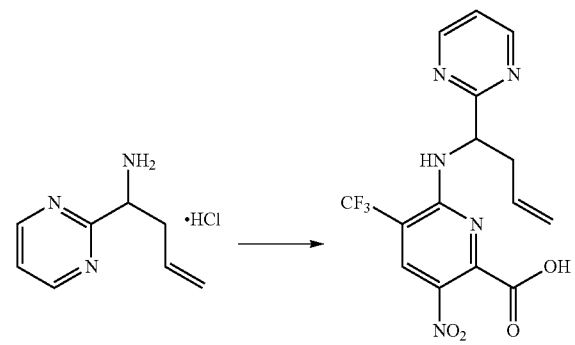 [SMILES: C=CCC(N)c1ncccn1 ; Cl ; C=CCC(Nc1nc(C(=O)O)c([N+](=O)[O-])cc1C(F)(F)F)c1ncccn1]

In a reaction vial, methyl 6-chloro-3-nitro-5-(trifluoromethyl)pyridine-2-carboxylate (270 mg, 0.9488 mmol) was mixed with 1-pyrimidin-2-ylbut-3-en-1-amine (hydrochloride salt) (253 mg, 1.139 mmol) and DIEA (785 μL, 4.507 mmol) in acetonitrile (7.8 mL). The reaction was heated at 80° C. for 1 h then solvent was removed under vacuum. The residue was diluted with ethyl acetate and washed with a saturated aqueous NaHCO$_3$ solution (3×) followed by brine. The organic layer was isolated, dried over anhydrous Na₂SO₄, filtered, and evaporated to dryness. The crude material was purified by silica gel chromatography using a gradient from 10% to 60% ethyl acetate in hexanes giving a gray solid. This gray solid was dissolved in THF (4.8 mL), MeOH (4.8 mL) and water (2.4 mL) and LiOH (340.8 mg, 14.23 mmol) was added. The reaction was stirred at room temperature for 2 h then evaporated to dryness. The solid residue was acidified with 1 N HCl and extracted with ethyl acetate. The organic layer was isolated, dried over anhydrous Na₂SO₄, filtered, and evaporated to dryness. The crude material was purified by recrystallization from ethyl acetate/hexanes to provide as a tan solid, 3-nitro-6-(1-pyrimidin-2-ylbut-3-enylamino)-5-(trifluoromethyl)pyridine-2-carboxylic acid (203 mg, 47%). ESI-MS m/z calc. 383.08414, found 384.2 (M+1)⁺; Retention time: 0.55 minutes (LC Method S).

Step 5: N'-[(2R)-2-Benzyloxy-2-(trifluoromethyl)hex-5-enoyl]-3-nitro-6-(1-pyrimidin-2-ylbut-3-enylamino)-5-(trifluoromethyl)pyridine-2-carbohydrazide

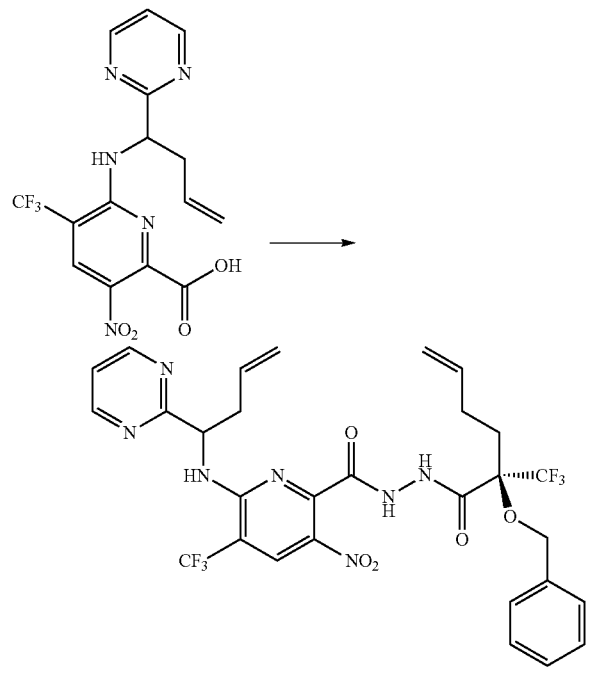

A solution of 3-nitro-6-(1-pyrimidin-2-ylbut-3-enylamino)-5-(trifluoromethyl)pyridine-2-carboxylic acid (202 mg, 0.4691 mmol) and (2R)-2-benzyloxy-2-(trifluoromethyl)hex-5-enehydrazide (184 mg, 0.5886 mmol) in DMF (5 mL) was cooled in an ice bath and treated successively with HATU (255 mg, 0.6706 mmol) and DIPEA (140.98 mg, 0.19 mL, 1.0908 mmol). After 5 minutes, the ice bath was removed and the reaction was stirred at room temperature for 19 h. The reaction was transferred to a 125 mL separatory funnel with water (50 mL) and the aqueous mixture was extracted with ethyl acetate (3×25 mL). The combined organic layer was washed with water (2×25 mL) then brine (25 mL), dried over sodium sulfate, filtered and concentrated under reduced pressure. The residue was purified by silica gel chromatography using a gradient from 0% to 50% ethyl acetate in heptanes to afford as a yellow oil and a ~1:1 mixture of diastereomers of N'-[(2R)-2-benzyloxy-2-(trifluoromethyl)hex-5-enoyl]-3-nitro-6-(1-pyrimidin-2-ylbut-3-enylamino)-5-(trifluoromethyl)pyridine-2-carbohydrazide (215 mg, 63%). ¹H NMR (400 MHz, CDCl₃) δ 9.57 (d, J=17.1 Hz, 1H), 9.41-9.16 (m, 1H), 8.73 (dd, J=4.9, 2.7 Hz, 2H), 8.21 (d, J=6.6 Hz, 1H), 7.48-7.31 (m, 5H), 7.23 (t, J=4.9 Hz, 1H), 7.03-6.86 (m, 1H), 5.84 (ddt, J=16.9, 10.4, 6.1 Hz, 1H), 5.70 (ddt, J=17.3, 9.8, 7.2 Hz, 1H), 5.57-5.43 (m, 1H), 5.16-5.00 (m, 4H), 4.88-4.81 (m, 1H), 4.77-4.71 (m, 1H), 2.99-2.86 (m, 1H), 2.86-2.76 (m, 1H), 2.51-2.35 (m, 1H), 2.32-2.16 (m, 3H) ppm. Retention time: 2.4 minutes (LC Method E).

Step 6: 6-[5-[(1R)-1-Benzyloxy-1-(trifluoromethyl)pent-4-enyl]-1,3,4-oxadiazol-2-yl]-5-nitro-N-(1-pyrimidin-2-ylbut-3-enyl)-3-(trifluoromethyl)pyridin-2-amine

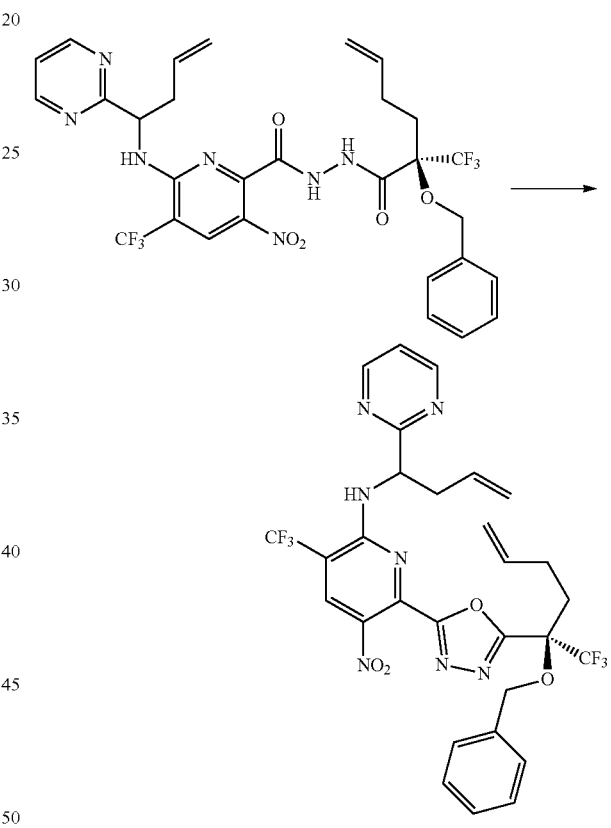

A solution of N'-[(2R)-2-benzyloxy-2-(trifluoromethyl)hex-5-enoyl]-3-nitro-6-(1-pyrimidin-2-ylbut-3-enylamino)-5-(trifluoromethyl)pyridine-2-carbohydrazide (215 mg, 0.2969 mmol) and DIPEA (133.56 mg, 0.18 mL, 1.0334 mmol) in acetonitrile (5 mL) was heated in an oil bath set at 60° C. and treated with tosyl chloride (70 mg, 0.3672 mmol). After 90 minutes, the reaction was cooled down to room temperature and concentrated under reduced pressure to remove most of the acetonitrile. Transferred to a 125 mL separatory funnel containing saturated aqueous sodium bicarbonate (50 mL) and the aqueous layer was extracted with ethyl acetate (2×40 mL). The combined organic layers were washed with brine (40 mL), dried over sodium sulfate, filtered and concentrated under reduced pressure. The residue was purified by silica gel chromatography using a gradient from 0% to 50% ethyl acetate in heptanes to afford as a thick amber oil and a ~1:1 mixture of diastereomers, 6-[5-[(1R)-1-benzyloxy-1-(trifluoromethyl)pent-4-enyl]-1,3,4-oxadiazol-2-yl]-5-nitro-N-(1-pyrimidin-2-ylbut-3-enyl)-3-(trifluoromethyl)pyridin-2-amine (176 mg, 85%). $^1$H NMR (400 MHz, CDCl$_3$) δ 8.75 (d, J=4.9 Hz, 2H), 8.60 (s, 1H), 7.66 (br. s., 1H), 7.45-7.28 (m, 5H), 7.25 (td, J=4.9, 1.0 Hz, 1H), 5.88-5.76 (m, 1H), 5.72-5.65 (m, 1H), 5.58 (ddtd, J=17.1, 9.9, 7.4, 2.3 Hz, 1H), 5.10 (dt, J=17.1, 1.5 Hz, 1H), 5.05-4.92 (m, 3H), 4.83 (dd, J=10.6, 6.2 Hz, 1H), 4.67 (dd, J=10.5, 4.9 Hz, 1H), 3.02-2.92 (m, 1H), 2.85-2.75 (m, 1H), 2.59-2.22 (m, 4H) ppm. ESI-MS m/z calc. 649.1872, found 650.2 (M+1)$^+$; Retention time: 4.16 minutes (LC Method BB).

Step 7: (6R)-6-Benzyloxy-17-nitro-12-pyrimidin-2-yl-6,15-bis(trifluoromethyl)-19-oxa-3,4,13,18-tetrazatricyclo[12.3.1.1²,⁵]nonadeca-1(17),2,4,9,14(18),15-hexaene (E/Z mixture)

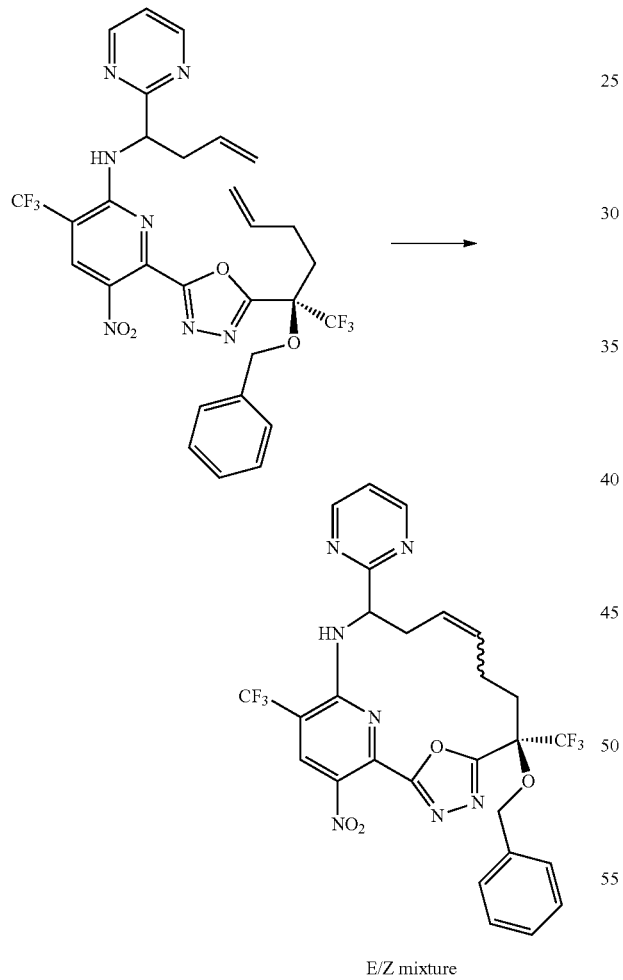

E/Z mixture

A 100-mL three-necked flask equipped with a reflux condenser (with an adaptor at the top that is attached with tubbing to a glass bubbler) was charged with dichloroethane (40 mL) and purged with nitrogen gas while heating in an oil bath set at 50° C. for 45 to 60 minutes. Added Zhan catalyst-1B (22 mg, 0.0300 mmol), stirred for 5 minutes, then added a solution of 6-[5-[(1R)-1-benzyloxy-1-(trifluoromethyl)pent-4-enyl]-1,3,4-oxadiazol-2-yl]-5-nitro-N-(1-pyrimidin-2-ylbut-3-enyl)-3-(trifluoromethyl)pyridin-2-amine (84 mg, 0.1199 mmol) in dichloroethane (5 mL) over a period of ~5 minutes. Heating was increased to 83° C. (oil bath temperature) and the reaction was stirred for 16 h while continuing to bubble with nitrogen gas. After cooling to room temperature, the reaction mixture was quenched with DMSO (3 drops) and concentrated under reduced pressure. The residue was directly adsorbed on silica gel and was purified by silica gel chromatography using a gradient from 0% to 50% ethyl acetate in heptanes to afford as an amber oil, (6R)-6-benzyloxy-17-nitro-12-pyrimidin-2-yl-6,15-bis(trifluoromethyl)-19-oxa-3,4,13,18-tetrazatricyclo[12.3.1.1²,⁵]nonadeca-1(17),2,4,9,14(18),15-hexaene (E/Z mixture) (39 mg, 49%). ESI-MS m/z calc. 621.1559, found 622.2 (M+1)$^+$; Retention time: 4.0 minutes (LC Method BB).

Step 8: (6R)-17-Amino-12-pyrimidin-2-yl-6,15-bis(trifluoromethyl)-19-oxa-3,4,13,18-tetrazatricyclo[12.3.1.1²,⁵]nonadeca-1(18),2,4,14,16-pentaen-6-ol

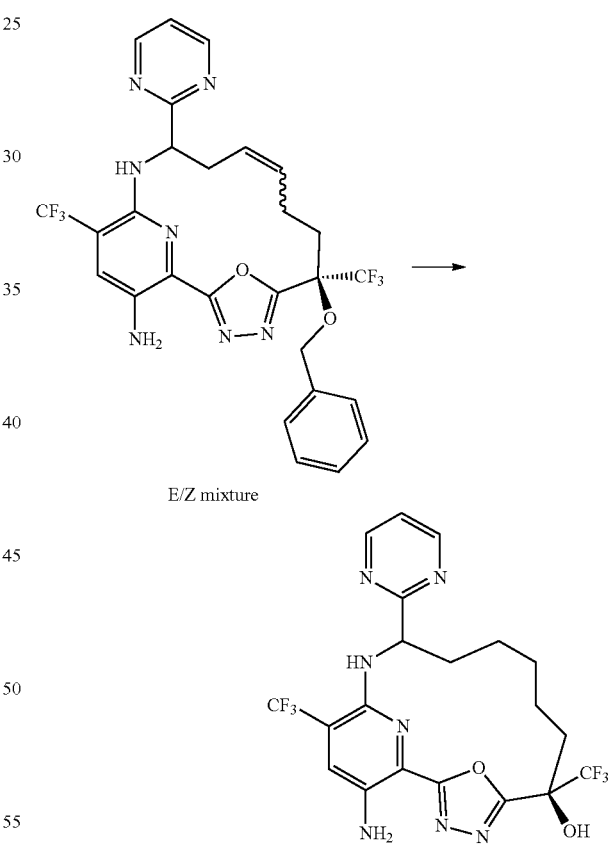

(6R)-6-benzyloxy-17-nitro-12-pyrimidin-2-yl-6,15-bis(trifluoromethyl)-19-oxa-3,4,13,18-tetrazatricyclo[12.3.1.1²,⁵]nonadeca-1(17),2,4,9,14(18),15-hexaene (E/Z mixture) (32 mg, 0.0477 mmol) was dissolved in anhydrous methanol (3 mL). Nitrogen was bubbled into the mixture for 5 minutes and then palladium on carbon (35 mg, 5 w/w, 0.0164 mmol) was added. Hydrogen was then bubbled into the mixture with a balloon for 5 minutes and the reaction mixture was stirred at room temperature under hydrogen overnight. The mixture was filtered using a nylon 0.45 micron filter (on a syringe) rinsing with methanol (2×µL, 0.4 mL). The filtrate was concentrated by evaporation under reduced pressure to give as a dark yellow oil, (6R)-17-amino-12-pyrimidin-2-yl-6,15-bis(trifluoromethyl)-19-oxa-3,4,13,18-tetrazatricyclo[12.3.1.12,5]nonadeca-1(18),2,4,14,16-pentaen-6-ol (30 mg, 86%, 69% purity). ESI-MS m/z calc. 503.1504, found 503.9 (M+1)$^+$; Retention time: 3.13 minutes (LC Method C).

Step 9: (6R)-17-Amino-12-pyrimidin-2-yl-6,15-bis(trifluoromethyl)-19-oxa-3,4,13,18-tetrazatricyclo [12.3.1.12,5]nonadeca-1(18),2,4,14,16-pentaen-6-ol (enantiomer 1) (Compound 201) and (6R)-17-amino-12-pyrimidin-2-yl-6,15-bis(trifluoromethyl)-19-oxa-3,4,13,18-tetrazatricyclo[12.3.1.12,5]nonadeca-1(18),2,4,14,16-pentaen-6-ol (enantiomer 2) (Compound 202)

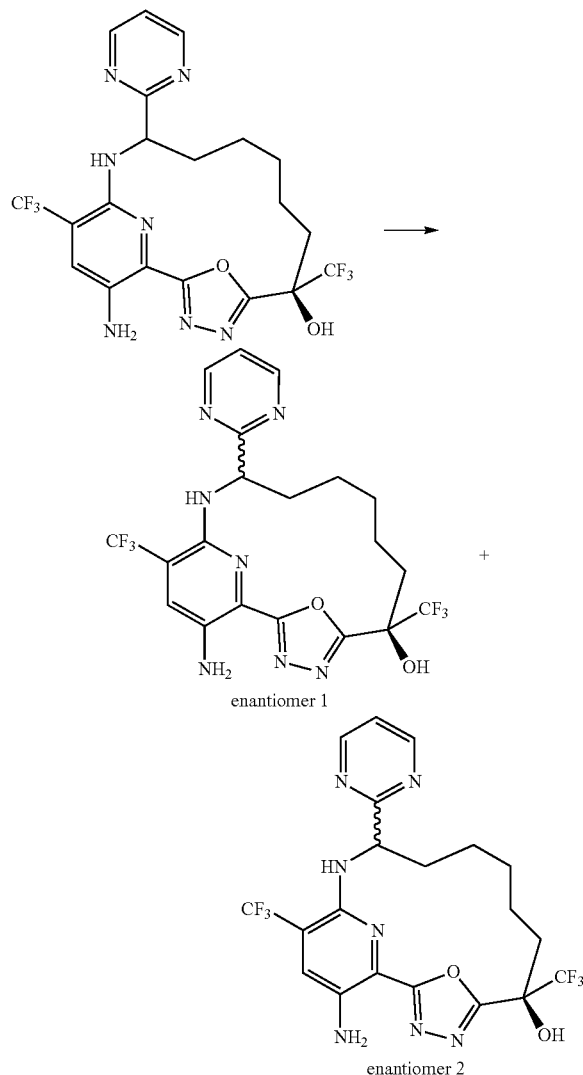

Racemic (6R)-17-amino-12-pyrimidin-2-yl-6,15-bis(trifluoromethyl)-19-oxa-3,4,13,18-tetrazatricyclo[12.3.1.12,5]nonadeca-1(18),2,4,14,16-pentaen-6-ol (45 mg, 0.0614 mmol, 69% purity) was directly adsorbed on silica gel and was purified by silica gel chromatography using a gradient from 0% to 50% ethyl acetate in heptanes to give 28 mg of material enriched to 89% purity. This material was then adsorbed on silica gel and again purified by silica gel chromatography using a gradient from 0% to 30% ethyl acetate in heptanes to give 19.5 mg of material enriched to 95.9% purity. This diastereoisomeric mixture was subjected to SFC separation using a Lux Cellulose 1 column, (150× 21.2 mm, 5 µm particle size) at 40° C. eluting with 20% MeOH in CO$_2$, flow rate: 75 mL/min, injection volume: 1500 µL, pressure: 100 bar, wavelength: 210 nm which provided two single enantiomer products:

The first enantiomer to elute was isolated as a yellow solid, (6R)-17-amino-12-pyrimidin-2-yl-6,15-bis(trifluoromethyl)-19-oxa-3,4,13,18-tetrazatricyclo[12.3.1.12,5] nonadeca-1(18),2,4,14,16-pentaen-6-ol (enantiomer 1) (4 mg, 12%). $^1$H NMR (400 MHz, DMSO-d6) δ 8.82 (d, J=4.9 Hz, 2H), 7.62 (s, 1H), 7.53 (s, 1H), 7.44 (t, J=5.0 Hz, 1H), 6.22 (d, J=5.4 Hz, 1H), 6.04 (s, 2H), 5.02-4.95 (m, 1H), 2.31-2.22 (m, 1H), 2.13-2.02 (m, 1H), 1.96-1.85 (m, 1H), 1.71-1.31 (m, 7H) ppm. $^{19}$F NMR (377 MHz, DMSO-d6) δ−62.80 (s, 3F), −76.54 (s, 3F) ppm. ESI-MS m/z calc. 503.1504, found 504.2 (M+1)$^+$; Retention time: 3.17 minutes (LC Method C).

The second enantiomer to elute was isolated as a yellow solid, (6R)-17-amino-12-pyrimidin-2-yl-6,15-bis(trifluoromethyl)-19-oxa-3,4,13,18-tetrazatricyclo[12.3.1.12,5] nonadeca-1(18),2,4,14,16-pentaen-6-ol (enantiomer 2) (3.5 mg, 11%). $^1$H NMR (400 MHz, DMSO-d6) δ 8.82 (d, J=4.9 Hz, 2H), 7.63 (s, 1H), 7.53 (s, 1H), 7.44 (t, J=4.9 Hz, 1H), 6.27 (d, J=4.4 Hz, 1H), 6.06 (s, 2H), 4.91-4.84 (m, 1H), 2.60-2.50 (m, 1H), 2.24-2.13 (m, 1H), 2.12-1.99 (m, 1H), 1.74-1.47 (m, 5H), 1.46-1.25 (m, 2H) ppm. $^{19}$F NMR (377 MHz, DMSO-d6) δ−62.81 (s, 3F), −79.02 (s, 3F) ppm. ESI-MS m/z calc. 503.1504, found 504.2 (M+1)$^+$; Retention time: 3.12 minutes (LC Method C).

Example 112: Preparation of (6R)-17-amino-12,12-dimethyl-6,15-bis(trifluoromethyl)-19-oxa-3,4,13, 18-tetrazatricyclo[12.3.1.12,5]nonadeca-1(18),2,4, 14,16-pentaene-6,11-diol (enantiomer 1) (Compound 203) and (6R)-17-amino-12,12-dimethyl-6,15-bis(trifluoromethyl)-19-oxa-3,4,13,18-tetrazatricyclo[12.3.1.12,5]nonadeca-1(18),2,4,14, 16-pentaene-6,11-diol (enantiomer 2) (Compound 204)

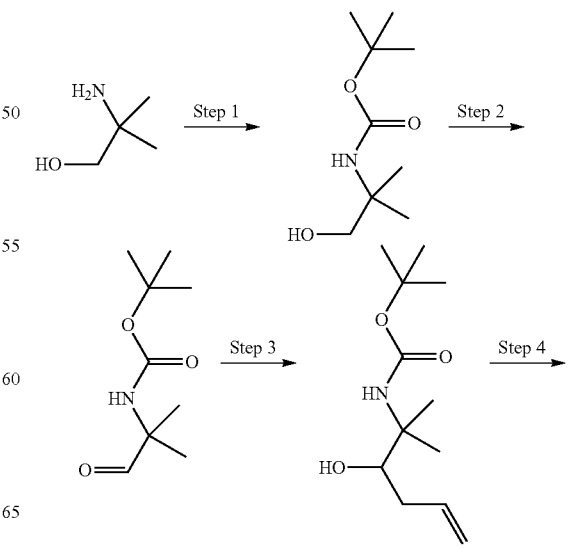

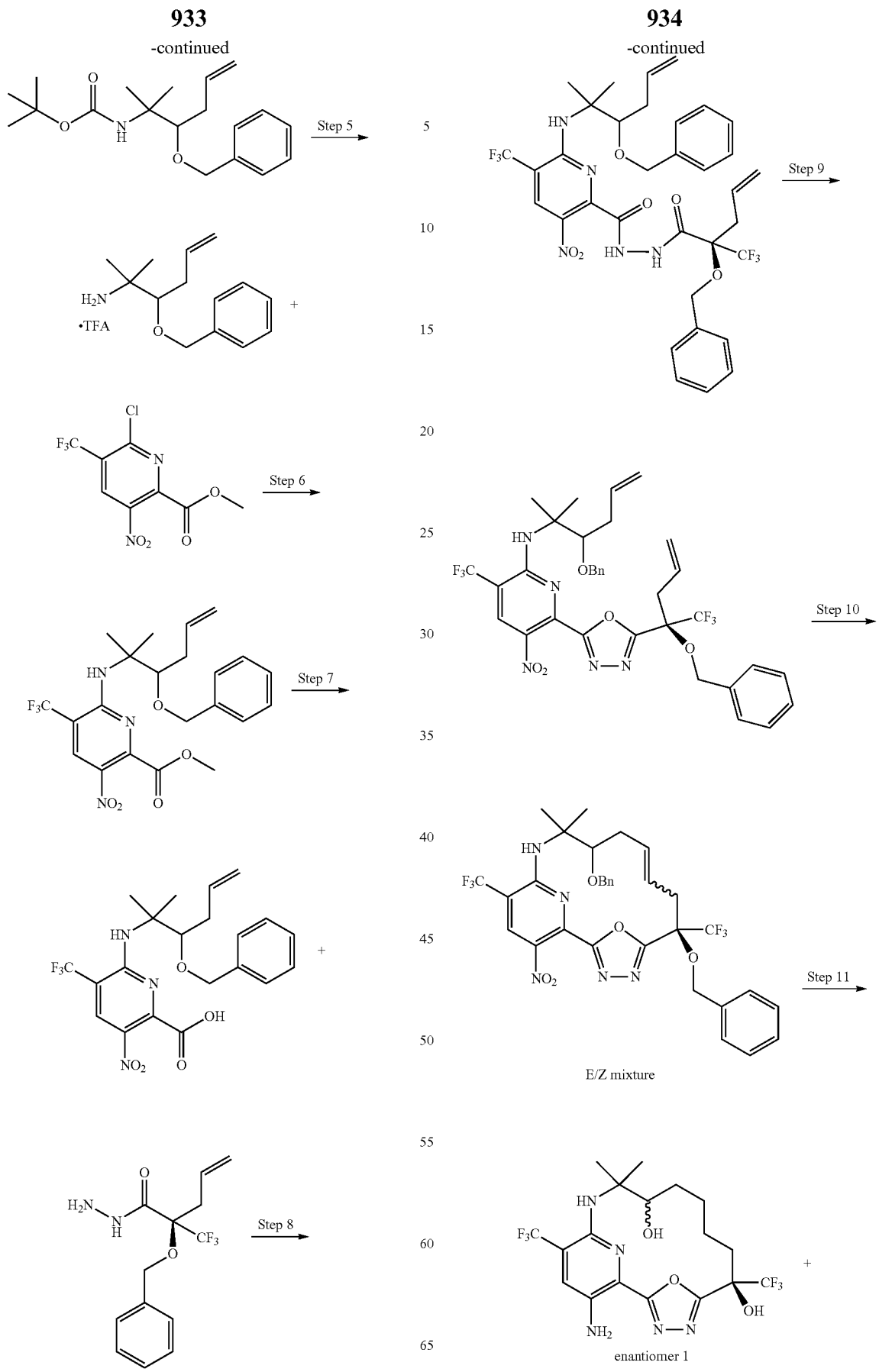

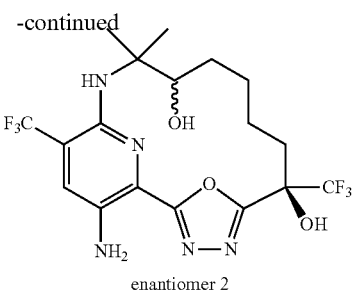

enantiomer 2

Step 1: tert-Butyl
N-(2-hydroxy-1,1-dimethyl-ethyl)carbamate

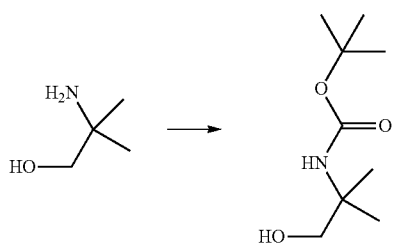

To a solution of 2-amino-2-methyl-propan-1-ol (13.45 g, 16 mL, 135.8 mmol) and triethylamine (13.794 g, 19 mL, 136.32 mmol) in dichloromethane (70 mL) was added di-tert-butyl dicarbonate (27 g, 123.71 mmol) over 10 min and the mixture was stirred at room temperature for 3 h. The reaction mixture was concentrated under reduced pressure and diluted with a 10% aqueous solution of citric acid (200 mL), followed by extraction with ethyl acetate (2×100 mL). The organic layer was washed with water (150 mL) and brine (150 mL) then dried over anhydrous magnesium sulfate, filtered and concentrated under reduced pressure to give as a white solid, tert-butyl N-(2-hydroxy-1,1-dimethyl-ethyl)carbamate (19.5 g, 83%). $^1$H NMR (400 MHz, Chloroform-d) δ 4.71 (br s, 1H), 4.27-3.96 (m, 1H), 3.57 (d, J=5.4 Hz, 2H), 1.43 (s, 9H), 1.25 (s, 6H) ppm.

Step 2: tert-Butyl
N-(1,1-dimethyl-2-oxo-ethyl)carbamate

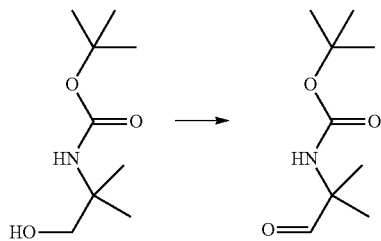

A solution of tert-butyl N-(2-hydroxy-1,1-dimethyl-ethyl)carbamate (5 g, 26.42 mmol) in DMSO (80 mL) and Et$_3$N (8.02 g, 11.05 mL, 79.26 mmol) was treated with a solution of sulfur trioxide pyridine complex (12.62 g, 6.573 mL, 79.26 mmol) in DMSO (66 mL). The reaction mixture was then allowed to stir at room temperature for 1 h, then poured into Et$_2$O. The organics were washed with 10% citric acid, saturated NaHCO$_3$ and brine. The organics were then dried over Na$_2$SO$_4$, filtered and concentrated to give as a solid, tert-butyl N-(1,1-dimethyl-2-oxo-ethyl)carbamate (6.0269 g) which was taken directly to the next step.

Step 3: tert-Butyl
N-(2-hydroxy-1,1-dimethyl-pent-4-enyl)carbamate

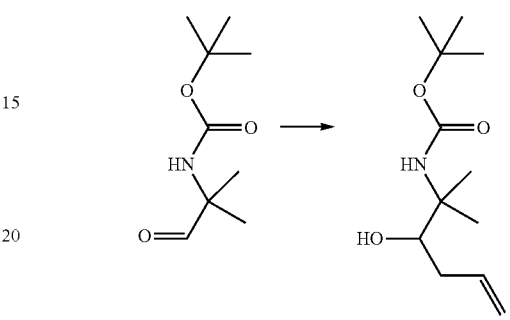

A solution of tert-butyl N-(1,1-dimethyl-2-oxo-ethyl)carbamate (1 g, 5.3409 mmol) was cooled to −78° C. and treated dropwise with allylmagnesium chloride (5.4 mL of 2 M, 10.8 mmol) over 5 minutes and then held at this temperature for an additional 5 minutes. The dry ice bath was removed, and the flask was placed into an ice water bath (0° C. to 5° C.). The solution was stirred at this temperature for 1 h and then poured into a mixture of an aqueous solution of NH$_4$Cl (100 mL) over ice (100 g). The mixture was extracted with EtOAc (5×75 mL) and the combined organic layers were washed with brine (25 mL), dried over Na$_2$SO$_4$, filtered and concentrated. The residue was purified by silica gel chromatography (80 g column) using a gradient from 0% to 20% EtOAc in hexanes over 10 minutes giving as a colorless solid, tert-butyl N-(2-hydroxy-1,1-dimethyl-pent-4-enyl)carbamate (980 mg, 80%). $^1$H NMR (500 MHz, Chloroform-d) δ 6.00-5.89 (m, 1H), 5.15-5.08 (m, 2H), 4.67 (s, 1H), 3.84 (s, 1H), 3.57 (d, J=10.1 Hz, 1H), 2.39-2.30 (m, 1H), 2.11-2.01 (m, 1H), 1.44 (s, 9H), 1.37 (s, 3H), 1.23 (s, 3H) ppm. ESI-MS m/z calc. 229.1678, found 230.7 (M+1)$^+$; Retention time: 4.15 minutes (LC Method DD).

Step 4: tert-Butyl
N-(2-benzyloxy-1,1-dimethyl-pent-4-enyl)carbamate

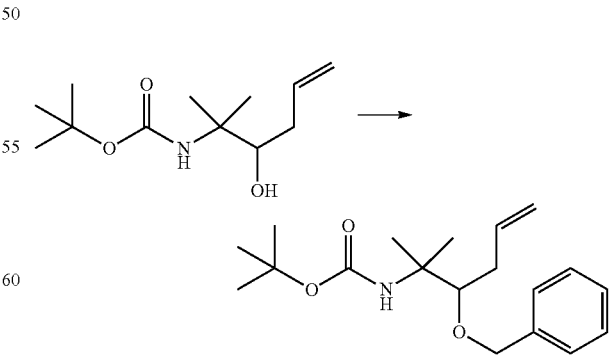

A flask was charged with NaH in mineral oil (2.12 g, 60% w/w, 53.005 mmol) under argon and washed with hexanes (55 mL) and the supernatant layer was decanted (53 mL)

through a needle and syringe. The solids were treated with THF (23 mL) and cooled to 0° C. The slurry was then treated dropwise with a solution of tert-butyl N-(2-hydroxy-1,1-dimethyl-pent-4-enyl)carbamate (4.06 g, 17.705 mmol) in THF (26 mL) over 35 minutes at 0° C. and stirred for an additional 30 min. The reaction was then treated with benzyl bromide (7.4776 g, 5.2 mL, 43.72 mmol) dropwise over 10 minutes, followed by TBAI (654 mg, 1.7706 mmol) in one portion and stirred at 0° C. for an additional 3 h. The ice bath was removed, and the reaction was warmed to room temperature over 90 min and stirred for an additional 1 h. The mixture was diluted with Et$_2$O (50 mL) and the resulting mixture was added carefully (5 mL portions) to a stirred mixture of saturated aqueous NH$_4$Cl solution (300 mL) in ice (300 g). The reaction was diluted with EtOAc (400 mL) and the layers were separated. The aqueous phase was extracted with EtOAc (4×150 mL) and the combined organic layers were washed with brine (50 mL), dried over Na$_2$SO$_4$, filtered and concentrated. The crude residue was purified by silica gel chromatography using a gradient from 100% hexanes to 5% ethyl acetate in hexanes to provide as a colorless liquid tert-butyl N-(2-benzyloxy-1,1-dimethyl-pent-4-enyl)carbamate (4.47 g, 78%). $^1$H NMR (500 MHz, Chloroform-d) δ 7.36-7.31 (m, 4H), 7.31-7.26 (m, 1H), 5.99-5.89 (m, 1H), 5.13 (dq, J=17.1, 1.6 Hz, 1H), 5.06-5.02 (m, 1H), 4.71-4.64 (m, 2H), 4.54 (d, J=11.1 Hz, 1H), 3.95-3.76 (m, 1H), 2.44-2.35 (m, 1H), 2.30-2.23 (m, 1H), 1.43 (s, 9H), 1.31 (d, J=9.4 Hz, 6H) ppm. ESI-MS m/z calc. 319.2147, found 320.4 (M+1)$^+$; Retention time: 7.06 minutes (LC Method DD).

Step 5: 3-Benzyloxy-2-methyl-hex-5-en-2-amine (trifluoroacetate Salt)

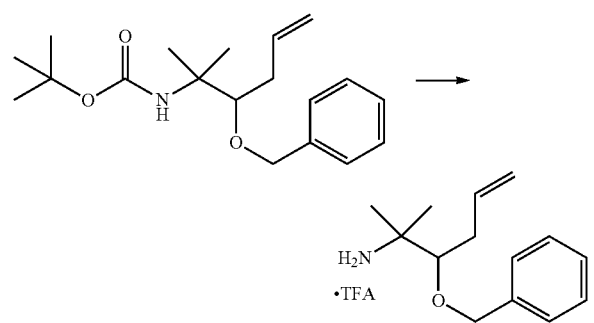

A solution of tert-butyl N-(2-benzyloxy-1,1-dimethyl-pent-4-enyl)carbamate (400 mg, 1.2522 mmol) in DCM (7 mL) was cooled to 0° C. under nitrogen and treated dropwise with a chilled (0° C. to 5° C.) solution of TFA (888 mg, 0.6 mL, 7.7879 mmol) in DCM (4 mL) over 5 minutes. The bath was removed, and the reaction was warmed to room temperature for 150 minutes. The reaction was concentrated at room temperature and dried under vacuum for 5 days to give as a colorless brittle solid, 3-benzyloxy-2-methyl-hex-5-en-2-amine (trifluoroacetate salt) (431 mg, 100%). $^1$H NMR (500 MHz, DMSO-d6) δ 7.81 (s, 3H), 7.42-7.32 (m, 4H), 7.34-7.26 (m, 1H), 5.96-5.84 (m, 1H), 5.21-5.12 (m, 1H), 5.07 (d, J=9.8 Hz, 1H), 4.64 (d, J=11.2 Hz, 1H), 4.55 (d, J=11.3 Hz, 1H), 3.50 (dd, J=7.4, 4.0 Hz, 1H), 2.48-2.42 (m, 1H), 2.30-2.23 (m, 1H), 1.24 (d, J=19.7 Hz, 6H) ppm. ESI-MS m/z calc. 219.1623, found 220.6 (M+1)$^+$; Retention time: 3.18 minutes (LC Method DD).

Step 6: Methyl 6-[(2-benzyloxy-1,1-dimethyl-pent-4-enyl)amino]-3-nitro-5-(trifluoromethyl)pyridine-2-carboxylate

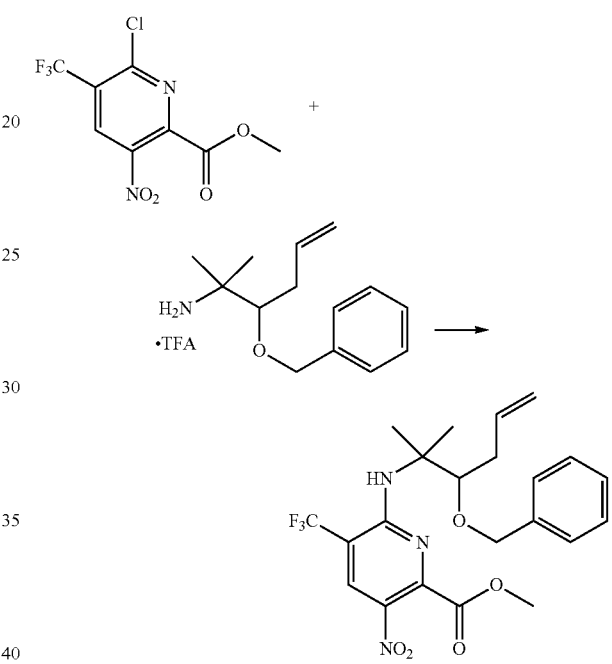

To a solution of methyl 6-chloro-3-nitro-5-(trifluoromethyl)pyridine-2-carboxylate (4.65 g, 16.34 mmol) and 3-benzyloxy-2-methyl-hex-5-en-2-amine (trifluoroacetate salt) (6.11 g, 18.329 mmol) in DCM (43 mL) under argon was added Et$_3$N (6.534 g, 9 mL, 64.572 mmol) at room temperature and the reaction was stirred for 160 min. The reaction was treated with additional Et$_3$N (3.993 g, 5.5 mL, 39.46 mmol) dropwise over 3 minutes and heated at 40° C., then at 30° C. for 18 h. The reaction was diluted with DCM (150 ml) and washed with brine (20 ml). The brine layer was extracted with DCM (30 mL). The organic layers were combined and dried over Na$_2$SO$_4$, filtered, and concentrated under reduced pressure. The residue was purified by silica gel chromatography using a gradient from 0% to 5% EtOAc in hexanes to obtain as a thick yellow oil, methyl 6-[(2-benzyloxy-1,1-dimethyl-pent-4-enyl)amino]-3-nitro-5-(trifluoromethyl)pyridine-2-carboxylate (6.18 g, 76%). $^1$H NMR (500 MHz, Chloroform-d) δ 8.40 (s, 1H), 7.34-7.25 (m, 5H), 6.27 (s, 1H), 5.98-5.85 (m, 1H), 5.19-5.11 (m, 1H), 5.08 (d, J=10.3 Hz, 1H), 4.76 (d, J=11.3 Hz, 1H), 4.49 (d, J=11.4 Hz, 1H), 4.02 (s, 3H), 3.81-3.75 (m, 1H), 2.55-2.46 (m, 1H), 2.42-2.32 (m, 1H), 1.53 (s, 6H) ppm. ESI-MS m/z calc. 467.1668, found 468.2 (M+1)$^+$; Retention time: 7.64 minutes (LC Method DD).

Step 7: 6-[(2-Benzyloxy-1,1-dimethyl-pent-4-enyl)amino]-3-nitro-5-(trifluoromethyl)pyridine-2-carboxylic Acid

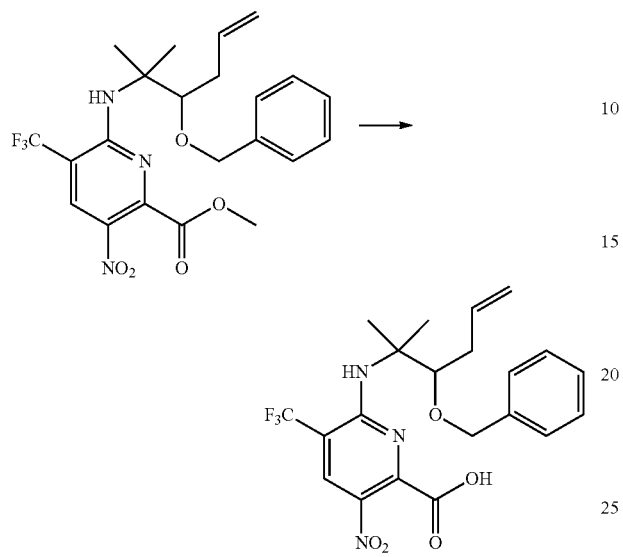

To a solution of methyl 6-[(2-benzyloxy-1,1-dimethyl-pent-4-enyl)amino]-3-nitro-5-(trifluoromethyl)pyridine-2-carboxylate (6.18 g, 12.428 mmol) in THF (30 mL) was added lithium hydroxide (monohydrate) (5.2 g, 123.92 mmol) followed by water (6 mL) and MeOH (2.8 mL). The reaction mixture was then stirred at 30° C. in an oil bath for 5 h. The reaction was then diluted with MTBE (300 mL) washed with water (200 mL) and 1 M NaOH (100 mL). The organic layer was further washed with brine (200 mL), dried over anhydrous sodium sulfate, filtered and concentrated under reduced pressure to provide as a light yellow foam, 6-[(2-benzyloxy-1,1-dimethyl-pent-4-enyl)amino]-3-nitro-5-(trifluoromethyl)pyridine-2-carboxylic acid (5.5 g, 93%). $^1$H NMR (500 MHz, DMSO-d6) δ 8.26 (s, 1H), 7.36-7.24 (m, 5H), 6.00 (s, 1H), 5.97-5.85 (m, 1H), 5.14 (dd, J=17.1, 2.0 Hz, 1H), 5.03 (d, J=10.1 Hz, 1H), 4.70 (d, J=11.4 Hz, 1H), 4.49 (d, J=11.4 Hz, 1H), 3.91 (dd, J=7.1, 3.9 Hz, 1H), 3.30 (s, 1H), 2.30 (dt, J=14.7, 7.2 Hz, 1H), 1.49 (s, 6H) ppm. One exchangeable proton not observed in NMR. ESI-MS m/z calc. 453.15115, found 454.4 (M+1)$^+$; Retention time: 6.61 minutes (LC Method DD).

Step 8: 6-[(2-Benzyloxy-1,1-dimethyl-pent-4-enyl)amino]-N'-[(2R)-2-benzyloxy-2-(trifluoromethyl)pent-4-enoyl]-3-nitro-5-(trifluoromethyl)pyridine-2-carbohydrazide

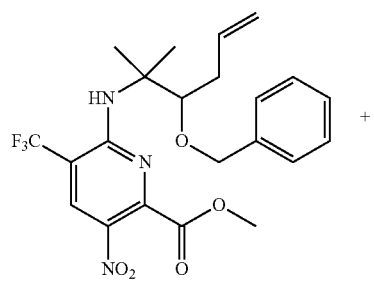

+

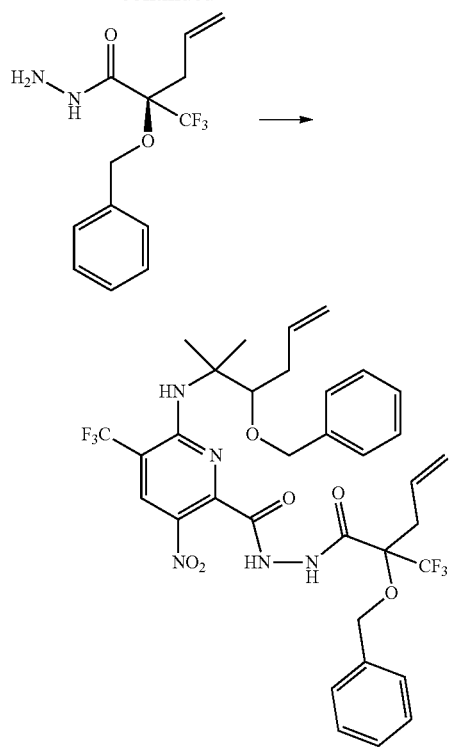

To a solution of 6-[(2-benzyloxy-1,1-dimethyl-pent-4-enyl)amino]-3-nitro-5-(trifluoromethyl)pyridine-2-carboxylic acid (349 mg, 0.7697 mmol) and 2-benzyloxy-2-(trifluoromethyl)pent-4-enehydrazide (222 mg, 0.7701 mmol) in dry EtOAc (2.8 mL) was added propylphosphonic anhydride solution (686 mg, 50% in EtOAc, 1.078 mmol) then pyridine (273.84 mg, 0.280 mL, 3.462 mmol) and the mixture was stirred at room temperature for 6 h. The reaction was diluted with EtOAc (20 mL), quenched with NH$_4$Cl (20 mL) and extracted with EtOAc (2×20 mL). The combined organic layers were washed with brine (2×40 mL), dried over Na$_2$SO$_4$, filtered and concentrated. The residue was purified by silica gel chromatography using a gradient from 0% to 15% EtOAc in hexanes to provide as a white foam, 6-[(2-benzyloxy-1,1-dimethyl-pent-4-enyl)amino]-N'-[(2R)-2-benzyloxy-2-(trifluoromethyl)pent-4-enoyl]-3-nitro-5-(trifluoromethyl)pyridine-2-carbohydrazide (385 mg, 68%). $^1$H NMR (500 MHz, Chloroform-d) δ 9.23-9.16 (m, 1H), 8.58 (dd, J=28.2, 5.4 Hz, 1H), 8.24 (d, J=1.5 Hz, 1H), 7.44-7.34 (m, 5H), 7.28-7.26 (m, 1H), 7.26-7.20 (m, 3H), 6.09 (s, 1H), 6.00-5.77 (m, 2H), 5.40-5.25 (m, 2H), 5.14 (dt, J=17.1, 1.6 Hz, 1H), 5.07 (d, J=10.1 Hz, 1H), 4.85 (s, 2H), 4.75 (d, J=11.6 Hz, 1H), 4.51 (d, J=11.6 Hz, 1H), 3.85 (dd, J=6.6, 4.3 Hz, 1H), 3.21-3.11 (m, 1H), 3.02 (ddd, J=15.3, 7.8, 3.5 Hz, 1H), 2.50 (t, J=10.6 Hz, 1H), 2.38 (dt, J=14.6, 7.1 Hz, 1H), 1.54-1.50 (m, 6H) ppm. One proton not observed in NMR or masked by solvent. ESI-MS m/z calc. 723.24915, found 724.6 (M+1)$^+$; Retention time: 7.9 minutes (LC Method DD).

Step 9: N-(2-Benzyloxy-1,1-dimethyl-pent-4-enyl)-6-[5-[(1R)-1-benzyloxy-1-(trifluoromethyl)but-3-enyl]-1,3,4-oxadiazol-2-yl]-5-nitro-3-(trifluoromethyl)pyridin-2-amine

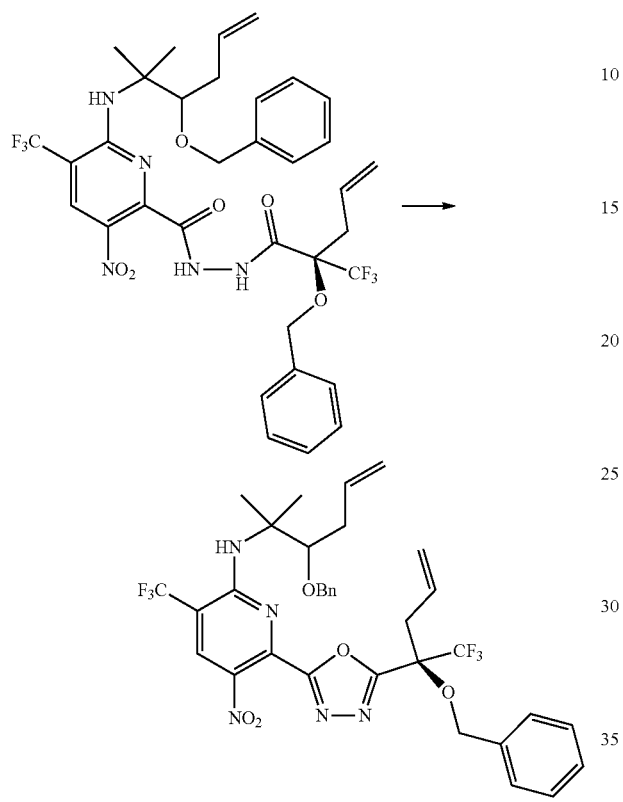

To a solution of 6-[(2-benzyloxy-1,1-dimethyl-pent-4-enyl)amino]-N'-[(2R)-2-benzyloxy-2-(trifluoromethyl)pent-4-enoyl]-3-nitro-5-(trifluoromethyl)pyridine-2-carbohydrazide (385 mg, 0.5267 mmol) in CH$_3$CN (5 mL) was added p-TsCl (115 mg, 0.6032 mmol) then DIPEA (204.05 mg, 0.275 mL, 1.5788 mmol) and the mixture was stirred at room temperature for 30 minutes. The reaction was diluted with EtOAc (30 mL) then washed with NH$_4$Cl (30 mL) and brine (30 mL). The organic layer was dried over Na$_2$SO$_4$, filtered and concentrated. The residue was purified by silica gel chromatography using a gradient from 0% to 100% EtOAc in hexanes to provide as a pale green oil, N-(2-benzyloxy-1,1-dimethyl-pent-4-enyl)-6-[5-[(1R)-1-benzyloxy-1-(trifluoromethyl)but-3-enyl]-1,3,4-oxadiazol-2-yl]-5-nitro-3-(trifluoromethyl)pyridin-2-amine (293 mg, 78%). $^1$H NMR (500 MHz, Chloroform-d) δ 8.44 (d, J=2.6 Hz, 1H), 7.41-7.25 (m, 8H), 7.27-7.19 (m, 2H), 6.33 (d, J=7.1 Hz, 1H), 6.02-5.84 (m, 2H), 5.32-5.18 (m, 2H), 5.18-5.03 (m, 2H), 4.78 (ddd, J=34.0, 11.0, 1.9 Hz, 2H), 4.68-4.60 (m, 1H), 4.46 (dd, J=11.4, 4.1 Hz, 1H), 3.76 (dt, J=6.5, 4.0 Hz, 1H), 3.30-3.15 (m, 2H), 2.54-2.44 (m, 1H), 2.37 (dt, J=14.6, 7.1 Hz, 1H), 1.49 (s, 6H) ppm. ESI-MS m/z calc. 705.2386, found 706.4 (M+1)$^+$; Retention time: 8.79 minutes (LC Method DD).

Step 10: (6R)-6,11-Dibenzyloxy-12,12-dimethyl-17-nitro-6,15-bis(trifluoromethyl)-19-oxa-3,4,13,18-tetrazatricyclo[12.3.1.12,5]nonadeca-1(18),2,4,8,14,16-hexaene (E/Z mixture)

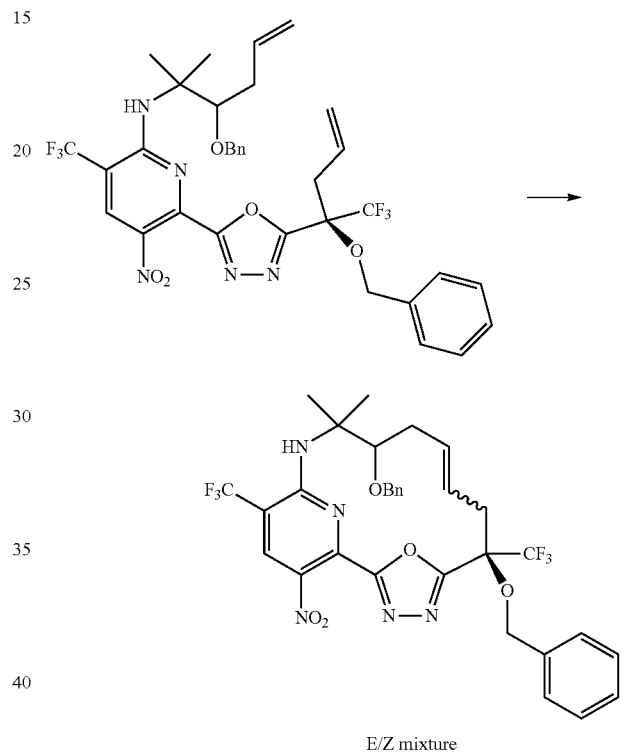

E/Z mixture

A solution of N-(2-benzyloxy-1,1-dimethyl-pent-4-enyl)-6-[5-[(1R)-1-benzyloxy-1-(trifluoromethyl)but-3-enyl]-1,3,4-oxadiazol-2-yl]-5-nitro-3-(trifluoromethyl)pyridin-2-amine (100 mg, 0.1417 mmol) in 1,2-dichloroethane (60 mL) was degassed by sparging with argon gas and then Zhan catalyst-1B (12.491 mg, 0.017 mmol) was added and further degassed for 1 h. The mixture was heated at 70° C. for 18 h. The reaction was cooled to room temperature and concentrated. The residue was purified by silica gel chromatography using a gradient from 0% to 10% EtOAc in hexanes to provide as a white foam, (6R)-6,11-dibenzyloxy-12,12-dimethyl-17-nitro-6,15-bis(trifluoromethyl)-19-oxa-3,4,13,18-tetrazatricyclo[12.3.1.12,5]nonadeca-1(18),2,4,8,14,16-hexaene (E/Z mixture) (77 mg, 76%). ESI-MS m/z calc. 677.2073, found 678.5 (M+1)$^+$; Retention time: 8.16 minutes (LC Method DD).

Step 11: (6R)-17-Amino-12,12-dimethyl-6,15-bis(trifluoromethyl)-19-oxa-3,4,13,18-tetrazatricyclo[12.3.1.12,5]nonadeca-1(18),2,4,14,16-pentaene-6,11-diol (enantiomer 1) (Compound 203) and (6R)-17-amino-12,12-dimethyl-6,15-bis(trifluoromethyl)-19-oxa-3,4,13,18-tetrazatricyclo[12.3.1.12,5]nonadeca-1(18),2,4,14,16-pentaene-6,11-diol (enantiomer 2) (Compound 204)

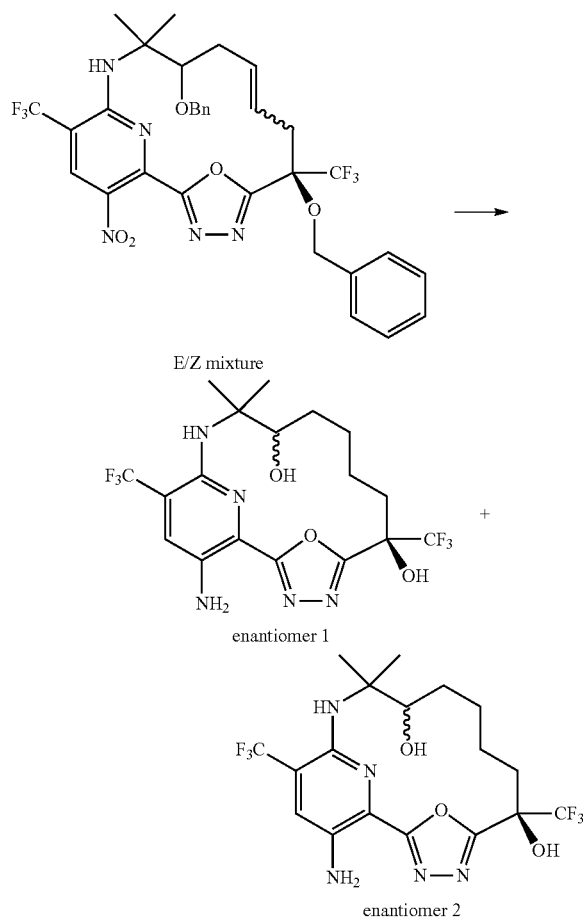

To a solution of (6R)-6,11-dibenzyloxy-12,12-dimethyl-17-nitro-6,15-bis(trifluoromethyl)-19-oxa-3,4,13,18-tetrazatricyclo[12.3.1.12,5]nonadeca-1(18),2,4,8,14,16-hexaene (E/Z mixture) (69 mg, 0.0967 mmol) in EtOH (3.5 mL) was added Pd/C (7 mg, 10% w/w, 0.0066 mmol) under $N_2$ and the mixture was stirred for 15 minutes. The reaction vessel was purged with hydrogen gas and stirred at 1 atm of hydrogen using a hydrogen balloon at room temperature for 36 h. Additional Pd/C (7 mg, 10% w/w, 0.0066 mmol) was added and the mixture was stirred at room temperature for another 48 h. The mixture was diluted with EtOH (14 mL) filtered through a plug of Celite and to the filtrate was added Pd/C (39 mg, 10% w/w, 0.0366 mmol) under $N_2$ then added to a reaction vessel which was purged with hydrogen gas and stirred under 1 atm of hydrogen (balloon) at room temperature for 1.5 h. The reaction was then filtered through a pad of Celite and the filtrate was concentrated. The residue was purified by silica gel chromatography using a gradient from 0% to 30% EtOAc in n-pentane which provided two diastereomeric products The first diastereomer to elute was isolated as a yellow glassy material, (6R)-17-amino-12,12-dimethyl-6,15-bis(trifluoromethyl)-19-oxa-3,4,13,18-tetrazatricyclo[12.3.1.12,5]nonadeca-1(18),2,4,14,16-pentaene-6,11-diol (enantiomer 1) (11.2 mg, 49%). $^1$H NMR (500 MHz, CD$_3$OD) δ 7.50 (d, J=0.8 Hz, 1H), 5.79 (dd, J=10.4, 2.0 Hz, 1H), 2.61-2.49 (m, 1H), 2.08-1.97 (m, 1H), 1.83-1.68 (m, 4H), 1.65-1.58 (m, 1H), 1.52 (s, 3H), 1.46-1.37 (m, 1H), 1.23 (s, 3H) ppm. ESI-MS m/z calc. 469.1549, found 470.5 (M+1)$^+$; Retention time: 2.33 minutes (LC Method H).

The second diastereomer to elute was isolated as a yellow foam, (6R)-17-amino-12,12-dimethyl-6,15-bis(trifluoromethyl)-19-oxa-3,4,13,18-tetrazatricyclo[12.3.1.12,5]nonadeca-1(18),2,4,14,16-pentaene-6,11-diol (enantiomer 2) (10 mg, 44%). $^1$H NMR (500 MHz, CD$_3$OD) δ 7.49 (s, 1H), 5.83-5.77 (m, 1H), 2.52 (td, J 13.8, 2.4 Hz, 1H), 1.98-1.85 (m, 2H), 1.81-1.72 (m, 2H), 1.56 (s, 3H), 1.53-1.36 (m, 3H), 1.22 (s, 3H) ppm. ESI-MS m/z calc. 469.1549, found 470.5 (M+1)$^+$; Retention time: 2.62 minutes (LC Method H).

Example 113: Preparation of (6R)-17-amino-6,15-bis(trifluoromethyl)spiro[19-oxa-3,4,13,18-tetrazatricyclo[12.3.1.12,5]nonadeca-1(18),2,4,14,16-pentaene-12,4'-tetrahydropyran]-6-ol (Compound 205) and (6R)-17-(methylamino)-6,15-bis(trifluoromethyl)spiro[19-oxa-3,4,13,18-tetrazatricyclo[12.3.1.12,5]nonadeca-1(17),2,4,14(18),15-pentaene-12,4'-tetrahydropyran]-6-ol (Compound 206)

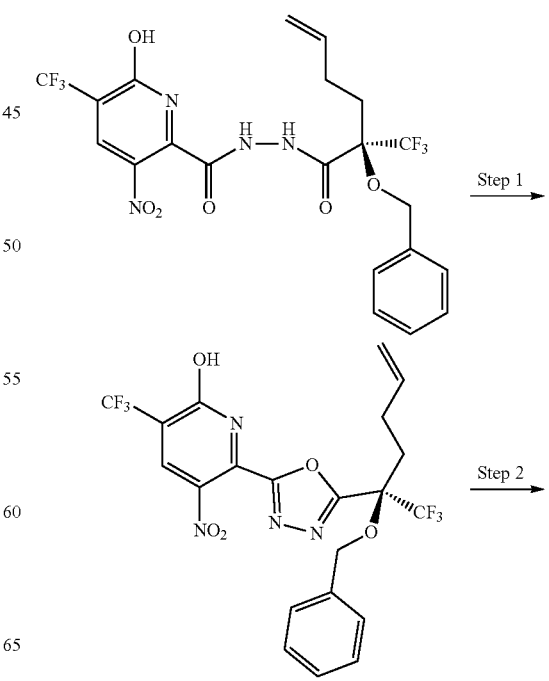

945

-continued

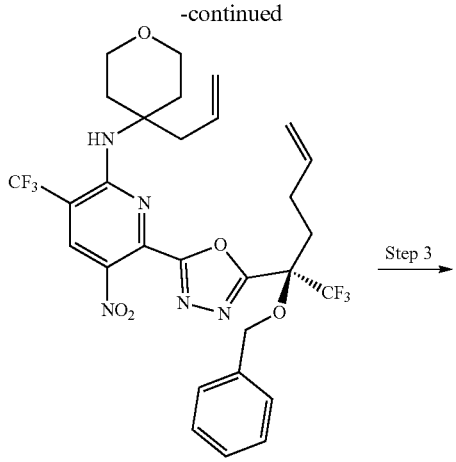

E/Z mixture

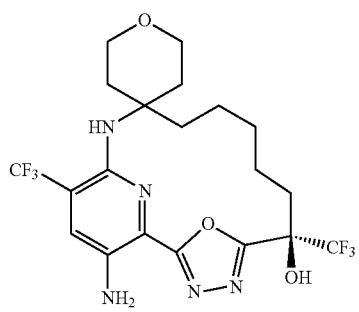

+

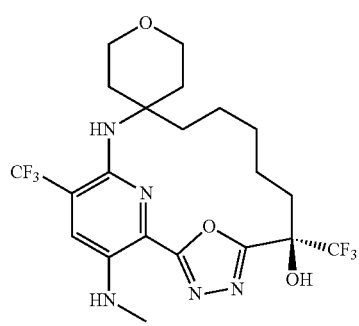

946

Step 1: 2-[(1R)-1-Benzyloxy-1-(trifluoromethyl)
pent-4-enyl]-5-[6-chloro-3-nitro-5-(trifluoromethyl)-
2-pyridyl]-1,3,4-oxadiazole

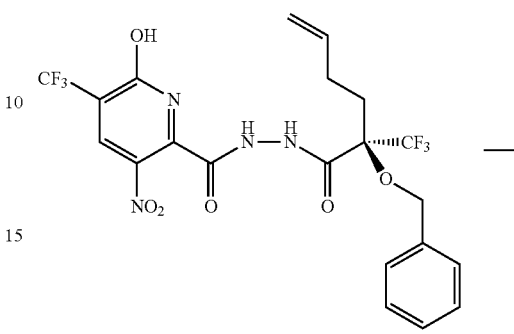

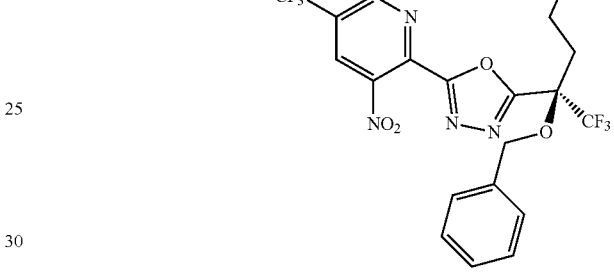

N'-[(2R)-2-Benzyloxy-2-(trifluoromethyl)hex-5-enoyl]-6-hydroxy-3-nitro-5-(trifluoromethyl)pyridine-2-carbohydrazide (30 g, 42.507 mmol) was dissolved in a mixture of phosphoryl trichloride (60 mL) and acetonitrile (60 mL). Dimethylformamide (30 mL) was then added and the mixture was heated at 70° C. for 1 h. The mixture was then quenched in a 1M aqueous potassium bicarbonate solution (900 mL) between 20° C. and 40° C., monitoring the pH during the quench and adjusting using sodium hydroxide (6 M solution, 240 mL in total). The aqueous phase was then extracted with ethyl acetate (2×450 mL) and the organic phases were combined, dried over sodium sulfate (100 g), filtered and evaporated. The residue was then dissolved in ethyl acetate and dry packed using silica (100 g). The dry packed silica gel was added on silica gel (500 g, dry basis) wet with heptanes and then eluted with heptanes (2 L) followed by 10% methyl tert-butyl ether in heptanes (4 L) then 20% methyl tert-butyl ether in heptanes (2 L), and finally with ethyl acetate (2 L). The fractions containing pure product were evaporated and combined to give as a light yellow oil, 2-[(1R)-1-benzyloxy-1-(trifluoromethyl)pent-4-enyl]-5-[6-chloro-3-nitro-5-(trifluoromethyl)-2-pyridyl]-1,3,4-oxadiazole (12.5 g, 54%). ESI-MS m/z calc. 536.0686, found 537.0 (M+1)+; Retention time: 3.898 minutes (LC Method C).

947

Step 2: N-(4-Allyltetrahydropyran-4-yl)-6-[5-[(1R)-1-benzyloxy-1-(trifluoromethyl)pent-4-enyl]-1,3,4-oxadiazol-2-yl]-5-nitro-3-(trifluoromethyl)pyridin-2-amine

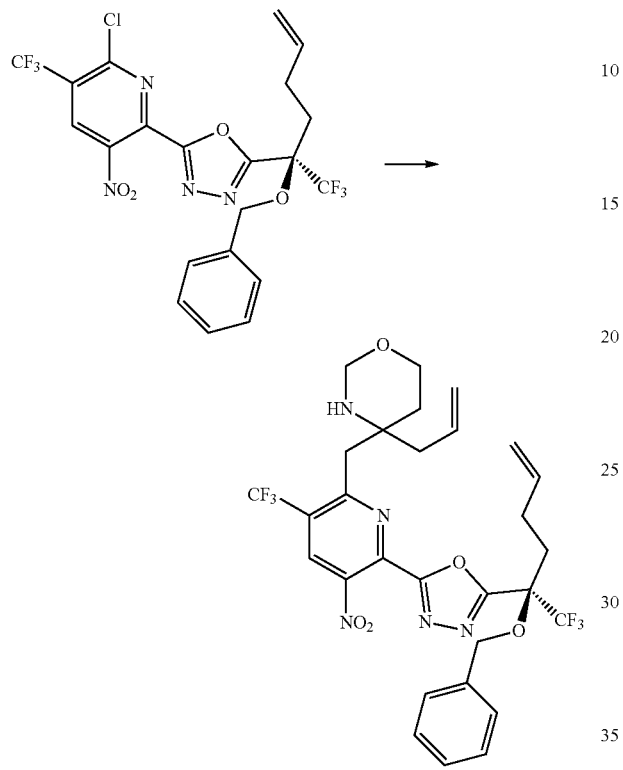

A solution of 2-[(1R)-1-benzyloxy-1-(trifluoromethyl)pent-4-enyl]-5-[6-chloro-3-nitro-5-(trifluoromethyl)-2-pyridyl]-1,3,4-oxadiazole (222 mg, 0.4136 mmol), 4-allyltetrahydropyran-4-amine (92 mg, 0.6515 mmol) and DIPEA (148.40 mg, 0.2 mL, 1.1482 mmol) in acetonitrile (5 mL) was stirred in an oil bath set at 65° C. for ~4 h. Once cooled, the reaction mixture was transferred to a 125 mL separatory funnel with saturated aqueous sodium bicarbonate (40 mL) and the aqueous layer was extracted with ethyl acetate (3×25 mL). The combined organic layers were washed with brine (25 mL), dried over sodium sulfate, filtered and concentrated under reduced pressure. The residue was purified by silica gel chromatography using a gradient from 0% to 25% ethyl acetate in heptanes to afford a dark red oily residue. This material was further purified by reverse-phase $C_{18}$ chromatography, eluting from 5% to 80% acetonitrile in water (+10 mM ammonium bicarbonate/ammonium hydroxide buffer, pH=10) to afford as an orange oil, N-(4-allyltetrahydropyran-4-yl)-6-[5-[(1R)-1-benzyloxy-1-(trifluoromethyl)pent-4-enyl]-1,3,4-oxadiazol-2-yl]-5-nitro-3-(trifluoromethyl)pyridin-2-amine (60.4 mg, 23%). $^1$H NMR (400 MHz, CDCl$_3$) δ 8.55 (s, 1H), 7.44-7.29 (m, 5H), 5.87-5.74 (m, 1H), 5.67 (ddt, J=17.1, 9.9, 7.4 Hz, 1H), 5.43 (br. s., 1H), 5.13-4.95 (m, 4H), 4.84 (d, J=10.5 Hz, 1H), 4.66 (d, J=10.5 Hz, 1H), 3.80 (dt, J=11.9, 3.6 Hz, 2H), 3.65-3.53 (m, 2H), 2.77 (d, J=7.3 Hz, 2H), 2.58-2.16 (m, 6H), 1.93-1.81 (m, 2H) ppm. $^{19}$F NMR (377 MHz, CDCl$_3$)

948

δ −64.52 (s, 3F), −73.15 (s, 3F) ppm. ESI-MS m/z calc. 641.2073, found 642.2 (M+1)$^+$; Retention time: 4.14 minutes (LC Method BB).

Step 3: (6'R)-6'-(benzyloxy)-17'-nitro-6',15'-bis(trifluoromethyl)-19'-oxa-3',4',13',18'-tetraazaspiro[oxane-4,12'-tricyclo[12.3.1.1²,⁵]nonadecane]-1'(18'),2',4',9',14',16'-hexaene (E/Z Mixture)

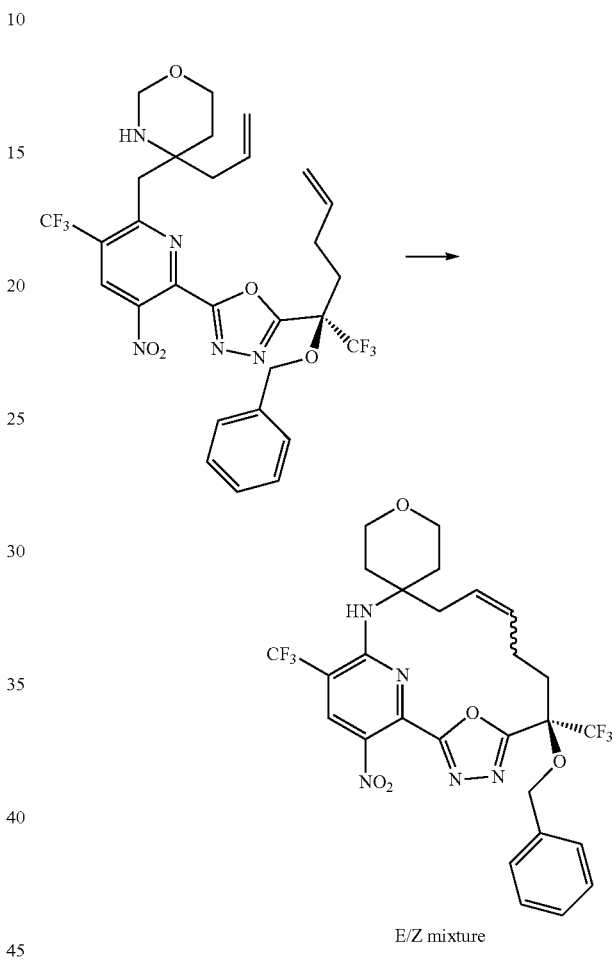

A solution of N-(4-allyltetrahydropyran-4-yl)-6-[5-[(1R)-1-benzyloxy-1-(trifluoromethyl)pent-4-enyl]-1,3,4-oxadiazol-2-yl]-5-nitro-3-(trifluoromethyl)pyridin-2-amine (60.4 mg, 0.0940 mmol) in dichloroethane (30 mL) was bubbled with nitrogen gas for 60 minutes. The solution was then placed in an oil bath set at 60° C. and a first portion of Zhan catalyst-1B (4.6 mg, 0.0063 mmol) was added. After 45 minutes, a second lot of Zhan catalyst-1B (4.5 mg, 0.0061 mmol) was added and heating was continued for another 3 hours. Once cooled to room temperature, the reaction was quenched with DMSO (2 drops), the volatiles were removed under reduced pressure and the residue was directly adsorbed on silica gel. The material was purified by silica gel chromatography using a gradient from 0% to 30% ethyl acetate in heptanes to afford as an off-white solid, (6'R)-6'-(benzyloxy)-17'-nitro-6',15'-bis(trifluoromethyl)-19'-oxa-3',4',13',18'-tetraazaspiro[oxane-4,12'-tricyclo[12.3.1.1²,⁵]nonadecane]-1'(18'),2',4',9',14',16'-hexaene (E/Z mixture) (46.4 mg, 80%). $^1$H NMR (400 MHz, CDCl$_3$) δ 8.59 (s, 1H), 7.41-7.28 (m, 5H), 5.74-5.64 (m, 1H), 5.61-5.47 (m, 2H), 5.18 (d, J=11.0 Hz, 1H), 4.98 (d, J=10.8 Hz, 1H), 3.91-3.81

(m, 2H), 3.57-3.43 (m, 2H), 3.10 (dd, J=13.6, 8.9 Hz, 1H), 2.86 (dd, J=13.6, 7.7 Hz, 1H), 2.44-1.85 (m, 8H) ppm. ESI-MS m/z calc. 613.176, found 614.2 (M+1)$^+$; Retention time: 3.96 minutes (LC Method BB).

Step 4: (6R)-17-Amino-6,15-bis(trifluoromethyl) spiro[19-oxa-3,4,13,18-tetrazatricyclo[12.3.1.12,5] nonadeca-1(18),2,4,14,16-pentaene-12,4'-tetrahydropyran]-6-ol (Compound 205) and (6R)-17-(methylamino)-6,15-bis(trifluoromethyl)spiro[19-oxa-3,4,13,18-tetrazatricyclo[12.3.1.12,5]nonadeca-1(17),2,4,14(18),15-pentaene-12,4'-tetrahydropyran]-6-ol (Compound 206)

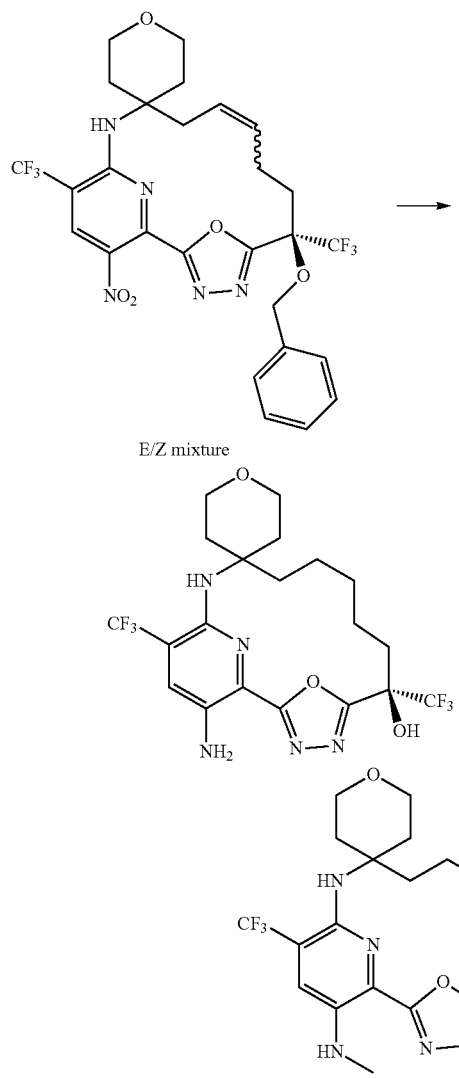

E/Z mixture

A solution of (6'R)-6'-(benzyloxy)-17'-nitro-6',15'-bis(trifluoromethyl)-19'-oxa-3',4',13',18'-tetraazaspiro[oxane-4,12'-tricyclo[12.3.1.12,5]nonadecane]-1'(18'),2',4',9',14',16'-hexaene (E/Z mixture) (46.4 mg, 0.0748 mmol) in methanol (3 mL) was purged three times with nitrogen gas. Added palladium on carbon (48.5 mg, 5% w/w, 0.0228 mmol) then purged the reaction twice with hydrogen gas and the reaction was left to stir under one atmosphere of hydrogen for ~19 hours. The reaction was purged twice with nitrogen gas then filtered over a pad of Celite and the cake was washed with methanol (~30 mL). The volatiles were removed under reduced pressure and the residue was purified by reverse phase C18 chromatography eluting with a gradient from 5% to 70% of acetonitrile in water (+10 mM ammonium bicarbonate/ammonium hydroxide buffer pH=10) to afford two products:

The first product to elute was isolated as a yellow solid, (6R)-17-amino-6,15-bis(trifluoromethyl)spiro[19-oxa-3,4,13,18-tetrazatricyclo[12.3.1.12,5]nonadeca-1(18),2,4,14,16-pentaene-12,4'-tetrahydropyran]-6-ol (16.7 mg, 44%). $^1$H NMR (400 MHz, DMSO-d6) δ 7.62 (s, 1H), 7.58 (s, 1H), 6.01 (s, 2H), 4.79 (s, 1H), 3.70-3.56 (m, 2H), 3.55-3.38 (m, 2H), 2.75-2.62 (m, 1H), 2.23-2.03 (m, 3H), 2.00-1.86 (m, 2H), 1.86-1.61 (m, 3H), 1.60-1.37 (m, 5H) ppm. $^{19}$F NMR (377 MHz, DMSO-d6) δ −62.21 (s, 3F), −78.07 (br. s., 3F) ppm. ESI-MS m/z calc. 495.1705, found 496.2 (M+1)$^+$; Retention time: 3.52 minutes (LC Method BB).

The second product to elute was isolated as a yellow solid, (6R)-17-(methylamino)-6,15-bis(trifluoromethyl)spiro[19-oxa-3,4,13,18-tetrazatricyclo[12.3.1.12,5]nonadeca-1(17),2,4,14(18),15-pentaene-12,4'-tetrahydropyran]-6-ol (7.4 mg, 19%). $^1$H NMR (400 MHz, DMSO-d6) δ 7.60 (s, 1H), 7.45 (s, 1H), 6.16 (q, J=4.6 Hz, 1H), 4.81 (s, 1H), 3.70-3.57 (m, 2H), 3.56-3.39 (m, 2H), 2.95 (d, J=5.1 Hz, 3H), 2.74-2.63 (m, 1H), 2.24-2.04 (m, 3H), 2.01-1.87 (m, 2H), 1.86-1.61 (m, 3H), 1.59-1.37 (m, 5H) ppm. $^{19}$F NMR (377 MHz, DMSO-d6) δ−61.86 (s, 3F), −78.05 (br. s., 3F) ppm. ESI-MS m/z calc. 509.1862, found 510.2 (M+1)$^+$; Retention time: 3.79 minutes (LC Method BB).

Example 114: Preparation of (6R)-17-amino-6,15-bis(trifluoromethyl)spiro[19-oxa-3,4,13,18-tetrazatricyclo[12.3.1.12,5]nonadeca-1(18),2,4,14,16-pentaene-12,3'-tetrahydrofuran]-6-ol (enantiomer 1) (Compound 207) and (6R)-17-amino-6,15-bis(trifluoromethyl)spiro[19-oxa-3,4,13,18-tetrazatricyclo [12.3.1.12,5]nonadeca-1(18),2,4,14,16-pentaene-12,3'-tetrahydrofuran]-6-ol (enantiomer 2) (Compound 208)

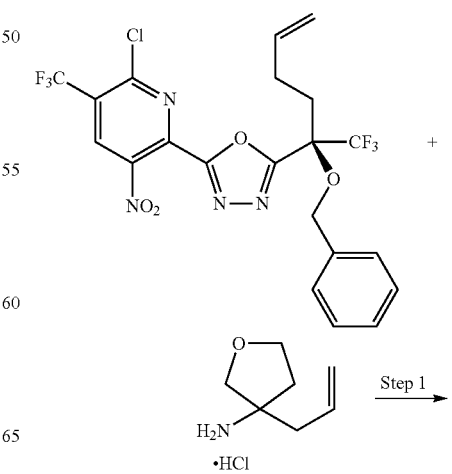

Step 1

951
-continued

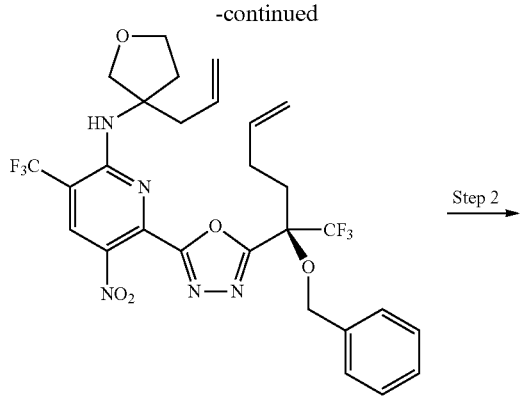

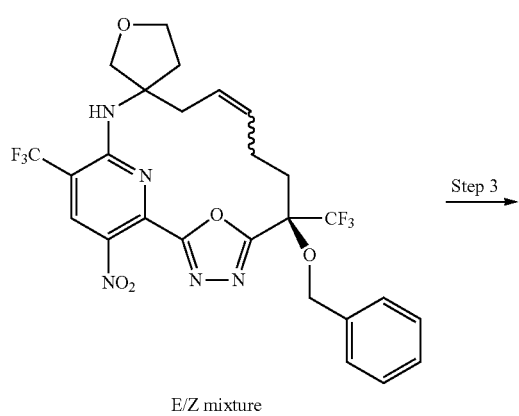
E/Z mixture

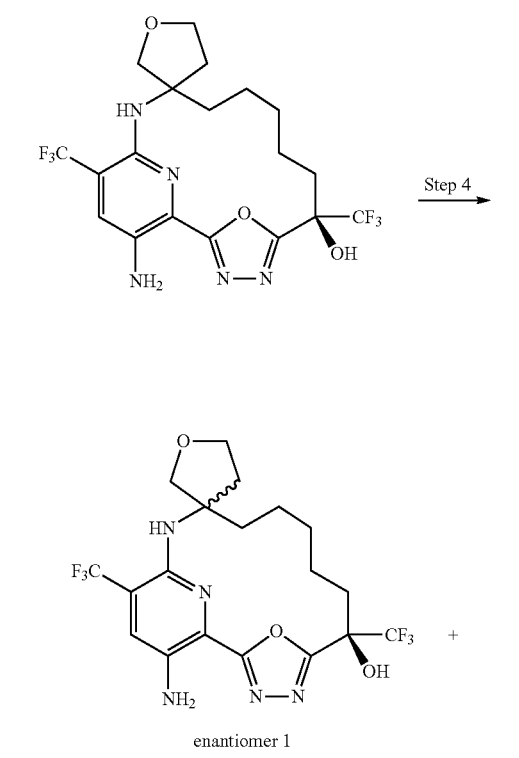
enantiomer 1

952
-continued

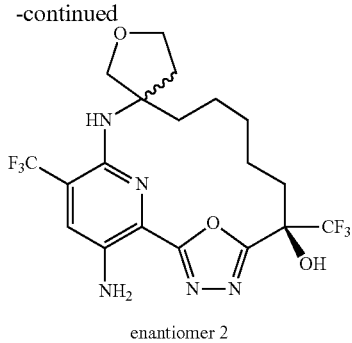
enantiomer 2

Step 1: N-(3-Allyltetrahydrofuran-3-yl)-6-[5-[(1R)-1-benzyloxy-1-(trifluoromethyl)pent-4-enyl]-1,3,4-oxadiazol-2-yl]-5-nitro-3-(trifluoromethyl)pyridin-2-amine

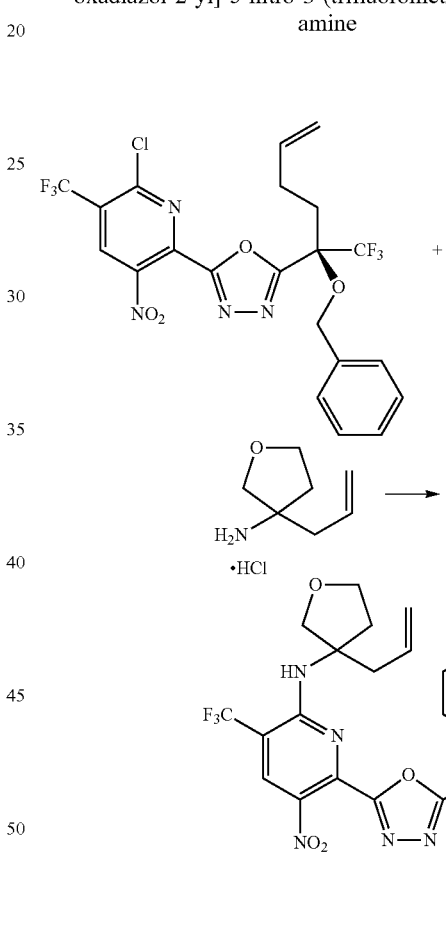

A solution of 2-[(1R)-1-benzyloxy-1-(trifluoromethyl)pent-4-enyl]-5-[6-chloro-3-nitro-5-(trifluoromethyl)-2-pyridyl]-1,3,4-oxadiazole (234 mg, 0.4359 mmol), 3-allyltetrahydrofuran-3-amine (hydrochloride salt) (99 mg, 0.605 mmol) and DIPEA (222.6 mg, 0.3 mL, 1.7223 mmol) in acetonitrile (5 mL) was stirred at 65° C. for 2 h, then at room temperature for 19 h. The reaction mixture was transferred to a 125 mL separatory funnel with a saturated aqueous solution of sodium bicarbonate (50 mL) and the aqueous layer was extracted with ethyl acetate (3×25 mL). The combined organic layers were washed with brine (25 mL), dried over sodium sulfate, filtered and concentrated under reduced pressure. The residue was purified by silica gel chromatography using a gradient from 0% to 30% ethyl acetate in heptanes to afford as an orange-red oil, N-(3-allyltetrahydrofuran-3-yl)-6-[5-[(1R)-1-benzyloxy-1-(trifluoromethyl)pent-4-enyl]-1,3,4-oxadiazol-2-yl]-5-nitro-3-(trifluoromethyl)pyridin-2-amine (220 mg, 80%). $^1$H NMR (400 MHz, Chloroform-d) δ 8.55 (s, 1H), 7.44-7.28 (m, 5H), 5.87-5.66 (m, 3H), 5.14 (dd, J=10.0, 1.2 Hz, 1H), 5.12-5.08 (m, 1H), 5.07-5.04 (m, 1H), 5.02 (dd, J=10.1, 1.3 Hz, 1H), 4.84 (d, J=10.8 Hz, 1H), 4.67 (dd, J=10.6, 1.6 Hz, 1H), 4.02 (d, J=9.5 Hz, 1H), 3.98-3.92 (m, 2H), 3.85 (dd, J=9.5, 1.5 Hz, 1H), 2.79 (d, J=7.3 Hz, 2H), 2.58-2.21 (m, 5H), 2.20-2.09 (m, 1H) ppm. $^{19}$F NMR (377 MHz, Chloroform-d) δ −64.46 (s, 3F), −73.13 (s, 3F, diastereomer A), −73.17 (s, 3F, diastereomer B) ppm. ESI-MS m/z calc. 627.1916, found 628.2 (M+1)$^+$; Retention time: 4.09 minutes (LC Method BB).

Step 2: (6R)-6-Benzyloxy-17-nitro-6,15-bis(trifluoromethyl)spiro[19-oxa-3,4,13,18-tetrazatricyclo[12.3.1.1²,⁵]nonadeca-1(17),2,4,9,14(18),15-hexaene-12,3'-tetrahydrofuran] (E/Z Mixture)

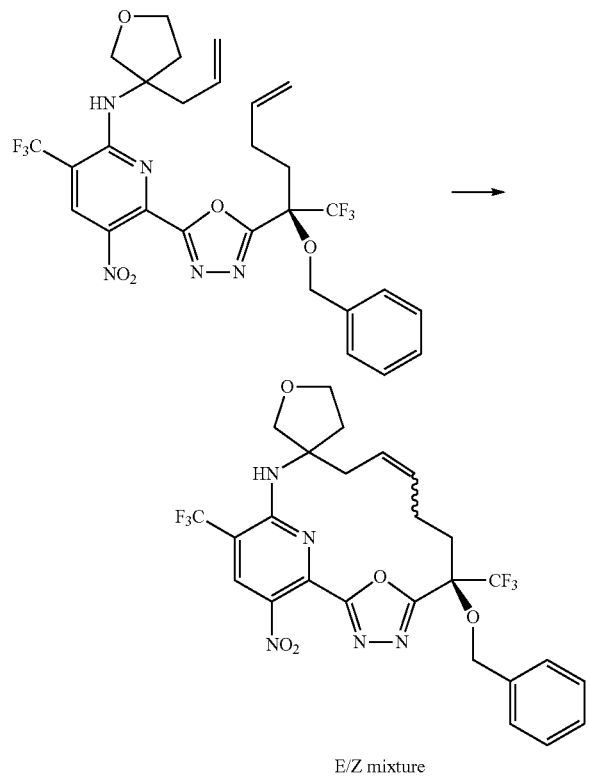

E/Z mixture

A solution of N-(3-allyltetrahydrofuran-3-yl)-6-[5-[(1R)-1-benzyloxy-1-(trifluoromethyl)pent-4-enyl]-1,3,4-oxadiazol-2-yl]-5-nitro-3-(trifluoromethyl)pyridin-2-amine (220 mg, 0.3485 mmol) in dichloroethane (110 mL) was bubbled with nitrogen gas for 22 h. The solution was heated at 60° C. and a first portion of Zhan catalyst-1B (17.9 mg, 0.0244 mmol) was added. After 45 minutes, a second portion of Zhan catalyst-1B (18.2 mg, 0.0248 mmol) was added and heating was continued for another 3 h. The reaction mixture was cooled to room temperature and quenched with DMSO (8 drops). The mixture was concentrated under reduced pressure and the residue was purified by silica gel chromatography using a gradient from 0% to 35% ethyl acetate in heptanes to afford as a pale amber semi-solid, (6R)-6-benzyloxy-17-nitro-6,15-bis(trifluoromethyl)spiro[19-oxa-3,4,13,18-tetrazatricyclo[12.3.1.1²,⁵]nonadeca-1(17),2,4,9,14(18),15-hexaene-12,3'-tetrahydrofuran] (E/Z mixture) (173.9 mg, 82%). ESI-MS m/z calc. 599.1603, found 600.2 (M+1)$^+$; Retention time: 3.88 minutes (LC Method BB).

Step 3: (6R)-17-Amino-6,15-bis(trifluoromethyl)spiro[19-oxa-3,4,13,18-tetrazatricyclo[12.3.1.1²,⁵]nonadeca-1(18),2,4,14,16-pentaene-12,3'-tetrahydrofuran]-6-ol

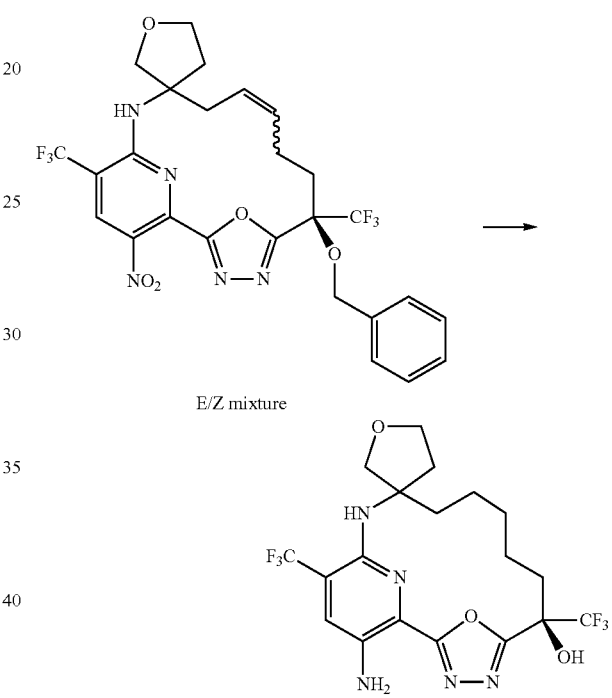

A solution of (6R)-6-benzyloxy-17-nitro-6,15-bis(trifluoromethyl)spiro[19-oxa-3,4,13,18-tetrazatricyclo[12.3.1.1²,5]nonadeca-1(17),2,4,9,14(18),15-hexaene-12,3'-tetrahydrofuran] (E/Z mixture) (131.7 mg, 0.2171 mmol) in ethanol (9 mL) was purged three times with nitrogen gas. Added palladium on carbon (131.5 mg, 5 w/w, 0.0618 mmol) then purged the reaction twice with hydrogen gas and the reaction was stirred under one atmosphere of hydrogen for about 22 h. The reaction was purged twice with nitrogen gas then filtered over a pad of Celite and the cake was washed with ethanol (about 30 mL). The volatiles of the filtrate were removed under reduced pressure to afford as an intense yellow oil and mixture of diastereomers, (6R)-17-amino-6,15-bis(trifluoromethyl)spiro[19-oxa-3,4,13,18-tetrazatricyclo[12.3.1.1²,5]nonadeca-1(18),2,4,14,16-pentaene-12,3'-tetrahydrofuran]-6-ol (103 mg, 96%). ESI-MS m/z calc. 481.1549, found 482.2 (M+1)$^+$; Retention time: 3.39 minutes (LC Method BB).

Step 4: (6R)-17-Amino-6,15-bis(trifluoromethyl) spiro[19-oxa-3,4,13,18-tetrazatricyclo[12.3.1.1²,⁵] nonadeca-1(18),2,4,14,16-pentaene-12,3'-tetrahydrofuran]-6-ol (enantiomer 1) (Compound 207) and (6R)-17-amino-6,15-bis(trifluoromethyl)spiro[19-oxa-3,4,13,18-tetrazatricyclo[12.3.1.1²,⁵]nonadeca-1(18),2,4,14,16-pentaene-12,3'-tetrahydrofuran]-6-ol (enantiomer 2) (Compound 208)

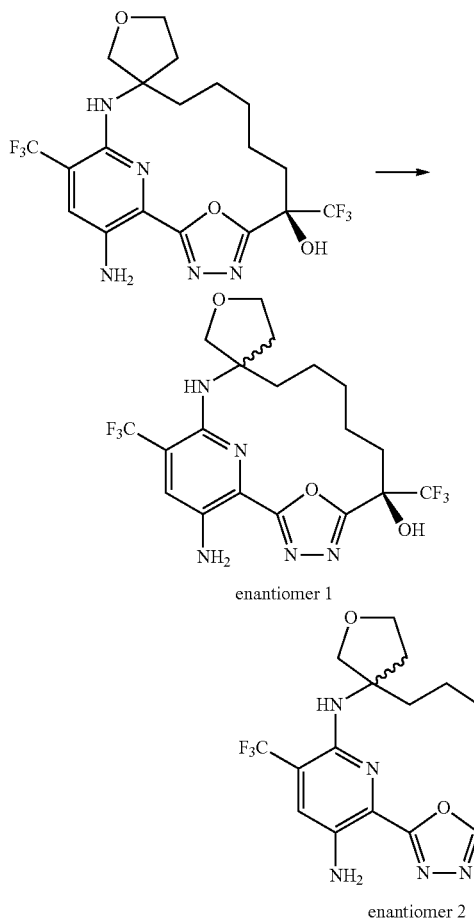

enantiomer 1 enantiomer 2

(6R)-17-Amino-6,15-bis(trifluoromethyl)spiro[19-oxa-3,4,13,18-tetrazatricyclo[12.3.1.1²,⁵]nonadeca-1(18),2,4,14,16-pentaene-12,3'-tetrahydrofuran]-6-ol (103 mg) was purified by reverse phase chromatography using an AQ $C_{18}$ column (50 g) and eluting with a gradient from 5% to 70% of acetonitrile in basic water (10 mM ammonium bicarbonate/ammonium hydroxide buffer, pH=10). The resultant yellow solid was further purified by SFC using a LUX-5 column (250×21.2 mm, 5 um particle size) sold by Phenomenex using a gradient of 7% EtOH (+0.1% diethylamine) in $CO_2$ which gave two diastereomeric products:

The first diastereomer to elute was isolated then taken up in ethyl acetate (10 mL) and the organic layer was washed successively with 1 N aqueous HCl (10 mL), a saturated aqueous solution of sodium bicarbonate (10 mL) and brine (10 mL). The organic layer was dried over sodium sulfate, filtered, concentrated under reduced pressure then lyophilized from acetonitrile/water to afford as an intense yellow solid, (6R)-17-amino-6,15-bis(trifluoromethyl)spiro[19-oxa-3,4,13,18-tetrazatricyclo[12.3.1.1²,⁵]nonadeca-1(18),2,4,14,16-pentaene-12,3'-tetrahydrofuran]-6-ol (enantiomer 1) (44.5 mg, 33%). $^1$H NMR (400 MHz, DMSO-d6) δ 7.61 (s, 1H), 7.60 (s, 1H), 6.02 (s, 2H), 5.41 (s, 1H), 4.11 (d, J=9.5 Hz, 1H), 3.81 (td, J=8.4, 3.5 Hz, 1H), 3.71-3.58 (m, 2H), 2.74 (t, J=11.1 Hz, 1H), 2.31-2.15 (m, 2H), 2.13-1.95 (m, 2H), 1.80-1.59 (m, 2H), 1.57-1.35 (m, 5H) ppm. $^{19}$F NMR (377 MHz, DMSO-d6) δ −62.26 (s, 3F), −78.52 (br. s., 3F) ppm. ESI-MS m/z calc. 481.1549, found 482.2 (M+1)⁺; Retention time: 3.0 minutes (LC Method C).

The second diastereomer to elute was isolated then taken up in ethyl acetate (10 mL) and the organic layer was washed successively with 1 N aqueous HCl (10 mL), a saturated aqueous solution of sodium bicarbonate (10 mL) and brine (10 mL). The organic layer was dried over sodium sulfate, filtered, concentrated under reduced pressure and lyophilized from acetonitrile/water to afford as an intense yellow solid, (6R)-17-amino-6,15-bis(trifluoromethyl)spiro[19-oxa-3,4,13,18-tetrazatricyclo[12.3.1.1²,⁵]nonadeca-1(18),2,4,14,16-pentaene-12,3'-tetrahydrofuran]-6-ol (enantiomer 2) (45.5 mg, 34%). $^1$H NMR (400 MHz, DMSO-d6) δ 7.61 (s, 1H), 7.60 (s, 1H), 6.04 (s, 2H), 5.26 (s, 1H), 3.90 (d, J=9.3 Hz, 1H), 3.81-3.65 (m, 3H), 2.46-2.35 (m, 1H), 2.23-2.06 (m, 5H), 1.68-1.36 (m, 6H) ppm. $^{19}$F NMR (377 MHz, DMSO-d6) δ −62.32 (s, 3F), −77.72 (br. s., 3F) ppm. ESI-MS m/z calc. 481.1549, found 482.2 (M+1)⁺; Retention time: 3.06 minutes (LC Method C).

Example 115: Preparation of 17-amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,7-diol (enantiomer 1, trans diol) (Compound 209) and 17-amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,7-diol (enantiomer 2, trans diol) (Compound 210)

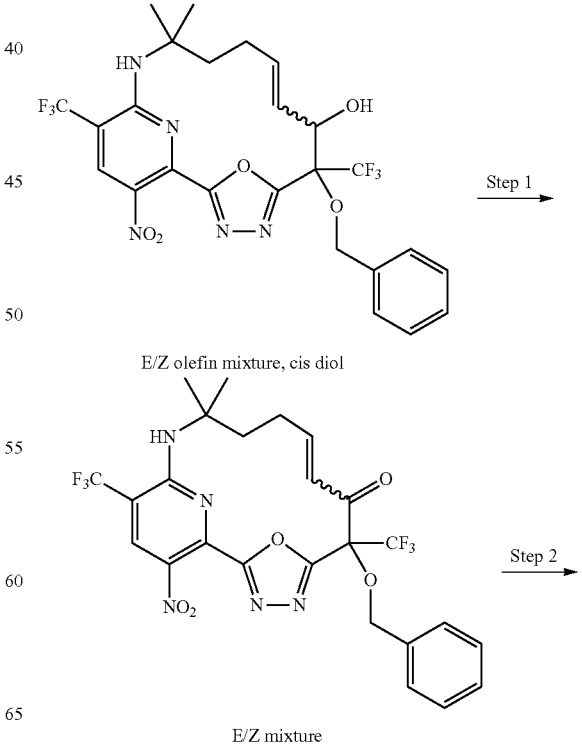

E/Z olefin mixture, cis diol

E/Z mixture

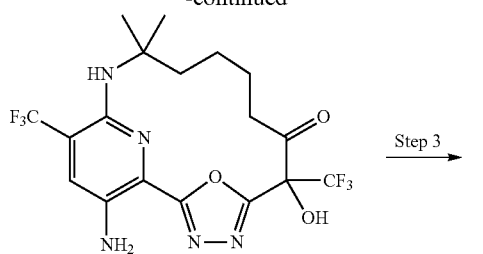

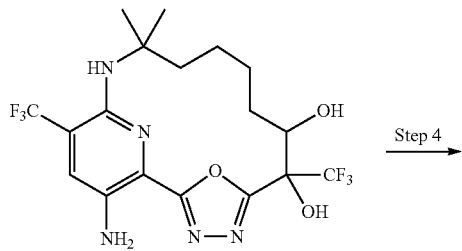

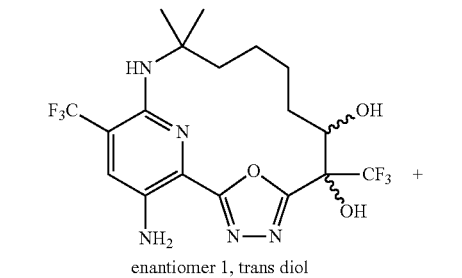

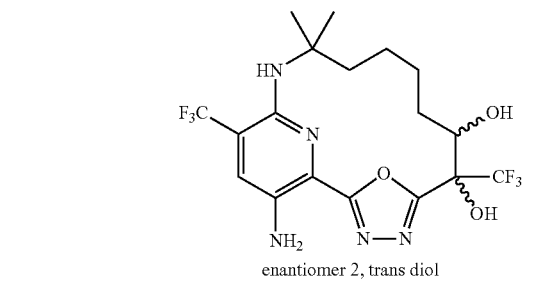

enantiomer 1, trans diol enantiomer 2, trans diol

Step 1: 6-Benzyloxy-12,12-dimethyl-17-nitro-6,15-bis(trifluoromethyl)-19-oxa-3,4,13,18-tetrazatricyclo[12.3.1.1²,⁵]nonadeca-1(18),2,4,8,14,16-hexaen-7-one (E/Z mixture)

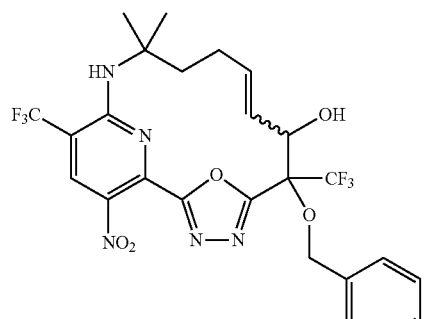

E/Z olefin mixture, cis diol

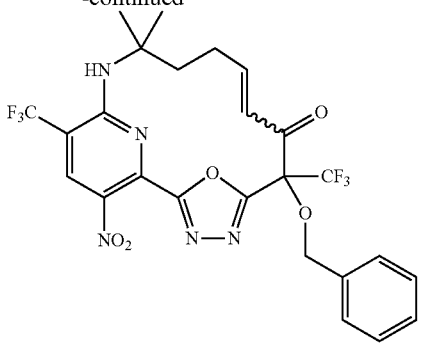

E/Z mixture

To a solution of 6-benzyloxy-12,12-dimethyl-17-nitro-6,15-bis(trifluoromethyl)-19-oxa-3,4,13,18-tetrazatricyclo[12.3.1.1²,⁵]nonadeca-1(18),2,4,8,14,16-hexaen-7-ol (E/Z olefin mixture, cis diol) (22 mg, 0.0374 mmol) in dichloromethane (2 mL) at 0° C. was added Dess-Martin periodinane (25 mg, 0.0589 mmol). The resulting mixture was stirred at room temperature for 10 minutes and then refluxed for 2 h. The mixture was cooled to room temperature, filtered and the filtrate was concentrated under reduced pressure. The residue was purified by silica gel chromatography using a gradient from 0% to 30% ethyl acetate in heptanes to provide as a pale solid, 6-benzyloxy-12,12-dimethyl-17-nitro-6,15-bis(trifluoromethyl)-19-oxa-3,4,13,18-tetrazatricyclo[12.3.1.1²,⁵]nonadeca-1(18),2,4,8,14,16-hexaen-7-one (E/Z mixture) (20 mg, 91%). ESI-MS m/z calc. 585.1447, found 586.2 (M+1)⁺; Retention time: 1.94 minutes (LC Method BB).

Step 2: 17-Amino-6-hydroxy-12,12-dimethyl-6,15-bis(trifluoromethyl)-19-oxa-3,4,13,18-tetrazatricyclo[12.3.1.1²,⁵]nonadeca-1(18),2,4,14,16-pentaen-7-one

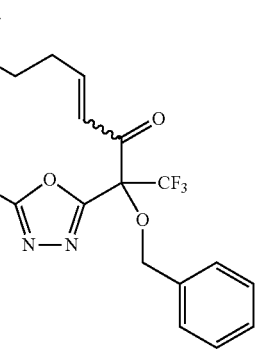

E/Z mixture

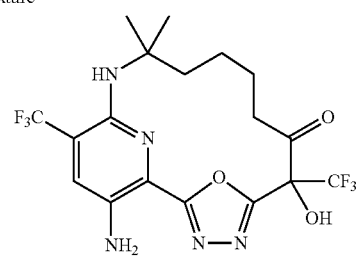

A solution of 6-benzyloxy-12,12-dimethyl-17-nitro-6,15-bis(trifluoromethyl)-19-oxa-3,4,13,18-tetrazatricyclo[12.3.1.1²,⁵]nonadeca-1(18),2,4,8,14,16-hexaen-7-one (E/Z mixture) (120 mg, 0.205 mmol) in methanol (12 mL) was bubbled with nitrogen for 5 min and then palladium on carbon (131 mg, 5% w/w, 0.0615 mmol) was added. The resulting mixture was bubbled with a balloon of hydrogen for 5 min and then the mixture was stirred at room temperature under 1 atm of hydrogen overnight. The mixture was filtered through a pad of Celite, washed with methanol (25 mL) and concentrated under reduced pressure. The resulting residue was purified by silica gel chromatography using a gradient from 0% to 30% ethyl acetate in heptanes to afford as a fluorescent yellow solid, 17-amino-6-hydroxy-12,12-dimethyl-6,15-bis(trifluoromethyl)-19-oxa-3,4,13,18-tetrazatricyclo[12.3.1.1²,⁵]nonadeca-1(18),2,4,14,16-pentaen-7-one (66 mg, 69%). $^1$H NMR (400 MHz, Chloroform-d) δ 7.31 (s, 1H), 5.22 (br. s., 1H), 5.08 (br. s., 2H), 4.40 (br. s., 1H), 3.48 (ddd, J=19.6, 8.4, 5.0 Hz, 1H), 3.06-2.92 (m, 1H), 2.71 (dt, J=19.3, 5.1 Hz, 1H), 2.22-2.07 (m, 1H), 1.78-1.60 (m, 3H), 1.53-1.41 (m, 1H), 1.32 (s, 3H), 1.30 (s, 3H) ppm. $^{19}$F NMR (377 MHz, Chloroform-d) δ −63.91 (s, 3F), −74.29 (s, 3F) ppm. ESI-MS m/z calc. 467.1392, found 468.1 (M+1)$^+$; Retention time: 4.65 minutes (LC Method AA).

Step 3: 17-Amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,7-diol

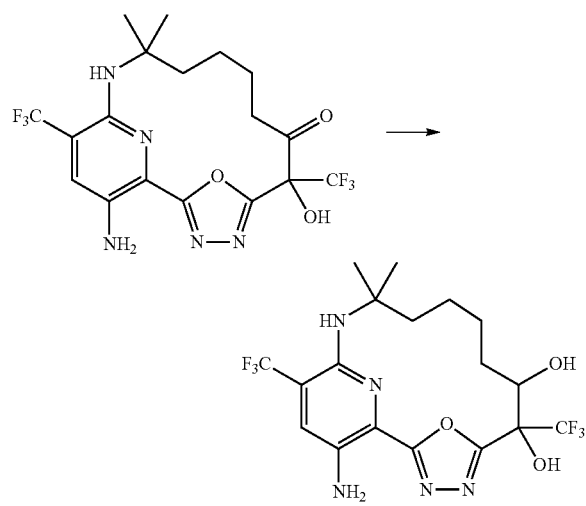

To a solution of 17-amino-6-hydroxy-12,12-dimethyl-6,15-bis(trifluoromethyl)-19-oxa-3,4,13,18-tetrazatricyclo[12.3.1.1²,⁵]nonadeca-1(18),2,4,14,16-pentaen-7-one (36 mg, 0.077 mmol) in tetrahydrofuran (2 mL) at 0° C. was added tetramethylammonium borohydride (28 mg, 0.3147 mmol). The mixture was stirred while allowing to warm from 0° C. to room temperature overnight. The mixture was cooled to 0° C. and then acetone (5 mL) was added. The mixture was stirred at 0° C. for 10 min and then treated with a saturated aqueous solution of sodium bicarbonate (25 mL). The mixture was extracted with ethyl acetate (2×20 mL). The combined organic layers were dried over sodium sulfate, filtered and concentrated to afford as a brownish oil, 17-amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,7-diol (33 mg, 80%) (87.1% purity). ESI-MS m/z calc. 469.1549, found 470.2 (M+1)$^+$; Retention time: 3.52 minutes (LC Method BB).

Step 4: 17-Amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,7-diol (enantiomer 1, trans diol) (Compound 209) and 17-amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,7-diol (enantiomer 2, trans diol) (Compound 210)

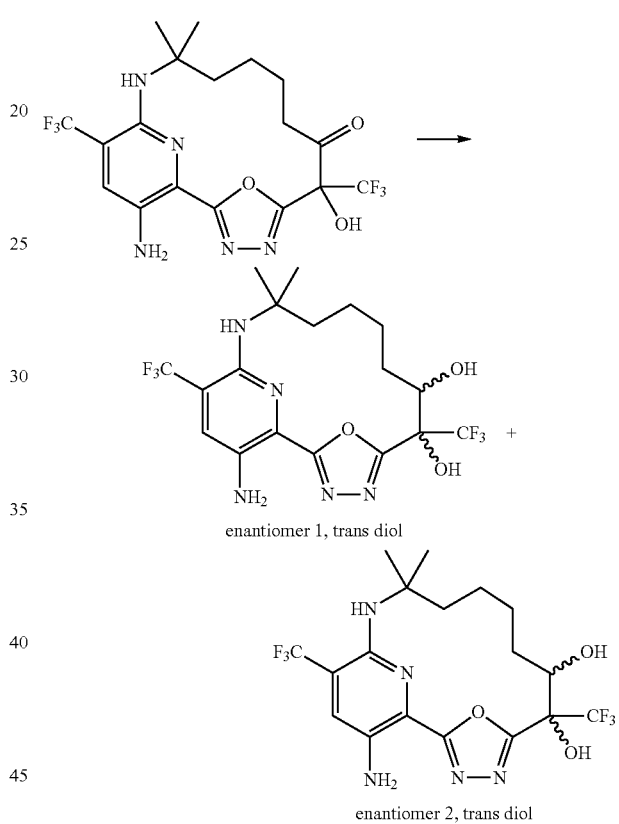

17-Amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,7-diol (72 mg, 0.1534 mmol) was purified by SFC using a LUX-5 column (250×21.2 mm, 5 µm particle size) sold by Phenomenex using a gradient of 10% ethanol (+0.1% diethylamine) in CO$_2$ giving two single enantiomer products:

The first enantiomer was isolated as an intense yellow solid, 17-amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,7-diol (enantiomer 1, trans diol) (16 mg, 22%). $^1$H NMR (400 MHz, DMSO-d6) δ 7.59 (s, 1H), 7.40 (br. s., 1H), 6.00 (s, 2H), 5.45 (d, J=6.6 Hz, 1H), 4.59 (s, 1H), 4.17 (q, J=6.8 Hz, 1H), 3.17-3.03 (m, 1H), 2.02-1.89 (m, 2H), 1.70-1.52 (m, 2H), 1.47-1.34 (m, 6H), 1.24 (s, 3H) ppm. $^{19}$F NMR (377 MHz, DMSO-d6) δ −62.36 (s, 3F), −72.91 (br. s., 3F) ppm. ESI-MS m/z calc. 469.1549, found 470.1 (M+1)$^+$; Retention time: 3.51 minutes (LC Method BB).

The second enantiomer to elute was isolated as an intense yellow solid, 17-amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,7-diol (enantiomer 2, trans diol) (15.5 mg, 22%). $^1$H NMR (400 MHz, DMSO-d6) δ 7.59 (s, 1H), 7.41 (br. s., 1H), 6.00 (s, 2H), 5.45 (d, J=6.8 Hz, 1H), 4.59 (s, 1H), 4.17 (q, J=6.4 Hz, 1H), 3.16-3.03 (m, 1H), 2.01-1.90 (m, 2H), 1.69-1.52 (m, 2H), 1.49-1.34 (m, 6H), 1.24 (s, 3H) ppm. $^{19}$F NMR (377 MHz, DMSO-d6) δ −62.36 (s, 3F), −72.91 (br. s., 3F) ppm. ESI-MS m/z calc. 469.1549, found 470.1 (M+1)$^+$; Retention time: 3.51 minutes (LC Method BB).

Example 116: Preparation of (6R)-17-amino-12-(methoxymethyl)-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (Compound 211) and (6R)-17-amino-12-(methoxymethyl)-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (Compound 212)

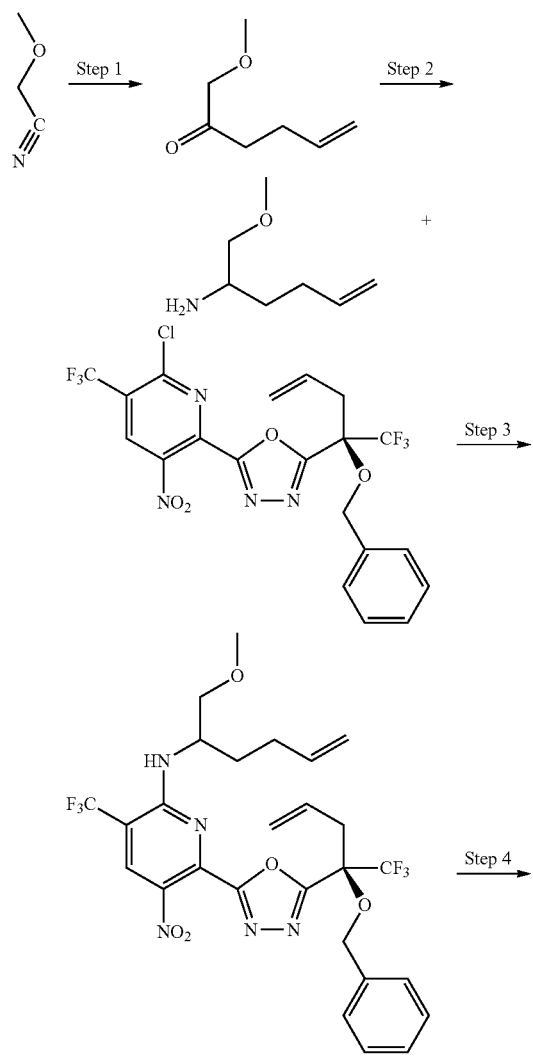

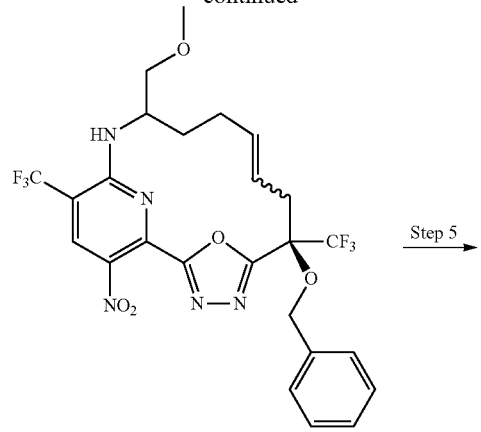

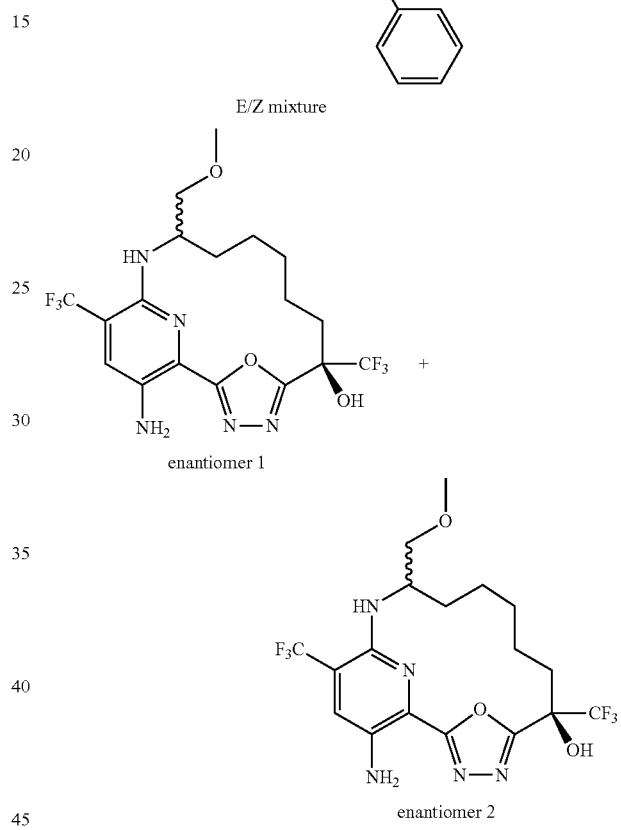

Step 1: 1-Methoxyhex-5-en-2-one

2-Methoxyacetonitrile (1.434 g, 1.5 mL, 20.175 mmol) was added dropwise over 7 min at room temperature to bromo(but-3-enyl)magnesium (40.35 mL of 0.5 M, 20.175 mmol). The dark red reaction mixture was stirred at reflux for 2 h. The mixture was then cooled and quenched with a saturated solution of aqueous ammonium chloride (20 mL). The product was extracted with diethyl ether (2×30 mL). The combined organic layers were washed with water, brine, and dried over anhydrous sodium sulfate then filtered. The filtrate was removed under reduced pressure to give as a brown residue, 1-methoxyhex-5-en-2-one (1.4 g, 44%) which was used directly in the subsequent step.

Step 2: 1-Methoxyhex-5-en-2-amine

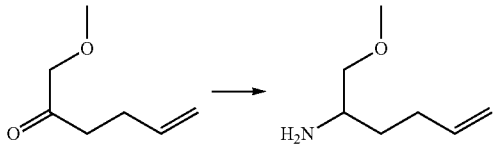

To a solution of 1-methoxyhex-5-en-2-one (1.4 g, 8.8695 mmol) in methanol (40 mL) was added ammonium acetate (12.44 g, 161.39 mmol) and sodium cyanoborohydride (761 mg, 12.11 mmol) at room temperature. The mixture was stirred for 48 h and concentrated HCl was added carefully until pH<2 was reached and the solvent was removed under reduced pressure. The residue was dissolved in water (15 mL) and extracted with diethyl ether (20 mL). The aqueous solution was brought to pH>12 with solid KOH and then extracted with diethyl ether (3×20 mL). The combined organic extracts were dried over anhydrous sodium sulfate, filtered and concentrated under reduced pressure. The residue was purified by silica gel chromatography using a gradient from of 0% to 20% methanol in dichloromethane giving as a colorless oil, 1-methoxyhex-5-en-2-amine (60 mg, 4%). $^1$H NMR (400 MHz, Chloroform-d) δ 5.89-5.72 (m, 1H), 5.11-4.92 (m, 2H), 3.43-3.32 (m, 4H), 3.26-3.18 (m, 1H), 3.08-2.98 (m, 1H), 2.43-2.24 (m, 2H), 2.24-2.07 (m, 2H), 1.63-1.37 (m, 2H) ppm. ESI-MS m/z calc. 129.1154, found 130.2 (M+1)$^+$; Retention time: 2.0 minutes (LC Method BB).

Step 3: 6-[5-[(1R)-1-Benzyloxy-1-(trifluoromethyl) but-3-enyl]-1,3,4-oxadiazol-2-yl]-N-[1-(methoxymethyl)pent-4-enyl]-5-nitro-3-(trifluoromethyl)pyridin-2-amine

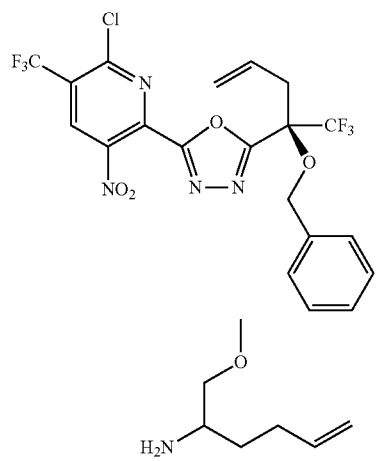

To a solution of 1-methoxyhex-5-en-2-amine (60 mg, 0.3947 mmol) and 2-[(1R)-1-benzyloxy-1-(trifluoromethyl)but-3-enyl]-5-[6-chloro-3-nitro-5-(trifluoromethyl)-2-pyridyl]-1,3,4-oxadiazole (253 mg, 0.5089 mmol) in acetonitrile (2 mL) was added dropwise DIPEA (296.8 mg, 0.4 mL, 2.2964 mmol) and the mixture was stirred at room temperature for 18 h. The volatiles were removed under reduced pressure. The residue was purified by reverse phase chromatography using a gradient from of 5% to 80% acetonitrile in water (+0.1% formic acid) to give as a light yellow oil, 6-[5-[(1R)-1-benzyloxy-1-(trifluoromethyl)but-3-enyl]-1,3,4-oxadiazol-2-yl]-N-[1-(methoxymethyl)pent-4-enyl]-5-nitro-3-(trifluoromethyl)pyridin-2-amine (80 mg, 32%). $^1$H NMR (400 MHz, Chloroform-d) δ 8.57 (s, 1H), 7.41-7.27 (m, 5H), 6.14 (d, J=8.3 Hz, 1H), 6.04-5.90 (m, 1H), 5.82-5.68 (m, 1H), 5.34-5.20 (m, 2H), 5.02-4.88 (m, 2H), 4.81 (d, J=10.5 Hz, 1H), 4.64 (dd, J=10.5, 5.1 Hz, 1H), 4.60-4.51 (m, 1H), 3.55-3.45 (m, 2H), 3.40-3.37 (m, 3H), 3.28-3.20 (m, 2H), 2.13-2.04 (m, 2H), 1.84-1.73 (m, 2H) ppm. $^{19}$F NMR (377 MHz, Chloroform-d) δ−64.72 (s, 3F), −73.49 (s, 3F, diastereomer A), −73.60 (s, 3F, diastereomer B) ppm. ESI-MS m/z calc. 615.1916, found 616.2 (M+1)$^+$; Retention time: 3.82 minutes (LC Method AA).

Step 4: (6R)-6-Benzyloxy-12-(methoxymethyl)-17-nitro-6,15-bis(trifluoromethyl)-19-oxa-3,4,13,18-tetrazatricyclo[12.3.1.12,5]nonadeca-1(18),2,4,8,14,16-hexaene (E/Z Mixture)

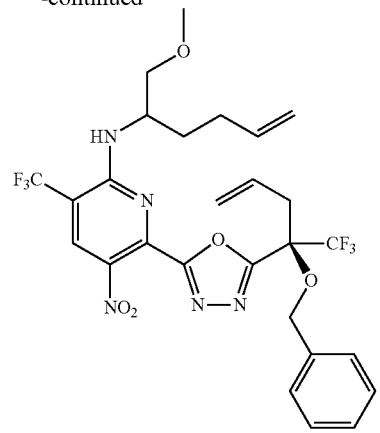

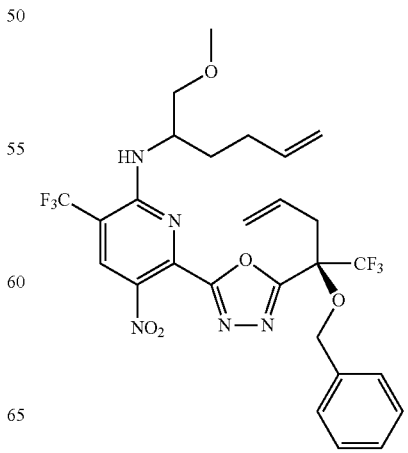

-continued

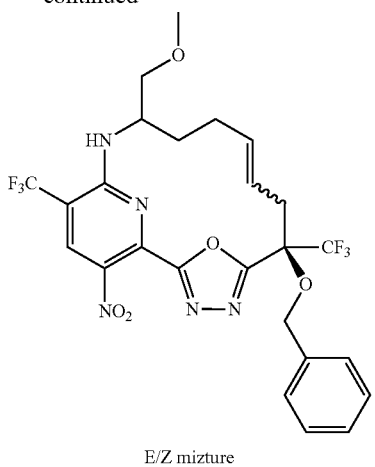

E/Z mizture

Nitrogen gas was bubbled in to a solution of 6-[5-[(1R)-1-benzyloxy-1-(trifluoromethyl)but-3-enyl]-1,3,4-oxadiazol-2-yl]-N-[1-(methoxymethyl)pent-4-enyl]-5-nitro-3-(trifluoromethyl)pyridin-2-amine (80 mg, 0.1261 mmol) in 1,2-dichloroethane (40 mL) for 20 h. The solution was then placed in an oil bath, set at 60° C. and a first portion of Zhan-1B catalyst (6.5 mg, 0.0089 mmol) was added. After 45 minutes, a second portion of Zhan-1B catalyst (6.5 mg, 0.0089 mmol) was added and heating was continued for another 5 h. Once cooled to room temperature, the reaction was quenched with DMSO (3 drops), the volatiles were removed under reduced pressure and the residue was purified by silica gel chromatography using a gradient from of 0% to 35% ethyl acetate in heptanes to afford as a pale yellow foam, (6R)-6-benzyloxy-12-(methoxymethyl)-17-nitro-6,15-bis(trifluoromethyl)-19-oxa-3,4,13,18-tetrazatricyclo[12.3.1.12,5]nonadeca-1(18),2,4,8,14,16-hexaene (E/Z mixture) (37 mg, 48%). $^1$H NMR (400 MHz, Chloroform-d) δ 8.52-8.43 (m, 1H), 7.41-7.28 (m, 5H), 6.40-6.24 (m, 1H), 5.85-5.75 (m, 1H), 5.74-5.56 (m, 1H), 4.90 (d, J=11.0 Hz, 1H), 4.72-4.52 (m, 1H), 4.27-4.18 (m, 1H), 3.66-3.56 (m, 2H), 3.49-3.43 (m, 3H), 3.17-2.64 (m, 2H), 2.32-2.17 (m, 1H), 1.85-1.76 (m, 1H), 1.70-1.61 (m, 1H), 1.48-1.37 (m, 1H) ppm. ESI-MS m/z calc. 587.1603, found 588.2 (M+1)$^+$; Retention time: 3.7 minutes (LC Method C).

Step 5: (6R)-17-Amino-12-(methoxymethyl)-6,15-bis(trifluoromethyl)-19-oxa-3,4,13,18-tetrazatricyclo[12.3.1.12,5]nonadeca-1(18),2,4,14,16-pentaen-6-ol (enantiomer 1) (Compound 211) and (6R)-17-amino-12-(methoxymethyl)-6,15-bis(trifluoromethyl)-19-oxa-3,4,13,18-tetrazatricyclo[12.3.1.12,5]nonadeca-1(18),2,4,14,16-pentaen-6-ol (Enantiomer 2) (Compound 212)

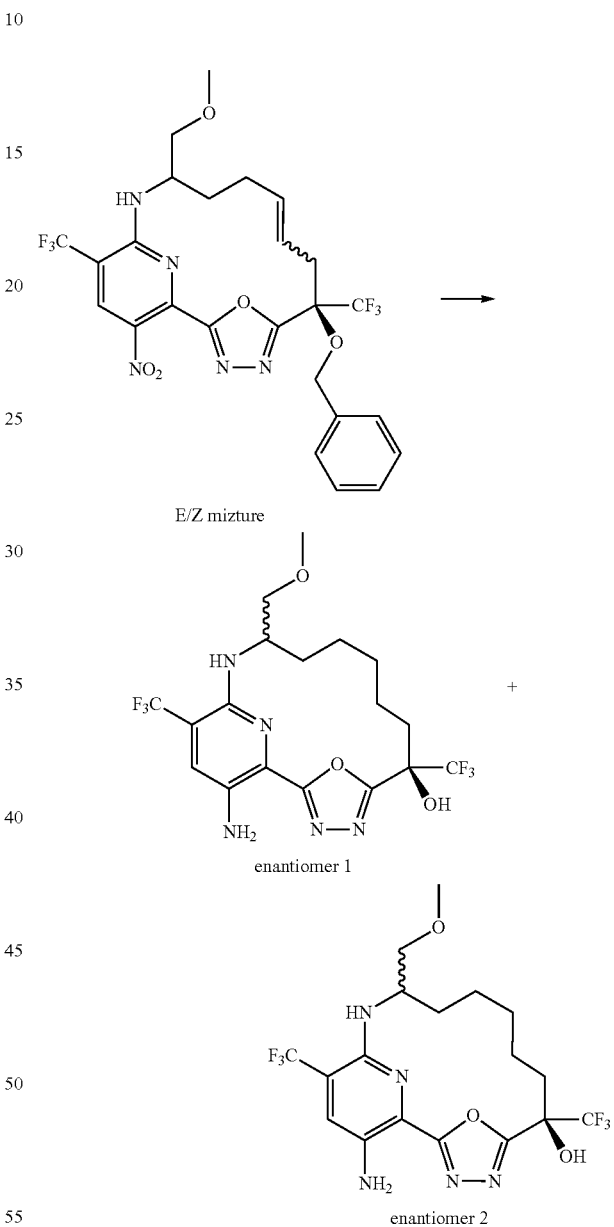

A solution of (6R)-6-benzyloxy-12-(methoxymethyl)-17-nitro-6,15-bis(trifluoromethyl)-19-oxa-3,4,13,18-tetrazatricyclo[12.3.1.12,5]nonadeca-1(18),2,4,8,14,16-hexaene (E/Z mixture) (37 mg, 0.0608 mmol) in tetrahydrofuran (3 mL) was bubbled with nitrogen gas for 5 minutes. Added palladium on carbon (39 mg, 5% w/w, 0.0183 mmol) and hydrogen gas was bubbled in the reaction mixture for 5 minutes, and then the reaction was left to stir under one atmosphere of hydrogen for 96 h. The mixture was filtered over a pad of Celite and the cake was washed with ethyl acetate (30 mL). The filtrate was concentrated under reduced pressure. The yellow residue was purified by silica gel chromatography eluting with 19% ethyl acetate in heptanes giving two diastereomeric products:

The first diastereomer to elute was isolated as a yellow solid, (6R)-17-amino-12-(methoxymethyl)-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (5.67 mg, 19%). ¹H NMR (400 MHz, DMSO-d6) δ 7.64 (s, 1H), 7.59 (s, 1H), 6.09 (s, 2H), 5.11 (d, J 2.4 Hz, 1H), 3.74-3.65 (m, 1H), 3.61-3.55 (m, 1H), 3.53-3.46 (m, 1H), 3.31 (s, 3H), 2.44-2.35 (m, 1H), 2.29-2.19 (m, 1H), 2.08-1.96 (m, 1H), 1.68-1.56 (m, 2H), 1.55-1.37 (m, 4H), 1.07-0.95 (m, 1H) ppm. ¹⁹F NMR (377 MHz, DMSO-d6) δ −62.76 (s, 3F), −79.12 (s, 3F) ppm. ESI-MS m/z calc. 469.1549, found 470.2 (M+1)⁺; Retention time: 4.55 minutes (LC Method AA).

The second diastereomer to elute was isolated as a yellow solid (6R)-17-amino-12-(methoxymethyl)-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (4.97 mg, 17%). ¹H NMR (400 MHz, DMSO-d6) δ 7.64 (s, 1H), 7.56 (s, 1H), 6.08 (s, 2H), 5.13 (d, J 3.2 Hz, 1H), 3.80-3.72 (m, 1H), 3.61-3.55 (m, 1H), 3.54-3.47 (m, 1H), 3.31 (s, 3H), 2.39-2.23 (m, 2H), 2.12-2.00 (m, 1H), 1.75-1.61 (m, 2H), 1.58-1.35 (m, 4H), 1.12-1.01 (m, 1H) ppm. ¹⁹F NMR (377 MHz, DMSO-d6) δ −62.75 (s, 3F), −76.32 (s, 3F) ppm. ESI-MS m/z calc. 469.1549, found 470.2 (M+1)⁺; Retention time: 4.56 minutes (LC Method AA).

Example 117: Preparation of (6R)-17-amino-15-(difluoromethyl)-12,12-dimethyl-6-(trifluoromethyl)-19-oxa-3,4,13,18-tetrazatricyclo[12.3.1.1²,⁵]nonadeca-1(18),2,4,14,16-pentaen-6-ol (Compound 213)

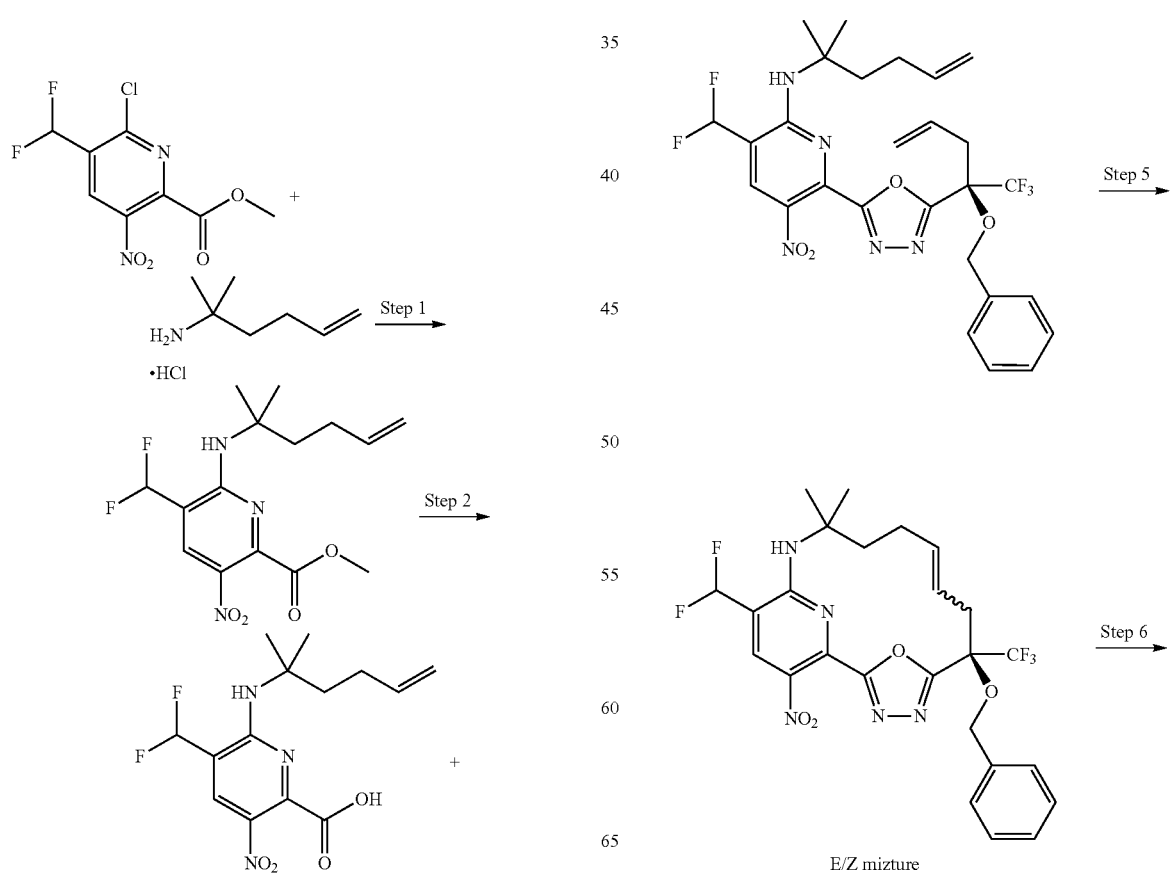

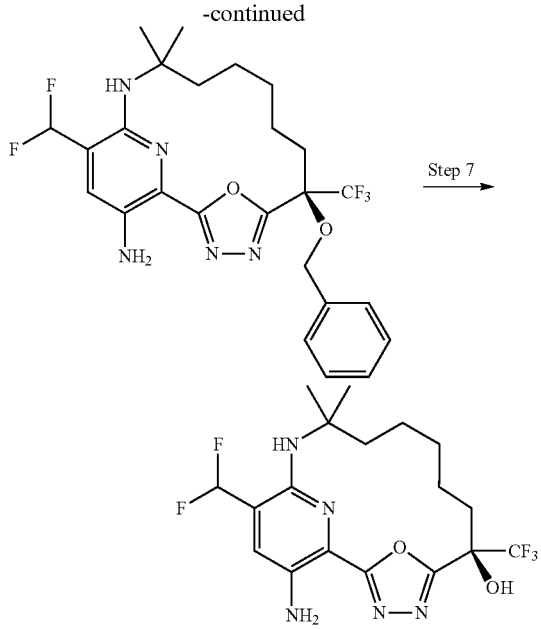

Step 1: Methyl 5-(difluoromethyl)-6-(1,1-dimethyl-pent-4-enylamino)-3-nitro-pyridine-2-carboxylate

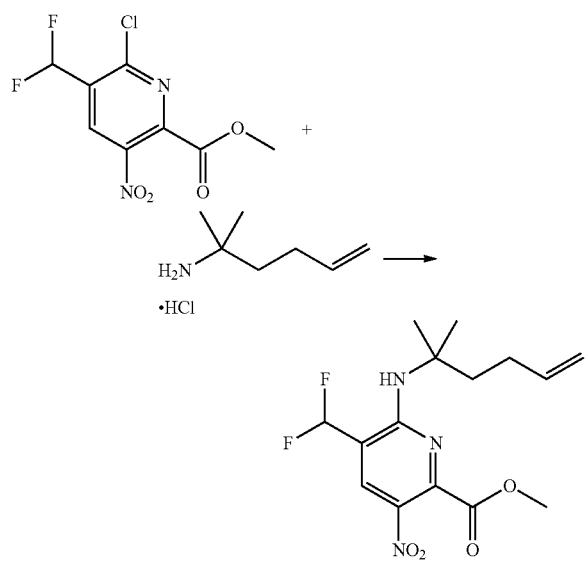

A solution of 2-methylhex-5-en-2-amine (hydrochloride salt) (1.40 g, 9.3544 mmol), methyl 6-chloro-5-(difluoromethyl)-3-nitro-pyridine-2-carboxylate (1.9 g, 6.293 mmol) and DIPEA (4.081 g, 5.5 mL, 31.576 mmol) in acetonitrile (28 mL) was stirred at 80° C. in a sealed tube for 1 h. The dark solution was cooled to room temperature. The solvent was evaporated, and the residue was dissolved in MTBE (40 mL) and 0.5 M hydrochloric acid solution (60 mL). The aqueous solution was extracted with MTBE (3×30 mL). The combined organic layers were washed with 50% aqueous saturated ammonium chloride solution (1×40 mL), water (30 mL), brine (20 mL), then dried over anhydrous sodium sulfate, filtered and concentrated under vacuum to give as an orange film, methyl 5-(difluoromethyl)-6-(1,1-dimethyl-pent-4-enylamino)-3-nitro-pyridine-2-carboxylate (2.4 g, 76%). ESI-MS m/z calc. 343.1344, found 344.2 (M+1)$^+$; Retention time: 2.16 minutes (LC Method E).

Step 2: 5-(Difluoromethyl)-6-(1,1-dimethylpent-4-enylamino)-3-nitro-pyridine-2-carboxylic Acid

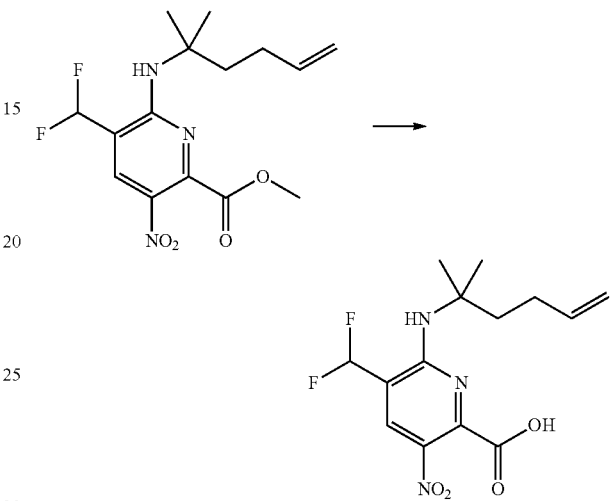

A solution of lithium hydroxide (monohydrate) (2.8 g, 66.725 mmol) in water (18 mL) was added to an orange solution of methyl 5-(difluoromethyl)-6-(1,1-dimethylpent-4-enylamino)-3-nitro-pyridine-2-carboxylate (2.4 g, 4.7815 mmol) in THF (18 mL) and methanol (9 mL) at room temperature. The yellow suspension was stirred at room temperature for 1 h. The resulting red dark solution was cooled to room temperature and organic solvents were removed under vacuum. The residual methanol was co-evaporated with acetonitrile (20 mL) then MTBE (60 mL) and hydrochloric acid solution (1 M, 80 mL) were added and the mixture was stirred for 10 min. The aqueous solution was separated and extracted with MTBE (3×30 mL). Combined organic layers were concentrated and the residue was purified by reverse phase chromatography using a gradient from 5% to 90% acetonitrile in water (+0.1% formic acid) which afforded as an orange solid, 5-(difluoromethyl)-6-(1,1-dimethylpent-4-enylamino)-3-nitro-pyridine-2-carboxylic acid (1.4 g, 60%). $^1$H NMR (400 MHz, Chloroform-d) δ 8.23 (s, 1H), 6.75-6.39 (m, 1H), 6.18 (br. s., 1H), 5.86-5.74 (m, 1H), 5.73-5.65 (m, 1H), 5.10-4.99 (m, 1H), 4.96 (d, J=10.1 Hz, 1H), 2.14-1.96 (m, 4H), 1.53 (br. s, 6H) ppm. $^{19}$F NMR (377 MHz, Chloroform-d) δ−115.13 to −115.65 (m, 2F) ppm. ESI-MS m/z calc. 329.1187, found 328.6 (M−1)$^-$; Retention time: 1.94 minutes (LC Method C).

Step 3: N'-[(2R)-2-Benzyloxy-2-(trifluoromethyl) pent-4-enoyl]-5-(difluoromethyl)-6-(1,1-dimethyl-pent-4-enylamino)-3-nitro-pyridine-2-carbohydrazide

Step 4: 6-[5-[(1R)-1-Benzyloxy-1-(trifluoromethyl) but-3-enyl]-1,3,4-oxadiazol-2-yl]-3-(difluoromethyl)-N-(1,1-dimethylpent-4-enyl)-5-nitro-pyridin-2-amine

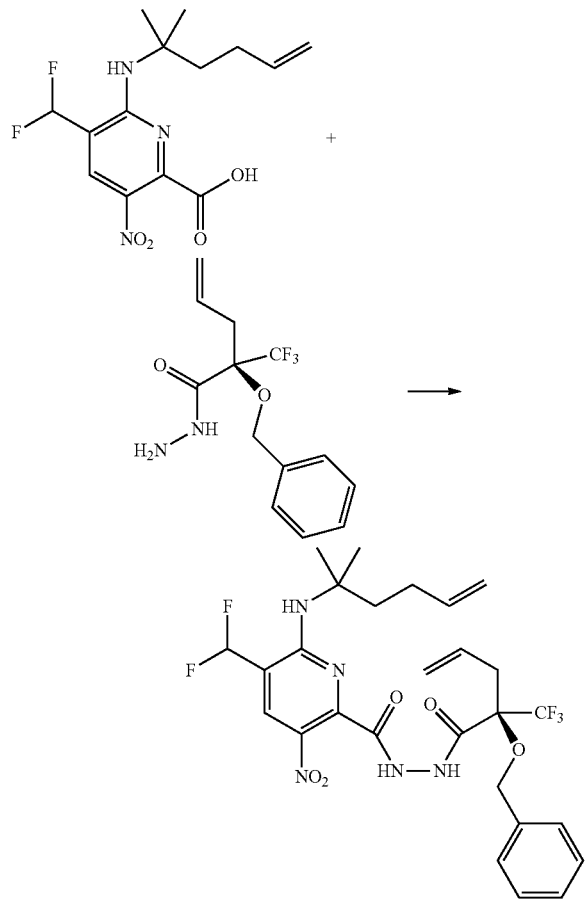

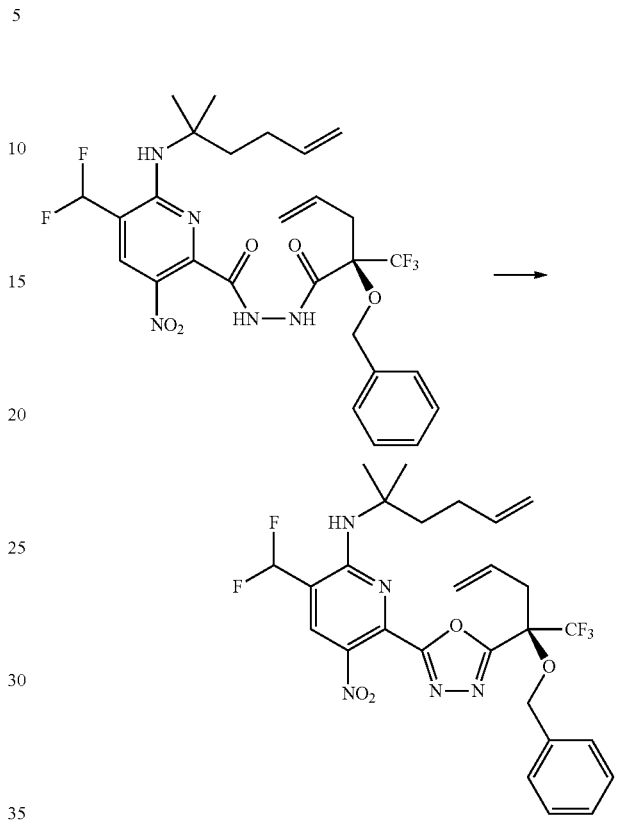

HATU (2.0 g, 5.2600 mmol) was added to an orange solution of 5-(difluoromethyl)-6-(1,1-dimethylpent-4-enylamino)-3-nitro-pyridine-2-carboxylic acid (1.4 g, 2.8697 mmol), (2R)-2-benzyloxy-2-(trifluoromethyl)pent-4-enehydrazide (1.45 g, 5.0301 mmol) and DIPEA (2.6712 g, 3.6 mL, 20.668 mmol) in DMF (7 mL) at room temperature. The solution was stirred at room temperature for 1.5 h. The DMF solution was directly purified by reverse phase chromatography using a gradient from 5% to 75% acetonitrile in water (+0.1% formic acid) to give as a light yellow solid, N'-[(2R)-2-benzyloxy-2-(trifluoromethyl)pent-4-enoyl]-5-(difluoromethyl)-6-(1,1-dimethylpent-4-enylamino)-3-nitro-pyridine-2-carbohydrazide (2.26 g, quant.). $^{19}$F NMR (377 MHz, Chloroform-d) δ−73.76 (s, 3F), −115.07 to −116.18 (m, 2F) ppm. ESI-MS m/z calc. 599.2167, found 600.3 (M+1)$^+$; Retention time: 3.75 minutes (LC Method BB).

A solution of N'-[(2R)-2-benzyloxy-2-(trifluoromethyl) pent-4-enoyl]-5-(difluoromethyl)-6-(1,1-dimethylpent-4-enylamino)-3-nitro-pyridine-2-carbohydrazide (2.26 g, 3.7695 mmol) and 1,4-diazabicyclo[2.2.2]octane (715 mg, 6.3741 mmol) in DCM (100 mL) was treated with a solution of 2-chloro-1,3-dimethyl-4,5-dihydroimidazol-1-ium; chloride (895 mg, 5.2942 mmol) in DCM (80 mL) at room temperature. The formation of the imidazolium intermediate was completed in 15 min. The DCM was evaporated, and the residue was dissolved in toluene (250 mL). The mixture was stirred at 100° C. overnight. The dark brown mixture was quenched with water (150 mL) and the aqueous solution was separated and then extracted with MTBE (3×80 mL). The combined organic layers were dried over sodium sulfate, filtrated and concentrated under vacuum to give an orange oil (2.39 g). Purification of this oil by silica gel chromatography using a gradient from 1% to 35% MTBE in heptanes gave as a light yellow solid, 6-[5-[(1R)-1-benzyloxy-1-(trifluoromethyl)but-3-enyl]-1,3,4-oxadiazol-2-yl]-3-(difluoromethyl)-N-(1,1-dimethylpent-4-enyl)-5-nitro-pyridin-2-amine (1.75 g, 80%). $^1$H NMR (400 MHz, Chloroform-d) δ 8.30 (s, 1H), 7.44-7.23 (m, 5H), 6.81-6.44 (m, 1H), 6.05-5.89 (m, 1H), 5.83-5.63 (m, 2H), 5.30-5.18 (m, 2H), 5.04-4.88 (m, 2H), 4.82 (d, J=10.5 Hz, 1H), 4.65 (d, J=10.5 Hz, 1H), 3.22 (d, J=6.4 Hz, 2H), 2.12-1.86 (m, 4H), 1.48 (s, 6H) ppm. $^{19}$F NMR (377 MHz, Chloroform-d) δ−73.46 (s, 3F), −115.13 to −116.66 (m, 2F) ppm. ESI-MS m/z calc. 581.2061, found 582.3 (M+1)$^+$; Retention time: 2.43 minutes (LC Method E).

Step 5: (6R)-6-Benzyloxy-15-(difluoromethyl)-12,12-dimethyl-17-nitro-6-(trifluoromethyl)-19-oxa-3,4,13,18-tetrazatricyclo[12.3.1.12,5]nonadeca-1(18),2,4,8,14,16-hexaene (E/Z Mixture)

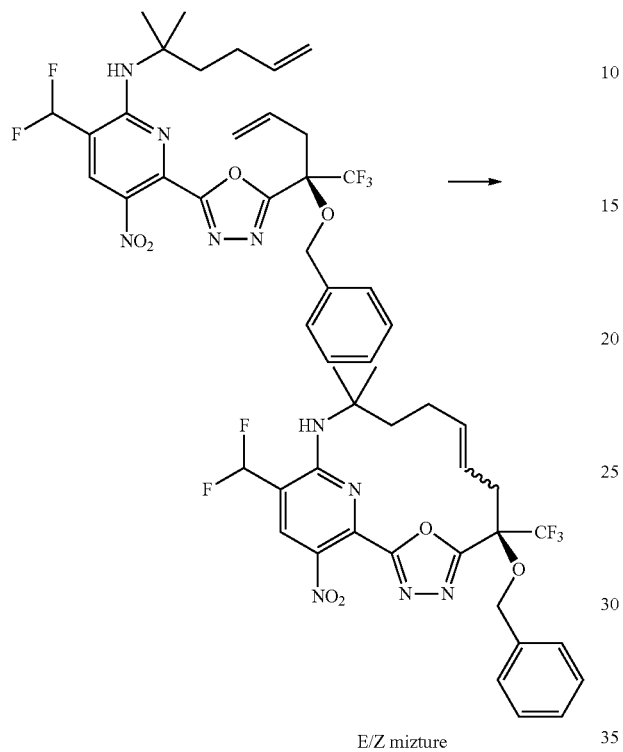

E/Z mixture

Nitrogen was bubbled through a light yellow solution of 6-[5-[(1R)-1-benzyloxy-1-(trifluoromethyl)but-3-enyl]-1,3,4-oxadiazol-2-yl]-3-(difluoromethyl)-N-(1,1-dimethylpent-4-enyl)-5-nitro-pyridin-2-amine (1.75 g, 3.0063 mmol) in DCE (530 mL) overnight. Zhan catalyst-1B (60 mg, 0.0818 mmol) was added at room temperature and nitrogen was bubbled for 5 min. Then, the light green solution was stirred at 65° C. for 30 min and again Zhan catalyst-1B (120 mg, 0.1696 mmol) was added at 65° C. in two portions with 30 min intervals and the mixture was stirred for 3.5 h. The brown solution was cooled to room temperature, then DMSO (6 mL) was added to quench the catalyst. The solvent was removed under reduced pressure and the residue was purified by silica gel chromatography using a gradient from 1% to 100% MTBE in heptanes to give the crude product which was further purified by reverse phase chromatography using a gradient from 5% to 100% acetonitrile in water (+0.1% formic acid) to give as a yellow solid, (6R)-6-benzyloxy-15-(difluoromethyl)-12,12-dimethyl-17-nitro-6-(trifluoromethyl)-19-oxa-3,4,13,18-tetrazatricyclo[12.3.1.12,5]nonadeca-1(18),2,4,8,14,16-hexaene (E/Z mixture) (341 mg, 20%). $^1$H NMR (400 MHz, Chloroform-d) δ 8.27 (s, 1H), 7.45-7.24 (m, 5H), 6.82-6.41 (m, 1H), 5.79-5.57 (m, 3H), 4.86 (d, J=10.9 Hz, 1H), 4.54 (d, J=11.0 Hz, 1H), 3.08 (dd, J=14.1, 3.7 Hz, 1H), 2.70 (dd, J=14.2, 8.5 Hz, 1H), 2.60-2.48 (m, 1H), 2.22-2.08 (m, 1H), 2.05-1.91 (m, 2H), 1.44 (d, J=9.4 Hz, 6H) ppm. $^{19}$F NMR (377 MHz, Chloroform-d) δ −73.01 (s, 3F), −115.34 (dd, J=53.1, 12.3 Hz, 2F) ppm. ESI-MS m/z calc. 553.1748, found 554.2 (M+1)$^+$; Retention time: 2.34 minutes (LC Method E).

Step 6: (6R)-6-Benzyloxy-15-(difluoromethyl)-12,12-dimethyl-6-(trifluoromethyl)-19-oxa-3,4,13,18-tetrazatricyclo[12.3.1.12,5]nonadeca-1(18),2,4,14,16-pentaen-17-amine

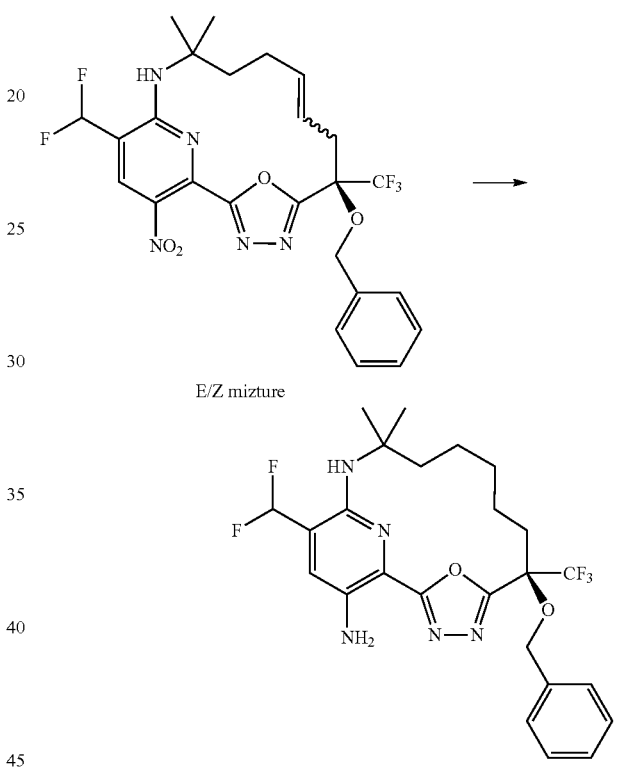

E/Z mixture

Palladium on carbon (66 mg, 5% w/w, 0.062 mmol) was added to a degassed solution of (6R)-6-benzyloxy-15-(difluoromethyl)-12,12-dimethyl-17-nitro-6-(trifluoromethyl)-19-oxa-3,4,13,18-tetrazatricyclo[12.3.1.12,5]nonadeca-1(18),2,4,8,14,16-hexaene (E/Z mixture) (340 mg, 0.6112 mmol) in THF (7 mL). The black suspension was purged with nitrogen for 5 min, then hydrogen was bubbled through the suspension for 5 min. Then the mixture was stirred at room temperature for two nights under hydrogen atmosphere. Again, palladium on carbon (85 mg, 5% w/w, 0.7987 mmol) was added and the mixture was stirred for two more nights under hydrogen atmosphere. The black suspension was purged with nitrogen and then filtered through a plug of Celite. The cake was washed with DCM (3×5 mL), and the filtrate was concentrated under reduced pressure to give as a fluorescent yellow oil, (6R)-6-benzyloxy-15-(difluoromethyl)-12,12-dimethyl-6-(trifluoromethyl)-19-oxa-3,4,13,18-tetrazatricyclo[12.3.1.12,5]nonadeca-1(18),2,4,14,16-pentaen-17-amine (290 mg, 24%). ESI-MS m/z calc. 525.22, found 526.4 (M+1)$^+$; Retention time: 2.40 minutes (LC Method E).

Step 7: (6R)-17-Amino-15-(difluoromethyl)-12,12-dimethyl-6-(trifluoromethyl)-19-oxa-3,4,13,18-tetrazatricyclo[12.3.1.1²,⁵]nonadeca-1(18),2,4,14,16-pentaen-6-ol (Compound 213)

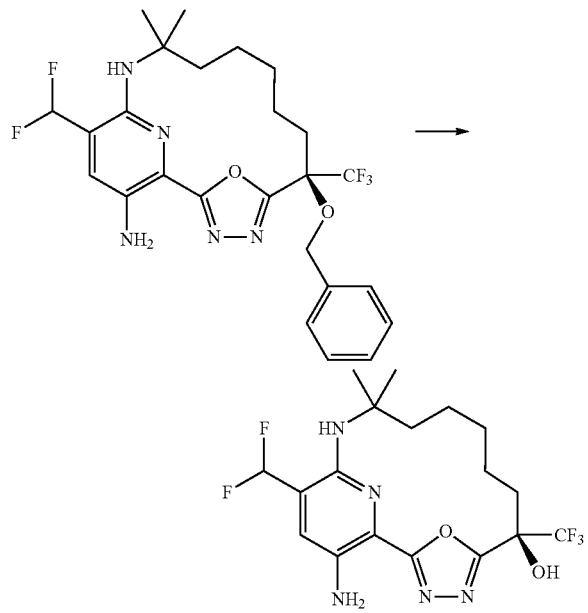

Palladium on carbon (160 mg, 5% w/w, 0.1503 mmol) was added to a degassed solution of (6R)-6-benzyloxy-15-(difluoromethyl)-12,12-dimethyl-6-(trifluoromethyl)-19-oxa-3,4,13,18-tetrazatricyclo[12.3.1.1²,⁵]nonadeca-1(18), 2,4,14,16-pentaen-17-amine (290 mg, 0.4304 mmol) in THF (8 mL) at room temperature. The black suspension was purged with nitrogen for 5 min, then hydrogen was bubbled through the suspension for 5 min. The mixture was stirred at room temperature overnight under hydrogen atmosphere. The black suspension was purged with nitrogen and then filtered through a plug of Celite and the cake was washed with DCM (3×5 mL). The filtrate was concentrated under vacuum to give a fluorescent yellow oil which was purified by reverse phase chromatography using a gradient from 5% to 80% acetonitrile in water (+0.02% HCl) to give the intended product as a yellow solid after lyophilization (45 mg, 94.5% purity). This solid was further purified by silica gel chromatography using a gradient from 1% to 10% EtOAc in DCM to give as a yellow solid, (6R)-17-amino-15-(difluoromethyl)-12,12-dimethyl-6-(trifluoromethyl)-19-oxa-3,4,13,18-tetrazatricyclo[12.3.1.1²,⁵]nonadeca-1(18),2,4,14,16-pentaen-6-ol (29 mg, 15%). $^1$H NMR (400 MHz, DMSO-d6) δ 7.58 (s, 1H), 7.41 (s, 1H), 7.18 (t, J=53.7 Hz, 1H), 5.86 (s, 2H), 5.20 (s, 1H), 2.90-2.75 (m, 1H), 2.27-2.14 (m, 1H), 2.12-1.98 (m, 1H), 1.89-1.75 (m, 1H), 1.71-1.57 (m, 1H), 1.54-1.37 (m, 5H), 1.34 (s, 3H), 1.29 (s, 3H) ppm. $^{19}$F NMR (377 MHz, DMSO-d6) δ −78.22 (s, 3F), −114.57 to −115.76 (m, 1F), −115.76 to −116.87 (m, 1F) ppm. ESI-MS m/z calc. 435.1694, found 436.3 (M+1)$^+$; Retention time: 3.21 minutes (LC Method C).

Example 118: Preparation of (6R)-17-Amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,10-diol (diastereomer 1) (Compound 214) and (6R)-17-Amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,10-diol (diastereomer 2) (Compound 215)

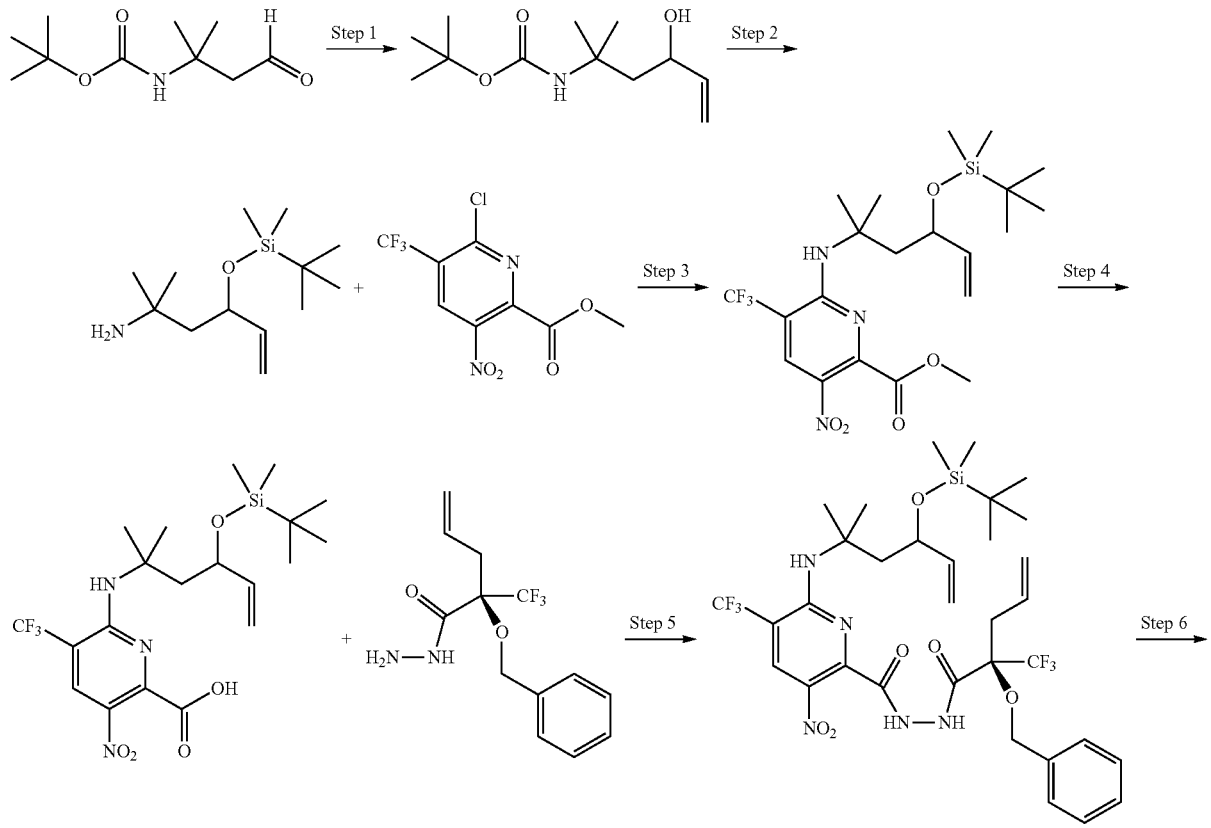

-continued

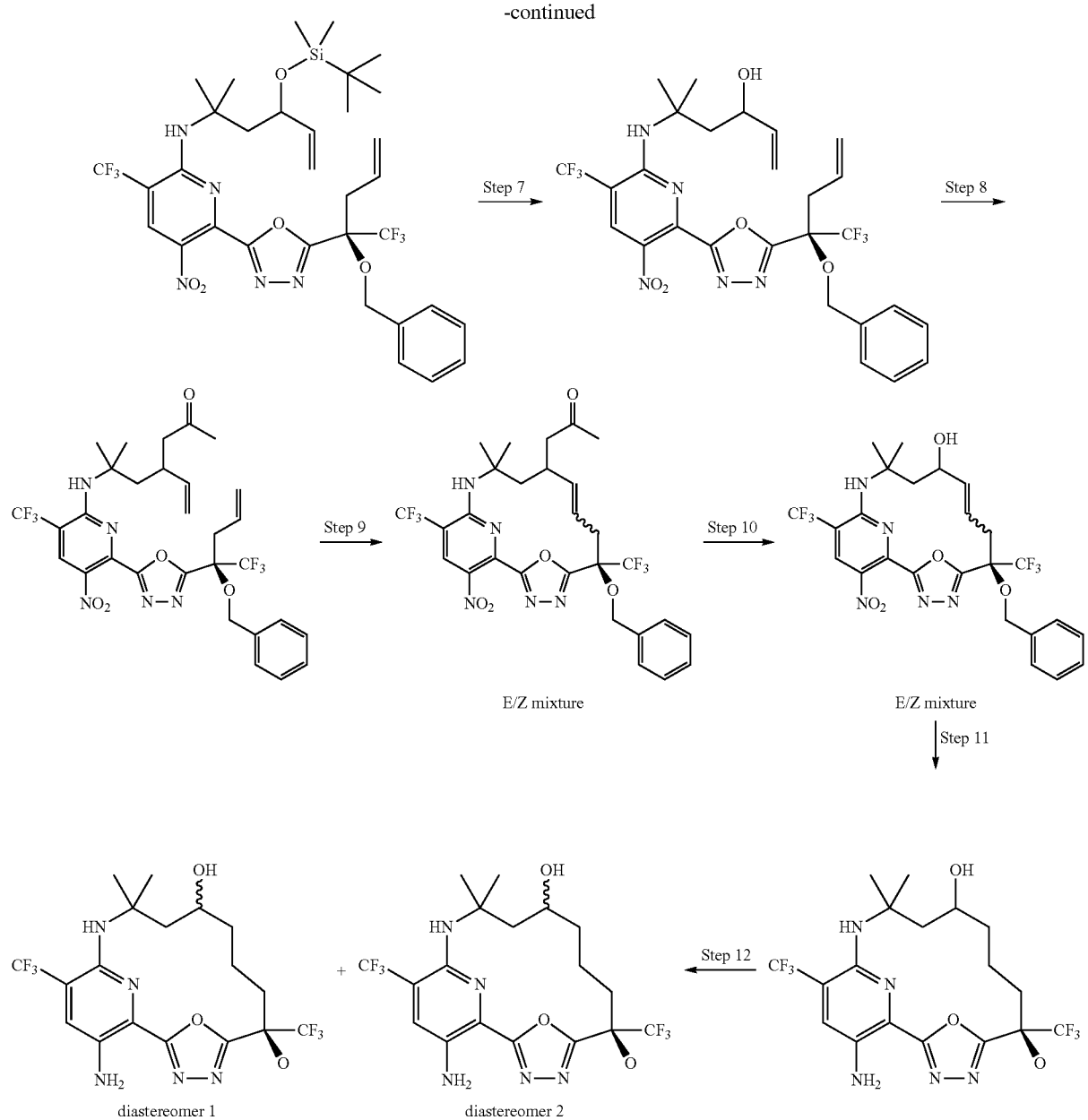

E/Z mixture

E/Z mixture diastereomer 1 diastereomer 2

Step 1: tert-Butyl N-(3-hydroxy-1,1-dimethyl-pent-4-enyl) carbamate

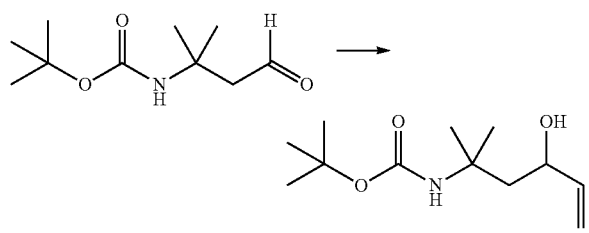

A solution of tert-butyl N-(1,1-dimethyl-3-oxo-propyl) carbamate (3.29 g, 14.712 mmol) was cooled to −78° C. under an atmosphere of nitrogen and treated dropwise with bromo(vinyl)magnesium (35 mL of 1 M, 35 mmol) over 30 minutes. The reaction mixture was held at this temperature for 30 min and then transferred to a 0° C. ice bath and held at this temperature for 3 h. The mixture was then quenched with 200 mL of saturated aqueous NH$_4$Cl solution. The mixture was extracted with diethyl ether (3×100 mL). The combined organic layers were washed with brine (200 mL), dried over Na$_2$SO$_4$, filtered, and concentrated under reduced pressure. The residue was purified by silica gel chromatography (120 g, dry loaded, eluted with 0% to 45% diethyl ether in hexanes over 40 minutes) which gave as a clear liquid, tert-butyl N-(3-hydroxy-1,1-dimethyl-pent-4-enyl) carbamate (1.9 g, 47%). $^1$H NMR (500 MHz, CDCl$_3$) δ 5.96-5.81 (m, 1H), 5.30-5.19 (m, 2H (vinylic proton and OH)), 5.12-5.05 (m, 1H), 4.39-4.31 (m, 1H), 1.84-1.71 (m, 2H), 1.43 (s, 9H), 1.38 (s, 3H), 1.36 (s, 3H).

Step 2: 4-[tert-Butyl(dimethyl)silyl]oxy-2-methyl-hex-5-en-2-amine

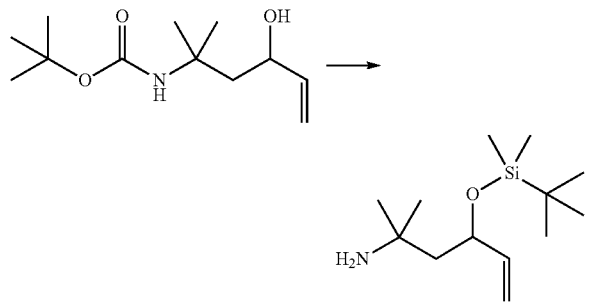

A solution of tert-butyl N-(3-hydroxy-1,1-dimethyl-pent-4-enyl) carbamate (2.23 g, 9.7246 mmol) and 2,6-lutidine (4.2559 g, 4.6 mL, 39.718 mmol) in dry DCM (60 mL) was cooled to 0° C. tert-Butyldimethylsilyl trifluoromethanesulfonate (15.539 g, 13.5 mL, 58.785 mmol) was then added dropwise over 15 min. The reaction mixture was warmed to room temperature and stirred for 2 h then diluted with dichloromethane (100 mL) and added saturated sodium bicarbonate solution (150 mL). The biphasic mixture was stirred for 15 min and the layers were separated. The aqueous layer was further extracted with dichloromethane (3×100 mL) and the combined organic layers were dried over anhydrous sodium sulfate, filtered, and evaporated. The residue was purified by reverse phase chromatography (buffer A: water buffered with 0.05 TFA; buffer B: acetonitrile buffered with 0.05 TFA, eluting from 30% buffer B to 90% buffer B over 40 minutes) which gave as a clear yellow oil, 4-[tert-butyl(dimethyl)silyl] oxy-2-methyl-hex-5-en-2-amine (0.91 g, 38%). $^1$H NMR (500 MHz, DMSO-d6) δ 5.88 (ddd, J=17.2, 10.2, 7.0 Hz, 1H), 5.23-5.14 (m, 1H), 5.08-5.00 (m, 1H), 4.38 (dd, J=12.2, 6.6 Hz, 1H), 1.61 (dd, J=14.0, 7.2 Hz, 1H), 1.47 (dd, J=14.0, 4.9 Hz, 1H), 1.09 (s, 3H), 1.07 (s, 3H), 0.90 (s, 9H), 0.11 (s, 3H), 0.06 (s, 3H). ESI-MS m/z calc. 243.2018, found 244.4 (M+1)$^+$; Retention time: 2.82 minutes (LC Method G).

Step 3: Methyl 6-[[3-[tert-butyl(dimethyl)silyl]oxy-1,1-dimethyl-pent-4-enyl]amino]-3-nitro-5-(trifluoromethyl)pyridine-2-carboxylate

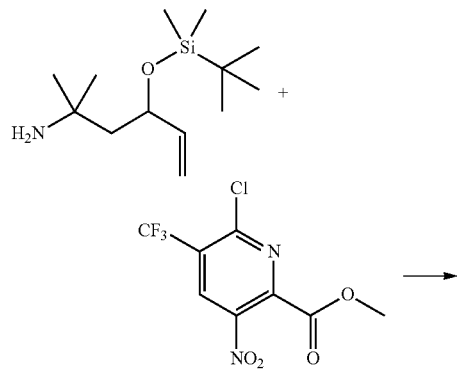

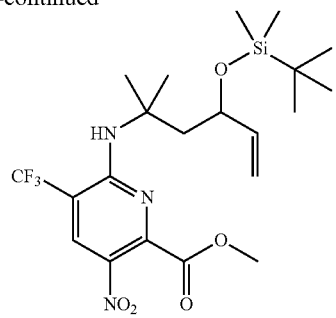

To a solution of methyl 6-chloro-3-nitro-5-(trifluoromethyl)pyridine-2-carboxylate (1 g, 3.514 mmol) in acetonitrile (40 mL) was added 4-[tert-butyl(dimethyl)silyl] oxy-2-methyl-hex-5-en-2-amine (0.91 g, 3.7378 mmol) and DIEA (1.4098 g, 1.9 mL, 10.908 mmol). The resulting yellow solution was stirred at room temperature for 24 h and then heated at 40° C. overnight. After cooling to room temperature, the solvent was removed under reduced pressure and the residue was purified by silica gel chromatography (120 g, dry loaded, eluted from 0% to 10% diethyl ether in hexanes over 45 minutes) giving as a white solid, methyl 6-[[3-[tert-butyl(dimethyl)silyl] oxy-1,1-dimethyl-pent-4-enyl] amino]-3-nitro-5-(trifluoromethyl)pyridine-2-carboxylate (0.96 g, 56%). ESI-MS m/z calc. 491.2063, found 492.0 (M+1)$^+$; Retention time: 4.56 minutes (LC Method G).

Step 4: 6-[[3-[tert-Butyl(dimethyl)silyl]oxy-1,1-dimethyl-pent-4-enyl]amino]-3-nitro-5-(trifluoromethyl)pyridine-2-carboxylic Acid

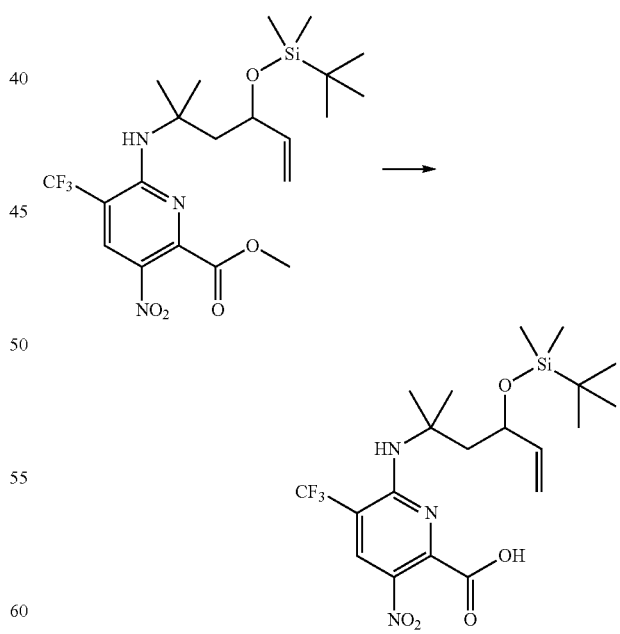

To a solution of methyl 6-[[3-[tert-butyl(dimethyl)silyl] oxy-1,1-dimethyl-pent-4-enyl] amino]-3-nitro-5-(trifluoromethyl)pyridine-2-carboxylate (0.96 g, 1.9529 mmol) in THF (30 mL) and MeOH (9 mL) was added a solution of LiOH (0.6 g, 25.054 mmol) in water (15 mL). The reaction mixture was stirred at room temperature overnight and acidified with 5% aqueous citric acid solution to pH=2. The aqueous layer was extracted with diethyl ether (3×75 mL). The combined organic layers were washed with brine (100 mL), dried over anhydrous sodium sulfate and concentrated under vacuum to furnish as a yellow solid, 6-[[3-[tert-butyl (dimethyl)silyl] oxy-1,1-dimethyl-pent-4-enyl] amino]-3-nitro-5-(trifluoromethyl)pyridine-2-carboxylic acid (0.95 g, 100%). ESI-MS m/z calc. 477.1907, found 477.9 (M+1)$^+$; Retention time: 4.18 minutes (LC Method G).

Step 5: N'-[(2R)-2-Benzyloxy-2-(trifluoromethyl) pent-4-enoyl]-6-[[3-[tert-butyl(dimethyl)silyl]oxy-1, 1-dimethyl-pent-4-enyl]amino]-3-nitro-5-(trifluoromethyl)pyridine-2-carbohydrazide

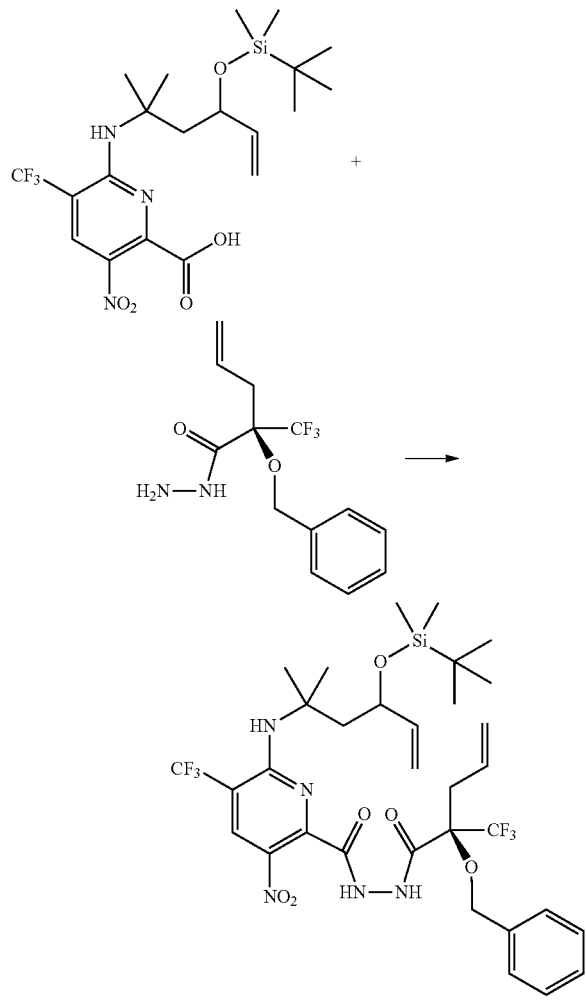

To a mixture of (2R)-2-benzyloxy-2-(trifluoromethyl) pent-4-enehydrazide (0.7 g, 2.4283 mmol) and 6-[[3-[tert-butyl(dimethyl)silyl] oxy-1,1-dimethyl-pent-4-enyl] amino]-3-nitro-5-(trifluoromethyl)pyridine-2-carboxylic acid (0.95 g, 1.9495 mmol) in EtOAc (30 mL) was added pyridine (782.4 mg, 0.8 mL, 9.8913 mmol) and propylphosphonic anhydride solution (2.5656 g, 2.4 mL of 50% w/w in EtOAc, 4.0316 mmol). The reaction mixture was stirred at room temperature overnight. To the reaction mixture 1 M aqueous NaHCO$_3$ solution (200 mL) was added and stirred for 15 min. The mixture was extracted with EtOAc (3×100 mL) and the combined organic layers were washed with brine (100 mL), dried (Na$_2$SO$_4$), filtered, and concentrated. The oily residue was purified by silica gel chromatography (40 g, dry loaded, eluting from 0% to 45% diethyl ether in hexanes over 30 minutes) which gave as a yellow solid, N-[(2R)-2-benzyloxy-2-(trifluoromethyl) pent-4-enoyl]-6-[[3-[tert-butyl(dimethyl)silyl]oxy-1,1-dimethyl-pent-4-enyl]amino]-3-nitro-5-(trifluoromethyl)pyridine-2-carbohydrazide (1 g, 69%). ESI-MS m/z calc. 747.2887, found 748.4 (M+1)$^+$; Retention time: 4.52 minutes (LC Method G).

Step 6: 6-[5-[(1R)-1-Benzyloxy-1-(trifluoromethyl) but-3-enyl]-1,3,4-oxadiazol-2-yl]-N-[3-[tert-butyl (dimethyl)silyl]oxy-1,1-dimethyl-pent-4-enyl]-5-nitro-3-(trifluoromethyl)pyridin-2-amine

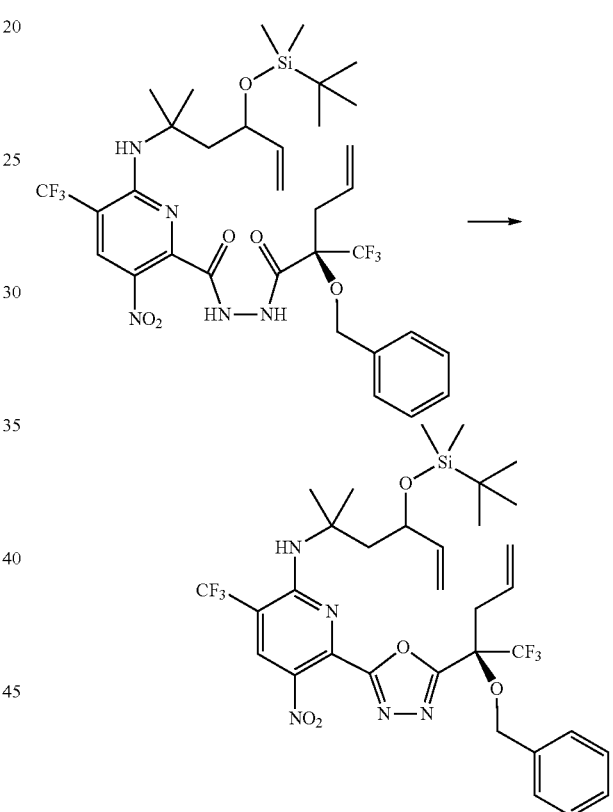

To a solution of N-[(2R)-2-benzyloxy-2-(trifluoromethyl) pent-4-enoyl]-6-[[3-[tert-butyl(dimethyl)silyl]oxy-1,1-dimethyl-pent-4-enyl]amino]-3-nitro-5-(trifluoromethyl)pyridine-2-carbohydrazide (0.32 g, 0.4279 mmol) and DIEA (185.5 mg, 0.25 mL, 1.4353 mmol) in acetonitrile (7 mL) was added TsCl (125 mg, 0.6557 mmol) and the mixture was stirred at room temperature for 1 h. The reaction mixture was concentrated, and the residue was dissolved in ethyl acetate (75 mL). The organic layer was washed with aqueous 5% NaHCO$_3$(2×75 mL), water (2×75 mL), brine (75 mL), dried (sodium sulfate), filtered and concentrated. The residue was purified by silica gel chromatography (12 g, dry loaded, and eluted with 0% to 15% diethyl ether in hexanes over 30 minutes) which gave as a clear yellow oil, 6-[5-[(1R)-1-benzyloxy-1-(trifluoromethyl)but-3-enyl]-1,3,4-oxadiazol-2-yl]-N-[3-[tert-butyl(dimethyl)silyl]oxy-1,1-dimethylpent-4-enyl]-5-nitro-3-(trifluoromethyl)pyridin-2-amine (311 mg, 100%). ESI-MS m/z calc. 729.2781, found 730.4 (M+1)+; Retention time: 4.9 minutes (LC Method G).

Step 7: 5-[[6-[5-[(1R)-1-Benzyloxy-1-(trifluoromethyl)but-3-enyl]-1,3,4-oxadiazol-2-yl]-5-nitro-3-(trifluoromethyl)-2-pyridyl]amino]-5-methyl-hex-1-en-3-ol

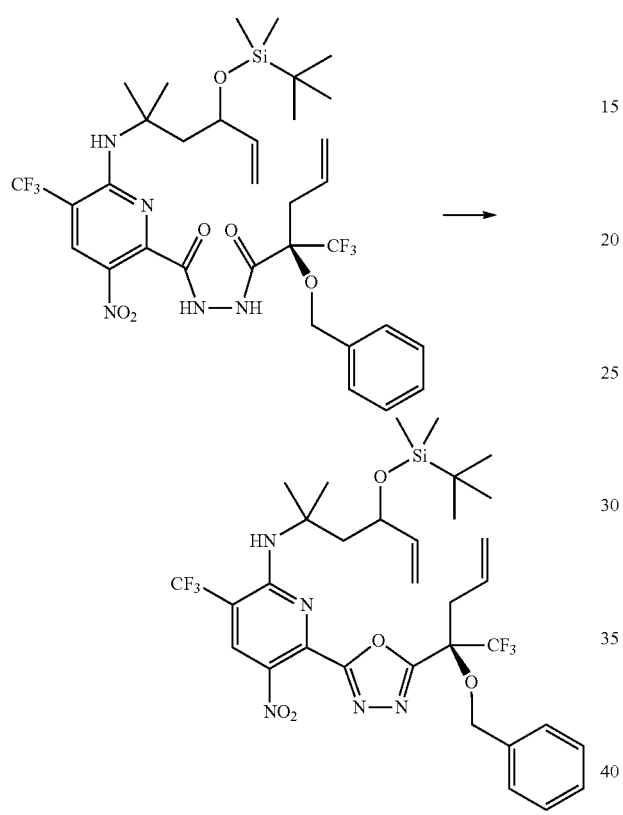

To a solution of 6-[5-[(1R)-1-benzyloxy-1-(trifluoromethyl)but-3-enyl]-1,3,4-oxadiazol-2-yl]-N-[3-[tert-butyl(dimethyl)silyl]oxy-1,1-dimethyl-pent-4-enyl]-5-nitro-3-(trifluoromethyl)pyridin-2-amine (790 mg, 1.0825 mmol) in methanol (25 mL) was added aqueous 1 N HCl (1.6 mL of 1 M, 1.6 mmol) at room temperature. The reaction was stirred at room temperature for 6 h. The reaction mixture was diluted with saturated sodium bicarbonate solution (100 mL) and extracted with diethyl ether (3×100 mL). The combined organic layers were washed with brine (100 mL), dried over anhydrous sodium sulfate, filtered and concentrated under vacuum to furnish as a yellow solid, 5-[[6-[5-[(1R)-1-benzyloxy-1-(trifluoromethyl)but-3-enyl]-1,3,4-oxadiazol-2-yl]-5-nitro-3-(trifluoromethyl)-2-pyridyl]amino]-5-methyl-hex-1-en-3-ol (0.67 g, 100%). ESI-MS m/z calc. 615.1916, found 616.3 (M+1)+; Retention time: 4.06 minutes (LC Method G).

Step 8: [3-[[6-[5-[(1R)-1-Benzyloxy-1-(trifluoromethyl) but-3-enyl]-1,3,4-oxadiazol-2-yl]-5-nitro-3-(trifluoromethyl)-2-pyridyl]amino]-3-methyl-1-vinyl-butyl] acetate

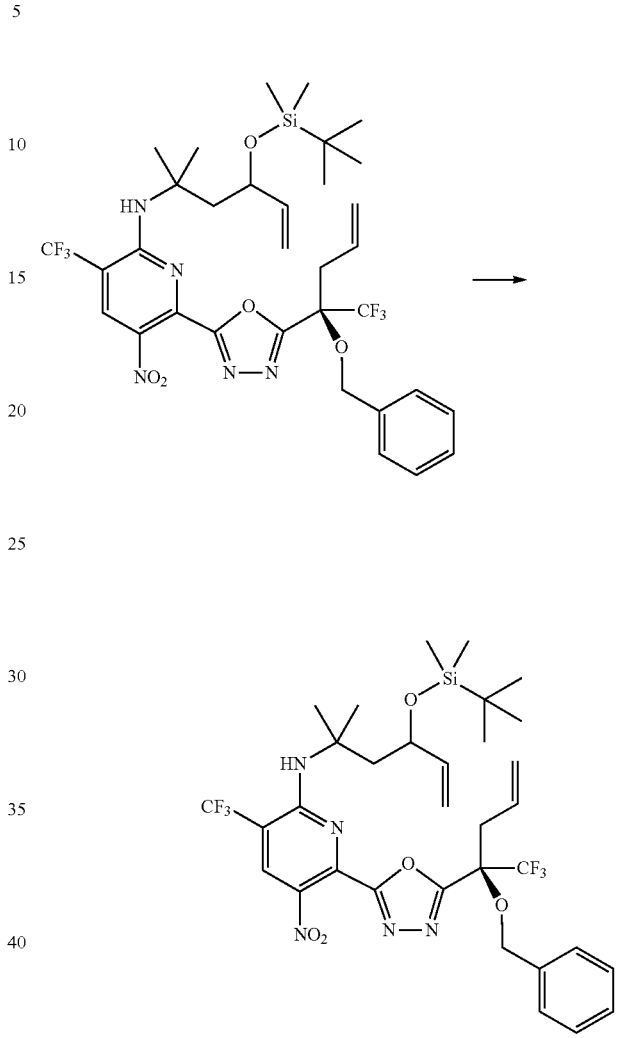

To a solution of 5-[[6-[5-[(1R)-1-benzyloxy-1-(trifluoromethyl)but-3-enyl]-1,3,4-oxadiazol-2-yl]-5-nitro-3-(trifluoromethyl)-2-pyridyl]amino]-5-methyl-hex-1-en-3-ol (146.5 mg, 0.238 mmol) in anhydrous dichloromethane (3 mL) was added pyridine (58.68 mg, 60 µL, 0.7418 mmol), acetic anhydride (43.28 mg, 40 µL, 0.4239 mmol) and a catalytic amount of DMAP (7.9 mg, 0.0647 mmol). The reaction mixture was stirred at room temperature for 24 h and then concentrated under vacuum. The residue was purified by silica gel chromatography using a gradient from 0% to 20% ethyl acetate in hexane to furnish as a light-yellow gel, [3-[[6-[5-[(1R)-1-benzyloxy-1-(trifluoromethyl) but-3-enyl]-1,3,4-oxadiazol-2-yl]-5-nitro-3-(trifluoromethyl)-2-pyridyl] amino]-3-methyl-1-vinyl-butyl] acetate (154.5 mg, 99%). ESI-MS m/z calc. 657.2022, found 658.7 (M+1)+; Retention time: 4.11 minutes (LC Method G).

Step 9: [(6R)-6-Benzyloxy-12,12-dimethyl-17-nitro-6,15-bis(trifluoromethyl)-19-oxa-3,4,13,18-tetrazatricyclo[12.3.1.12,5]nonadeca-1(17),2,4,8,14(18),15-hexaen-10-yl]acetate (E/Z Mixture)

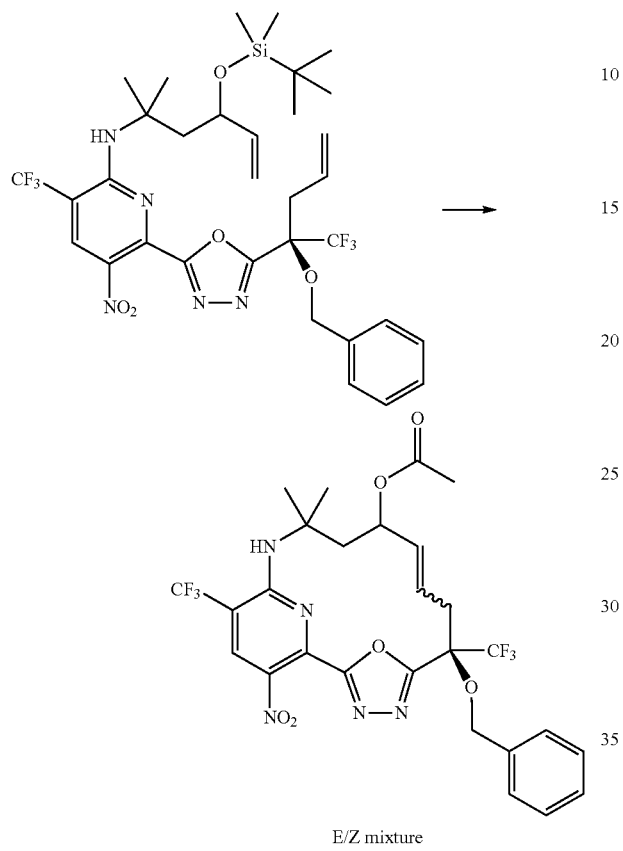

E/Z mixture

Zhan catalyst-1B (145 mg, 0.1973 mmol) was mixed in toluene (40 mL) at room temperature and degassed with $N_2$ for 30 minutes. Separately, [3-[[6-[5-[(1R)-1-benzyloxy-1-(trifluoromethyl) but-3-enyl]-1,3,4-oxadiazol-2-yl]-5-nitro-3-(trifluoromethyl)-2-pyridyl] amino]-3-methyl-1-vinyl-butyl] acetate (353 mg, 0.5315 mmol) in toluene (10 mL) was degassed with $N_2$ for 15 minutes and then added portion-wise to a pre-heated (110° C.) flask containing the catalyst in the toluene with efficient stirring. The mixture was heated at 110° C. for 16 h. More Zhan catalyst-1B (64 mg, 0.0871 mmol) was added and the reaction was continued at the same temperature for another 3 h. The reaction mixture was cooled to room temperature and then added EtOAc (50 ml) and brine (40 ml). The organic layer was separated and dried over anhydrous $MgSO_4$, filtered and concentrated. The residue was purified by silica gel chromatography (40 g column) using a gradient from 0% to 20% ethyl acetate in hexanes which gave as a brown oil, [(6R)-6-benzyloxy-12,12-dimethyl-17-nitro-6,15-bis(trifluoromethyl)-19-oxa-3,4,13,18-tetrazatricyclo[12.3.1.12,5]nonadeca-1(17),2,4,8,14(18),15-hexaen-10-yl] acetate (E/Z mixture) (149 mg, 20%). ESI-MS m/z calc. 629.1709, found 630.5 (M+1)$^+$; Retention time: 3.96 minutes (LC Method G).

Step 10: (6R)-6-Benzyloxy-12,12-dimethyl-17-nitro-6,15-bis(trifluoromethyl)-19-oxa-3,4,13,18-tetrazatricyclo[12.3.1.12,5]nonadeca-1(18),2,4,8,14,16-hexaen-10-ol (E/Z Mixture)

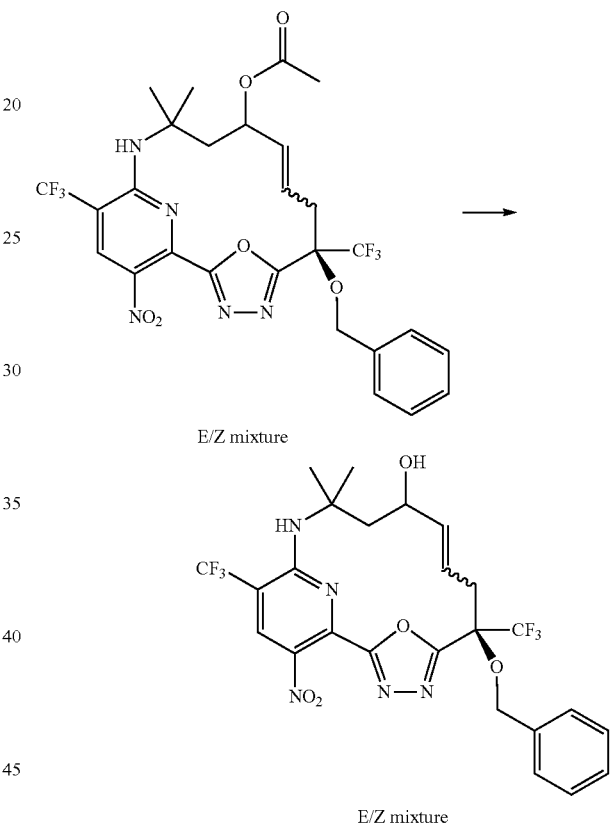

E/Z mixture

To a solution of [(6R)-6-benzyloxy-12,12-dimethyl-17-nitro-6,15-bis(trifluoromethyl)-19-oxa-3,4,13,18-tetrazatricyclo[12.3.1.12,5]nonadeca-1(17),2,4,8,14(18),15-hexaen-10-yl] acetate (E/Z mixture) (12 mg, 0.0191 mmol) in MeOH (0.5 mL) at room temperature was added $K_2CO_3$ (14 mg, 0.1013 mmol) and the mixture was stirred at room temperature for 3 h. Brine (15 mL) and dichloromethane (20 ml) were added and the layers were separated. The organic layer was concentrated. The residue was purified by silica gel chromatography (12 g column) using a gradient from 0% to 40% EtOAc in hexanes giving as a colorless oil, (6R)-6-benzyloxy-12,12-dimethyl-17-nitro-6,15-bis(trifluoromethyl)-19-oxa-3,4,13,18-tetrazatricyclo[12.3.1.12,5]nonadeca-1(18),2,4,8,14,16-hexaen-10-ol (E/Z mixture) (11 mg, 93%). ESI-MS m/z calc. 587.1603, found 588.5 (M+1)$^+$; Retention time: 4.12 minutes (LC Method G).

Step 11: (6R)-17-Amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,10-diol

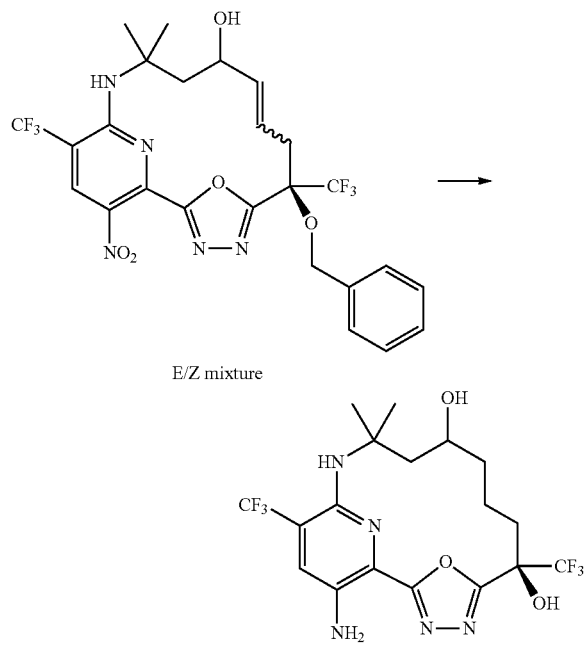

E/Z mixture

To a solution of (6R)-6-benzyloxy-12,12-dimethyl-17-nitro-6,15-bis(trifluoromethyl)-19-oxa-3,4,13,18-tetrazatricyclo[12.3.1.1²,⁵]nonadeca-1(18),2,4,8,14,16-hexaen-10-ol (E/Z mixture) (110 mg, 0.1779 mmol) in EtOH (5 mL) was added 5 Pd/C (180 mg, 0.0846 mmol). The mixture was purged with hydrogen gas several times and then hydrogenated at 50 psi on a Parr shaker for 6 h. The reaction mixture was filtered through a celite pad washing with methanol. The filtrate was concentrated to provide as a green-yellow foam, (6R)-17-amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,10-diol (77 mg, 88%). ESI-MS m/z calc. 469.1549, found 470.5 (M+1)⁺; Retention time: 3.61 minutes (LC Method G).

Step 12: (6R)-17-Amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,10-diol (diastereomer 1) (Compound 214) and (6R)-17-amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,10-diol (diastereomer 2) (Compound 215)

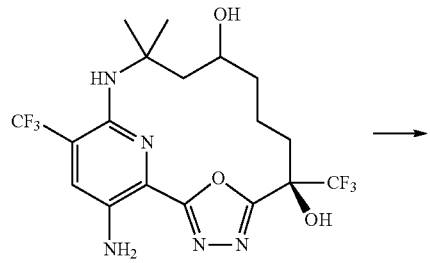

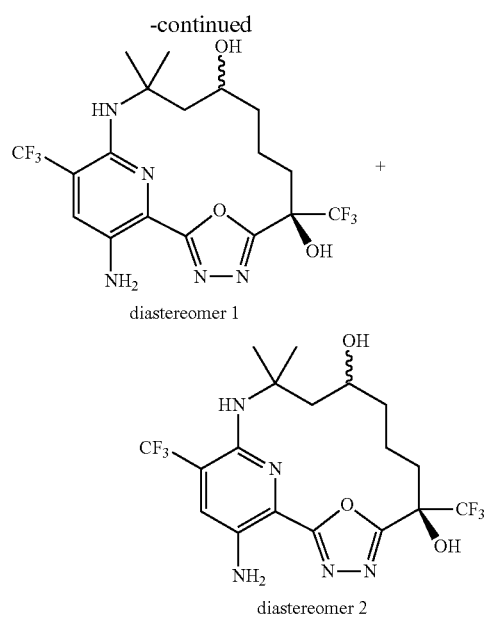

diastereomer 1 diastereomer 2

Racemic (6R)-17-amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,10-diol (75 mg, 0.1358 mmol) was purified by chiral SFC using Chiral Cel OJ column (250×21.2 mm, 5 μm particle size) eluting with 12% MeOH (20 mM NH₃) in 88% CO₂ with flow rate of 70 mL/min which gave as a yellow solid and the first peak to elute, (6R)-17-amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,10-diol (diastereomer 1) (19.9 mg, 62%). ¹H NMR (400 MHz, DMSO-d6) δ 7.63 (s, 1H), 7.60 (s, 1H), 5.97 (s, 2H), 4.47 (s, 1H), 4.28 (d, J=5.4 Hz, 1H), 3.89-3.76 (m, 1H), 3.60 (d, J=13.7 Hz, 1H), 2.37 (t, J=13.1 Hz, 1H), 1.95 (tt, J=11.3, 5.6 Hz, 1H), 1.75-1.60 (m, 1H), 1.59-1.47 (m, 3H), 1.47 (s, 3H), 1.40 (s, 3H), 1.03 (dd, J=13.7, 9.8 Hz, 1H). ESI-MS m/z calc. 469.15485, found 470.2 (M+1)⁺; Retention time: 1.52 minutes (LC Method A).

The second peak to elute provided as a yellow solid, (6R)-17-amino-12,12-dimethyl-6,15-bis(trifluoromethyl)-19-oxa-3,4,13,18-tetrazatricyclo[12.3.1.1²,⁵]nonadeca-1(18),2,4,14,16-pentaene-6,10-diol (diastereomer 2) (25.5 mg, 79%). ¹H NMR (400 MHz, DMSO-d6) δ 7.60 (s, 1H), 7.59 (s, 1H), 6.00 (s, 2H), 4.48 (s, 1H), 4.31 (d, J=5.3 Hz, 1H), 3.76 (d, J=14.2 Hz, 1H), 3.65 (d, J=12.9 Hz, 1H), 2.44 (t, J=12.9 Hz, 2H), 1.97 (dd, J=13.6, 9.5 Hz, 1H), 1.70-1.52 (m, 3H), 1.45 (s, 3H), 1.39 (s, 3H), 1.11 (dd, J=13.8, 8.9 Hz, 1H). ESI-MS m/z calc. 469.15485, found 470.2 (M+1)⁺; Retention time: 1.49 minutes (LC Method A).

Example 119; Preparation of 17-amino-7-fluoro-12,
12-dimethyl-15-(trifluoromethyl)-19-oxa-3,4,13,18-
tetrazatricyclo[12.3.1.12,5]nonadeca-1(18),2,4,14,
16-pentaen-6-ol (mixture of diastereomers)
(Compound 216), 17-amino-12,12-dimethyl-15-
(trifluoromethyl)-19-oxa-3,4,13,18-tetrazatricyclo
[12.3.1.12,5]nonadeca-1(18),2,4,14,16-pentaen-6-ol
(Compound 217), 17-amino-7,7-difluoro-12,12-
dimethyl-15-(trifluoromethyl)-19-oxa-3,4,13,18-
tetrazatricyclo[12.3.1.12,5]nonadeca-1(18),2,4,14,
16-pentaen-6-ol (enantiomer 1) (Compound 218)
and 17-amino-7,7-difluoro-12,12-dimethyl-15-(trif-
luoromethyl)-19-oxa-3,4,13,18-tetrazatricyclo
[12.3.1.12,5]nonadeca-1(18),2,4,14,16-pentaen-6-ol
(enantiomer 2) (Compound 219)

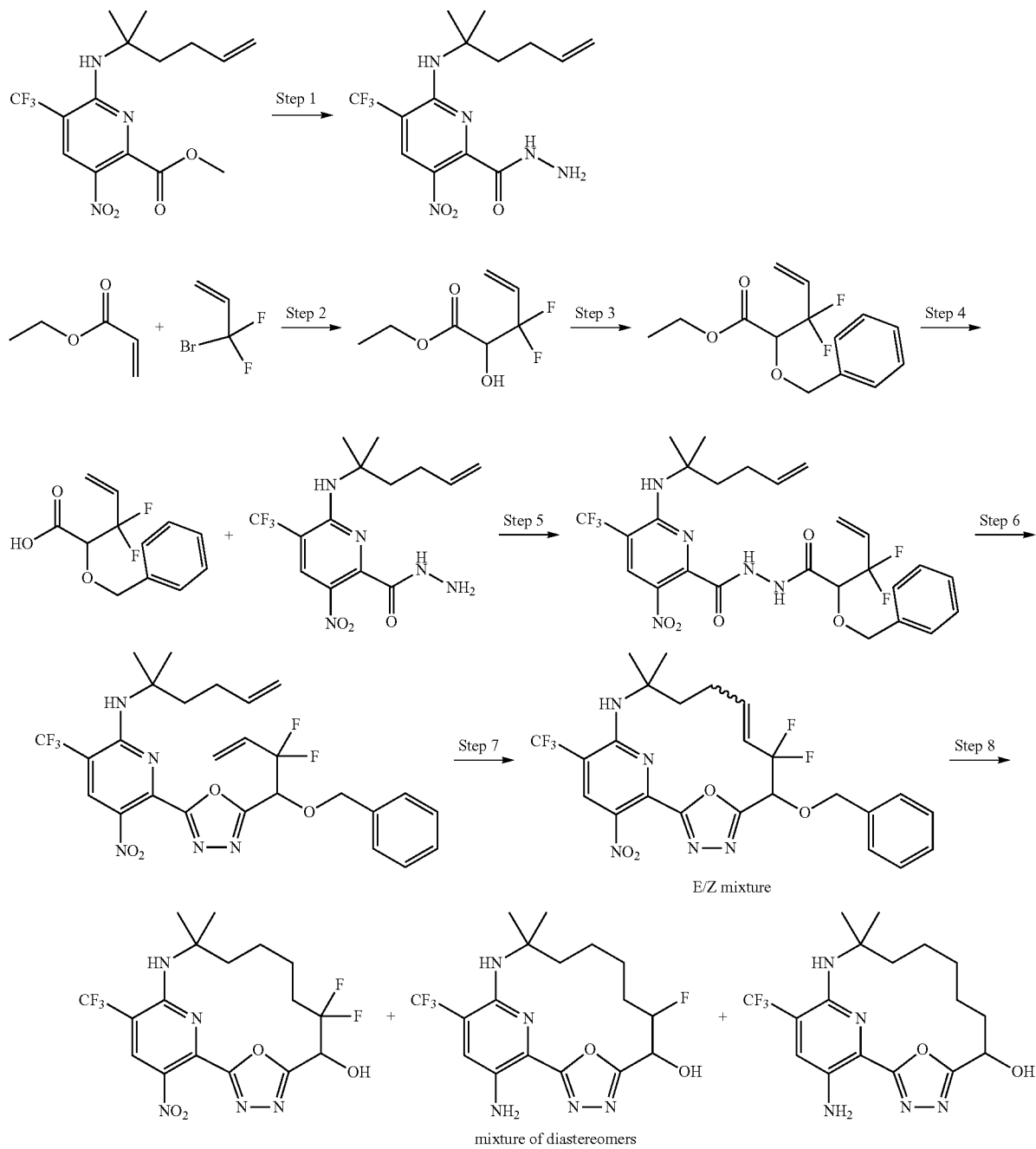

-continued

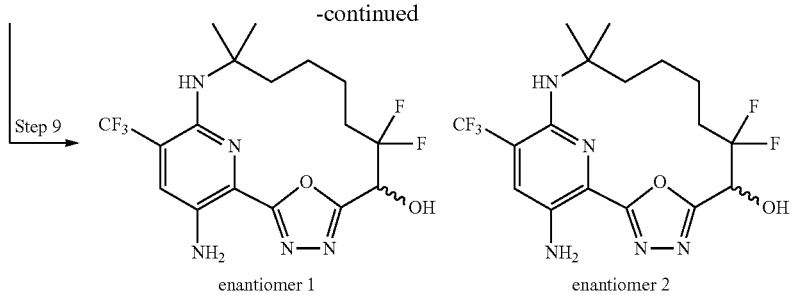

enantiomer 1      enantiomer 2

Step 1: 6-(1,1-Dimethylpent-4-enylamino)-3-nitro-5-(trifluoromethyl)pyridine-2-carbohydrazide

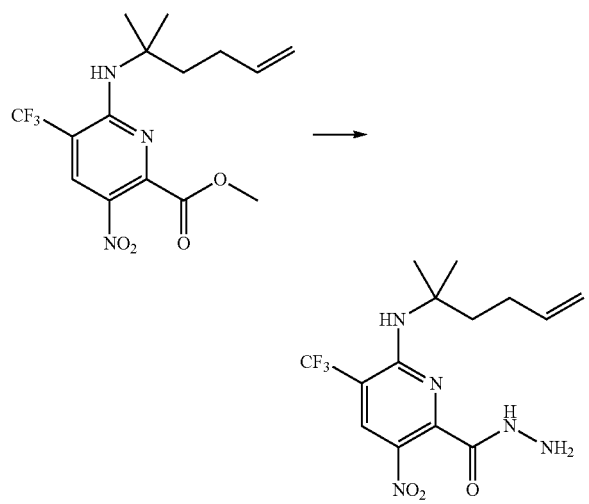

To a solution of methyl 6-(1,1-dimethylpent-4-enylamino)-3-nitro-5-(trifluoromethyl)pyridine-2-carboxylate (2.72 g, 7.5280 mmol) in MeOH (60 mL) in a pressure tube was added hydrazine monohydrate (3.35 g, 66.919 mmol). The mixture was stirred at 85° C. for 4 h, cooled to room temperature and concentrated. The residue was co-evaporated with toluene (2×20 mL) and purified by silica gel flash chromatography eluting with a gradient from 20% to 60% EtOAc in heptanes) to afford as a pale-yellow oil, 6-(1,1-dimethylpent-4-enylamino)-3-nitro-5-(trifluoromethyl)pyridine-2-carbohydrazide (2.7 g, 99%). $^1$H NMR (400 MHz, CDCl$_3$) δ 8.34 (s, 1H), 5.84-5.71 (m, 1H), 5.44 (br. s, 1H), 5.04-4.93 (m, 2H), 3.39 (br. s, 3H), 2.09-1.93 (m, 4H), 1.49 (s, 6H). $^{19}$F NMR (377 MHz, CDCl$_3$) δ−64.45 (s, 3F). ESI-MS m/z calc. 361.1362, found 362.2 (M+1)$^+$; Retention time: 1.96 minutes (LC Method E).

Step 2: Ethyl 3,3-difluoro-2-hydroxy-pent-4-enoate

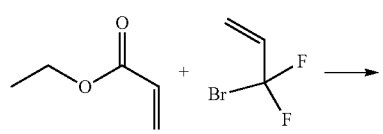

To a solution of 3-bromo-3,3-difluoro-prop-1-ene (4.8 g, 30.582 mmol) and ethyl 2-oxoacetate in toluene (5.9 mL of 50% w/v, 28.896 mmol) in DMF (60 mL) and water (18 mL) at 10° C. was added indium (7 g, 60.966 mmol). The mixture was stirred at room temperature overnight then ice-water (200 mL) was added. The resulted mixture was stirred for 30 min, diluted with tert-butyl methyl ether (100 mL), filtered through diatomaceous earth and the cake was washed with tert-butyl methyl ether. The aqueous phase was back extracted with $^t$BuOCH$_3$ (2×100 mL). The combined organic layers were dried with Na$_2$SO$_4$, filtered and concentrated. The residue (5.8 g) was purified by silica gel flash chromatography (50% to 100% dichloromethane in pentane) to afford as a colorless oil, ethyl 3,3-difluoro-2-hydroxy-pent-4-enoate (4.283 g, 82%). $^1$H NMR (400 MHz, CDCl$_3$) δ 6.10-5.93 (m, 1H), 5.82-5.72 (m, 1H), 5.58 (d, J=11.0 Hz, 1H), 4.43-4.27 (m, 3H), 3.22 (d, J=6.4 Hz, 1H), 1.34 (t, J=7.1 Hz, 3H). $^{19}$F NMR (377 MHz, CDCl$_3$) δ−107.00 to −107.85 (m, 1F), −108.89 to −109.75 (m, 1F). ESI-MS m/z calc. 180.0598, found 181.2 (M+1)$^+$; Retention time: 1.47 minutes. (LC Method E).

Step 3: Ethyl 2-benzyloxy-3,3-difluoro-pent-4-enoate

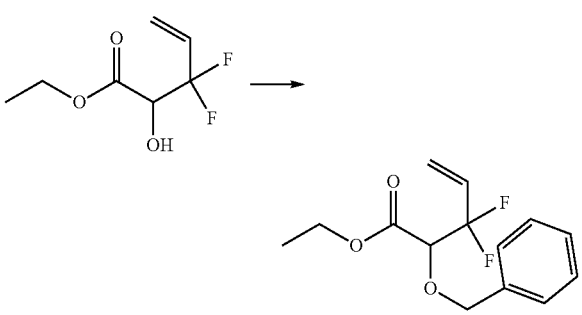

To a solution of ethyl 3,3-difluoro-2-hydroxy-pent-4-enoate (2.45 g, 11.832 mmol) in dichloromethane (19 mL) and anhydrous heptane (38 mL) at 0° C. was added benzyl 2,2,2-trichloroacetimidate (7 g, 27.72 mmol). The mixture was stirred at 0° C. for 5 min and triflic acid (400 mg, 2.6653 mmol) was added dropwise giving a white precipitate. The mixture was allowed to slowly warm up to room temperature and was stirred at room temperature (5 to 19° C.) overnight and then cooled to 0° C. and diluted with dichloromethane (50 mL). Saturated aqueous NaHCO₃ (20 mL) was added and the two layers were separated and the aqueous layer was extracted with dichloromethane (2×30 mL). The combined organic layers were dried with Na₂SO₄, filtered and concentrated under reduced pressure. Purification by silica gel chromatography (gradient: 0% to 10% EtOAc in heptanes) afforded ethyl 2-benzyloxy-3,3-difluoro-pent-4-enoate (1.56 g, 46%) as a clear oil. The product was not ionizable on LCMS. ¹H NMR (400 MHz, CDCl₃) δ 7.45-7.31 (m, 5H), 6.16-6.00 (m, 1H), 5.80-5.71 (m, 1H), 5.56 (d, J=11.2 Hz, 1H), 4.79 (d, J=12.0 Hz, 1H), 4.61 (d, J=12.0 Hz, 1H), 4.33-4.16 (m, 3H), 1.31 (t, J=7.1 Hz, 3H). ¹⁹F NMR (377 MHz, CDCl₃) δ −102.91 to −103.81 (m, 1F), −106.39 to −107.27 (m, 1F). Retention time: 4.4 minutes (LC Method AA).

Step 4: 2-Benzyloxy-3,3-difluoro-pent-4-enoic Acid

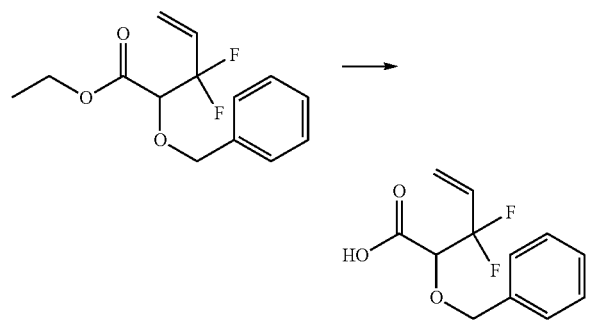

To a solution of ethyl 2-benzyloxy-3,3-difluoro-pent-4-enoate (1.55 g, 5.735 mmol) in DCE (60 mL) was added trimethyltin hydroxide (1.88 g, 10.397 mmol). The mixture was stirred at 82° C. for 30 h and cooled to room temperature. Silica gel (8 g) was added. The mixture was concentrated under reduced pressure. Purification by silica gel chromatography (gradient from 0% to 15% MeOH in dichloromethane) afforded 2-benzyloxy-3,3-difluoro-pent-4-enoic acid (1.14 g, 78%) as a colorless oil. The product was not ionizable on LCMS. ¹H NMR (400 MHz, CDCl₃) δ 7.42-7.31 (m, 5H), 6.13-5.97 (m, 1H), 5.77 (dt, J=17.4, 2.2 Hz, 1H), 5.58 (d, J=11.0 Hz, 1H), 4.83-4.70 (m, 2H), 4.25 (t, J=9.4 Hz, 1H). ¹⁹F NMR (377 MHz, CDCl₃) δ −103.47 to −104.44 (m, 1F), −106.04 to −106.95 (m, 1F). Retention time: 1.86 minutes (LC Method E).

Step 5: N'-(2-Benzyloxy-3,3-difluoro-pent-4-enoyl)-6-(1,1-dimethylpent-4-enylamino)-3-nitro-5-(trifluoromethyl)pyridine-2-carbohydrazide

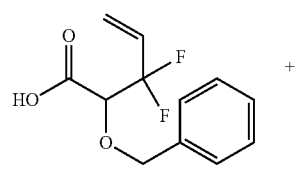

+

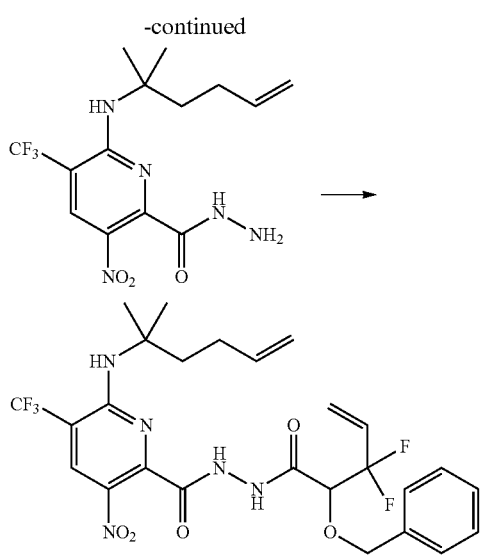

A 250-mL dried flask was charged with 2-benzyloxy-3,3-difluoro-pent-4-enoic acid (806 mg, 3.3276 mmol) and dichloromethane (20 mL). Oxalyl chloride (573 mg, 0.3938 mL, 4.5144 mmol) was added, followed by DMF (292 mg, 0.3093 mL, 3.9949 mmol) dropwise. The mixture was stirred at room temperature for 1 h. A solution of 6-(1,1-dimethylpent-4-enylamino)-3-nitro-5-(trifluoromethyl)pyridine-2-carbohydrazide (1.80 g, 4.9817 mmol) and DIEA (1.3 g, 1.752 mL, 10.059 mmol) in dichloromethane (10 mL) was added dropwise over 15 min. After addition, the reaction mixture was stirred at room temperature for 1 h. Saturated aqueous NaHCO₃ (15 mL) and water (15 mL) were added. The two layers were separated and the aqueous layer was extracted with dichloromethane (2×30 mL). The combined organic layer was dried with Na₂SO₄, filtered and concentrated. The residue was purified by silica gel flash chromatography (eluting from 5% to 40% EtOAc in heptanes) and a second silica gel flash chromatography (eluting with 5% EtOAc in dichloromethane) to afford N-(2-benzyloxy-3,3-difluoro-pent-4-enoyl)-6-(1,1-dimethylpent-4-enylamino)-3-nitro-5-(trifluoromethyl)pyridine-2-carbohydrazide (1.33 g, 68%) as a pale-yellow solid. ¹H NMR (400 MHz, CDCl₃) δ 9.05 (d, J=6.1 Hz, 1H), 8.74 (d, J=6.1 Hz, 1H), 8.31 (s, 1H), 7.45-7.31 (m, 5H), 6.12-5.96 (m, 1H), 5.85-5.71 (m, 2H), 5.57 (d, J=11.0 Hz, 1H), 5.46 (br. s, 1H), 5.08-4.91 (m, 2H), 4.88-4.77 (m, 2H), 4.26 (t, J=9.5 Hz, 1H), 2.11-1.96 (m, 4H), 1.52 (d, J=1.5 Hz, 6H). ¹⁹F NMR (377 MHz, CDCl₃) δ −64.50 (s, 3F), −104.56 to −105.38 (m, 1F), −106.39 to −107.22 (m, 1F). ESI-MS m/z calc. 585.2011, found 586.2 (M+1)⁺; Retention time: 2.23 minutes (LC Method E).

Step 6: 6-[5-(1-Benzyloxy-2,2-difluoro-but-3-enyl)-1,3,4-oxadiazol-2-yl]-N-(1,1-dimethylpent-4-enyl)-5-nitro-3-(trifluoromethyl)pyridin-2-amine

Step 7: 6-Benzyloxy-7,7-difluoro-12,12-dimethyl-17-nitro-15-(trifluoromethyl)-19-oxa-3,4,13,18-tetrazatricyclo[12.3.1.12,5]nonadeca-1(18),2,4,8,14,16-hexaene (E/Z mixture)

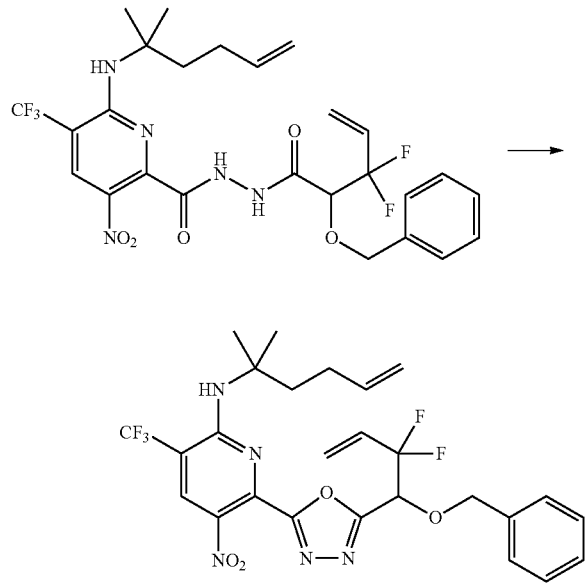

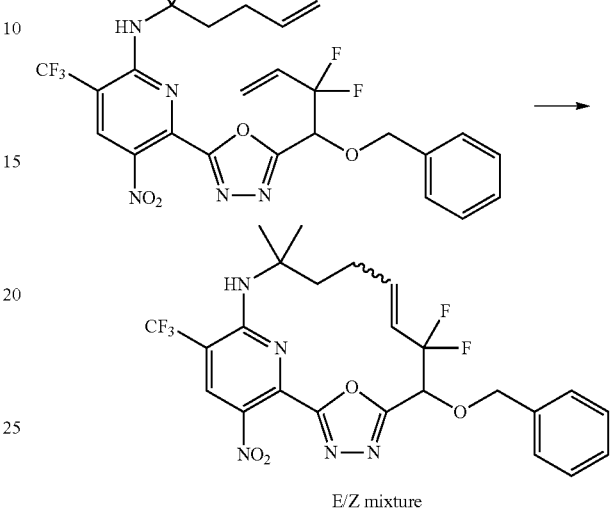

E/Z mixture

To a solution of N-(2-benzyloxy-3,3-difluoro-pent-4-enoyl)-6-(1,1-dimethylpent-4-enylamino)-3-nitro-5-(trifluoromethyl)pyridine-2-carbohydrazide (1.33 g, 2.2715 mmol) in dichloromethane (50 mL) at 0° C. was added DIEA (1.76 g, 2.3720 mL, 13.618 mmol), followed by trifluoromethanesulfonic anhydride (961 mg, 3.4061 mmol) dropwise. The mixture was stirred at 0° C. for 30 min. Morpholine (1.2 g) was added. The mixture was stirred at 0° C. for 5 min. Saturated aqueous NaHCO$_3$(25 mL) was added. The two layers were separated and the aqueous layer was extracted with dichloromethane (2×30 mL). The combined organic layers were dried with Na$_2$SO$_4$, filtered and concentrated. The residue was purified by silica gel flash chromatography (eluting with a gradient from 0% to 30% EtOAc in heptanes) to provide 6-[5-(1-benzyloxy-2,2-difluoro-but-3-enyl)-1,3,4-oxadiazol-2-yl]-N-(1,1-dimethylpent-4-enyl)-5-nitro-3-(trifluoromethyl)pyridin-2-amine (938 mg, 73%) as a pale-yellow oil. $^1$H NMR (400 MHz, CDCl$_3$) δ 8.52 (s, 1H), 7.41-7.29 (m, 5H), 6.08 (dq, J=17.5, 11.5 Hz, 1H), 5.81-5.69 (m, 2H), 5.62-5.52 (m, 2H), 5.11-4.90 (m, 3H), 4.80 (d, J=11.7 Hz, 1H), 4.59 (d, J=11.7 Hz, 1H), 2.10-1.92 (m, 4H), 1.49 (s, 6H). $^{19}$F NMR (377 MHz, CDCl$_3$) δ −64.56 (s, 3F), −103.99 to −104.84 (m, 1F), −107.22 to −108.19 (m, 1F). ESI-MS m/z calc. 567.1905, found 568.2 (M+1)$^+$; Retention time: 2.39 minutes (LC Method E).

A dried 1-L flask was charged with 6-[5-(1-benzyloxy-2,2-difluoro-but-3-enyl)-1,3,4-oxadiazol-2-yl]-N-(1,1-dimethylpent-4-enyl)-5-nitro-3-(trifluoromethyl)pyridin-2-amine (420 mg, 0.7401 mmol) and 1,2-dichloroethane (400 mL). The solution was bubbled with nitrogen for 1 h and heated to 75° C. A solution of Grubbs catalyst 2nd generation (130 mg, 0.1531 mmol) in 1,2-dichloroethane (5 mL) was added quickly. The mixture was stirred at 75° C. for 40 min. More Grubbs catalyst 2nd generation (60 mg, 0.0707 mmol) in 1,2-dichloroethane (5 mL) was added. The mixture was stirred at 75° C. for 1 h and cooled to room temperature. DMSO (385 mg) was added. The mixture was stirred at room temperature for 10 min and concentrated on silica gel (20 g). The residue was purified by silica gel flash chromatography (eluting with a gradient from 0% to 30% EtOAc in heptanes) to afford crude 6-benzyloxy-7,7-difluoro-12,12-dimethyl-17-nitro-15-(trifluoromethyl)-19-oxa-3,4,13,18-tetrazatricyclo[12.3.1.12,5]nonadeca-1(18),2,4,8,14,16-hexaene (180 mg) as a crude pale-yellow oil. This material was further purified by reversed-phase chromatography (Column: 100 g Aq C$_{18}$. Gradient: 5% to 95% MeCN in water with 0.1% formic acid modifier). The fractions containing the product were concentrated under reduced pressure to remove most of acetonitrile. The residue was treated with saturated aqueous NaHCO$_3$(10 mL) and extracted with EtOAc (3×20 mL). The organic layers were combined and dried with Na$_2$SO$_4$, filtered and concentrated under reduced pressure to give 6-benzyloxy-7,7-difluoro-12,12-dimethyl-17-nitro-15-(trifluoromethyl)-19-oxa-3,4,13,18-tetrazatricyclo[12.3.1.12,5]nonadeca-1(18),2,4,8,14,16-hexaene (E/Z mixture) (160.2 mg, 40%) as a pale-yellow oil. $^1$H NMR (400 MHz, CDCl$_3$) δ 8.46 (s, 1H), 7.40-7.30 (m, 5H), 6.36-6.25 (m, 1H), 6.06-5.93 (m, 1H), 5.57 (br. s, 1H), 5.21 (dd, J=8.1, 2.0 Hz, 1H), 4.77-4.66 (m, 2H), 2.84 (t, J=12.5 Hz, 1H), 2.40-2.28 (m, 1H), 2.17-2.07 (m, 1H), 1.86 (dd, J=14.2, 6.8 Hz, 1H), 1.46 (s, 6H). $^{19}$F NMR (377 MHz, CDCl$_3$) δ −64.14 (s, 3F), −92.09 to −92.96 (m, 1F), −110.61

(dd, J=254.8, 20.4 Hz, 1F). ESI-MS m/z calc. 539.1592, found 540.2 (M+1)⁺; Retention time: 2.3 minutes (LC Method E).

Step 8: 17-Amino-7,7-difluoro-12,12-dimethyl-15-(trifluoromethyl)-19-oxa-3,4,13,18-tetrazatricyclo[12.3.1.12,5]nonadeca-1(18),2,4,14,16-pentaen-6-ol, 17-amino-7-fluoro-12,12-dimethyl-15-(trifluoromethyl)-19-oxa-3,4,13,18-tetrazatricyclo[12.3.1.12,5]nonadeca-1(18),2,4,14,16-pentaen-6-ol (mixture of diastereomers) (Compound 216) and 17-amino-12,12-dimethyl-15-(trifluoromethyl)-19-oxa-3,4,13,18-tetrazatricyclo[12.3.1.12,5]nonadeca-1(18),2,4,14,16-pentaen-6-ol (Compound 217)

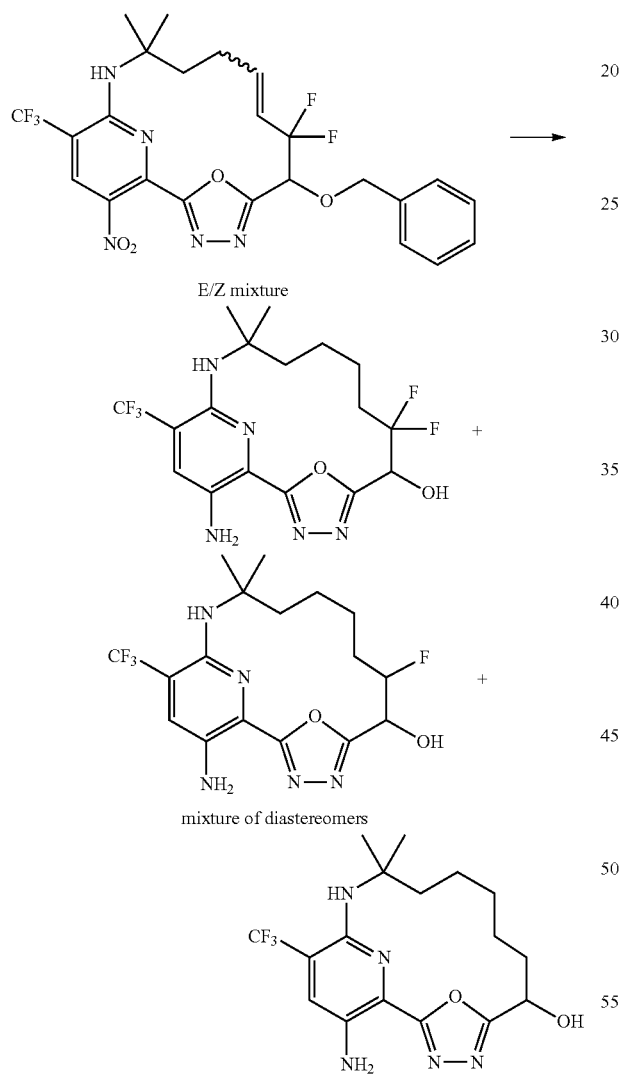

To a solution of 6-benzyloxy-7,7-difluoro-12,12-dimethyl-17-nitro-15-(trifluoromethyl)-19-oxa-3,4,13,18-tetrazatricyclo[12.3.1.12,5]nonadeca-1(18),2,4,8,14,16-hexaene (E/Z mixture) (175 mg, 0.3244 mmol) in MeOH (15 mL) in a 100 mL flask was added 10% Pd/C (50% wet, 82 mg, 5% w/w, 0.0385 mmol). Air in the flask was replaced by nitrogen through vacuum three times. Nitrogen was replaced by hydrogen through vacuum six times. The reaction mixture was stirred at room temperature under hydrogen (balloon) for 16 h. The mixture was filtered through diatomaceous earth and the cake was washed with EtOAc. The filtrate was concentrated and the residue was purified by silica gel flash chromatography (eluting 10% to 50% EtOAc in heptanes) to afford three products.

The major product 17-amino-7,7-difluoro-12,12-dimethyl-15-(trifluoromethyl)-19-oxa-3,4,13,18-tetrazatricyclo[12.3.1.12,5]nonadeca-1(18),2,4,14,16-pentaen-6-ol (102 mg, 73%) was isolated as a yellow solid. ¹H NMR (400 MHz, CDCl₃) δ 7.28 (s, 1H), 5.38-5.27 (m, 1H), 4.94 (br. s, 2H), 4.46 (br. s, 1H), 3.29 (d, J=7.3 Hz, 1H), 2.54-2.10 (m, 4H), 1.97-1.73 (m, 2H), 1.64-1.49 (m, 2H), 1.39 (s, 3H), 1.36 (s, 3H). ¹⁹F NMR (377 MHz, CDCl₃) δ−63.87 (s, 3F), −101.77 to −103.92 (m, 2F). ESI-MS m/z calc. 421.1537, found 422.3 (M+1)⁺; Retention time: 3.15 minutes (LC Method C).

The mono-defluorinated byproduct (20 mg) was further purified by silica gel chromatography (gradient from 20% to 50% EtOAc in heptanes). The desired fractions were concentrated under reduced pressure and the residue was freeze-dried to give 17-amino-7-fluoro-12,12-dimethyl-15-(trifluoromethyl)-19-oxa-3,4,13,18-tetrazatricyclo[12.3.1.12,5]nonadeca-1(18),2,4,14,16-pentaen-6-ol (mixture of diastereomers) (16 mg, 12%) as a yellow solid. ¹H NMR (400 MHz, DMSO-d6) δ 7.56 (s, 1H), 6.58 (d, J=6.1 Hz, 0.5H), 6.52 (d, J=6.6 Hz, 0.5H), 6.00-5.85 (m, 2H), 5.29-4.77 (m, 2H), 4.62 (s, 0.5H), 4.56 (s, 0.5H), 3.05-2.80 (m, 1H), 2.17-1.97 (m, 1H), 1.95-1.62 (m, 3H), 1.60-1.41 (m, 3H), 1.39-1.27 (m, 6H). ¹⁹F NMR (377 MHz, DMSO-d₆) δ−62.22 (s, 3F), −184.41 to −186.39 (m, 1F). ESI-MS m/z calc. 403.1631, found 404.2 (M+1)⁺; Retention time: 3.09 minutes (LC Method C).

The bis-defluorinated byproduct (10 mg) was purified by silica gel chromatography (gradient from 20%-70% MTBE in heptanes) and freeze dried to afford 17-amino-12,12-dimethyl-15-(trifluoromethyl)-19-oxa-3,4,13,18-tetrazatricyclo[12.3.1.12,5]nonadeca-1(18),2,4,14,16-pentaen-6-ol (8 mg, 6%) as a yellow solid. ¹H NMR (400 MHz, DMSO-d6) δ 7.55 (s, 1H), 6.06 (d, J=6.1 Hz, 1H), 5.89 (s, 2H), 4.98-4.89 (m, 1H), 4.58 (s, 1H), 2.63-2.51 (m, 1H), 2.10-1.95 (m, 2H), 1.88-1.75 (m, 1H), 1.59-1.37 (m, 6H), 1.34 (s, 3H), 1.30 (s, 3H). ¹⁹F NMR (377 MHz, DMSO-d6) δ−62.18 (s, 3F). ESI-MS m/z calc. 385.1726, found 386.2 (M+1)⁺; Retention time: 3.62 minutes (LC Method BB).

Step 9: 17-Amino-7,7-difluoro-12,12-dimethyl-15-(trifluoromethyl)-19-oxa-3,4,13,18-tetrazatricyclo[12.3.1.12,5]nonadeca-1(18),2,4,14,16-pentaen-6-ol (enantiomer 1) (Compound 218) and 17-amino-7,7-difluoro-12,12-dimethyl-15-(trifluoromethyl)-19-oxa-3,4,13,18-tetrazatricyclo[12.3.1.12,5]nonadeca-1(18),2,4,14,16-pentaen-6-ol (enantiomer 2) (Compound 219)

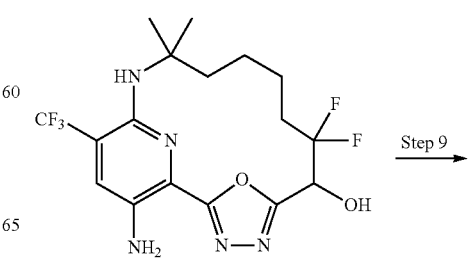

-continued

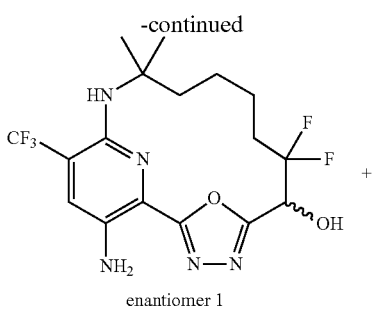

enantiomer 1

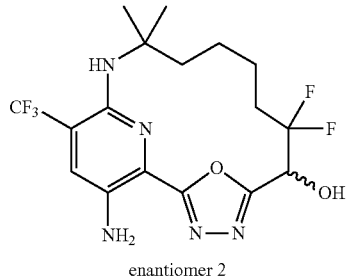

enantiomer 2

Racemic 17-amino-7,7-difluoro-12,12-dimethyl-15-(trifluoromethyl)-19-oxa-3,4,13,18-tetrazatricyclo[12.3.1.1²,⁵]nonadeca-1(18),2,4,14,16-pentaen-6-ol (102 mg, 0.2382 mmol) was subjected to SFC separation using the following conditions: Column Phenomenex Lux 5 μm, Cellulose 4 (250×21.2 mm); 6.7 mg/injection; Eluant: 10% EtOH (0.1% diethylamine) in 90% $CO_2$; Flow rate: 75 mL/min; Concentration: 22.2 mg/mL in methanol (no modifier); Injection volume: 300 μL; Outlet pressure: 100 bar; Wavelength: 250 nm; Temperature: 40° C.

The fractions containing the first eluting compound were concentrated under reduced pressure. The residue was taken up in acetonitrile (2.2 mL) and water (1.8 mL) was added. The resulting clear yellow solution was freeze dried to give material which was purified again by silica gel chromatography (gradient from 30%-50% EtOAc in heptane) followed by freeze drying to afford 17-amino-7,7-difluoro-12,12-dimethyl-15-(trifluoromethyl)-19-oxa-3,4,13,18-tetrazatricyclo[12.3.1.1²,⁵]nonadeca-1(18),2,4,14,16-pentaen-6-ol (enantiomer 1) (40 mg, 40%) as a yellow solid. $^1H$ NMR (400 MHz, DMSO-d6) δ 7.59 (s, 1H), 7.19 (d, J=6.4 Hz, 1H), 5.97 (s, 2H), 5.32-5.22 (m, 1H), 4.61 (s, 1H), 2.58-2.51 (m, 1H), 2.47-2.31 (m, 1H), 2.27-2.11 (m, 1H), 2.10-1.98 (m, 1H), 1.89-1.74 (m, 1H), 1.64-1.42 (m, 2H), 1.36 (s, 3H), 1.35-1.29 (m, 1H), 1.27 (s, 3H). $^{19}F$ NMR (377 MHz, DMSO-$d_6$) δ −62.30 (s, 3F), −99.00 to −100.99 (m, 2F). ESI-MS m/z calc. 421.1537, found 422.2 (M+1)⁺; Retention time: 4.45 minutes (LC Method AA).

The fractions containing the second eluting compound were concentrated under reduced pressure. The residue was taken up in acetonitrile (2.5 mL) and water (2.2 mL) was added. The resulting clear yellow solution was freeze dried to give material which was purified again by silica gel chromatography (gradient from 30%-50% EtOAc in heptane) followed by freeze drying to afford 17-amino-7,7-difluoro-12,12-dimethyl-15-(trifluoromethyl)-19-oxa-3,4,13,18-tetrazatricyclo[12.3.1.1²,⁵]nonadeca-1(18),2,4,14,16-pentaen-6-ol (enantiomer 2) (41 mg, 41%) as a yellow solid. $^1H$ NMR (400 MHz, DMSO-d6) δ 7.59 (s, 1H), 7.19 (d, J=6.4 Hz, 1H), 5.97 (s, 2H), 5.32-5.23 (m, 1H), 4.61 (s, 1H), 2.58-2.51 (m, 1H), 2.46-2.31 (m, 1H), 2.28-2.11 (m, 1H), 2.10-1.99 (m, 1H), 1.89-1.75 (m, 1H), 1.63-1.42 (m, 2H), 1.36 (s, 3H), 1.35-1.29 (m, 1H), 1.27 (s, 3H). $^{19}F$ NMR (377 MHz, DMSO-$d_6$) δ −62.29 (s, 3F), −99.01 to −100.95 (m, 2F). ESI-MS m/z calc. 421.1537, found 422.2 (M+1)⁺; Retention time: 4.45 minutes (LC Method AA).

Example 120: Preparation of [(6R)-6-hydroxy-12,12-dimethyl-6,15-bis(trifluoromethyl)-19-oxa-3,4,13,18-tetrazatricyclo[12.3.1.1²,⁵]nonadeca-1(17),2,4,14(18),15-pentaen-17-yl]boronic Acid (Compound 220)

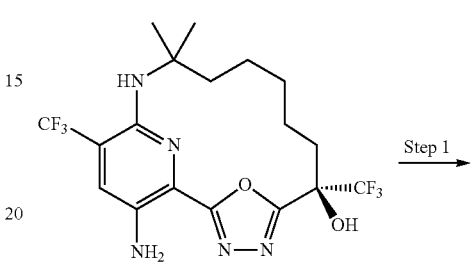

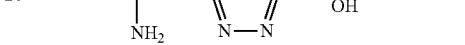

Step 1

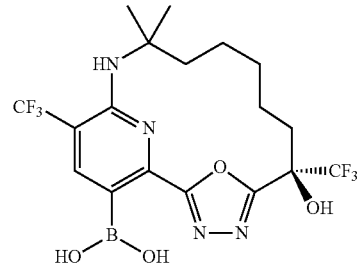

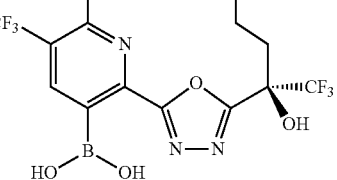

Step 1: [(6R)-6-Hydroxy-12,12-dimethyl-6,15-bis(trifluoromethyl)-19-oxa-3,4,13,18-tetrazatricyclo[12.3.1.1²,⁵]nonadeca-1(17),2,4,14(18),15-pentaen-17-yl]boronic Acid (Compound 220)

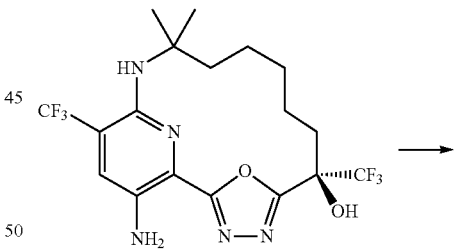

To a solution of (6R)-17-amino-12,12-dimethyl-6,15-bis(trifluoromethyl)-19-oxa-3,4,13,18-tetrazatricyclo[12.3.1.1²,⁵]nonadeca-1(18),2,4,14,16-pentaen-6-ol (225 mg, 0.4963 mmol) and bis(pinacolato)diboron (375 mg, 1.4767 mmol) in acetonitrile (6 mL) was added tert-butyl nitrite (346.80 mg, 0.4 mL, 3.3631 mmol) and the mixture was stirred at 80° C. for 15 minutes. The volatiles were removed under reduced pressure and the crude material was combined with another batch of this same reaction utilizing (6R)-17-amino-12,12-dimethyl-6,15-bis(trifluoromethyl)-19-oxa-3,4,13,18-tetrazatricyclo[12.3.1.1²,⁵]nonadeca-1(18),2,4,14,16-pentaen-6-ol (117 mg, 0.2581 mmol), bis(pinacolato)diboron (160 mg, 0.6301 mmol), tert-butyl nitrite (108.38 mg, 0.125 mL, 1.051 mmol) and acetonitrile (3 mL). The combined crude products were purified by reversed-phase chromatography ($C_{18}$ column, gradient from 5%-100% methanol in water with 0.1% formic acid modifier) during which time the pinacol boronic ester hydrolyzed to the boronic acid, affording [(6R)-6-hydroxy-12,12-dimethyl-6,15-bis(trifluoromethyl)-19-oxa-3,4,13,18-tetrazatricyclo[12.3.1.1²,⁵]nonadeca-1(17),2,4,14(18),15-pentaen-17-yl]boronic acid (37 mg, 42% purity) as a yellow solid. This material (0.0322 mmol) was combined with two other lots of the same material made from analogous syntheses (12 mg, 78% purity, 0.0194 mmol) and 17 mg, 60% purity, 0.0212 mmol) and the combined material was further purified by reversed-phase chromatography ($C_{18}$ column, gradient from 5% to 100% acetonitrile in basic water (ammonium bicarbonate/ammonium hydroxide buffer pH=10)) to afford after lyophilization, [(6R)-6-hydroxy-12,12-dimethyl-6,15-bis(trifluoromethyl)-19-oxa-3,4,13,18-tetrazatricyclo[12.3.1.1²,⁵]nonadeca-1(17),2,4,14(18),15-pentaen-17-yl]boronic acid (8.8 mg, 2% overall yield) as a light yellow solid. $^1$H NMR (400 MHz, DMSO-d6) δ 8.73 (s, 2H), 8.14 (s, 1H), 7.72 (s, 1H), 5.52 (s, 1H), 2.97-2.84 (m, 1H), 2.34-2.21 (m, 1H), 2.09-1.96 (m, 1H), 1.74-1.65 (m, 1H), 1.63-1.53 (m, 1H), 1.43 (br. s., 7H), 1.36 (s, 3H), 1.29-1.18 (m, 1H). $^{19}$F NMR (377 MHz, DMSO-d6) δ −62.02 (s, 3F), −78.34 (s, 3F). ESI-MS m/z calc. 482.156, found 481.2 (M−1)⁻; Retention time: 3.81 minutes (LC Method BB).

Example 121: Preparation of 17-amino-10,10-dimethyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 1) (Compound 221) and 17-amino-10,10-dimethyl-6,15-bis(trifluoromethyl)-19-oxa-3,4,13,18-tetrazatricyclo[12.3.1.1²,⁵]nonadeca-1(18),2,4,14,16-pentaen-6-ol (enantiomer 2) (Compound 222)

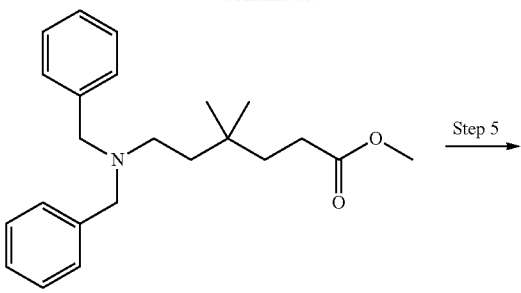

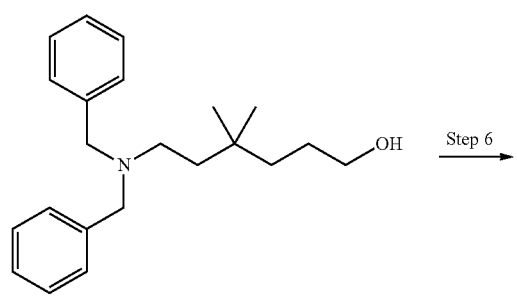

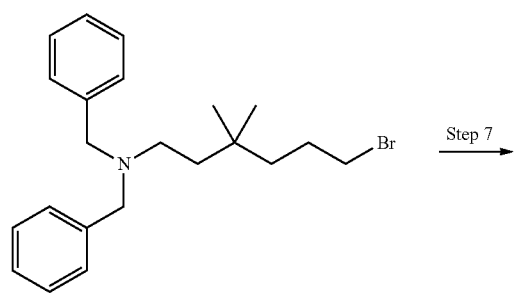

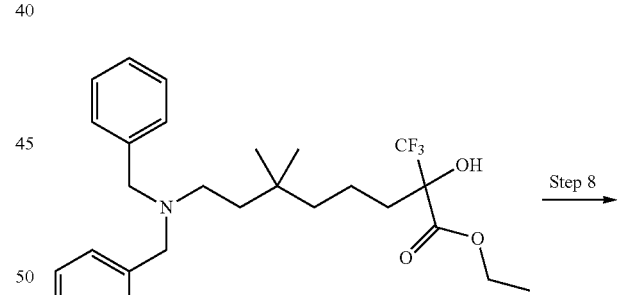

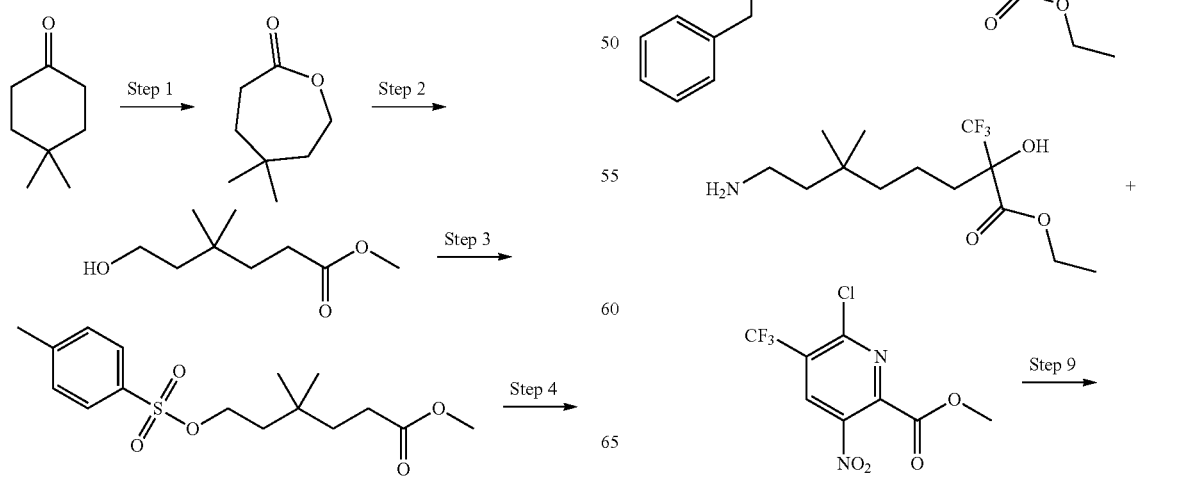

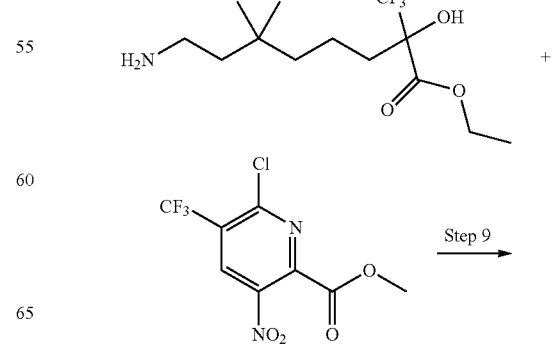

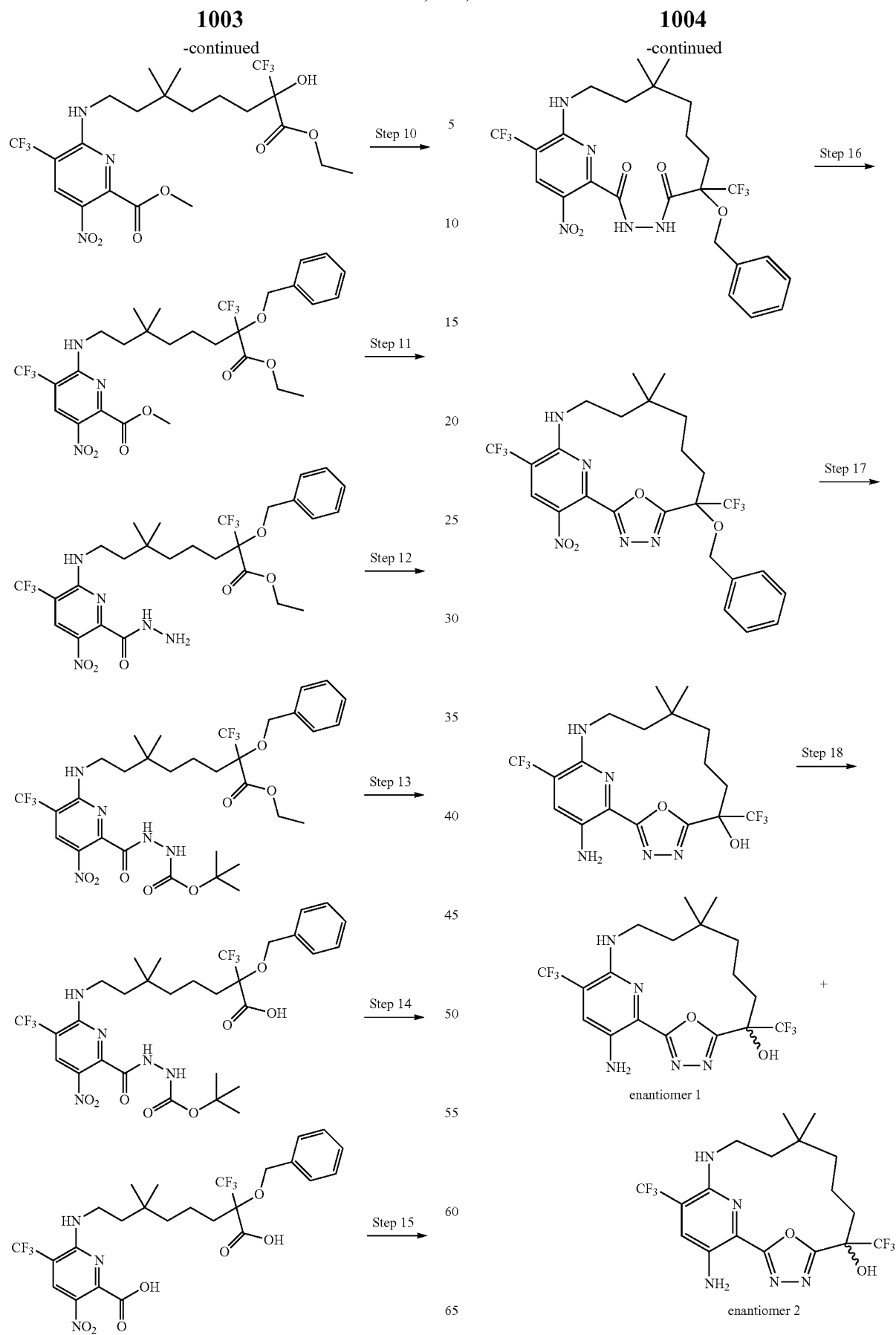

Step 1: 5,5-Dimethyloxepan-2-one

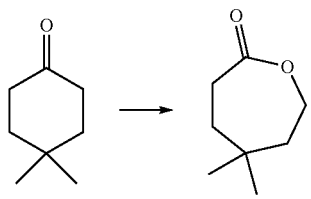

To a solution of 4,4-dimethylcyclohexanone (6.1 g, 48.338 mmol) in dichloromethane (120 mL) was added meta-chloroperoxybenzoic acid (17.5 g, 75% w/w, 76.058 mmol). The mixture was stirred in the dark at room temperature for 2 days and filtered. The cake was washed with dichloromethane-pentane (1:1, 20 mL). The filtrate was added to a mixture of sodium carbonate (6 g, 56 mmol), water (50 mL) and 10% aqueous sodium thiosulfate (50 mL) at 0° C. The resulting mixture was stirred at 0° C. for 10 min and transferred to a separatory funnel. The organic layer was washed with saturated NaHCO$_3$(50 mL) and brine (20 mL) and dried with Na$_2$SO$_4$, filtered and concentrated to give as a white solid, 5,5-dimethyloxepan-2-one (6.87 g, 100%). $^1$H NMR (400 MHz, CDCl$_3$) δ 4.22-4.18 (m, 2H), 2.62-2.58 (m, 2H), 1.67-1.63 (m, 2H), 1.58-1.54 (m, 2H), 1.02 (s, 6H). ESI-MS m/z calc. 142.0994, found 143.2 (M+1)$^+$; Retention time: 1.54 minutes. (LC Method E).

Step 2: Methyl 6-hydroxy-4,4-dimethyl-hexanoate

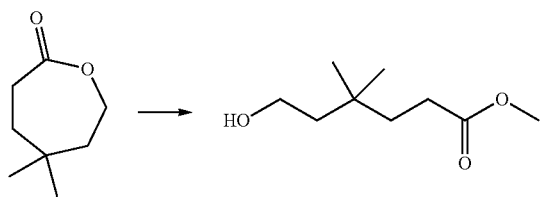

To a solution of 5,5-dimethyloxepan-2-one (6.87 g, 48.314 mmol) in MeOH (100 mL) was added sulfuric acid (0.8 g, 0.4348 mL of 95% w/w, 7.7488 mmol). The mixture was stirred at reflux for 1 h. The mixture was concentrated and the residue was taken up with diethyl ether (100 mL). The resulting solution was washed with saturated NaHCO$_3$ (50 mL), brine (20 mL) and dried with Na$_2$SO$_4$, filtered and concentrated. The residue was dissolved in dichloromethane (100 mL) and dried again with Na$_2$SO$_4$, filtered and concentrated to give 8.02 g of a colorless oil which consisted of a 5:1 mixture of the desired product, methyl 6-hydroxy-4,4-dimethyl-hexanoate, and impurity, (6-methoxy-3,3-dimethyl-6-oxo-hexyl) 6-hydroxy-4,4-dimethyl-hexanoate. Desired product, methyl 6-hydroxy-4,4-dimethyl-hexanoate, characterization: ESI-MS m/z calc. 316.225, found 317.3 (M+1)$^+$; Retention time: 1.98 minutes (LC Method E). The impure product mixture was taken directly to the ensuing step.

Step 3: Methyl 4,4-dimethyl-6-(n-tolylsulfonyloxy)hexanoate

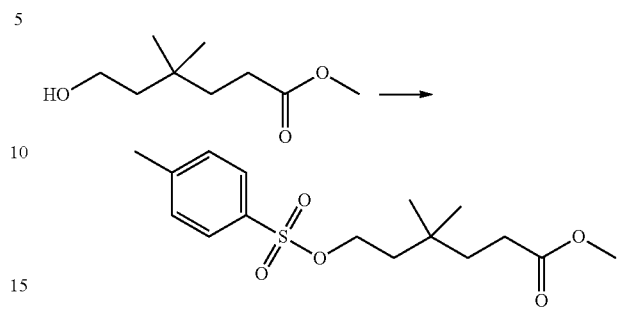

To a solution of a 5:1 mixture of 7.2 g of methyl 6-hydroxy-4,4-dimethyl-hexanoate and impurity (6-methoxy-3,3-dimethyl-6-oxo-hexyl) 6-hydroxy-4,4-dimethyl-hexanoate in dichloromethane (100 mL) at 0° C. was added Et$_3$N (10 g, 83.98 mmol), followed by tosyl chloride (10 g, 52.453 mmol). The mixture was stirred at room temperature overnight. Ice water (100 mL) was added. The mixture was extracted with dichloromethane (3×50 mL). The combined organic layers were washed with saturated NaHCO$_3$(20 mL), dried with Na$_2$SO$_4$, filtered and concentrated. The residue was purified by silica gel chromatography eluting with a gradient from 0% to 30% ethyl acetate in heptanes to afford 11.8 g of a colorless oil consisting of a 5:1 mixture of the desired product, methyl 4,4-dimethyl-6-(p-tolylsulfonyloxy)hexanoate, and impurity, 6-[4,4-dimethyl-6-(p-tolylsulfonyloxy)hexanoyl]oxy-4,4-dimethyl-hexanoate. Desired product, methyl 4,4-dimethyl-6-(p-tolylsulfonyloxy)hexanoate, characterization: ESI-MS m/z calc. 470.2338, found 471.3 (M+1)$^+$; Retention time: 2.27 minutes (LC Method E). The impure product mixture was taken directly to the ensuing step.

Step 4: Methyl 6-(dibenzylamino)-4,4-dimethyl-hexanoate

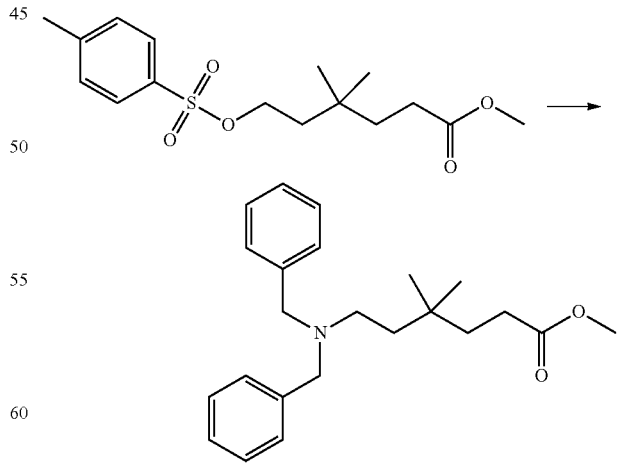

To a solution of a 5:1 mixture of 11.8 g of methyl 4,4-dimethyl-6-(p-tolylsulfonyloxy)hexanoate and impurity 6-[4,4-dimethyl-6-(p-tolylsulfonyloxy)hexanoyl]oxy-4,4-dimethyl-hexanoate in n-butanol (150 mL) was added dibenzylamine (21 g, 106.45 mmol), followed by DIEA (4 g, 5.3908 mL, 30.949 mmol). The mixture was stirred at 100° C. for 45 h, cooled and concentrated. The residue (47 g) was dissolved in ethyl acetate (300 mL) and washed with saturated NaHCO$_3$(200 mL). The organic layer was dried with Na$_2$SO$_4$, filtered and concentrated. The residue was purified by silica gel chromatography eluting with a gradient from 0% to 20% ethyl acetate in heptanes to afford as a colorless oil, methyl 6-(dibenzylamino)-4,4-dimethyl-hexanoate (7.59 g, 50% (3 steps)). ESI-MS m/z calc. 353.2355, found 354.3 (M+1)$^+$; Retention time: 1.8 minutes (LC Method E).

Step 5: 6-(Dibenzylamino)-4,4-dimethyl-hexan-1-ol

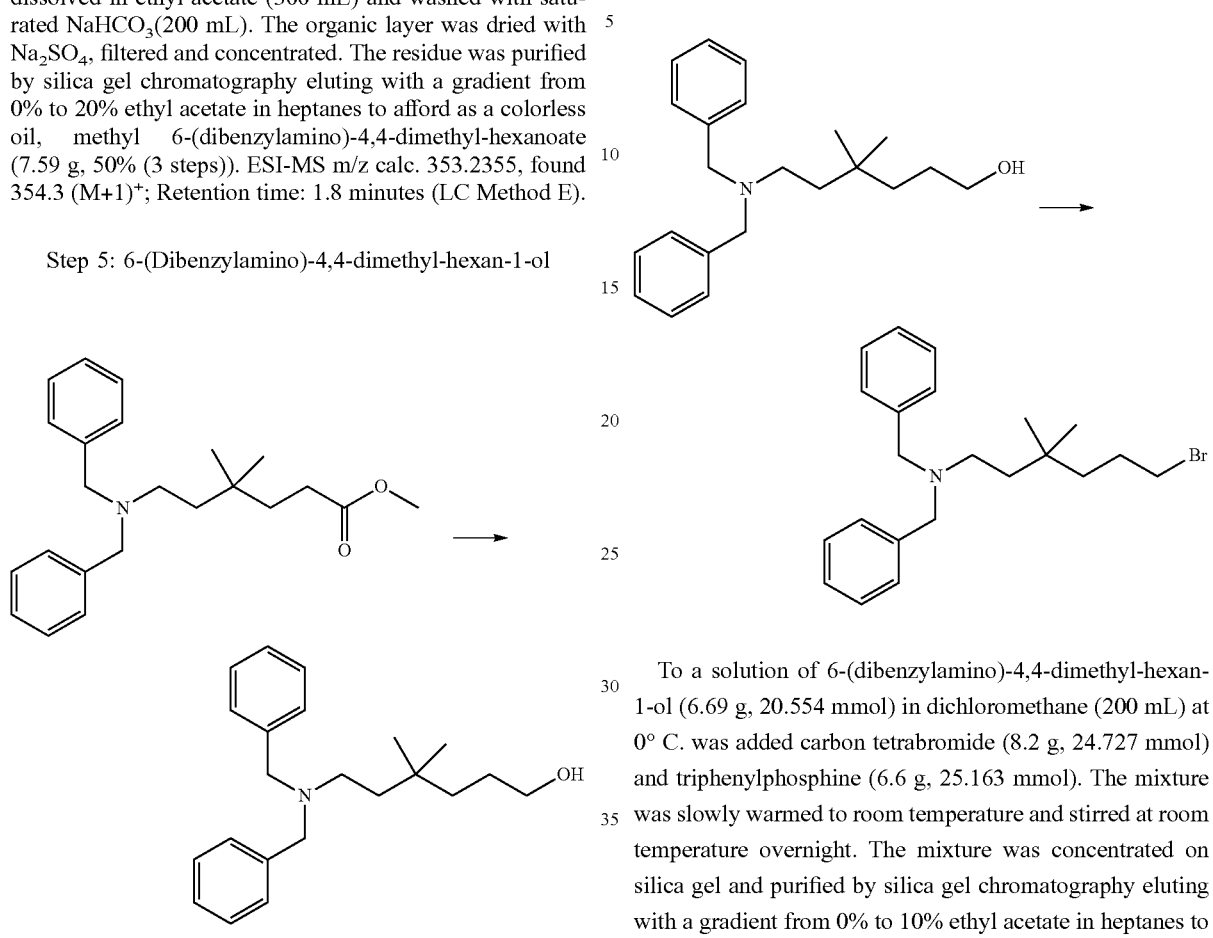

To a suspension of LiAlH$_4$ (1.13 g, 29.773 mmol) in THF (100 mL) at 0° C. was added a solution of methyl 6-(dibenzylamino)-4,4-dimethyl-hexanoate (7.59 g, 21.471 mmol) in THF (100 mL) over 10 min. The mixture was stirred at room temperature overnight and cooled to 0° C. THF (150 mL) was added, followed by a solution of water (1.2 g) in THF (10 mL) slowly, 25% aqueous NaOH (1.2 g) and water (3.6 g). The resulting mixture was stirred at room temperature for 30 min, filtered through diatomaceous earth and the filter cake was washed with THF. The filtrate was dried with Na$_2$SO$_4$, filtered and concentrated. The residue was purified by silica gel chromatography eluting with a gradient from 0% to 40% ethyl acetate in heptanes to afford as a colorless oil, 6-(dibenzylamino)-4,4-dimethyl-hexan-1-ol (6.69 g, 96%). $^1$H NMR (400 MHz, CDCl$_3$) δ 7.49-7.16 (m, 10H), 3.57 (br. s, 4H), 3.51-3.37 (m, 3H), 2.52-2.30 (m, 2H), 1.62-1.51 (m, 3H), 1.42-1.30 (m, 3H), 0.80 (s, 6H). ESI-MS m/z calc. 325.2406, found 326.3 (M+1)$^+$; Retention time: 1.72 minutes (LC Method E).

Step 6:
N,N-Dibenzyl-6-bromo-3,3-dimethyl-hexan-1-amine

To a solution of 6-(dibenzylamino)-4,4-dimethyl-hexan-1-ol (6.69 g, 20.554 mmol) in dichloromethane (200 mL) at 0° C. was added carbon tetrabromide (8.2 g, 24.727 mmol) and triphenylphosphine (6.6 g, 25.163 mmol). The mixture was slowly warmed to room temperature and stirred at room temperature overnight. The mixture was concentrated on silica gel and purified by silica gel chromatography eluting with a gradient from 0% to 10% ethyl acetate in heptanes to afford as a colorless oil, N,N-dibenzyl-6-bromo-3,3-dimethyl-hexan-1-amine (6.04 g, 76%). $^1$H NMR (400 MHz, CDCl$_3$) δ 7.42-7.28 (m, 8H), 7.26-7.19 (m, 2H), 3.57 (s, 4H), 3.25 (t, J=6.8 Hz, 2H), 2.47-2.38 (m, 2H), 1.76-1.65 (m, 2H), 1.49-1.42 (m, 2H), 1.23-1.15 (m, 2H), 0.80 (s, 6H). ESI-MS m/z calc. 387.1562, found 388.2 (M+1)$^+$; Retention time: 1.95 minutes (LC Method E).

Step 7: Ethyl 8-(dibenzylamino)-2-hydroxy-6,6-dimethyl-2-(trifluoromethyl)octanoate

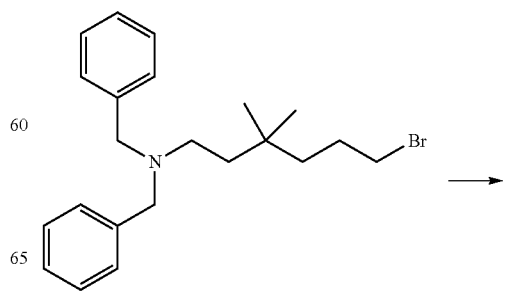

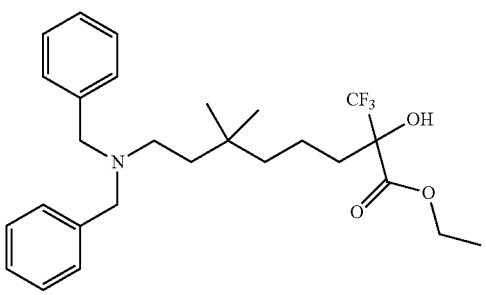

A dried 100 mL three-neck flask equipped with a reflux condenser under nitrogen was charged with magnesium (581 mg, 23.905 mmol) and iodine (185 mg, 0.7289 mmol) and the mixture was stirred neat at room temperature for 10 minutes and then heated to 40° C. A solution of N,N-dibenzyl-6-bromo-3,3-dimethyl-hexan-1-amine (4.61 g, 11.87 mmol) in diethyl ether (7 mL) was added dropwise over 8 minutes. The mixture was stirred at 40° C. for 10 minutes and then at 30° C. for 1 h. The resulting mixture was cooled to room temperature and diluted with diethyl ether (7 mL) then was added dropwise by a syringe over 15 minutes to a cooled solution of ethyl trifluoropyruvate (2 g, 11.759 mmol) in THF (45 mL) at −78° C. The mixture was stirred at −78° C. for 10 minutes. The reaction mixture was allowed to warm up slowly to room temperature over 1 h and stirred at room temperature for 1.5 h. The reaction mixture was cooled to 0° C. and quenched with saturated aqueous ammonium chloride (100 mL). The resulting mixture was extracted with ethyl acetate (3×100 mL). The combined organic layers were washed with brine (50 mL), dried over sodium sulfate, filtered and concentrated. The residue (6.5 g) was purified by silica gel chromatography eluting with a gradient from 0% to 40% ethyl acetate in heptanes to afford as a colorless oil, ethyl 8-(dibenzylamino)-2-hydroxy-6,6-dimethyl-2-(trifluoromethyl)octanoate (2.13 g, 37%). $^1$H NMR (400 MHz, CDCl$_3$) δ 7.38-7.27 (m, 8H), 7.25-7.18 (m, 2H), 4.34 (q, J=7.1 Hz, 2H), 3.76 (s, 1H), 3.60-3.49 (m, 4H), 2.39 (dd, J=79.8, 5.1 Hz, 2H), 1.93-1.81 (m, 1H), 1.80-1.69 (m, 1H), 1.47-1.37 (m, 3H), 1.32 (t, J=7.1 Hz, 3H), 1.13-1.03 (m, 2H), 1.01-0.90 (m, 1H), 0.75 (s, 6H). $^{19}$F NMR (377 MHz, CDCl$_3$) δ−78.65 (s, 3F). ESI-MS m/z calc. 479.2647, found 480.3 (M+1)$^+$; Retention time: 2.05 minutes (LC Method E).

Step 8: Ethyl 8-amino-2-hydroxy-6,6-dimethyl-2-(trifluoromethyl)octanoate

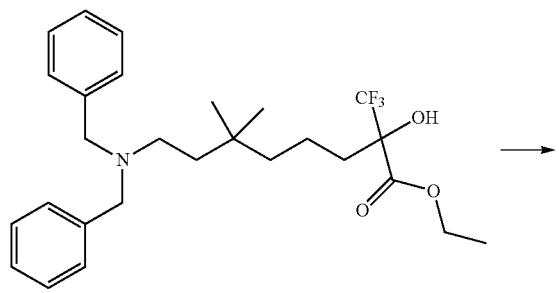

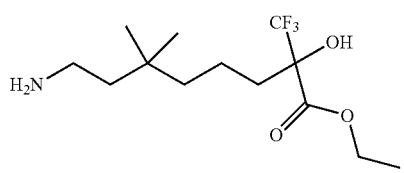

A mixture of ethyl 8-(dibenzylamino)-2-hydroxy-6,6-dimethyl-2-(trifluoromethyl)octanoate (2.13 g, 4.4414 mmol) and 20% palladium hydroxide on carbon (360 mg, 50% wet, 10% w/w, 0.2563 mmol) in EtOH (60 mL) was stirred under hydrogen (balloon) at room temperature for 24 h. More 20% palladium hydroxide on carbon (360 mg, 50% wet, 10% w/w, 0.2563 mmol) was added. The mixture was stirred under hydrogen (balloon) at room temperature for 2 days. The mixture was filtered through diatomaceous earth and washed with EtOAc. The filtrate was concentrated and co-evaporated with heptanes/EtOAc (to remove trace of EtOH) to give as a colorless oil ethyl 8-amino-2-hydroxy-6,6-dimethyl-2-(trifluoromethyl)octanoate (1.32 g, 99%). $^1$H NMR (400 MHz, CDCl$_3$) δ 4.43-4.31 (m, 2H), 2.68 (dd, J=10.3, 6.1 Hz, 2H), 2.15 (br. s, 3H), 1.99-1.90 (m, 1H), 1.87-1.76 (m, 1H), 1.55-1.42 (m, 1H), 1.34 (t, J=7.1 Hz, 3H), 1.30-1.14 (m, 4H), 1.10-0.99 (m, 1H), 0.85 (s, 6H). $^{19}$F NMR (377 MHz, CDCl$_3$) δ−78.64 (s, 3F). ESI-MS m/z calc. 299.1708, found 300.2 (M+1)$^+$; Retention time: 1.69 minutes (LC Method E).

Step 9: Methyl 6-[(7-ethoxycarbonyl-8,8,8-trifluoro-7-hydroxy-3,3-dimethyl-octyl)amino]-3-nitro-5-(trifluoromethyl)pyridine-2-carboxylate

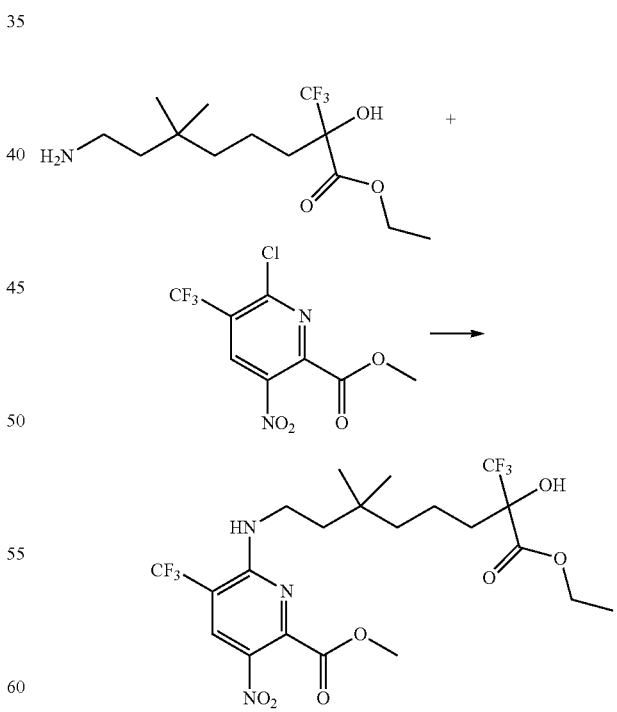

To a solution of ethyl 8-amino-2-hydroxy-6,6-dimethyl-2-(trifluoromethyl)octanoate (1.32 g, 4.4098 mmol) in acetonitrile (25 mL) were added methyl 6-chloro-3-nitro-5-(trifluoromethyl)pyridine-2-carboxylate (1.3 g, 4.5682 mmol) and DIEA (2.8 g, 3.7736 mL, 21.665 mmol). The mixture was stirred at 60 to 65° C. for 2.5 h. The mixture was cooled to room temperature and concentrated on silica gel. The residue was purified by silica gel chromatography eluting with a gradient from 0% to 20% ethyl acetate in heptanes to afford as a pale yellow solid, methyl 6-[(7-ethoxycarbonyl-8,8,8-trifluoro-7-hydroxy-3,3-dimethyl-octyl)amino]-3-nitro-5-(trifluoromethyl)pyridine-2-carboxylate (1.86 g, 77%). $^1$H NMR (400 MHz, CDCl$_3$) δ 8.47 (d, J=0.7 Hz, 1H), 5.59 (br. s, 1H), 4.37 (q, J=6.9 Hz, 2H), 4.02 (s, 3H), 3.85 (s, 1H), 3.63-3.54 (m, 2H), 2.01-1.91 (m, 1H), 1.90-1.80 (m, 1H), 1.54-1.44 (m, 2H), 1.33 (t, J=7.2 Hz, 3H), 1.31-1.18 (m, 3H), 1.13-1.01 (m, 1H), 0.92 (d, J=2.4 Hz, 6H). $^{19}$F NMR (377 MHz, CDCl$_3$) δ −64.31 (s, 3F), −78.63 (s, 3F). ESI-MS m/z calc. 547.1753, found 548.2 (M+1)$^+$; Retention time: 2.24 minutes (LC Method E).

Step 10: Methyl 6-[(7-benzyloxy-7-ethoxycarbonyl-8,8,8-trifluoro-3,3-dimethyl-octyl)amino]-3-nitro-5-(trifluoromethyl)pyridine-2-carboxylate

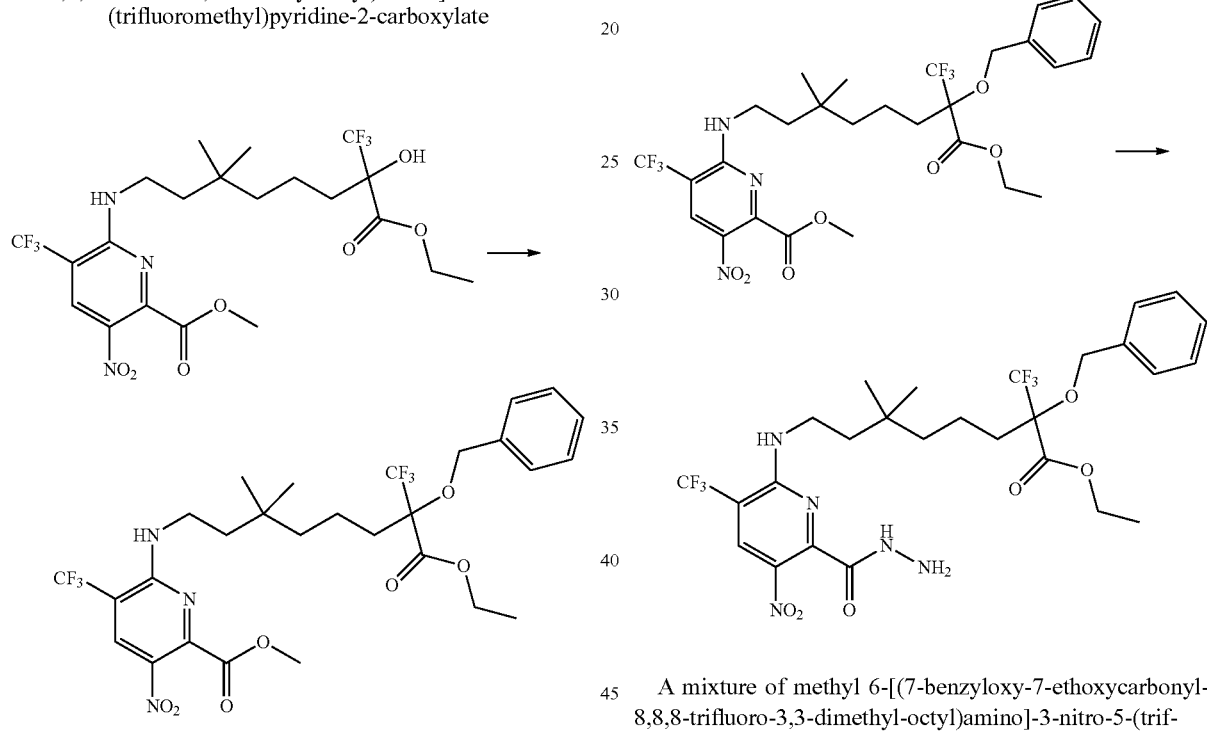

To a solution of methyl 6-[(7-ethoxycarbonyl-8,8,8-trifluoro-7-hydroxy-3,3-dimethyl-octyl)amino]-3-nitro-5-(trifluoromethyl)pyridine-2-carboxylate (1.63 g, 2.9775 mmol) in DMF (16 mL) at 0° C. was added NaH (253 mg, 60% w/w, 6.3256 mmol) portionwise. The mixture was stirred at 0° C. for 20 min. Benzyl bromide (766 mg, 4.4786 mmol) was added. The mixture was slowly warmed up to room temperature and stirred at room temperature for 3 h. The mixture was cooled to 0° C. and NH$_4$Cl (0.6 g) was added. The mixture was stirred at 0° C. for 30 min. Crushed ice (80 g) was added. The mixture was stirred until most of the ice melted. The precipitate was collected by filtration and dissolved in EtOAc (20 mL). The filtrate was extracted with tert-butylmethyl ether/heptanes (2:1, 2×80 mL). All of the organic layers (precipitate dissolved in EtOAc and the tert-butylmethyl ether/heptanes washes) were combined and dried with Na$_2$SO$_4$, filtered and concentrated. The residue was purified by silica gel chromatography eluting with a gradient from 0% to 20% ethyl acetate in heptanes to afford as a pale-yellow oil, methyl 6-[(7-benzyloxy-7-ethoxycarbonyl-8,8,8-trifluoro-3,3-dimethyl-octyl)amino]-3-nitro-5-(trifluoromethyl)pyridine-2-carboxylate (1.965 g, 95%). $^1$H NMR (400 MHz, CDCl$_3$) δ 8.46 (s, 1H), 7.44-7.27 (m, 5H), 5.56 (br. s, 1H), 4.81 (d, J=10.8 Hz, 1H), 4.64 (d, J=11.0 Hz, 1H), 4.33 (qd, J=7.1, 0.9 Hz, 2H), 4.01 (s, 3H), 3.58-3.49 (m, 2H), 2.01-1.92 (m, 2H), 1.54-1.44 (m, 4H), 1.33 (t, J=7.1 Hz, 3H), 1.25-1.18 (m, 2H), 0.90 (s, 6H). $^{19}$F NMR (377 MHz, CDCl$_3$) δ−64.31 (s, 3F), −70.52 (s, 3F). ESI-MS m/z calc. 637.2223, found 638.3 (M+1)$^+$; Retention time: 2.47 minutes (LC Method E).

Step 11: Ethyl 2-benzyloxy-8-[[6-(hydrazinecarbonyl)-5-nitro-3-(trifluoromethyl)-2-pyridyl]amino]-6,6-dimethyl-2-(trifluoromethyl)octanoate

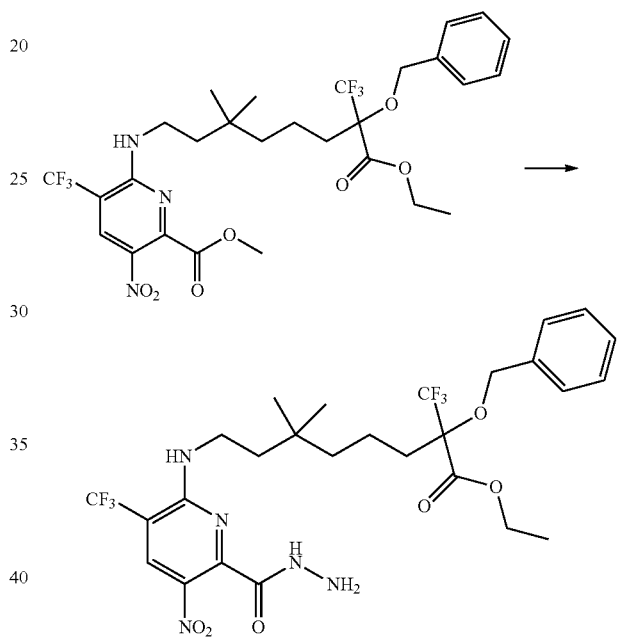

A mixture of methyl 6-[(7-benzyloxy-7-ethoxycarbonyl-8,8,8-trifluoro-3,3-dimethyl-octyl)amino]-3-nitro-5-(trifluoromethyl)pyridine-2-carboxylate (1.96 g, 2.8282 mmol) and hydrazine monohydrate (1.23 g, 24.57 mmol) in MeOH (30 mL) in a pressure tube was stirred at 80° C. overnight. The mixture was concentrated and the residue was dissolved in EtOAc and washed with water (20 mL). The organic layer was dried with Na$_2$SO$_4$, filtered and concentrated. The residue was purified by silica gel chromatography eluting with a gradient from 20% to 60% ethyl acetate in heptanes to afford as a pale-yellow solid, ethyl 2-benzyloxy-8-[[6-(hydrazinecarbonyl)-5-nitro-3-(trifluoromethyl)-2-pyridyl]amino]-6,6-dimethyl-2-(trifluoromethyl)octanoate (1.67 g, 93%). $^1$H NMR (400 MHz, CDCl$_3$) δ 8.33 (s, 1H), 7.43-7.29 (m, 5H), 5.48 (br. s, 1H), 4.82 (d, J=10.5 Hz, 1H), 4.64 (d, J=10.8 Hz, 1H), 4.38-4.29 (m, 2H), 4.11 (br. s, 2H), 3.55-3.45 (m, 2H), 2.03-1.93 (m, 2H), 1.60-1.42 (m, 4H), 1.33 (t, J=7.1 Hz, 3H), 1.28-1.20 (m, 3H), 0.92 (s, 6H). $^{19}$F NMR (377 MHz, CDCl$_3$) δ −64.28 (s, 3F), −70.40 (s, 3F). ESI-MS m/z calc. 637.2335, found 638.3 (M+1)$^+$; Retention time: 2.27 minutes (LC Method E).

1013

Step 12: Ethyl 2-benzyloxy-8-[[6-[(tert-butoxycarbonylamino)carbamoyl]-5-nitro-3-(trifluoromethyl)-2-pyridyl]amino]-6,6-dimethyl-2-(trifluoromethyl)octanoate

1014

Step 13: 2-Benzyloxy-8-[[6-[(tert-butoxycarbonylamino)carbamoyl]-5-nitro-3-(trifluoromethyl)-2-pyridyl]amino]-6,6-dimethyl-2-(trifluoromethyl)octanoic Acid

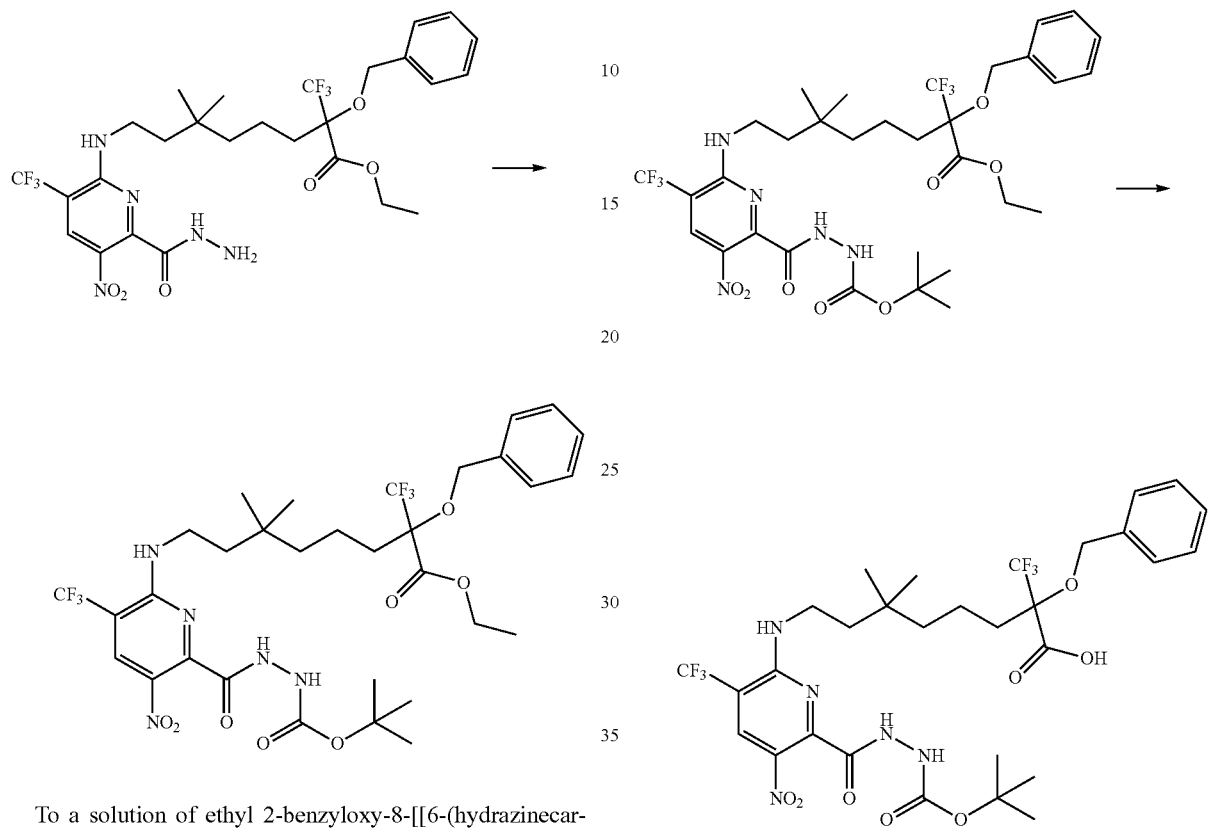

To a solution of ethyl 2-benzyloxy-8-[[6-(hydrazinecarbonyl)-5-nitro-3-(trifluoromethyl)-2-pyridyl]amino]-6,6-dimethyl-2-(trifluoromethyl)octanoate (1.67 g, 2.6193 mmol), 4-(dimethylamino)pyridine (55 mg, 0.4502 mmol) and diisopropylethylamine (1.1 g, 1.4825 mL, 8.5111 mmol) in dichloromethane (50 mL) was added di-tert-butyl dicarbonate (1.5 g, 1.5789 mL, 6.8729 mmol). The mixture was stirred at room temperature overnight then concentrated on silica gel. The residue was purified by silica gel eluting with a gradient from 0% to 30% ethyl acetate in heptanes to afford as a pale-yellow oil, ethyl 2-benzyloxy-8-[[6-[(tert-butoxycarbonylamino)carbamoyl]-5-nitro-3-(trifluoromethyl)-2-pyridyl]amino]-6,6-dimethyl-2-(trifluoromethyl)octanoate (1.21 g, 63%). $^1$H NMR (400 MHz, CDCl$_3$) δ 8.50 (s, 1H), 7.44-7.28 (m, 5H), 5.50 (br. s, 1H), 4.80 (d, J=10.8 Hz, 1H), 4.64 (d, J=10.3 Hz, 1H), 4.38-4.28 (m, 2H), 3.58-3.47 (m, 2H), 2.00-1.88 (m, 2H), 1.58 (s, 9H), 1.55-1.47 (m, 6H), 1.39-1.30 (m, 5H), 0.89 (s, 6H). $^{19}$F NMR (377 MHz, CDCl$_3$) δ −63.97 (s, 3F), −70.41−−70.51 (m, 3F). ESI-MS m/z calc. 737.2859, found 682.3 (M−55)$^+$; Retention time: 2.68 minutes (LC Method E).

To a solution of ethyl 2-benzyloxy-8-[[6-[(tert-butoxycarbonylamino)carbamoyl]-5-nitro-3-(trifluoromethyl)-2-pyridyl]amino]-6,6-dimethyl-2-(trifluoromethyl)octanoate (1 g, 1.3556 mmol) in MeOH (20 mL) was added a solution of NaOH (230 mg, 5.7504 mmol) in water (5 mL). The mixture was stirred at 45° C. for 5 h and at 43° C. for 16 h. The mixture was cooled to room temperature and concentrated under reduced pressure to remove most of the MeOH. The residue was diluted with water (10 mL) and cooled to 0° C. Aqueous HCl (1 N, 5.3 mL) was added dropwise. The resulting mixture was extracted with EtOAc (3×20 mL). The combined organic layers were dried with Na$_2$SO$_4$, filtered and concentrated under reduced pressure to give as a pale-yellow foam, 2-benzyloxy-8-[[6-[(tert-butoxycarbonylamino)carbamoyl]-5-nitro-3-(trifluoromethyl)-2-pyridyl]amino]-6,6-dimethyl-2-(trifluoromethyl)octanoic acid (914 mg, 95%) contaminated with some bis-Boc side product. ESI-MS m/z calc. 709.25464, found 654.2 (M−55)$^+$; Retention time: 4.9 minutes (LC Method AA).

1015

Step 14: 6-[(7-Benzyloxy-7-carboxy-8,8,8-trifluoro-3,3-dimethyl-octyl)amino]-3-nitro-5-(trifluoromethyl)pyridine-2-carboxylic Acid

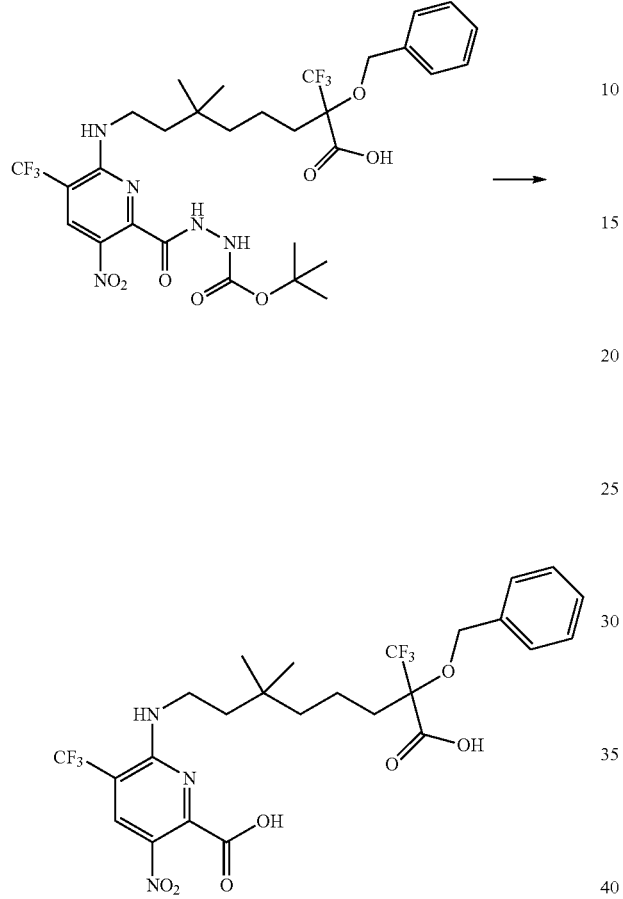

To a solution of 2-benzyloxy-8-[[6-[(tert-butoxycarbonylamino)carbamoyl]-5-nitro-3-(trifluoromethyl)-2-pyridyl]amino]-6,6-dimethyl-2-(trifluoromethyl)octanoic acid (914 mg, 1.2880 mmol) in 1,4-dioxane (5 mL) was added HCl in 1,4-dioxane (10 mL of 4 M, 40 mmol) dropwise. The mixture was stirred at room temperature overnight. The reaction mixture was concentrated under reduced pressure at 30° C. and co-evaporated with EtOAc (3×20 mL). The residue was purified by reversed-phase chromatography (gradient from 5% to 80% acetonitrile in water). The desired fractions were concentrated under reduced pressure and the residue was freeze dried to afford as a pale-yellow solid, 6-[(7-benzyloxy-7-carboxy-8,8,8-trifluoro-3,3-dimethyl-octyl)amino]-3-nitro-5-(trifluoromethyl)pyridine-2-carboxylic acid (450 mg, 57%). $^{19}$F NMR (377 MHz, DMSO-d6) δ −63.16 to −63.54 (m, 3F), −70.23 to −70.52 (m, 3F). ESI-MS m/z calc. 595.1753, found 596.3 (M+1)$^+$; Retention time: 3.2 minutes (LC Method C).

1016

Step 15: 9-Benzyloxy-5,5-dimethyl-15-nitro-9,17-bis(trifluoromethyl)-2,11,12,18-tetrazabicyclo[12.3.1]octadeca-1(17),14(18),15-triene-10,13-dione

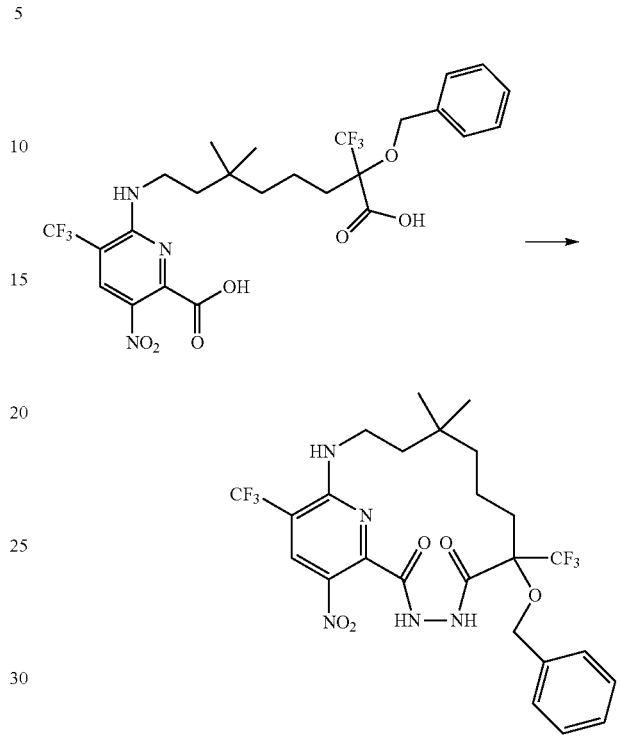

To a solution of 6-[(7-benzyloxy-7-carboxy-8,8,8-trifluoro-3,3-dimethyl-octyl)amino]-3-nitro-5-(trifluoromethyl)pyridine-2-carboxylic acid (42 mg, 0.0635 mmol) in DMF (30 mL) was added DIEA (60 mg, 0.4642 mmol), 1-hydroxy-7-azabenzotriazole in dimethylacetamide (0.16 mL of 1 M, 0.16 mmol) and (benzotriazol-1-yloxy)tris(dimethylamino)phosphonium hexafluorophosphate (80 mg, 0.1809 mmol). The mixture was stirred at 30° C. and a solution of hydrazine in THF (0.08 mL of 1 M, 0.08 mmol) diluted with DMF (5 mL) was added dropwise over a period of 16 h. After addition, the reaction mixture was stirred at 30° C. for 3 h and concentrated under reduced pressure. Purification by silica gel chromatography using a gradient from 0% to 40% ethyl acetate in heptane afforded as a pale-yellow oil, 9-benzyloxy-5,5-dimethyl-15-nitro-9,17-bis(trifluoromethyl)-2,11,12,18-tetrazabicyclo[12.3.1]octadeca-1(17),14(18),15-triene-10,13-dione (37 mg, 84%, purity=85%). $^1$H NMR (400 MHz, CDCl$_3$) δ 8.39 (br. s, 1H), 8.06 (br. s, 1H), 7.49-7.28 (m, 4H), 7.03-6.89 (m, 2H), 5.44 (br. s, 1H), 4.69-4.51 (m, 1H), 4.46-4.18 (m, 2H), 3.28-3.13 (m, 1H), 2.38-2.24 (m, 1H), 2.17-2.06 (m, 1H), 1.92-1.74 (m, 1H), 1.45-1.29 (m, 5H), 0.99 (s, 3H), 0.93 (s, 3H). $^{19}$F NMR (377 MHz, CDCl$_3$) δ −63.92 (s, 3F), −74.18 (s, 3F). ESI-MS m/z calc. 591.1916, found 592.2 (M+1)$^+$; Retention time: 4.62 minutes (LC Method AA).

1017

Step 16: 6-Benzyloxy-10,10-dimethyl-17-nitro-6,15-bis(trifluoromethyl)-19-oxa-3,4,13,18-tetrazatricyclo[12.3.1.1²,⁵]nonadeca-1(18),2,4,14,16-pentaene

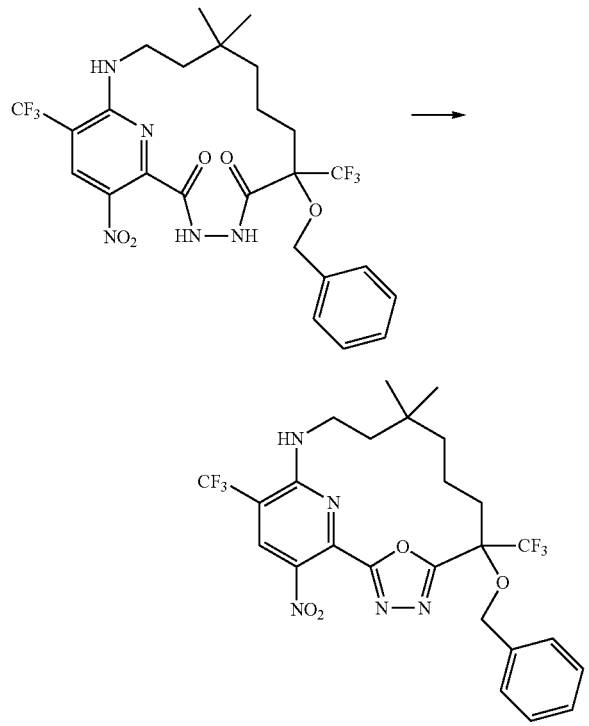

To a solution of 9-benzyloxy-5,5-dimethyl-15-nitro-9,17-bis(trifluoromethyl)-2,11,12,18-tetrazabicyclo[12.3.1]octadeca-1(17),14(18),15-triene-10,13-dione (55 mg, 0.0895 mmol) in dichloromethane (3 mL) at 0° C. was added DIEA (70 mg, 0.5416 mmol), followed by trifluoromethanesulfonic anhydride (51 mg, 0.1808 mmol) dropwise. The mixture was stirred at 0° C. for 50 min. Morpholine (150 mg) was added to quench the reaction. After stirring for 5 min at 0° C., the mixture was treated with saturated aqueous NaHCO₃ (6 mL) and extracted with dichloromethane (3×10 mL). The combined organic layers were dried with Na₂SO₄, filtered and concentrated under reduced pressure. Purification by silica gel chromatography (gradient from 0% to 30% ethyl acetate in heptane) afforded as a pale-yellow oil, 6-benzyloxy-10,10-dimethyl-17-nitro-6,15-bis(trifluoromethyl)-19-oxa-3,4,13,18-tetrazatricyclo[12.3.1.1²,⁵]nonadeca-1(18),2,4,14,16-pentaene (46 mg, 87%). ¹H NMR (400 MHz, CDCl₃) δ 8.54 (s, 1H), 7.37-7.27 (m, 5H), 5.99-5.88 (m, 1H), 5.00-4.90 (m, 2H), 3.68-3.54 (m, 1H), 3.51-3.39 (m, 1H), 2.41-2.30 (m, 1H), 2.29-2.18 (m, 1H), 1.70-1.59 (m, 1H), 1.51-1.31 (m, 5H, overlapped with heptanes), 0.89 (s, 3H, overlapped with heptanes), 0.87 (s, 3H, overlapped with heptanes). ¹⁹F NMR (377 MHz, CDCl₃) δ −64.16 (s, 3F), −73.53 (s, 3F). ESI-MS m/z calc. 573.1811, found 574.2 (M+1)⁺; Retention time: 5.19 minutes (LC Method AA).

1018

Step 17: 17-Amino-10,10-dimethyl-6,15-bis(trifluoromethyl)-19-oxa-3,4,13,18-tetrazatricyclo[12.3.1.1²,⁵]nonadeca-1(18),2,4,14,16-pentaen-6-ol

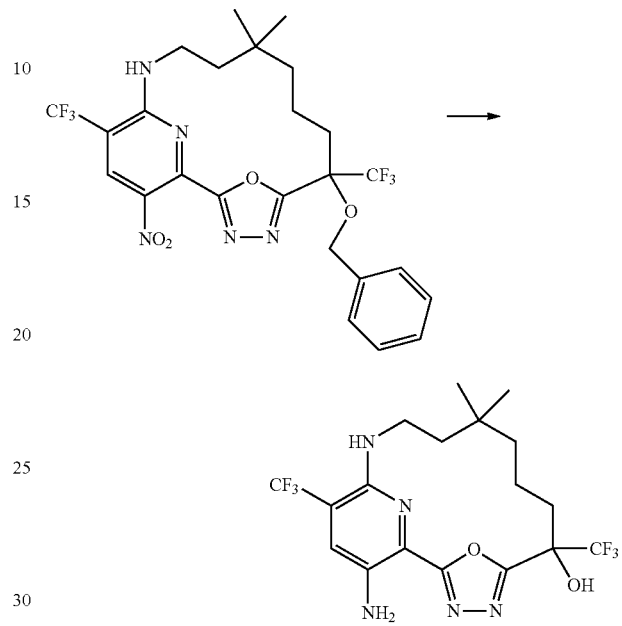

To a solution of 6-benzyloxy-10,10-dimethyl-17-nitro-6,15-bis(trifluoromethyl)-19-oxa-3,4,13,18-tetrazatricyclo[12.3.1.1²,⁵]nonadeca-1(18),2,4,14,16-pentaene (46 mg, 0.0779 mmol) in MeOH (5 mL) was added 10% palladium on carbon (46 mg, 50% wet, 5% w/w, 0.0216 mmol). Air in the flask was replaced by nitrogen through vacuum 3 times. Nitrogen in the flask was replaced by hydrogen through vacuum 6 times. Ammonia in MeOH (0.38 mL of 2 M, 0.76 mmol) was added by a syringe. The reaction mixture was stirred under hydrogen atmosphere (balloon) at room temperature overnight. The mixture was filtered through Celite, washing with EtOAc, and the filtrate was concentrated in vacuo. The residue was dissolved in MeOH (5 mL). 10% Pd/C (60 mg, 50% wet, 5 w/w, 0.0282 mmol) was added. Air in the flask was replaced by nitrogen through vacuum 3 times. Nitrogen in the flask was replaced by hydrogen through vacuum 6 times. Ammonia in MeOH (0.38 mL of 2 M, 0.76 mmol) was added by a syringe. The reaction mixture was stirred under hydrogen atmosphere (balloon) at room temperature overnight. The mixture was filtered through Celite, washing with EtOAc, and the filtrate was concentrated in vacuo. Purification by silica gel chromatography (gradient from 10% to 40% EtOAc in heptanes) afforded as a yellow solid, 17-amino-10,10-dimethyl-6,15-bis(trifluoromethyl)-19-oxa-3,4,13,18-tetrazatricyclo[12.3.1.1²,⁵]nonadeca-1(18),2,4,14,16-pentaen-6-ol (25 mg, 71%). NMR (400 MHz, CDCl₃) δ 7.32 (s, 1H), 4.82 (br. s, 1H), 3.77 (br. s, 1H), 3.56 (td, J=12.8, 4.2 Hz, 1H), 3.33 (td, J=12.9, 4.5 Hz, 1H), 2.33-2.16 (m, 2H), 1.88-1.61 (m, 3H), 1.59-1.41 (m, 3H), 1.33-1.14 (m, 2H), 0.92 (s, 3H), 0.87 (s, 3H). ¹⁹F NMR (377 MHz, CDCl₃) δ −64.09 (s, 3F), −79.37 (s, 3F). ESI-MS m/z calc. 453.1599, found 454.2 (M+1)⁺; Retention time: 4.67 minutes (LC Method AA).

Step 18: 17-Amino-10,10-dimethyl-6,15-bis(trifluoromethyl)-19-oxa-3,4,13,18-tetrazatricyclo[12.3.1.1².⁵]nonadeca-1(18),2,4,14,16-pentaen-6-ol (enantiomer 1) (Compound 221) and 17-amino-10,10-dimethyl-6,15-bis(trifluoromethyl)-19-oxa-3,4,13,18-tetrazatricyclo[12.3.1.1².⁵]nonadeca-1(18),2,4,14,16-pentaen-6-ol (enantiomer 2) (Compound 222)

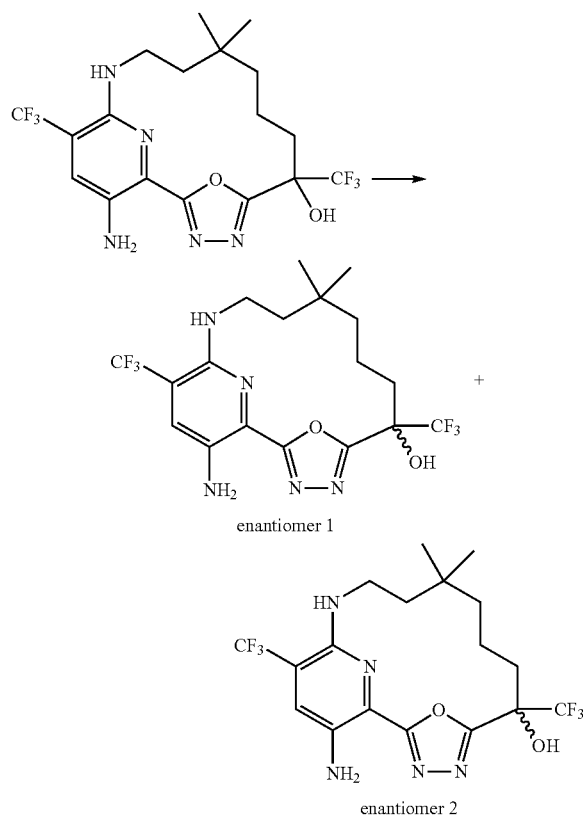

enantiomer 1 enantiomer 2

Racemic 17-amino-10,10-dimethyl-6,15-bis(trifluoromethyl)-19-oxa-3,4,13,18-tetrazatricyclo[12.3.1.12,5]nonadeca-1(18),2,4,14,16-pentaen-6-ol (41 mg, 0.0905 mmol) was purified by SFC using the following conditions: Phenomenex Lux 5 μm, Cellulose 4 column (250×21.2 mm); 9.6 mg/injection; Eluant: 10% MeOH, 90% $CO_2$; Flow rate: 75 mL/min; Concentration: 13.7 mg/mL in methanol (no modifier); Injection volume: 700 μL; Outlet pressure: 100 bar; Wavelength: 220 nm; Temperature: 40° C.

The fractions containing the first eluting compound from the chiral SFC separation were concentrated under reduced pressure. The residue was purified again by silica gel chromatography (gradient from 0% to 40% EtOAc in heptanes) and freeze dried to afford as a yellow solid, 17-amino-10,10-dimethyl-6,15-bis(trifluoromethyl)-19-oxa-3,4,13,18-tetrazatricyclo[12.3.1.12,5]nonadeca-1(18),2,4,14,16-pentaen-6-ol (enantiomer 1) (13 mg, 32%, 99.9% ee). $^1$H NMR (400 MHz, DMSO-d6) δ 7.57 (s, 1H), 7.55 (s, 1H), 6.18 (t, J=5.3 Hz, 1H), 5.89-5.79 (m, 2H), 3.48-3.35 (m, 1H), 3.28-3.15 (m, 1H), 2.24-2.12 (m, 1H), 2.11-2.00 (m, 1H), 1.77-1.57 (m, 3H), 1.55-1.44 (m, 1H), 1.43-1.26 (m, 2H), 0.87 (s, 3H), 0.83 (s, 3H). $^{19}$F NMR (377 MHz, DMSO-d6) δ −62.94 (s, 3F), −78.03 (s, 3F). ESI-MS m/z calc. 453.15994, found 454.2 (M+1)$^+$; Retention time: 4.68 minutes (LC Method AA).

The fractions containing the second eluting compound from the chiral SFC separation were concentrated under reduced pressure. The residue was purified again by silica gel chromatography (gradient from 0% to 40% EtOAc in heptanes) and freeze dried to afford as a yellow solid, 17-amino-10,10-dimethyl-6,15-bis(trifluoromethyl)-19-oxa-3,4,13,18-tetrazatricyclo[12.3.1.12,5]nonadeca-1(18),2,4,14,16-pentaen-6-ol (enantiomer 2) (18 mg, 44%, 99.9% ee). $^1$H NMR (400 MHz, DMSO-d6) δ 7.57 (s, 1H), 7.55 (s, 1H), 6.18 (t, J=5.1 Hz, 1H), 5.91-5.76 (m, 2H), 3.47-3.35 (m, 1H), 3.28-3.16 (m, 1H), 2.24-2.12 (m, 1H), 2.11-2.00 (m, 1H), 1.77-1.57 (m, 3H), 1.54-1.44 (m, 1H), 1.43-1.26 (m, 2H), 0.87 (s, 3H), 0.83 (s, 3H). $^{19}$F NMR (377 MHz, DMSO-d6) δ −62.94 (s, 3F), −78.03 (s, 3F). ESI-MS m/z calc. 453.15994, found 454.2 (M+1)$^+$; Retention time: 4.68 minutes (LC Method AA).

Example 122: Bioactivity Assay

Ussing Chamber Assay of CFTR-Mediated Short-Circuit Currents

Ussing chamber experiments were performed using human bronchial epithelial (HBE) cells derived from CF subjects heterozygous for F508del and a minimal function CFTR mutation (F508del/MF-HBE) and cultured as previously described (Neuberger T, Burton B, Clark H, Van Goor F Methods Mol Biol 2011:741:39-54). After four days the apical media was removed, and the cells were grown at an air liquid interface for >14 days prior to use. This resulted in a monolayer of fully differentiated columnar cells that were ciliated, features that are characteristic of human bronchial airway epithelia.

To isolate the CFTR-mediated short-circuit ($I_{SC}$) current, F508del/MF-HBE grown on Costar® Snapwell™ cell culture inserts were mounted in an Ussing chamber and the transepithelial $I_{SC}$ was measured under voltage-clamp recording conditions ($V_{hold}$=0 mV) at 37° C. The basolateral solution contained (in mM) 145 NaCl, 0.83 $K_2HPO_4$, 3.3 $KH_2PO_4$, 1.2 $MgCl_2$, 1.2 $CaCl_2$), 10 Glucose, 10 HEPES (pH adjusted to 7.4 with NaOH) and the apical solution contained (in mM) 145 NaGluconate, 1.2 $MgCl_2$, 1.2 $CaCl_2$), 10 glucose, 10 HEPES (pH adjusted to 7.4 with NaOH) and 30 μM amiloride to block the epithelial sodium channel. Forskolin (20 μM) was added to the apical surface to activate CFTR, followed by apical addition of a CFTR inhibitor cocktail consisting of BPO, GlyH-101 and CFTR inhibitor 172 (each at 20 μM final assay concentration) to specifically isolate CFTR currents. The CFTR-mediated $I_{SC}$ (μA/cm$^2$) for each condition was determined from the peak forskolin response to the steady-state current following inhibition.

Identification of Potentiator Compounds

The activity of the CFTR potentiator compounds on the CFTR-mediated $I_{SC}$ was determined in Ussing chamber studies as described above. The F508del/MF-HBE cell cultures were incubated with the potentiator compounds at a range of concentrations in combination with 10 μM (14S)-8-[3-(2-{dispiro[2.0.2.1]heptan-7-yl}ethoxy)-1H-pyrazol-1-yl]-12,12-dimethyl-2λ$^6$-thia-3,9,11,18,23-pentaazatetracyclo [17.3.1.1¹¹,¹⁴.0⁵,¹⁰]tetracosa-1(22),5,7,9,19(23),20-hexaene-2,2,4-trione for 18-24 hours at 37° C. and in the presence of 20% human serum. The concentration of potentiator compounds and (14S)-8-[3-(2-{dispiro[2.0.2.1]heptan-7-yl}ethoxy)-1H-pyrazol-1-yl]-12,12-dimethyl-2λ$^6$-thia-3,9,11,18,23-pentaazatetracyclo [17.3.1.1¹¹,¹⁴.0⁵,¹⁰] tetracosa-1(22),5,7,9,19(23),20-hexaene-2,2,4-trione used during the 18-24 hours incubations was kept constant throughout the Ussing chamber measurement of the CFTR-mediated $I_{SC}$ to ensure compounds were present throughout the entire experiment. The efficacy and potency of the putative F508del potentiators was compared to that of the known Vertex potentiator, ivacaftor (N-[2,4-bis(1,1-dimethylethyl)-5-hydroxyphenyl]-1,4-dihydro-4-oxoquinoline-3-carboxamide).

The following table represents CFTR modulating activity for representative compounds of the invention generated using the assay described in this example ($EC_{50}$: +++ is <500 nM; ++ is 500 nM-1 µM; + is >1 µM; and ND is "not determined in this assay").

TABLE 10

| Bioactivity | | |
|---|---|---|
| Compound No. | Structure | EC50 |
| 1 | (structure) | ND |
| 2 | (structure) | ND |
| 3 | (structure) | ND |
| 4 | (structure) | +++ |

TABLE 10-continued

| Bioactivity | | |
|---|---|---|
| Compound No. | Structure | EC50 |
| 5 | (structure) | + |
| 6 | (structure) | ++ |
| 7 | (structure) | +++ |
| 8 | (structure) | +++ |
| 9 | (structure) | +++ |

TABLE 10-continued

| Compound No. | Structure | EC50 |
|---|---|---|
| 10 | | + |
| 11 | | + |
| 12 | | ND |
| 13 | | +++ |
| 14 | | +++ |
| 15 | 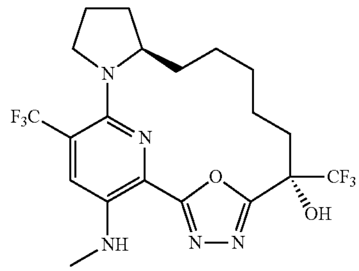 | + |
| 16 | 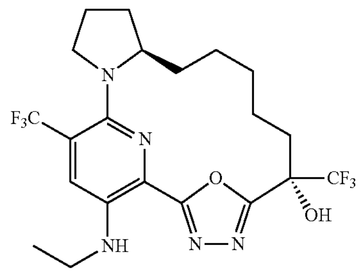 [SMILES: CCNc1cc(C(F)(F)F)c2nc1C1=NN=C(O1)[C@](O)(C(F)(F)F)CCCCC[C@@H]1CCCN21] | + |
| 17 | 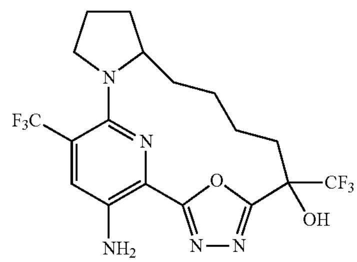 [SMILES: Nc1cc(C(F)(F)F)c2nc1-c1nnc(o1)C(O)(C(F)(F)F)CCCCC1CCCN21] | +++ |
| 18 | 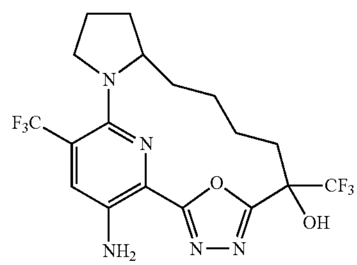 [SMILES: Nc1cc(C(F)(F)F)c2nc1-c1nnc(o1)C(O)(C(F)(F)F)CCCCC1CCCN21] | +++ |
| 19 | 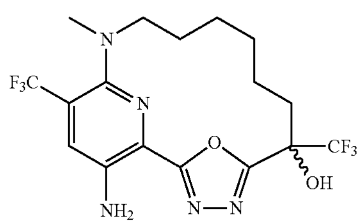 [SMILES: CN1CCCCCCC(O)(C(F)(F)F)C2=NN=C(O2)c2nc1c(C(F)(F)F)cc2N] | +++ |
| 20 | 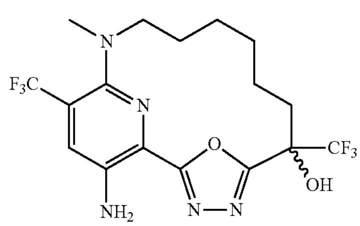 [SMILES: CN1CCCCCCC(O)(C(F)(F)F)C2=NN=C(O2)c2nc1c(C(F)(F)F)cc2N] | ++ |

TABLE 10-continued

| Compound No. | Structure | EC50 |
|---|---|---|
| 21 | | +++ |
| 22 | | ND |
| 23 | | +++ |
| 24 | | +++ |
| 25 | | +++ |
| 26 | | + |
| 27 | | ND |
| 28 | | ND |
| 29 | | +++ |
| 30 | | ND |

TABLE 10-continued

| Compound No. | Structure | EC50 |
|---|---|---|
| 31 | | +++ |
| 32 | | +++ |
| 33 | | + |
| 34 | | +++ |
| 35 | | + |
| 36 | | +++ |
| 37 | | +++ |
| 38 | | + |
| 39 | | +++ |
| 40 | | ++ |

TABLE 10-continued

Bioactivity

| Compound No. | Structure | EC50 |
|---|---|---|
| 41 | 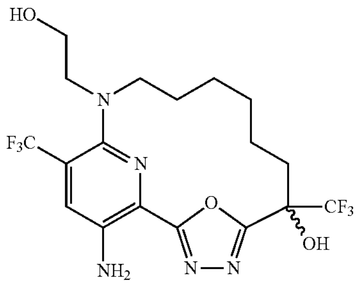 [SMILES: Nc1cc(C(F)(F)F)c2nc1C1=NN=C(O1)C(O)(C(F)(F)F)CCCCCCN2CCO] | +++ |
| 42 | 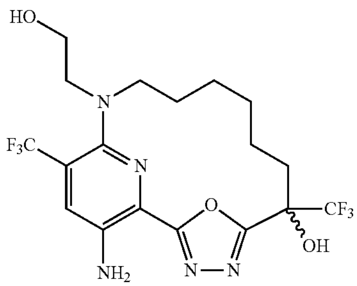 [SMILES: Nc1cc(C(F)(F)F)c2nc1C1=NN=C(O1)C(O)(C(F)(F)F)CCCCCCN2CCO] | ND |
| 43 | 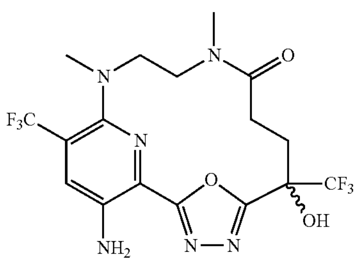 [SMILES: CN1CCN(C)c2nc(c(N)cc2C(F)(F)F)C2=NN=C(O2)C(O)(C(F)(F)F)CCC1=O] | ND |
| 44 | 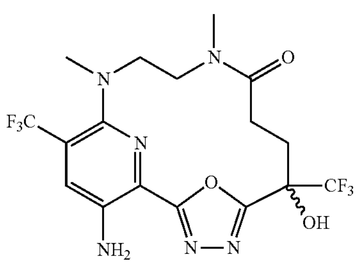 [SMILES: CN1CCN(C)c2nc(c(N)cc2C(F)(F)F)C2=NN=C(O2)C(O)(C(F)(F)F)CCC1=O] | ++ |
| 45 | 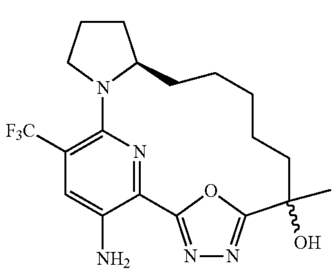 [SMILES: CC1(O)CCCCC[C@@H]2CCCN2c2nc(c(N)cc2C(F)(F)F)-c2nnc1o2] | +++ |
| 46 | | +++ |
| 47 | | ND |
| 48 | | +++ |
| 49 | | ND |
| 50 | | ND |

TABLE 10-continued

| Compound No. | Structure | Bioactivity EC50 |
|---|---|---|
| 51 | 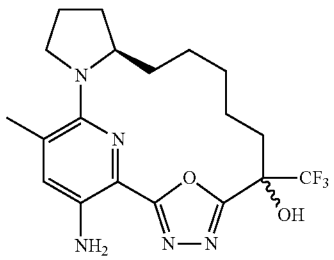 [SMILES: Cc1cc(N)c2nc1N1CCC[C@H]1CCCCCC(O)(C(F)(F)F)c1nnc-2o1] | +++ |
| 52 | 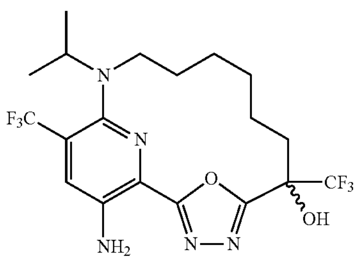 [SMILES: CC(C)N1CCCCCCC(O)(C(F)(F)F)C2=NN=C(O2)c2nc1c(C(F)(F)F)cc2N] | +++ |
| 53 | 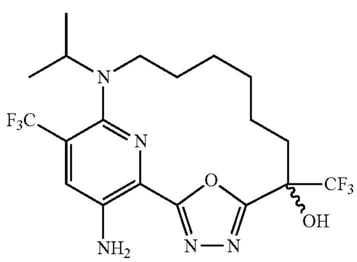 [SMILES: CC(C)N1CCCCCCC(O)(C(F)(F)F)C2=NN=C(O2)c2nc1c(C(F)(F)F)cc2N] | + |
| 54 | 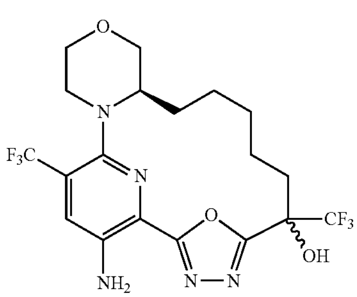 [SMILES: Nc1cc(C(F)(F)F)c2nc1-c1nnc(o1)C(O)(C(F)(F)F)CCCCC[C@@H]1COCCN21] | +++ |
| 55 | 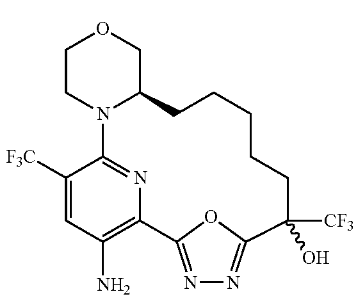 [SMILES: Nc1cc(C(F)(F)F)c2nc1-c1nnc(o1)C(O)(C(F)(F)F)CCCCC[C@@H]1COCCN21] | + |
| 56 | 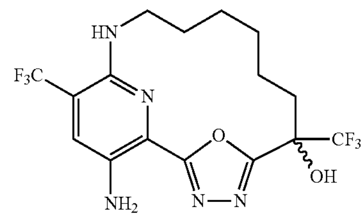 | +++ |
| 57 | 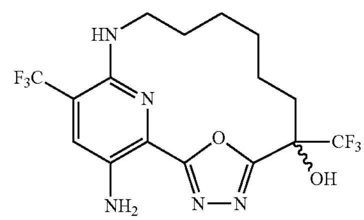 | ND |
| 58 | 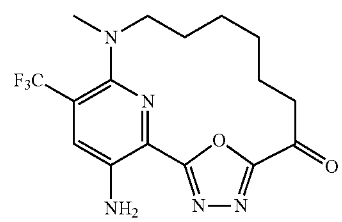 | +++ |
| 59 | 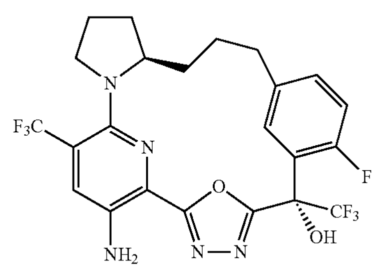 [SMILES: Nc1cc(C(F)(F)F)c2nc1-c1nnc(o1)[C@](O)(C(F)(F)F)c1cc(ccc1F)CCC[C@@H]1CCCN21] | +++ |
| 60 | 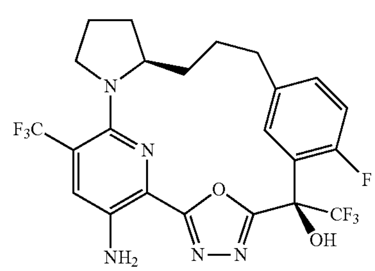 [SMILES: Nc1cc(C(F)(F)F)c2nc1-c1nnc(o1)[C@@](O)(C(F)(F)F)c1cc(ccc1F)CCC[C@@H]1CCCN21] | +++ |
| 61 | 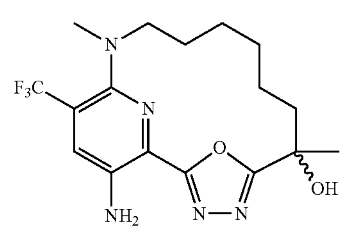 [SMILES: CN1CCCCCCC(C)(O)C2=NN=C(O2)c2nc1c(C(F)(F)F)cc2N] | +++ |

TABLE 10-continued

Bioactivity

| Compound No. | Structure | EC50 |
|---|---|---|
| 62 | | +++ |
| 63 | | +++ |
| 64 | | ND |
| 65 | | +++ |
| 66 | | +++ |
| 67 | | ND |
| 68 | | ND |
| 69 | | ND |
| 70 | | +++ |
| 71 | | +++ |

TABLE 10-continued

| Compound No. | Structure | EC50 |
|---|---|---|
| 72 | (structure) | + |
| 73 | (structure) | +++ |
| 74 | (structure) | ND |
| 75 | (structure) | +++ |
| 76 | (structure) | +++ |
| 77 | (structure) | + |
| 78 | (structure) | +++ |
| 79 | (structure) | + |
| 80 | (structure) | +++ |
| 81 | (structure) | + |
| 82 | (structure) | +++ |
| 83 | (structure) | ++ |

TABLE 10-continued

Bioactivity

| Compound No. | Structure | EC50 |
|---|---|---|
| 84 | 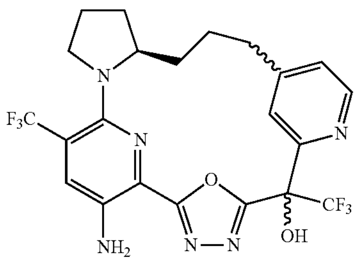 [SMILES: Nc1cc(C(F)(F)F)c2nc1-c1nnc(o1)C(O)(C(F)(F)F)c1cc(ccn1)CCC[C@@H]1CCCN21] | +++ |
| 85 | 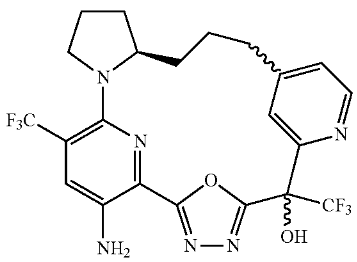 [SMILES: Nc1cc(C(F)(F)F)c2nc1-c1nnc(o1)C(O)(C(F)(F)F)c1cc(ccn1)CCC[C@@H]1CCCN21] | + |
| 86 | 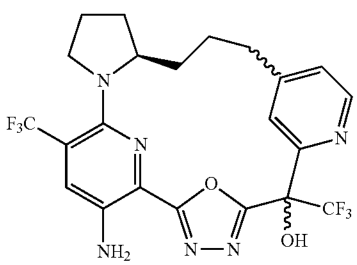 | + |
| 87 | 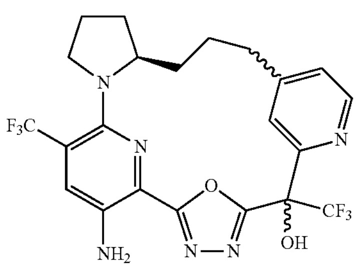 [SMILES: Nc1cc(C(F)(F)F)c2nc1-c1nnc(o1)C(O)(C(F)(F)F)c1cc(ccn1)CCC[C@@H]1CCCN21] | +++ |
| 88 | 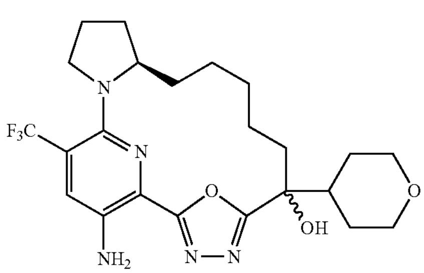 [SMILES: Nc1cc(C(F)(F)F)c2nc1-c1nnc(o1)C(O)(C1CCOCC1)CCCCC[C@@H]1CCCN21] | +++ |
| 89 | | + |
| 90 | | +++ |
| 91 | | + |
| 92 | | + |
| 93 | | +++ |

TABLE 10-continued

| Compound No. | Structure | EC50 |
|---|---|---|
| 94 | 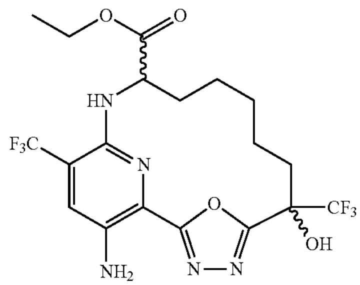 [SMILES: CCOC(=O)C1CCCCCC(O)(C(F)(F)F)C2=NN=C(O2)c2nc(c(C(F)(F)F)cc2N)N1] | +++ |
| 95 | 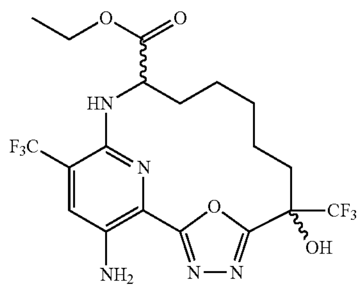 [SMILES: CCOC(=O)C1CCCCCC(O)(C(F)(F)F)C2=NN=C(O2)c2nc(c(C(F)(F)F)cc2N)N1] | +++ |
| 96 | 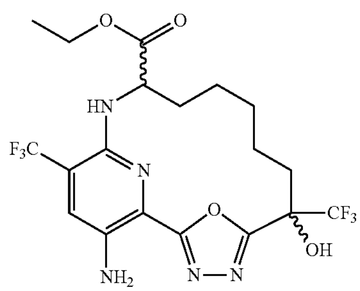 [SMILES: CCOC(=O)C1CCCCCC(O)(C(F)(F)F)C2=NN=C(O2)c2nc(c(C(F)(F)F)cc2N)N1] | ND |
| 97 | 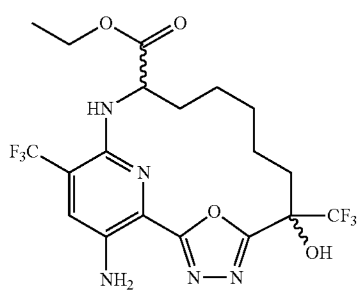 [SMILES: CCOC(=O)C1CCCCCC(O)(C(F)(F)F)C2=NN=C(O2)c2nc(c(C(F)(F)F)cc2N)N1] | + |
| 98 | 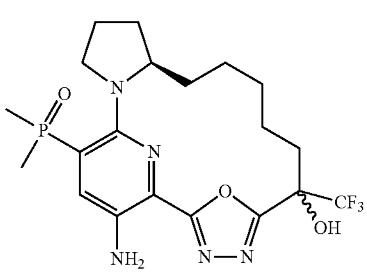 [SMILES: CP(C)(=O)c1cc(N)c2nc1N1CCC[C@H]1CCCCCC(O)(C(F)(F)F)c1nnc-2o1] | + |
| 99 | 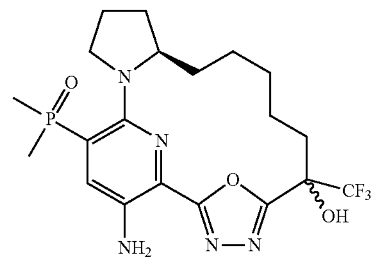 [SMILES: CP(C)(=O)c1cc(N)c2nc1N1CCC[C@H]1CCCCCC(O)(C(F)(F)F)c1nnc-2o1] | + |
| 100 | 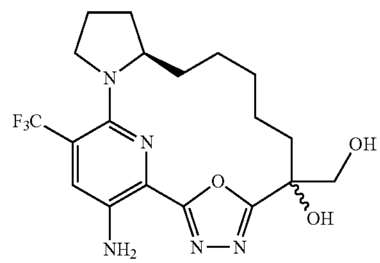 [SMILES: Nc1cc(C(F)(F)F)c2nc1-c1nnc(o1)C(O)(CO)CCCCC[C@@H]1CCCN21] | ++ |
| 101 | 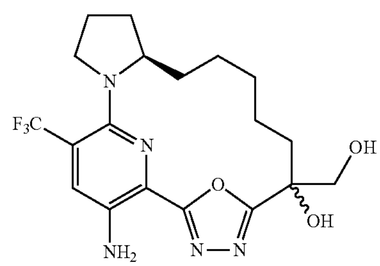 [SMILES: Nc1cc(C(F)(F)F)c2nc1-c1nnc(o1)C(O)(CO)CCCCC[C@@H]1CCCN21] | +++ |
| 102 | 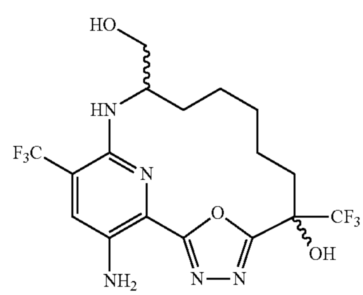 [SMILES: Nc1cc(C(F)(F)F)c2nc1C1=NN=C(O1)C(O)(C(F)(F)F)CCCCCC(CO)N2] | +++ |
| 103 | 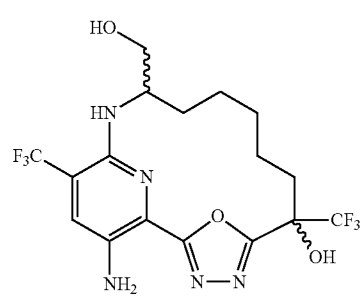 [SMILES: Nc1cc(C(F)(F)F)c2nc1C1=NN=C(O1)C(O)(C(F)(F)F)CCCCCC(CO)N2] | +++ |

TABLE 10-continued

| Compound No. | Structure | Bioactivity EC50 |
|---|---|---|
| 104 | 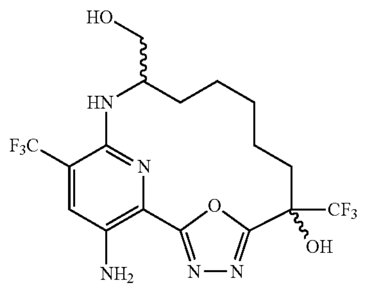 [SMILES: Nc1cc(C(F)(F)F)c2nc1C1=NN=C(O1)C(O)(C(F)(F)F)CCCCCC(CO)N2] | +++ |
| 105 | 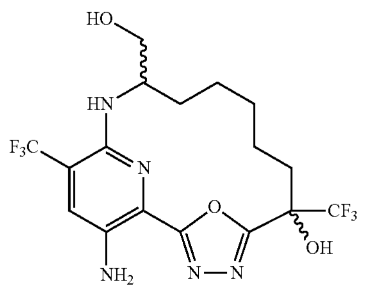 [SMILES: Nc1cc(C(F)(F)F)c2nc1C1=NN=C(O1)C(O)(C(F)(F)F)CCCCCC(CO)N2] | + |
| 106 | 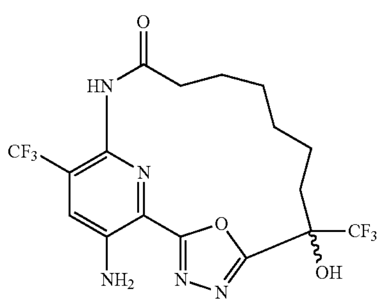 [SMILES: Nc1cc(C(F)(F)F)c2nc1C1=NN=C(O1)C(O)(C(F)(F)F)CCCCCCC(=O)N2] | +++ |
| 107 | 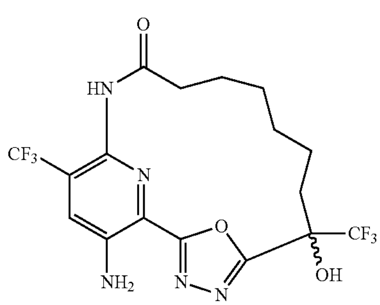 [SMILES: Nc1cc(C(F)(F)F)c2nc1C1=NN=C(O1)C(O)(C(F)(F)F)CCCCCCC(=O)N2] | + |
| 108 | 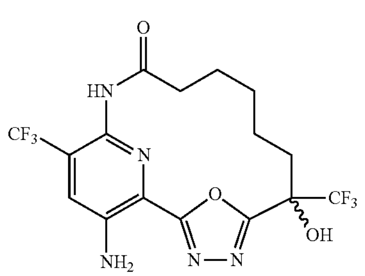 [SMILES: Nc1cc(C(F)(F)F)c2nc1C1=NN=C(O1)C(O)(C(F)(F)F)CCCCCC(=O)N2] | +++ |
| 109 | | + |
| 110 | | +++ |
| 111 | | + |
| 112 | | ++ |
| 113 | | + |

TABLE 10-continued

| Compound No. | Structure | EC50 |
|---|---|---|
| 114 | | +++ |
| 115 | | + |
| 116 | | +++ |
| 117 | | + |
| 118 | | + |
| 119 | | +++ |
| 120 | | +++ |
| 121 | | ND |
| 122 | | + |

TABLE 10-continued

| Compound No. | Structure | EC50 |
|---|---|---|
| 123 | 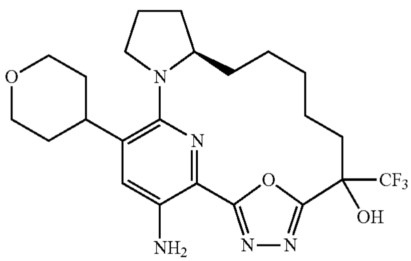 [SMILES: Nc1cc(C2CCOCC2)c2nc1-c1nnc(o1)C(O)(C(F)(F)F)CCCCC[C@@H]1CCCN21] | + |
| 124 | 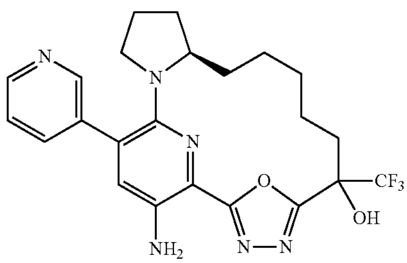 [SMILES: Nc1cc(-c2cccnc2)c2nc1-c1nnc(o1)C(O)(C(F)(F)F)CCCCC[C@@H]1CCCN21] | ND |
| 125 | 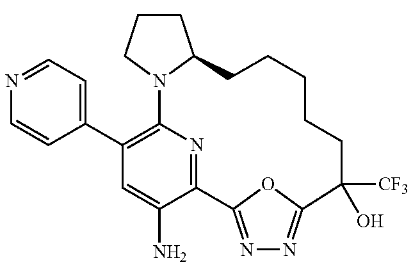 [SMILES: Nc1cc(-c2ccncc2)c2nc1-c1nnc(o1)C(O)(C(F)(F)F)CCCCC[C@@H]1CCCN21] | + |
| 126 | 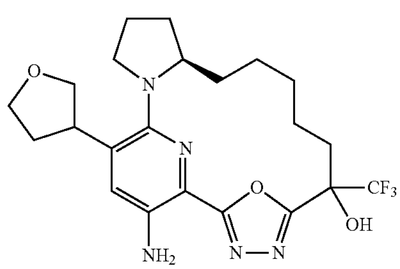 [SMILES: Nc1cc(C2CCOC2)c2nc1-c1nnc(o1)C(O)(C(F)(F)F)CCCCC[C@@H]1CCCN21] | + |
| 127 | 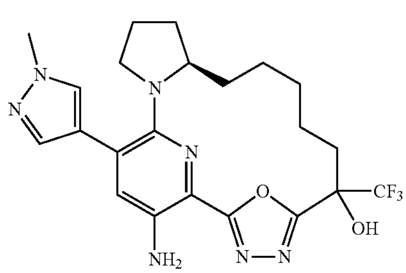 [SMILES: Cn1cc(-c2cc(N)c3nc2N2CCC[C@H]2CCCCCC(O)(C(F)(F)F)c2nnc-3o2)cn1] | +++ |
| 128 | 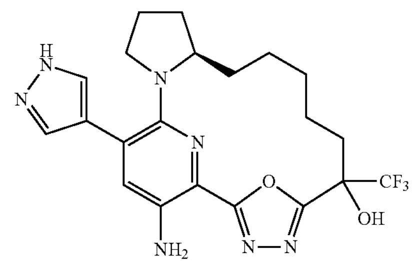 [SMILES: Nc1cc(-c2cn[nH]c2)c2nc1-c1nnc(o1)C(O)(C(F)(F)F)CCCCC[C@@H]1CCCN21] | +++ |
| 129 | 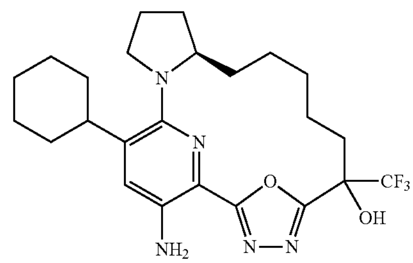 [SMILES: Nc1cc(C2CCCCC2)c2nc1-c1nnc(o1)C(O)(C(F)(F)F)CCCCC[C@@H]1CCCN21] | +++ |
| 130 | 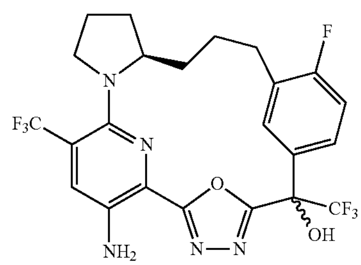 [SMILES: Nc1cc(C(F)(F)F)c2nc1-c1nnc(o1)C(O)(C(F)(F)F)c1ccc(F)c(c1)CCC[C@@H]1CCCN21] | + |
| 131 | 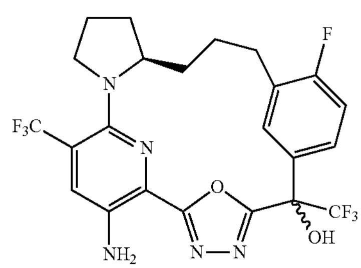 [SMILES: Nc1cc(C(F)(F)F)c2nc1-c1nnc(o1)C(O)(C(F)(F)F)c1ccc(F)c(c1)CCC[C@@H]1CCCN21] | +++ |
| 132 | 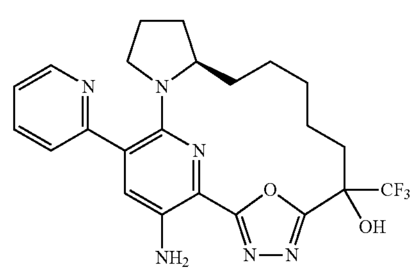 | + |

TABLE 10-continued

| Compound No. | Structure | Bioactivity EC50 |
|---|---|---|
| 133 | | +++ |
| 134 | | + |
| 135 | | +++ |
| 136 | | +++ |
| 137 | | +++ |//
| 138 | 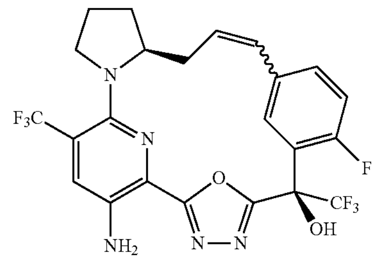 [SMILES: Nc1cc(C(F)(F)F)c2nc1-c1nnc(o1)[C@@](O)(C(F)(F)F)c1cc(ccc1F)C=CC[C@@H]1CCCN21] | +++ |
| 139 | 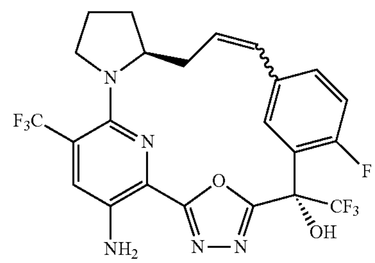 [SMILES: Nc1cc(C(F)(F)F)c2nc1-c1nnc(o1)[C@](O)(C(F)(F)F)c1cc(ccc1F)C=CC[C@@H]1CCCN21] | + |
| 140 | 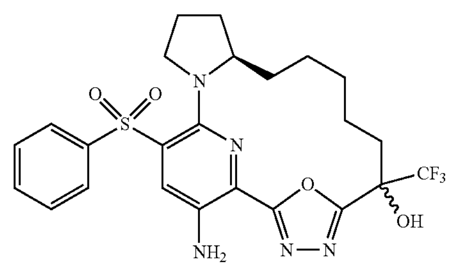 [SMILES: Nc1cc(S(=O)(=O)c2ccccc2)c2nc1-c1nnc(o1)C(O)(C(F)(F)F)CCCCC[C@@H]1CCCN21] | + |
| 141 | 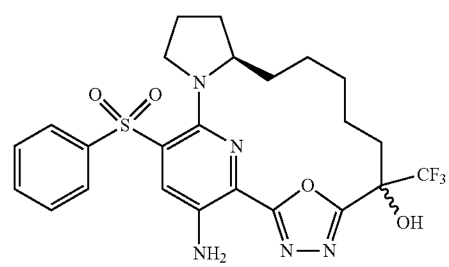 [SMILES: Nc1cc(S(=O)(=O)c2ccccc2)c2nc1-c1nnc(o1)C(O)(C(F)(F)F)CCCCC[C@@H]1CCCN21] | +++ |
| 142 | 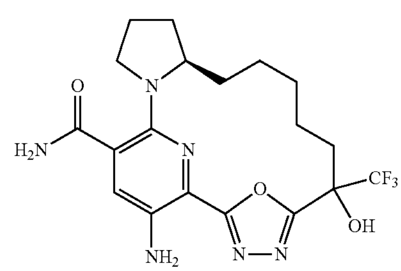 [SMILES: NC(=O)c1cc(N)c2nc1N1CCC[C@H]1CCCCCC(O)(C(F)(F)F)c1nnc-2o1] | + |

TABLE 10-continued

Bioactivity

| Compound No. | Structure | EC50 |
|---|---|---|
| 143 | 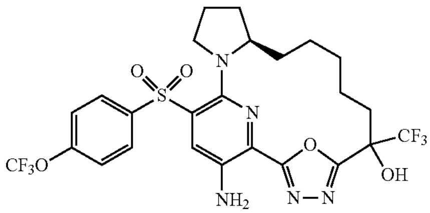 | +++ |
| 144 | 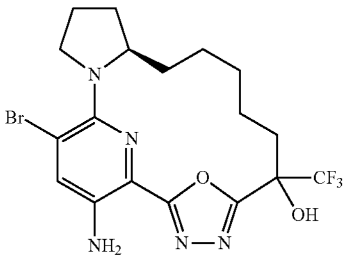 [SMILES: Nc1cc(Br)c2nc1-c1nnc(o1)C(O)(C(F)(F)F)CCCCC[C@@H]1CCCN21] | +++ |
| 145 | 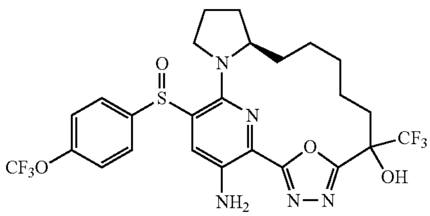 | +++ |
| 146 | 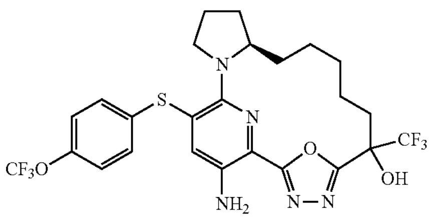 | +++ |
| 147 | 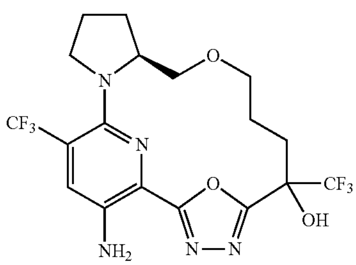 | +++ |
| 148 | 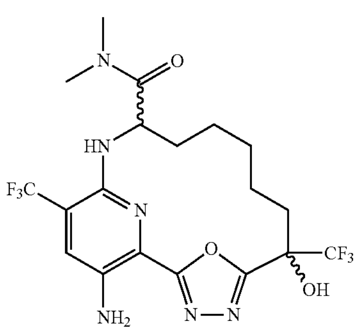 [SMILES: CN(C)C(=O)C1CCCCCC(O)(C(F)(F)F)C2=NN=C(O2)c2nc(c(C(F)(F)F)cc2N)N1] | +++ |
| 149 | | + |
| 150 | | + |
| 151 | | + |
| 152 | | +++ |
| 153 | | + |

TABLE 10-continued

Bioactivity

| Compound No. | Structure | EC50 |
|---|---|---|
| 154 | | + |
| 155 | | + |
| 156 | | +++ |
| 157 | | +++ |
| 158 | | + |
| 159 | | + |
| 160 | | + |
| 161 | | +++ |
| 162 | | ND |

TABLE 10-continued

| Compound No. | Structure | EC50 |
|---|---|---|
| 163 | | +++ |
| 164 | | + |
| 165 | | + |
| 166 | | +++ |
| 167 | | +++ |
| 168 | 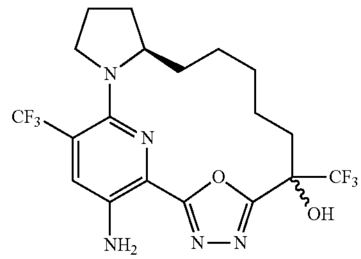 [SMILES: Nc1cc(C(F)(F)F)c2nc1-c1nnc(o1)C(O)(C(F)(F)F)CCCCC[C@@H]1CCCN21] | + |
| 169 | 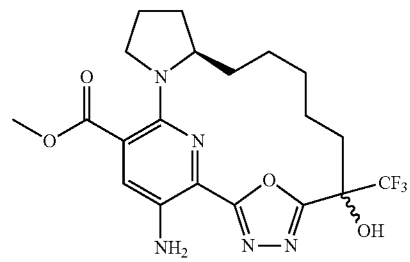 [SMILES: COC(=O)c1cc(N)c2nc1N1CCC[C@H]1CCCCCC(O)(C(F)(F)F)c1nnc-2o1] | + |
| 170 | 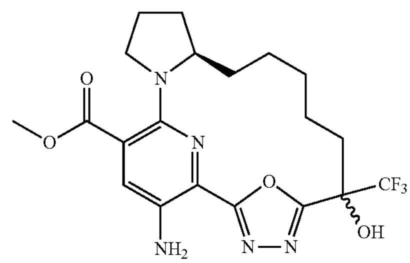 [SMILES: COC(=O)c1cc(N)c2nc1N1CCC[C@H]1CCCCCC(O)(C(F)(F)F)c1nnc-2o1] | +++ |
| 171 | 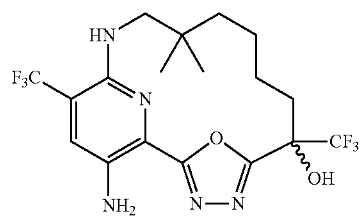 [SMILES: CC1(C)CCCCC(O)(C(F)(F)F)C2=NN=C(O2)c2nc(c(C(F)(F)F)cc2N)NC1] | +++ |
| 172 | 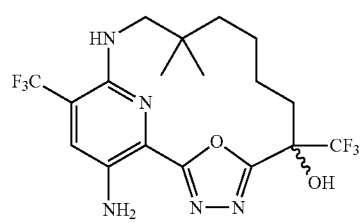 | +++ |
| 173 | 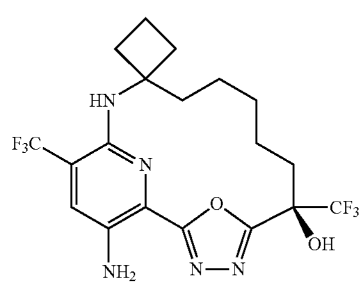 | +++ |

TABLE 10-continued

| Compound No. | Structure | Bioactivity EC50 |
|---|---|---|
| 174 | 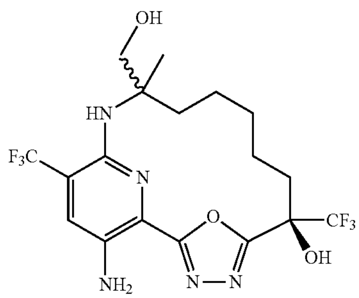 [SMILES: CC1(CO)CCCCC[C@](O)(C(F)(F)F)C2=NN=C(O2)c2nc(c(C(F)(F)F)cc2N)N1] | +++ |
| 175 | 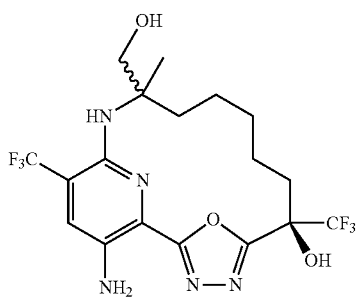 [SMILES: CC1(CO)CCCCC[C@](O)(C(F)(F)F)C2=NN=C(O2)c2nc(c(C(F)(F)F)cc2N)N1] | +++ |
| 176 | 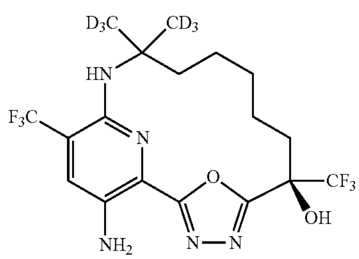 [SMILES: [2H]C([2H])([2H])C1(C([2H])([2H])[2H])CCCCC[C@](O)(C(F)(F)F)C2=NN=C(O2)c2nc(c(C(F)(F)F)cc2N)N1] | +++ |
| 177 | 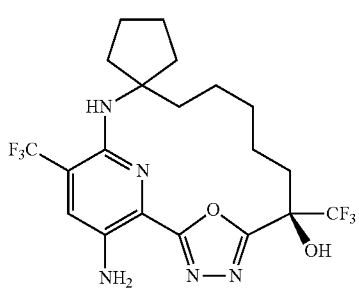 [SMILES: Nc1cc(C(F)(F)F)c2nc1C1=NN=C(O1)[C@@](O)(C(F)(F)F)CCCCCC1(CCCC1)N2] | +++ |
| 178 | 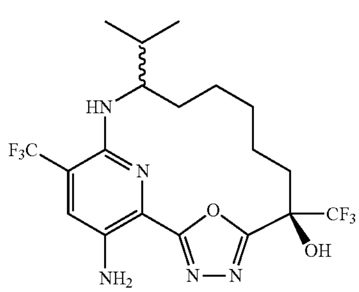 [SMILES: CC(C)C1CCCCC[C@](O)(C(F)(F)F)C2=NN=C(O2)c2nc(c(C(F)(F)F)cc2N)N1] | +++ |
| 179 | 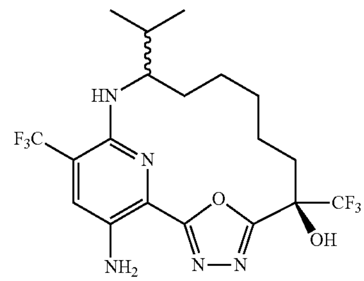 [SMILES: CC(C)C1CCCCC[C@](O)(C(F)(F)F)C2=NN=C(O2)c2nc(c(C(F)(F)F)cc2N)N1] | +++ |
| 180 | 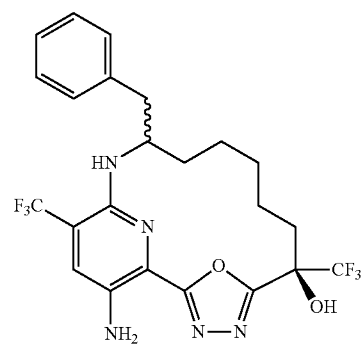 [SMILES: Nc1cc(C(F)(F)F)c2nc1C1=NN=C(O1)[C@@](O)(C(F)(F)F)CCCCCC(Cc1ccccc1)N2] | +++ |
| 181 | 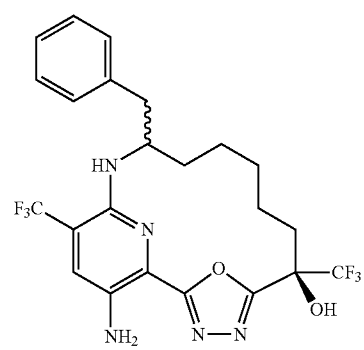 [SMILES: Nc1cc(C(F)(F)F)c2nc1C1=NN=C(O1)[C@@](O)(C(F)(F)F)CCCCCC(Cc1ccccc1)N2] | ND |
| 182 | 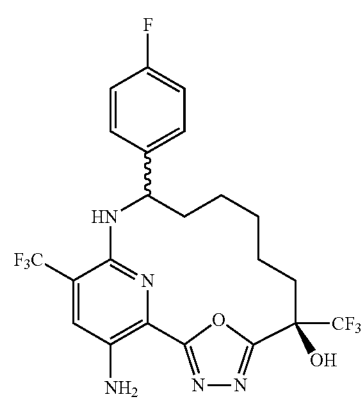 [SMILES: Nc1cc(C(F)(F)F)c2nc1C1=NN=C(O1)[C@@](O)(C(F)(F)F)CCCCCC(c1ccc(F)cc1)N2] | +++ |

TABLE 10-continued

| Compound No. | Structure | EC50 |
|---|---|---|
| 183 | 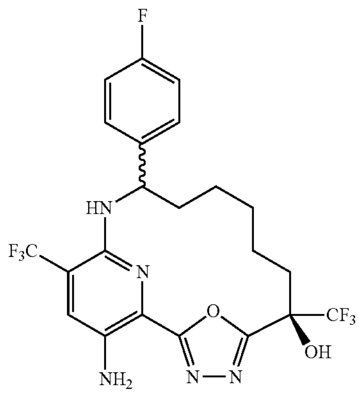 [SMILES: Nc1cc(C(F)(F)F)c2nc1C1=NN=C(O1)[C@@](O)(C(F)(F)F)CCCCCC(c1ccc(F)cc1)N2] | ND |
| 184 | 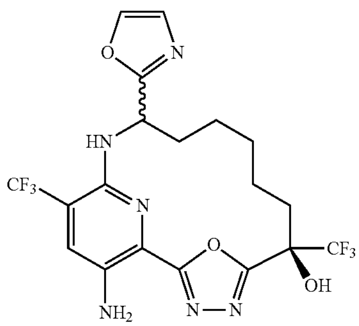 [SMILES: Nc1cc(C(F)(F)F)c2nc1C1=NN=C(O1)[C@@](O)(C(F)(F)F)CCCCCC(c1ncco1)N2] | +++ |
| 185 | 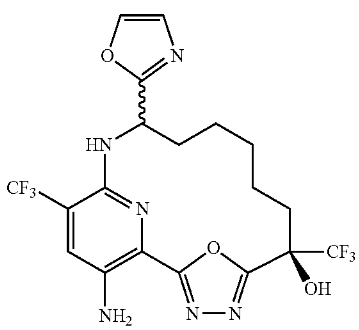 [SMILES: Nc1cc(C(F)(F)F)c2nc1C1=NN=C(O1)[C@@](O)(C(F)(F)F)CCCCCC(c1ncco1)N2] | ND |
| 186 | 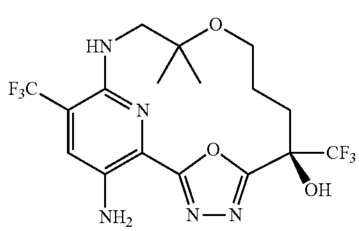 | +++ |
| 187 | 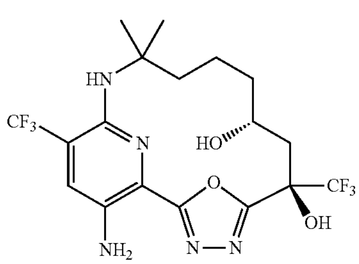 [SMILES: CC1(C)CCC[C@@H](O)C[C@](O)(C(F)(F)F)C2=NN=C(O2)c2nc(c(C(F)(F)F)cc2N)N1] | +++ |
| 188 | | +++ |
| 189 | | + |
| 190 | | +++ |
| 191 | | +++ |
| 192 | | +++ |

TABLE 10-continued

Bioactivity

| Compound No. | Structure | EC50 |
|---|---|---|
| 193 | 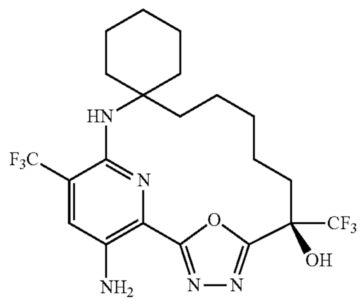 [SMILES: Nc1cc(C(F)(F)F)c2nc1C1=NN=C(O1)[C@@](O)(C(F)(F)F)CCCCCC1(CCCCC1)N2] | +++ |
| 194 | 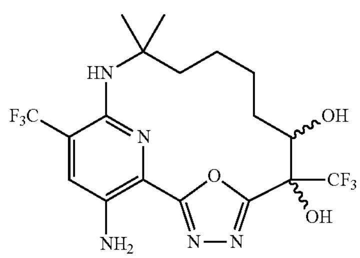 [SMILES: CC1(C)CCCCC(O)C(O)(C(F)(F)F)C2=NN=C(O2)c2nc(c(C(F)(F)F)cc2N)N1] | +++ |
| 195 | 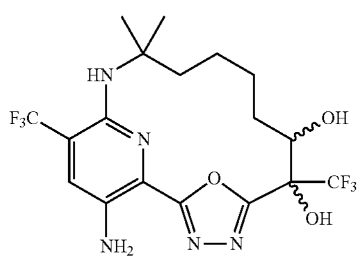 | + |
| 196 | 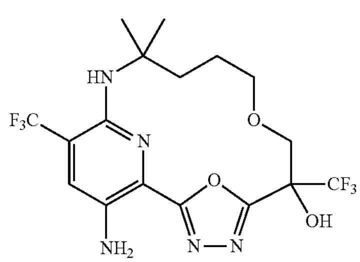 | ND |
| 197 | 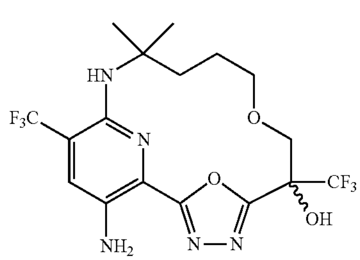 [SMILES: CC1(C)CCCOCC(O)(C(F)(F)F)C2=NN=C(O2)c2nc(c(C(F)(F)F)cc2N)N1] | +++ |
| 198 | | ND |
| 199 | | +++ |
| 200 | | ND |
| 201 | | +++ |
| 202 | | ND |

TABLE 10-continued

| Compound No. | Structure | EC50 |
|---|---|---|
| 203 | 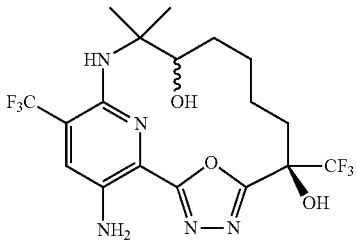 [SMILES: CC1(C)Nc2nc(c(N)cc2C(F)(F)F)C2=NN=C(O2)[C@@](O)(C(F)(F)F)CCCCC1O] | +++ |
| 204 | 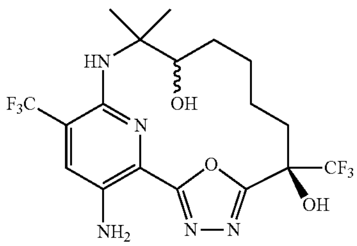 | +++ |
| 205 | 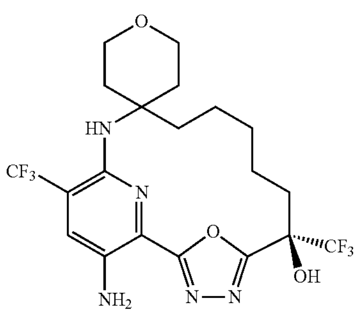 [SMILES: Nc1cc(C(F)(F)F)c2nc1C1=NN=C(O1)[C@@](O)(C(F)(F)F)CCCCCC1(CCOCC1)N2] | +++ |
| 206 | 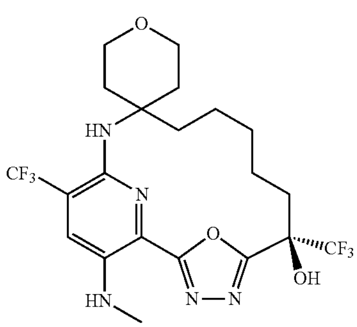 [SMILES: CNc1cc(C(F)(F)F)c2nc1C1=NN=C(O1)[C@@](O)(C(F)(F)F)CCCCCC1(CCOCC1)N2] | ND |
| 207 | 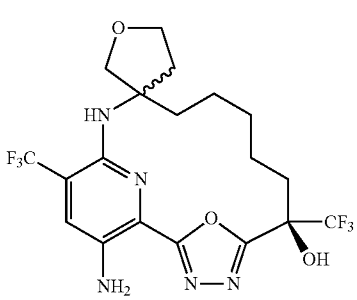 [SMILES: Nc1cc(C(F)(F)F)c2nc1C1=NN=C(O1)[C@@](O)(C(F)(F)F)CCCCCC1(CCOC1)N2] | +++ |
| 208 | 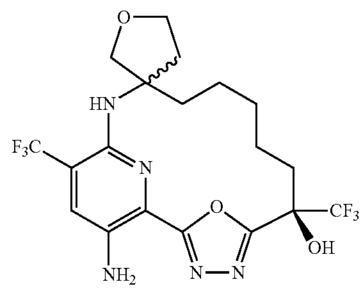 [SMILES: Nc1cc(C(F)(F)F)c2nc1C1=NN=C(O1)[C@@](O)(C(F)(F)F)CCCCCC1(CCOC1)N2] | +++ |
| 209 | 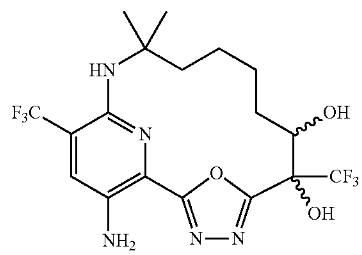 [SMILES: CC1(C)CCCCC(O)C(O)(C(F)(F)F)C2=NN=C(O2)c2nc(c(C(F)(F)F)cc2N)N1] | ND |
| 210 | 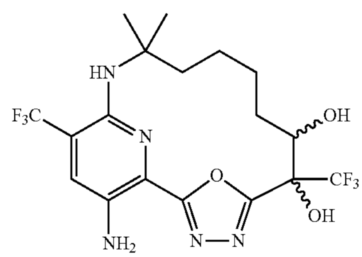 | ND |
| 211 | 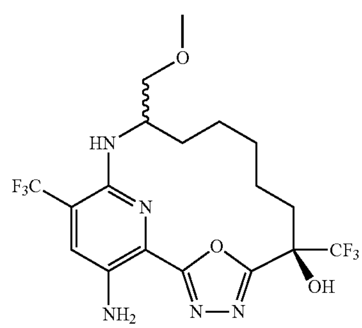 [SMILES: COCC1CCCCC[C@](O)(C(F)(F)F)C2=NN=C(O2)c2nc(c(C(F)(F)F)cc2N)N1] | ND |
| 212 | 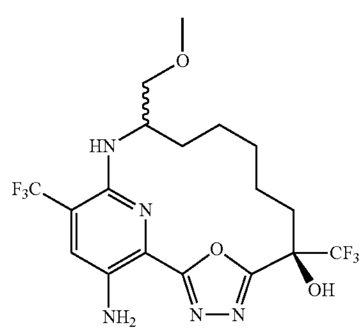 [SMILES: COCC1CCCCC[C@](O)(C(F)(F)F)C2=NN=C(O2)c2nc(c(C(F)(F)F)cc2N)N1] | ND |

TABLE 10-continued

| Compound No. | Structure | EC50 |
|---|---|---|
| 213 | 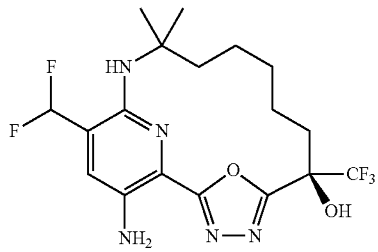 [SMILES: CC1(C)CCCCC[C@](O)(C(F)(F)F)C2=NN=C(O2)c2nc(c(C(F)F)cc2N)N1] | ND |
| 214 | diastereomer 1 | ND |
| 215 | diastereomer 2 | ND |
| 216 | mixture of diastereomers | ND |
| 217 | 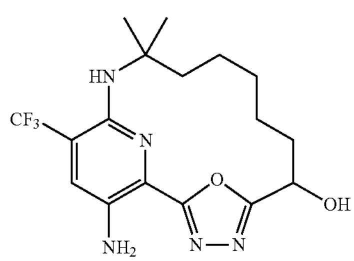 [SMILES: CC1(C)CCCCCC(O)C2=NN=C(O2)c2nc(c(C(F)(F)F)cc2N)N1] | ND |
| 218 | enantiomer 1 | ND |
| 219 | enantiomer 2 | ND |
| 220 | | ND |
| 221 | enantiomer 1 | ND |
| 222 | enantiomer 2 | ND |

Other Embodiments

The foregoing discussion discloses and describes merely exemplary embodiments of this disclosure. One skilled in the art will readily recognize from such discussion and from the accompanying drawings and claims, that various changes, modifications and variations can be made therein without departing from the spirit and scope of this disclosure as defined in the following claims.

The invention claimed is:
1. A compound of Formula I:

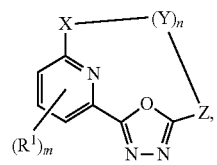

I and a deuterated derivative thereof, or a pharmaceutically acceptable salt of the foregoing, wherein:
X is selected from —N($R^{X1}$)— and

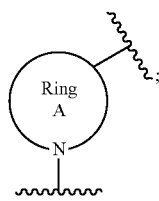

;

Ring A is a 4- to 6-membered heterocyclyl optionally substituted with 1-3 groups independently selected from $C_1$-$C_6$ alkyl and oxo;
$R^{X1}$ is selected from H, $C_1$-$C_6$ alkyl (optionally substituted with 1-3 groups independently selected from hydroxy, oxo, —$OR^{X2}$, and —N($R^{X2}$)$_2$), and $C_3$-$C_8$ cycloalkyl;
each $R^{X2}$ is independently selected from H and $C_1$-$C_6$ alkyl;
each Y is independently selected from —C($R^Y$)$_2$—, —O—, —CO—, —$NR^{YN}$—, and

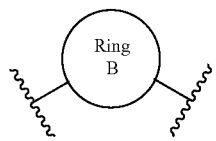

, wherein each $R^{YN}$ is independently selected from H, $C_1$-$C_4$ alkyl, and $CO_2R^{YN1}$, wherein each $R^{YN1}$ is independently selected from $C_1$-$C_4$ alkyl and $C_3$-$C_6$ cycloalkyl;
  each $R^Y$ is independently selected from hydrogen, hydroxy, halogen, $C_1$-$C_6$ alkyl (optionally substituted with 1-3 groups independently selected from hydroxy, $C_1$-$C_6$ alkoxy, and Q), $C_3$-$C_8$ cycloalkyl, $C_6$-$C_{10}$ aryl (optionally substituted with 1-3 groups independently selected from halogen), 5- to 10-membered heteroaryl, —$OR^{Y1}$, —$CO_2R^{Y1}$, —$COR^{Y1}$, —CON($R^{Y1}$)$_2$, and —N($R^{Y1}$)$_2$;

or two $R^Y$ on the same atom are taken together to form a ring selected from $C_3$-$C_8$ cycloalkyl and 3- to 7-membered heterocyclyl; or two $R^Y$, one of which is on one atom and the second of which is on an adjacent atom, are taken together to form a pi bond;
each $R^{Y1}$ is independently selected from hydrogen and $C_1$-$C_6$ alkyl, or two $R^{Y1}$ bonded to the same nitrogen taken together form a 3- to 6-membered heterocyclyl;
Ring B is selected from:
  $C_6$-$C_{10}$ aryl (optionally substituted with 1-3 groups independently selected from halogen, $C_1$-$C_6$ alkyl, and $C_1$-$C_6$ alkoxy),
  $C_3$-$C_8$ cycloalkyl,
  5- to 10-membered heteroaryl, and
  3- to 6-membered heterocyclyl (optionally substituted with 1-3 groups independently selected from $C_1$-$C_6$ alkyl);
each Q is independently selected from:
  $C_1$-$C_6$ alkyl optionally substituted with 1-3 groups independently selected from:
    halogen,
    oxo,
    $C_6$-$C_{10}$ aryl (optionally substituted with 1-3 groups independently selected from halogen and —$OCF_3$), and
    $C_3$-$C_8$ cycloalkyl,
  $C_3$-$C_8$ cycloalkyl optionally substituted with 1-3 groups independently selected from:
    halogen,
    CN,
    $C_1$-$C_6$ alkyl (optionally substituted with 1-3 groups independently selected from halogen, —$NH_2$, and —NHCOMe),
    $C_1$-$C_6$ alkoxy,
    $C_6$-$C_{10}$ aryl (optionally substituted with 1-3 groups independently selected from $C_1$-$C_6$ alkyl), and
    $C_3$-$C_8$ cycloalkyl,
  $C_6$-$C_{10}$ aryl optionally substituted with 1-3 groups independently selected from:
    halogen,
    CN,
    $C_1$-$C_6$ alkyl (optionally substituted with 1-3 groups independently selected from halogen and hydroxy),
    $C_1$-$C_6$ alkoxy optionally substituted with 1-4 groups independently selected from:
      halogen,
      $C_3$-$C_8$ cycloalkyl (optionally substituted with $CF_3$),
    $C_3$-$C_8$ cycloalkyl (optionally substituted with 1-3 groups independently selected from halogen, $CF_3$, $OCF_3$, and $C_1$-$C_6$ alkyl), and
    $C_6$-$C_{10}$ aryl,
  5- to 10-membered heteroaryl optionally substituted with 1-3 groups independently selected from:
    halogen,
    $C_1$-$C_6$ alkyl (optionally substituted with 1-3 groups independently selected from halogen),
    $C_3$-$C_8$ cycloalkyl (optionally substituted with 1-3 $CF_3$ groups), and
    3- to 10-membered heterocyclyl,
  3- to 10-membered heterocyclyl optionally substituted with 1-3 groups independently selected from:
    $C_1$-$C_6$ alkyl (optionally substituted with 1-3 groups independently selected from oxo and $C_3$-$C_8$ cycloalkyl), and
    oxo;

each $R^1$ is independently selected from halogen, $C_1$-$C_6$ fluoroalkyl, $C_1$-$C_6$ alkyl (optionally substituted with a group selected from hydroxy, $C_6$-$C_{10}$ aryl, and 5- to 6-membered heteroaryl), —$OR^2$, —$N(R^2)_2$, —$CO_2R^2$, —CO—$N(R^2)_2$, —CN, $C_3$-$C_8$ cycloalkyl, $C_6$-$C_{10}$ aryl, 5- to 6-membered heteroaryl (optionally substituted with 1-3 groups independently selected from $C_1$-$C_6$ alkyl), 3- to 6-membered heterocyclyl, —$B(OR^2)_2$, —$SO_2R^2$, —$SR^2$, —$SOR^2$, —$PO(OR^2)_2$, and —PO$(R^2)_2$;

each $R^2$ is independently selected from hydrogen, $C_1$-$C_6$ alkyl (optionally substituted with 1-6 groups independently selected from halogen), $C_1$-$C_6$ fluoroalkyl, and $C_6$-$C_{10}$ aryl (optionally substituted with 1-3 groups independently selected from $C_1$-$C_6$ fluoroalkyl and $C_1$-$C_6$ fluoroalkoxy);

Z is selected from

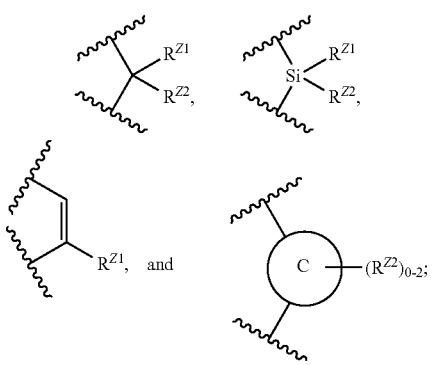

wherein Ring C is selected from $C_6$-$C_{10}$ aryl and 5- to 10-membered heteroaryl;

$R^{Z1}$ is selected from hydrogen, —CN, $C_1$-$C_6$ alkyl (optionally substituted with 1-3 hydroxy), $C_1$-$C_6$ fluoroalkyl, 3- to 6-membered heterocyclyl, $C_3$-$C_6$ cycloalkyl, $C_6$-$C_{10}$ aryl, and 5- to 6-membered heteroaryl;

$R^{Z2}$ is selected from hydrogen, halogen, hydroxy, $NH_2$, NH(CO) ($C_1$-$C_6$ alkyl), and $C_1$-$C_6$ alkoxy (optionally substituted with 1-3 groups independently selected from $C_3$-$C_{10}$ cycloalkyl), or $R^{Z1}$ and $R^{Z2}$ taken together form a group selected from oxo and =N—OH;

each $R^{Z3}$ is independently selected from hydroxy, $C_1$-$C_6$ alkoxy, $C_1$-$C_6$ alkyl, and $C_6$-$C_{10}$ aryl; or two $R^{Z3}$ are taken together to form a 3- to 6-membered heterocyclyl;

n is selected from 4, 5, 6, 7, and 8; and m is selected from 0, 1, 2, and 3.

2. The compound, deuterated derivative, or pharmaceutically acceptable salt according to claim 1, wherein X is —$N(R^{X1})$—.

3. The compound, deuterated derivative, or pharmaceutically acceptable salt according to claim 1, wherein X is

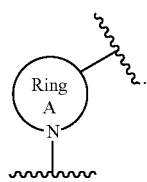

4. The compound, deuterated derivative, or pharmaceutically acceptable salt according to claim 1, wherein X is selected from:

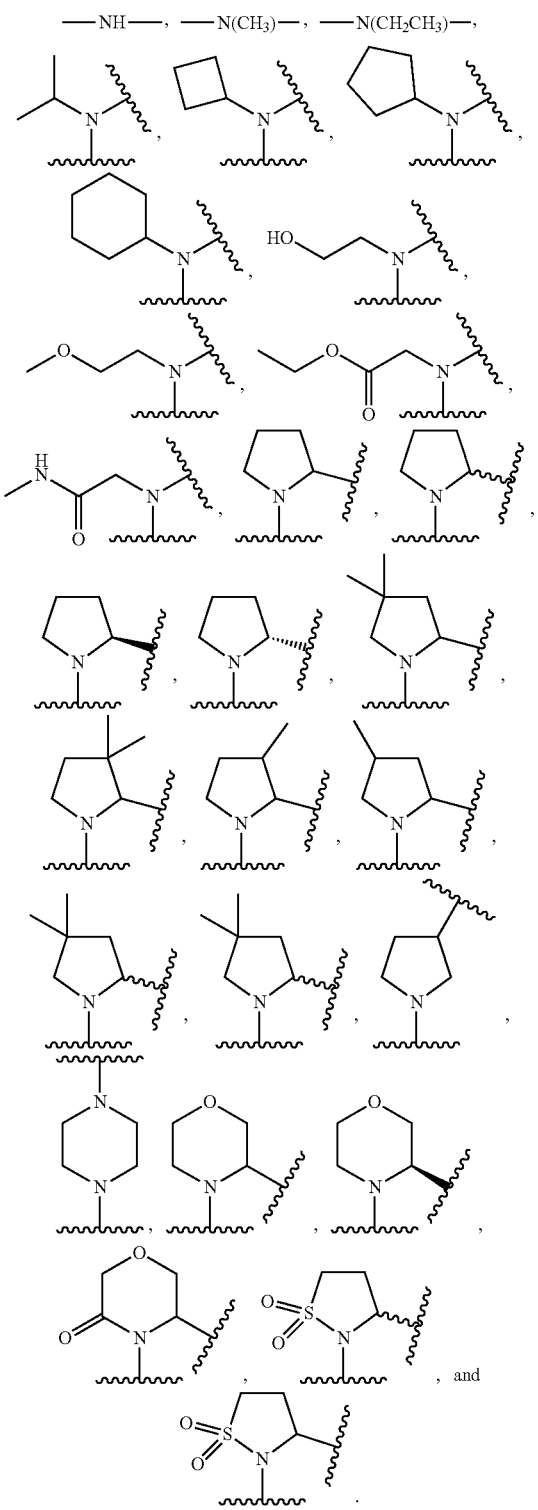

5. The compound, deuterated derivative, or pharmaceutically acceptable salt according to claim 1, wherein:
each $R^Y$ is independently selected from hydrogen, hydroxy, halogen, $C_1$-$C_6$ alkyl (optionally substituted with 1-3 groups independently selected from hydroxy, $C_1$-$C_6$ alkoxy, and Q), $C_3$-$C_8$ cycloalkyl, $C_6$-$C_{10}$ aryl (optionally substituted with 1-3 groups independently selected from halogen), 5- to 10-membered heteroaryl, —$CO_2R^{Y1}$, and —$CON(R^{Y1})_2$;

or two $R^Y$ on the same atom are taken together to form a ring selected from $C_3$-$C_8$ cycloalkyl and 3- to 7-membered heterocyclyl;

or two $R^Y$, one of which is on one atom and the second of which is on an adjacent atom, are taken together to form a pi bond.

6. The compound, deuterated derivative, or pharmaceutically acceptable salt according to claim 1, wherein each $R^{Y1}$ is independently selected from hydrogen and $C_1$-$C_6$ alkyl, or two $R^{Y1}$ bonded to the same nitrogen taken together form a 3- to 6-membered heterocyclyl.

7. The compound, deuterated derivative, or pharmaceutically acceptable salt according to claim 1, wherein each Q is independently selected from $C_6$-$C_{10}$ aryl.

8. The compound, deuterated derivative, or pharmaceutically acceptable salt according to claim 1, wherein each Q is phenyl.

9. The compound, deuterated derivative, or pharmaceutically acceptable salt according to claim 1, wherein:
each $R^Y$ is independently selected from:

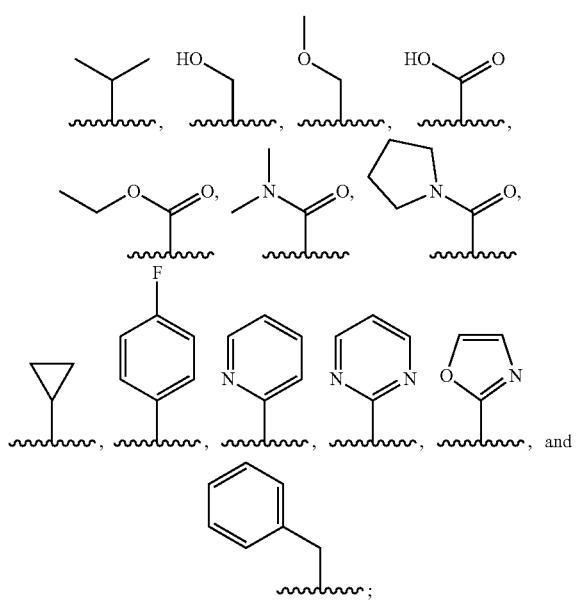

or two $R^Y$ on the same atom are taken together to form a ring selected from cyclobutyl, cyclopentyl, cyclohexyl, tetrahydropyryl, and tetrahydrofuryl;

or two $R^Y$, one of which is on one atom and the second of which is on an adjacent atom, are taken together to form a pi bond.

10. The compound, deuterated derivative, or pharmaceutically acceptable salt according to claim 1, wherein Ring B is selected from $C_6$-$C_{10}$ aryl (optionally substituted with 1-3 groups independently selected from halogen and $C_1$-$C_6$ alkoxy) and 5- to 10-membered heteroaryl.

11. The compound, deuterated derivative, or pharmaceutically acceptable salt according to claim 1, wherein Ring B is selected from phenyl (optionally substituted with 1-3 groups independently selected from halogen and $C_1$-$C_6$ alkoxy) and pyridyl.

12. The compound, deuterated derivative, or pharmaceutically acceptable salt according to claim 1, wherein Ring B is selected from:

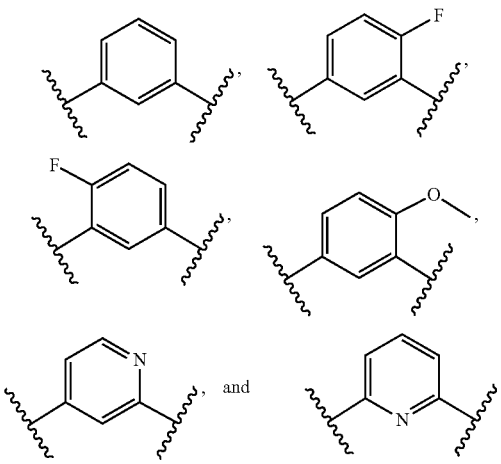

13. The compound, deuterated derivative, or pharmaceutically acceptable salt according to claim 1, wherein n is selected from 4, 5, 6, and 7.

14. The compound, deuterated derivative, or pharmaceutically acceptable salt according to claim 1, wherein —$(Y)_n$— is a group selected from:

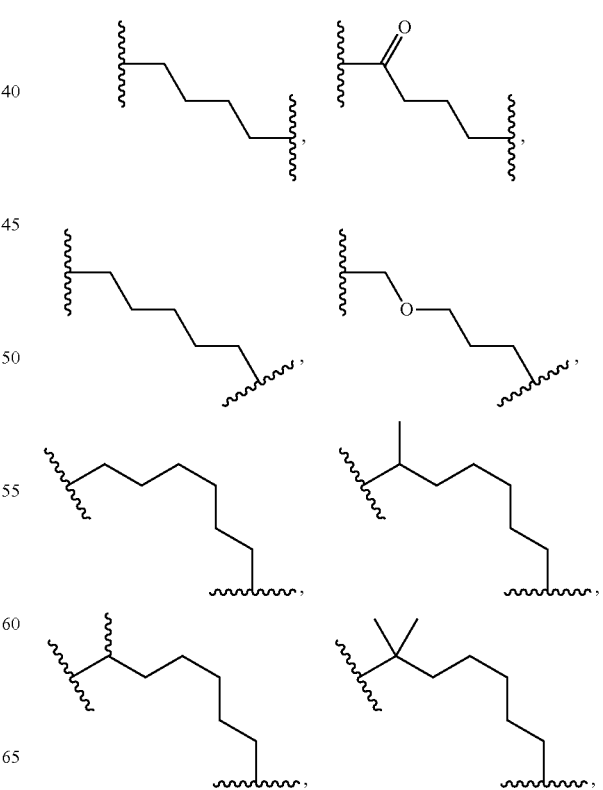

1071
-continued
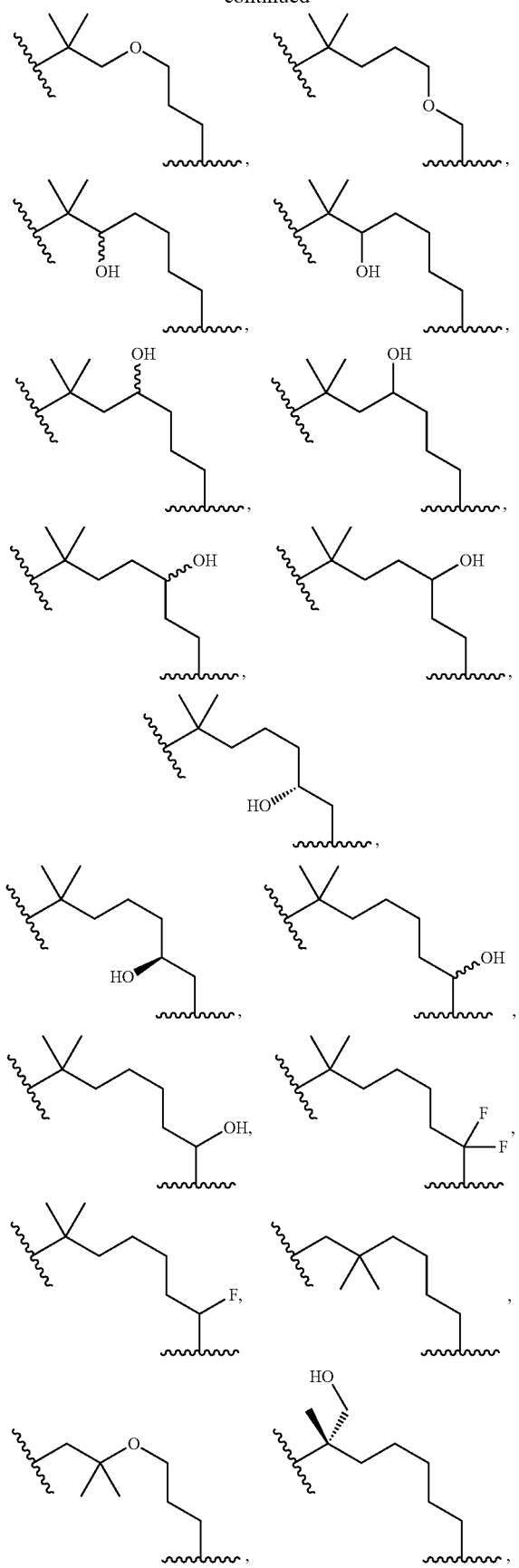
1072
-continued
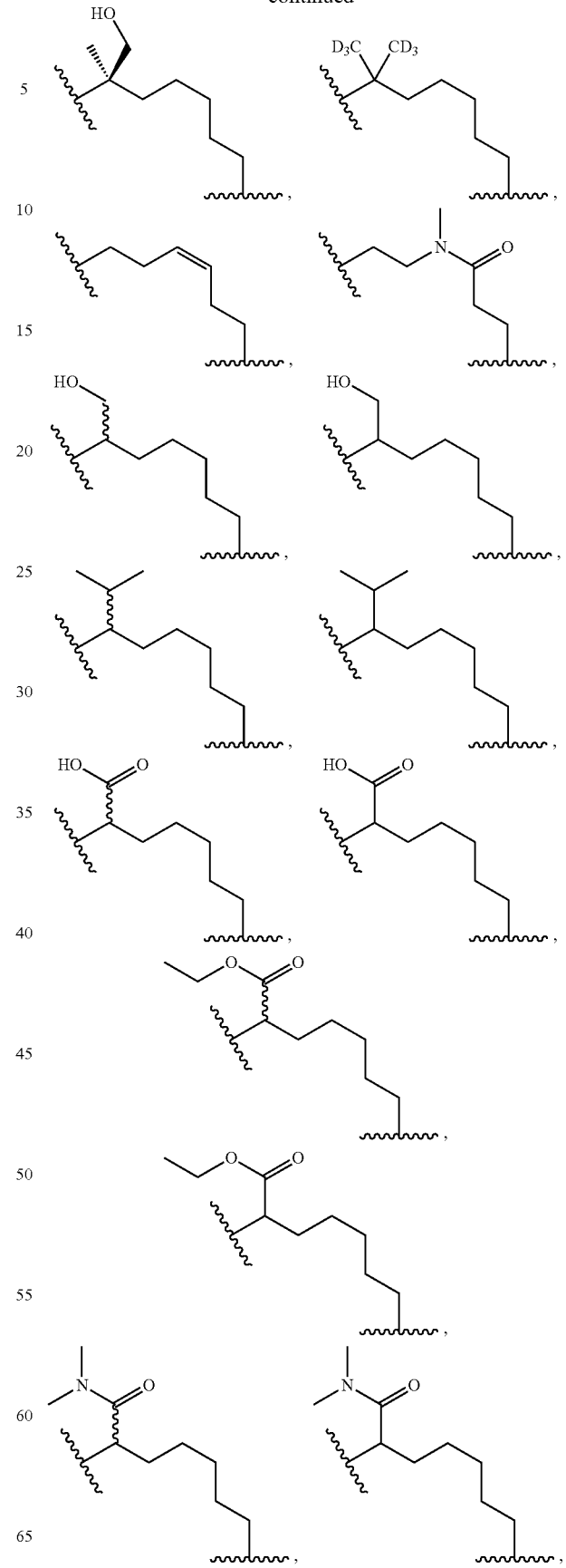

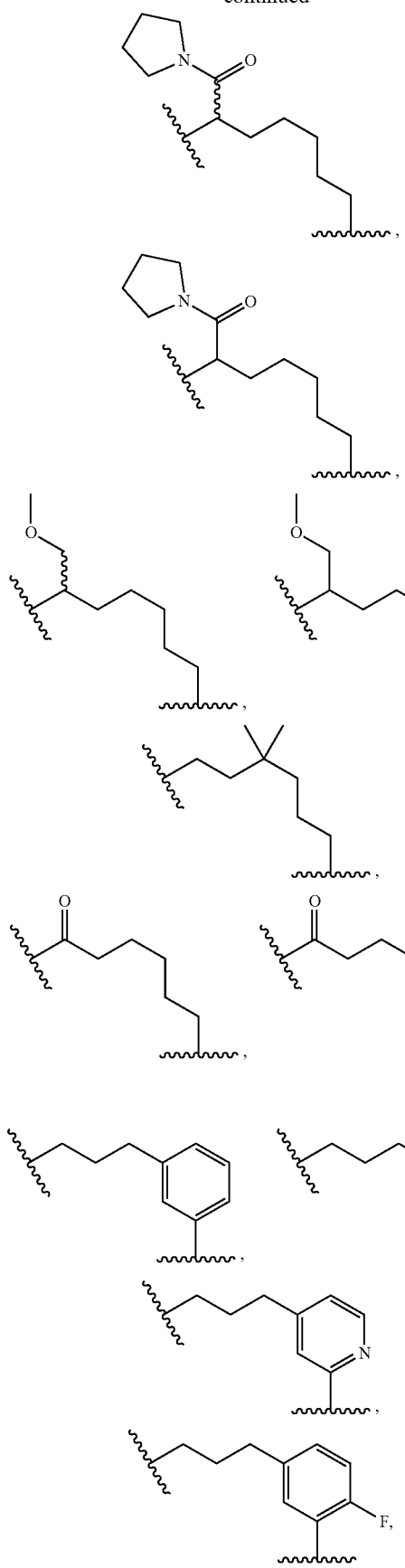
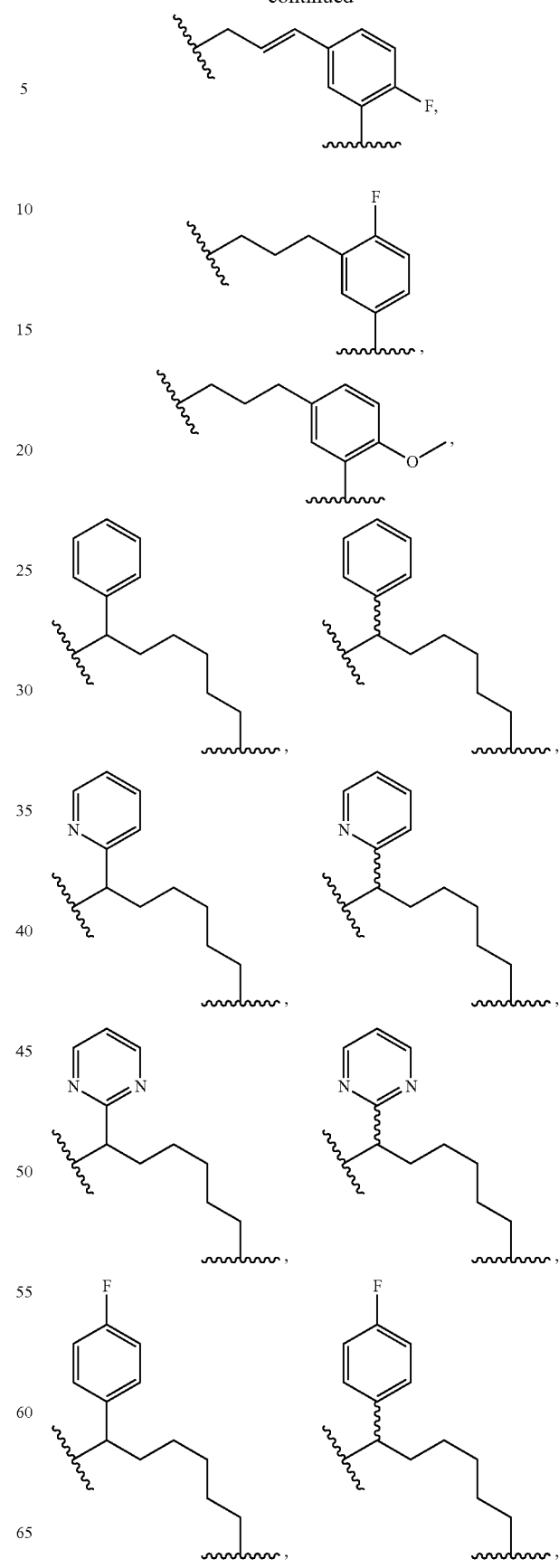

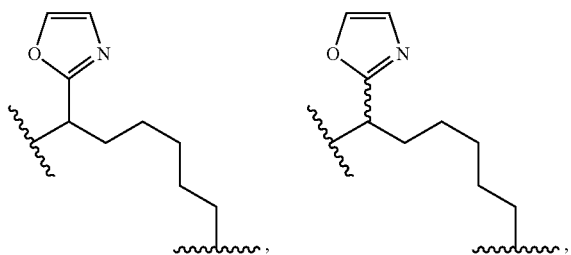,

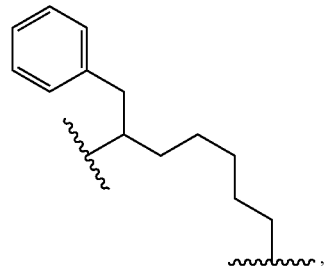,

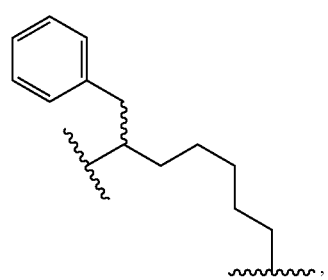,

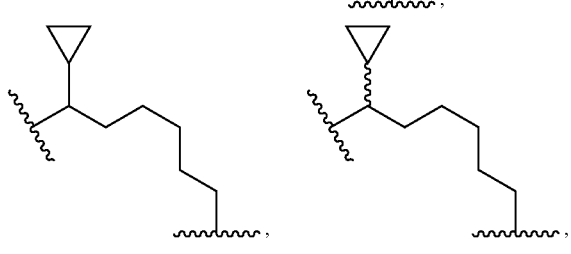,

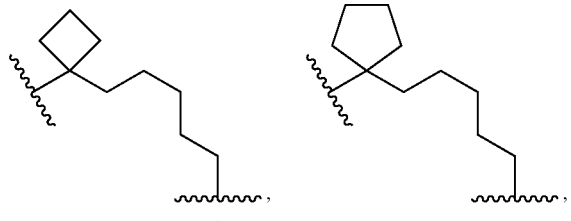,

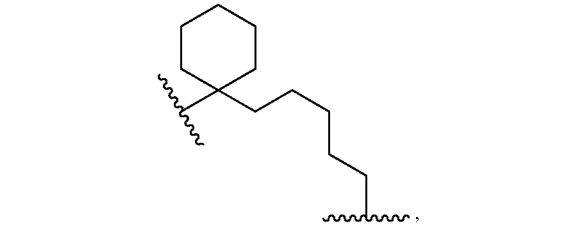,

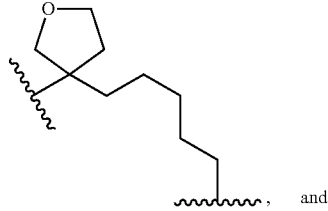, and

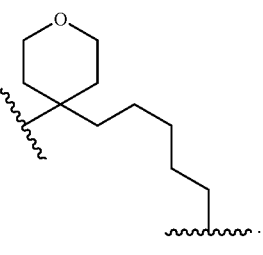.

15. The compound, deuterated derivative, or pharmaceutically acceptable salt according to claim 1, wherein each $R^1$ is independently selected from halogen, $C_1$-$C_6$ fluoroalkyl, $C_1$-$C_6$ alkyl (optionally substituted with a group selected from $C_6$-$C_{10}$ aryl), —$OR^2$, —$N(R^2)_2$, —$CO_2R^2$, —CO—N$(R^2)_2$, —CN, $C_1$-$C_6$ alkoxy, $C_3$-$C_8$ cycloalkyl, $C_6$-$C_{10}$ aryl, 5- to 6-membered heteroaryl (optionally substituted with 1-3 groups independently selected from $C_1$-$C_6$ alkyl), 3- to 6-membered heterocyclyl, —$B(OR^2)_2$, —$SO_2R^2$, —$SR^2$, —$SOR^2$, and —$PO(R^2)_2$.

16. The compound, deuterated derivative, or pharmaceutically acceptable salt according to claim 1, wherein each $R^2$ is independently selected from hydrogen and $C_6$-$C_{10}$ aryl (optionally substituted with 1-3 groups independently selected from $C_1$-$C_6$ fluoroalkoxy).

17. The compound, deuterated derivative, or pharmaceutically acceptable salt according to claim 1, wherein each $R^1$ is independently selected from —Br, —$CF_3$, —$NH_2$, —$CH_3$, —$CH(CH_3)_2$, —CN, —OH, —$OCH_3$, —$NH(CH_3)$, —$NH(CH_2CH_3)$, —$CONH_2$, —$CO_2CH_3$, —$SO_2CH_3$, —$SO_2Ph$, $PO(CH_3)_2$, $B(OH)_2$, phenyl, pyridyl, tetrahydropyranyl, tetrahydrofuranyl, cyclopropyl, cyclohexyl, imidazolyl.

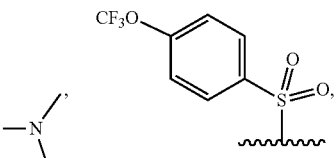

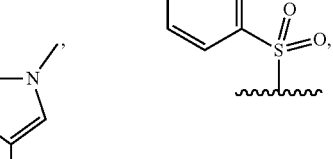

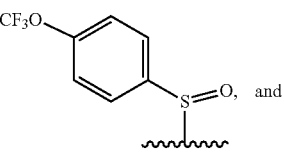, and

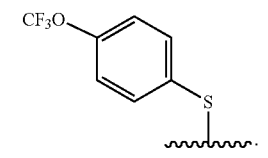.

18. The compound, deuterated derivative, or pharmaceutically acceptable salt according to claim 1, wherein Z is selected from

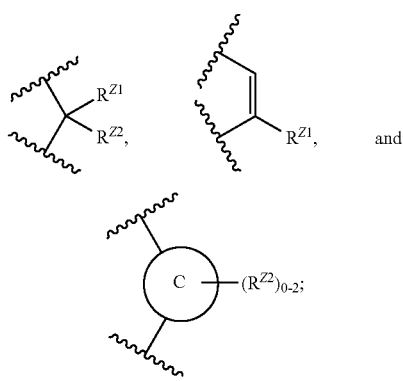

wherein Ring C is selected from $C_6$-$C_{10}$ aryl.

19. The compound, deuterated derivative, or pharmaceutically acceptable salt according to claim 1, wherein the group:

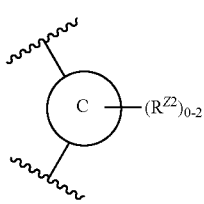

is selected from:

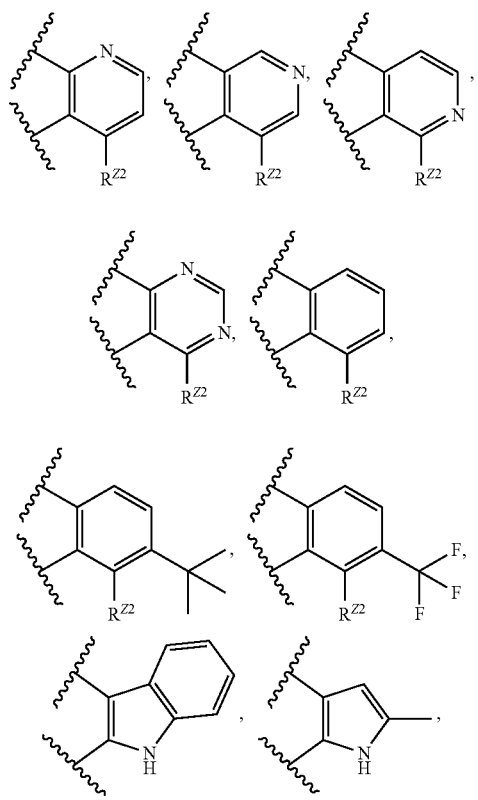

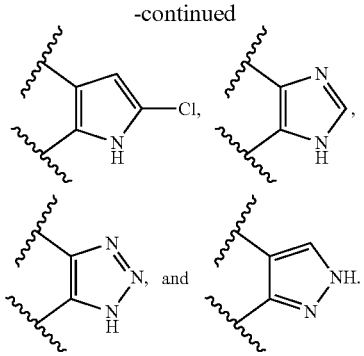

20. The compound, deuterated derivative, or pharmaceutically acceptable salt according to claim 1, wherein the group:

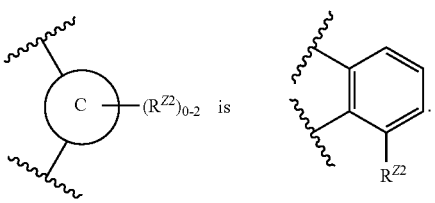

21. The compound, deuterated derivative, or pharmaceutically acceptable salt according to claim 1, wherein $R^{Z1}$ is selected from hydrogen, $C_1$-$C_6$ alkyl (optionally substituted with 1-3 hydroxy), $C_1$-$C_6$ fluoroalkyl, 3- to 6-membered heterocyclyl, $C_3$-$C_6$ cycloalkyl, $C_6$-$C_{10}$ aryl, and 5- to 6-membered heteroaryl.

22. The compound, deuterated derivative, or pharmaceutically acceptable salt according to claim 1, wherein $R^{Z2}$ is selected from hydrogen, halogen, hydroxy, and $C_1$-$C_6$ alkoxy (optionally substituted with 1-3 groups independently selected from $C_3$-$C_{10}$ cycloalkyl).

23. The compound, deuterated derivative, or pharmaceutically acceptable salt according to claim 1, wherein:

$R^{Z1}$ is selected from hydrogen, $C_1$-$C_6$ alkyl (optionally substituted with 1-3 hydroxy), $C_1$-$C_6$ fluoroalkyl, 3- to 6-membered heterocyclyl, $C_3$-$C_6$ cycloalkyl, and $C_6$-$C_{10}$ aryl; and $R^{Z2}$ is selected from hydrogen, halogen, and hydroxy;

or $R^{Z1}$ and $R^{Z2}$ taken together form a group selected from oxo and =N—OH.

24. The compound, deuterated derivative, or pharmaceutically acceptable salt according to claim 1, wherein:

$R^{Z1}$ is selected from hydrogen, $CH_3$, $CF_3$, $CH_2OH$, phenyl, cyclopropyl, and tetrahydropyranyl; and $R^{Z2}$ is selected from hydrogen, halogen, and hydroxy;

or $R^{Z1}$ and $R^{Z2}$ taken together form a group selected from oxo and =N—OH.

25. The compound, deuterated derivative, or pharmaceutically acceptable salt according to claim 1, wherein $R^{Z2}$ is hydroxy.

26. The compound, deuterated derivative, or pharmaceutically acceptable salt according to claim 1, wherein Z is selected from:

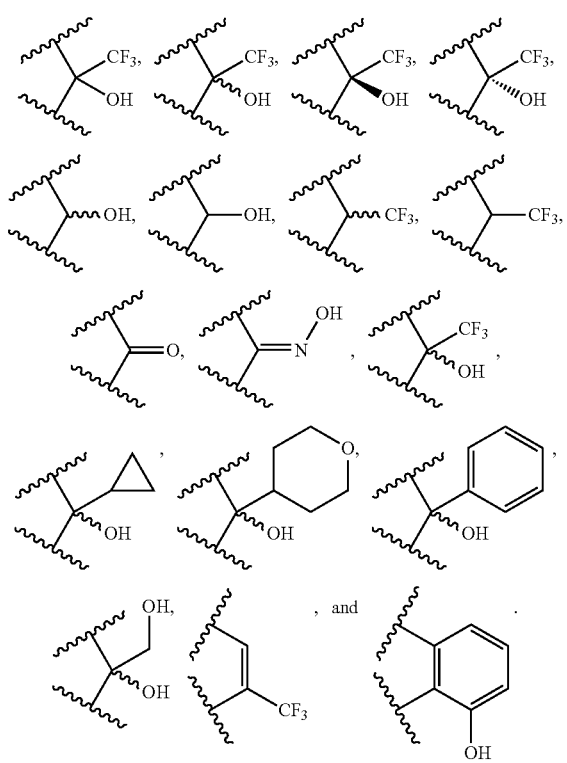
27. The compound, deuterated derivative, or pharmaceutically acceptable salt according to claim 1, wherein m is selected from 1 and 2.
28. A compound selected from:
| Compound No. | Structure |
|---|---|
| 1 | 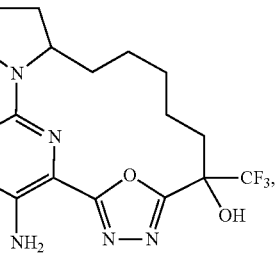mixture of 4 stereoisomers |
| 2 | 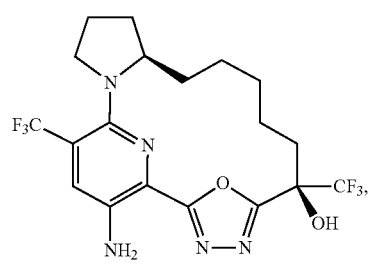 [SMILES: Nc1cc(C(F)(F)F)c2nc1-c1nnc(o1)[C@@](O)(C(F)(F)F)CCCCC[C@@H]1CCCN21]diastereomer pair 1 |
| 3 | 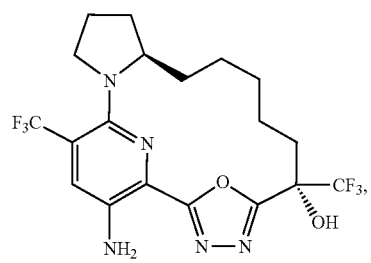diastereomer pair 2 |
| 4 | 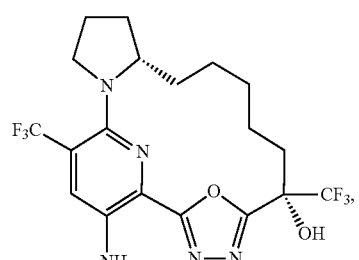 |
| 5 | 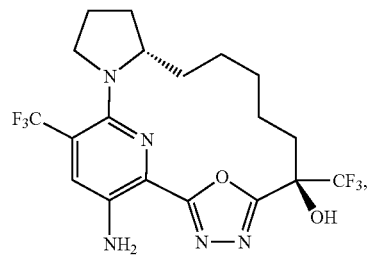 |
| 6 | 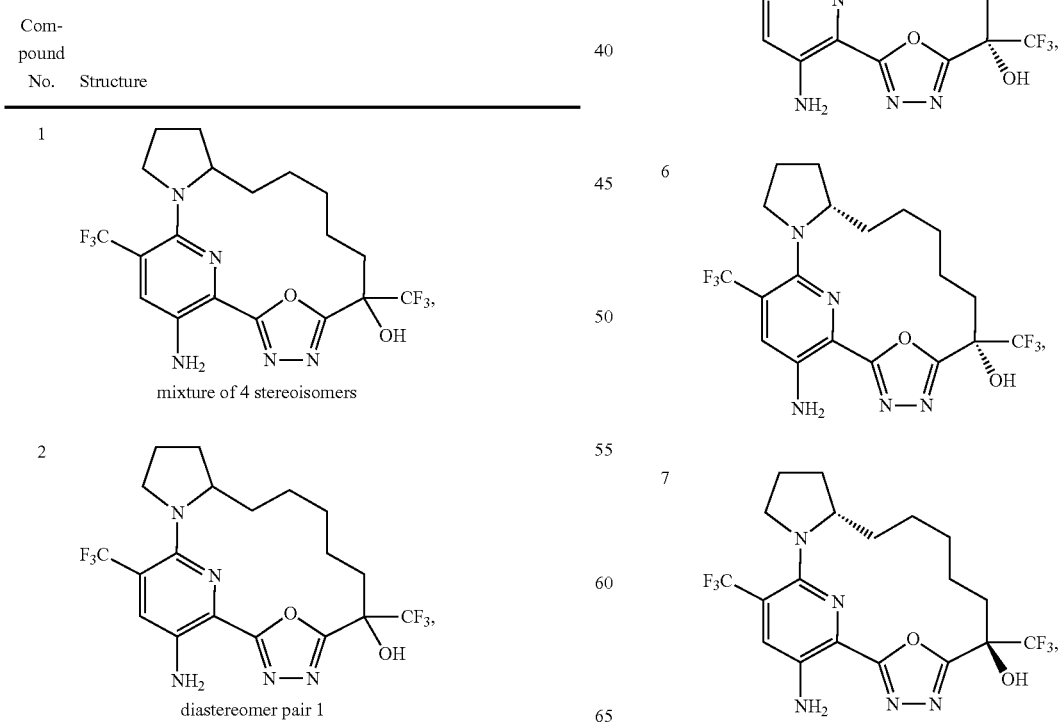 |
| 7 | 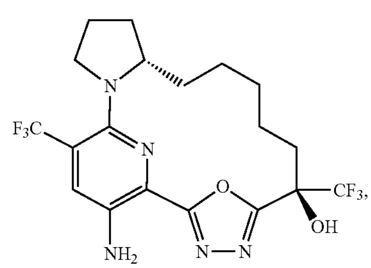 [SMILES: Nc1cc(C(F)(F)F)c2nc1-c1nnc(o1)[C@@](O)(C(F)(F)F)CCCCC[C@H]1CCCN21] |

1081
-continued
| Compound No. | Structure |
|---|---|
| 8 | 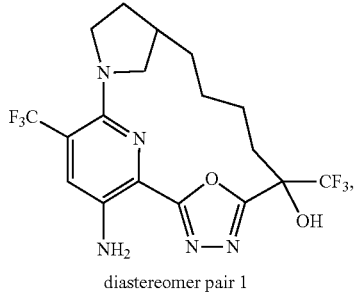 [SMILES: Nc1cc(C(F)(F)F)c2nc1-c1nnc(o1)C(O)(C(F)(F)F)CCCCC1CCN2C1]<br>diastereomer pair 1 |
| 9 | 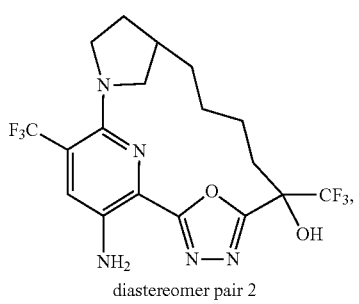 [SMILES: Nc1cc(C(F)(F)F)c2nc1-c1nnc(o1)C(O)(C(F)(F)F)CCCCC1CCN2C1]<br>diastereomer pair 2 |
| 10 | 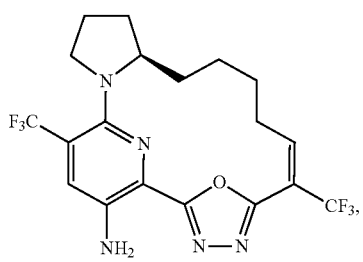 [SMILES: Nc1cc(C(F)(F)F)c2nc1-c1nnc(o1)/C(C(F)(F)F)=C\CCCC[C@@H]1CCCN21] |
| 11 | 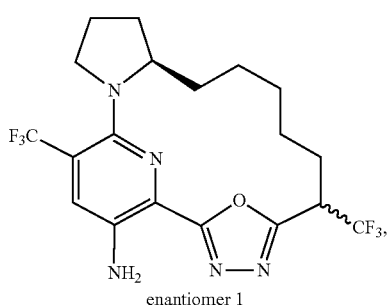 [SMILES: Nc1cc(C(F)(F)F)c2nc1-c1nnc(o1)C(C(F)(F)F)CCCCC[C@@H]1CCCN21]<br>enantiomer 1 |
| 12 | 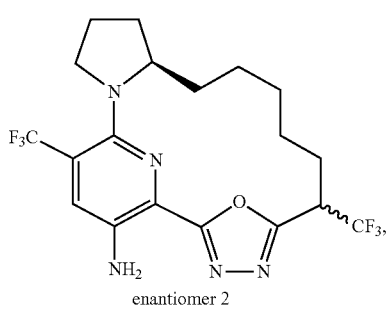 [SMILES: Nc1cc(C(F)(F)F)c2nc1-c1nnc(o1)C(C(F)(F)F)CCCCC[C@@H]1CCCN21]<br>enantiomer 2 |
1082
-continued
| Compound No. | Structure |
|---|---|
| 13 | 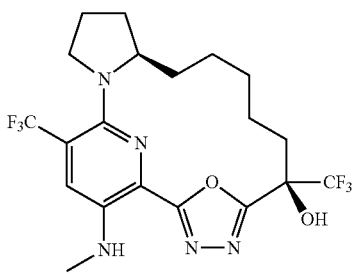 [SMILES: CNc1cc(C(F)(F)F)c2nc1C1=NN=C(O1)[C@@](O)(C(F)(F)F)CCCCC[C@@H]1CCCN21] |
| 14 | 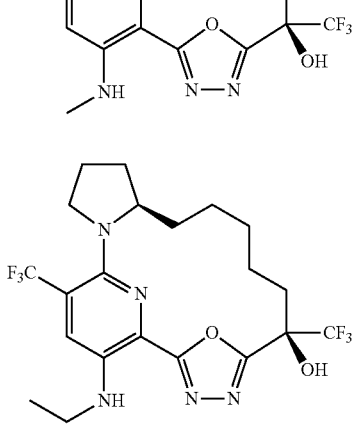 |
| 15 | 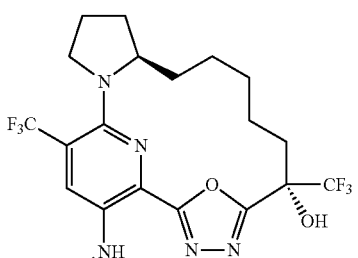 |
| 16 | 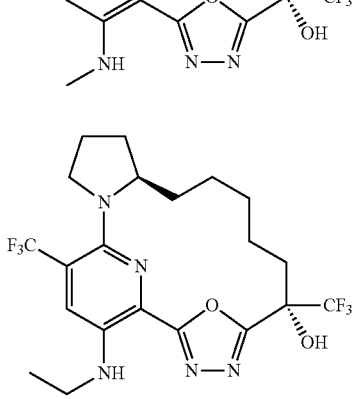 |
| 17 | 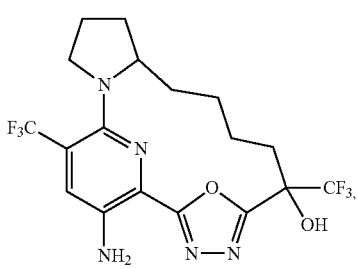<br>diastereomer pair 1 |

-continued
| Compound No. | Structure |
|---|---|
| 18 | 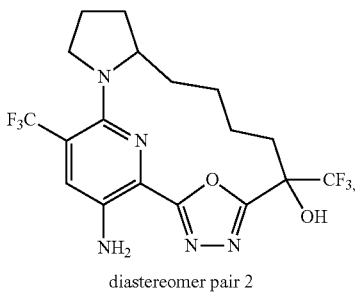 [SMILES: Nc1cc(C(F)(F)F)c2nc1C1=NN=C(O1)C(O)(C(F)(F)F)CCCCC1CCCN21] diastereomer pair 2 |
| 19 | 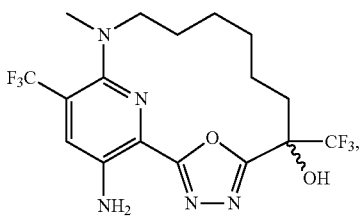 enantiomer 1 |
| 20 | 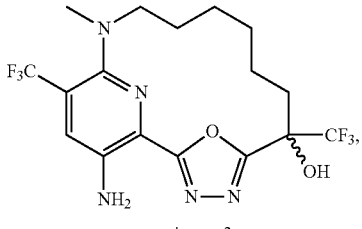 enantiomer 2 |
| 21 | 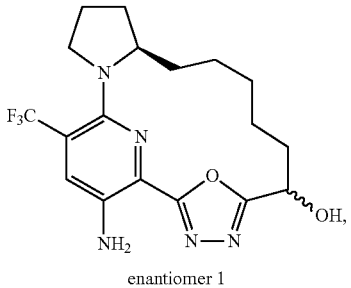 [SMILES: Nc1cc(C(F)(F)F)c2nc1C1=NN=C(O1)C(O)CCCCC[C@@H]1CCCN21] enantiomer 1 |
| 22 | 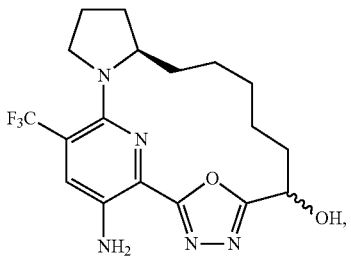 enantiomer 2 |
-continued
| Compound No. | Structure |
|---|---|
| 23 | 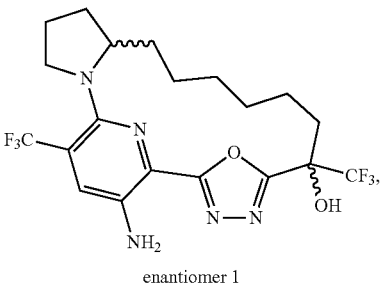 [SMILES: Nc1cc(C(F)(F)F)c2nc1-c1nnc(o1)C(O)(C(F)(F)F)CCCCCCC1CCCN21] enantiomer 1 |
| 24 | 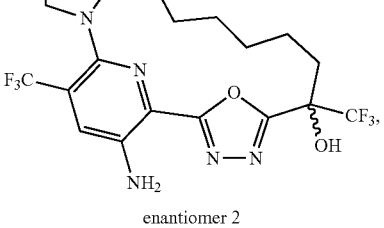 enantiomer 2 |
| 25 | 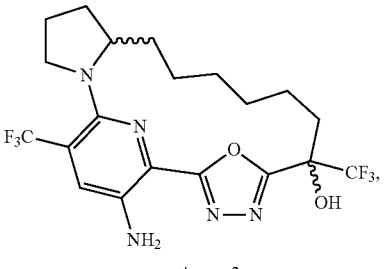 enantiomer 3 |
| 26 | 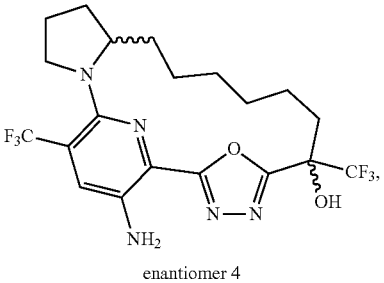 [SMILES: Nc1cc(C(F)(F)F)c2nc1-c1nnc(o1)C(O)(C(F)(F)F)CCCCCCC1CCCN21] enantiomer 4 |
| 27 | enantiomer 1 |

-continued
| Compound No. | Structure |
|---|---|
| 28 | 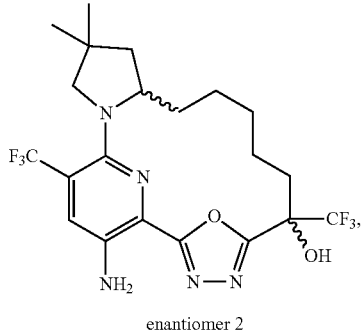 [SMILES: CC1(C)CC2CCCCCC(O)(C(F)(F)F)c3nnc(o3)-c3nc(c(C(F)(F)F)cc3N)N2C1] enantiomer 2 |
| 29 | 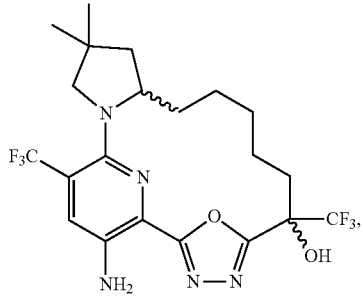 enantiomer 3 |
| 30 | 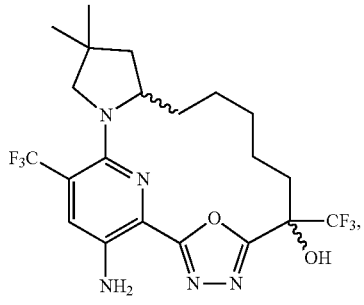 enantiomer 4 |
| 31 | 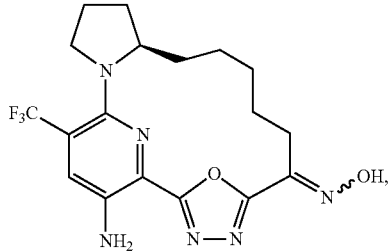 [SMILES: Nc1cc(C(F)(F)F)c2nc1-c1nnc(o1)C(=NO)CCCCC[C@@H]1CCCN21] |
-continued
| Compound No. | Structure |
|---|---|
| 32 | 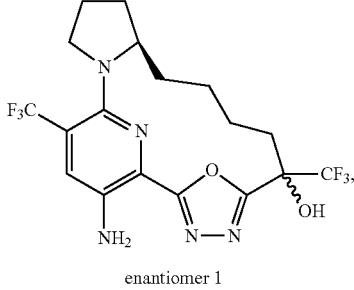 [SMILES: Nc1cc(C(F)(F)F)c2nc1-c1nnc(o1)C(O)(C(F)(F)F)CCCC[C@@H]1CCCN21] enantiomer 1 |
| 33 | 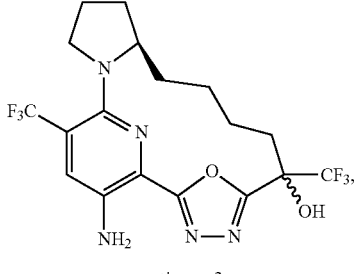 enantiomer 2 |
| 34 | 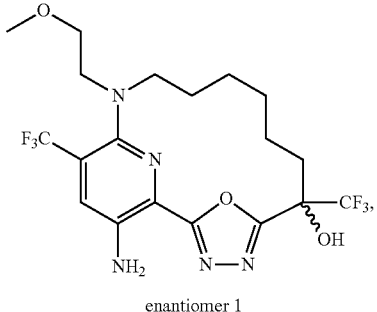 [SMILES: COCCN1CCCCCCC(O)(C(F)(F)F)C2=NN=C(O2)c2nc1c(C(F)(F)F)cc2N] enantiomer 1 |
| 35 | 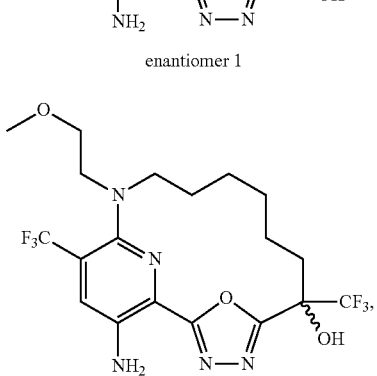 enantiomer 2 |
| 36 | 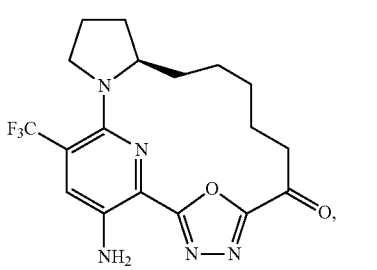 [SMILES: Nc1cc(C(F)(F)F)c2nc1-c1nnc(o1)C(=O)CCCCC[C@@H]1CCCN21] |

| Compound No. | Structure |
|---|---|
| 37 | 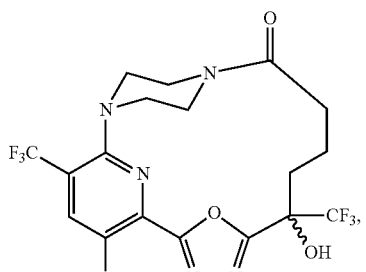
enantiomer 1 |
| 38 | 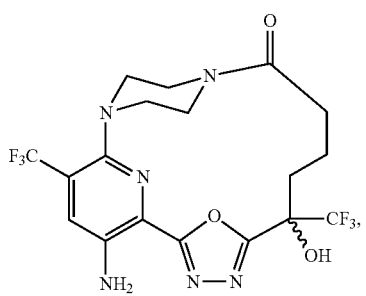
enantiomer 2 |
| 39 | 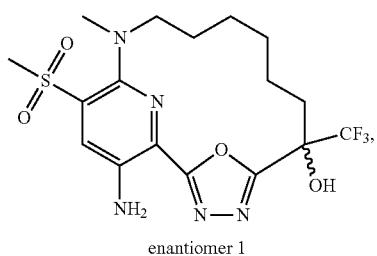 [SMILES: CN1CCCCCCC(O)(C(F)(F)F)c2nnc(o2)-c2nc1c(S(C)(=O)=O)cc2N]
enantiomer 1 |
| 40 | 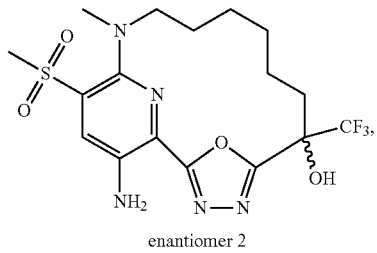 [SMILES: CN1CCCCCCC(O)(C(F)(F)F)c2nnc(o2)-c2nc1c(S(C)(=O)=O)cc2N]
enantiomer 2 |
| 41 | 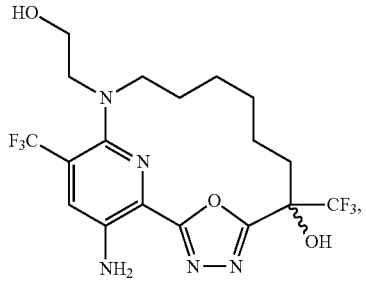
enantiomer 1 |
| Compound No. | Structure |
|---|---|
| 42 | 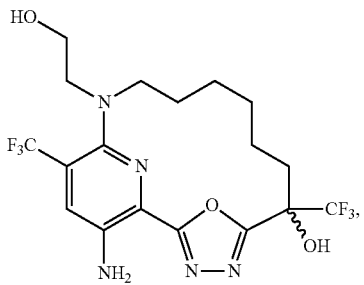
enantiomer 2 |
| 43 | 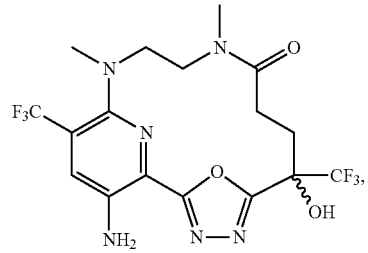
enantiomer 1 |
| 44 | 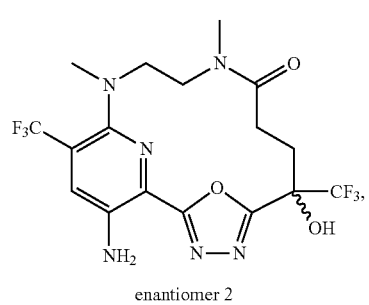 [SMILES: CN1CCN(C)c2nc(c(N)cc2C(F)(F)F)C2=NN=C(O2)C(O)(C(F)(F)F)CCC1=O]
enantiomer 2 |
| 45 | 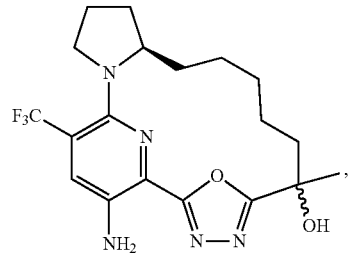 |
| 46 | 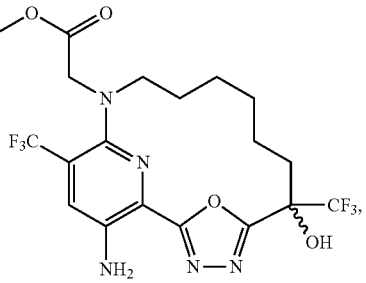
enantiomer 1 |

TABLE-continued
| Compound No. | Structure |
|---|---|
| 47 | 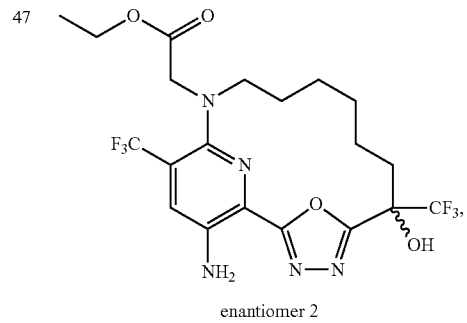enantiomer 2 |
| 48 | 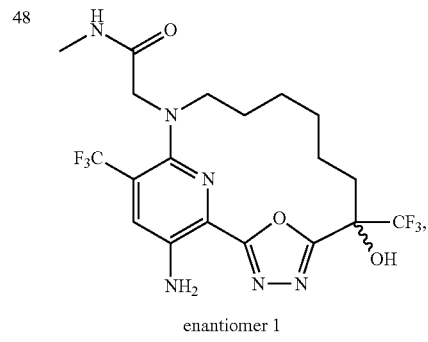enantiomer 1 |
| 49 | 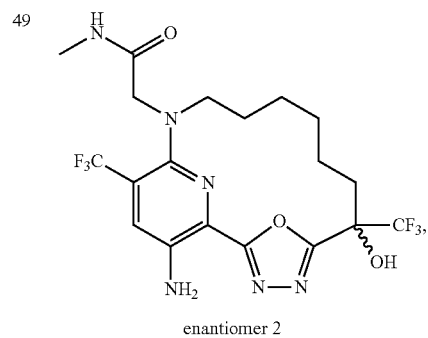enantiomer 2 |
| 50 | 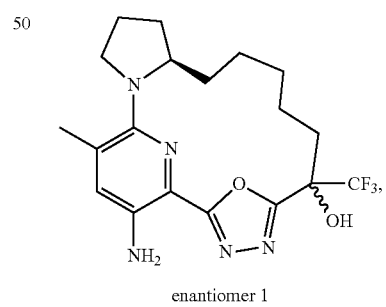enantiomer 1 |
| 51 | 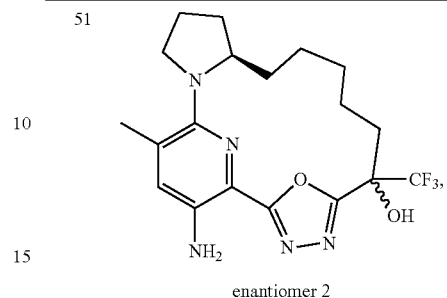enantiomer 2 |
| 52 | 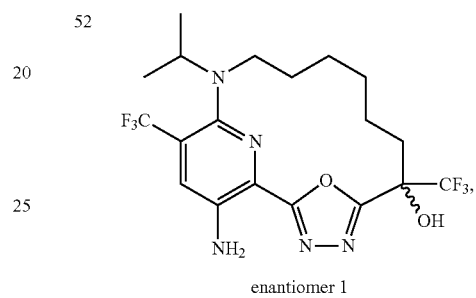enantiomer 1 |
| 53 | 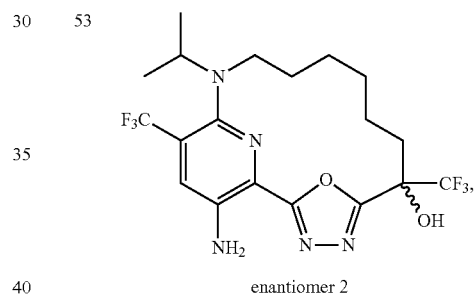enantiomer 2 |
| 54 | 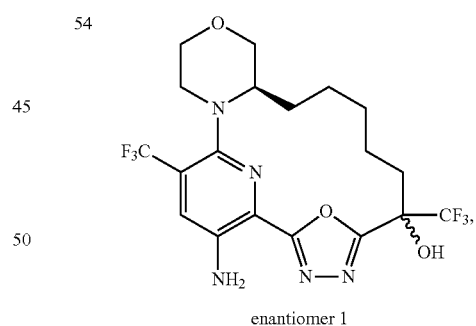enantiomer 1 |
| 55 | 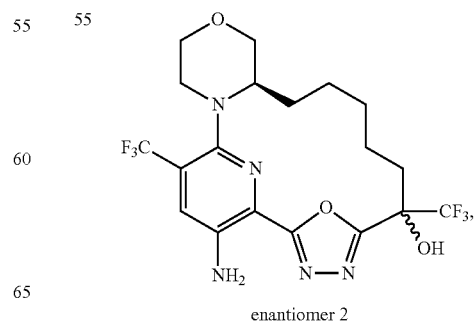enantiomer 2 |

-continued
| Compound No. | Structure |
|---|---|
| 56 | 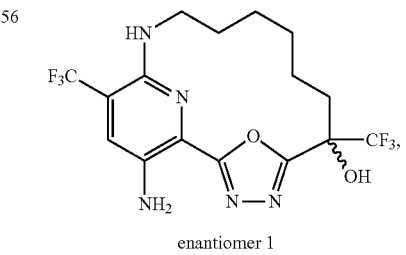 enantiomer 1 |
| 57 | 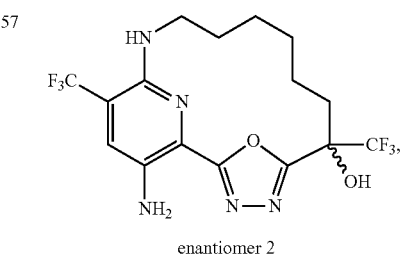 enantiomer 2 |
| 58 | 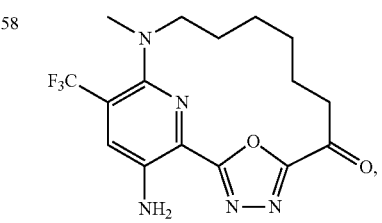 |
| 59 | 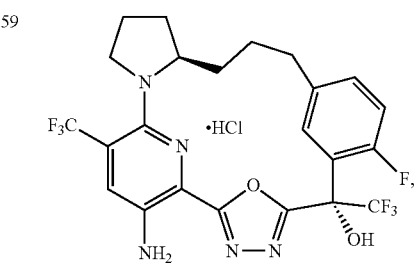 |
| 60 | 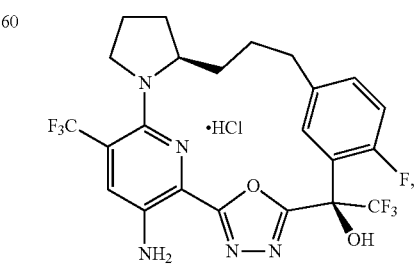 |
| 61 | 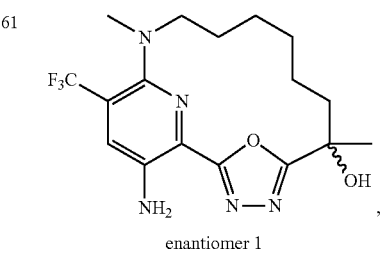 enantiomer 1 |
-continued
| Compound No. | Structure |
|---|---|
| 62 | 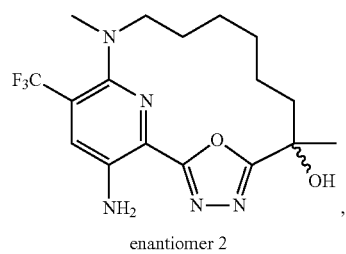 [SMILES: CN1CCCCCCC(C)(O)C2=NN=C(O2)c2nc1c(C(F)(F)F)cc2N] enantiomer 2 |
| 63 | 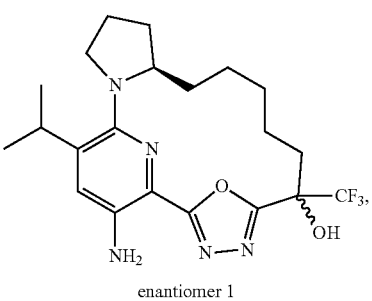 [SMILES: CC(C)c1cc(N)c2nc1N1CCC[C@H]1CCCCCC(O)(C(F)(F)F)C1=NN=C2O1] enantiomer 1 |
| 64 | 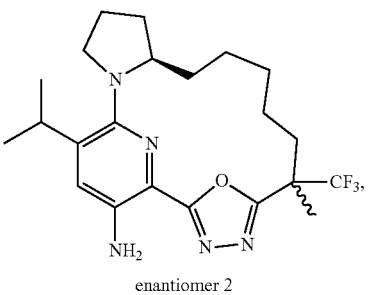 [SMILES: CC(C)c1cc(N)c2nc1N1CCC[C@H]1CCCCCC(C)(C(F)(F)F)c1nnc-2o1] enantiomer 2 |
| 65 | 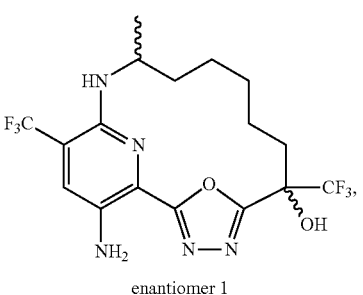 enantiomer 1 |
| 66 | 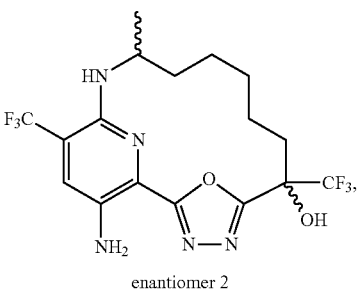 enantiomer 2 |

-continued
| Compound No. | Structure |
|---|---|
| 67 | 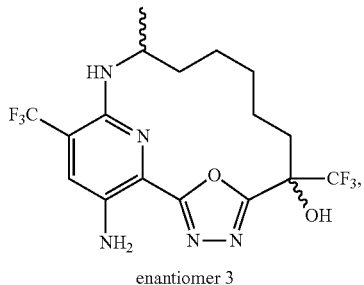 [SMILES: CC1CCCCCC(O)(C(F)(F)F)C2=NN=C(O2)c2nc(c(C(F)(F)F)cc2N)N1]<br>enantiomer 3 |
| 68 | 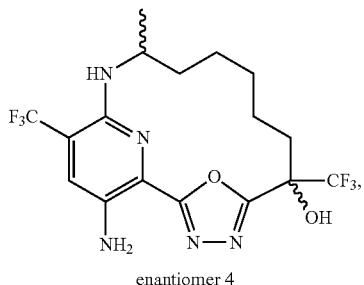 [SMILES: CC1CCCCCC(O)(C(F)(F)F)C2=NN=C(O2)c2nc(c(C(F)(F)F)cc2N)N1]<br>enantiomer 4 |
| 69 | 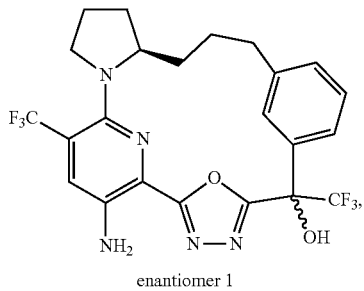 [SMILES: Nc1cc(C(F)(F)F)c2nc1-c1nnc(o1)C(O)(C(F)(F)F)c1cccc(c1)CCC[C@@H]1CCCN21]<br>enantiomer 1 |
| 70 | 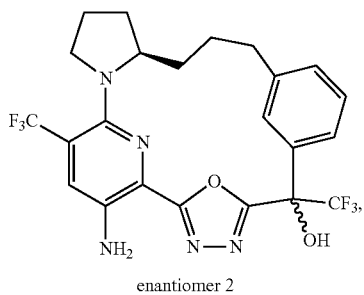 [SMILES: Nc1cc(C(F)(F)F)c2nc1-c1nnc(o1)C(O)(C(F)(F)F)c1cccc(c1)CCC[C@@H]1CCCN21]<br>enantiomer 2 |
| 71 | 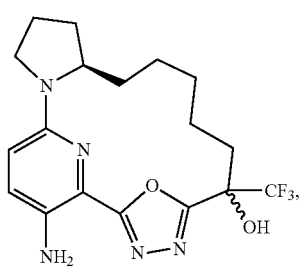<br>enantiomer 2 |
-continued
| Compound No. | Structure |
|---|---|
| 72 | 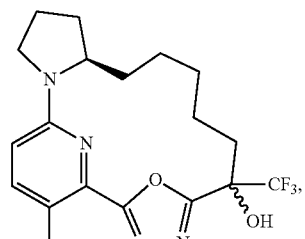<br>enantiomer 2 |
| 73 | 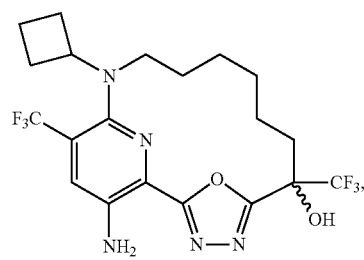<br>enantiomer 1 |
| 74 | 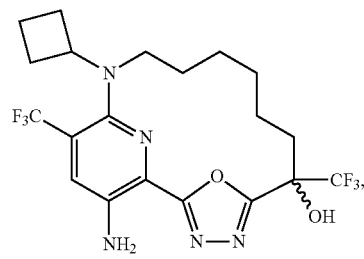<br>enantiomer 2 |
| 75 | 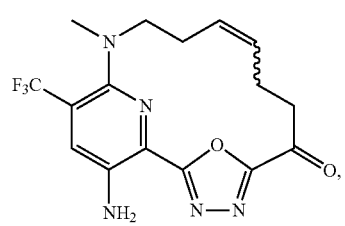 |
| 76 | 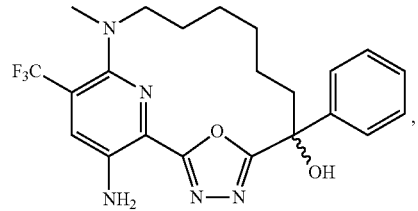<br>enantiomer 1 |

TABLE -continued
| Compound No. | Structure |
|---|---|
| 77 | 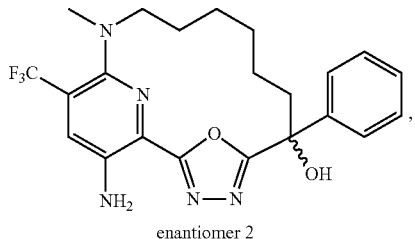 [SMILES: CN1CCCCCCC(O)(c2ccccc2)C2=NN=C(O2)c2nc1c(C(F)(F)F)cc2N] enantiomer 2 |
| 78 | 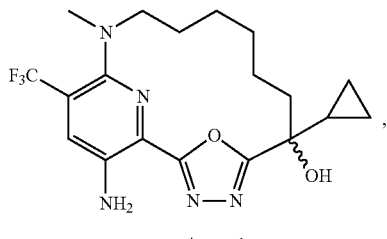 enantiomer 1 |
| 79 | 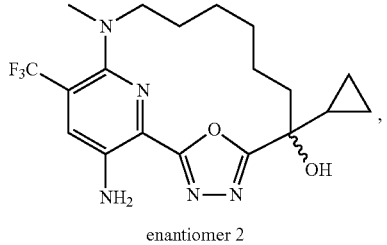 [SMILES: CN1CCCCCCC(O)(C2CC2)C2=NN=C(O2)c2nc1c(C(F)(F)F)cc2N] enantiomer 2 |
| 80 | 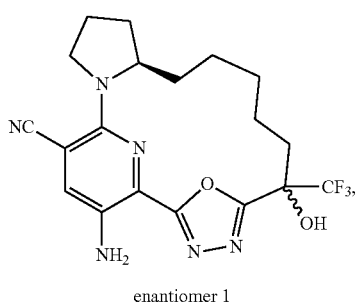 [SMILES: N#Cc1cc(N)c2nc1N1CCC[C@H]1CCCCCC(O)(C(F)(F)F)C1=NN=C2O1] enantiomer 1 |
| 81 | 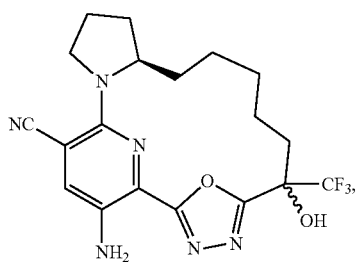 enantiomer 2 |
| 82 | 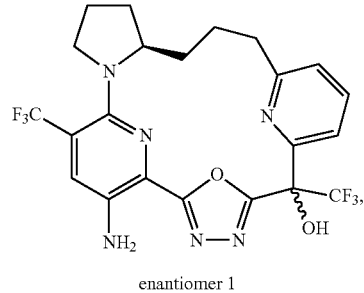 [SMILES: Nc1cc(C(F)(F)F)c2nc1C1=NN=C(O1)C(O)(C(F)(F)F)c1cccc(n1)CCC[C@@H]1CCCN21] enantiomer 1 |
| 83 | 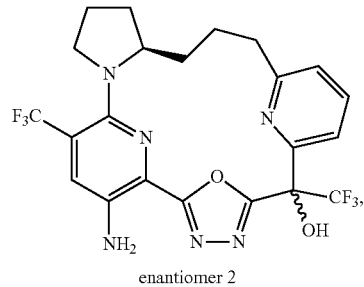 [SMILES: Nc1cc(C(F)(F)F)c2nc1C1=NN=C(O1)C(O)(C(F)(F)F)c1cccc(n1)CCC[C@@H]1CCCN21] enantiomer 2 |
| 84 | 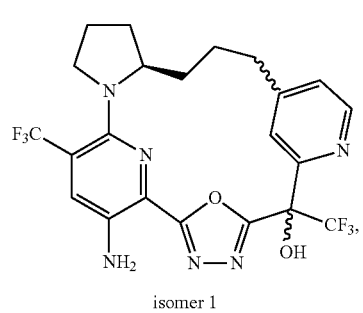 [SMILES: Nc1cc(C(F)(F)F)c2nc1C1=NN=C(O1)C(O)(C(F)(F)F)c1cc(ccn1)CCC[C@@H]1CCCN21] isomer 1 |
| 85 | 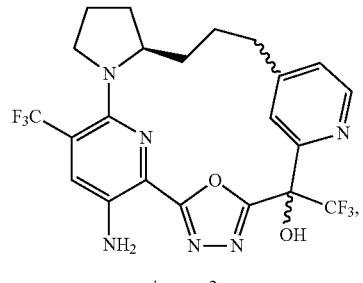 isomer 2 |
| 86 | 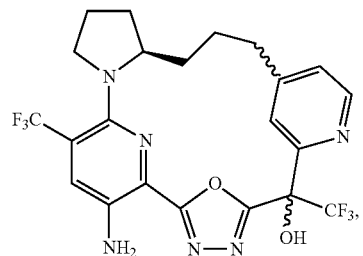 isomer 3 |

1097
-continued
| Compound No. | Structure |
|---|---|
| 87 | 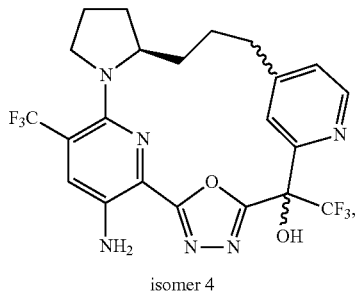 [SMILES: Nc1cc(C(F)(F)F)c2nc1C1=NN=C(O1)C(O)(C(F)(F)F)c1cc(ccn1)CCC[C@@H]1CCCN21]<br>isomer 4 |
| 88 | 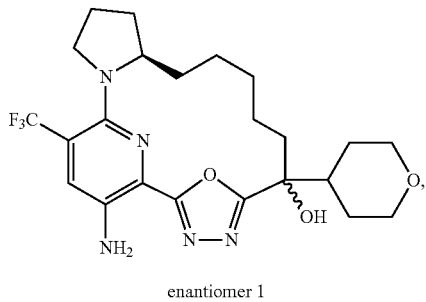 [SMILES: Nc1cc(C(F)(F)F)c2nc1-c1nnc(o1)C(O)(C1CCOCC1)CCCCC[C@@H]1CCCN21]<br>enantiomer 1 |
| 89 | 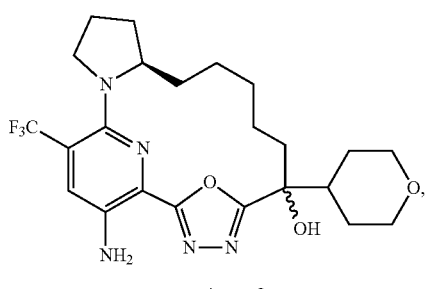<br>enantiomer 2 |
| 90 | 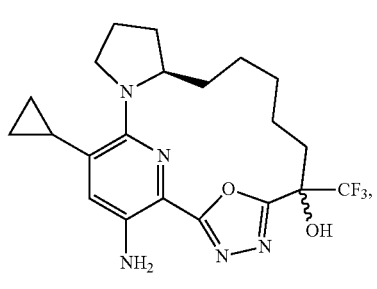<br>enantiomer 1 |
| 91 | 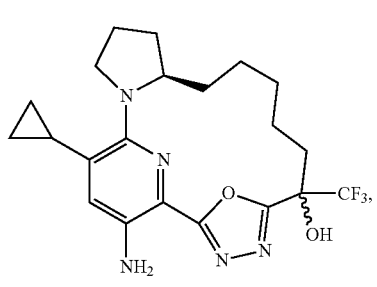<br>enantiomer 2 |
1098
-continued
| Compound No. | Structure |
|---|---|
| 92 | 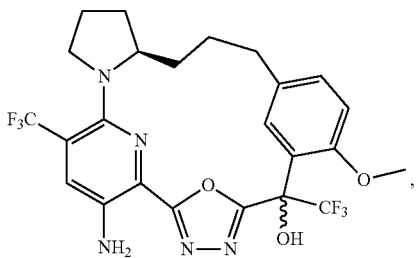<br>enantiomer 1 |
| 93 | 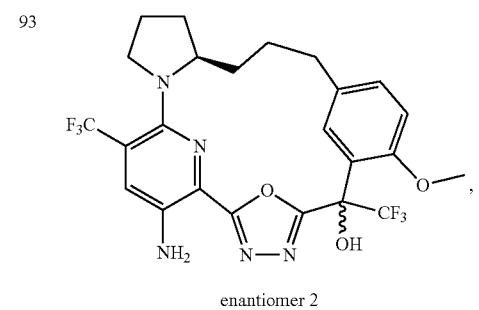<br>enantiomer 2 |
| 94 | 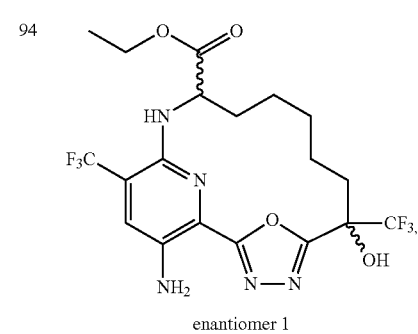<br>enantiomer 1 |
| 95 | 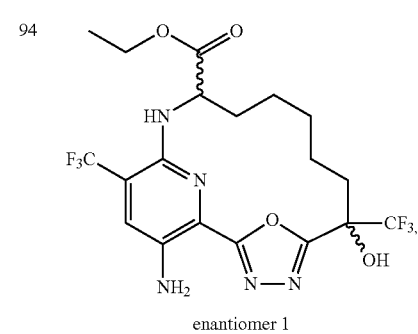<br>enantiomer 2 |

-continued
| Compound No. | Structure |
|---|---|
| 96 | 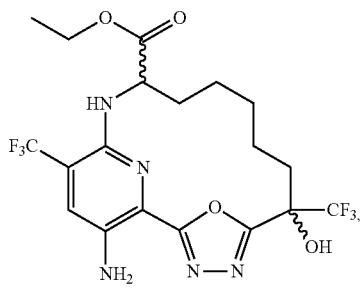<br>enantiomer 3 |
| 97 | 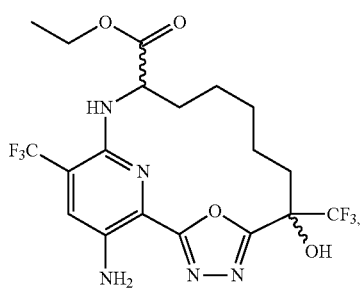<br>enantiomer 4 |
| 98 | 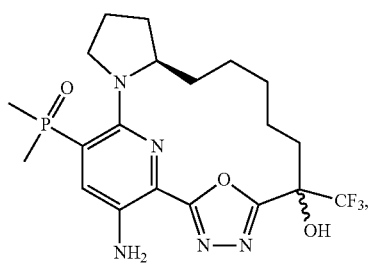<br>enantiomer 1 |
| 99 | 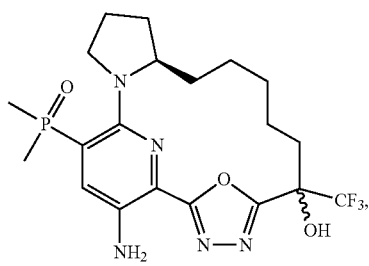<br>enantiomer 2 |
-continued
| Compound No. | Structure |
|---|---|
| 100 | 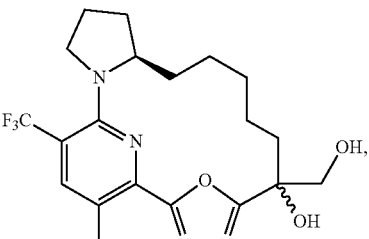<br>enantiomer 1 |
| 101 | 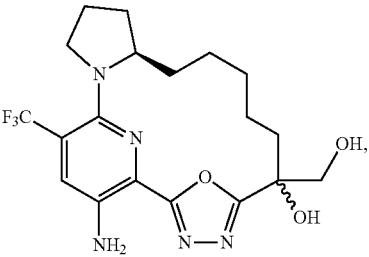<br>enantiomer 2 |
| 102 | 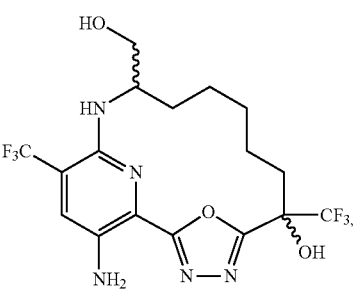<br>enantiomer 1 |
| 103 | 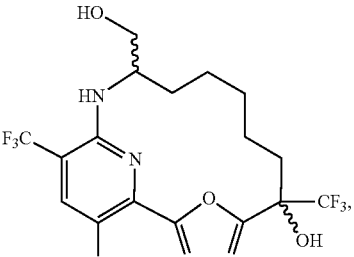<br>enantiomer 2 |

| Compound No. | Structure |
|---|---|
| 104 | 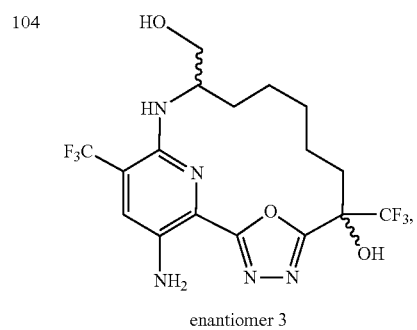<br>enantiomer 3 |
| 105 | 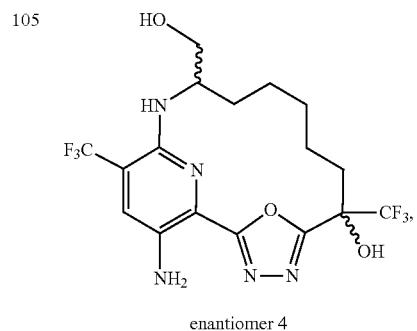<br>enantiomer 4 |
| 106 | 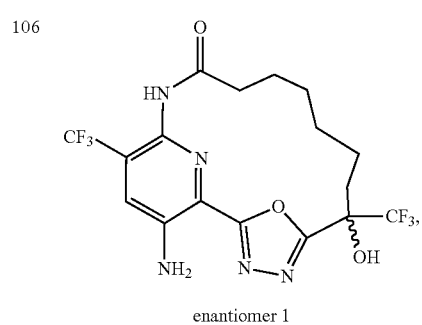<br>enantiomer 1 |
| 107 | 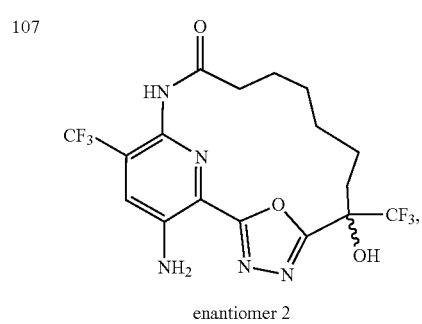<br>enantiomer 2 |
| Compound No. | Structure |
|---|---|
| 108 | 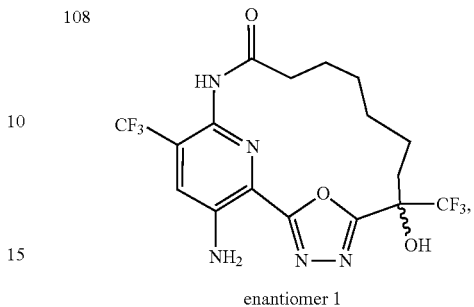<br>enantiomer 1 |
| 109 | 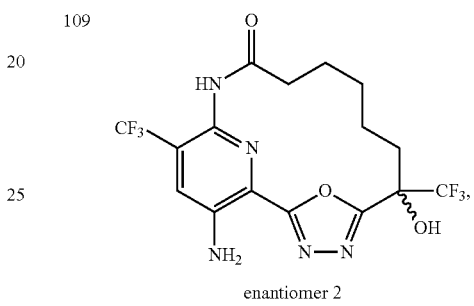<br>enantiomer 2 |
| 110 | 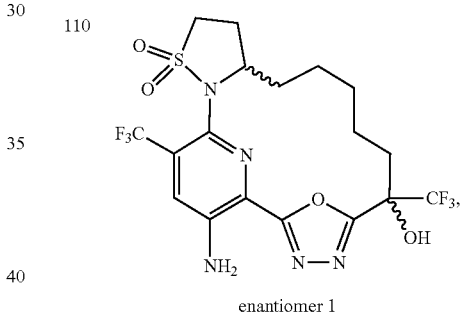<br>enantiomer 1 |
| 111 | 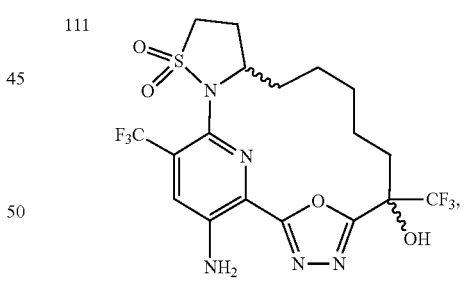<br>enantiomer 2 |
| 112 | 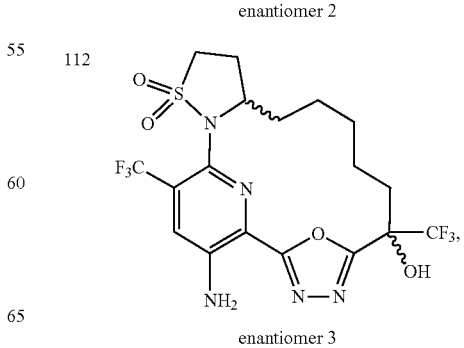<br>enantiomer 3 |

| Compound No. | Structure |
|---|---|
| 113 | 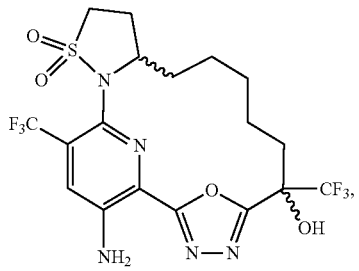<br>enantiomer 4 |
| 114 | 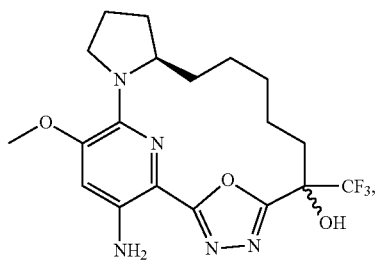<br>enantiomer 1 |
| 115 | 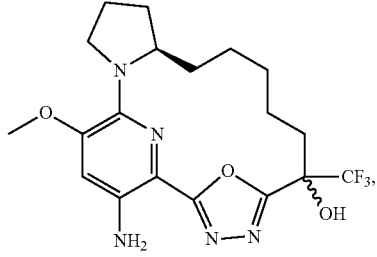<br>enantiomer 2 |
| 116 | 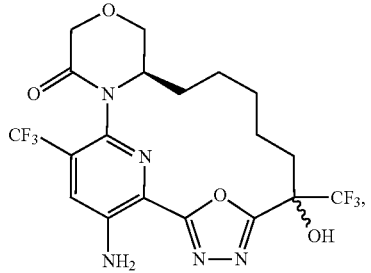<br>enantiomer 1 |
| Compound No. | Structure |
|---|---|
| 117 | 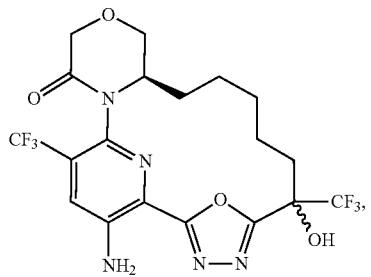<br>enantiomer 2 |
| 118 | 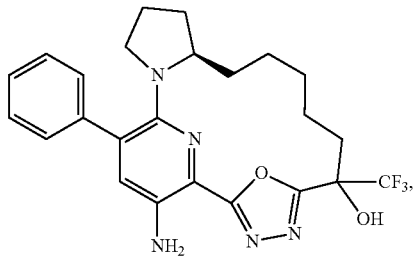 [SMILES: Nc1cc(-c2ccccc2)c2nc1C1=NN=C(O1)C(O)(C(F)(F)F)CCCCC[C@@H]1CCCN21]<br>  |
| 119 | 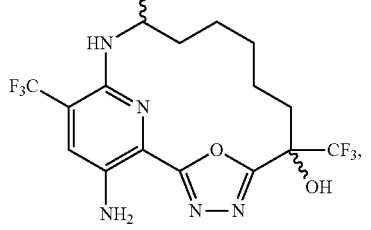<br>enantiomer 1 |
| 120 | <br>enantiomer 2 |

| Compound No. | Structure |
|---|---|
| 121 | 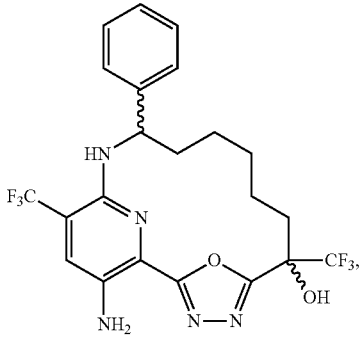 enantiomer 3 |
| 122 | 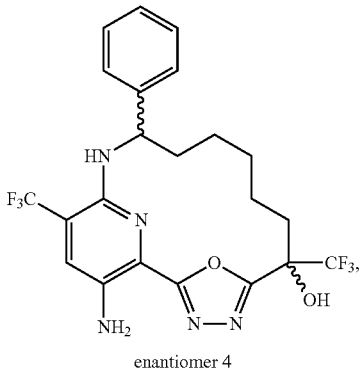 [SMILES: Nc1cc(C(F)(F)F)c2nc1-c1nnc(o1)C(O)(C(F)(F)F)CCCCCC(c1ccccc1)N2] enantiomer 4 |
| 123 | 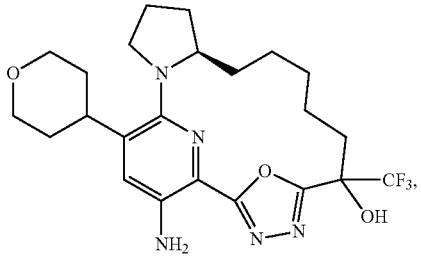 [SMILES: Nc1cc(C2CCOCC2)c2nc1C1=NN=C(O1)C(O)(C(F)(F)F)CCCCC[C@@H]1CCCN21] |
| 124 | 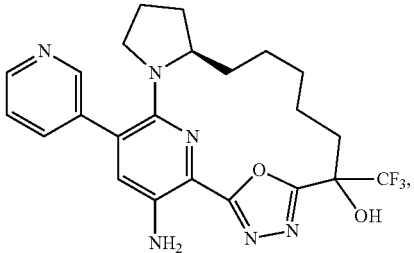 [SMILES: Nc1cc(-c2cccnc2)c2nc1C1=NN=C(O1)C(O)(C(F)(F)F)CCCCC[C@@H]1CCCN21] |
| 125 | 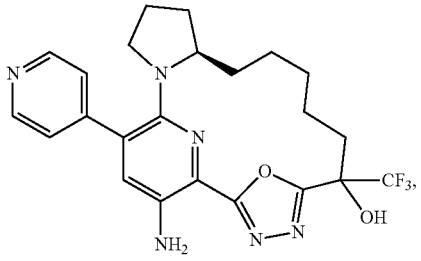 [SMILES: Nc1cc(-c2ccncc2)c2nc1C1=NN=C(O1)C(O)(C(F)(F)F)CCCCC[C@@H]1CCCN21] |
| Compound No. | Structure |
|---|---|
| 126 | 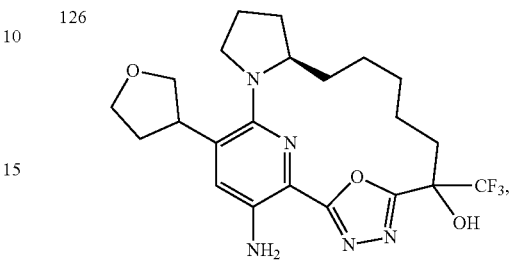 |
| 127 | 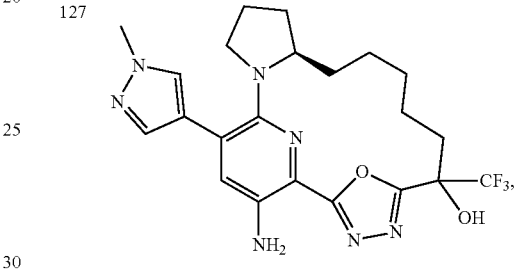 |
| 128 | 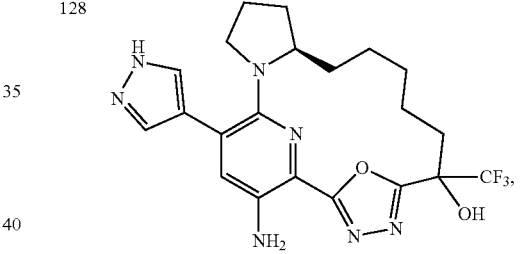 |
| 129 | 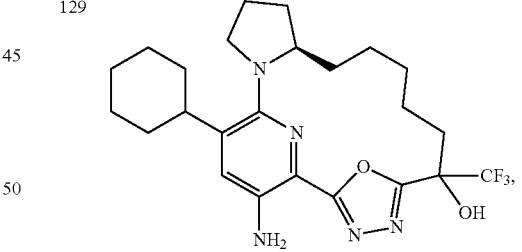 |
| 130 | 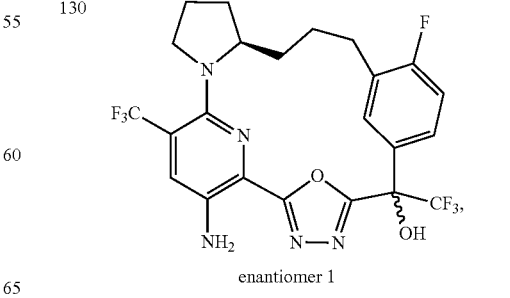 enantiomer 1 |

| Compound No. | Structure |
|---|---|
| 131 | 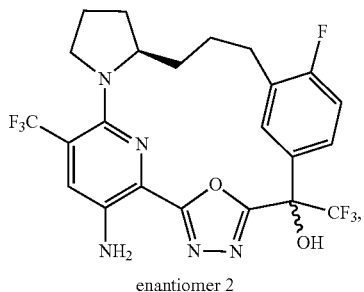 [SMILES: Nc1cc(C(F)(F)F)c2nc1-c1nnc(o1)C(O)(C(F)(F)F)c1ccc(F)c(c1)CCC[C@@H]1CCCN21]<br>enantiomer 2 |
| 132 | 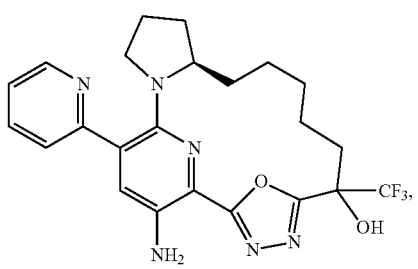 |
| 133 | 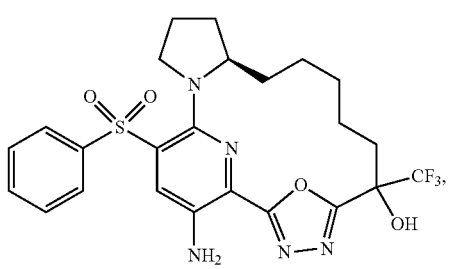 [SMILES: Nc1cc(S(=O)(=O)c2ccccc2)c2nc1C1=NN=C(O1)C(O)(C(F)(F)F)CCCCC[C@@H]1CCCN21] |
| 134 | 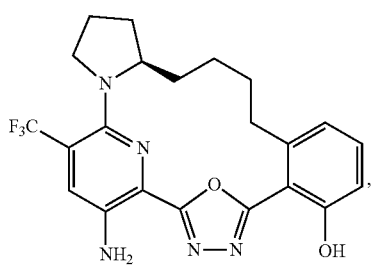 [SMILES: Nc1cc(C(F)(F)F)c2nc1C1=NN=C(O1)c1c(O)cccc1CCCC[C@@H]1CCCN21] |
| 135 | 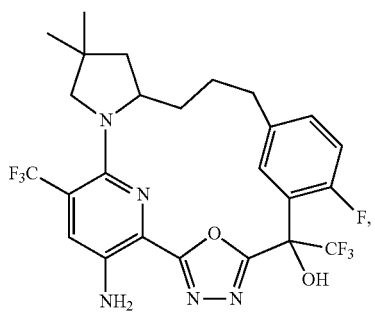<br>diastereomer pair 1 |
| Compound No. | Structure |
|---|---|
| 136 | 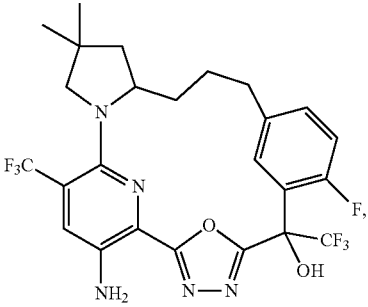<br>diastereomer pair 2 |
| 137 | 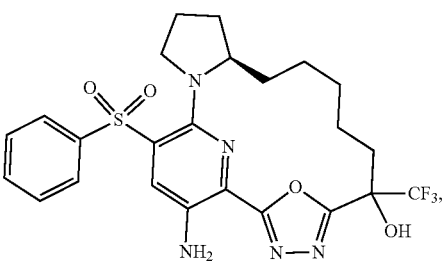 [SMILES: Nc1cc(S(=O)(=O)c2ccccc2)c2nc1C1=NN=C(O1)C(O)(C(F)(F)F)CCCCC[C@@H]1CCCN21] |
| 138 | 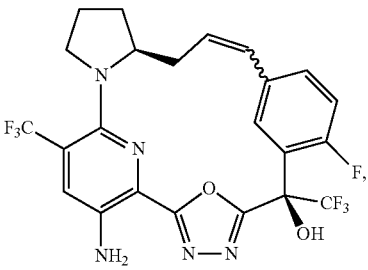 [SMILES: Nc1cc(C(F)(F)F)c2nc1-c1nnc(o1)[C@@](O)(C(F)(F)F)c1cc(ccc1F)C=CC[C@@H]1CCCN21] |
| 139 | 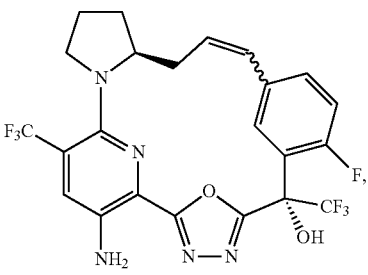 [SMILES: Nc1cc(C(F)(F)F)c2nc1-c1nnc(o1)[C@](O)(C(F)(F)F)c1cc(ccc1F)C=CC[C@@H]1CCCN21] |
| 140 | 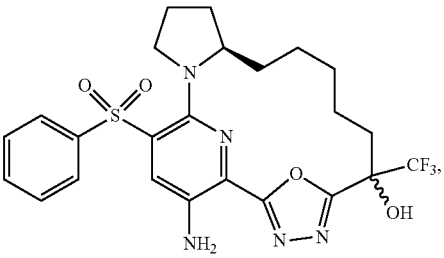<br>enantiomer 1 |

| Compound No. | Structure |
|---|---|
| 141 | 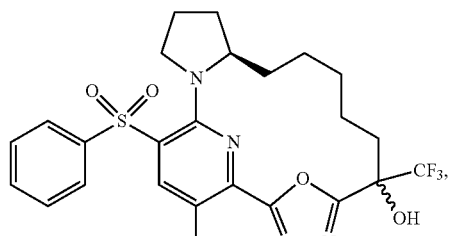 enantiomer 2 |
| 142 | 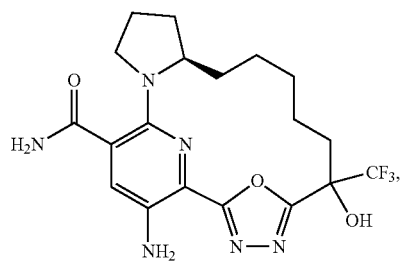 [SMILES: NC(=O)c1cc(N)c2nc1N1CCC[C@H]1CCCCCC(O)(C(F)(F)F)C1=NN=C2O1] |
| 143 | 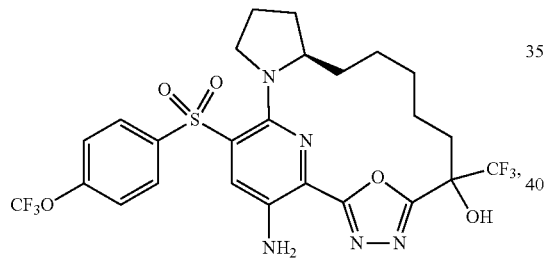 |
| 144 | 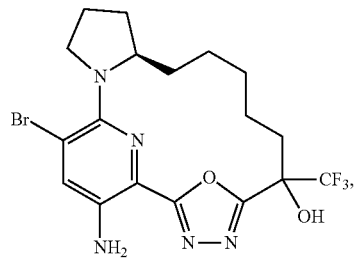 [SMILES: Nc1cc(Br)c2nc1C1=NN=C(O1)C(O)(C(F)(F)F)CCCCC[C@@H]1CCCN21] |
| 145 | 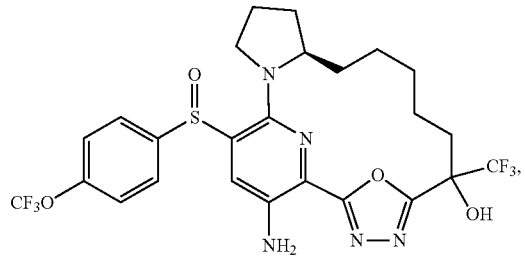 |
| Compound No. | Structure |
|---|---|
| 146 | 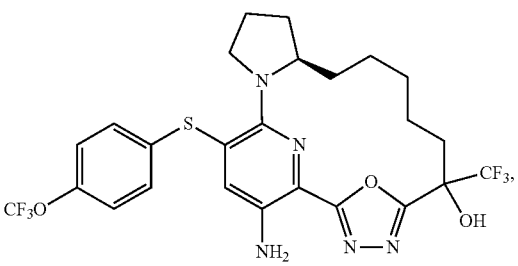 |
| 147 | 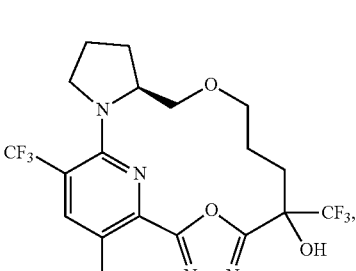 |
| 148 | 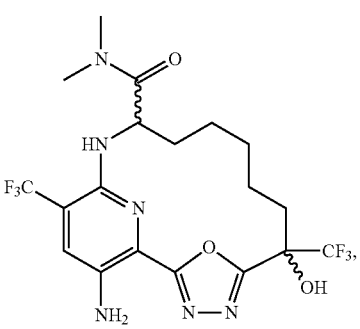 enantiomer 1 |
| 149 | 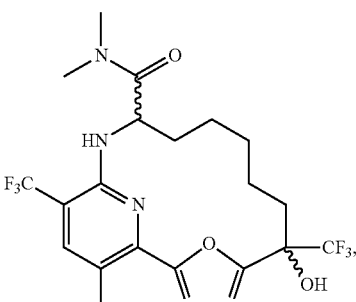 enantiomer 2 |

| Compound No. | Structure |
|---|---|
| 150 | 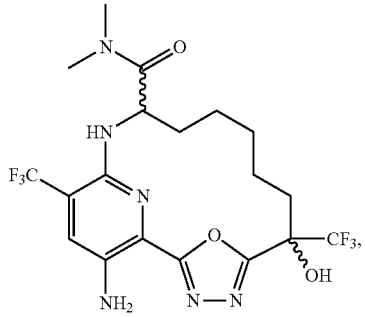<br>enantiomer 3 |
| 151 | 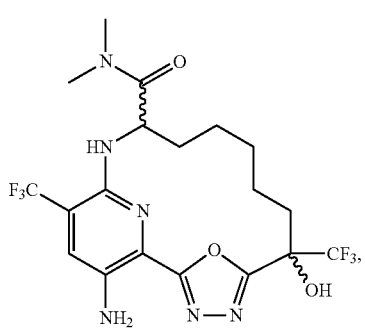<br>enantiomer 4 |
| 152 | 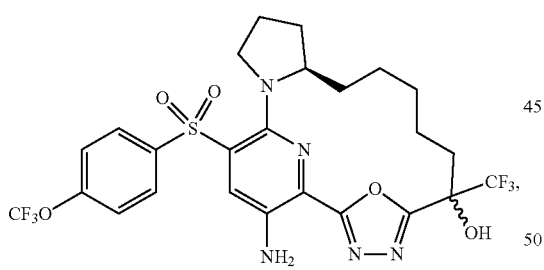<br>enantiomer 1 |
| 153 | 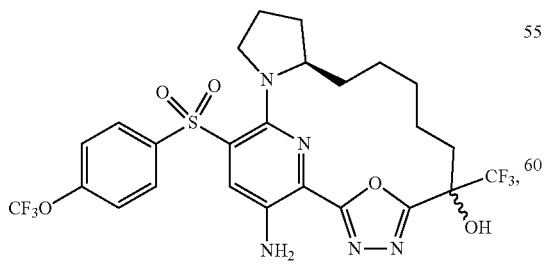<br>enantiomer 2 |
| Compound No. | Structure |
|---|---|
| 154 | 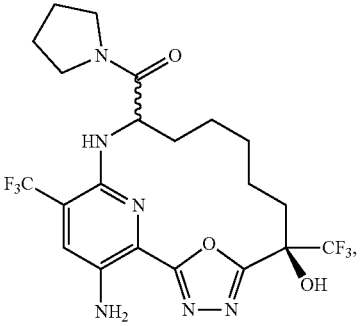 [SMILES: Nc1cc(C(F)(F)F)c2nc1C1=NN=C(O1)[C@@](O)(C(F)(F)F)CCCCCC(C(=O)N1CCCC1)N2] |
| 155 | 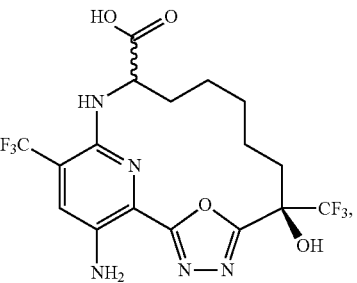<br>enantiomer 1 |
| 156 | 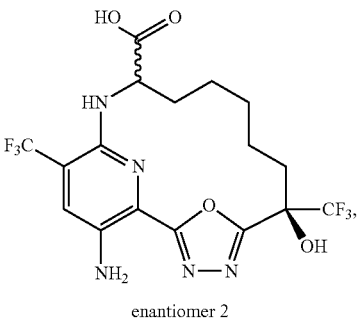 [SMILES: Nc1cc(C(F)(F)F)c2nc1C1=NN=C(O1)[C@@](O)(C(F)(F)F)CCCCCC(C(=O)O)N2]<br>enantiomer 2 |
| 157 | 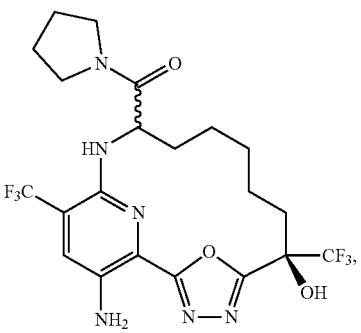<br>enantiomer 1 |

| Compound No. | Structure |
|---|---|
| 158 | 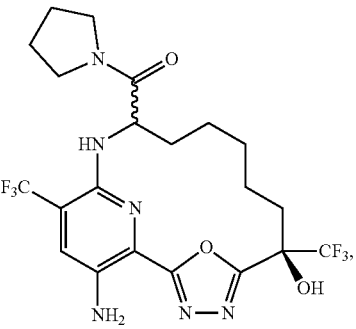<br>enantiomer 2 |
| 159 | 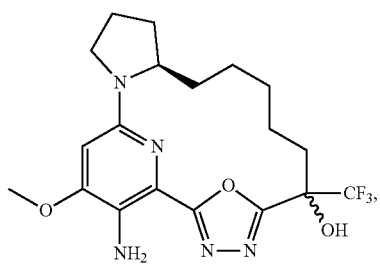<br>enantiomer 1 |
| 160 | 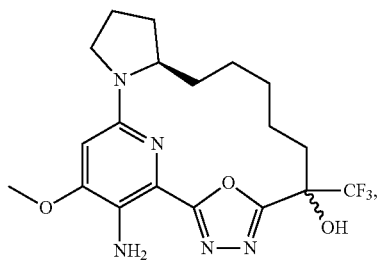<br>enantiomer 2 |
| 161 | 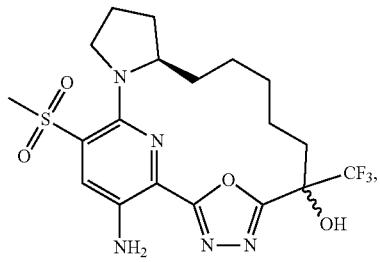<br>enantiomer 1 |
| Compound No. | Structure |
|---|---|
| 162 | 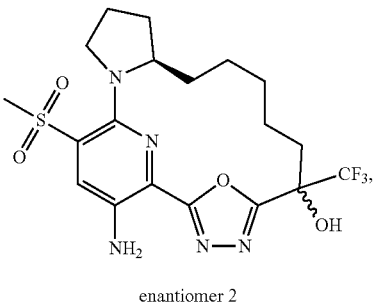 [SMILES: CS(=O)(=O)c1cc(N)c2nc1N1CCC[C@H]1CCCCCC(O)(C(F)(F)F)C1=NN=C2O1]<br>enantiomer 2 |
| 163 | 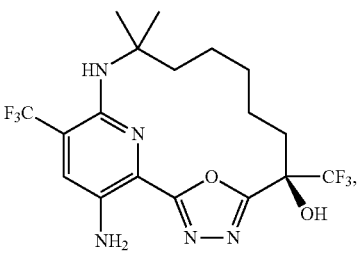 |
| 164 | 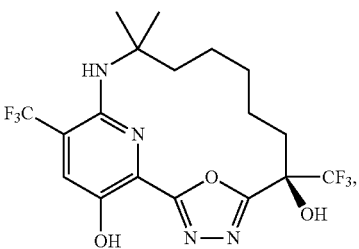 [SMILES: CC1(C)CCCCC[C@](O)(C(F)(F)F)c2nnc(o2)-c2nc(c(C(F)(F)F)cc2O)N1] |
| 165 | 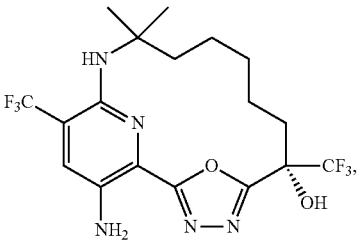 [SMILES: CC1(C)CCCCC[C@@](O)(C(F)(F)F)c2nnc(o2)-c2nc(c(C(F)(F)F)cc2N)N1] |
| 166 | 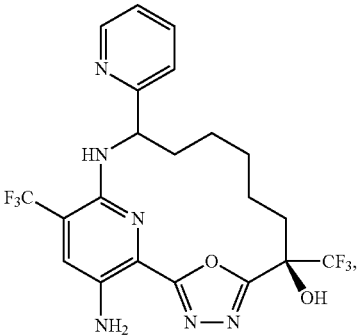 [SMILES: Nc1cc(C(F)(F)F)c2nc1-c1nnc(o1)[C@@](O)(C(F)(F)F)CCCCCC(c1ccccn1)N2] |

| Compound No. | Structure |
|---|---|
| 167 | 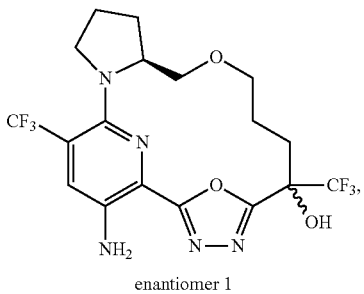 [SMILES: Nc1cc(C(F)(F)F)c2nc1-c1nnc(o1)C(O)(C(F)(F)F)CCCOC[C@@H]1CCCN21]<br>enantiomer 1 |
| 168 | 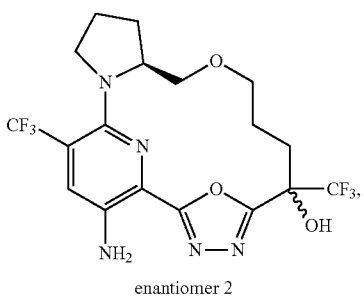 [SMILES: Nc1cc(C(F)(F)F)c2nc1-c1nnc(o1)C(O)(C(F)(F)F)CCCOC[C@@H]1CCCN21]<br>enantiomer 2 |
| 169 | 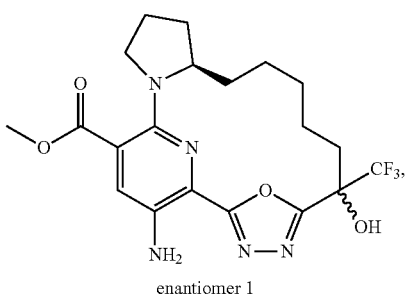 [SMILES: COC(=O)c1cc(N)c2nc1N1CCC[C@H]1CCCCCC(O)(C(F)(F)F)c1nnc-2o1]<br>enantiomer 1 |
| 170 | 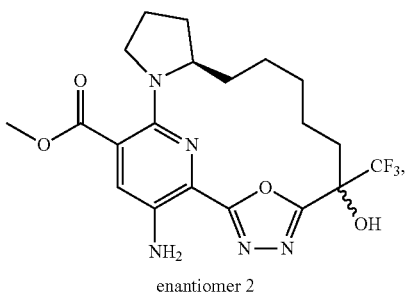 [SMILES: COC(=O)c1cc(N)c2nc1N1CCC[C@H]1CCCCCC(O)(C(F)(F)F)c1nnc-2o1]<br>enantiomer 2 |
| 171 | 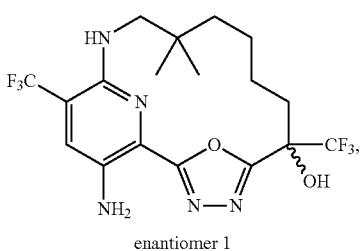 [SMILES: CC1(C)CCCCC(O)(C(F)(F)F)c2nnc(o2)-c2nc(c(C(F)(F)F)cc2N)NC1] |
| Compound No. | Structure |
|---|---|
| 172 | 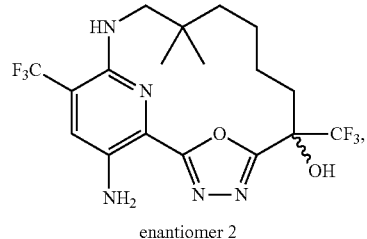 [SMILES: CC1(C)CCCCC(O)(C(F)(F)F)c2nnc(o2)-c2nc(c(C(F)(F)F)cc2N)NC1]<br>enantiomer 2 |
| 173 | 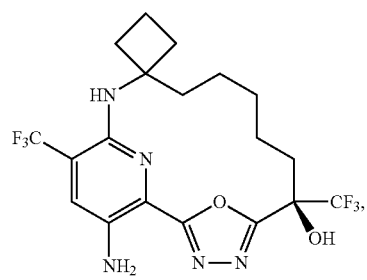 |
| 174 | 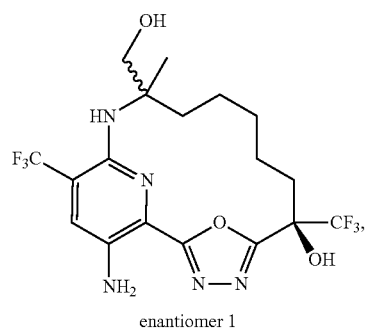 [SMILES: CC1(CO)CCCCC[C@](O)(C(F)(F)F)c2nnc(o2)-c2nc(c(C(F)(F)F)cc2N)N1]<br>enantiomer 1 |
| 175 | 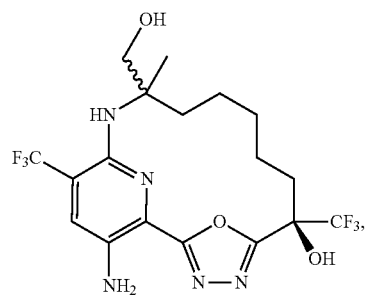<br>enantiomer 2 |
| 176 | 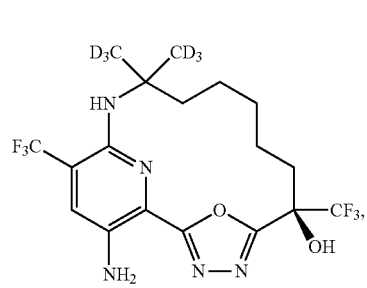 [SMILES: [2H]C([2H])([2H])C1(C([2H])([2H])[2H])CCCCC[C@](O)(C(F)(F)F)c2nnc(o2)-c2nc(c(C(F)(F)F)cc2N)N1] |

| Compound No. | Structure |
|---|---|
| 177 | 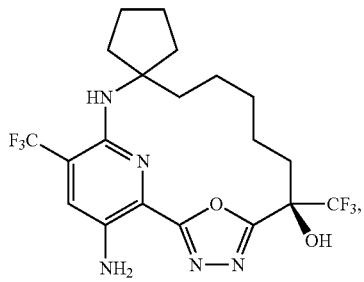 [SMILES: Nc1cc(C(F)(F)F)c2nc1-c1nnc(o1)[C@@](O)(C(F)(F)F)CCCCCC1(CCCC1)N2] |
| 178 | 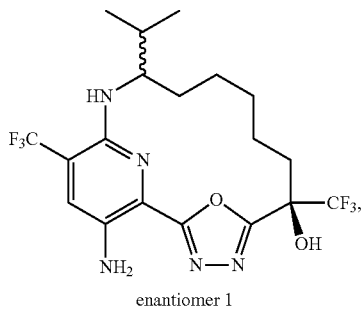 [SMILES: CC(C)C1CCCCC[C@](O)(C(F)(F)F)C2=NN=C(O2)c2nc(c(C(F)(F)F)cc2N)N1]<br>enantiomer 1 |
| 179 | 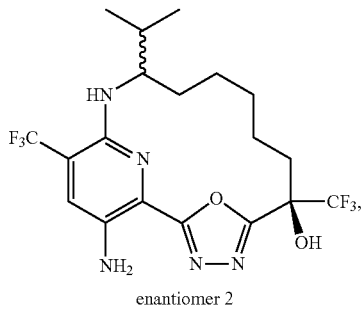 [SMILES: CC(C)C1CCCCC[C@](O)(C(F)(F)F)C2=NN=C(O2)c2nc(c(C(F)(F)F)cc2N)N1]<br>enantiomer 2 |
| 180 | 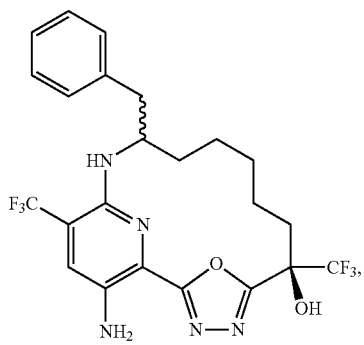<br>enantiomer 1 |
| Compound No. | Structure |
|---|---|
| 181 | 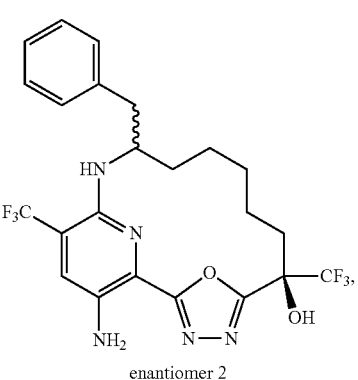 [SMILES: Nc1cc(C(F)(F)F)c2nc1C1=NN=C(O1)[C@@](O)(C(F)(F)F)CCCCCC(Cc1ccccc1)N2]<br>enantiomer 2 |
| 182 | 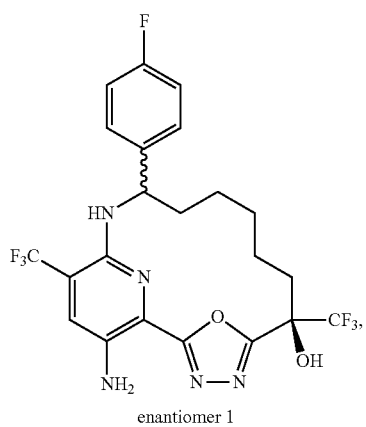 [SMILES: Nc1cc(C(F)(F)F)c2nc1C1=NN=C(O1)[C@@](O)(C(F)(F)F)CCCCCC(c1ccc(F)cc1)N2]<br>enantiomer 1 |
| 183 | 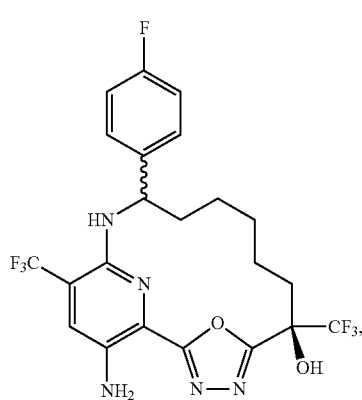<br>enantiomer 2 |

| Compound No. | Structure |
|---|---|
| 184 | enantiomer 1 |
| 185 | enantiomer 2 |
| 186 | 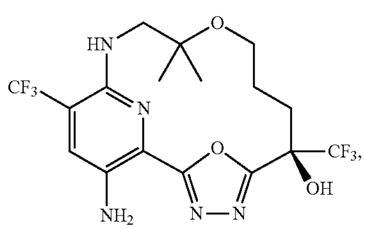 [SMILES: CC1(C)CNc2nc(c(N)cc2C(F)(F)F)C2=NN=C(O2)[C@@](O)(C(F)(F)F)CCCO1] |
| 187 | 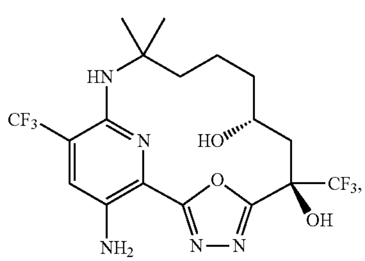 [SMILES: CC1(C)CCC[C@@H](O)C[C@](O)(C(F)(F)F)C2=NN=C(O2)c2nc(c(C(F)(F)F)cc2N)N1] |
| 188 | 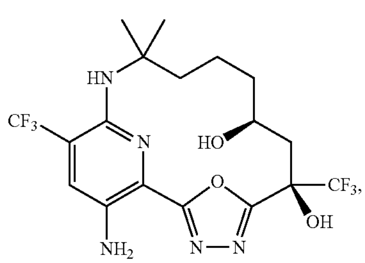 [SMILES: CC1(C)CCC[C@H](O)C[C@](O)(C(F)(F)F)C2=NN=C(O2)c2nc(c(C(F)(F)F)cc2N)N1] |
| 189 | enantiomer 1 |
| 190 | enantiomer 2 |
| 191 | enantiomer 1 |
| 192 | enantiomer 2 |
| 193 | |

| Compound No. | Structure |
|---|---|
| 194 | 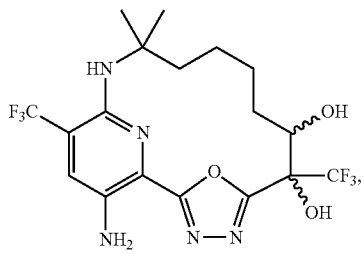<br>enantiomer 1, cis diol |
| 195 | 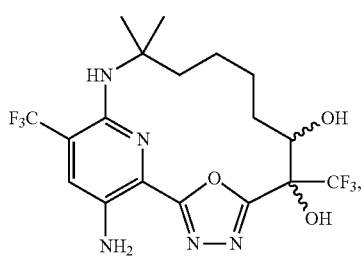<br>enantiomer 2, cis diol |
| 196 | 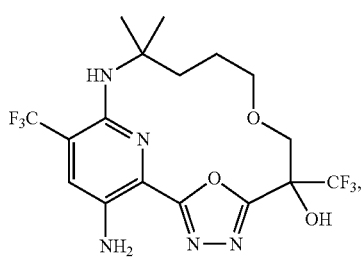 [SMILES: CC1(C)CCCOCC(O)(C(F)(F)F)C2=NN=C(O2)c2nc(c(C(F)(F)F)cc2N)N1] |
| 197 | 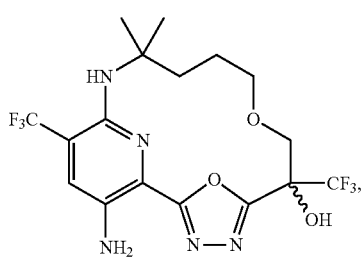<br>enantiomer 1 |
| 198 | 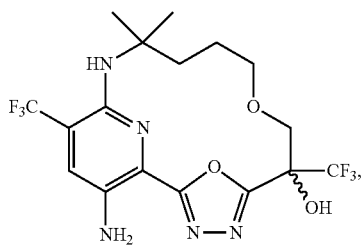<br>enantiomer 2 |
| Compound No. | Structure |
|---|---|
| 199 | 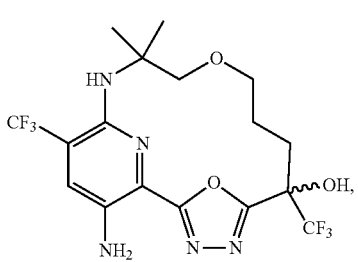<br>enantiomer 1 |
| 200 | 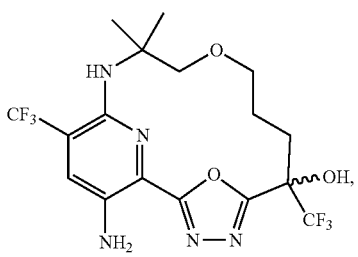<br>enantiomer 2 |
| 201 | 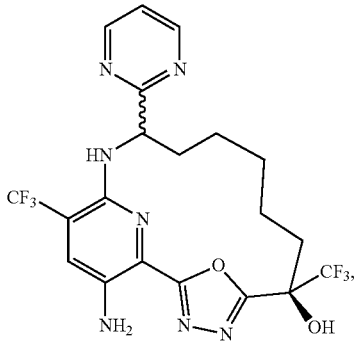<br>enantiomer 1 |
| 202 | 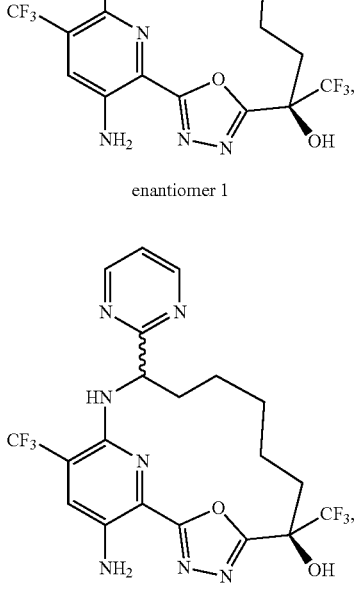<br>enantiomer 2 |

| Compound No. | Structure |
|---|---|
| 203 | 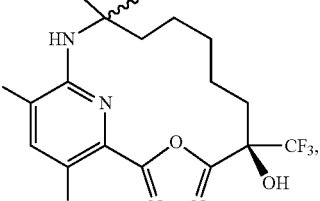<br>enantiomer 1 |
| 204 | enantiomer 2 |
| 205 | 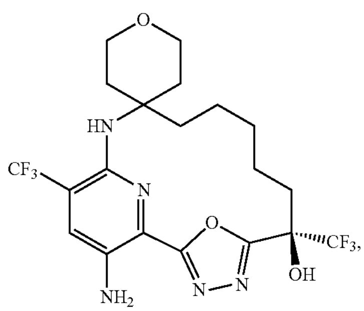 [SMILES: Nc1cc(C(F)(F)F)c2nc1C1=NN=C(O1)[C@@](O)(C(F)(F)F)CCCCCC1(CCOCC1)N2] |
| 206 | 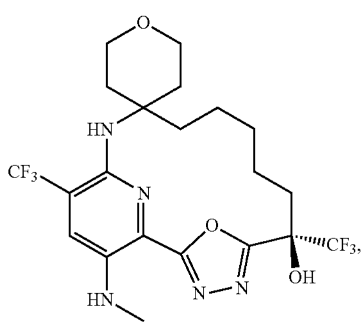 [SMILES: CNc1cc(C(F)(F)F)c2nc1C1=NN=C(O1)[C@@](O)(C(F)(F)F)CCCCCC1(CCOCC1)N2] |
| 207 | enantiomer 1 |
| 208 | 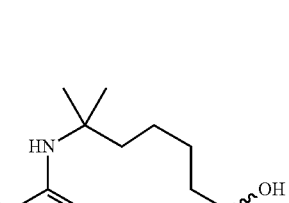<br>enantiomer 2 |
| 209 | enantiomer 1, trans diol |
| 210 | enantiomer 2, trans diol |
| 211 | enantiomer 1 |

| Compound No. | Structure |
|---|---|
| 212 | 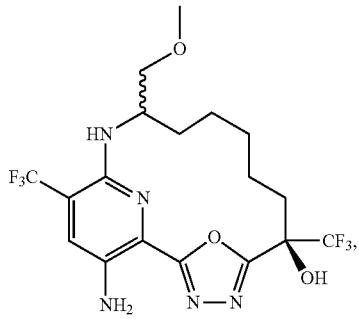<br>enantiomer 2 |
| 213 | 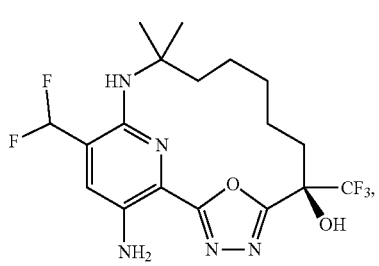 [SMILES: CC1(C)CCCCC[C@](O)(C(F)(F)F)c2nnc(o2)-c2nc(c(C(F)F)cc2N)N1] |
| 214 | 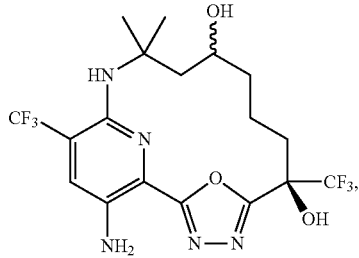<br>diastereomer 1 |
| 215 | 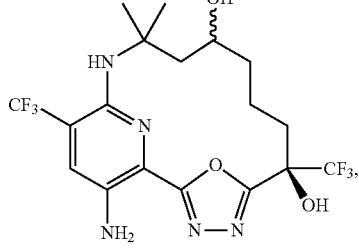<br>diastereomer 2 |
| 216 | 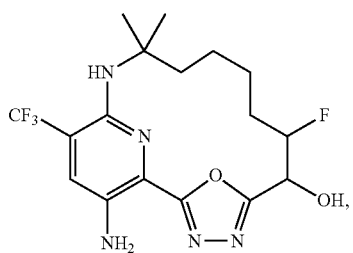 [SMILES: CC1(C)CCCCCC(O)c2nnc(o2)-c2nc(c(C(F)(F)F)cc2N)N1]<br>mixture of diastereomers |
| Compound No. | Structure |
|---|---|
| 217 | 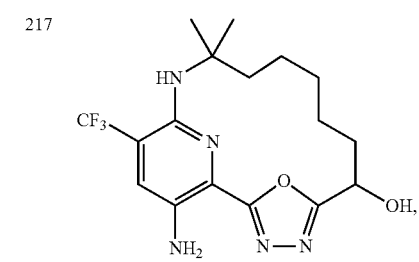 |
| 218 | 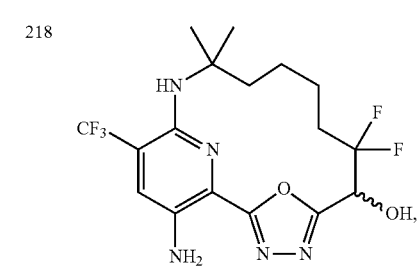<br>enantiomer 1 |
| 219 | 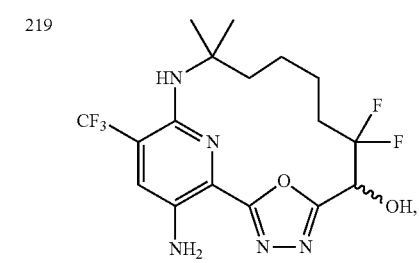<br>enantiomer 2 |
| 220 | 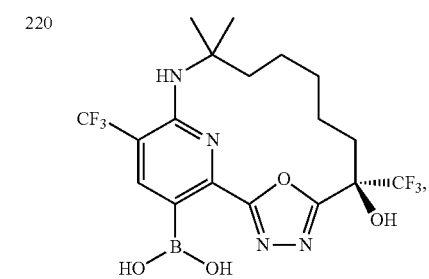 |
| 221 | 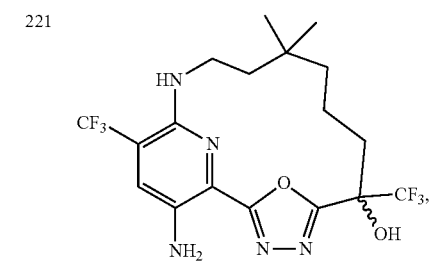<br>enantiomer 1 |

| Compound No. | Structure |
|---|---|
| 222 | (structure shown, enantiomer 2) | a deuterated derivative thereof, or a pharmaceutically acceptable salt of any of the forgoing.

29. A compound according to claim 28, wherein the compound is:

| Comp. No. | Structure |
|---|---|
| 4 | (structure shown) |
| 19 | (structure shown, enantiomer 1) |
| 32 | (structure shown, enantiomer 1) |
| 138 | (structure shown) |
| 163 | (structure shown) |
| 173 | (structure shown) |
| 176 | (structure shown) |
| 177 | (structure shown) |

| Comp. No. | Structure |
|---|---|
| 178 | 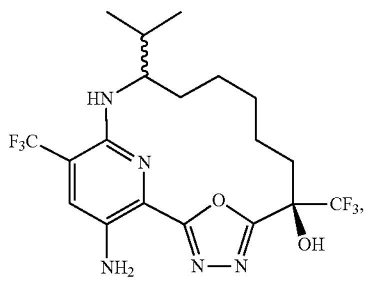 [SMILES: CC(C)C1CCCCC[C@](O)(C(F)(F)F)c2nnc(o2)-c2nc(c(C(F)(F)F)cc2N)N1] |
| 182 | 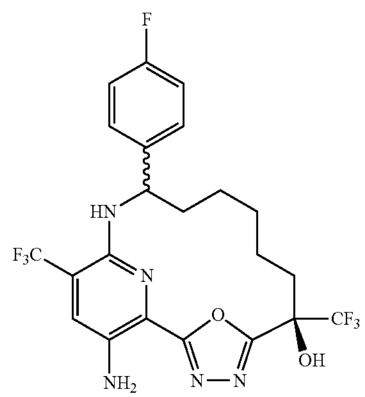 [SMILES: Nc1cc(C(F)(F)F)c2nc1C1=NN=C(O1)[C@@](O)(C(F)(F)F)CCCCCC(c1ccc(F)cc1)N2] |
| 192 | 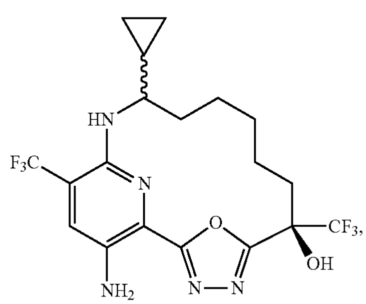 |
| 193 | 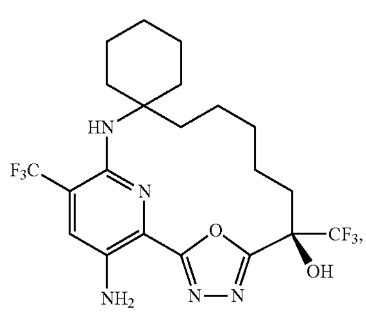 [SMILES: Nc1cc(C(F)(F)F)c2nc1C1=NN=C(O1)[C@@](O)(C(F)(F)F)CCCCCC1(CCCCC1)N2] |

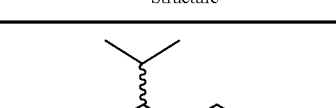

| Comp. No. | Structure |
|---|---|
| 205 | 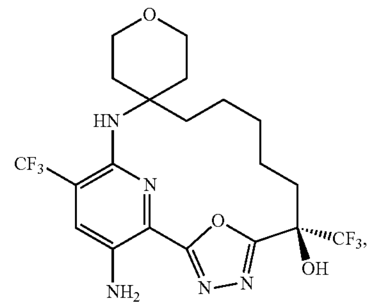 [SMILES: Nc1cc(C(F)(F)F)c2nc1C1=NN=C(O1)[C@@](O)(C(F)(F)F)CCCCCC1(CCOCC1)N2] |

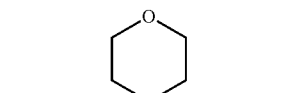

a deuterated derivative thereof, or a pharmaceutically acceptable salt of any of the forgoing.

30. A pharmaceutical composition comprising a compound, salt, or deuterated derivative according to claim 1 and a pharmaceutically acceptable carrier.

31. The pharmaceutical composition according to claim 30, further comprising one or more additional therapeutic agent(s).

32. A method of treating cystic fibrosis, comprising administering an effective amount of the compound, salt, or deuterated derivative according to claim 1.

33. The method according to claim 32, further comprising administering one or more additional therapeutic agent(s).

34. A compound according to claim 1, wherein the compound is:

| Compound No. | Structure |
|---|---|
| 4 | 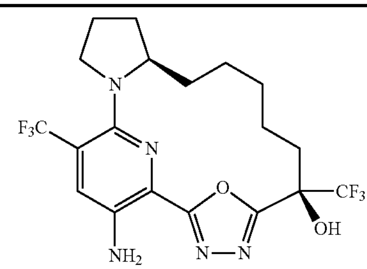 |
| 5 | 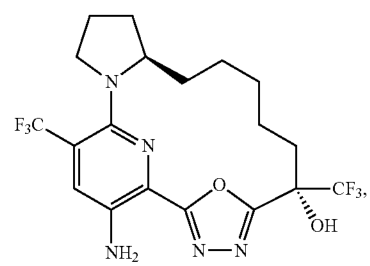 [SMILES: Nc1cc(C(F)(F)F)c2nc1C1=NN=C(O1)[C@](O)(C(F)(F)F)CCCCC[C@@H]1CCCN21] |
| 19 | 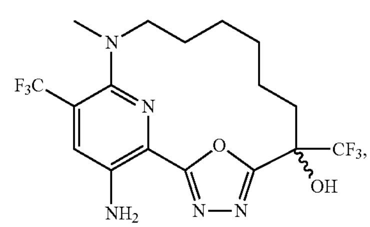 |

| Compound No. | Structure |
|---|---|
| 41 | (structure) |
| 52 | (structure) |
| 60 | (structure) |
| 70 | (structure) |
| 163 | (structure) |

| Compound No. | Structure |
|---|---|
| 173 | (structure) |
| 175 | (structure) |
| 188 | (structure) | a deuterated derivative thereof, or a pharmaceutically acceptable salt of any of the forgoing.

35. A compound according to claim 34, wherein Compound 4 is substantially amorphous Compound 4.

36. A compound according to claim 34, wherein Compound 5 is substantially crystalline Compound 5 Form A.

37. A compound according to claim 34, wherein Compound 19 is substantially amorphous Compound 19.

38. A compound according to claim 34, wherein Compound 41 is substantially crystalline Compound 41 Form A.

39. A compound according to claim 34, wherein Compound 52 is substantially crystalline Compound 52 Form A.

40. A compound according to claim 34, wherein Compound 60 is substantially amorphous Compound 60.

41. A compound according to claim 34, wherein Compound 70 is substantially amorphous Compound 70.

42. A compound according to claim 34, wherein Compound 163 is substantially crystalline Compound 163 Form A.

43. A compound according to claim 34, wherein Compound 173 is substantially amorphous Compound 173.

44. A compound according to claim 34, wherein Compound 173 is substantially crystalline Compound 173 Form A.

45. A compound according to claim 34, wherein Compound 175 is substantially crystalline Compound 175 Form A.

46. A compound according to claim 34, wherein Compound 188 is substantially crystalline Compound 188 dichloromethane solvate Form A.

47. A process for preparing a compound of Formula 7-7:

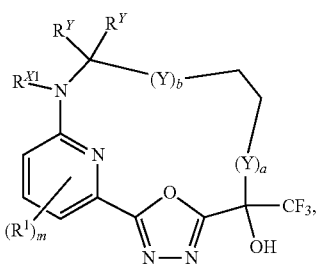

comprising converting a compound of Formula 7-6:

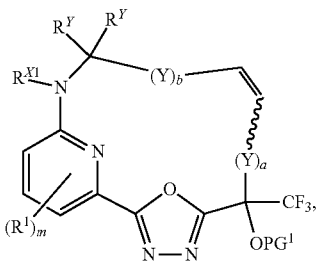

into a compound of Formula 7-7, wherein:
R$^{X1}$ is selected from H, C$_1$-C$_6$ alkyl (optionally substituted with 1-3 groups independently selected from hydroxy, oxo, —OR$^{X2}$, and —N(R$^{X2}$)$_2$), and C$_3$-C$_8$ cycloalkyl;
each R$^{X2}$ is independently selected from H and C$_1$-C$_6$ alkyl;
each Y is independently selected from —C(R$^Y$)$_2$—, —O—, —CO—, —NR$^{YN}$—, and

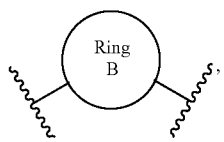

wherein each R$^{YN}$ is independently selected from H, C$_1$-C$_4$ alkyl, and CO$_2$R$^{YN1}$, wherein each R$^{YN1}$ is independently selected from C$_1$-C$_4$ alkyl and C$_3$-C$_6$ cycloalkyl;
each R$^Y$ is independently selected from hydrogen, hydroxy, halogen, C$_1$-C$_6$ alkyl (optionally substituted with 1-3 groups independently selected from hydroxy, C$_1$-C$_6$ alkoxy, and Q), C$_3$-C$_8$ cycloalkyl, C$_6$-C$_{10}$ aryl (optionally substituted with 1-3 groups independently selected from halogen), 5- to 10-membered heteroaryl, —OR$^{Y1}$, —CO$_2$R$^{Y1}$, —COR$^{Y1}$, —CON(R$^{Y1}$)$_2$, and —N(R$^{Y1}$)$_2$;
or two R$^Y$ on the same atom are taken together to form a ring selected from C$_3$-C$_8$ cycloalkyl and 3- to 7-membered heterocyclyl; or two R$^Y$, one of which is on one atom and the second of which is on an adjacent atom, are taken together to form a pi bond;
each R$^{Y1}$ is independently selected from hydrogen and C$_1$-C$_6$ alkyl, or two R$^{Y1}$ bonded to the same nitrogen taken together form a 3- to 6-membered heterocyclyl;

Ring B is selected from:
C$_6$-C$_{10}$ aryl (optionally substituted with 1-3 groups independently selected from halogen, C$_1$-C$_6$ alkyl, and C$_1$-C$_6$ alkoxy),
C$_3$-C$_8$ cycloalkyl,
5- to 10-membered heteroaryl, and
3- to 6-membered heterocyclyl (optionally substituted with 1-3 groups independently selected from C$_1$-C$_6$ alkyl);
each Q is independently selected from:
C$_1$-C$_6$ alkyl optionally substituted with 1-3 groups independently selected from:
halogen,
oxo,
C$_6$-C$_{10}$ aryl (optionally substituted with 1-3 groups independently selected from halogen and —OCF$_3$), and
C$_3$-C$_8$ cycloalkyl,
C$_3$-C$_8$ cycloalkyl optionally substituted with 1-3 groups independently selected from:
halogen,
CN,
C$_1$-C$_6$ alkyl (optionally substituted with 1-3 groups independently selected from halogen, —NH$_2$, and —NHCOMe),
C$_1$-C$_6$ alkoxy,
C$_6$-C$_{10}$ aryl (optionally substituted with 1-3 groups independently selected from C$_1$-C$_6$ alkyl), and
C$_3$-C$_8$ cycloalkyl,
C$_6$-C$_{10}$ aryl optionally substituted with 1-3 groups independently selected from:
halogen,
CN,
C$_1$-C$_6$ alkyl (optionally substituted with 1-3 groups independently selected from halogen and hydroxy),
C$_1$-C$_6$ alkoxy optionally substituted with 1-4 groups independently selected from:
halogen,
C$_3$-C$_8$ cycloalkyl (optionally substituted with CF$_3$),
C$_3$-C$_8$ cycloalkyl (optionally substituted with 1-3 groups independently selected from halogen, CF$_3$, OCF$_3$, and C$_1$-C$_6$ alkyl), and
C$_6$-C$_{10}$ aryl,
5- to 10-membered heteroaryl optionally substituted with 1-3 groups independently selected from:
halogen,
C$_1$-C$_6$ alkyl (optionally substituted with 1-3 groups independently selected from halogen),
C$_3$-C$_8$ cycloalkyl (optionally substituted with 1-3 CF$_3$ groups), and
3- to 10-membered heterocyclyl,
3- to 10-membered heterocyclyl optionally substituted with 1-3 groups independently selected from:
C$_1$-C$_6$ alkyl (optionally substituted with 1-3 groups independently selected from oxo and C$_3$-C$_8$ cycloalkyl), and
oxo;
each R$^1$ is independently selected from halogen, C$_1$-C$_6$ fluoroalkyl, C$_1$-C$_6$ alkyl (optionally substituted with a group selected from hydroxy, C$_6$-C$_{10}$ aryl, and 5- to 6-membered heteroaryl), —OR$^2$, —N(R$^2$)$_2$, —NO$_2$, —CO$_2$R$^2$, —CO—N(R$^2$)$_2$, —CN, C$_3$-C$_8$ cycloalkyl, C$_6$-C$_{10}$ aryl, 5- to 6-membered heteroaryl (optionally substituted with 1-3 groups independently selected from $C_1$-$C_6$ alkyl), 3- to 6-membered heterocyclyl, —B(OR$^2$)$_2$, —SO$_2$R$^2$, —SR$^2$, —SOR$^2$, —PO(OR$^2$)$_2$, and —PO(R$^2$)$_2$;

each R$^2$ is independently selected from hydrogen, $C_1$-$C_6$ alkyl (optionally substituted with 1-6 groups independently selected from halogen), $C_1$-$C_6$ fluoroalkyl, and $C_6$-$C_{10}$ aryl (optionally substituted with 1-3 groups independently selected from $C_1$-$C_6$ fluoroalkyl and $C_1$-$C_6$ fluoroalkoxy);

m is selected from 0, 1, 2, and 3;

each of a and b is an integer independently selected from 0, 1, 2, and 3, provided that the sum of a and b is not greater than 4; and PG$^1$ is selected from suitable oxygen protecting groups.

48. A compound of the formula:

(Compound 163)

a deuterated derivative thereof, or a pharmaceutically acceptable salt of any of the foregoing.

49. A compound of the formula:

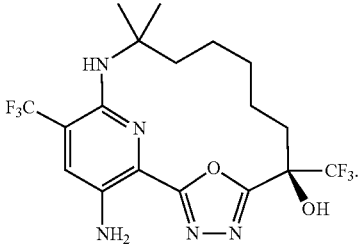

(Compound 163)

50. A pharmaceutical composition comprising the compound, deuterated derivative, or pharmaceutically acceptable salt according to claim 48, and a pharmaceutically acceptable carrier.

51. The pharmaceutical composition according to claim 50, further comprising one or more additional therapeutic agent(s).

52. A method of treating cystic fibrosis, comprising administering an effective amount of the compound, deuterated derivative, or pharmaceutically acceptable salt according to claim 48.

53. The method of claim 52, further comprising administering one or more additional therapeutic agent(s).

\* \* \* \* \*